United States Patent
Yamaki et al.

(10) Patent No.: US 10,290,815 B2
(45) Date of Patent: May 14, 2019

(54) COMPOSITION, COMPOUND, MATERIAL FOR ORGANIC ELECTROLUMINESCENCE ELEMENT, INK COMPOSITION, ORGANIC ELECTROLUMINESCENCE ELEMENT, AND ELECTRONIC DEVICE

(71) Applicant: IDEMITSU KOSAN CO., LTD., Chiyoda-ku (JP)

(72) Inventors: Taro Yamaki, Chiba (JP); Kiyoshi Ikeda, Sodegaura (JP); Hironori Kawakami, Katsushika-ku (JP)

(73) Assignee: IDEMITSU KOSAN CO., LTD., Chiyoda-ku (JP)

( * ) Notice: Subject to any disclaimer, the term of this patent is extended or adjusted under 35 U.S.C. 154(b) by 135 days.

(21) Appl. No.: 15/125,085

(22) PCT Filed: Mar. 12, 2015

(86) PCT No.: PCT/JP2015/057392
§ 371 (c)(1),
(2) Date: Sep. 9, 2016

(87) PCT Pub. No.: WO2015/137472
PCT Pub. Date: Sep. 17, 2015

(65) Prior Publication Data
US 2017/0062733 A1    Mar. 2, 2017

(30) Foreign Application Priority Data

Mar. 12, 2014 (JP) .................................. 2014-049545
Mar. 12, 2014 (JP) .................................. 2014-049546
(Continued)

(51) Int. Cl.
*H01L 51/50* (2006.01)
*H01L 51/00* (2006.01)
(Continued)

(52) U.S. Cl.
CPC ........ *H01L 51/0072* (2013.01); *C07D 209/86* (2013.01); *C07D 251/24* (2013.01);
(Continued)

(58) Field of Classification Search
None
See application file for complete search history.

(56) References Cited

U.S. PATENT DOCUMENTS

2012/0235133 A1    9/2012  Kai et al.
2013/0112952 A1*   5/2013  Adamovich ........ H01L 51/0054
                                                      257/40
(Continued)

FOREIGN PATENT DOCUMENTS

CN    102265424 A    11/2011
CN    102439004 A    5/2012
(Continued)

OTHER PUBLICATIONS

Yamoto et al., Synthesis of Novel Carbazole Dendrimers Having a Metal Coordination Site, 2003, Chemistry Letters vol. 32, No. 8, pp. 674-675). (Year: 2003).*

(Continued)

*Primary Examiner* — Gregory D Clark
(74) *Attorney, Agent, or Firm* — Oblon, McClelland, Maier & Neustadt, L.L.P.

(57) ABSTRACT

A composition or a compound suitable for use in forming the layer of organic EL device by a coating method, a material for organic electroluminescence devices including the composition or the compound, an ink composition including the composition or the compound, an organic electroluminescence device employing the composition or the compound, and an electronic device including the organic electroluminescence device are provided. The compound includes a nitrogen-containing hetero aromatic hydrocarbon group (Continued)

which has a substituent with a specific structure. The composition includes the compound.

18 Claims, 1 Drawing Sheet

(30) Foreign Application Priority Data

| Mar. 12, 2014 | (JP) | ................................ | 2014-049547 |
|---|---|---|---|
| Mar. 12, 2014 | (JP) | ................................ | 2014-049548 |
| Mar. 26, 2014 | (JP) | ................................ | 2014-064788 |

(51) Int. Cl.

| *C07D 403/14* | (2006.01) |
|---|---|
| *C07D 405/14* | (2006.01) |
| *C07D 409/14* | (2006.01) |
| *C07D 491/048* | (2006.01) |
| *C07D 495/04* | (2006.01) |
| *C09D 5/24* | (2006.01) |
| *C09K 11/02* | (2006.01) |
| *C07D 403/12* | (2006.01) |
| *C07D 401/14* | (2006.01) |
| *C07D 333/76* | (2006.01) |
| *C07D 401/04* | (2006.01) |
| *C07D 403/04* | (2006.01) |
| *C07D 405/10* | (2006.01) |
| *C07D 251/24* | (2006.01) |
| *C07D 471/04* | (2006.01) |
| *C07D 487/04* | (2006.01) |
| *C07D 209/86* | (2006.01) |
| *C07D 307/91* | (2006.01) |

(52) U.S. Cl.
CPC ......... *C07D 307/91* (2013.01); *C07D 333/76* (2013.01); *C07D 401/04* (2013.01); *C07D 401/14* (2013.01); *C07D 403/04* (2013.01); *C07D 403/12* (2013.01); *C07D 403/14* (2013.01); *C07D 405/10* (2013.01); *C07D 405/14* (2013.01); *C07D 409/14* (2013.01); *C07D 471/04* (2013.01); *C07D 487/04* (2013.01); *C07D 491/048* (2013.01); *C07D 495/04* (2013.01); *C09D 5/24* (2013.01); *C09K 11/025* (2013.01); *H01L 51/006* (2013.01); *H01L 51/0058* (2013.01); *H01L 51/0061* (2013.01); *H01L 51/0067* (2013.01); *H01L 51/0071* (2013.01); *H01L 51/0073* (2013.01); *H01L 51/0074* (2013.01); *H01L 51/0085* (2013.01); *H01L 51/5012* (2013.01); *H01L 51/5016* (2013.01)

(56) References Cited

U.S. PATENT DOCUMENTS

| 2013/0306959 A1 | 11/2013 | Ikeda et al. |
|---|---|---|
| 2014/0048745 A1 | 2/2014 | Anemian et al. |

FOREIGN PATENT DOCUMENTS

| CN | 102448946 A | 5/2012 |
|---|---|---|
| CN | 103254113 A | 8/2013 |
| CN | 103270032 A | 8/2013 |
| WO | WO 2010/136109 A1 | 12/2010 |
| WO | WO 2011/080972 A1 | 7/2011 |
| WO | WO 2011/136755 A1 | 11/2011 |
| WO | WO 2011/137072 A1 | 11/2011 |
| WO | WO 2012/086170 A1 | 6/2012 |
| WO | WO 2013/081088 A1 | 6/2013 |
| WO | WO 2015/020217 A1 | 2/2015 |

OTHER PUBLICATIONS

International Search Report dated May 26, 2015, in PCT/JP2015/057392 filed Mar. 12, 2015.
Combined Chinese Office Action and Search Report dated Jul. 10, 2018 in Patent Application No. 201580013540.6.
Office Action as received in the corresponding Chinese patent application No. 201580013540.6 dated Jan. 24, 2019 w/English translation.

* cited by examiner

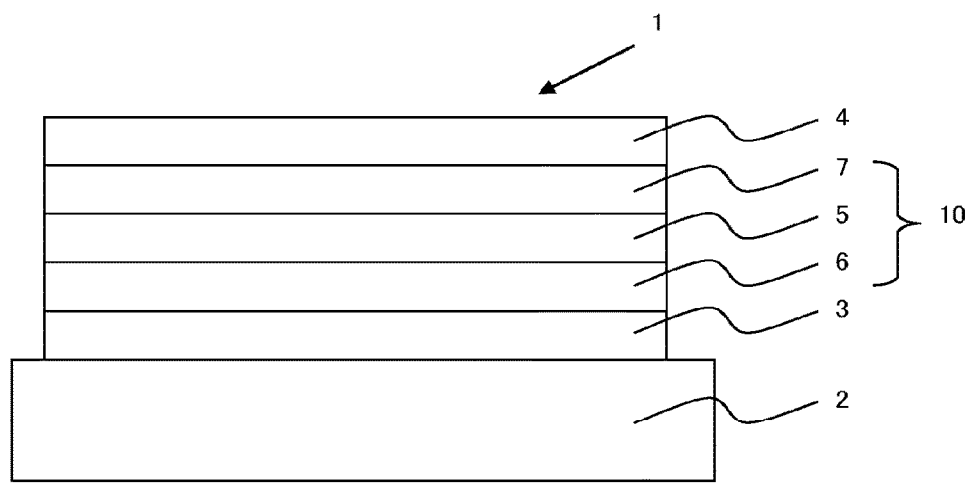

COMPOSITION, COMPOUND, MATERIAL FOR ORGANIC ELECTROLUMINESCENCE ELEMENT, INK COMPOSITION, ORGANIC ELECTROLUMINESCENCE ELEMENT, AND ELECTRONIC DEVICE

TECHNICAL FIELD

The present invention relates to compositions, compounds, materials for organic electroluminescence devices, ink compositions, organic electroluminescence devices, and electronic devices.

BACKGROUND ART

Organic electroluminescence devices (hereinafter also referred to as "organic EL device") have been known, in which an organic thin film layer including a light emitting layer is disposed between an anode and a cathode, and the energy of exciton generated by the recombination of hole and electron which are injected into a light emitting layer is converted into light.

Utilizing its advantages as the spontaneous emitting device, the organic EL device has been expected to provide a light emitting device excellent in the emission efficiency, the image quality, the power consumption, and the freedom of design. It has been known to make the light emitting layer into a host/dopant emitting layer in which a host is doped with an emission material as a dopant.

In a host/dopant emitting layer, excitons can be efficiently generated from charges injected into a host. The energy of generated excitons is transferred to the dopant, and the light emission from the dopant with high efficiency can be obtained.

To improve the performance of organic EL devices, the recent study is directed also to the host/dopant system, and the search for a suitable host material and other materials for organic EL devices has been continued.

The method for forming each layer of an organic EL device is classified roughly into a vapor deposition method, such as a vacuum vapor deposition method and a molecular beam evaporation method, and a coating method, such as a dipping method, a spin coating method, a casting method, a bar coating method, and a roll coating method. The material for use in forming the layer by a coating method is required to satisfy the properties not required in the material for use in the vapor deposition method, for example, temperature resistance and solubility in solvents. Therefore, a material useful in the vapor deposition method is not necessarily useful in the coating method. In addition, the material is required to be capable of forming the layer by a coating method and further required to meet various performances necessary for organic EL devices.

Particularly, since the coating method for forming the layer is applicable to the production of a large-sized organic EL display and lighting panel, an material for organic EL devices applicable to the coating method has been desired to develop.

CITATION LIST

Patent Literature

Patent Literature 1: WO 2012/086170

SUMMARY OF INVENTION

Technical Problem

An object of the invention is to provide a composition or a compound suitable for use in forming the layer of organic EL device by a coating method. Another object is to provide a material for organic electroluminescence devices comprising the composition or the compound, an ink composition comprising the composition or the compound, an organic electroluminescence device employing the composition or the compound, and an electronic device comprising the organic electroluminescence device.

Solution to Problem

As a result of extensive research, the inventors have found that the above problem is solved by a compound comprising a nitrogen-containing heteroaromatic hydrocarbon group which has a substituent with a specific structure or a composition comprising such a compound.

In an aspect of the invention, the following (1) to (6) are provided:

(1) a composition comprising a compound represented by formula (1) and at least one compound selected from compounds represented by any of formulae (CH1), (CH3), (CH4), (CH5), (CH6), (CH14), and (CH15):

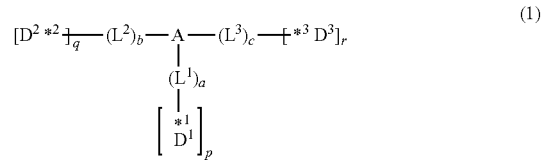

in formula (1),

A represents a substituted or unsubstituted nitrogen-containing heteroaromatic hydrocarbon group having 5 to 30 ring atoms;

$L^1$ to $L^3$ each independently represent a substituted or unsubstituted aromatic hydrocarbon group having 6 to 30 ring carbon atoms, a substituted or unsubstituted heterocyclic group having 5 to 30 ring atoms, or a group wherein 2 to 4 groups selected from the preceding groups are bonded to each other;

a to c each independently represent 0 or 1;

p to r each independently represent an integer of 0 to 3, p+q+r=3, and two or more groups $D^1$, two or more groups $D^2$ and two or more groups $D^3$ when p, q or r is 2 or 3 may be the same or different, respectively; and

*1 to *3 are respectively bonded to $D^1$ to $D^3$, and $D^1$ to $D^3$ each independently represent a substituent selected from Group A to Group D each respectively represented by formulae ($D^A$) to ($D^D$);

Group A

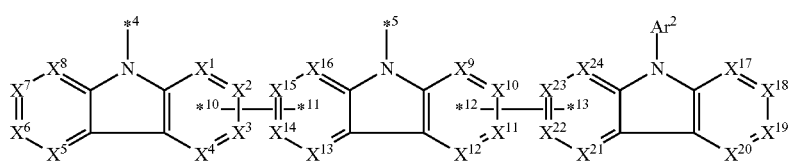

(D⁴)

Group B

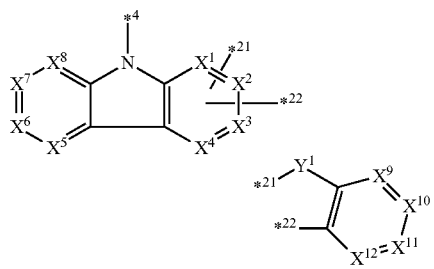

-continued

Group C

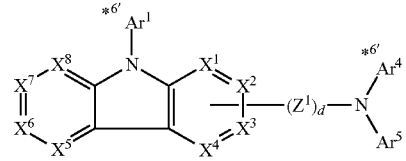

Group D

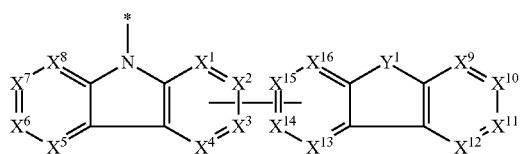

in formula ($D^A$) which represents the substituent belonging to Group A, one of *4 and *5 is bonded to one of *1 to *3 of formula (1) and the other is bonded to $Ar^1$;

$Ar^1$ and $Ar^2$ each independently represent a substituted or unsubstituted aryl group having 6 to 30 ring carbon atoms or a substituted or unsubstituted heteroaryl group having 5 to 30 ring atoms one of $X^1$ to $X^4$ and one of $X^{13}$ to $X^{16}$ represent carbon atoms which are respectively bonded to *10 and *11, and the other six each independently represent C(R) or a nitrogen atom;

one of $X^9$ and $X^{12}$ and one of $X^{21}$ to $X^{24}$ represent carbon atoms which are respectively bonded to *12 and *13, and the other six each independently represent C(R) or a nitrogen atom;

$X^5$ to $X^8$ and $X^{17}$ to $X^{20}$ each independently represent C(R) or a nitrogen atom; and R represents a hydrogen atom or a substituent, two or more groups R may be the same or different, and two selected from groups R may be bonded to each other to form a ring;

in formula ($D^B$) which represents the substituent belonging to Group B, two of $X^1$ to $X^4$ represent carbon atoms which are respectively bonded to *21 and *22, and the other two independently represent C(R) or a nitrogen atom;

$X^5$ to $X^{12}$ each independently represent C(R) or a nitrogen atom;

R represents a hydrogen atom or a substituent, two or more groups R may be the same or different, and two selected from groups R may be bonded to each other to form a ring;

$Y^1$ represents an oxygen atom, a sulfur atom, —C($R^A$)($R^B$)—, —Si($R^C$)($R^D$)—, —P($R^E$)—, —P(=O)($R^F$)—, —S(=O)$_2$—, —P(=S)($R^G$)—, or —N($R^H$)—;

$R^A$ to $R^H$ each independently represent a hydrogen atom or a substituent, and $R^A$ and $R^B$, and $R^C$ and $R^D$ may be bonded to each other to form a ring; and

* is bonded to one of *1 to *3 of formula (1);

in formula ($D^C$) which represents the substituent belonging to Group C, $X^1$ to $X^8$ each represent C($R^1$) to C($R^8$), respectively, or a nitrogen atom;

$R^1$ to $R^8$ each independently represent a hydrogen atom or a substituent, provided that one of $X^1$ to $X^4$ represents a carbon atom which is directly bonded to $Z^1$ or the nitrogen atom to which $Ar^4$ and $Ar^5$ are bonded, and two selected from $R^1$ to $R^8$ not involved in the above direct bonding may be bonded to each other to form a ring;

$Ar^1$, $Ar^4$ and $Ar^5$ each independently represent a substituted or unsubstituted aryl group having 6 to 30 ring carbon atoms or a substituted or unsubstituted heteroaryl group having 5 to 30 ring atoms;

$Z^1$ independently represents a substituted or unsubstituted aromatic hydrocarbon group having 6 to 30 ring carbon atoms, a substituted or unsubstituted heterocyclic group having 5 to 30 ring atoms, or a group wherein 2 to 4 groups selected from the preceding groups are bonded to each other;

d is 0 or 1; and one of *1 to *3 of formula (1) is directly bonded to a nitrogen atom from which one of $Ar^1$ and $Ar^4$ indicated by *6' is removed;

in formula ($D^D$) which represents the substituent belonging to Group D, $X^1$ to $X^{16}$ each represent C($R^1$) to C($R^{16}$), respectively, or a nitrogen atom;

$R^1$ to $R^{16}$ each independently represent a hydrogen atom or a substituent, provided that one of $X^1$ to $X^4$ represents a carbon atom which is directly bonded to a carbon atom represented by one of $X^{13}$ to $X^{16}$, and tow selected from $R^1$ to $R^8$ and two selected from $R^9$ to $R^{16}$, each not involved in the above direct bonding, may be bonded to each other to form a ring $Y^1$ represents an oxygen atom, a sulfur atom, C($R^A$)($R^B$), Si($R^C$)($R^D$), P($R^E$), P(=O)($R^F$), S(=O)$_2$, P(=S)($R^G$), or —N($R^H$)—;

$R^A$ to $R^H$ each independently represent a hydrogen atom or a substituent;

$R^A$ and $R^B$, and $R^C$ and $R^D$ may be bonded to each other to form a ring; and

* is bonded to one of *1 to *3 of formula (1);

$$A\text{---}(L^1\text{-}B)_m \qquad (CH1)$$

in formula (CH1),

A represents a substituted or unsubstituted aromatic heterocyclic group;

L¹ represents a single bond, a substituted or unsubstituted aromatic hydrocarbon group, or a substituted or unsubstituted aromatic heterocyclic group;

B represents a residue of a structure represented by formula (CH2);

m represents an integer of 2 or more:

two or more groups L¹ may be the same or different; and two or more groups B may be the same or different;

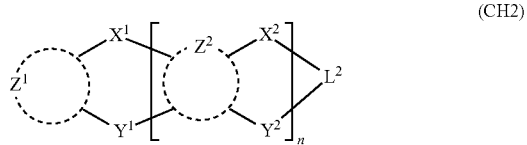
(CH2)

in formula (CH2), one of X¹ and Y¹ represents a single bond, —CR₂—, —NR—, —O—, —S—, or —SiR₂— and the other represents —NR—, —O—, —S— or —SiR₂—;

one of X² and Y² represents a single bond, —CR₂—, —NR—, —O—, —S—, or —SiR₂— and the other represents —NR—, —O—, —S—, or —SiR₂—;

R represents a hydrogen atom, a substituted or unsubstituted alkyl group, a substituted or unsubstituted cycloalkyl group, a substituted or unsubstituted aromatic hydrocarbon group, or a substituted or unsubstituted aromatic heterocyclic group;

Z¹ and Z² each independently represent a substituted or unsubstituted aliphatic hydrocarbon group, a substituted or unsubstituted aliphatic heterocyclic group, a substituted or unsubstituted aromatic hydrocarbon group, or a substituted or unsubstituted aromatic heterocyclic group;

L² represents a linking group; and n represents an integer of 0 to 5, and when n is two or more, two or more groups Z² may be the same or different, two or more groups X² may be the same or different, and two or more groups Y² may be the same or different;

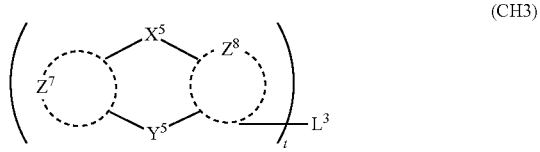
(CH3)

in formula (CH3),

X⁵ and Y⁵ each represent a single bond, —CR₂—, —NR—, —O—, —S—, or —SiR₂—, and X⁵ and Y⁵ cannot all be single bonds;

R is as defined above;

Z⁷ and Z⁸ are as defined above with respect to Z¹ and Z², provided that each of Z⁷ and Z⁸ cannot be an aliphatic hydrocarbon ring group having 3 or more fused rings, an aliphatic heterocyclic group having 3 or more fused rings, an aromatic hydrocarbon ring group having 3 or more fused rings, or a aromatic heterocyclic group having 3 or more fused rings;

t represents an integer of 1 or more; and

L³ represents a single bond, a substituted or unsubstituted aromatic hydrocarbon group, a substituted or unsubstituted aromatic heterocyclic group, or a combination thereof, provided that when t is 1, L³ is not a single bond;

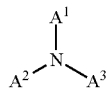
(CH4)

in formula (CH4),

A¹ to A³ each represent a substituted or unsubstituted aromatic hydrocarbon group or a substituted or unsubstituted aromatic heterocyclic group;

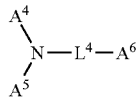
(CH5)

in formula (CH5),

L⁴ represents a substituted or unsubstituted divalent group wherein 1 to 4 aromatic hydrocarbon rings are bonded to each other or included or a substituted or unsubstituted divalent group wherein 1 to 4 aromatic heterocyclic rings are bonded to each other;

A⁴ to A⁶ each represent a substituted or unsubstituted aromatic hydrocarbon group or a substituted or unsubstituted aromatic heterocyclic group; and A⁴ and A⁵ may be bonded to each other to form a ring structure;

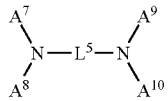
(CH6)

in formula (CH6),

L⁵ represents a substituted or unsubstituted divalent group wherein 1 to 6 aromatic hydrocarbon rings are bonded to each other or included or a substituted or unsubstituted divalent group wherein 1 to 6 aromatic heterocyclic rings are bonded to each other; and A⁷ to A¹⁰ each represent a substituted or unsubstituted group wherein 1 to 10 aromatic hydrocarbon rings are bonded to each other or a substituted or unsubstituted group wherein 1 to 10 aromatic heterocyclic rings are bonded to each other;

Ar¹—Ar²—Ar³ (CH7)

in formula (CH7),

Ar¹ and Ar³ each represent a substituted or unsubstituted monovalent aromatic hydrocarbon ring group or a substituted or unsubstituted monovalent aromatic heterocyclic group; and Ar² represents a substituted or unsubstituted group wherein 1 to 10 divalent aromatic hydrocarbon rings are bonded to each other or a substituted or unsubstituted group wherein 1 to 10 divalent aromatic heterocyclic rings are bonded to each other;

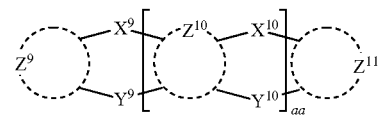
(CH14)

in formula (CH14), $X^9$, $X^{10}$, $Y^9$, and $Y^{10}$ each represent a single bond, —$CR_2$—, —NR—, —O—, —S—, —PR—, or —$SiR_2$—, and cannot all be single bonds;

R is as defined above with respect to R of $X^1$, $X^2$, $Y^1$, and $Y^2$ in formula (CH2);

$Z^9$, $Z^{10}$, and $Z^{11}$ are as defined above with respect to $Z^1$ and $Z^2$ of formula (CH2); and aa is an integer of 1 to 5, and when aa is an integer of 2 or more, two or more groups $Z^{10}$ may be the same or different, two or more groups $X^{10}$ may be the same or different, and two or more groups $Y^{10}$ may be the same or different; and

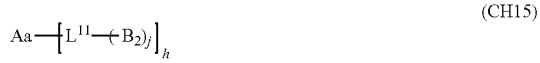

(CH15)

in formula (CH15),

Aa is as defined above with respect to A of formula (CH1);

$L^{11}$ is as defined above with respect to $L^1$ of formula (CH1);

$B_2$ is a residue of the above structure represented by formula (CH2);

h is an integer of 1 or more and an upper limit of h is not particularly limited and determined according to a structure of Aa, with 1 to 10 being preferred, 1 to 3 being more preferred, and 1 or 2 being still more preferred;

j is an integer of 1 or more and an upper limit of j is not particularly limited and determined according to a structure of $L^{11}$, with 2 or 3 being preferred;

provided that h+j is an integer of 3 or more; and two or more groups $L^{11}$ may be the same or different and two or more groups $B_2$ may be the same or different;

(2) a compound represented by formula (1);
(3) a material for organic electroluminescence devices comprising the composition of item (1) or the compound of item (2);
(4) an ink composition comprising a solvent and the composition of item (1) or the compound of item (2);
(5) an organic electroluminescence device comprising a cathode, an anode, and at least one organic thin film layer between the cathode and the anode, wherein the at least one organic thin film layer comprises a light emitting layer and at least one layer of the at least one organic thin film layer comprises the composition of item (1) or the compound of item (2); and
(6) an electronic device comprising the organic electroluminescence device of item (5).

Advantageous Effects of Invention

The present invention provides a composition or a compound suitable for use in forming the layer of organic EL device by a coating method.

BRIEF DESCRIPTION OF DRAWINGS

FIG. 1 is a schematic view of the structure of the organic EL device according to an embodiment of the invention.

DESCRIPTION OF EMBODIMENTS

The term of "XX to YY carbon atoms" referred to by "a substituted or unsubstituted group ZZ having XX to YY carbon atoms" used herein is the number of carbon atoms of the unsubstituted group ZZ and does not include any carbon atom in the substituent of the substituted group ZZ. "YY" is larger than "XX" and each of "XX" and "YY" represents an integer of 1 or more.

The term of "XX to YY atoms" referred to by "a substituted or unsubstituted group ZZ having XX to YY atoms" used herein is the number of atoms of the unsubstituted group ZZ and does not include any atom in the substituent of the substituted group ZZ. "YY" is larger than "XX" and each of "XX" and "YY" represents an integer of 1 or more.

The number of "ring carbon atoms" referred to herein means the number of the carbon atoms included in the atoms which are members forming the ring itself of a compound in which a series of atoms is bonded to form the ring (for example, a monocyclic compound, a fused ring compound, a cross-linked compound, a carbocyclic compound, and a heterocyclic compound). If the ring has a substituent, the carbon atom in the substituent is not included in the ring carbon atom. The same applies to the number of "ring carbon atom" described below, unless otherwise noted. For example, a benzene ring has 6 ring carbon atoms, a naphthalene ring has 10 ring carbon atoms, a pyridinyl group has 5 ring carbon atoms, and a furanyl group has 4 ring carbon atoms. If a benzene ring or a naphthalene ring has, for example, an alkyl substituent, the carbon atom in the alkyl substituent is not counted as the ring carbon atom of the benzene or naphthalene ring. In case of a fluorene ring to which a fluorene substituent is bonded (inclusive of a spirofluorene ring), the carbon atom in the fluorene substituent is not counted as the ring carbon atom of the fluorene ring.

The number of "ring atom" referred to herein means the number of the atoms which are members forming the ring itself (for example, a monocyclic ring, a fused ring, and a ring assembly) of a compound in which a series of atoms is bonded to form the ring (for example, a monocyclic compound, a fused ring compound, a cross-linked compound, a carbocyclic compound, and a heterocyclic compound). The atom not forming the ring (for example, hydrogen atom(s) for saturating the valence of the atom which forms the ring) and the atom in a substituent, if the ring is substituted, are not counted as the ring atom. The same applies to the number of "ring atoms" described below, unless otherwise noted. For example, a pyridine ring has 6 ring atoms, a quinazoline ring has 10 ring atoms, and a furan ring has 5 ring atoms. The hydrogen atom on the ring carbon atom of a pyridine ring or a quinazoline ring and the atom in a substituent are not counted as the ring atom. In case of a fluorene ring to which a fluorene substituent is bonded (inclusive of a spirofluorene ring), the atom in the fluorene substituent is not counted as the ring atom of the fluorene ring.

The definition of "hydrogen atom" used herein includes isotopes different in the neutron numbers, i.e., light hydrogen (protium), heavy hydrogen (deuterium), and tritium.

The terms of "heteroaryl group" and "heteroarylene group" used herein means a group having at least one hetero atom as a ring atom. The hetero atom is preferably at least one selected from a nitrogen atom, an oxygen atom, a sulfur atom, a silicon atom, and a selenium atom.

A "substituted or unsubstituted carbazolyl group" referred to herein includes the following carbazolyl groups:

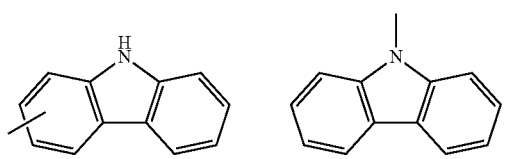

and a substituted carbazolyl group, wherein each of the above groups has an optional substituent.

The optional substituents may be bonded to each other to form a fused ring structure, may include a hetero atom, such as a nitrogen atom, an oxygen atom, a silicon atom, and selenium atom, and may be bonded to any of 1- to 9-positions. Examples of such substituted carbazolyl groups are shown below.

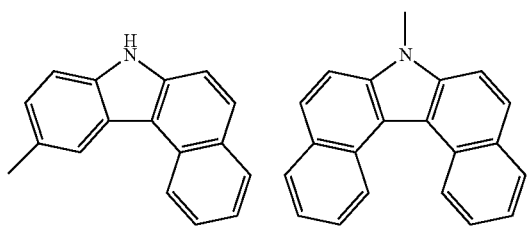

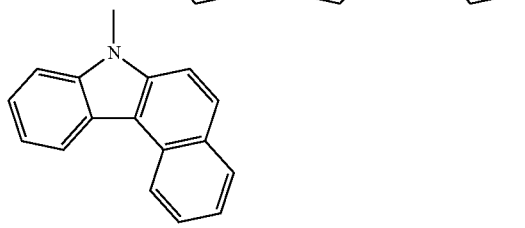

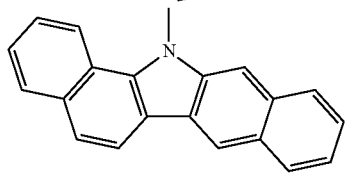

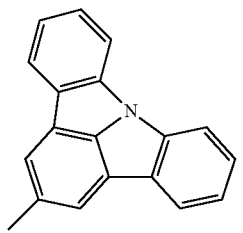

A "substituted or unsubstituted dibenzofuranyl group" and a "substituted or unsubstituted dibenzothiophenyl group" referred to herein include the following dibenzofuranyl group and the following dibenzothiophenyl group:

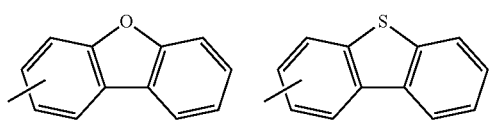

and a substituted dibenzofuranyl group and a substituted dibenzothiophenyl group, wherein each of the above groups has an optional substituent.

The optional substituents may be bonded to each other to form a fused ring structure, may include a hetero atom, such as a nitrogen atom, an oxygen atom, a silicon atom, and selenium atom, and may be bonded to any of 1- to 8-positions. Examples of such substituted dibenzofuranyl groups and substituted dibenzothiophenyl groups are shown below:

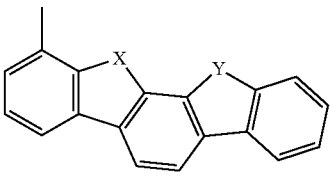

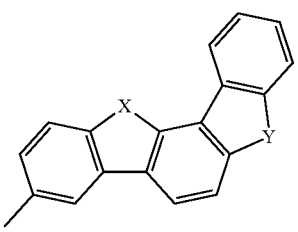

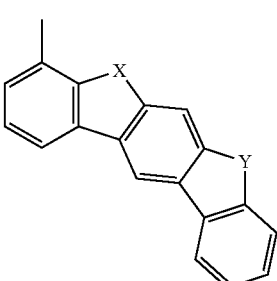

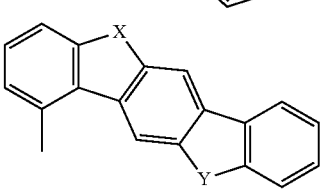

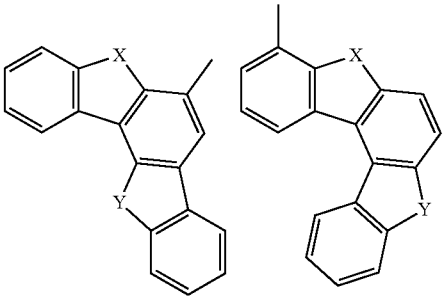

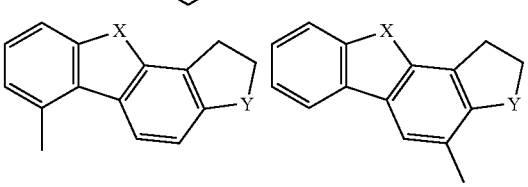

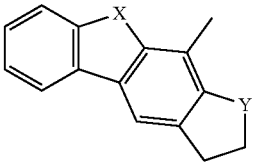

-continued

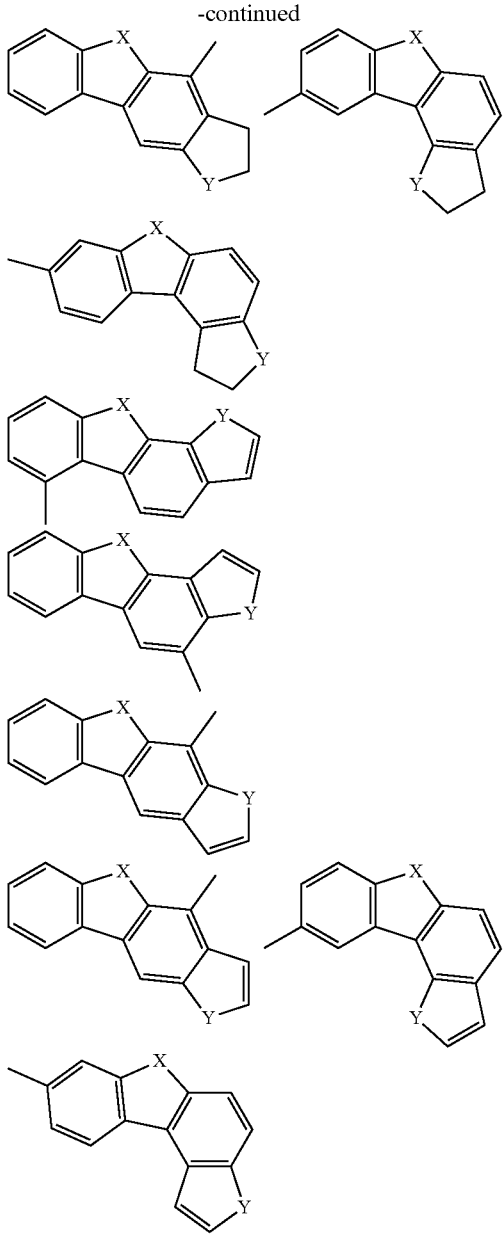

wherein X represents an oxygen atom or a sulfur atom and Y represents an oxygen atom, a sulfur atom, NH, NR$^a$ wherein R$^a$ represents an alkyl group or an aryl group, CH$_2$, or CR$^b_2$ wherein R$^b$ represents an alkyl group or an aryl group.

The substituent referred to by "a substituent" or "a substituted or unsubstituted" used herein is preferably selected from the group consisting of an alkyl group having 1 to 50, preferably 1 to 18, more preferably 1 to 8 carbon atoms; a cycloalkyl group having 3 to 50, preferably 3 to 10, more preferably 3 to 8, still more preferably 5 or 6 ring carbon atoms; an aryl group having 6 to 50, preferably 6 to 25, more preferably 6 to 18 ring carbon atoms; an aralkyl group having 7 to 51, preferably 7 to 30, more preferably 7 to 20 carbon atoms which includes an aryl group having 6 to 50, preferably 6 to 25, more preferably 6 to 18 ring carbon atoms; an amino group; a mono- or di-substituted amino group, wherein the substituent is selected from an alkyl group having 1 to 50, preferably 1 to 18, more preferably 1 to 8 carbon atoms and an aryl group having 6 to 50, preferably 6 to 25, more preferably 6 to 18 ring carbon atoms; an alkoxy group having an alkyl group having 1 to 50, preferably 1 to 18, more preferably 1 to 8 carbon atoms; an aryloxy group having an aryl group having 6 to 50, preferably 6 to 25, more preferably 6 to 18 ring carbon atoms; a mono-, di- or tri-substituted silyl group, wherein the substituent is selected from an alkyl group having 1 to 50, preferably 1 to 18, more preferably 1 to 8 carbon atoms and an aryl group having 6 to 50, preferably 6 to 25, more preferably 6 to 18 ring carbon atoms; a heteroaryl group having 5 to 50, preferably 5 to 24, more preferably 5 to 13 ring atoms; a haloalkyl group having 1 to 50, preferably 1 to 18, more preferably 1 to 8 carbon atoms; a halogen atom selected from a fluorine atom, a chlorine atom, a bromine atom and an iodine atom; a cyano group; a nitro group; a substituted sulfonyl group, wherein the substituent is selected from an alkyl group having 1 to 50, preferably 1 to 18, more preferably 1 to 8 carbon atoms and an aryl group having 6 to 50, preferably 6 to 25, more preferably 6 to 18 ring carbon atoms; a di-substituted phosphoryl group, wherein the substituent is selected from an alkyl group having 1 to 50, preferably 1 to 18, more preferably 1 to 8 carbon atoms and an aryl group having 6 to 50, preferably 6 to 25, more preferably 6 to 18 ring carbon atoms; an alkylsulfonyloxy group; an arylsulfonyloxy group; an alkylcarbonyloxy group; an arylcarbonyloxy group; a boron-containing group; a zinc-containing group; a tin-containing group; a silicon-containing group; a magnesium-containing group; a lithium-containing group; a hydroxyl group; an alkyl-substituted or aryl-substituted carbonyl group; a carboxyl group; a vinyl group; a (meth)acryloyl group; an epoxy group; and an oxetanyl group.

These substituents may have the substituent mentioned above. The substituents may be bonded to each other to form a ring.

The term "unsubstituted" referred to by "a substituted or unsubstituted" means that a hydrogen atom is not substituted by the substituent mentioned above.

Of the above substituents, more preferred are an alkyl group having 1 to 50, preferably 1 to 18, more preferably 1 to 8 carbon atoms; a cycloalkyl group having 3 to 50, preferably 3 to 10, more preferably 3 to 8, still more preferably 5 or 6 ring carbon atoms; an aryl group having 6 to 50, preferably 6 to 25, more preferably 6 to 18 ring carbon atoms; a mono- or di-substituted amino group, wherein the substituent is selected from an alkyl group having 1 to 50, preferably 1 to 18, more preferably 1 to 8 carbon atoms and an aryl group having 6 to 50, preferably 6 to 25, more preferably 6 to 18 ring carbon atoms; a heteroaryl group having 5 to 50, preferably 5 to 24, more preferably 5 to 13 ring atoms; a halogen atom; and a cyano group.

In the present invention, the features which are defined as being preferred can be selected arbitrarily and a combination thereof is a more preferred embodiment.

Composition

In an aspect, the invention provides a composition comprising a compound represented by formula (1) and at least one compound selected from compounds represented by any of formulae (CH1), (CH3), (CH4), (CH5), (CH6), (CH14), and (CH15). The composition is suitable for use in forming the layer of organic EL device by a coating method and is useful as a material for organic electroluminescence devices.

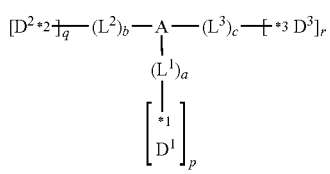

(1)

In formula (1),

A represents a substituted or unsubstituted nitrogen-containing heteroaromatic hydrocarbon group having 5 to 30 ring atoms;

$L^1$ to $L^3$ each independently represent a substituted or unsubstituted aromatic hydrocarbon group having 6 to 30 ring carbon atoms, a substituted or unsubstituted heterocyclic group having 5 to 30 ring atoms or a group wherein 2 to 4 groups selected from the preceding groups are bonded to each other;

a to c each independently represent 0 or 1;

p to r each independently represent an integer of 0 to 3, p+q+r=3, and two or more groups $D^1$, two or more groups $D^2$ and two or more groups $D^3$ when p, q or r is 2 or 3 may be the same or different, respectively; and

*1 to *3 are respectively bonded to $D^1$ to $D^3$, and $D^1$ to $D^3$ each independently represent a substituent selected from Group A to group D each independently represented by formulae $(D^A)$ to $(D^D)$.

In formula $(D^A)$ which represents the substituent belonging to Group A, one of *4 and *5 is bonded to one of *1 to *3 of formula (1) and the other is bonded to $Ar^1$;

$Ar^1$ and $Ar^2$ each independently represent a substituted or unsubstituted aryl group having 6 to 30 ring carbon atoms or a substituted or unsubstituted heteroaryl group having 5 to 30 ring atoms;

one of $X^1$ to $X^4$ and one of $X^{13}$ to $X^{16}$ represent carbon atoms which are respectively bonded to *10 and *11, and the other six each independently represent C(R) or a nitrogen atom;

one of $X^9$ and $X^{12}$ and one of $X^{21}$ to $X^{24}$ represent carbon atoms which are respectively bonded to *12 and *13, and the other six each independently represent C(R) or a nitrogen atom;

$X^5$ to $X^8$ and $X^{17}$ to $X^{20}$ each independently represent C(R) or a nitrogen atom; and R represents a hydrogen atom or a substituent, two or more groups R may be the same or different, and two selected from groups R may be bonded to each other to form a ring.

In formula $(D^B)$ which represents the substituent belonging to Group B, two of $X^1$ to $X^4$ represent carbon atoms which are respectively bonded to *21 and *22, and the other two independently represent C(R) or a nitrogen atom;

Group A

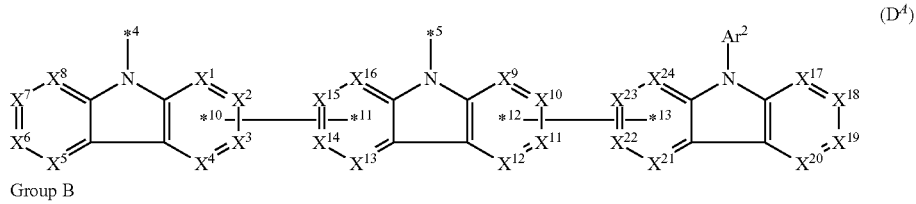

$(D^A)$

Group B

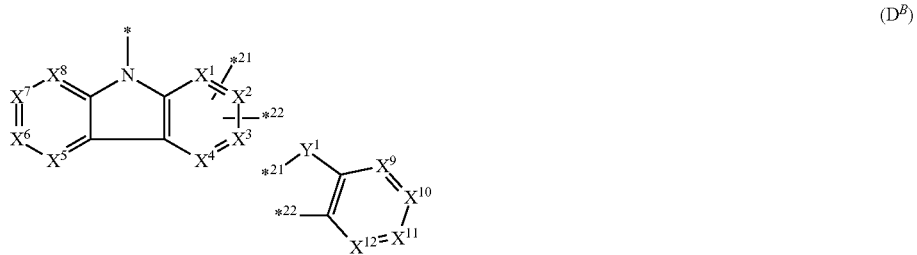

$(D^B)$

Group C

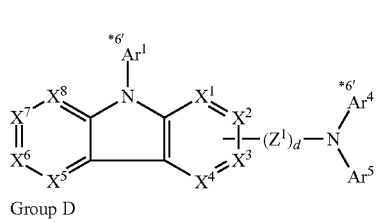

$(D^C)$

Group D

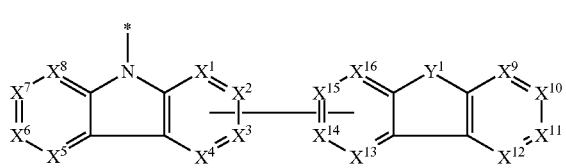

$(D^D)$ $X^5$ to $X^{12}$ each independently represent C(R) or a nitrogen atom;

R represents a hydrogen atom or a substituent, two or more groups R may be the same or different, and two selected from groups R may be bonded to each other to form a ring;

$Y^1$ represents an oxygen atom, a sulfur atom, —C($R^A$)($R^B$)—, —Si($R^C$)($R^D$)—, —P($R^E$)—, —P(=O)($R^F$)—, —S(=O)$_2$—, —P(=S)($R^G$)—, or —N($R^H$)—;

$R^A$ to $R^H$ each independently represent a hydrogen atom or a substituent, and $R^A$ and $R^B$, and $R^C$ and $R^D$ may be bonded to each other to form a ring; and

* is bonded to one of *1 to *3 of formula (1).

In formula ($D^C$) which represents the substituent belonging to Group C, $X^1$ to $X^8$ each represent C($R^1$) to C($R^8$), respectively, or a nitrogen atom;

$R^1$ to $R^8$ each independently represent a hydrogen atom or a substituent, provided that one of $X^1$ to $X^4$ represents a carbon atom which is directly bonded to $Z^1$ or the nitrogen atom to which $Ar^4$ and $Ar^5$ are bonded, and two selected from $R^1$ to $R^8$ not involved in the above direct bonding may be bonded to each other to form a ring;

$Ar^1$, $Ar^4$ and $Ar^5$ each independently represent a substituted or unsubstituted aryl group having 6 to 30 ring carbon atoms or a substituted or unsubstituted heteroaryl group having 5 to 30 ring atoms;

$Z^1$ independently represents a substituted or unsubstituted aromatic hydrocarbon group having 6 to 30 ring carbon atoms, a substituted or unsubstituted heterocyclic group having 5 to 30 ring atoms, or a group wherein 2 to 4 groups selected from the preceding groups are bonded to each other;

d is 0 or 1; and one of *1 to *3 of formula (1) is directly bonded to a nitrogen atom from which one of $Ar^1$ and $Ar^4$ indicated by *6' is removed.

In formula ($D^D$) which represents the substituent belonging to Group D, $X^1$ to $X^{16}$ each represent C($R^1$) to C($R^{16}$), respectively, or a nitrogen atom;

$R^1$ to $R^{16}$ each independently represent a hydrogen atom or a substituent, provided that one of $X^1$ to $X^4$ represents a carbon atom which is directly bonded to a carbon atom represented by one of $X^{13}$ to $X^{16}$, and tow selected from $R^1$ to $R^8$ and two selected from $R^9$ to $R^{16}$, each not involved in the above direct bonding, may be bonded to each other to form a ring;

$Y^1$ represents an oxygen atom, a sulfur atom, C($R^A$)($R^B$), Si($R^C$)($R^D$), P($R^E$), P(=O)($R^F$), S(=O)$_2$, P(=S)($R^G$), or —N($R^H$)—;

$R^A$ to $R^H$ each independently represent a hydrogen atom or a substituent, $R^A$ and $R^B$, and $R^C$ and $R^D$ may be bonded to each other to form a ring; and

* is bonded to one of *1 to *3 of formula (1).

The details of each group in formula (1) and a preferred embodiment thereof are the same as those of each group indicated by the same symbol in formula 1[V] mentioned below.

In an aspect, the invention provides an composition comprising a compound represented by formula 1[I] and at least one compound selected from compounds represented by any of formulae (CH1), (CH3), (CH4), (CH5), (CH6), (CH14), and (CH15), provided that each of the compound (CH1), the compound (CH3), the compound (CH4), the compound (CH5), the compound (CH6), the compound (CH14), and the compound (CH15) is not the same as the compound represented by formula 1[I]. Namely, the compound overlapped with the compound represented by formula 1[I] is removed from the scope of each of the formulae (CH1), (CH3), (CH4), (CH5), (CH6), (CH14), and (CH15).

In an aspect, the invention provides a composition comprising a compound represented by formula 1[II] and at least one compound selected from compounds represented by any of formulae (CH1), (CH3), (CH4), (CH5), (CH6), (CH14), and (CH15), provided that each of the compound (CH1), the compound (CH3), the compound (CH4), the compound (CH5), the compound (CH6), the compound (CH14), and the compound (CH15) is not the same as the compound represented by formula 1[II]. Namely, the compound overlapped with the compound represented by formula 1[II] is removed from the scope of each of the formulae (CH1), (CH3), (CH4), (CH5), (CH6), (CH14), and (CH15).

In an aspect, the invention provides a composition comprising a compound represented by formula 1[III] and at least one compound selected from compounds represented by any of formulae (CH1), (CH3), (CH4), (CH5), (CH6), (CH14), and (CH15), provided that each of the compound (CH1), the compound (CH3), the compound (CH4), the compound (CH5), the compound (CH6), the compound (CH14), and the compound (CH15) is not the same as the compound represented by formula 1[III]. Namely, the compound overlapped with the compound represented by formula 1[III] is removed from the scope of each of the formulae (CH1), (CH3), (CH4), (CH5), (CH6), (CH14), and (CH15).

In an aspect, the invention provides a composition comprising a compound represented by formula 1[IV] and at least one compound selected from compounds represented by any of formulae (CH1), (CH3), (CH4), (CH5), (CH6), (CH14), and (CH15), provided that each of the compound (CH1), the compound (CH3), the compound (CH4), the compound (CH5), the compound (CH6), the compound (CH14), and the compound (CH15) is not the same as the compound represented by formula 1[IV]. Namely, the compound overlapped with the compound represented by formula 1[IV] is removed from the scope of each of the formulae (CH1), (CH3), (CH4), (CH5), (CH6), (CH14), and (CH15).

In an aspect, the invention provides a composition comprising a compound represented by formula 1[V] and at least one compound selected from compounds represented by any of formulae (CH1), (CH3), (CH4), (CH5), (CH6), (CH14), and (CH15), provided that each of the compound (CH1), the compound (CH3), the compound (CH4), the compound (CH5), the compound (CH6), the compound (CH14), and the compound (CH15) is not the same as the compound represented by formula 1[V]. Namely, the compound overlapped with the compound represented by formula 1[V] is removed from the scope of each of the formulae (CH1), (CH3), (CH4), (CH5), (CH6), (CH14), and (CH15).

These compositions are suitable for use in forming the layer of organic EL device by a coating method and are useful as a material for organic electroluminescence devices.

Compound Represented by Formula (1)

In an aspect, the invention provides a compound represented by formula (1), which is suitable for use in forming the layer of organic EL device by a coating method and is useful as a material for organic electroluminescence devices.

The compound represented by formula (1) is preferably the compound represented by formula 1[I], the compound represented by formula 1[II], the compound represented by formula 1[III], the compound represented by formula 1[IV], and the compound represented by formula 1[V], each described below.

Compound Represented by Formula 1[I]

In an aspect, the invention provides the compound represented by formula 1[I] (also referred to as "compound 1[I]"), which is suitable for use in forming the layer of organic EL device by a coating method and is useful as a material for organic electroluminescence devices.

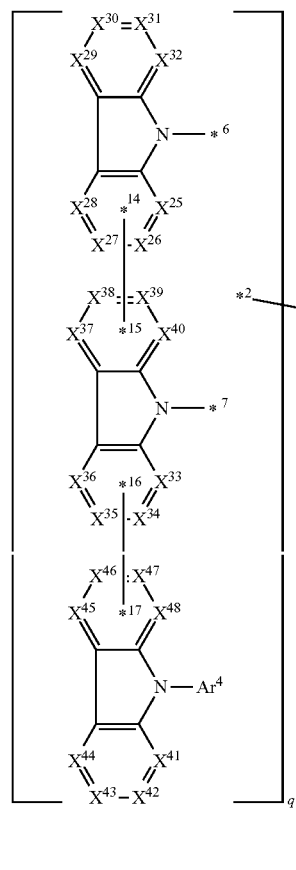
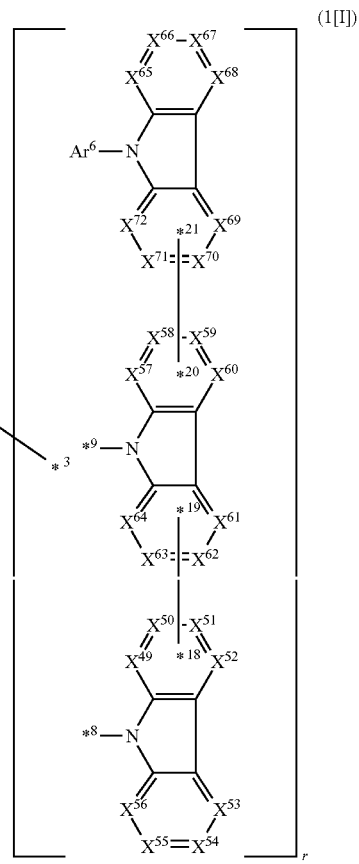
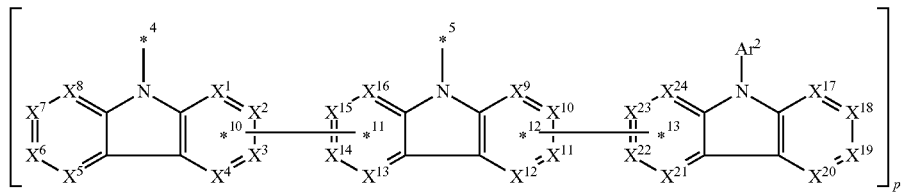

(1[I])

In formula 1[I],

A represents a substituted or unsubstituted nitrogen-containing heteroaromatic hydrocarbon group having 5 to 30 ring atoms;

$L^1$ to $L^3$ each independently represent a substituted or unsubstituted aromatic hydrocarbon group having 6 to 30 ring carbon atoms, a substituted or unsubstituted heterocyclic group having 5 to 30 ring atoms, or a group wherein 2 to 4 groups selected from the preceding groups are bonded to each other;

a to c each independently represent 0 or 1;

one of *4 and *5 is bonded to *1 and the other is bonded to $Ar^1$;

one of *6 and *7 is bonded to *2 and the other is bonded to $Ar^3$;

one of *8 and *9 is bonded to *3 and the other is bonded to $Ar^5$;

$Ar^1$ to $Ar^6$ each independently represent a substituted or unsubstituted aryl group having 6 to 30 ring carbon atoms or a substituted or unsubstituted heteroaryl group having 5 to 30 ring atoms;

one of $X^1$ to $X^4$ and one of $X^{13}$ to $X^{16}$ represent carbon atoms which are respectively bonded to *10 and *11, and the other six each independently represent C(R) or a nitrogen atom;

one of $X^9$ and $X^{12}$ and one of $X^{21}$ to $X^{24}$ represent carbon atoms which are respectively bonded to *12 and *13, and the other six each independently represent C(R) or a nitrogen atom;

one of $X^{25}$ to $X^{28}$ and one of $X^{37}$ to $X^{40}$ represent carbon atoms which are respectively bonded to *14 and *15, and the other six each independently represent C(R) or a nitrogen atom;

one of X³³ to X³⁶ and one of X⁴⁵ to X⁴⁸ represent carbon atoms which are respectively bonded to *16 and *17, and the other six each independently represent C(R) or a nitrogen atom;

one of X⁴⁹ to X⁵² and one of X⁶¹ to X⁶⁴ represent carbon atoms which are respectively bonded to *18 and *19, and the other six each independently represent C(R) or a nitrogen atom;

one of X⁵⁷ to X⁶⁰ and one of X⁶⁹ to X⁷² represent carbon atoms which are respectively bonded to *20 and *21, and the other six each independently represent C(R) or a nitrogen atom;

X⁶ to X⁸, X¹⁷ to X²⁰, X²⁹ to X³², X⁴¹ to X⁴⁴, X⁵³ to X⁵⁶, and X⁶⁵ to X⁶⁸ each independently represent C(R) or a nitrogen atom;

R represents a hydrogen atom or a substituent, two or more groups R may be the same or different, and two selected from groups R may be bonded to each other to form a ring; and p to r each independently represent an integer of 0 to 3, p+q+r=3, and when p, q or r is 2 or 3, 2 or 3 groups in each [ ] may be the same or different, respectively.

Description of Each Group in Formula 1[I]

The nitrogen-containing heteroaromatic hydrocarbon group for A of formula 1[I] has 5 to 30, preferably 6 and 20, and more preferably 6 to 14 ring carbon atoms.

The nitrogen-containing heteroaromatic hydrocarbon group is preferably a monocyclic group or a fused ring group comprising two or three fused rings.

The nitrogen-containing heteroaromatic hydrocarbon group contains preferably 1 to 3 and more preferably 2 or 3 nitrogen atoms. Particularly, the nitrogen-containing heteroaromatic hydrocarbon group contains preferably 2 or 3 and more preferably 3 nitrogen atoms when it is a monocyclic group, and preferably 2 nitrogen atoms when it is a fused ring group having two or three fused rings.

The nitrogen-containing heteroaromatic hydrocarbon group may contain a hetero atom other than a nitrogen atom, such as an oxygen atom, a sulfur atom, a silicon atom, and selenium atom, but preferably contains only a nitrogen atom as the heteroatom.

Examples of the nitrogen-containing heteroaromatic hydrocarbon group for A in formula 1[I] includes residues of compounds selected from pyrrole, pyridine, pyridazine, pyrimidine, pyrazine, triazine, imidazole, pyrazole, oxadiazole, thiadiazole, triazole, tetrazole, indole, isoindole, indolizine, quinolizine, quinoline, isoquinoline, naphthyridine, cinnoline, phthalazine, quinazoline, benzo[f]quinazoline, benzo[h]quinazoline, quinoxaline, benzimidazole, indazole, carbazole, biscarbazole, phenanthridine, acridine, phenanthroline, phenazine, azatriphenylene, diazatriphenylene, hexaazatriphenylene, azacarbazole, azadibenzofuran, azadibenzothiophene, and dinaphtho[2',3': 2,3:2',3': 6,7]carbazole.

The residue is a mono valent or more valent group obtained by removing one or more hydrogen atoms from the above compound. The valency of the nitrogen-containing heteroaromatic hydrocarbon group, i.e., the valency of "A" corresponds to the value of "a+b+c" in formula 1[I].

The nitrogen-containing heteroaromatic hydrocarbon group mentioned above is preferably a residue of the following compounds:

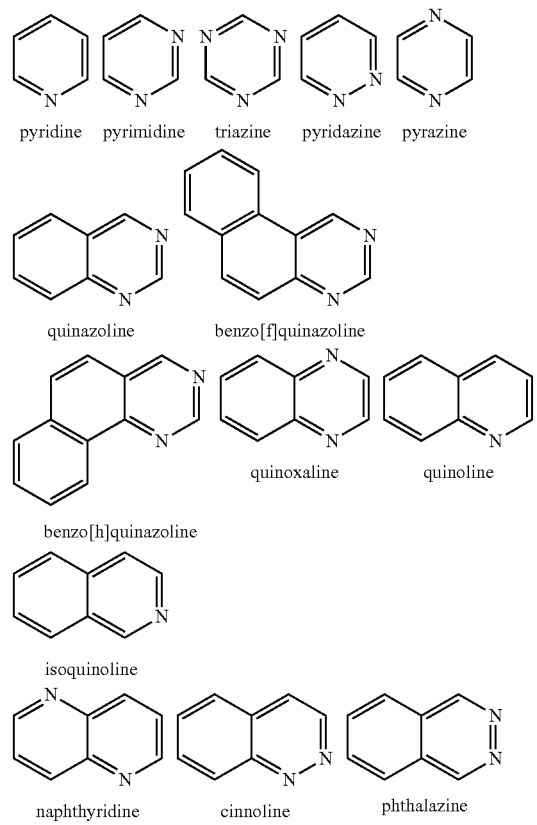

In an aspect of the invention, the nitrogen-containing heteroaromatic hydrocarbon group for A is preferably a residue of the nitrogen-containing heterocyclic ring represented by formula (A1):

(A1)

in formula (A1), X¹⁰¹ to X¹⁰⁴ each represent C(R¹⁰¹) to C(R¹⁰⁴), respectively, or a nitrogen atom; R¹⁰¹ to R¹⁰⁴ each independently represent a hydrogen atom or a substituent; and two selected from R¹⁰² to R¹⁰⁴ may be bonded to each other to form a ring.

In an aspect of the invention, the nitrogen-containing heteroaromatic hydrocarbon group for A is more preferably a residue of the nitrogen-containing heterocyclic ring represented by any of formulae (A2) to (A4):

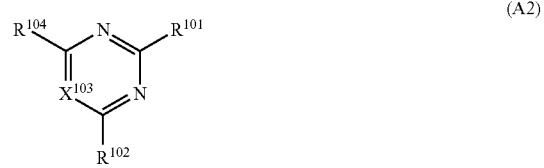

(A2)

in formula (A2), X¹⁰³ represents C(R¹⁰³) or a nitrogen atom; R¹⁰¹ to R¹⁰⁴ each independently represent a hydrogen atom or a substituent; and two selected from $R^{102}$ to $R^{104}$ may be bonded to each other to form a ring.

(A3)

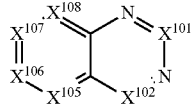

in formula (A3), $X^{101}$, $X^{102}$, and $X^{105}$ to $X^{108}$ each represent $C(R^{101})$, $C(R^{102})$, or $C(R^{105})$ to $C(R^{108})$, respectively, or a nitrogen atom; $R^{101}$, $R^{102}$, and $R^{105}$ to $R^{108}$ each independently represent a hydrogen atom or a substituent; and two selected from $R^{102}$ and $R^{105}$ to $R^{108}$ may be bonded to each other to form a ring.

(A4)

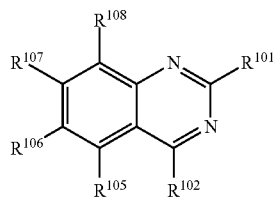

in formula (A4), $R^{101}$, $R^{102}$, and $R^{105}$ to $R^{108}$ each independently represent a hydrogen atom or a substituent; and two selected from $R^{102}$ and $R^{105}$ to $R^{108}$ may be bonded to each other to form a ring.

The nitrogen-containing heteroaromatic hydrocarbon group for A in formula 1[I] may have a substituent. Examples of the substituent of the nitrogen-containing heteroaromatic hydrocarbon group include the substituents mentioned above and also include "an (aza)carbazolyl group having two (aza)carbazolyl substituents," for example, a group represented by formula (D1) described below, and "an aryl group or a heteroaryl group each having an (aza) carbazolyl substituent which further has two (aza)carbazolyl substituents," for example, an aryl group or a heteroaryl group each having a group represented by formula (D1) as a substituent.

In formula 1[I], the aromatic hydrocarbon group for $L^1$ to $L^3$ has 6 to 30, preferably 6 to 18, more preferably 6 to 13, still more preferably 6 to 12, and particularly preferably 6 to 10 ring carbon atoms.

In an aspect of the invention, at least one of the aromatic hydrocarbon groups for $L^1$ to $L^3$ is preferably a di- to tetravalent residue of any of the following compounds, and more preferably $L^1$ to $L^3$ are all di- to tetravalent residues of any of the following compounds:

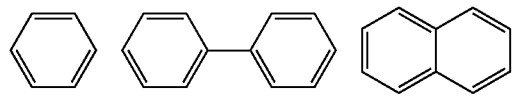

wherein each carbon atom in the compound may have a substituent.

In an aspect of the invention, at least one of the aromatic hydrocarbon groups for $L^1$ to $L^3$ is preferably a group represented by any of the following formulae, and more preferably $L^1$ to $L^3$ are all groups represented by any of the following formulae:

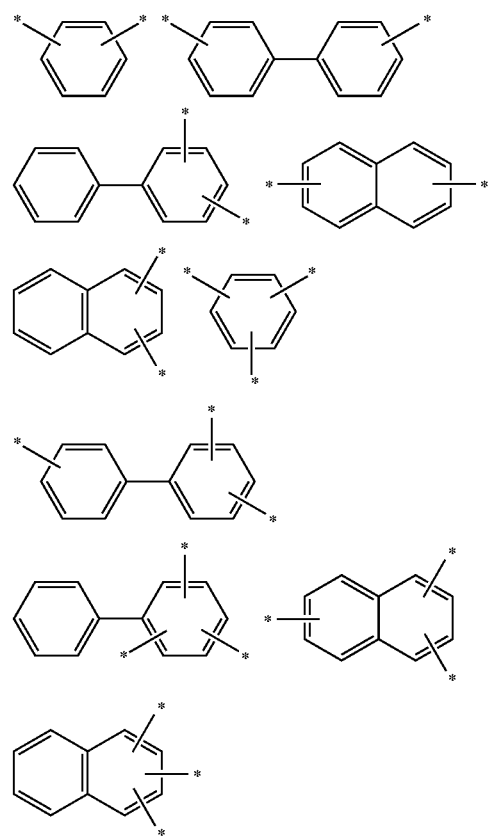

wherein * indicates a bonding site and each carbon atom other than that at the bonding site may have a substituent.

More preferably, at least one of the aromatic hydrocarbon groups for $L^1$ to $L^3$ is a group represented by any of the following formulae, and still more preferably $L^1$ to $L^3$ are all groups represented by any of the following formulae:

wherein * indicates a bonding site and each carbon atom other than that at the bonding site may have a substituent.

More preferably, at least one of the aromatic hydrocarbon groups for $L^1$ to $L^3$ is a group represented by any of the following formulae, and still more preferably $L^1$ to $L^3$ are all groups represented by any of the following formulae:

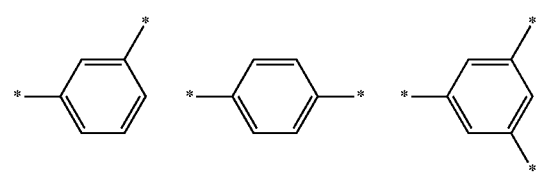

wherein * indicates a bonding site and each carbon atom other than that at the bonding site may have a substituent.

In addition to the above groups, the aromatic hydrocarbon group for $L^1$ to $L^3$ may include the groups represented by the following formulae:
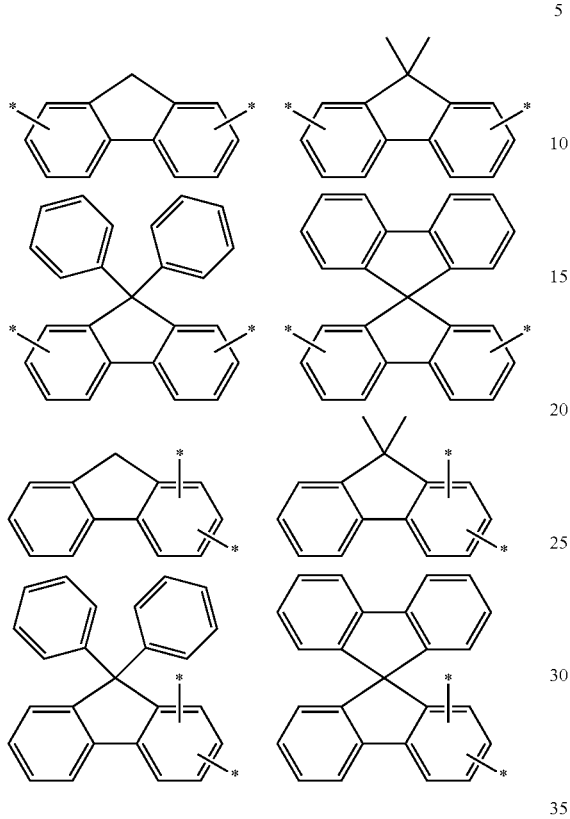
wherein * indicates a bonding site and each carbon atom other than that at the bonding site may have a substituent.
Examples of the divalent aromatic hydrocarbon group for $L^1$ to $L^3$ include the following groups:
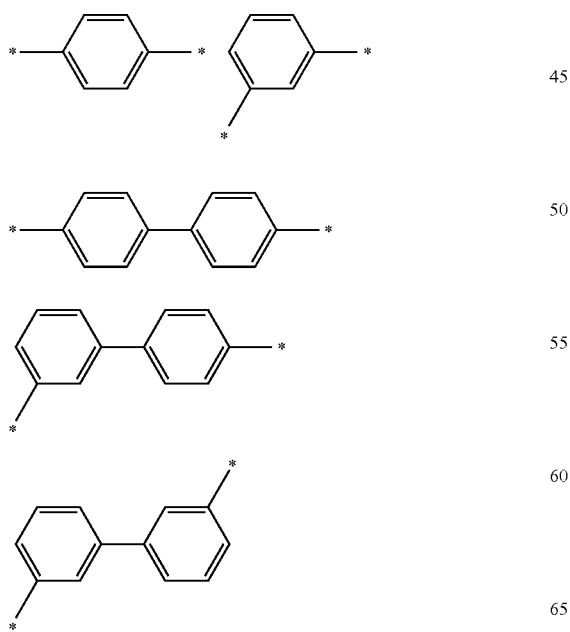
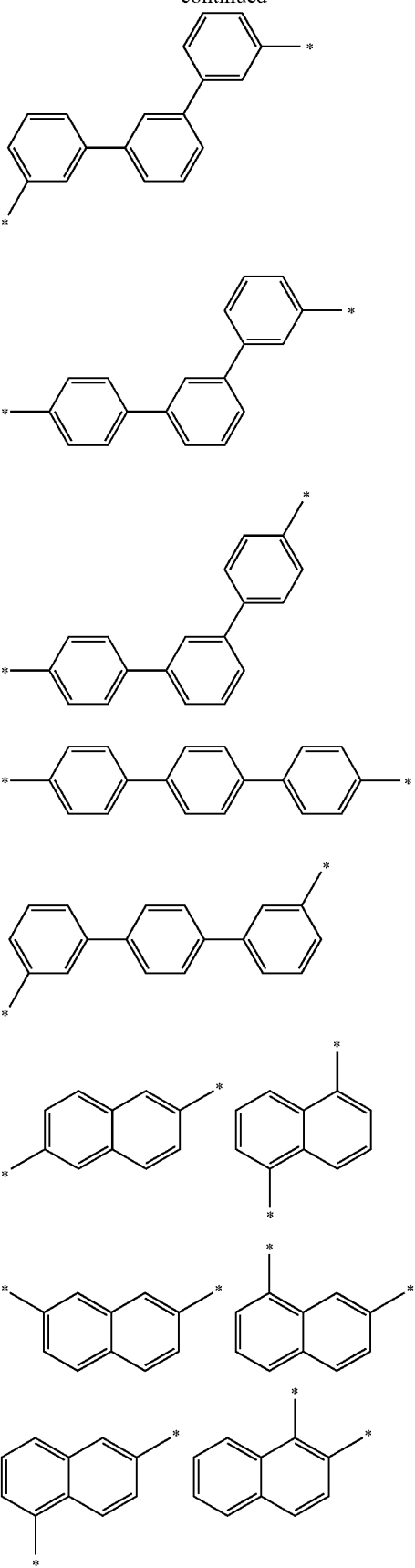

-continued

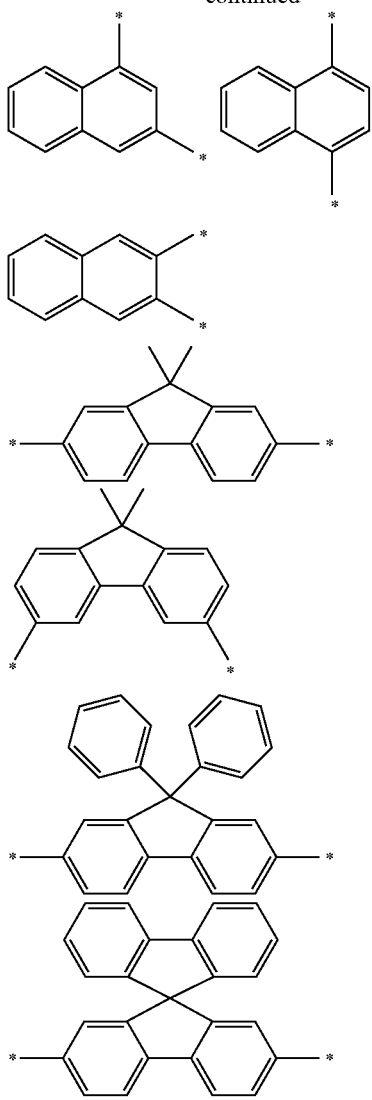

wherein * indicates a bonding site and each carbon atom other than that at the bonding site may have a substituent.

In formula 1[I], the heterocyclic group for $L^1$ to $L^3$ has 5 to 30, preferably 5 to 18, more preferably 5 to 13, particularly preferably 5 to 10 ring atoms.

Examples of the heterocyclic group include a residue of a nitrogen-containing heterocyclic compound, such as pyrrole, pyridine, imidazopyridine, pyrazole, triazole, tetrazole, indole, isoindole, and carbazole; a residue of an oxygen-containing heterocyclic compound, such as furan, benzofuran, isobenzofuran, dibenzofuran, oxazole, oxadiazole, benzoxazole, benzonaphthofuran, and dinaphthofuran; and a residue of a sulfur-containing heterocyclic compound, such as thiophene, benzothiophene, dibenzothiophene, thiazole, thiadiazole, benzothiazole, benzonaphthothiophene, and dinaphthothiophene.

The "group wherein 2 to 4 groups selected from the preceding groups are bonded to each other" for $L^1$ to $L^3$ is a group wherein 2 to 4 groups selected from a substituted or unsubstituted aromatic hydrocarbon group having 6 to 30 ring carbon atoms and a substituted or unsubstituted heterocyclic group having 5 to 30 ring atoms are bonded to each other. The 2 to 4 groups to be selected may be bonded to each other to form a ring structure. The order of bonding the groups selected from the aromatic hydrocarbon group and heterocyclic group is not particularly limited.

In particular, each of $L^1$ to $L^3$ is preferably a substituted or unsubstituted aromatic hydrocarbon group having 6 to 30 ring carbon atoms. The aromatic hydrocarbon group more preferred is as described above.

In formula 1[I], a to c each independently represent 0 or 1.

When a is zero, $L^1$ is not present, i.e., A is directly bonded to the group in [ ]. When a is 1, A is bonded to the group in [ ] via $L^1$. The same applies to b and c.

In formula 1[I], one of *4 and *5 is bonded to *1 and the other is bonded to $Ar^1$, one of *6 and *7 is bonded to *2 and the other is bonded to $Ar^3$, and one of *8 and *9 is bonded to *3 and the other is bonded to $Ar^5$.

In an aspect of the invention, a compound of formula 1[I] wherein *5 is bonded to *1, *4 is bonded to $Ar^1$, *7 is bonded to *2, *6 is bonded to $Ar^3$, *9 is bonded to *3, and *8 is bonded to $Ar^5$ is preferred.

$Ar^1$ to $Ar^6$ each independently represent a substituted or unsubstituted aryl group having 6 to 30 ring carbon atoms or a substituted or unsubstituted heteroaryl group having 5 to 30 ring atoms.

The aryl group for $Ar^1$ to $Ar^6$ has 6 to 30, preferably 6 to 18, more preferably 6 to 15, still more preferably 6 to 12, particularly preferably 6 to 10 ring carbon atoms.

The aryl group may be any of a non-fused aryl group, a fused aryl group, and a combination thereof.

Examples of the aryl group include a phenyl group, a biphenylyl group, a terphenylyl group, a quaterphenylyl group, a quinquephenylyl group, a naphthyl group (a 1-naphthyl group, a 2-naphthyl group), an acenaphthylenyl group, an anthryl group, a benzanthryl group, an aceanthryl group, a phenanthryl group, a benzophenanthryl group, a phenalenyl group, a fluorenyl group (inclusive of a 9,9-dimethylfluorenyl group, a 9,9-diphenylfluorenyl group, and a 9,9'-spirobifluorenyl group), a benzofluorenyl group, a dibenzofluorenyl group, a picenyl group, a pentaphenyl group, a pentacenyl group, a pyrenyl group, a chrysenyl group, a benzochrysenyl group, a fluoranthenyl group, a benzofluoranthenyl group, a tetracenyl group, a perylenyl group, a coronyl group, a dibenzanthryl group, a naphthylphenyl group, a s-indanyl group, an as-indanyl group, a triphenylenyl group, and a benzotriphenylenyl group. The above groups include isomeric groups, if any.

The aryl group for $Ar^1$ to $Ar^6$ is preferably selected from the following groups:

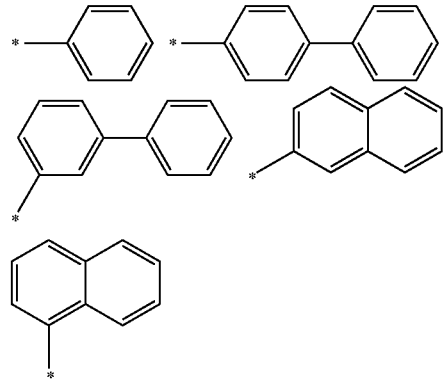

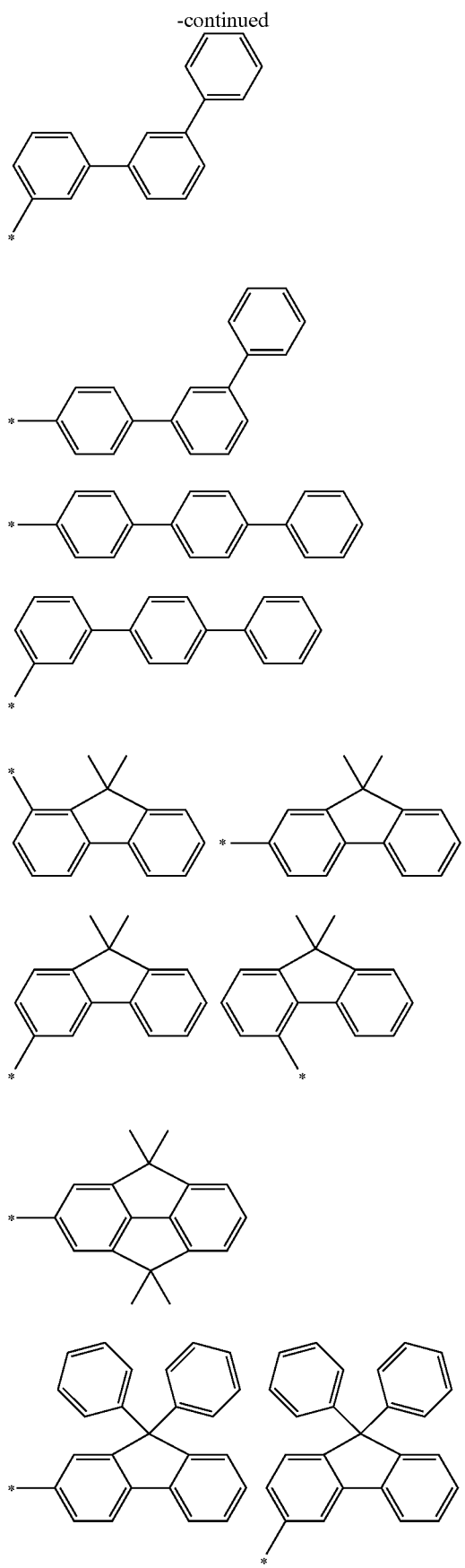
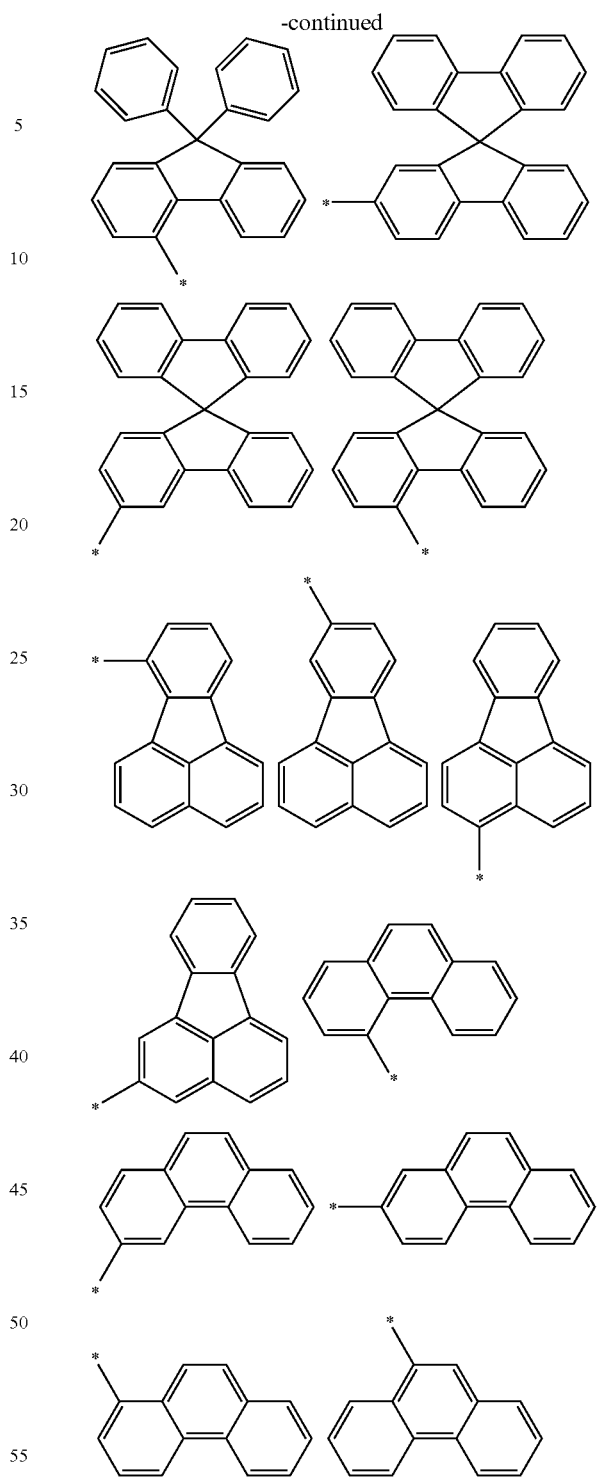

wherein * indicates a bonding site and each carbon atom other than that at the bonding site may have a substituent.

The heteroaryl group for $Ar^1$ to $Ar^6$ has 5 to 30, preferably 5 to 20, more preferably 5 to 14, and still more preferably 5 to 10 ring atoms.

The heteroaryl group contains at least one, preferably 1 to 5, more preferably 1 to 3, and still more preferably 1 to 2 hetero atoms which may be the same or different.

Examples of the heteroaryl group include a pyrrolyl group, a furyl group, a thienyl group, a pyridyl group, a pyridazinyl group, a pyrimidinyl group, a pyrazinyl group, a triazinyl group, an imidazolyl group, an oxazolyl group, a thiazolyl group, a pyrazolyl group, an isoxazolyl group, an isothiazolyl group, an oxadiazolyl group, a thiadiazolyl group, a triazolyl group, a tetrazolyl group, an indolyl group, an isoindolyl group, a benzofuranyl group, an isobenzofuranyl group, a benzothiophenyl group, an isobenzothiophenyl group, an indolizinyl group, a quinolizinyl group, a quinolyl group, an isoquinolyl group, a cinnolyl group, a phthalazinyl group, a quinazolinyl group, a quinoxalinyl group, a benzimidazolyl group, a benzoxazolyl group, a benzothiazolyl group, an indazolyl group, a benzisoxazolyl group, a benzisothiazolyl group, a dibenzofuranyl group, a dibenzothiophenyl group, a carbazolyl group, a biscarbazolyl group, a phenanthridinyl group, an acridinyl group, a phenanthrolinyl group, a phenazinyl group, a phenothiazinyl group, a phenoxazinyl group, an azatriphenylenyl group, a diazatriphenylenyl group, a xanthenyl group, an azacarbazolyl group, an azadibenzofuranyl group, an azadibenzothiophenyl group, a benzofuranobenzothiophenyl group, a benzothienobenzothiophenyl group, a dibenzofuranonaphthyl group, a dibenzothienonaphthyl group, a dinaphthothienothiophenyl group, and a dinaphtho[2',3': 2,3:2',3': 6,7]carbazolyl group.

Each of $Ar^1$ to $Ar^6$ is preferably a substituted or unsubstituted aryl group having 6 to 30 ring carbon atoms. More preferred examples of the aryl group are as described above.

In formula 1[I],
one of $X^1$ to $X^4$ and one of $X^{13}$ to $X^{16}$ represent carbon atoms which are respectively bonded to *10 and *11, and the other six each independently represent C(R) or a nitrogen atom;
one of $X^9$ and $X^{12}$ and one of $X^{21}$ to $X^{24}$ represent carbon atoms which are respectively bonded to *12 and *13, and the other six each independently represent C(R) or a nitrogen atom;
one of $X^{25}$ to $X^{28}$ and one of $X^{37}$ to $X^{40}$ represent carbon atoms which are respectively bonded to *14 and *15, and the other six each independently represent C(R) or a nitrogen atom;
one of $X^{33}$ to $X^{36}$ and one of $X^{46}$ to $X^{48}$ represent carbon atoms which are respectively bonded to *16 and *17, and the other six each independently represent C(R) or a nitrogen atom;
one of $X^{49}$ to $X^{52}$ and one of $X^{61}$ to $X^{64}$ are carbon atoms which are respectively bonded to *18 and *19, and the other six each independently represent C(R) or a nitrogen atom; and
one of $X^{57}$ to $X^{60}$ and one of $X^{69}$ to $X^{72}$ are carbon atoms which are respectively bonded to *20 and *21, and the other six each independently represent C(R) or a nitrogen atom.

The above limitations are described below with reference to, for example, the limitation to "$X^1$ to $X^4$ and $X^{13}$ to $X^{16}$." Assuming that $X^1$ is a carbon atom bonded to *10 and $X^{13}$ is a carbon atom bonded to *11, two carbon atoms represented by $X^1$ and $X^{13}$ are bonded to each other, thereby linking two (aza)carbazolyl groups. The other six, i.e., $X^2$ to $X^4$ and $X^{14}$ to $X^{16}$ each independently represent C(R) or a nitrogen atom. The same applies to the other limitations.

Namely, each of *10, *12, *14, *16, *18, and *20 in formula 1[I] is bonded to a carbon atom at 1-position, 2-position, 3-position or 4-position of the respective (aza)carbazolyl group, i.e., one of $X^1$ to $X^4$, one of $X^9$ to $X^{12}$, one of $X^{25}$ to $X^{28}$, one of $X^{49}$ to $X^{52}$, one of $X^{57}$ to $X^{60}$, and one of $X^{57}$ to $X^{60}$, respectively.

On the other hand, each of *11, *13, *15, *17, *19, and *21 in formula 1[I] is bonded to a carbon atom at 5-position, 6-position, 7-position, or 8-position of the respective (aza)carbazolyl group, i.e., one of $X^{13}$ to $X^{16}$, one of $X^{21}$ to $X^{24}$, one of $X^{37}$ to $X^{40}$, one of $X^{45}$ to $X^{48}$, one of $X^{61}$ to $X^{64}$, and one of $X^{69}$ to $X^{72}$, respectively.

Thus, two (aza)carbazolyl groups are linked by each of *10-*11, *12-*13, *14-*15, *16-*17, *18-*19, and *20-*21.

In formula 1[I], $X^5$ to $X^8$, $X^{17}$ to $X^{20}$, $X^{29}$ to $X^{32}$, $X^{41}$ to $X^{44}$, $X^{53}$ to $X^{56}$, and $X^{65}$ to $X^{68}$ each independently represent C(R) or a nitrogen atom.

Namely, $X^1$ to $X^{72}$ not involved in the linking between two (aza)carbazolyl groups each independently represent C(R) or a nitrogen atom, with each being preferably C(R) in an aspect of the invention.

R represents a hydrogen atom or a substituent, two or more groups R may be the same or different, and two selected from groups R may be bonded to each other to form a ring.

In the compound in an aspect of the invention, two selected from groups R are preferably not bonded to each other, thereby failing to form a ring.

In the compound in an aspect of the invention, the group in [ ] of formula 1[I] is preferably represented by formula (D1):

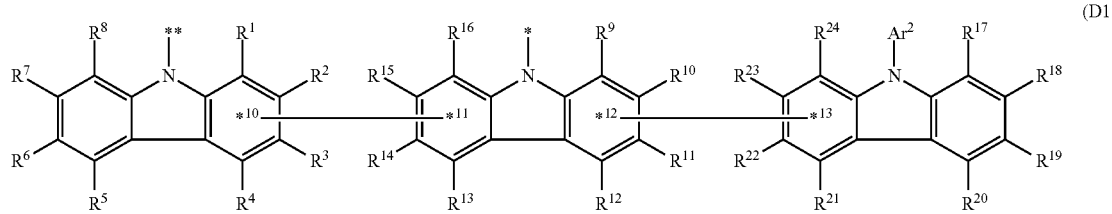

(D1)

in formula (D1), $R^1$ to $R^{24}$ may be the same or different and each independently represent a hydrogen atom or a substituent; two selected from $R^1$ to $R^{24}$ may be bonded to each other to form a ring; and one of * and ** is bonded to one of *1 to *3 of formula 1[I] and the other is bonded to $Ar^1$.

$Ar^1$ is as defined above in formula 1[I].

*10-*11 is a bond between carbon atoms from which one of $R^1$ to $R^4$ and one of $R^{13}$ to $R^{16}$ are removed, and *12-*13 is a bond between carbon atoms from which one of $R^9$ to $R^{12}$ and one of $R^{21}$ to $R^{24}$ are removed.

Namely, each of *10 and *12 is bonded to a carbon atom at 1-position, 2-position, 3-position or 4-position of a carbazolyl group, and each of *11 and *13 is bonded to a carbon atom at 5-position, 6-position, 7-position or 8-position of another carbazolyl group, thereby linking two carbazolyl groups via *10-*11 and *12-*13, respectively.

When two selected from $R^1$ to $R^{24}$ in formula (D1) are bonded to each other to form a ring, one or more pairs selected from $R^5$ and $R^6$, $R^6$ and $R^7$, $R^7$ and $R^8$, $R^{17}$ and $R^{18}$, $R^{18}$ and $R^{19}$, and $R^{19}$ and $R^{20}$ are preferably bonded to each other to form a ring.

In the compound in an aspect of the invention, two selected from $R^1$ to $R^{24}$ in formula (D1) are preferably not bonded to each other, thereby failing to form a ring, and the group in [ ] of formula 1[I] is preferably represented by formula (D2)

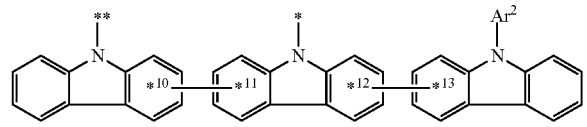

in formula (D2), each of *10-*11 and *12-*13 is a bond between carbon atoms in each benzene ring from which hydrogen atoms are removed, and * and ** are as defined above in formula (D1).

In the compound in an aspect of the invention, the group represented by formula (D1) in [ ] of formula 1[I] is preferably a group represented by formula (D3):

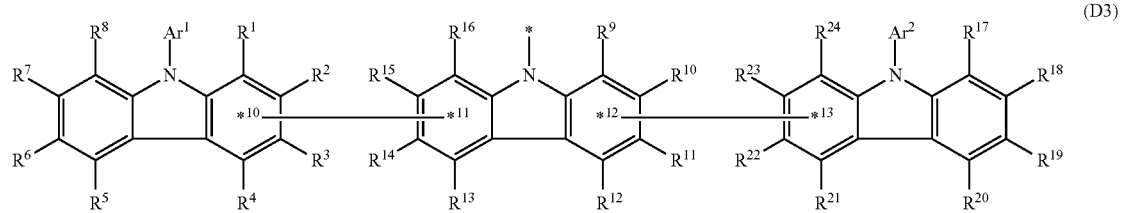

(D3)

in formula (D3), $R^1$ to $R^{24}$, $Ar^1$, *10-*11, and *12-*13 are as defined above in formula (D1), and * is bonded to one of *1 to *3 in formula 1[I].

The group represented by formula (D3) is more preferably represented by any of formulae (D3-i) to (D3-vi):

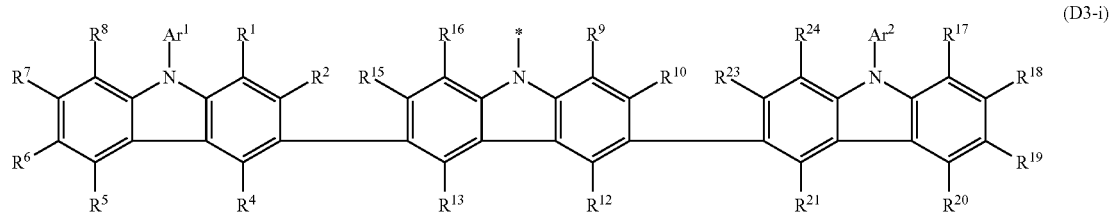

(D3-i)

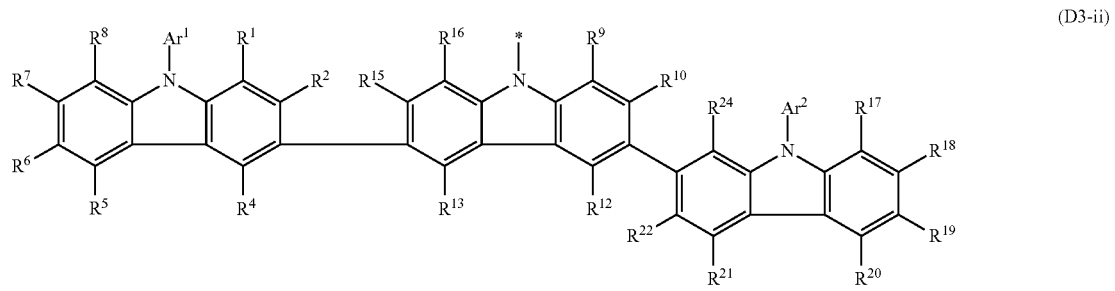

(D3-ii)

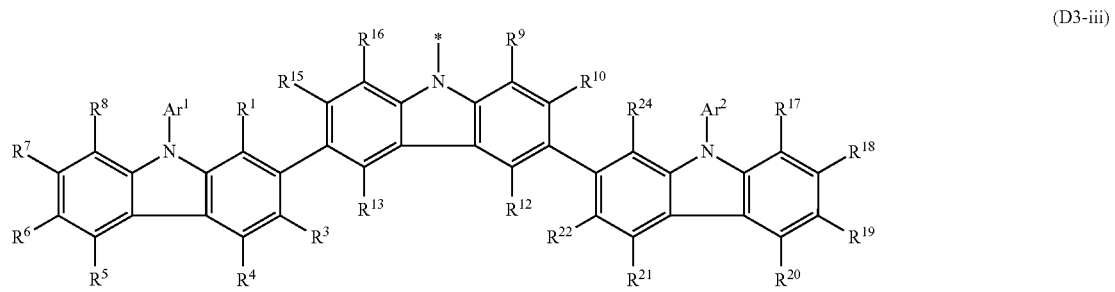

(D3-iii)

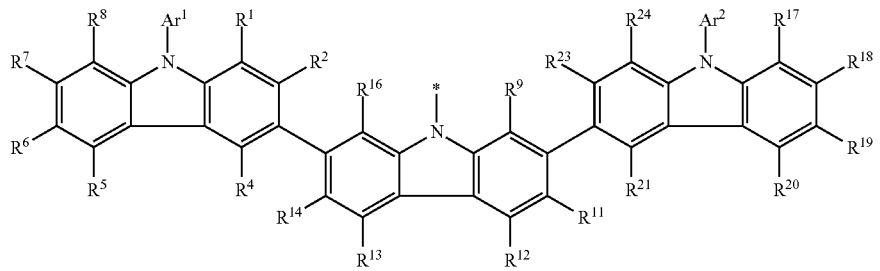
(D3-iv)
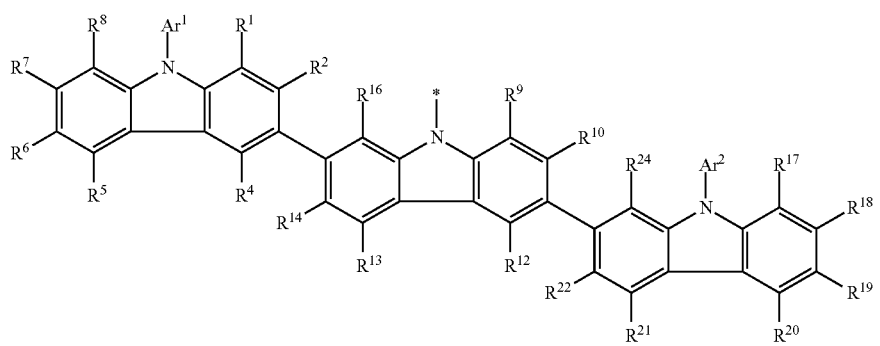
(D3-v)
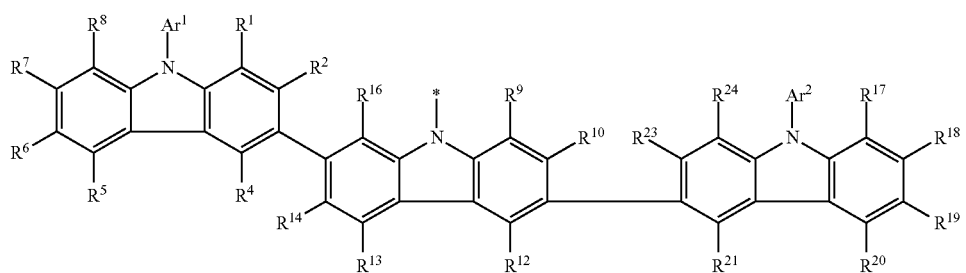
(D3-vi)
in formula (D3-i) to (D3-vi), $R^1$ to $R^{24}$, $Ar^1$, *10-*11, *12-*13, and * are as defined above in formula (D3).
Examples of the group in [ ] of formula 1[I] are preferably selected from the following groups. In the following groups, * is the bonding site to one of *1 to *3 in formula 1[I], and a hydrogen atom bonded to a carbon atom may be substituted with the substituent mentioned above.
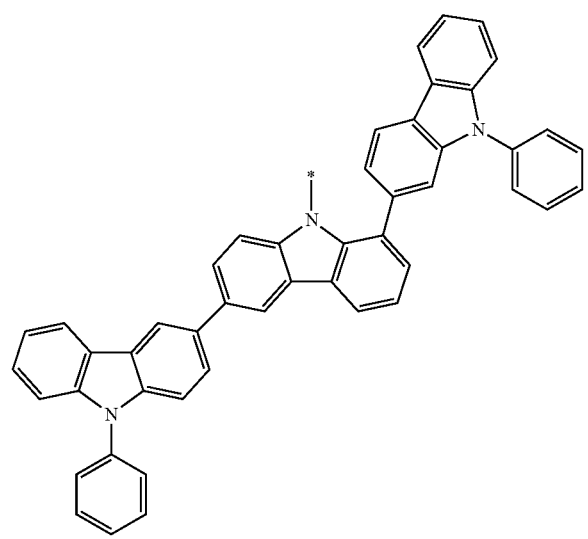
-continued
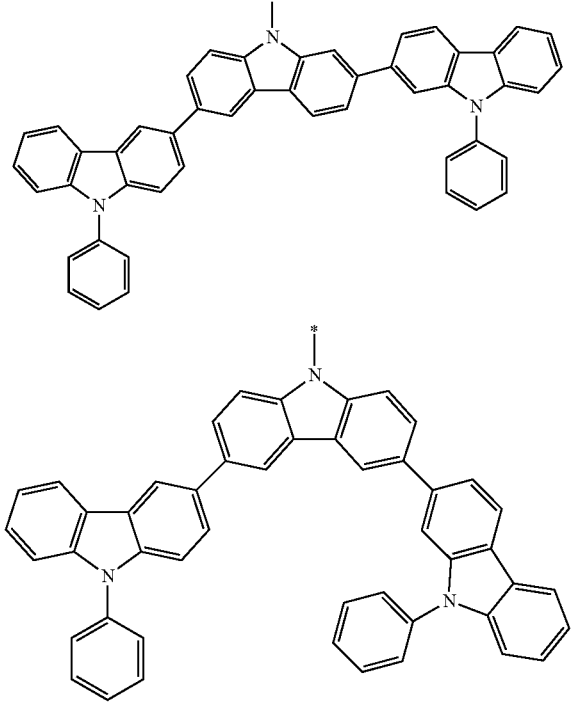

-continued
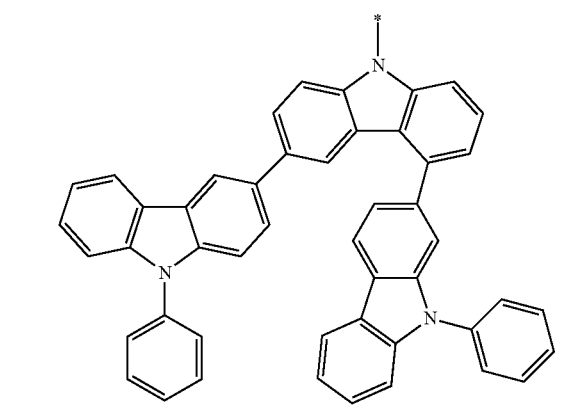
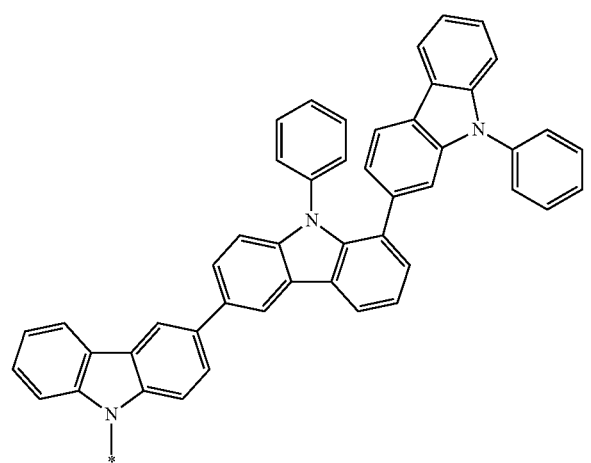
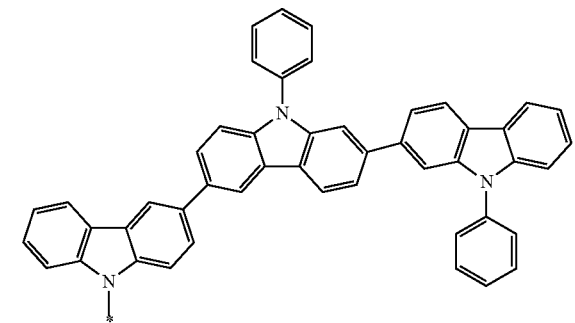
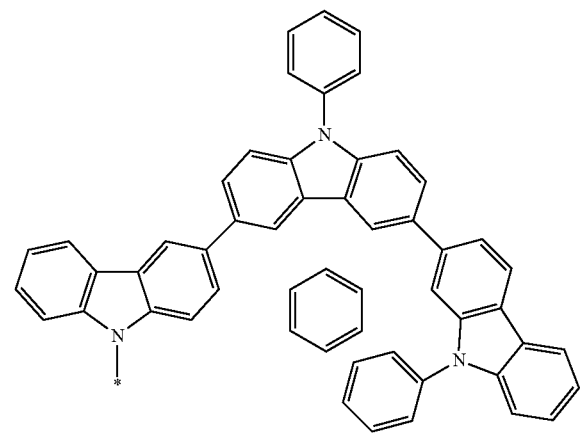
-continued
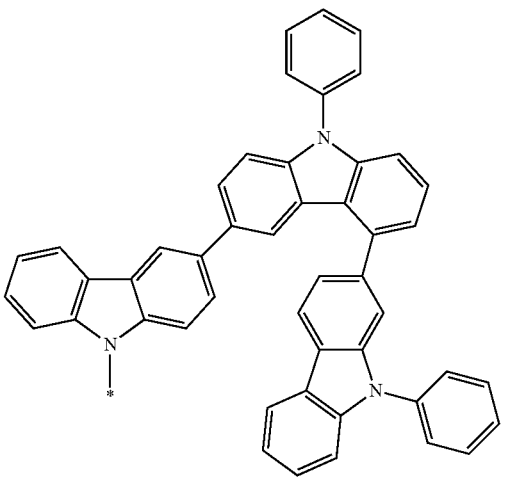
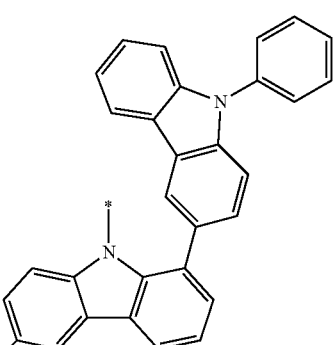
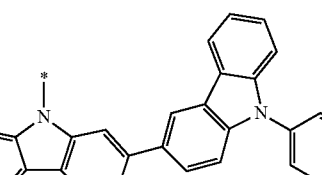

37
-continued
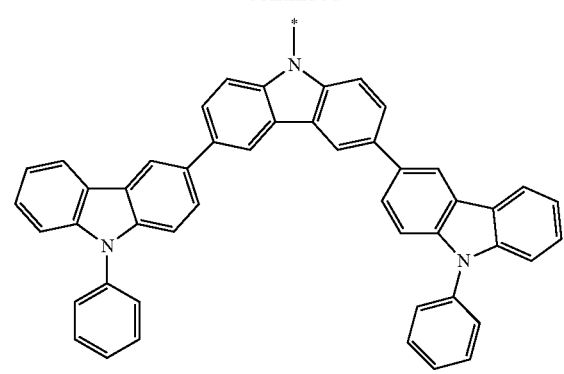
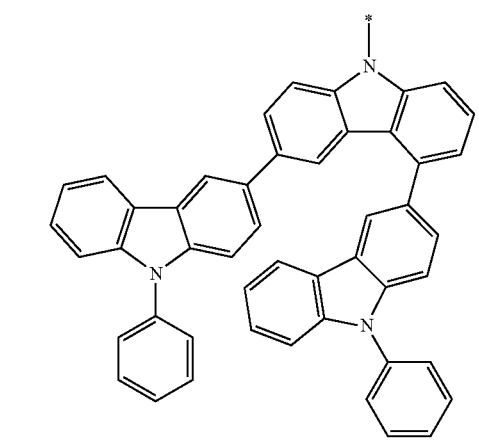
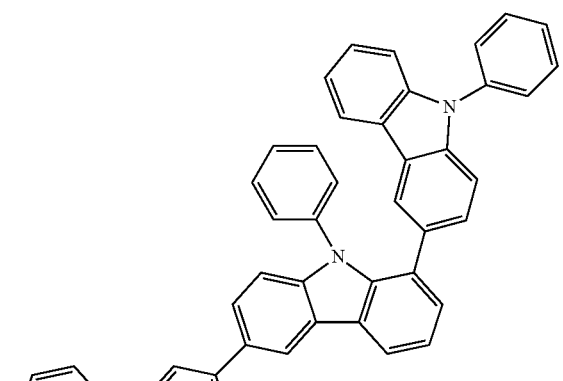
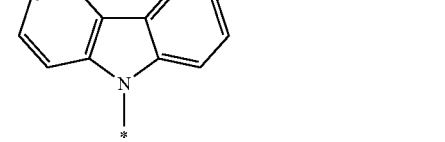
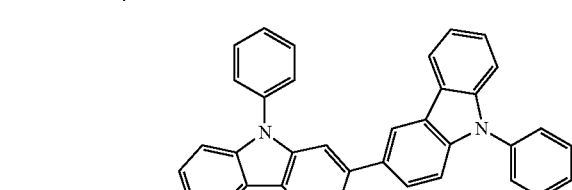
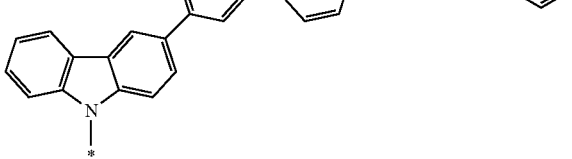
38
-continued
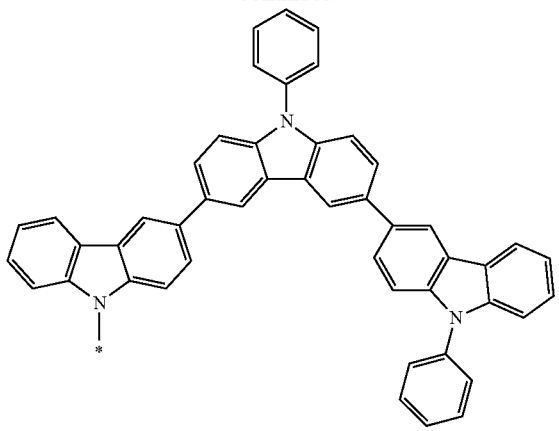
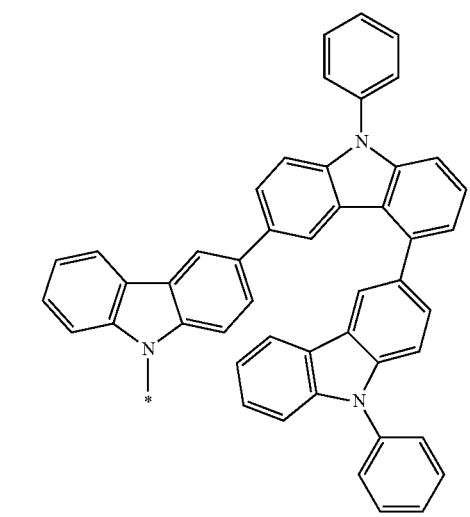
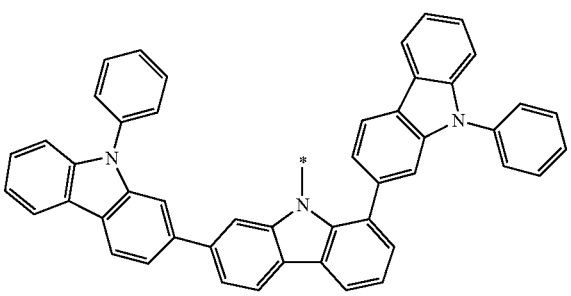
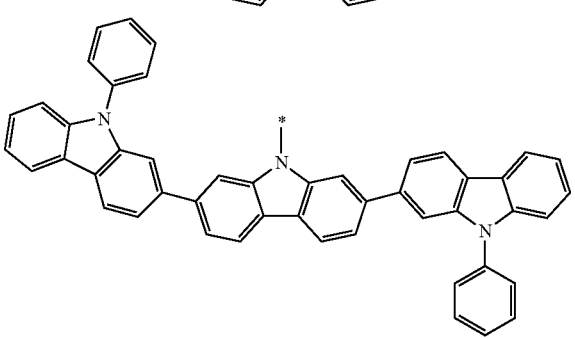

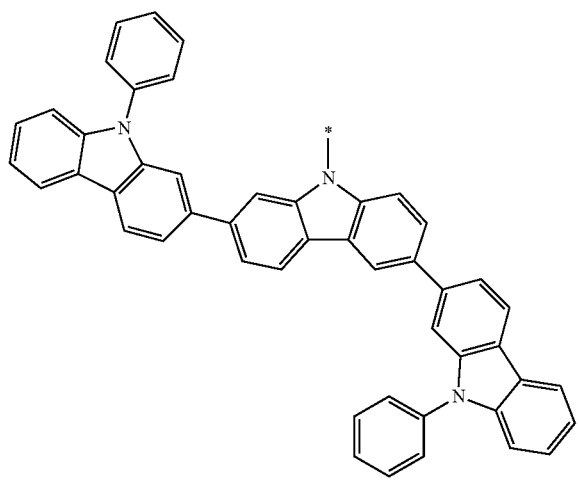
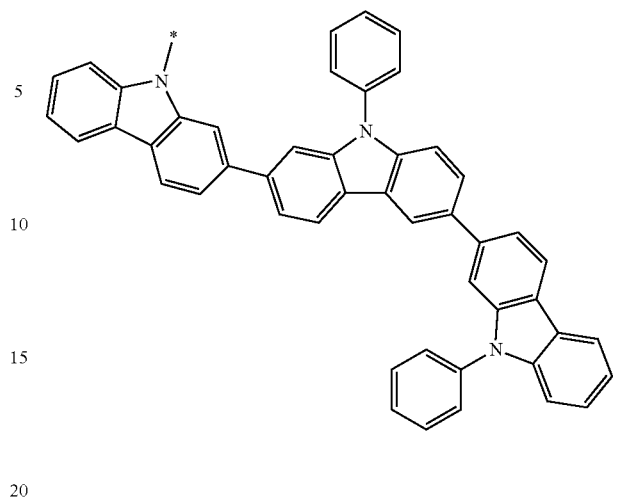
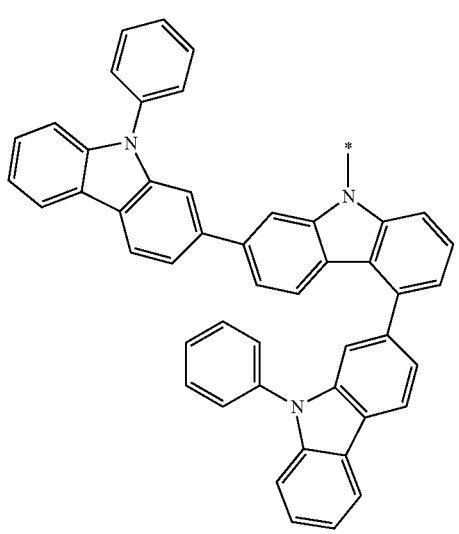
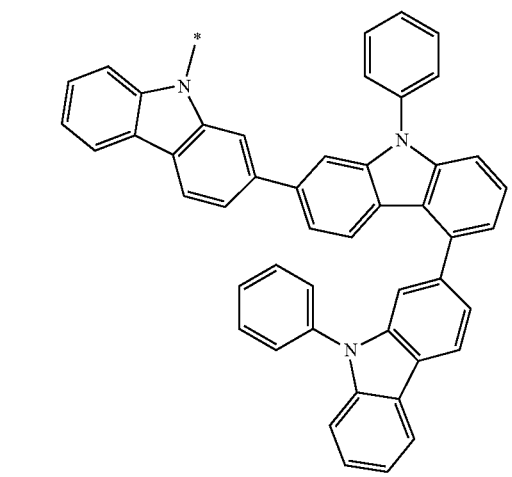
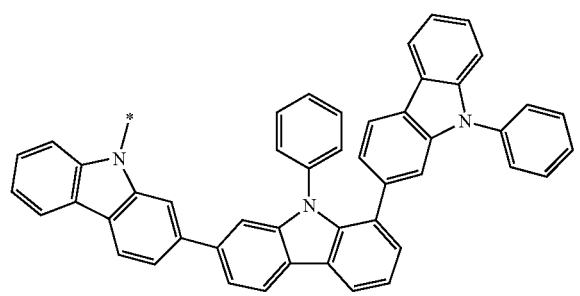
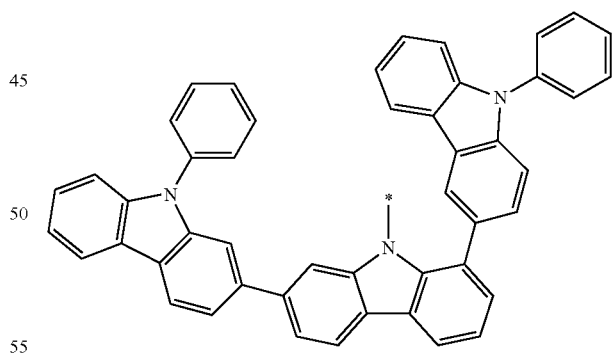
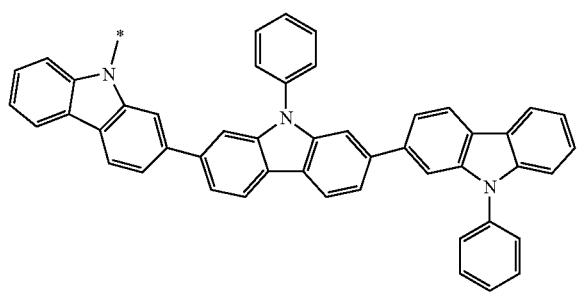
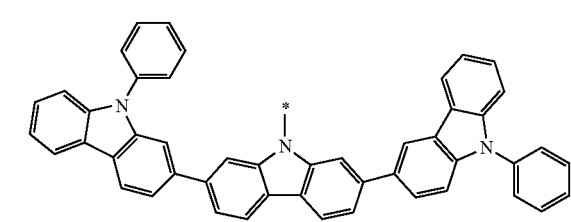

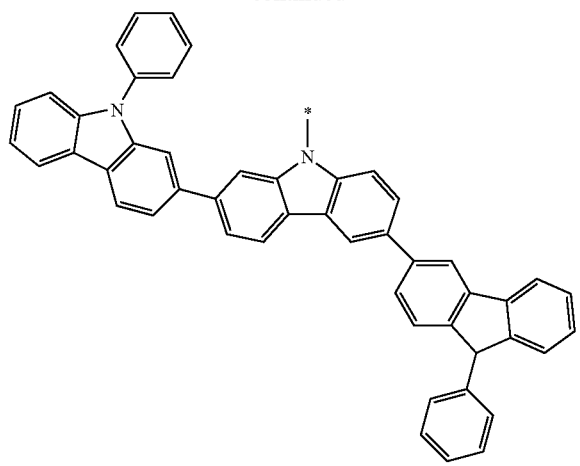
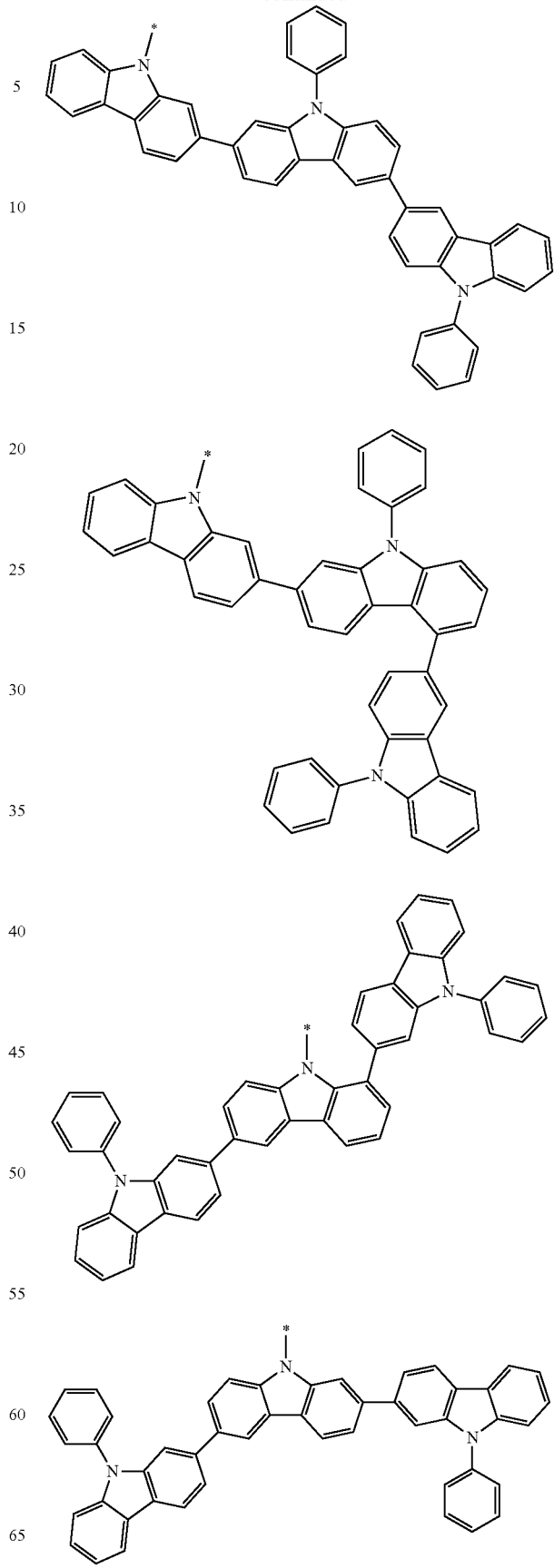

-continued
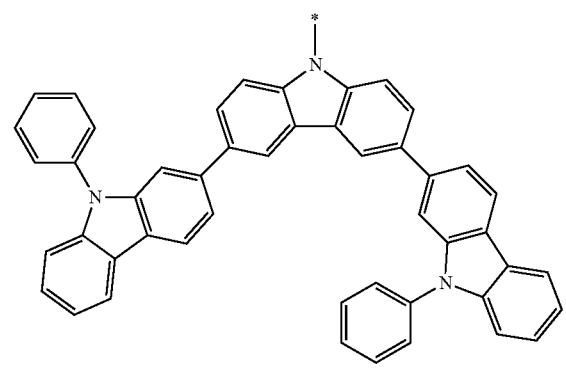
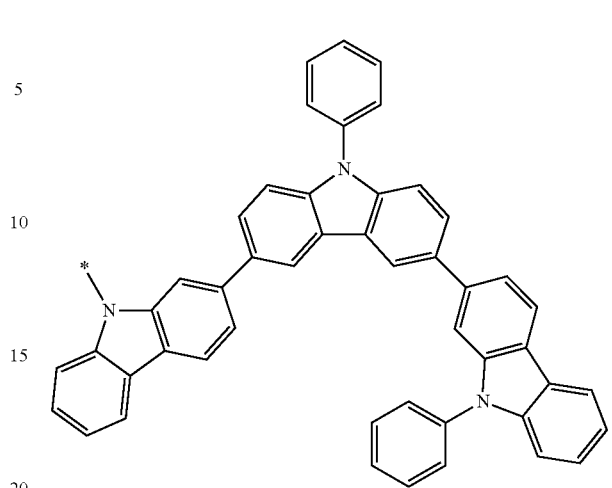
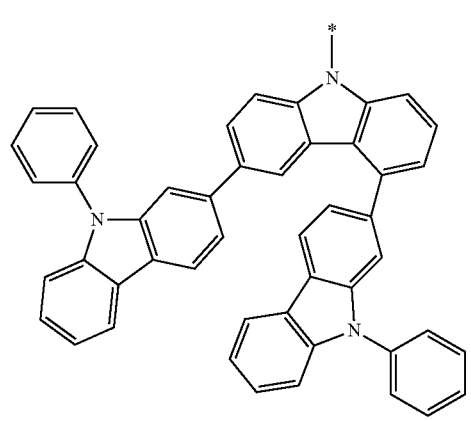
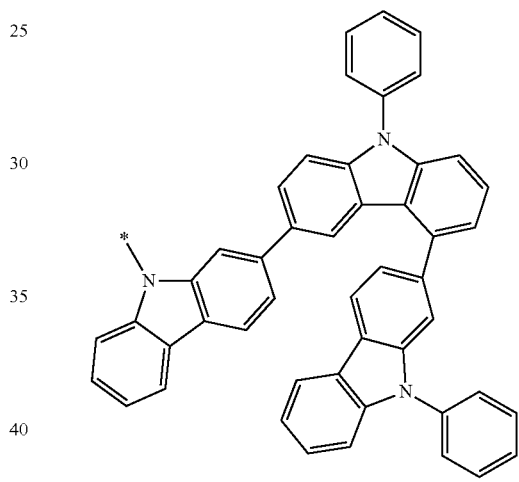
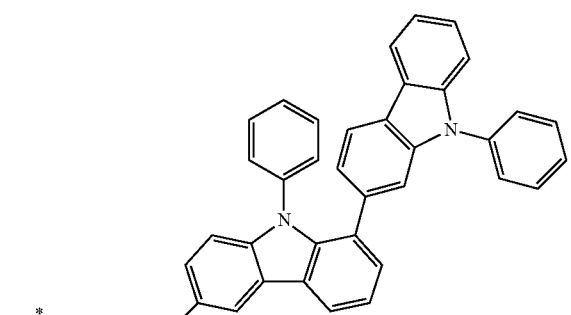
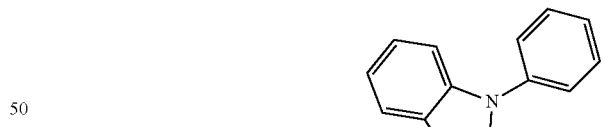
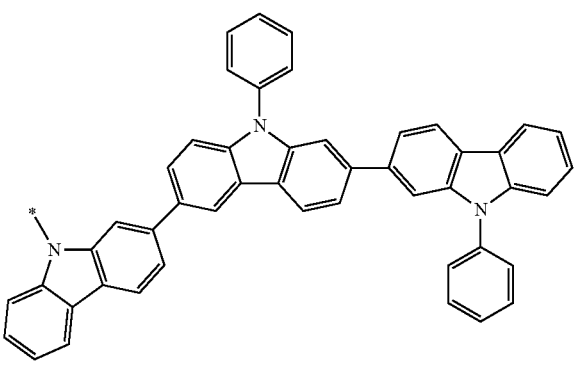
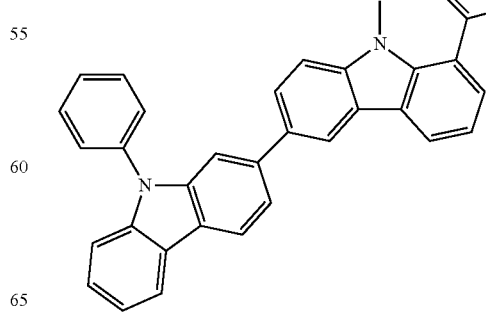

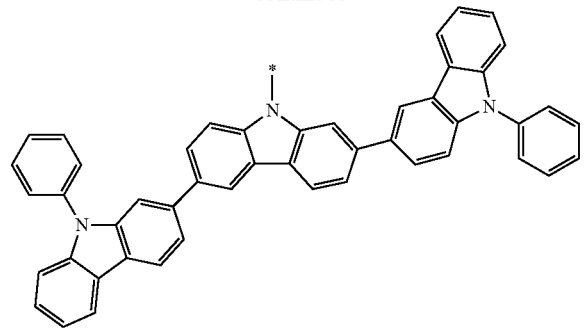
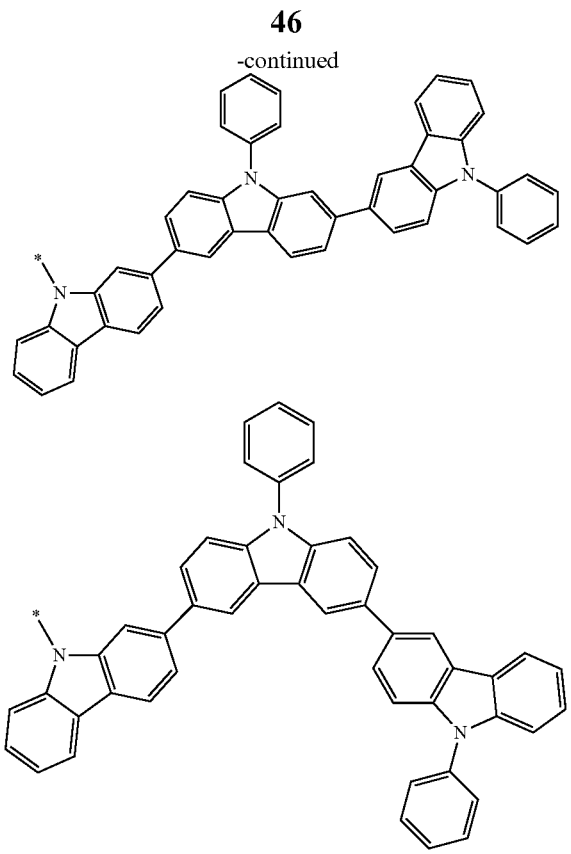
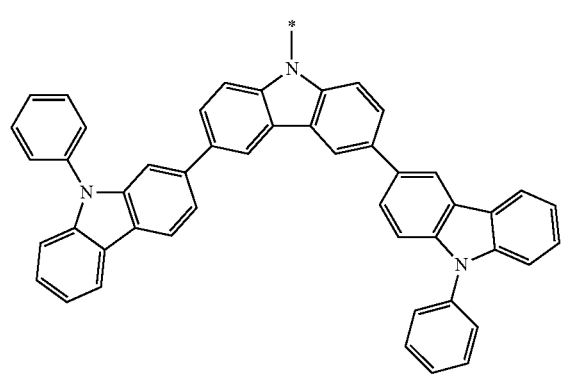
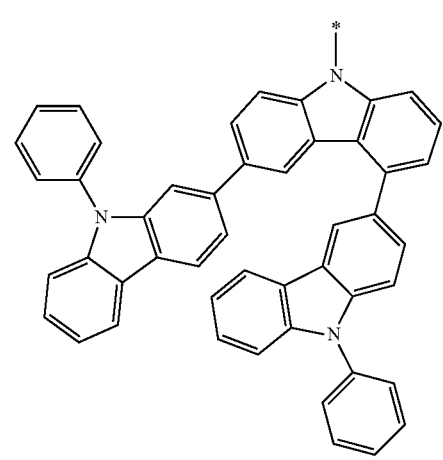
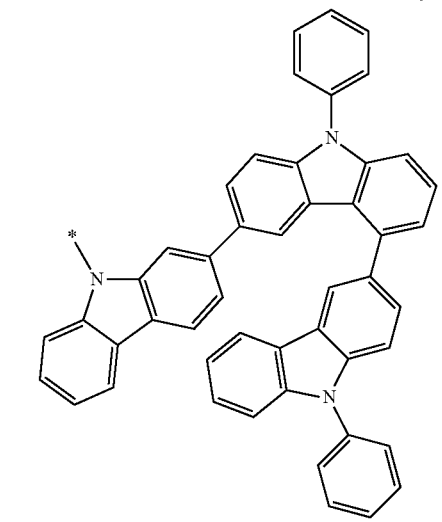
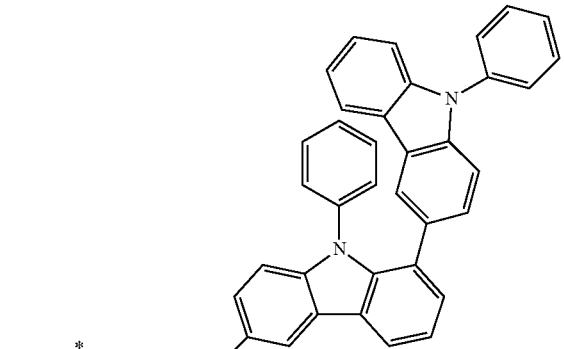
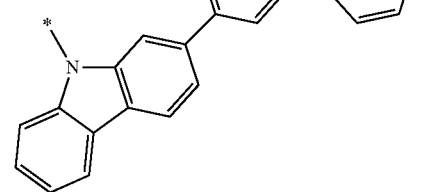
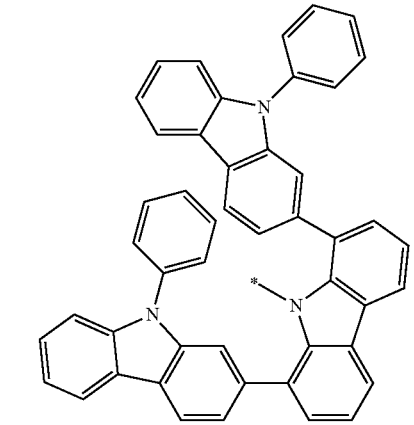

-continued
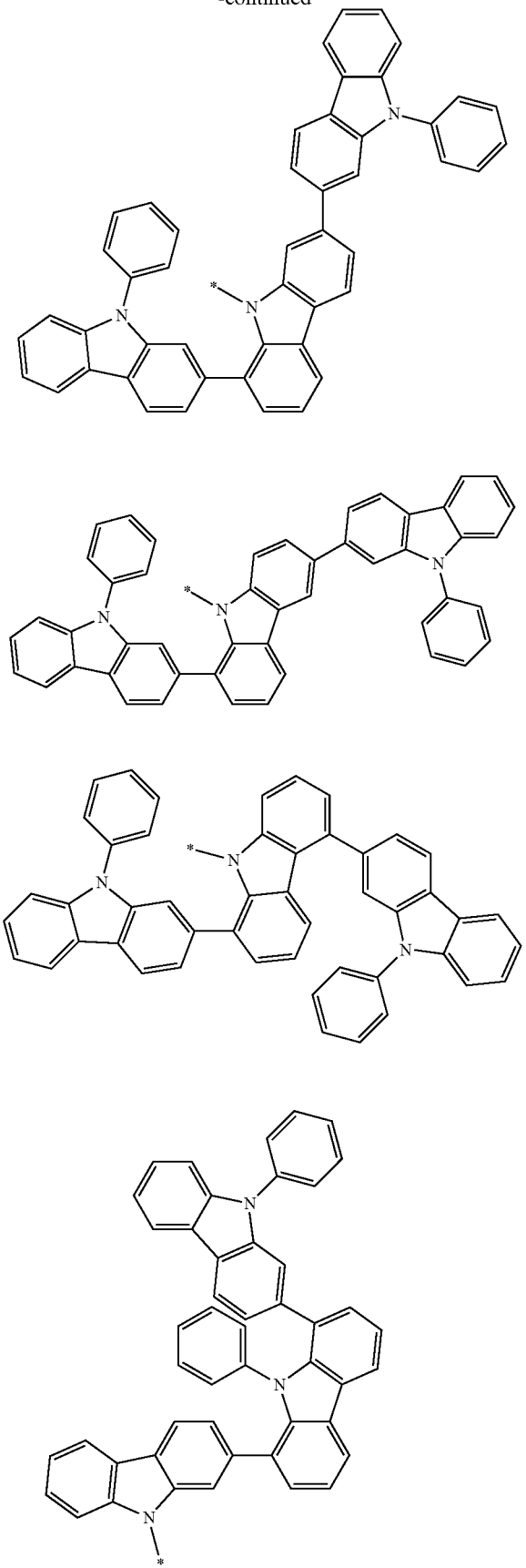
-continued
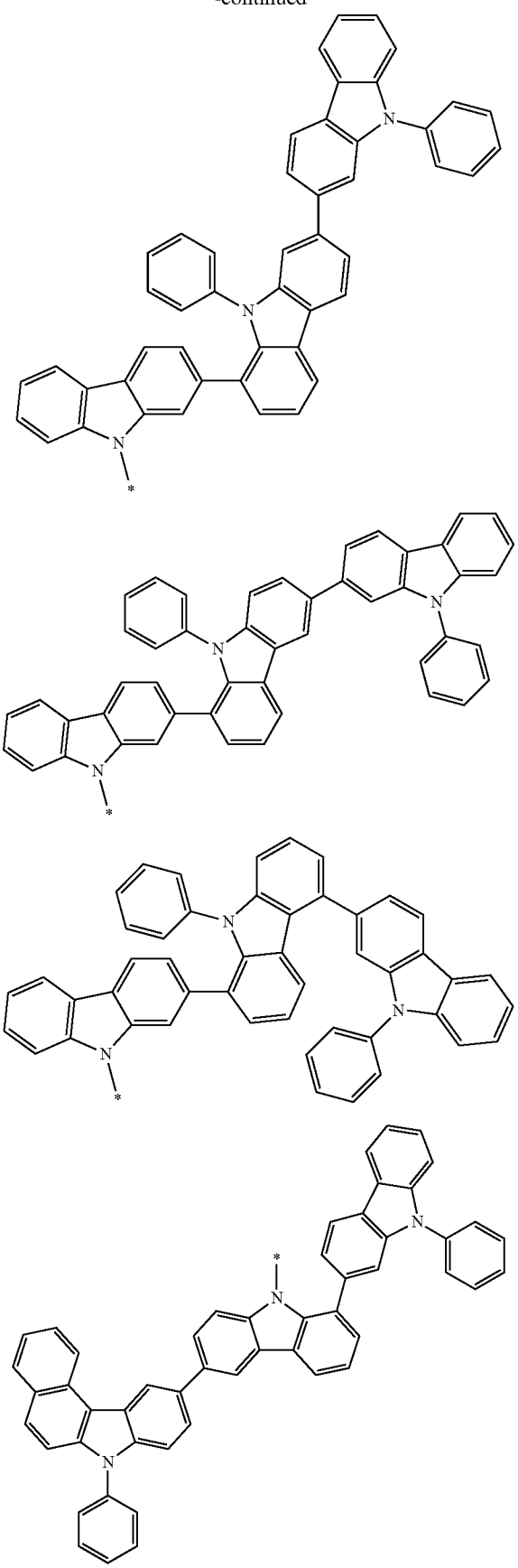

49
-continued
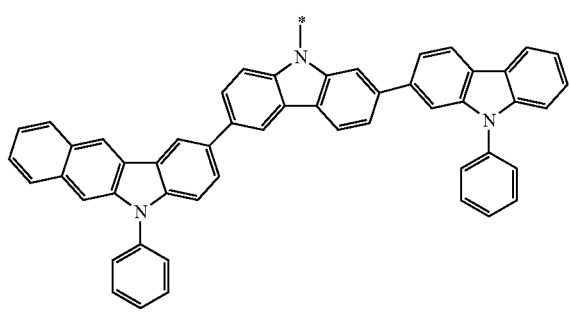
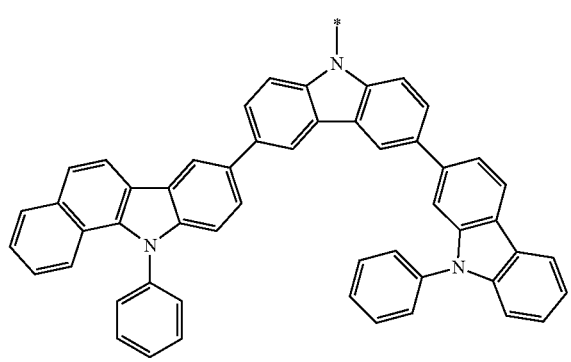
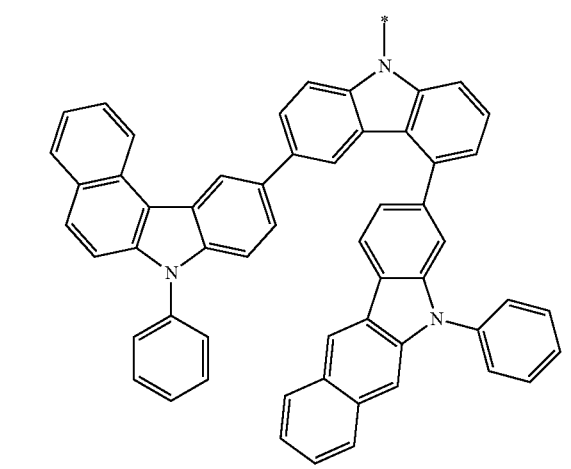
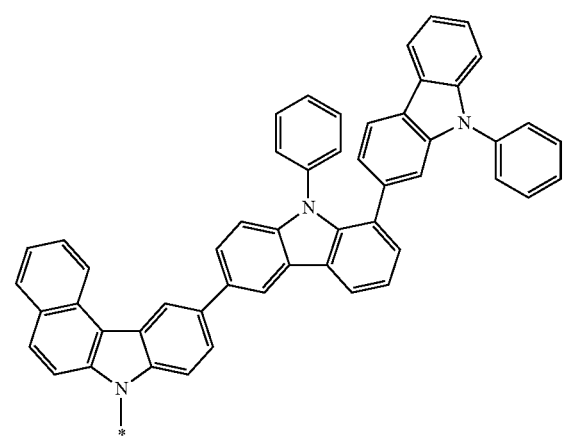
50
-continued
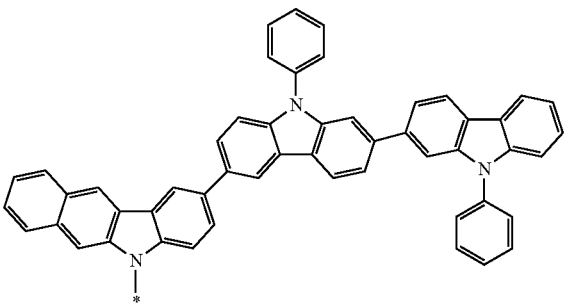
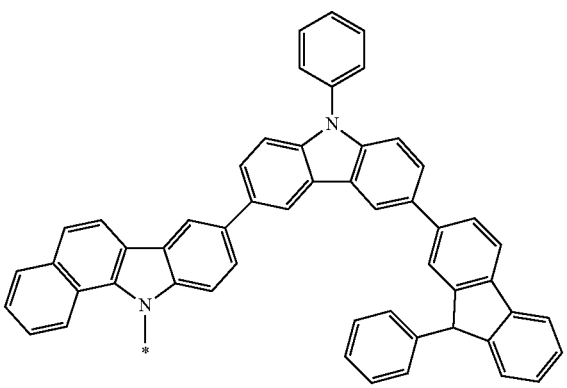
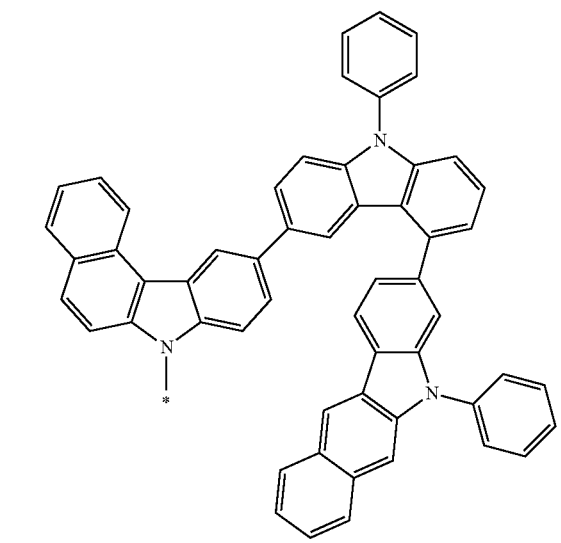

51
-continued
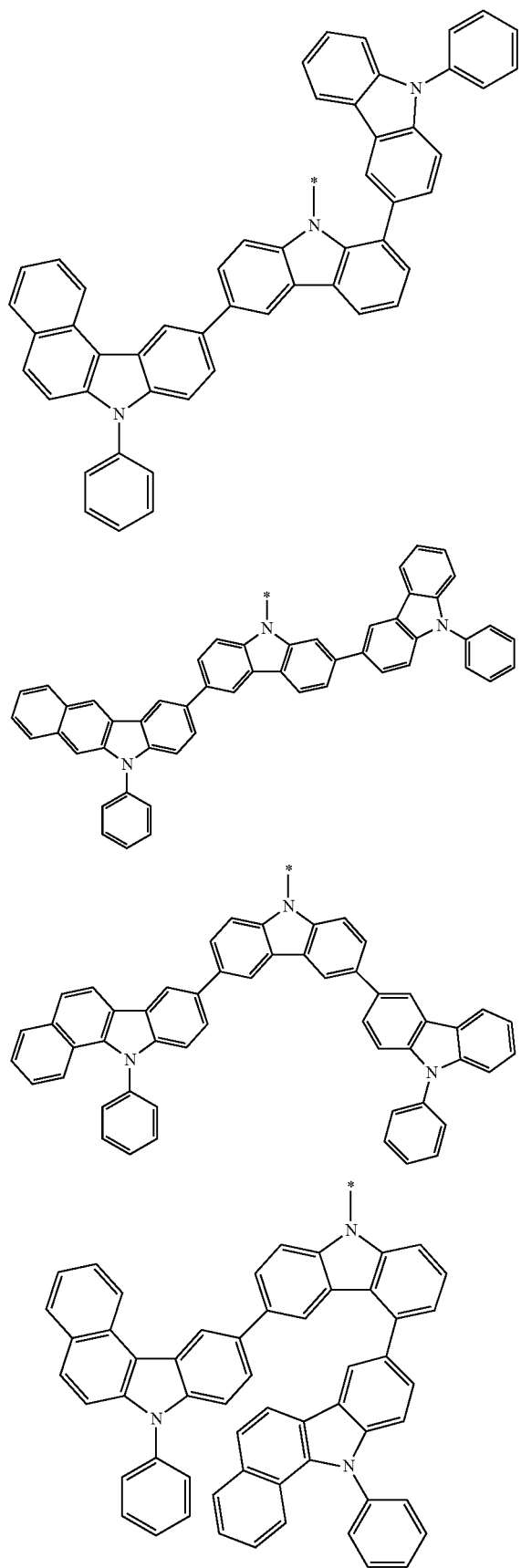 [SMILES: Cn1c2ccc(-c3ccc4c(c3)c3c5ccccc5ccc3n4-c3ccccc3)cc2c2cccc(-c3ccc4c(c3)c3ccccc3n4-c3ccccc3)c21 ; Cn1c2ccc(-c3ccc4c(c3)c3cc5ccccc5cc3n4-c3ccccc3)cc2c2ccc(-c3ccc4c(c3)c3ccccc3n4-c3ccccc3)cc21 ; Cn1c2ccc(-c3ccc4c(c3)c3ccccc3n4-c3ccccc3)cc2c2cc(-c3ccc4c(c3)c3ccc5ccccc5c3n4-c3ccccc3)ccc21 ; Cn1c2ccc(-c3ccc4c(c3)c3c5ccccc5ccc3n4-c3ccccc3)cc2c2c(-c3ccc4c(c3)c3ccc5ccccc5c3n4-c3ccccc3)cccc21]
52
-continued
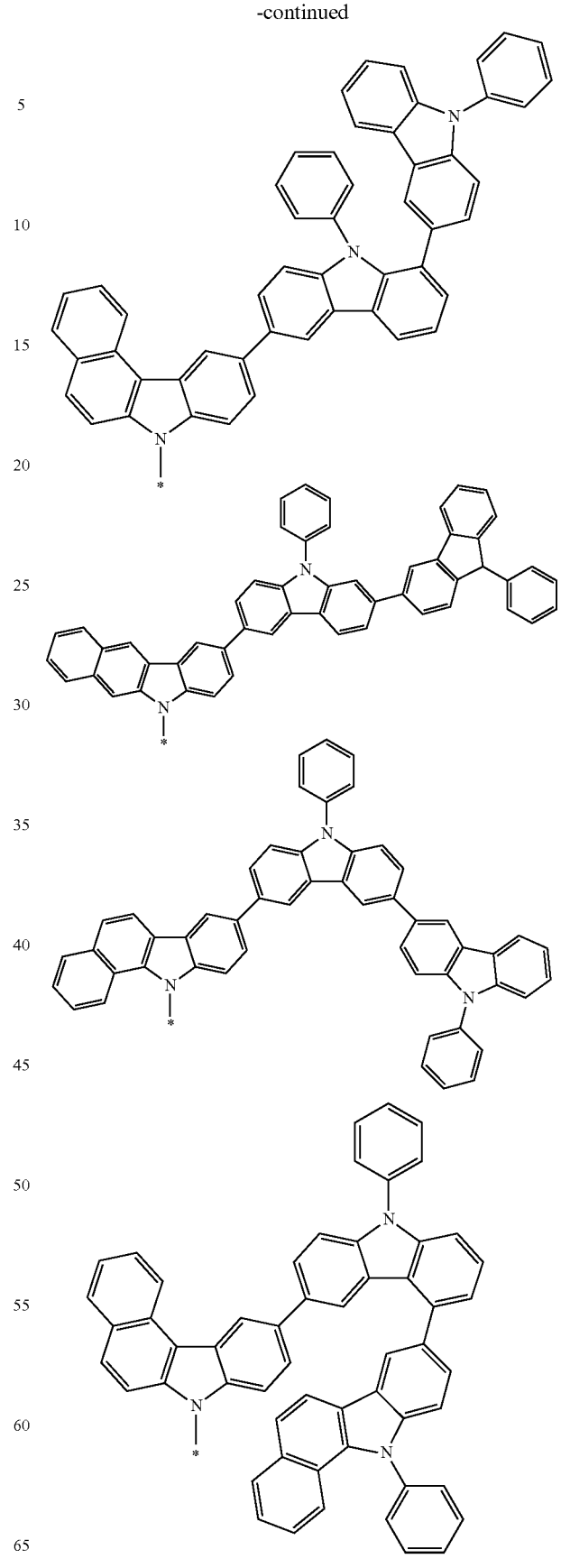

As described above, p to r in formula 1[I] each independently represent an integer of 0 to 3, and p+q+r is 3. Preferably, two selected from p to r cannot be 0 at the same time, although not particularly limited thereto.

When p, q or r is 2 or 3, 2 or 3 groups in each [ ] may be the same or different.

Compound in an Aspect of the Invention

In an aspect of the invention, the compound is preferably a compound represented by formula 1a[I] (also referred to as "compound 1a[I]"):

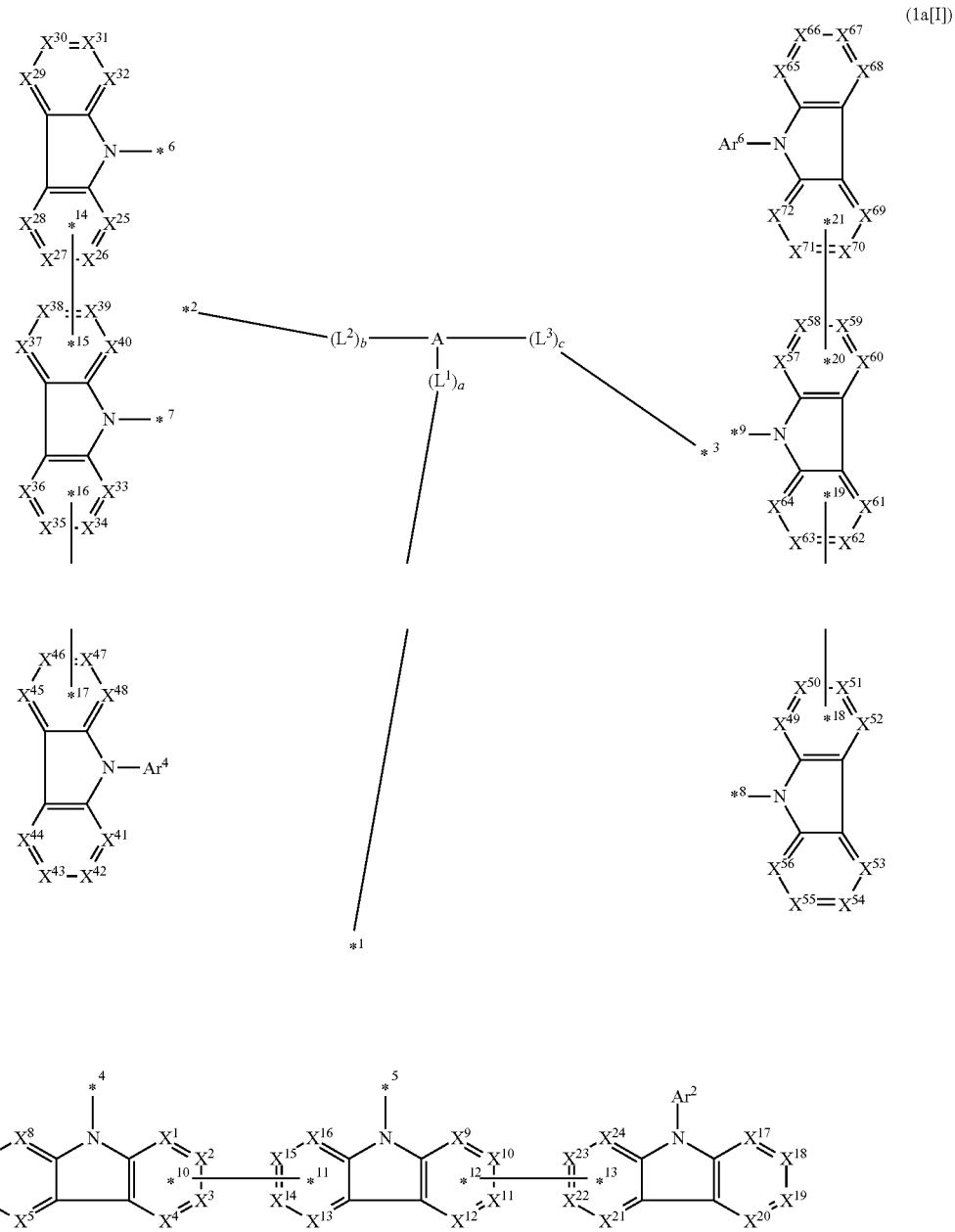

(1a[I])

in formula 1a[I], A, $L^1$ to $L^3$, a to c, $X^1$ to $X^{72}$, *1 to *21, $Ar^2$, $Ar^4$, and $Ar^6$ are as described above in formula 1[I].

In an aspect of the invention, the compound 1a[I] is more preferably a compound represented by formula 1a-i[I] (also referred to as "compound 1a-i[I]"):

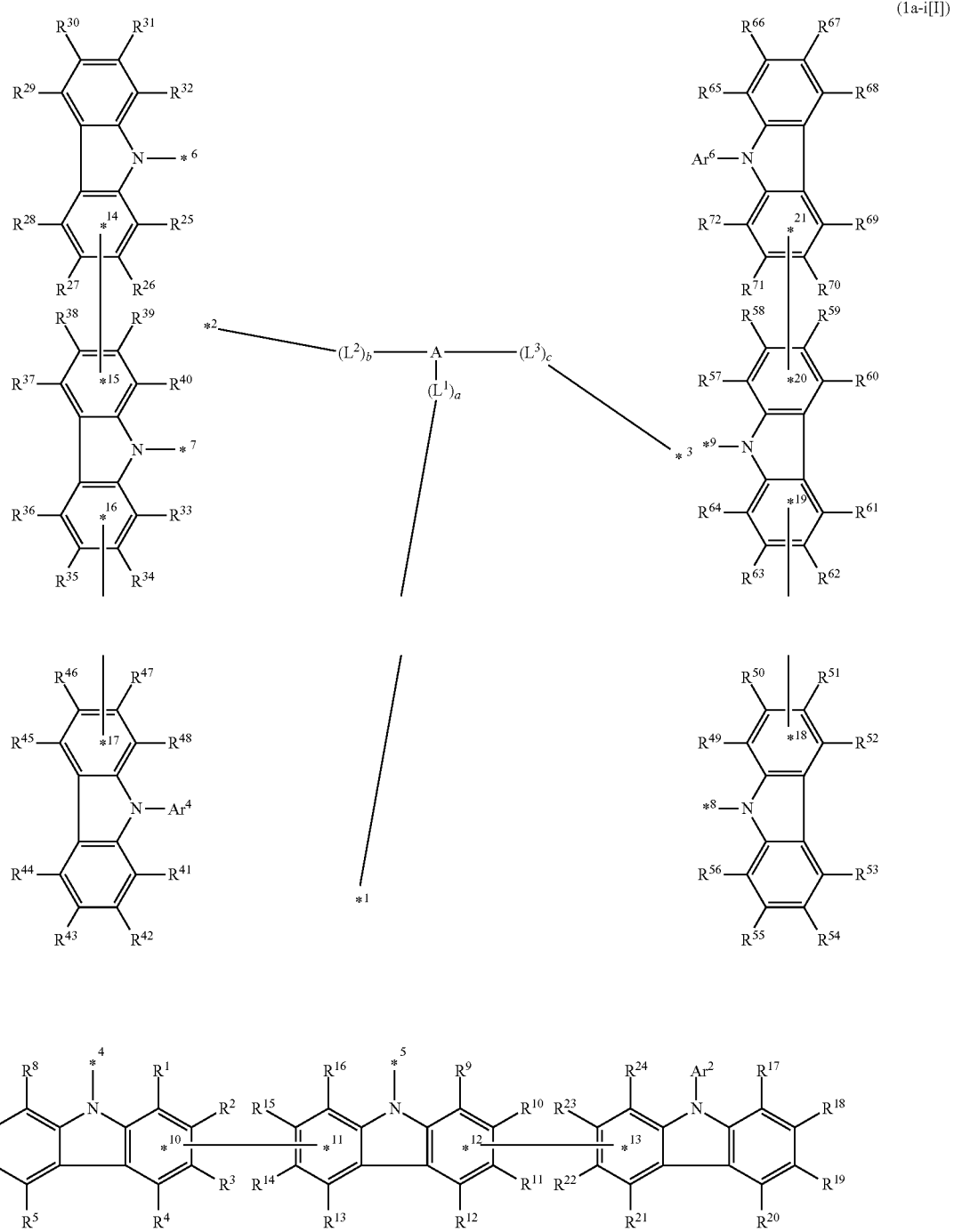

(1a-i[I])

in formula 1a-i[I], A, $L^1$ to $L^3$, a to c, *1 to *9, $Ar^2$, $Ar^4$, and $Ar^6$ are as described above in formula 1[I]; $R^1$ to $R^{72}$ are as described above with respect to R of formula 1[I], i.e., $R^1$ to $R^{72}$ may be the same or different and each independently represent a hydrogen atom or a substituent; and two selected from $R^1$ to $R^{72}$ may be bonded to each other to form a ring.

In formula 1a-i[I],

*10-*11 is a bond between carbon atoms from which one of $R^1$ to $R^4$ and one of $R^{13}$ to $R^{16}$ are removed;

*12-*13 is a bond between carbon atoms from which one of $R^9$ to $R^{12}$ and one of $R^{21}$ to $R^{24}$ are removed;

*14-*15 is a bond between carbon atoms from which one of $R^{25}$ to $R^{28}$ and one of $R^{37}$ to $R^{40}$ are removed;

*16-*17 is a bond between carbon atoms from which one of $R^{33}$ to $R^{36}$ and one of $R^{46}$ to $R^{48}$ are removed;

*18-*19 is a bond between carbon atoms from which one of $R^{49}$ to $R^{52}$ and one of $R^{61}$ to $R^{64}$ are removed; and

*20-*21 is a bond between carbon atoms from which one of $R^{57}$ to $R^{60}$ and one of $R^{69}$ to $R^{72}$ are removed.

Namely, each of *10, *12, *14, *16, *18, and *20 is bonded to a carbon atom at 1-position, 2-position, 3-position, or 4-position of a carbazolyl group, and each of *11, *13, *15, *17, *19, and *21 is bonded to a carbon atom at 5-position, 6-position, 7-position, or 8-position of another carbazolyl group, thereby linking two carbazolyl groups by *10-*11, *12-*13, *14-*15, *16-*17, *18-*19, and *20-*21, respectively.

In an aspect of the invention, the compound 1a-i[I] is preferably a compound wherein two selected from $R^1$ to $R^{72}$ are not bonded to each other, thereby failing to form a ring and more preferably represented by formula 1a-vi[I]:

in formula 1a-vi[I], A, $L^1$ to $L^3$, a to c, *1 to *9, $Ar^2$, $Ar^4$, and $Ar^6$ are as described above in formula 1[I], and each of *10-*11, *12-*13, *14-*15, *16-*17, *18-*19, and *20-*21 is a bond between carbon atoms in each benzene ring from which hydrogen atoms are removed.

Namely, each of *10, *12, *14, *16, *18, and *20 is bonded to a carbon atom at 1-position, 2-position, 3-position, or 4-position of a carbazolyl group, and each of *11, *13, *15, *17, *19, and *21 is bonded to a carbon atom at 5-position, 6-position, 7-position, or 8-position of another carbazolyl group, thereby linking two carbazolyl groups by *10-*11, *12-*13, *14-*15, *16-*17, *18-*19, and *20-*21, respectively In an aspect of the invention, the compound 1a-i[I] is more preferably a compound represented by formula 1a-ii[I] (also referred to as "compound 1a-ii[I]"):

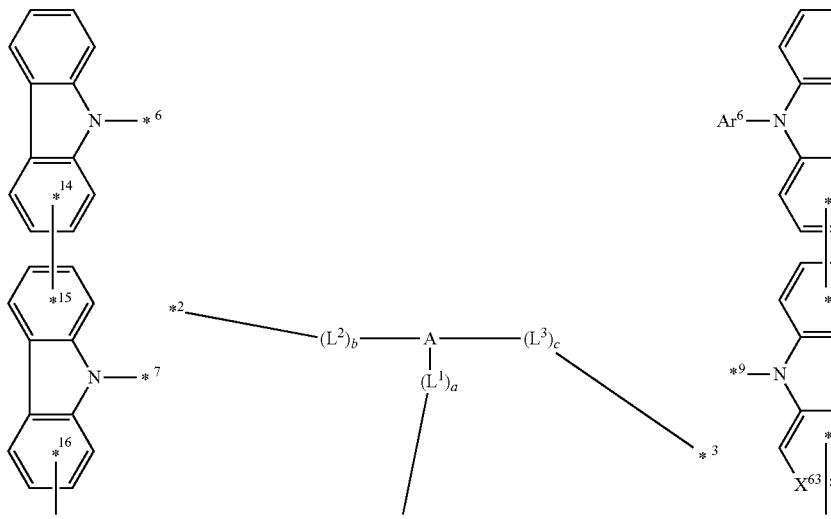

(1a-vi[I])

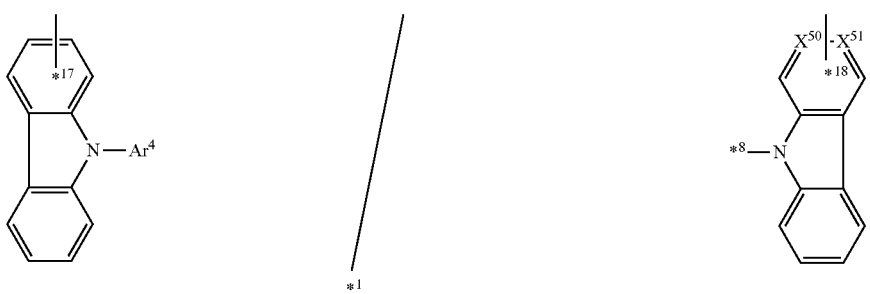

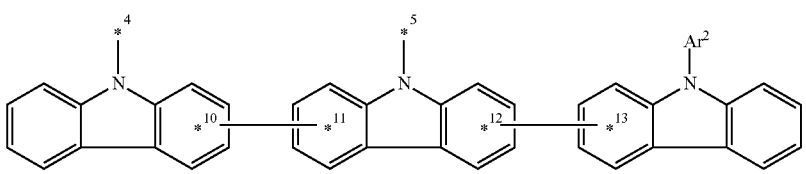

(1a-ii[I])
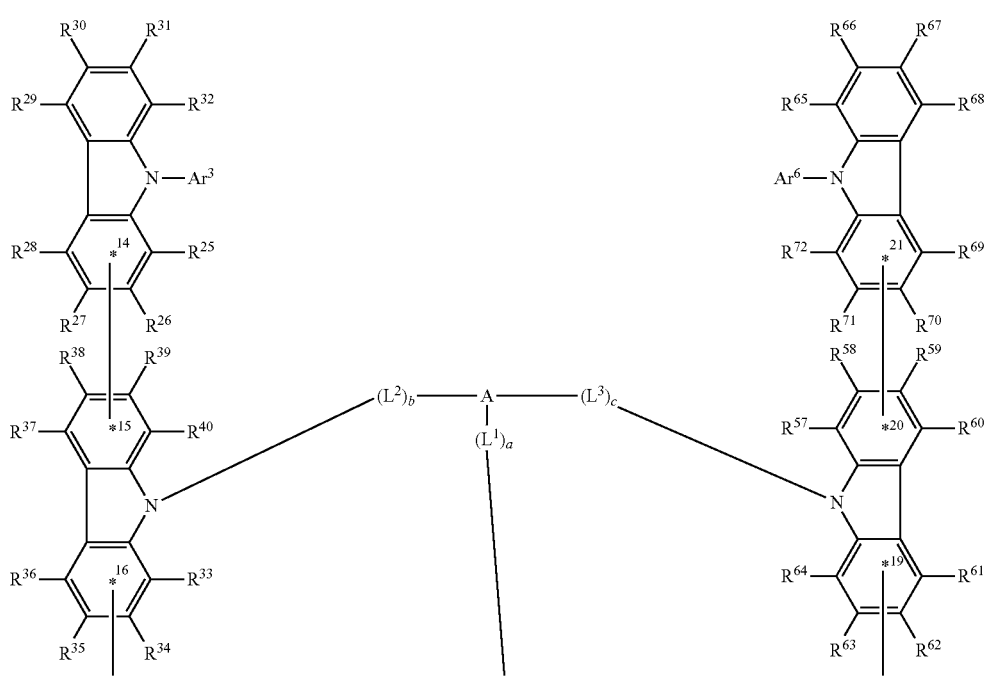
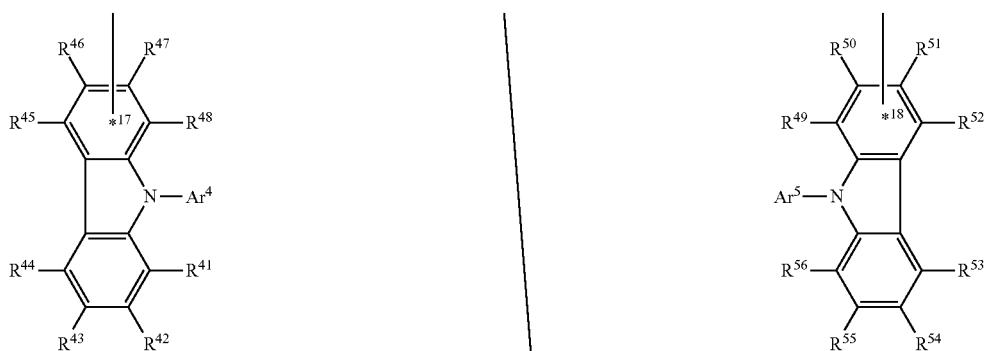
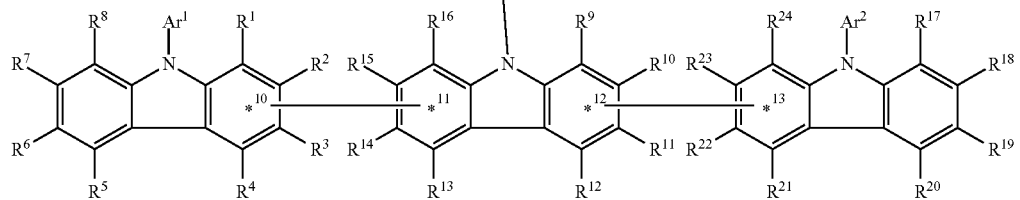
in formula 1a-ii[I], A, $L^1$ to $L^3$, a to c, and $Ar^1$ to $Ar^6$ are as described above in formula 1[I], and $R^1$ to $R^{72}$ and *10 to *21 are as described above in formula 1a-i[i].
Further, in an aspect of the invention, the compound 1a-ii[I] is more preferably a compound represented by any of formulae 1a-ii-1[I] to 1a-ii-6[I] (also referred to as "compounds 1a-ii-1[I] to 1a-ii-6[I]"):

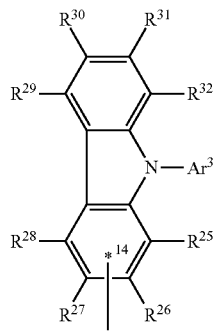
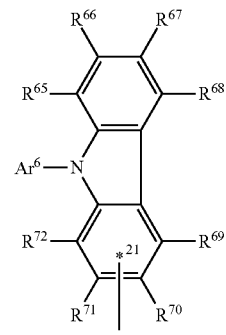
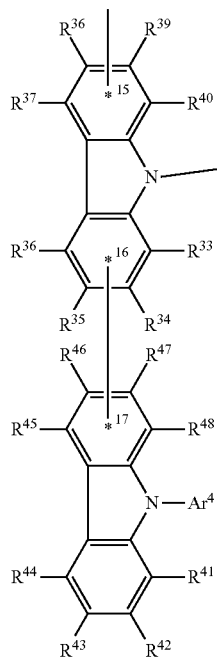
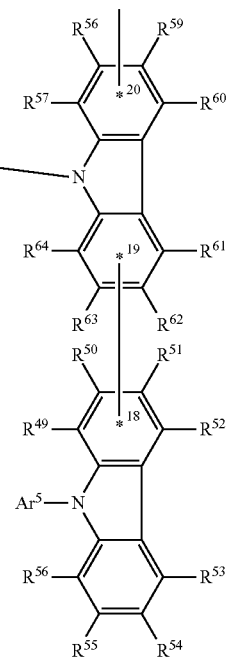
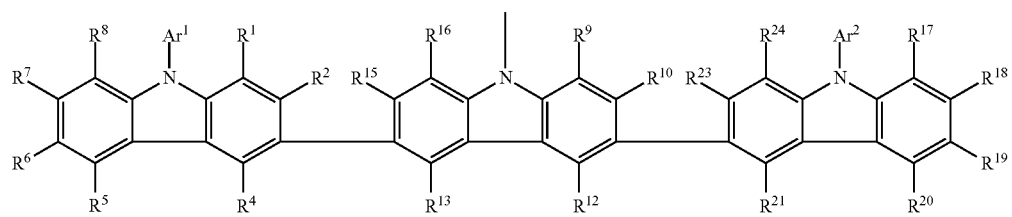
(1a-ii-1[I])
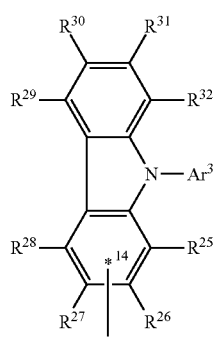
(1a-ii-2[I])

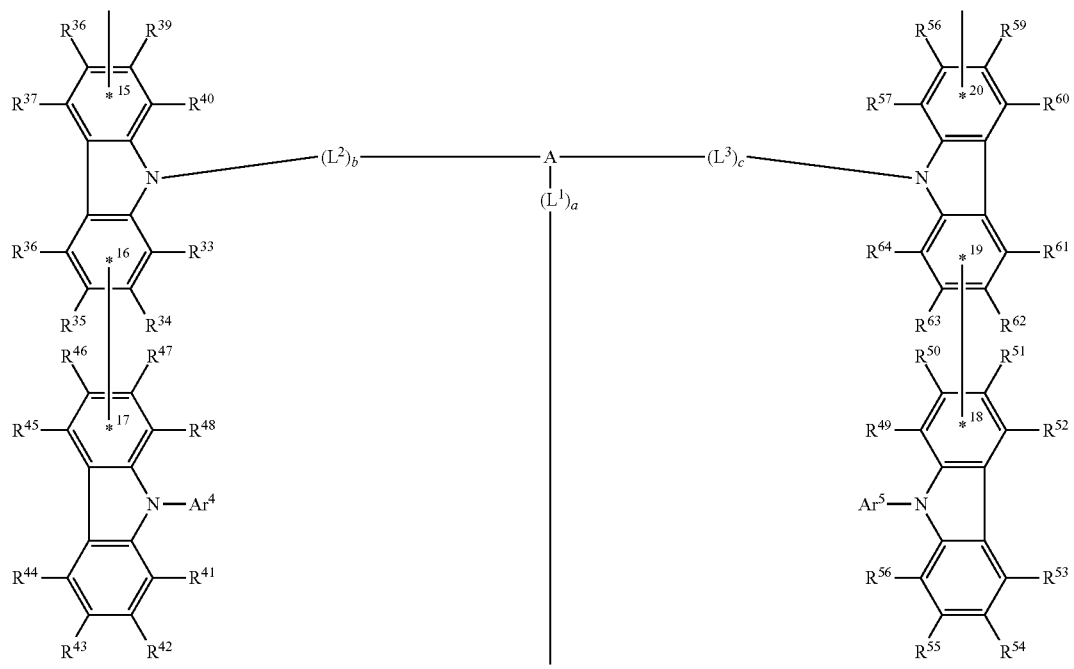
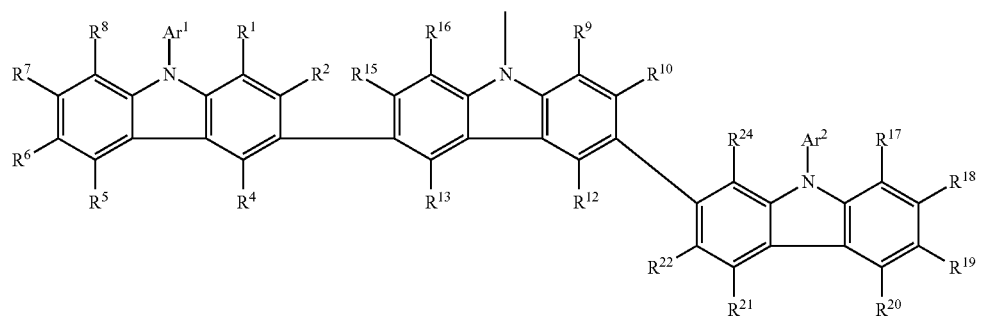
(1a-ii-3[I])
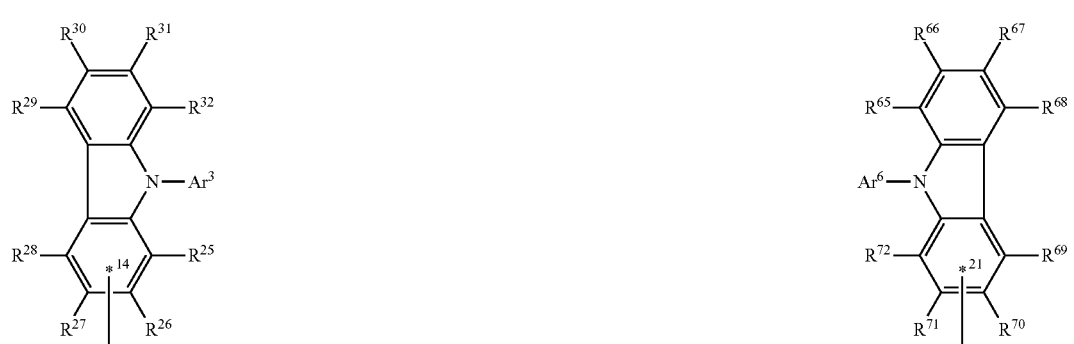
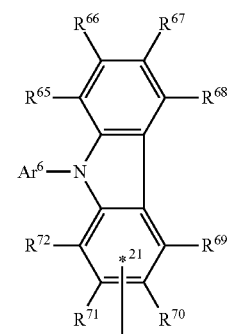

-continued
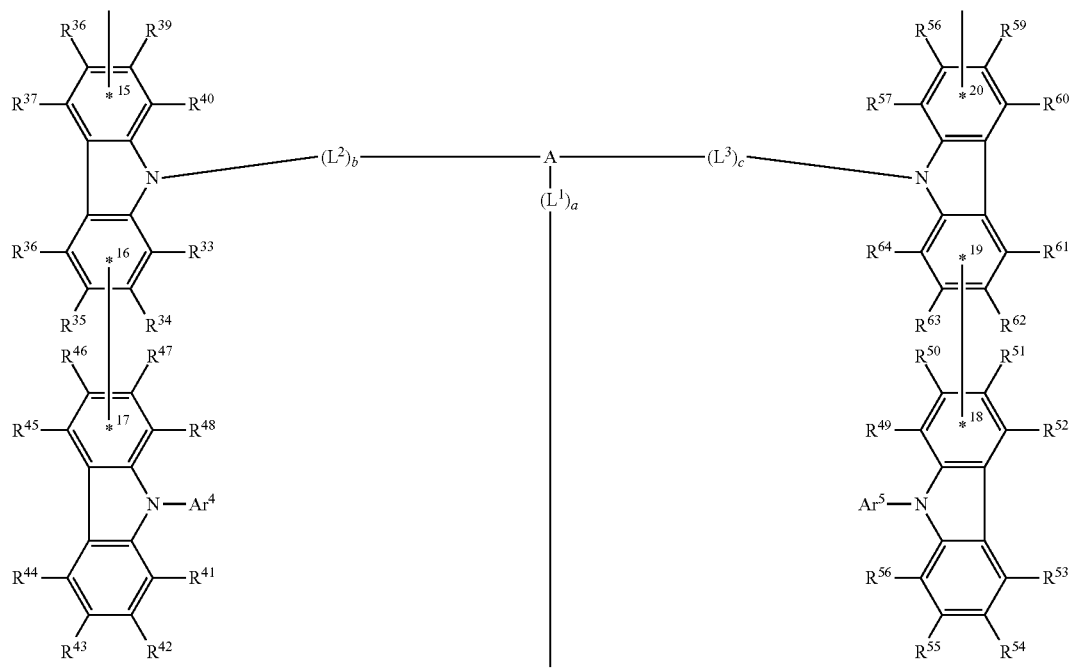
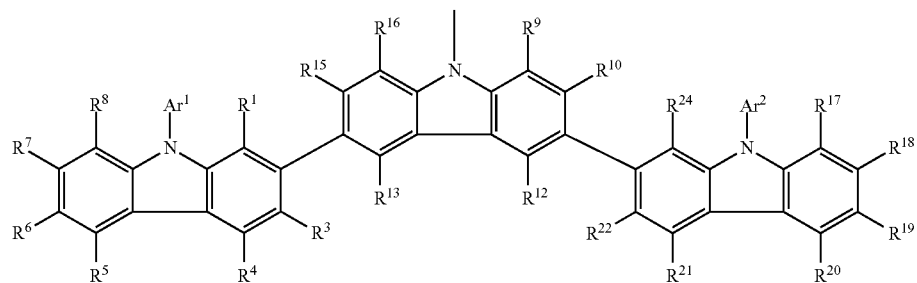
(1a-ii-4[I])
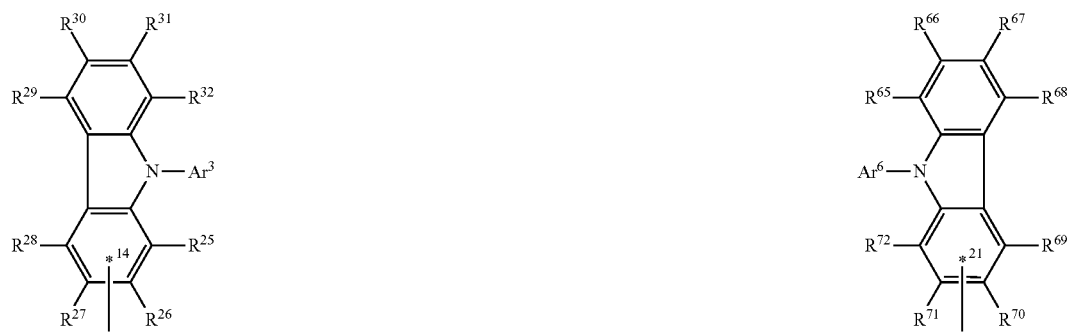

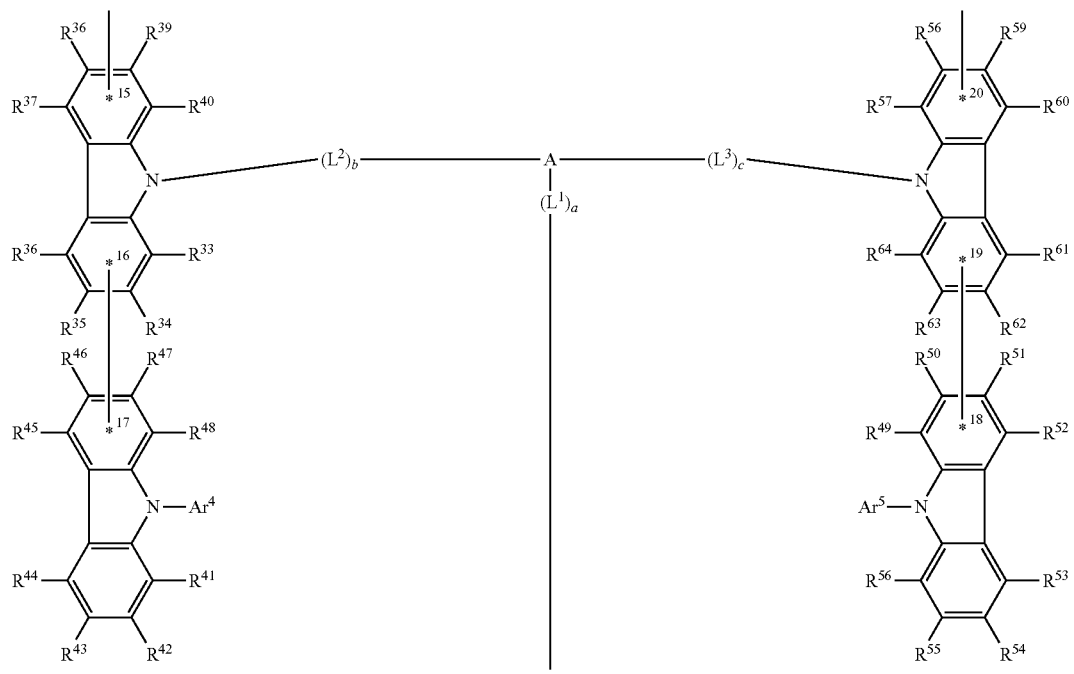
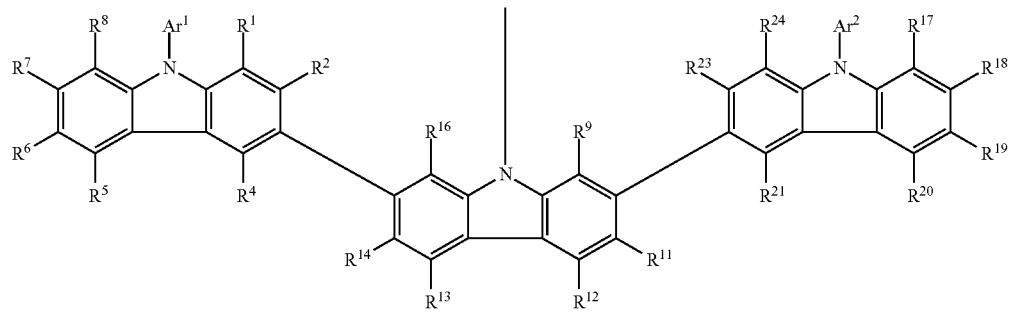
(1a-ii-5[I])
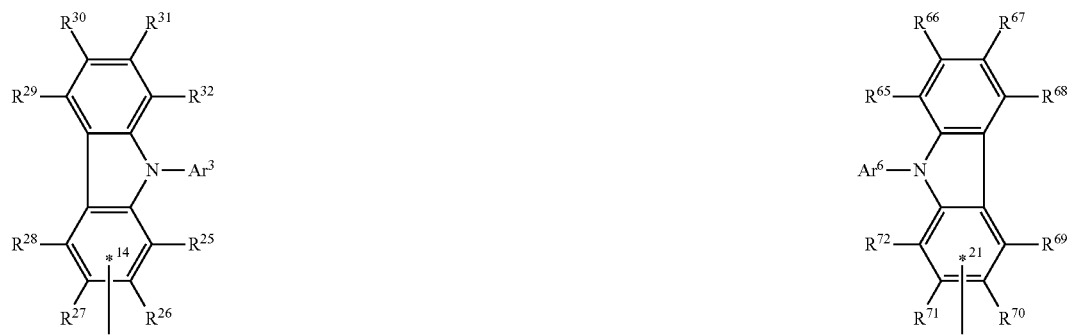

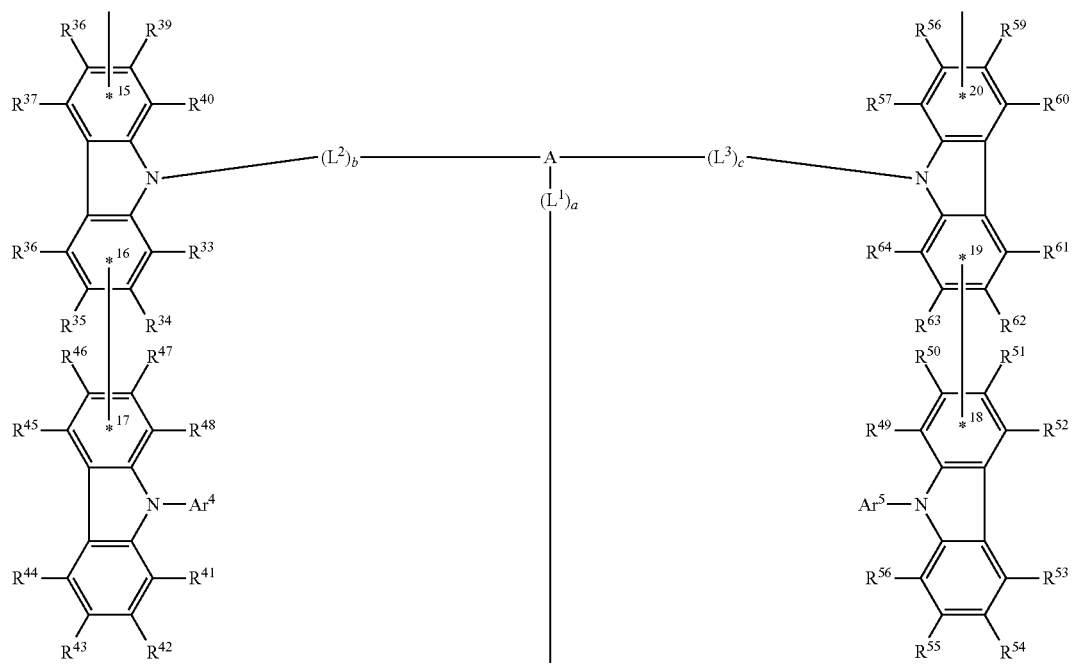
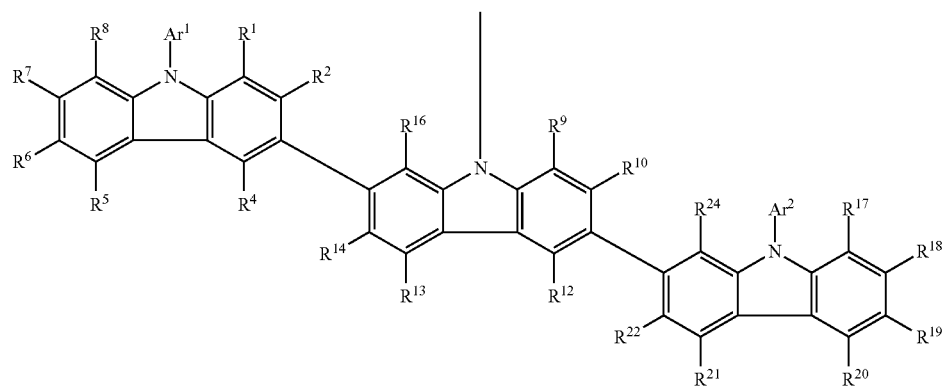
(1a-ii-6[I])
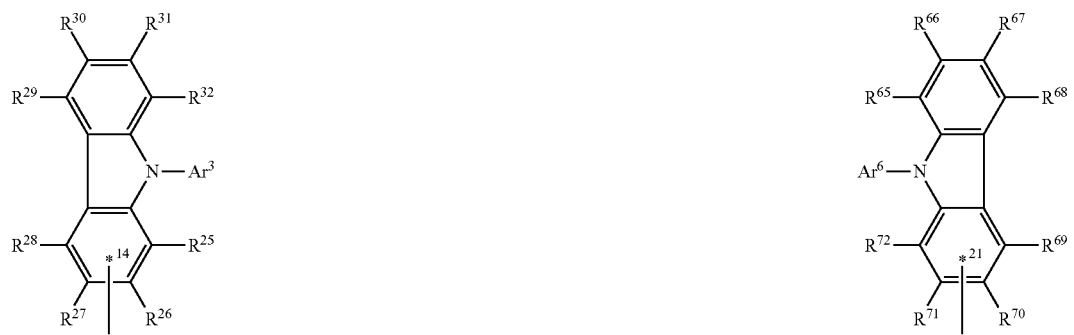

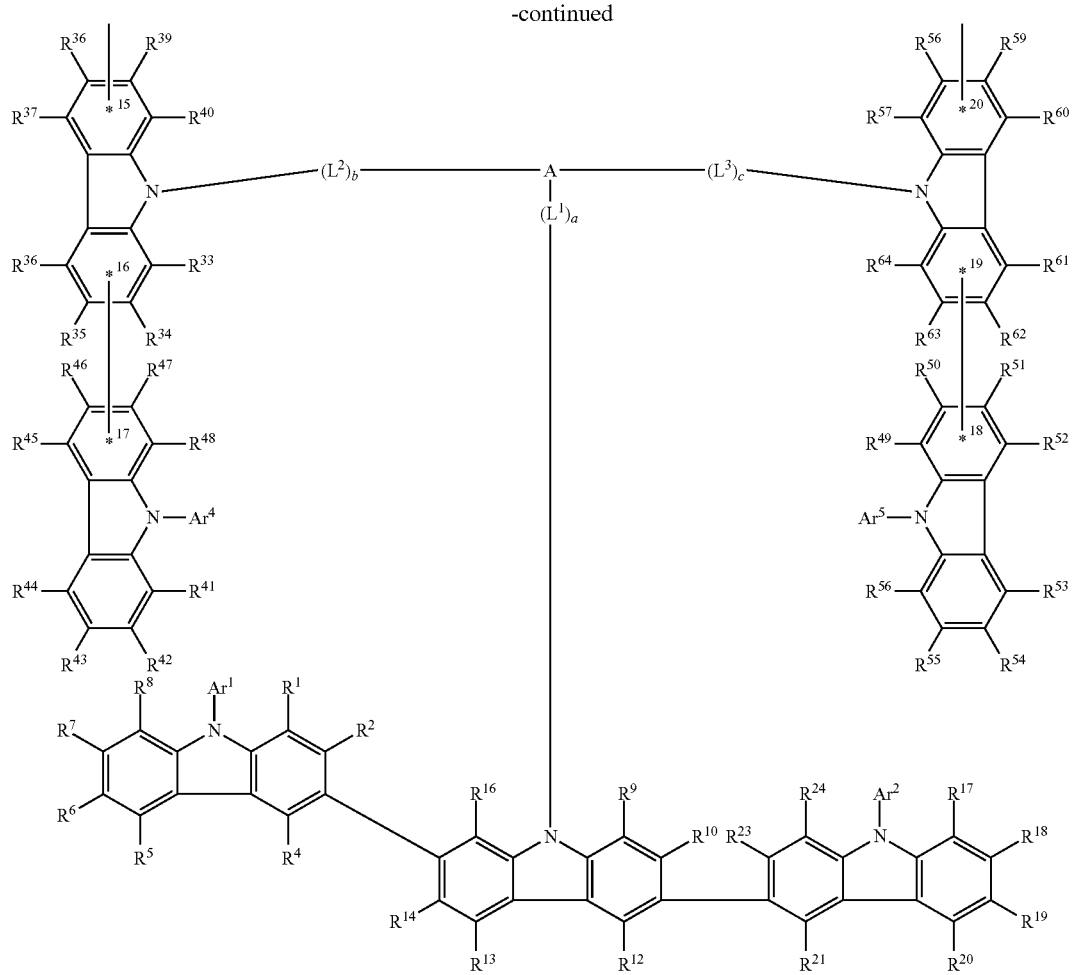
in formula 1a-ii-1[I] to 1a-ii-6[I], A, $L^1$ to $L^3$, a to c, and $Ar^1$ to $Ar^6$ are as described above in formula 1[I], and $R^1$ to $R^{72}$ and *10 to *21 are as described above in formula 1a-i[I].
In an aspect of the invention, the compound 1a-i[I] is more preferably a compound represented by formula 1a-iii [I] (also referred to as "compound 1a-iii[I]"):
(1a-iii[I])
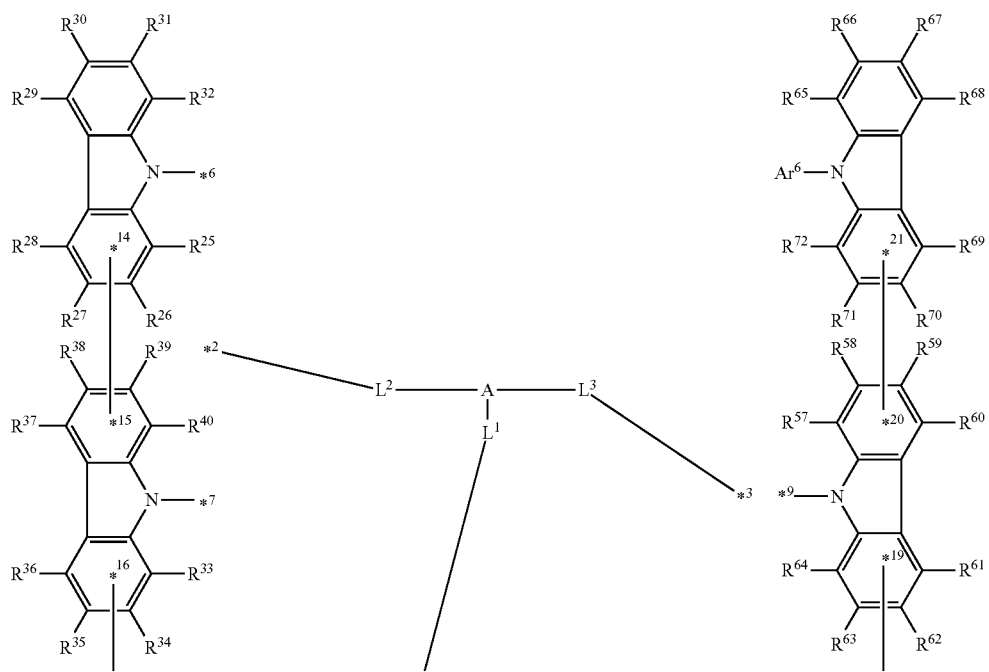

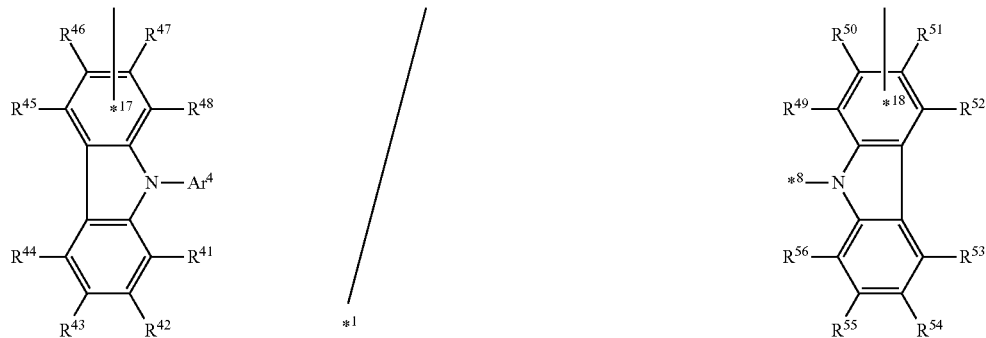
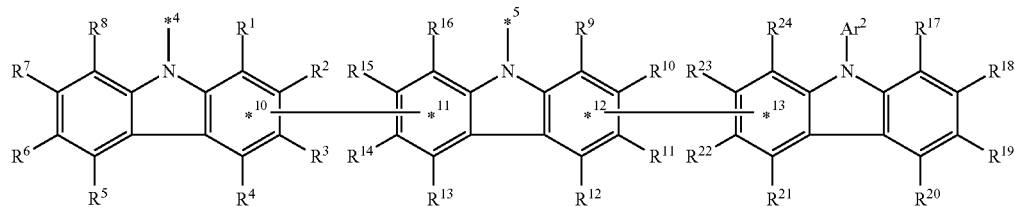
in formula 1a-iii[I], A, $L^1$ to $L^3$, *1 to *9, $Ar^2$, $Ar^4$, and $Ar^6$ are as described above in formula 1[I], and $R^1$ to $R^{72}$ and *10 to *21 are as described above in formula 1a-i[I].
Further, in an aspect of the invention, the compound 1a-i[I] is preferably a compound represented by formula 1a-iv[I] (also referred to as "compound 1a-iv[I]"):
(1a-iv[I])
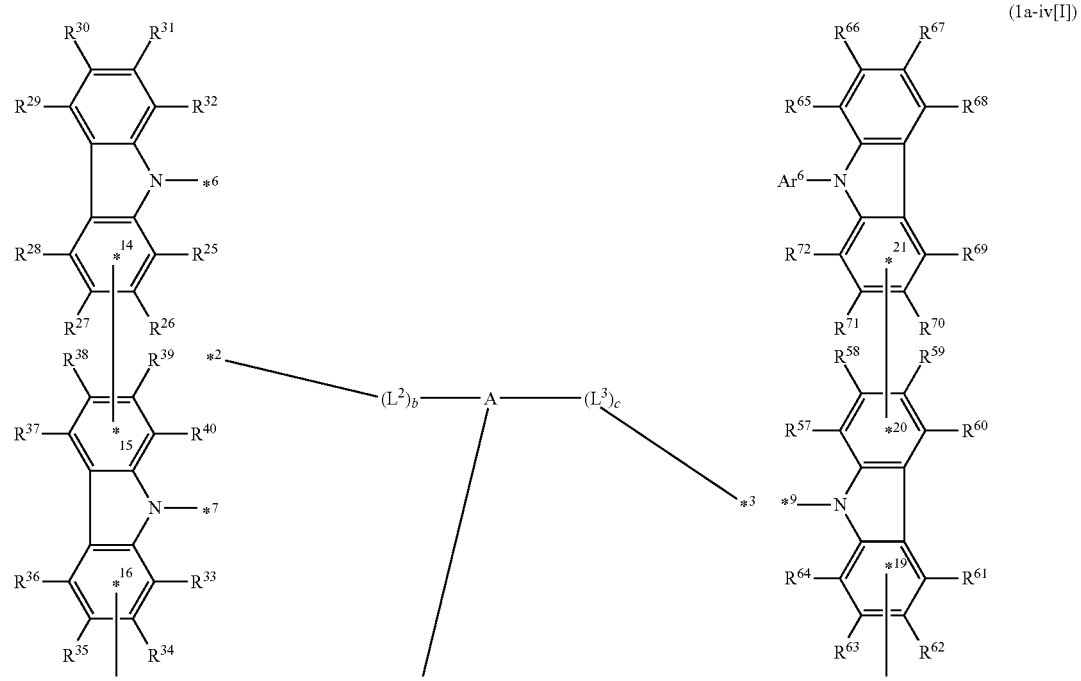

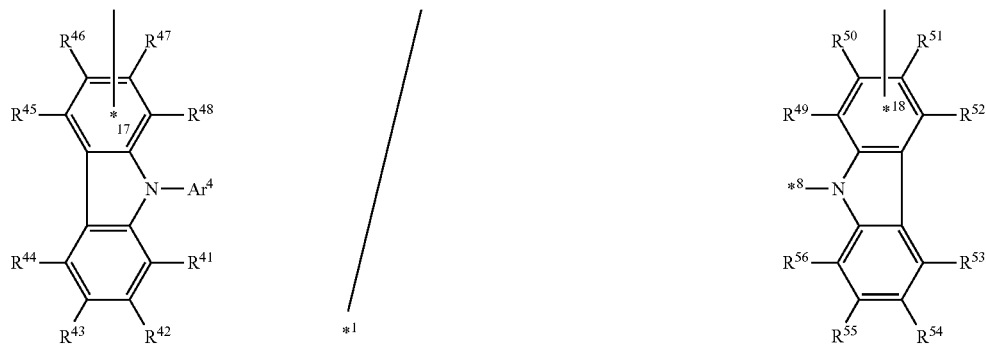
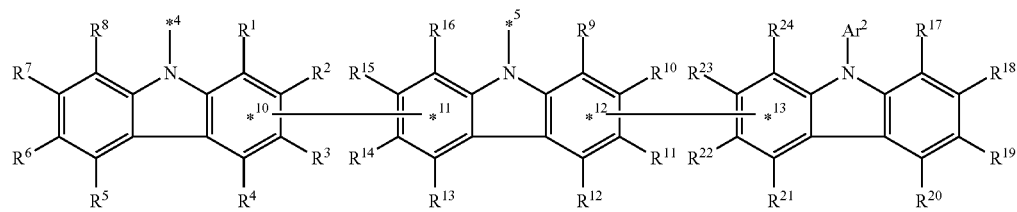
in formula 1a-iv[I], A, $L^2$, $L^3$, b, c, *1 to *9, $Ar^2$, $Ar^4$, and $Ar^6$ are as described above in formula 1[I], and $R^1$ to $R^{72}$ and *10 to *21 are as described above in formula 1a-i[I].
Further, in an aspect of the invention, the compound 1a-i[I] is more preferably a compound represented by formula 1a-v[I] (also referred to as "compound 1a-v[I]"):
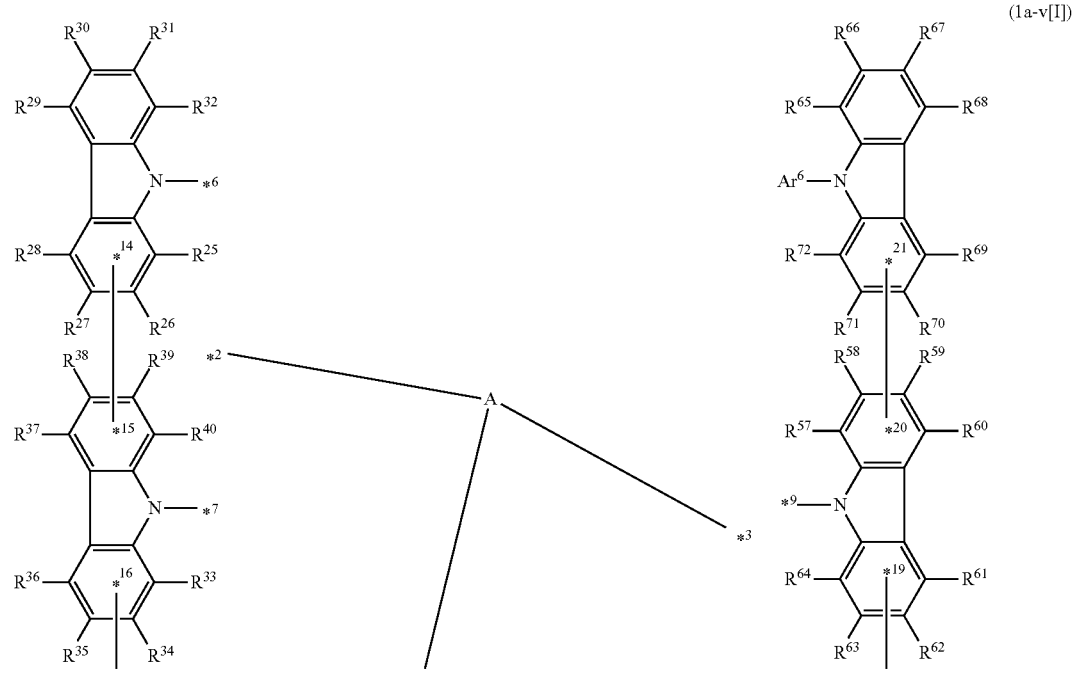
(1a-v[I])

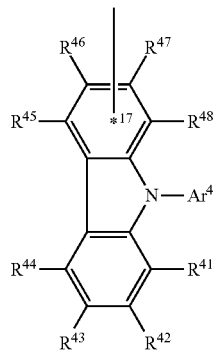
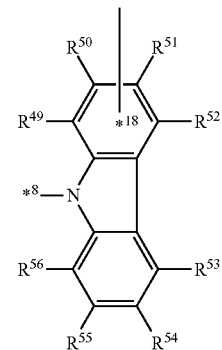
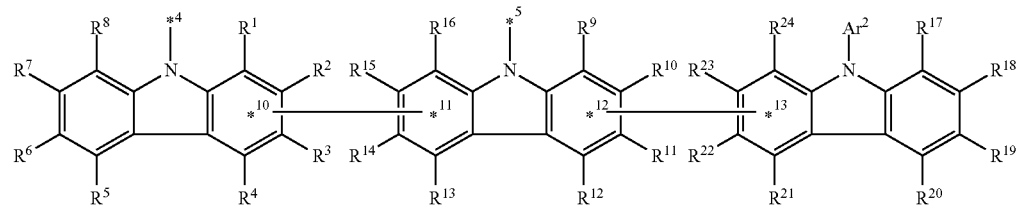
in formula 1a-v[I], A, *1 to *9, $Ar^2$, $Ar^4$, and $Ar^6$ are as described above in formula 1[I], and $R^1$ to $R^{72}$ and *10 to *21 are as described above in formula 1a-i[I].
In an aspect of the invention, the compound is preferably a compound represented by formula 1b[I] (also referred to as "compound 1b[I]"):
(1b[I])
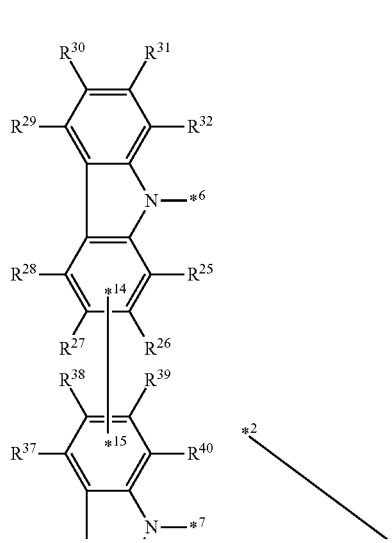
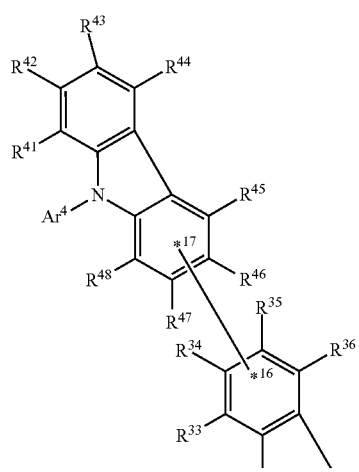

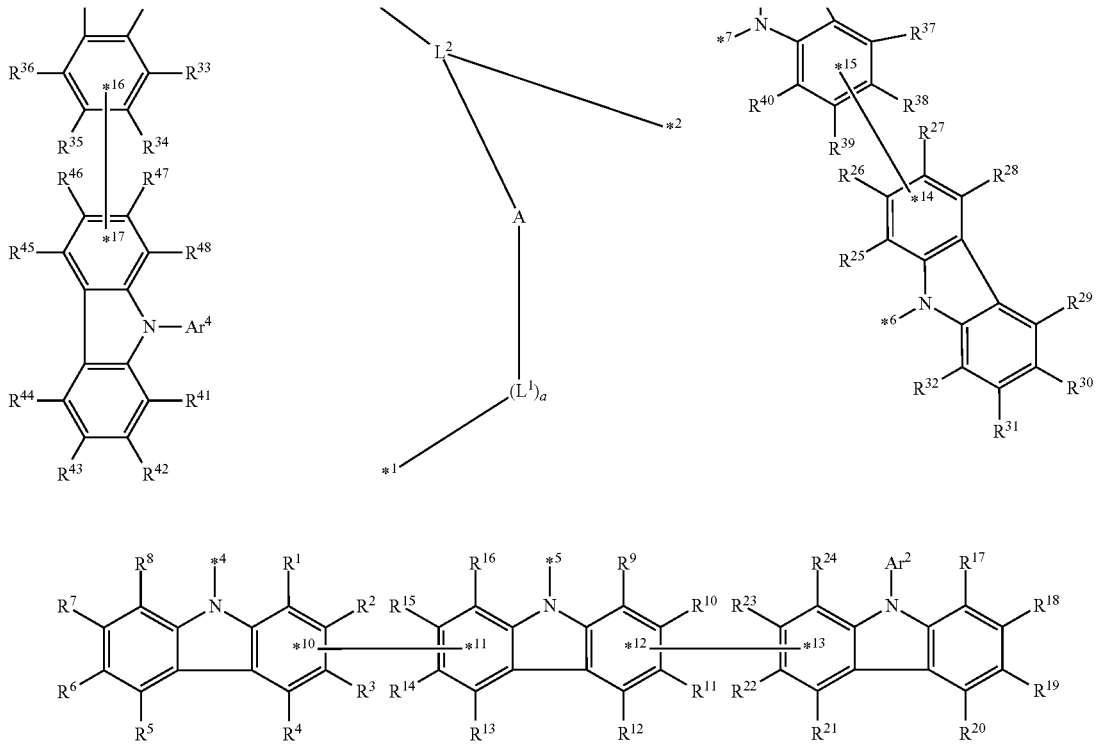

in formula 1b[I], A, $L^1$, $L^2$, a, *1 to *7, $Ar^2$, and $Ar^4$ are as described above in formula 1[I], and $R^1$ to $R^{48}$ are as described above with respect to R of formula 1[I].

In formula 1b[I],

*10-*11 is a bond between carbon atoms from which one of $R^1$ to $R^4$ and one of $R^{13}$ to $R^{16}$ are removed;

*12-*13 is a bond between carbon atoms from which one of $R^9$ to $R^{12}$ and one of $R^{21}$ to $R^{24}$ are removed;

*14-*15 is a bond between carbon atoms from which one of $R^{25}$ to $R^{28}$ and one of $R^{37}$ to $R^{40}$ are removed; and

*16-*17 is a bond between carbon atoms from which one of $R^{33}$ to $R^{36}$ and one of $R^{45}$ to $R^{48}$ are removed.

Namely, each of *10, *12, *14, and *16 is bonded to a carbon atom at 1-position, 2-position, 3-position, or 4-position of a carbazolyl group, and each of *11, *13, *15, and *17 is bonded to a carbon atom at 5-position, 6-position, 7-position, or 8-position of another carbazolyl group, thereby linking two carbazolyl groups by *10-*11, *12-*13, *14-*15, and *16-*17, respectively.

In an aspect of the invention, the compound 1b[I] is preferably a compound wherein two selected from $R^1$ to $R^{48}$ are not bonded to each other, thereby failing to form a ring, and more preferably a compound represented by formula 1b-i[I]:

(1b-i[I])

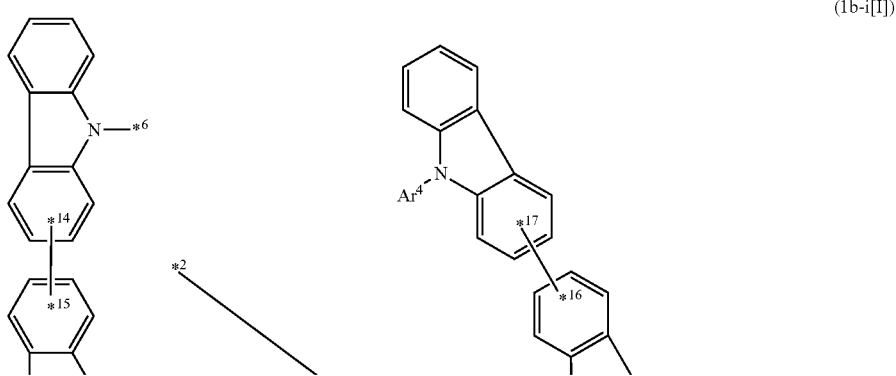

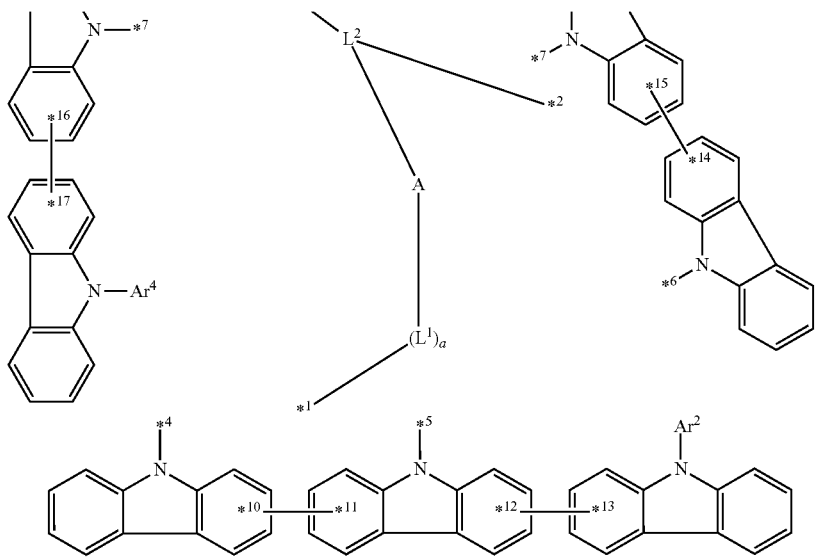

in formula 1b-i[I], A, $L^1$, $L^2$, a, *1 to *7, $Ar^2$, and $Ar^1$ are as described above in formula 1[I], and each of *10-*11, *12-*13, *14-*15, and *16-*17 is a bond between carbon atoms in each benzene ring from which hydrogen atoms are removed.

Namely, each of *10, *12, *14, cs and *16 is bonded to a carbon atom at 1-position, 2-position, 3-position, or 4-position of a carbazolyl group, and each of *11, *13, *15, and *17 is bonded to a carbon atom at 5-position, 6-position, 7-position, or 8-position of another carbazolyl group, thereby linking two carbazolyl groups by *10-*11, *12-*13, *14-*15, and *16-*17, respectively.

In an aspect of the invention, the compound is preferably a compound represented by any of formulae 1c-i[I] to 1c-iv[I] (also referred to as "compounds 1c-i[I] to 1c-iv[I]").

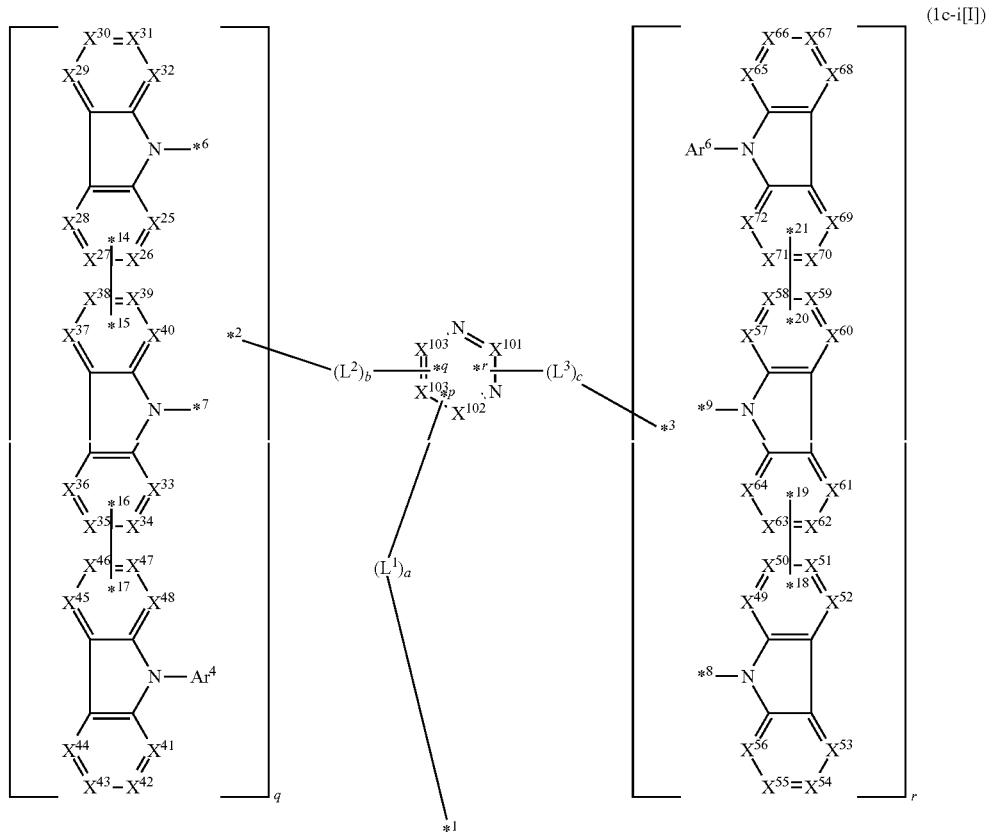

(1c-i[I])

-continued

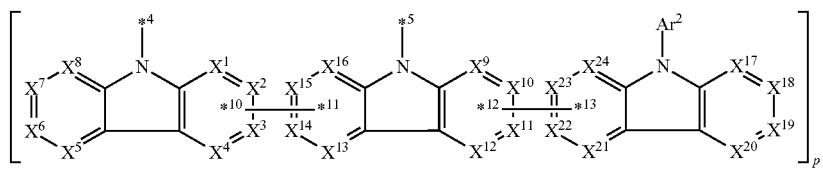

in formula 1c-i[I],

L¹ to L³, a to c, $X^1$ to $X^{72}$, *1 to *21, $Ar^2$, $Ar^1$, and $Ar^6$ are as described above in formula 1[I];

$X^{101}$ to $X^{104}$ each represent a carbon atom bonded to one of *p to *r, C(Rx), or a nitrogen atom; and Rx represents a hydrogen atom or a substituent, two or more groups Rx may be the same or different, and two selected from groups Rx may be bonded to each other to form a ring;

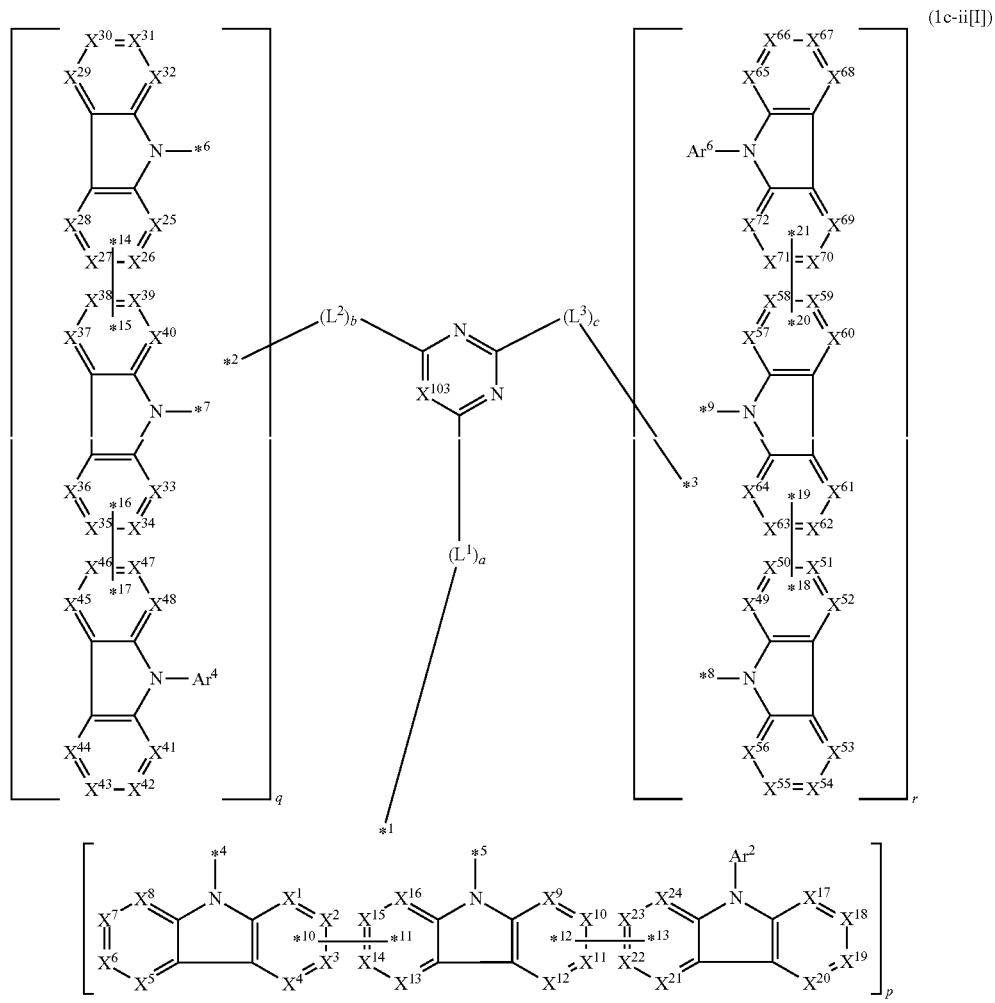

(1c-ii[I])

in formula 1c-ii[I],

L¹ to L³, a to c, $X^1$ to $X^{72}$, *1 to *21, $Ar^2$, $Ar^4$, and $A^6$ are as described above in formula 1[I];

$X^{103}$ represents C(Rx) or a nitrogen atom; and

Rx represents a hydrogen atom or a substituent;

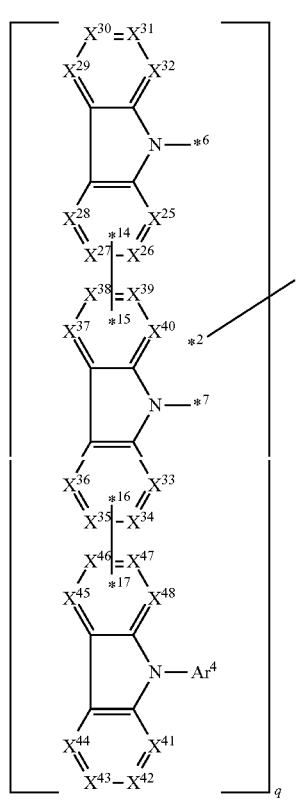
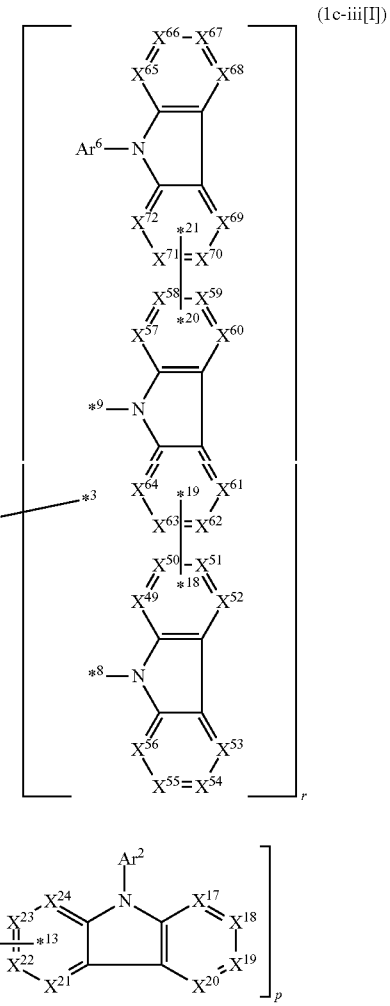
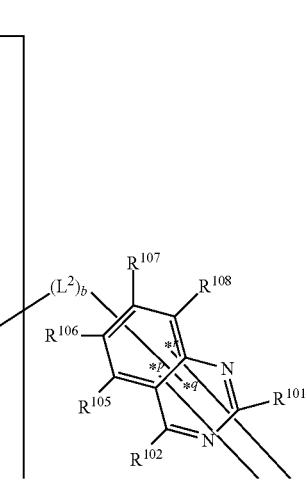

(1c-iii[I])

in formula 1c-iii[I], $L^1$ to $L^3$, a to c, $X^1$ to $X^{72}$, *1 to *21, $Ar^2$, $Ar^4$, and $Ar^6$ are as described above in formula 1[I];

$X^{101}$, $X^{102}$, and $X^{105}$ to $X^{108}$ each represent a carbon atom bonded to one of *p to *r, C(Rx), or a nitrogen atom; and Rx represents a hydrogen atom or a substituent, two or more groups Rx may be the same or different, and two selected from groups Rx may be bonded to each other to form a ring; and

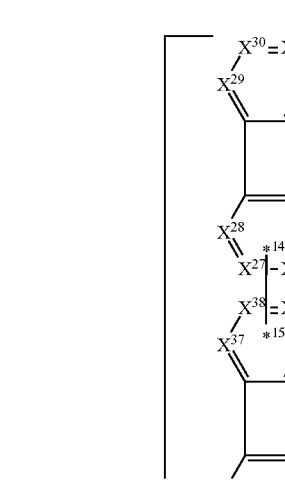
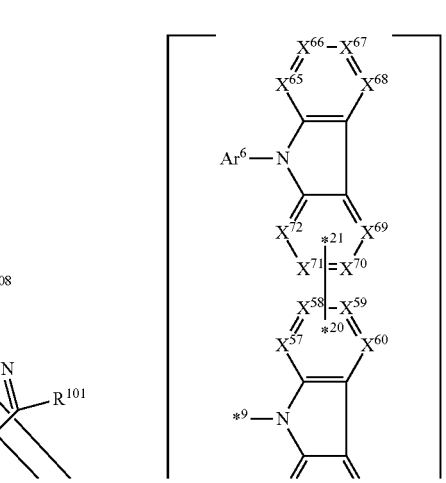

(1c-iv[I])

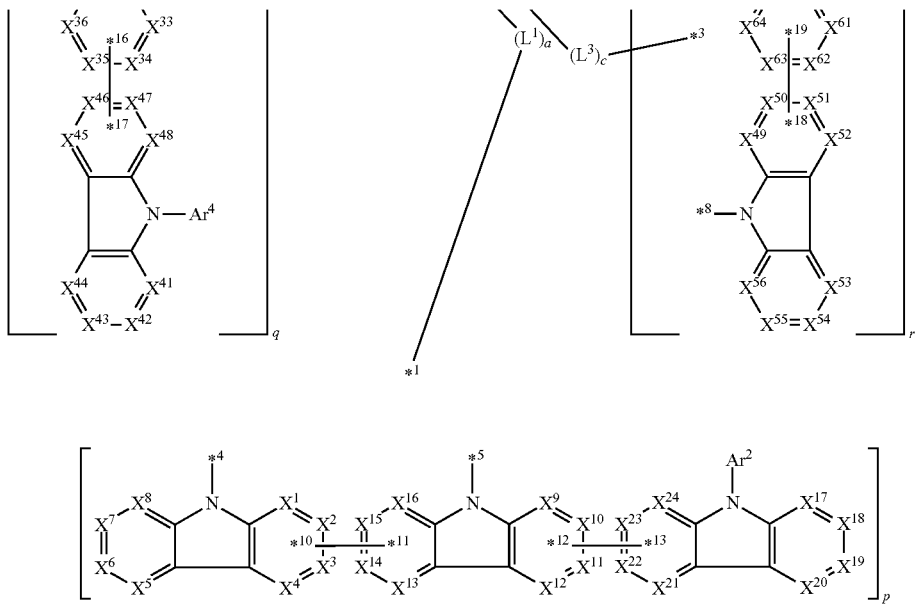

in formula 1c-iv[I], $L^1$ to $L^3$, a to c, $X^1$ to $X^{72}$, *1 to *21, $Ar^2$, $Ar^4$, and $Ar^6$ are as described above in formula 1[I];

1 to 3 carbon atoms from which one to three selected from $R^{101}$, $R^{102}$, and $R^{105}$ to $R^{108}$ are removed are each bonded to one of *p to *r, and the others each independently represent a hydrogen atom or a substituent; and two selected from $R^{102}$ and $R^{105}$ to $R^{108}$ may be bonded to each other to form a ring.

Examples of the compound 1[I] in an aspect of the invention are shown below, although not limited thereto.

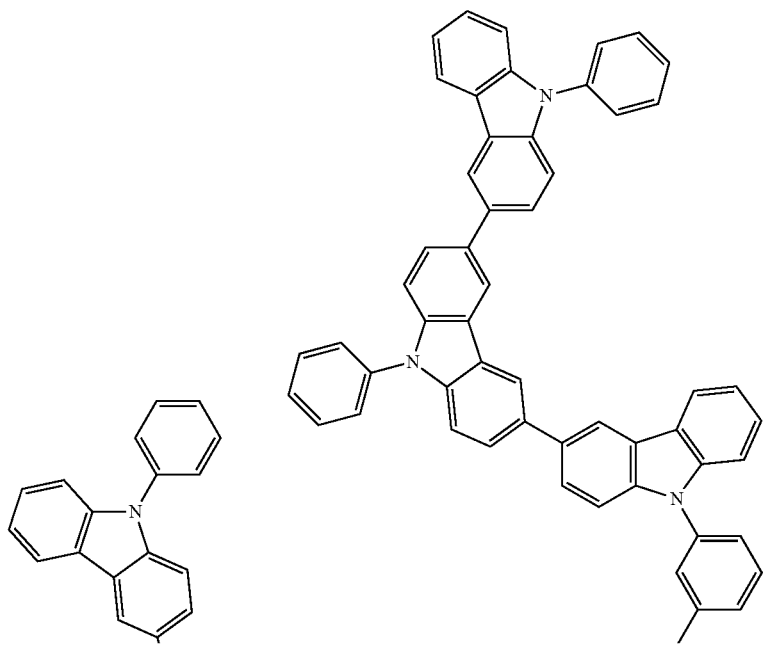

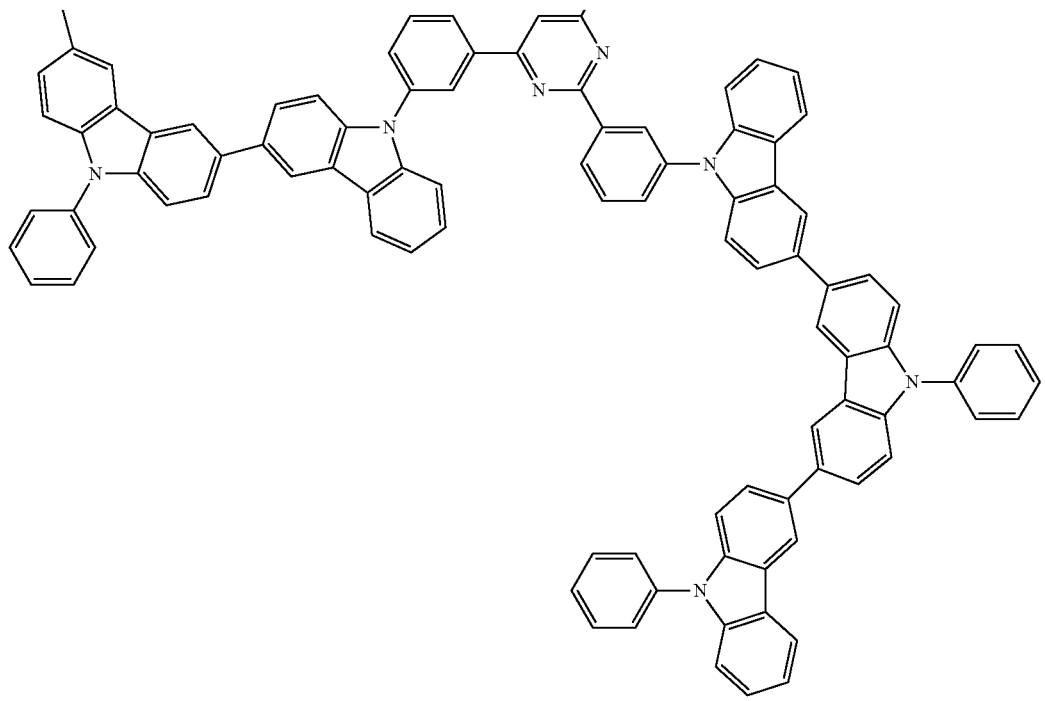
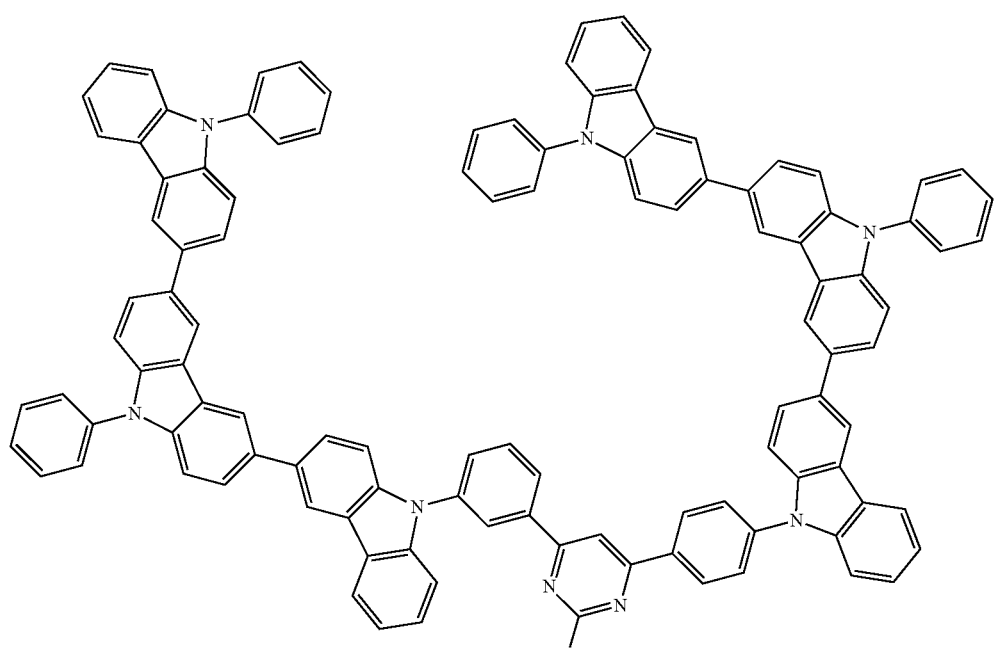

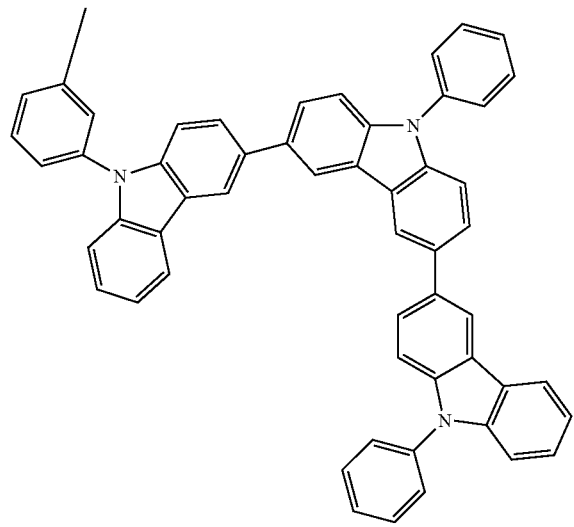
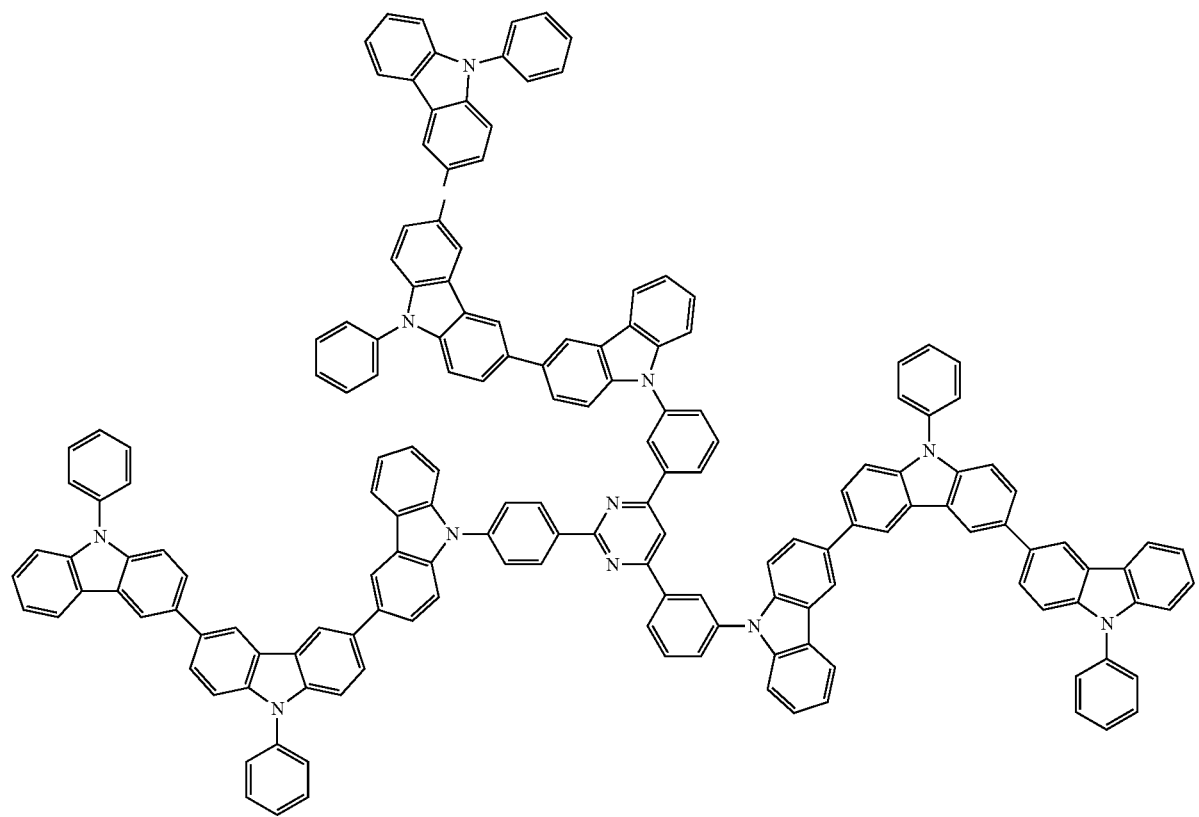

-continued
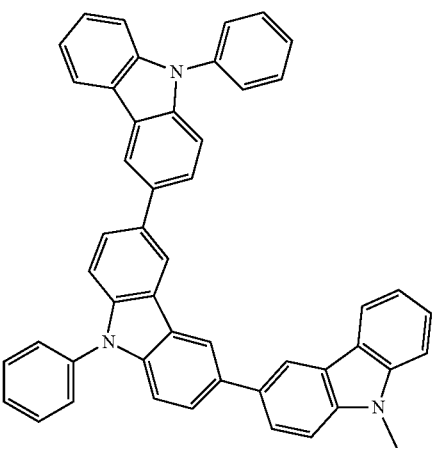
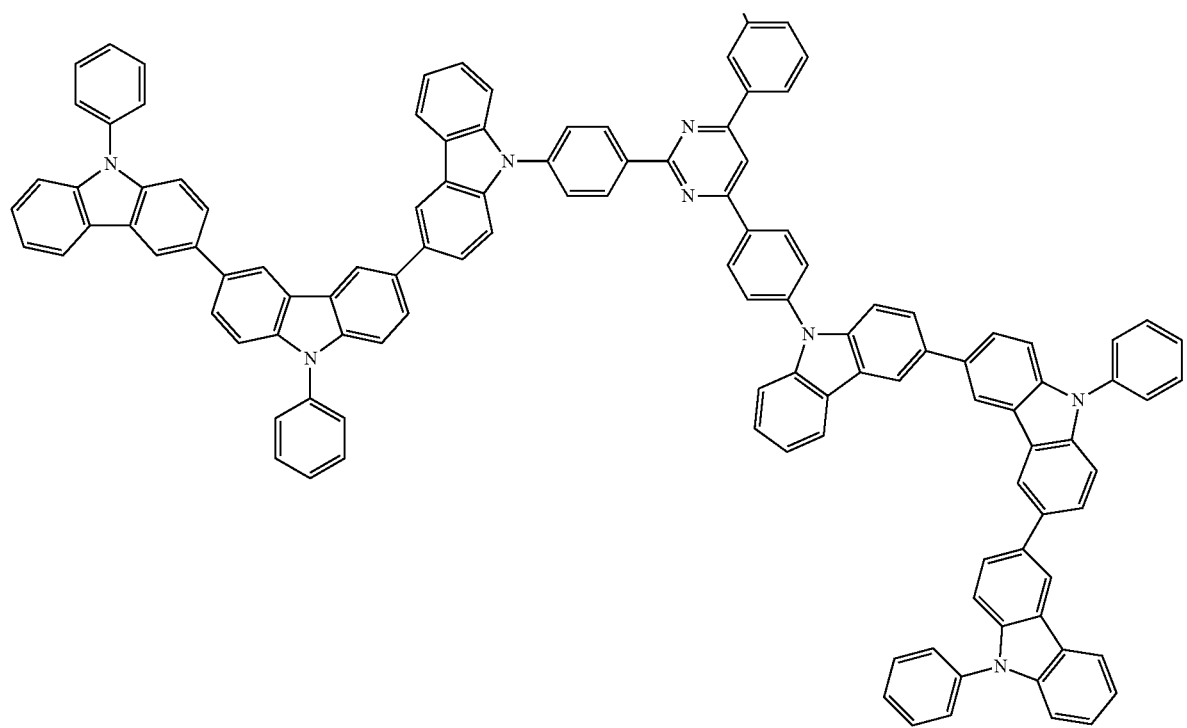
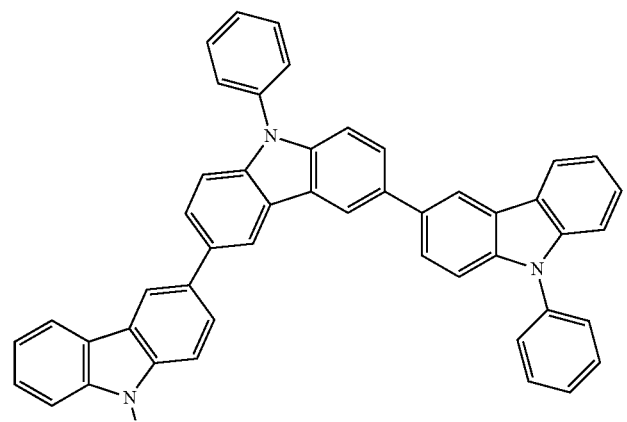

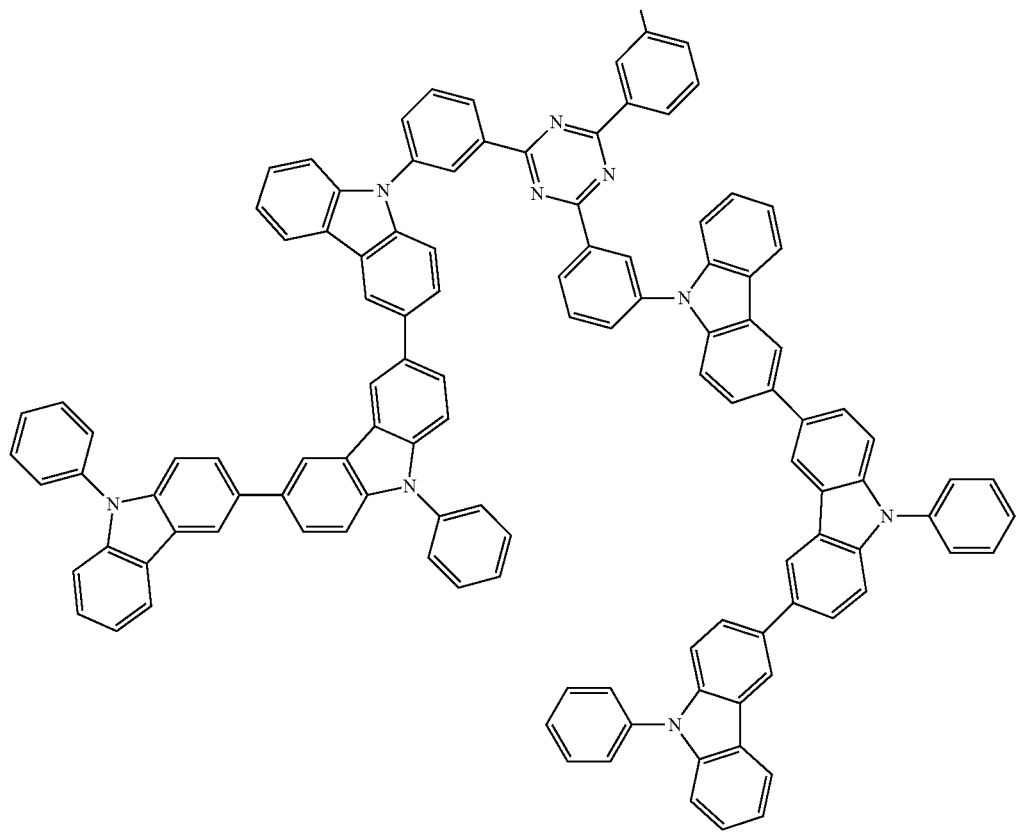
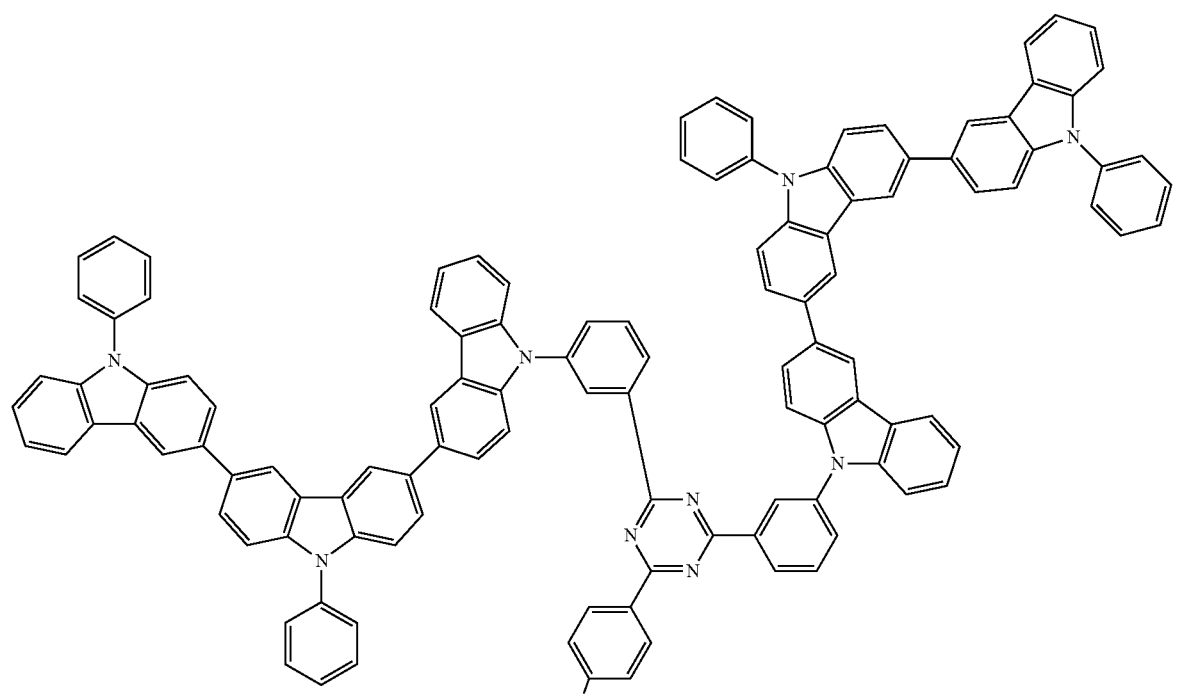

-continued
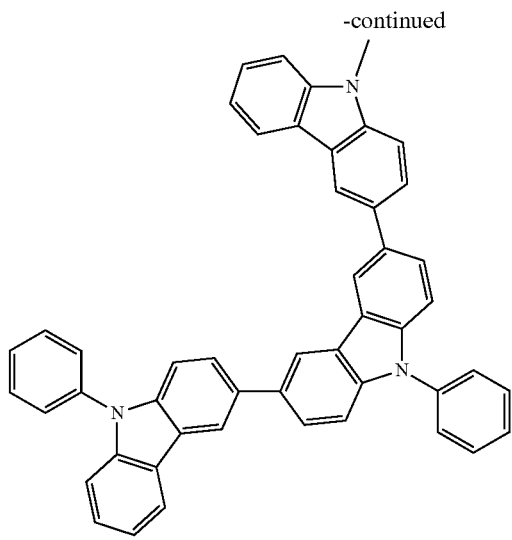
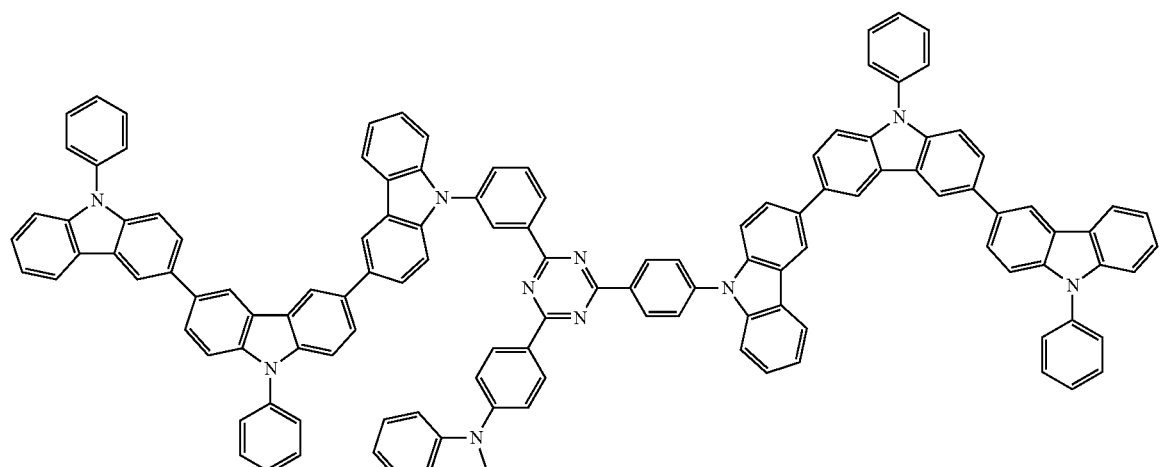
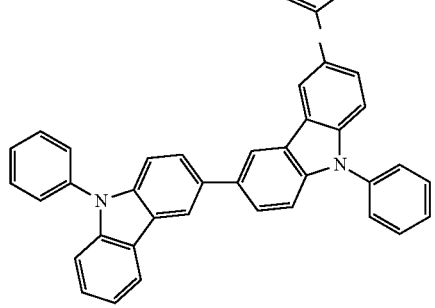
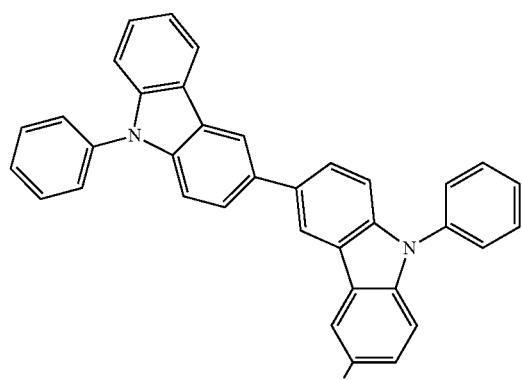

-continued
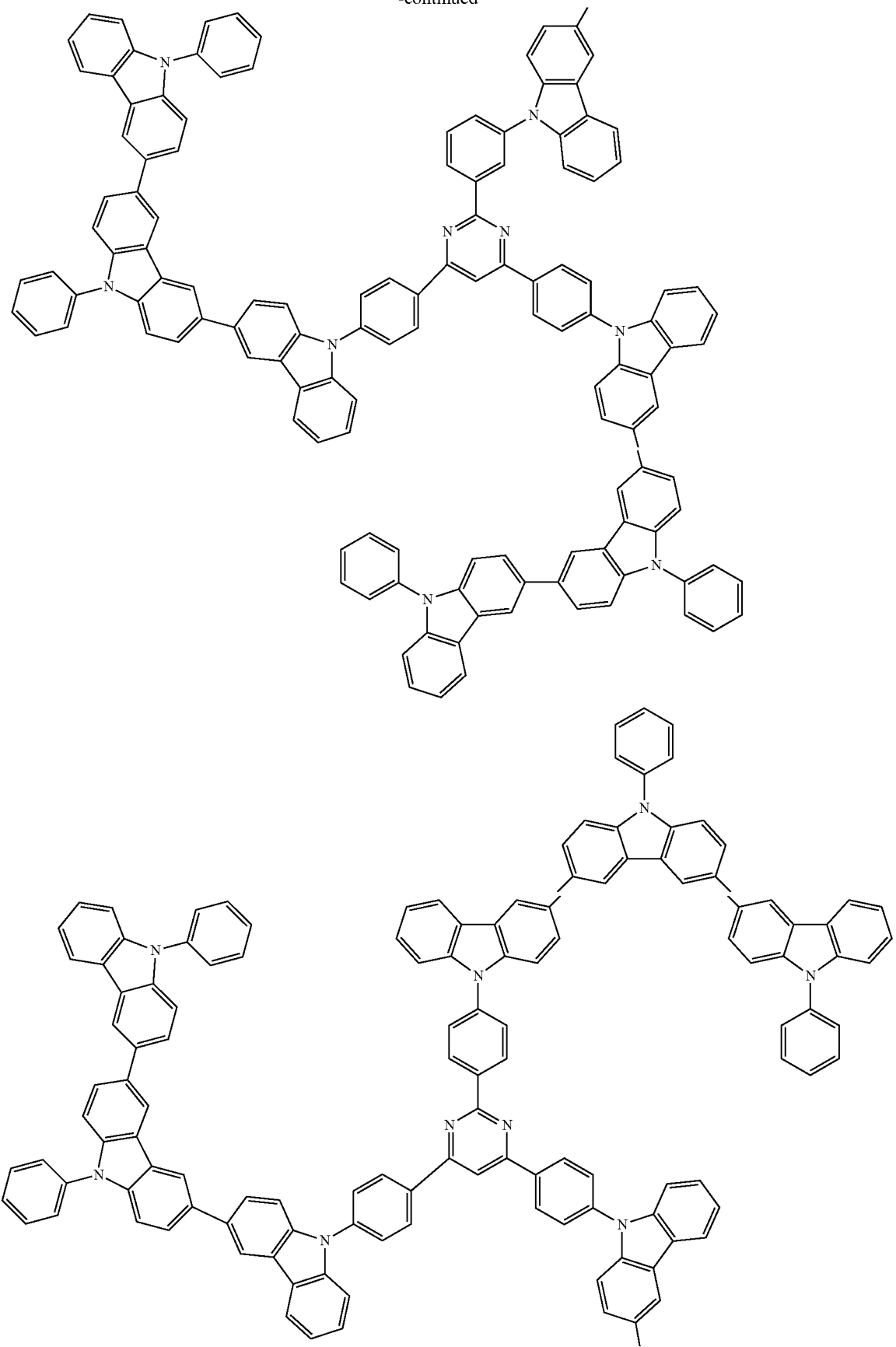

-continued
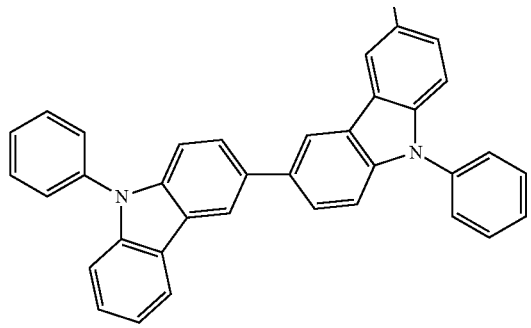
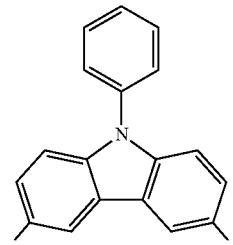
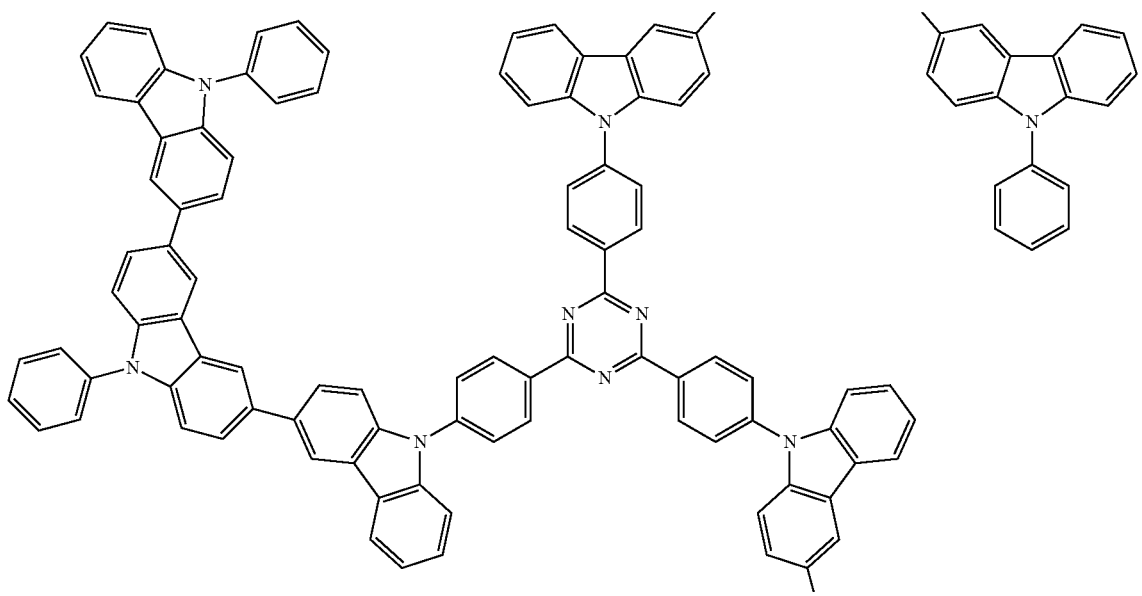
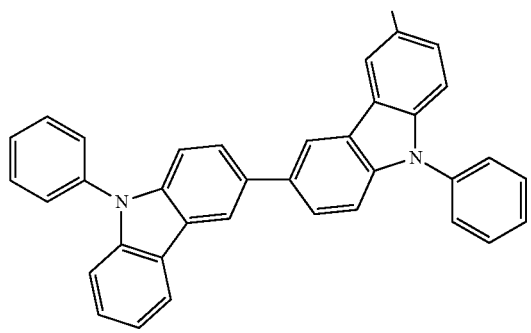

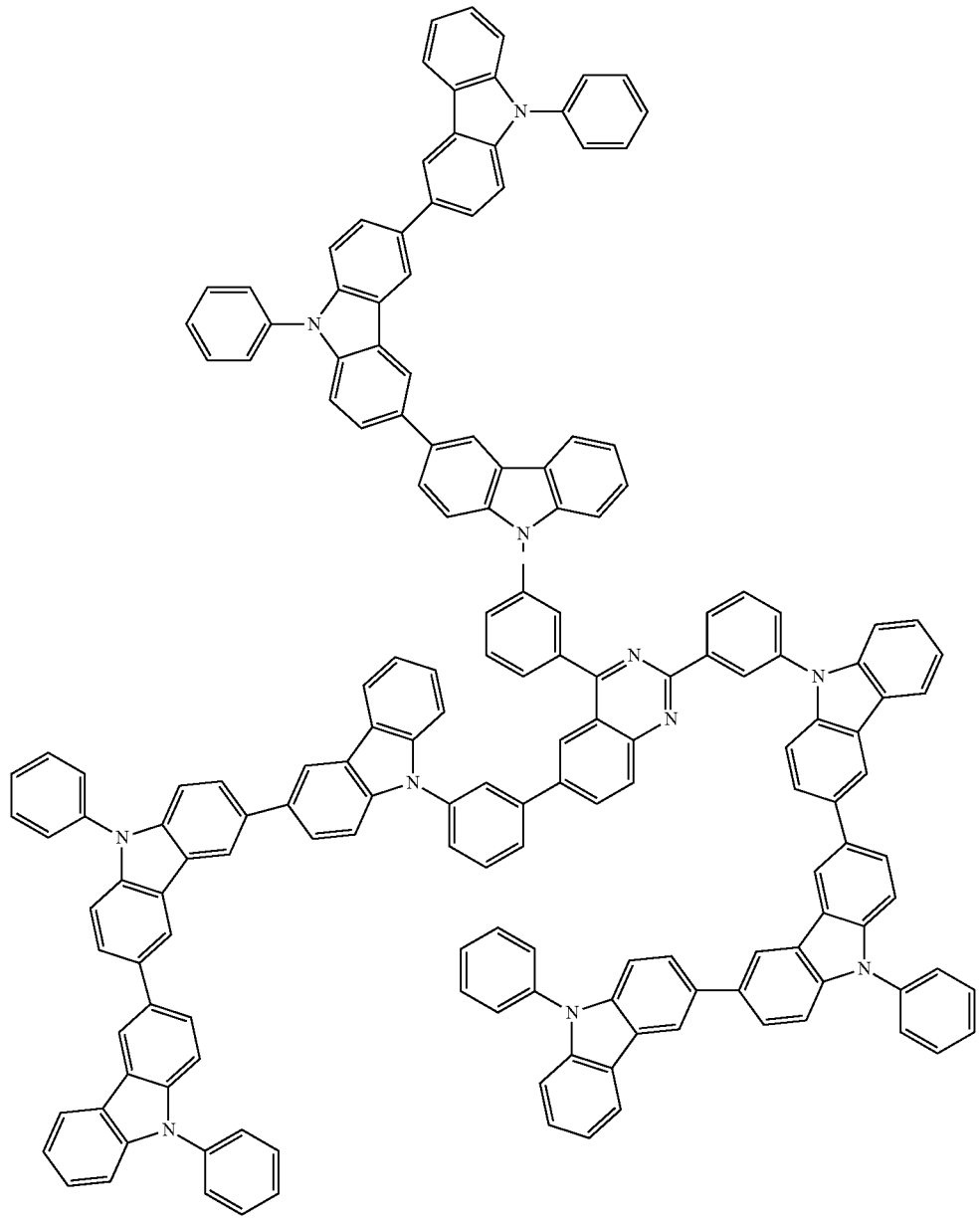 [SMILES: c1ccc(-n2c3ccccc3c3cc(-c4ccc5c(c4)c4cc(-c6ccc7c(c6)c6ccccc6n7-c6cccc(-c7ccc8nc(-c9cccc(-n%10c%11ccccc%11c%11cc(-c%12ccc%13c(c%12)c%12cc(-c%14ccc%15c(c%14)c%14ccccc%14n%15-c%14ccccc%14)ccc%12n%13-c%12ccccc%12)ccc%11%10)c9)nc(-c9cccc(-n%10c%11ccccc%11c%11cc(-c%12ccc%13c(c%12)c%12cc(-c%14ccc%15c(c%14)c%14ccccc%14n%15-c%14ccccc%14)ccc%12n%13-c%12ccccc%12)ccc%11%10)c9)c8c7)c6)ccc4n5-c4ccccc4)ccc32)cc1]
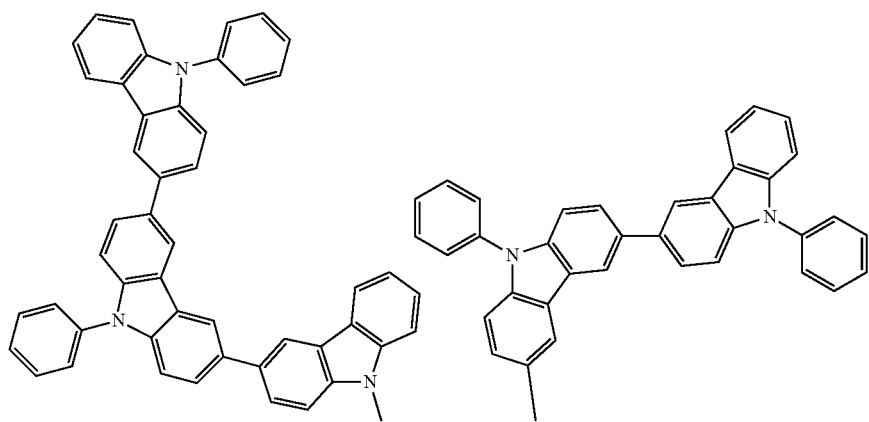

-continued
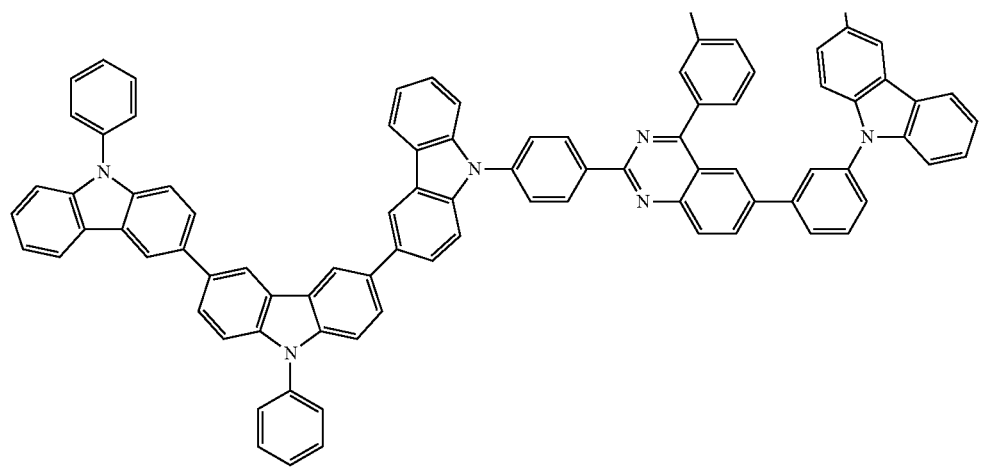
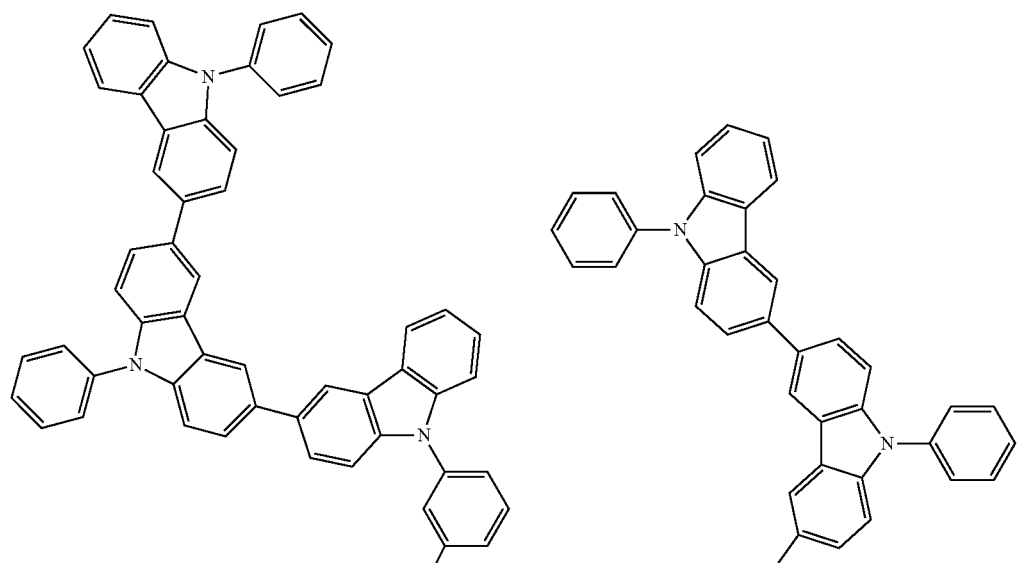
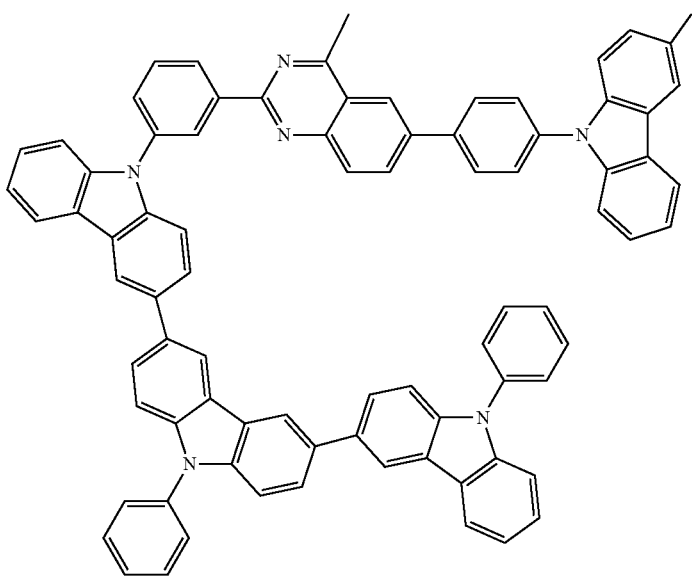

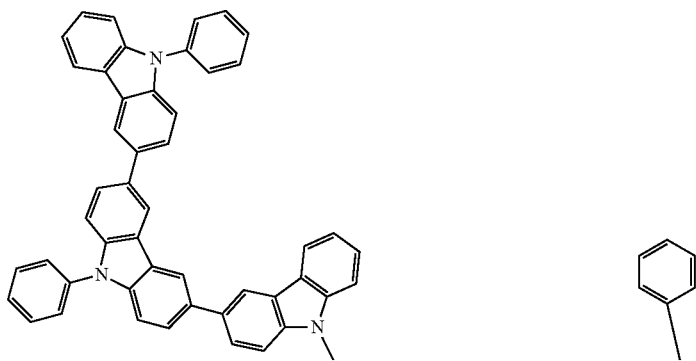
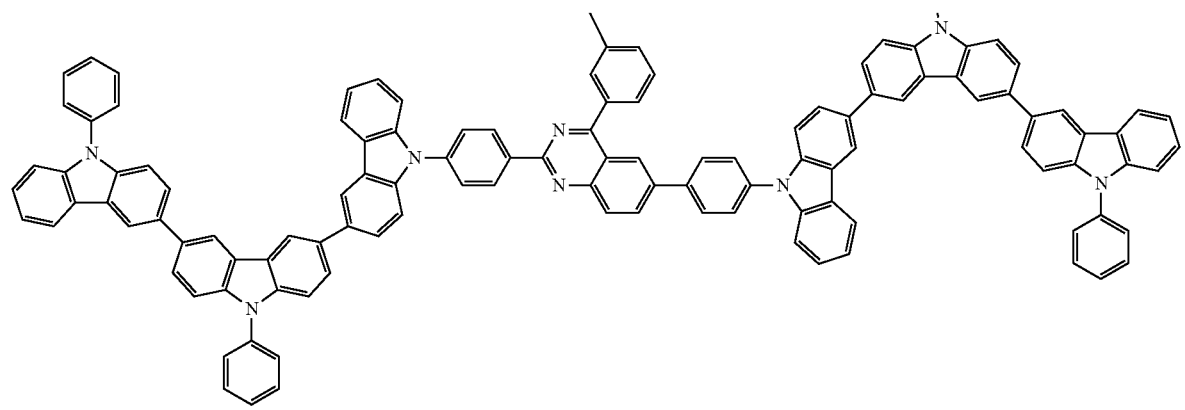

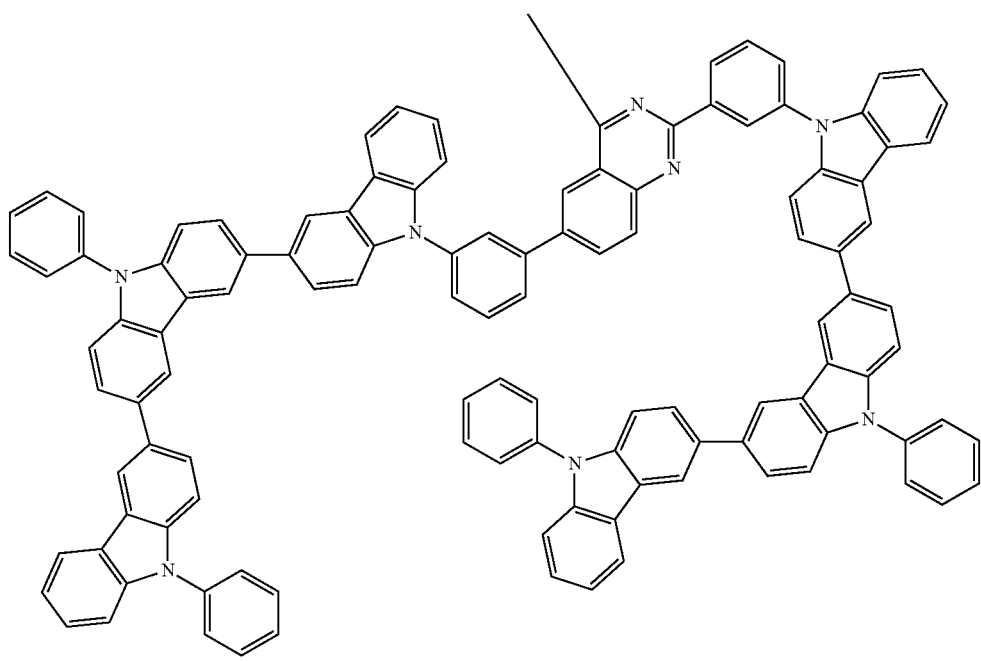
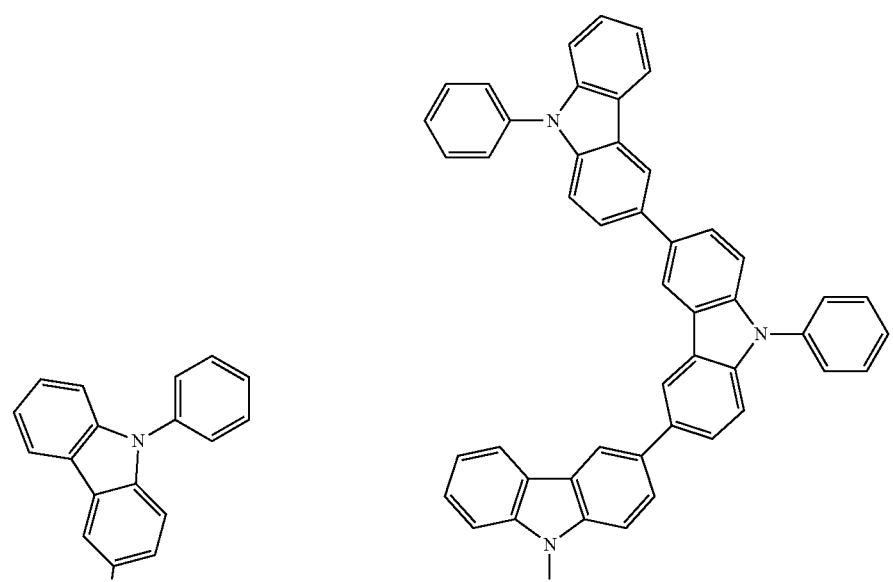

111 112
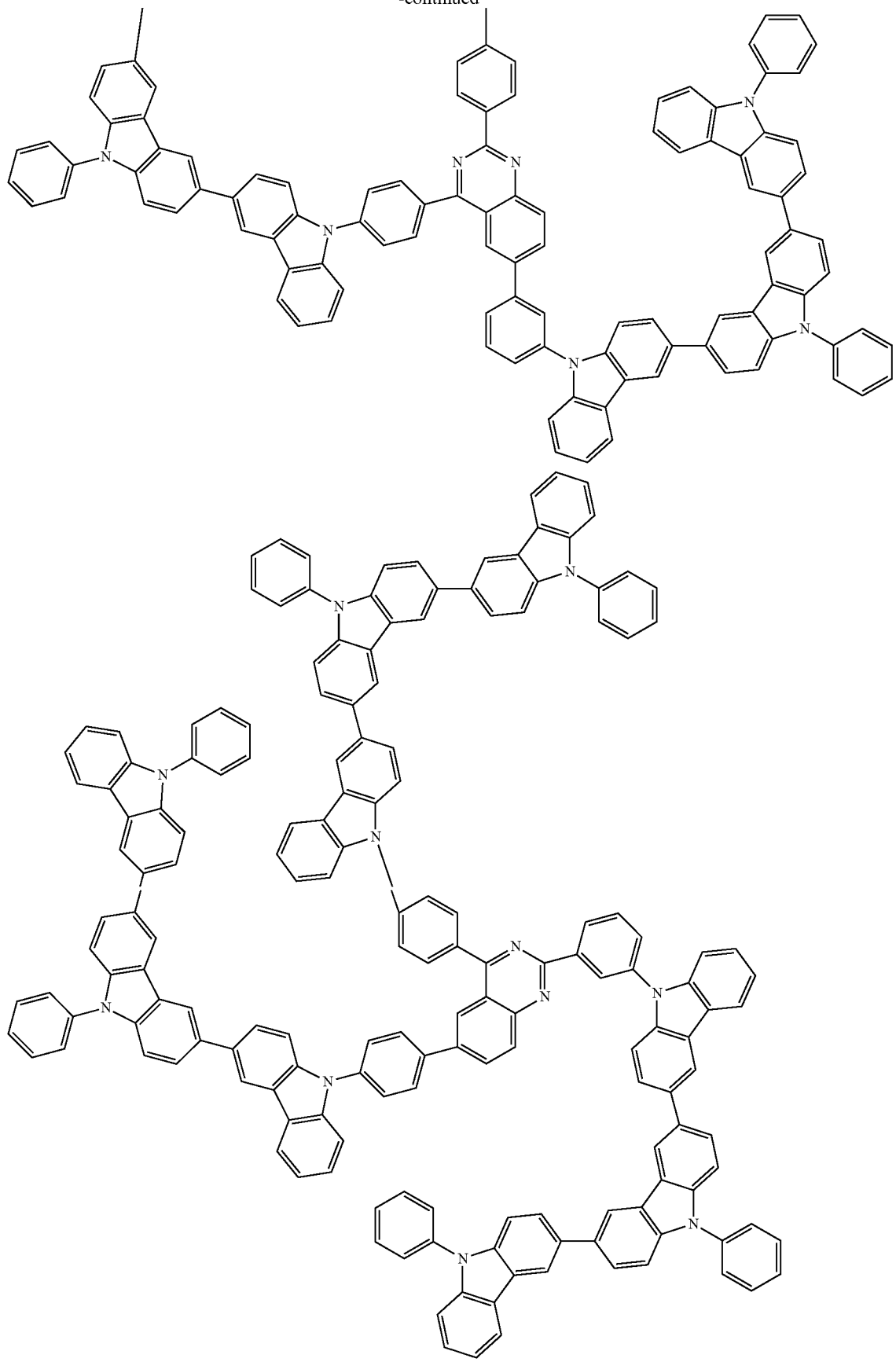

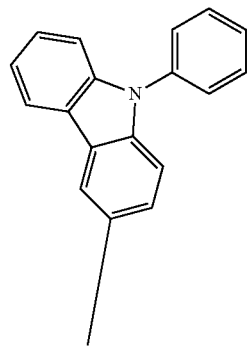
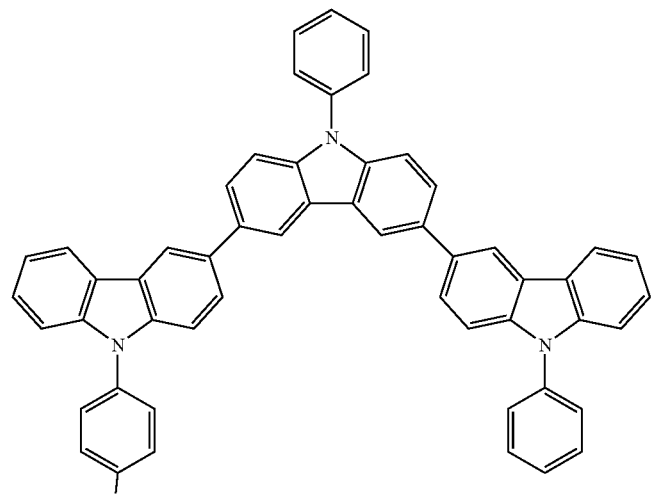
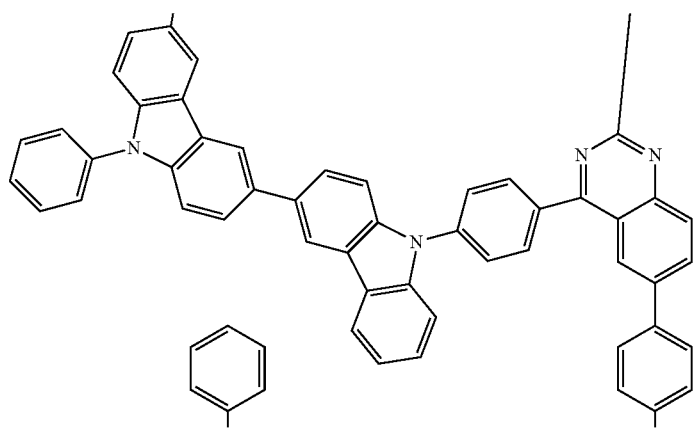
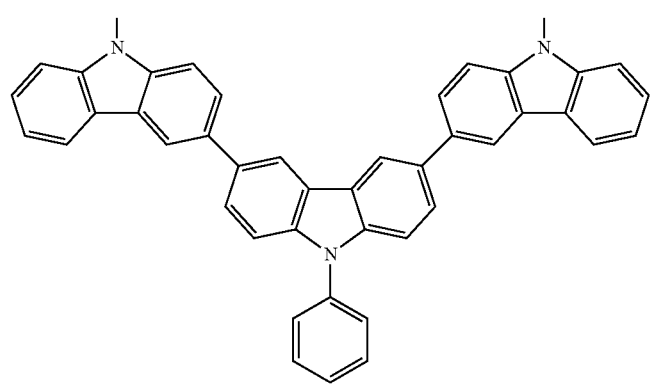

-continued
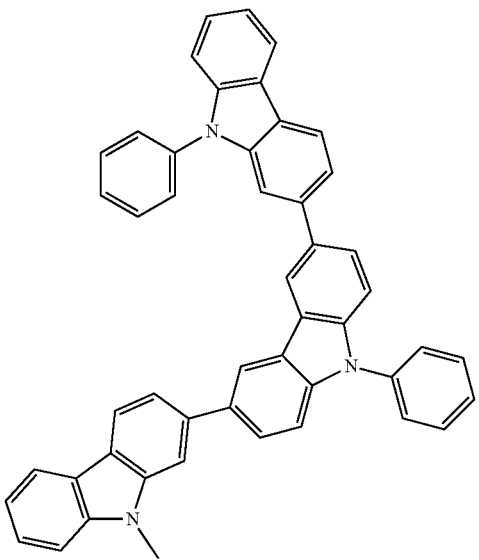
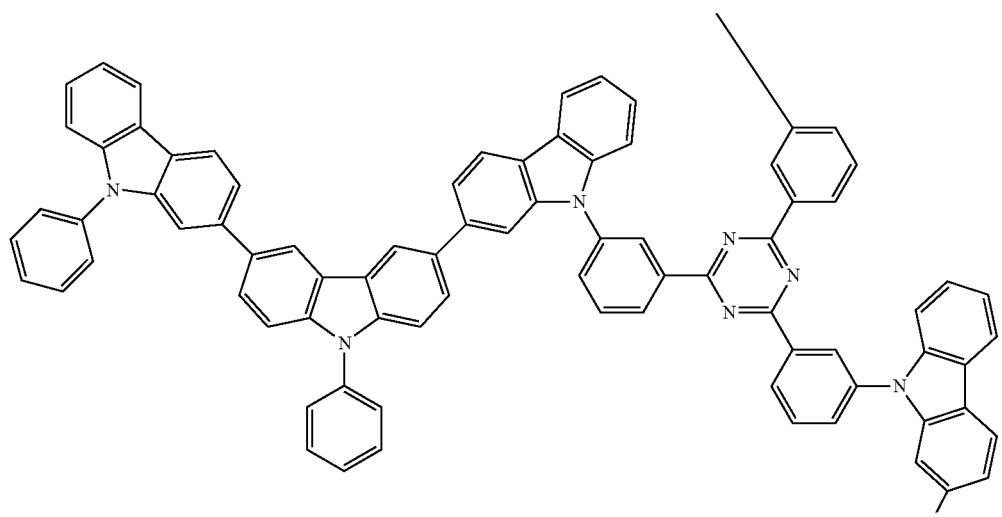
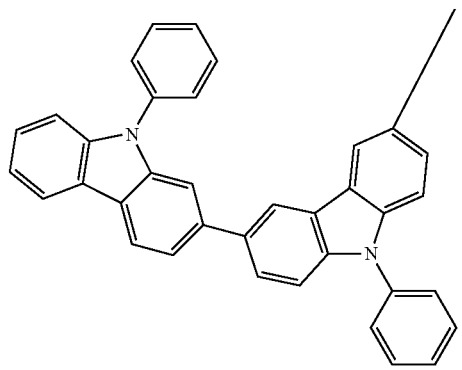

-continued
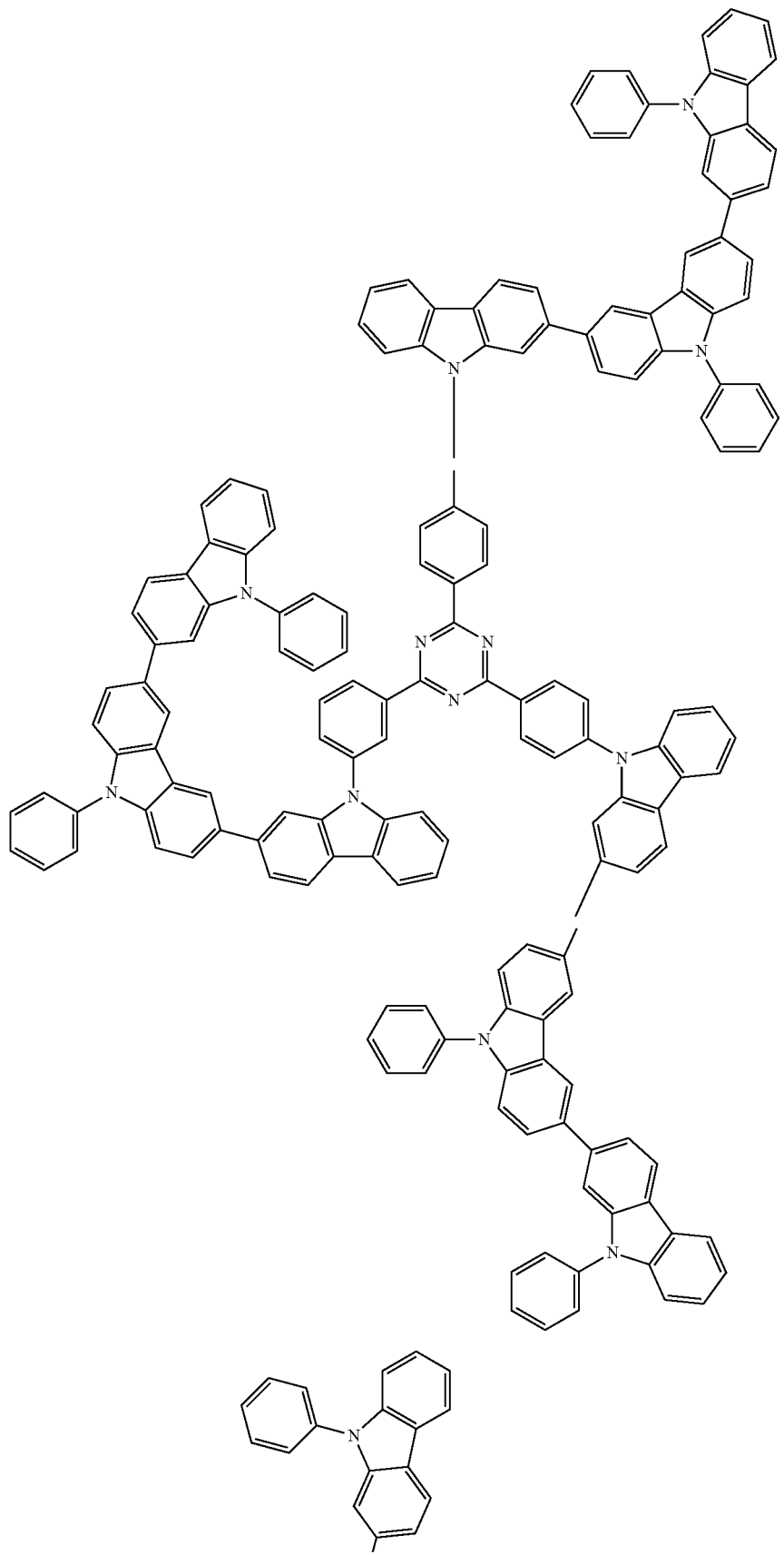

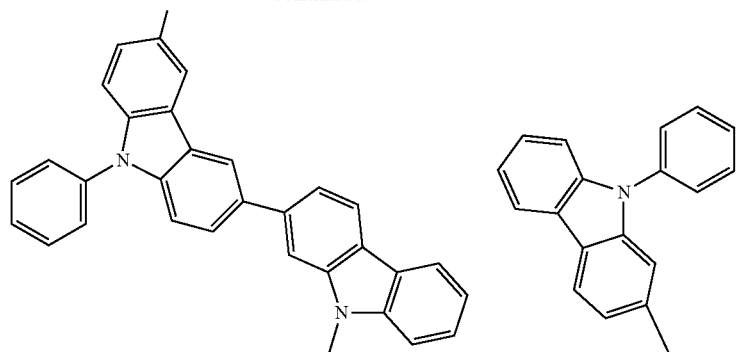
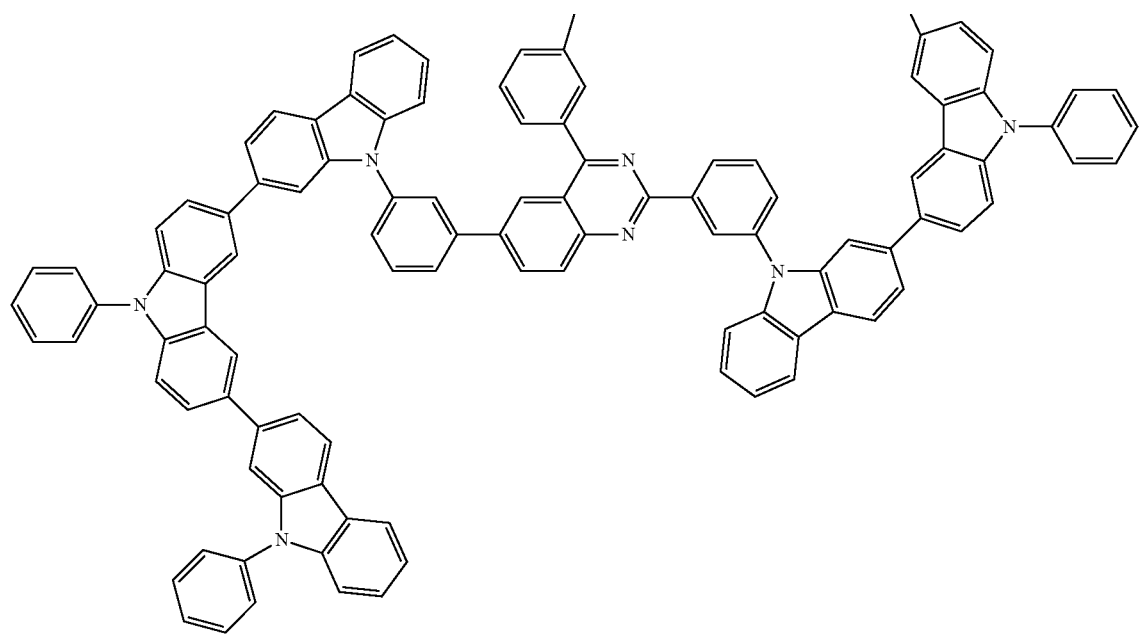
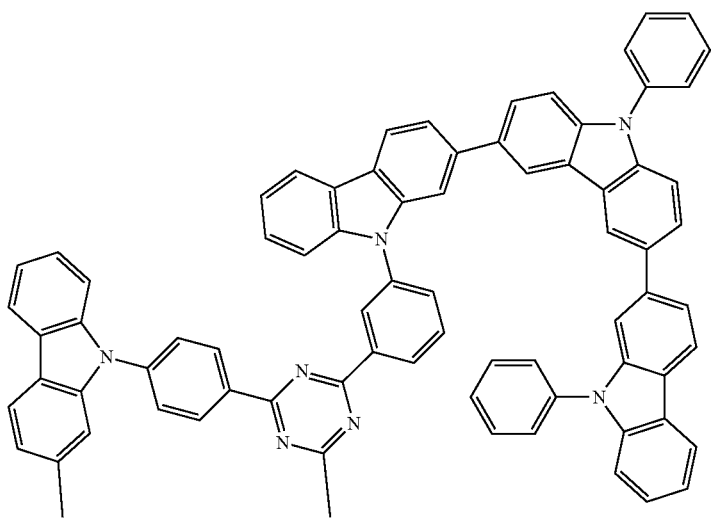

-continued
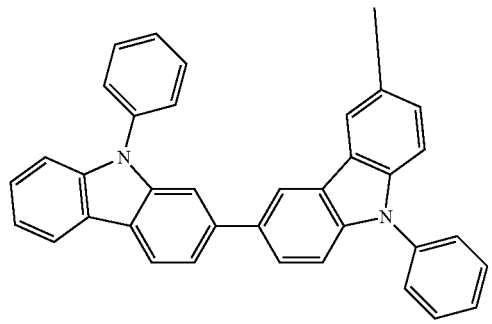
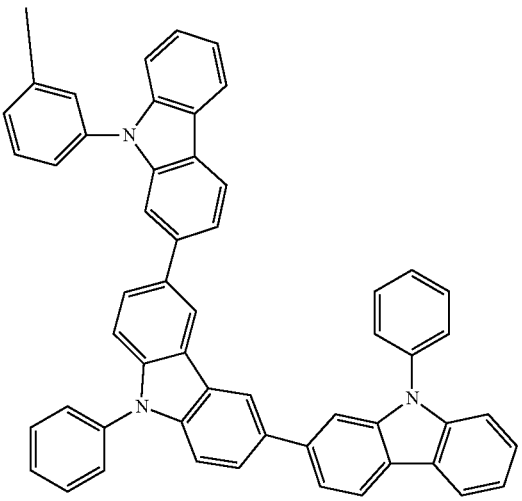
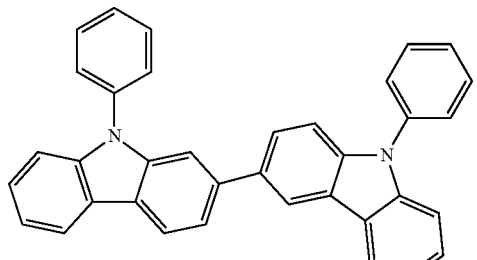
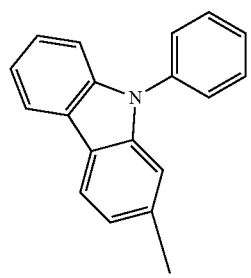
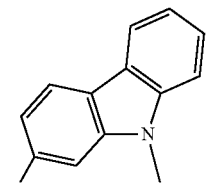
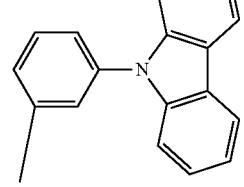
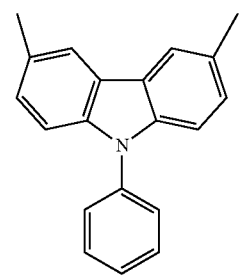
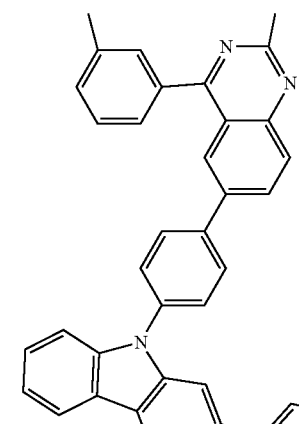
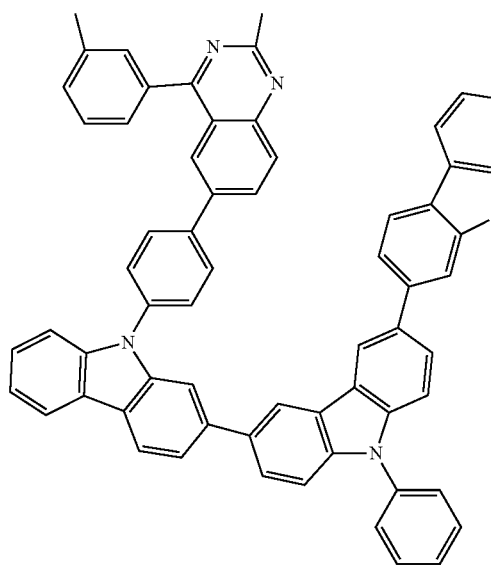

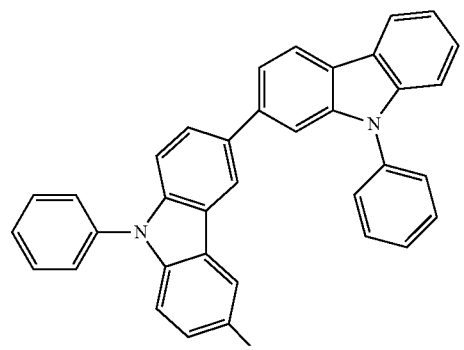
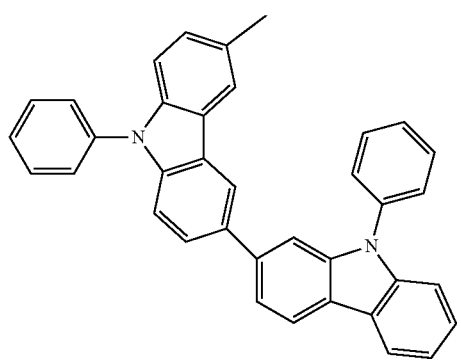

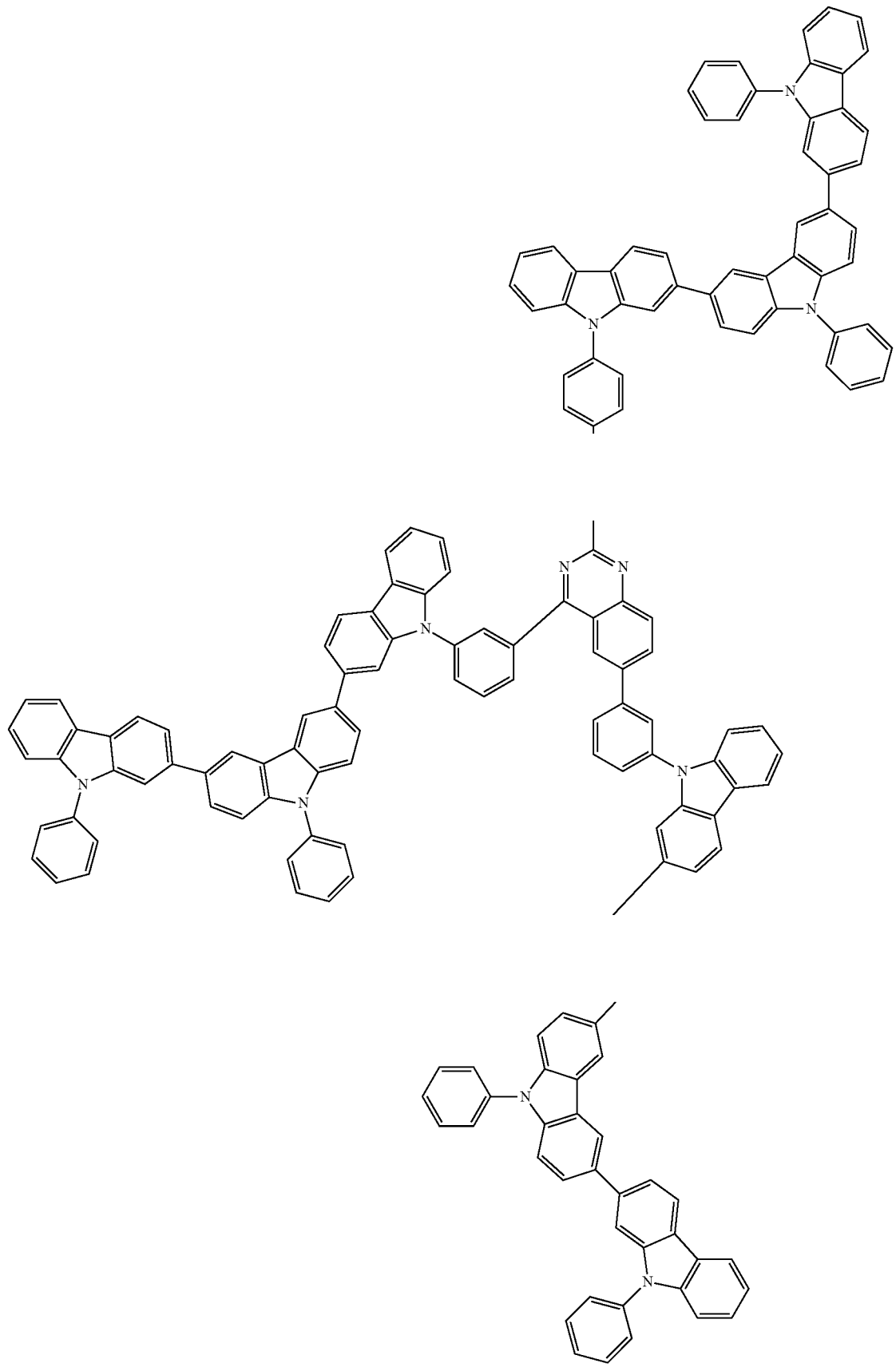

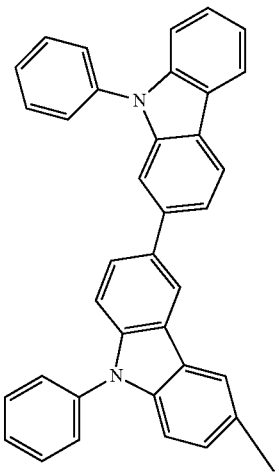
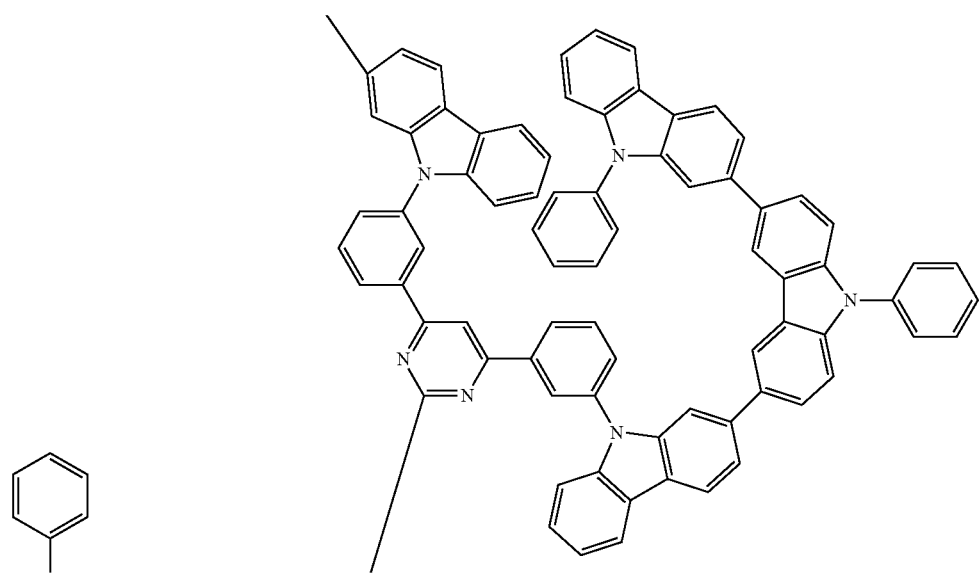
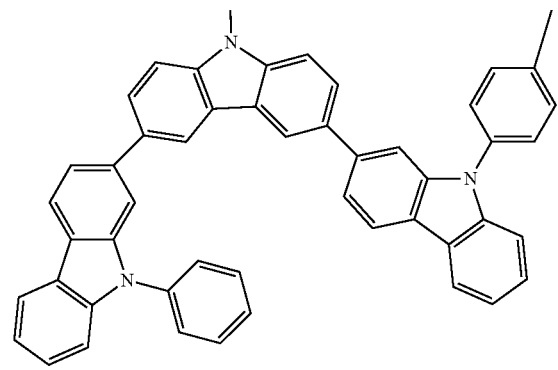

-continued
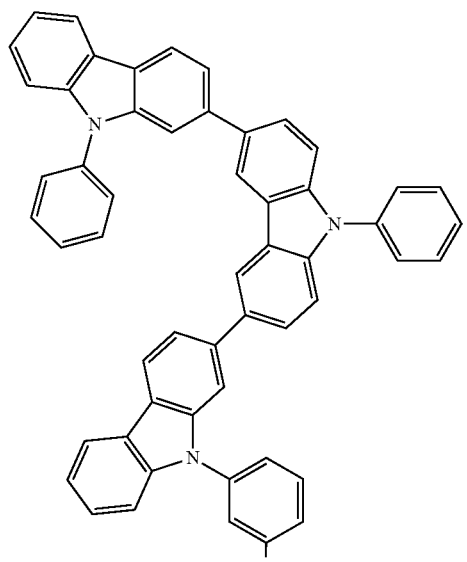
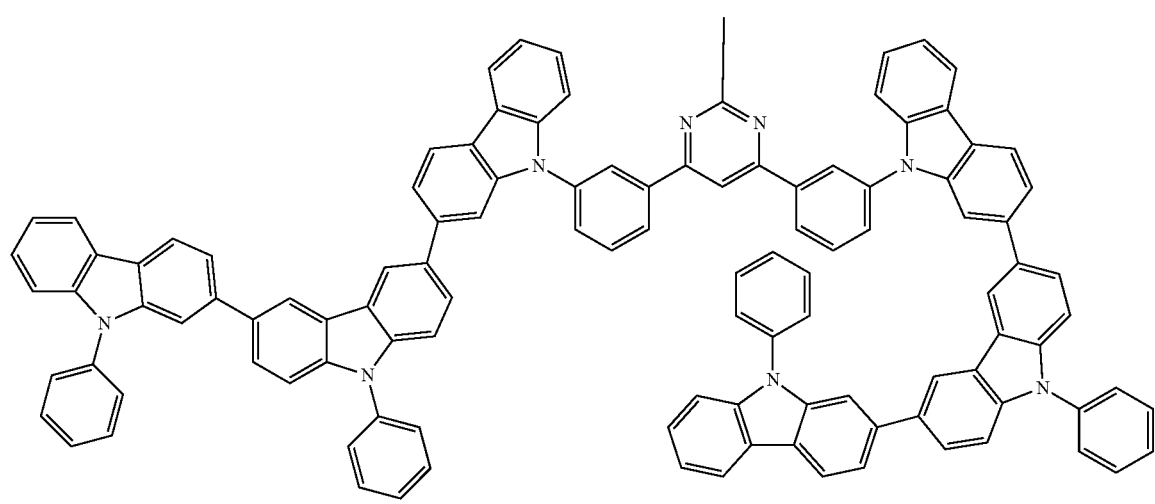
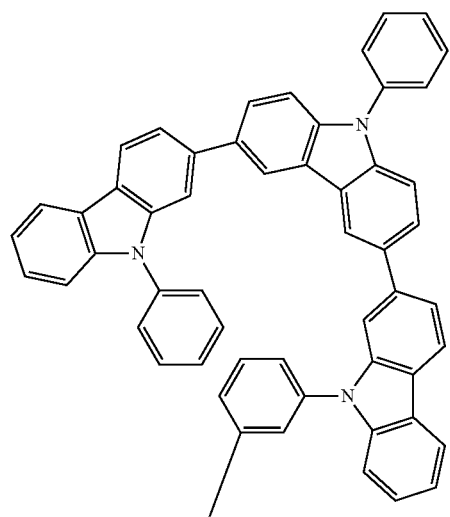

-continued
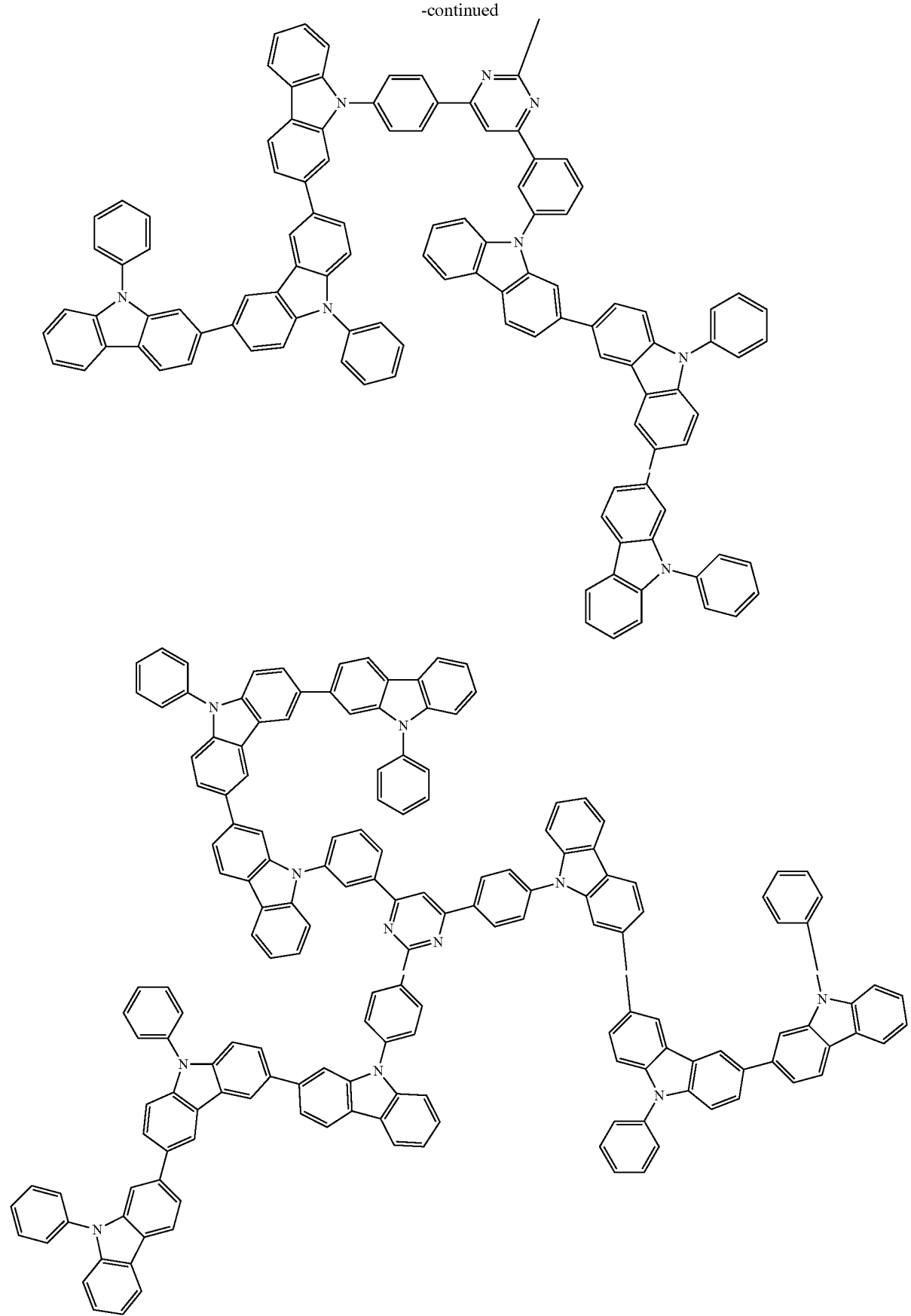

-continued
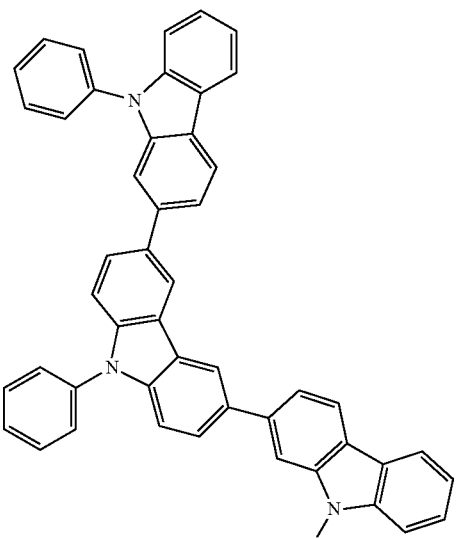
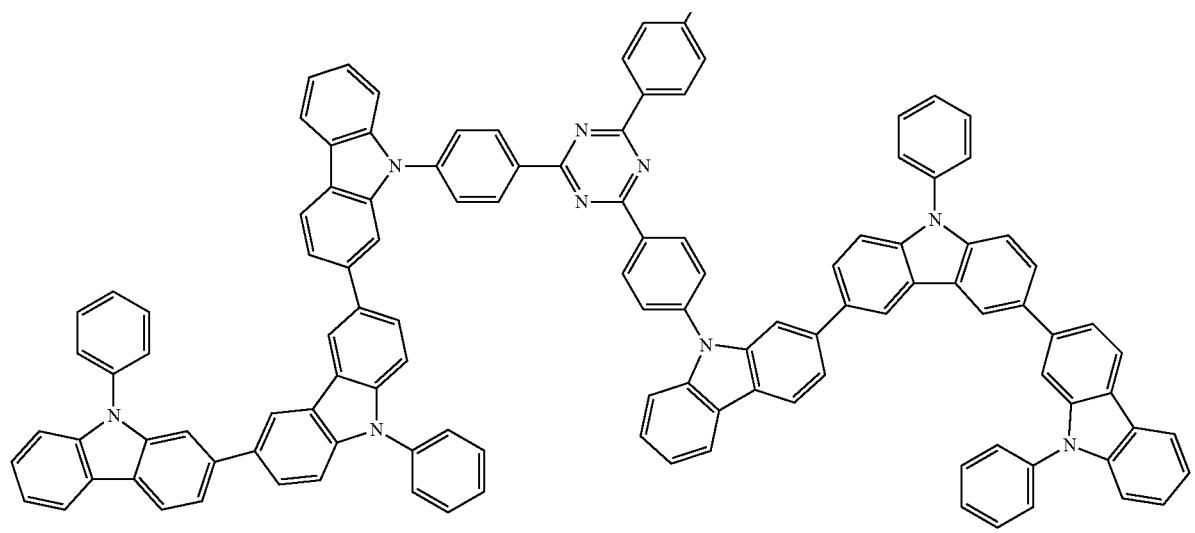
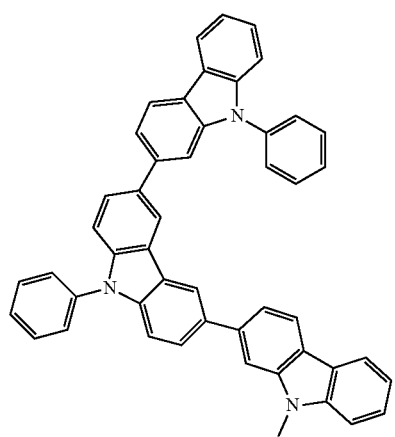

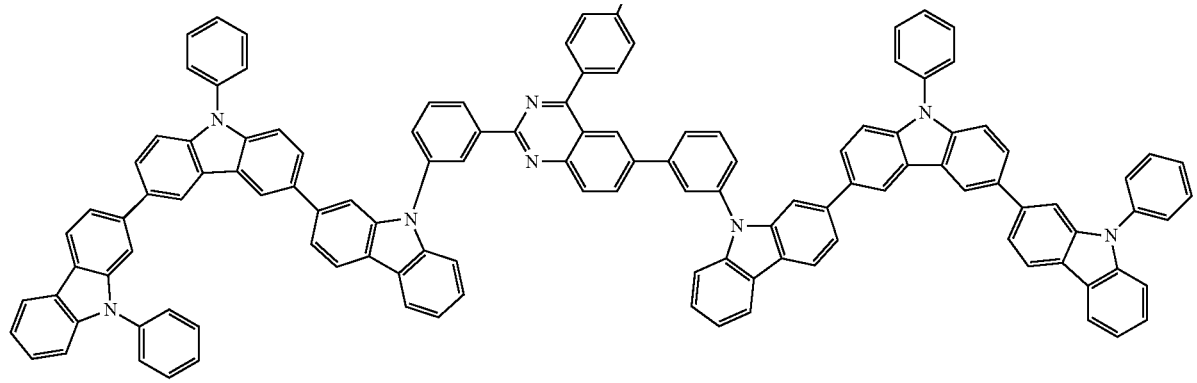
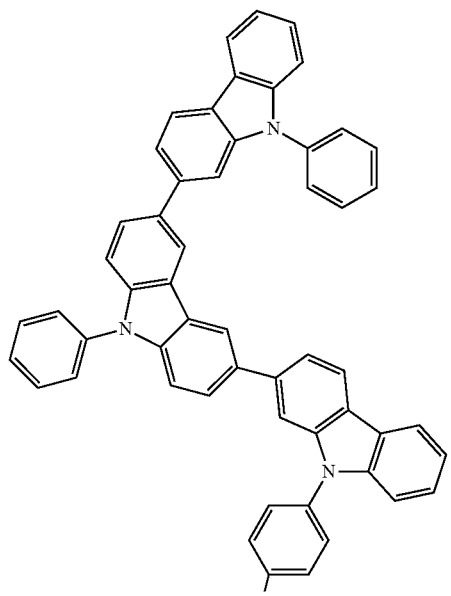
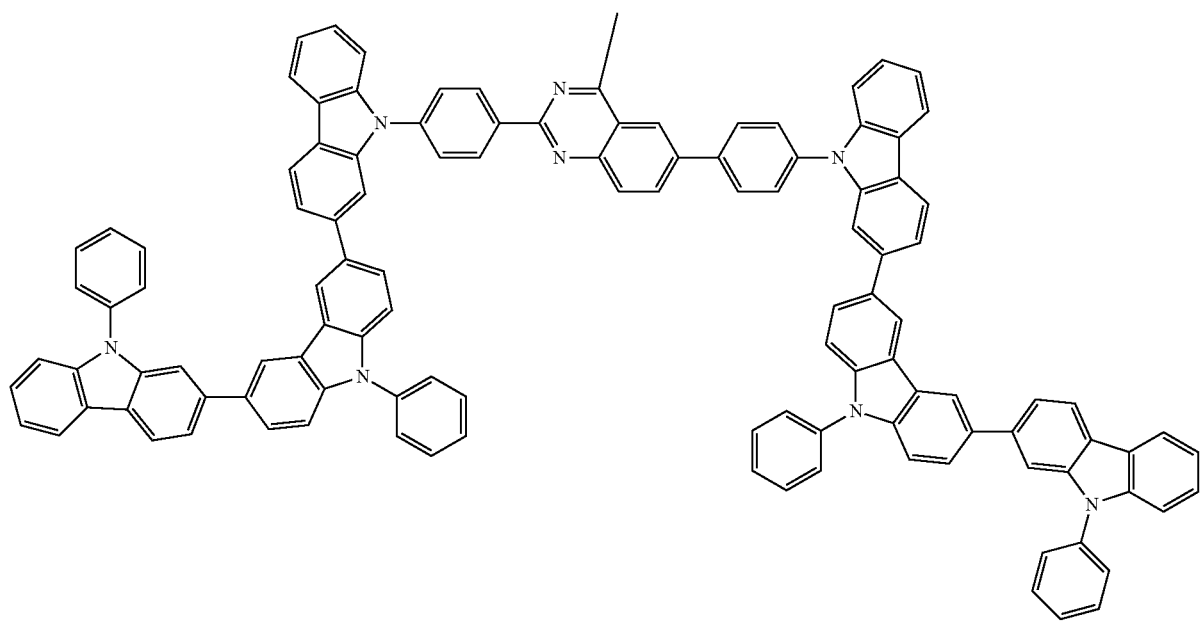

137 138
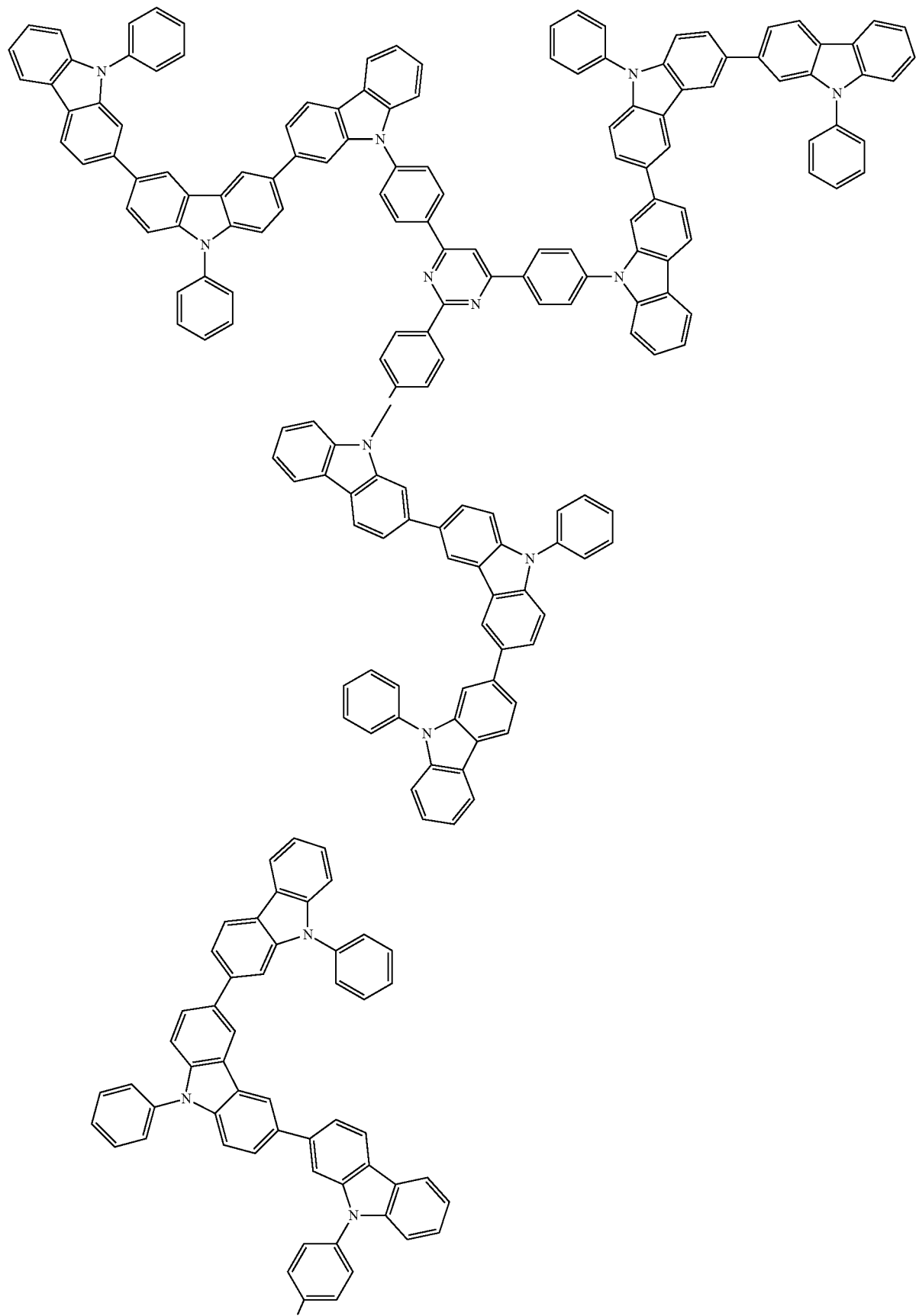

-continued
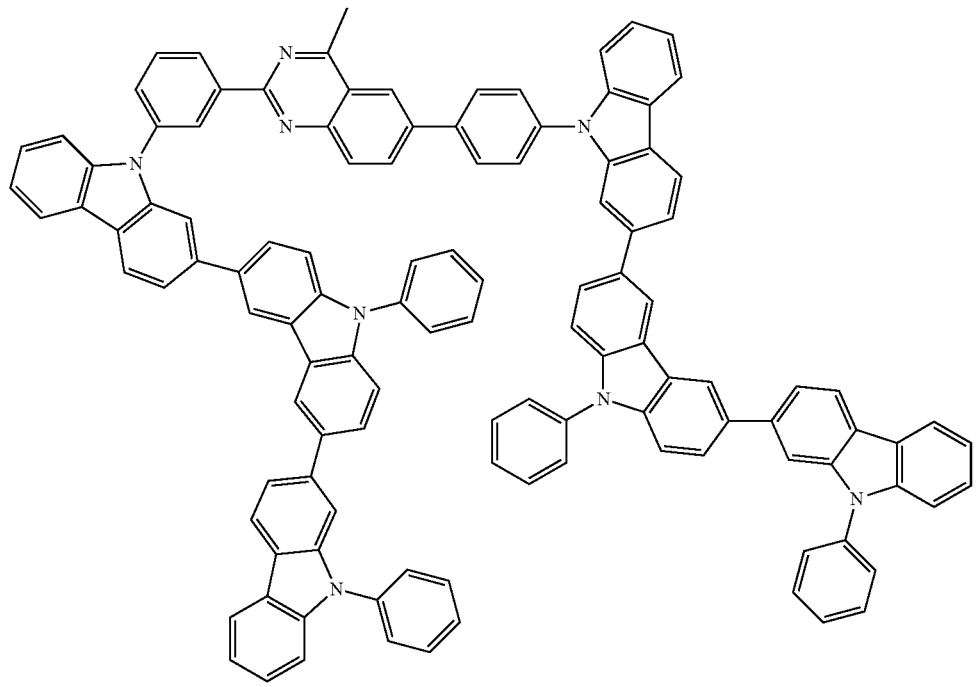
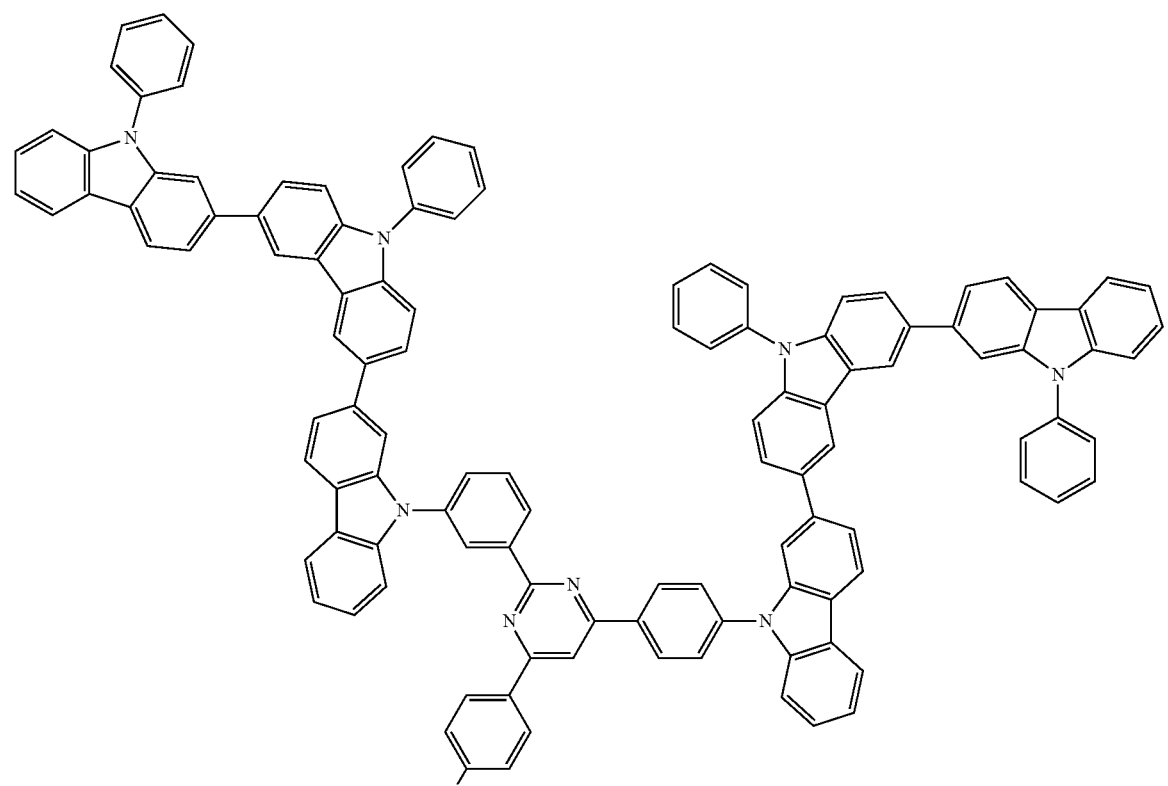

-continued
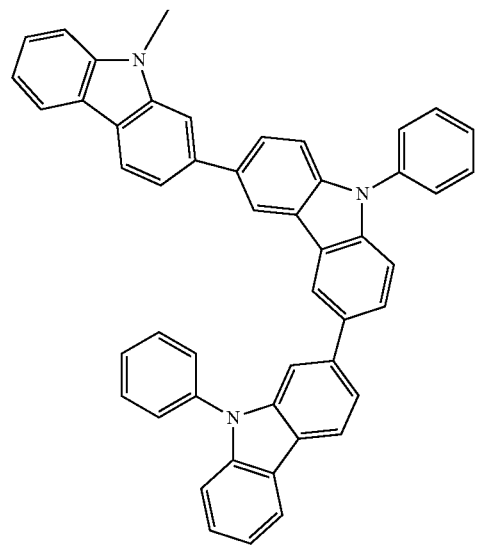
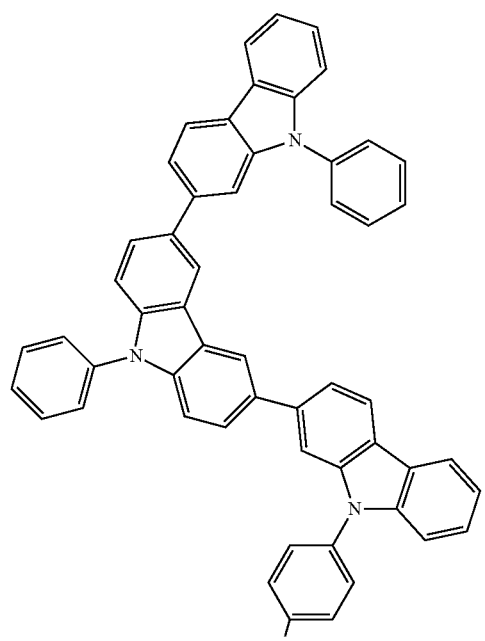

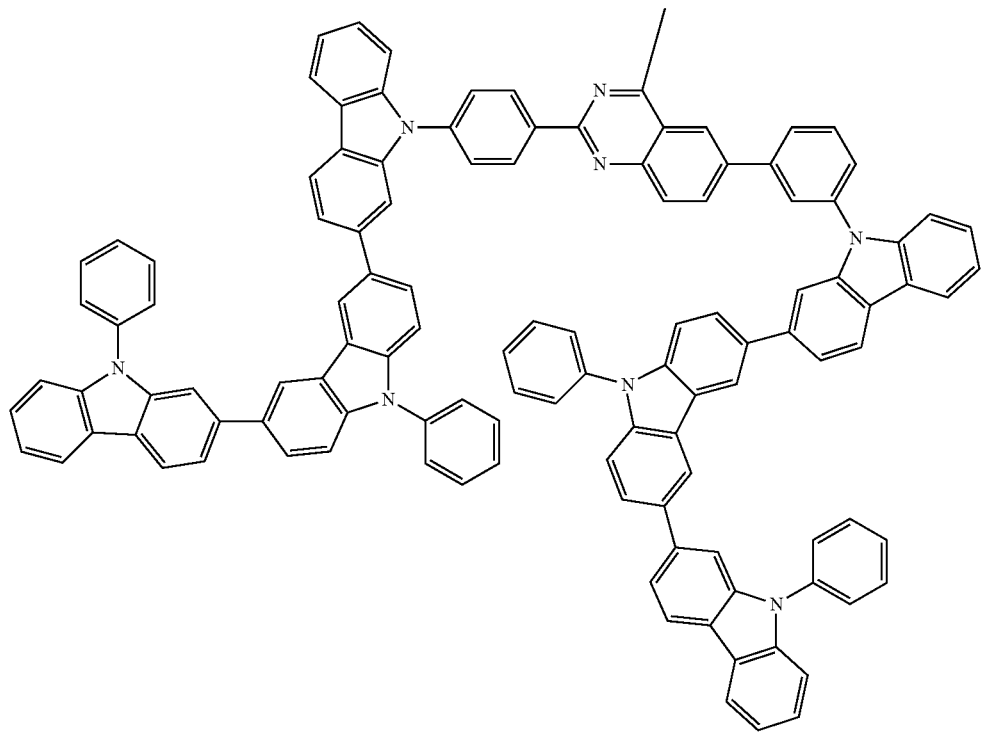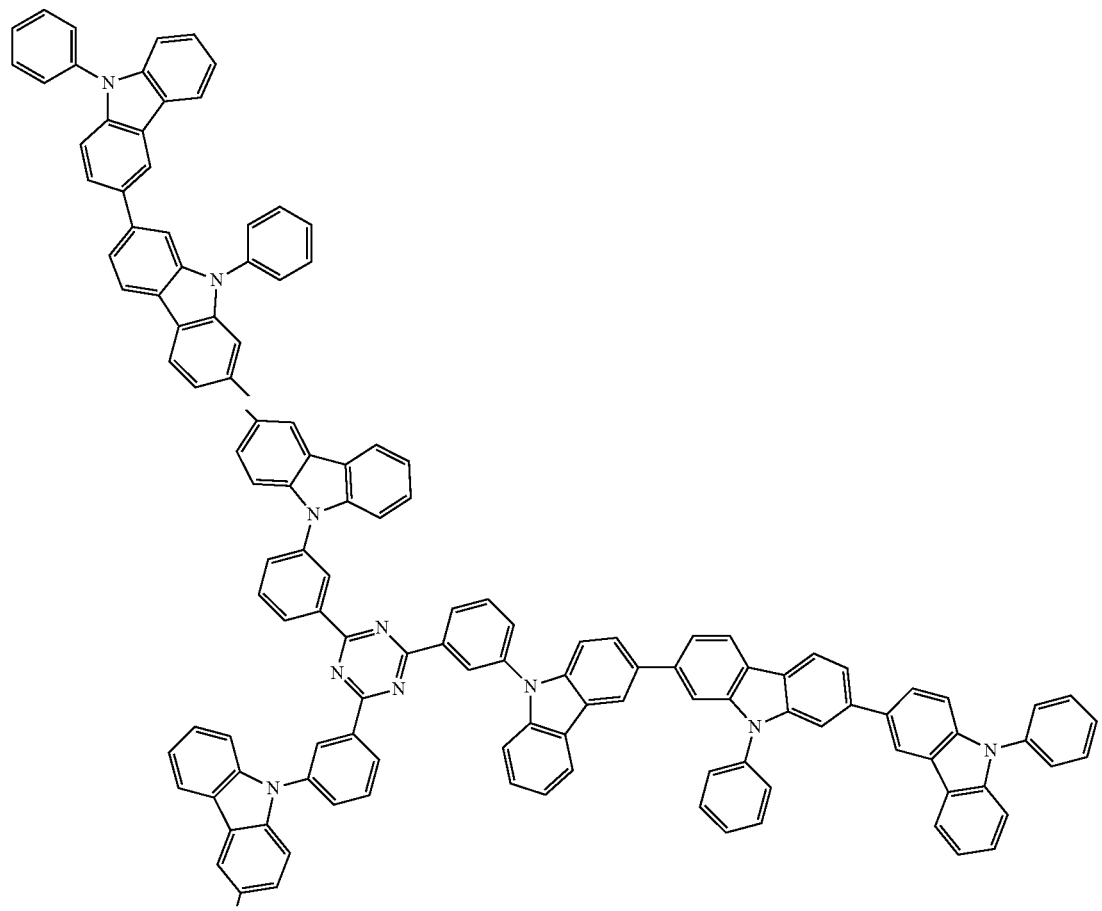

-continued
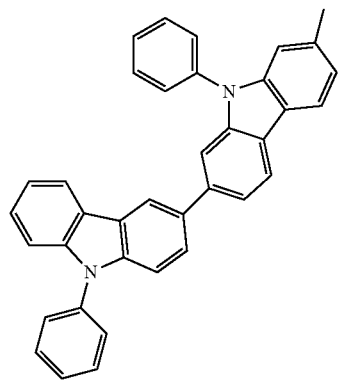
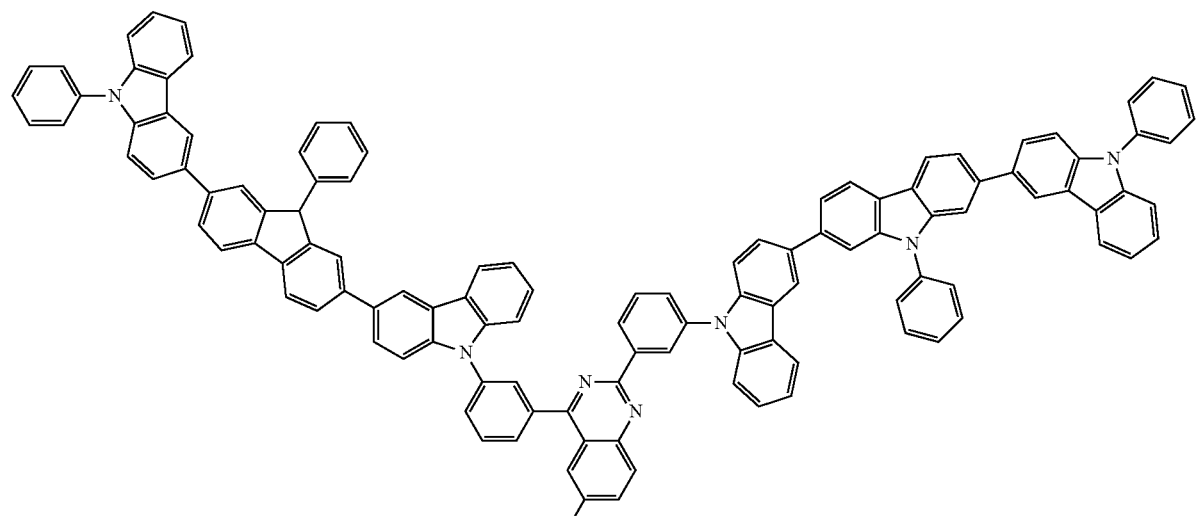
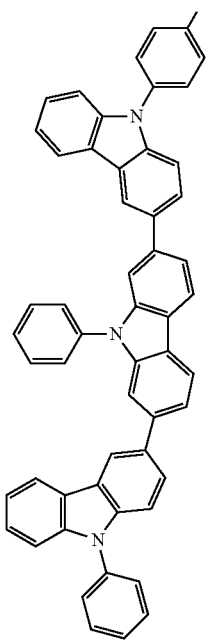

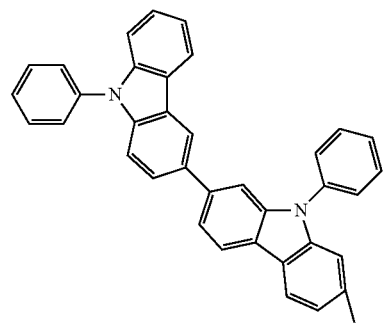
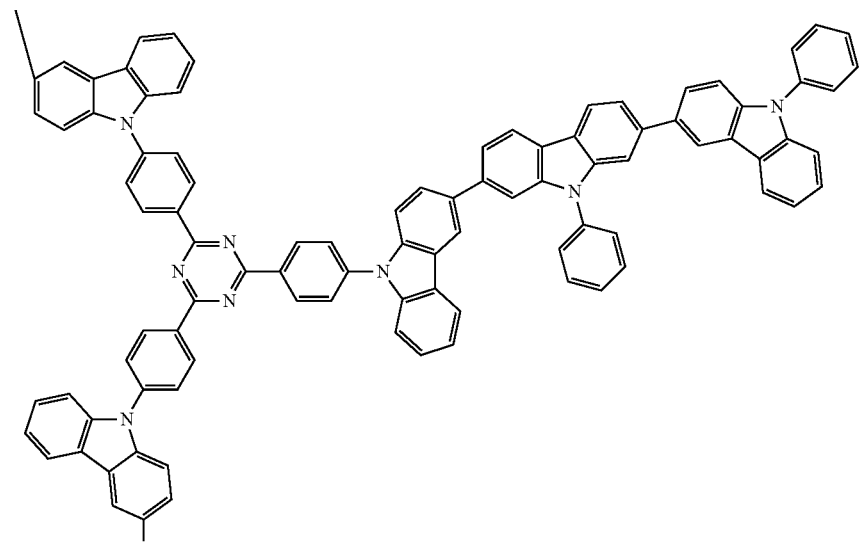
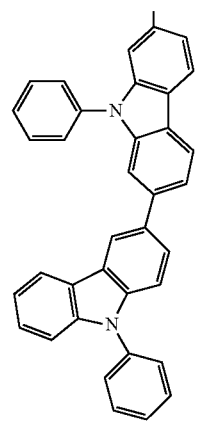

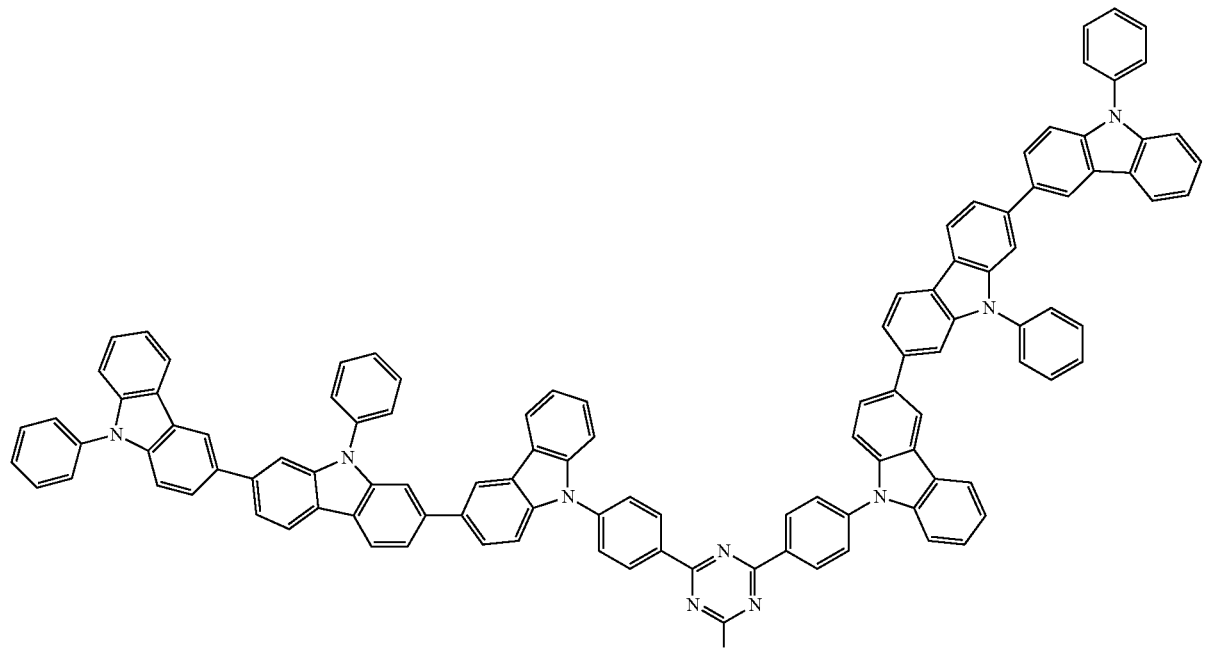
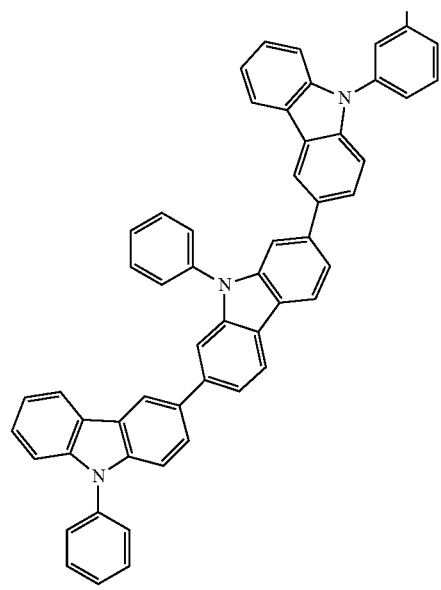
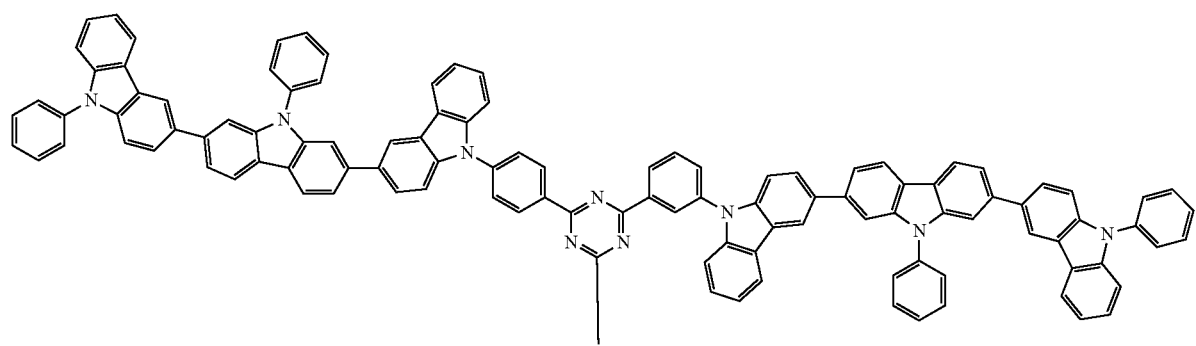

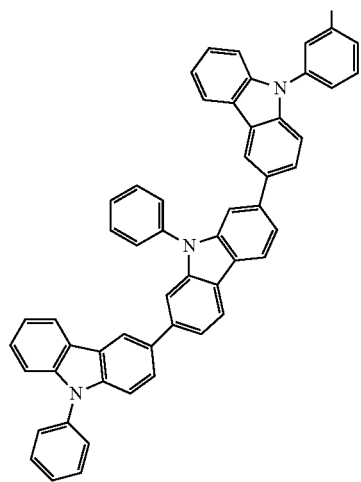
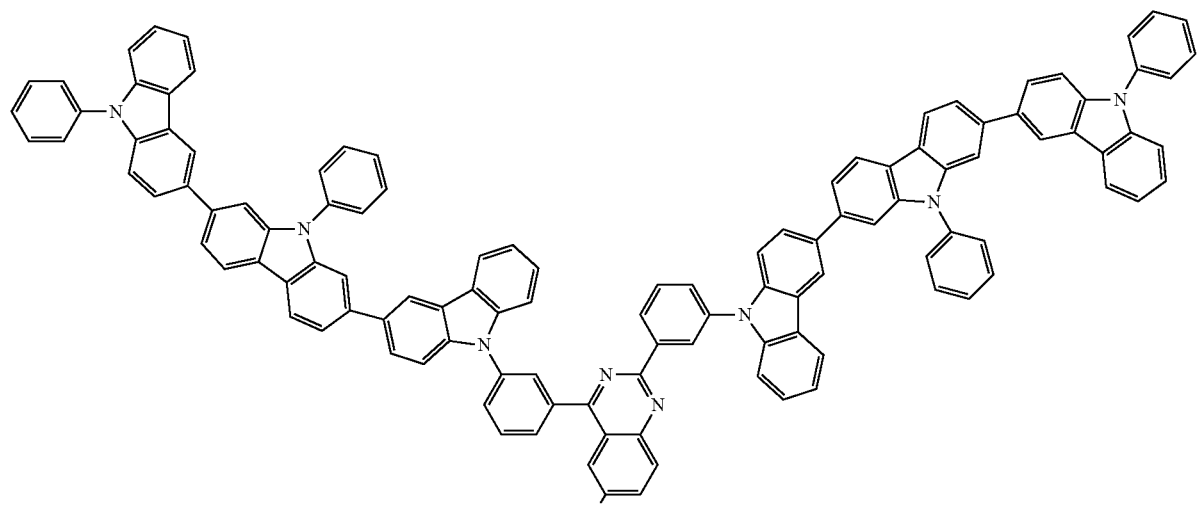
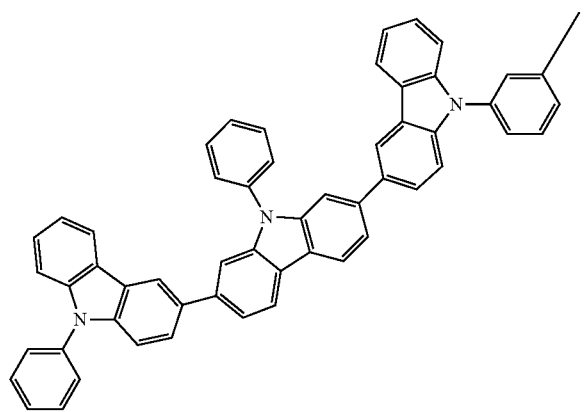

-continued
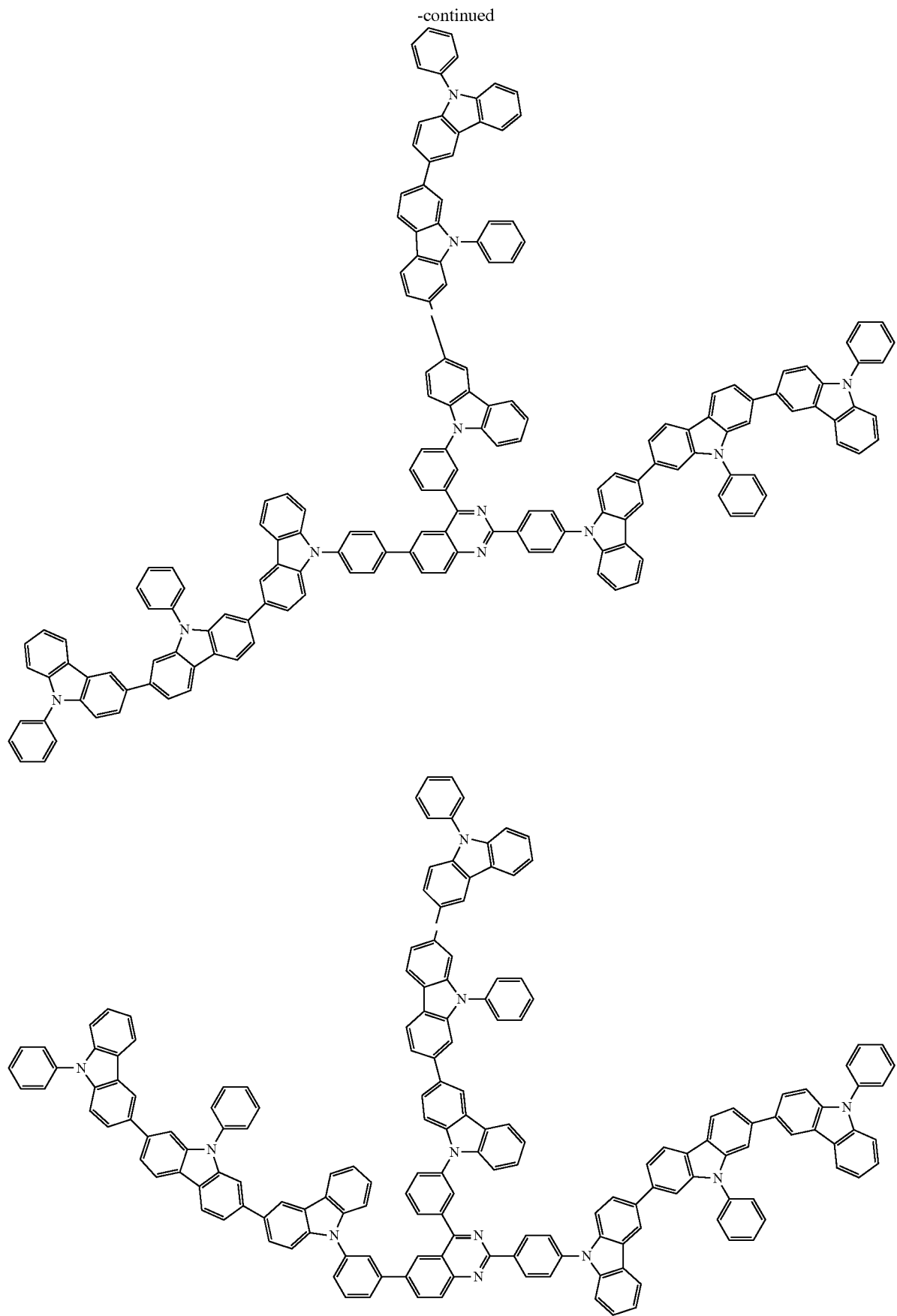

-continued
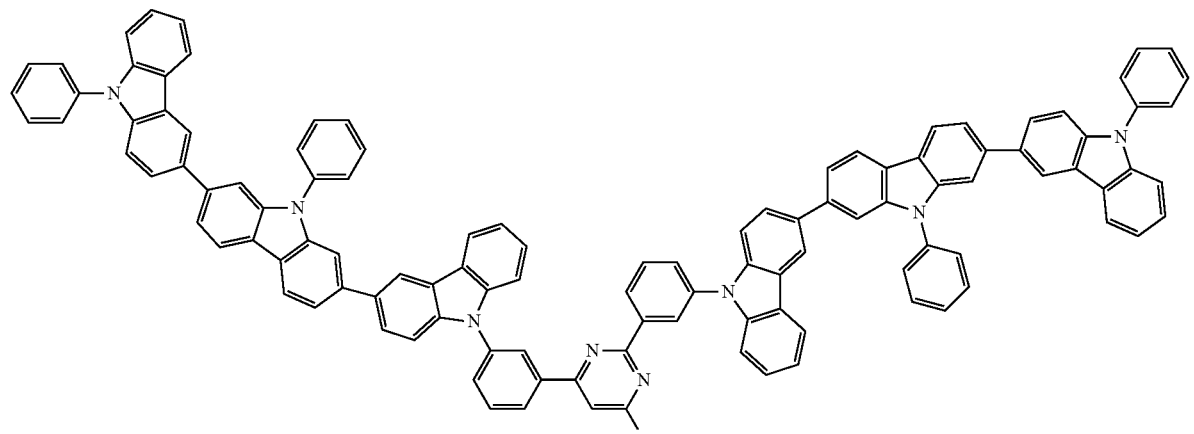
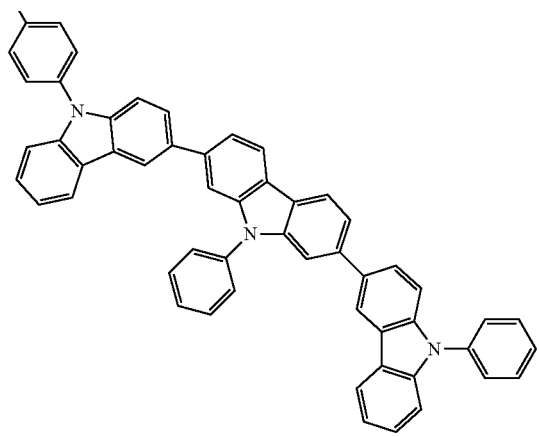
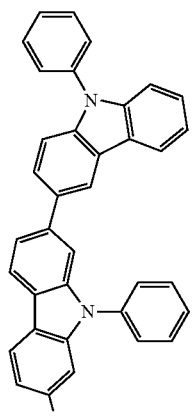

-continued
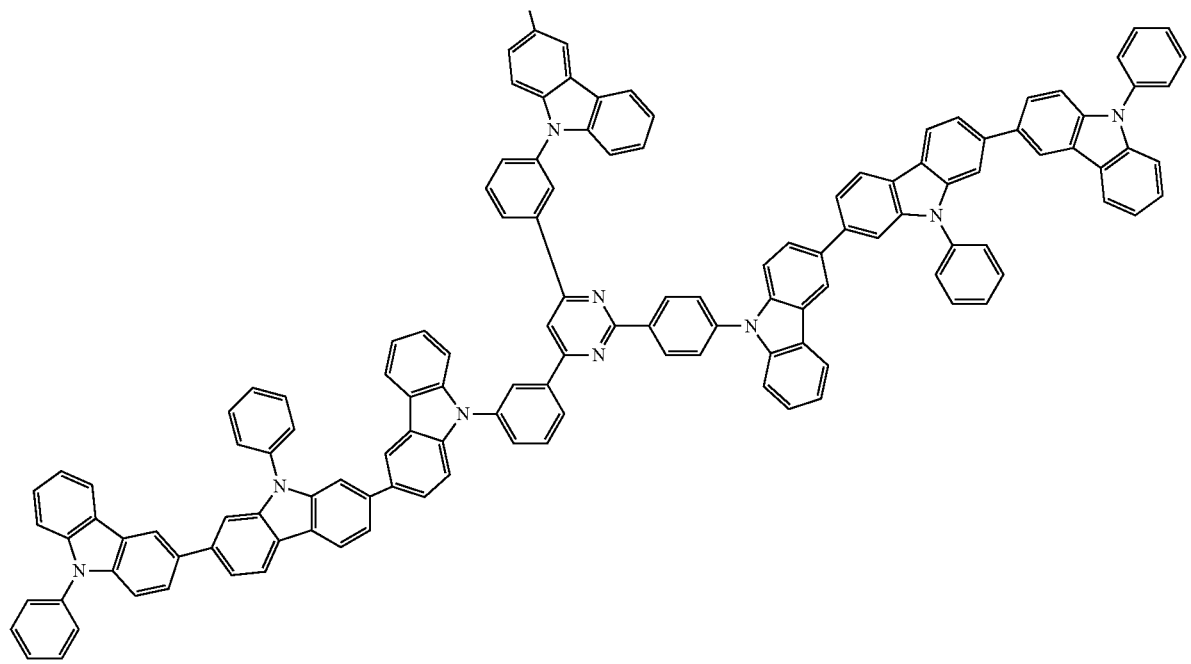
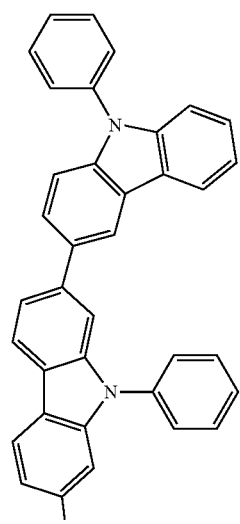

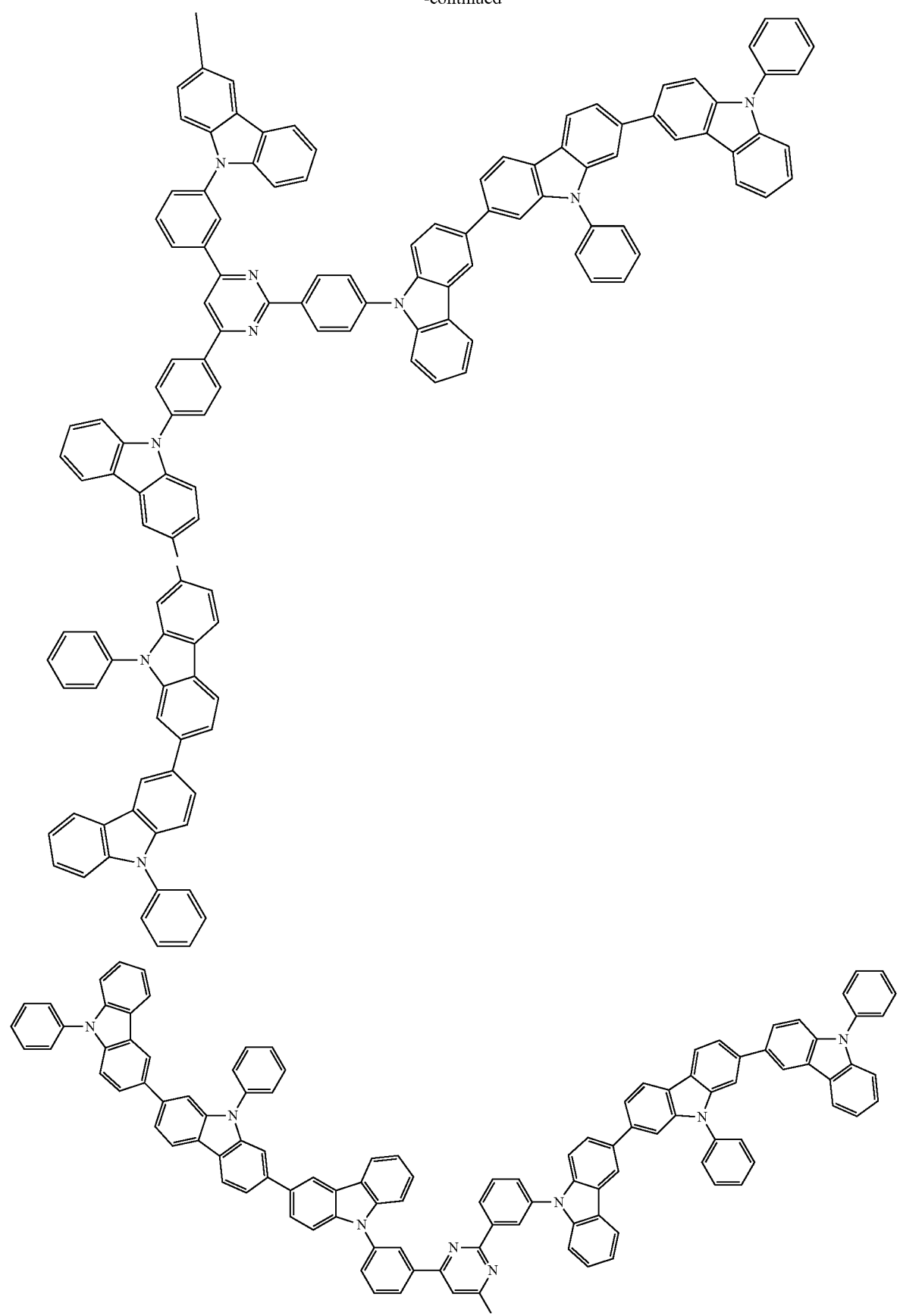

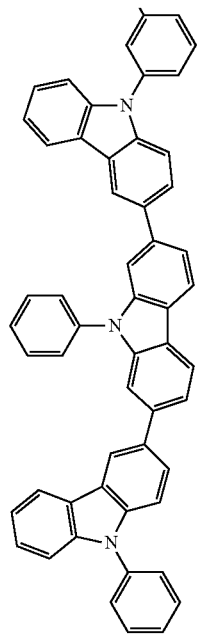
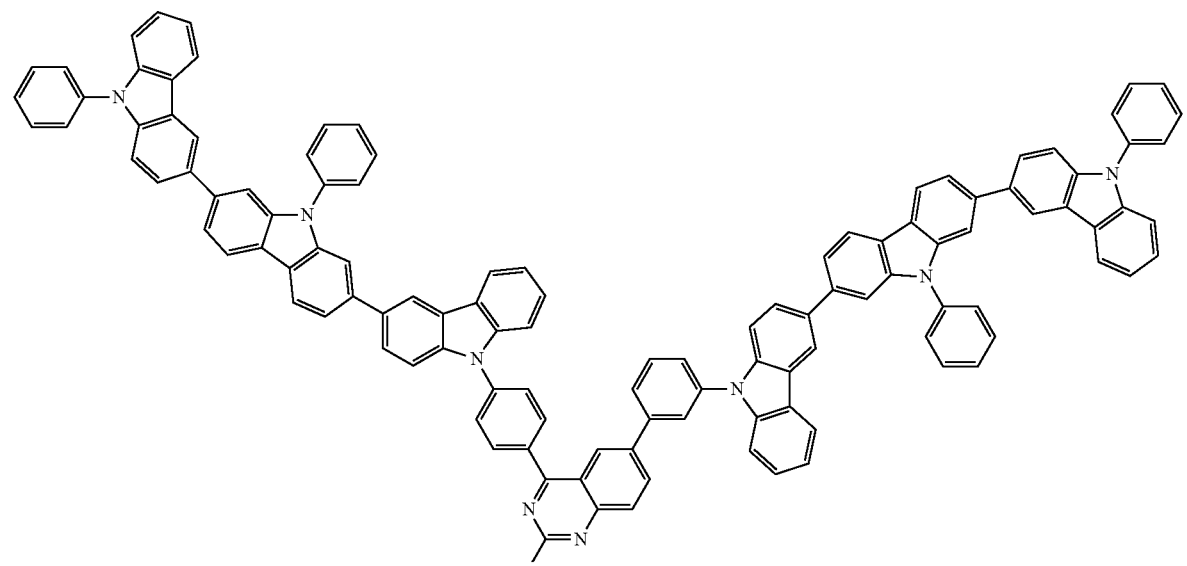

-continued
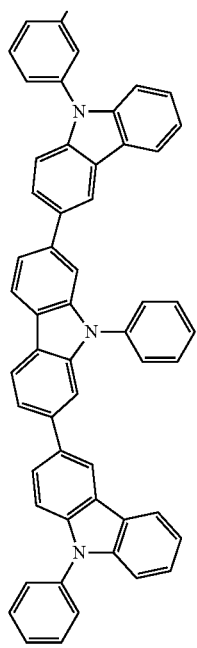
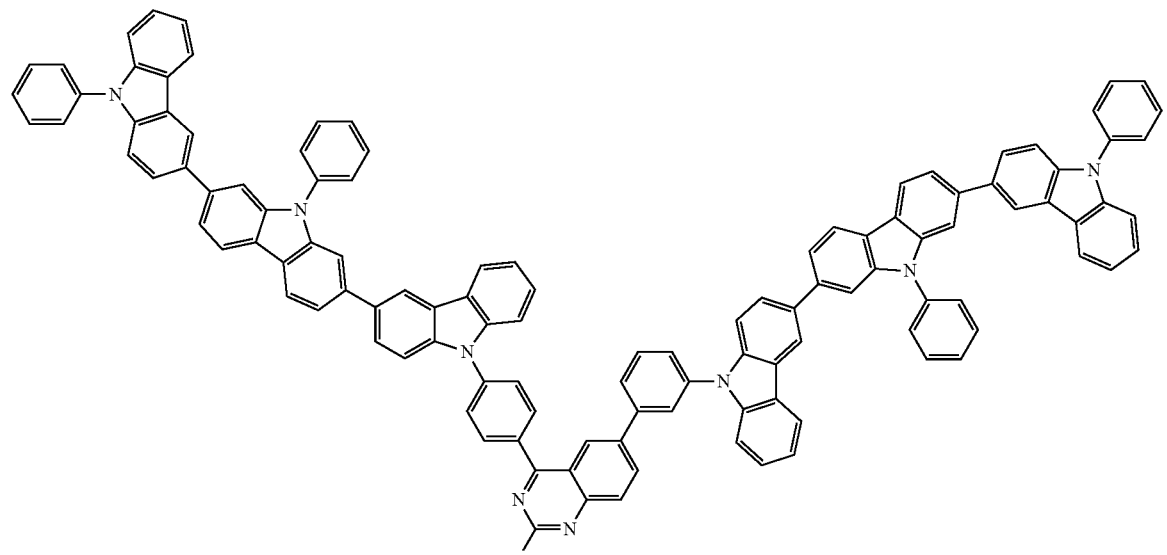
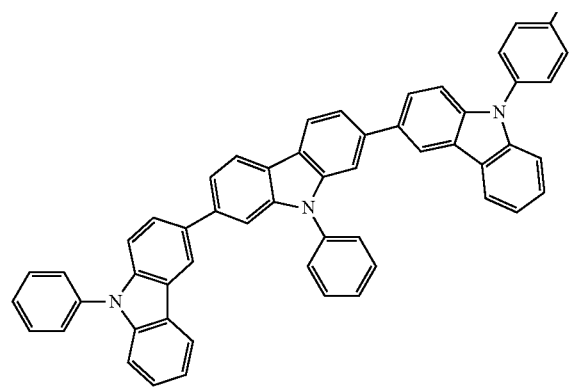

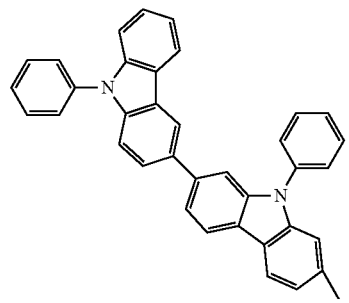
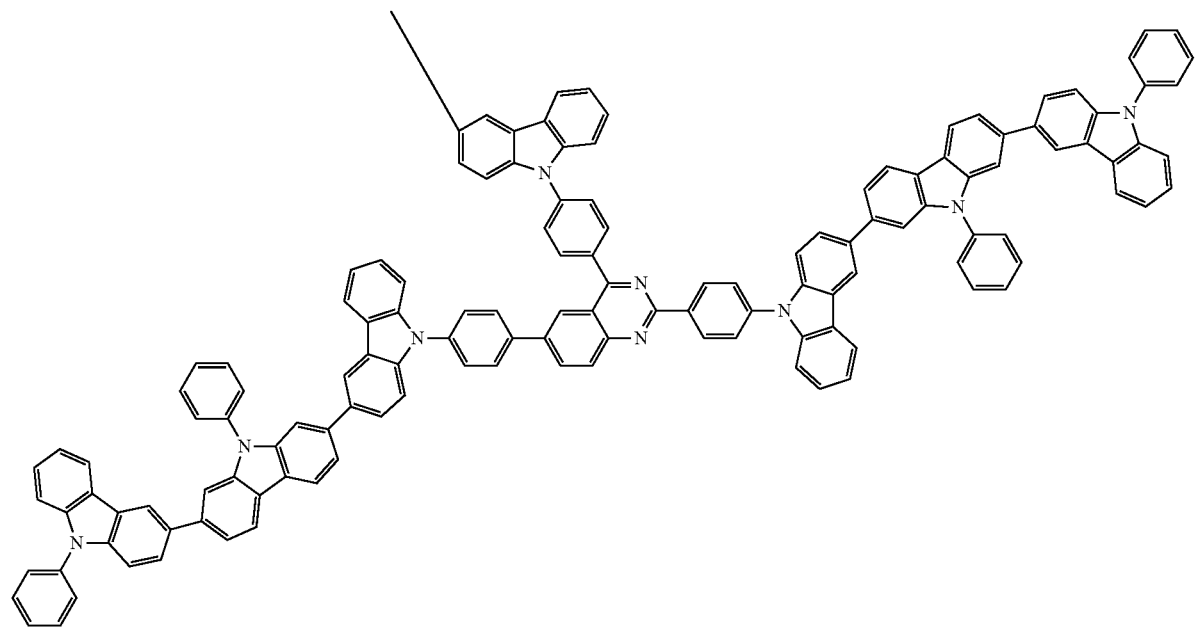
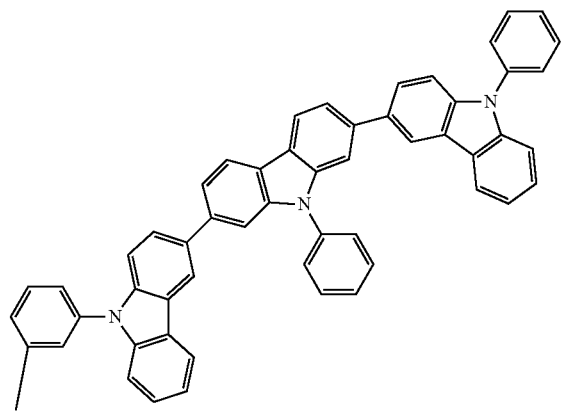

-continued
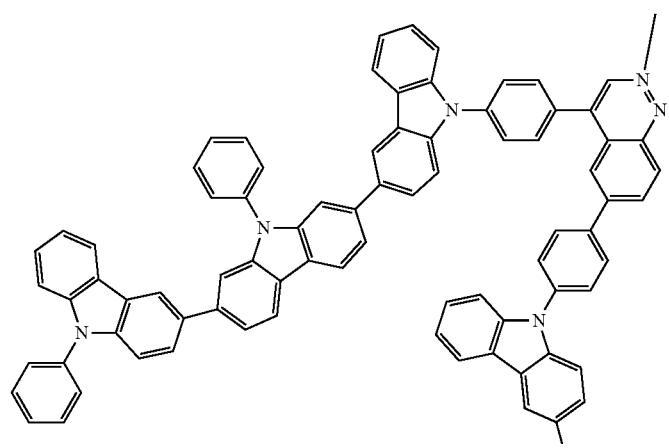
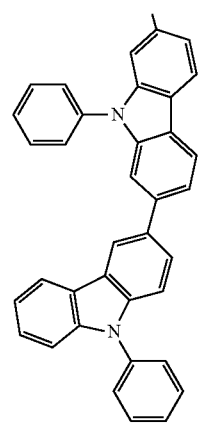
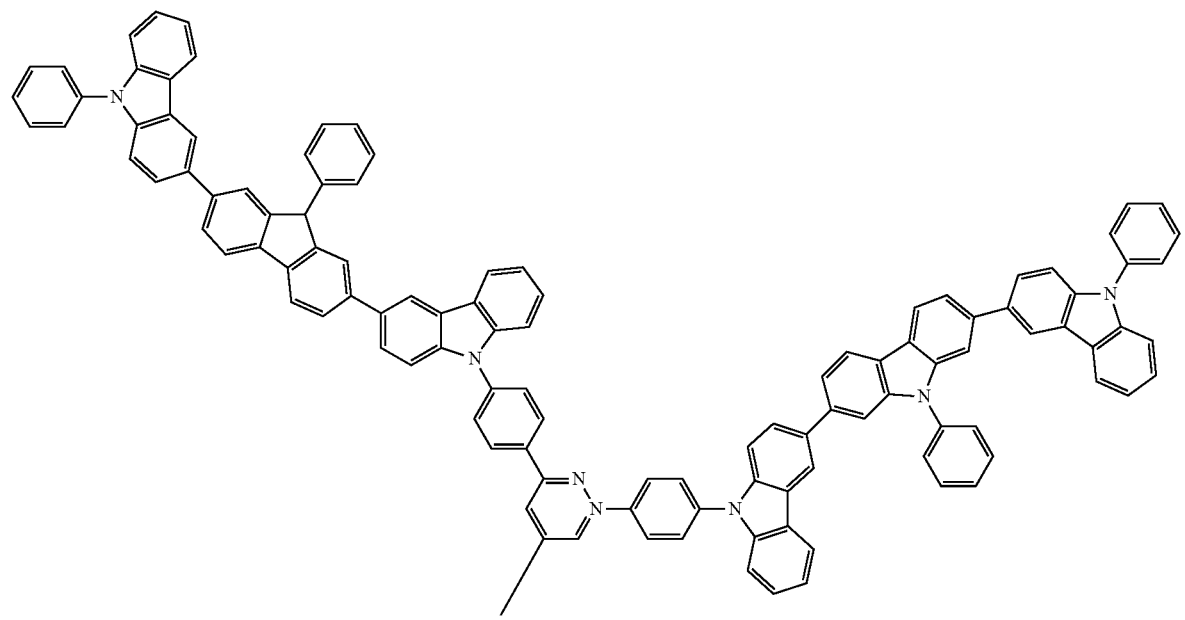

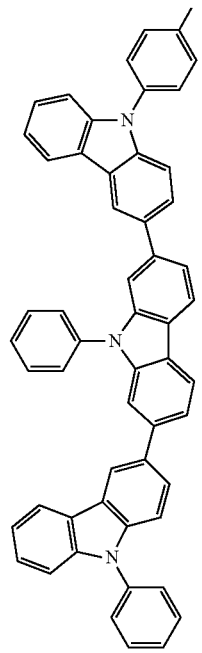
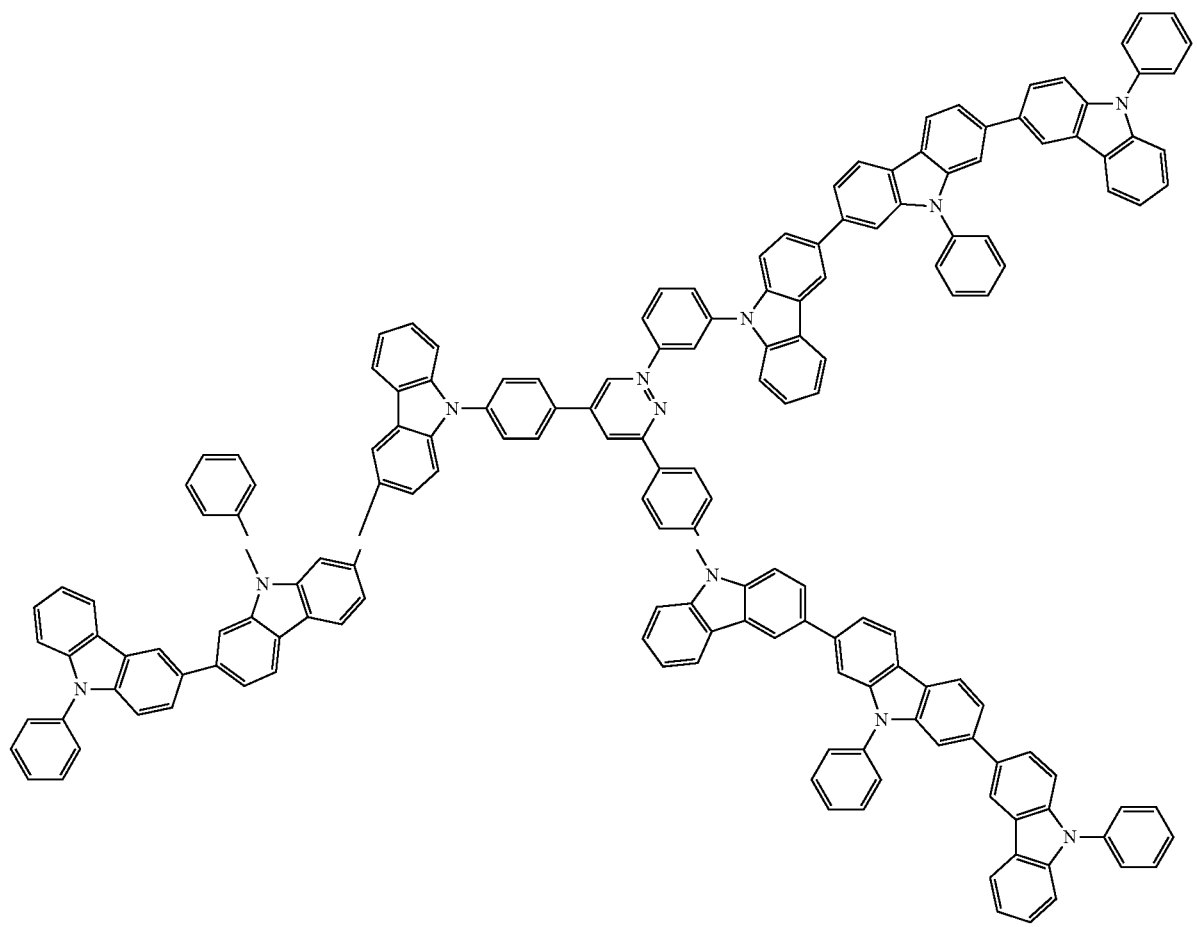

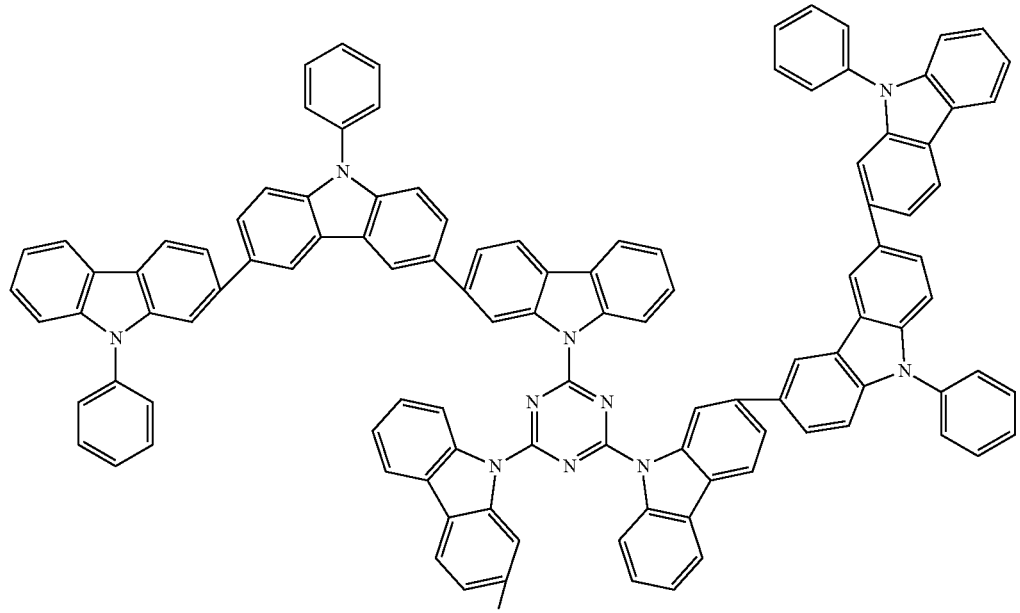
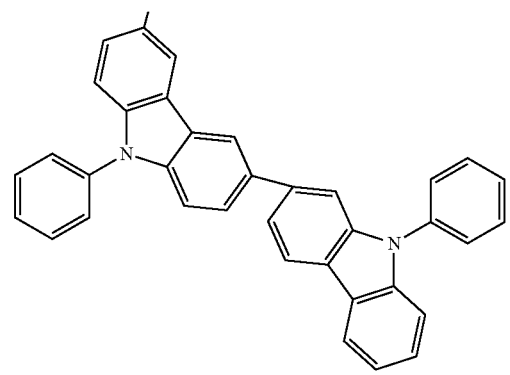
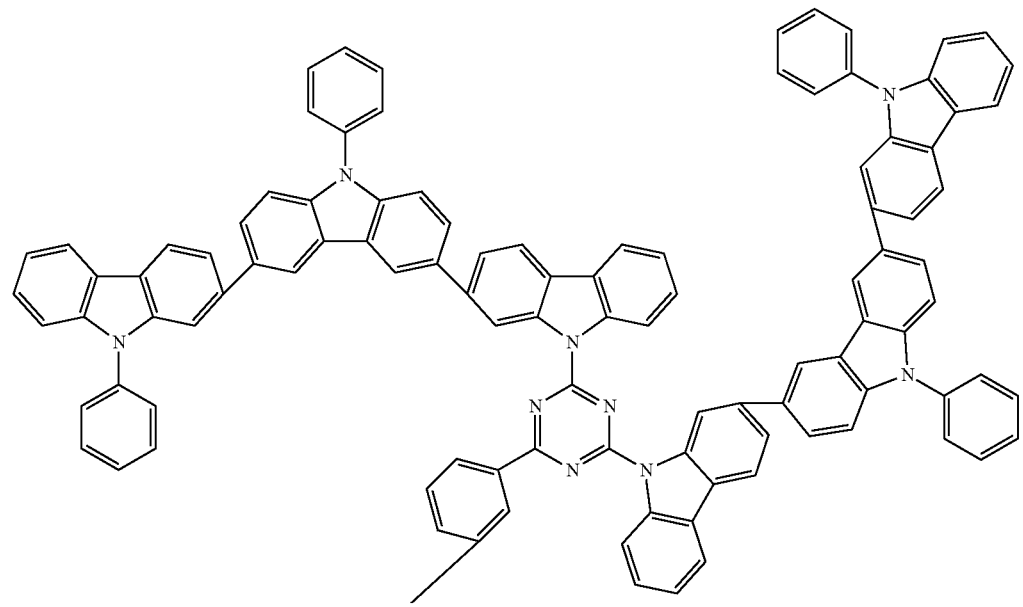

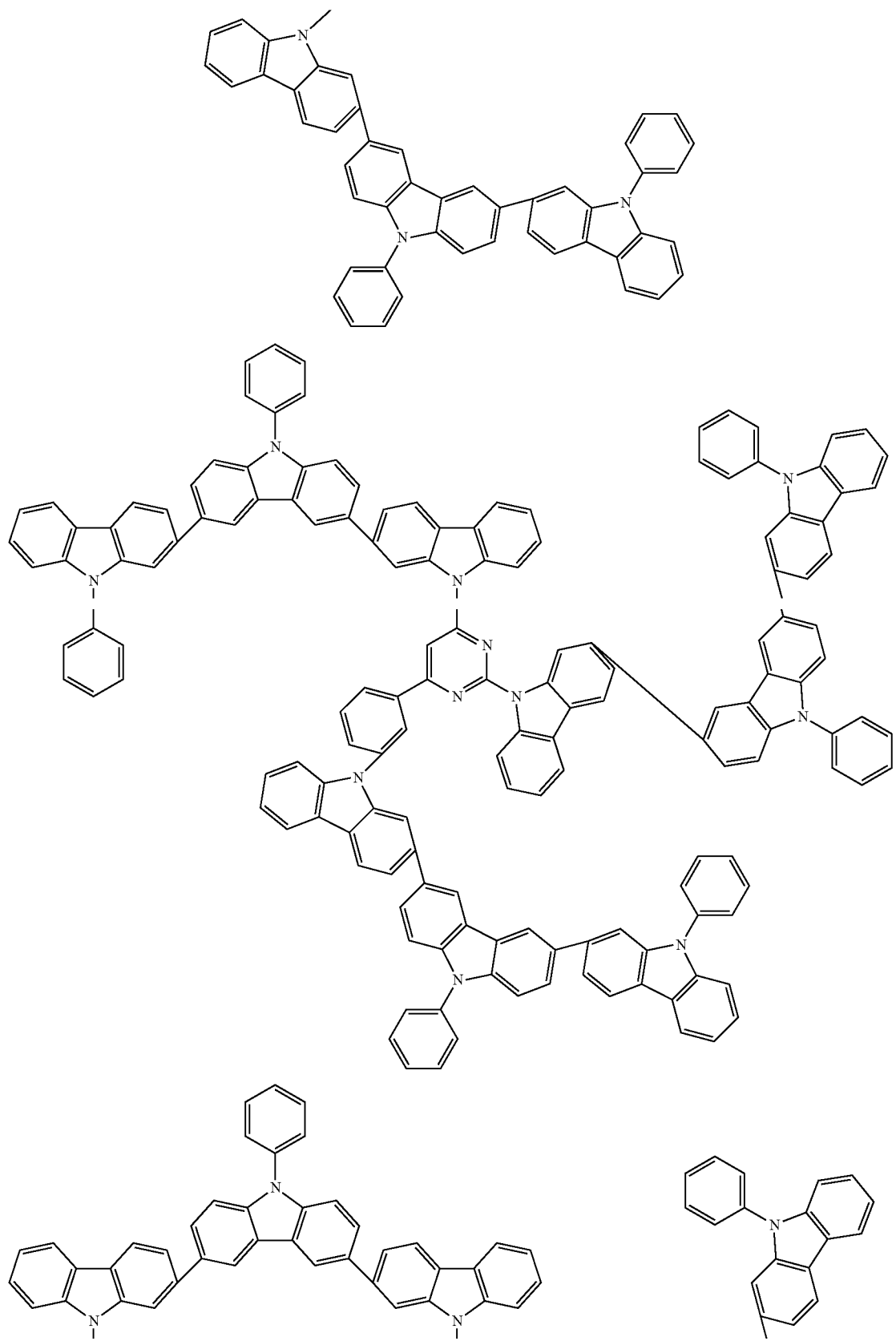

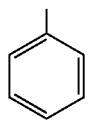
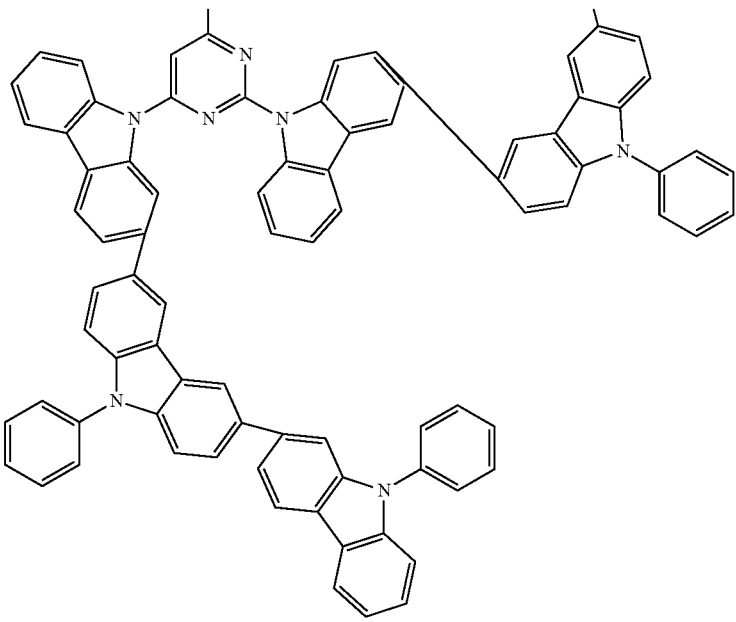
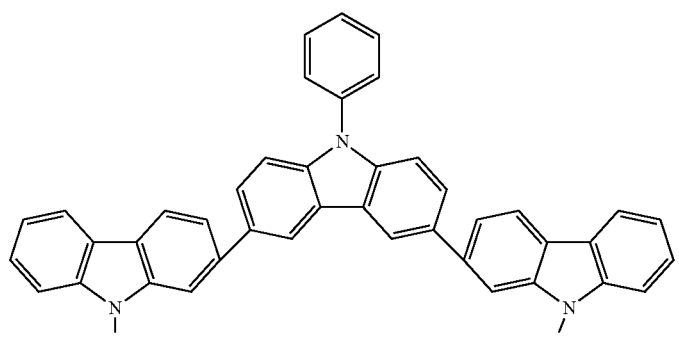
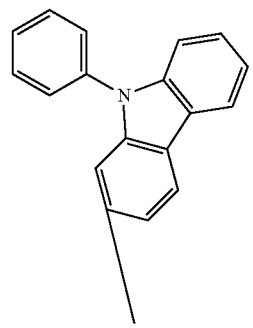
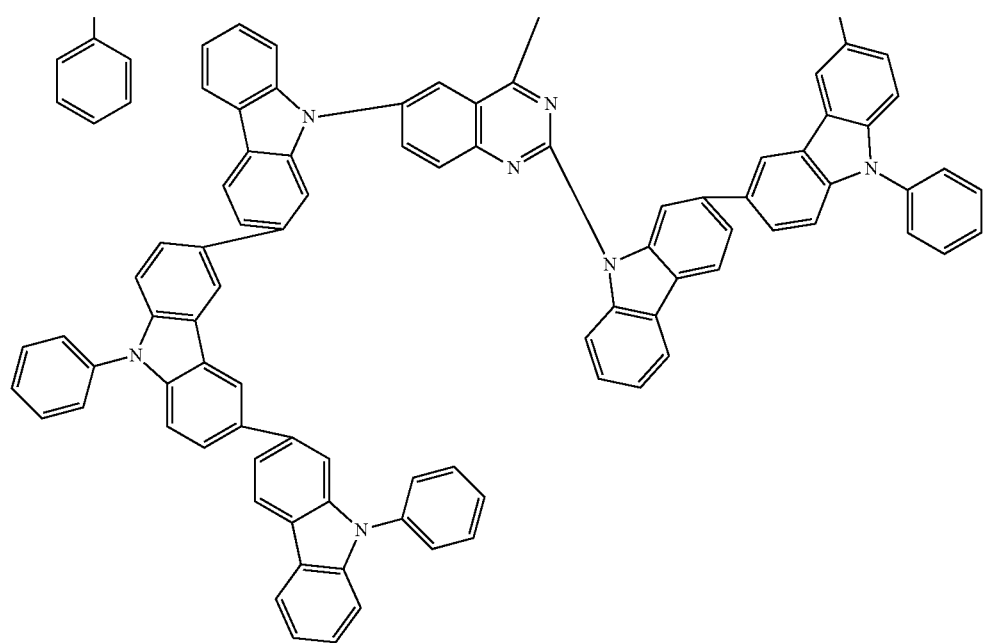

-continued
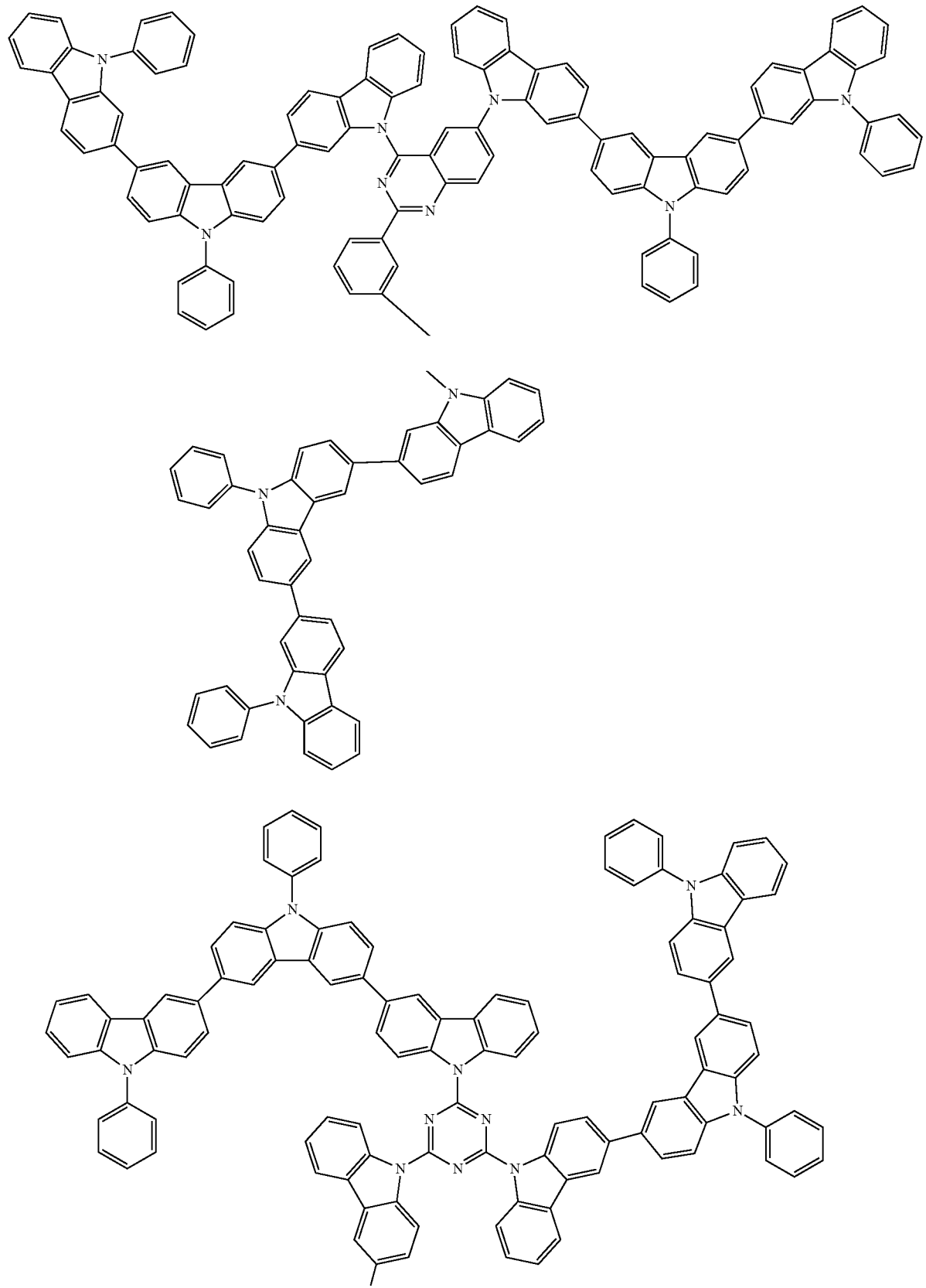

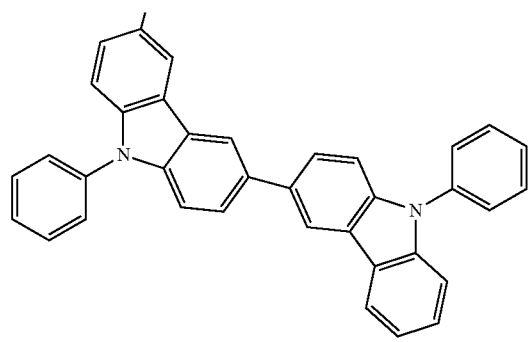
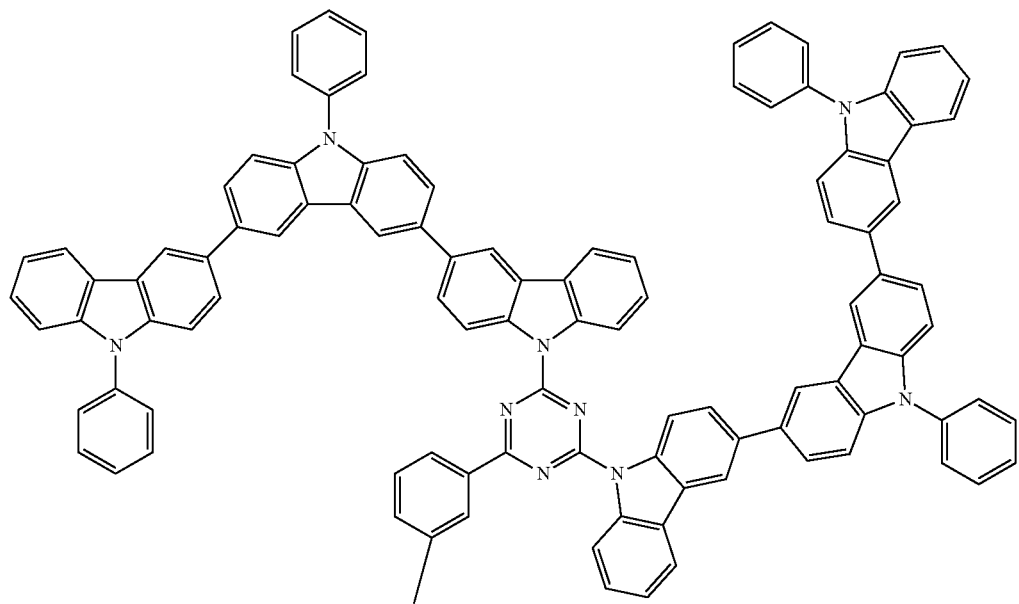
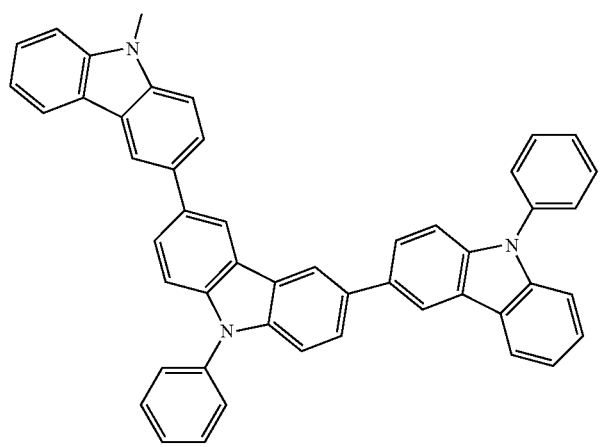

-continued
181
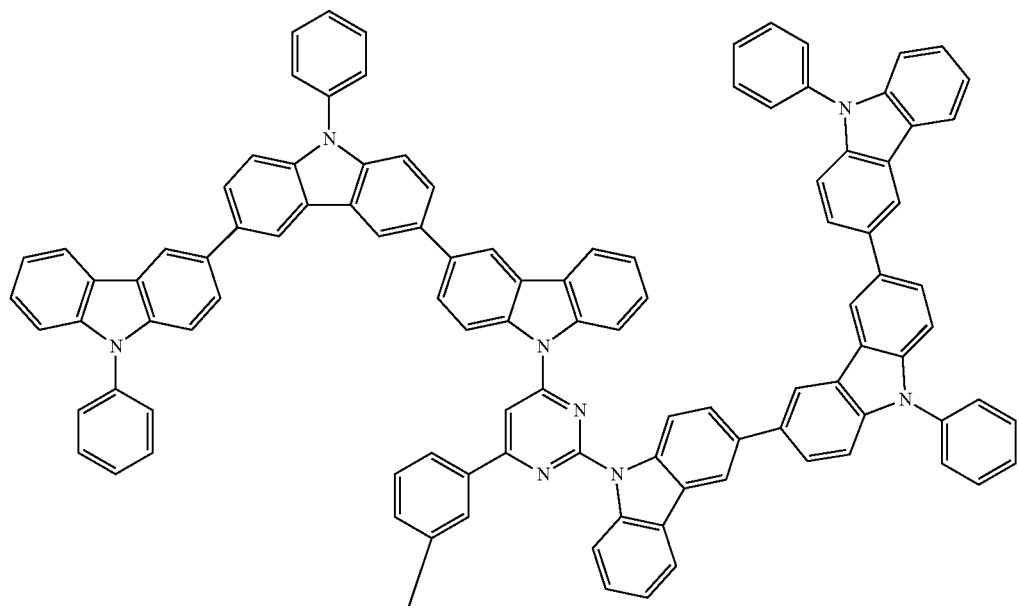
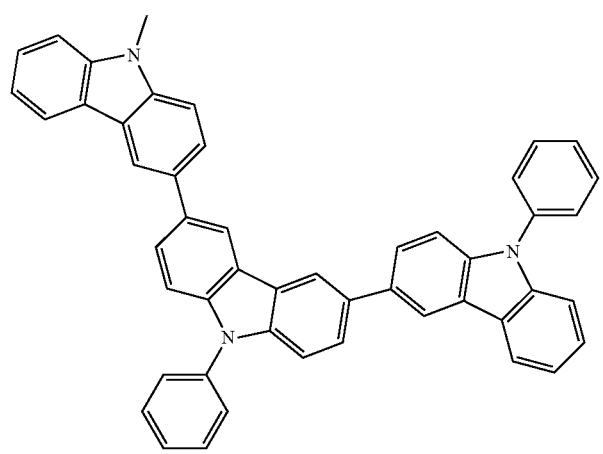
182
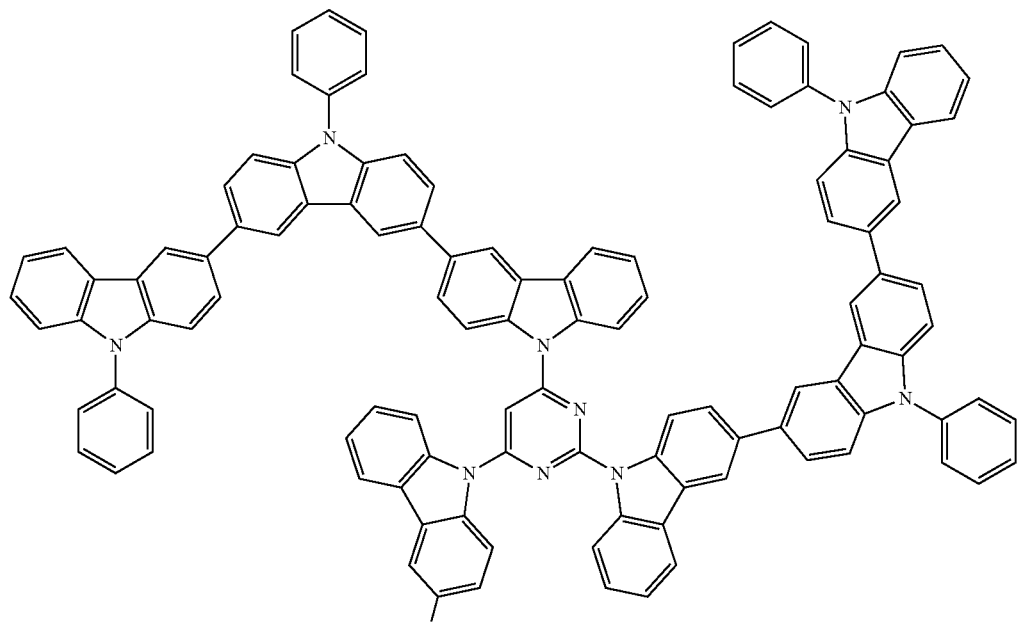

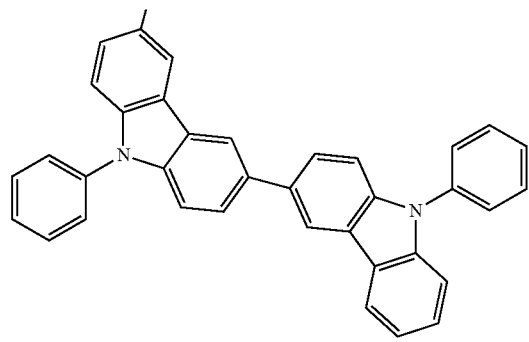
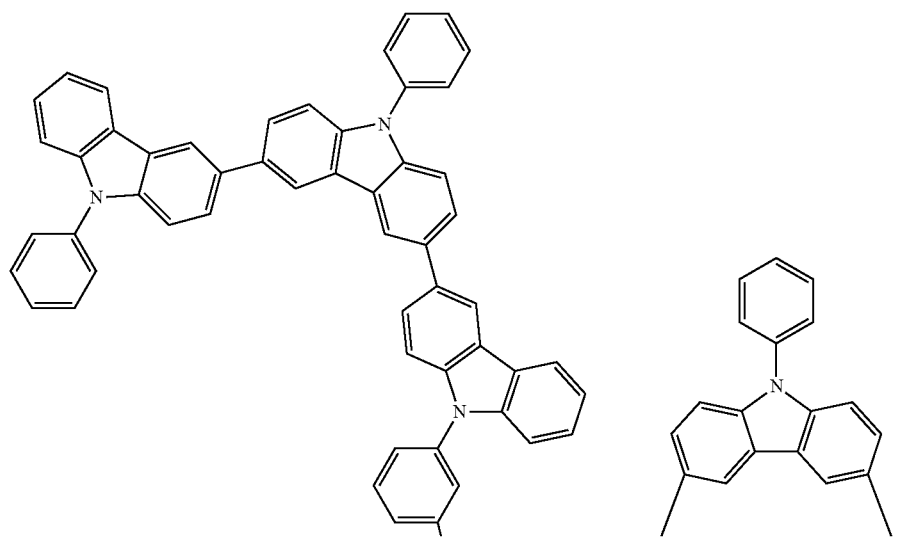
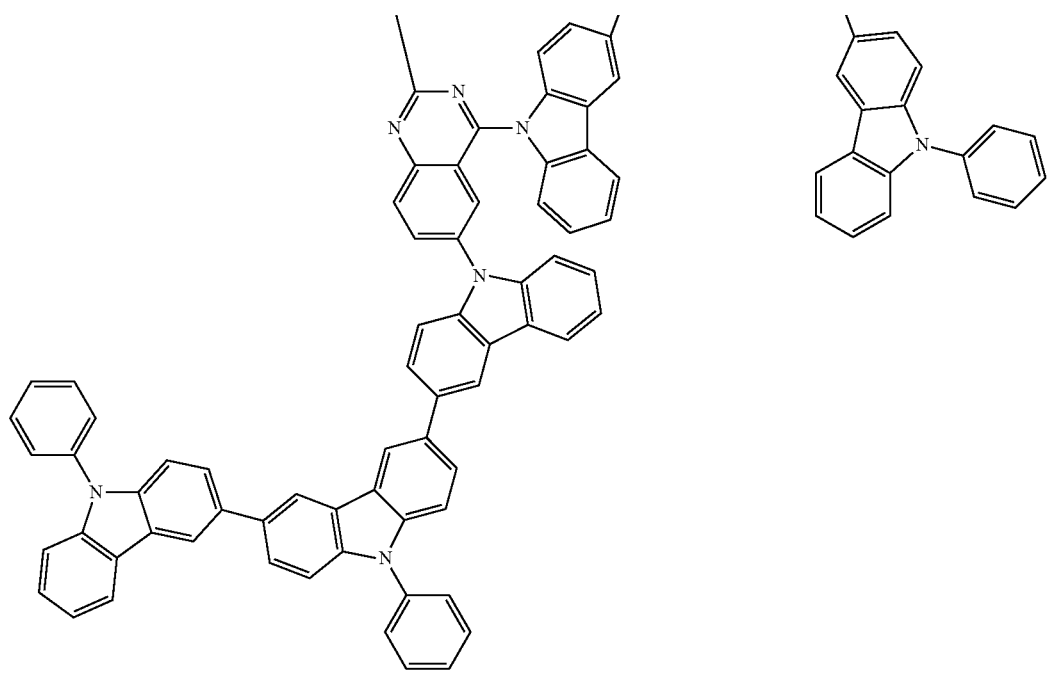

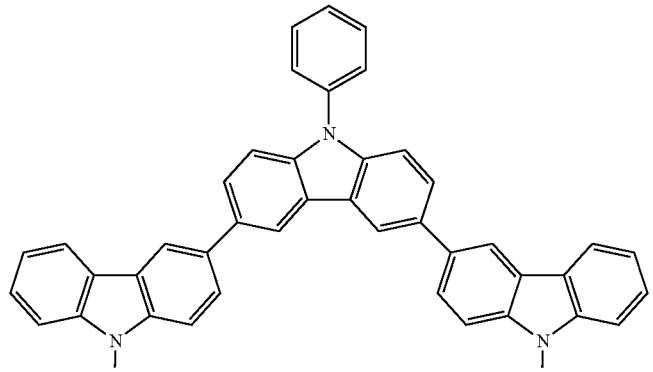
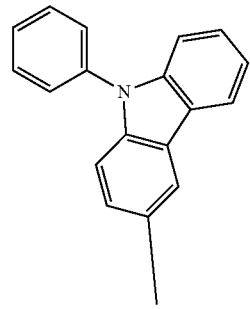
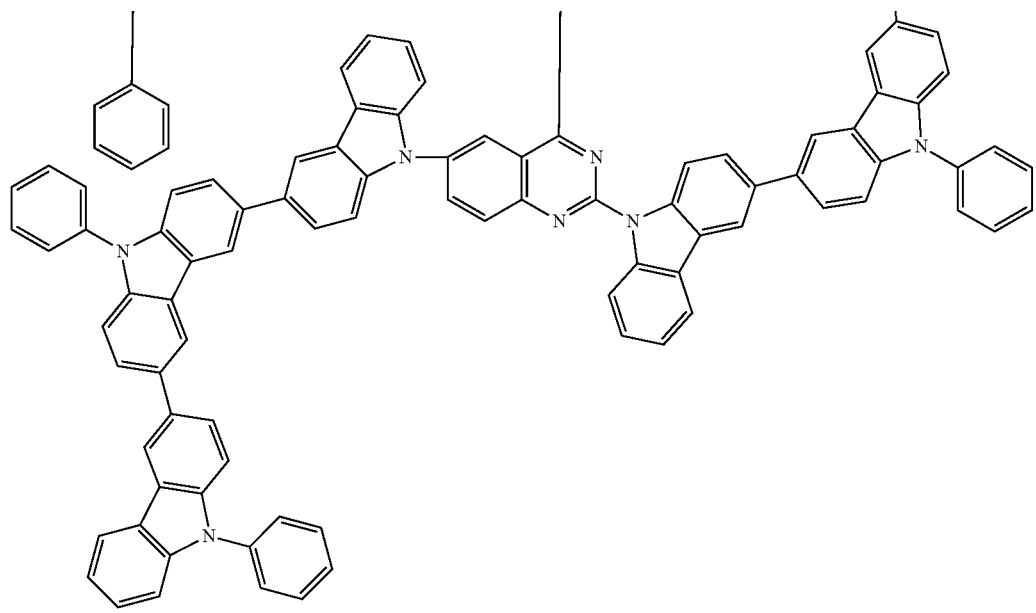
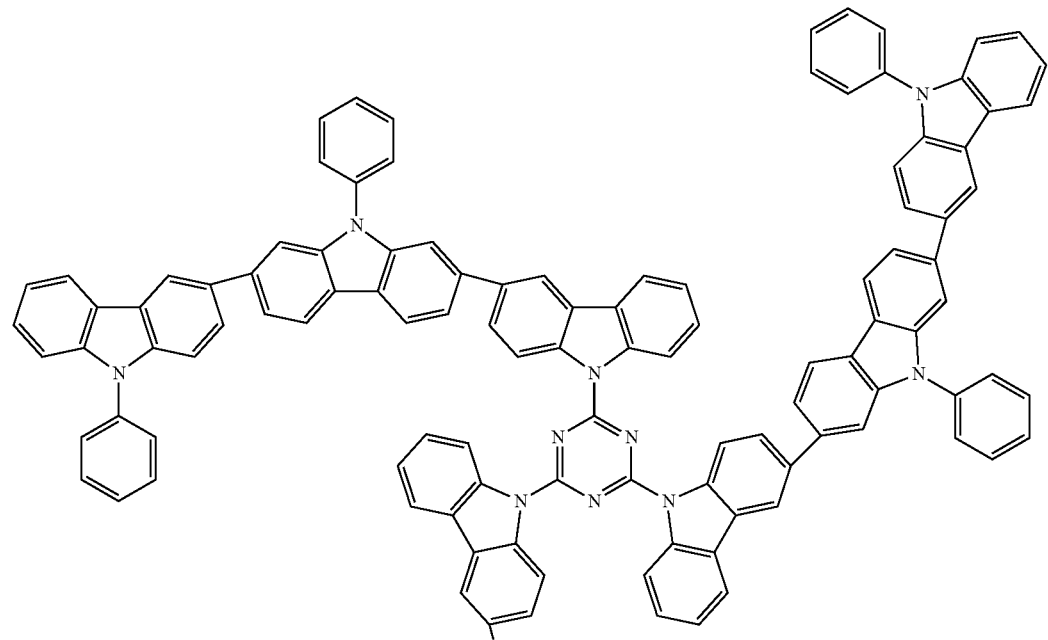

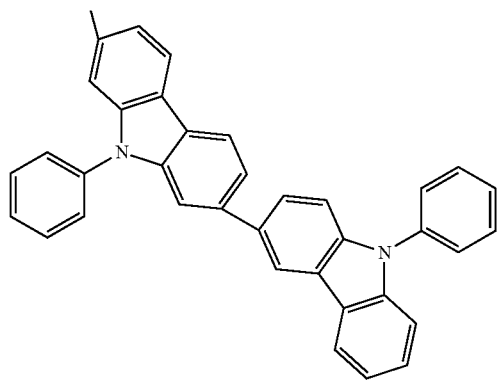
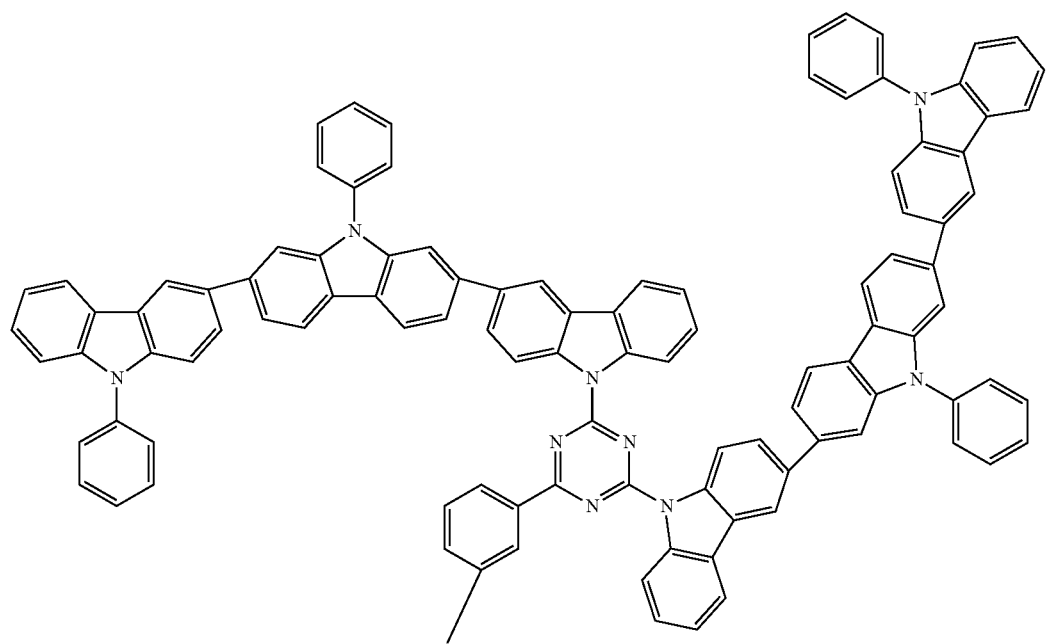
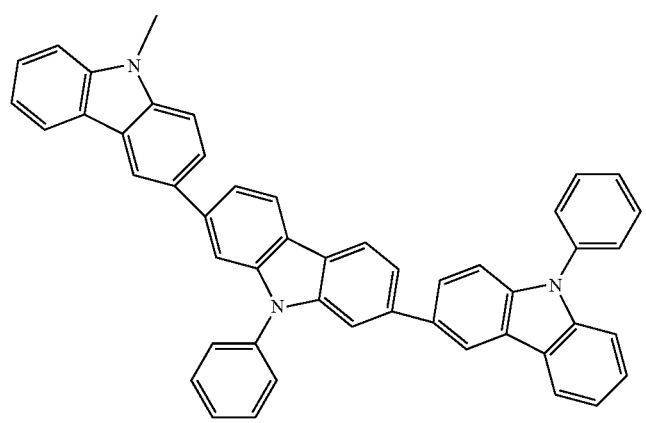

-continued
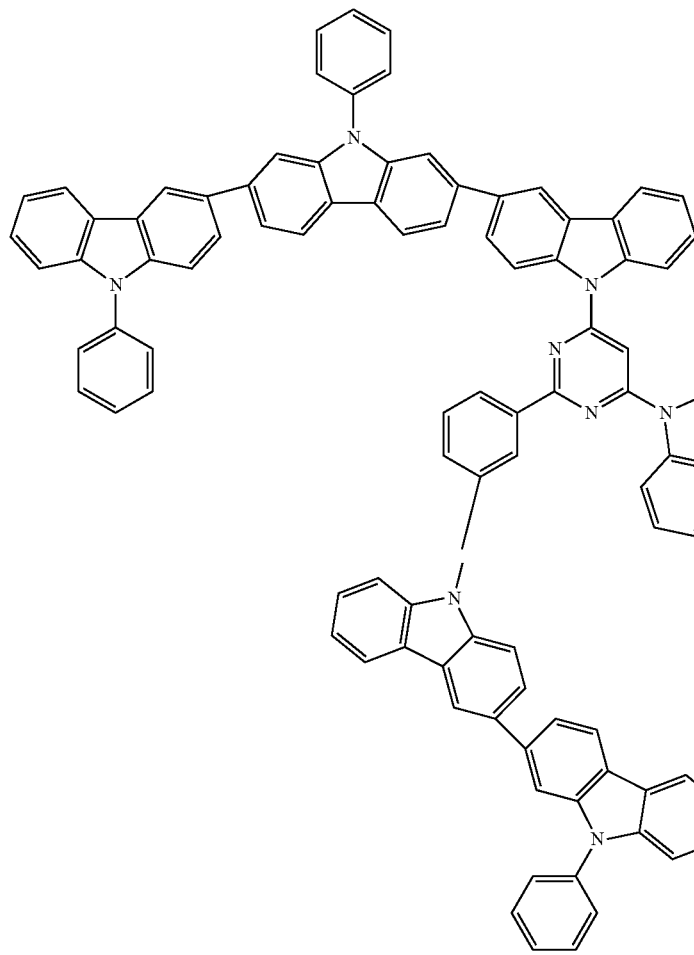
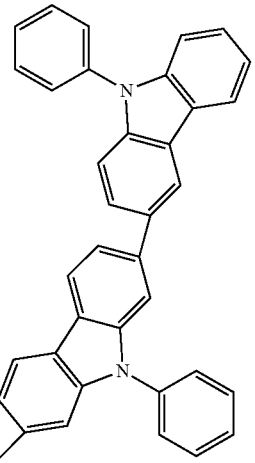
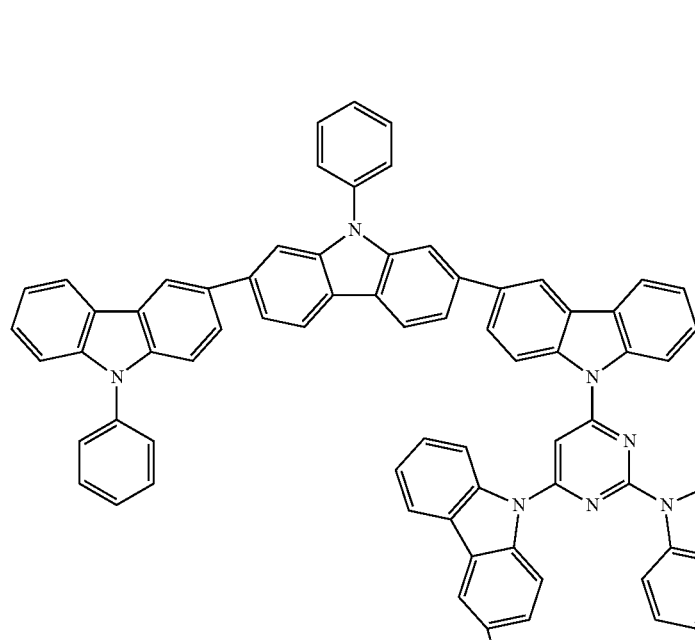
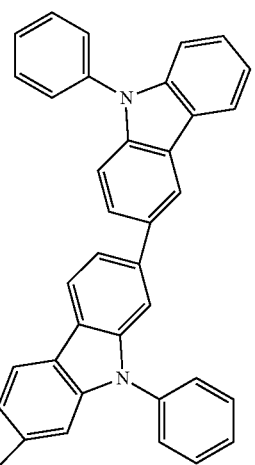

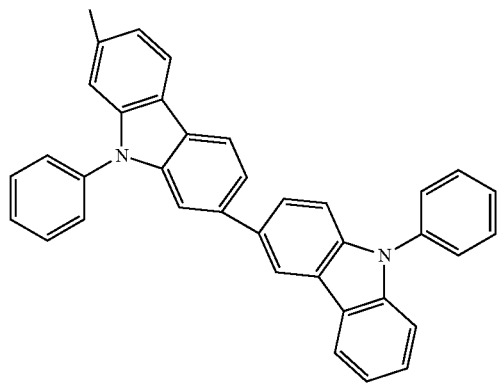
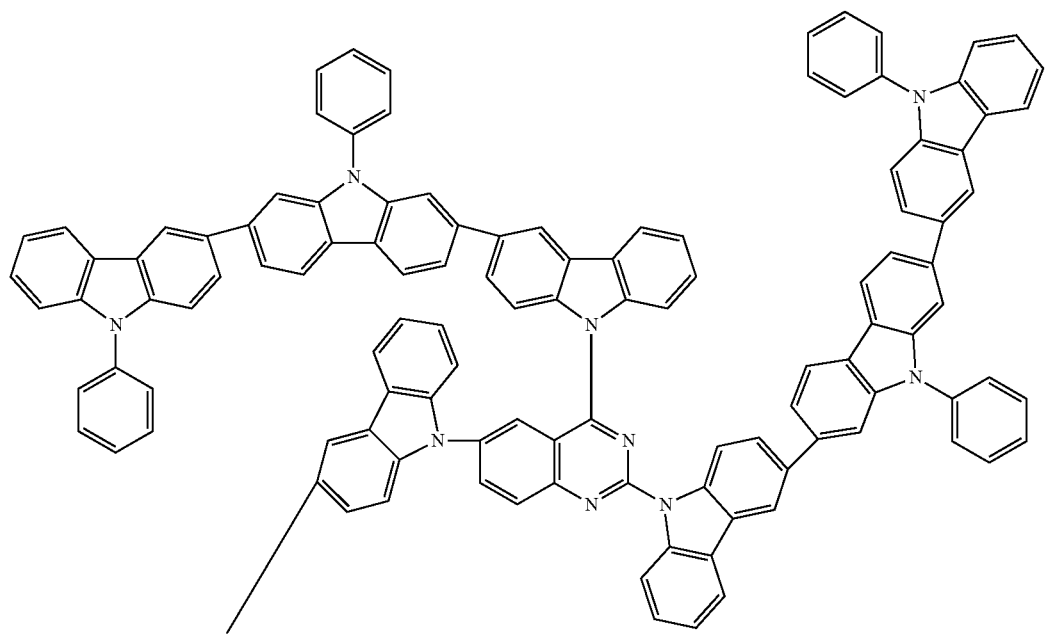
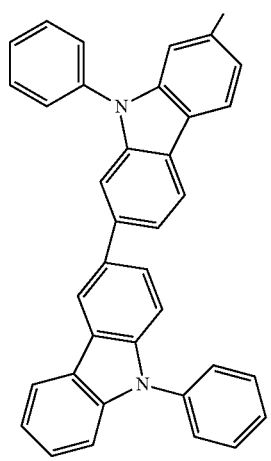

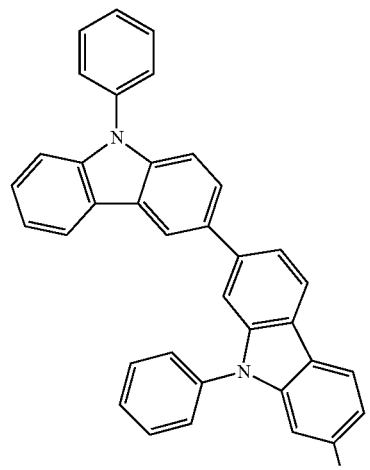
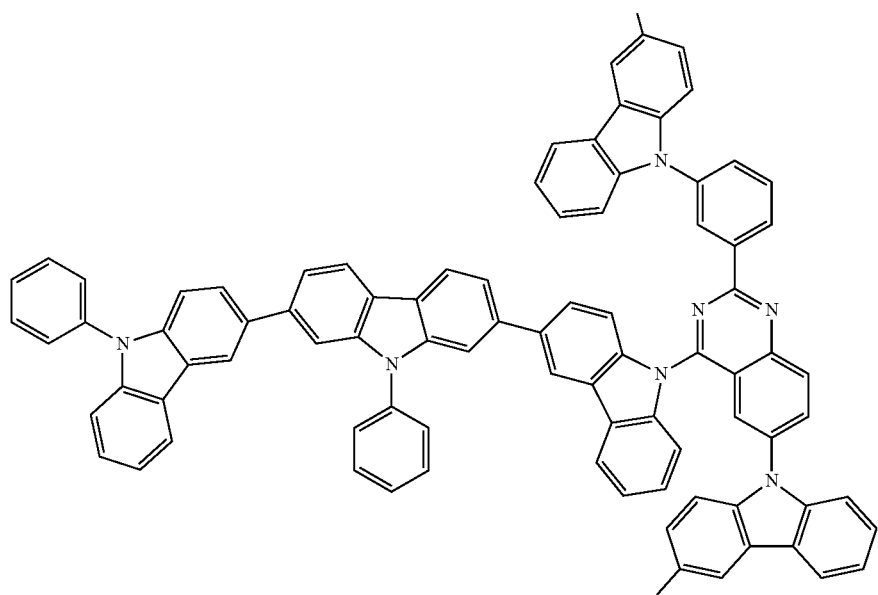
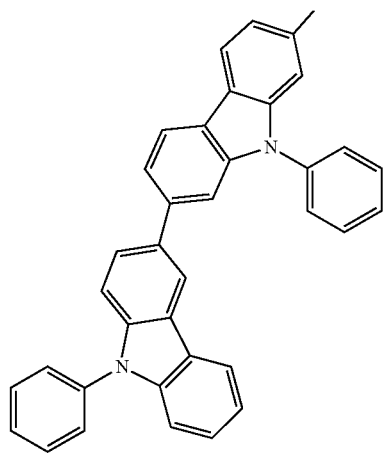

-continued
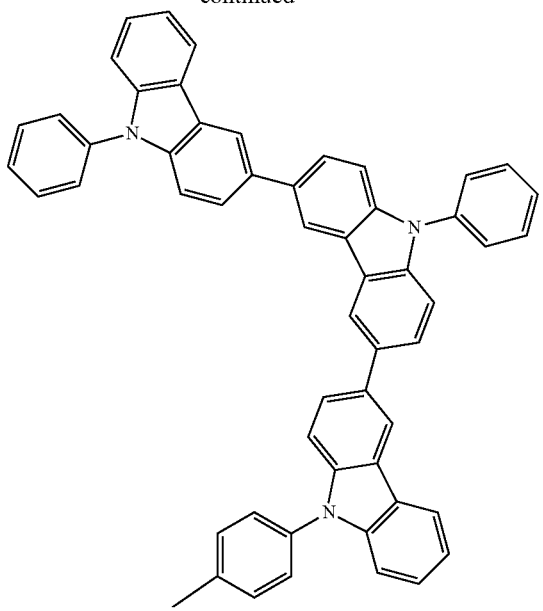
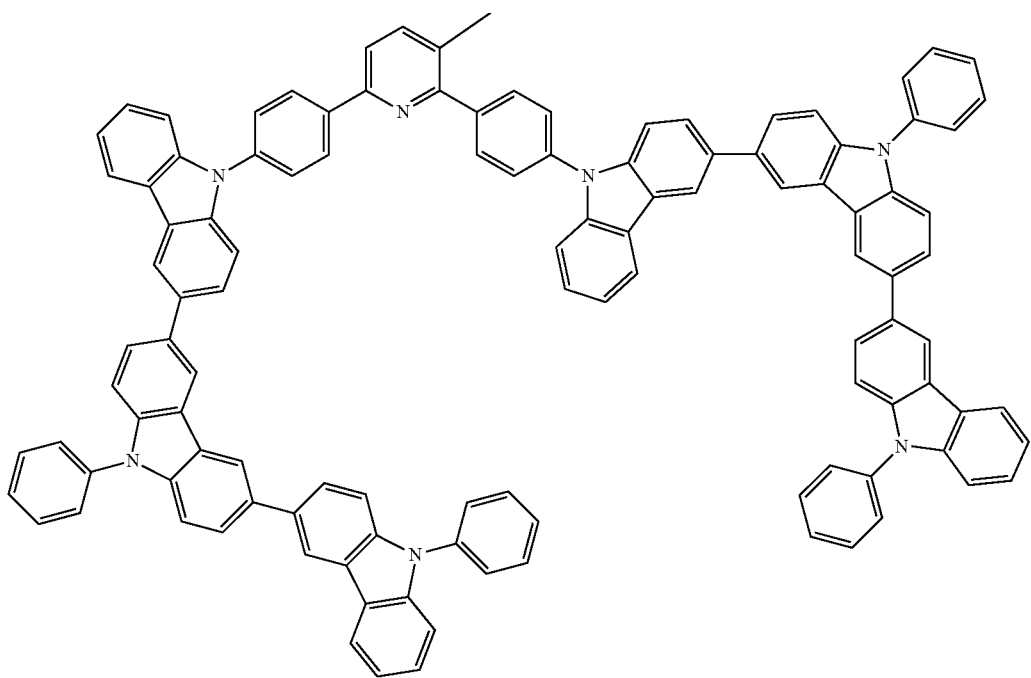
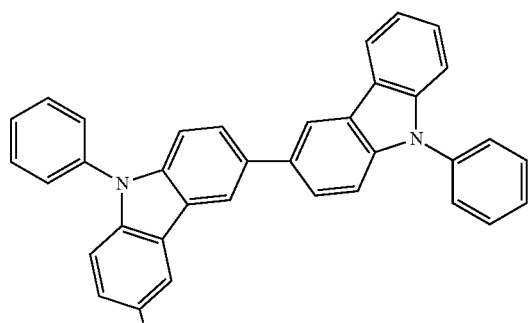

197 198
-continued
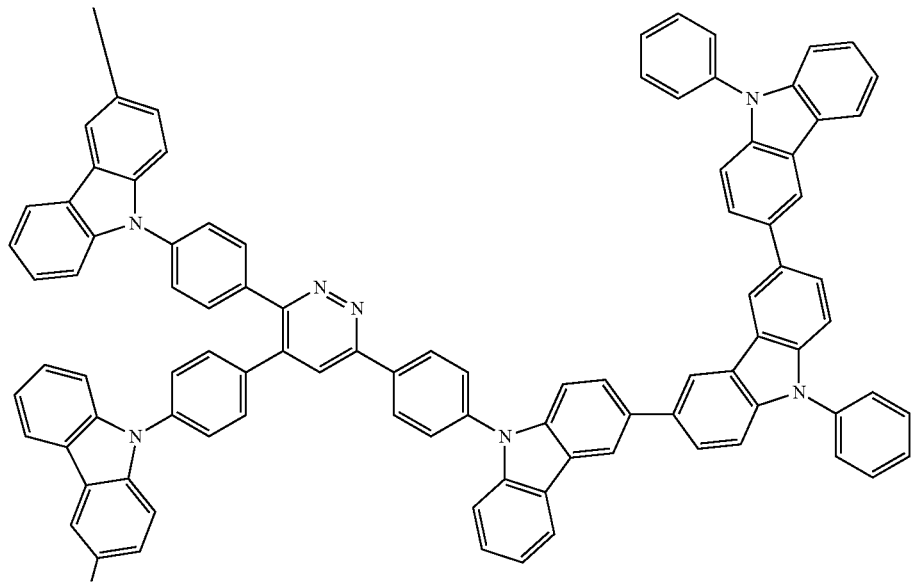
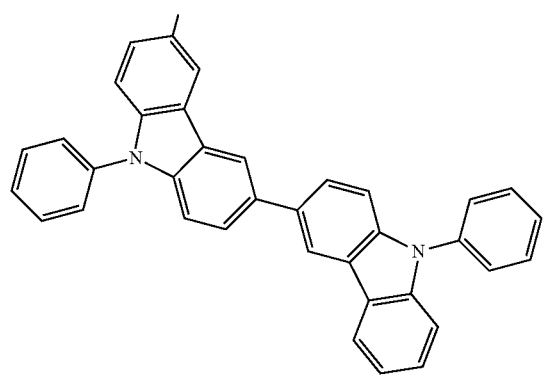
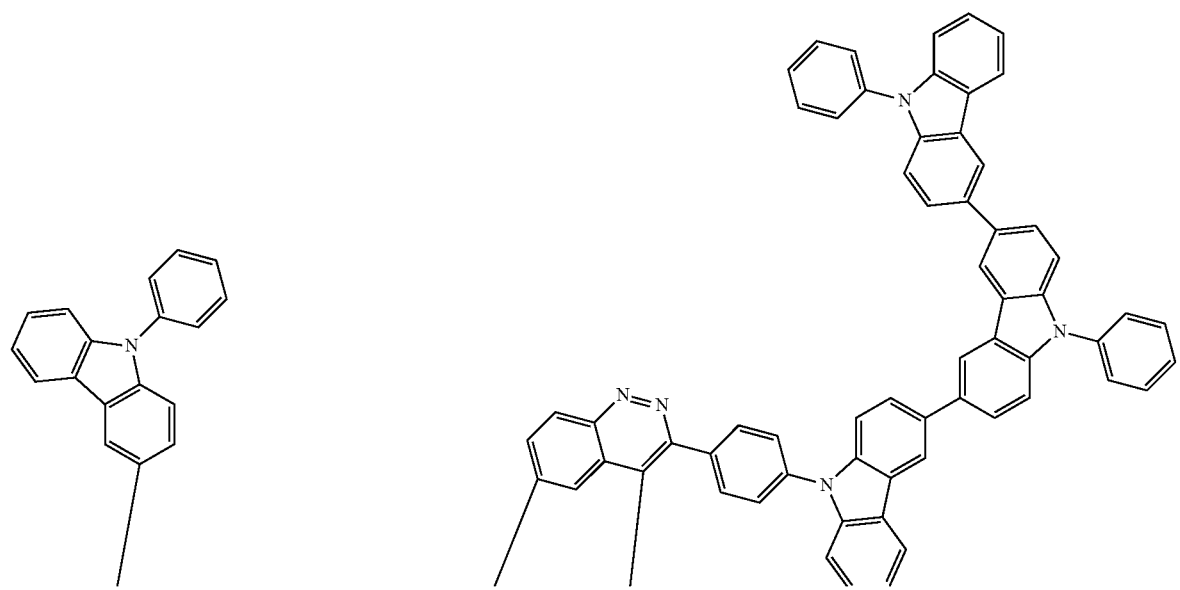

-continued
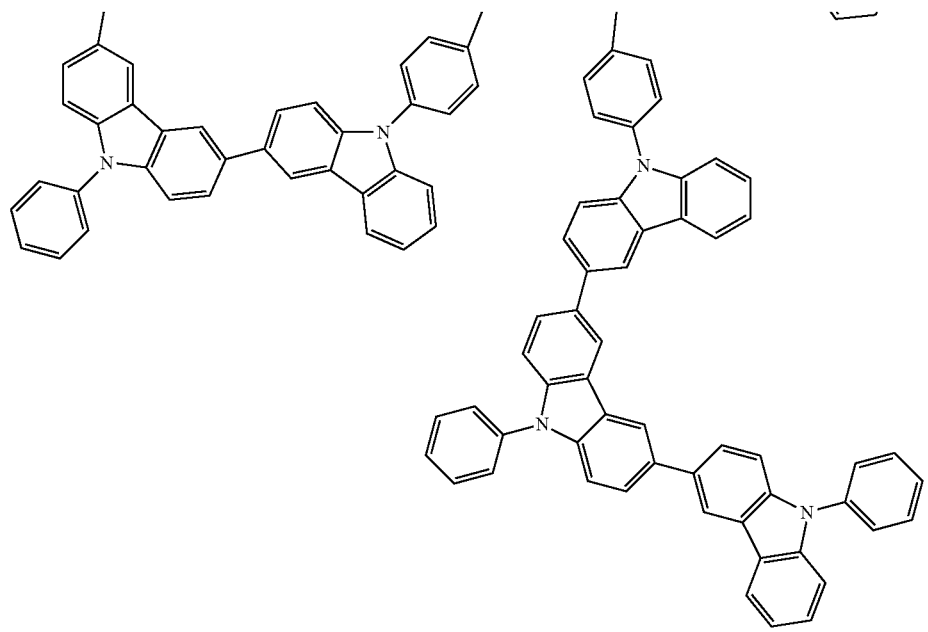
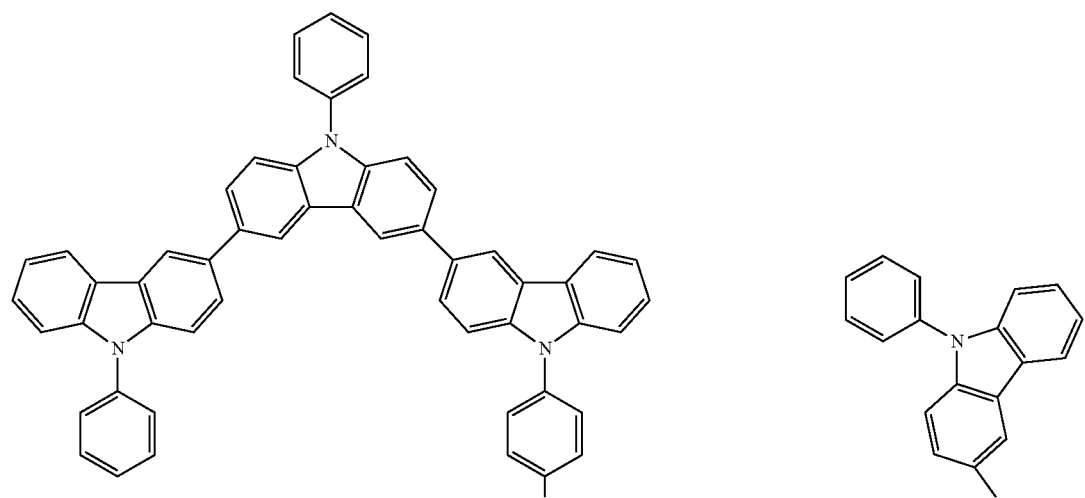

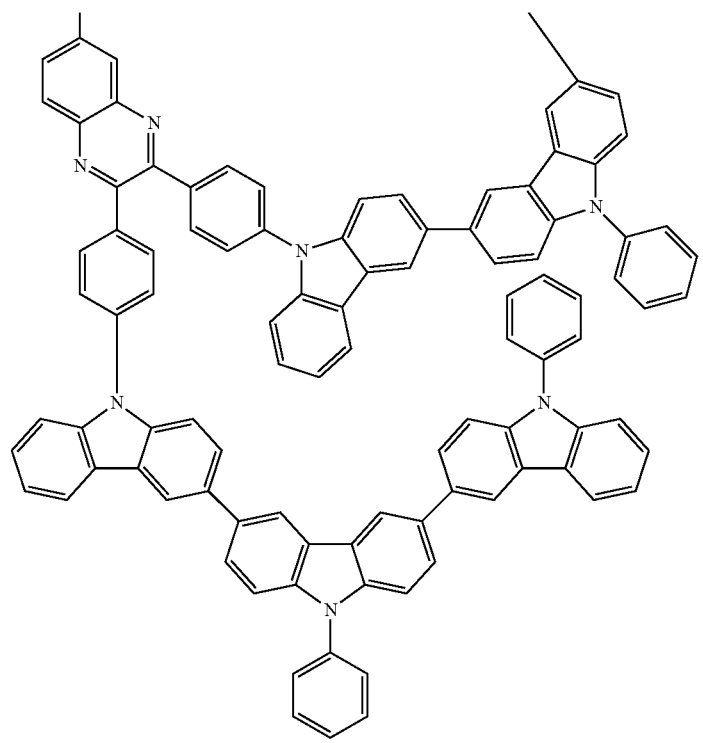
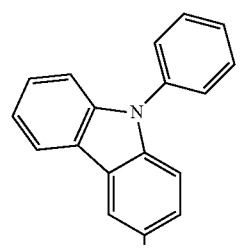
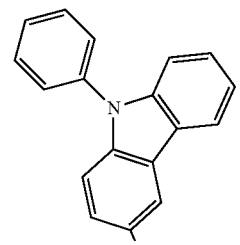
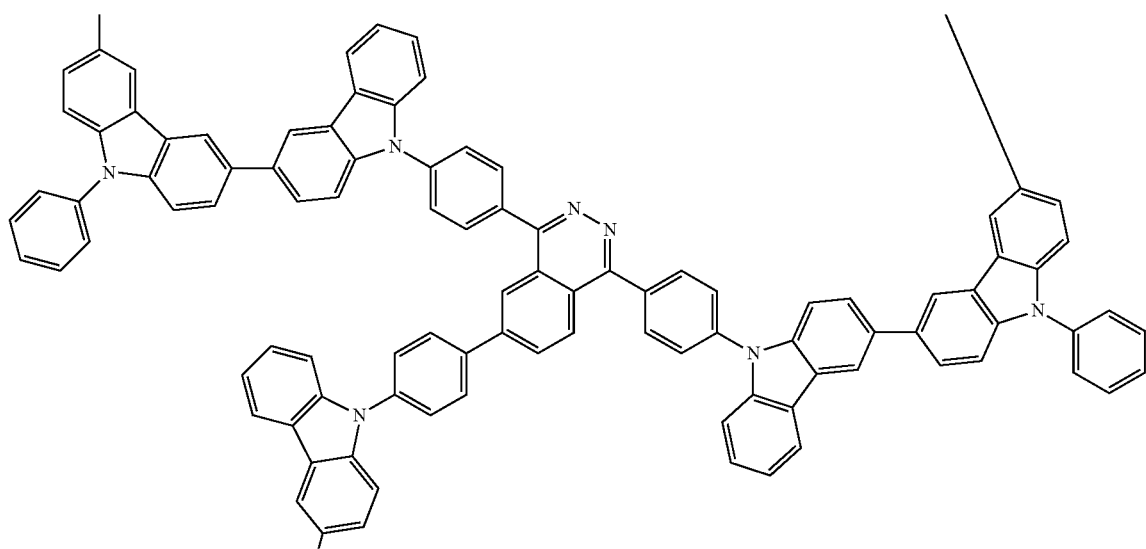

203
-continued
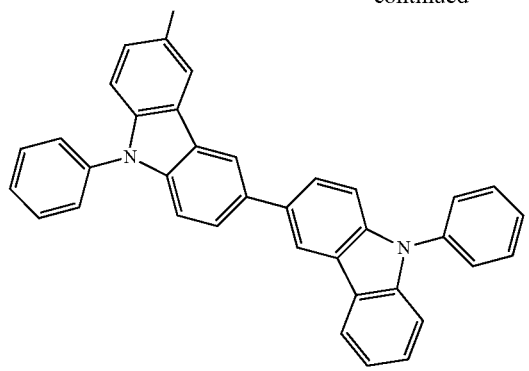
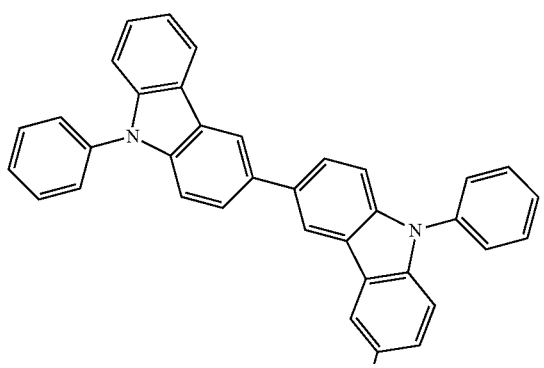
204
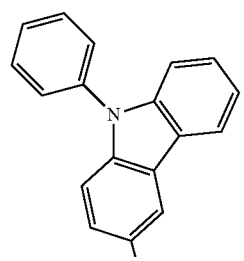
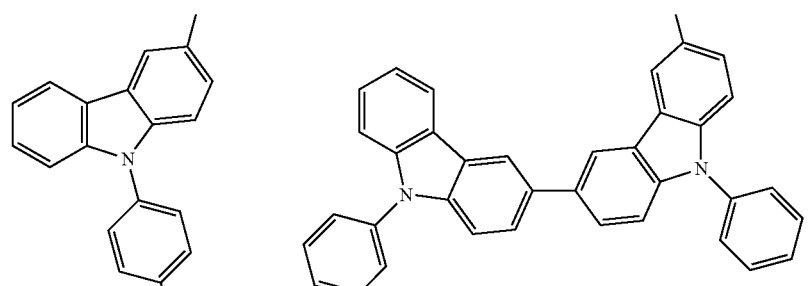
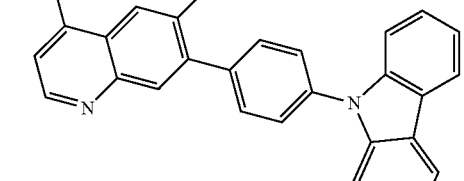
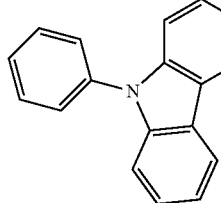

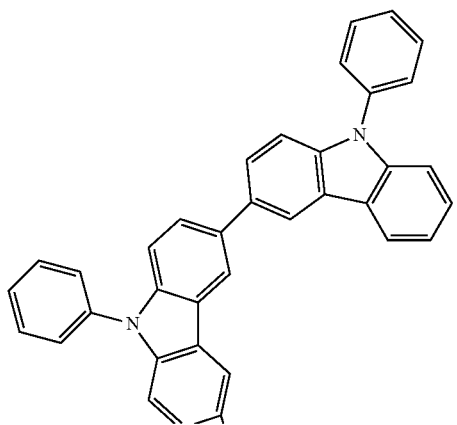
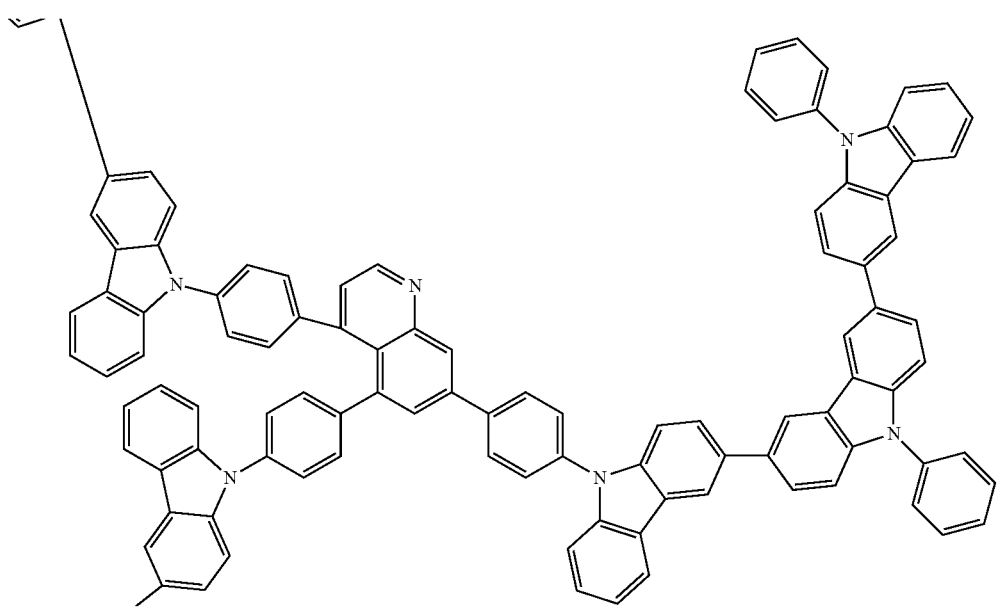
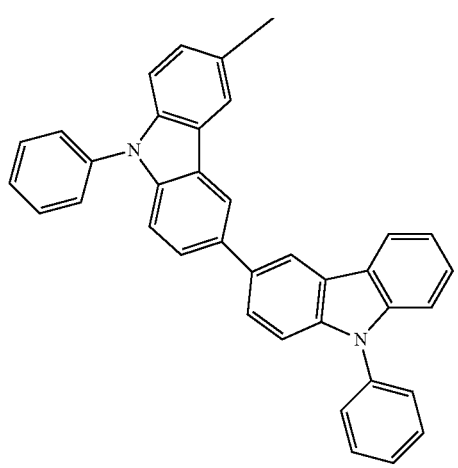

-continued
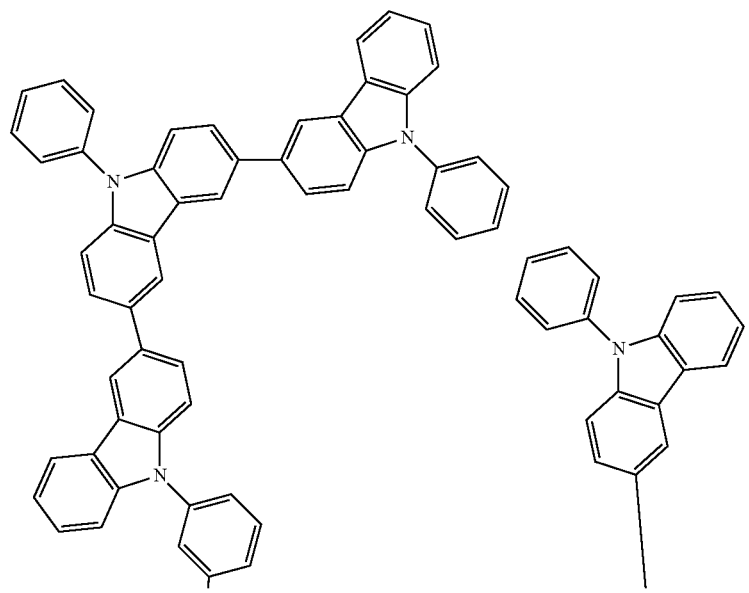
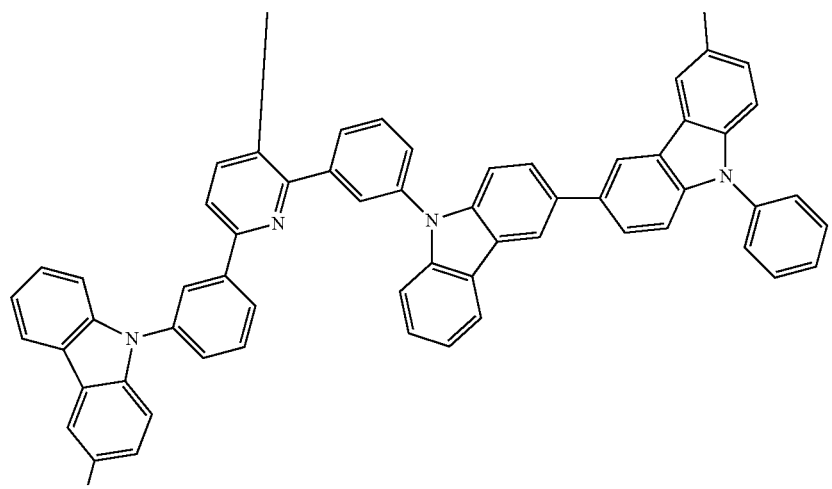
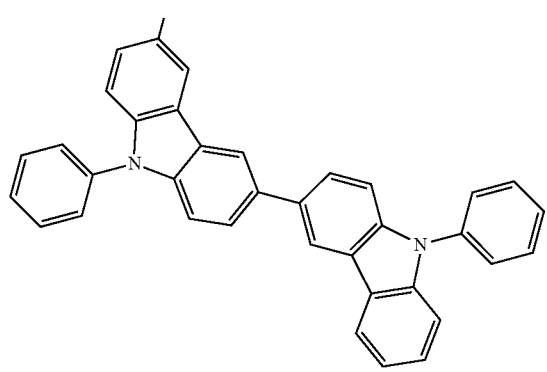

-continued
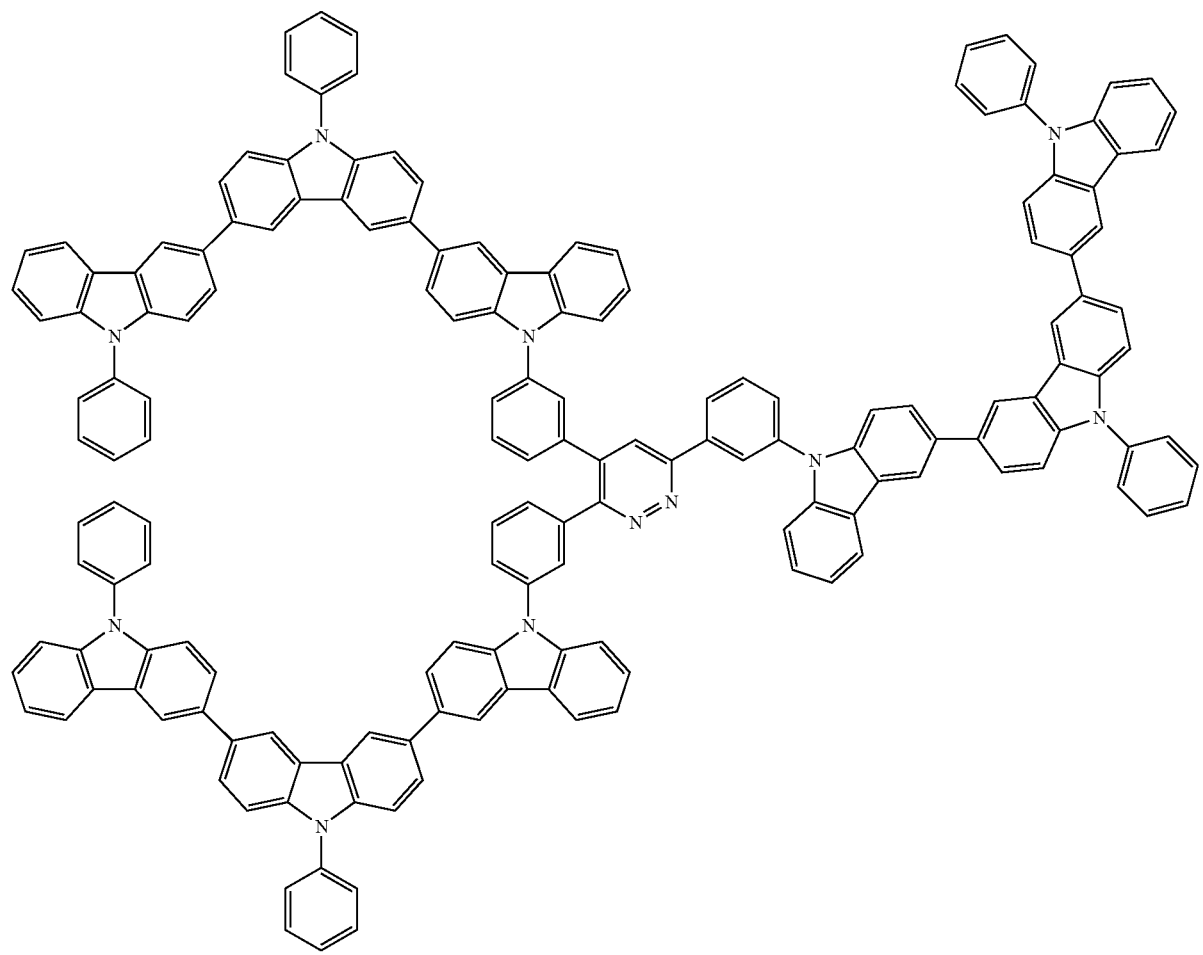

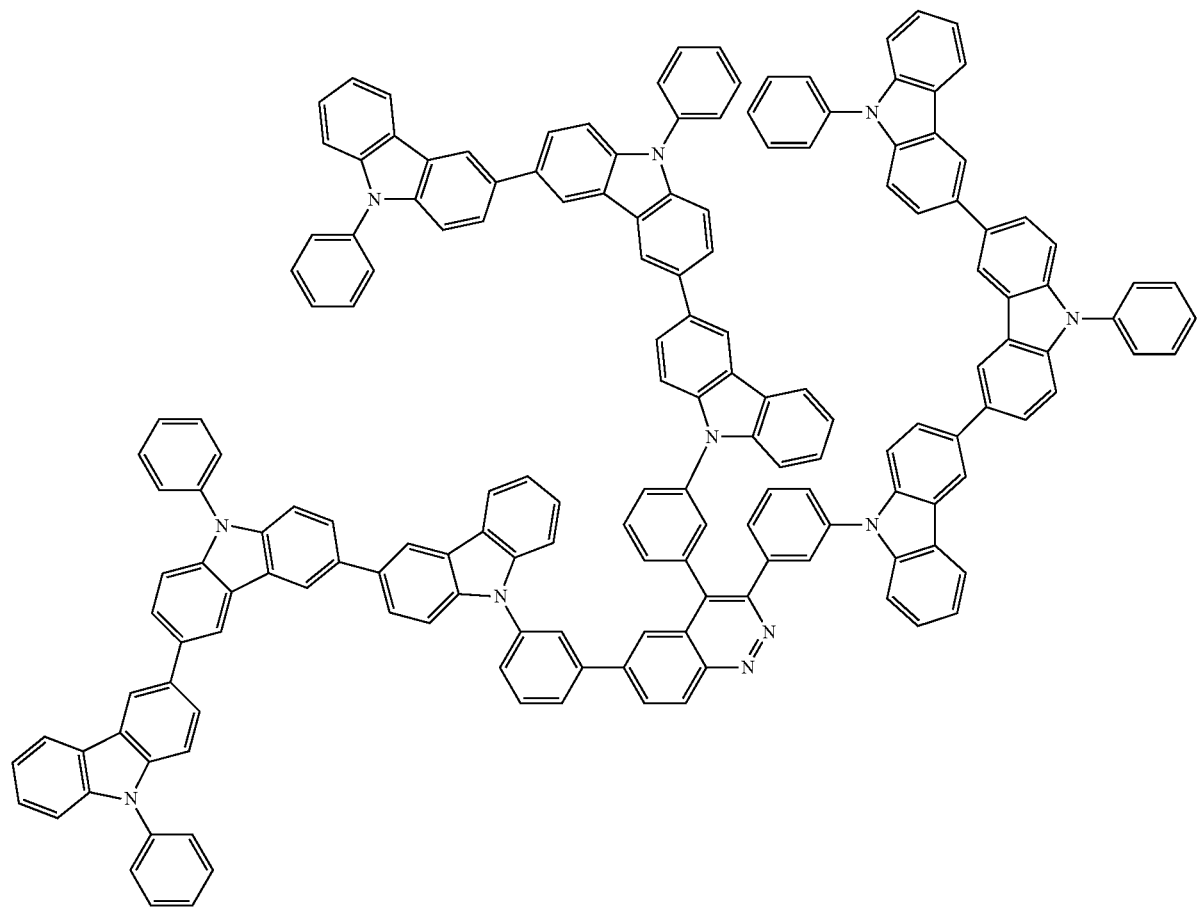
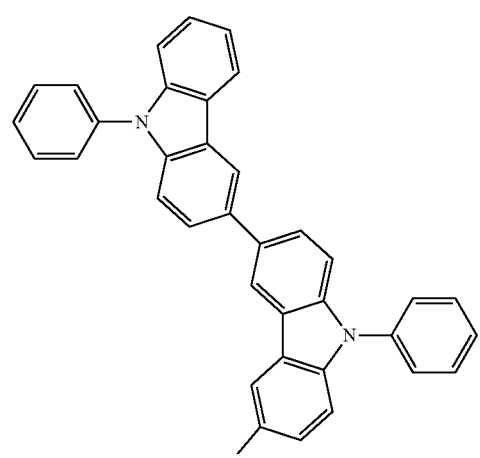

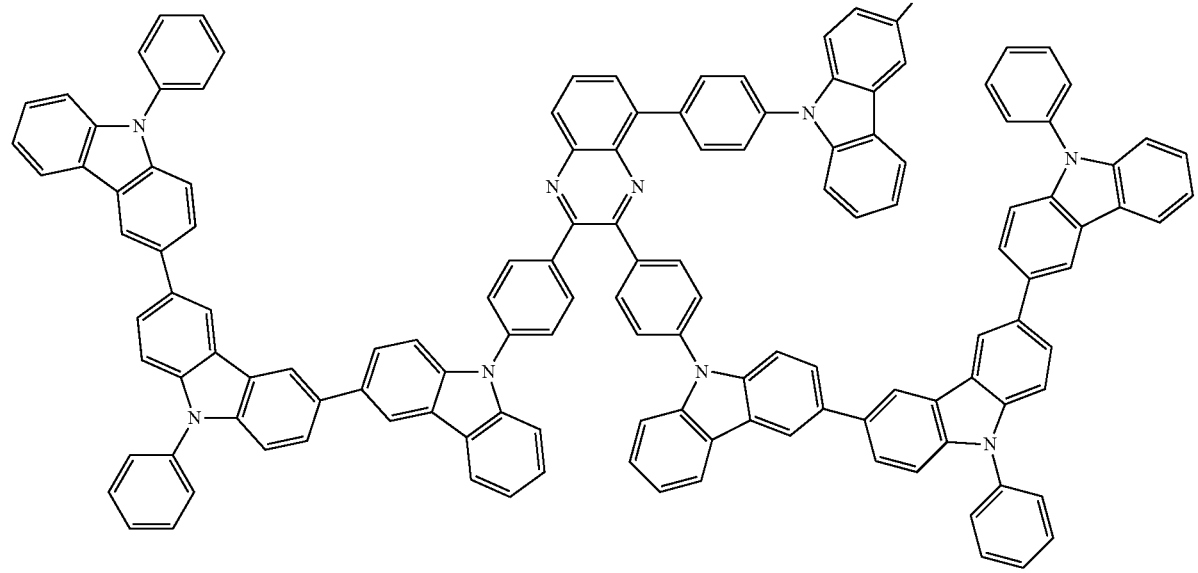
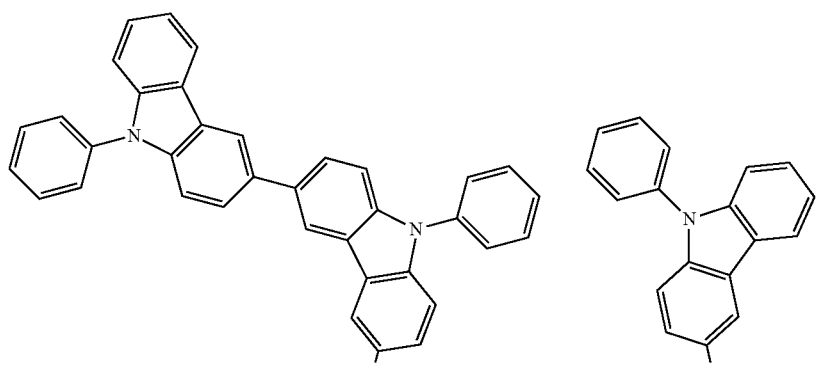
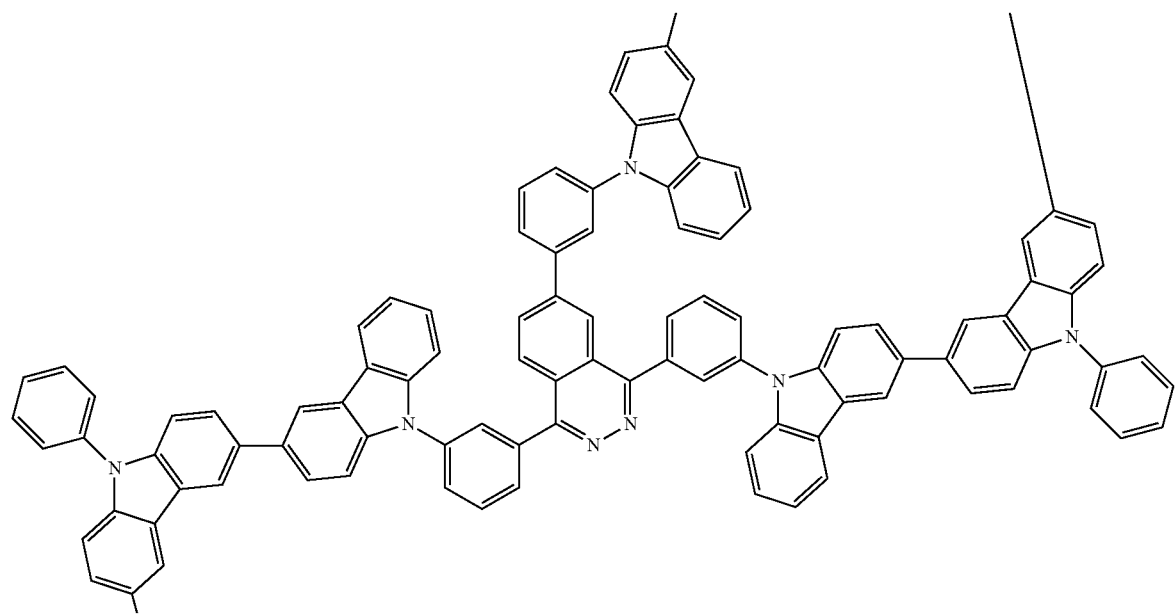

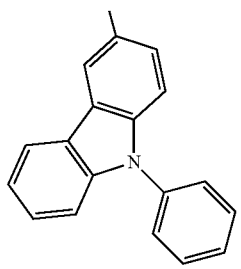
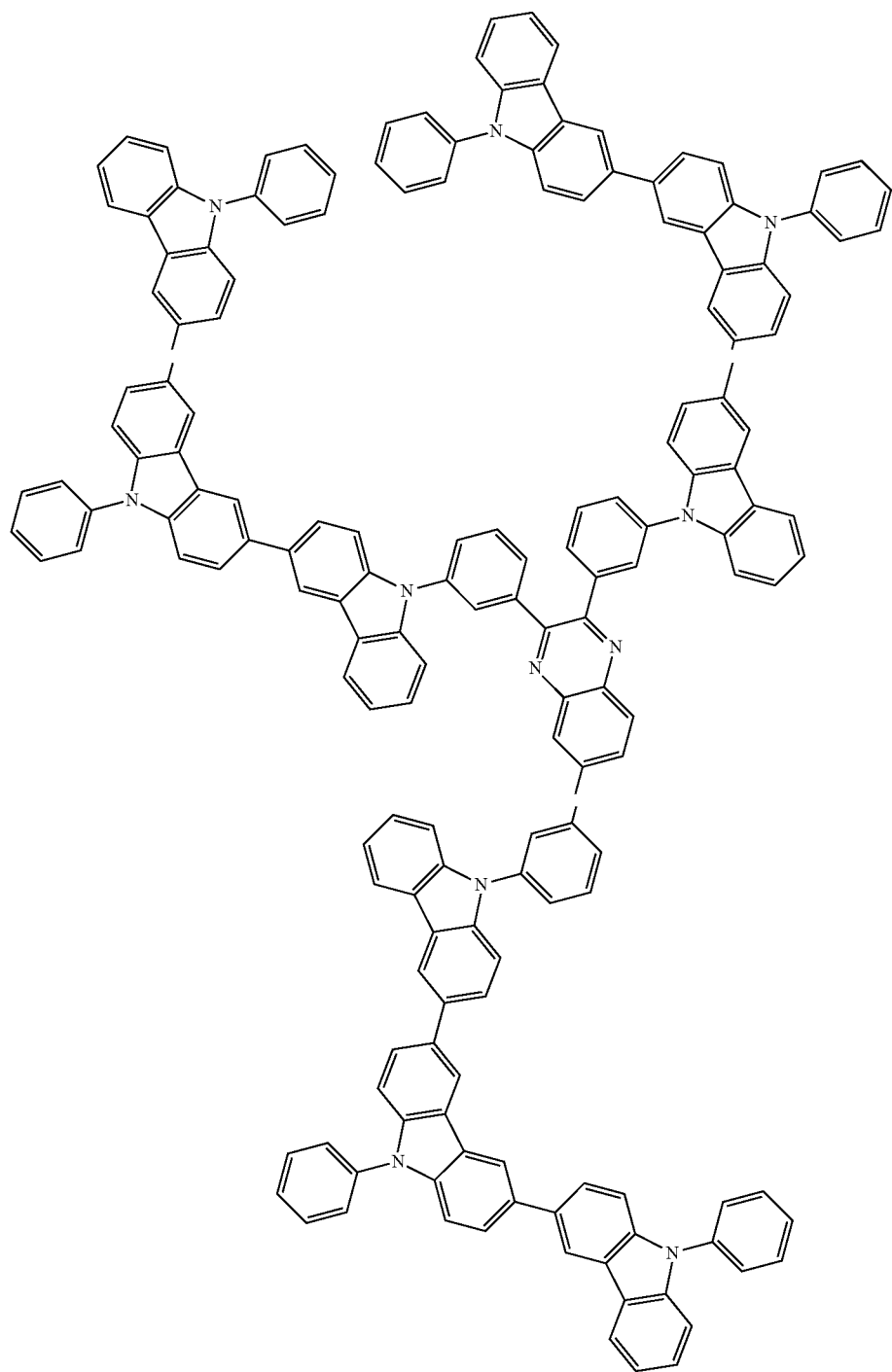 [SMILES: c1ccc(-n2c3ccccc3c3cc(-c4ccc5c(c4)c4cc(-c6ccc7c(c6)c6ccccc6n7-c6cccc(-c7ccc8nc(-c9cccc(-n%10c%11ccccc%11c%11cc(-c%12ccc%13c(c%12)c%12cc(-c%14ccc%15c(c%14)c%14ccccc%14n%15-c%14ccccc%14)ccc%12n%13-c%12ccccc%12)ccc%11%10)c9)c(-c9cccc(-n%10c%11ccccc%11c%11cc(-c%12ccc%13c(c%12)c%12cc(-c%14ccc%15c(c%14)c%14ccccc%14n%15-c%14ccccc%14)ccc%12n%13-c%12ccccc%12)ccc%11%10)c9)nc8c7)c6)ccc4n5-c4ccccc4)ccc32)cc1]

-continued
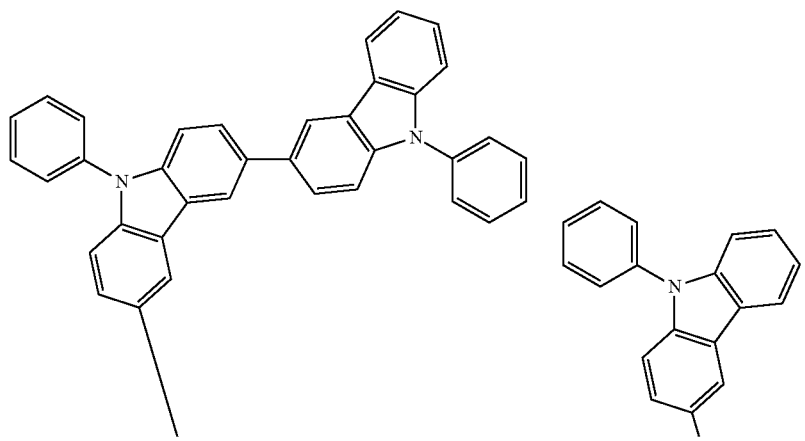
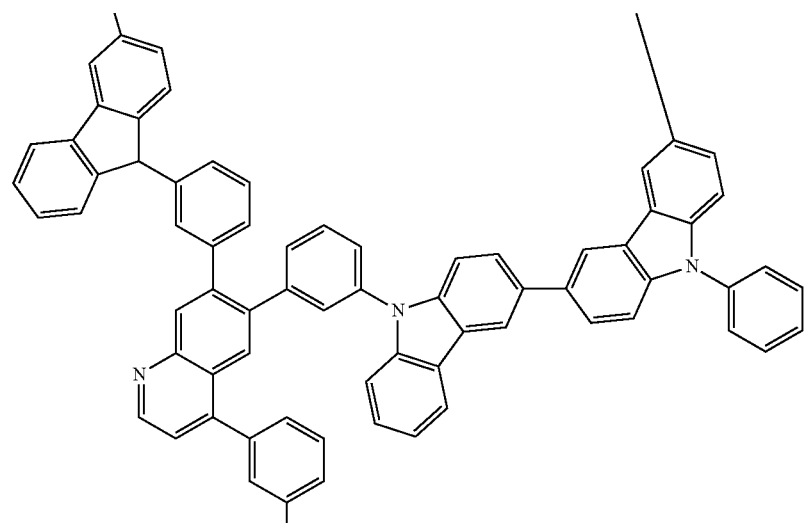
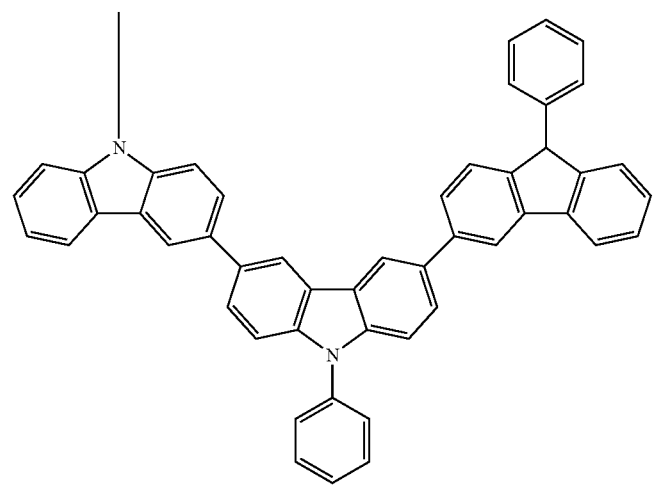

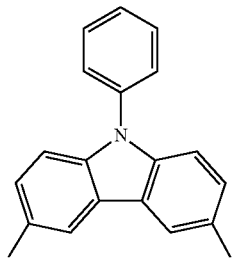
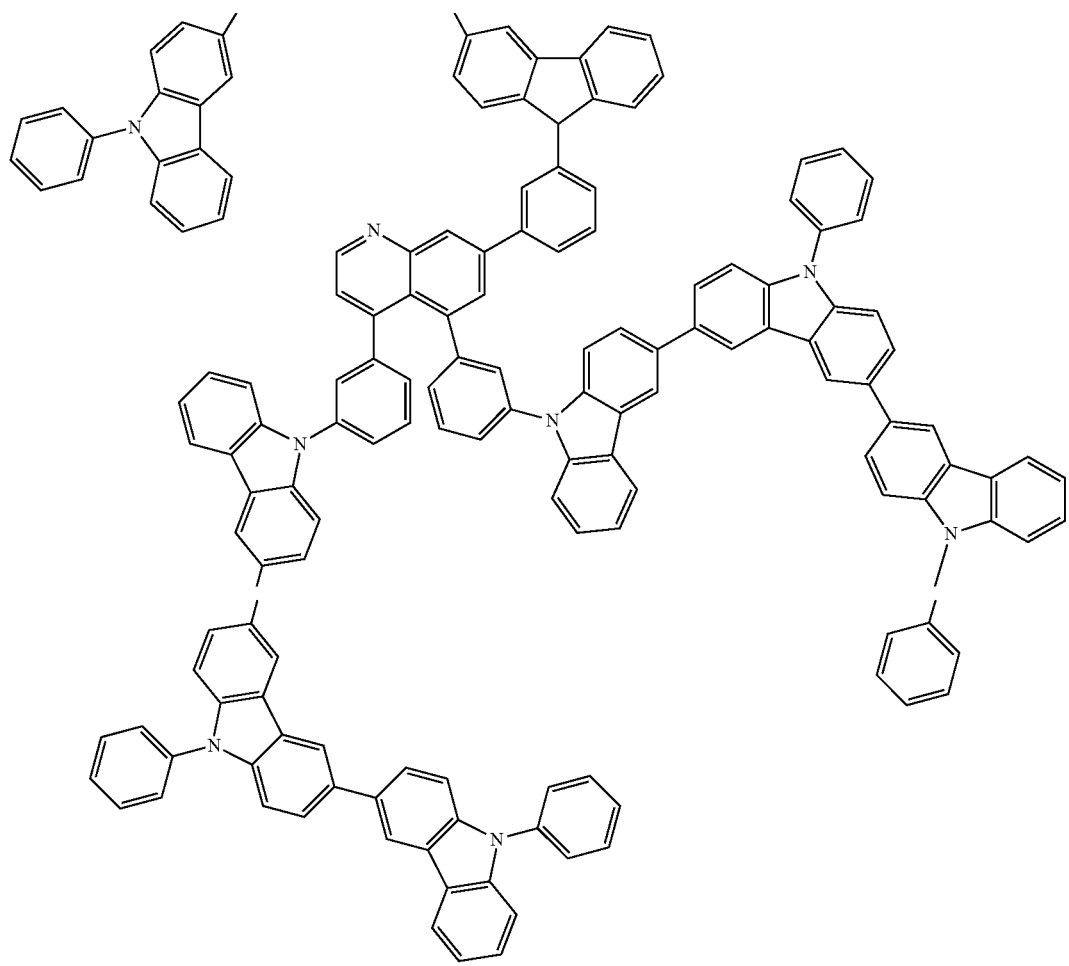

221 222
-continued
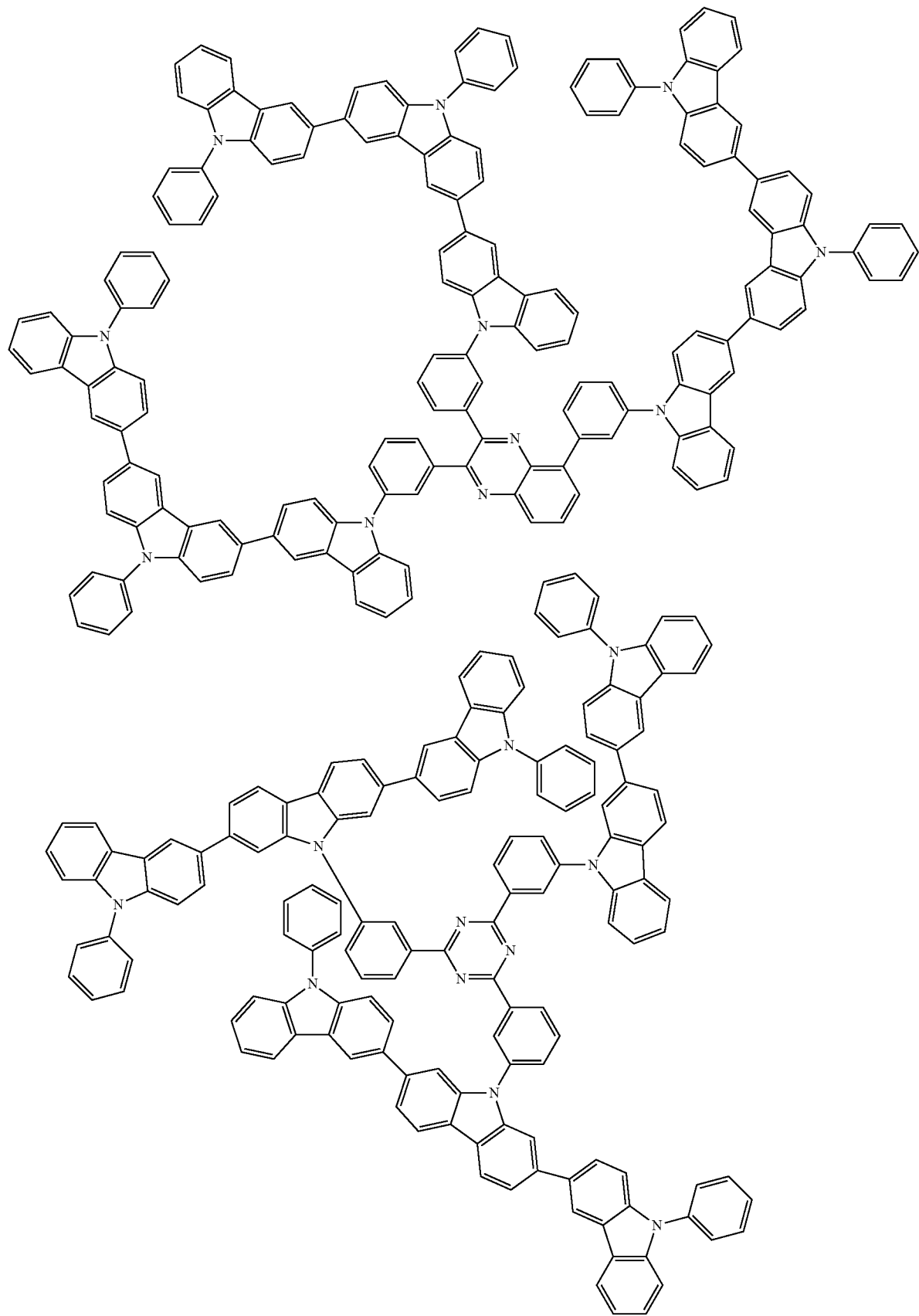

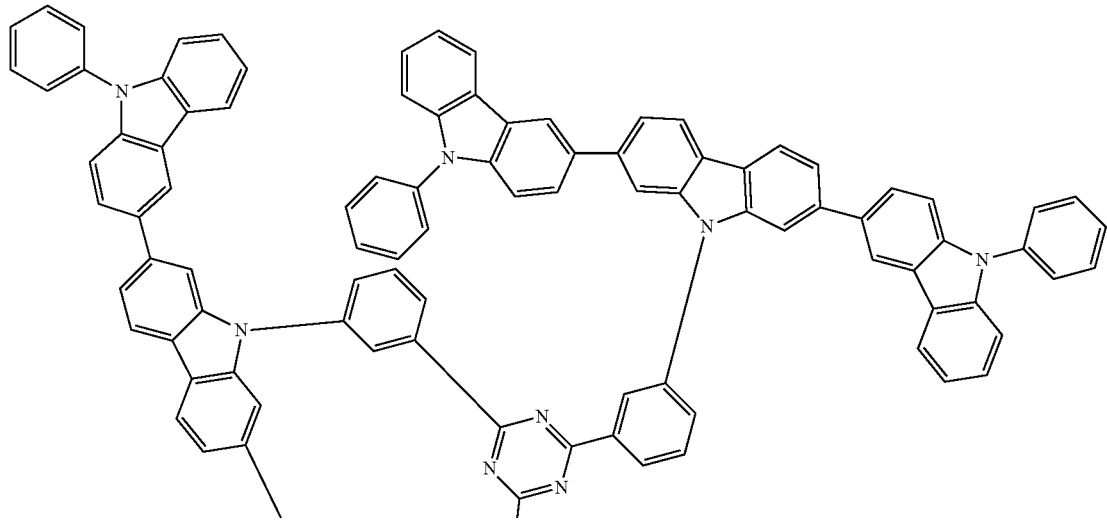
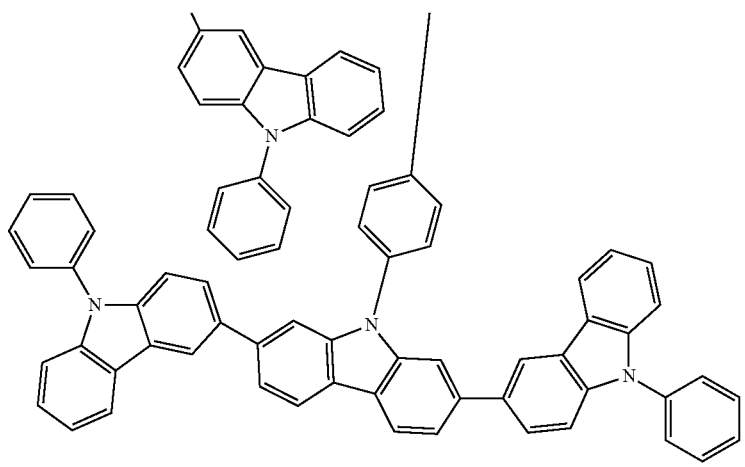
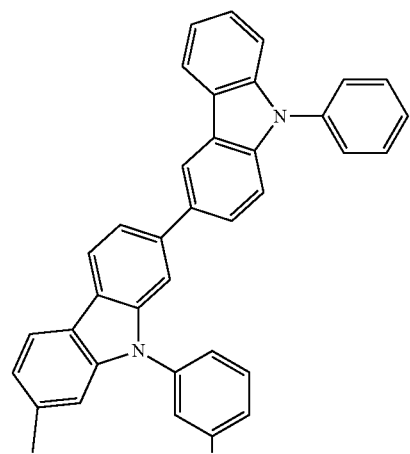

225 226
-continued
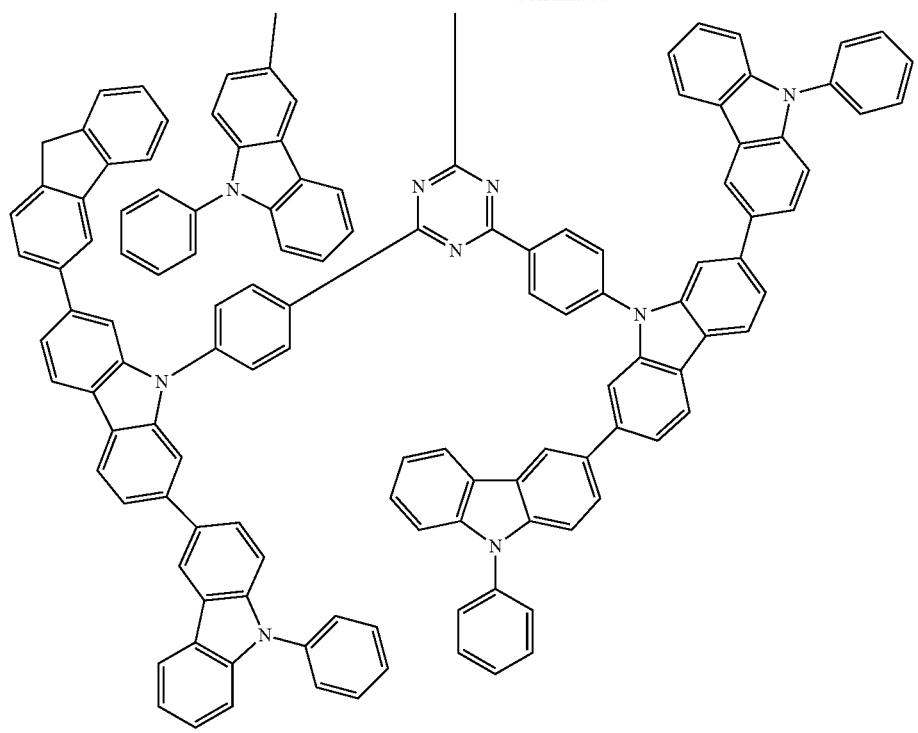
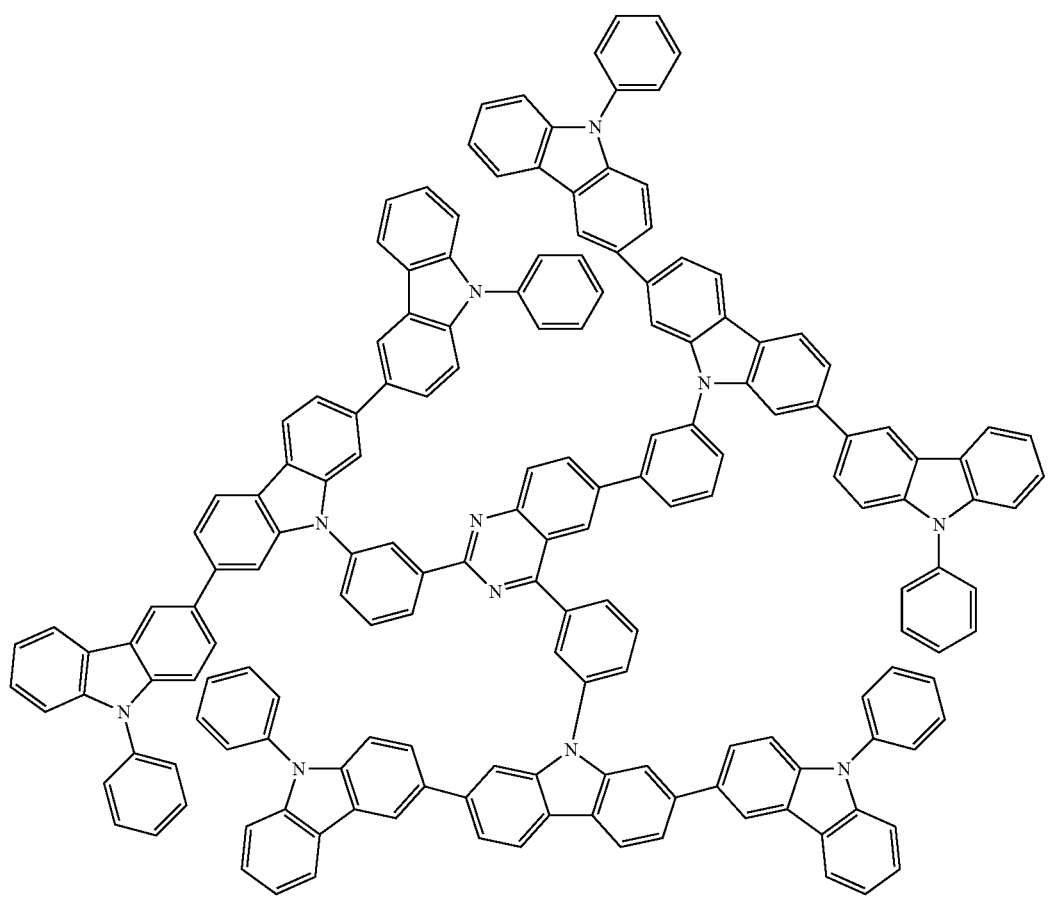

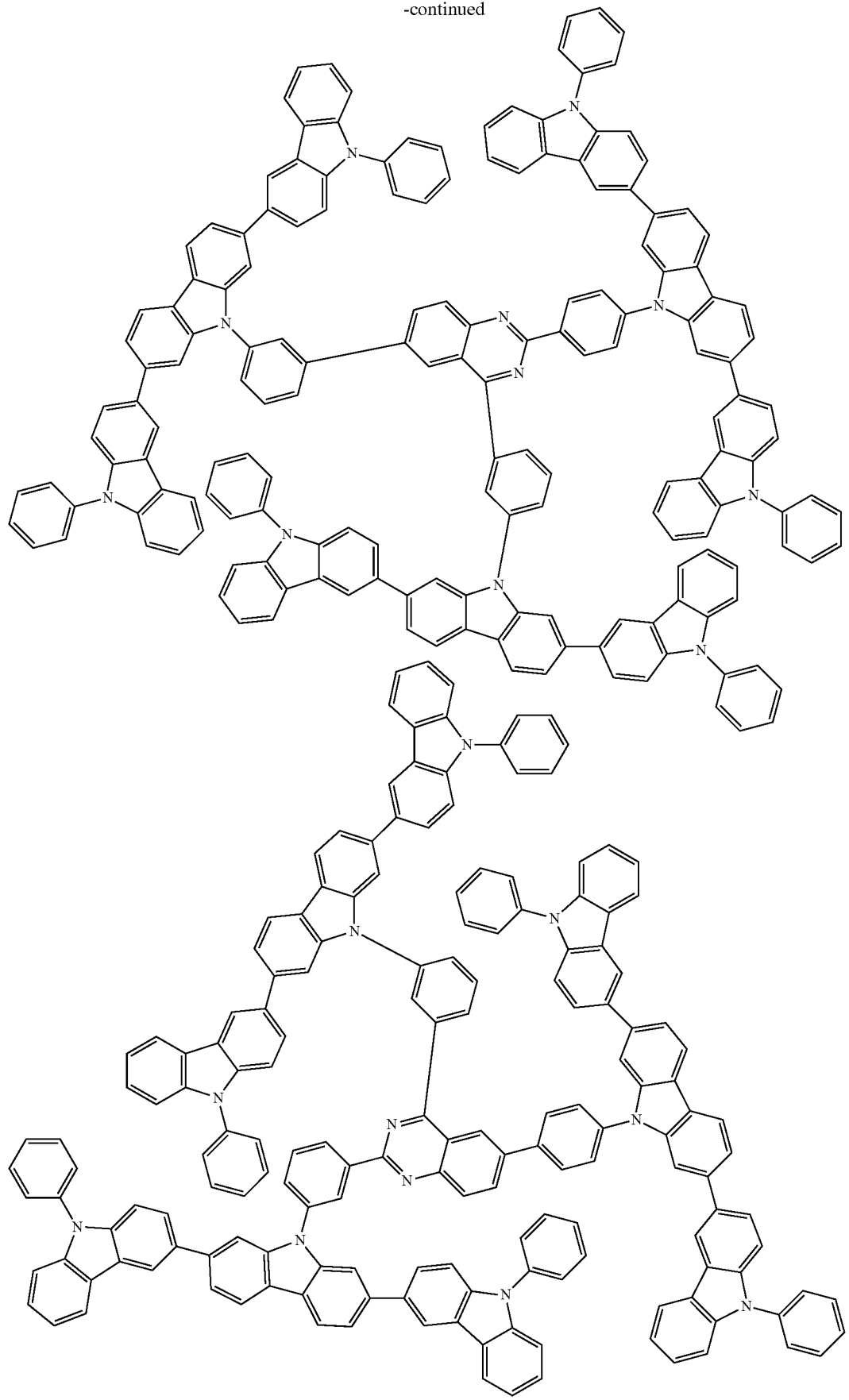

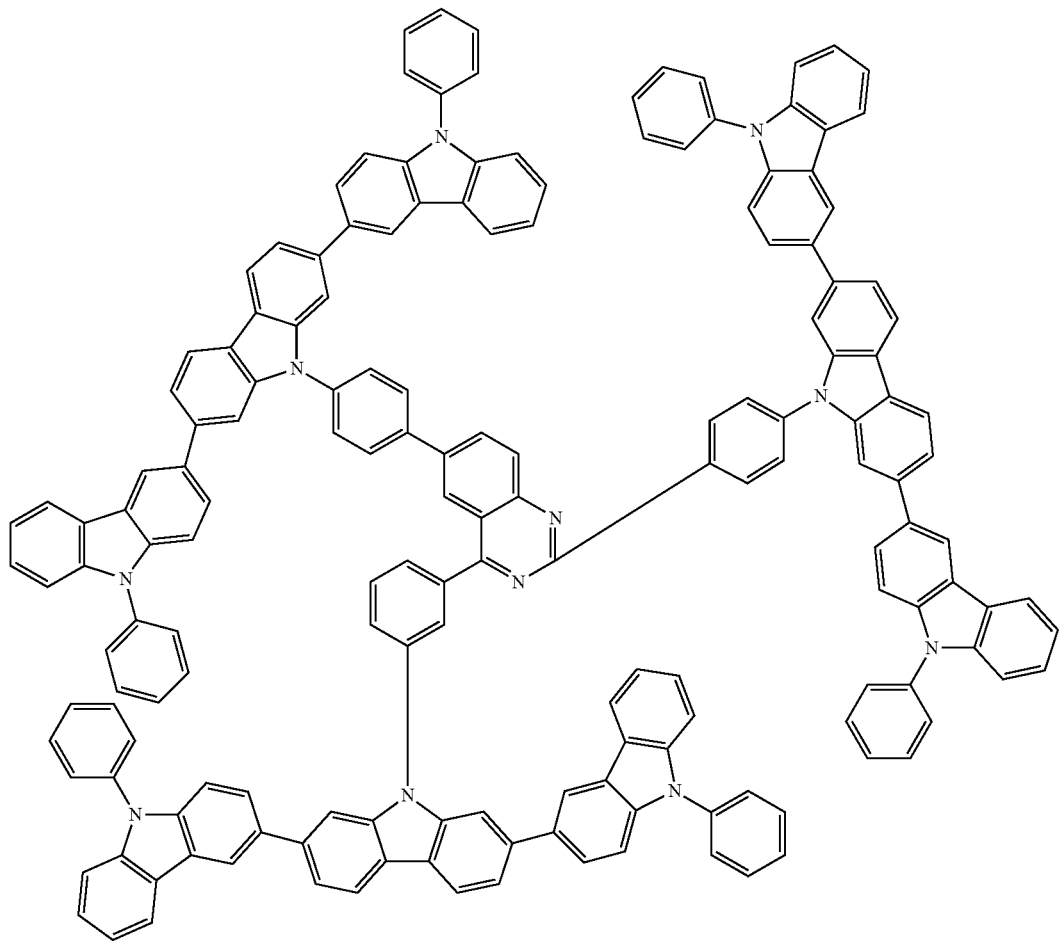
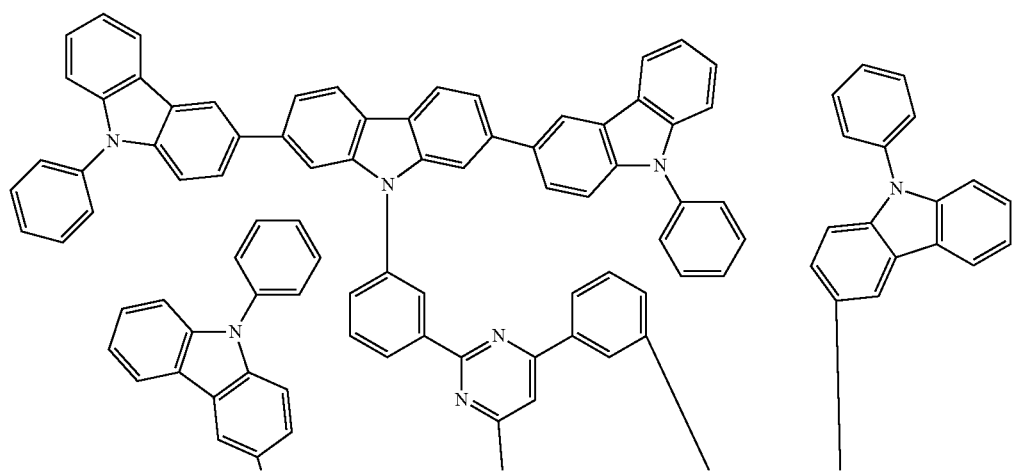

231    232
-continued
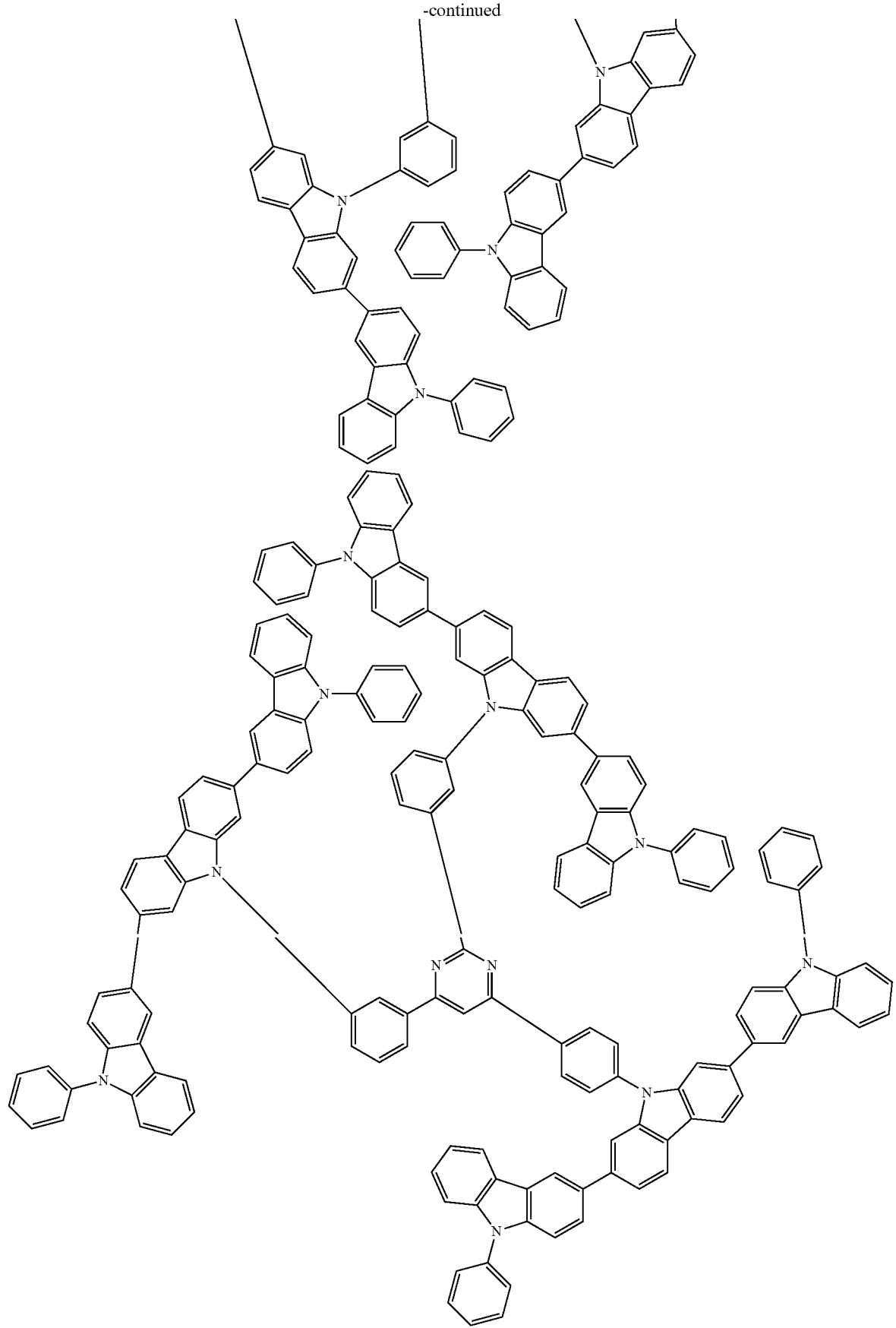

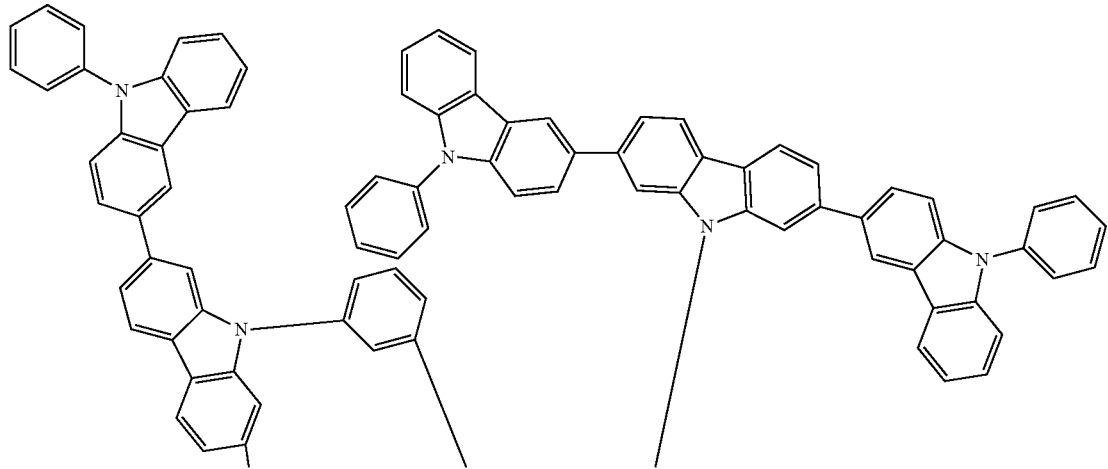
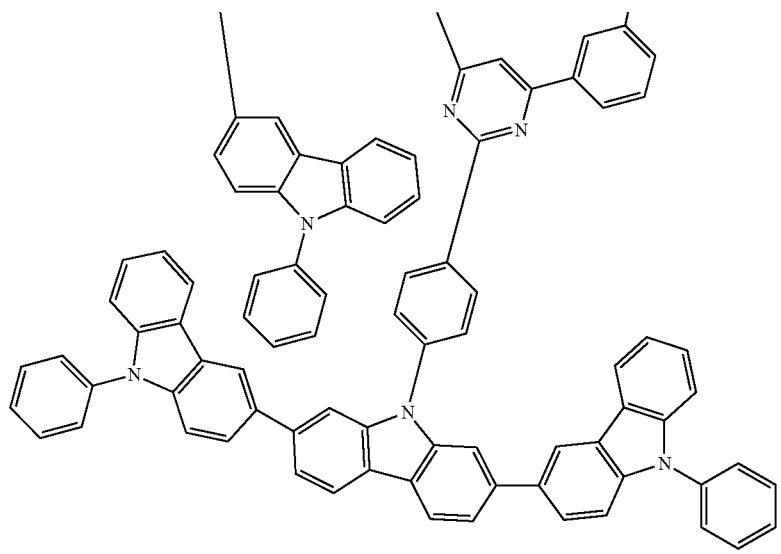
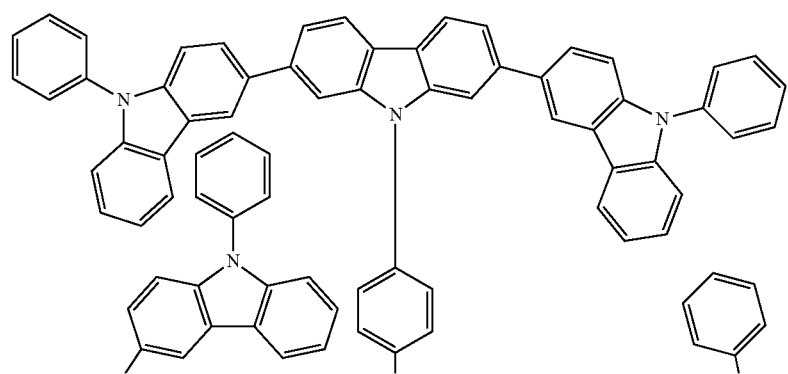

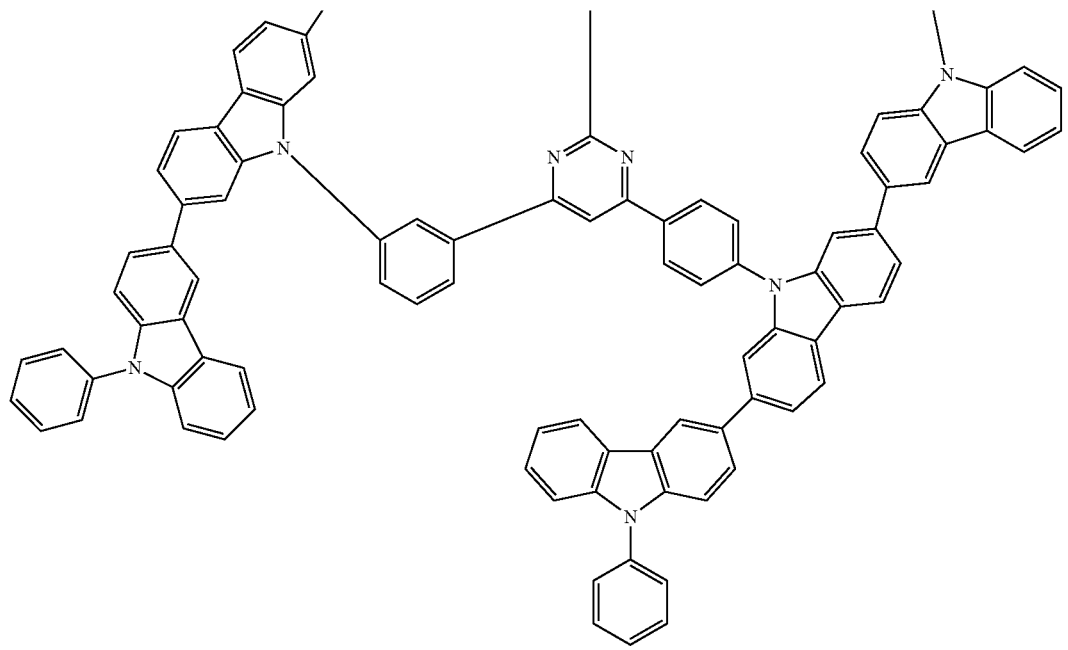
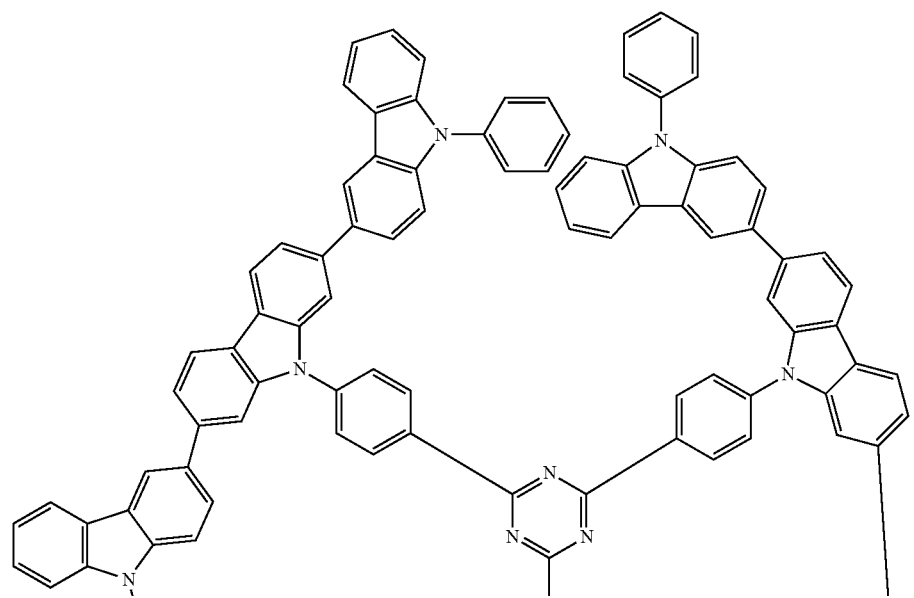

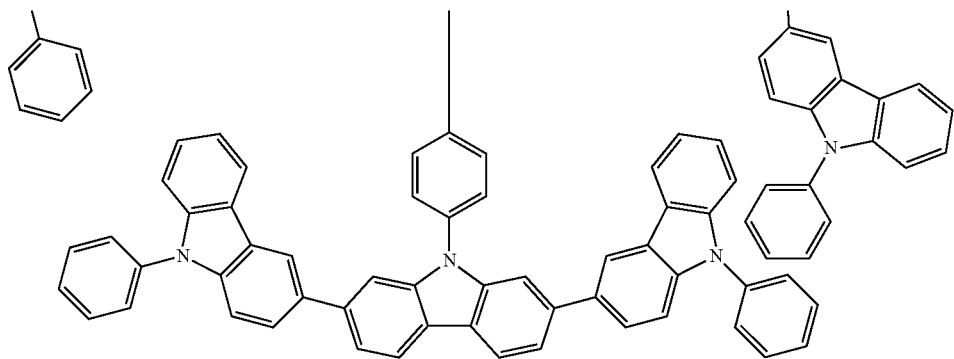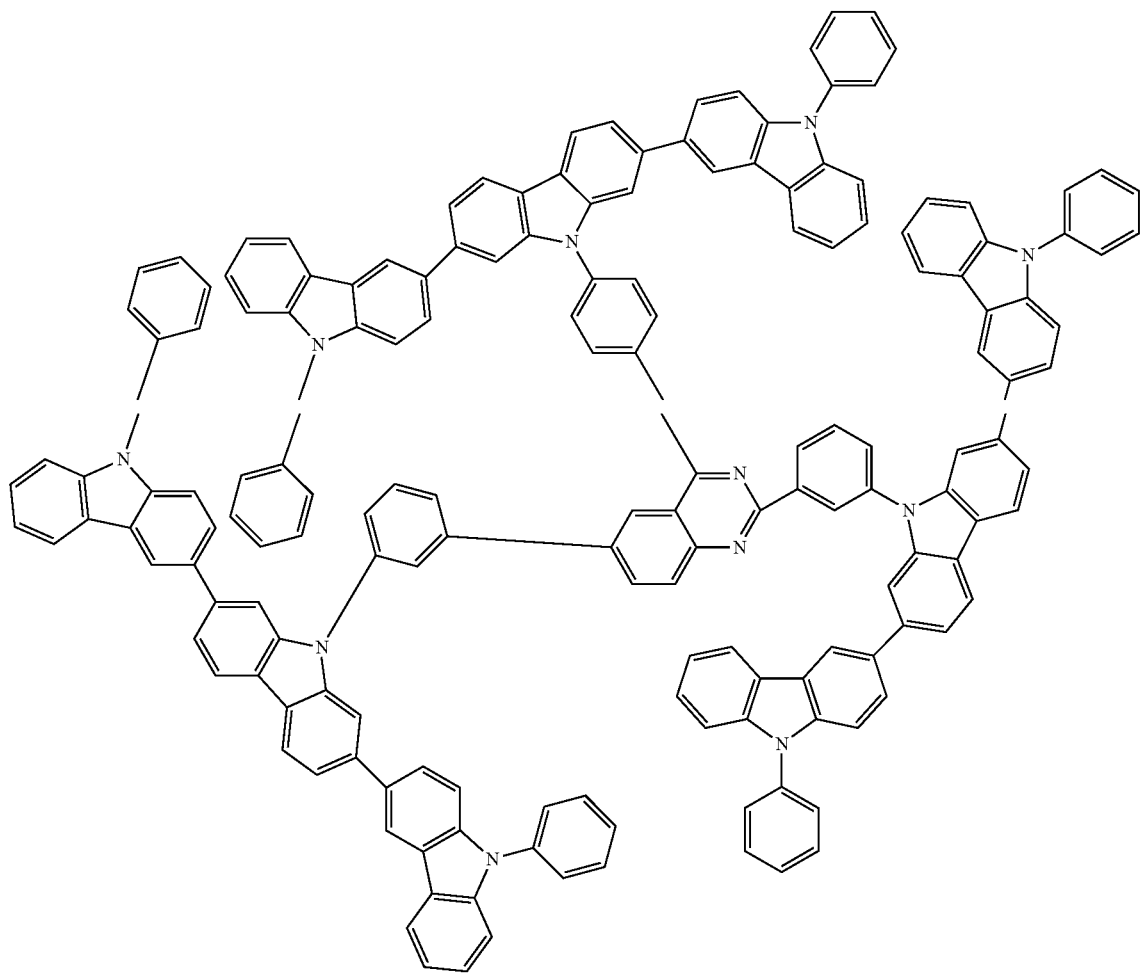 [SMILES: c1ccc(-n2c3ccccc3c3cc(-c4ccc5c6ccc(-c7ccc8c(c7)c7ccccc7n8-c7ccccc7)cc6n(-c6ccc(-c7nc(-c8cccc(-n9c%10cc(-c%11ccc%12c(c%11)c%11ccccc%11n%12-c%11ccccc%11)ccc%10c%10ccc(-c%11ccc%12c(c%11)c%11ccccc%11n%12-c%11ccccc%11)cc%109)c8)nc8ccc(-c9cccc(-n%10c%11cc(-c%12ccc%13c(c%12)c%12ccccc%12n%13-c%12ccccc%12)ccc%11c%11ccc(-c%12ccc%13c(c%12)c%12ccccc%12n%13-c%12ccccc%12)cc%11%10)c9)cc78)cc6)c5c4)ccc32)cc1]

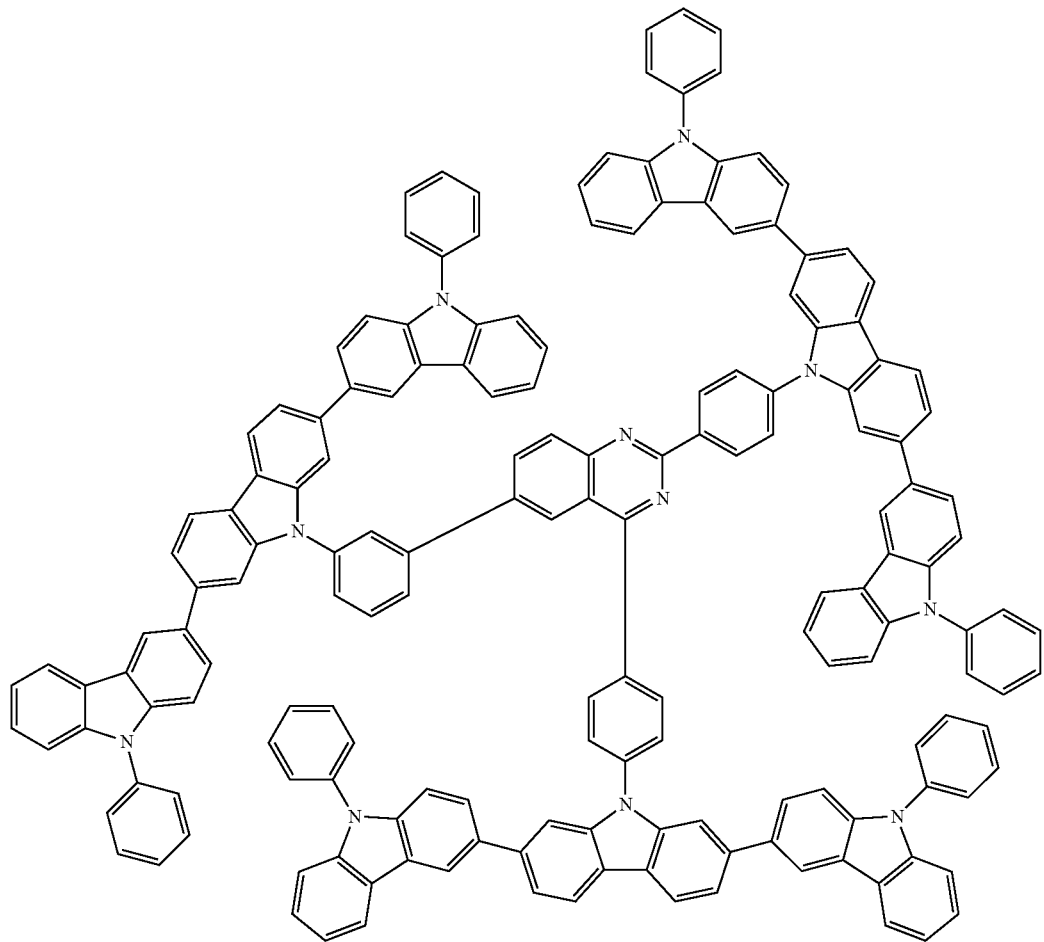

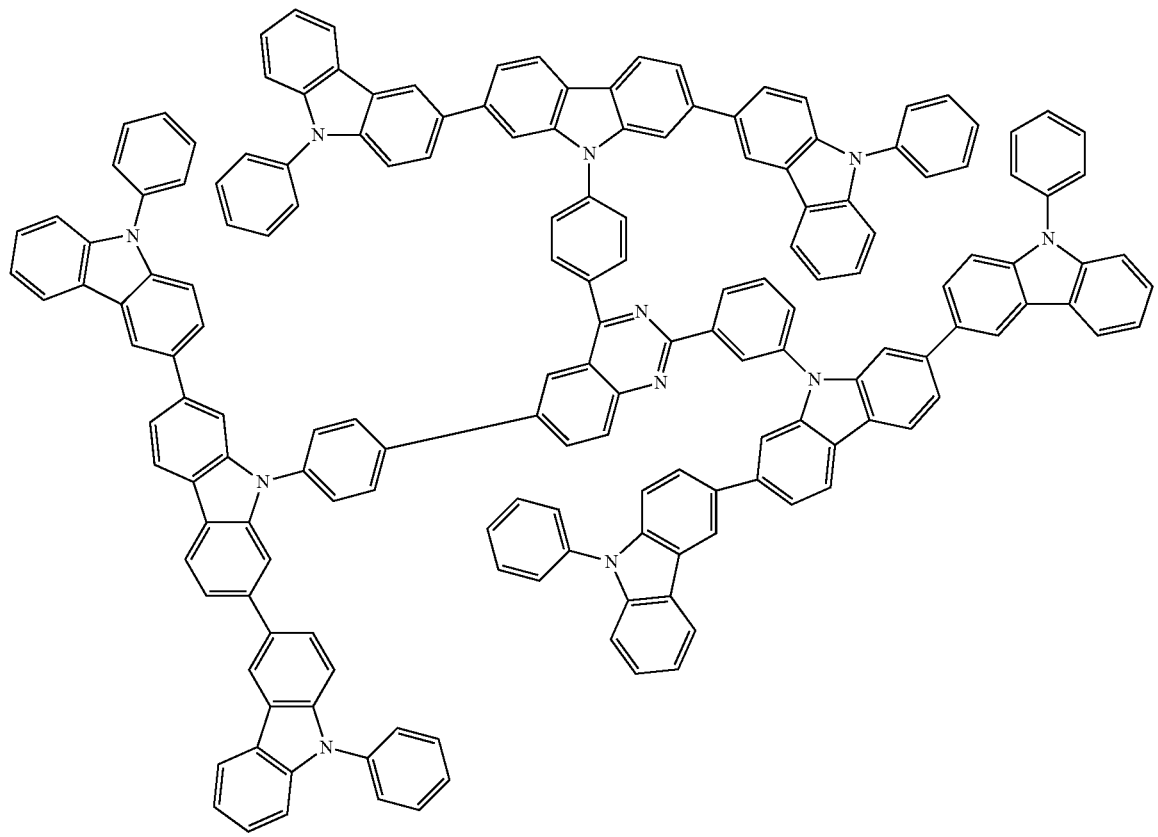
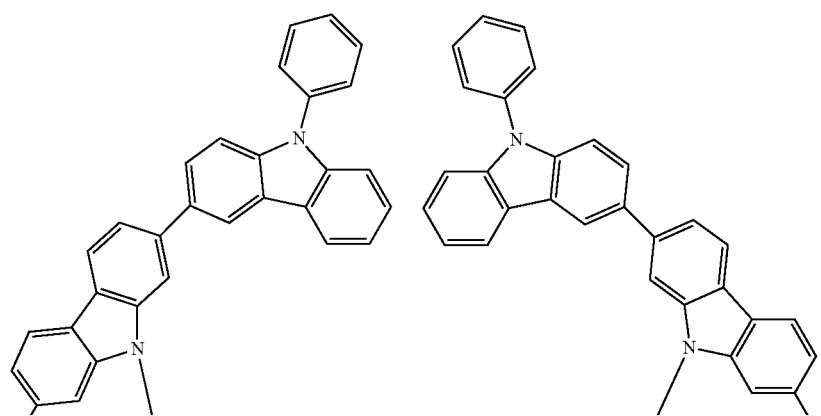

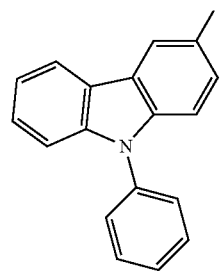
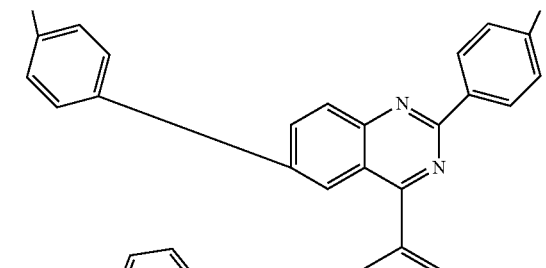
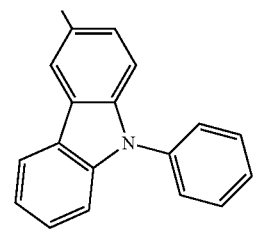
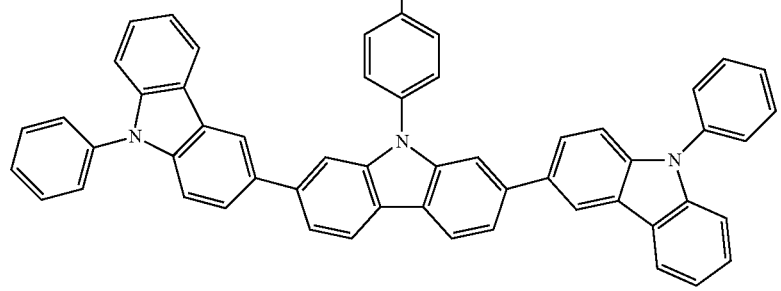
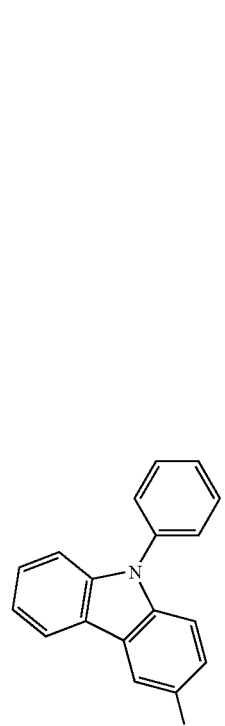
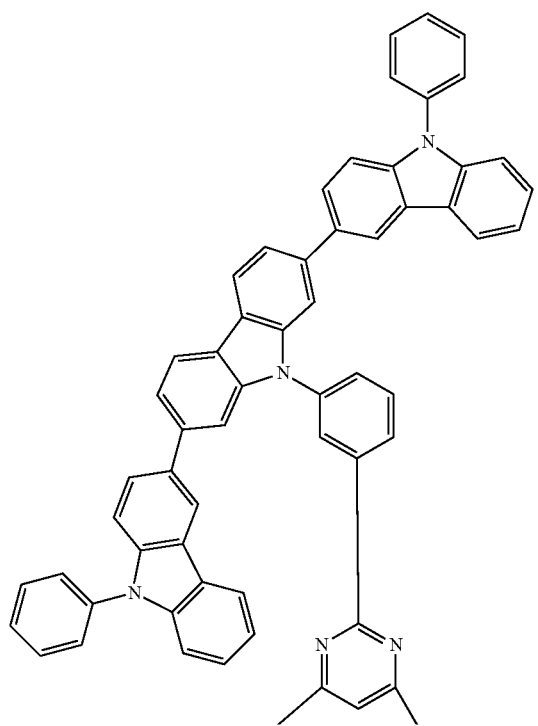
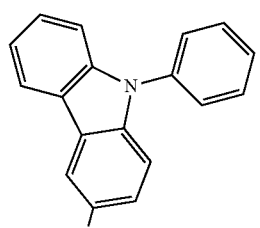

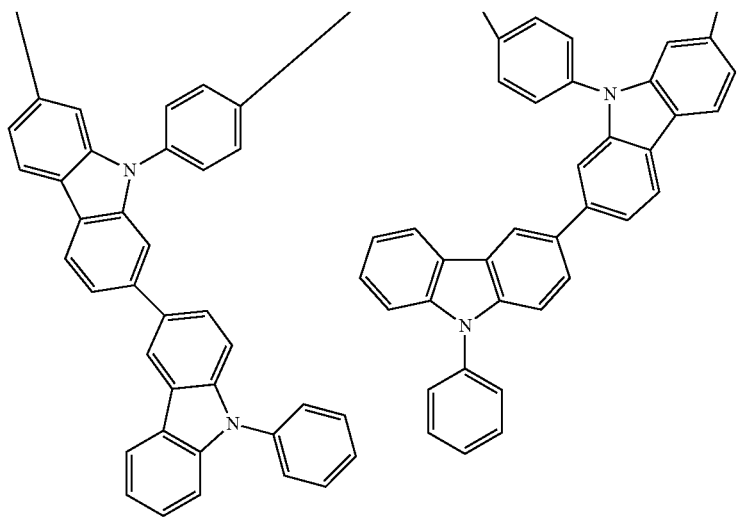
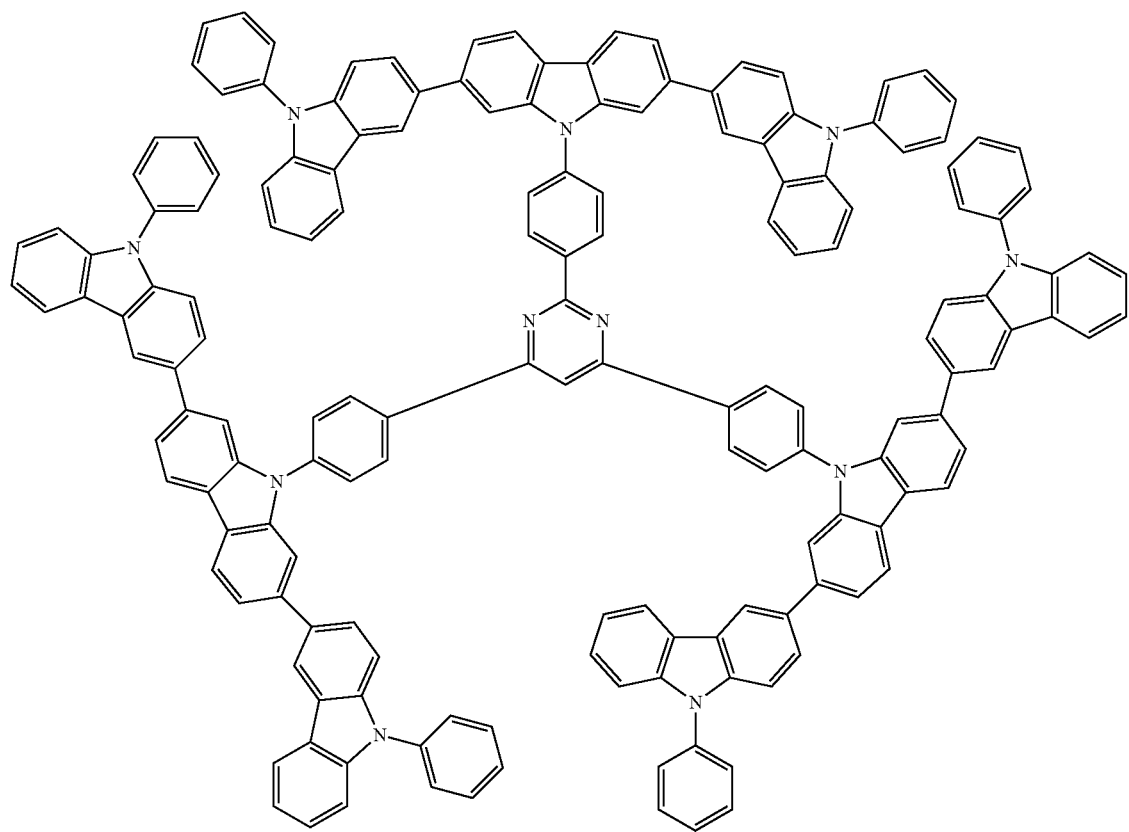

-continued
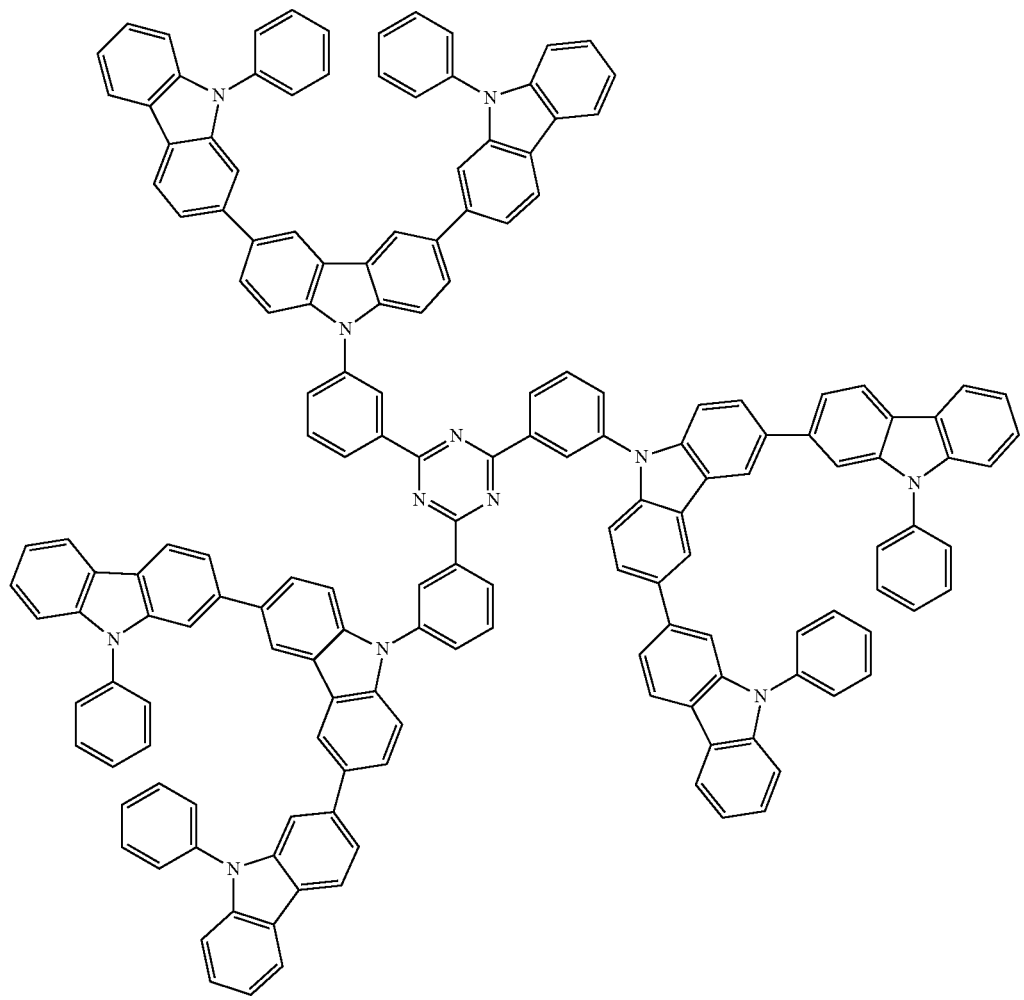
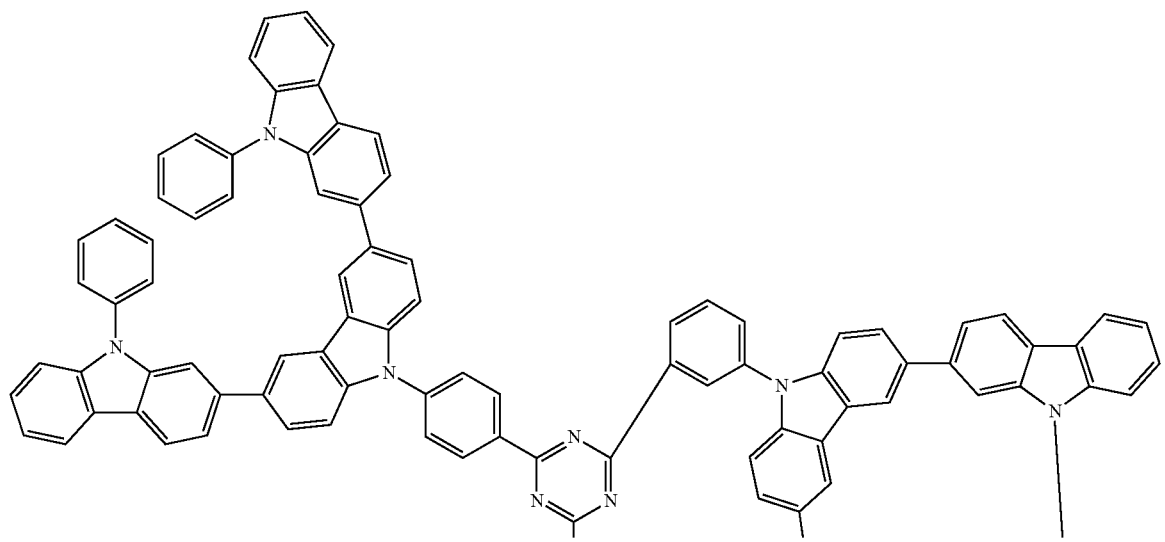

249 250
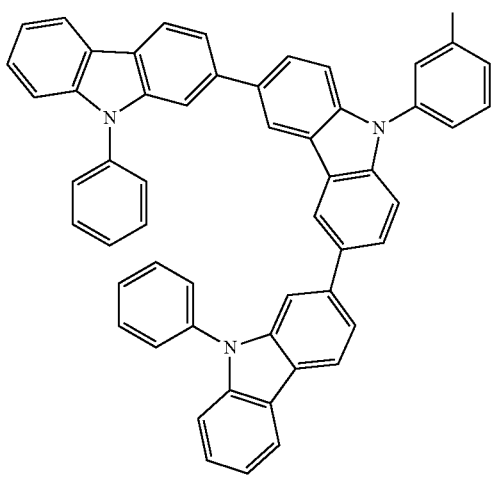
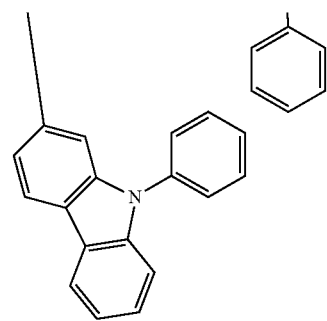
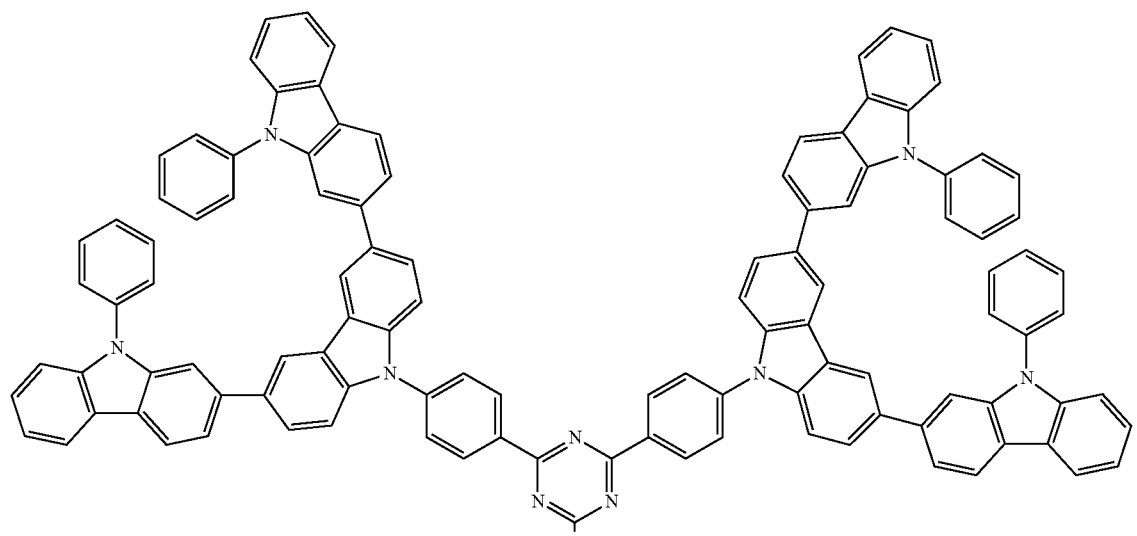
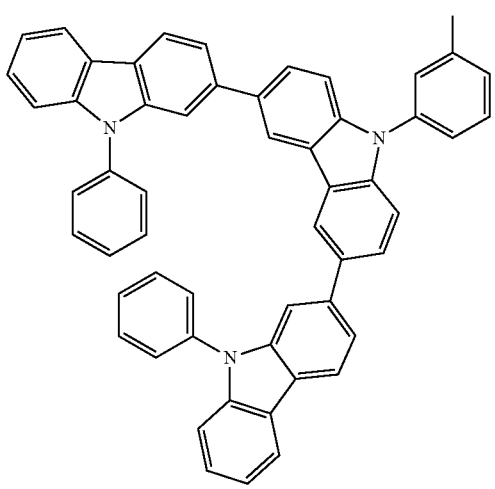

-continued
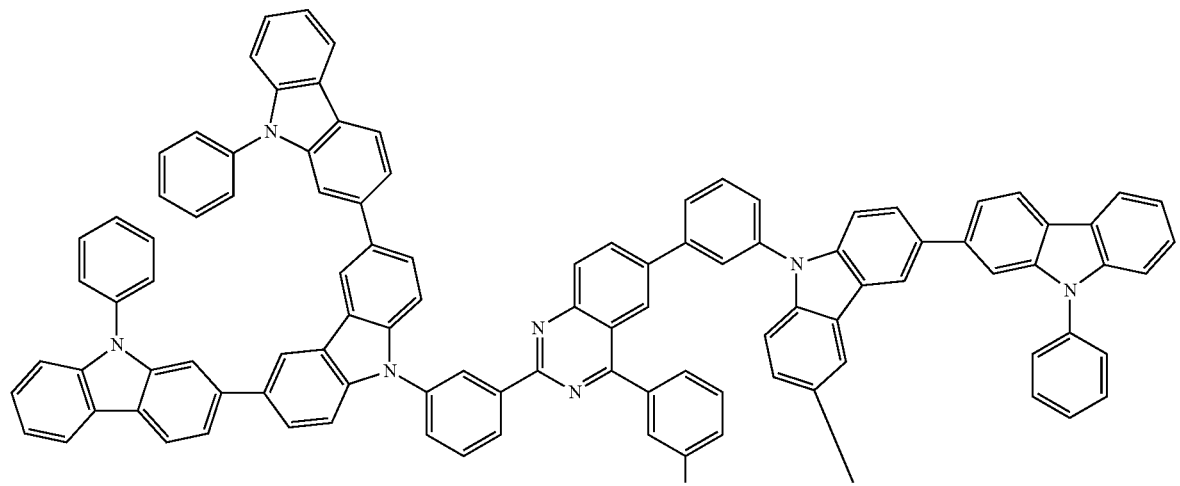
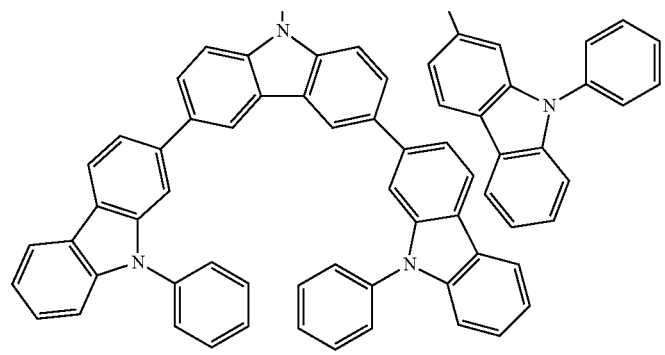
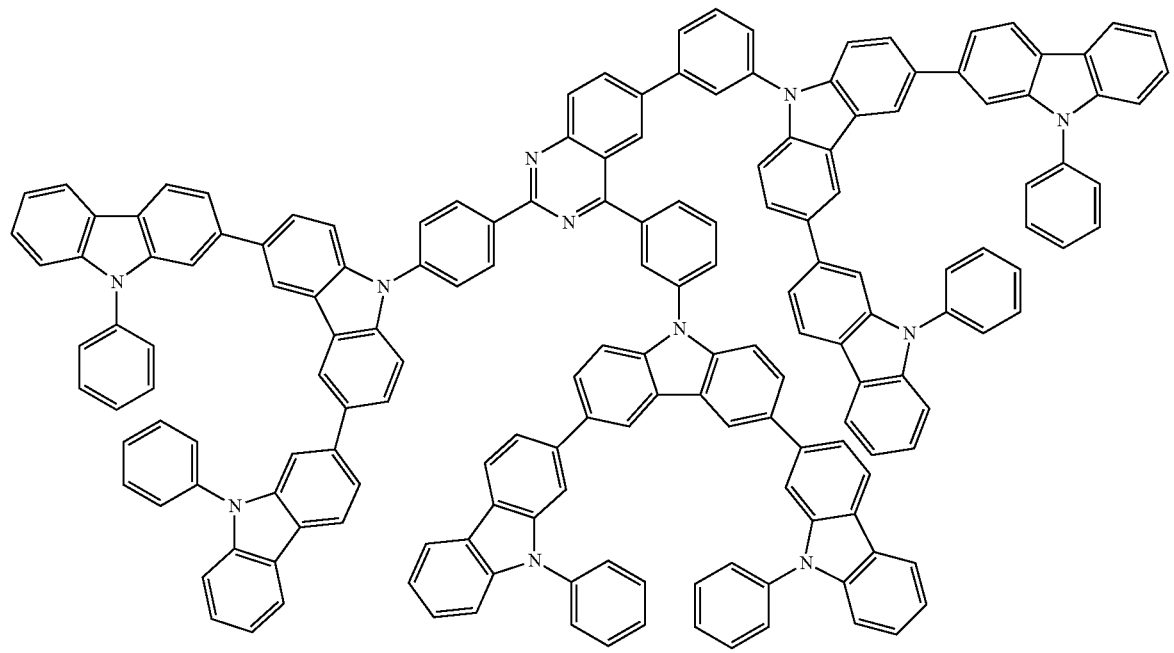

-continued
253
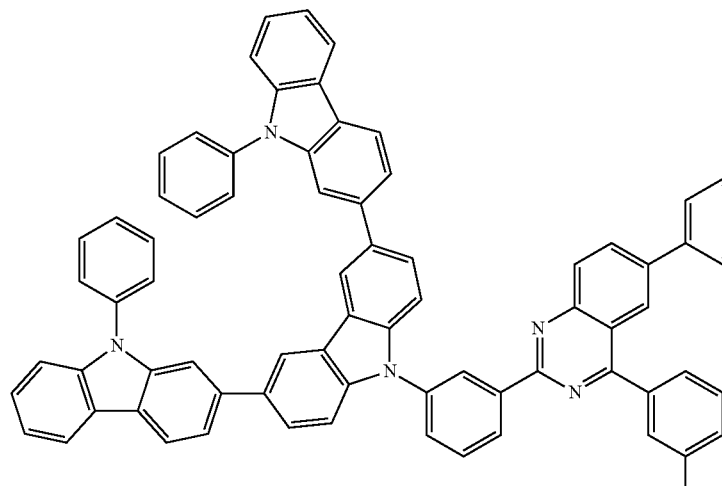
254
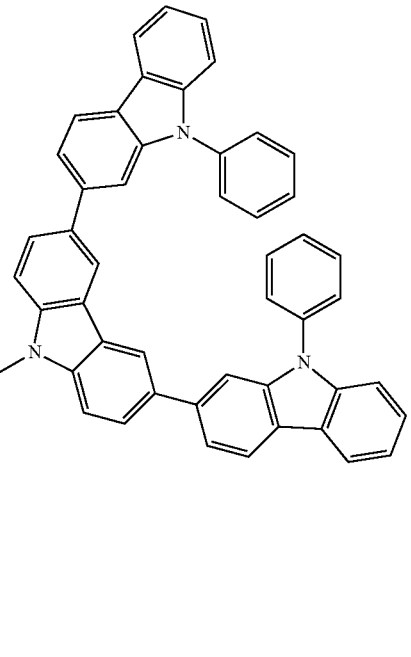
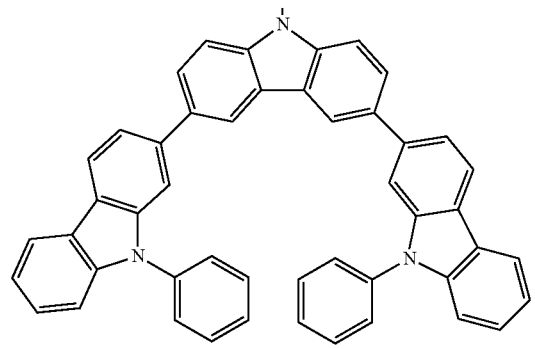
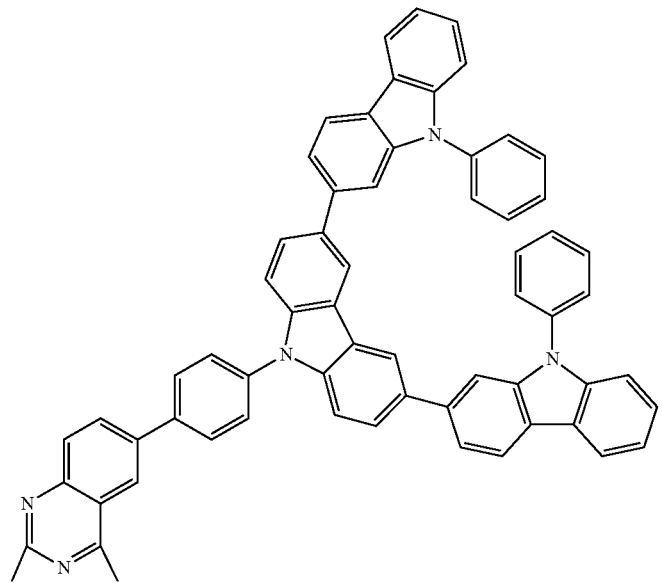

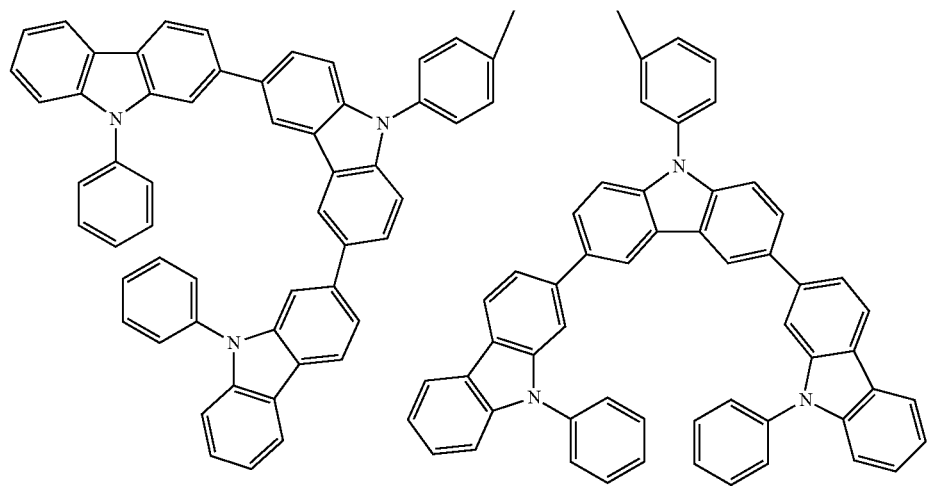
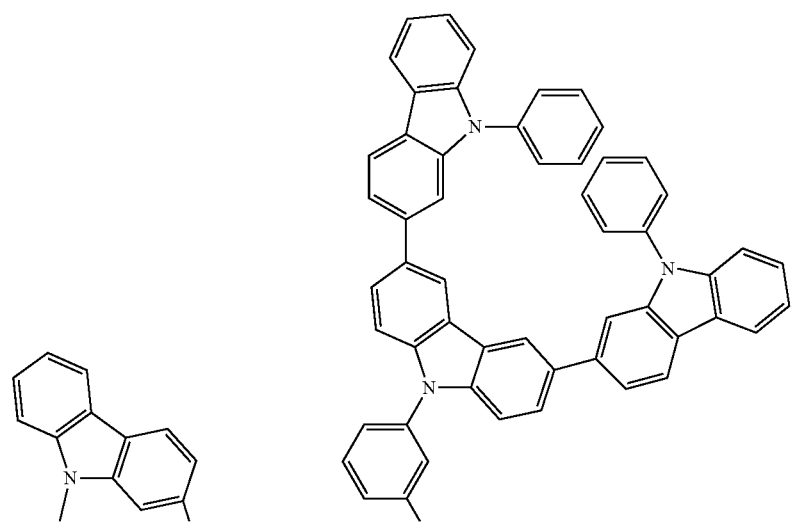
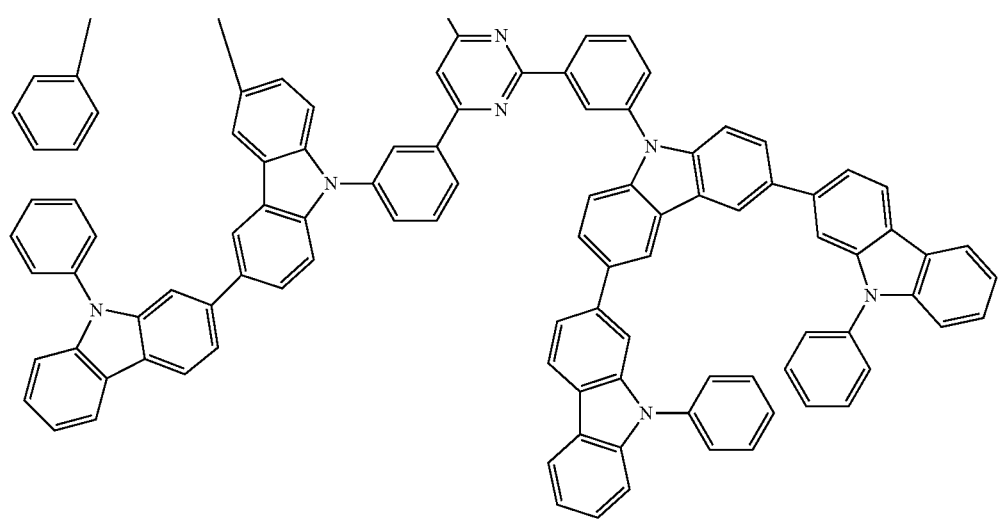

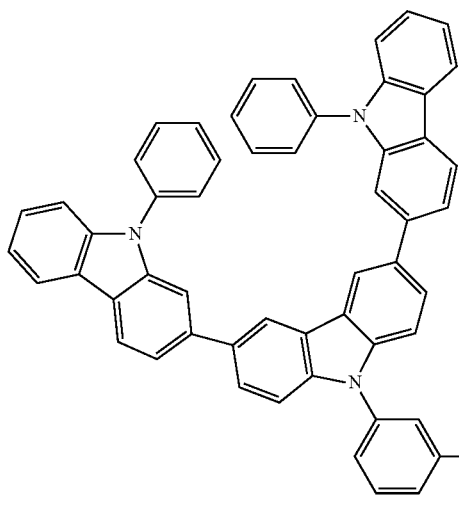
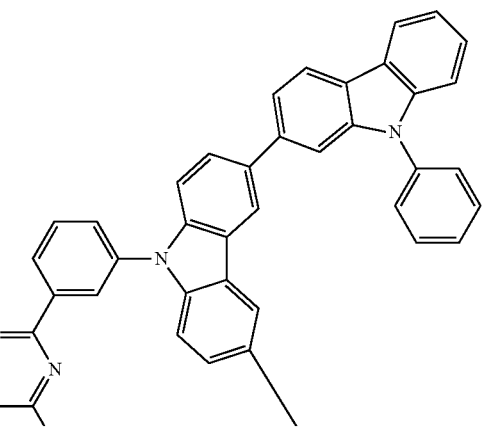
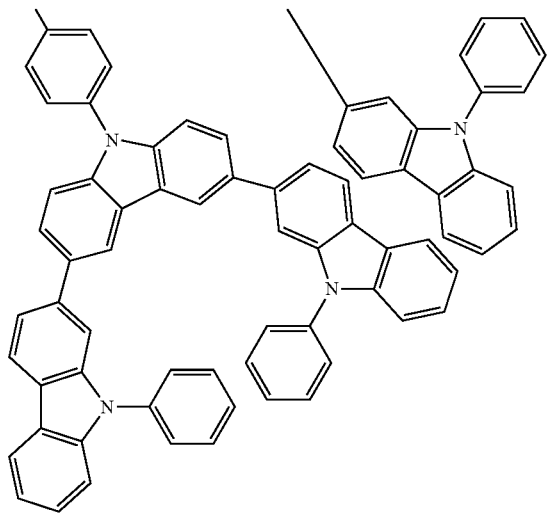
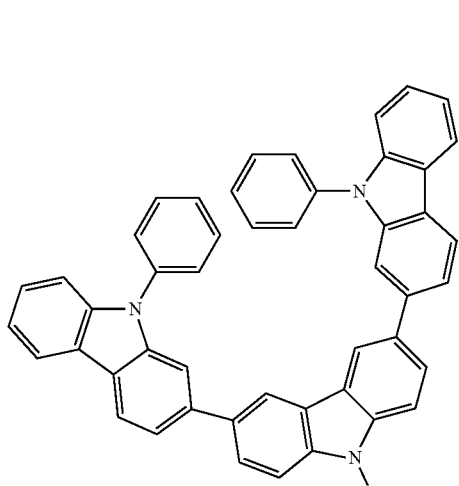
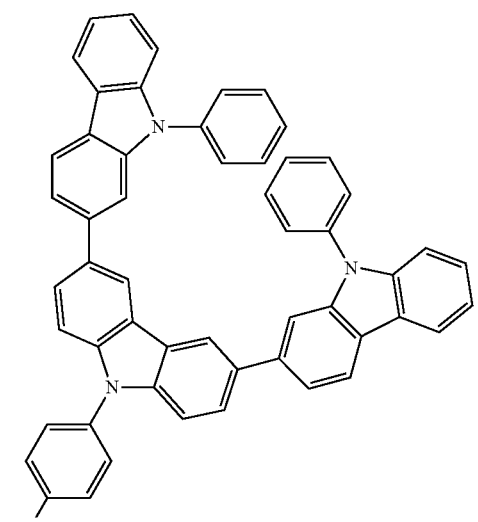

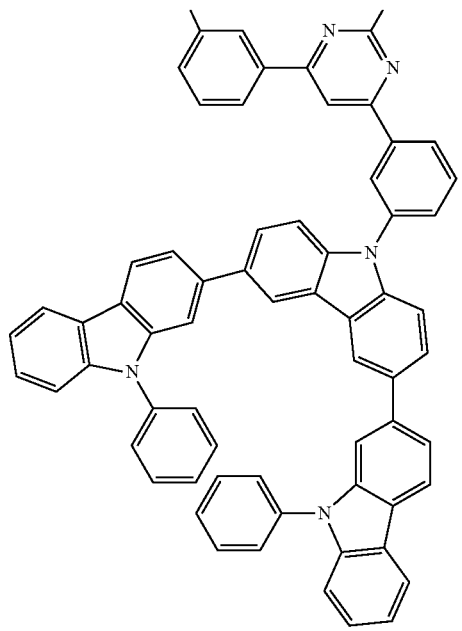
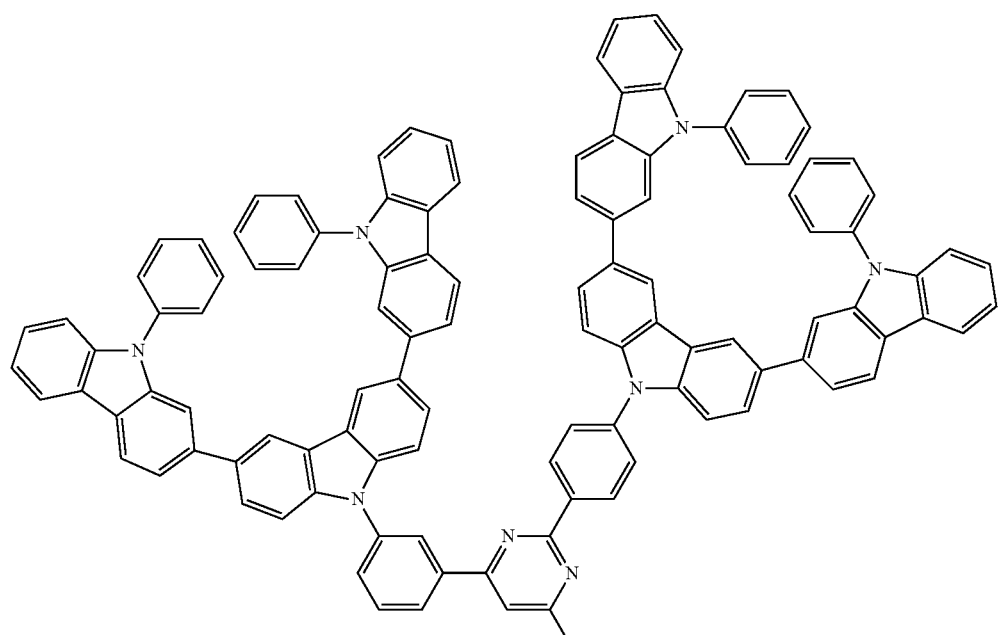

-continued
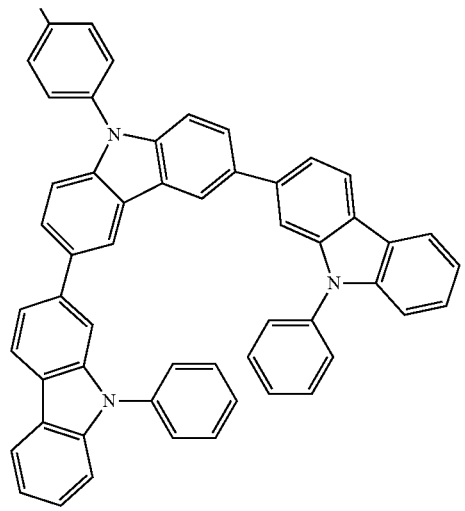
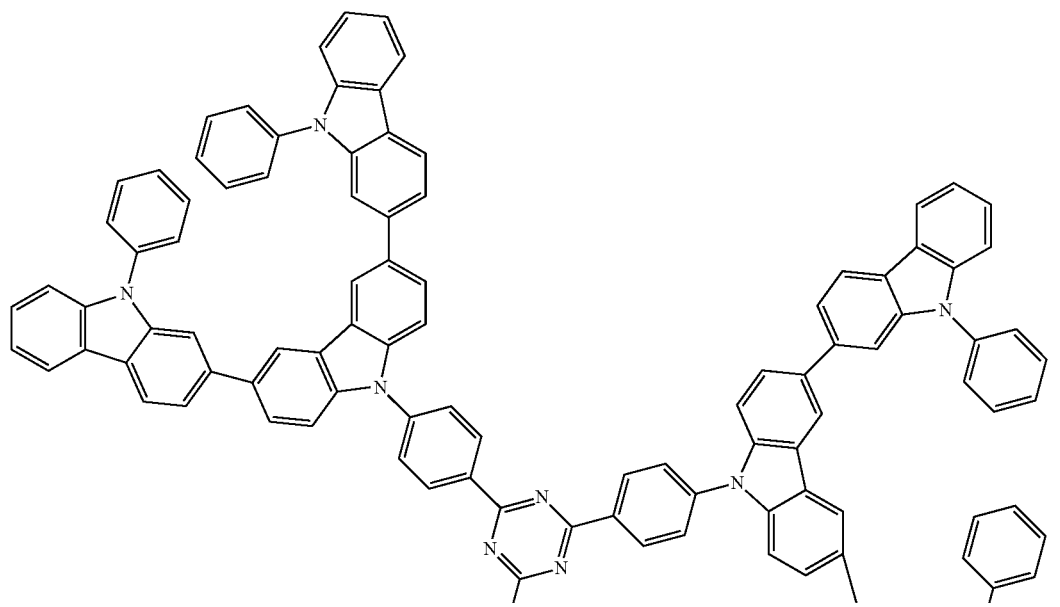
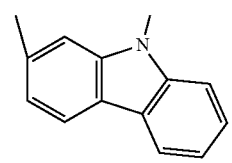
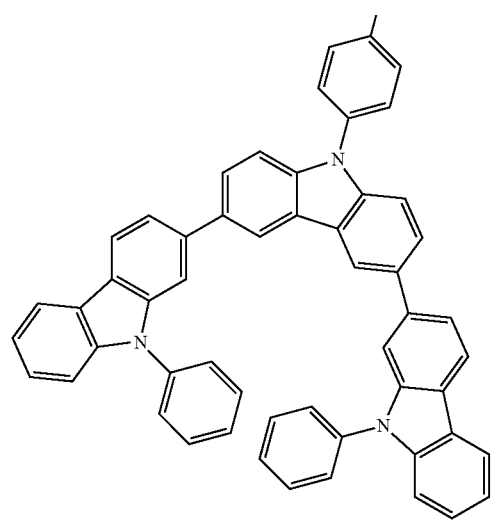

263 264
-continued
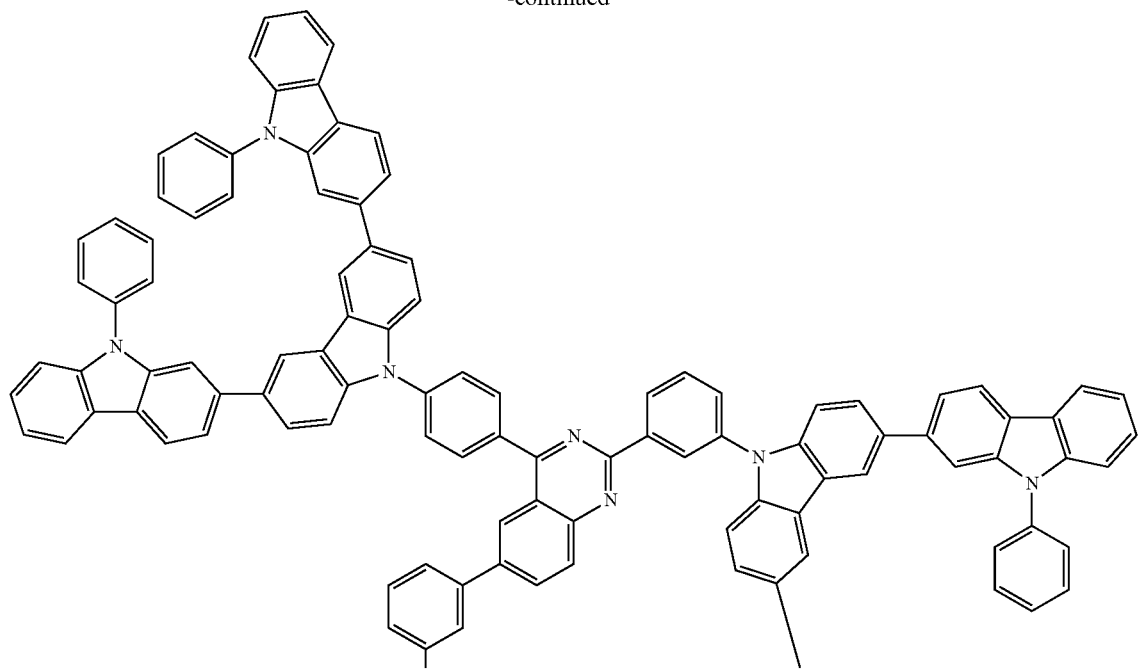
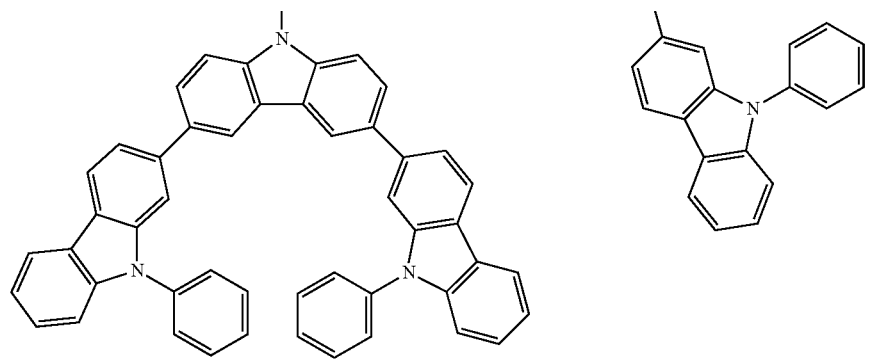
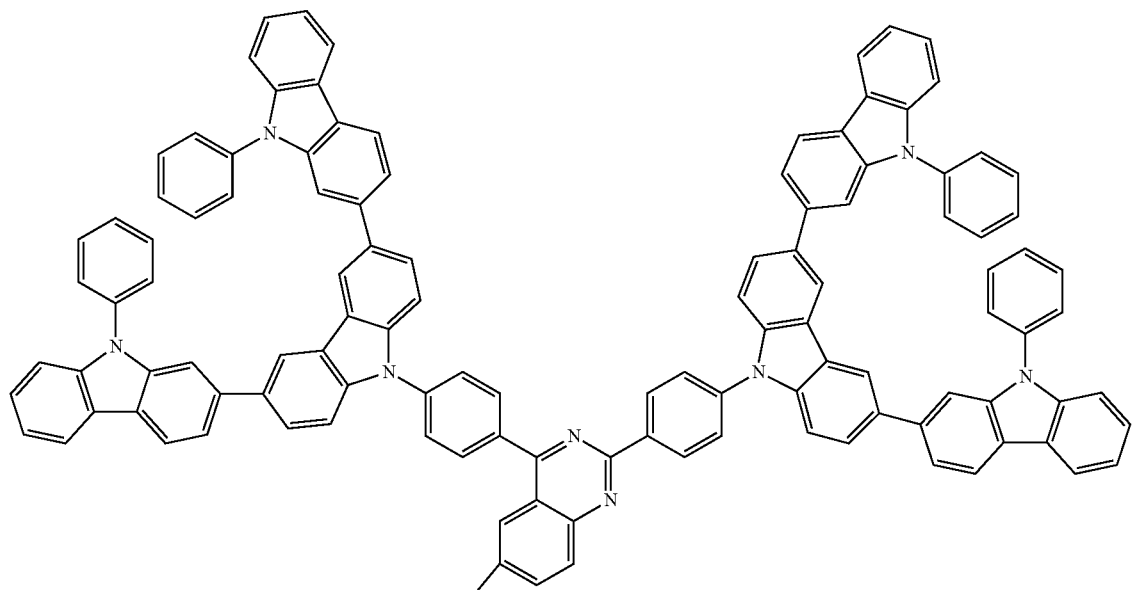

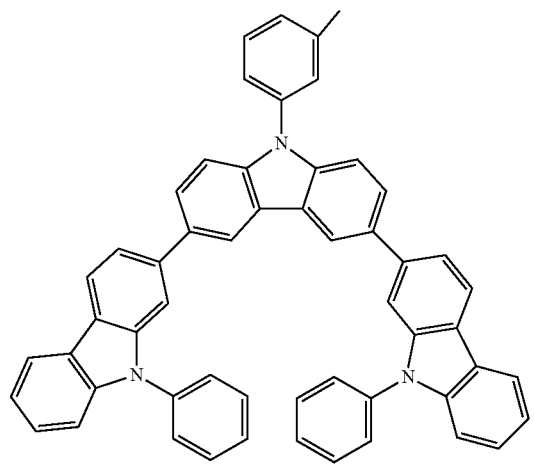
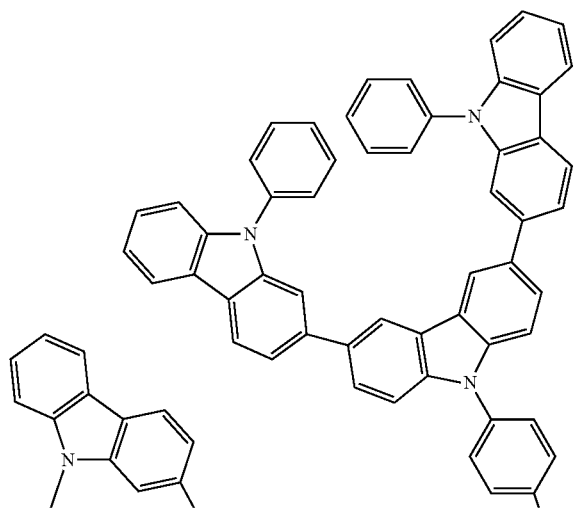
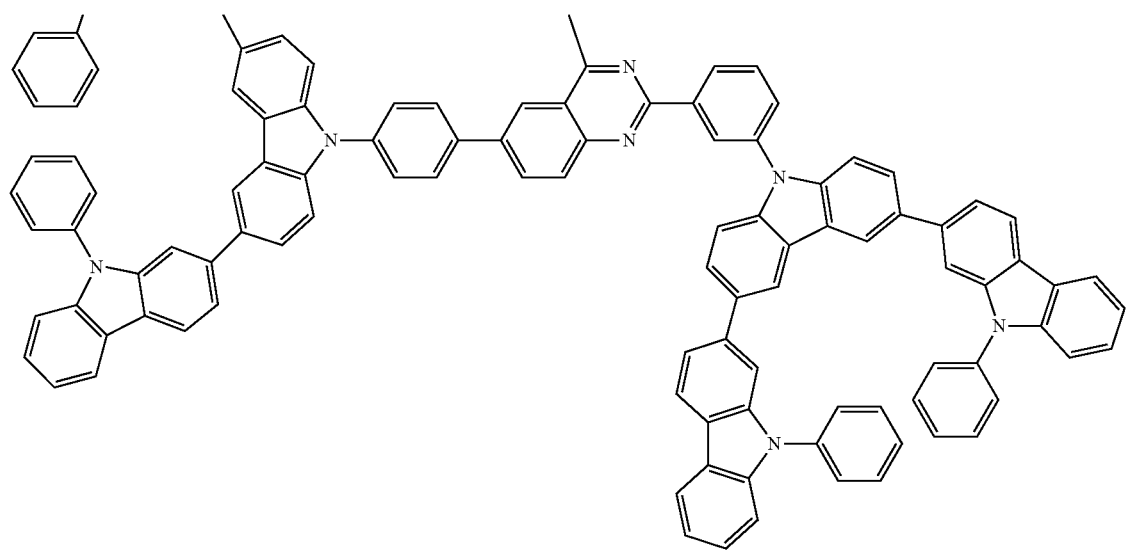

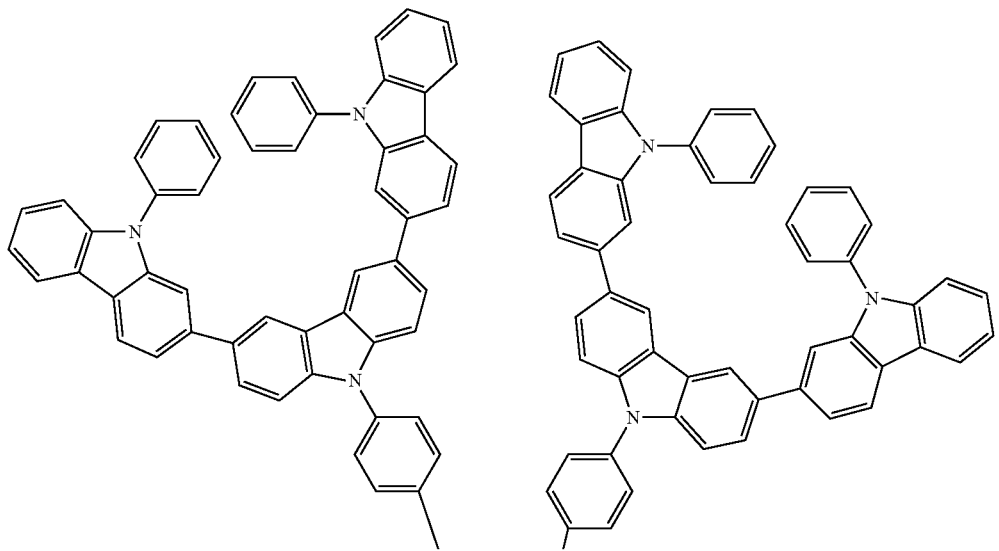
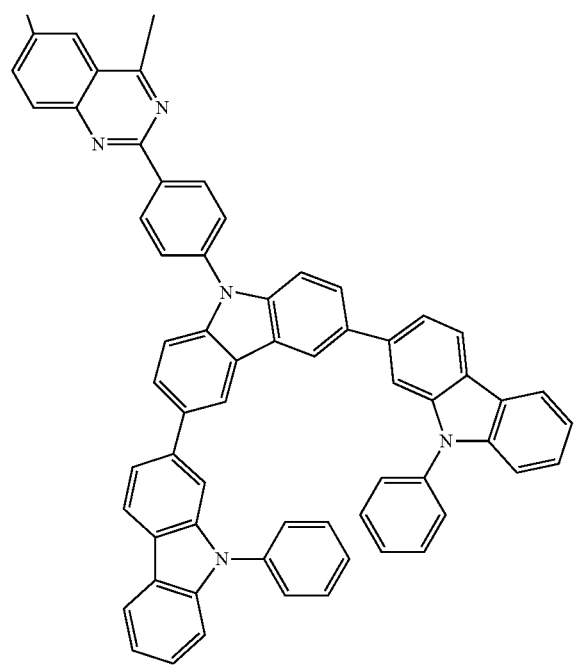

269
270
-continued
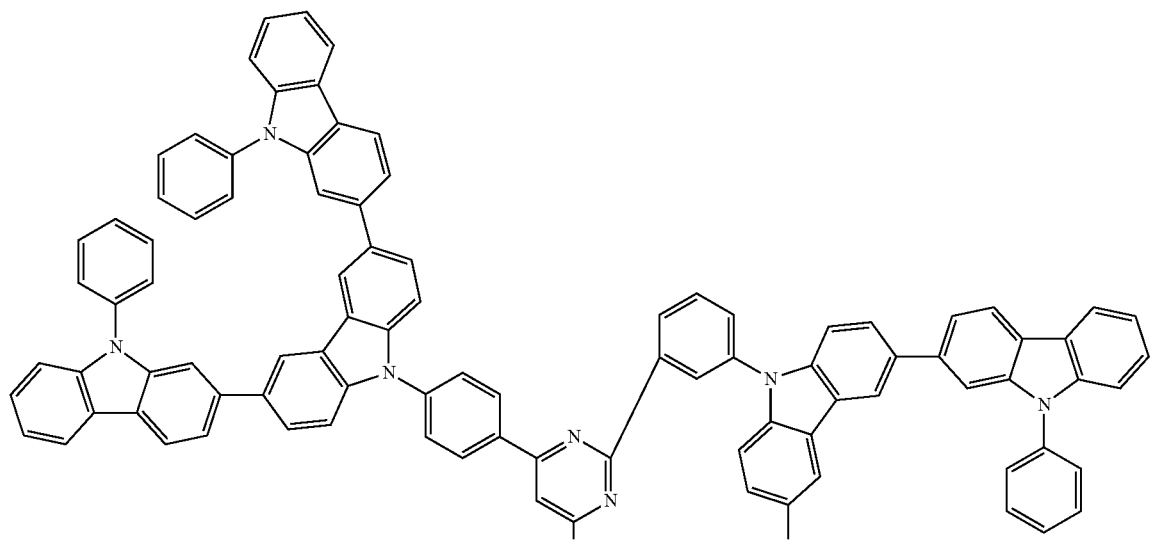
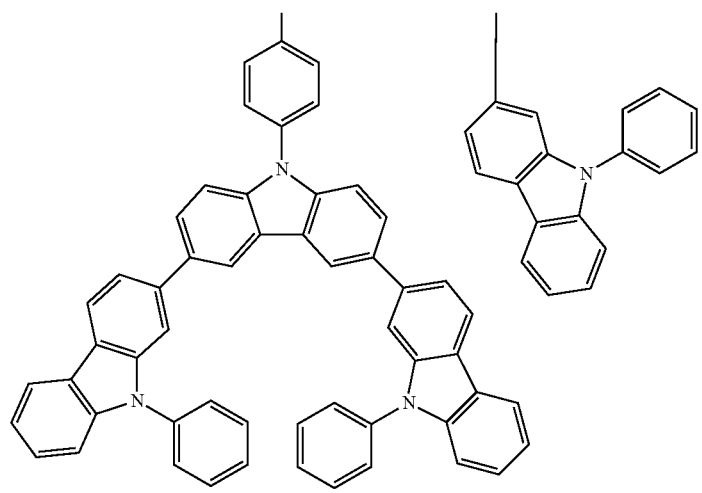
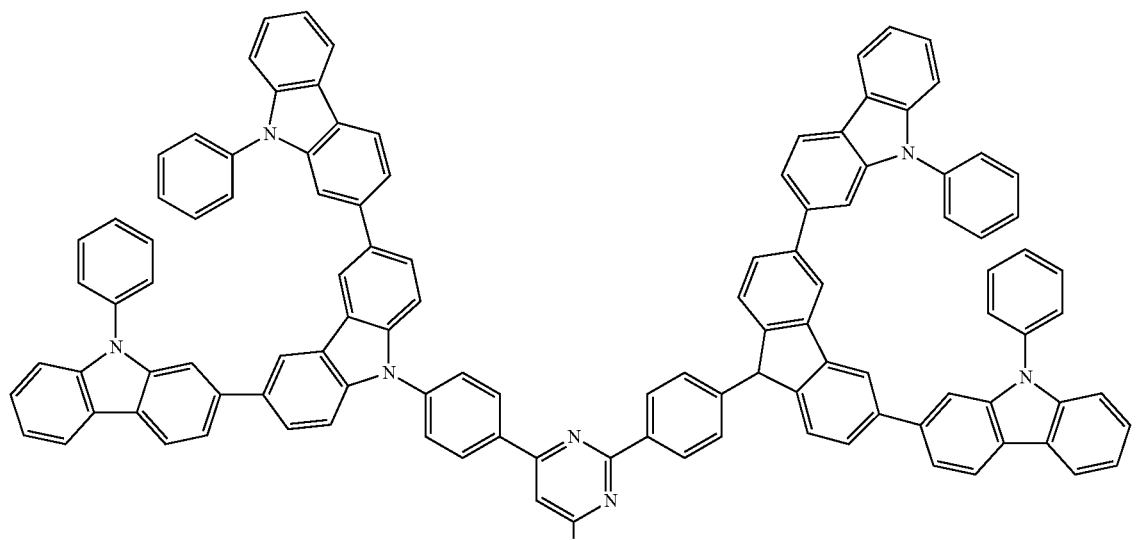

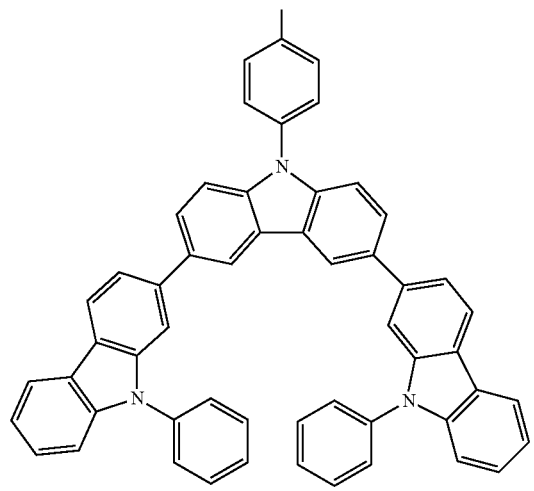
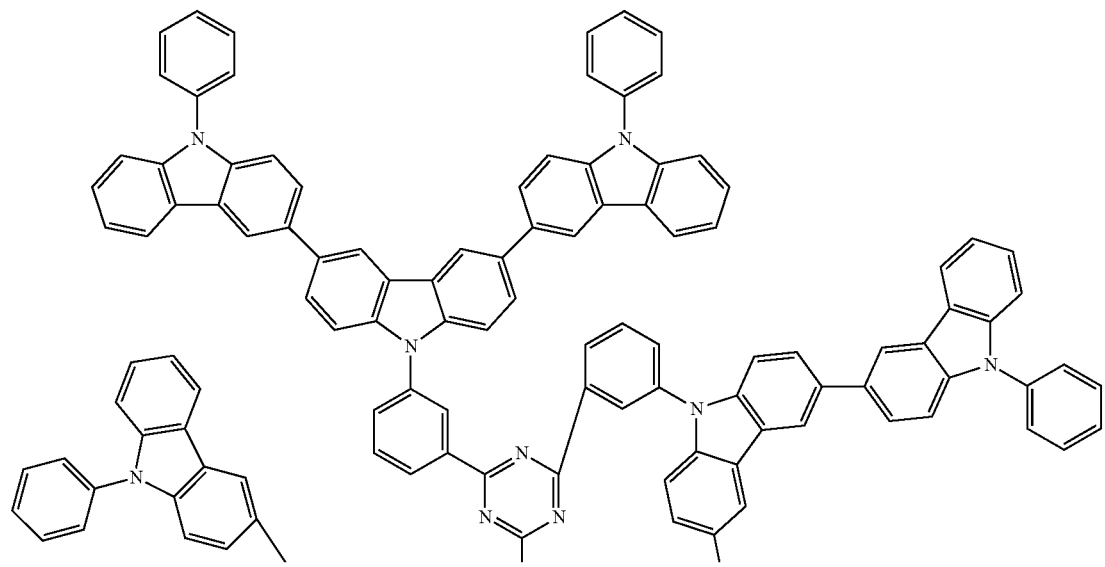
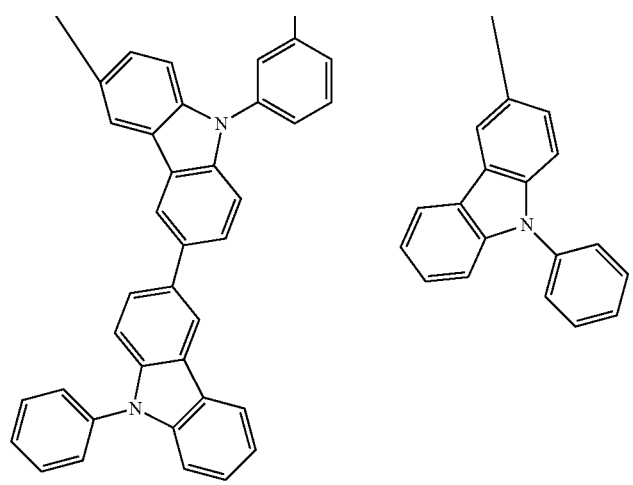

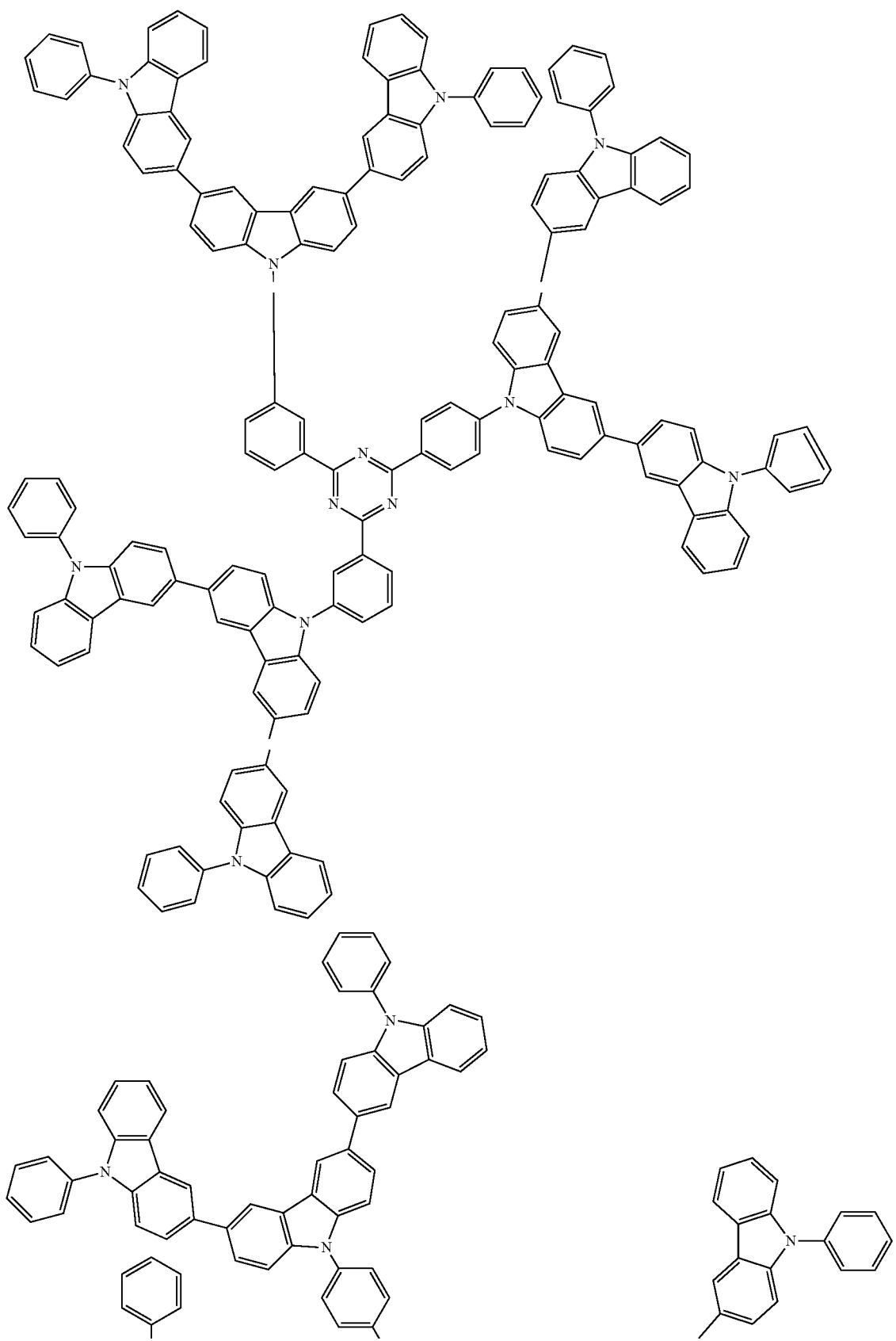

275 276
-continued
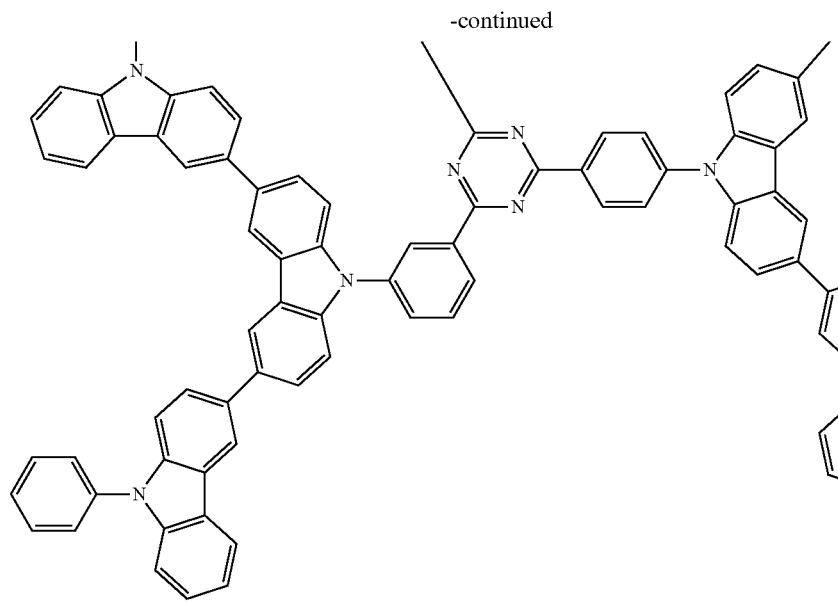
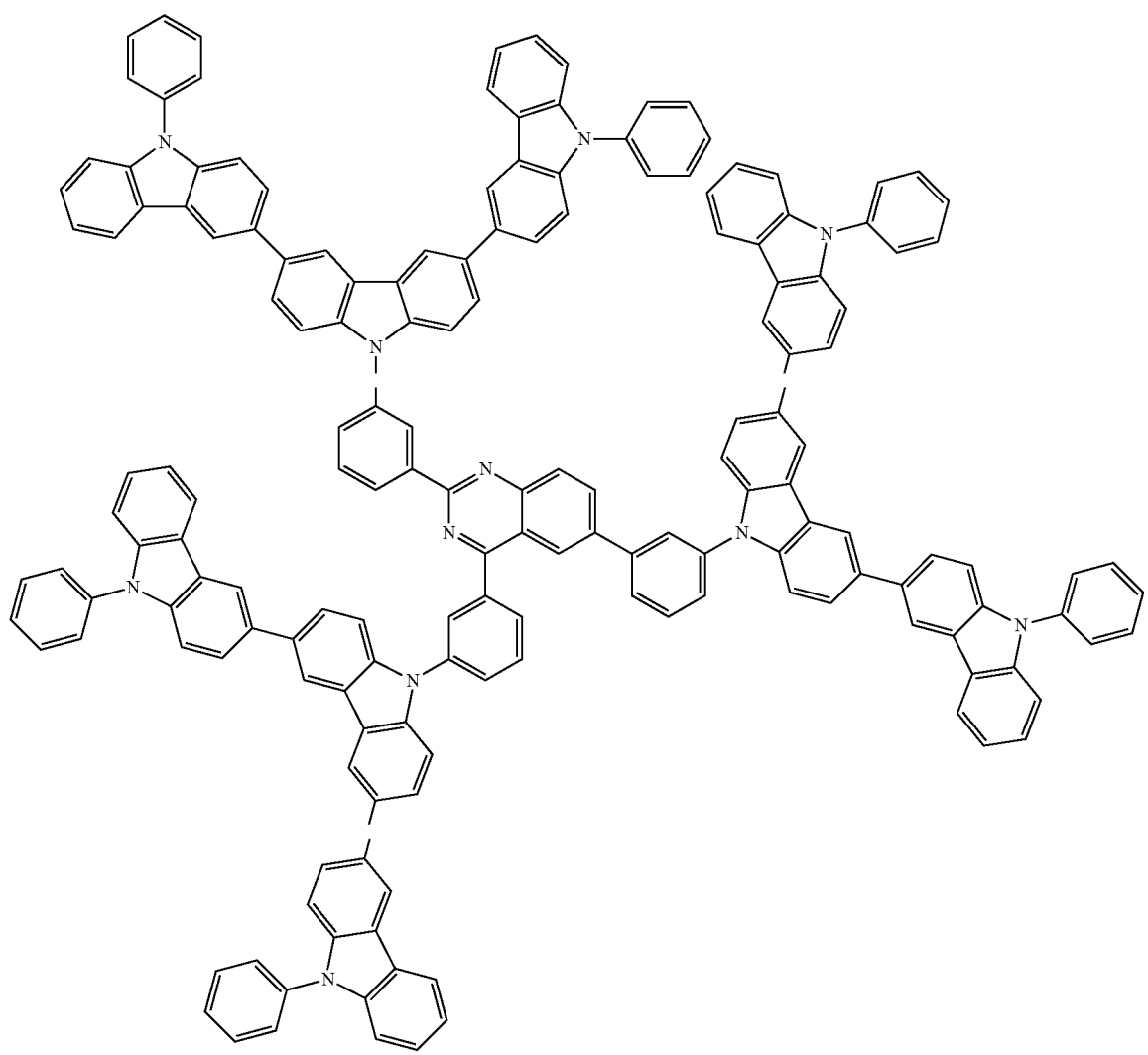 [SMILES: c1ccc(-n2c3ccccc3c3cc(-c4ccc5c(c4)c4cc(-c6ccc7c(c6)c6ccccc6n7-c6ccccc6)ccc4n5-c4cccc(-c5ccc6nc(-c7cccc(-n8c9ccc(-c%10ccc%11c(c%10)c%10ccccc%10n%11-c%10ccccc%10)cc9c9cc(-c%10ccc%11c(c%10)c%10ccccc%10n%11-c%10ccccc%10)ccc98)c7)nc(-c7cccc(-n8c9ccc(-c%10ccc%11c(c%10)c%10ccccc%10n%11-c%10ccccc%10)cc9c9cc(-c%10ccc%11c(c%10)c%10ccccc%10n%11-c%10ccccc%10)ccc98)c7)c6c5)c4)ccc32)cc1]

-continued
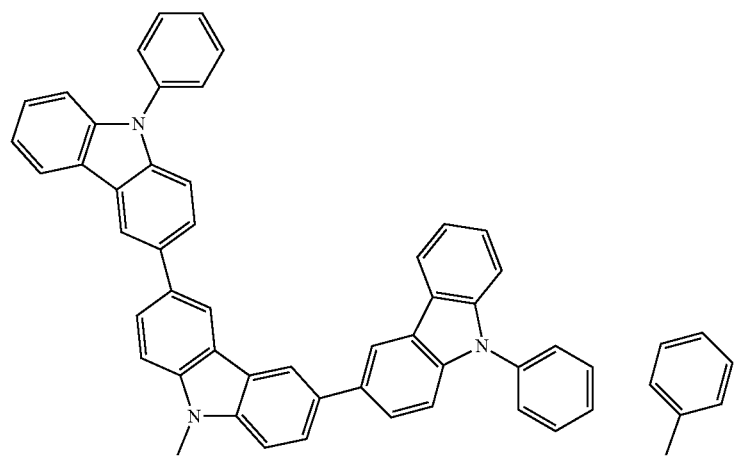
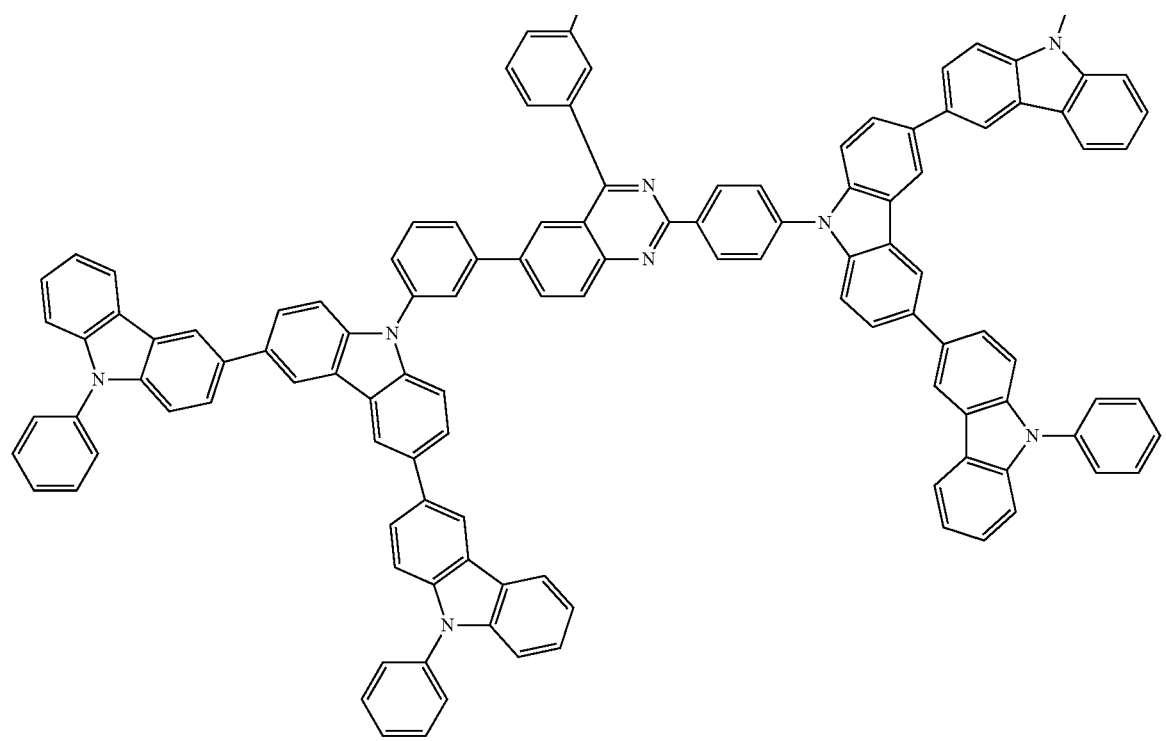
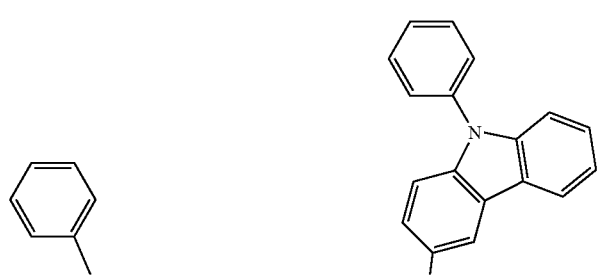
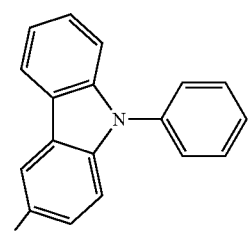

279 280
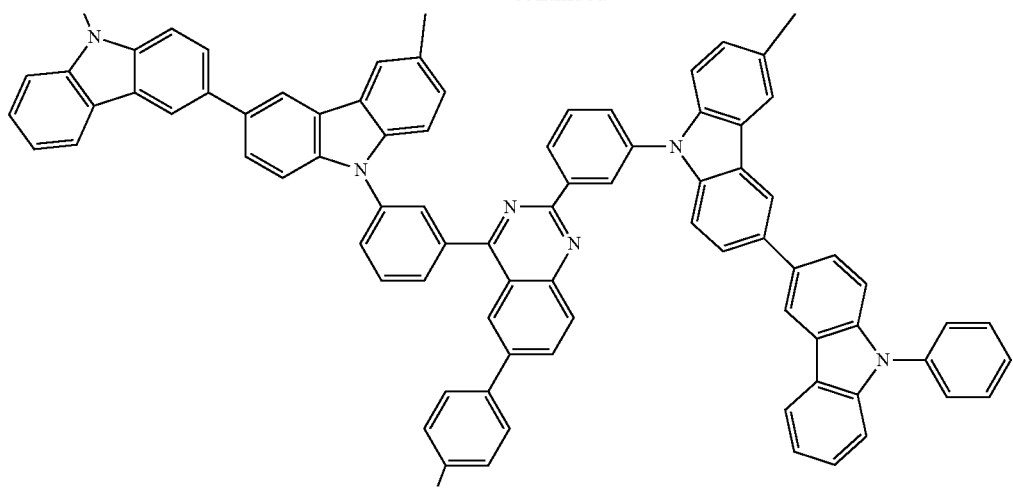
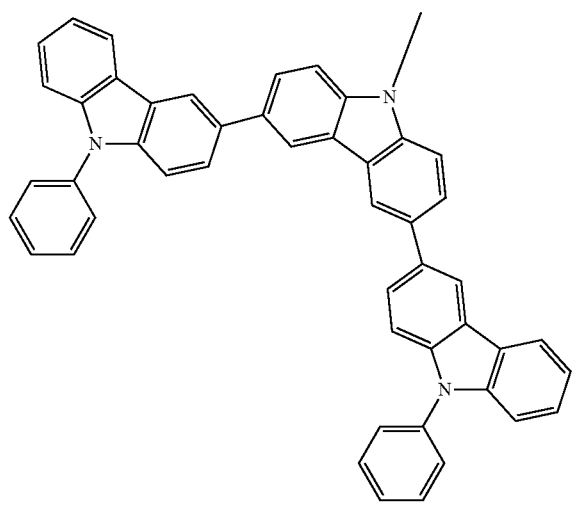
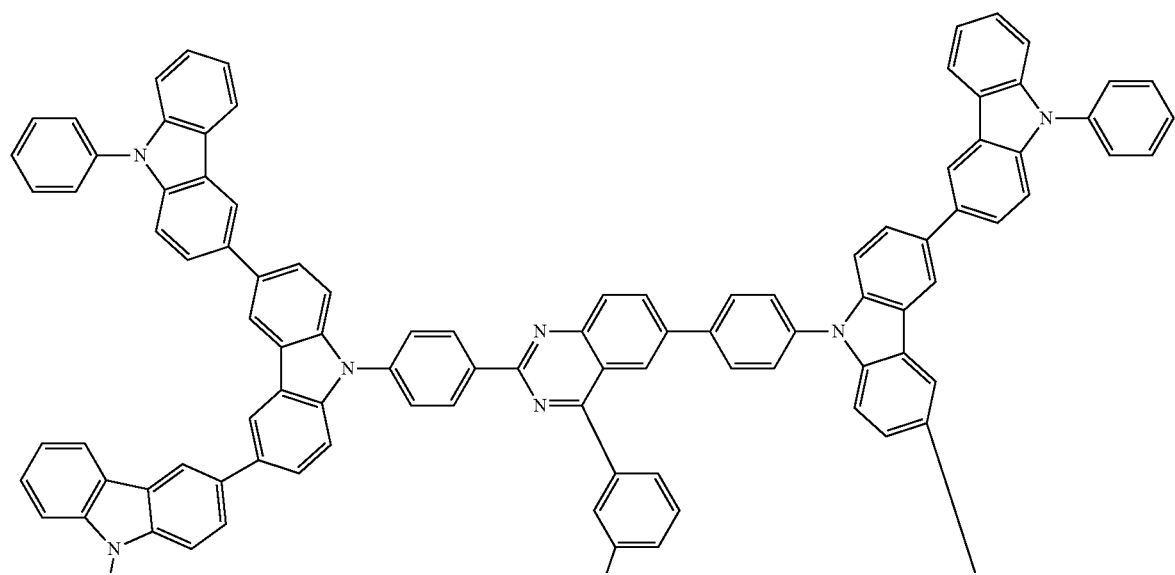

281
-continued
282
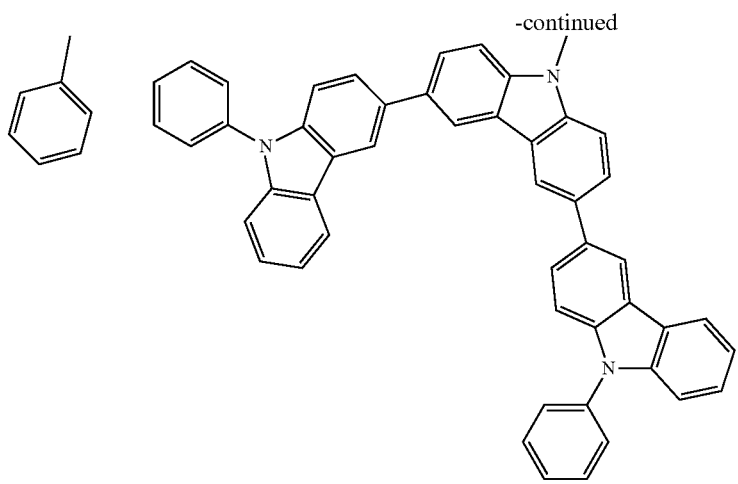
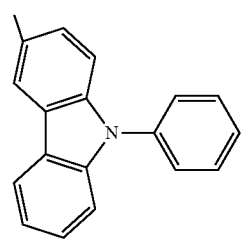
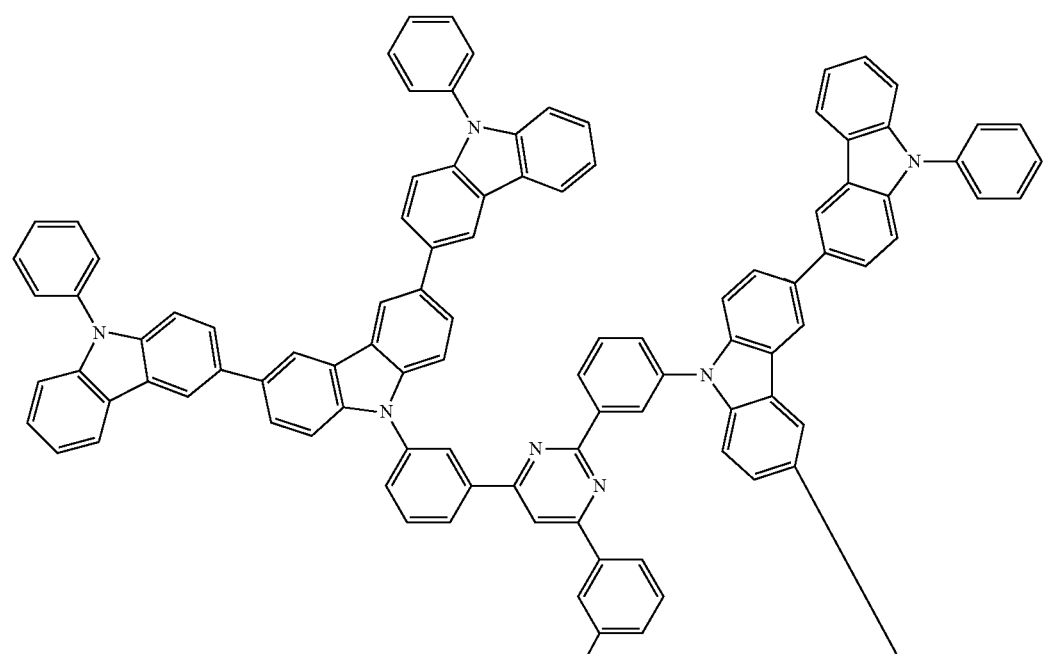
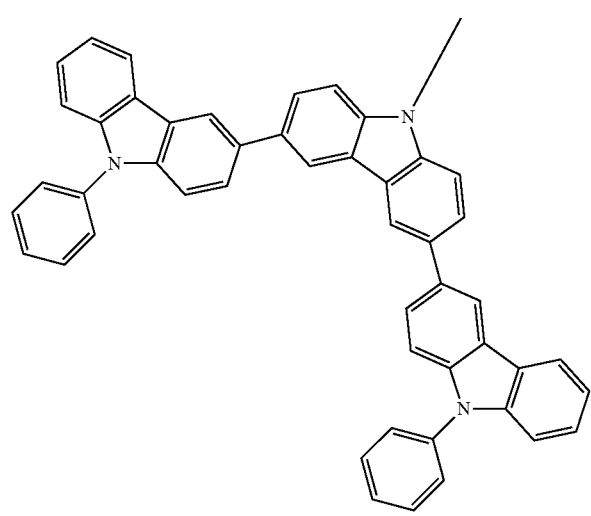
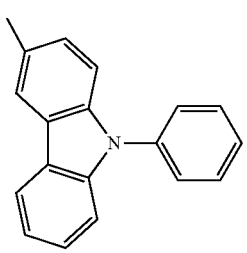

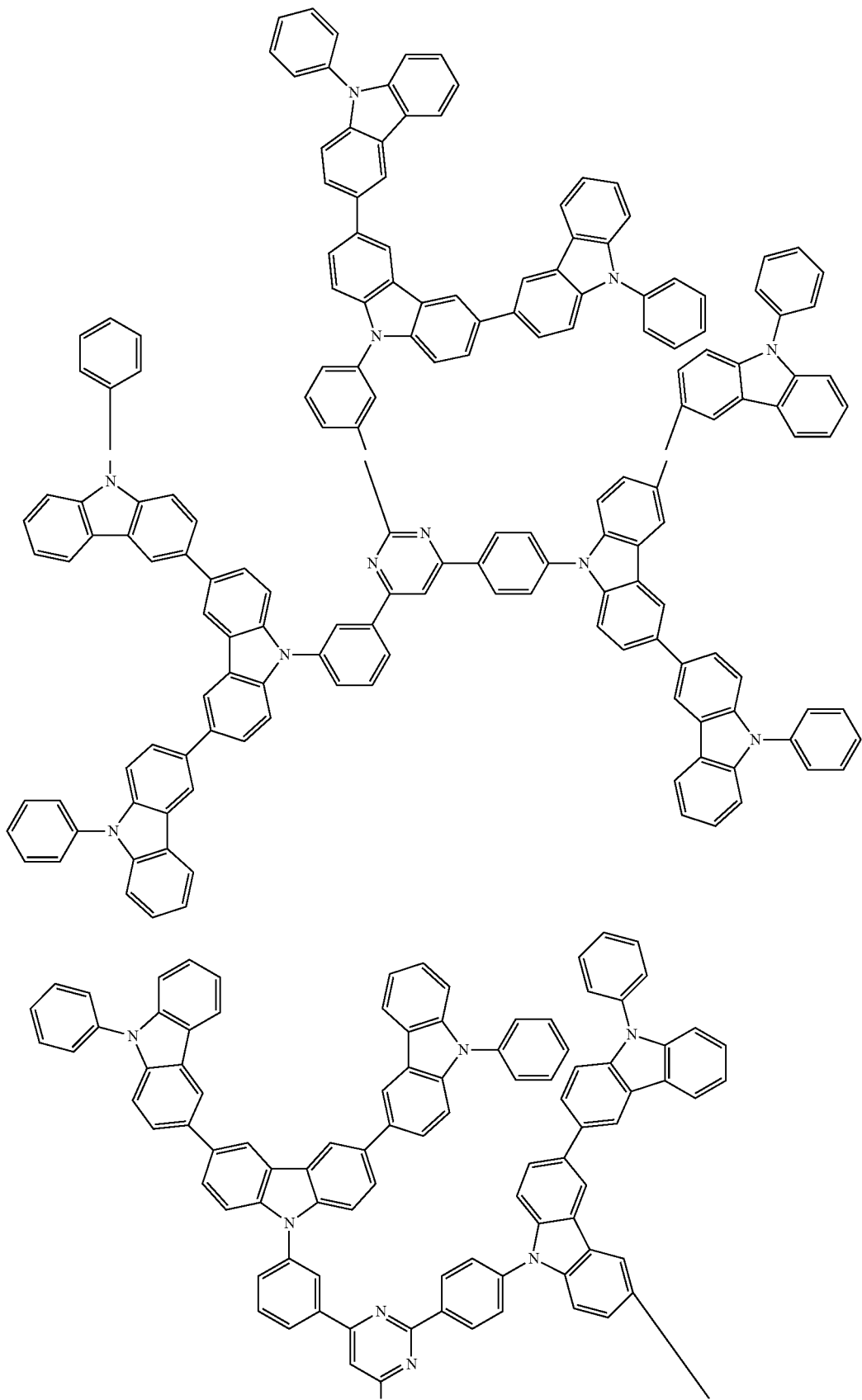

-continued
285
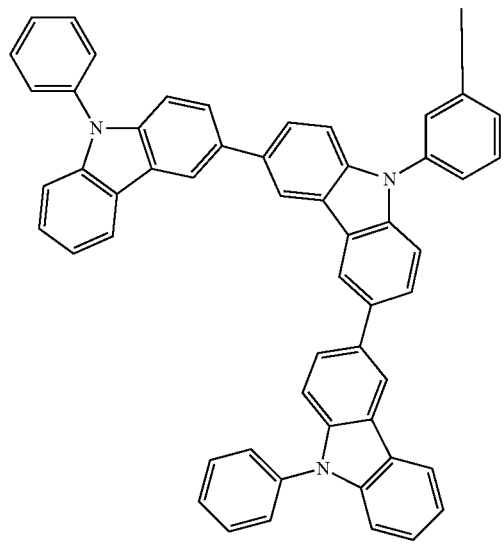
286
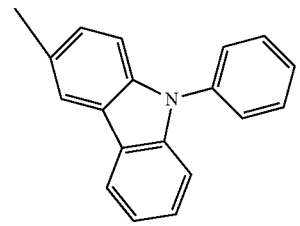
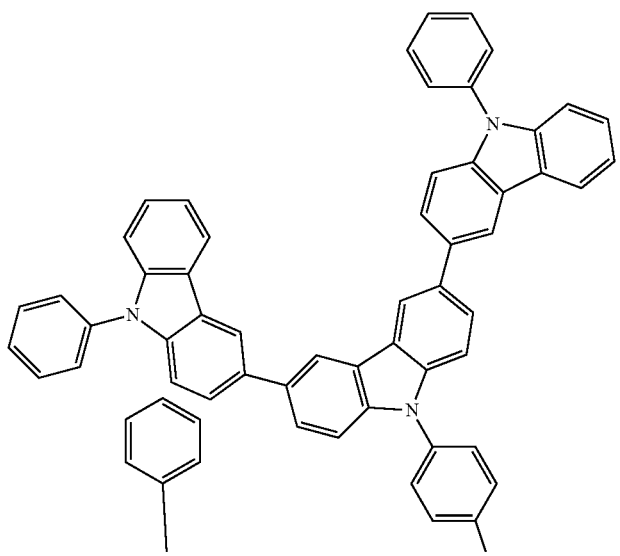
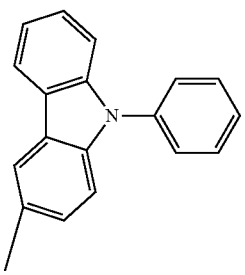
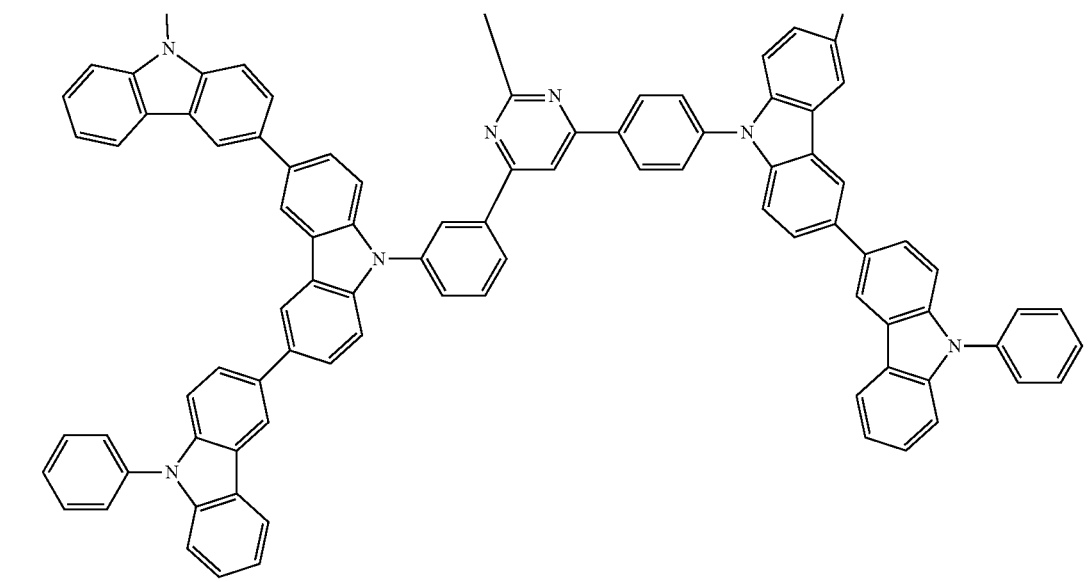

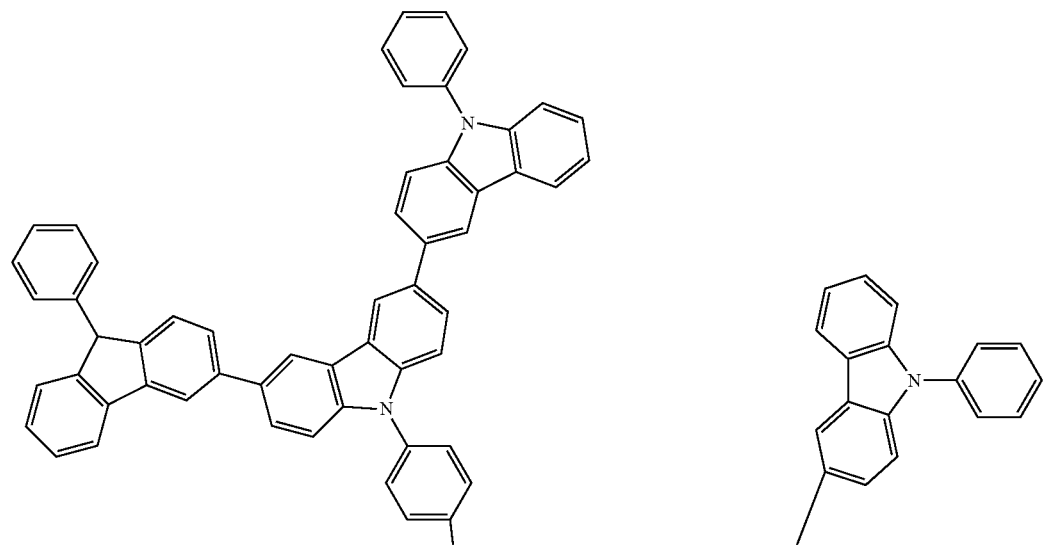
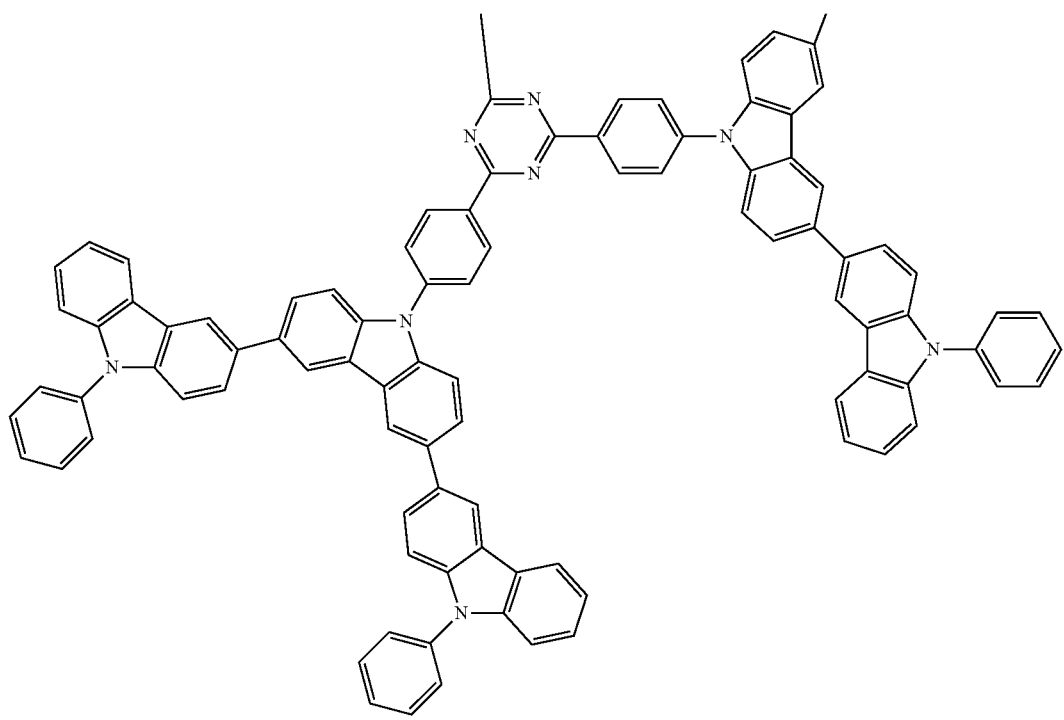
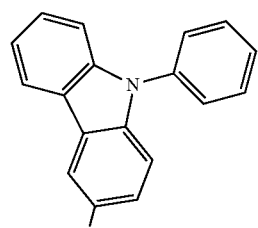

-continued
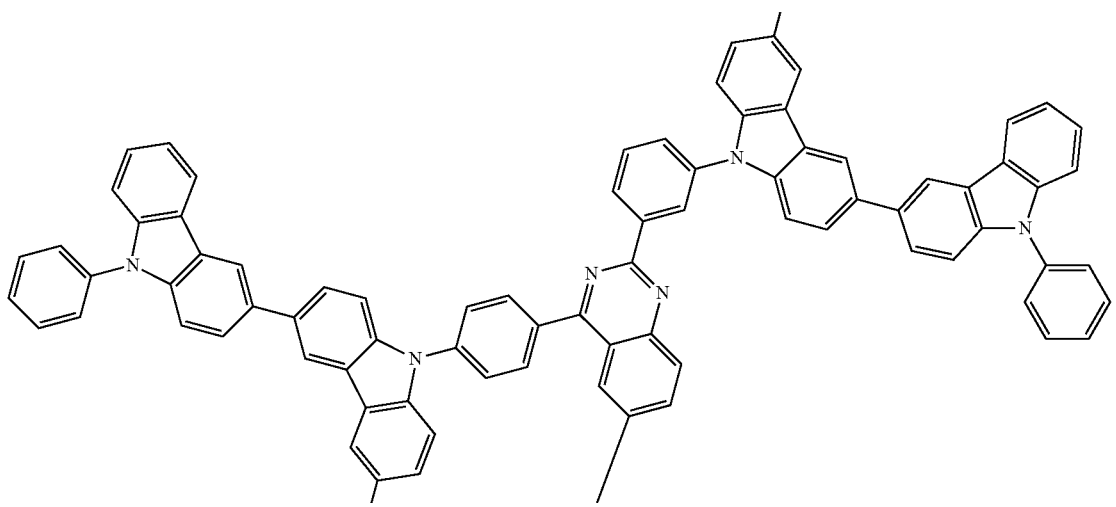
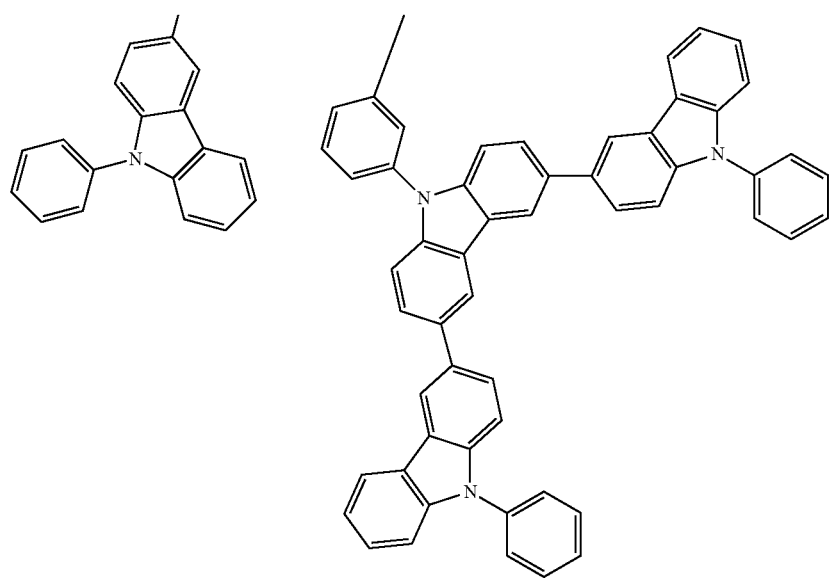
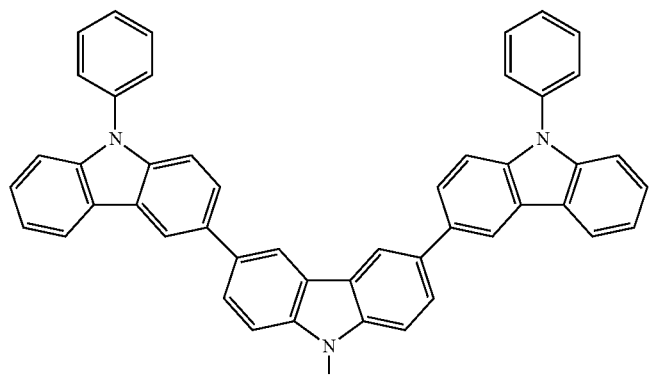

-continued
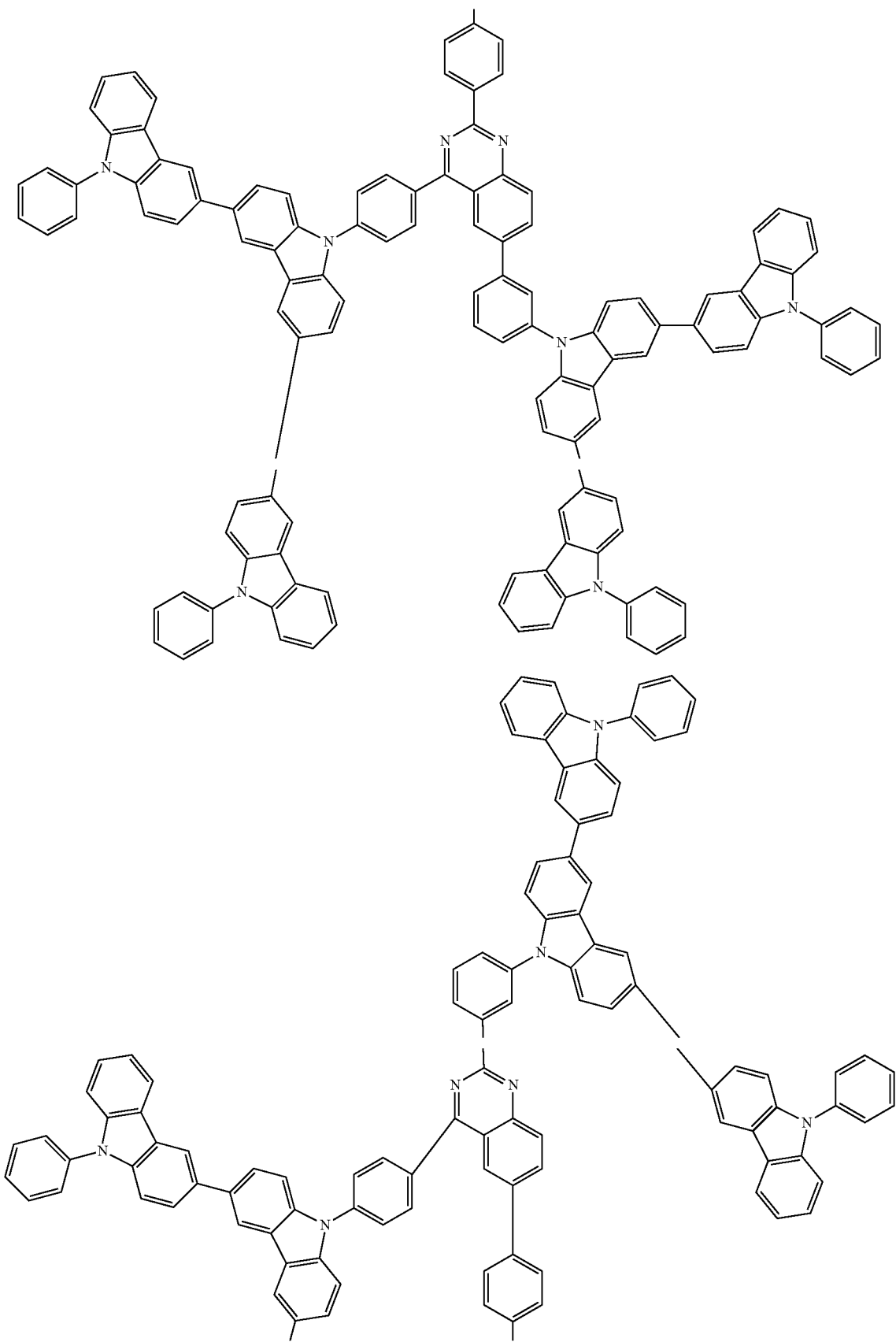

-continued
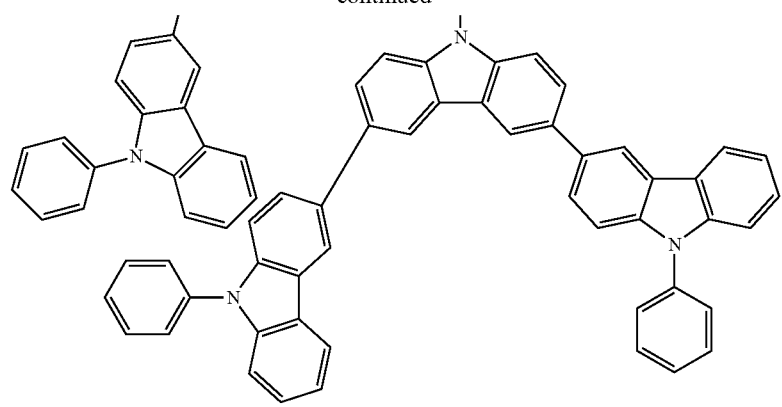
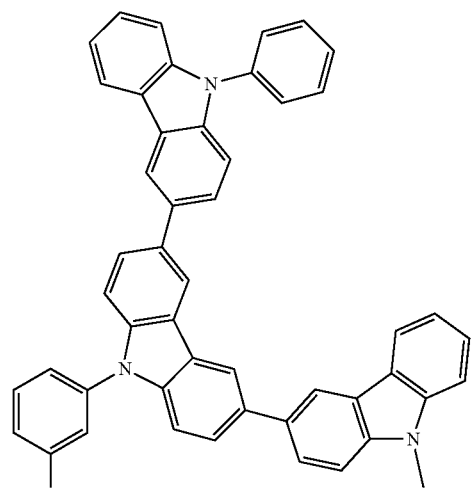
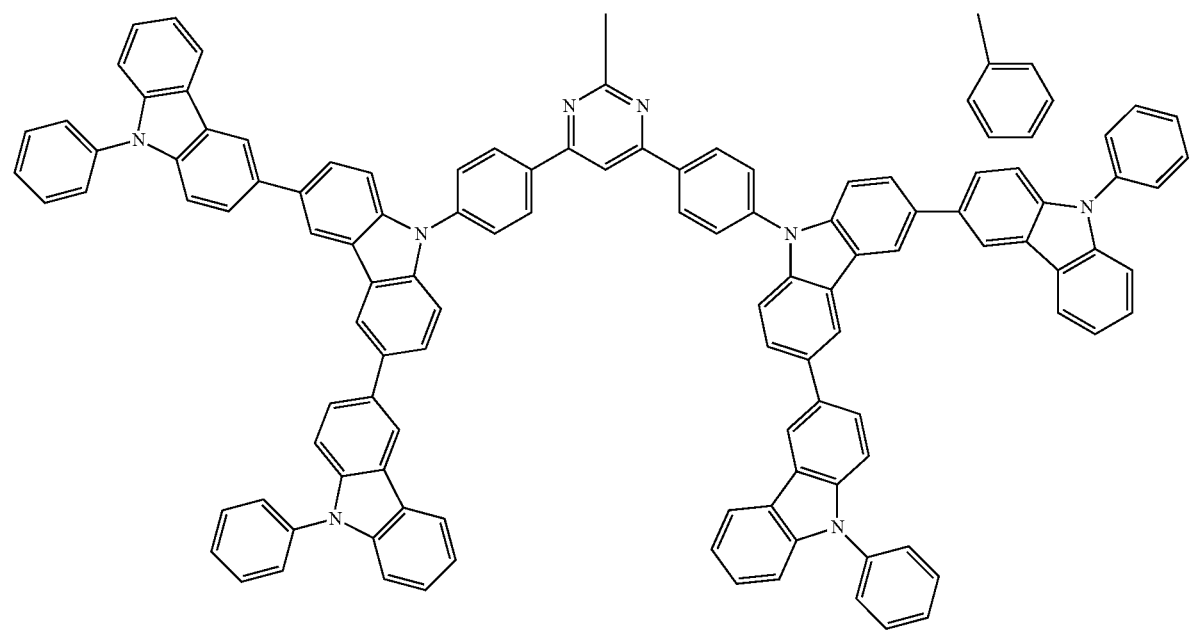

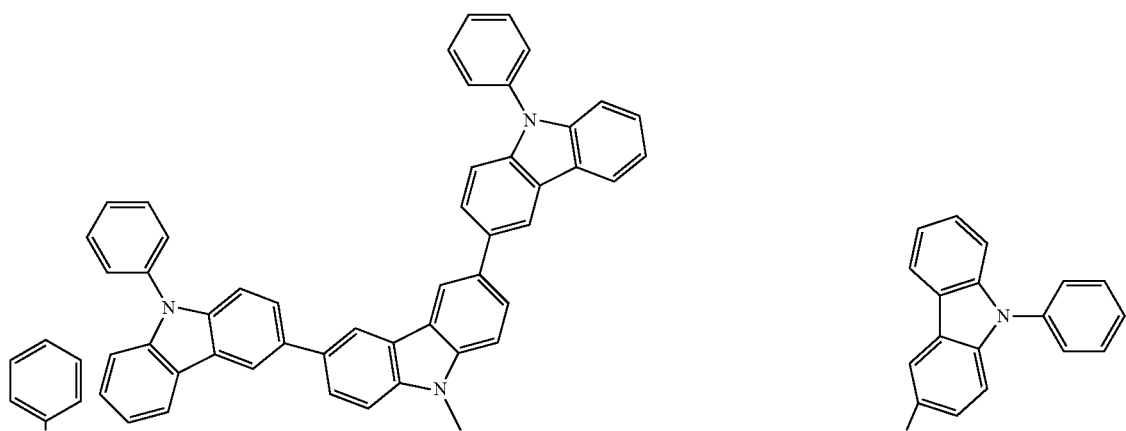
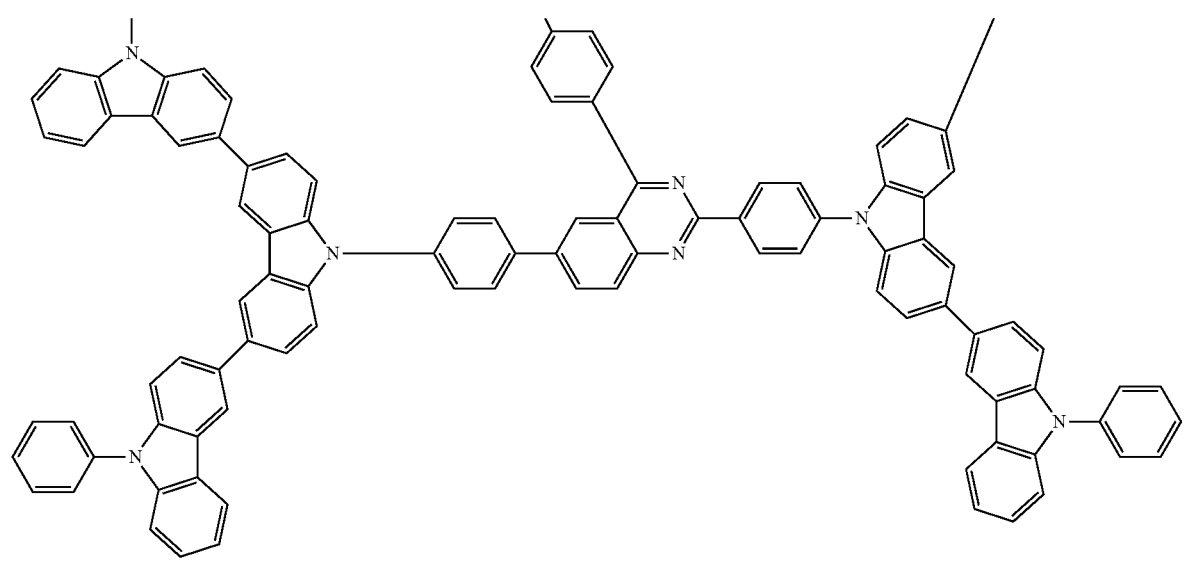
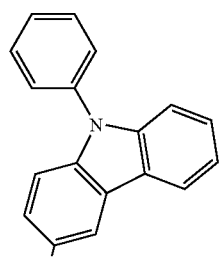

297
298
-continued
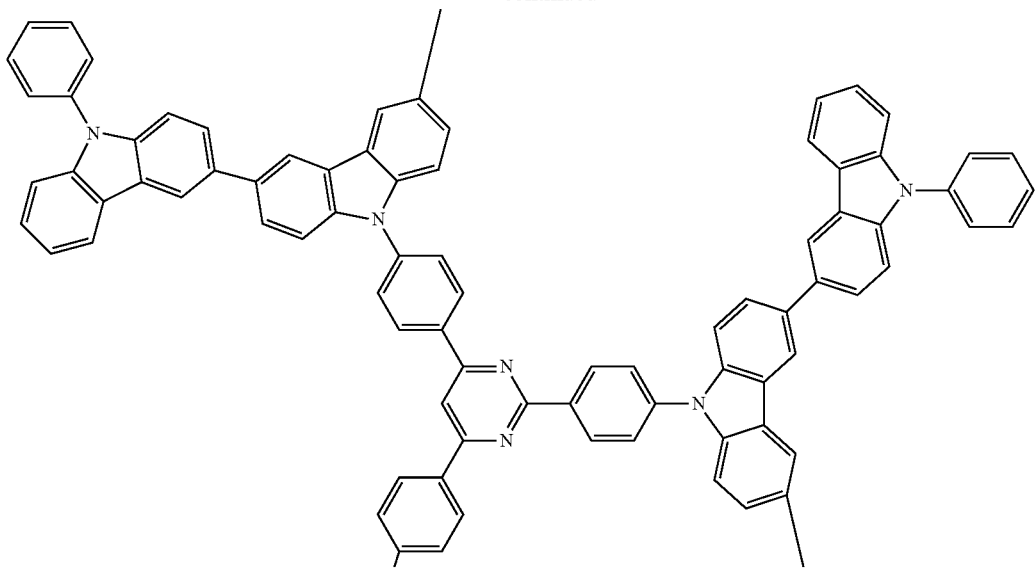
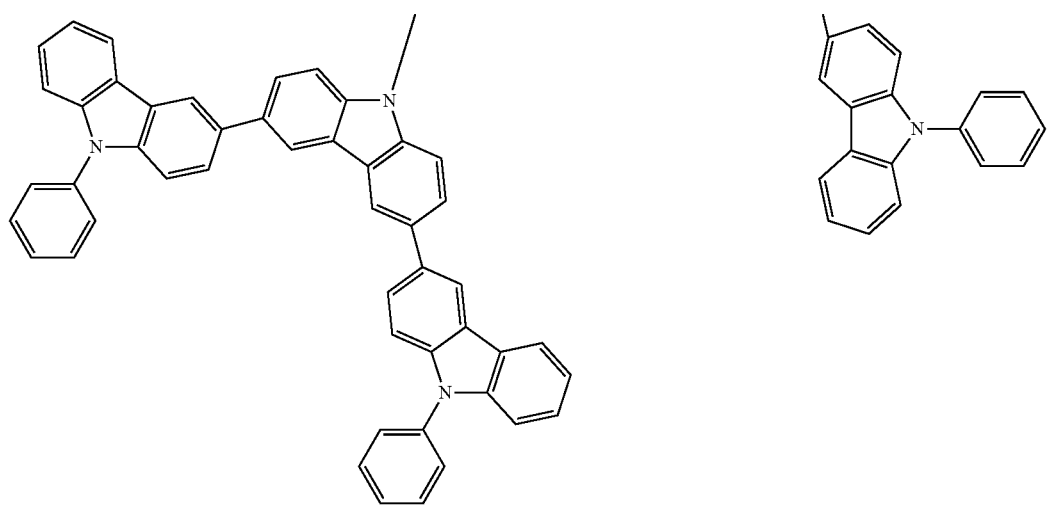
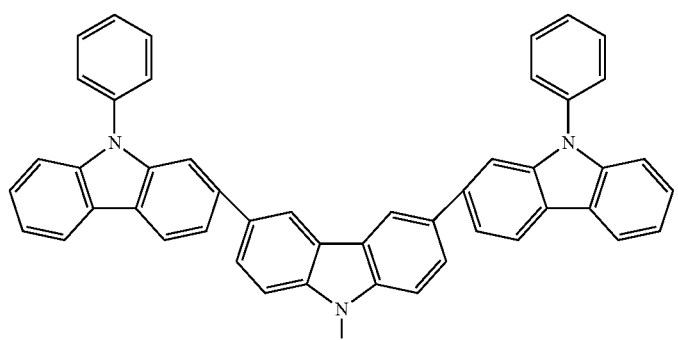

299 300
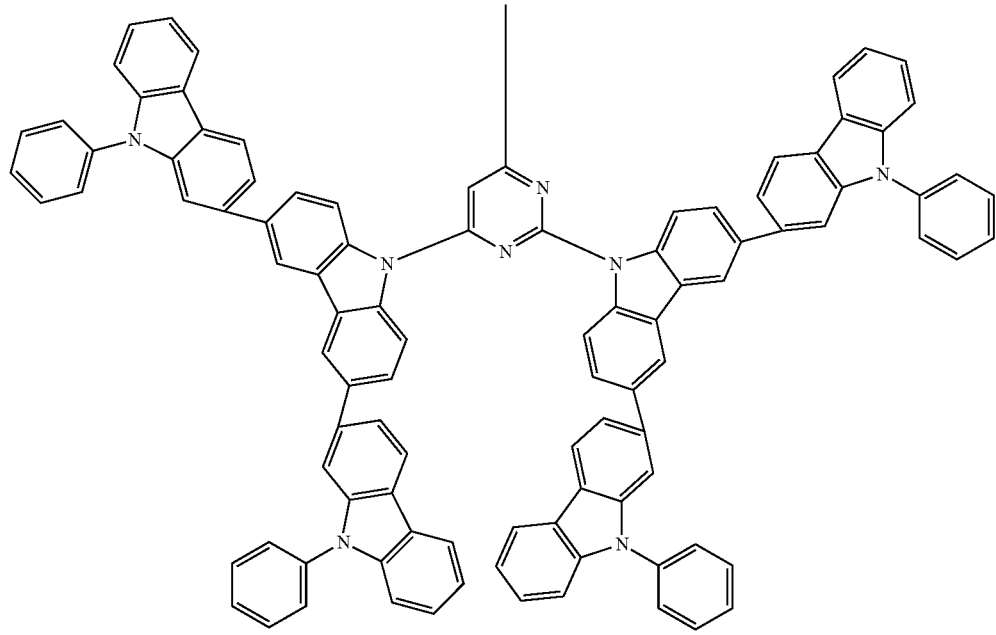
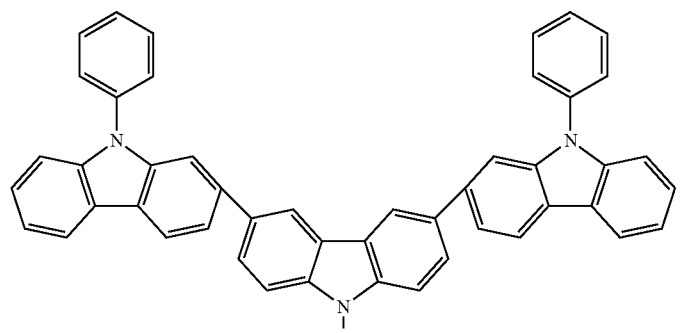
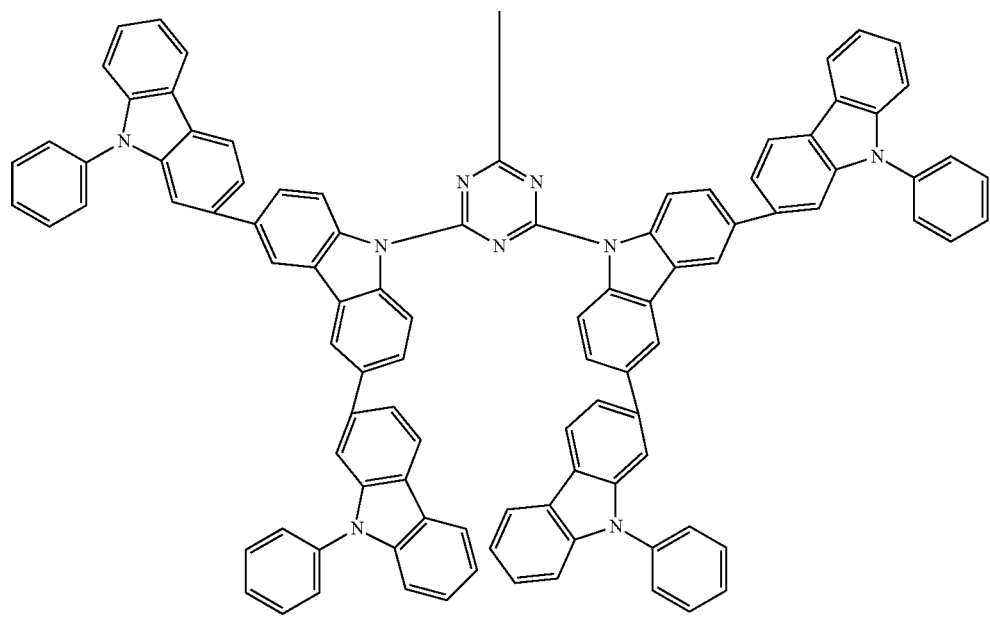

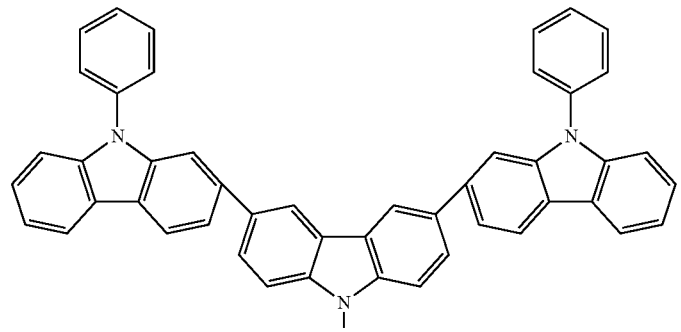
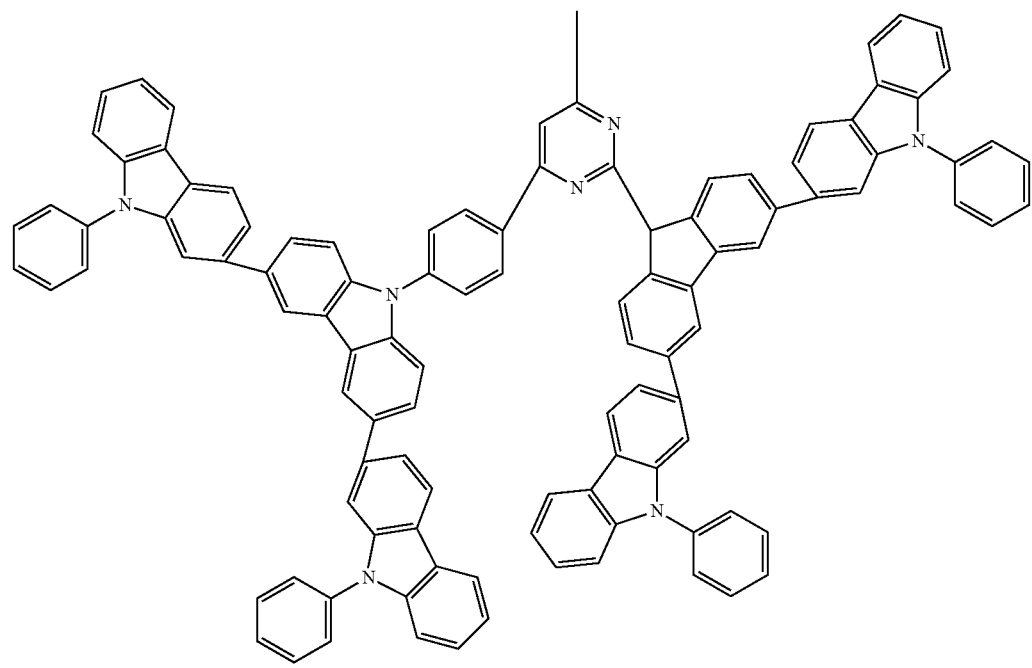
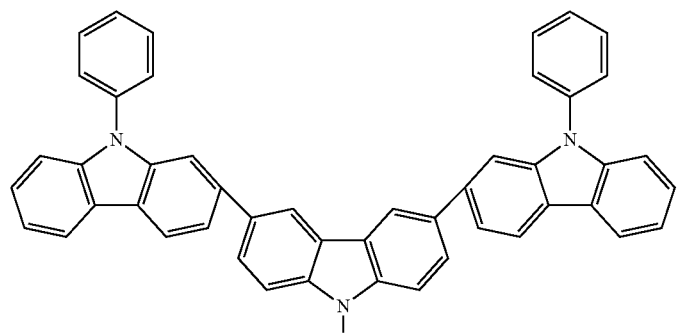

-continued
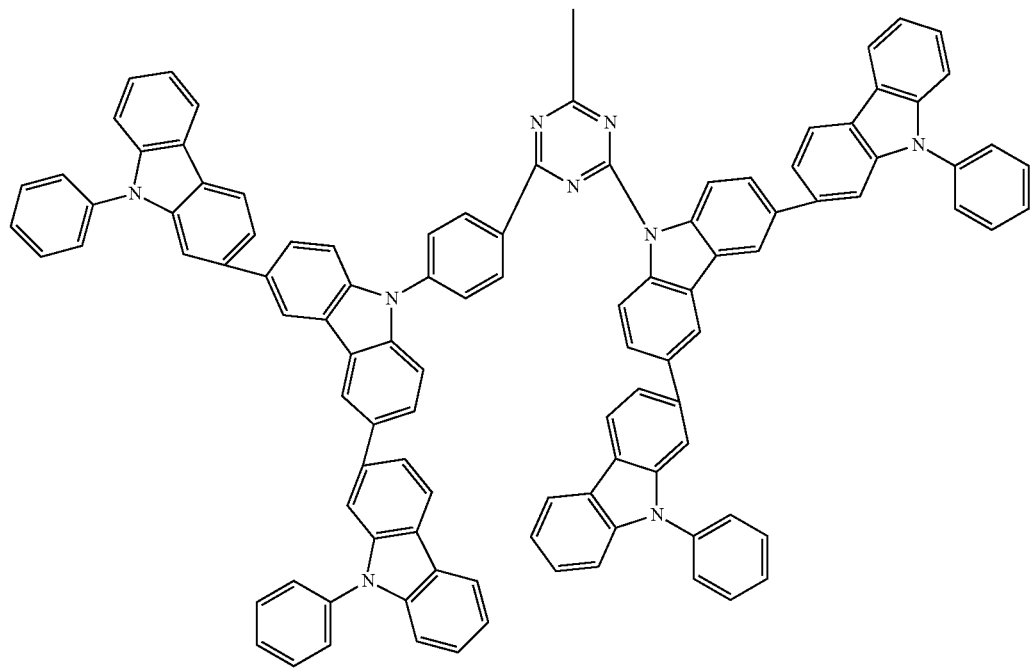
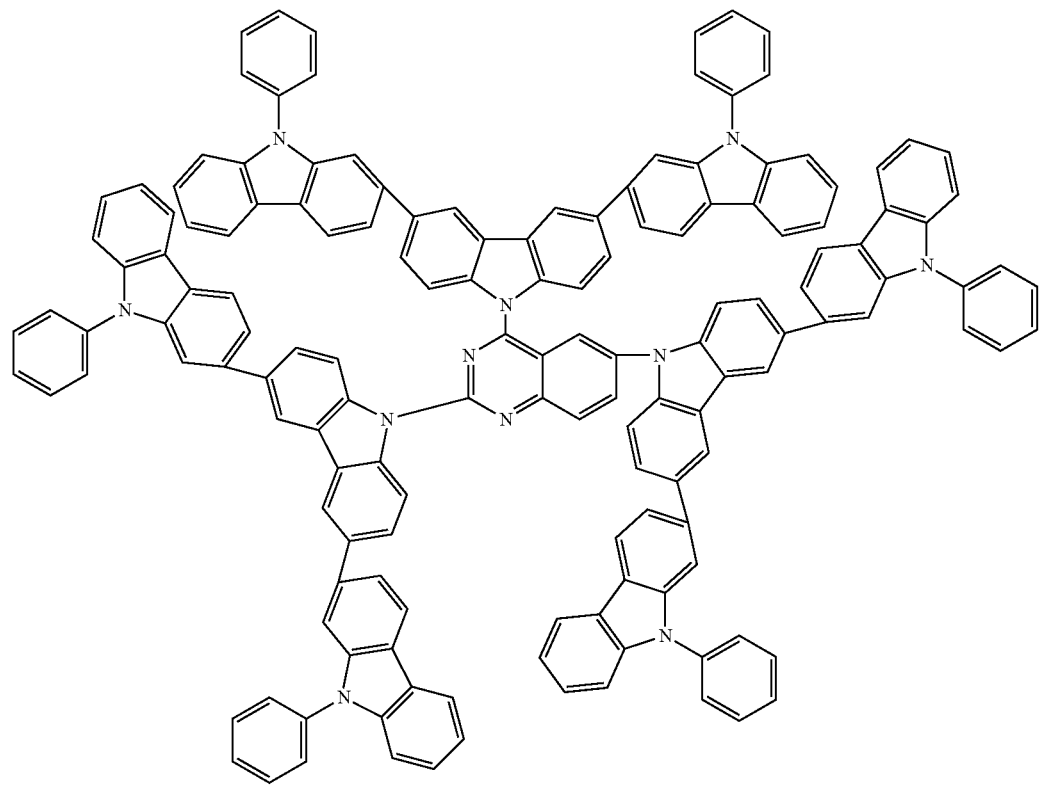

-continued
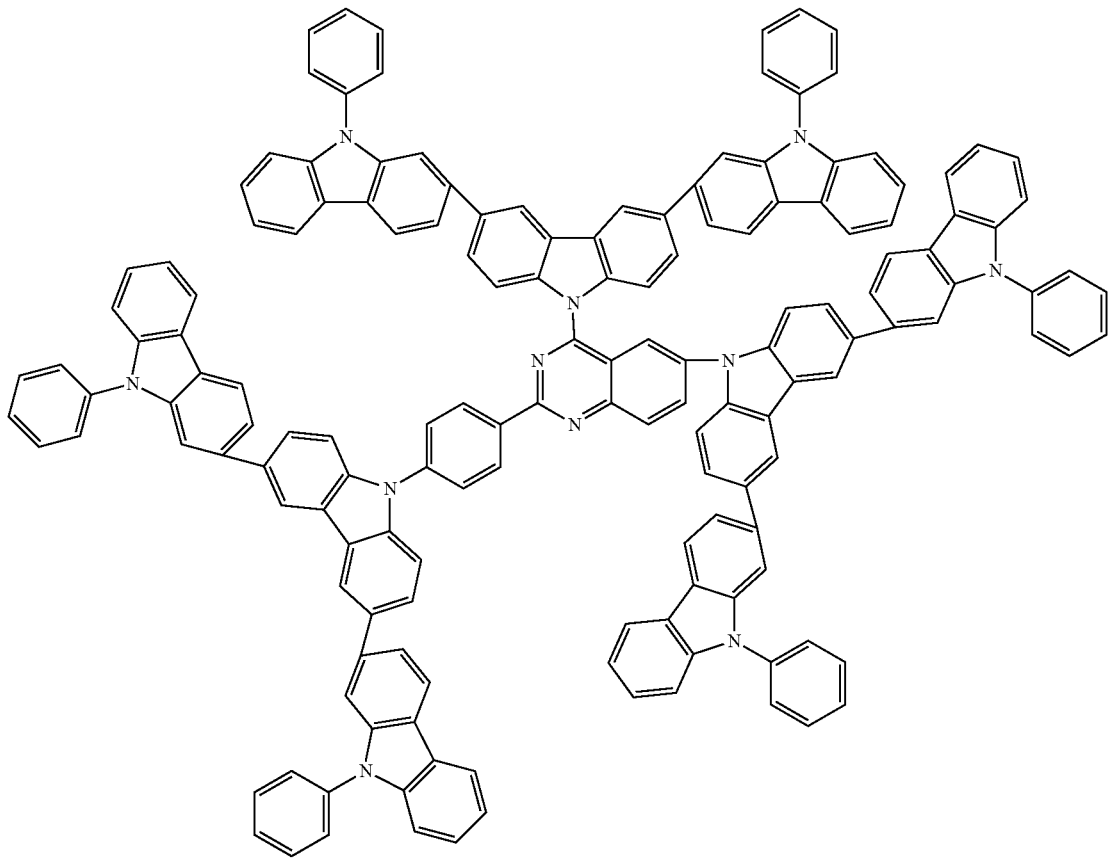
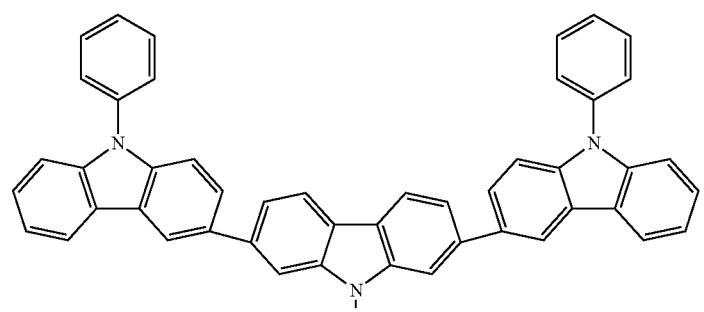

307
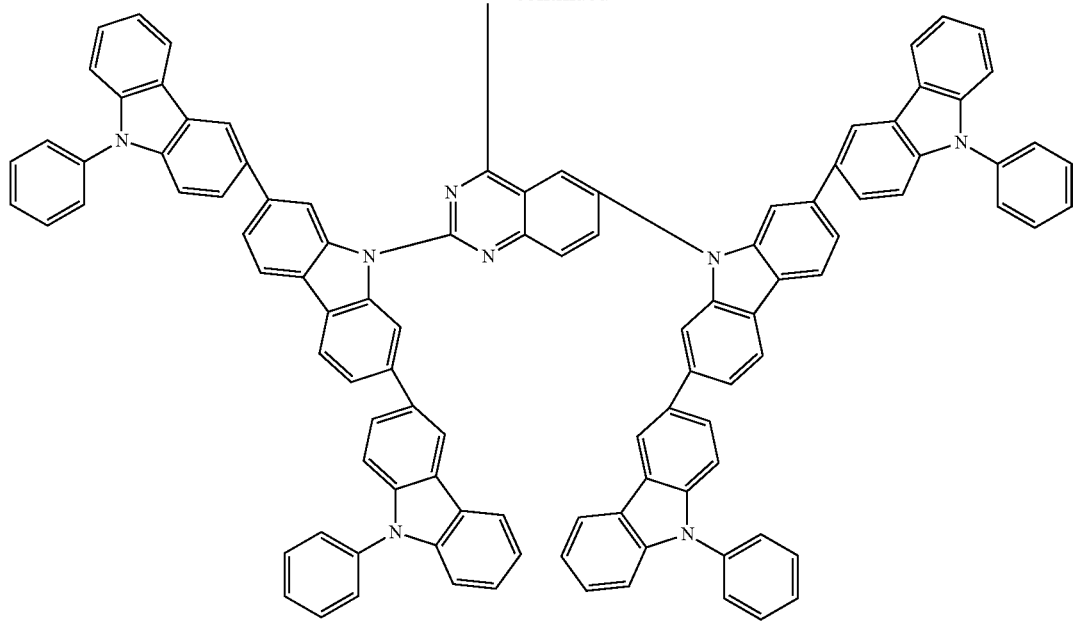
308
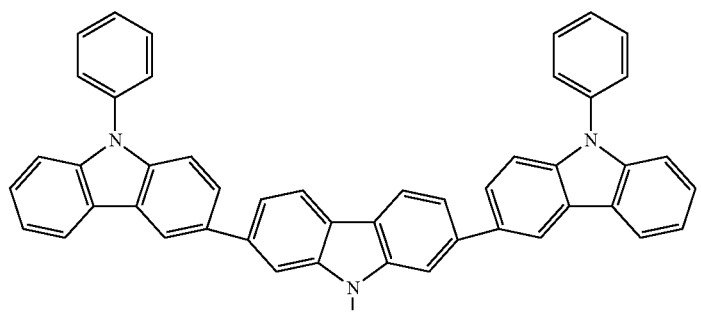

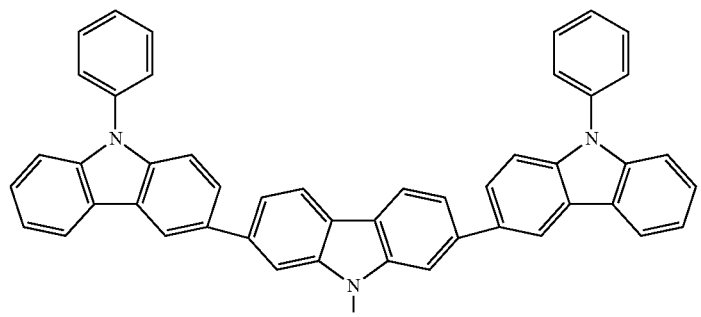
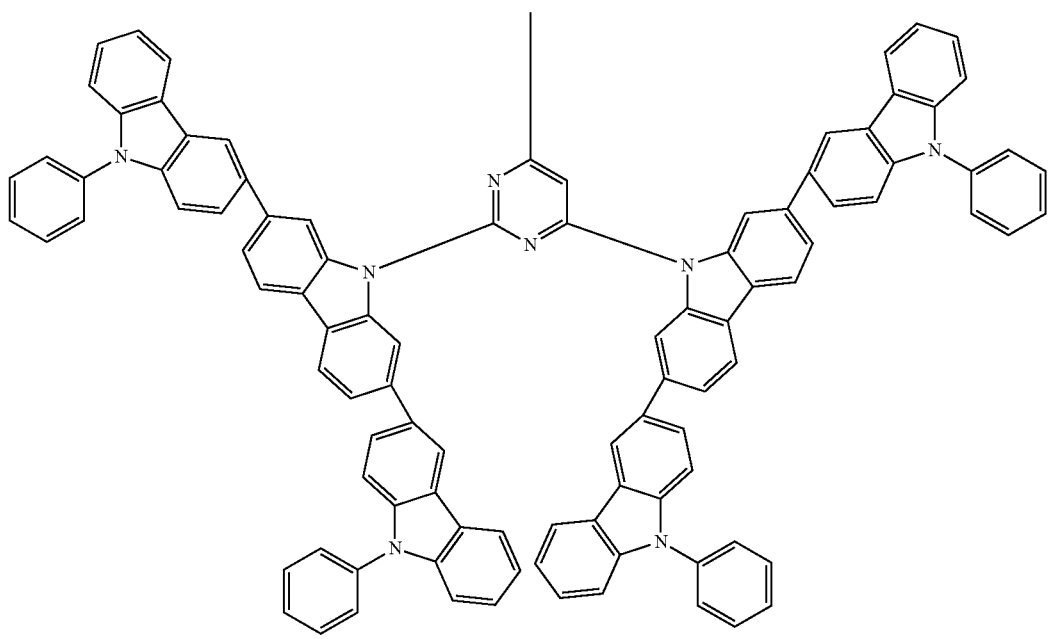
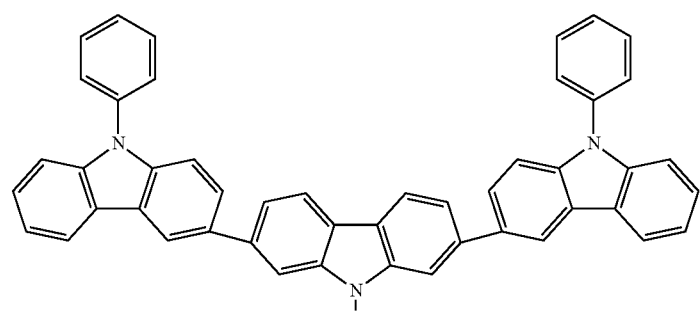

-continued
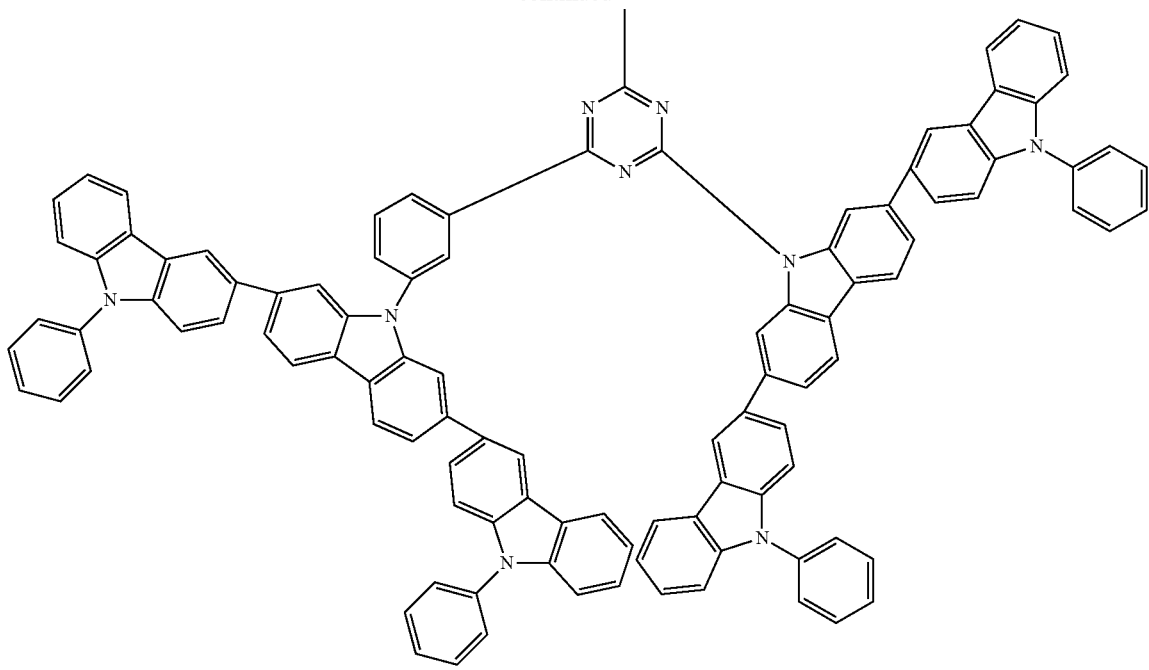
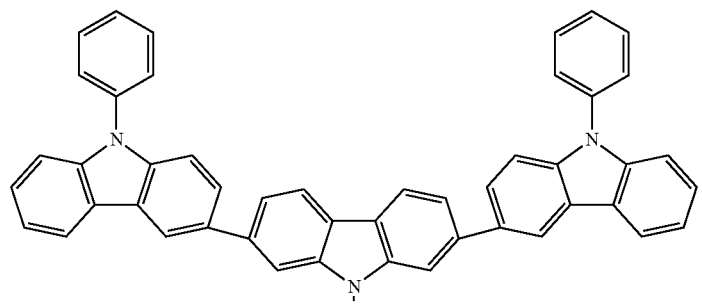
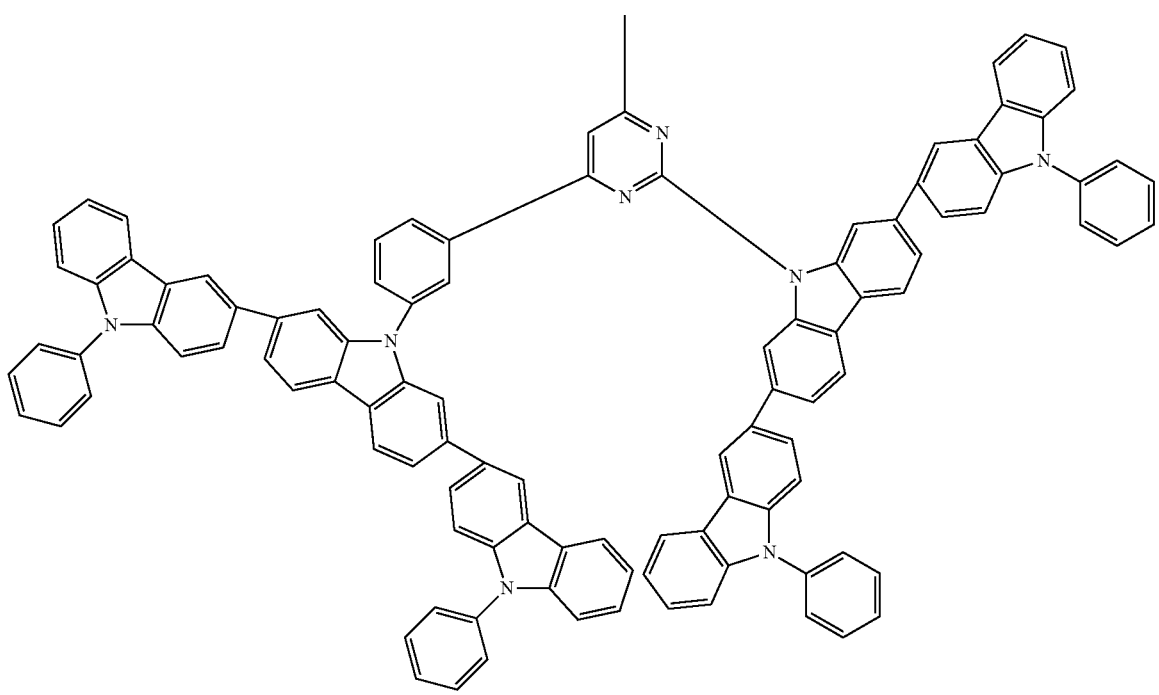

-continued
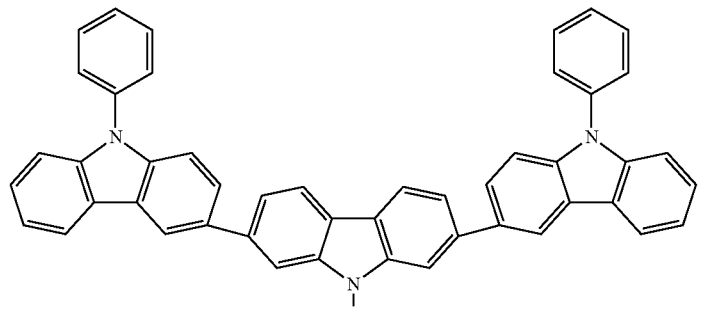
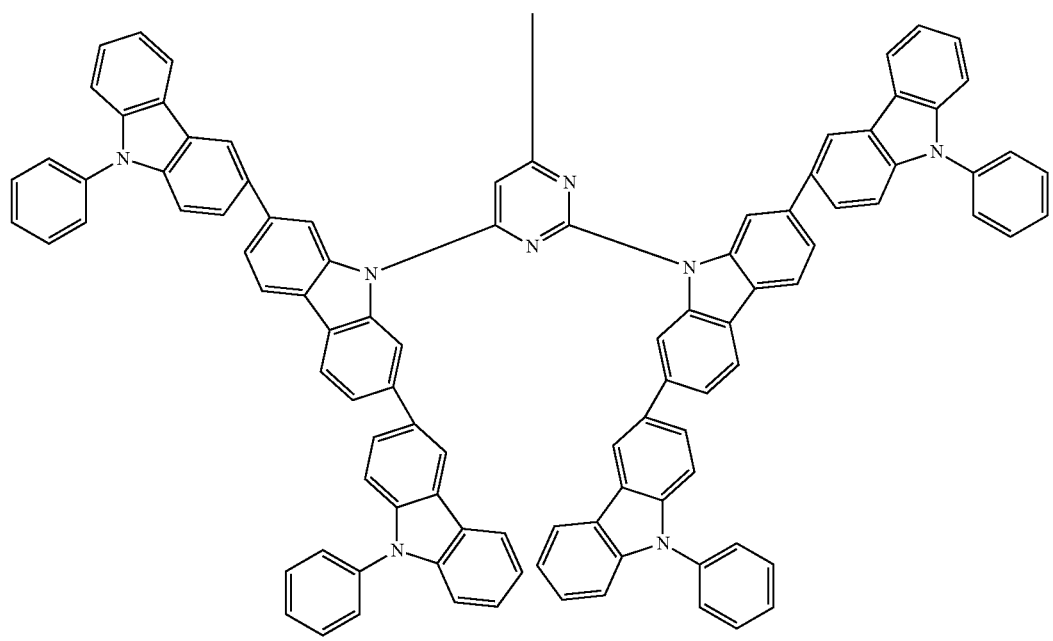
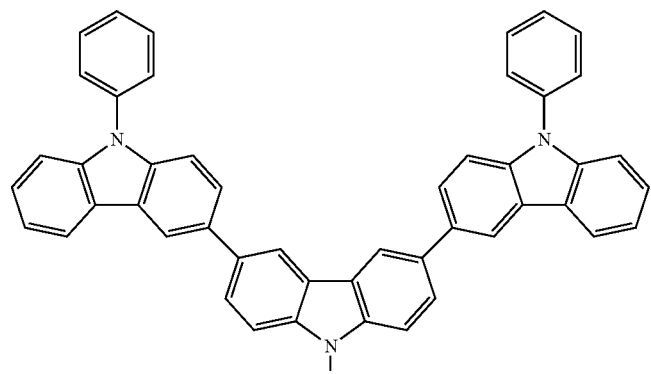

-continued
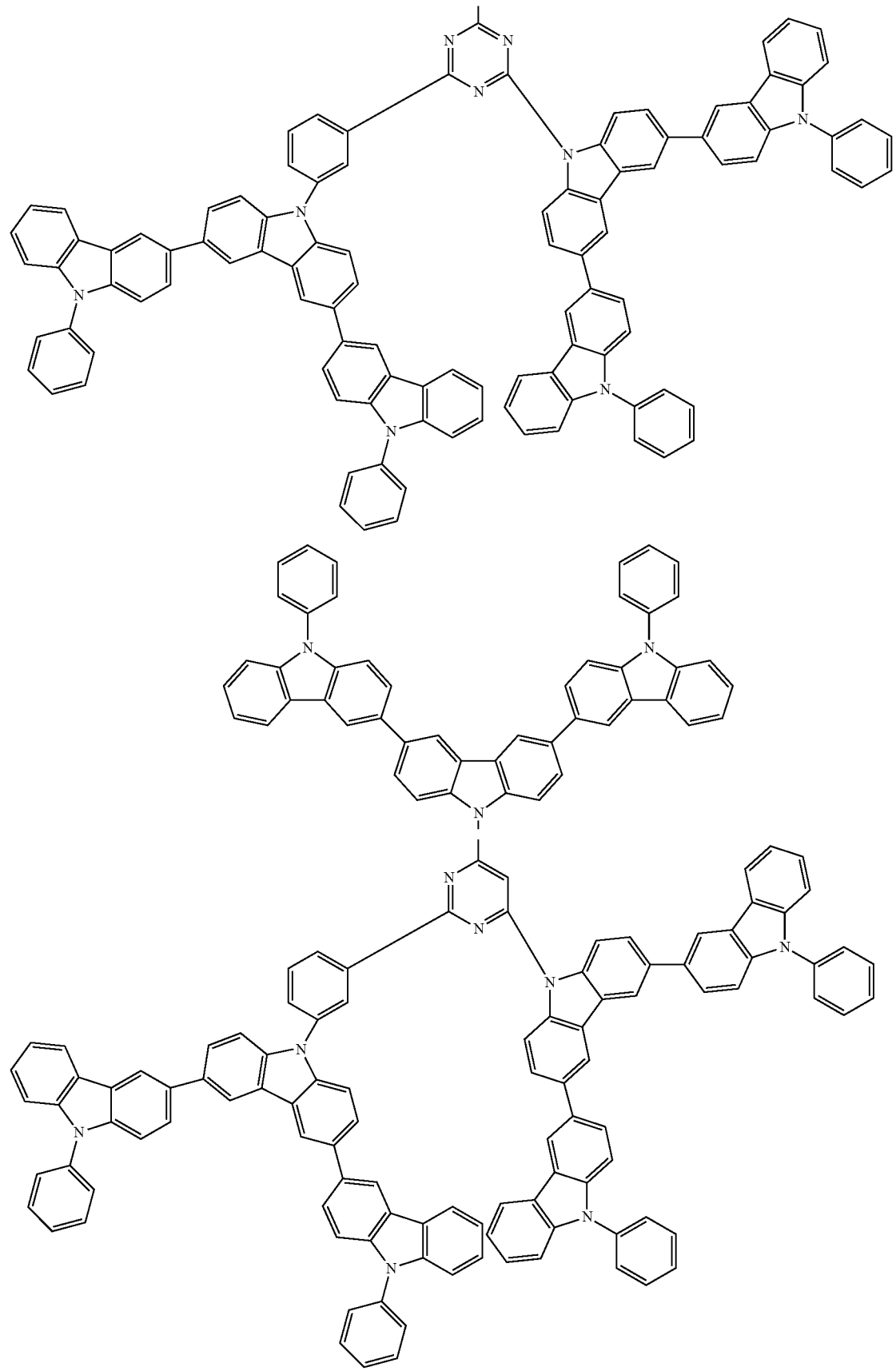

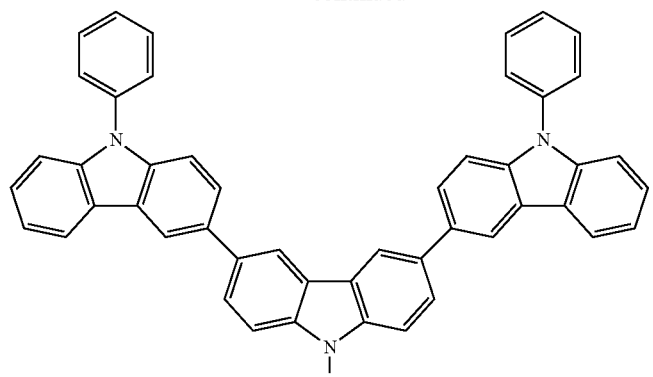
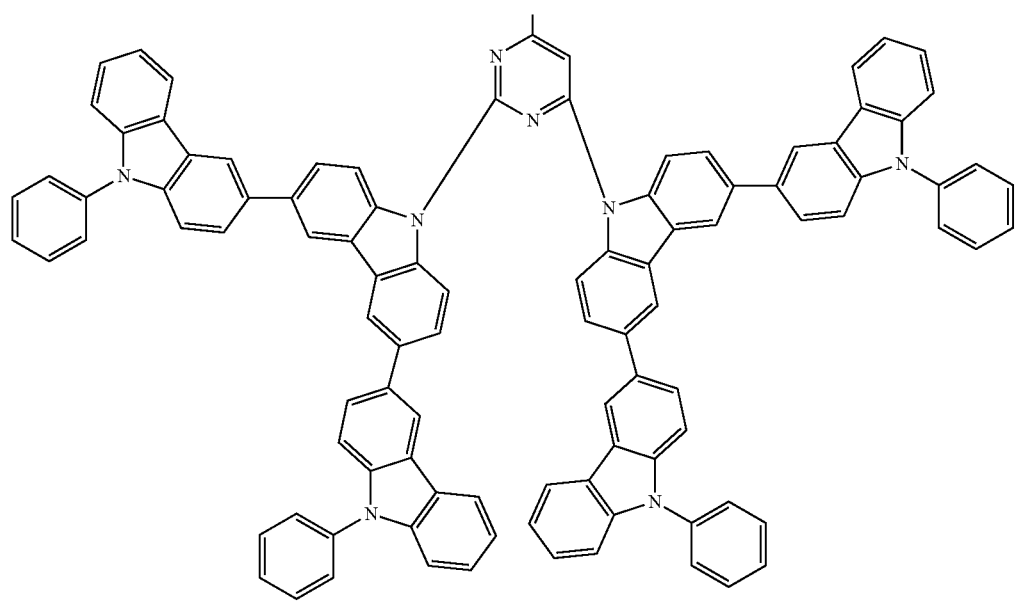
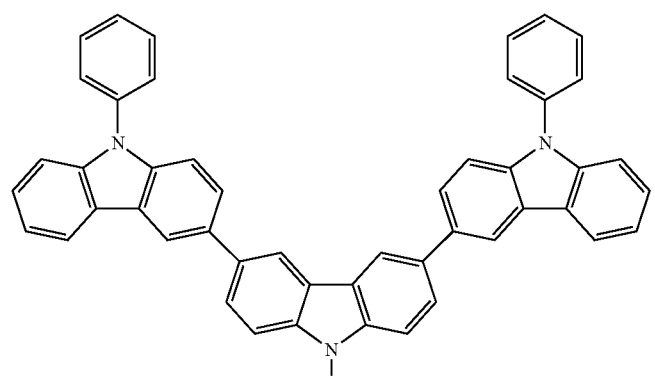

319
-continued
320
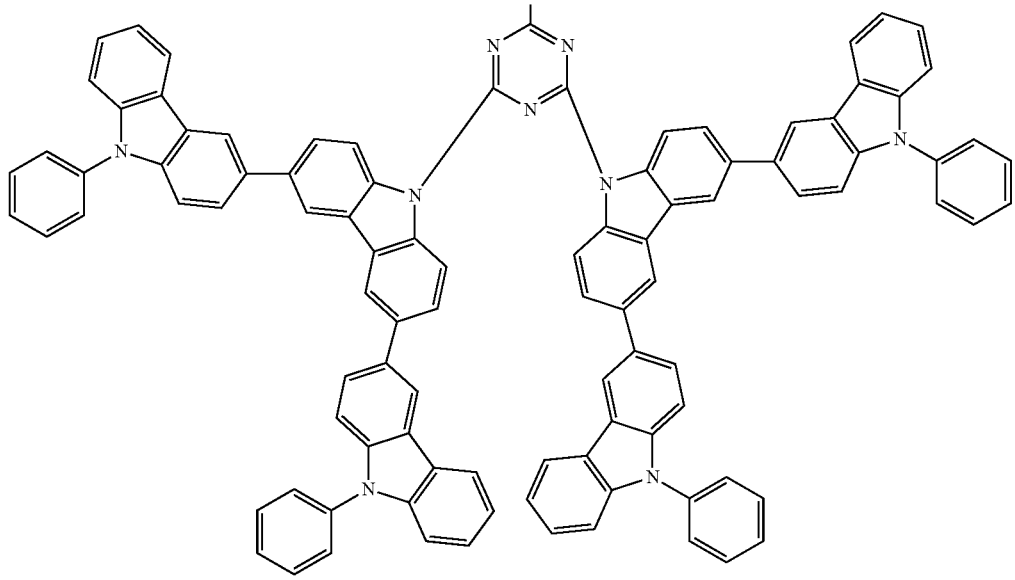
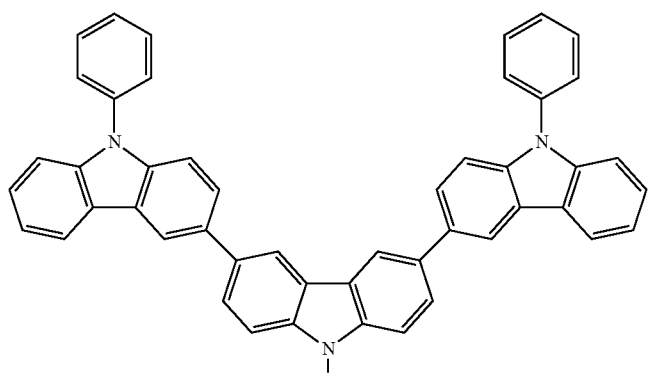
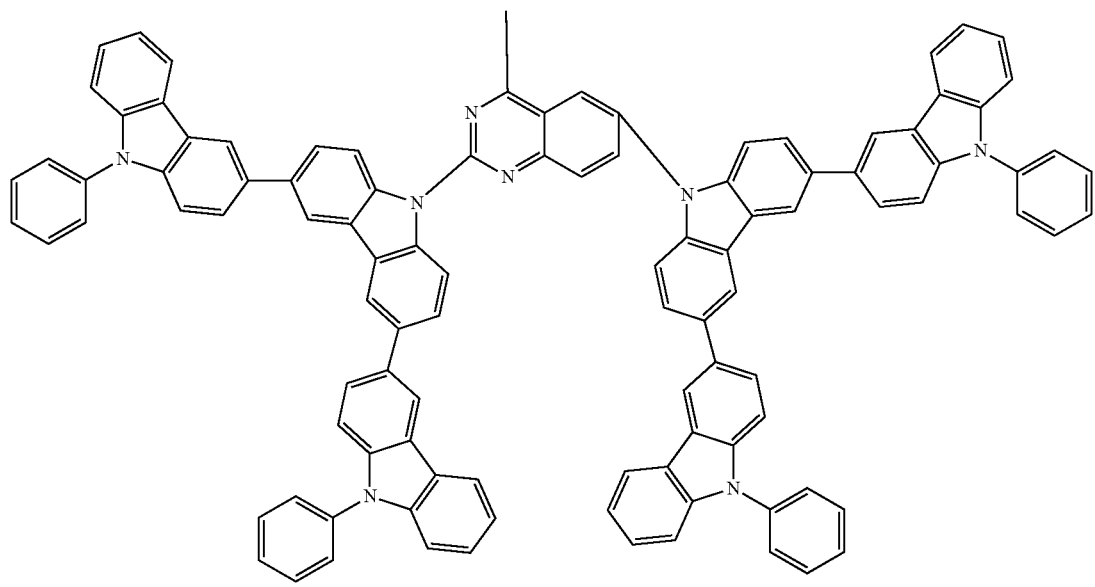

321
322
-continued
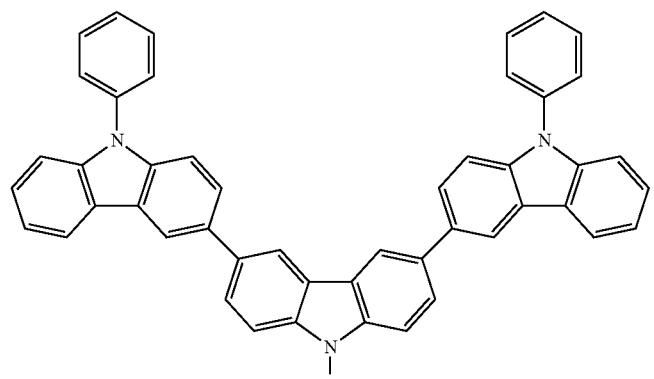
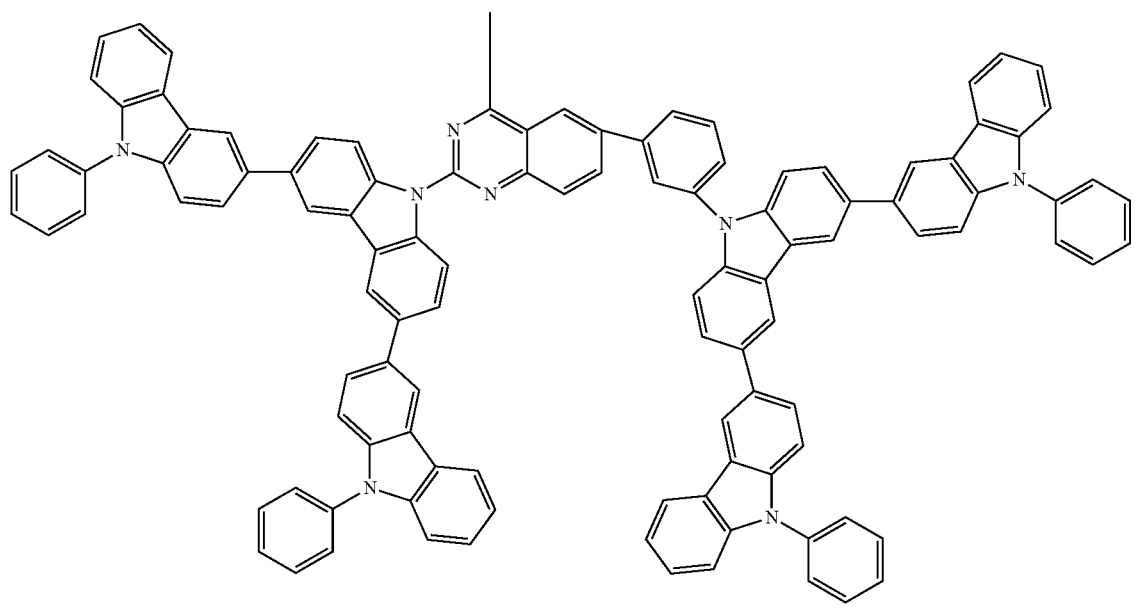
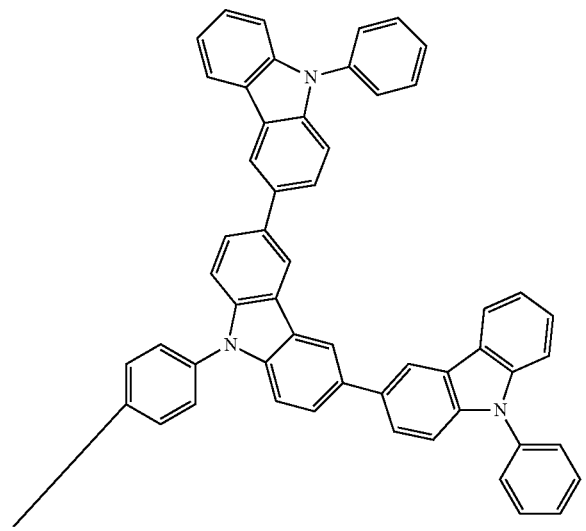

323
324
-continued
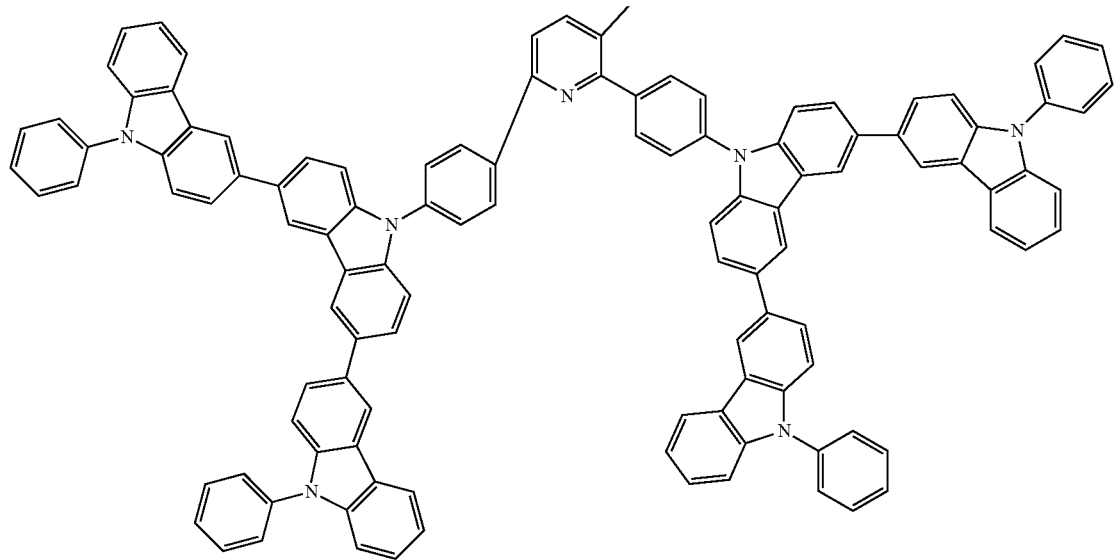
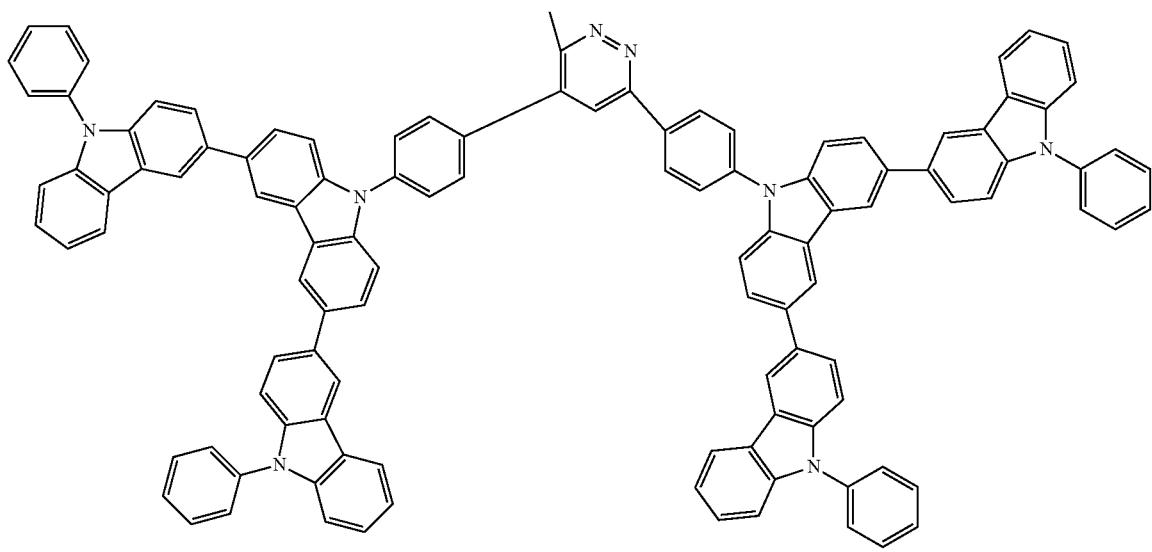

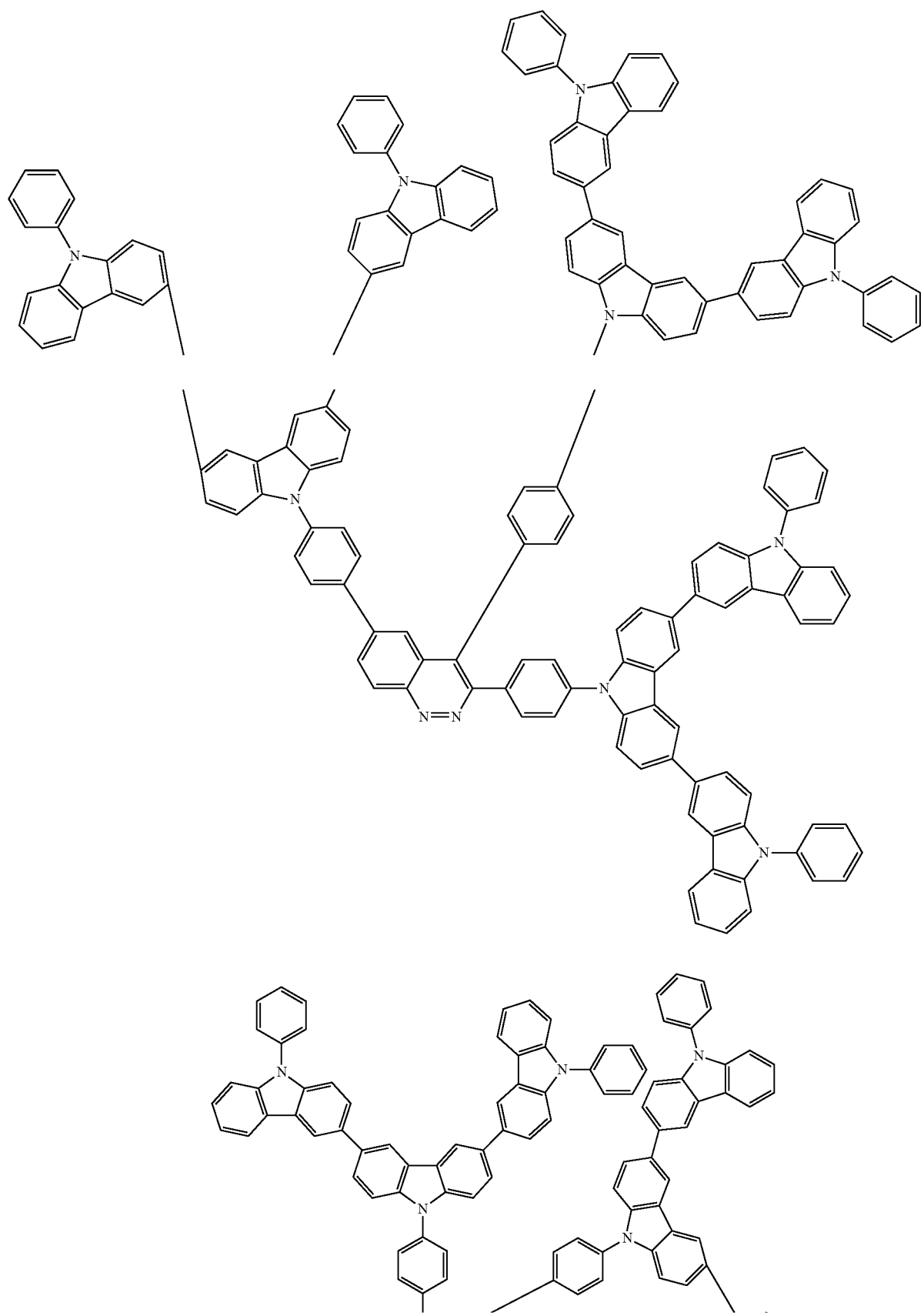

-continued
327
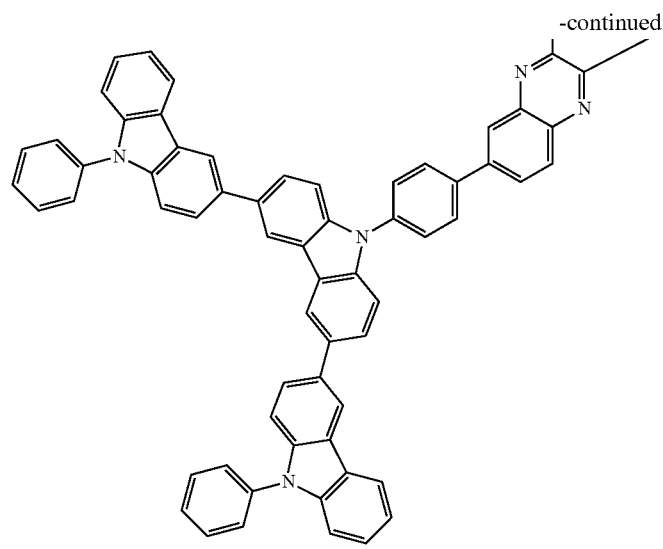
328
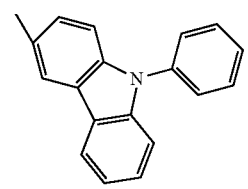
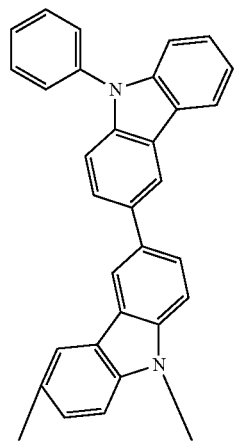
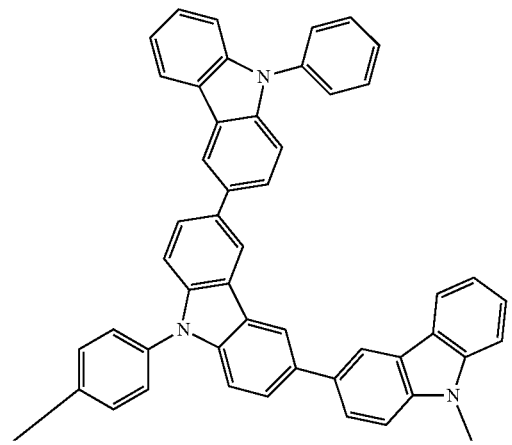
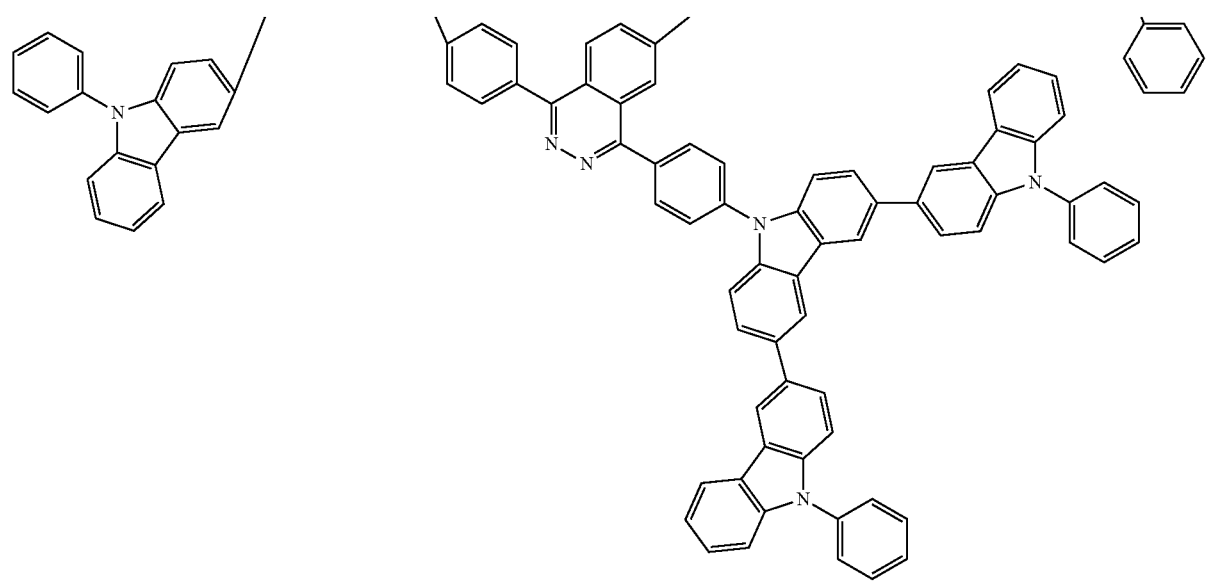

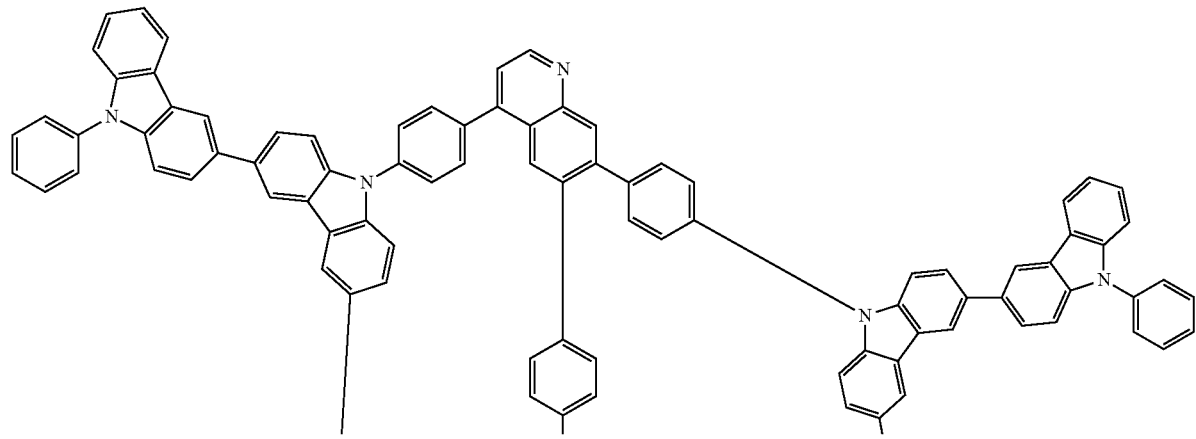
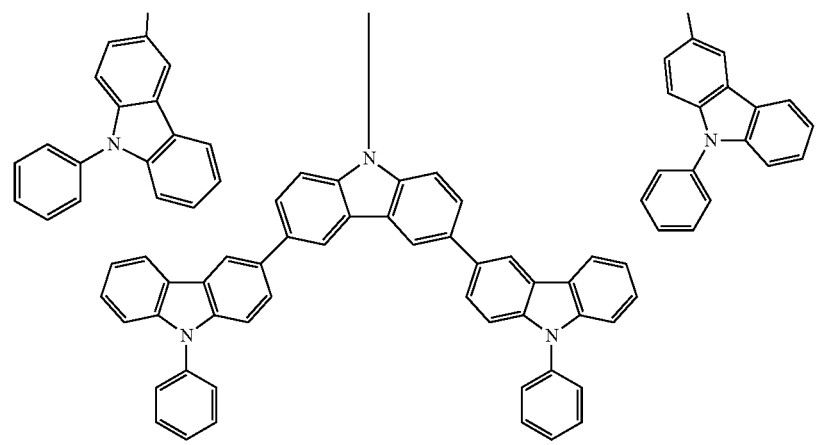
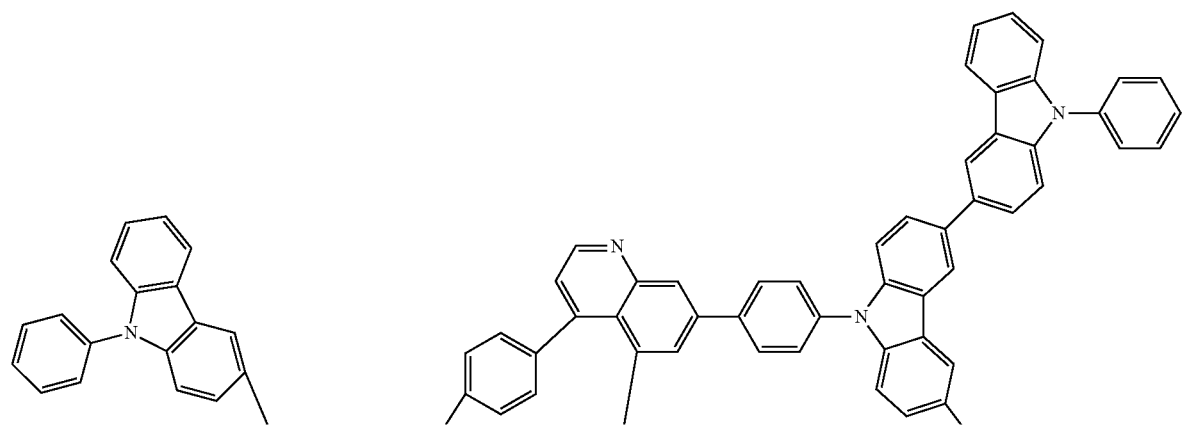

331 332
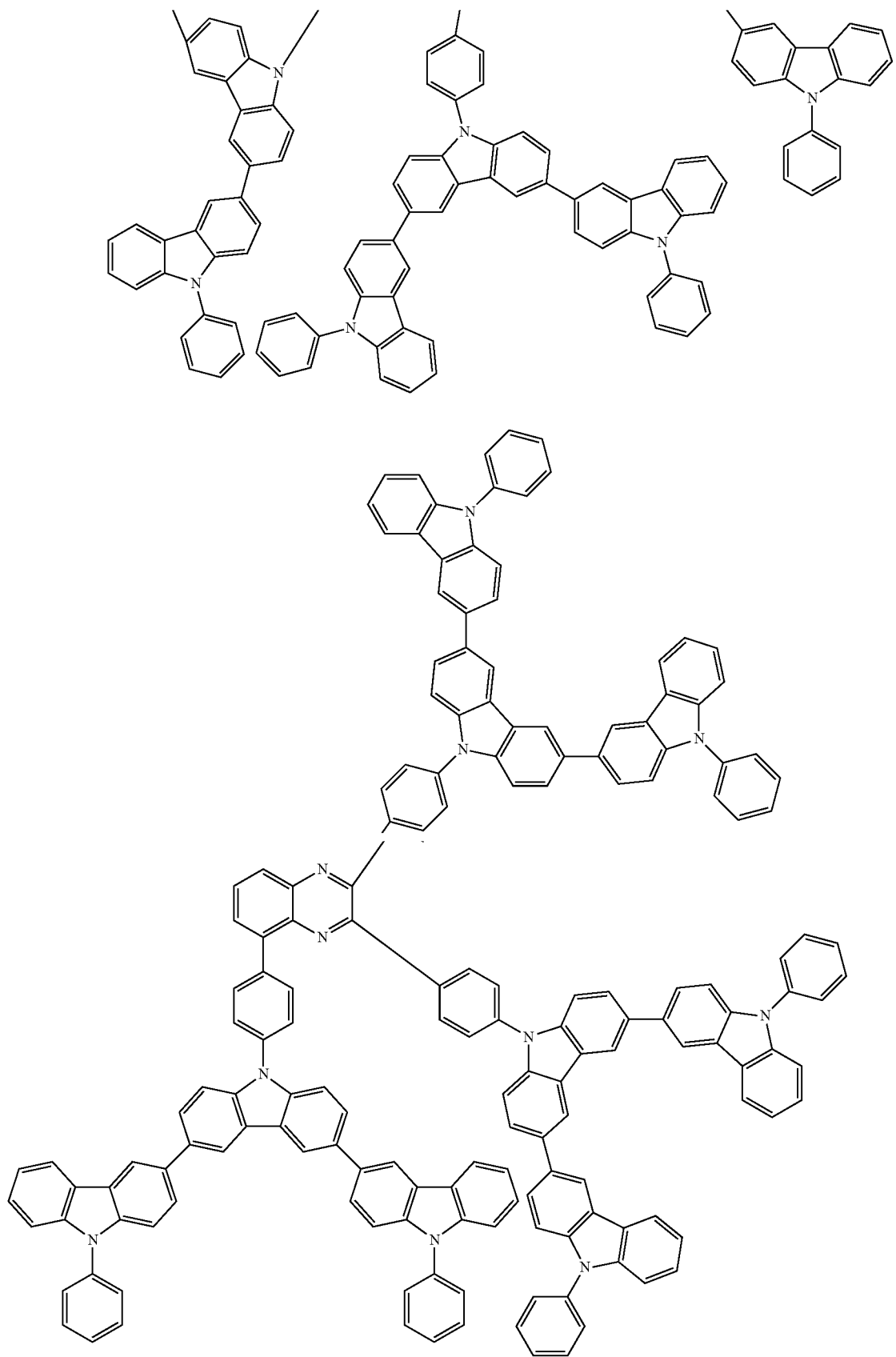

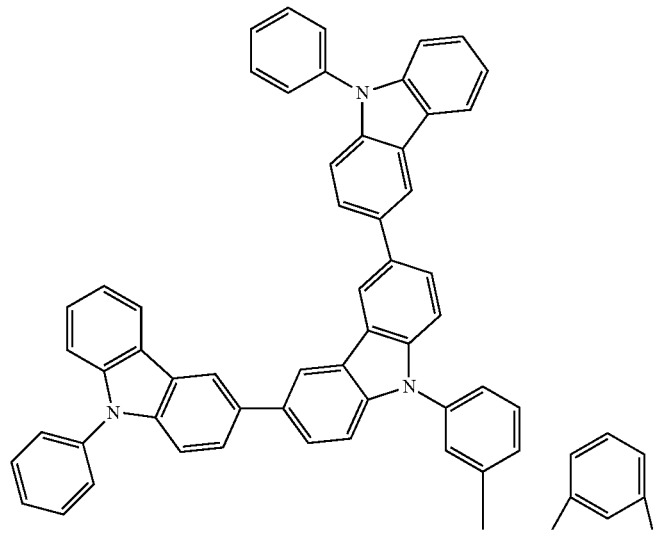
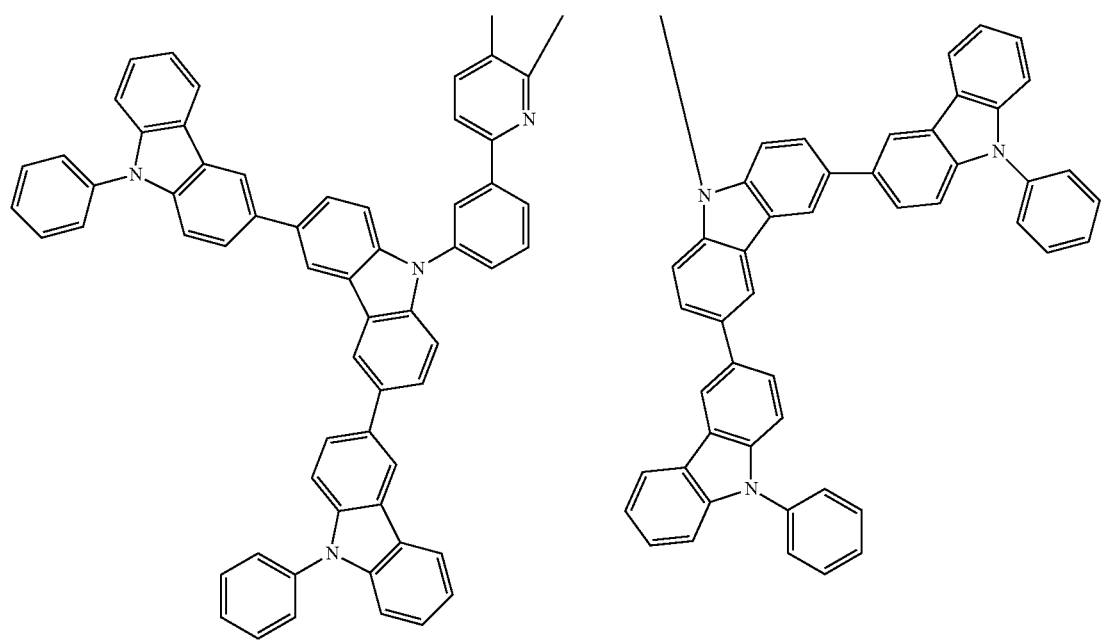
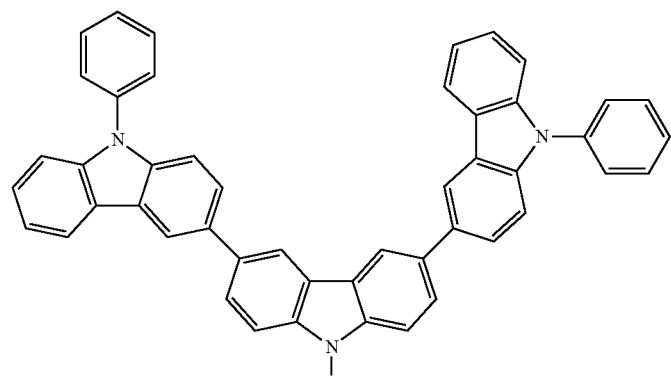

-continued
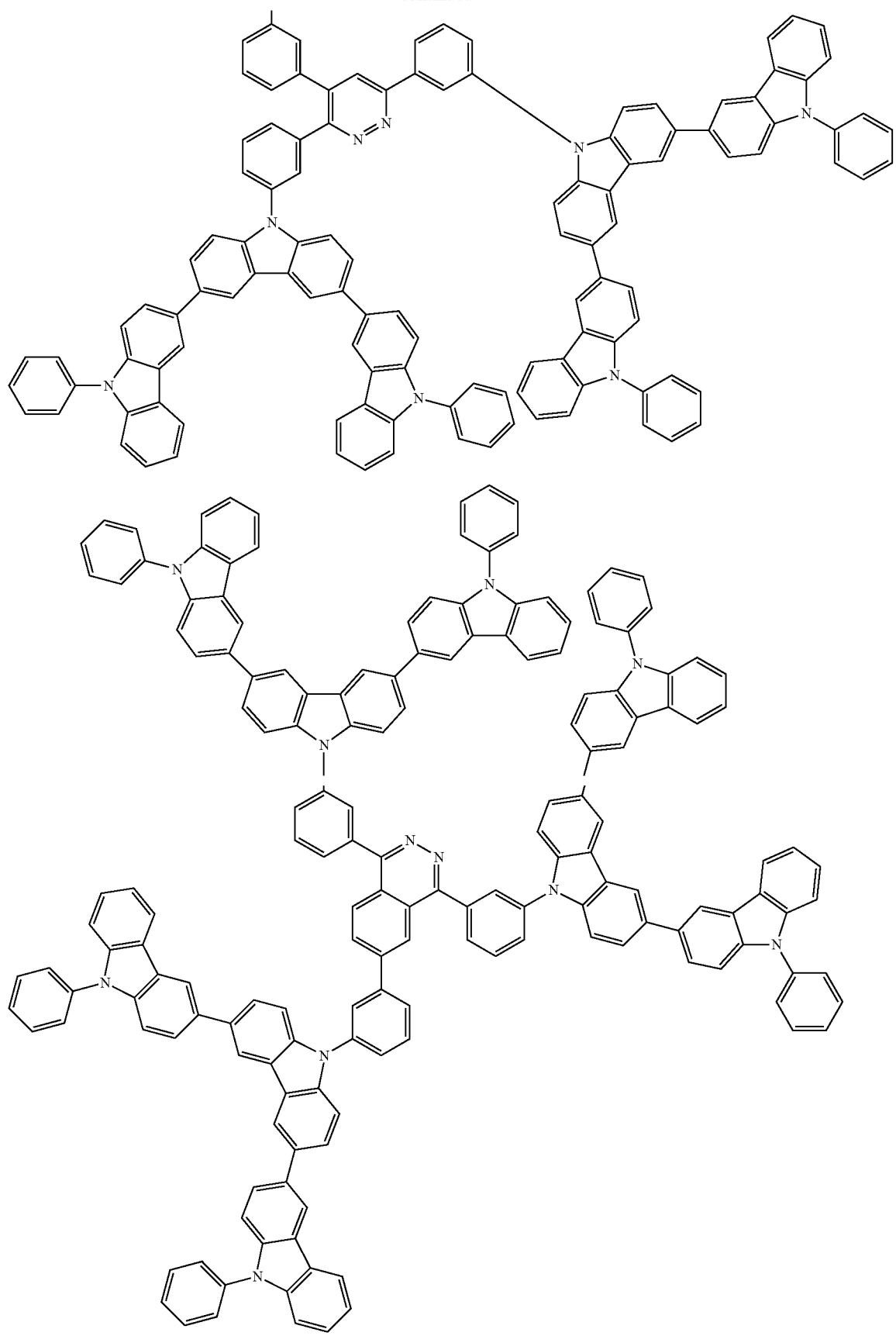

-continued
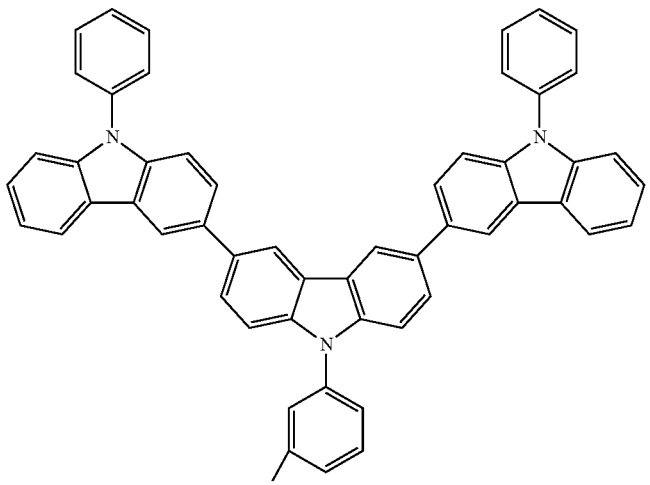
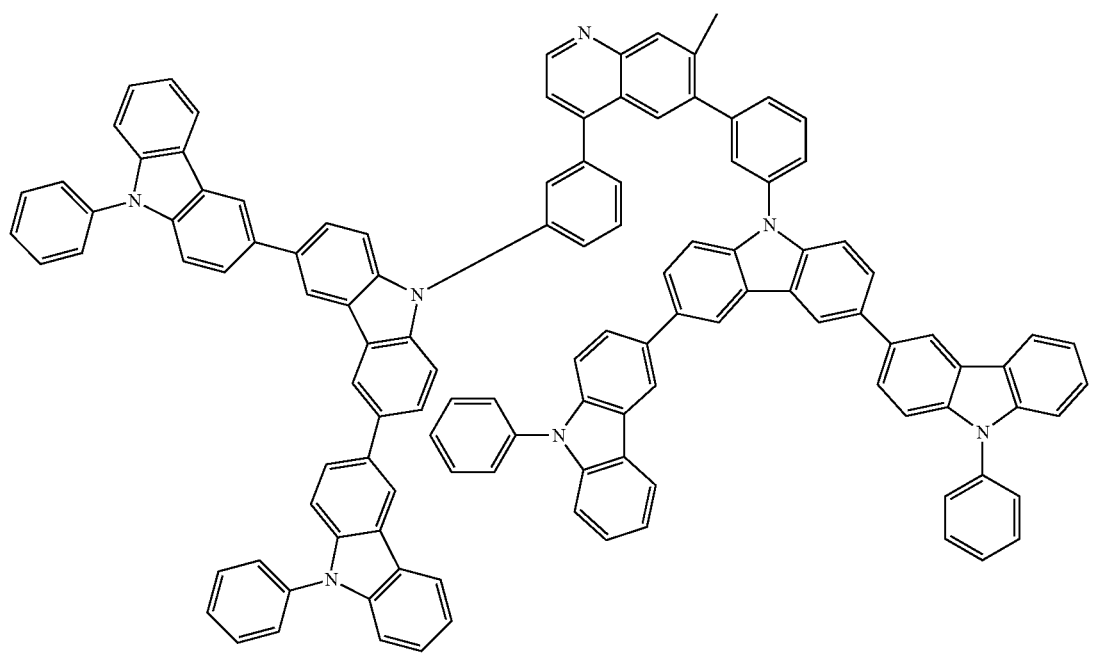
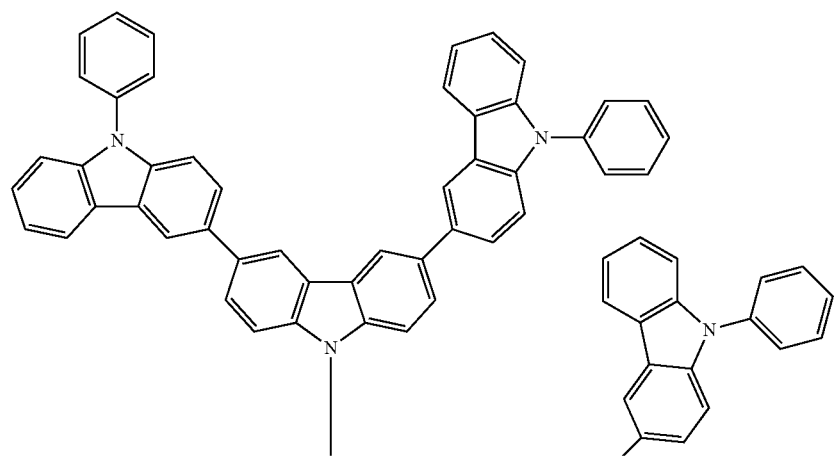

-continued
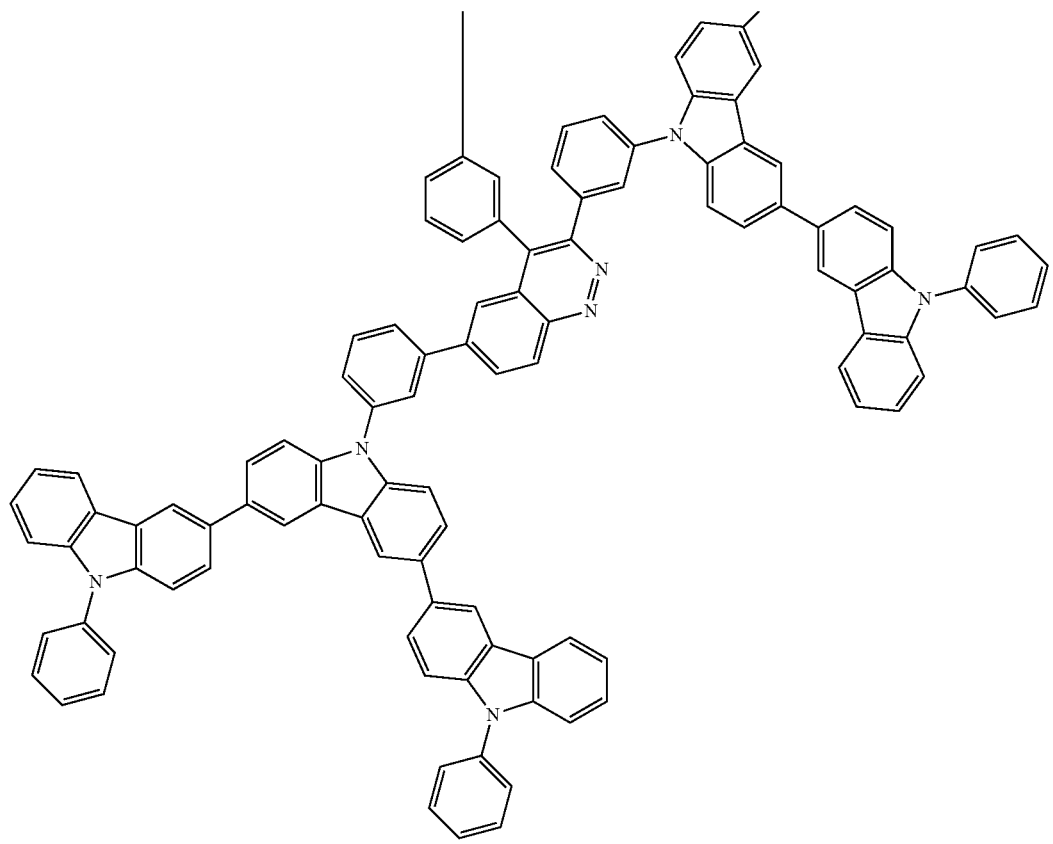
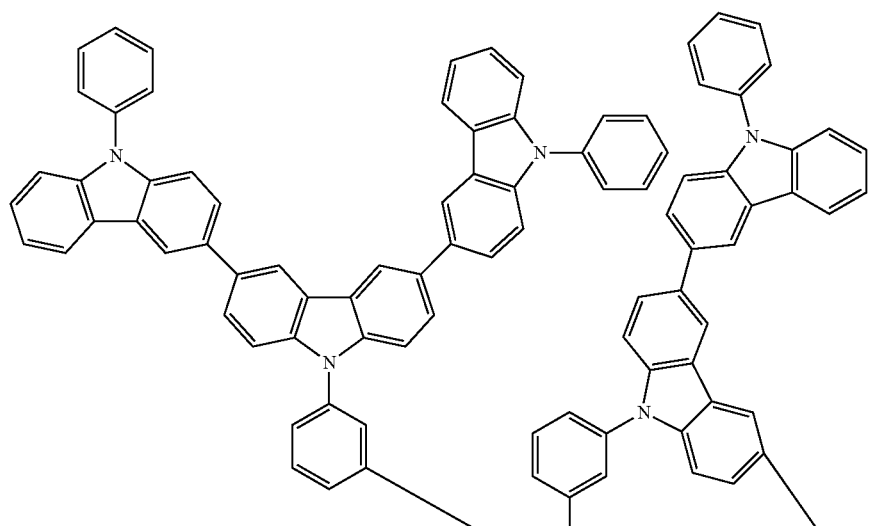

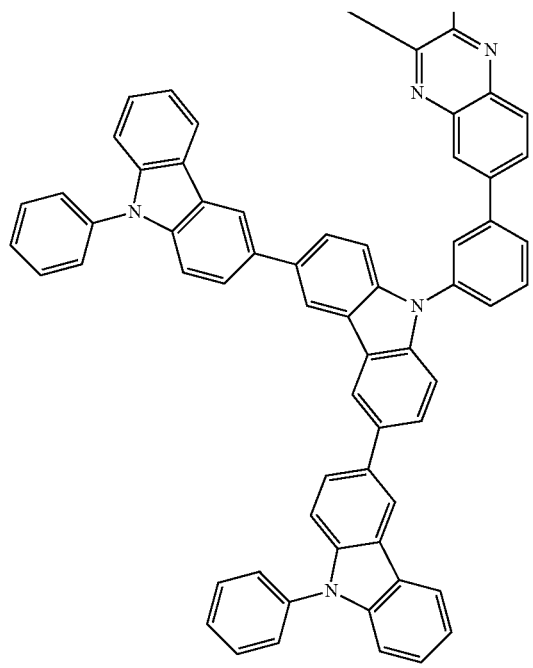
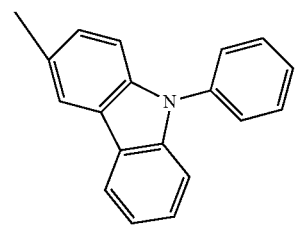
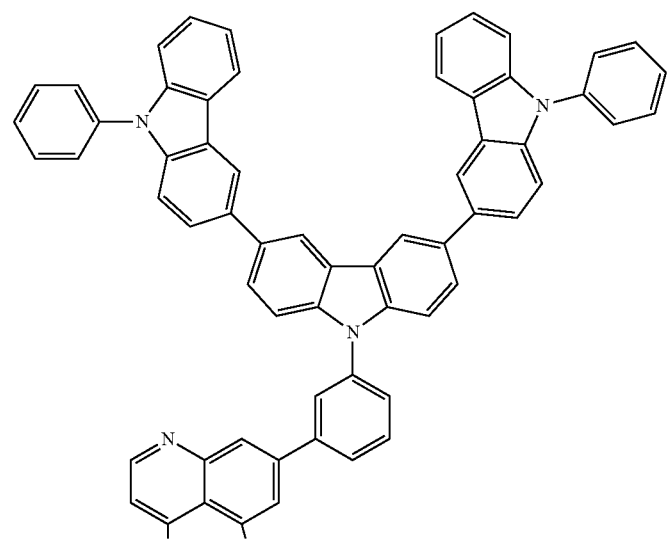

-continued
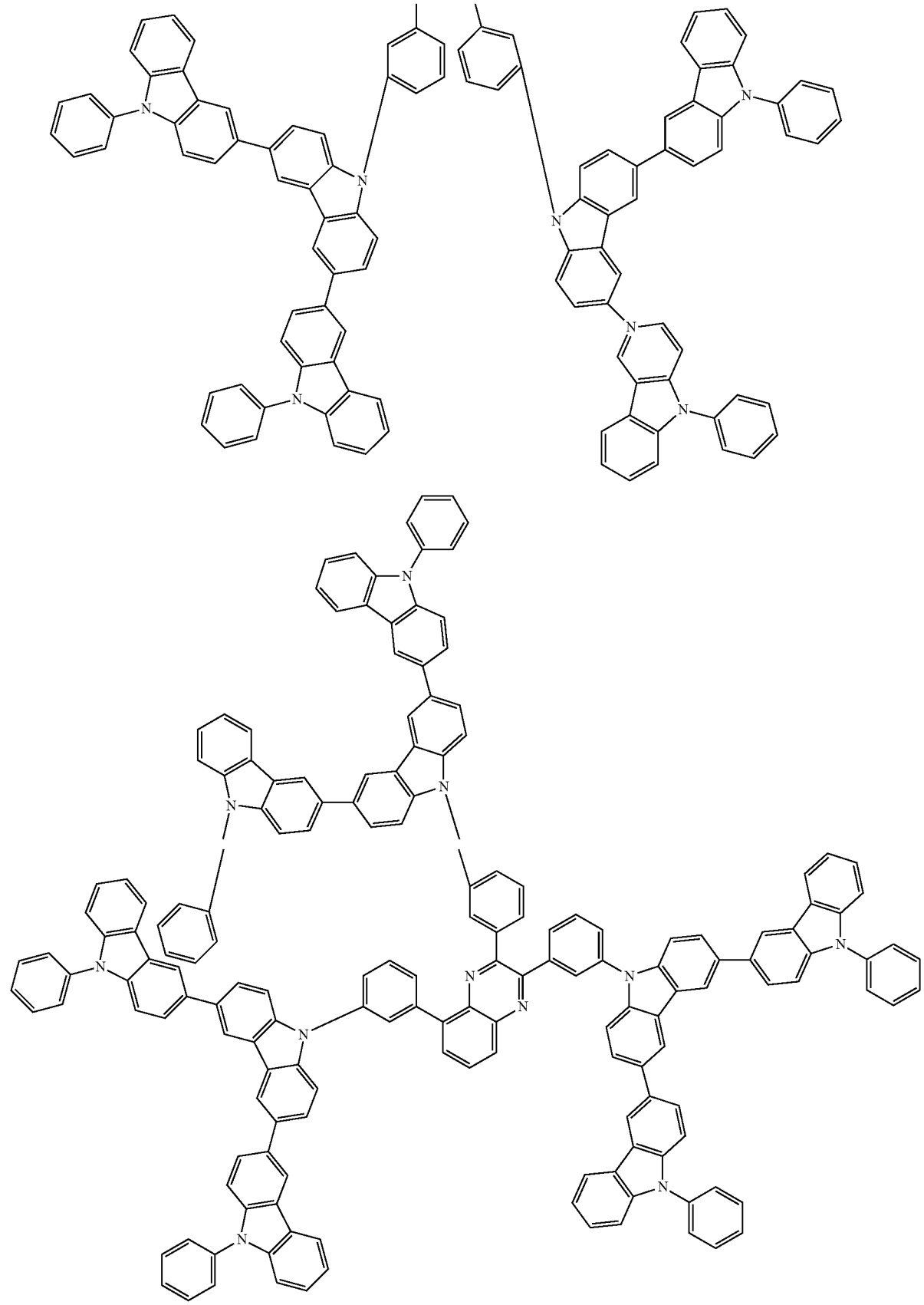

-continued
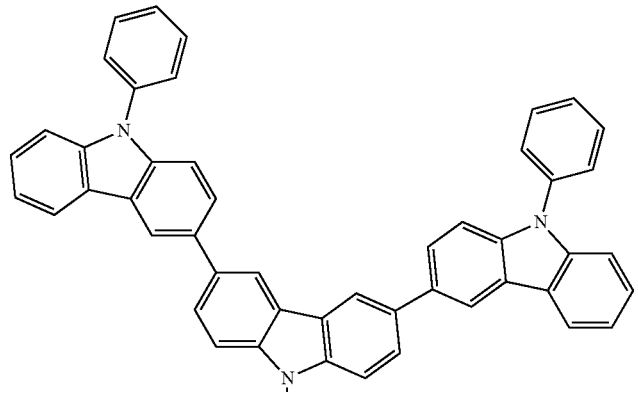
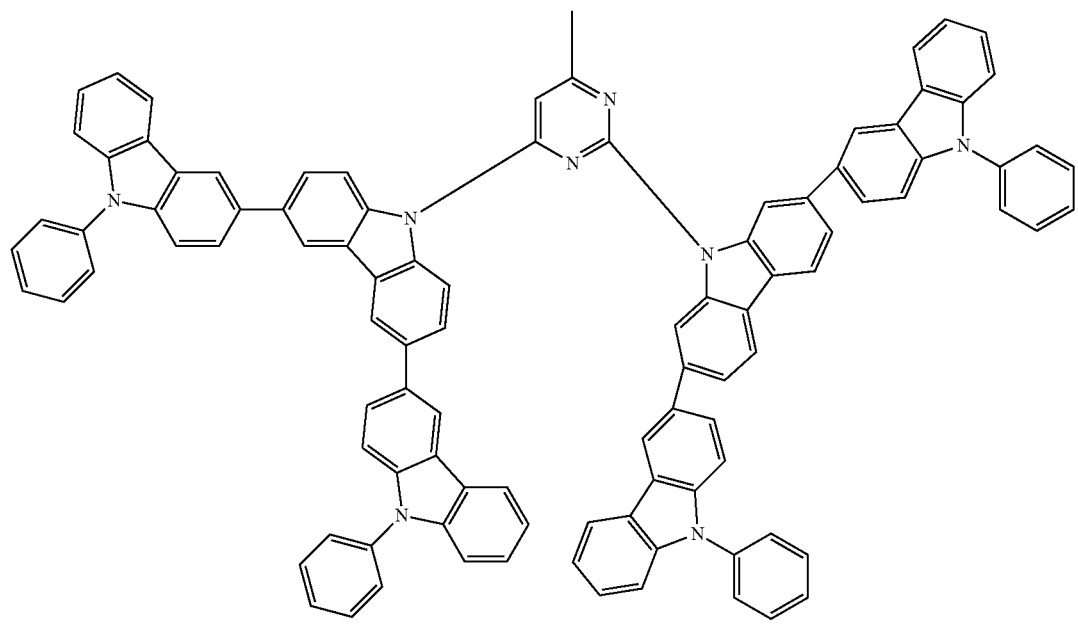
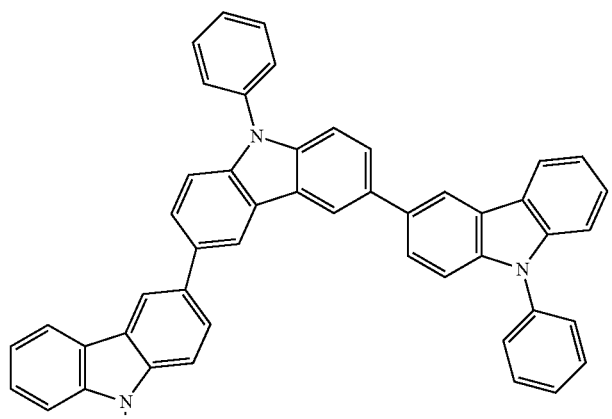

-continued
347
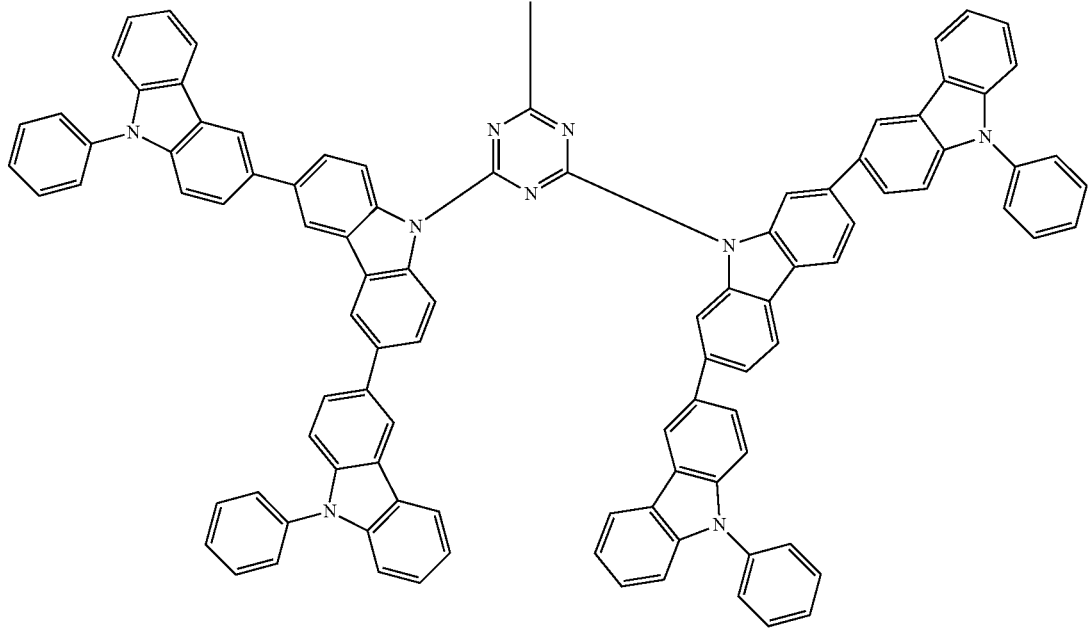
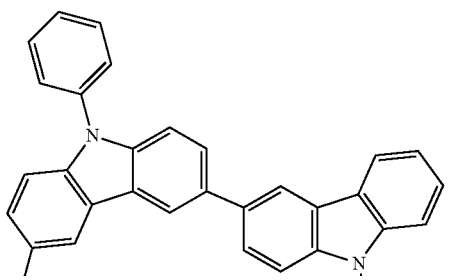
348
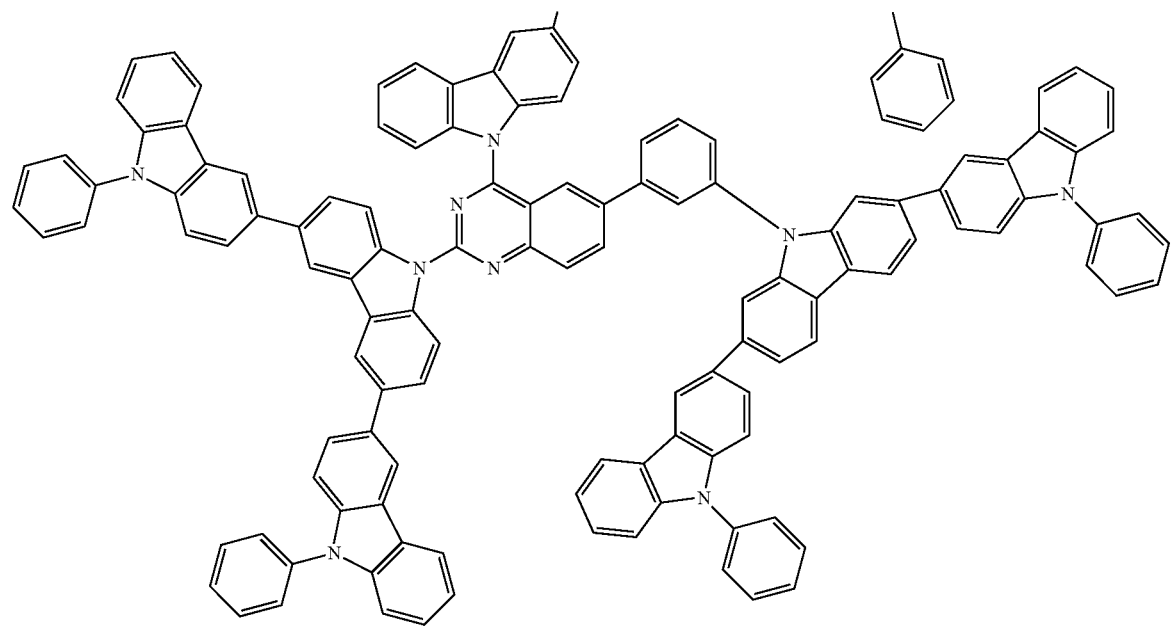

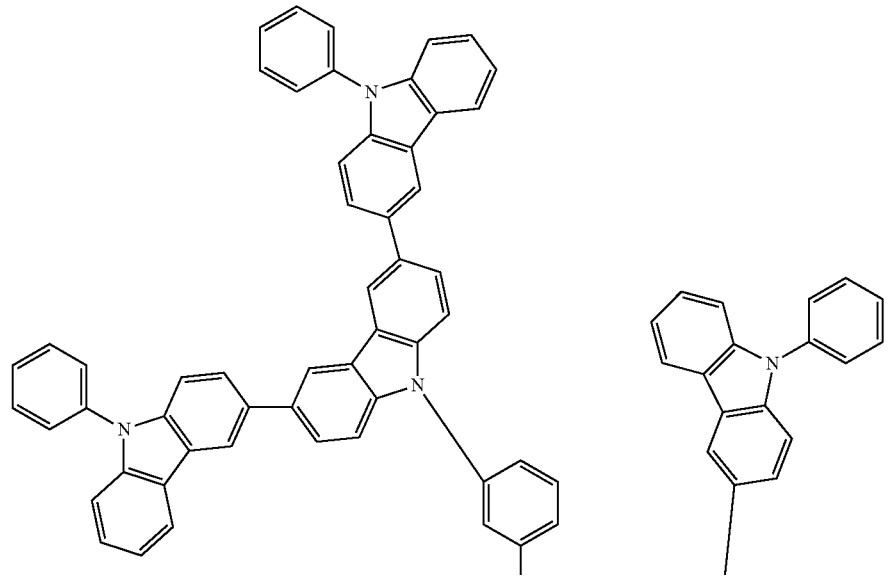
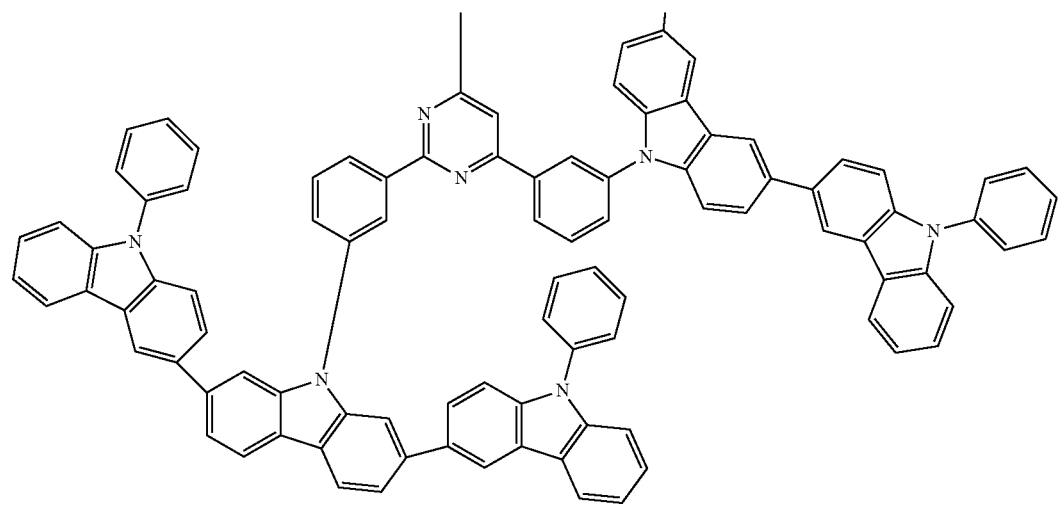
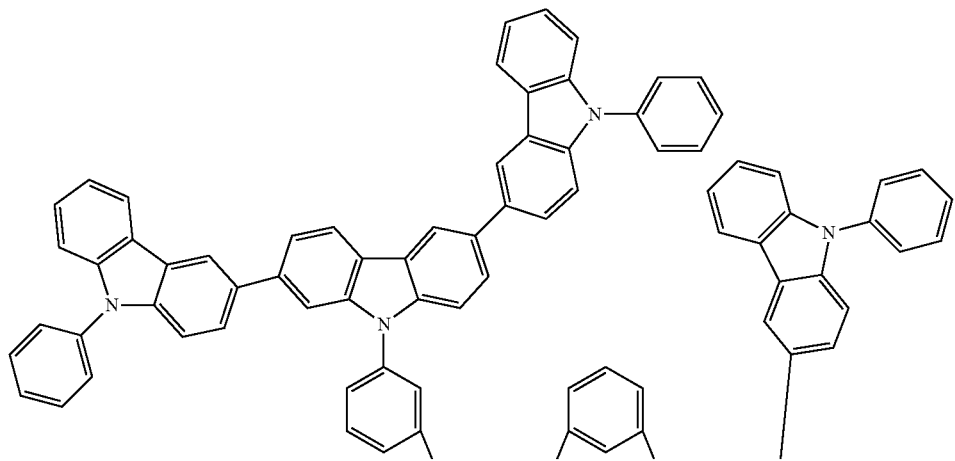

351 352
-continued
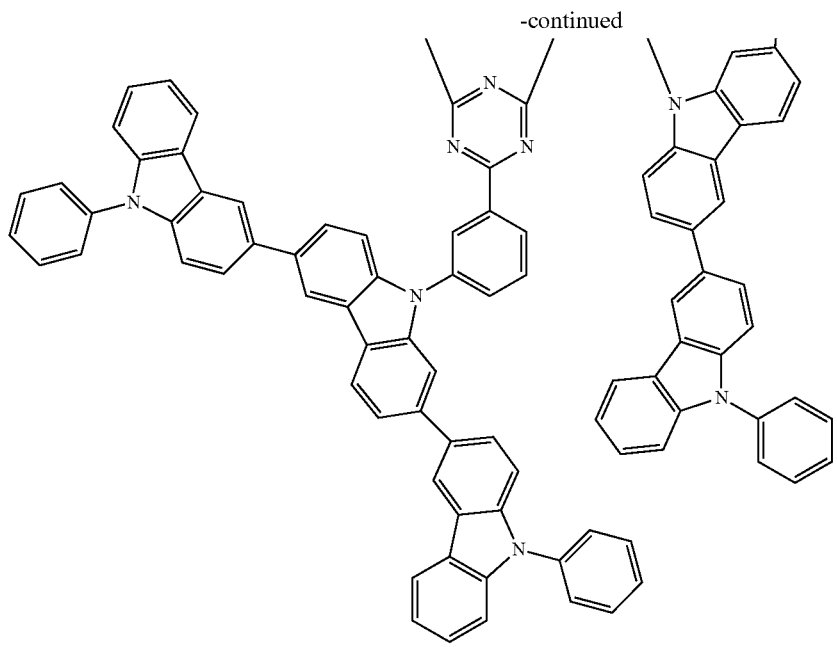
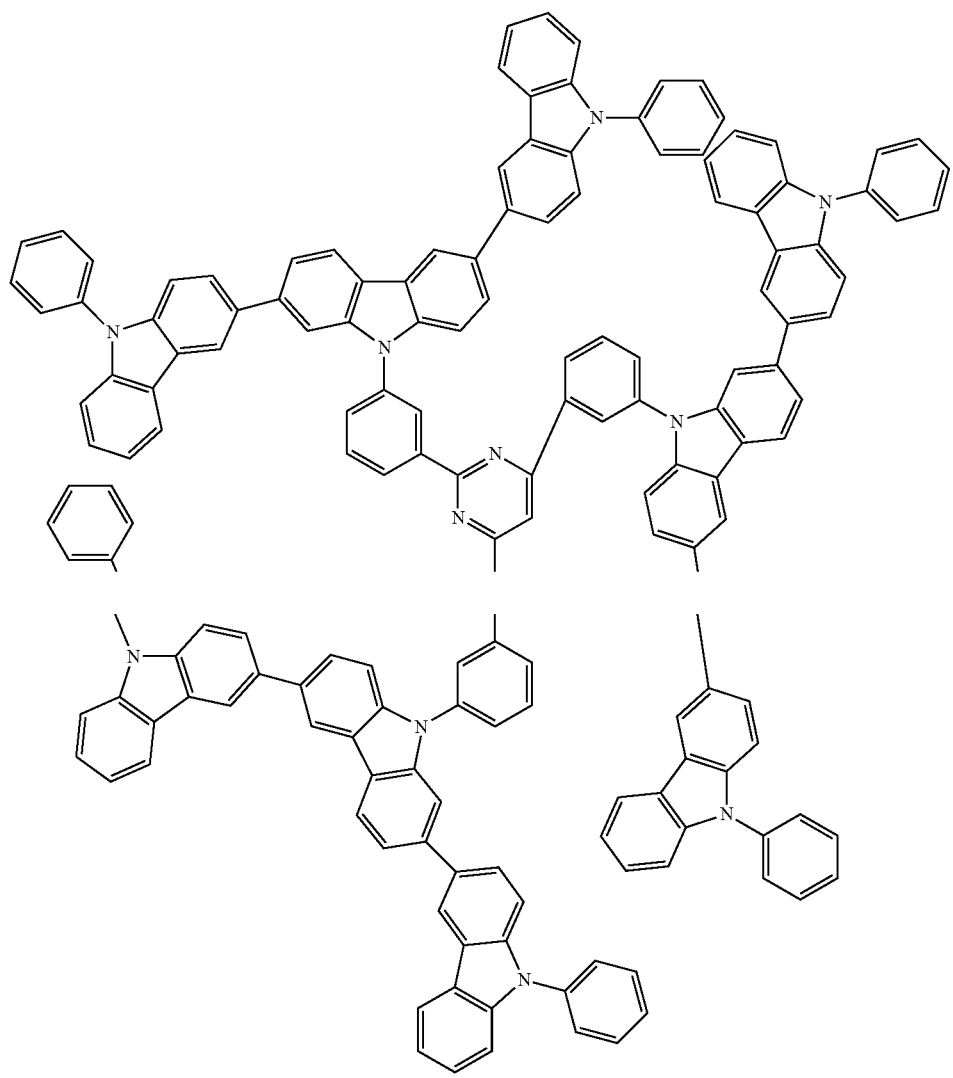

-continued
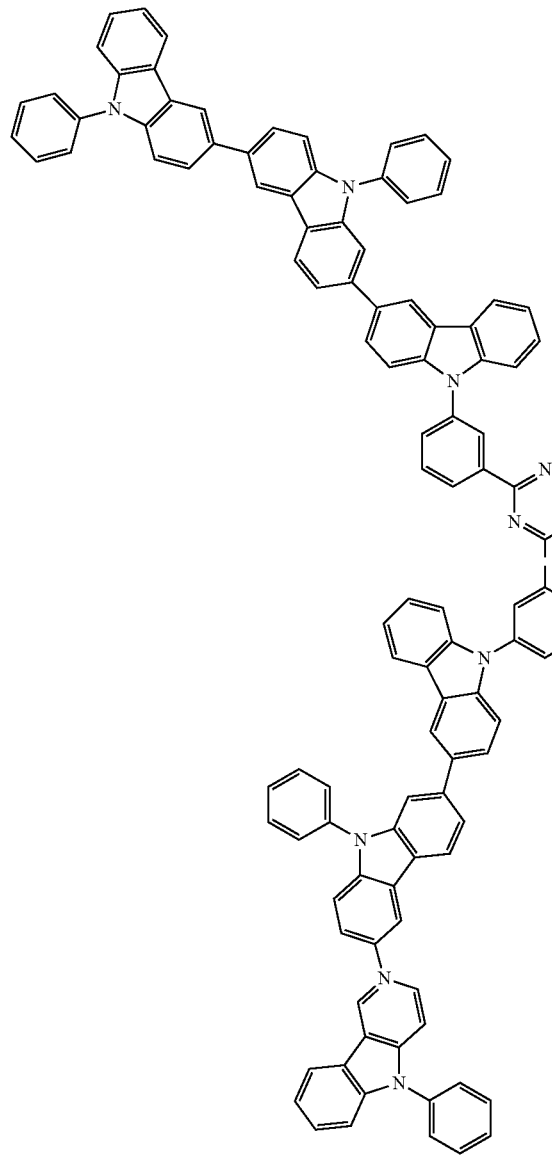
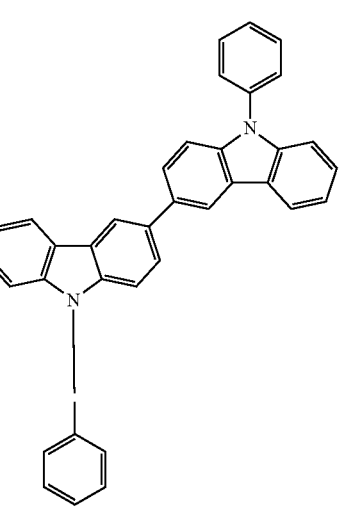
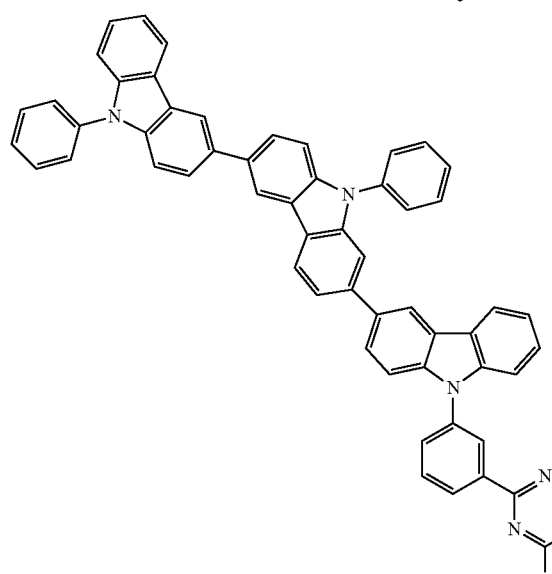

-continued
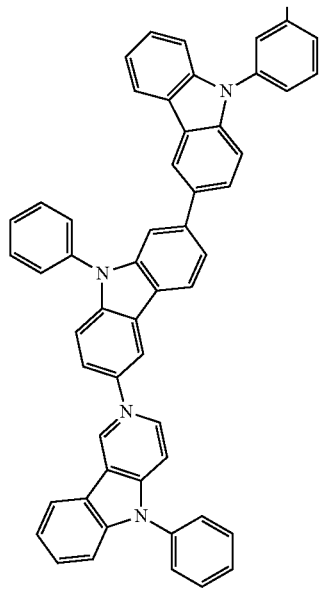
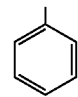
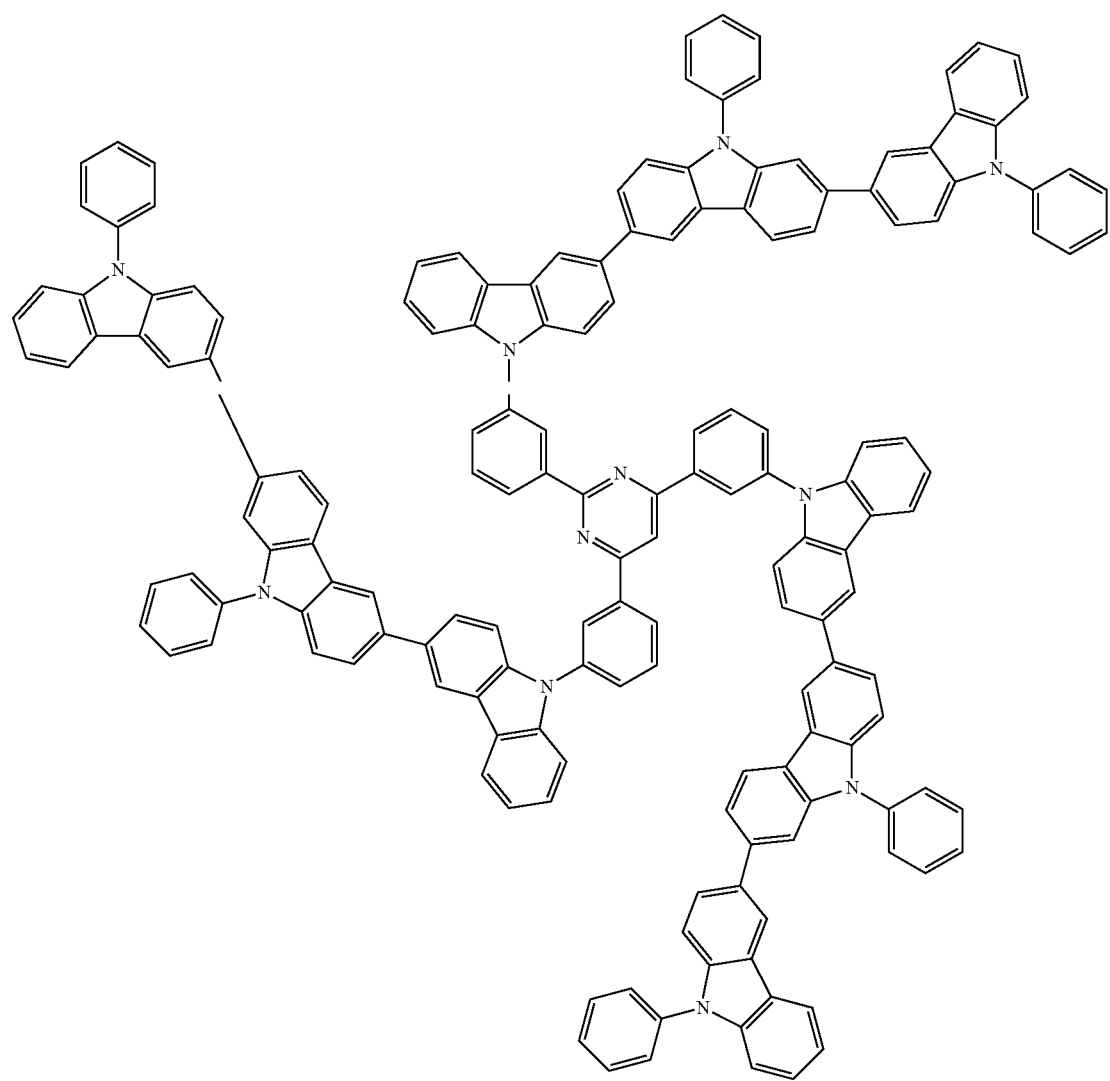 [SMILES: c1ccc(-n2c3ccccc3c3cc(-c4ccc5c6cc(-c7ccc8c(c7)c7ccccc7n8-c7cccc(-c8cc(-c9cccc(-n%10c%11ccccc%11c%11cc(-c%12ccc%13c(c%12)c%12ccc(-c%14ccc%15c(c%14)c%14ccccc%14n%15-c%14ccccc%14)cc%12n%13-c%12ccccc%12)ccc%11%10)c9)nc(-c9cccc(-n%10c%11ccccc%11c%11cc(-c%12ccc%13c(c%12)c%12ccc(-c%14ccc%15c(c%14)c%14ccccc%14n%15-c%14ccccc%14)cc%12n%13-c%12ccccc%12)ccc%11%10)c9)n8)c7)ccc6n(-c6ccccc6)c5c4)ccc32)cc1]

357 358
-continued
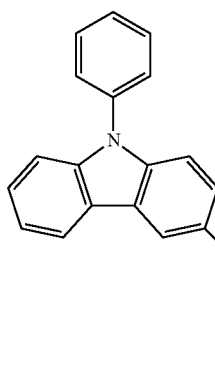
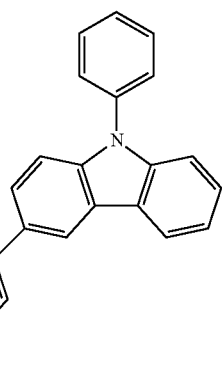
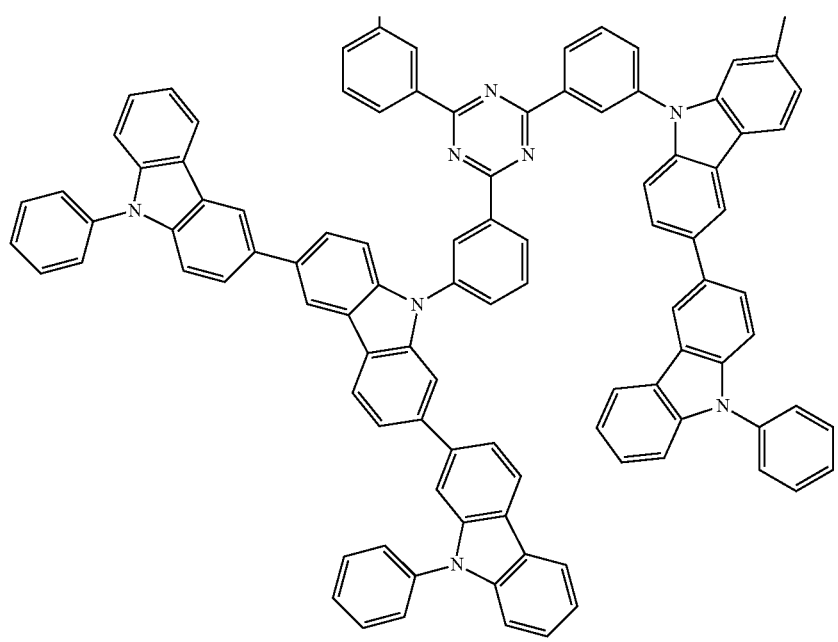
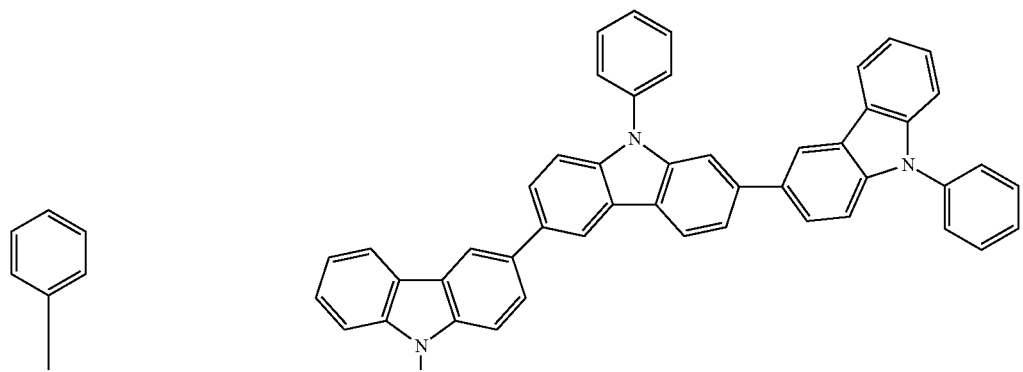

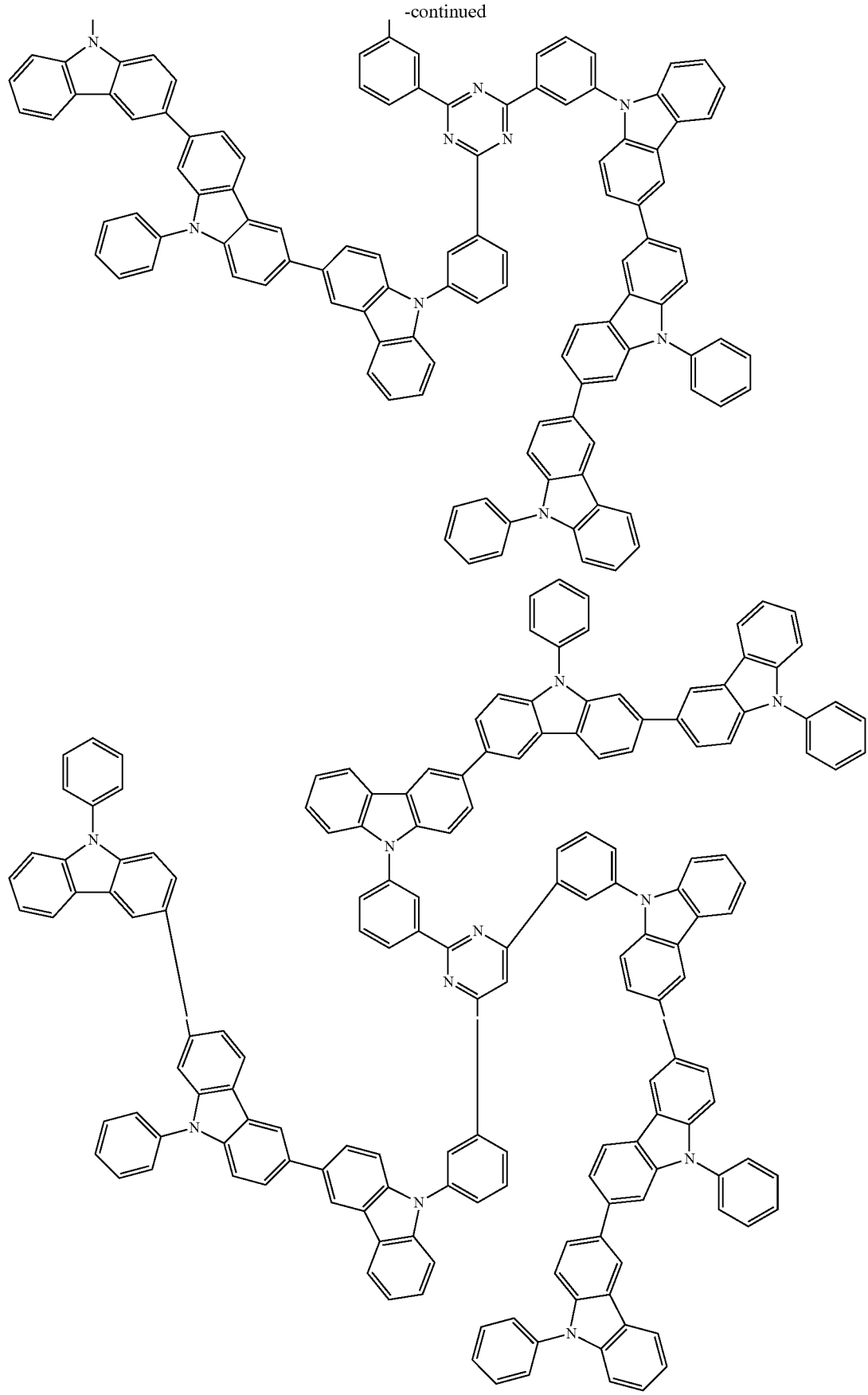

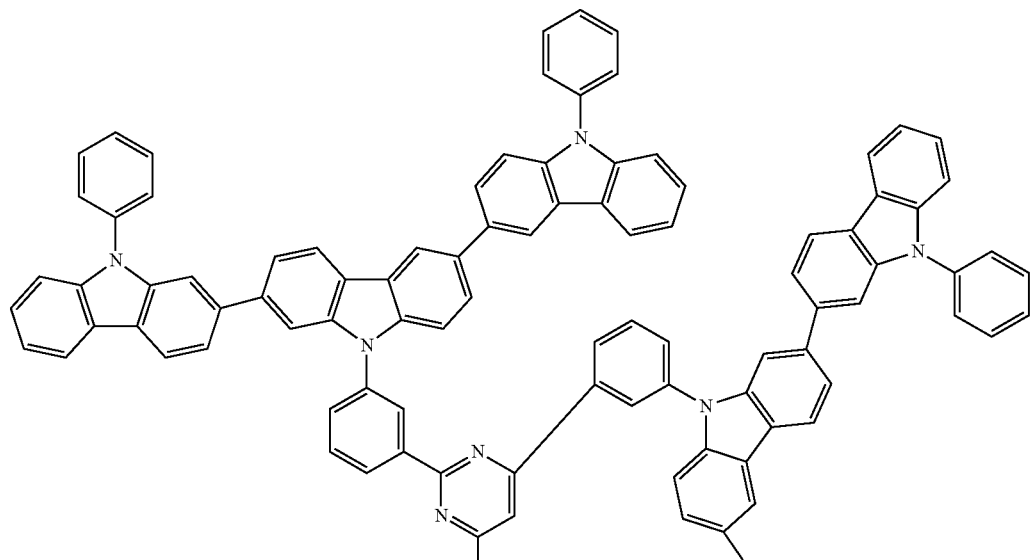
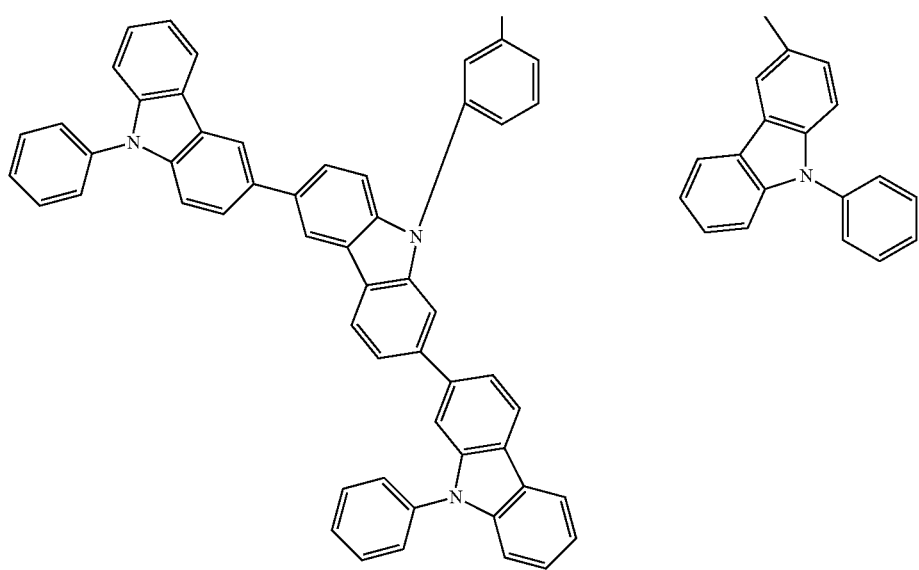

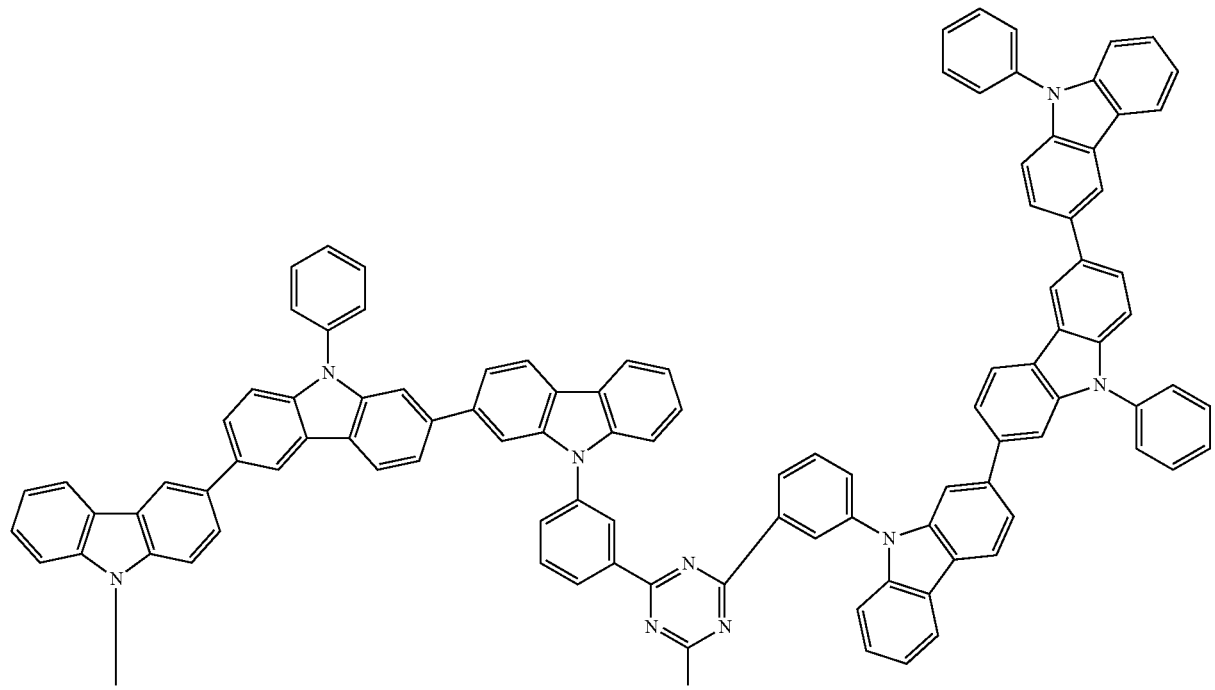
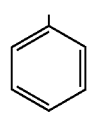
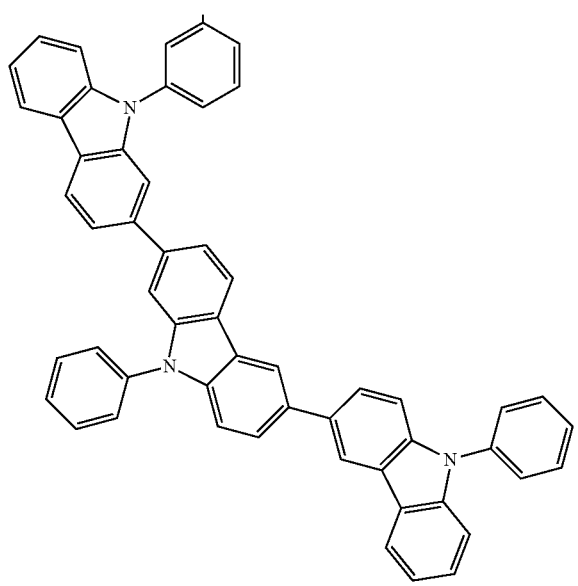

365
366
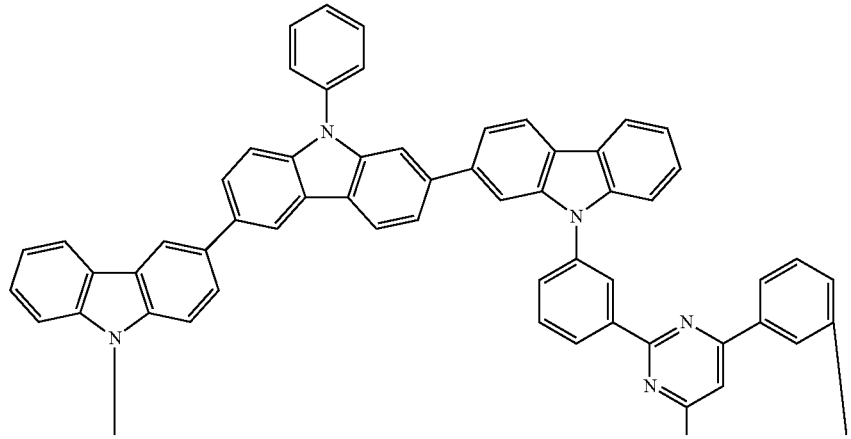
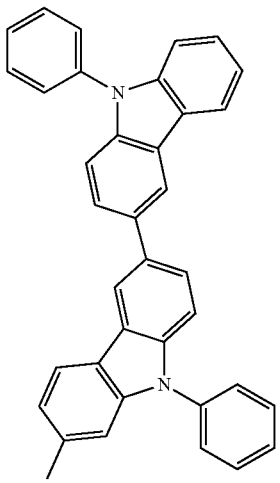
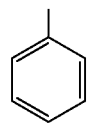
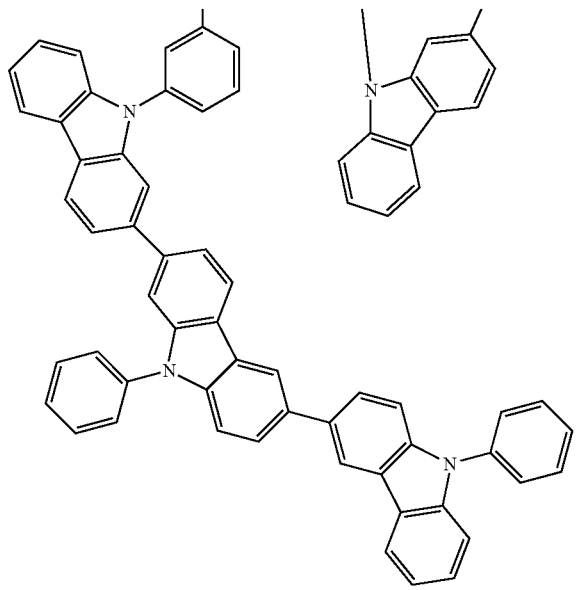
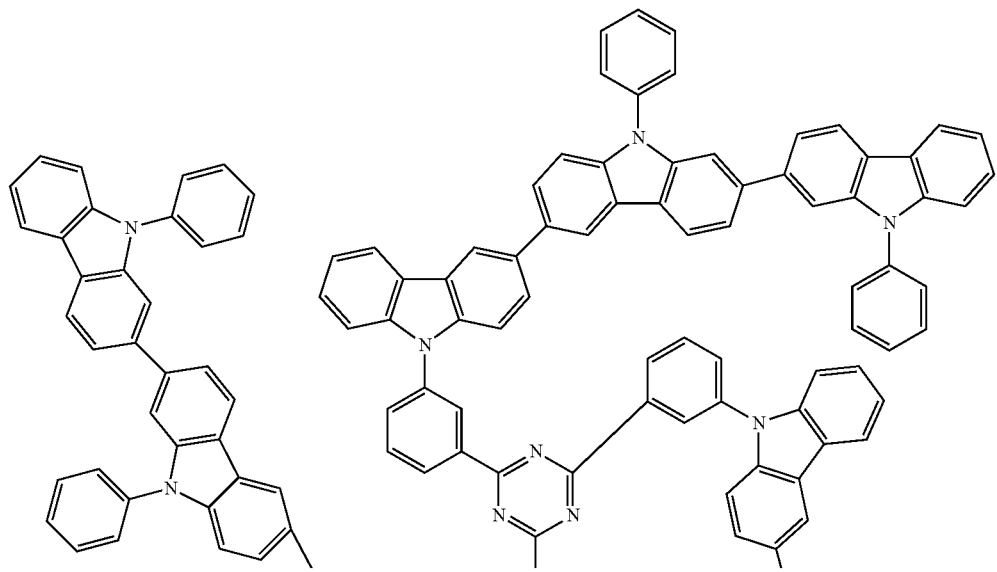

-continued
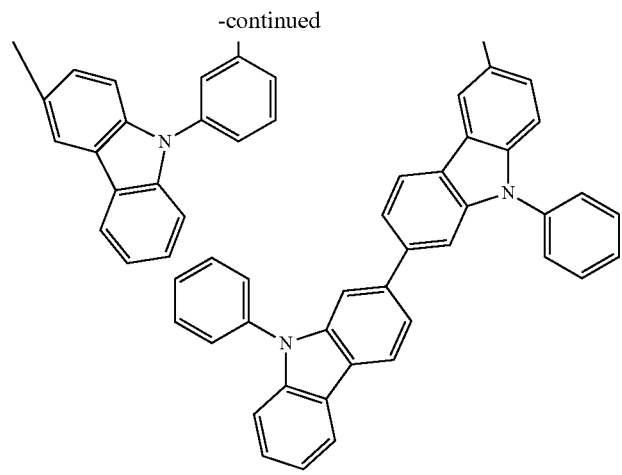
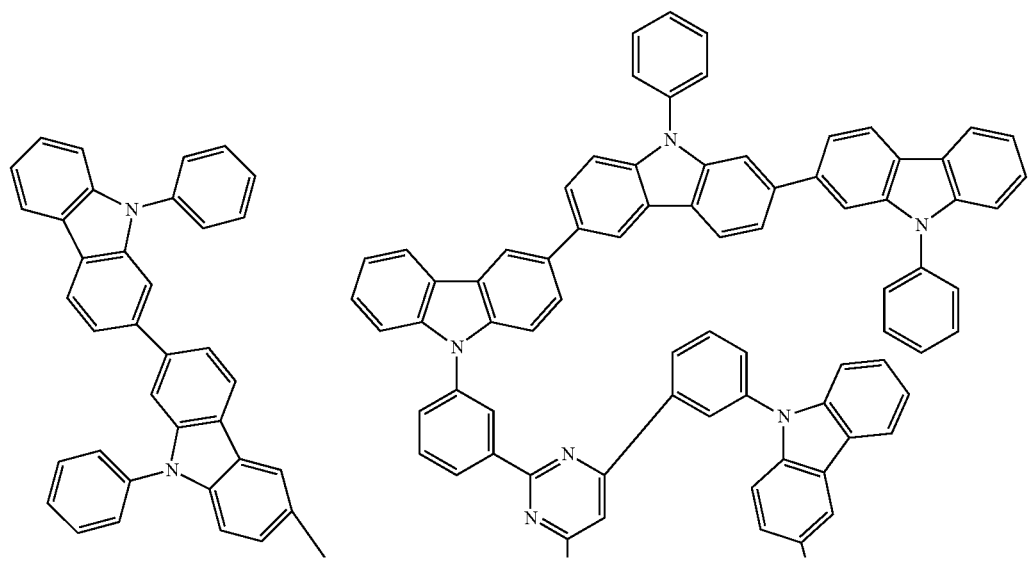
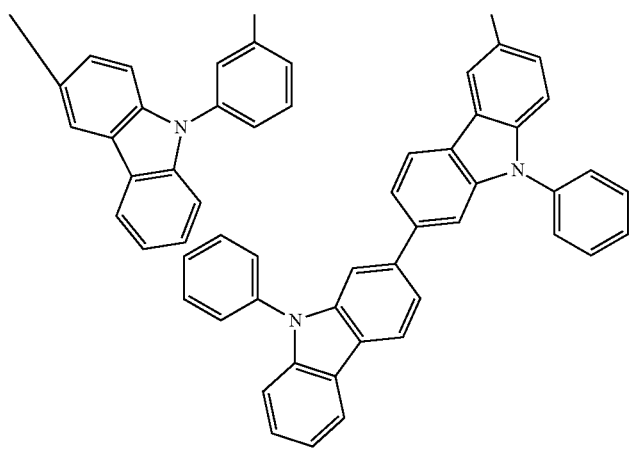

-continued
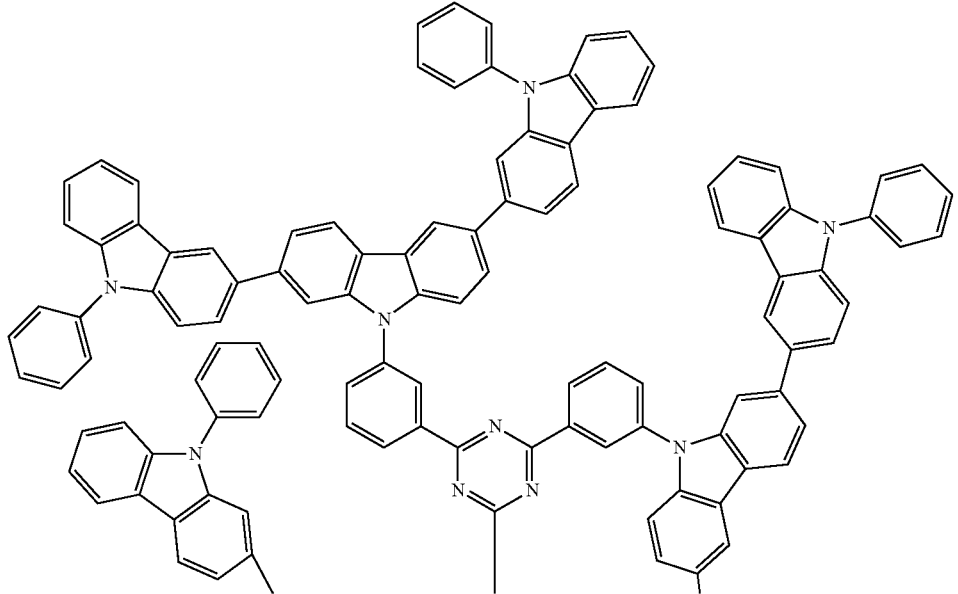
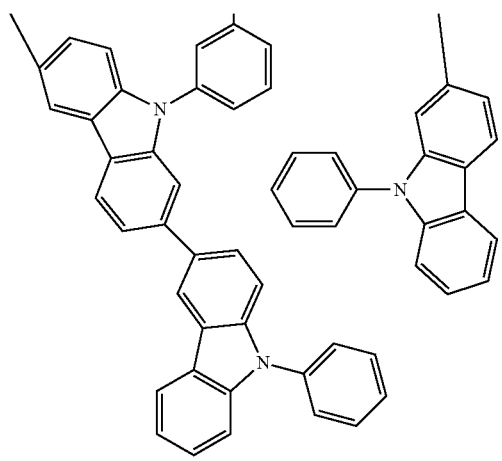
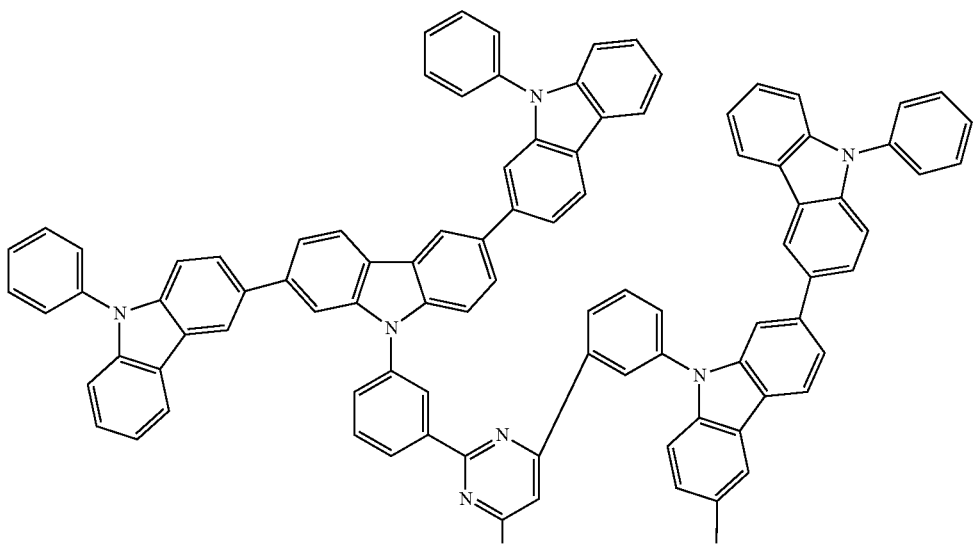

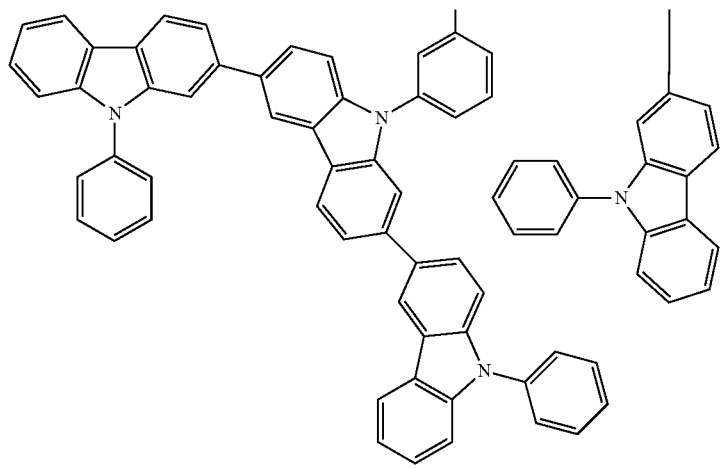
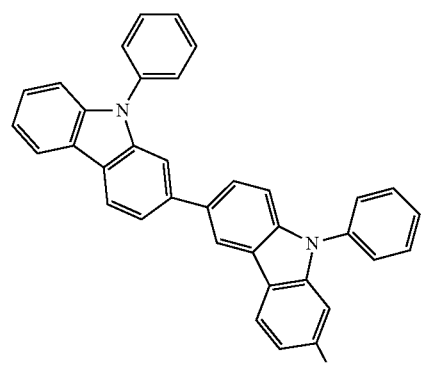
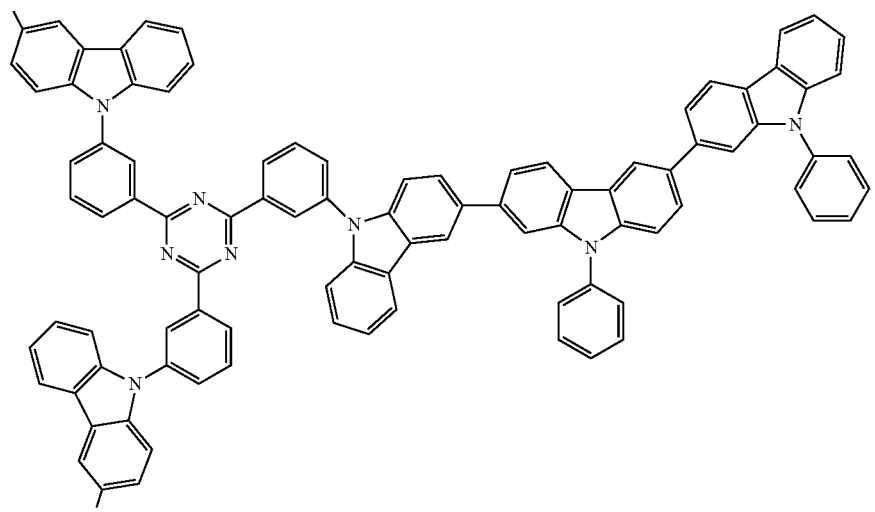

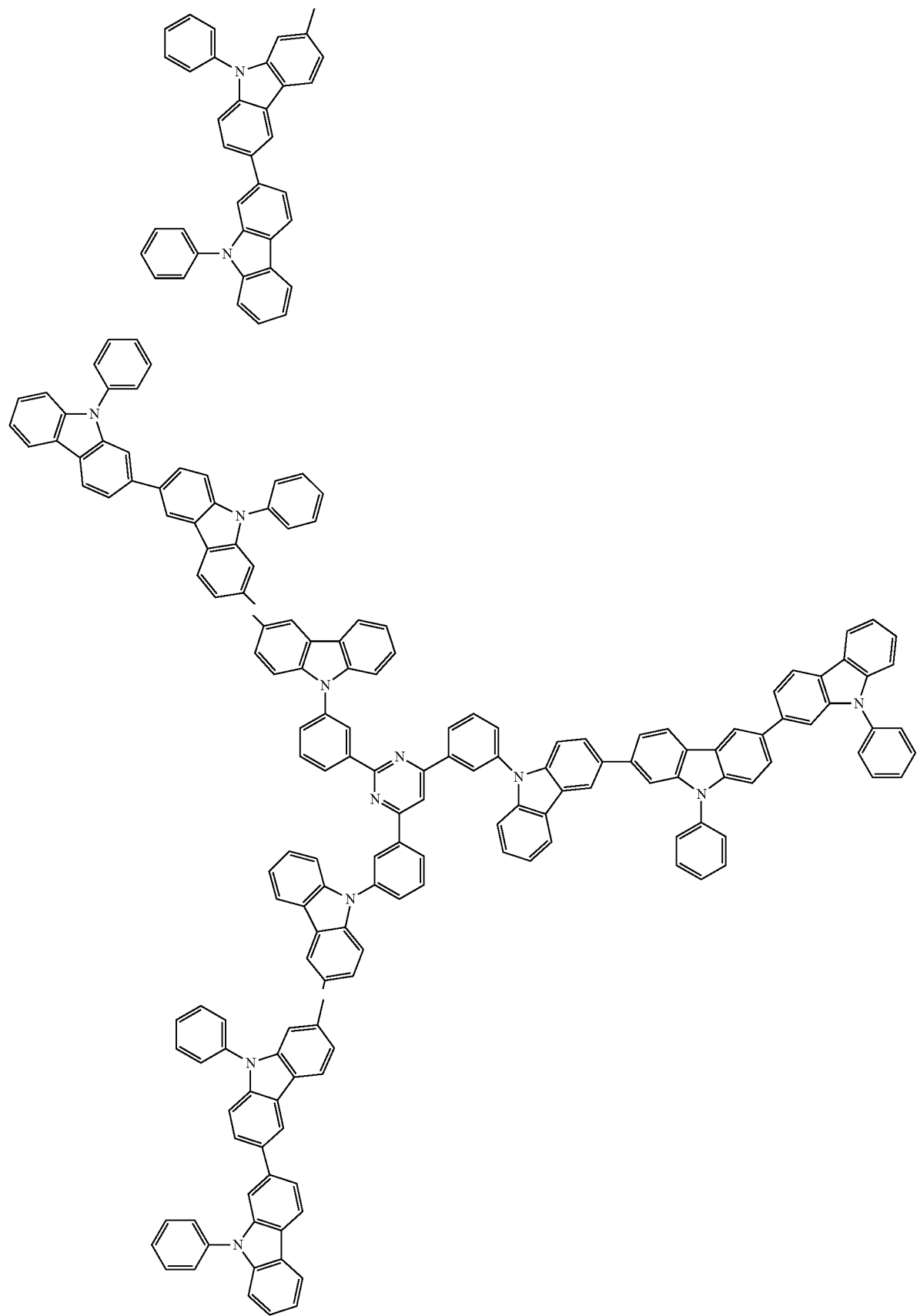

375
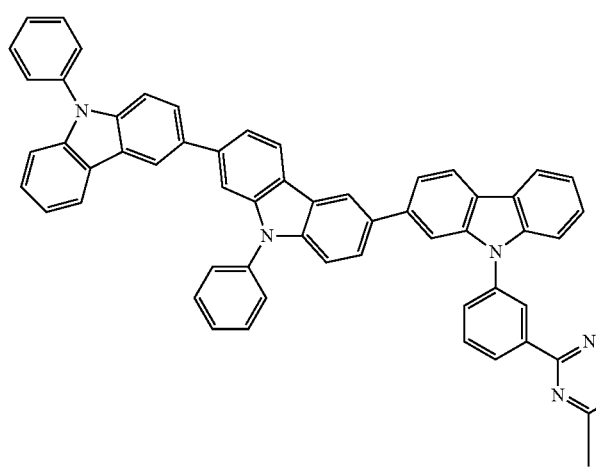
376
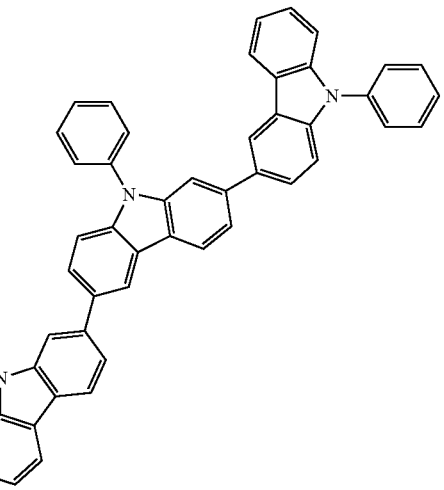
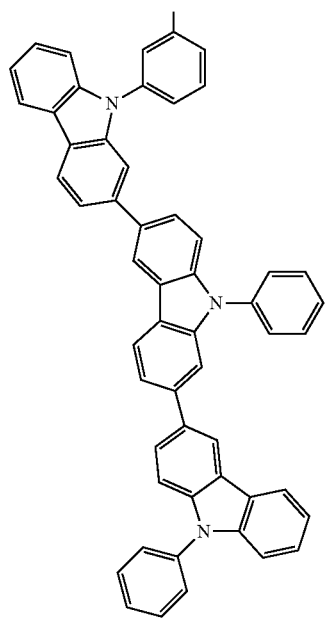
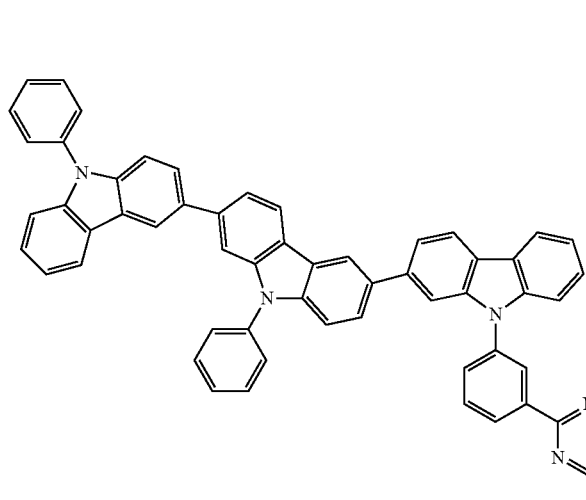
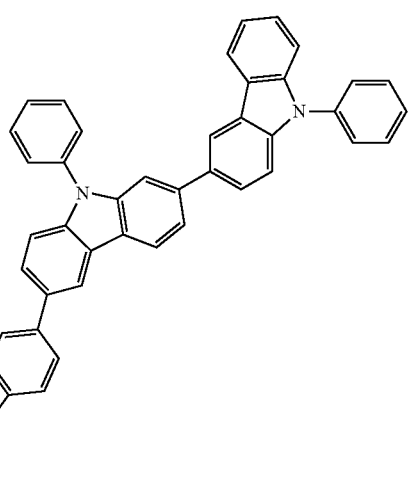

-continued
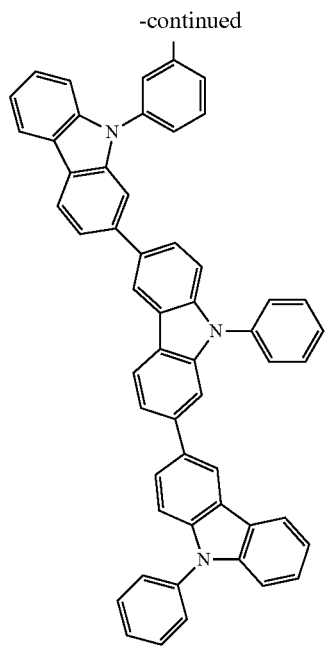
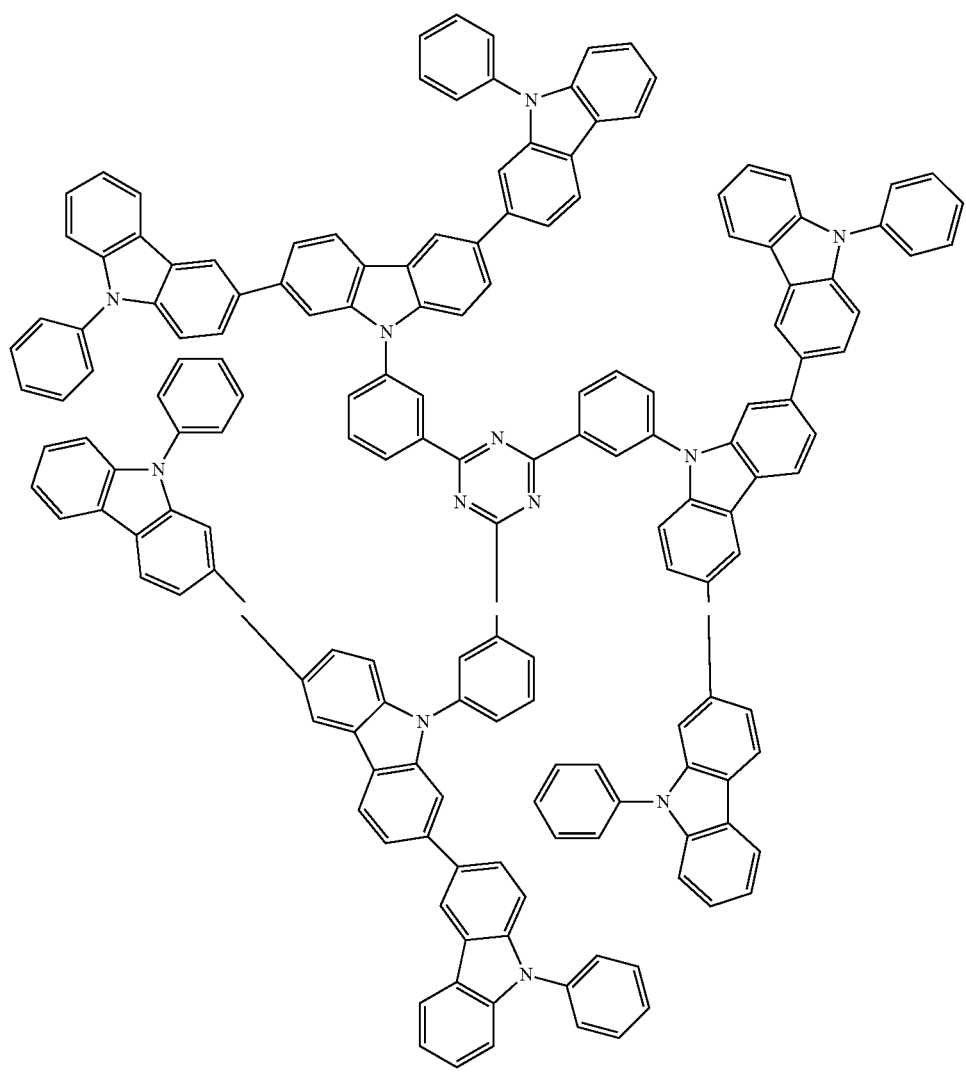 [SMILES: c1ccc(-n2c3ccccc3c3cc(-c4ccc5c6cc(-c7ccc8c9ccccc9n(-c9ccccc9)c8c7)ccc6n(-c6cccc(-c7nc(-c8cccc(-n9c%10ccc(-c%11ccc%12c%13ccccc%13n(-c%13ccccc%13)c%12c%11)cc%10c%10ccc(-c%11ccc%12c(c%11)c%11ccccc%11n%12-c%11ccccc%11)cc%109)c8)nc(-c8cccc(-n9c%10ccc(-c%11ccc%12c%13ccccc%13n(-c%13ccccc%13)c%12c%11)cc%10c%10ccc(-c%11ccc%12c(c%11)c%11ccccc%11n%12-c%11ccccc%11)cc%109)c8)n7)c6)c5c4)ccc32)cc1]

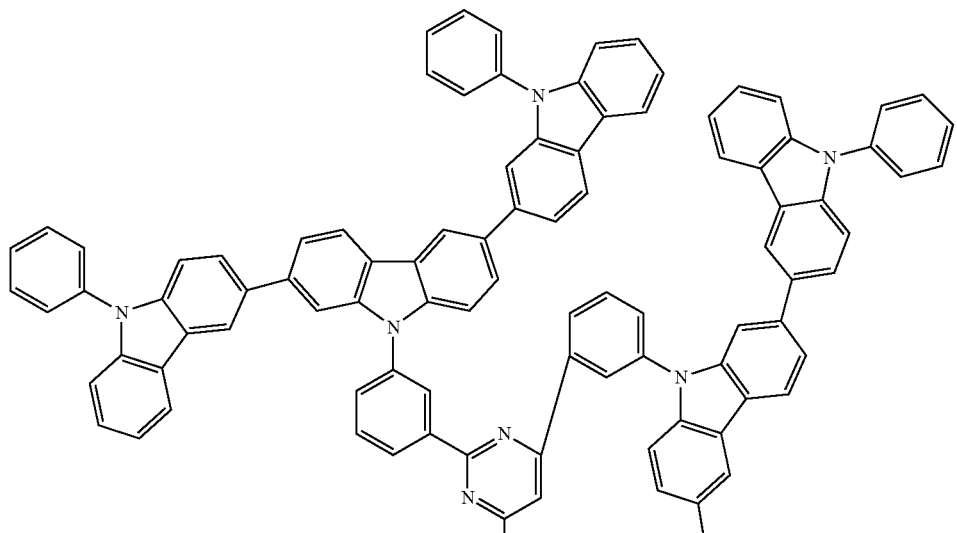
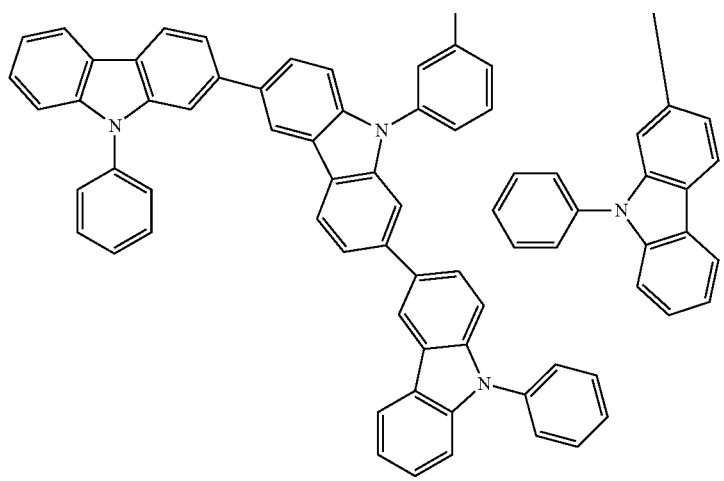
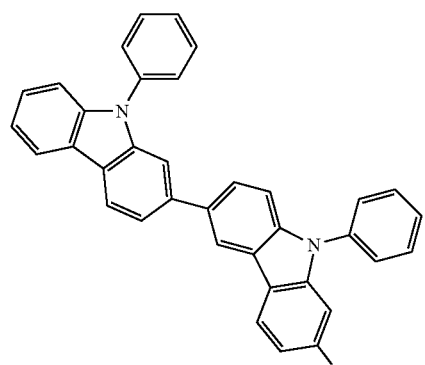

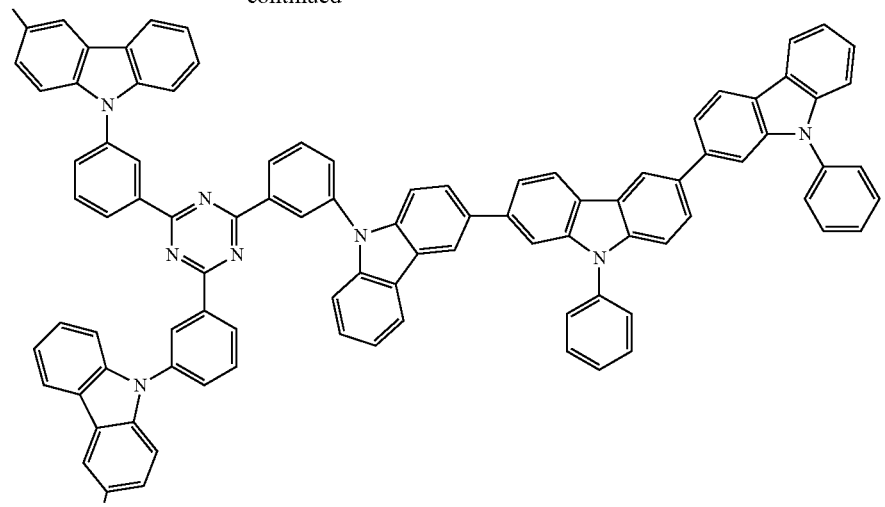
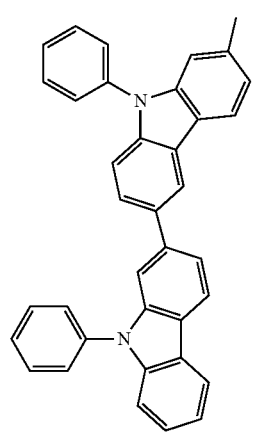
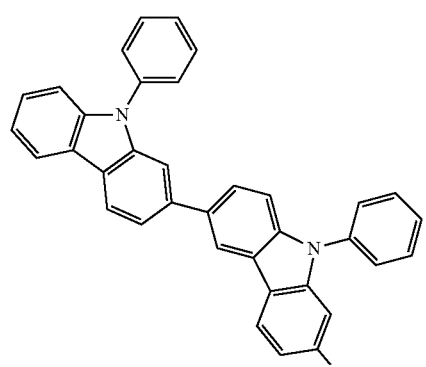

-continued
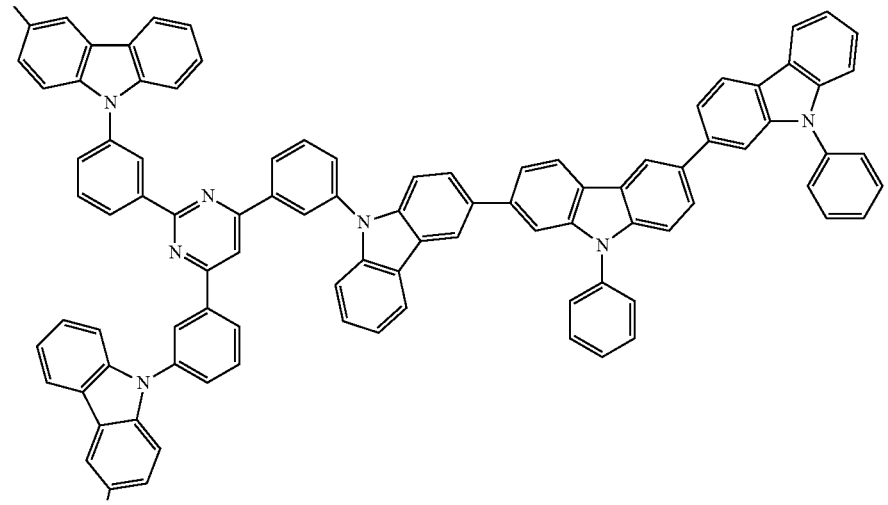
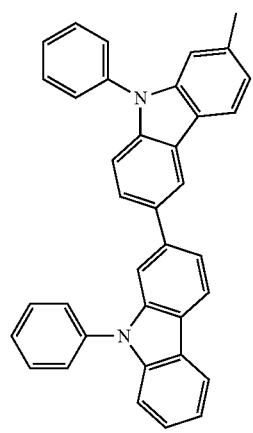
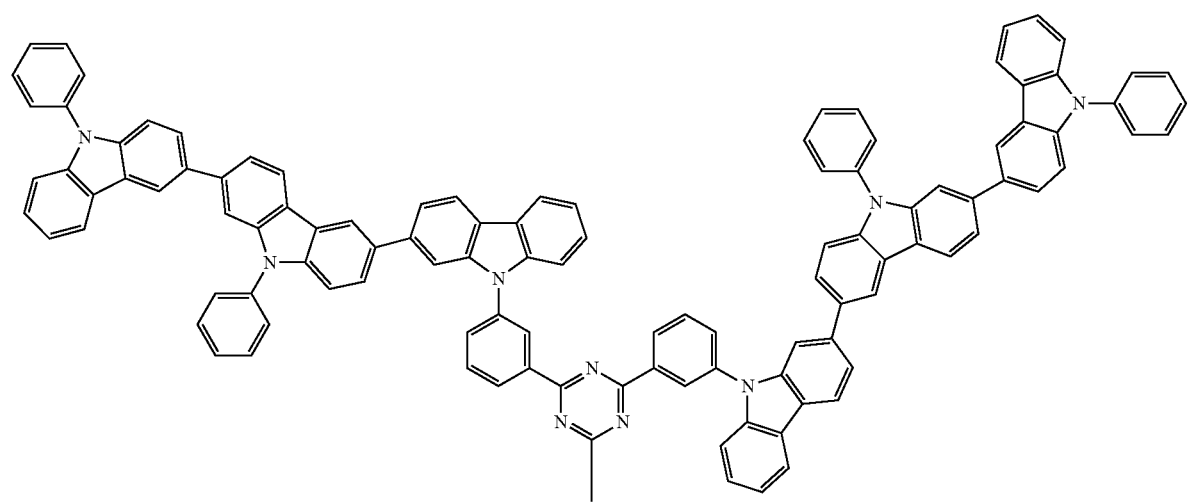

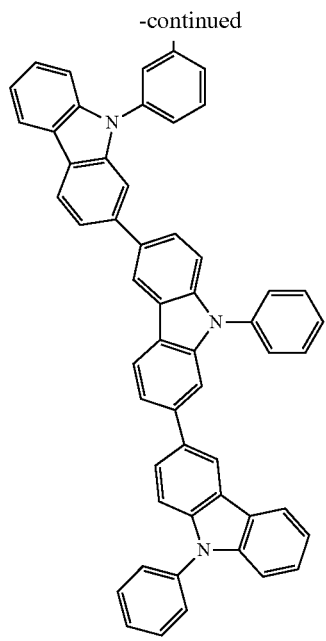
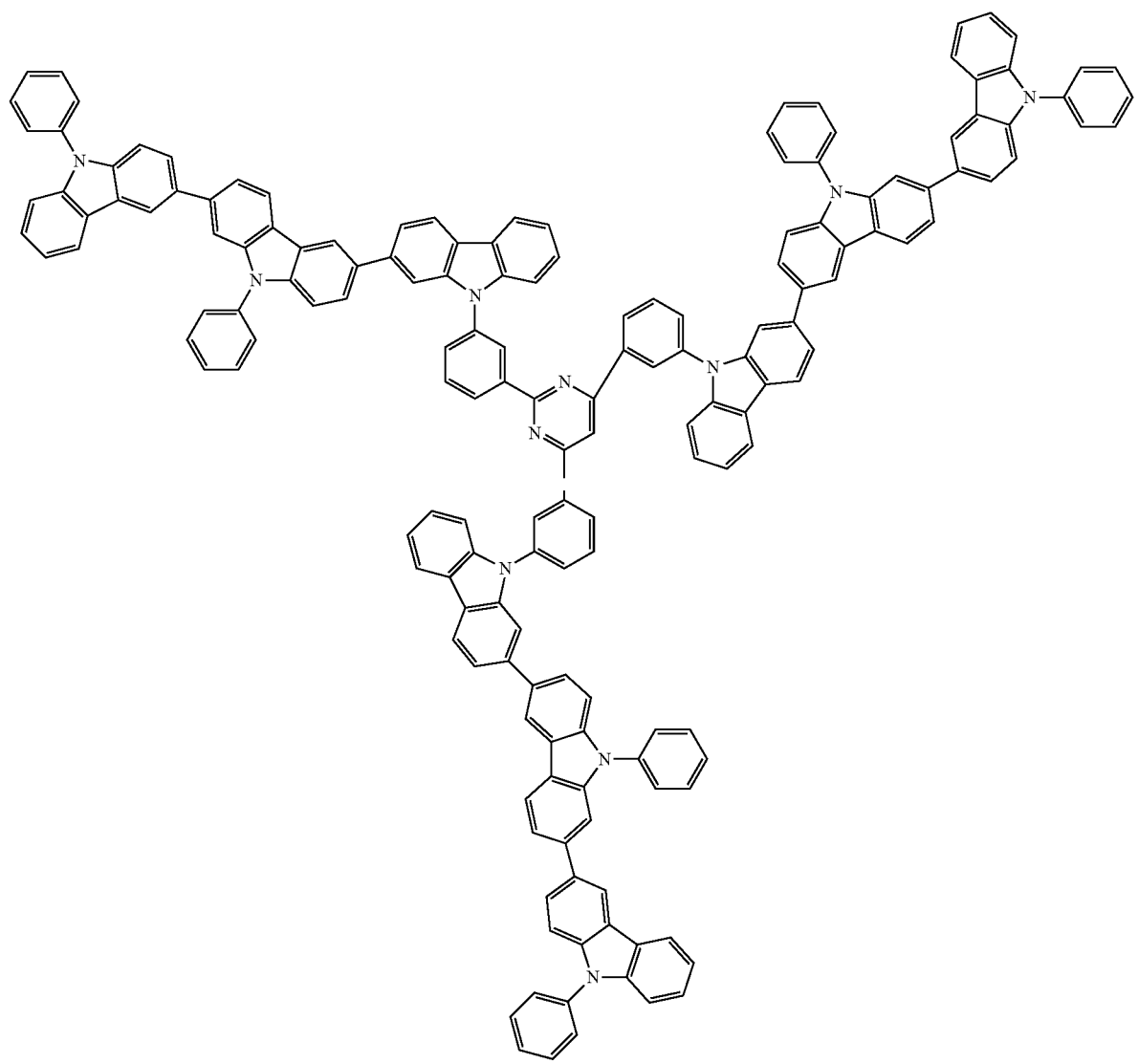 [SMILES: c1ccc(-n2c3ccccc3c3cc(-c4ccc5c6cc(-c7ccc8c9ccccc9n(-c9cccc(-c%10cc(-c%11cccc(-n%12c%13ccccc%13c%13ccc(-c%14ccc%15c(c%14)c%14ccc(-c%16ccc%17c(c%16)c%16ccccc%16n%17-c%16ccccc%16)cc%14n%15-c%14ccccc%14)cc%13%12)c%11)nc(-c%11cccc(-n%12c%13ccccc%13c%13ccc(-c%14ccc%15c(c%14)c%14ccc(-c%16ccc%17c(c%16)c%16ccccc%16n%17-c%16ccccc%16)cc%14n%15-c%14ccccc%14)cc%13%12)c%11)n%10)c9)c8c7)ccc6n(-c6ccccc6)c5c4)ccc32)cc1]

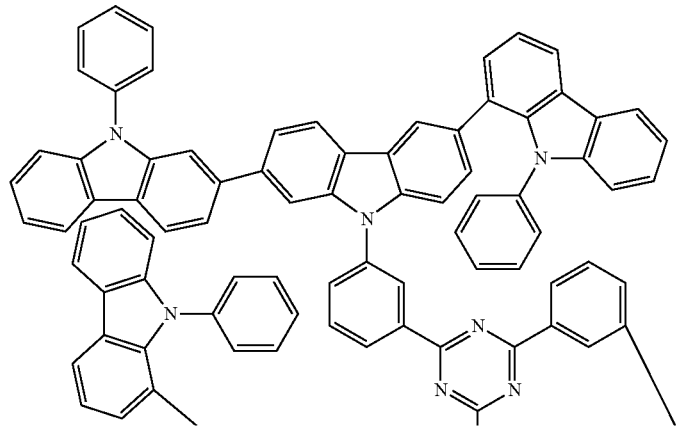
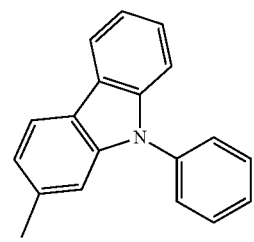
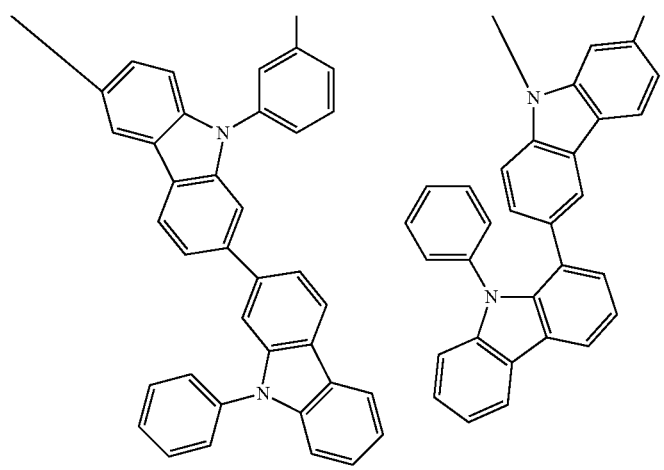

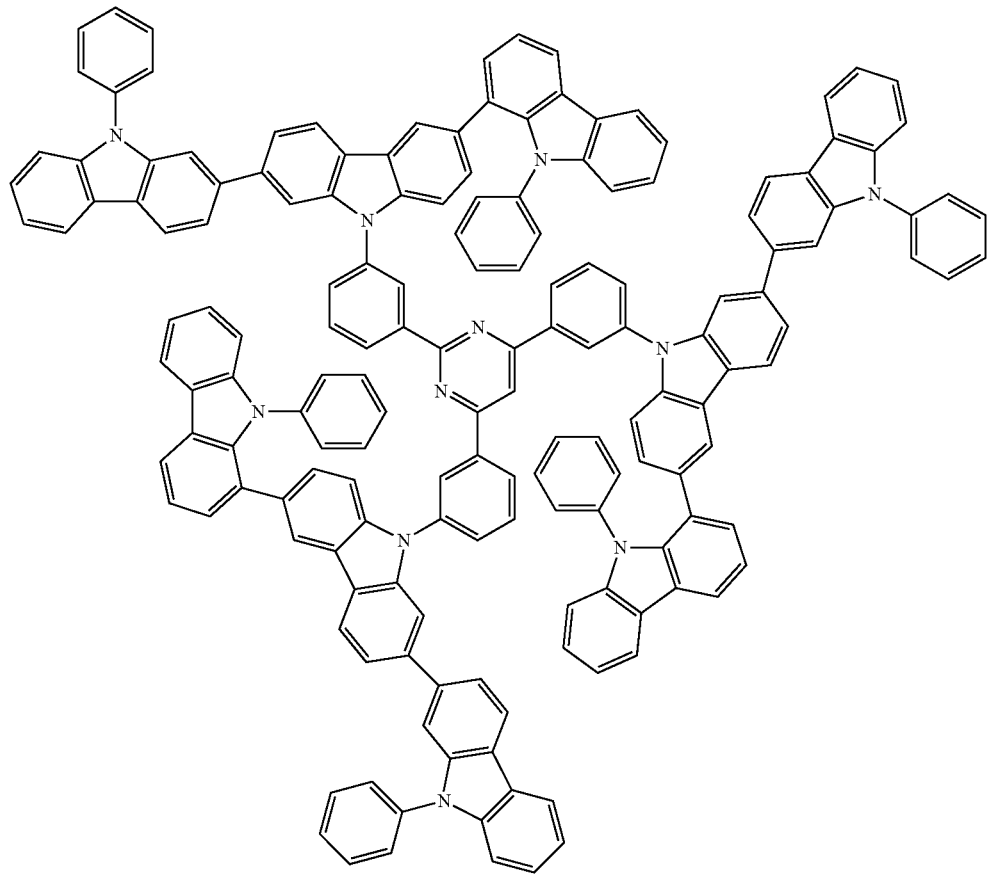
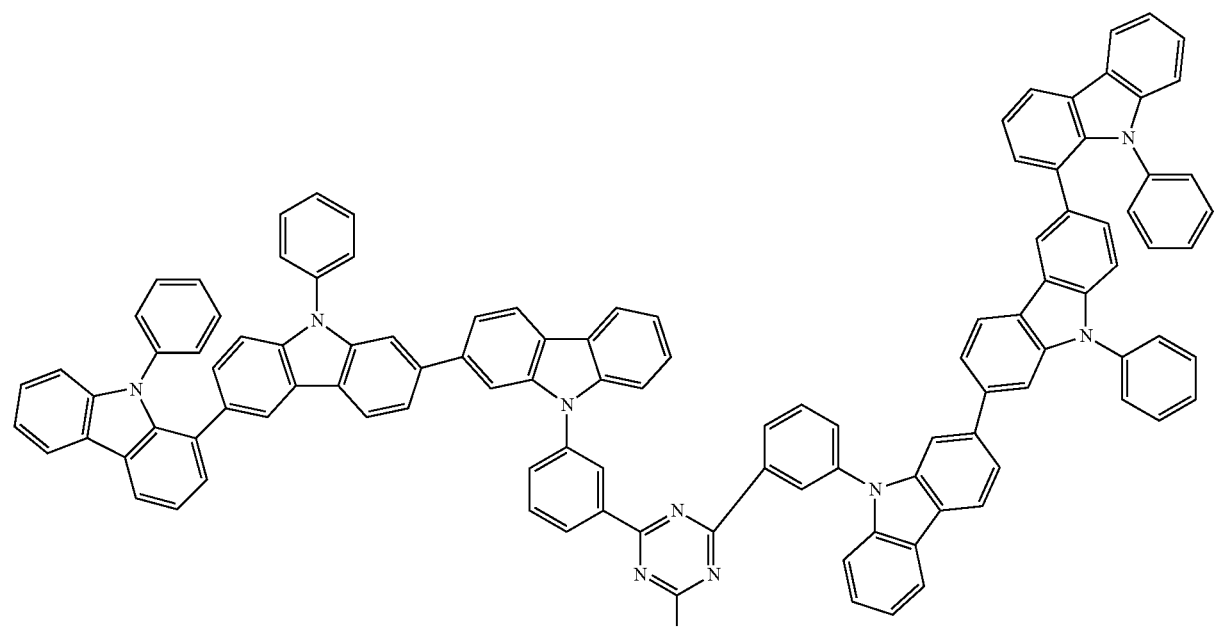

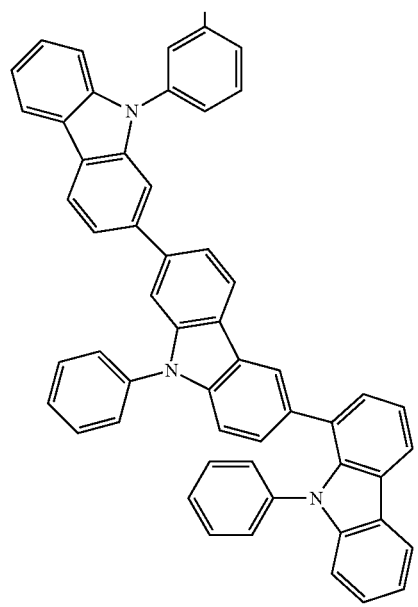
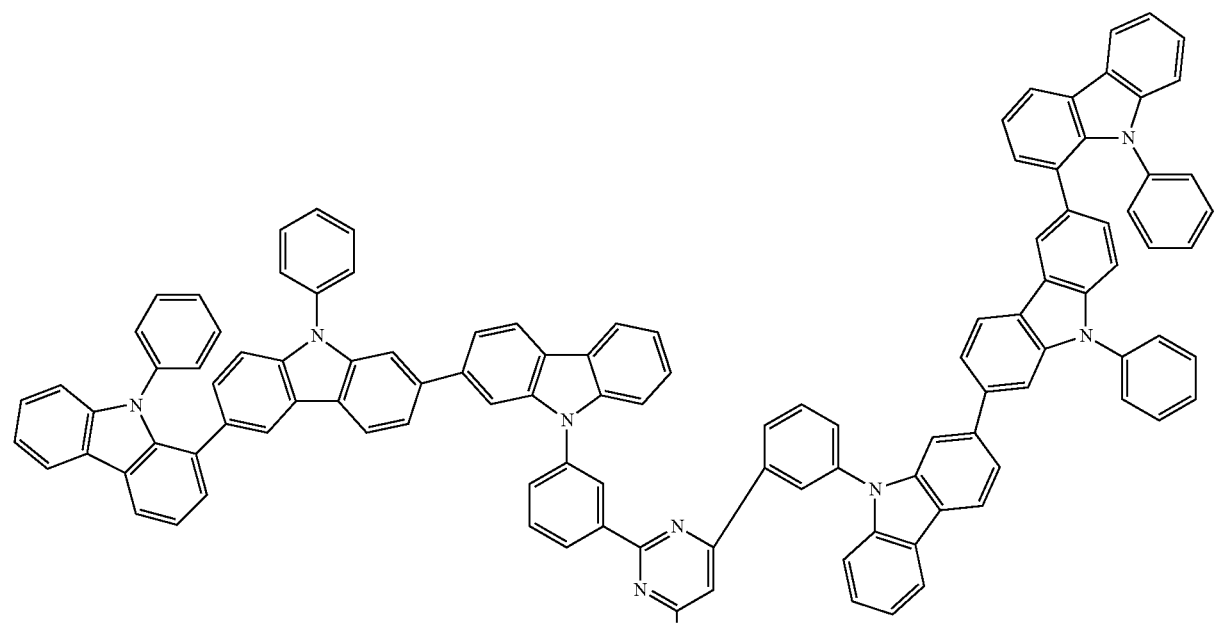

-continued
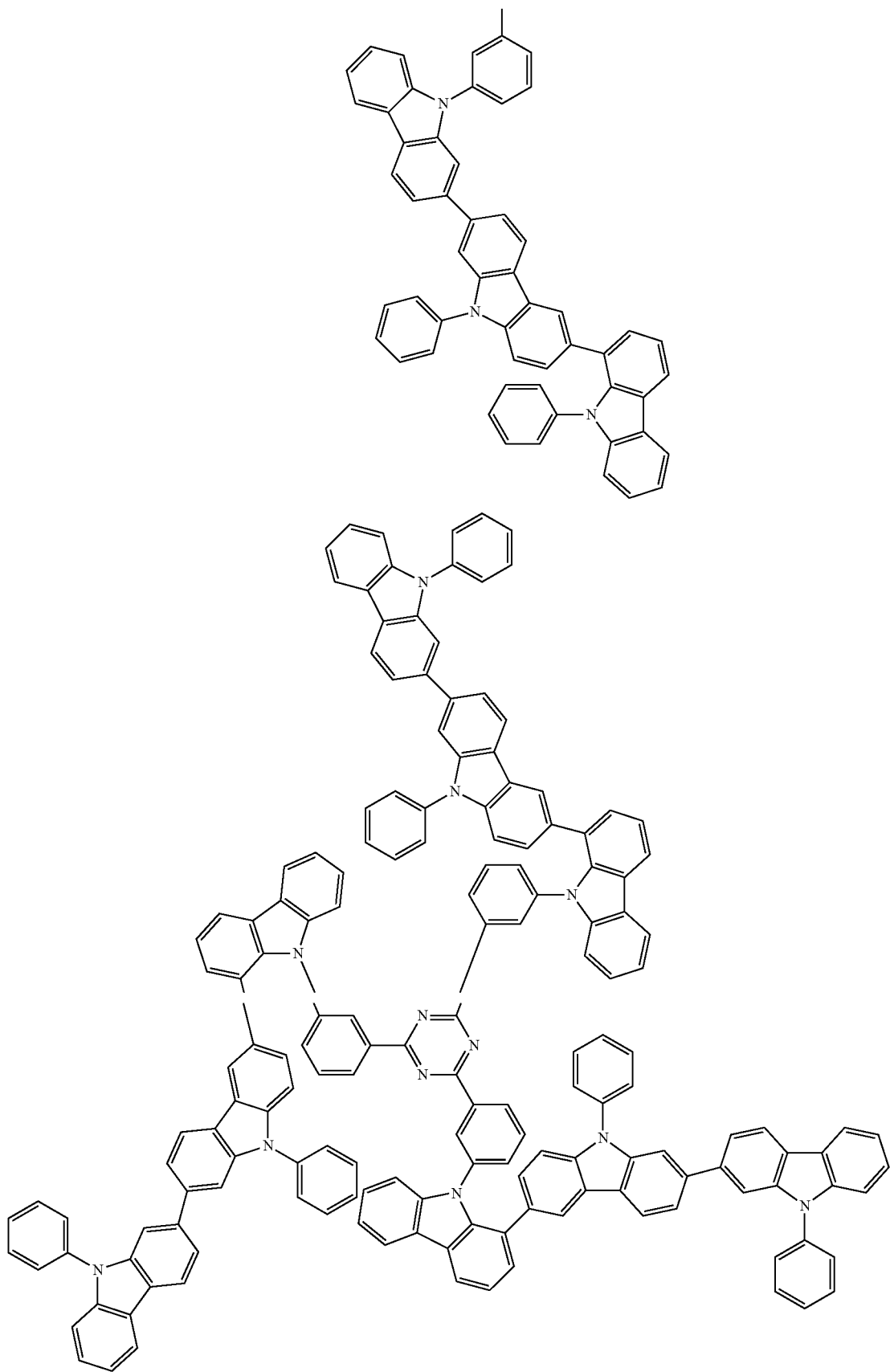

-continued
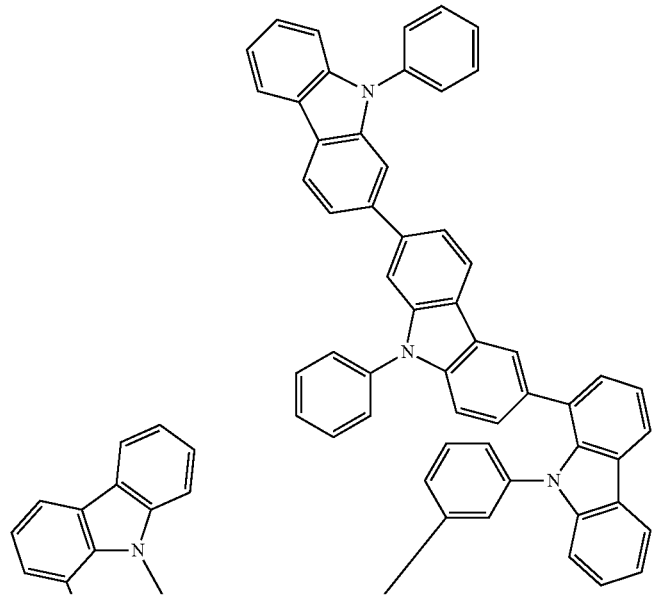
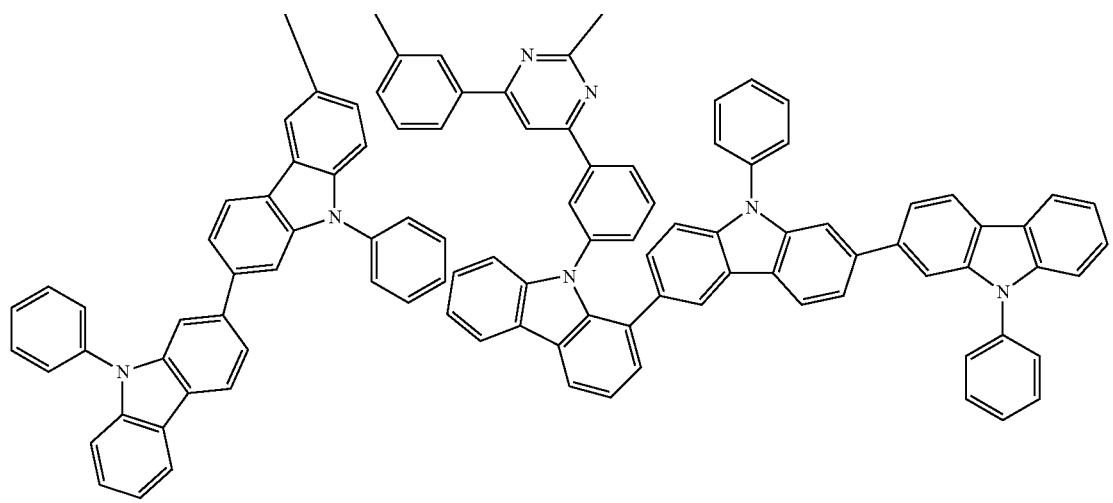
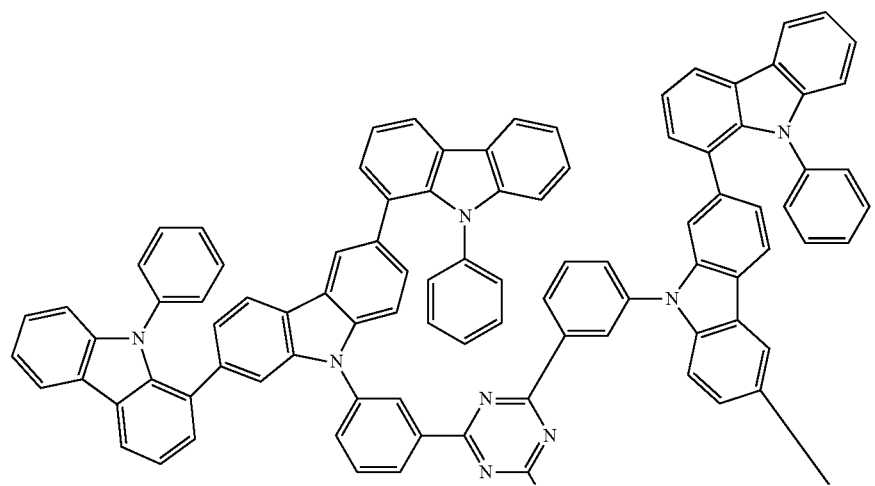

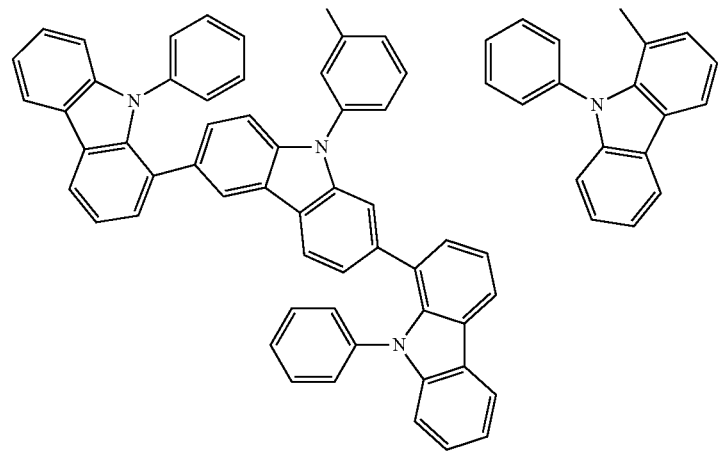
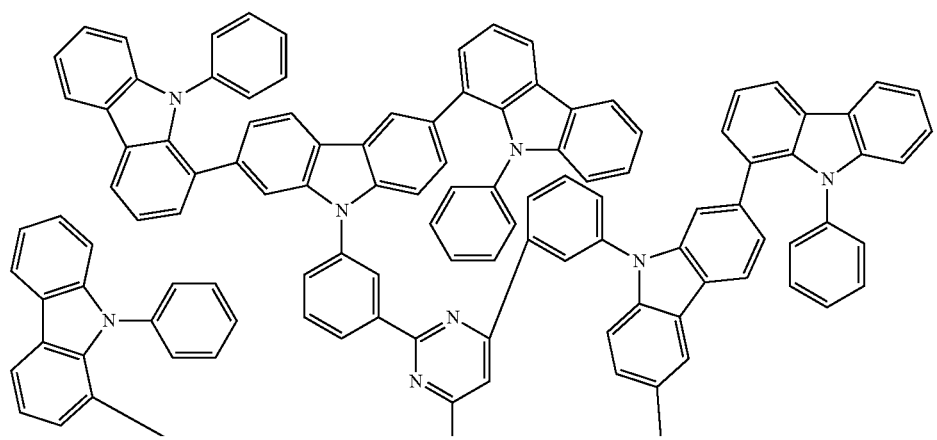
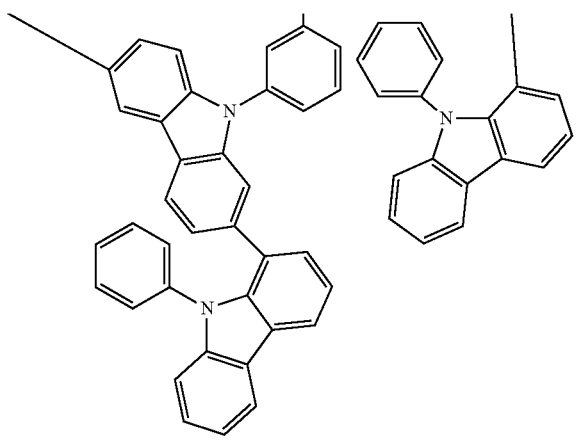

-continued
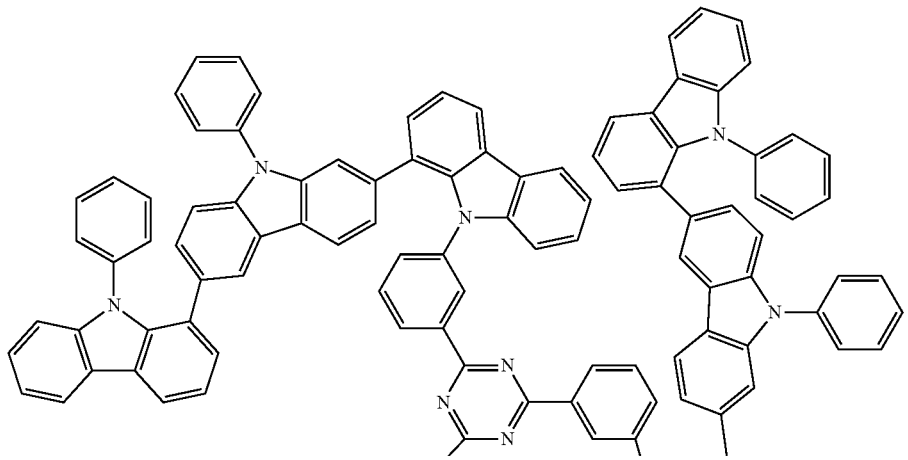
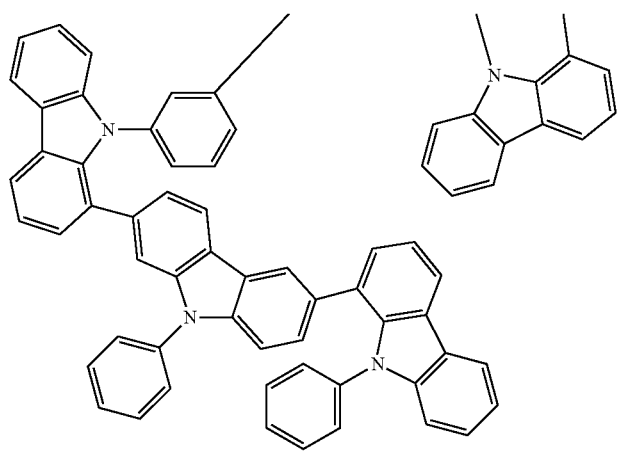
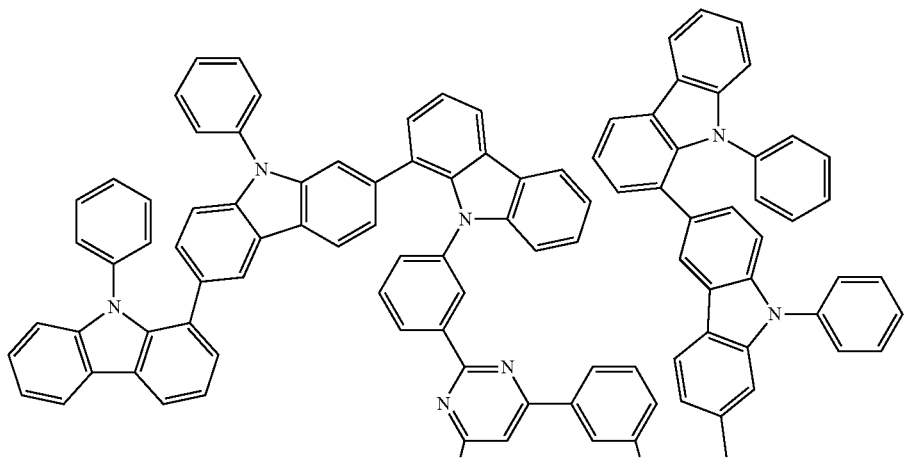

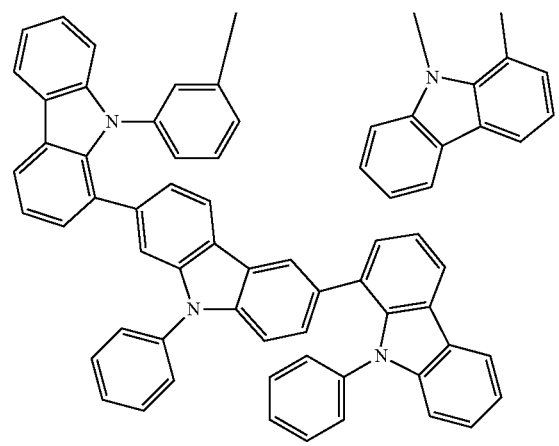
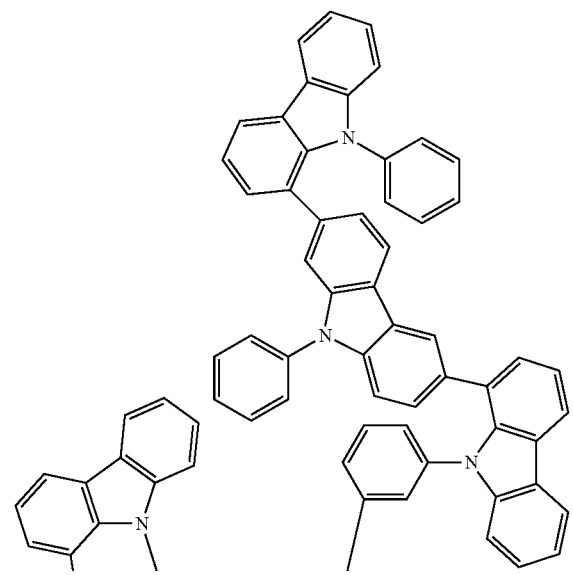
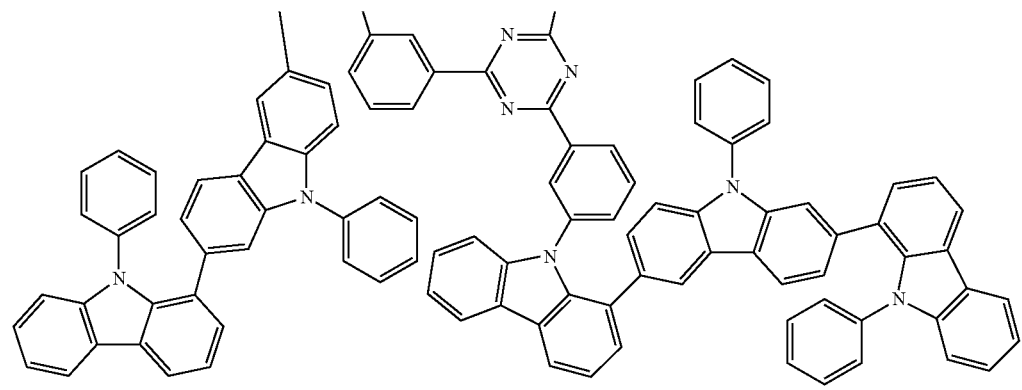

-continued
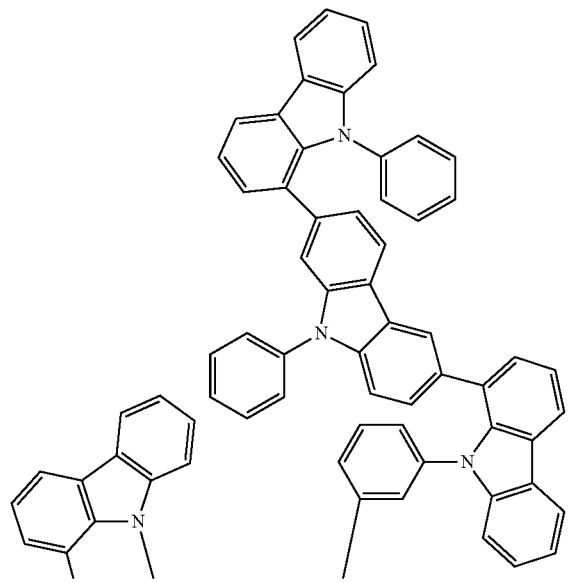
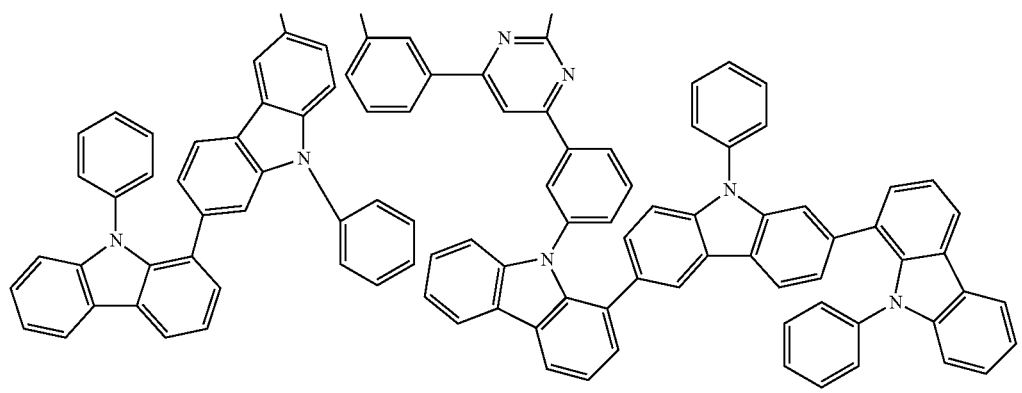
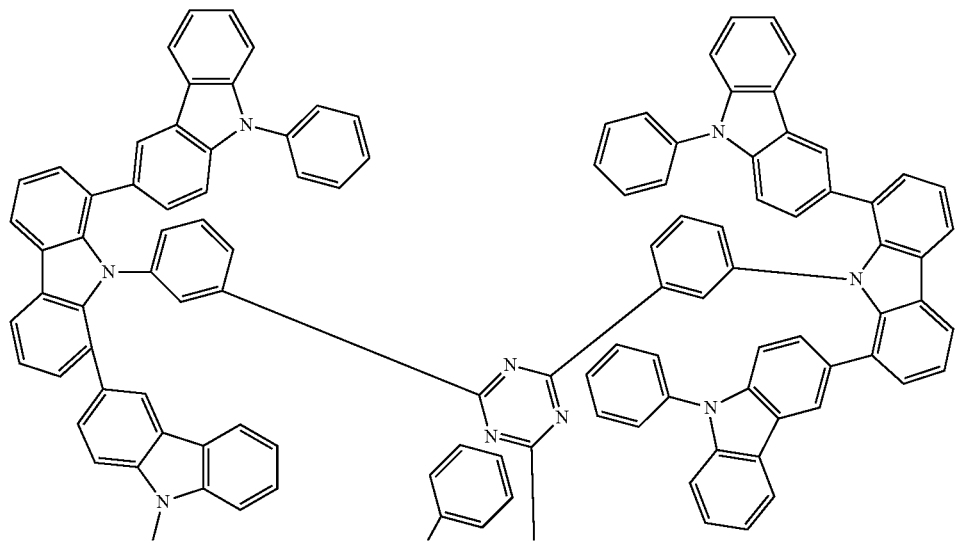

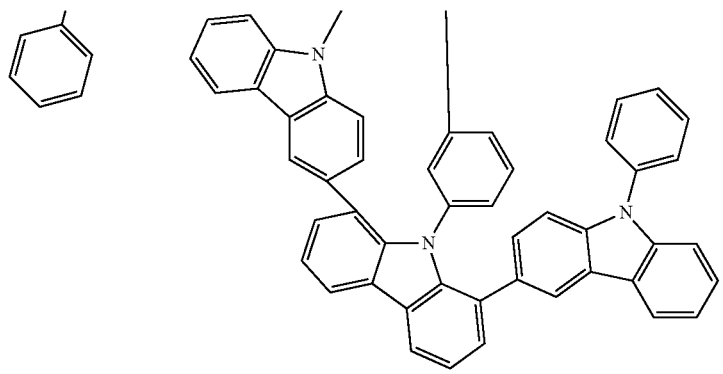
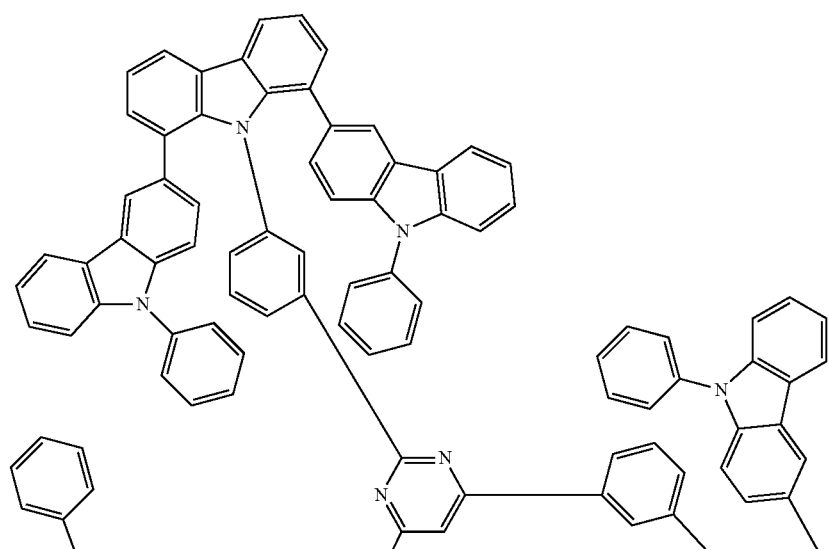
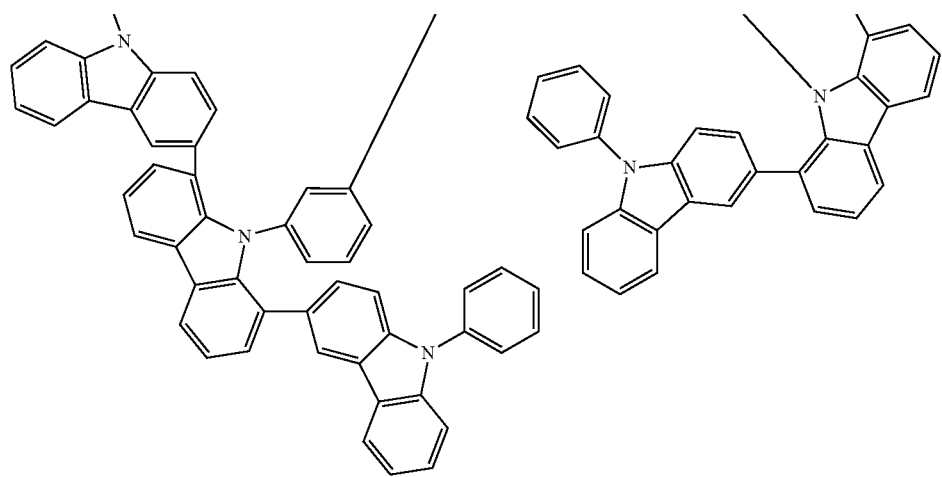

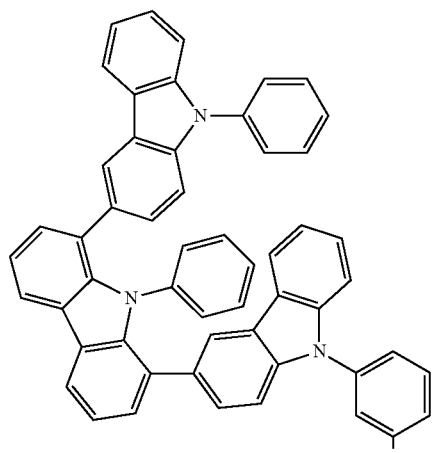
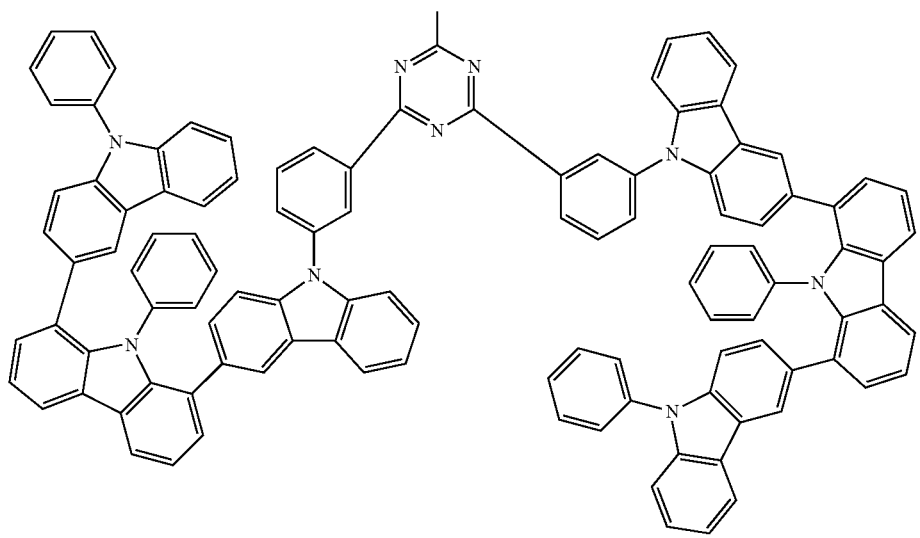
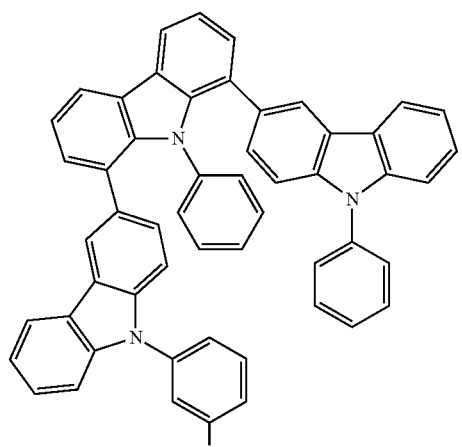

-continued
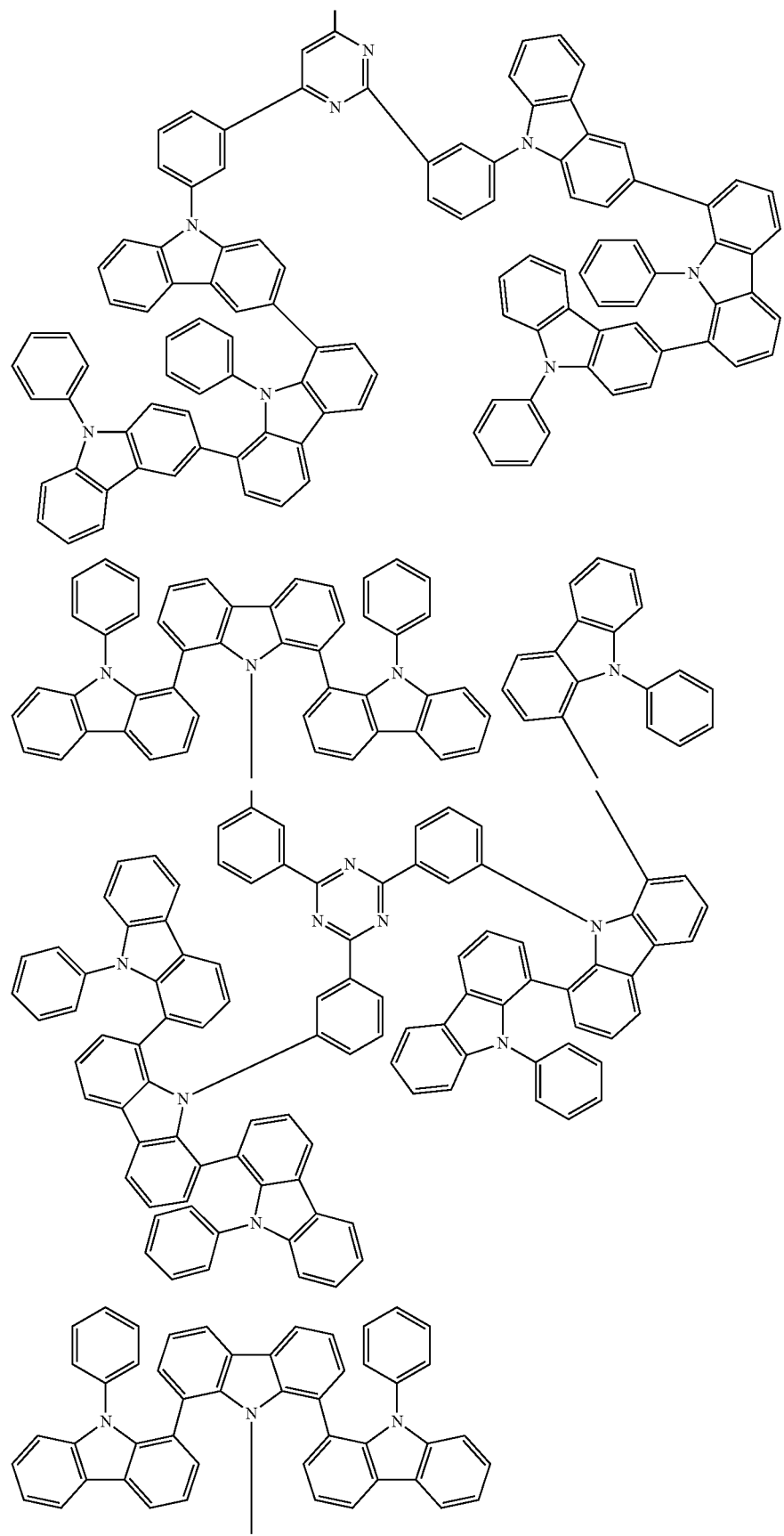

-continued
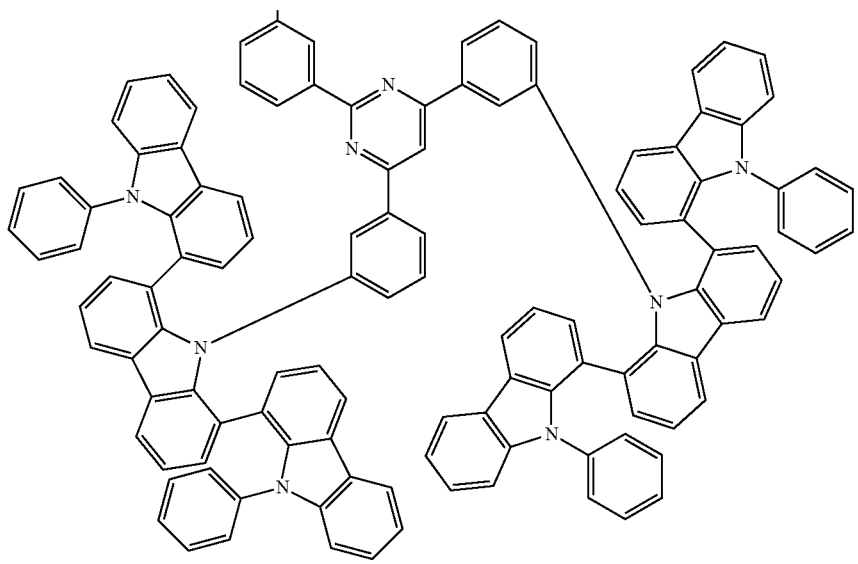
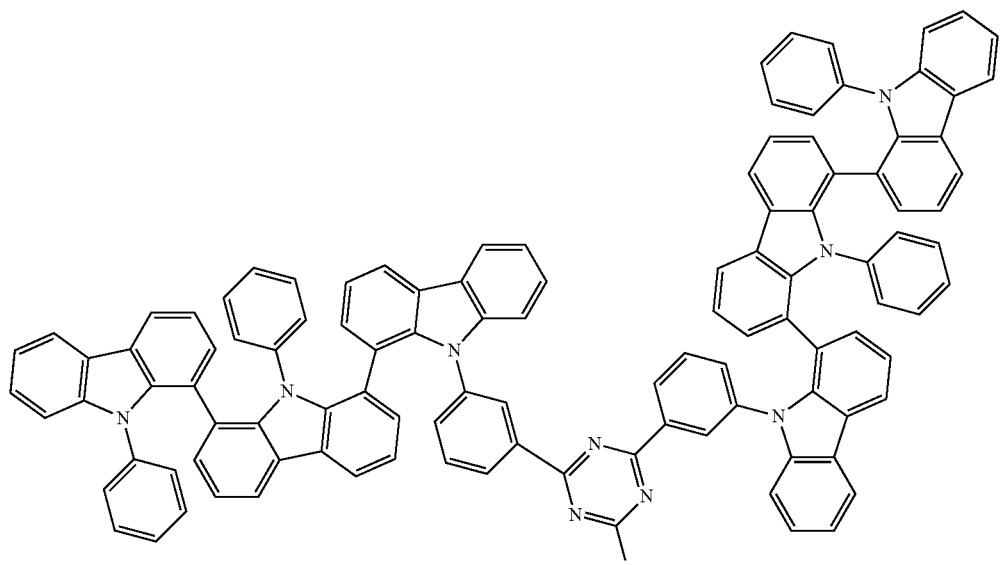
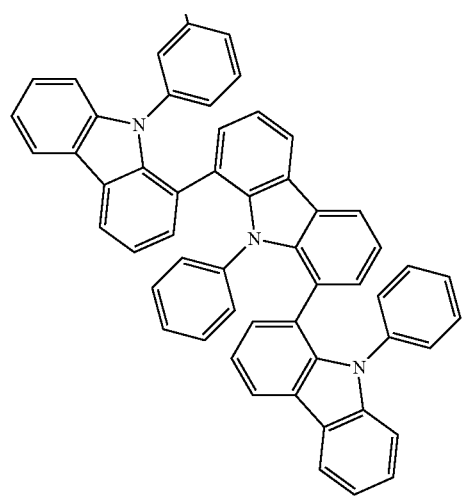

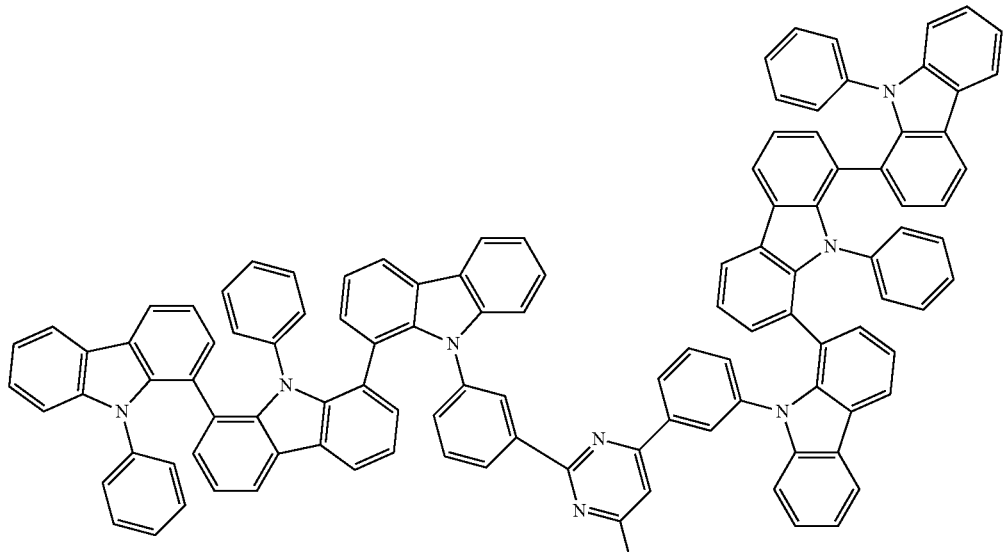
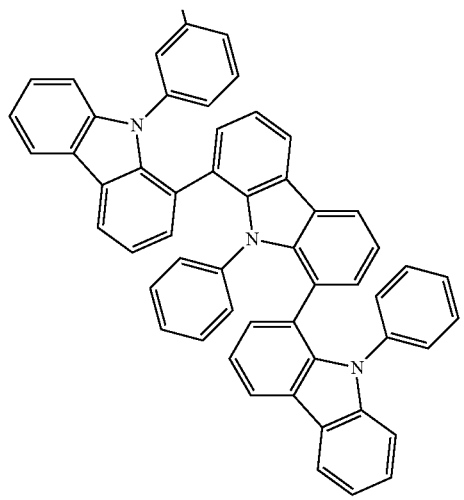
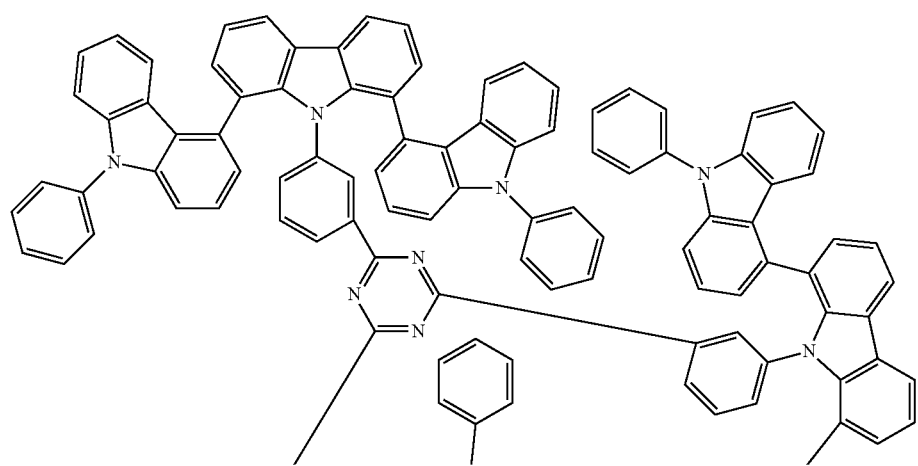

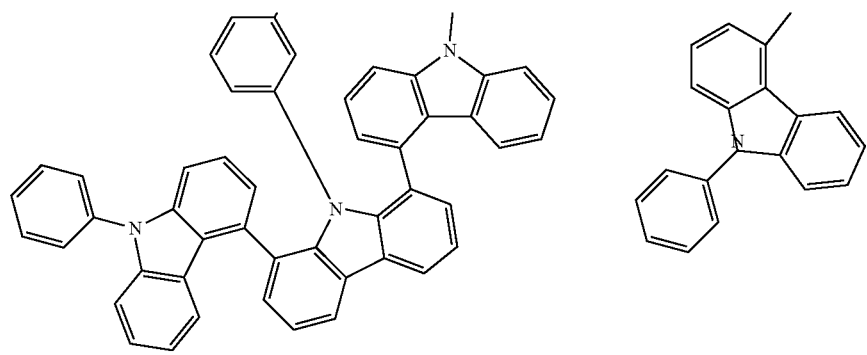
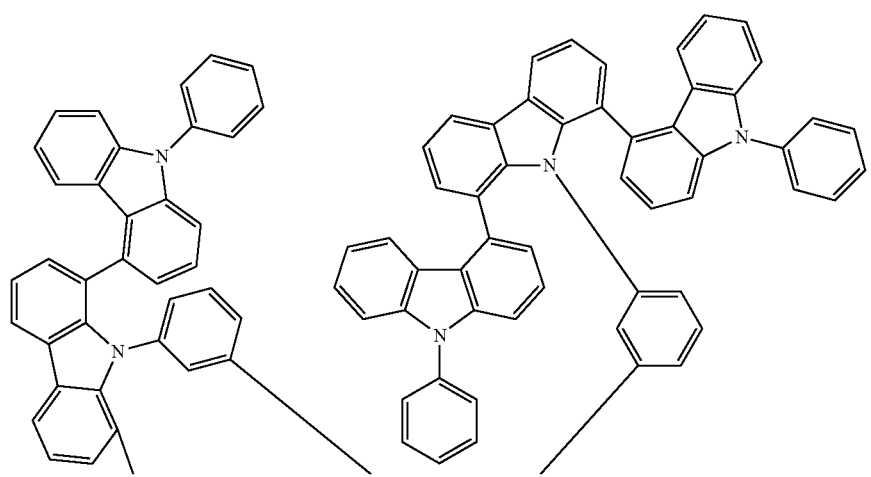
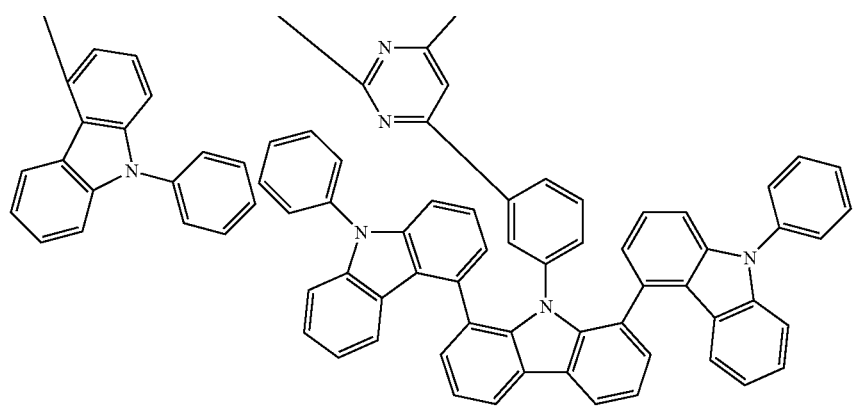

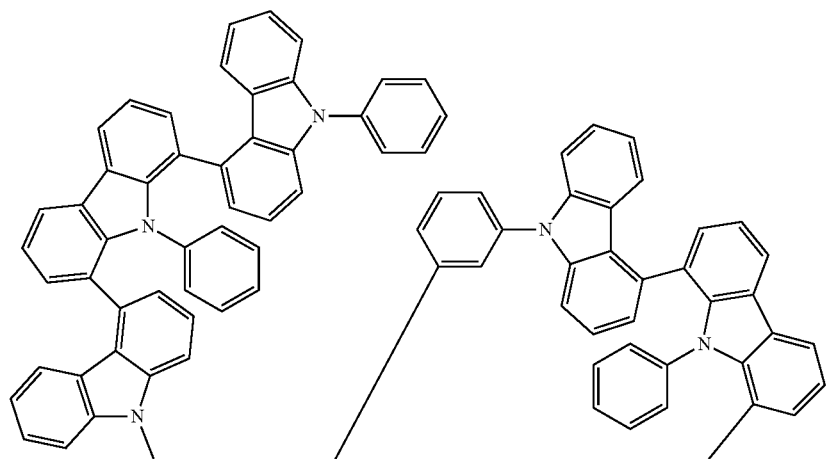
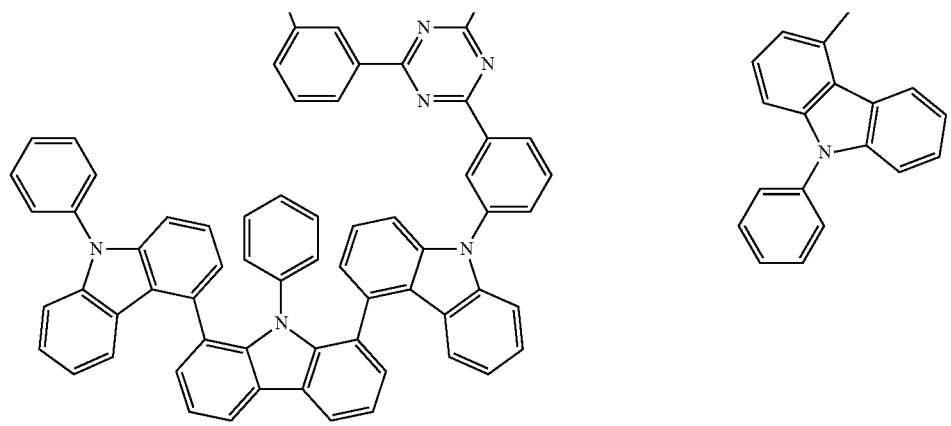
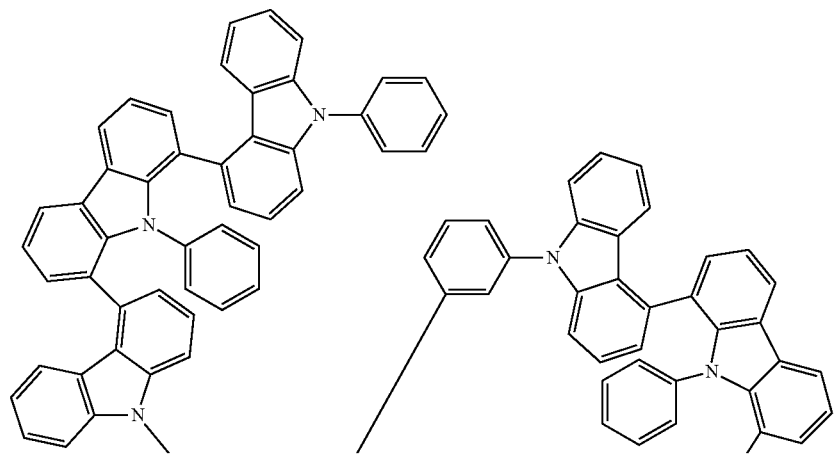

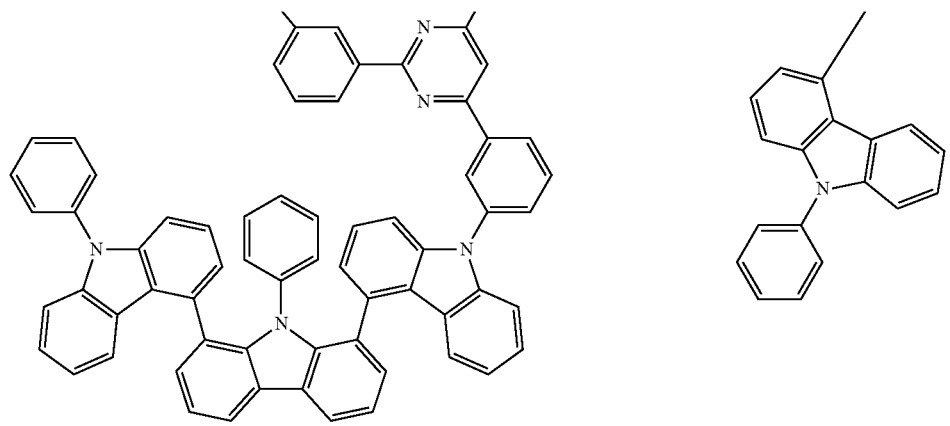
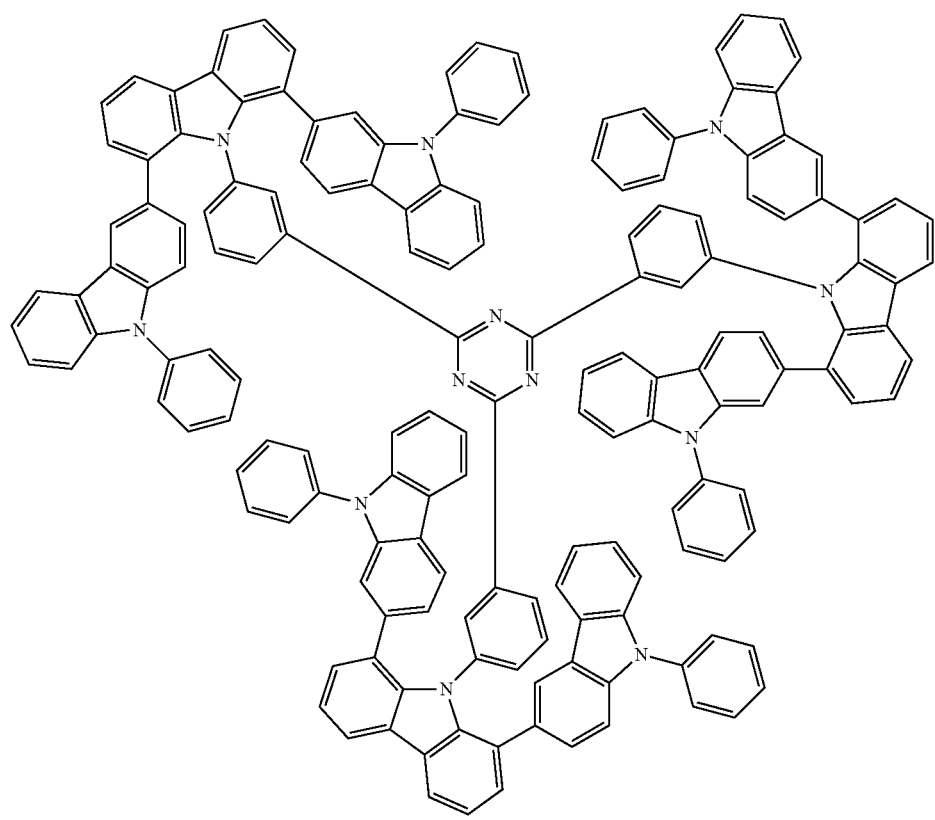

-continued
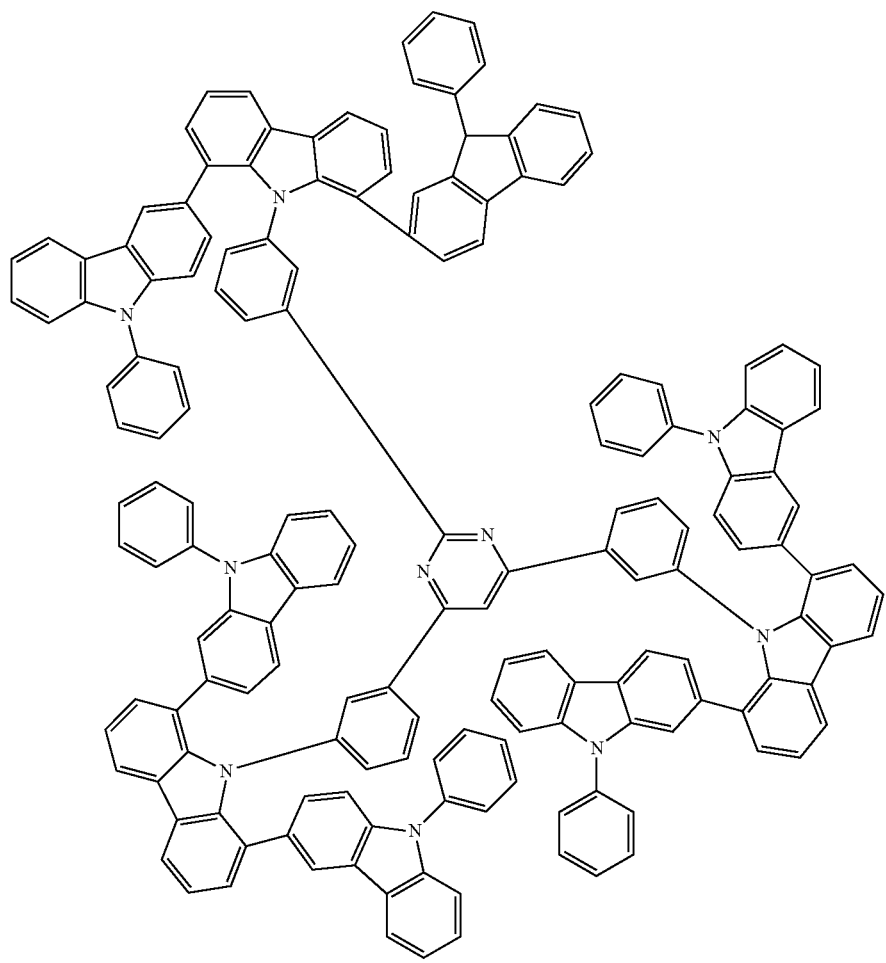

-continued
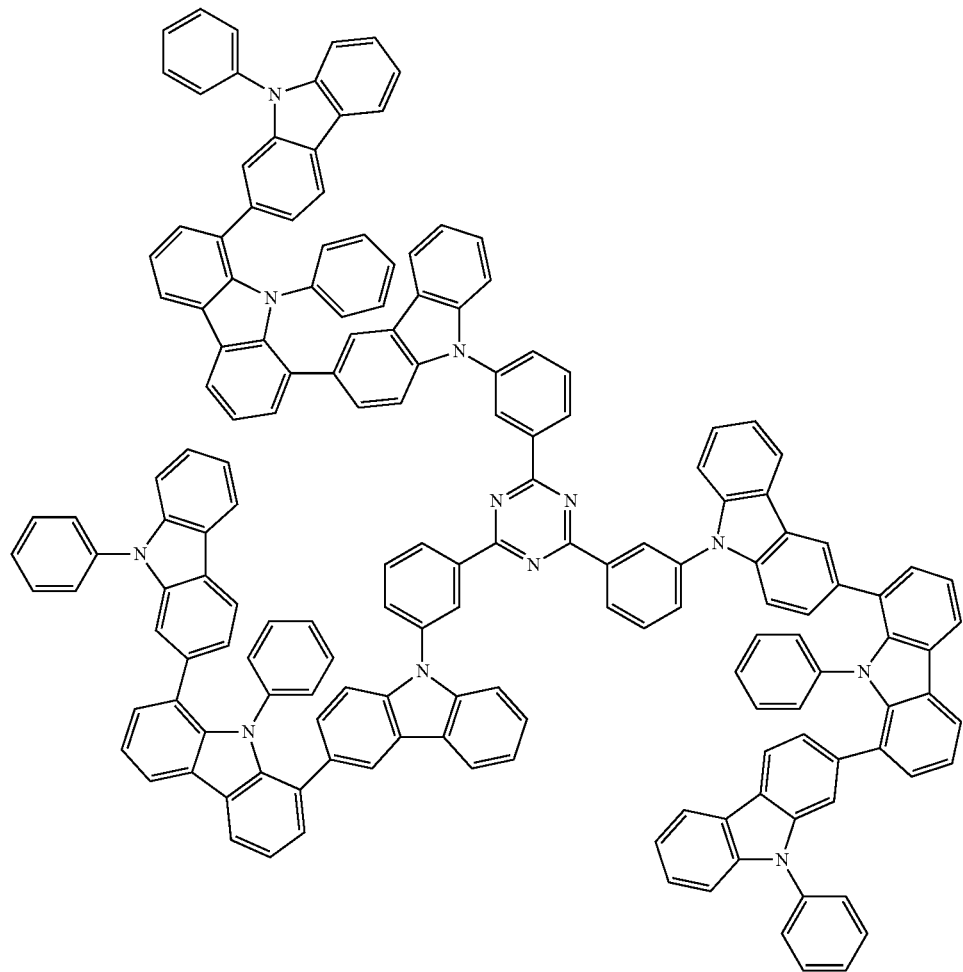 [SMILES: c1ccc(-n2c3ccccc3c3ccc(-c4cccc5c6cccc(-c7ccc8c(c7)c7ccccc7n8-c7cccc(-c8nc(-c9cccc(-n%10c%11ccccc%11c%11cc(-c%12cccc%13c%14cccc(-c%15ccc%16c%17ccccc%17n(-c%17ccccc%17)c%16c%15)c%14n(-c%14ccccc%14)c%12%13)ccc%11%10)c9)nc(-c9cccc(-n%10c%11ccccc%11c%11cc(-c%12cccc%13c%14cccc(-c%15ccc%16c%17ccccc%17n(-c%17ccccc%17)c%16c%15)c%14n(-c%14ccccc%14)c%12%13)ccc%11%10)c9)n8)c7)c6n(-c6ccccc6)c45)cc32)cc1]

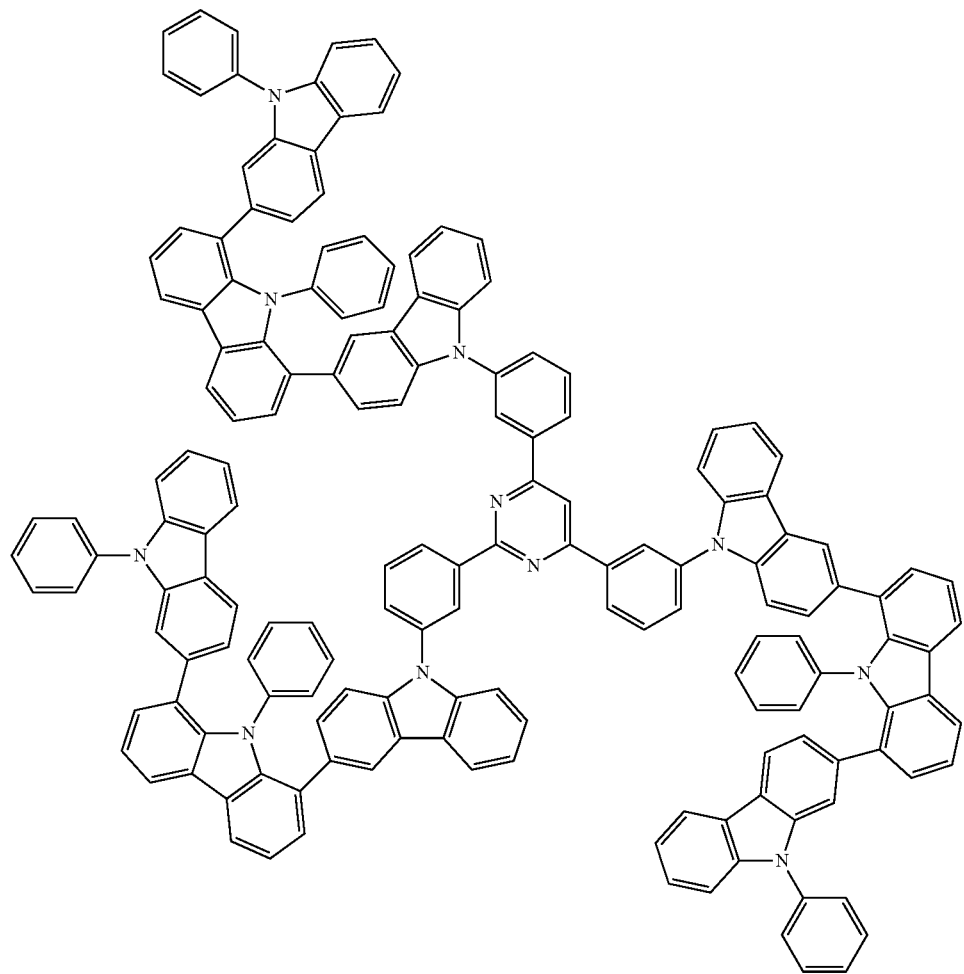

-continued
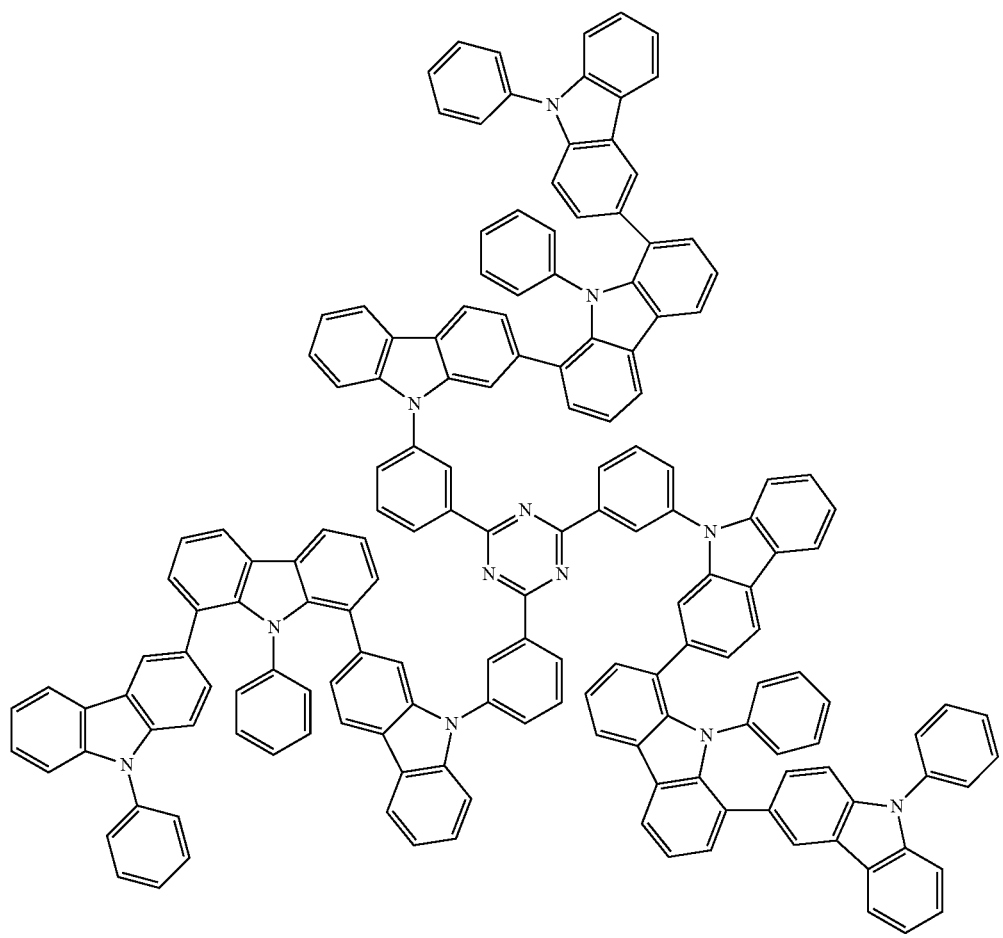 [SMILES: c1ccc(-n2c3ccccc3c3cc(-c4cccc5c6cccc(-c7ccc8c9ccccc9n(-c9cccc(-c%10nc(-c%11cccc(-n%12c%13ccccc%13c%13ccc(-c%14cccc%15c%16cccc(-c%17ccc%18c(c%17)c%17ccccc%17n%18-c%17ccccc%17)c%16n(-c%16ccccc%16)c%14%15)cc%13%12)c%11)nc(-c%11cccc(-n%12c%13ccccc%13c%13ccc(-c%14cccc%15c%16cccc(-c%17ccc%18c(c%17)c%17ccccc%17n%18-c%17ccccc%17)c%16n(-c%16ccccc%16)c%14%15)cc%13%12)c%11)n%10)c9)c8c7)c6n(-c6ccccc6)c45)ccc32)cc1]

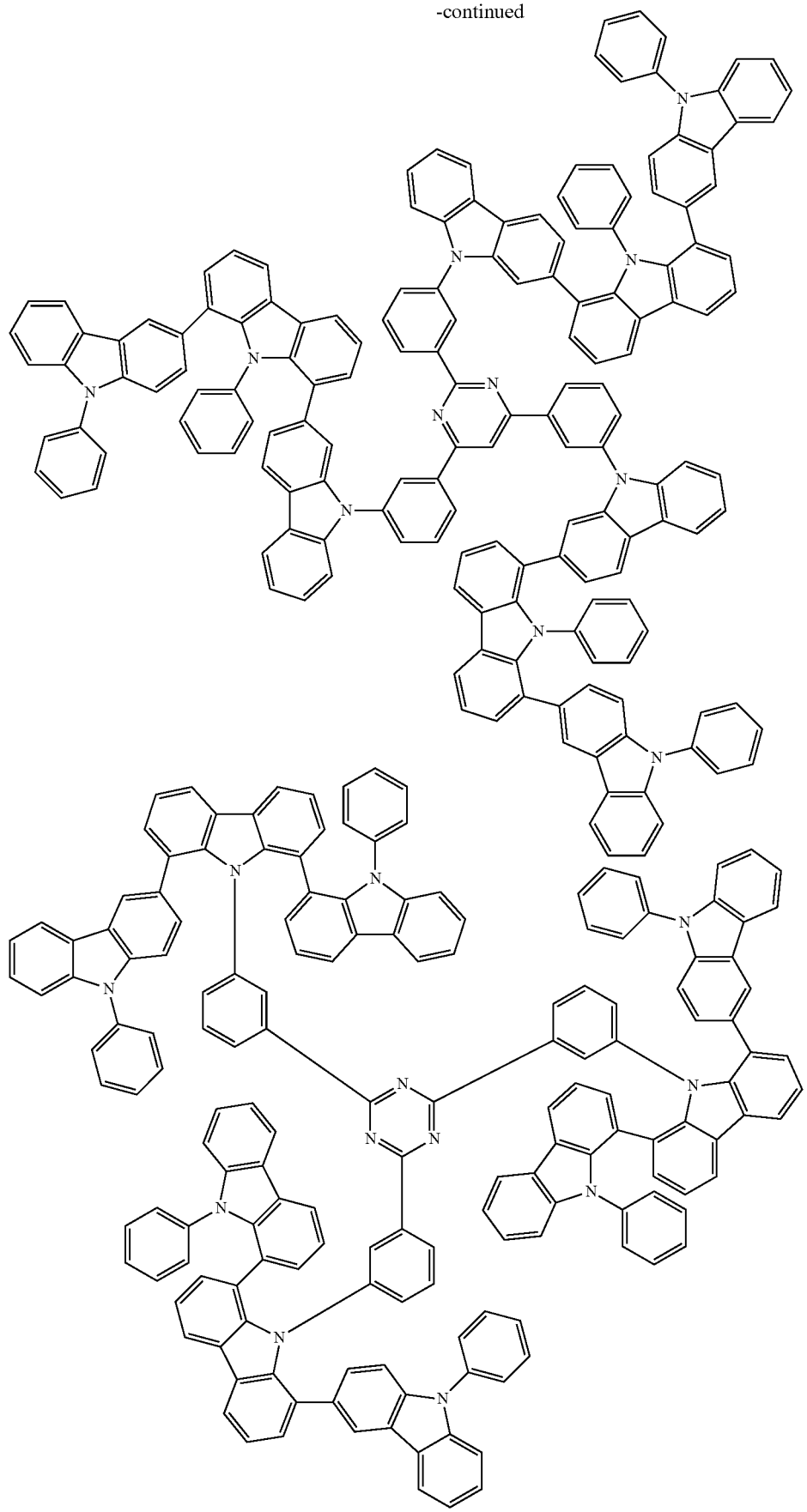

-continued
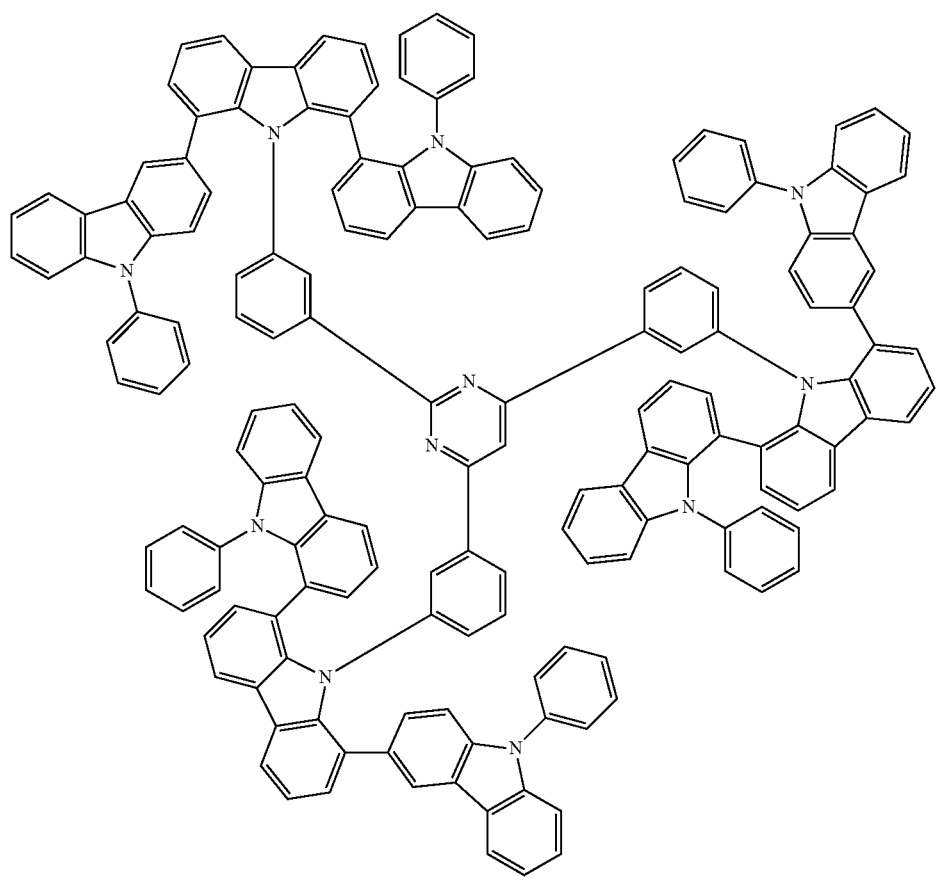 [SMILES: c1ccc(-n2c3ccccc3c3cc(-c4cccc5c6cccc(-c7cccc8c9ccccc9n(-c9ccccc9)c78)c6n(-c6cccc(-c7cc(-c8cccc(-n9c%10c(-c%11ccc%12c(c%11)c%11ccccc%11n%12-c%11ccccc%11)cccc%10c%10cccc(-c%11cccc%12c%13ccccc%13n(-c%13ccccc%13)c%11%12)c%109)c8)nc(-c8cccc(-n9c%10c(-c%11ccc%12c(c%11)c%11ccccc%11n%12-c%11ccccc%11)cccc%10c%10cccc(-c%11cccc%12c%13ccccc%13n(-c%13ccccc%13)c%11%12)c%109)c8)n7)c6)c45)ccc32)cc1]

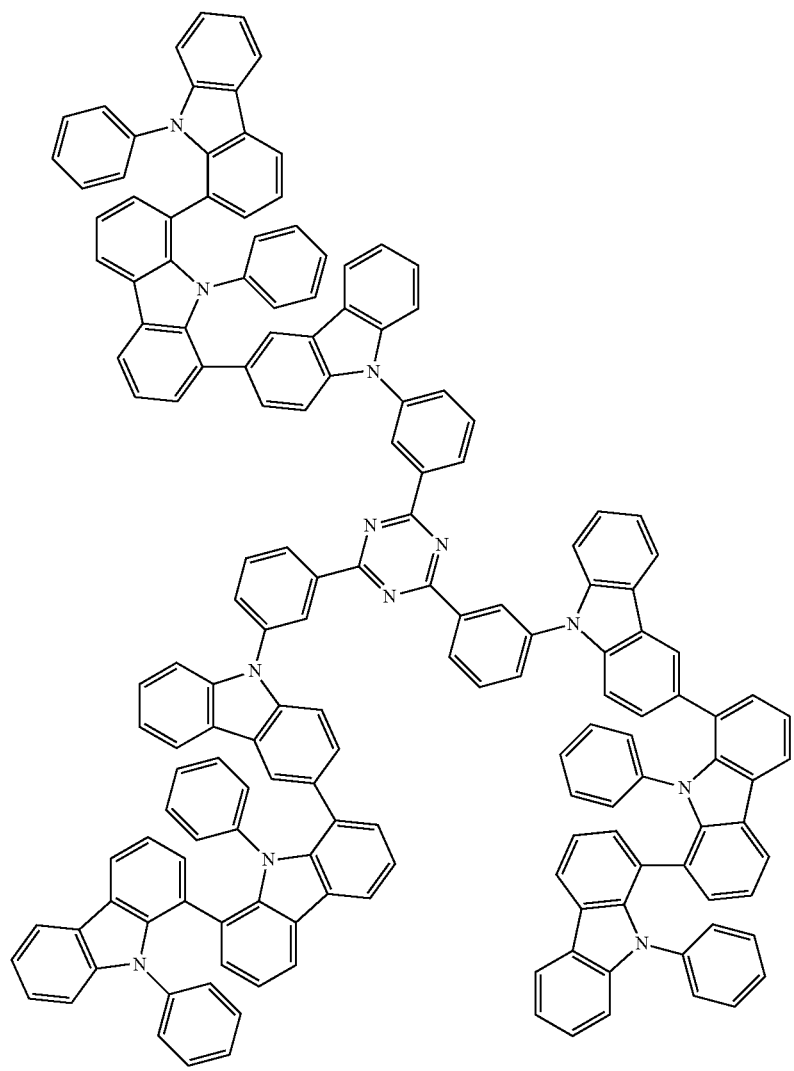 [SMILES: c1ccc(-n2c3ccccc3c3cccc(-c4cccc5c6cccc(-c7ccc8c(c7)c7ccccc7n8-c7cccc(-c8nc(-c9cccc(-n%10c%11ccccc%11c%11cc(-c%12cccc%13c%14cccc(-c%15cccc%16c%17ccccc%17n(-c%17ccccc%17)c%15%16)c%14n(-c%14ccccc%14)c%12%13)ccc%11%10)c9)nc(-c9cccc(-n%10c%11ccccc%11c%11cc(-c%12cccc%13c%14cccc(-c%15cccc%16c%17ccccc%17n(-c%17ccccc%17)c%15%16)c%14n(-c%14ccccc%14)c%12%13)ccc%11%10)c9)n8)c7)c6n(-c6ccccc6)c45)c32)cc1]

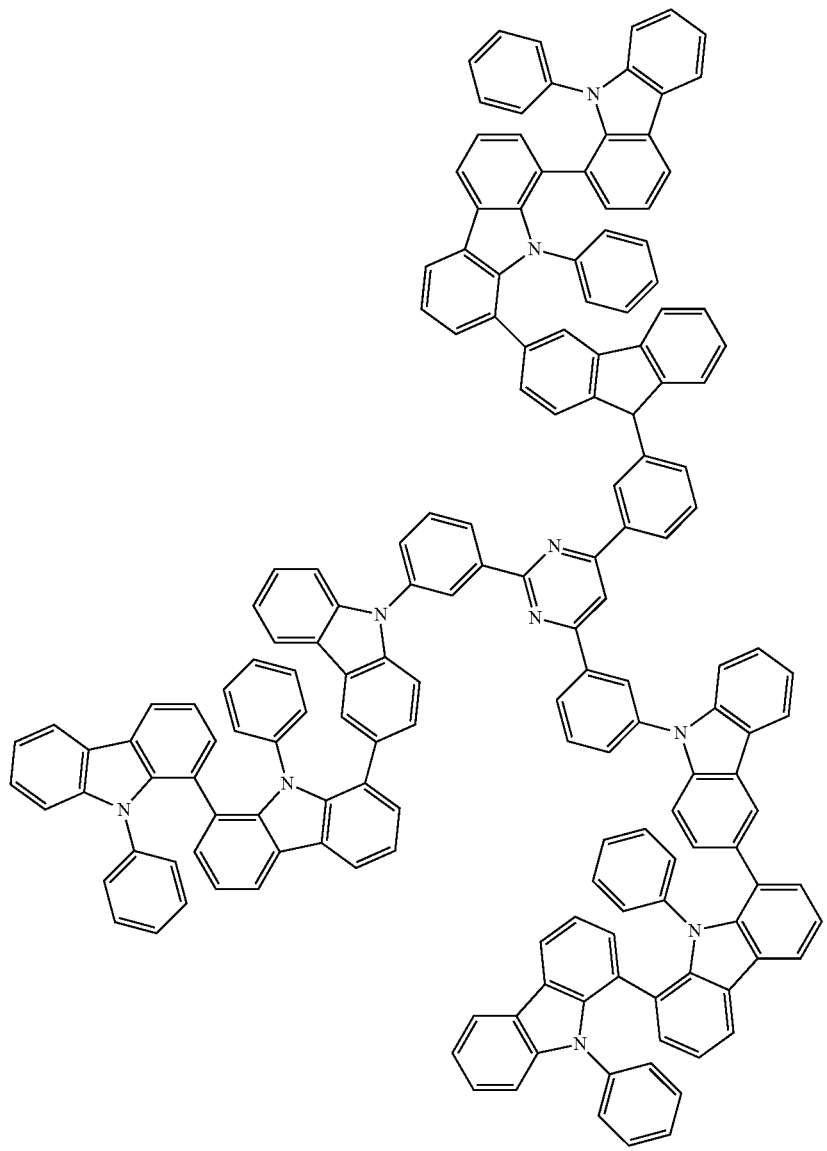 [SMILES: c1ccc(-n2c3ccccc3c3cccc(-c4cccc5c6cccc(-c7ccc8c(c7)-c7ccccc7C8c7cccc(-c8cc(-c9cccc(-n%10c%11ccccc%11c%11cc(-c%12cccc%13c%14cccc(-c%15cccc%16c%17ccccc%17n(-c%17ccccc%17)c%15%16)c%14n(-c%14ccccc%14)c%12%13)ccc%11%10)c9)nc(-c9cccc(-n%10c%11ccccc%11c%11cc(-c%12cccc%13c%14cccc(-c%15cccc%16c%17ccccc%17n(-c%17ccccc%17)c%15%16)c%14n(-c%14ccccc%14)c%12%13)ccc%11%10)c9)n8)c7)c6n(-c6ccccc6)c45)c32)cc1]

-continued
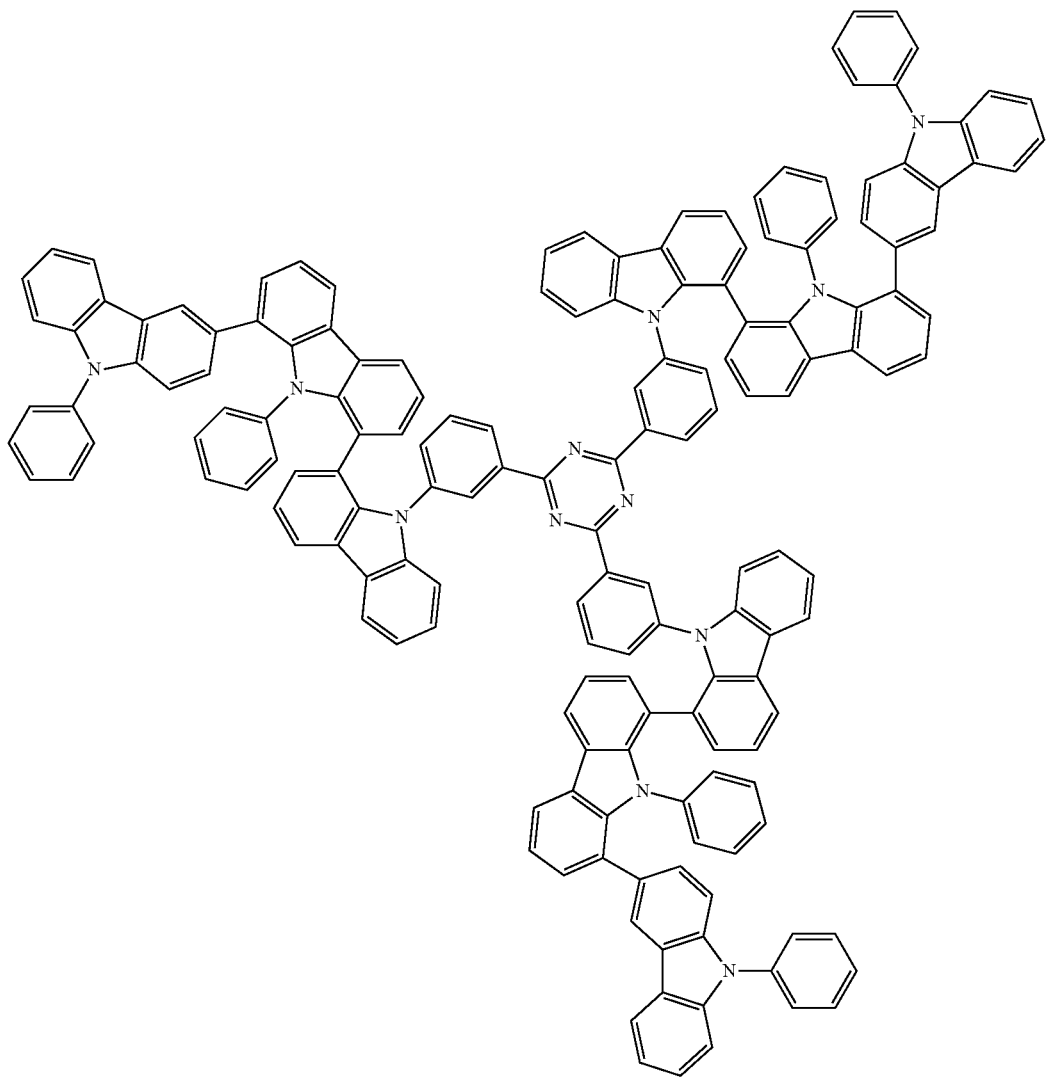 [SMILES: c1ccc(-n2c3ccccc3c3cc(-c4cccc5c6cccc(-c7cccc8c9ccccc9n(-c9cccc(-c%10nc(-c%11cccc(-n%12c%13ccccc%13c%13cccc(-c%14cccc%15c%16cccc(-c%17ccc%18c(c%17)c%17ccccc%17n%18-c%17ccccc%17)c%16n(-c%16ccccc%16)c%14%15)c%13%12)c%11)nc(-c%11cccc(-n%12c%13ccccc%13c%13cccc(-c%14cccc%15c%16cccc(-c%17ccc%18c(c%17)c%17ccccc%17n%18-c%17ccccc%17)c%16n(-c%16ccccc%16)c%14%15)c%13%12)c%11)n%10)c9)c78)c6n(-c6ccccc6)c45)ccc32)cc1]

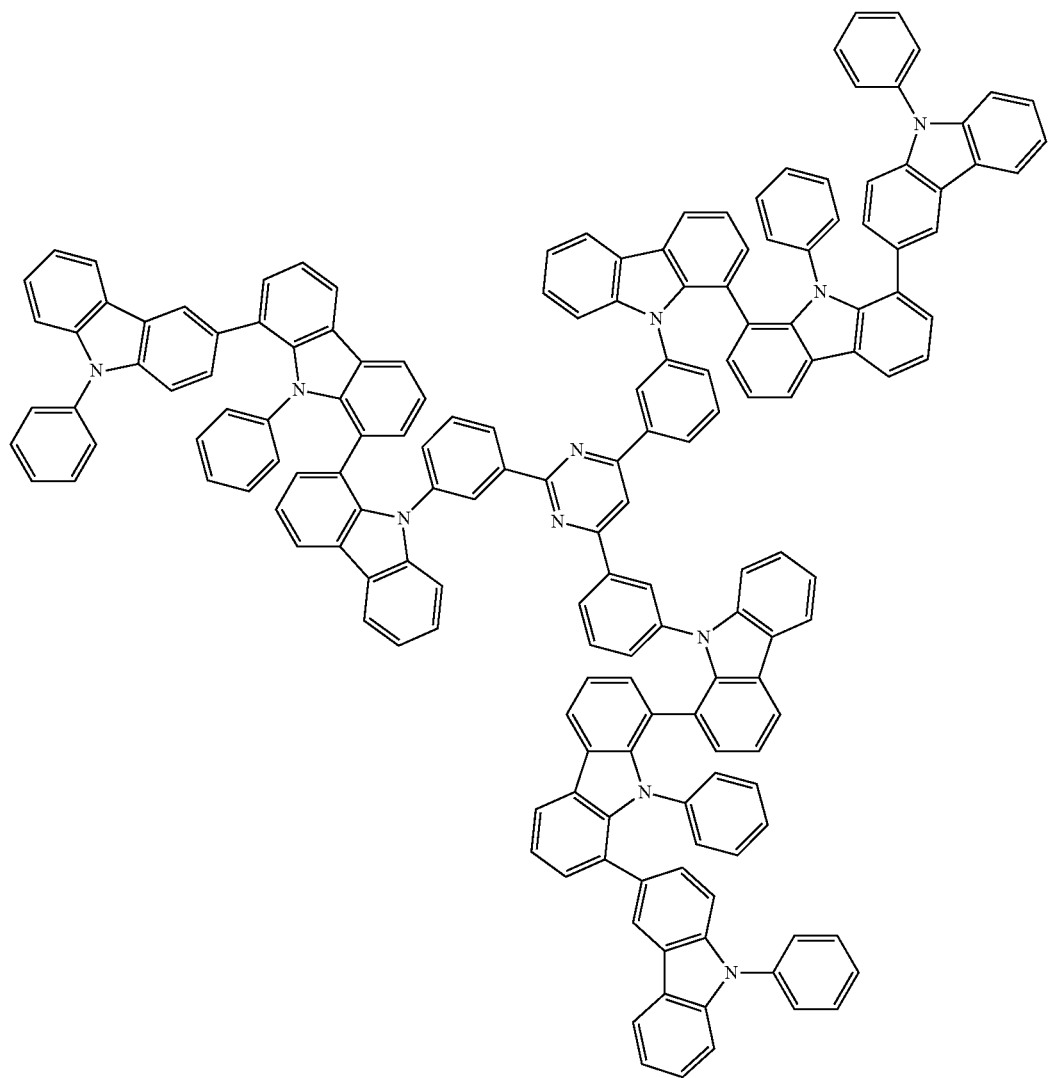

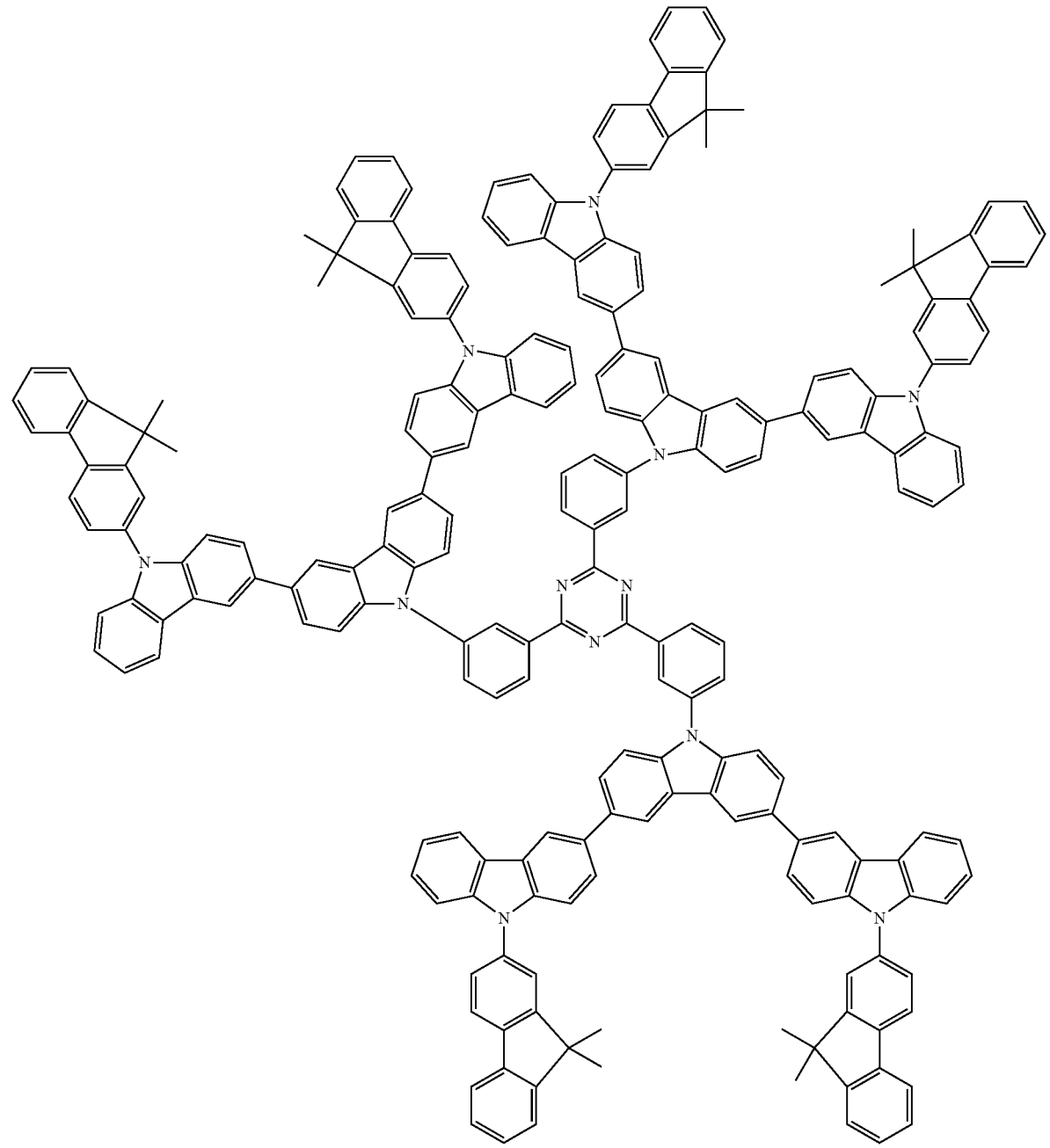

-continued
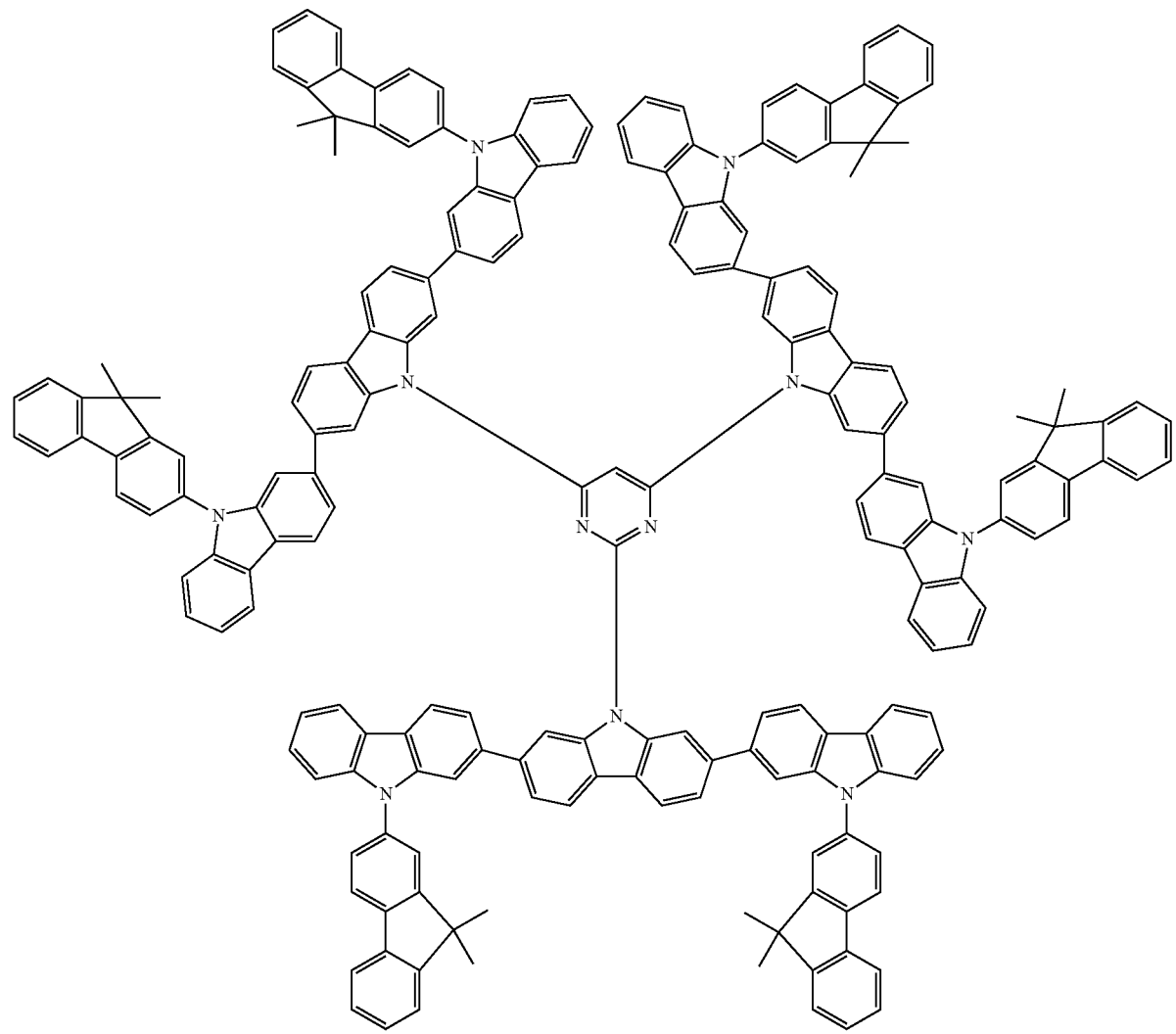 [SMILES: CC1(C)c2ccccc2-c2ccc(-n3c4ccccc4c4ccc(-c5ccc6c7ccc(-c8ccc9c%10ccccc%10n(-c%10ccc%11c(c%10)C(C)(C)c%10ccccc%10-%11)c9c8)cc7n(-c7cc(-n8c9cc(-c%10ccc%11c%12ccccc%12n(-c%12ccc%13c(c%12)C(C)(C)c%12ccccc%12-%13)c%11c%10)ccc9c9ccc(-c%10ccc%11c%12ccccc%12n(-c%12ccc%13c(c%12)C(C)(C)c%12ccccc%12-%13)c%11c%10)cc98)nc(-n8c9cc(-c%10ccc%11c%12ccccc%12n(-c%12ccc%13c(c%12)C(C)(C)c%12ccccc%12-%13)c%11c%10)ccc9c9ccc(-c%10ccc%11c%12ccccc%12n(-c%12ccc%13c(c%12)C(C)(C)c%12ccccc%12-%13)c%11c%10)cc98)n7)c6c5)cc43)cc21]

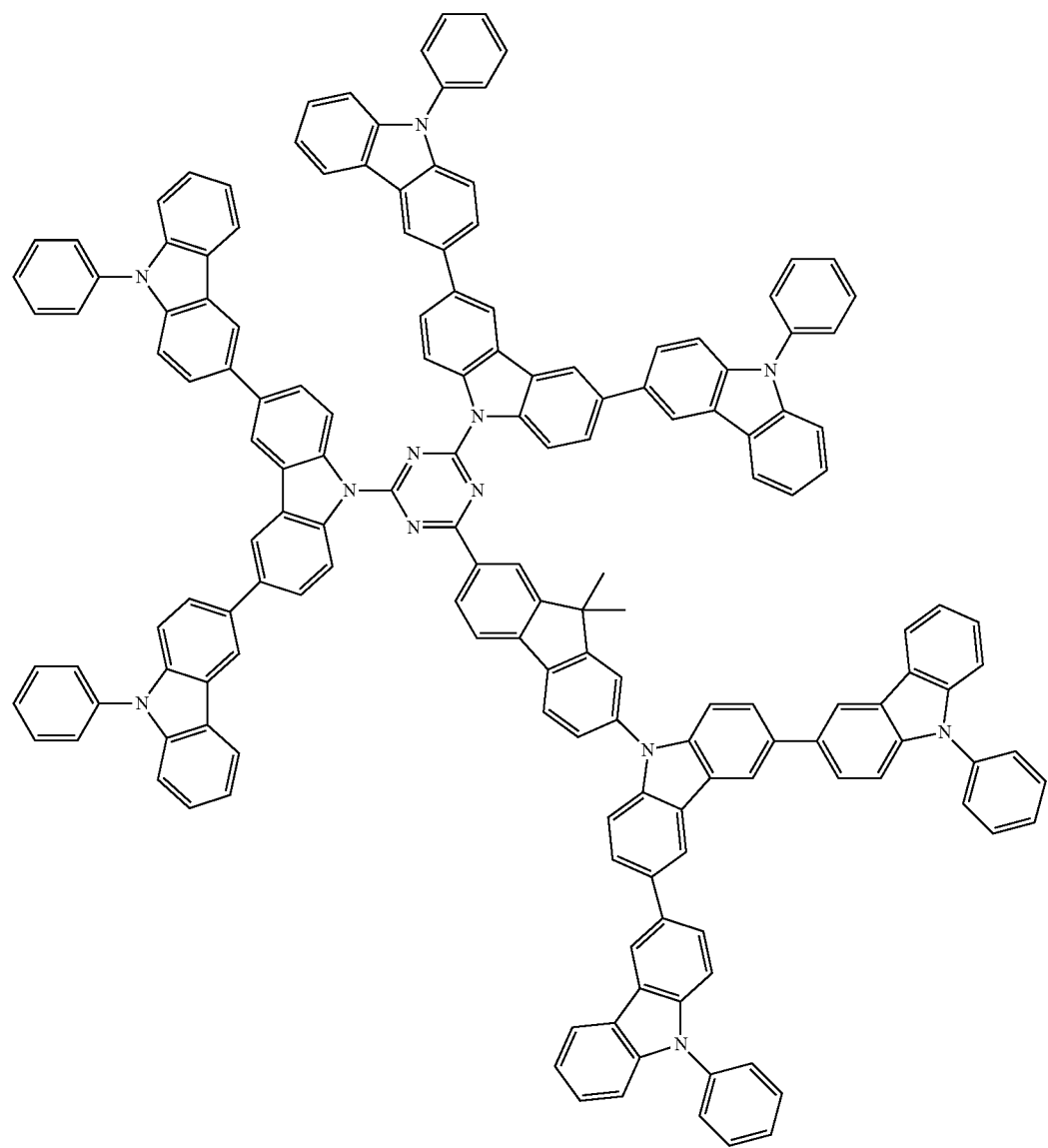 [SMILES: CC1(C)c2cc(-c3cc(-n4c5ccc(-c6ccc7c(c6)c6ccccc6n7-c6ccccc6)cc5c5cc(-c6ccc7c(c6)c6ccccc6n7-c6ccccc6)ccc54)nc(-n4c5ccc(-c6ccc7c(c6)c6ccccc6n7-c6ccccc6)cc5c5cc(-c6ccc7c(c6)c6ccccc6n7-c6ccccc6)ccc54)n3)ccc2-c2ccc(-n3c4ccc(-c5ccc6c(c5)c5ccccc5n6-c5ccccc5)cc4c4cc(-c5ccc6c(c5)c5ccccc5n6-c5ccccc5)ccc43)cc21]

-continued
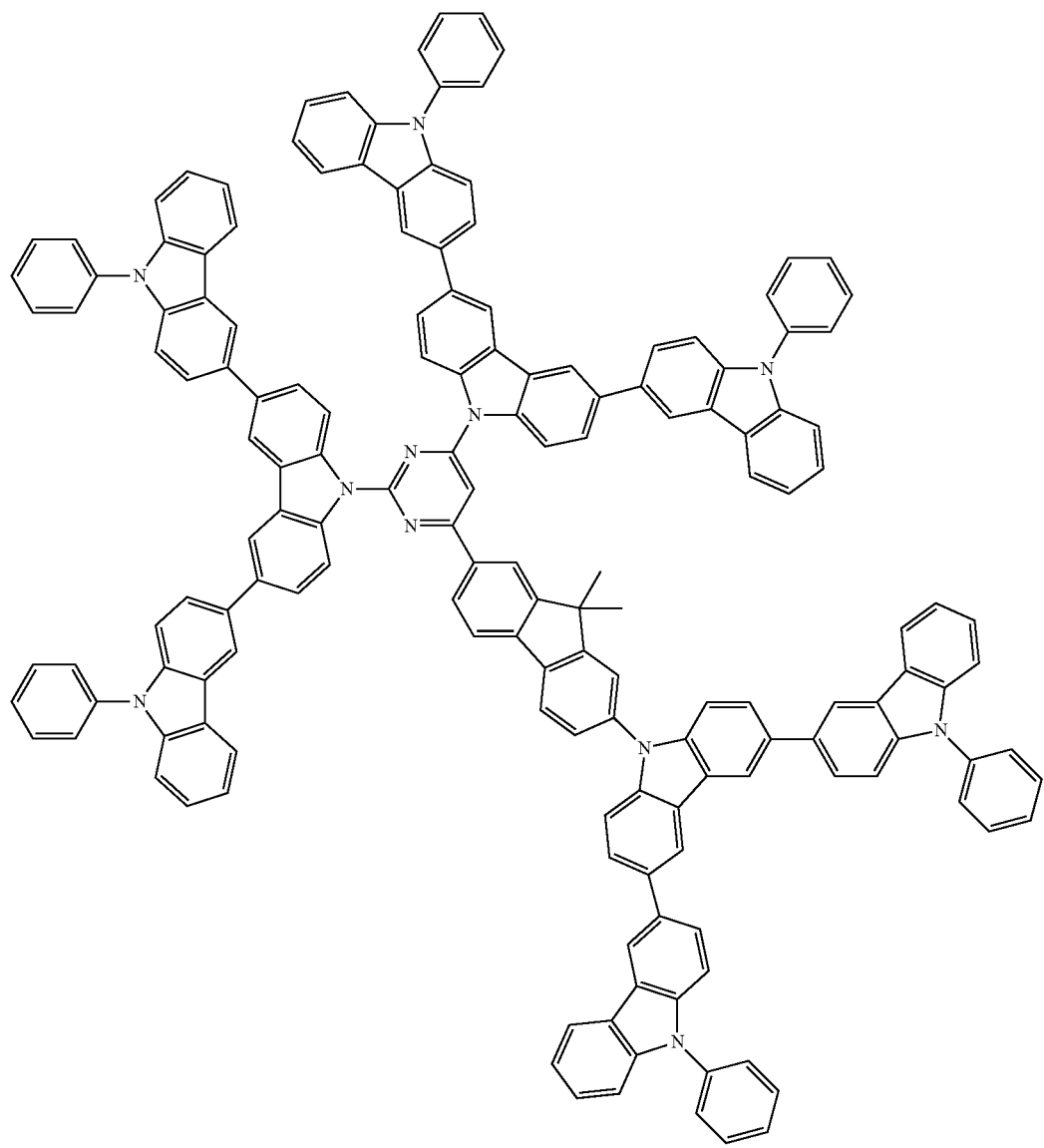

-continued
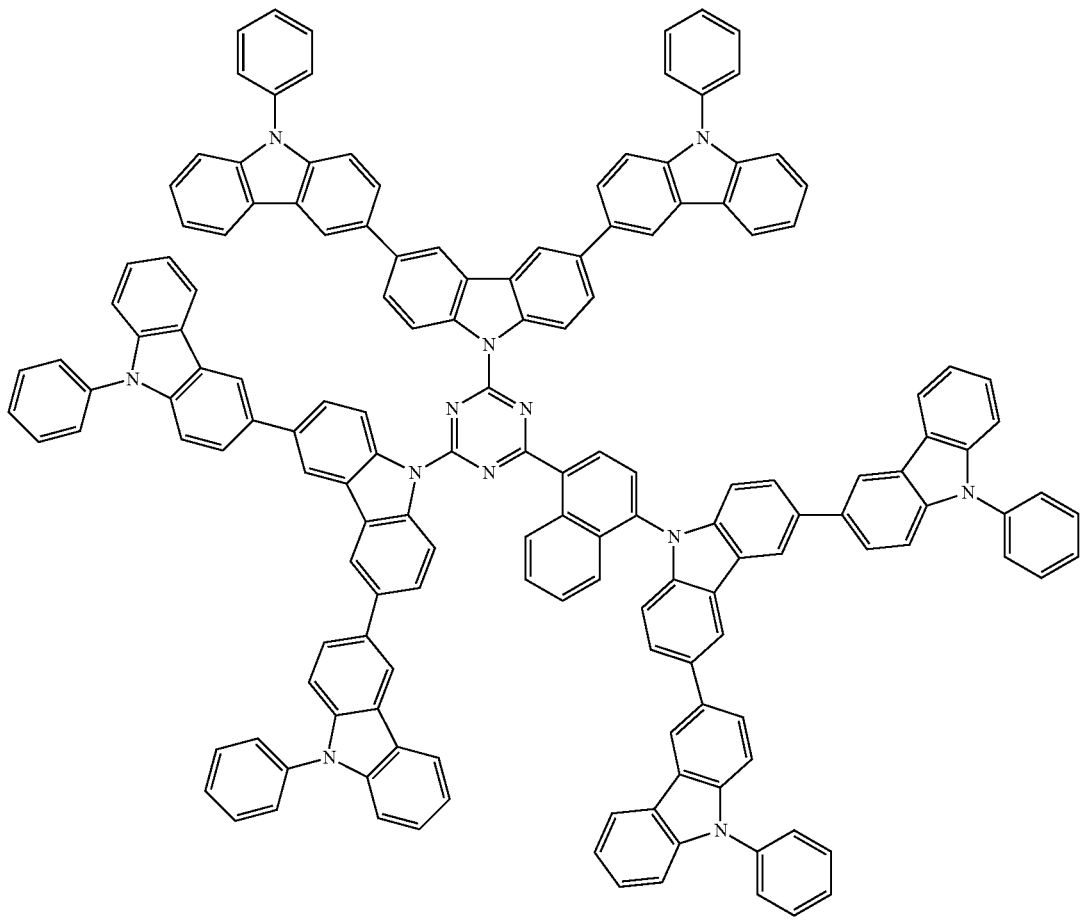

-continued
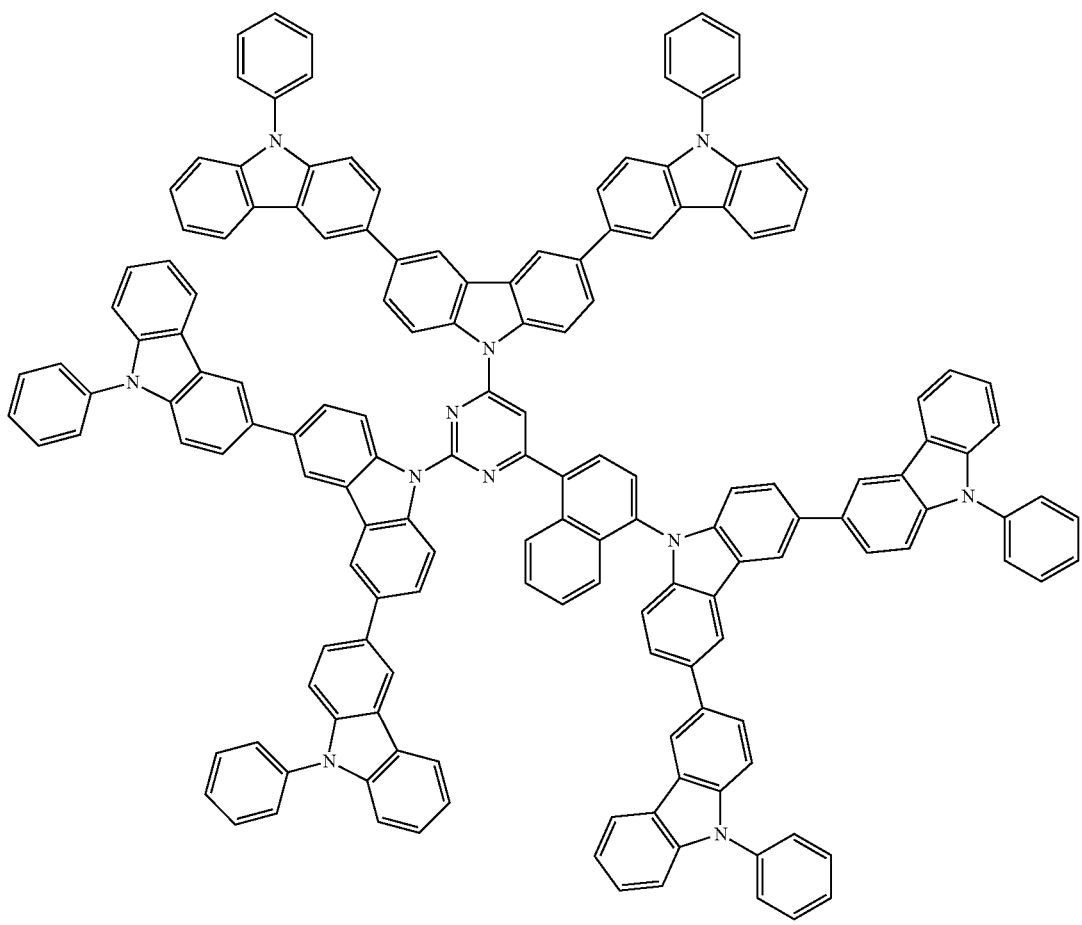

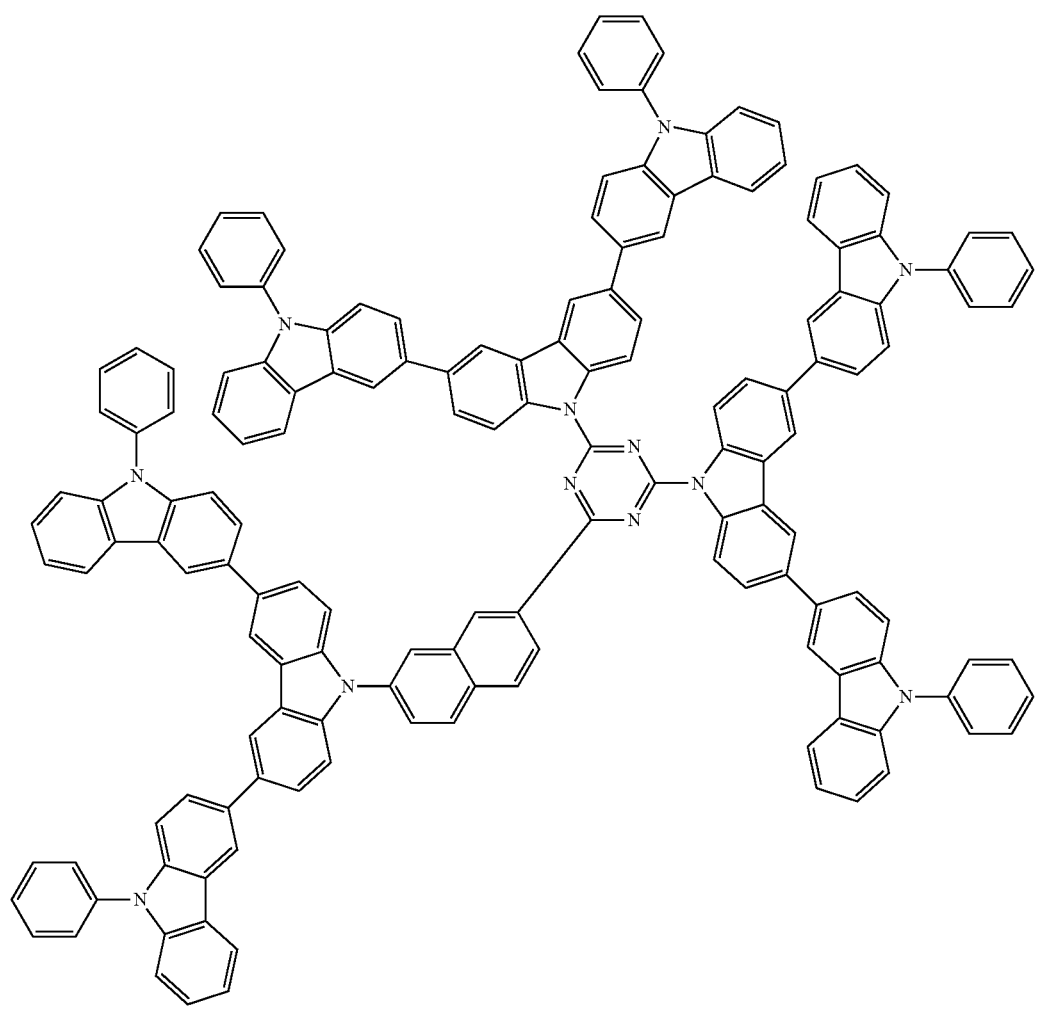 [SMILES: c1ccc(-n2c3ccccc3c3cc(-c4ccc5c(c4)c4cc(-c6ccc7c(c6)c6ccccc6n7-c6ccccc6)ccc4n5-c4ccc5ccc(-c6nc(-n7c8ccc(-c9ccc%10c(c9)c9ccccc9n%10-c9ccccc9)cc8c8cc(-c9ccc%10c(c9)c9ccccc9n%10-c9ccccc9)ccc87)nc(-n7c8ccc(-c9ccc%10c(c9)c9ccccc9n%10-c9ccccc9)cc8c8cc(-c9ccc%10c(c9)c9ccccc9n%10-c9ccccc9)ccc87)n6)cc5c4)ccc32)cc1]

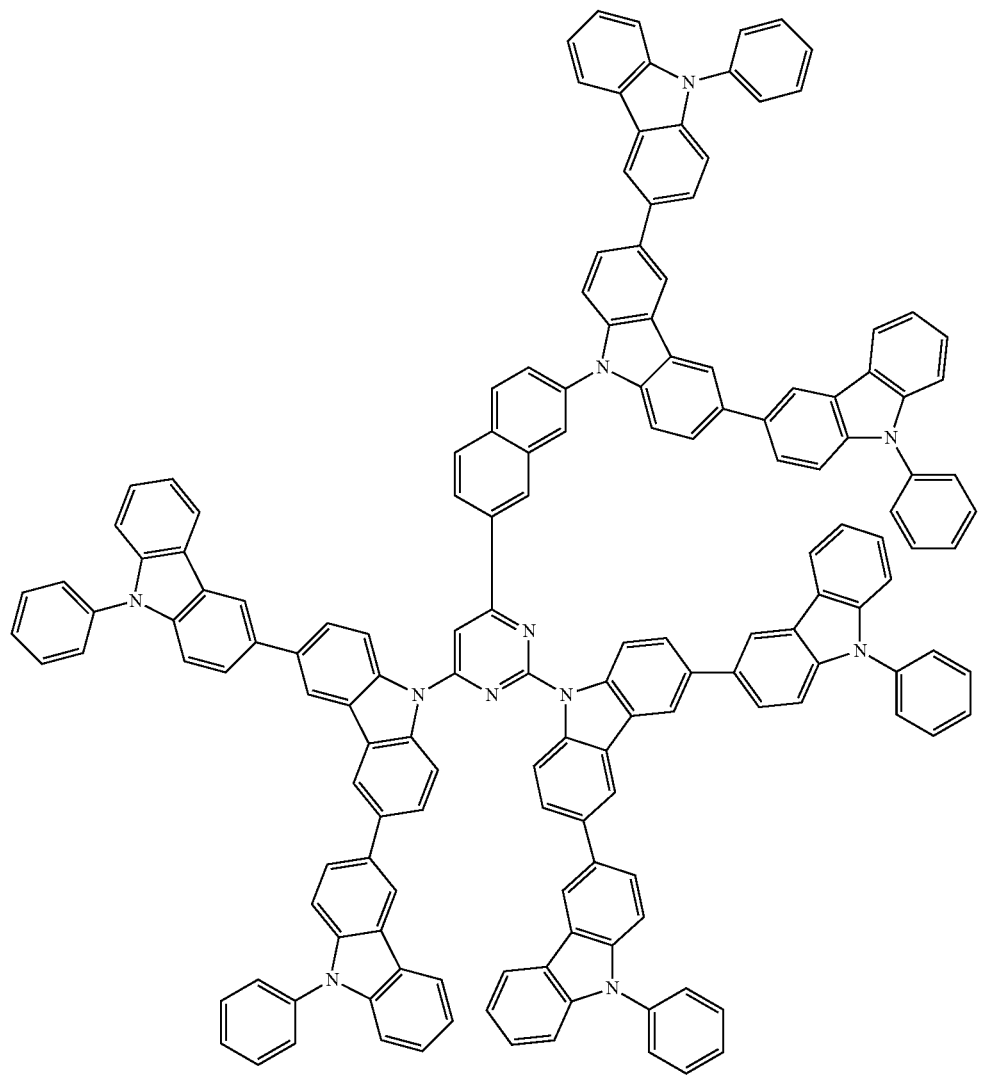 [SMILES: c1ccc(-n2c3ccccc3c3cc(-c4ccc5c(c4)c4cc(-c6ccc7c(c6)c6ccccc6n7-c6ccccc6)ccc4n5-c4ccc5ccc(-c6cc(-n7c8ccc(-c9ccc%10c(c9)c9ccccc9n%10-c9ccccc9)cc8c8cc(-c9ccc%10c(c9)c9ccccc9n%10-c9ccccc9)ccc87)nc(-n7c8ccc(-c9ccc%10c(c9)c9ccccc9n%10-c9ccccc9)cc8c8cc(-c9ccc%10c(c9)c9ccccc9n%10-c9ccccc9)ccc87)n6)cc5c4)ccc32)cc1]

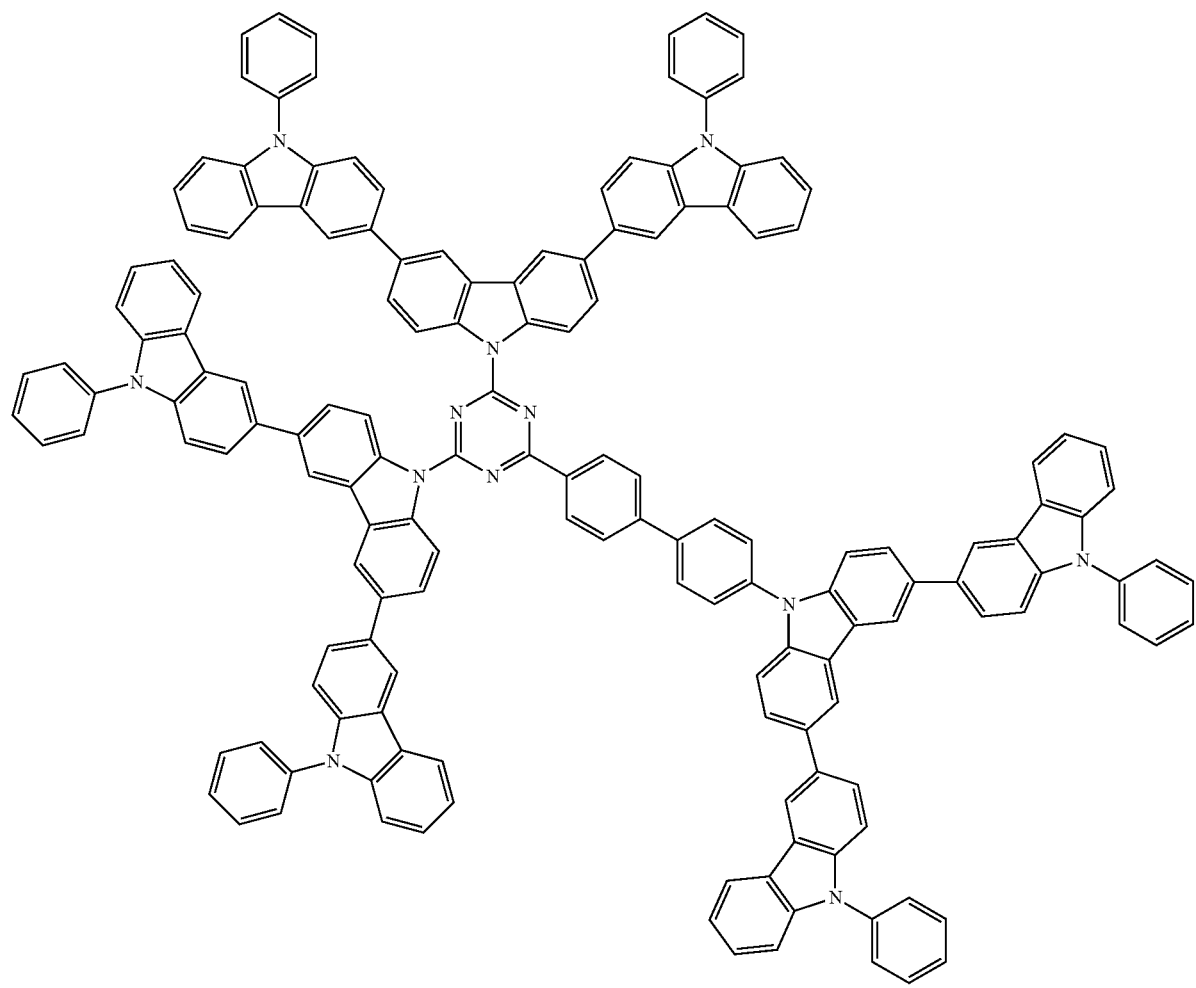

-continued
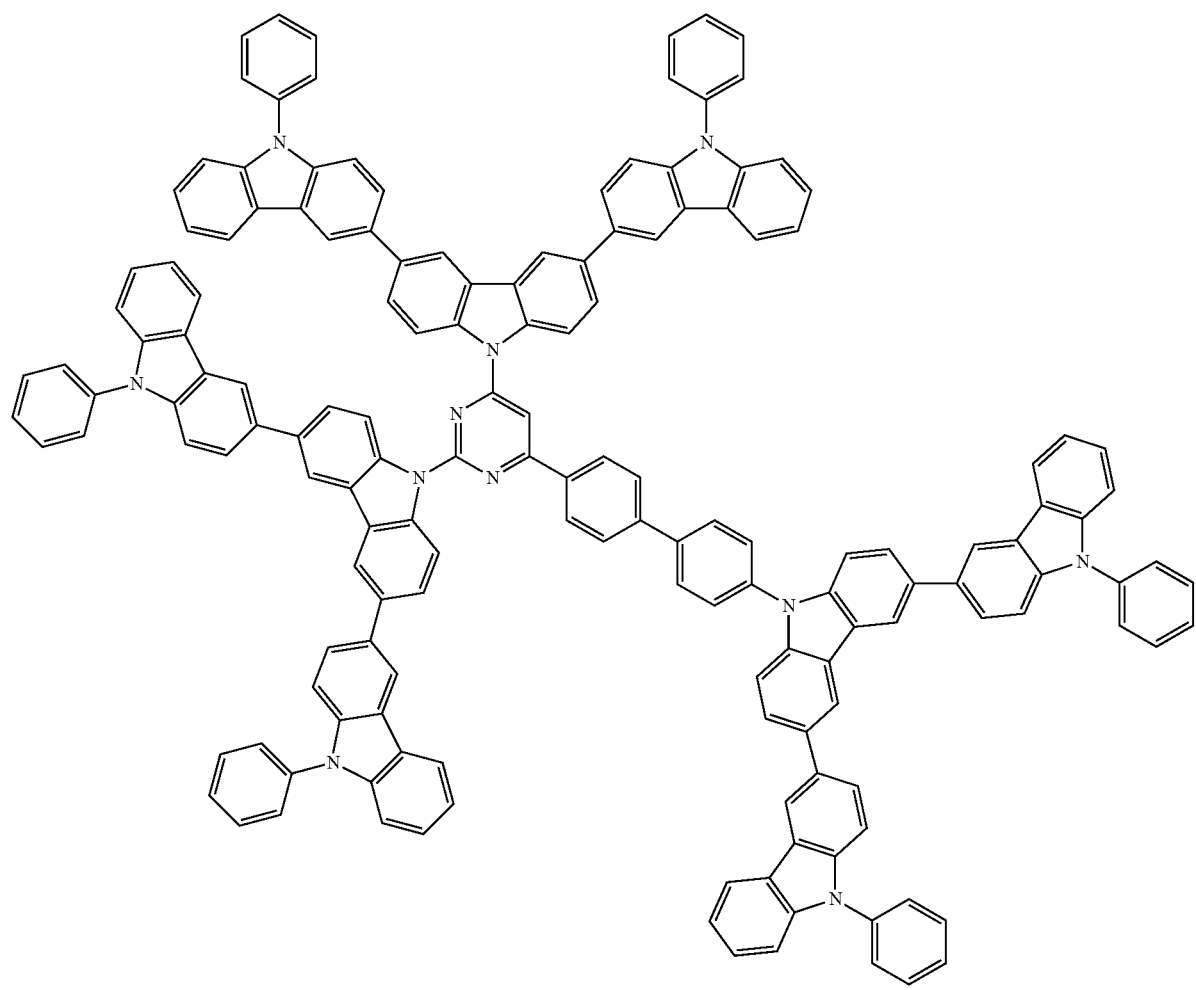

-continued
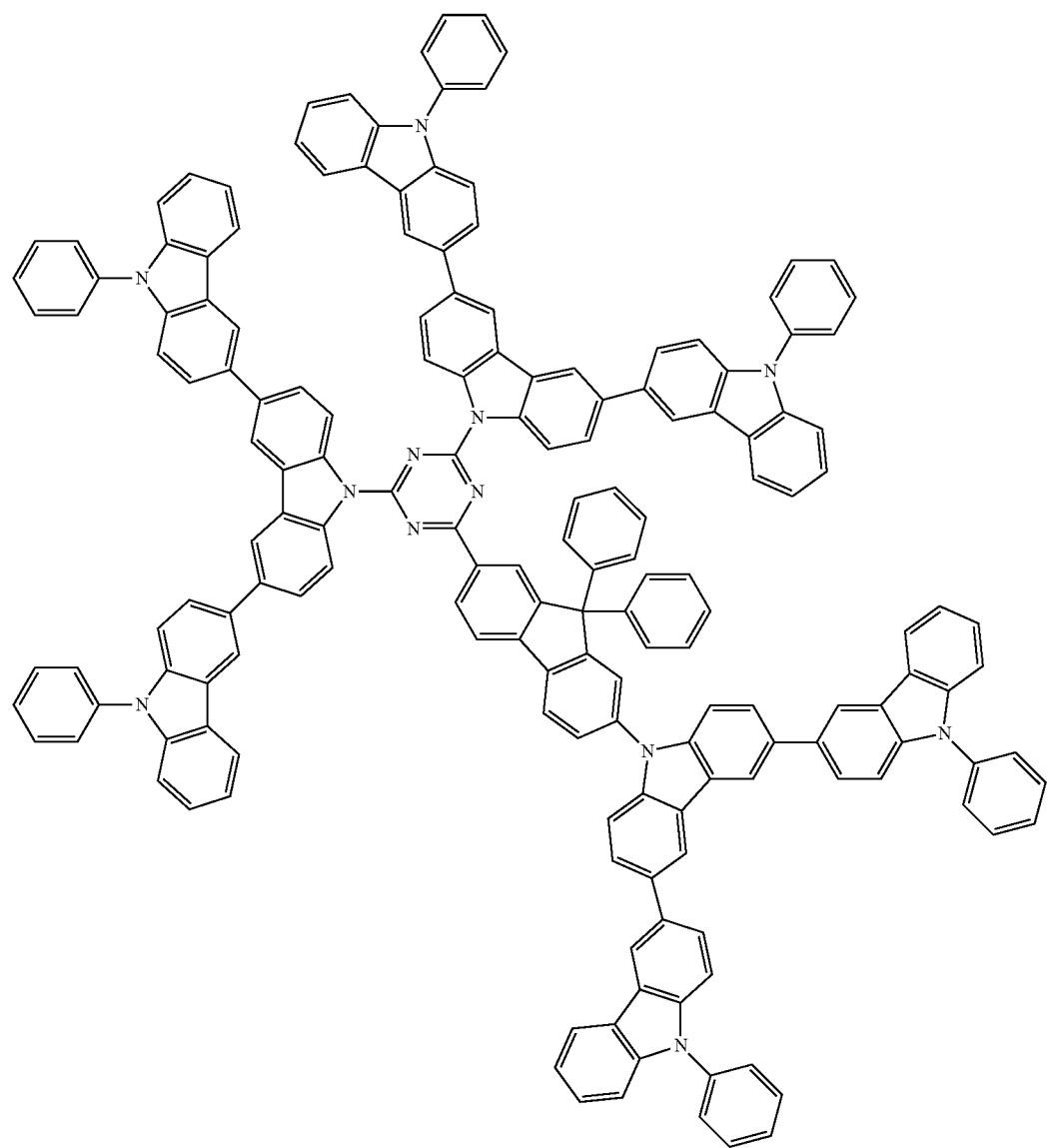 [SMILES: c1ccc(-n2c3ccccc3c3cc(-c4ccc5c(c4)c4cc(-c6ccc7c(c6)c6ccccc6n7-c6ccccc6)ccc4n5-c4ccc5c(c4)C(c4ccccc4)(c4ccccc4)c4cc(-c6nc(-n7c8ccc(-c9ccc%10c(c9)c9ccccc9n%10-c9ccccc9)cc8c8cc(-c9ccc%10c(c9)c9ccccc9n%10-c9ccccc9)ccc87)nc(-n7c8ccc(-c9ccc%10c(c9)c9ccccc9n%10-c9ccccc9)cc8c8cc(-c9ccc%10c(c9)c9ccccc9n%10-c9ccccc9)ccc87)n6)ccc4-5)ccc32)cc1]

-continued
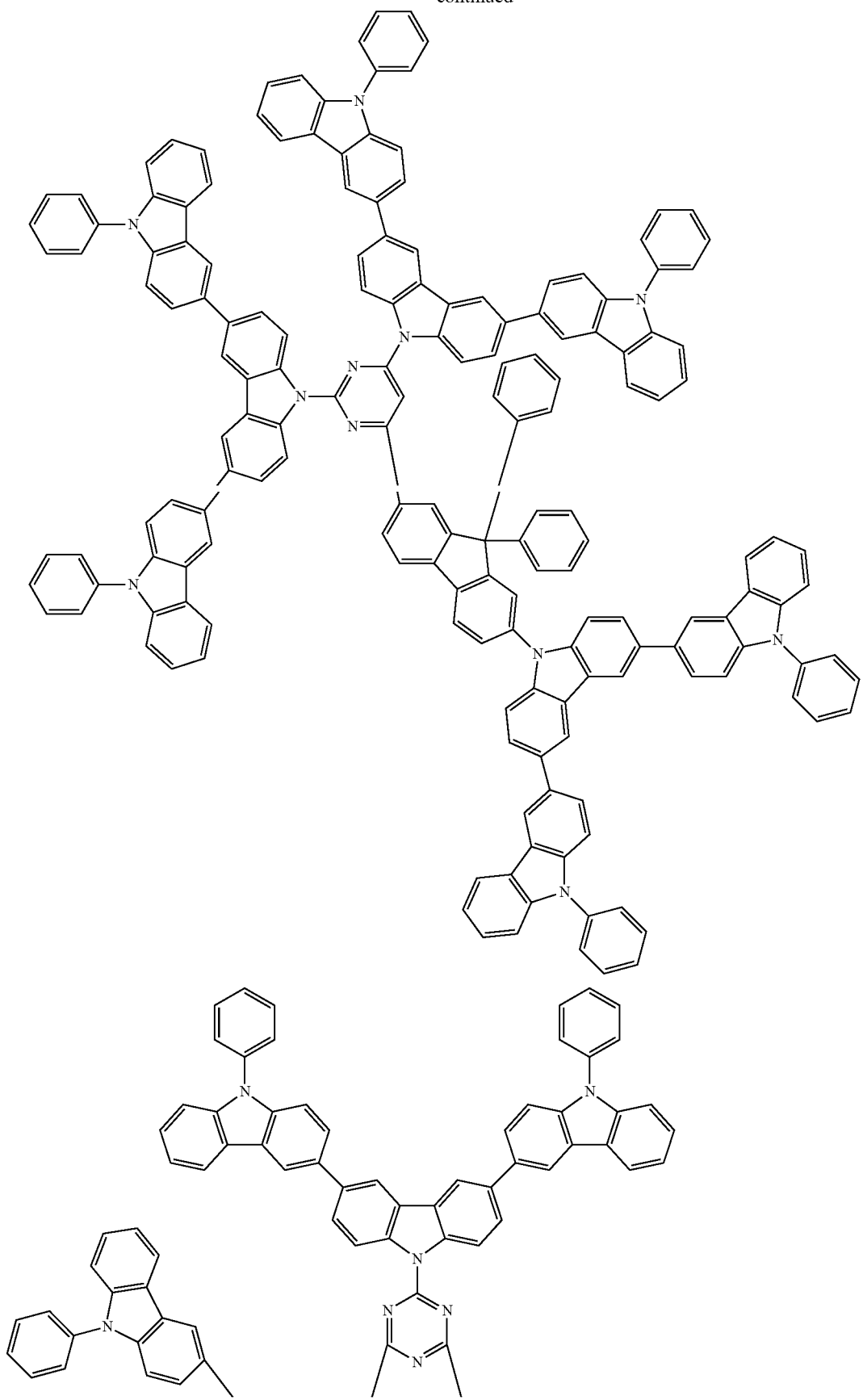

465 466
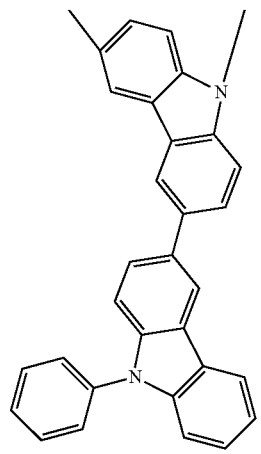
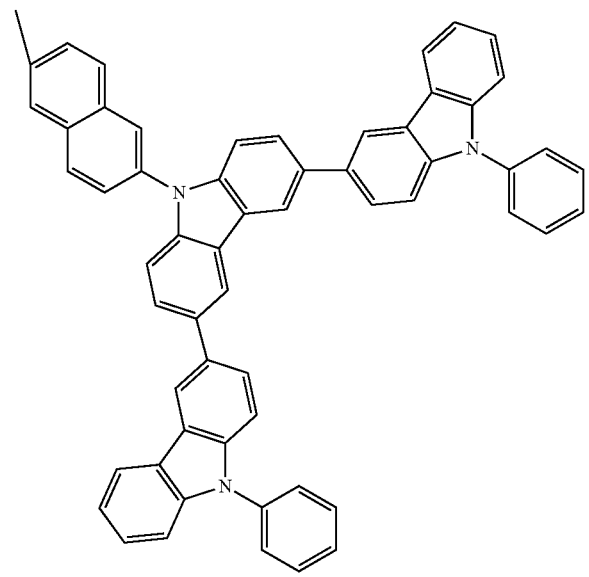
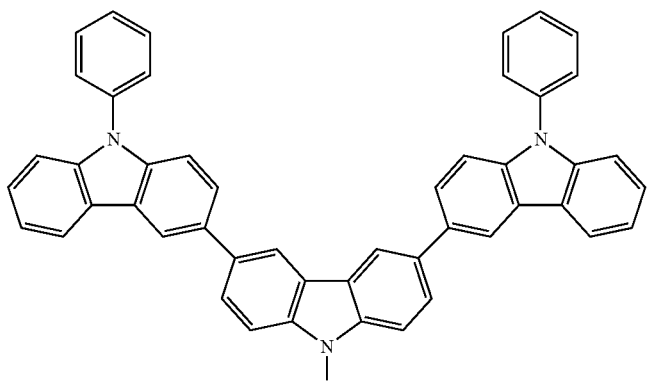
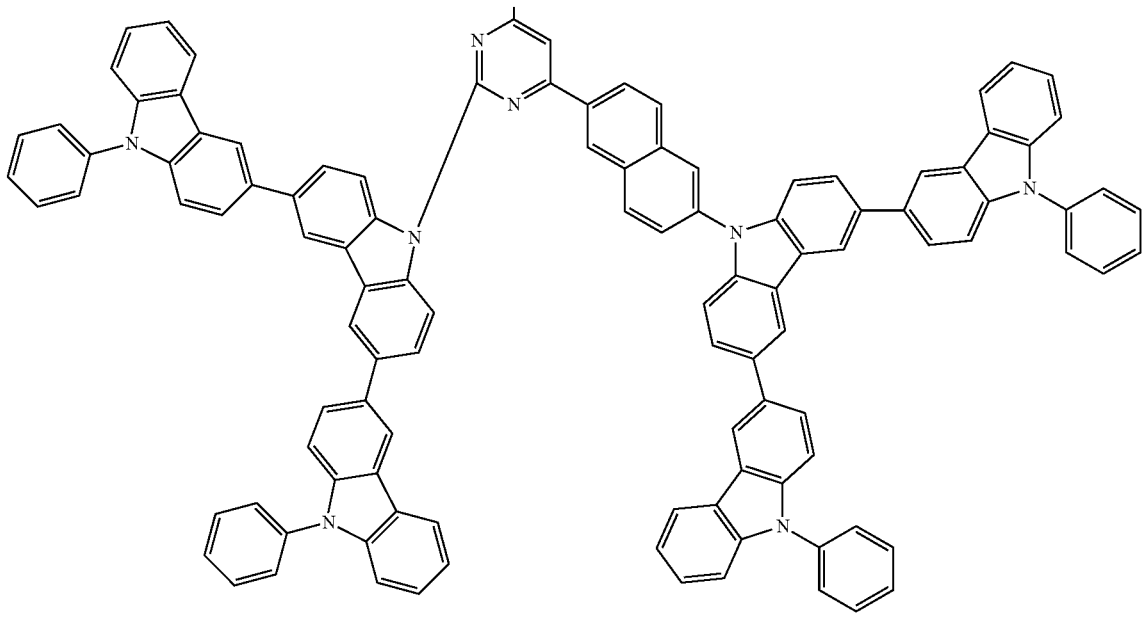

Compound represented by formula 1[II]

In an aspect, the invention provides a compound represented by formula 1[II] (also referred to as "compound 1[II]"). The compound 1[II] is suitable for use in forming the layer of organic EL device by a coating method and is useful as a material for organic electroluminescence devices.

Description of Each Group in Formula 1[II]

The nitrogen-containing heteroaromatic hydrocarbon group for A of formula 1[II] has 5 to 30, preferably 6 and 20, and more preferably 6 to 14 ring carbon atoms.

The nitrogen-containing heteroaromatic hydrocarbon group is preferably a monocyclic group or a fused ring group comprising two or three fused rings.

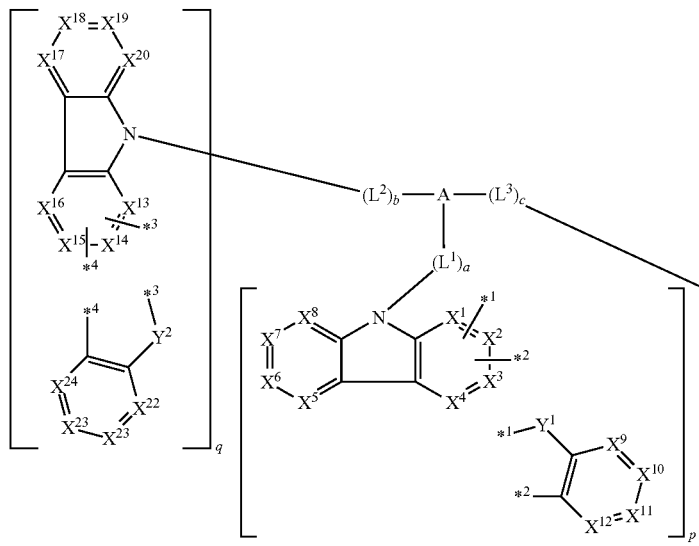

(1[II])

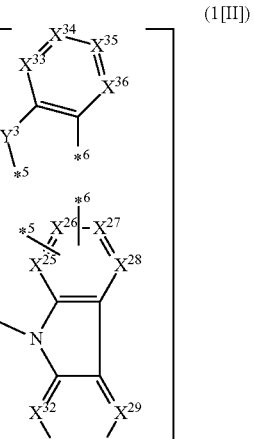

in formula 1[II],

A represents a substituted or unsubstituted nitrogen-containing heterocyclic group having 5 to 30 ring atoms;

$L^1$ to $L^3$ each independently represent a substituted or unsubstituted aromatic hydrocarbon group having 6 to 30 ring carbon atoms, a substituted or unsubstituted heterocyclic group having 5 to 30 ring atoms, or a group wherein 2 to 4 groups selected from the preceding groups are bonded to each other;

a to c each independently represent 0 or 1;

two of $X^1$ to $X^4$ represent carbon atoms which are respectively bonded to *1 and *2, and the other two independently represent C(R) or a nitrogen atom;

two of $X^{13}$ to $X^{16}$ represent carbon atoms which are respectively bonded to *3 and *4, and the other two independently represent C(R) or a nitrogen atom;

two of $X^{25}$ to $X^{28}$ represent carbon atoms which are respectively bonded to *5 and *6, and the other two independently represent C(R) or a nitrogen atom;

$X^5$ to $X^{12}$, $X^{17}$ to $X^{24}$, and $X^{29}$ to $X^{36}$ each independently represent C(R) or a nitrogen atom;

R represents a hydrogen atom or a substituent, two or more groups R may be the same or different, and two selected from groups R may be bonded to each other to form a ring;

$Y^1$ to $Y^3$ each independently represent an oxygen atom, a sulfur atom, —C($R^A$)($R^B$)—, —Si($R^C$)($R^D$)—, —P($R^E$)—, —P(O)($R^F$)—, —S(=O)$_2$—, or —P(=S)($R^G$)—;

$R^A$ to $R^G$ each independently represent a hydrogen atom or a substituent and two selected from $R^A$ to $R^G$ may be bonded to each other to form a ring; and p to r each independently represent an integer of 0 to 3, p+q+r=3, and when p, q or r is 2 or 3, 2 or 3 groups in each [ ] may be the same or different, respectively.

The nitrogen-containing heteroaromatic hydrocarbon group contains preferably 1 to 3 and more preferably 2 or 3 nitrogen atoms. Particularly, the nitrogen-containing heteroaromatic hydrocarbon group contains preferably 2 or 3 and more preferably 3 nitrogen atoms when it is a monocyclic group, and preferably 2 nitrogen atoms when it is a fused ring group having two or three fused rings.

The nitrogen-containing heteroaromatic hydrocarbon group may contain a hetero atom other than a nitrogen atom, such as an oxygen atom, a sulfur atom, a silicon atom, and selenium atom, but preferably contains only a nitrogen atom as the heteroatom.

Examples of the nitrogen-containing heteroaromatic hydrocarbon group for A in formula 1[II] include residues of compounds selected from pyrrole, pyridine, pyridazine, pyrimidine, pyrazine, triazine, imidazole, pyrazole, oxadiazole, thiadiazole, triazole, tetrazole, indole, isoindole, indolizine, quinolizine, quinoline, isoquinoline, naphthyridine, cinnoline, phthalazine, quinazoline, benzo[f]quinazoline, benzo[h]quinazoline, quinoxaline, benzimidazole, indazole, carbazole, biscarbazole, phenanthridine, acridine, phenanthroline, phenazine, azatriphenylene, diazatriphenylene, hexaazatriphenylene, azacarbazole, azadibenzofuran, azadibenzothiophene, and dinaphtho[2',3': 2,3:2',3': 6,7]carbazole.

The residue is a mono valent or more valent group obtained by removing one or more hydrogen atoms from the above compound. The valency of the nitrogen-containing heteroaromatic hydrocarbon group, i.e., the valency of "A" corresponds to the value of "a+b+c" in formula 1[II].

The nitrogen-containing heteroaromatic hydrocarbon group mentioned above is preferably a residue of the following compounds:

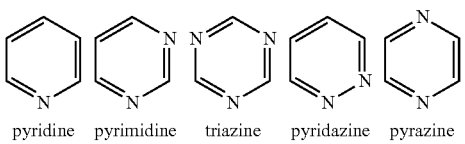

pyridine  pyrimidine  triazine  pyridazine  pyrazine

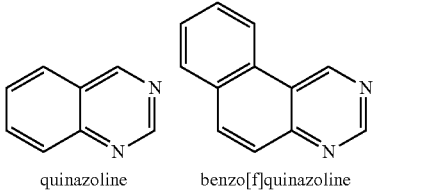

quinazoline     benzo[f]quinazoline

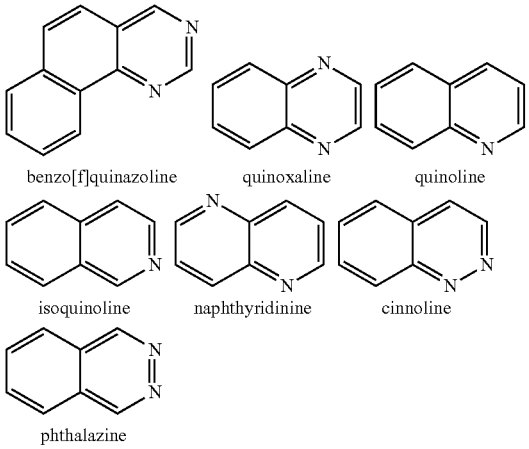

benzo[f]quinazoline   quinoxaline   quinoline isoquinoline   naphthyridinine   cinnoline

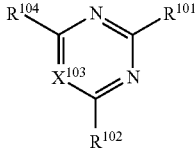

phthalazine

In an aspect of the invention, the nitrogen-containing heteroaromatic hydrocarbon group for A is preferably a residue of the nitrogen-containing heterocyclic ring represented by formula (A1):

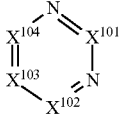

(A1)

in formula (A1), $X^{101}$ to $X^{104}$ each represent $C(R^{101})$ to $C(R^{104})$, respectively, or a nitrogen atom; $R^{101}$ to $R^{104}$ each independently represent a hydrogen atom or a substituent; and two selected from $R^{102}$ to $R^{104}$ may be bonded to each other to form a ring.

In an aspect of the invention, the nitrogen-containing heteroaromatic hydrocarbon group for A is more preferably a residue of the nitrogen-containing heterocyclic ring represented by any of formulae (A2) to (A4):

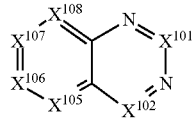

(A2)

in formula (A2), $X^{103}$ represents $C(R^{103})$ or a nitrogen atom; $R^{101}$ to $R^{104}$ each independently represent a hydrogen atom or a substituent; and two selected from $R^{102}$ to $R^{104}$ may be bonded to each other to form a ring;

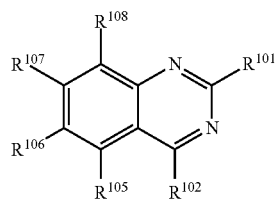

(A3)

in formula (A3), $X^{101}$, $X^{102}$, and $X^{105}$ to $X^{108}$ each represent $C(R^{101})$, $C(R^{102})$, or $C(R^{105})$ to $C(R^{108})$, respectively, or a nitrogen atom; $R^{101}$, $R^{102}$, and $R^{105}$ to $R^{108}$ each independently represent a hydrogen atom or a substituent; and two selected from $R^{102}$ and $R^{105}$ to $R^{108}$ may be bonded to each other to form a ring; and (A4)

in formula (A4), $R^{101}$, $R^{102}$, and $R^{105}$ to $R^{108}$ each independently represent a hydrogen atom or a substituent; and two selected from $R^{102}$ and $R^{105}$ to $R^{108}$ may be bonded to each other to form a ring.

The nitrogen-containing heteroaromatic hydrocarbon group for A in formula 1[II] may have a substituent.

Examples of the substituent of the nitrogen-containing heteroaromatic hydrocarbon group include the substituents mentioned above and also include, for example, an (aza) carbazolyl group wherein two substituents are bonded to each other to form a ring, and an aryl group or a heteroaryl group each having an (aza) carbazolyl substituent wherein two substituents are bonded to each other to form a ring.

In formula 1[II], the aromatic hydrocarbon group for $L^1$ to $L^3$ has 6 to 30, preferably 6 to 18, more preferably 6 to 13, still more preferably 6 to 12, and particularly preferably 6 to 10 ring carbon atoms.

In an aspect of the invention, at least one of the aromatic hydrocarbon groups for $L^1$ to $L^3$ is preferably a di- to tetravalent residue of any of the following compounds, and more preferably $L^1$ to $L^3$ are all di- to tetravalent residues of any of the following compounds:

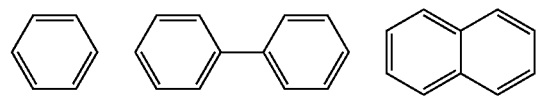

wherein each carbon atom in the compound may have a substituent.

In an aspect of the invention, at least one of the aromatic hydrocarbon groups for $L^1$ to $L^3$ is preferably a group represented by any of the following formulae, and more preferably $L^1$ to $L^3$ are all groups represented by any of the following formulae:

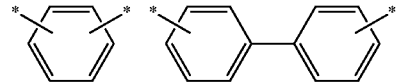

-continued

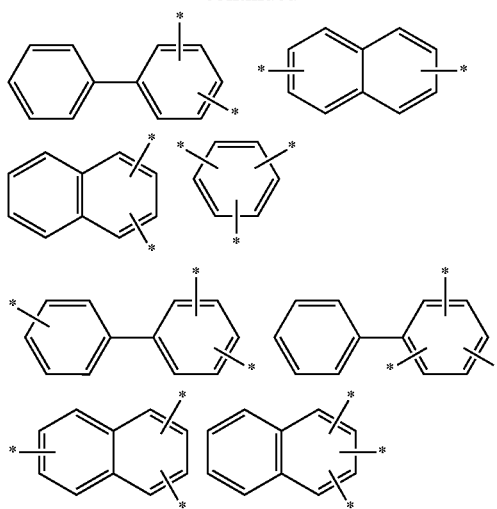

wherein * indicates a bonding site and each carbon atom other than that at the bonding site may have a substituent.

More preferably, at least one of the aromatic hydrocarbon groups for $L^1$ to $L^3$ is a group represented by any of the following formulae, and still more preferably $L^1$ to $L^3$ are all groups represented by any of the following formulae:

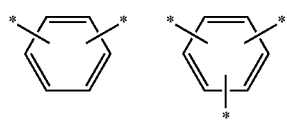

wherein * indicates a bonding site and each carbon atom other than that at the bonding site may have a substituent.

More preferably, at least one of the aromatic hydrocarbon groups for $L^1$ to $L^3$ is a group represented by any of the following formulae, and still more preferably $L^1$ to $L^3$ are all groups represented by any of the following formulae:

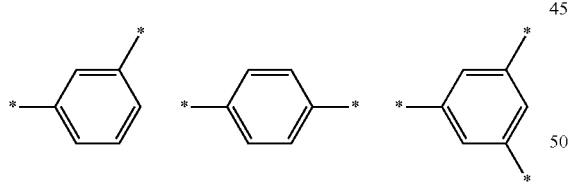

wherein * indicates a bonding site and each carbon atom other than that at the bonding site may have a substituent.

In addition to the above groups, the aromatic hydrocarbon group for $L^1$ to $L^3$ may include the groups represented by the following formulae:

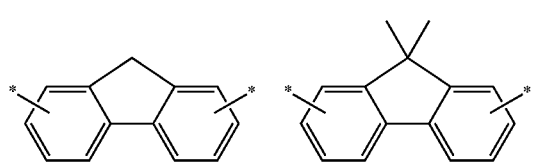

-continued

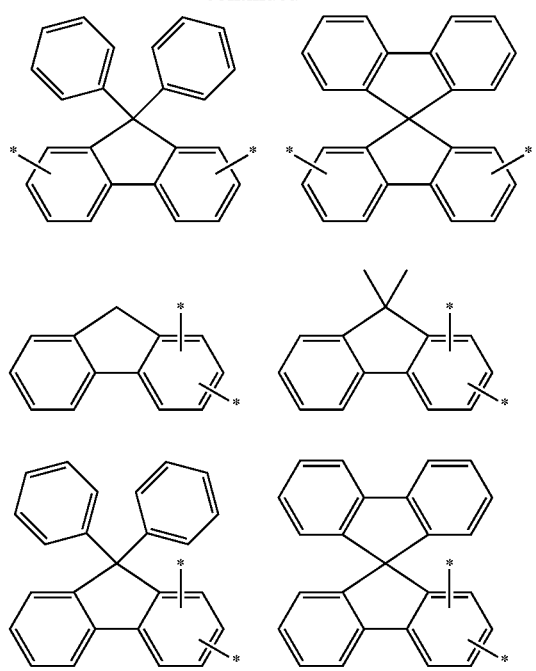

wherein * indicates a bonding site and each carbon atom other than that at the bonding site may have a substituent.

Examples of the divalent aromatic hydrocarbon group for $L^1$ to $L^3$ include the following groups:

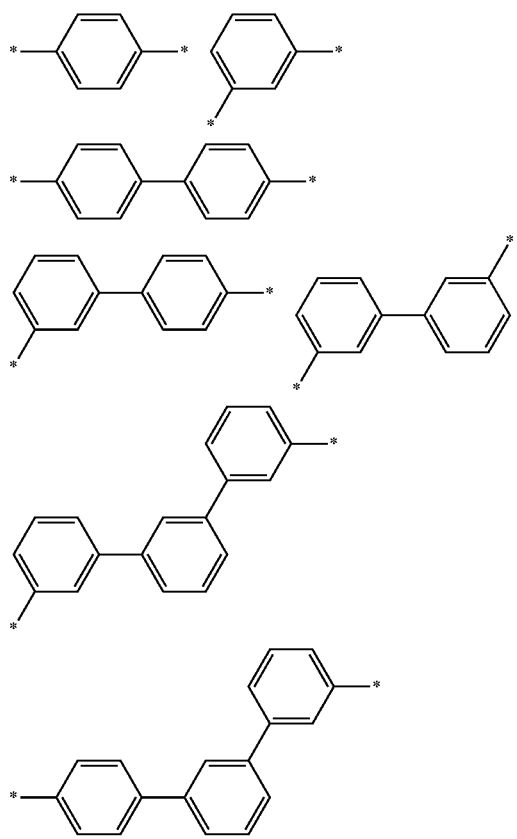

-continued

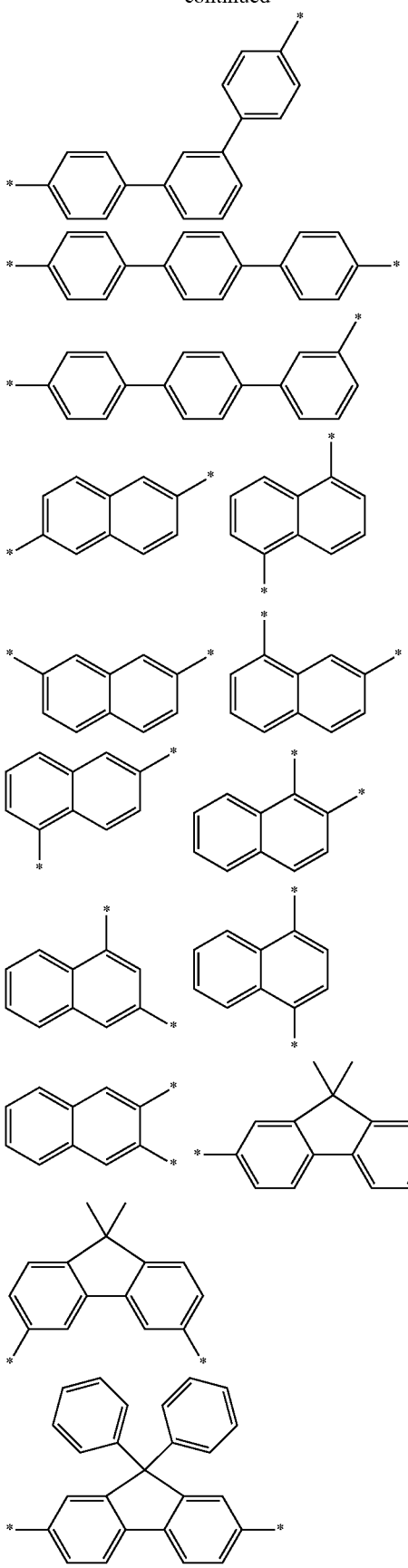

-continued wherein * indicates a bonding site and each carbon atom other than that at the bonding site may have a substituent.

In formula 1[I], the heterocyclic group for $L^1$ to $L^3$ has 5 to 30, preferably 5 to 18, more preferably 5 to 13, particularly preferably 5 to 10 ring atoms.

Examples of the heterocyclic group include a residue of a nitrogen-containing heterocyclic compound, such as pyrrole, pyridine, imidazopyridine, pyrazole, triazole, tetrazole, indole, isoindole, and carbazole; a residue of an oxygen-containing heterocyclic compound, such as furan, benzofuran, isobenzofuran, dibenzofuran, oxazole, oxadiazole, benzoxazole, benzonaphthofuran, and dinaphthofuran; and a residue of a sulfur-containing heterocyclic compound, such as thiophene, benzothiophene, dibenzothiophene, thiazole, thiadiazole, benzothiazole, benzonaphthothiophene, and dinaphthothiophene.

The "group wherein 2 to 4 groups selected from the preceding groups are bonded to each other" for $L^1$ to $L^3$ is a group wherein 2 to 4 groups selected from a substituted or unsubstituted aromatic hydrocarbon group having 6 to 30 ring carbon atoms and a substituted or unsubstituted heterocyclic group having 5 to 30 ring atoms are bonded to each other. The 2 to 4 groups to be selected may be bonded to each other to form a ring structure. The order of bonding the groups selected from the aromatic hydrocarbon group and heterocyclic group is not particularly limited.

In particular, each of $L^1$ to $L^3$ is preferably a substituted or unsubstituted aromatic hydrocarbon group having 6 to 30 ring carbon atoms. The aromatic hydrocarbon group more preferred is as described above.

In formula 1[I], a to c each independently represent 0 or 1.

When a is zero, $L^1$ is not present, i.e., A is directly bonded to the group in [ ]. When a is 1, A is bonded to the group in [ ] via $L^1$. The same applies to b and c.

In formula 1[II],
two of $X^1$ to $X^4$ are carbon atoms which are respectively bonded to *1 and *2, and the other two independently represent C(R) or a nitrogen atom;
two of $X^{13}$ to $X^{16}$ are carbon atoms which are respectively bonded to *3 and *4, and the other two independently represent C(R) or a nitrogen atom; and
two of $X^{25}$ to $X^{28}$ are carbon atoms which are respectively bonded to *5 and *6, and the other two independently represent C(R) or a nitrogen atom In an aspect of the invention, a pair of $X^1$ and $X^2$, $X^2$ and $X^3$, or $X^3$ and $X^4$ selected from $X^1$ to $X^4$ are preferably carbon atoms which are respectively bonded to *1 and *2.

Similarly, a pair of $X^{13}$ and $X^{14}$, $X^{14}$ and $X^{15}$, or $X^{15}$ and $X^{16}$ selected from $X^{13}$ to $X^{16}$ are preferably carbon atoms which are respectively bonded to *3 and *4.

In addition, a pair of $X^{25}$ and $X^{26}$, $X^{26}$ and $X^{27}$, or $X^{27}$ and $X^{28}$ are preferably carbon atoms which are respectively bonded to *5 and *6.

$X^5$ to $X^{12}$, $X^{17}$ to $X^{24}$, and $X^{29}$ to $X^{36}$ each independently represent C(R) or a nitrogen atom.

Namely, $X^1$ to $X^{36}$ not involved in forming the ring structure shown in formula 1[II] each independently represent C(R) or a nitrogen atom and preferably all represent C(R) in an aspect of the invention.

R represents a hydrogen atom or a substituent, two or more groups R may be the same or different, and two selected from groups R may be bonded to each other to form a ring.

In an aspect of the invention, a compound wherein two selected from groups R are not bonded to each other, thereby failing to form a ring is preferred.

$Y^1$ to $Y^3$ in formula 1[II] each independently represent an oxygen atom, a sulfur atom, —C($R^A$)($R^B$)—, —Si($R^C$)($R^D$)—, —P($R^E$)—, —P(=O)($R^F$)—, —S(=O)$_2$—, or —P(=S)($R^G$)—.

$R^A$ to $R^G$ each independently represent a hydrogen atom or a substituent and two selected from $R^A$ to $R^G$ may be bonded to each other to form a ring.

The substituent for $R^A$ to $R^G$ is selected from those mentioned above, preferably a substituted or unsubstituted aryl group having 6 to 30 ring carbon atoms or a substituted or unsubstituted heteroaryl group having 5 to 30 ring atoms, and more preferably a substituted or unsubstituted aryl group having 6 to 30 ring carbon atoms.

The aryl group for $R^A$ to $R^G$ has 6 to 30, preferably 6 to 18, more preferably 6 to 13, still more preferably 6 to 12, and particularly preferably 6 to 10 ring carbon atoms. The aryl group may be any of a non-fused aryl group, a fused aryl group, and a combination thereof.

Examples of the aryl group include a phenyl group, a biphenylyl group, a terphenylyl group, a quaterphenylyl group, a quinquephenylyl group, a naphthyl group (a 1-naphthyl group, a 2-naphthyl group), an acenaphthylenyl group, an anthryl group, a benzanthryl group, an aceanthryl group, a phenanthryl group, a benzophenanthryl group, a phenalenyl group, a fluorenyl group (inclusive of a 9,9-dimethylfluorenyl group, a 9,9-diphenylfluorenyl group, and a 9,9'-spirobifluorenyl group), a benzofluorenyl group, a dibenzofluorenyl group, a picenyl group, a pentaphenyl group, a pentacenyl group, a pyrenyl group, a chrysenyl group, a benzochrysenyl group, a fluoranthenyl group, a benzofluoranthenyl group, a tetracenyl group, a perylenyl group, a coronyl group, a dibenzanthryl group, a naphthylphenyl group, a s-indanyl group, an as-indanyl group, a triphenylenyl group, and a benzotriphenylenyl group. The above groups include isomeric groups, if any.

The aryl group for $R^A$ to $R^G$ is preferably selected from the following groups:

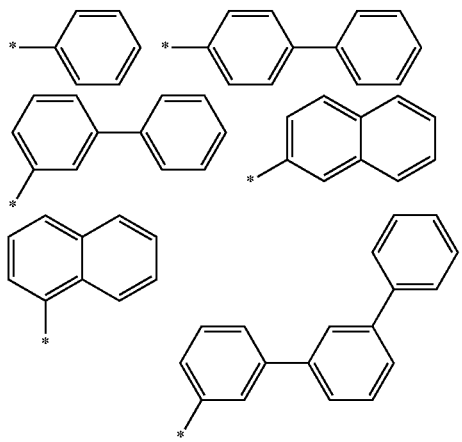

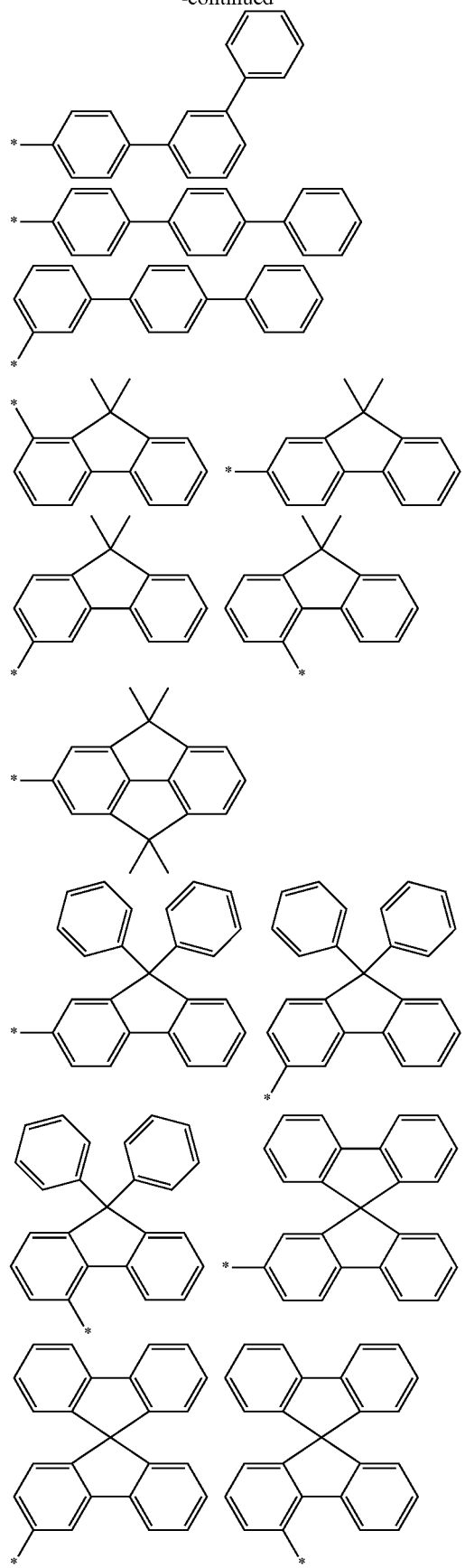

-continued

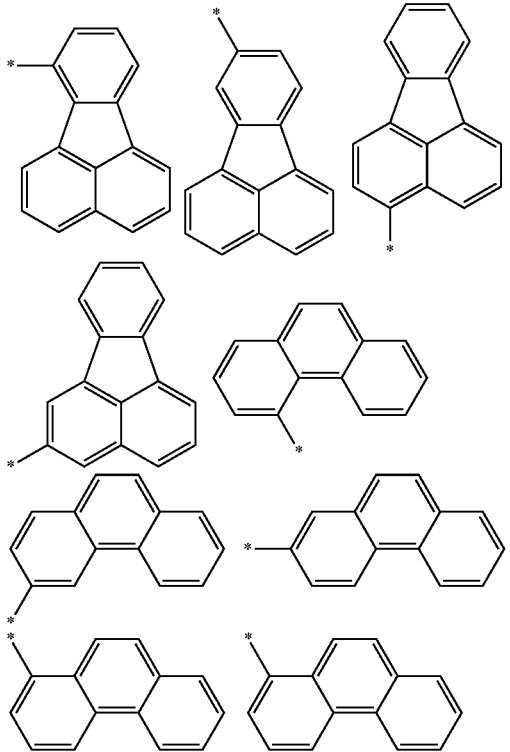

wherein * indicates a bonding site and each carbon atom other than that at the bonding site may have a substituent.

The heteroaryl group for $R^A$ to $R^G$ has 5 to 30, preferably 5 to 20, more preferably 5 to 14, and still more preferably 5 to 10 ring atoms.

The heteroaryl group contains at least one, preferably 1 to 5, more preferably 1 to 3, and still more preferably 1 to 2 hetero atoms which may be the same or different.

Examples of the heteroaryl group include a pyrrolyl group, a furyl group, a thienyl group, a pyridyl group, a pyridazinyl group, a pyrimidinyl group, a pyrazinyl group, a triazinyl group, an imidazolyl group, an oxazolyl group, a thiazolyl group, a pyrazolyl group, an isoxazolyl group, an isothiazolyl group, an oxadiazolyl group, a thiadiazolyl group, a triazolyl group, a tetrazolyl group, an indolyl group, an isoindolyl group, a benzofuranyl group, an isobenzofuranyl group, a benzothiophenyl group, an isobenzothiophenyl group, an indolizinyl group, a quinolizinyl group, a quinolyl group, an isoquinolyl group, a cinnolyl group, a phthalazinyl group, a quinazolinyl group, a quinoxalinyl group, a benzimidazolyl group, a benzoxazolyl group, a benzothiazolyl group, an indazolyl group, a benzisoxazolyl group, a benzisothiazolyl group, a dibenzofuranyl group, a dibenzothiophenyl group, a carbazolyl group, a biscarbazolyl group, a phenanthridinyl group, an acridinyl group, a phenanthrolinyl group, a phenazinyl group, a phenothiazinyl group, a phenoxazinyl group, an azatriphenylenyl group, a diazatriphenylenyl group, a xanthenyl group, an azacarbazolyl group, an azadibenzofuranyl group, an azadibenzothiophenyl group, a benzofuranobenzothiophenyl group, a benzothienobenzothiophenyl group, a dibenzofuranonaphthyl group, a dibenzothienonaphthyl group, a dinaphthothienothiophenyl group, and a dinaphtho[2',3': 2,3:2',3': 6,7]carbazolyl group.

In the compound in an aspect of the invention, the group in [ ] of formula 1[II] is preferably a group represented by formula (D1):

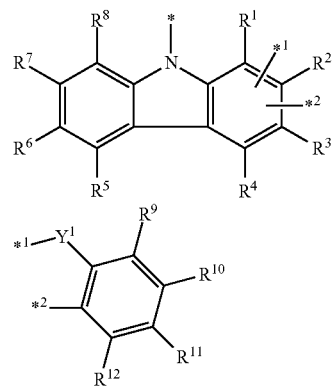

in formula (D1), $R^1$ to $R^{12}$ may be the same or different and each independently represent a hydrogen atom or a substituent;

two selected from $R^1$ to $R^{12}$ may be bonded to each other to form a ring;

two carbon atoms from which two selected from $R^1$ to $R^4$ are removed are bonded to *1 and *2, respectively;

$Y^1$ is as described above in formula 1[II]; and

* represents a bonding site to any of $L^1$ to $L^3$ and A in formula 1[II].

In an aspect of the invention, the group represented by formula (D1) is more preferably a compound represented by any of formulae (D1-i) to (D1-vi):

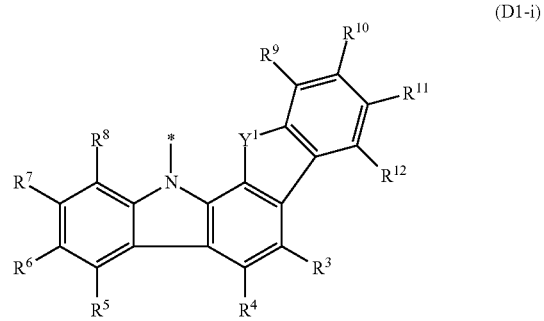

(D1-i)

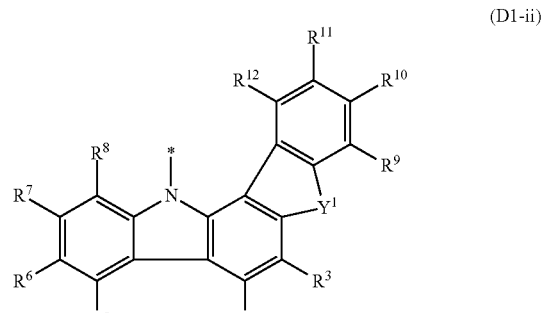

(D1-ii)

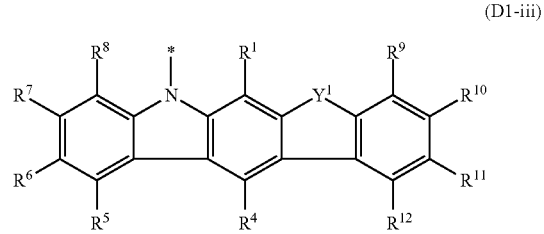

(D1-iii)

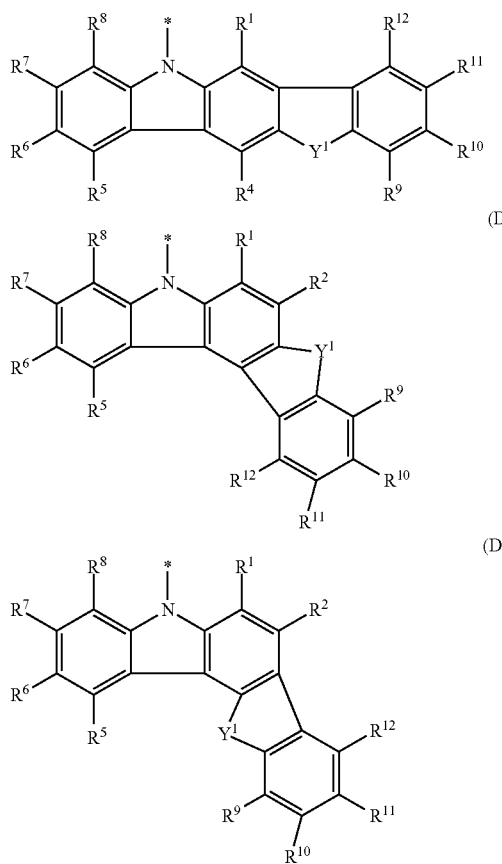

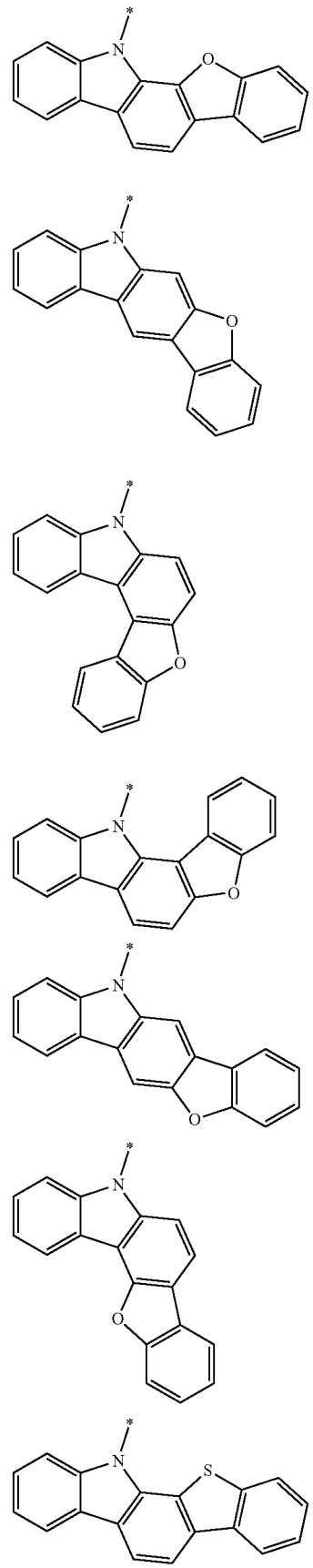

in formulae (D1-i) to (D1-vi), $R^1$ to $R^{12}$, $Y^1$, and * are as defined above in formula (D1).

When two selected from $R^1$ to $R^{24}$ in formula (D1) are bonded to each other to form a ring, one or more pairs selected from $R^5$ and $R^6$, $R^6$ and $R^7$, and $R^7$ and $R^8$ are preferably bonded to each other to form a ring.

In the compound in an aspect of the invention, two selected from $R^1$ to $R^{24}$ in formula (D1) are preferably not bonded to each other, thereby failing to form a ring, and the group in [ ] of formula 1[II] is preferably represented by formula (D2):

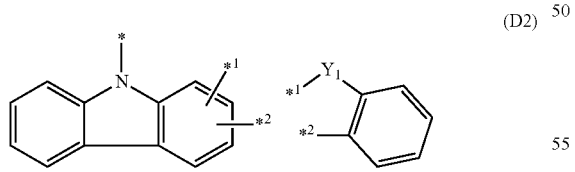

in formula (D2), two of the carbon atoms at 1-position, 2-position, 3-position and 4-position of the carbazolyl group from which hydrogen atoms are removed are bonded to *1 and *2, respectively, and $Y^1$ and * are as defined above in formula (D1).

The group in [ ] of formula 1[II] is preferably selected from the following groups, wherein * represents a bonding site to any of $L^1$ to $L^3$ and A in formula 1[II]. In the following groups, a hydrogen atom bonded to a carbon atom may be substituted with the substituent mentioned above.

481
-continued
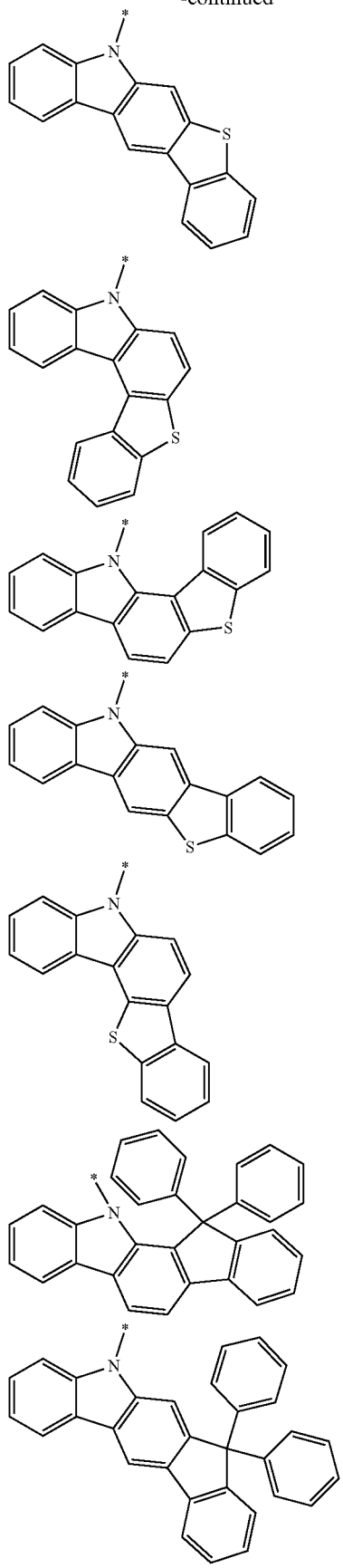
482
-continued
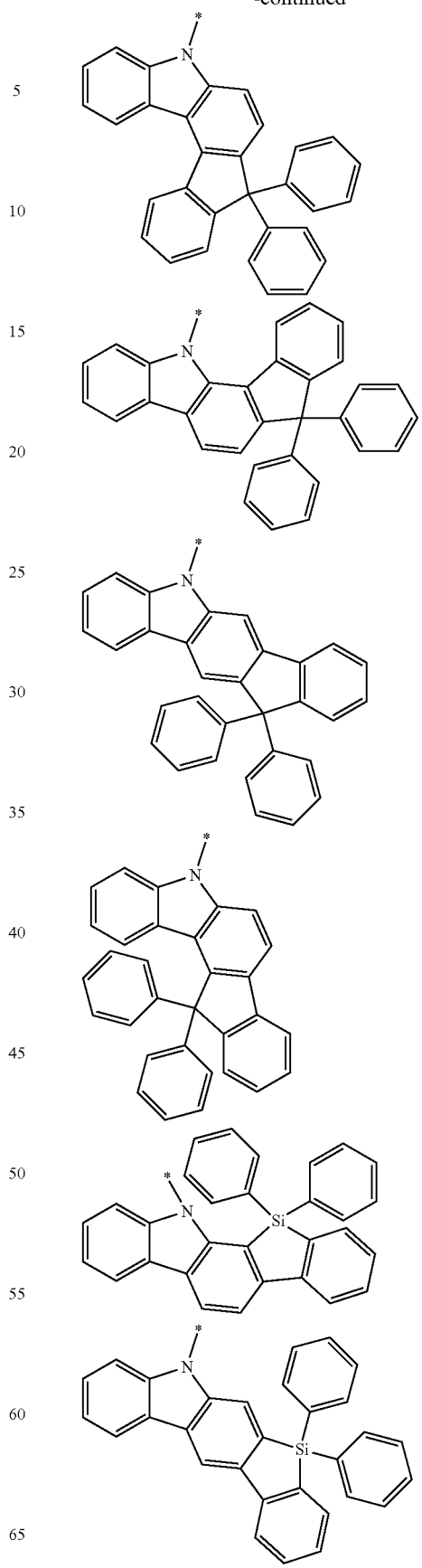

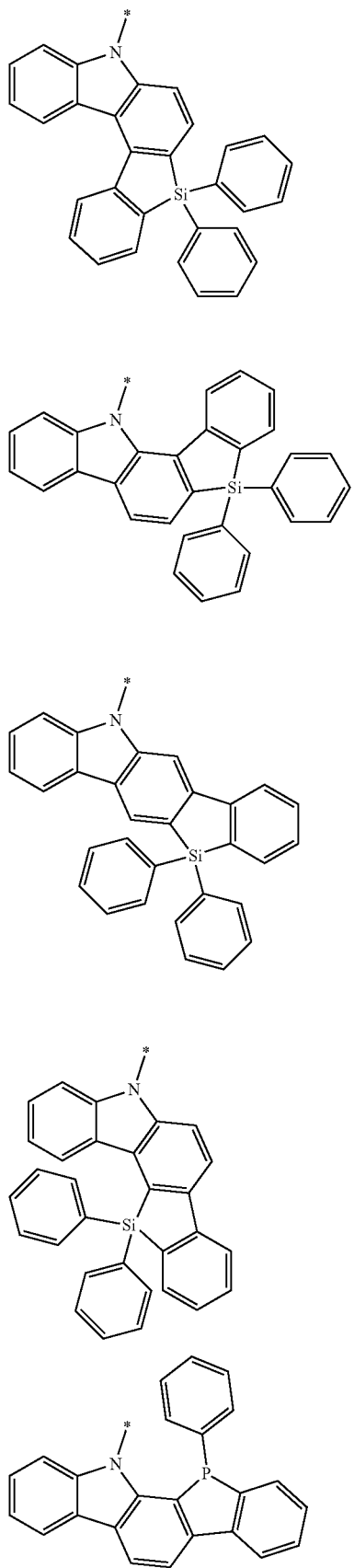
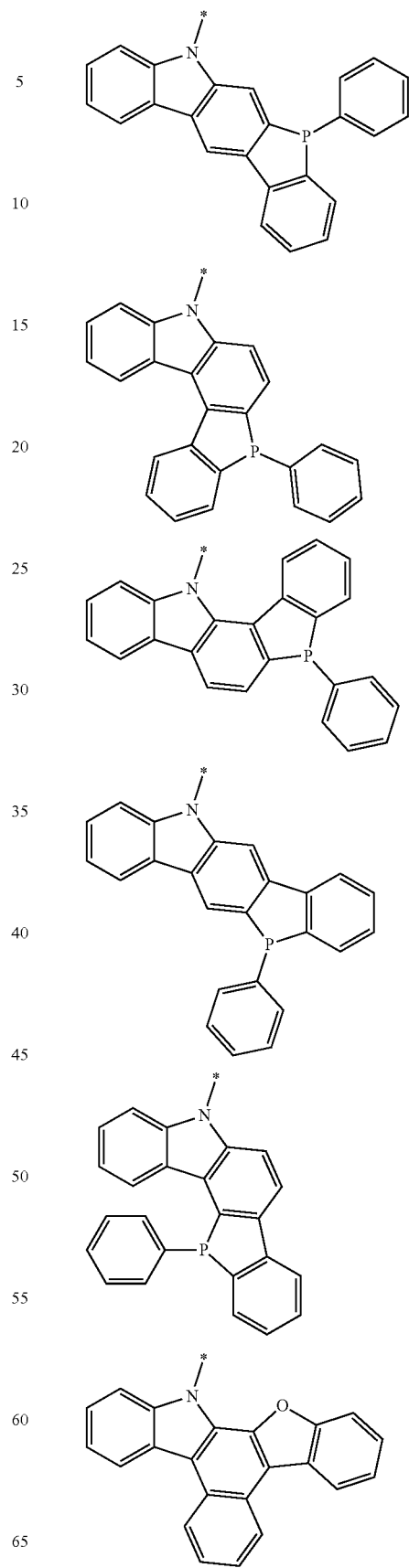

485
-continued
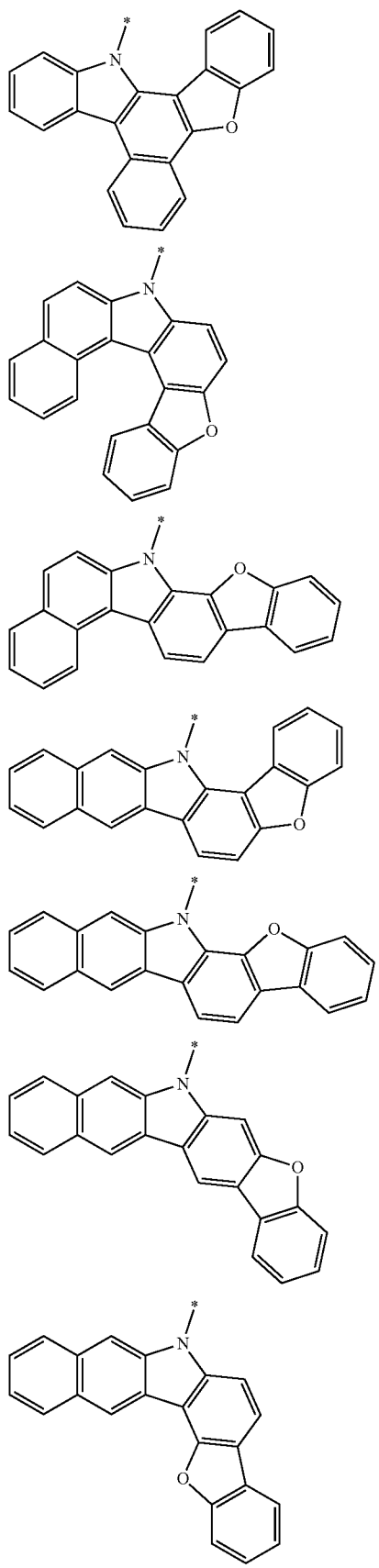
486
-continued
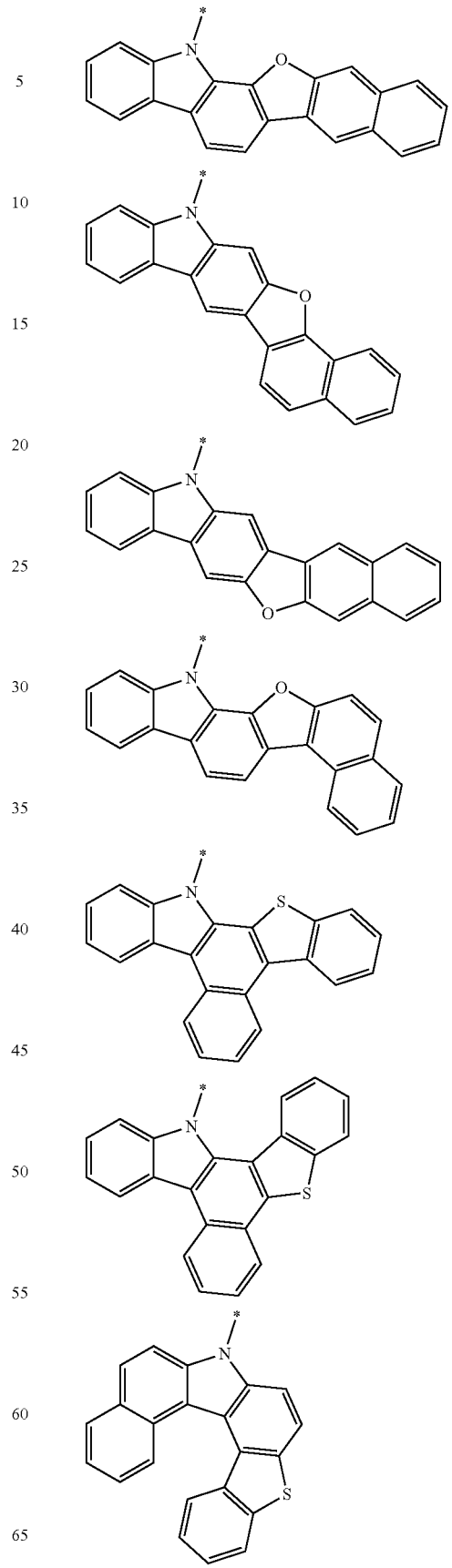

487
-continued
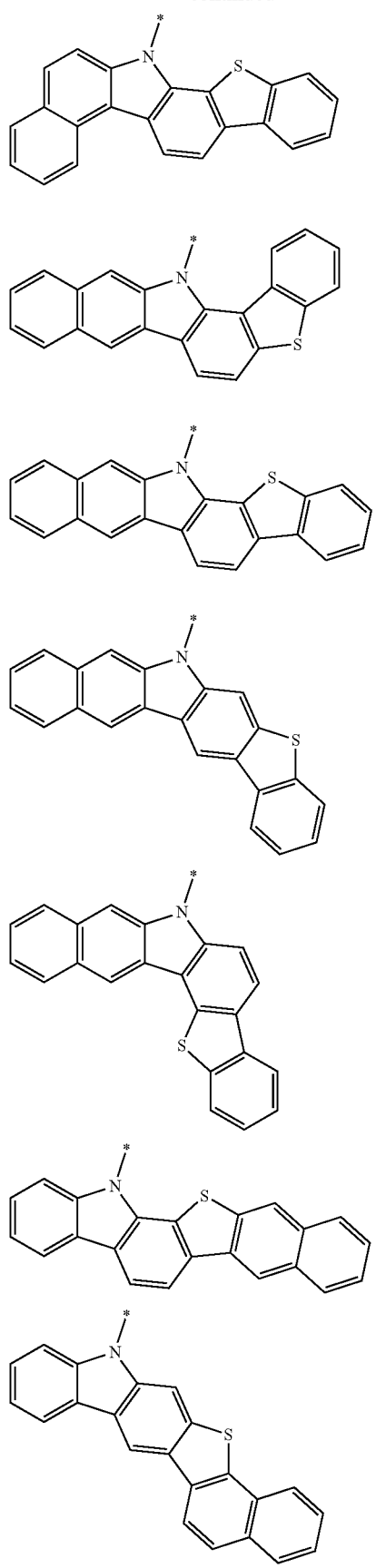
488
-continued
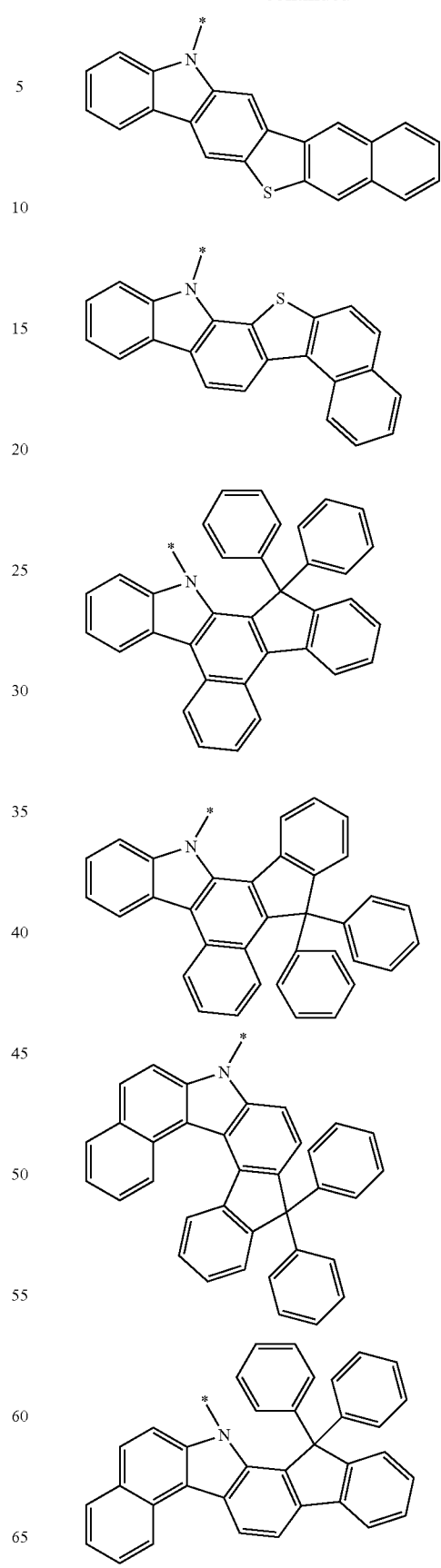

489
-continued
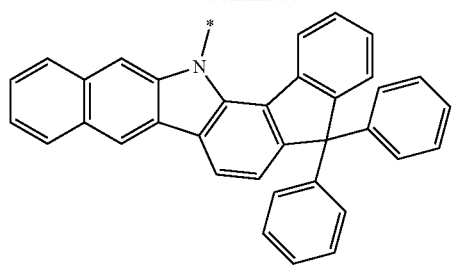
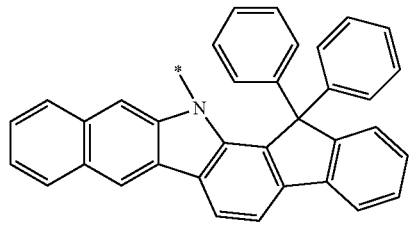
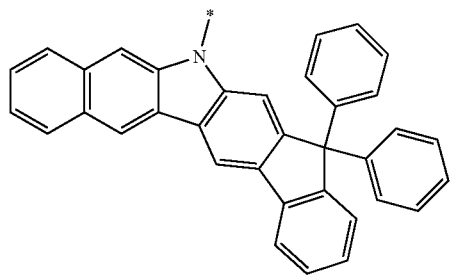
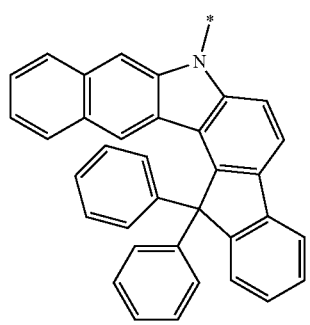
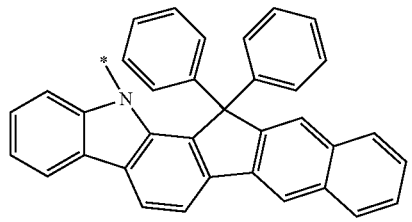
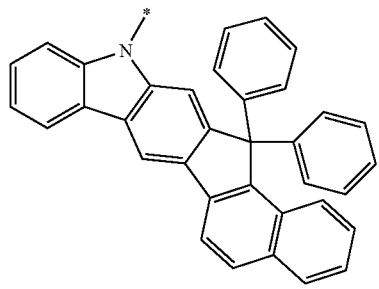
490
-continued
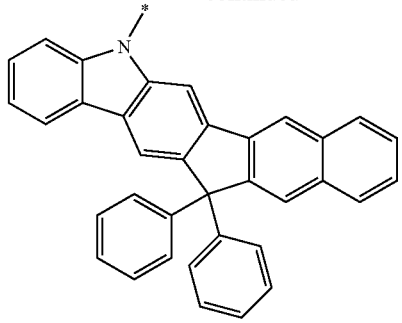
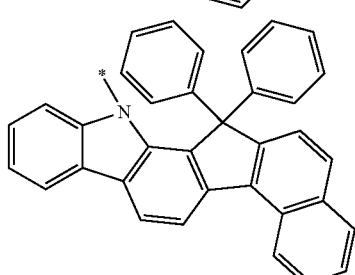
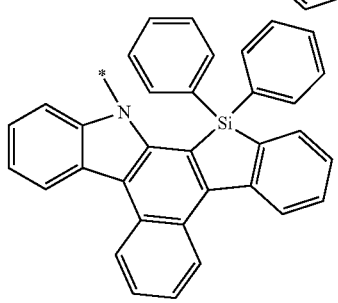
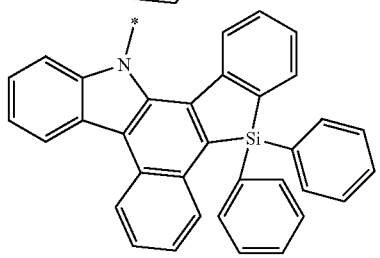
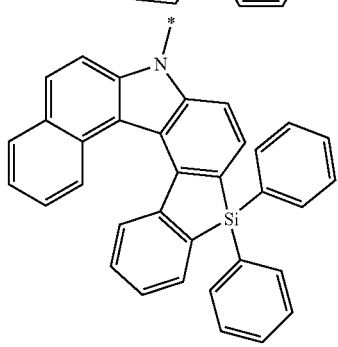
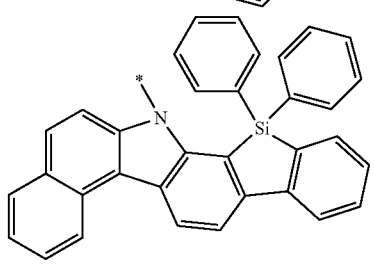

US 10,290,815 B2
491
-continued
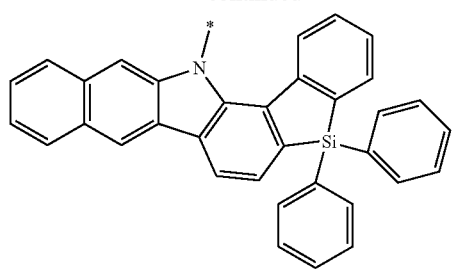
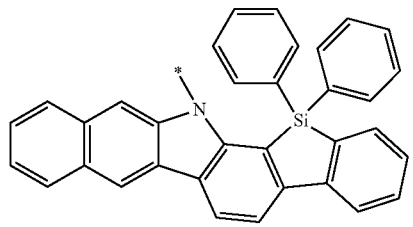
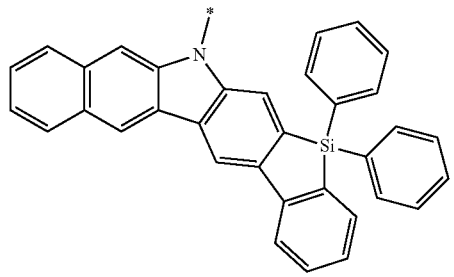
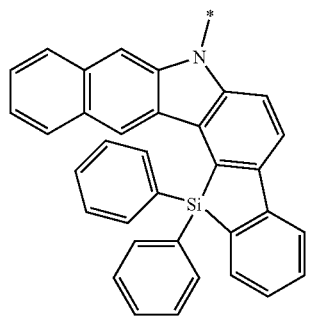
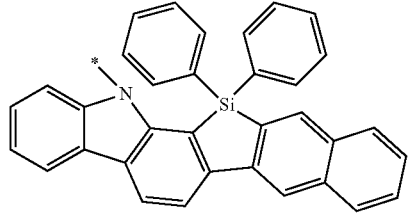
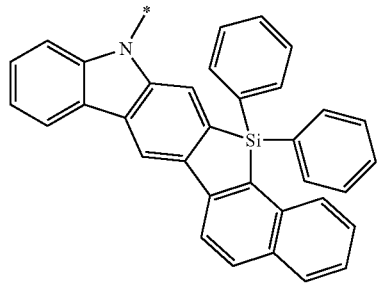
492
-continued
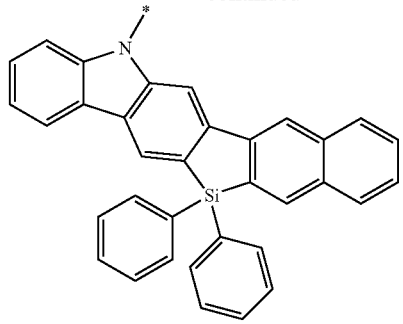
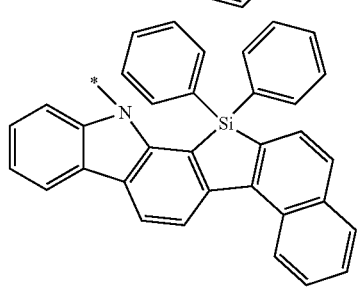
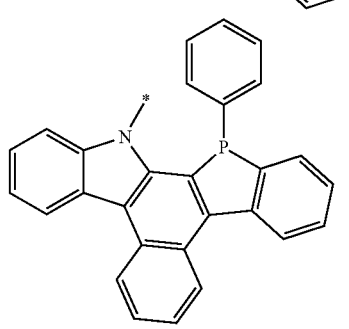
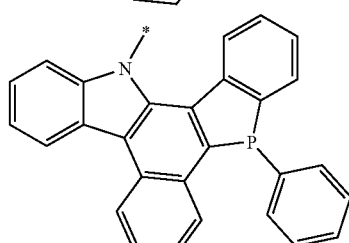
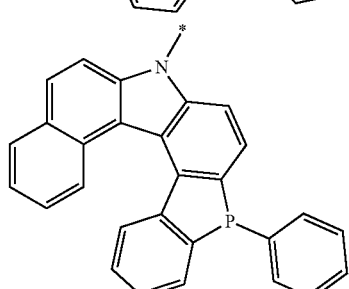
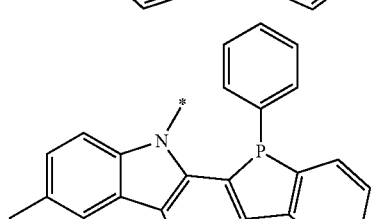

493
-continued
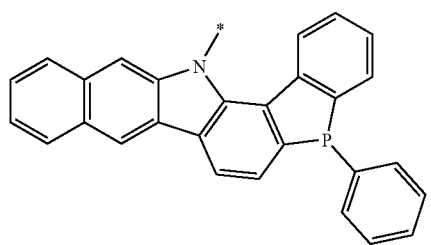
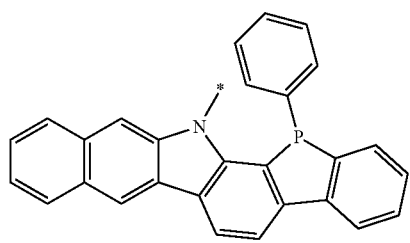
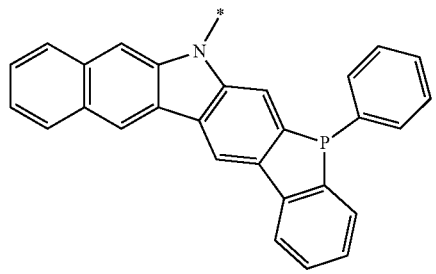
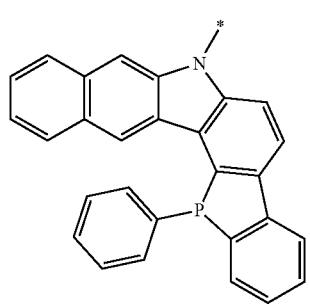
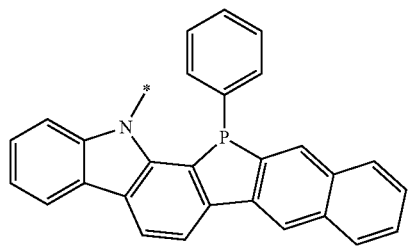
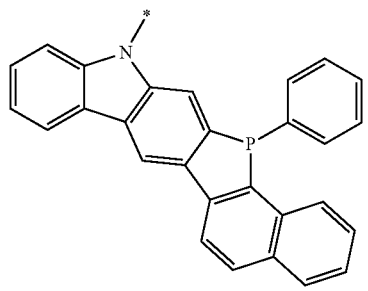
494
-continued
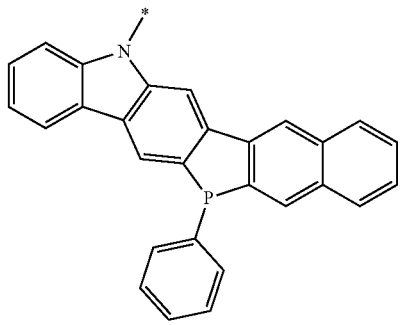
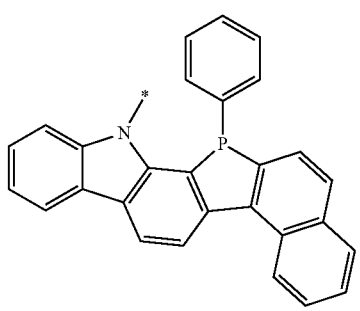
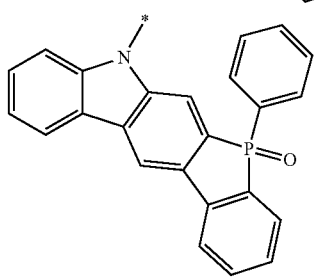
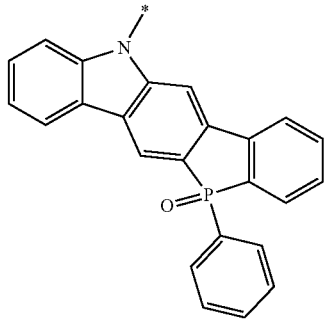
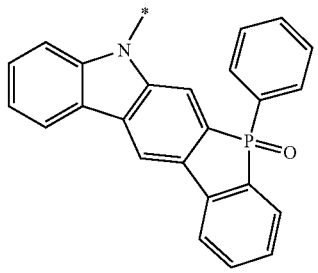
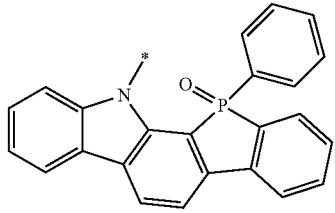

495
-continued
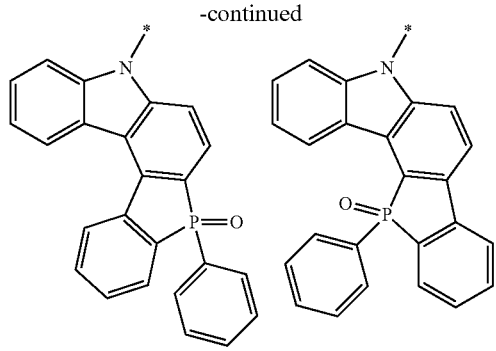
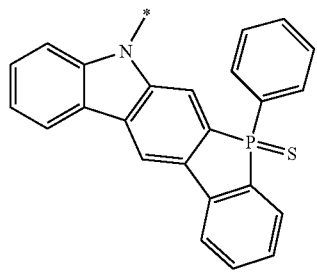
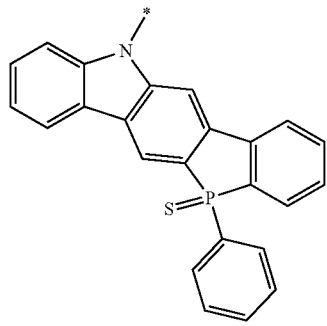
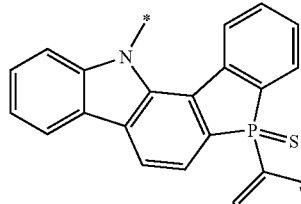
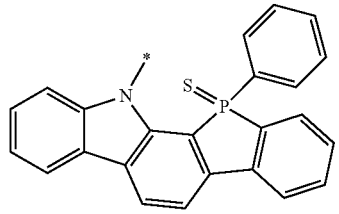
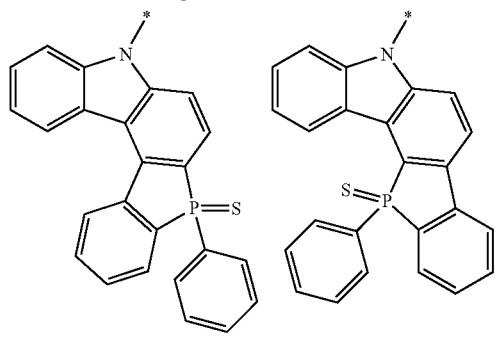
496
-continued
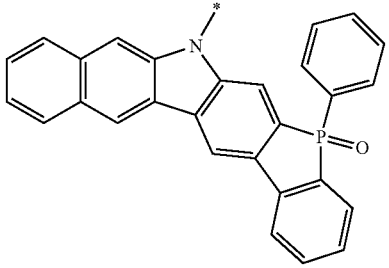
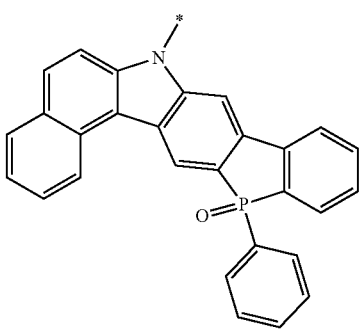
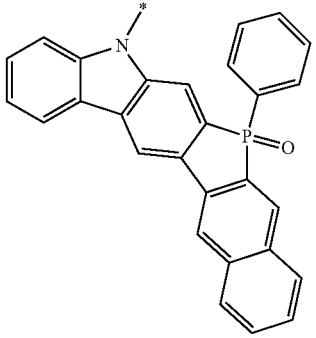
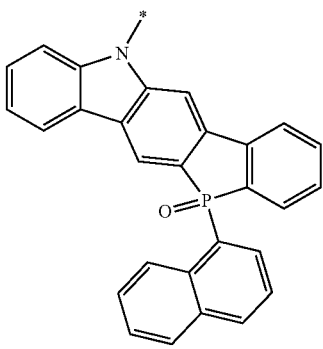
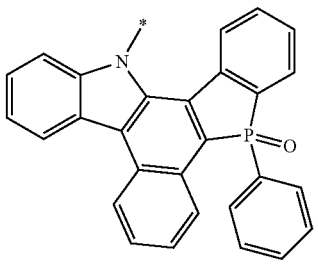

497
-continued
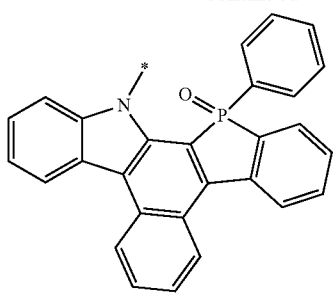
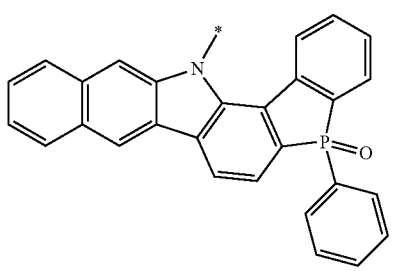
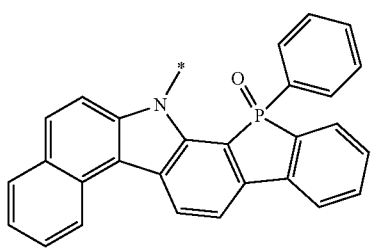
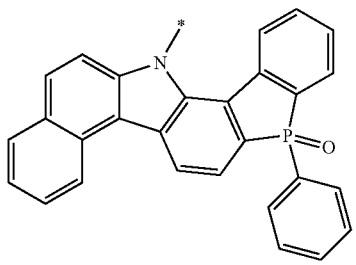
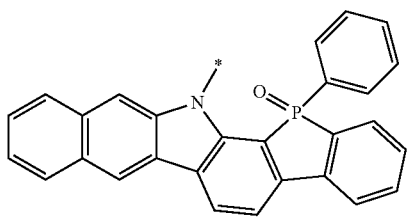
498
-continued
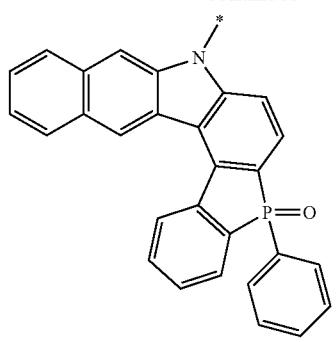
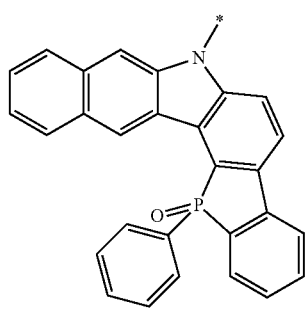
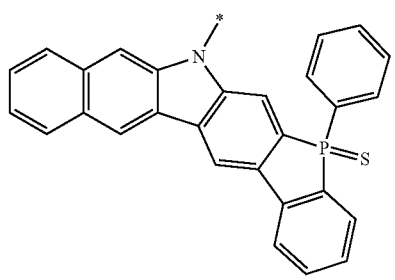
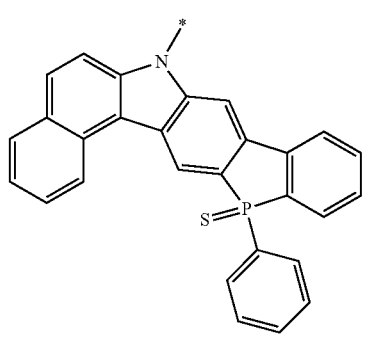
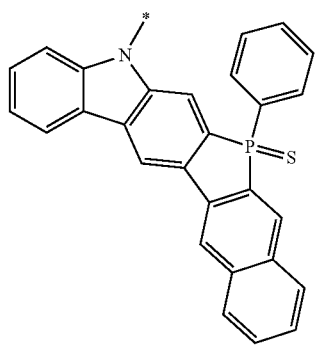

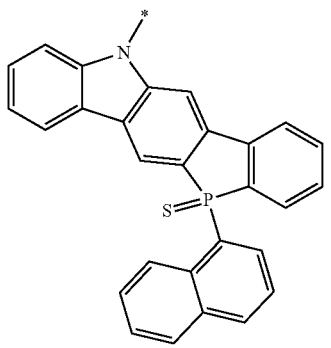

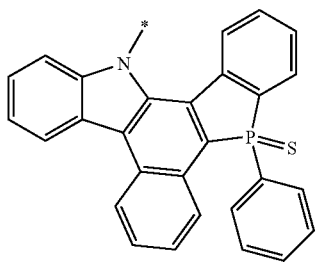

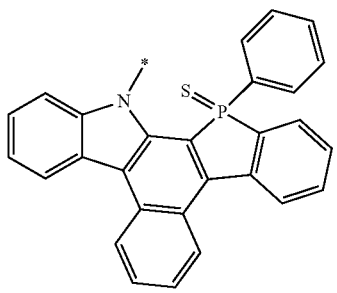

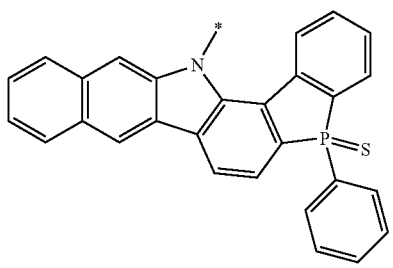

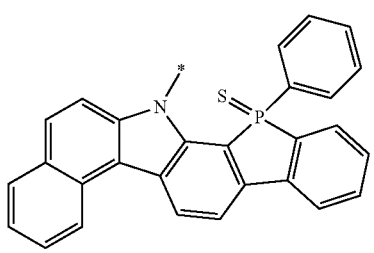

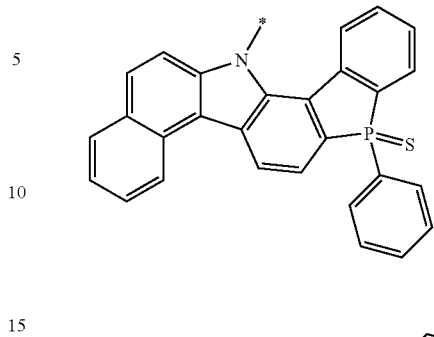

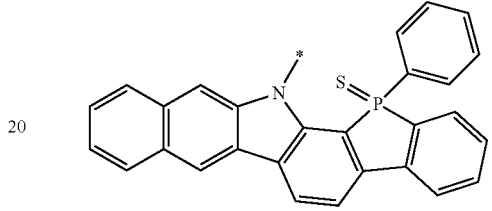

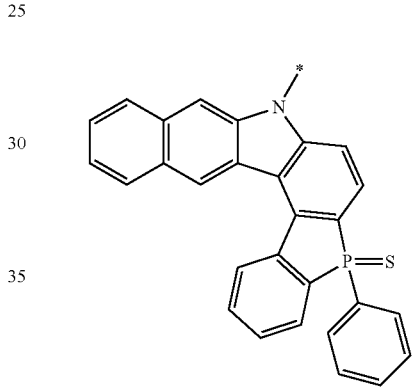

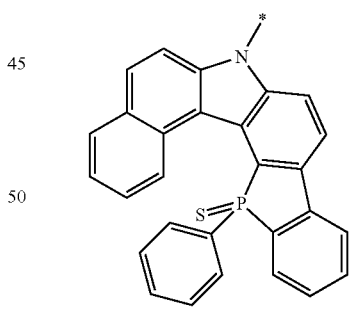

As described above, p to r in formula 1[II] each independently represent an integer of 0 to 3 and p+q+r is 3. Preferably, two selected from p to r cannot be 0 at the same time, although not particularly limited thereto.

When p, q or r is 2 or 3, 2 or 3 groups in each [ ] may be the same or different.

Compound in an Aspect of the Invention

In an aspect, the compound of the invention is preferably a compound represented by formula 1a[II] (also referred to as "compound 1a[II]").

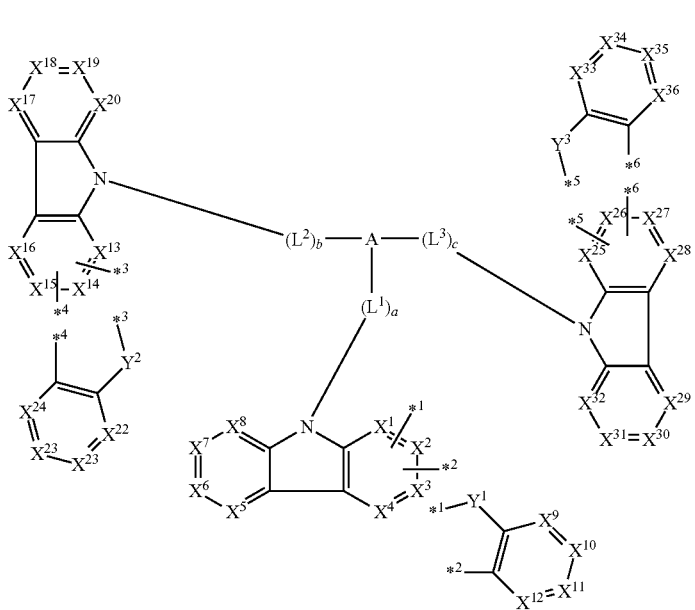

(1a[II])

in formula 1a[II], A, $L^1$ to $L^3$, a to c, $X^1$ to $X^3$, and $Y^1$ to $Y^3$ are as described above in formula 1[II].

In an aspect of the invention, the compound 1a[II] is preferably a compound represented by formula 1a-i[II] (also referred to as "compound 1a-i[II]").

In formula 1a-i[II], two carbon atoms from which two selected from $R^1$ to $R^4$ are removed are respectively bonded to *1 and *2; two carbon atoms from which two selected from $R^{13}$ to $R^{16}$ are removed are respectively bonded to *3 and *4; and two carbon atoms from which two selected from $R^{25}$ to $R^{28}$ are removed are respectively bonded to *5 and *6.

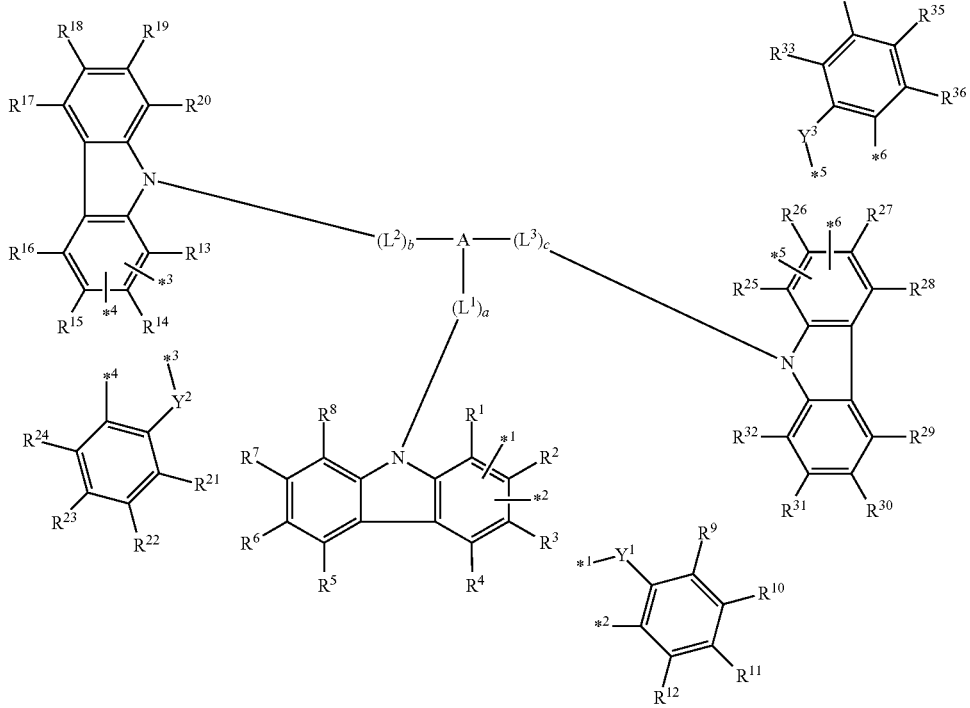

(1a-i[II])

in formula 1a-i[II], A, $L^1$ to $L^3$, a to c, and $Y^1$ to $Y^3$ are as described above in formula 1[II] and $R^1$ to $R^{36}$ are as described above with respect to R of formula 1[II], namely, $R^1$ to $R^{36}$ may be the same or different and each independently represent a hydrogen atom or a substituent, and two selected from $R^1$ to $R^{36}$ may be bonded to each other to form a ring.

In an aspect of the invention, the compound 1a-i[II] is preferably a compound wherein two selected from $R^1$ to $R^{36}$ are not bonded to each other, thereby failing to form a ring, and more preferably a compound represented by formula 1a-v[II]:

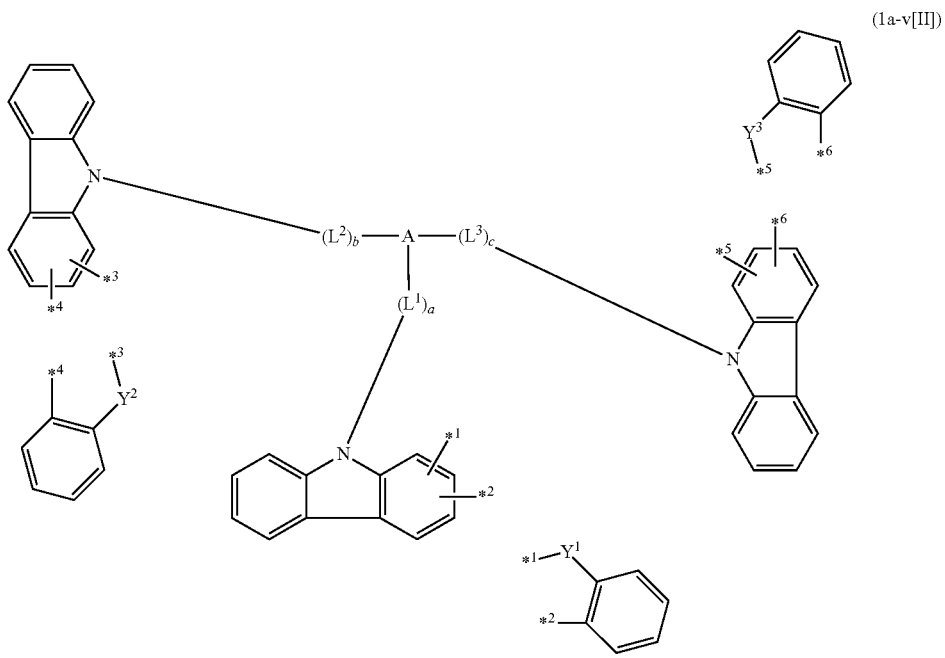

(1a-v[II])

in formula 1a-v[II],

A, $L^1$ to $L^3$, a to c, and $Y^1$ to $Y^3$ are as described above in formula 1[II]; and two of the carbon atoms at 1-position, 2-position, 3-position and 4-position of the carbazolyl group from which hydrogen atoms are removed are bonded to *1 and *2, *3 and *4, or *5 and *6, respectively.

In an aspect of the invention, the compound 1a-i[II] is more preferably a compound represented by any of formulae 1a-i-1[II] to 1a-i-6[II] (also referred to as "compounds 1a-i-1[II] to 1a-i-6[II]"):

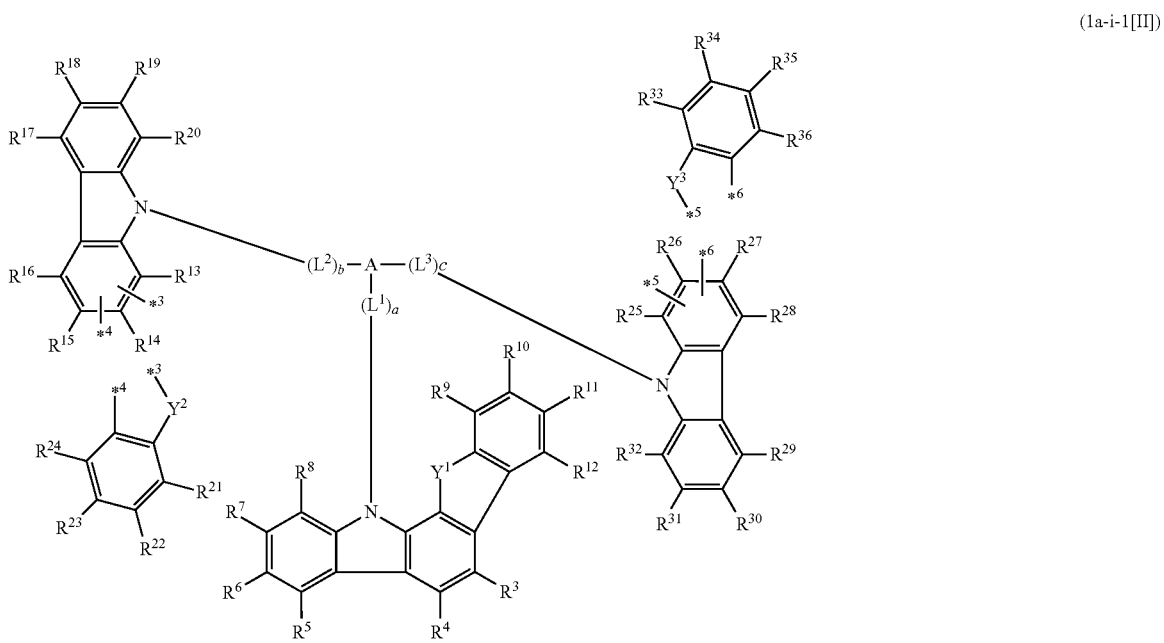

(1a-i-1[II])

-continued
(1a-i-2[II])
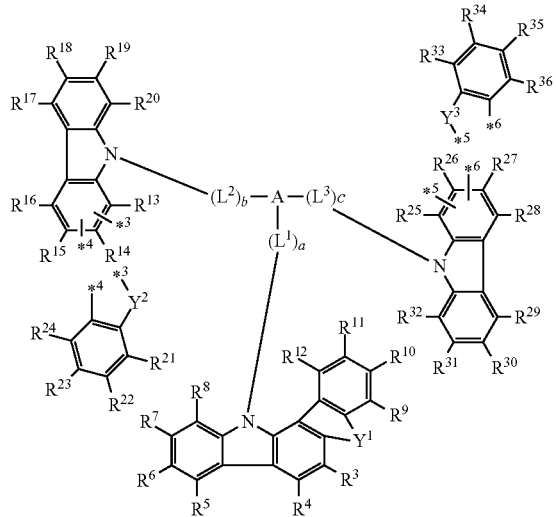
(1a-i-3[II])
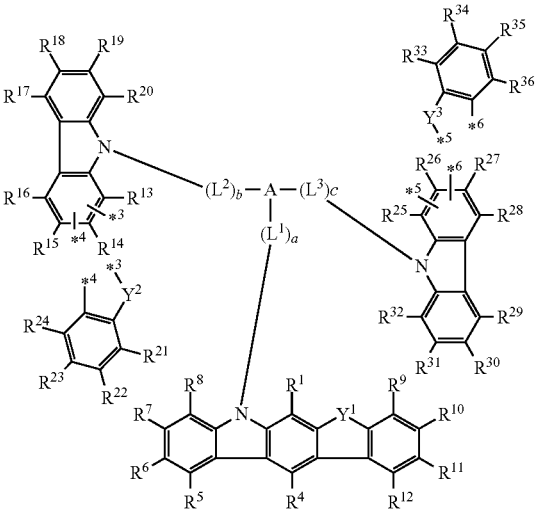
(1a-i-4[II])
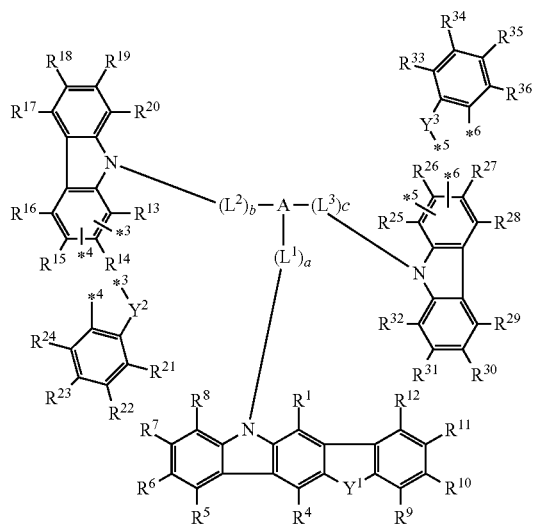
(1a-i-5[II])
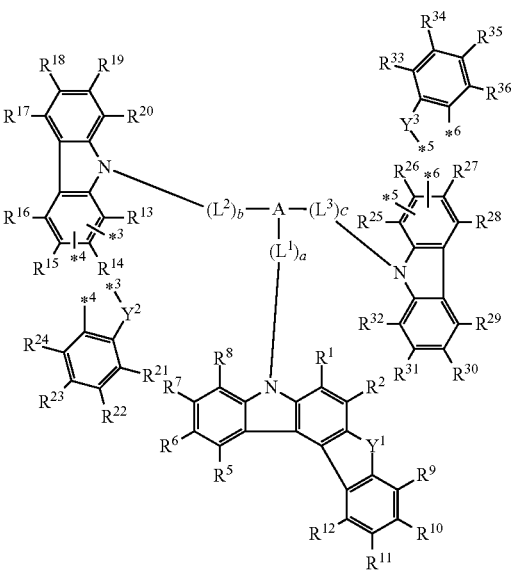
(1a-i-6[II])
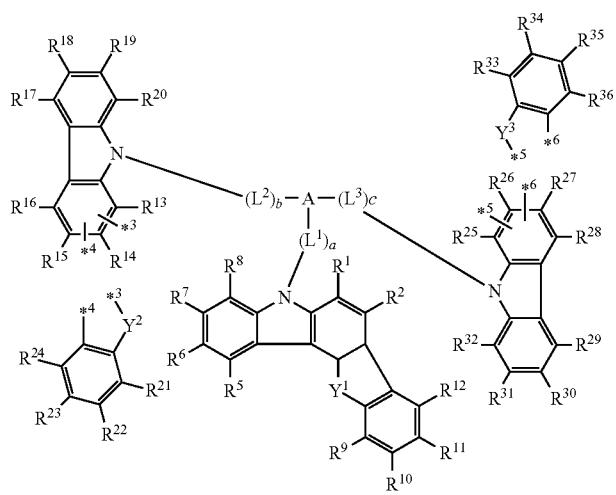

in formulae 1a-i-1[II] to 1a-i-6[II],

A, $L^1$ to $L^3$, a to c, and $Y^1$ to Y are as described above in formula 1[II];

$R^1$ to $R^{36}$ are as described above with respect R of formula 1[II];

two carbon atoms from which two selected from $R^{13}$ to $R^{16}$ are removed are bonded to *3 and *4, respectively; and two carbon atoms from which two selected from $R^{25}$ to $R^{28}$ are removed are bonded to *3 and *4, respectively.

In an aspect, the compound of the invention is more preferably a compound represented by formula 1a-ii[II] (also referred to as "compound 1a-ii[II]"):

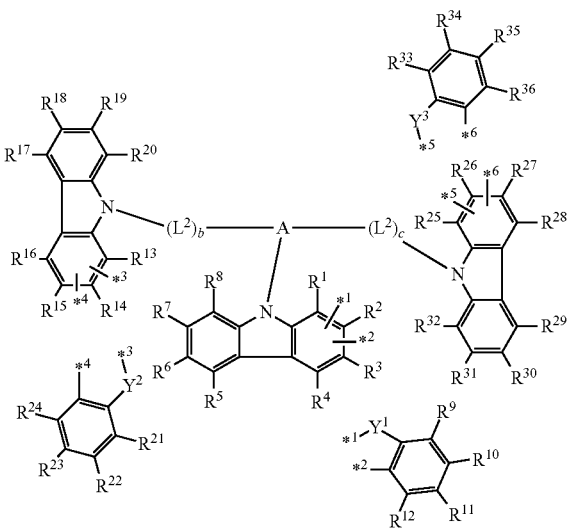

(1a-iii[II])

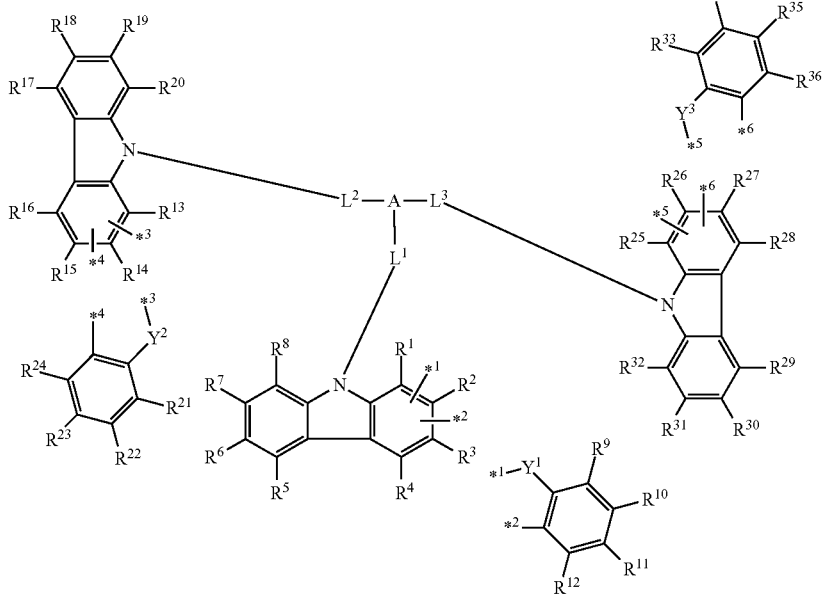

(1a-ii[II])

in formula 1a-ii[II],

A, $L^1$ to $L^3$, and $Y^1$ to $Y^3$ are as described above in formula 1[II];

$R^1$ to $R^{36}$ are as described above with respect R of formula 1[II];

two carbon atoms from which two selected from $R^1$ to $R^4$ are removed are bonded to *1 and *2, respectively;

two carbon atoms from which two selected from $R^{13}$ to $R^{16}$ are removed are bonded to *3 and *4, respectively; and two carbon atoms from which two selected from $R^{25}$ to $R^{28}$ are removed are bonded to *5 and *6, respectively.

In an aspect, the compound of the invention is more preferably a compound represented by formula 1a-iii[II] (also referred to as "compound 1a-iii[II]"):

in formula 1a-iii[II],

A, $L^2$ to $L^3$, b to c, and $Y^1$ to $Y^3$ are as described above in formula 1[II];

$R^1$ to $R^{36}$ are as described above with respect R of formula 1[II];

two carbon atoms from which two selected from $R^1$ to $R^4$ are removed are bonded to *1 and *2, respectively;

two carbon atoms from which two selected from $R^{13}$ to $R^{16}$ are removed are bonded to *3 and *4, respectively; and two carbon atoms from which two selected from $R^{25}$ to $R^{28}$ are removed are bonded to *5 and *6, respectively.

In an aspect, the compound of the invention is more preferably a compound represented by formula 1a-iv[II] (also referred to as "compound 1a-iv[II]"):

(1a-iv[II])

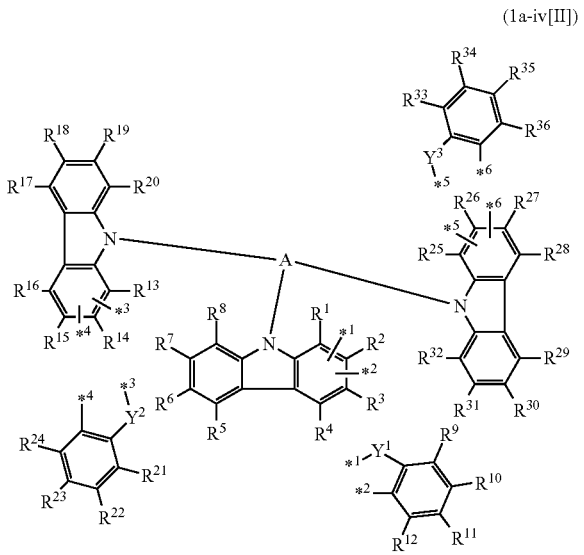

in formula 1a-iv[II],

A and $Y^1$ to $Y^3$ are as described above in formula 1[II];
$R^1$ to $R^{36}$ are as described above with respect R of formula 1[II];
two carbon atoms from which two selected from $R^1$ to $R^4$ are removed are bonded to *1 and *2, respectively;
two carbon atoms from which two selected from $R^{13}$ to $R^{16}$ are removed are bonded to *3 and *4, respectively; and
two carbon atoms from which two selected from $R^{25}$ to $R^{28}$ are removed are bonded to *5 and *6, respectively.

In an aspect, the compound of the invention is more preferably a compound represented by formula 1b[II] (also referred to as "compound 1b[II]"):

(1b[II])

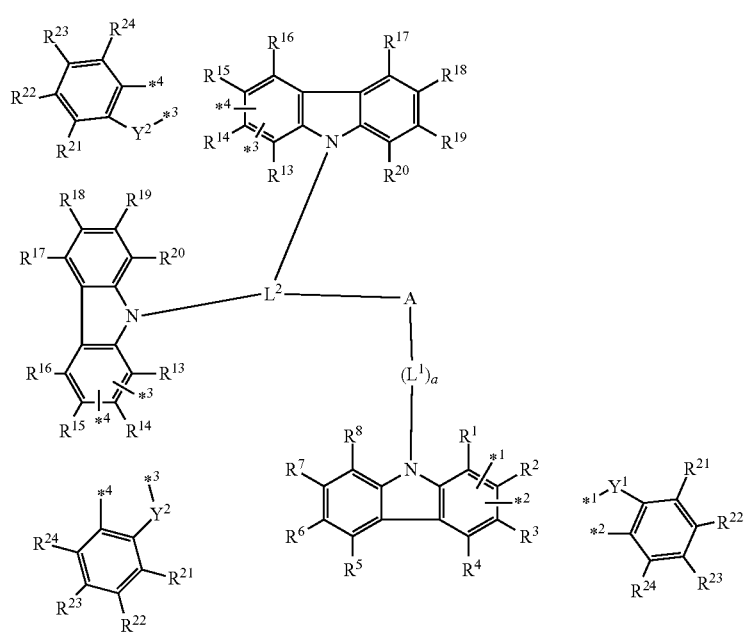

in formula 1b[II],

A, $L^1$ to $L^2$, a, and $Y^1$ to $Y^2$ are as described above in formula 1[II];

$R^1$ to $R^{24}$ are as described above with respect R of formula 1[II];
two carbon atoms from which two selected from $R^1$ to $R^4$ are removed are bonded to *1 and *2, respectively; and
two carbon atoms from which two selected from $R^{13}$ to $R^{16}$ are removed are bonded to *3 and *4, respectively.

In an aspect of the invention, the compound 1b[II] is preferably a compound wherein two selected from $R^1$ to $R^{24}$ are not bonded to each other, thereby failing to form a ring and more preferably a compound represented by formula 1b-i[II]:

(1b-i[II])

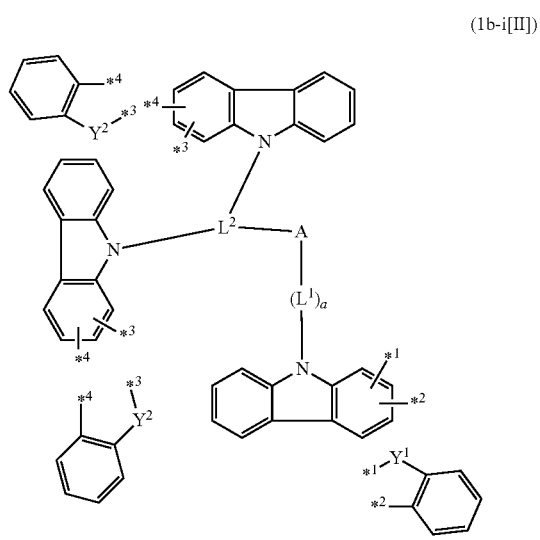

in formula 1b-i[II],

A, $L^1$ to $L^2$, a, and $Y^1$ to $Y^2$ are as described above in formula 1[II]; and two of the carbon atoms at 1-position, 2-position, 3-position and 4-position of the carbazolyl group from which hydrogen atoms are removed are bonded to *1 and *2, *3 and *4, or *5 and *6, respectively.

In an aspect, the compound of the invention is preferably a compound represented by any of formulae 1c-i[II] to 1c-iv[II] (also referred to as "compounds 1c-i[II] to 1c-iv [II]"):

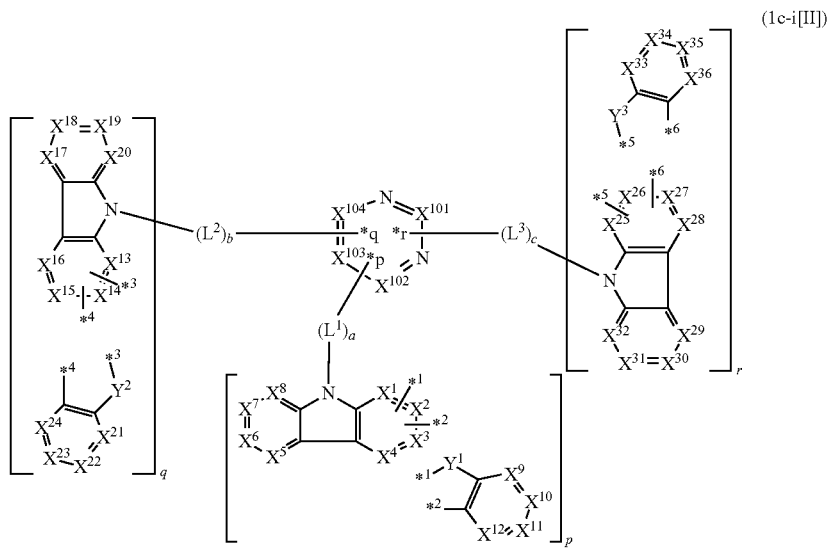
(1c-i[II])

in formula 1c-i[II],
$L^1$ to $L^3$, a to c, p to r, $X^1$ to $X^{36}$, and $Y^1$ to $Y^3$ are as described above in formula 1[II];
$X^{101}$ to $X^{104}$ each represent a carbon atom bonded to one of *p to *r, C(Rx), or a nitrogen atom; and
Rx represents a hydrogen atom or a substituent, two or more groups Rx may be the same or different, and two selected from groups Rx may be bonded to each other to form a ring;

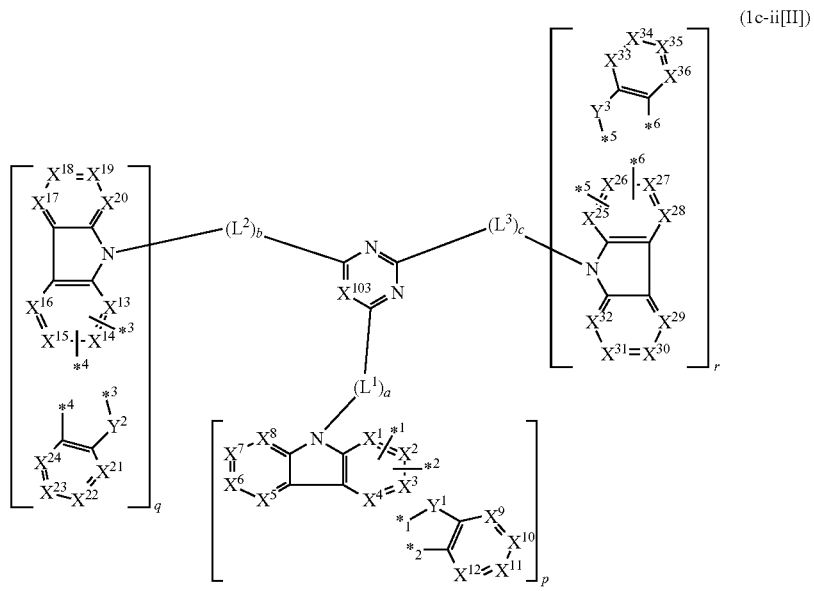
(1c-ii[II])

in formula 1c-ii[II],
$L^1$ to $L^3$, a to c, p to r, $X^1$ to $X^{36}$, and $Y^1$ to $Y^3$ are as described above in formula 1[II]; and
$X^{103}$ represents C(Rx) or a nitrogen atom; and
Rx represents a hydrogen atom or a substituent;

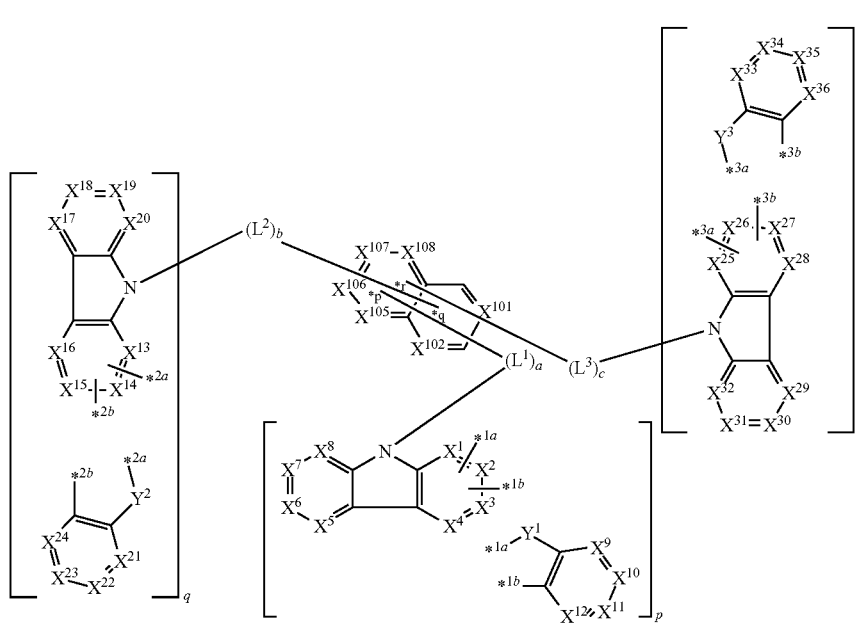

(1c-iii[II])

in formula 1c-iii[II], $L^1$ to $L^3$, a to c, p to r, $X^1$ to $X^{36}$, and $Y^1$ to $Y^3$ are as described above in formula 1[II];

$X^{101}$, $X^{102}$, and $X^{105}$ to $X^{108}$ each represent a carbon atom bonded to one of *p to *r, C(Rx), or a nitrogen atom; and Rx represents a hydrogen atom or a substituent, two or more groups Rx may be the same or different, and two selected from groups Rx may be bonded to each other to form a ring; and in formula 1c-iv[II], $L^1$ to $L^3$, a to c, p to r, $X^1$ to $X^{36}$, and $Y^1$ to $Y^3$ are as described above in formula 1[II];

1 to 3 carbon atoms from which one to three selected from $R^{101}$, $R^{102}$, and $R^{105}$ to $R^{108}$ are removed are each bonded to one of *p to *r, and the others each independently represent a hydrogen atom or a substituent; and two selected from $R^{102}$ and $R^{105}$ to $R^{18}$ may be bonded to each other to form a ring.

Examples of the compound 1[II] in an aspect of the invention are shown below, although not limited thereto.

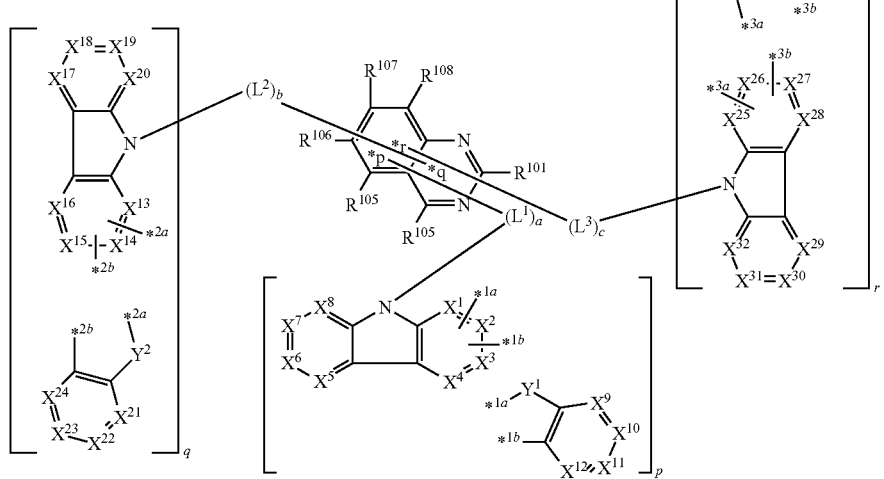

(1c-iv[II])

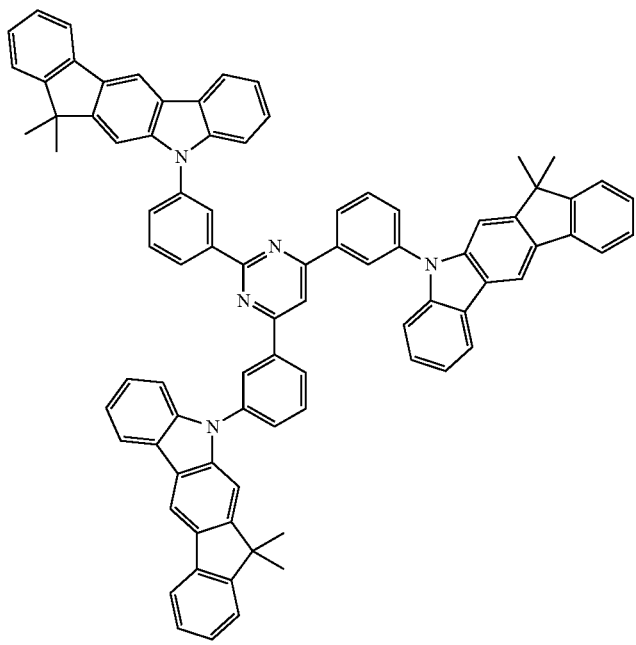
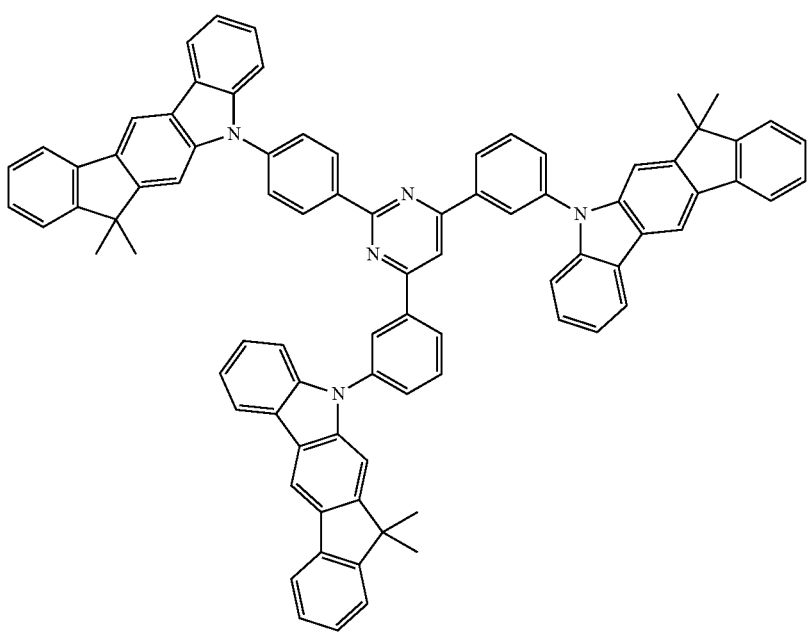

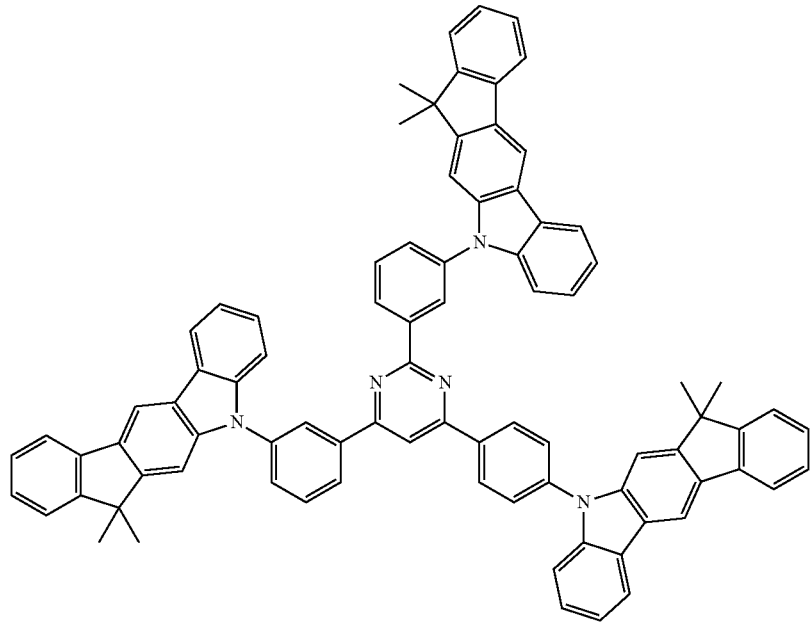
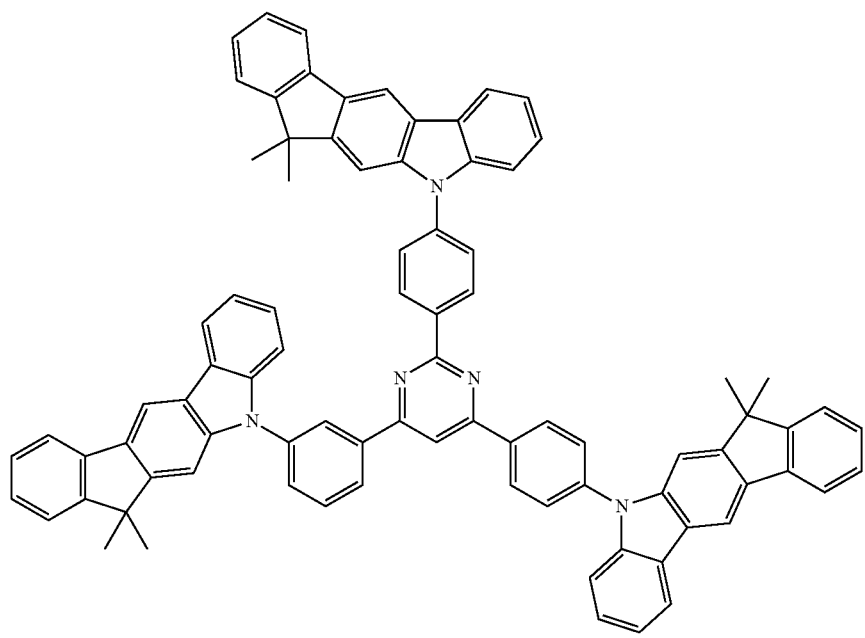

-continued
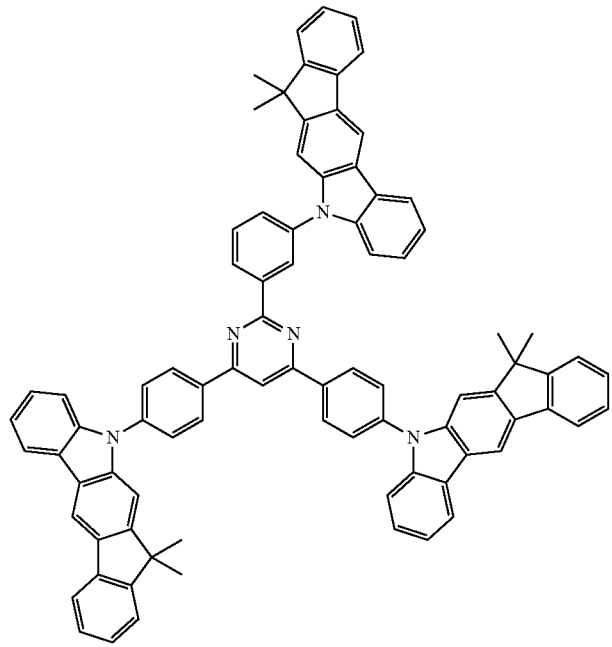
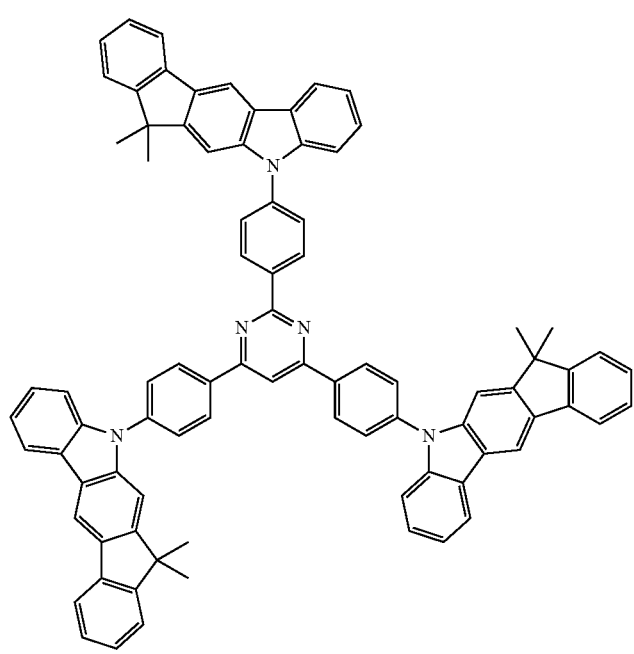

521
522
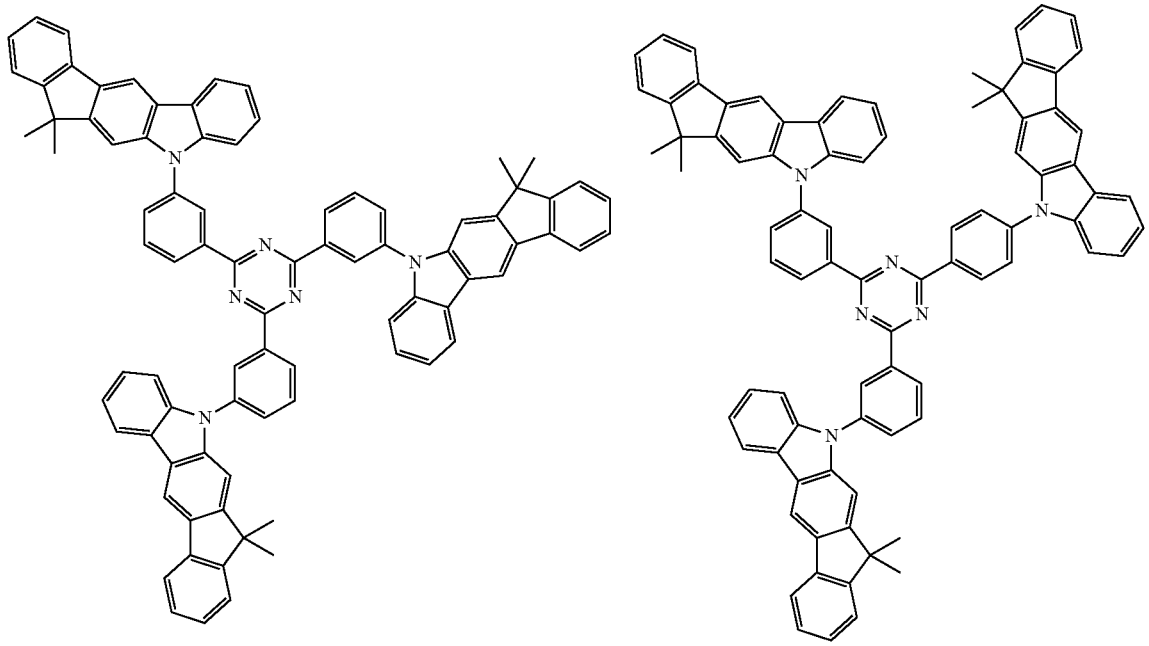
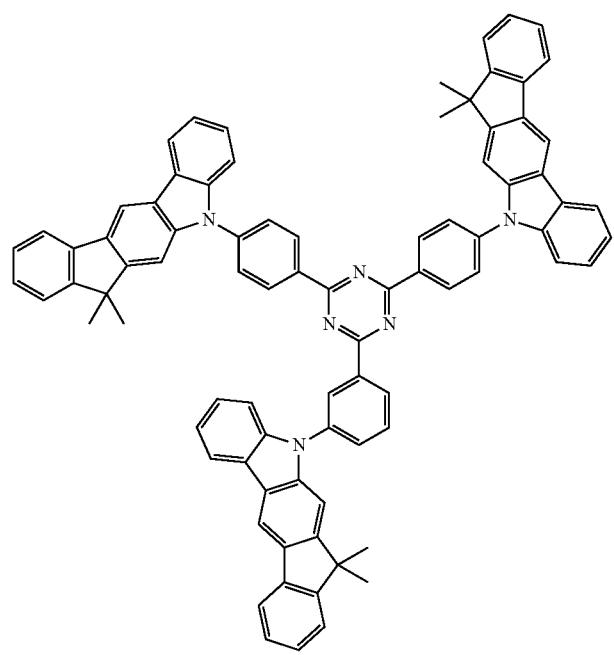

-continued
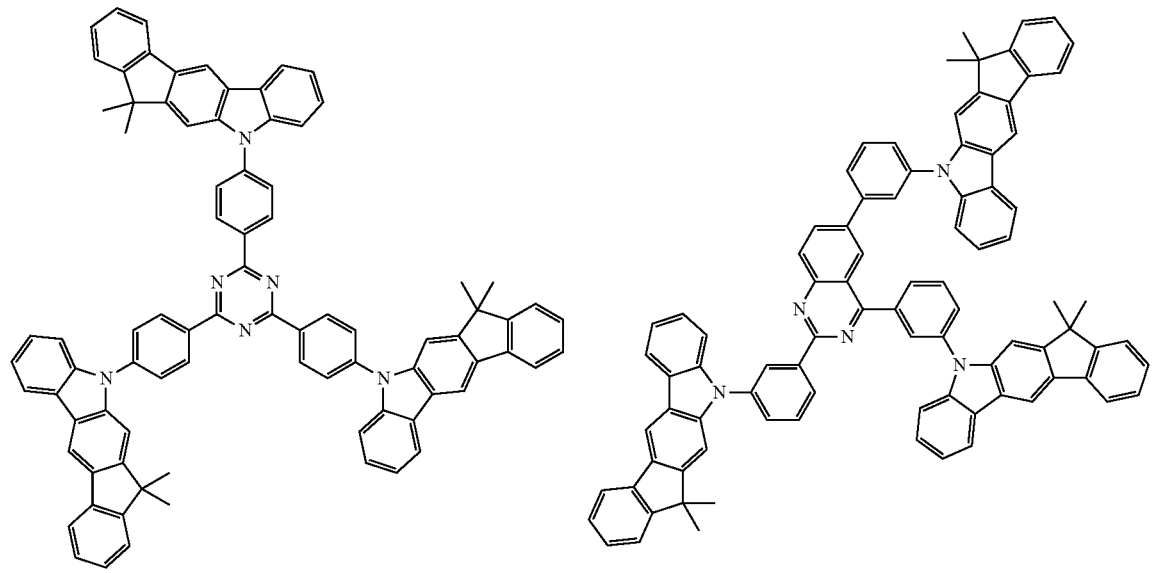

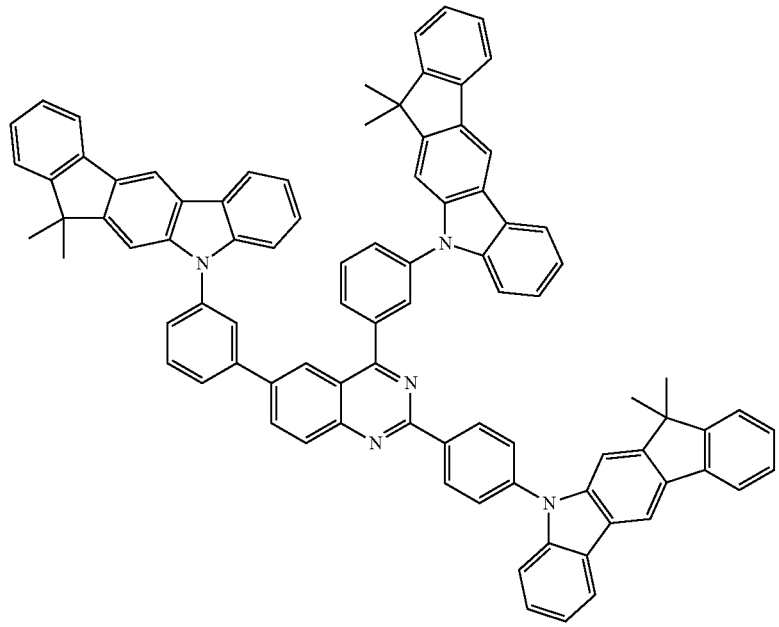
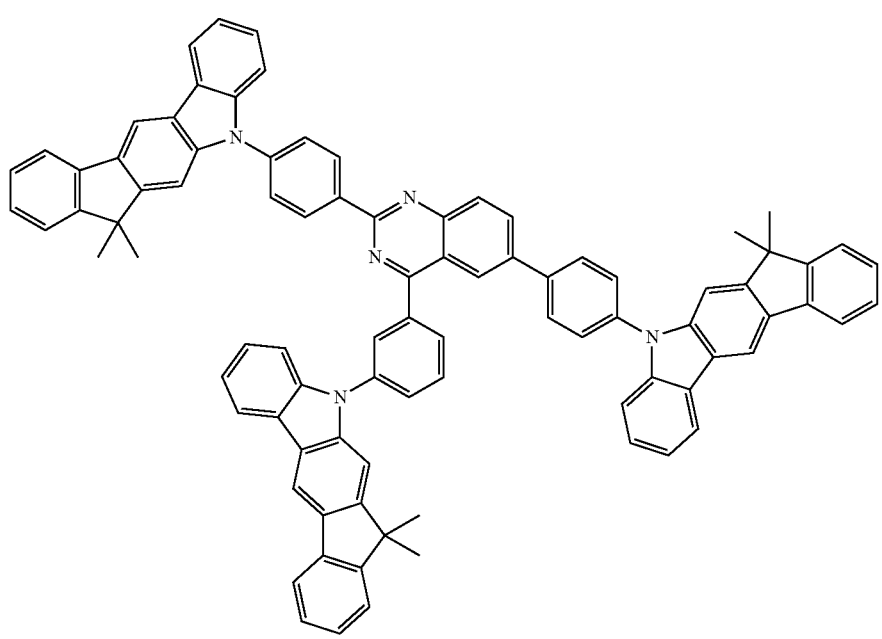

-continued
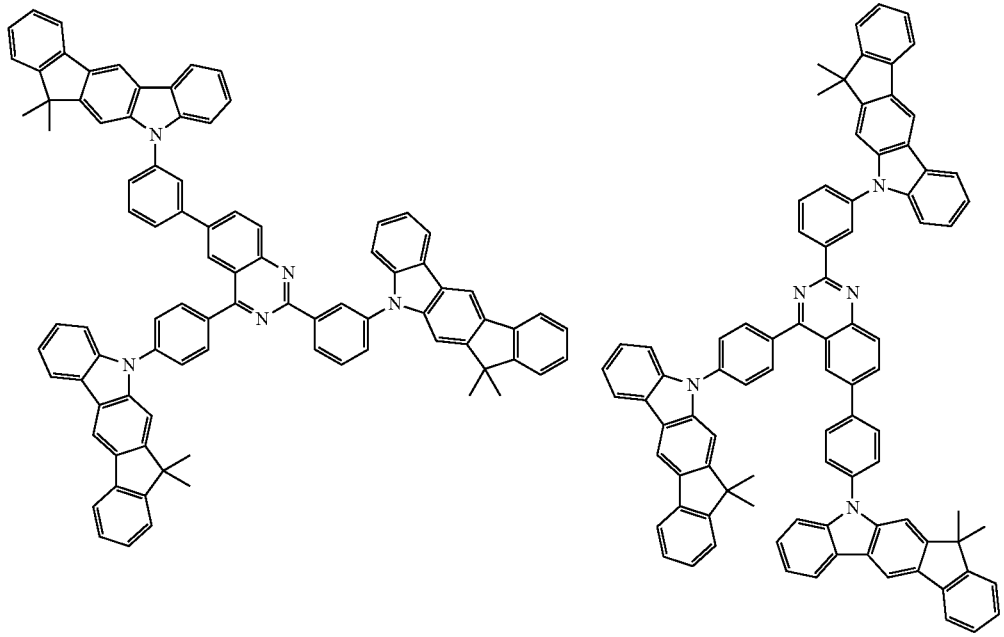
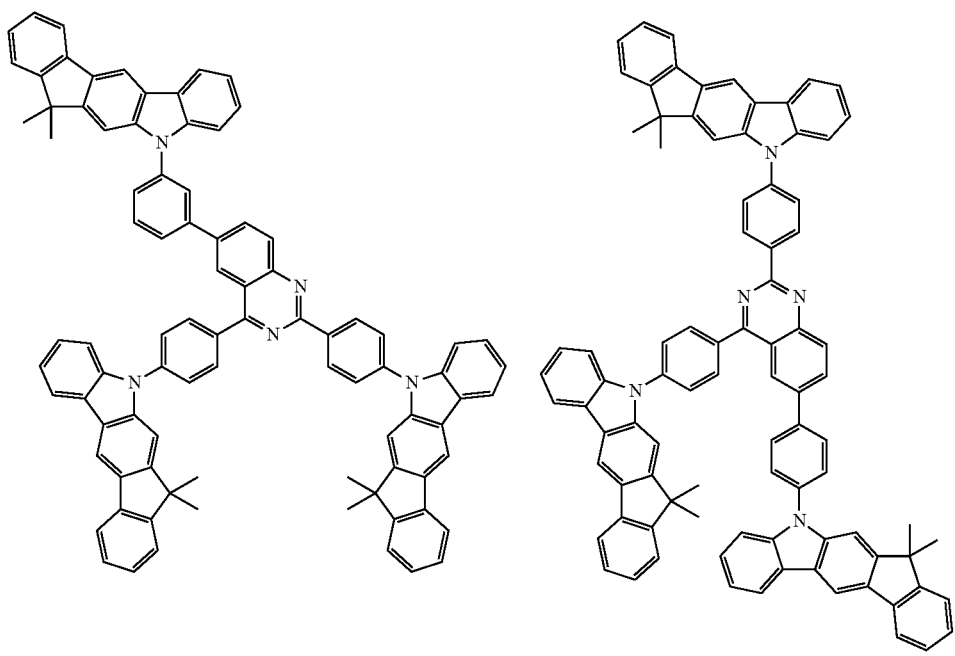

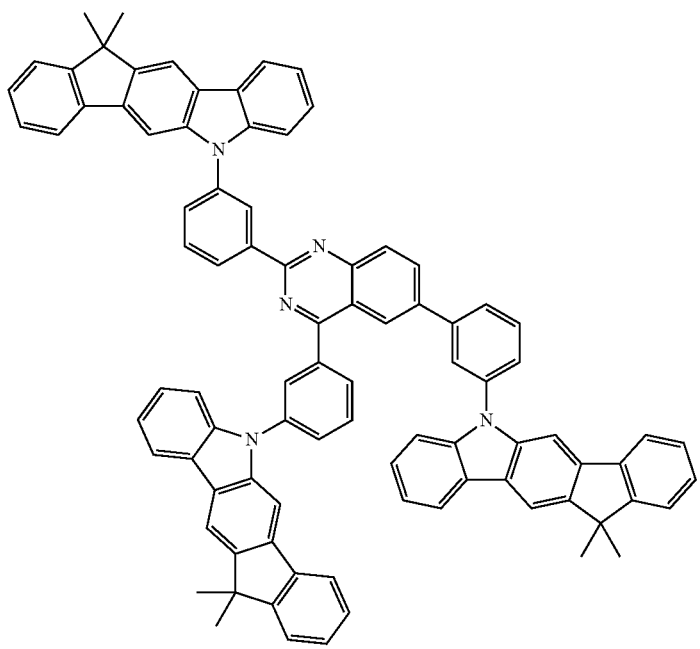
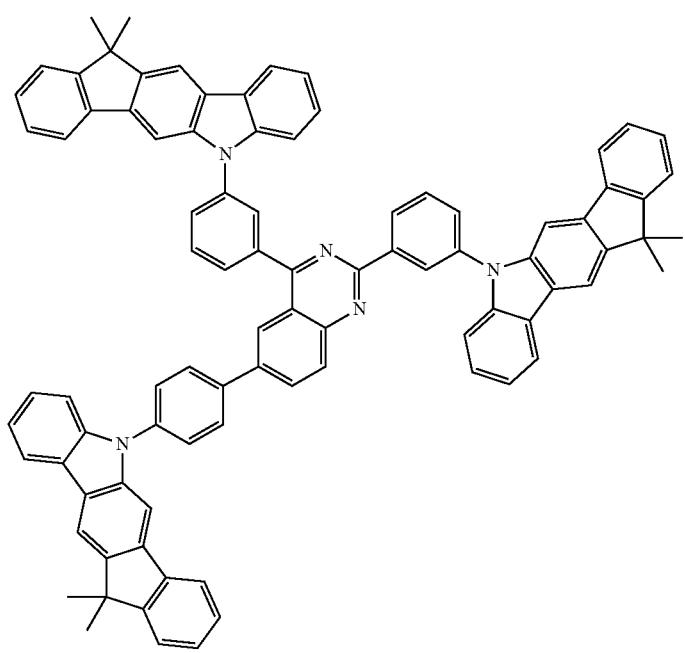

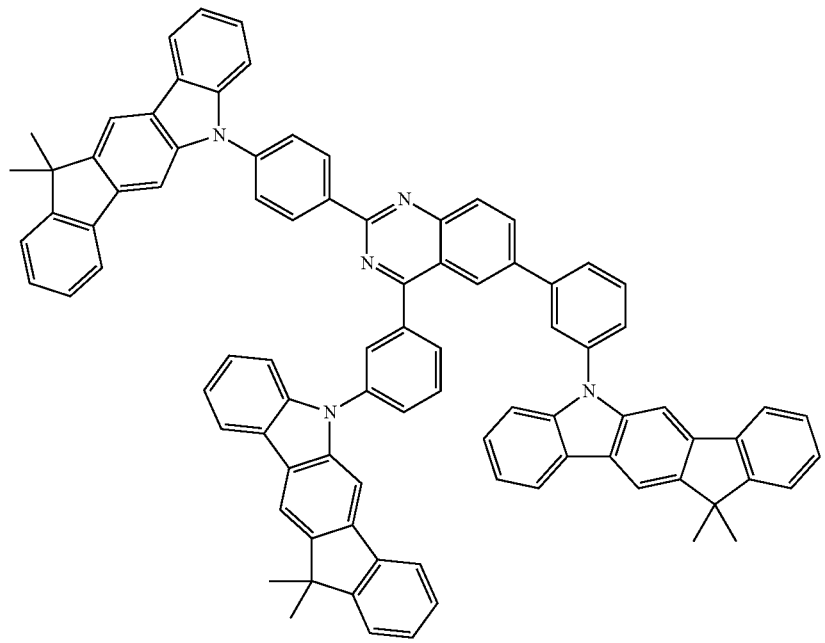
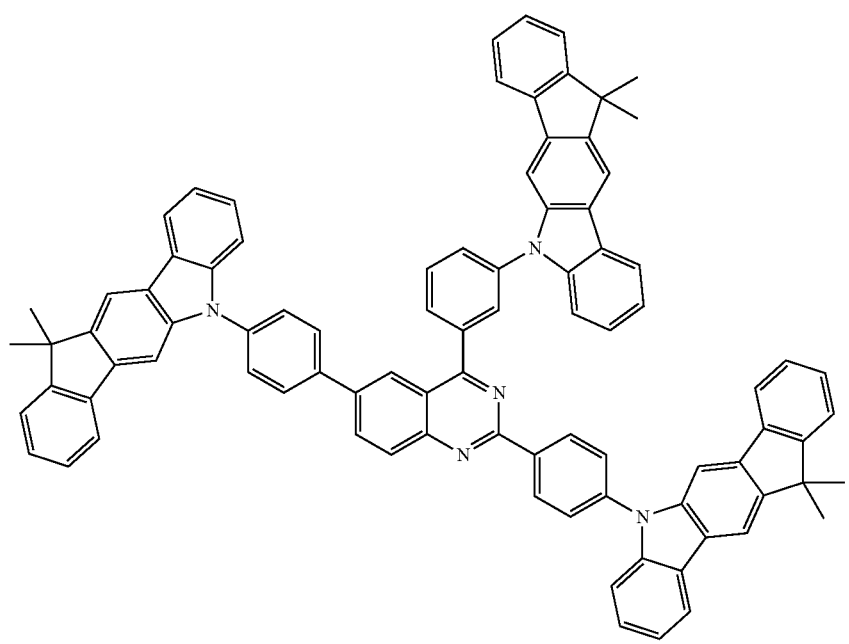

-continued
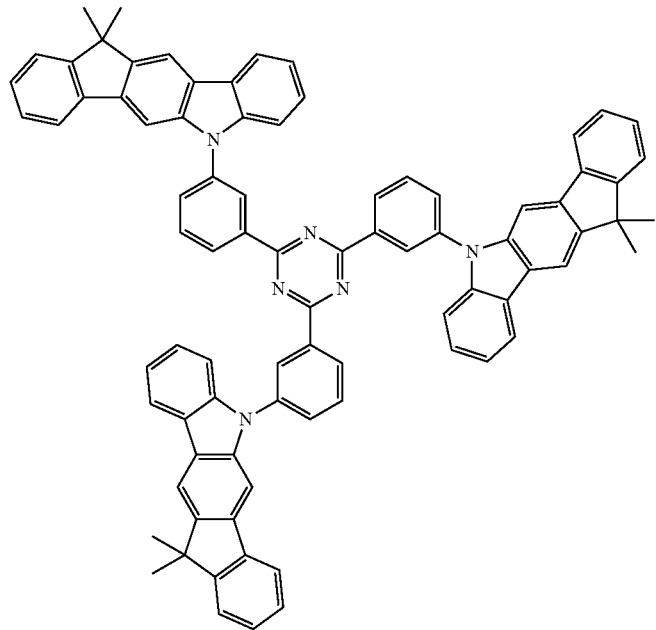
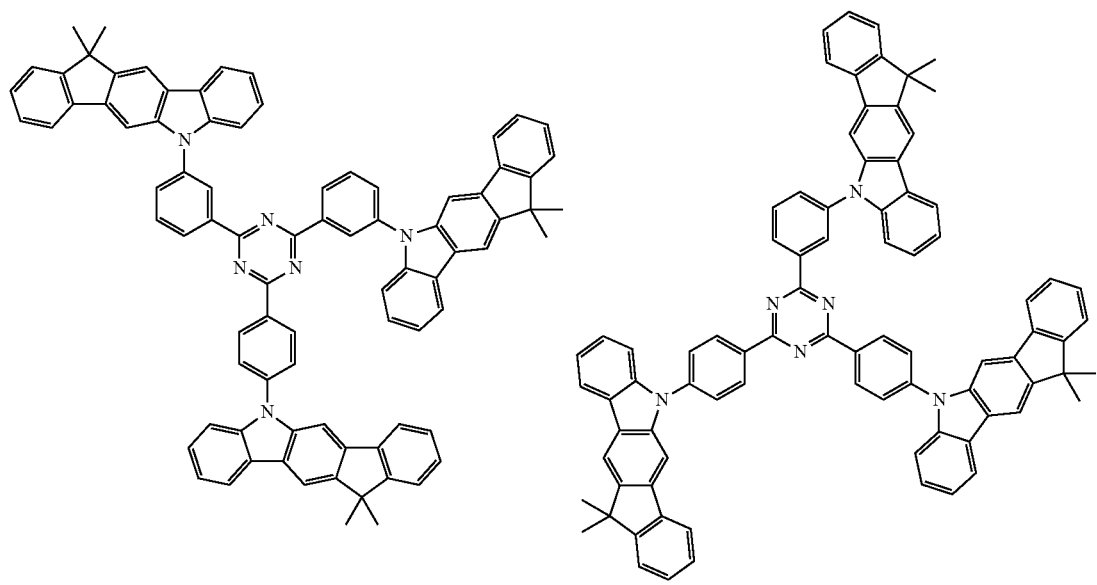

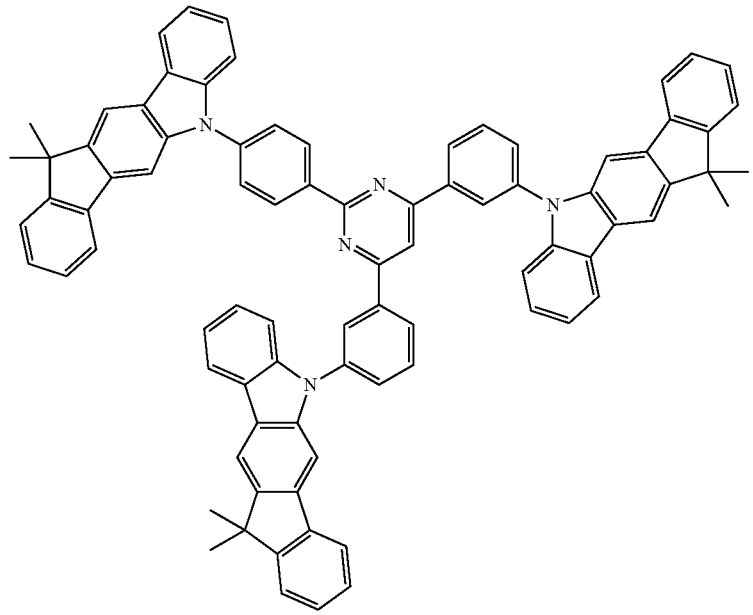
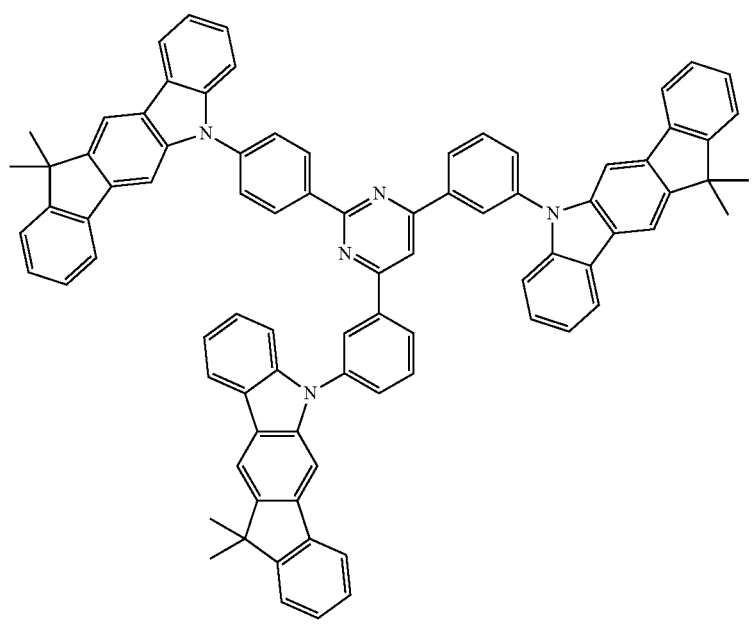

-continued
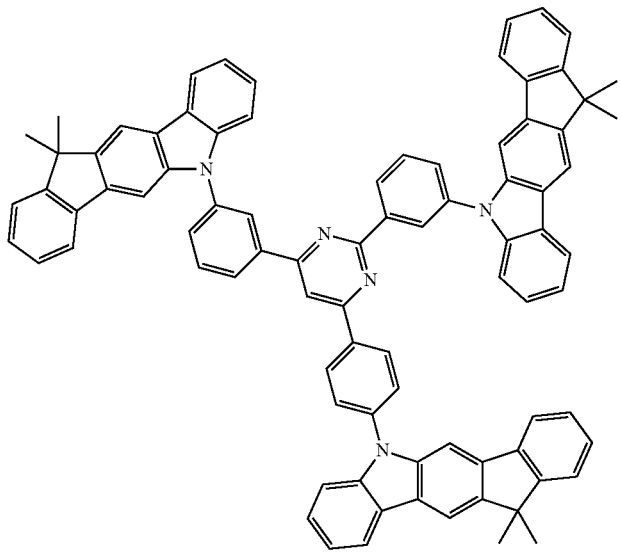
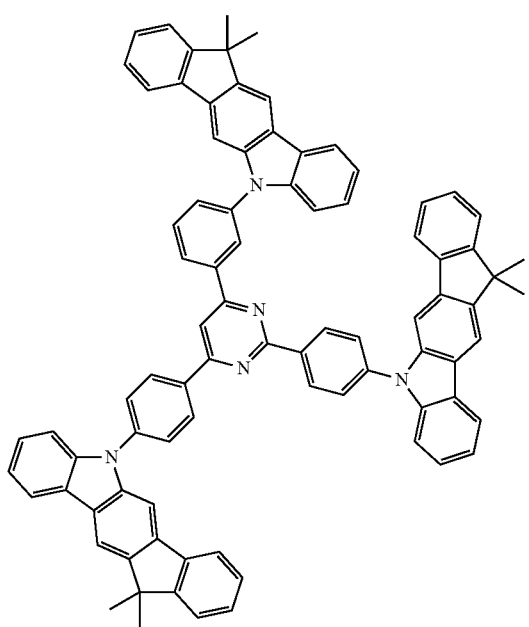

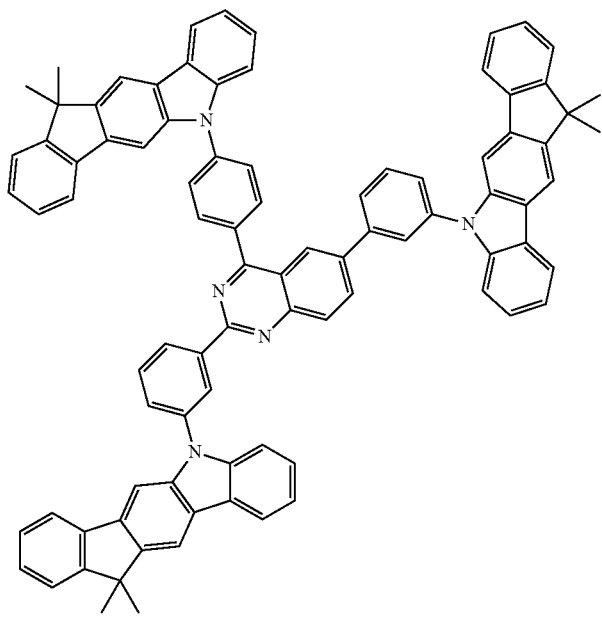
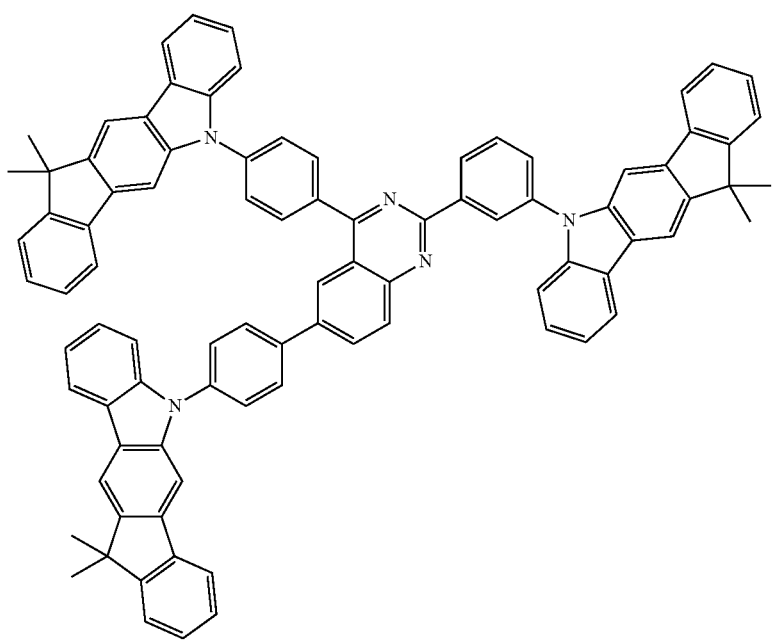

-continued
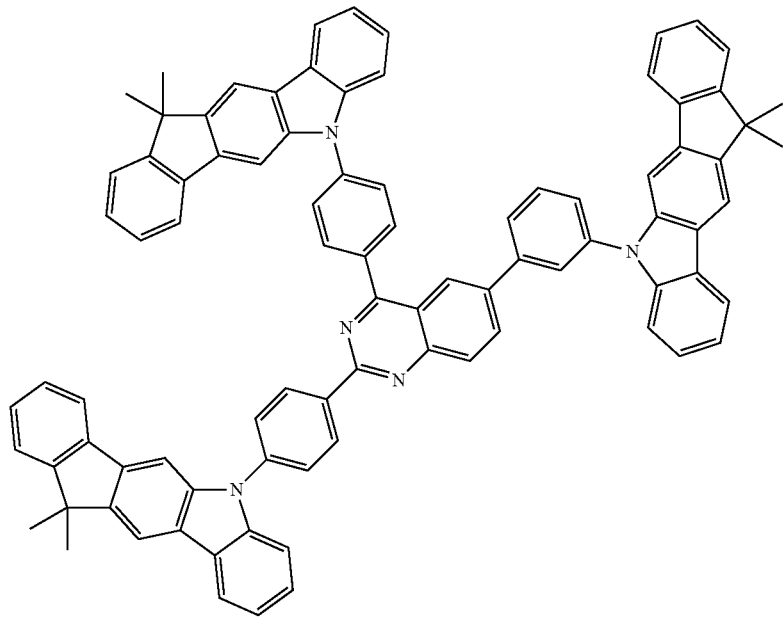
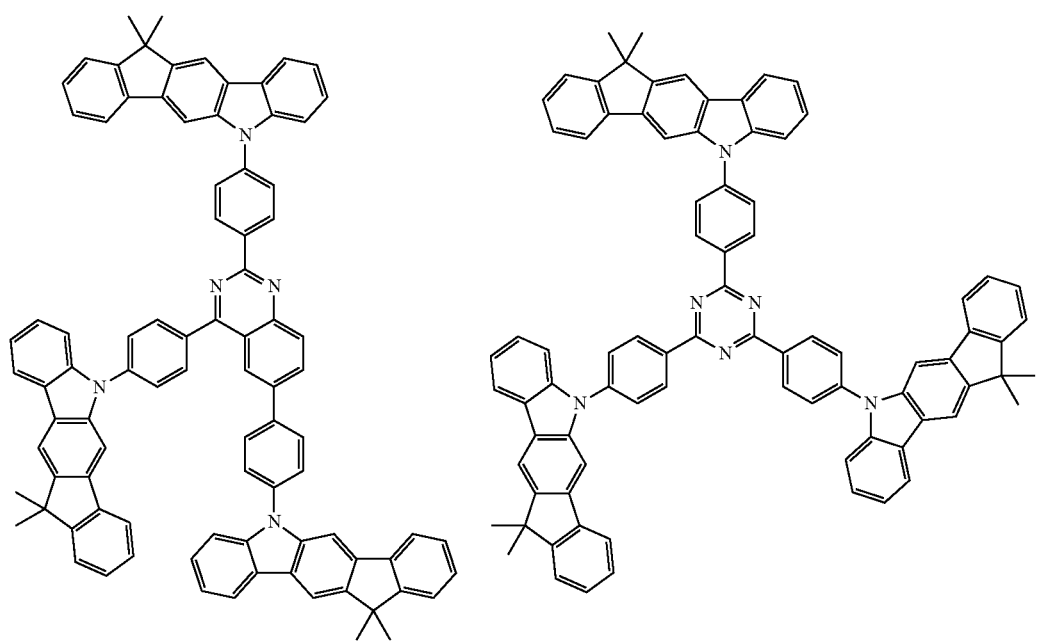

543 544
-continued
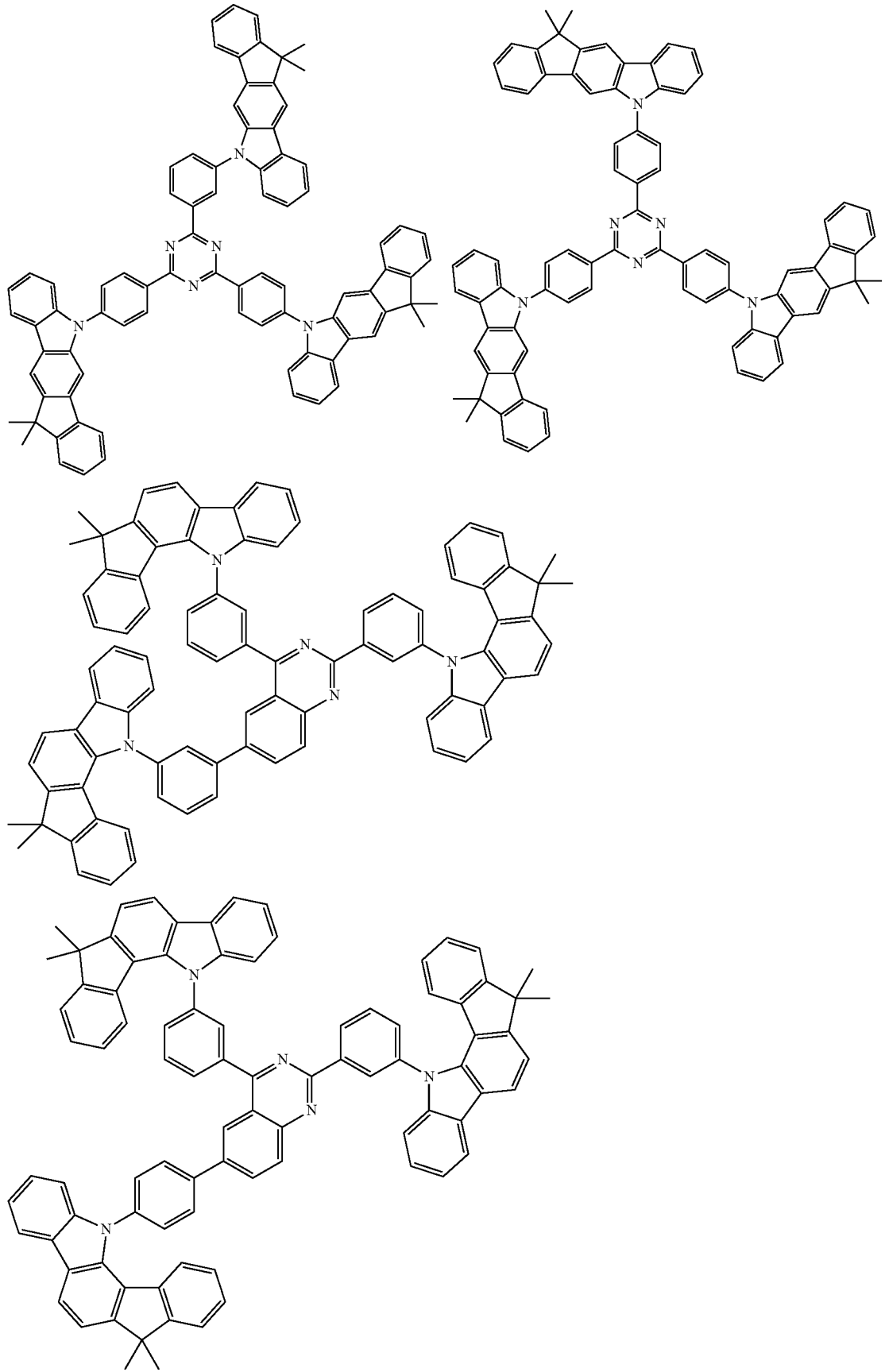

-continued
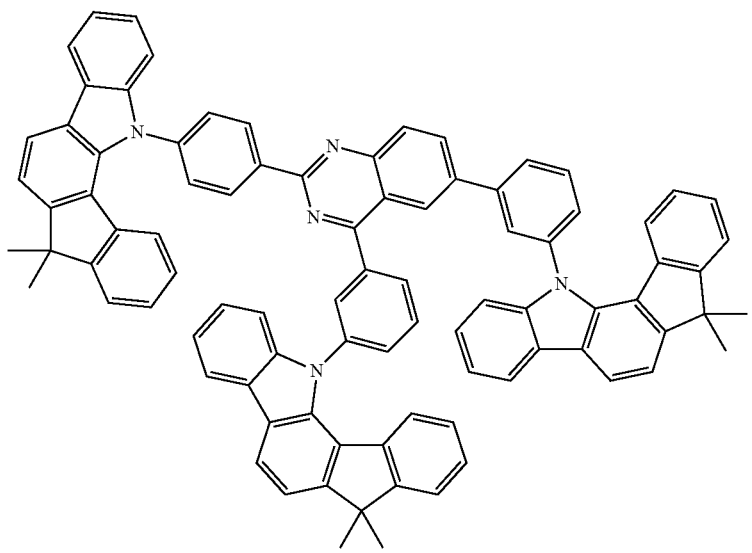
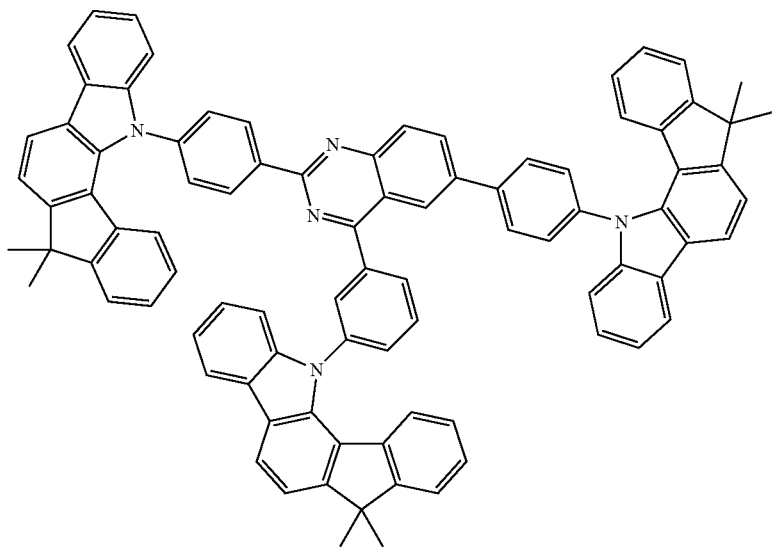
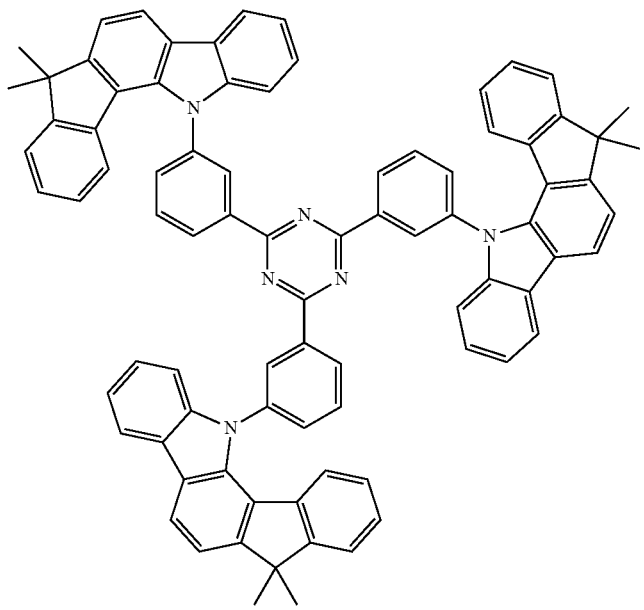

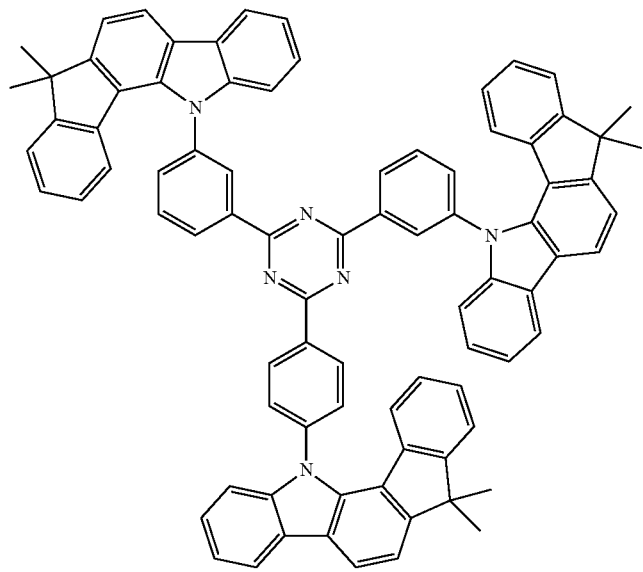
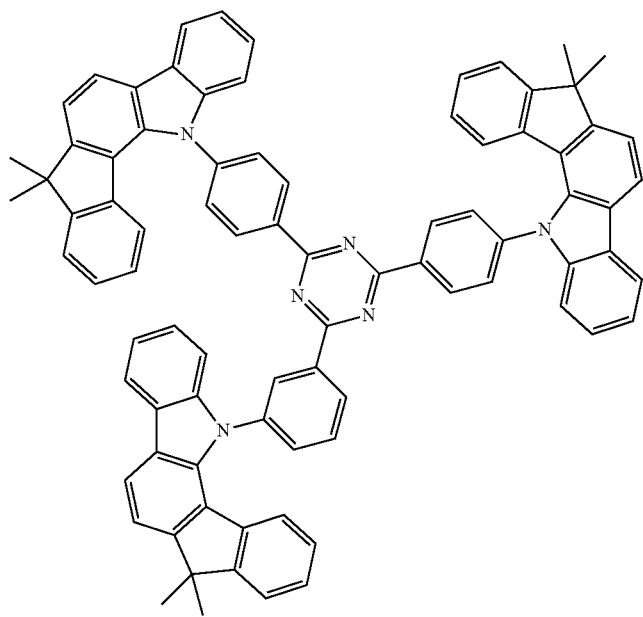

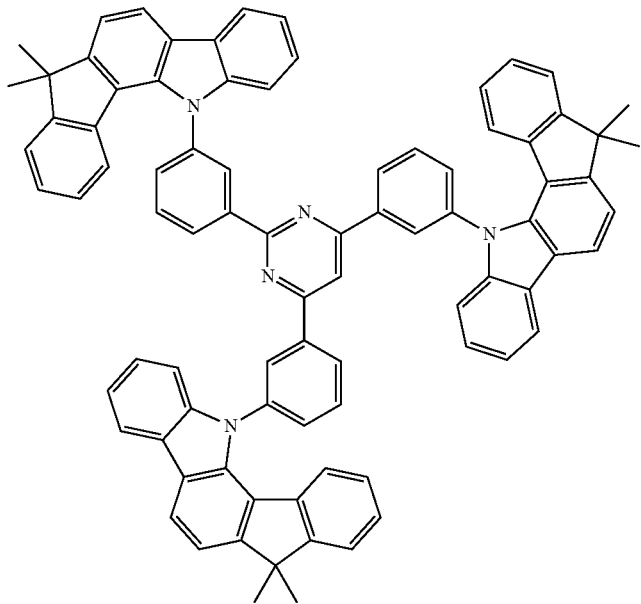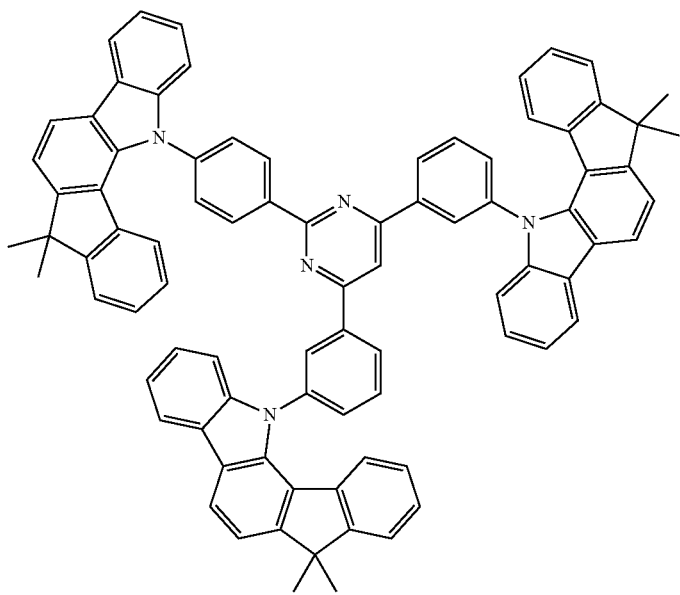

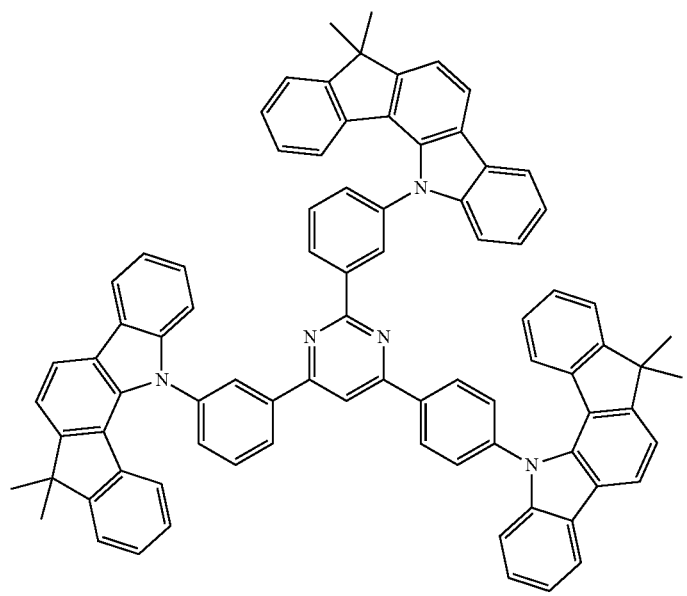
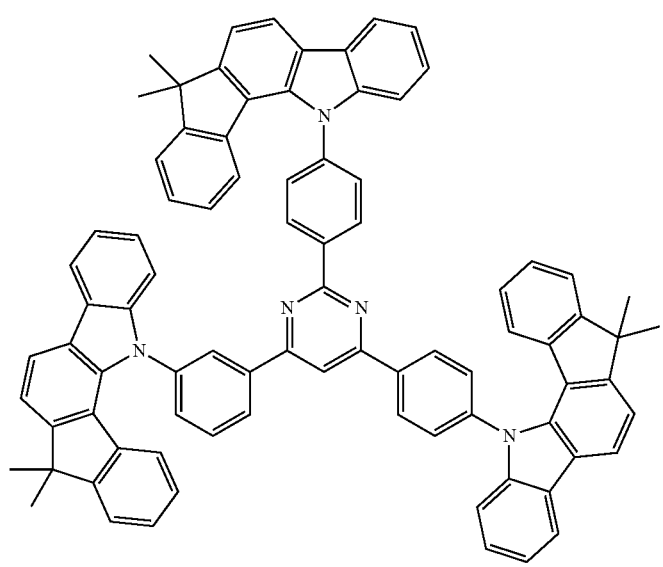

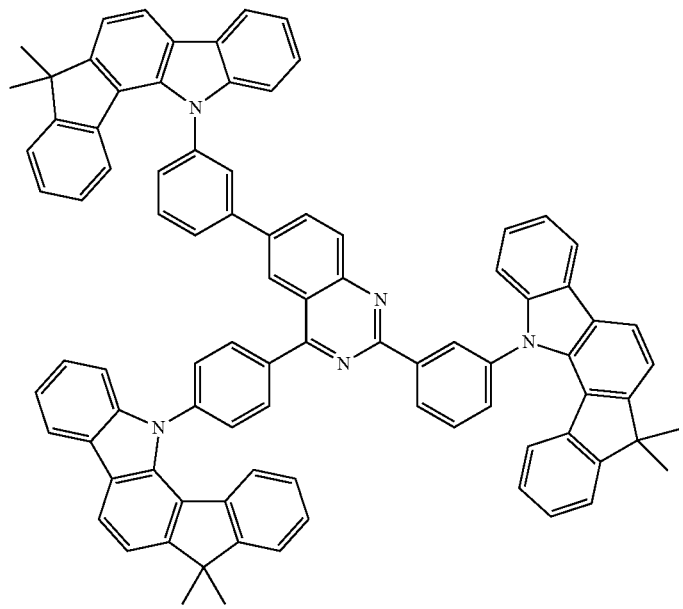
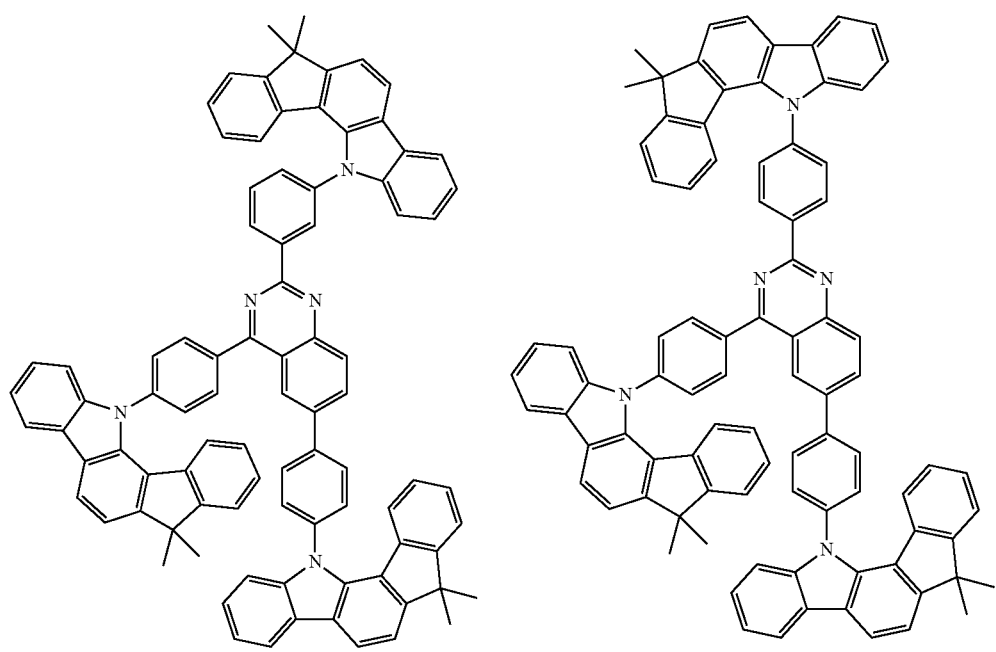

-continued
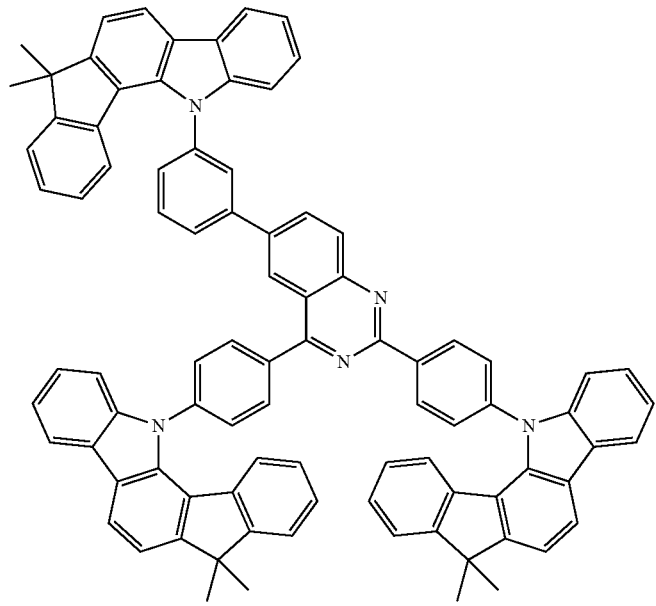
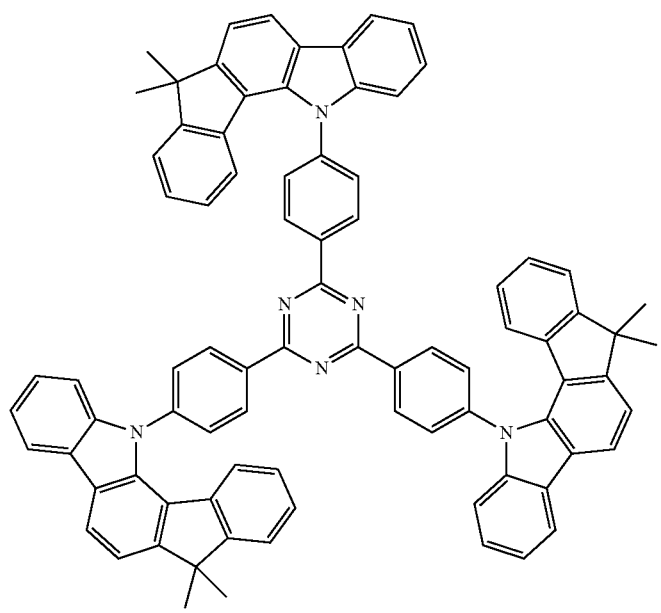

-continued
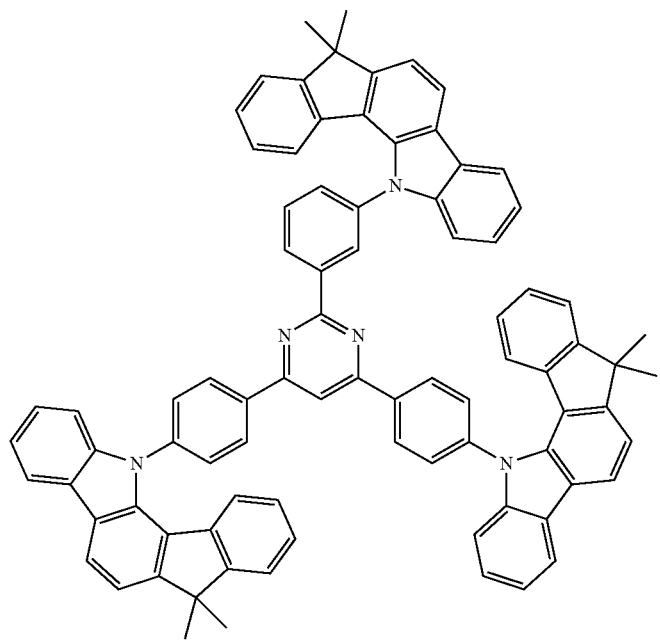
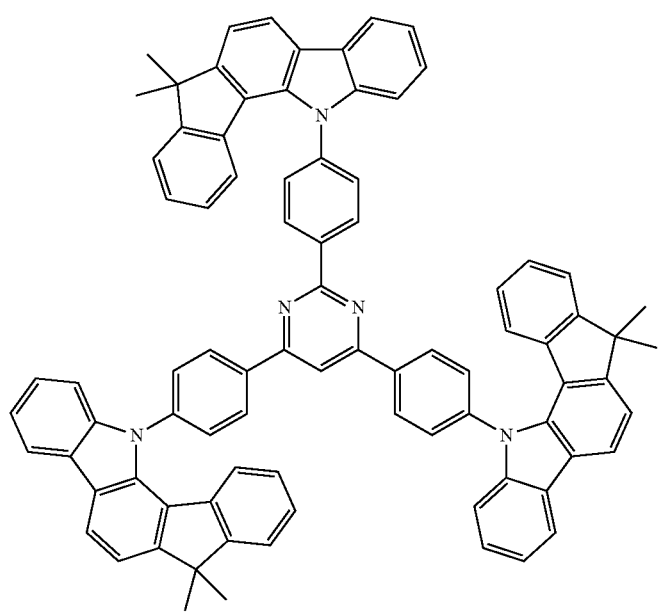

-continued
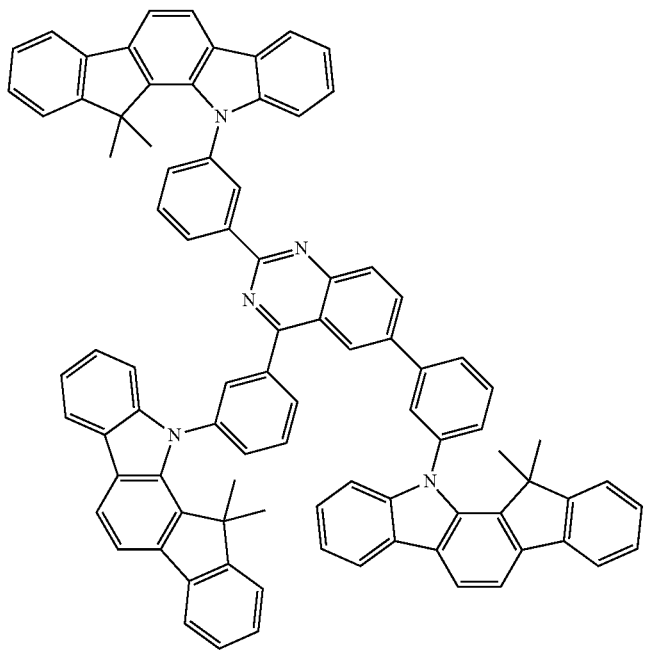
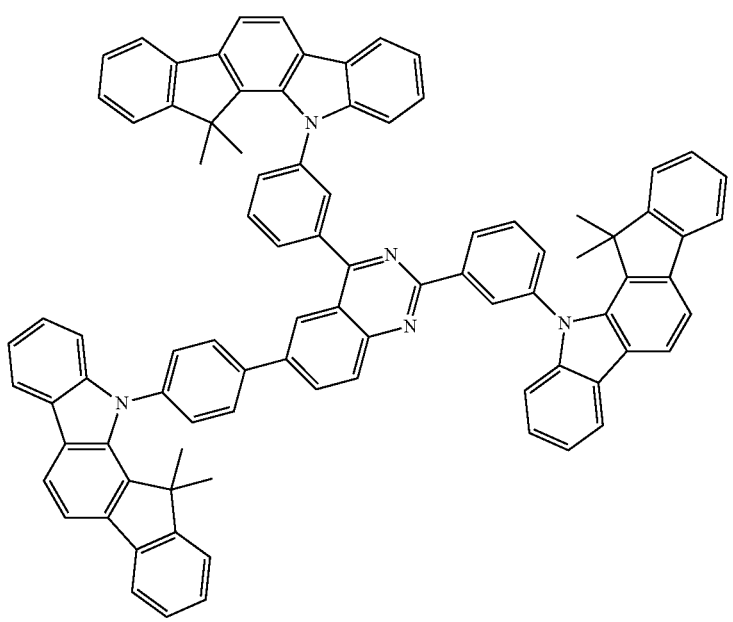

-continued
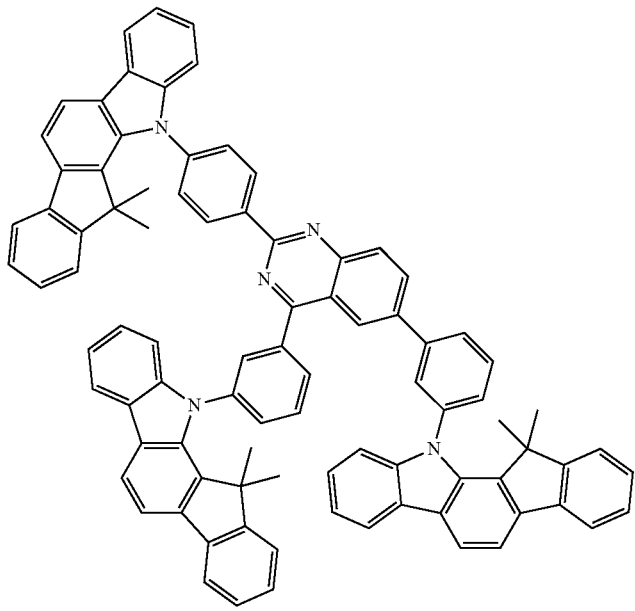
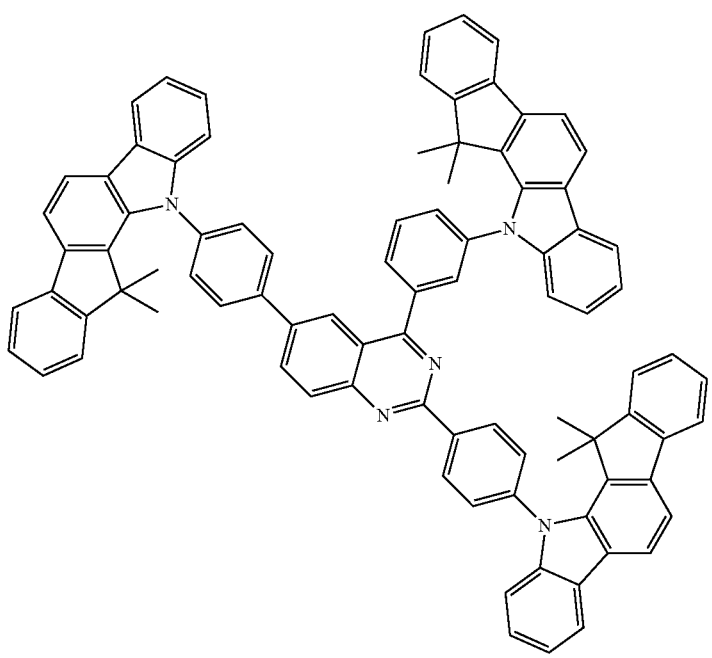

-continued
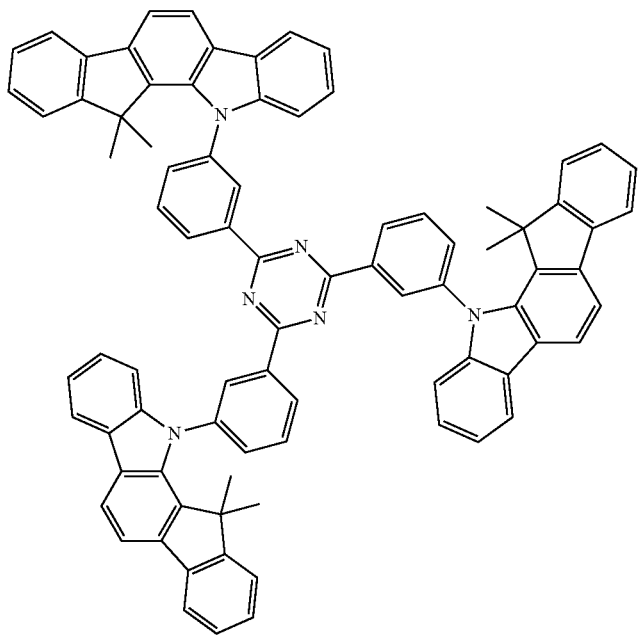
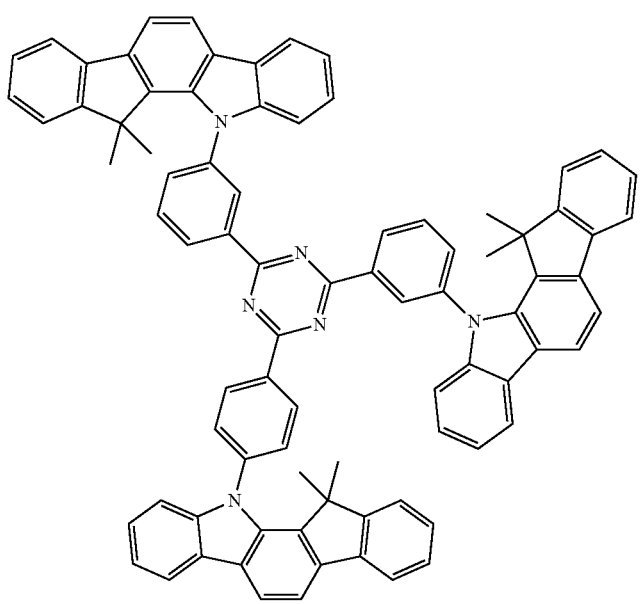

-continued
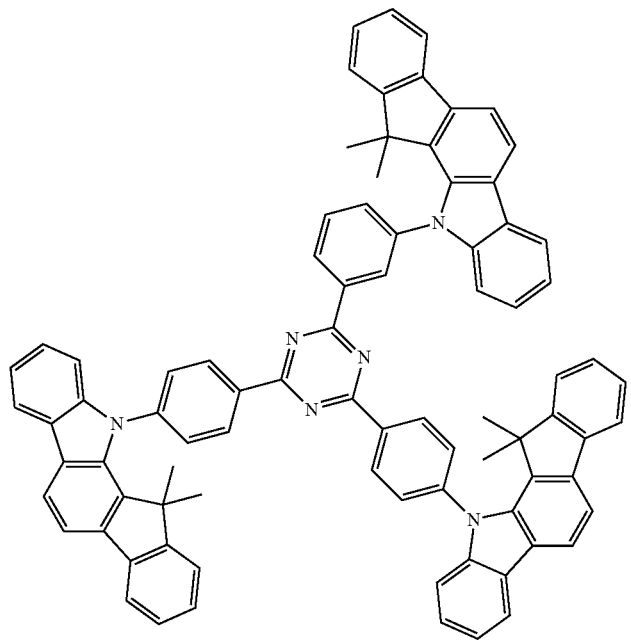
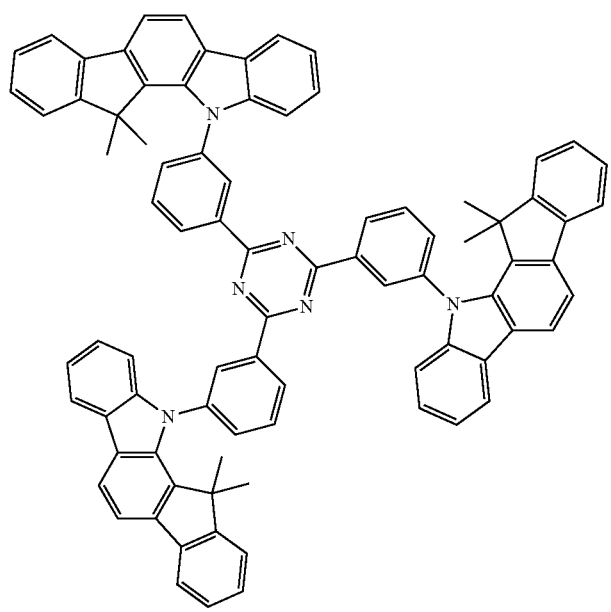

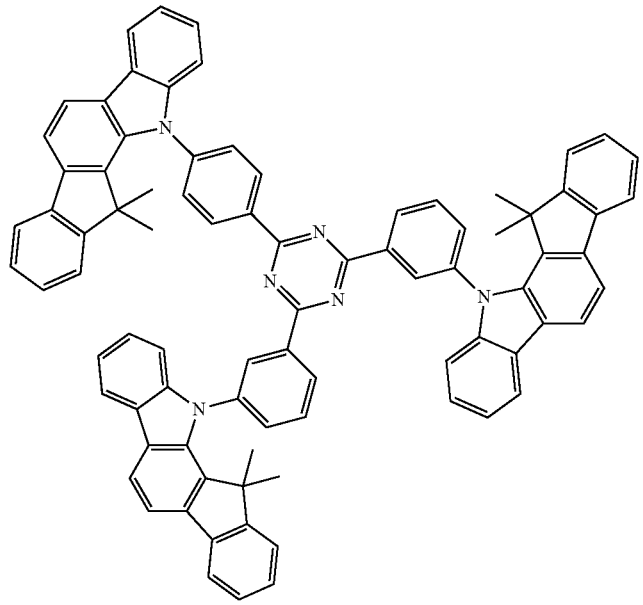
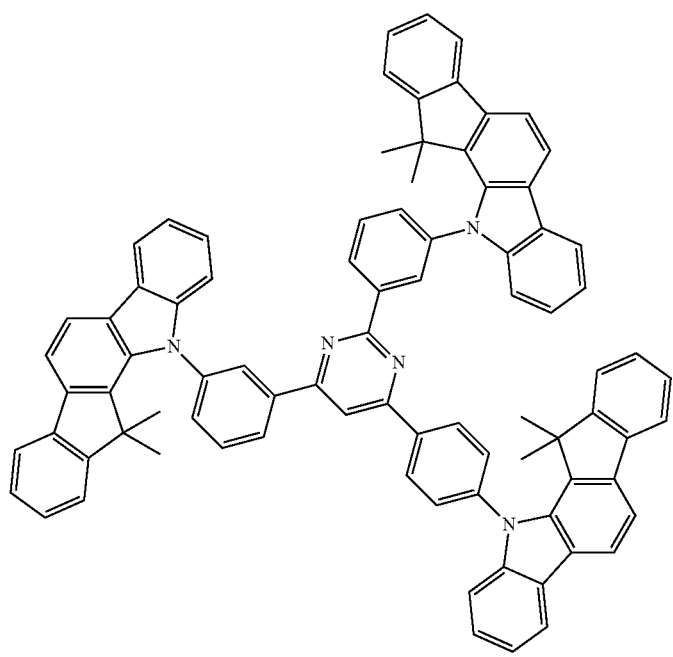

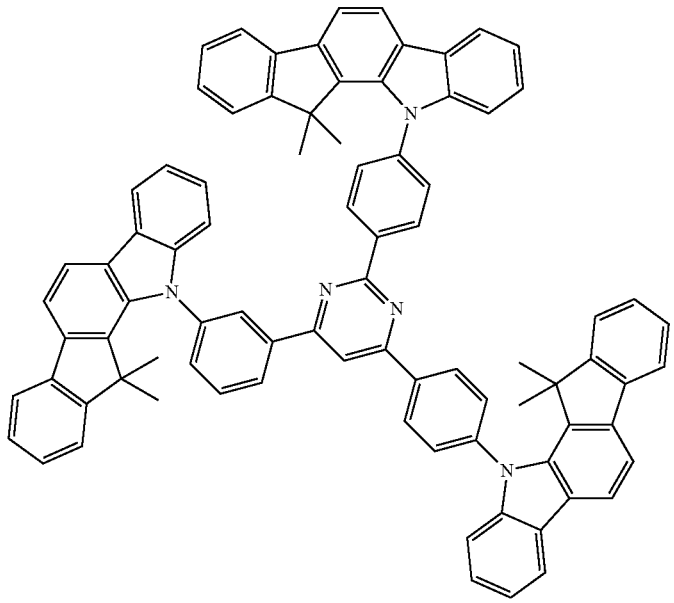
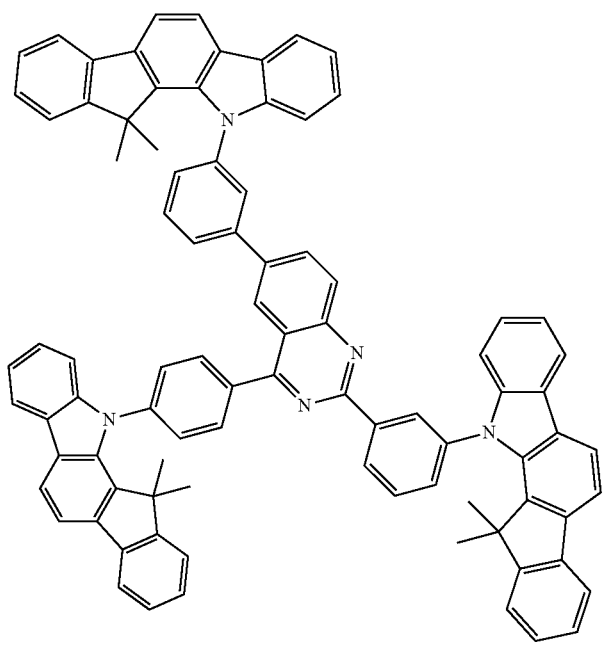

-continued
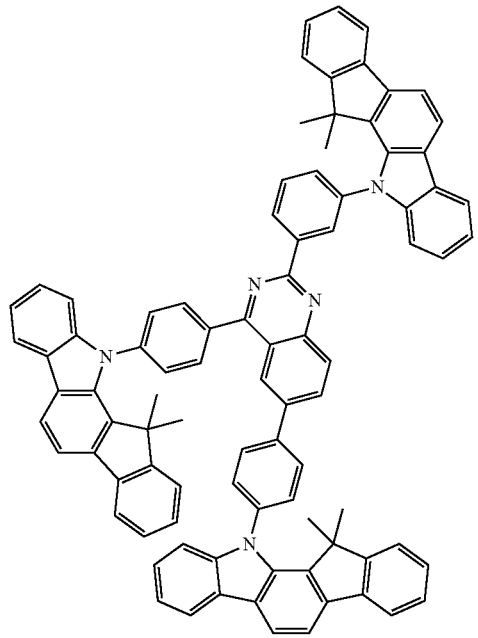
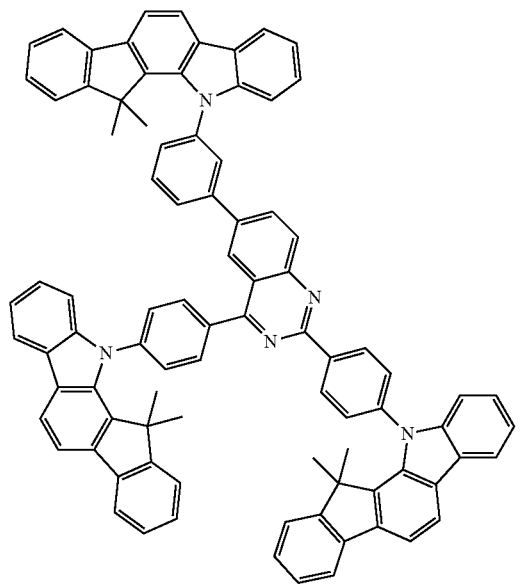
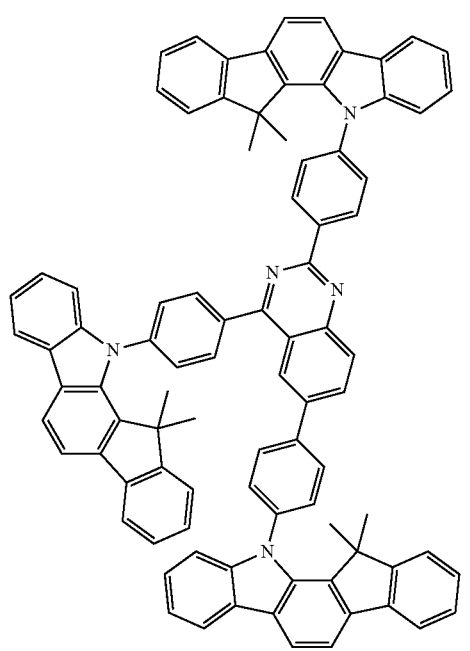
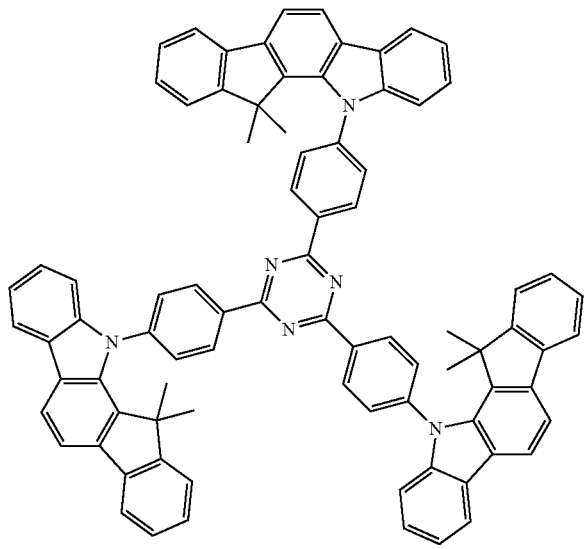

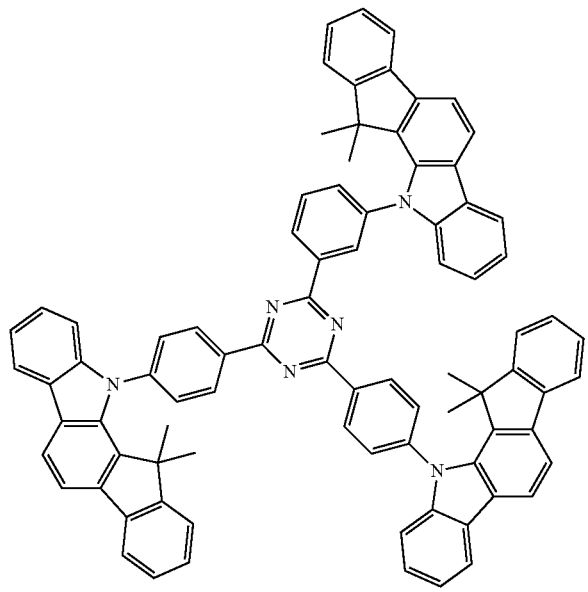
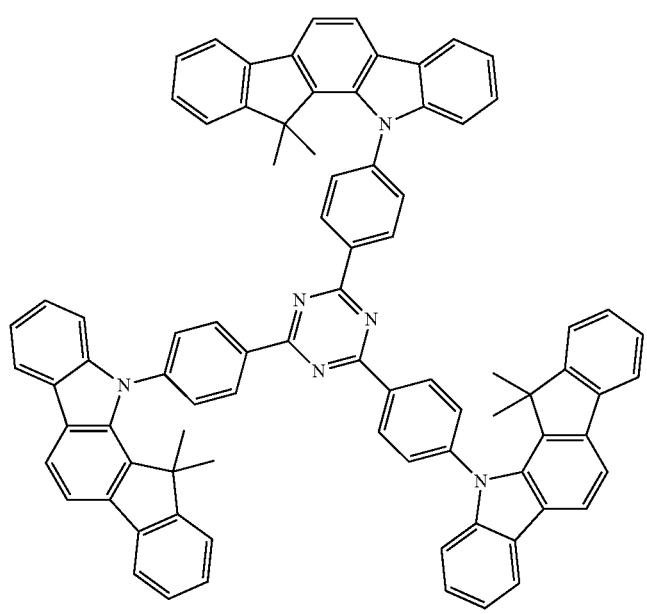

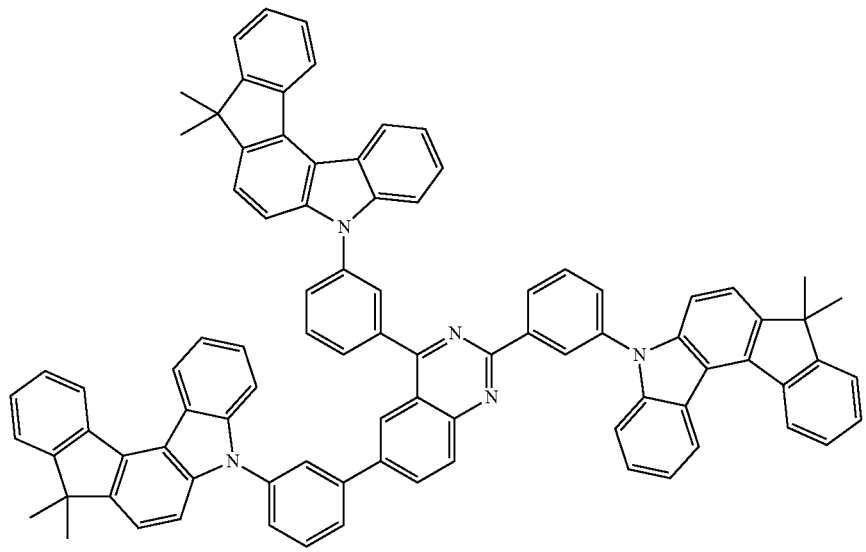
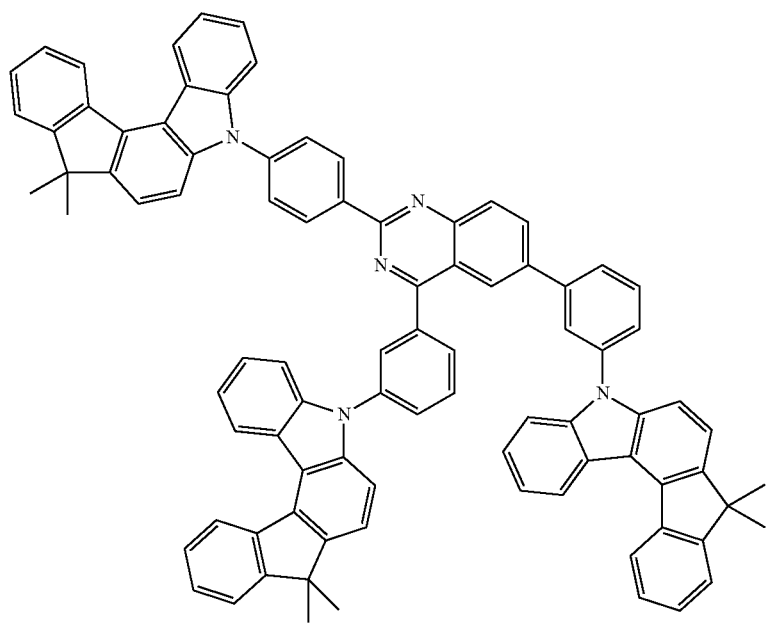

-continued
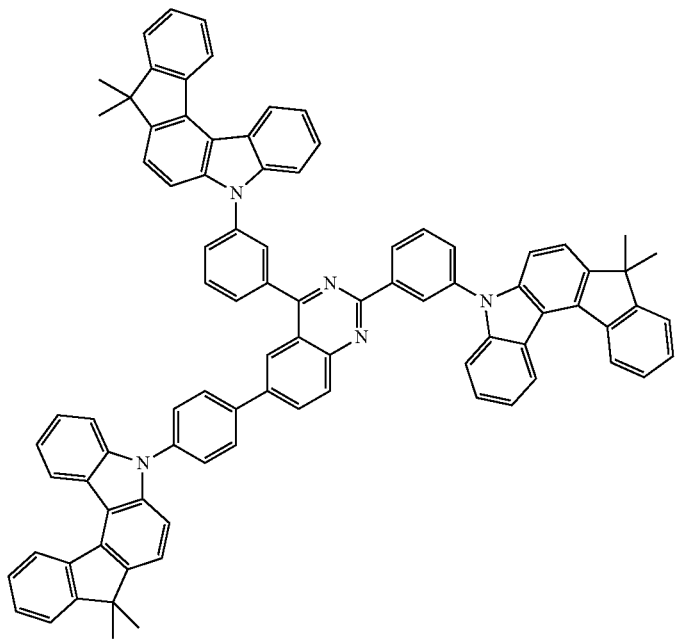
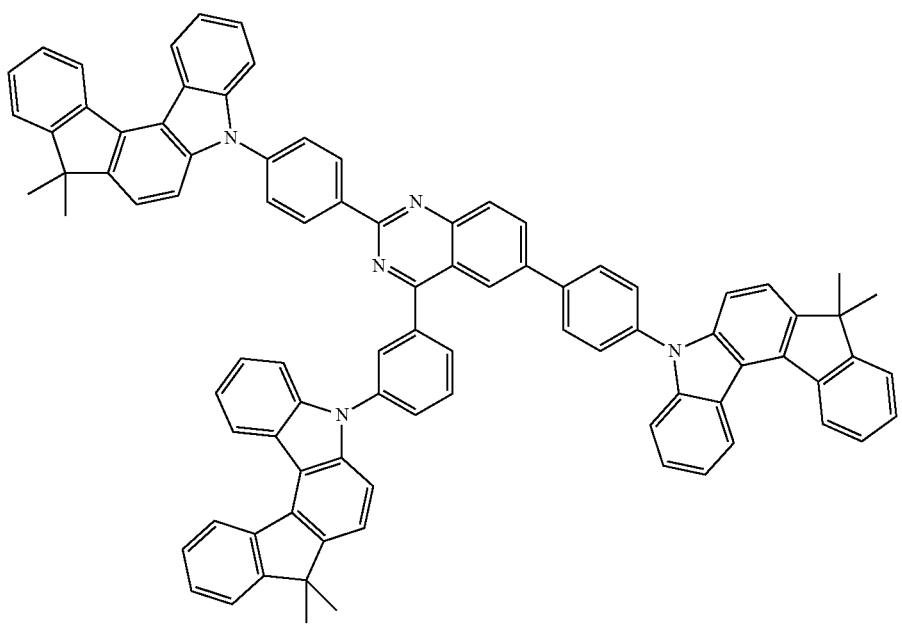

-continued
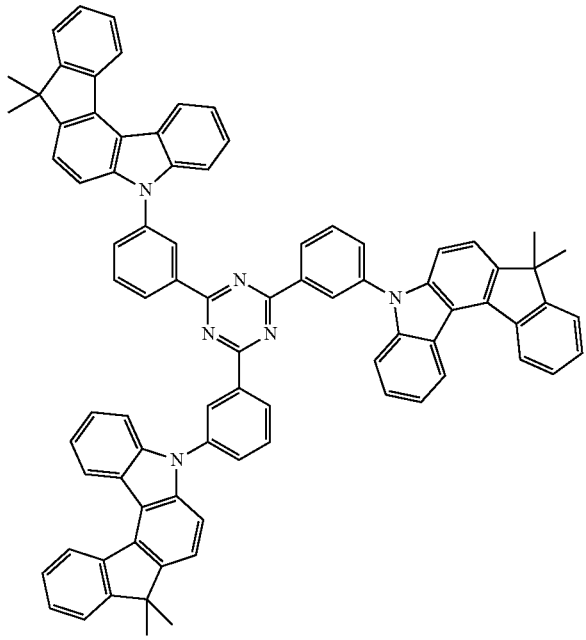
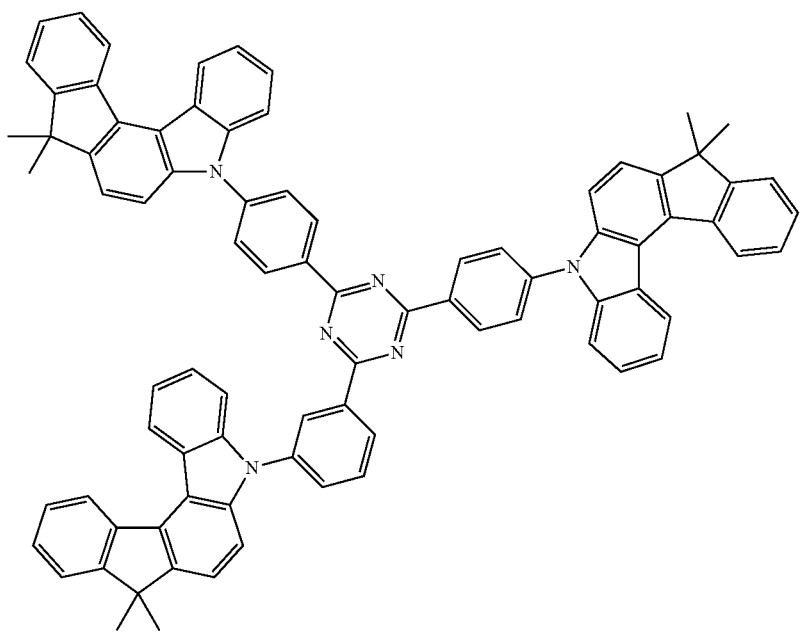

-continued
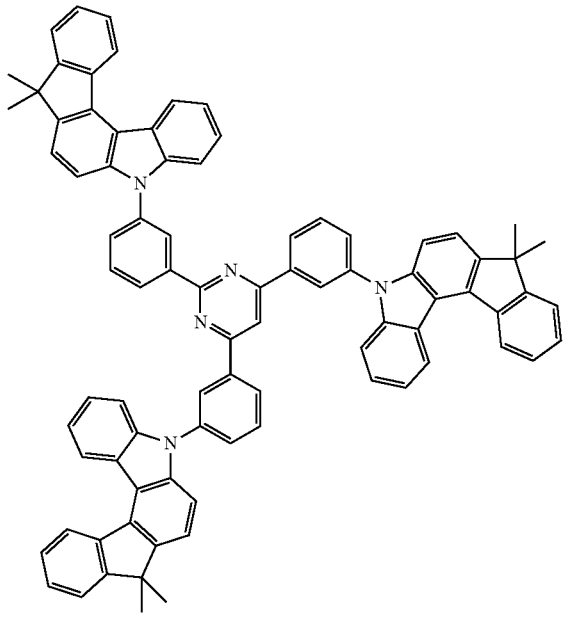
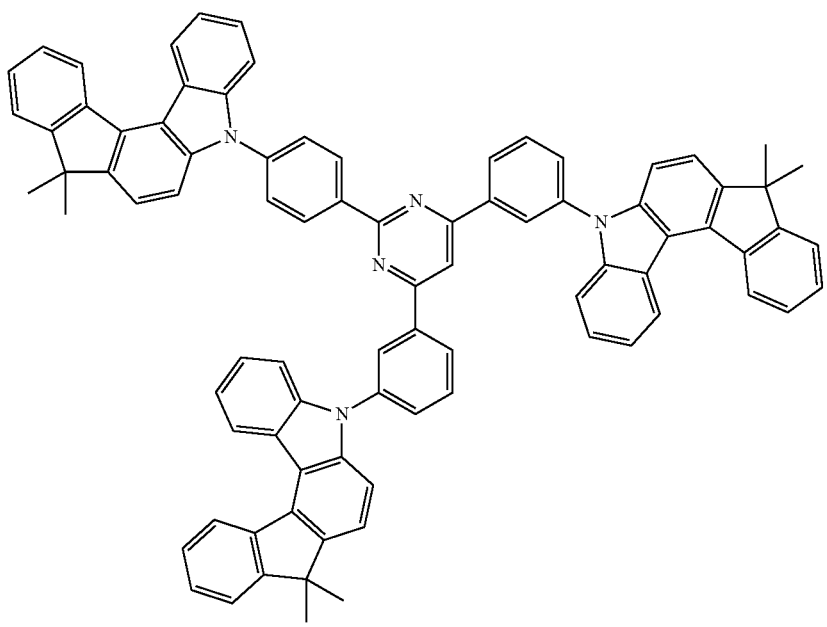

-continued
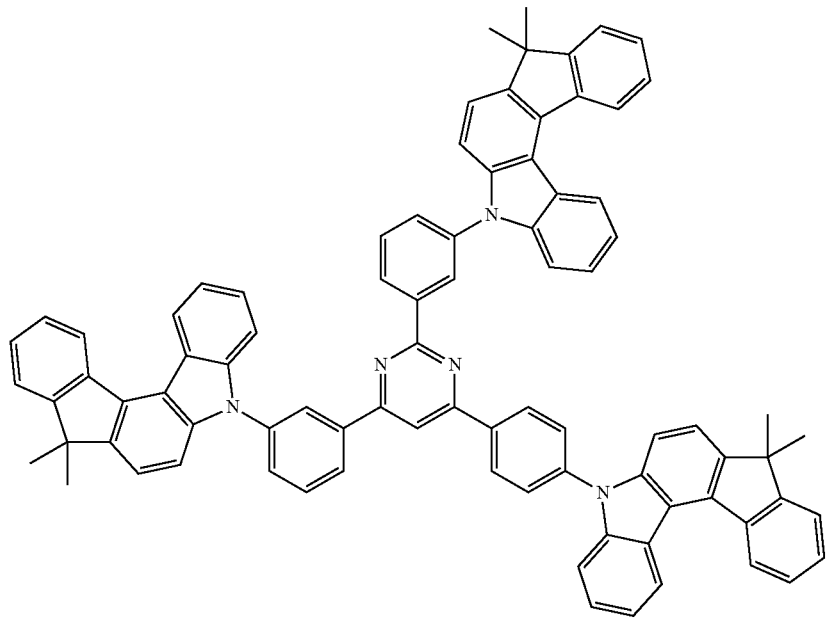
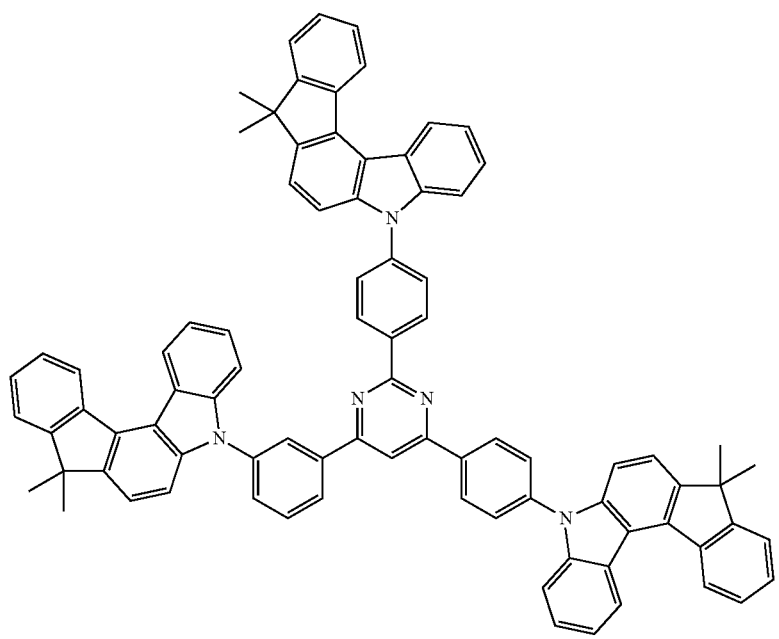

-continued
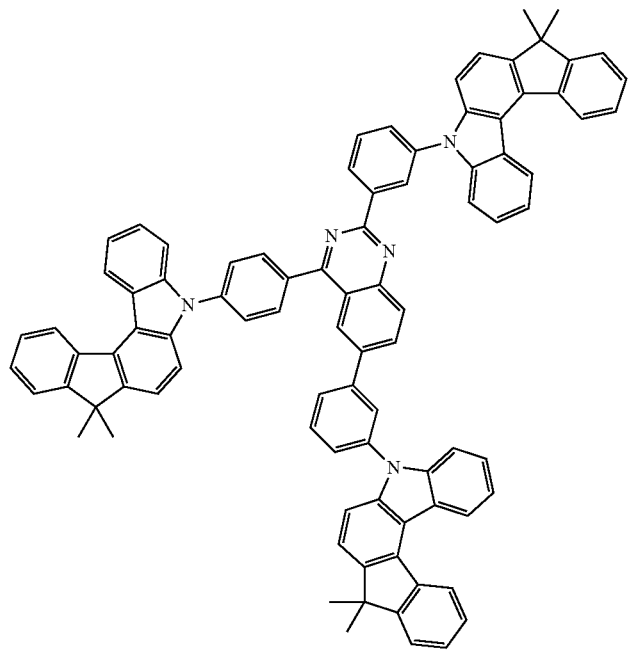
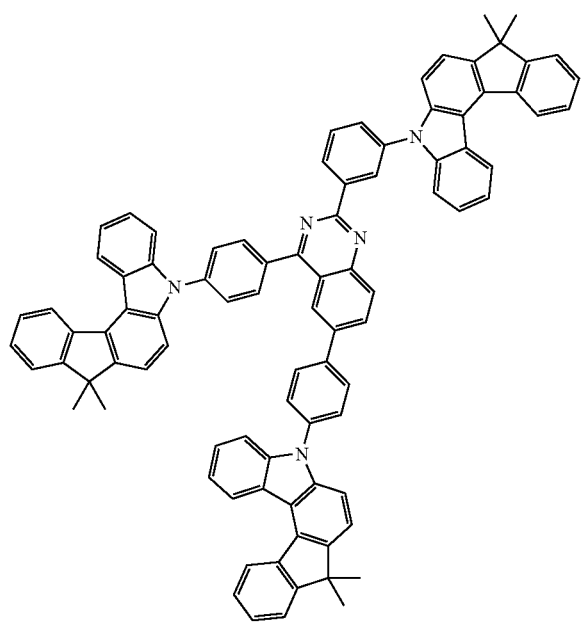

-continued
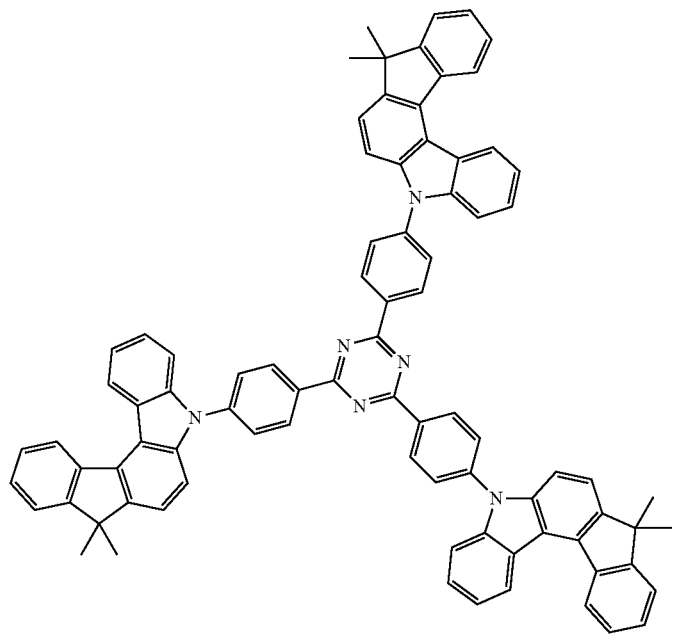
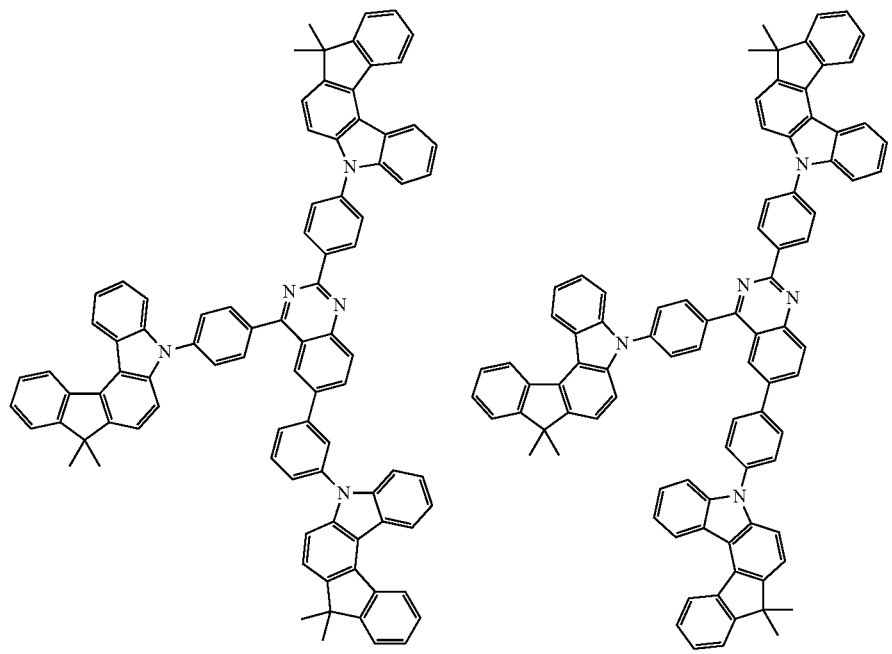

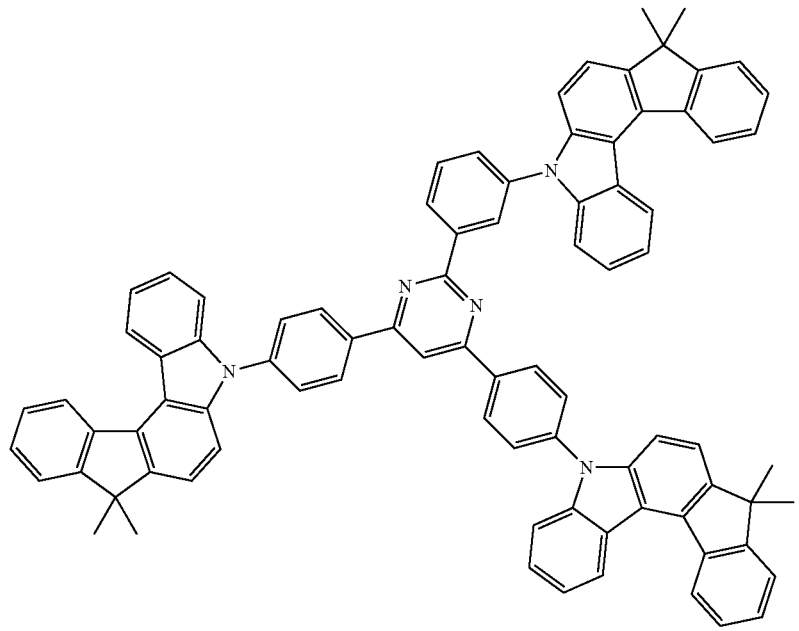
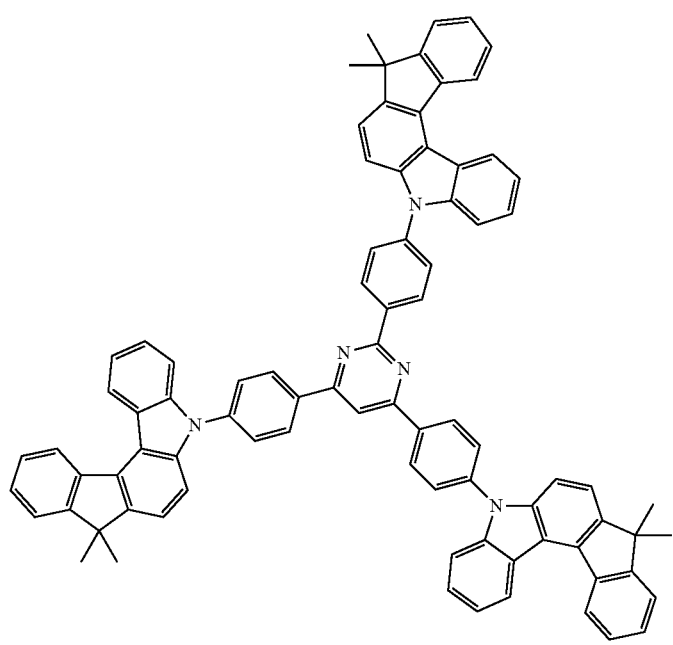

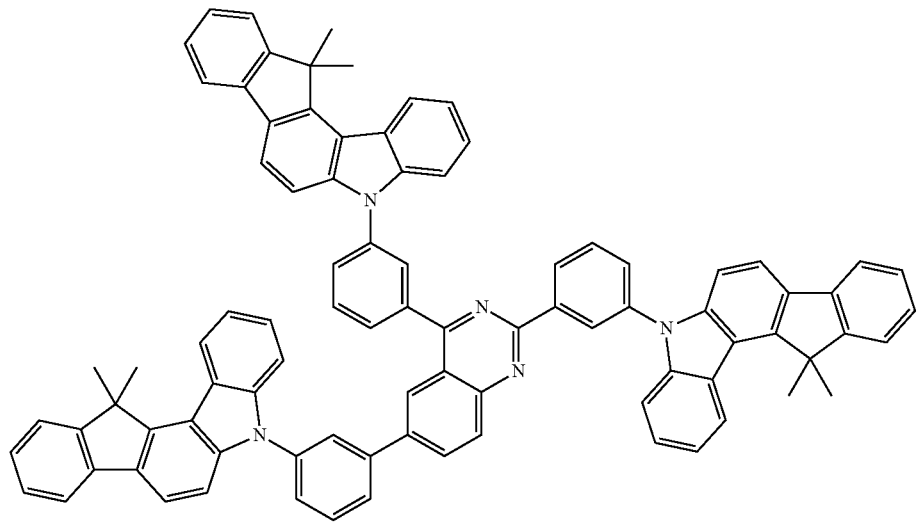
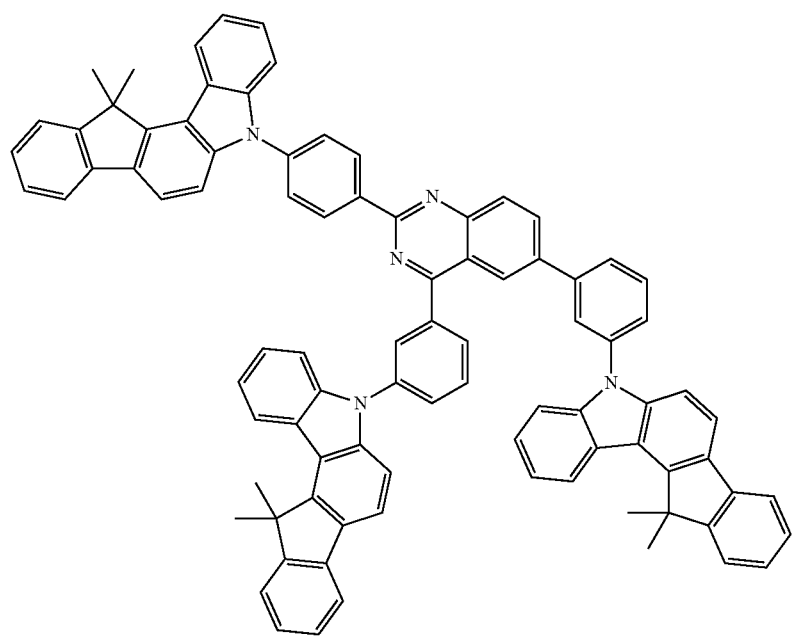

-continued
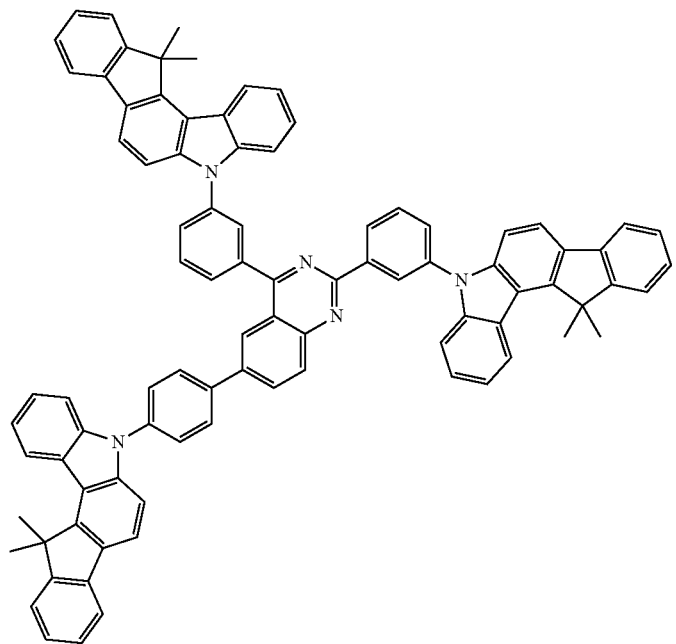
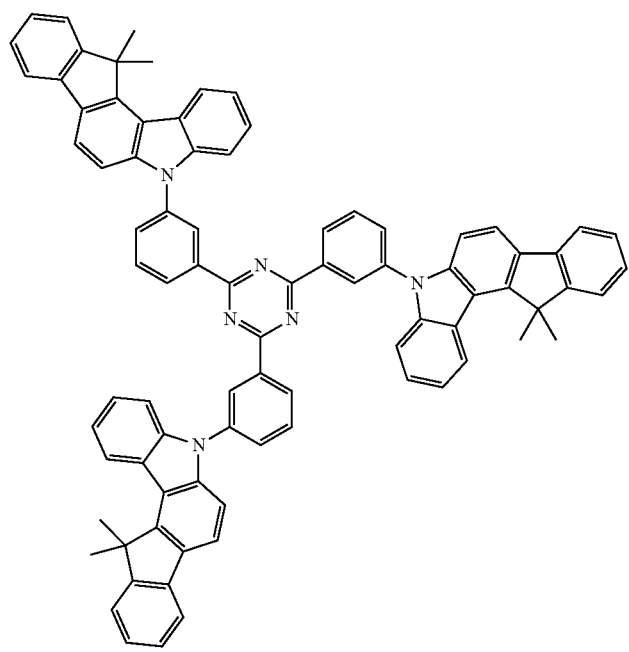

-continued
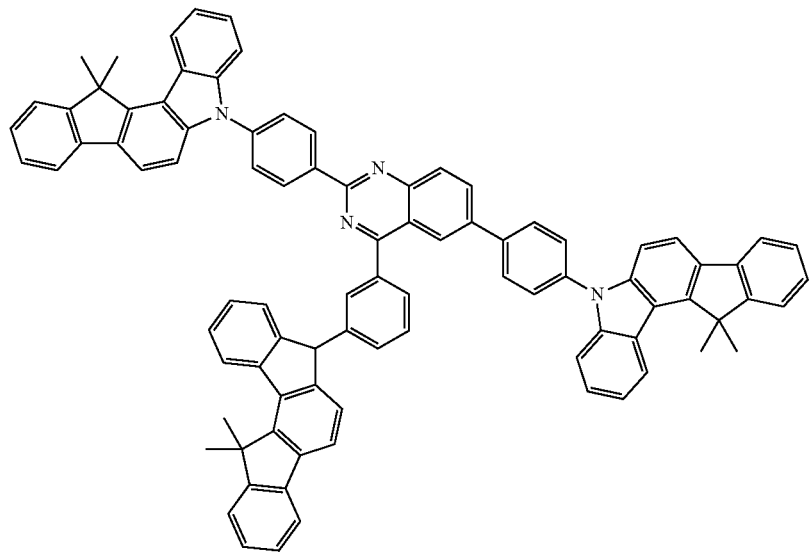
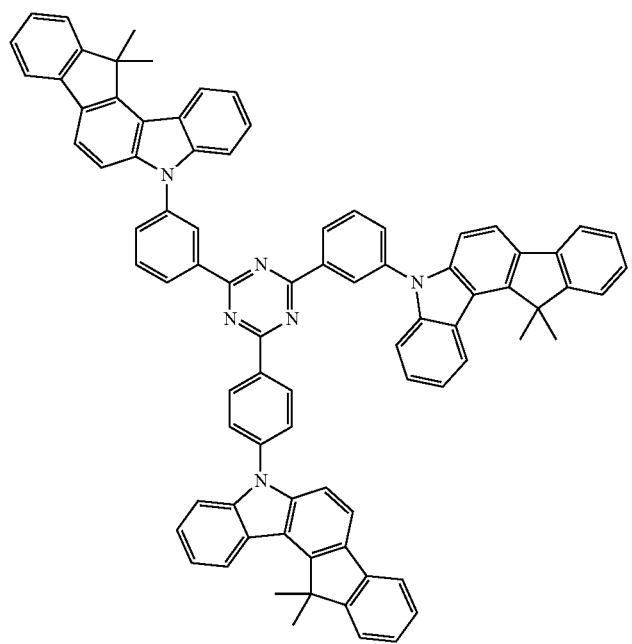

-continued
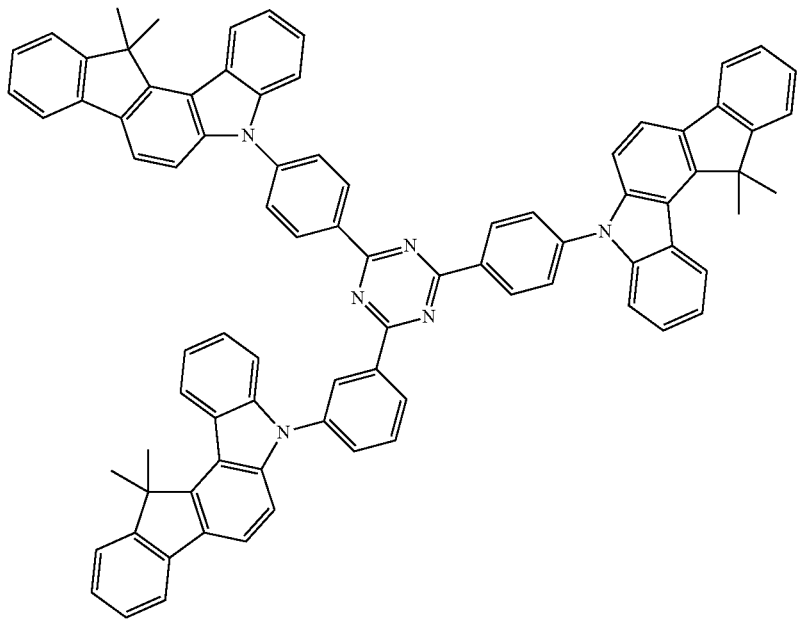
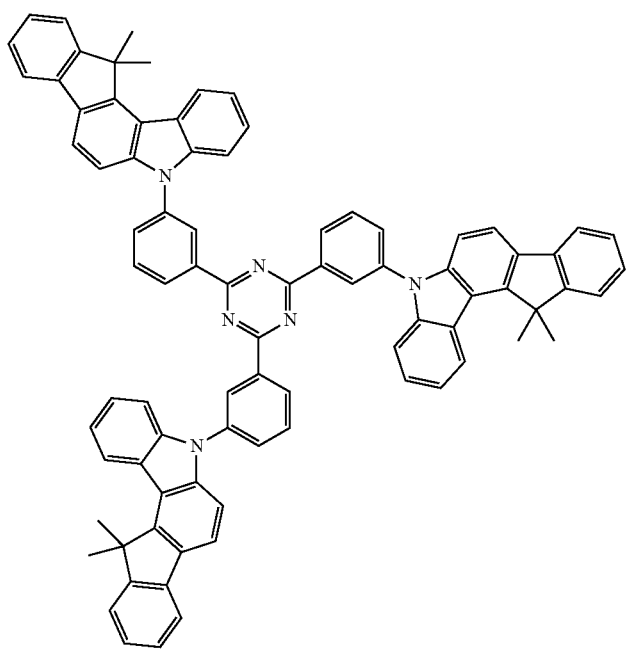

-continued
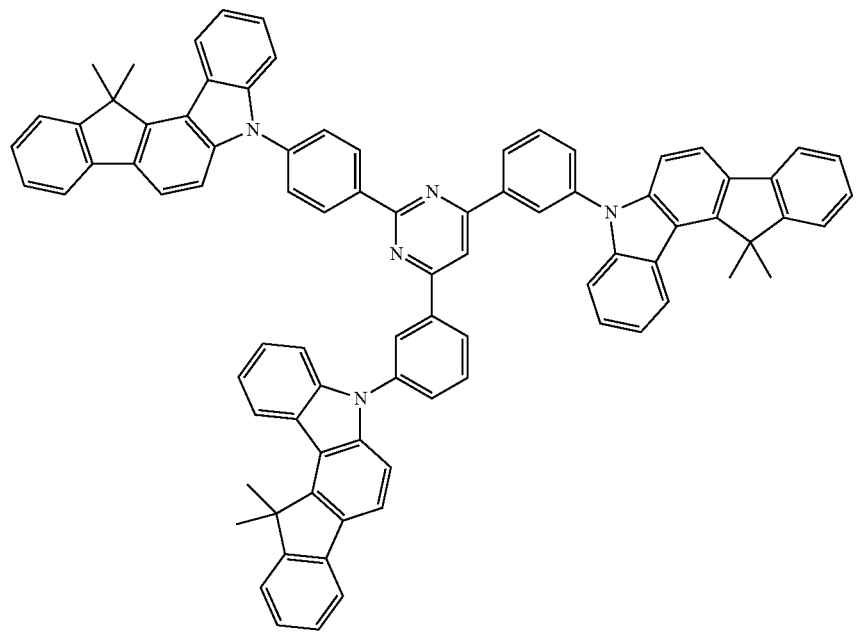
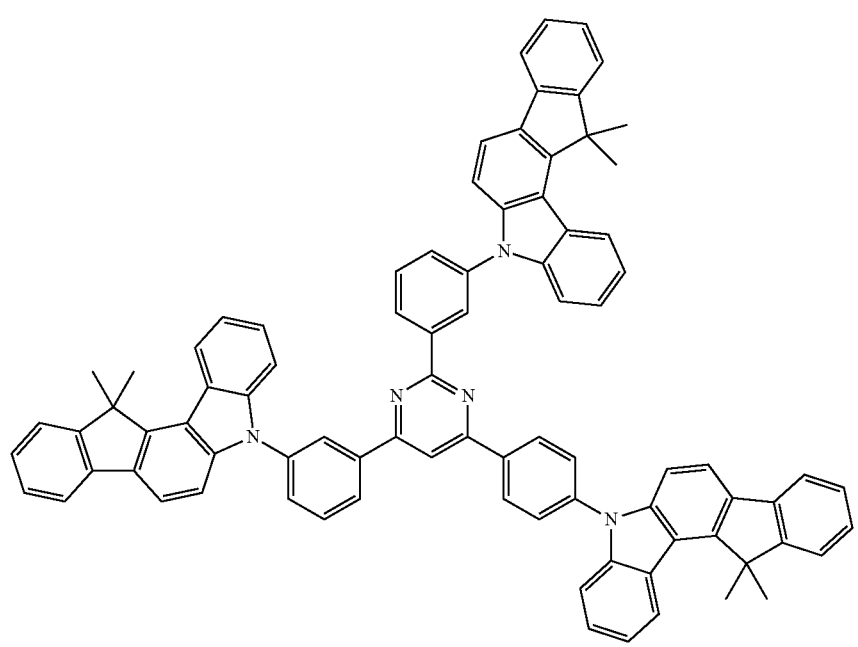

-continued
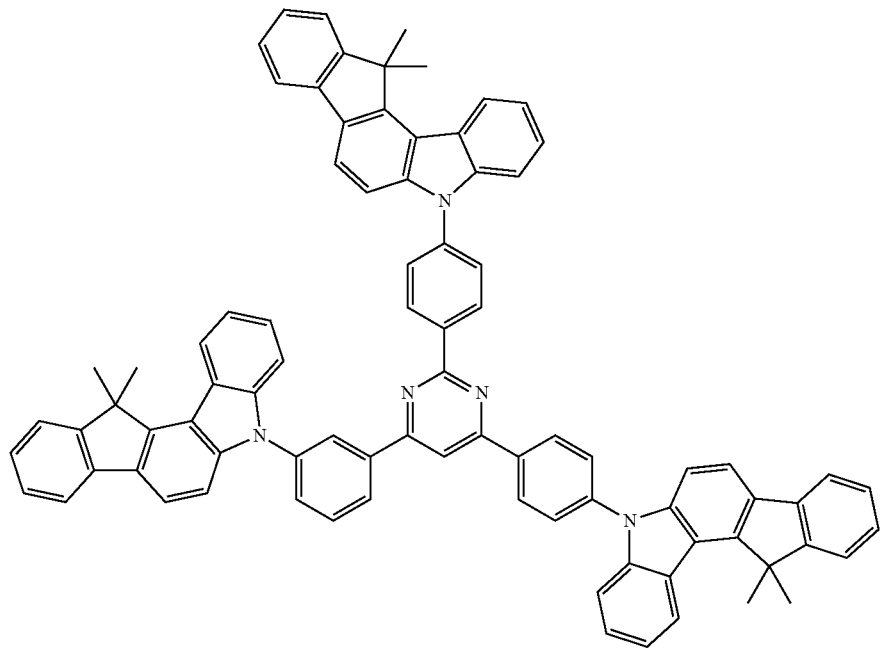
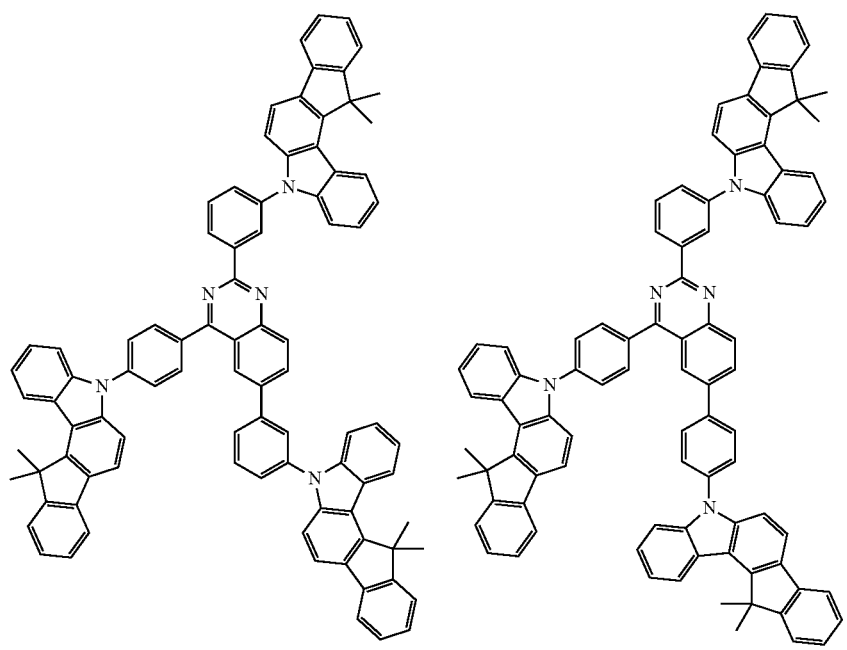

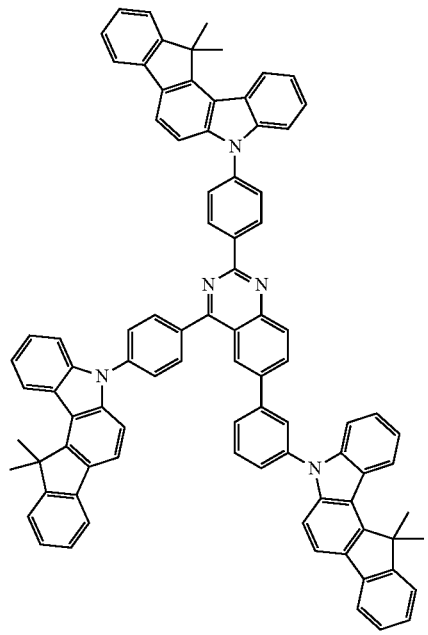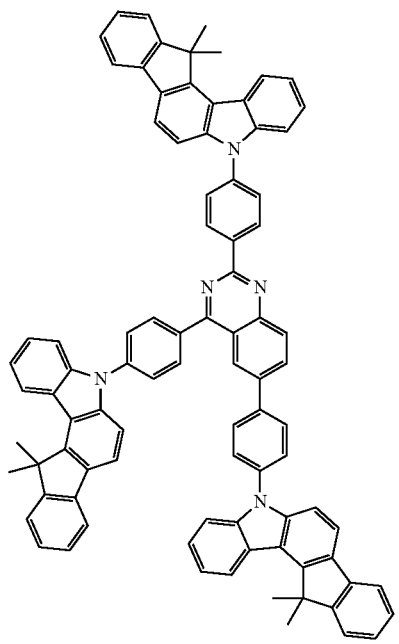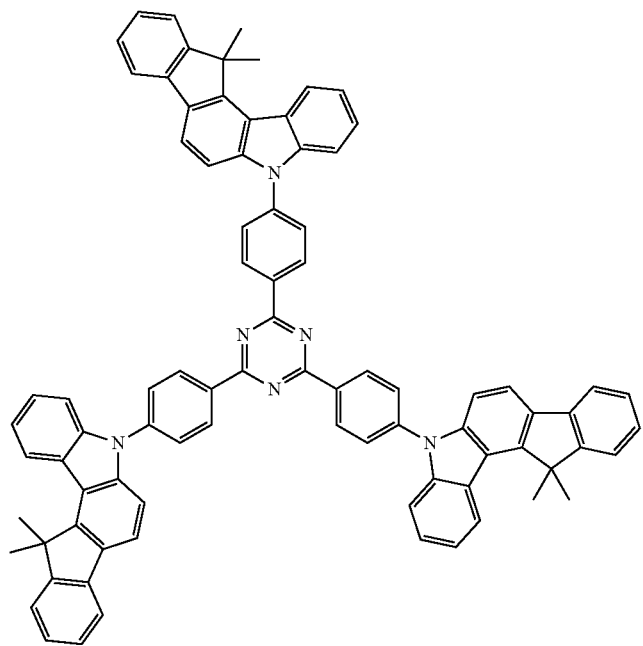

-continued
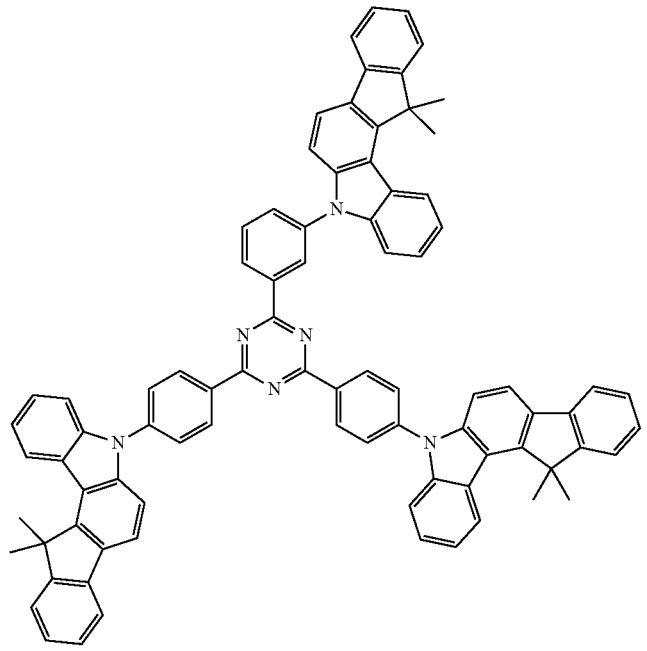
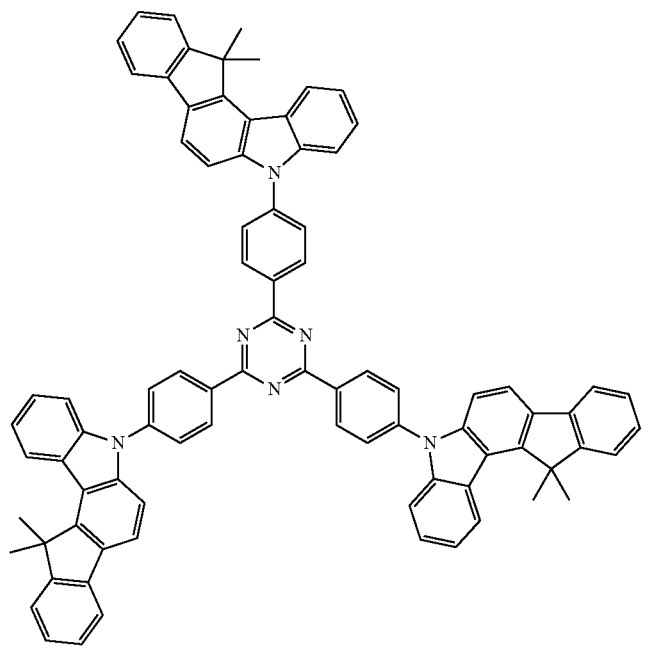

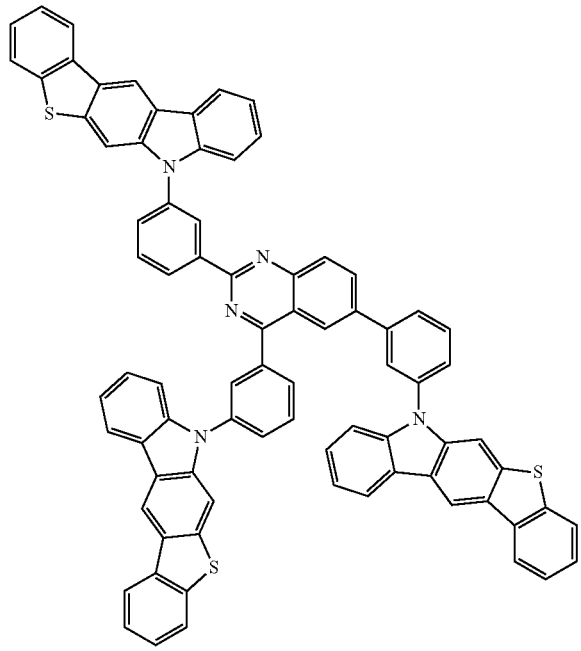
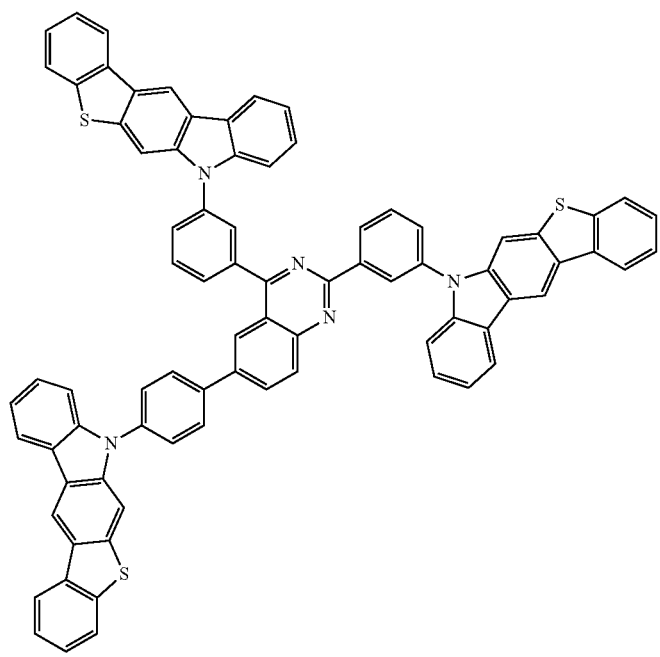

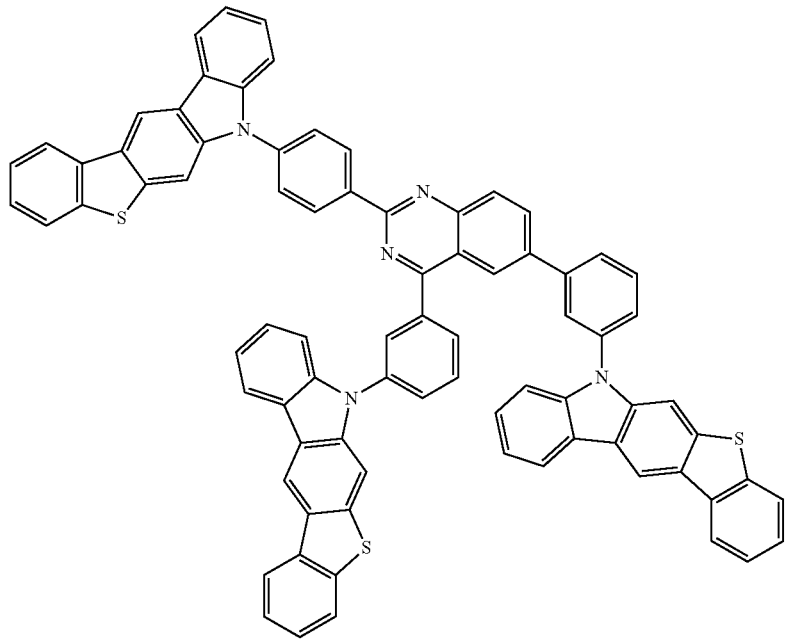
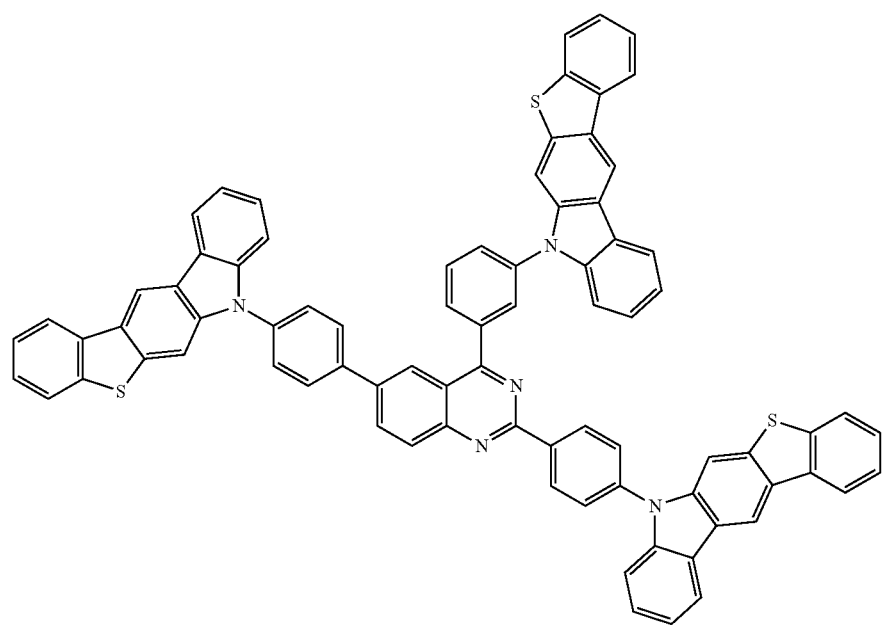

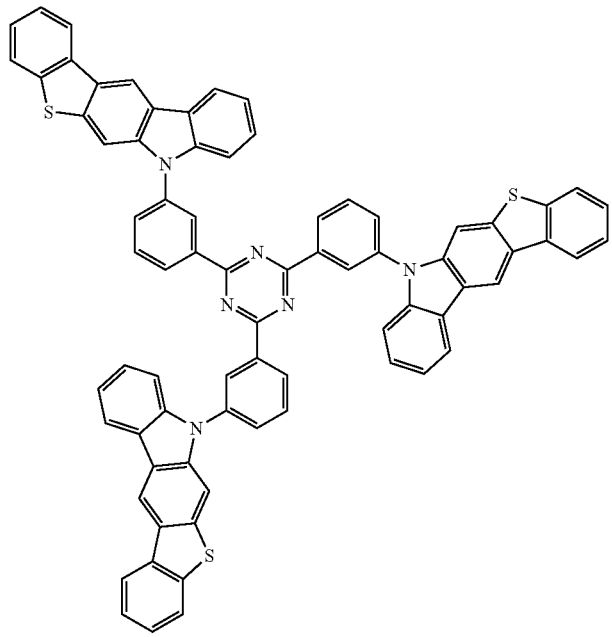
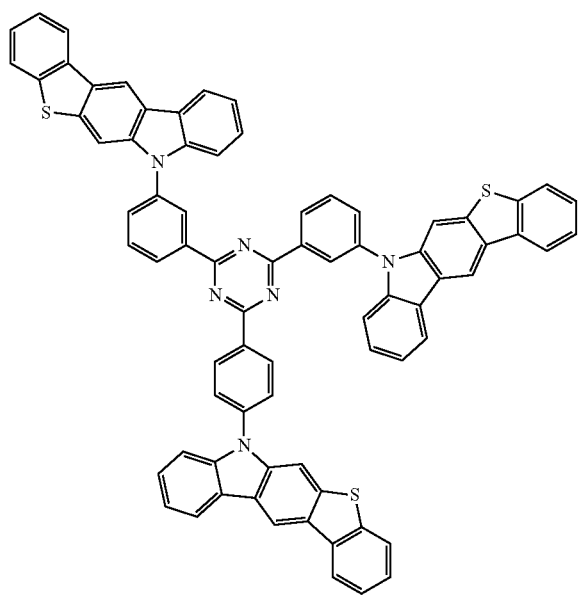

-continued
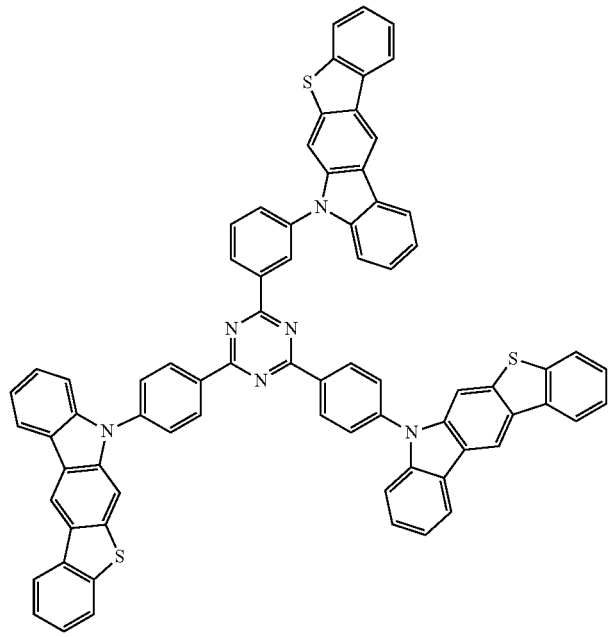
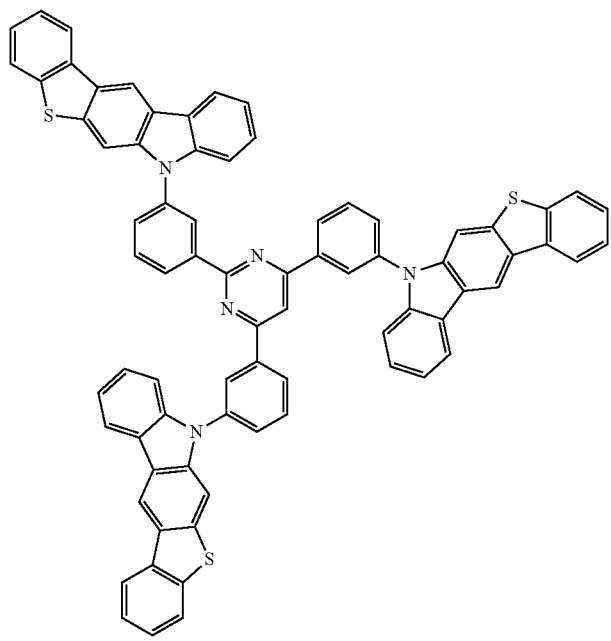

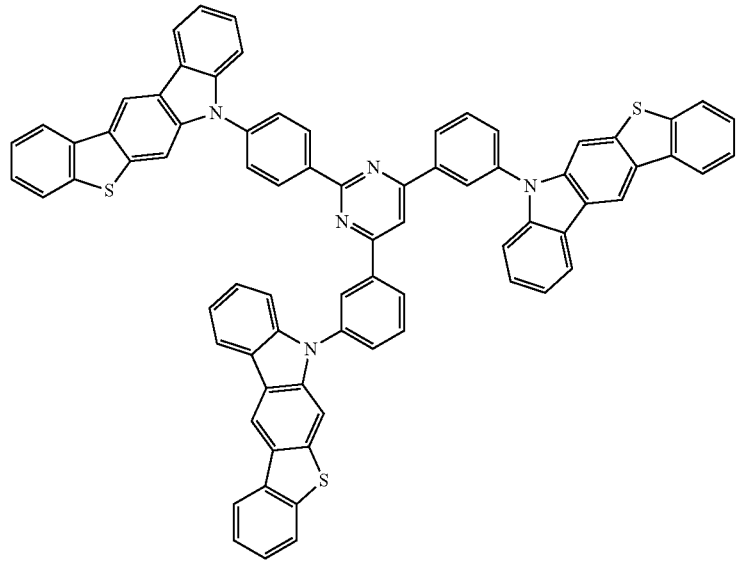
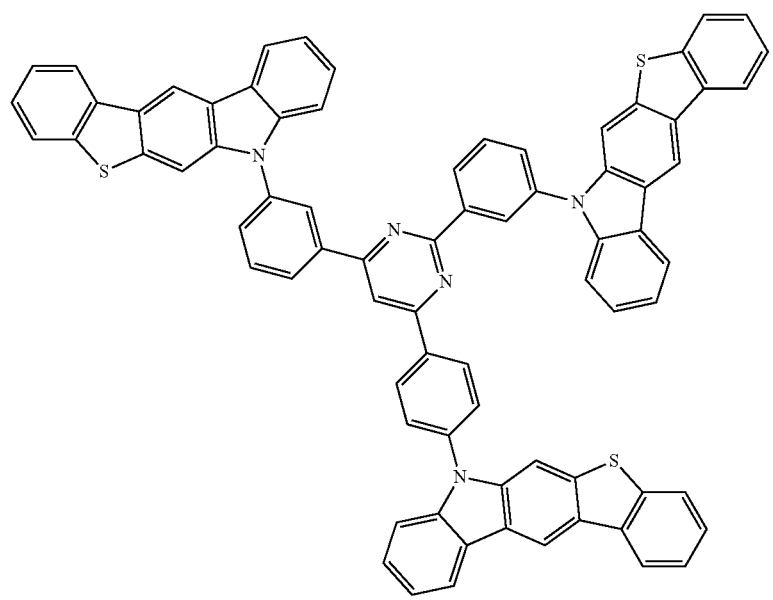

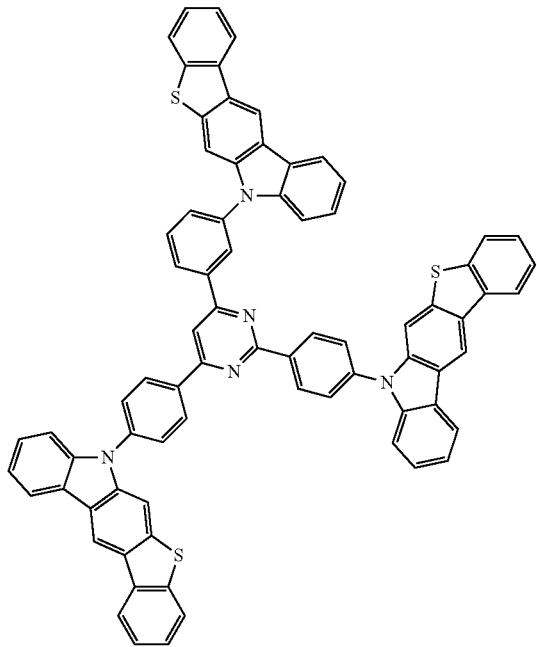
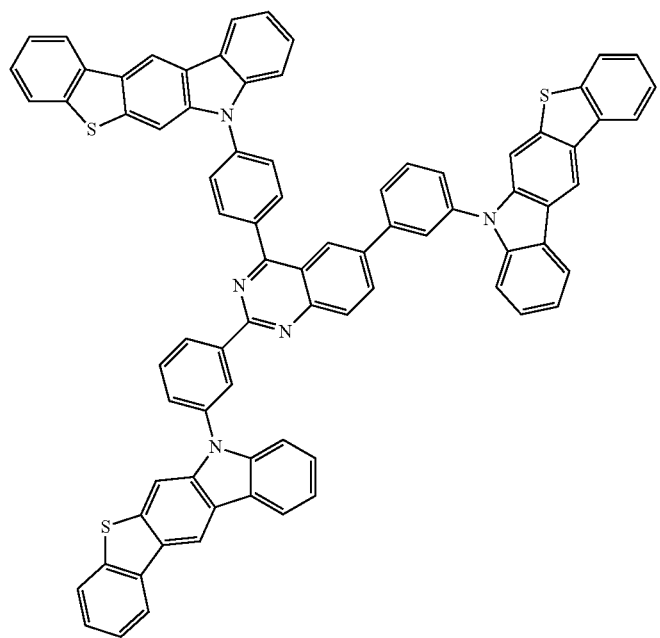

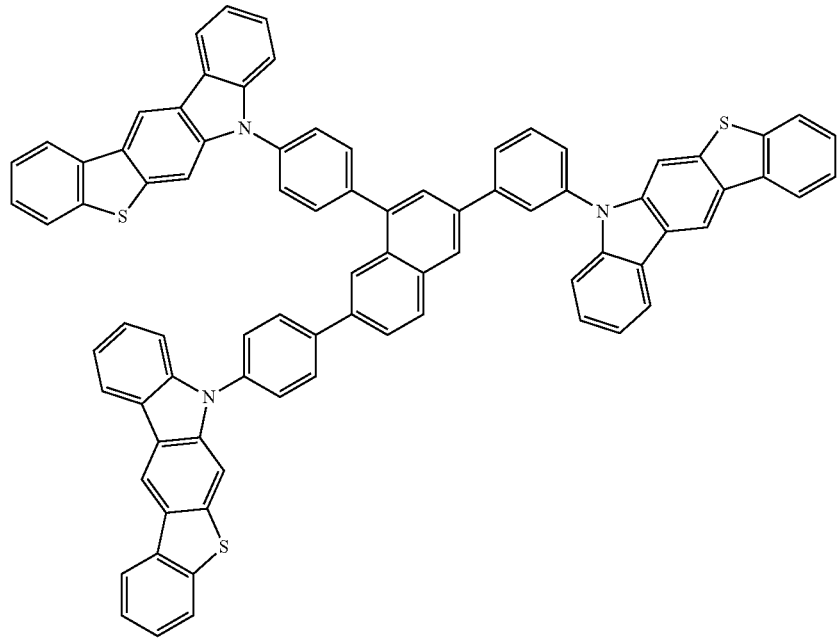
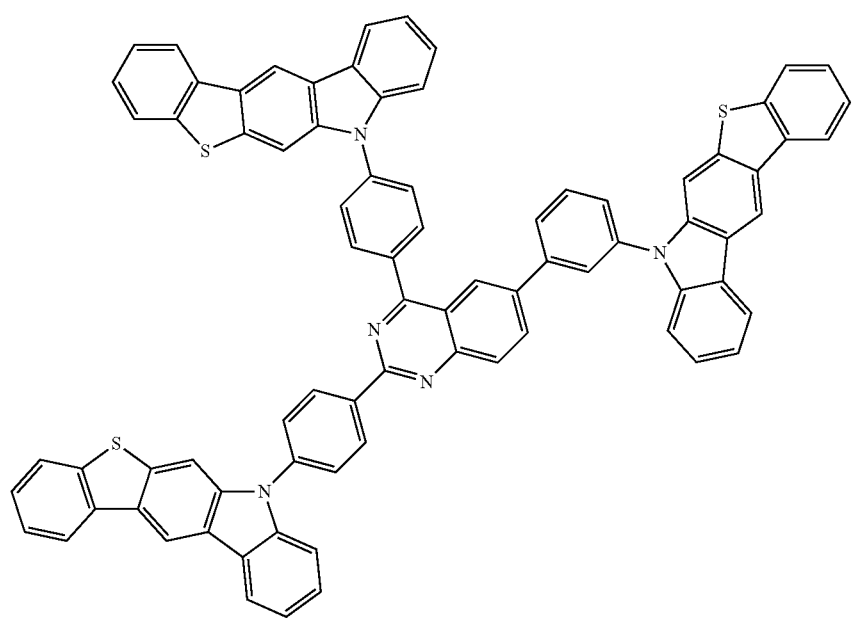

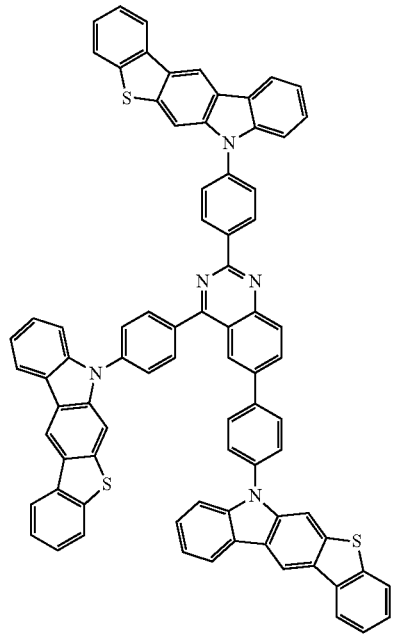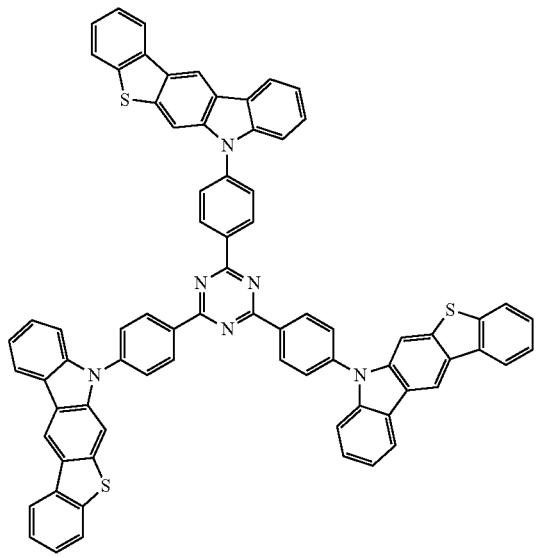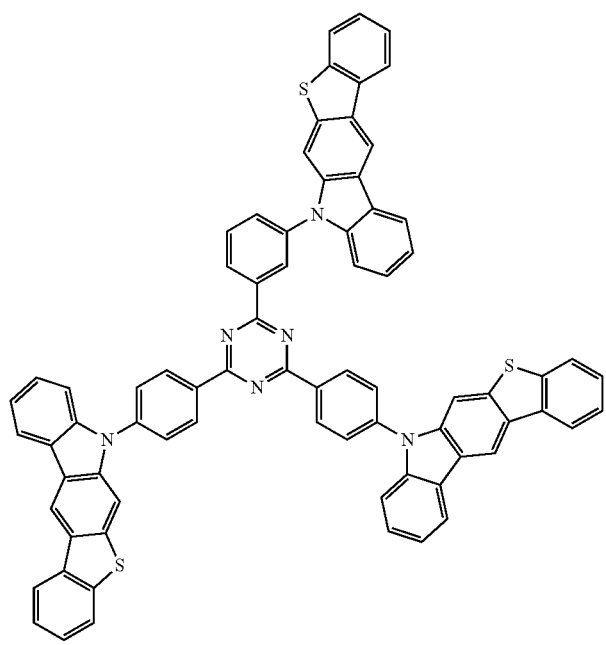

-continued
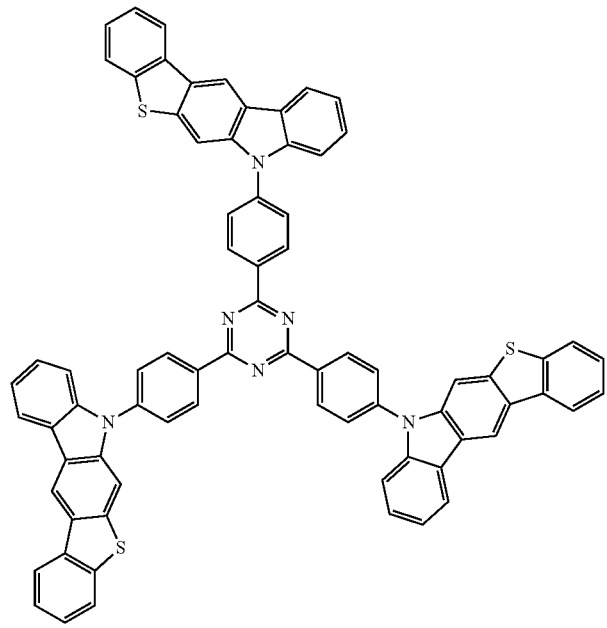
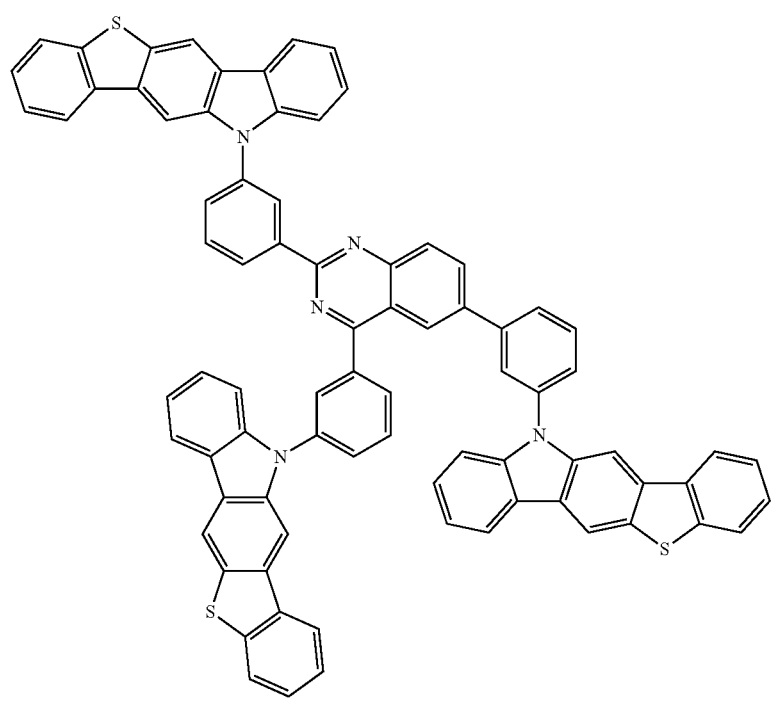

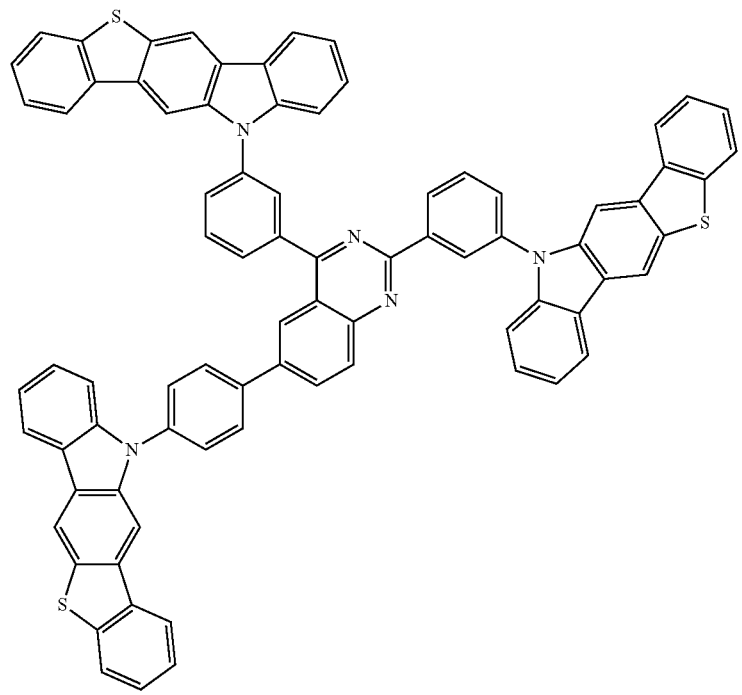
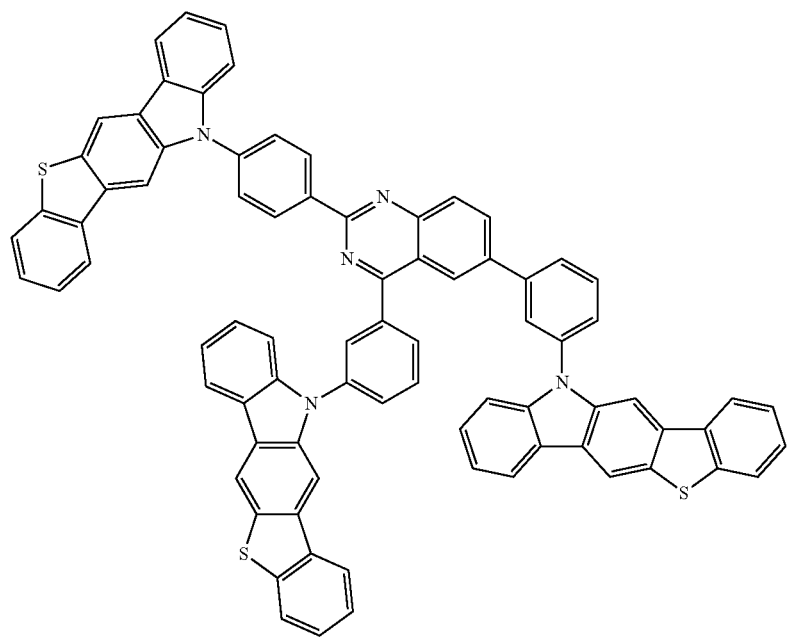

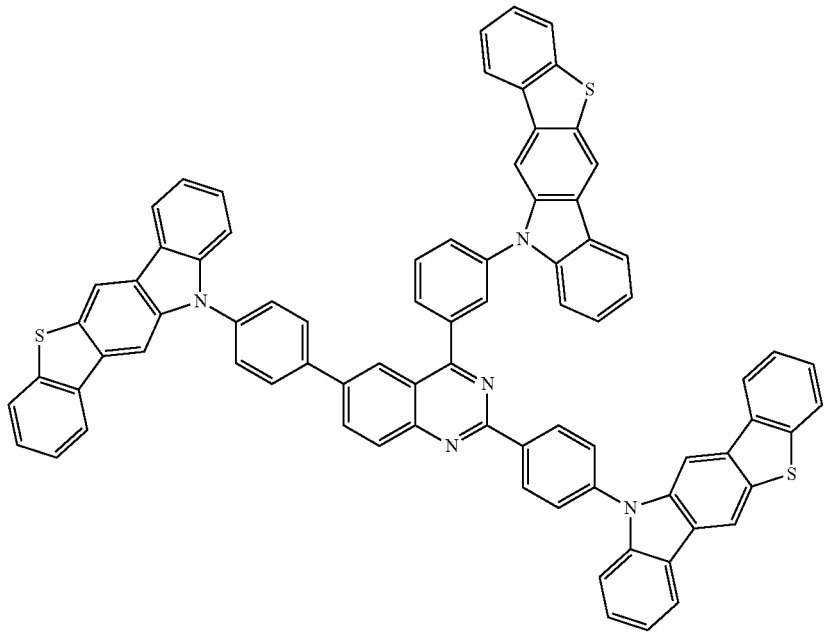
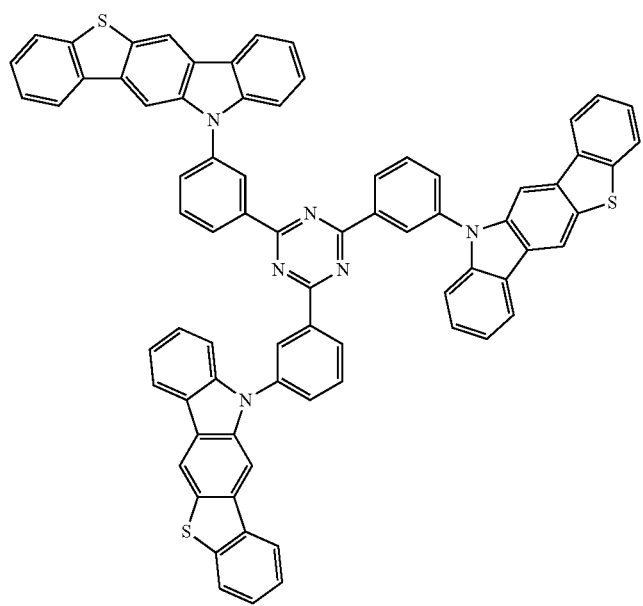

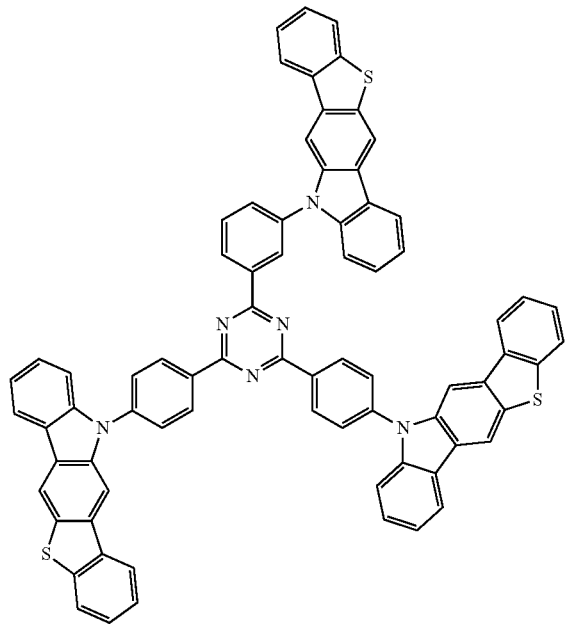
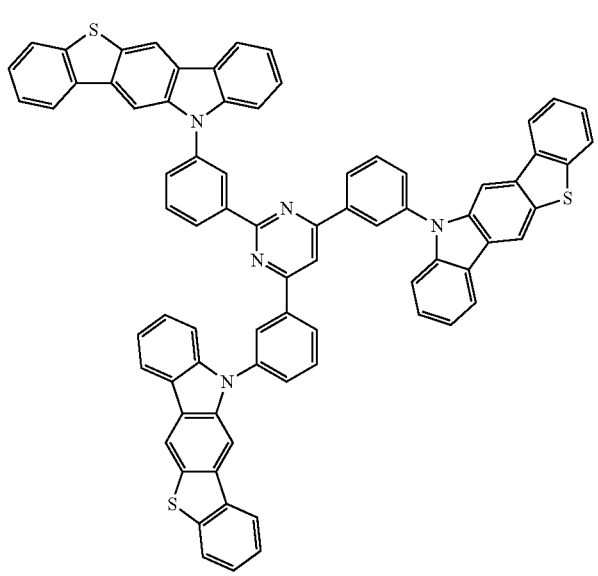
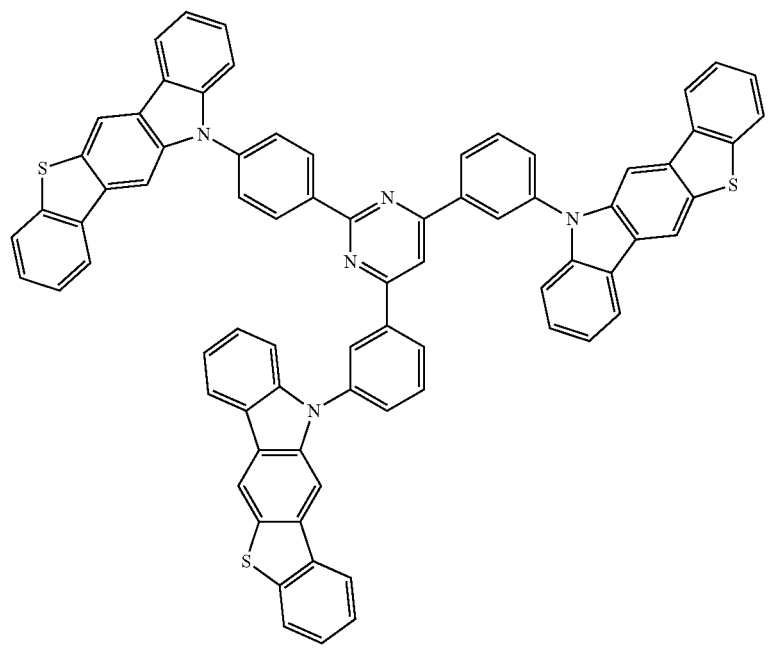

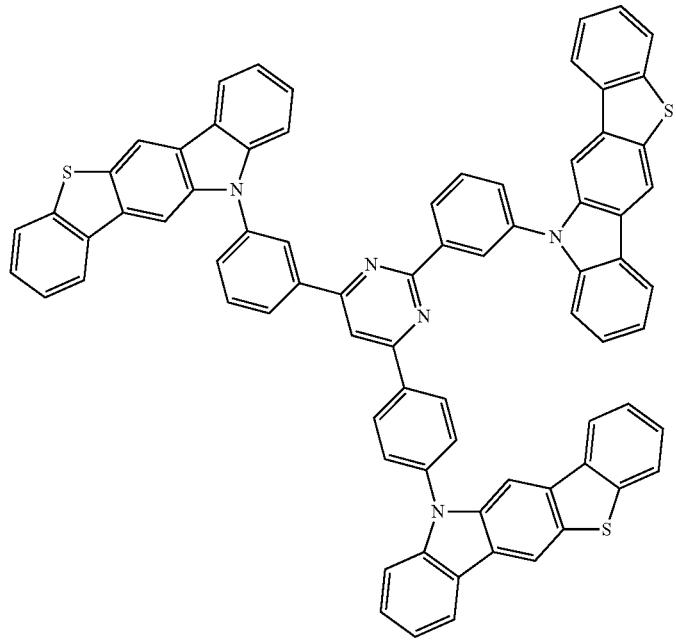
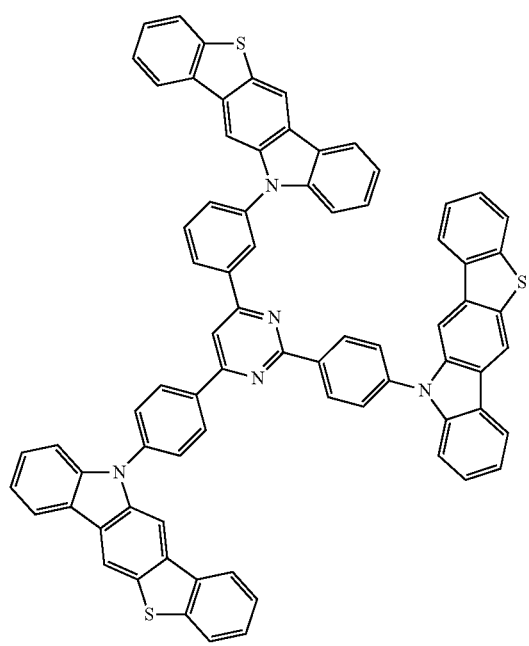

633
634
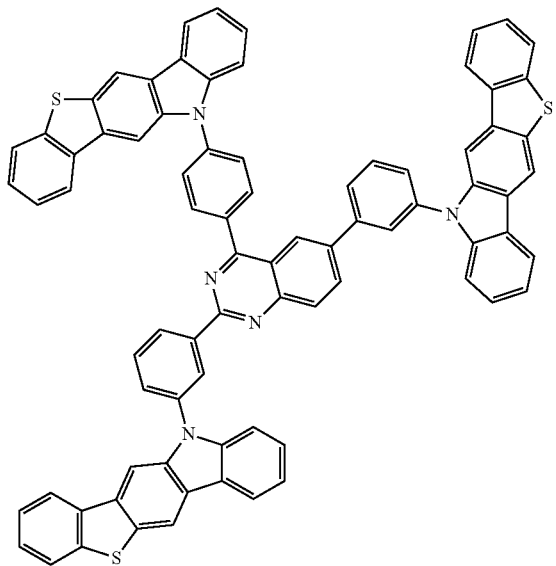
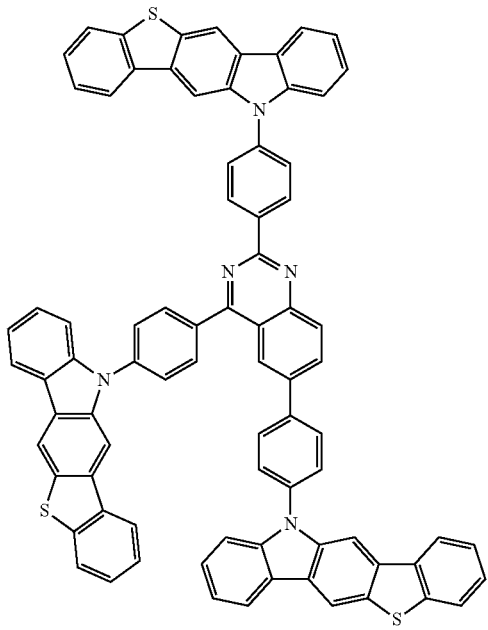
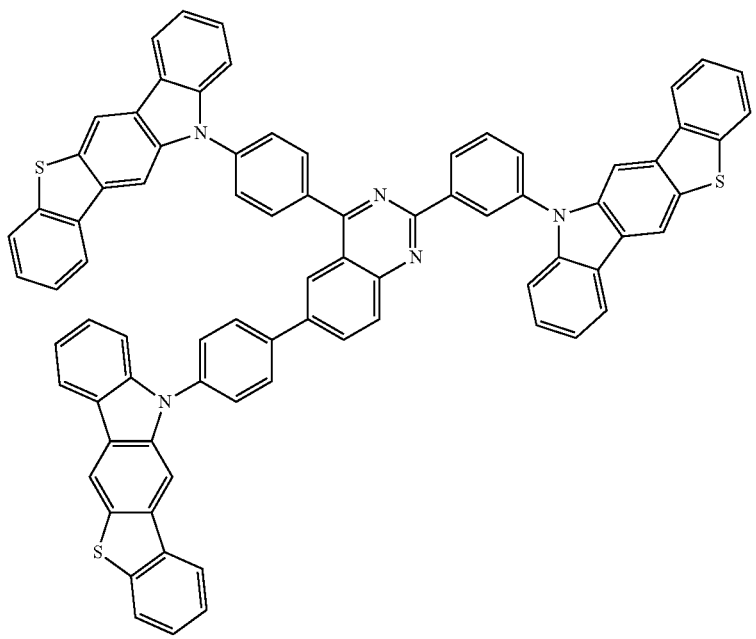

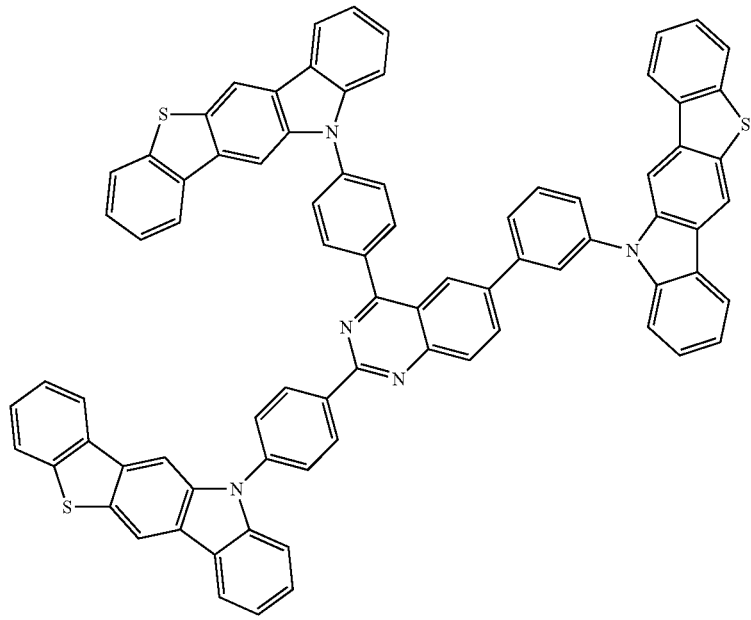
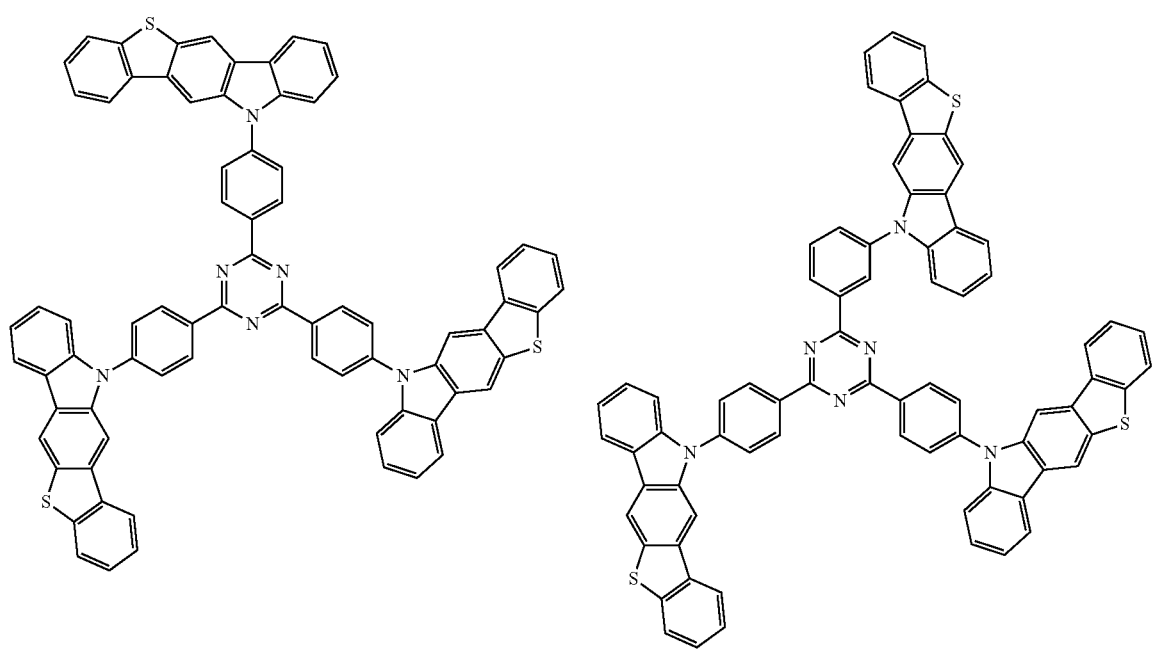

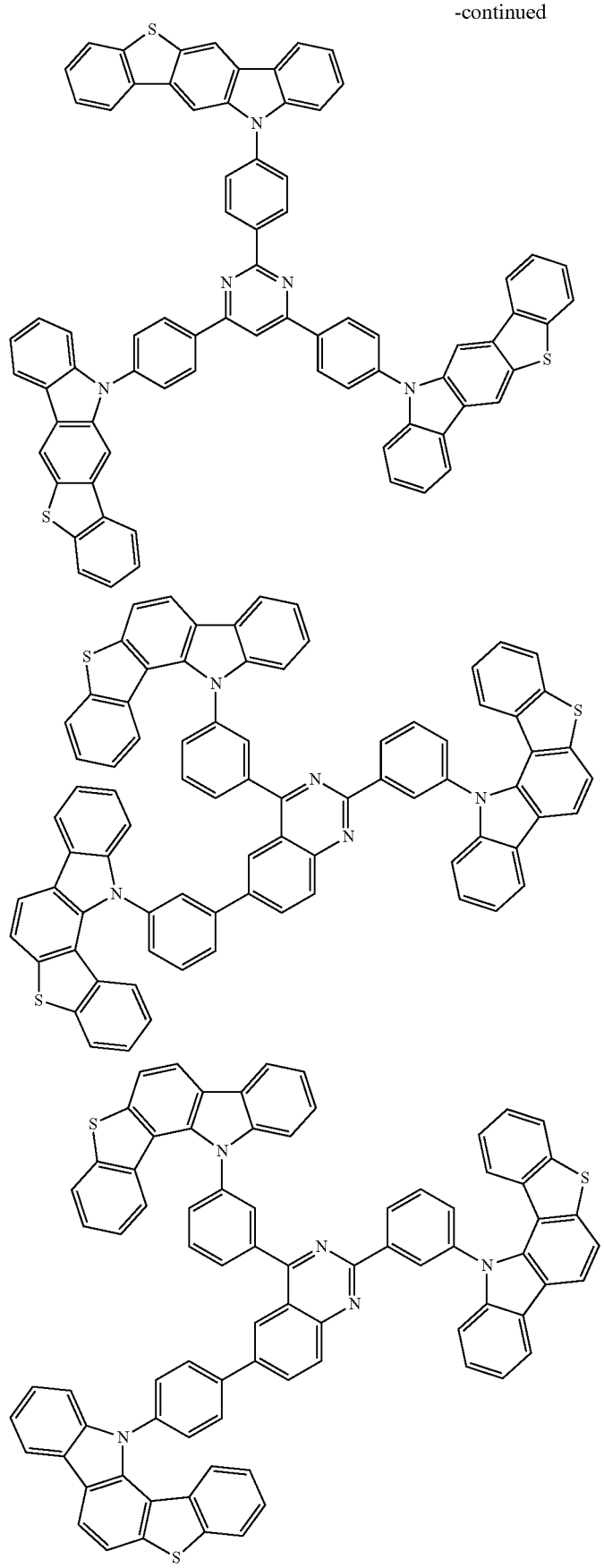

-continued
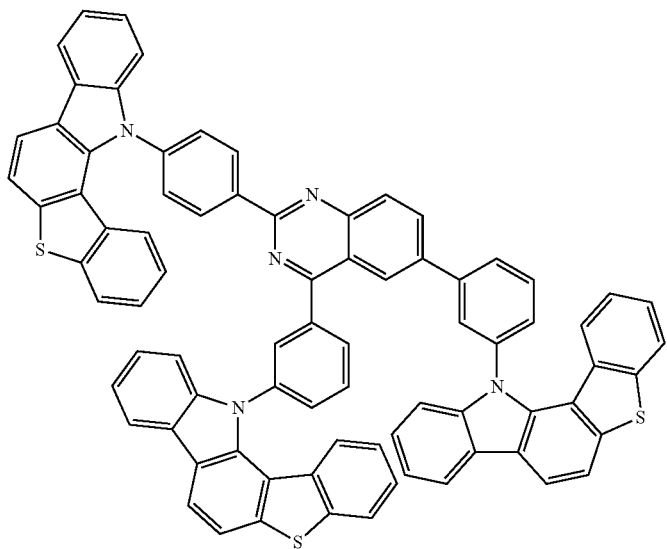
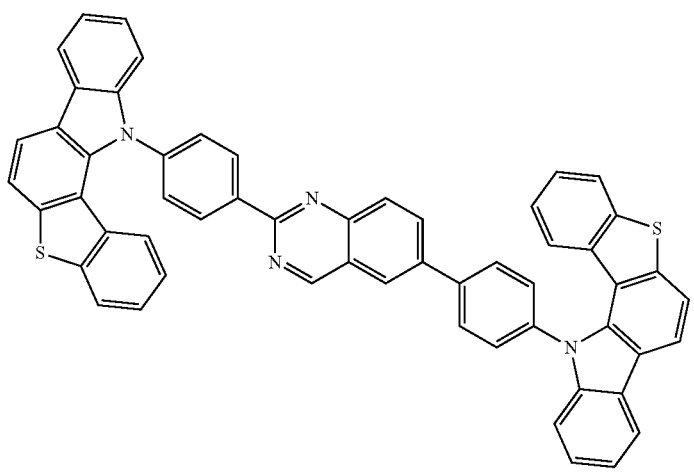
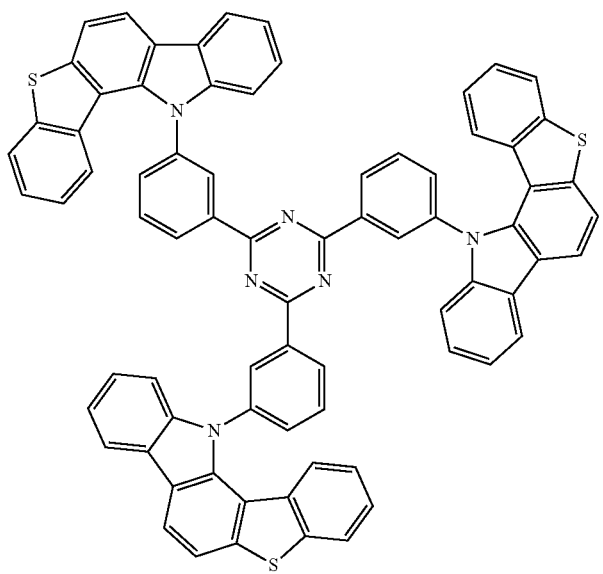

-continued
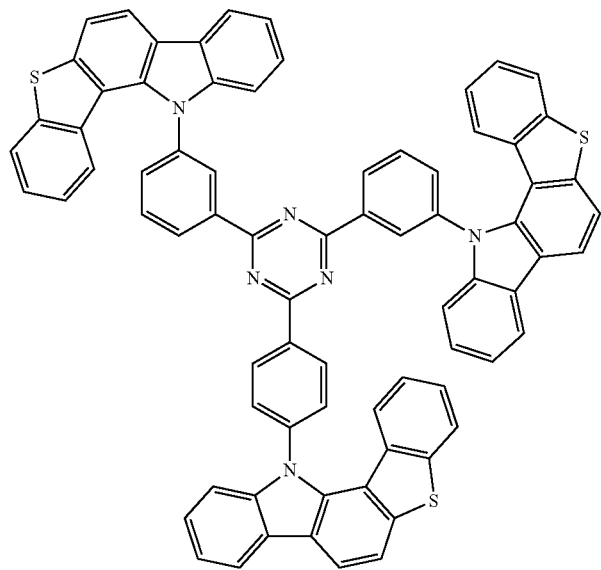
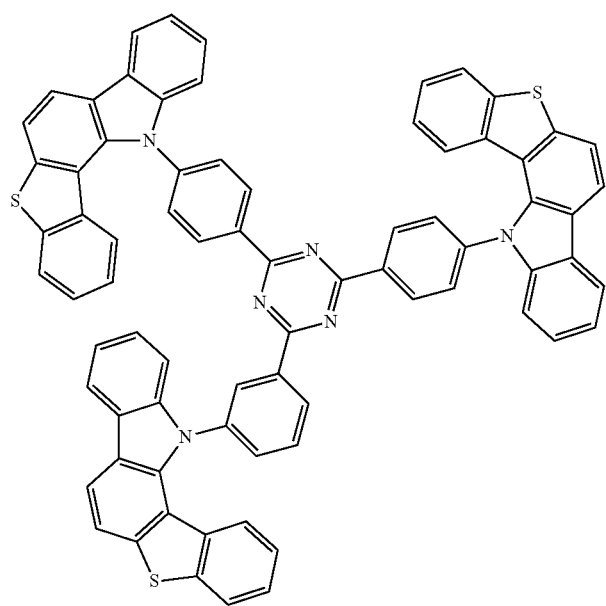

-continued
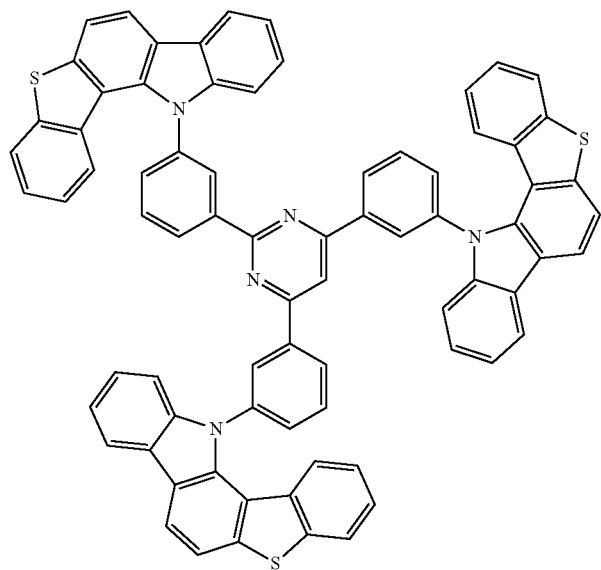
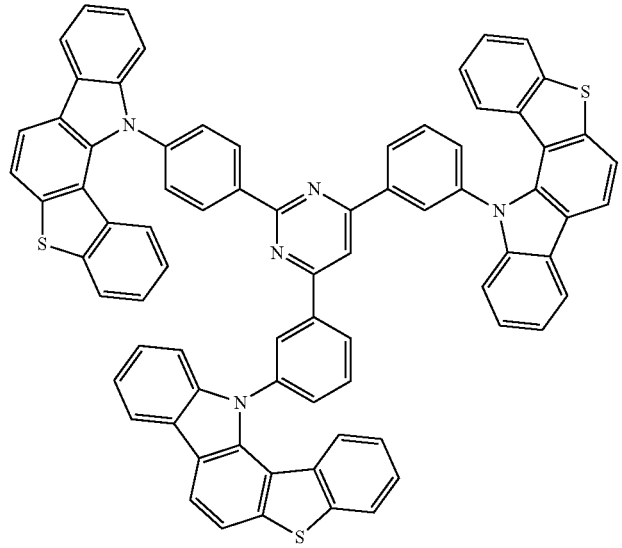
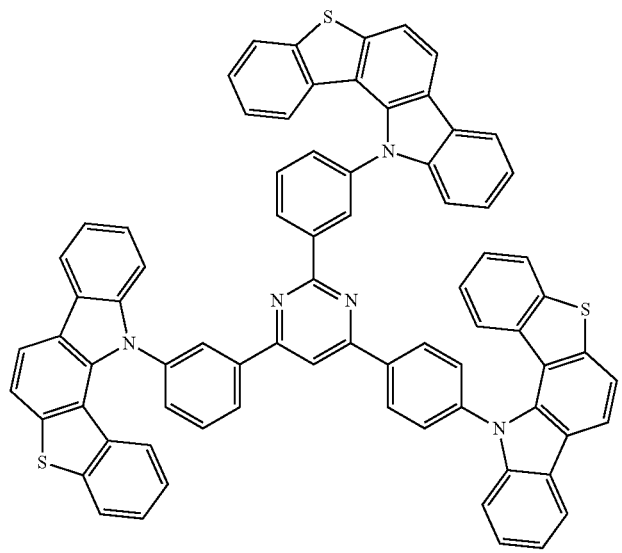

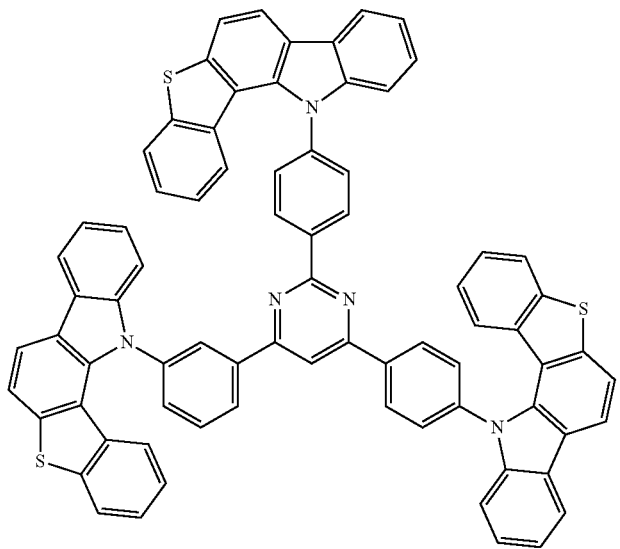
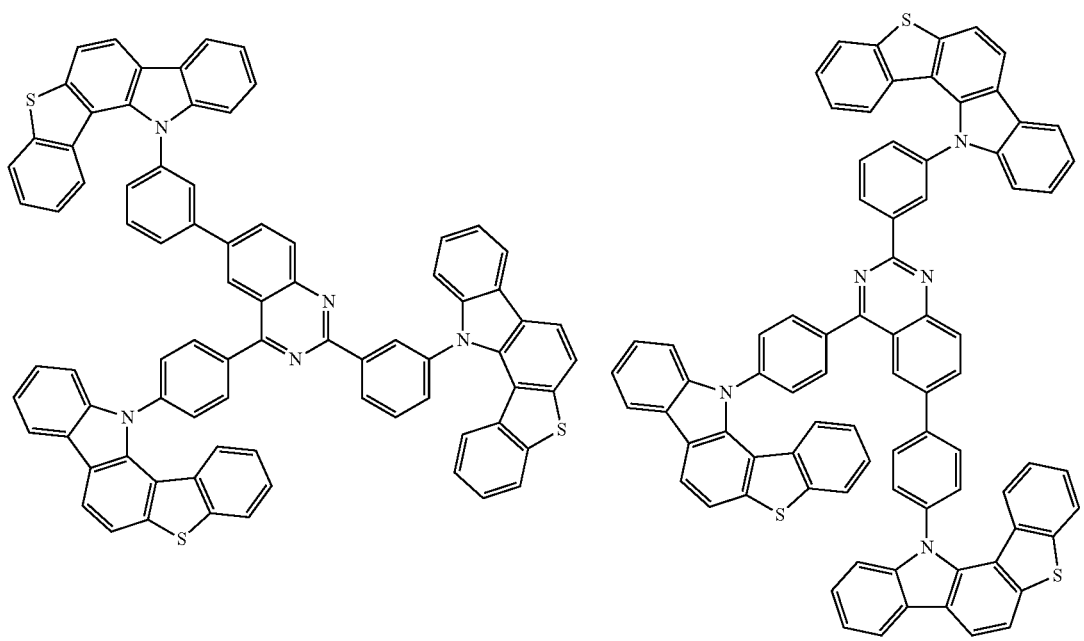

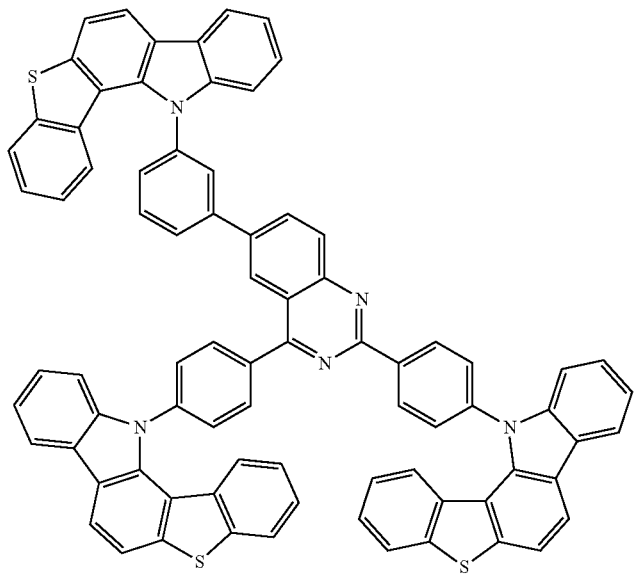
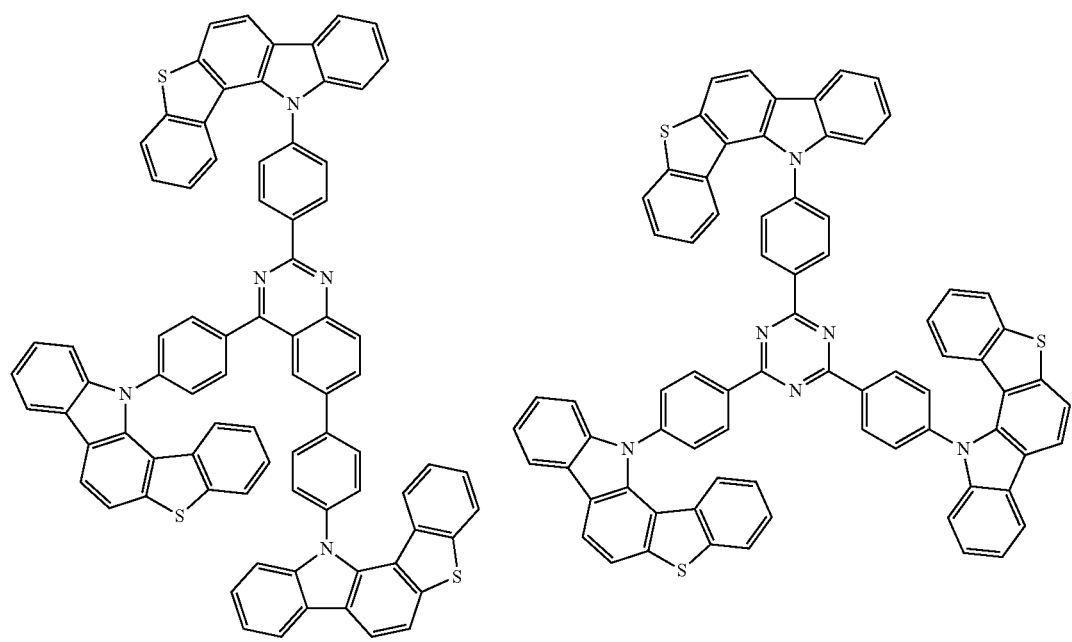

-continued
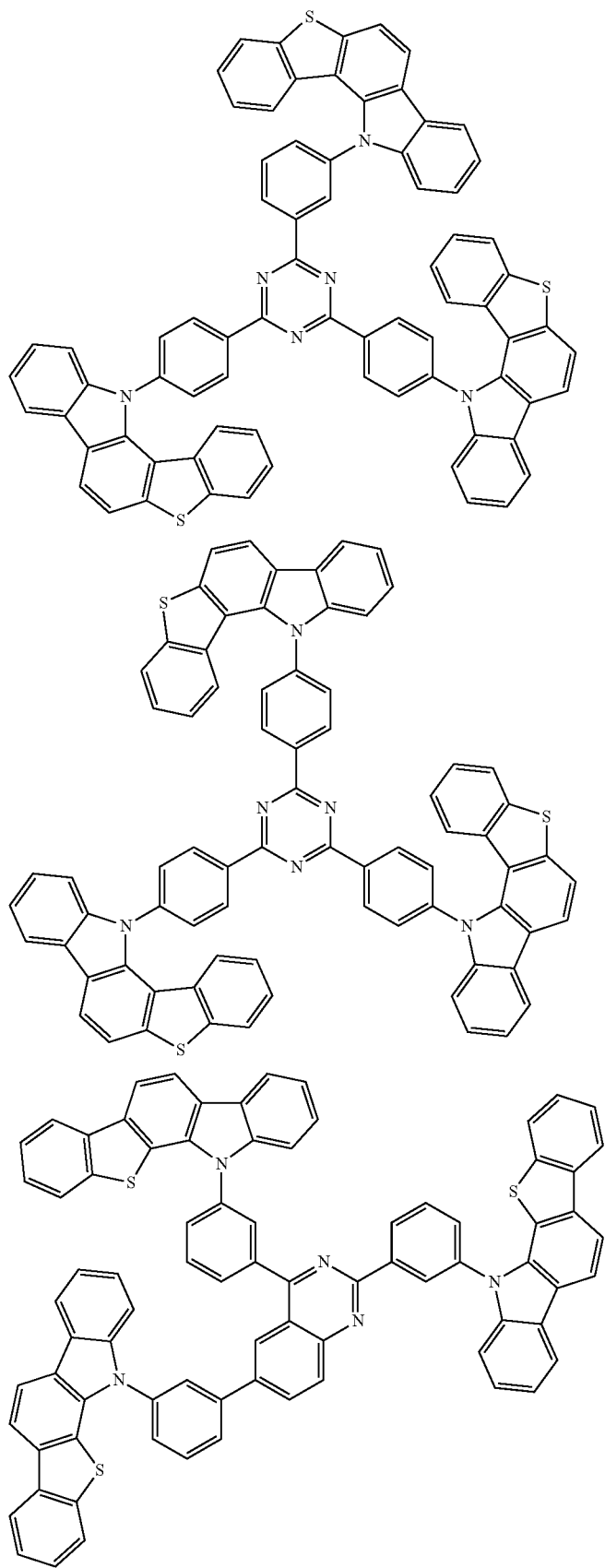

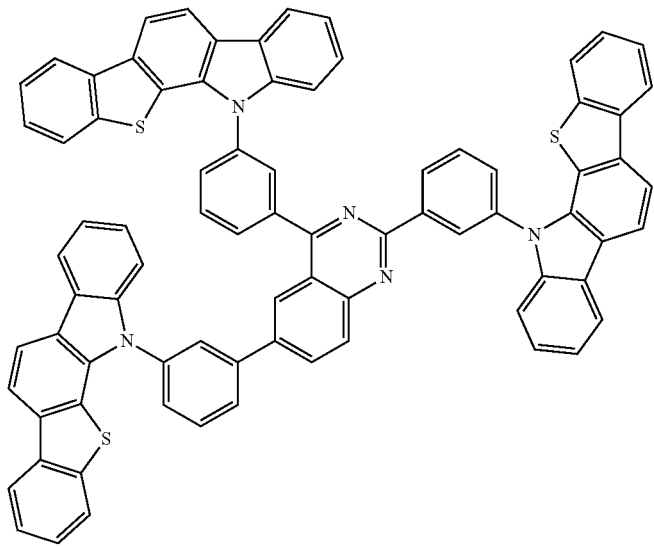
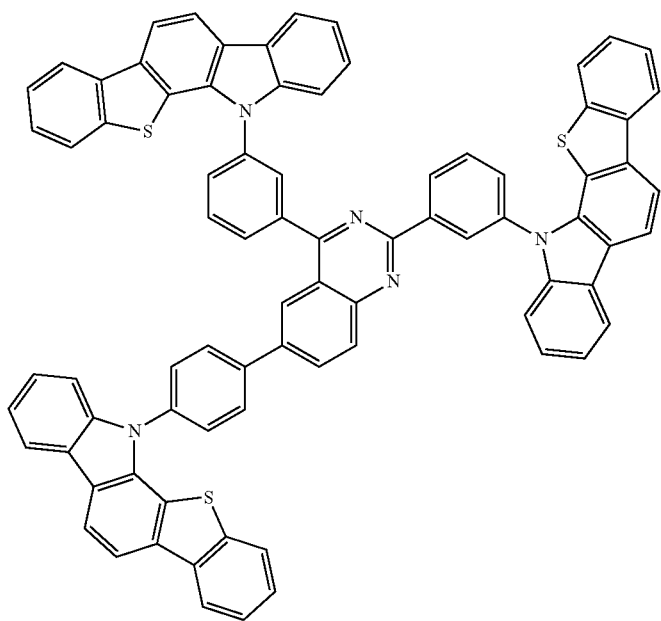

-continued
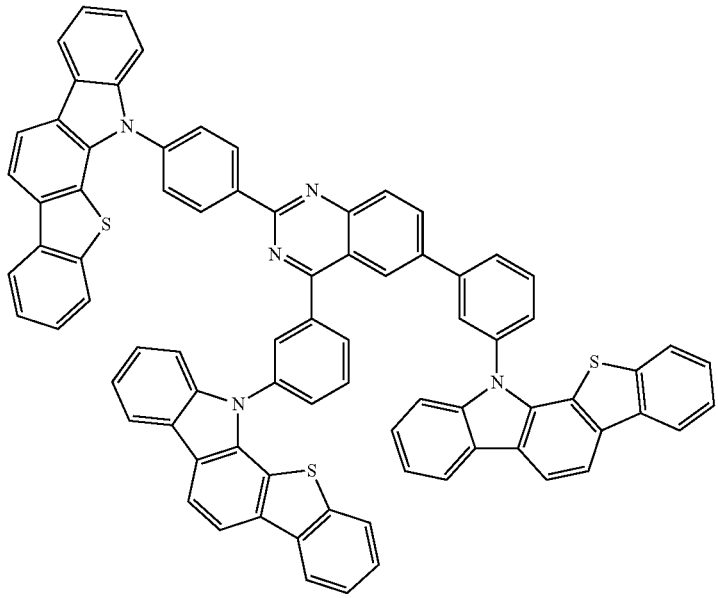
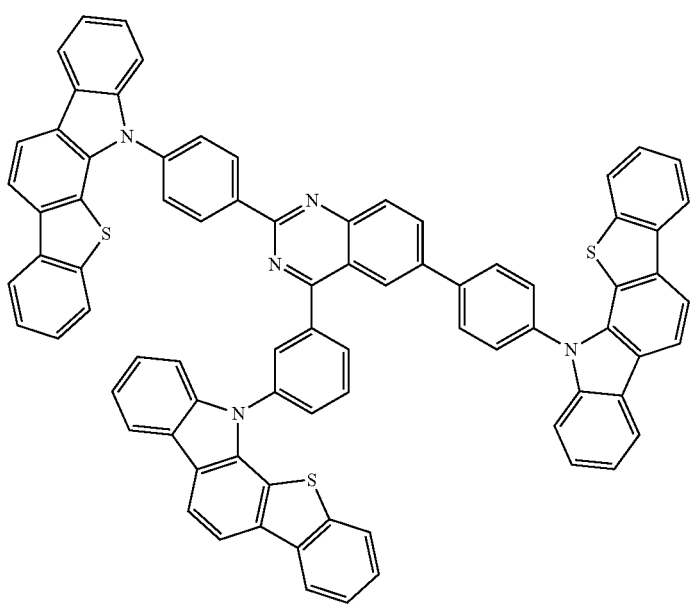

-continued
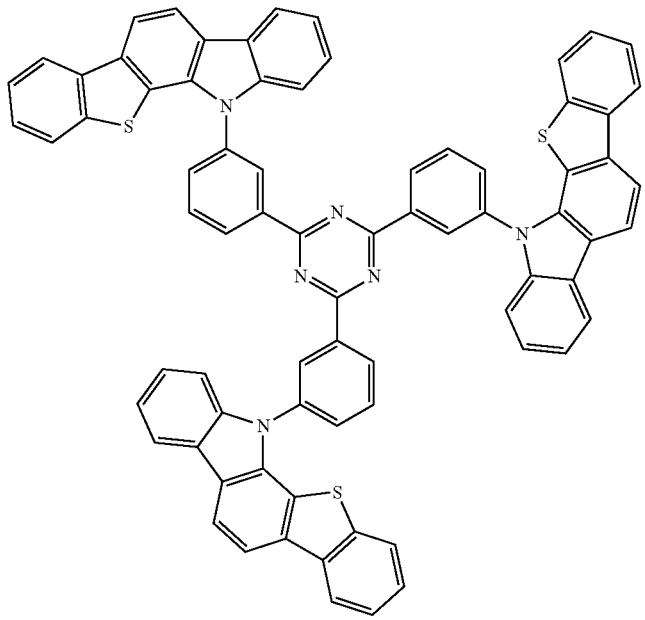
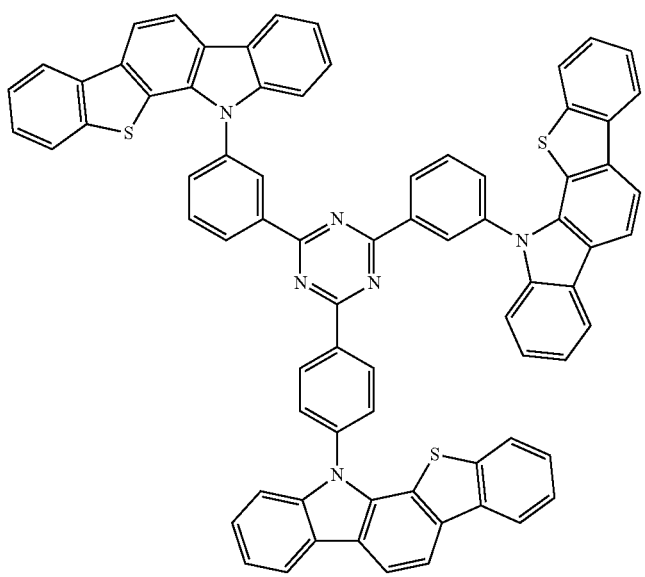

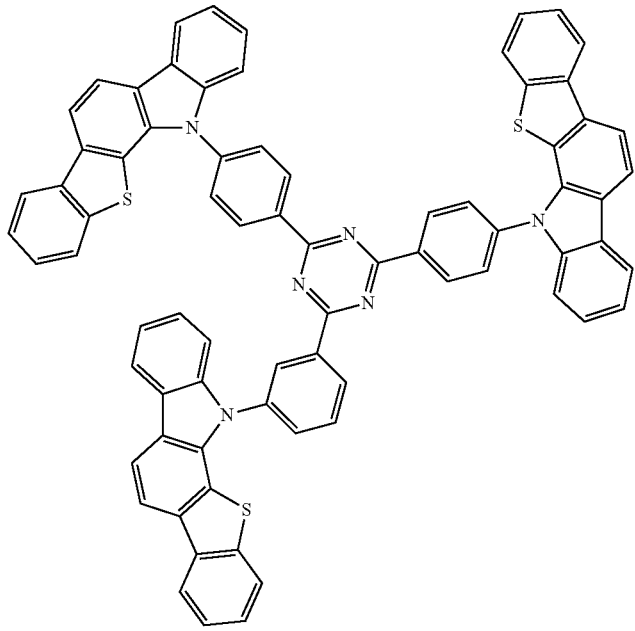
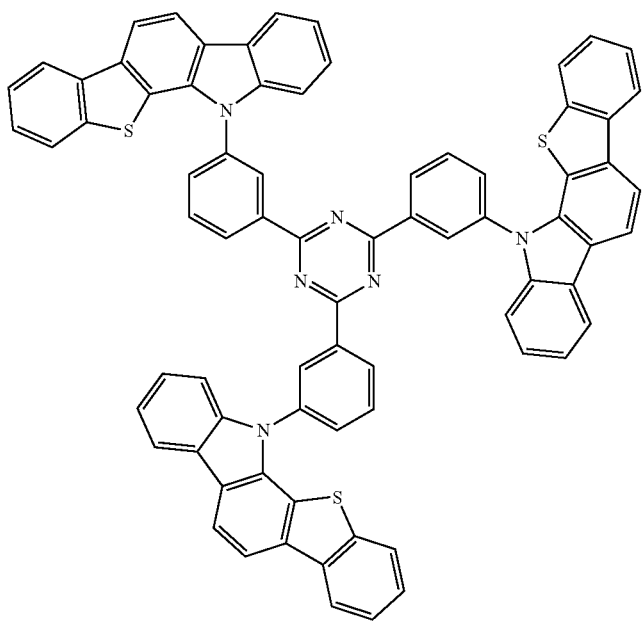

-continued
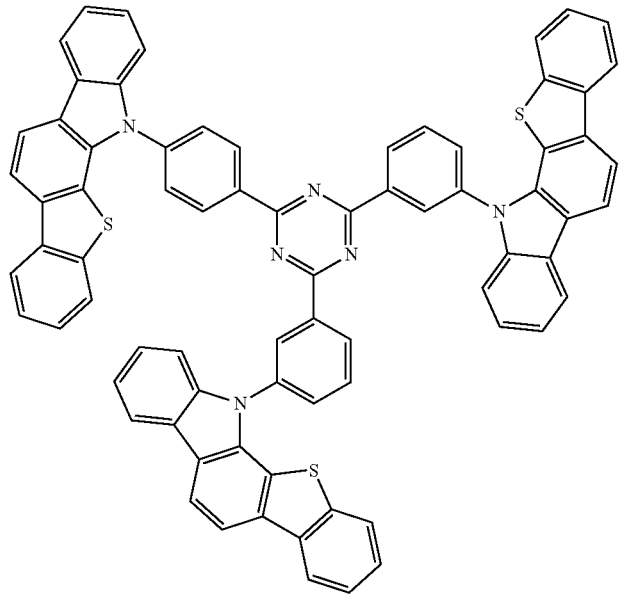
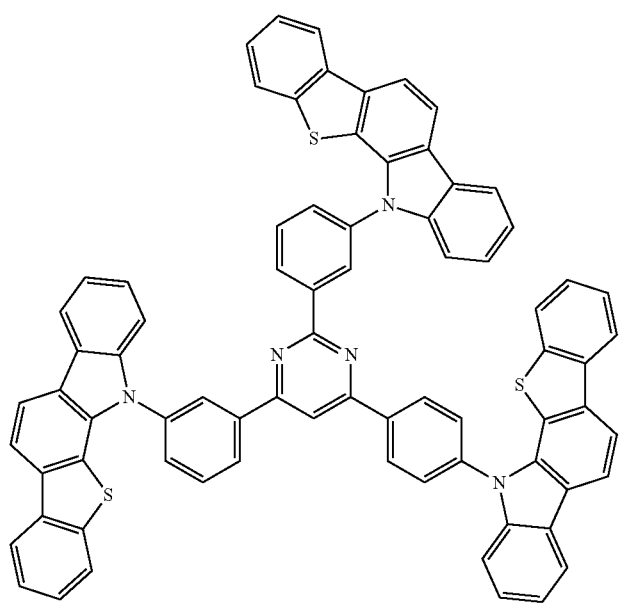

661
662
-continued
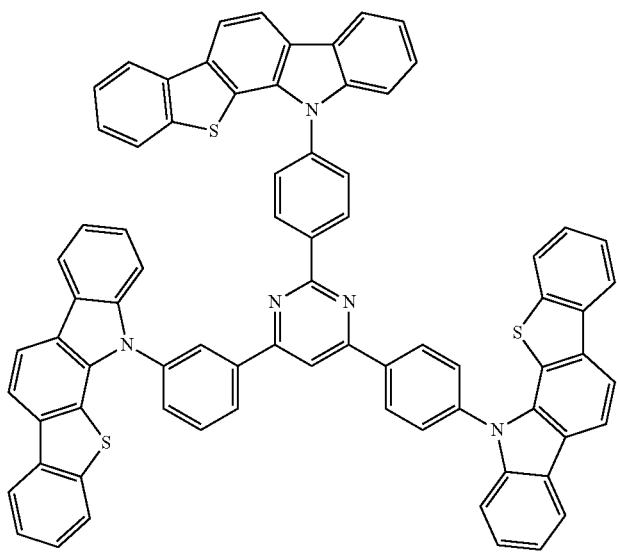
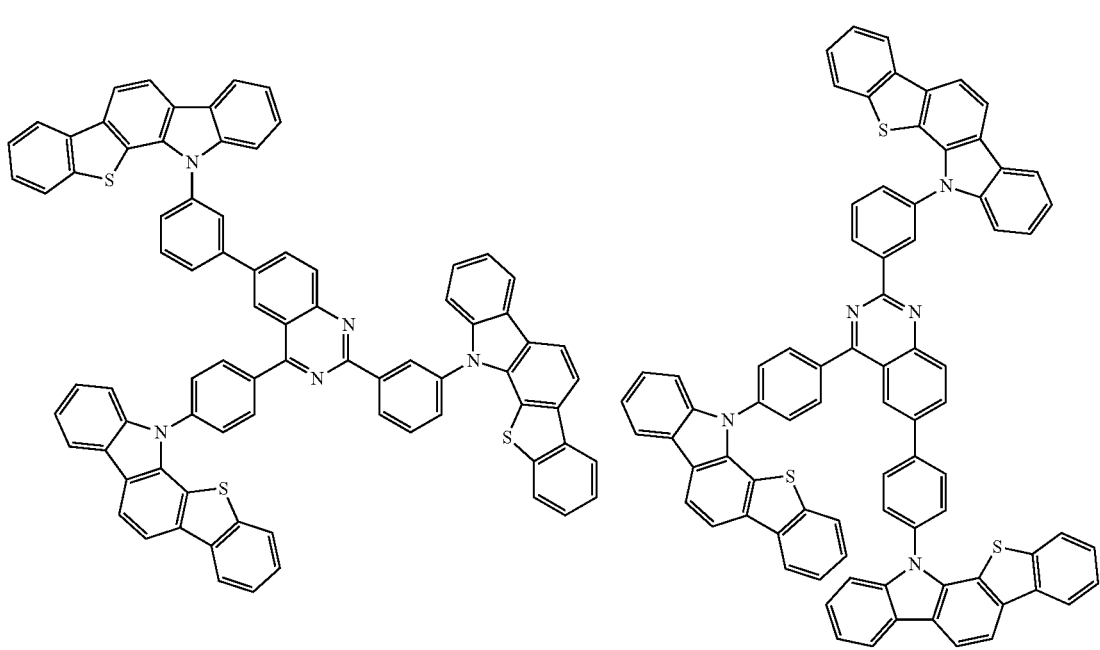

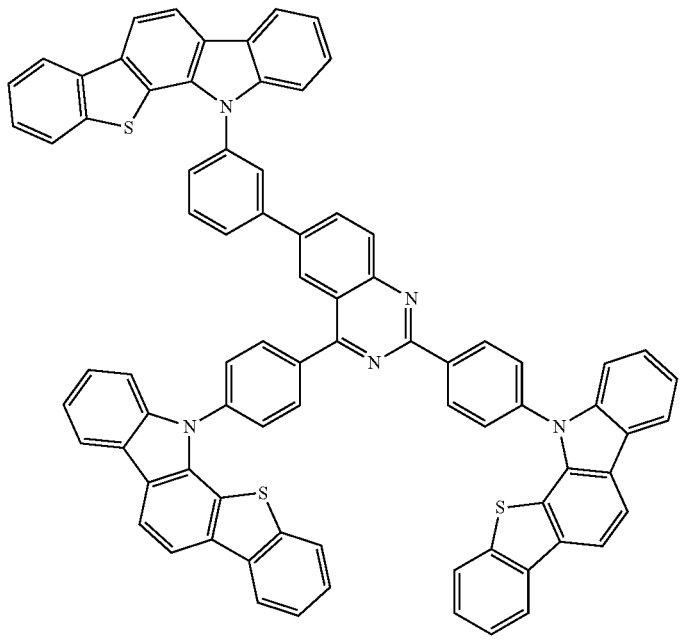
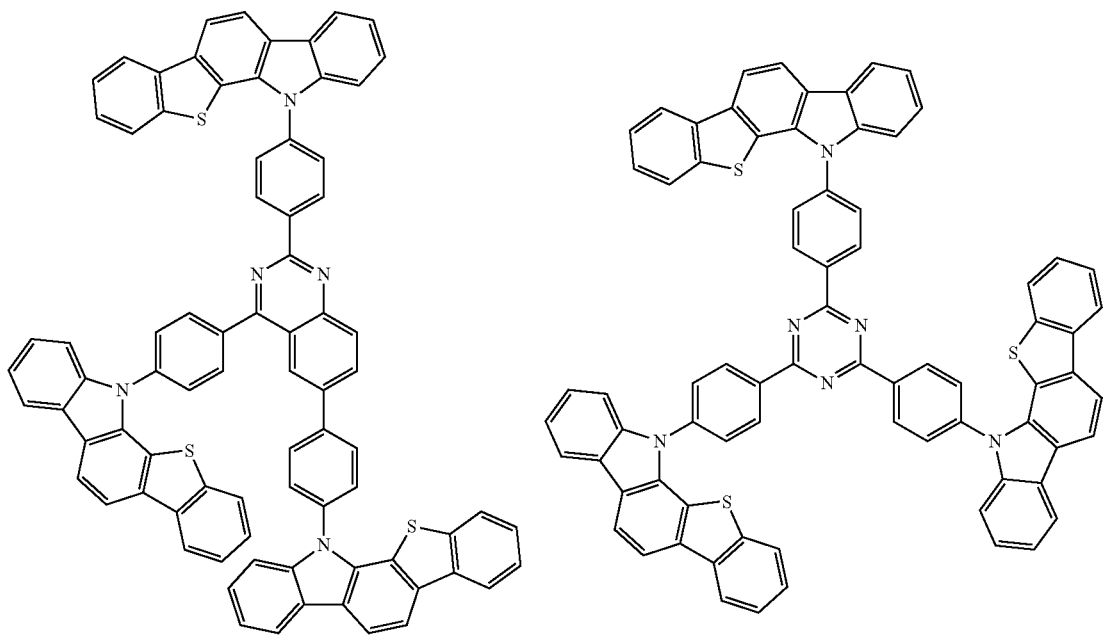

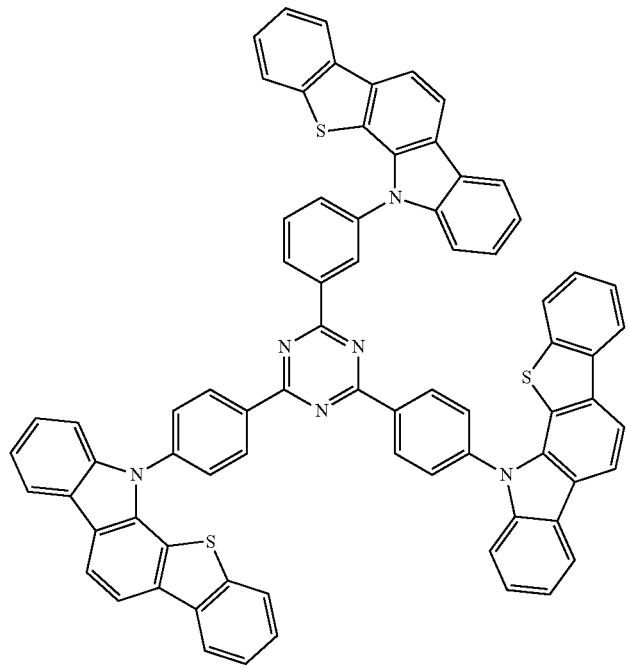
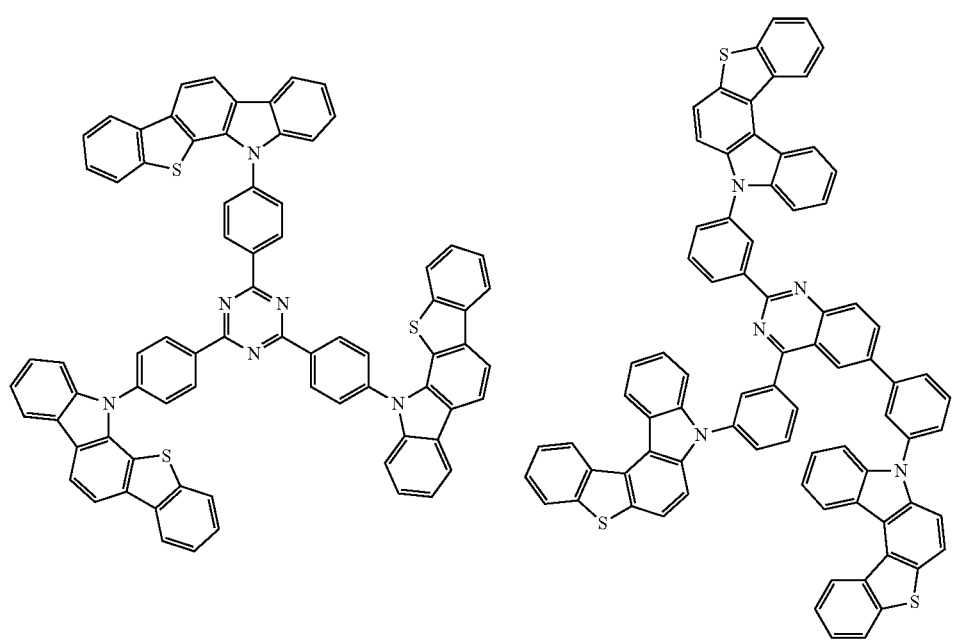

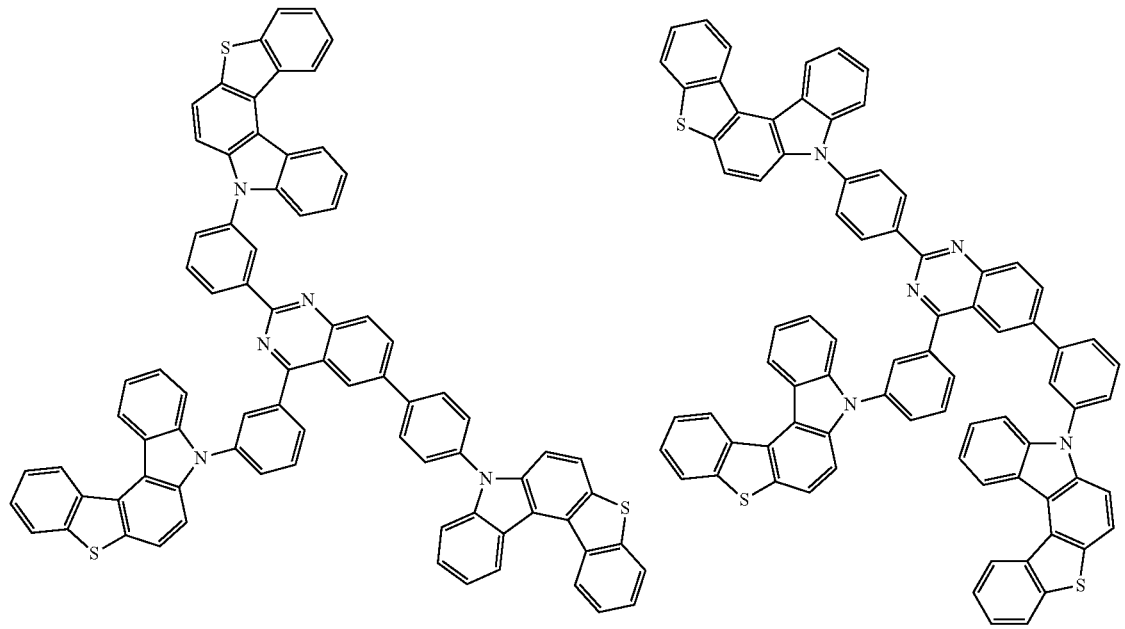
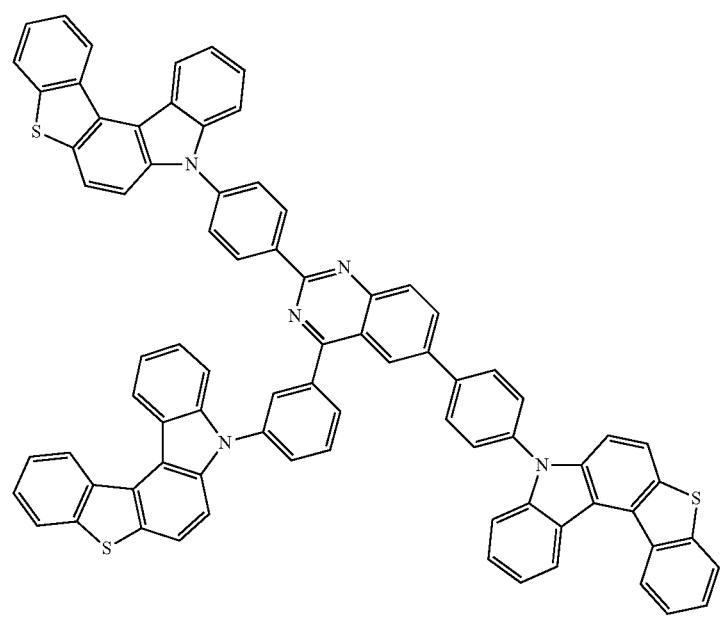

-continued
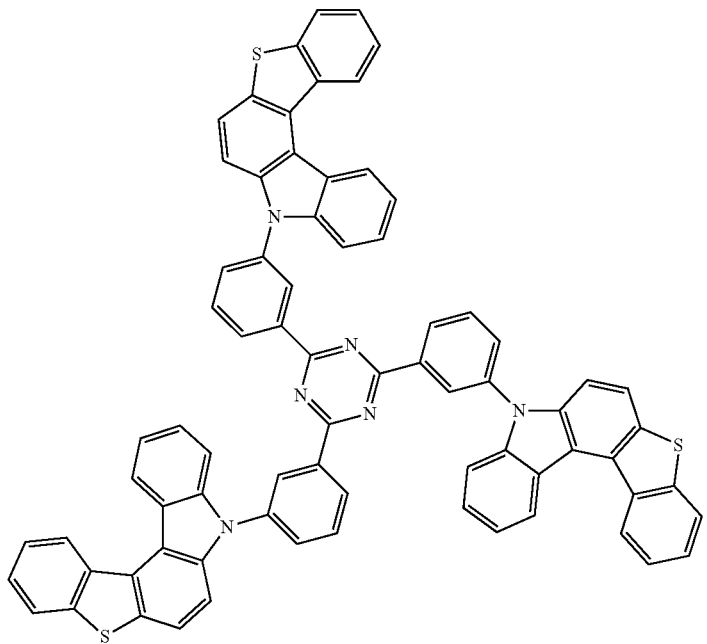
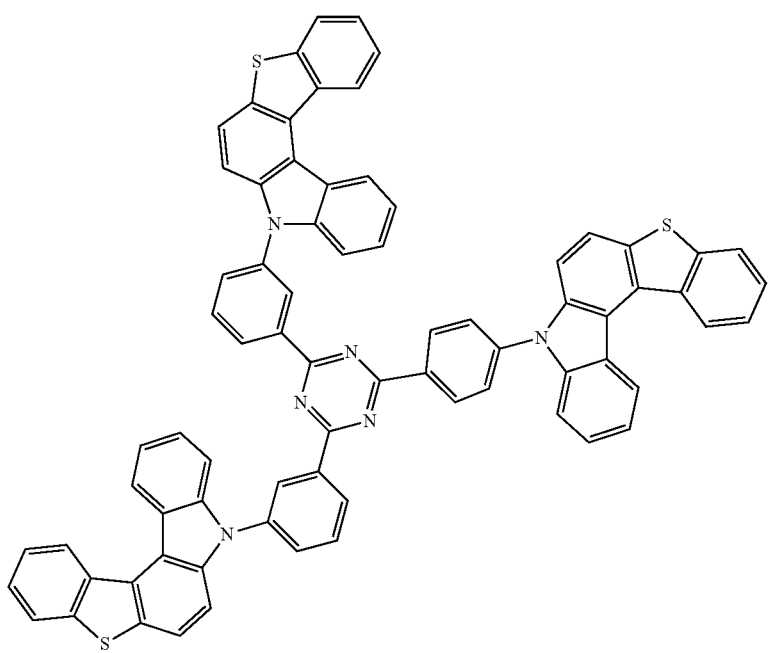

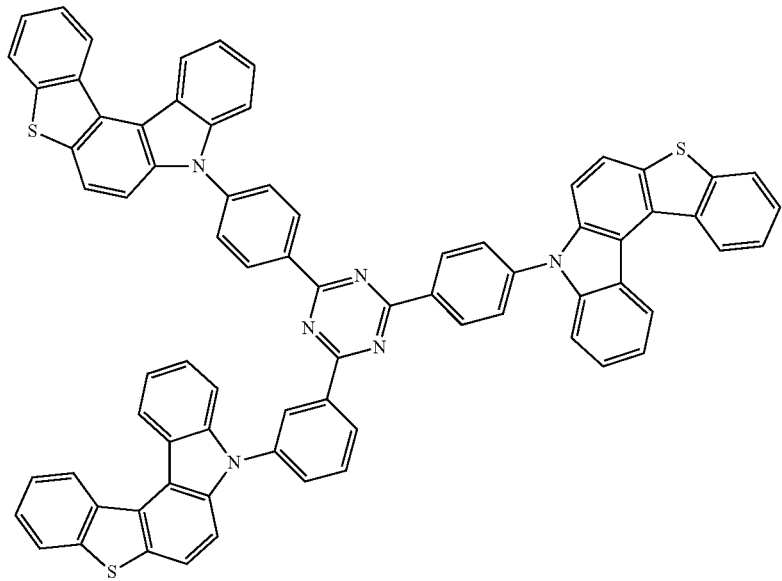
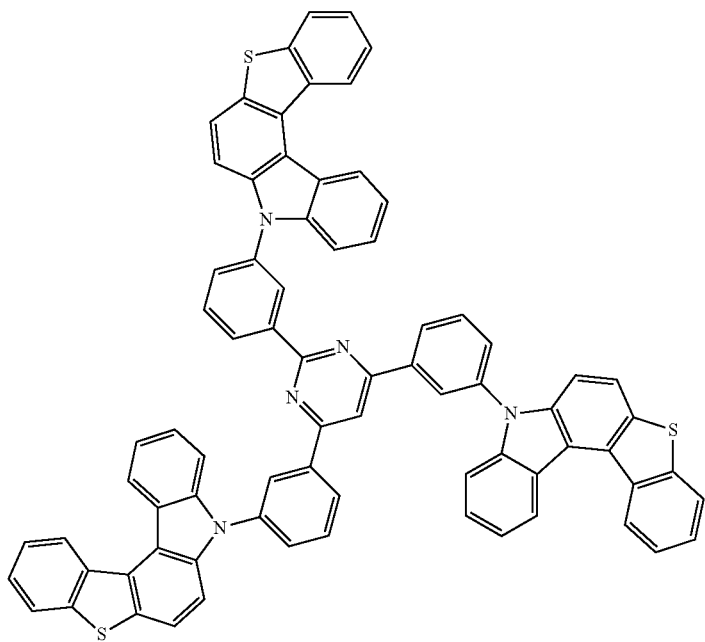

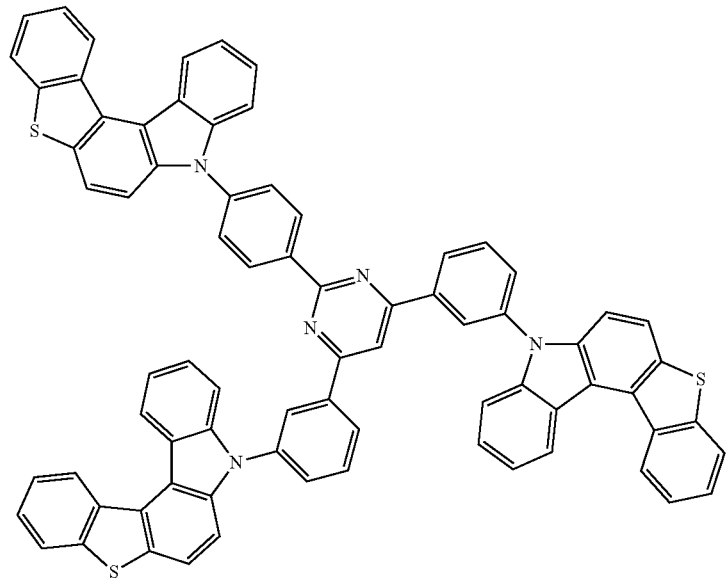
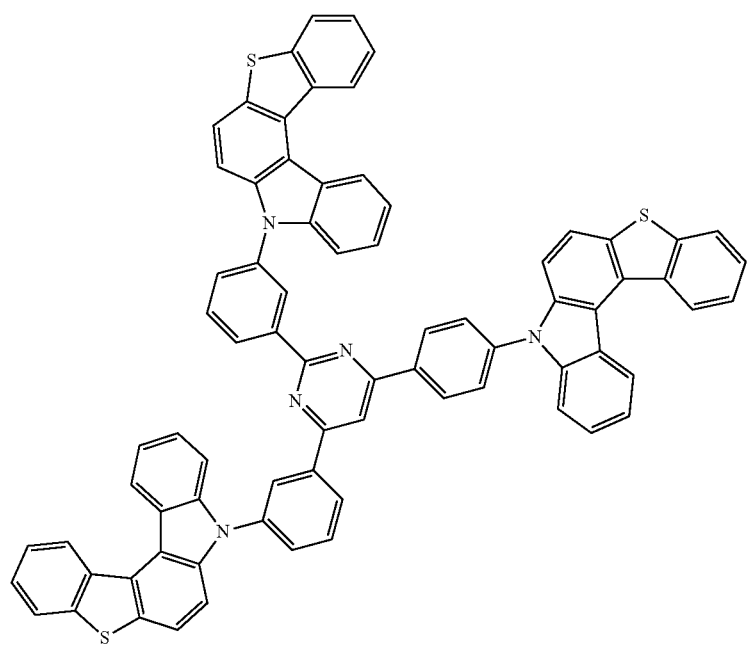

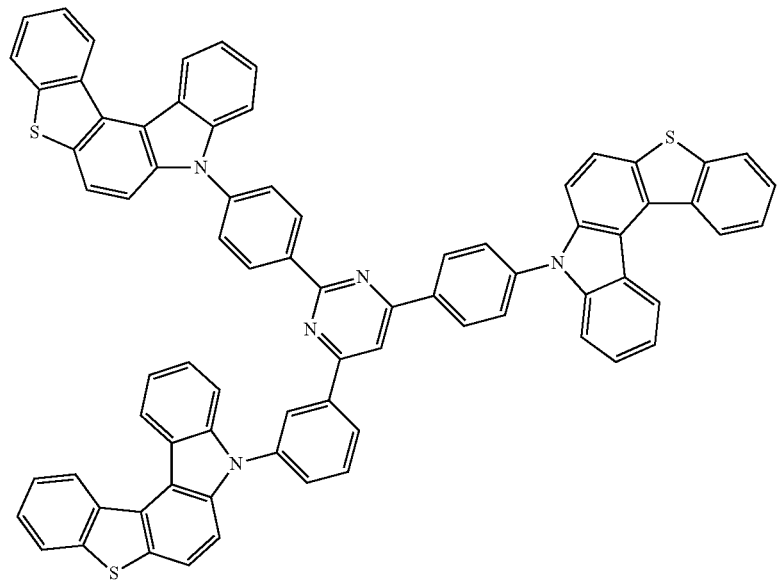
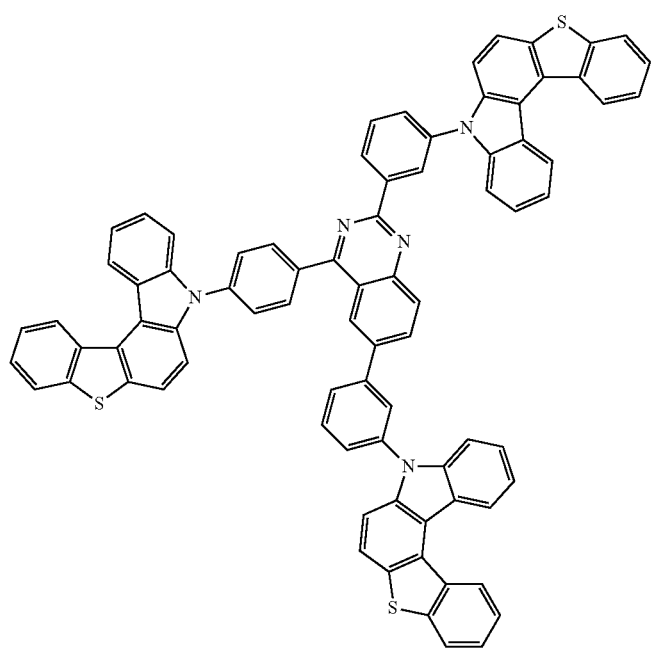

-continued
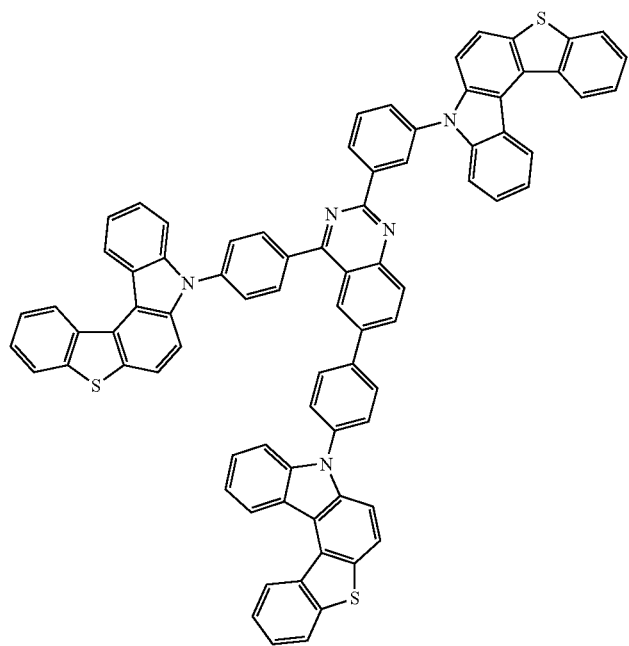
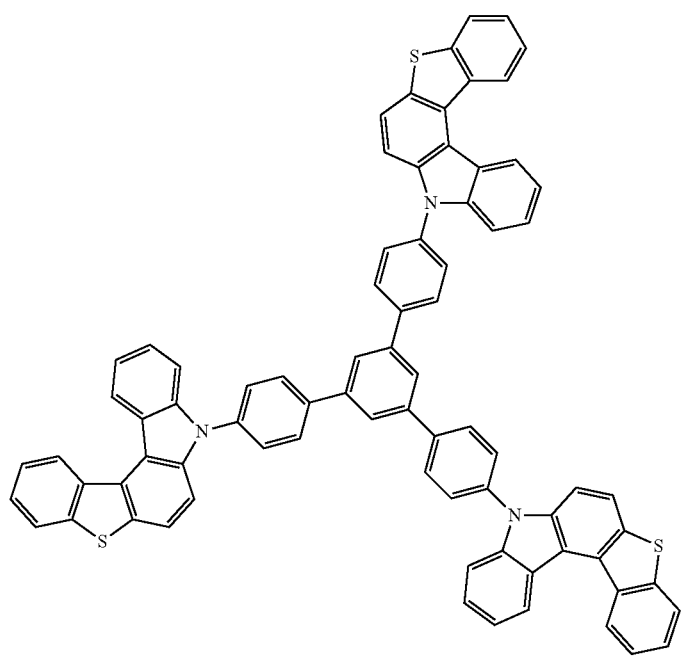

-continued
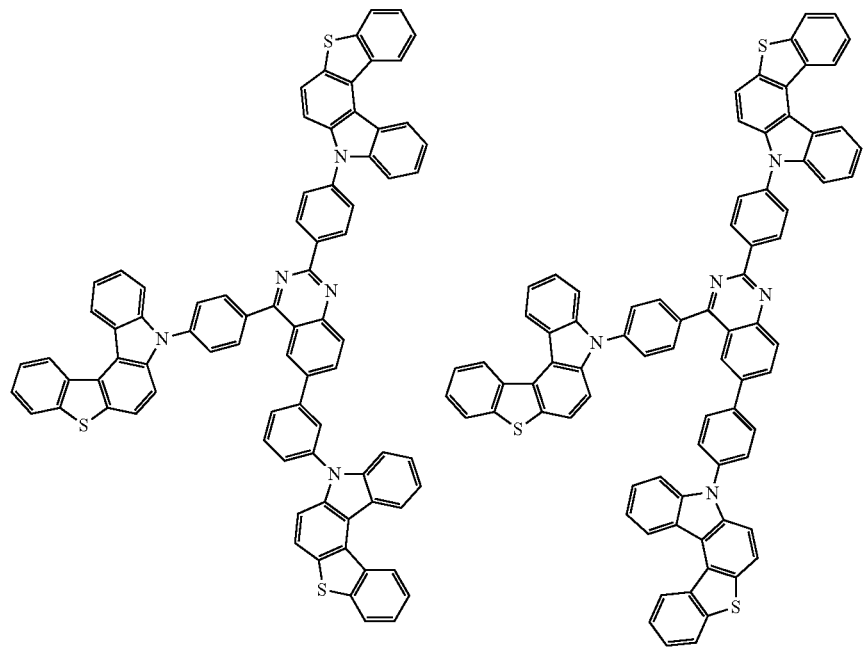
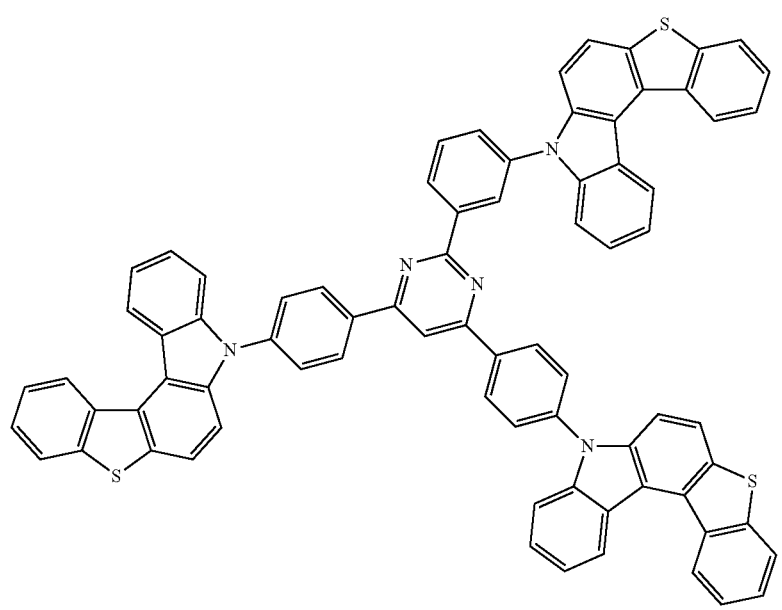

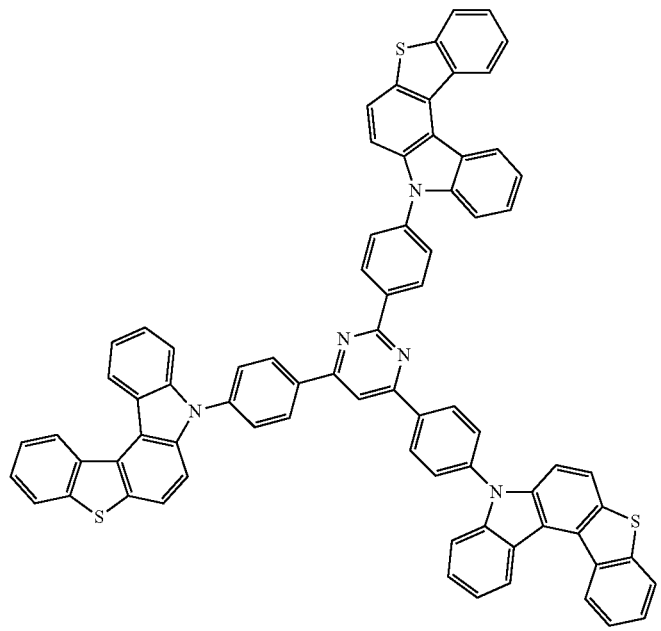
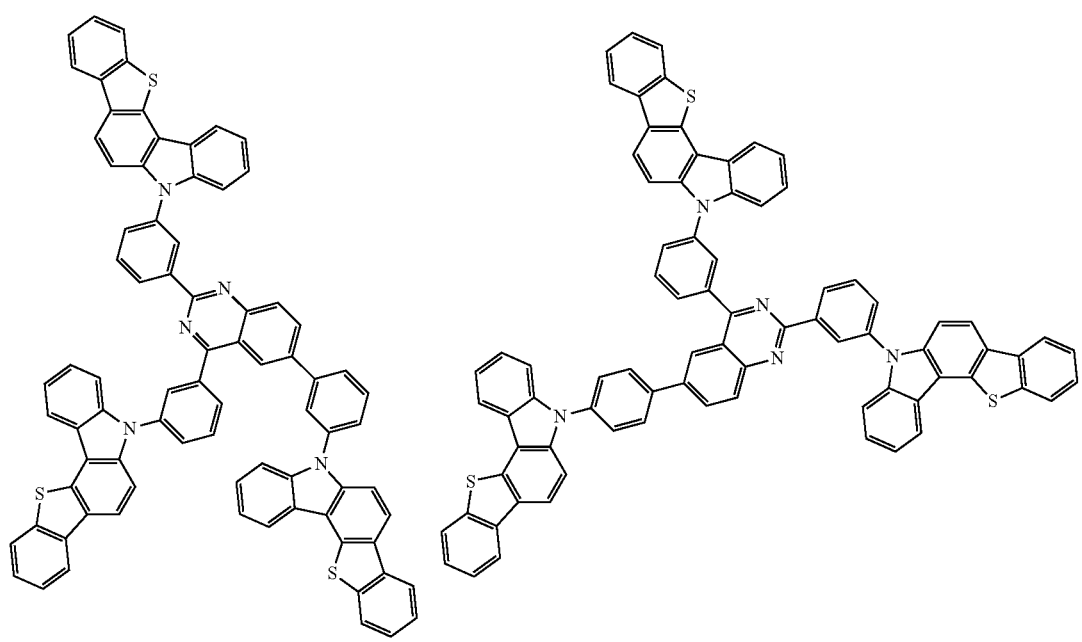

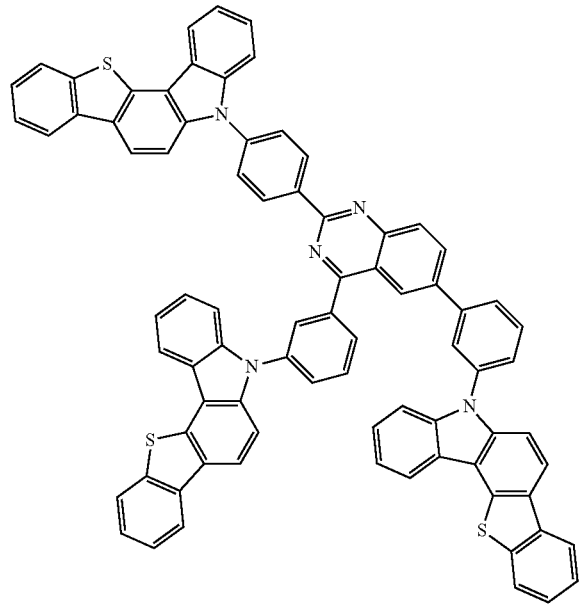
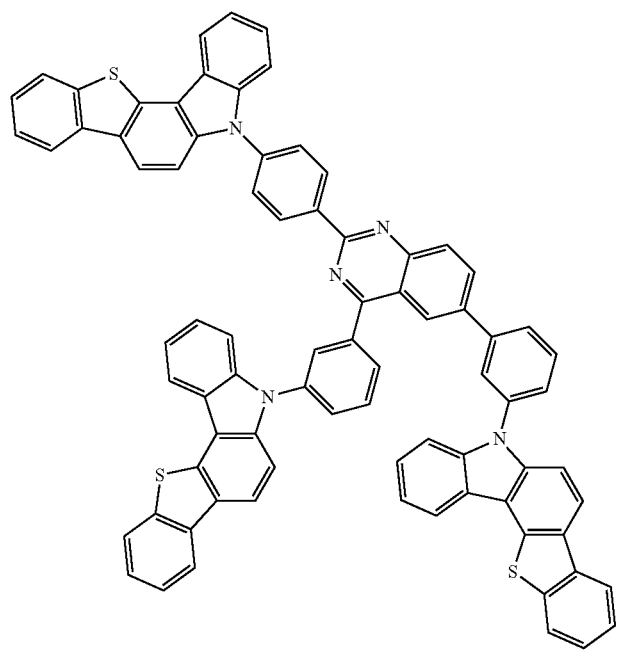

-continued
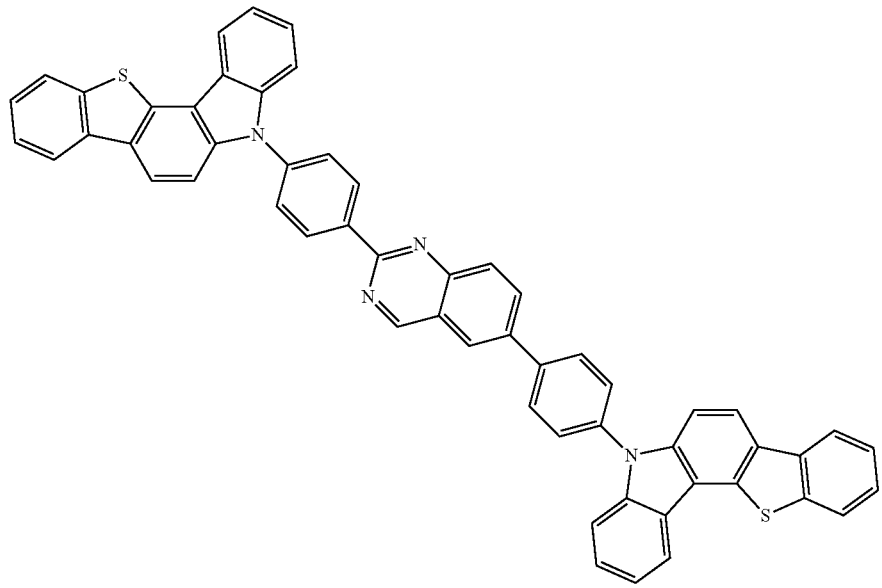
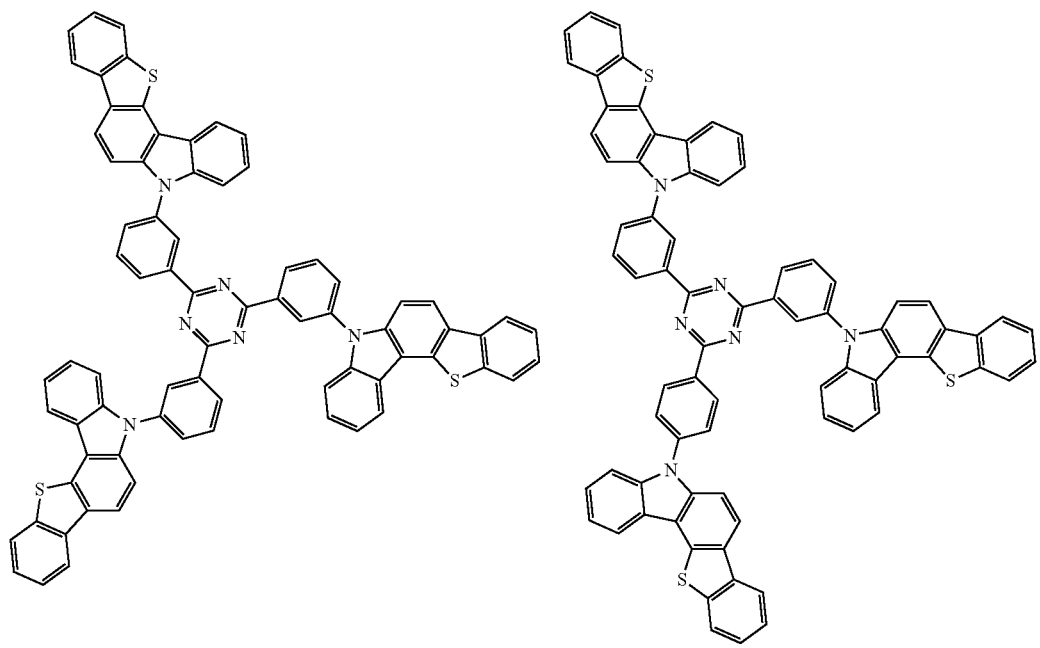

-continued
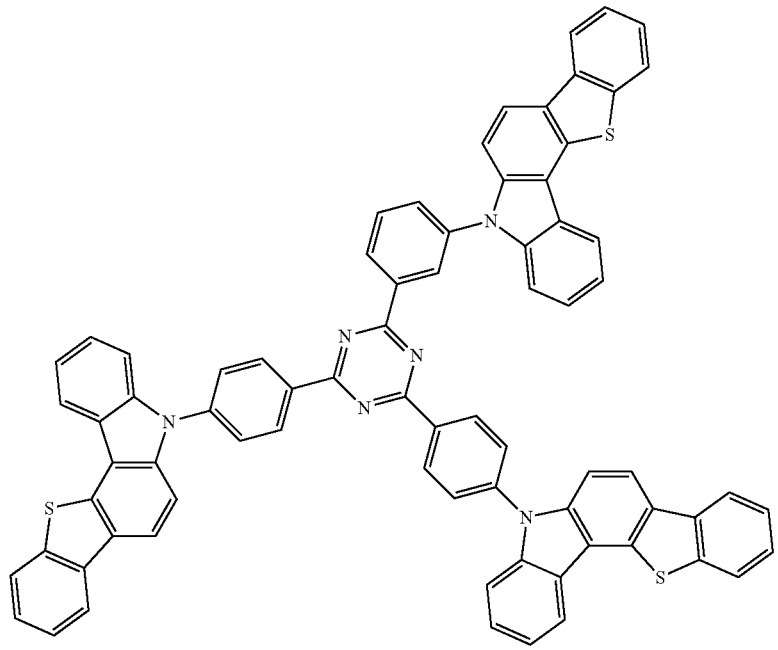
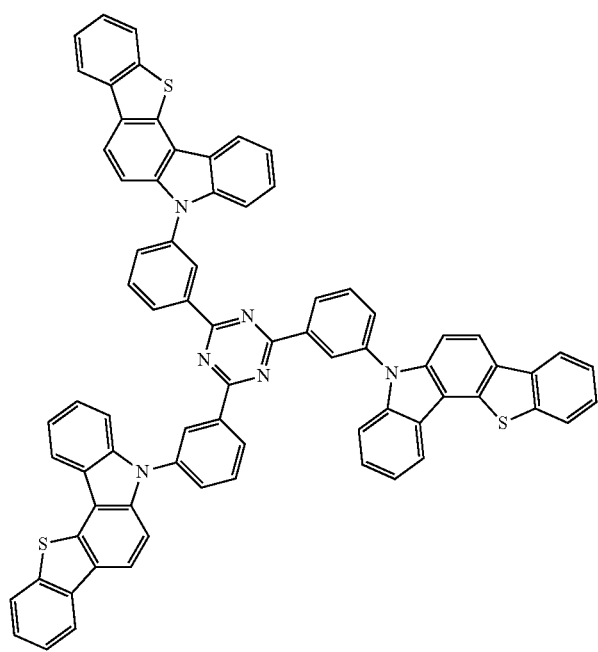

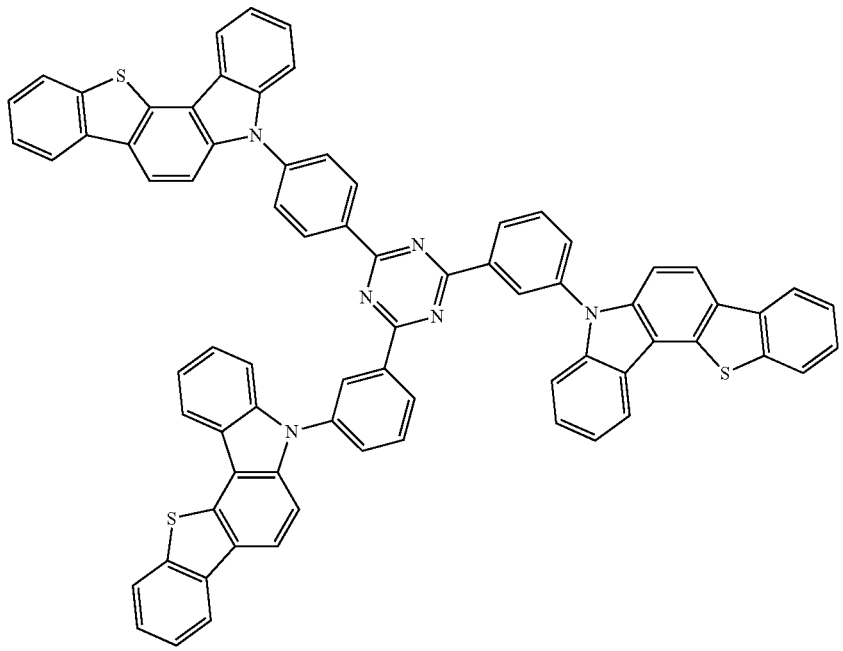
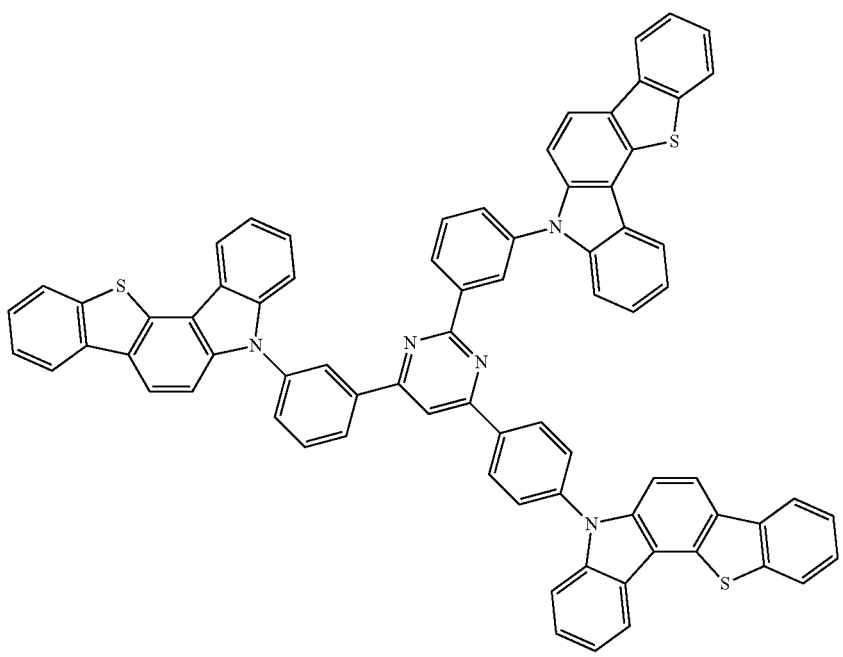

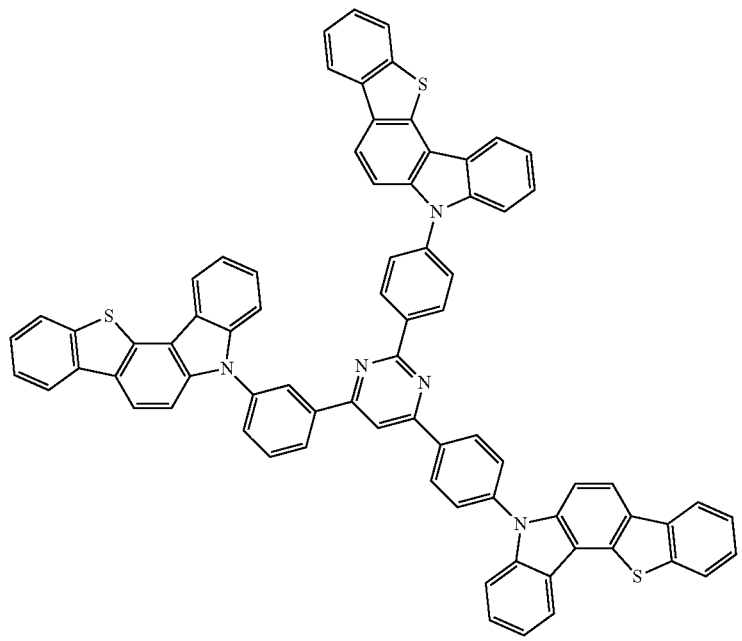
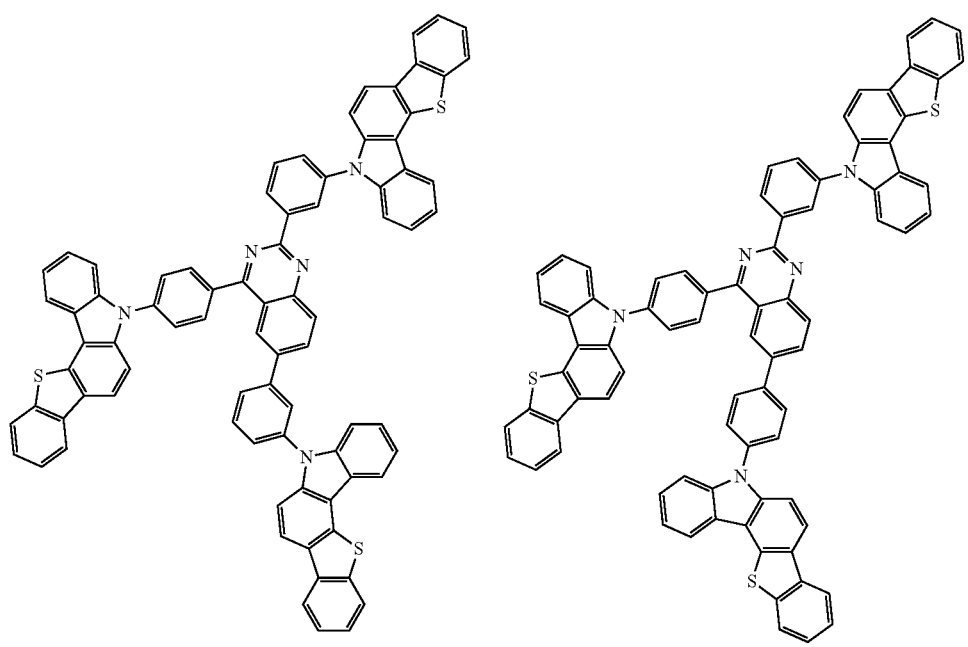

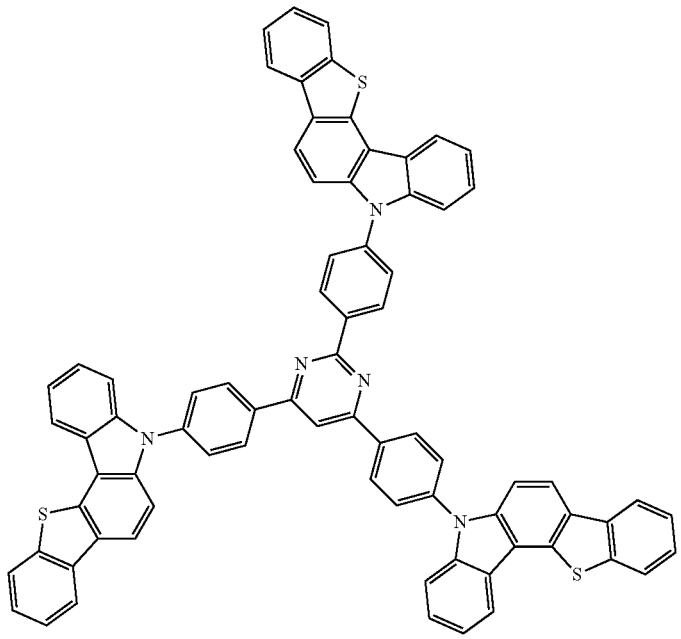
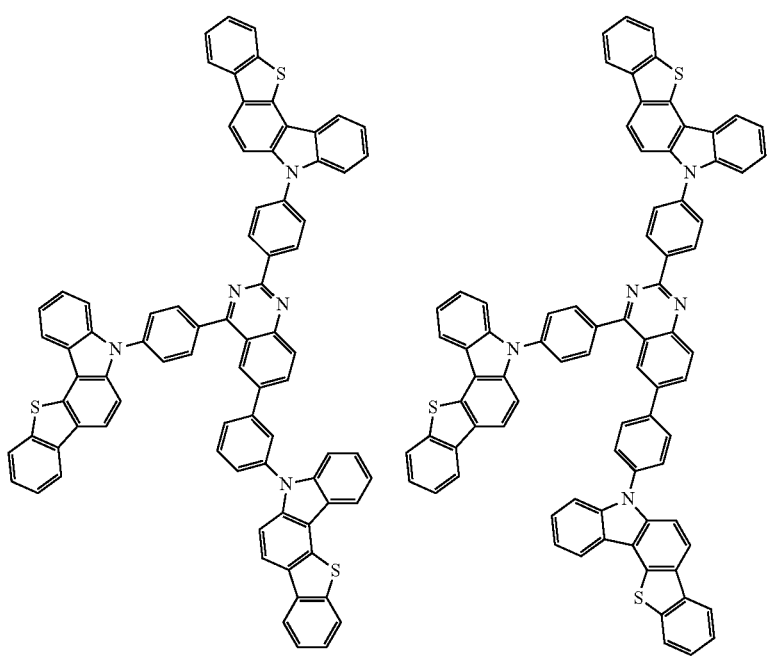

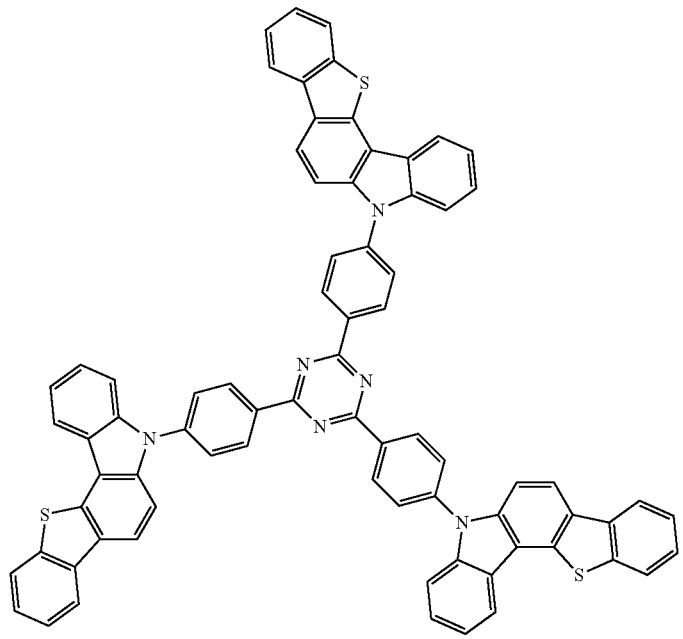
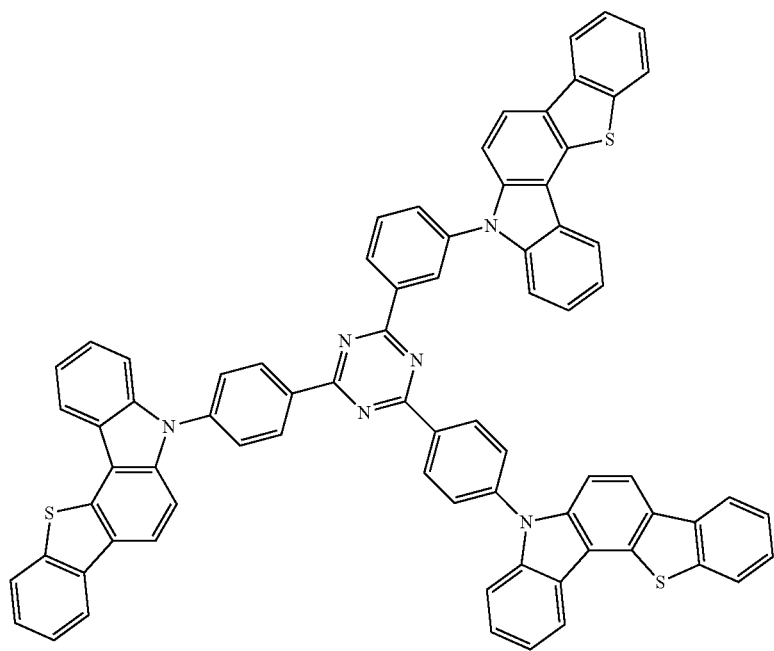

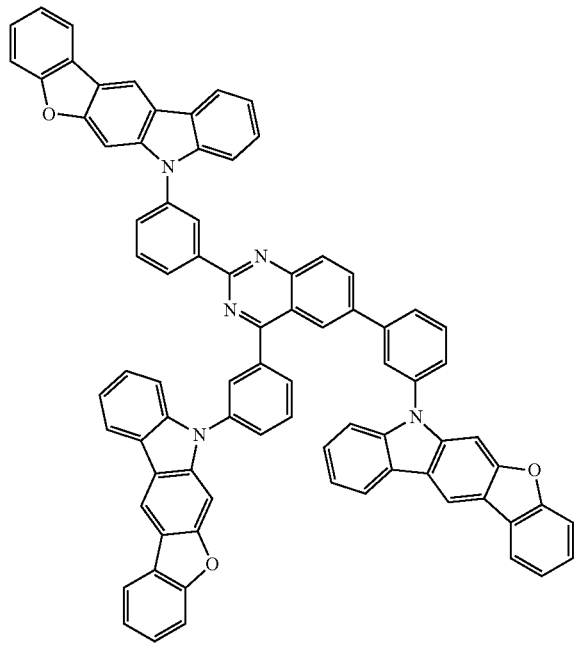
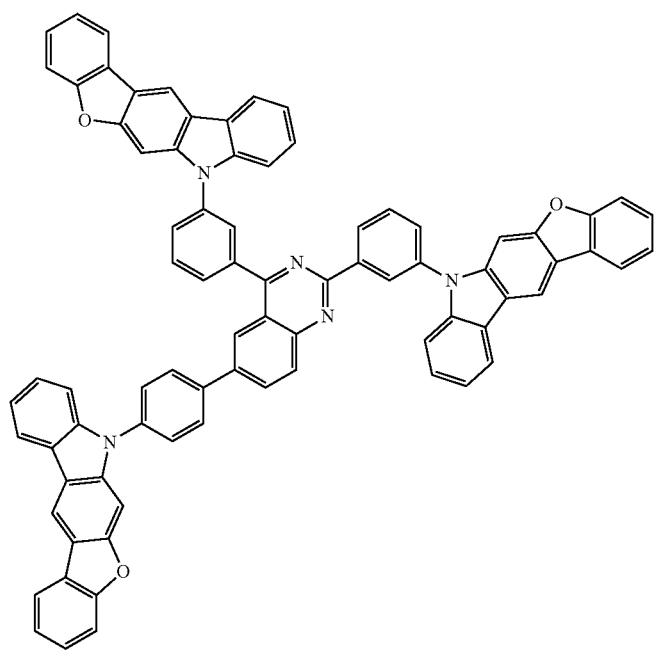

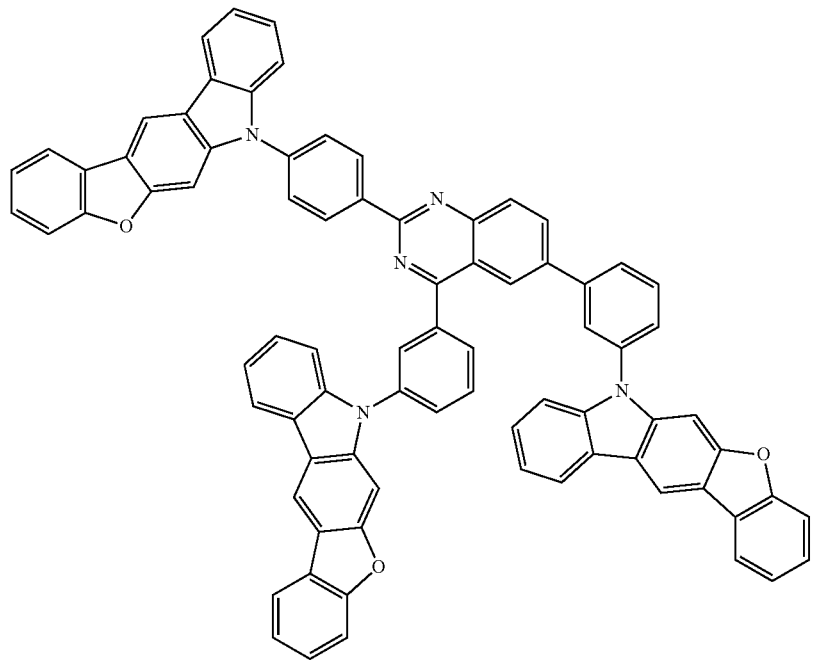
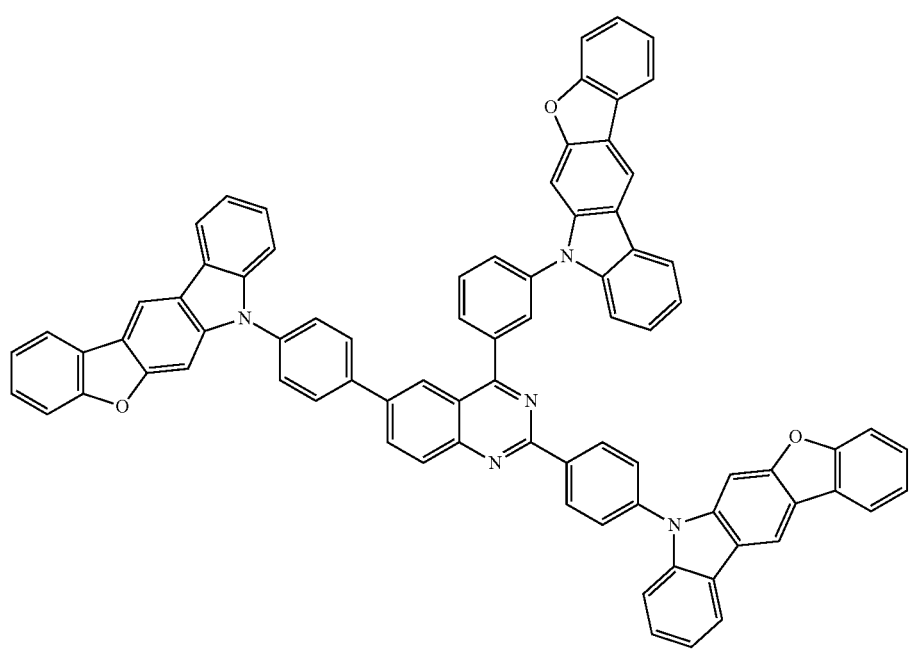

701 702
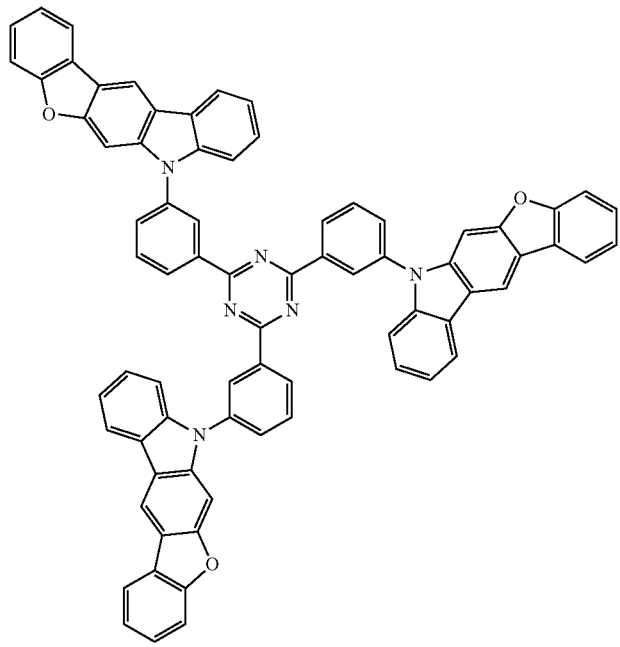
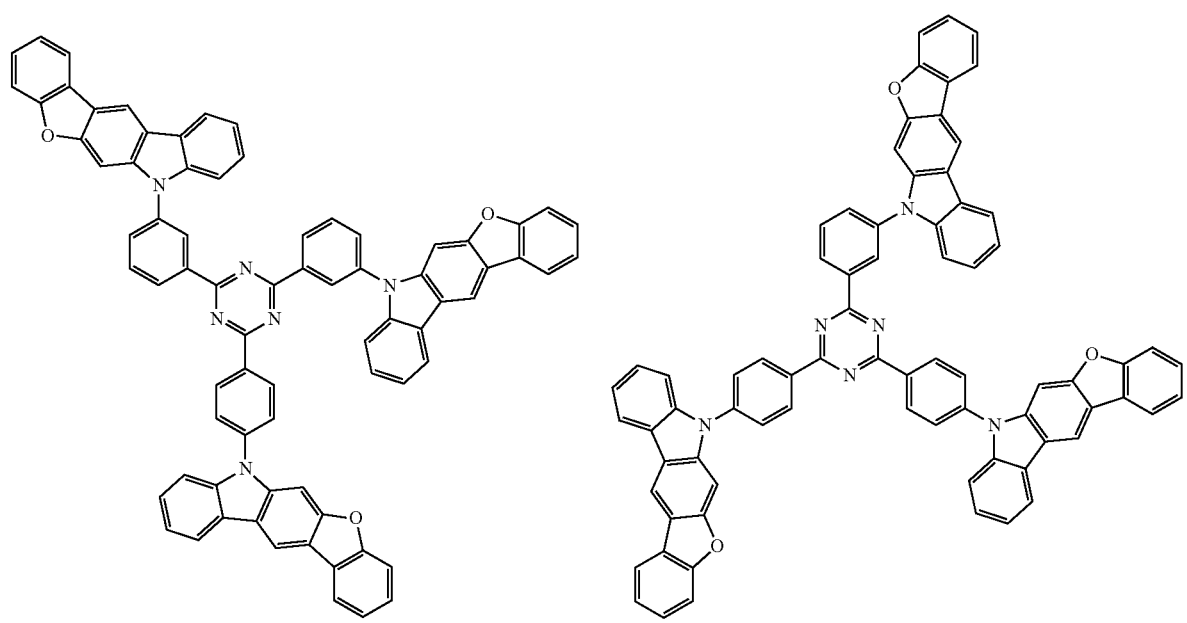

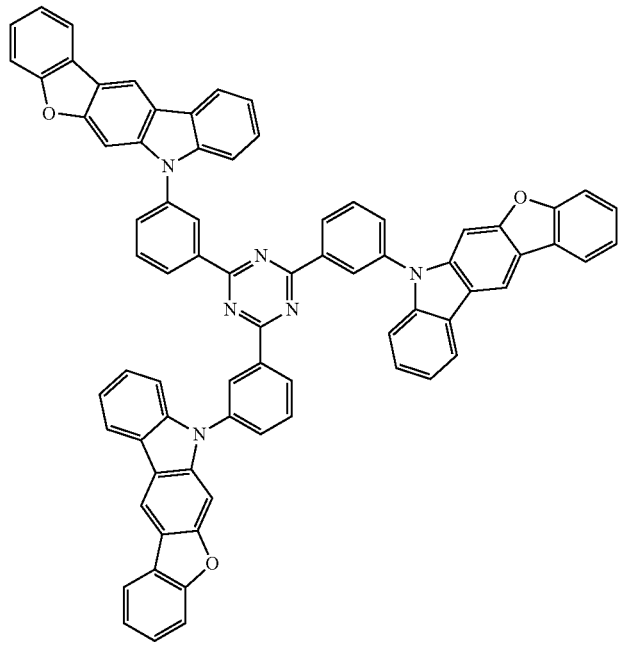
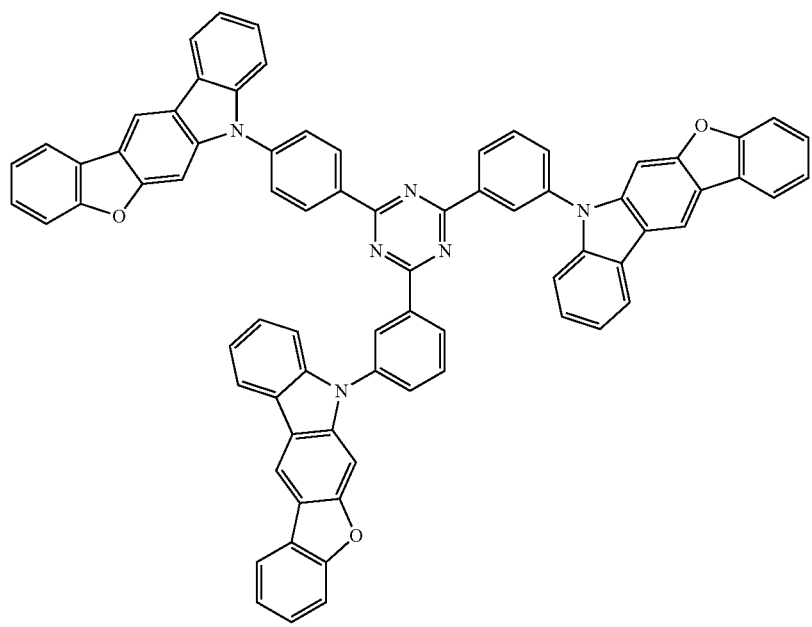

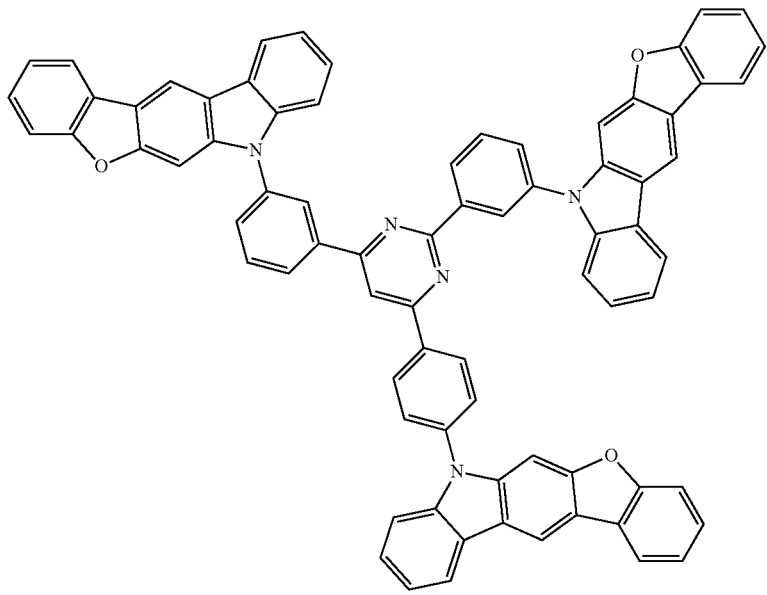
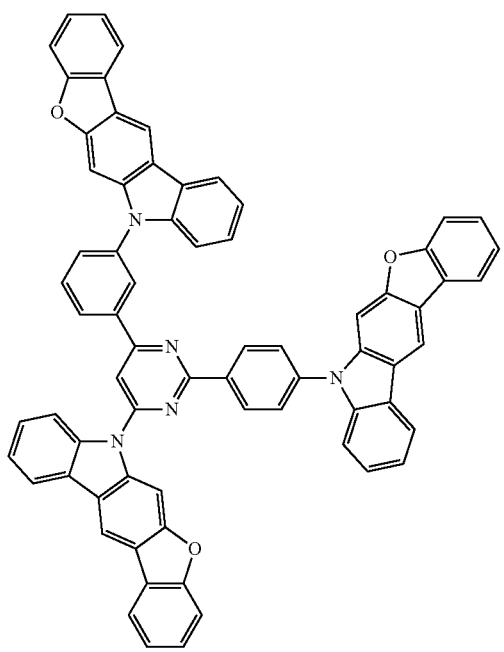

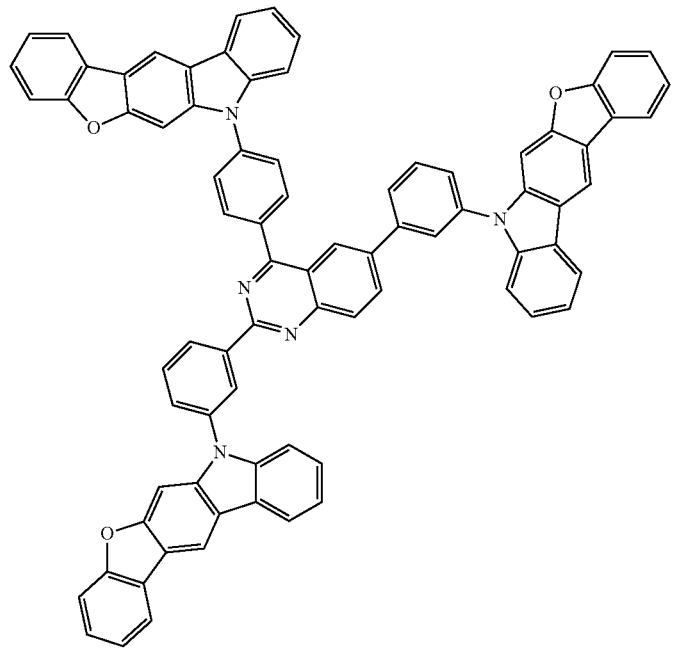
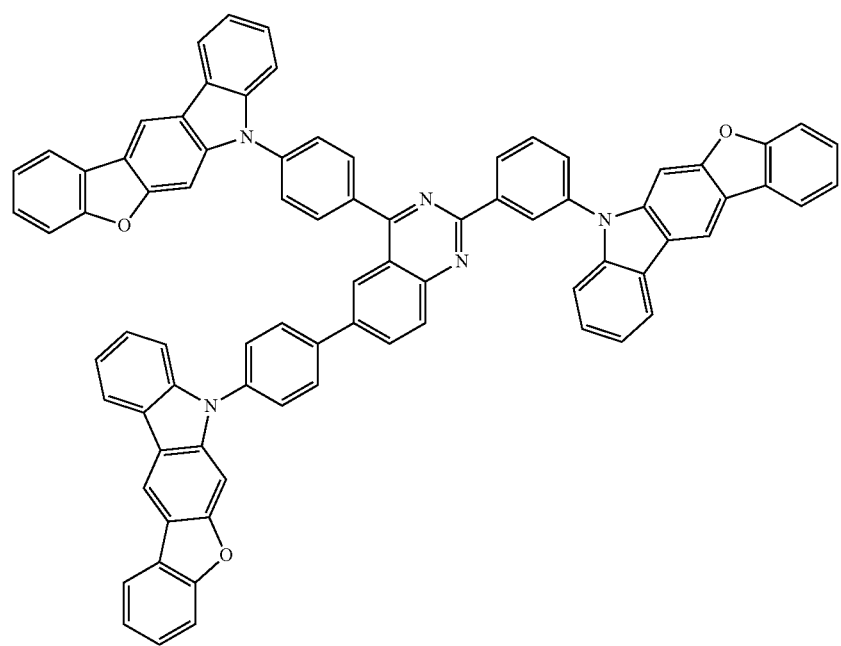

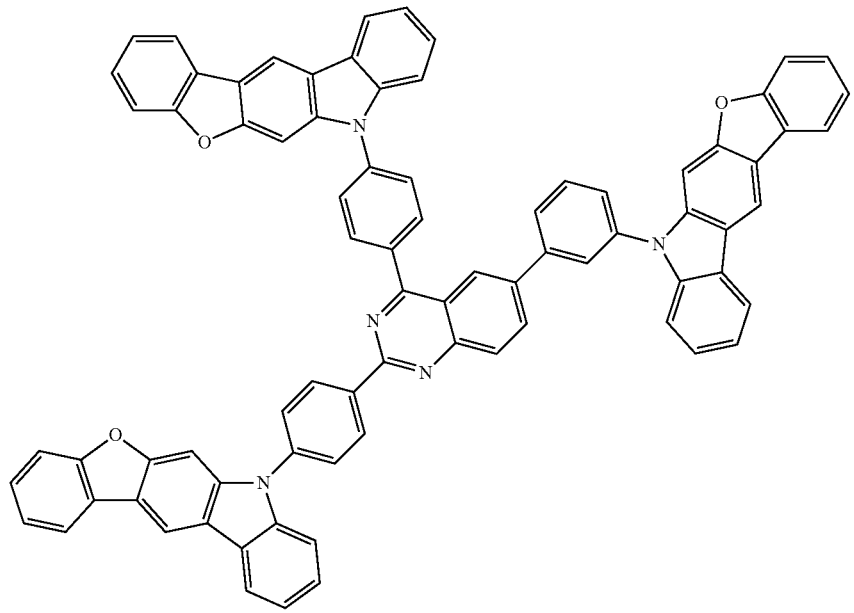
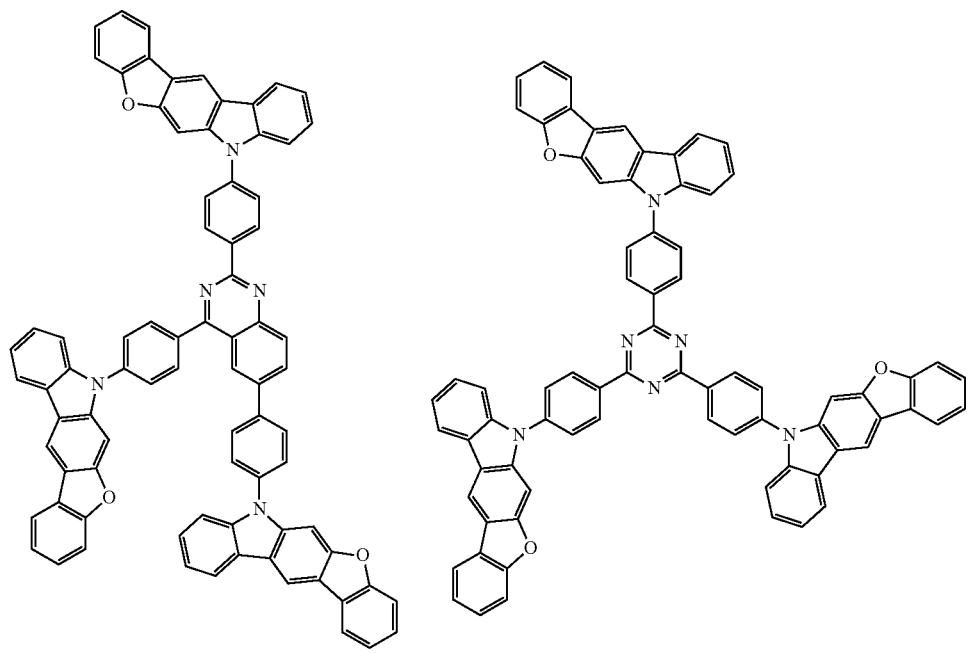

-continued
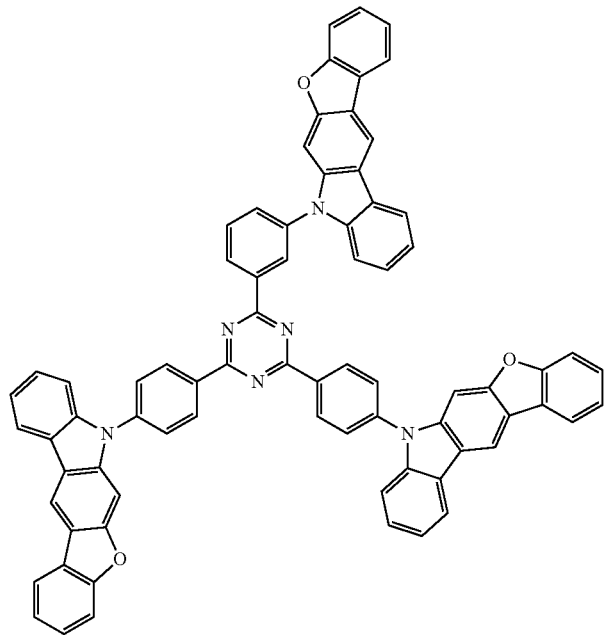
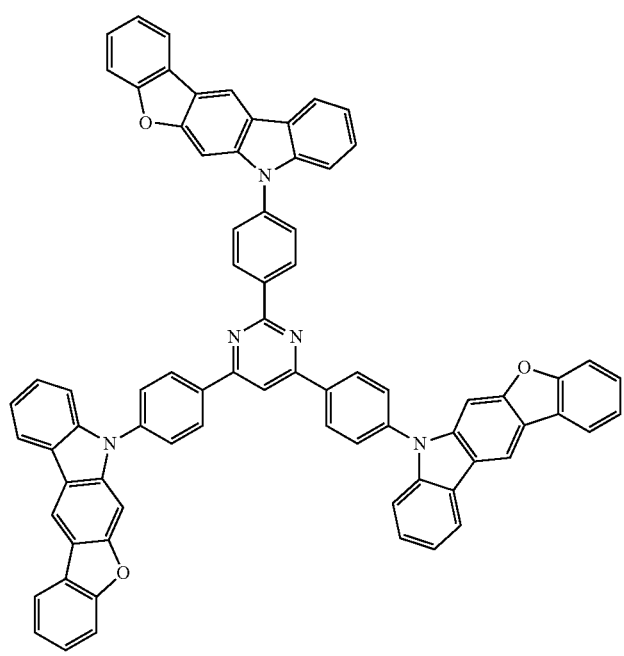

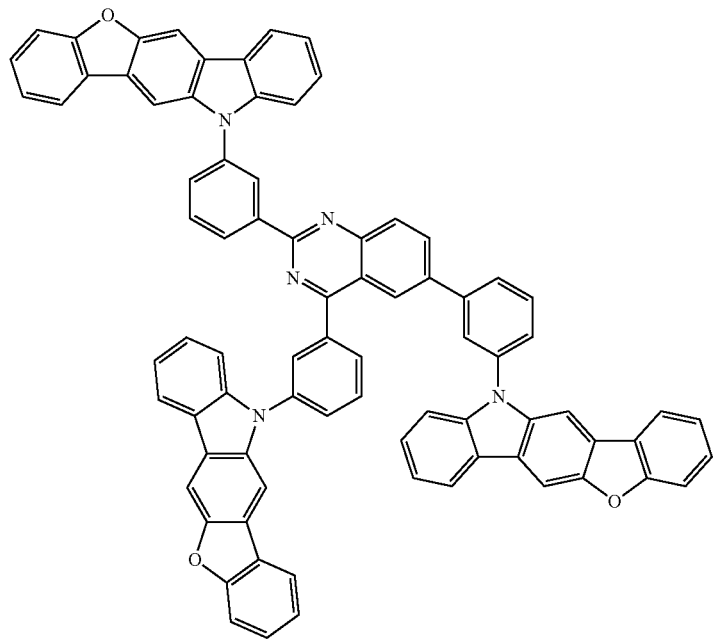
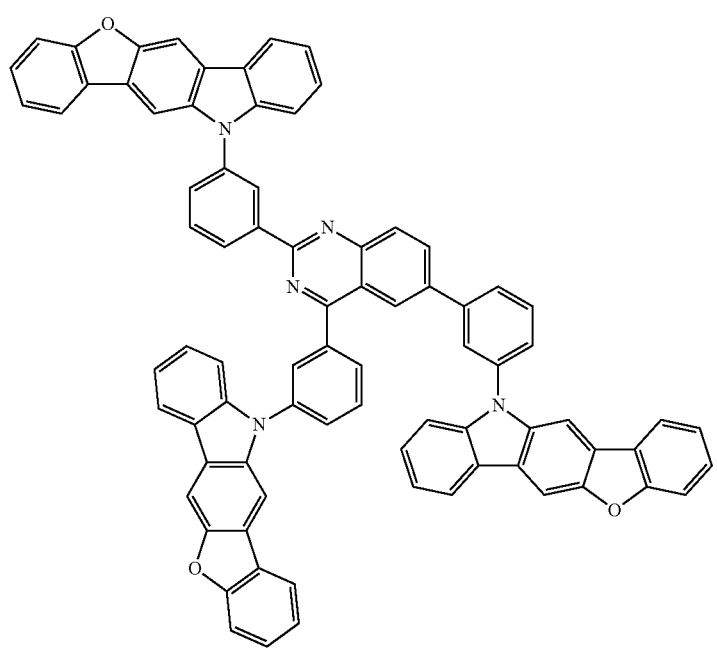

-continued
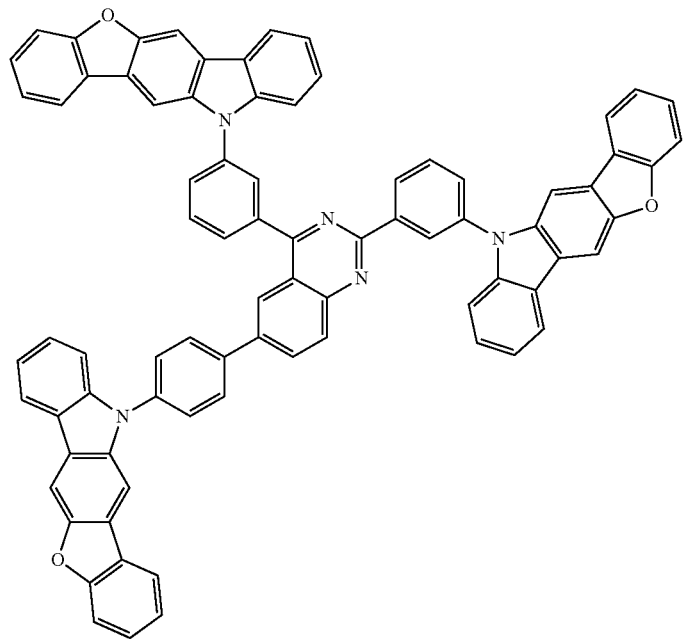

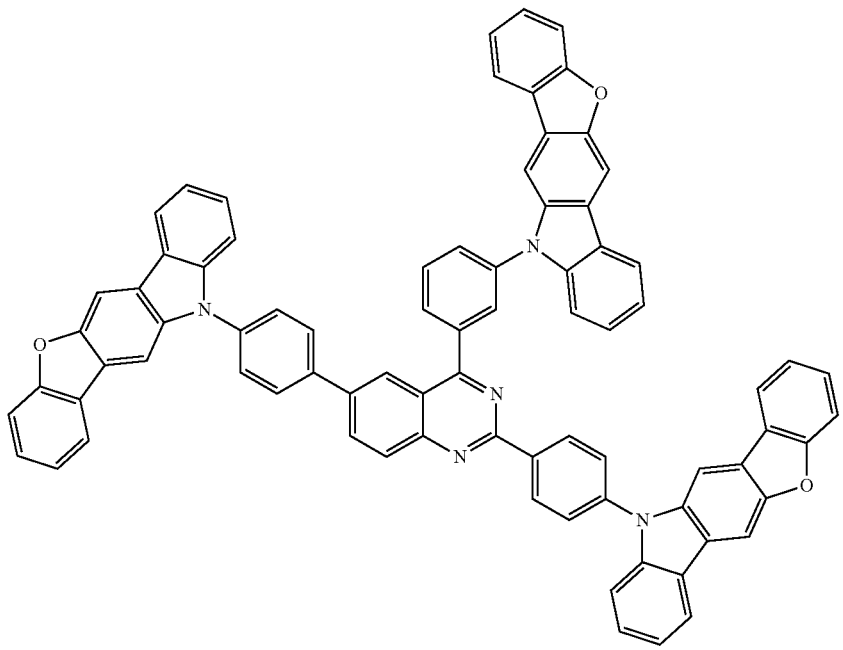
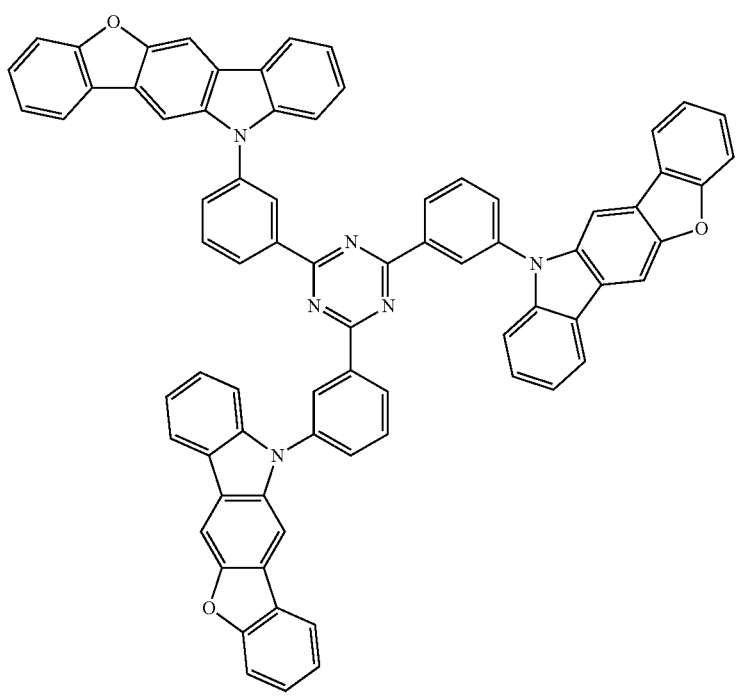

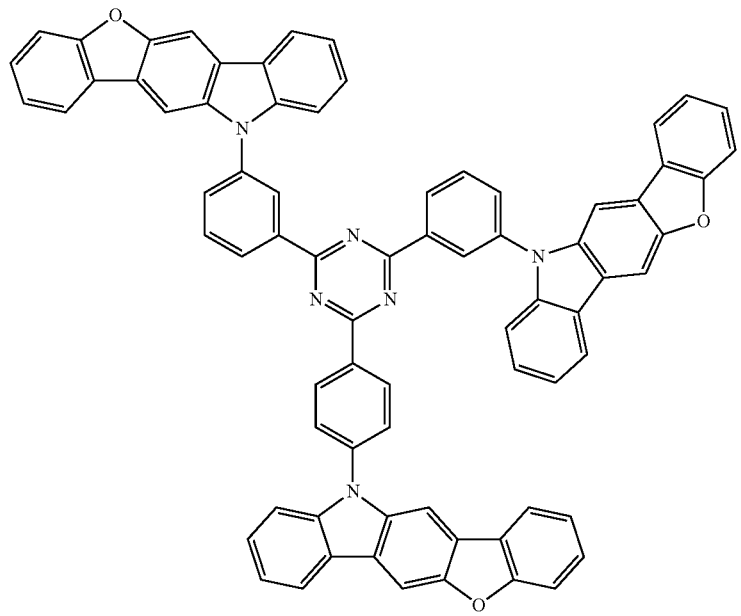
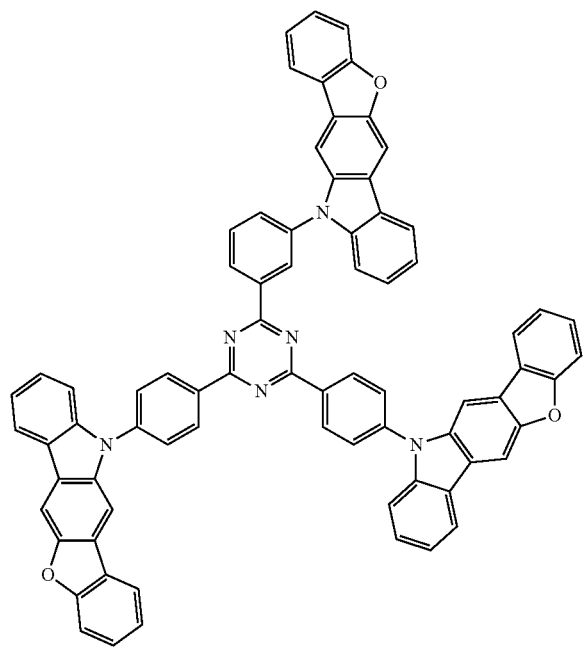

-continued
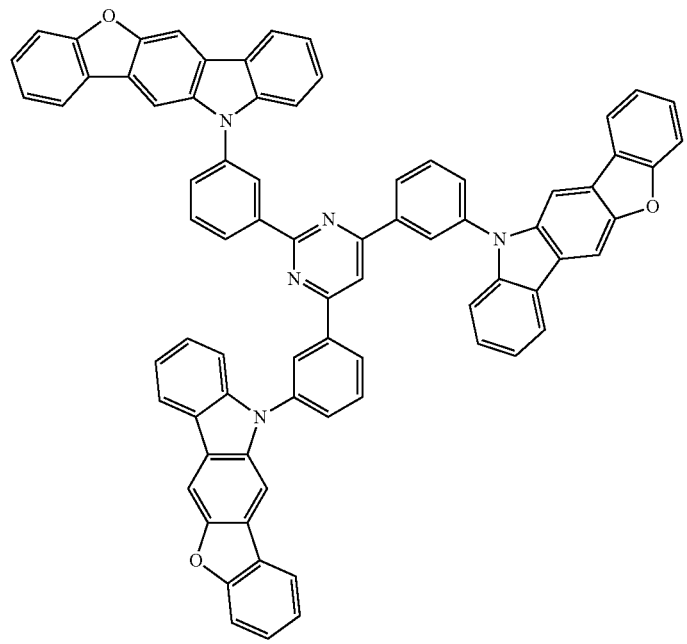
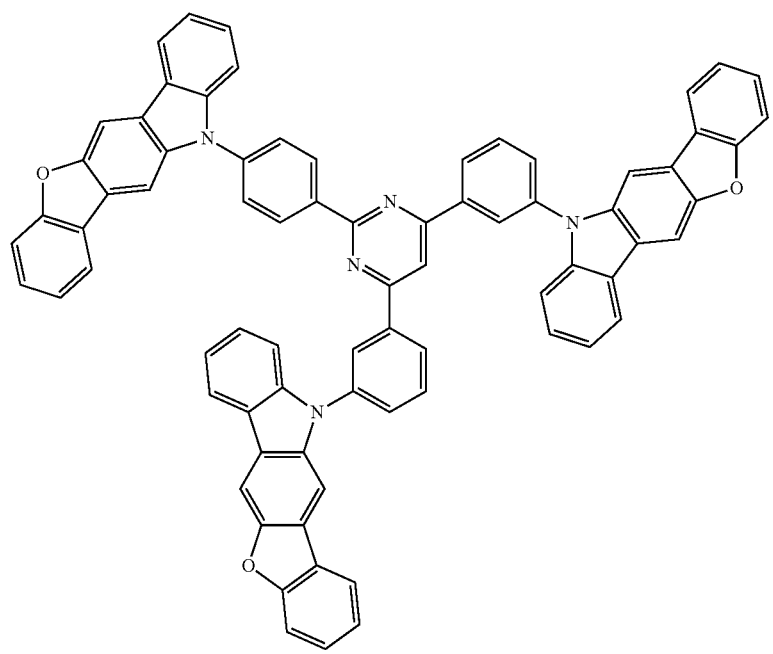

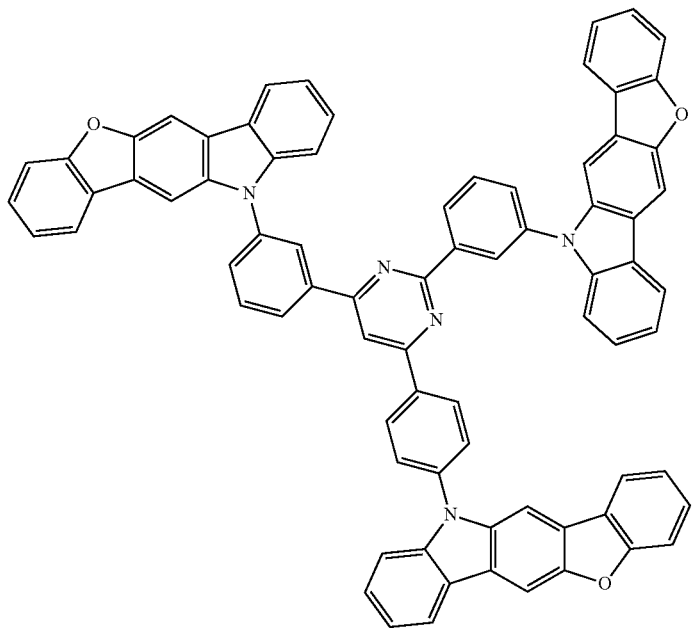

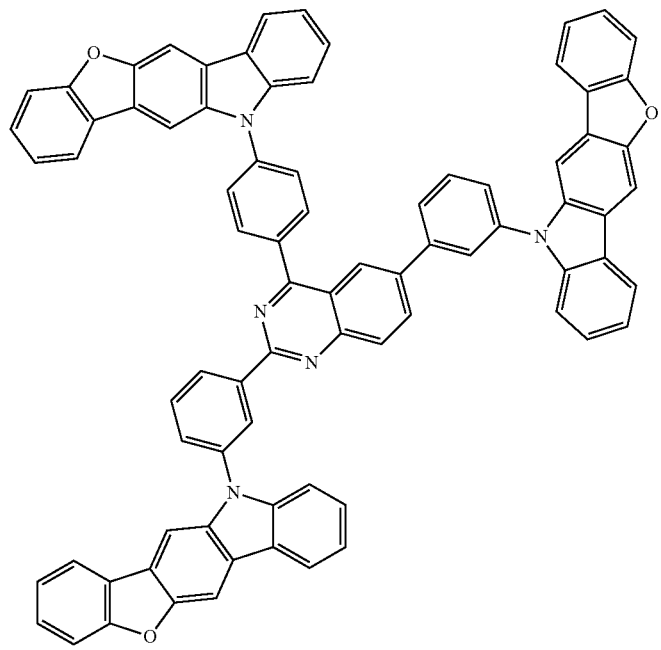
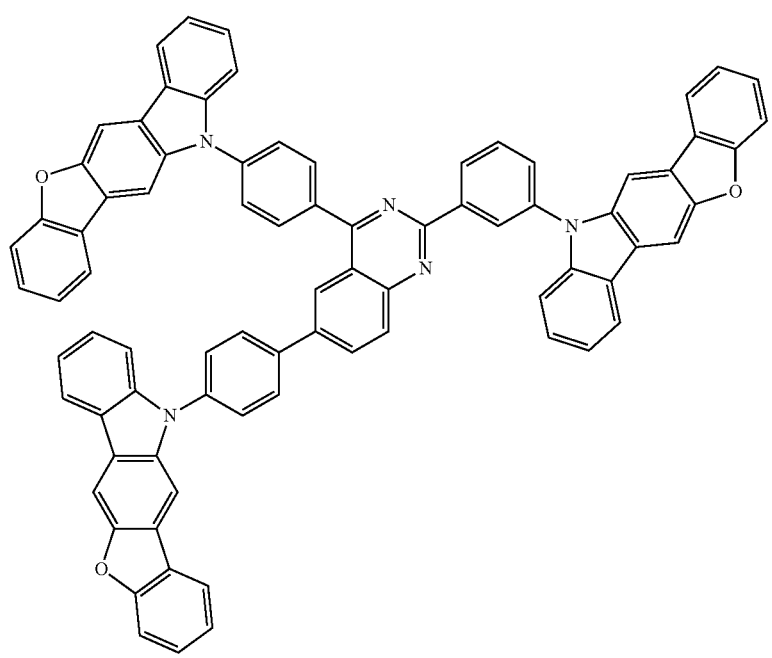

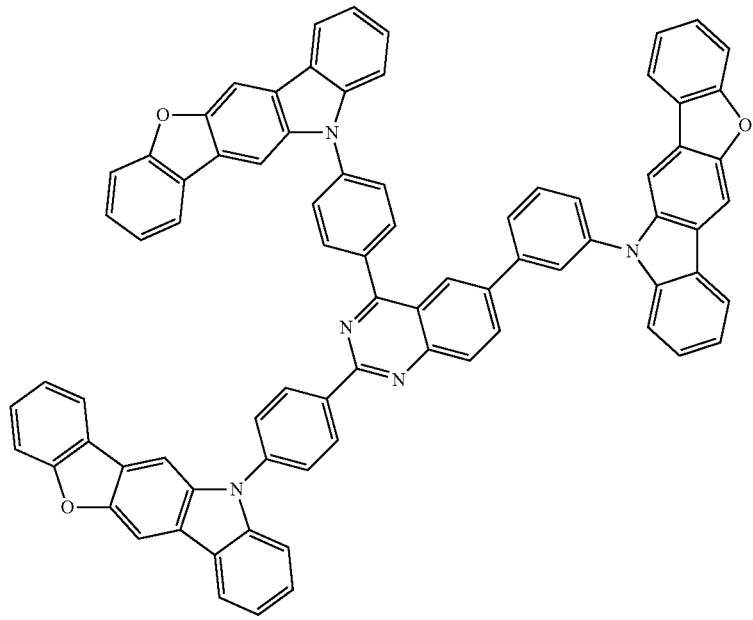
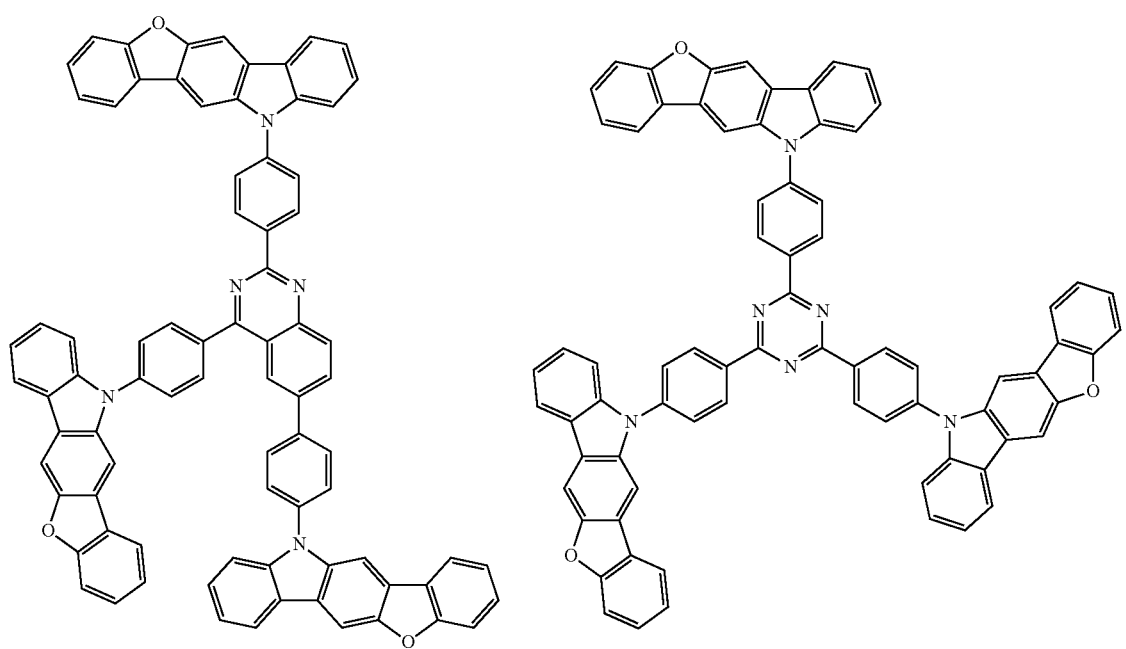

729 730
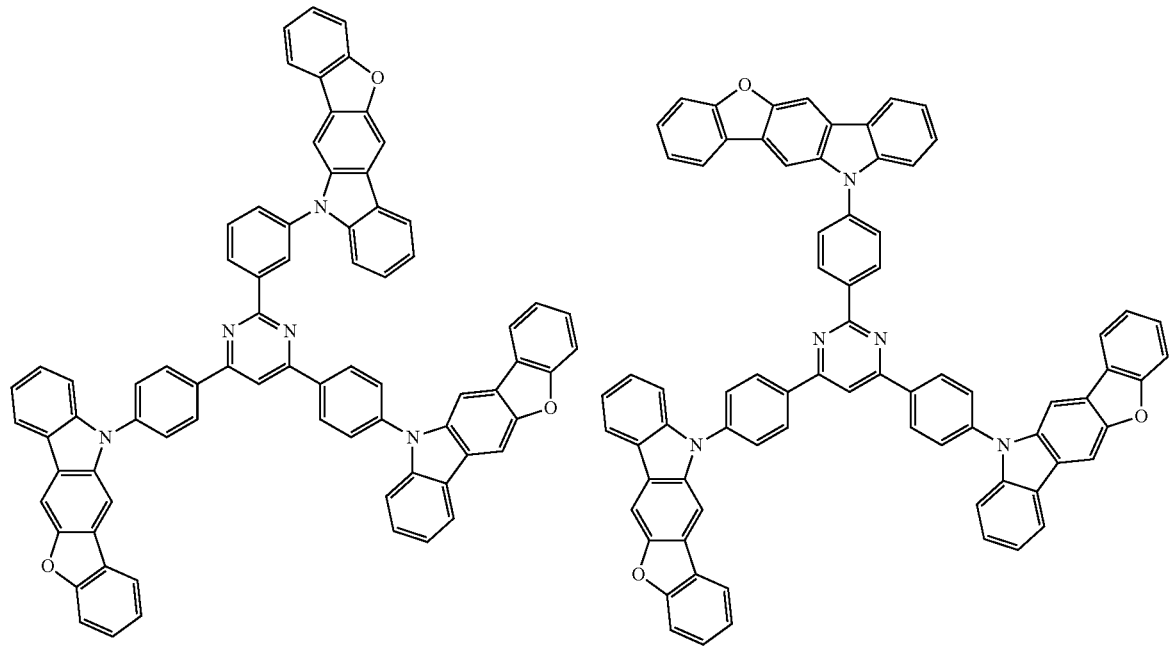
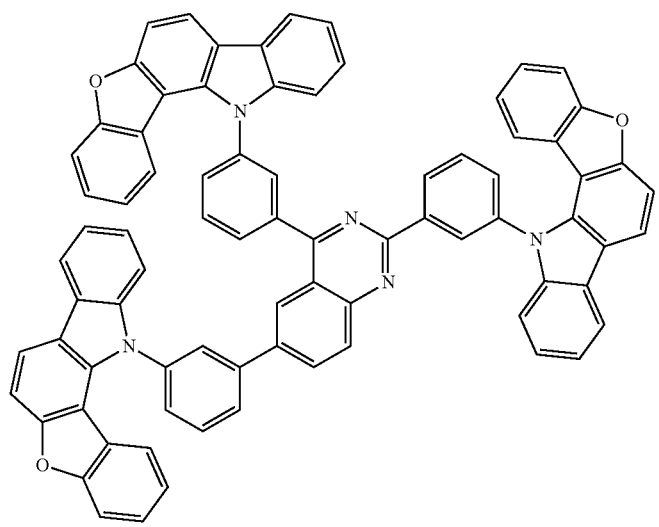

-continued
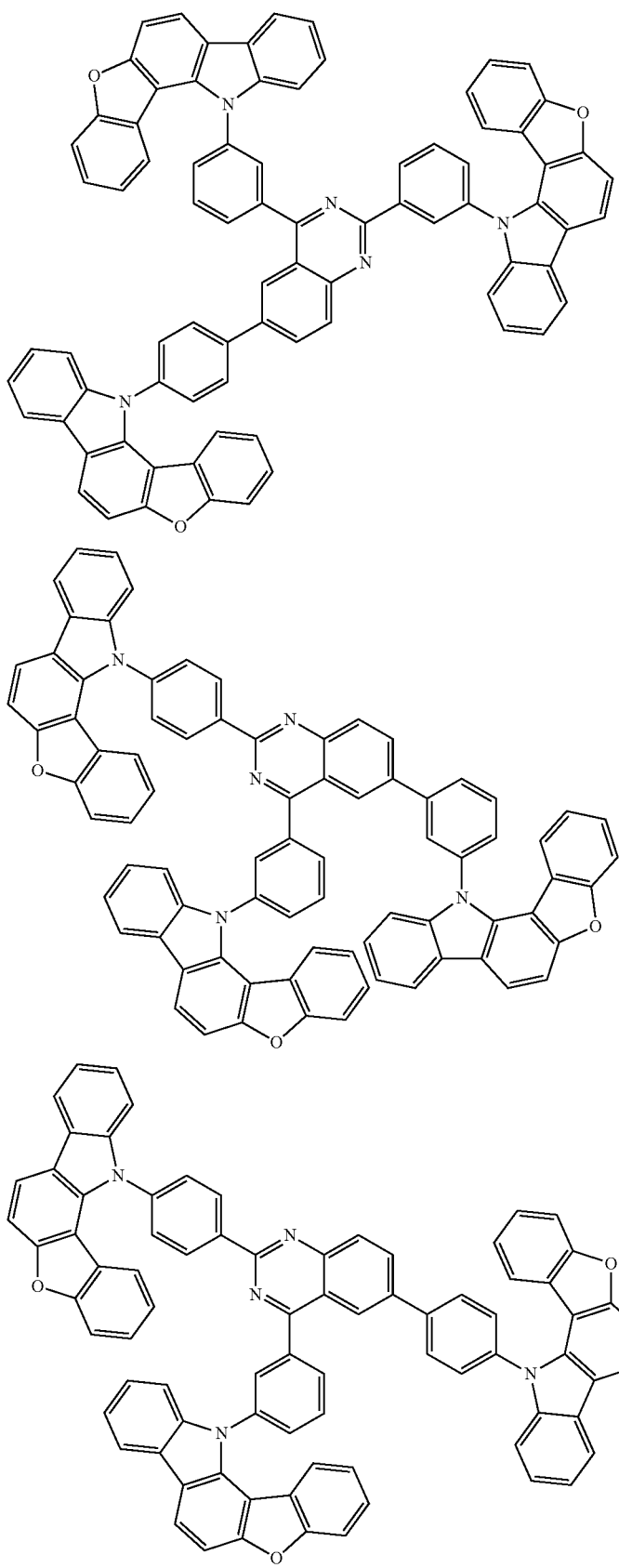

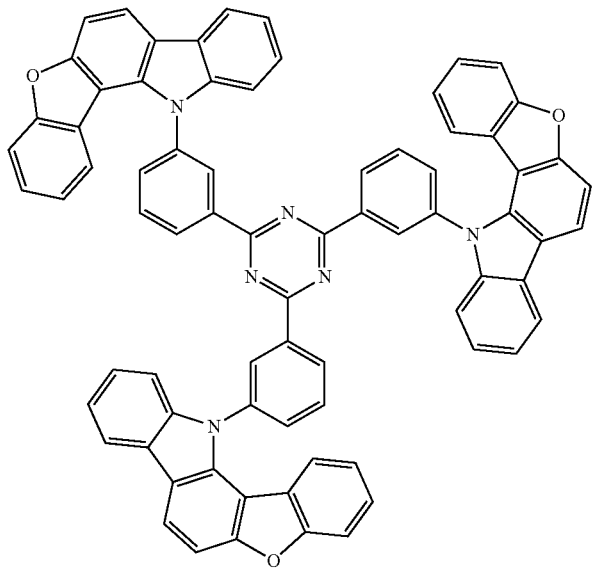
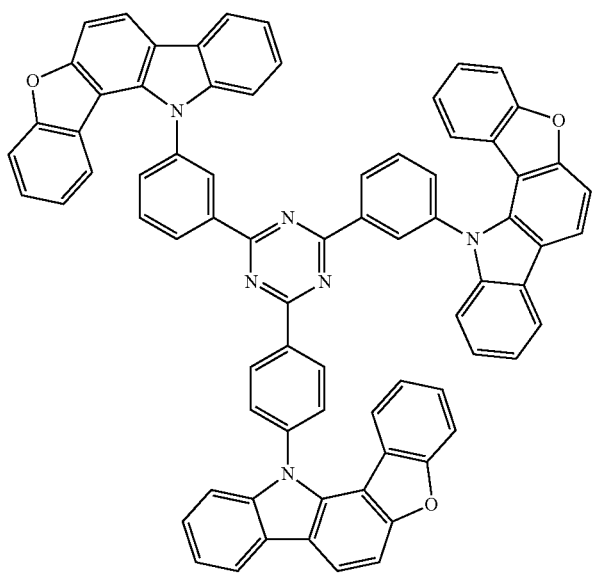

-continued
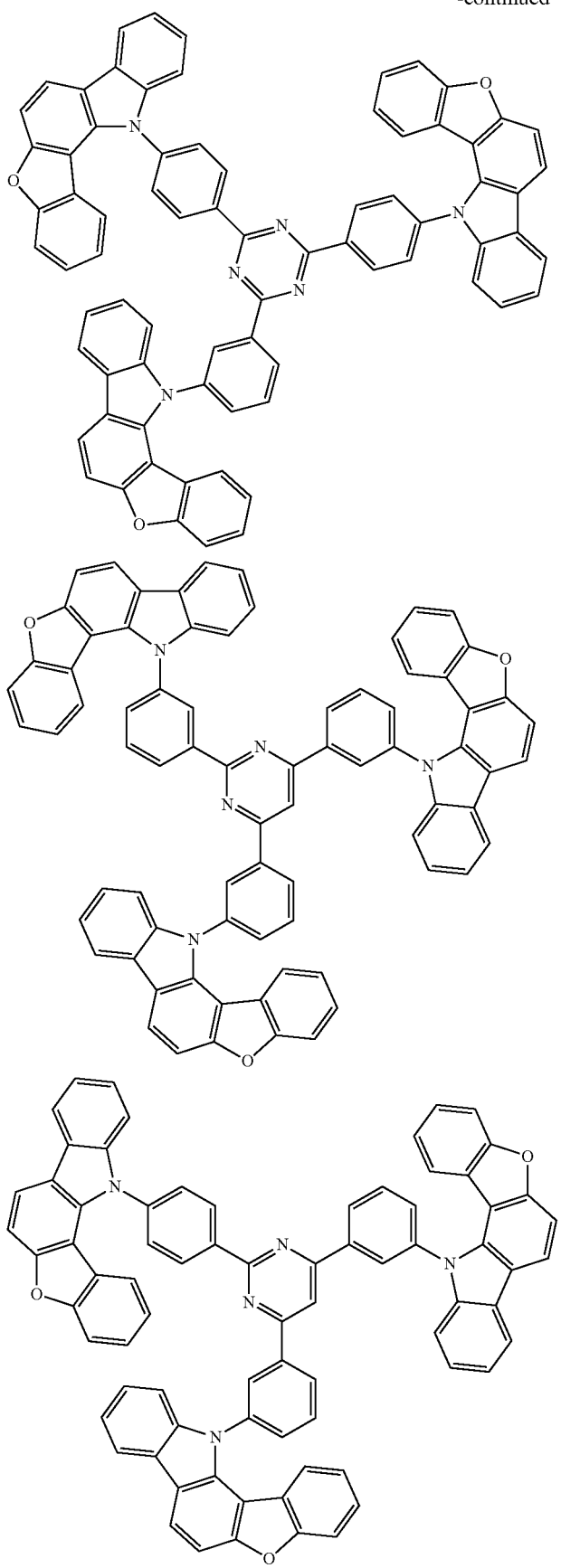

-continued
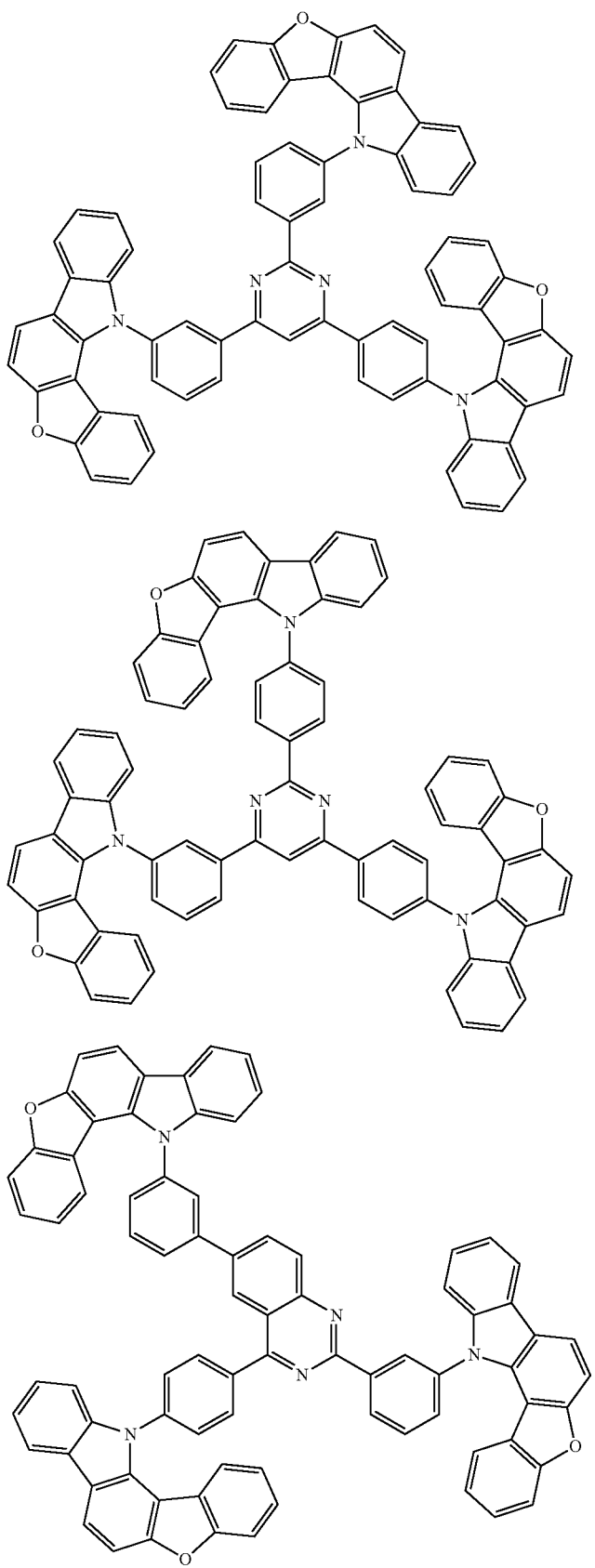

-continued
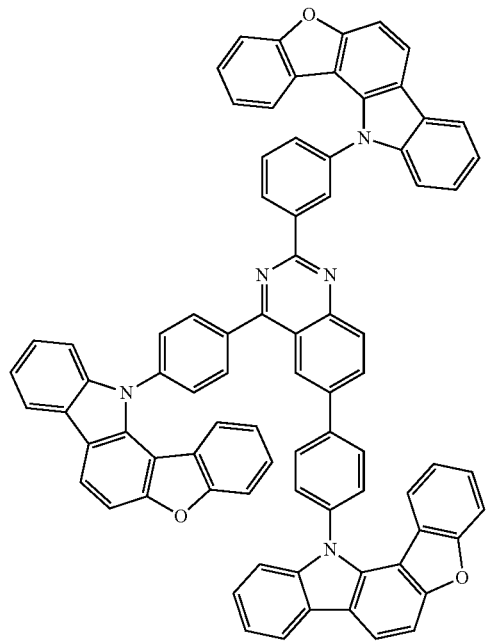
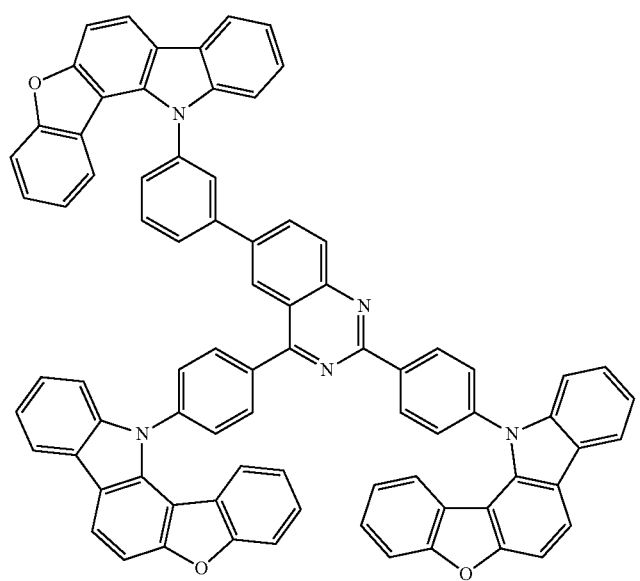

-continued
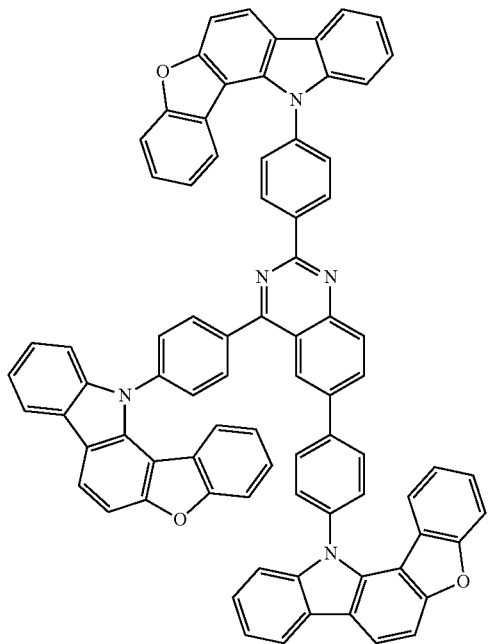
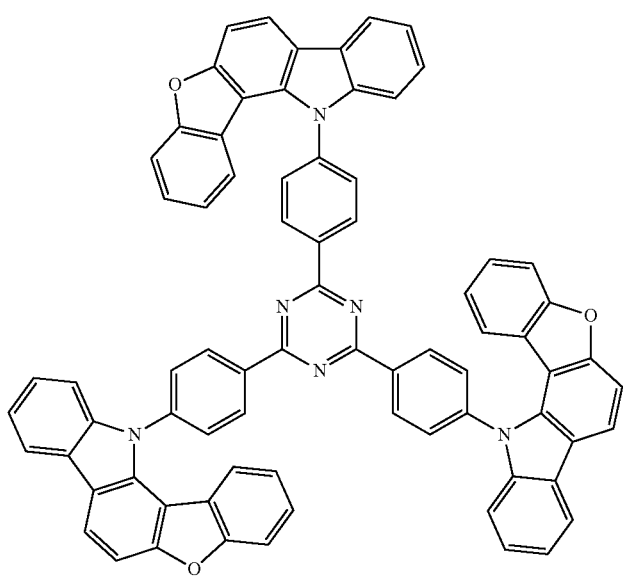

-continued
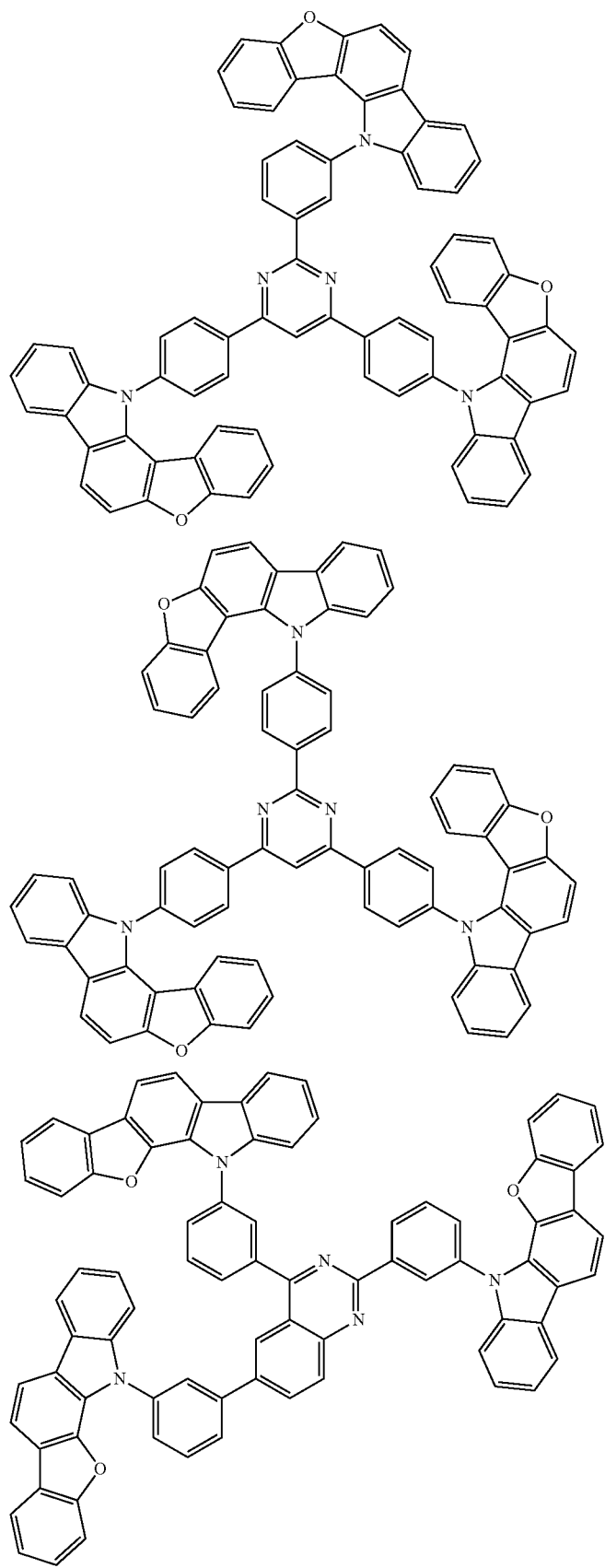

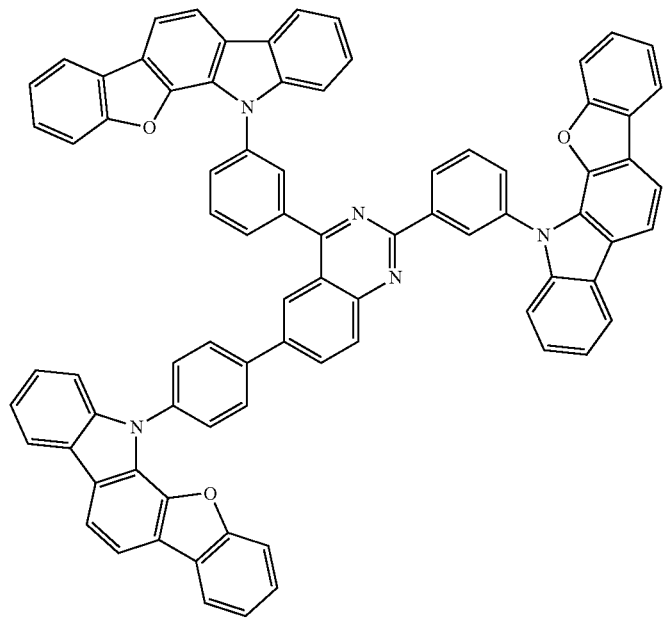
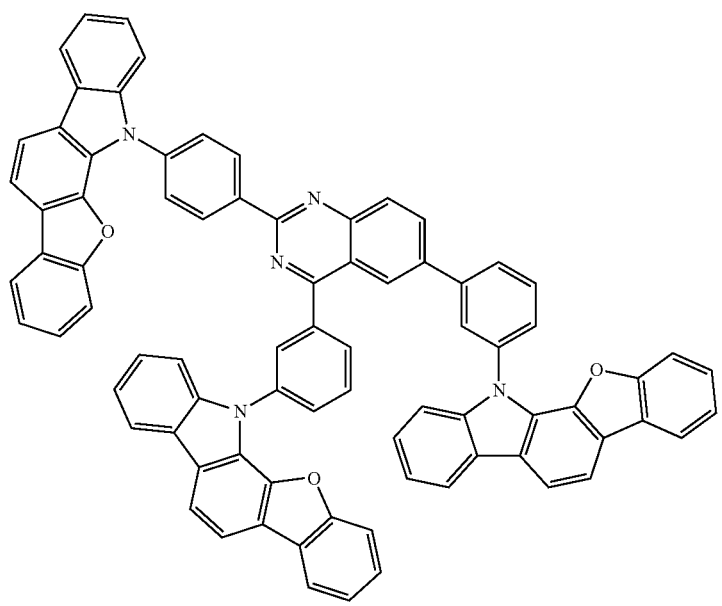

-continued
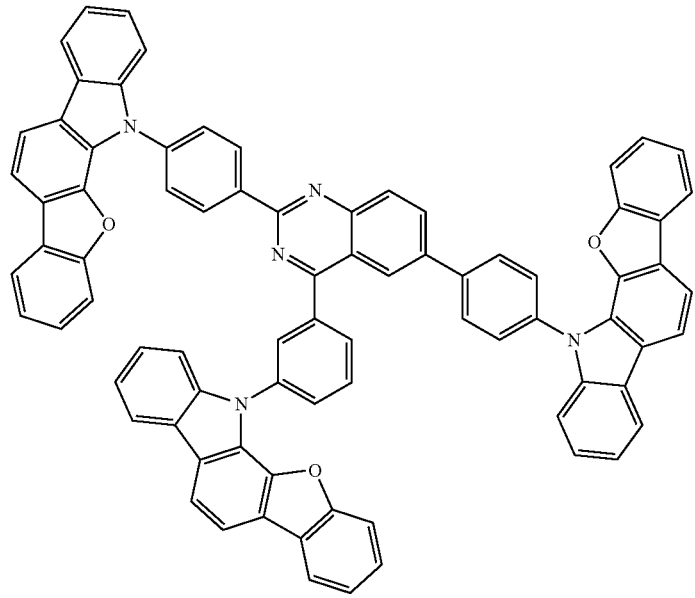
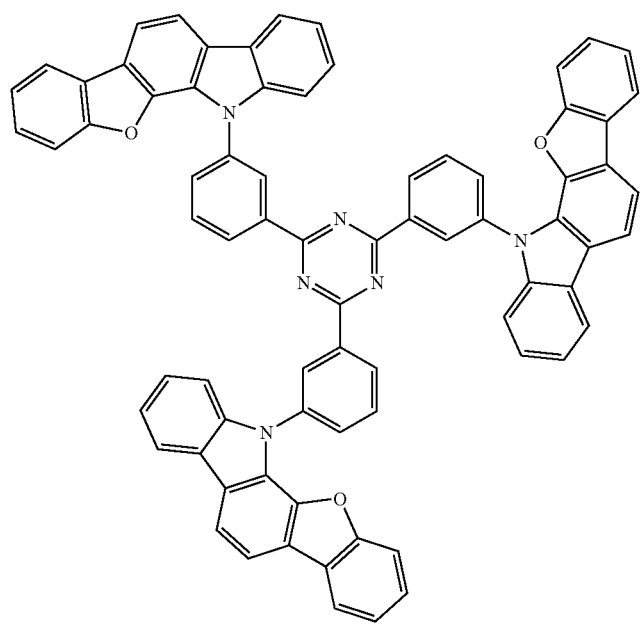

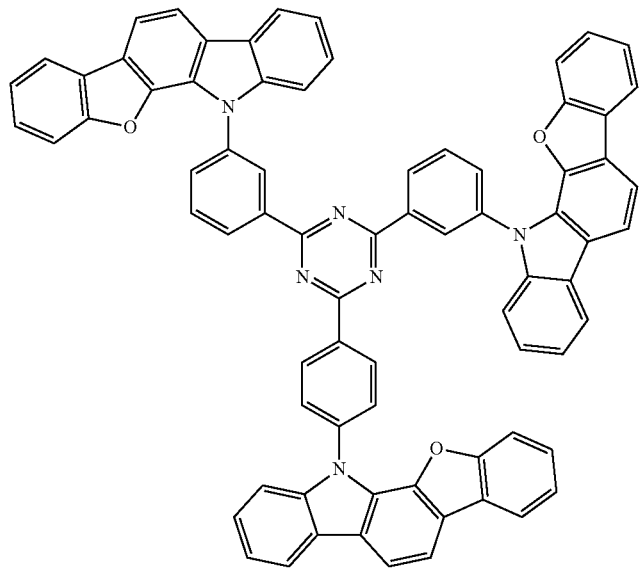
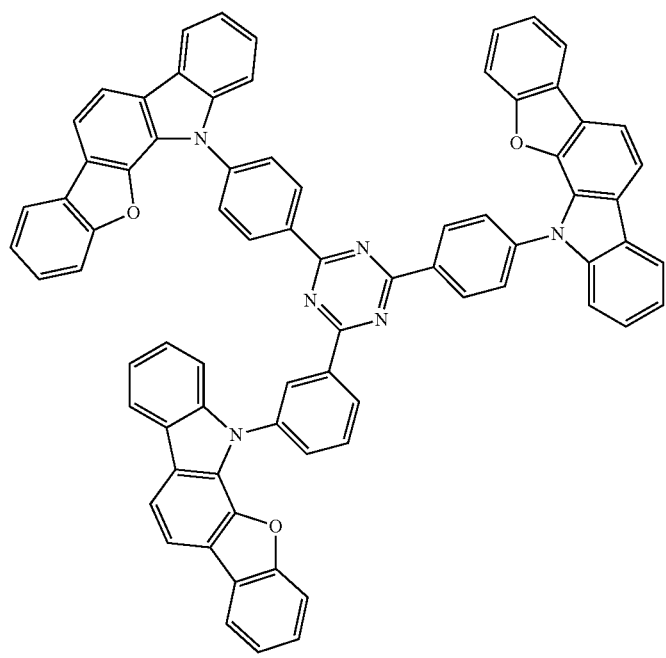

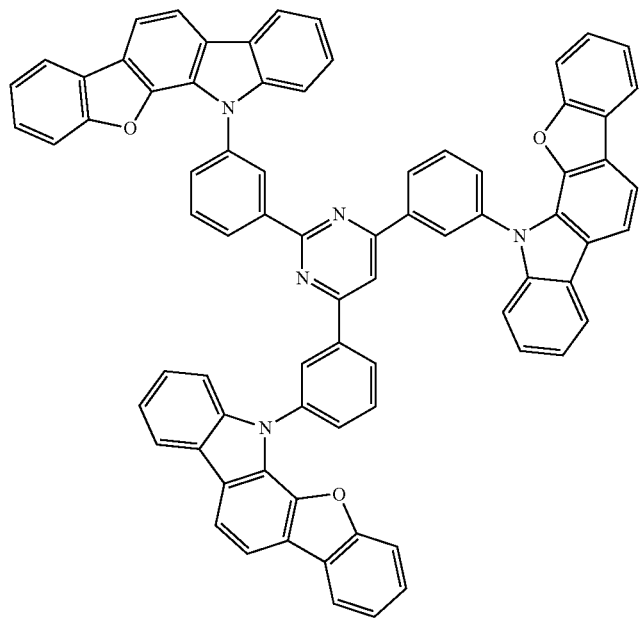
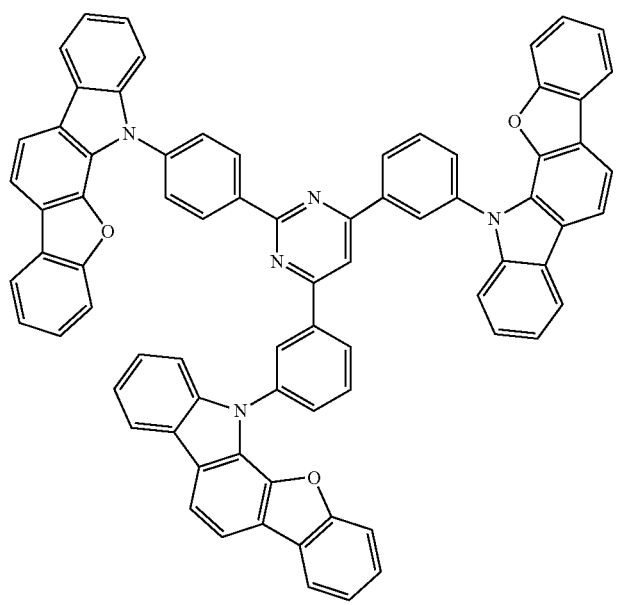

-continued
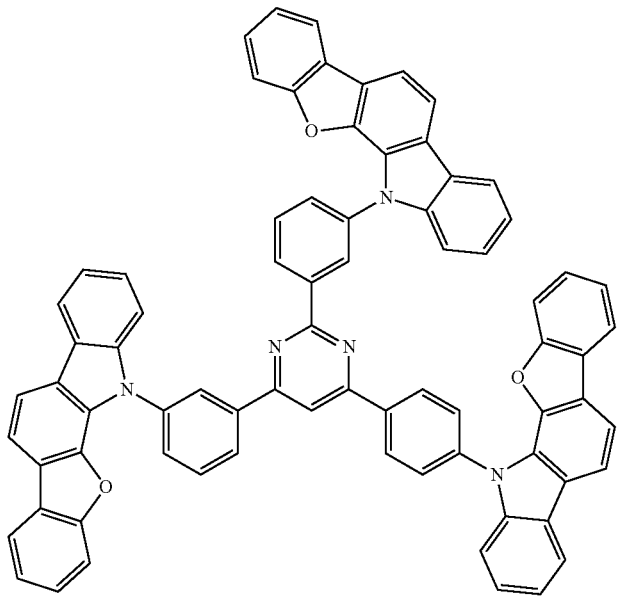
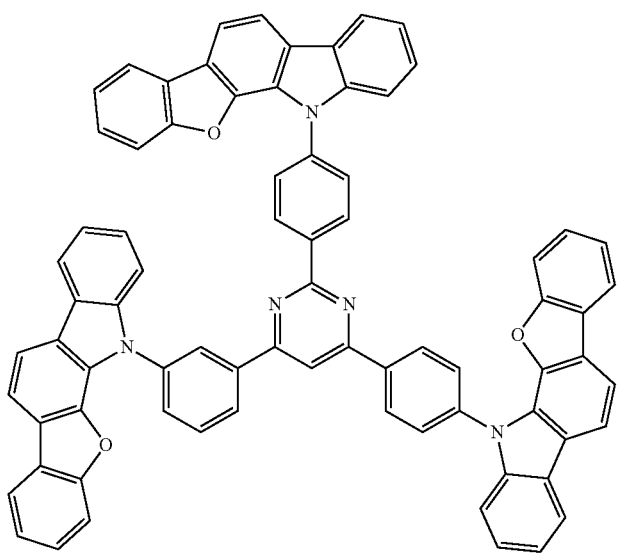

-continued
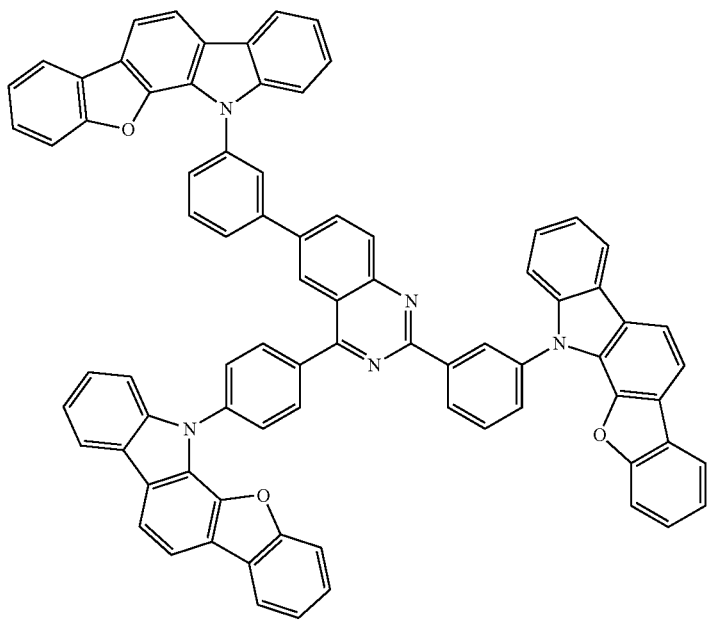
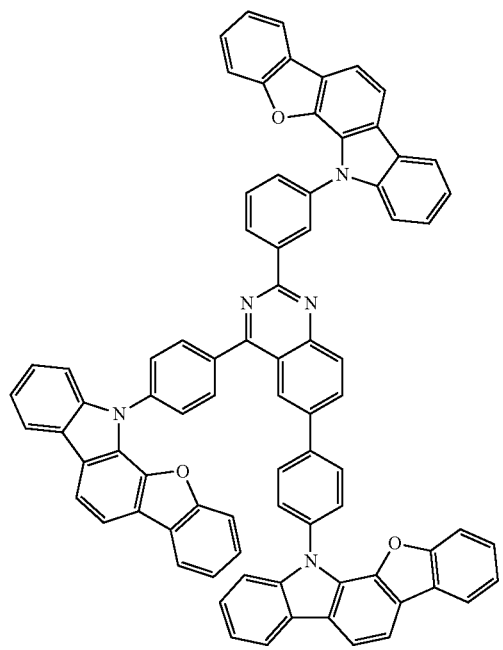

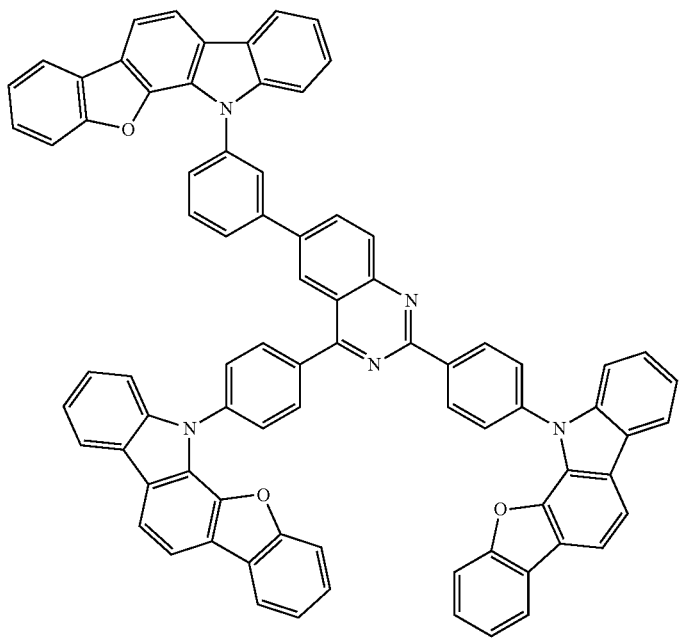
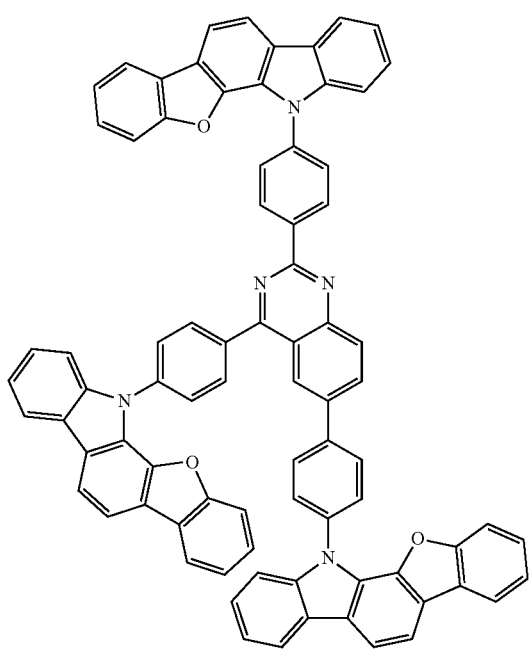

-continued
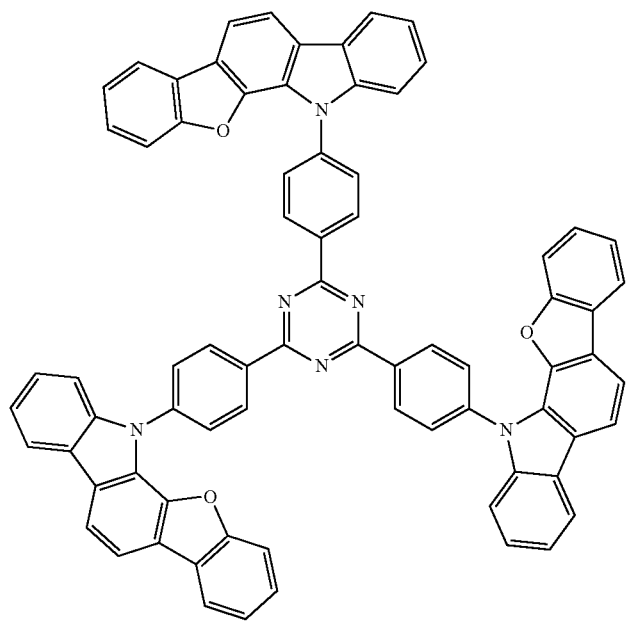
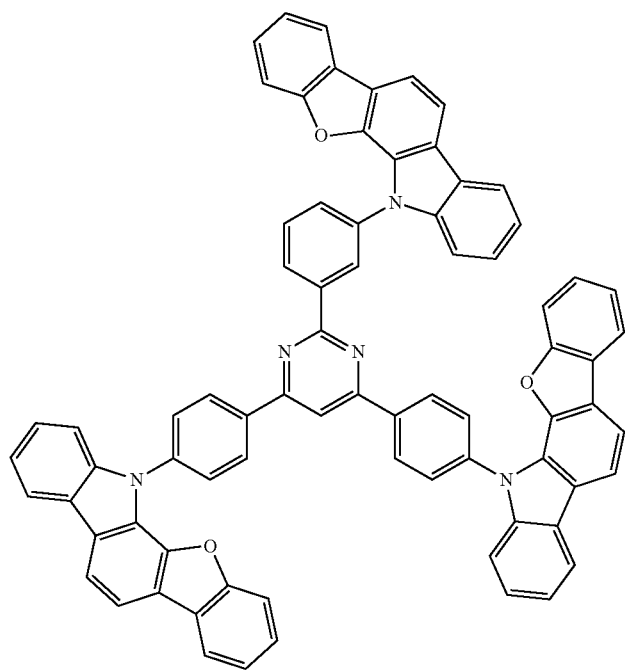

-continued
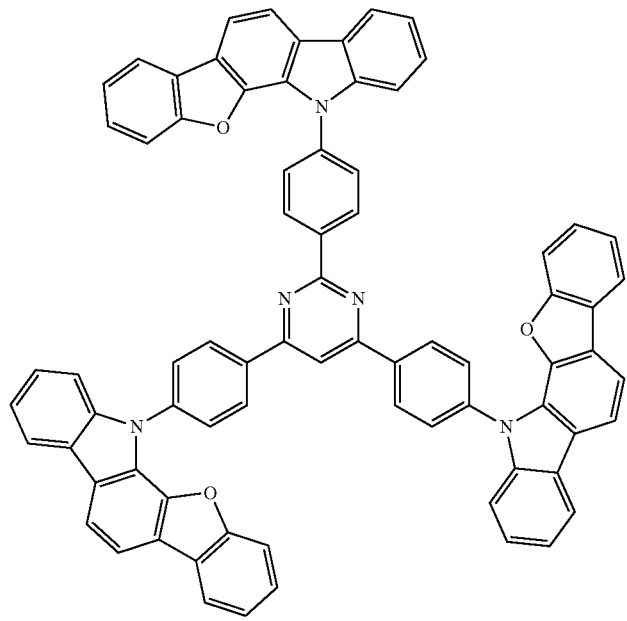
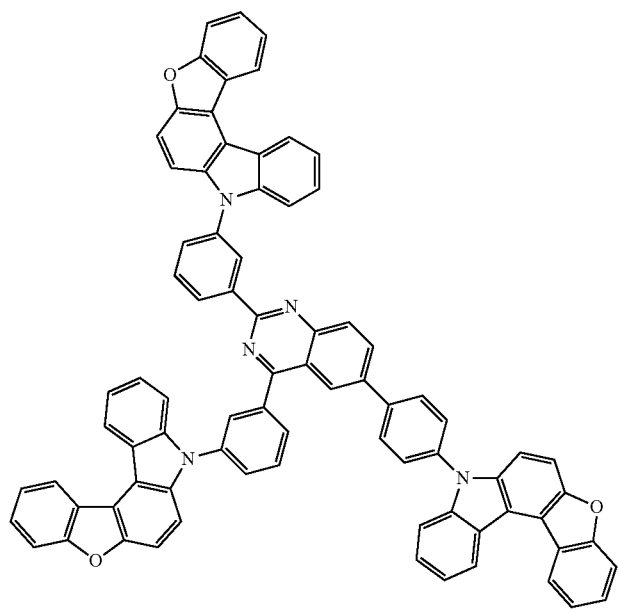

-continued
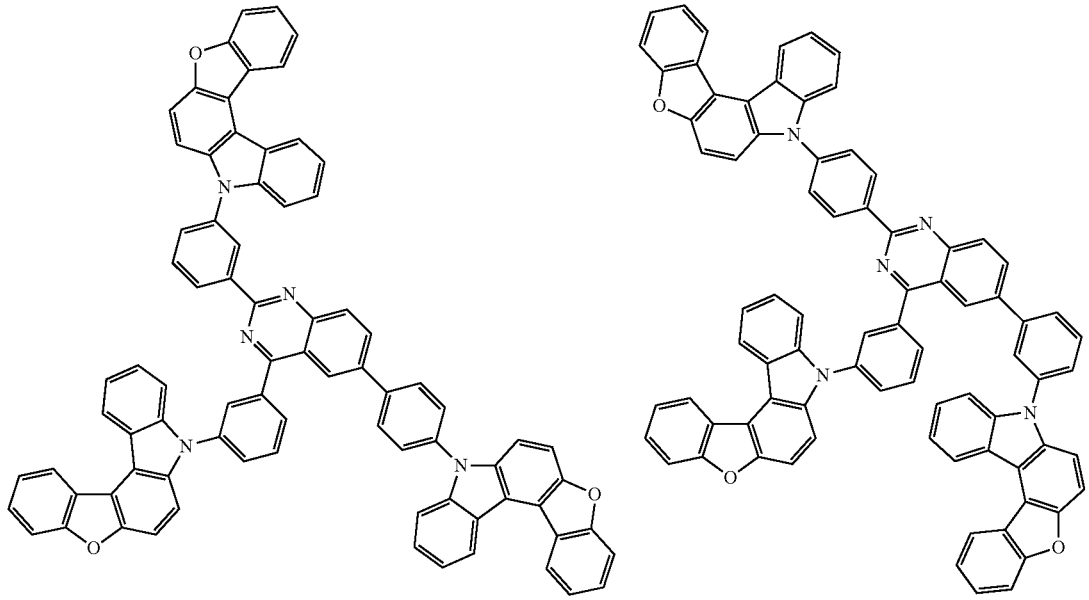
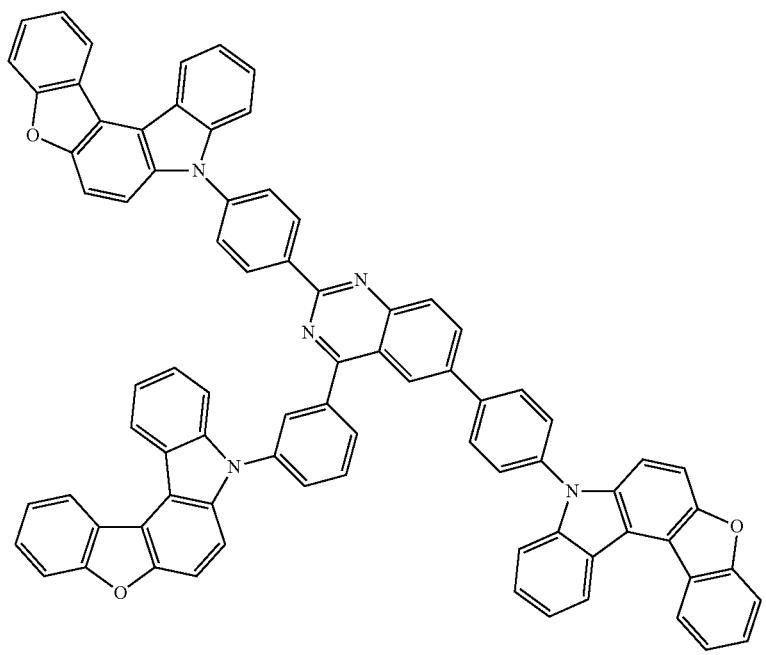

-continued
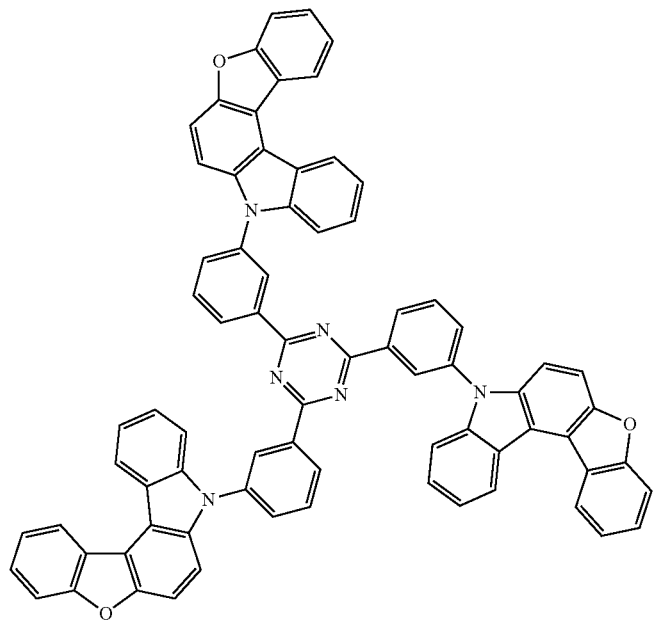
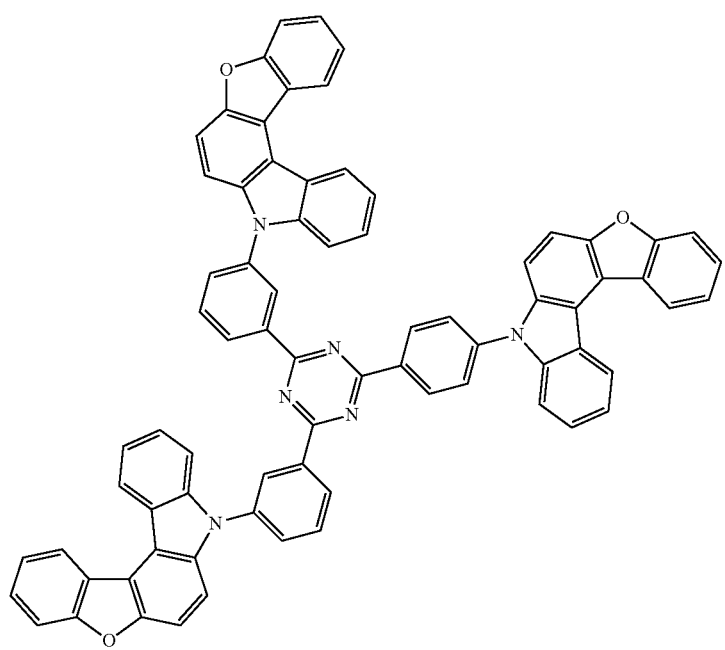

-continued
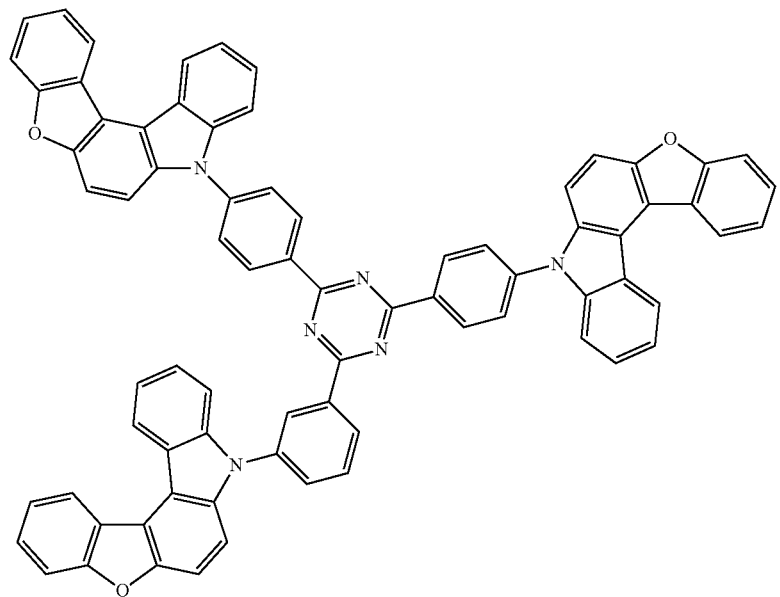
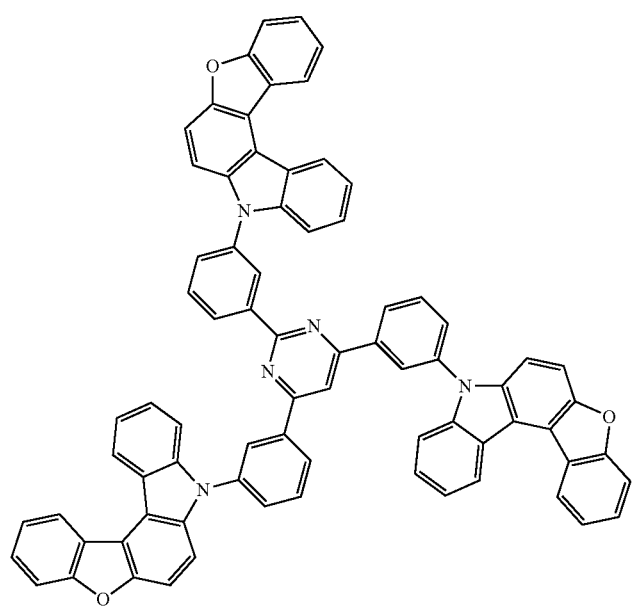

-continued
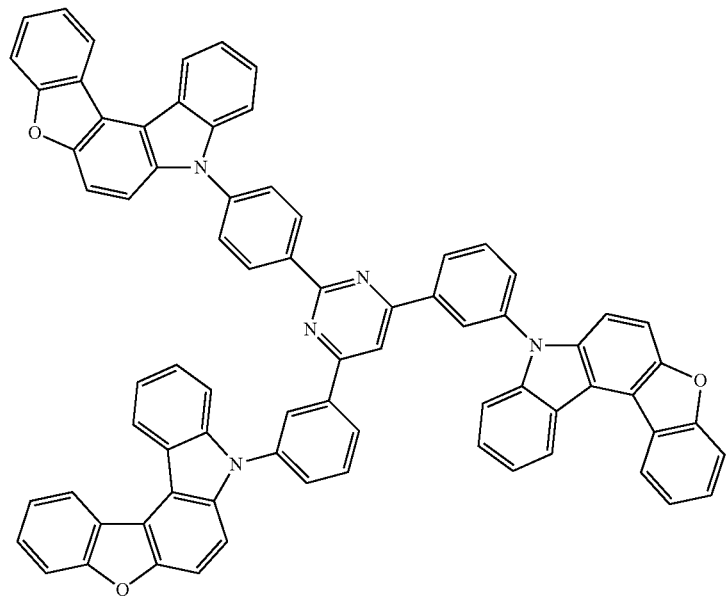
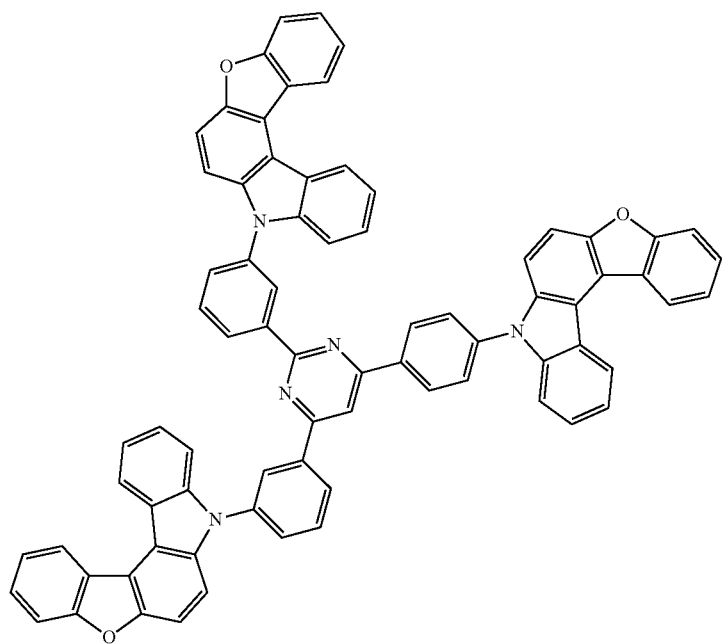

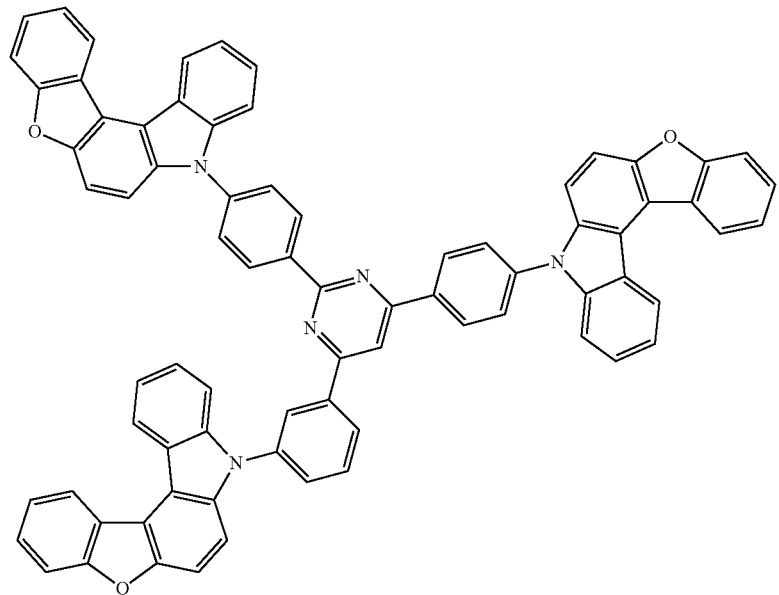
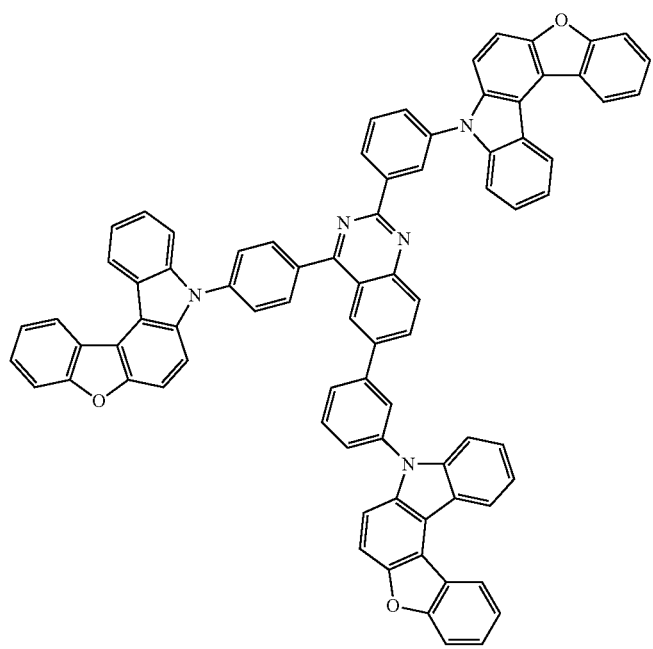

-continued
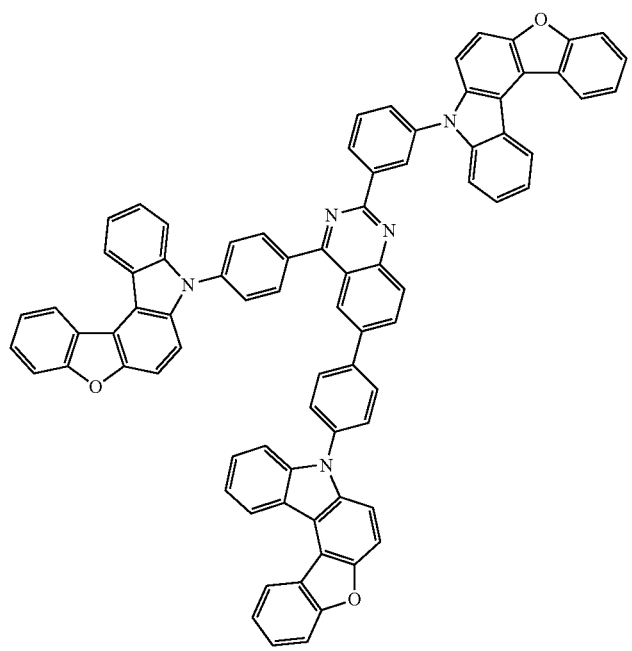
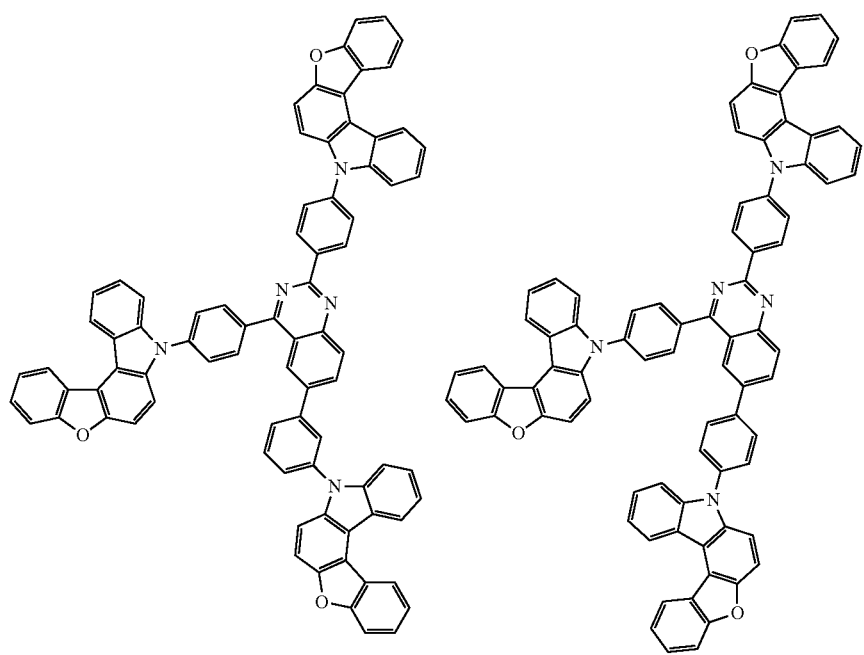

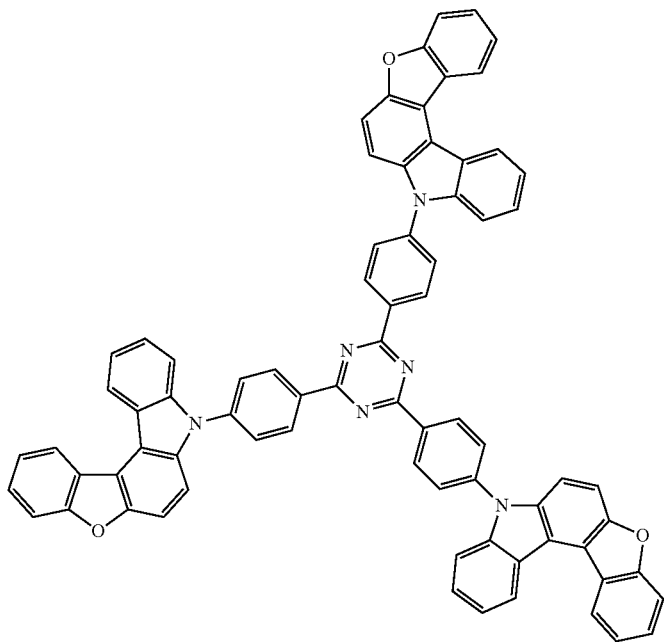
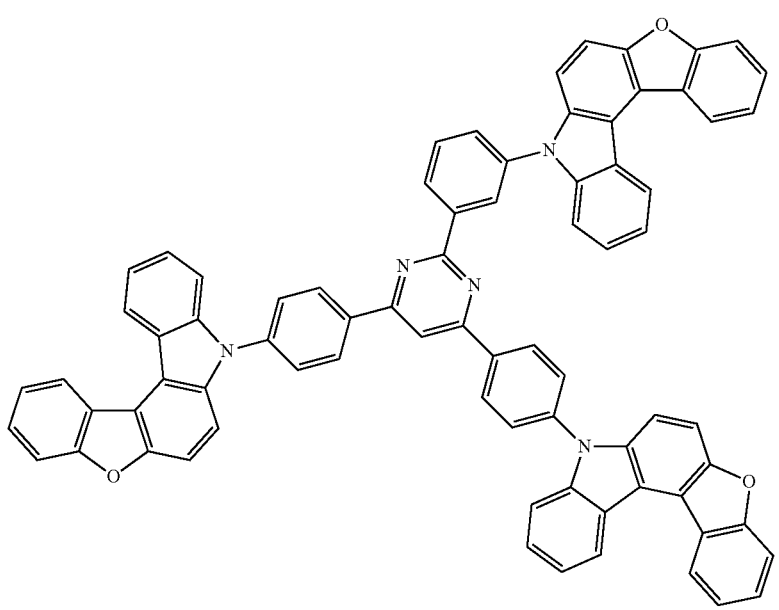

-continued
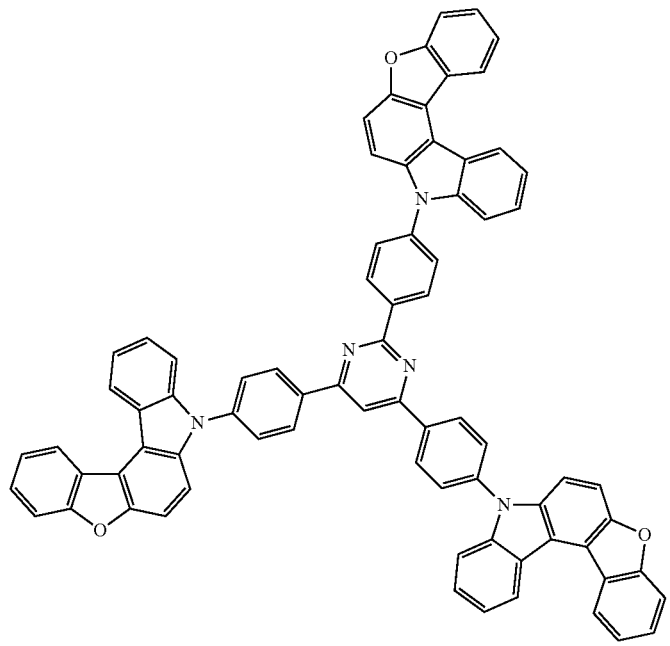
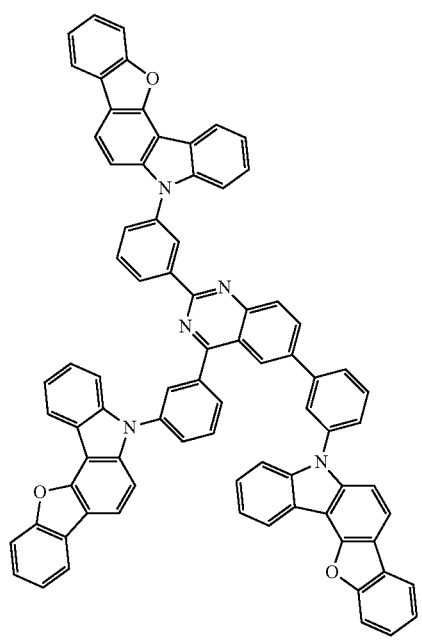

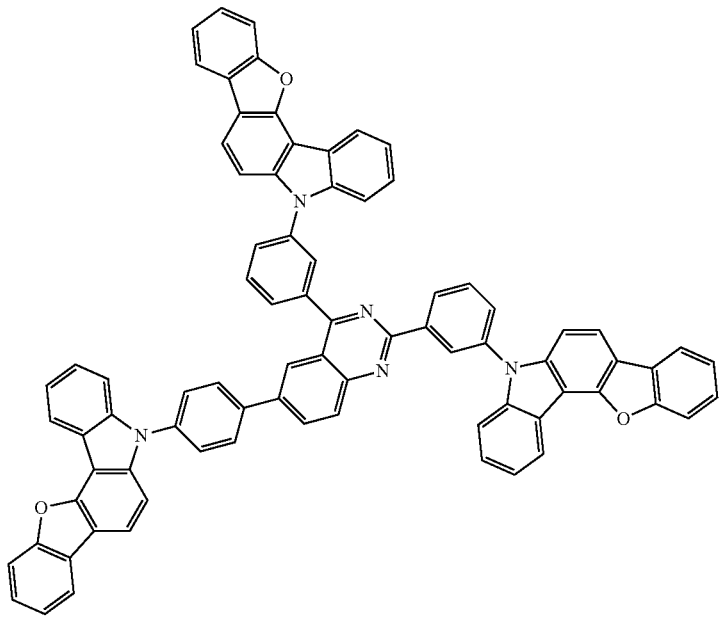
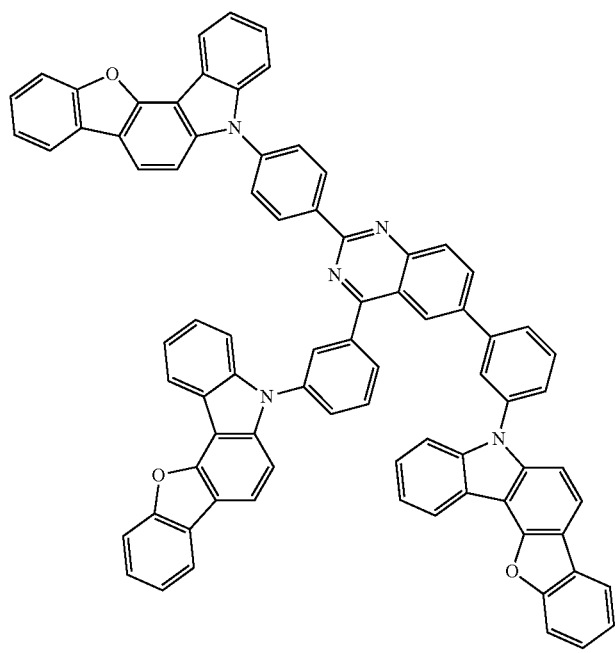

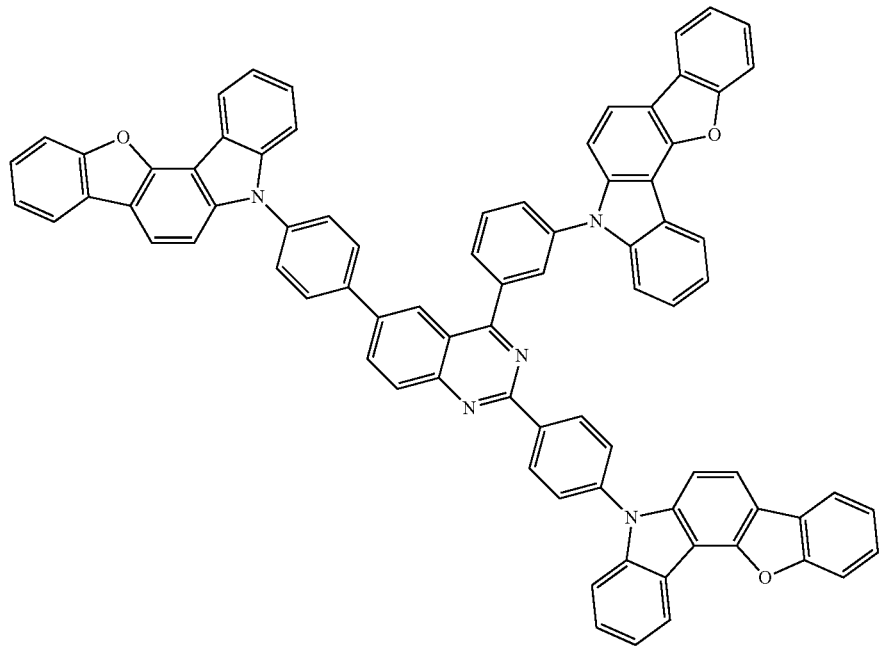
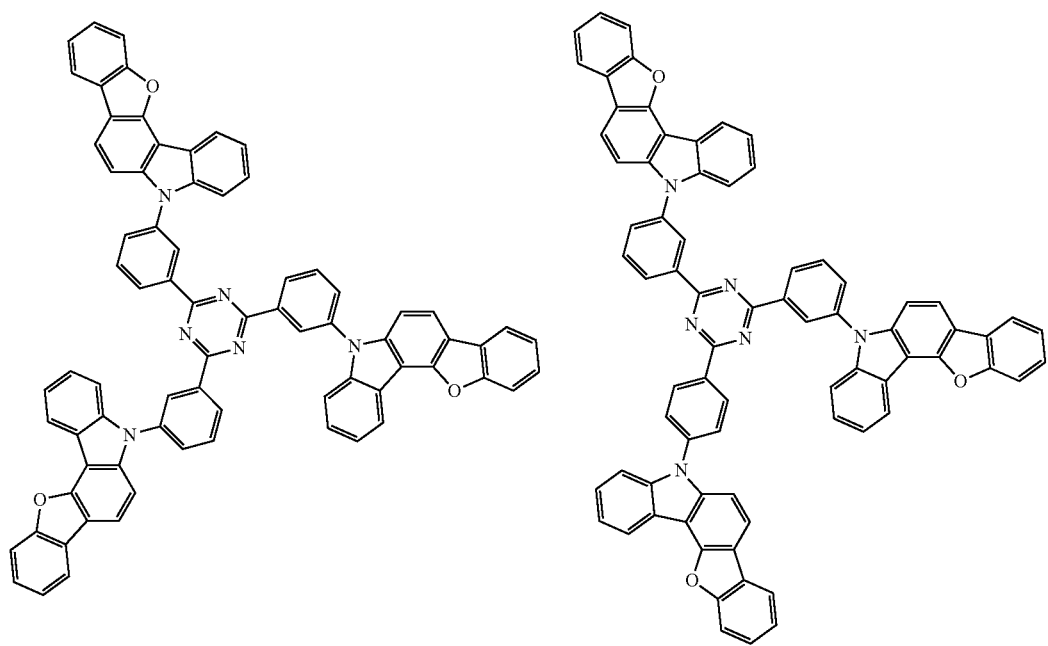

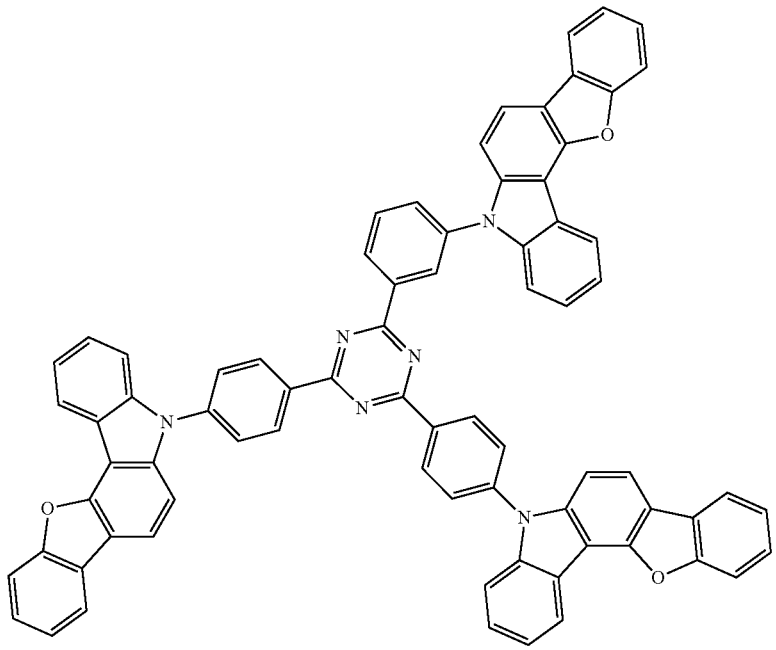
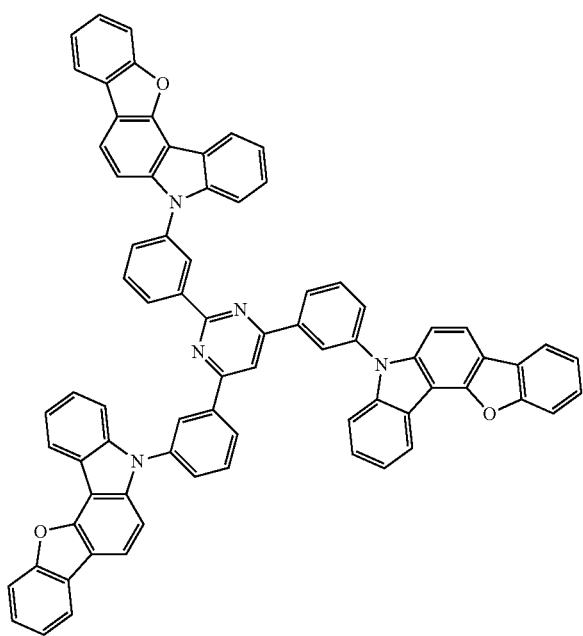

-continued
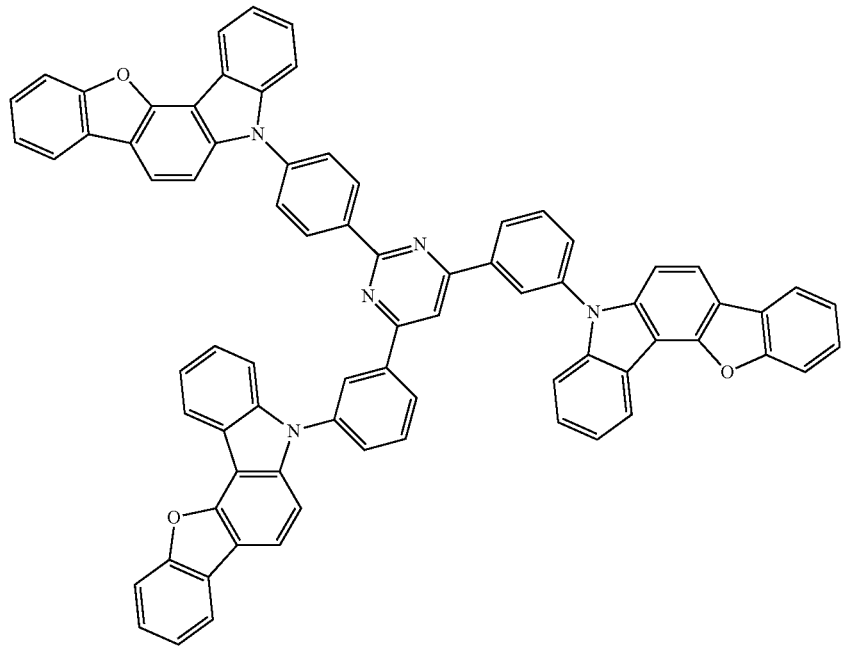
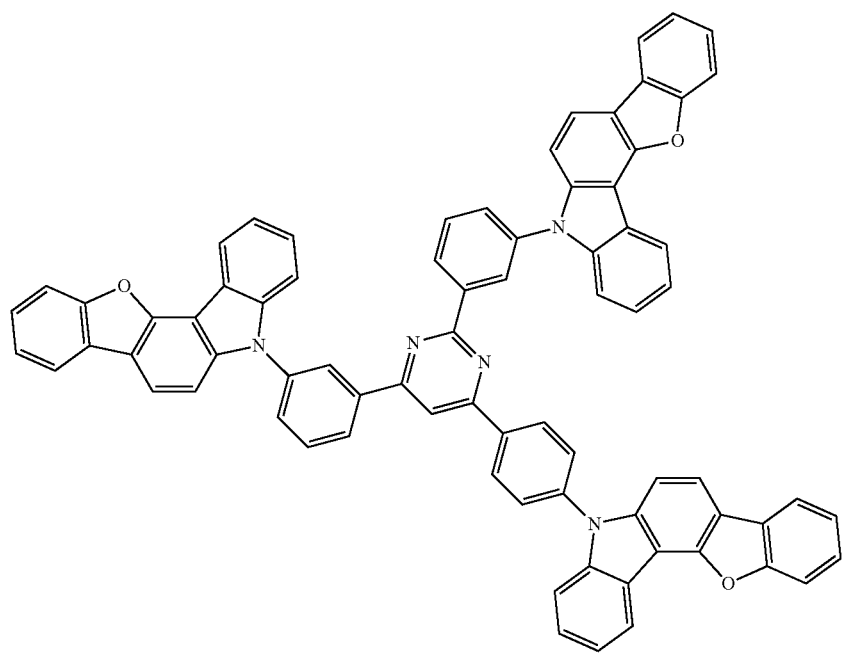

-continued
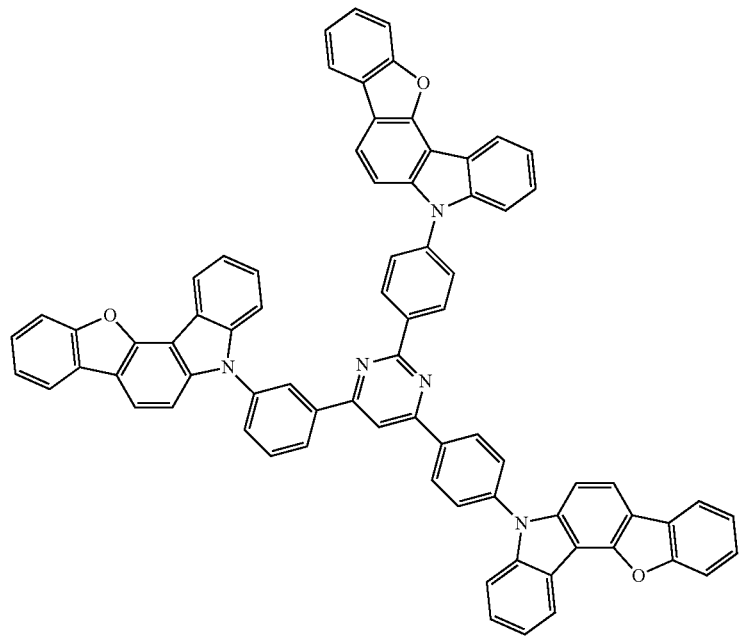
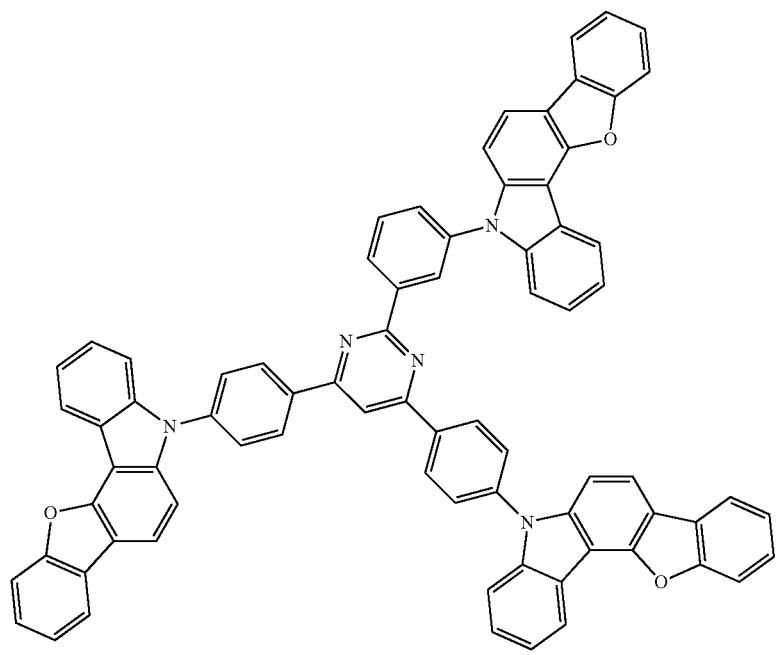

-continued
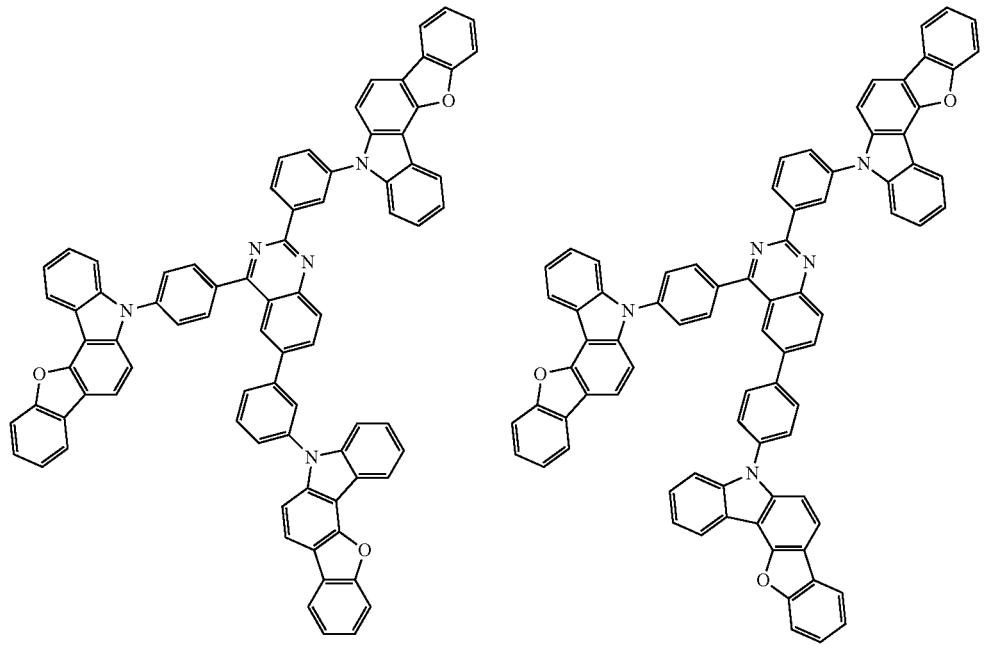
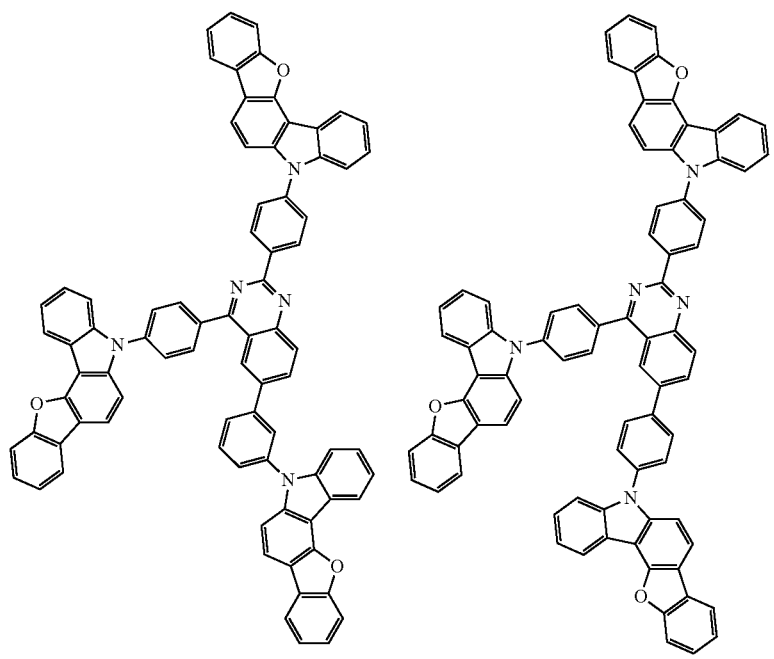

-continued
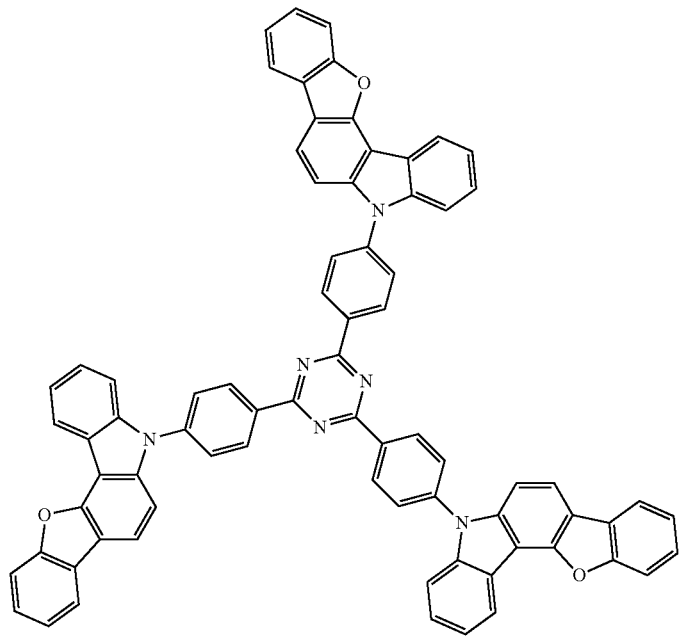
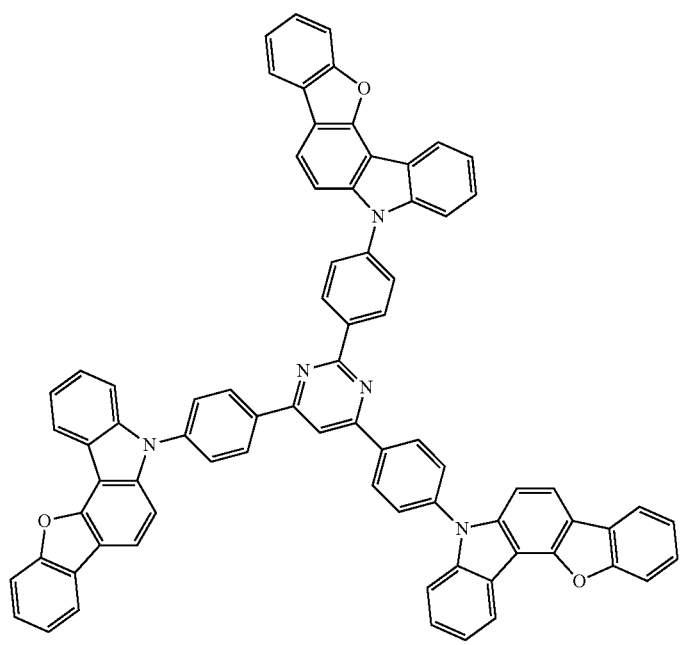

793 794
-continued
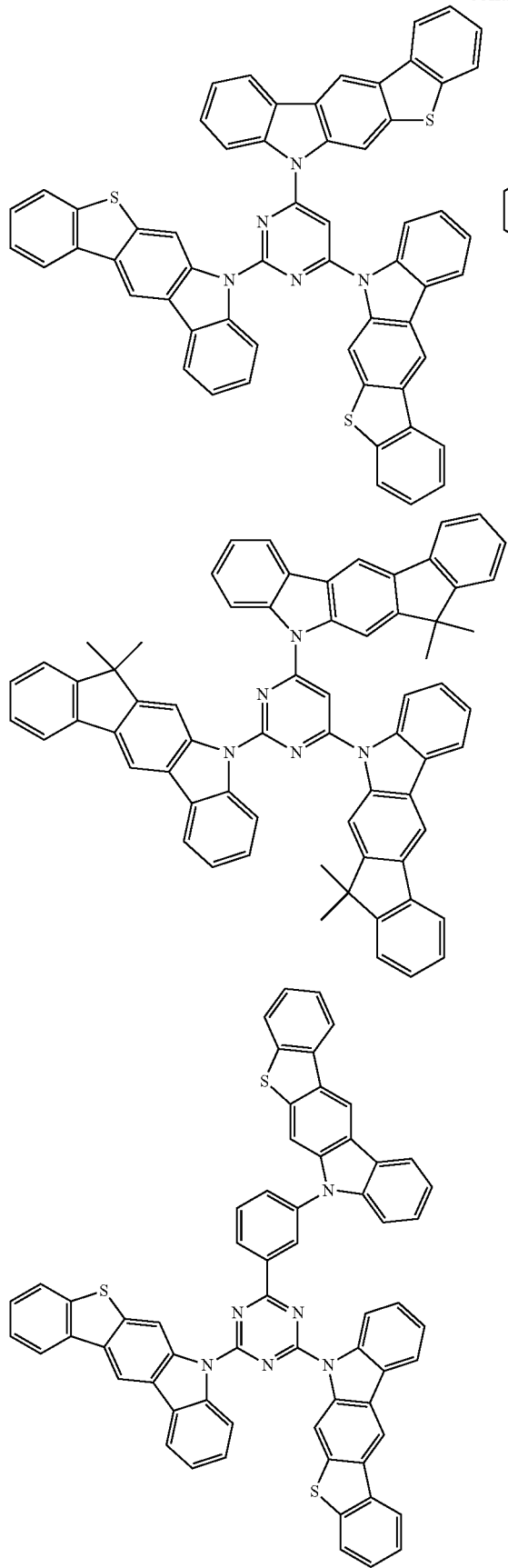

-continued
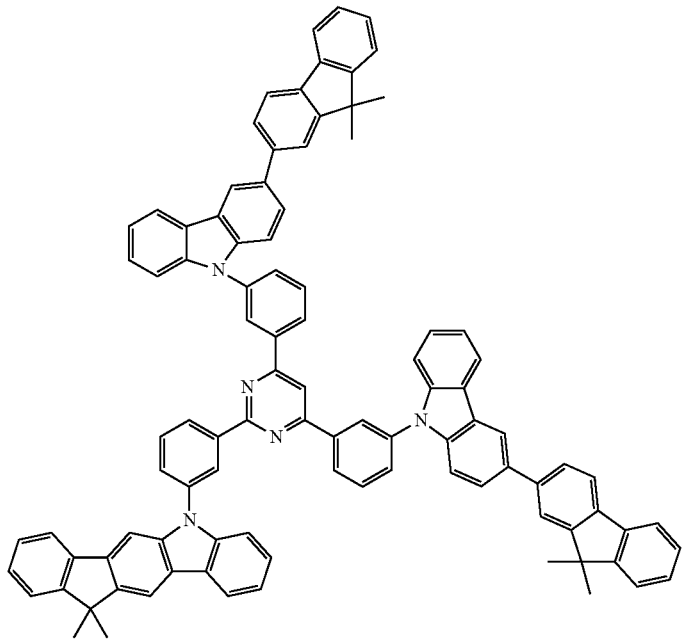
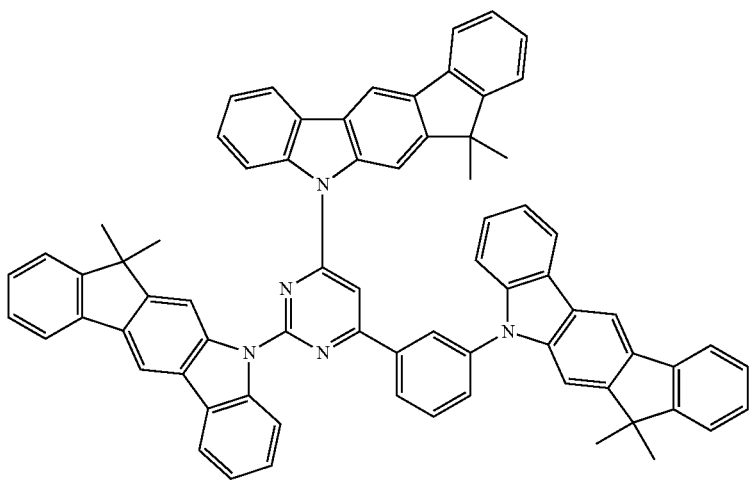

-continued
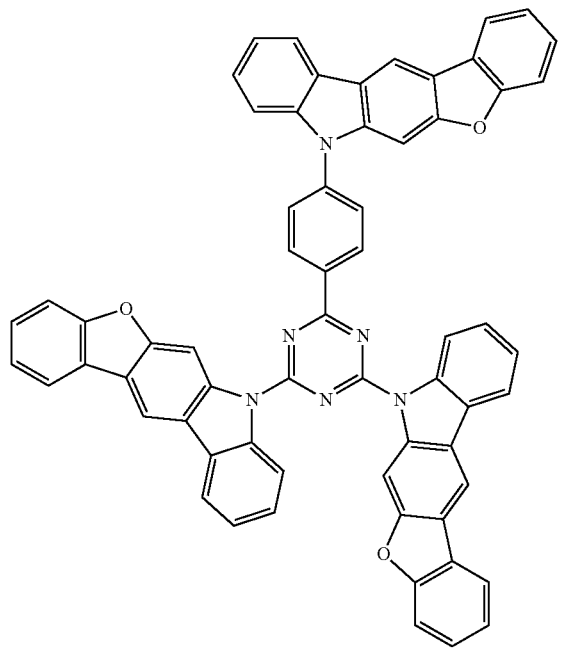
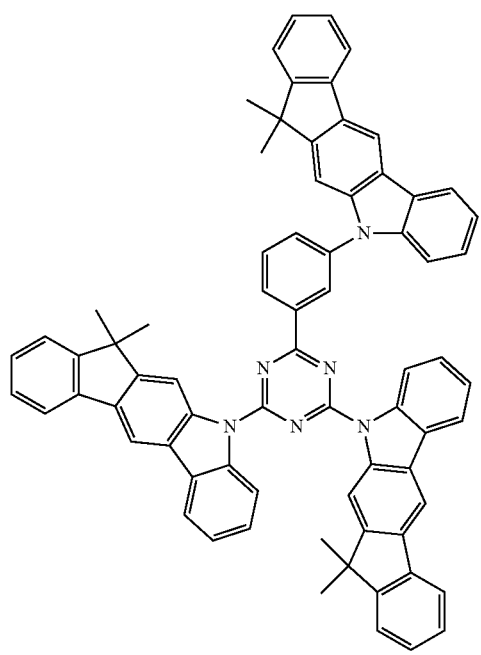

-continued
799 800
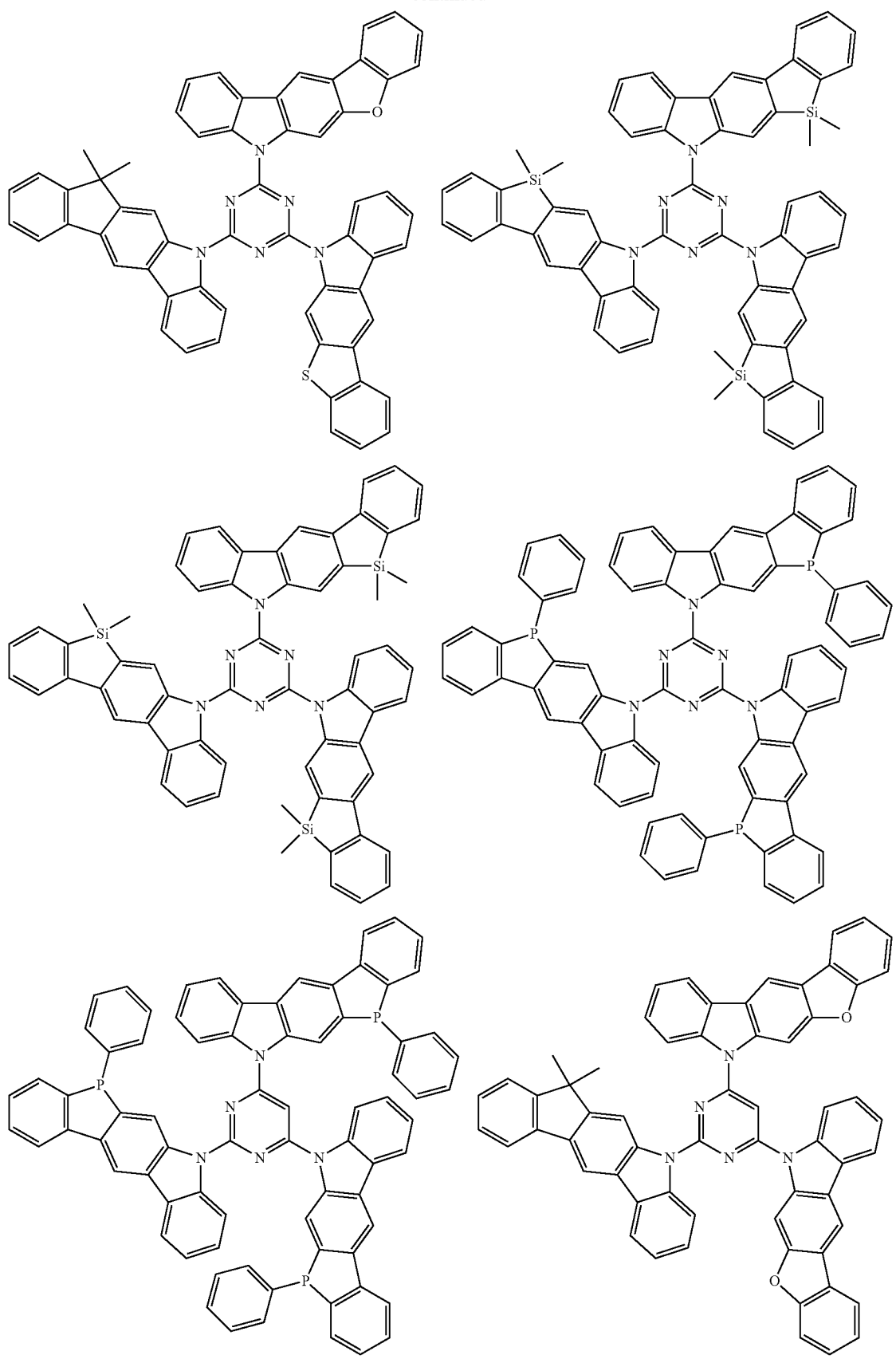

801
802
-continued
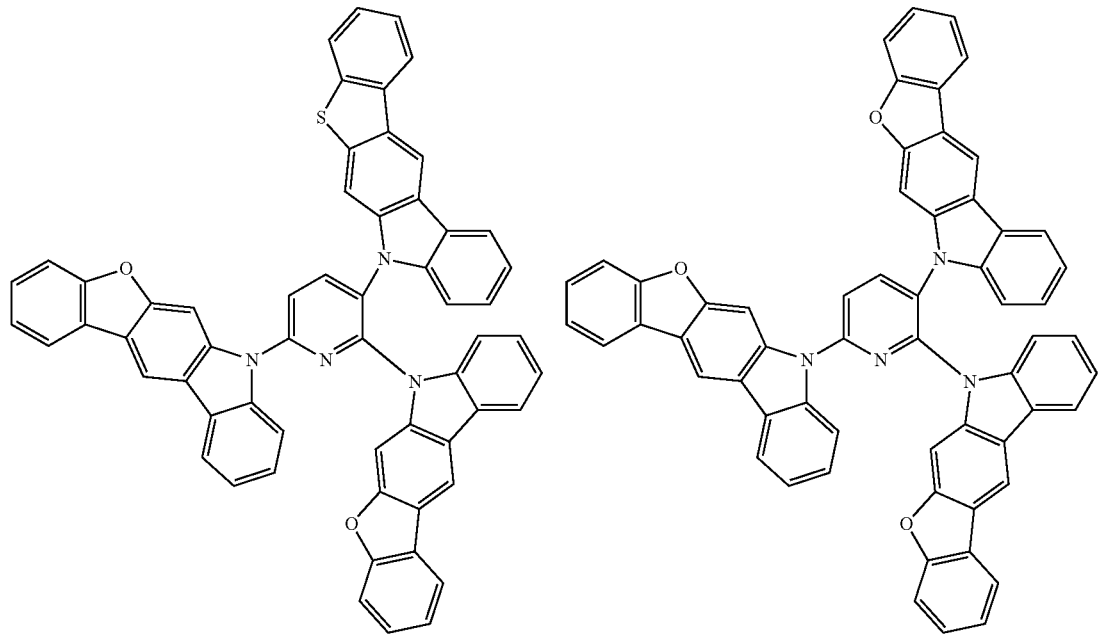
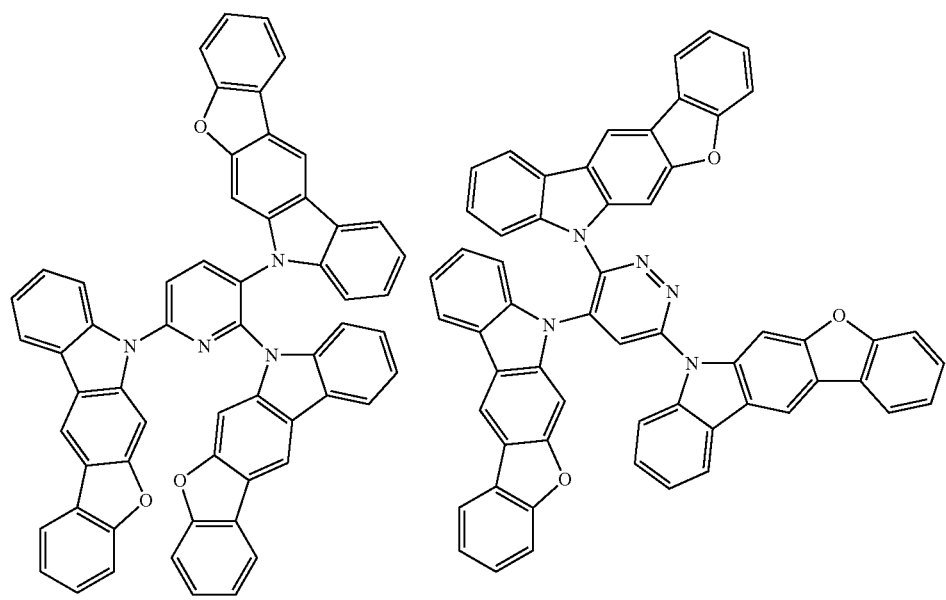

-continued
803
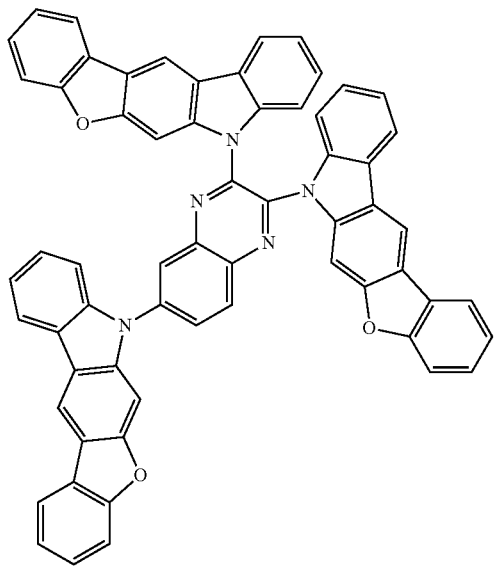
804
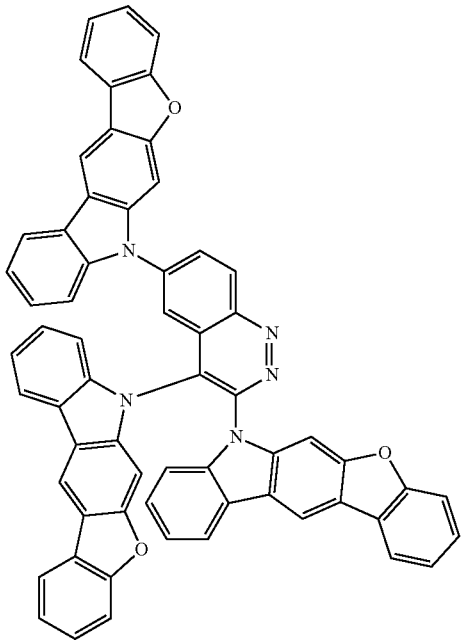
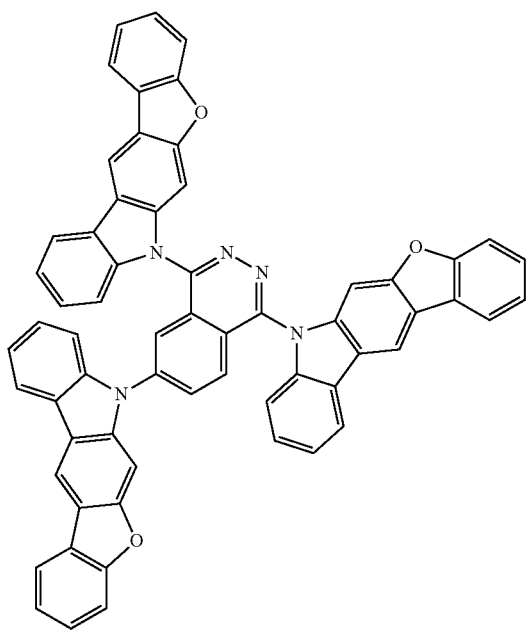

805 806
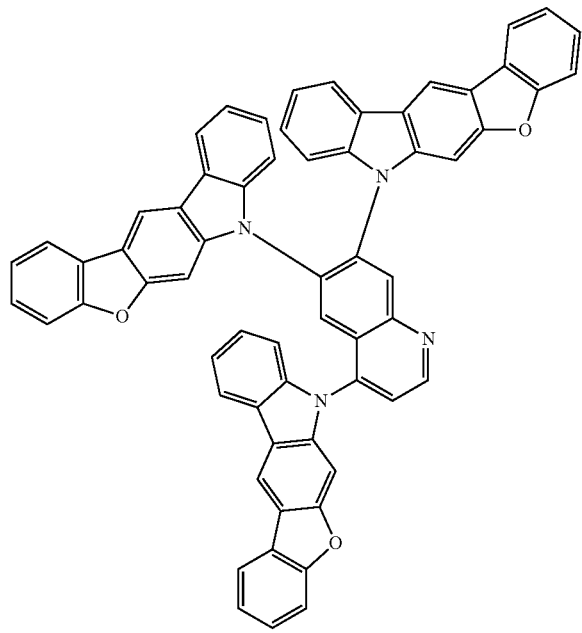
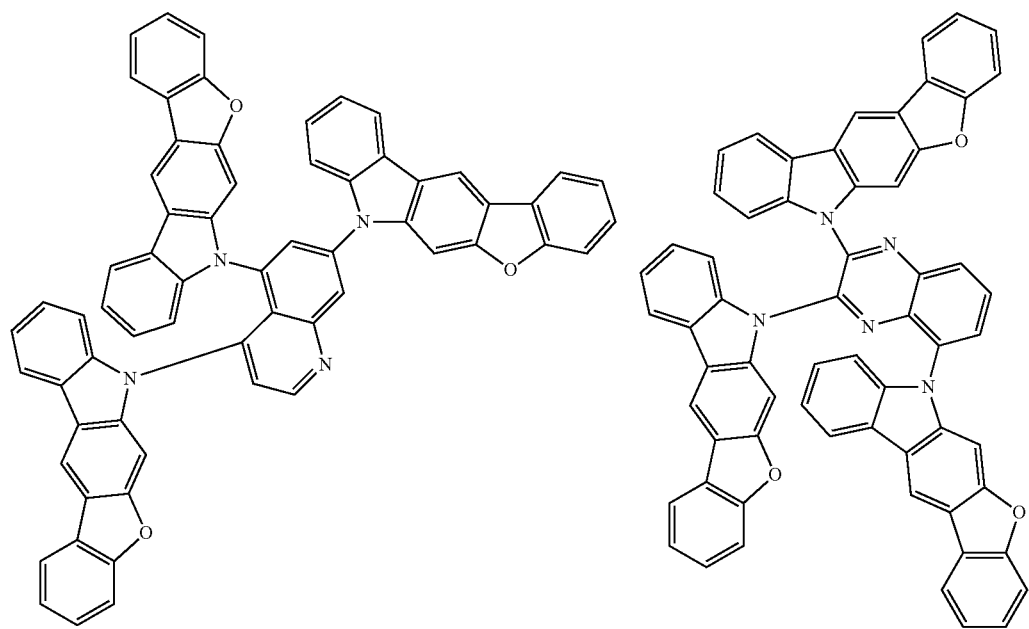

-continued
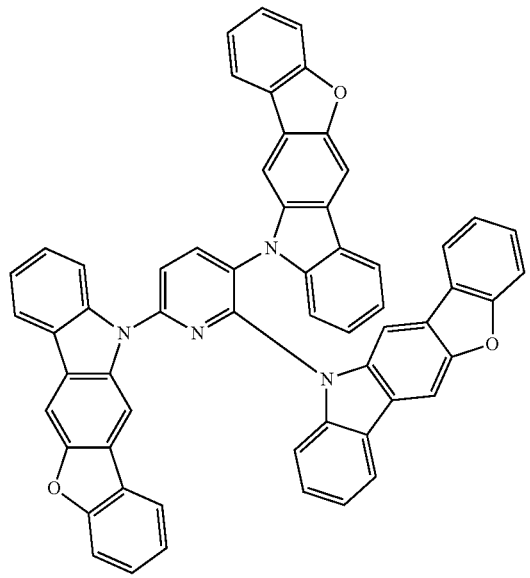
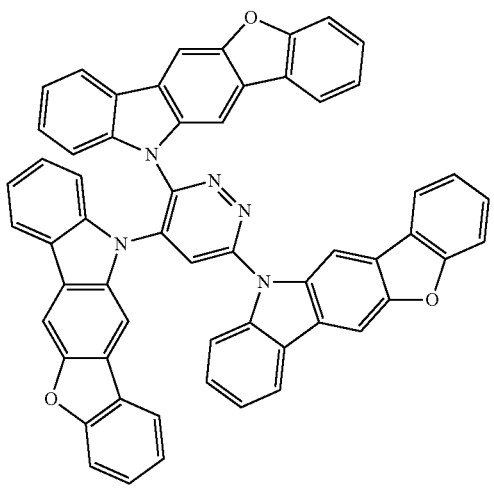
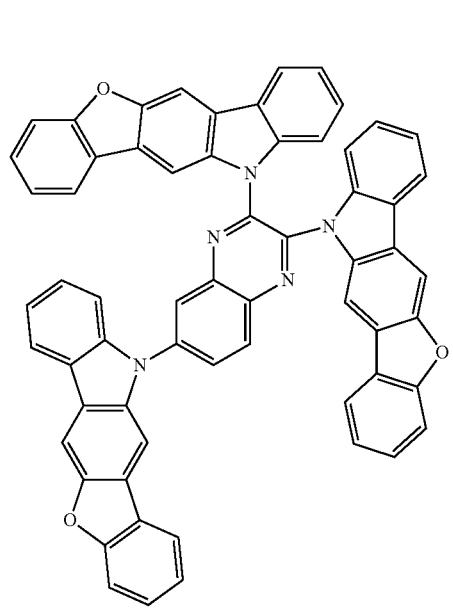
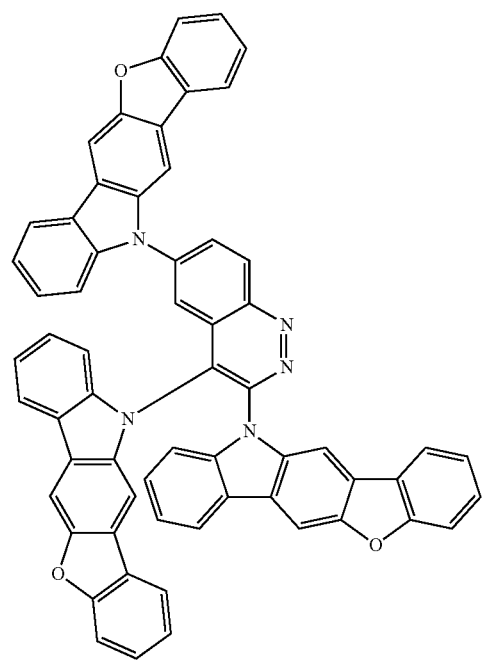

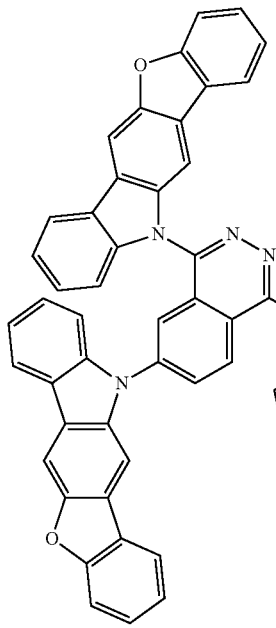
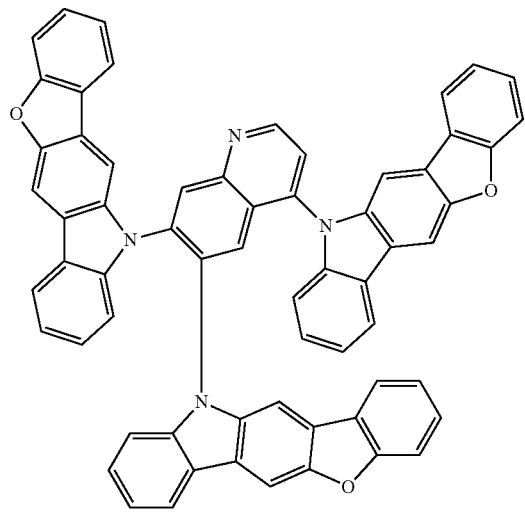
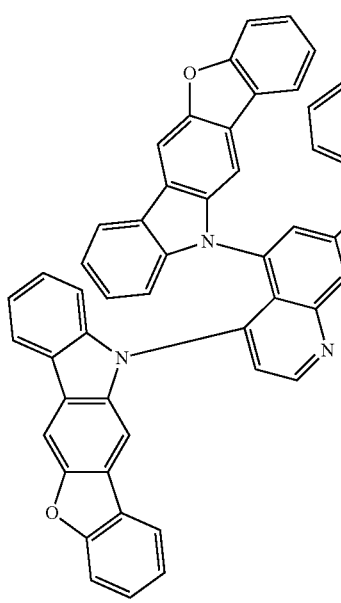
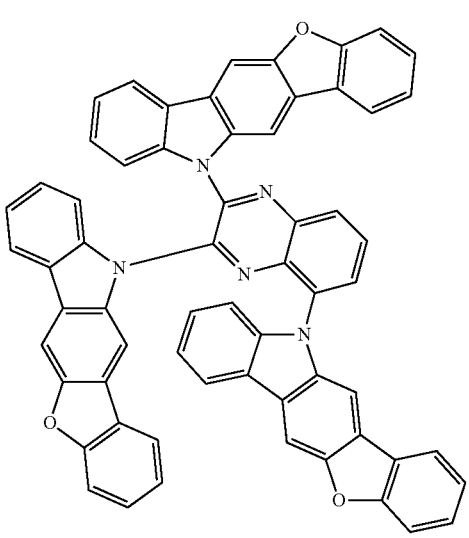

811 812
-continued
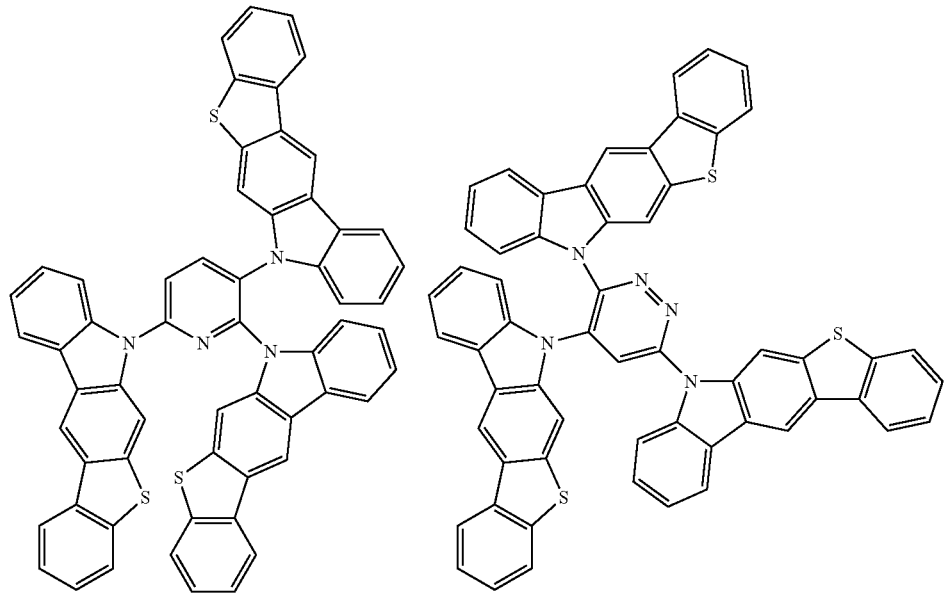
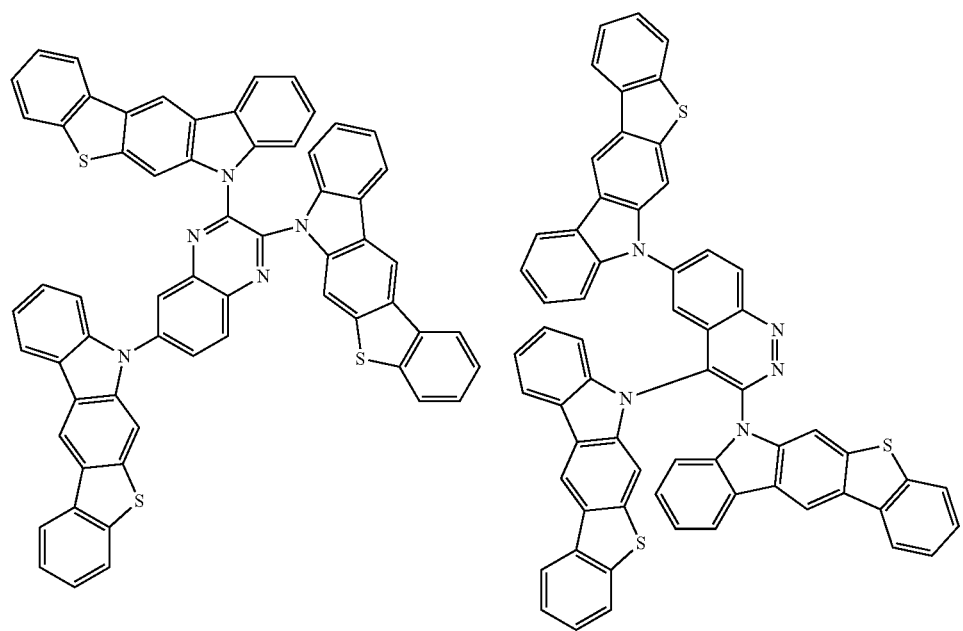

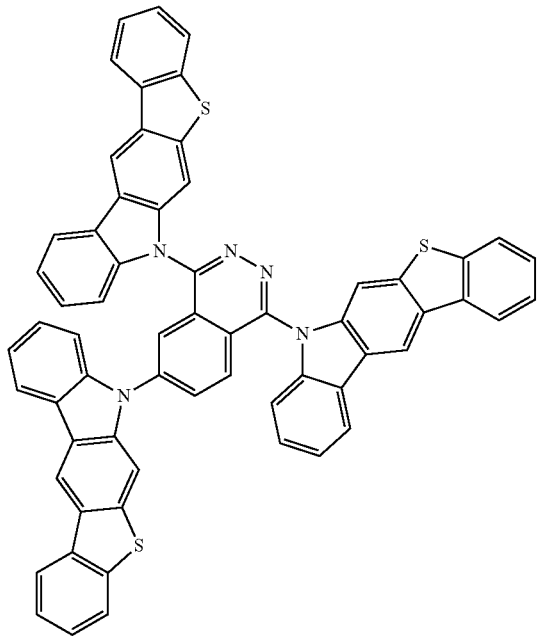
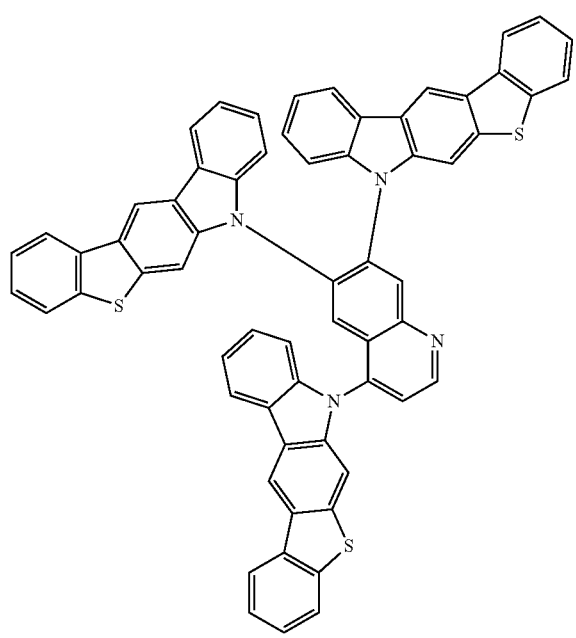

-continued
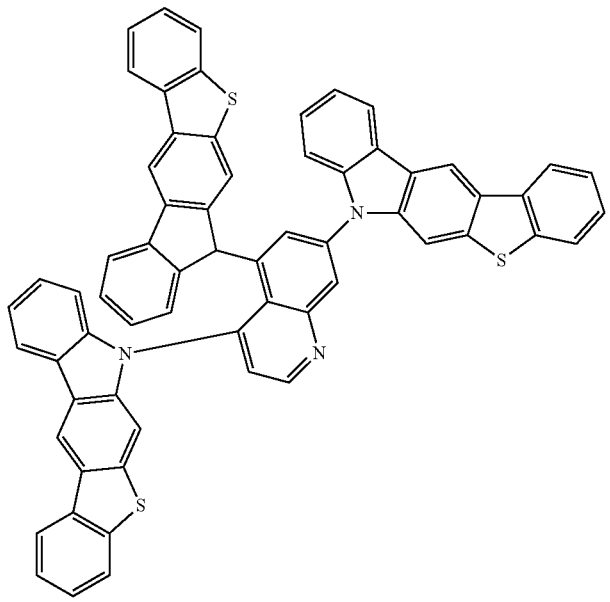
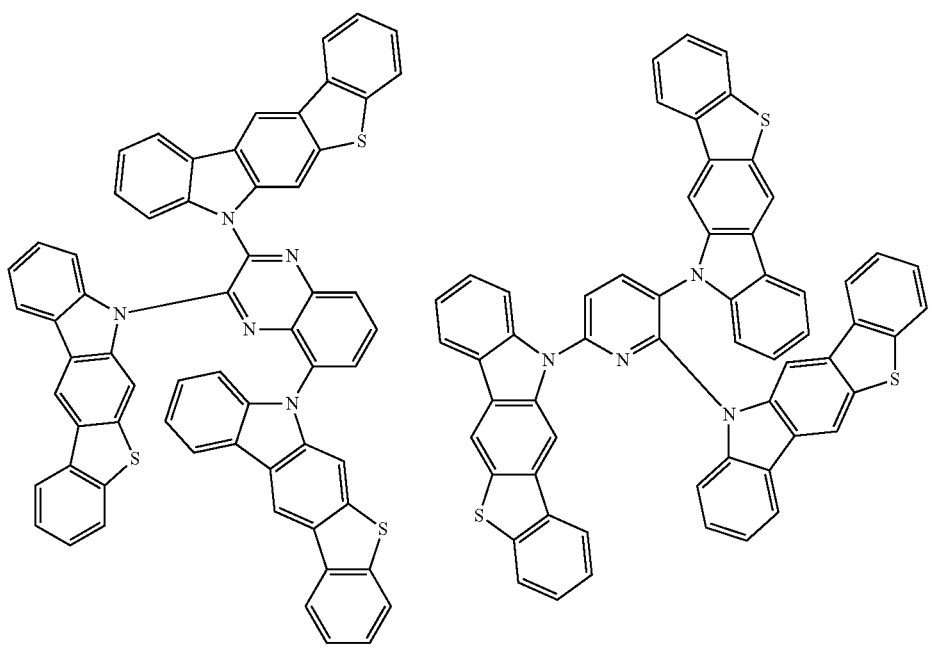

817 818
-continued
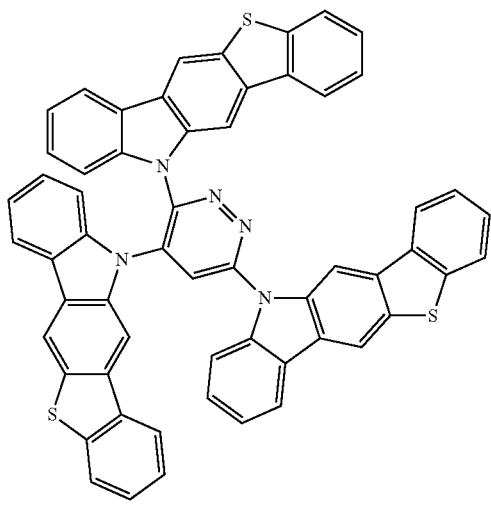
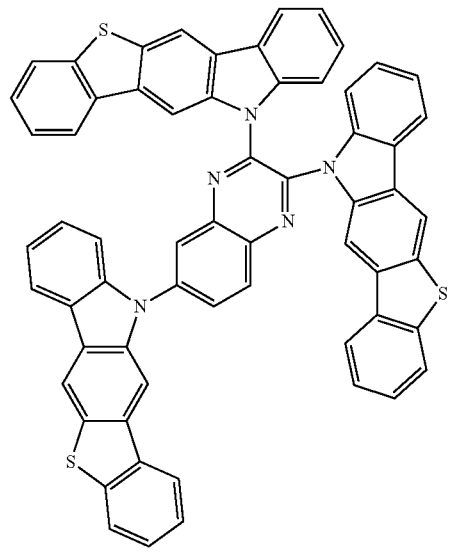
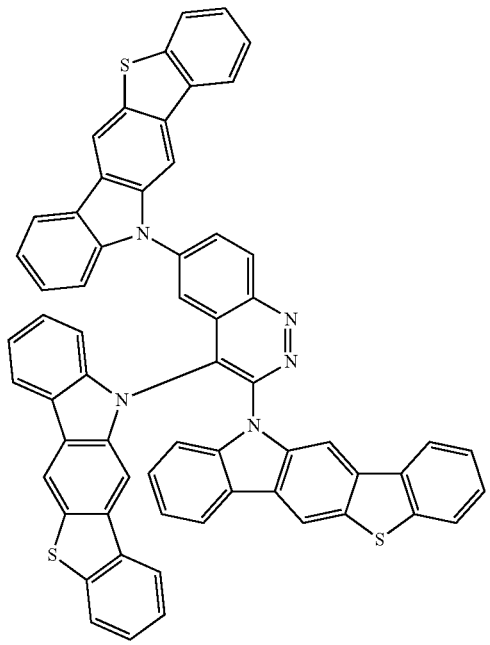
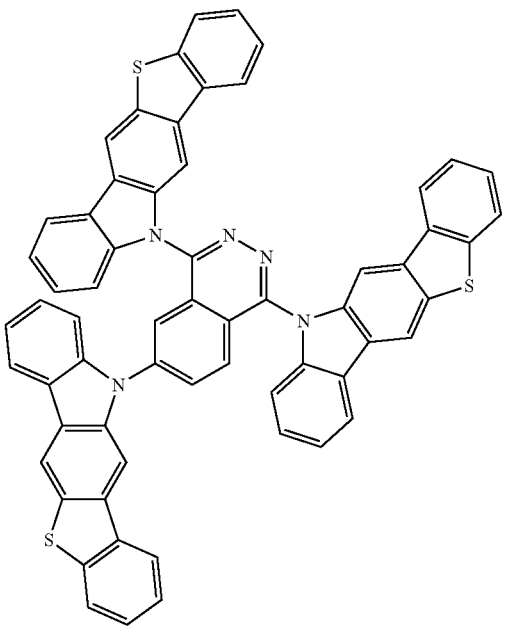

819
820
-continued
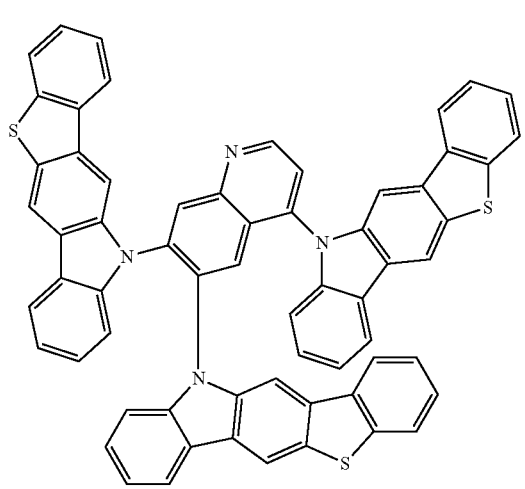
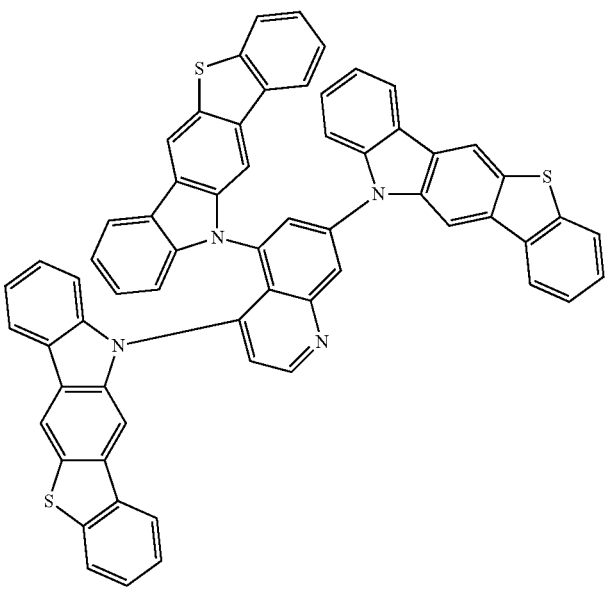
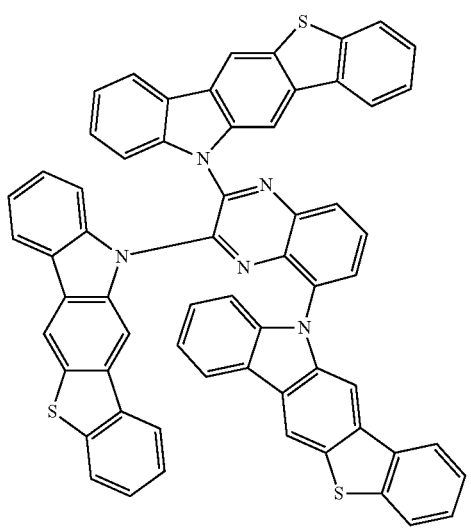
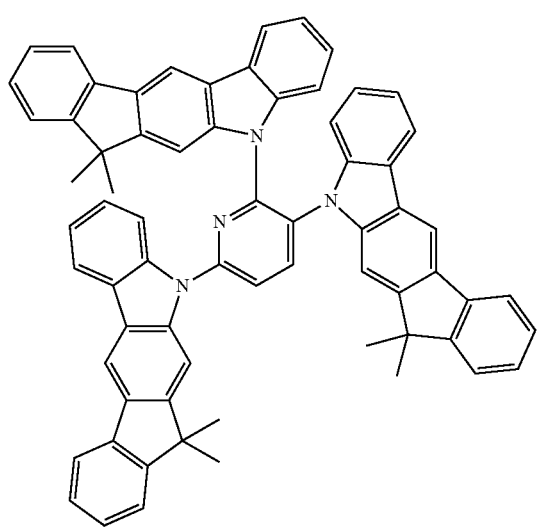
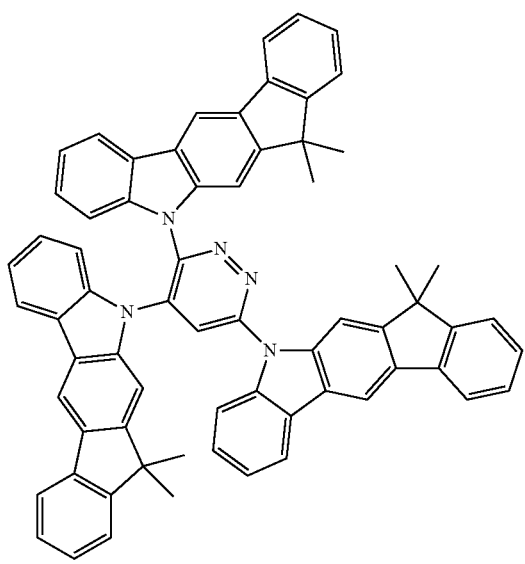
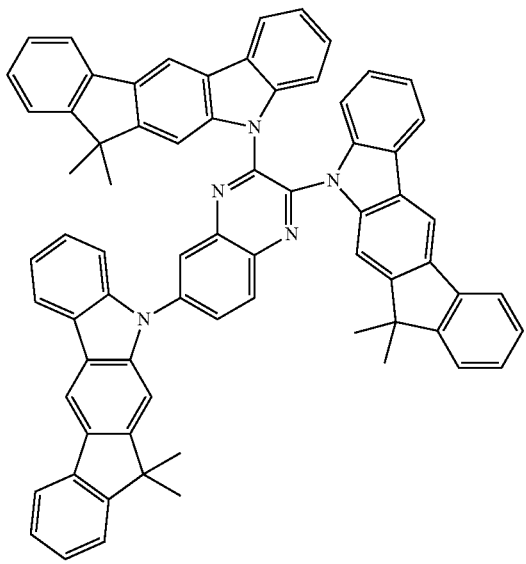

821 822
-continued
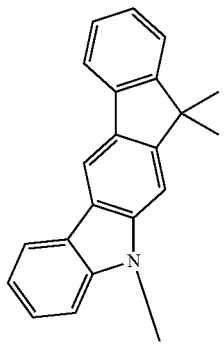 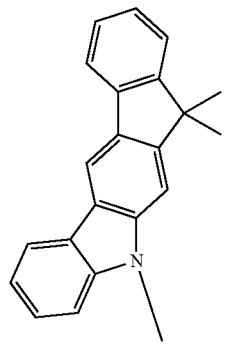
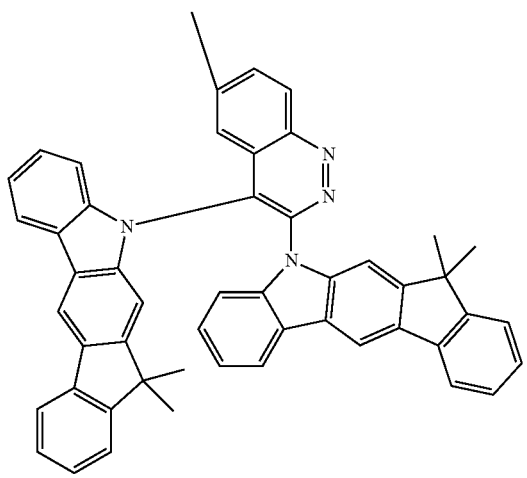 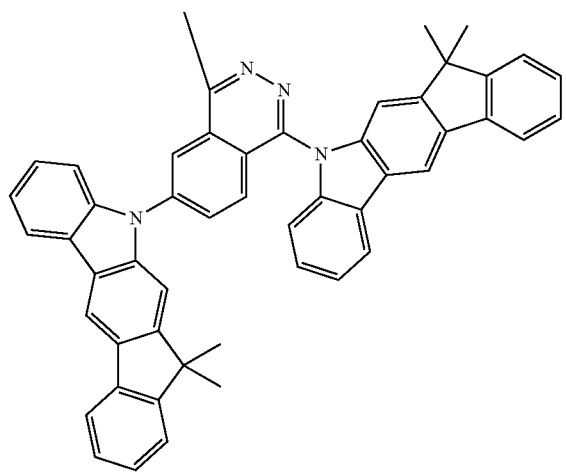
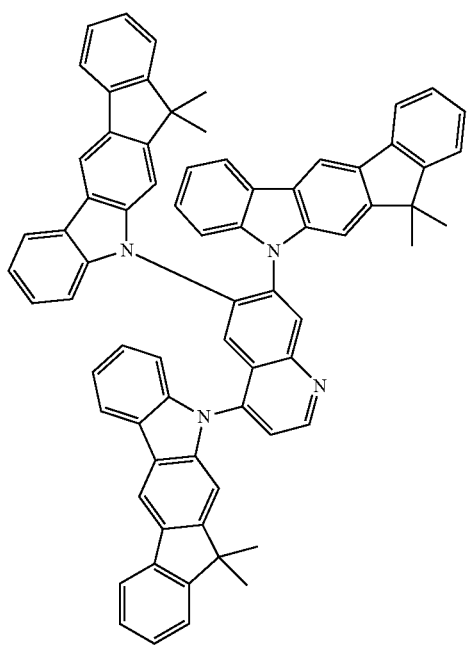 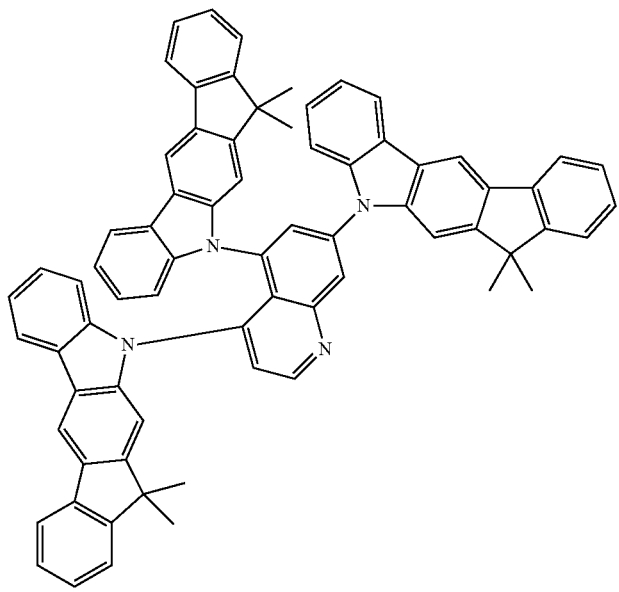

-continued
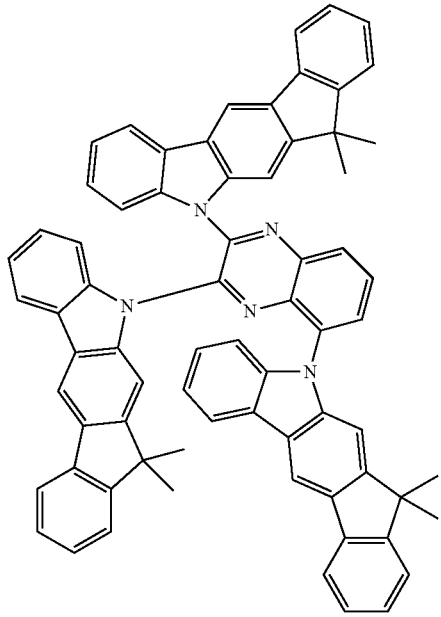
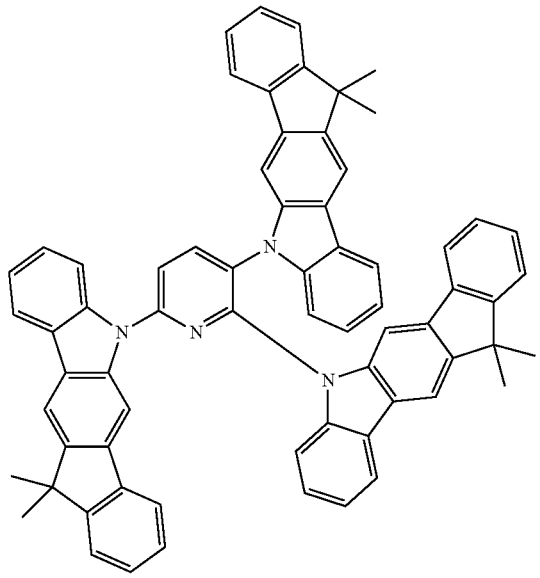
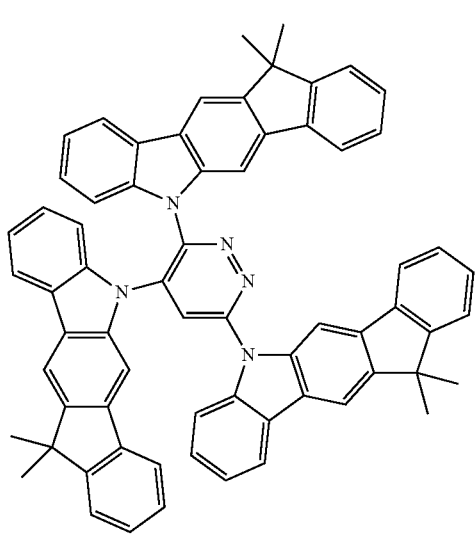
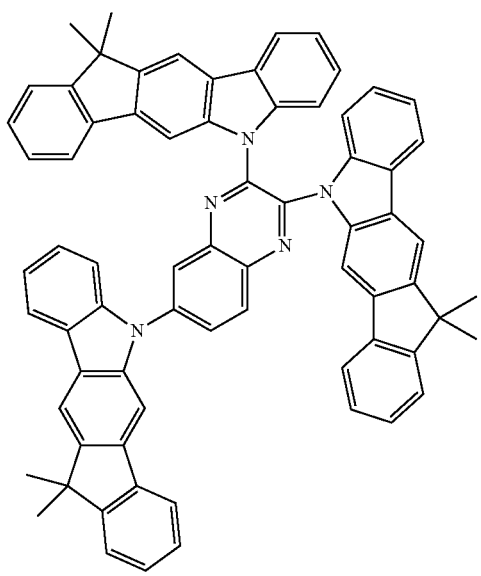

825 826
-continued
| 　 | 　 |
|---|---|
| 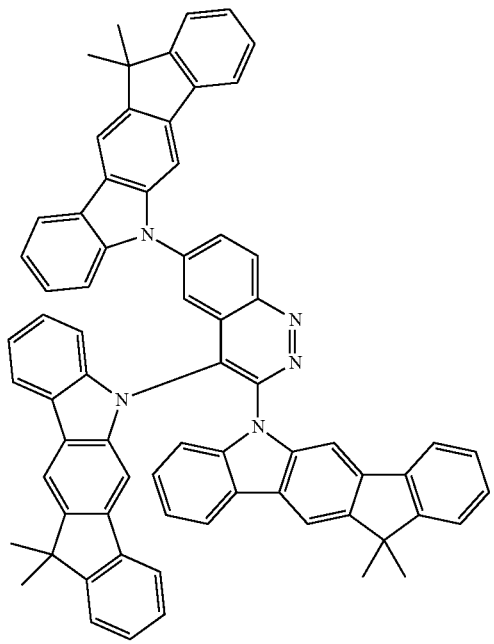 | 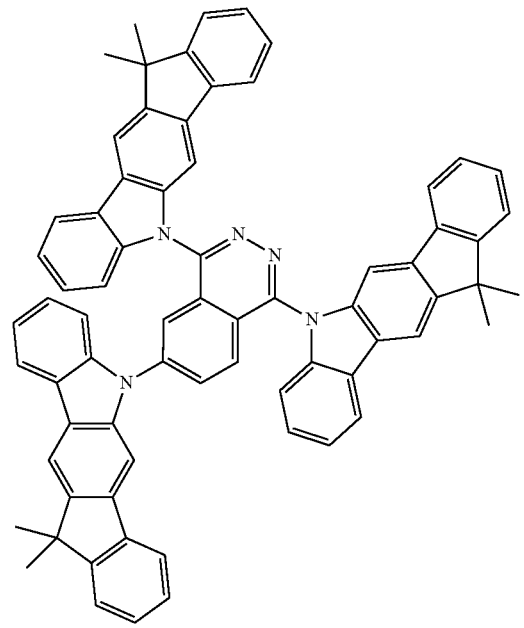 |
| 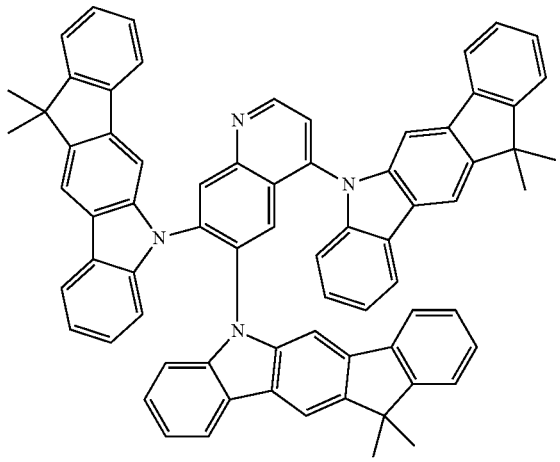 | 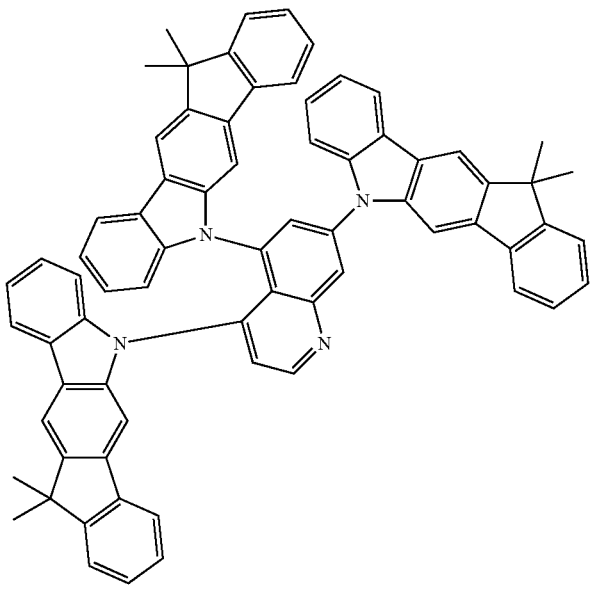 |

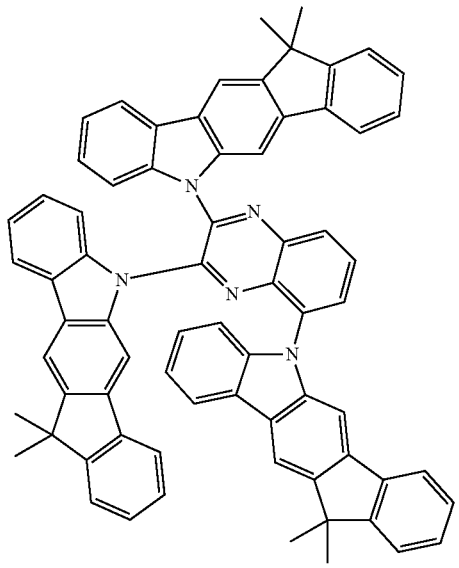
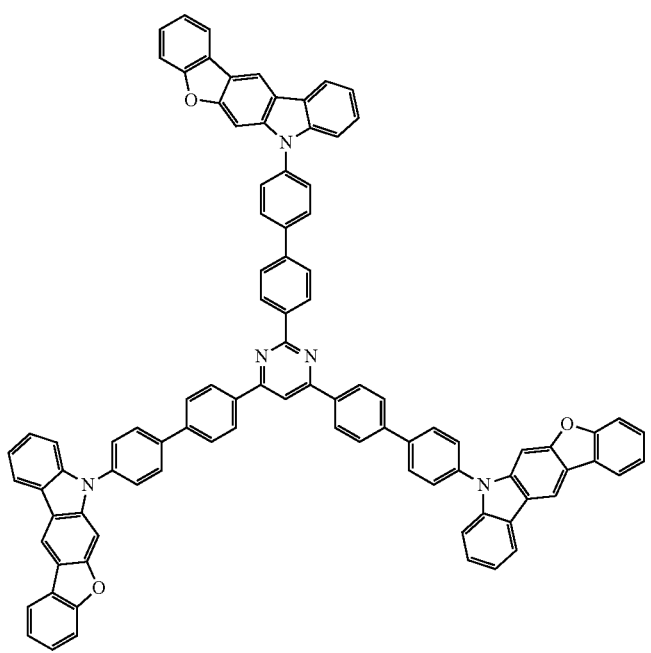

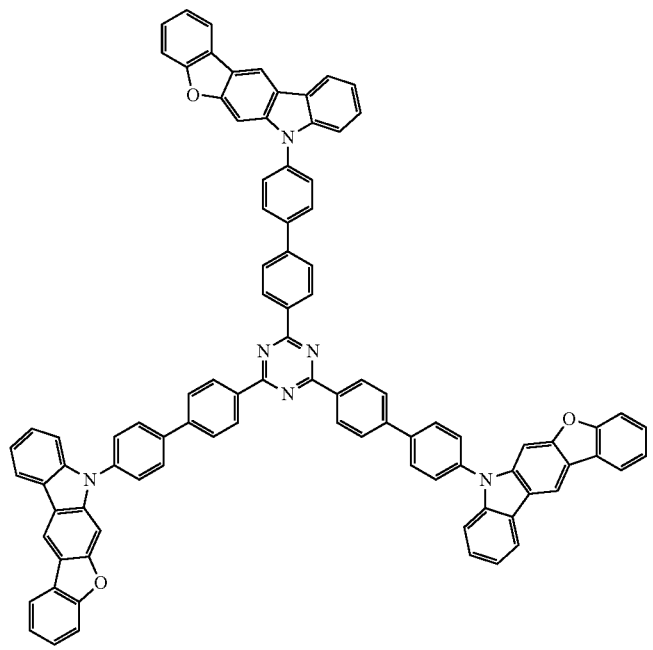
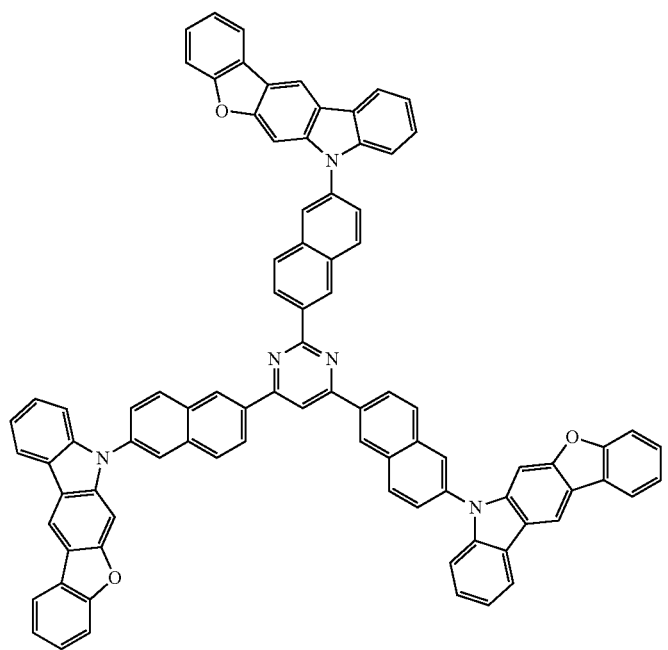

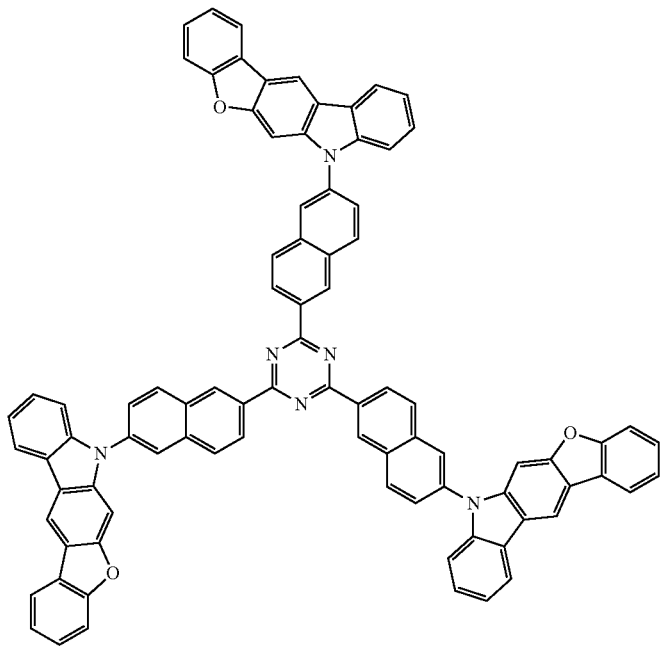
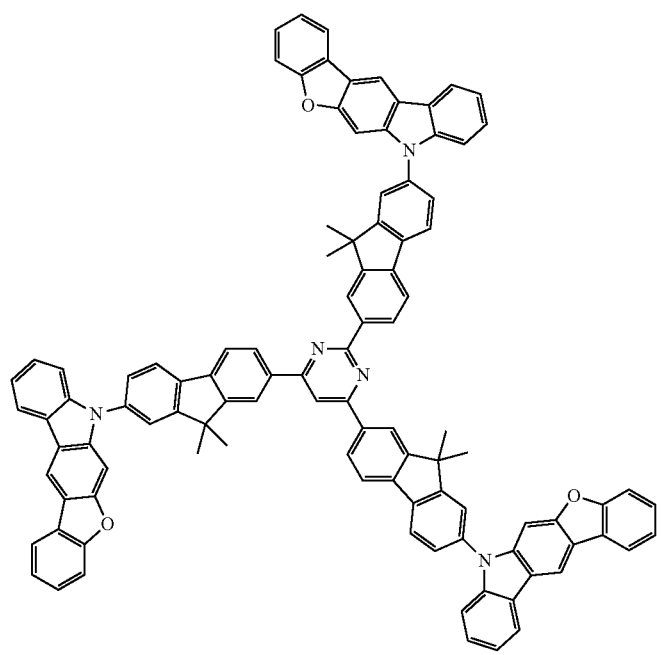

-continued
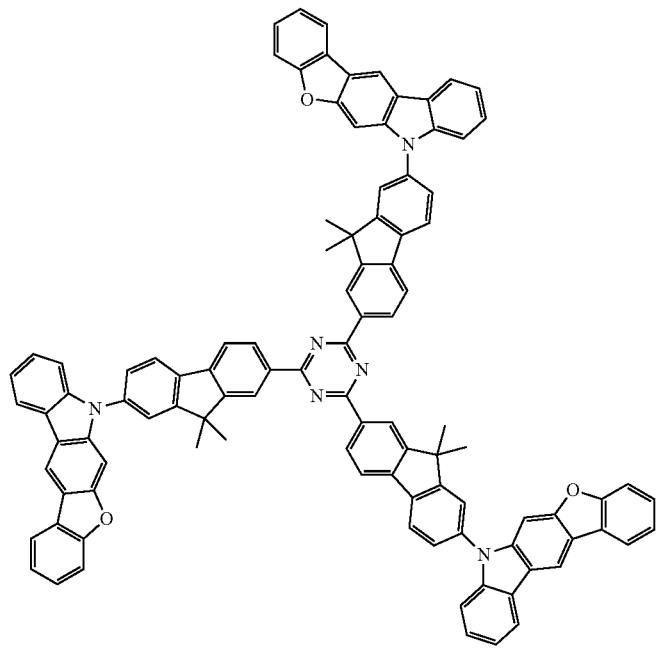
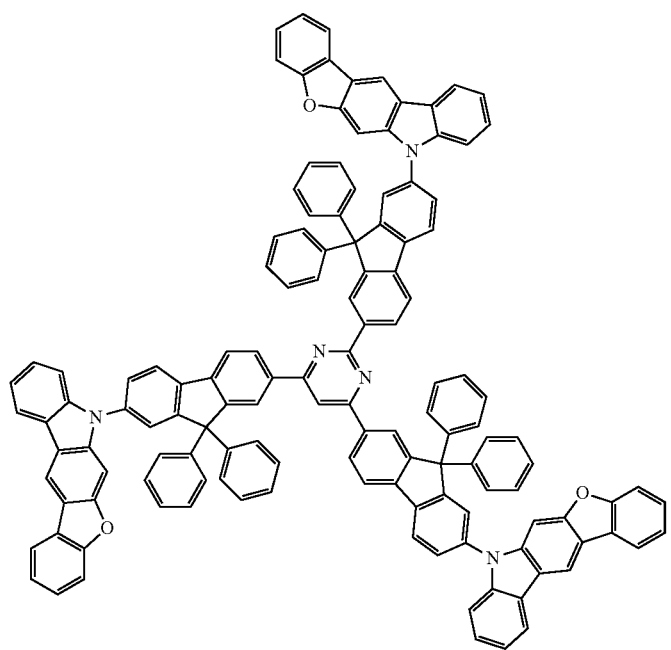

-continued
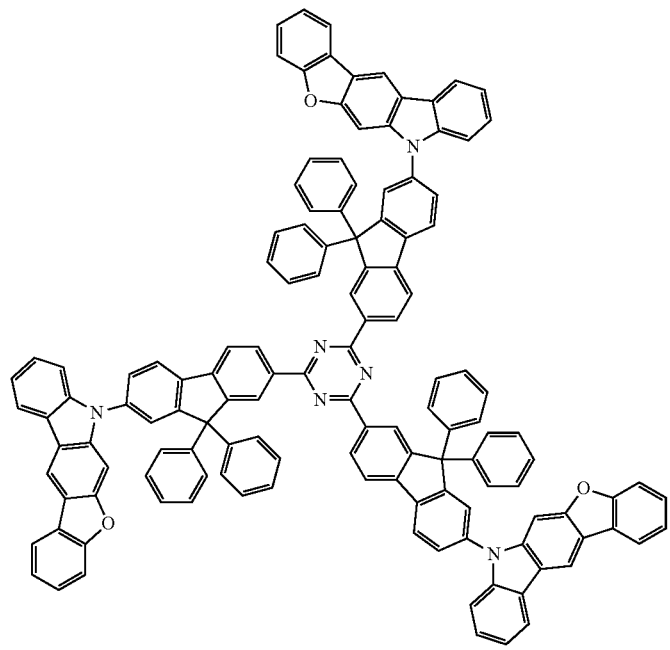
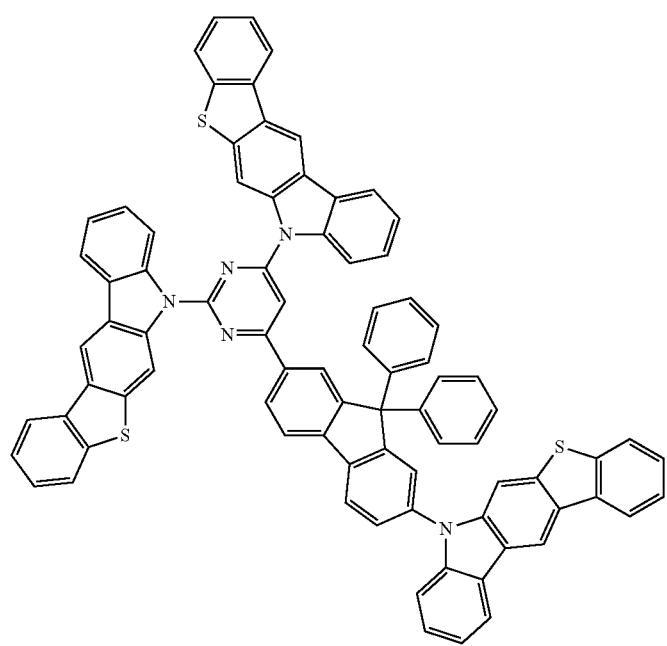

-continued
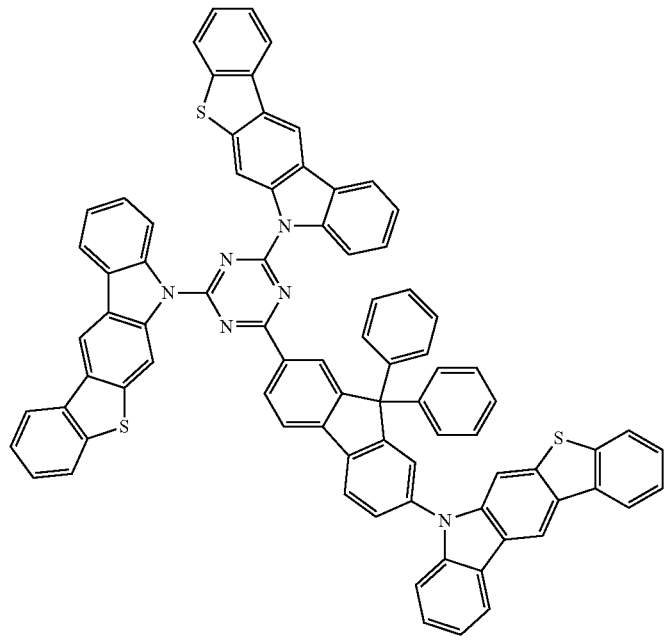
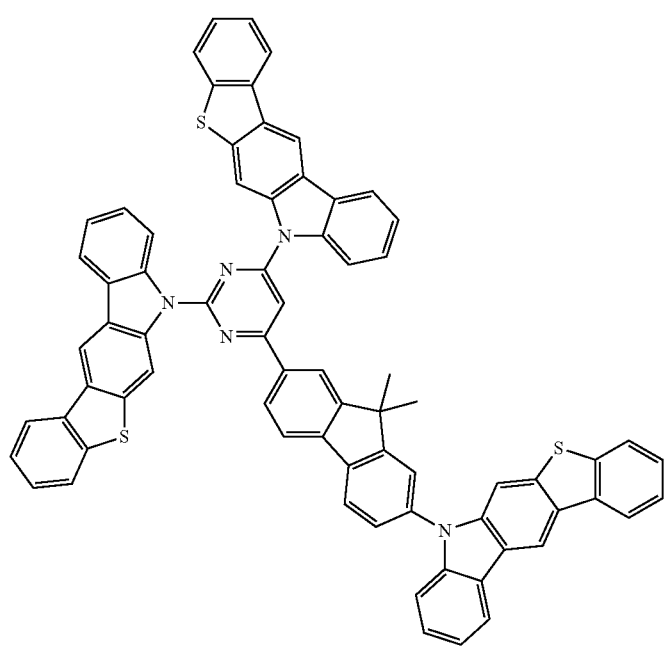

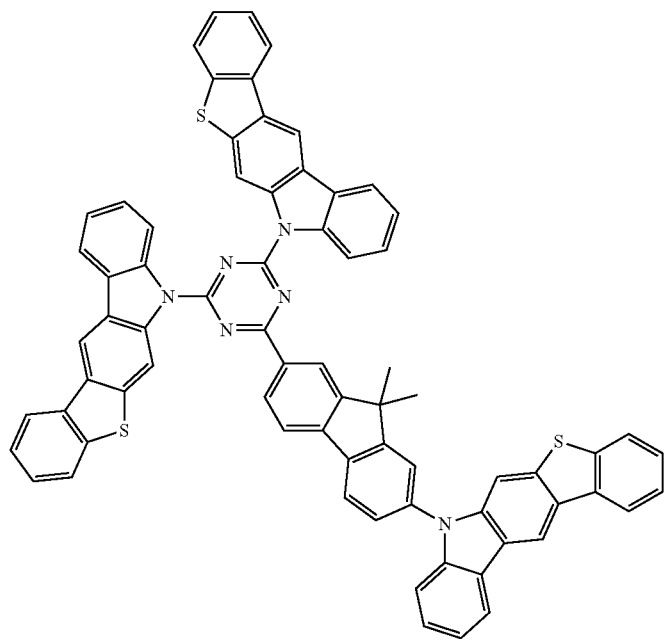
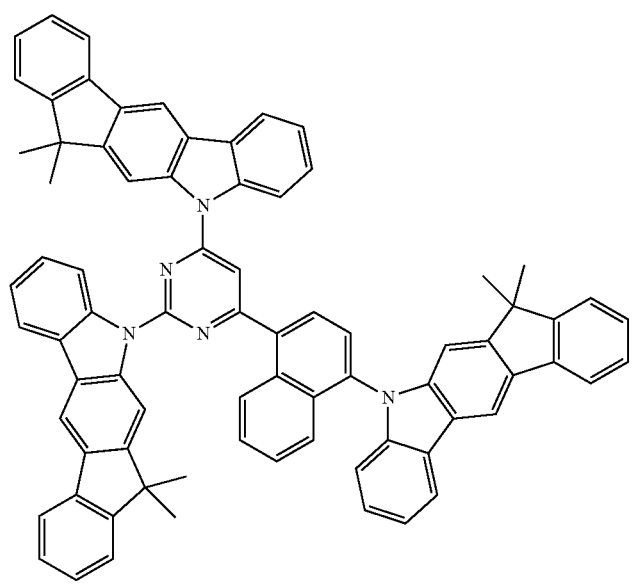

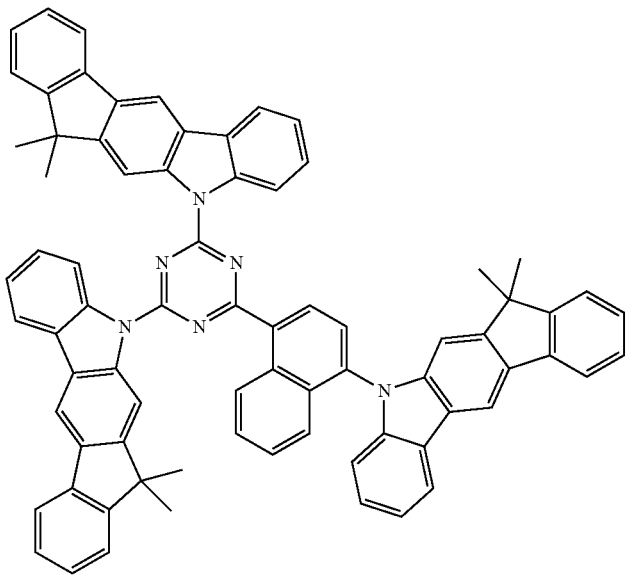
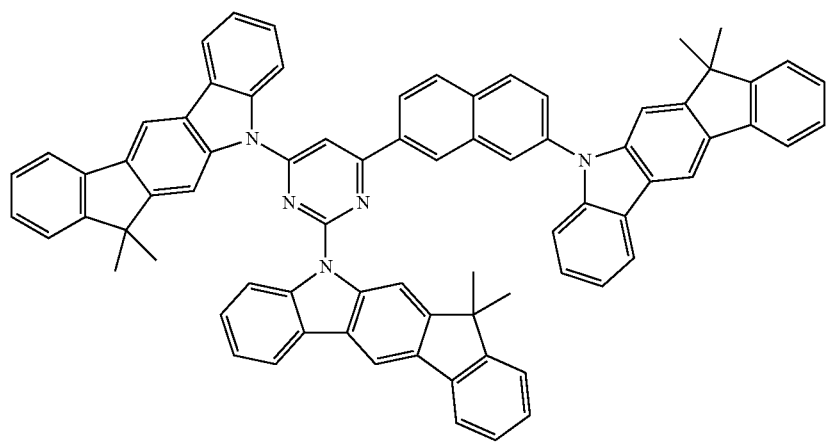
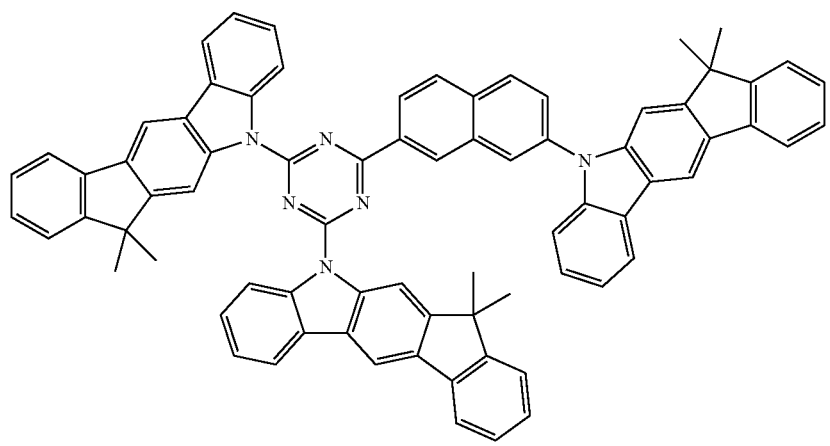

843
844
-continued
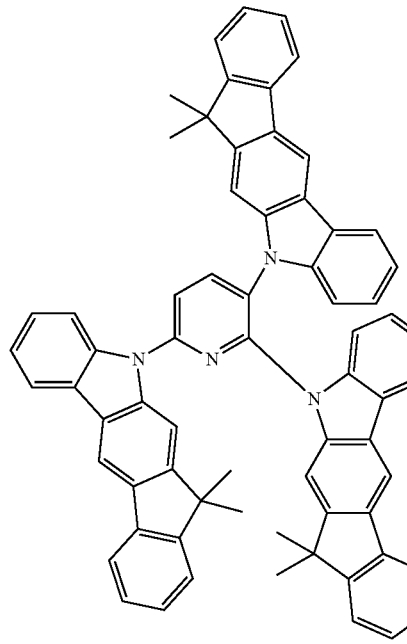
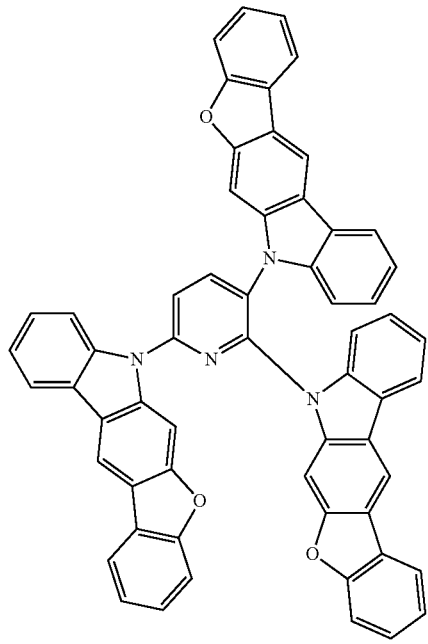
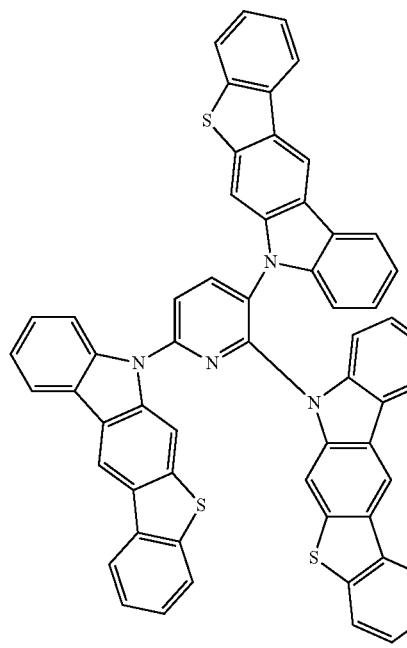
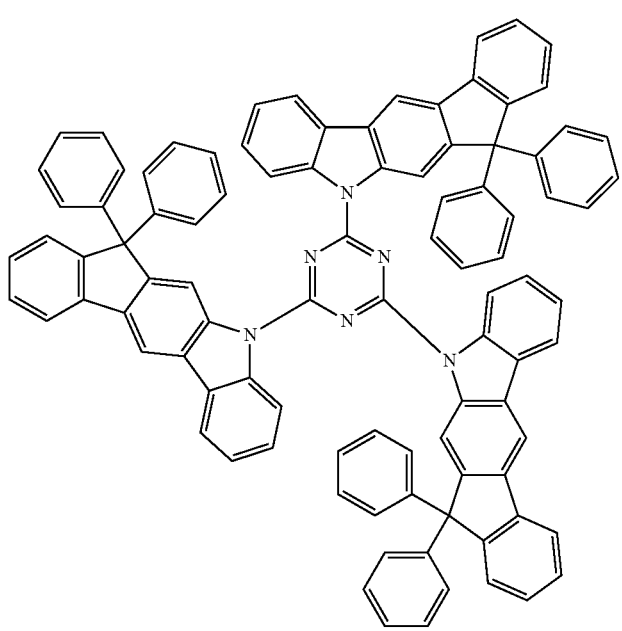

-continued
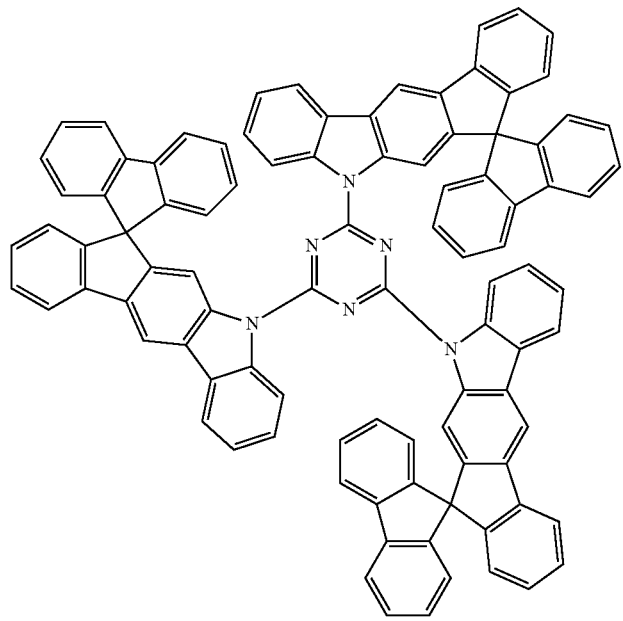
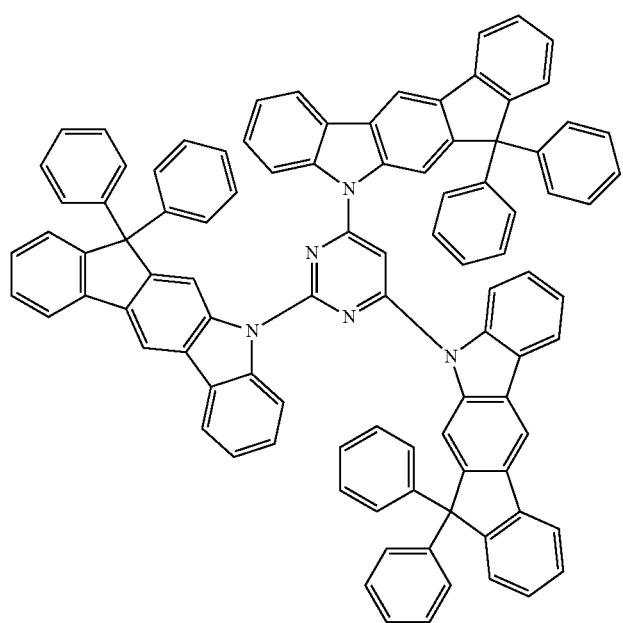

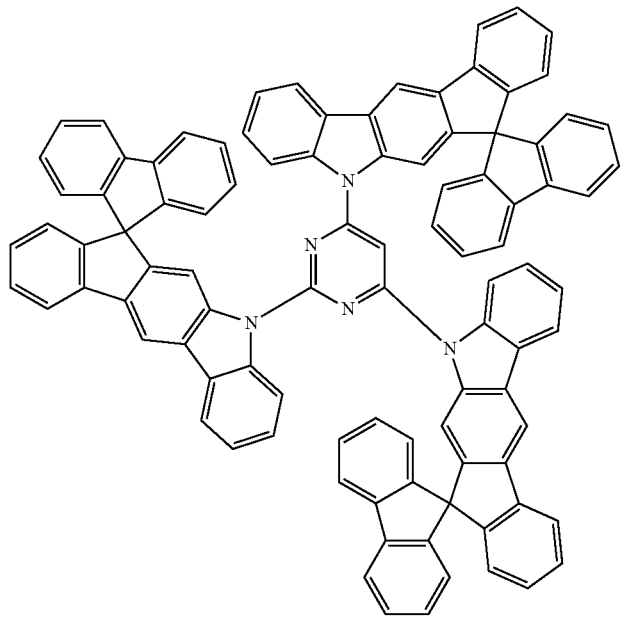
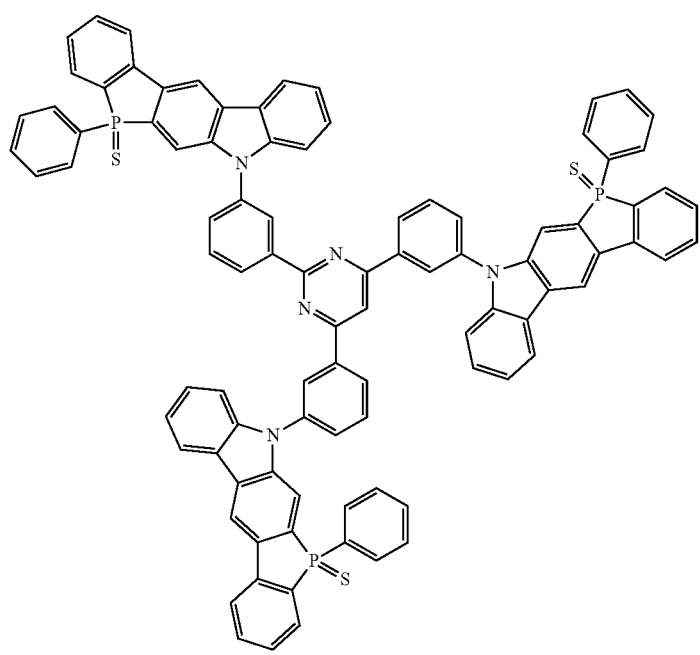

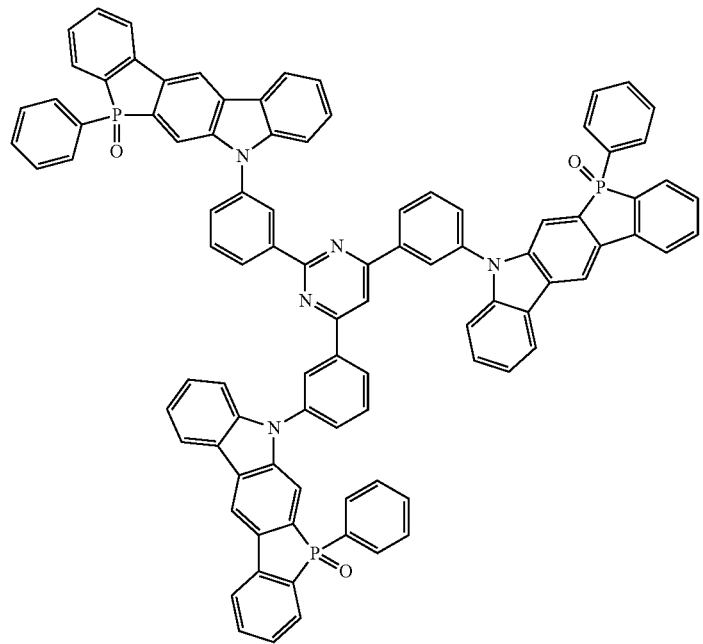
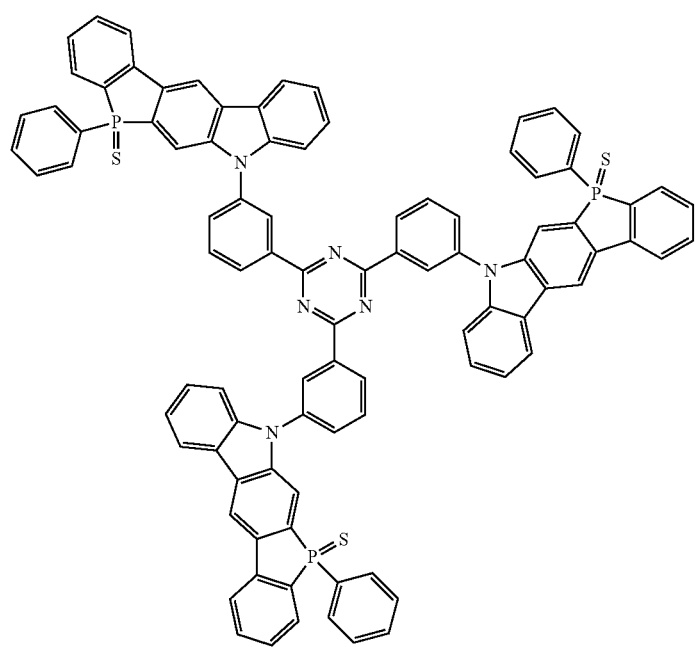

-continued

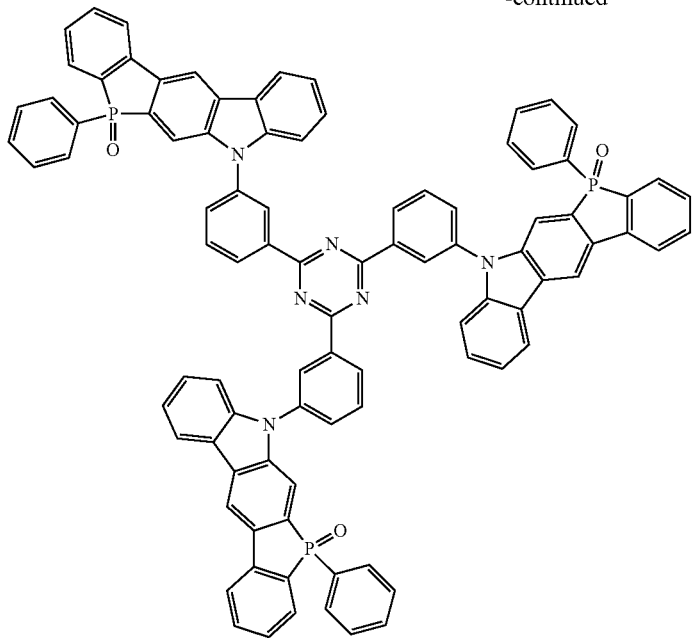

Compound Represented by Formula 1[III]

In an aspect, the invention provides a compound represented by formula 1[III] (also referred as "compound 1[III]"). The compound 1[III] is suitable for use in forming the layer of organic EL device by a coating method and is useful as a material for organic electroluminescence devices.

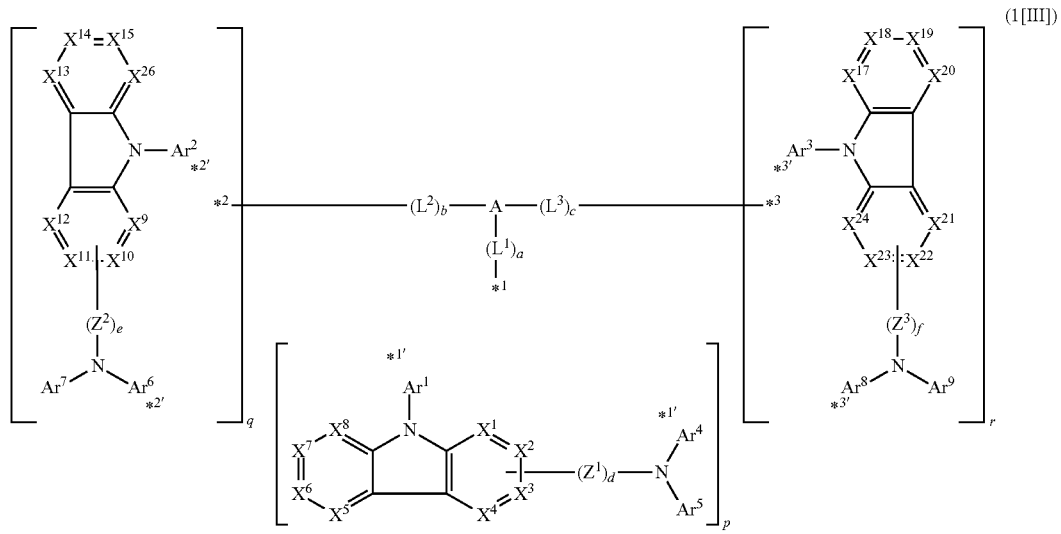

In formula 1[III],

A represents a substituted or unsubstituted nitrogen-containing heteroaromatic hydrocarbon group having 5 to 30 ring atoms;

$L^1$ to $L^3$ each independently represent a substituted or unsubstituted aromatic hydrocarbon group having 6 to 30 ring carbon atoms, a substituted or unsubstituted heterocyclic group having 5 to 30 ring atoms, or a group wherein 2 to 4 groups selected from the preceding groups are bonded to each other;

a to c each independently represent 0 or 1;

$X^1$ to $X^{24}$ each represent $C(R^1)$ to $C(R^{24})$, respectively, or a nitrogen atom;

$R^1$ to $R^{24}$ each independently represent a hydrogen atom or a substituent;

provided that one of $X^1$ to $X^4$ represents a carbon atom which is directly bonded to $Z^1$ or the nitrogen atom to which $Ar^4$ and $Ar^5$ are bonded, one of $X^9$ to $X^{12}$ represents a carbon atom which is directly bonded to $Z^2$ or the nitrogen atom to which $Ar^6$ and $Ar^7$ are bonded, one of $X^{21}$ to $X^{24}$ represents a carbon atom which is directly bonded to $Z^3$ or the nitrogen atom to which $Ar^8$ and $Ar^9$ are bonded, two selected from $R^1$ to $R^8$, two selected from $R^9$ to $R^{16}$, and two selected from $R^{17}$ to $R^{24}$, each not involved in the above direct bonding, may be bonded to each other to form a ring;

Ar$^1$ to Ar$^3$ each independently represent a substituted or unsubstituted aryl group having 6 to 30 ring carbon atoms or a substituted or unsubstituted heteroaryl group having 5 to 30 ring atoms;

Ar$^4$ to Ar$^9$ each independently represent a substituted or unsubstituted aryl group having 6 to 30 ring carbon atoms or a substituted or unsubstituted heteroaryl group having 5 to 30 ring atoms;

Z$^1$ to Z$^3$ each independently represent a substituted or unsubstituted aromatic hydrocarbon group having 6 to 30 ring carbon atoms, a substituted or unsubstituted heterocyclic group having 5 to 30 ring atoms, or a group wherein 2 to 4 groups selected from the preceding groups are bonded to each other;

d to f each independently represent 0 or 1;

p to r each independently represent an integer of 0 to 3, p+q+r=3, and when p, q or r is 2 or 3, 2 or 3 groups in each [ ] may be the same or different, respectively; and

*1 is directly bonded to a nitrogen atom from which one of Ar$^1$ and Ar$^4$ indicated by *1' is removed, *2 is directly bonded to a nitrogen atom from which one of Ar$^2$ and Ar$^6$ indicated by *2' is removed, and *3 is directly bonded to a nitrogen atom from which one of Ar$^3$ and Ar$^8$ indicated by *3' is removed.

Description of Each Group in Formula 1[III]

The nitrogen-containing heteroaromatic hydrocarbon group for A has 5 to 30, preferably 6 and 20, and more preferably 6 to 14 ring carbon atoms. The nitrogen-containing heteroaromatic hydrocarbon group is a monocyclic group or a fused ring group comprising two or three fused rings.

The nitrogen-containing heteroaromatic hydrocarbon group contains preferably 1 to 3 and more preferably 2 or 3 nitrogen atoms. Particularly, the nitrogen-containing heteroaromatic hydrocarbon group contains preferably 2 or 3 and more preferably 3 nitrogen atoms when it is a monocyclic group, and preferably 2 nitrogen atoms when it is a fused ring group having two or three fused rings. On one hand, the nitrogen-containing heteroaromatic hydrocarbon group may contain a hetero atom other than a nitrogen atom, such as an oxygen atom, a sulfur atom, a silicon atom, and selenium atom, bun on the other hand preferably contains only a nitrogen atom as the heteroatom.

Examples of the nitrogen-containing heteroaromatic hydrocarbon group for A include residues of compounds selected from pyrrole, pyridine, pyridazine, pyrimidine, pyrazine, triazine, imidazole, pyrazole, oxadiazole, thiadiazole, triazole, tetrazole, indole, isoindole, indolizine, quinolizine, quinoline, isoquinoline, naphthyridine, cinnoline, phthalazine, quinazoline, benzo[f]quinazoline, benzo[h]quinazoline, quinoxaline, benzimidazole, indazole, carbazole, biscarbazole, phenanthridine, acridine, phenanthroline, phenazine, azatriphenylene, diazatriphenylene, hexaazatriphenylene, azacarbazole, azadibenzofuran, azadibenzothiophene, and dinaphtho[2',3': 2,3:2',3': 6,7]carbazole.

The residue is a mono valent or more valent group obtained by removing one or more hydrogen atoms from the above compound. The valency of the nitrogen-containing heteroaromatic hydrocarbon group, i.e., the valency of "A" corresponds to the value of "a+b+c."

The nitrogen-containing heteroaromatic hydrocarbon group mentioned above is preferably a residue of the following compounds:

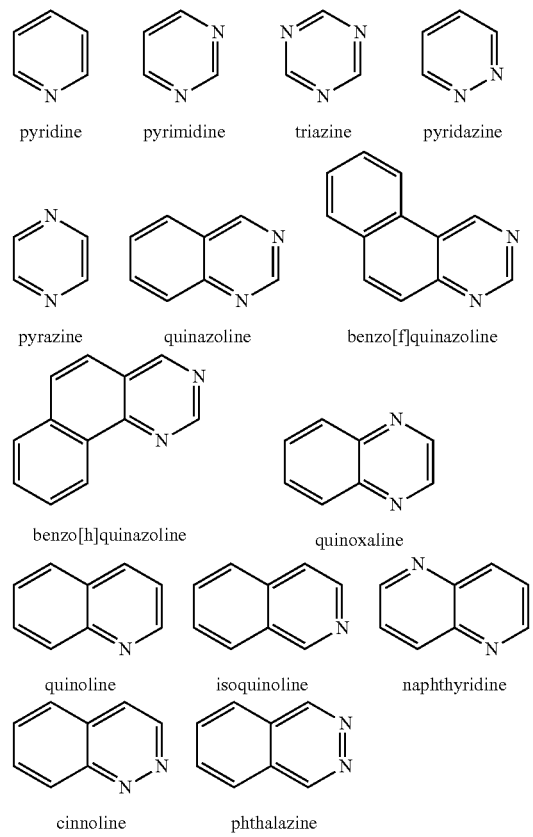

In an aspect of the invention, the nitrogen-containing heteroaromatic hydrocarbon group for A is preferably a residue of the nitrogen-containing heterocyclic ring represented by formula (A1):

in formula (A1), X$^{101}$ to X$^{104}$ each represent C(R$^{101}$) to C(R$^{104}$), respectively, or a nitrogen atom; R$^{101}$ to R$^{104}$ each independently represent a hydrogen atom or a substituent; and two selected from R$^{102}$ to R$^{104}$ may be bonded to each other to form a ring.

In an aspect of the invention, the nitrogen-containing heteroaromatic hydrocarbon group for A is more preferably a residue of the nitrogen-containing heterocyclic ring represented by any of formulae (A2) to (A4):

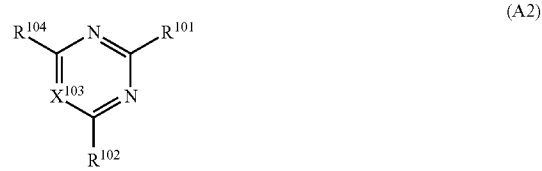

in formula (A2), X$^{103}$ represents C(R$^{103}$) or a nitrogen atom; R$^{101}$ to R$^{104}$ each independently represent a hydrogen atom or a substituent; and two selected from $R^{102}$ to $R^{104}$ may be bonded to each other to form a ring;

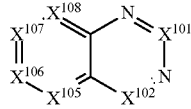
(A3)

in formula (A3), $X^{101}$, $X^{102}$, and $X^{105}$ to $X^{108}$ each represent $C(R^{101})$, $C(R^{102})$, or $C(R^{105})$ to $C(R^{108})$, respectively, or a nitrogen atom; $R^{101}$, $R^{102}$, and $R^{105}$ to $R^{108}$ each independently represent a hydrogen atom or a substituent; and two selected from $R^{102}$ and $R^{106}$ to $R^{108}$ may be bonded to each other to form a ring; and

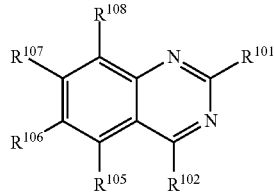
(A4)

in formula (A4), $R^{101}$, $R^{102}$, and $R^{105}$ to $R^{108}$ each independently represent a hydrogen atom or a substituent; and two selected from $R^{102}$ and $R^{105}$ to $R^{108}$ may be bonded to each other to form a ring.

The nitrogen-containing heteroaromatic hydrocarbon group for A in formula 1[III] may have a substituent.

Examples of the substituent of the nitrogen-containing heteroaromatic hydrocarbon group include the substituents mentioned above and also include, for example, a 9-carbazolyl group having a substituted amino substituent, a substituted amino group having a carbazolyl substituent, an aryl group having a substituted amino substituent, a 9-carbazolyl group having a heteroaryl substituent, an aryl group having a carbazolyl substituent, and a substituted amino group having a heteroaryl substituent.

In formula 1[II], the aromatic hydrocarbon group for $L^1$ to $L^3$ has 6 to 30, preferably 6 to 18, more preferably 6 to 13, still more preferably 6 to 12, and particularly preferably 6 to 10 ring carbon atoms.

The aromatic hydrocarbon group for $L^1$ to $L^3$ is preferably a di- to tetravalent residue of any of the following compounds. In an aspect of the invention, preferably at least one of $L^1$ to $L^3$ and more preferably all thereof are di- to tetravalent residues of any of the following compounds:

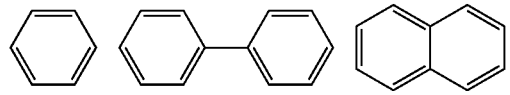

wherein each carbon atom in the compound may have a substituent.

The aromatic hydrocarbon group for $L^1$ to $L^3$ is more preferably a group represented by any of the following formulae. In an aspect of the invention, preferably at least one of $L^1$ to $L^3$ and more preferably all thereof are groups represented by any of the following formulae:

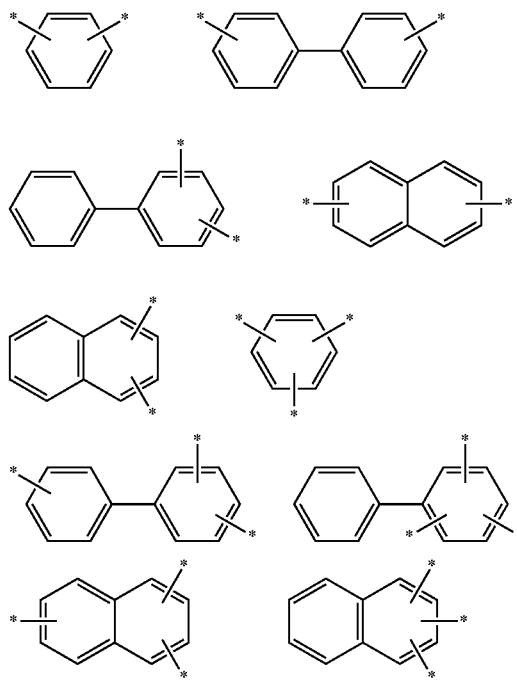

wherein * indicates a bonding site and each carbon atom other than that at the bonding site may have a substituent.

The aromatic hydrocarbon group for $L^1$ to $L^3$ is more preferably a group represented by any of the following formulae. Preferably at least one of $L^1$ to $L^3$ and more preferably all thereof are groups represented by any of the following formulae:

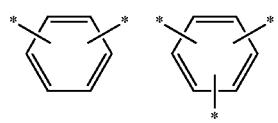

wherein * indicates a bonding site and each carbon atom other than that at the bonding site may have a substituent.

The aromatic hydrocarbon group for $L^1$ to $L^3$ is still more preferably a group represented by any of the following formulae. Preferably at least one of $L^1$ to $L^3$ and more preferably all thereof are groups represented by any of the following formulae:

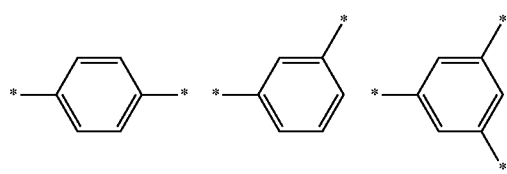

wherein * indicates a bonding site and each carbon atom other than that at the bonding site may have a substituent.

In addition to the above groups, the aromatic hydrocarbon group for $L^1$ to $L^3$ may include the groups represented by the following formulae:

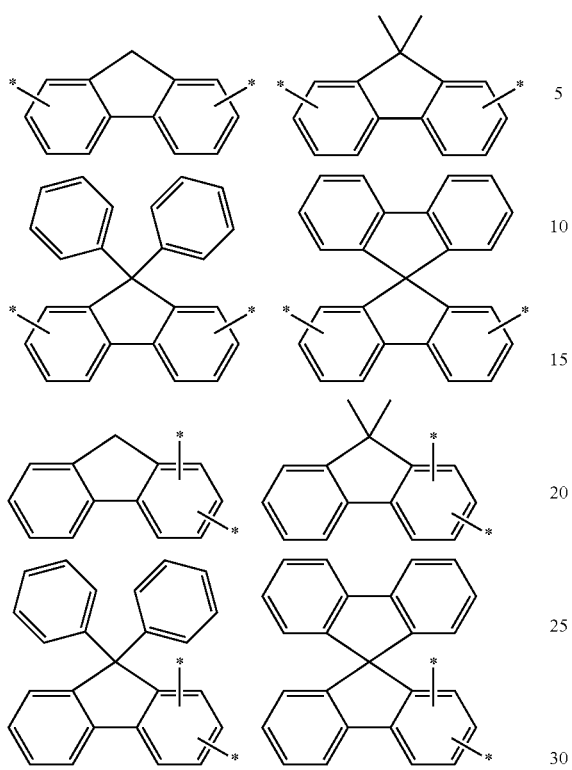
wherein * indicates a bonding site and each carbon atom other than that at the bonding site may have a substituent.
Examples of the divalent aromatic hydrocarbon group for $L^1$ to $L^3$ include the following groups:
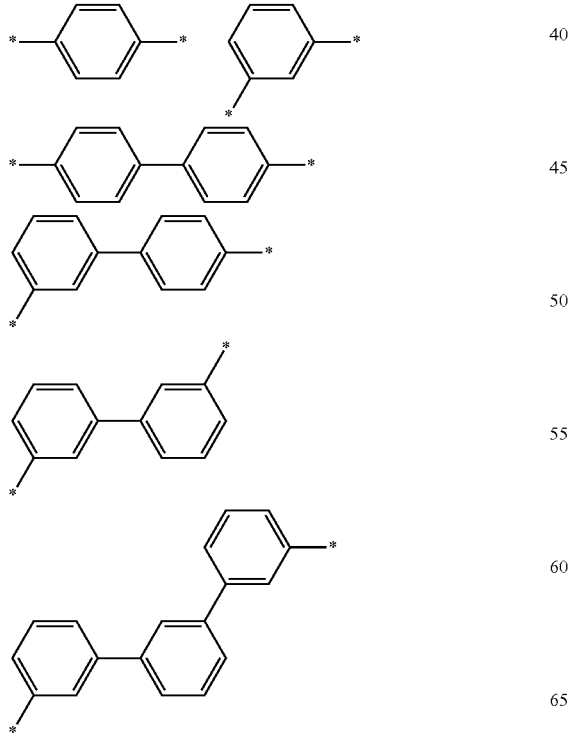
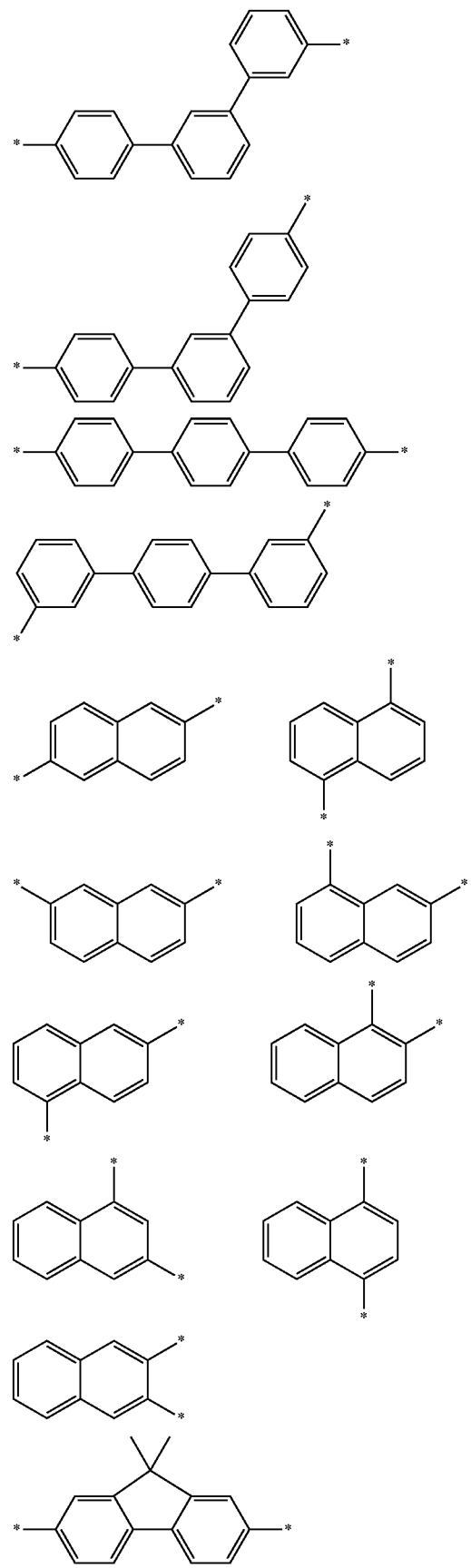

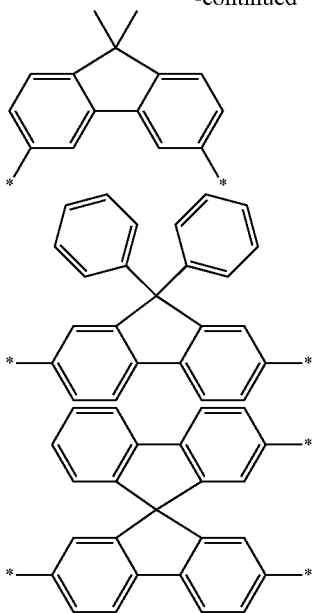

wherein * indicates a bonding site and each carbon atom other than that at the bonding site may have a substituent.

The heterocyclic group for $L^1$ to $L^3$ has 5 to 30, preferably 5 to 18, more preferably 5 to 13, particularly preferably 5 to 10 ring atoms.

Examples of the heterocyclic group include a residue of a nitrogen-containing heterocyclic compound, such as pyrrole, pyridine, imidazopyridine, pyrazole, triazole, tetrazole, indole, isoindole, and carbazole; a residue of an oxygen-containing heterocyclic compound, such as furan, benzofuran, isobenzofuran, dibenzofuran, oxazole, oxadiazole, benzoxazole, benzonaphthofuran, and dinaphthofuran; and a residue of a sulfur-containing heterocyclic compound, such as thiophene, benzothiophene, dibenzothiophene, thiazole, thiadiazole, benzothiazole, benzonaphthothiophene, and dinaphthothiophene.

The "group wherein 2 to 4 groups selected from the preceding groups are bonded to each other" for $L^1$ to $L^3$ is a group wherein 2 to 4 groups selected from a substituted or unsubstituted aromatic hydrocarbon group having 6 to 30 ring carbon atoms and a substituted or unsubstituted heterocyclic group having 5 to 30 ring atoms are bonded to each other. The order of bonding is not particularly limited.

In particular, each of $L^1$ to $L^3$ is preferably a substituted or unsubstituted aromatic hydrocarbon group having 6 to 30 ring carbon atoms. The aromatic hydrocarbon group more preferred is as described above.

$X^1$ to $X^{24}$ each represent $C(R^1)$ to $C(R^{24})$, respectively, or a nitrogen atom, and $R^1$ to $R^{24}$ each independently represent a hydrogen atom or a substituent.

One of $X^1$ to $X^4$ represents a carbon atom which is directly bonded to $Z^1$ or the nitrogen atom to which $Ar^4$ and $Ar^5$ are bonded. Namely, one of $X^1$ to $X^4$ is a carbon atom directly bonded to the nitrogen atom to which $Ar^4$ and $Ar^5$ are bonded when d is 0, and a carbon atom directly bonded to $Z^1$ when d is 1.

One of $X^9$ to $X^{12}$ is a carbon atom which is directly bonded to $Z^2$ or the nitrogen atom (N) to which $Ar^6$ and $Ar^7$ are bonded, and one of $X^{21}$ to $X^{24}$ is a carbon atom which is directly bonded to $Z^3$ or the nitrogen atom to which $Ar^8$ and $Ar^9$ are bonded. Namely, one of $X^9$ to $X^{12}$ is a carbon atom directly bonded to the nitrogen atom (N) to which $Ar^6$ and $Ar^7$ are bonded when e is 0, and a carbon atom directly bonded to $Z^2$ when e is 1. One of $X^{21}$ to $X^{24}$ is a carbon atom directly bonded to the nitrogen atom (N) to which $Ar^8$ and $Ar^9$ are bonded when f is 0, and a carbon atom directly bonded to $Z^3$ when f is 1.

Two selected from $R^1$ to $R^8$, two selected from $R^9$ to $R^{16}$, and two selected from $R^{17}$ to $R^{24}$, each not involved in the above direct bonding, may be bonded to each other to form a ring. In an aspect of the invention, two selected from $R^1$ to $R^8$, two selected from $R^9$ to $R^{16}$, and two selected from $R^{17}$ to $R^{24}$, each not involved in the above direct bonding, are preferably not bonded to each other, thereby failing to form a ring.

The "direct bond" used herein is generally called a "single bond" in some cases.

$X^1$ to $X^{24}$ are each preferably $C(R^1)$ to $C(R^{24})$, respectively, and more preferably $R^1$ to $R^{24}$ are all hydrogen atoms.

$Ar^1$ to $Ar^3$ each independently represent a substituted or unsubstituted aryl group having 6 to 30 ring carbon atoms or a substituted or unsubstituted heteroaryl group having 5 to 30 ring atoms.

$Ar^4$ to $Ar^9$ each independently represent a substituted or unsubstituted aryl group having 6 to 30 ring carbon atoms or a substituted or unsubstituted heteroaryl group having 5 to 30 ring atoms.

The aryl group for $Ar^1$ to $Ar^3$, and $Ar^4$ to $Ar^9$ has 6 to 30, preferably 6 to 18, more preferably 6 to 13, still more preferably 6 to 12, and particularly preferably 6 to 10 ring carbon atoms.

Examples of the aryl group include a phenyl group, a naphthyl group (a 1-naphthyl group, a 2-naphthyl group), a naphthylphenyl group, a biphenylyl group, a terphenylyl group, a quaterphenylyl group, a quinquephenylyl group, an acenaphthylenyl group, an anthryl group, a benzanthryl group, an aceanthryl group, a phenanthryl group, a benzophenanthryl group, a phenalenyl group, a fluorenyl group (inclusive of a 9,9-dimethylfluorenyl group, a 9,9-diphenylfluorenyl group, and a 9,9'-spirobifluorenyl group), a benzofluorenyl group, a dibenzofluorenyl group, a picenyl group, a pentaphenyl group, a pentacenyl group, a pyrenyl group, a chrysenyl group, a benzochrysenyl group, a s-indanyl group, an as-indanyl group, a fluoranthenyl group, a benzofluoranthenyl group, a tetracenyl group, a triphenylenyl group, a benzotriphenylenyl group, a perylenyl group, a coronyl group, and a dibenzanthryl group. The above groups include isomeric groups, if any.

In an aspect of the invention, the aryl group for $Ar^4$ to $Ar^9$ is preferably a fused ring group having 10 to 30, preferably 10 to 20, and more preferably 10 to 14 ring carbon atoms. Examples of the fused ring group include a naphthyl group (a 1-naphthyl group, a 2-naphthyl group), an acenaphthylenyl group, an anthryl group, a benzanthryl group, an aceanthryl group, a phenanthryl group, a benzophenanthryl group, a phenalenyl group, a fluorenyl group (inclusive of a 9,9-dimethylfluorenyl group, a 9,9-diphenylfluorenyl group, and a 9,9'-spirobifluorenyl group), a benzofluorenyl group, a dibenzofluorenyl group, a picenyl group, a pentacenyl group, a pyrenyl group, a chrysenyl group, a benzochrysenyl group, a fluoranthenyl group, a benzofluoranthenyl group, a tetracenyl group, a perylenyl group, a coronyl group, and a dibenzanthryl group.

The aryl group is preferably selected from the following groups:

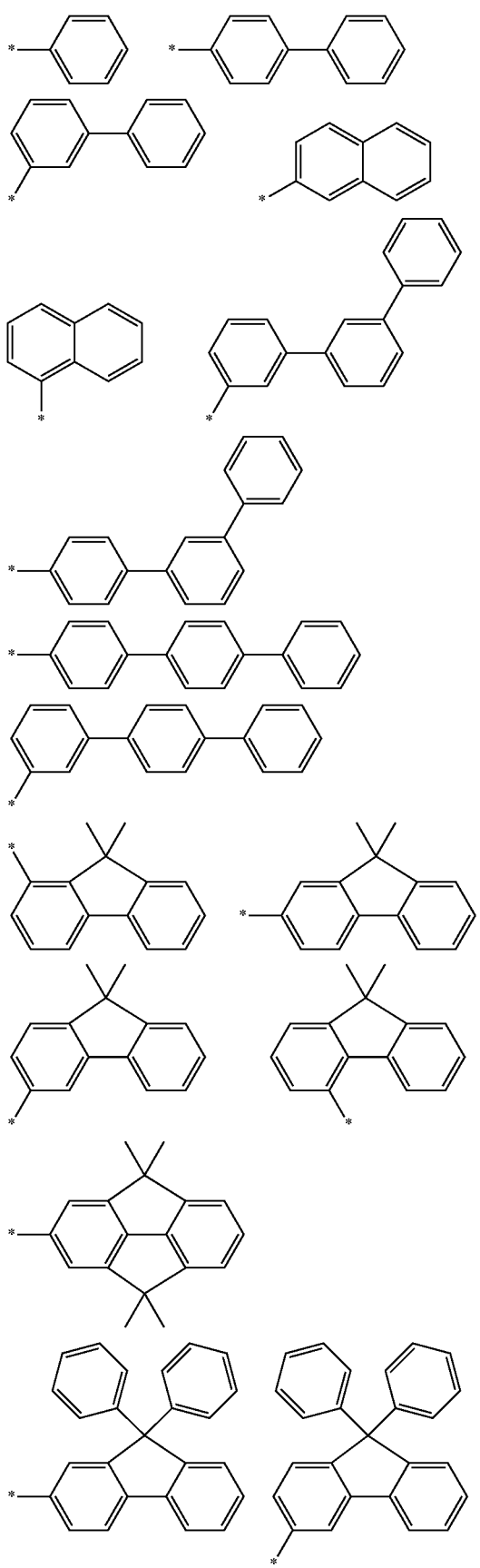
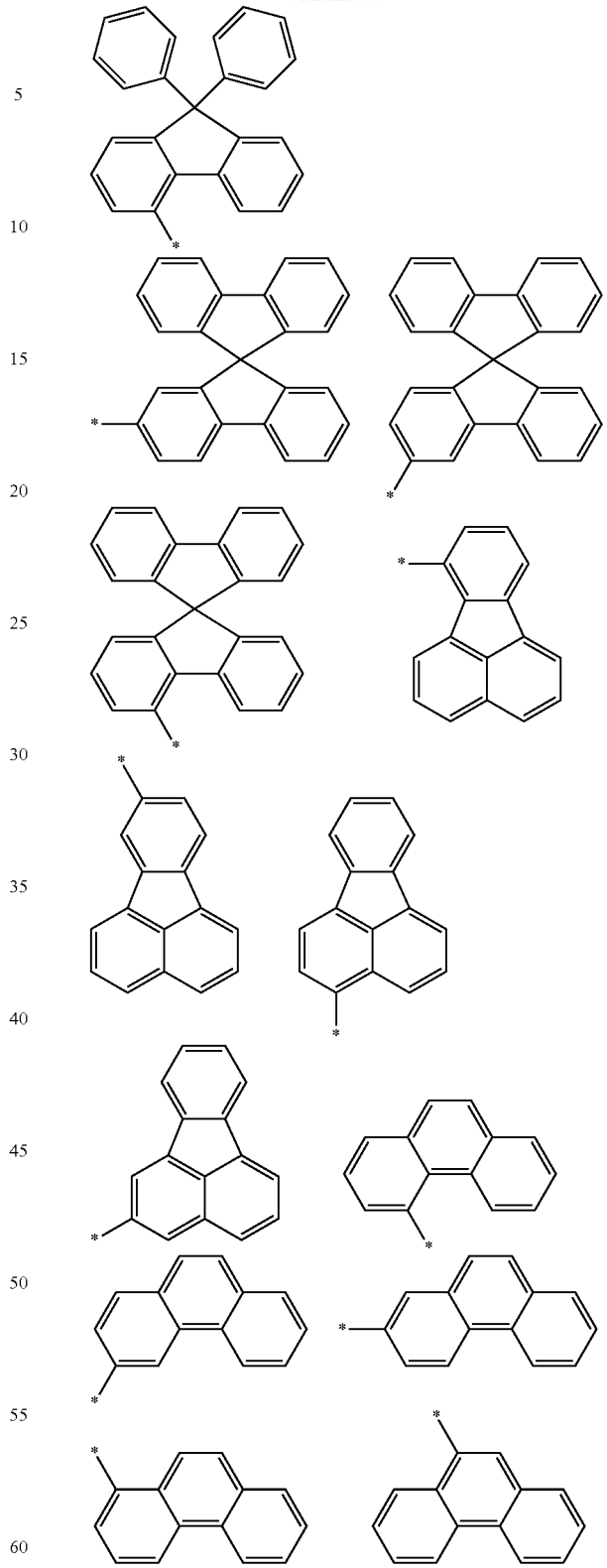
wherein * indicates a bonding site and each carbon atom other than that at the bonding site may have a substituent.
The heteroaryl group for $Ar^1$ to $Ar^3$, and $Ar^4$ to $Ar^9$ has 5 to 30, preferably 5 to 20, more preferably 5 to 14, and still more preferably 5 to 10 ring atoms.

The heteroaryl group contains at least one, preferably 1 to 5, more preferably 1 to 3, and still more preferably 1 to 2 hetero atoms which may be the same or different. The hetero atom may include, for example, a nitrogen atom, a sulfur atom, an oxygen atom, and a phosphorus atom, and preferably selected from these atoms.

Examples of the heteroaryl group include a pyrrolyl group, a furyl group, a thienyl group, a pyridyl group, a pyridazinyl group, a pyrimidinyl group, a pyrazinyl group, a triazinyl group, an imidazolyl group, an oxazolyl group, a thiazolyl group, a pyrazolyl group, an isoxazolyl group, an isothiazolyl group, an oxadiazolyl group, a thiadiazolyl group, a triazolyl group, a tetrazolyl group, an indolyl group, an isoindolyl group, a benzofuranyl group, an isobenzofuranyl group, a benzothiophenyl group, an isobenzothiophenyl group, an indolizinyl group, a quinolizinyl group, a quinolyl group, an isoquinolyl group, a cinnolyl group, a phthalazinyl group, a quinazolinyl group, a quinoxalinyl group, a benzimidazolyl group, a benzoxazolyl group, a benzothiazolyl group, an indazolyl group, a benzisoxazolyl group, a benzisothiazolyl group, a dibenzofuranyl group, a dibenzothiophenyl group, a carbazolyl group, a biscarbazolyl group, a phenanthridinyl group, an acridinyl group, a phenanthrolinyl group, a phenazinyl group, a phenothiazinyl group, a phenoxazinyl group, an azatriphenylenyl group, a diazatriphenylenyl group, a xanthenyl group, an azacarbazolyl group, an azadibenzofuranyl group, an azadibenzothiophenyl group, a benzofuranobenzothiophenyl group, a benzothienobenzothiophenyl group, a dibenzofuranonaphthyl group, a dibenzothienonaphthyl group, a dinaphthothienothiophenyl group, and dinaphtho[2',3': 2,3:2',3': 6,7]carbazolyl group.

Each of $Ar^1$ to $Ar^3$ and $Ar^4$ to $Ar^9$ is preferably a substituted or unsubstituted aryl group having 6 to 30 ring carbon atoms. More preferred examples of the aryl group are as described above.

The aromatic hydrocarbon group, the heterocyclic group, and the group wherein 2 to 4 groups selected from the preceding groups are bonded to each other for $Z^1$ to $Z^3$ in formula 1[III] and preferred examples thereof are as described above with respect to $L^1$ to $L^3$. The aromatic hydrocarbon group for $Z^1$ to $Z^3$ is preferably a phenylene group or a naphthylene group and more preferably a phenylene group.

Of the above, $Z^1$ to $Z^3$ is preferably a substituted or unsubstituted aromatic hydrocarbon group having 6 to 30 ring carbon atoms. The aromatic hydrocarbon group more preferred is as described above.

In formula 1[III], d to f are preferably all 0, all 1, or one is 0 and each of the other two is 1.

As described above, p to r in formula 1[III] each independently represent an integer of 0 to 3, and p+q+r is 3. Preferably, two selected from p to r cannot be 0 at the same time, although not particularly limited thereto.

In formula 1[III], *1 is directly bonded to a nitrogen atom from which one of $Ar^1$ and $Ar^4$ indicated by *1' is removed, *2 is directly bonded to a nitrogen atom from which one of $Ar^2$ and $Ar^6$ indicated by *2' is removed, and *3 is directly bonded to a nitrogen atom from which one of $Ar^3$ and $Ar^8$ indicated by *3' is removed.

For example, formula 1[III] wherein *1 is directly bonded to a nitrogen atom from which $Ar^1$ indicated by *1' is removed is represented by the following formula (shown partially):

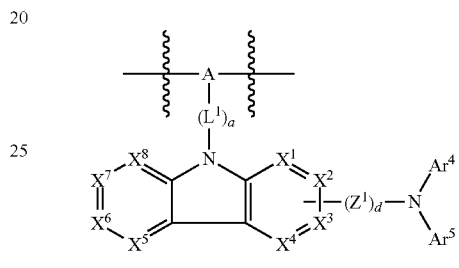

Formula 1[III] wherein *1 is directly bonded to a nitrogen atom from which $Ar^4$ indicated by *1' is removed is represented by the following formula (shown partially):

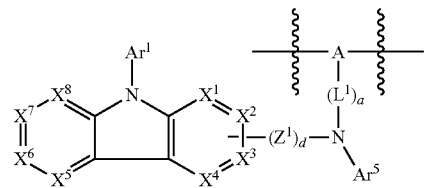

Examples of the group in [ ] of formula 1[III] are shown below, and the group can be arbitrarily selected from the following groups.

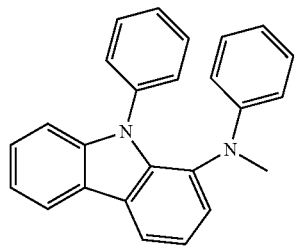
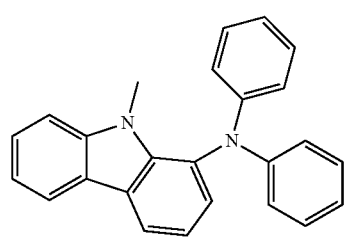
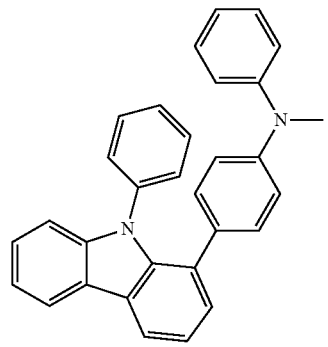

-continued
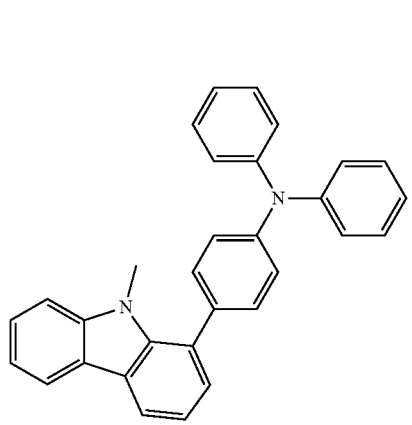
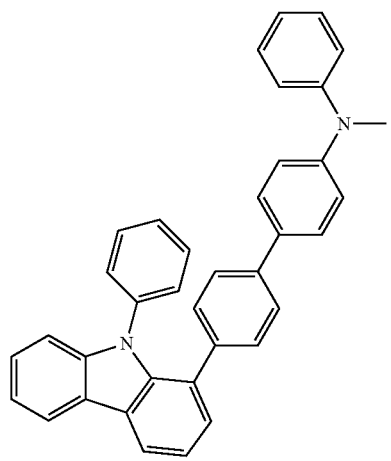
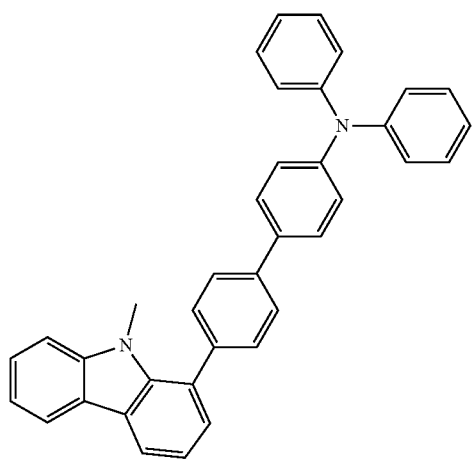
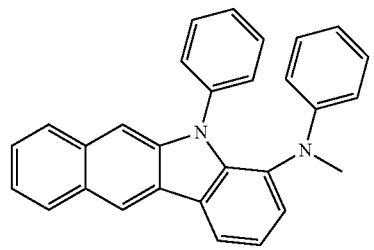
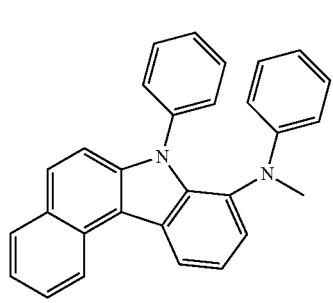
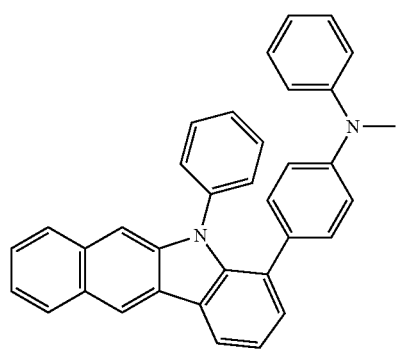
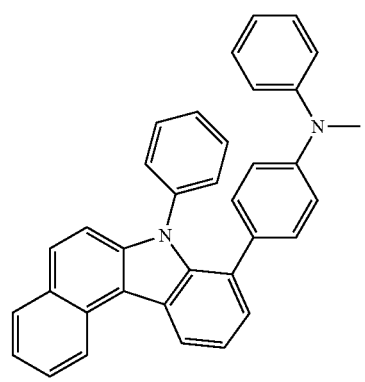

-continued
867
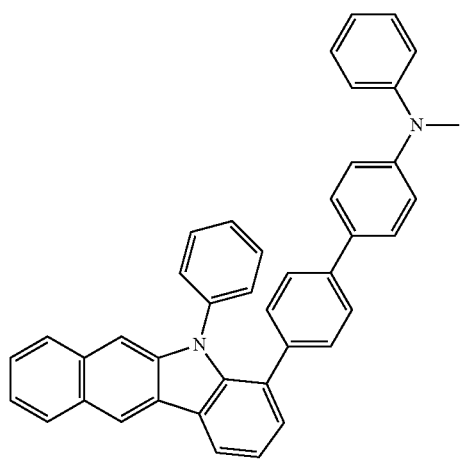
868
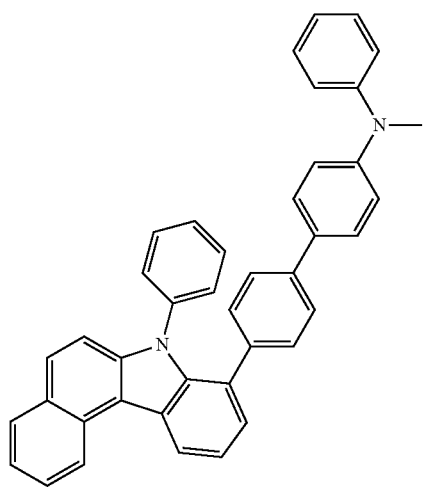
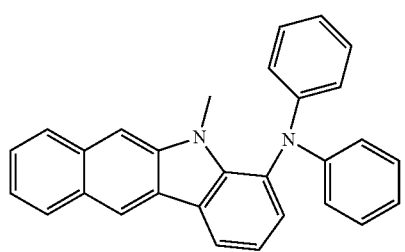
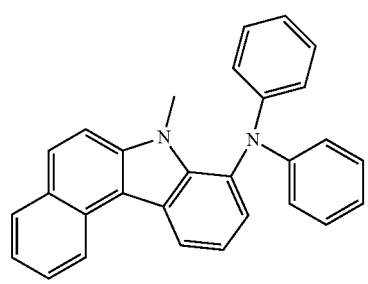
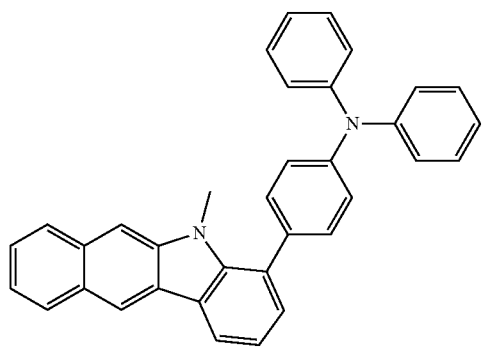
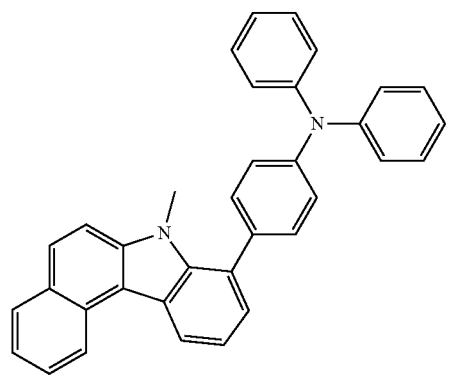
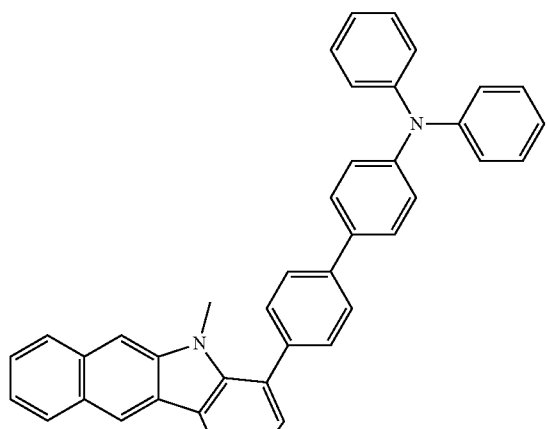
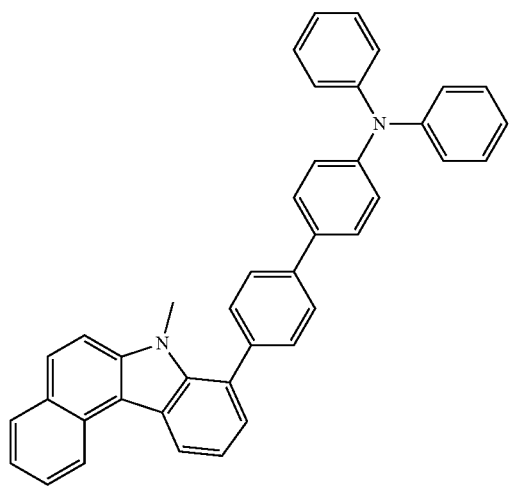

-continued
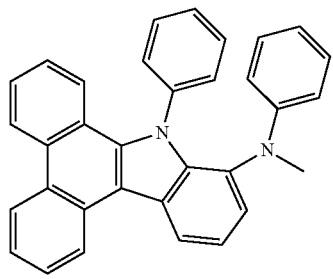 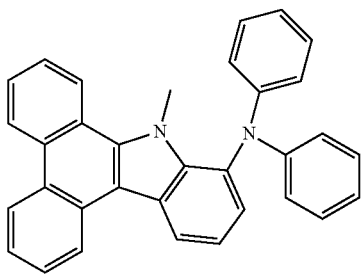 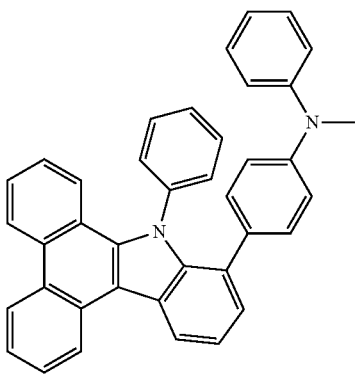
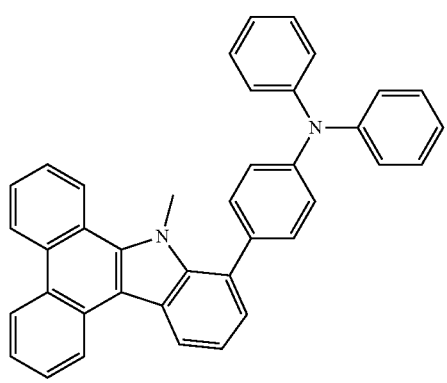 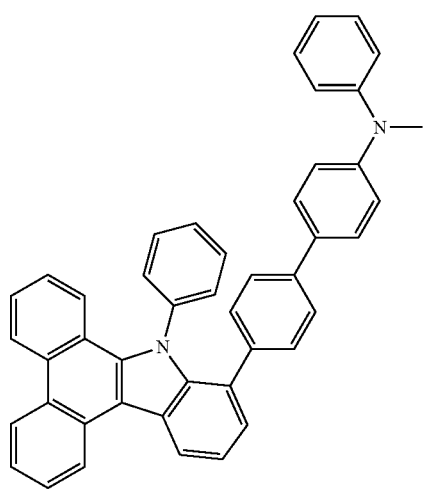
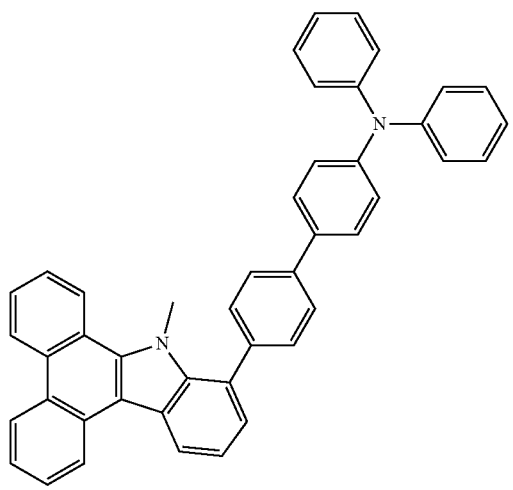 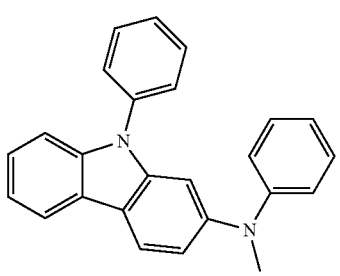
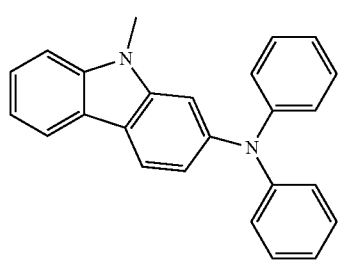 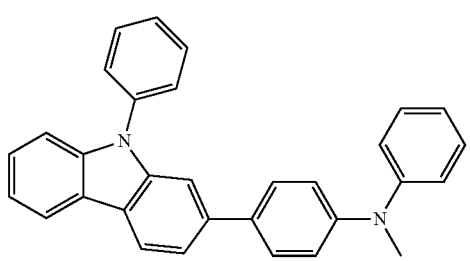

871 872
-continued
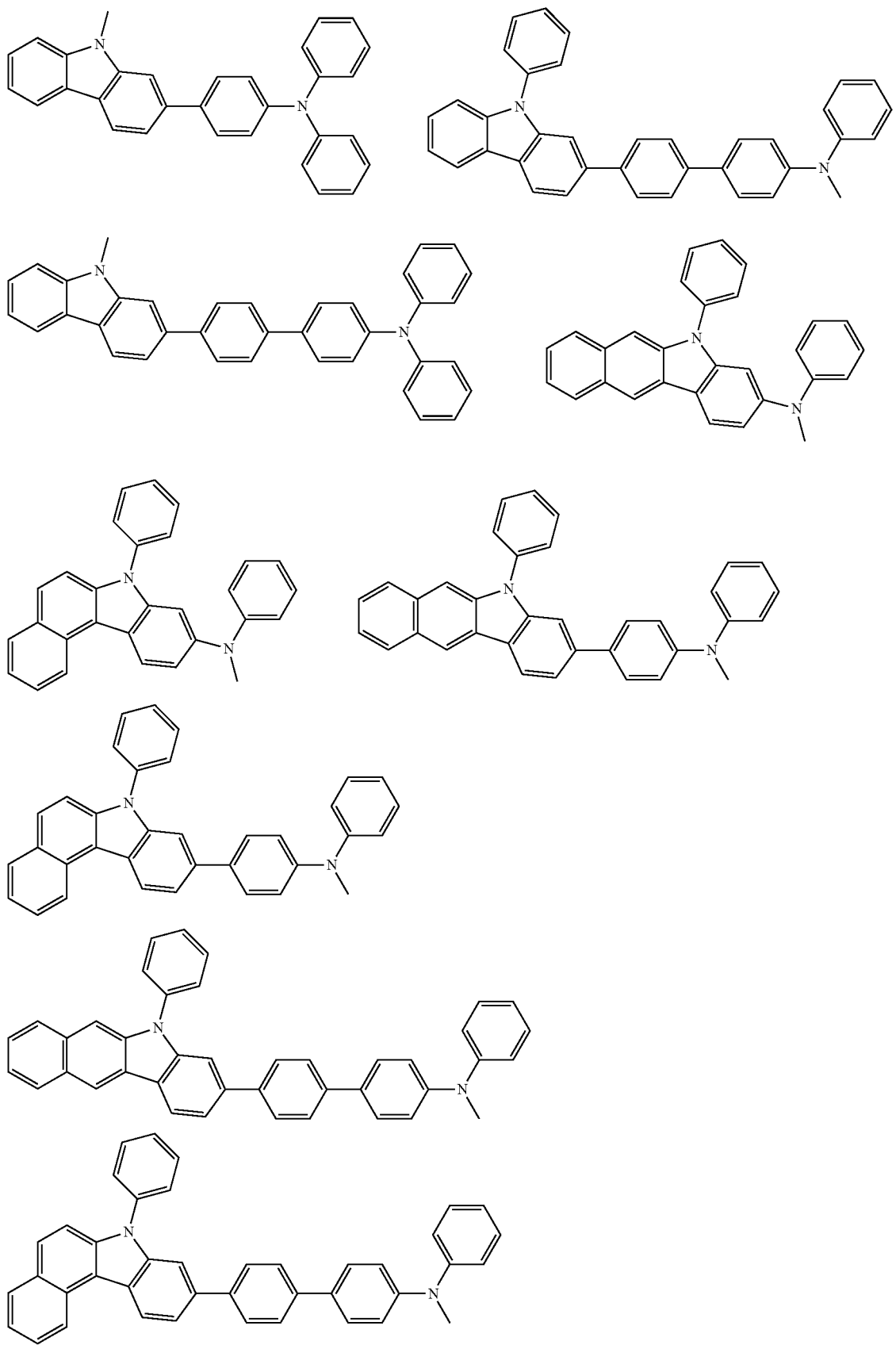

873
874
-continued
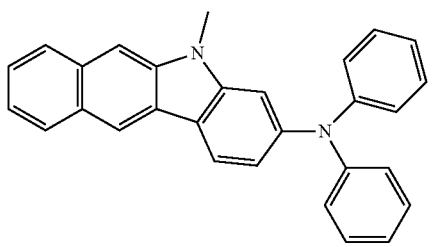
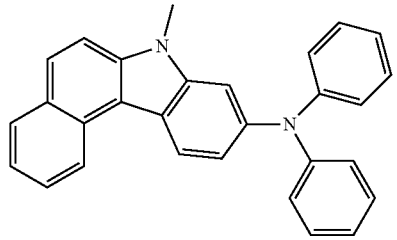
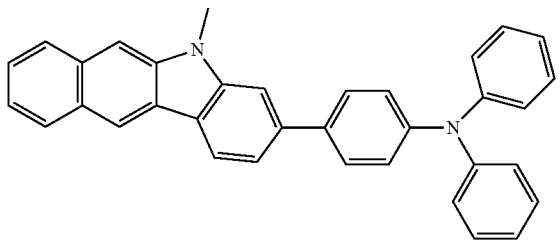
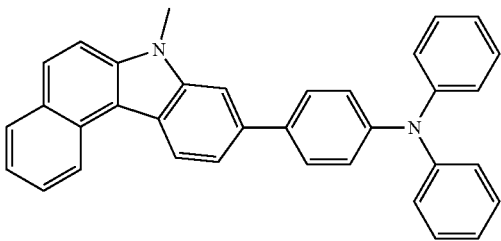
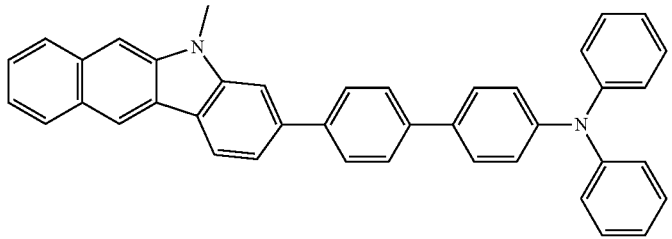
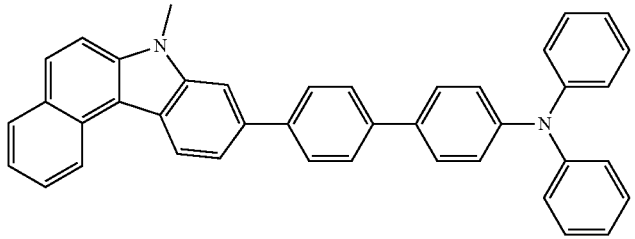
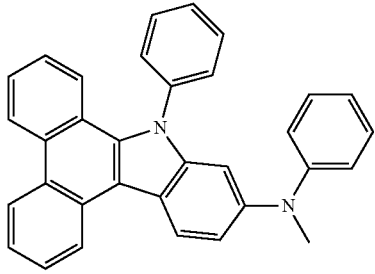
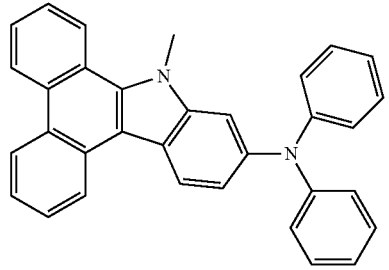
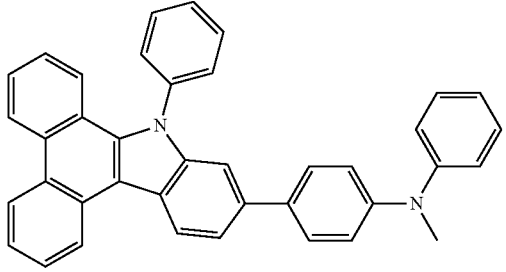
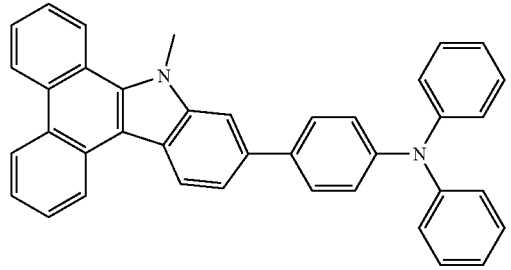

-continued
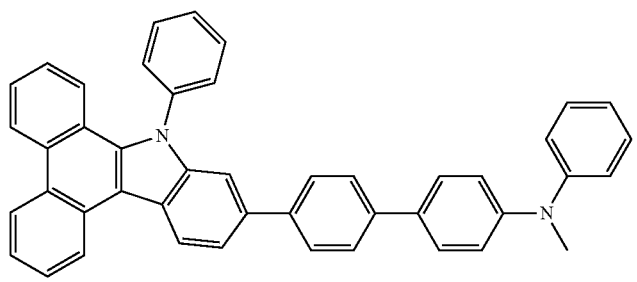
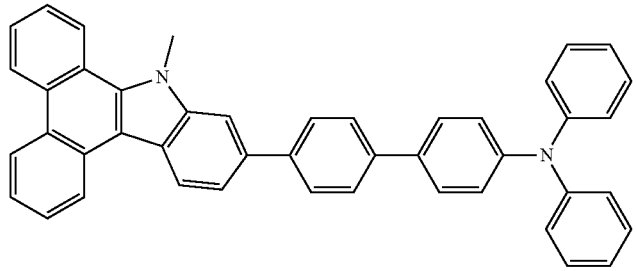
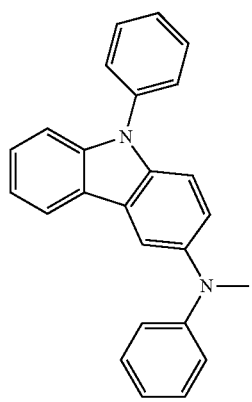 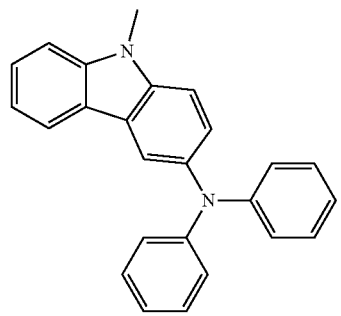 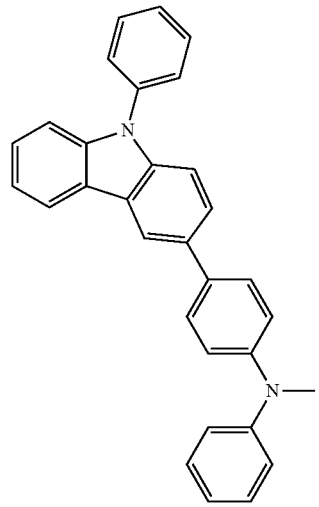
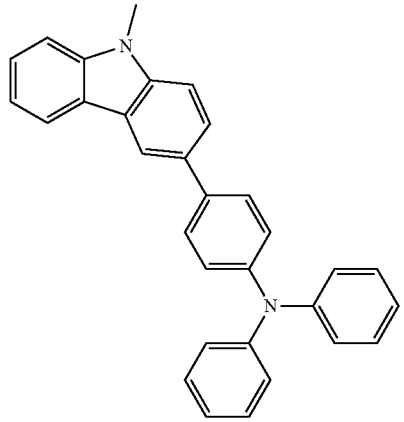 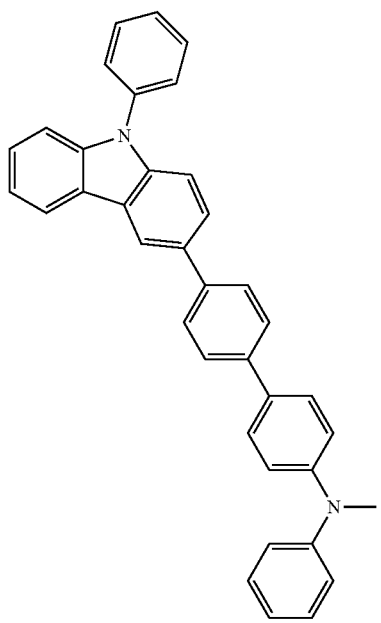

-continued
| 877 | 878 |
|---|---|
| 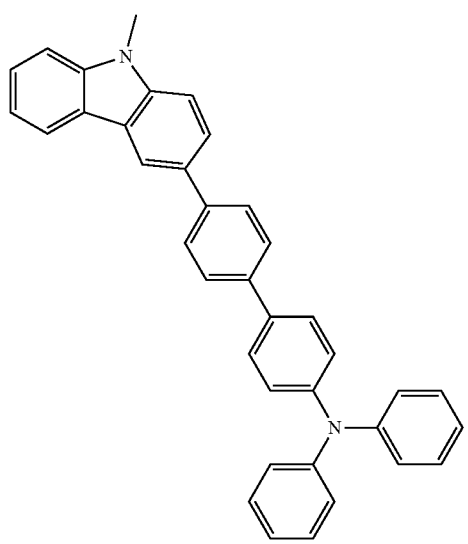 | 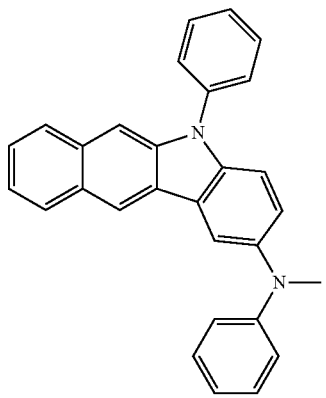 |
| 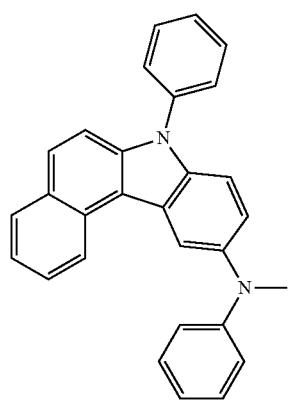 | 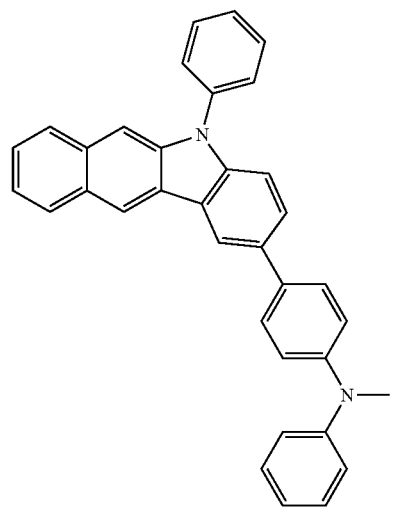 |
| | 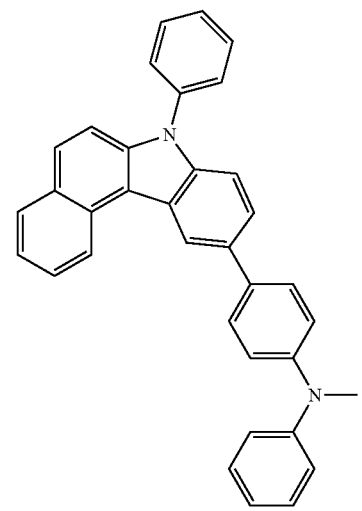 |
| 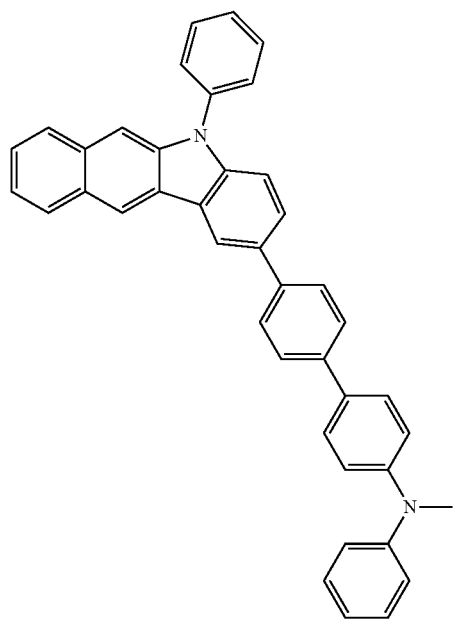 | 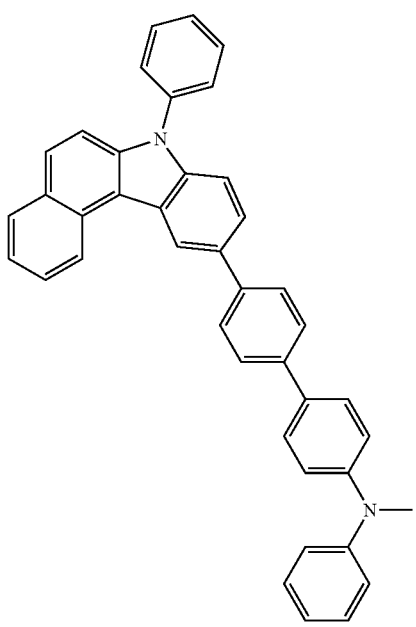 |

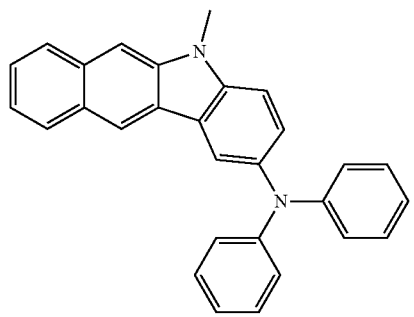
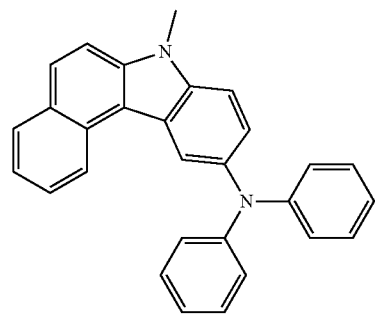
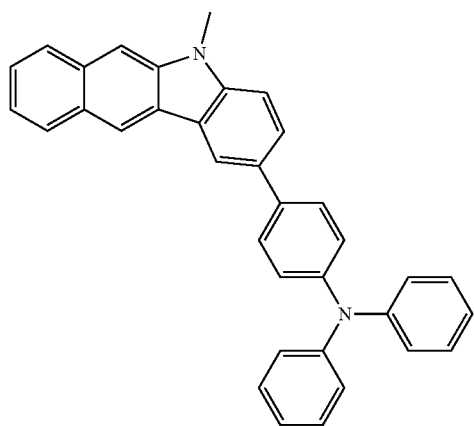
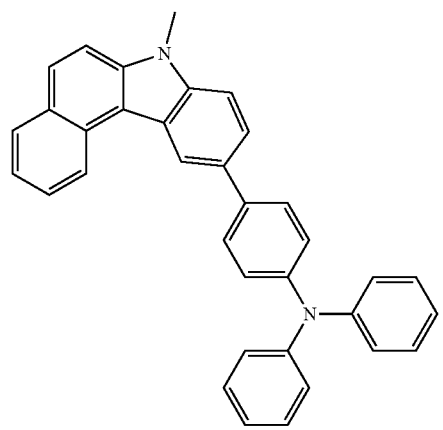
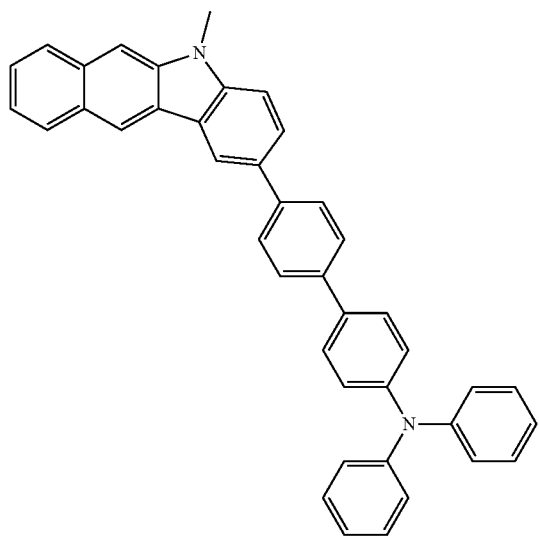
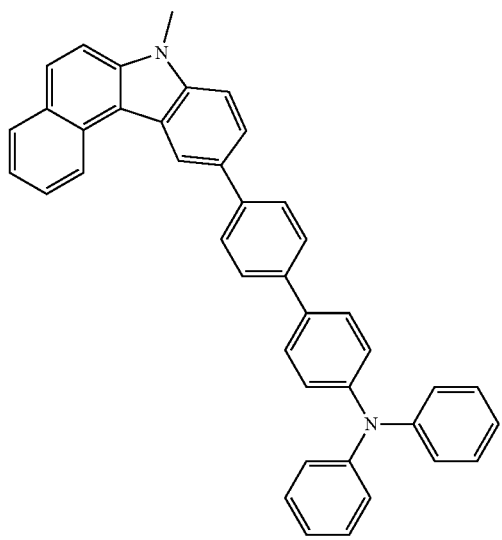

881 882
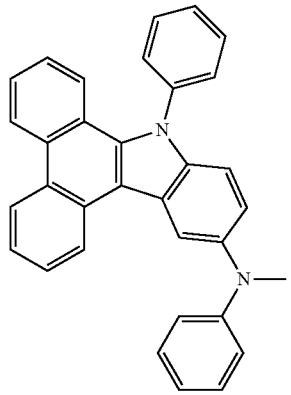
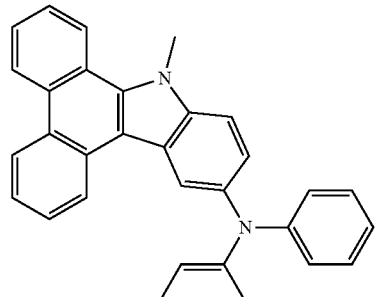
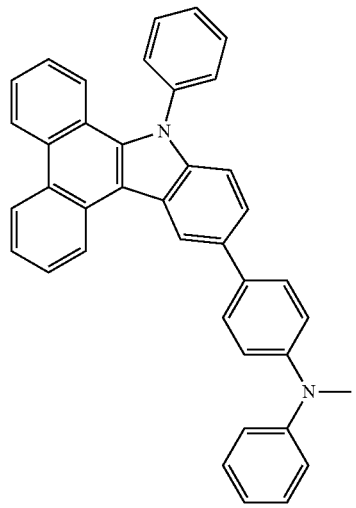
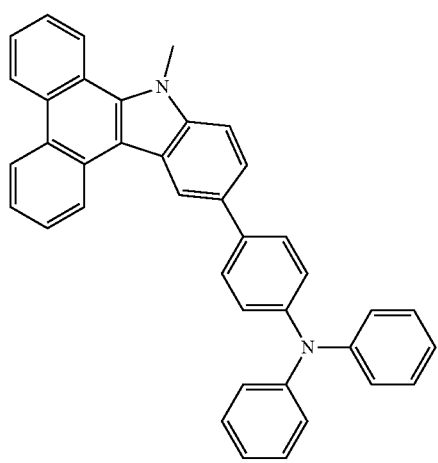
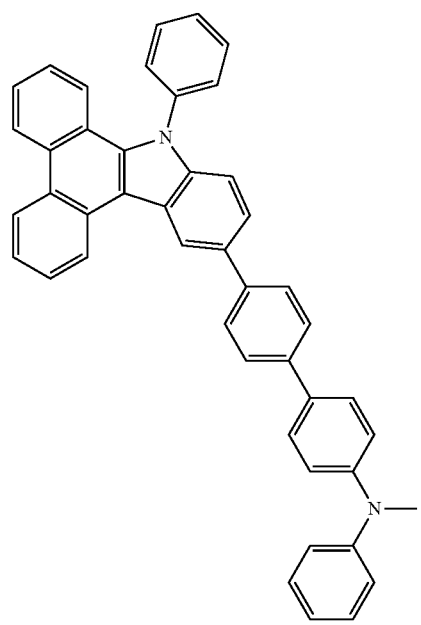
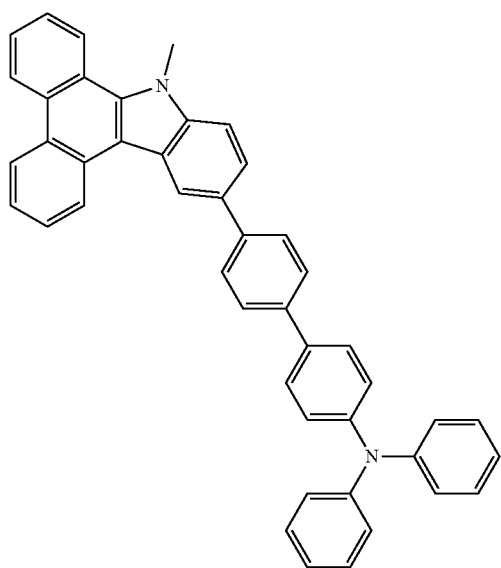
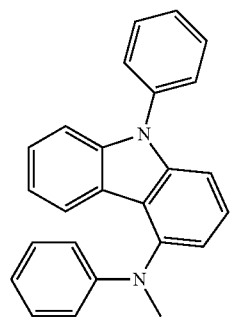
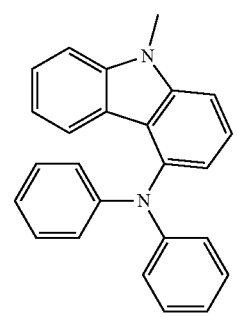

883 884
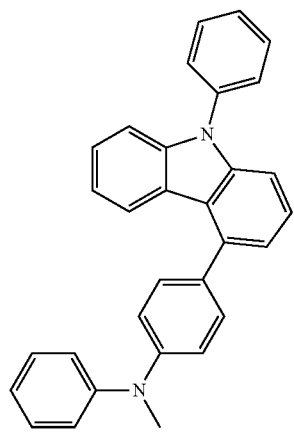 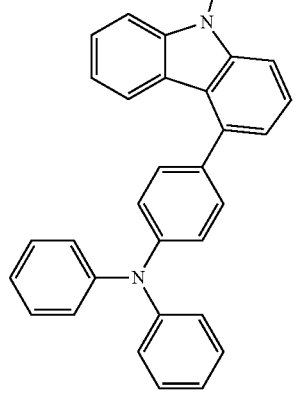 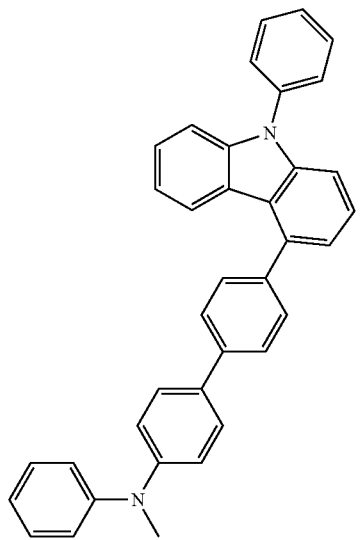
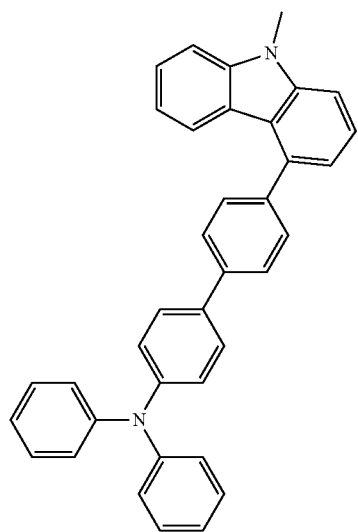 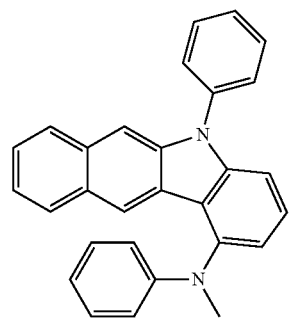 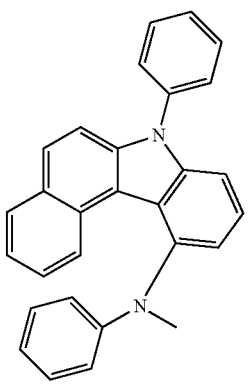
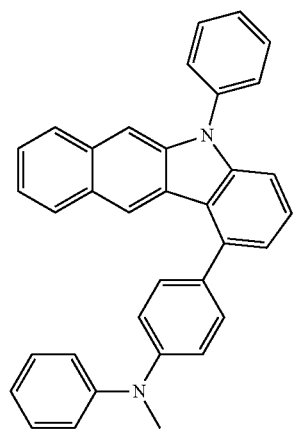 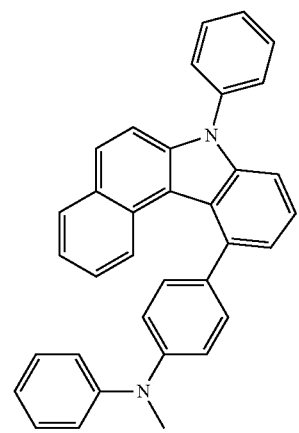 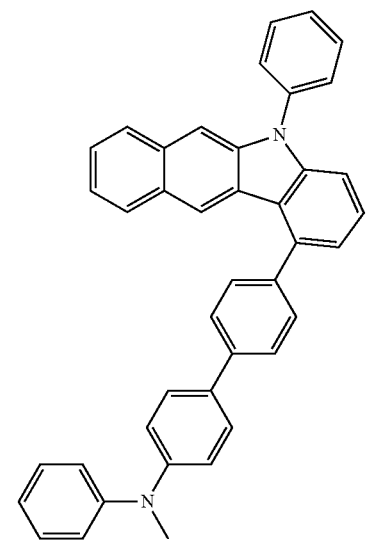

-continued
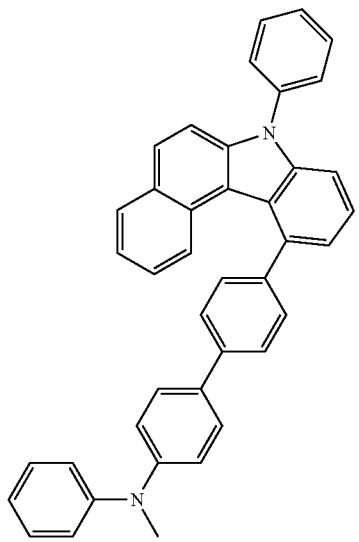
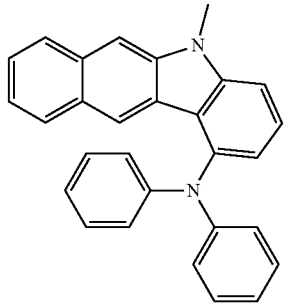
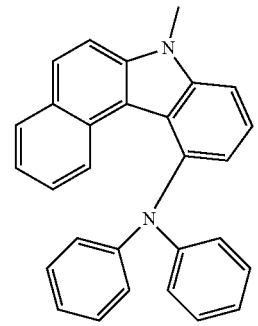
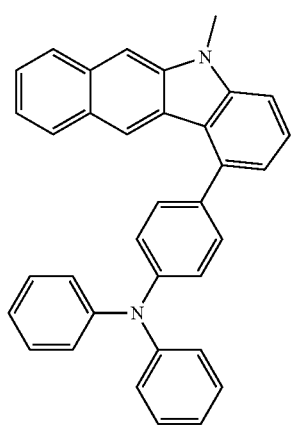
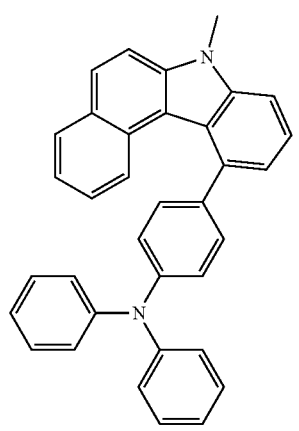
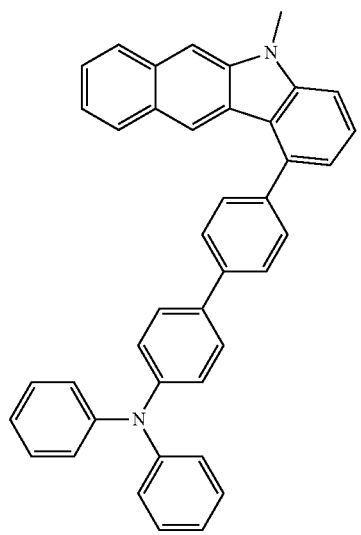
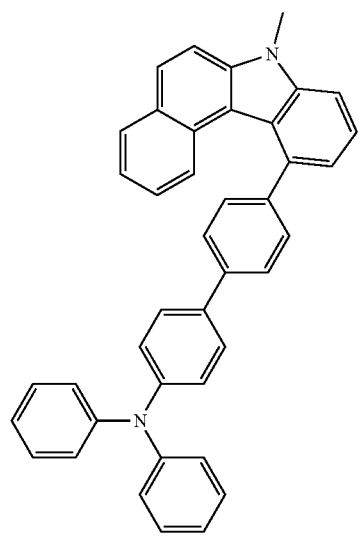
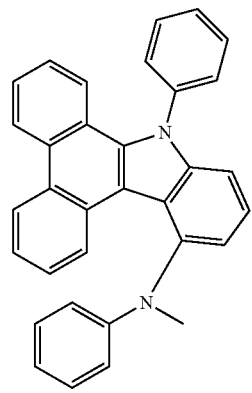
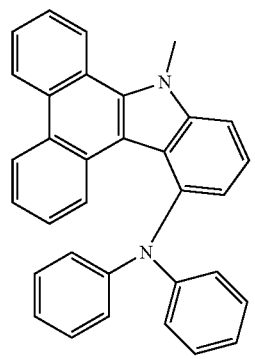

887 888
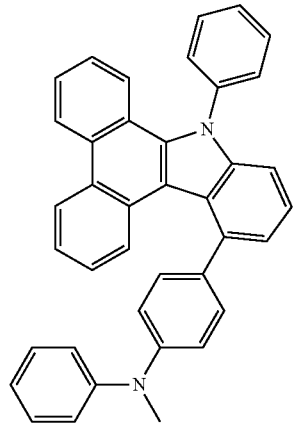 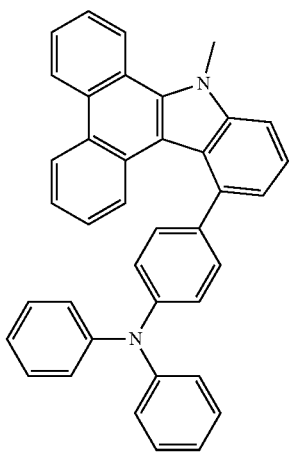 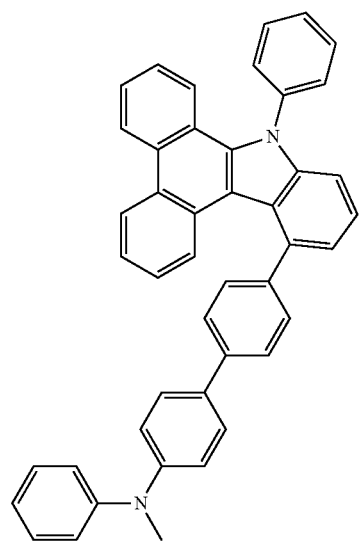
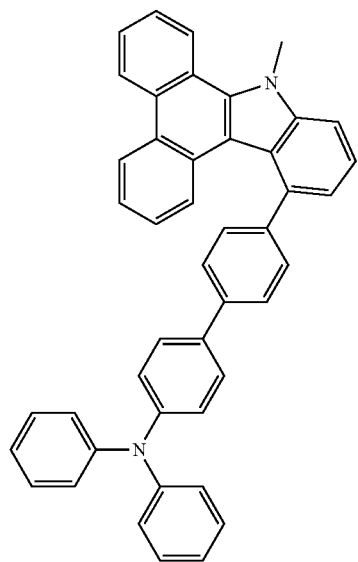 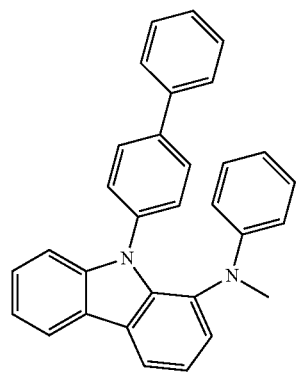 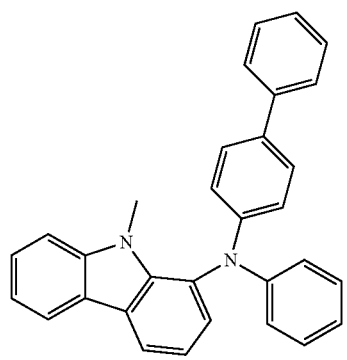
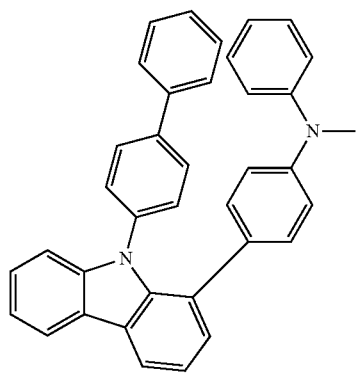 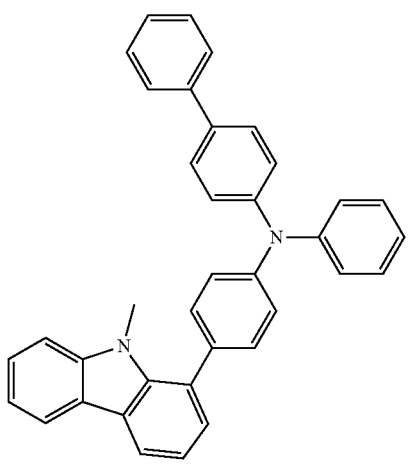

889
890
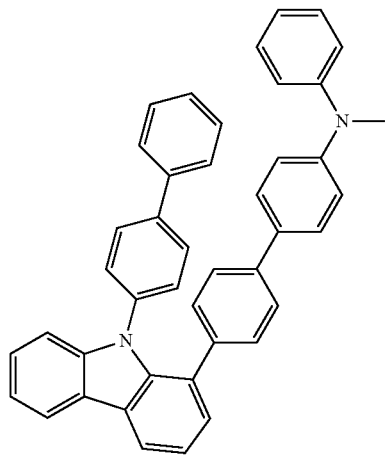
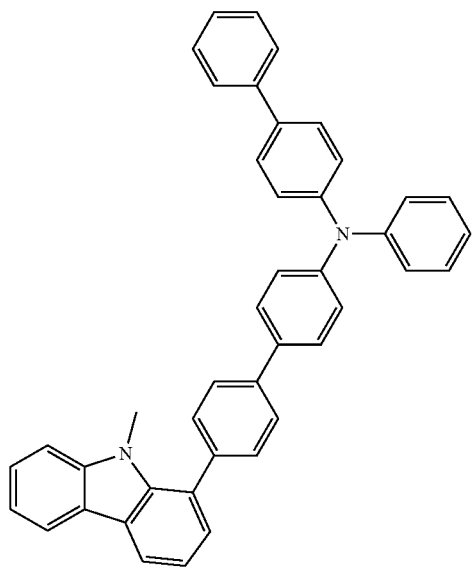
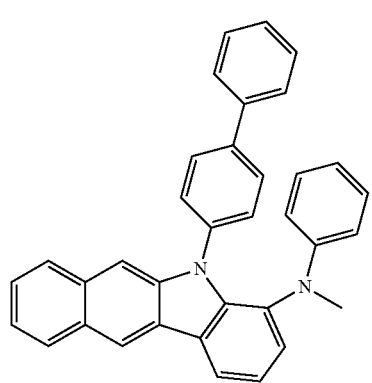
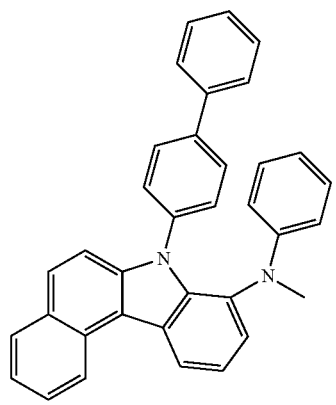
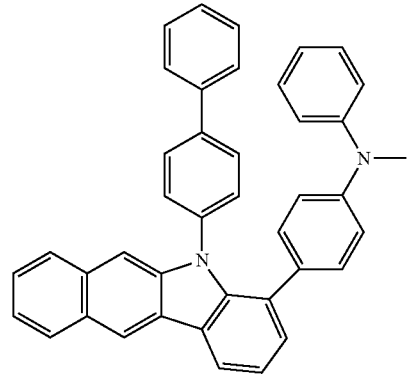
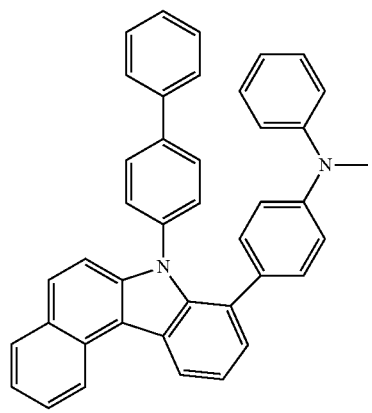
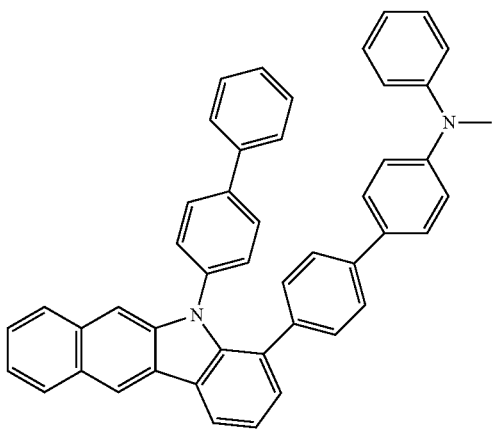

891
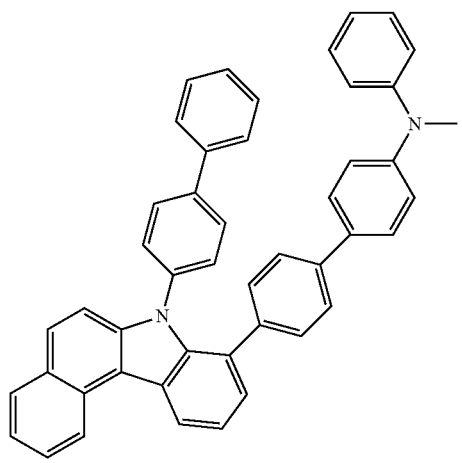
892
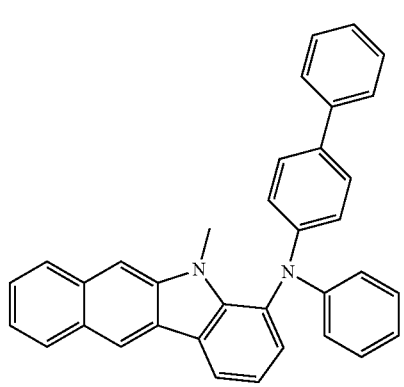
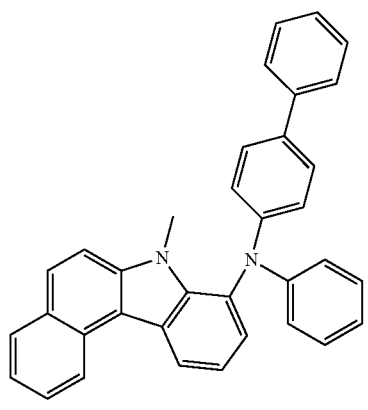
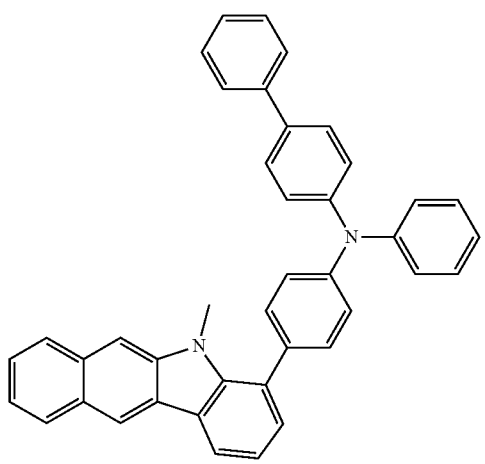
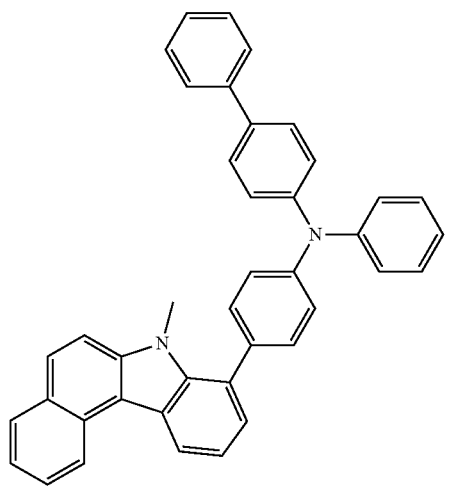
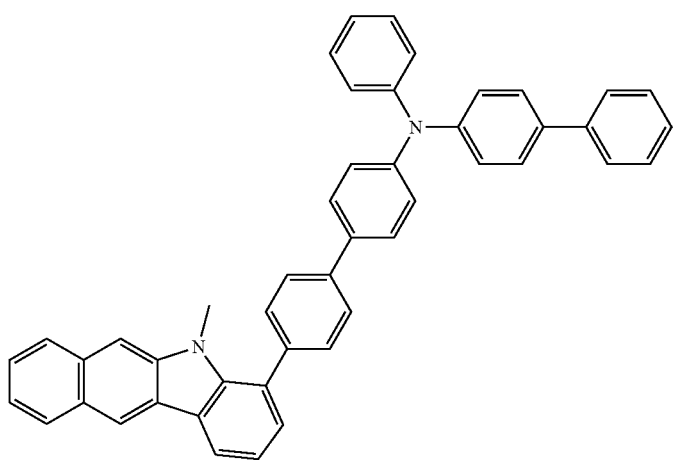

-continued
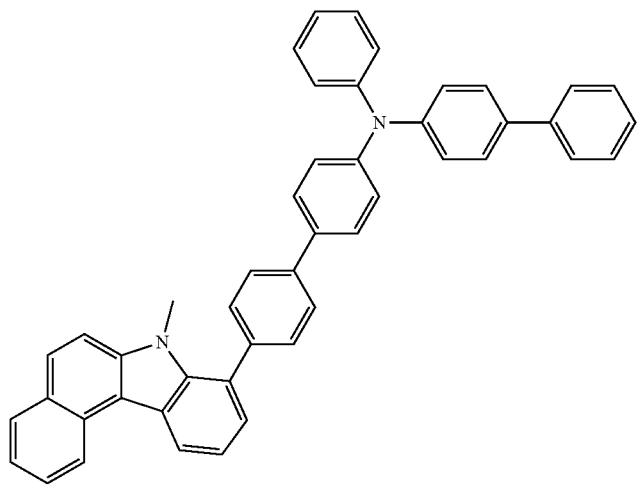
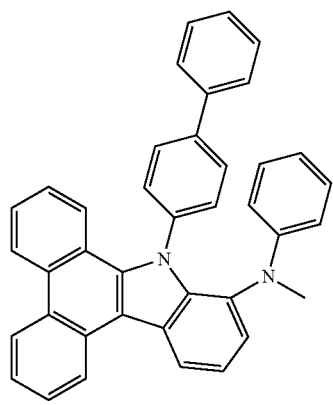
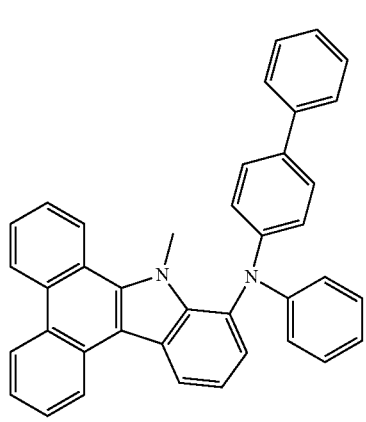
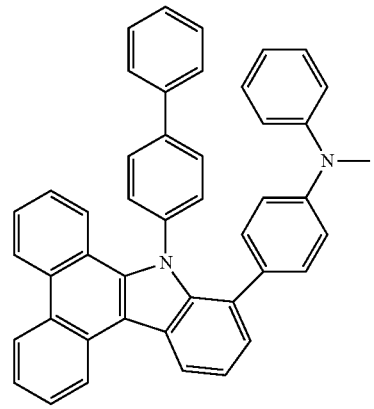
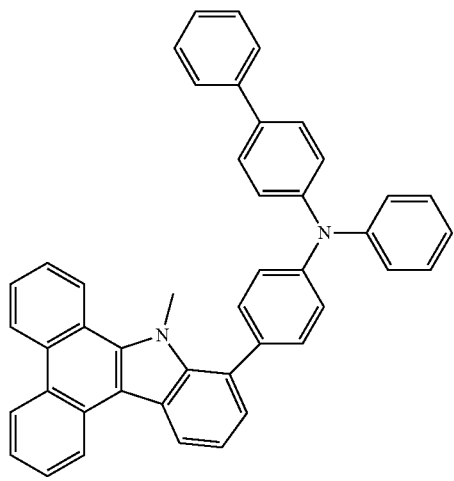
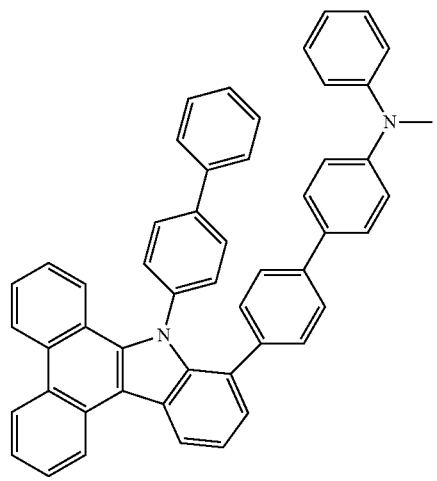

895 896
-continued
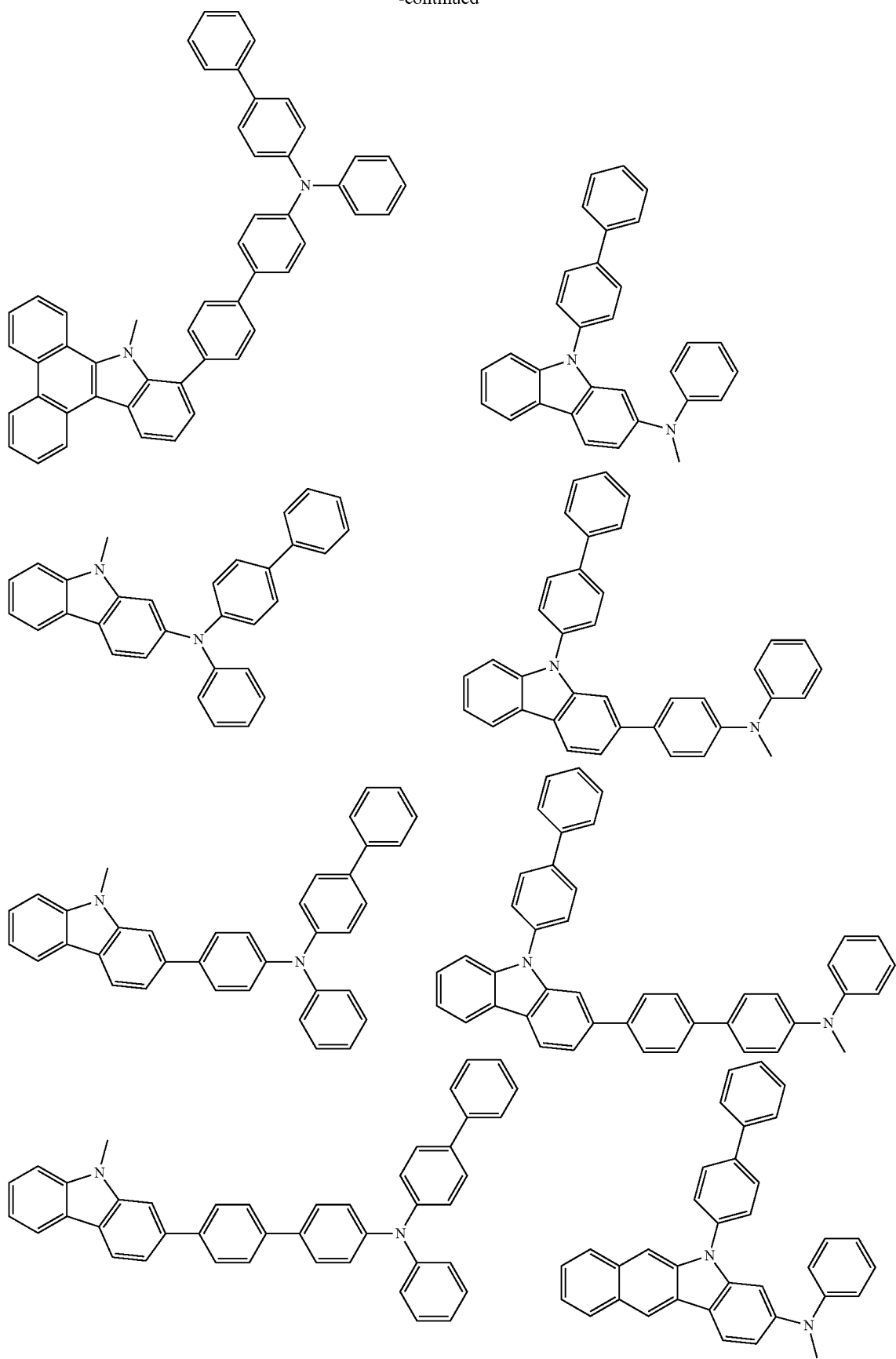

-continued
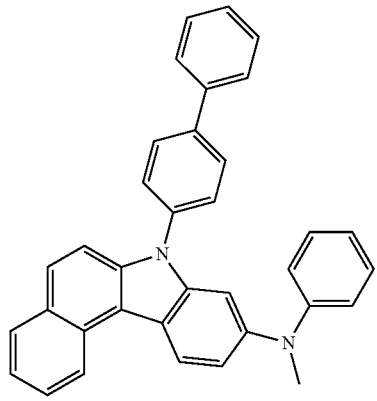
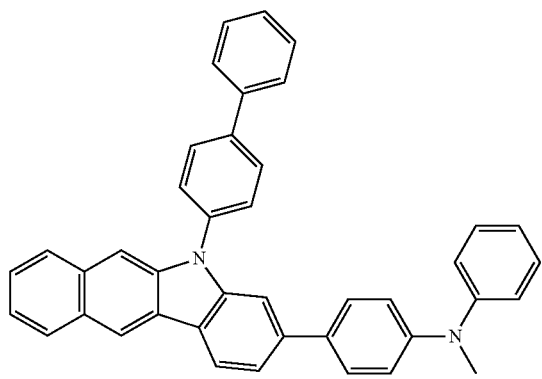
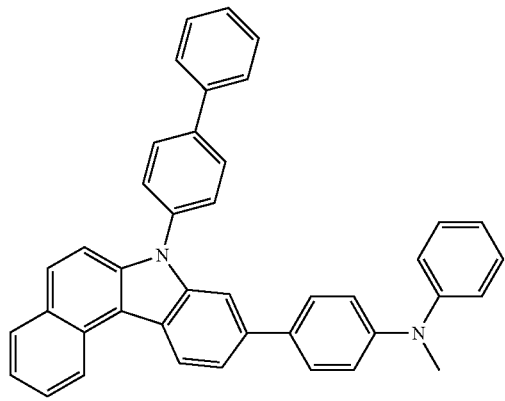
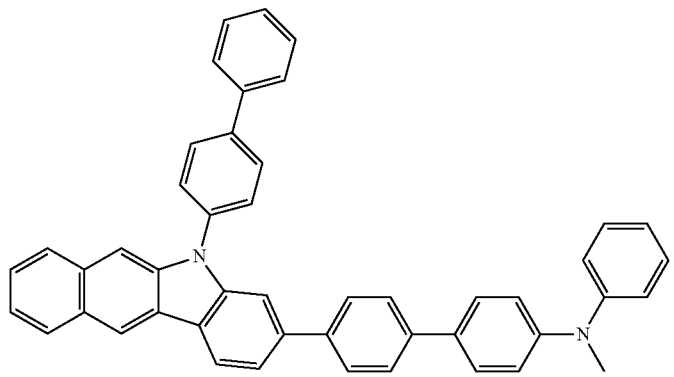
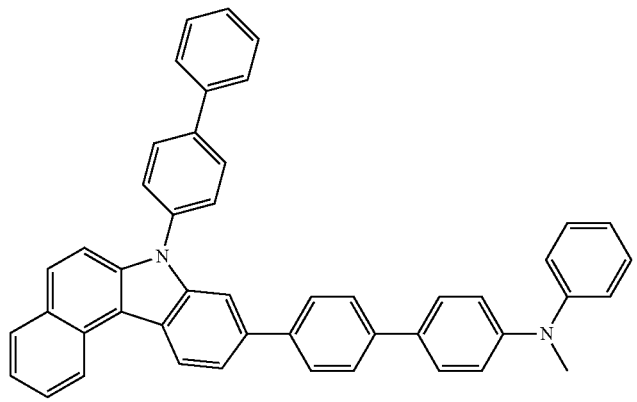
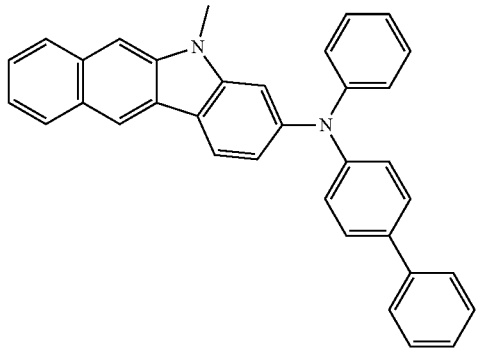

| 899 | 900 |
|---|---|
| 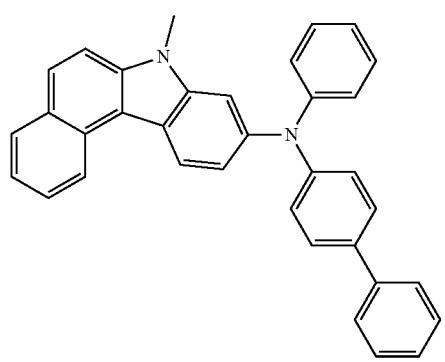 | 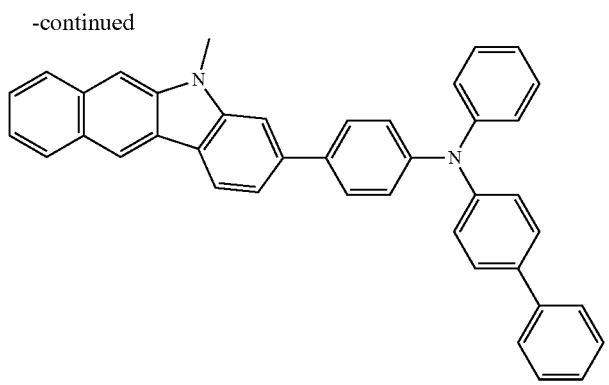 |
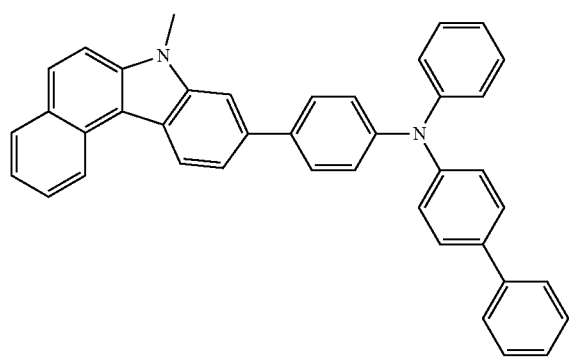
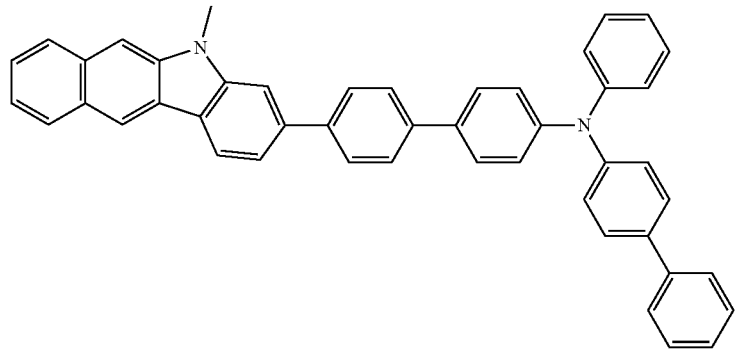
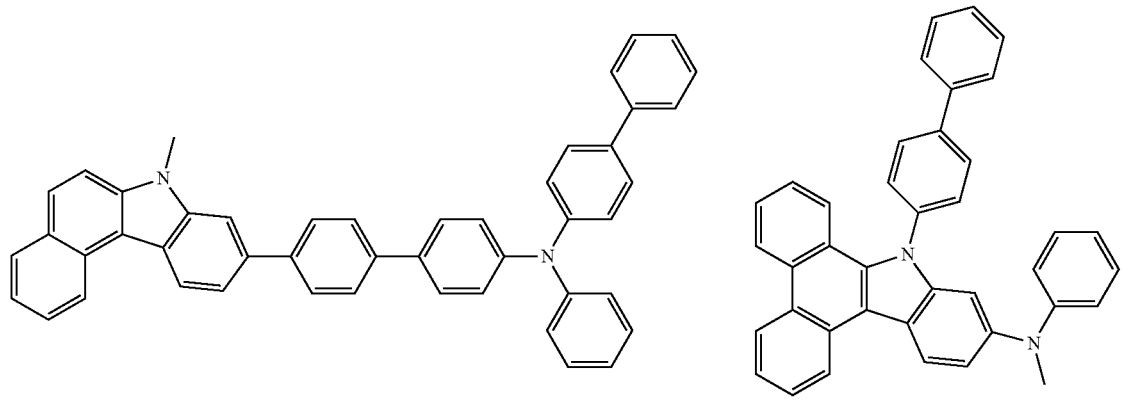

-continued
901
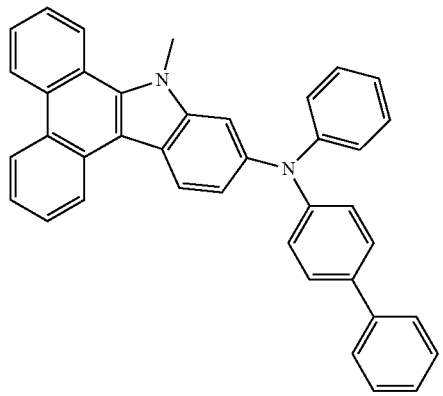
902
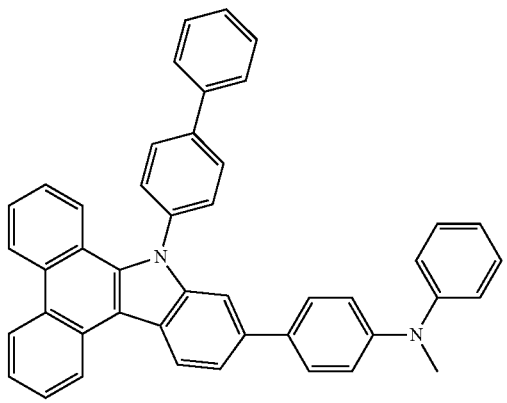
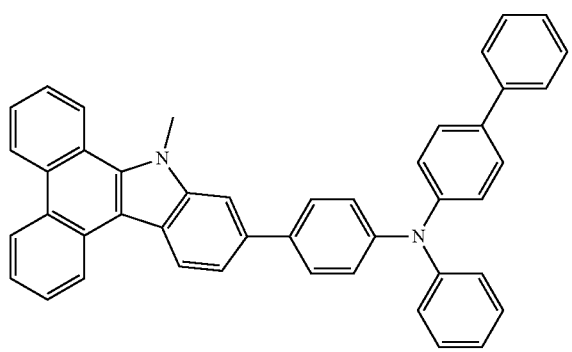
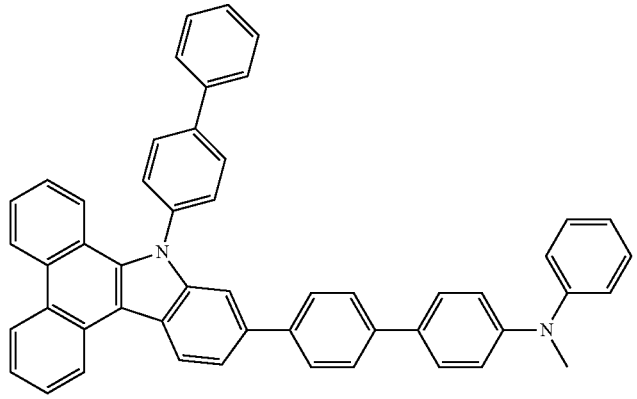
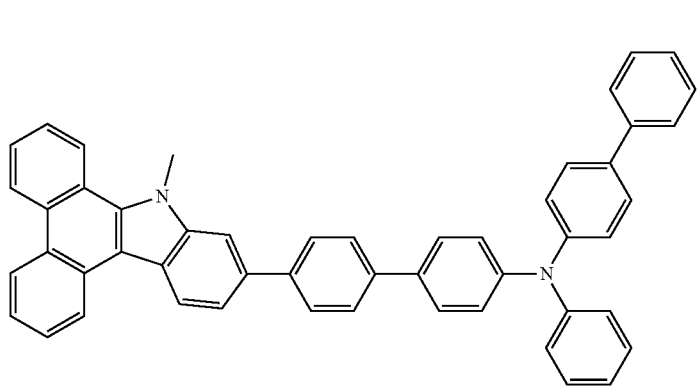
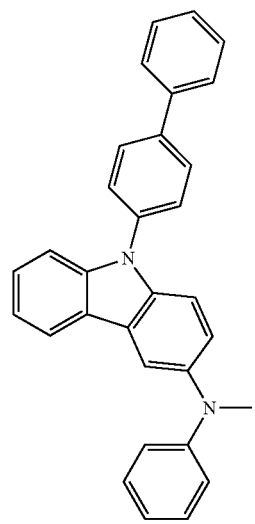

903
904
-continued
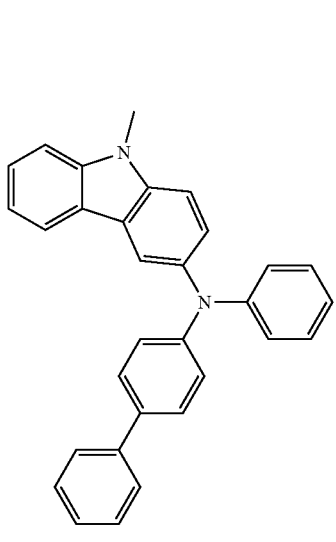
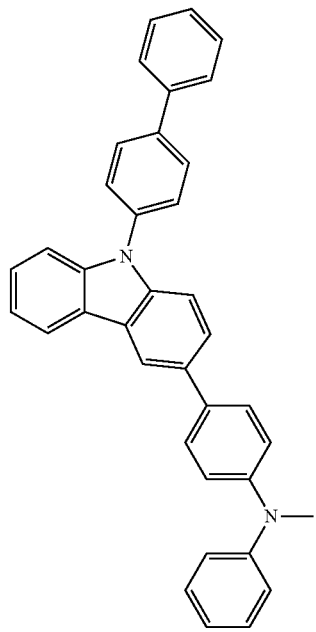
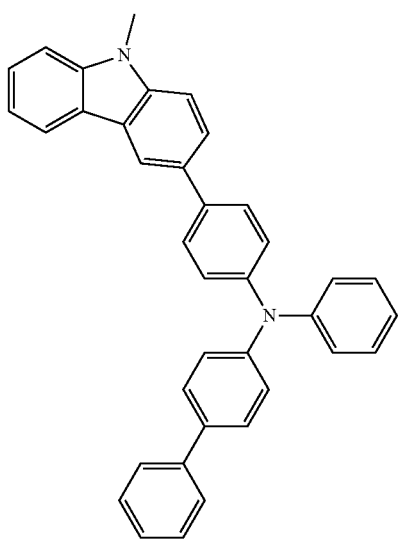
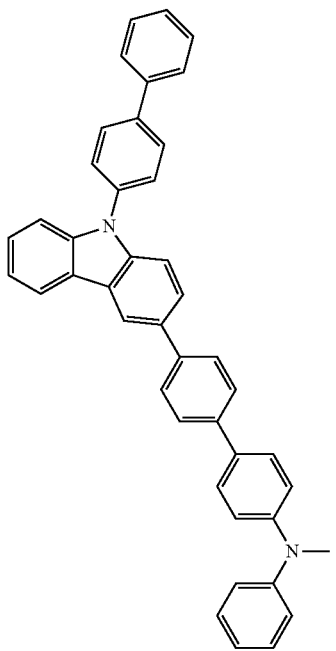
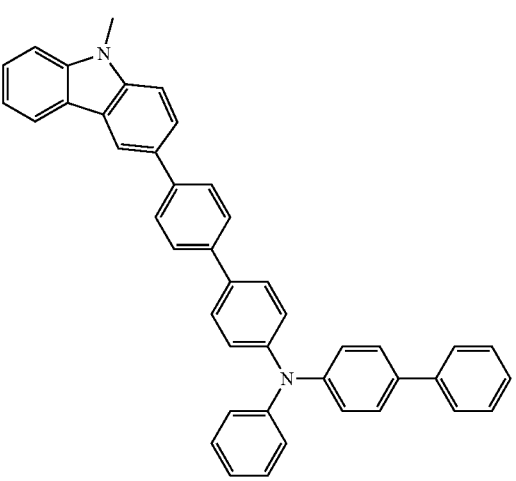

-continued
905
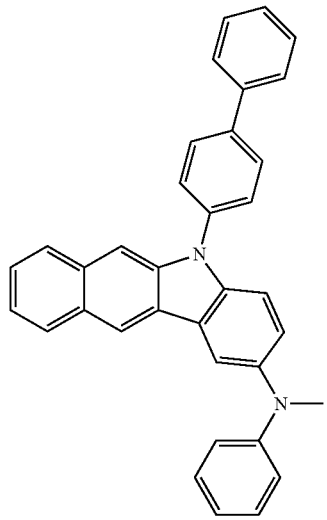
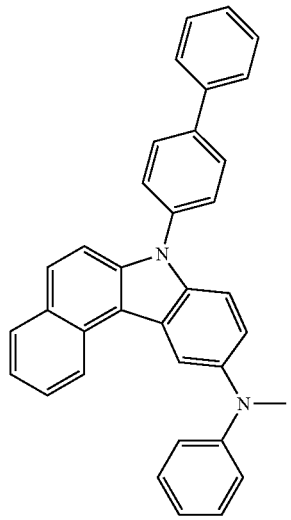
906
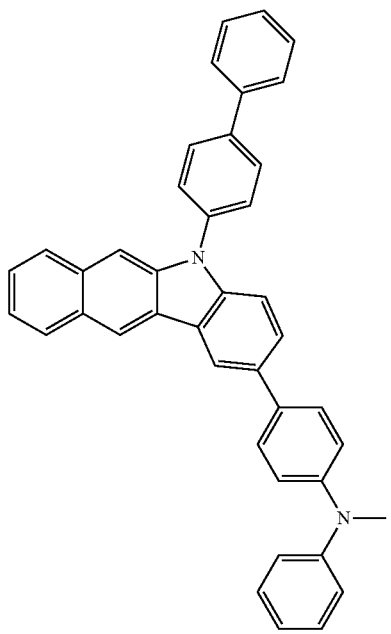
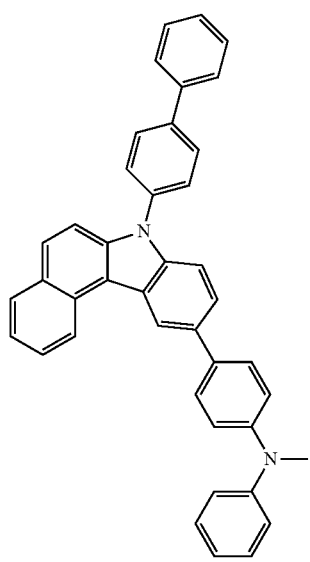
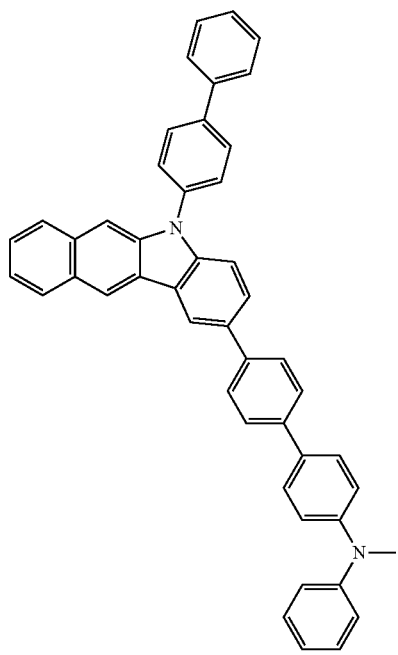
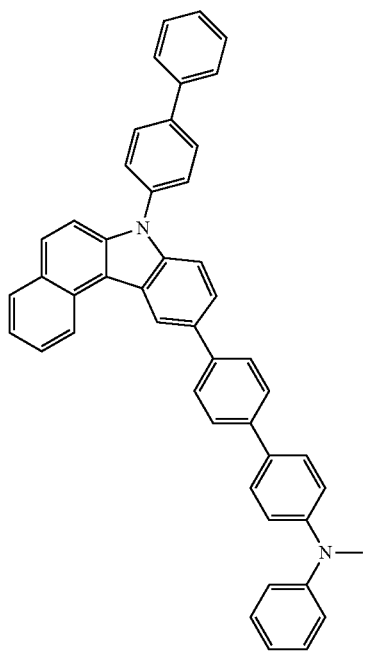
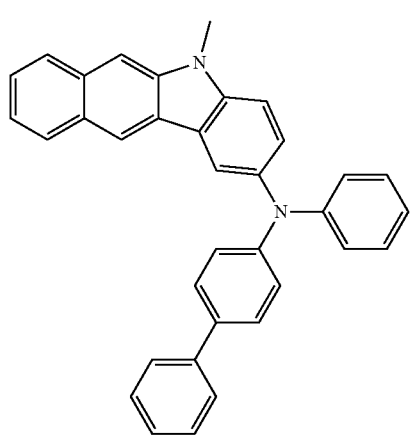
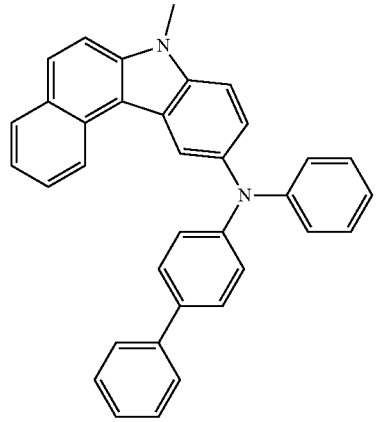

907
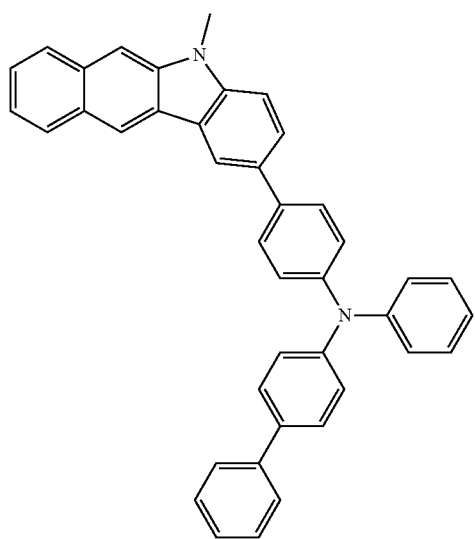
908
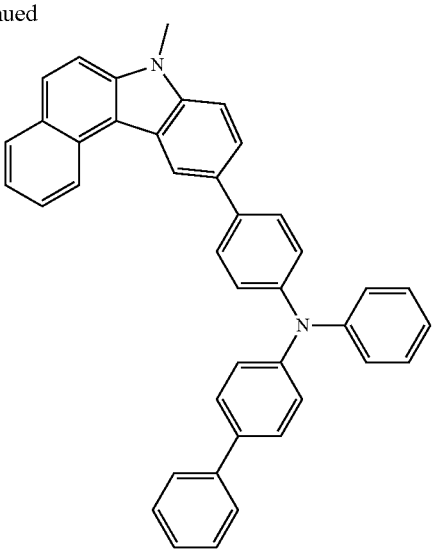
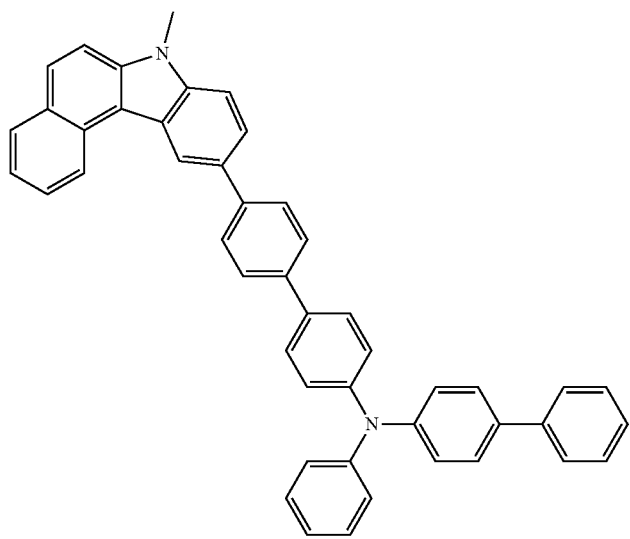
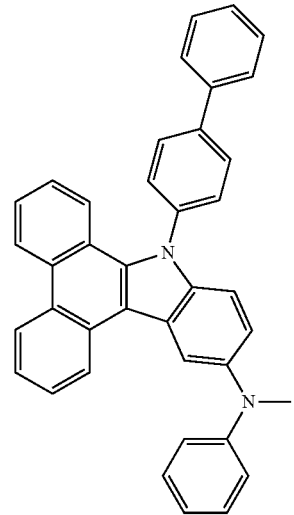

-continued
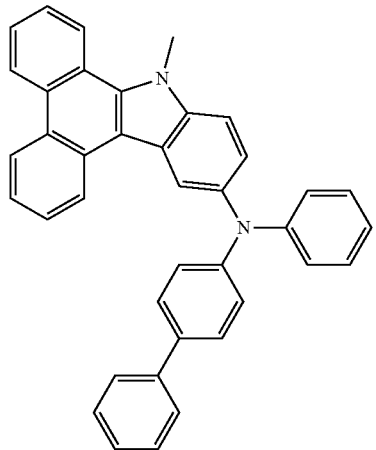
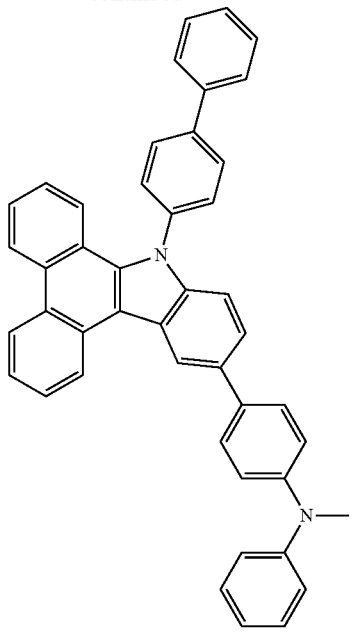
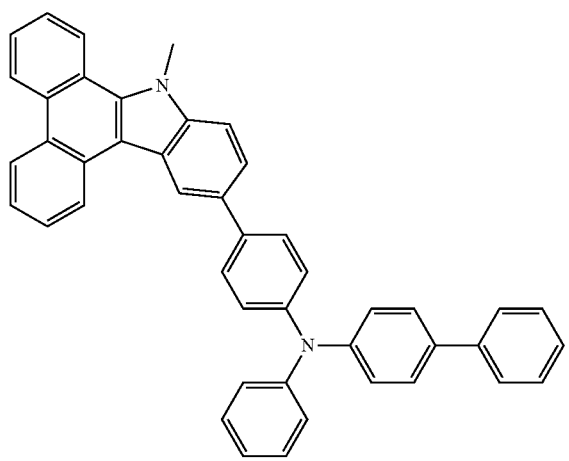
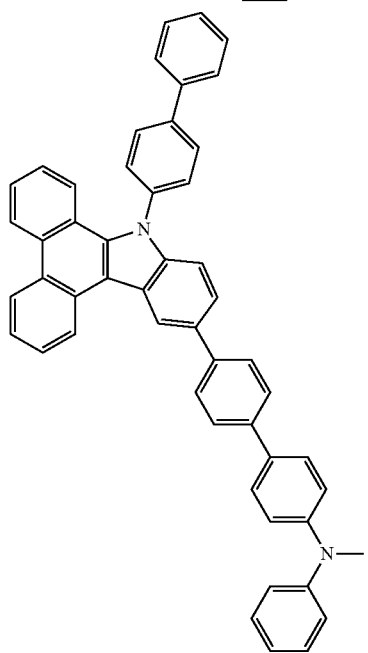
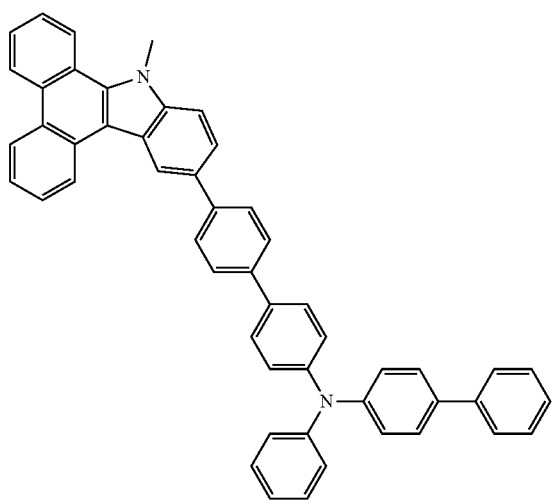

911 912
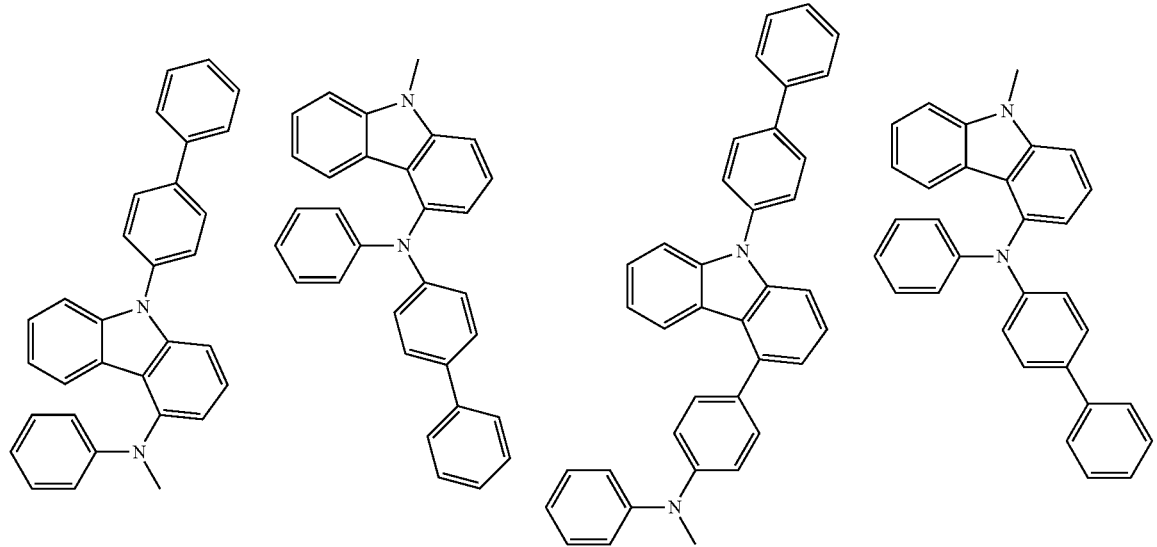
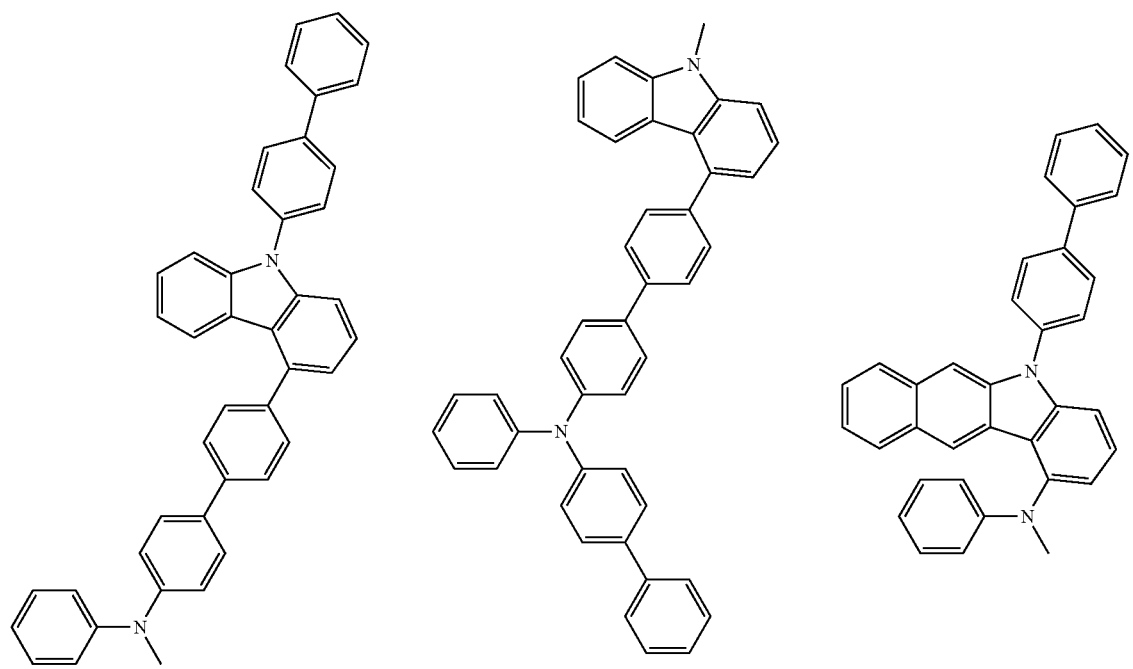

913
-continued
914
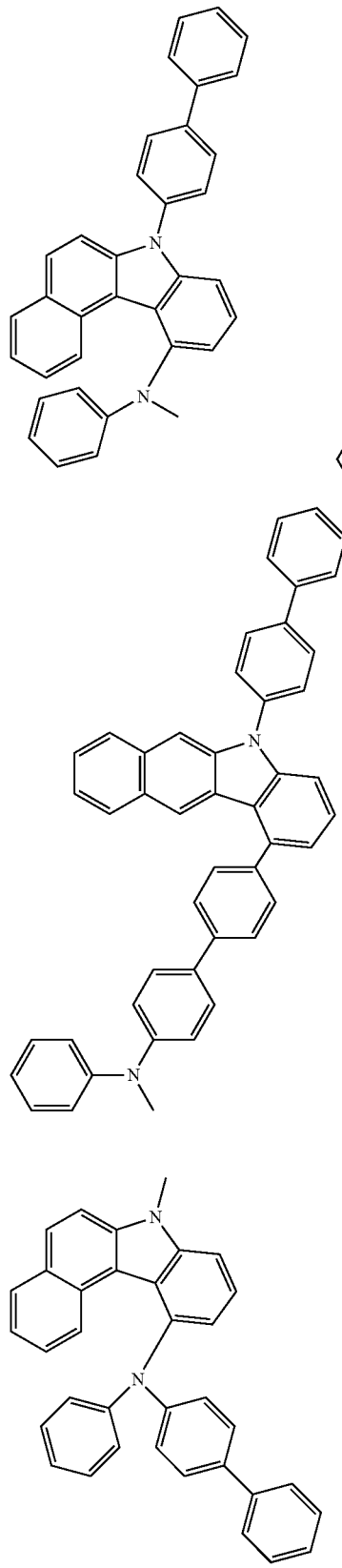
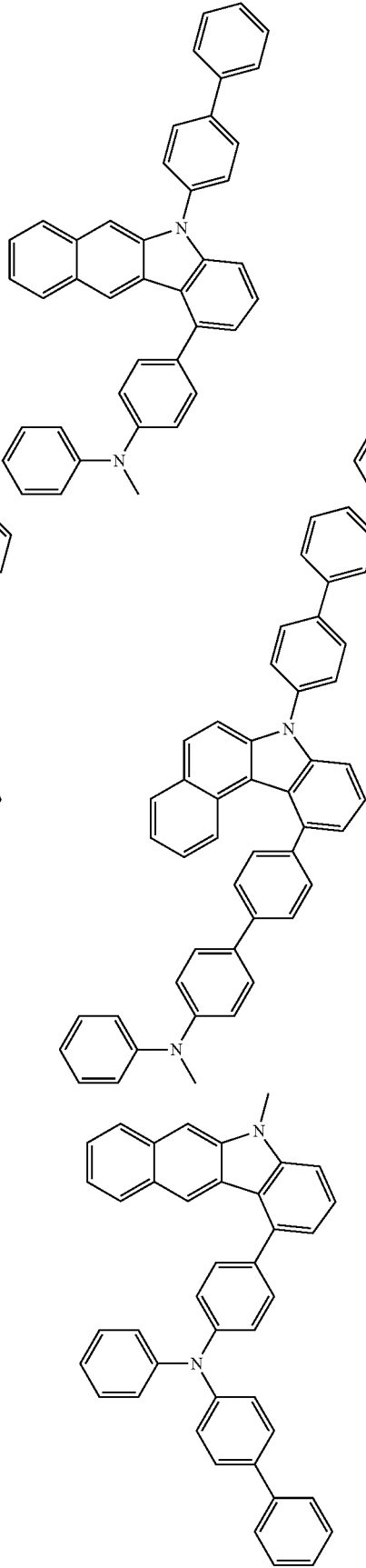
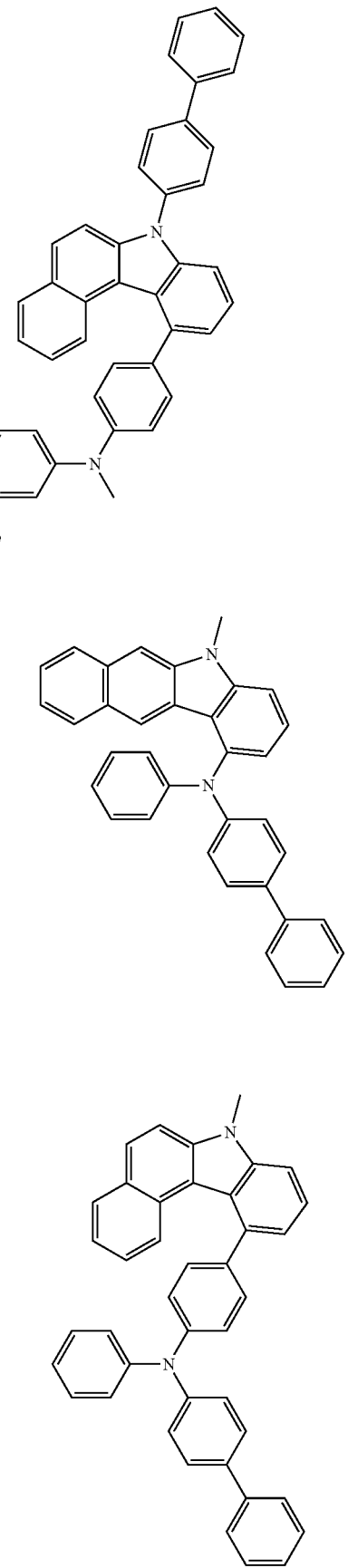

-continued
915
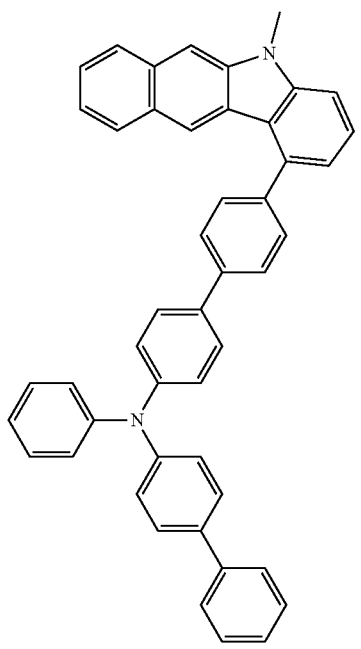
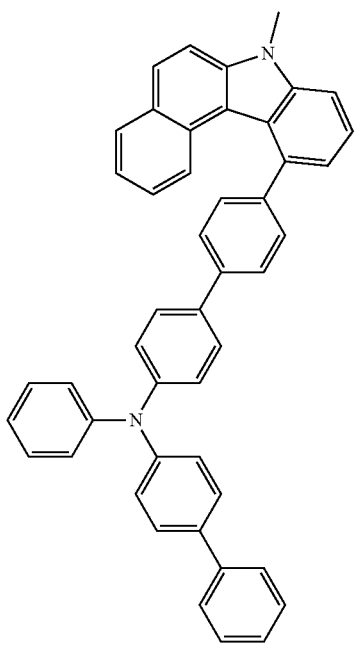
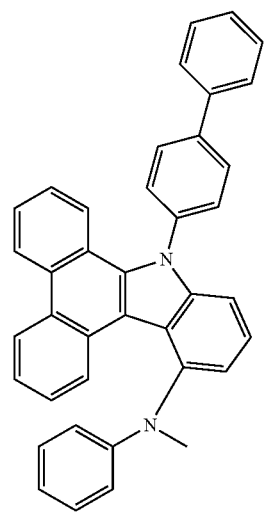
916
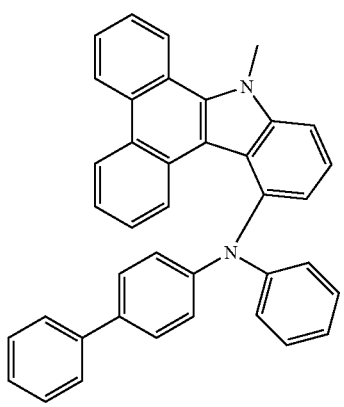
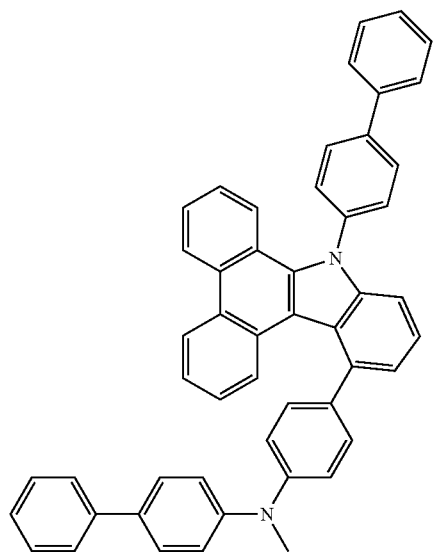
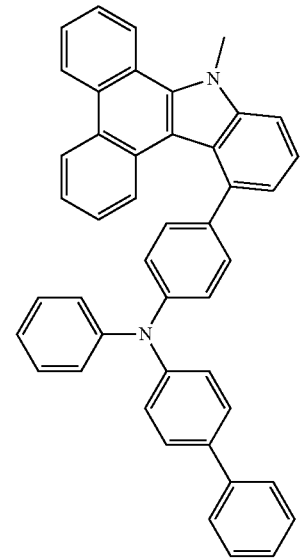

917 918
-continued
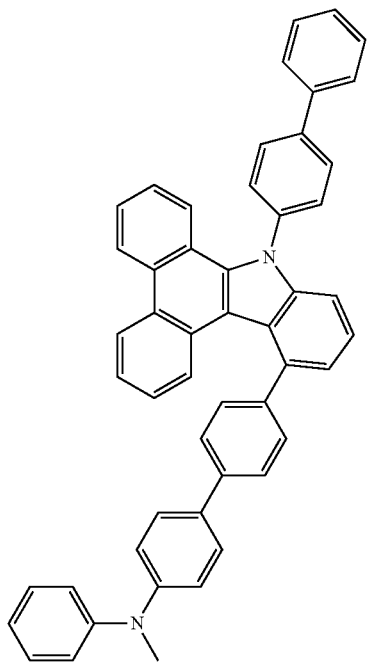
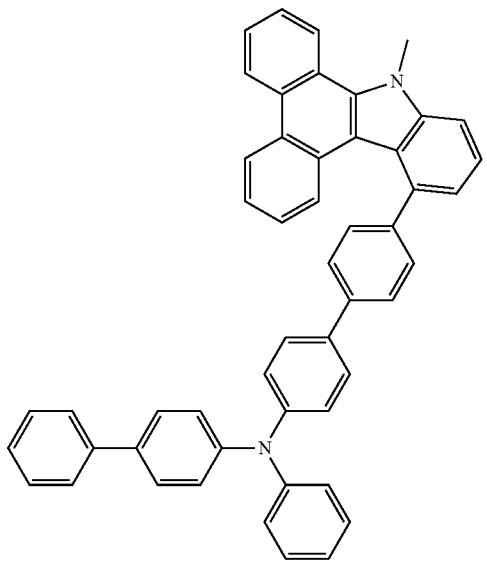
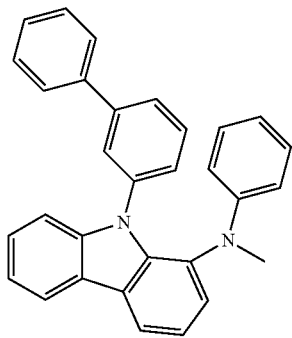
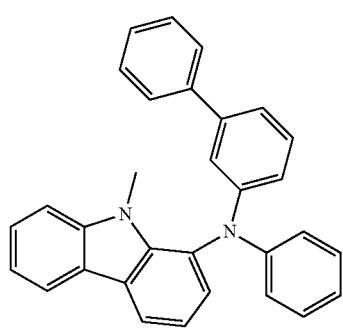
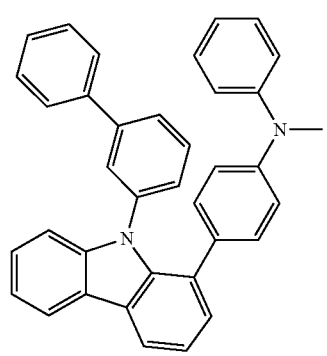
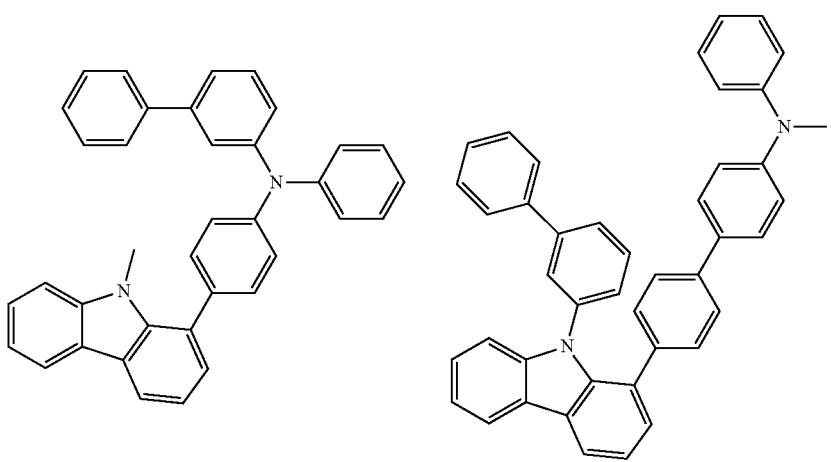

919 920
-continued
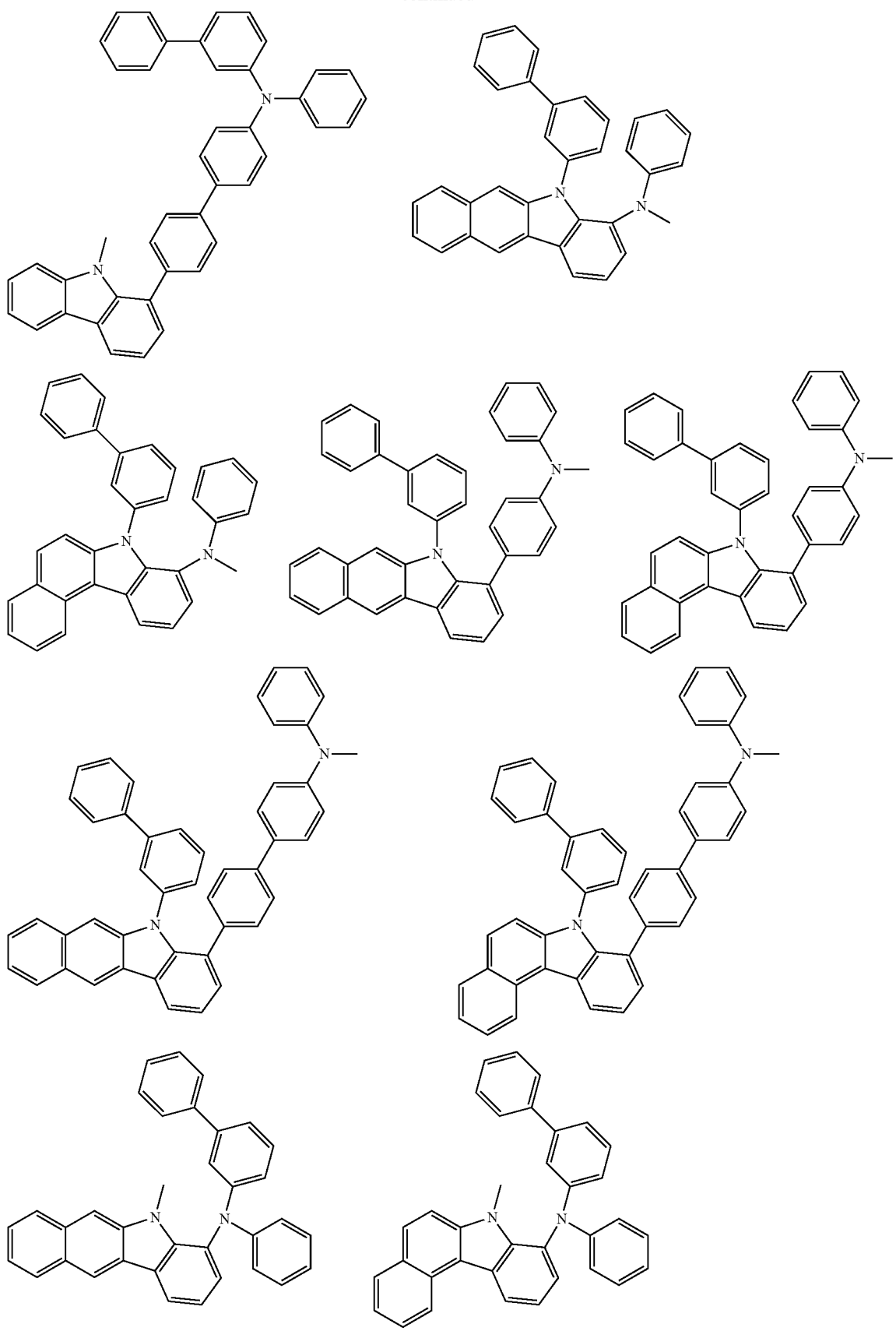

921 922
-continued
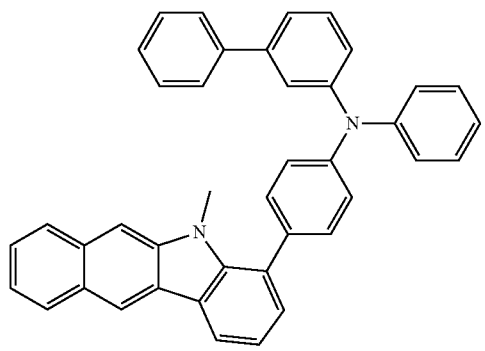
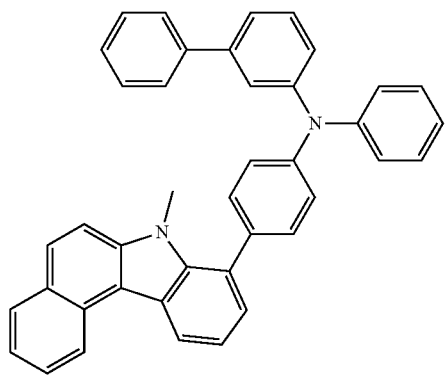
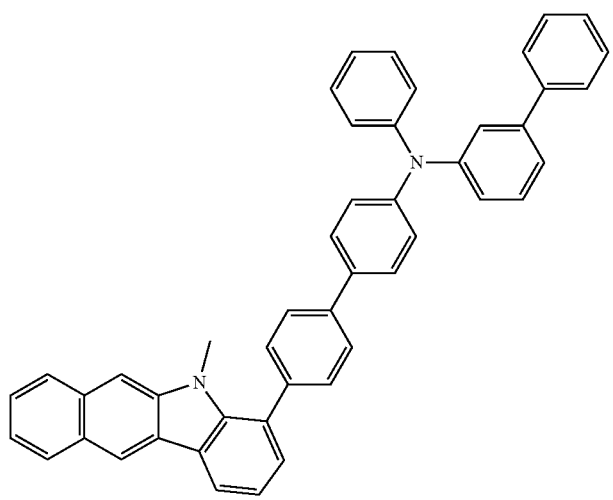
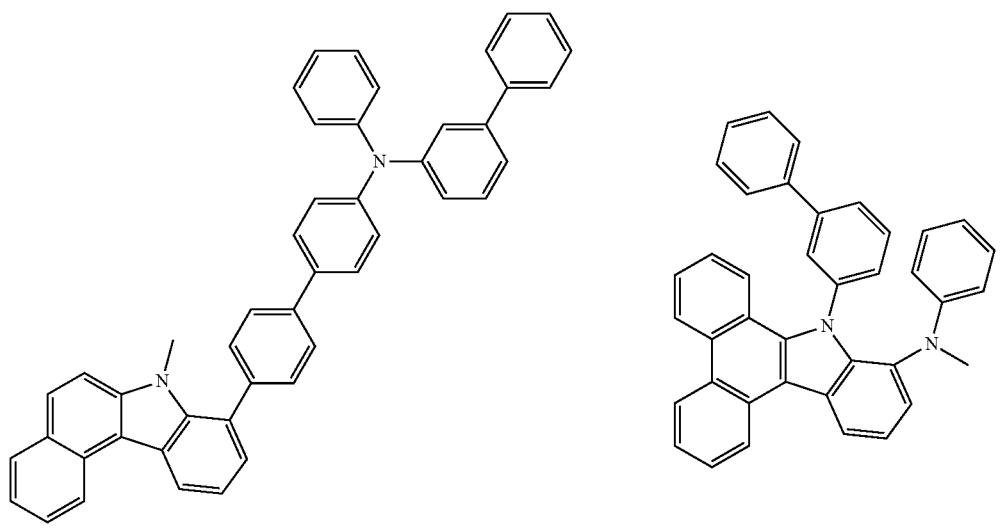

-continued
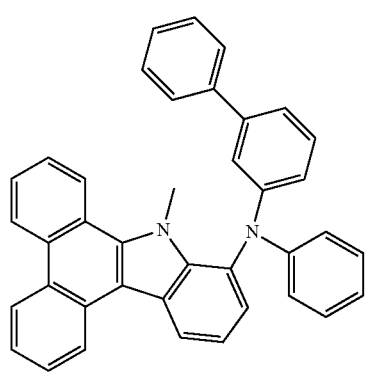
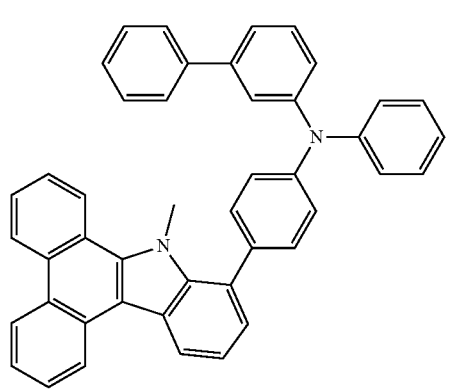
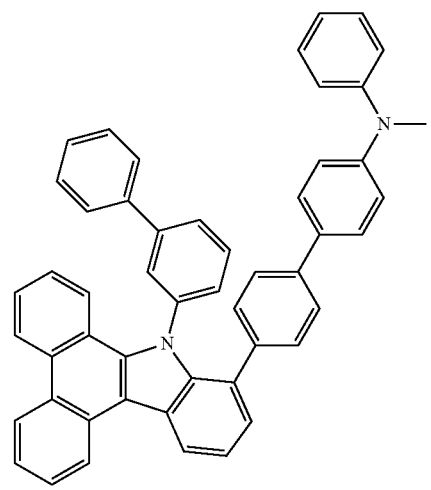
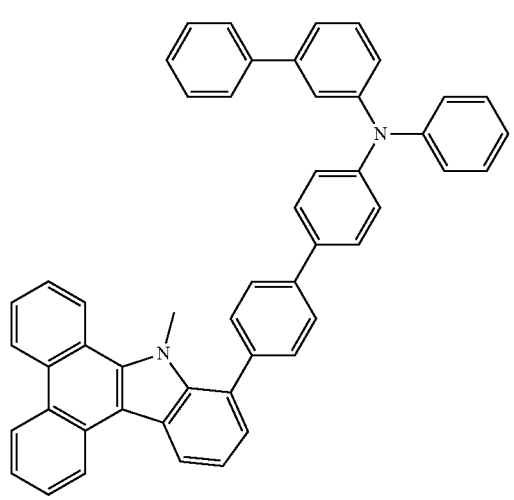
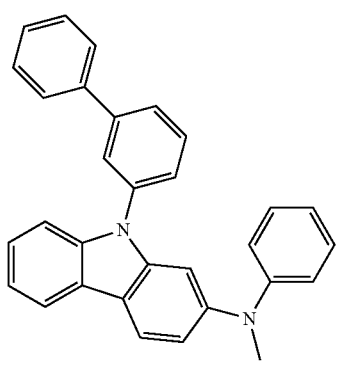
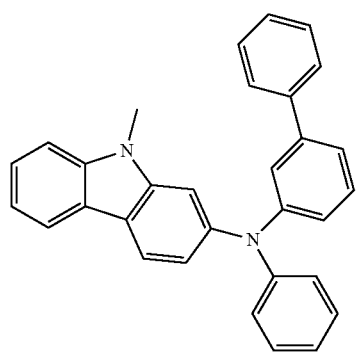
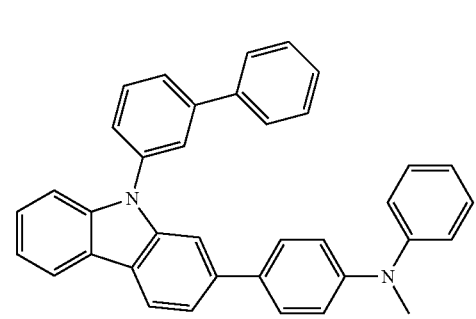

-continued
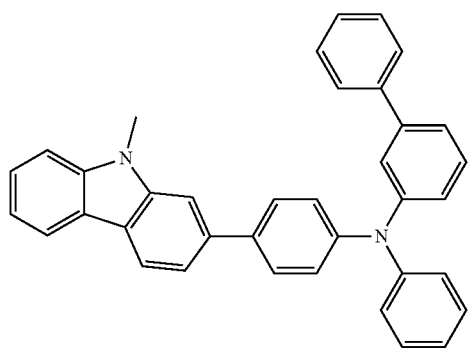
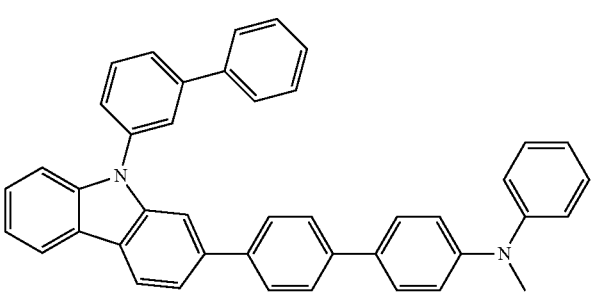
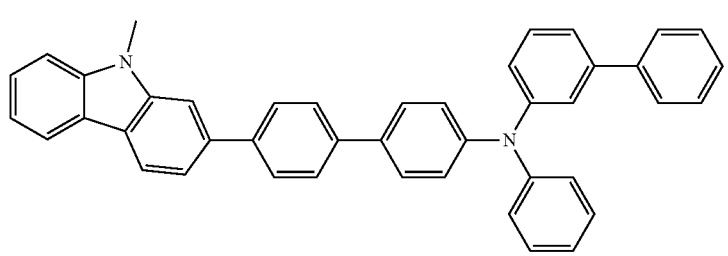
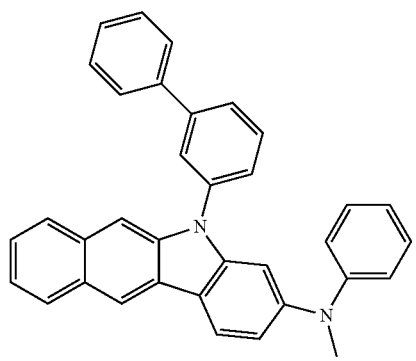
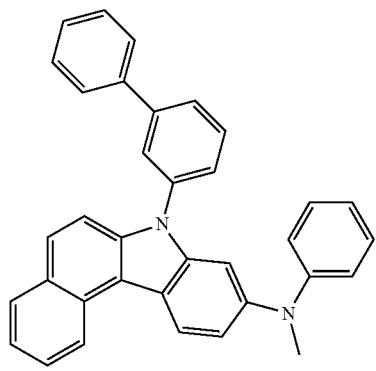
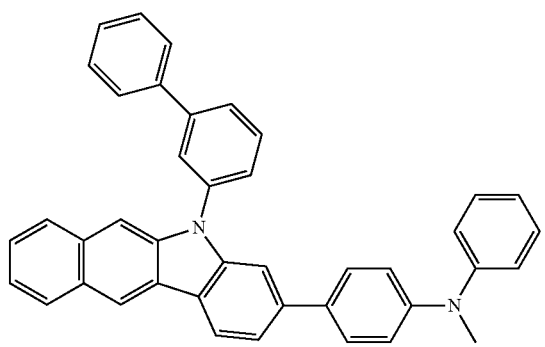
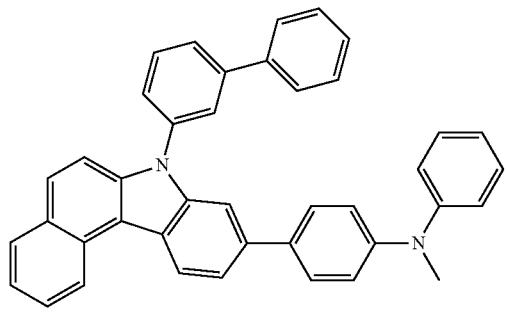
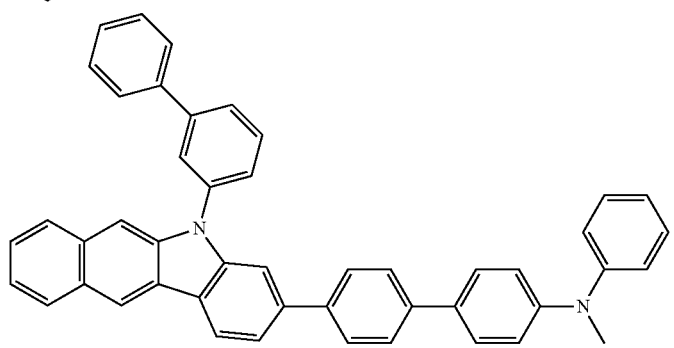

-continued
927
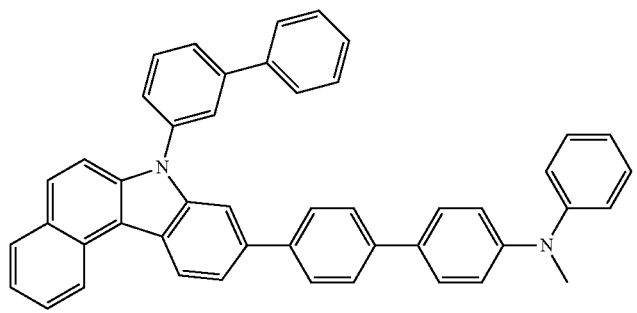
928
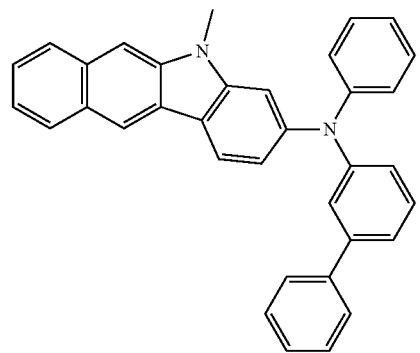
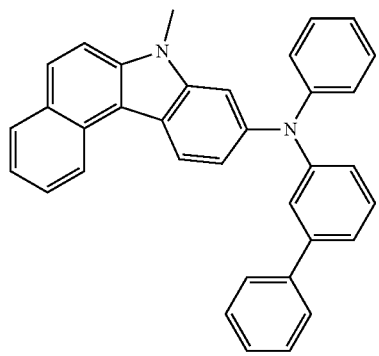
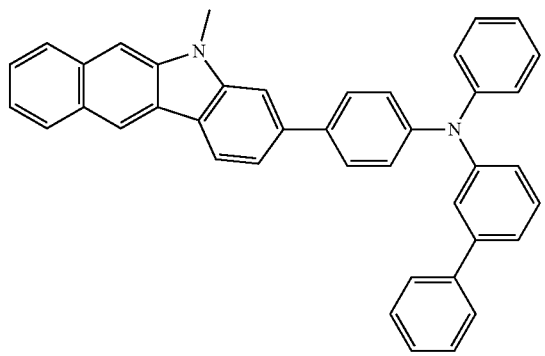
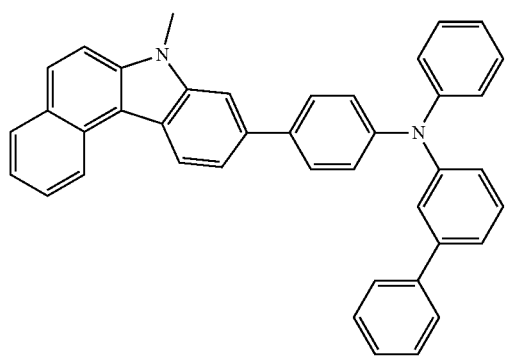
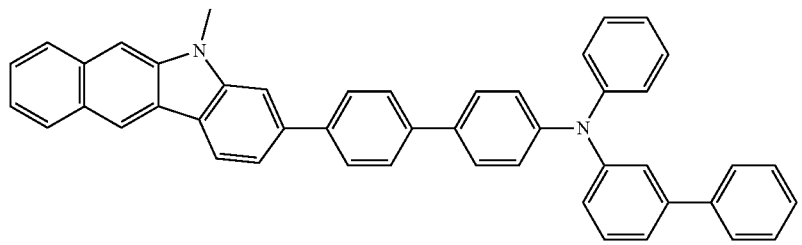
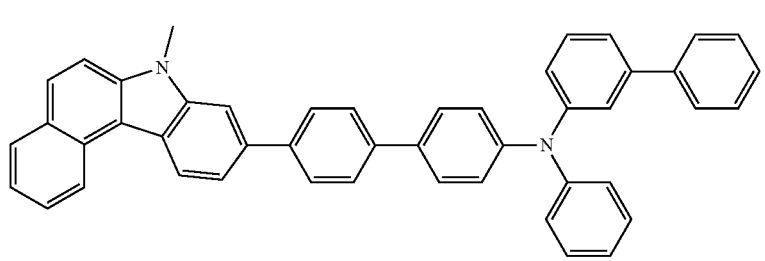
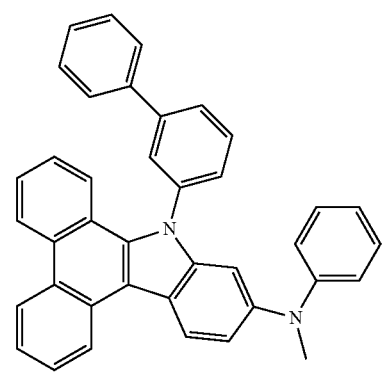

-continued
929
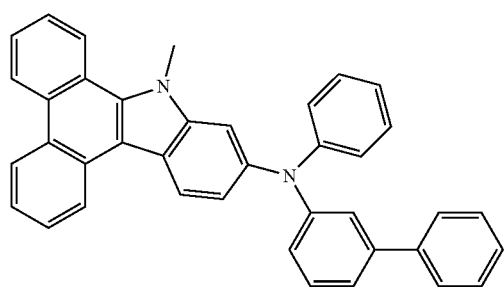
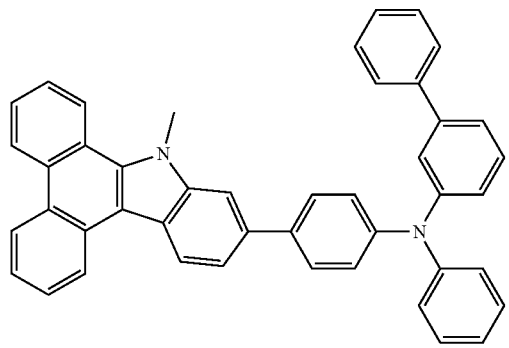
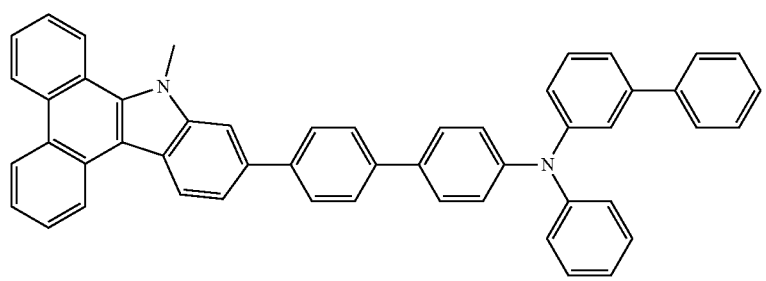
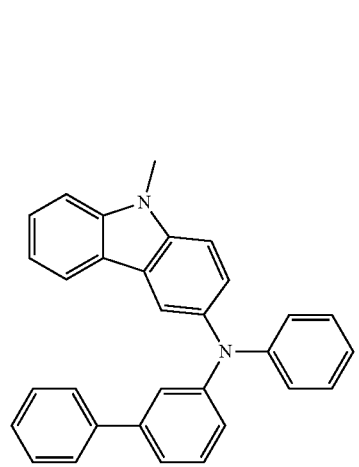
930
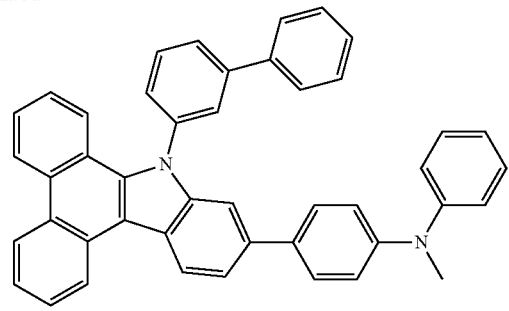
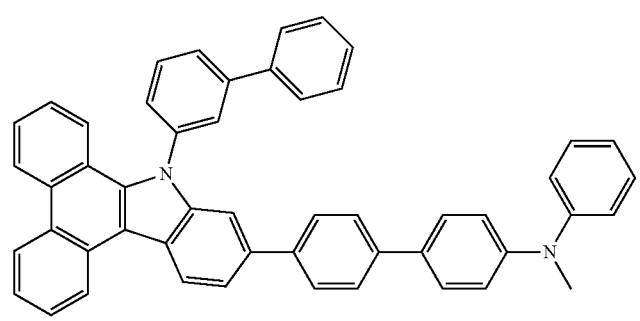
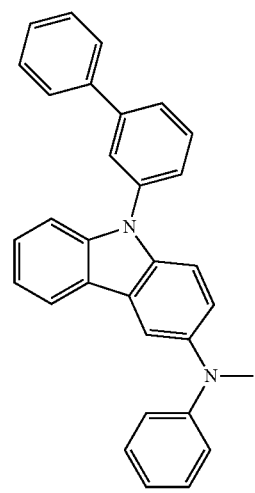
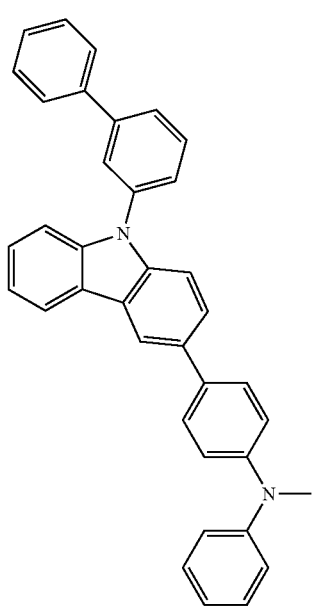
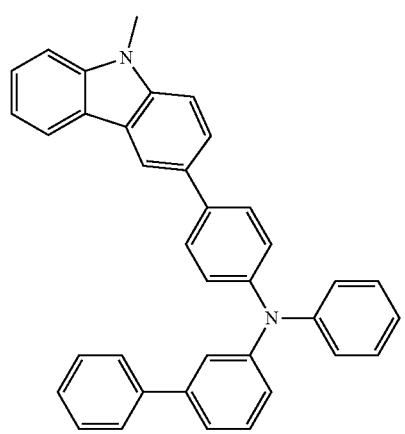

931
932
-continued
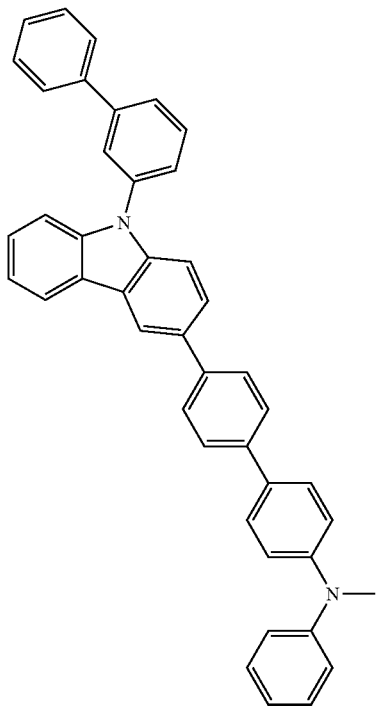
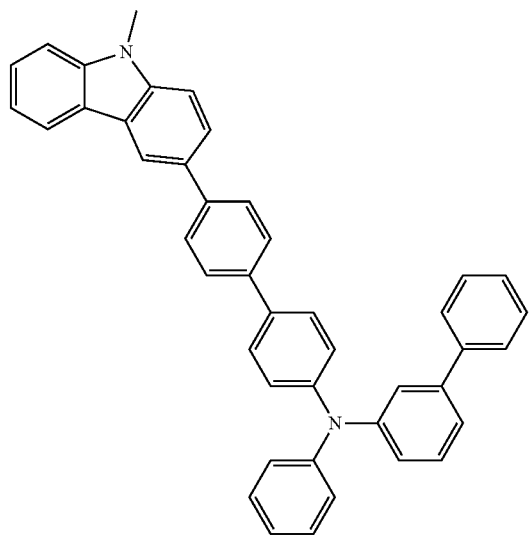
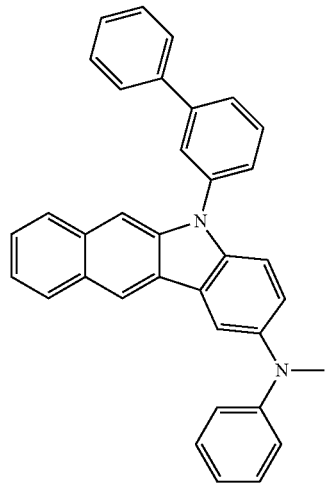
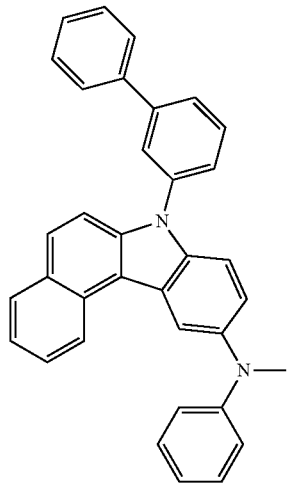
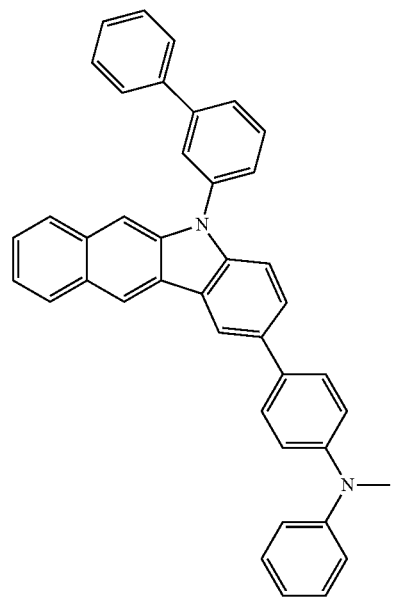

933
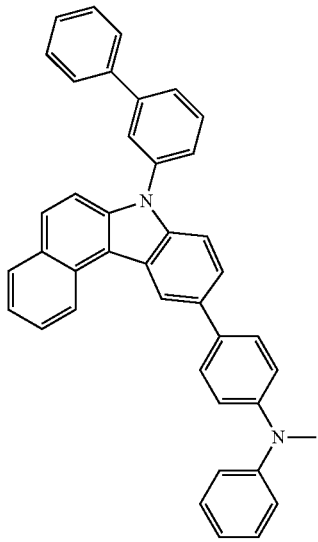
-continued
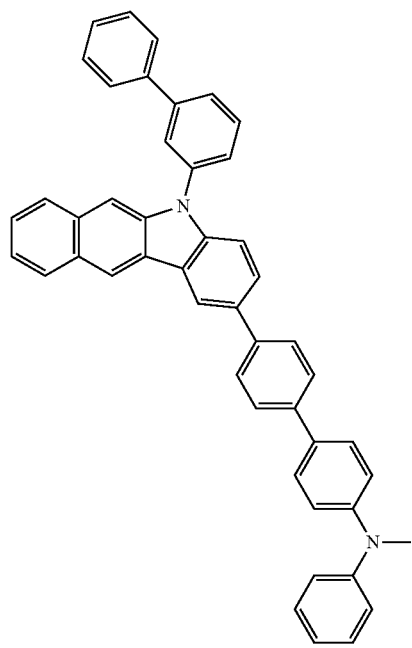
934
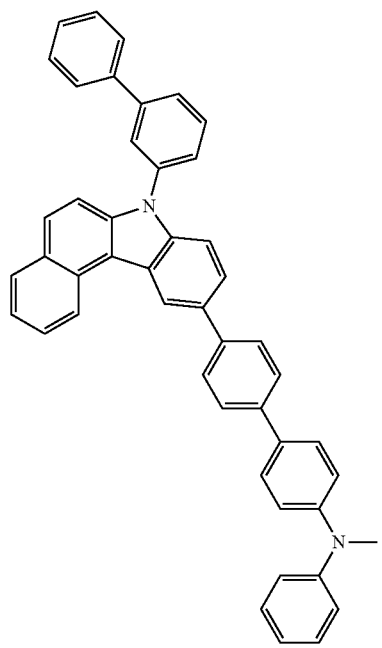
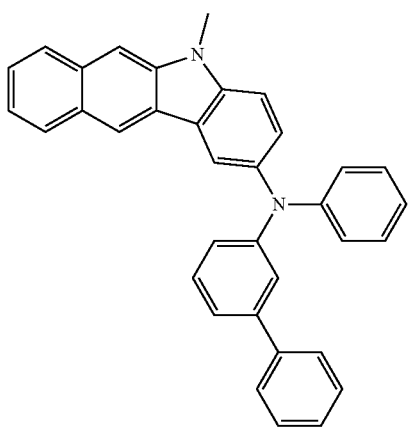
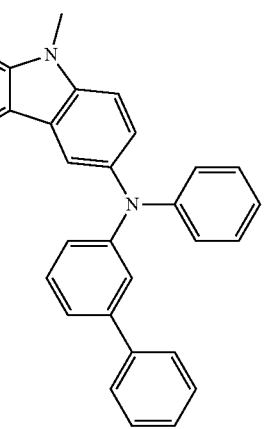
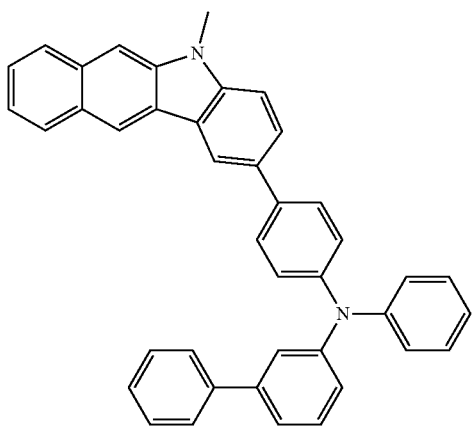
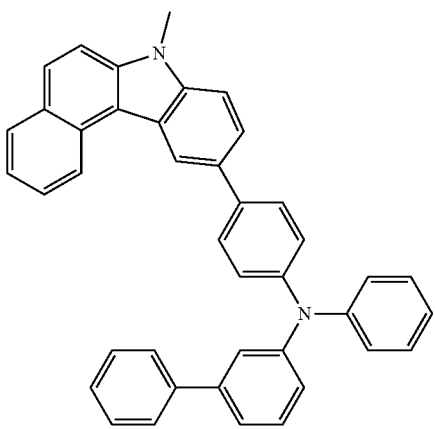

-continued
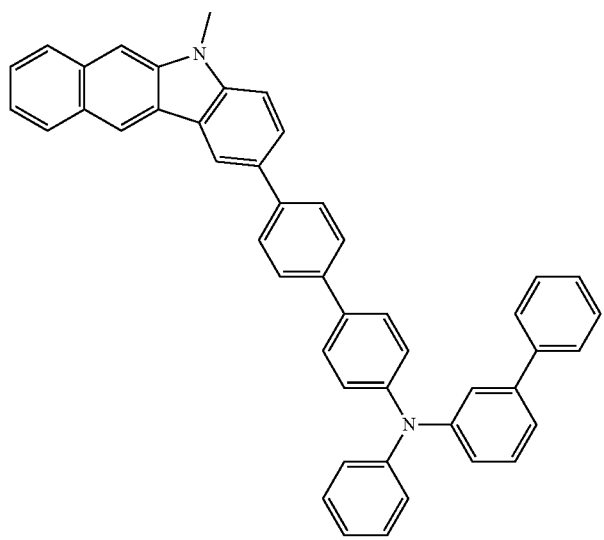
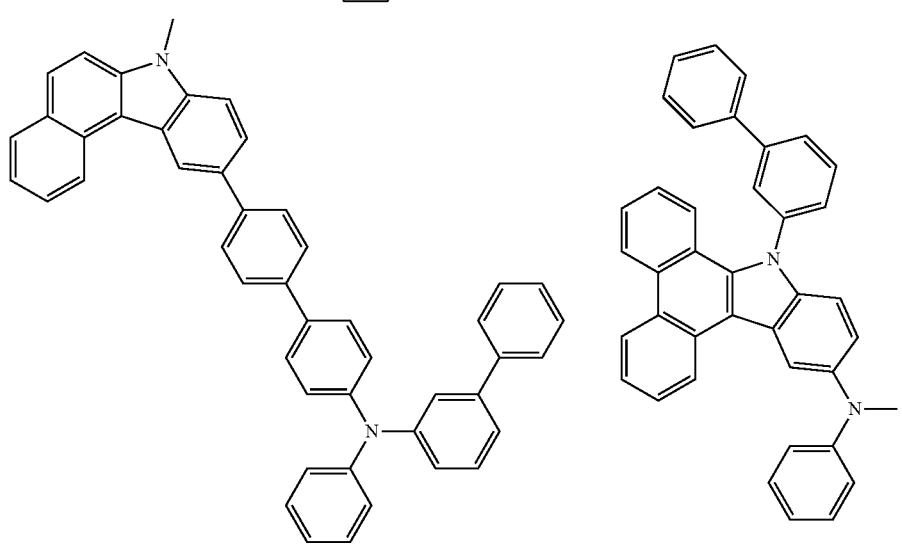
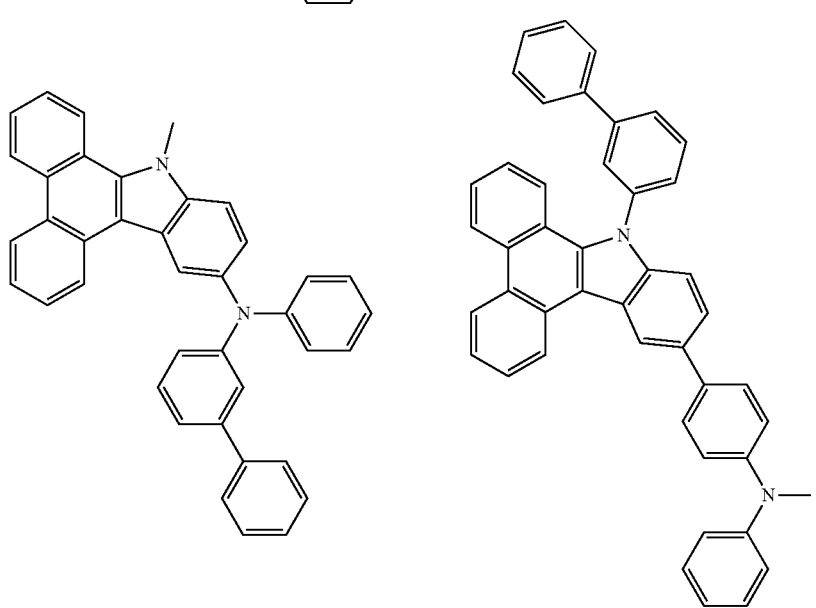

-continued
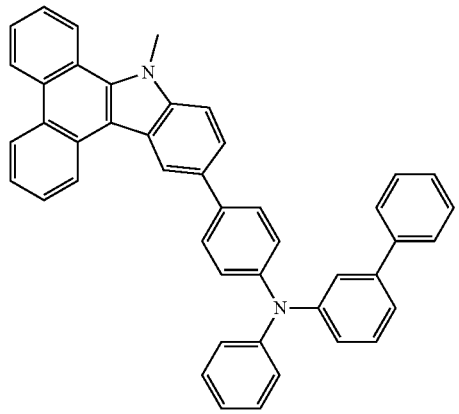
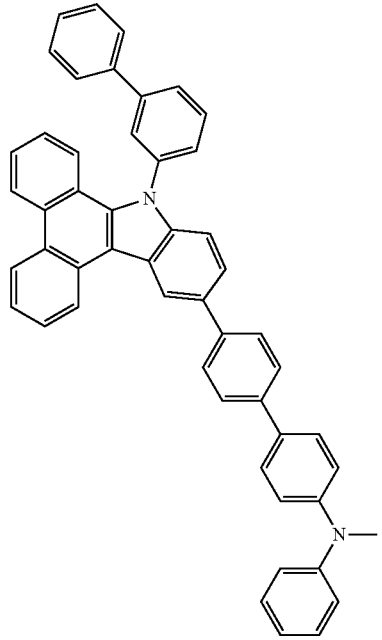
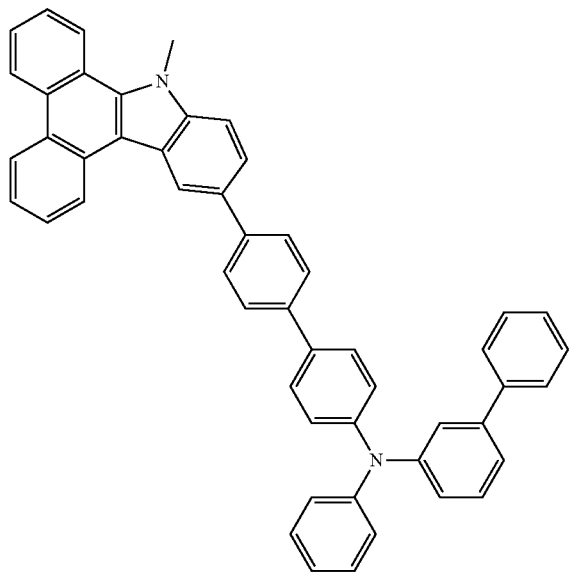
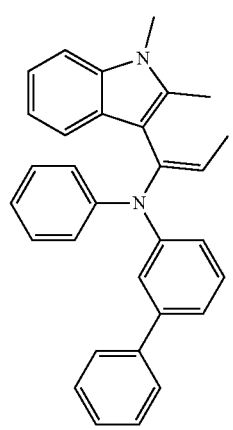

-continued
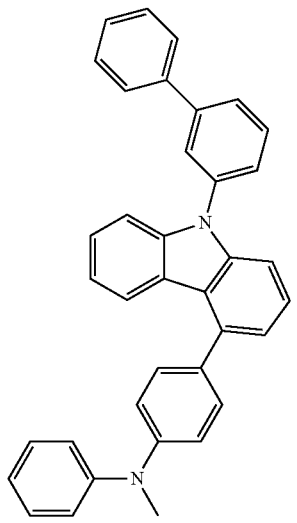 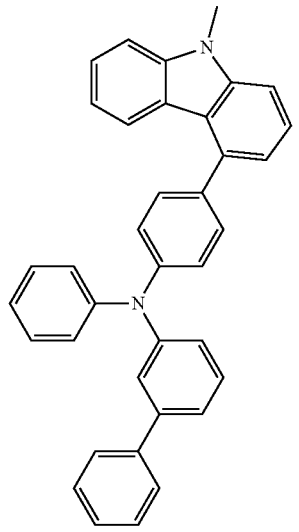 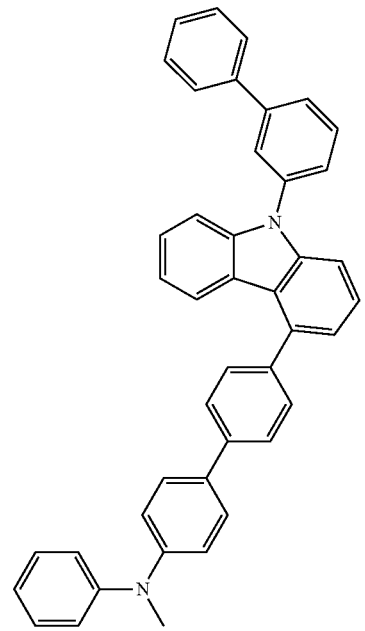
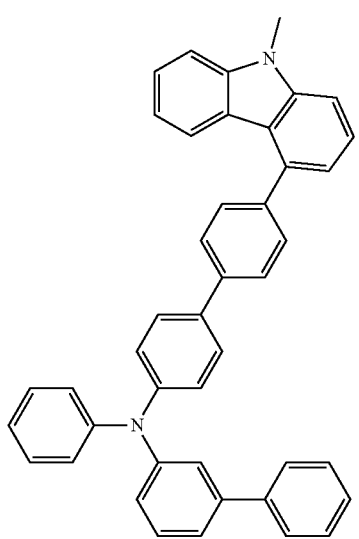 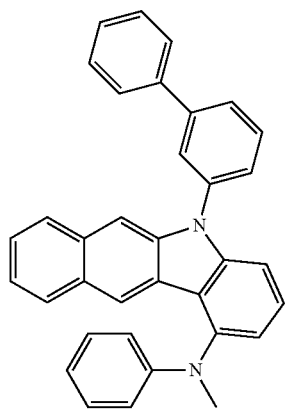 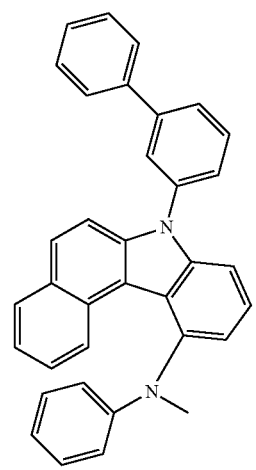

941 942
-continued
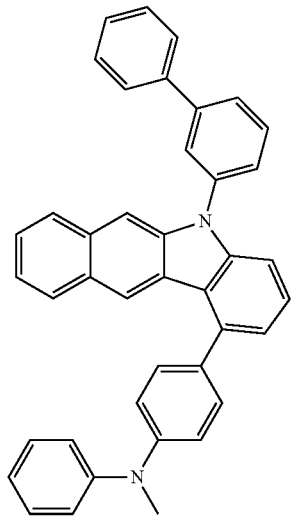 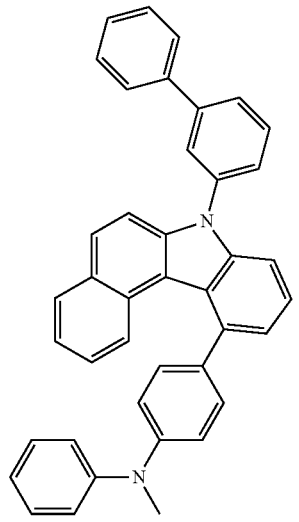 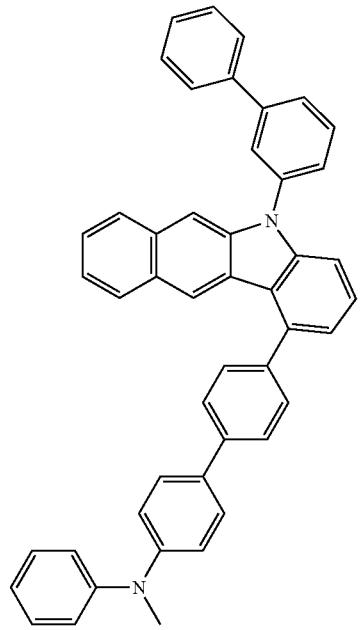
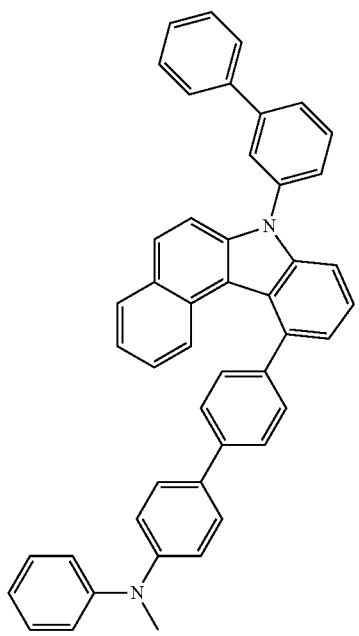 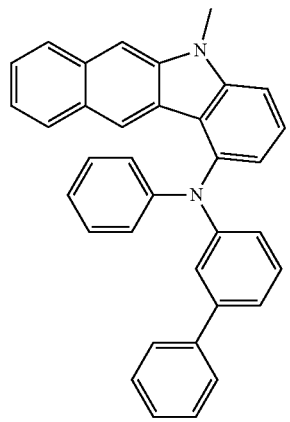 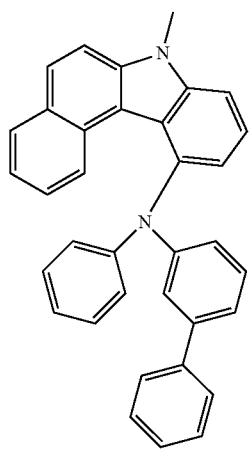

943 944
-continued
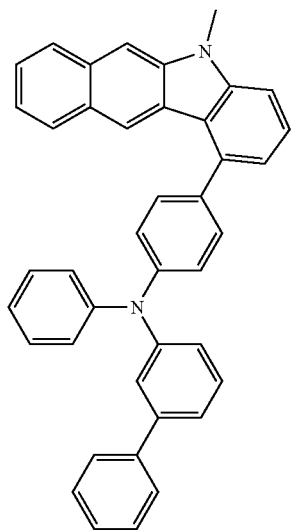 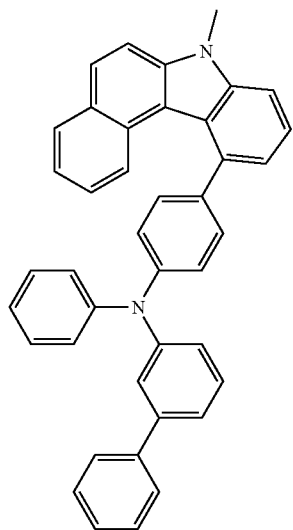 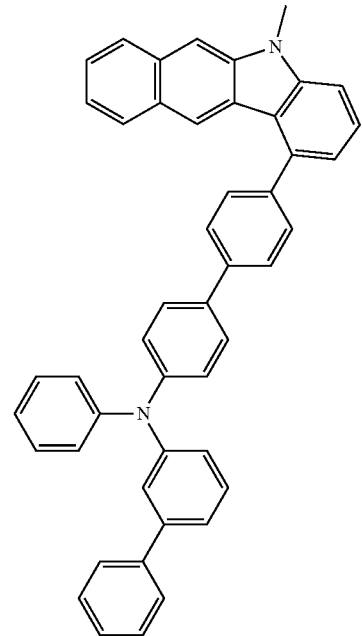
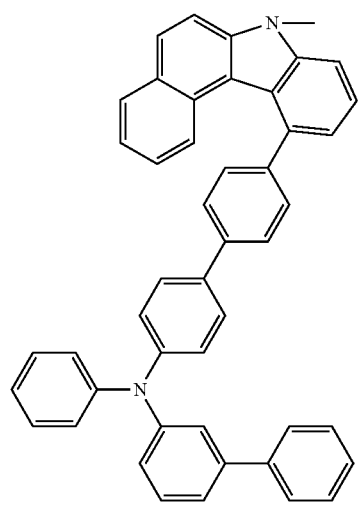 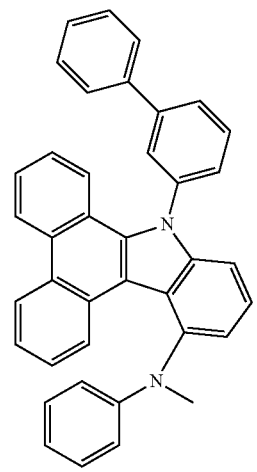 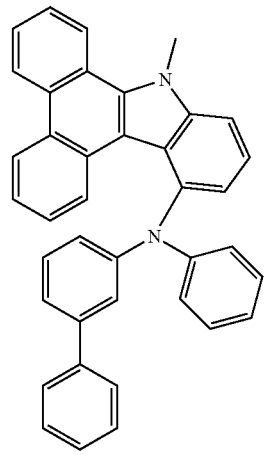

-continued
945 946
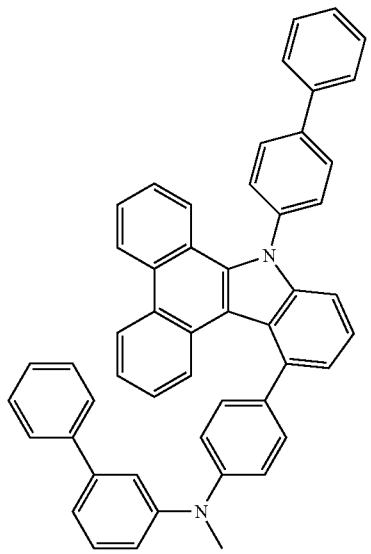
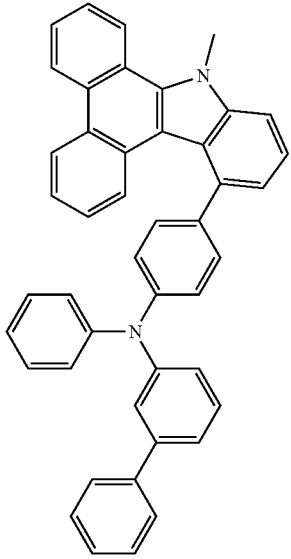
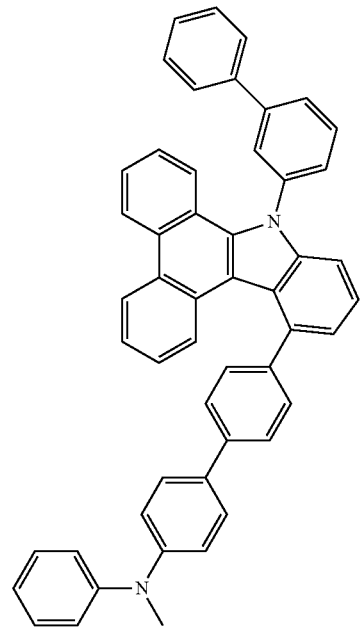
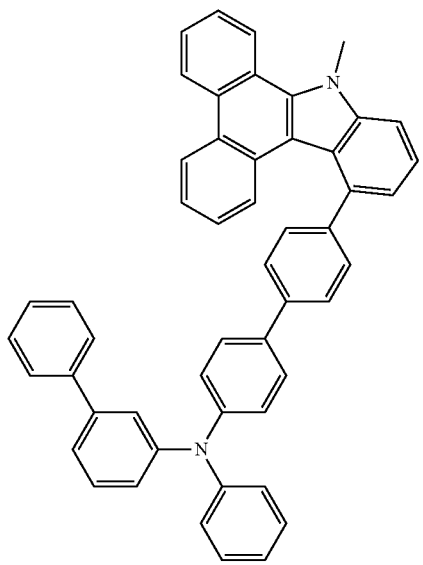
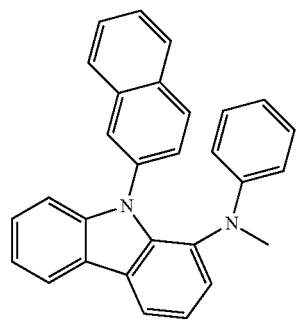
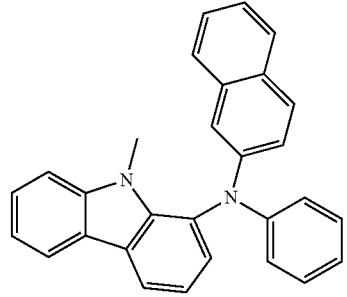
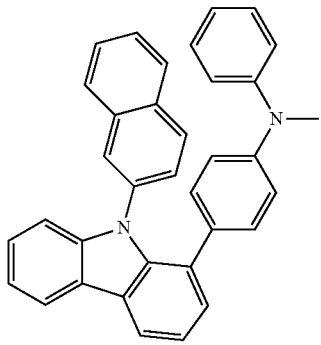
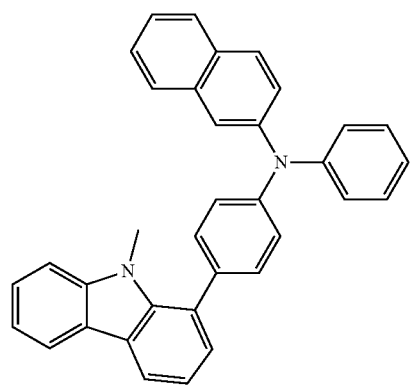
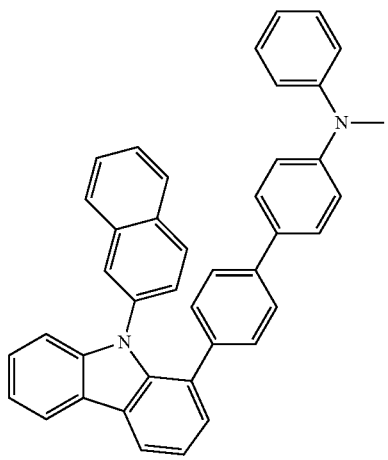

947 948
-continued
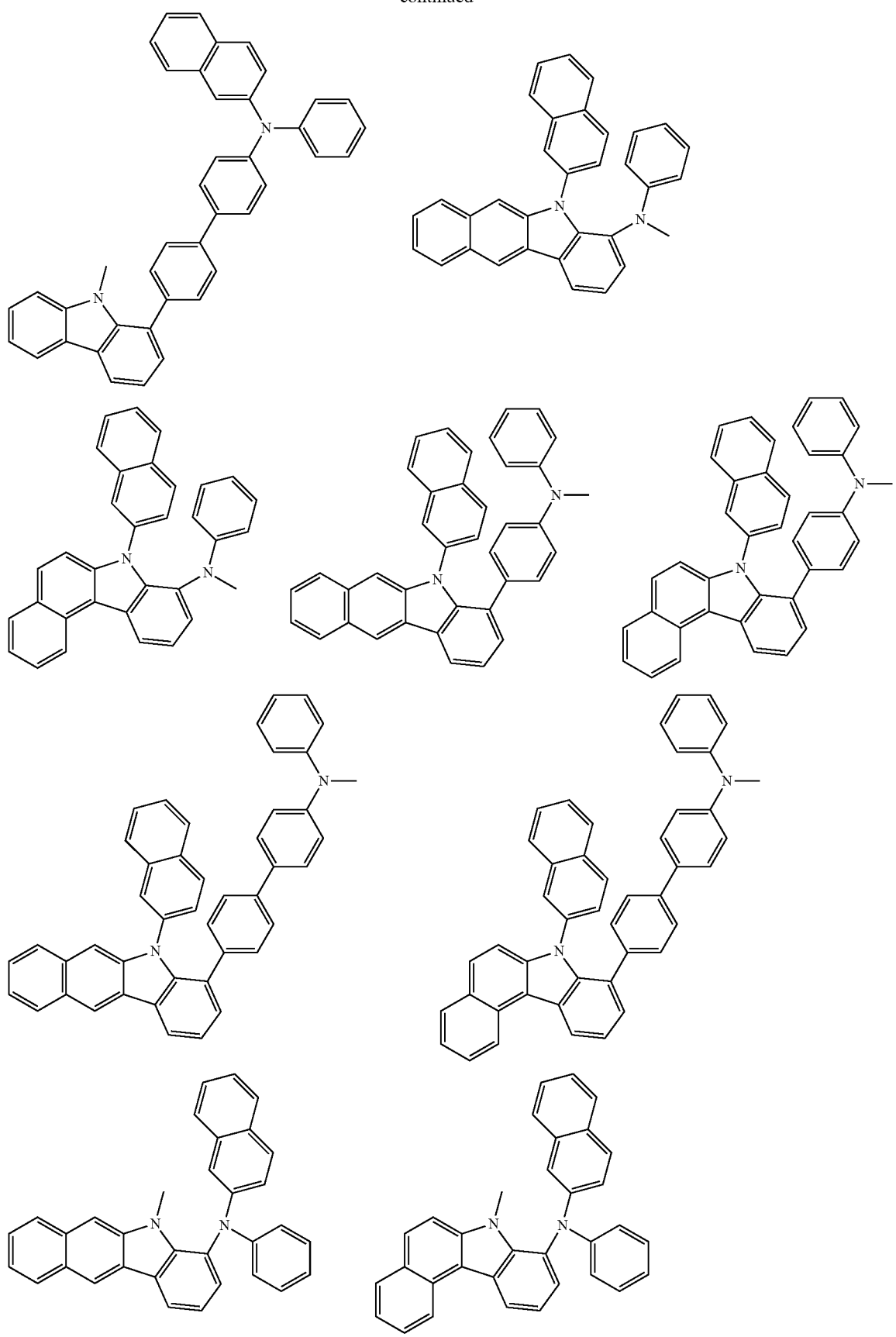

949 950
-continued
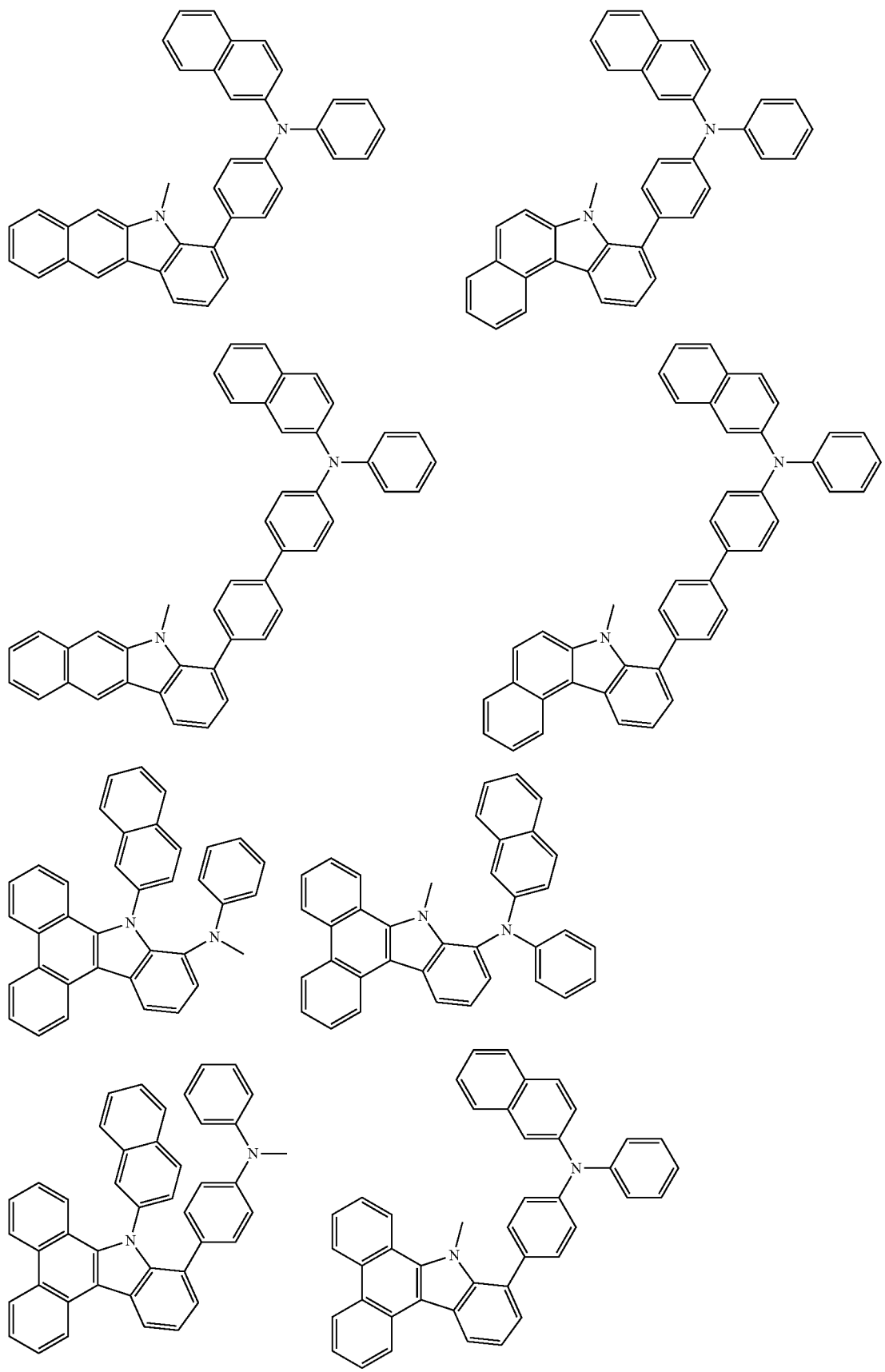

-continued
| 951 | 952 |
|---|---|
| 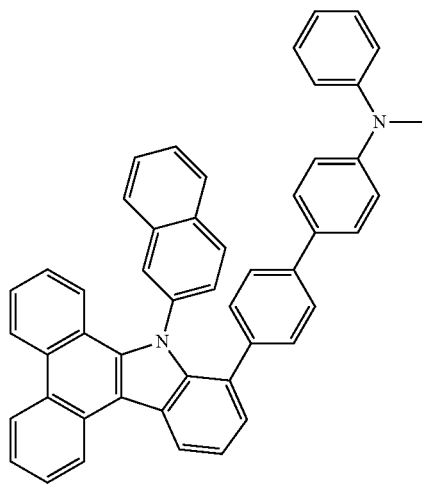 | 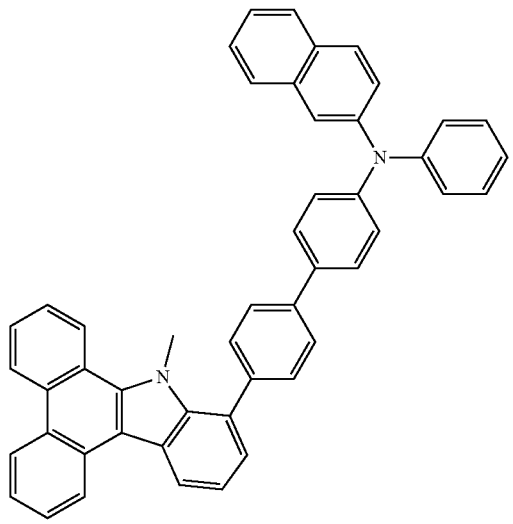 |
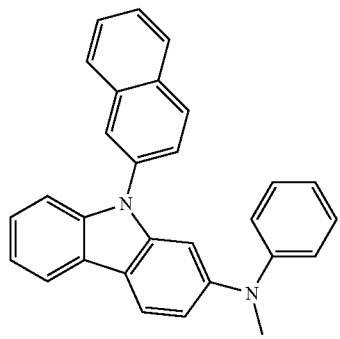
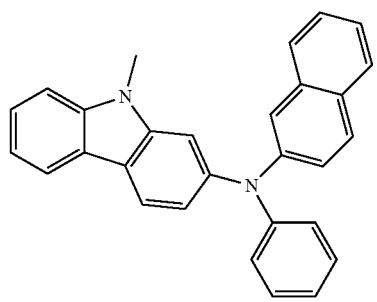
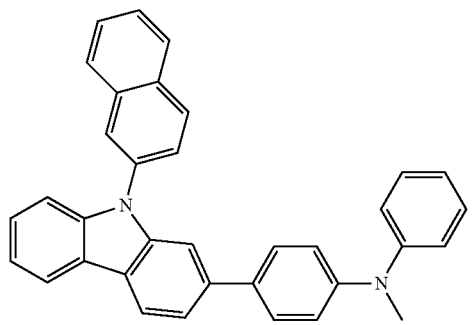
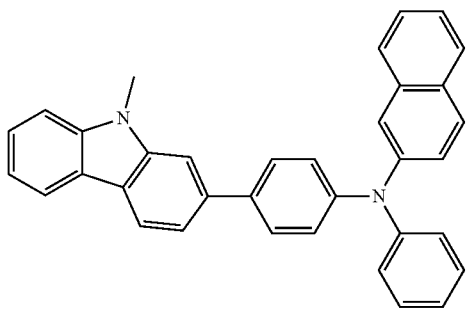
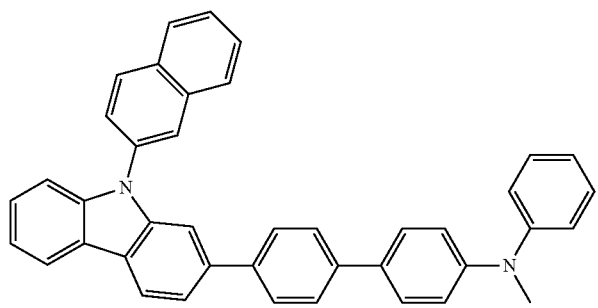

-continued
| 953 | 954 |
|---|---|
| 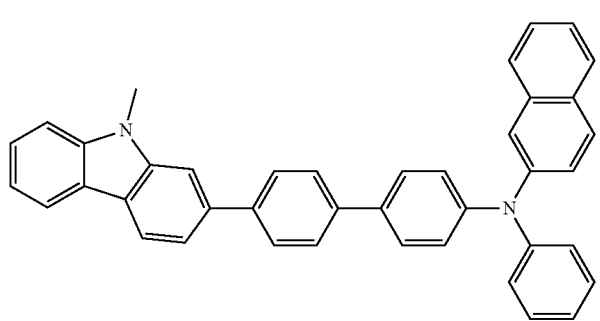 | 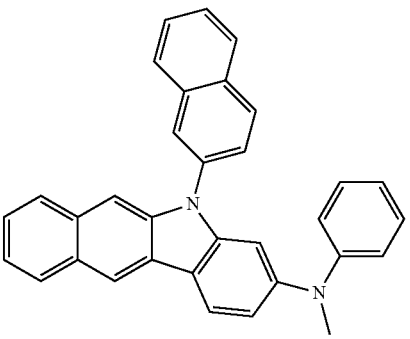 |
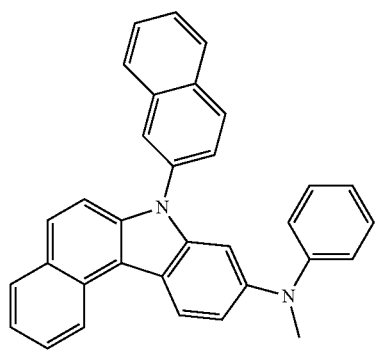
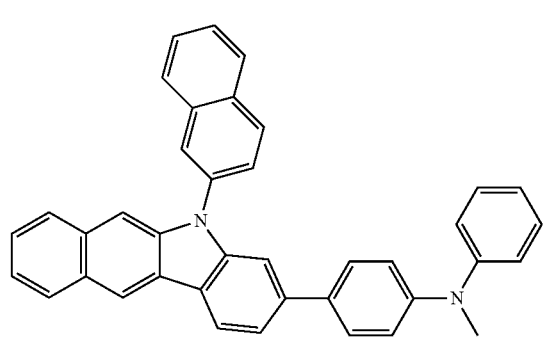
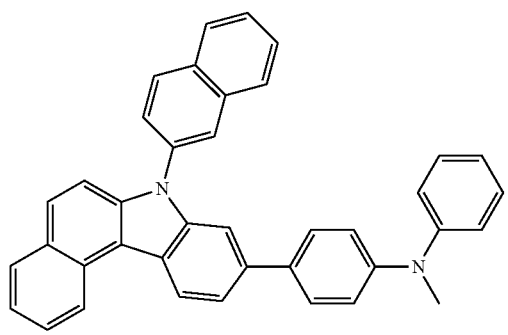
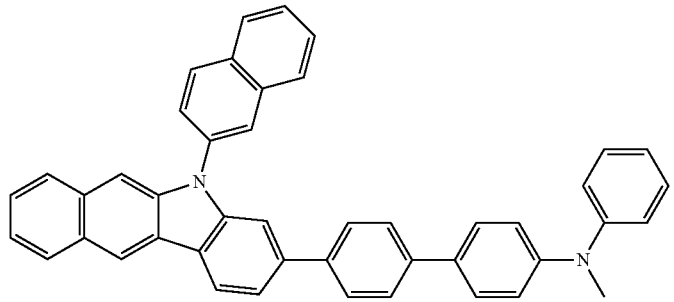
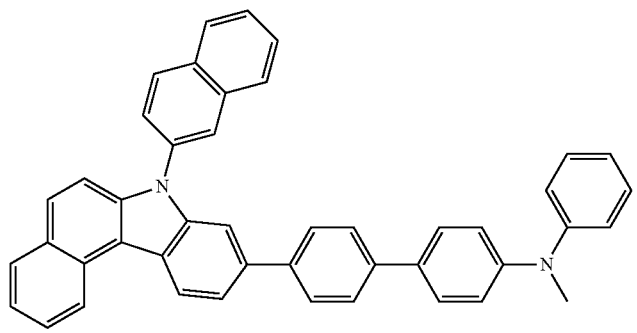

955
956
-continued
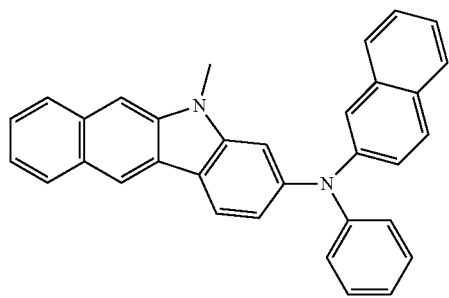
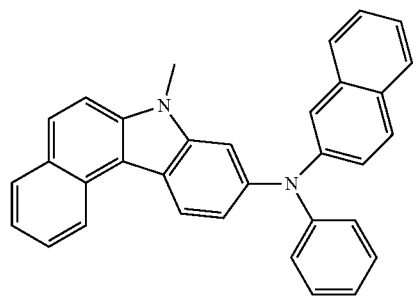
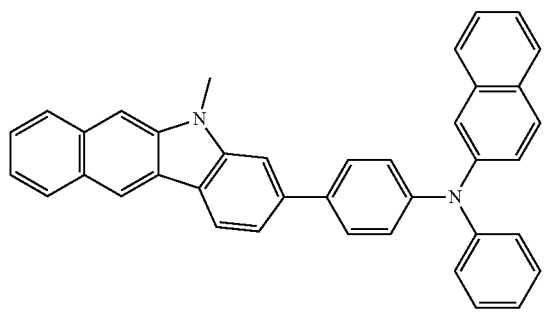
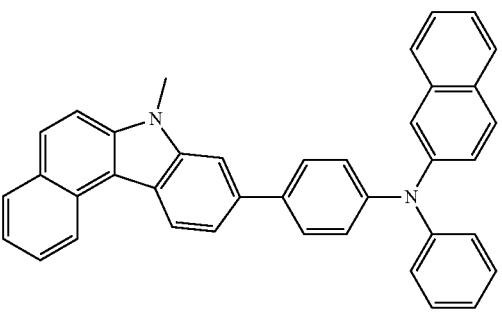
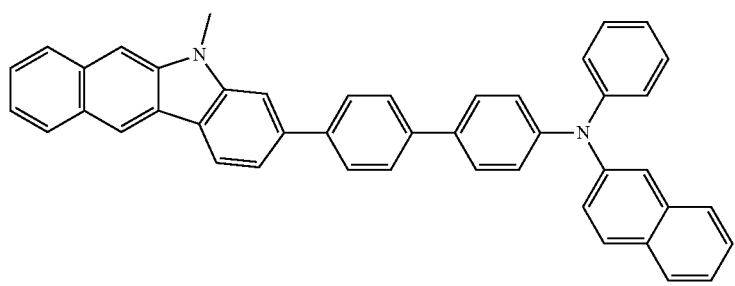
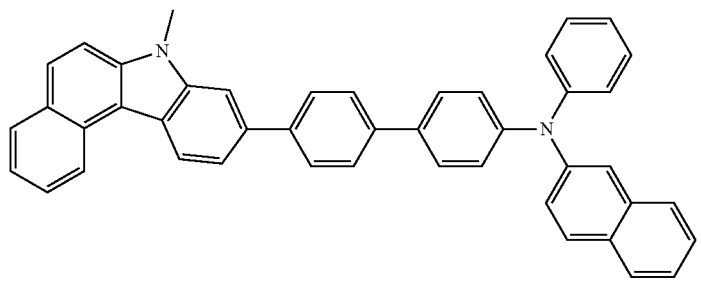
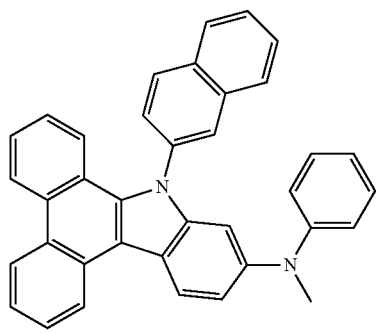
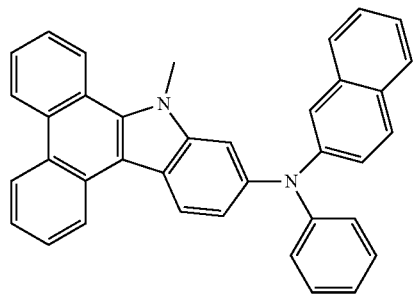

957
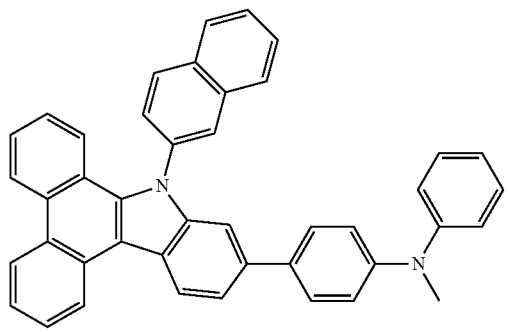
958
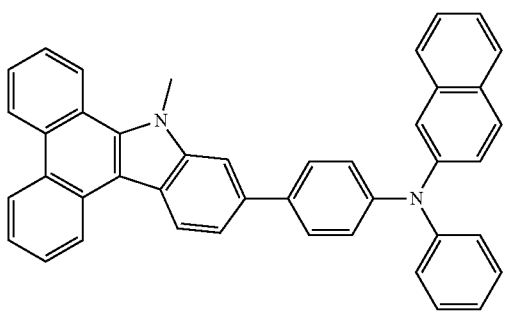
-continued
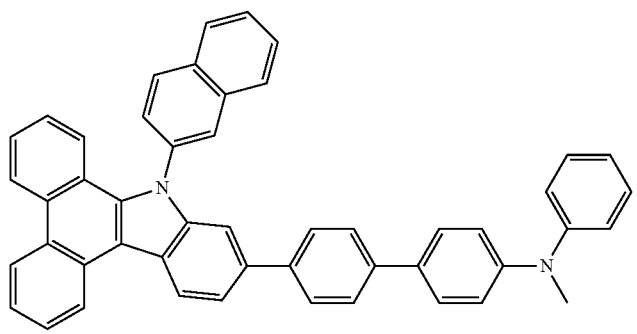
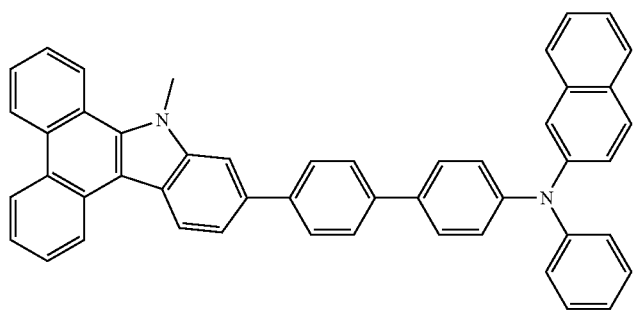
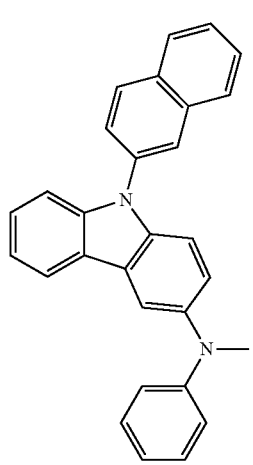
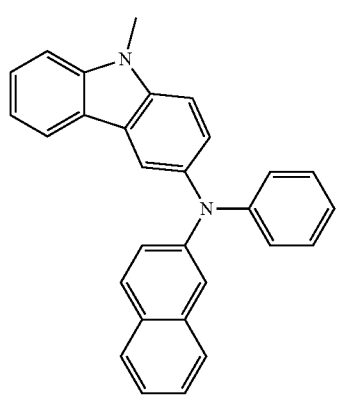
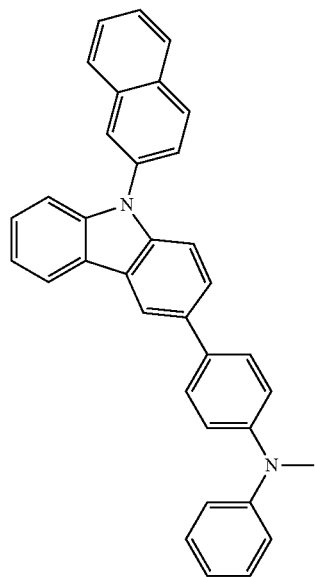

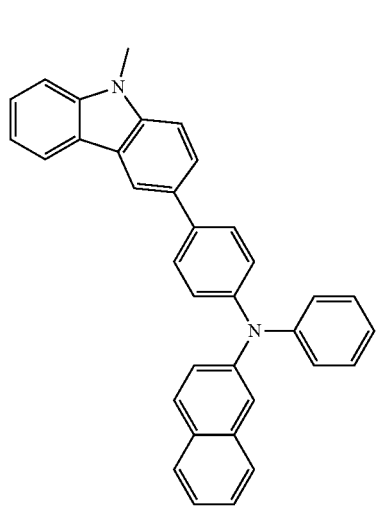
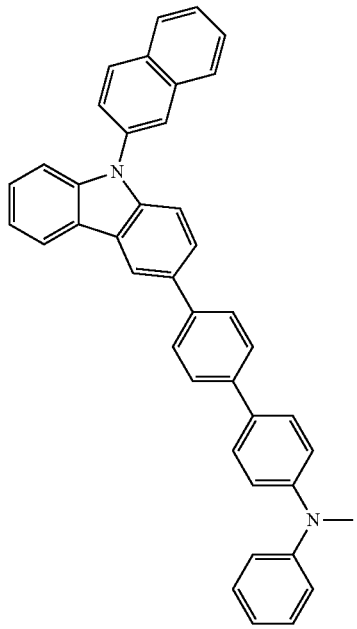
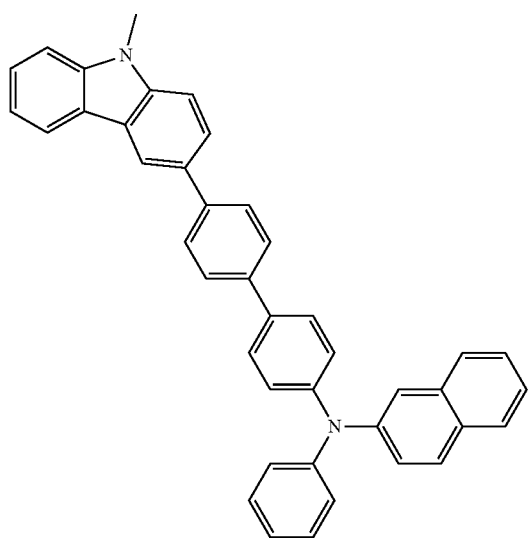
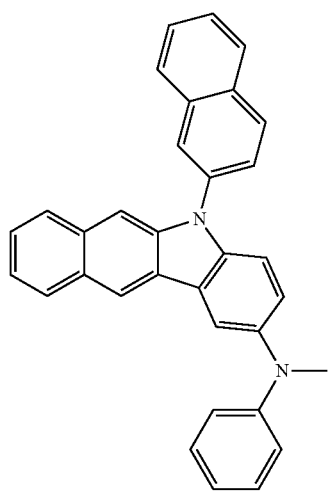

961
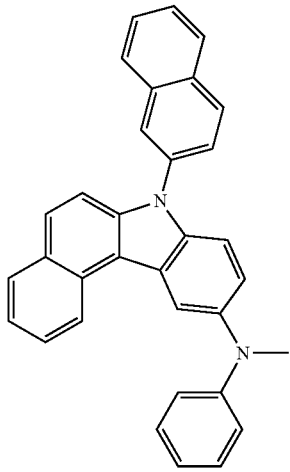
-continued
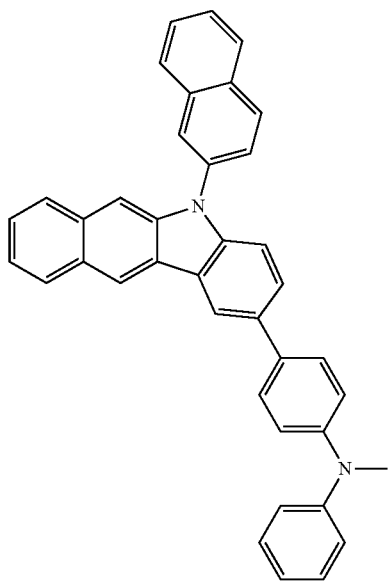
962
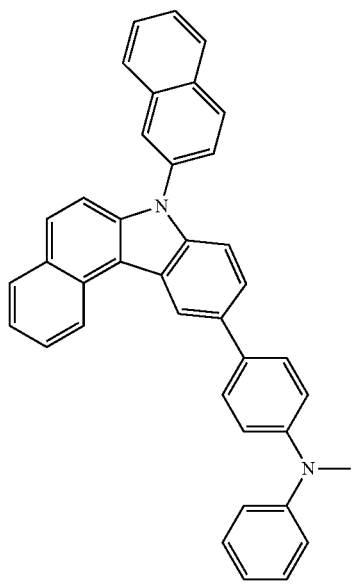
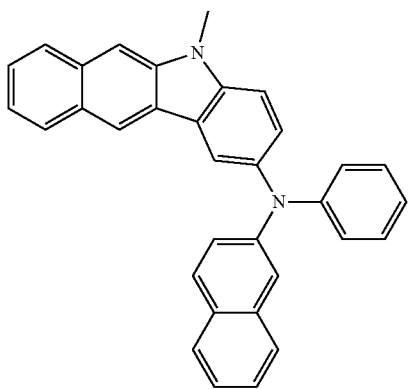
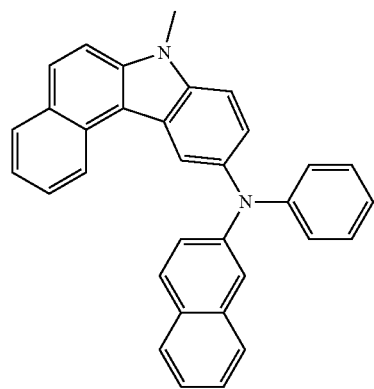
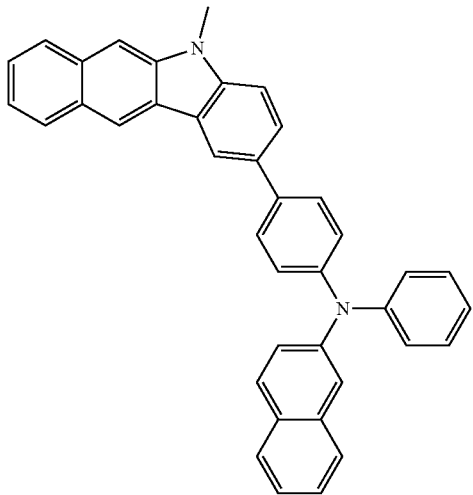
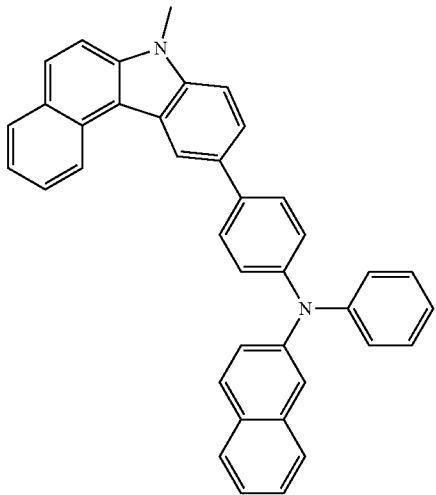

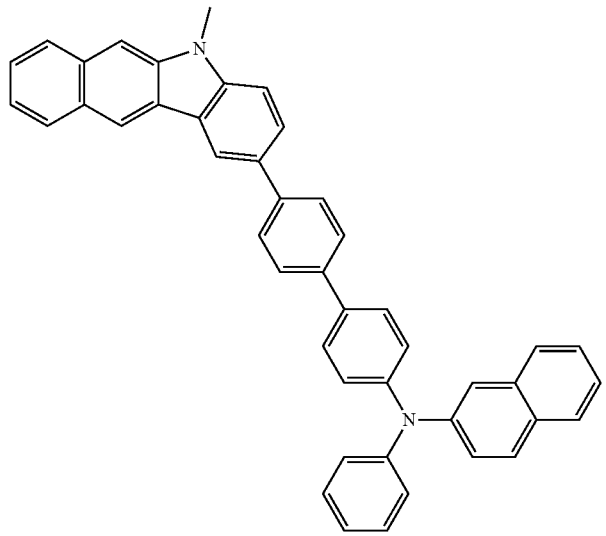
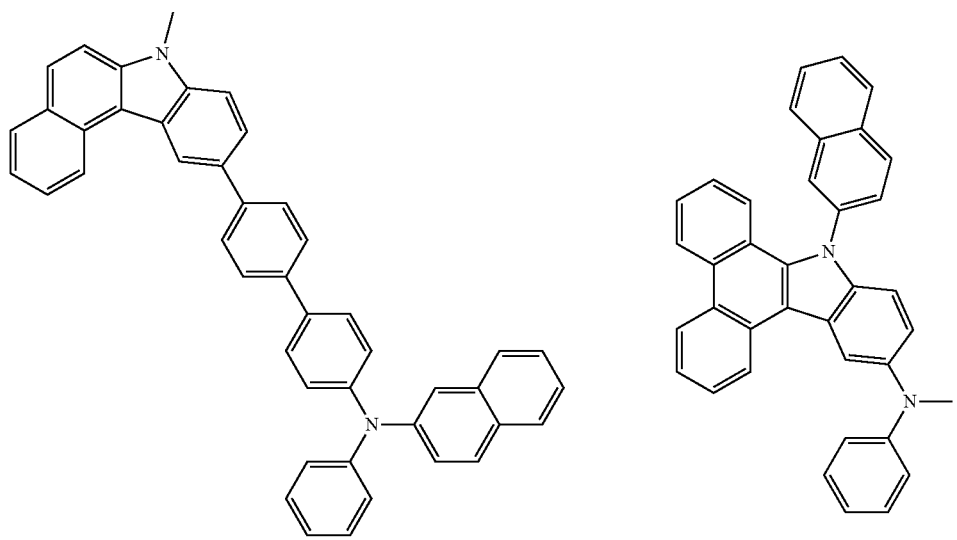
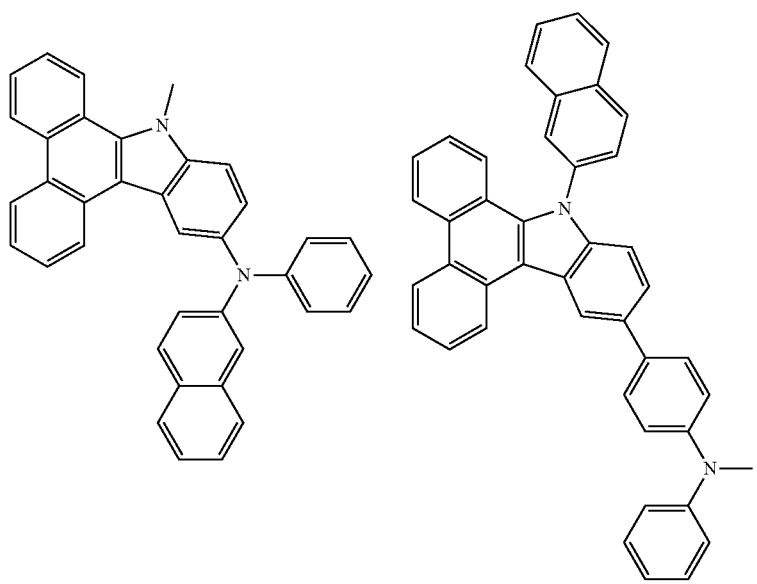

-continued
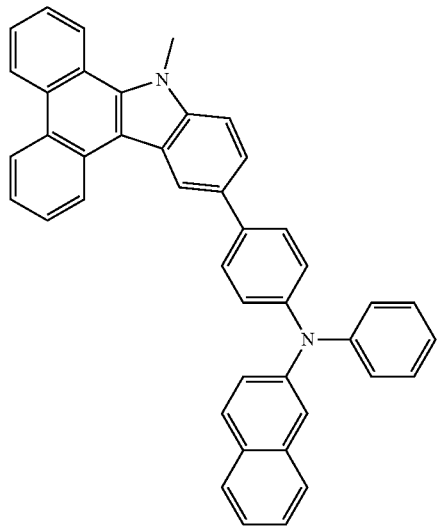
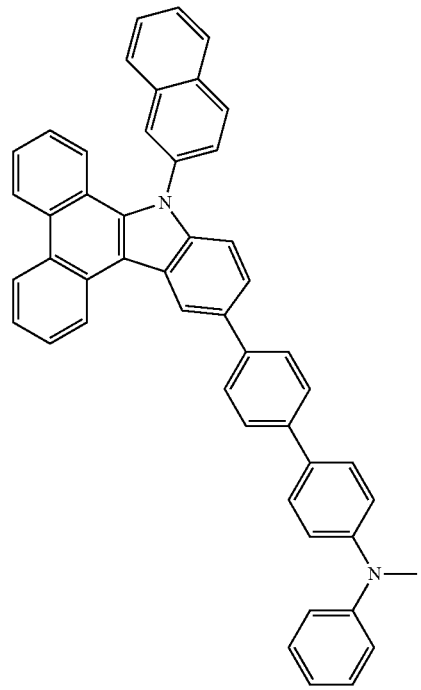
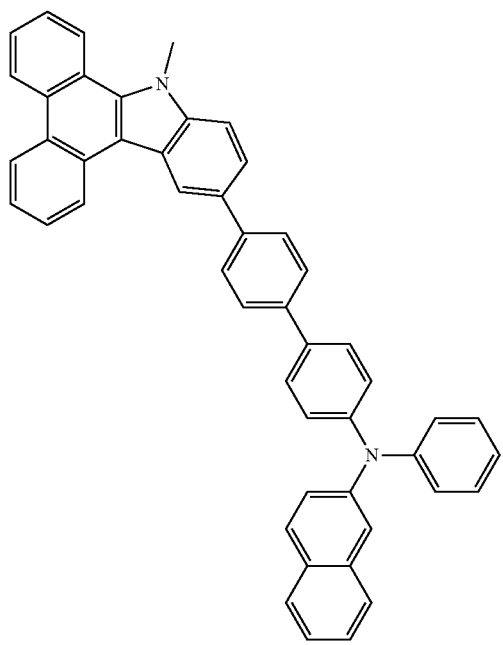
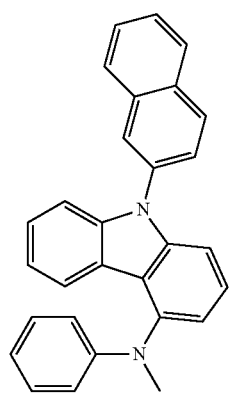
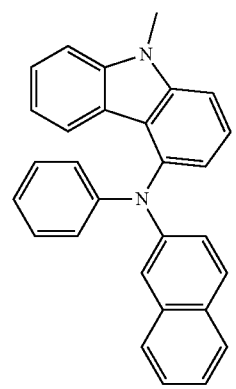

967 968
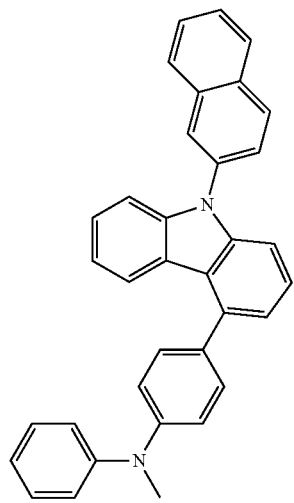 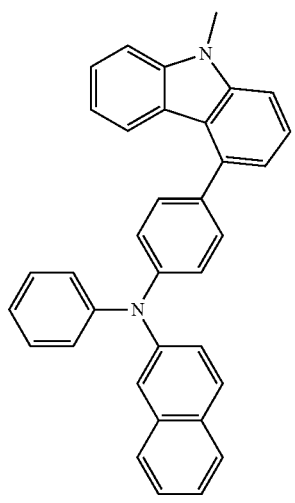 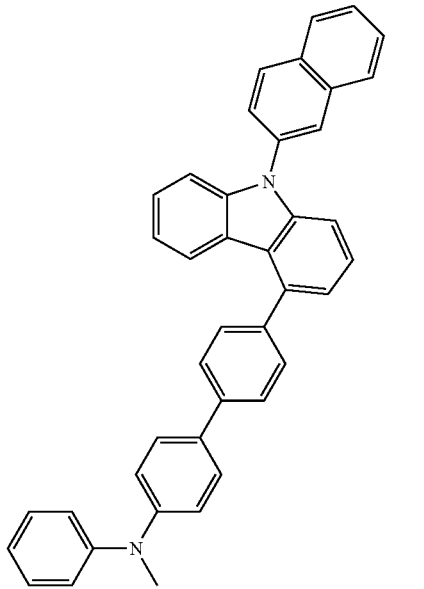
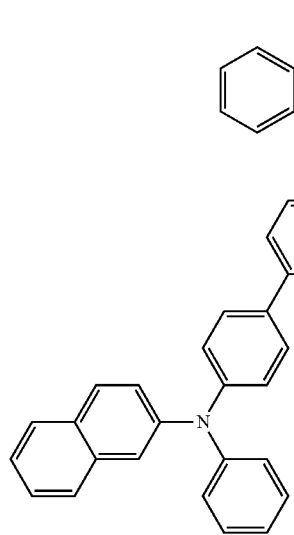 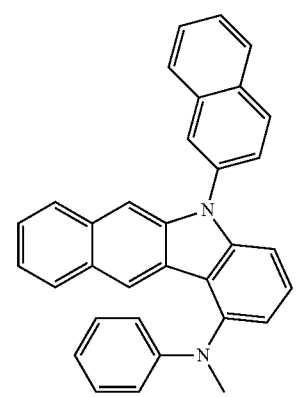 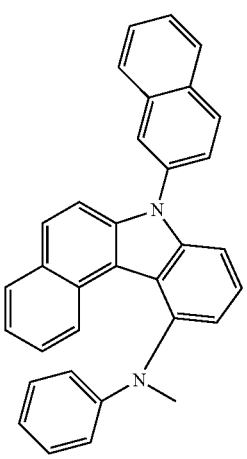
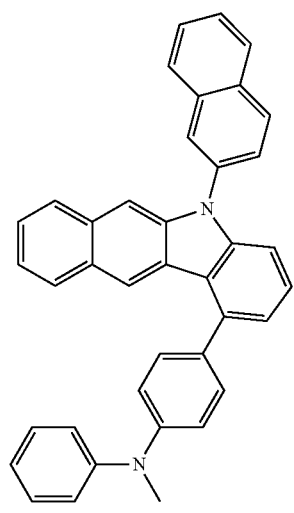 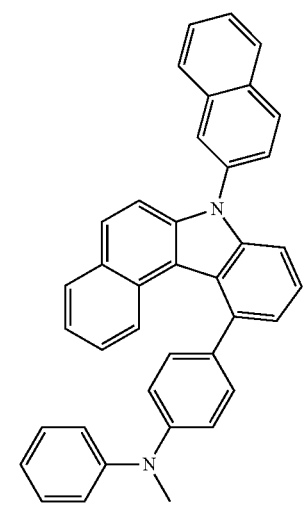 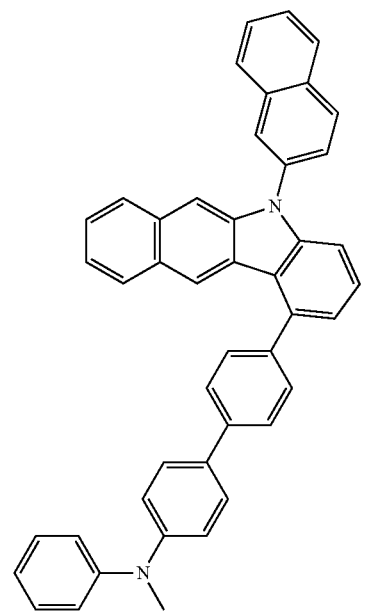

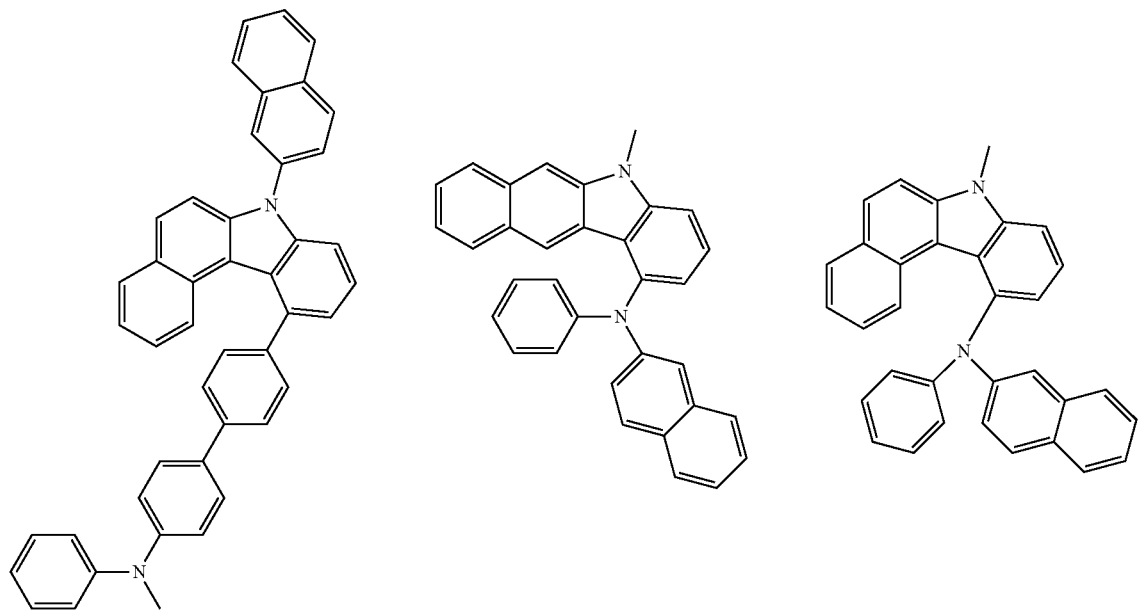
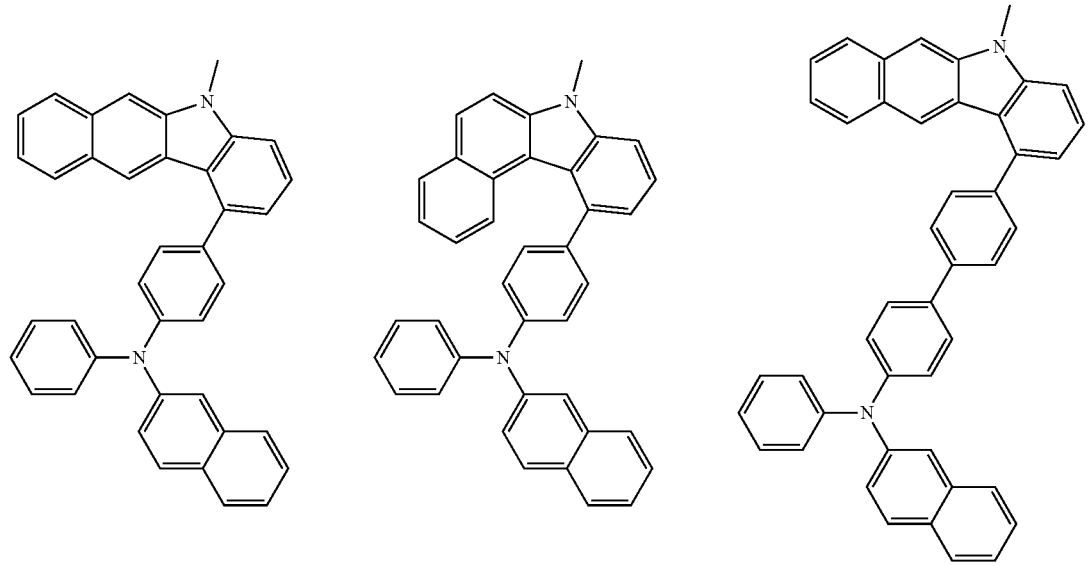

971
972
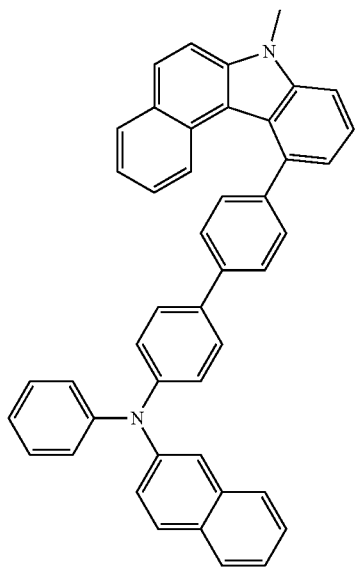
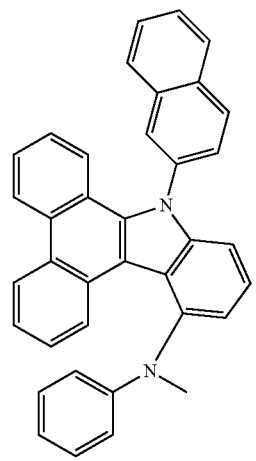
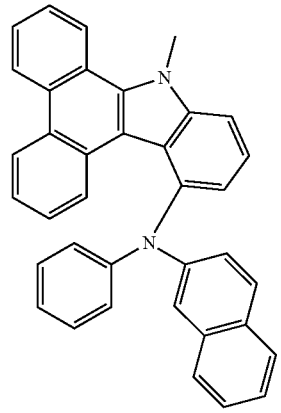
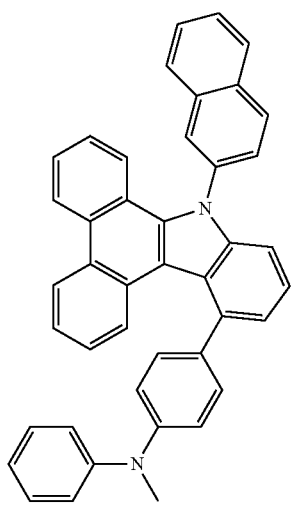
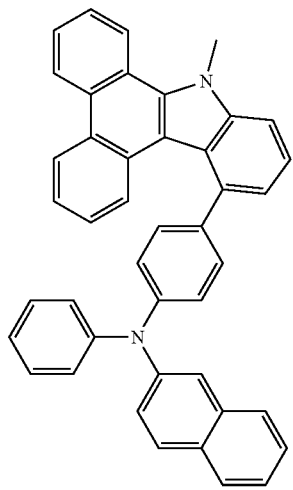
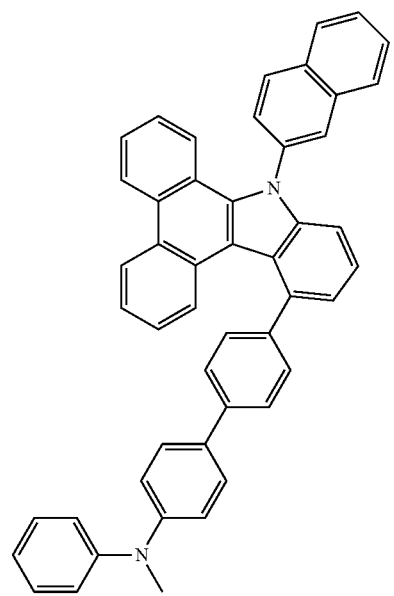

973 974
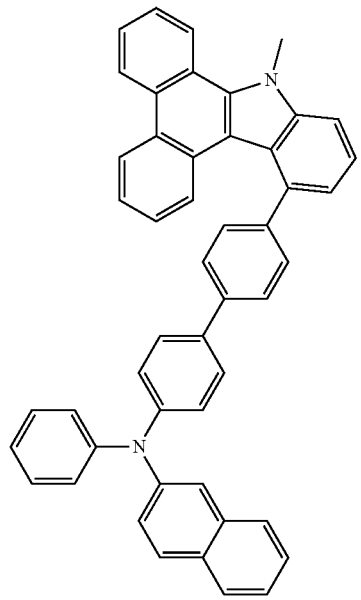
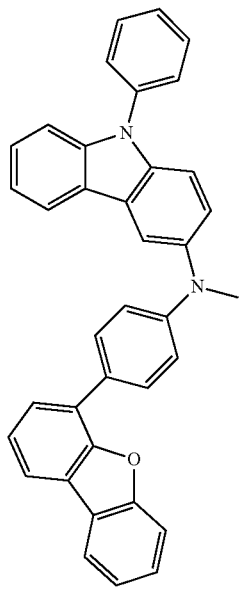
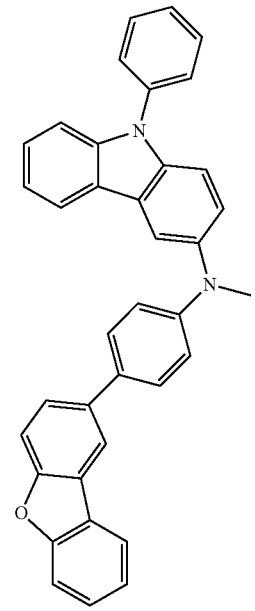
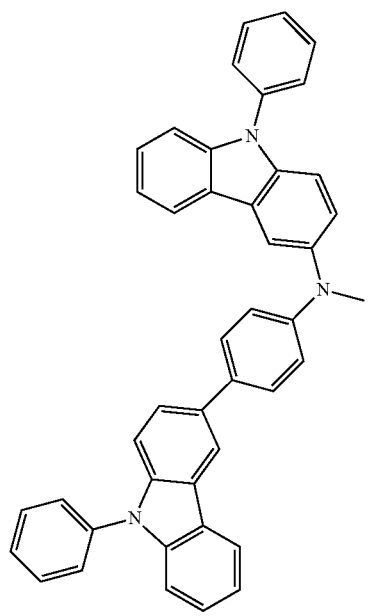
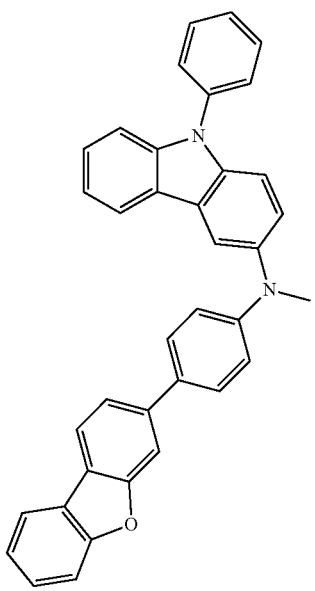
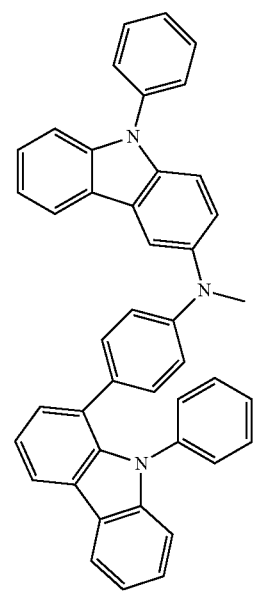

975
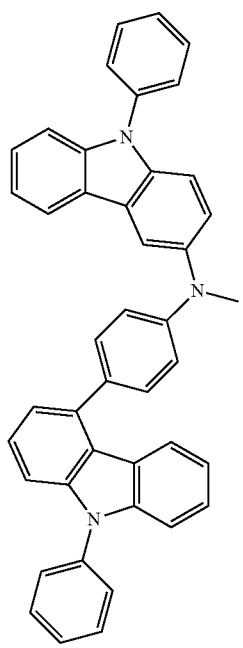
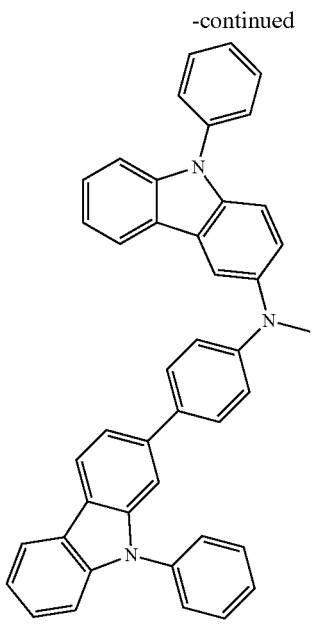
976
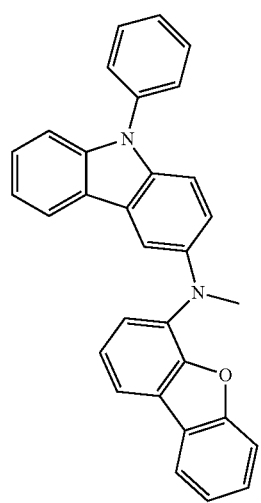
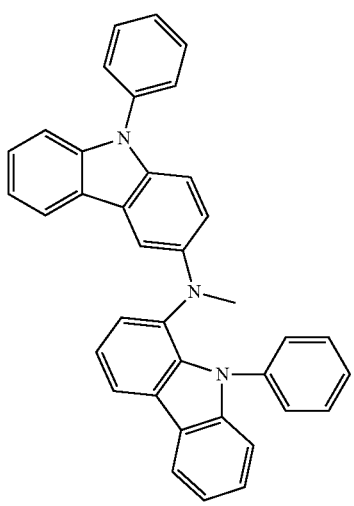
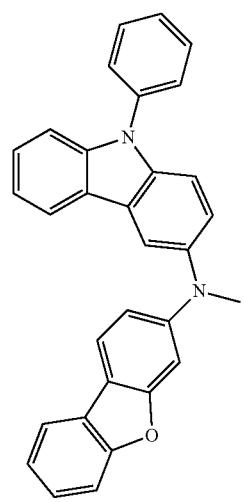
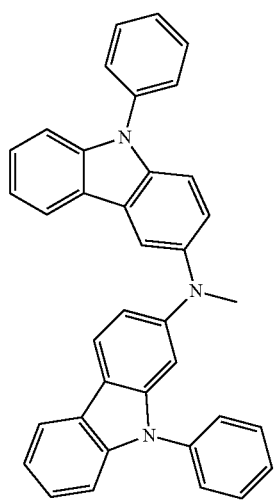
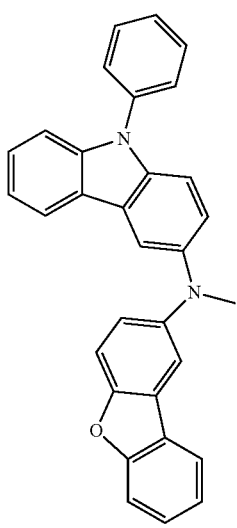
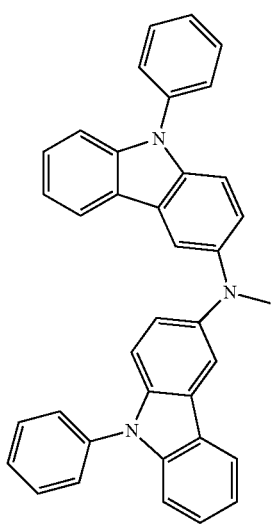
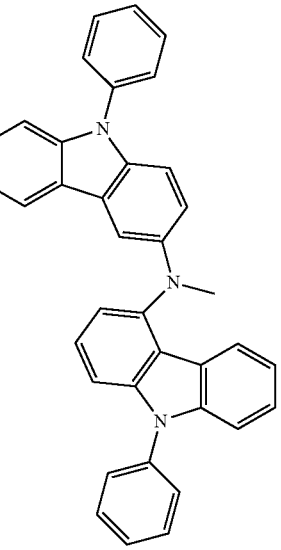

-continued
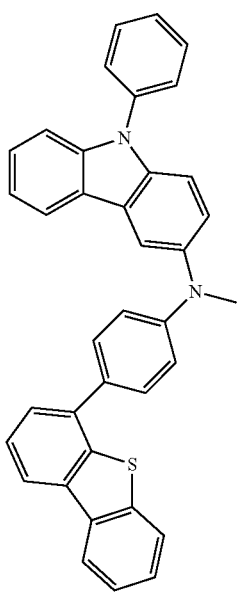 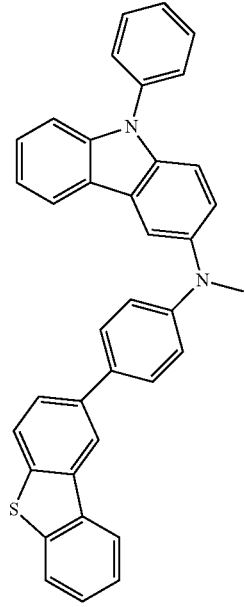 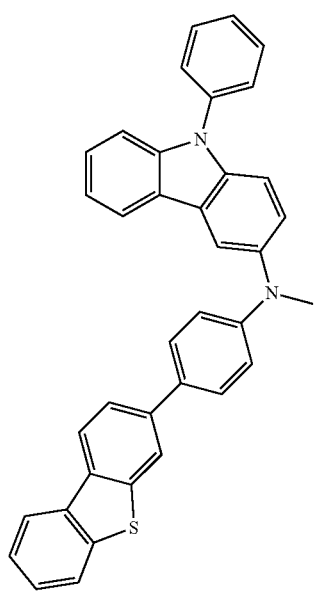
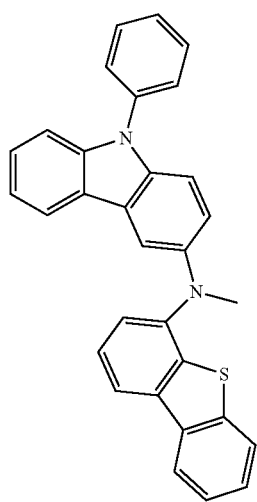 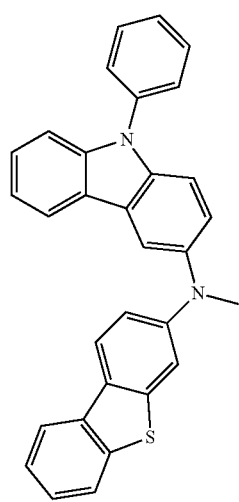 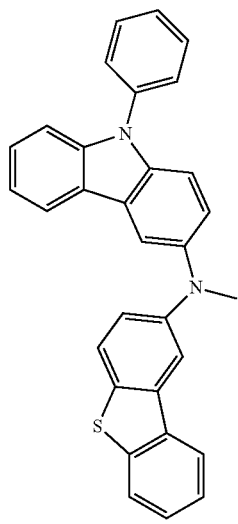
Preferred Examples of Compound 1[III]
Formulae of preferred examples of compound 1[III] are shown below, wherein the definition of each group and preferred example thereof are as described above in formula 1[III]:

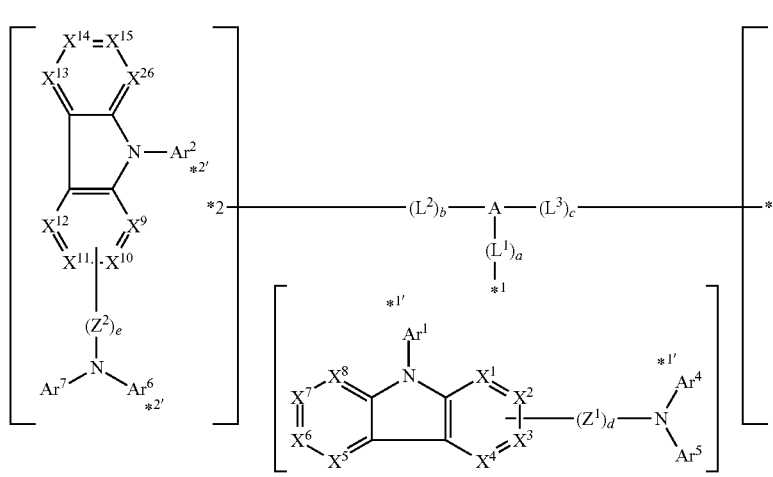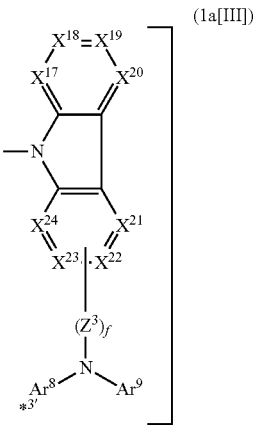
(1a[III])
in formula 1a[III], A, $L^1$ to $L^3$, a to f, $X^1$ to $X^{24}$, $Ar^1$ to $Ar^9$, $Z^1$ to $Z^3$, *1 to *3, *1' to *3', and preferred examples thereof are as described above in formula 1[III];
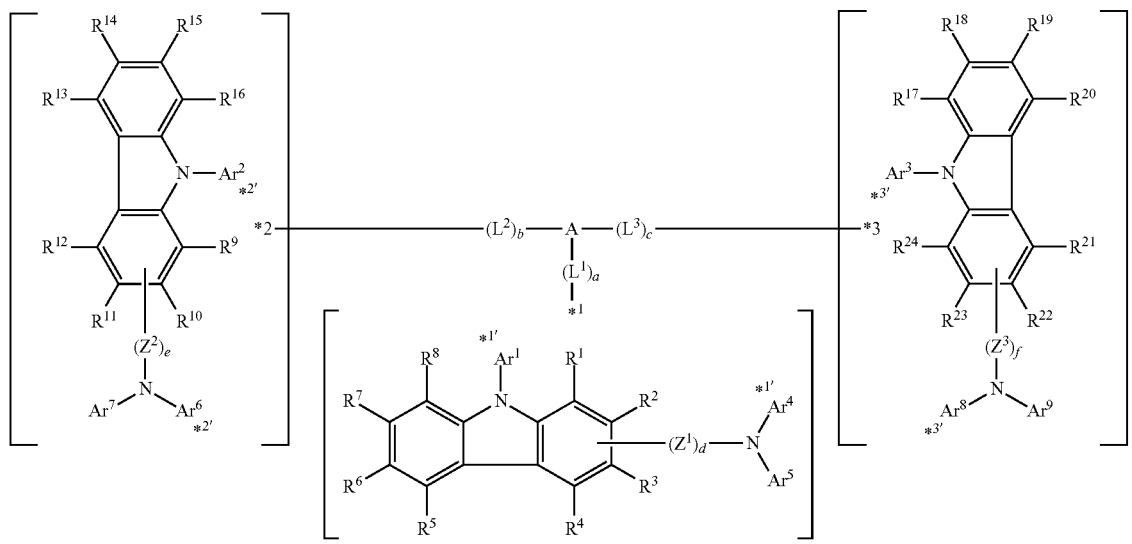
(1a'[III])
in formula 1a'[III], A, $L^1$ to $L^3$, a to f, $R^1$ to $R^{24}$, $Ar^1$ to $Ar^9$, $Z^1$ to $Z^3$, *1 to *3, *1' to *3', and preferred examples thereof are as described above in formula 1[III];

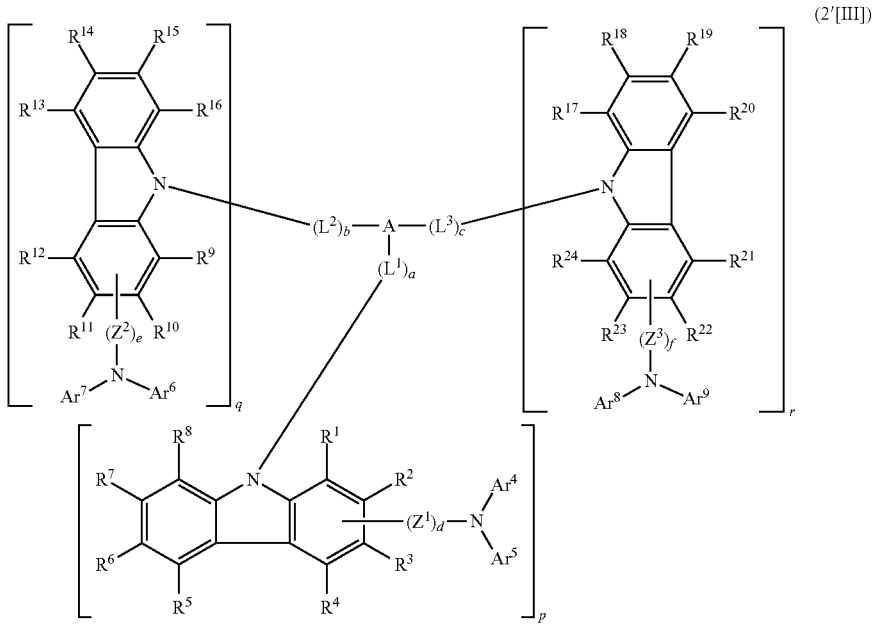

in formula 2'[III], A, $L^1$ to $L^3$, a to f, p to r, $R^1$ to $R^{24}$, $Ar^4$ to $Ar^9$, $Z^1$ to $Z^3$, and preferred examples thereof are as described above in formula 1[III]; and when p, q or r is 2 or 3, 2 or 3 groups in each [ ] may be the same or different;

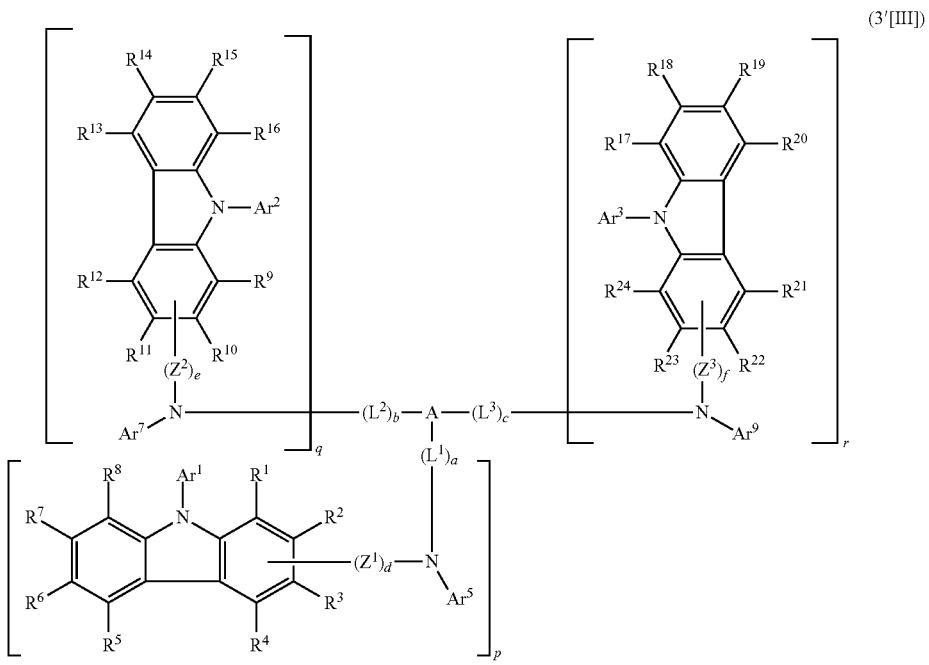

in formula 3'[III], A, $L^1$ to $L^3$, a to f, p to r, $R^1$ to $R^{24}$, $Ar^1$ to $Ar^3$, $Ar^5$, $Ar^7$, $Ar^9$, $Z^1$ to $Z^3$, and preferred examples thereof are as described above in formula 1[III]; and when p, q or r is 2 or 3, 2 or 3 groups in each [ ] may be the same or different;

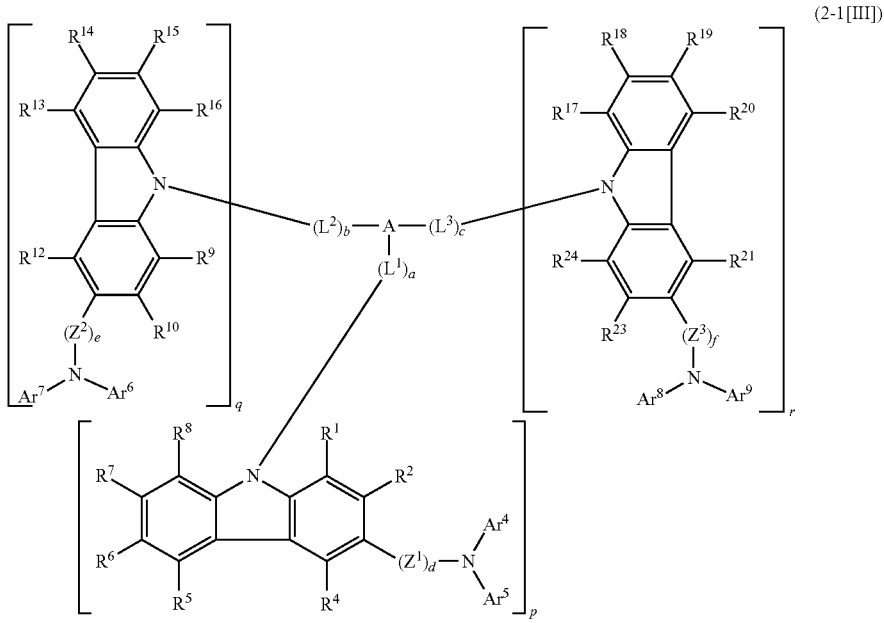

(2-1[III])

in formula 2-1[III], A, $L^1$ to $L^3$, a to f, p to r, $R^1$, $R^2$, $R^4$ to $R^{10}$, $R^{12}$ to $R^{21}$, $R^{23}$, $R^{24}$, $Ar^4$ to $Ar^9$, $Z^1$ to $Z^3$, and preferred examples thereof are as described above in formula 1[III]; and when p, q or r is 2 or 3, 2 or 3 groups in each [ ] may be the same or different;

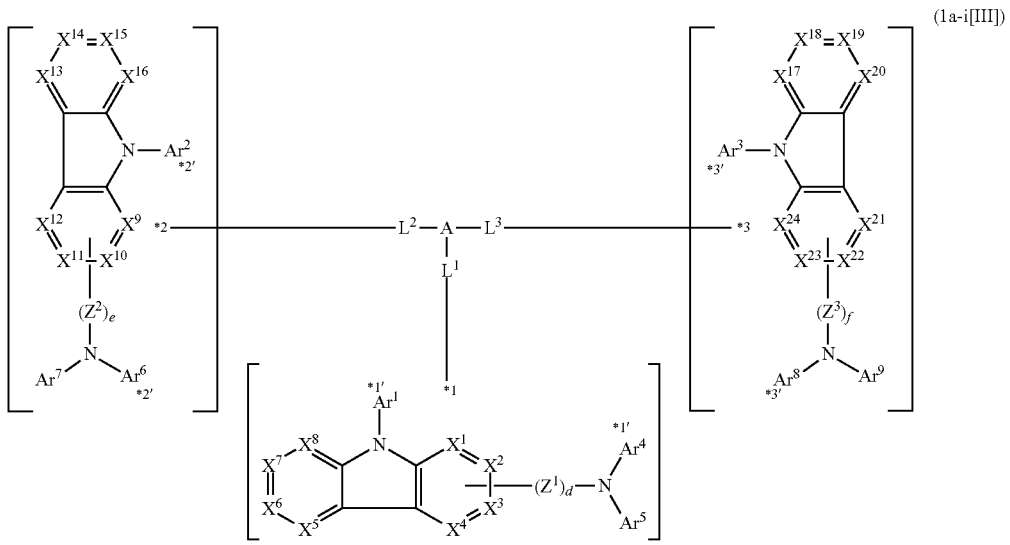

(1a-i[III])

in formula 1a-i[III], A, $L^1$ to $L^3$, d to f, $X^1$ to $X^{24}$, $Ar^1$ to $Ar^9$, $Z^1$ to $Z^3$, *1 to *3, *1' to *3', and preferred examples thereof are as described above in formula 1[III];

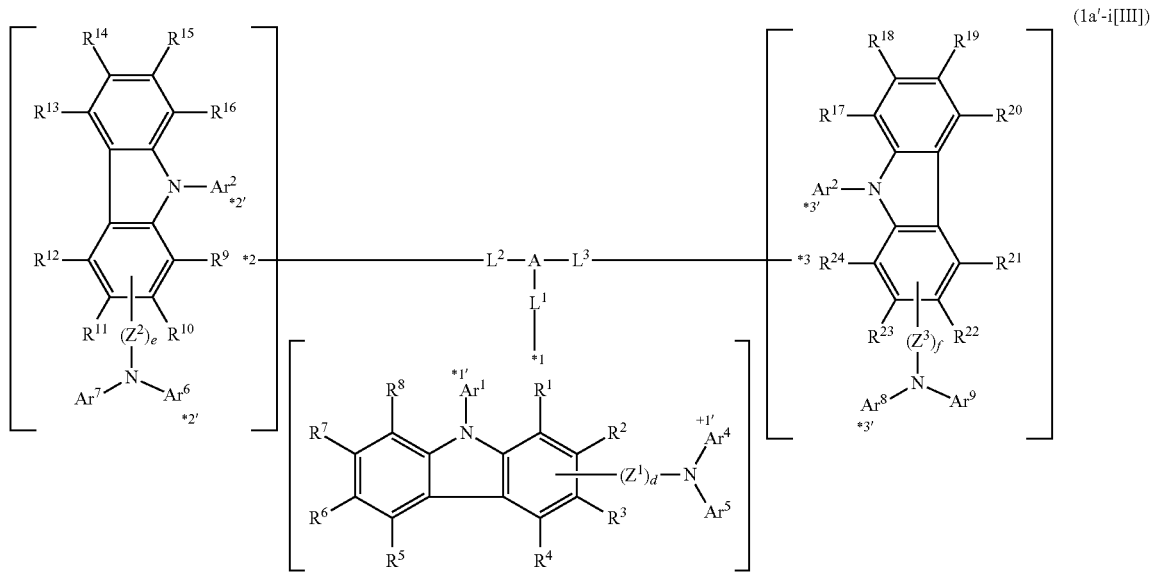

in formula 1a'-i[III], A, $L^1$ to $L^3$, d to f, $R^1$ to $R^{24}$, $Ar^1$ to $Ar^9$, $Z^1$ to $Z^3$, *1 to *3, *1' to *3', and preferred examples thereof are as described above in formula 1[III];

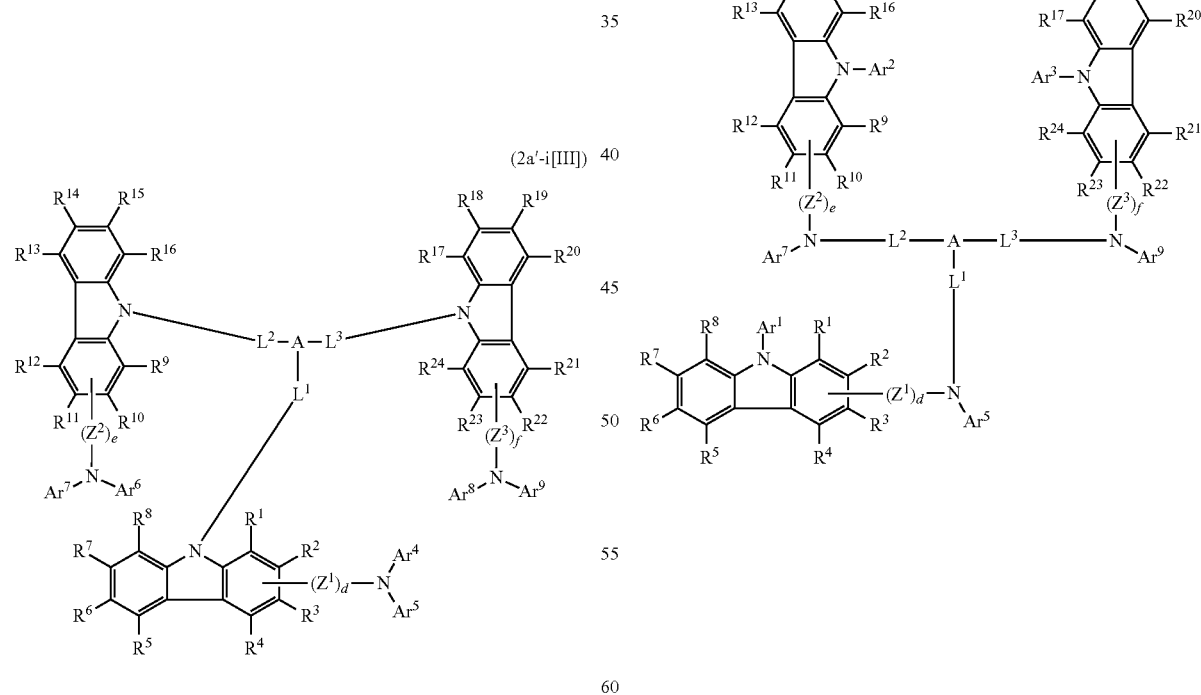

in formula 2a'-i[III], A, $L^1$ to $L^3$, d to f, $R^1$ to $R^{24}$, $Ar^4$ to $Ar^9$, $Z^1$ to $Z^3$, and preferred examples thereof are as described above in formula 1[III];

in formula 3a'-i[III], A, $L^1$ to $L^3$, d to f, $R^1$ to $R^{24}$, $Ar^1$ to $Ar^3$, $Ar^5$, $Ar^7$, $Ar^9$, $Z^1$ to $Z^3$, and preferred examples thereof are as described above in formula 1[III];

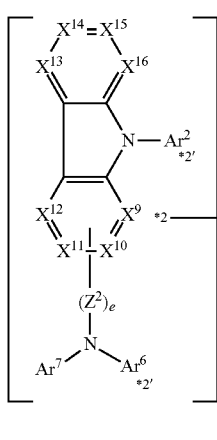 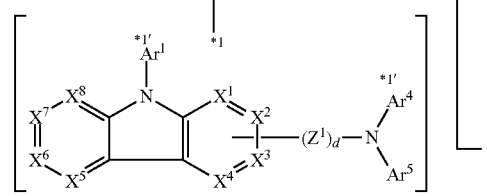 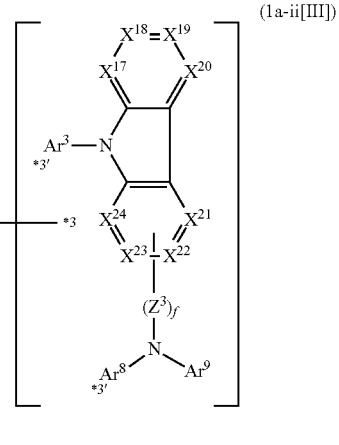

(1a-ii[III])

in formula 1a-ii[III], A, L², L³, b to f, X¹ to X²⁴, Ar¹ to Ar⁹, Z¹ to Z³, *1 to *3, *1' to *3', and preferred examples thereof are as described above in formula 1[III];

in formula 2a'-ii[III], A, L², L³, b to f, R¹ to R²⁴, Ar⁴ to Ar⁹, Z¹ to Z³, and preferred examples thereof are as described above in formula 1[III];

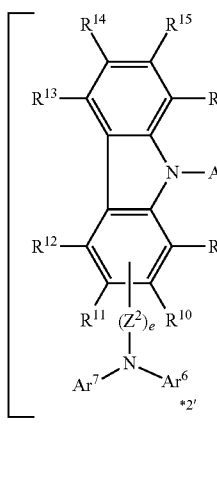 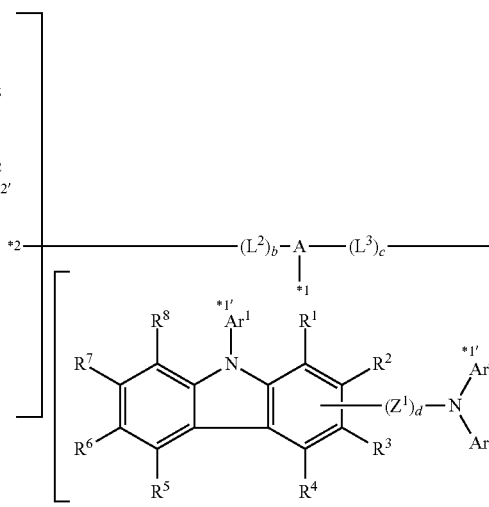 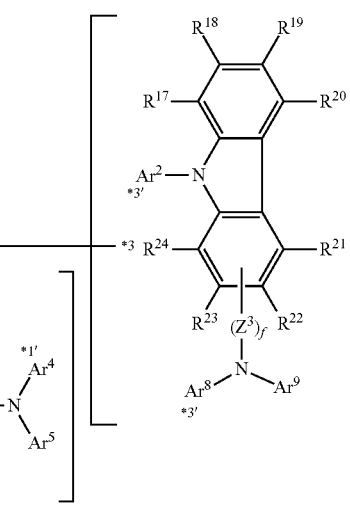

(1a'-ii[III])

in formula 1a'-ii[III], A, L², L³, b to f, R¹ to R²⁴, Ar¹ to Ar⁹, Z¹ to Z³, *1 to *3, *1' to *3', and preferred examples thereof are as described above in formula 1[III];

(2a'-ii[III])

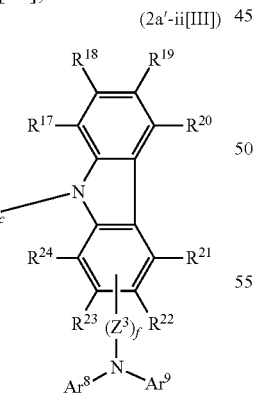

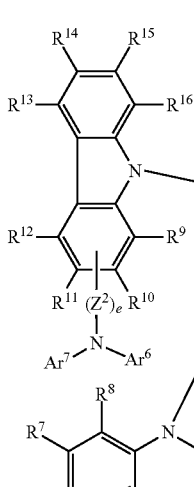

(3a'-ii[III])

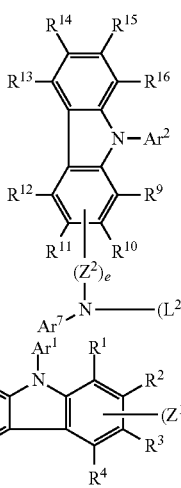 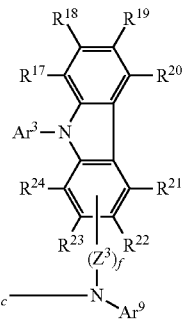

in formula 3a'-ii[III], A, L², L³, b to f, R¹ to R²⁴, Ar¹ to Ar³, Ar⁵, Ar⁷, Ar⁹, Z¹ to Z³, and preferred examples thereof are as described above in formula 1[III];

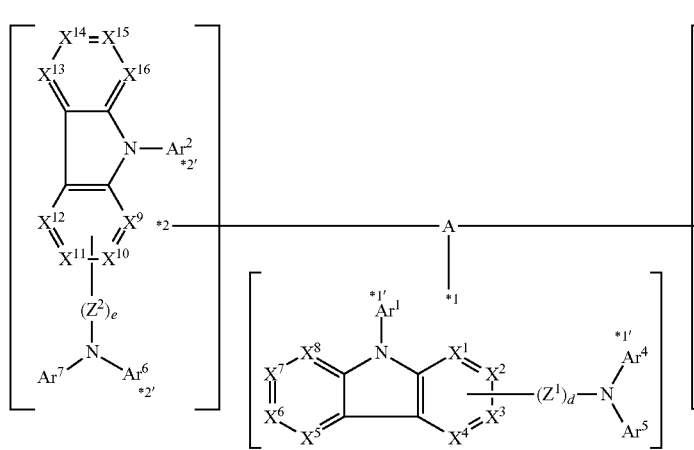
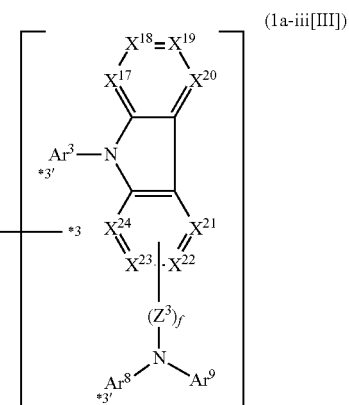
(1a-iii[III])
in formula 1a-iii[III], A, d to f, $X^1$ to $X^{24}$, $Ar^1$ to $Ar^9$, $Z^1$ to $Z^3$, *1 to *3, *1' to *3', and preferred examples thereof are as described above in formula 1[III];
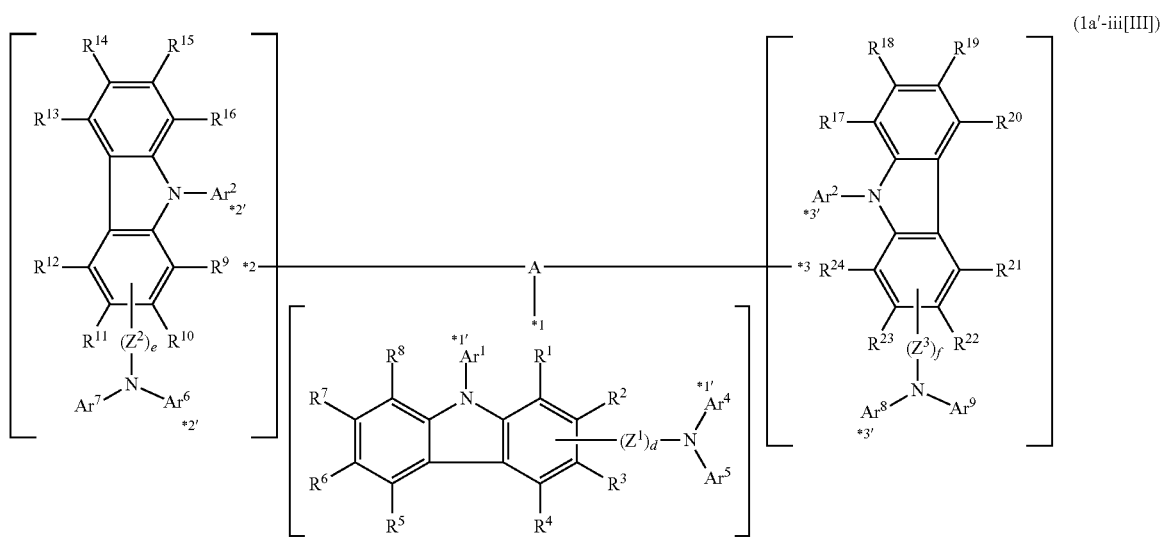
(1a'-iii[III])
in formula 1a'-iii[III], A, d to f, $R^1$ to $R^{24}$, $Ar^1$ to $Ar^{19}$, $Z^1$ to $Z^3$, *1 to *3, *1' to *3', and preferred examples thereof are as described above in formula 1[III];

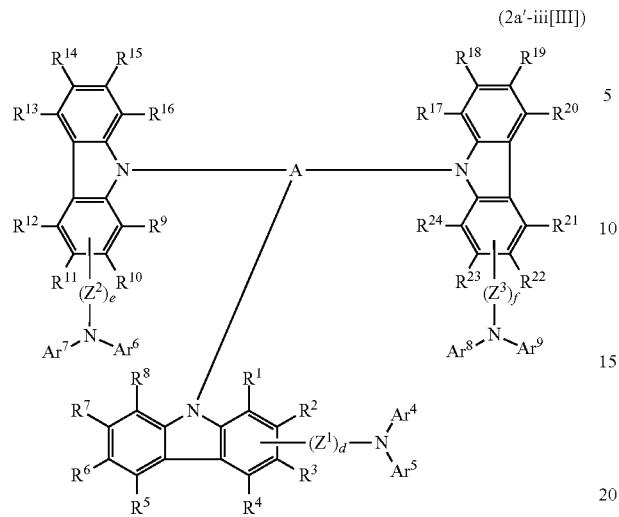

(2a'-iii[III])

in formula 2a'-iii[III], A, d to f, $R^1$ to $R^{24}$, $Ar^4$ to $Ar^9$, $Z^1$ to $Z^3$, and preferred examples thereof are as described above in formula 1[III];

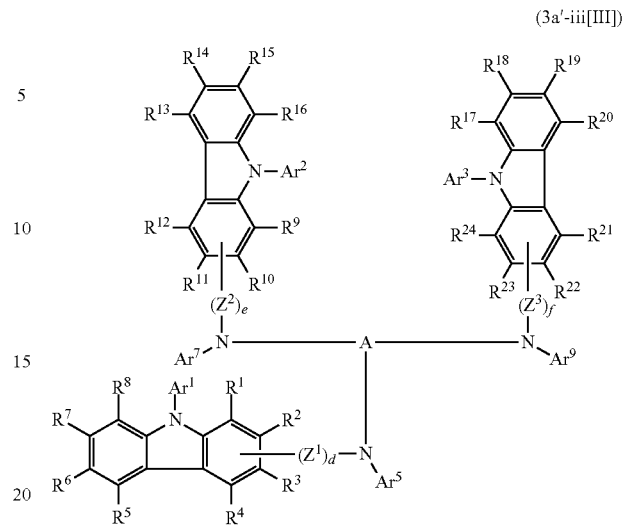

(3a'-iii[III])

in formula 3a'-iii[III], A, d to f, $R^1$ to $R^{24}$, $Ar^1$ to $Ar^3$, $Ar^5$, $Ar^7$, $Ar^9$, $Z^1$ to $Z^3$, and preferred examples thereof are as described above in formula 1[III];

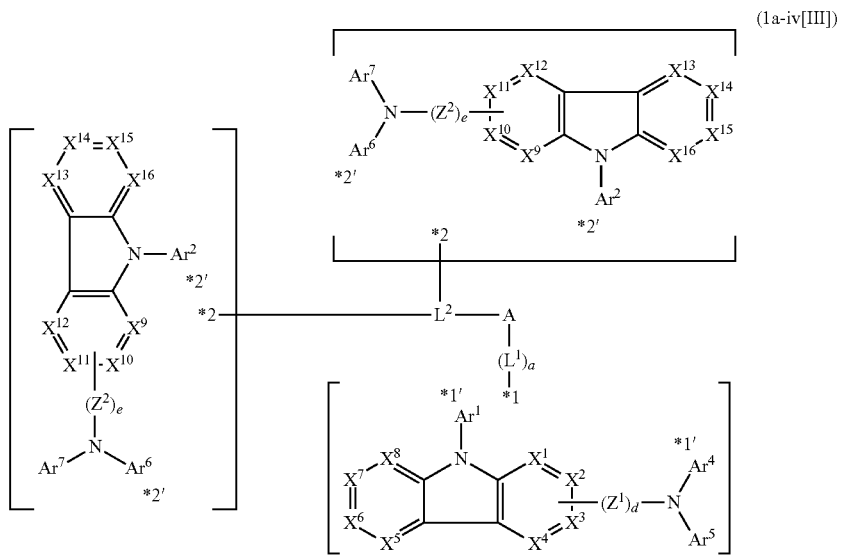

(1a-iv[III])

in formula 1a-iv[III], A, $L^1$, $L^2$, a, d, e, $X^1$ to $X^{16}$, $Ar^1$, $Ar^2$, $Ar^4$ to $Ar^7$, $Z^1$, $Z^2$, *1, *2, *1', *2', and preferred examples thereof are as described above in formula 1[III]; and two or more groups represented by the same symbol may be the same or different;

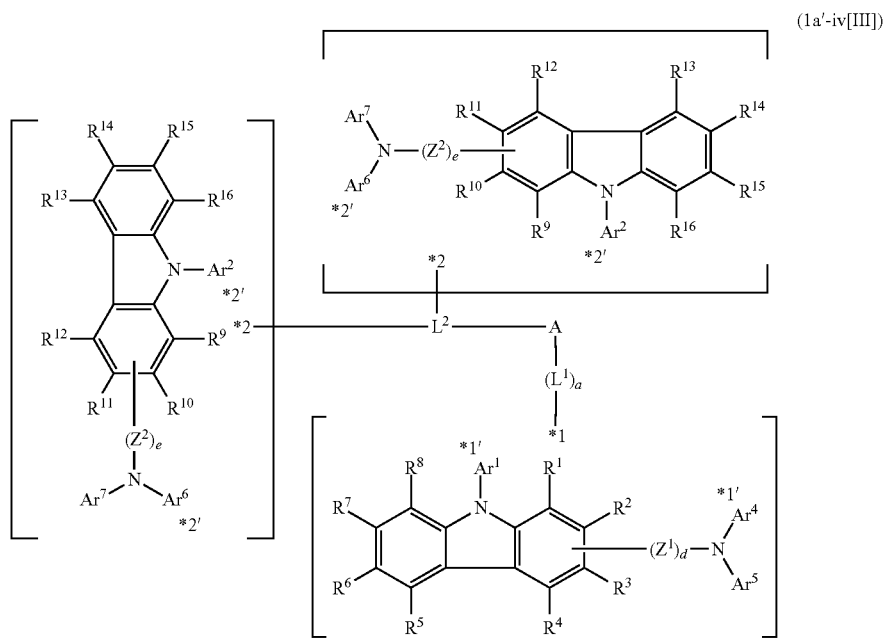

(1a'-iv[III])

in formula 1a'-iv[III], A, $L^1$, $L^2$, a, d, e, $R^1$ to $R^{16}$, $Ar^1$, $Ar^2$, $Ar^4$ to $Ar^7$, $Z^1$, $Z^2$, *1, *2, *1', *2', and preferred examples thereof are as described above in formula 1[III]; and two or more groups represented by the same symbol may be the same or different;

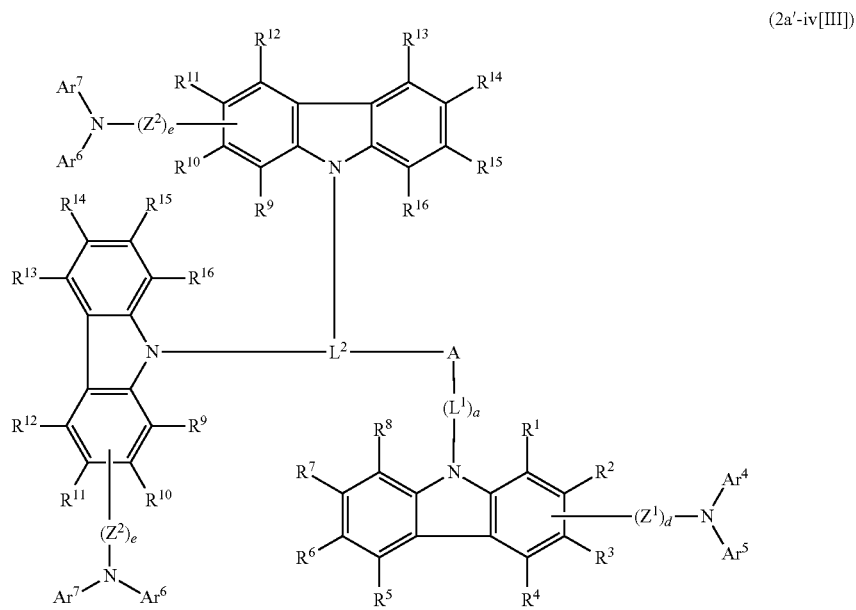

(2a'-iv[III])

in formula 2a'-iv[III], A, $L^1$, $L^2$, a, d, e, $R^1$ to $R^{16}$, $Ar^4$ to $Ar^7$, $Z^1$, $Z^2$, and preferred examples thereof are as described above in formula 1[III]; and two or more groups represented by the same symbol may be the same or different;

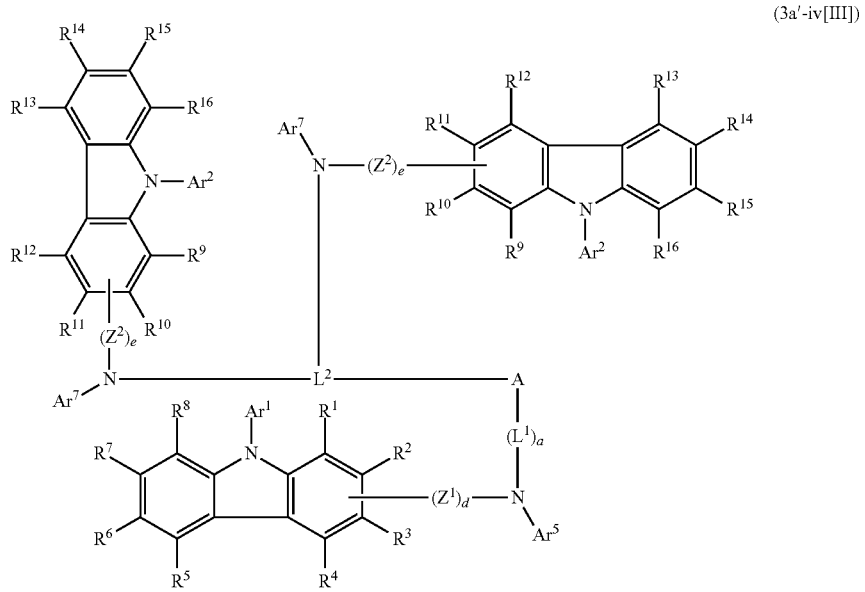

(3a'-iv[III])

in formula 3a'-iv[III], A, $L^1$, $L^2$, a, d, e, $R^1$ to $R^{16}$, $Ar^1$, $Ar^2$, $Ar^6$, $Ar^7$, $Z^1$, $Z^2$, and preferred examples thereof are as described above in formula 1[III]; and two or more groups represented by the same symbol may be the same or different;

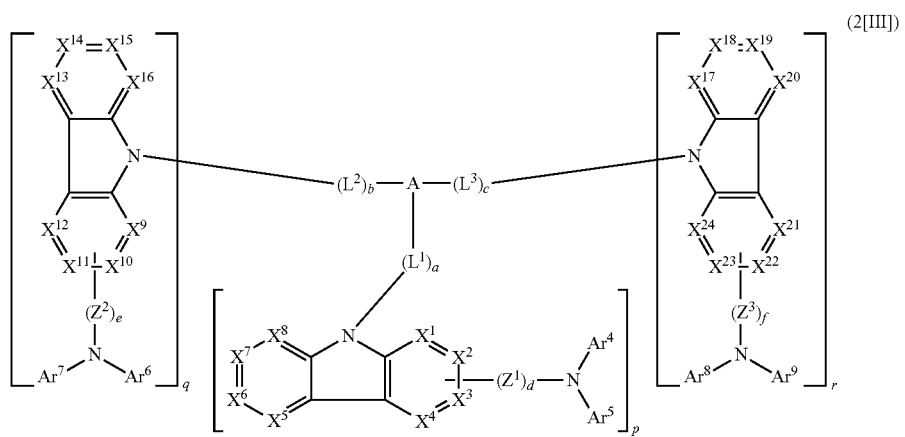

(2[III])

in formula 2[III], A, $L^1$ to $L^3$, a to f, p to r, $X^1$ to $X^{24}$, $Ar^4$ to $Ar^9$, $Z^1$ to $Z^3$, and preferred examples thereof are as described above in formula 1[III]; and when p, q or r is 2 or 3, 2 or 3 groups in each [ ] may be the same or different;

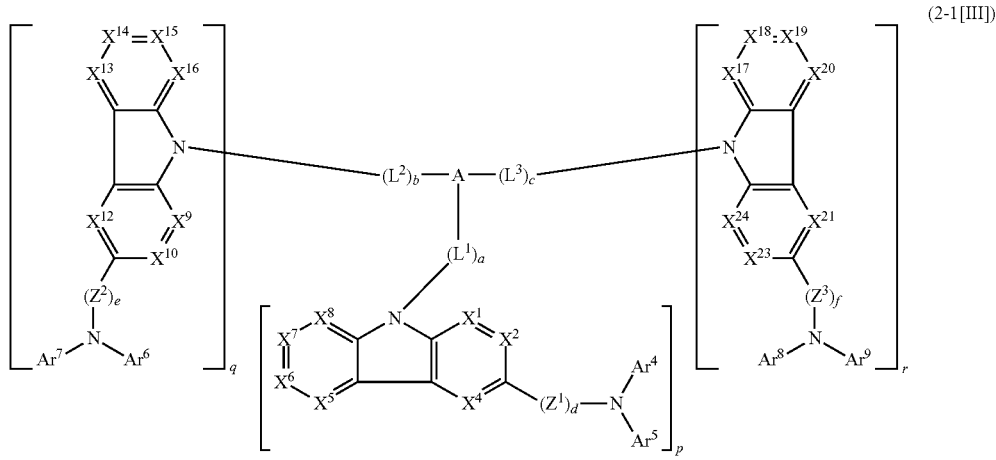

(2-1[III])

in formula 2-1[III], A, $L^1$ to $L^3$, a to f, p to r, $X^1$, $X^2$, $X^4$ to $X^{10}$, $X^{12}$ to $X^{21}$, $X^{23}$, $X^{24}$, $Ar^4$ to $Ar^9$, $Z^1$ to $Z^3$, and preferred examples thereof are as described above in formula 1[III]; and when p, q or r is 2 or 3, 2 or 3 groups in each [ ] may be the same or different;

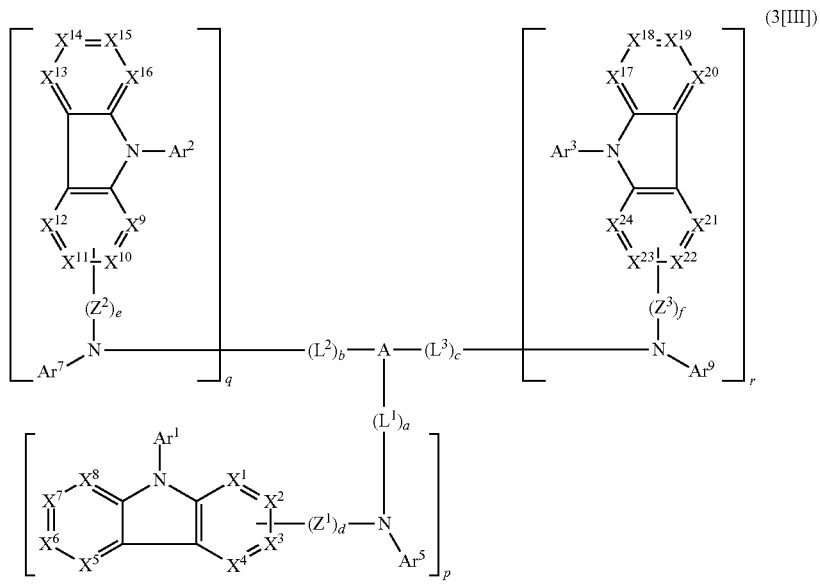

(3[III])

in formula 3[III], A, $L^1$ to $L^3$, a to f, p to r, $X^1$ to $X^{24}$, $Ar^1$ to $Ar^3$, $Ar^5$, $Ar^7$, $Ar^9$, $Z^1$ to $Z^3$, and preferred examples thereof are as described above in formula 1[III];

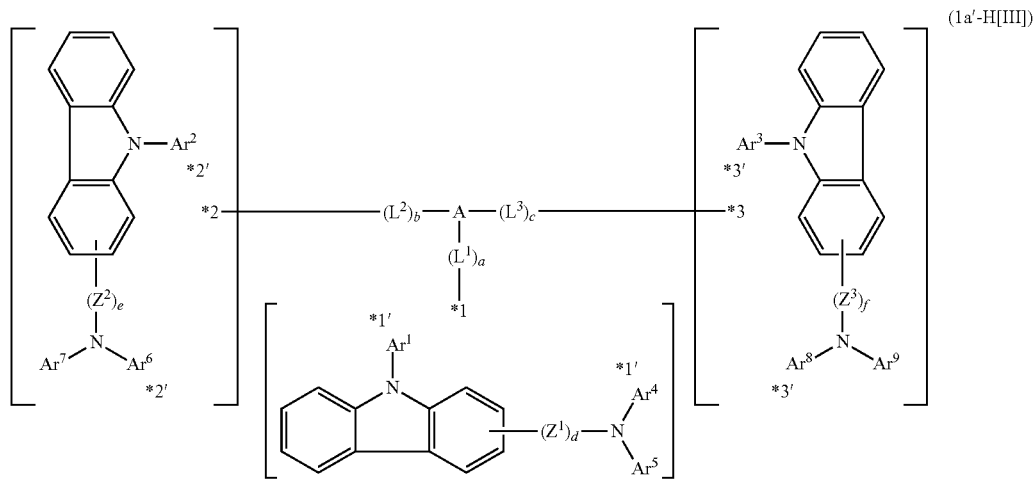

in formula 1a'-H[III], A, $L^1$ to $L^3$, a to f, $Ar^1$ to $Ar^9$, $Z^1$ to $Z^3$, *1 to *3, *1' to *3', and preferred examples thereof are as described above in formula 1[III]; and a bond extending from each of $Z^1$ to $Z^3$ toward a benzene ring is bonded to one of four carbon atoms of a benzene ring, which contains the terminal end of the bond, in place of a hydrogen atom removed therefrom;

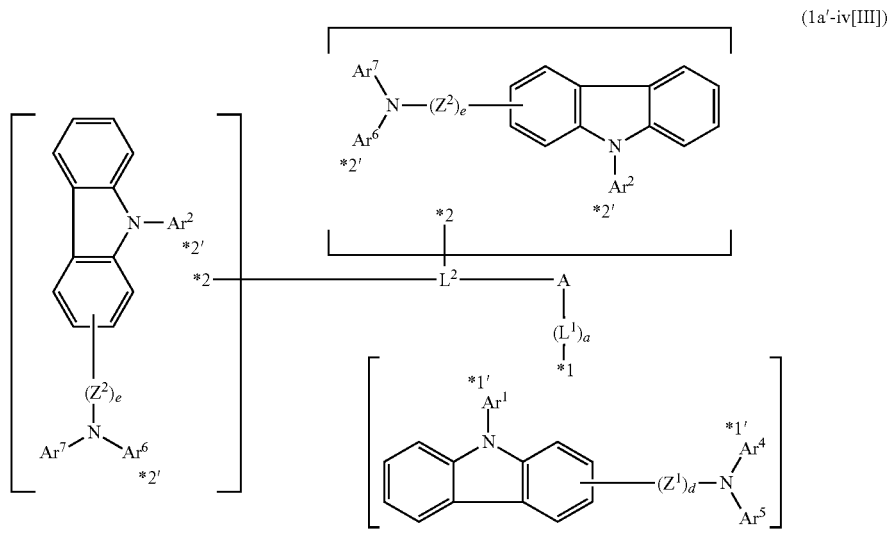

in formula 1a'-iv-H[III], A, $L^1$, $L^2$, a, d, e, $Ar^1$, $Ar^2$, $Ar^4$ to $Ar^7$, $Z^1$, $Z^2$, *1, *2, *1', *2', and preferred examples thereof are as described above in formula 1[III]; two or more groups represented by the same symbol may be the same or different; and a bond extending from each of $Z^1$ to $Z^3$ toward a benzene ring is bonded to one of four carbon atoms of a benzene ring, which contains the terminal end of the bond, in place of a hydrogen atom removed therefrom;

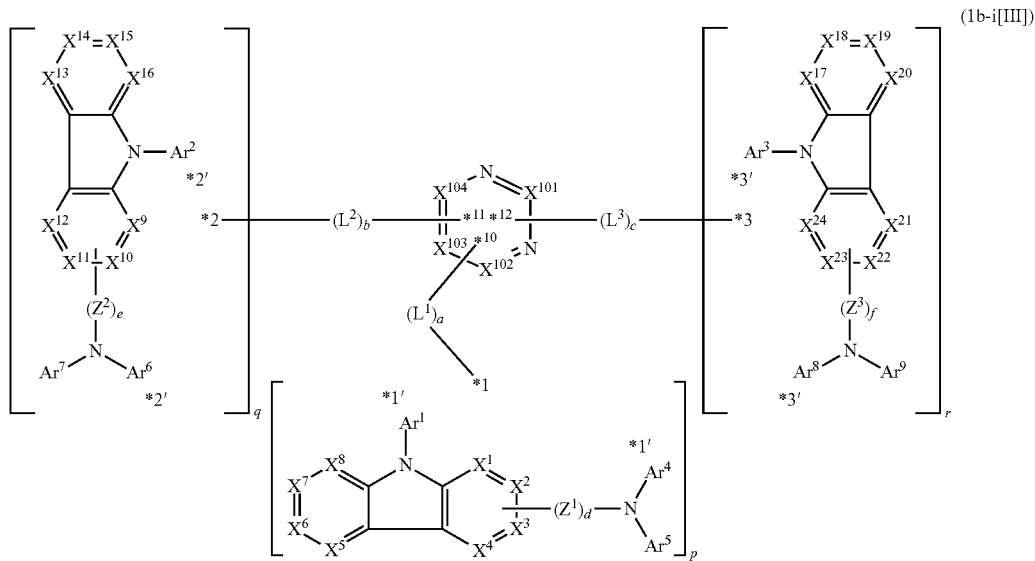

(1b-i[III])

in formula 1b-i[III], $L^1$ to $L^3$, a to f, p to r, $X^1$ to $X^{24}$, $Ar^1$ to $Ar^3$, $Ar^4$ to $Ar^9$, *1 to *3, *1' to *3', and preferred examples thereof are as described above in formula 1[III]; when p, q or r is 2 or 3, 2 or 3 groups in each [ ] may be the same or different; $X^{101}$ to $X^{104}$ each represent a carbon atom bonded to one of *10 to *12, C(Rx), or a nitrogen atom; Rx represents a hydrogen atom or a substituent; two or more groups Rx may be the same or different; and two selected from groups Rx may be bonded to each other to form a ring;

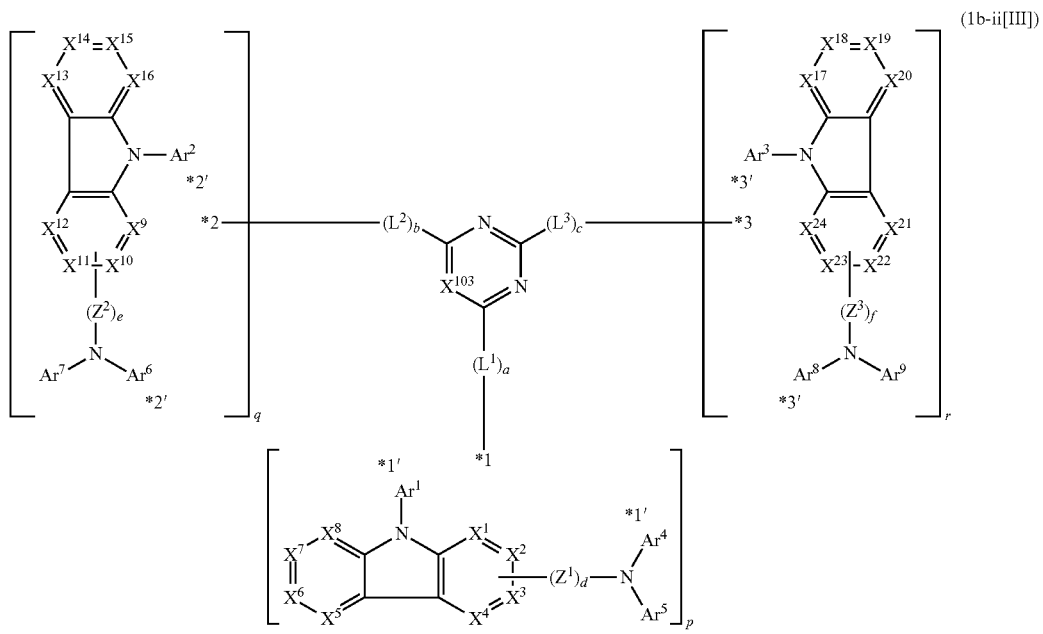

(1b-ii[III])

in formula 1b-ii[III], $L^1$ to $L^3$, a to f, p to r, $X^1$ to $X^{24}$, $Ar^1$ to $Ar^3$, $Ar^4$ to $Ar^9$, *1 to *3, *1' to *3', and preferred examples thereof are as described above in formula 1[III]; when p, q or r is 2 or 3, 2 or 3 groups in each [ ] may be the same or different; $X^{103}$ represents C(Rx) or a nitrogen atom; and Rx represents a hydrogen atom or a substituent;

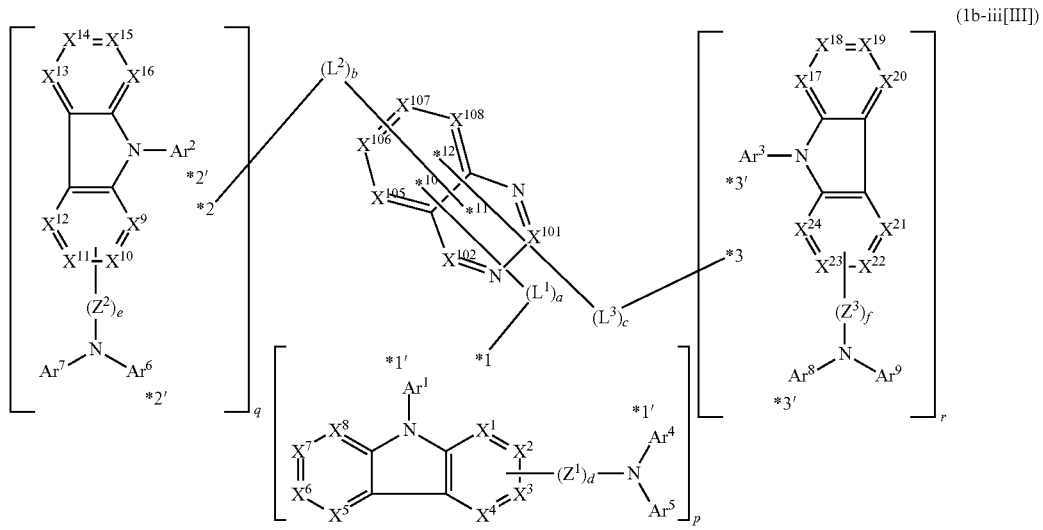

(1b-iii[III])

in formula 1b-iii[III], $L^1$ to $L^3$, a to f, p to r, $X^1$ to $X^{24}$, $Ar^1$ to $Ar^3$, $Ar^4$ to $Ar^9$, *1 to *3, *1' to *3', and preferred examples thereof are as described above in formula 1[III]; when p, q or r is 2 or 3, 2 or 3 groups in each [ ] may be the same or different; $X^{101}$, $X^{102}$, and $X^{105}$ to $X^{108}$ each represent a carbon atom bonded to one of *10 to *12, C(Rx), or a nitrogen atom; Rx represents a hydrogen atom or a substituent; two or more groups Rx may be the same or different; and two selected from groups Rx may be bonded to each other to form a ring; and

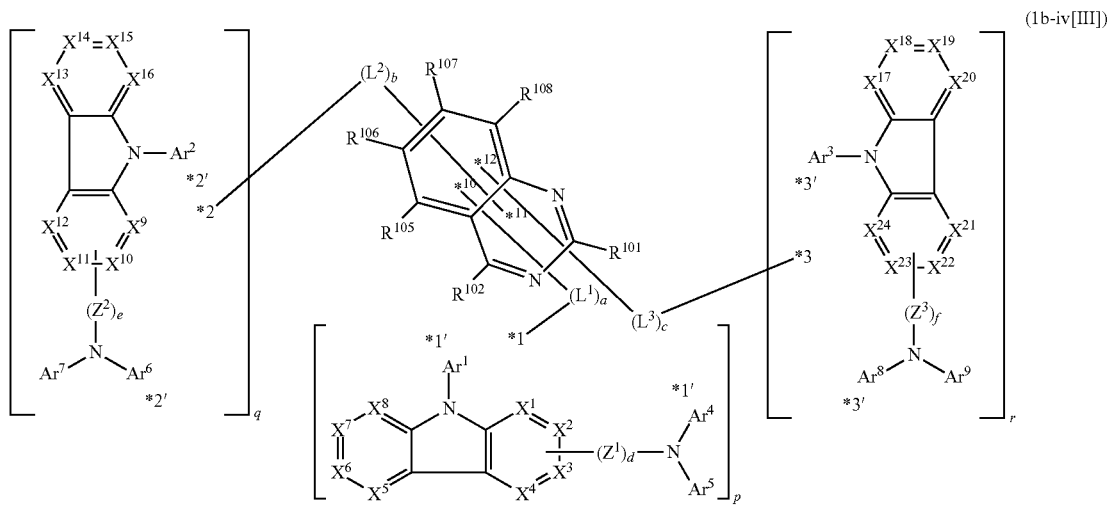

(1b-iv[III])

in formula 1b-iv[III], $L^1$ to $L^3$, a to f, p to r, $X^1$ to $X^{24}$, $Ar^1$ to $Ar^3$, $Ar^4$ to $Ar^9$, *1 to *3, *1' to *3', and preferred examples thereof are as described above in formula [III]; when p, q or r is 2 or 3, 2 or 3 groups in each [ ] may be the same or different; 1 to 3 carbon atoms from which one to three selected from $R^{101}$, $R^{102}$, and $R^{105}$ to $R^{108}$ are removed are each bonded to one of *10 to *12, and the others each independently represent a hydrogen atom or a substituent; and two selected from $R^{102}$ and $R^{105}$ to $R^{108}$ may be bonded to each other to form a ring.

Examples of compound 1[III] in an aspect of the invention are shown below, although not limited there to.
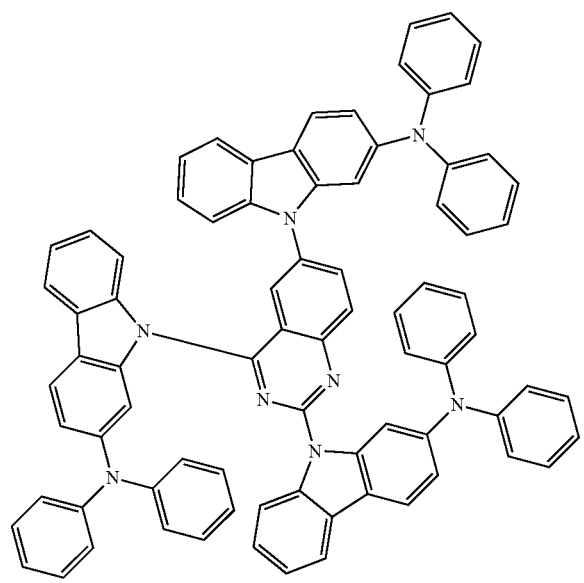
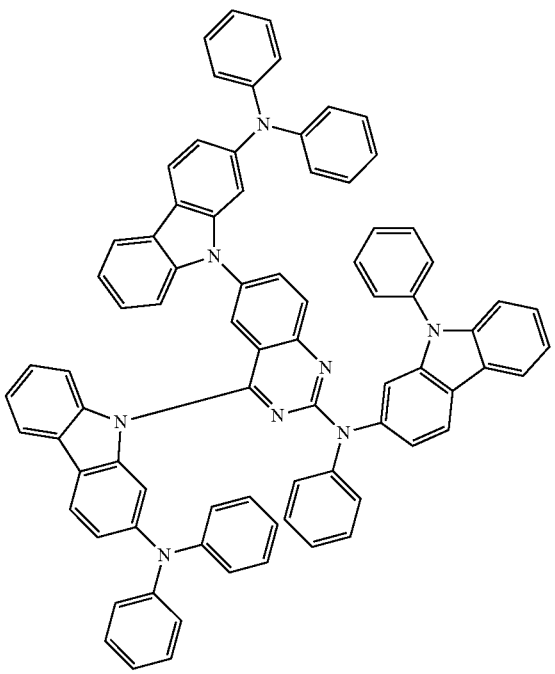
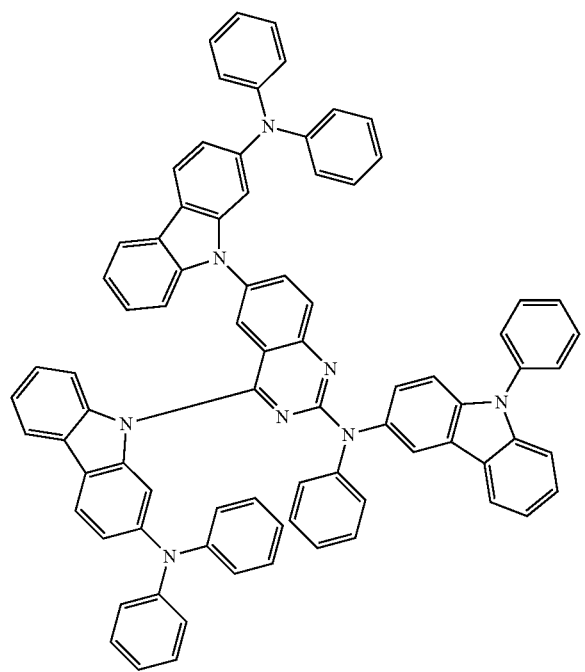
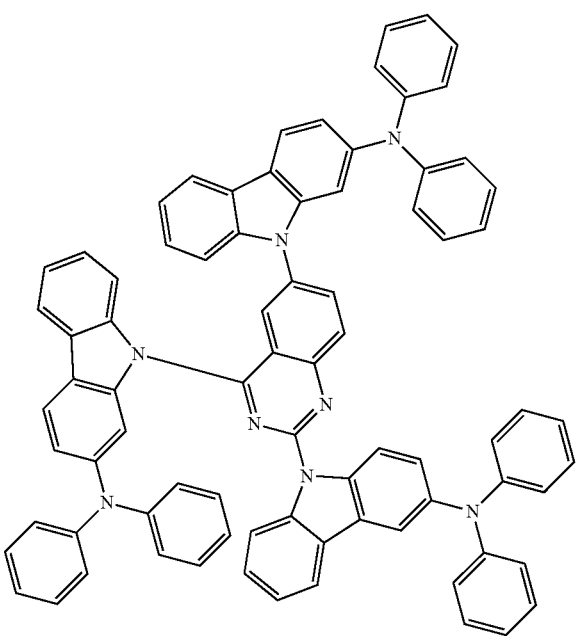

1007
-continued
1008
-continued
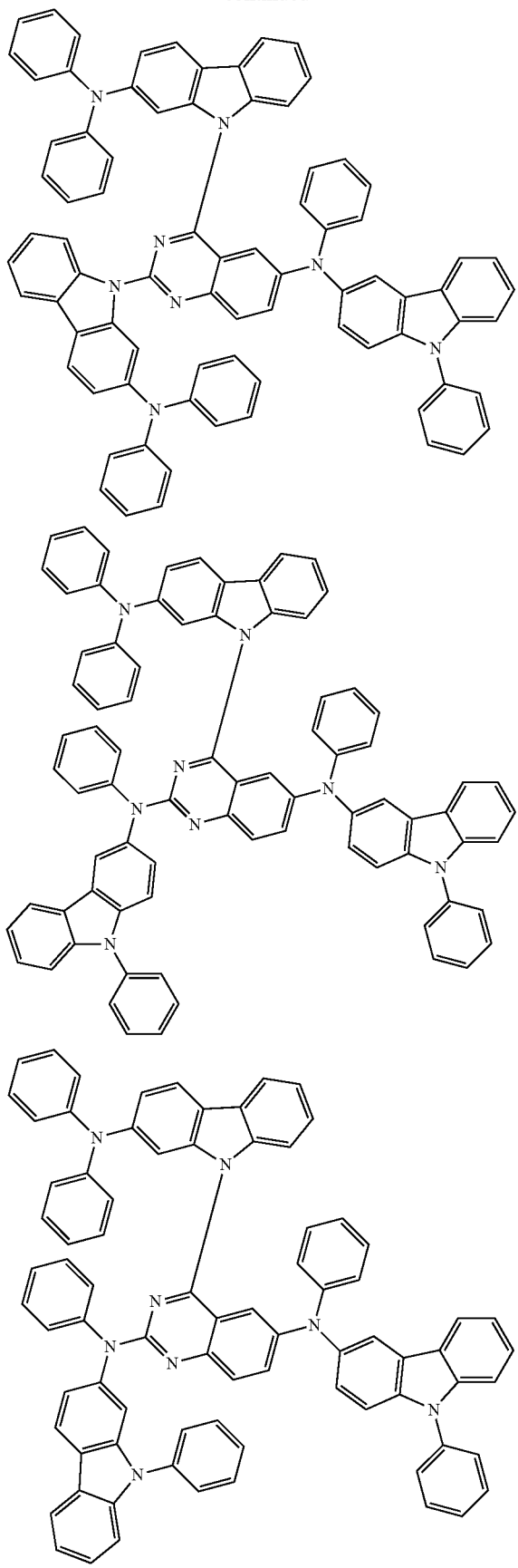
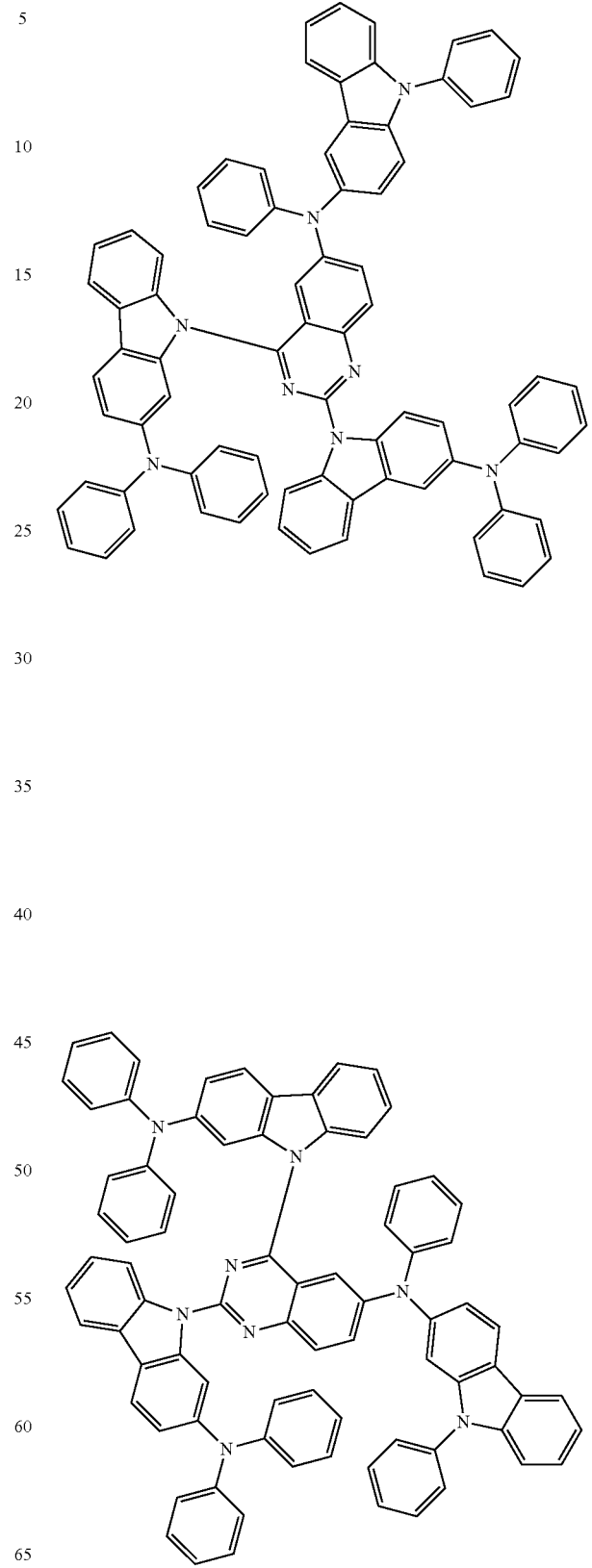

1009
-continued
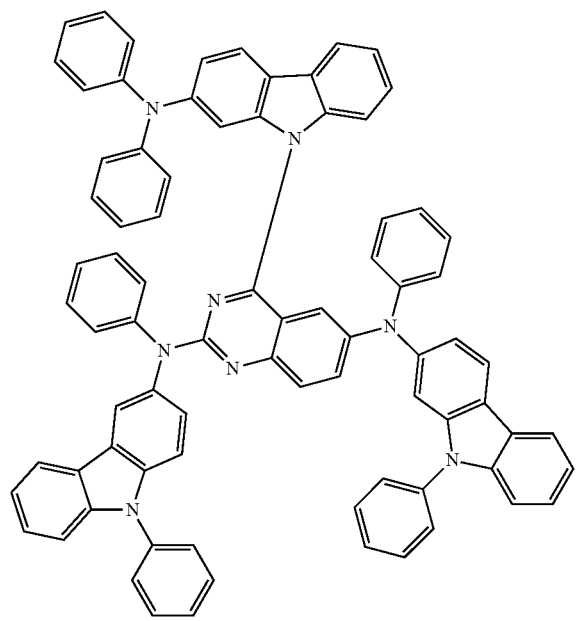
1010
-continued
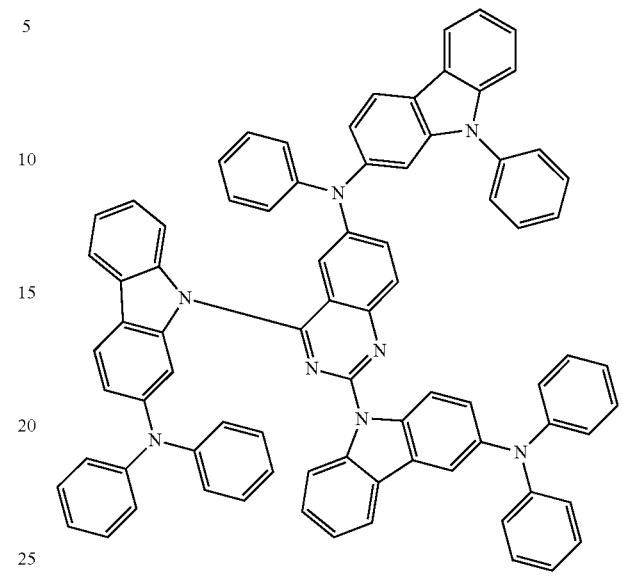
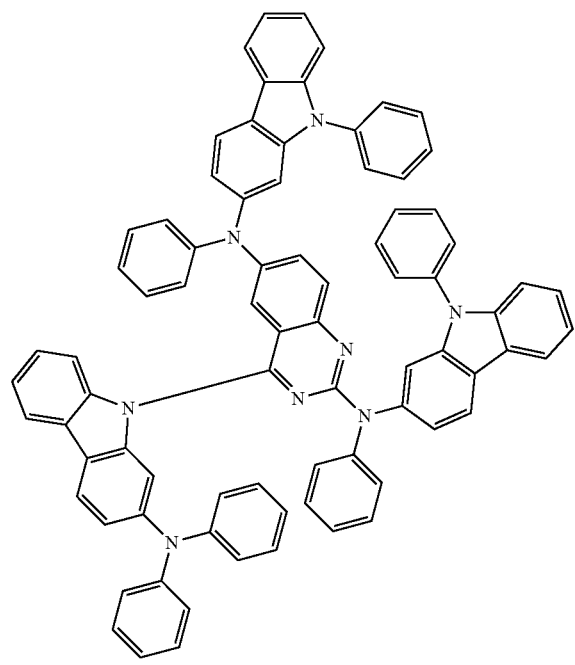
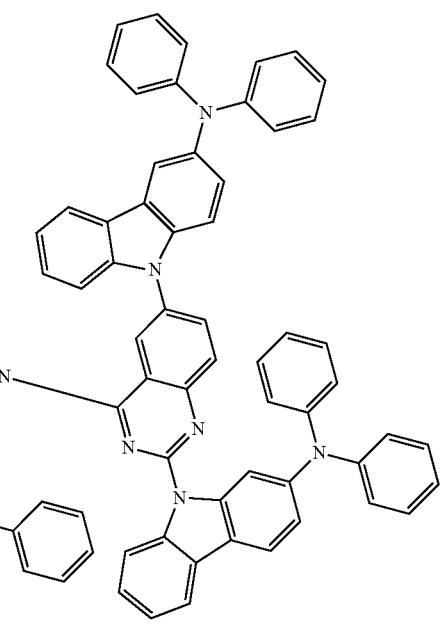

1011
-continued
1012
-continued
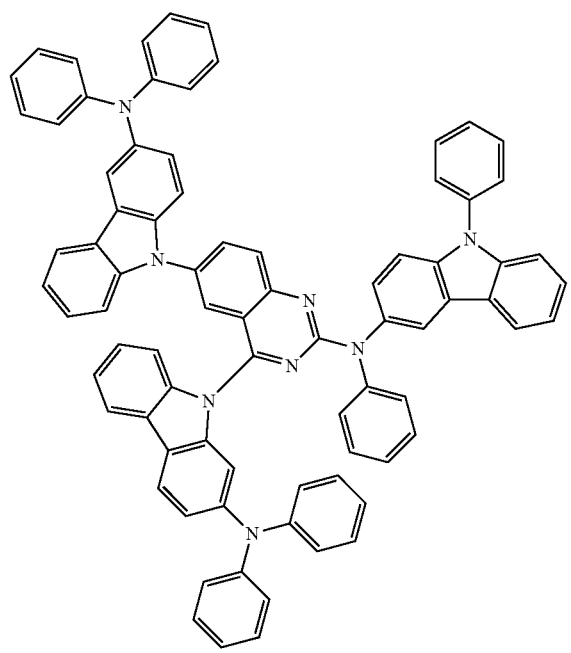
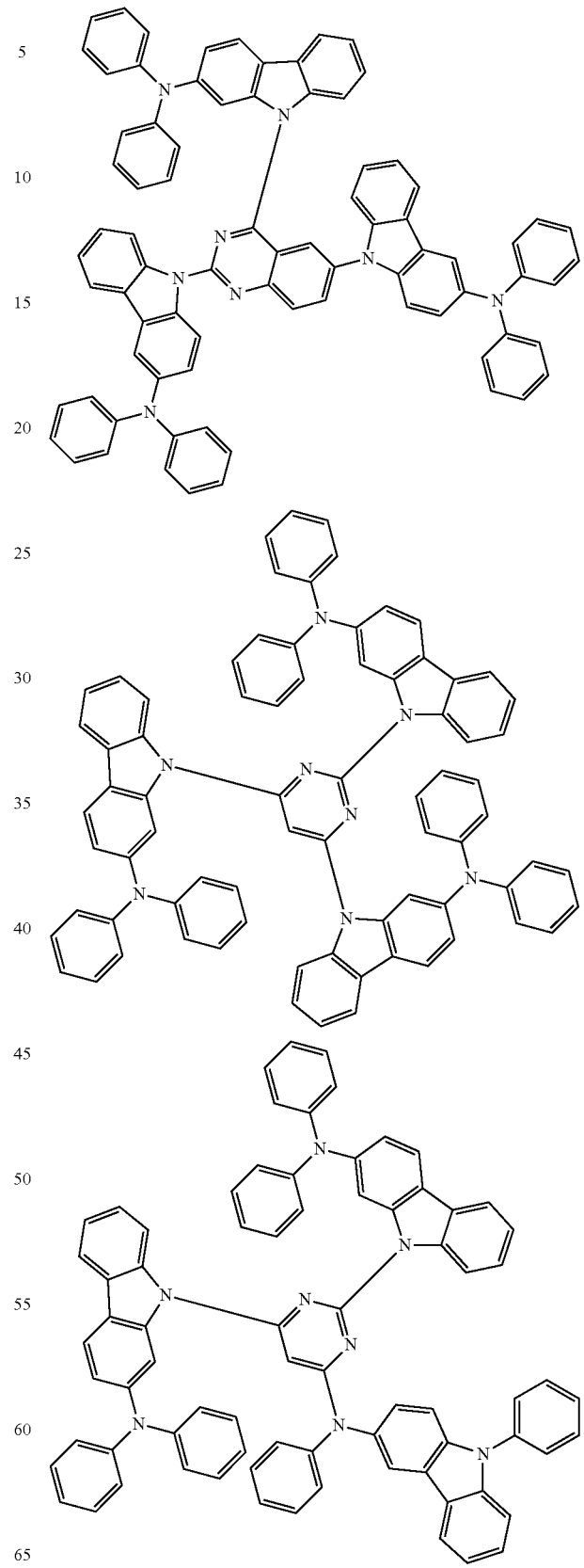

1013
-continued
1014
-continued
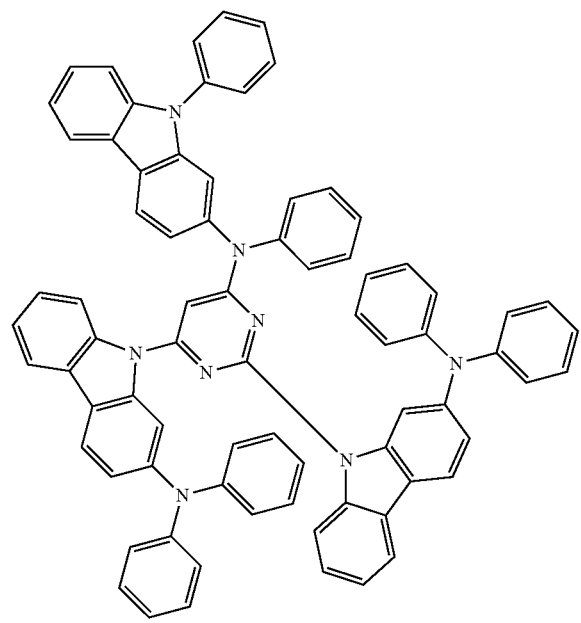
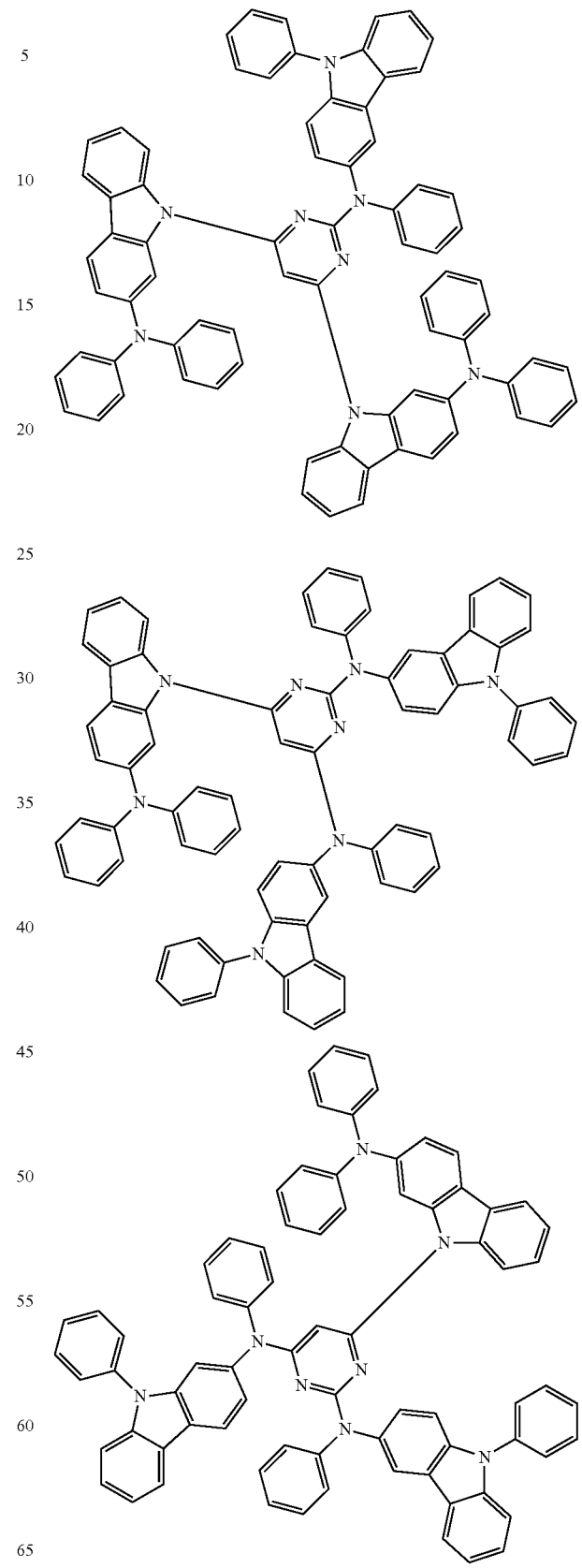

1015
-continued
1016
-continued
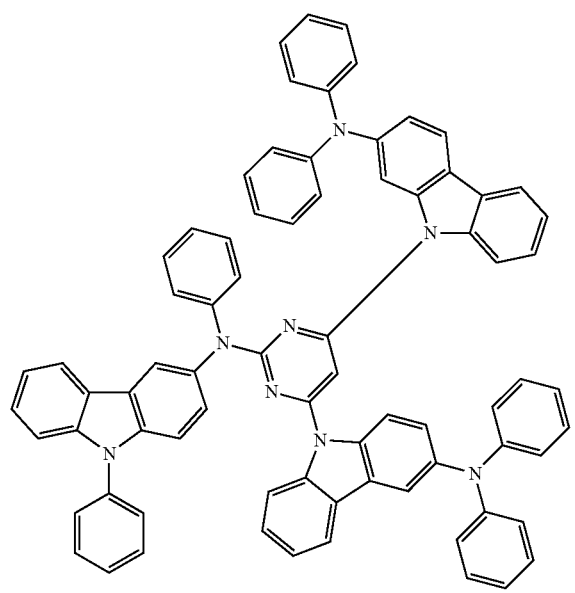
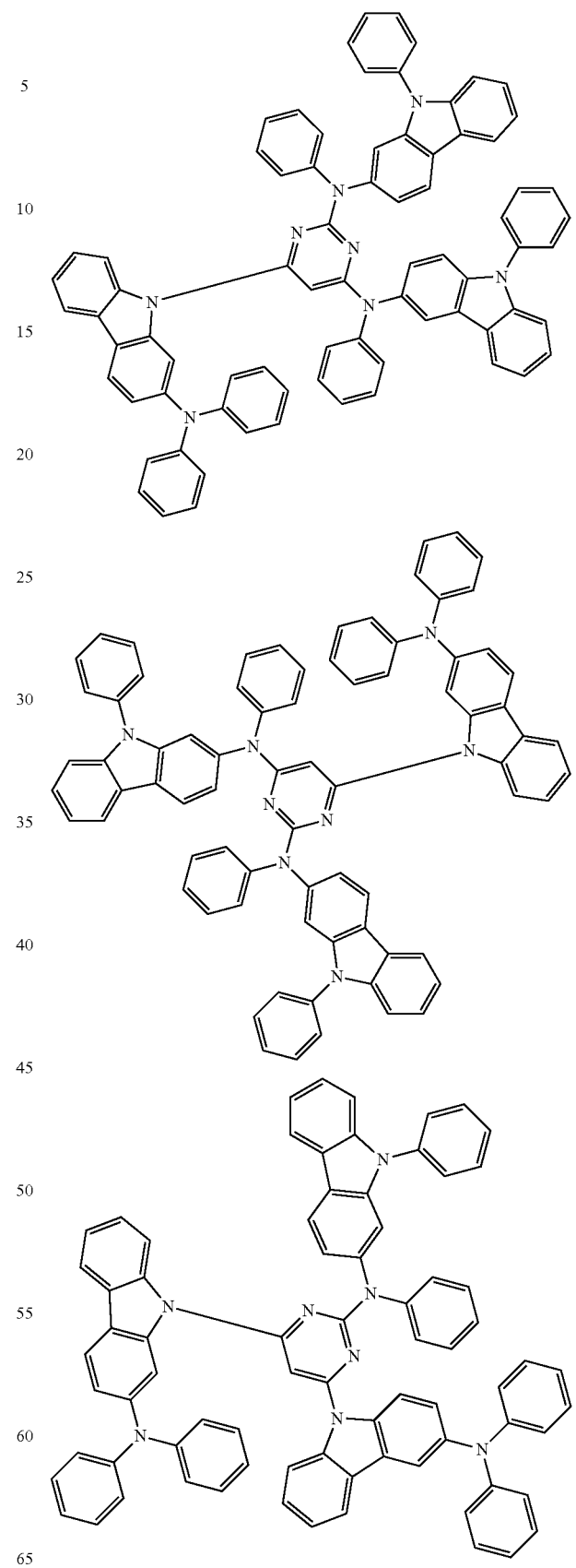

1017
-continued
1018
-continued
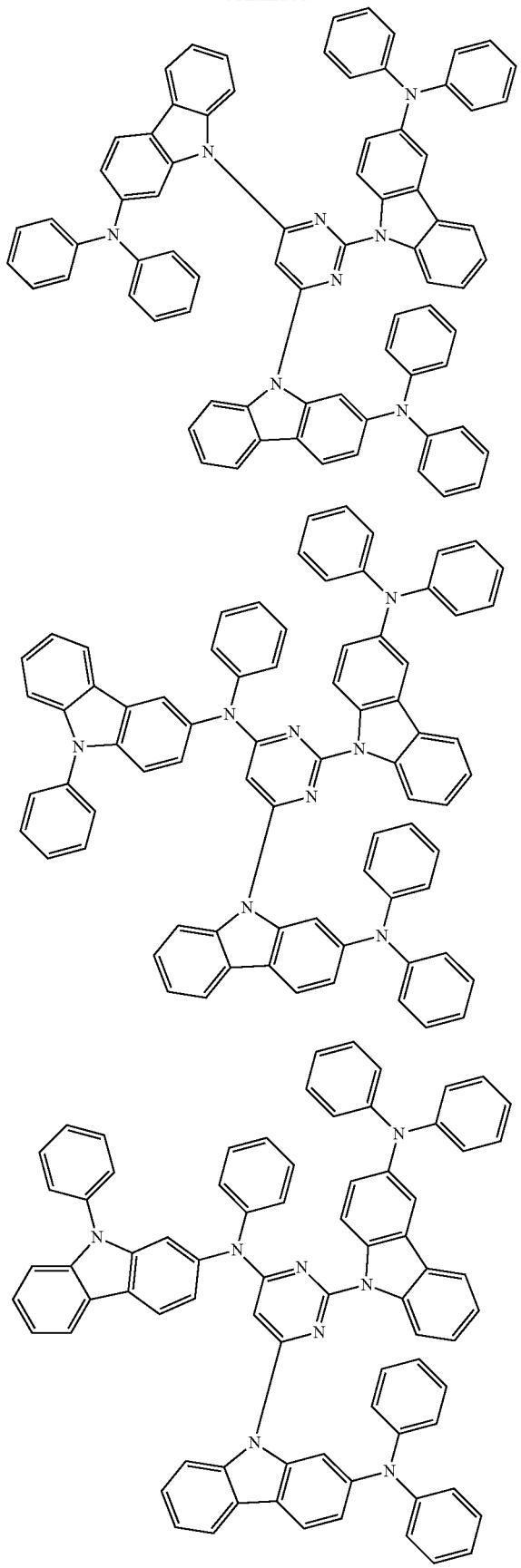
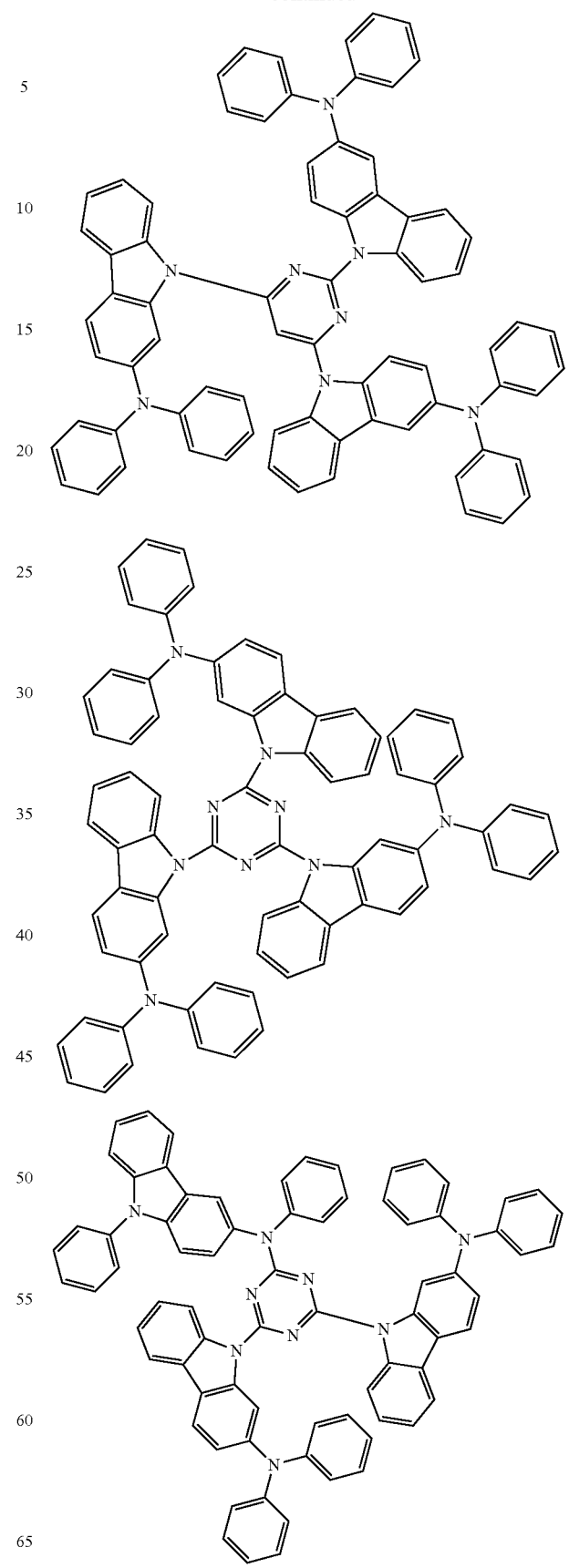

1019
-continued
1020
-continued
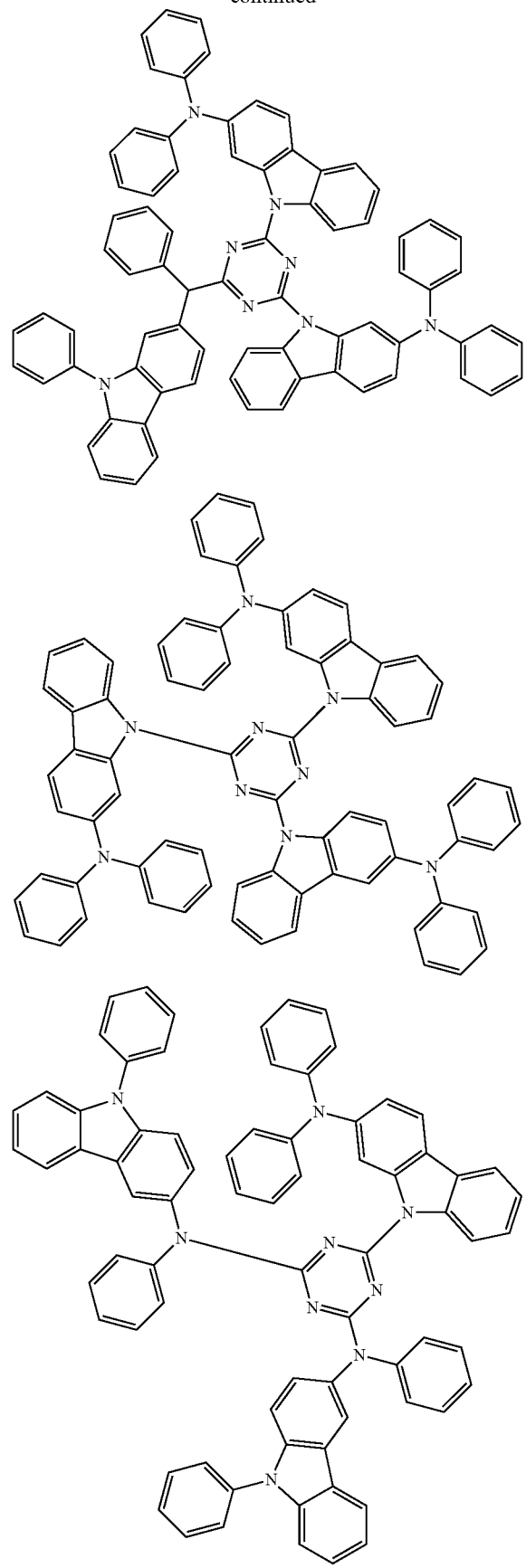
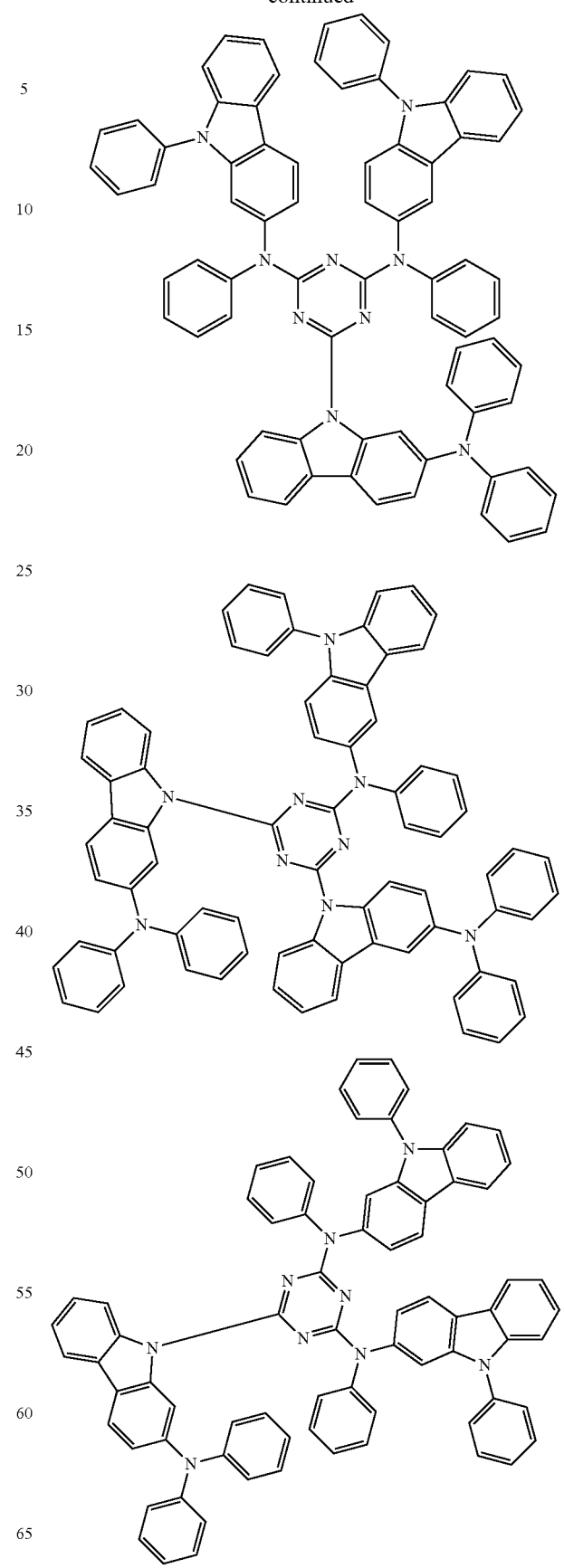

1021
-continued
1022
-continued
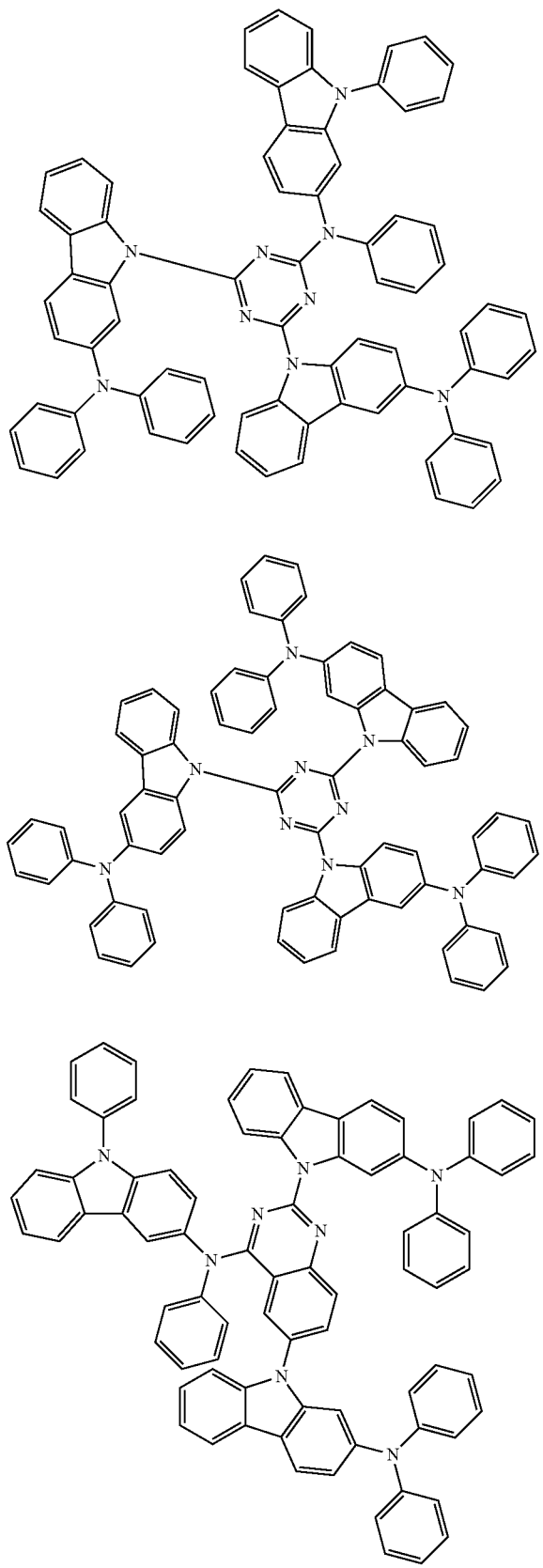
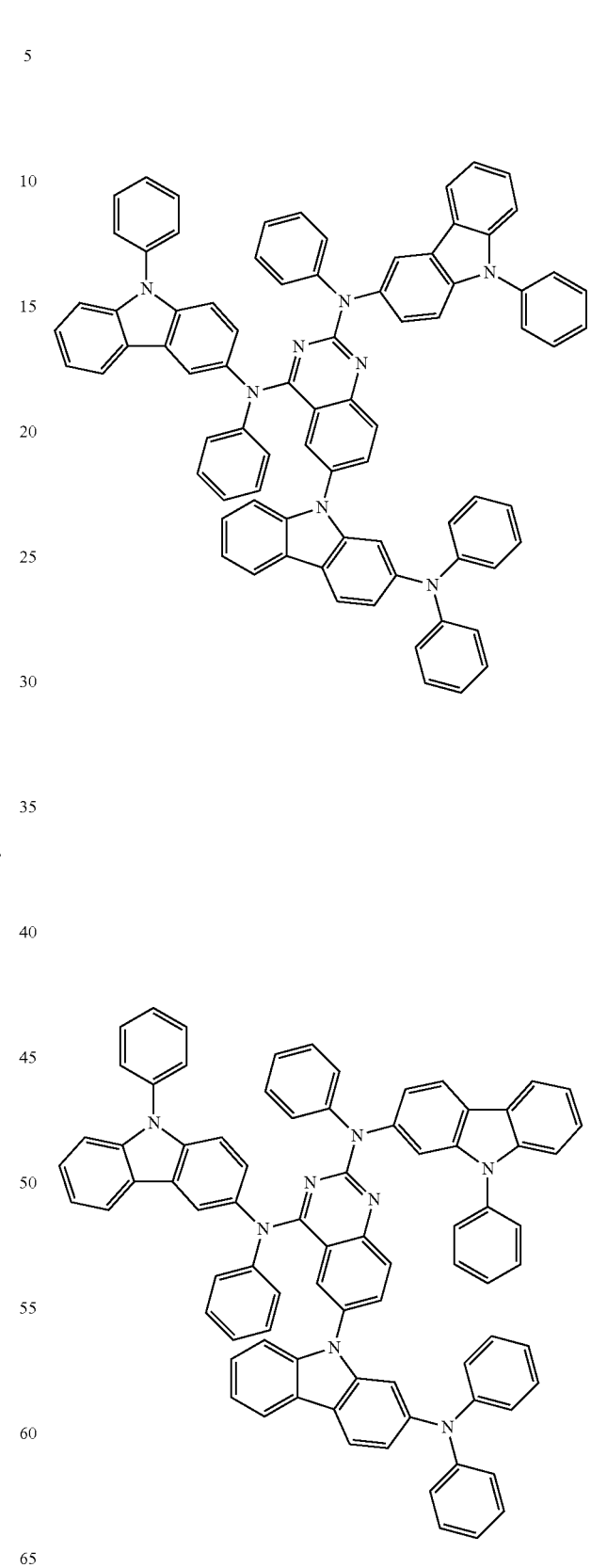

1023
-continued
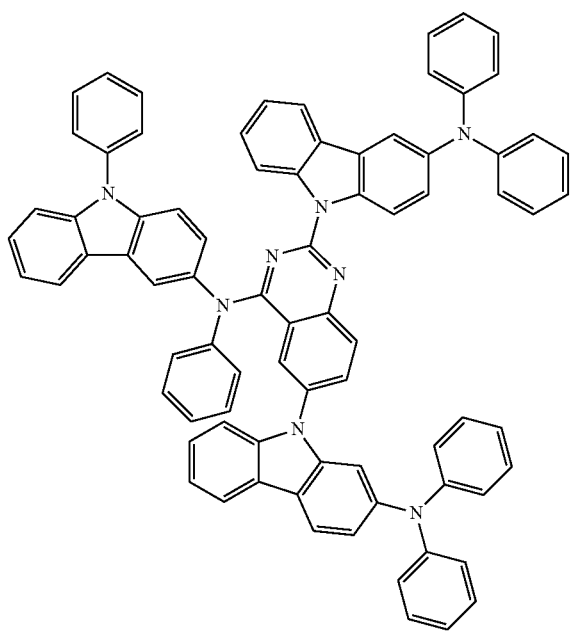
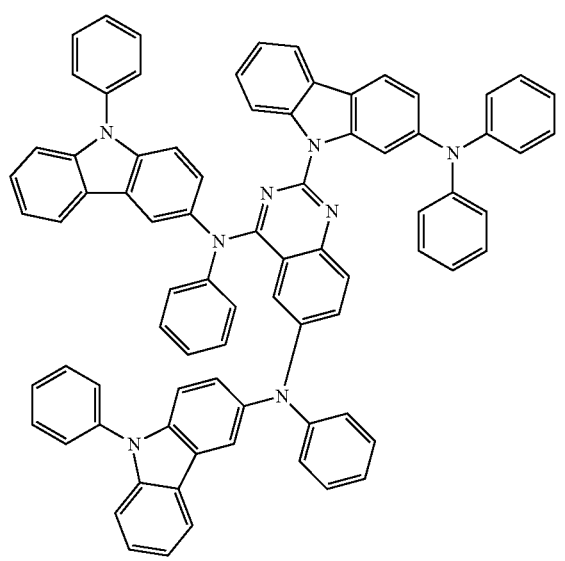
1024
-continued
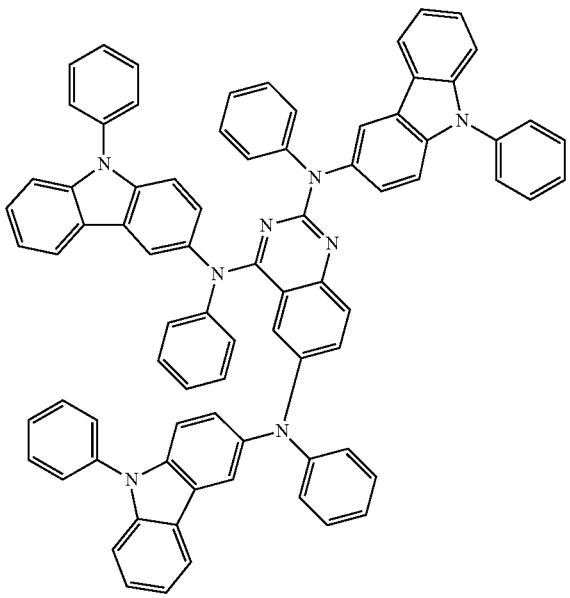
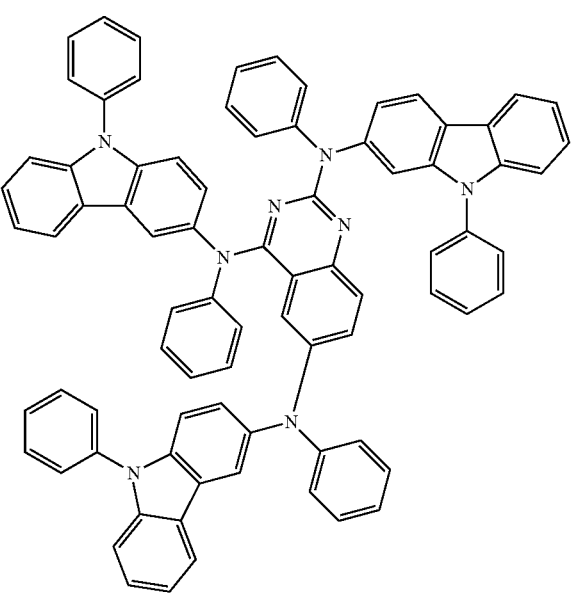

1025
-continued
1026
-continued
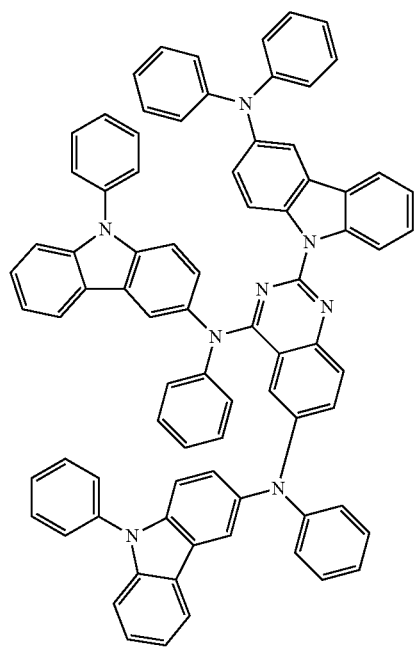
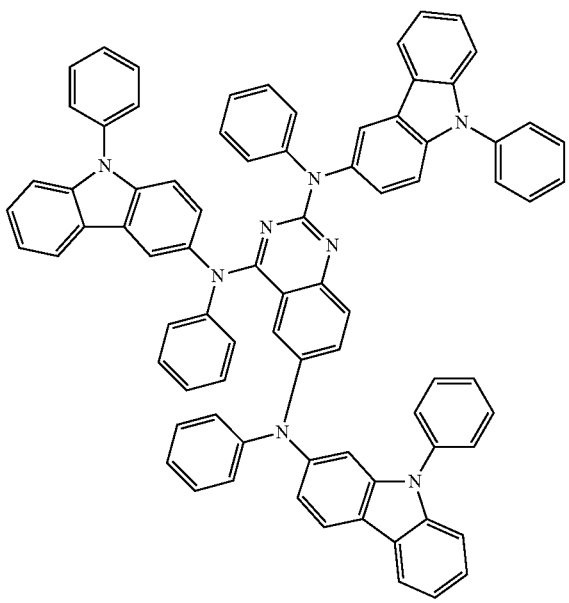
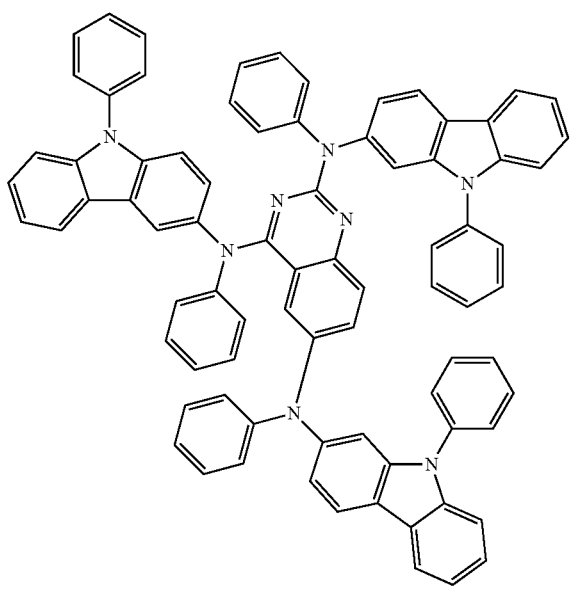

1027
-continued
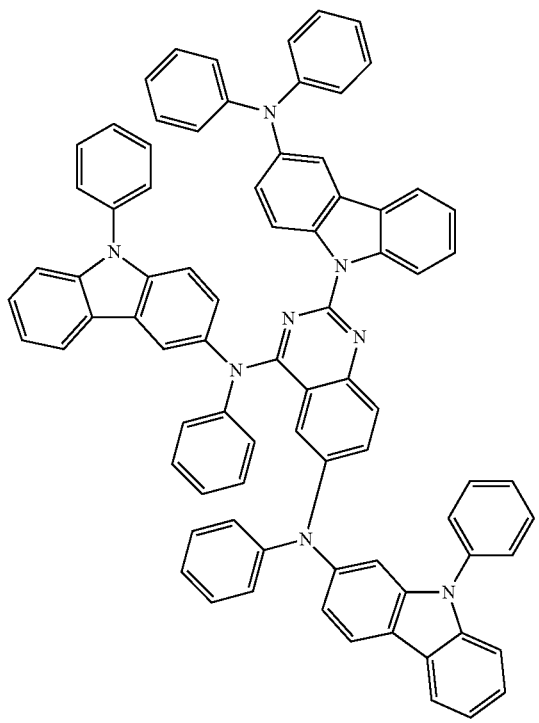
1028
-continued
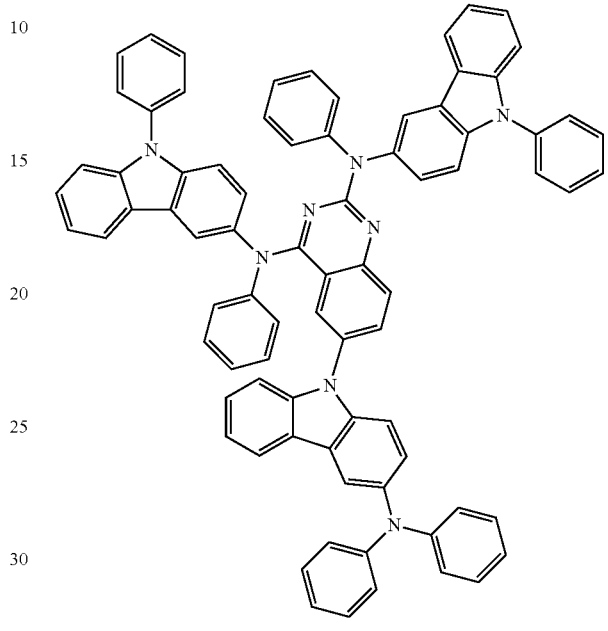
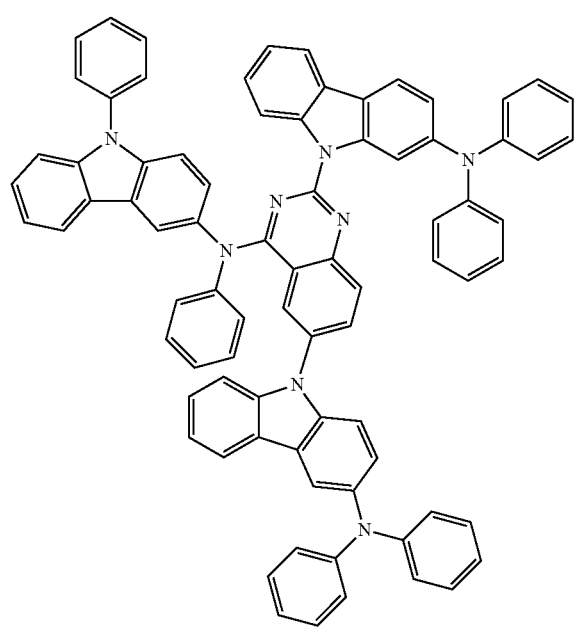
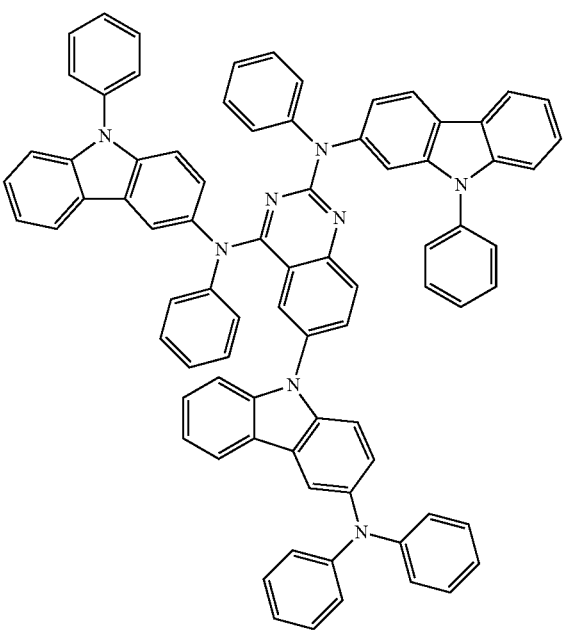

1029
-continued
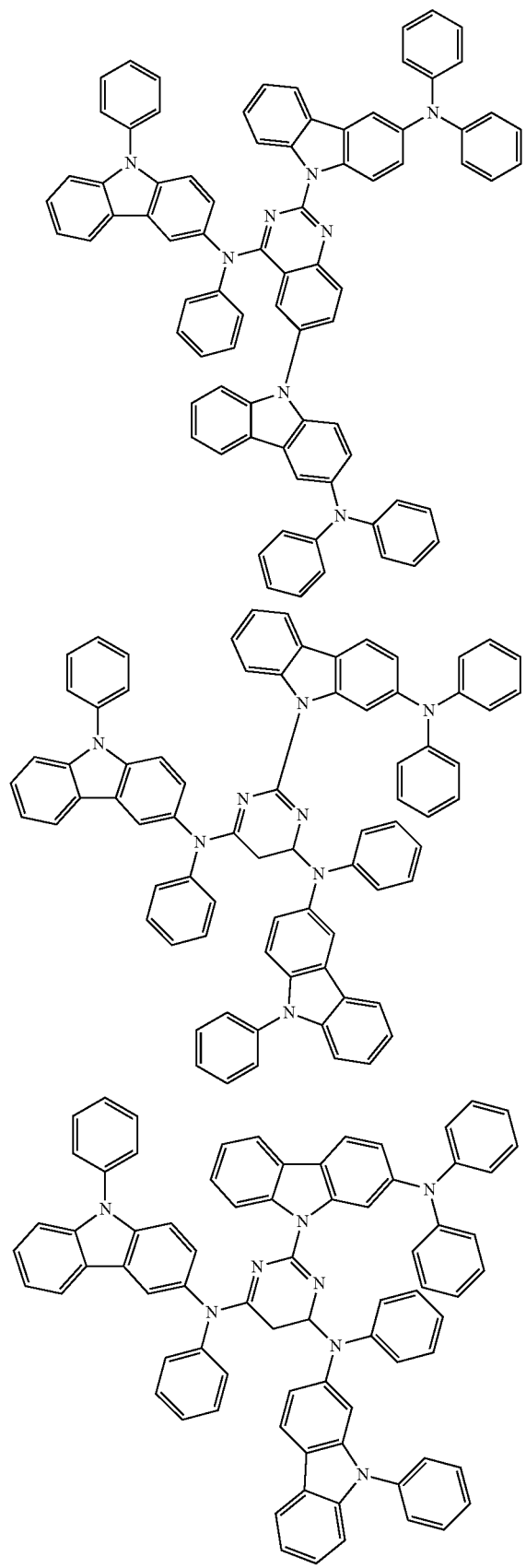
1030
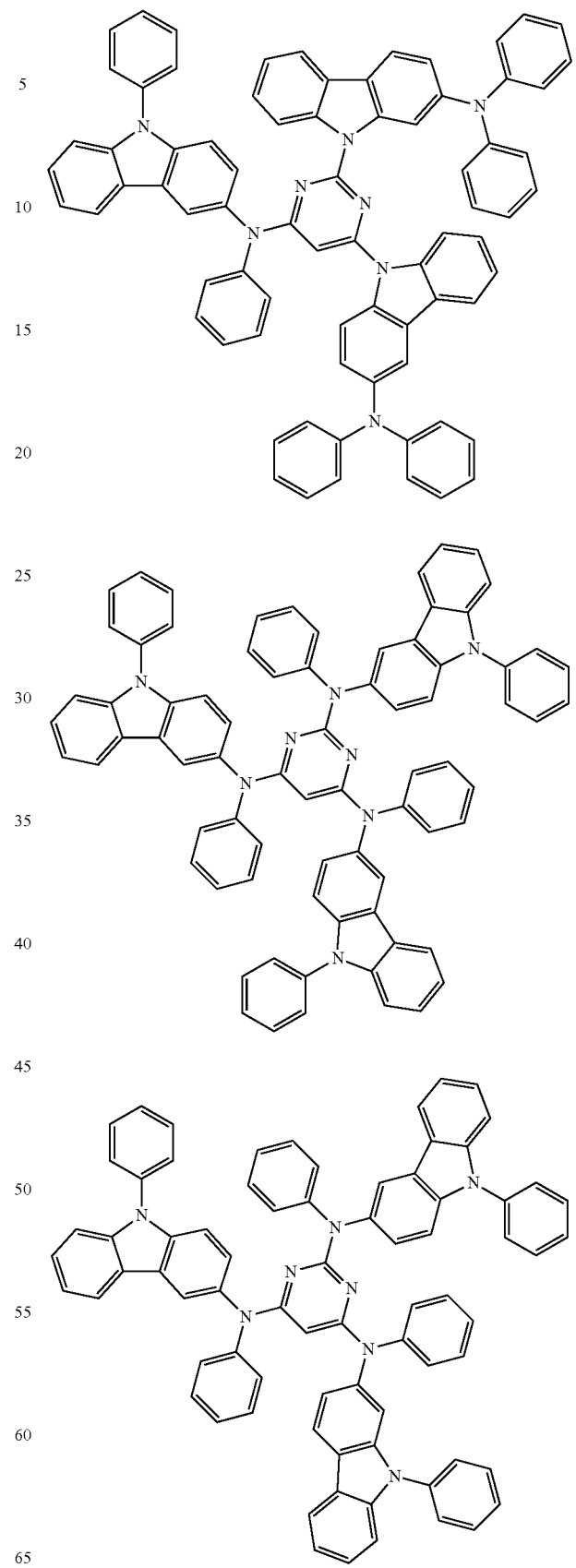

1031
-continued
1032
-continued
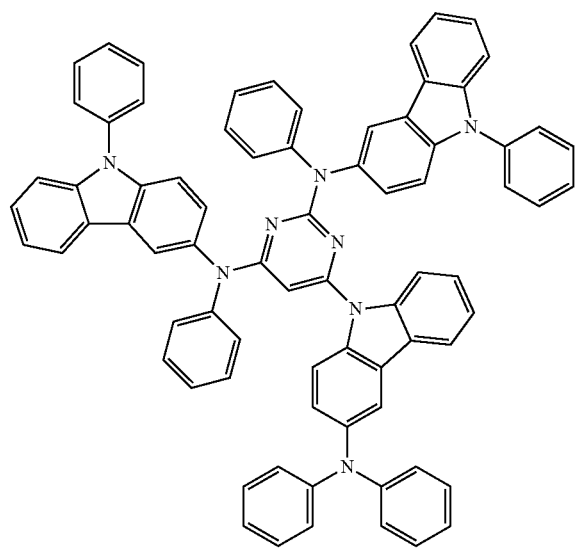
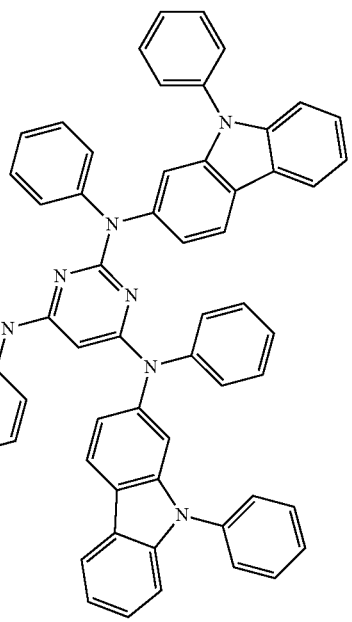
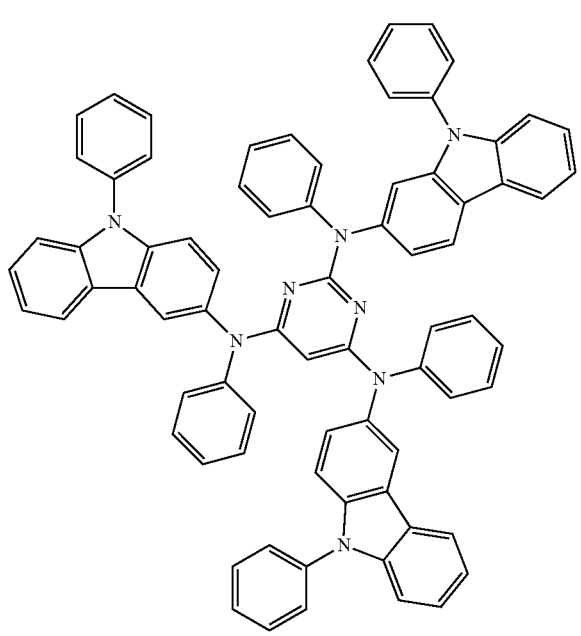
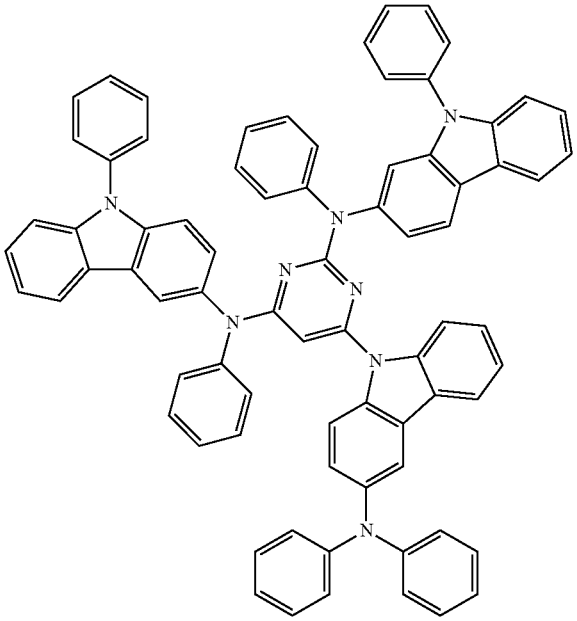

1033
-continued
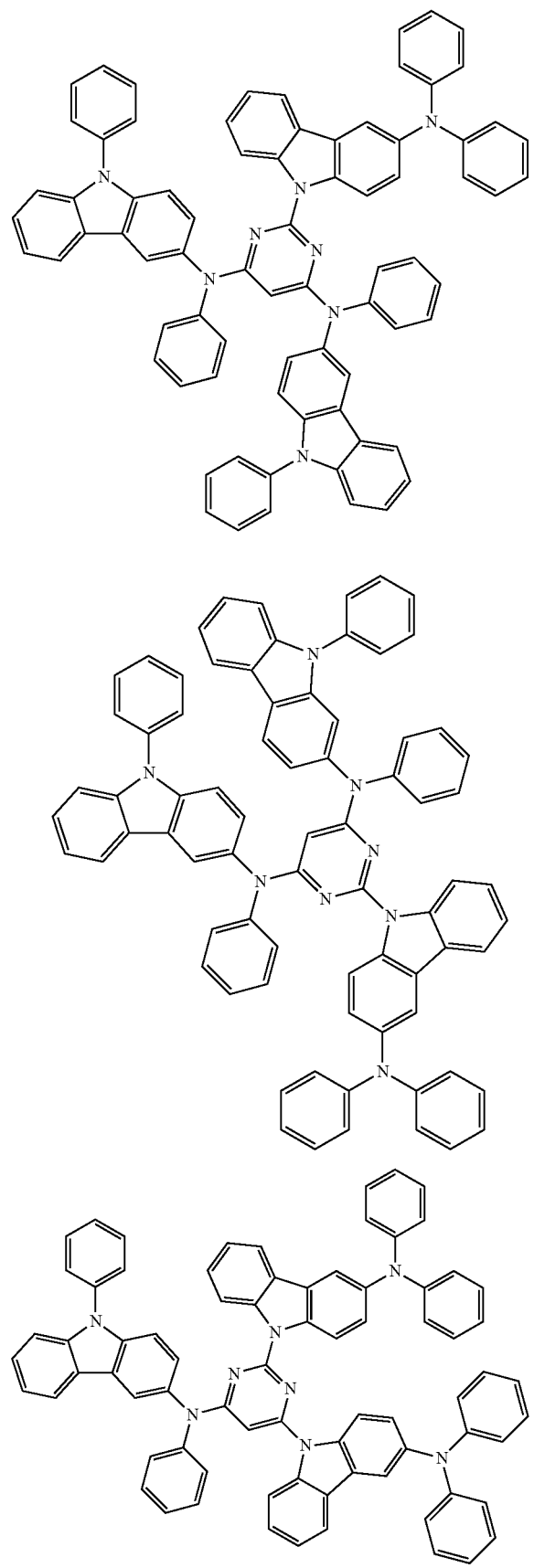
1034
-continued
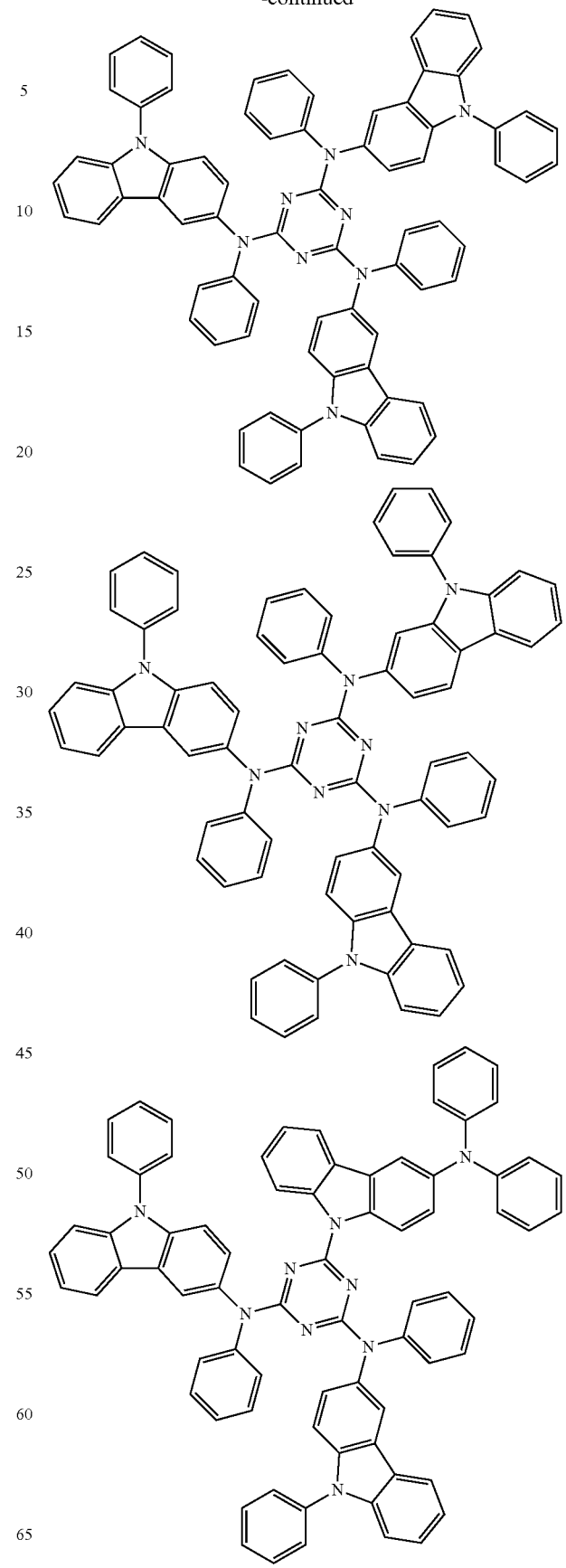

1035
-continued
1036
-continued
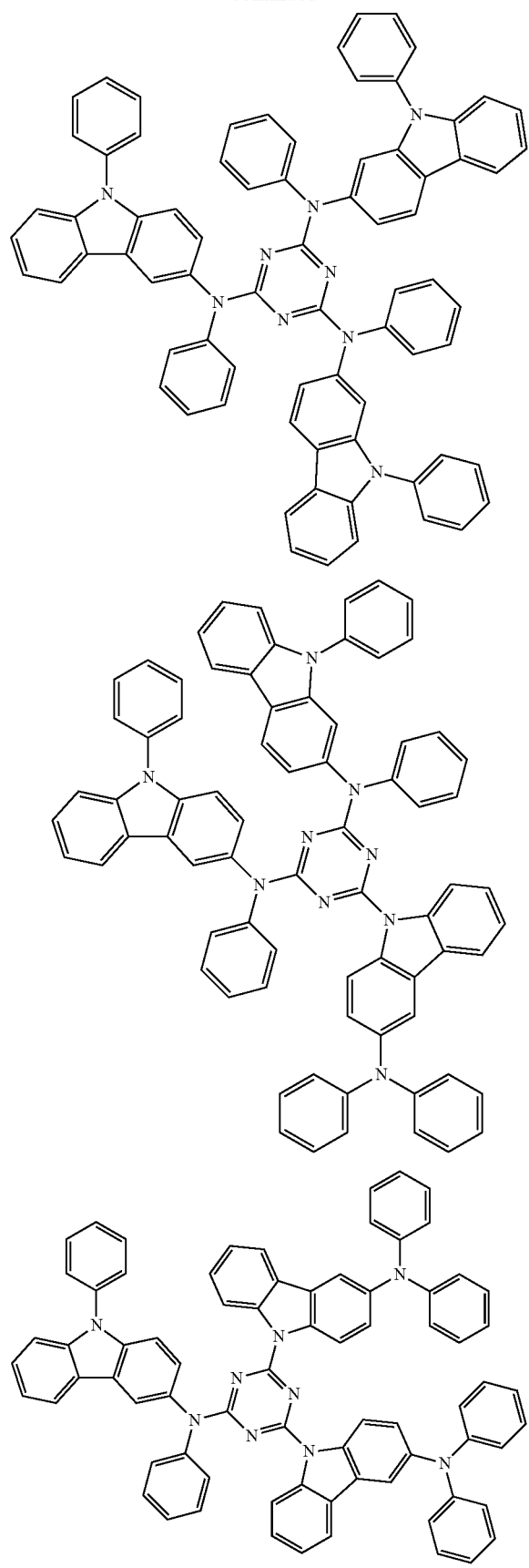
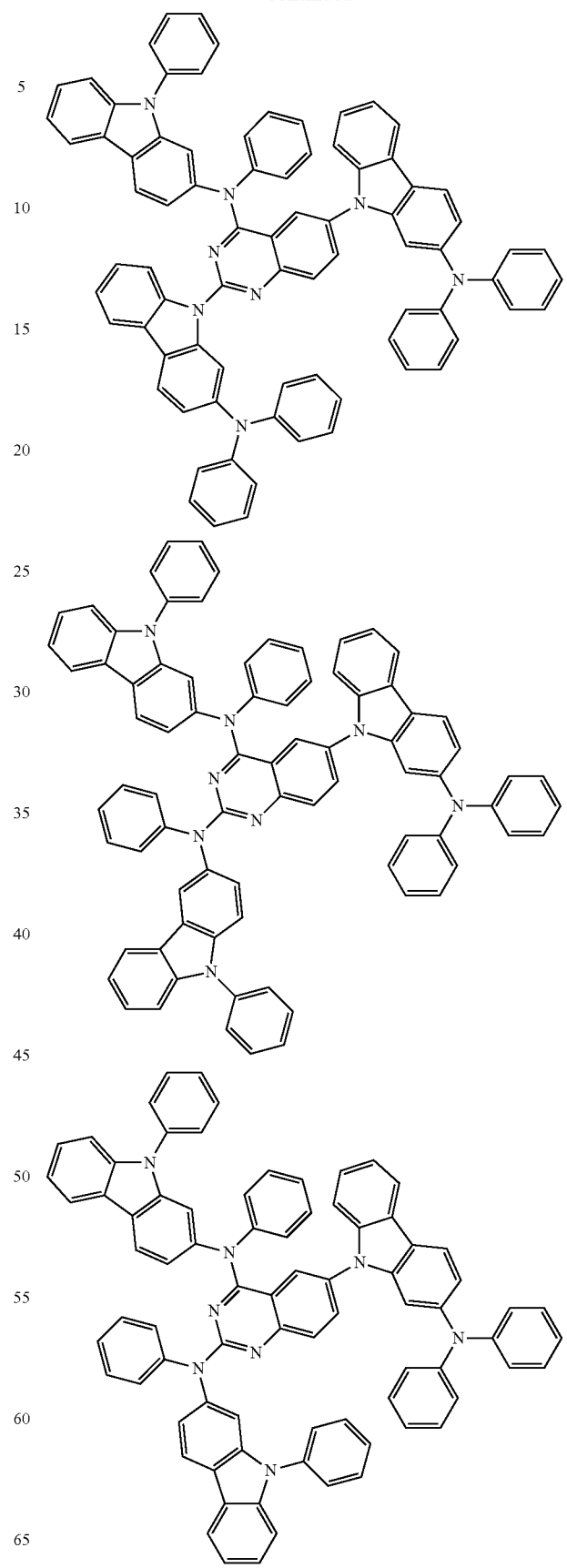

1037
-continued
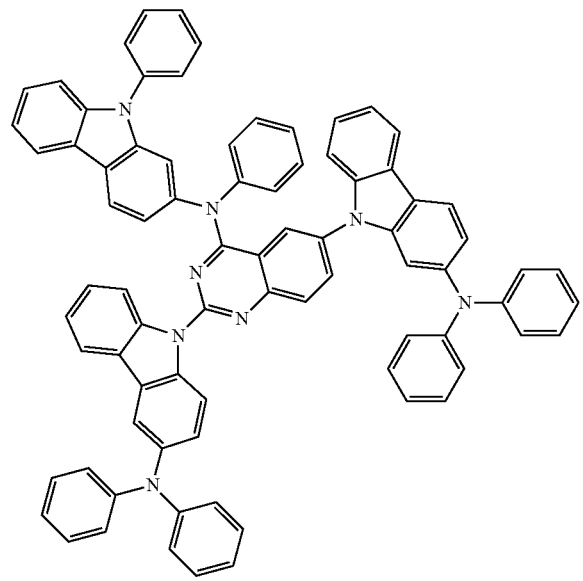
1038
-continued
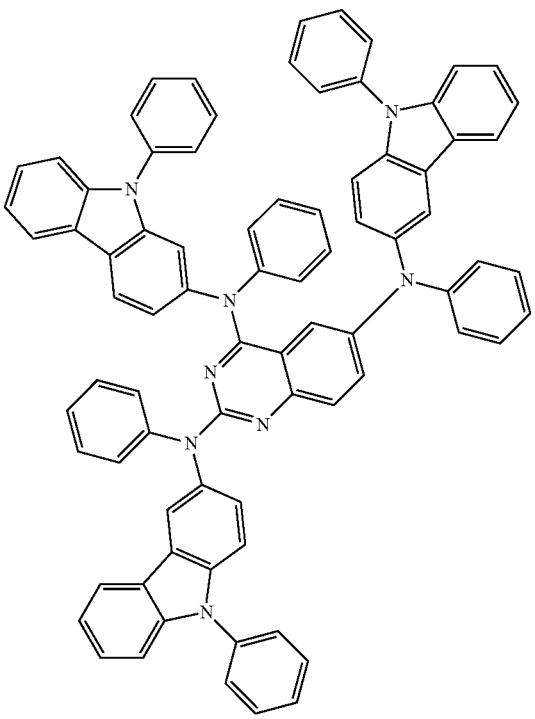
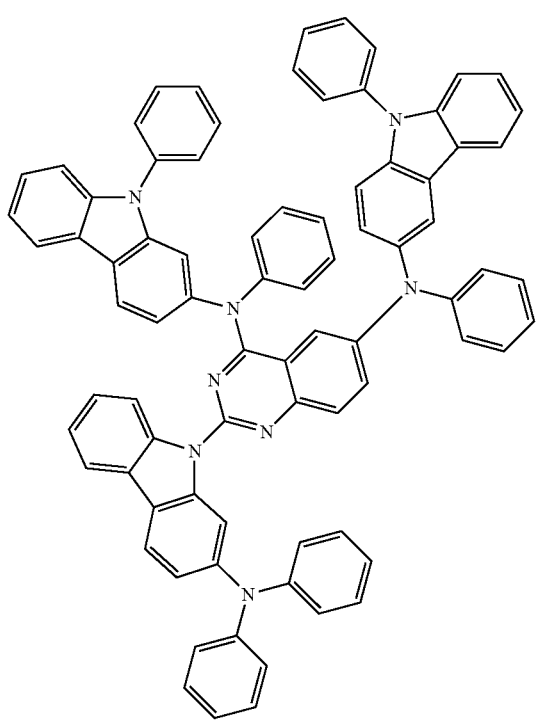
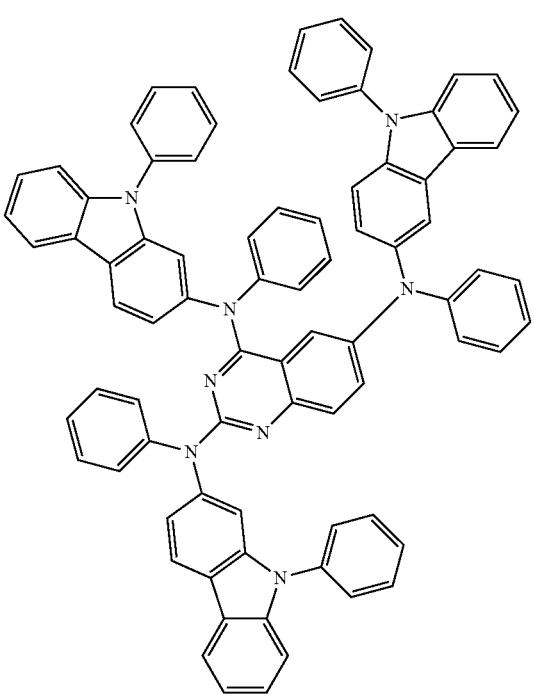

1039
-continued
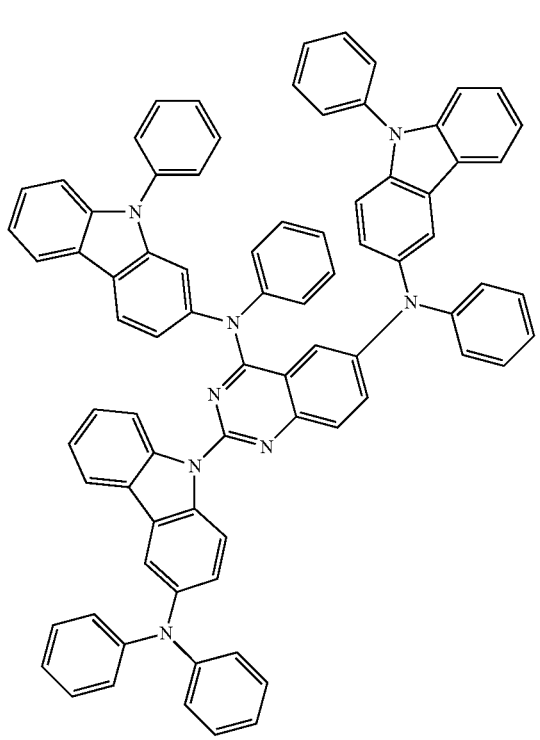
1040
-continued
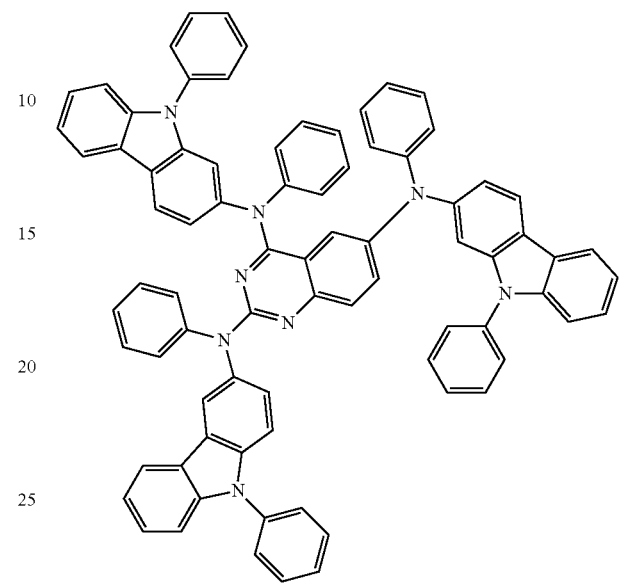
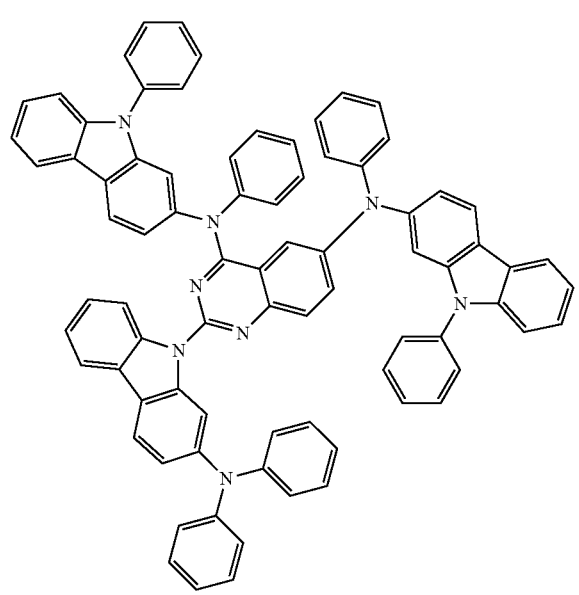
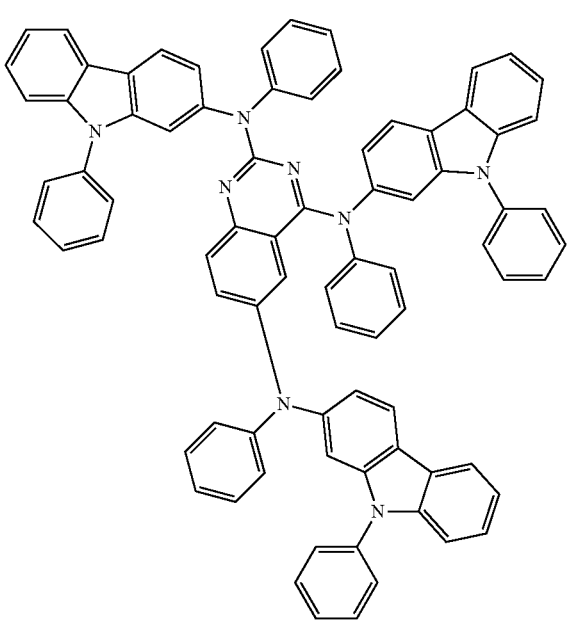

1041
-continued
1042
-continued
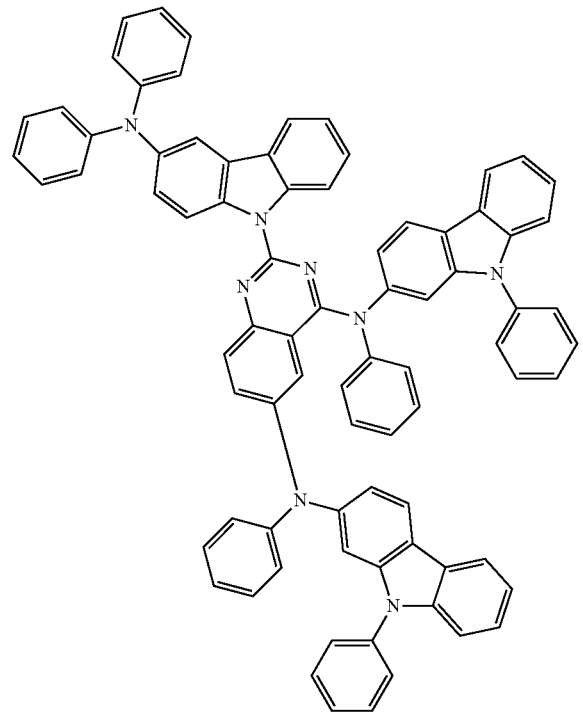
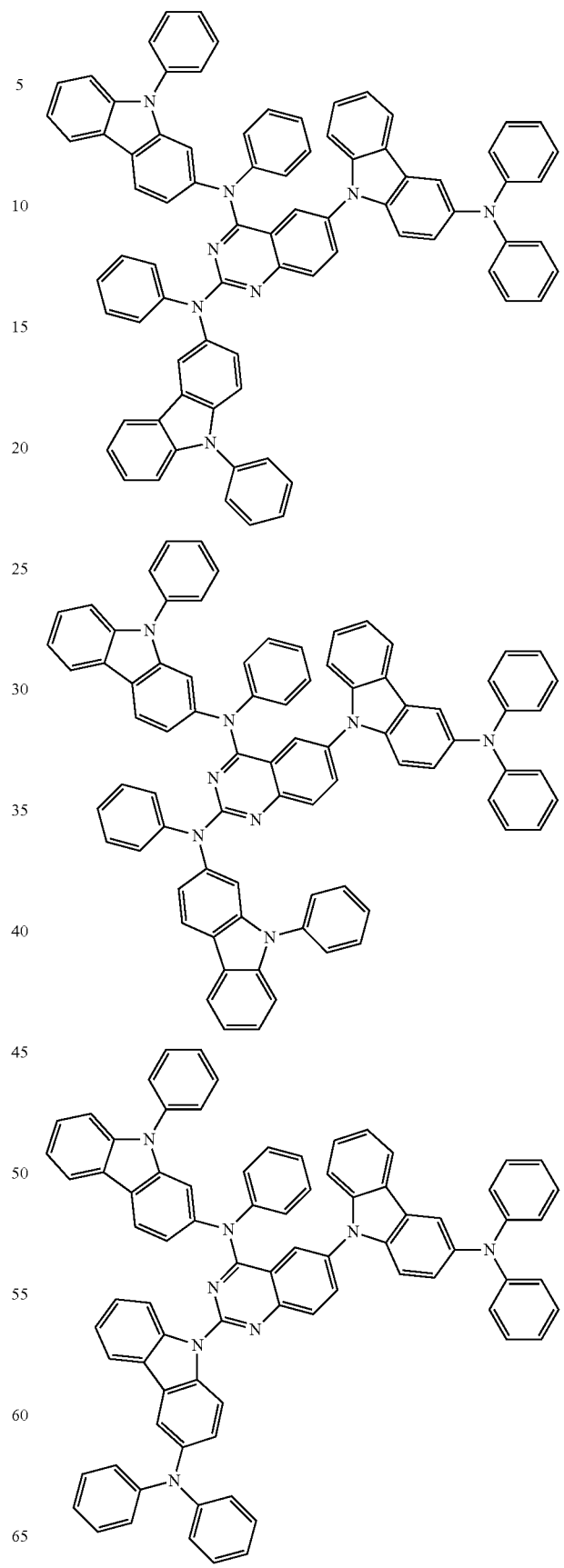

1043
-continued
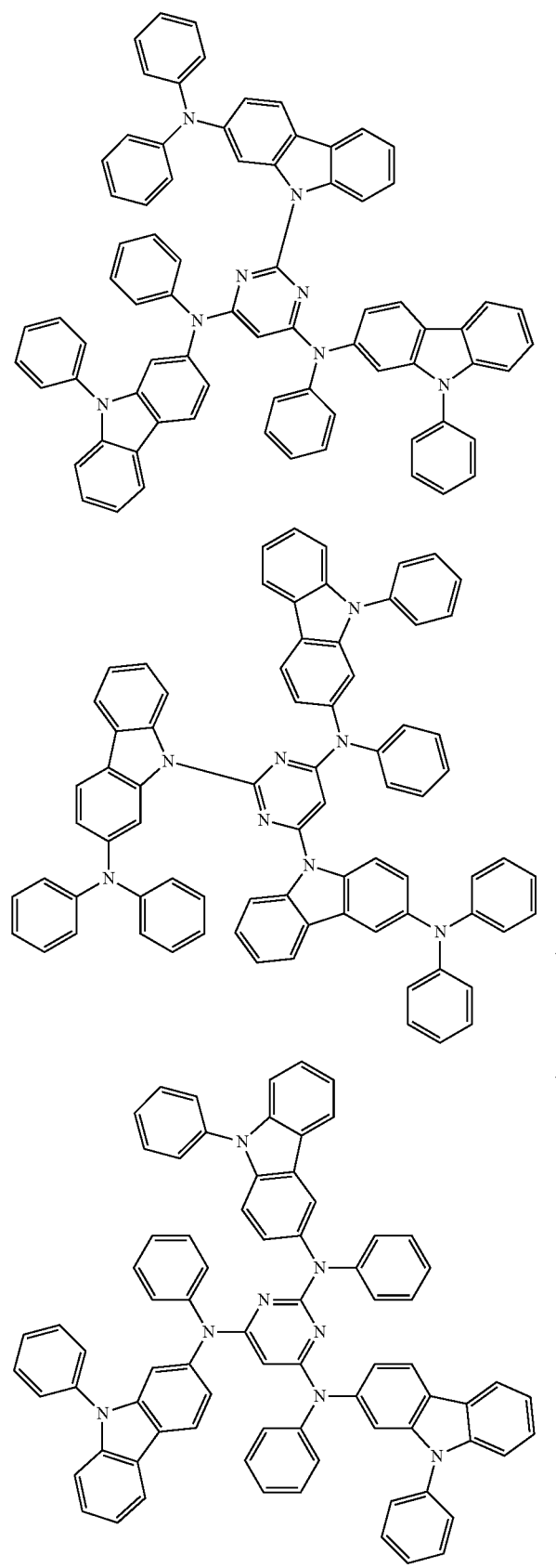
1044
-continued
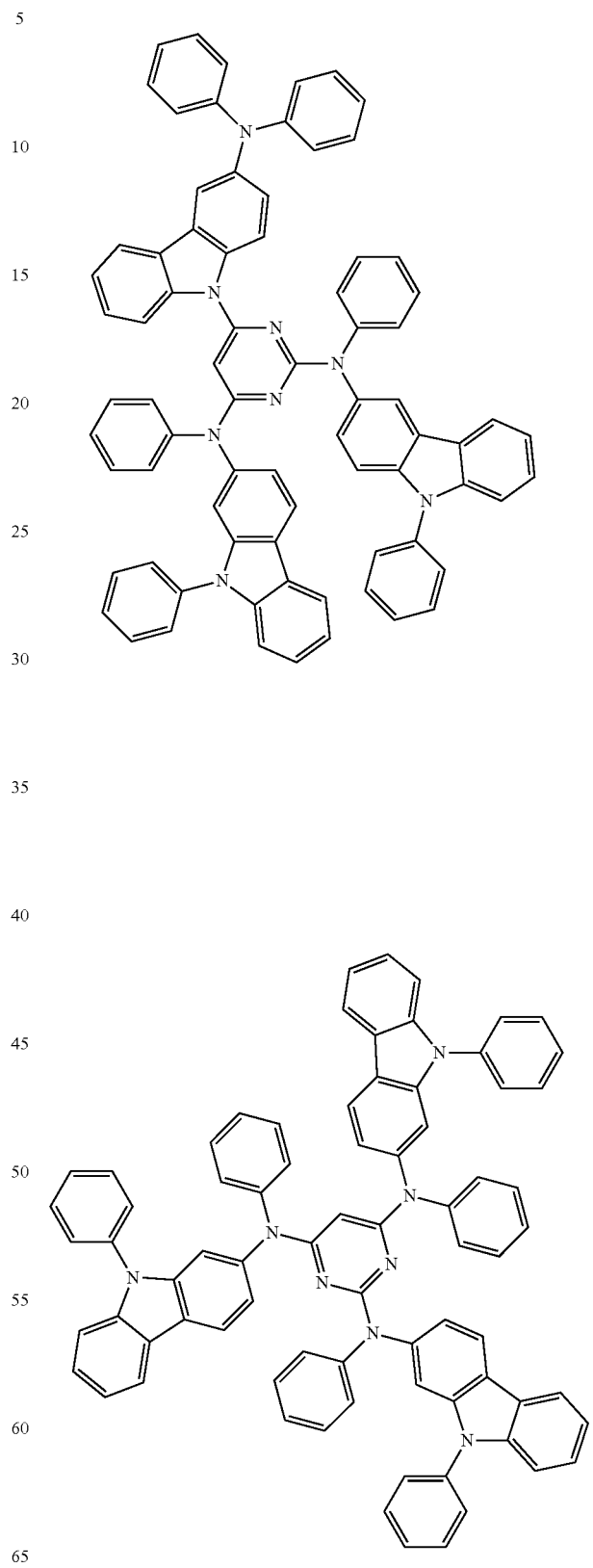

1045
-continued
1046
-continued
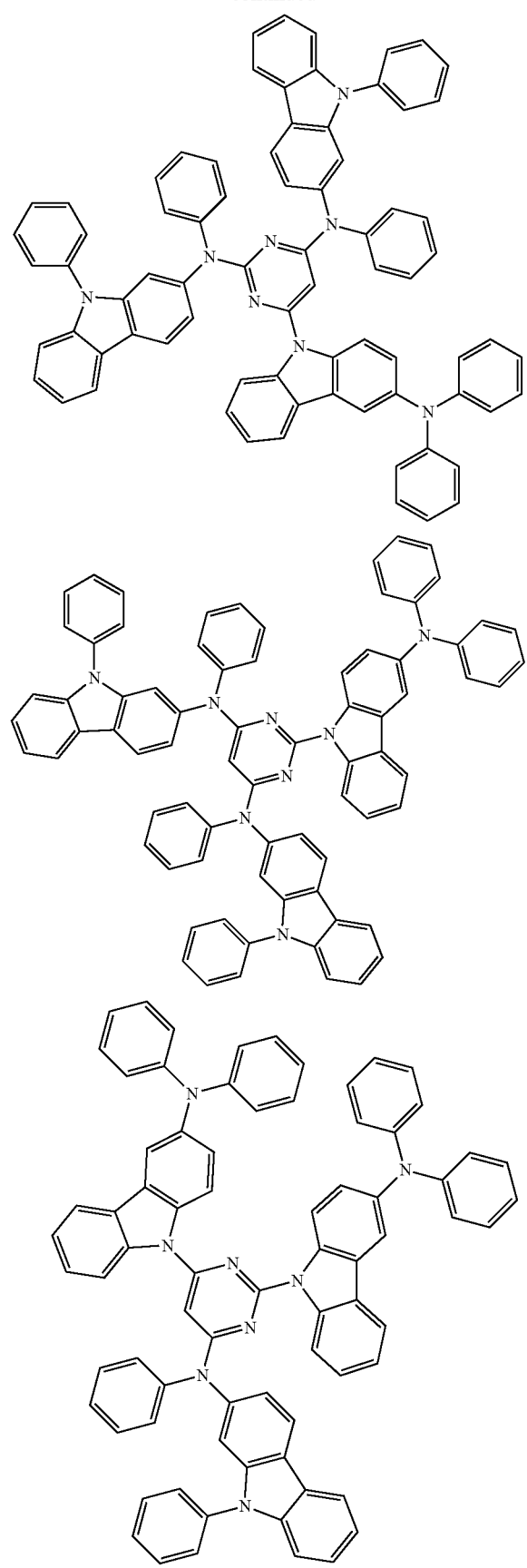
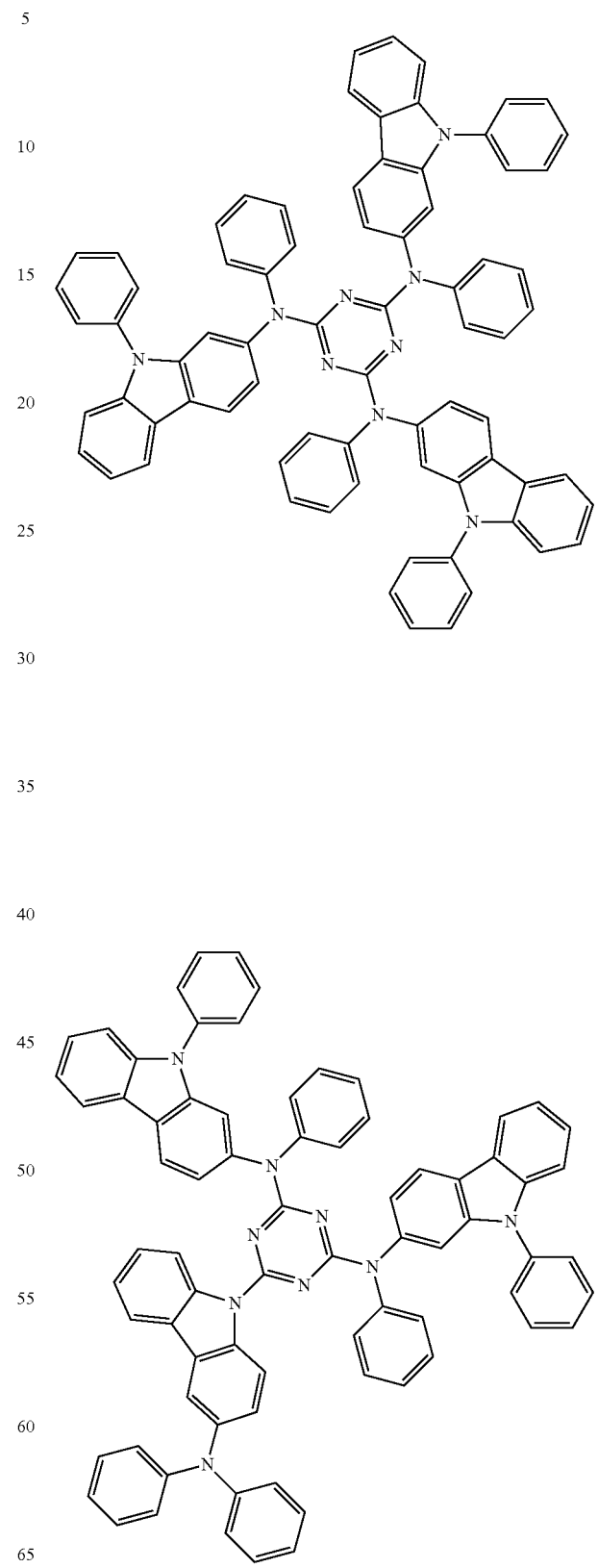

1047
-continued
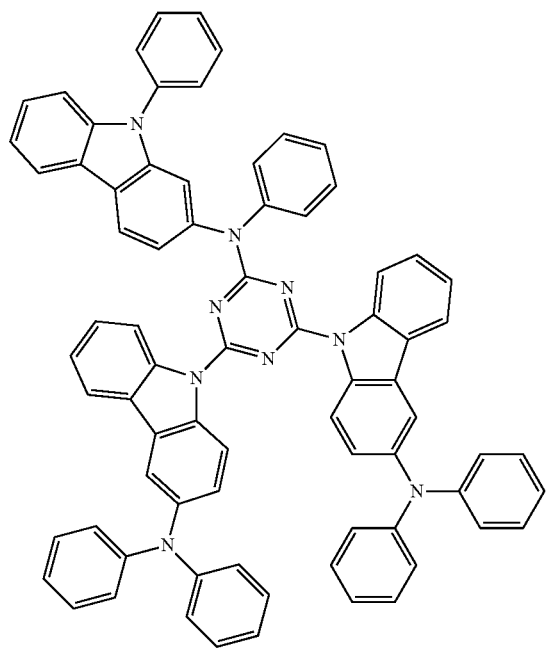
1048
-continued
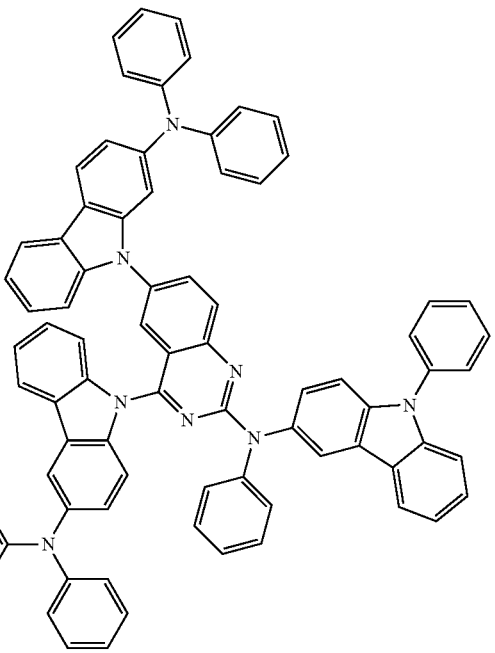
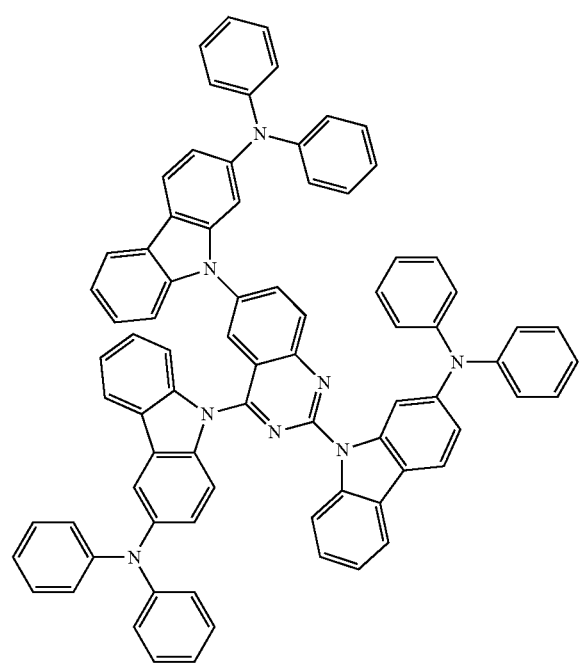
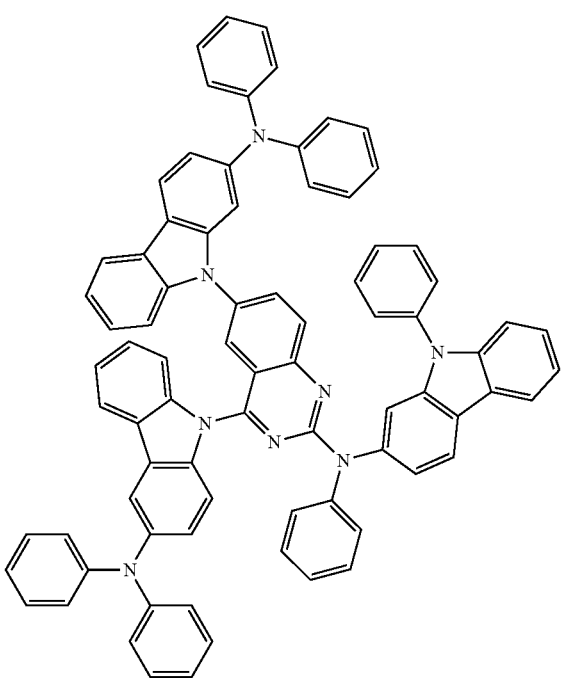

1049
-continued
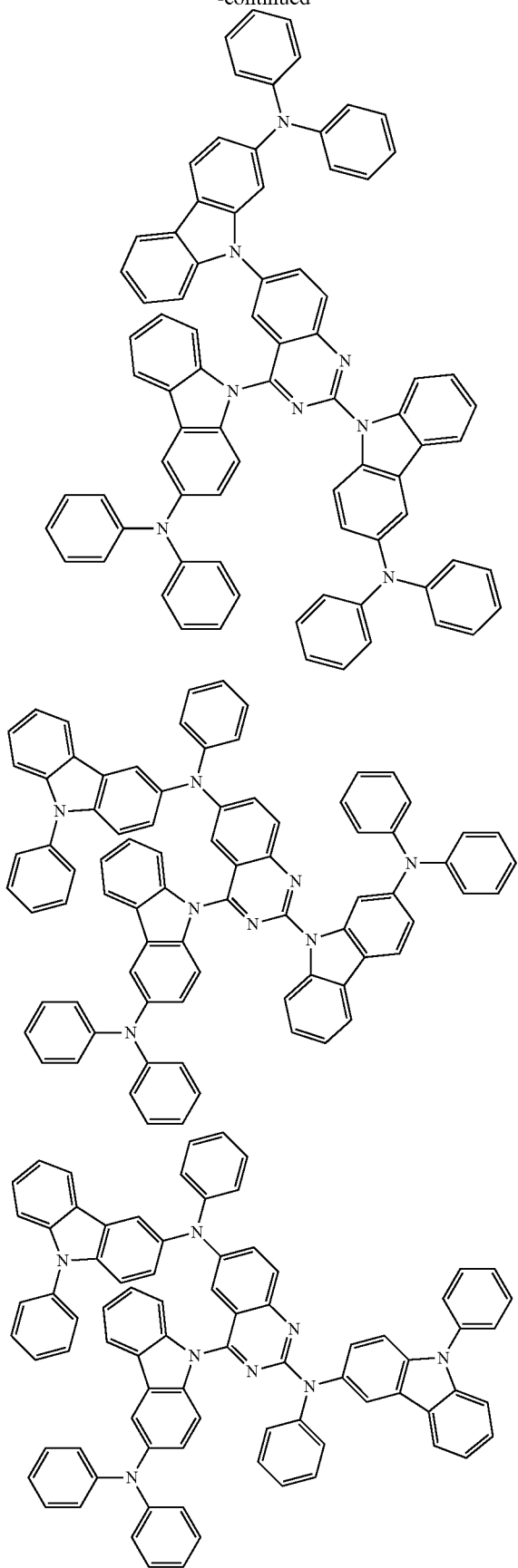
1050
-continued
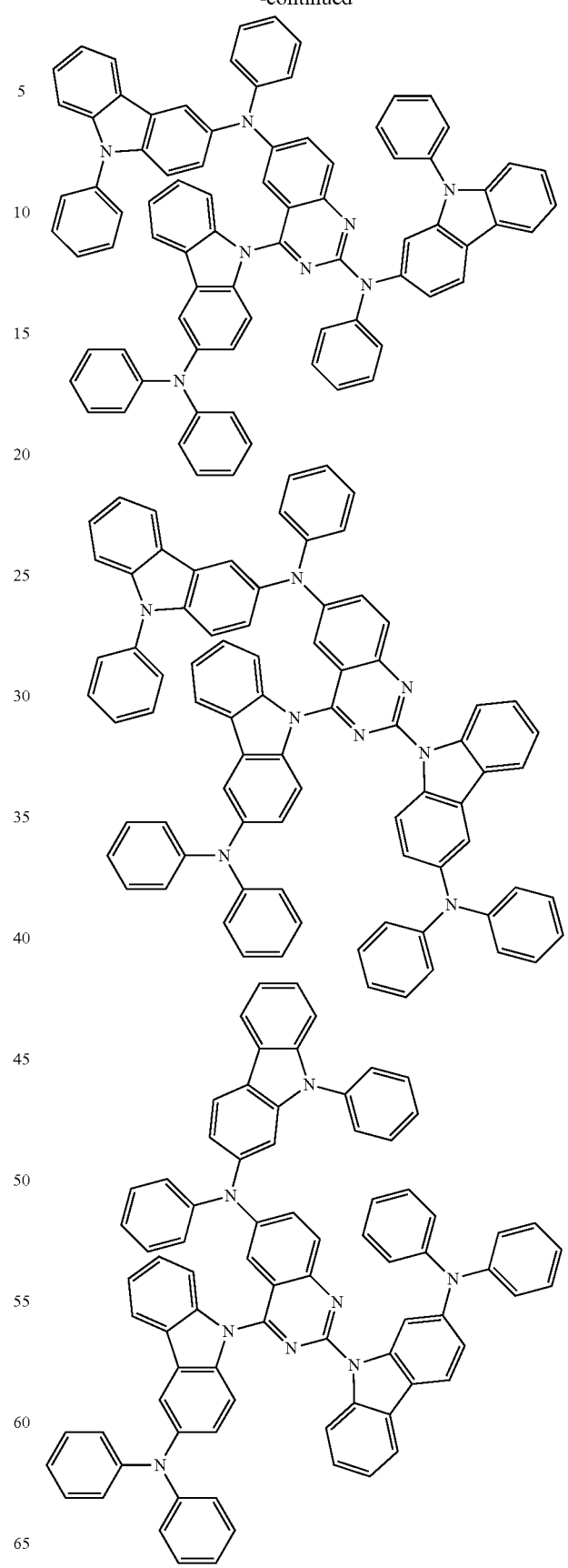

1051
-continued
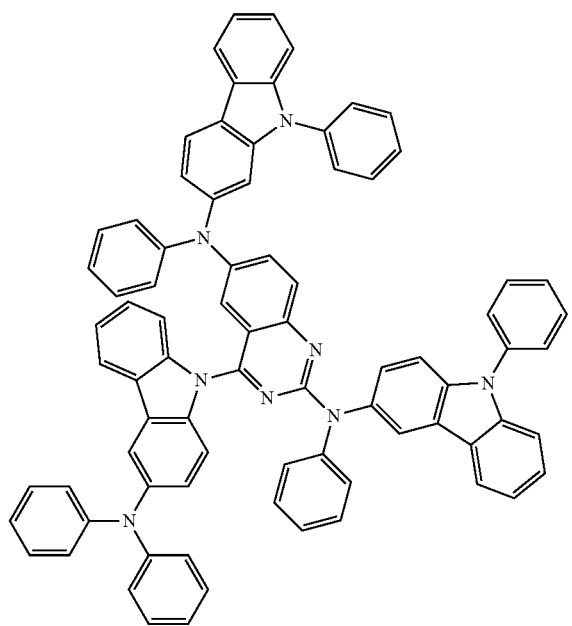
1052
-continued
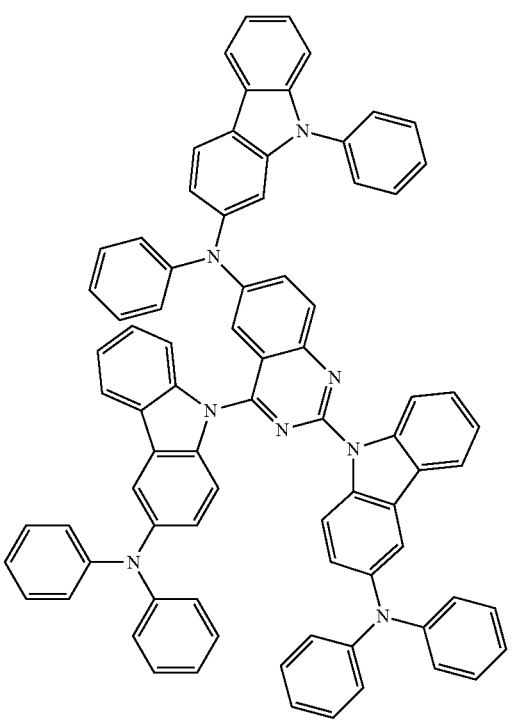
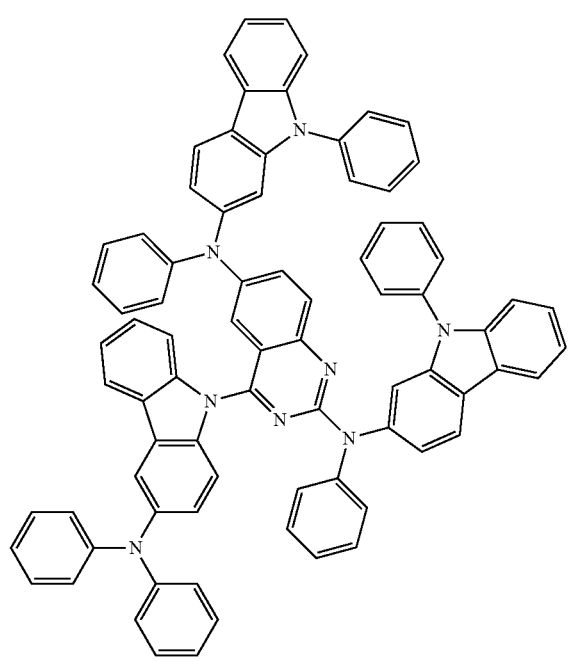
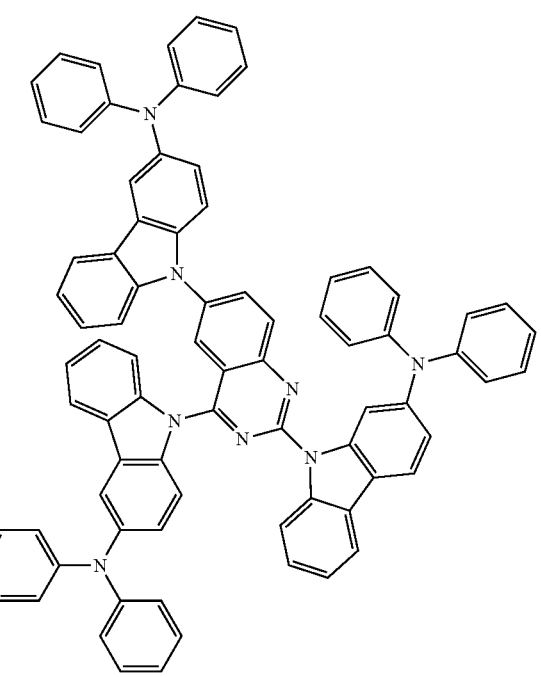

1053
-continued
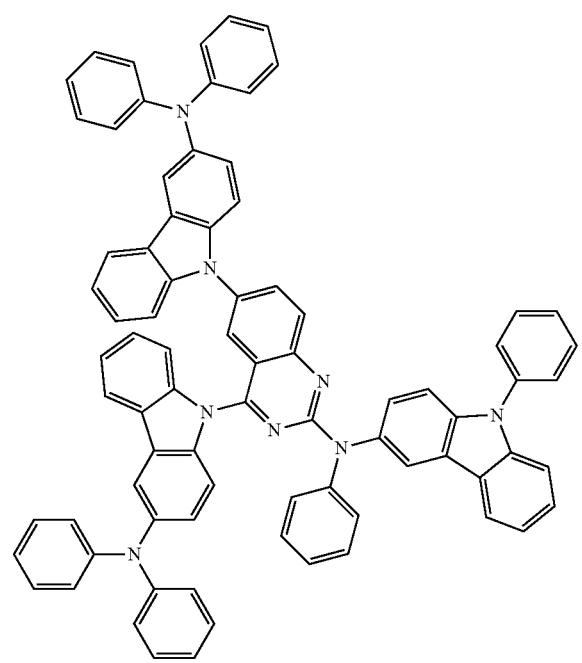
1054
-continued
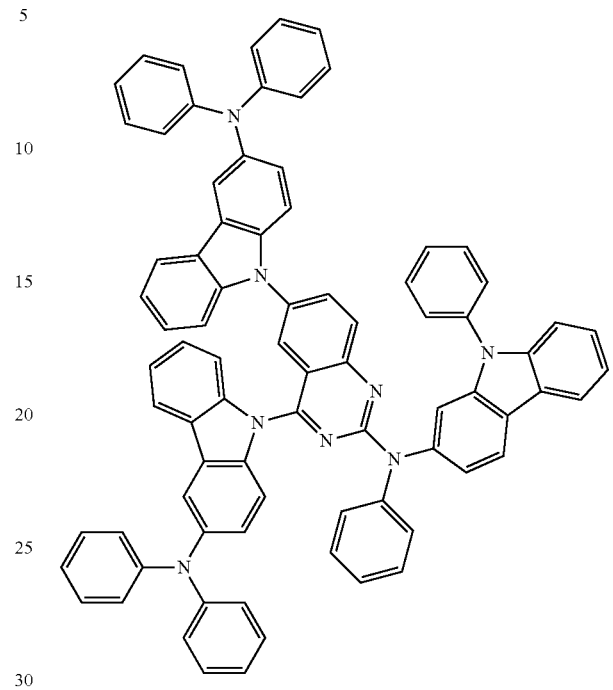
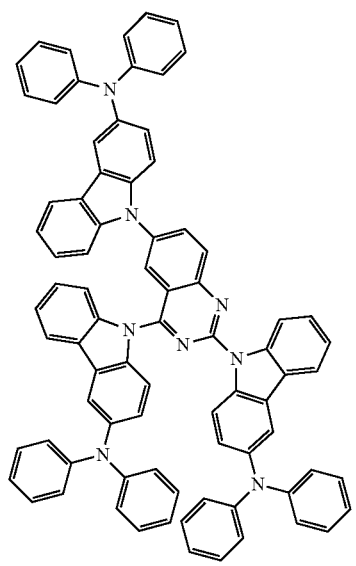
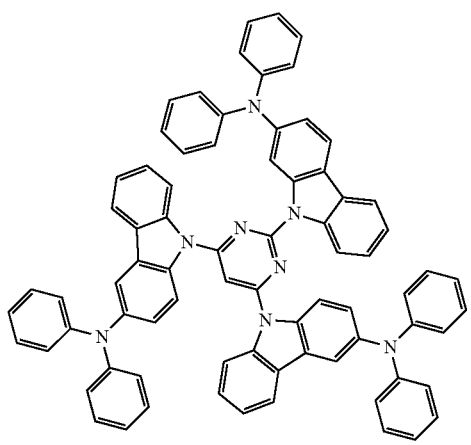

1055 1056
-continued
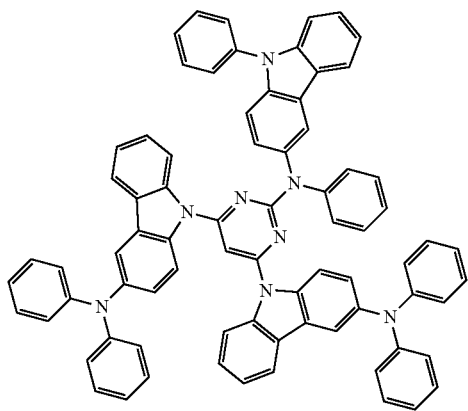
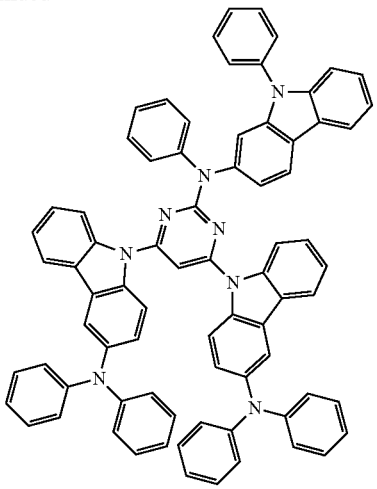
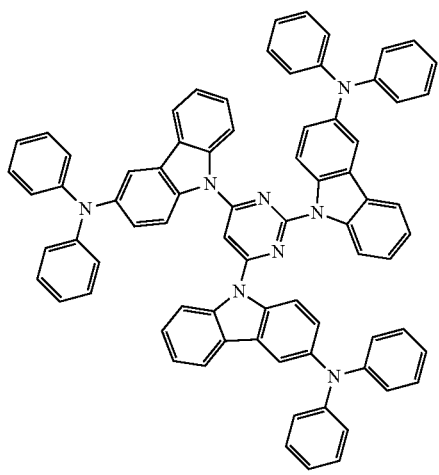
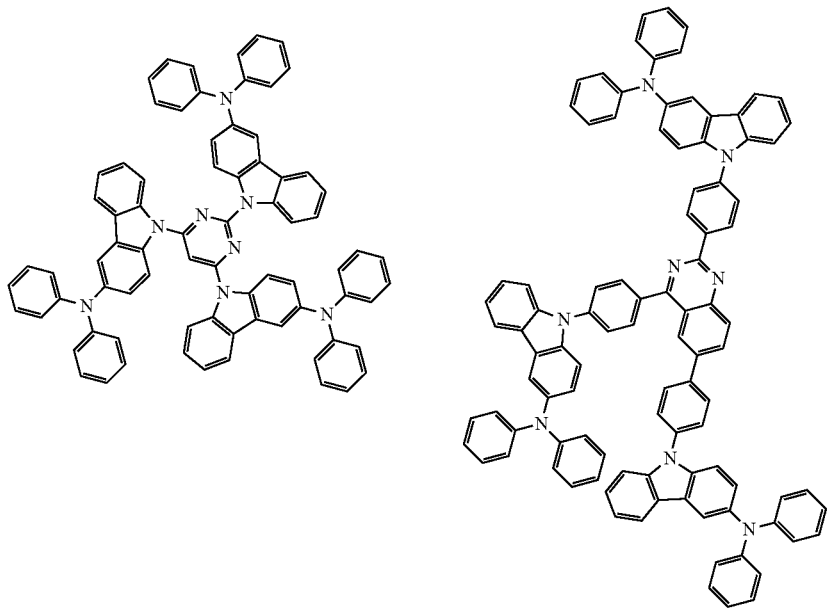

-continued
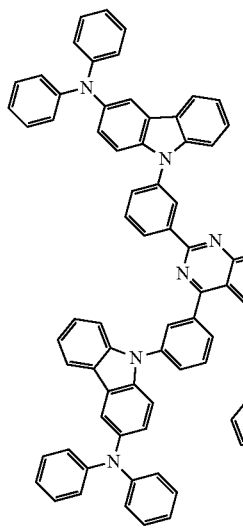
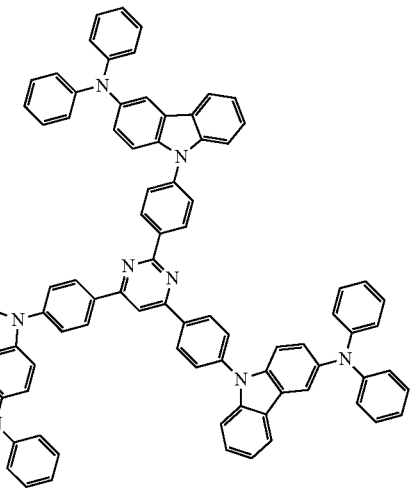
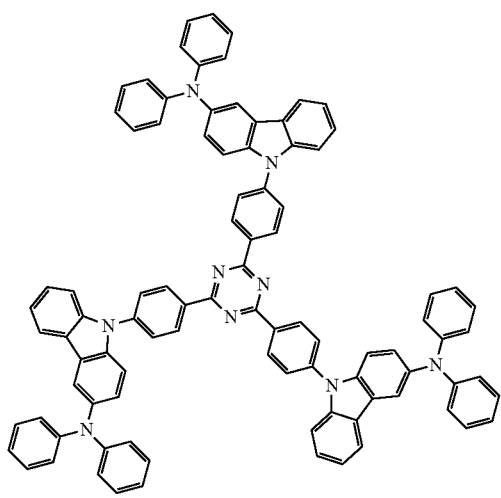
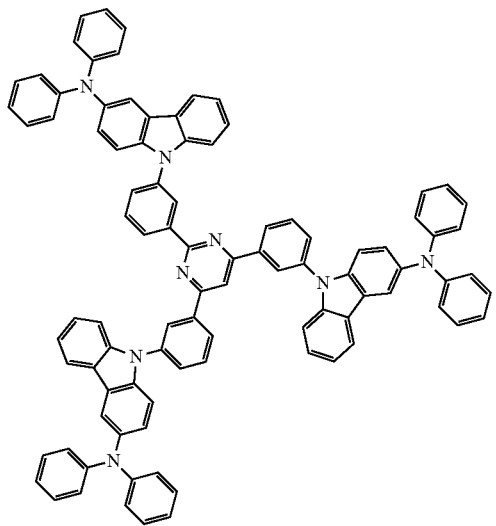

-continued
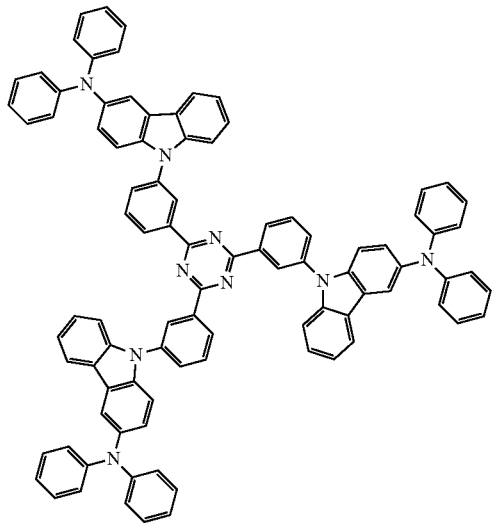
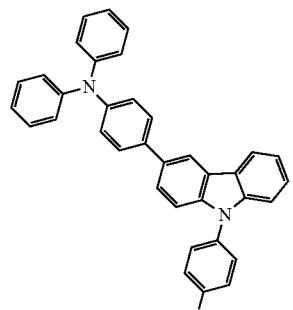
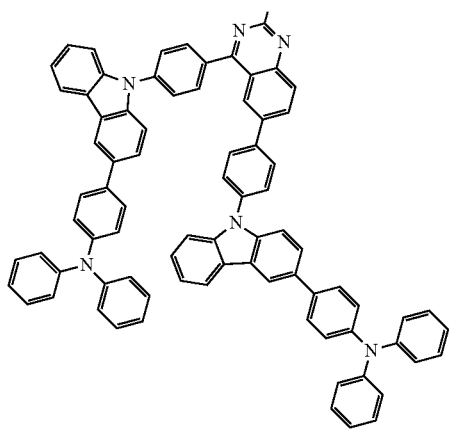

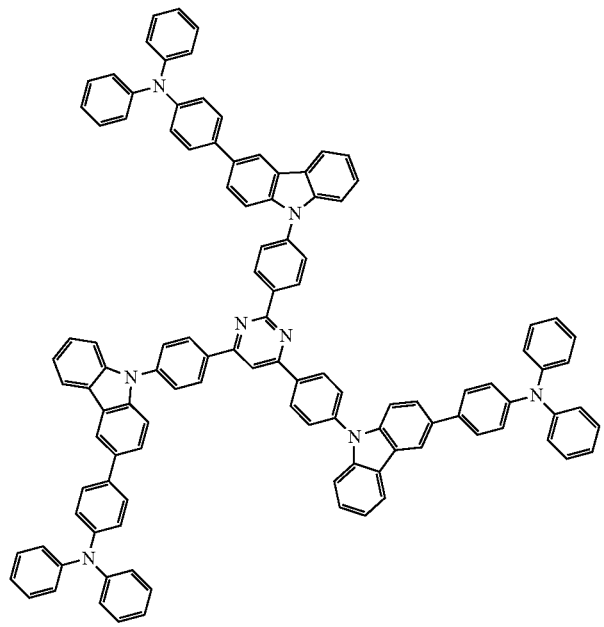
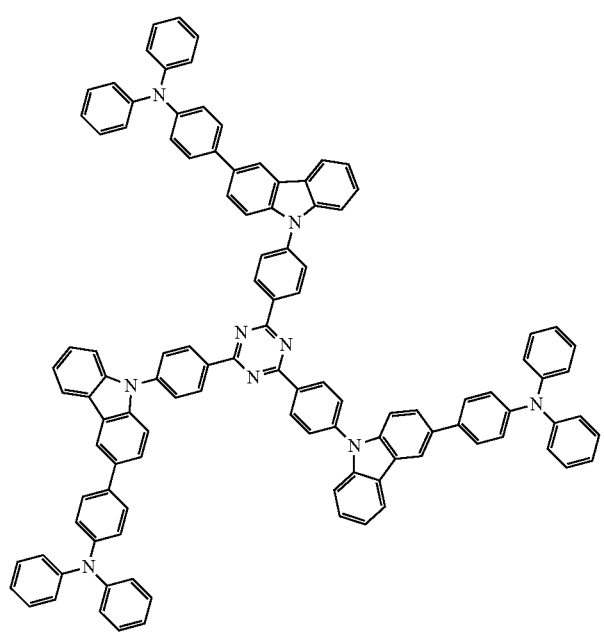

-continued
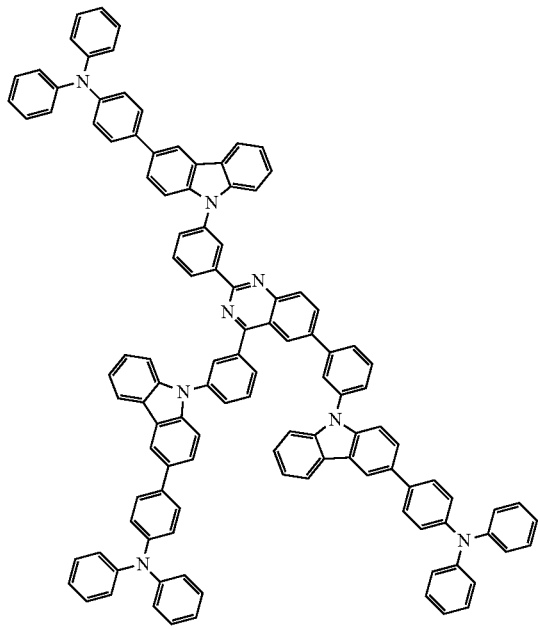
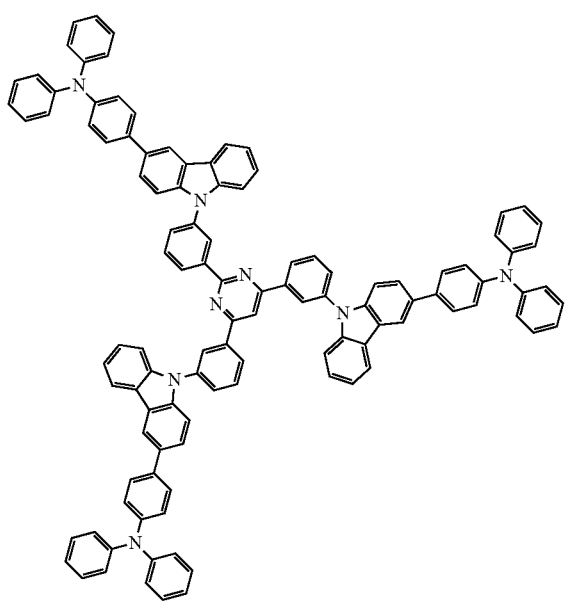

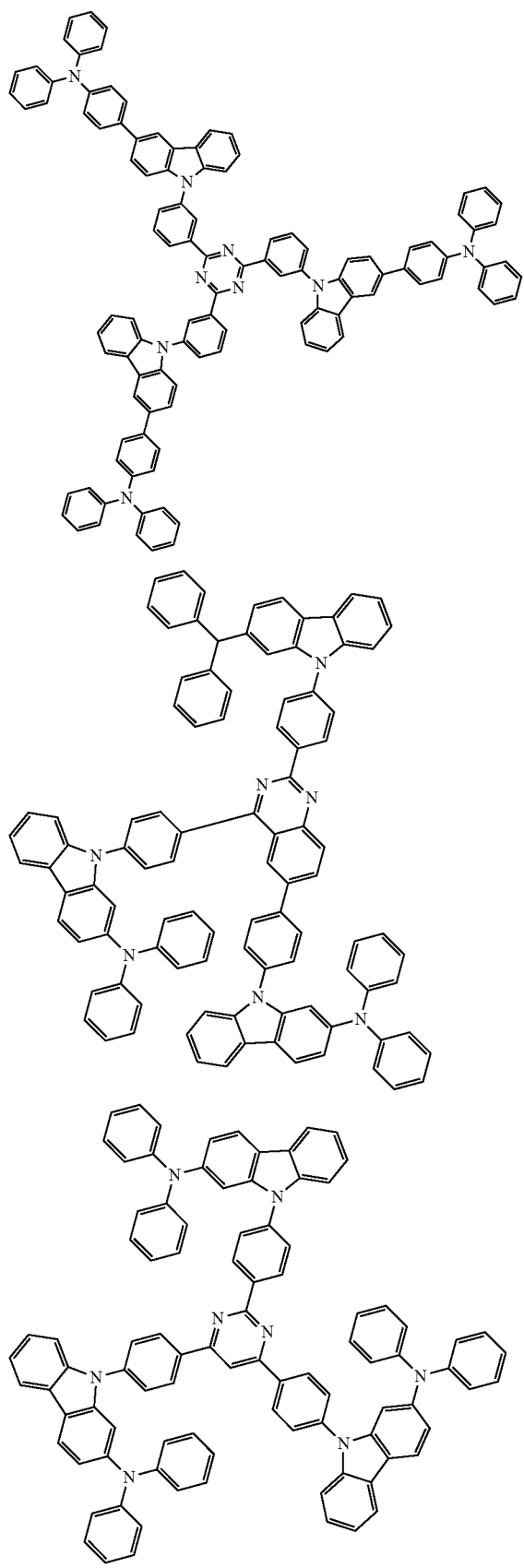

1067    1068
-continued
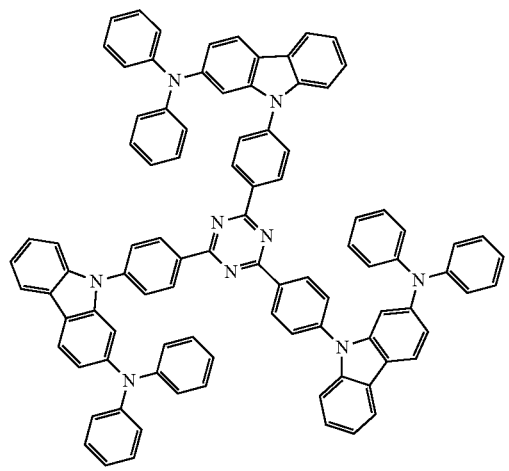
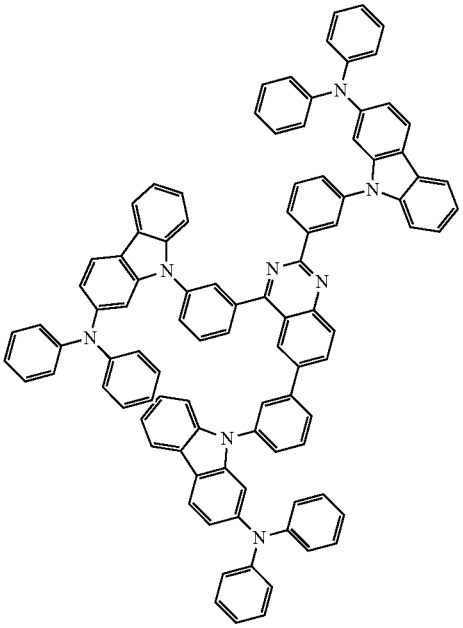
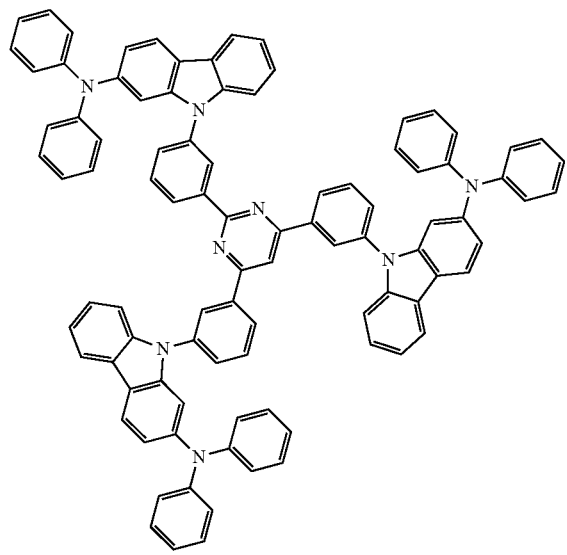
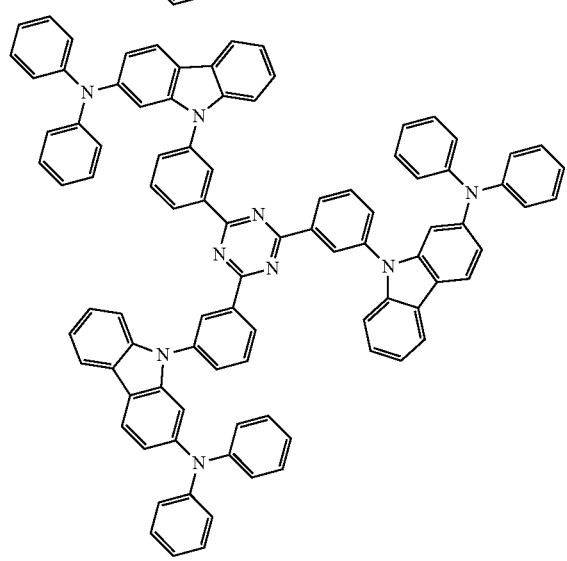

-continued
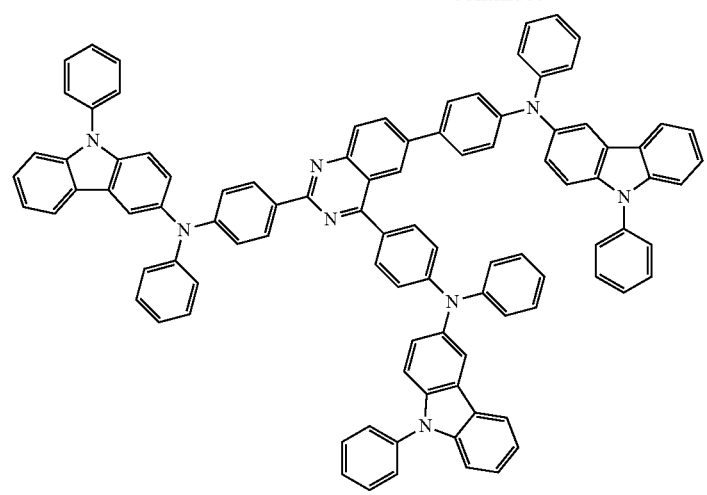
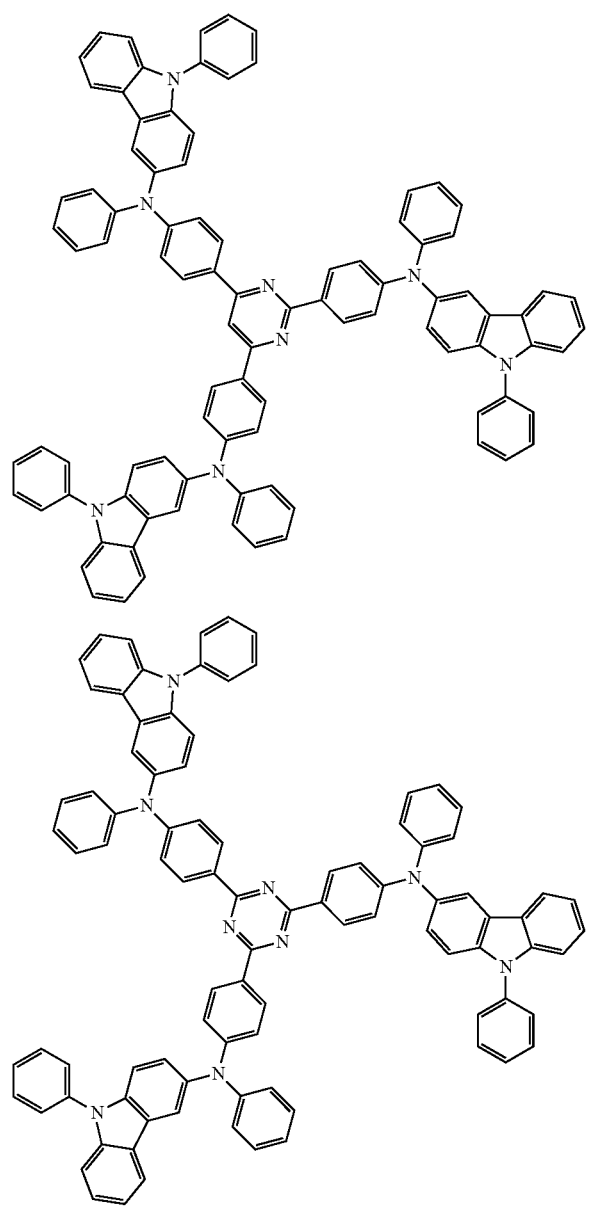

-continued
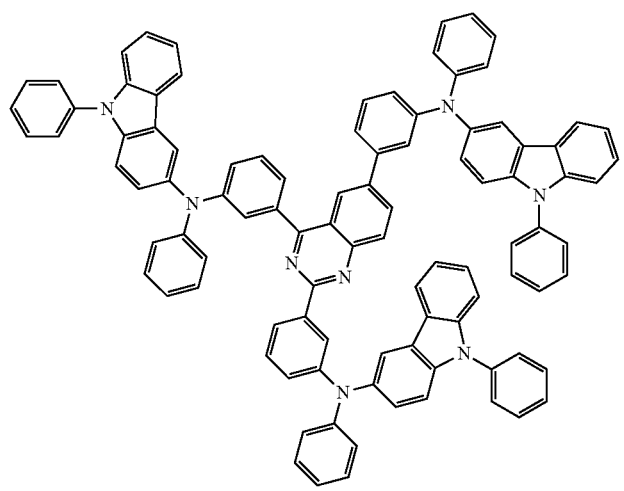
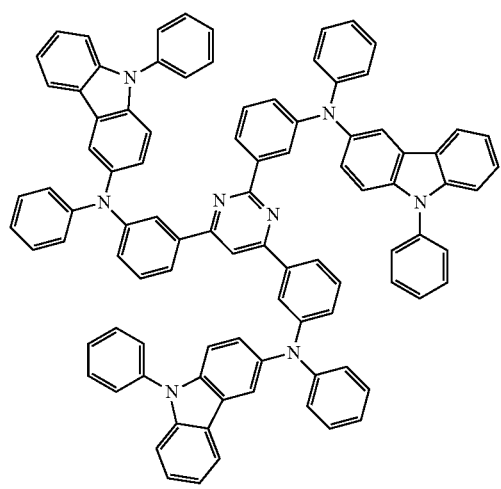
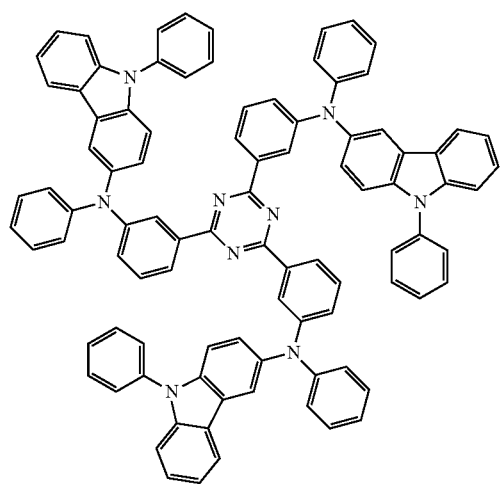

1073
-continued
1074
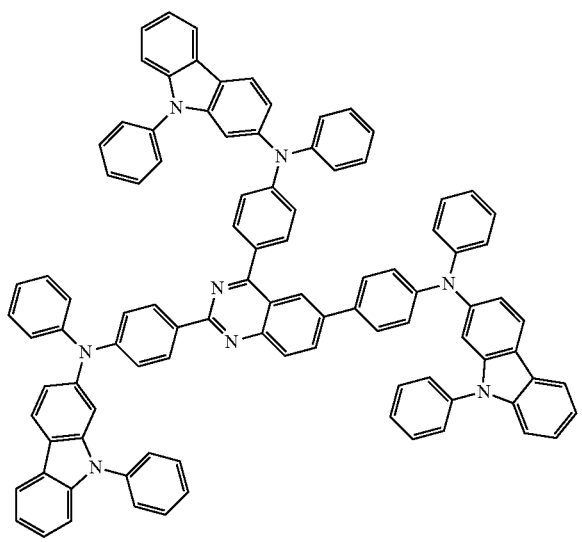
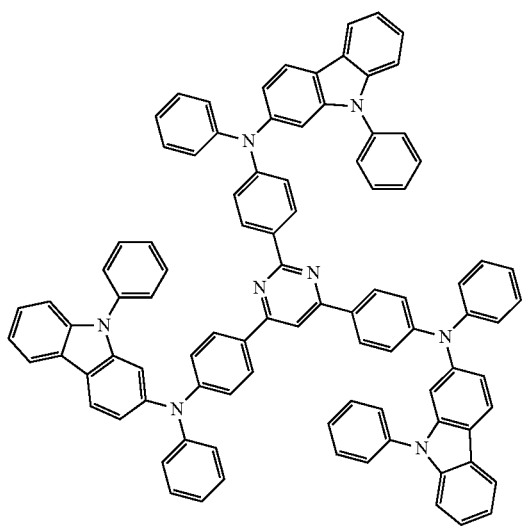
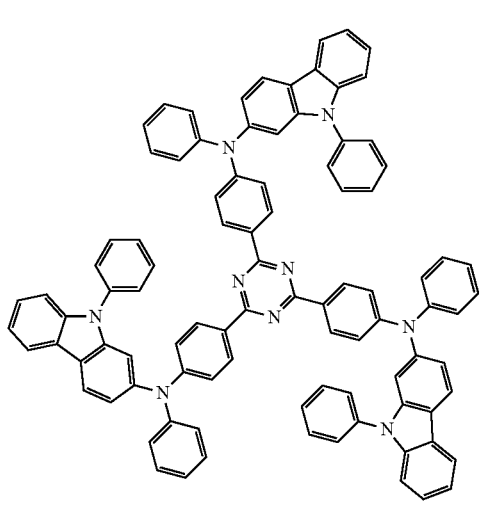
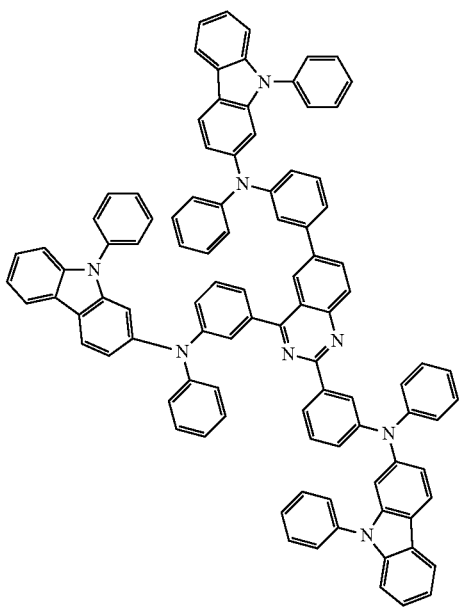

1075
1076
-continued
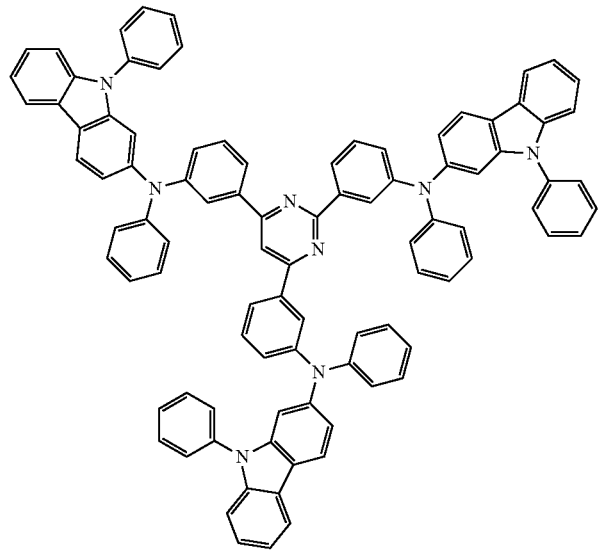
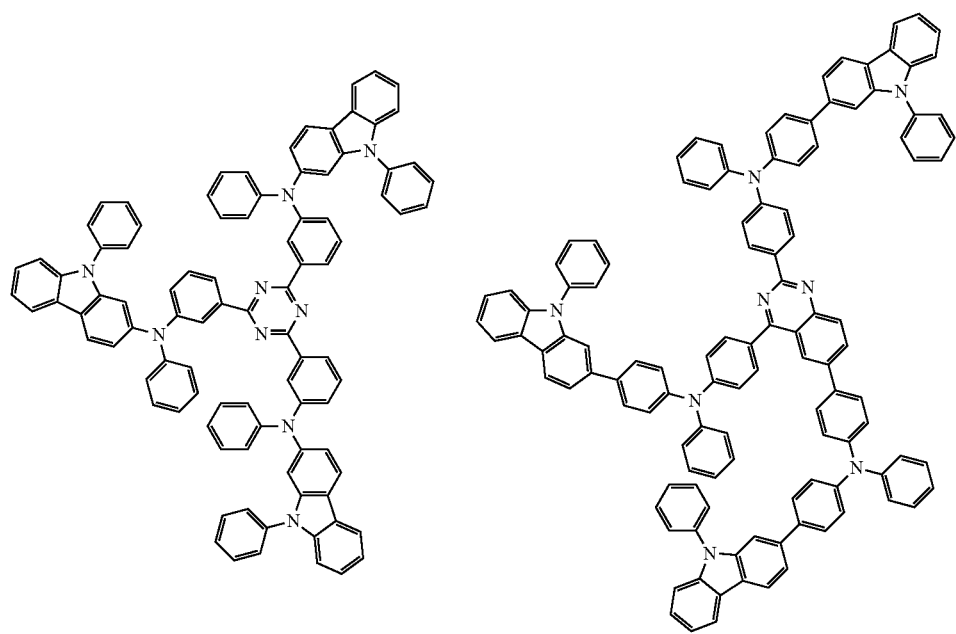

-continued
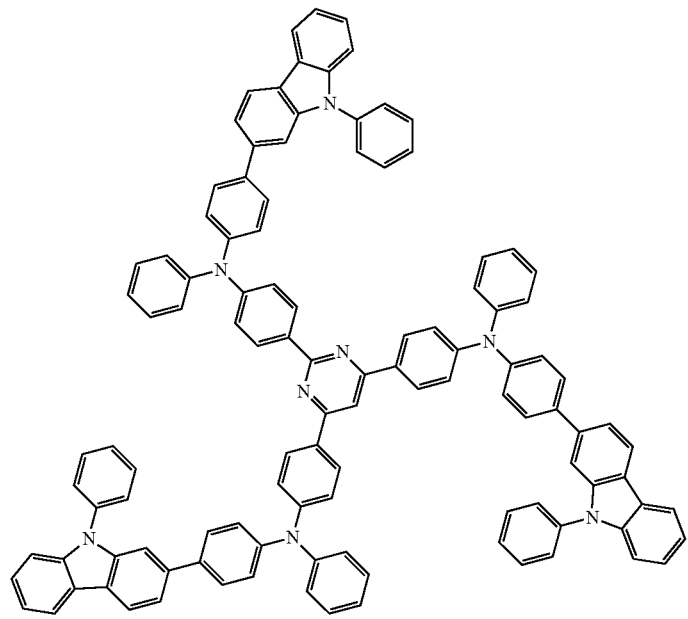
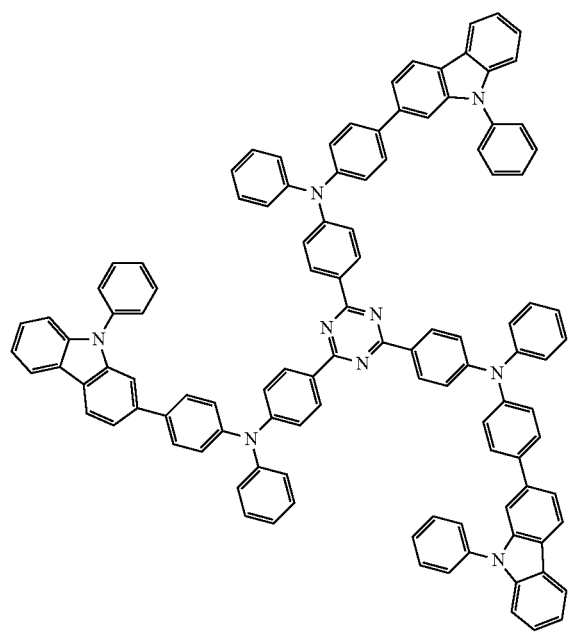

-continued
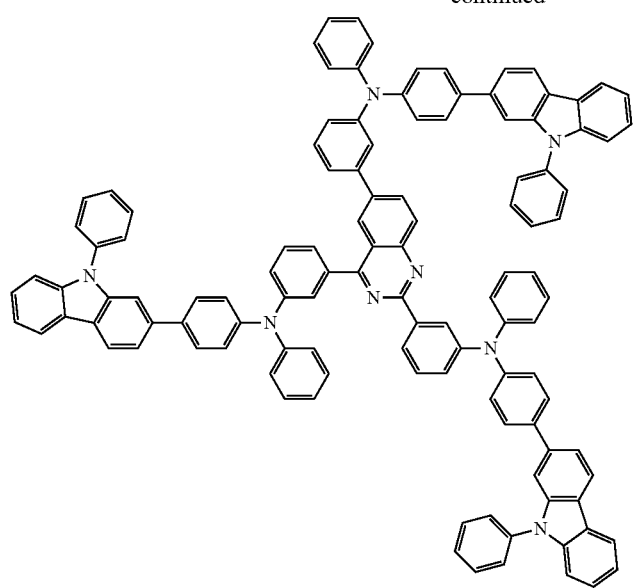
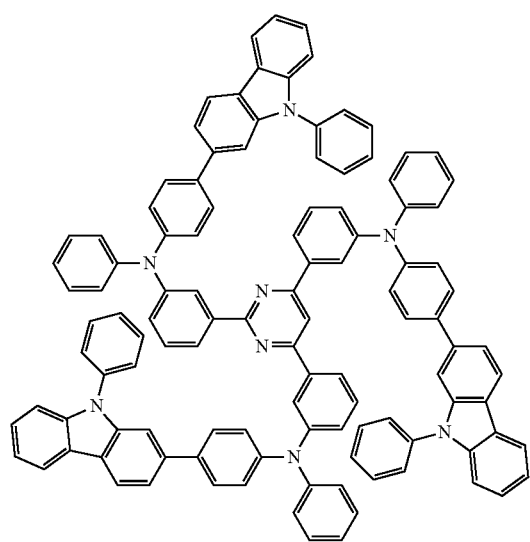
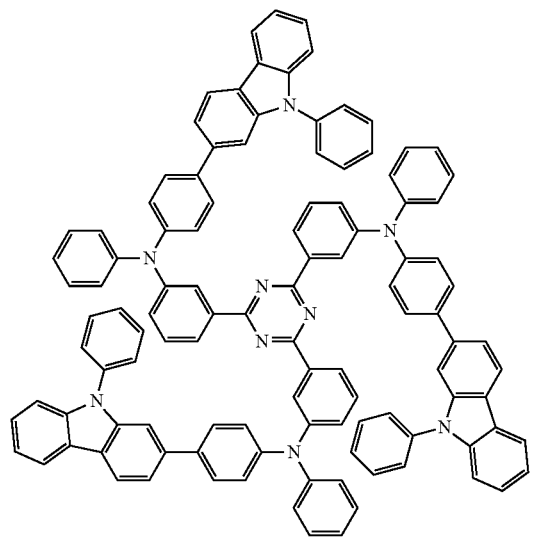

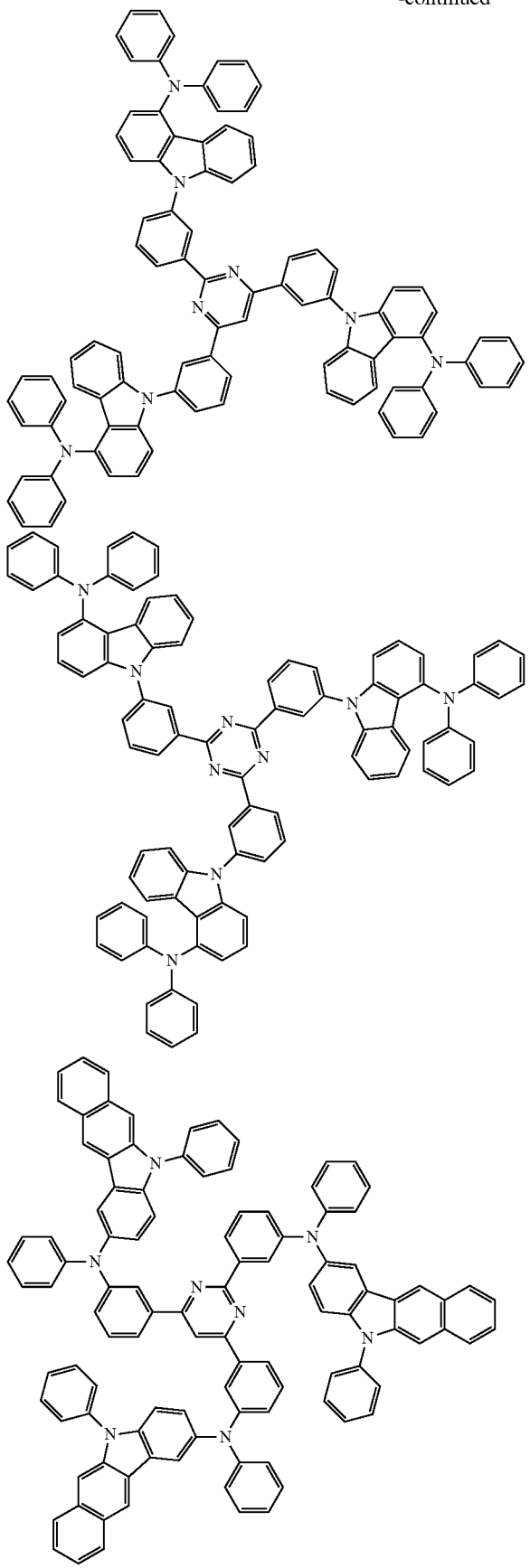

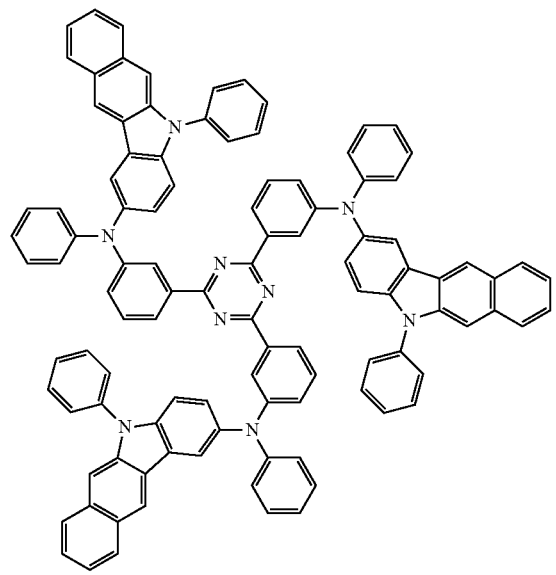
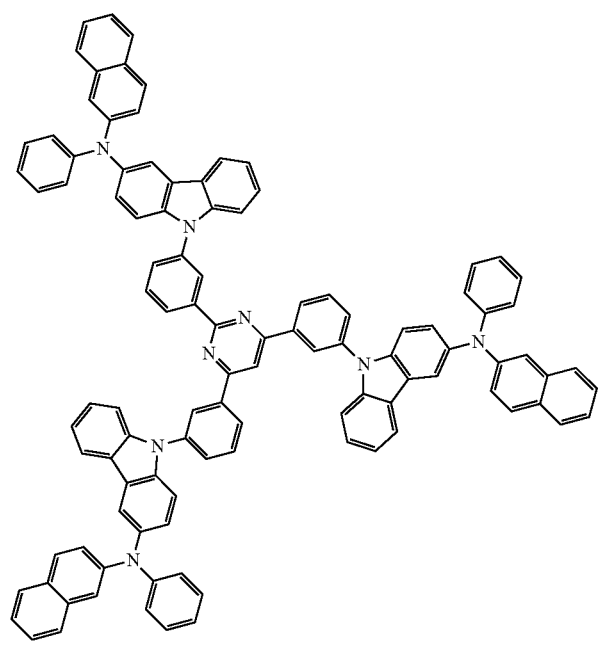

-continued
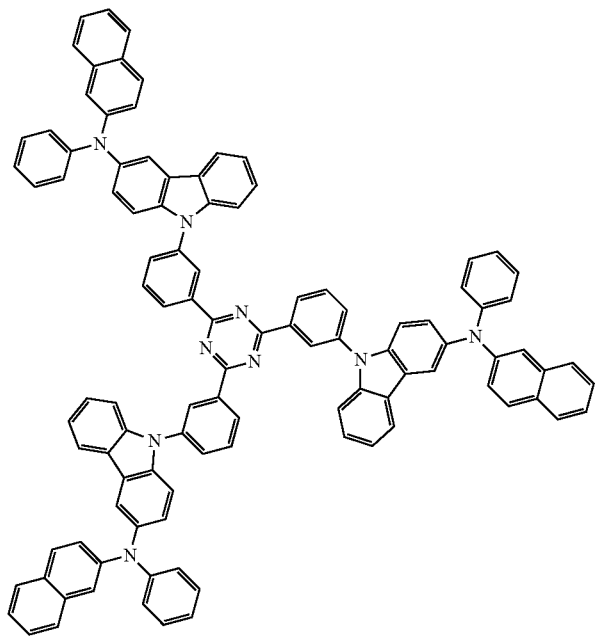
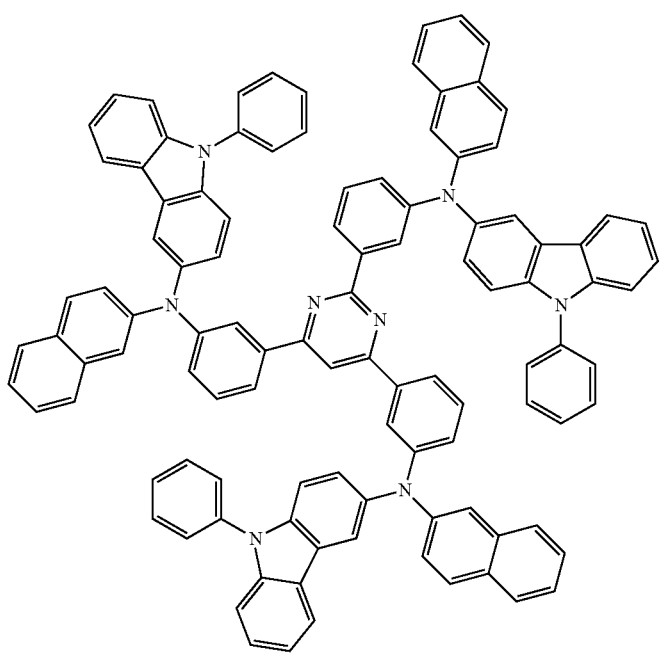

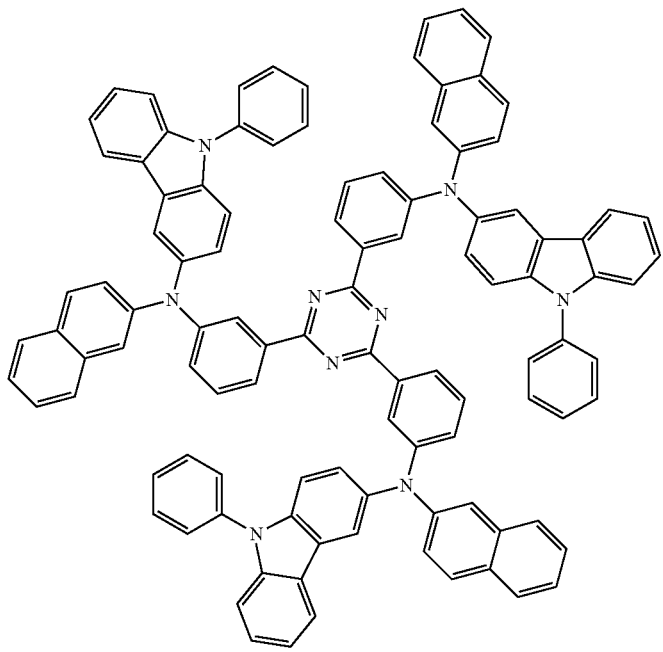
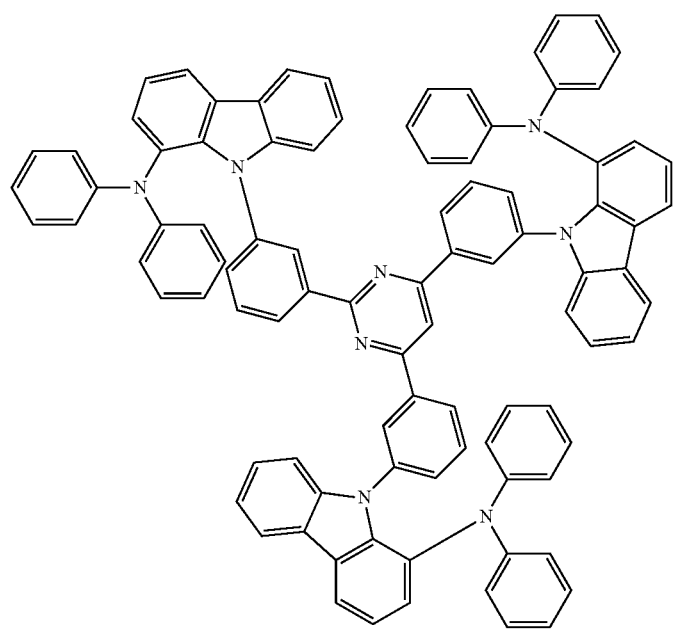

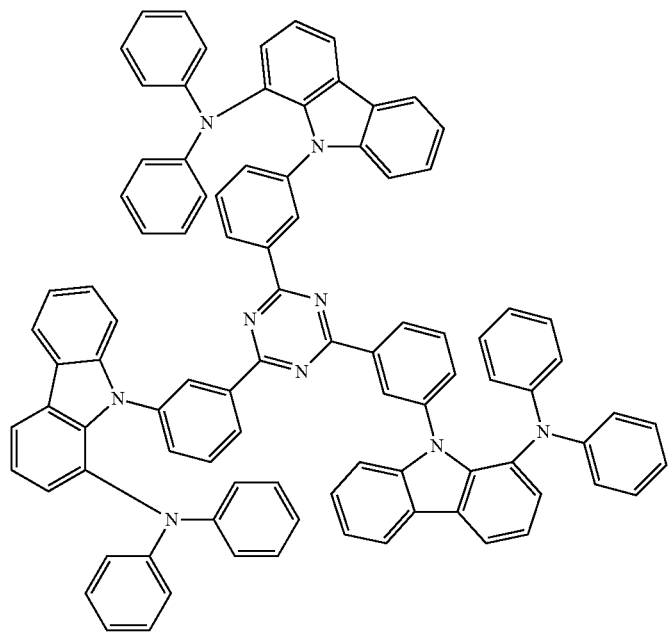
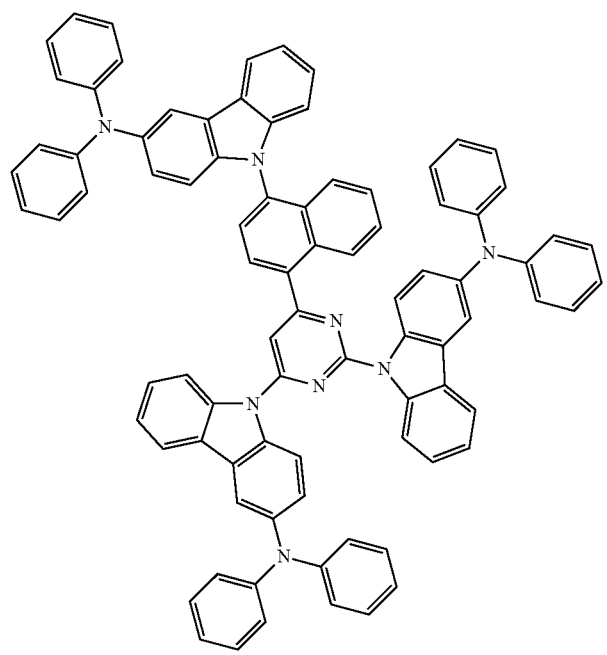

1091 1092
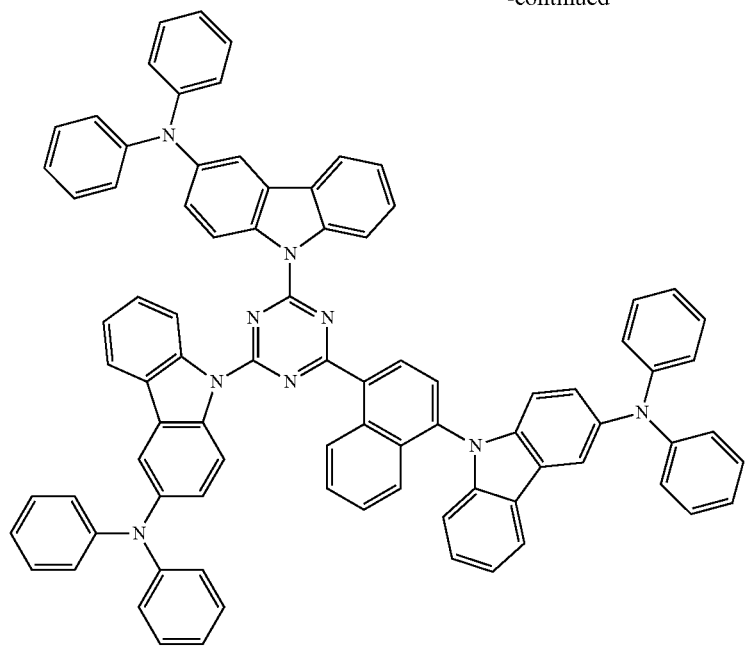
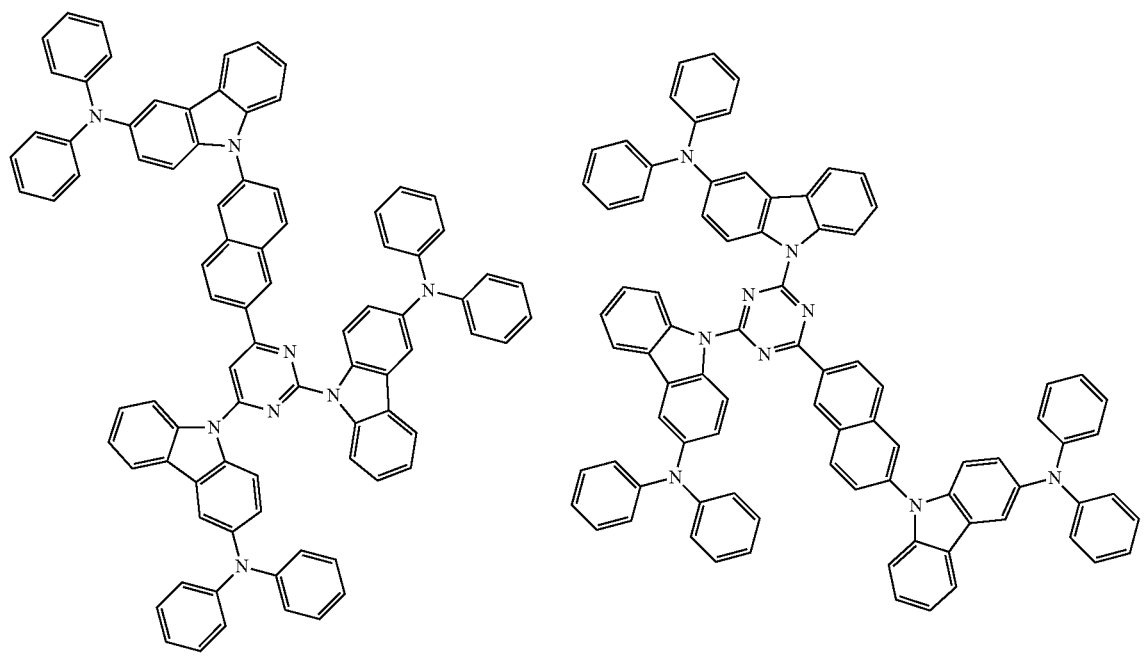
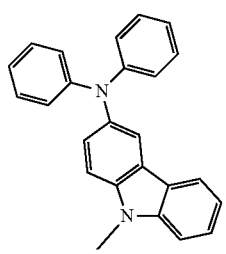

1093
1094
-continued
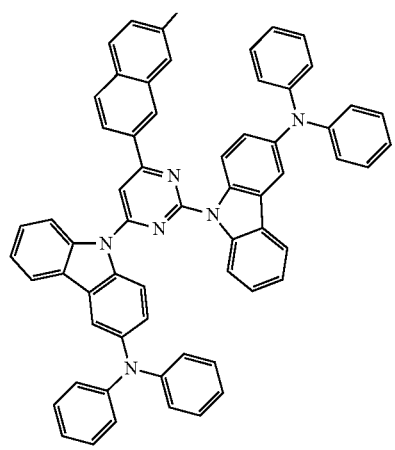
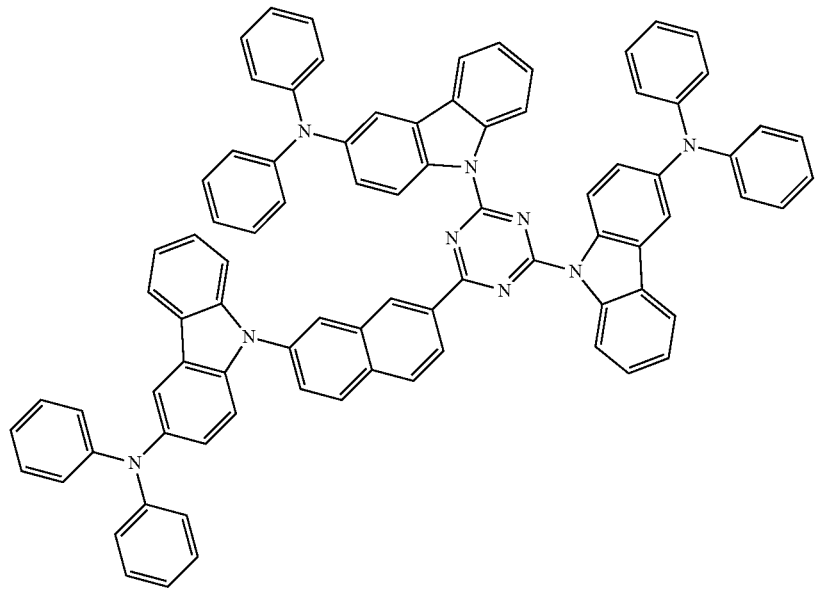
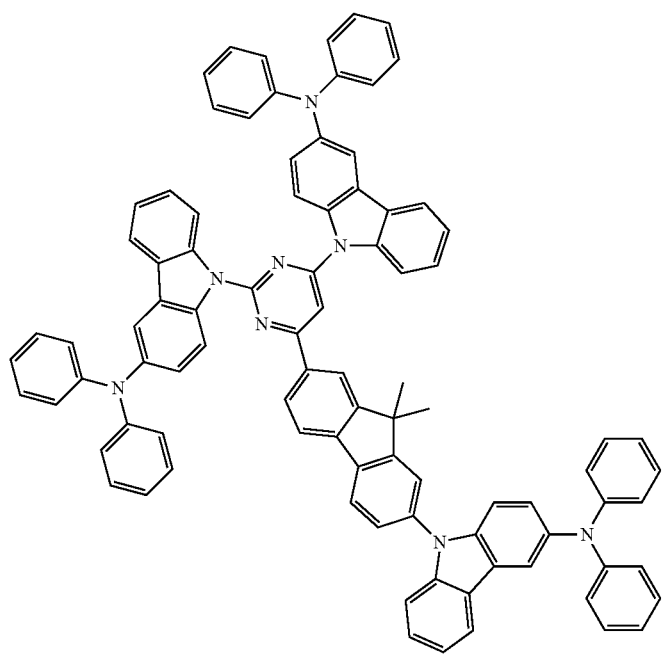

1095
1096
-continued
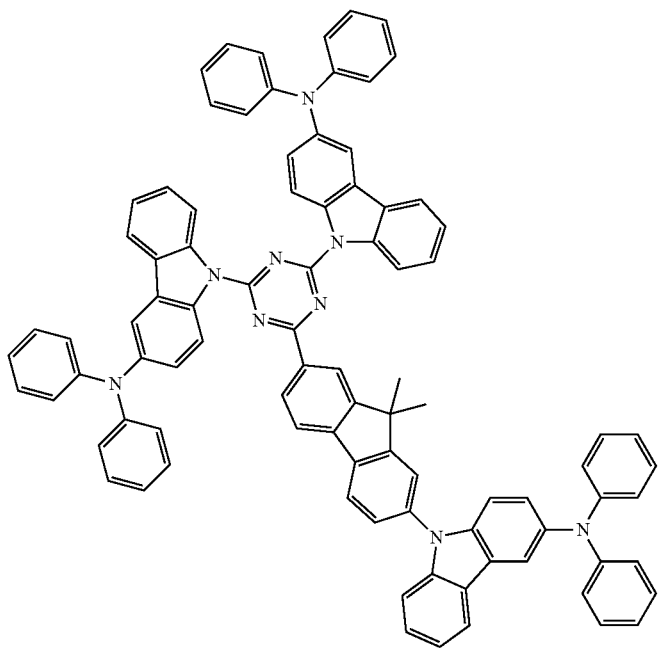
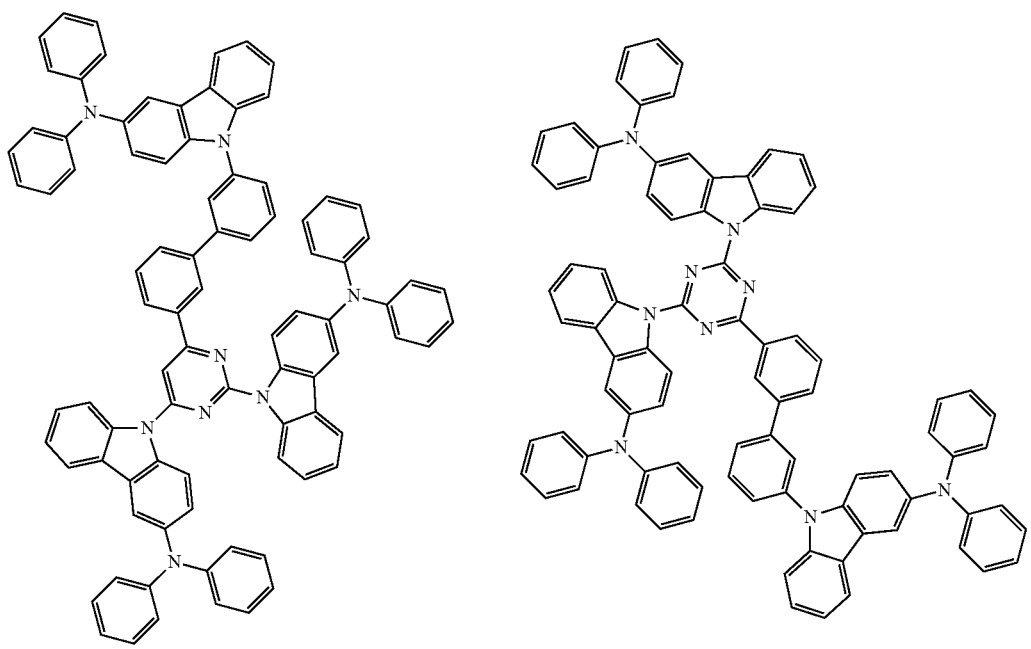

1097
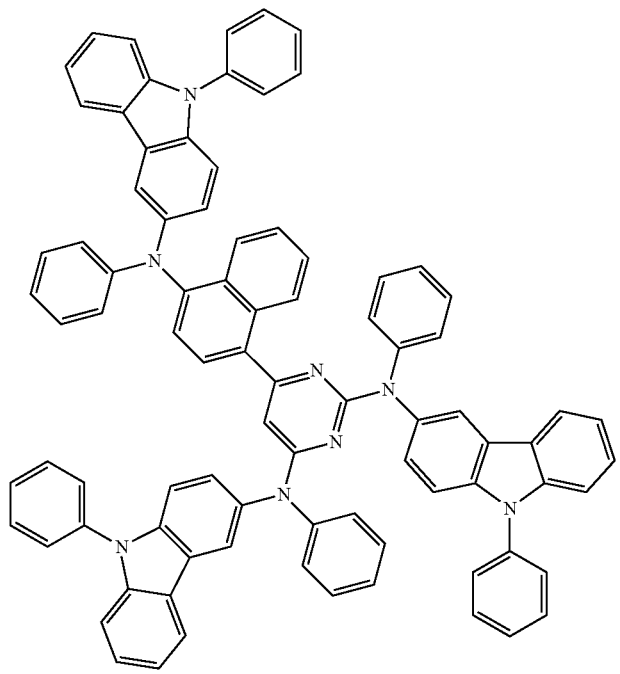
1098
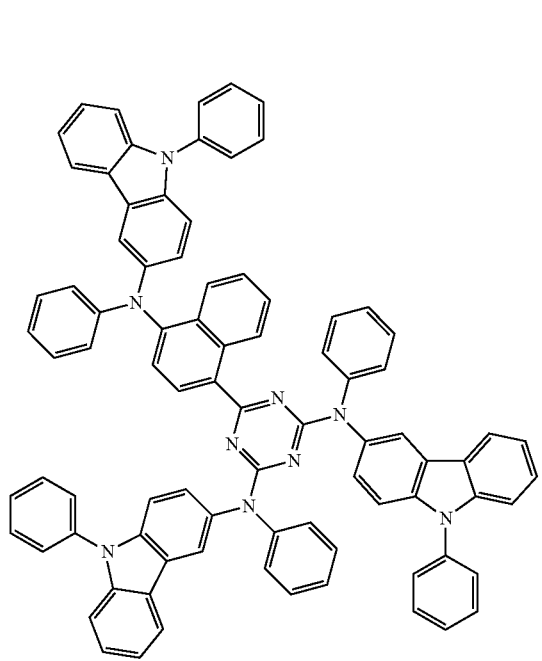
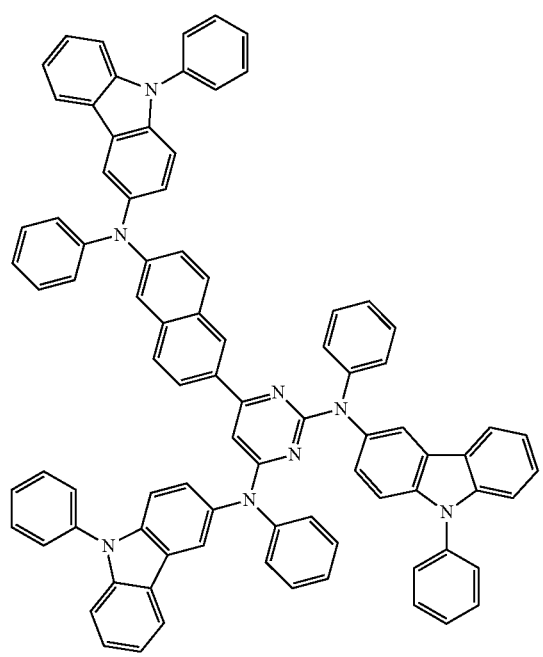

1099 1100
-continued
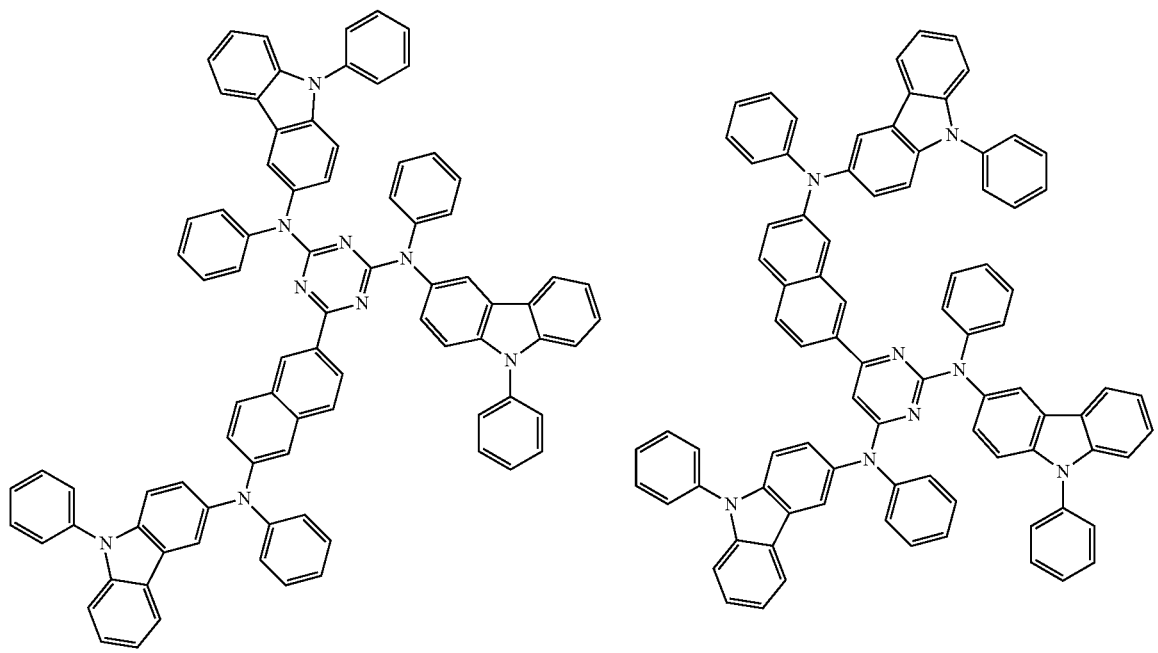
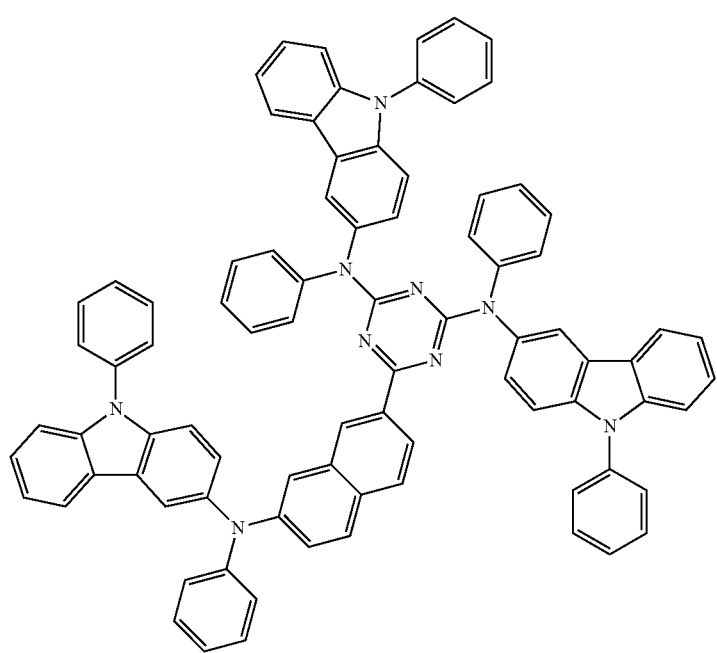 [SMILES: c1ccc(N(c2ccc3ccc(-c4nc(N(c5ccccc5)c5ccc6c(c5)c5ccccc5n6-c5ccccc5)nc(N(c5ccccc5)c5ccc6c(c5)c5ccccc5n6-c5ccccc5)n4)cc3c2)c2ccc3c(c2)c2ccccc2n3-c2ccccc2)cc1]

-continued
| 1101 | 1102 |
|---|---|
| 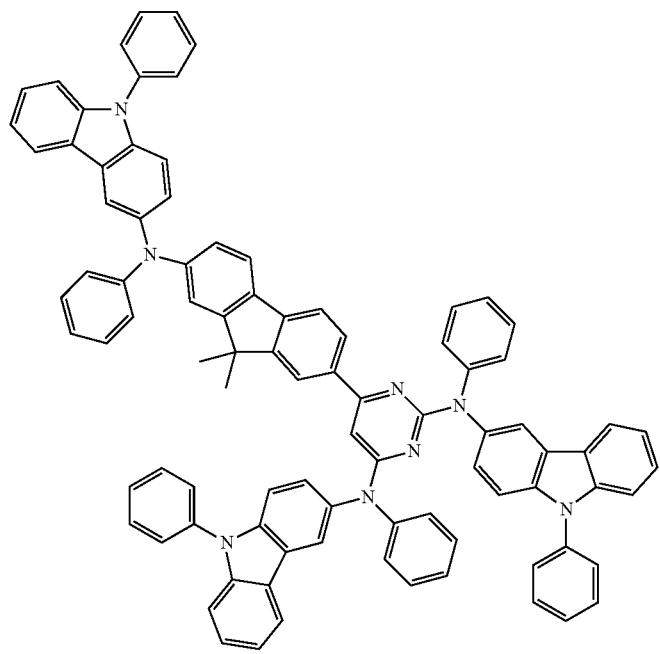 | 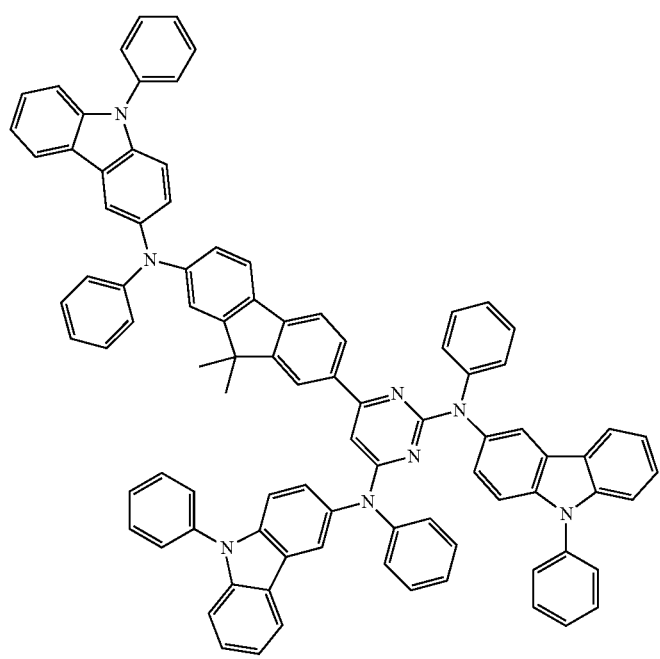 |

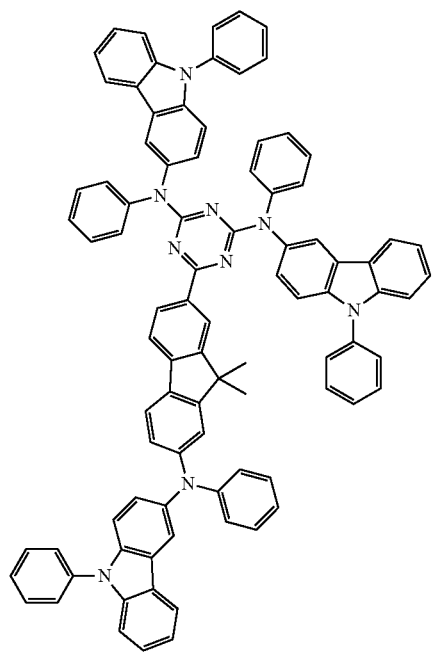
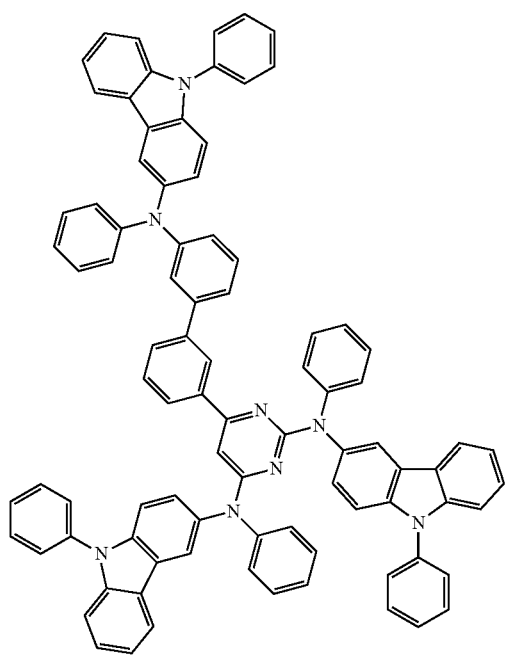

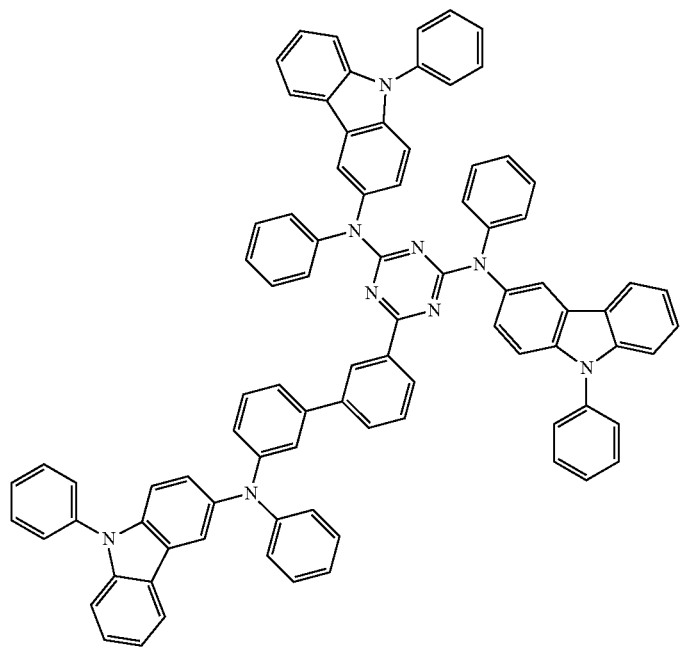
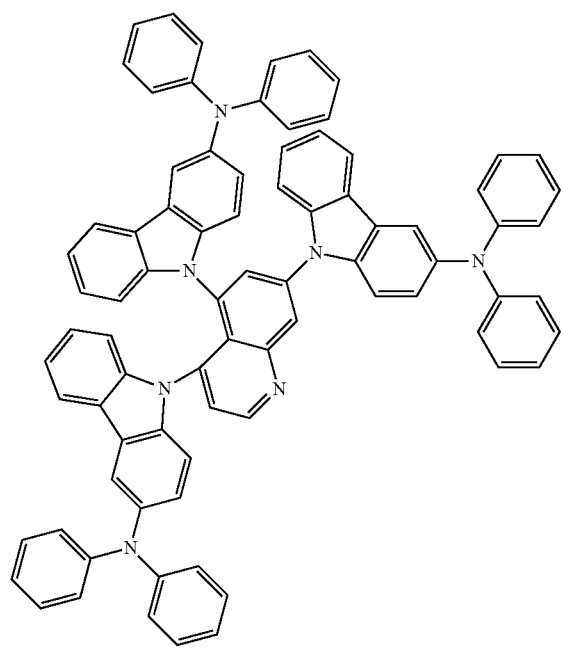

-continued
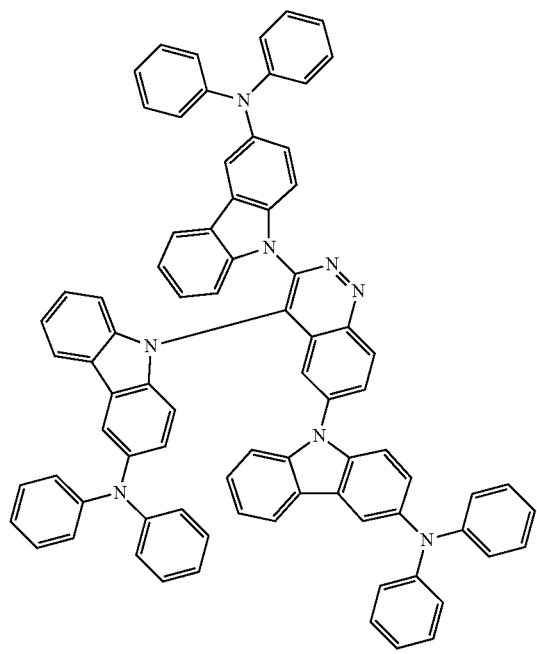
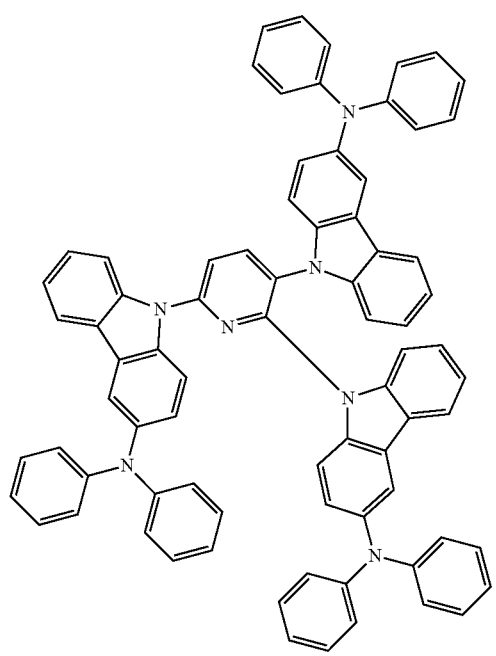

1109
1110
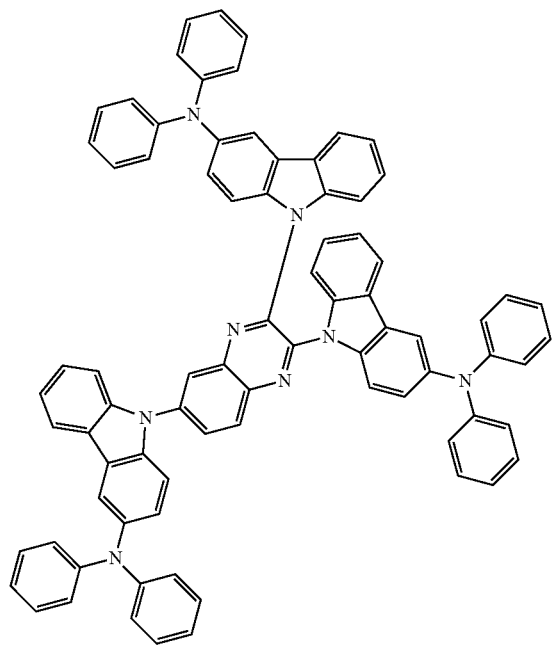
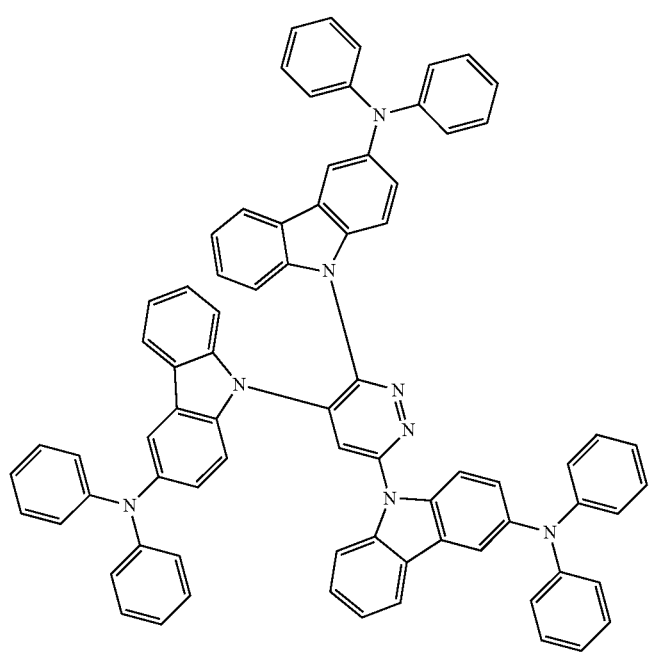

1111
1112
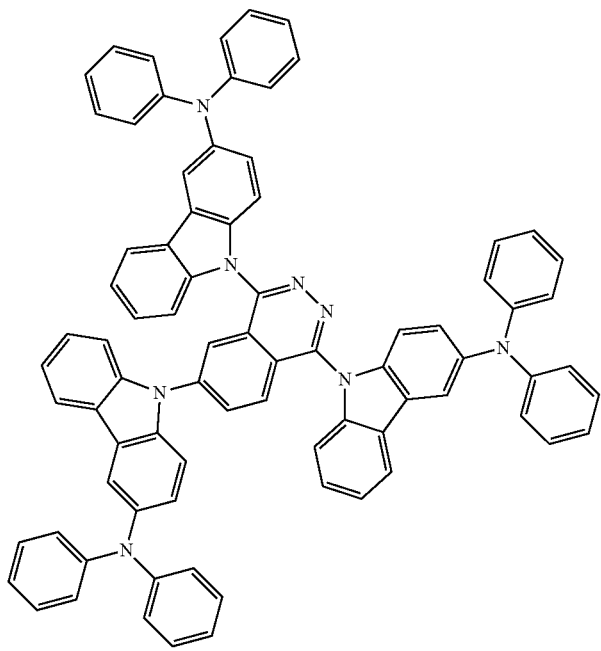
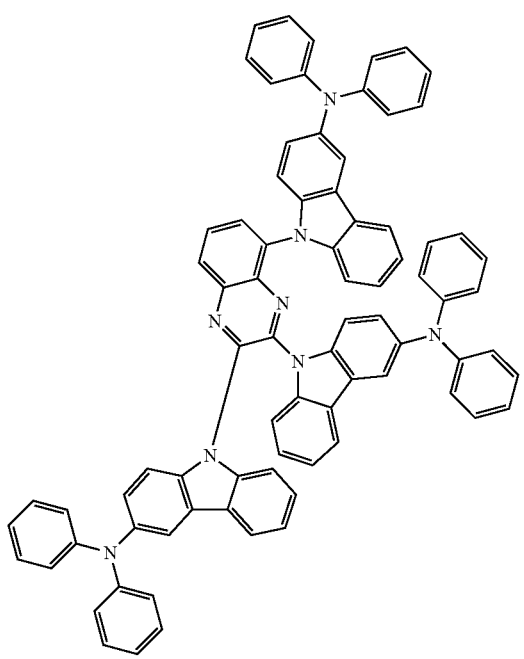

-continued
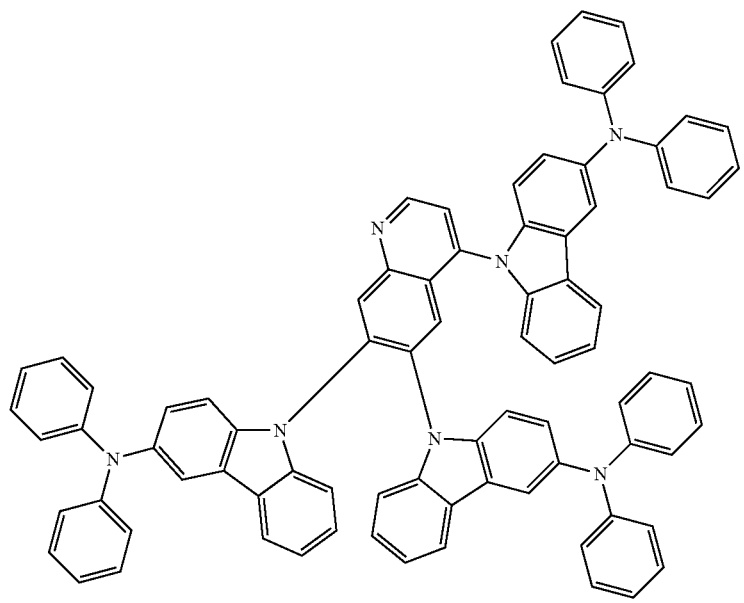
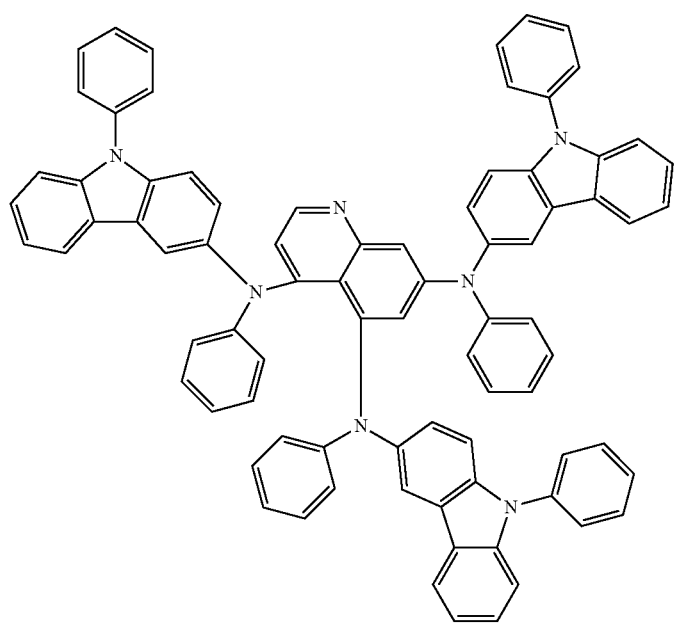

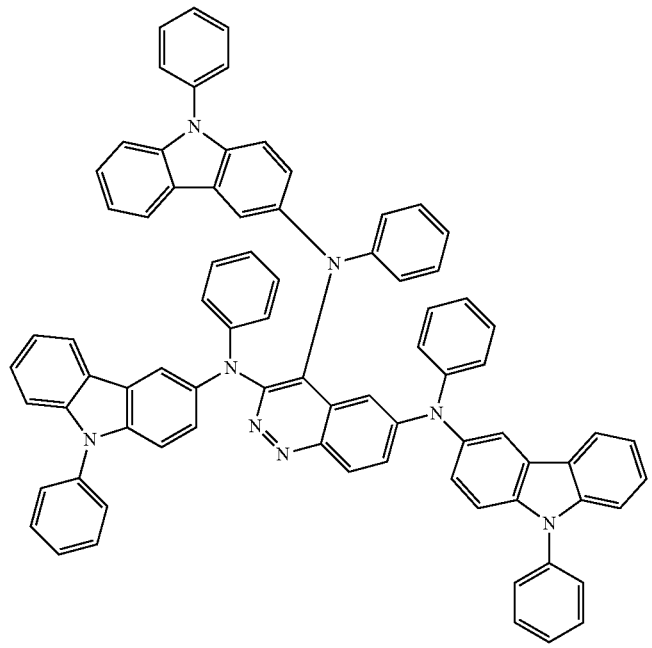
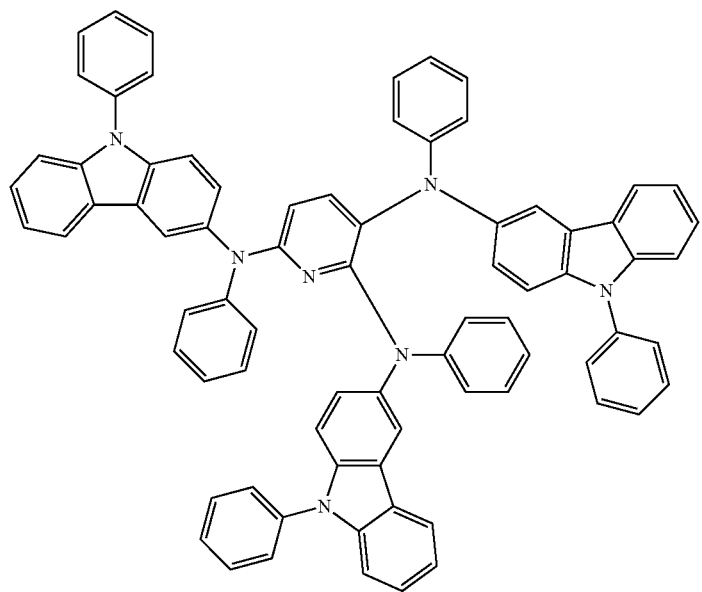

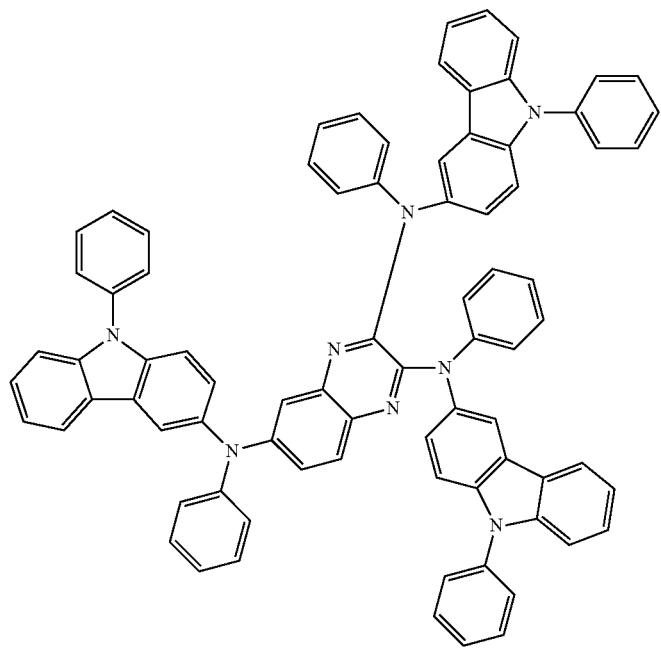
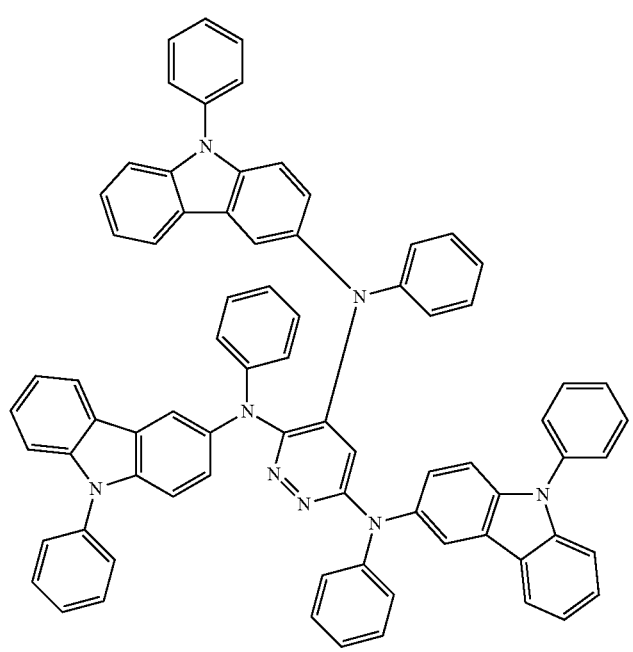

1119 1120
-continued
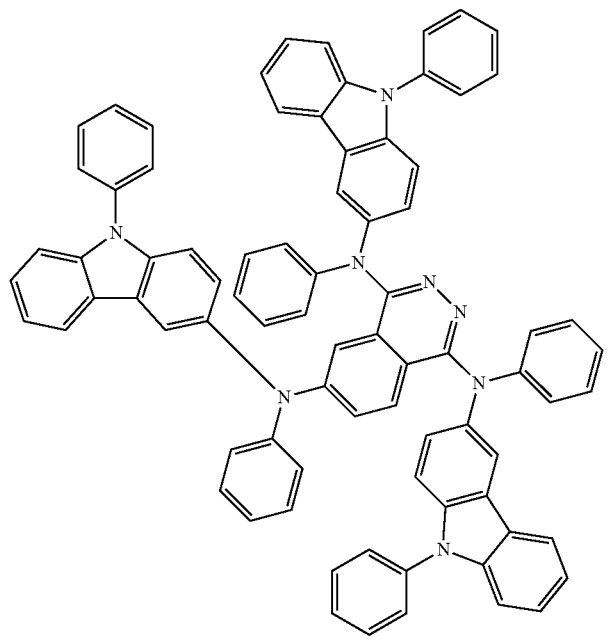
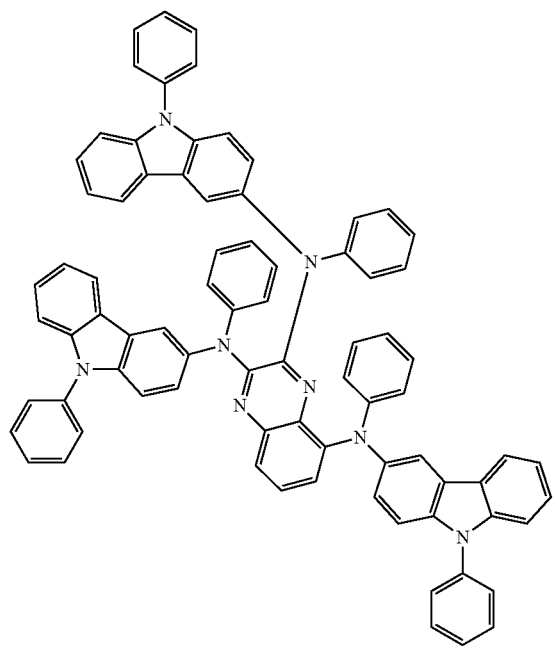 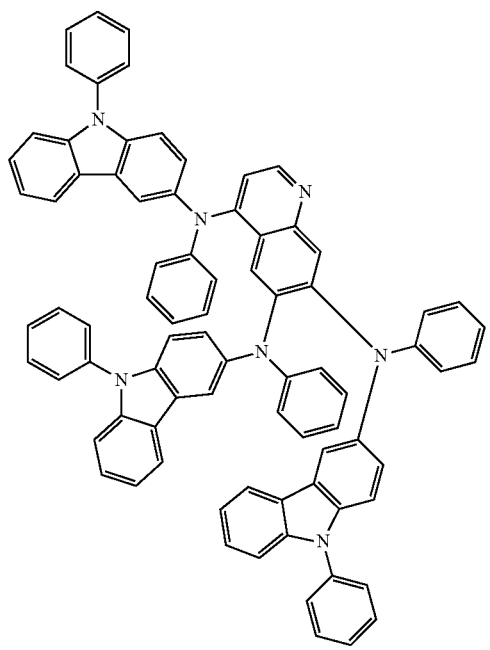

-continued
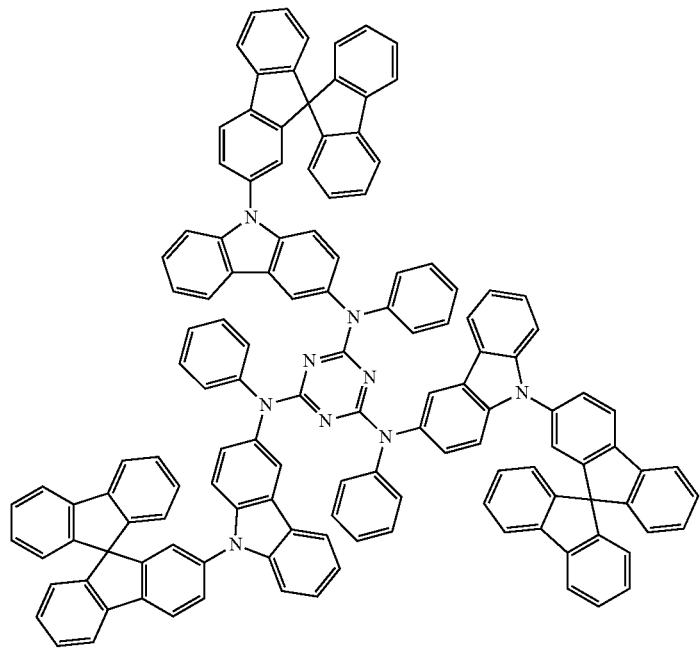
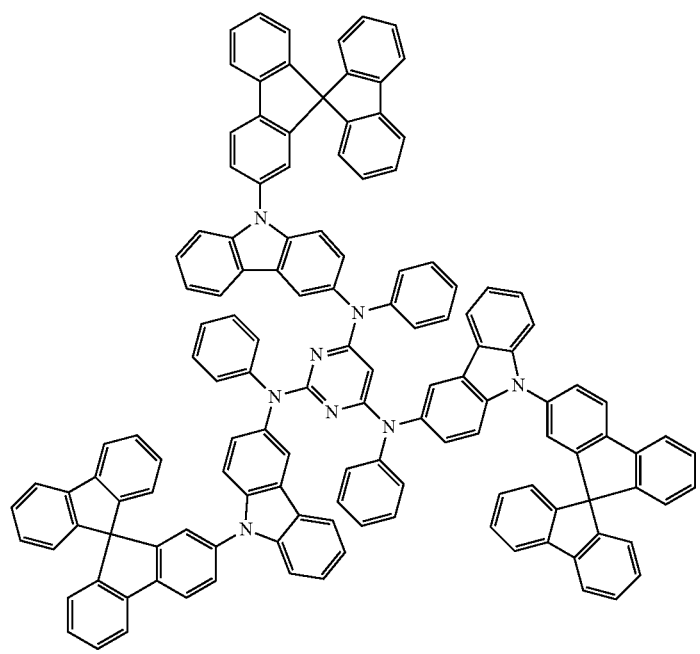

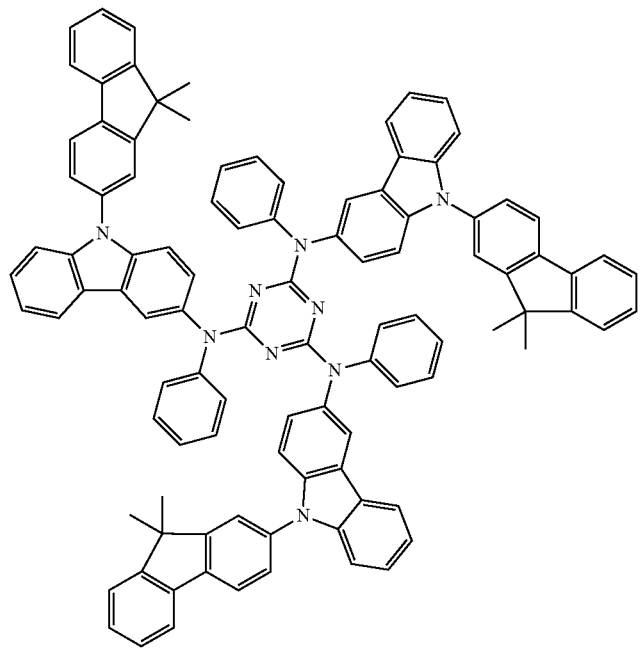

1125
-continued
1126
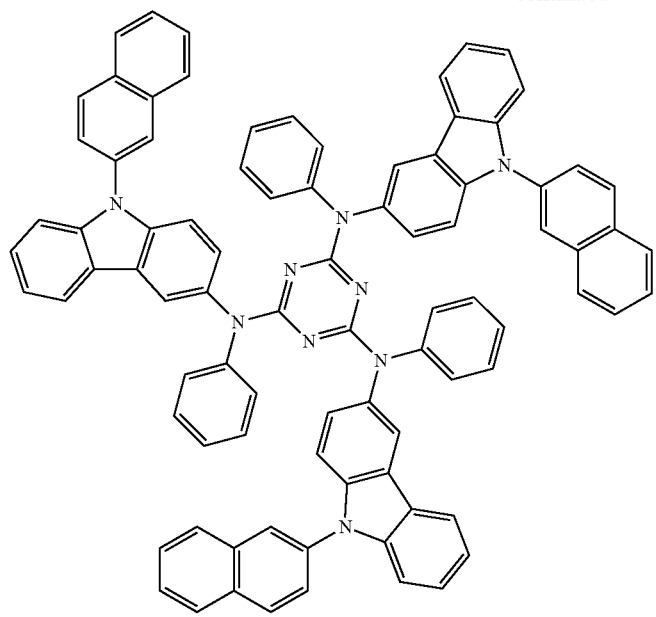
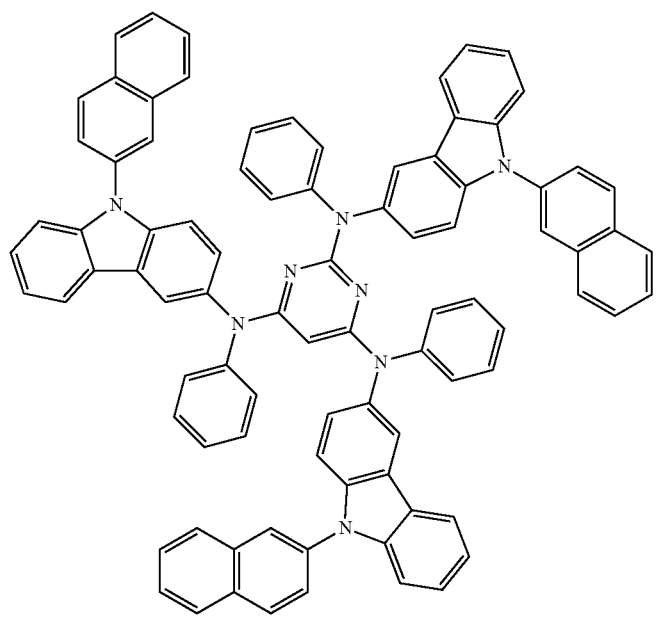
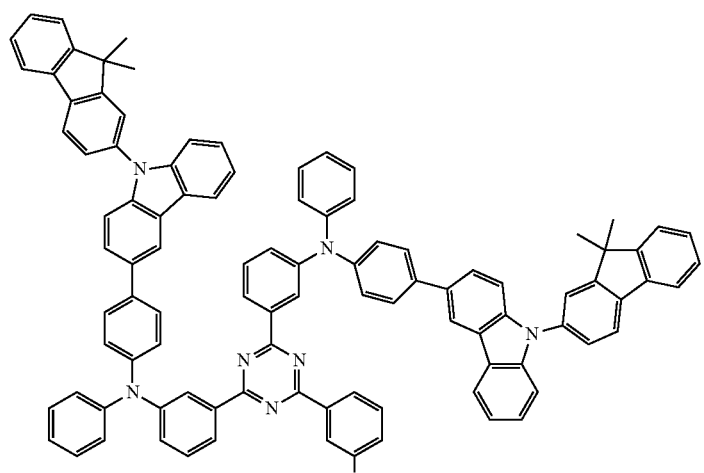

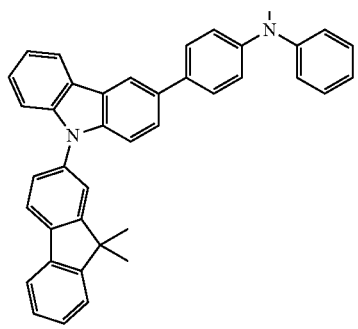
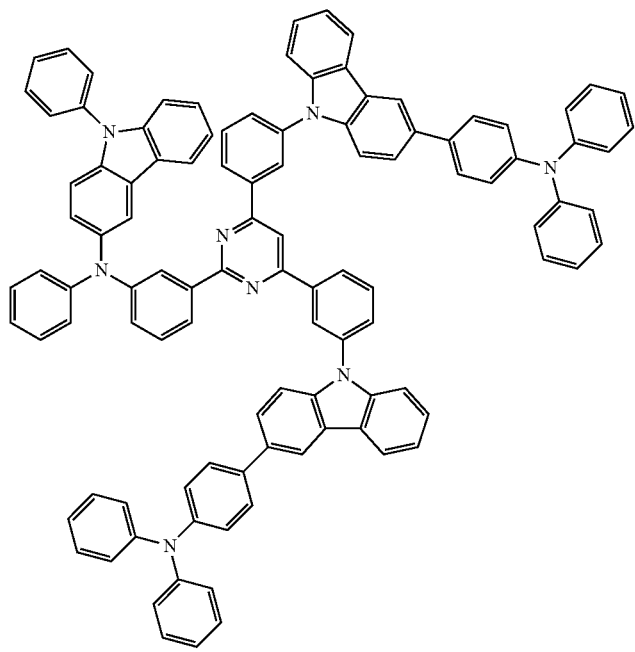
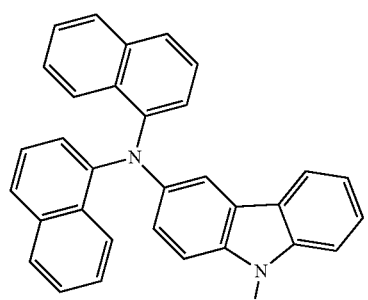

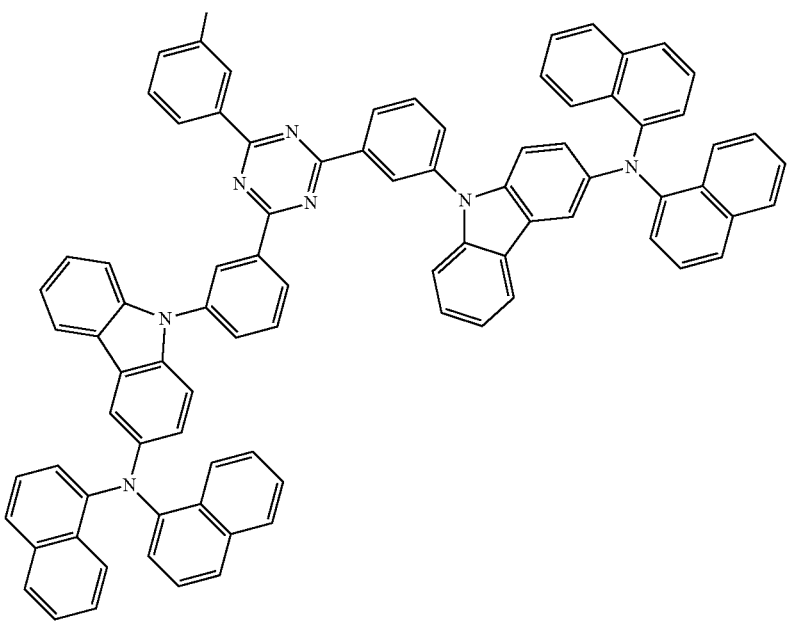
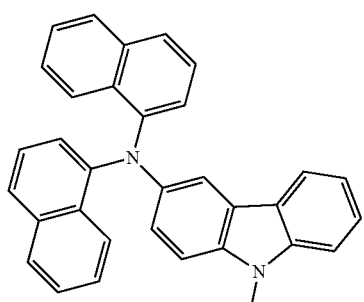
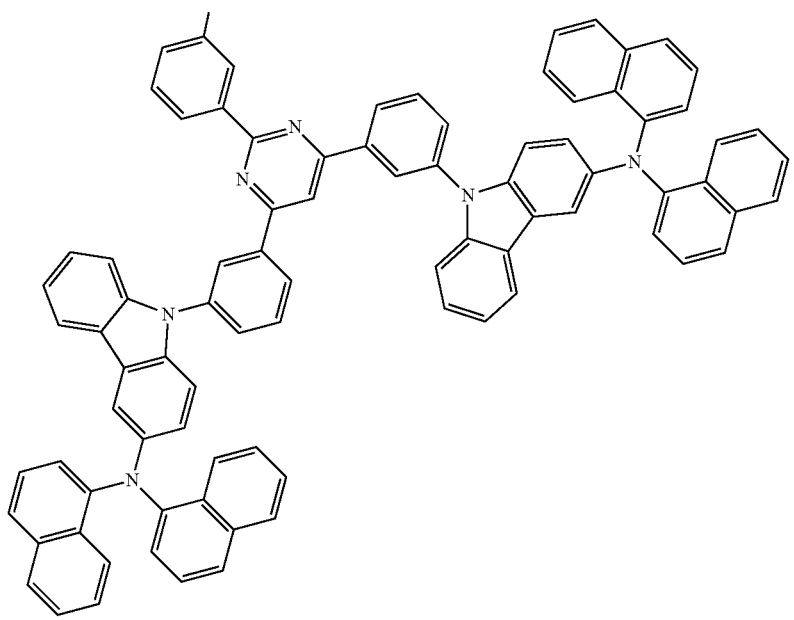

1131
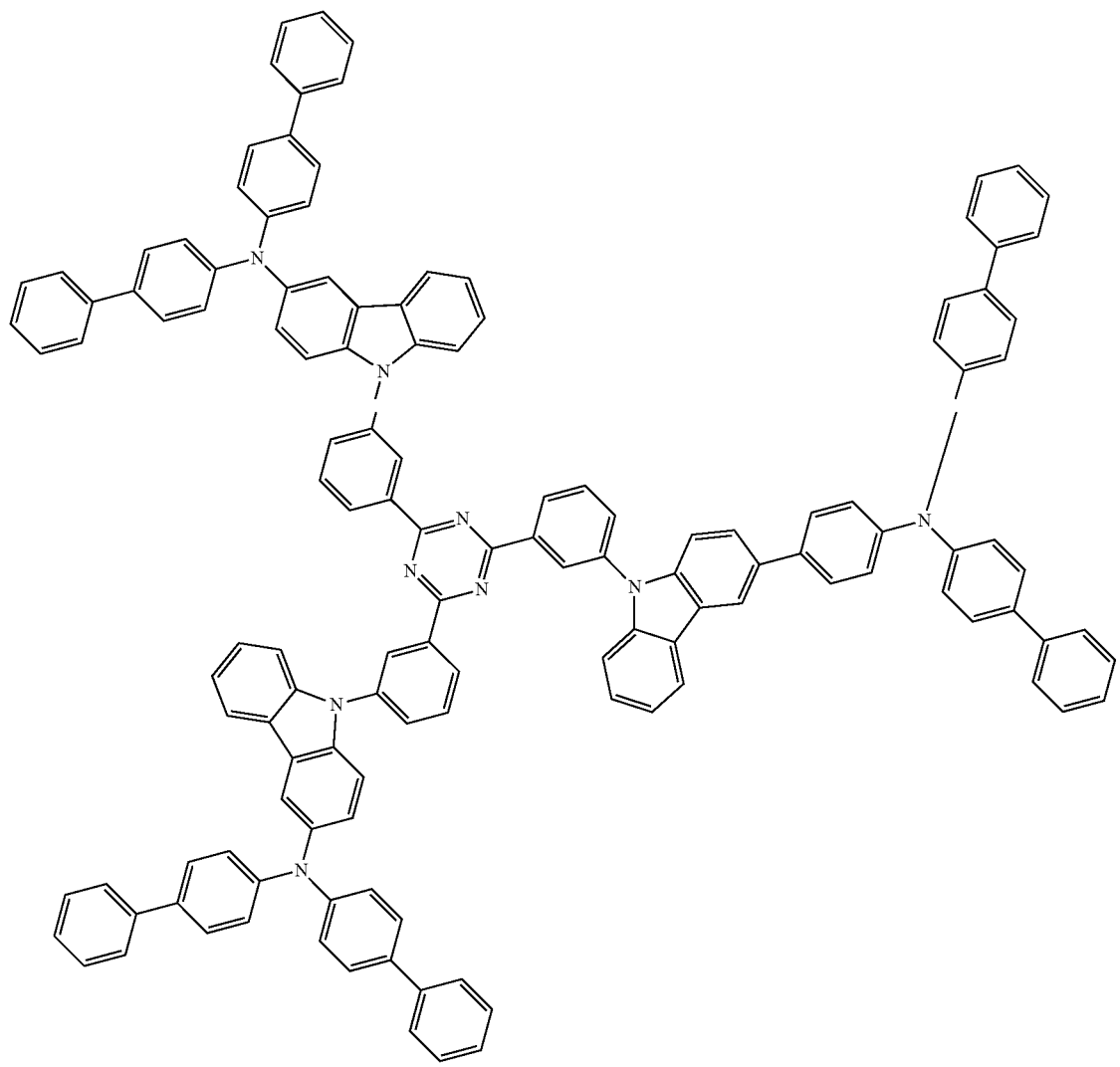 [SMILES: c1ccc(-c2ccc(N(c3ccc(-c4ccccc4)cc3)c3ccc(-c4ccc5c(c4)c4ccccc4n5-c4cccc(-c5nc(-c6cccc(-n7c8ccccc8c8cc(N(c9ccc(-c%10ccccc%10)cc9)c9ccc(-c%10ccccc%10)cc9)ccc87)c6)nc(-c6cccc(-n7c8ccccc8c8cc(N(c9ccc(-c%10ccccc%10)cc9)c9ccc(-c%10ccccc%10)cc9)ccc87)c6)n5)c4)cc3)cc2)cc1]
1132
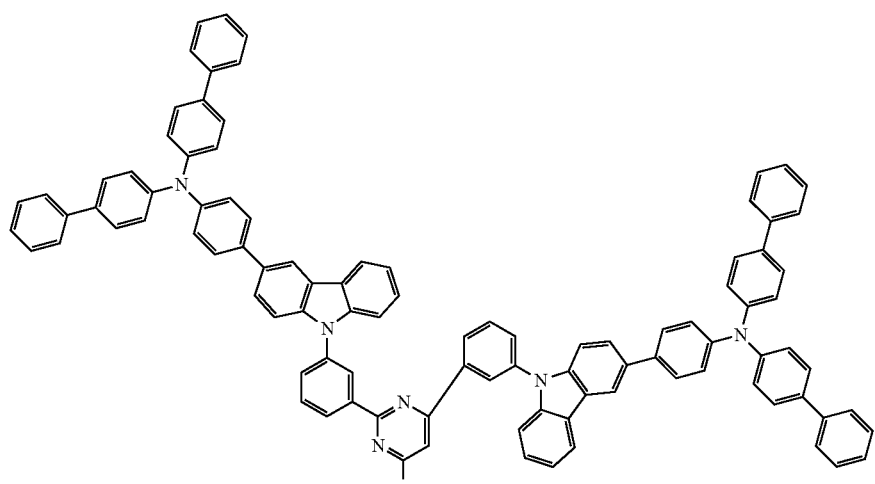

1133 1134
-continued
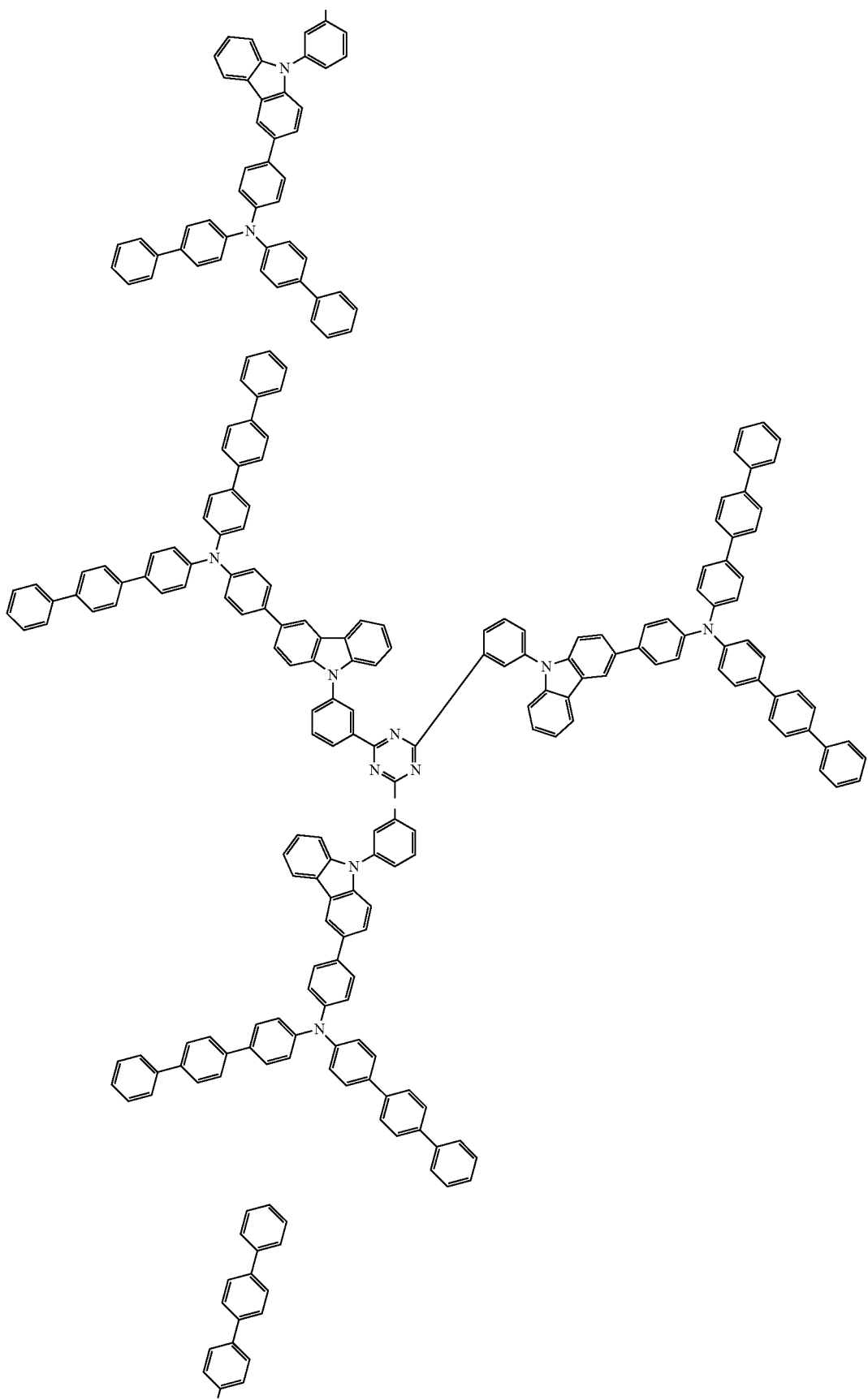

1135 1136
-continued
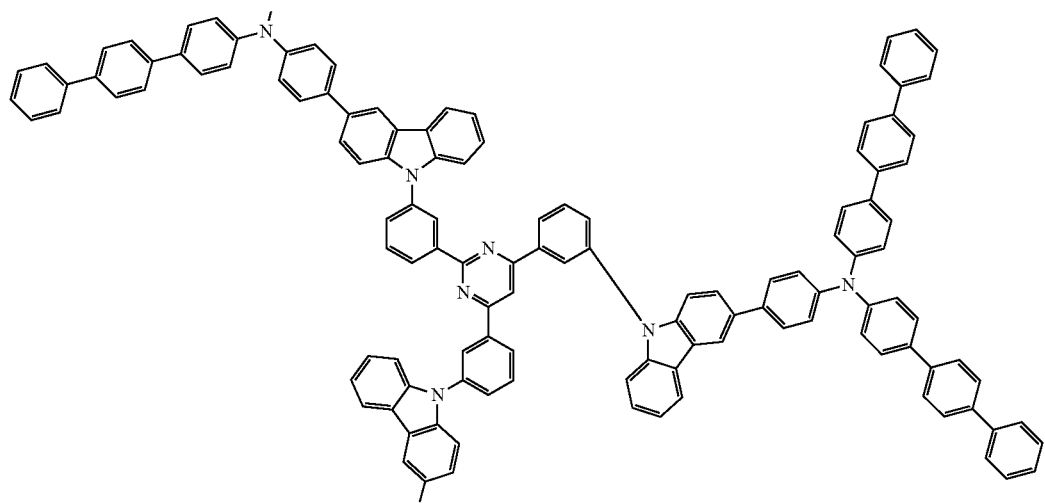
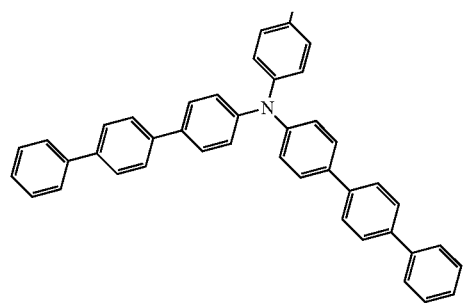
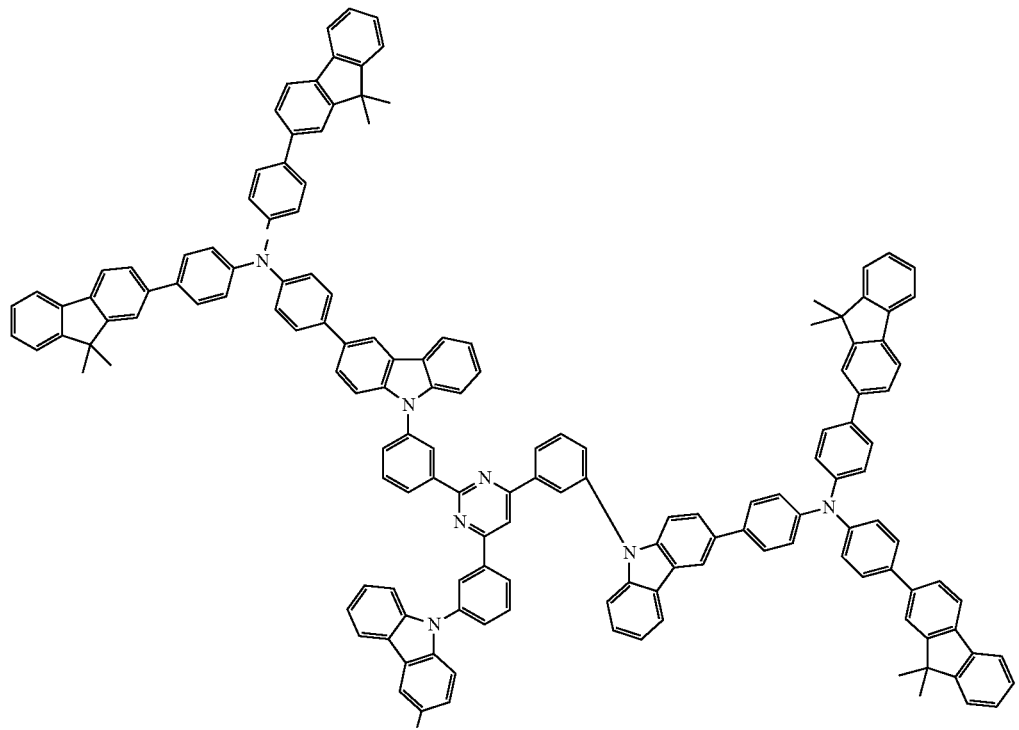

1137
1138
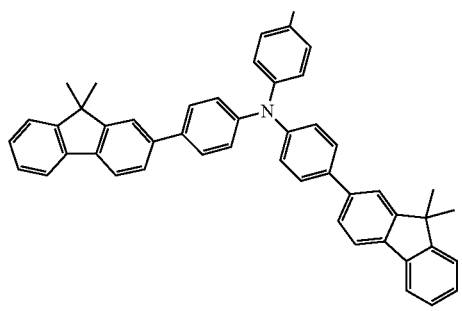
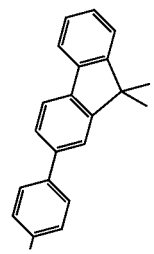
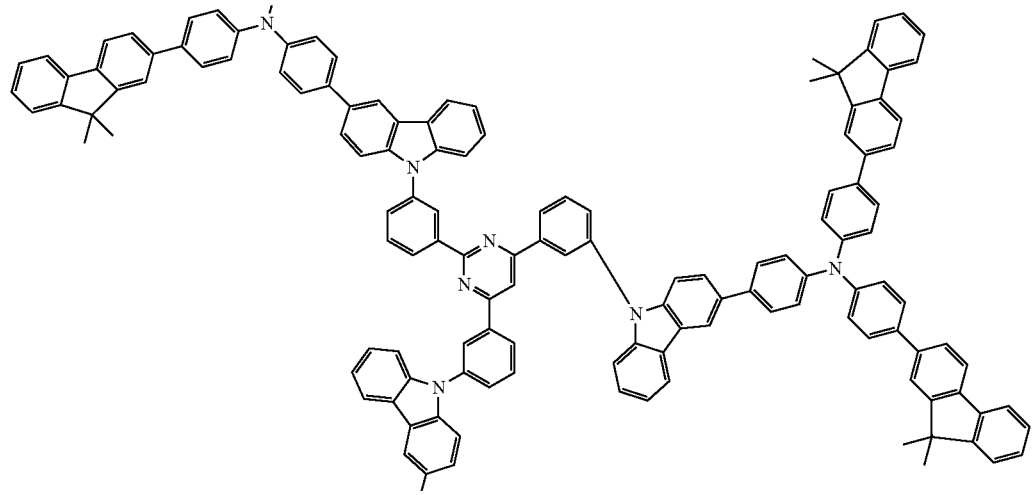

-continued
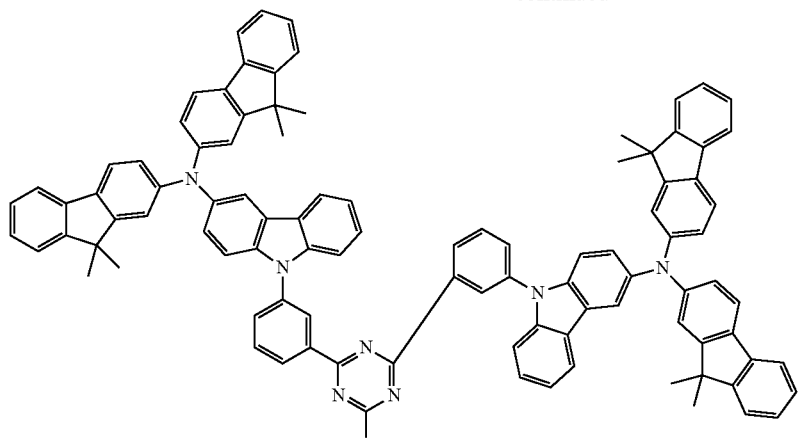
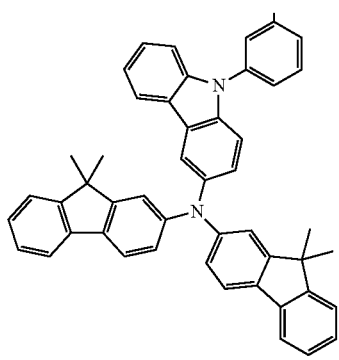
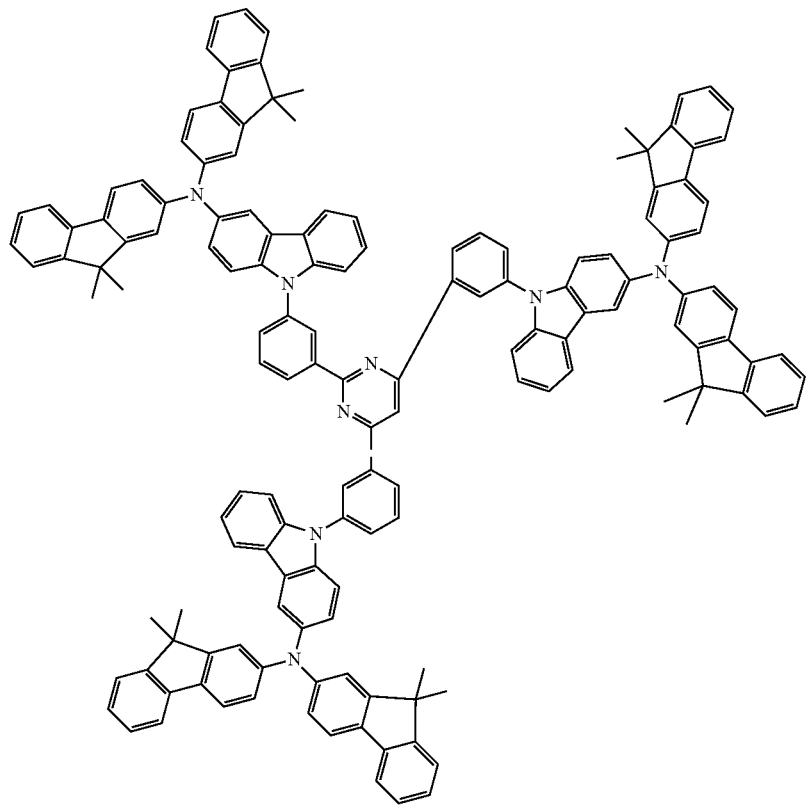

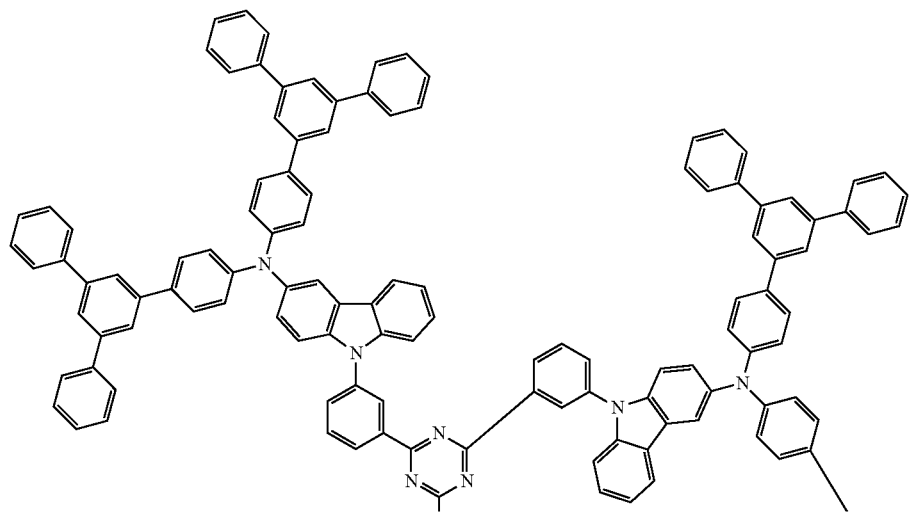
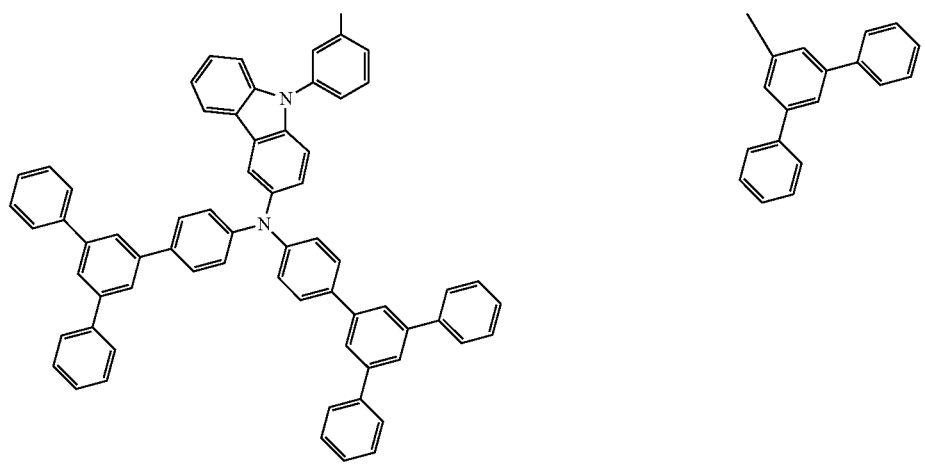
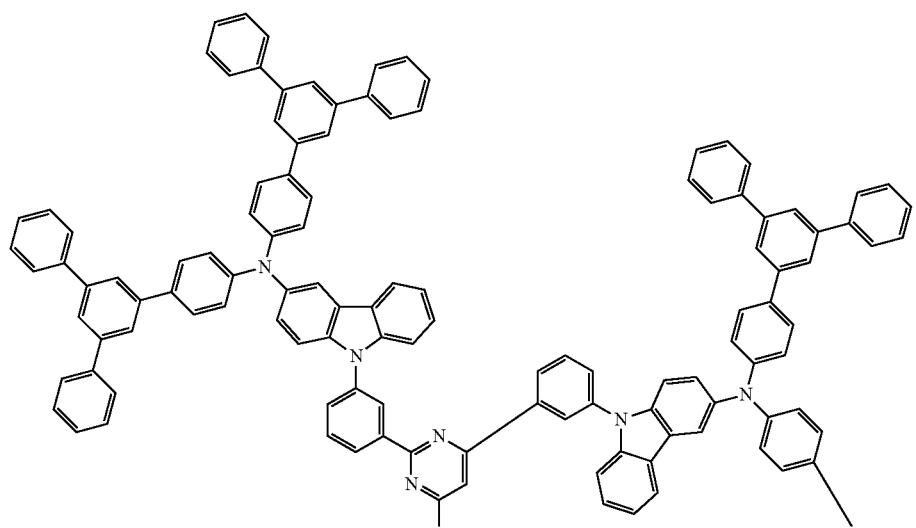

1143
1144
-continued
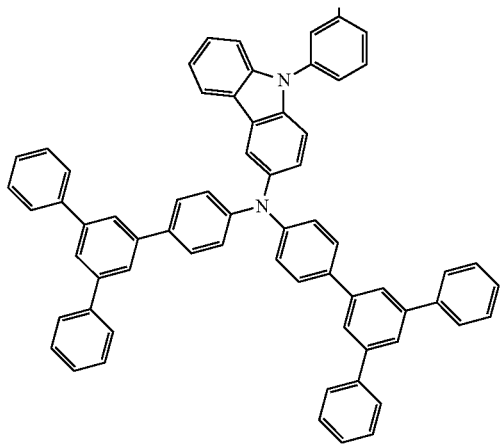
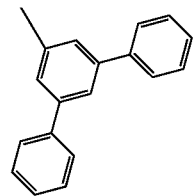
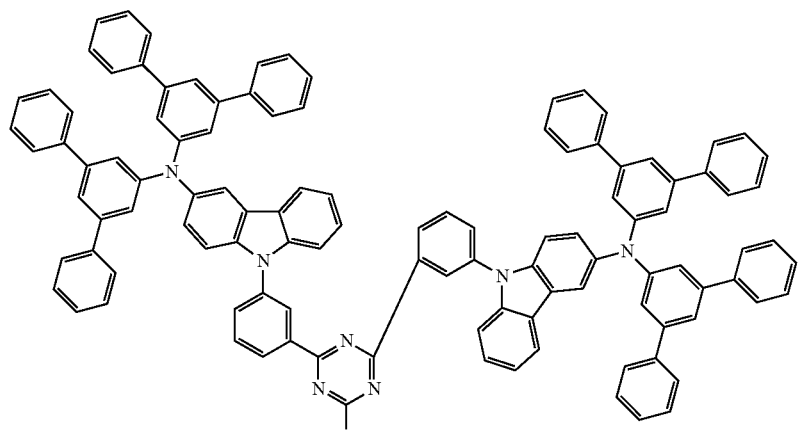
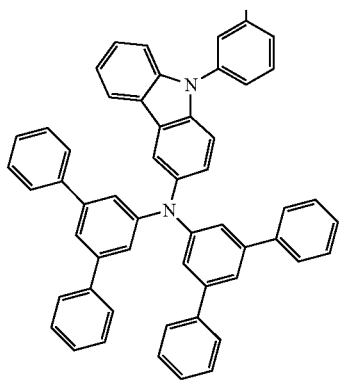
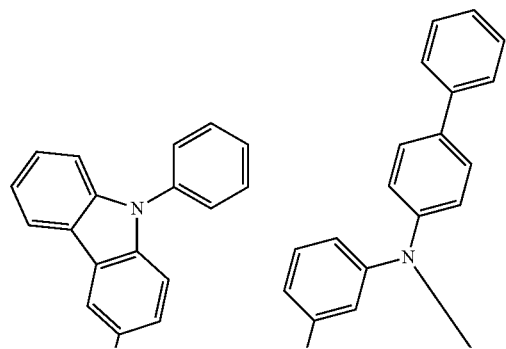

1145
-continued
1146
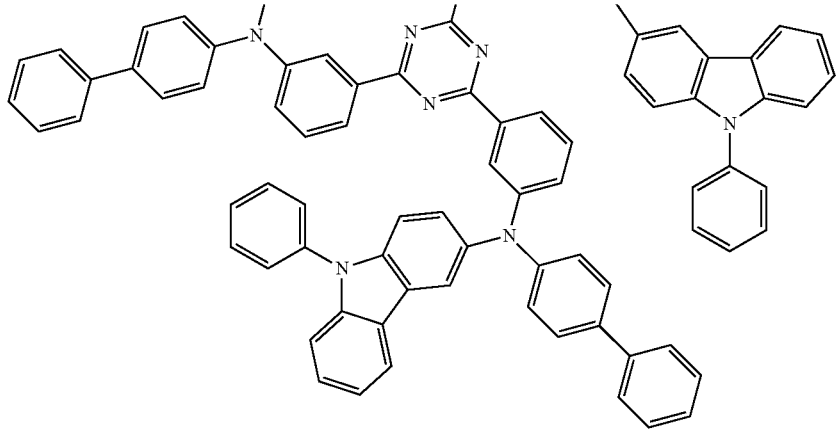
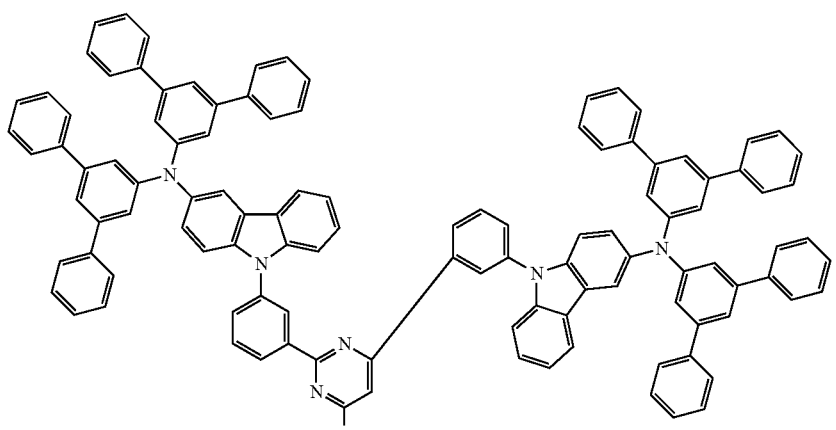
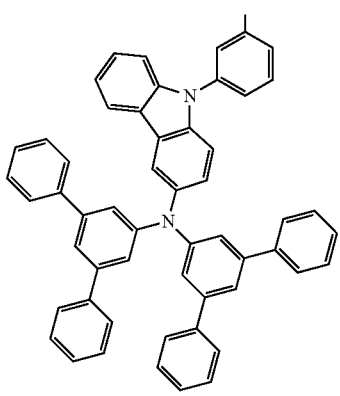
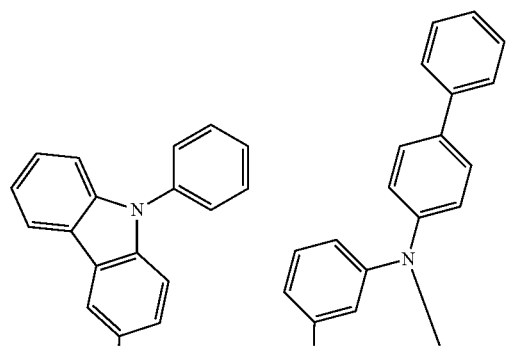

-continued
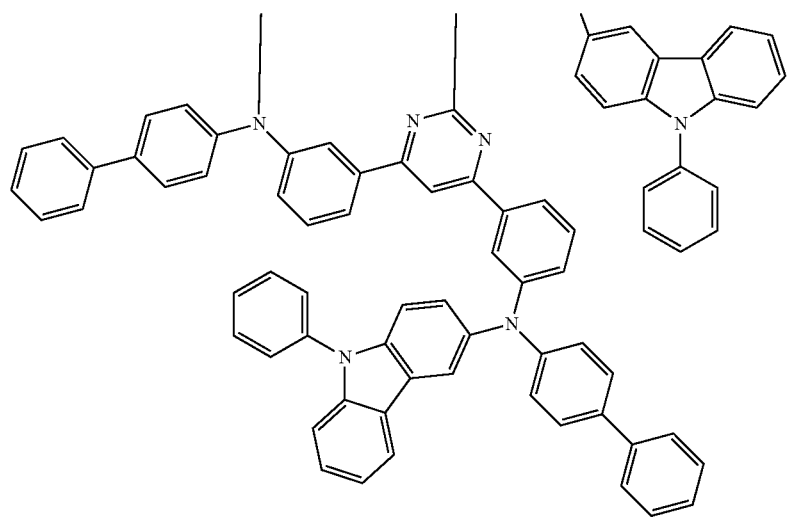
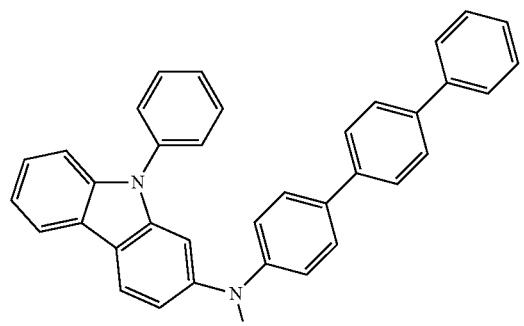
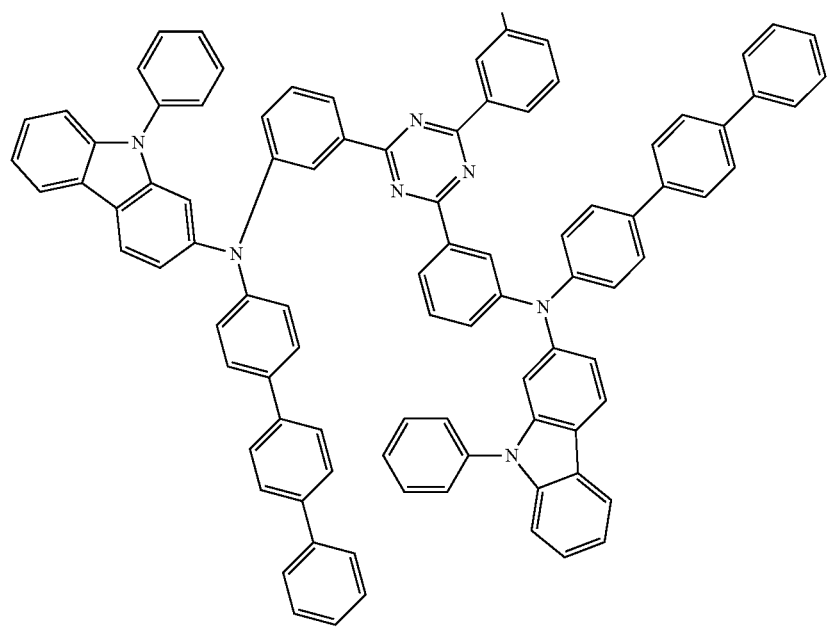

1149 1150
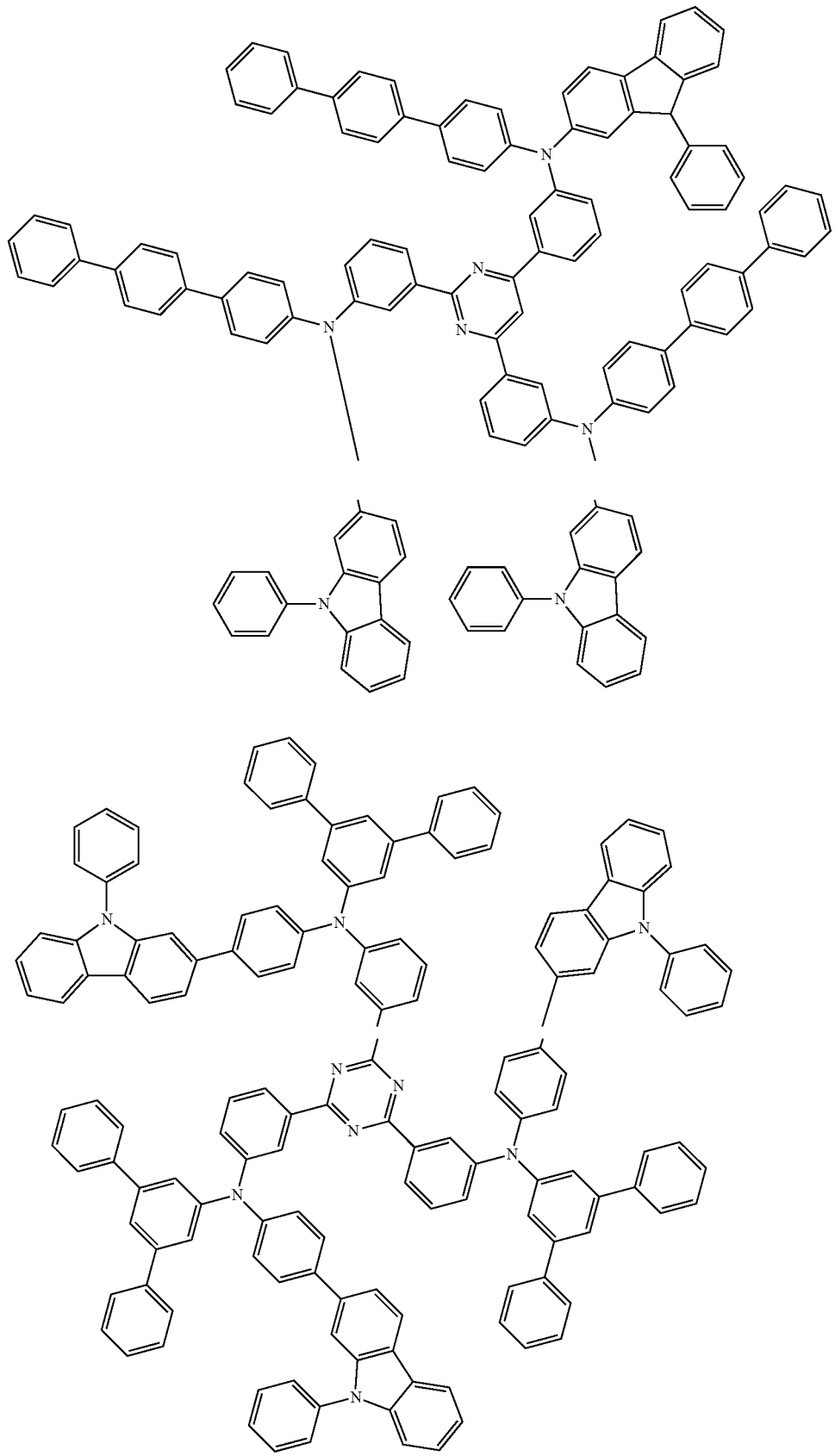

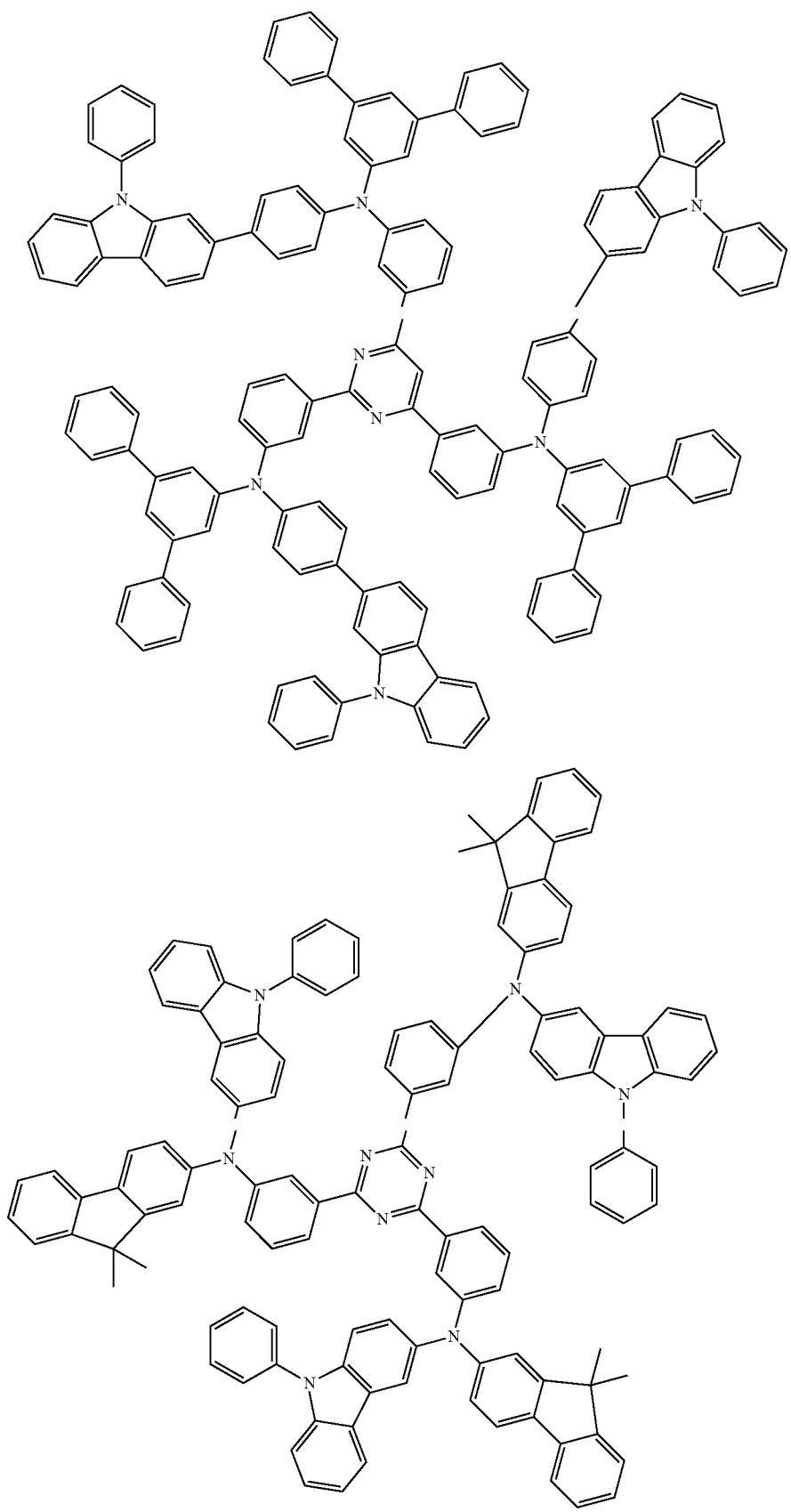

1153 1154
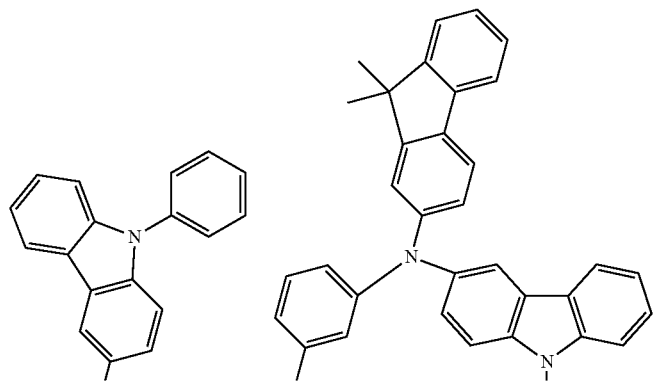
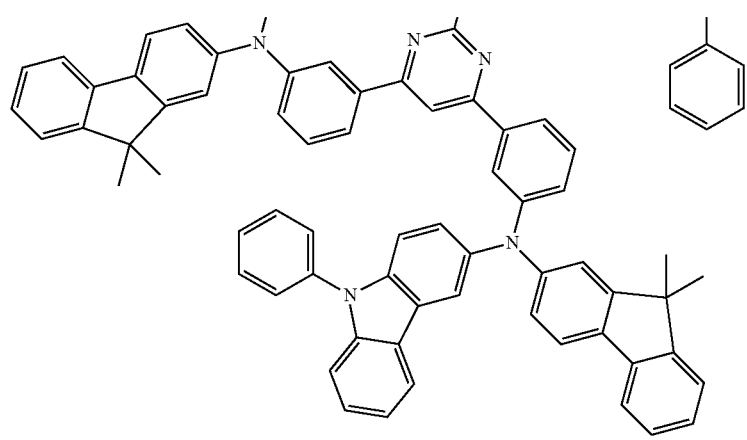
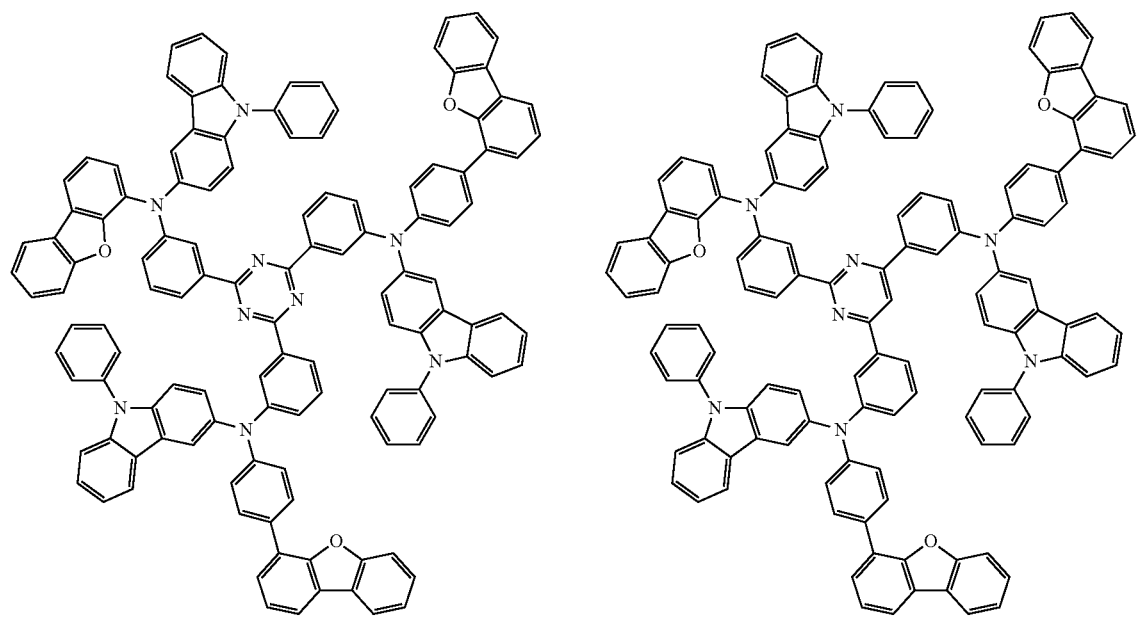

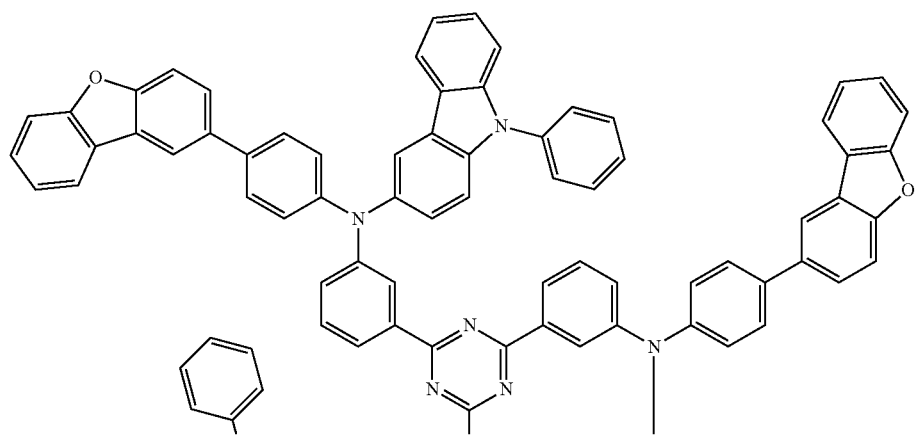
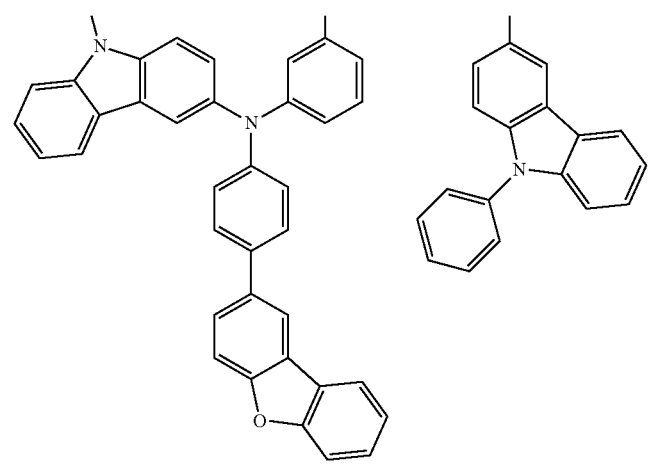
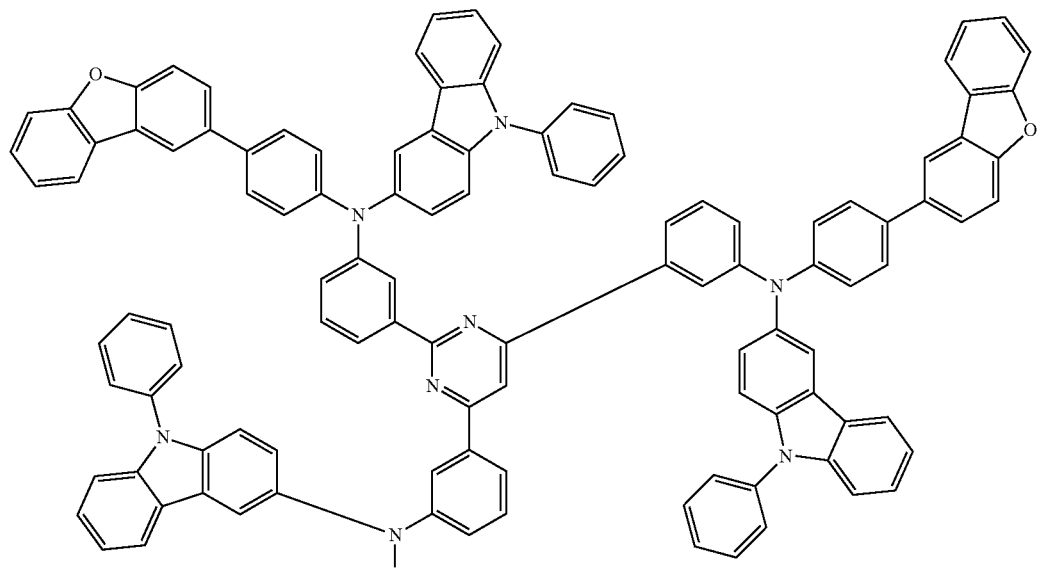

1157
1158
-continued
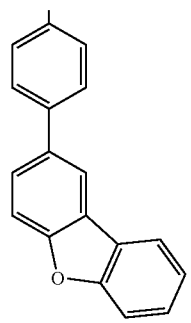
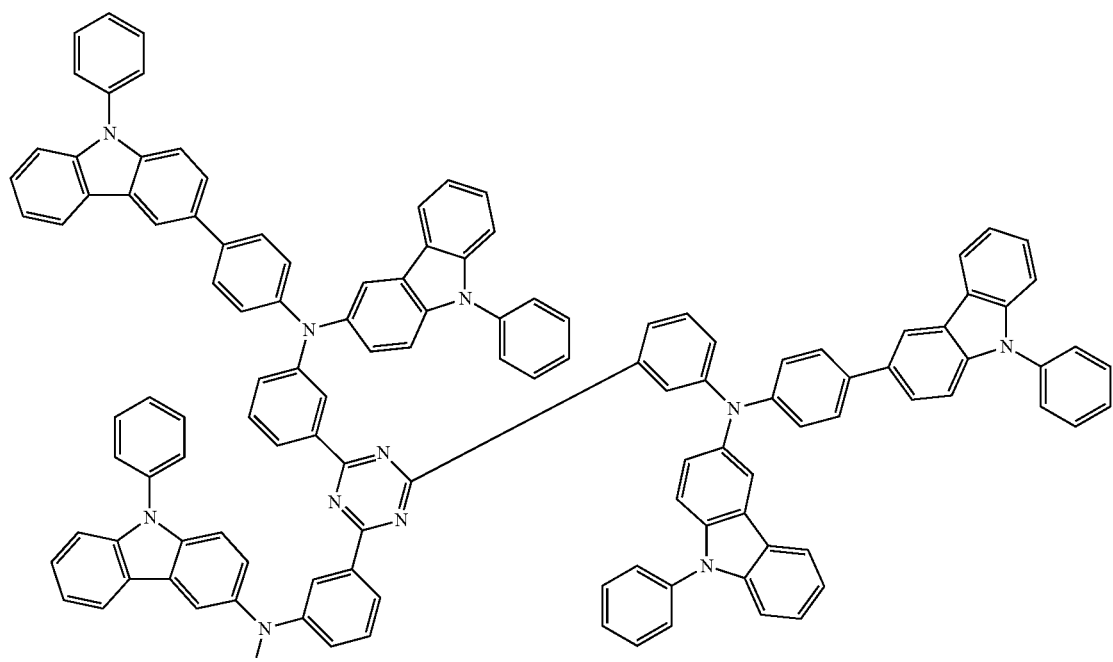
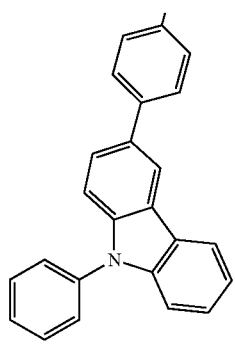

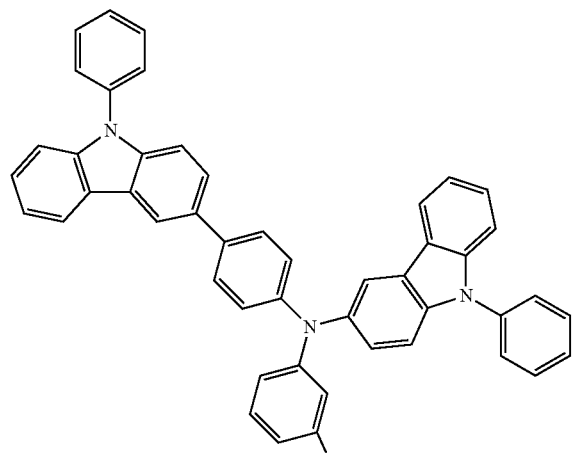
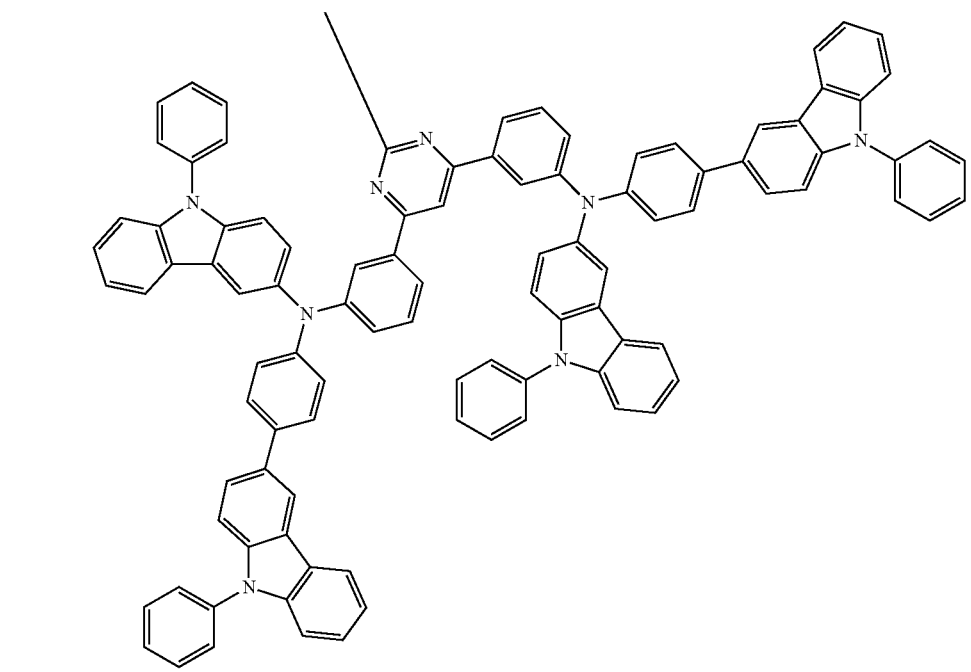
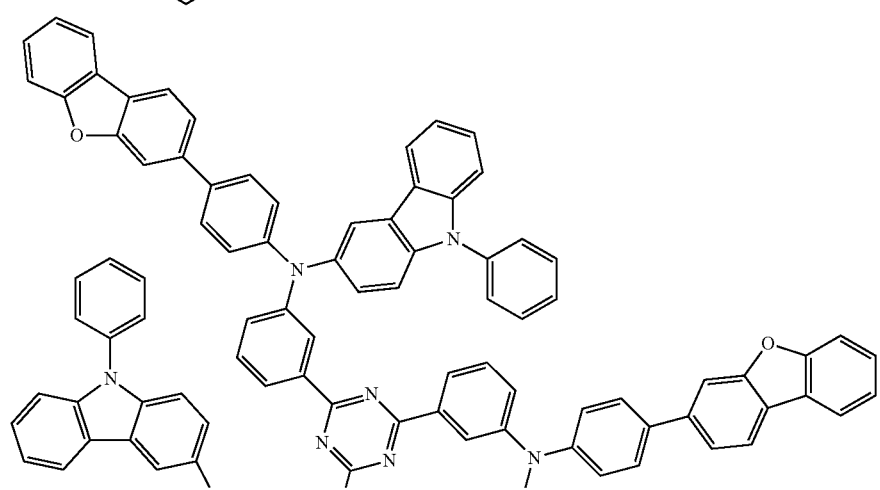

-continued
1161
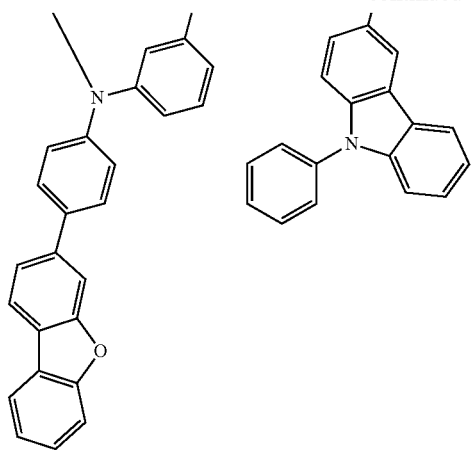
1162
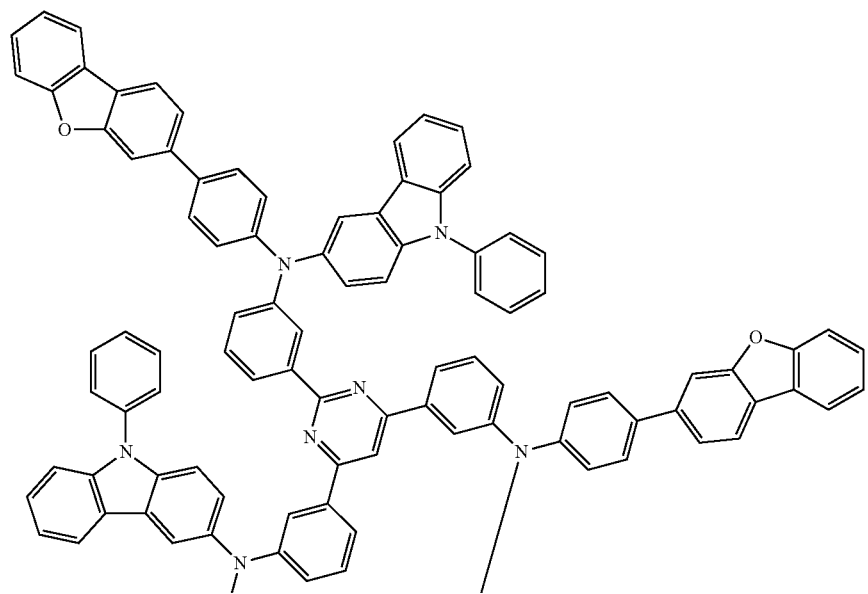
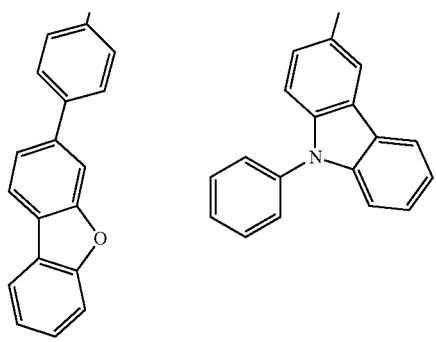

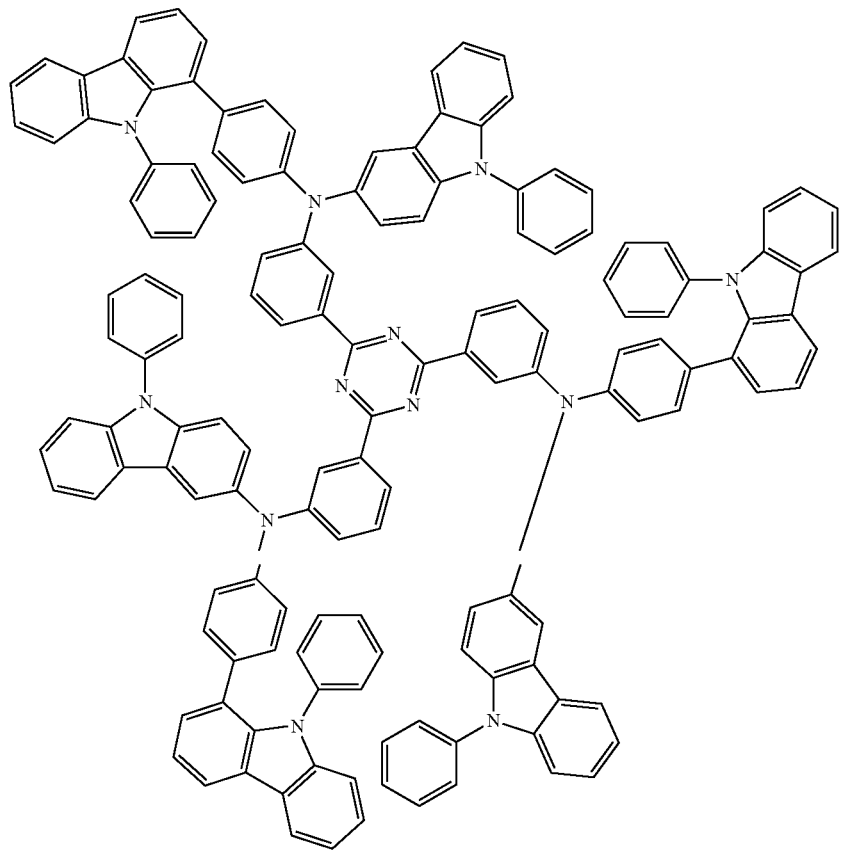
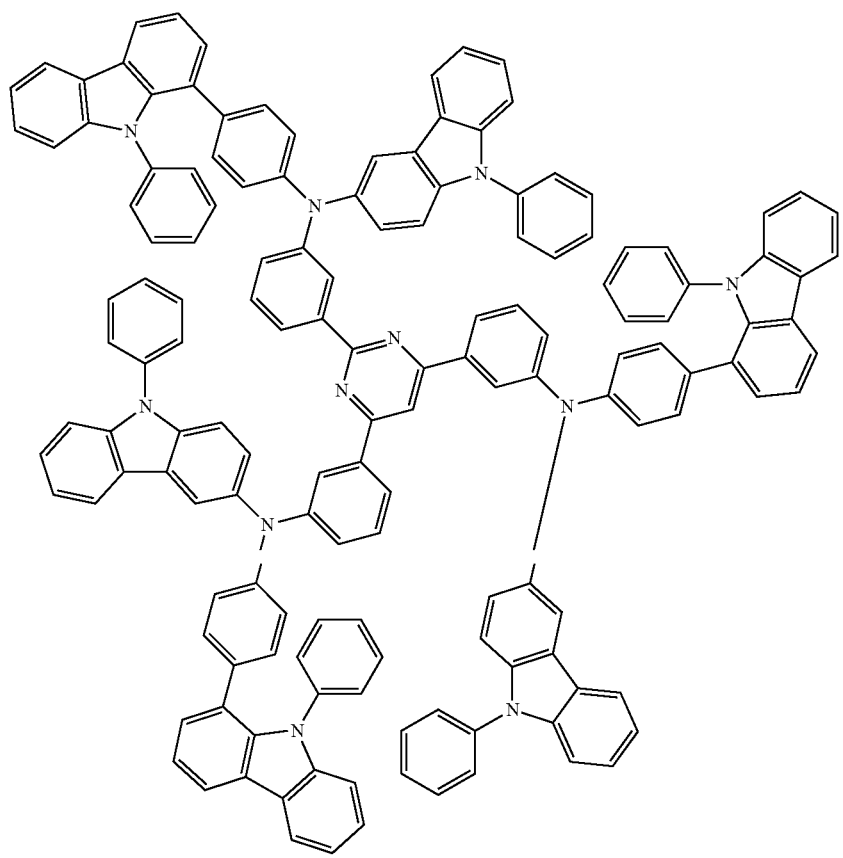

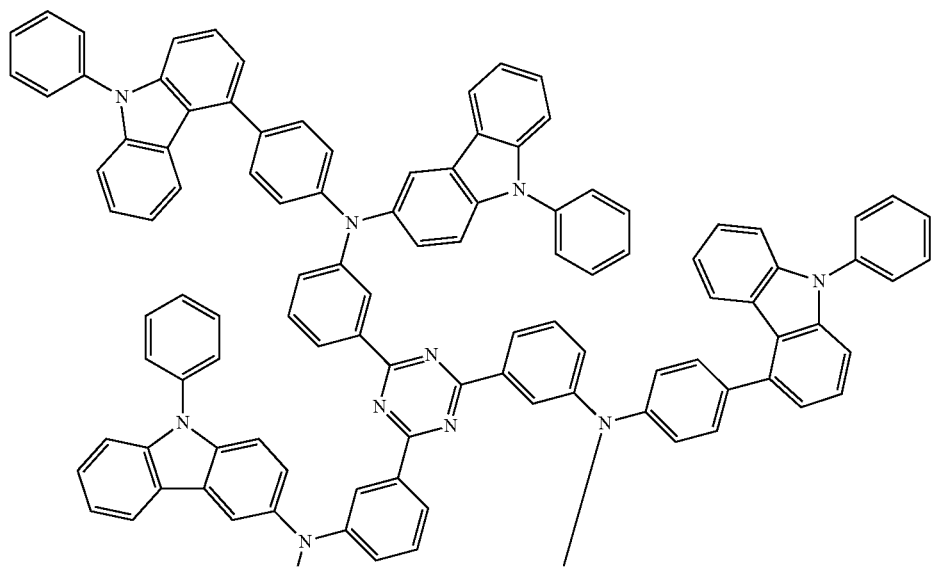
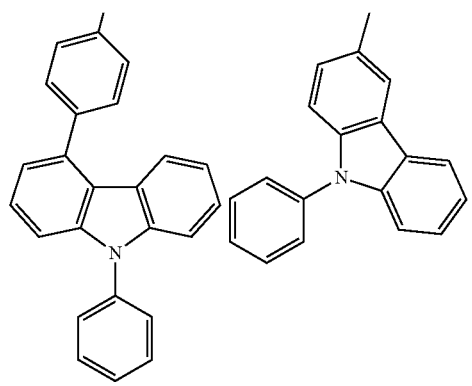
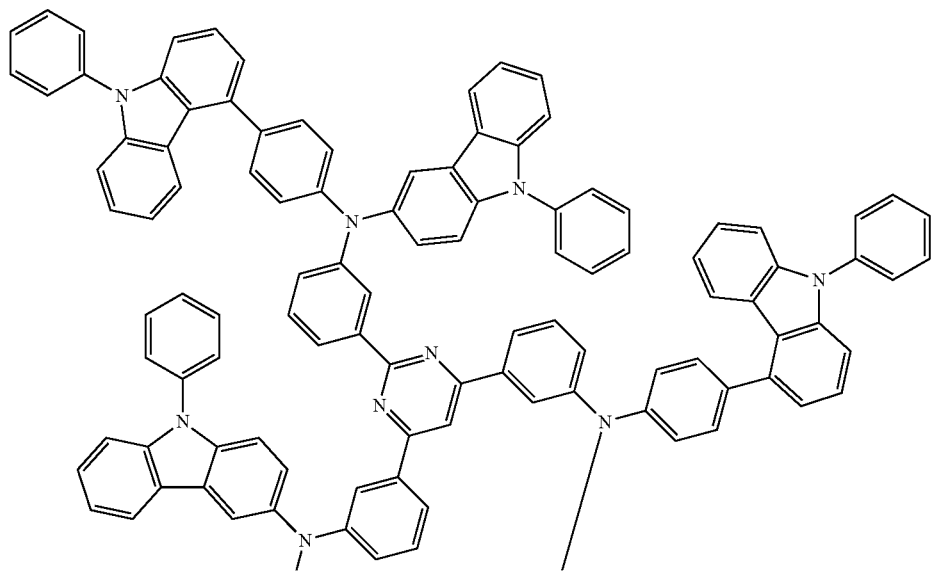

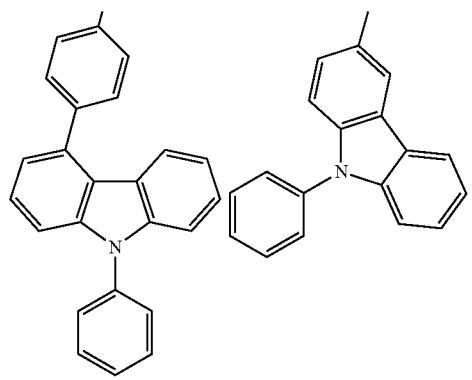
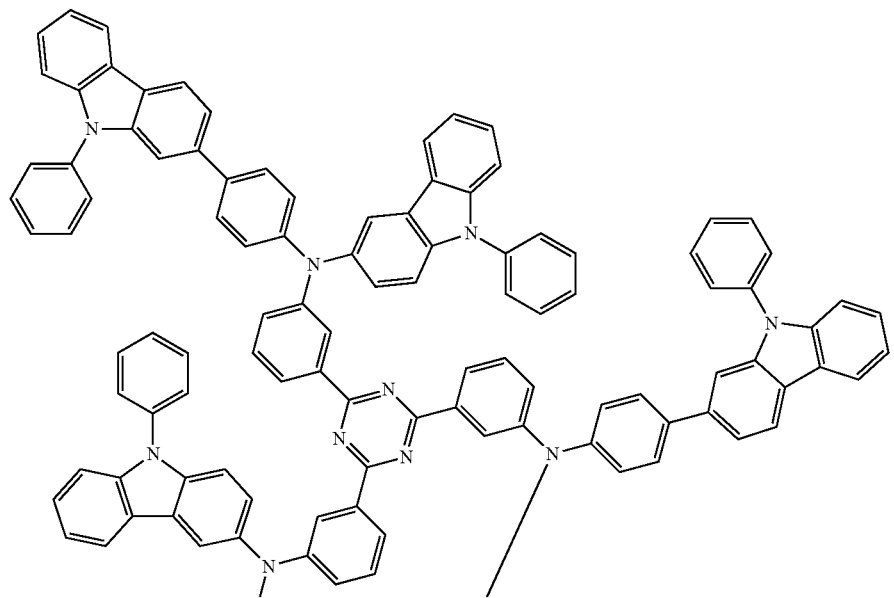
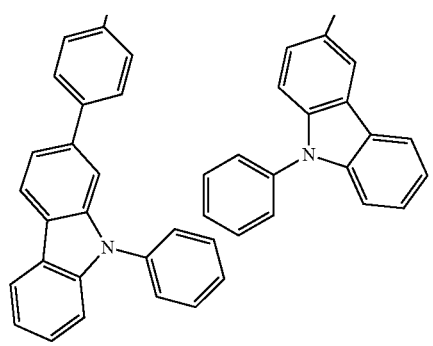
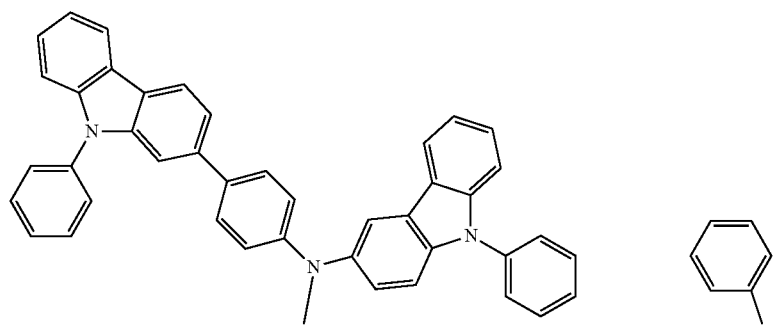
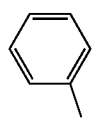

1169
1170
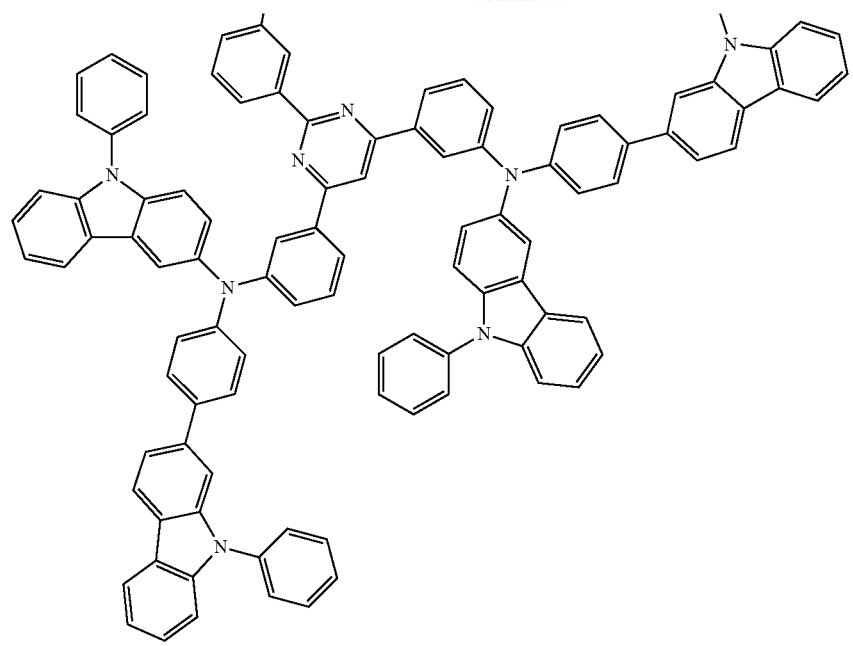
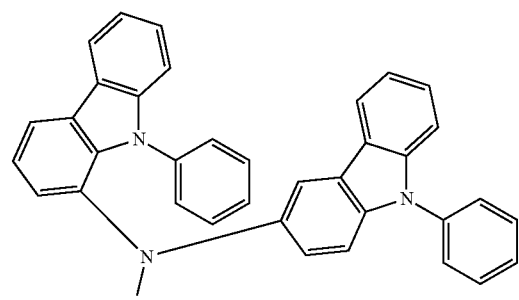
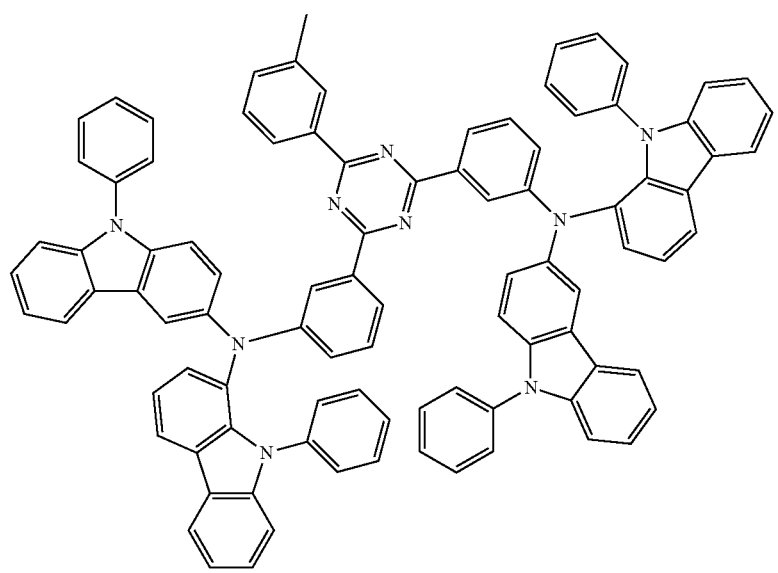

1171                  1172
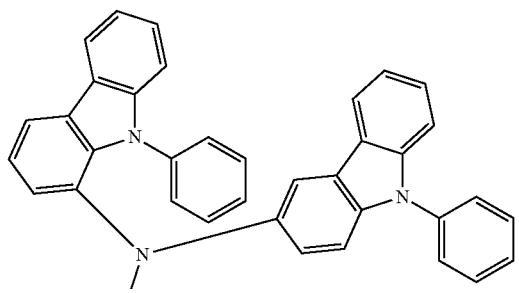
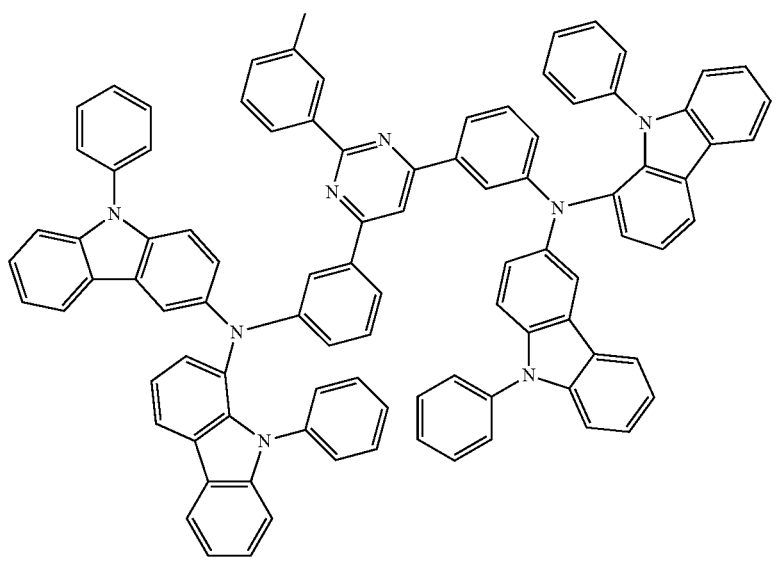
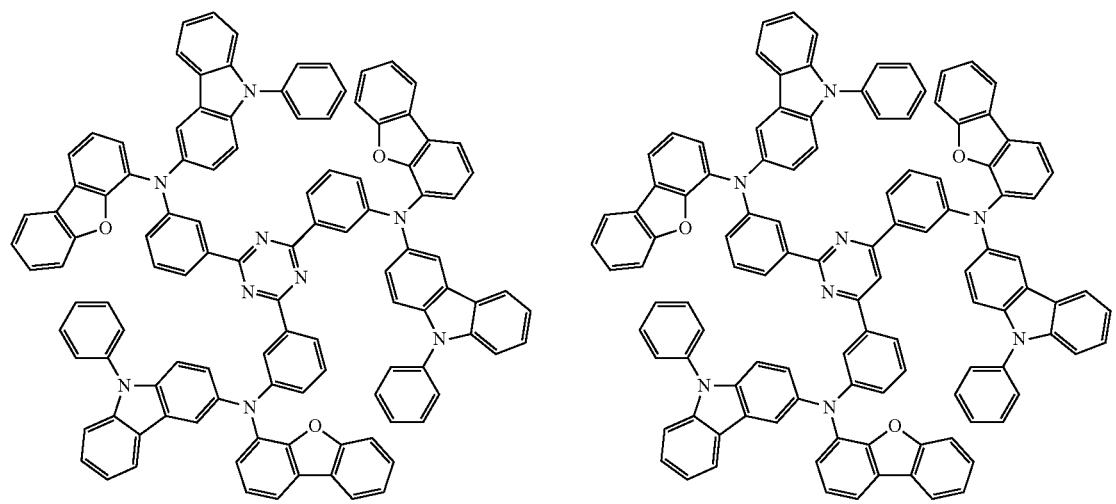

-continued
1173 1174
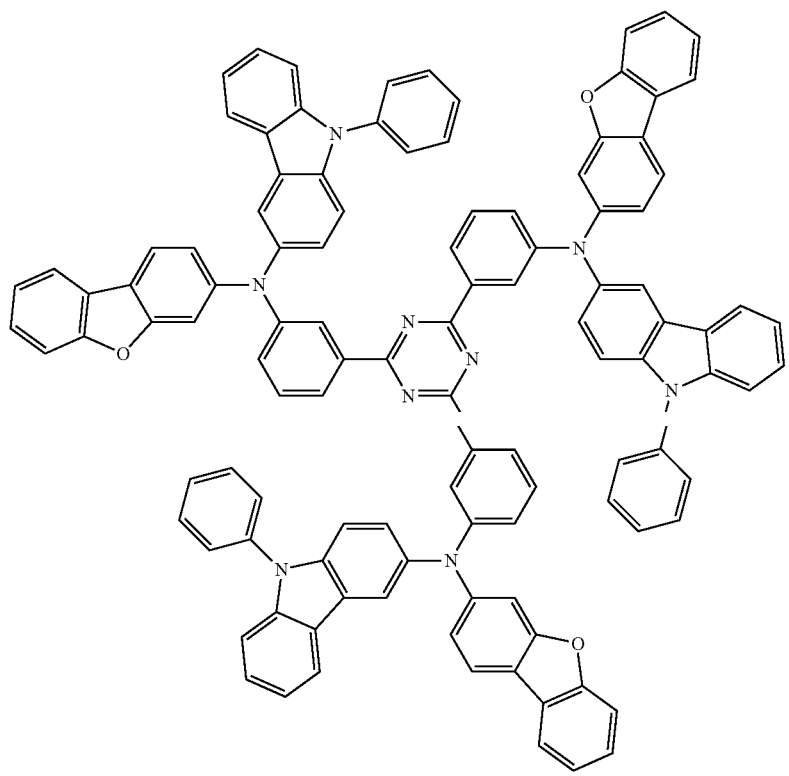
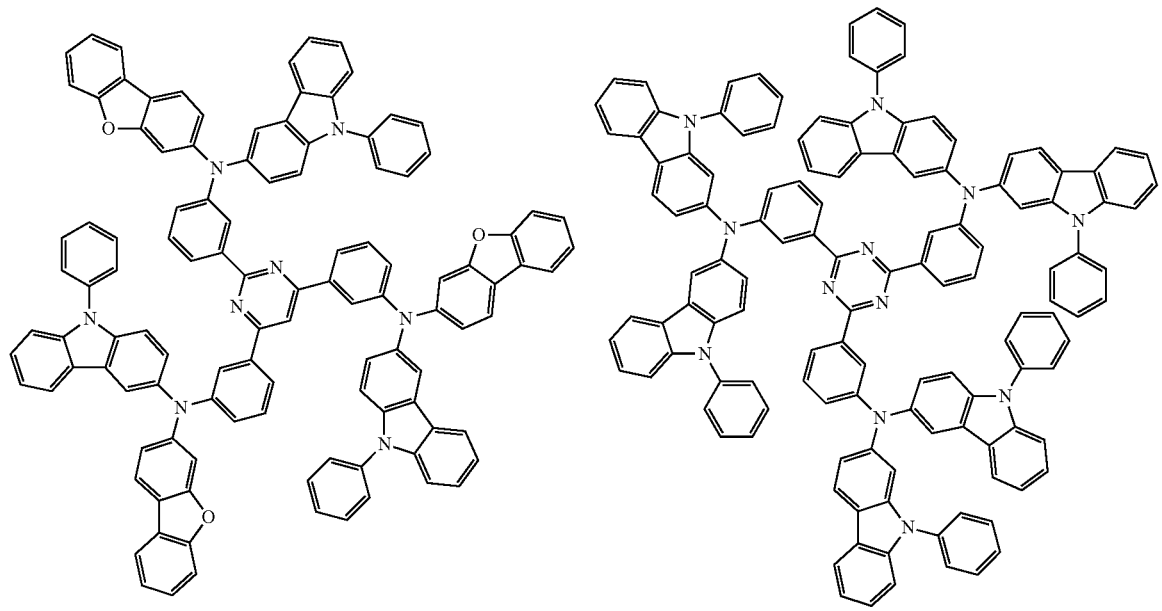
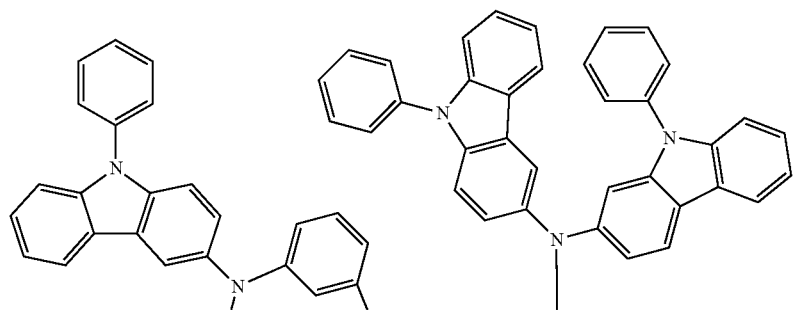

1175
1176
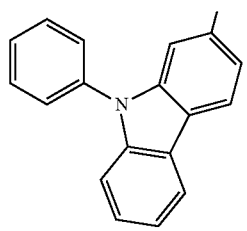
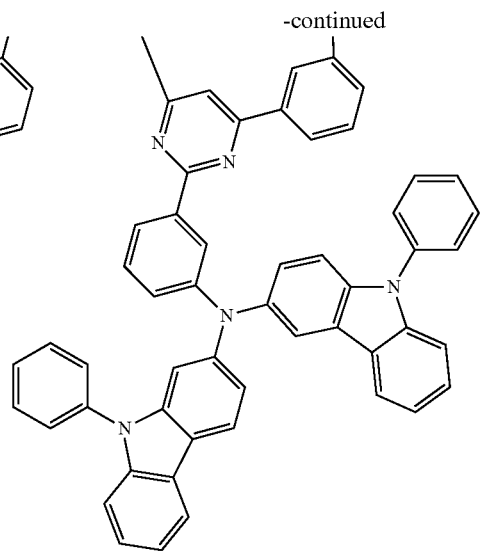
-continued
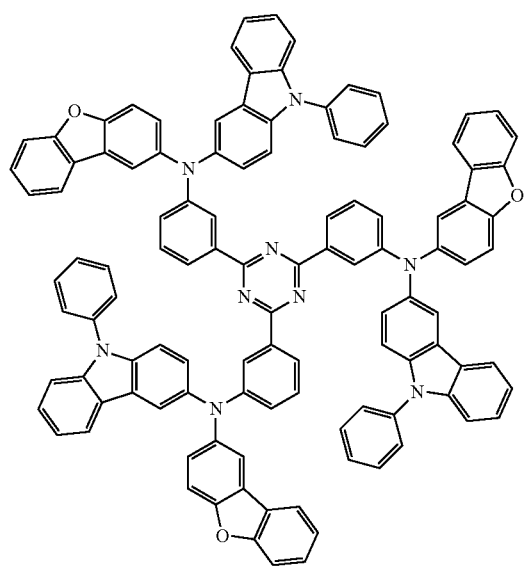
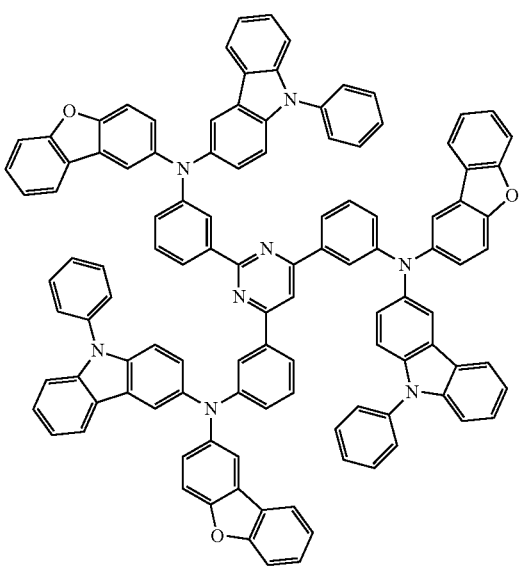
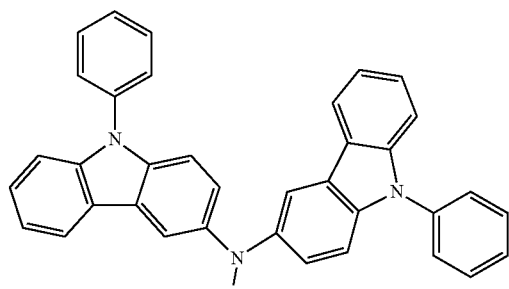

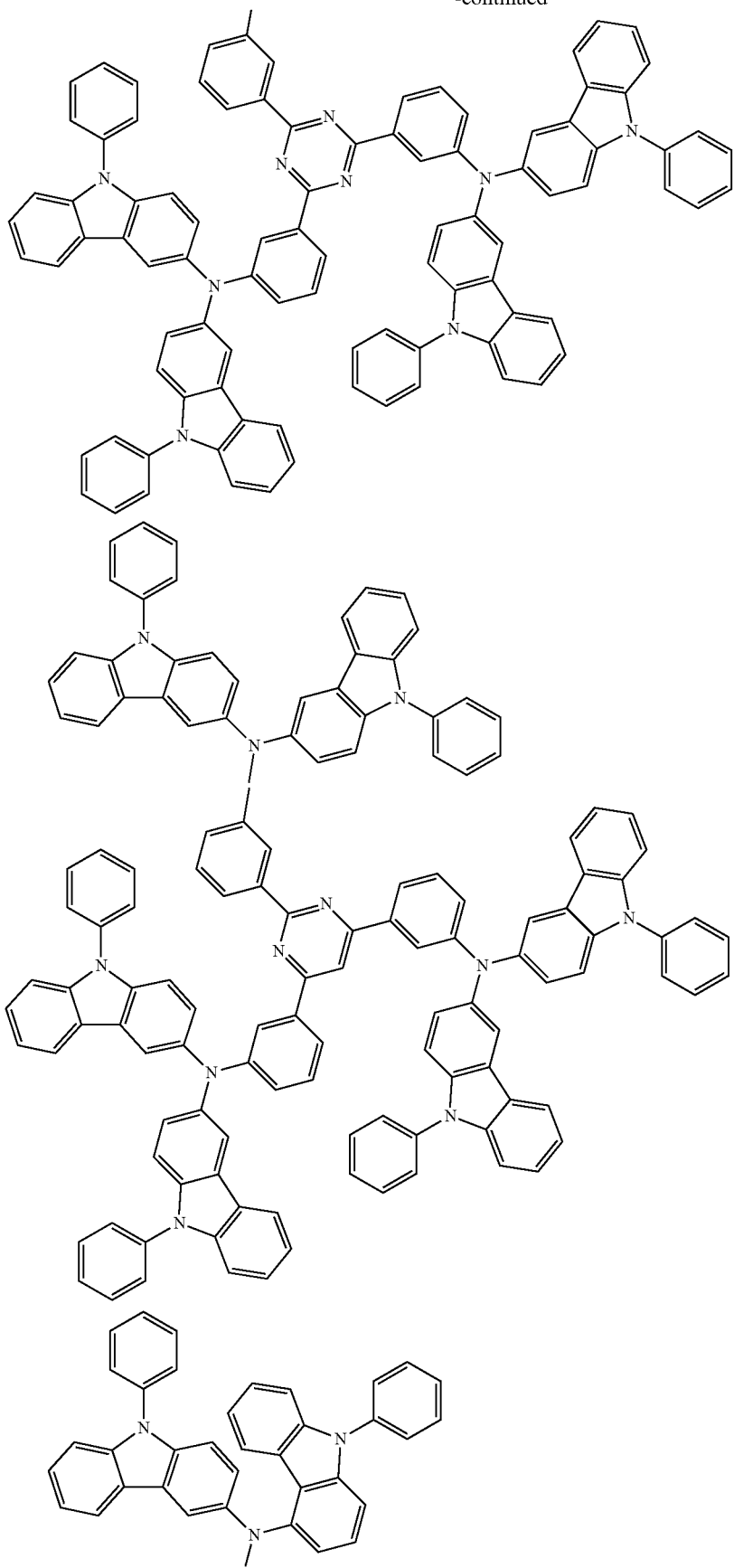

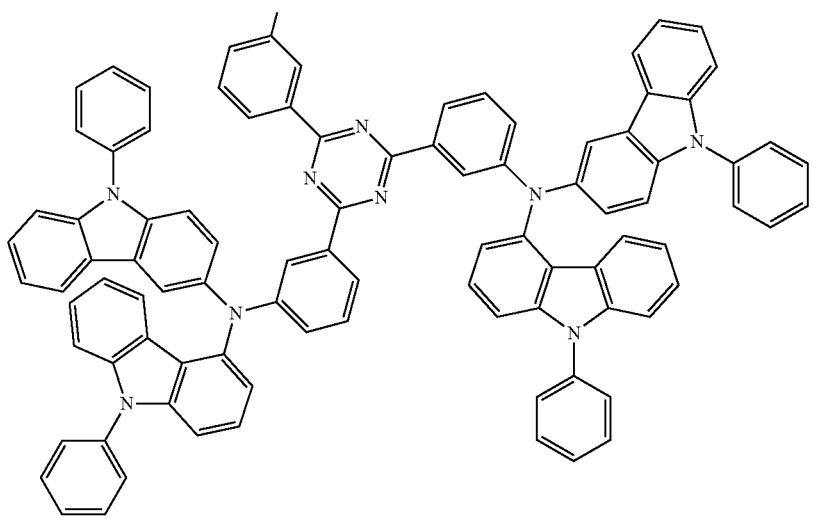

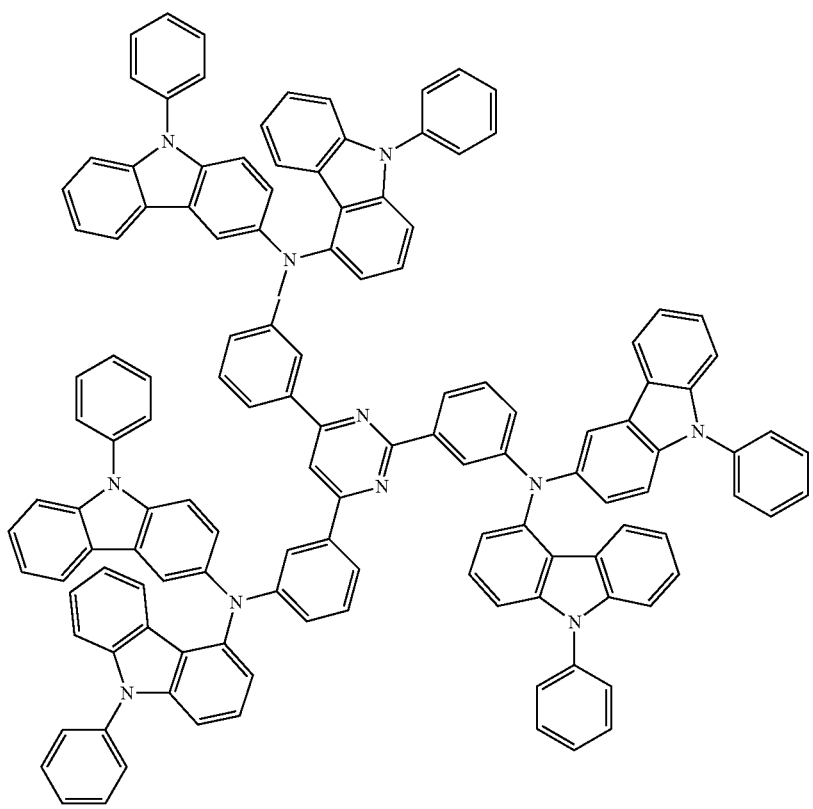

Compound Represented by Formula 1[IV]

In an aspect of the invention, a compound represented by formula 1[IV](also referred to as "compound 1[IV]") is used as material for organic electroluminescence devices. The compound is suitable for use in forming the layer of organic EL device by a coating method and is useful as a material for organic electroluminescence devices.

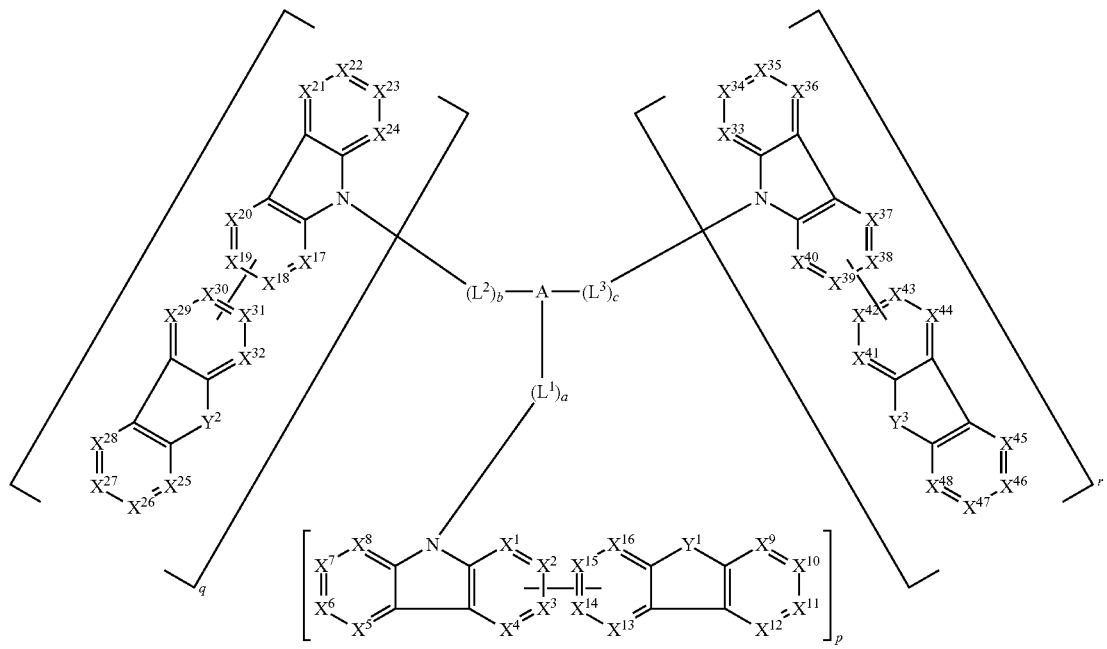

(1[IV])

in formula 1[IV],

A represents a substituted or unsubstituted nitrogen-containing heteroaromatic hydrocarbon group having 5 to 30 ring atoms;

$L^1$ to $L^3$ each independently represent a substituted or unsubstituted aromatic hydrocarbon group having 6 to 30 ring carbon atoms, a substituted or unsubstituted heterocyclic group having 5 to 30 ring atoms, or a group wherein 2 to 4 groups selected from the preceding groups are bonded to each other;

a to c each independently represent 0 or 1;

$X^1$ to $X^{48}$ each represent $C(R^1)$ to $C(R^{48})$, respectively, or a nitrogen atom;

$R^1$ to $R^{48}$ each independently represent a hydrogen atom or a substituent;

provided that one of $X^1$ to $X^4$ represents a carbon atom which is directly bonded to a carbon atom represented by one of $X^{13}$ to $X^{16}$, one of $X^{17}$ to $X^{20}$ represents a carbon atom which is directly bonded to a carbon atom represented by one of $X^{29}$ to $X^{32}$, one of $X^{37}$ to $X^{40}$ represents a carbon atom which is directly bonded to a carbon atom represented by one of $X^{41}$ to $X^{44}$, and two selected from $R^1$ to $R^{48}$ not involved in the above direct bonding may be bonded to each other to form a ring;

$Y^1$ to $Y^3$ each independently represent an oxygen atom, a sulfur atom, $C(R^A)(R^B)$, $Si(R^C)(R^D)$, $P(R^E)$, $P(=O)(R^F)$, $S(=O)_2$, or $P(=S)(R^G)$;

$R^A$, $R^B$, $R^C$, $R^D$, $R^E$, $R^F$, and $R^G$ each independently represent represents a hydrogen atom or a substituent, and $R^A$ and $R^B$, and $R^C$ and $R^D$ may be bonded to each other to form a ring; and p to r each independently represent an integer of 0 to 3, p+q+r=3, and when p, q or r is 2 or 3, 2 or 3 groups in each [ ] may be the same or different, respectively.

Description of Each Group in Formula 1[IV]

The nitrogen-containing heteroaromatic hydrocarbon group for A has 5 to 30, preferably 6 and 20, and more preferably 6 to 14 ring carbon atoms. The nitrogen-containing heteroaromatic hydrocarbon group is a monocyclic group or a fused ring group comprising two or three fused rings.

The nitrogen-containing heteroaromatic hydrocarbon group contains preferably 1 to 3 and more preferably 2 or 3 nitrogen atoms. Particularly, the nitrogen-containing heteroaromatic hydrocarbon group contains preferably 2 or 3 and more preferably 3 nitrogen atoms when it is a monocyclic group, and preferably 2 nitrogen atoms when it is a fused ring group having two or three fused rings. On one hand, the nitrogen-containing heteroaromatic hydrocarbon group may contain a hetero atom other than a nitrogen atom, such as an oxygen atom, a sulfur atom, a silicon atom, and selenium atom, burr on the other hand preferably contains only a nitrogen atom as the heteroatom.

Examples of the nitrogen-containing heteroaromatic hydrocarbon group for A include residues of compounds selected from pyrrole, pyridine, pyridazine, pyrimidine, pyrazine, triazine, imidazole, pyrazole, oxadiazole, thiadiazole, triazole, tetrazole, indole, isoindole, indolizine, quinolizine, quinoline, isoquinoline, naphthyridine, cinnoline, phthalazine, quinazoline, benzo[f]quinazoline, benzo[h]quinazoline, quinoxaline, benzimidazole, indazole, carbazole, biscarbazole, phenanthridine, acridine, phenanthroline, phenazine, azatriphenylene, diazatriphenylene, hexaazatriphenylene, azacarbazole, azadibenzofuran, azadibenzothiophene, and dinaphtho[2',3': 2,3:2',3': 6,7]carbazole. The valency of the nitrogen-containing heteroaromatic hydrocarbon group, i.e., the valency of "A" corresponds to the value of "a+b+c."

The nitrogen-containing heteroaromatic hydrocarbon group mentioned above is preferably a residue of the following compounds:

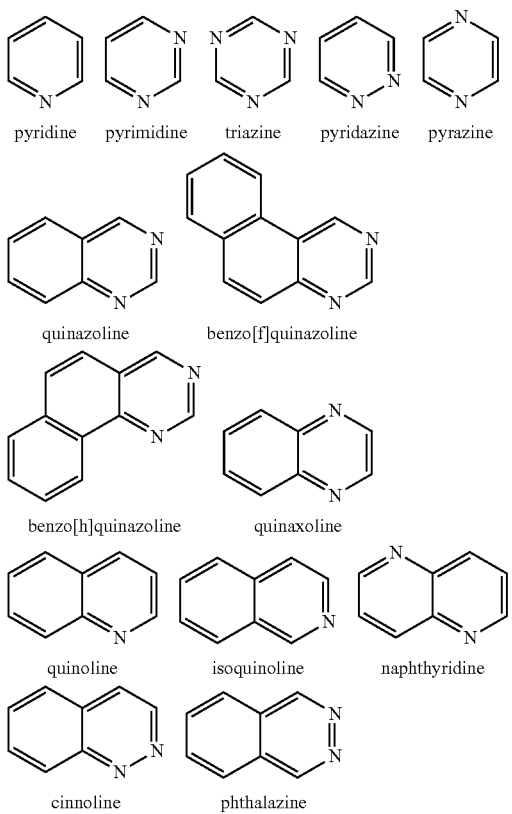

In an aspect of the invention, the nitrogen-containing heteroaromatic hydrocarbon group for A is preferably a residue of the nitrogen-containing heterocyclic ring represented by formula (A1):

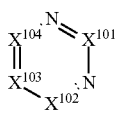

(A1)

in formula (A1), $X^{101}$ to $X^{104}$ each represent $C(R^{101})$ to $C(R^{104})$, respectively, or a nitrogen atom; $R^{101}$ to $R^{104}$ each independently represent a hydrogen atom or a substituent; and two selected from $R^{102}$ to $R^{104}$ may be bonded to each other to form a ring.

In an aspect of the invention, the nitrogen-containing heteroaromatic hydrocarbon group for A is more preferably a residue of the nitrogen-containing heterocyclic ring represented by any of formulae (A2) to (A4):

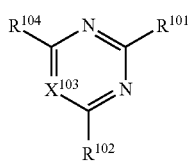

(A2)

in formula (A2), $X^{103}$ represents $C(R^{103})$ or a nitrogen atom; $R^{101}$ to $R^{104}$ each independently represent a hydrogen atom or a substituent; and two selected from $R^{102}$ to $R^{104}$ may be bonded to each other to form a ring;

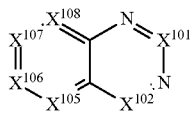

(A3)

in formula (A3), $X^{101}$, $X^{102}$, and $X^{105}$ to $X^{108}$ each represent $C(R^{101})$, $C(R^{102})$, or $C(R^{105})$ to $C(R^{108})$, respectively, or a nitrogen atom; $R^{101}$, $R^{102}$, and $R^{105}$ to $R^{108}$ each independently represent a hydrogen atom or a substituent; and two selected from $R^{102}$ and $R^{105}$ to $R^{108}$ may be bonded to each other to form a ring; and

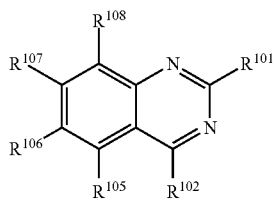

(A4)

in formula (A4), $R^{101}$, $R^{102}$, and $R^{105}$ to $R^{108}$ each independently represent a hydrogen atom or a substituent; and two selected from $R^{102}$ and $R^{105}$ to $R^{108}$ may be bonded to each other to form a ring.

The nitrogen-containing heteroaromatic hydrocarbon group for A in formula 1[IV] may have a substituent.

Examples of the substituent of the nitrogen-containing heteroaromatic hydrocarbon group include the substituents mentioned above and also include, for example, a 9-carbazolyl group having an aryl substituent or a heteroaryl substituent and an aryl group or a heteroaryl group each having a 9-carbazolyl substituent which further has an aryl substituent or a heteroaryl substituent.

In formula 1[IV], the aromatic hydrocarbon group for $L^1$ to $L^3$ has 6 to 30, preferably 6 to 18, more preferably 6 to 13, still more preferably 6 to 12, and particularly preferably 6 to 10 ring carbon atoms.

The aromatic hydrocarbon group for $L^1$ to $L^3$ is preferably a di- to tetravalent residue of any of the following compounds. In an aspect of the invention, preferably at least one of $L^1$ to $L^3$ and more preferably all thereof are di- to tetravalent residues of any of the following compounds:

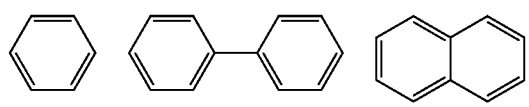

wherein each carbon atom in the compound may have a substituent.

The aromatic hydrocarbon group for $L^1$ to $L^3$ is more preferably a group represented by any of the following formulae. In an aspect of the invention, preferably at least one of $L^1$ to $L^3$ and more preferably all thereof are groups represented by any of the following formulae:

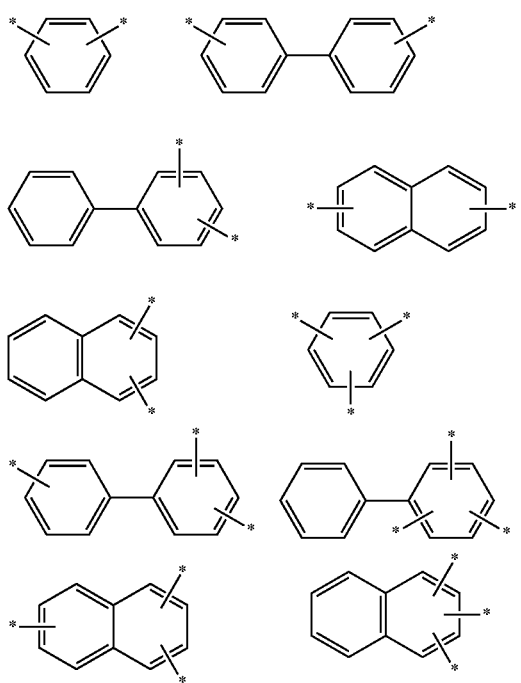

wherein * indicates a bonding site and each carbon atom other than that at the bonding site may have a substituent.

The aromatic hydrocarbon group for $L^1$ to $L^3$ is more preferably a group represented by any of the following formulae. Preferably at least one of $L^1$ to $L^3$ and more preferably all thereof are groups represented by any of the following formulae:

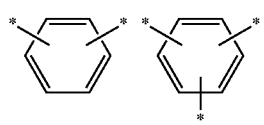

wherein * indicates a bonding site and each carbon atom other than that at the bonding site may have a substituent.

The aromatic hydrocarbon group for $L^1$ to $L^3$ is still more preferably a group represented by any of the following formulae. Preferably at least one of $L^1$ to $L^3$ and more preferably all thereof are groups represented by any of the following formulae:

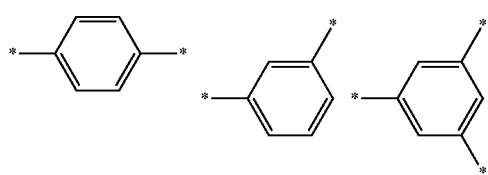

wherein * indicates a bonding site and each carbon atom other than that at the bonding site may have a substituent.

In addition to the above groups, the aromatic hydrocarbon group for $L^1$ to $L^3$ may include the groups represented by the following formulae:

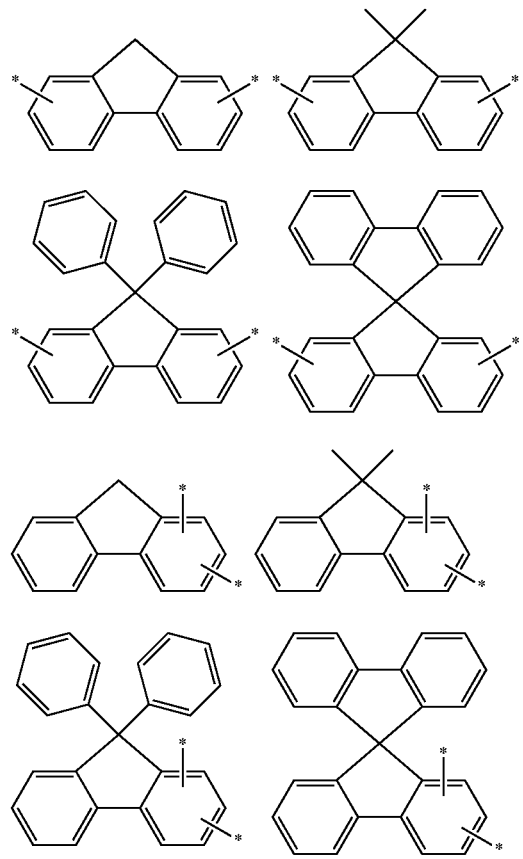

wherein * indicates a bonding site and each carbon atom other than that at the bonding site may have a substituent.

Examples of the divalent aromatic hydrocarbon group for $L^1$ to $L^3$ include the following groups:

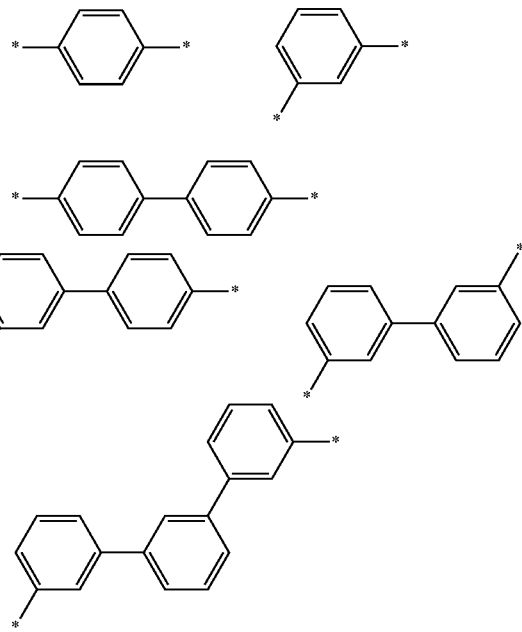

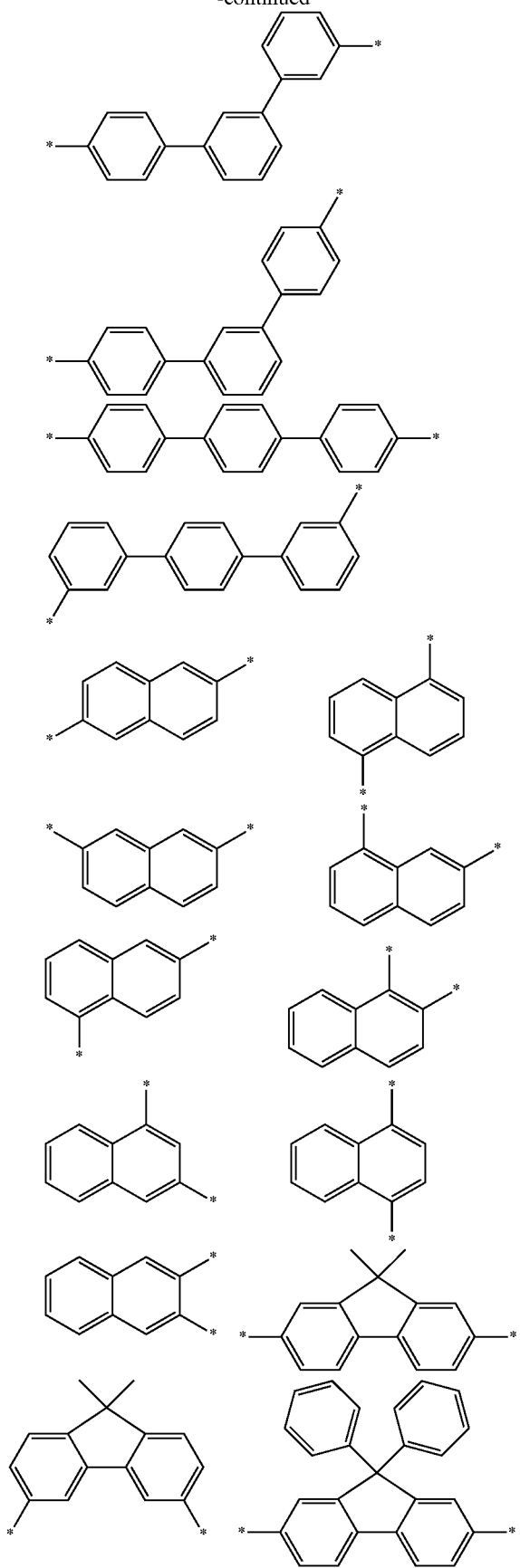

wherein * indicates a bonding site and each carbon atom other than that at the bonding site may have a substituent.

The heterocyclic group for $L^1$ to $L^3$ has 5 to 30, preferably 5 to 18, more preferably 5 to 13, particularly preferably 5 to 10 ring atoms.

Examples of the heterocyclic group include a residue of a nitrogen-containing heterocyclic compound, such as pyrrole, pyridine, imidazopyridine, pyrazole, triazole, tetrazole, indole, isoindole, and carbazole; a residue of an oxygen-containing heterocyclic compound, such as furan, benzofuran, isobenzofuran, dibenzofuran, oxazole, oxadiazole, benzoxazole, benzonaphthofuran, and dinaphthofuran; and a residue of a sulfur-containing heterocyclic compound, such as thiophene, benzothiophene, dibenzothiophene, thiazole, thiadiazole, benzothiazole, benzonaphthothiophene, and dinaphthothiophene.

The "group wherein 2 to 4 groups selected from the preceding groups are bonded to each other" for $L^1$ to $L^3$ is a group wherein 2 to 4 groups selected from a substituted or unsubstituted aromatic hydrocarbon group having 6 to 30 ring carbon atoms and a substituted or unsubstituted heterocyclic group having 5 to 30 ring atoms are bonded to each other. The order of bonding is not particularly limited.

In particular, each of $L^1$ to $L^3$ is preferably a substituted or unsubstituted aromatic hydrocarbon group having 6 to 30 ring carbon atoms. The aromatic hydrocarbon group more preferred is as described above.

$X^1$ to $X^{48}$ each represent $C(R^1)$ to $C(R^{48})$, respectively, or a nitrogen atom;

$R^1$ to $R^{48}$ each independently represent a hydrogen atom or a substituent;

provided that one of $X^1$ to $X^4$ represents a carbon atom which is directly bonded to a carbon atom represented by one of $X^{13}$ to $X^{16}$, one of $X^{17}$ to $X^{20}$ represents a carbon atom which is directly bonded to a carbon atom represented by one of $X^{29}$ to $X^{32}$, and one of $X^{37}$ to $X^{40}$ represents a carbon atom which is directly bonded to a carbon atom represented by one of $X^{41}$ to $X^{44}$.

Two selected from $R^1$ to $R^8$, two selected from $R^9$ to $R^{16}$, and two selected from $R^{17}$ to $R^{24}$, two selected from $R^{25}$ to $R^{32}$, two selected from $R^{33}$ to $R^{40}$, and two selected from $R^{41}$ to $R^{48}$, each not involved in the above direct bonding, may be bonded to each other to form a ring. In an aspect of the invention, two selected from $R^1$ to $R^8$, two selected from $R^9$ to $R^{16}$, two selected from $R^{17}$ to $R^{24}$, two selected from $R^{25}$ to $R^{32}$, two selected from $R^{33}$ to $R^{40}$, and two selected from $R^{41}$ to $R^{48}$, each not involved in the above direct bonding, are preferably not bonded to each other, thereby failing to form a ring.

The "direct bond" used herein is generally called a "single bond" in some cases.

$X^1$ to $X^{48}$ are each preferably $C(R^1)$ to $C(R^{48})$, respectively, and more preferably $R^1$ to $R^{48}$ are all hydrogen atoms.

$Y^1$ to $Y^3$ each independently represent an oxygen atom, a sulfur atom, $C(R^A)(R^B)$, $Si(R^C)(R^D)$, $P(R^E)$, $P(=O)(R^F)$, $S(=O)_2$, or $P(=S)(R^G)$. Preferably each of $Y^1$ to $Y^3$ represents an oxygen atom or a sulfur atom, more preferably all of $Y^1$ to $Y^3$ represent oxygen atoms or sulfur atoms, and still more preferably all of $Y^1$ to $Y^3$ represent oxygen atoms or all of $Y^1$ to $Y^3$ represent sulfur atoms.

$R^A$, $R^B$, $R^C$, $R^D$, $R^E$, $R^F$, and $R^G$ each independently represent a hydrogen atom or a substituent. $R^A$ and $R^B$, and $R^C$ and $R^D$ may be bonded to each other to form a ring.

$R^A$, $R^B$, $R^C$, $R^D$, $R^E$, $R^F$, and $R^G$ are preferably all aryl groups which are preferably selected from the following groups:

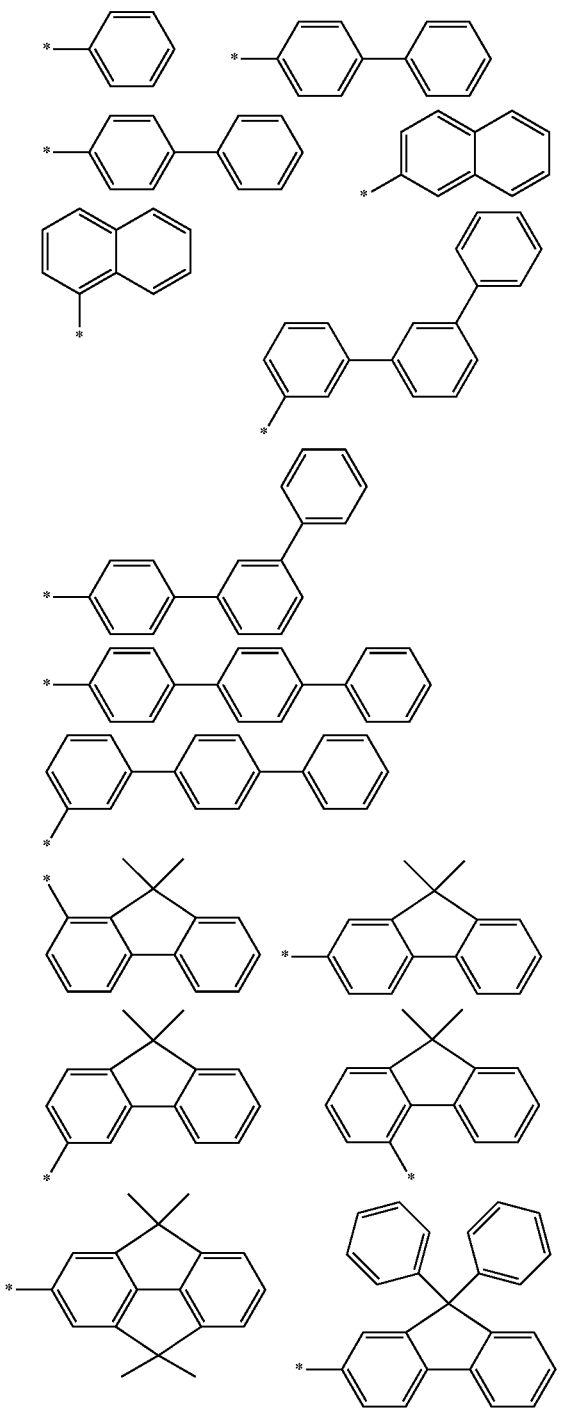

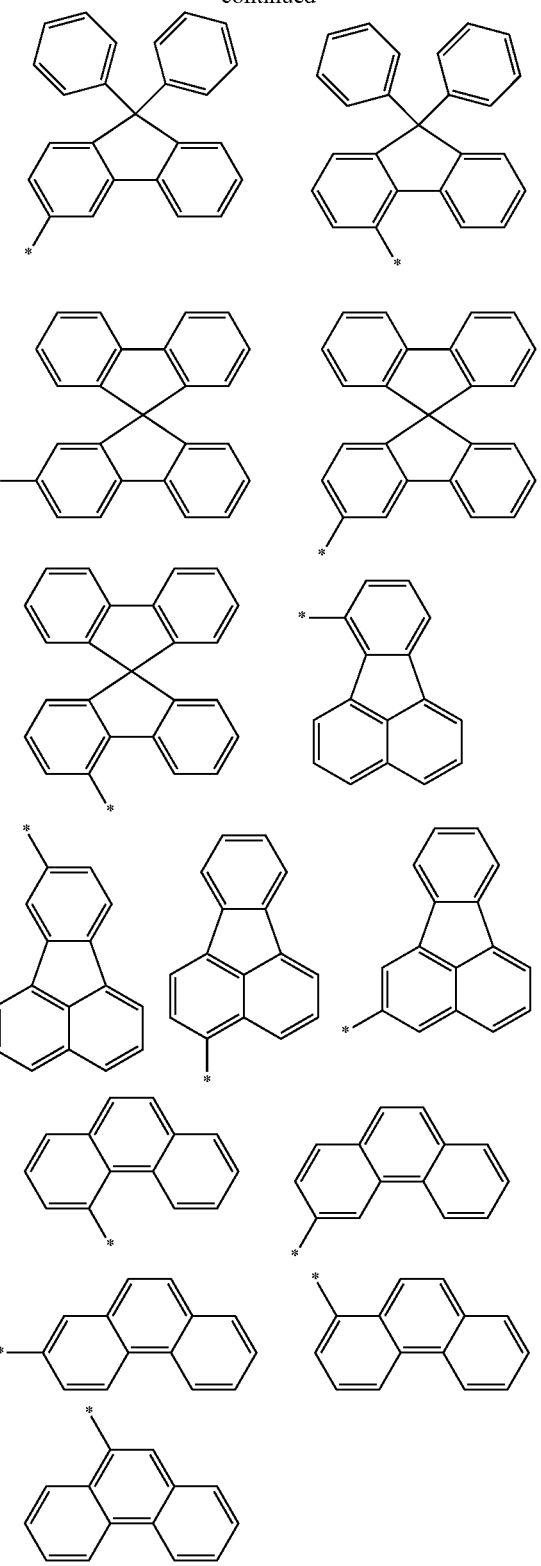

wherein * indicates a bonding site and each carbon atom other than that at the bonding site may have a substituent.

The structures wherein $R^A$ and $R^B$ in $C(R^A)(R^B)$ or $R^C$ and $R^D$ in $Si(R^C)(R^D)$ are bonded to each other to form a ring are shown below:

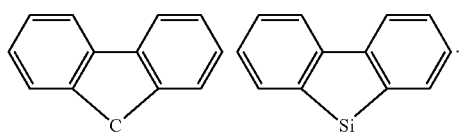
As described above, p to r in formula 1[IV] each independently represent an integer of 0 to 3, and p+q+r is 3. Preferably, two selected from p to r cannot be 0 at the same time, although not particularly limited thereto.
Examples of the group in [ ] of formula 1[IV] are shown below, and the group can be arbitrarily selected from the following groups.
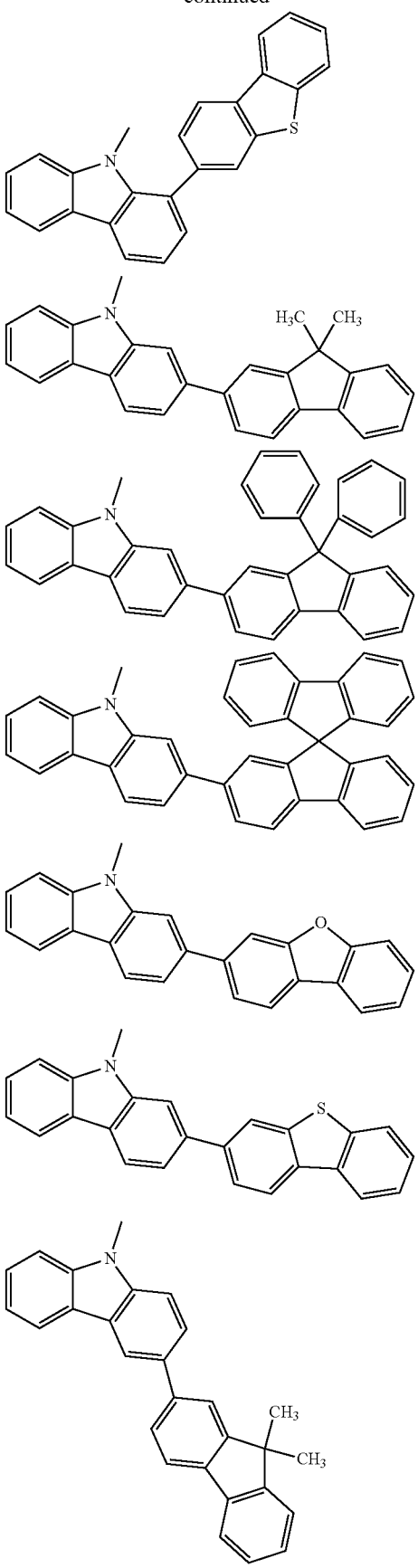

1193
-continued
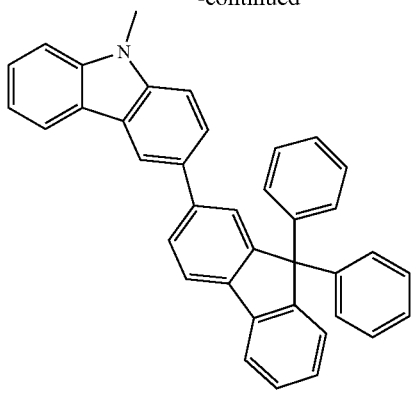
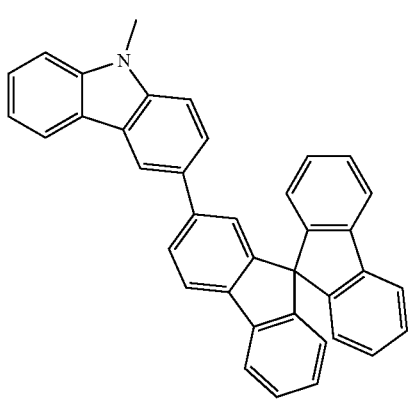
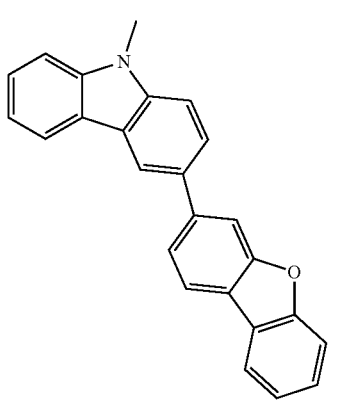
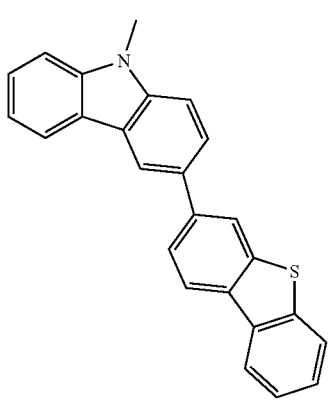
1194
-continued
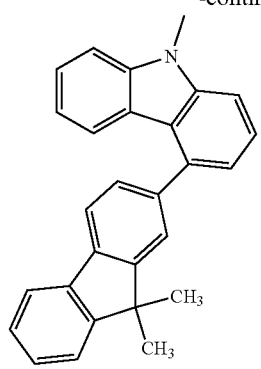
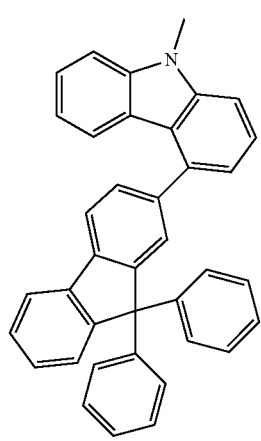
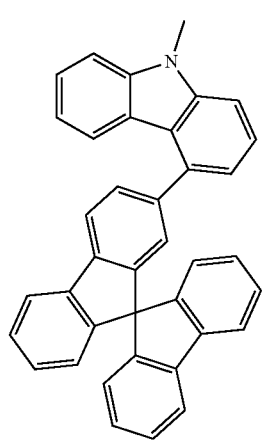
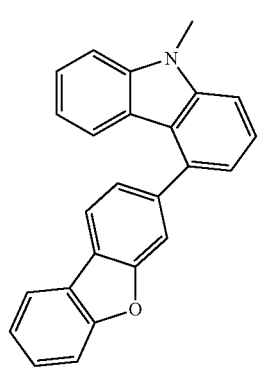

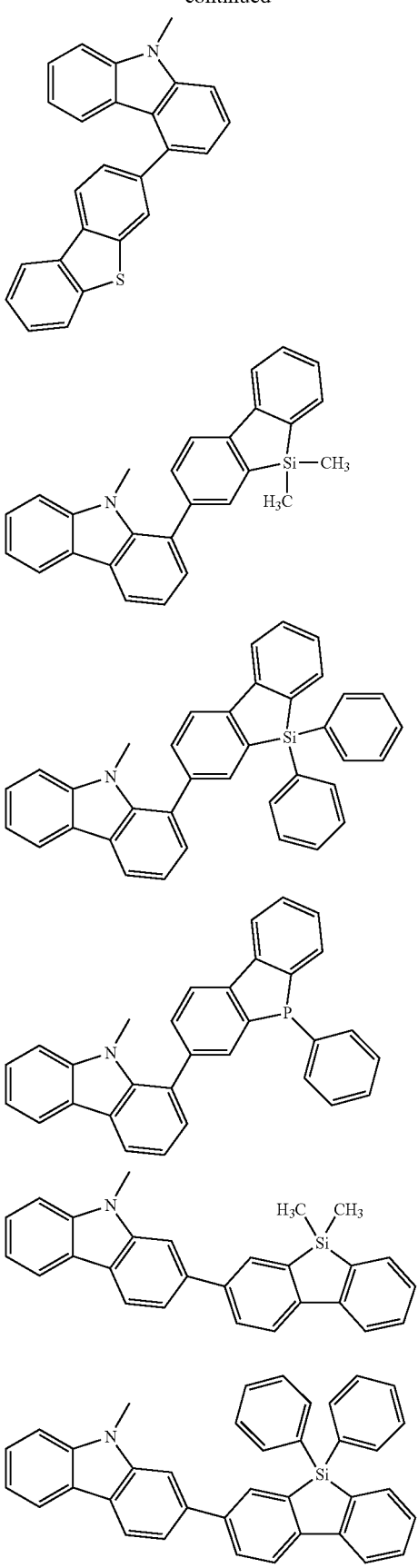
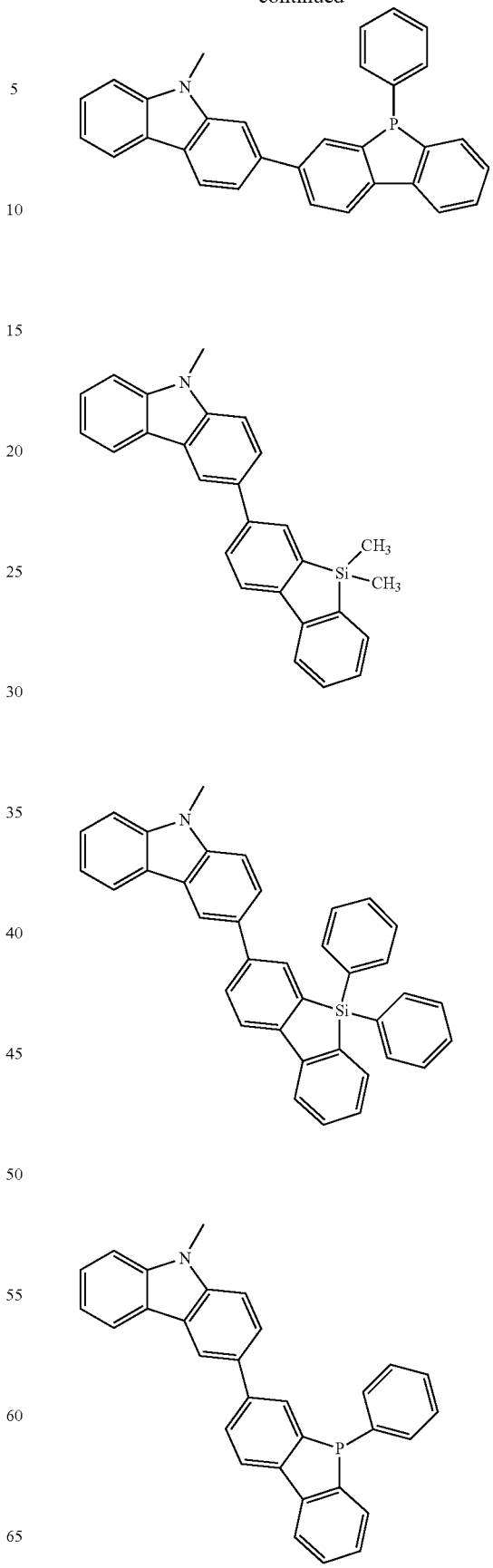

1197
-continued
1198
-continued
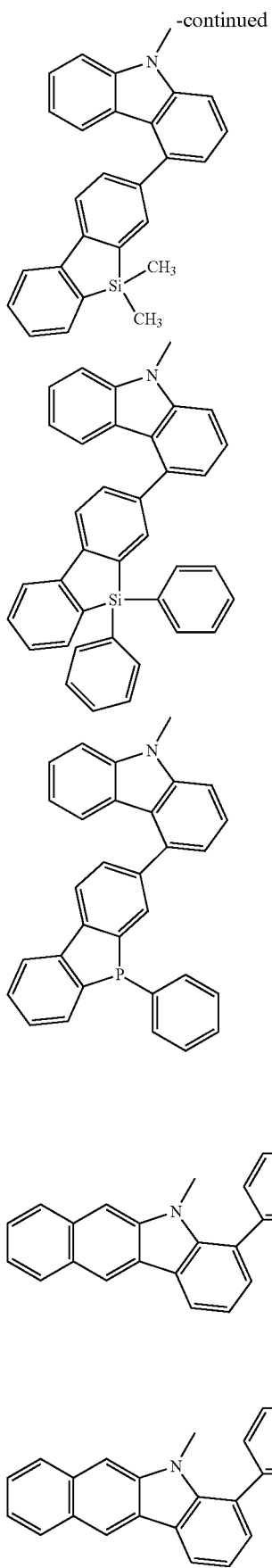
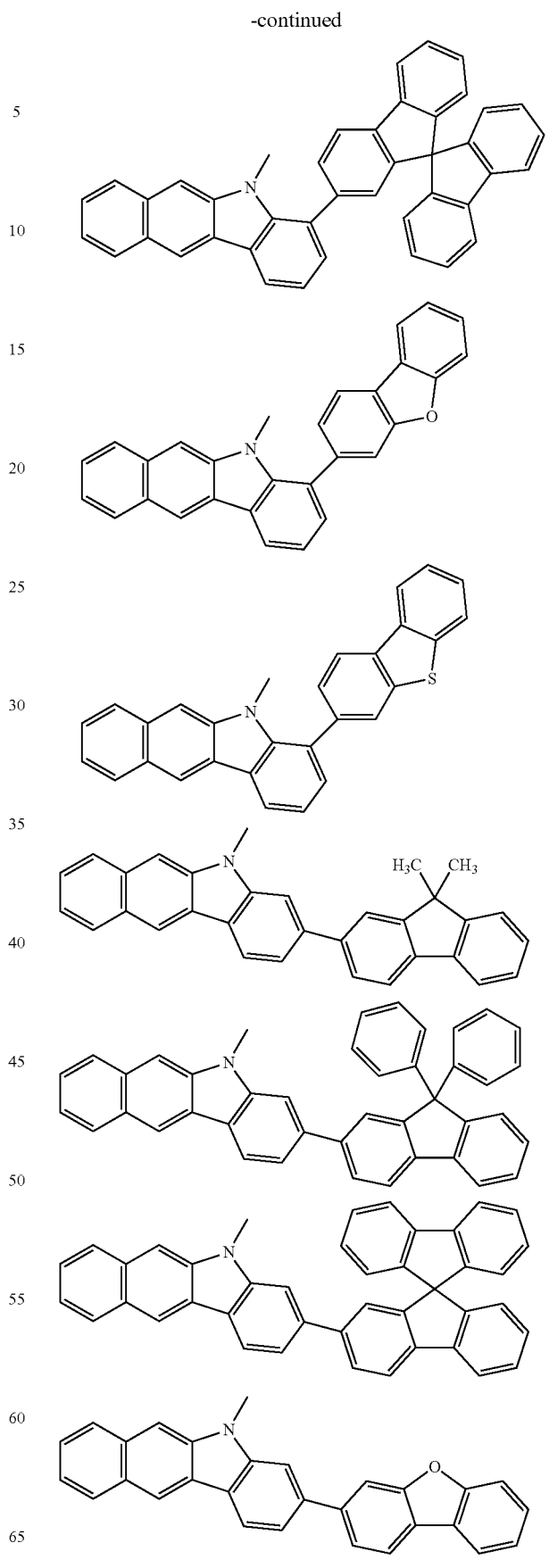

1199
-continued
1200
-continued
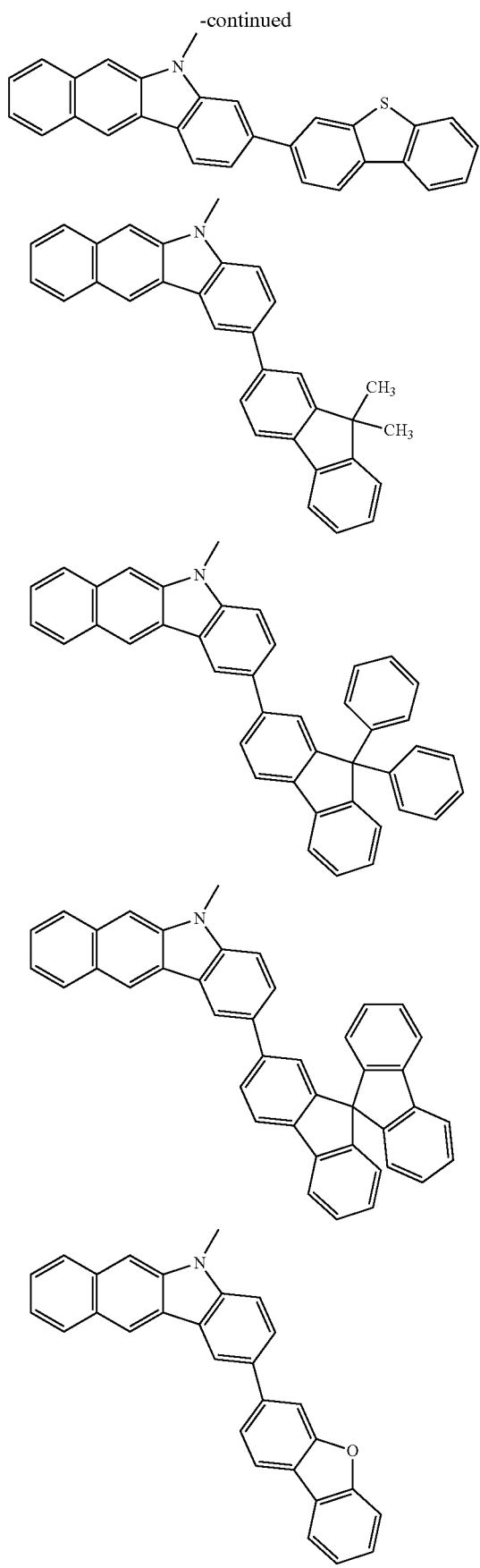

1201
-continued
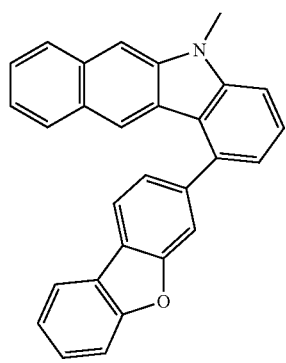
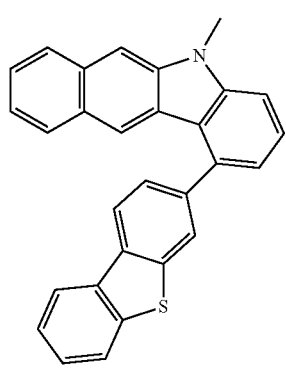
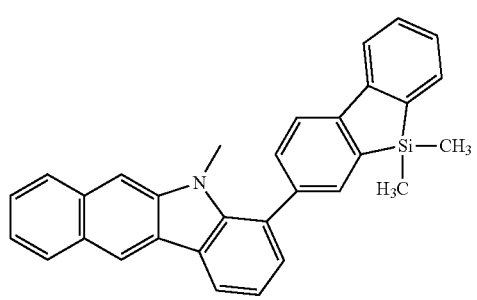
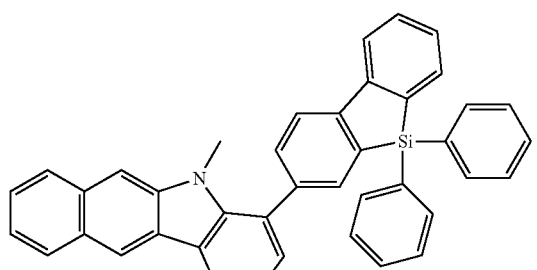
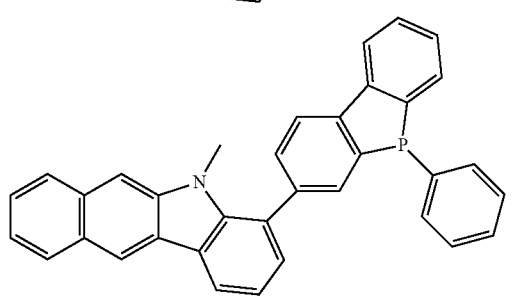
1202
-continued
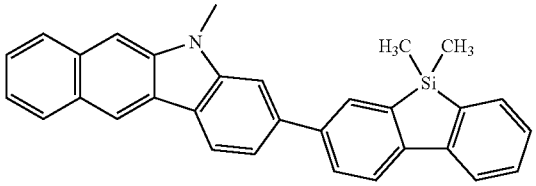
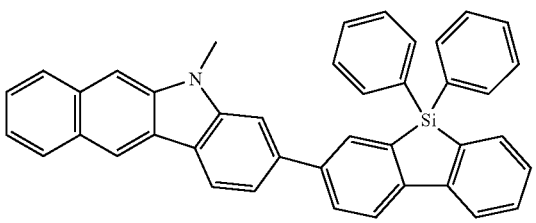
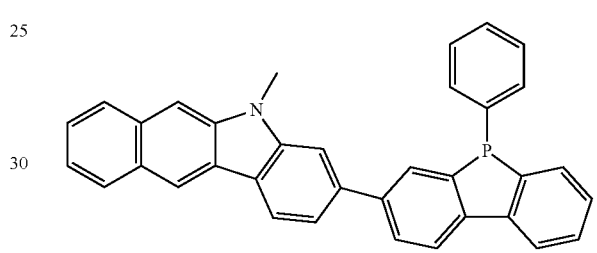
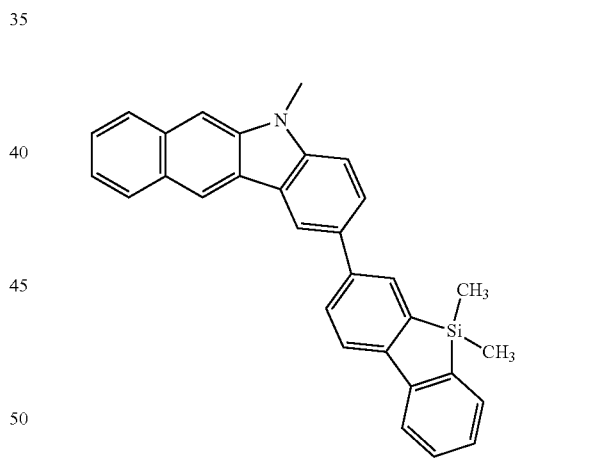
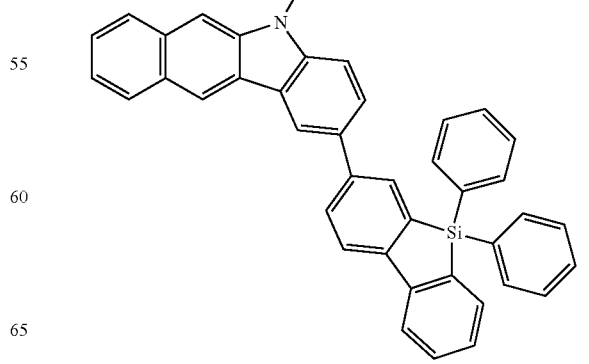

1203
-continued
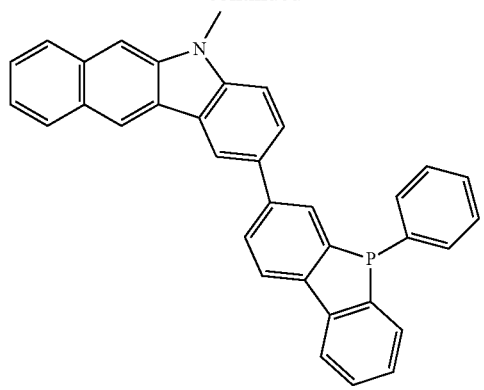
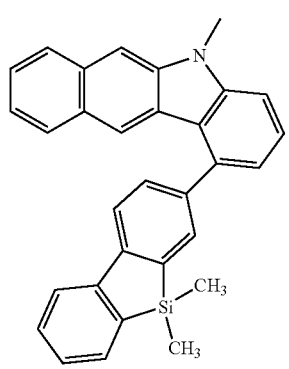
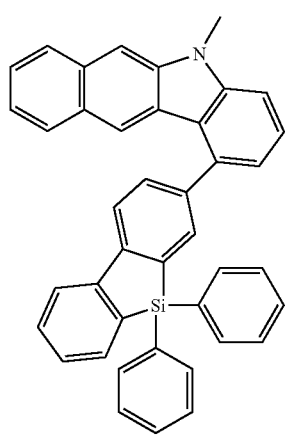
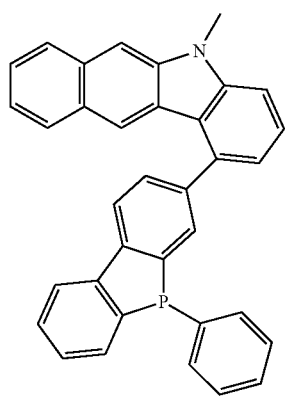
1204
-continued
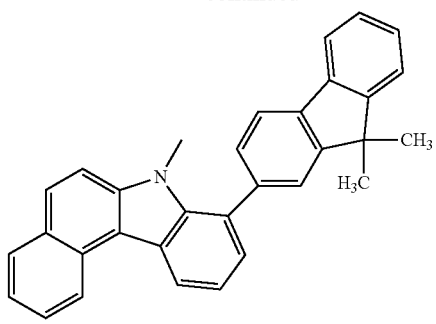
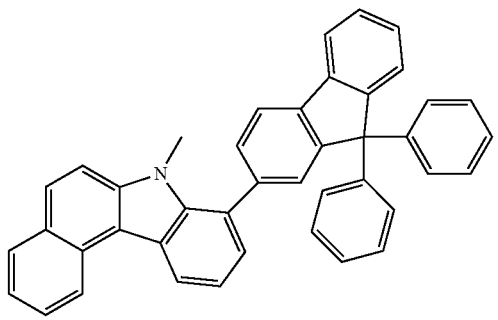
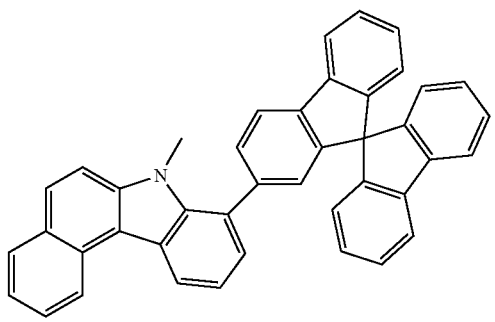
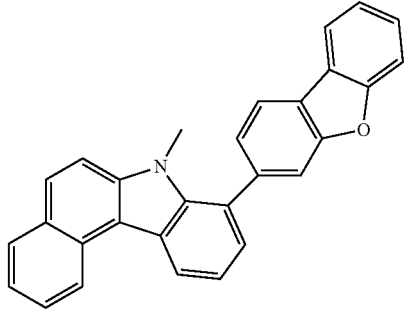
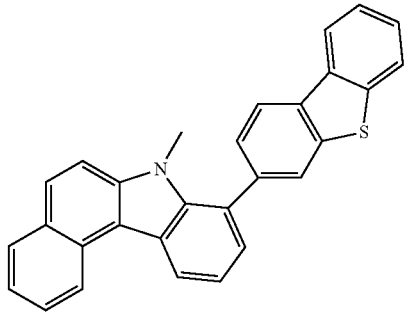

1205
-continued
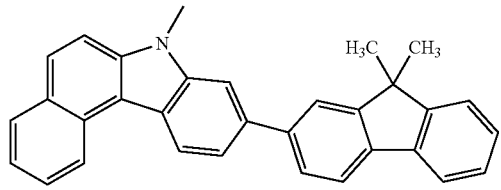
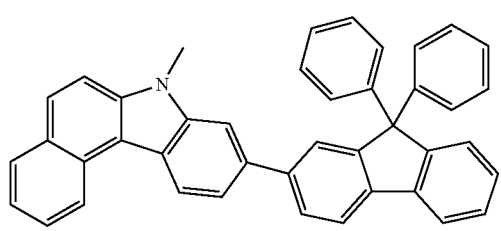
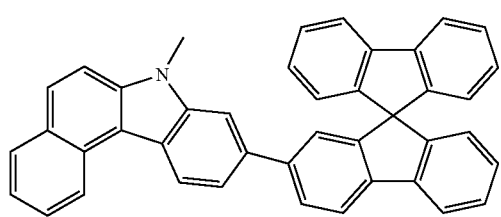
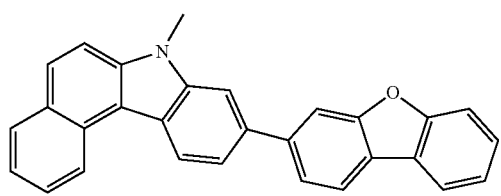
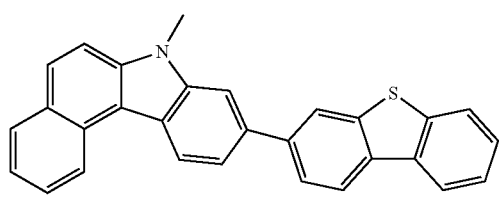
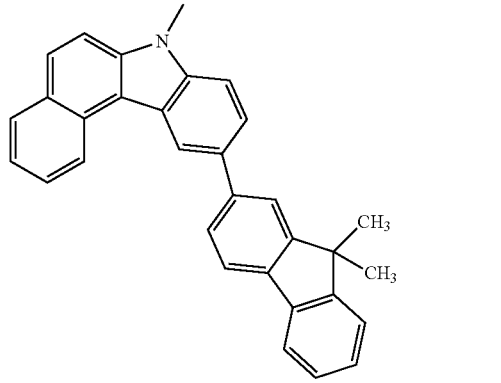
1206
-continued
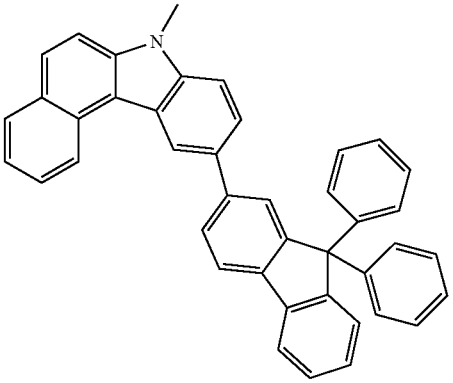
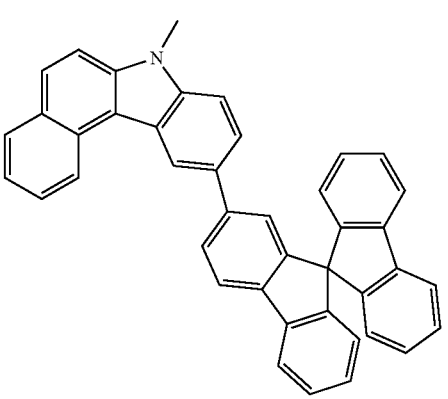
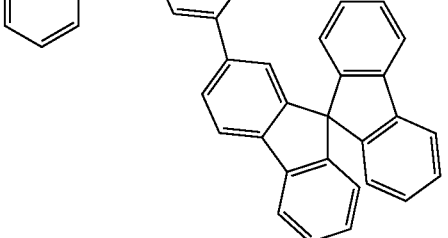
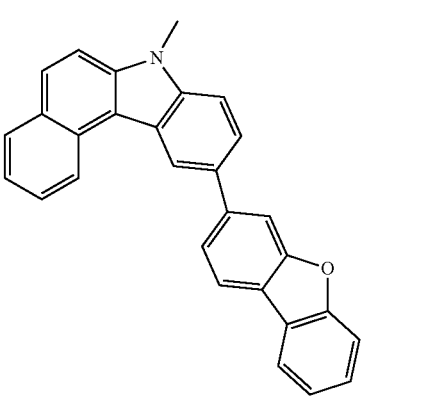
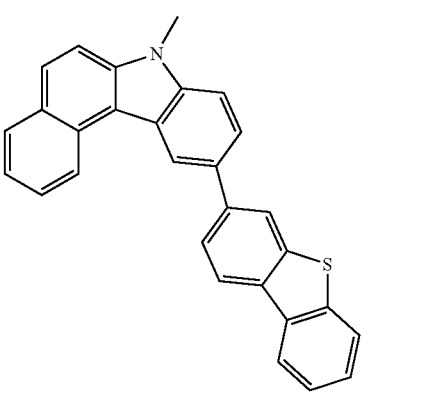

1207
-continued
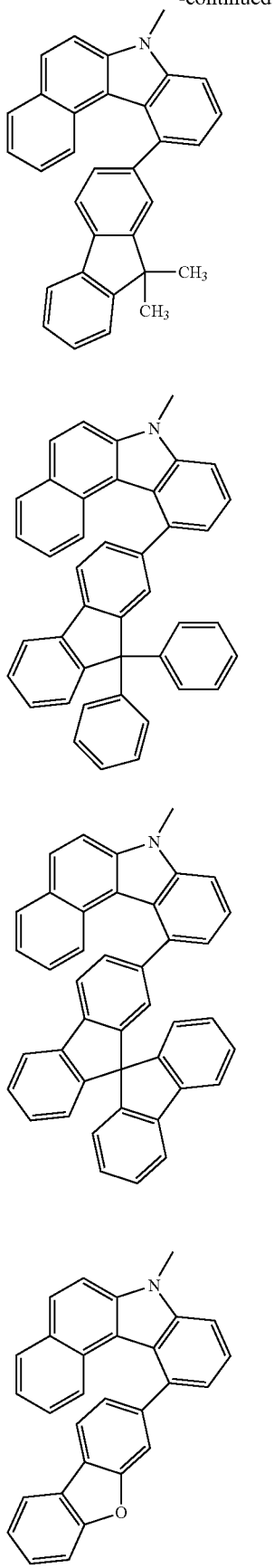
1208
-continued
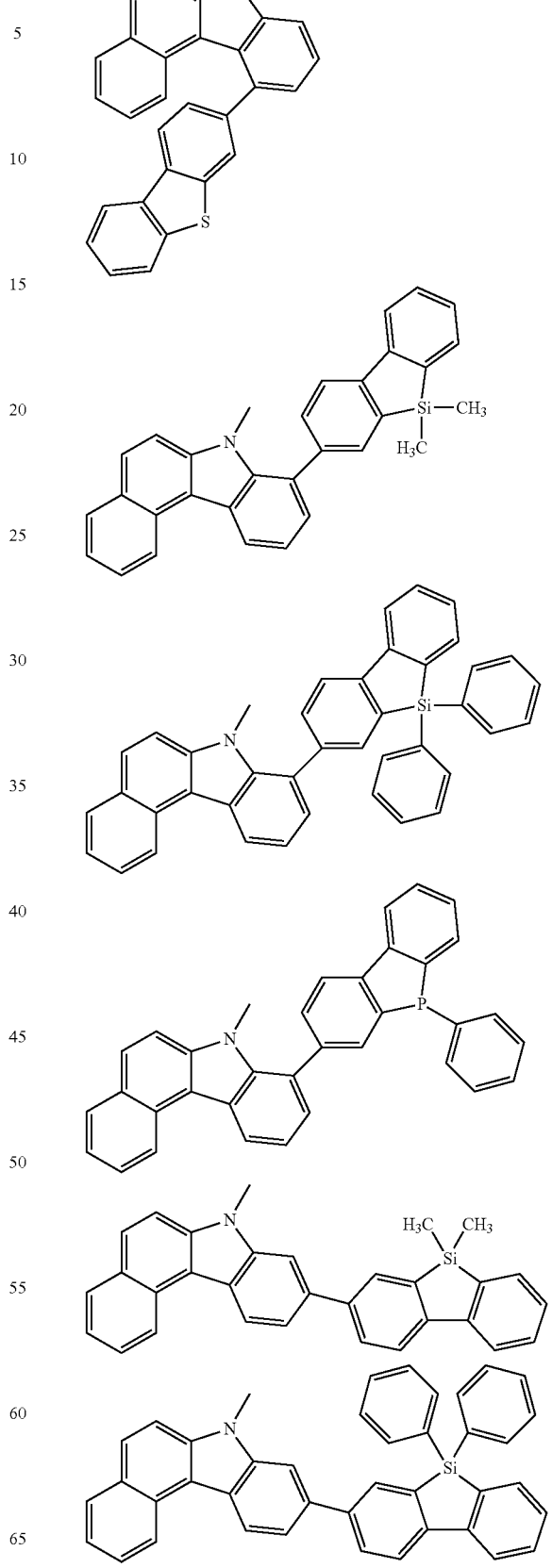

1209
-continued
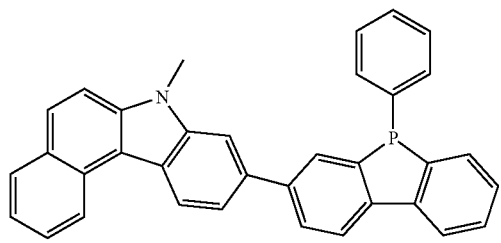
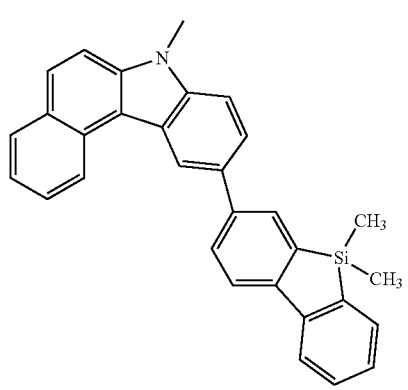
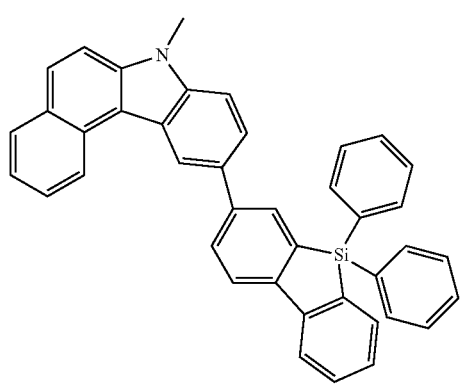
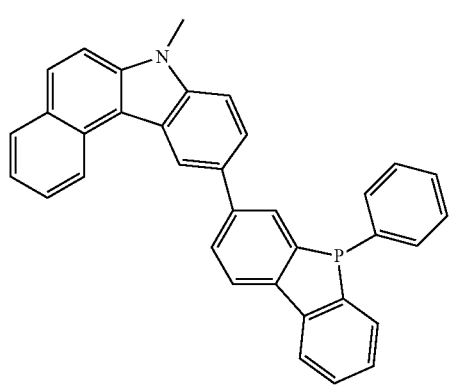
1210
-continued
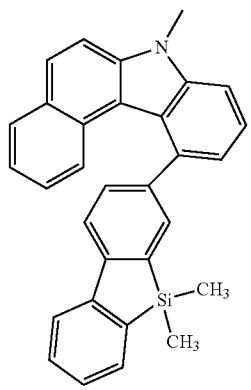
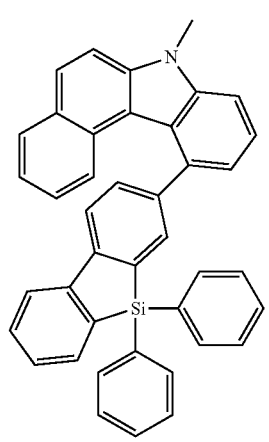
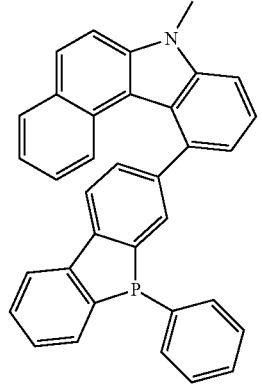
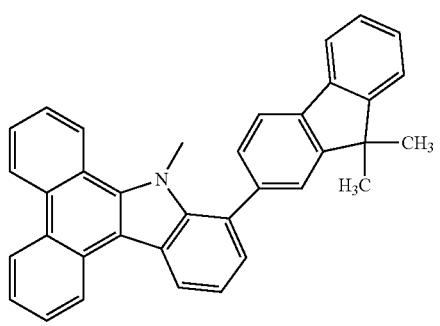

1211
-continued
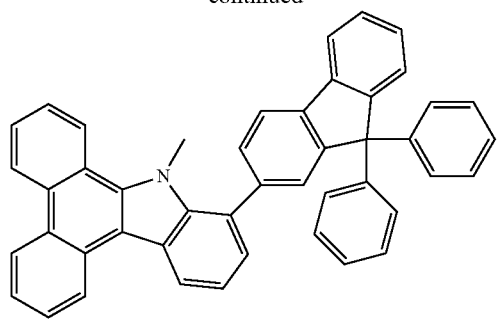
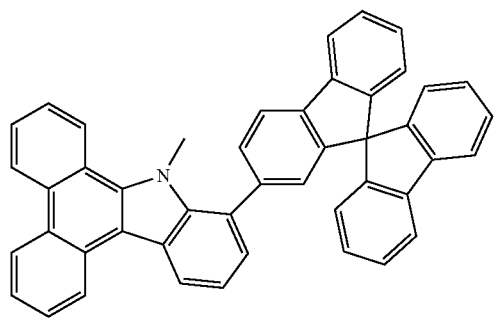
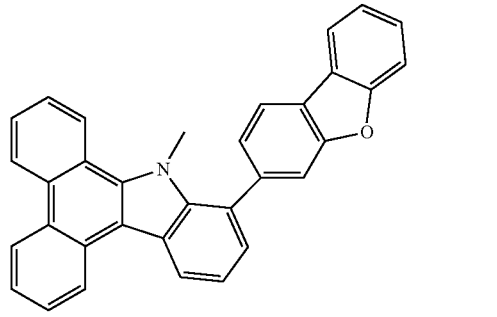
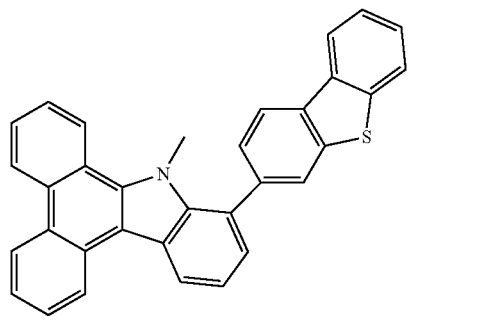

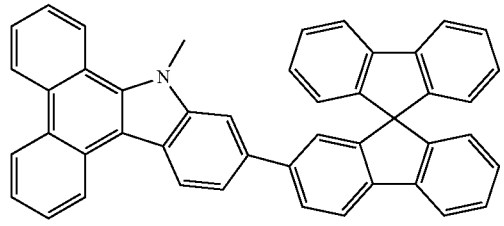
1212
-continued
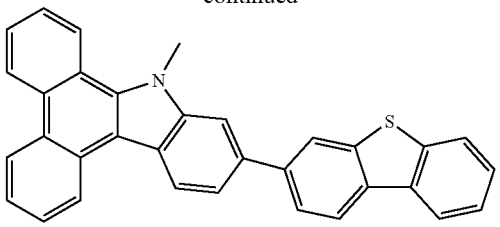
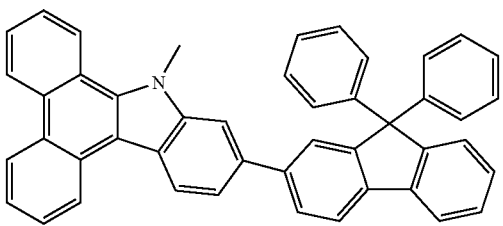
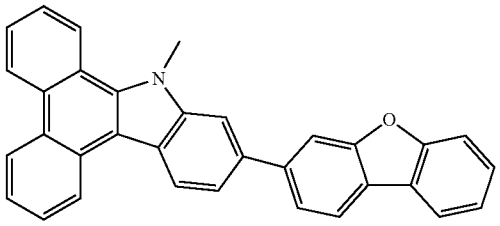
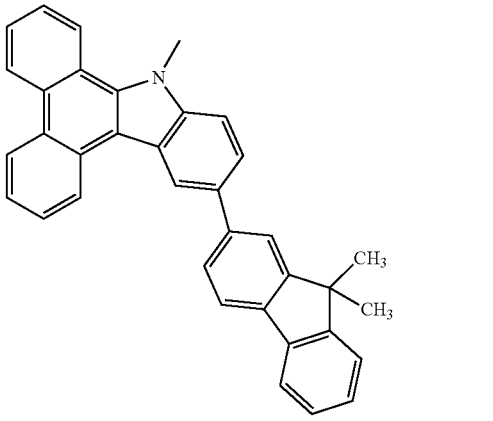
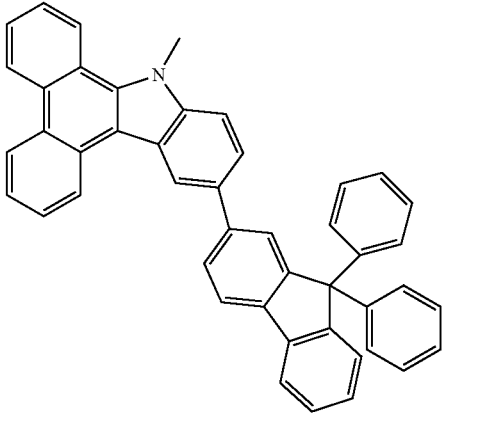

1213
-continued
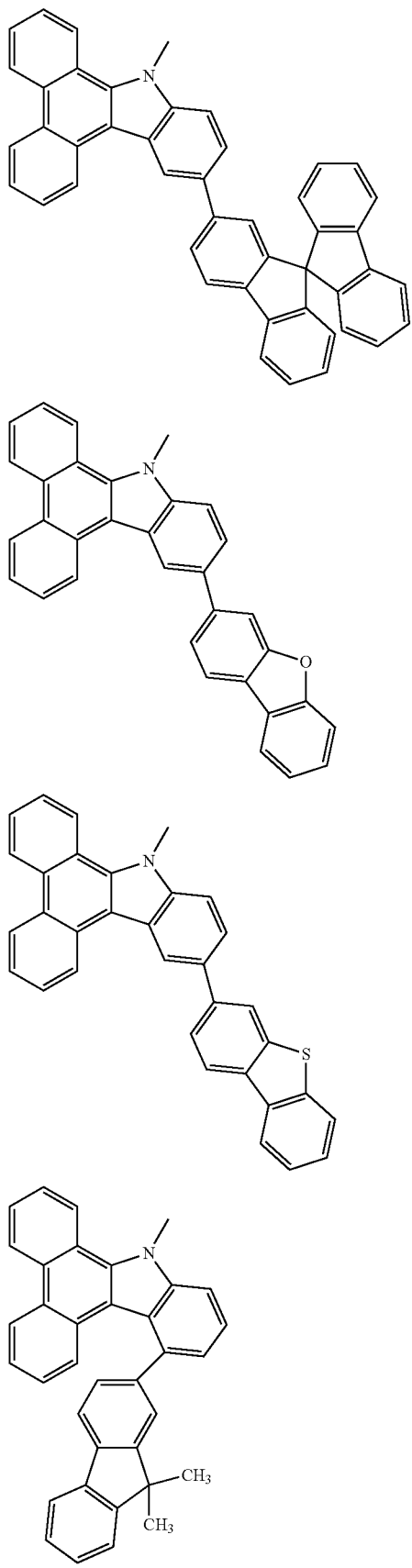
1214
-continued
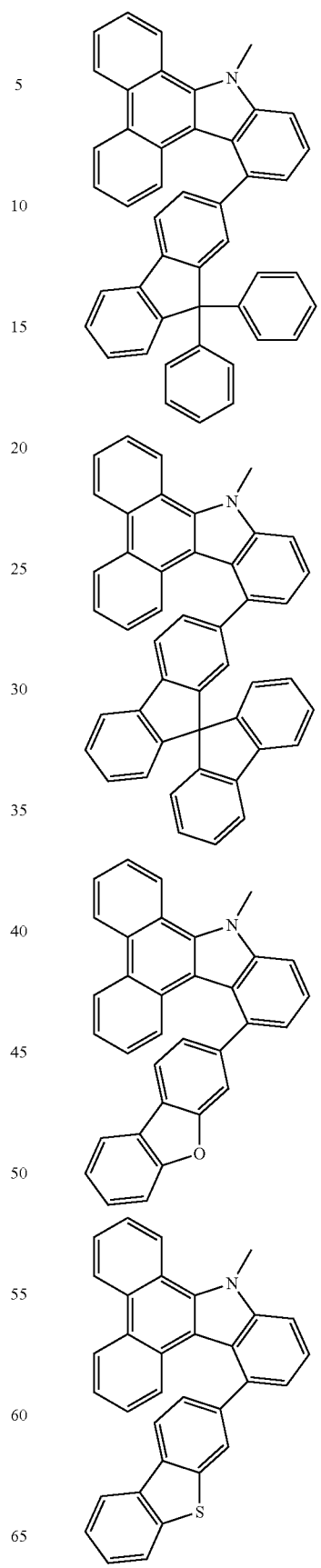

1215
-continued
1216
-continued
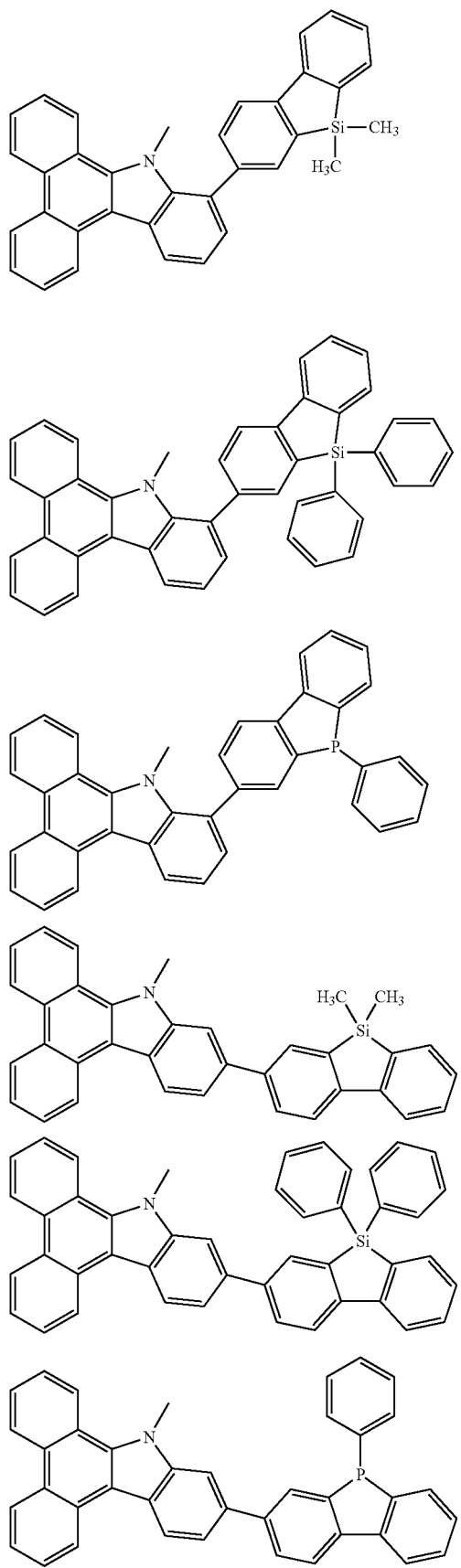
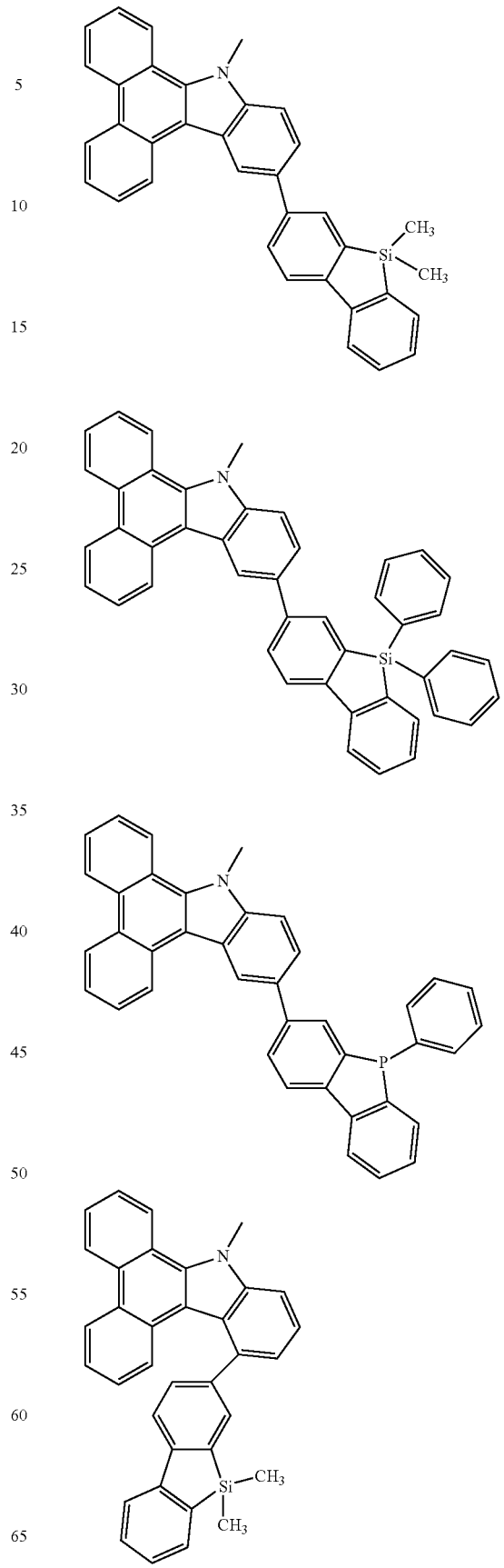

1217
-continued
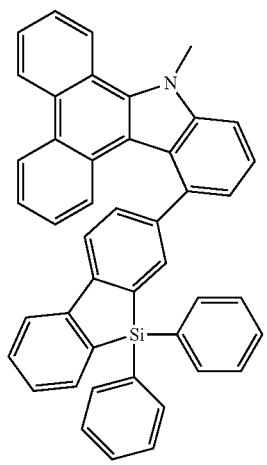
1218
-continued
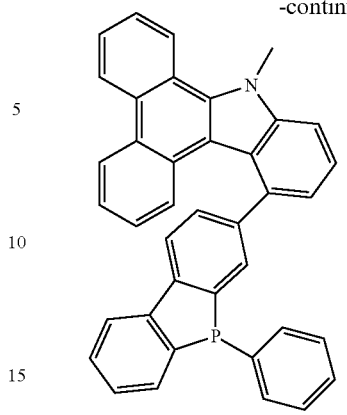
Preferred Examples of Compound 1[IV]
Formulae of preferred examples of compound 1[IV] are shown below, wherein the definition of each group and preferred examples thereof are as described above in formula 1[IV];
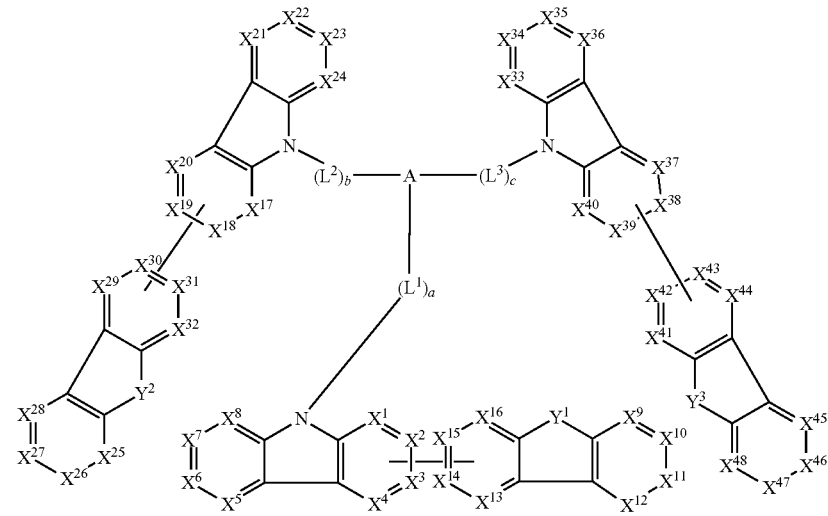
(1a[IV])
in formula 1a[IV], A, $L^1$ to $L^3$, a to c, $X^1$ to $X^{48}$, $Y^1$ to $Y^3$, and preferred examples thereof are as described above in formula 1[IV];
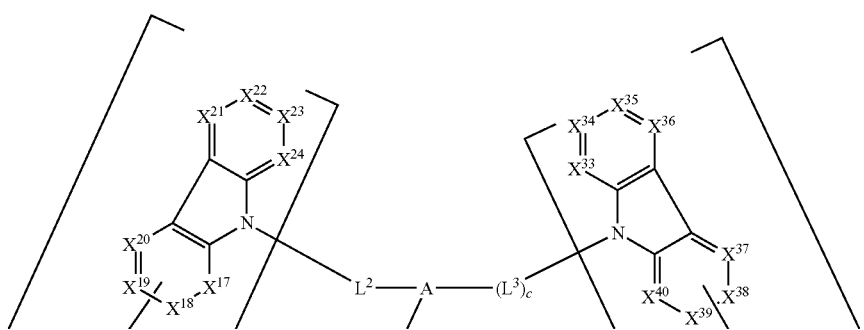
(1-ii-1[IV])

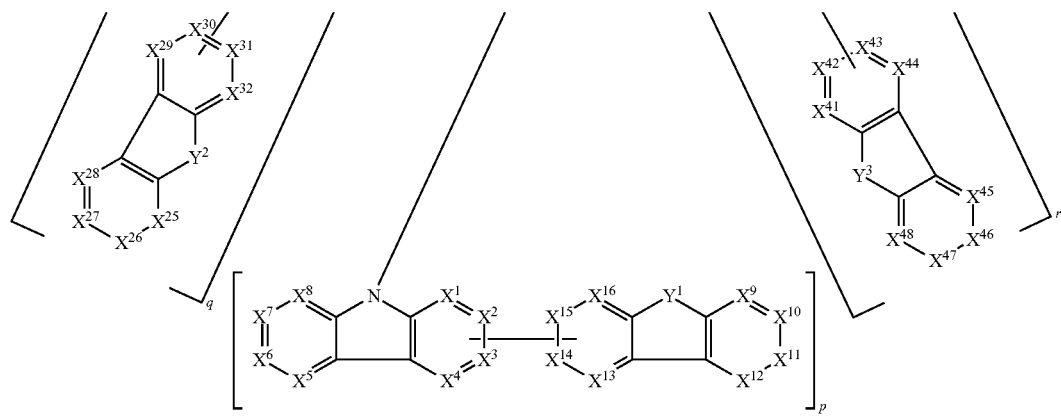
in formula 1-ii-1[IV], A, $L^2$, $L^3$, c, p to r, $X^1$ to $X^{48}$, $Y^1$ to $Y^3$, and preferred examples thereof are as described above in formula 1[IV]; and when p, q or r is 2 or 3, 2 or 3 groups in each [ ] may be the same or different;
(1a-ii-1[IV])
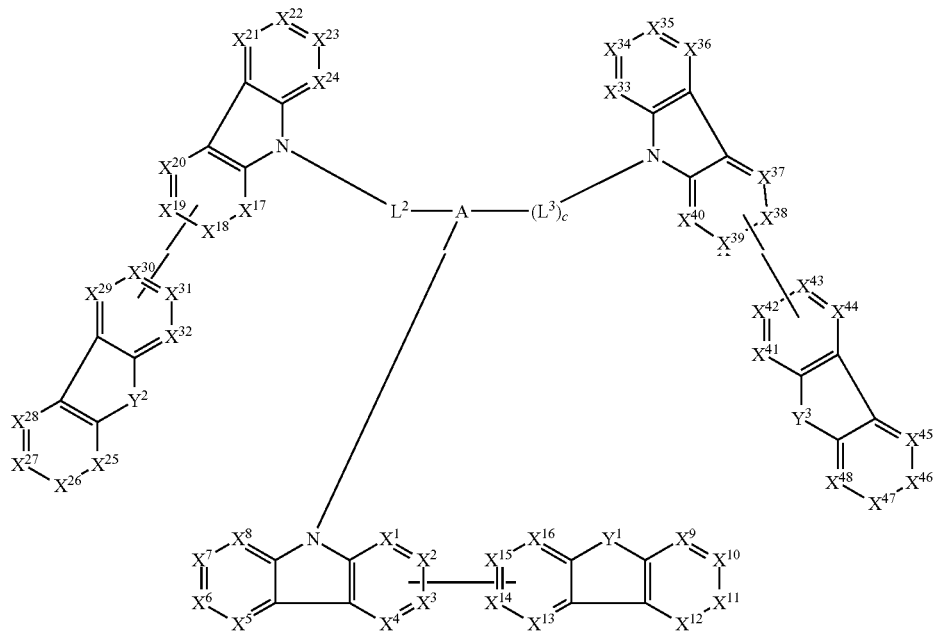
in formula 1a-ii-1[IV], A, $L^2$, $L^3$, c, $X^1$ to $X^{48}$, $Y^1$ to $Y^3$, and preferred examples thereof are as described above in formula 1[IV];

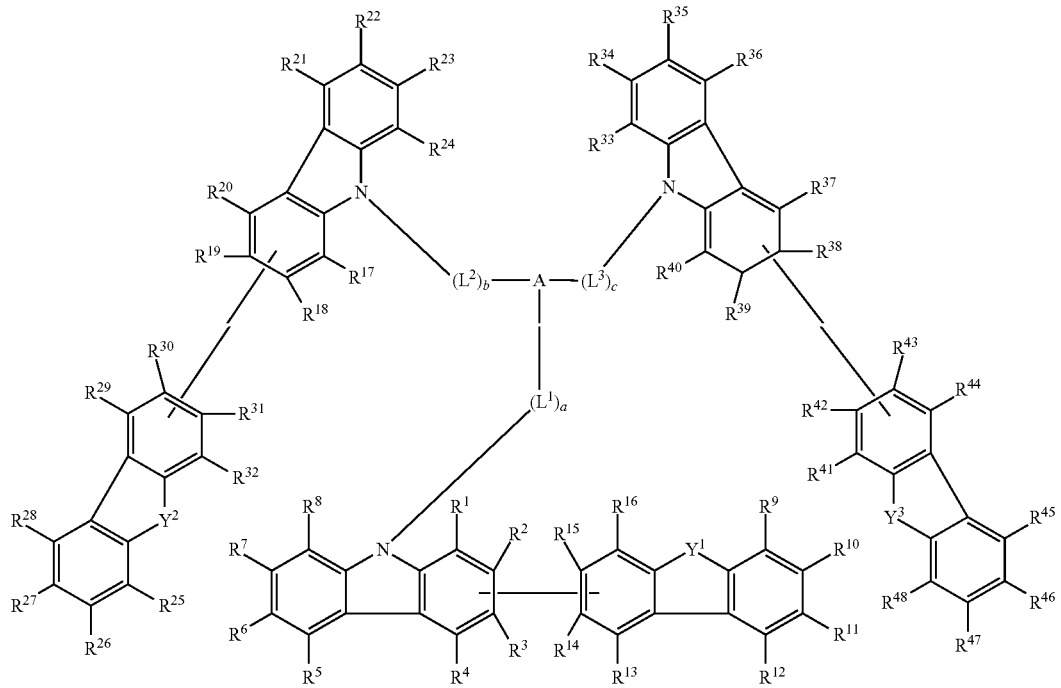
(1a'[IV])
in formula 1a'[IV], A, $L^1$ to $L^3$, a to c, $R^1$ to $R^{48}$, $Y^1$ to $Y^3$, and preferred examples thereof are as described above in formula 1[IV];
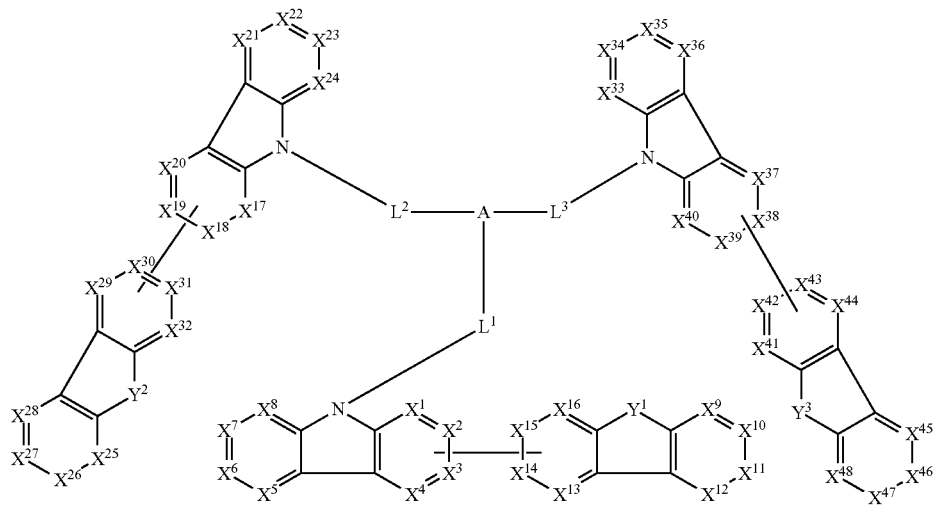
(1a-i[IV])
in formula 1a-i[IV], A, $L^1$ to $L^3$, $X^1$ to $X^{48}$, $Y^1$ to $Y^3$, and preferred examples thereof are as described above in formula 1[IV];

(1a'-i[IV])
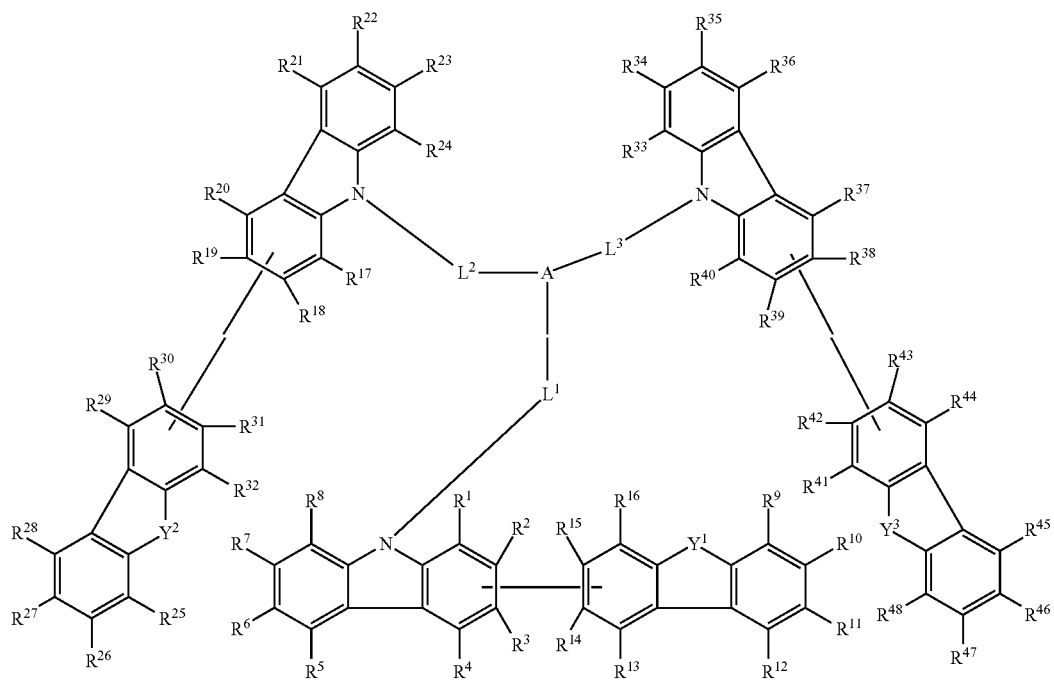
in formula 1a'-i[IV], A, $L^1$ to $L^3$, $R^1$ to $R^{48}$, $Y^1$ to $Y^3$, and preferred examples thereof are as described above in formula 1[IV];
(1a-ii[IV])
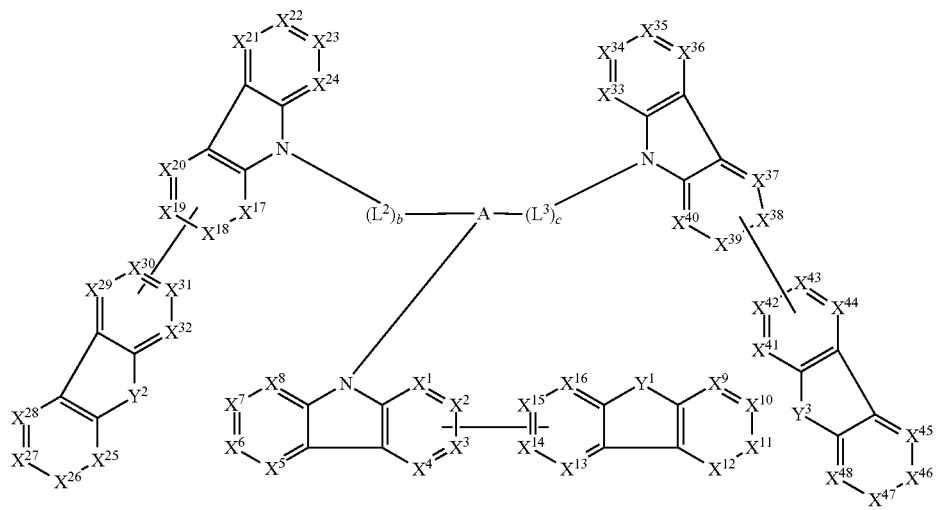
in formula 1a-ii[IV], A, $L^1$, $L^3$, b, c, $X^1$ to $X^{48}$, $Y^1$ to $Y^2$, and preferred examples thereof are as described above in formula 1[IV];

(1a'-ii[IV])
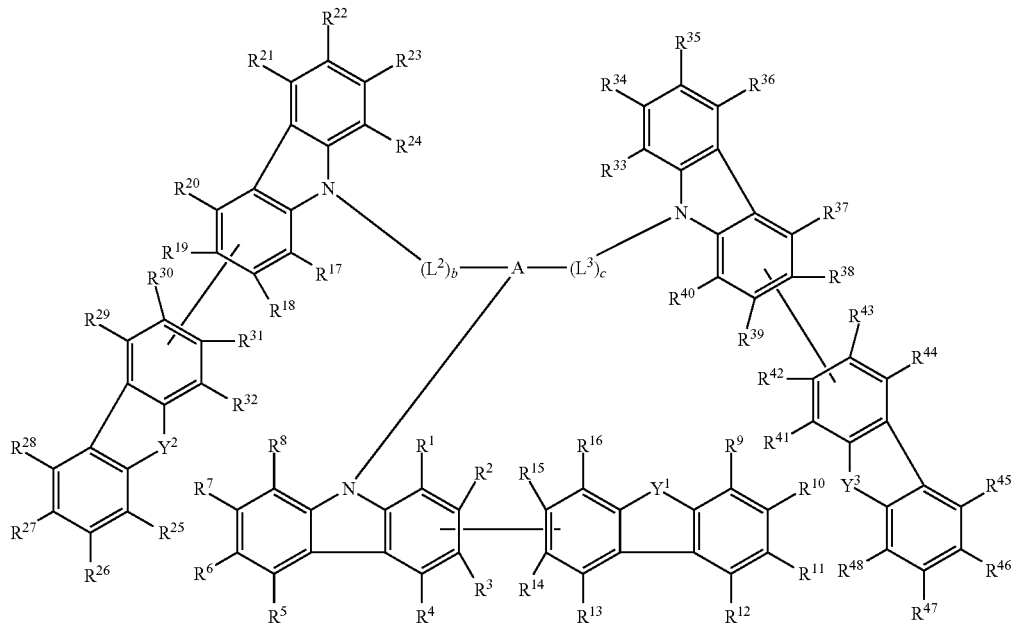
in formula 1a'-ii[IV], A, $L^2$, $L^3$, b, c, $R^1$ to $R^{48}$, $Y^1$ to $Y^3$, and preferred examples thereof are as described above in formula 1[IV];
(1a-iii[IV])
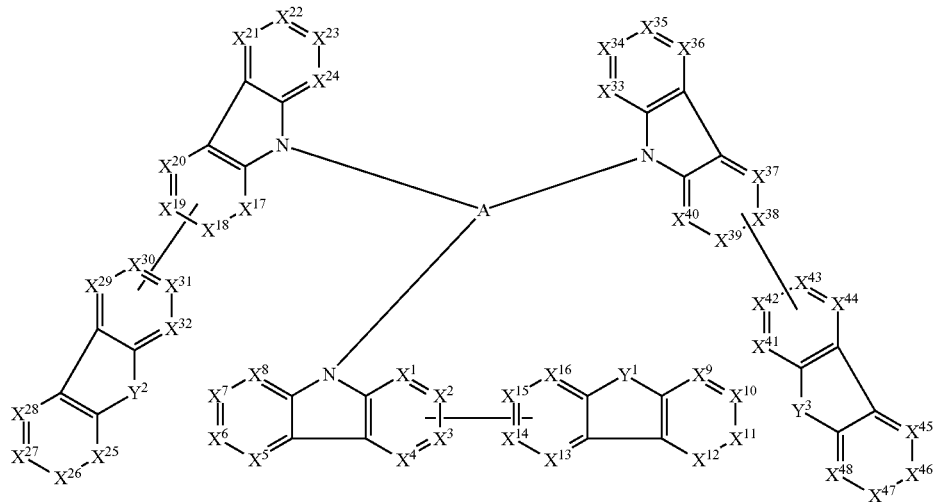
in formula 1a-iii[IV], A, $X^1$ to $X^{48}$, $Y^1$ to $Y^3$, and preferred examples thereof are as described above in formula 1[IV];

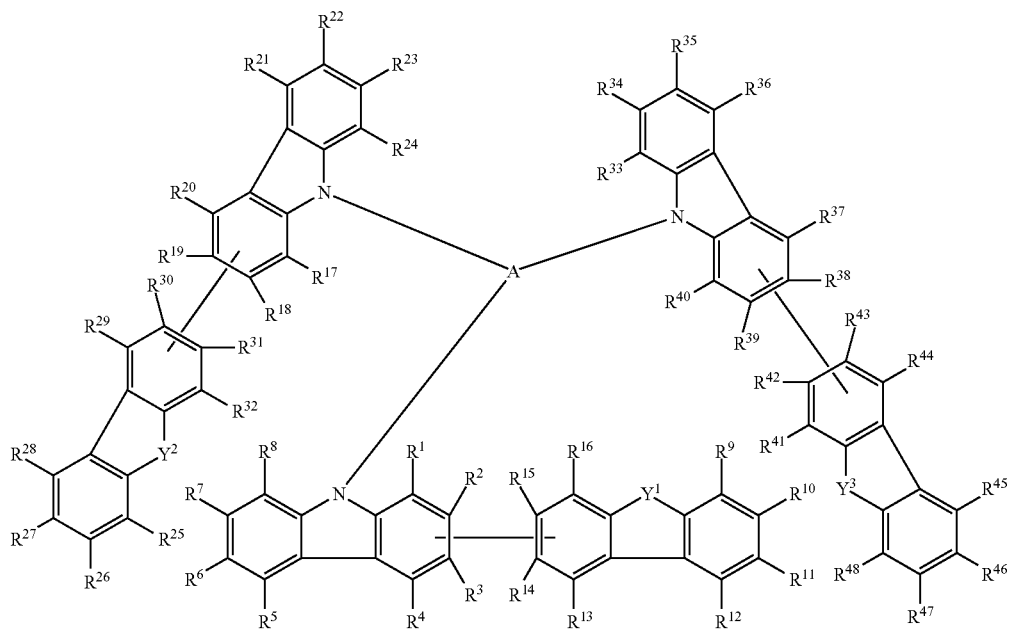
(1a'-iii[IV])
in formula 1a'-iii[IV], A, $R^1$ to $R^{48}$, $Y^1$ to $Y^3$, and preferred examples thereof are as described above in formula 1[IV];
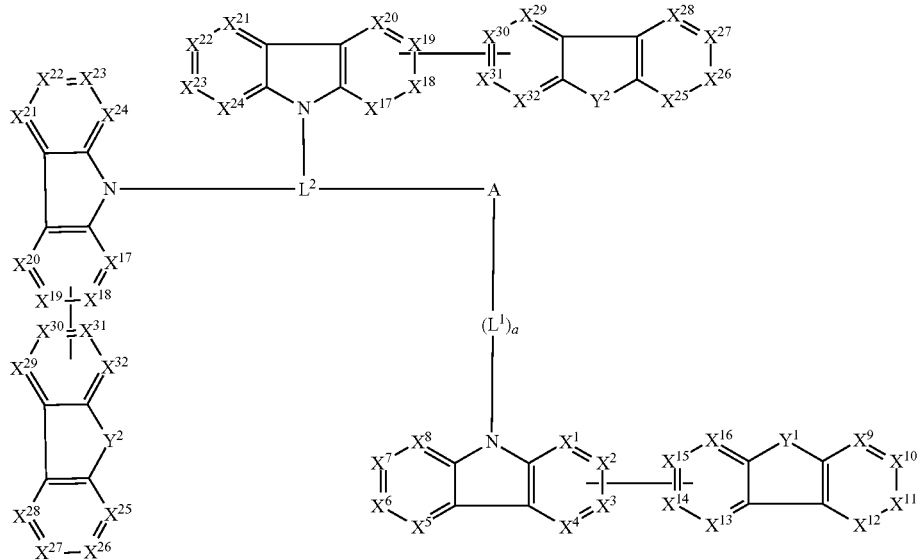
(1a-iv[IV])
in formula 1a-iv[IV], A, $L^1$, $L^2$, a, $X^1$ to $X^{32}$, $Y^1$ to $Y^3$, and preferred examples thereof are as described above in formula 1[IV]; and two or more groups represented by the same symbol may be the same or different;

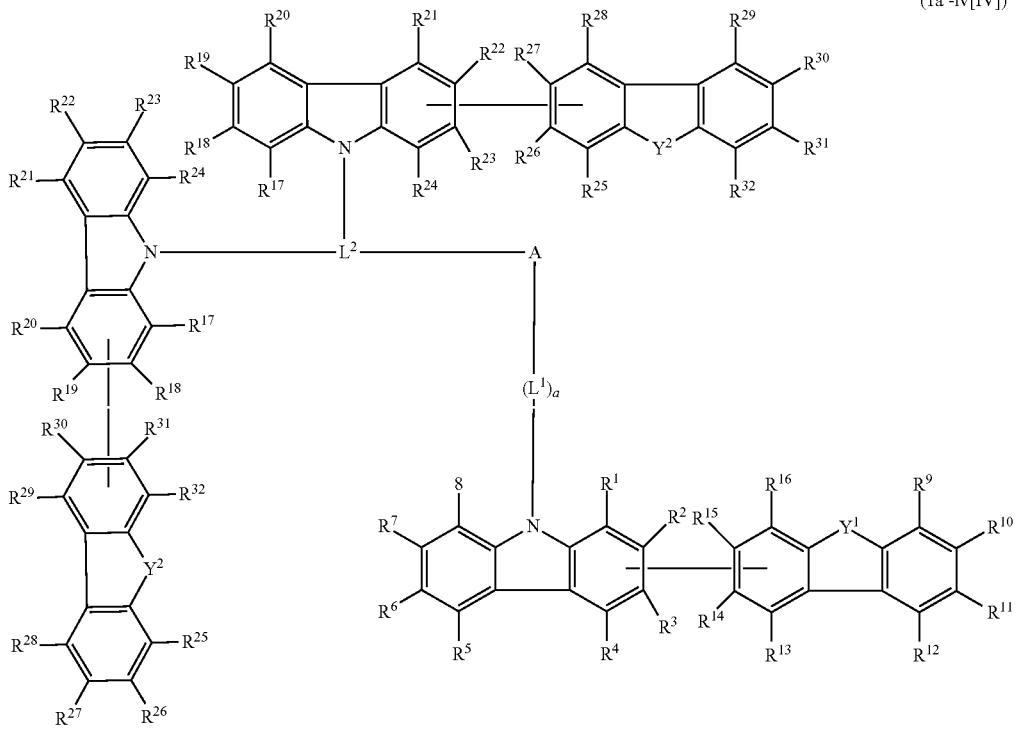

(1a'-iv[IV])

in formula 1a'-iv[IV], A, $L^1$, $L^2$, a, $R^1$ to $R^{32}$, $Y^1$, $Y^2$, and preferred examples thereof are as described above in formula 1[IV]; and two or more groups represented by the same symbol may be the same or different;

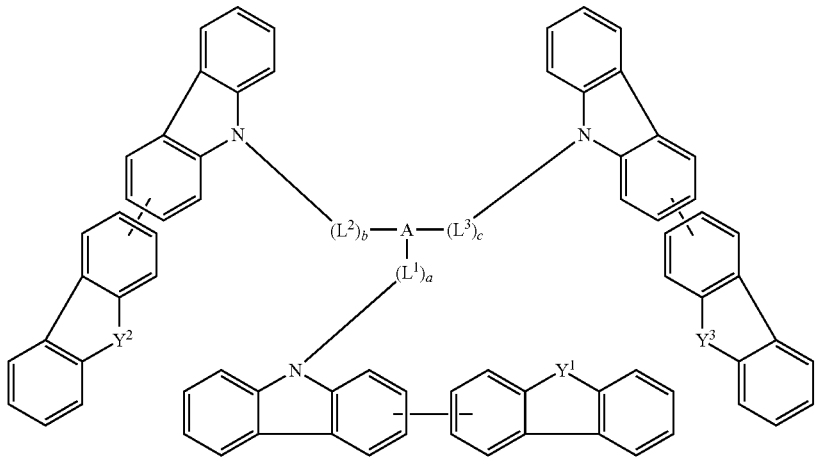

(1a'-H[IV])

in formula 1a'-H[IV], A, $L^1$ to $L^3$, a to c, $Y^1$ to $Y^3$, and preferred examples thereof are as described above in formula 1[IV]; and each terminal end of a bond extending from a benzene ring in a carbazolyl group is bonded to one of four carbon atoms of a benzene ring, each containing the terminal end of the bond, in place of a hydrogen atom removed therefrom;

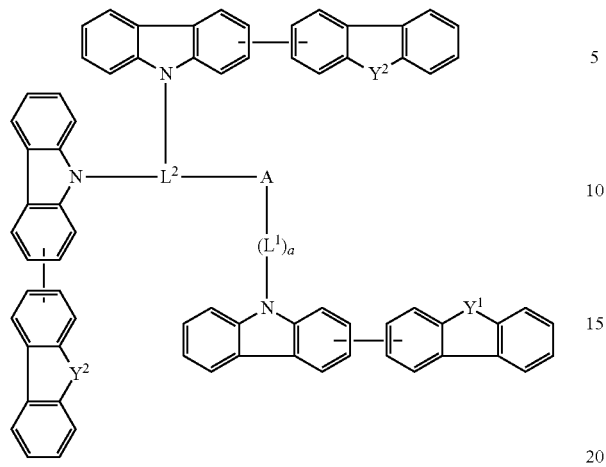

(1a'-iv-H[IV])

in formula 1a'-iv-H[IV], A, $L^1$, $L^2$, a, $Y^1$, $Y^2$, and preferred examples thereof are as described above in formula 1[IV]; two or more groups represented by the same symbol may be the same or different; and each terminal end of a bond extending from a benzene ring in a carbazolyl group is bonded to one of four carbon atoms of a benzene ring, each containing the terminal end of the bond, in place of a hydrogen atom removed therefrom;

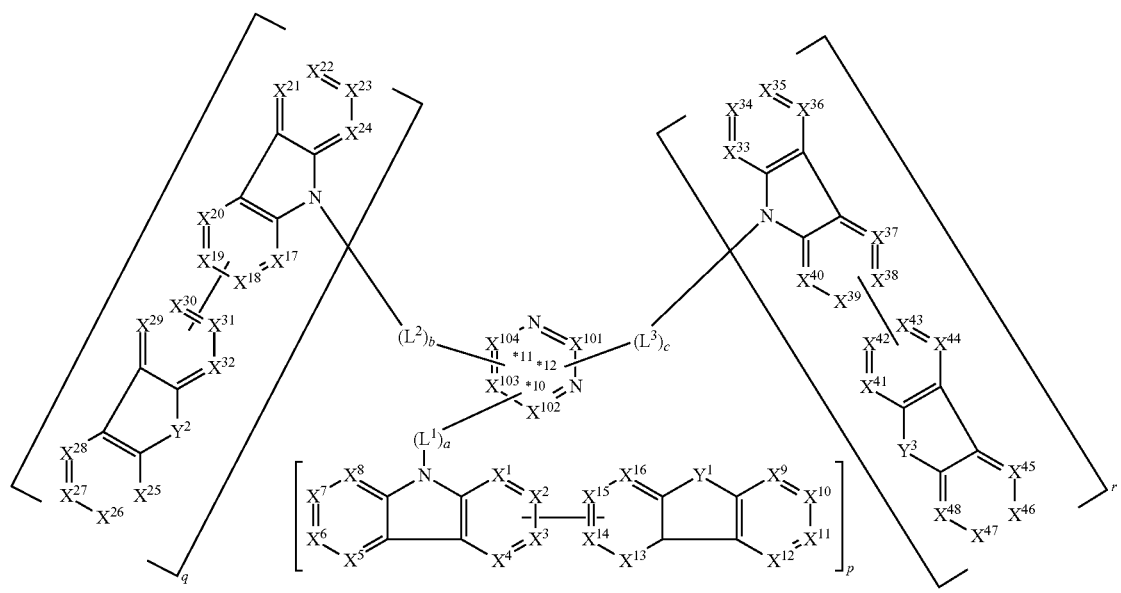

(1b-i[IV])

in formula 1b-i[IV], $L^1$ to $L^2$, a to c, p to r, $X^1$ to $X^{48}$, $Y^1$ to $Y^3$, and preferred examples thereof are as described above in formula 1[IV]; when p, q or r is 2 or 3, 2 or 3 groups in each [ ] may be the same or different;

$X^{101}$ to $X^{104}$ each represent a carbon atom bonded to one of *10 to *12, C(Rx), or a nitrogen atom; and Rx represents a hydrogen atom or a substituent, two or more groups Rx may be the same or different, and two selected from groups Rx may be bonded to each other to form a ring;

(1b-ii[IV])

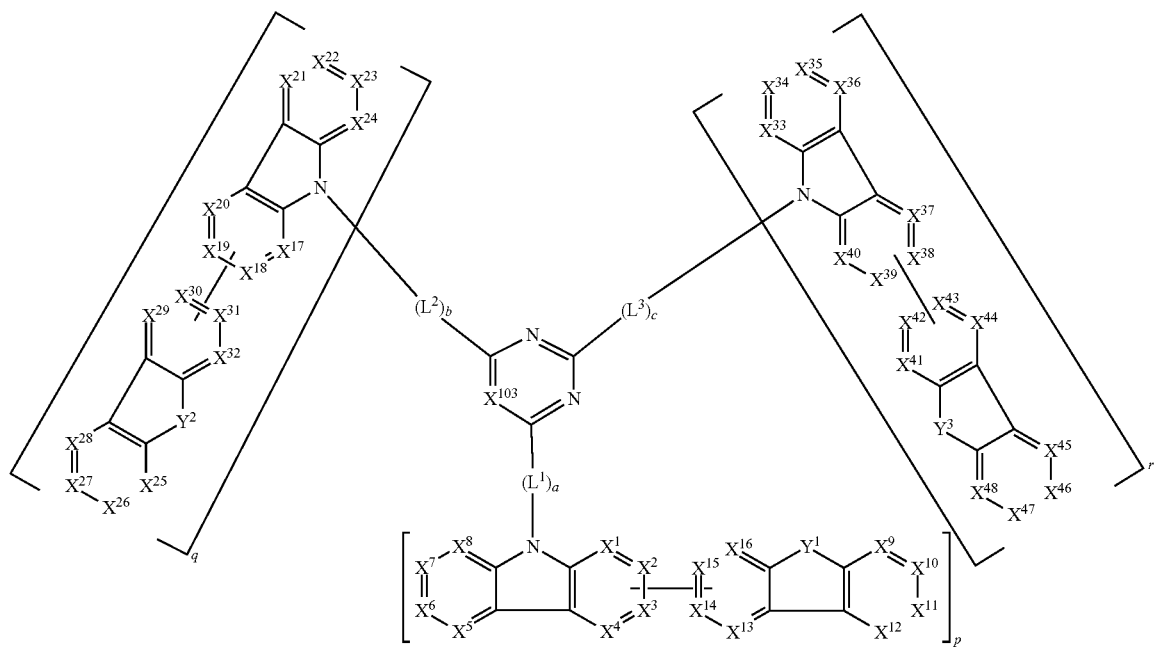

in formula 1b-ii[IV], $L^1$ to $L^3$, a to c, p to r, $X^1$ to $X^{48}$, $Y^1$ to $Y^3$, and preferred examples thereof are as described above in formula 1[IV]; when p, q or r is 2 or 3, 2 or 3 groups in each [ ] may be the same or different; $X^{103}$ represents C(Rx) or a nitrogen atom; and Rx represents a hydrogen atom or a substituent;

in formula 1b-iii[IV], $L^1$ to $L^3$, a to c, p to r, $X^1$ to $X^{48}$, $Y^1$ to $Y^3$, and preferred examples thereof are as described above in formula 1[IV];

when p, q or r is 2 or 3, 2 or 3 groups in each [ ] may be the same or different;

$X^{101}$, $X^{102}$, $X^{105}$ to $X^{108}$ each represent a carbon atom bonded to one of *10 to *12, C(Rx), or a nitrogen atom; and (1b-iii[IV])

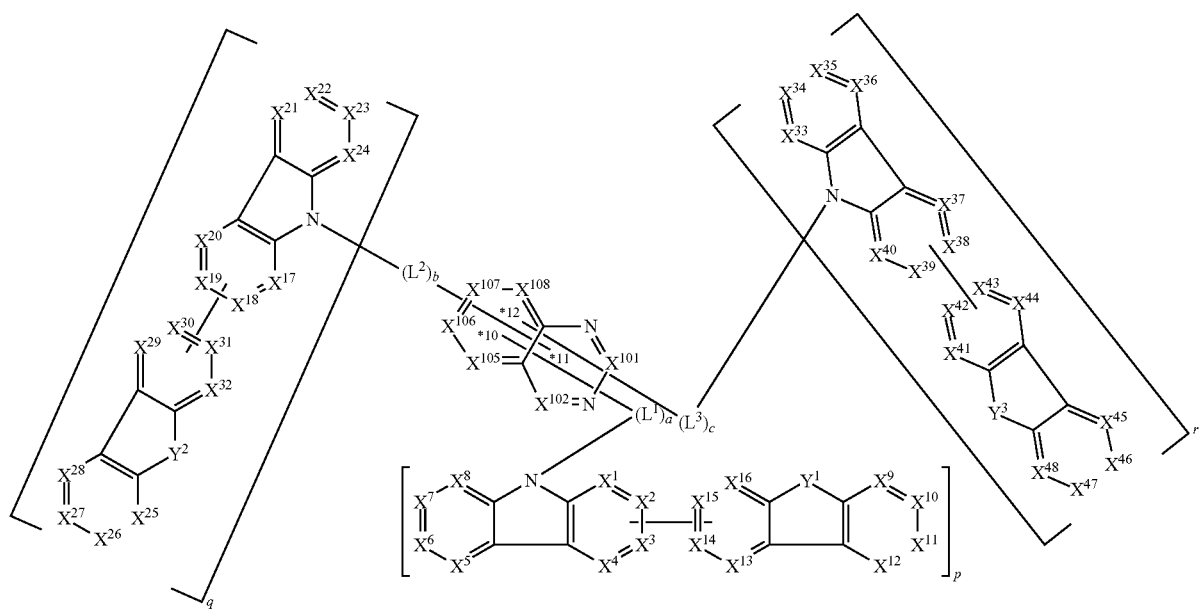

Rx represents a hydrogen atom or a substituent, two or more groups Rx may be the same or different, and two selected from groups Rx may be bonded to each other to form a ring; and 1 to 3 carbon atoms from which one to three selected from $R^{101}$, $R^{102}$, and $R^{105}$ to $R^{108}$ are removed are each bonded to one of *10 to *12 and the others each independently represent a hydrogen atom or a substituent; and (1b-iv[IV])

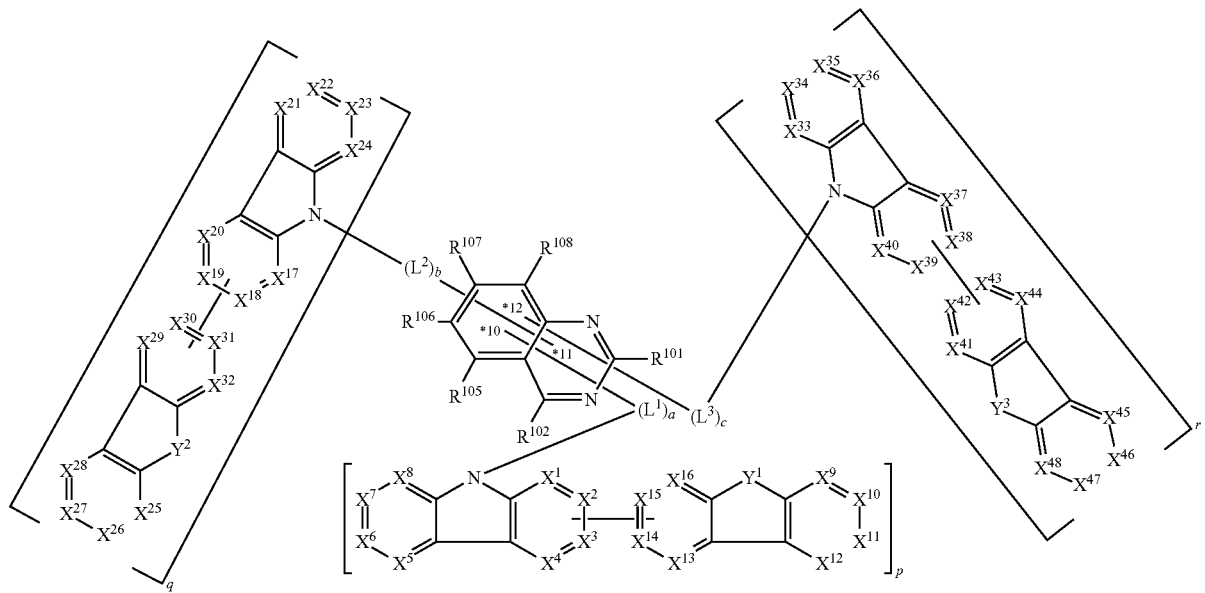

in formula 1b-iv[IV], $L^1$ to $L^3$, a to c, p to r, $X^1$ to $X^{48}$, $Y^1$ to $Y^3$, and preferred examples thereof are as described above in formula 1[IV];

when p, q or r is 2 or 3, 2 or 3 groups in each [ ] may be the same or different;

two selected from $R^{102}$ and $R^{105}$ to $R^{108}$ may be bonded to each other to form a ring.

The compounds represented by the following formulae are particularly preferably used as compound 1[IV]:

(1-ii-1[IV])

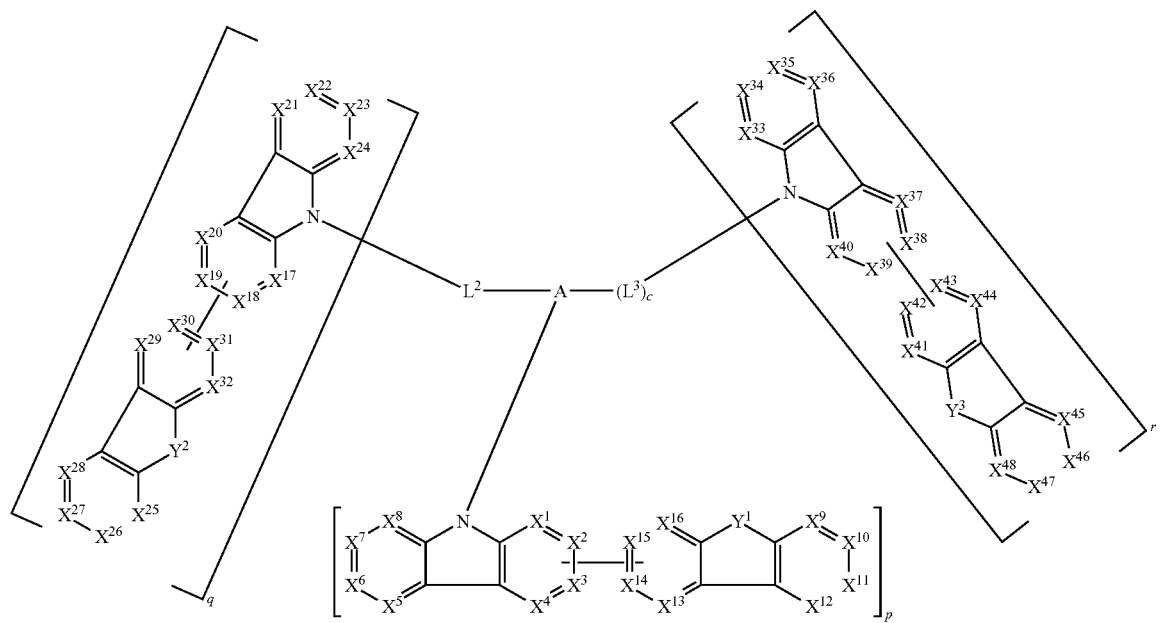

in formula 1-ii-1[IV],

A represents a substituted or unsubstituted nitrogen-containing heteroaromatic hydrocarbon group having 5 to 30 ring atoms;

$L^2$ and $L^3$ each independently represent a substituted or unsubstituted aromatic hydrocarbon group having 6 to 30 ring carbon atoms, a substituted or unsubstituted heterocyclic group having 5 to 30 ring atoms, or a group wherein 2 to 4 groups selected from the preceding groups are bonded to each other;

c represents 0 or 1;

$X^1$ to $X^{48}$ each represent $C(R^1)$ to $C(R^{48})$, respectively, or a nitrogen atom;

$R^1$ to $R^{48}$ each independently represent a hydrogen atom or a substituent, provided that one of $X^1$ to $X^4$ represents a carbon atom which is directly bonded to a carbon atom represented by one of $X^{13}$ to $X^{16}$, one of $X^{17}$ to $X^{20}$ represents a carbon atom which is directly bonded to a carbon atom represented by one of $X^{20}$ to $X^{32}$, one of $X^{37}$ to $X^{40}$ represents a carbon atom which is directly bonded to a carbon atom represented by one of $X^{41}$ to $X^{44}$, and two selected from $R^1$ to $R^8$, two selected from $R^9$ to $R^{16}$, two selected from $R^{17}$ to $R^{24}$, two selected from $R^{25}$ to $R^{32}$, two selected from $R^{33}$ to $R^{40}$, and two selected from $R^{41}$ to $R^{48}$, each not involved in the above direct bonding, may be bonded to each other to form a ring;

$Y^1$ to $Y^3$ each independently represent an oxygen atom, a sulfur atom, $C(R^A)(R^B)$, $Si(R^C)(R^D)$, $P(R^E)$, $P(=O)(R^F)$, $S(=O)_2$, or $P(=S)(R^G)$;

$R^A$, $R^B$, $R^C$, $R^D$, $R^E$, $R^F$, and $R^G$ each independently represent a hydrogen atom or a substituent, and $R^A$ and $R^B$, and $R^C$ and $R^D$ may be bonded to each other to form a ring; and p to r each independently represent an integer of 0 to 3, p+q+r=3, and when p, q or r is 2 or 3, 2 or 3 groups in each [ ] may be the same or different, respectively;

(1a-ii-1[IV])

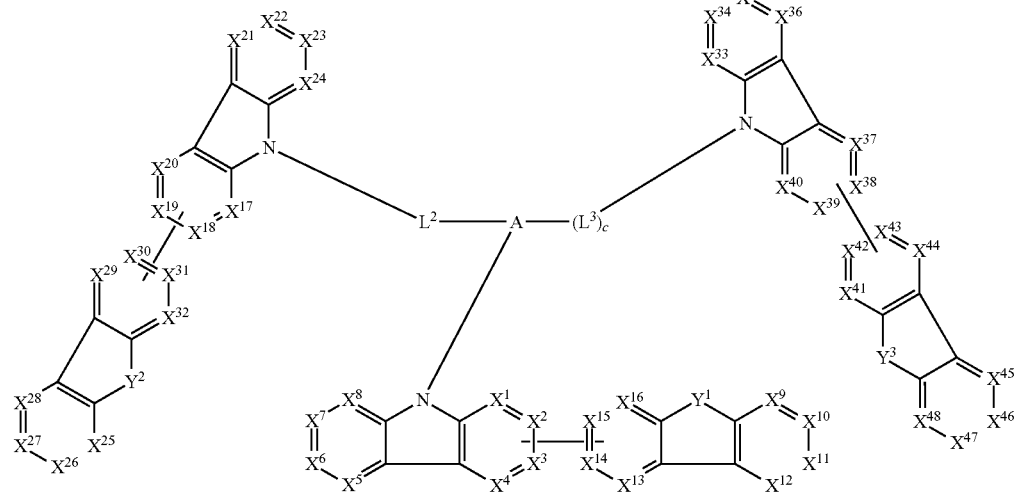

in formula 1a-ii-1[IV], A, $L^2$, $L^3$, c, $X^1$ to $X^{48}$, $Y^1$ to $Y^3$, and preferred examples thereof are as described above in formula 1-ii-1[IV];

(1a'-ii-1[IV])

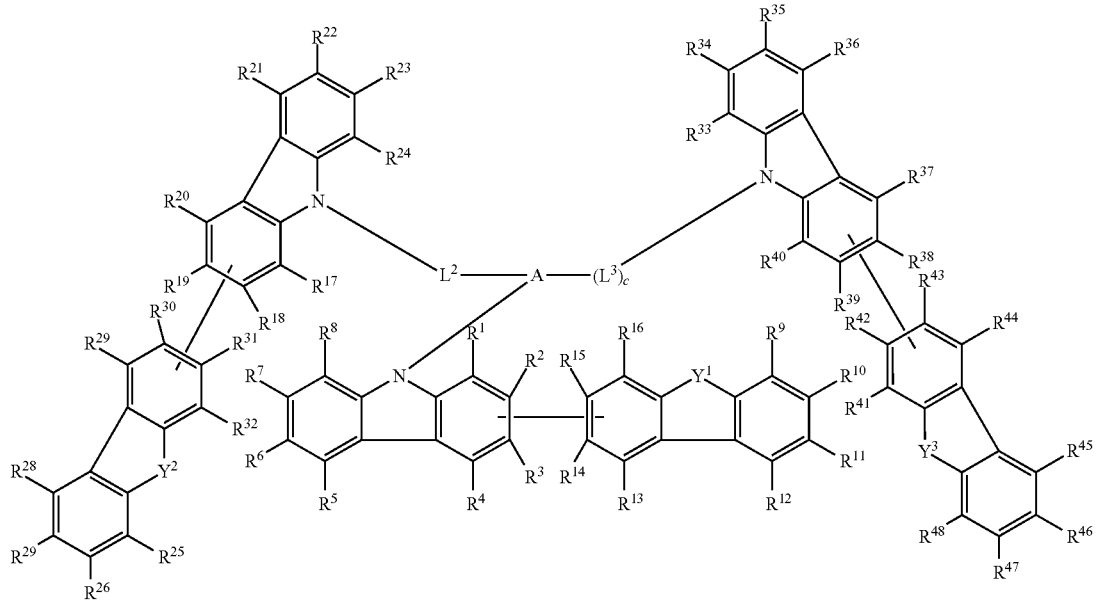

in formula 1a'-ii-1[IV], A, $L^2$, $L^3$, c, $R^1$ to $R^{48}$, $Y^1$ to $Y^3$, and preferred examples thereof are as described above in formula 1-ii-1[IV];

(1b-i-1[IV])

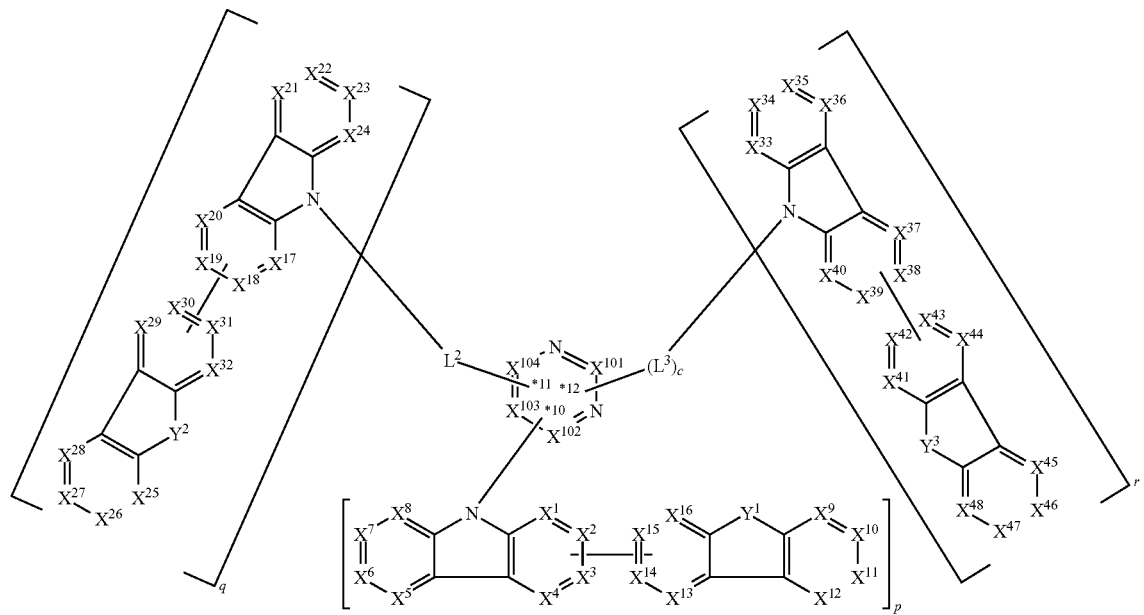

in formula 1b-i-1[IV], $L^2$, $L^3$, c, p to r, $X^1$ to $X^{48}$, $Y^1$ to $Y^3$, and preferred examples thereof are as described above in formula 1-ii-1 [IV];

when p, q or r is 2 or 3, 2 or 3 groups in each [ ] may be the same or different;

$X^{101}$ to $X^{104}$ each represent a carbon atom bonded to one of *10 to *12, C(Rx), or a nitrogen atom; and Rx represents a hydrogen atom or a substituent, two or more groups Rx may be the same or different, and two selected from groups Rx may be bonded to each other to form a ring;

(1b-ii-1[IV])

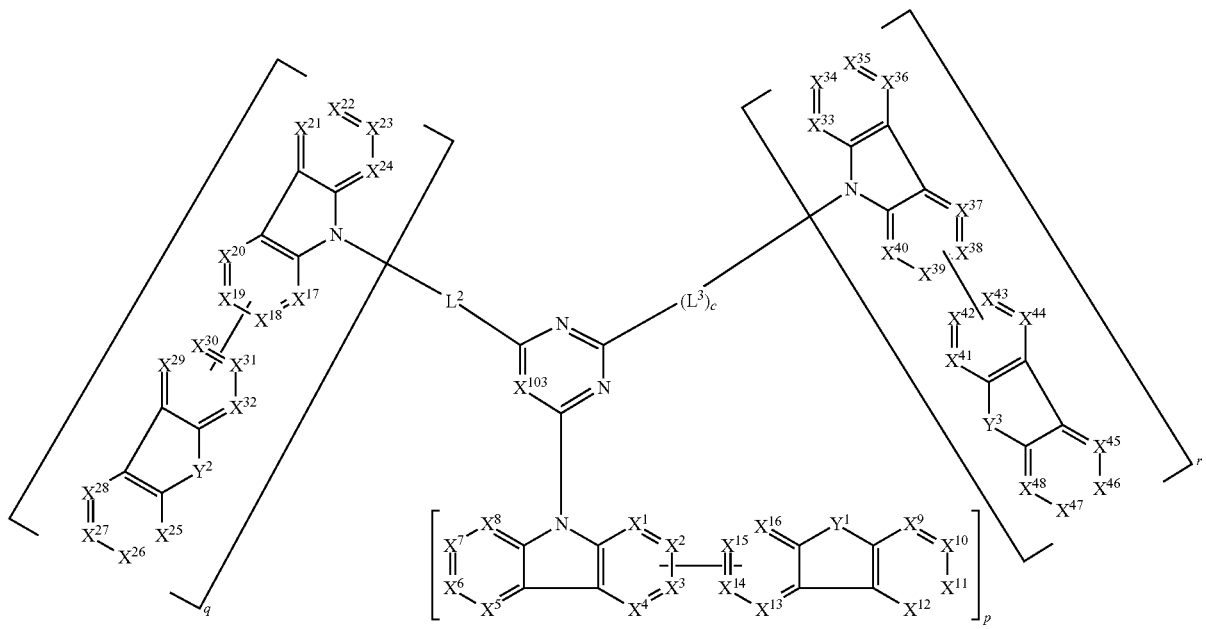

in formula 1b-ii-1[IV], $L^2$, $L^3$, c, p to r, $X^1$ to $X^4$, $Y^1$ to $Y^3$, and preferred examples thereof are as described above in formula 1-ii-1[IV]; when p, q or r is 2 or 3, 2 or 3 groups in each [ ] may be the same or different; $X^{103}$ represents C(Rx) or a nitrogen atom; and Rx represents a hydrogen atom or a substituent;

(1b-iii-1[IV])

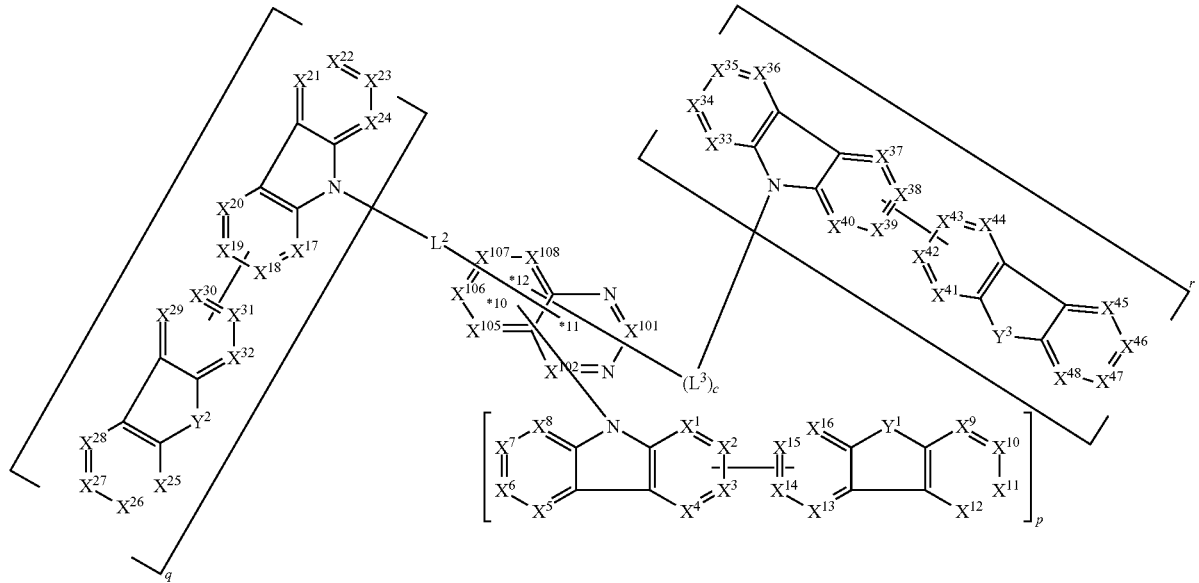

in formula 1b-iii-1[IV], $L^2$, $L^3$, c, p to r, $X^1$ to $X^4$, $Y^1$ to $Y^3$, and preferred examples thereof are as described above in formula 1-ii-1[IV];

when p, q or r is 2 or 3, 2 or 3 groups in each [ ] may be the same or different;

$X^{101}$, $X^{102}$, $X^{105}$ to $X^{108}$ each represent a carbon atom bonded to one of *10 to *12, C(Rx), or a nitrogen atom; and Rx represents a hydrogen atom or a substituent, two or more groups Rx may be the same or different, and two selected from groups Rx may be bonded to each other to form a ring; and (1b-iv-1[IV])

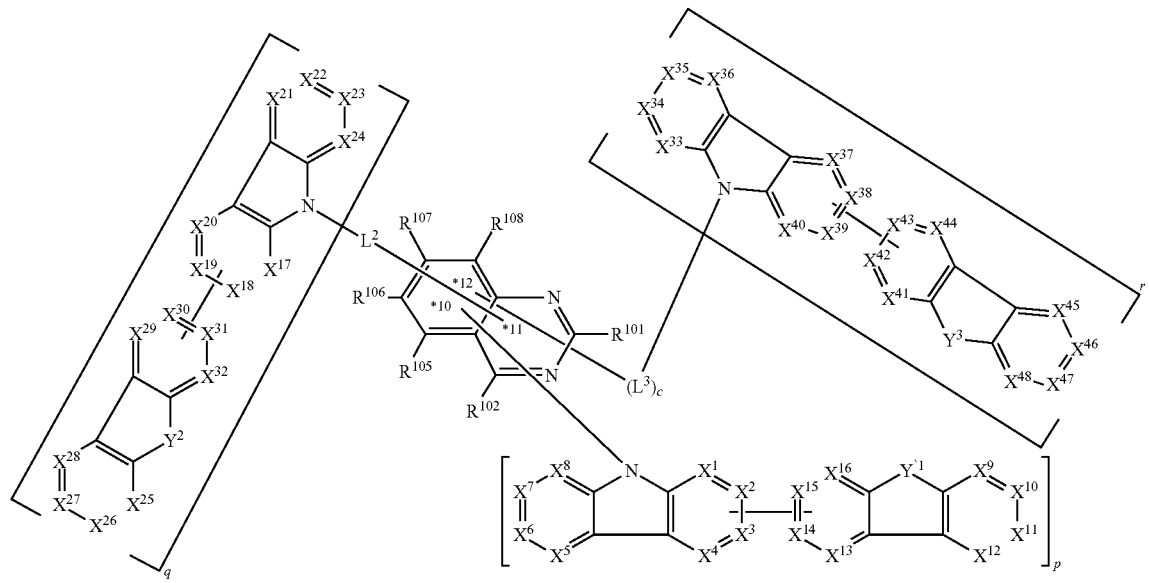

in formula 1b-iv-1[IV], $L^2$, $L^3$, c, p to r, $X^1$ to $X^{48}$, $Y^1$ to $Y^3$, and preferred examples thereof are as described above in formula 1-ii-1[IV];

when p, q or r is 2 or 3, 2 or 3 groups in each [ ] may be the same or different;

1 to 3 carbon atoms from which one to three selected from $R^{101}$, $R^{102}$, and $R^{105}$ to $R^{108}$ are removed are each bonded to one of *10 to *12, and the others each independently represent a hydrogen atom or a substituent; and two selected from $R^{102}$ and $R^{105}$ to $R^{108}$ may be bonded to each other to form a ring.

Examples of compound 1[IV] in an aspect of the invention are shown below, although not limited thereto.

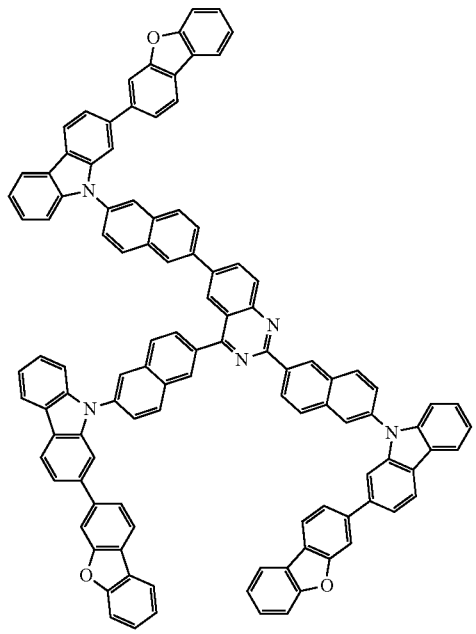
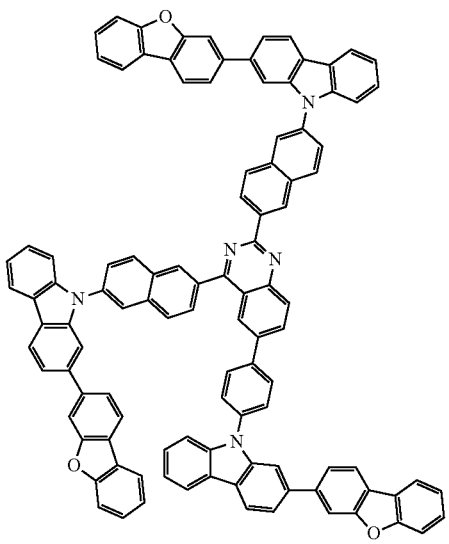
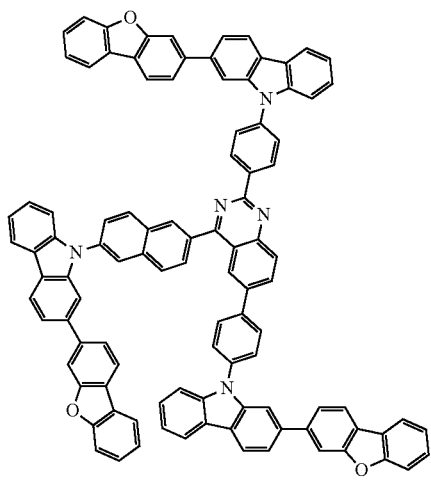
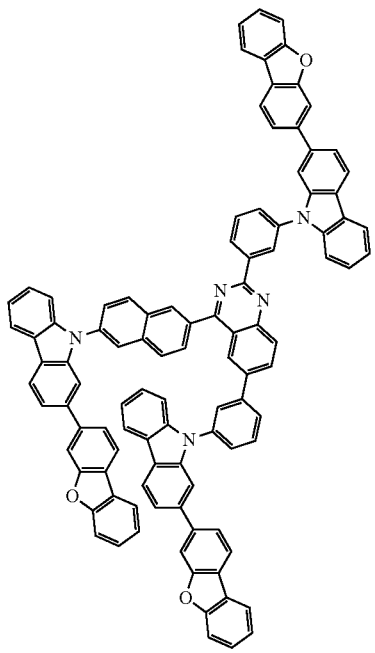

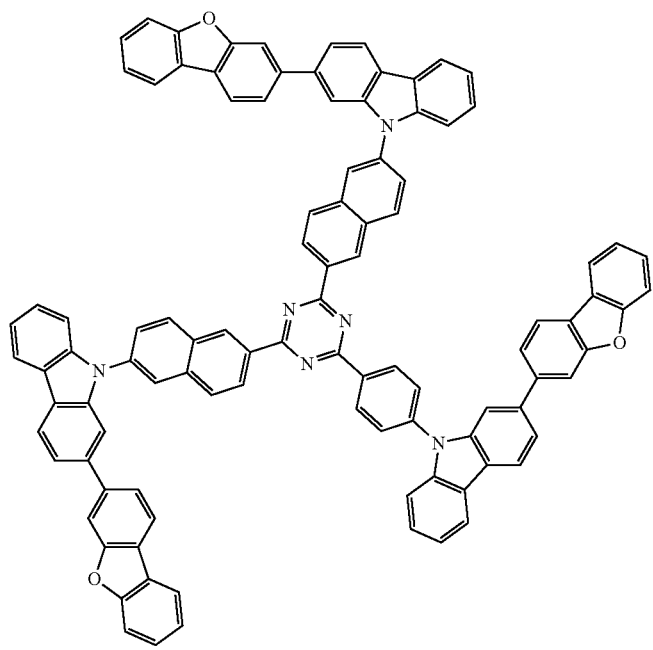
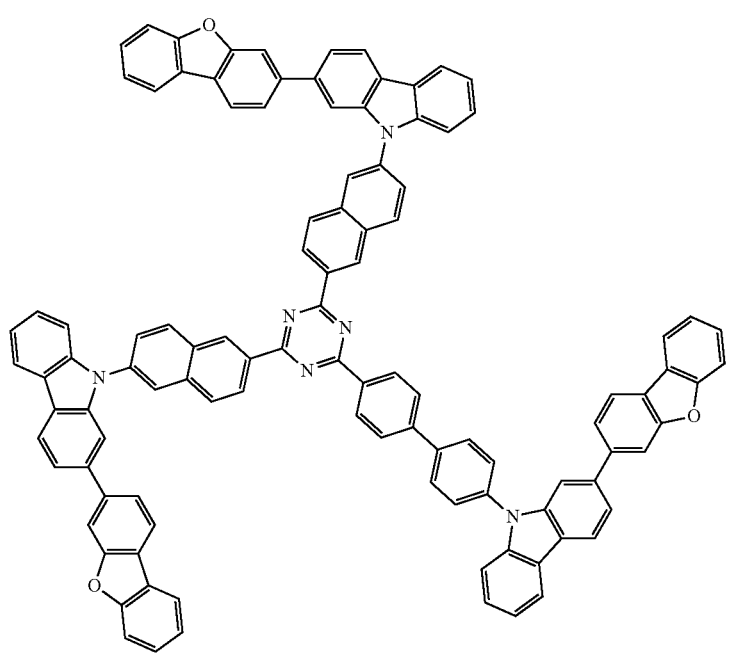

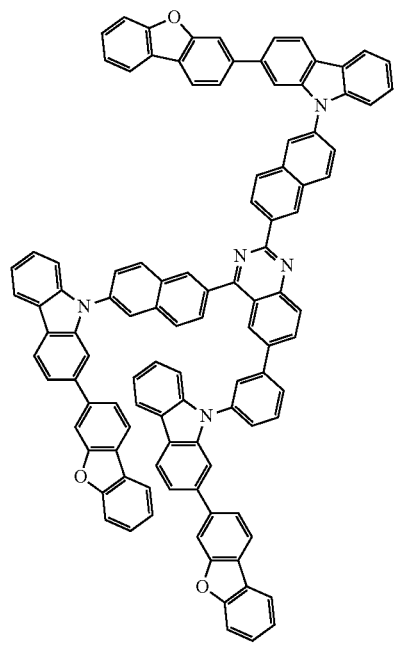
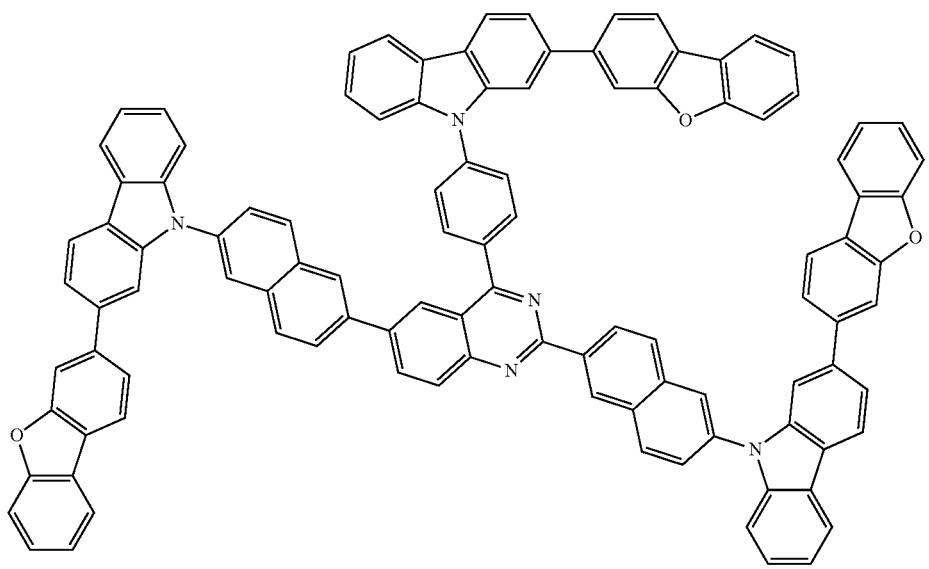

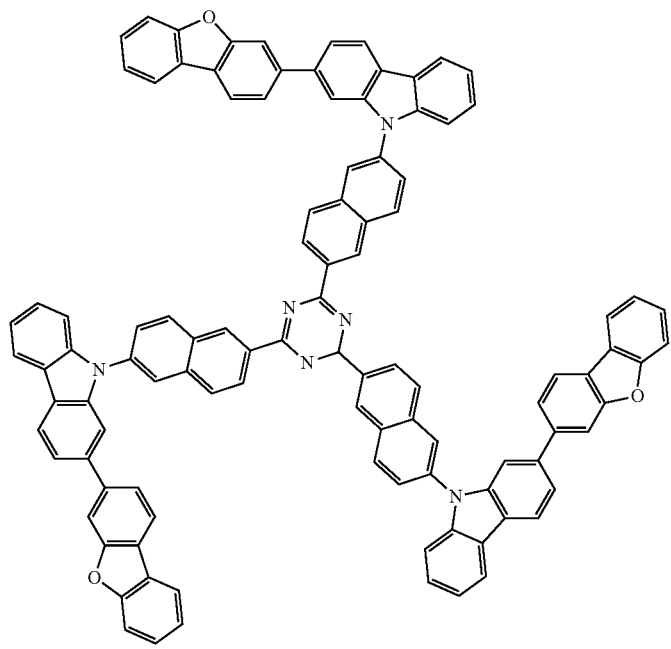
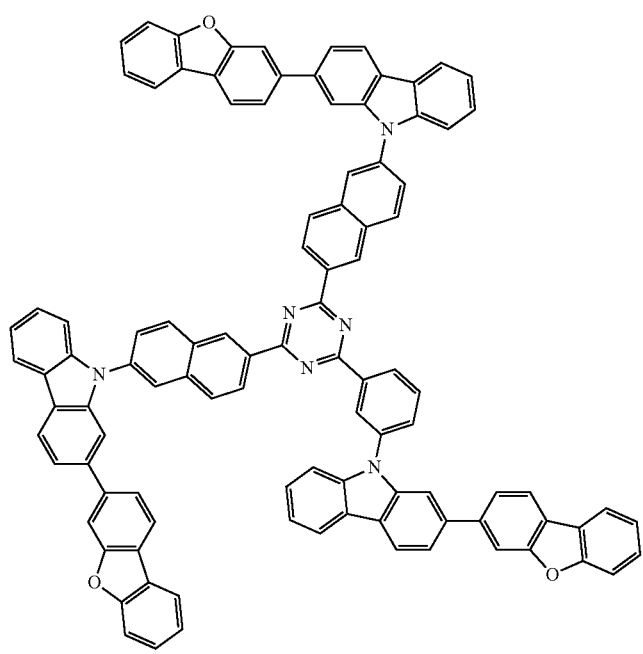

1251
1252
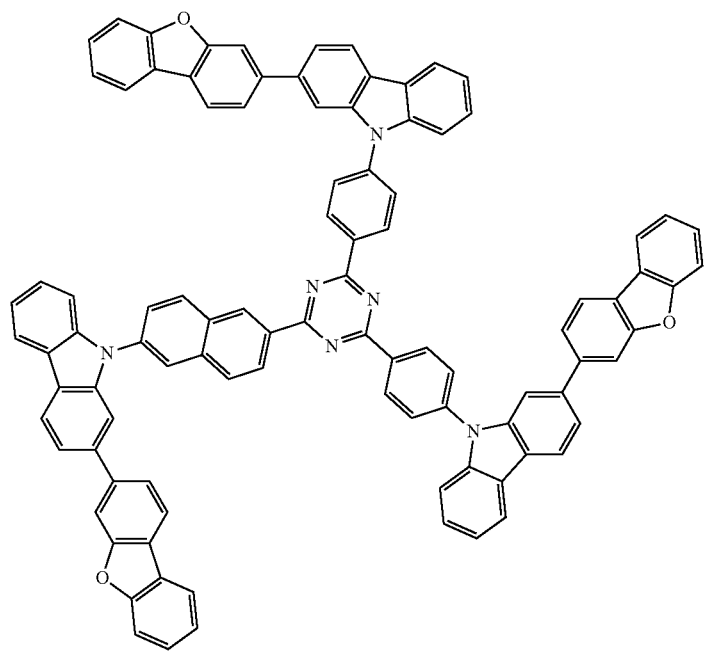
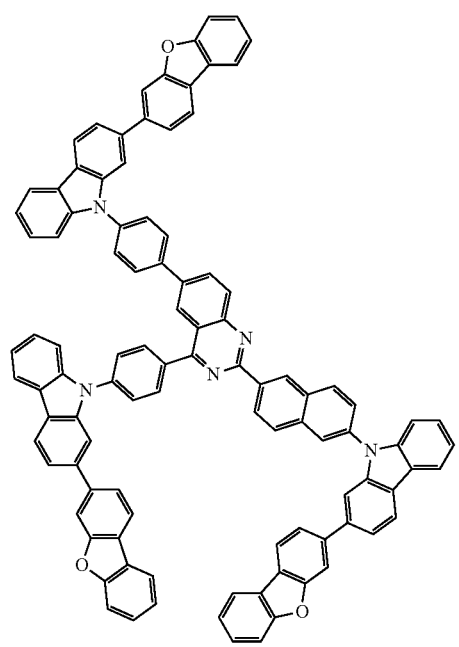

1253
1254
-continued
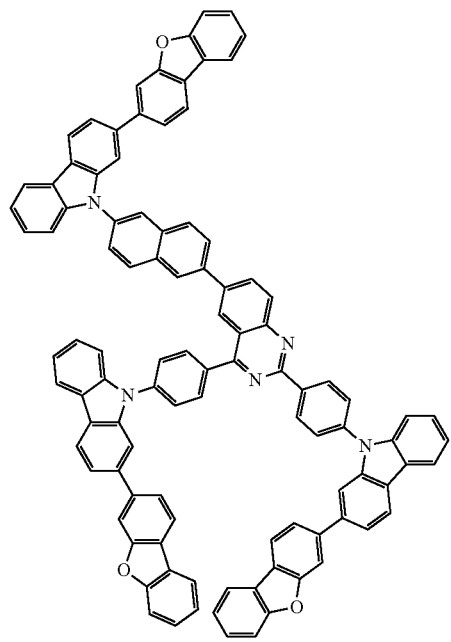
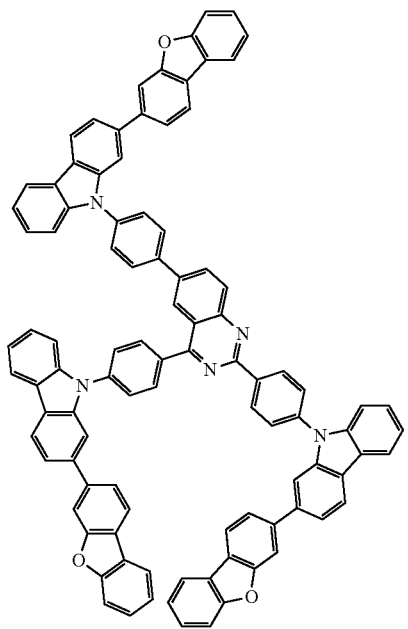
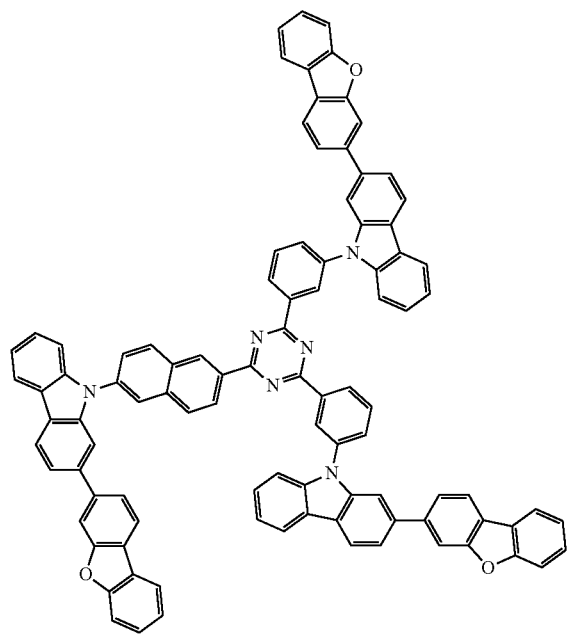
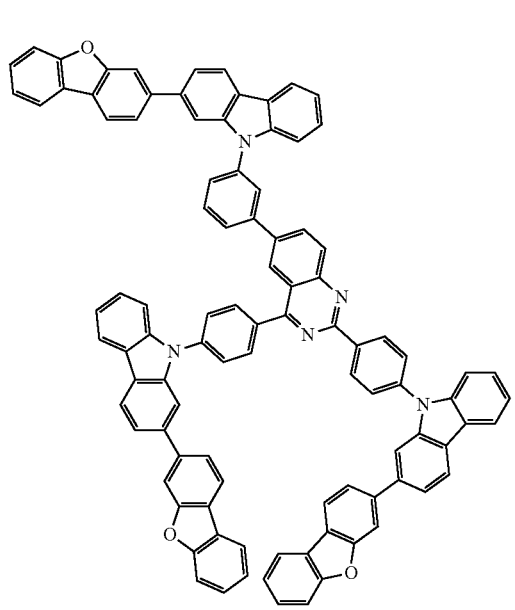

1255 1256
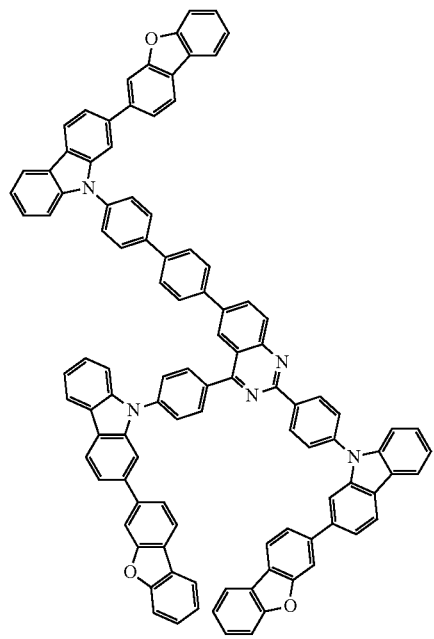
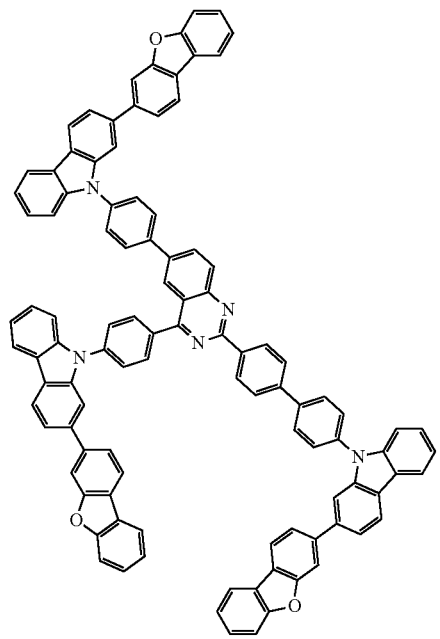
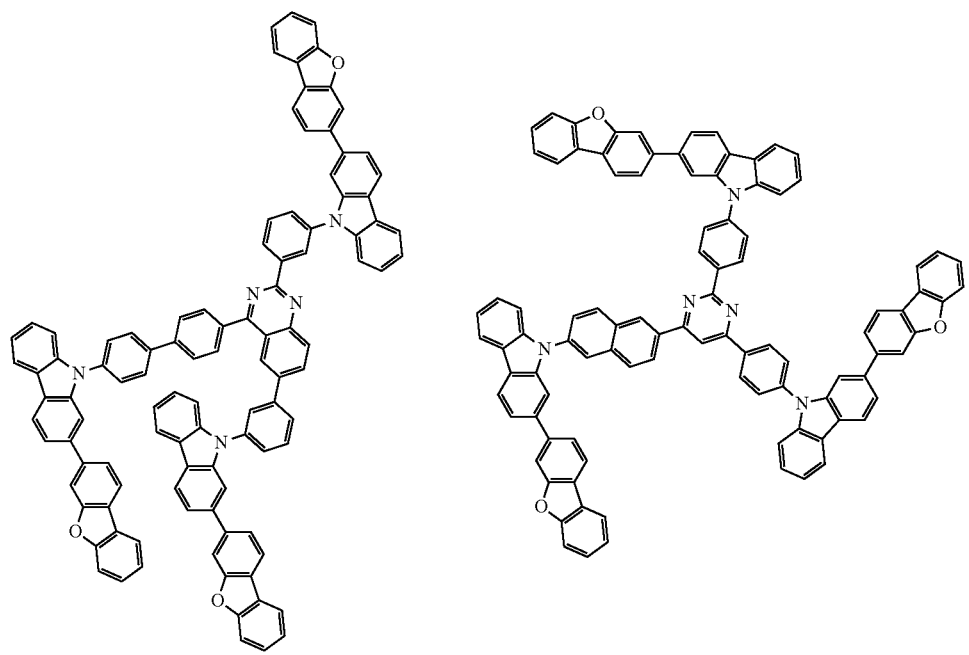 [SMILES: c1cc(-c2ccc3nc(-c4cccc(-n5c6ccccc6c6ccc(-c7ccc8c(c7)oc7ccccc78)cc65)c4)nc(-c4ccc(-c5ccc(-n6c7ccccc7c7ccc(-c8ccc9c(c8)oc8ccccc89)cc76)cc5)cc4)c3c2)cc(-n2c3ccccc3c3ccc(-c4ccc5c(c4)oc4ccccc45)cc32)c1 ; c1ccc2c(c1)oc1cc(-c3ccc4c5ccccc5n(-c5ccc(-c6cc(-c7ccc8cc(-n9c%10ccccc%10c%10ccc(-c%11ccc%12c(c%11)oc%11ccccc%11%12)cc%109)ccc8c7)nc(-c7ccc(-n8c9ccccc9c9ccc(-c%10ccc%11c(c%10)oc%10ccccc%10%11)cc98)cc7)n6)cc5)c4c3)ccc12]

1257 1258
-continued
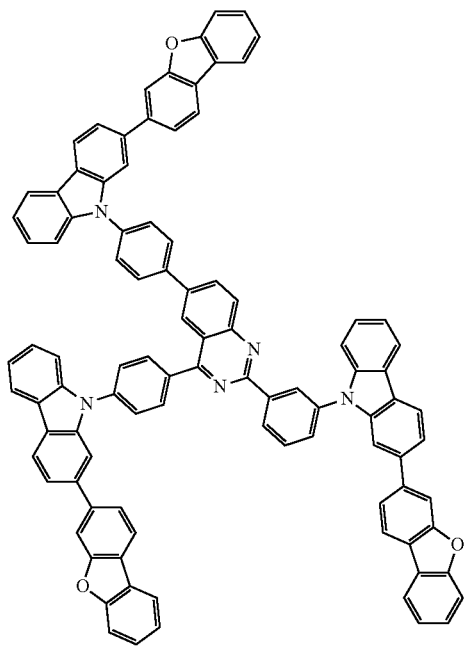
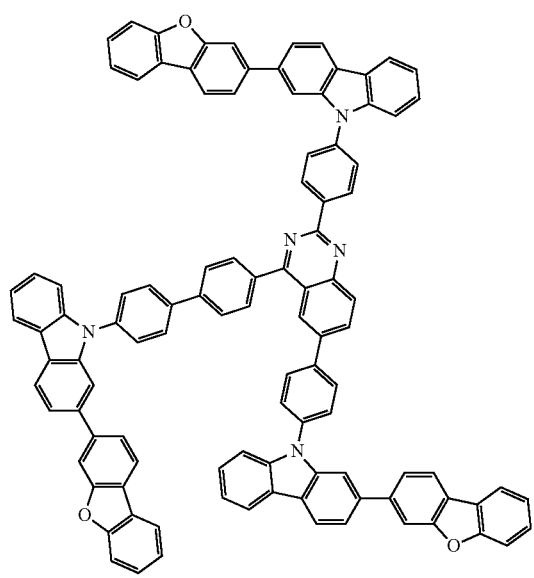
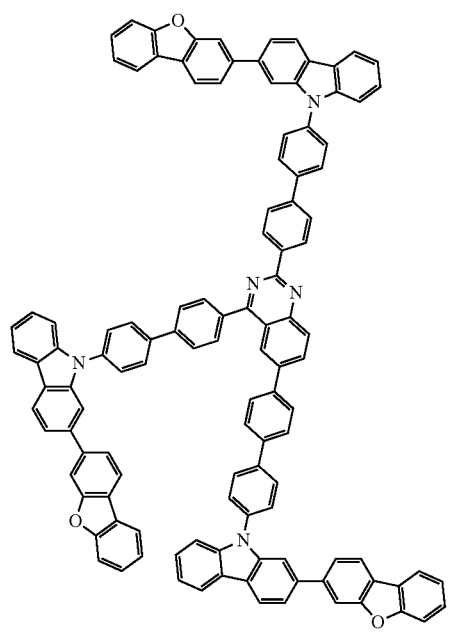
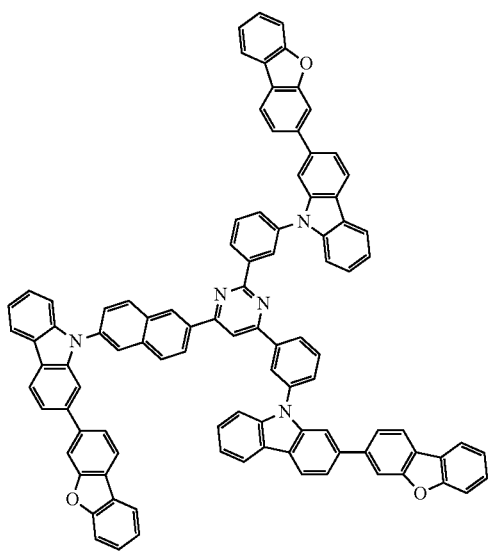

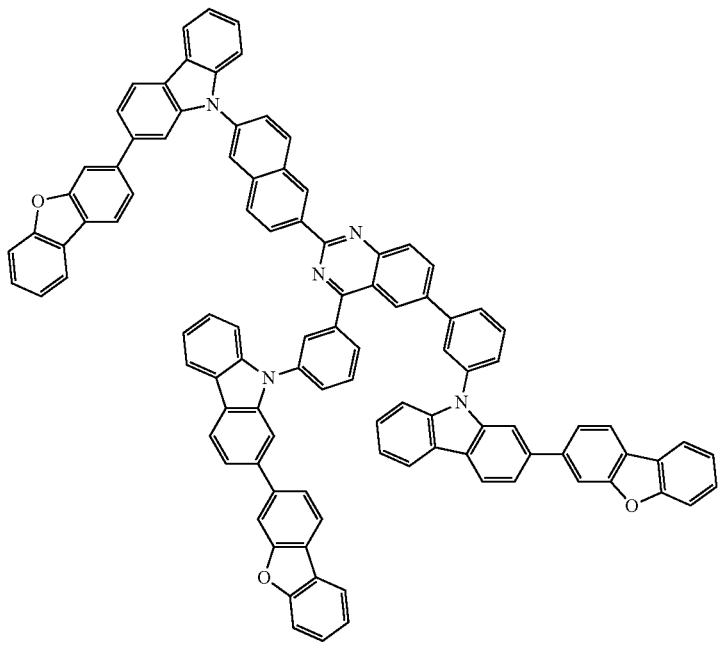
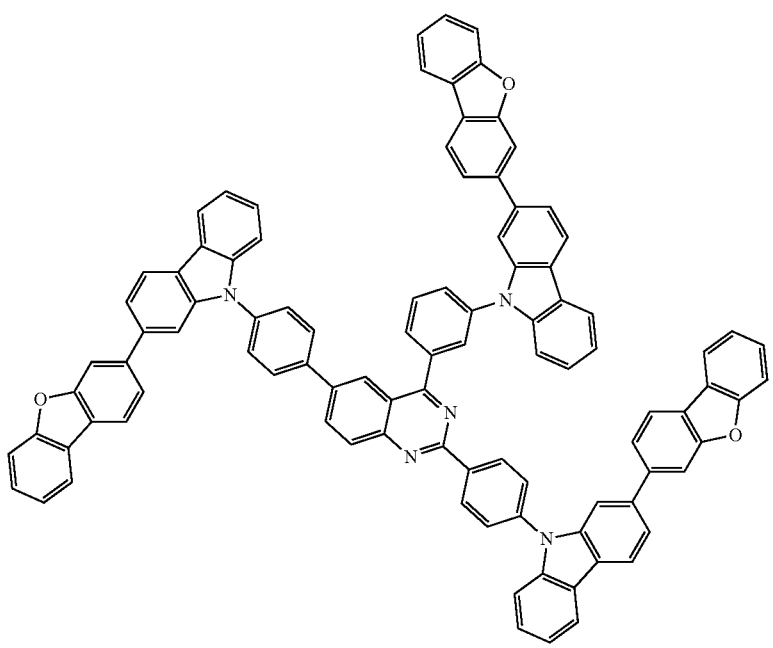

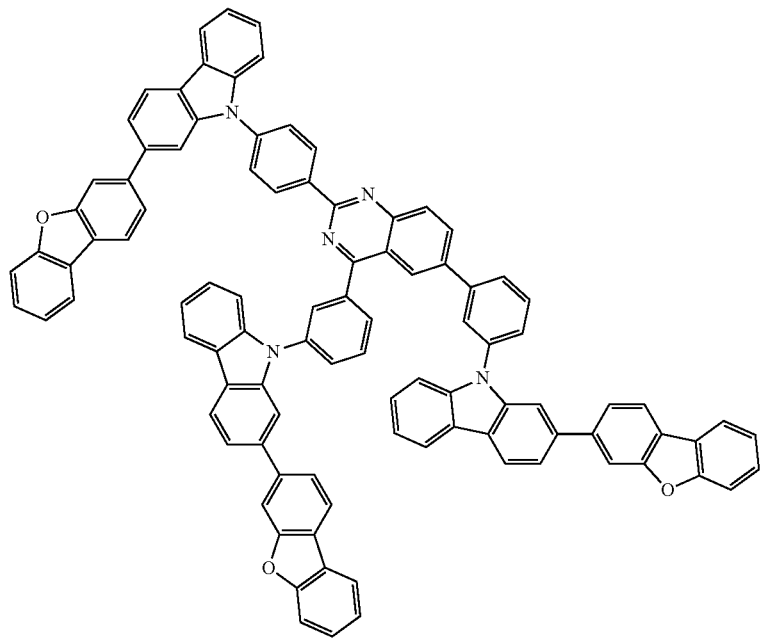
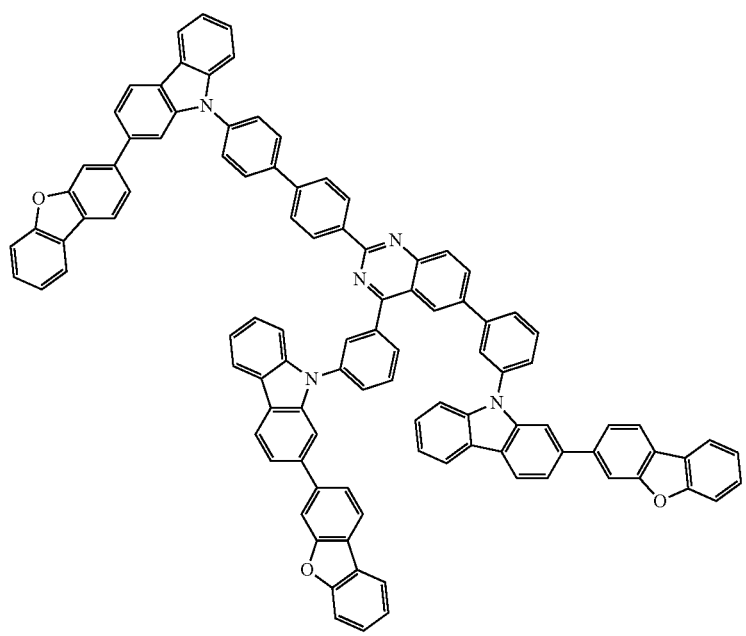

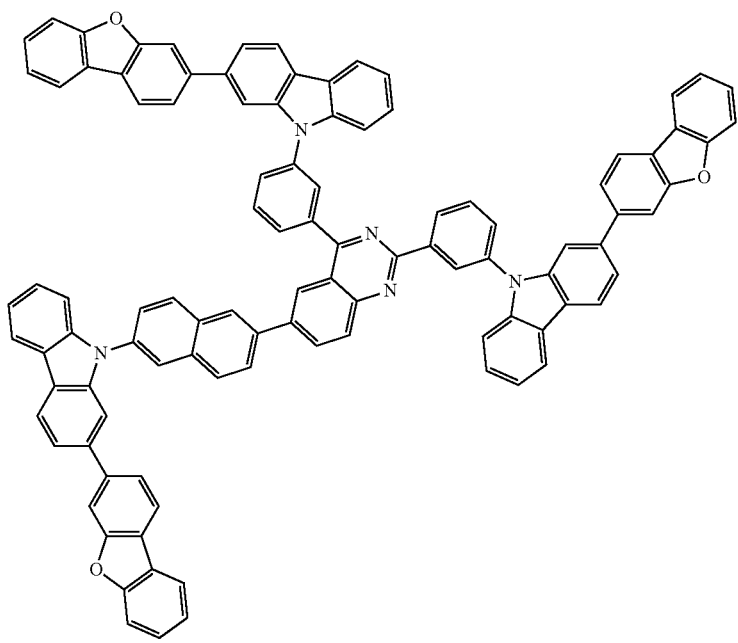
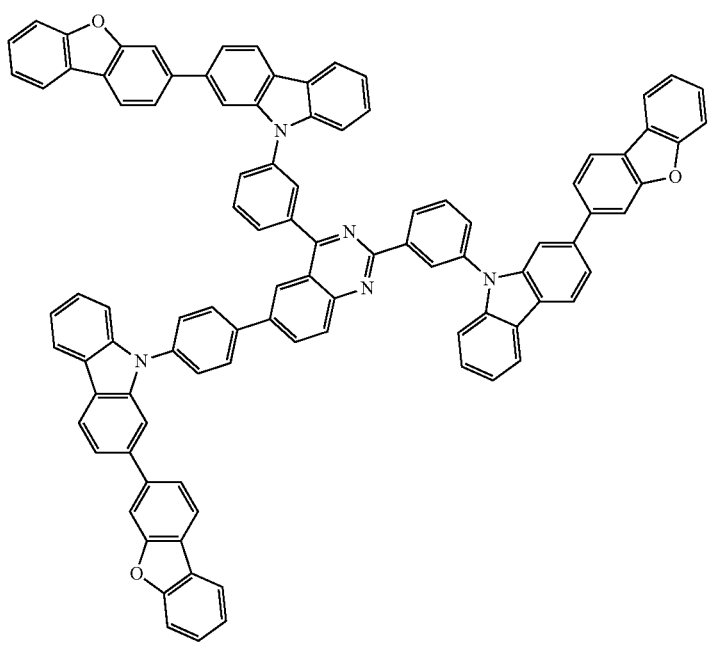

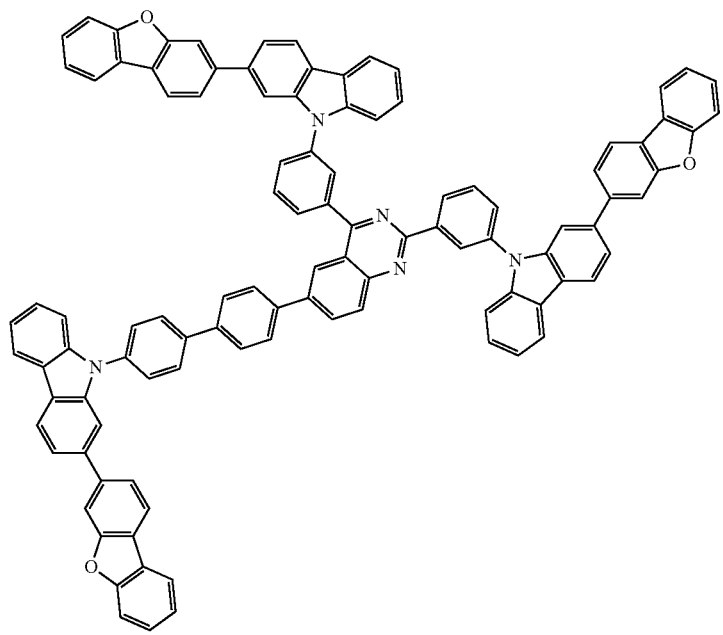
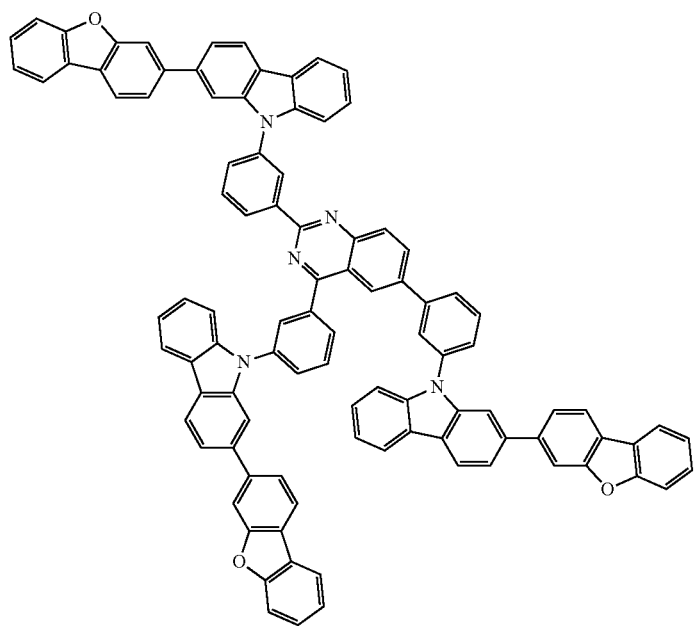

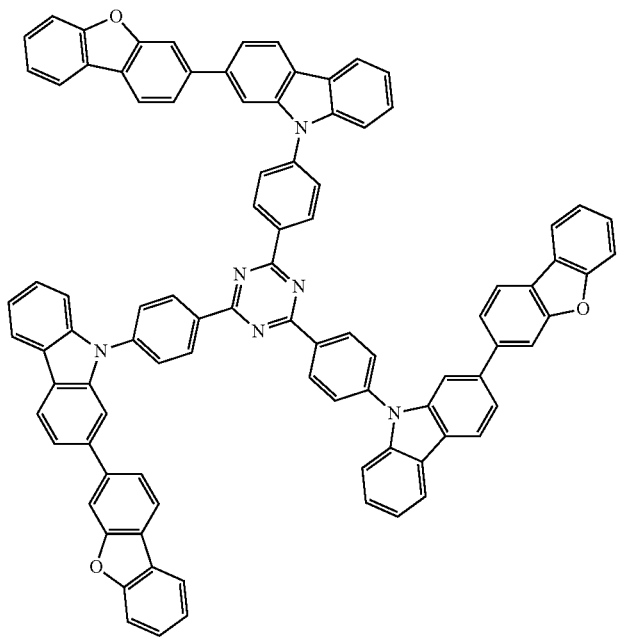
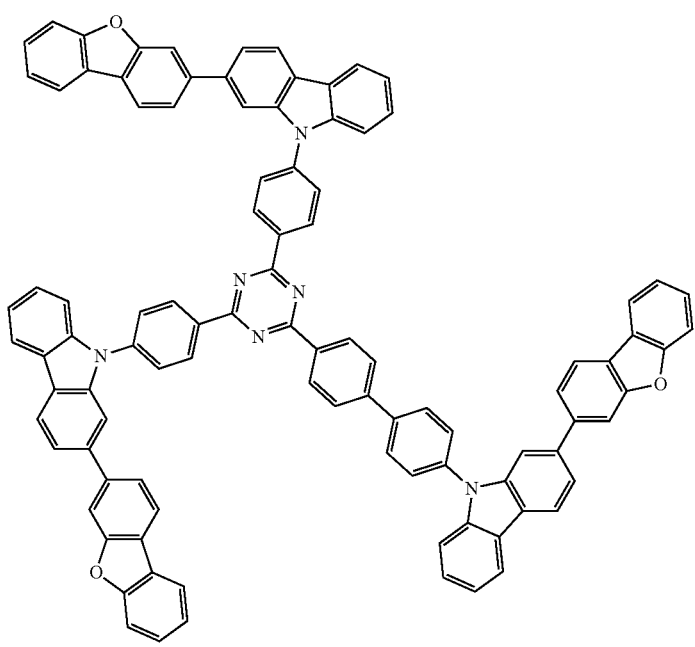

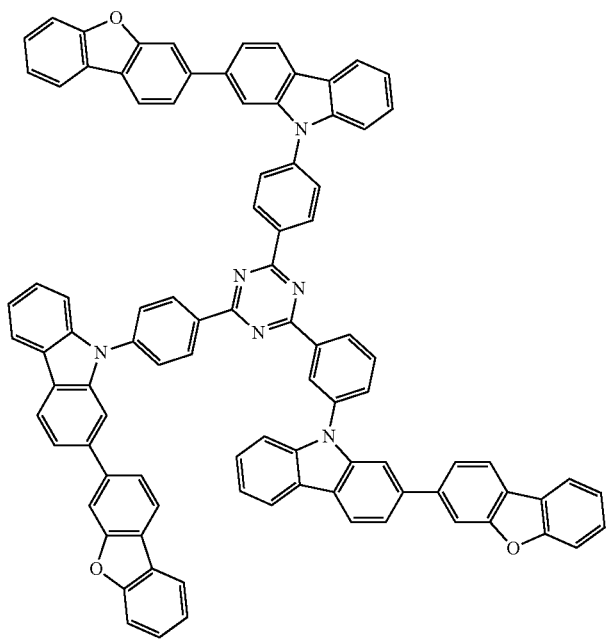
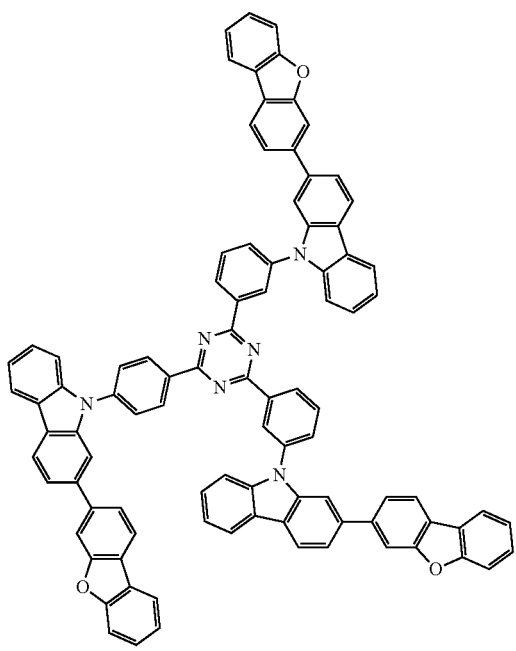

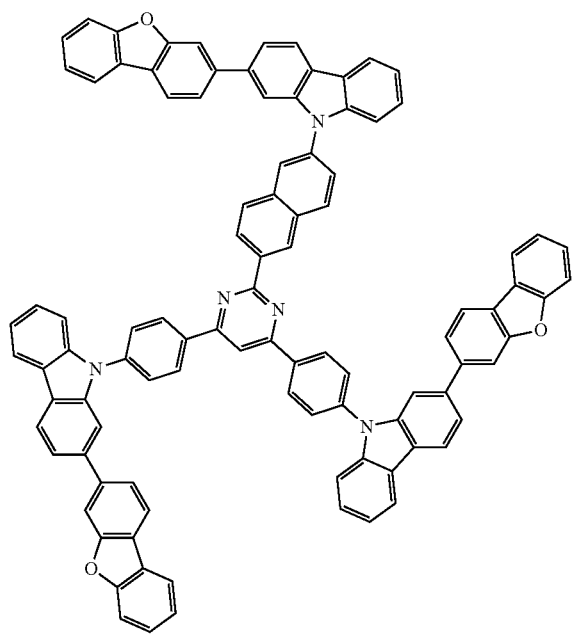
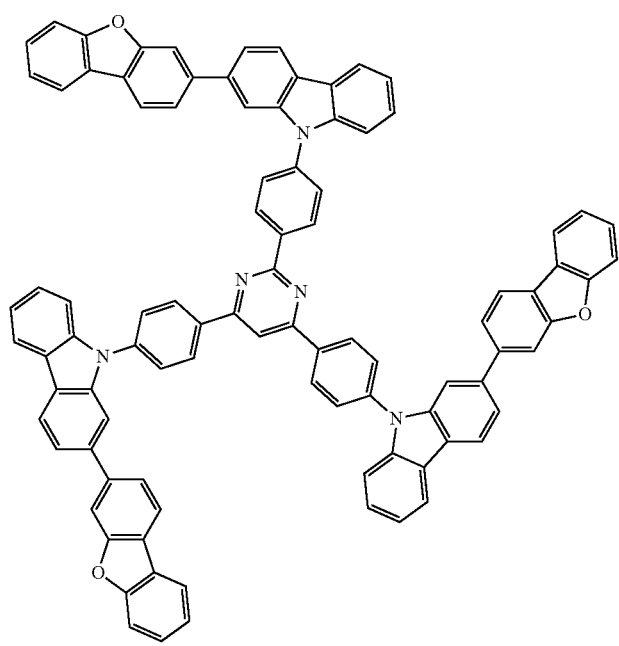

-continued
1273
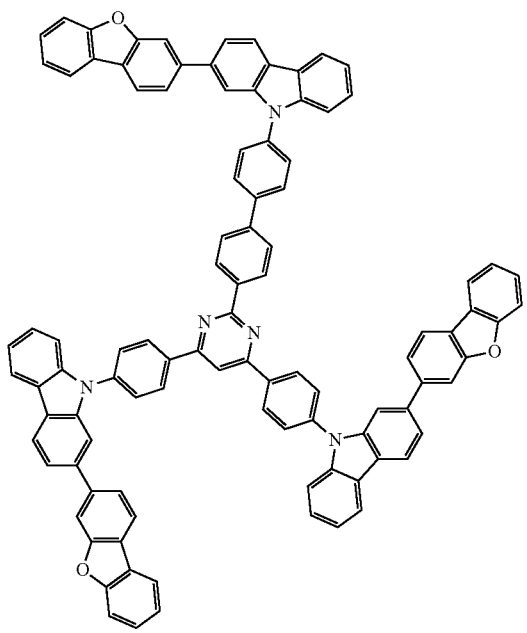
1274
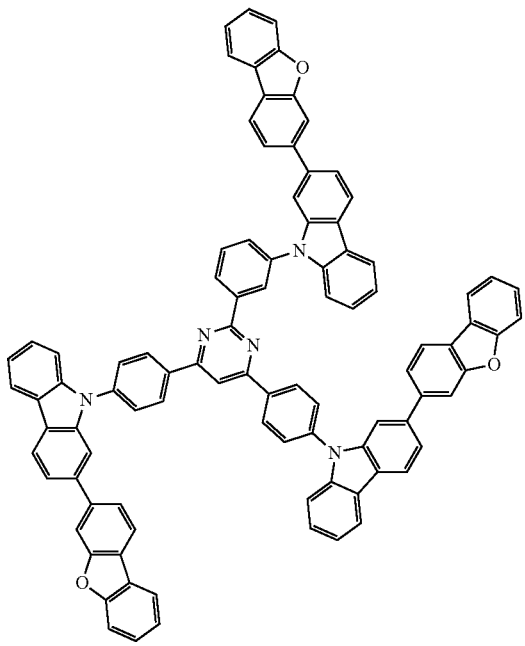
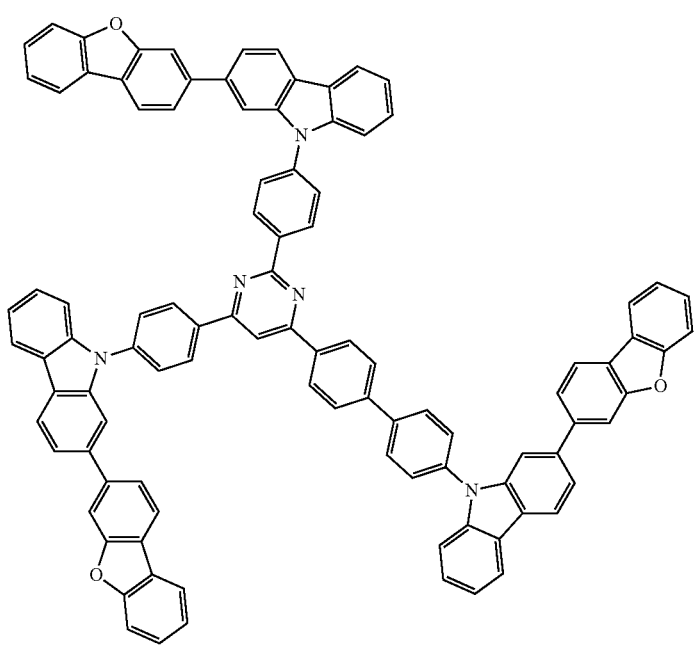

-continued
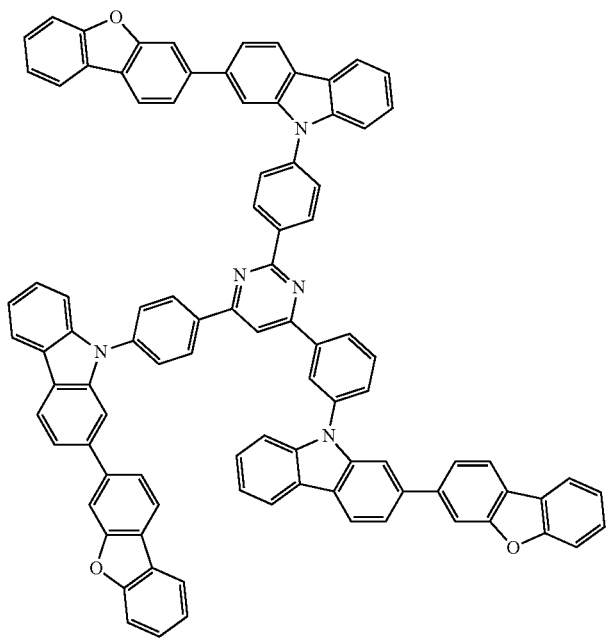
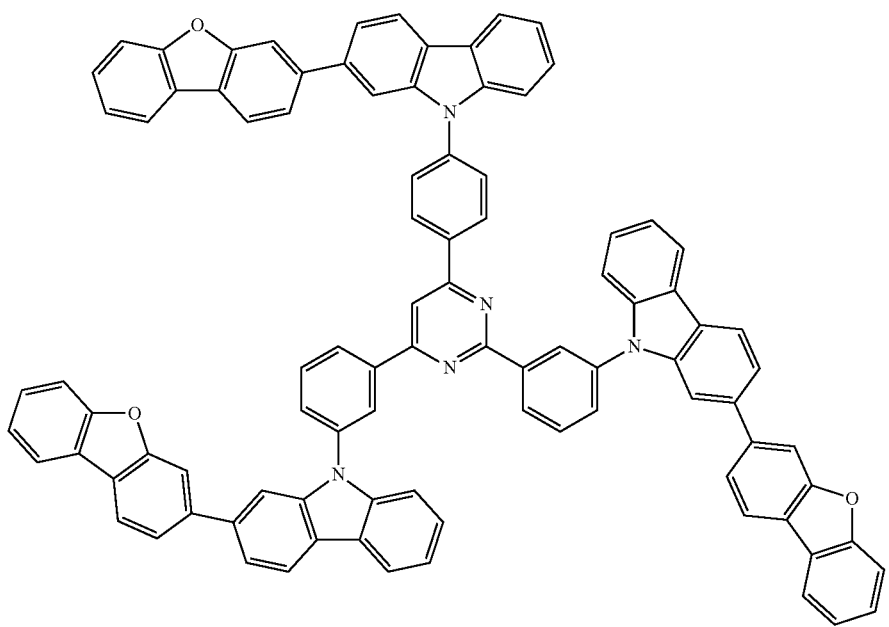

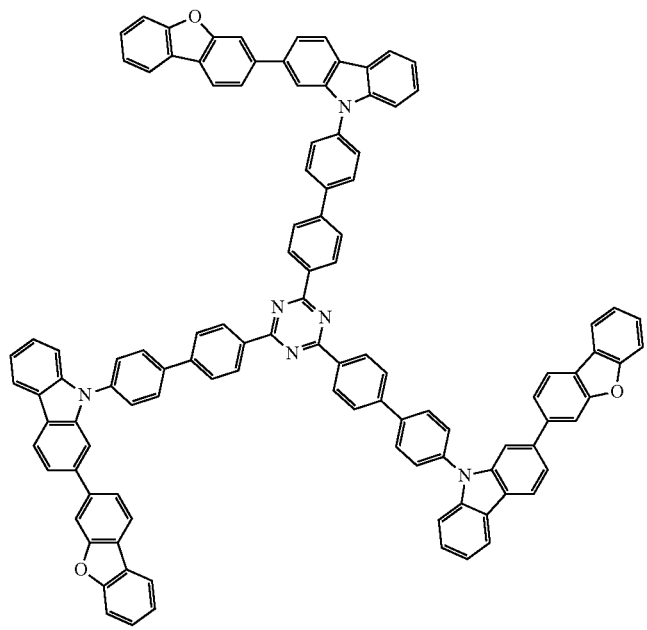
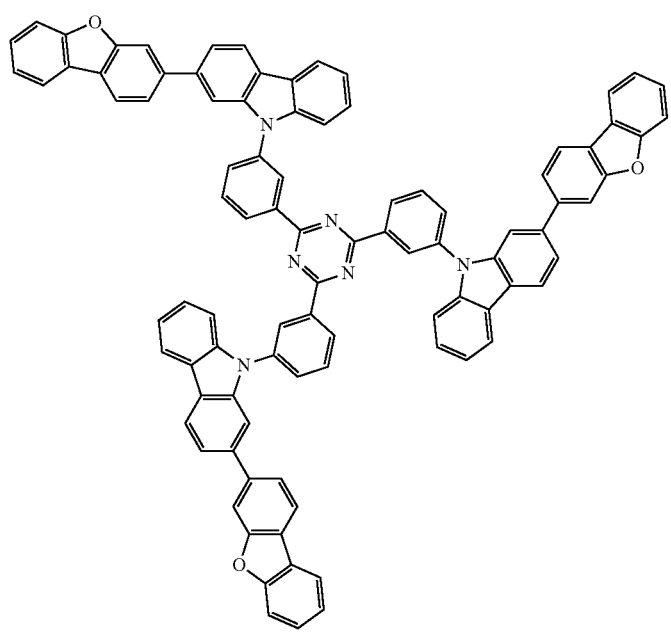

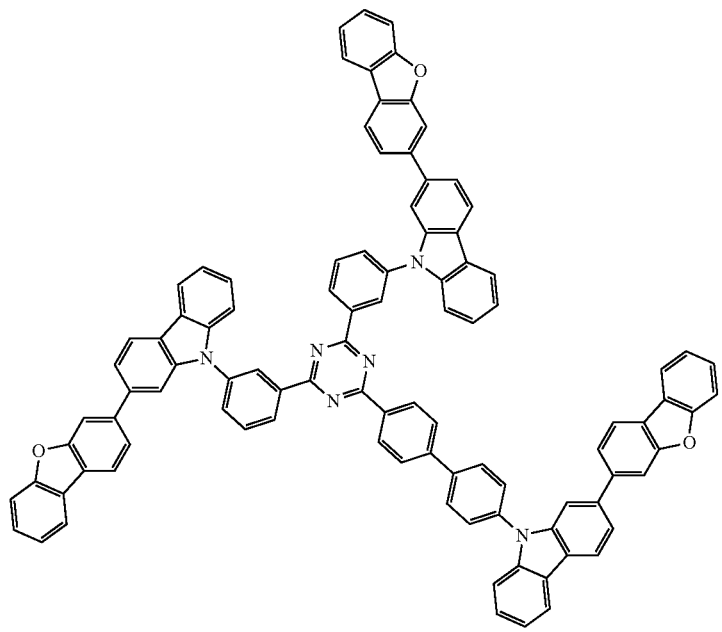
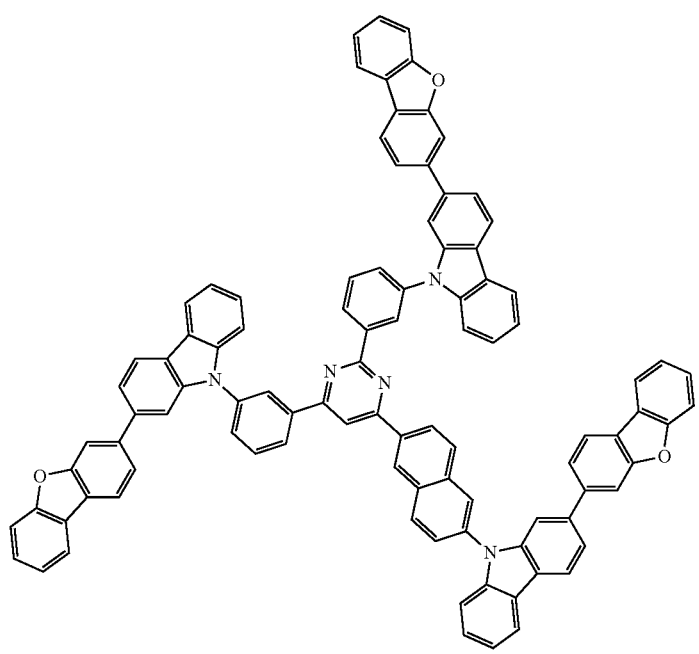

-continued
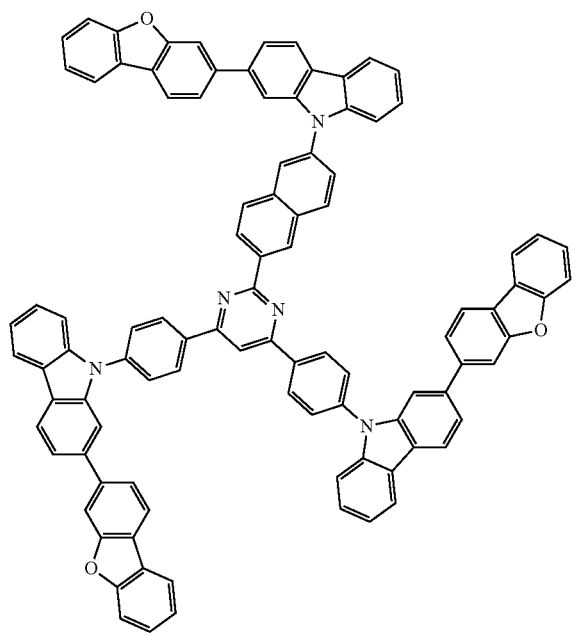
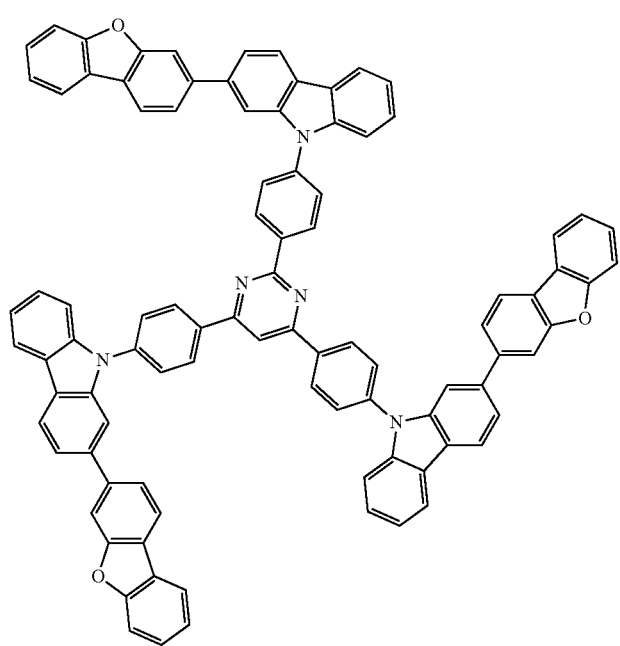

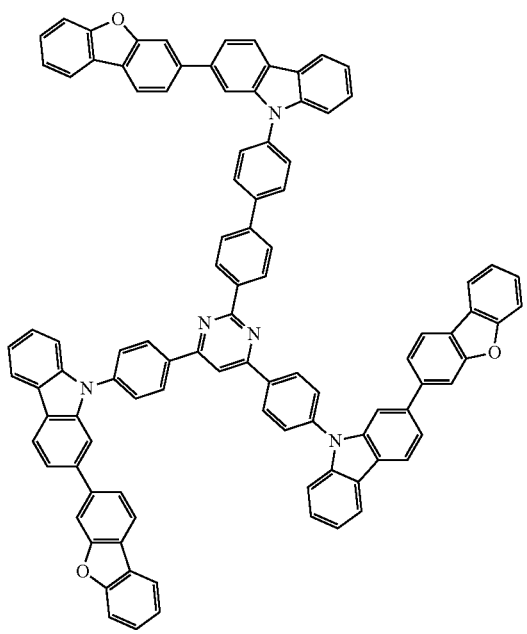
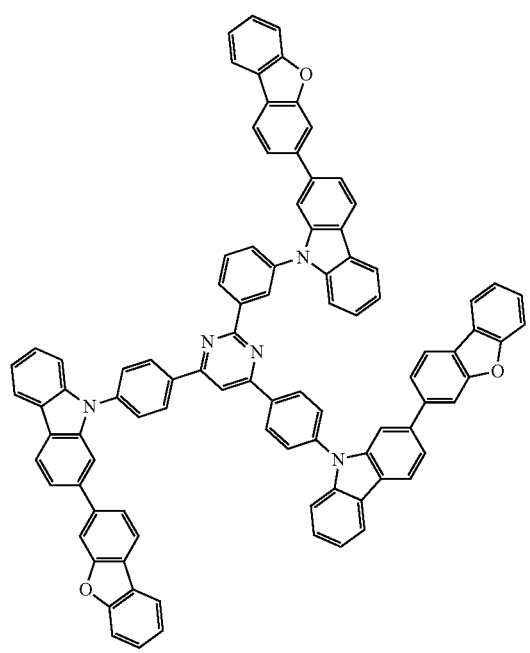

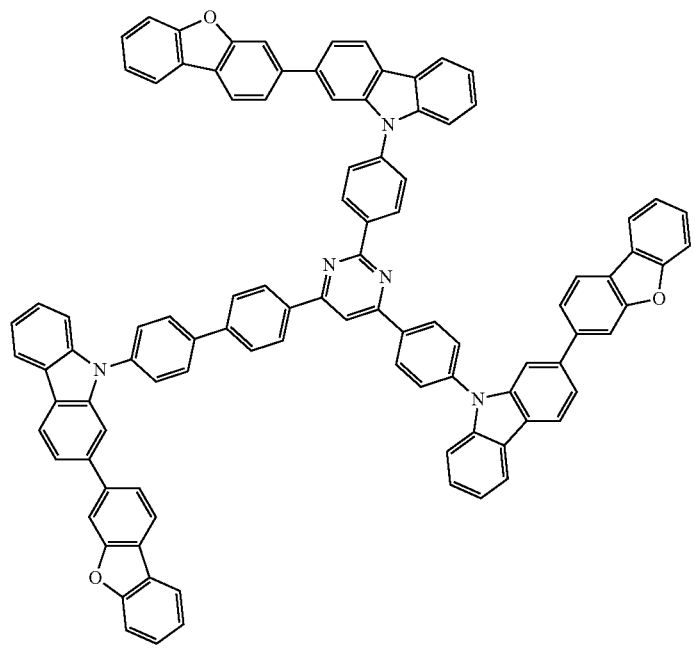
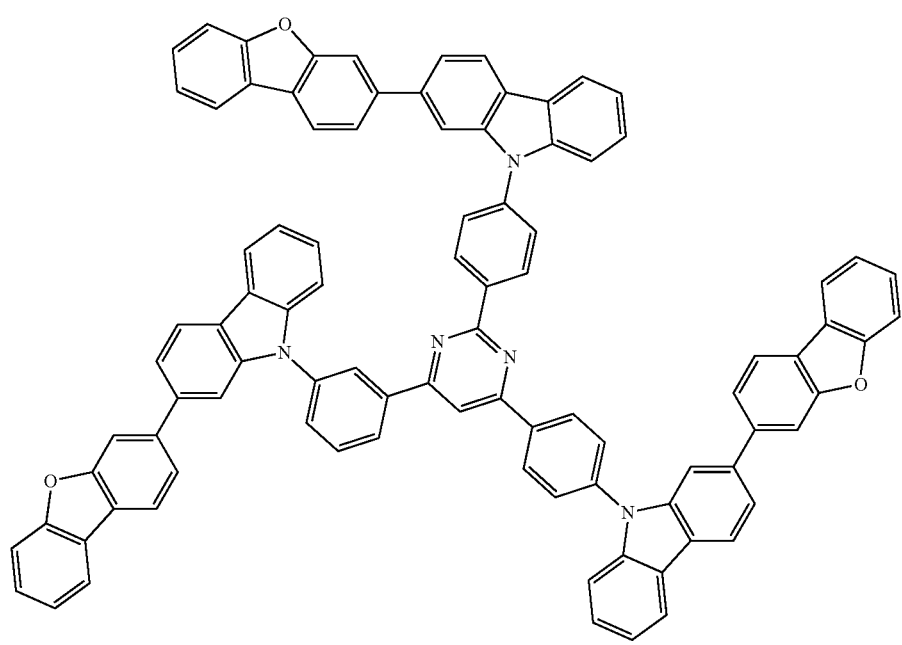

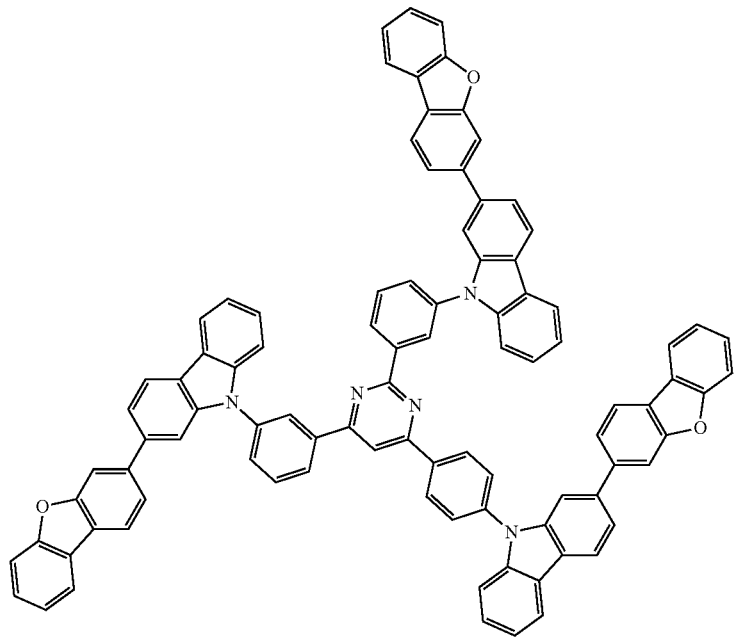
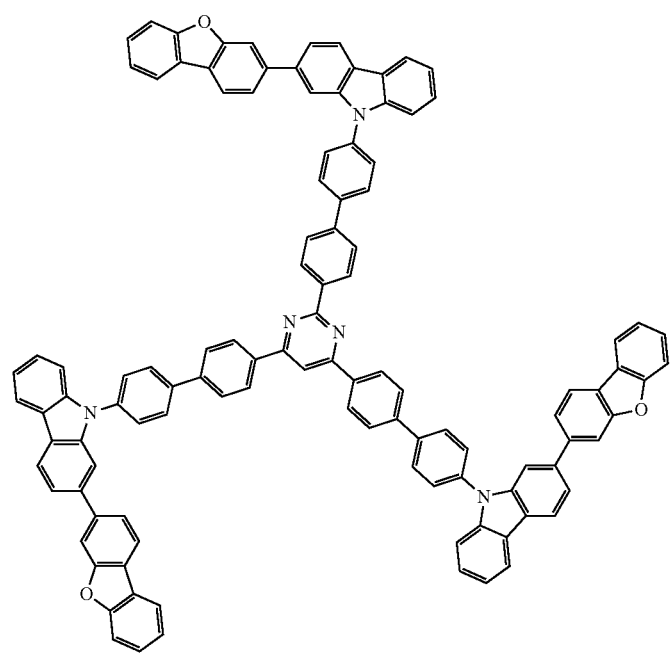

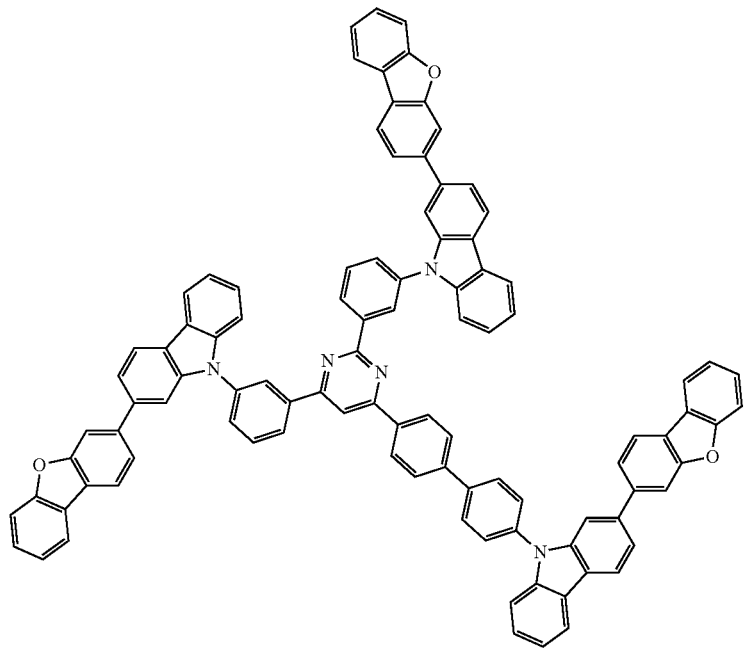
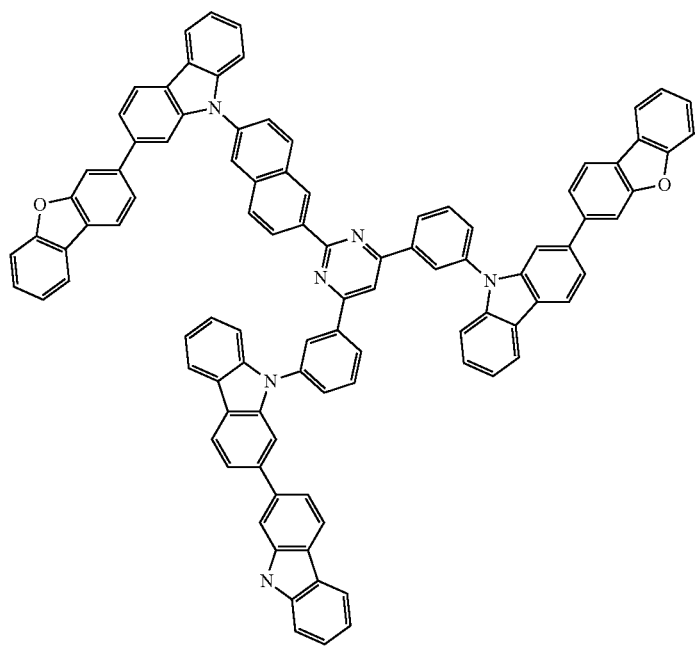

1291
1292
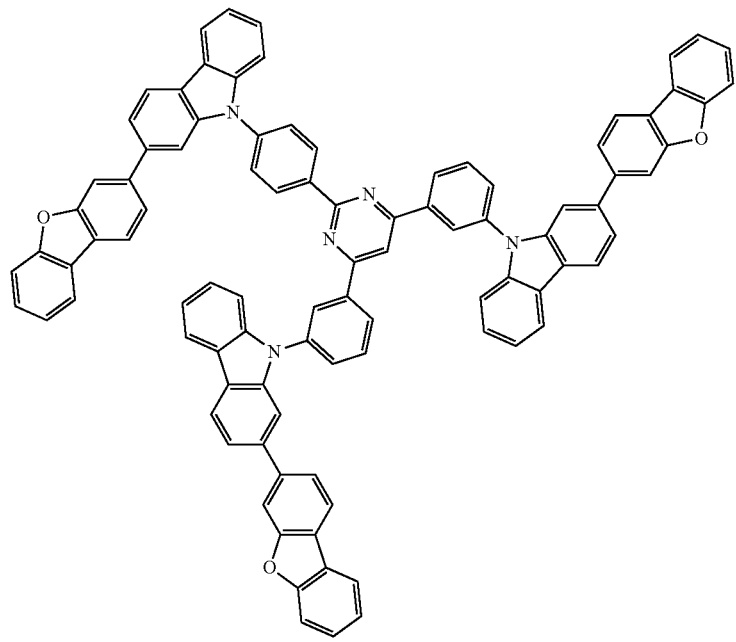
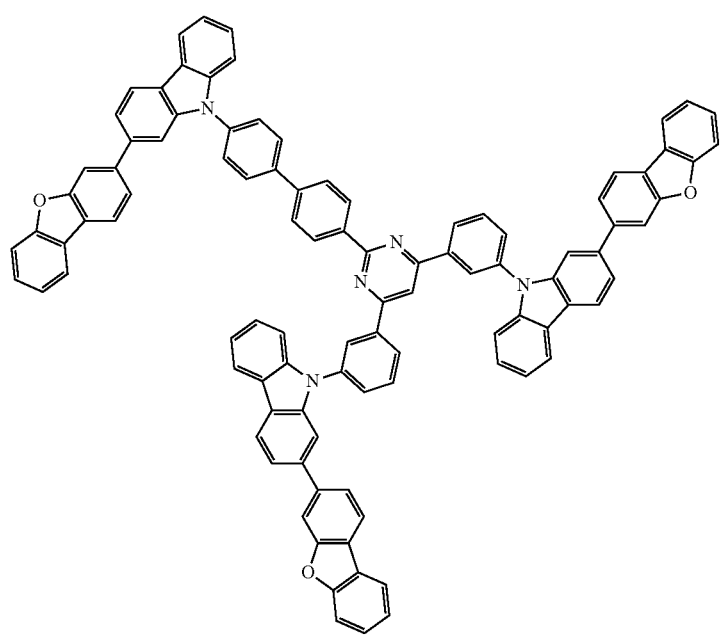

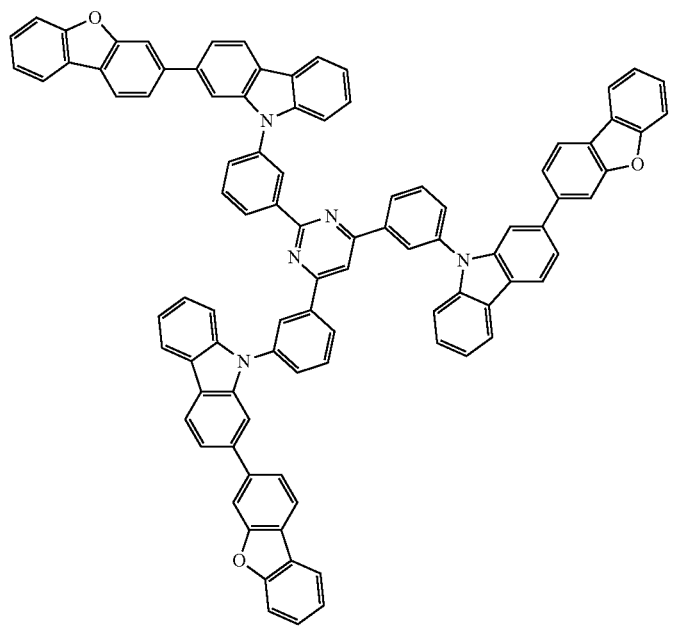
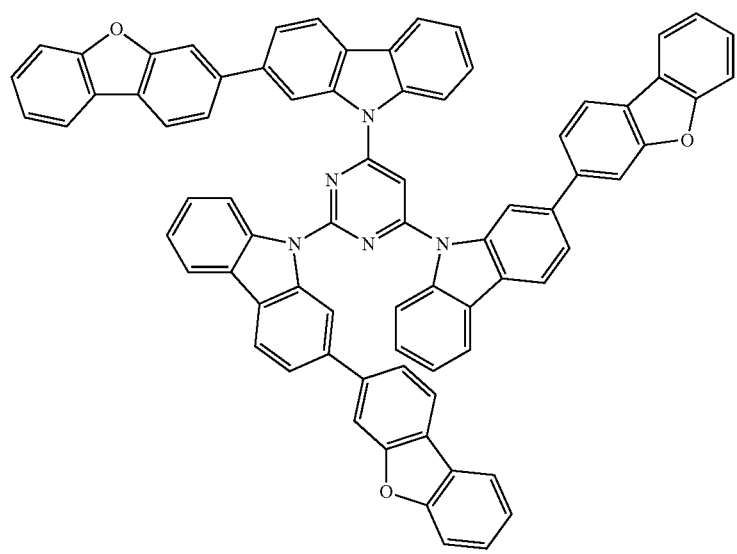

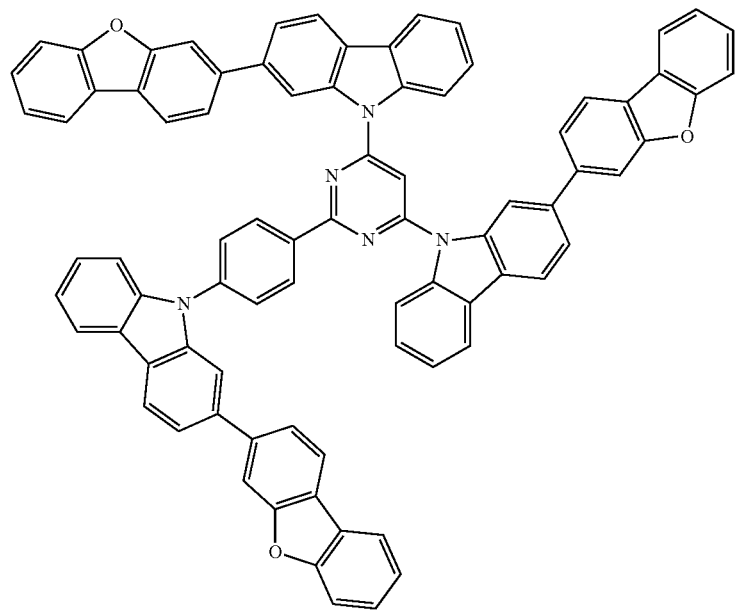
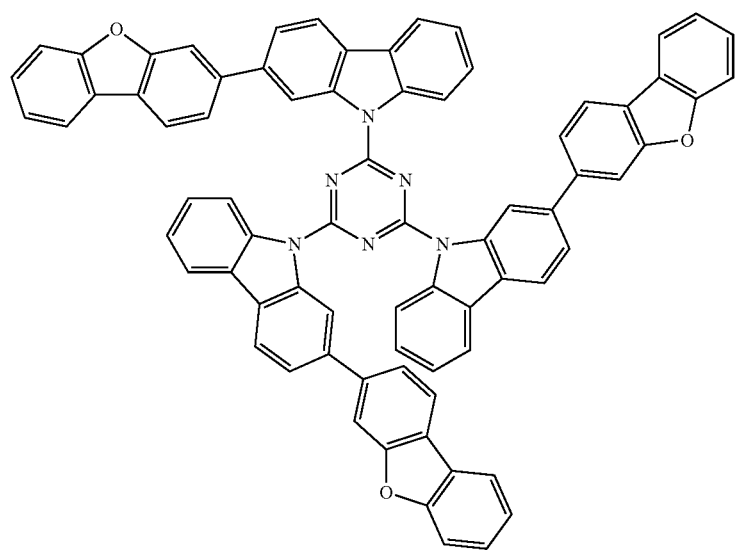

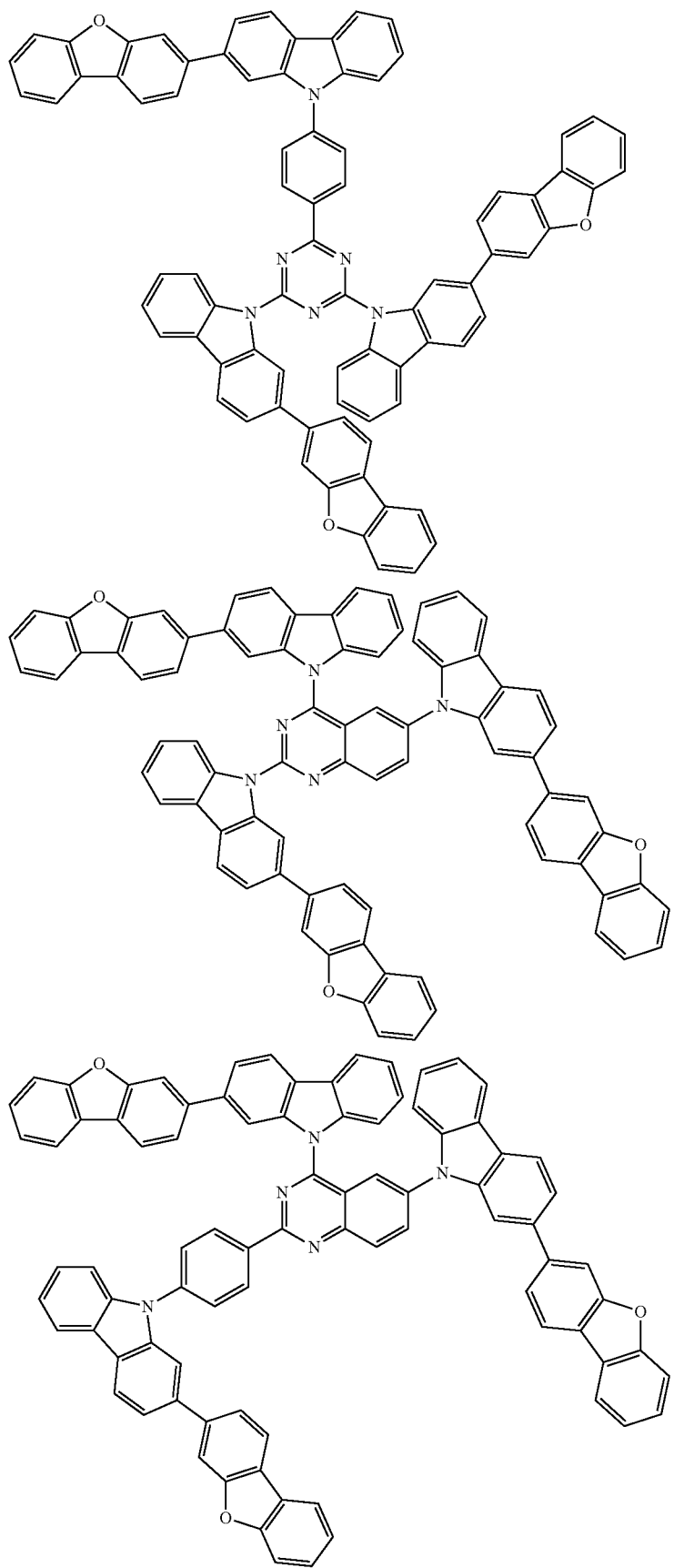

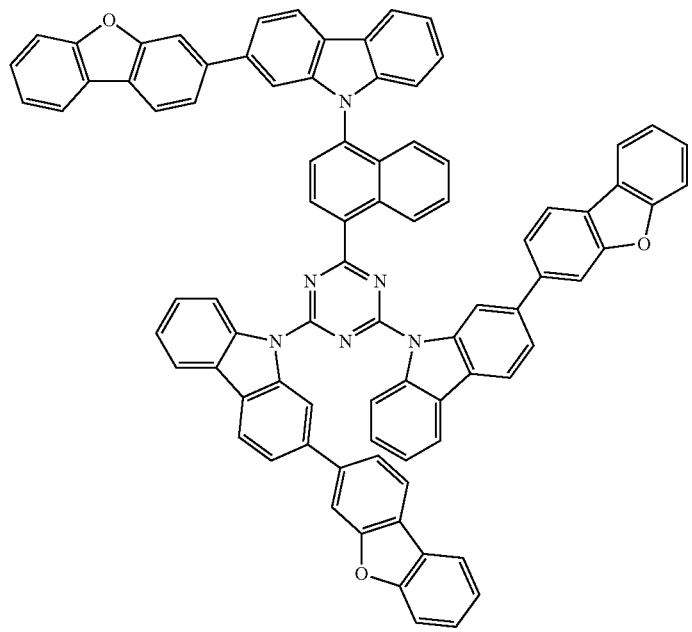
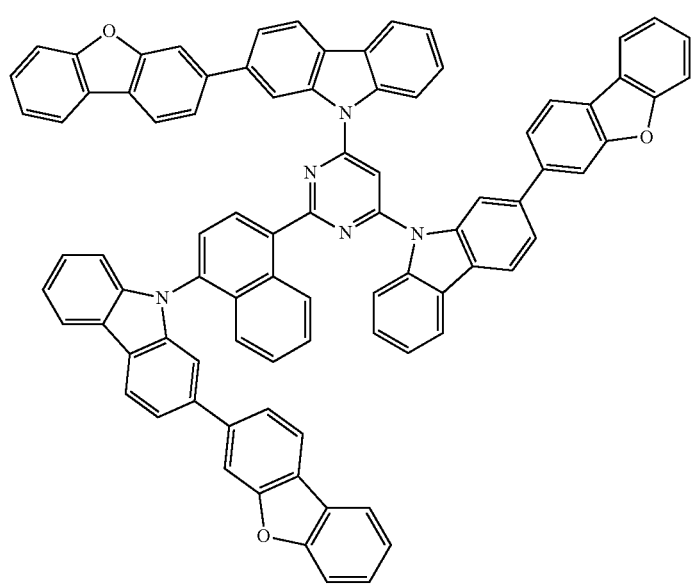

1301
1302
-continued
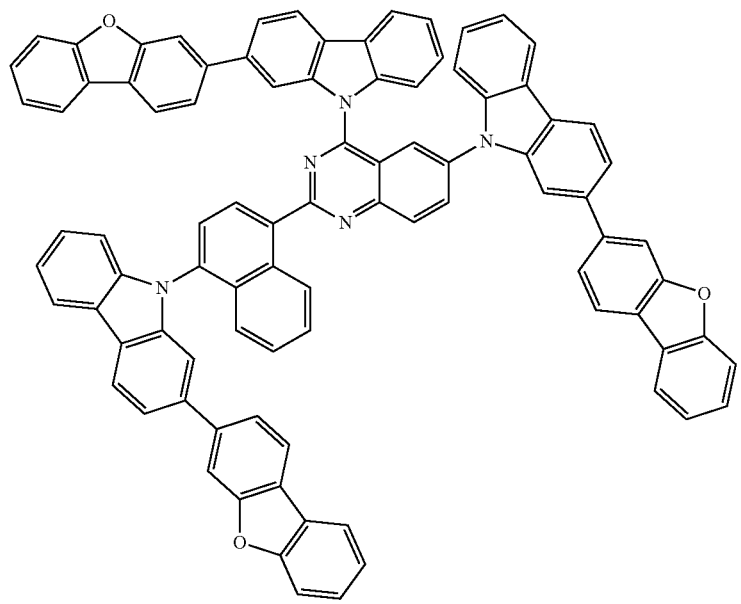
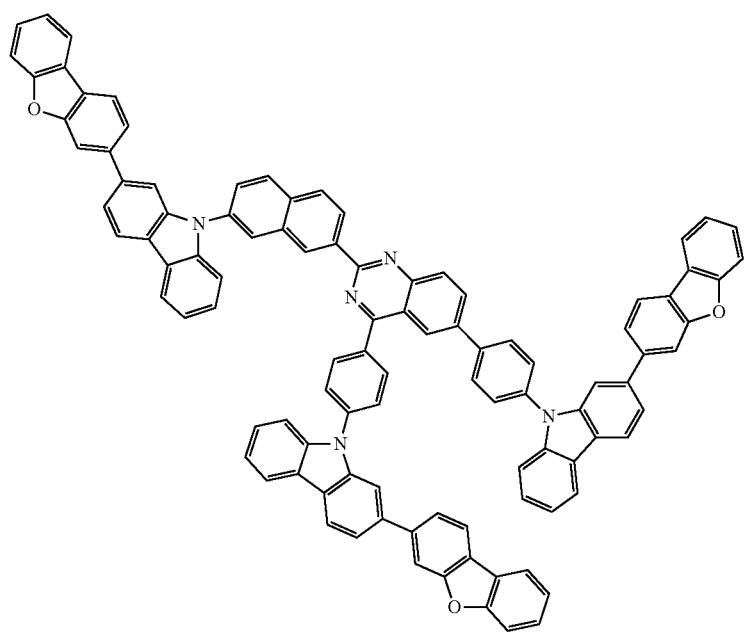

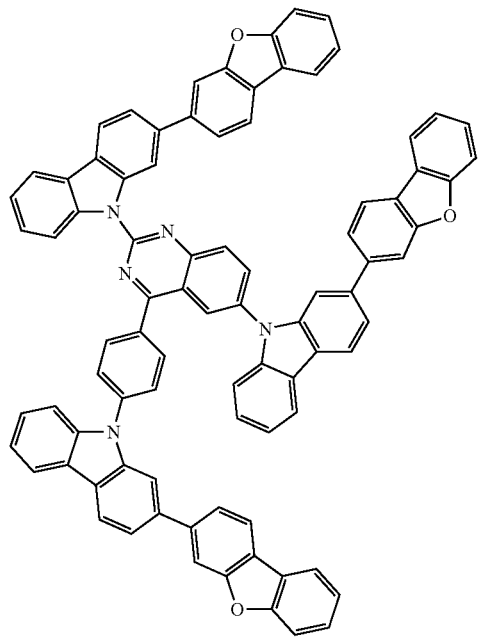
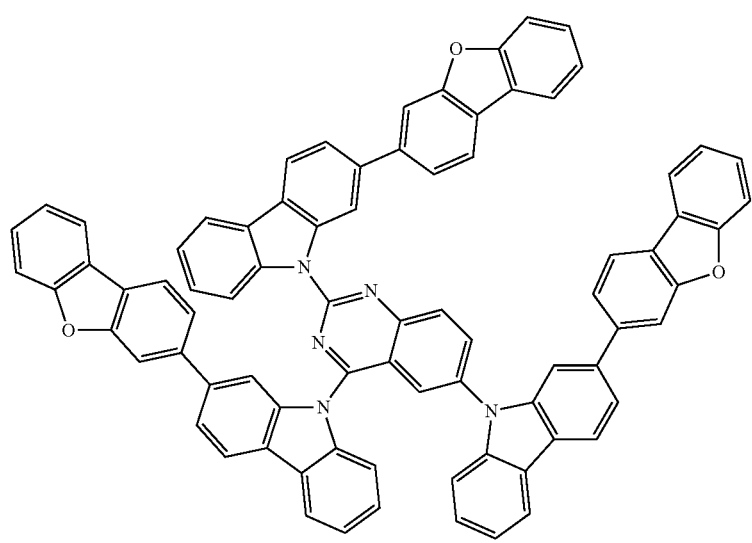

1305
1306
-continued
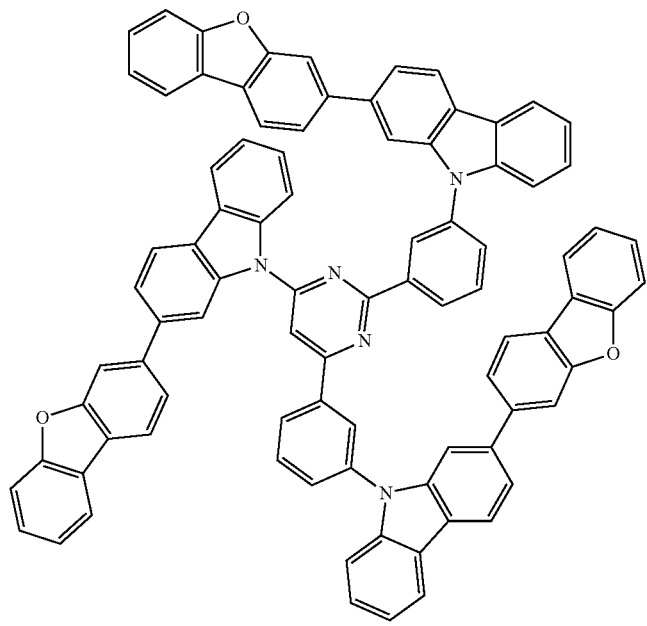
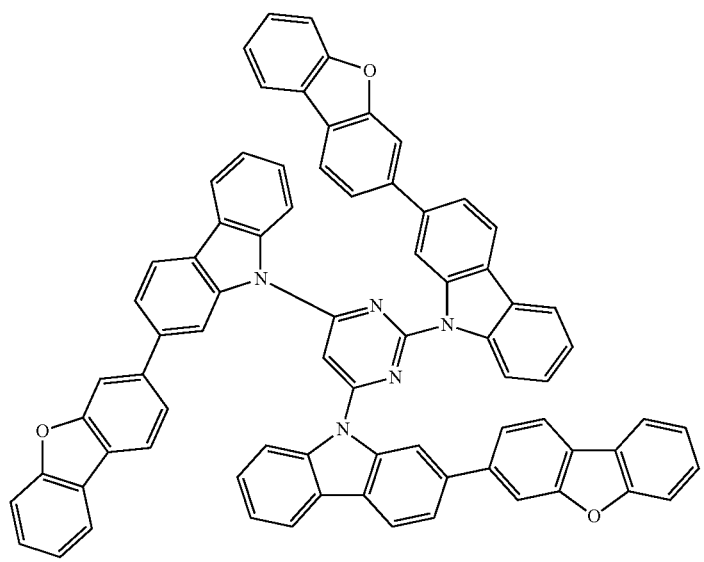

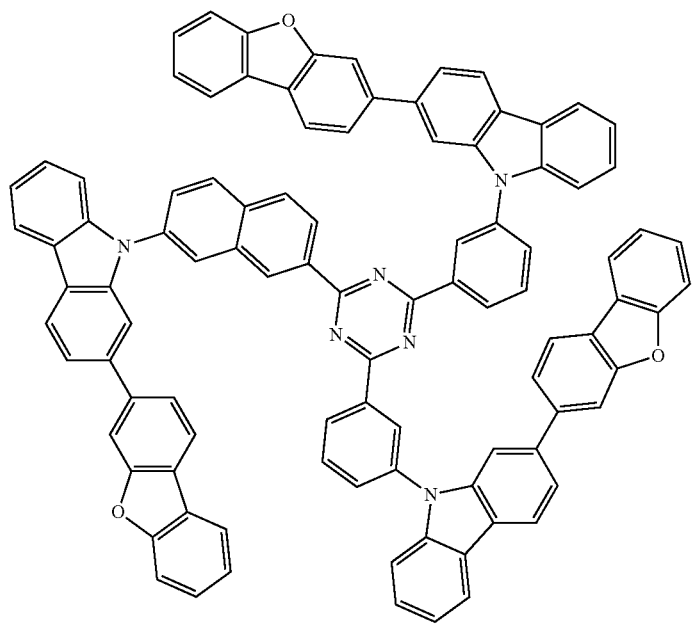
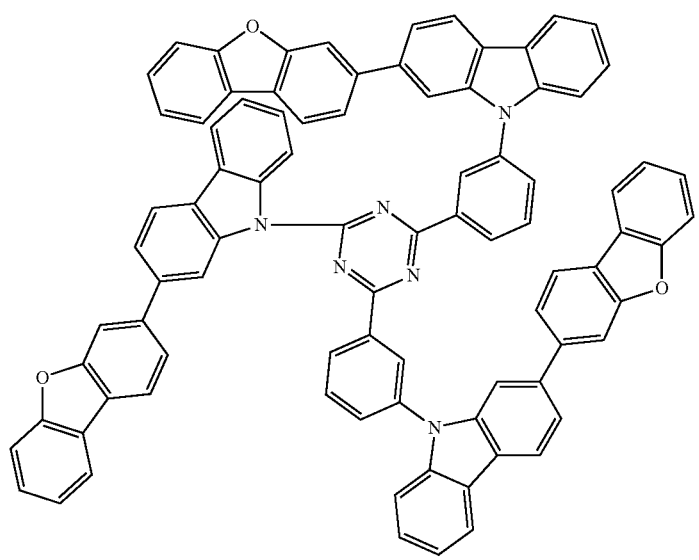

1309
1310
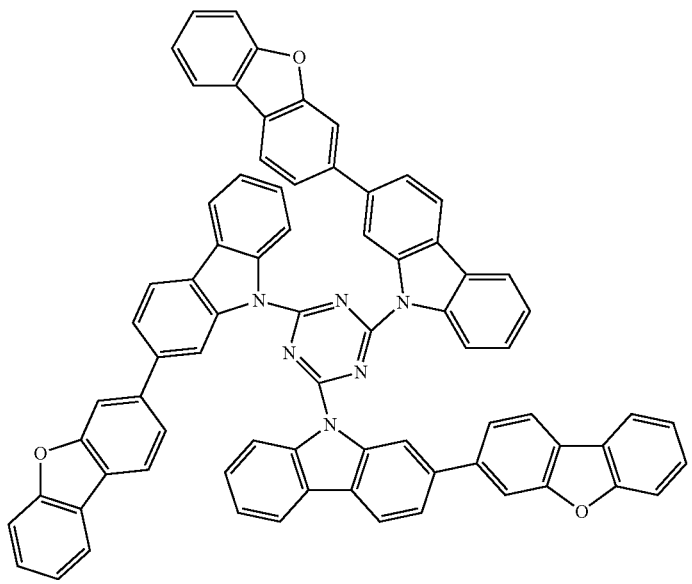
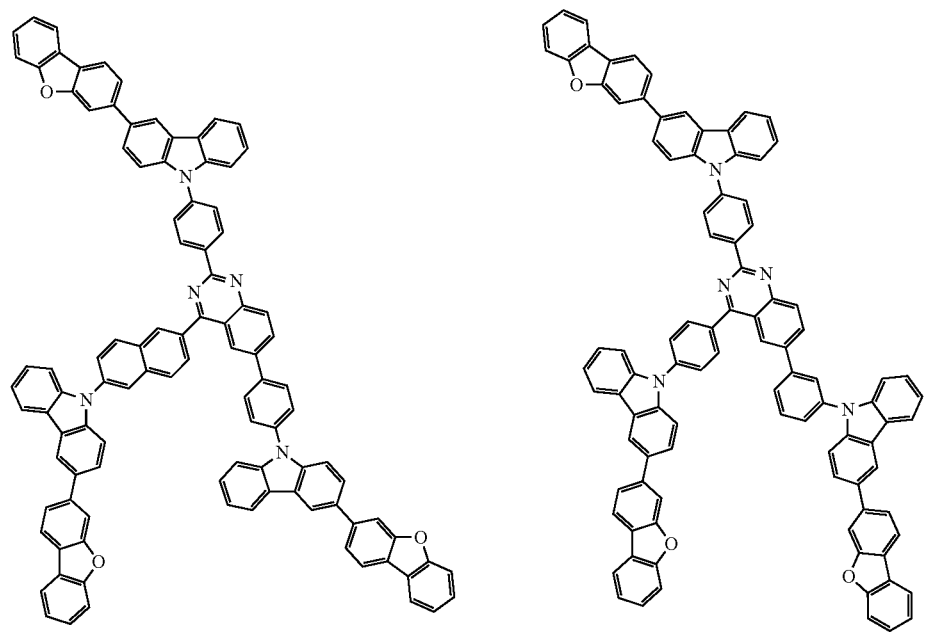

1311 1312
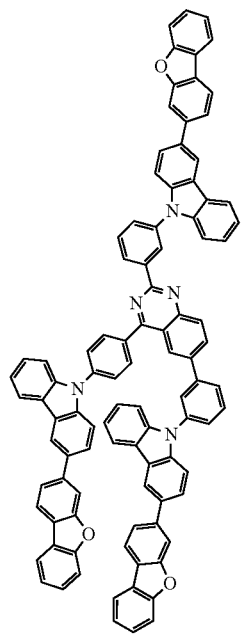
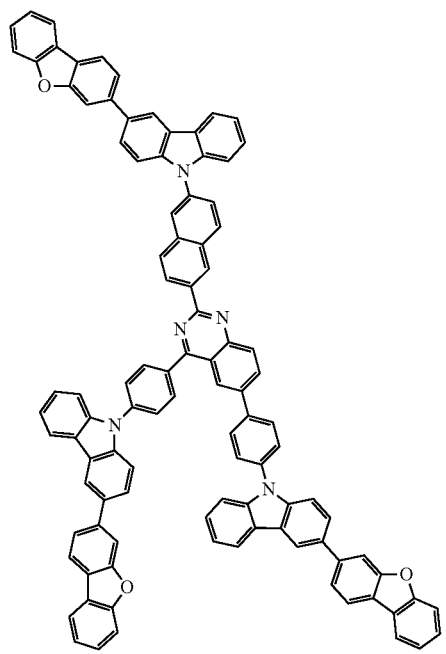 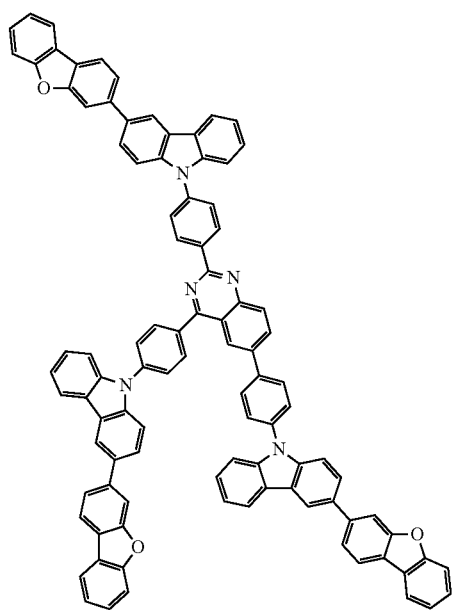

1313
1314
-continued
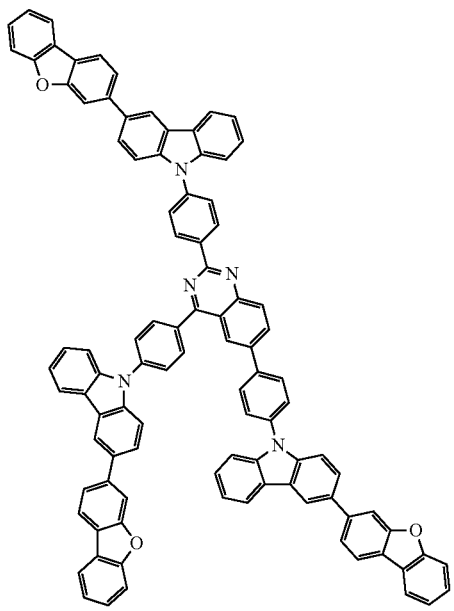
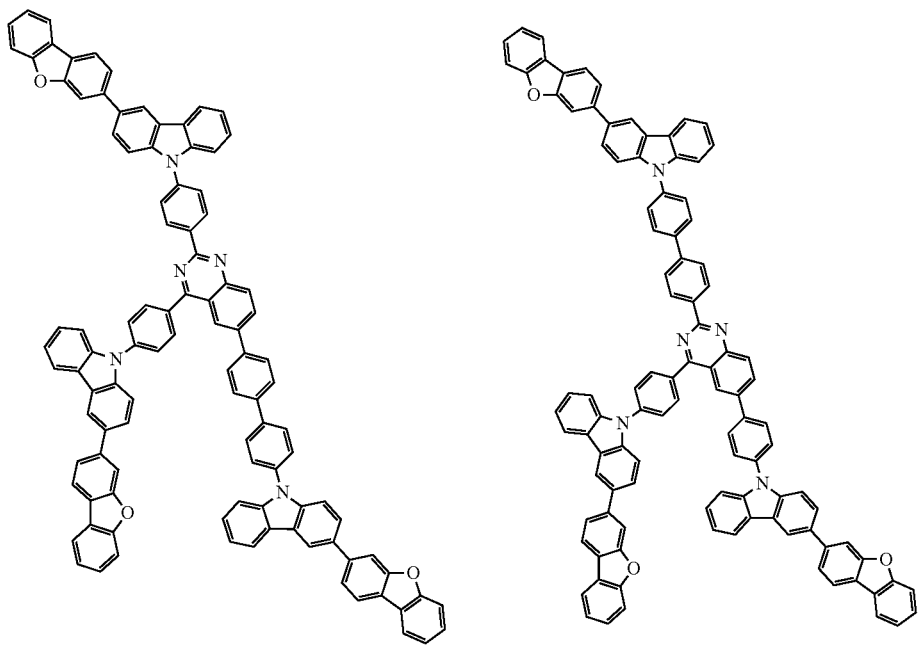

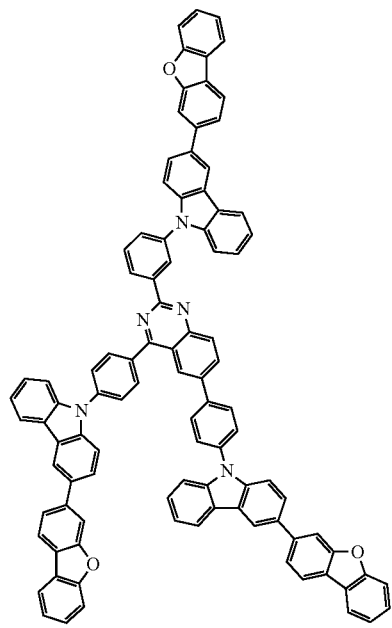
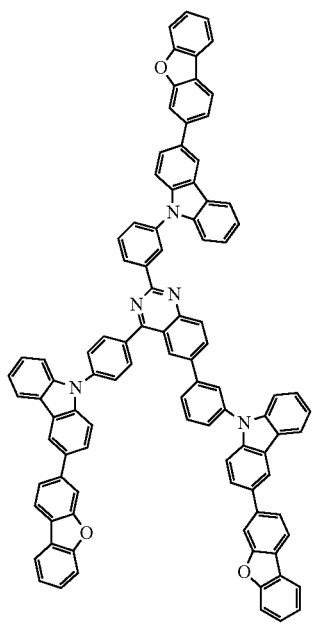
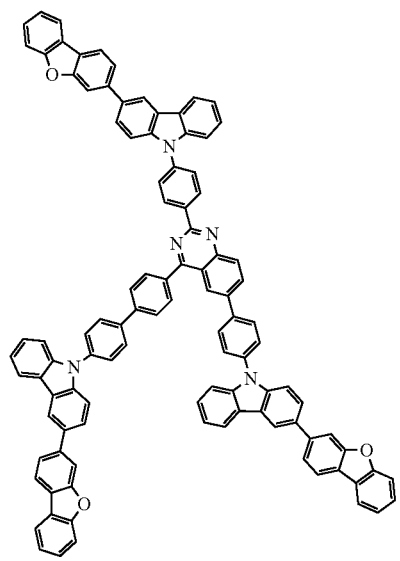
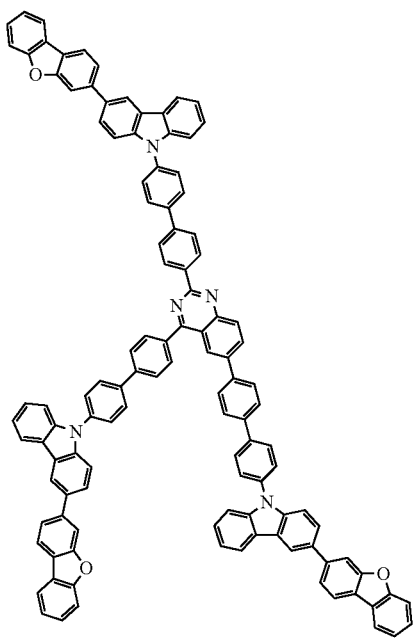

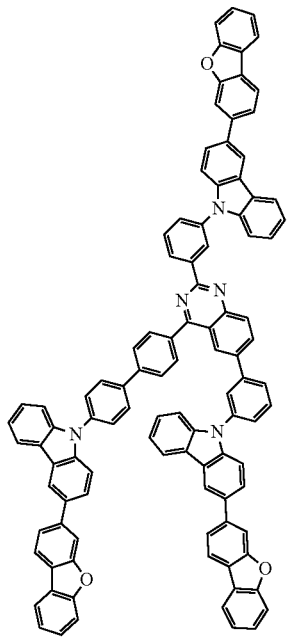
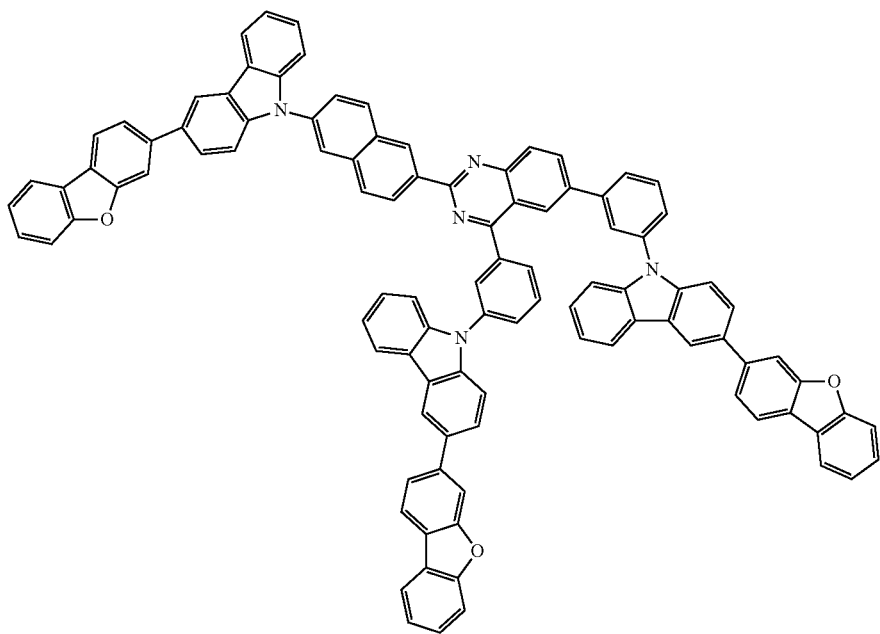

1319 1320
-continued
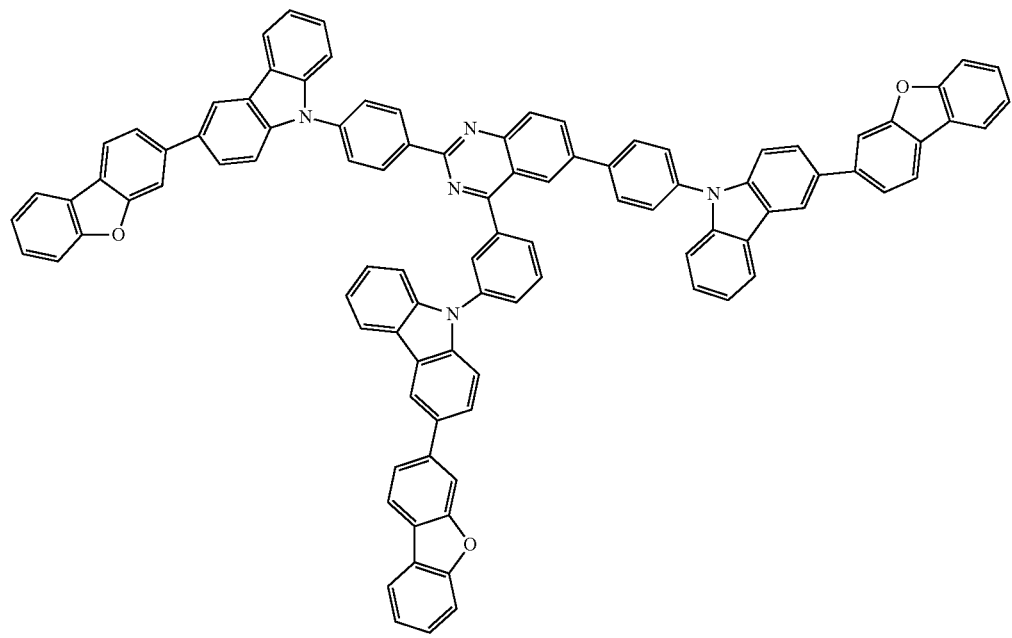
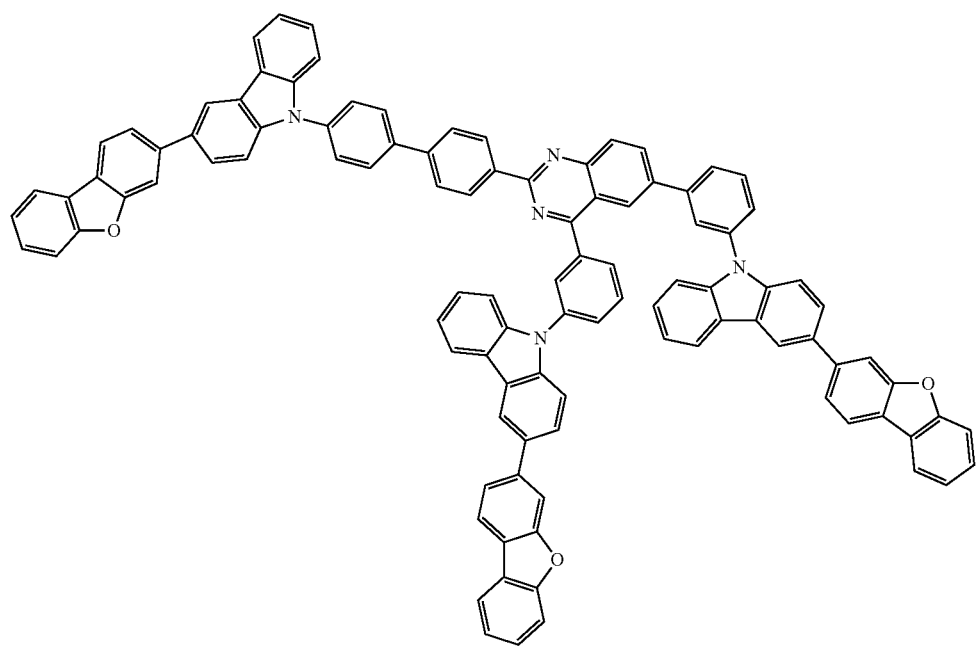

-continued
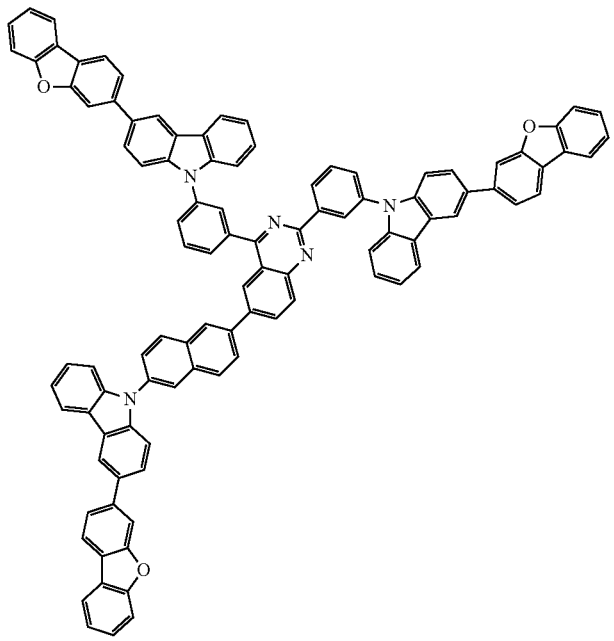
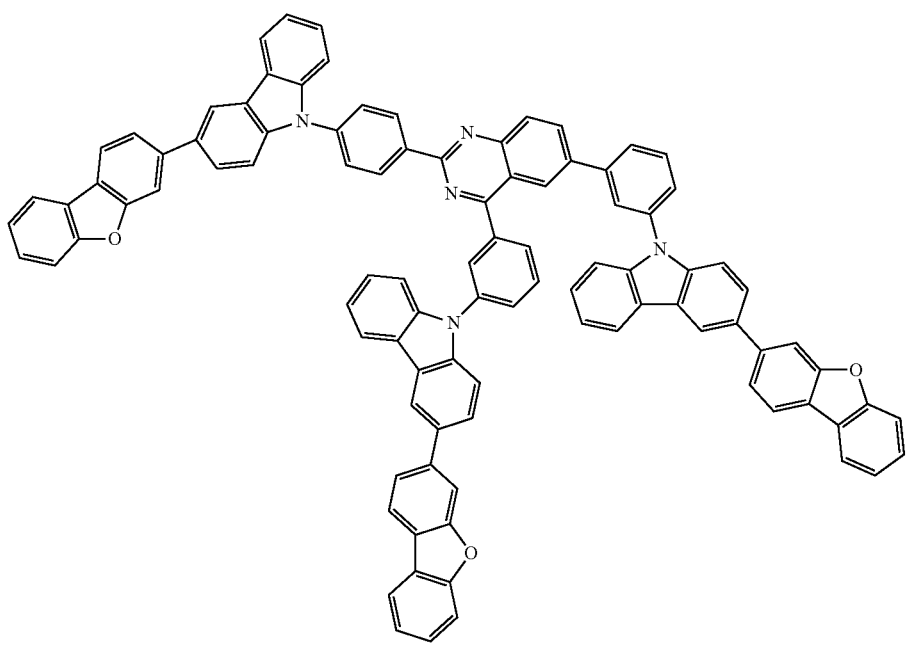

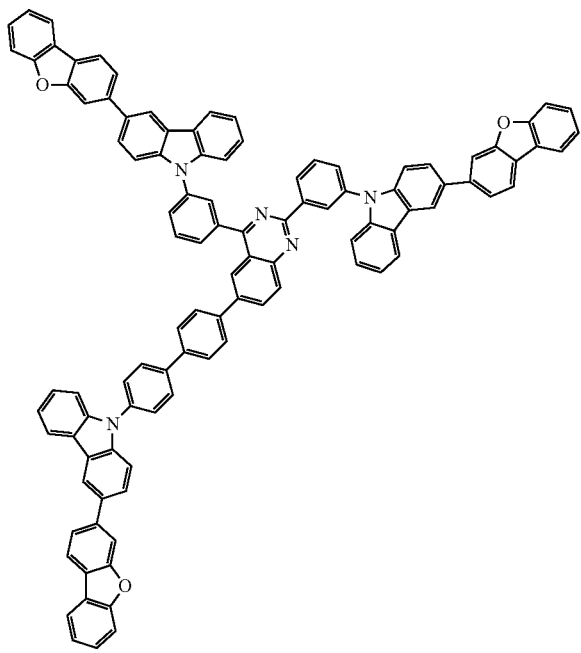

1325
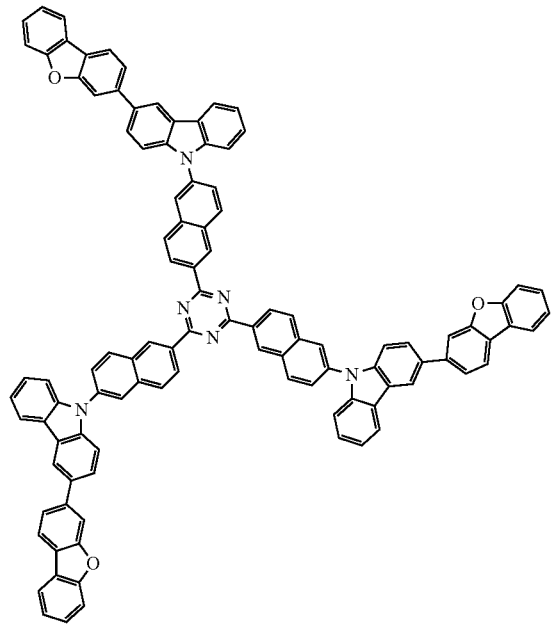
1326
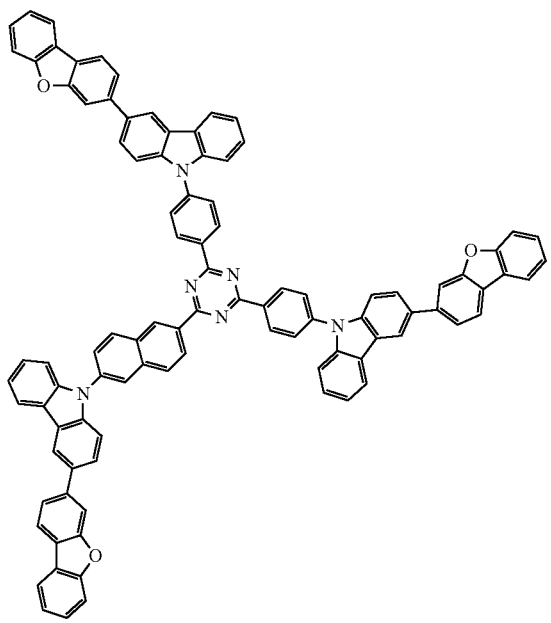
-continued
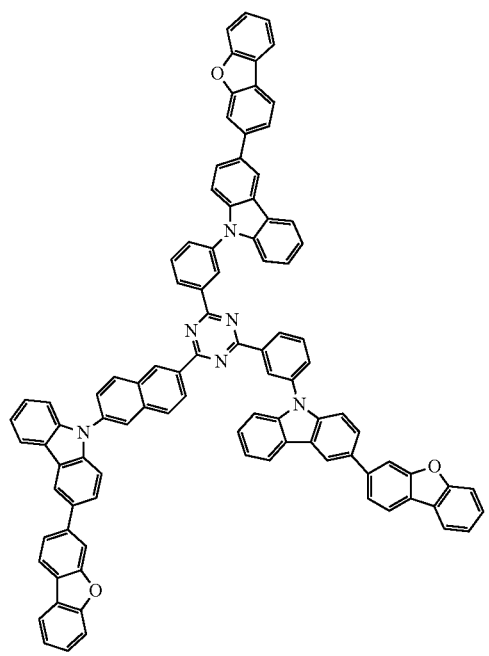
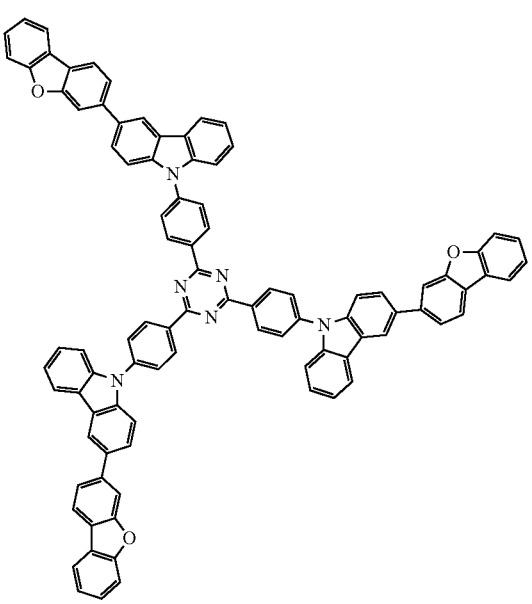

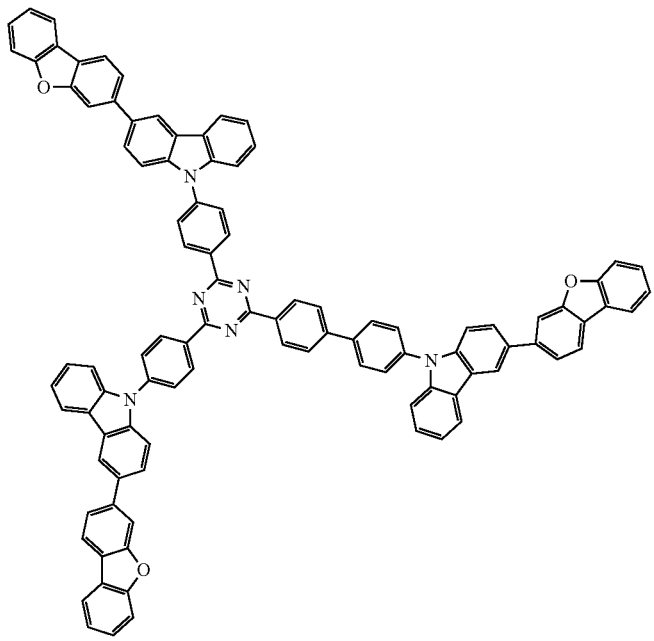
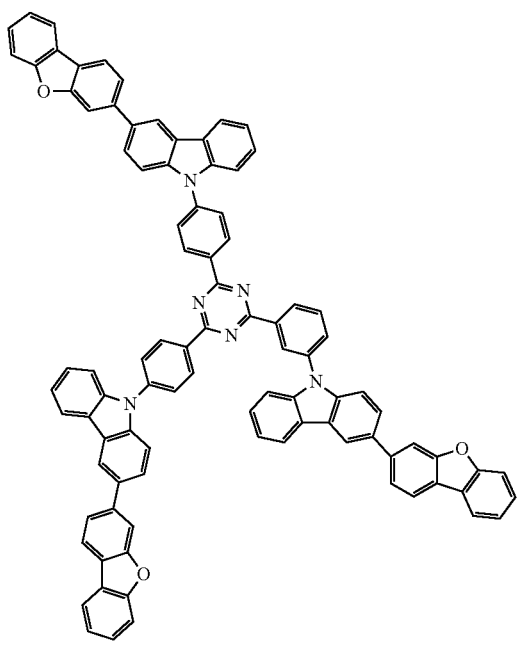

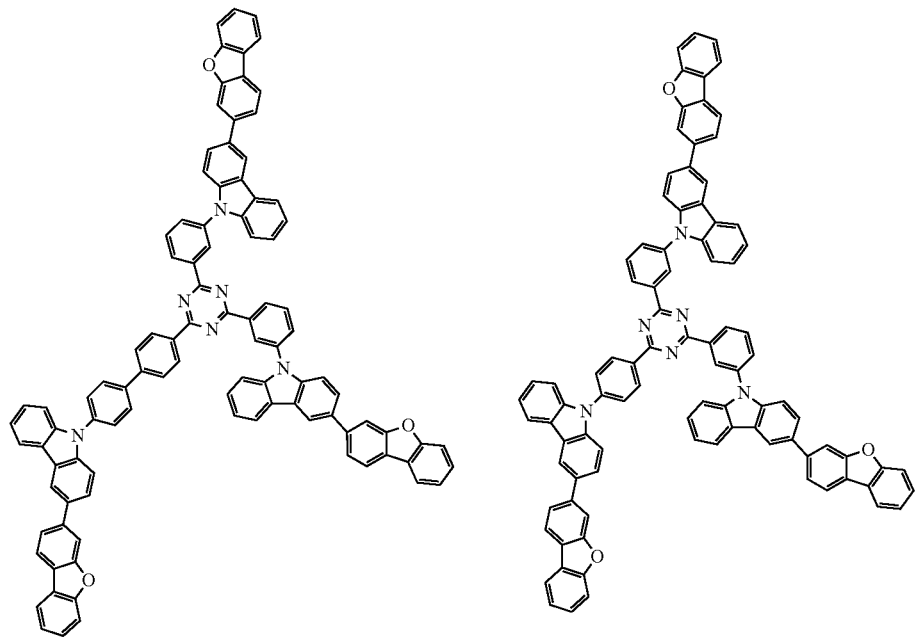 [SMILES: c1cc(-c2nc(-c3ccc(-c4ccc(-n5c6ccccc6c6cc(-c7ccc8c(c7)oc7ccccc78)ccc65)cc4)cc3)nc(-c3cccc(-n4c5ccccc5c5cc(-c6ccc7c(c6)oc6ccccc67)ccc54)c3)n2)cc(-n2c3ccccc3c3cc(-c4ccc5c(c4)oc4ccccc45)ccc32)c1 ; c1cc(-c2nc(-c3ccc(-n4c5ccccc5c5cc(-c6ccc7c(c6)oc6ccccc67)ccc54)cc3)nc(-c3cccc(-n4c5ccccc5c5cc(-c6ccc7c(c6)oc6ccccc67)ccc54)c3)n2)cc(-n2c3ccccc3c3cc(-c4ccc5c(c4)oc4ccccc45)ccc32)c1]
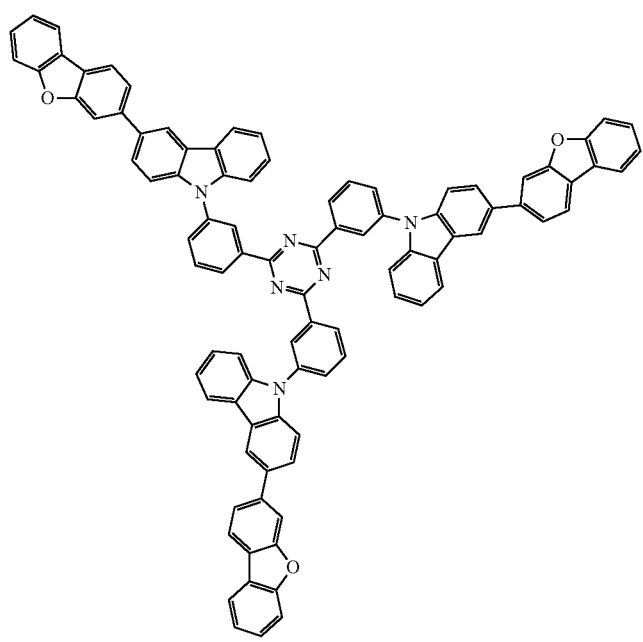

1331 1332
-continued
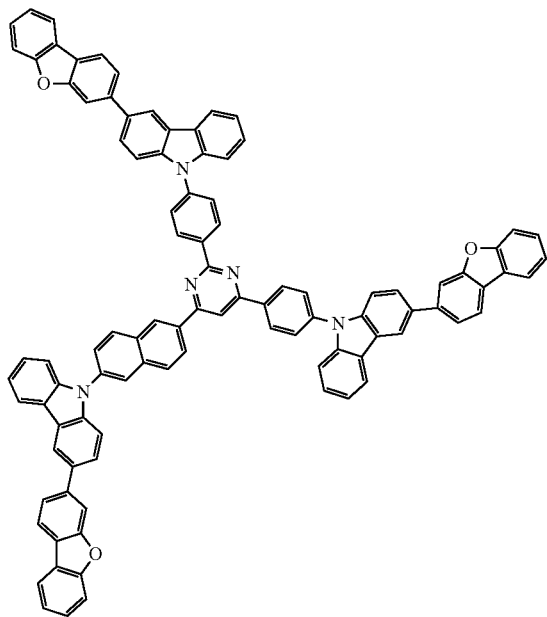
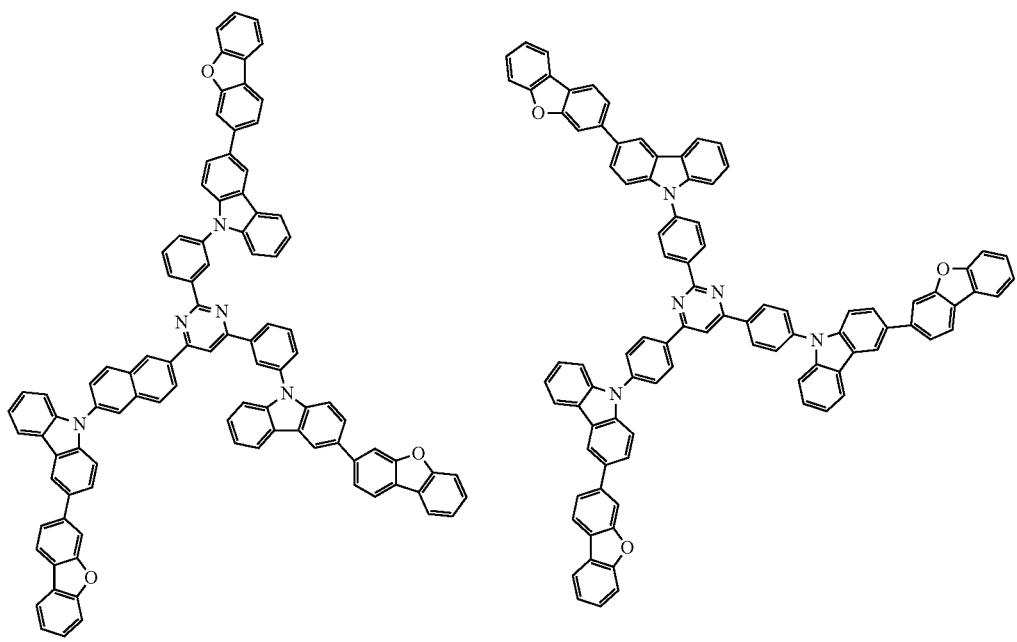 [SMILES: c1cc(-c2cc(-c3ccc4cc(-n5c6ccccc6c6cc(-c7ccc8c(c7)oc7ccccc78)ccc65)ccc4c3)nc(-c3cccc(-n4c5ccccc5c5cc(-c6ccc7c(c6)oc6ccccc67)ccc54)c3)n2)cc(-n2c3ccccc3c3cc(-c4ccc5c(c4)oc4ccccc45)ccc32)c1 ; c1ccc2c(c1)oc1cc(-c3ccc4c(c3)c3ccccc3n4-c3ccc(-c4cc(-c5ccc(-n6c7ccccc7c7cc(-c8ccc9c(c8)oc8ccccc89)ccc76)cc5)nc(-c5ccc(-n6c7ccccc7c7cc(-c8ccc9c(c8)oc8ccccc89)ccc76)cc5)n4)cc3)ccc12]

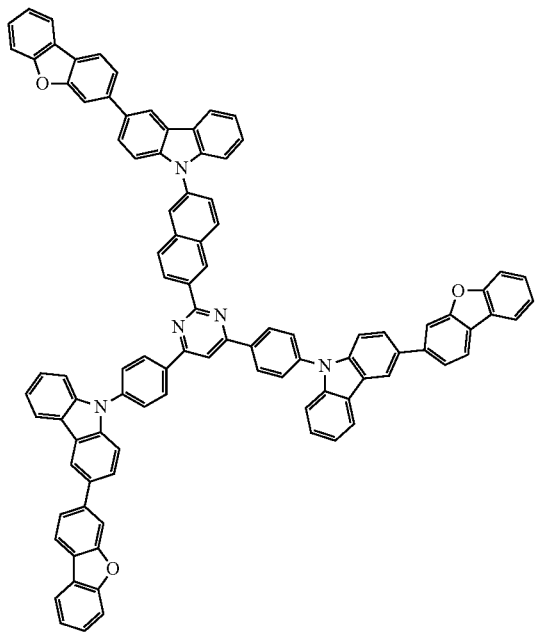
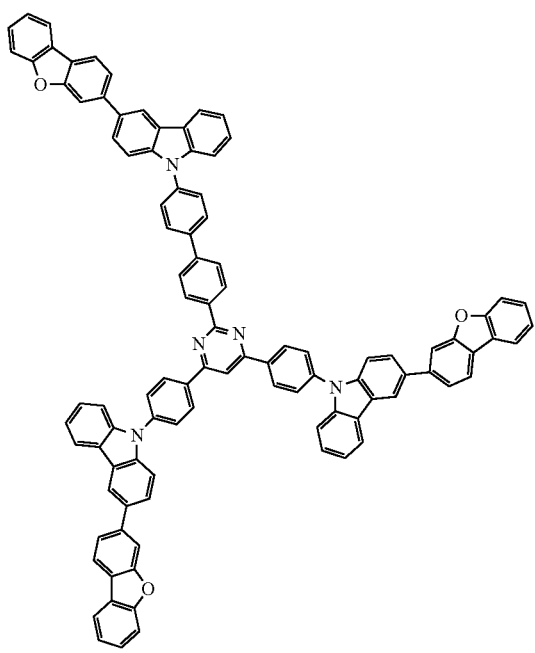

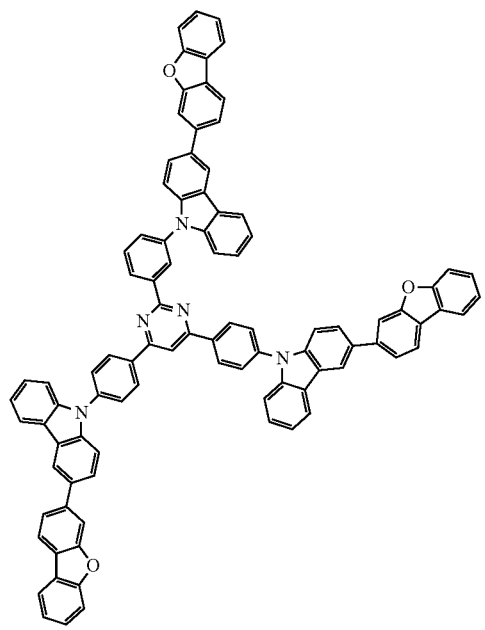
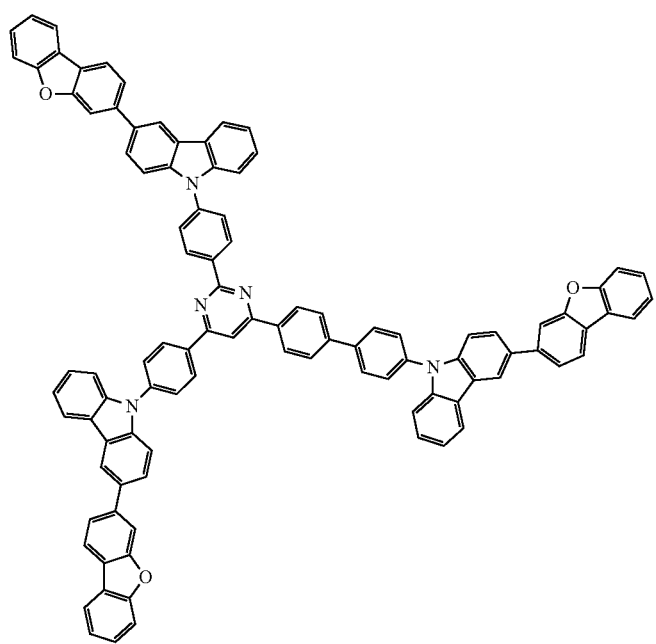

-continued
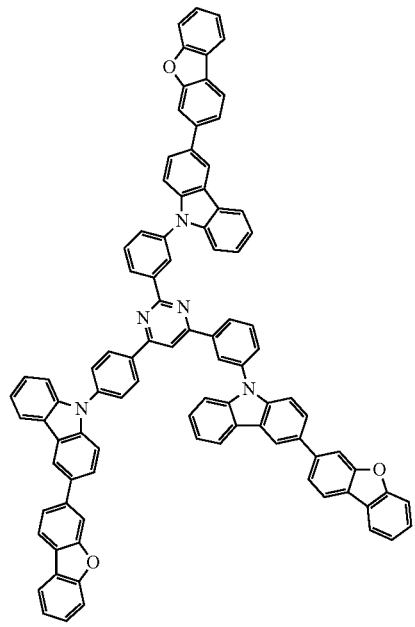
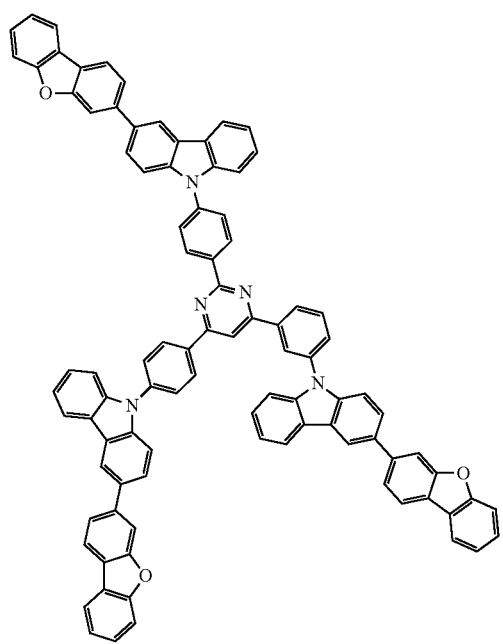

-continued
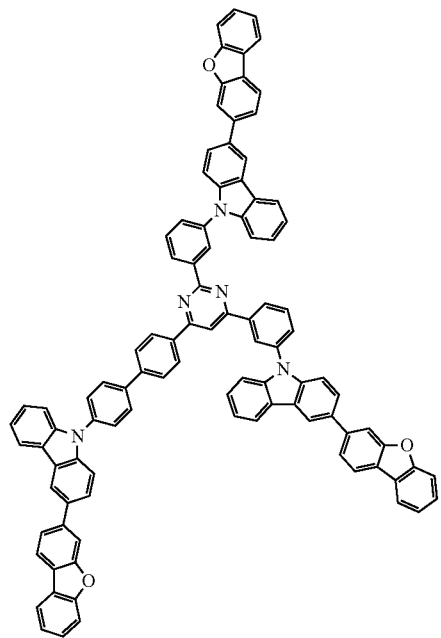
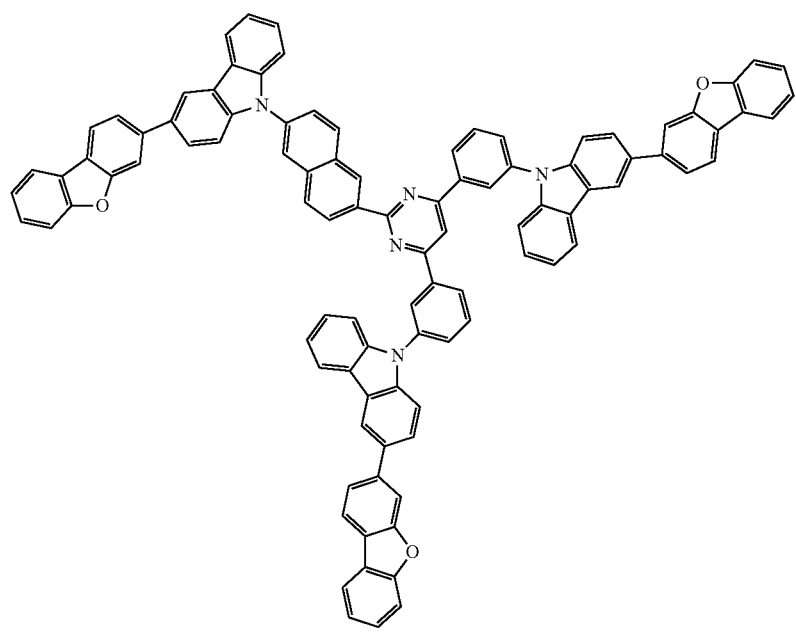

-continued
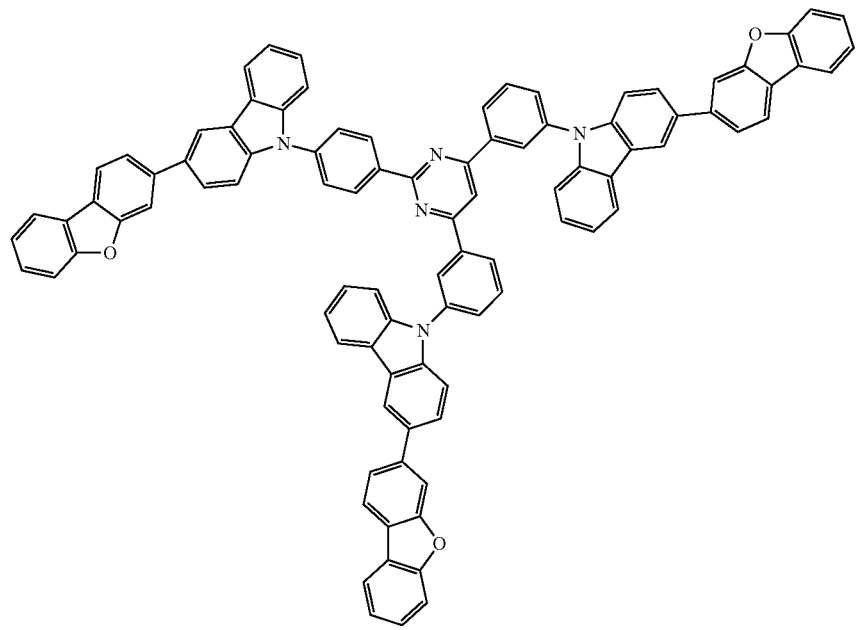
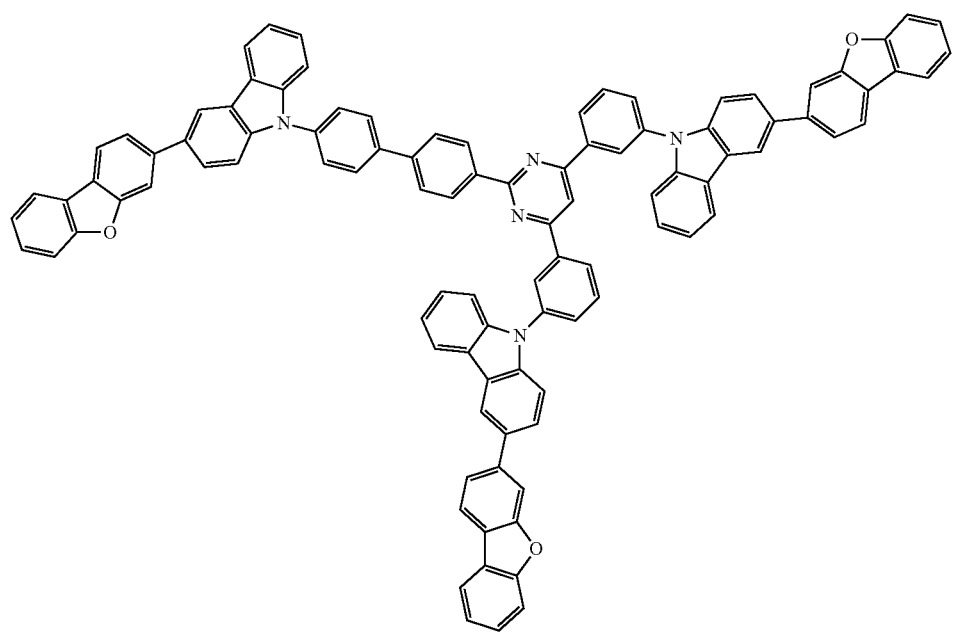

-continued
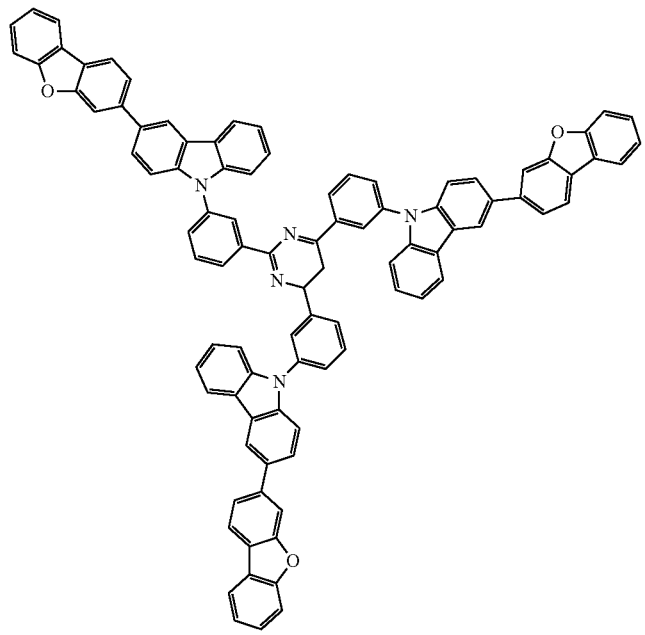
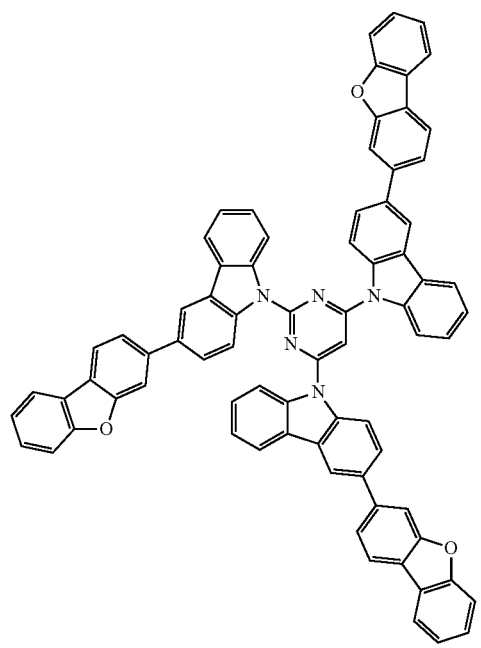

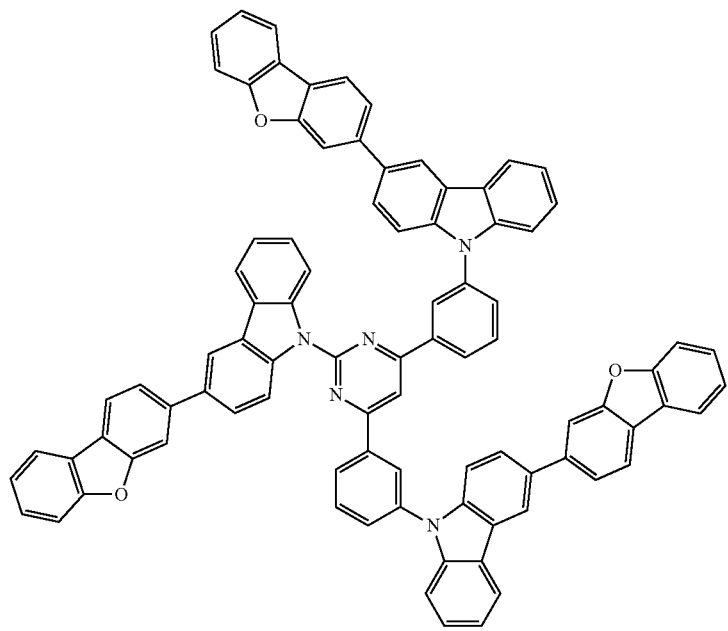
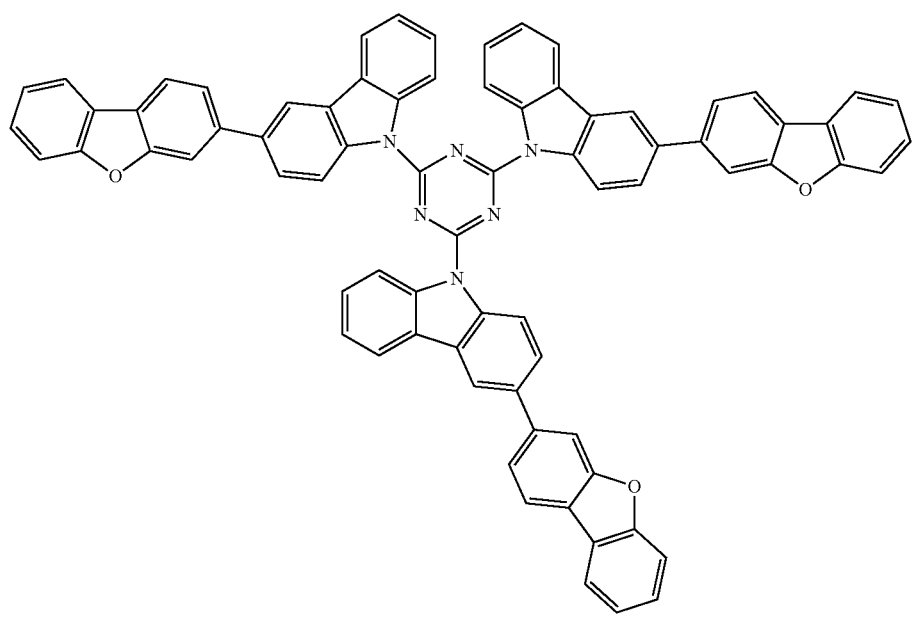

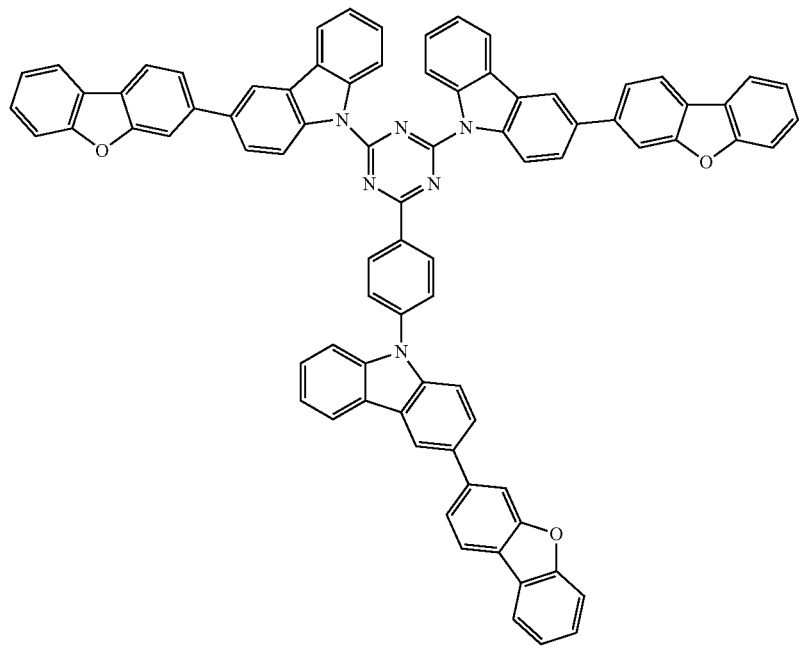
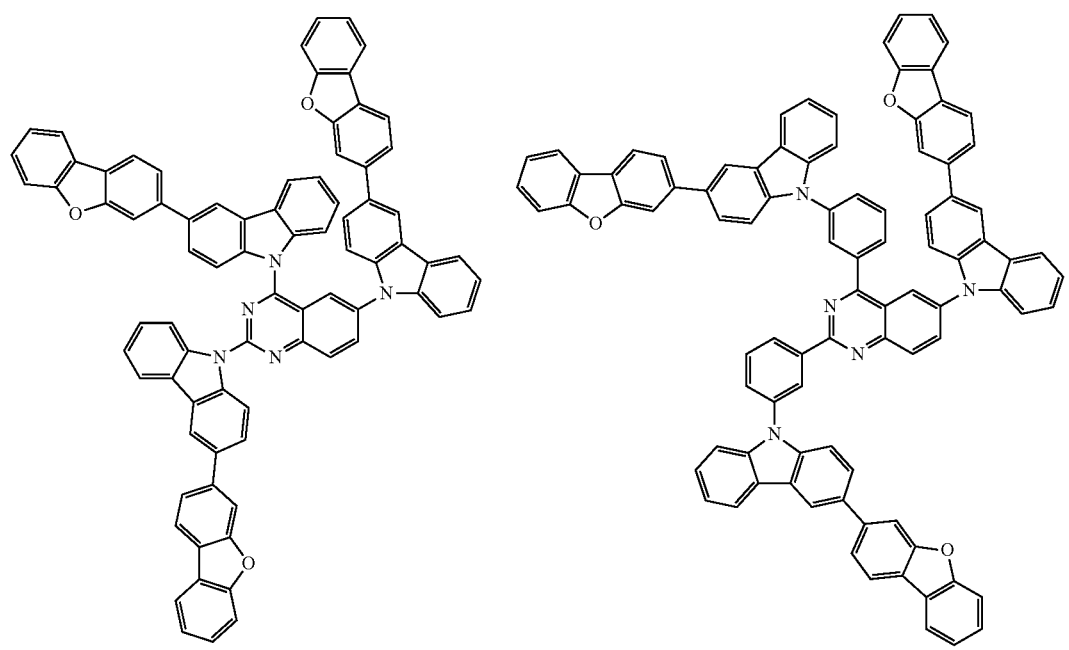

-continued
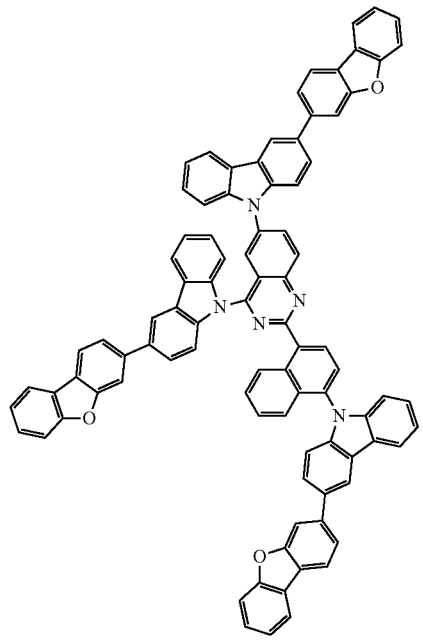
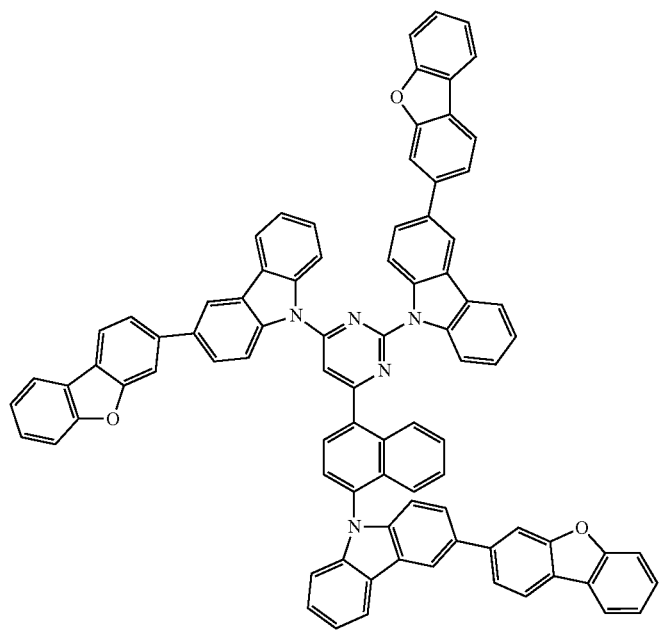

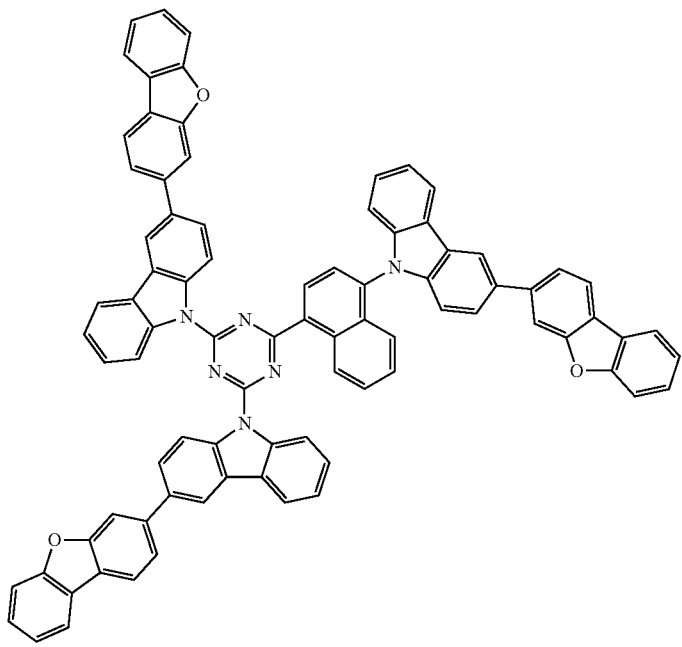
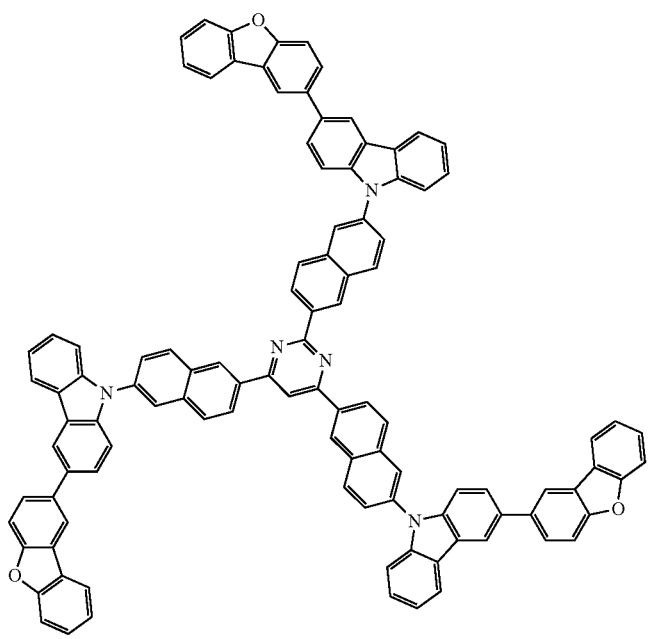

-continued
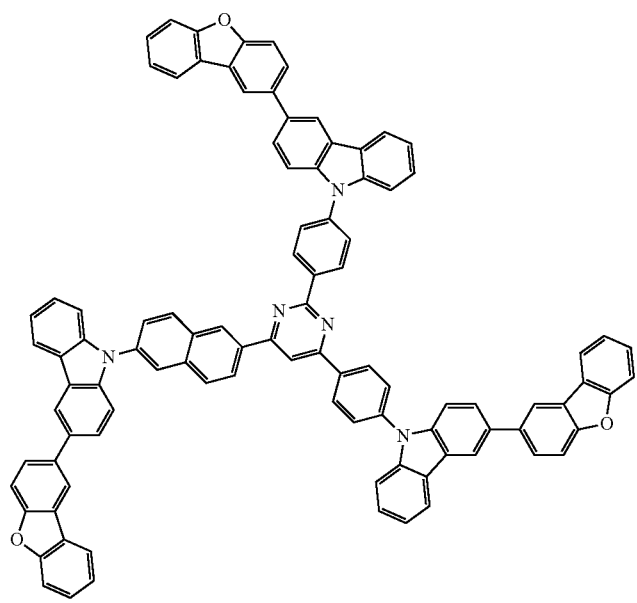
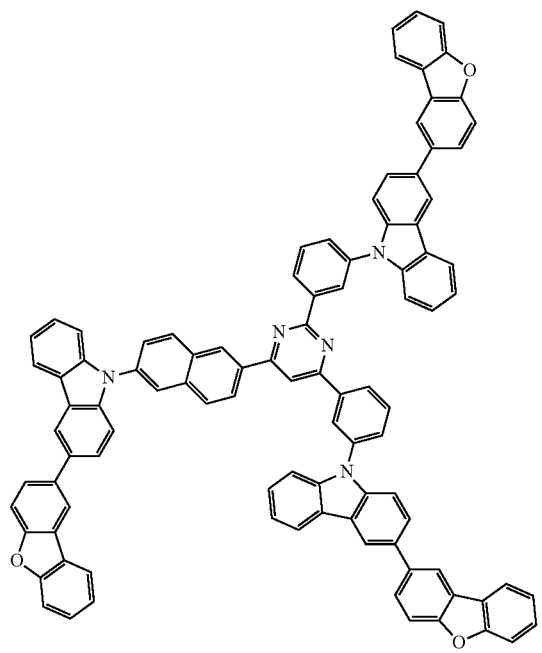

-continued
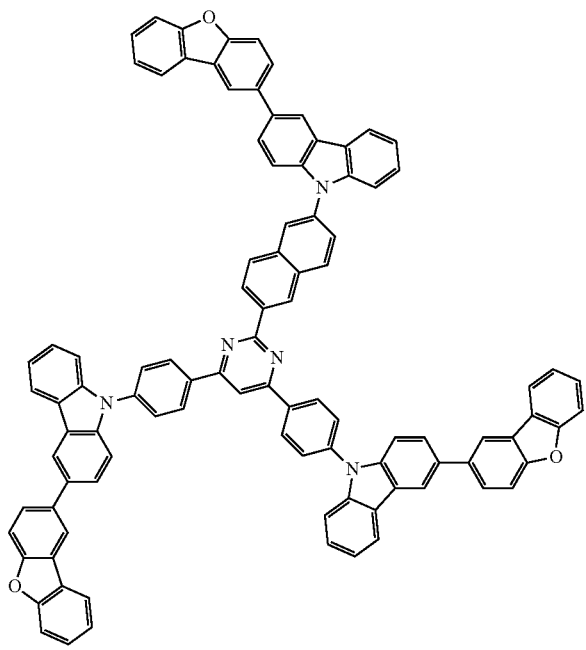
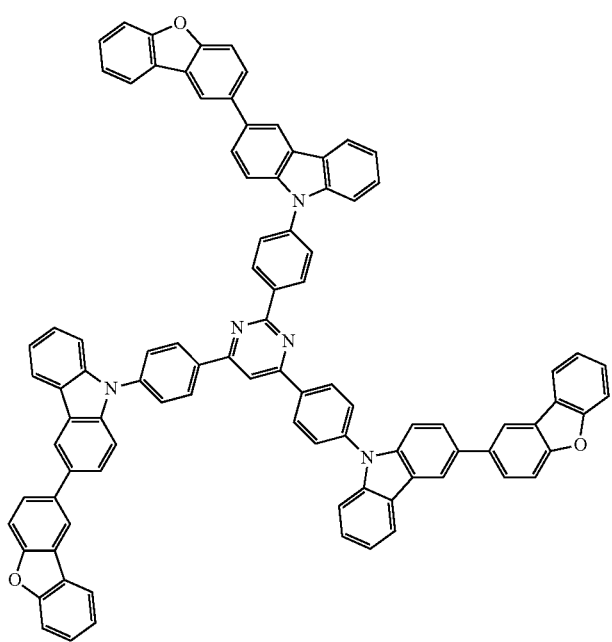

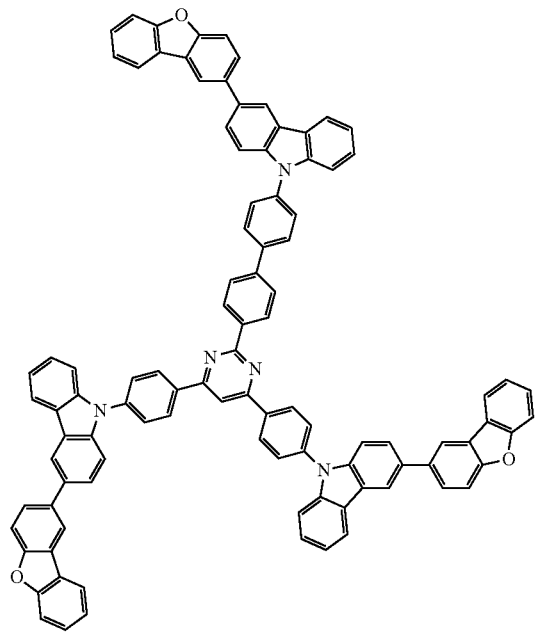
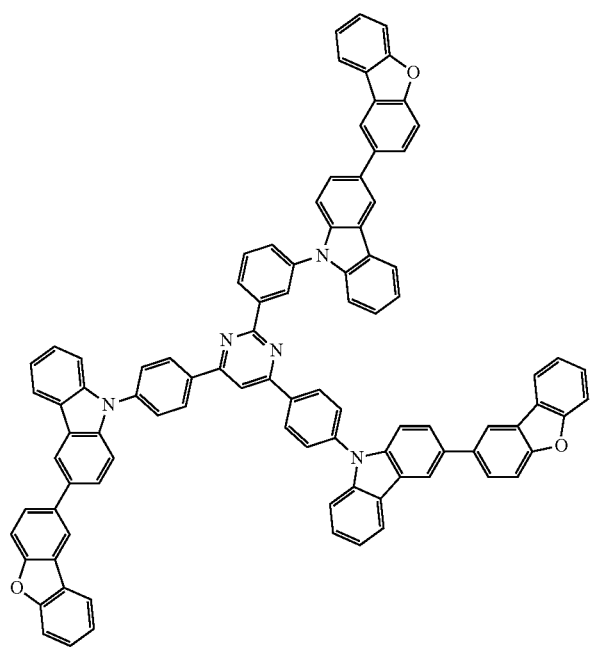

1359
1360
-continued
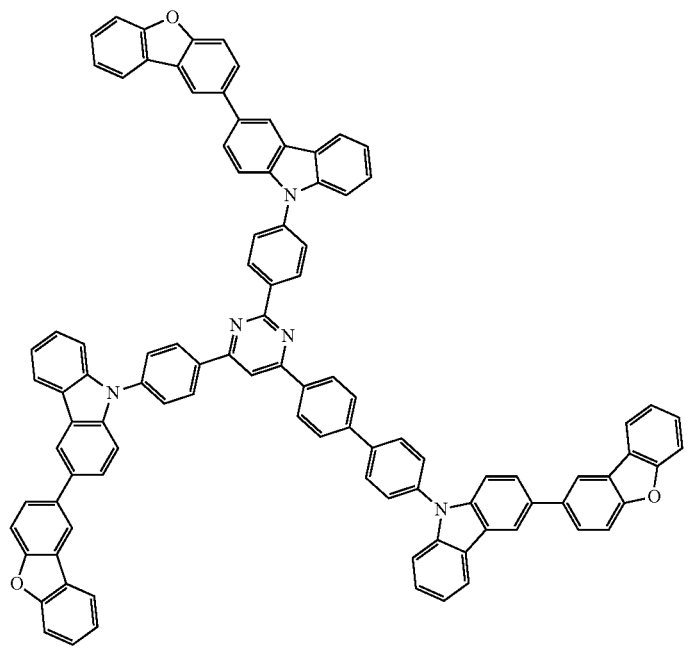
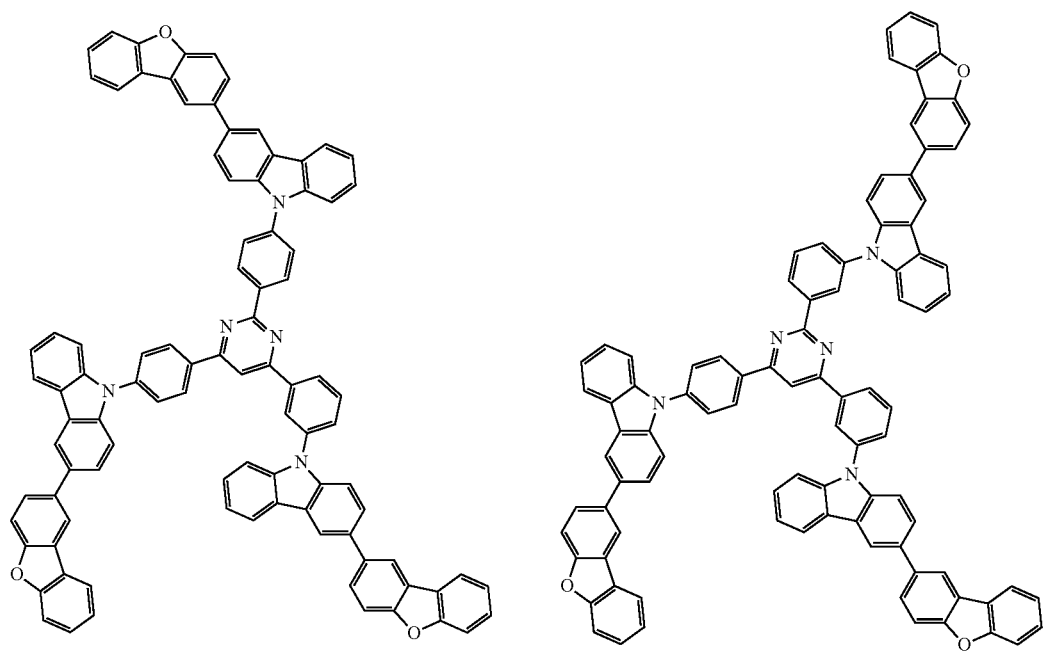

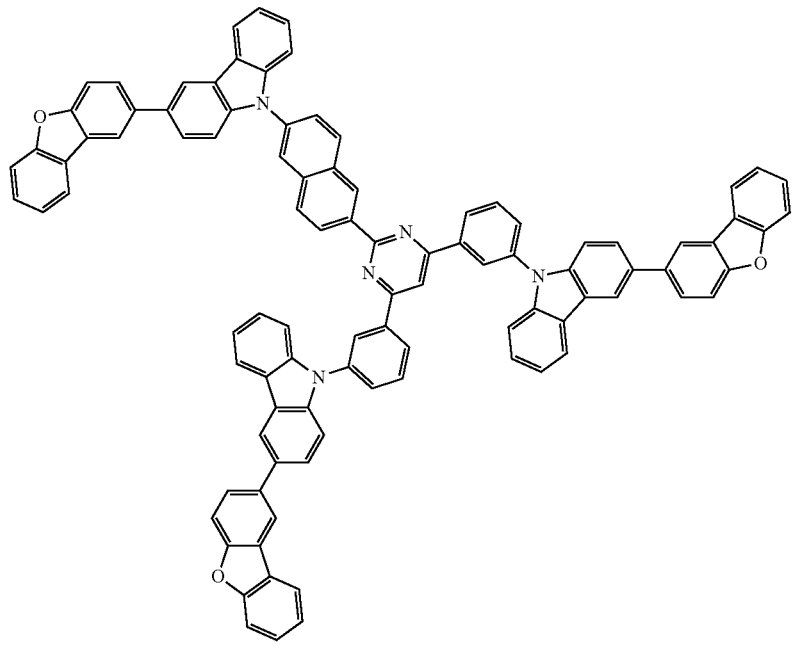
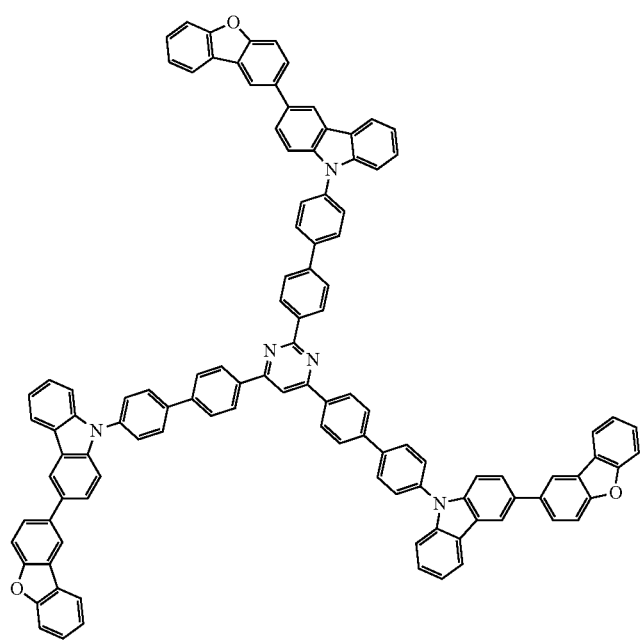

-continued
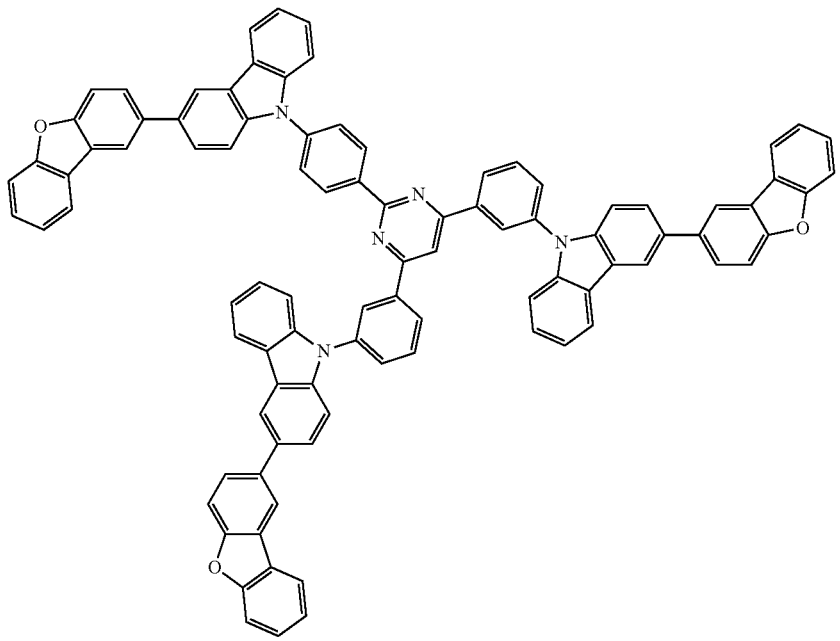
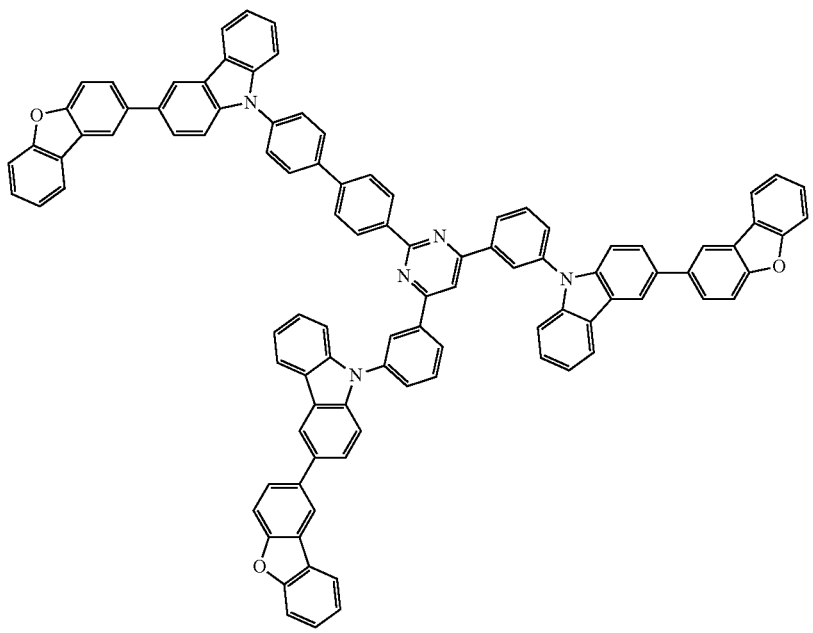

-continued
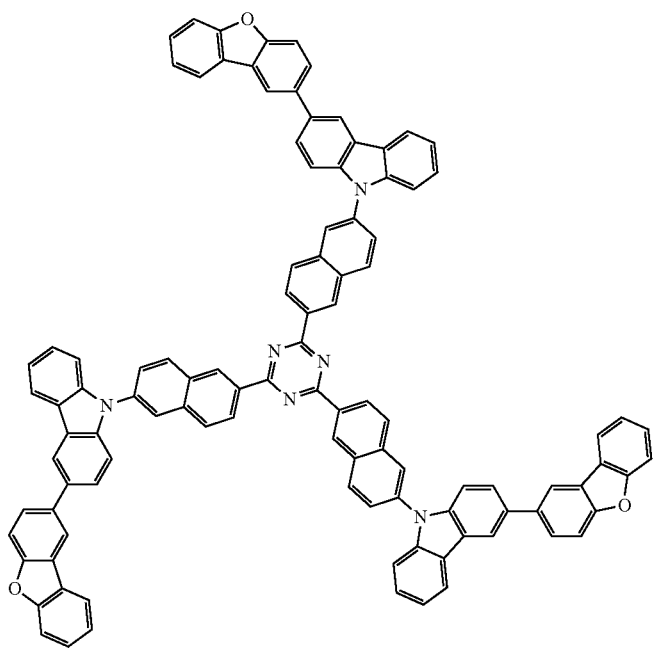
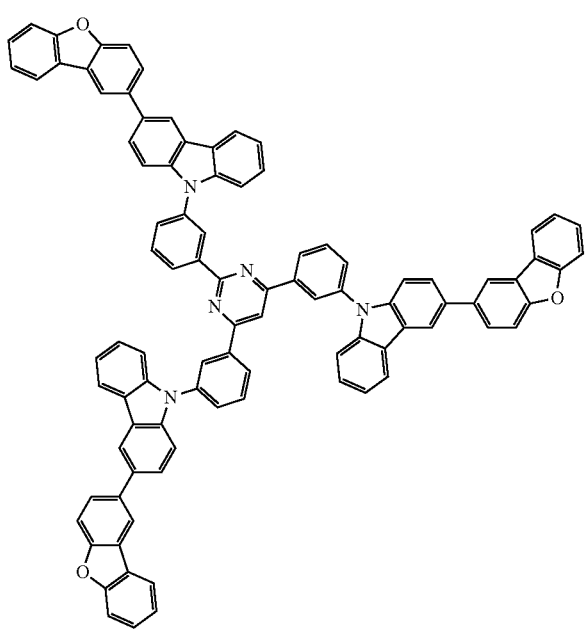

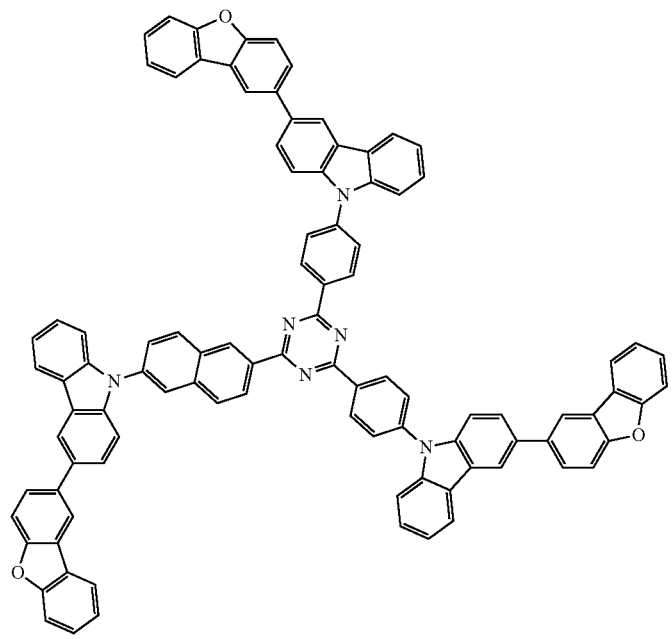
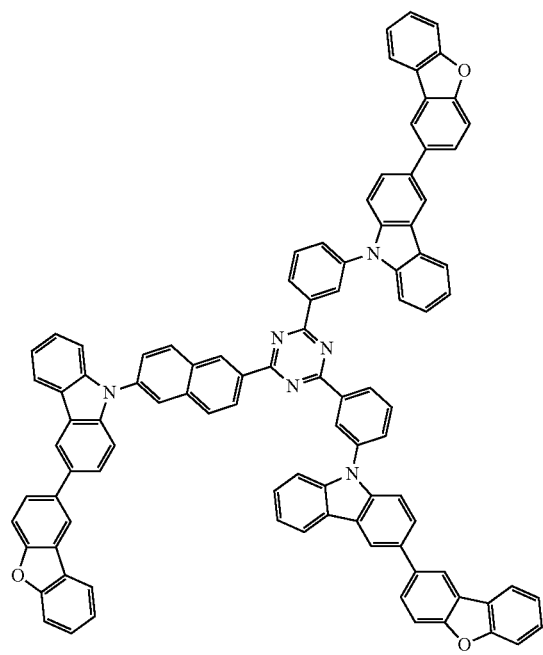

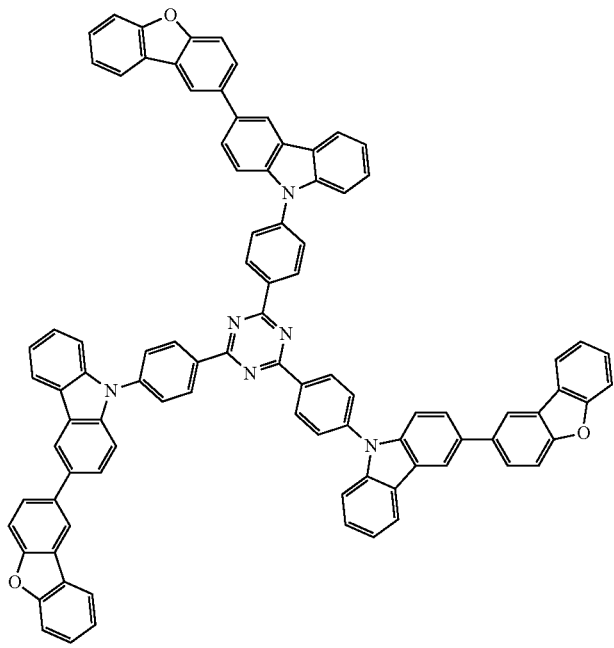
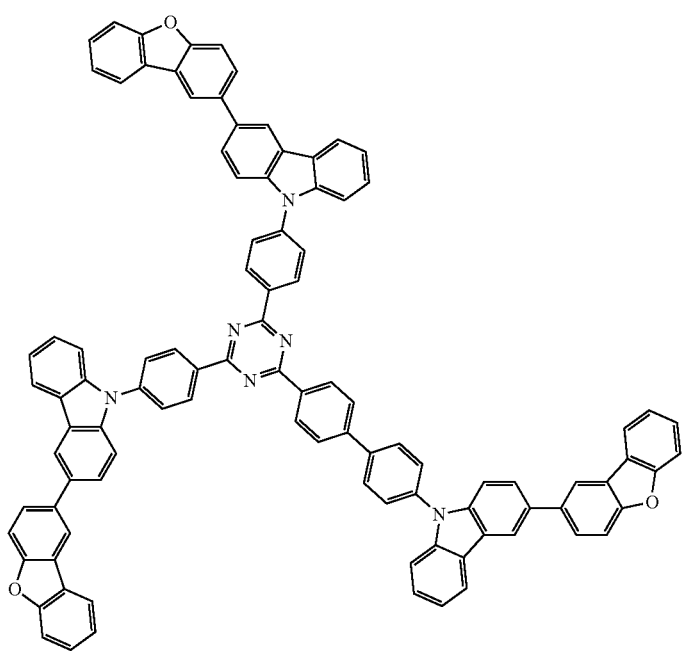

1371 1372
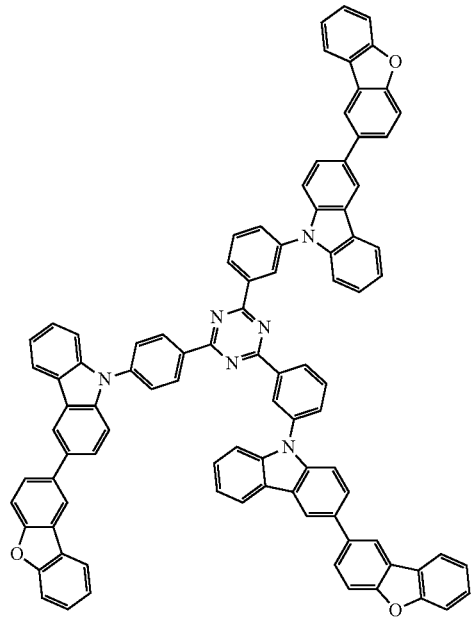
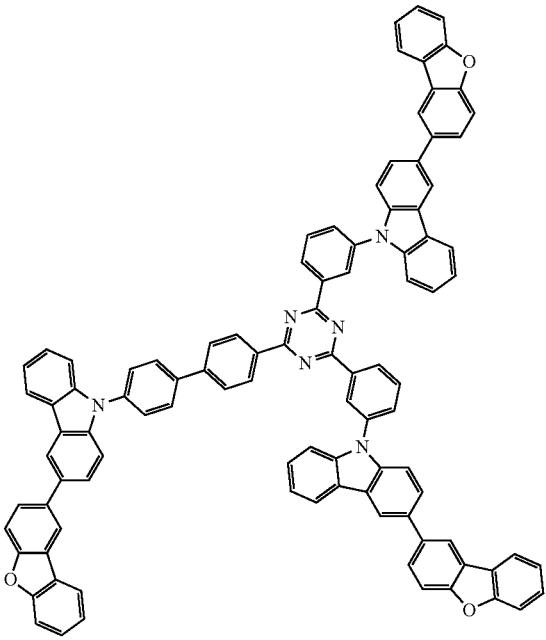
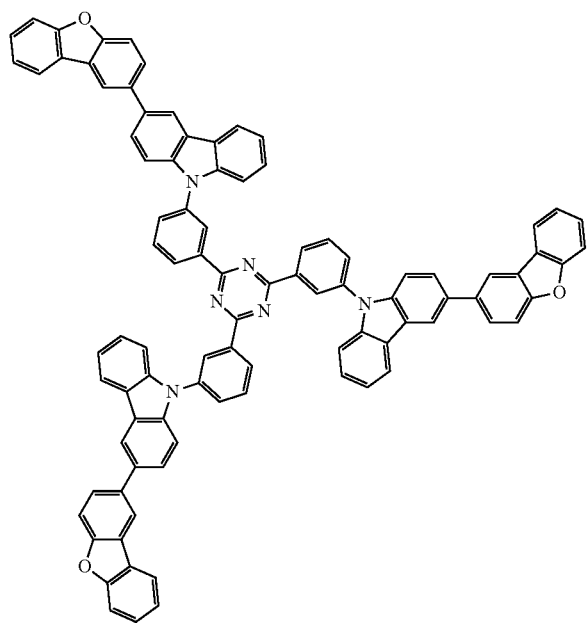

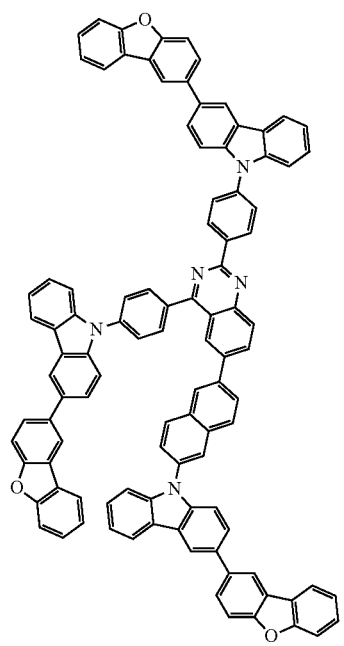
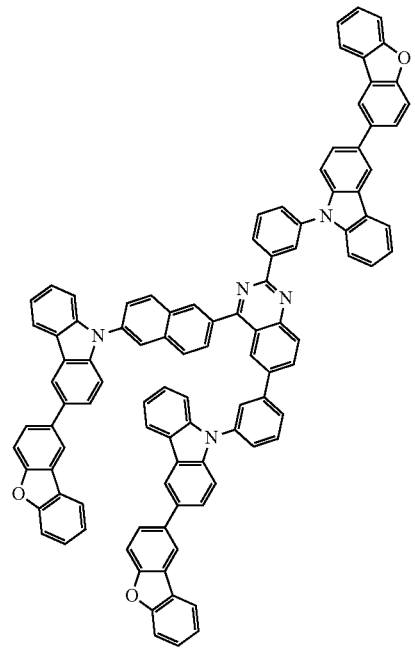
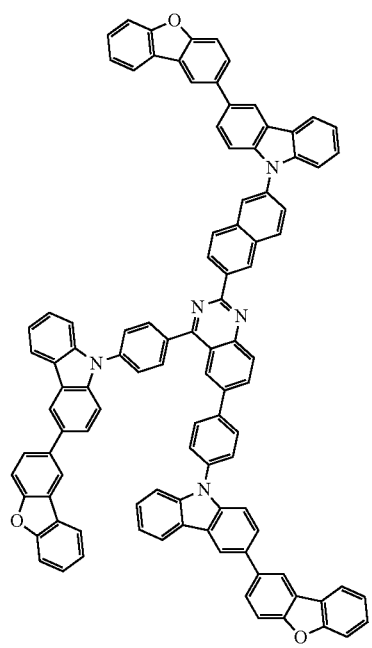
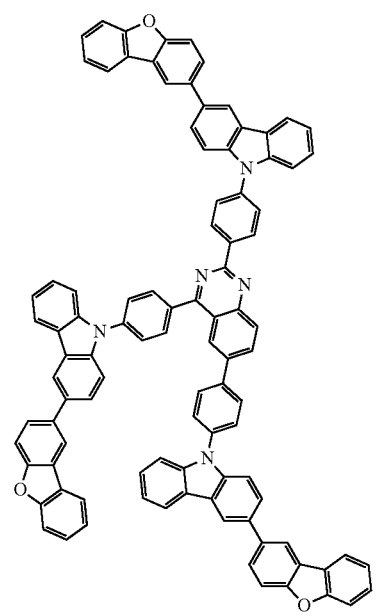

-continued
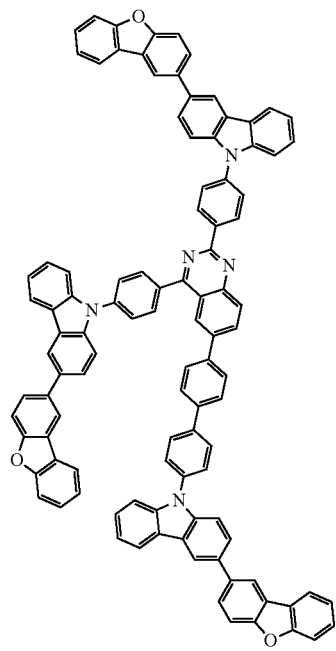
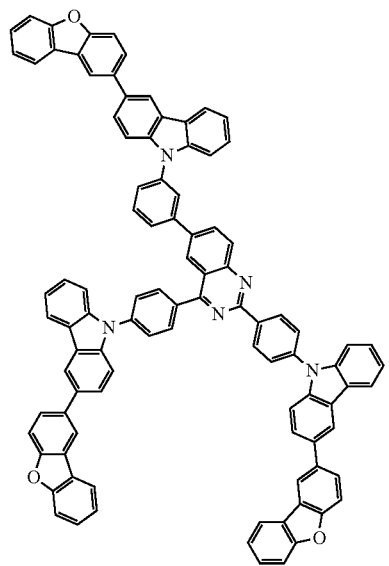
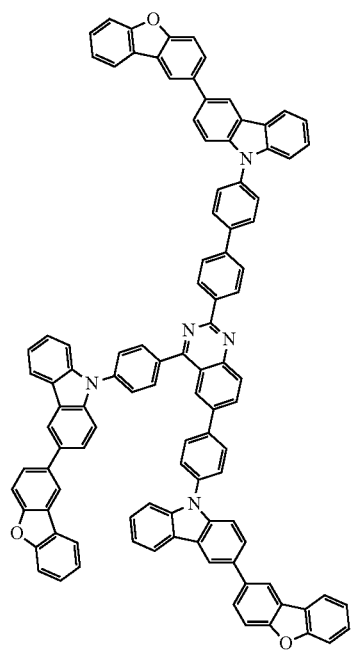
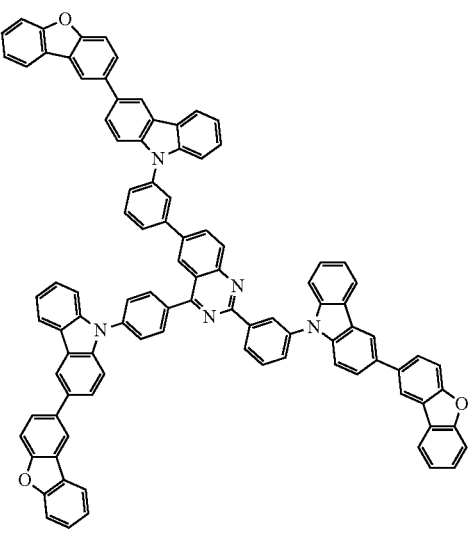

-continued
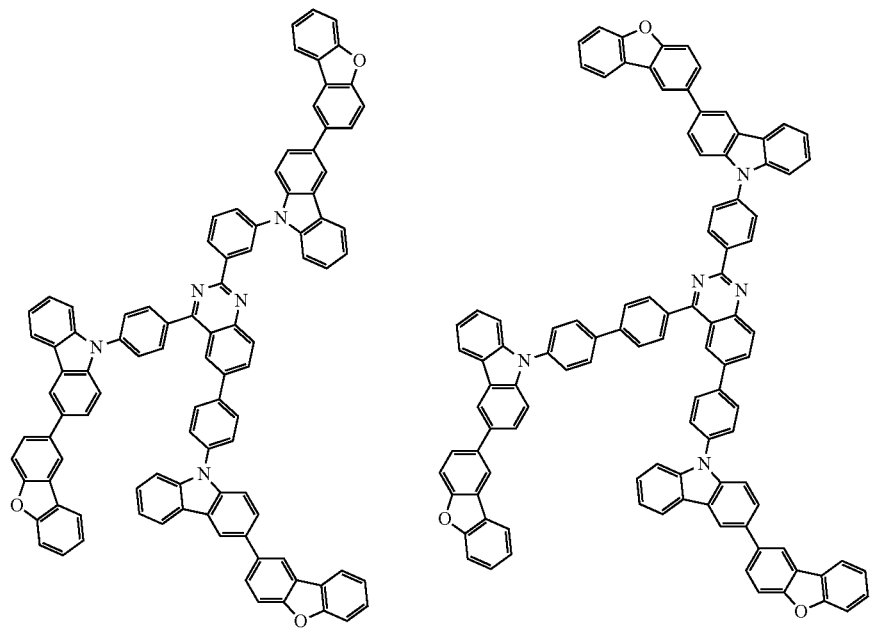 [SMILES: c1cc(-c2nc(-c3ccc(-n4c5ccccc5c5cc(-c6ccc7oc8ccccc8c7c6)ccc54)cc3)c3cc(-c4ccc(-n5c6ccccc6c6cc(-c7ccc8oc9ccccc9c8c7)ccc65)cc4)ccc3n2)cc(-n2c3ccccc3c3cc(-c4ccc5oc6ccccc6c5c4)ccc32)c1 ; c1ccc2c(c1)oc1ccc(-c3ccc4c(c3)c3ccccc3n4-c3ccc(-c4ccc(-c5nc(-c6ccc(-n7c8ccccc8c8cc(-c9ccc%10oc%11ccccc%11c%10c9)ccc87)cc6)nc6ccc(-c7ccc(-n8c9ccccc9c9cc(-c%10ccc%11oc%12ccccc%12c%11c%10)ccc98)cc7)cc56)cc4)cc3)cc12]
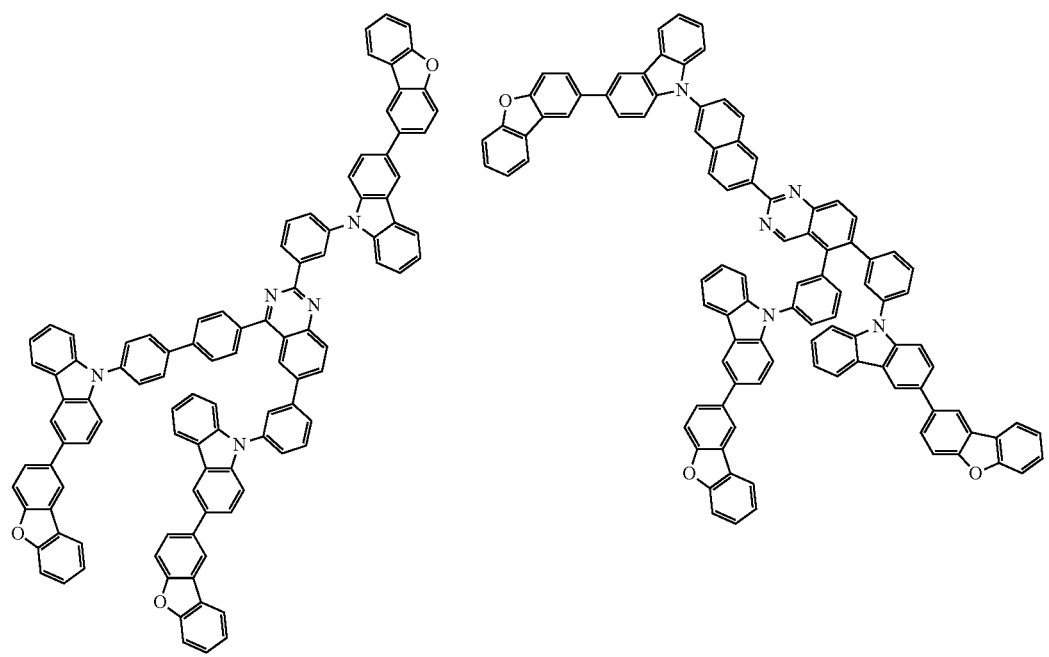 [SMILES: c1cc(-c2ccc3nc(-c4cccc(-n5c6ccccc6c6cc(-c7ccc8oc9ccccc9c8c7)ccc65)c4)nc(-c4ccc(-c5ccc(-n6c7ccccc7c7cc(-c8ccc9oc%10ccccc%10c9c8)ccc76)cc5)cc4)c3c2)cc(-n2c3ccccc3c3cc(-c4ccc5oc6ccccc6c5c4)ccc32)c1 ; c1cc(-c2ccc3nc(-c4ccc5cc(-n6c7ccccc7c7cc(-c8ccc9oc%10ccccc%10c9c8)ccc76)ccc5c4)ncc3c2-c2cccc(-n3c4ccccc4c4cc(-c5ccc6oc7ccccc7c6c5)ccc43)c2)cc(-n2c3ccccc3c3cc(-c4ccc5oc6ccccc6c5c4)ccc32)c1]

-continued
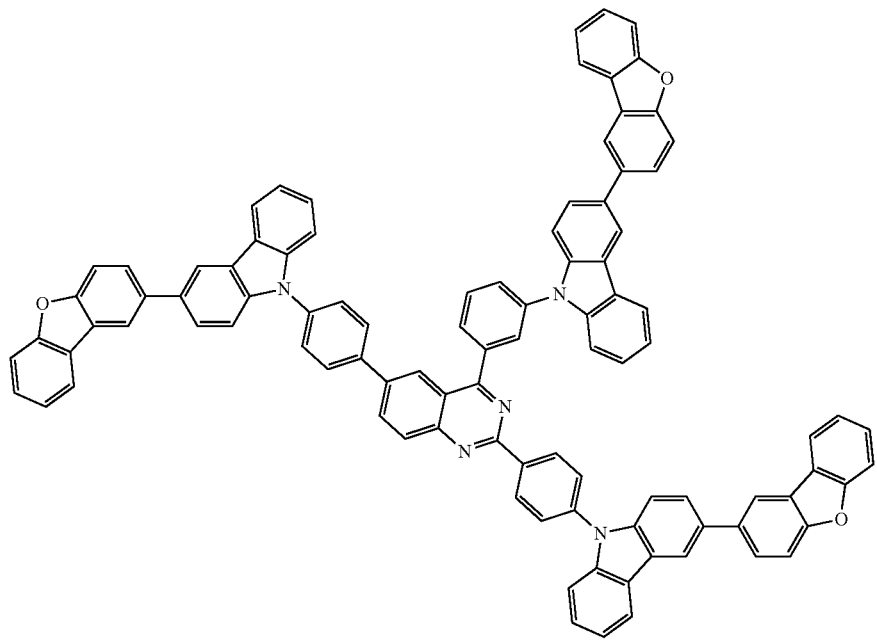
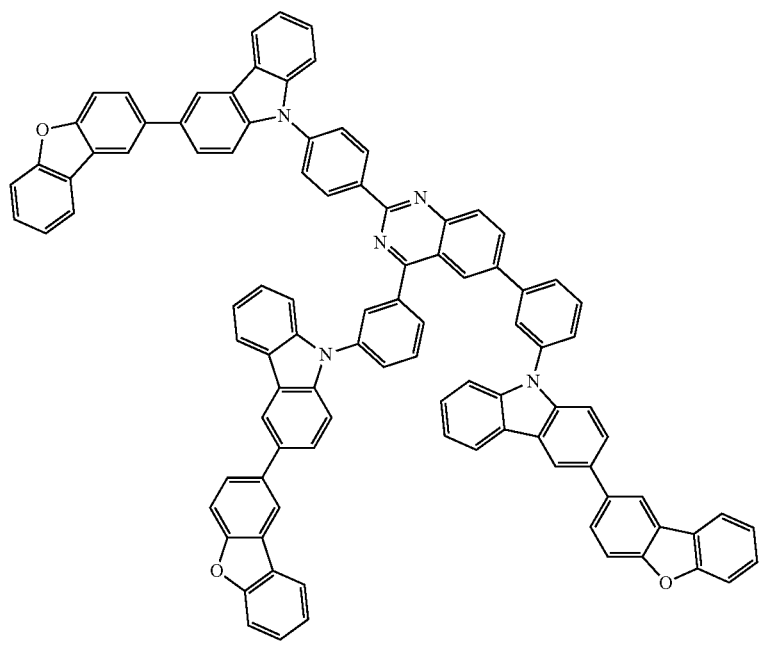

-continued
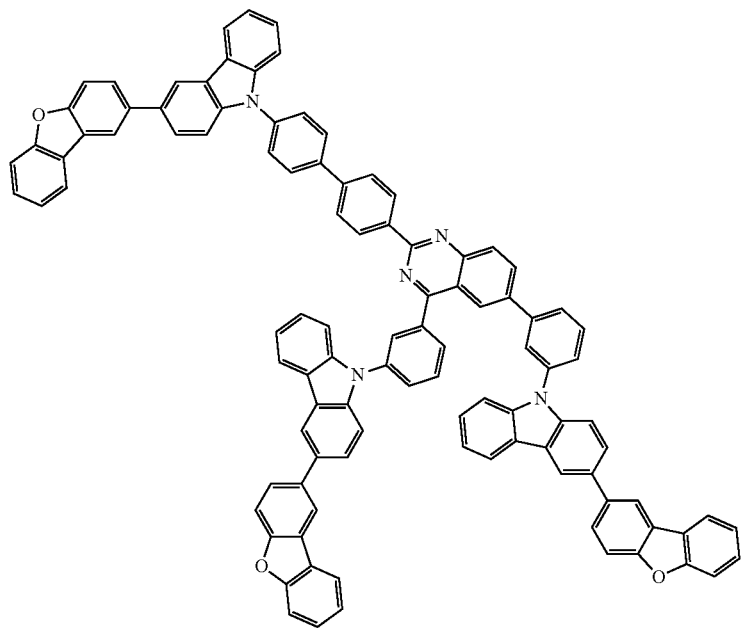
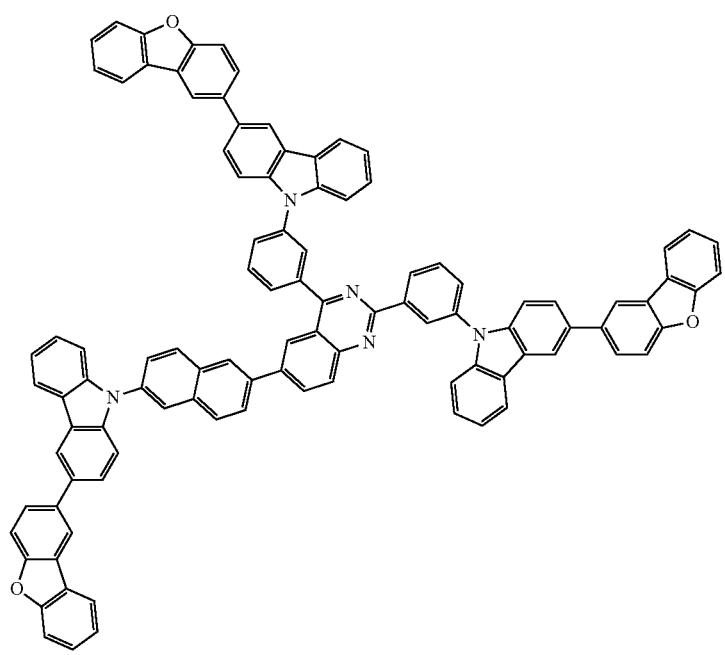

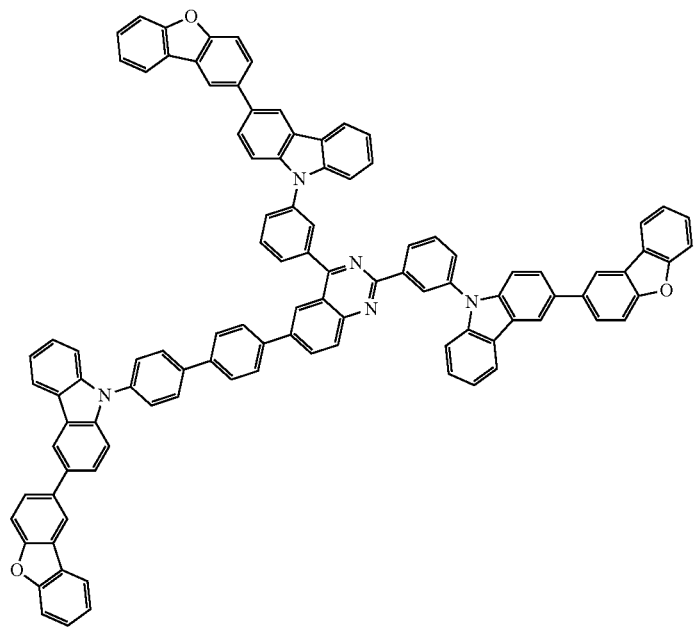
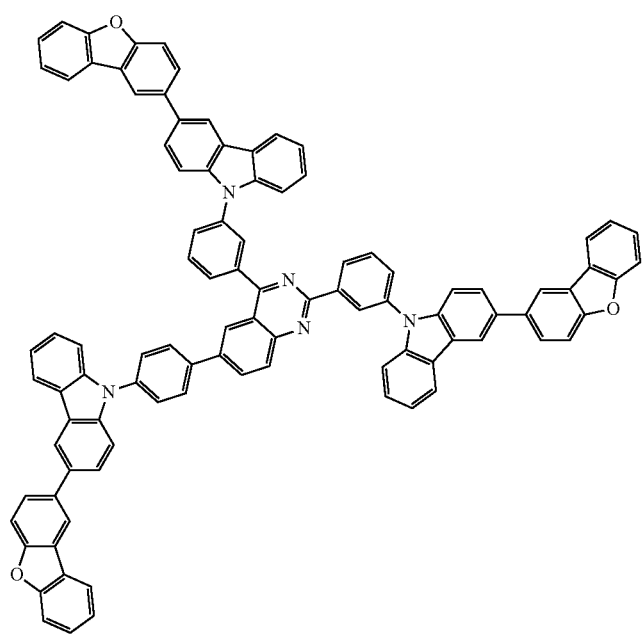

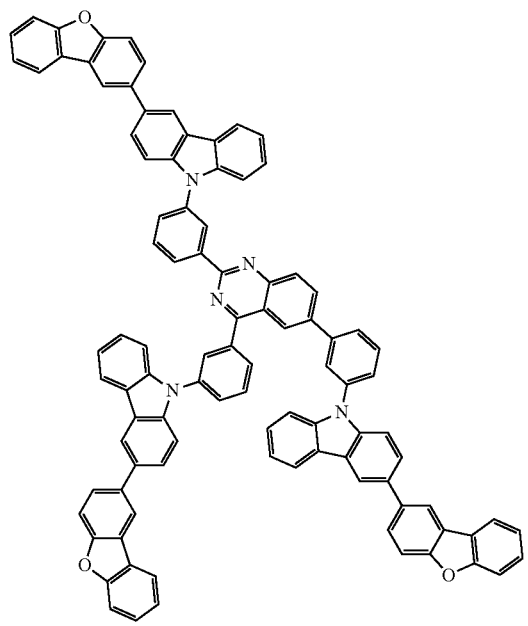
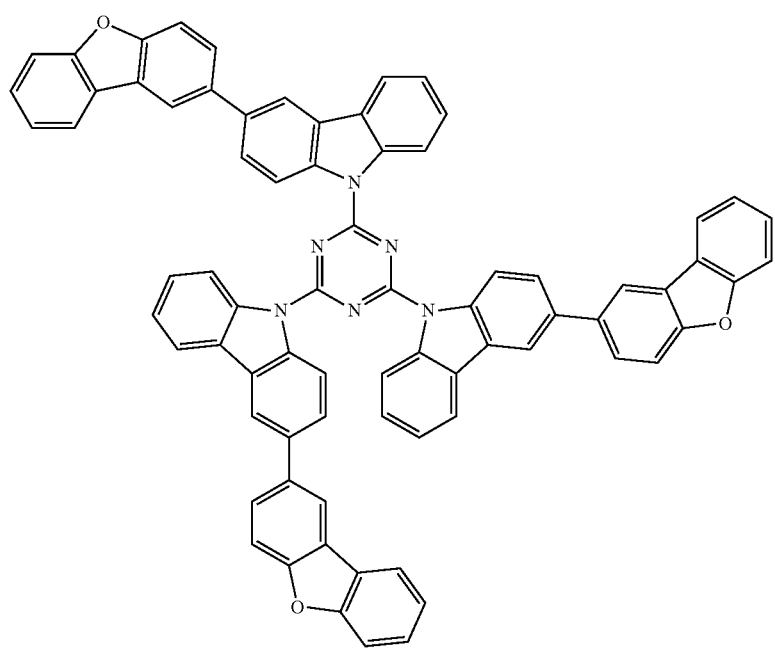

-continued
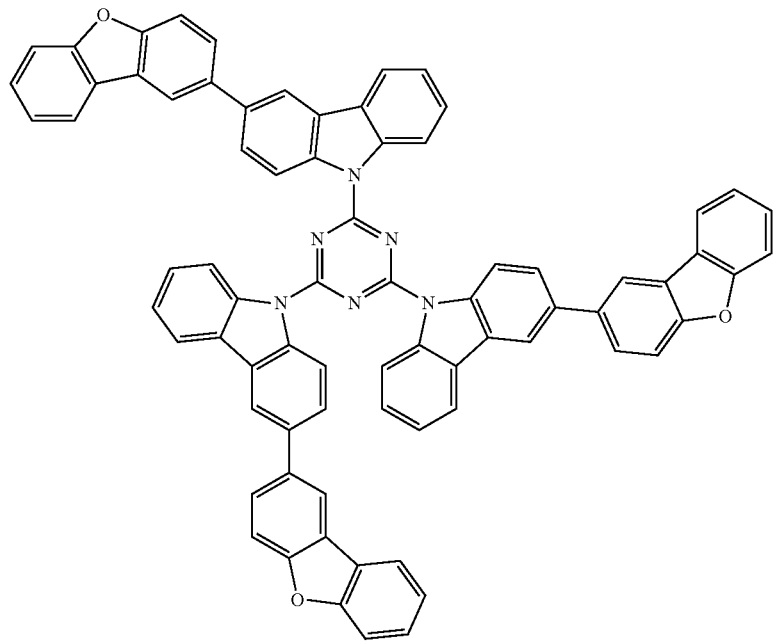
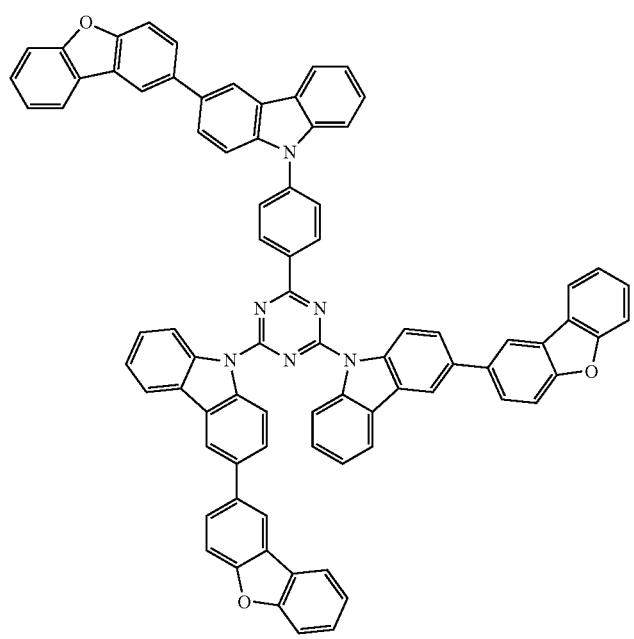

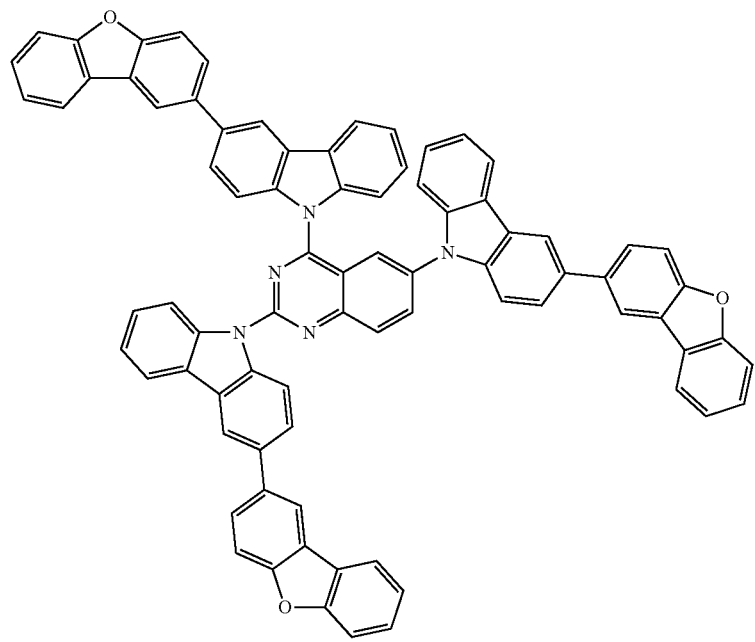
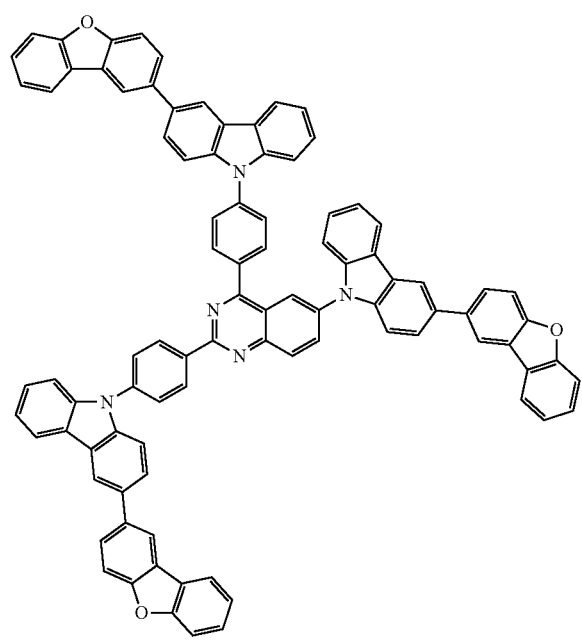

-continued
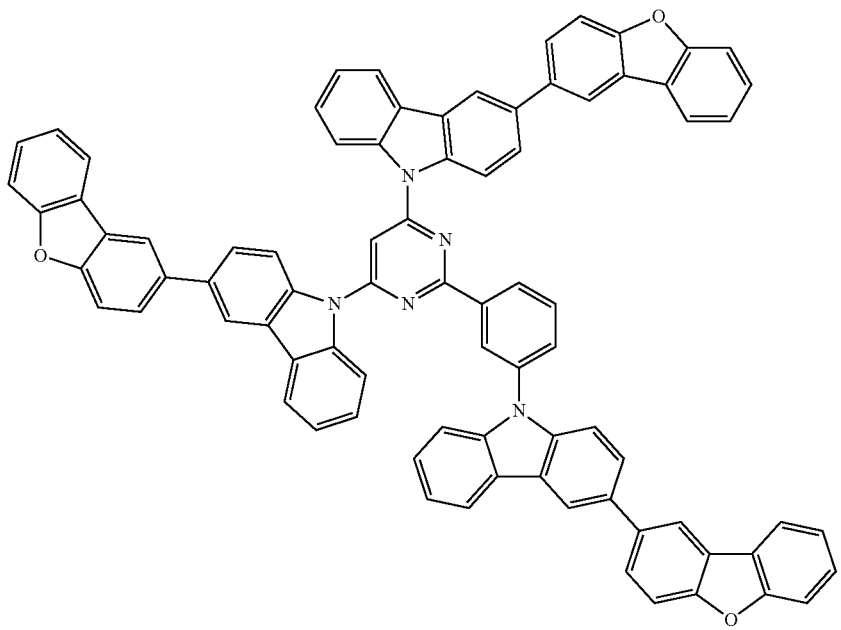
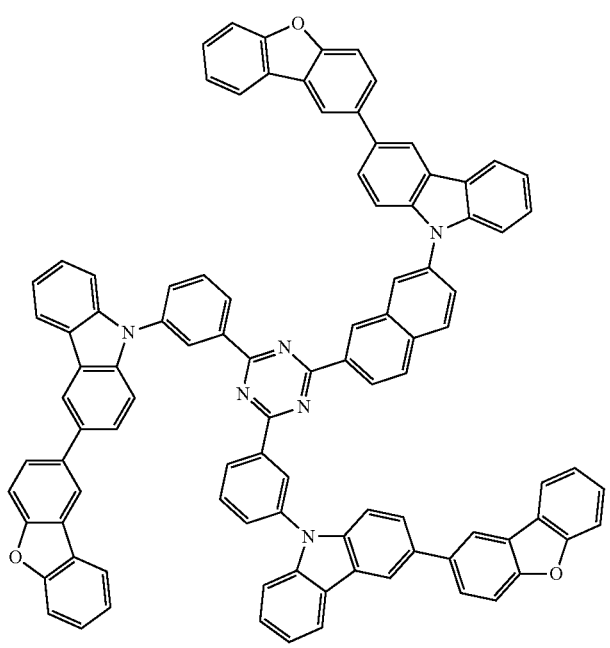

1393
1394
-continued
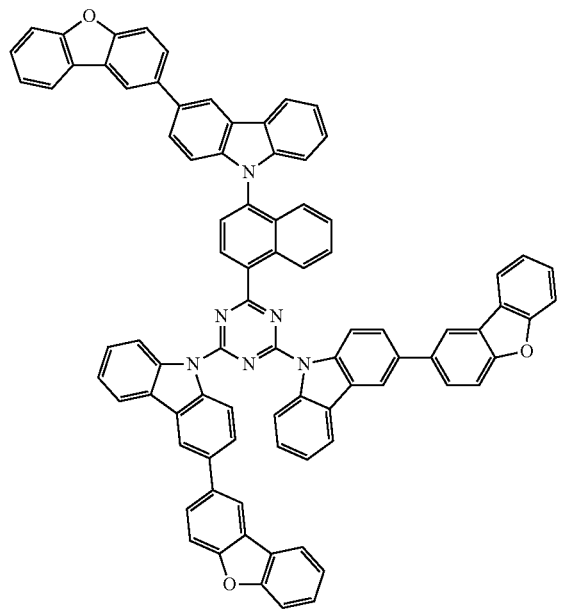
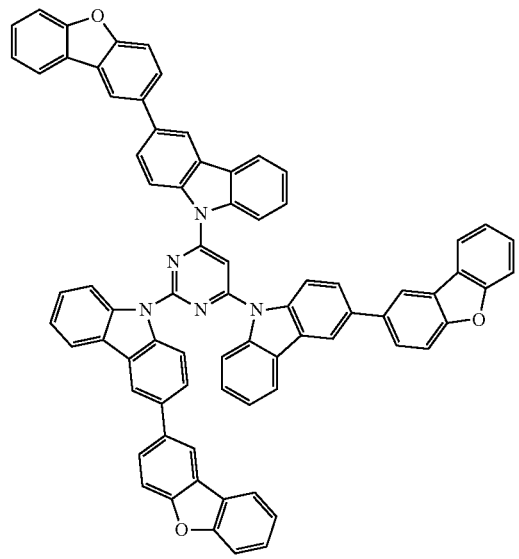
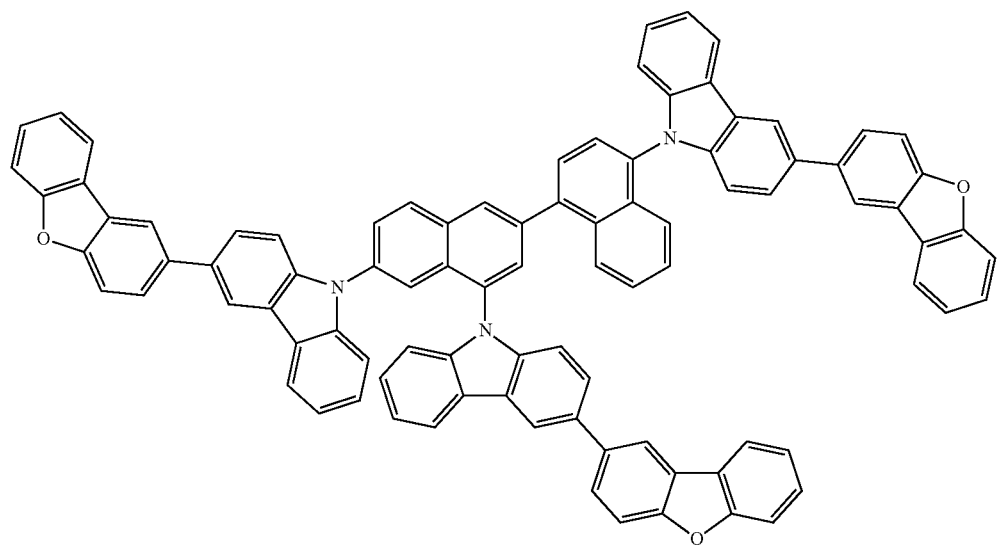 [SMILES: c1ccc2c(c1)oc1ccc(-c3ccc4c(c3)c3ccccc3n4-c3ccc4cc(-c5ccc(-n6c7ccccc7c7cc(-c8ccc9oc%10ccccc%10c9c8)ccc76)c6ccccc56)cc(-n5c6ccccc6c6cc(-c7ccc8oc9ccccc9c8c7)ccc65)c4c3)cc12]

1395
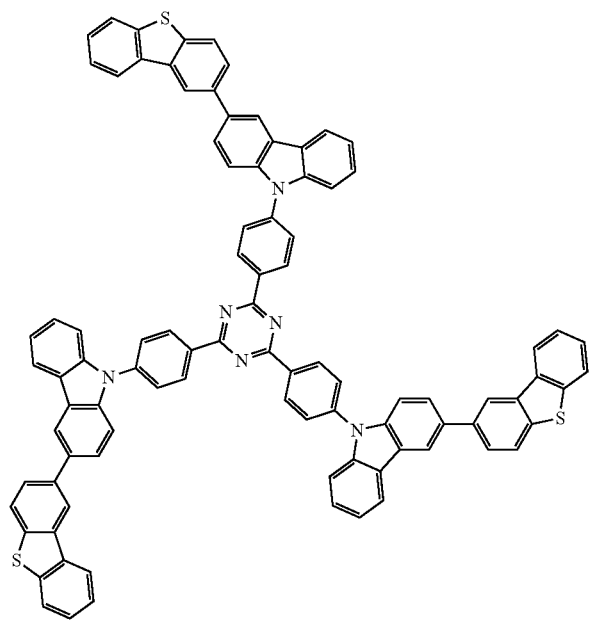
1396
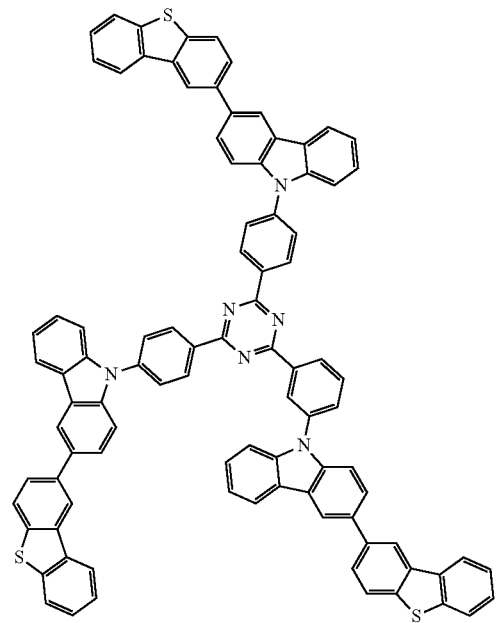
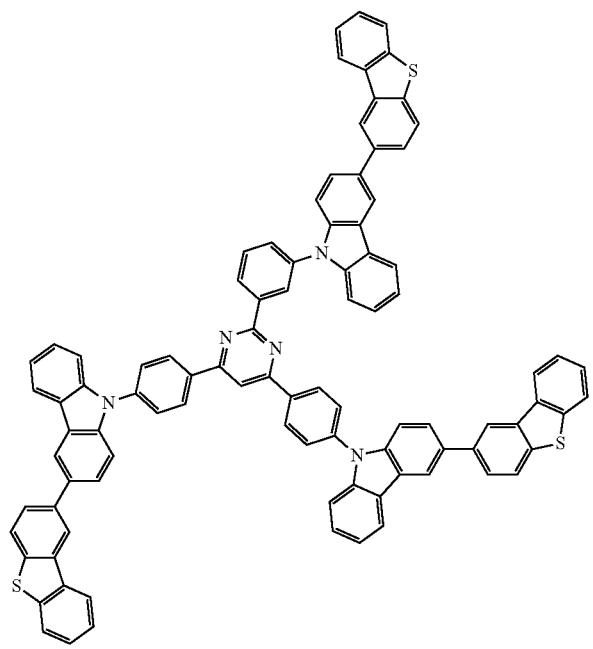
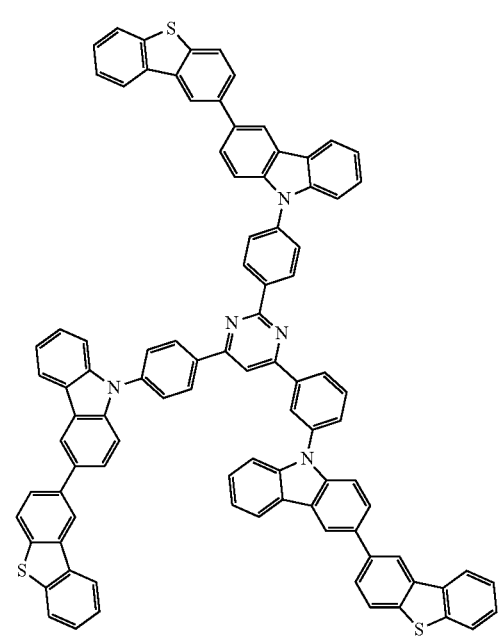

-continued
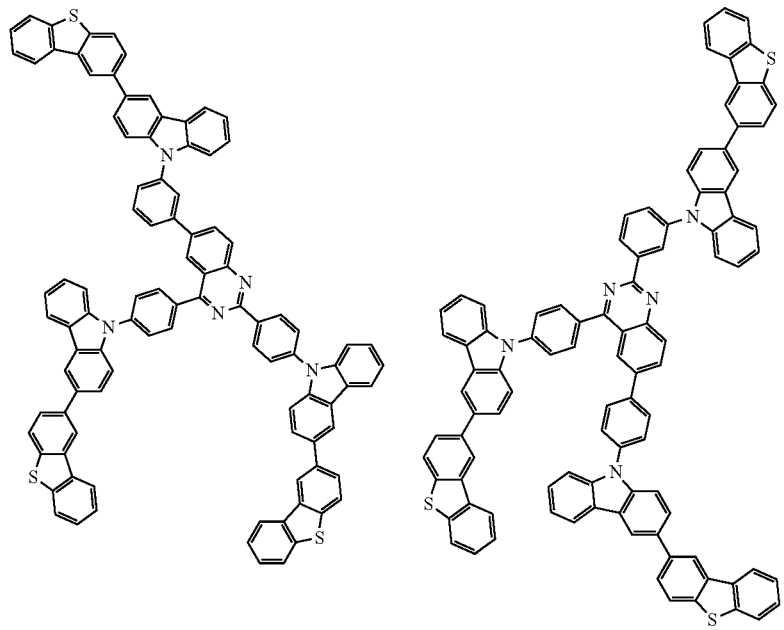
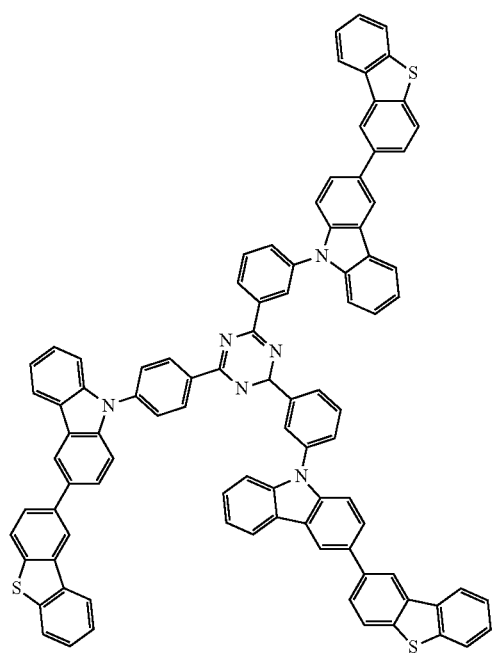

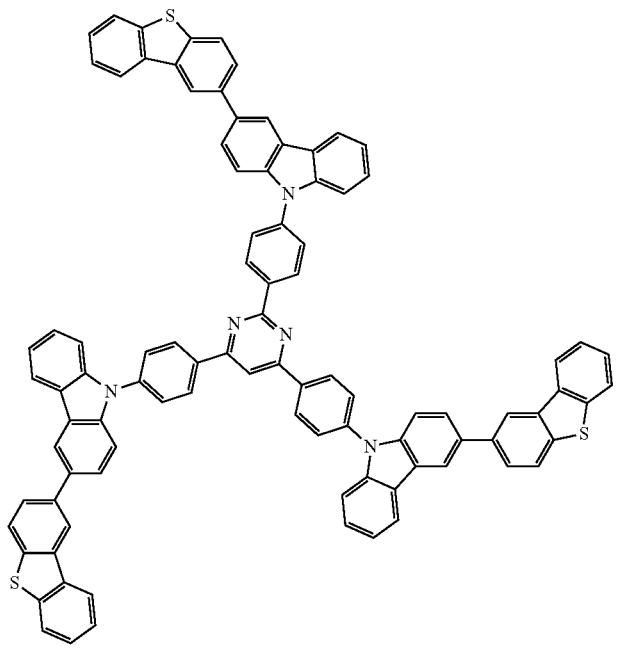
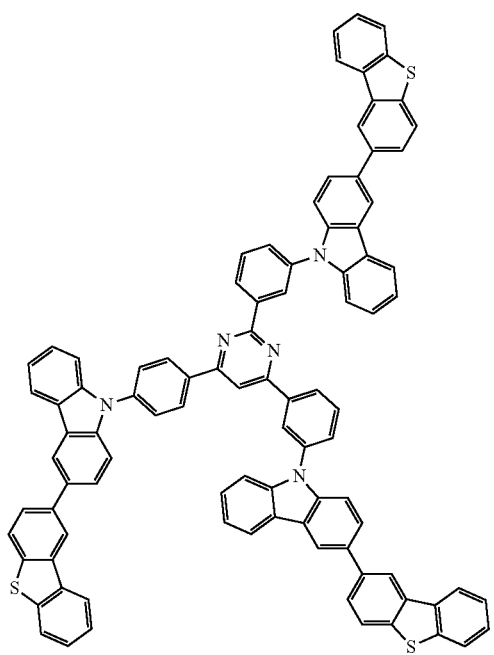

1401
1402
-continued
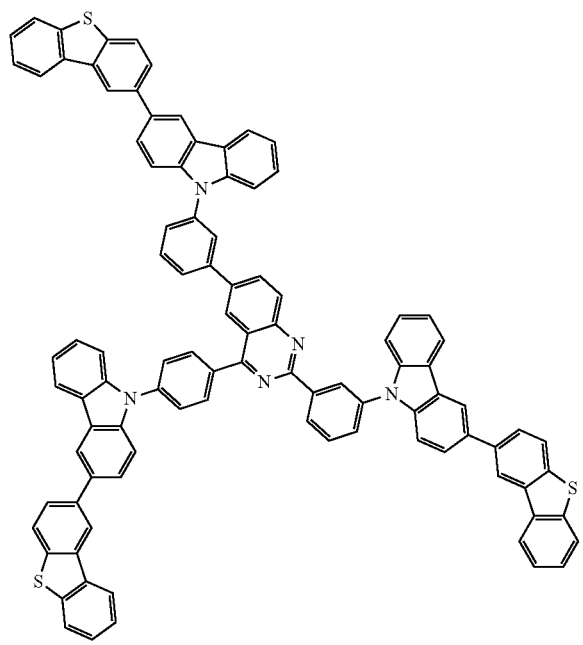
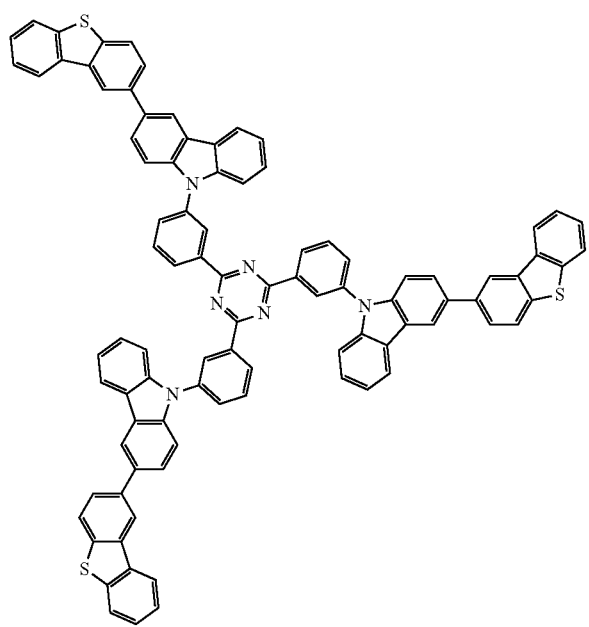

1403
1404
-continued
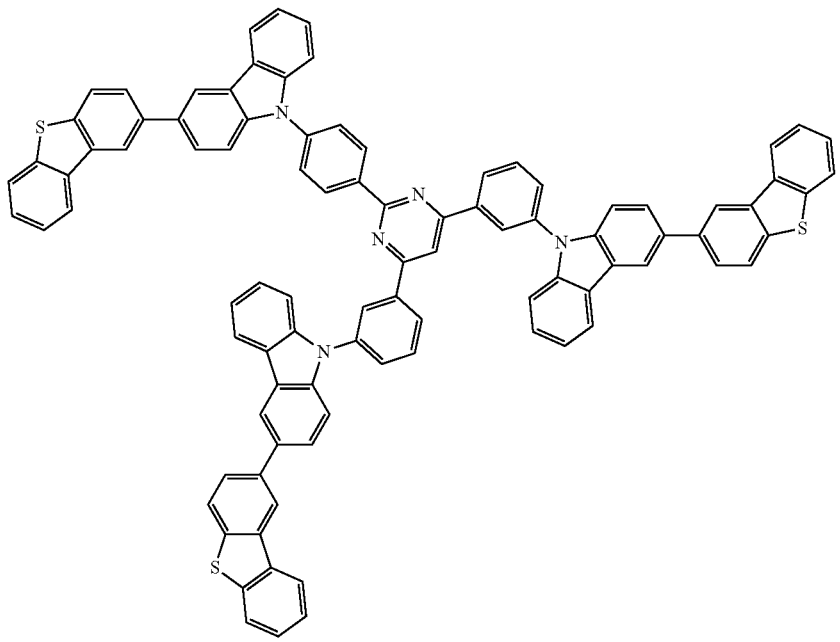
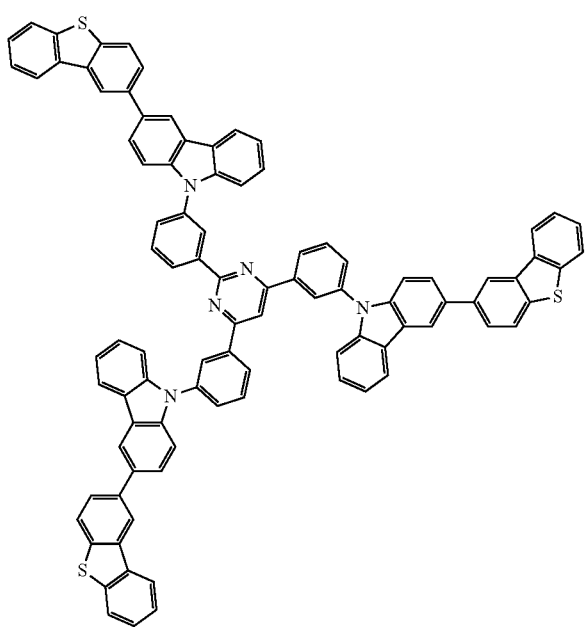

1405
1406
-continued
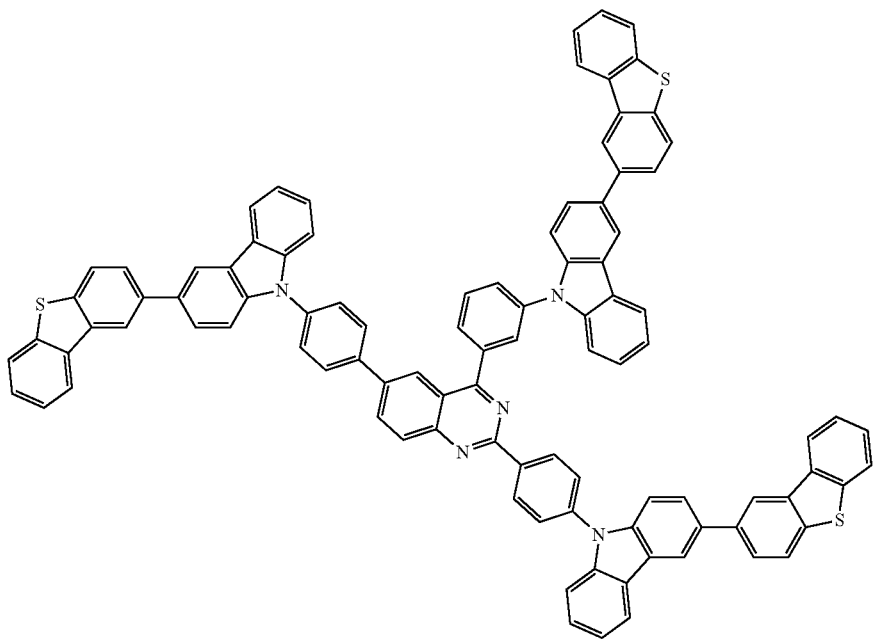
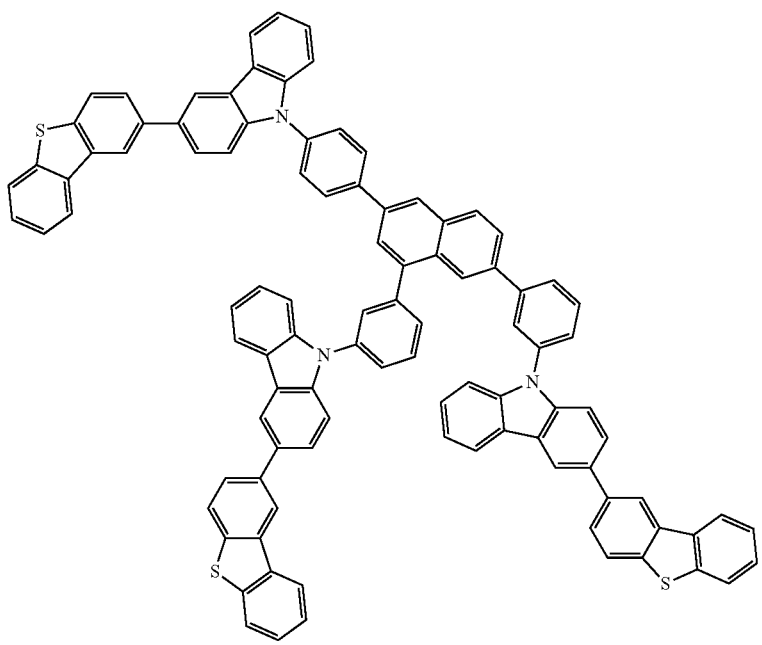

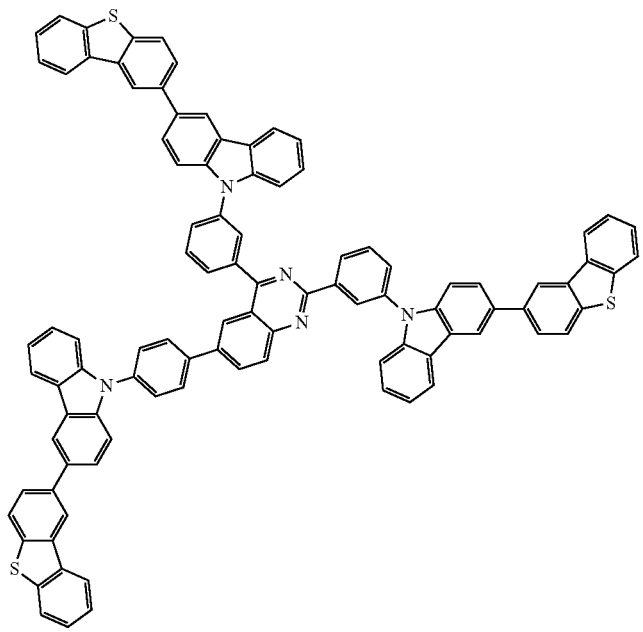
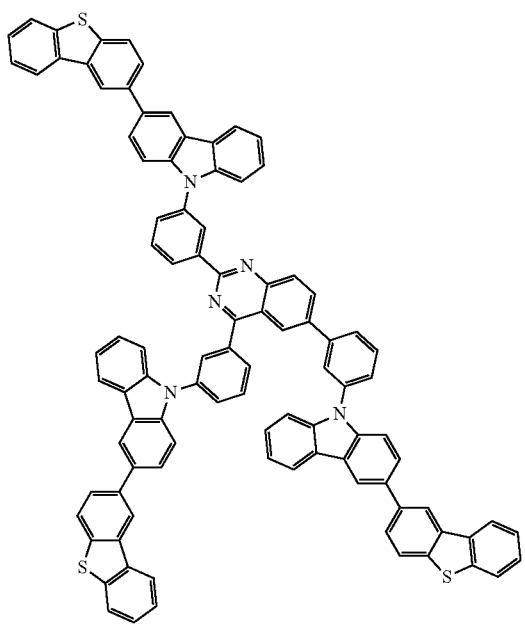

-continued
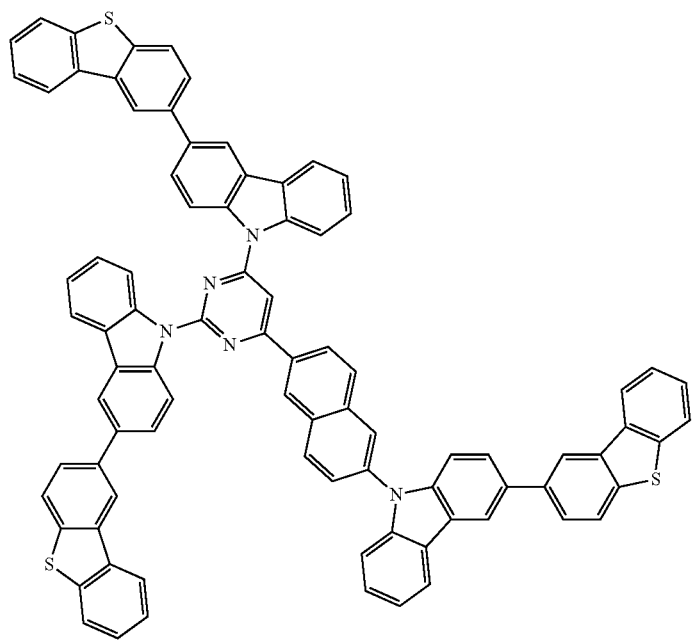
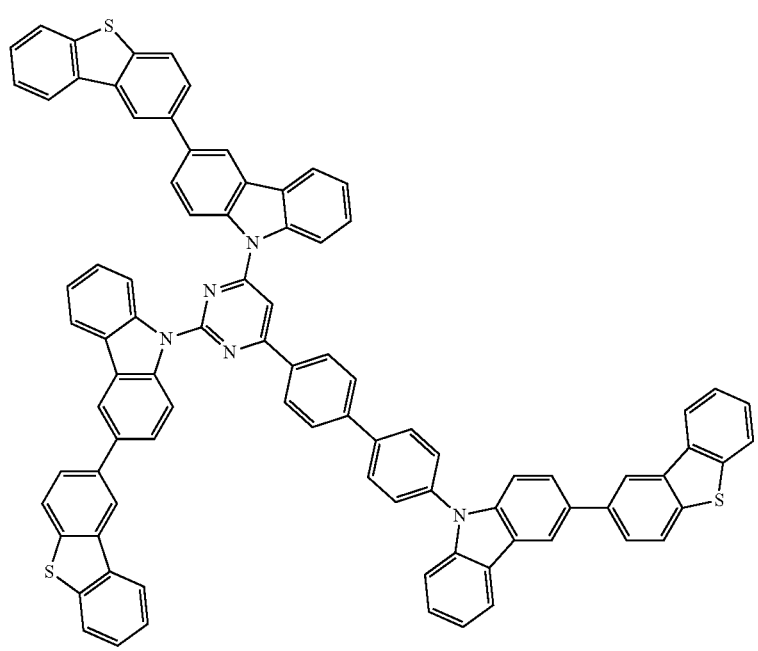

1411
1412
-continued
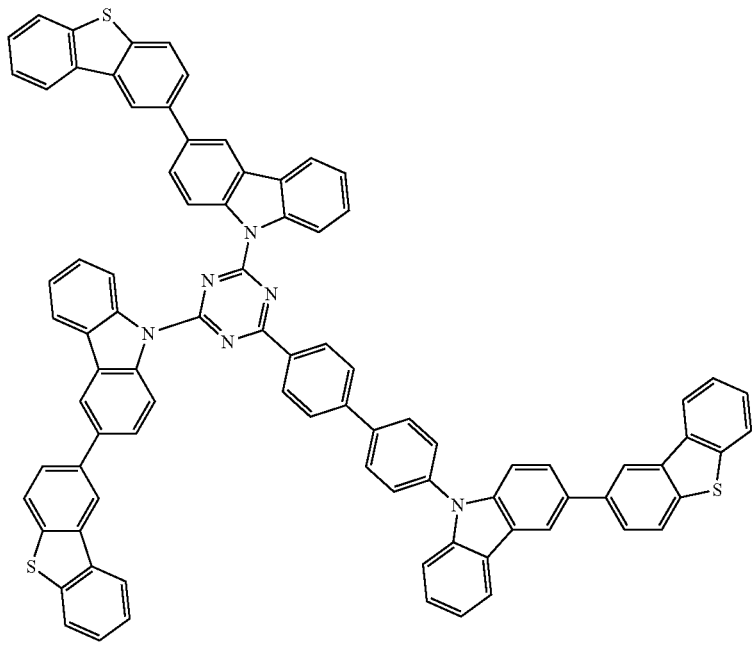
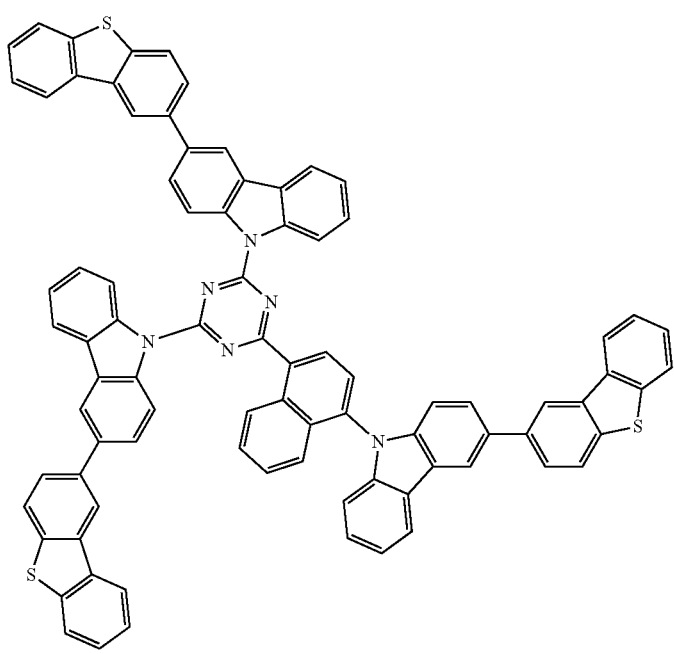

-continued
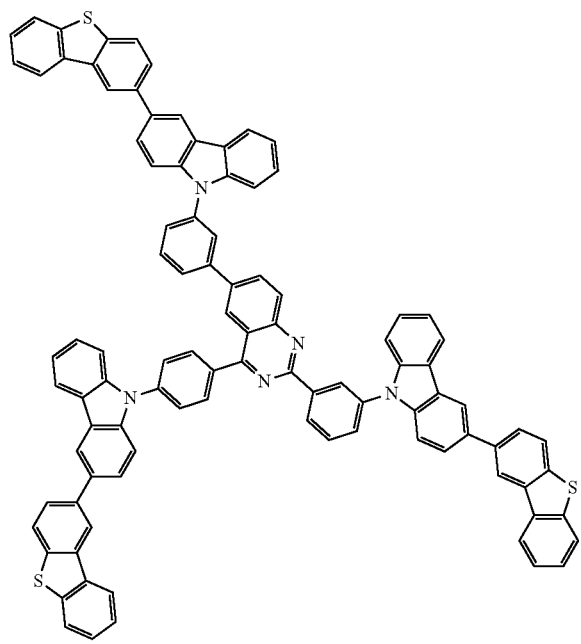
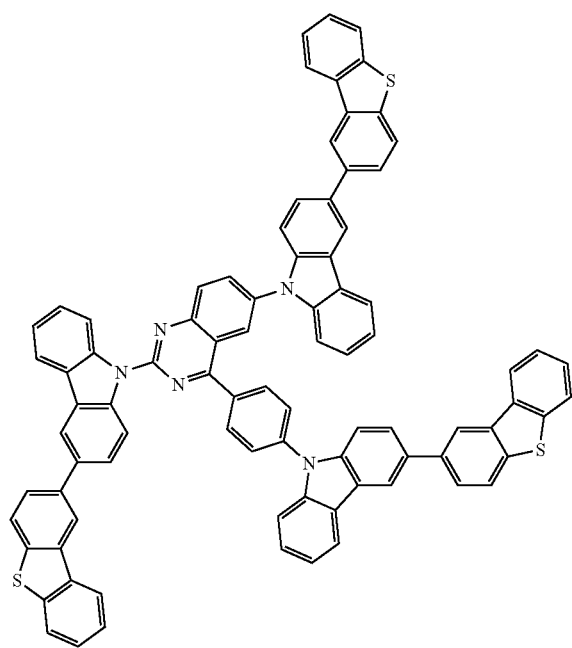

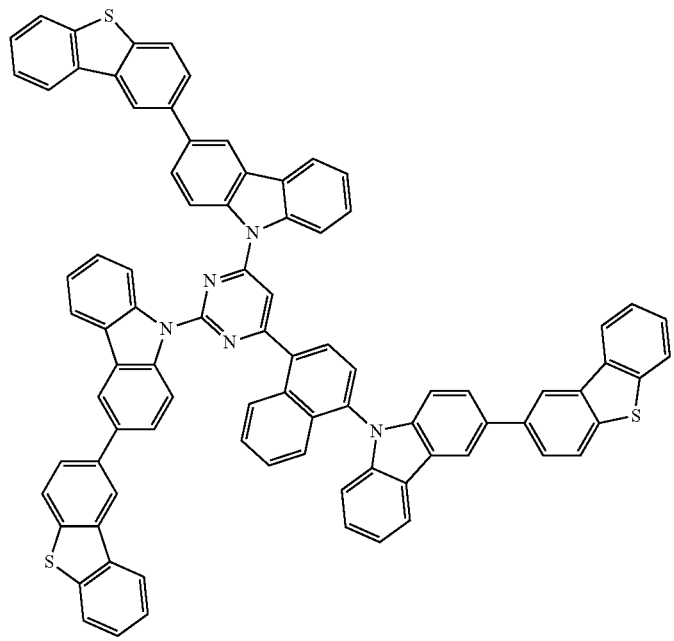
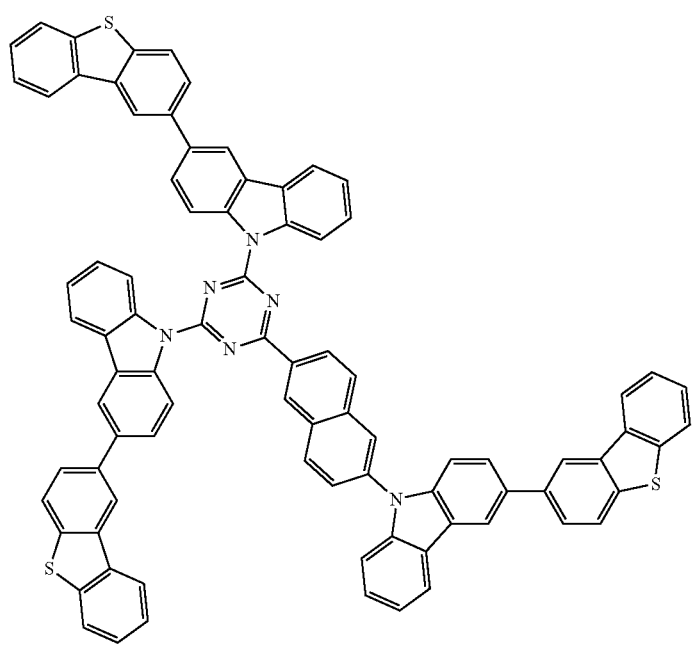

-continued
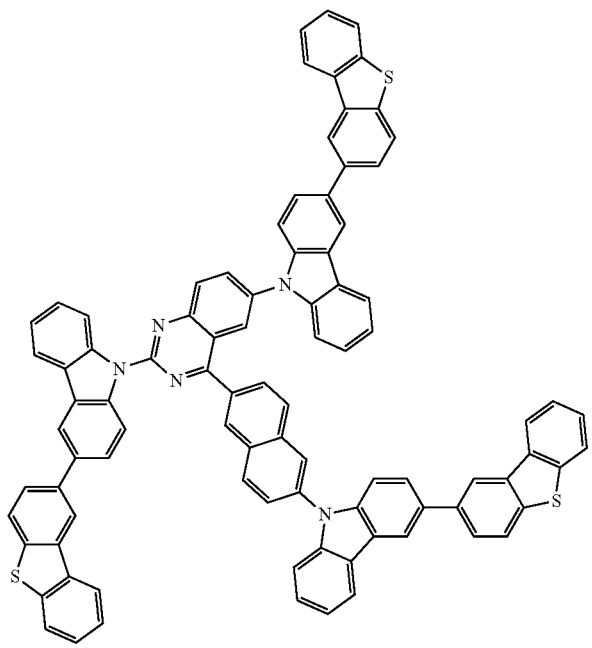
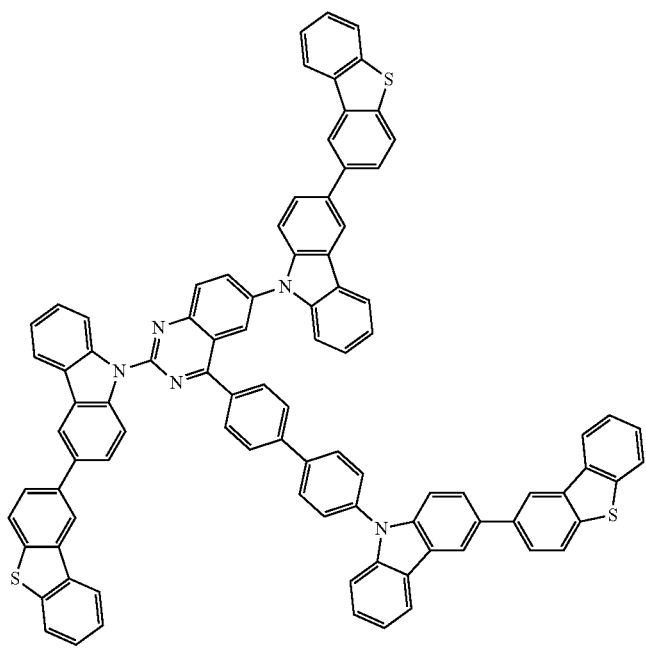

1419 1420
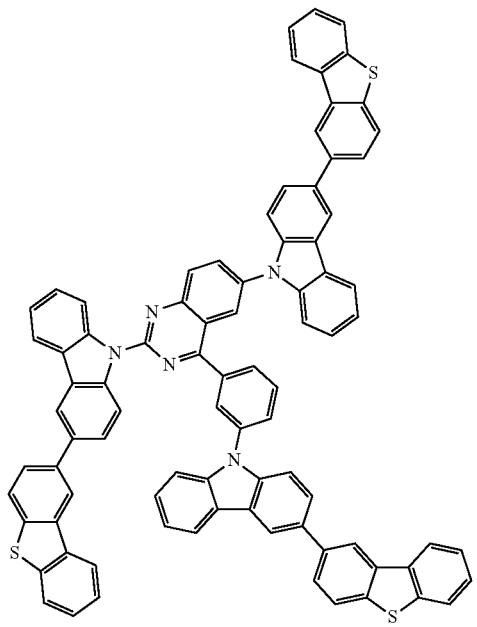
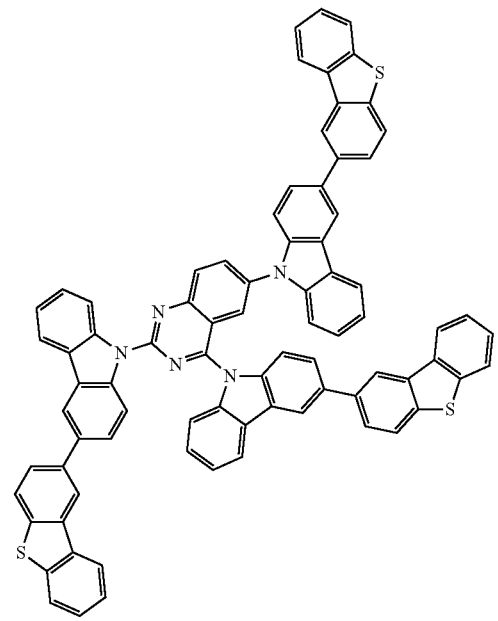
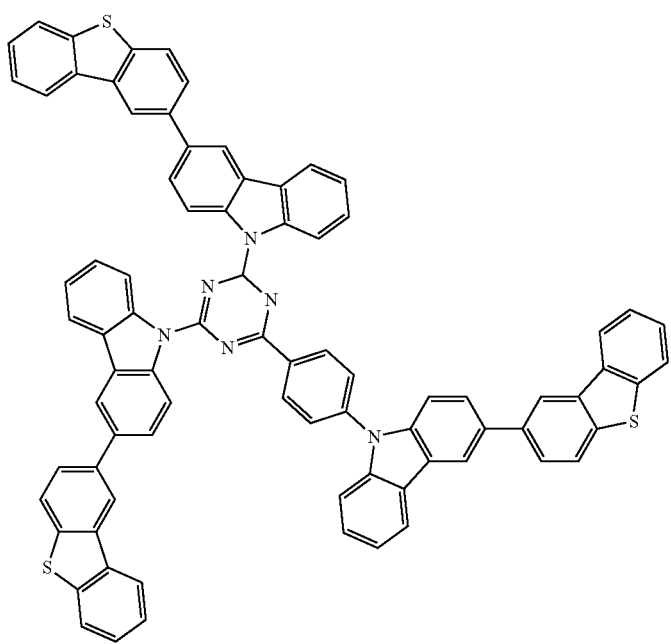

1421 1422
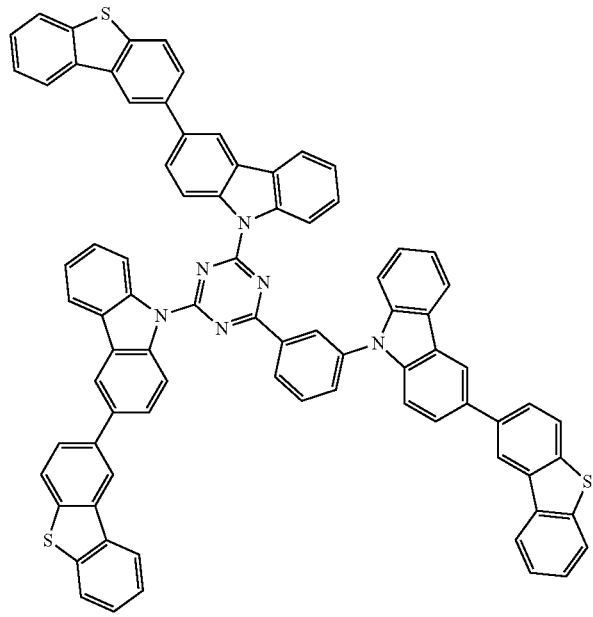 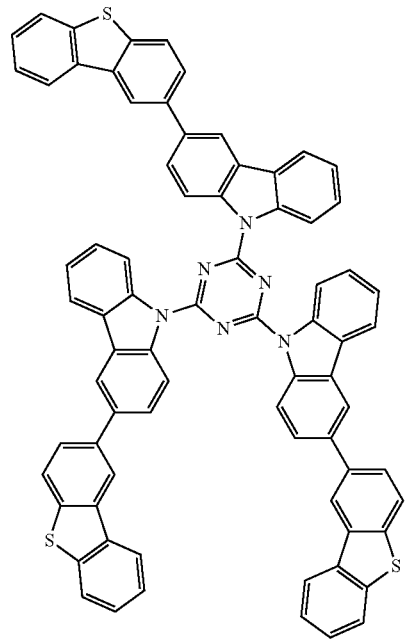
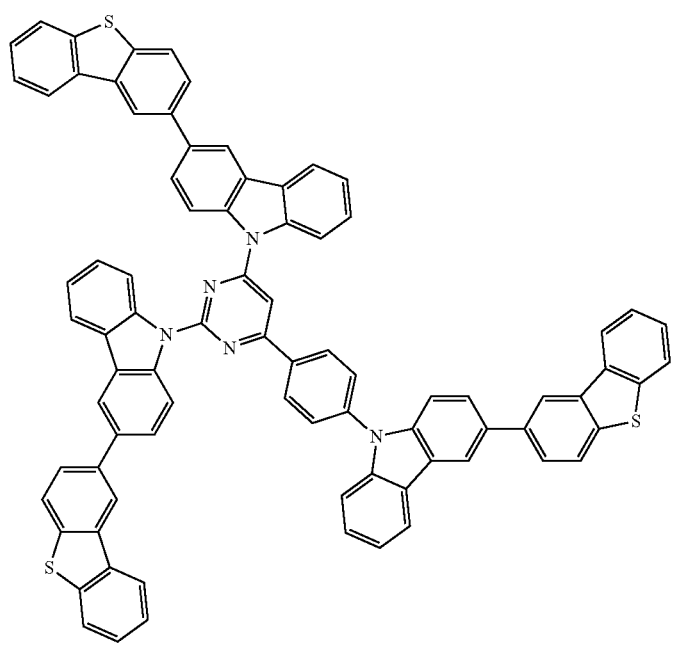

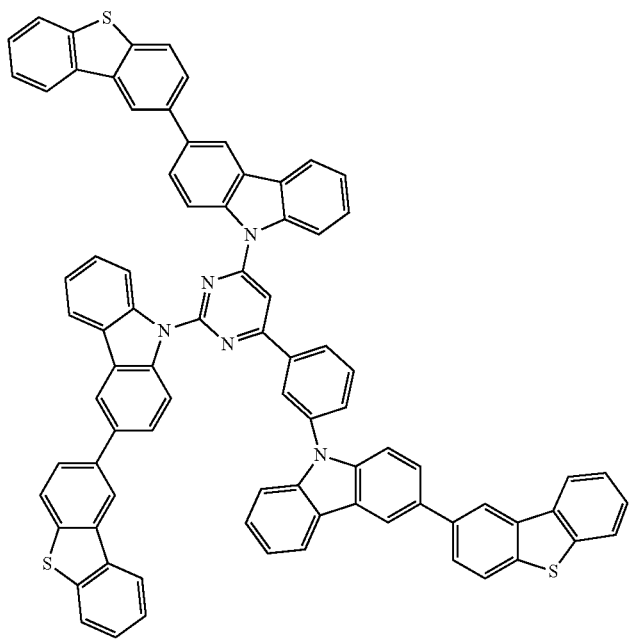
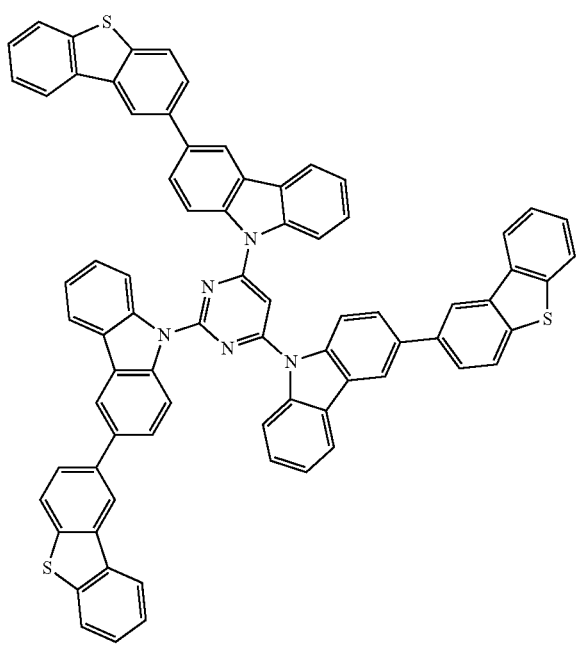

-continued
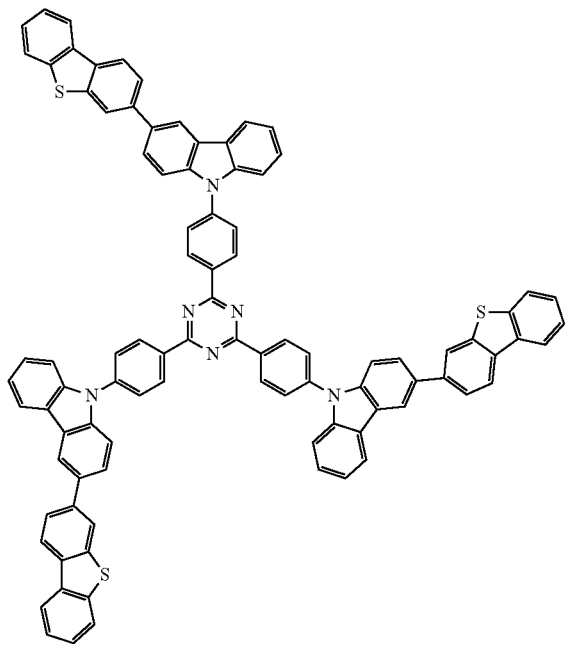
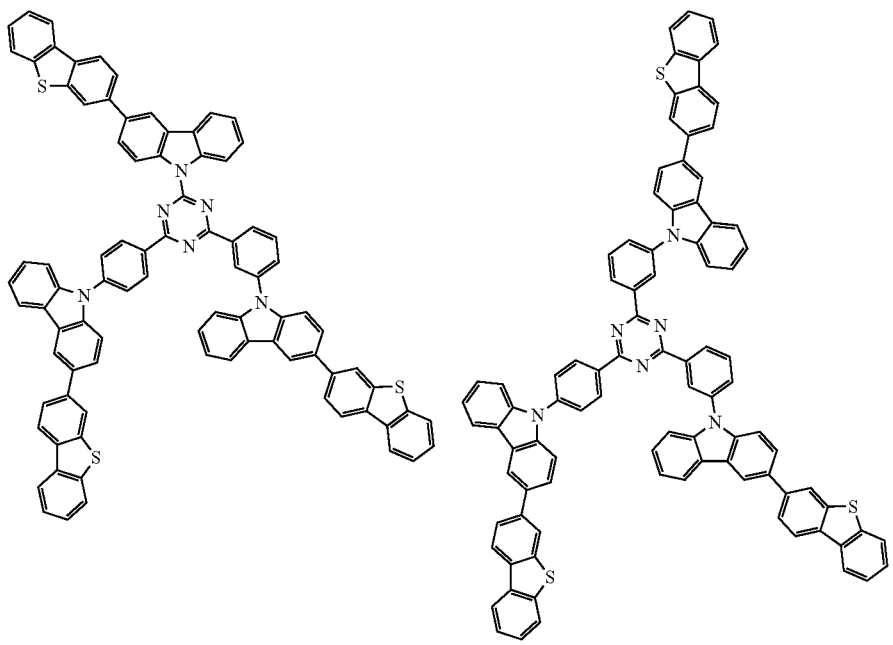

1427 1428
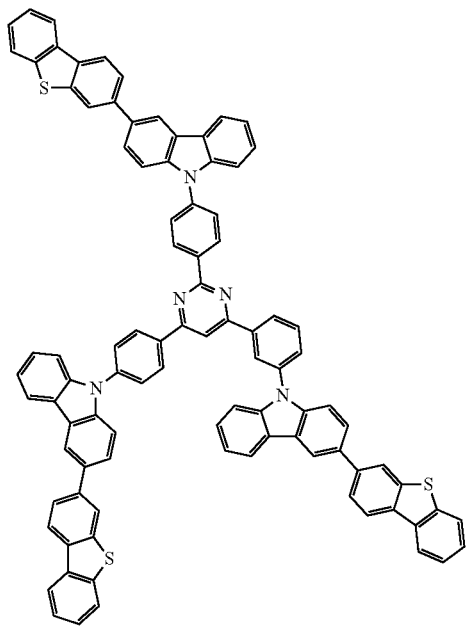
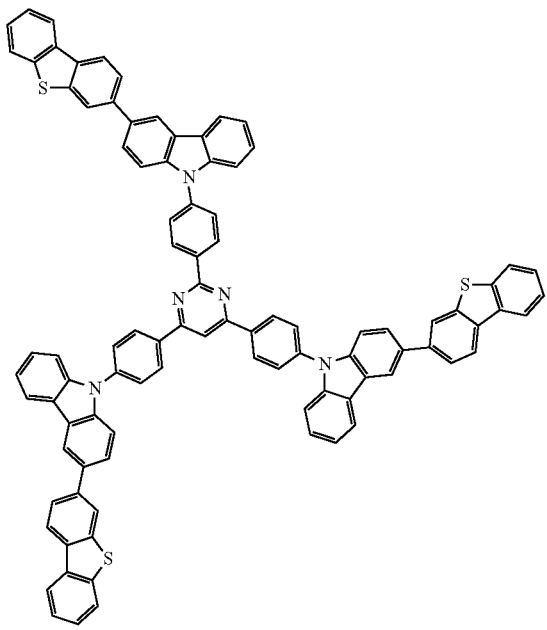
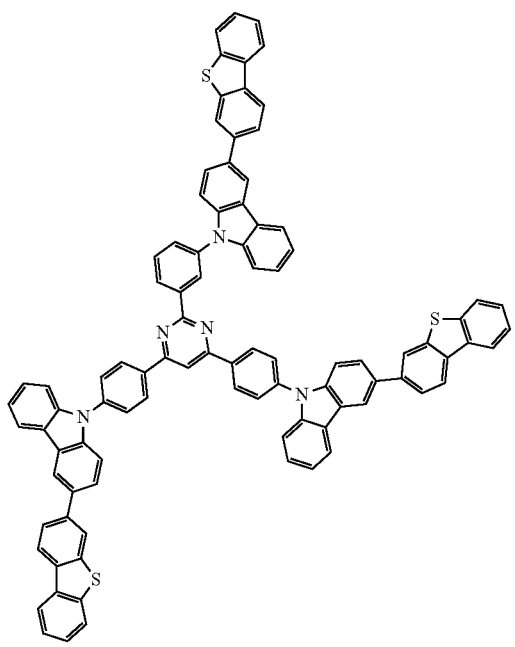
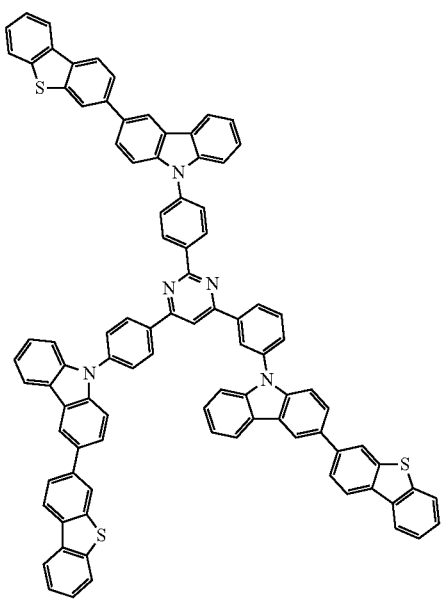

1429
1430
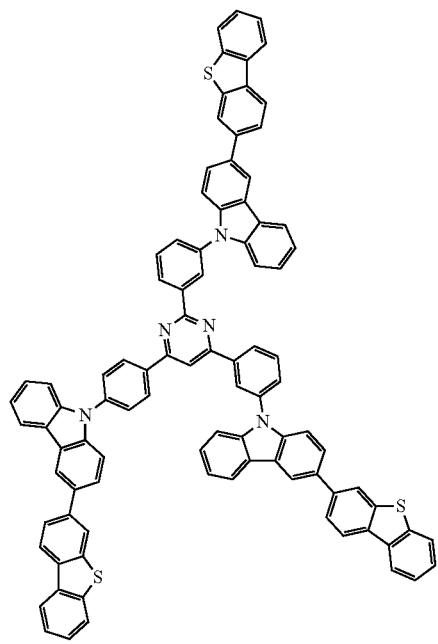
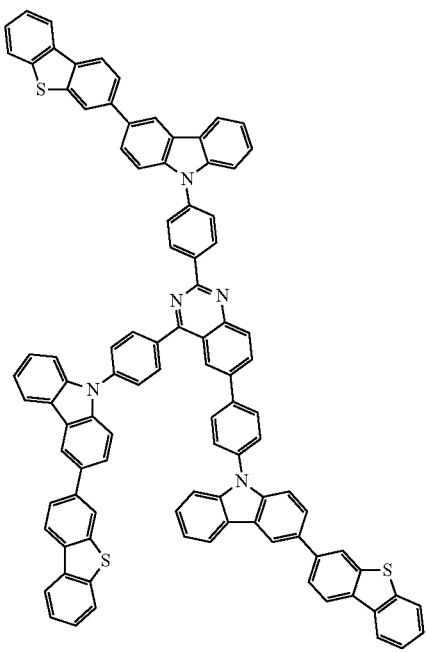
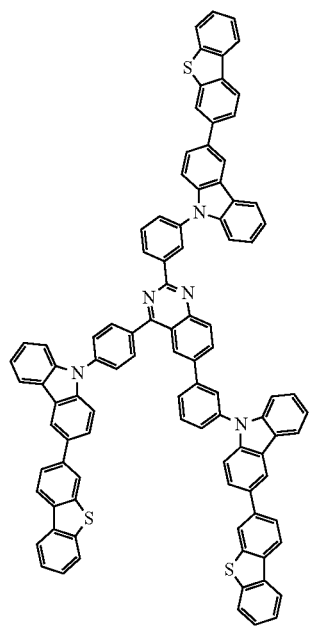
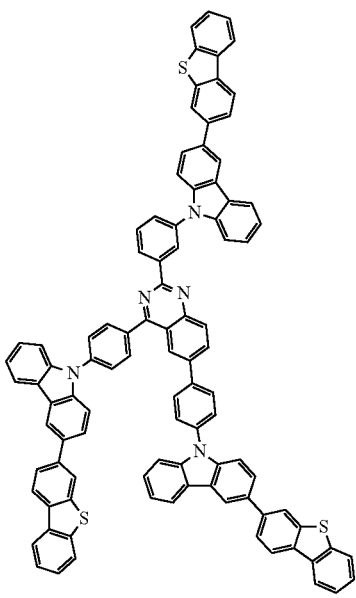

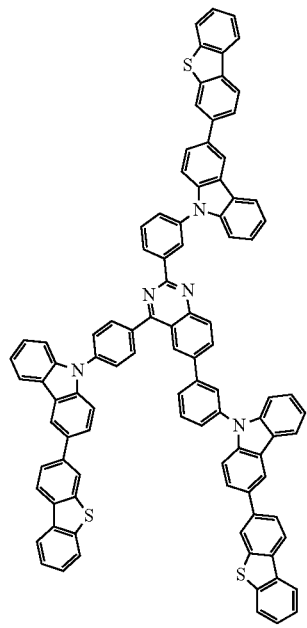
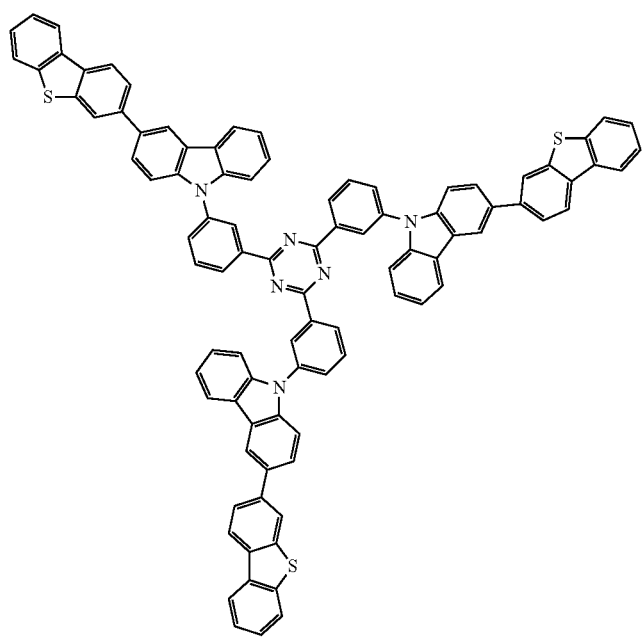

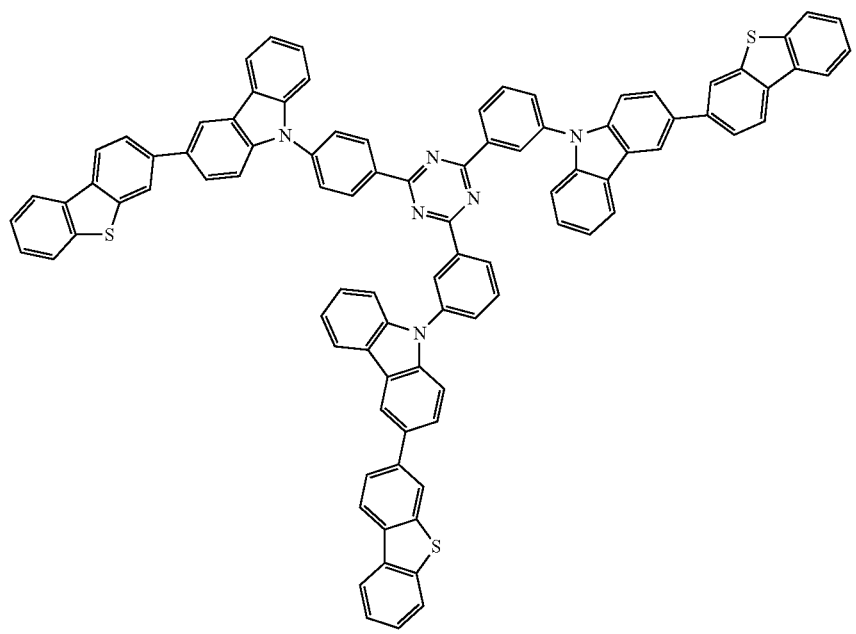
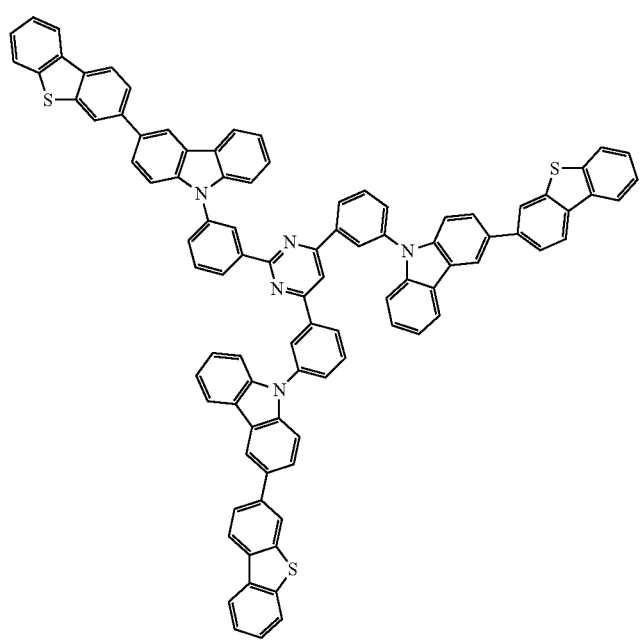

-continued
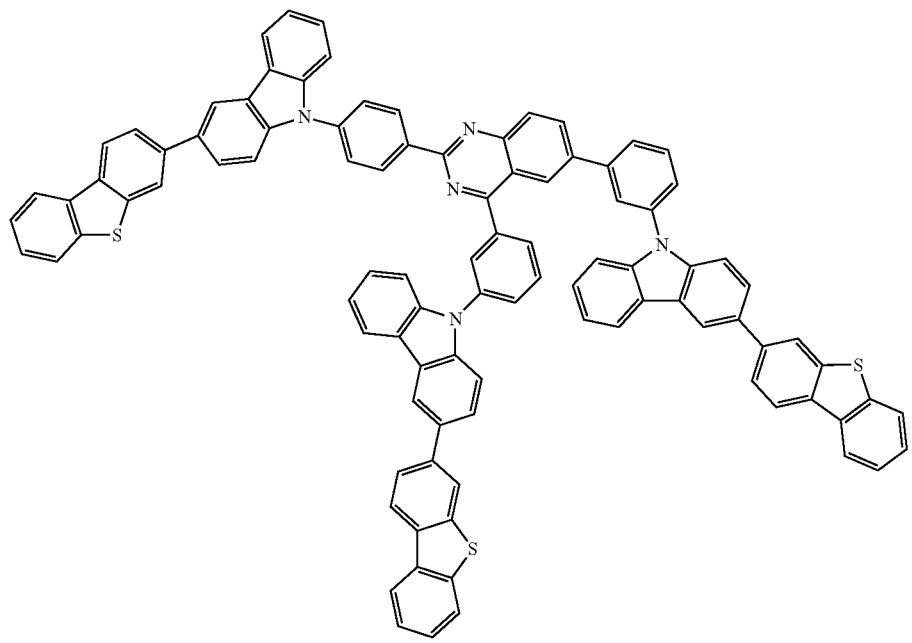
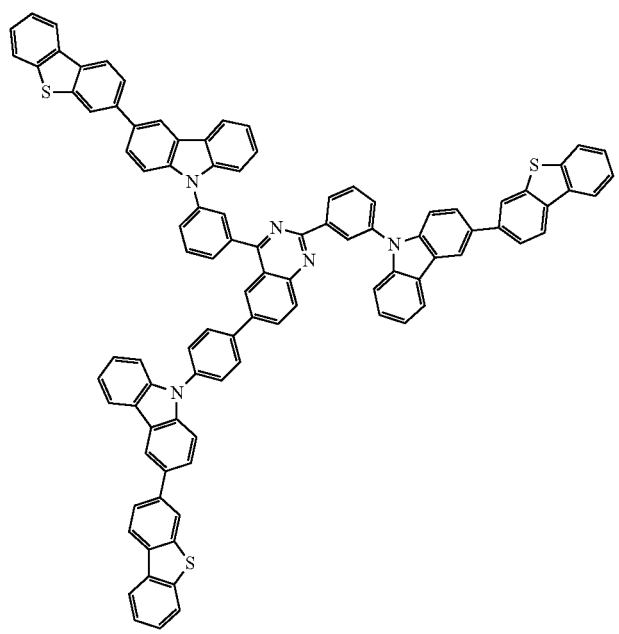

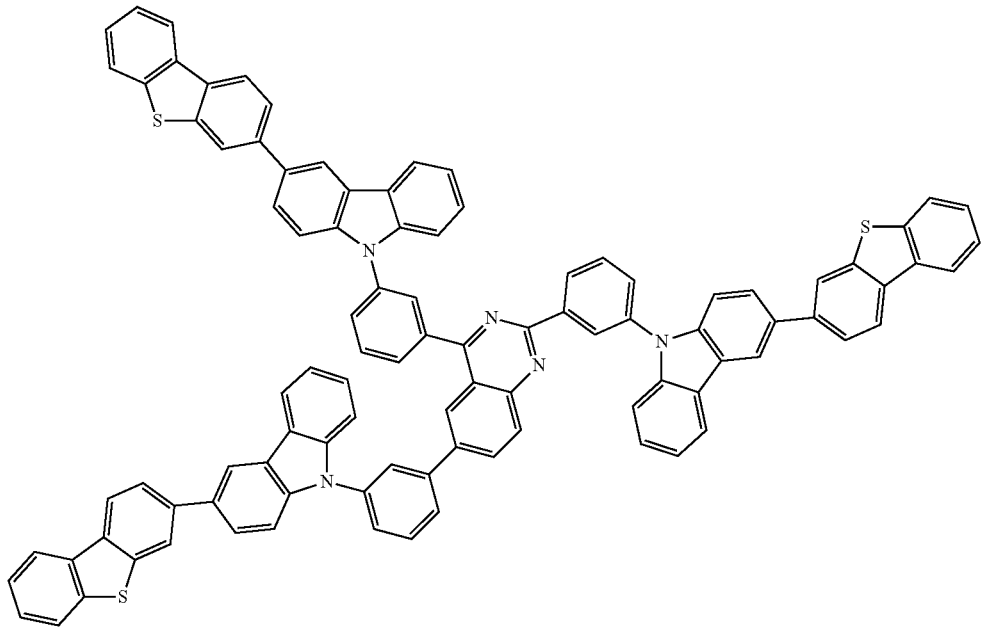
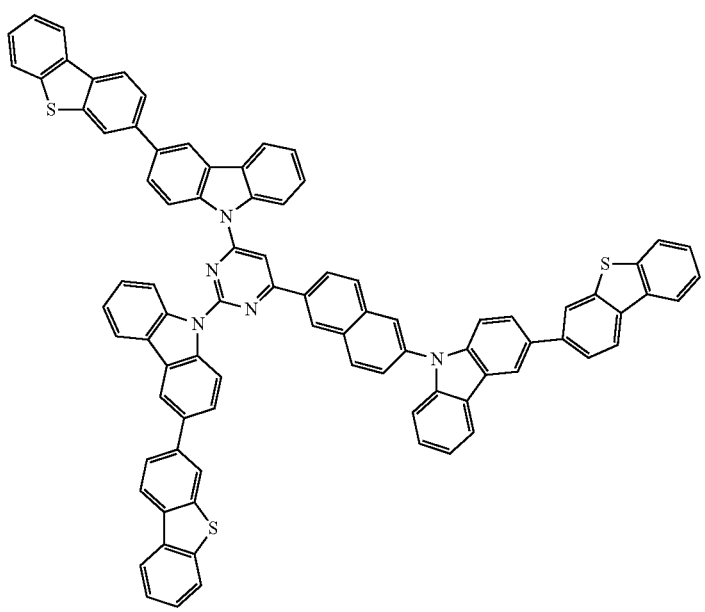

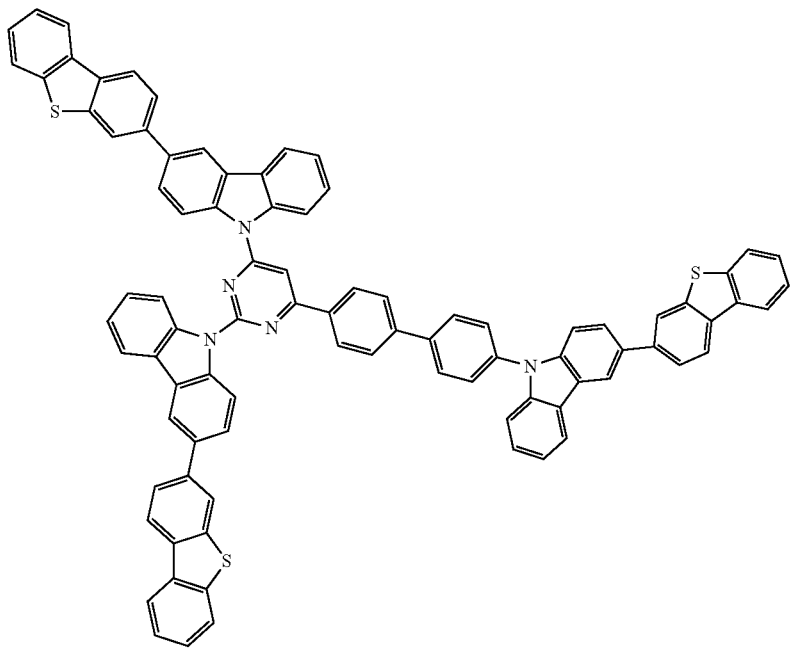
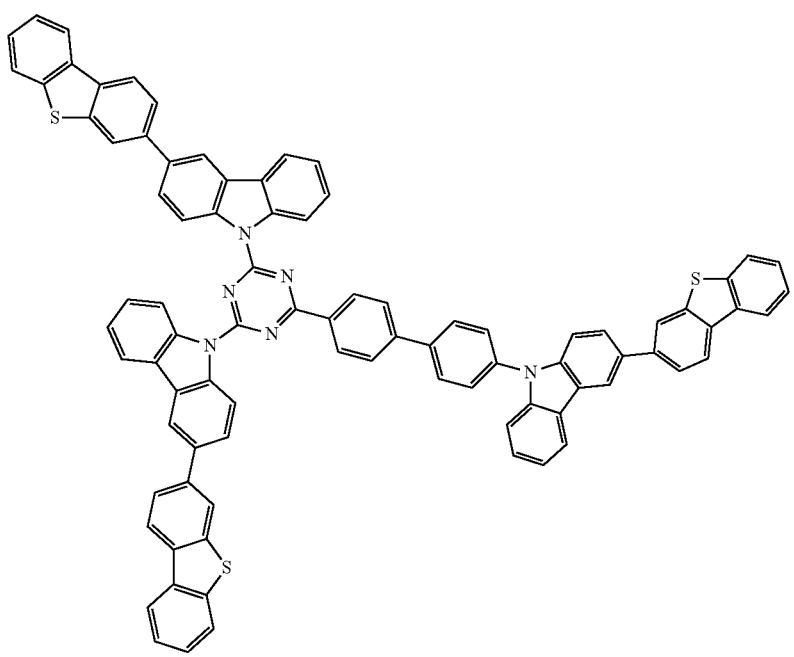

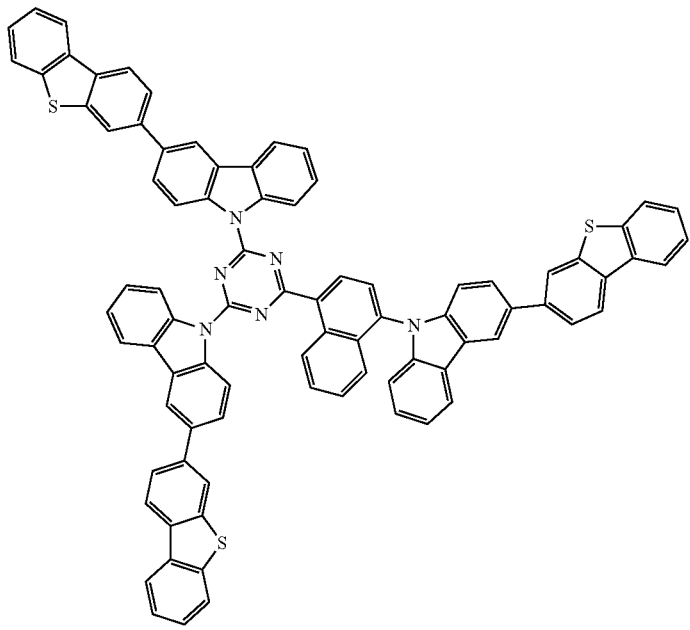
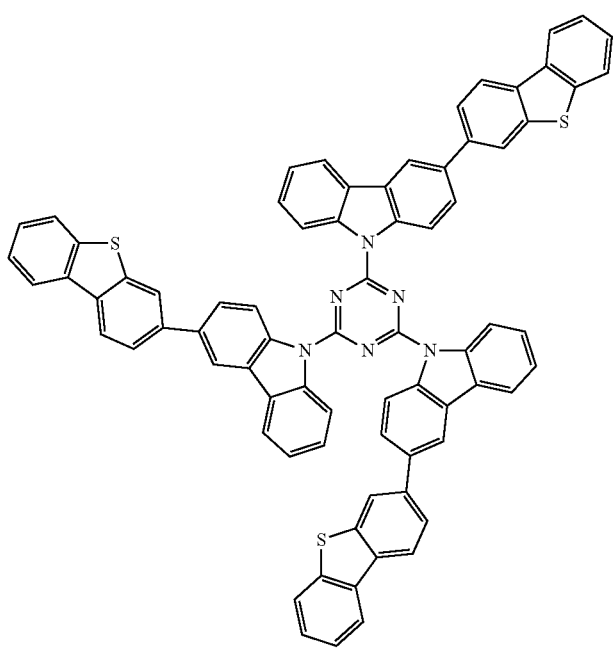

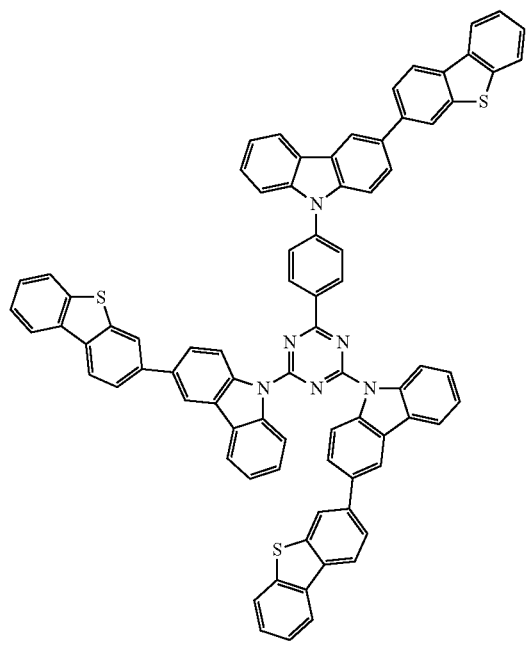
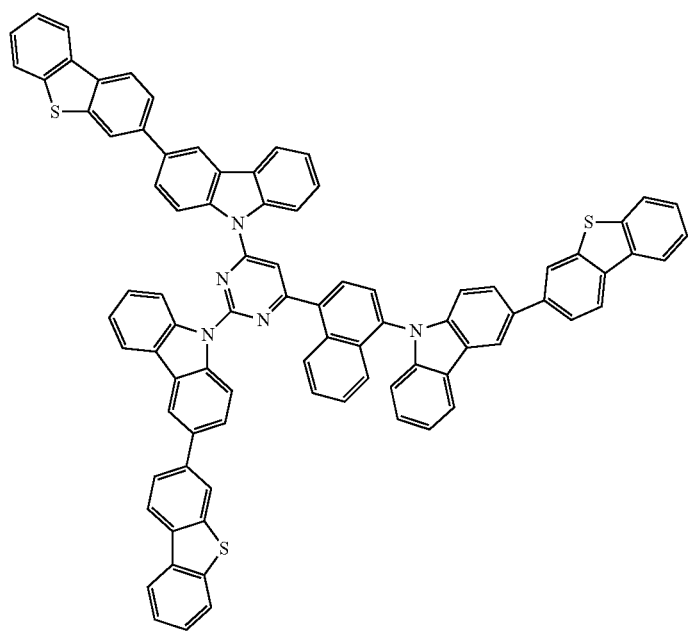

1445
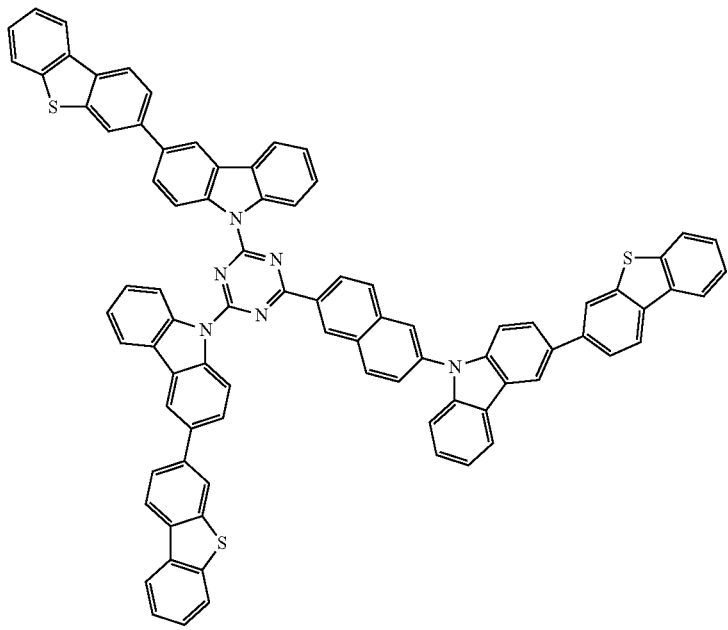
1446
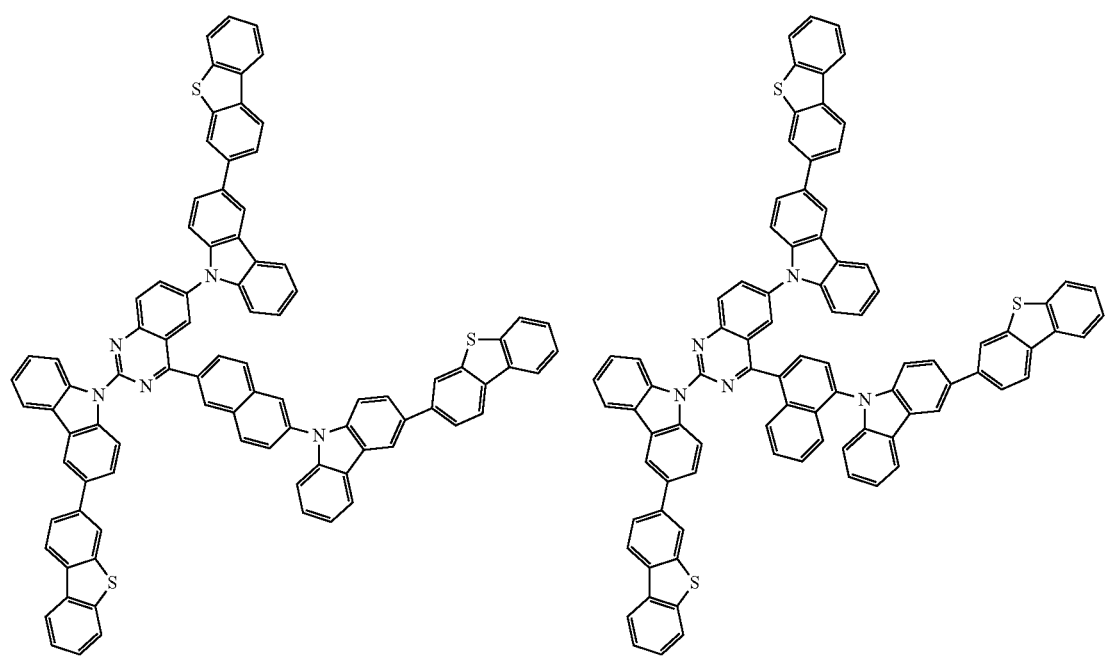

-continued
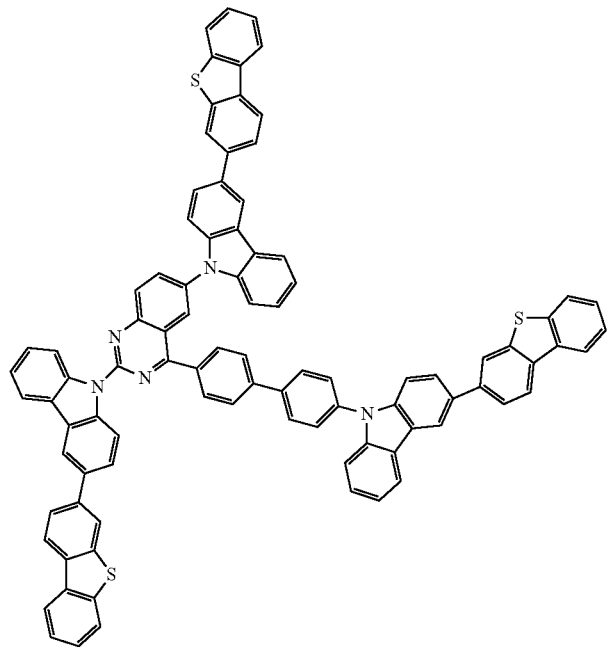 [SMILES: c1ccc2c(c1)sc1cc(-c3ccc4c(c3)c3ccccc3n4-c3ccc(-c4ccc(-c5nc(-n6c7ccccc7c7cc(-c8ccc9c(c8)sc8ccccc89)ccc76)nc6ccc(-n7c8ccccc8c8cc(-c9ccc%10c(c9)sc9ccccc9%10)ccc87)cc56)cc4)cc3)ccc12]
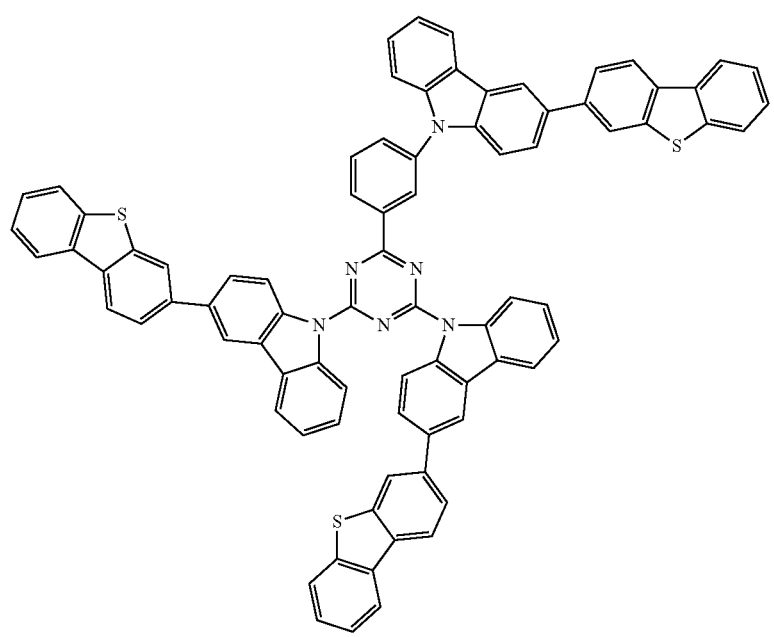

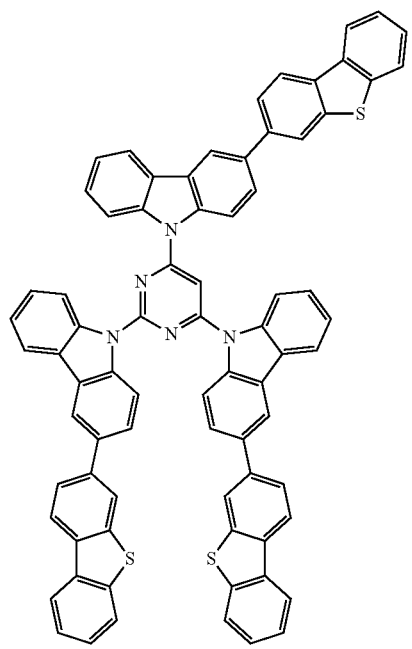
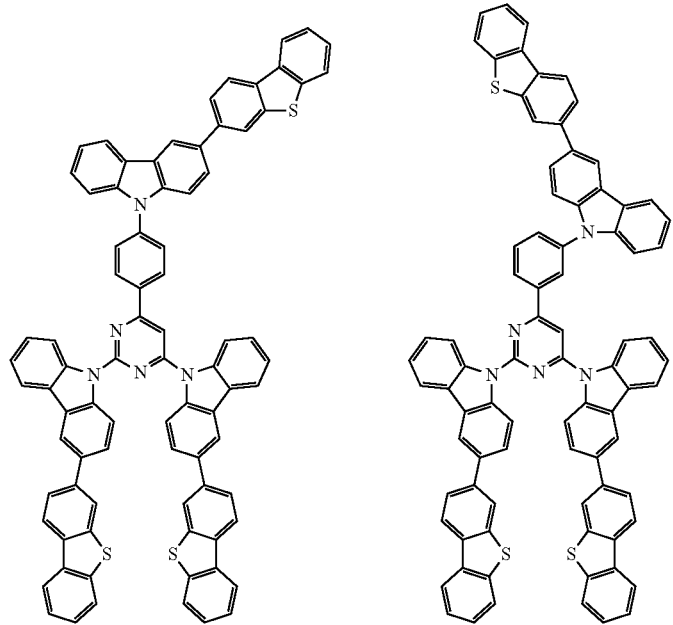

1451
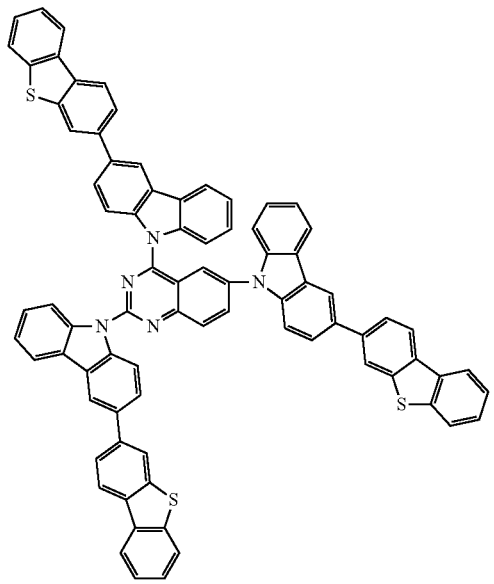
1452
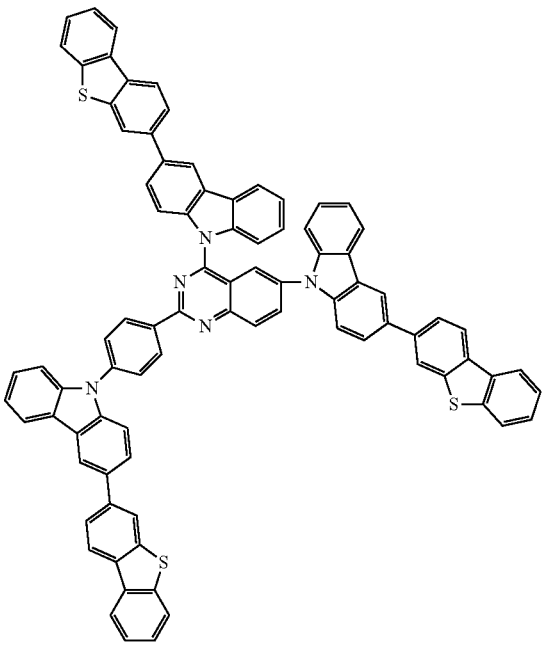
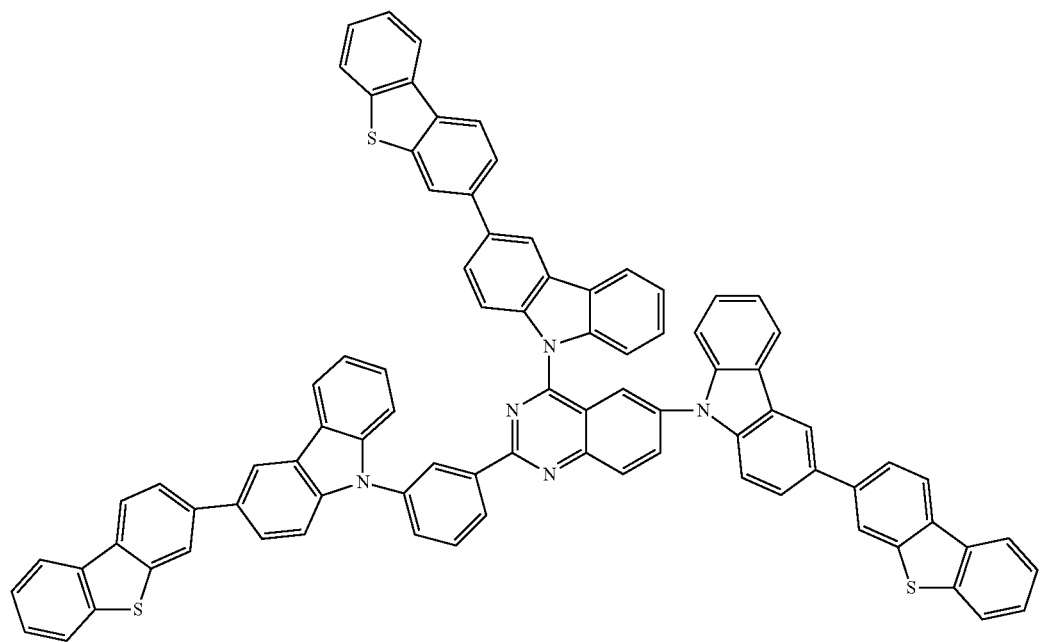 [SMILES: c1cc(-c2nc(-n3c4ccccc4c4cc(-c5ccc6c(c5)sc5ccccc56)ccc43)c3cc(-n4c5ccccc5c5cc(-c6ccc7c(c6)sc6ccccc67)ccc54)ccc3n2)cc(-n2c3ccccc3c3cc(-c4ccc5c(c4)sc4ccccc45)ccc32)c1]

-continued
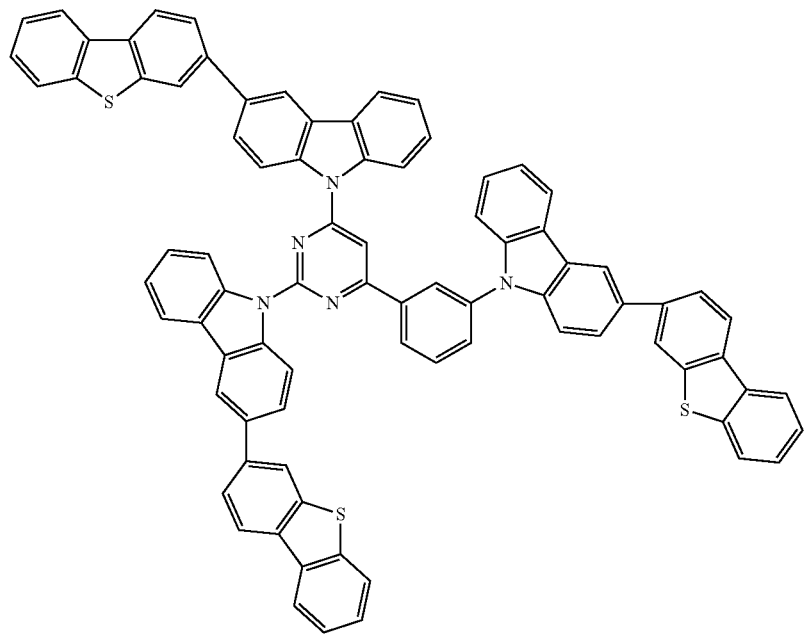
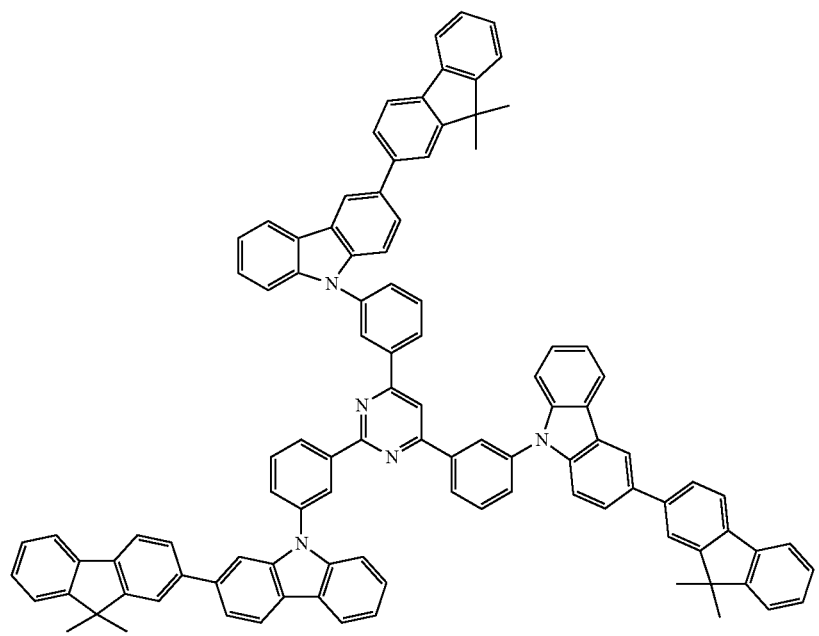

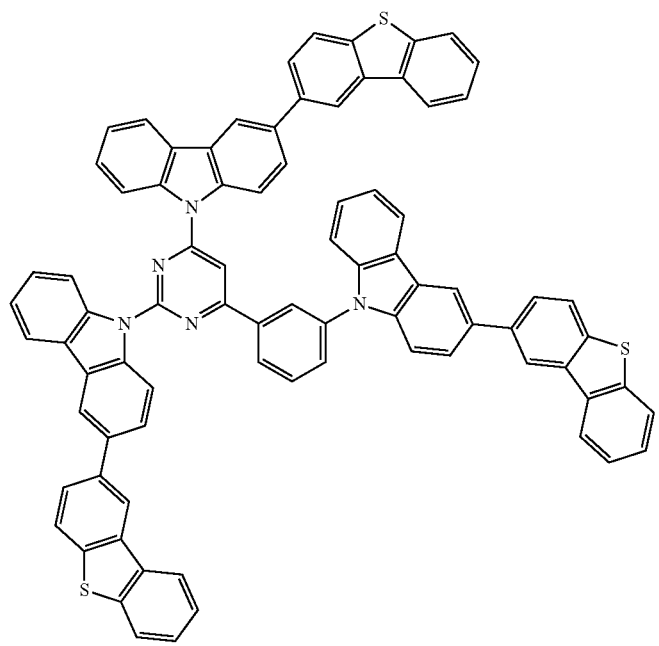
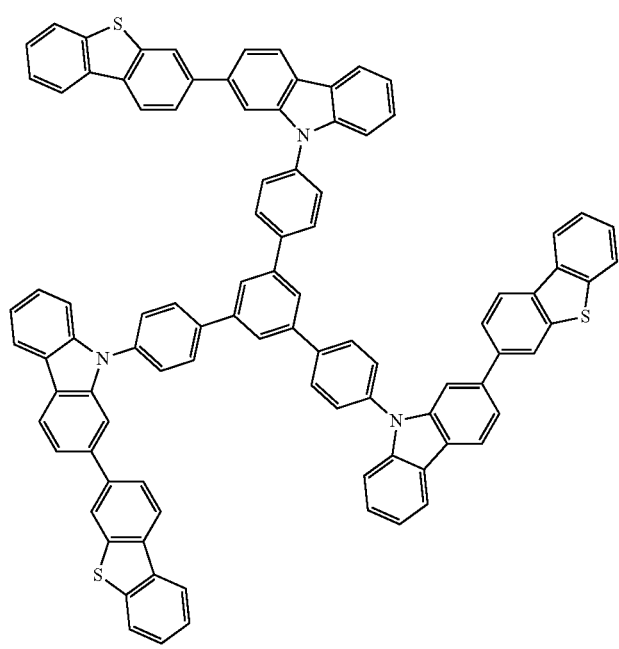

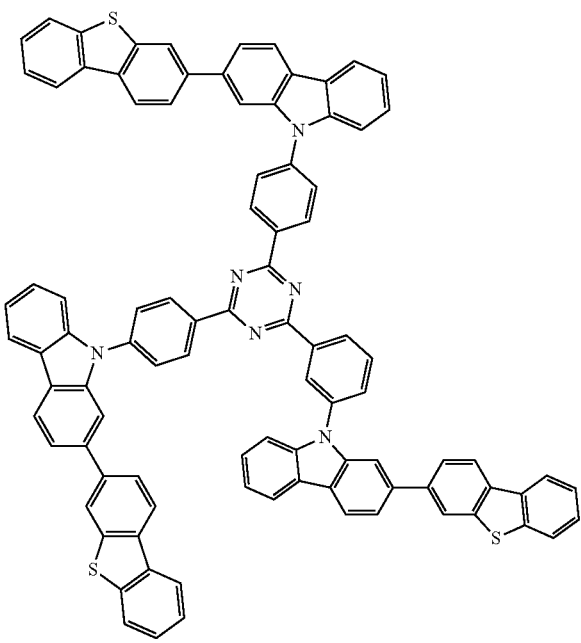
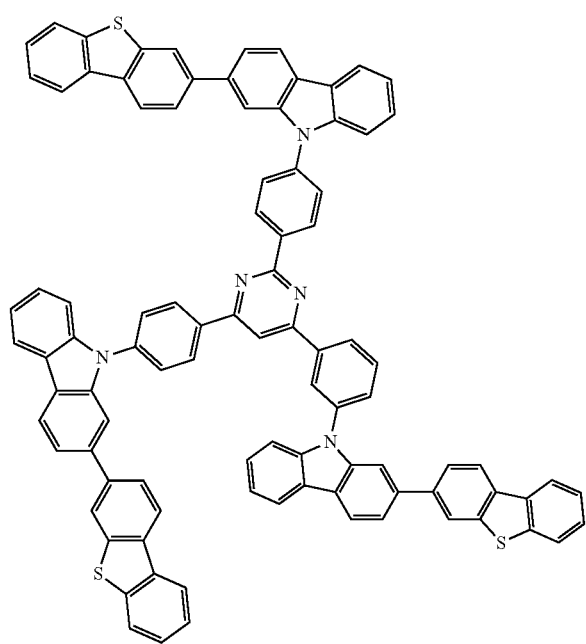

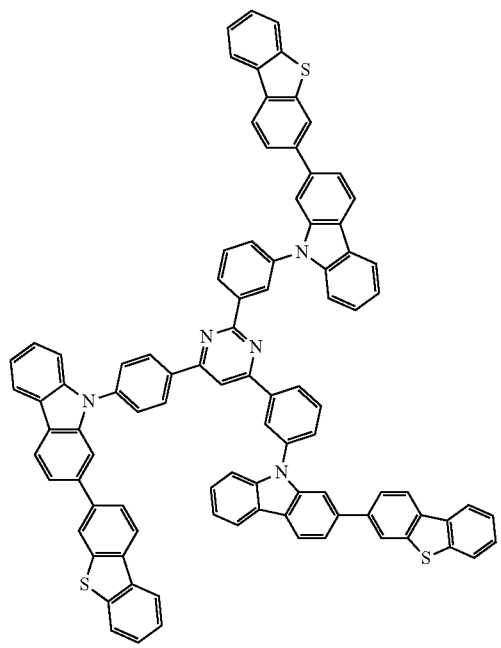
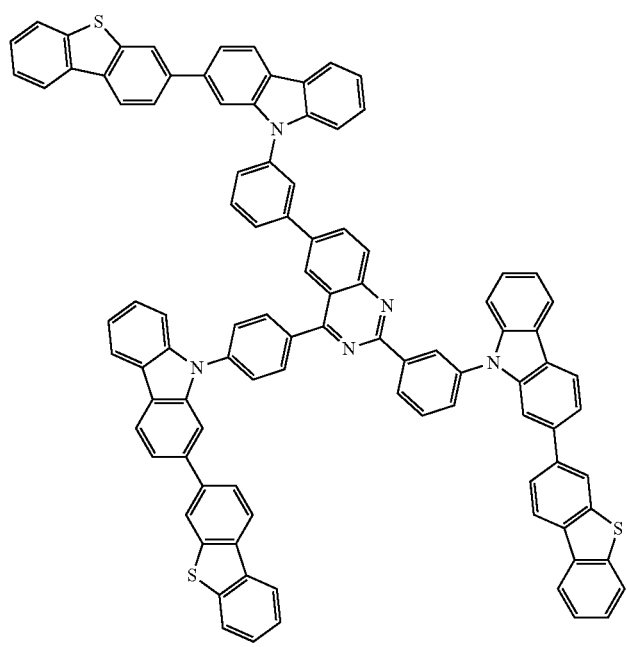

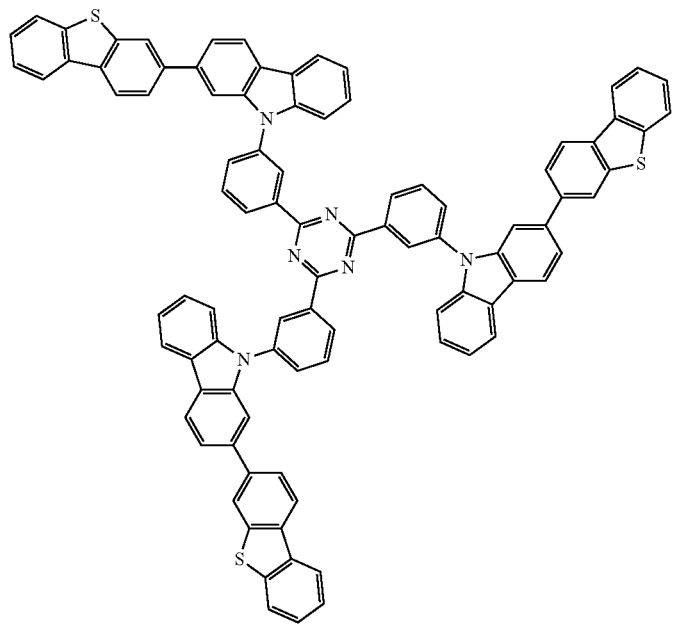
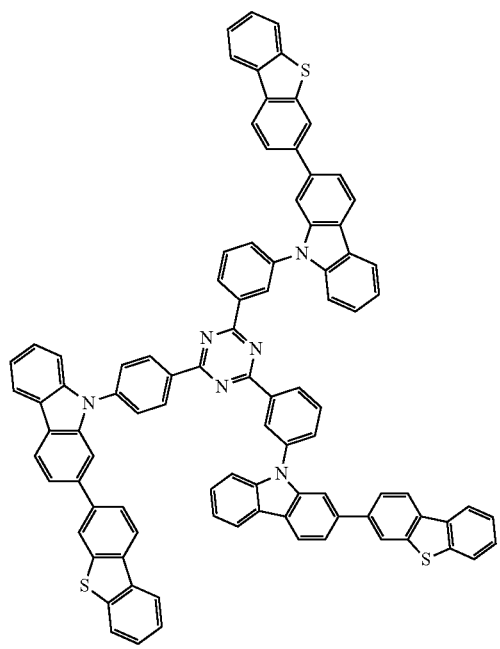

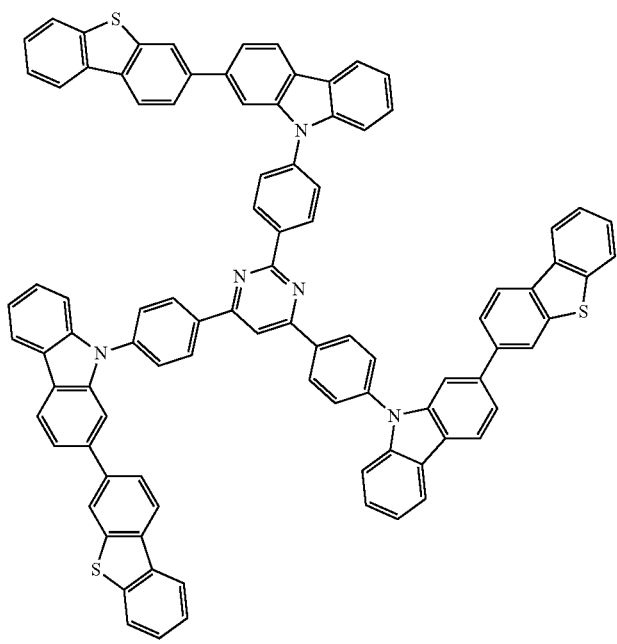
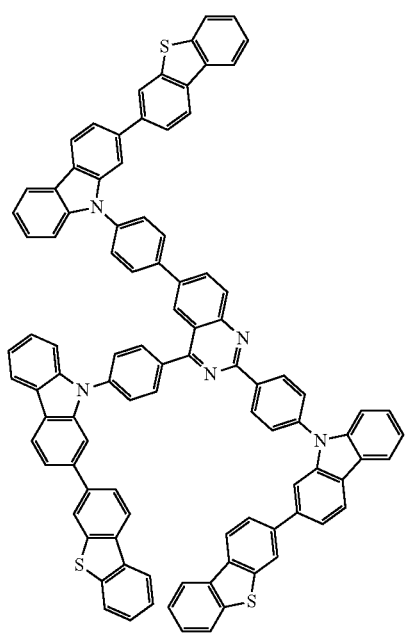

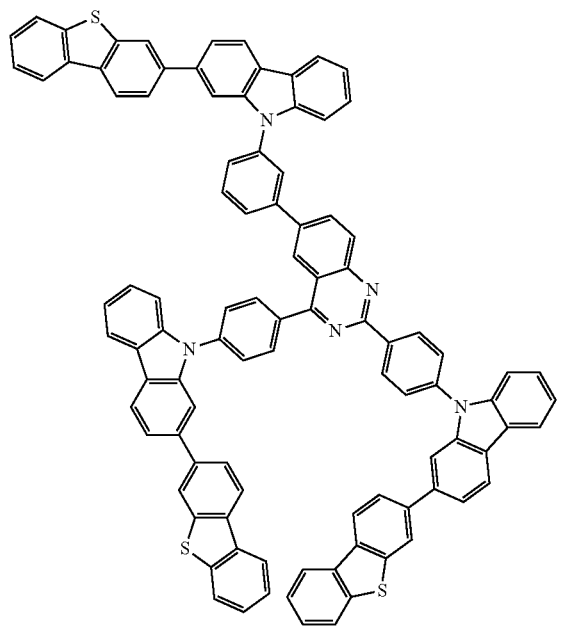
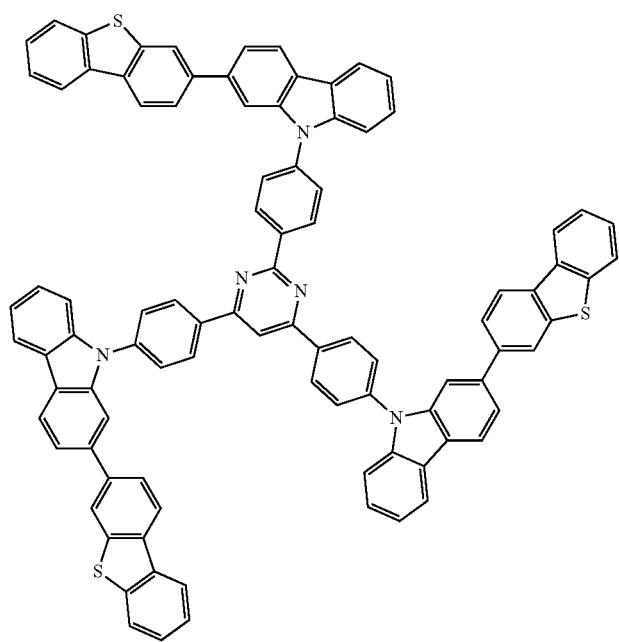

1467
1468
-continued
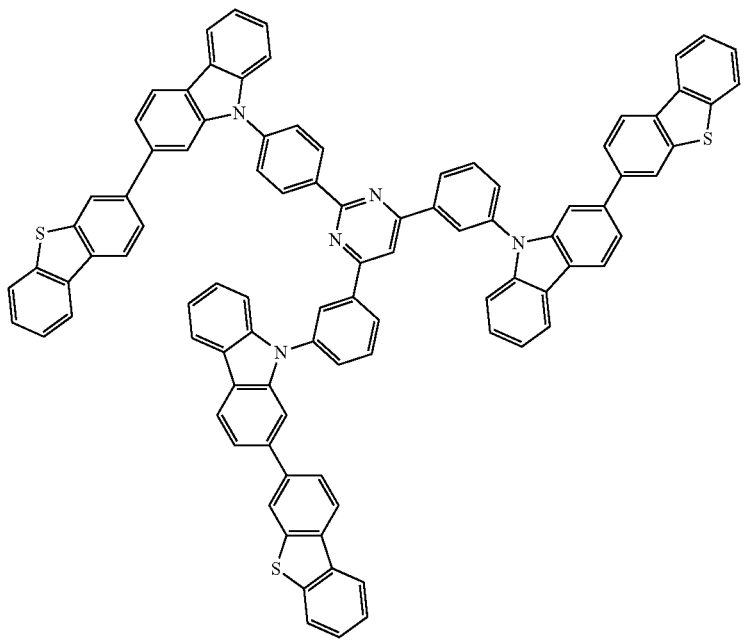
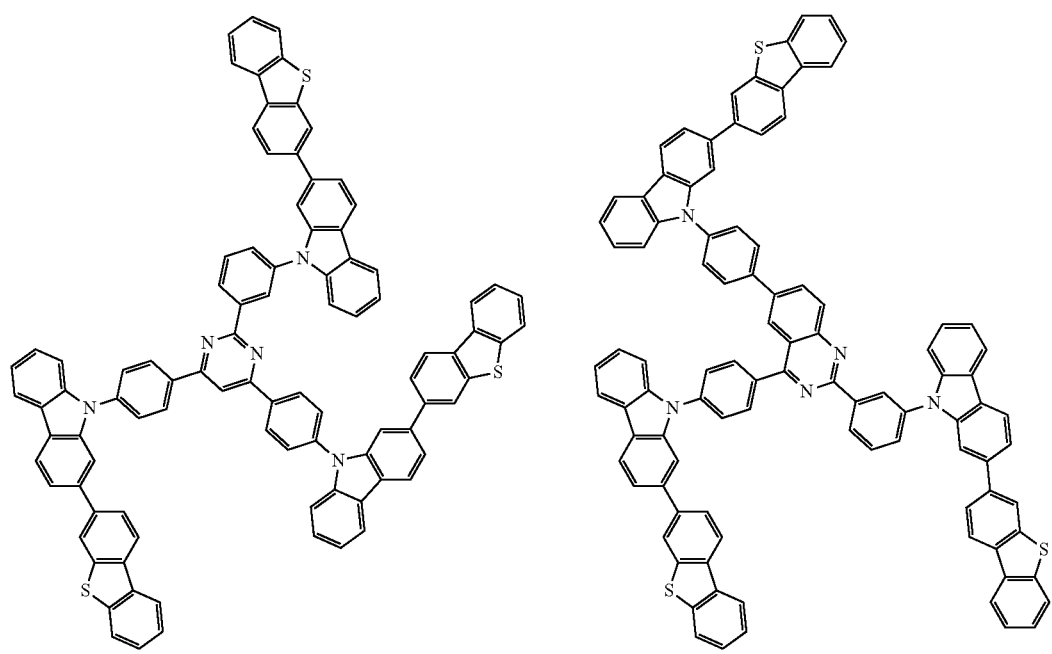 [SMILES: c1cc(-c2nc(-c3ccc(-n4c5ccccc5c5ccc(-c6ccc7c(c6)sc6ccccc67)cc54)cc3)cc(-c3ccc(-n4c5ccccc5c5ccc(-c6ccc7c(c6)sc6ccccc67)cc54)cc3)n2)cc(-n2c3ccccc3c3ccc(-c4ccc5c(c4)sc4ccccc45)cc32)c1 ; c1cc(-c2nc(-c3ccc(-n4c5ccccc5c5ccc(-c6ccc7c(c6)sc6ccccc67)cc54)cc3)c3cc(-c4ccc(-n5c6ccccc6c6ccc(-c7ccc8c(c7)sc7ccccc78)cc65)cc4)ccc3n2)cc(-n2c3ccccc3c3ccc(-c4ccc5c(c4)sc4ccccc45)cc32)c1]

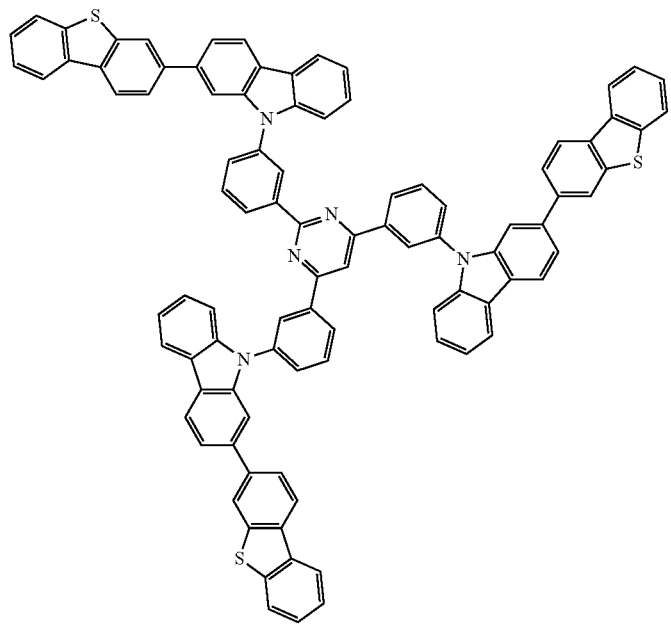 [SMILES: c1cc(-c2cc(-c3cccc(-n4c5ccccc5c5ccc(-c6ccc7c(c6)sc6ccccc67)cc54)c3)nc(-c3cccc(-n4c5ccccc5c5ccc(-c6ccc7c(c6)sc6ccccc67)cc54)c3)n2)cc(-n2c3ccccc3c3ccc(-c4ccc5c(c4)sc4ccccc45)cc32)c1]
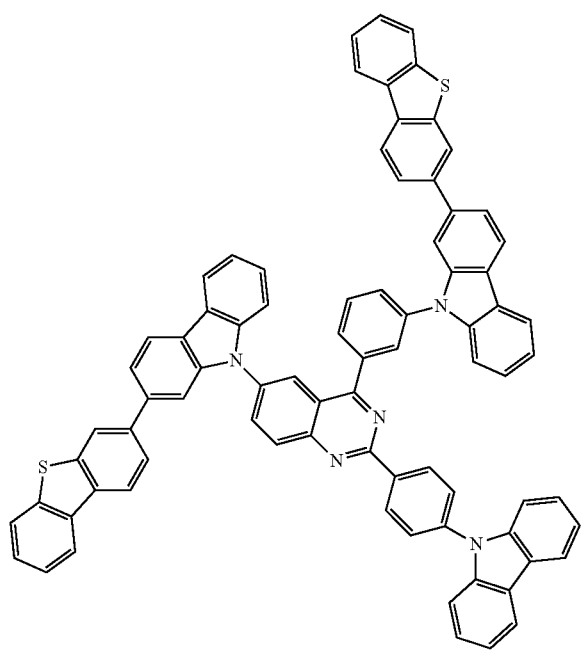

-continued
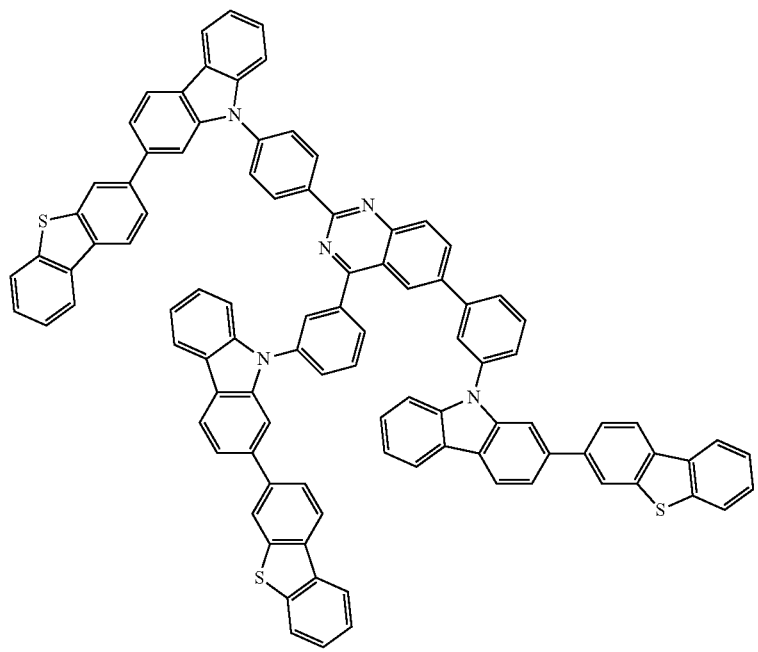
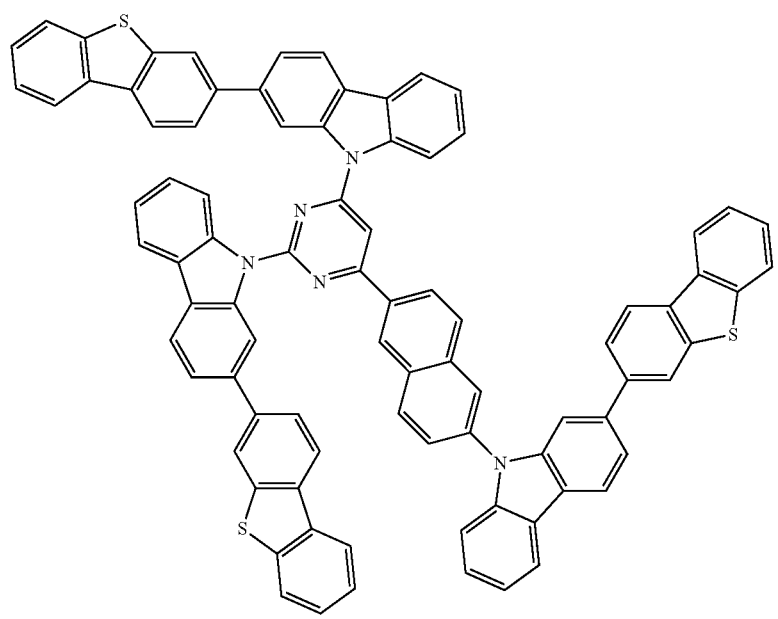

-continued
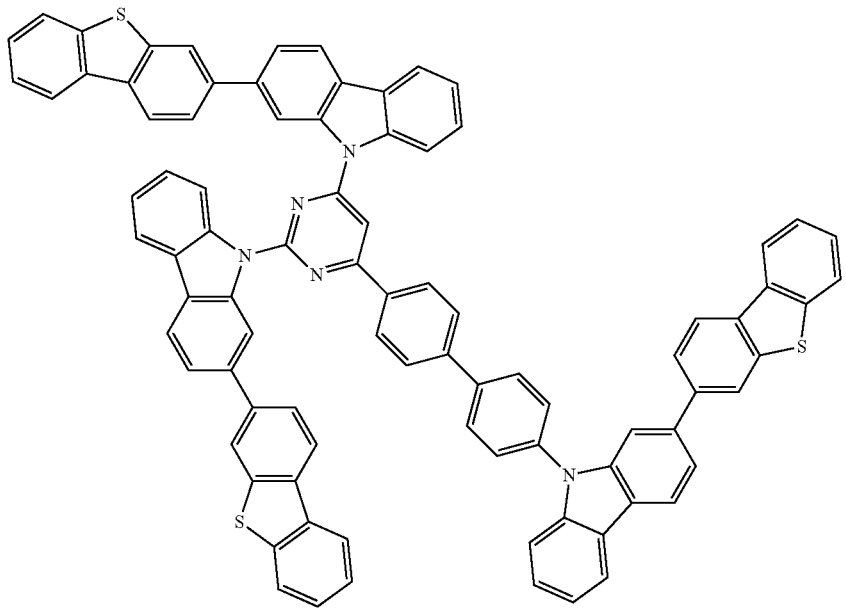
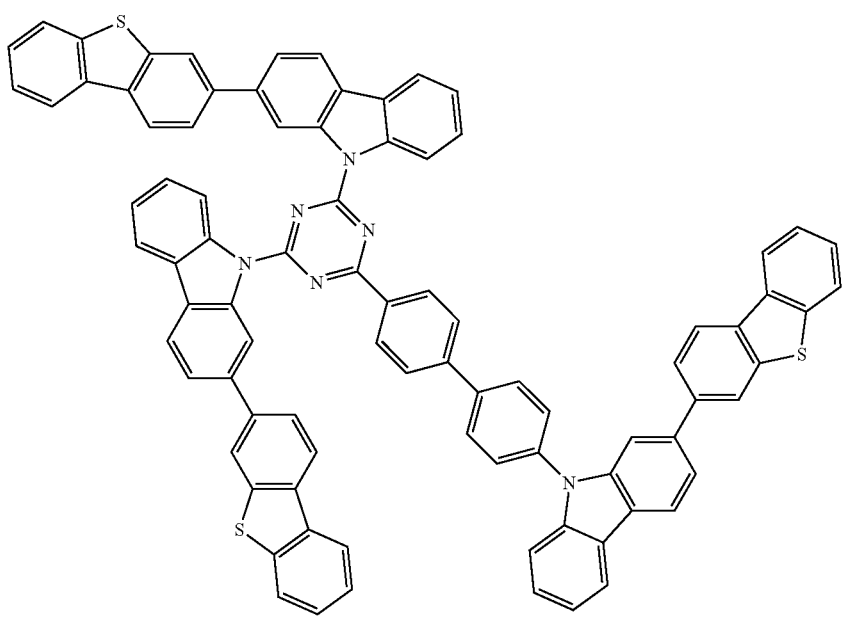

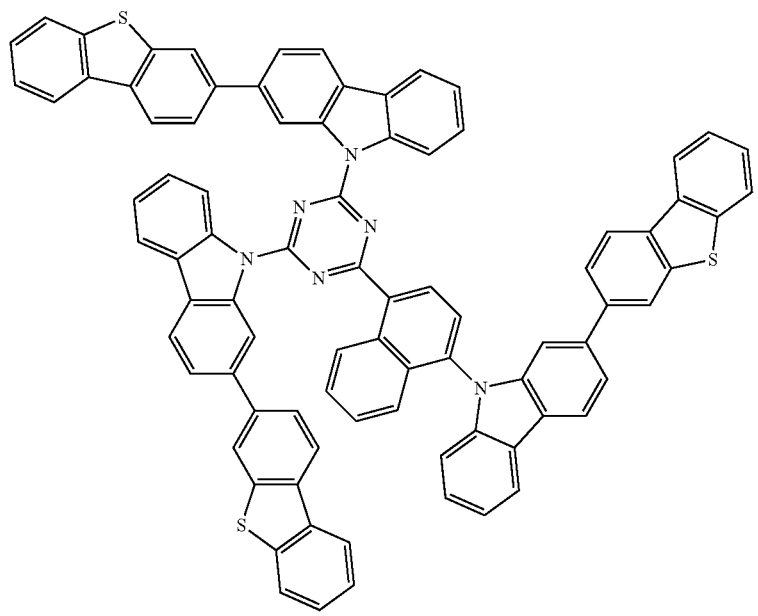
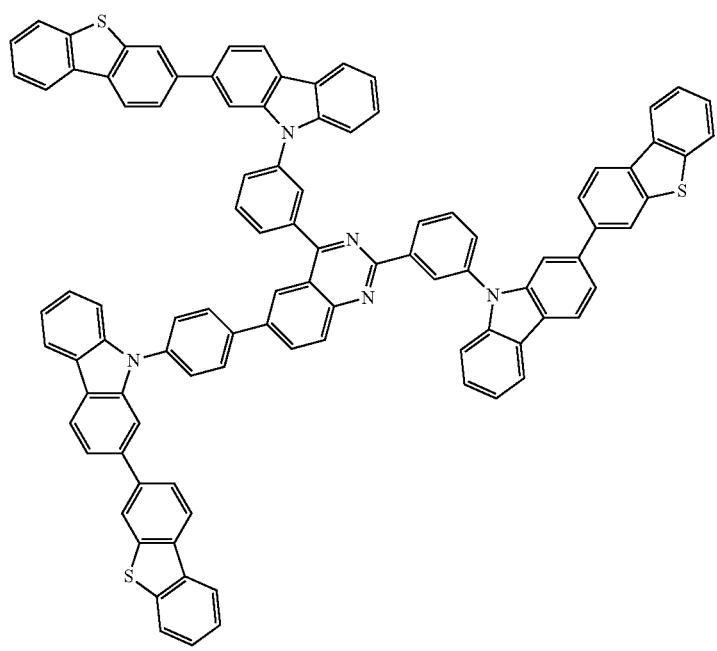

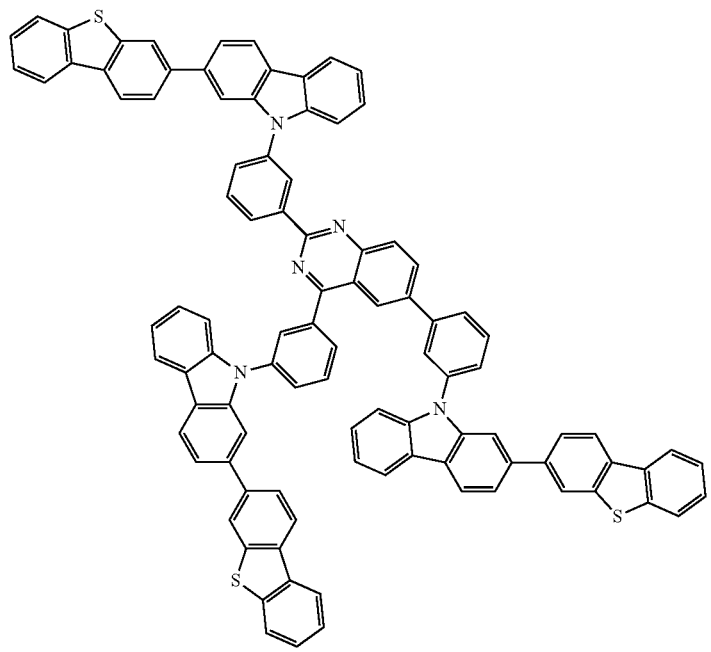
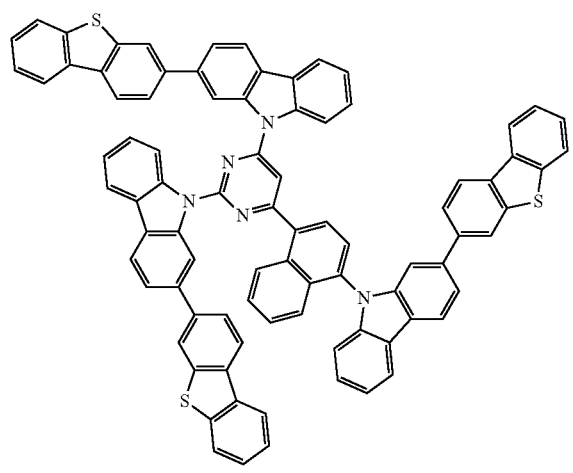
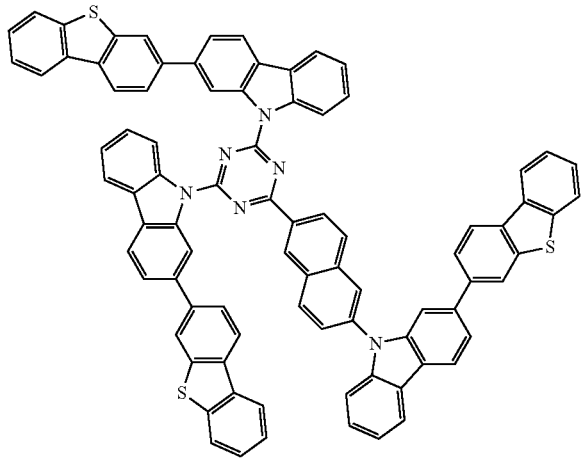

1479
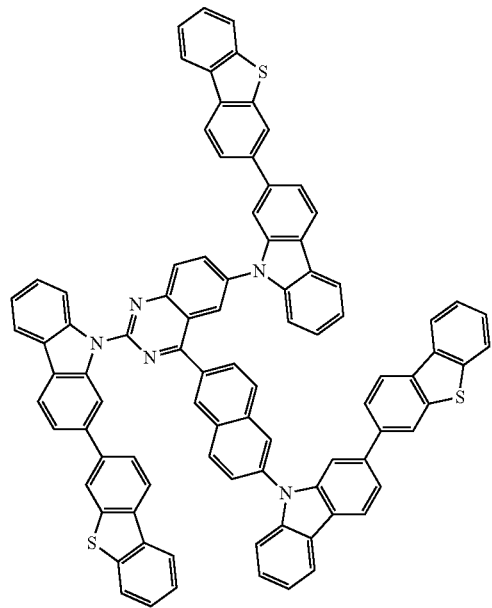
1480
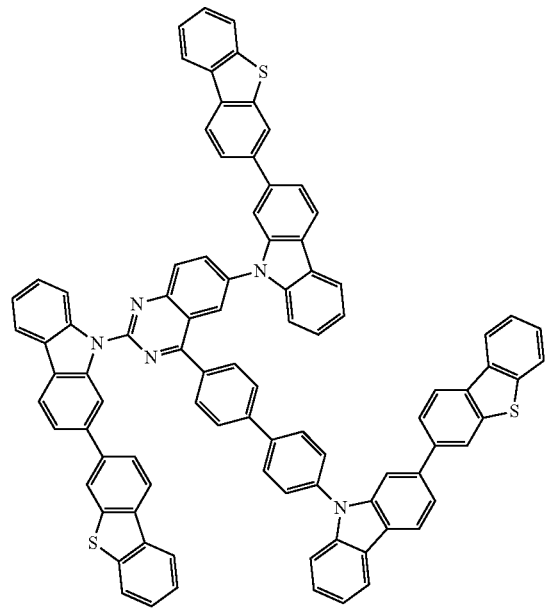
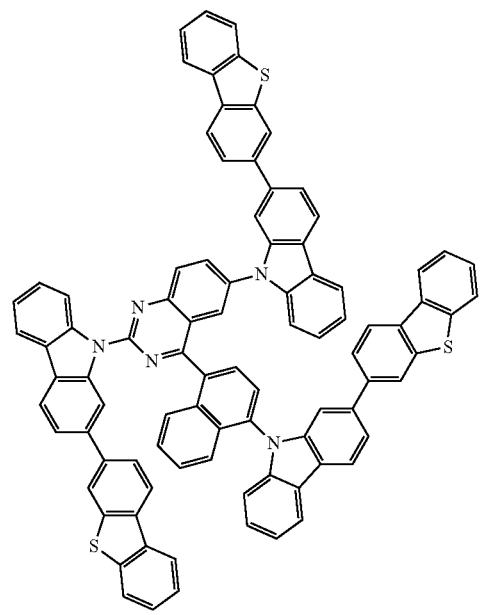
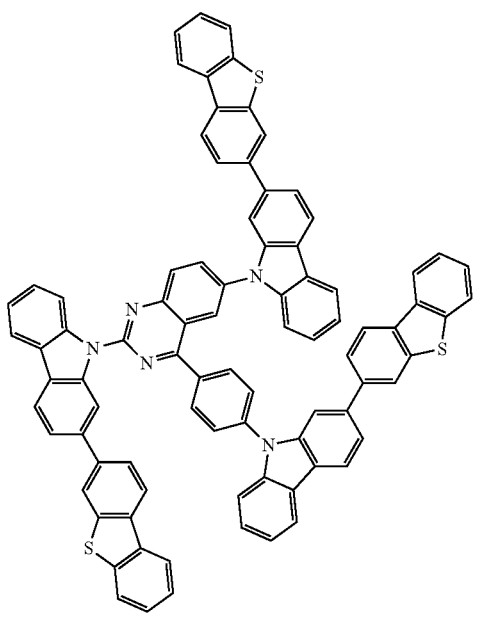

1481 1482
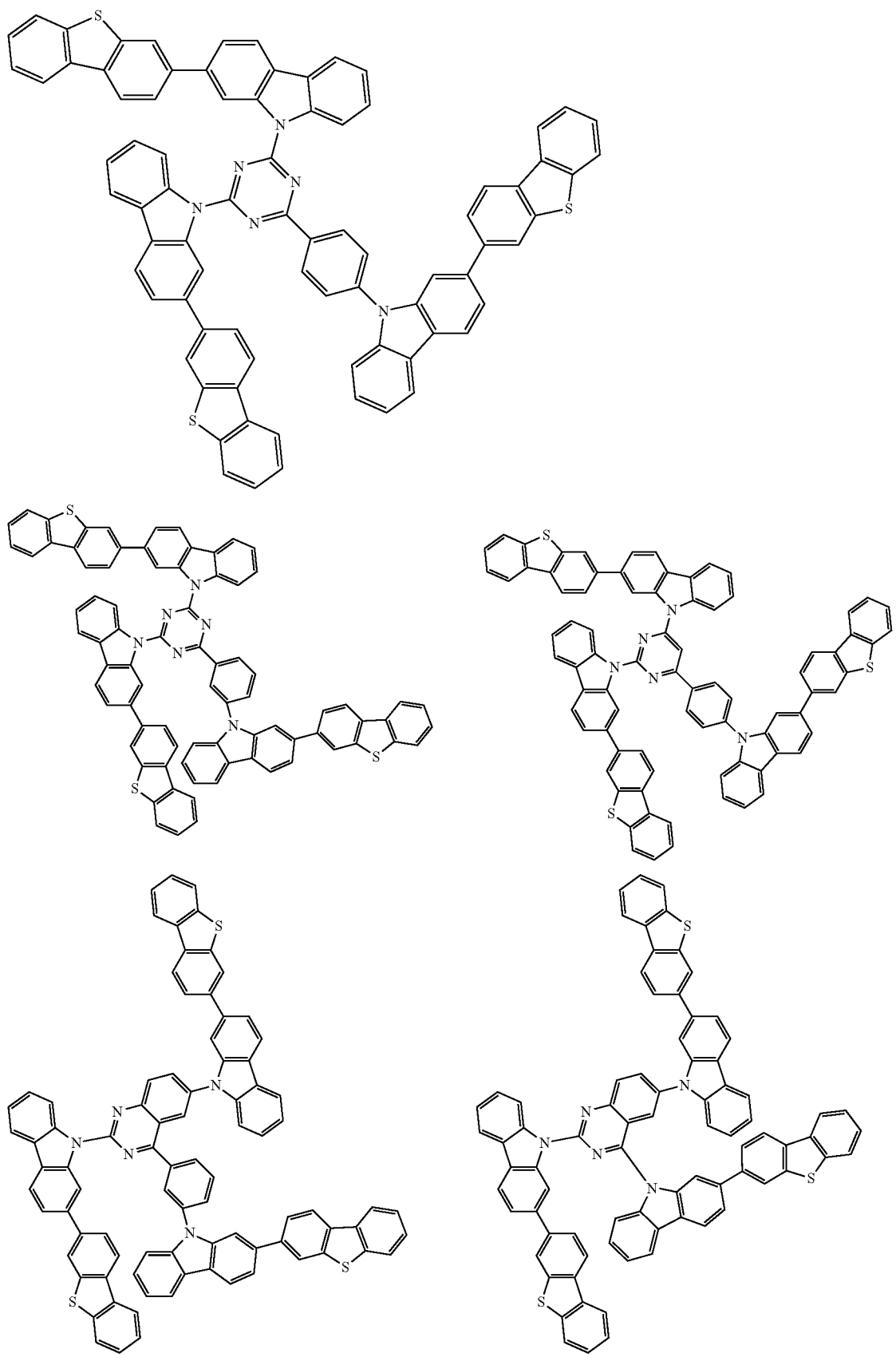

1483
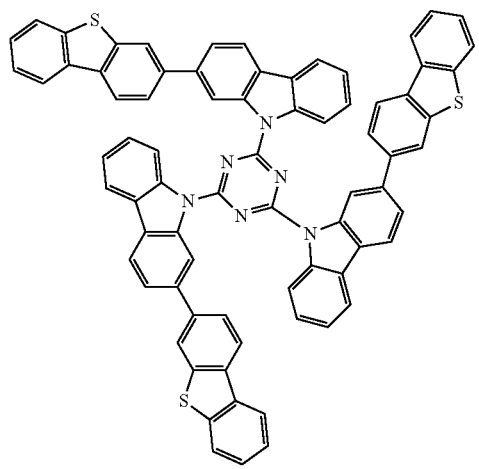
1484
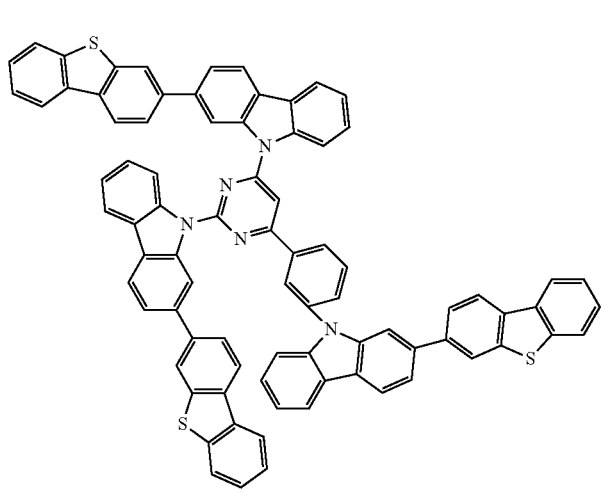
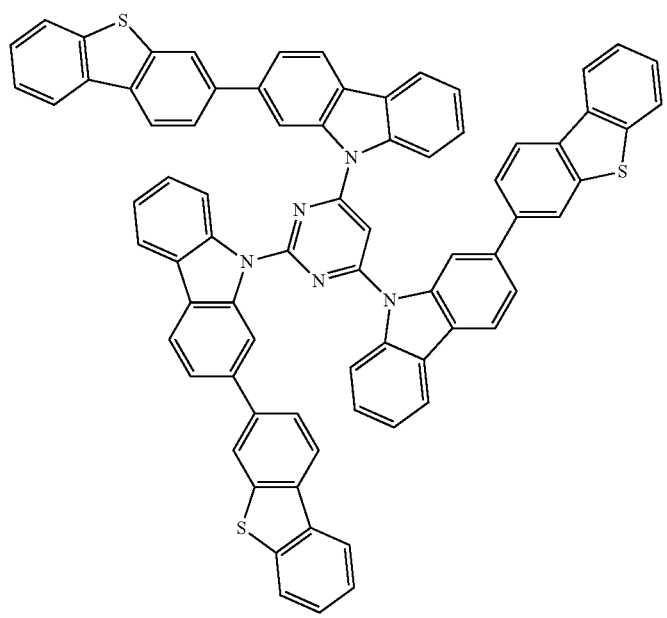
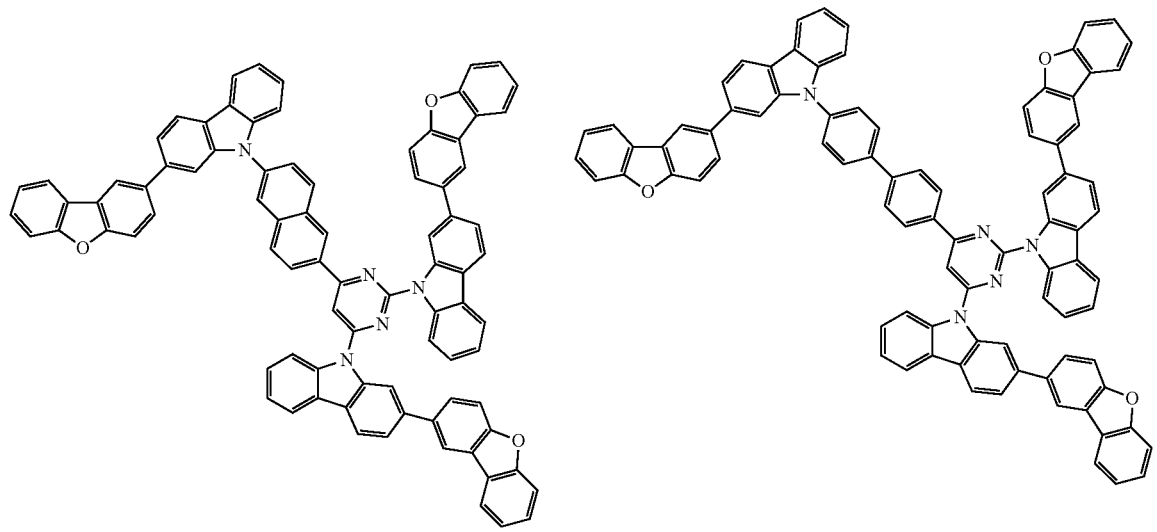 [SMILES: c1ccc2c(c1)oc1ccc(-c3ccc4c5ccccc5n(-c5ccc6cc(-c7cc(-n8c9ccccc9c9ccc(-c%10ccc%11oc%12ccccc%12c%11c%10)cc98)nc(-n8c9ccccc9c9ccc(-c%10ccc%11oc%12ccccc%12c%11c%10)cc98)n7)ccc6c5)c4c3)cc12 ; c1ccc2c(c1)oc1ccc(-c3ccc4c5ccccc5n(-c5ccc(-c6ccc(-c7cc(-n8c9ccccc9c9ccc(-c%10ccc%11oc%12ccccc%12c%11c%10)cc98)nc(-n8c9ccccc9c9ccc(-c%10ccc%11oc%12ccccc%12c%11c%10)cc98)n7)cc6)cc5)c4c3)cc12]

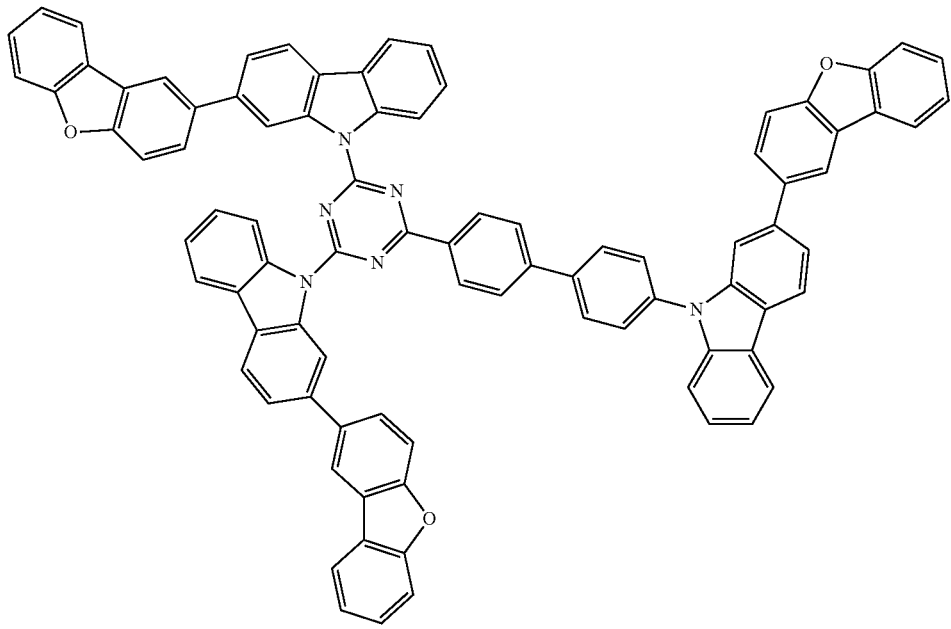
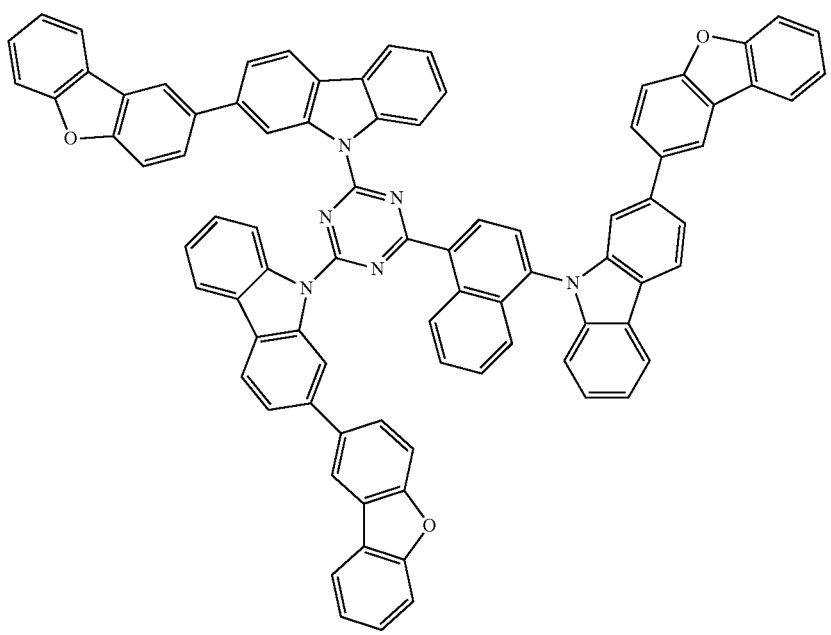

1487 1488
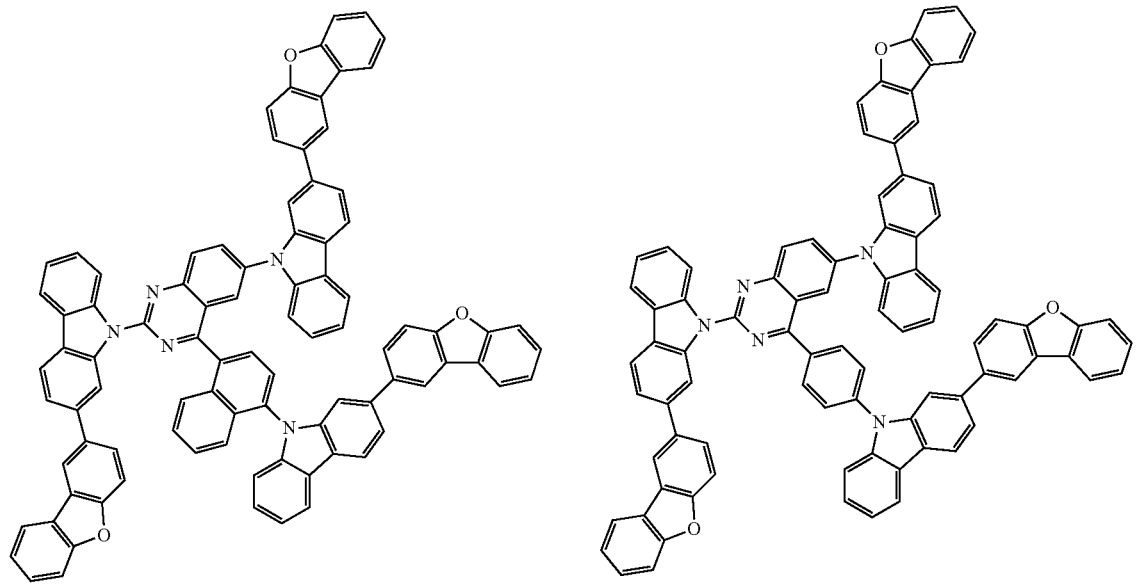
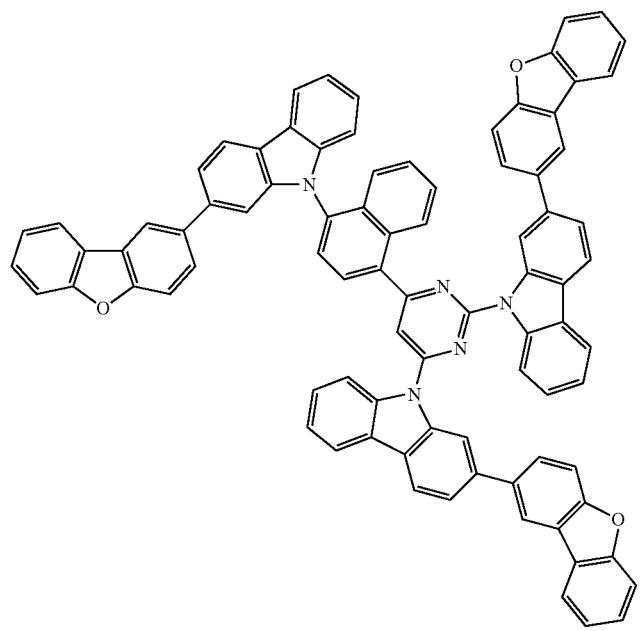

1489 1490
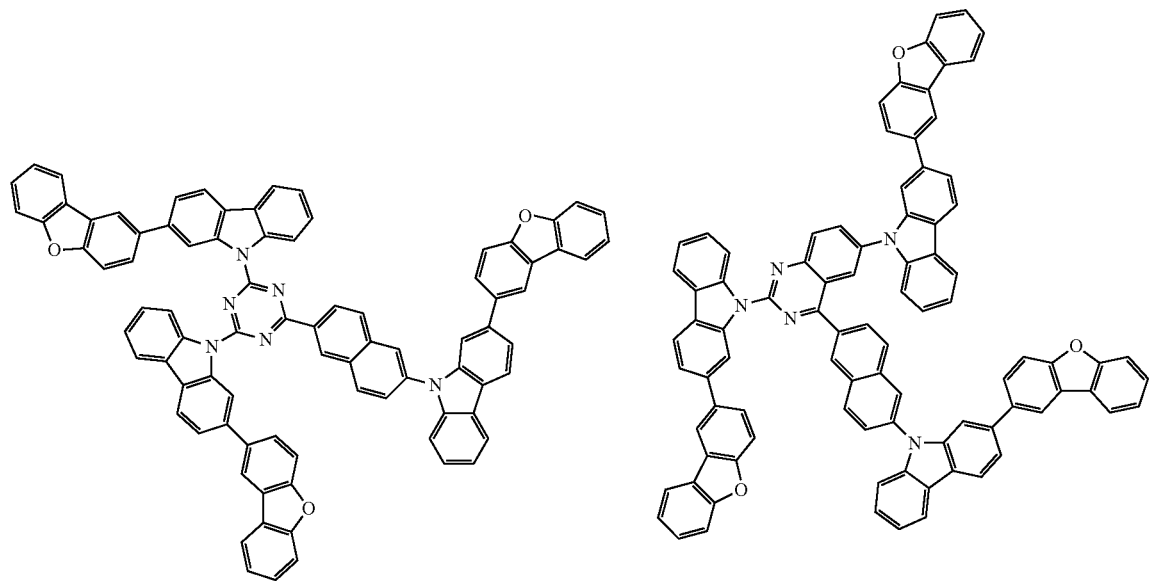 [SMILES: c1ccc2c(c1)oc1ccc(-c3ccc4c5ccccc5n(-c5ccc6cc(-c7nc(-n8c9ccccc9c9ccc(-c%10ccc%11oc%12ccccc%12c%11c%10)cc98)nc(-n8c9ccccc9c9ccc(-c%10ccc%11oc%12ccccc%12c%11c%10)cc98)n7)ccc6c5)c4c3)cc12 ; c1ccc2c(c1)oc1ccc(-c3ccc4c5ccccc5n(-c5ccc6cc(-c7nc(-n8c9ccccc9c9ccc(-c%10ccc%11oc%12ccccc%12c%11c%10)cc98)nc8ccc(-n9c%10ccccc%10c%10ccc(-c%11ccc%12oc%13ccccc%13c%12c%11)cc%109)cc78)ccc6c5)c4c3)cc12]
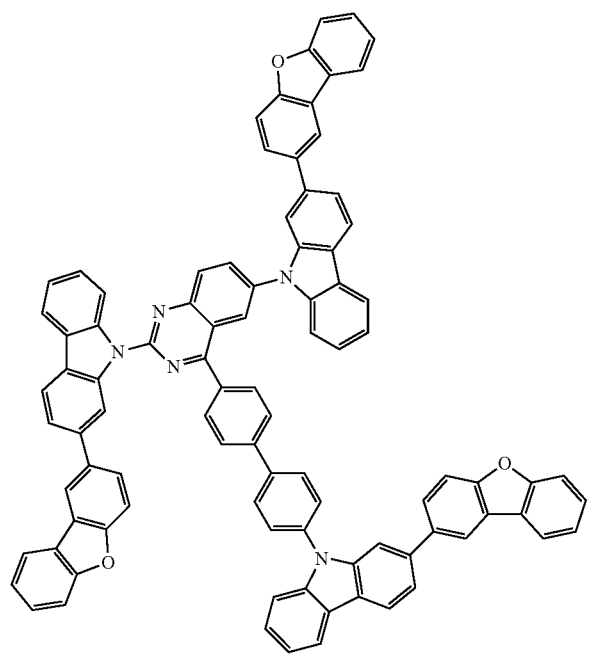

1491 1492
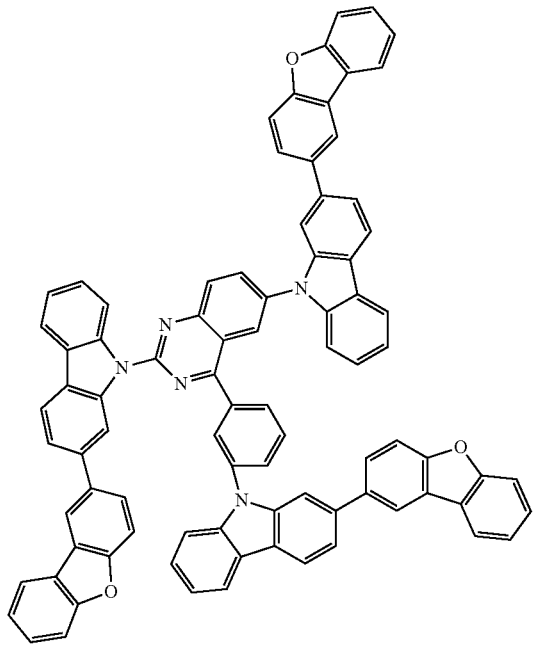
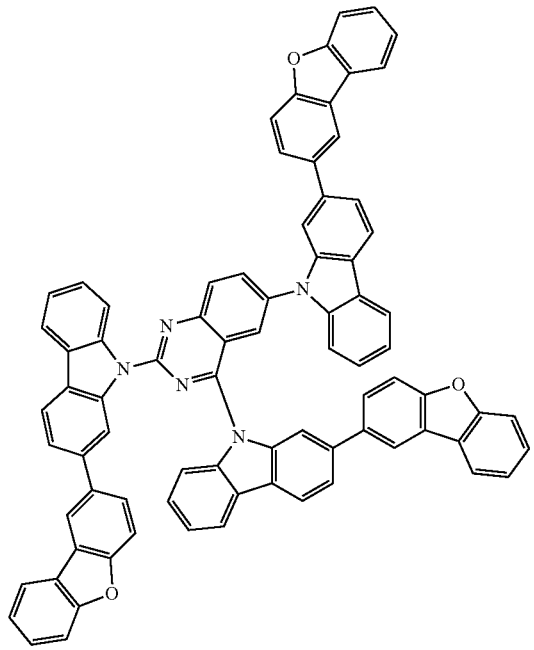
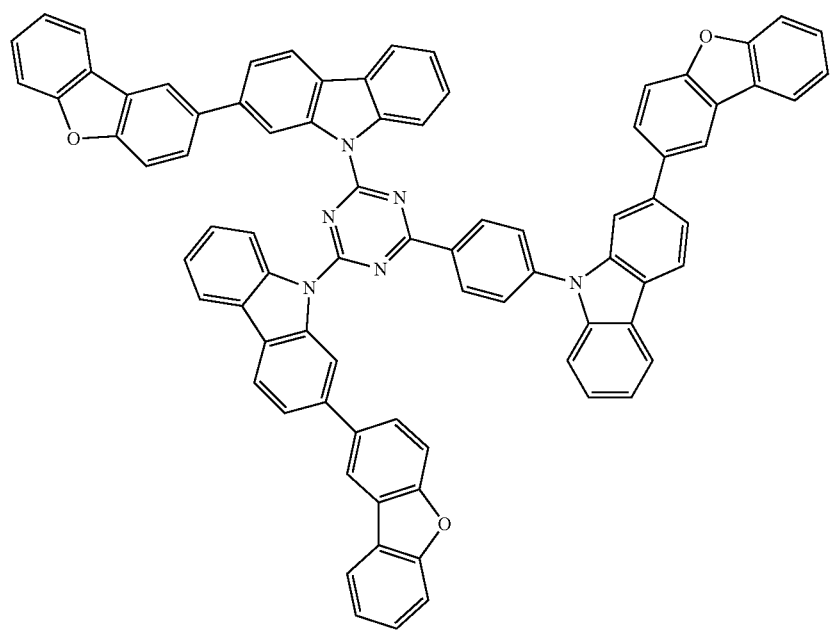

1493
1494
-continued
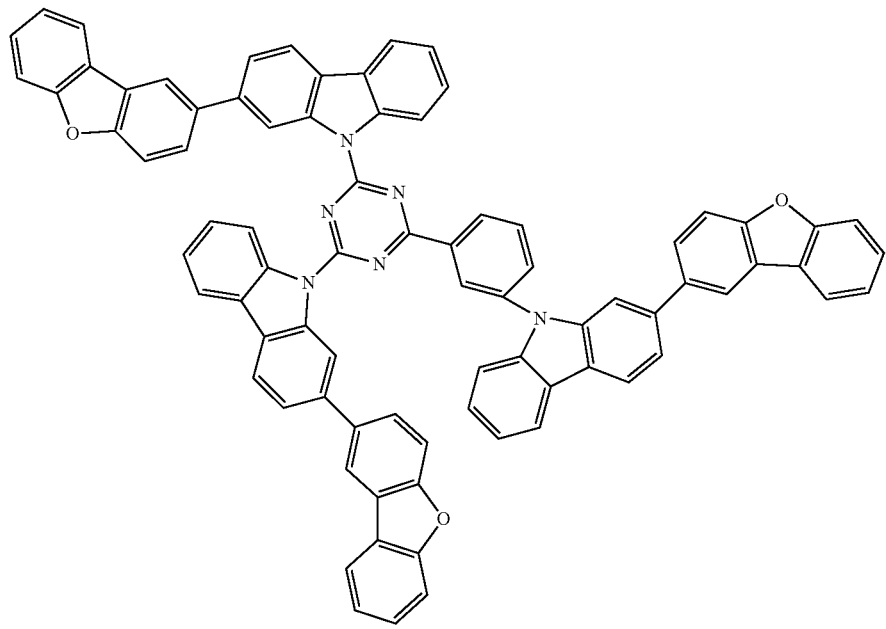
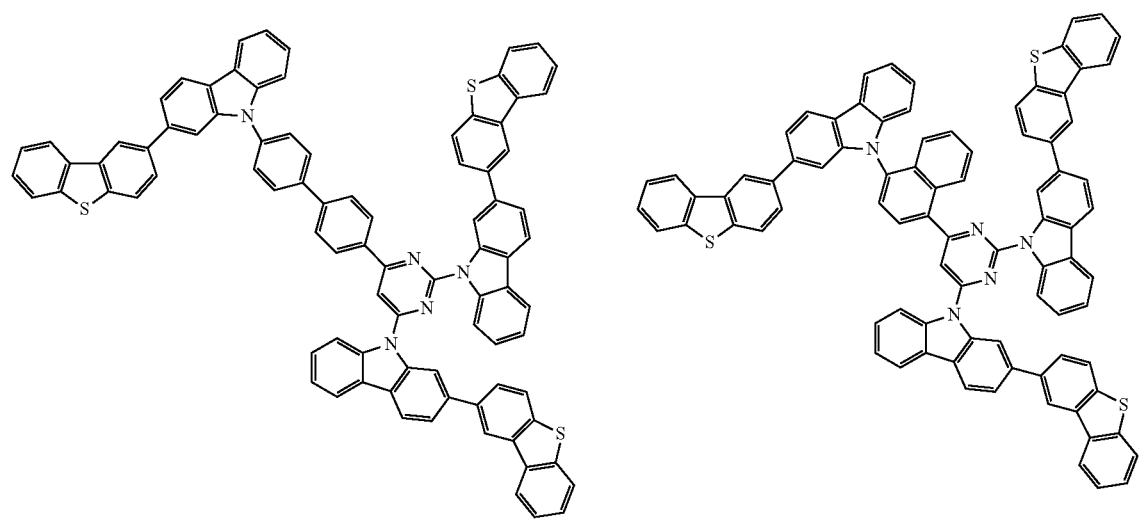 [SMILES: c1ccc2c(c1)sc1ccc(-c3ccc4c5ccccc5n(-c5ccc(-c6ccc(-c7cc(-n8c9ccccc9c9ccc(-c%10ccc%11sc%12ccccc%12c%11c%10)cc98)nc(-n8c9ccccc9c9ccc(-c%10ccc%11sc%12ccccc%12c%11c%10)cc98)n7)cc6)cc5)c4c3)cc12 ; c1ccc2c(c1)sc1ccc(-c3ccc4c5ccccc5n(-c5cc(-c6ccc(-n7c8ccccc8c8ccc(-c9ccc%10sc%11ccccc%11c%10c9)cc87)c7ccccc67)nc(-n6c7ccccc7c7ccc(-c8ccc9sc%10ccccc%10c9c8)cc76)n5)c4c3)cc12]

-continued
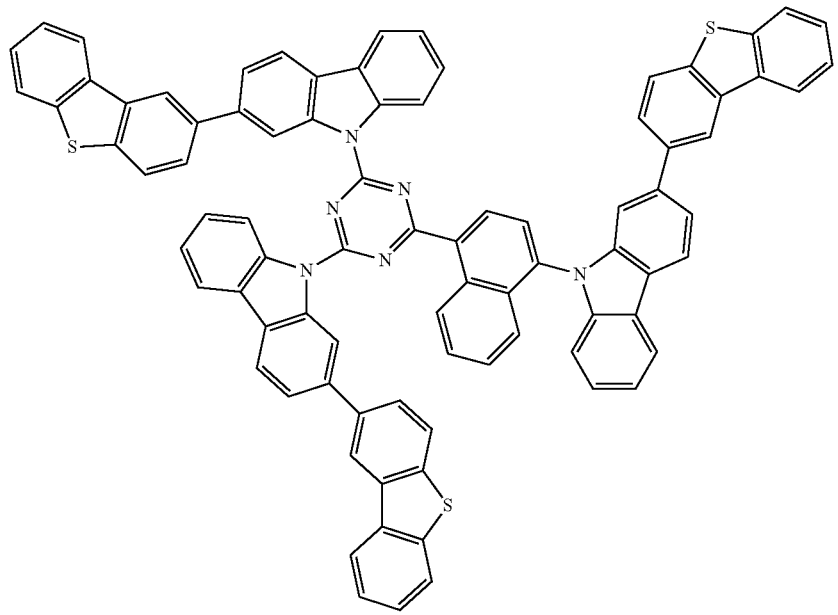
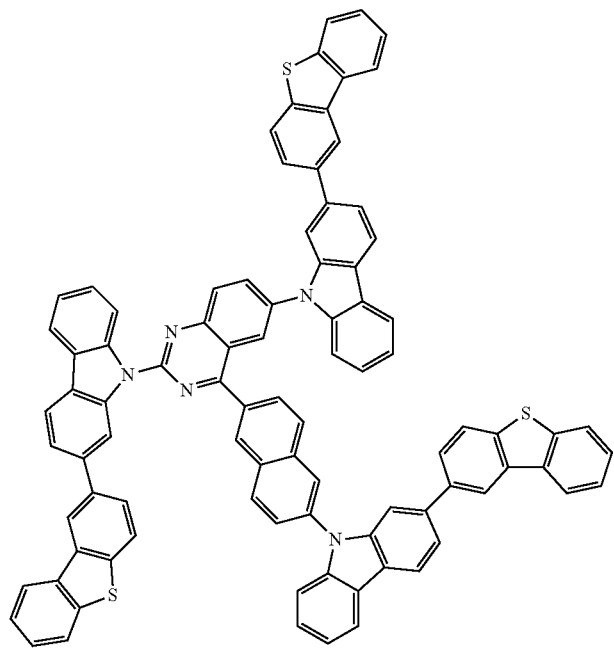

-continued

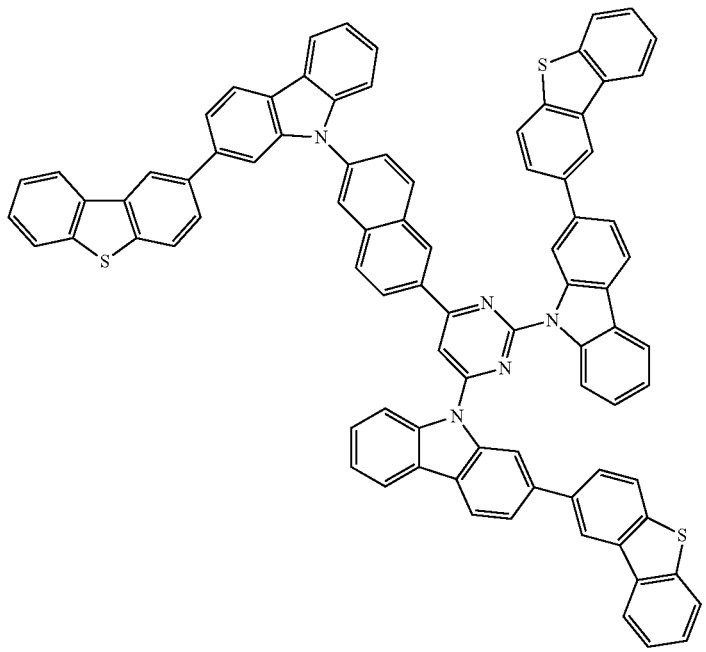
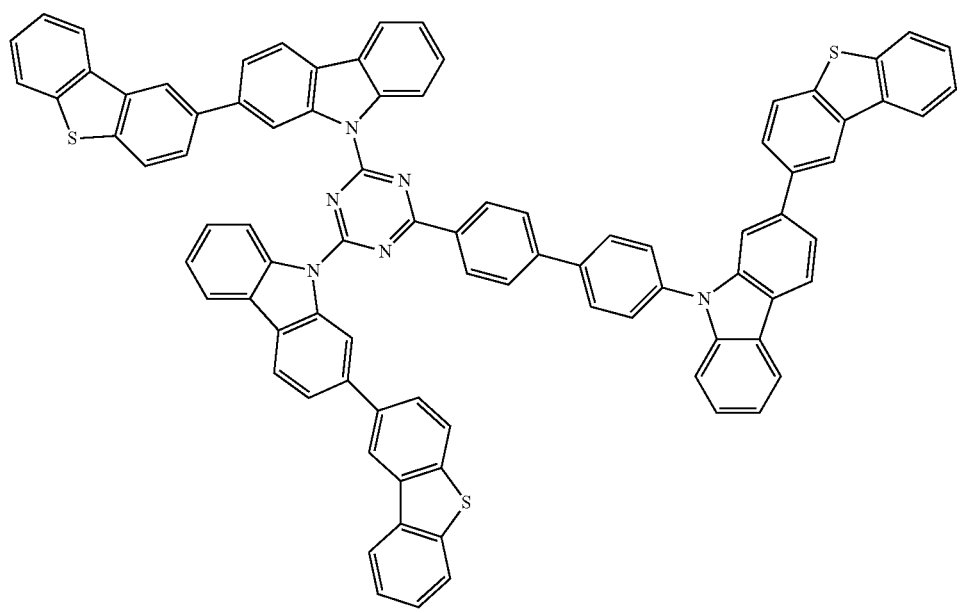

1501
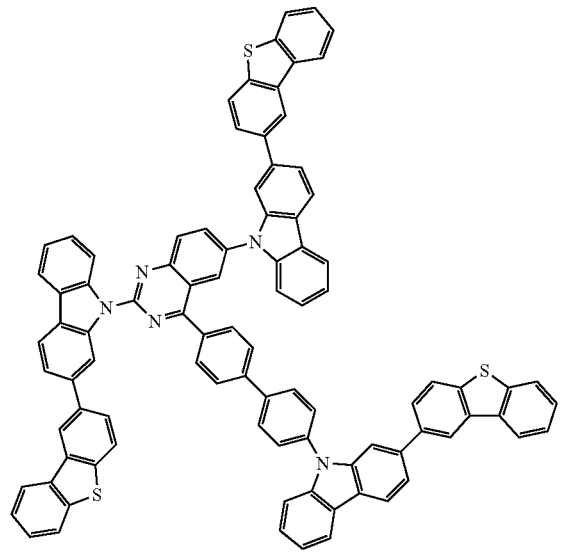
1502
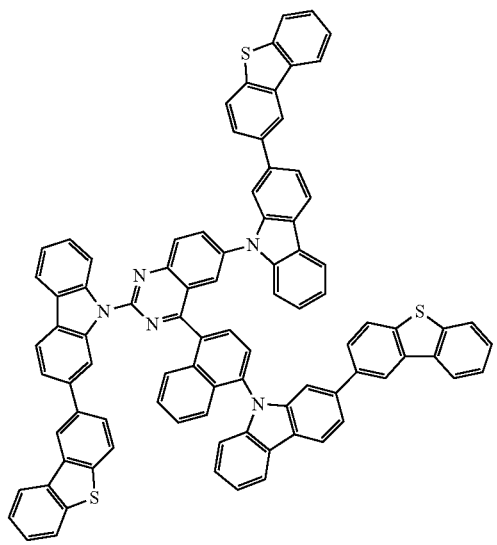
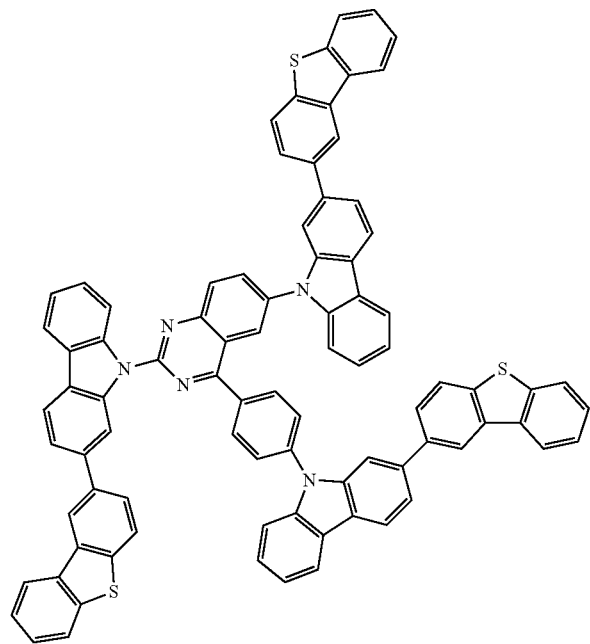
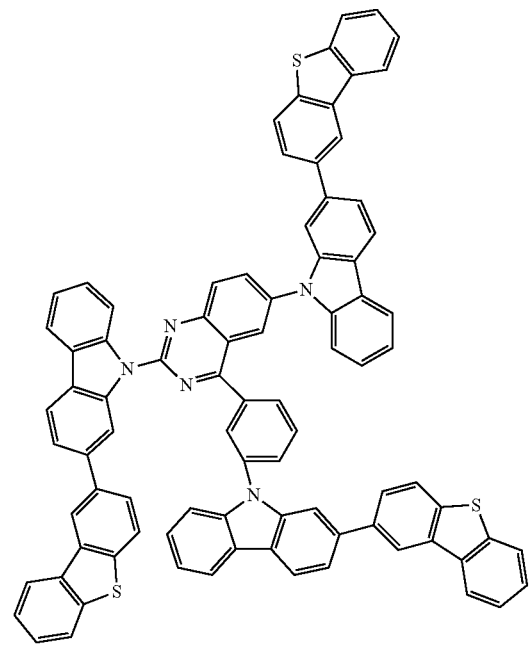

1503
1504
-continued
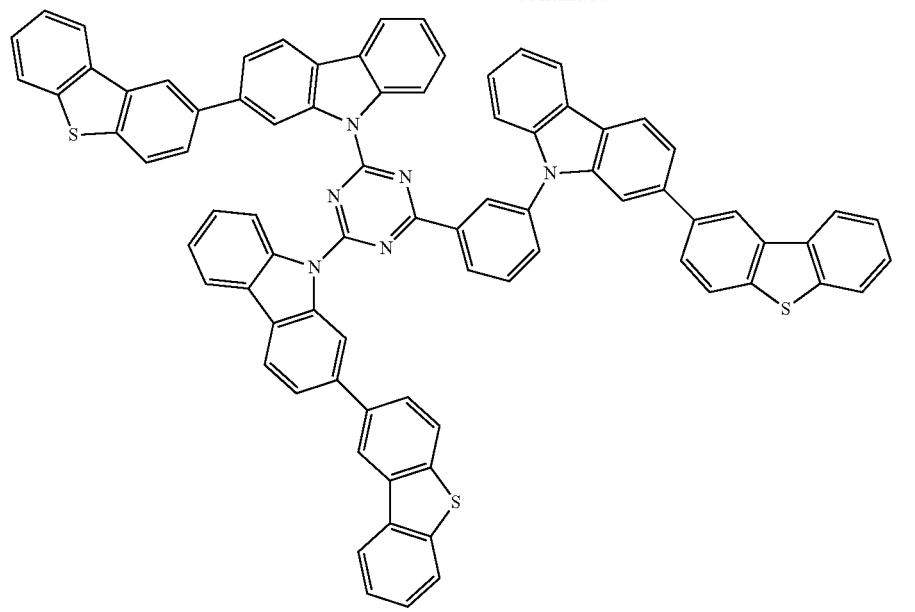
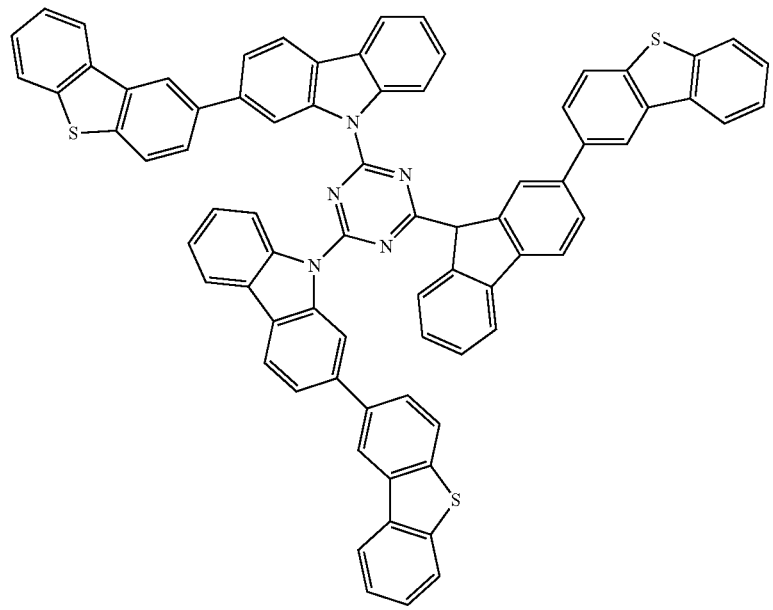
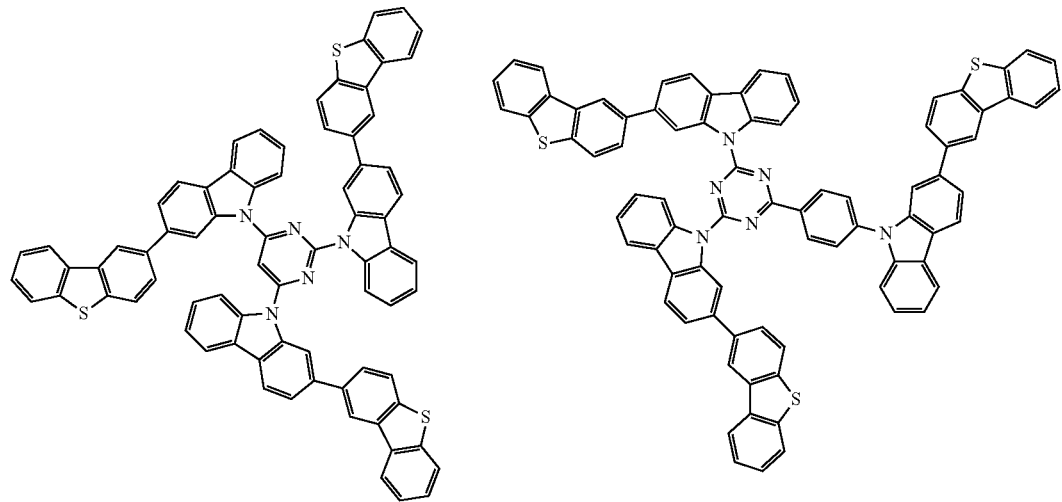 [SMILES: c1ccc2c(c1)sc1ccc(-c3ccc4c5ccccc5n(-c5cc(-n6c7ccccc7c7ccc(-c8ccc9sc%10ccccc%10c9c8)cc76)nc(-n6c7ccccc7c7ccc(-c8ccc9sc%10ccccc%10c9c8)cc76)n5)c4c3)cc12 ; c1ccc2c(c1)sc1ccc(-c3ccc4c5ccccc5n(-c5ccc(-c6nc(-n7c8ccccc8c8ccc(-c9ccc%10sc%11ccccc%11c%10c9)cc87)nc(-n7c8ccccc8c8ccc(-c9ccc%10sc%11ccccc%11c%10c9)cc87)n6)cc5)c4c3)cc12]

-continued
| 1505 | 1506 |
|---|---|
| 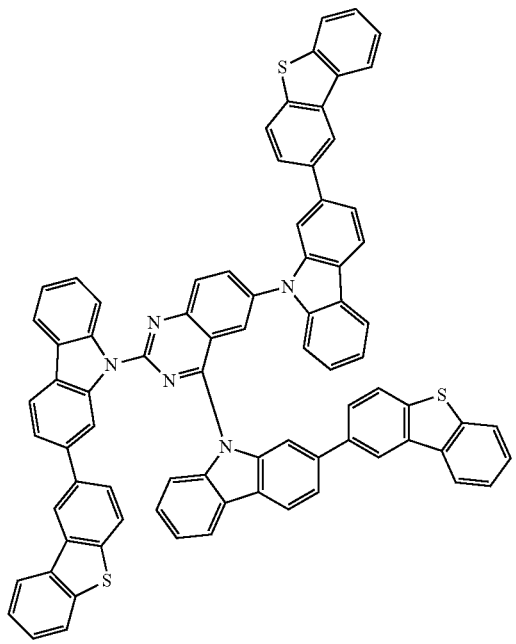 | 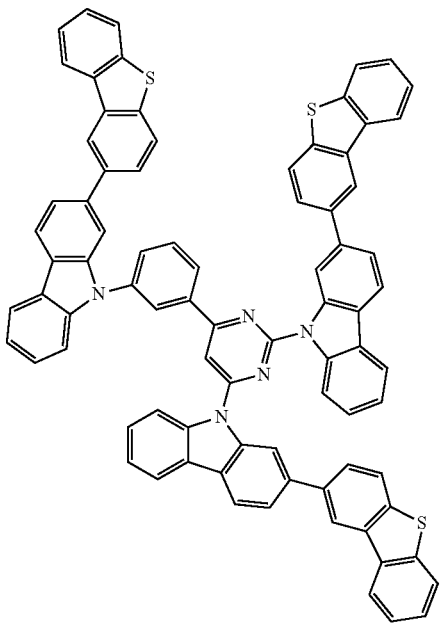 |
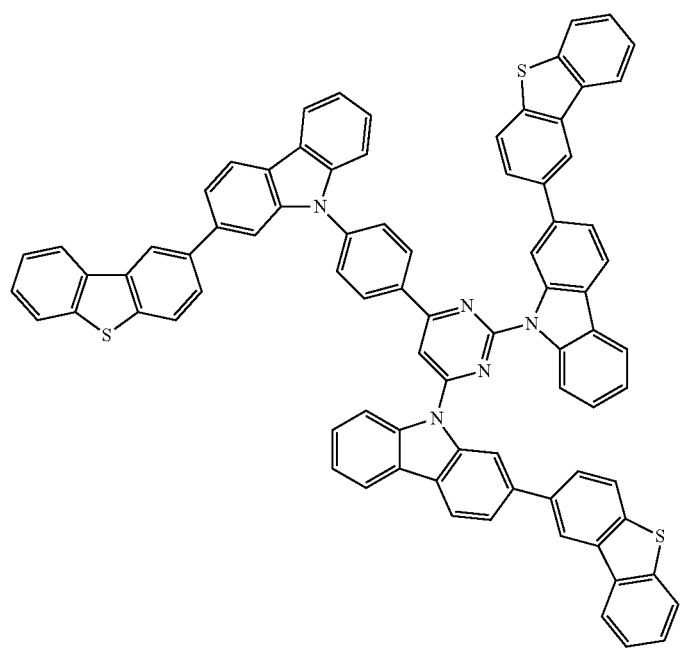

1507 1508
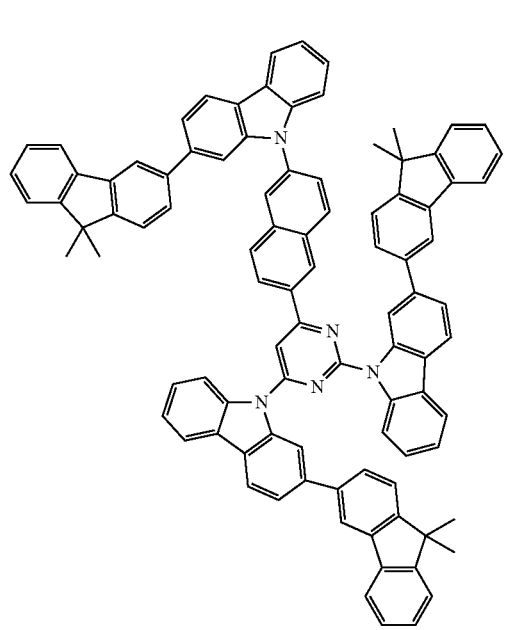
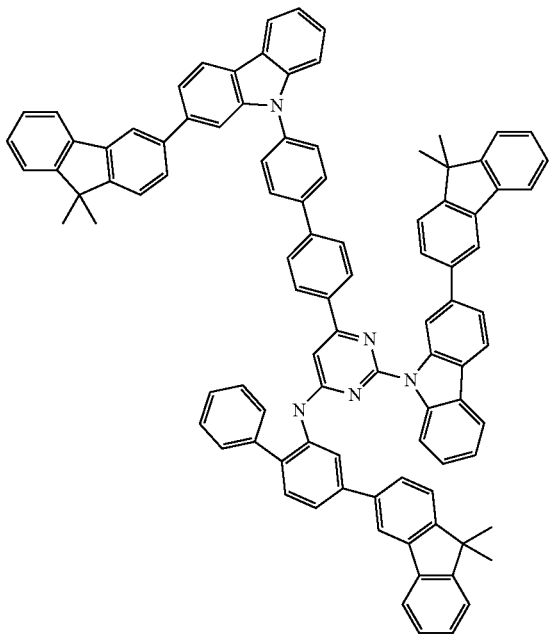
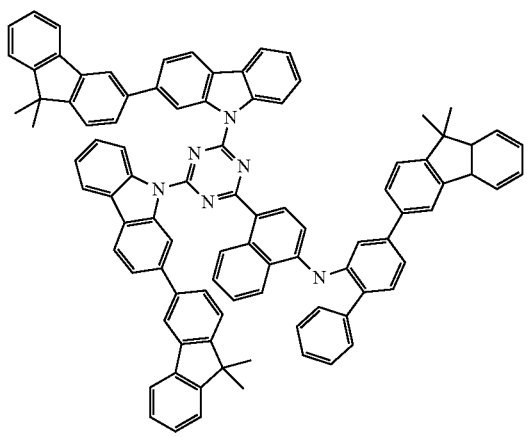
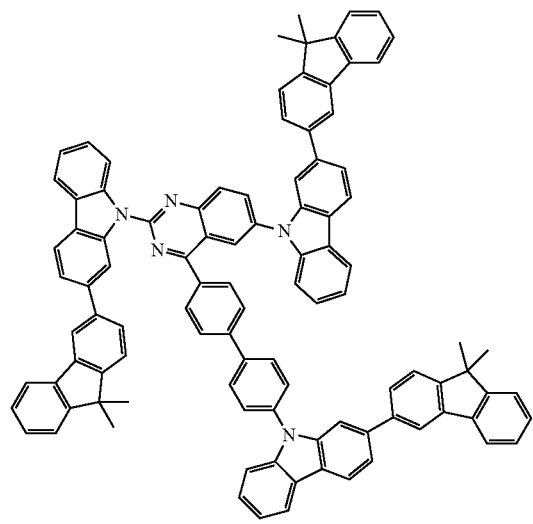
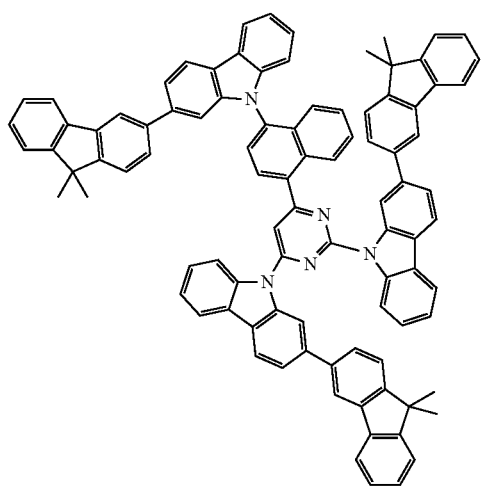

-continued
1509
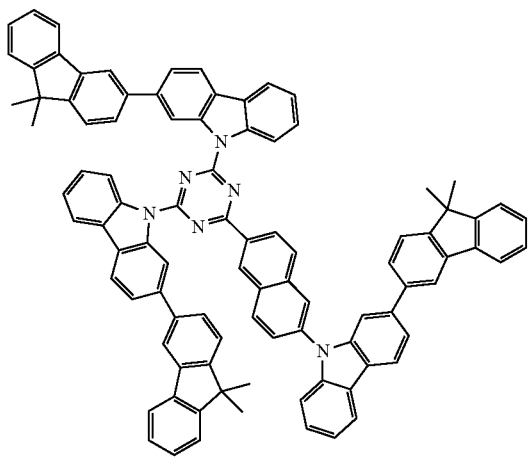
1510
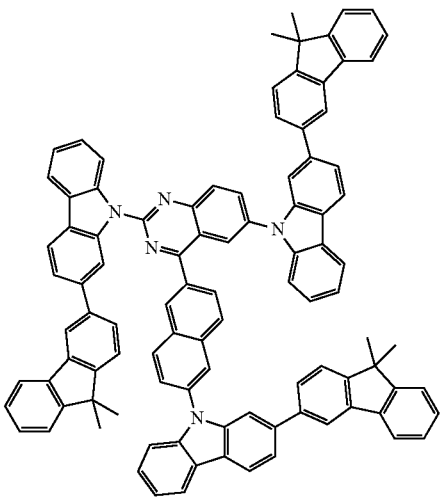
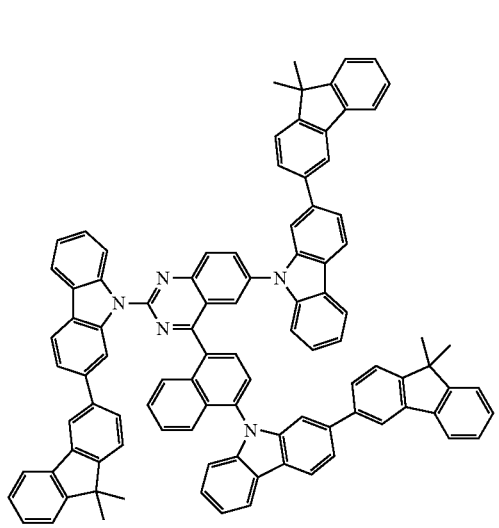
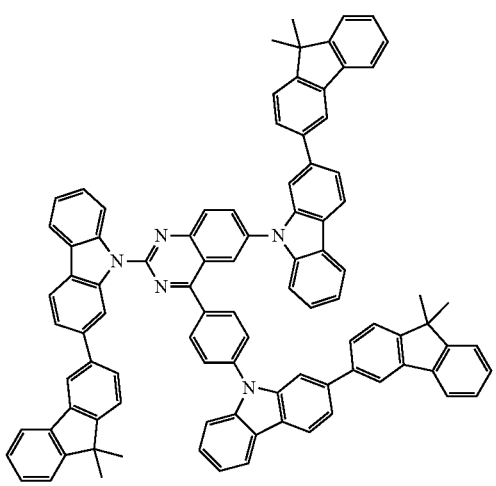
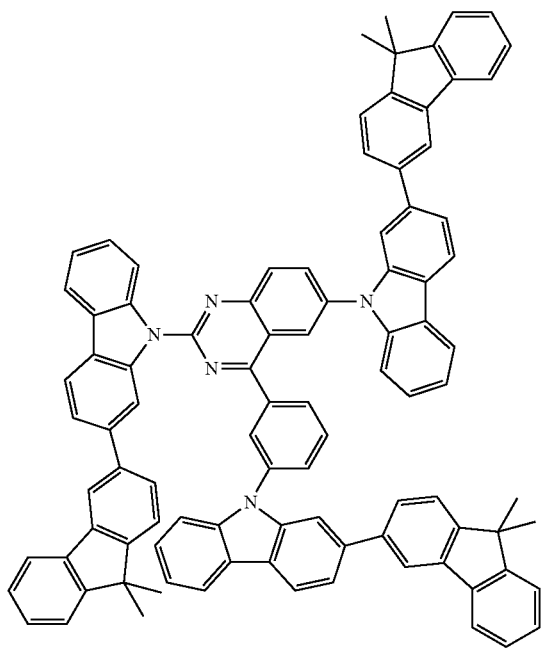
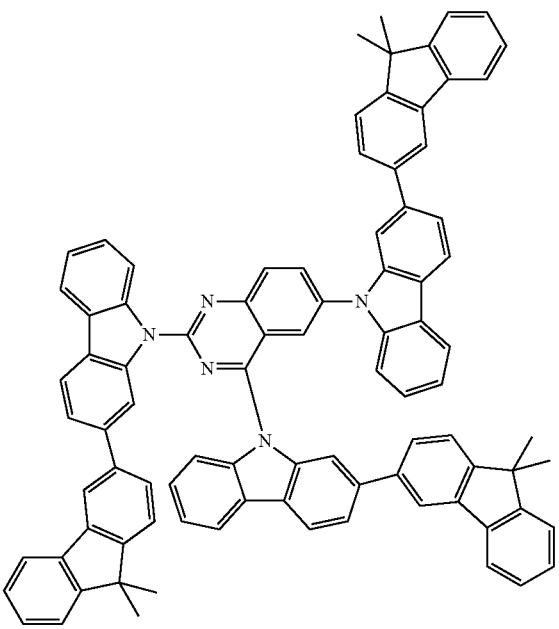

-continued
| 1511 | 1512 |
|---|---|
| 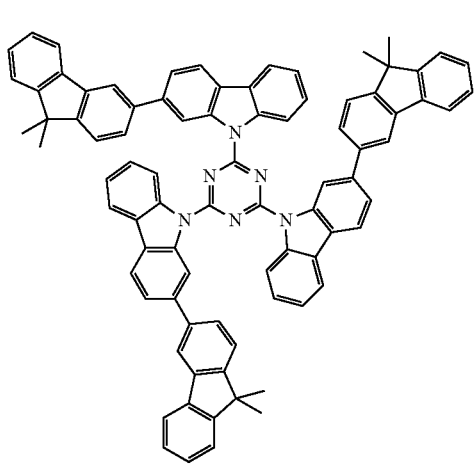 | 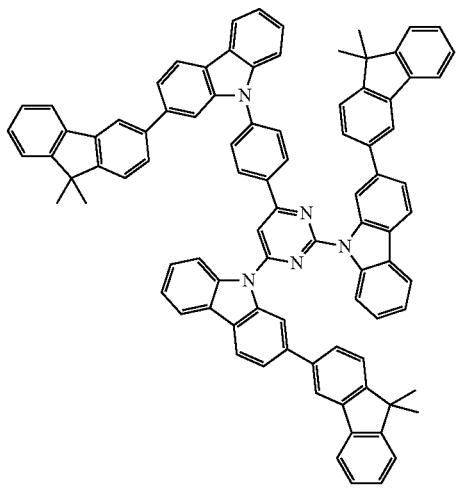 |
| 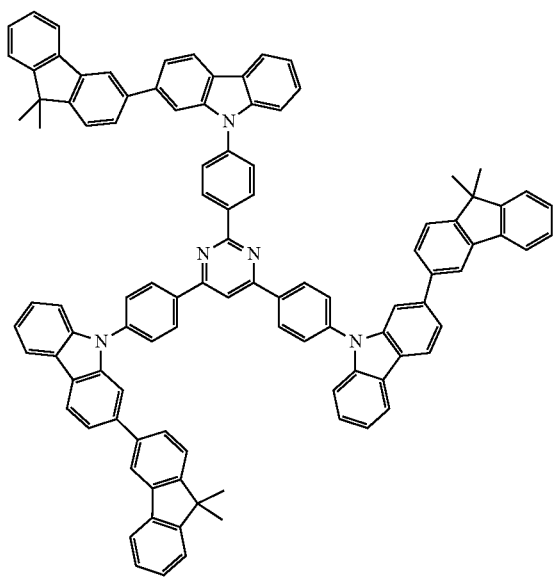 | 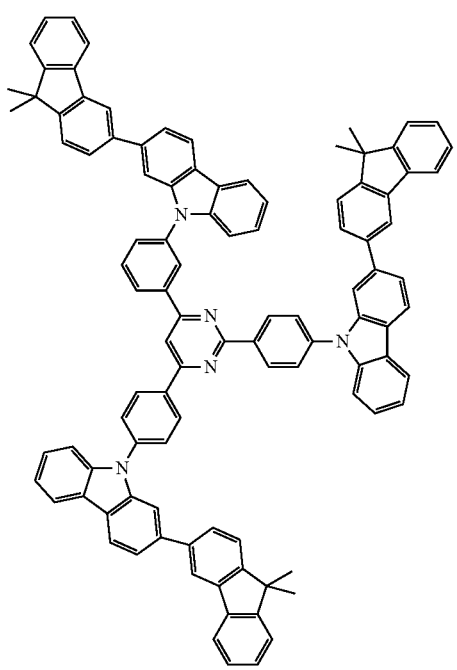 |
| 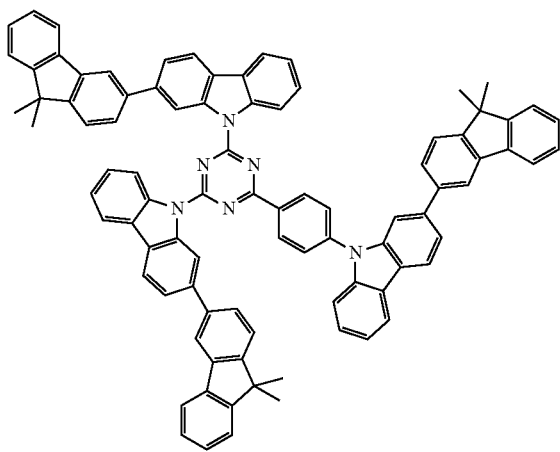 | 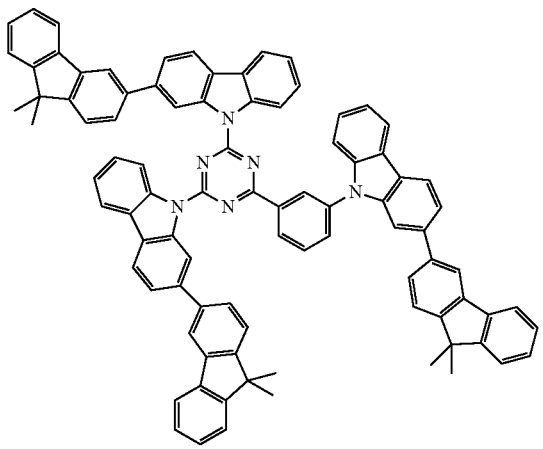 |

1513 1514
-continued
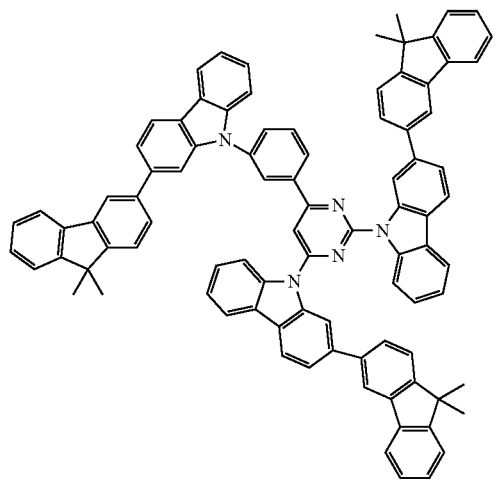
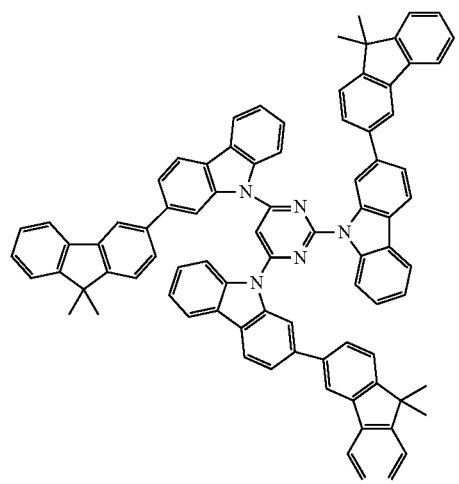
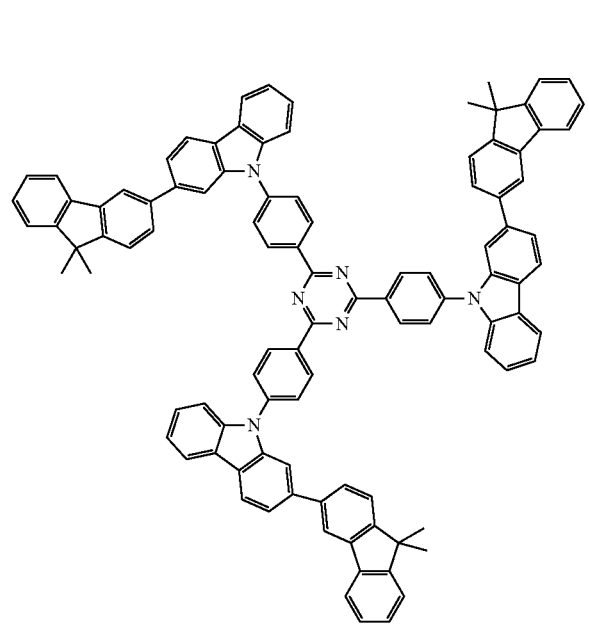
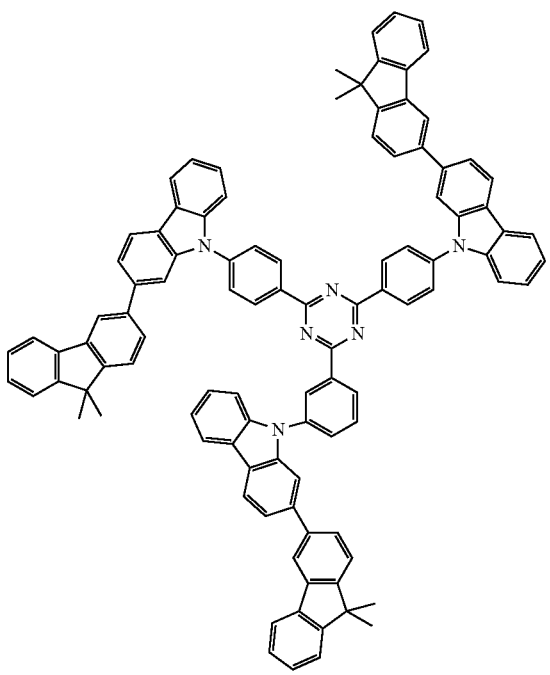

-continued
1515
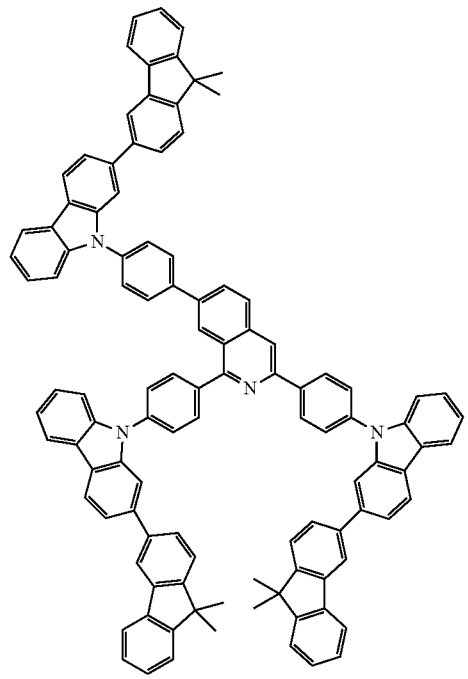
1516
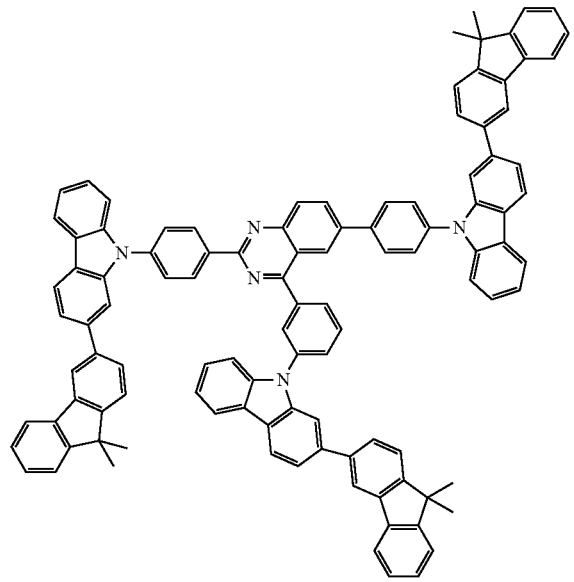
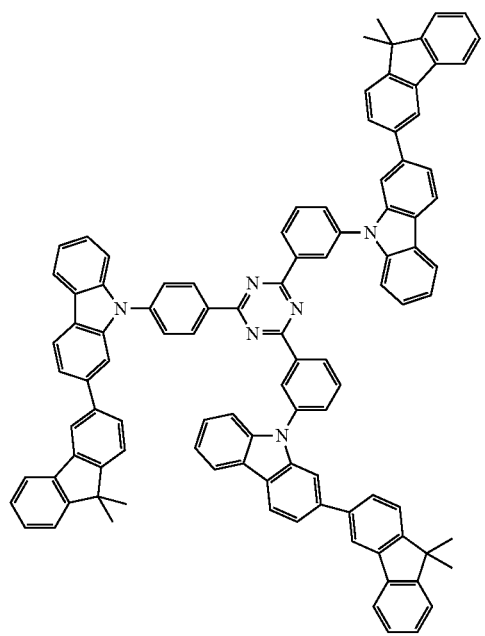
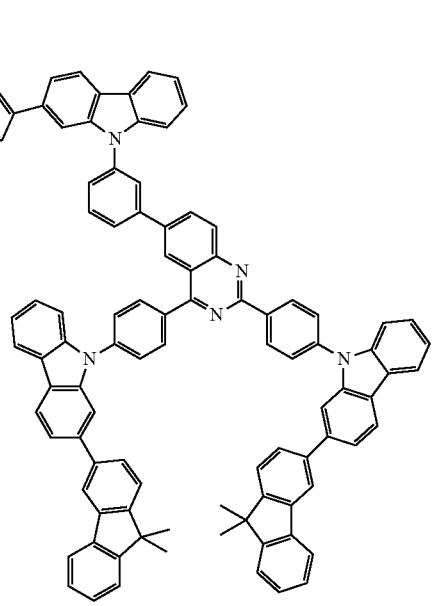

1517
1518
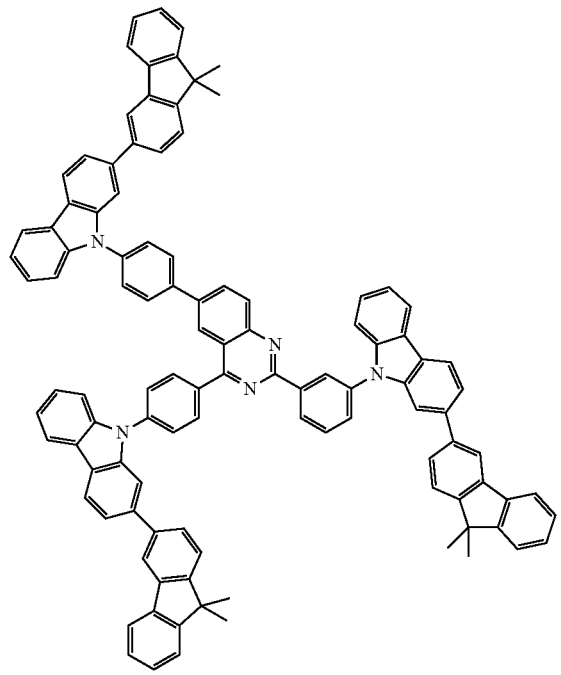
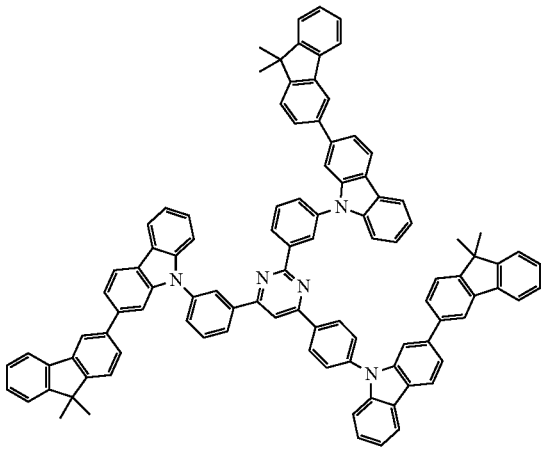
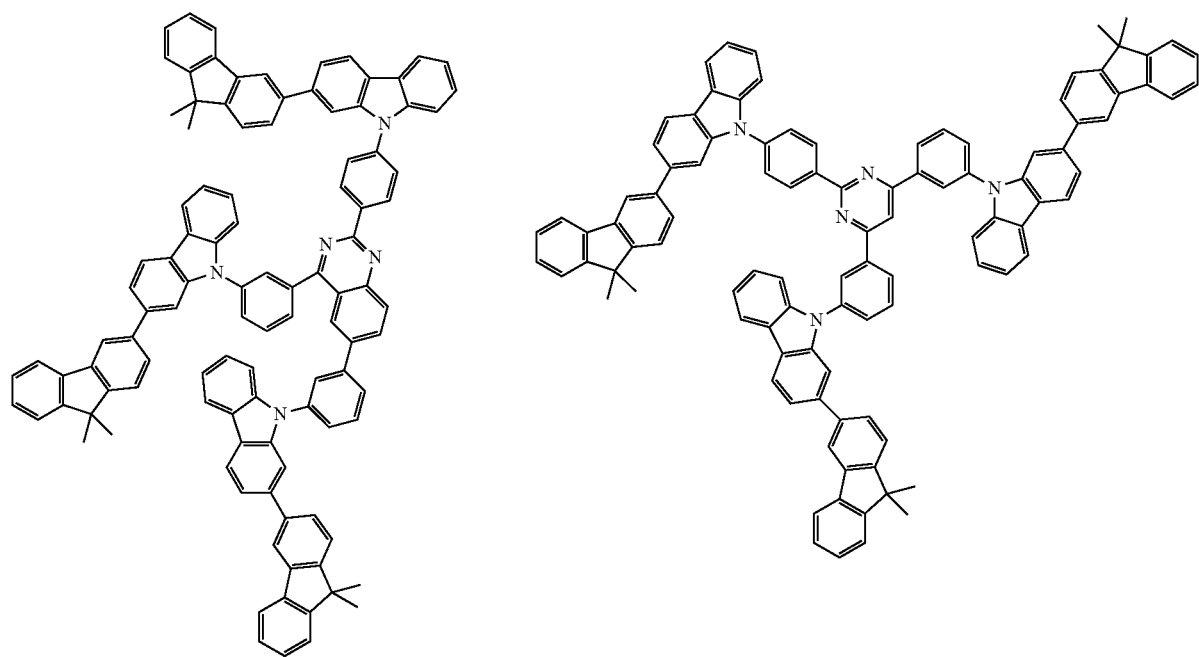 [SMILES: CC1(C)c2ccccc2-c2cc(-c3ccc4c5ccccc5n(-c5ccc(-c6nc(-c7cccc(-n8c9ccccc9c9ccc(-c%10ccc%11c(c%10)-c%10ccccc%10C%11(C)C)cc98)c7)c7cc(-c8cccc(-n9c%10ccccc%10c%10ccc(-c%11ccc%12c(c%11)-c%11ccccc%11C%12(C)C)cc%109)c8)ccc7n6)cc5)c4c3)ccc21 ; CC1(C)c2ccccc2-c2cc(-c3ccc4c5ccccc5n(-c5ccc(-c6nc(-c7cccc(-n8c9ccccc9c9ccc(-c%10ccc%11c(c%10)-c%10ccccc%10C%11(C)C)cc98)c7)cc(-c7cccc(-n8c9ccccc9c9ccc(-c%10ccc%11c(c%10)-c%10ccccc%10C%11(C)C)cc98)c7)n6)cc5)c4c3)ccc21]

-continued
| 1519 | 1520 |
|---|---|
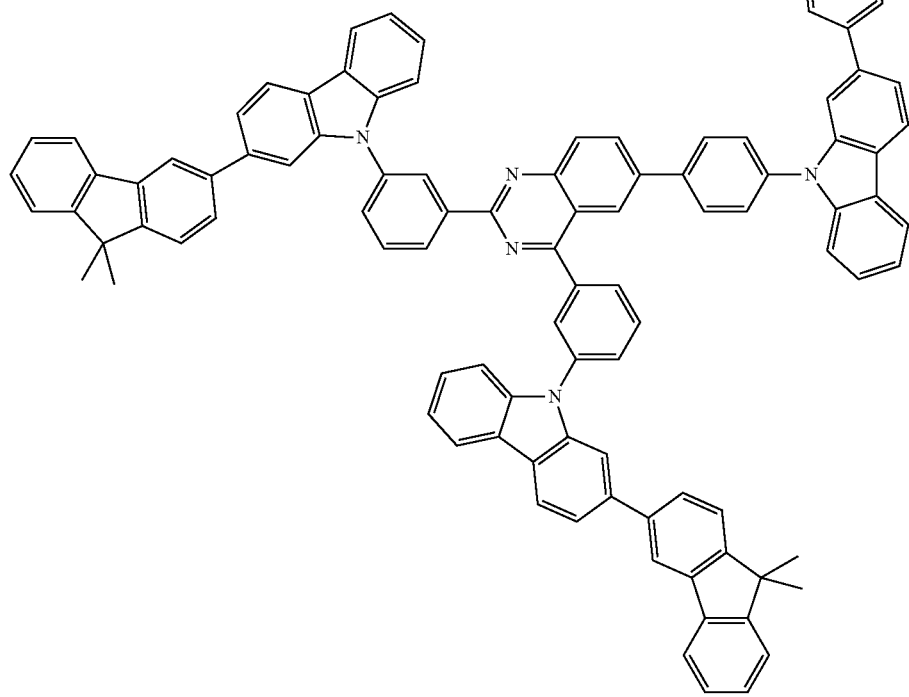
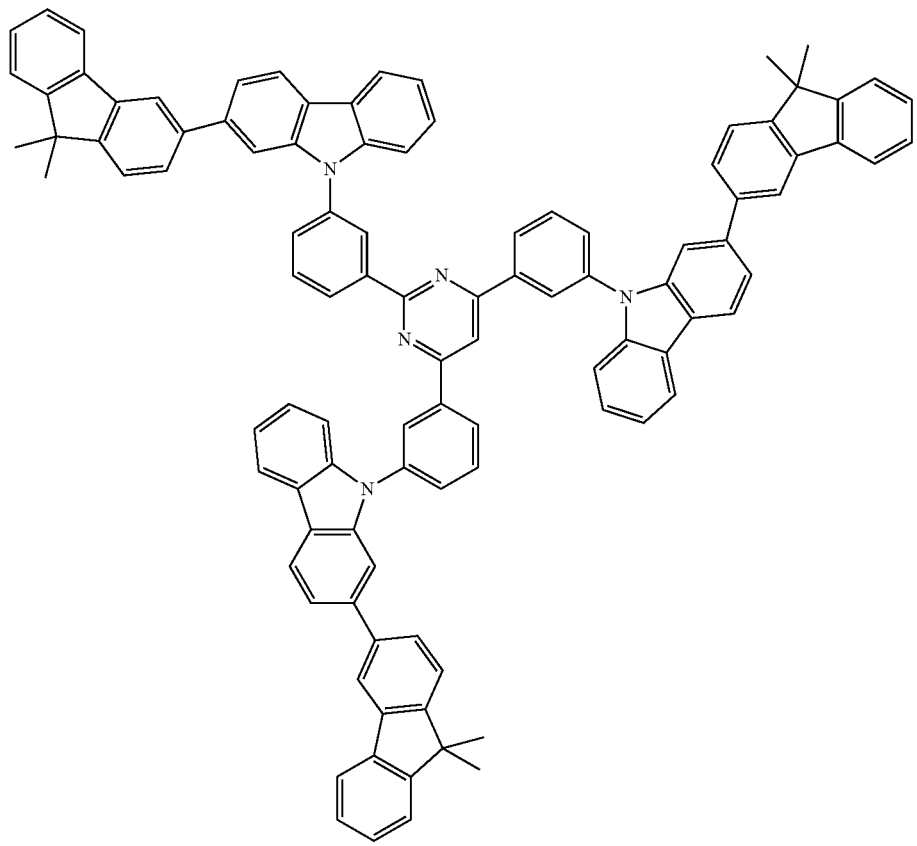 [SMILES: CC1(C)c2ccccc2-c2cc(-c3ccc4c5ccccc5n(-c5cccc(-c6cc(-c7cccc(-n8c9ccccc9c9ccc(-c%10ccc%11c(c%10)-c%10ccccc%10C%11(C)C)cc98)c7)nc(-c7cccc(-n8c9ccccc9c9ccc(-c%10ccc%11c(c%10)-c%10ccccc%10C%11(C)C)cc98)c7)n6)c5)c4c3)ccc21]

1521　　　　　　　　　　　　　　1522
-continued
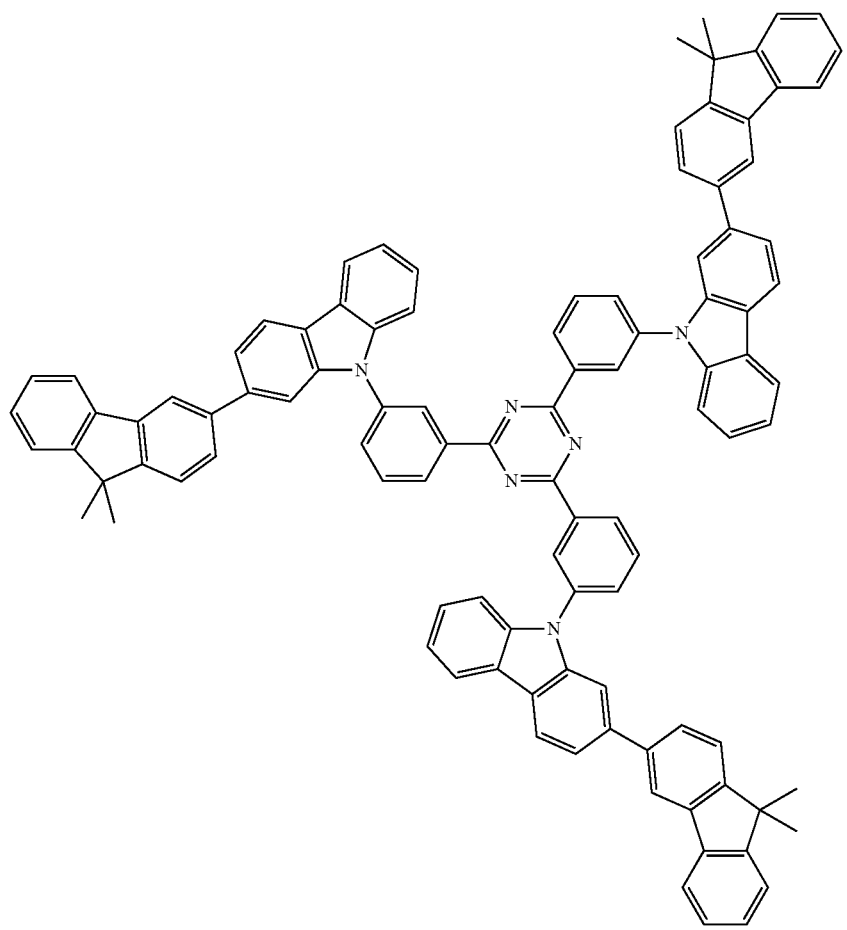 [SMILES: CC1(C)c2ccccc2-c2cc(-c3ccc4c5ccccc5n(-c5cccc(-c6nc(-c7cccc(-n8c9ccccc9c9ccc(-c%10ccc%11c(c%10)-c%10ccccc%10C%11(C)C)cc98)c7)nc(-c7cccc(-n8c9ccccc9c9ccc(-c%10ccc%11c(c%10)-c%10ccccc%10C%11(C)C)cc98)c7)n6)c5)c4c3)ccc21]
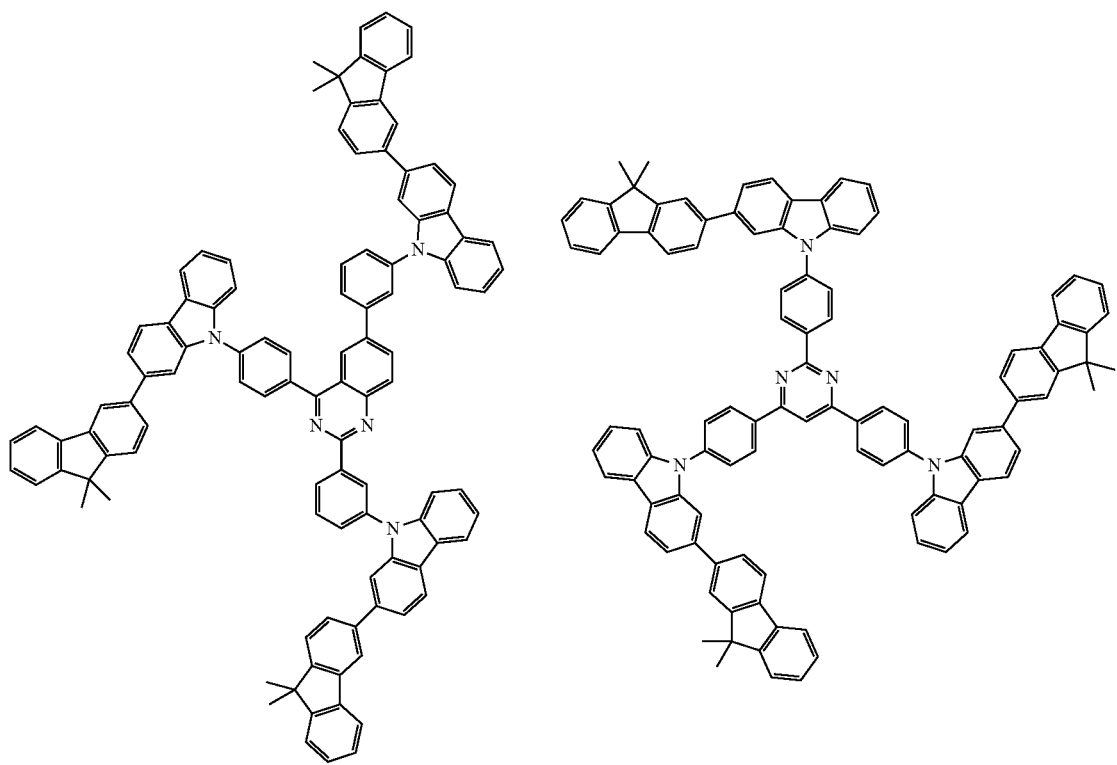 [SMILES: CC1(C)c2ccccc2-c2cc(-c3ccc4c5ccccc5n(-c5ccc(-c6nc(-c7cccc(-n8c9ccccc9c9ccc(-c%10ccc%11c(c%10)-c%10ccccc%10C%11(C)C)cc98)c7)nc7ccc(-c8cccc(-n9c%10ccccc%10c%10ccc(-c%11ccc%12c(c%11)-c%11ccccc%11C%12(C)C)cc%109)c8)cc67)cc5)c4c3)ccc21 ; CC1(C)c2ccccc2-c2ccc(-c3ccc4c5ccccc5n(-c5ccc(-c6cc(-c7ccc(-n8c9ccccc9c9ccc(-c%10ccc%11c(c%10)C(C)(C)c%10ccccc%10-%11)cc98)cc7)nc(-c7ccc(-n8c9ccccc9c9ccc(-c%10ccc%11c(c%10)C(C)(C)c%10ccccc%10-%11)cc98)cc7)n6)cc5)c4c3)cc21]

-continued
| 1523 | 1524 |
|---|---|
| 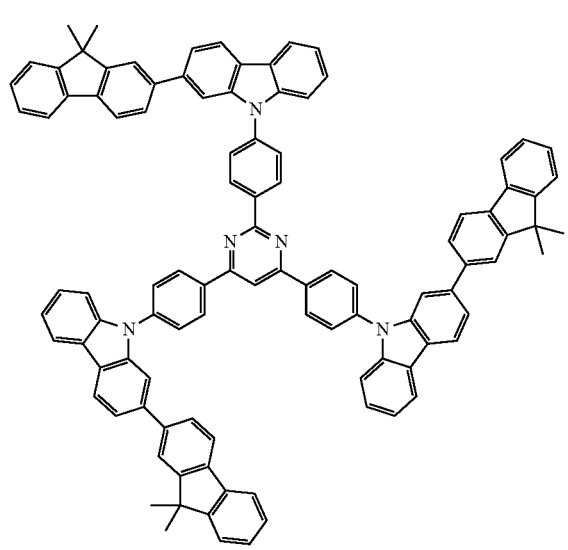 |  |
| 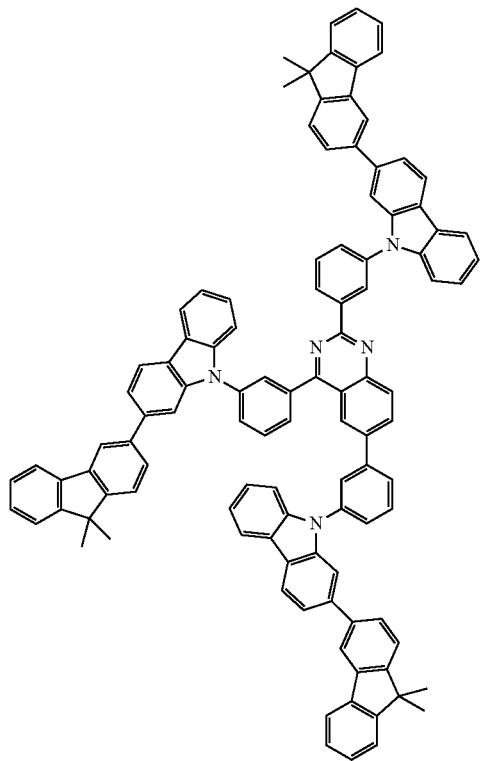 | 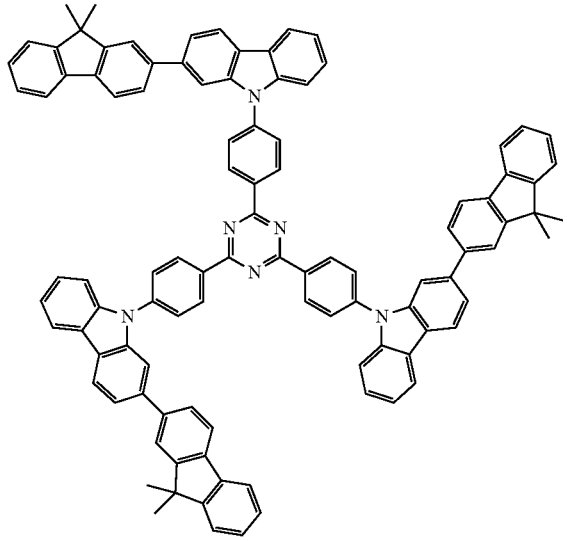 |

1525 1526
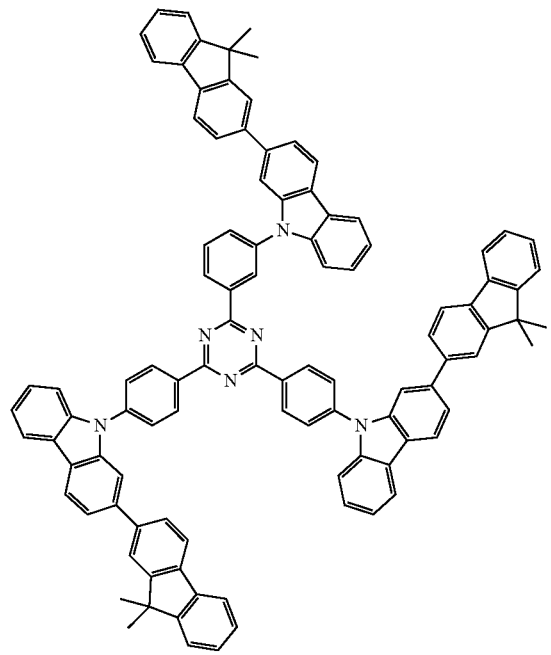 [SMILES: CC1(C)c2ccccc2-c2ccc(-c3ccc4c5ccccc5n(-c5ccc(-c6nc(-c7ccc(-n8c9ccccc9c9ccc(-c%10ccc%11c(c%10)C(C)(C)c%10ccccc%10-%11)cc98)cc7)nc(-c7cccc(-n8c9ccccc9c9ccc(-c%10ccc%11c(c%10)C(C)(C)c%10ccccc%10-%11)cc98)c7)n6)cc5)c4c3)cc21]
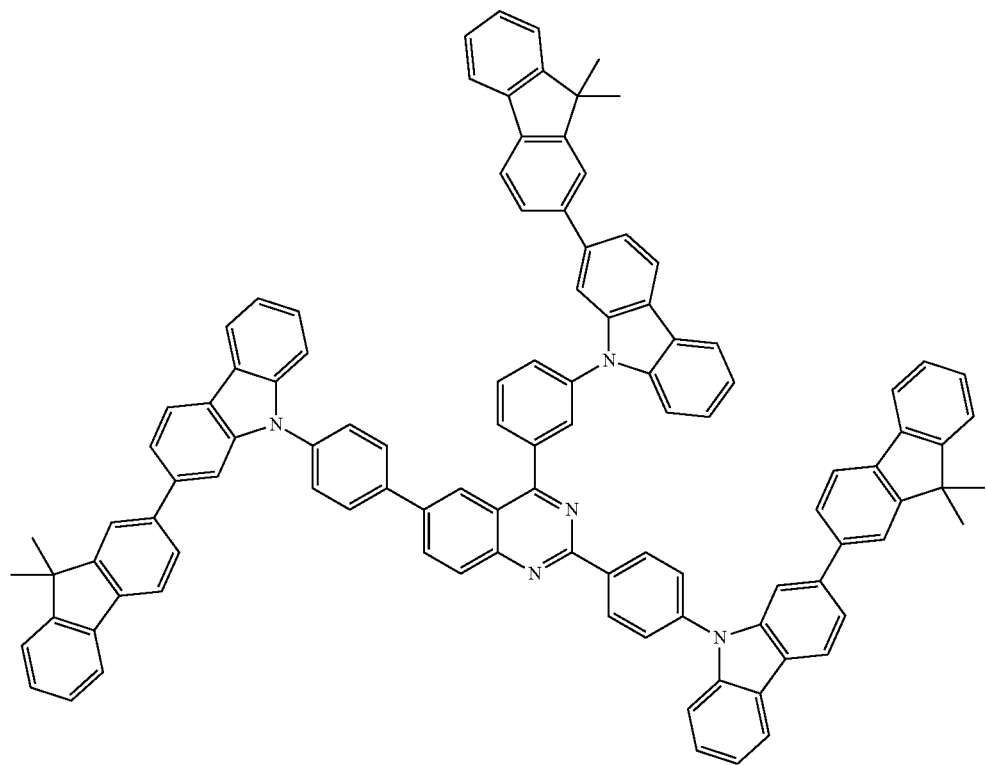

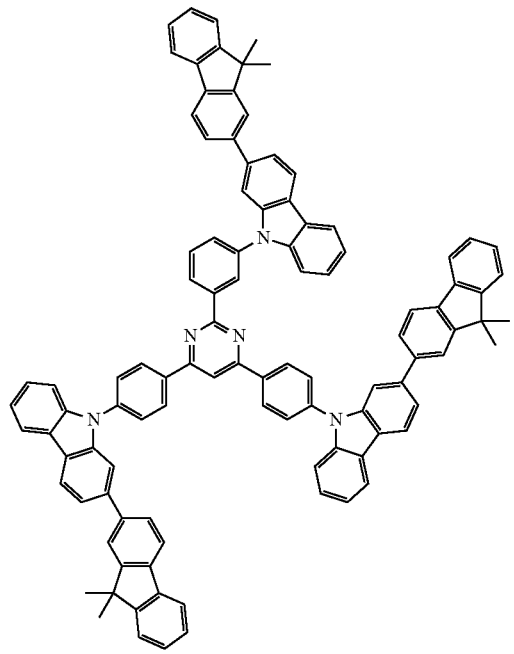 [SMILES: CC1(C)c2ccccc2-c2ccc(-c3ccc4c5ccccc5n(-c5ccc(-c6cc(-c7ccc(-n8c9ccccc9c9ccc(-c%10ccc%11c(c%10)C(C)(C)c%10ccccc%10-%11)cc98)cc7)nc(-c7cccc(-n8c9ccccc9c9ccc(-c%10ccc%11c(c%10)C(C)(C)c%10ccccc%10-%11)cc98)c7)n6)cc5)c4c3)cc21]
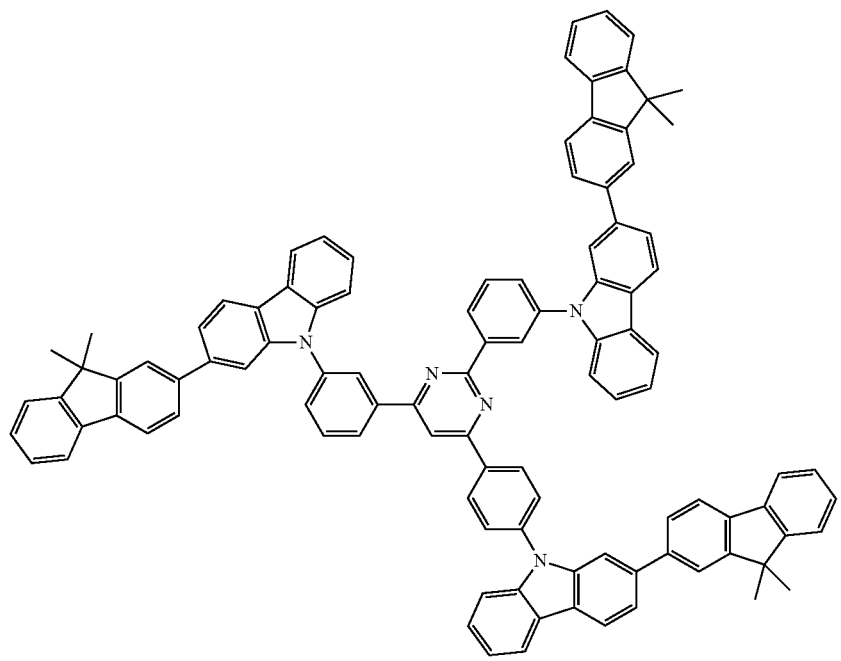

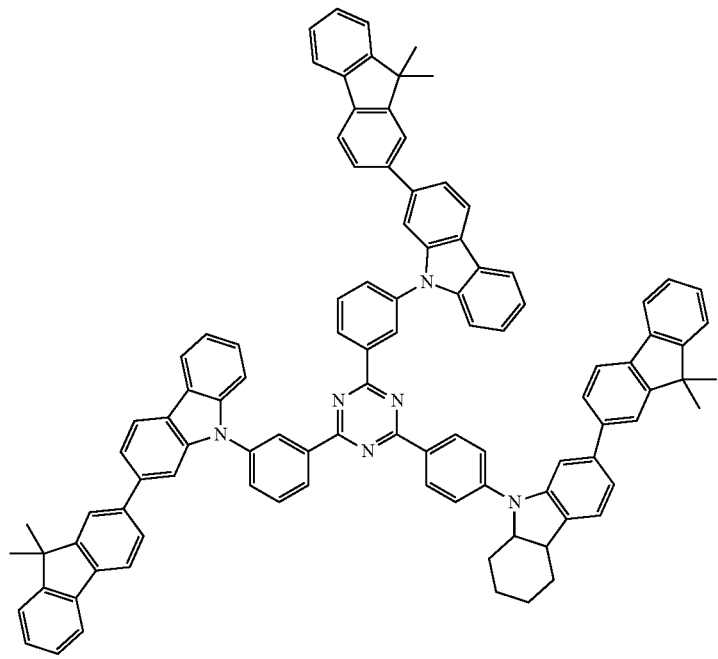
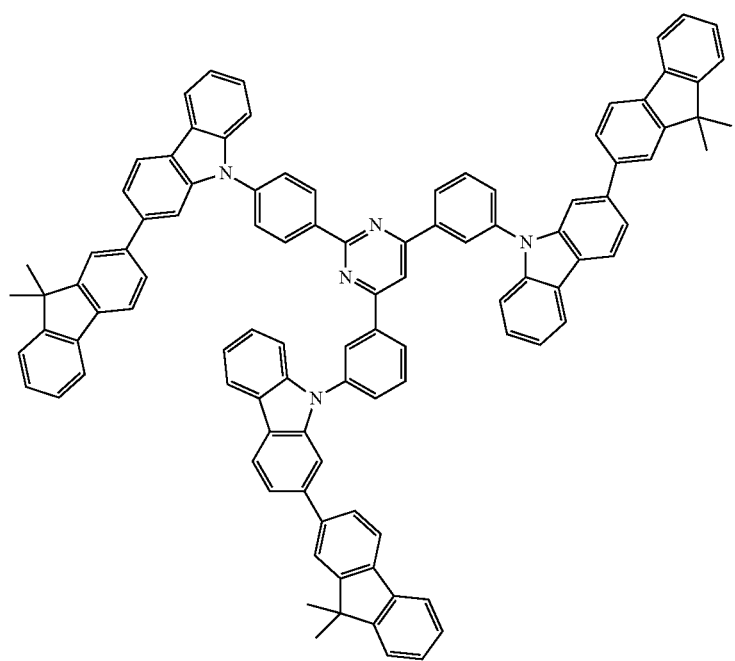

-continued
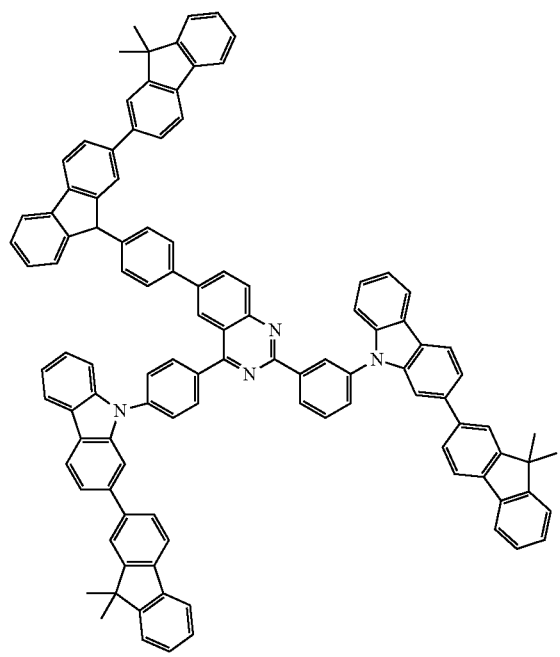
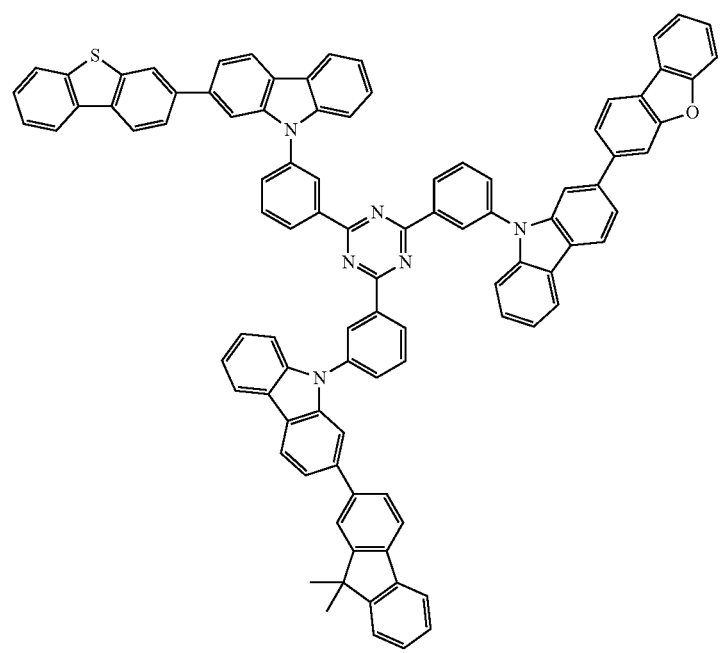

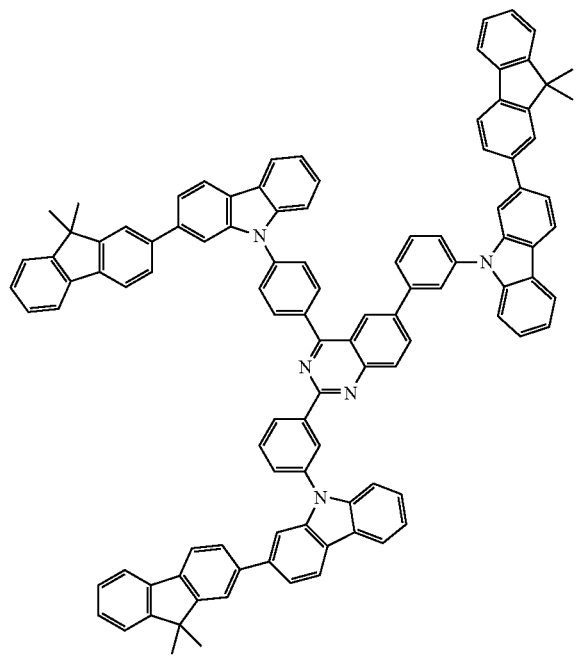
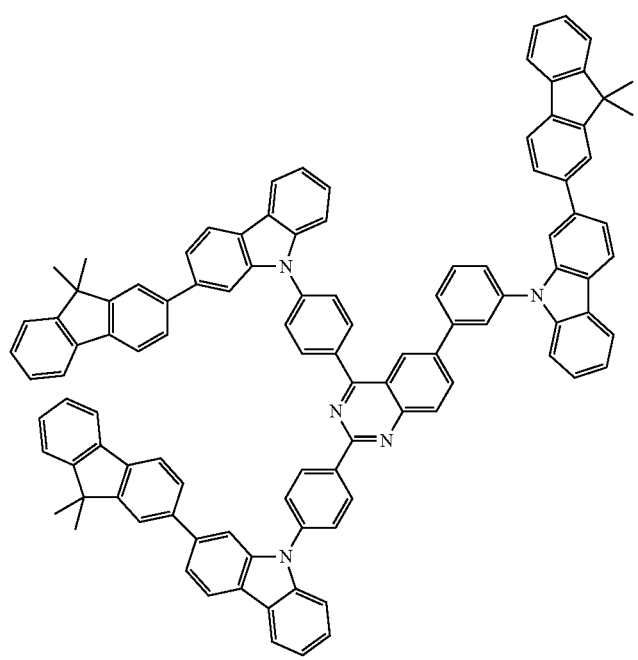

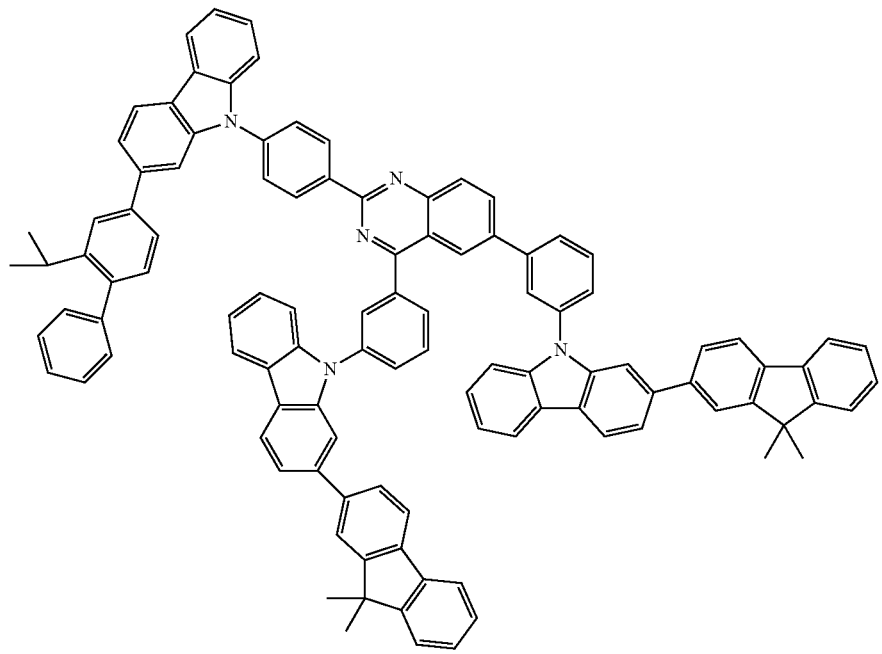
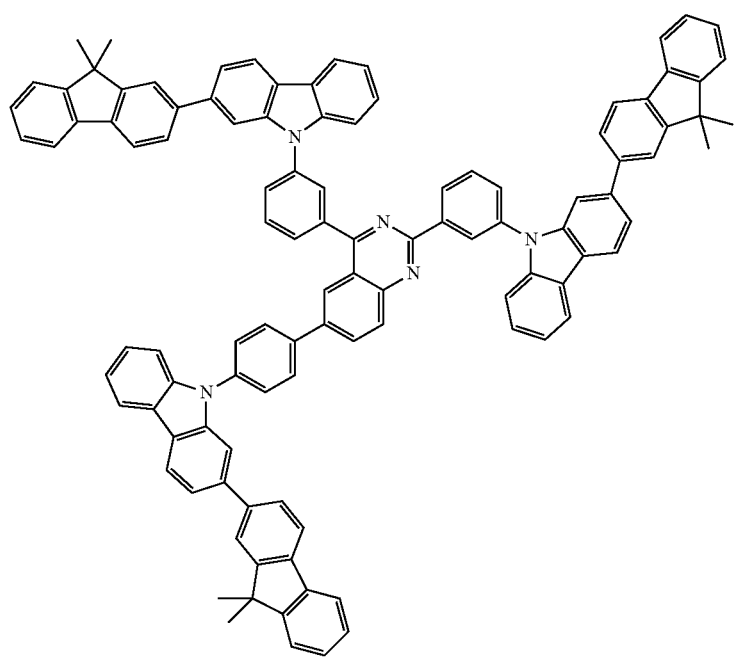

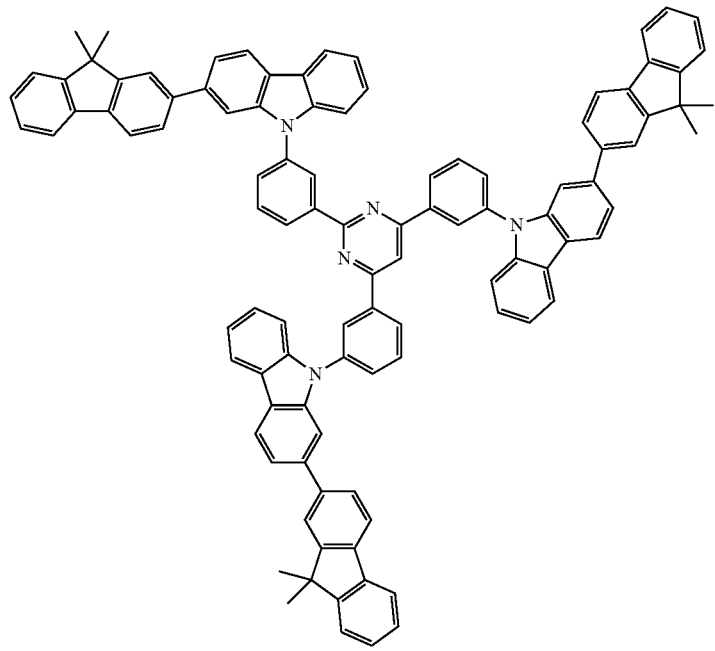
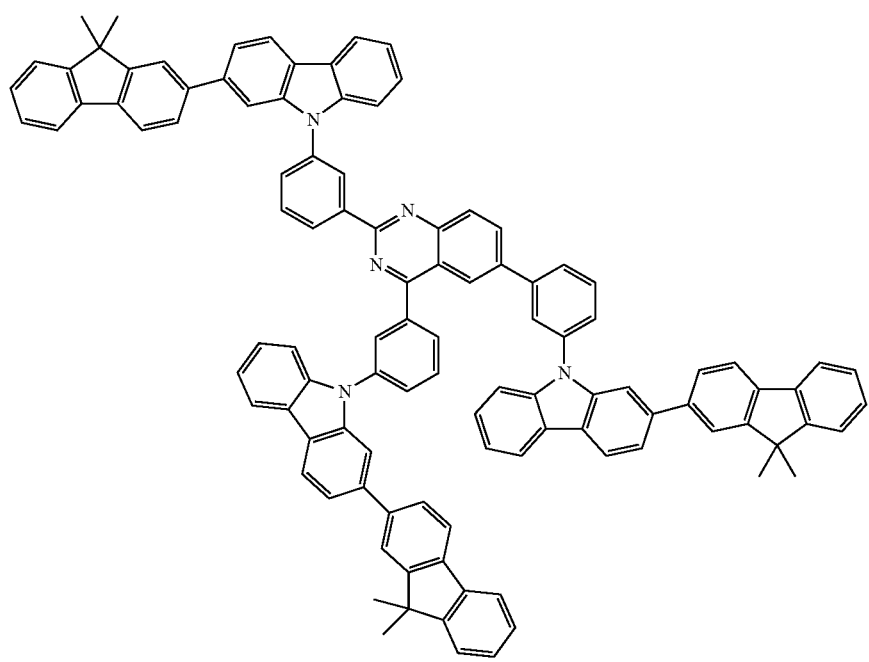

-continued
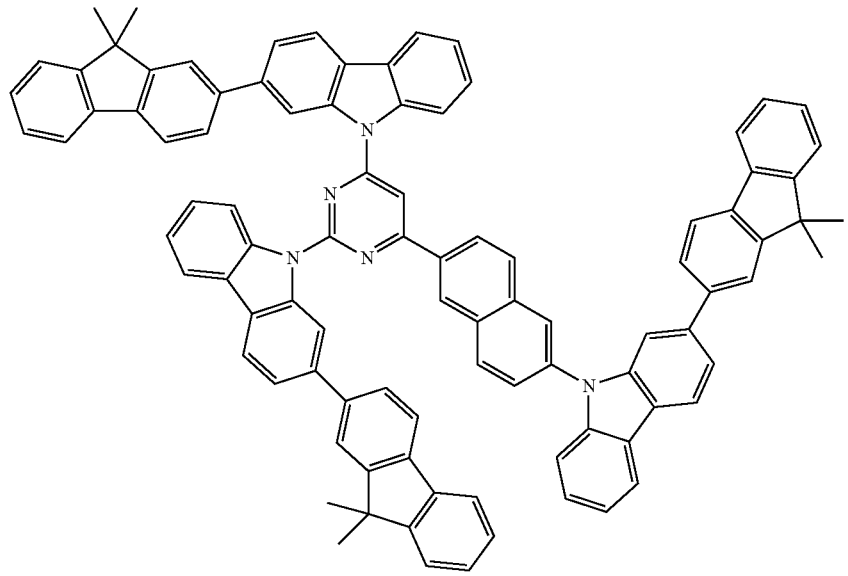
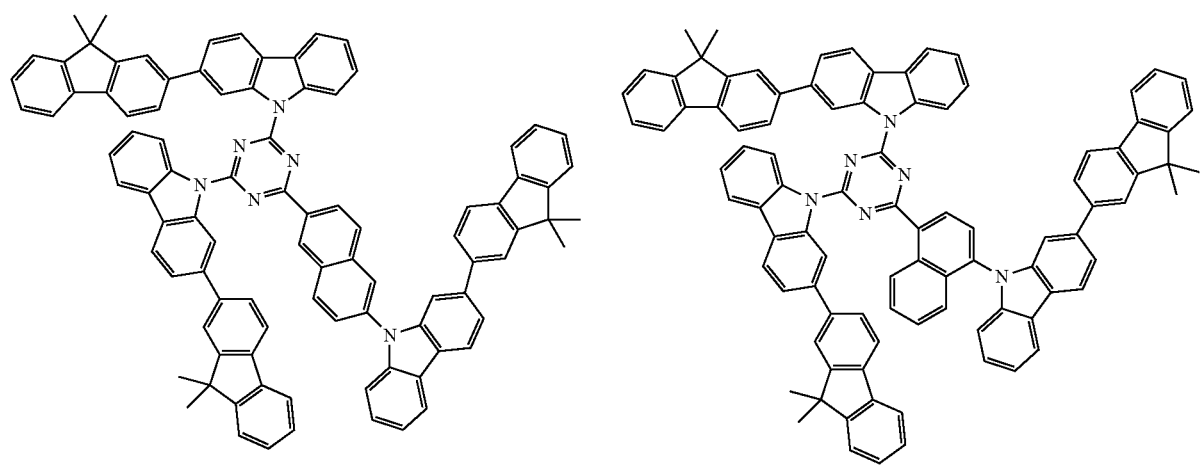 [SMILES: CC1(C)c2ccccc2-c2ccc(-c3ccc4c5ccccc5n(-c5ccc6cc(-c7nc(-n8c9ccccc9c9ccc(-c%10ccc%11c(c%10)C(C)(C)c%10ccccc%10-%11)cc98)nc(-n8c9ccccc9c9ccc(-c%10ccc%11c(c%10)C(C)(C)c%10ccccc%10-%11)cc98)n7)ccc6c5)c4c3)cc21 ; CC1(C)c2ccccc2-c2ccc(-c3ccc4c5ccccc5n(-c5nc(-c6ccc(-n7c8ccccc8c8ccc(-c9ccc%10c(c9)C(C)(C)c9ccccc9-%10)cc87)c7ccccc67)nc(-n6c7ccccc7c7ccc(-c8ccc9c(c8)C(C)(C)c8ccccc8-9)cc76)n5)c4c3)cc21]
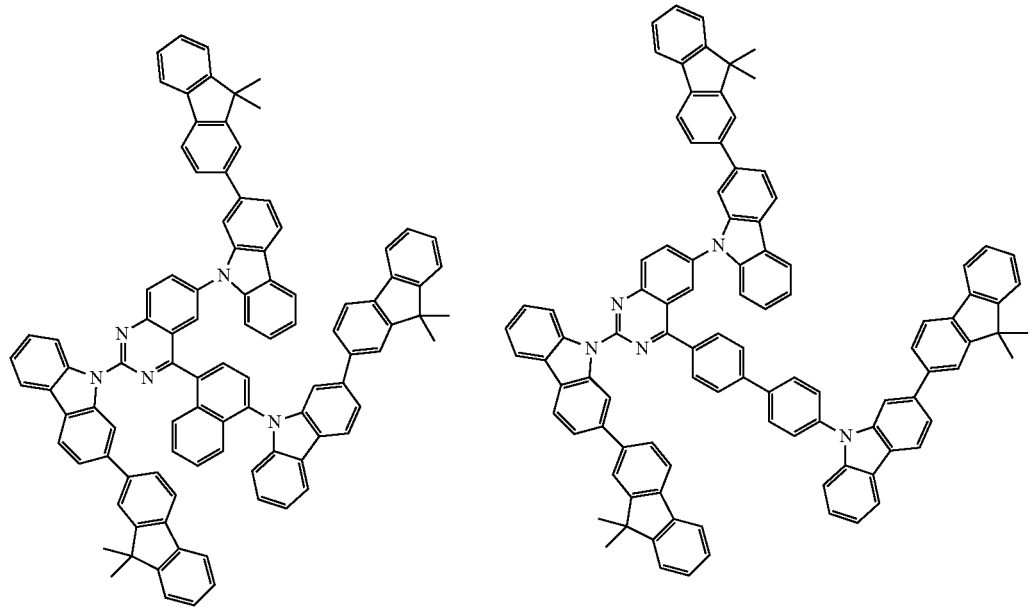 [SMILES: CC1(C)c2ccccc2-c2ccc(-c3ccc4c5ccccc5n(-c5ccc6nc(-n7c8ccccc8c8ccc(-c9ccc%10c(c9)C(C)(C)c9ccccc9-%10)cc87)nc(-c7ccc(-n8c9ccccc9c9ccc(-c%10ccc%11c(c%10)C(C)(C)c%10ccccc%10-%11)cc98)c8ccccc78)c6c5)c4c3)cc21 ; CC1(C)c2ccccc2-c2ccc(-c3ccc4c5ccccc5n(-c5ccc(-c6ccc(-c7nc(-n8c9ccccc9c9ccc(-c%10ccc%11c(c%10)C(C)(C)c%10ccccc%10-%11)cc98)nc8ccc(-n9c%10ccccc%10c%10ccc(-c%11ccc%12c(c%11)C(C)(C)c%11ccccc%11-%12)cc%109)cc78)cc6)cc5)c4c3)cc21]

1541
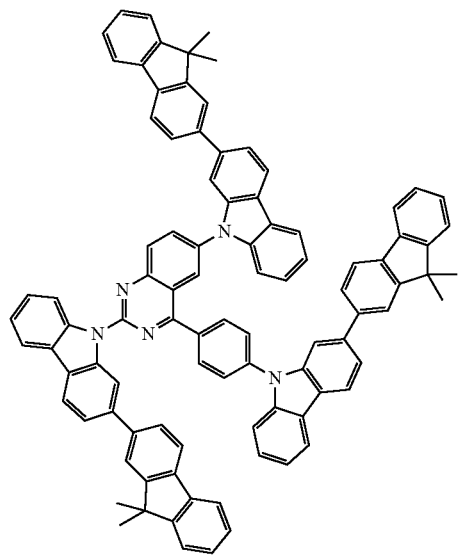
1542
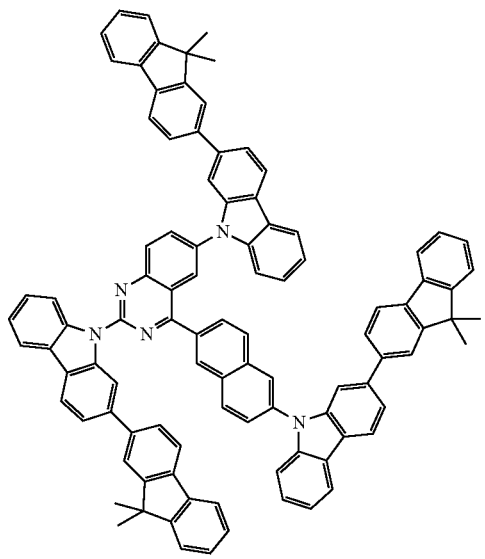
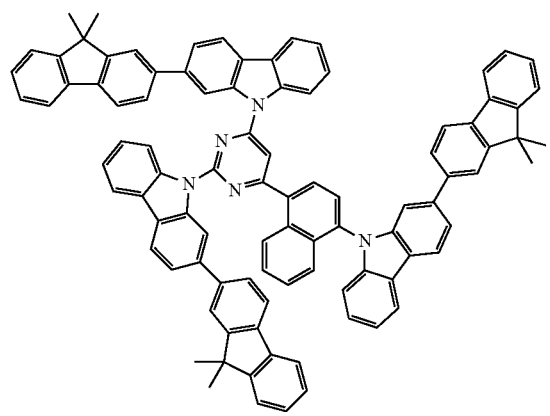
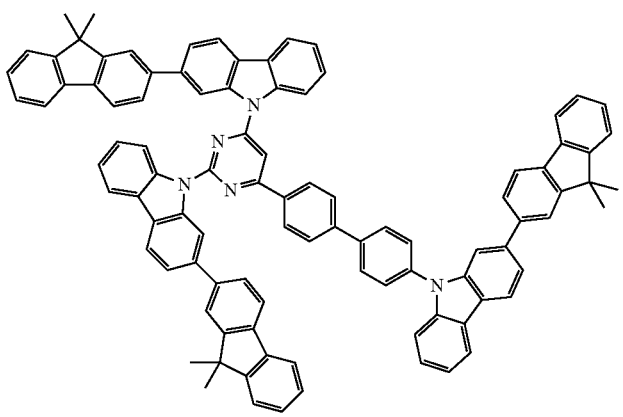
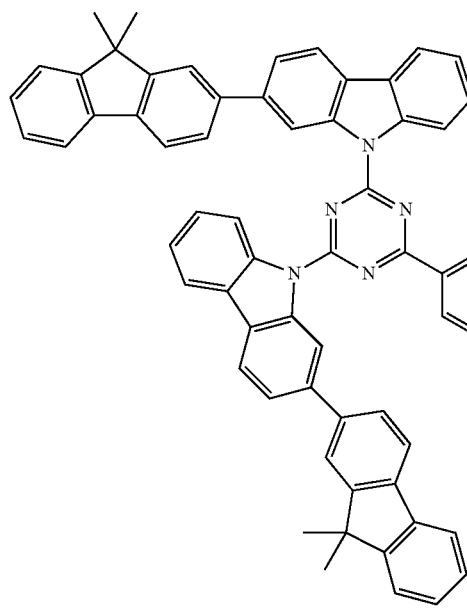
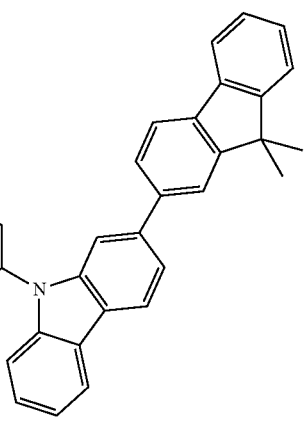

-continued
1543
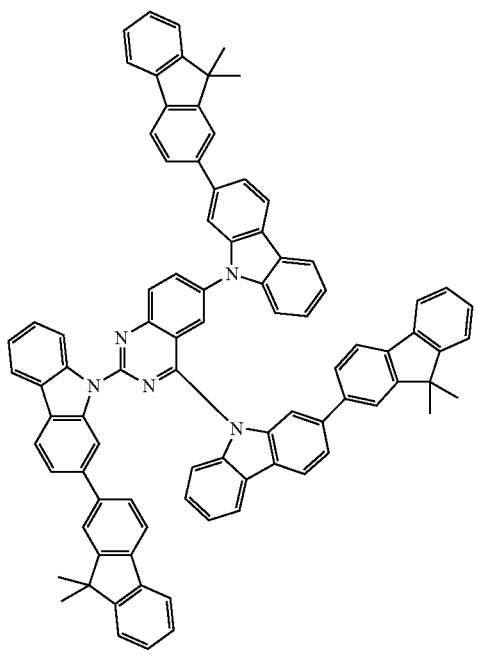
1544
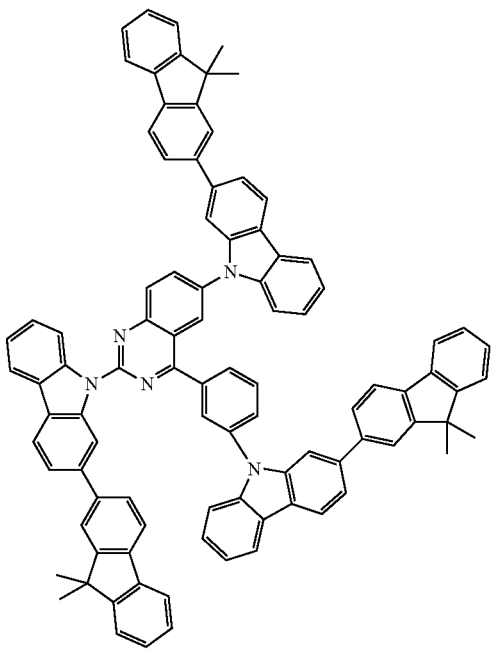
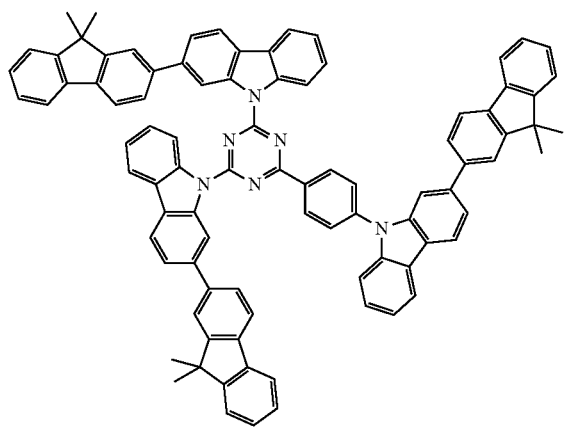
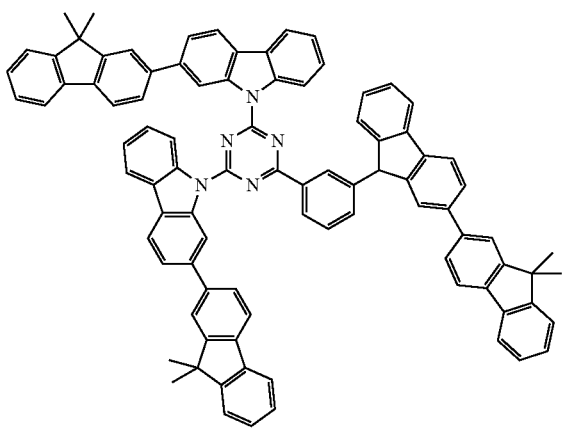
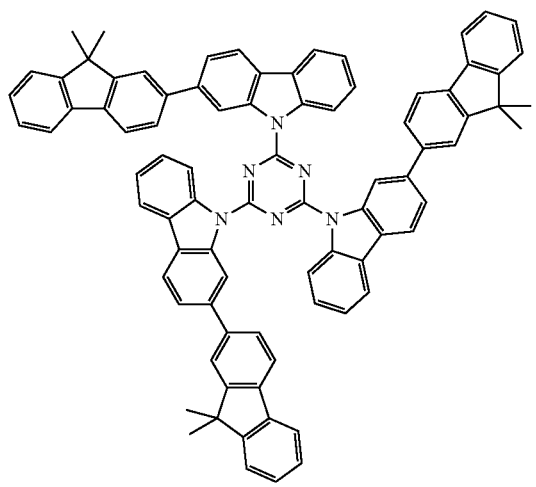
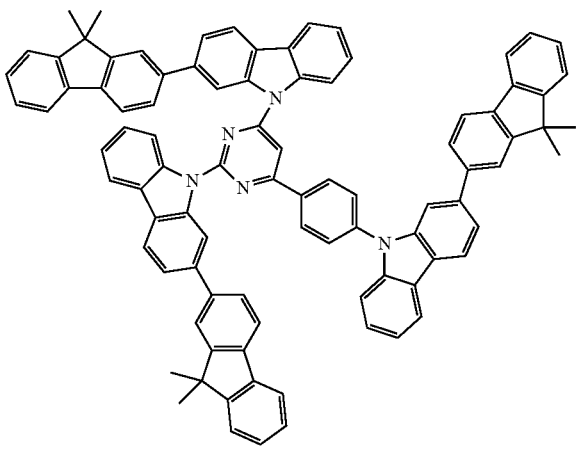

1545 1546
-continued
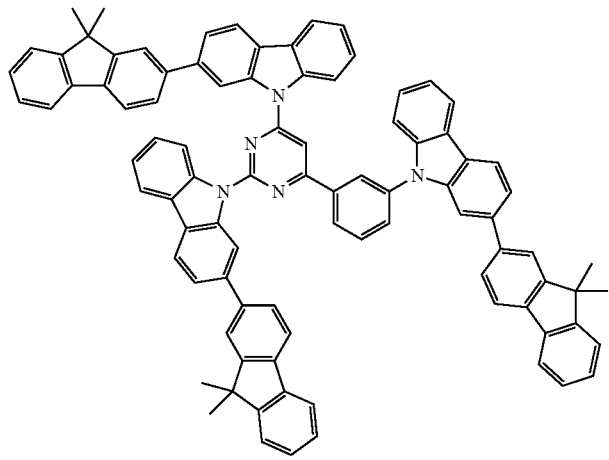
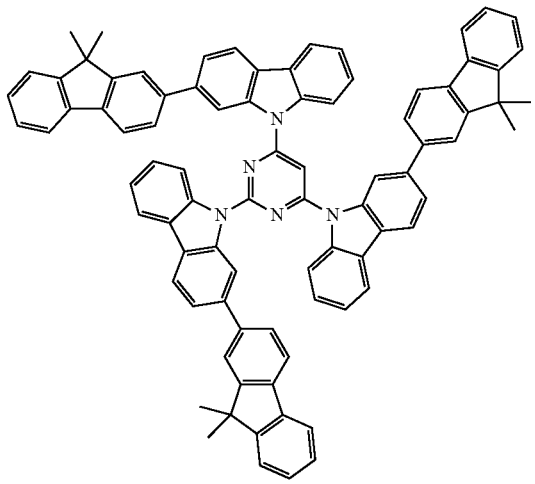
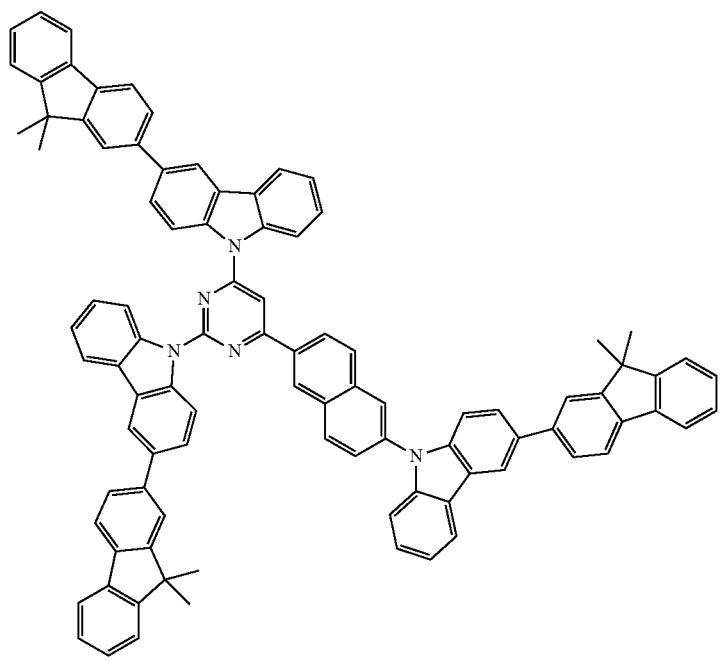

-continued
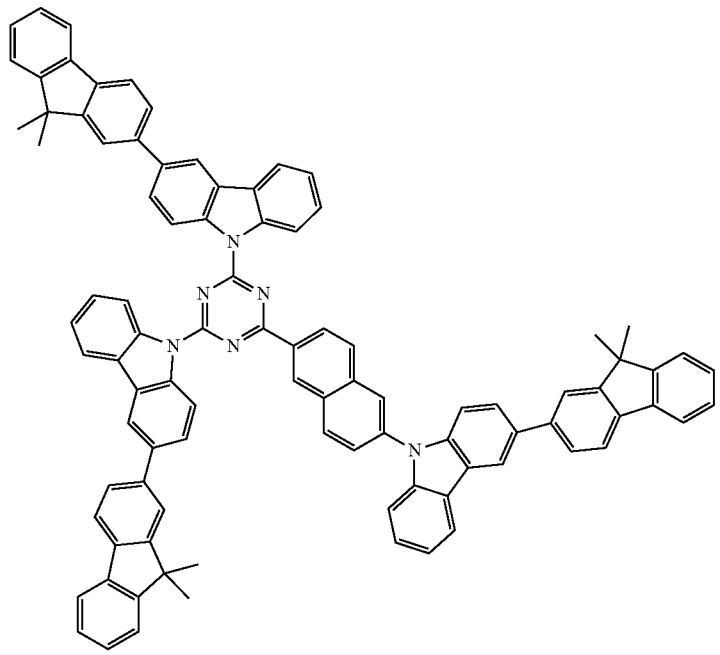
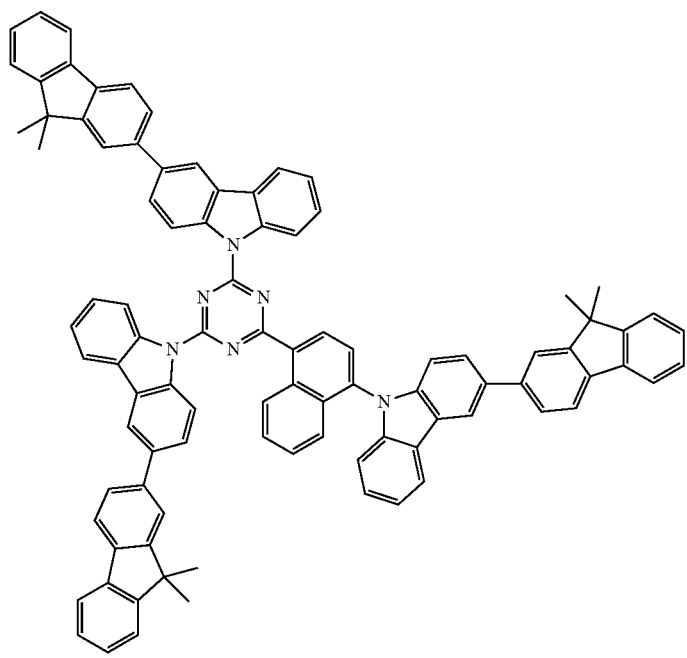

1549
1550
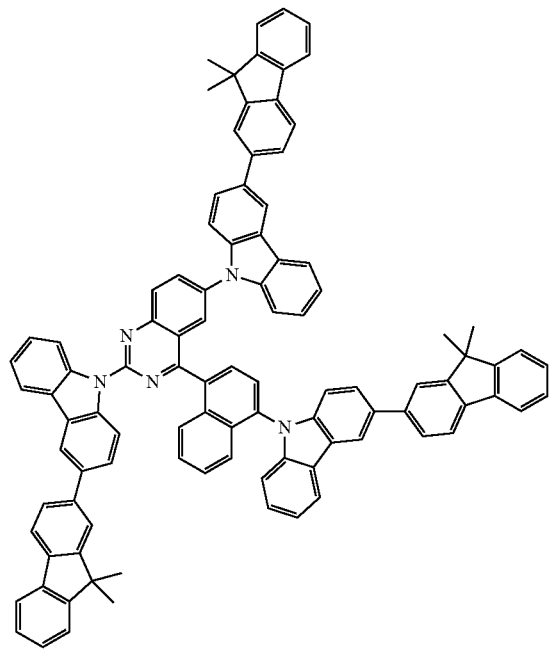
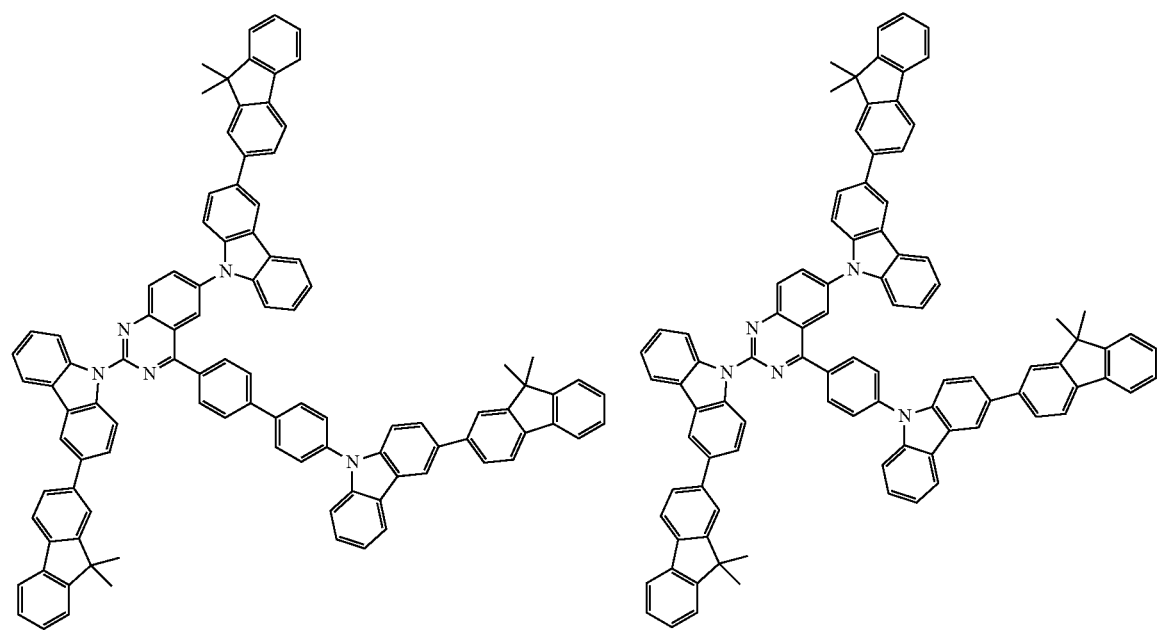 [SMILES: CC1(C)c2ccccc2-c2ccc(-c3ccc4c(c3)c3ccccc3n4-c3ccc(-c4ccc(-c5nc(-n6c7ccccc7c7cc(-c8ccc9c(c8)C(C)(C)c8ccccc8-9)ccc76)nc6ccc(-n7c8ccccc8c8cc(-c9ccc%10c(c9)C(C)(C)c9ccccc9-%10)ccc87)cc56)cc4)cc3)cc21 ; CC1(C)c2ccccc2-c2ccc(-c3ccc4c(c3)c3ccccc3n4-c3ccc(-c4nc(-n5c6ccccc6c6cc(-c7ccc8c(c7)C(C)(C)c7ccccc7-8)ccc65)nc5ccc(-n6c7ccccc7c7cc(-c8ccc9c(c8)C(C)(C)c8ccccc8-9)ccc76)cc45)cc3)cc21]

1551
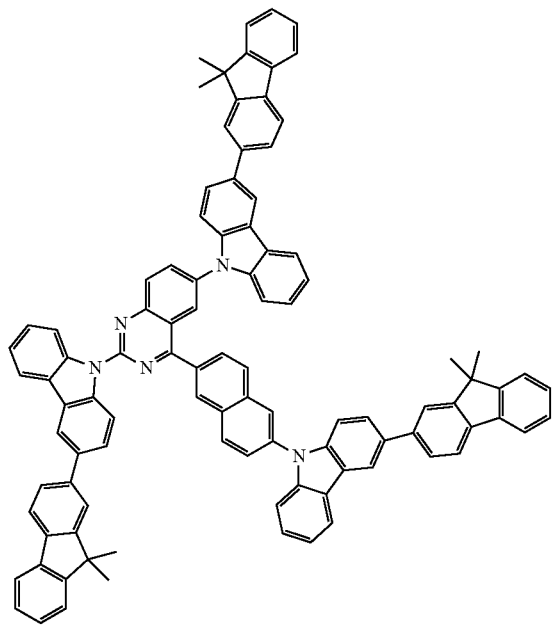
1552
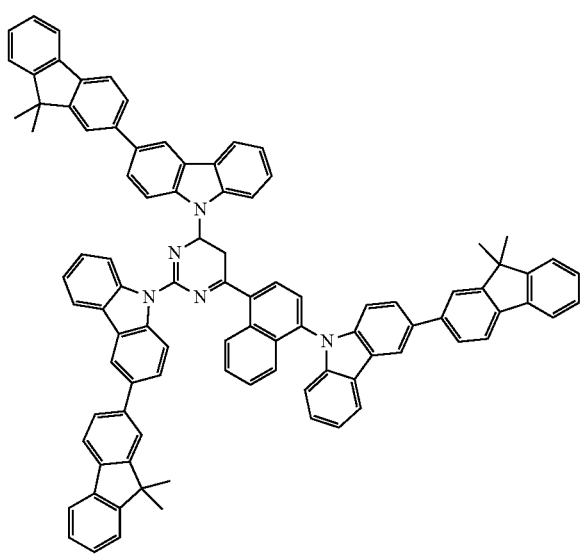
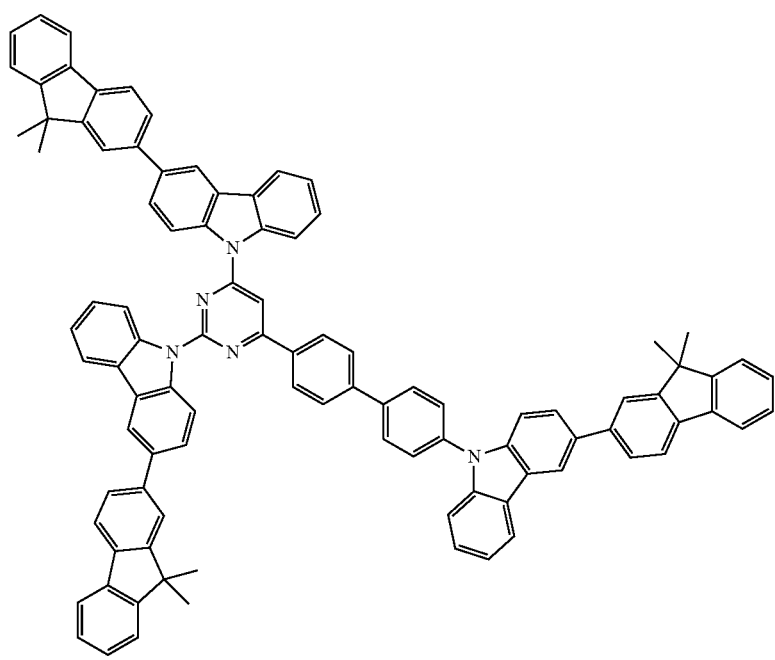

1553 1554
-continued
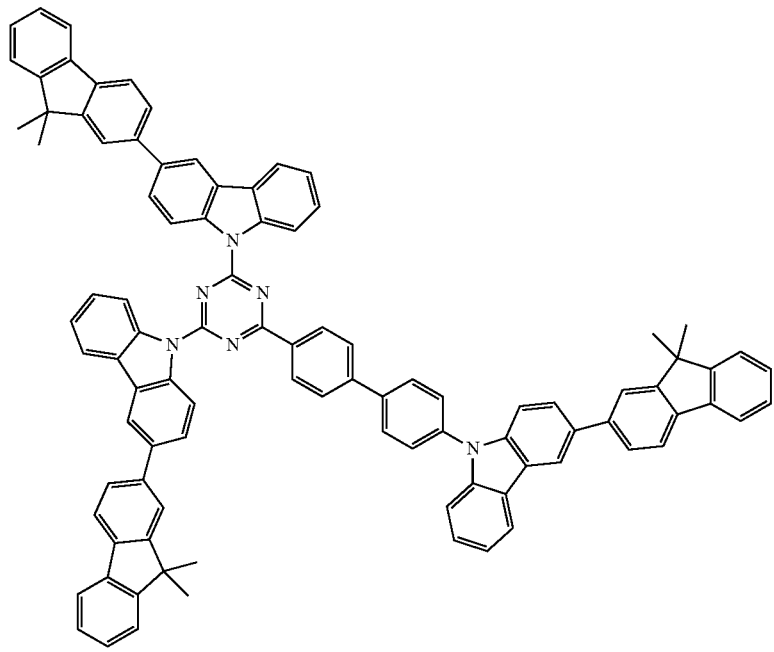
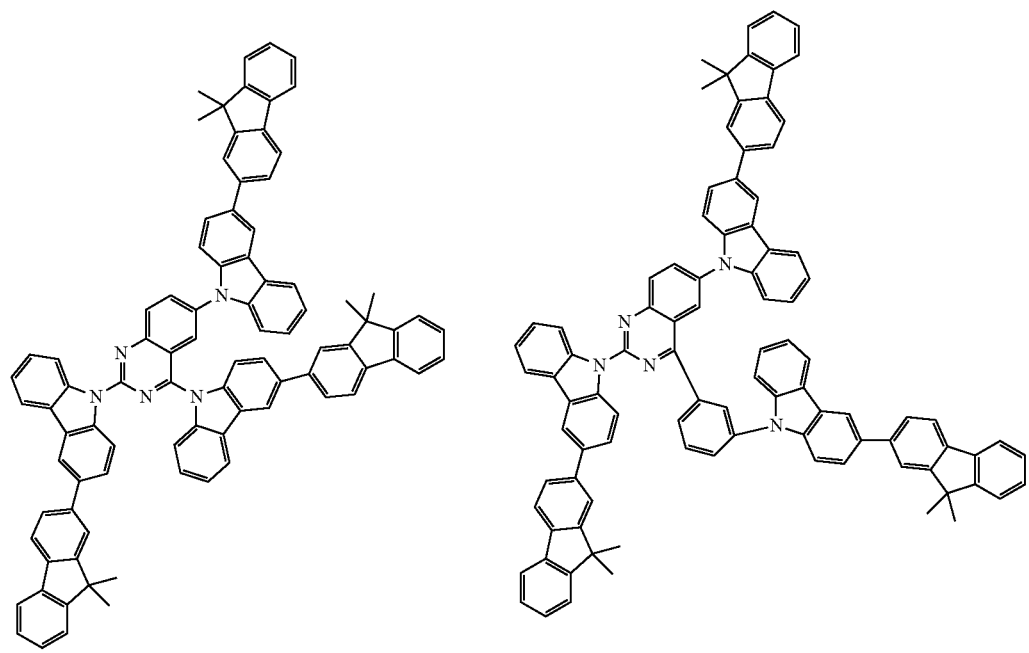

1555 1556
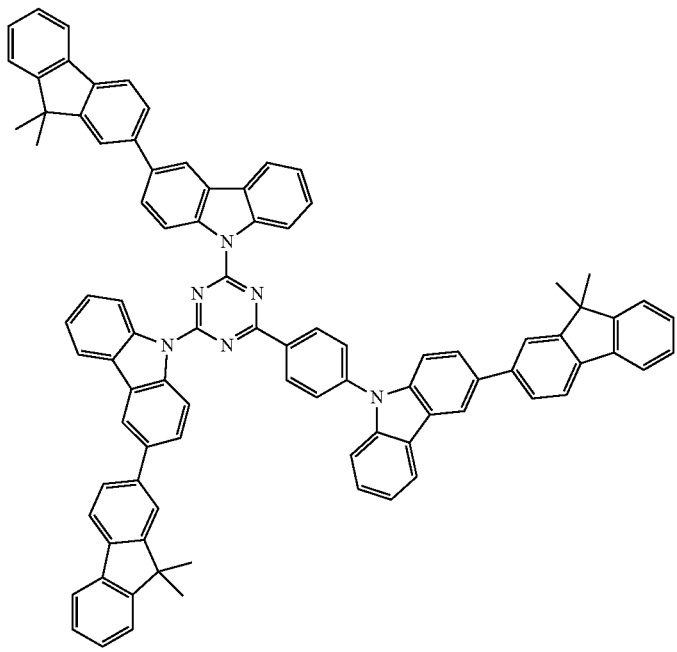
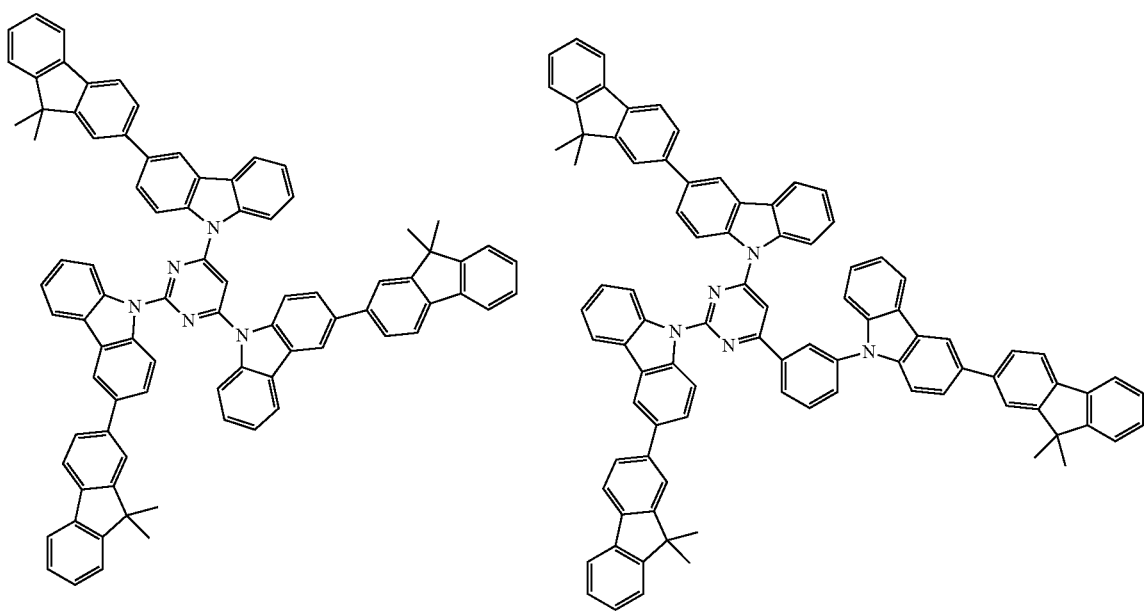

1557
1558
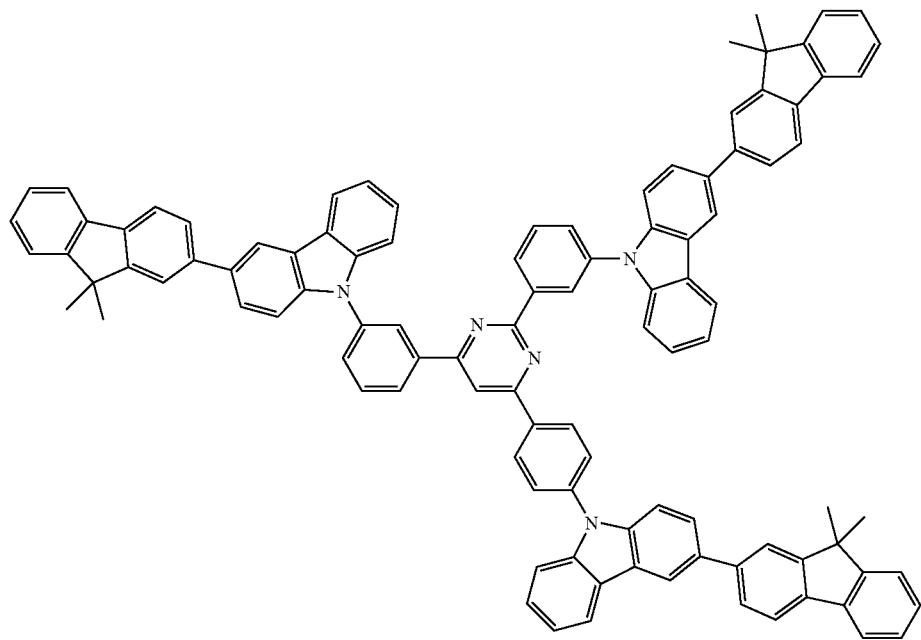
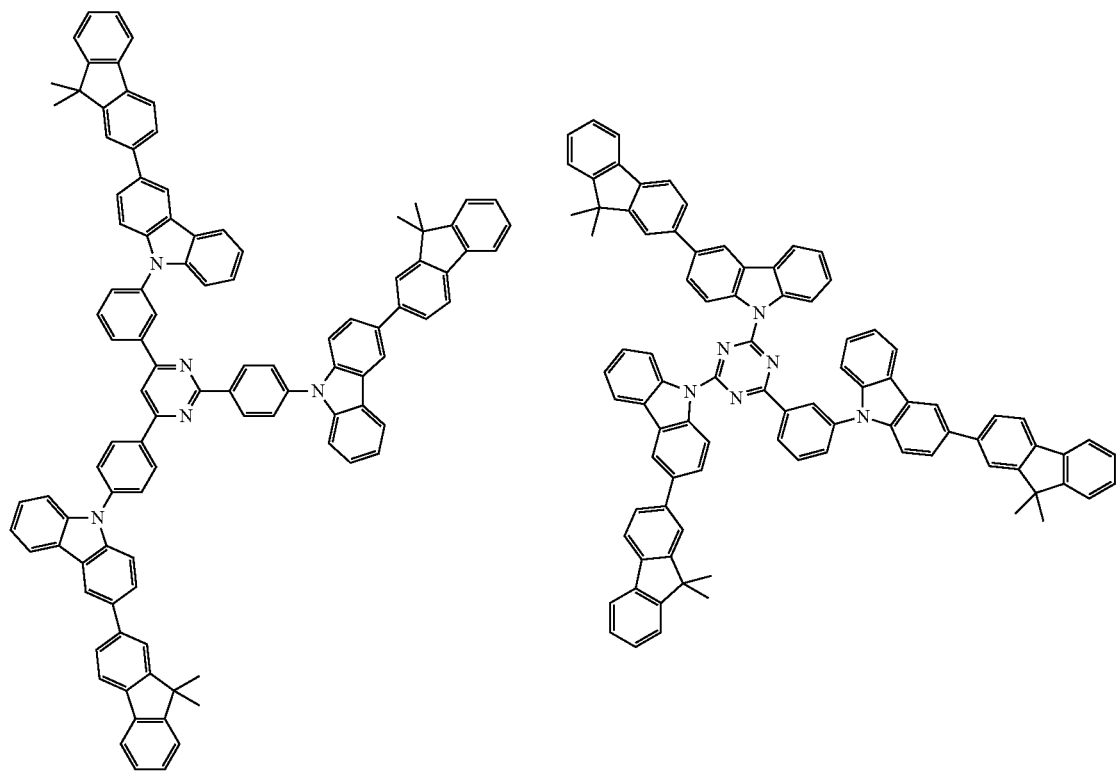 [SMILES: CC1(C)c2ccccc2-c2ccc(-c3ccc4c(c3)c3ccccc3n4-c3ccc(-c4cc(-c5cccc(-n6c7ccccc7c7cc(-c8ccc9c(c8)C(C)(C)c8ccccc8-9)ccc76)c5)nc(-c5ccc(-n6c7ccccc7c7cc(-c8ccc9c(c8)C(C)(C)c8ccccc8-9)ccc76)cc5)n4)cc3)cc21 ; CC1(C)c2ccccc2-c2ccc(-c3ccc4c(c3)c3ccccc3n4-c3cccc(-c4nc(-n5c6ccccc6c6cc(-c7ccc8c(c7)C(C)(C)c7ccccc7-8)ccc65)nc(-n5c6ccccc6c6cc(-c7ccc8c(c7)C(C)(C)c7ccccc7-8)ccc65)n4)c3)cc21]

-continued
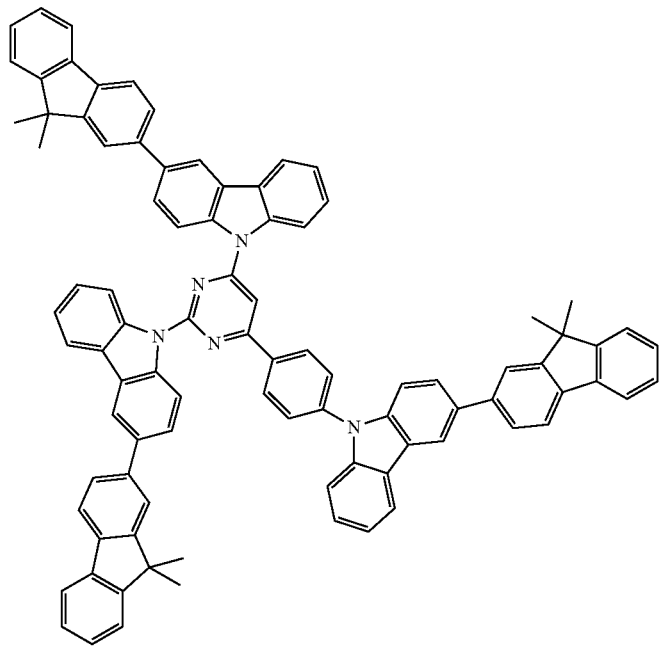 [SMILES: CC1(C)c2ccccc2-c2ccc(-c3ccc4c(c3)c3ccccc3n4-c3ccc(-c4cc(-n5c6ccccc6c6cc(-c7ccc8c(c7)C(C)(C)c7ccccc7-8)ccc65)nc(-n5c6ccccc6c6cc(-c7ccc8c(c7)C(C)(C)c7ccccc7-8)ccc65)n4)cc3)cc21]
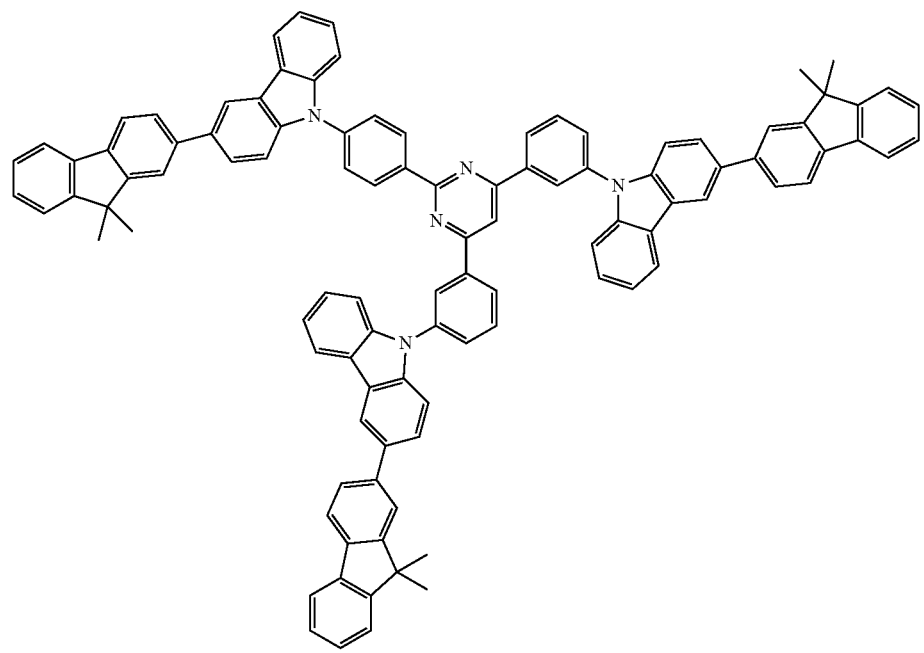

1561
1562
-continued
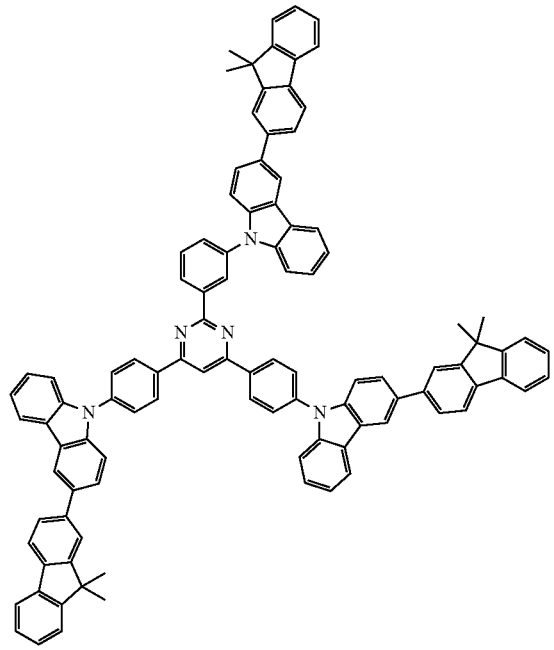
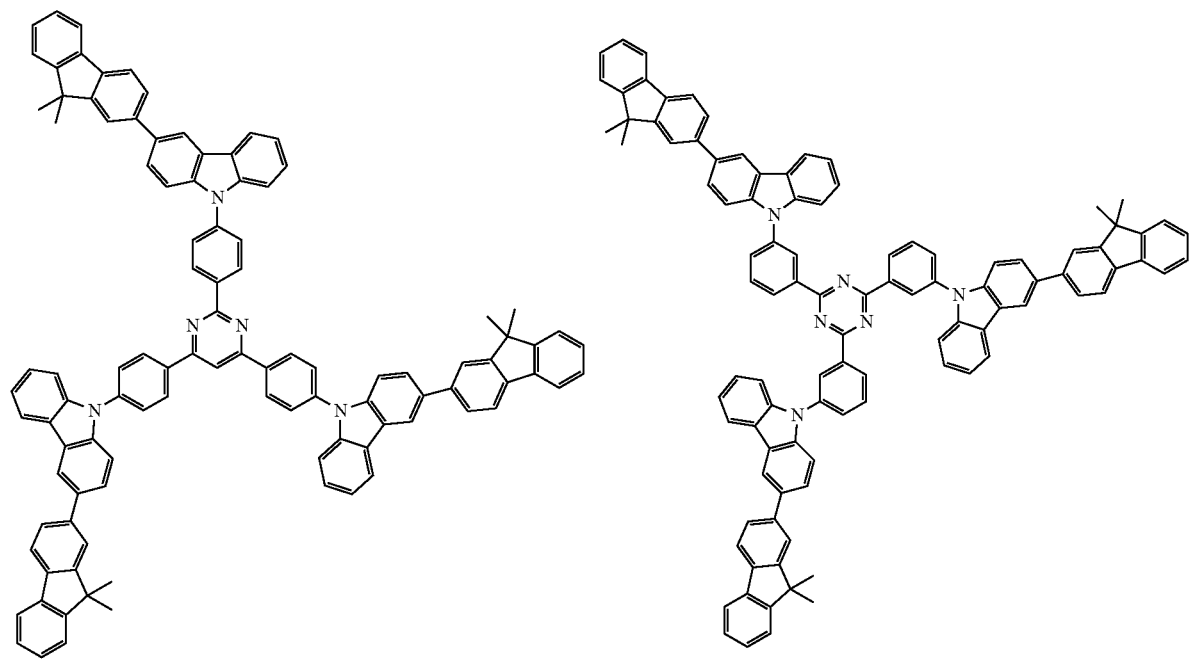 [SMILES: CC1(C)c2ccccc2-c2ccc(-c3ccc4c(c3)c3ccccc3n4-c3ccc(-c4cc(-c5ccc(-n6c7ccccc7c7cc(-c8ccc9c(c8)C(C)(C)c8ccccc8-9)ccc76)cc5)nc(-c5ccc(-n6c7ccccc7c7cc(-c8ccc9c(c8)C(C)(C)c8ccccc8-9)ccc76)cc5)n4)cc3)cc21 ; CC1(C)c2ccccc2-c2ccc(-c3ccc4c(c3)c3ccccc3n4-c3cccc(-c4nc(-c5cccc(-n6c7ccccc7c7cc(-c8ccc9c(c8)C(C)(C)c8ccccc8-9)ccc76)c5)nc(-c5cccc(-n6c7ccccc7c7cc(-c8ccc9c(c8)C(C)(C)c8ccccc8-9)ccc76)c5)n4)c3)cc21]

1563 1564
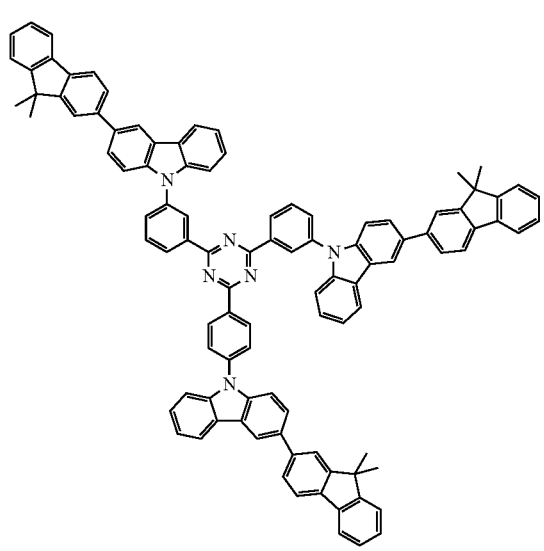
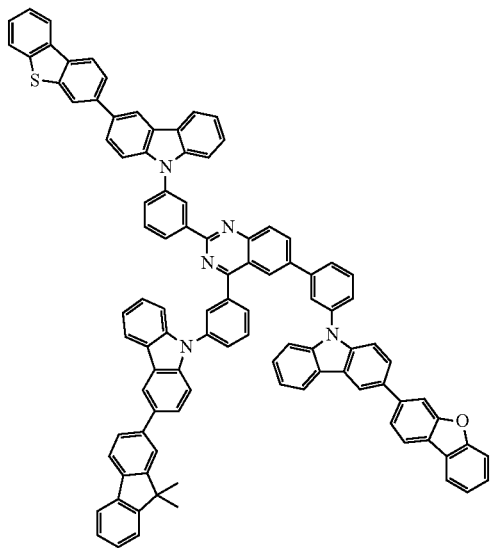
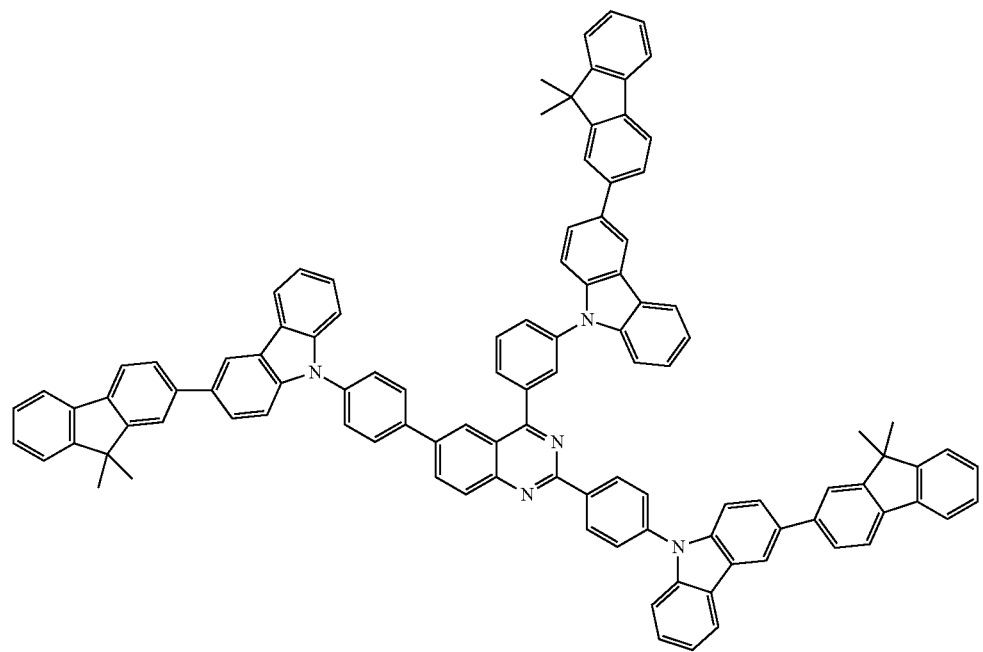 [SMILES: CC1(C)c2ccccc2-c2ccc(-c3ccc4c(c3)c3ccccc3n4-c3ccc(-c4ccc5nc(-c6ccc(-n7c8ccccc8c8cc(-c9ccc%10c(c9)C(C)(C)c9ccccc9-%10)ccc87)cc6)nc(-c6cccc(-n7c8ccccc8c8cc(-c9ccc%10c(c9)C(C)(C)c9ccccc9-%10)ccc87)c6)c5c4)cc3)cc21]

1565
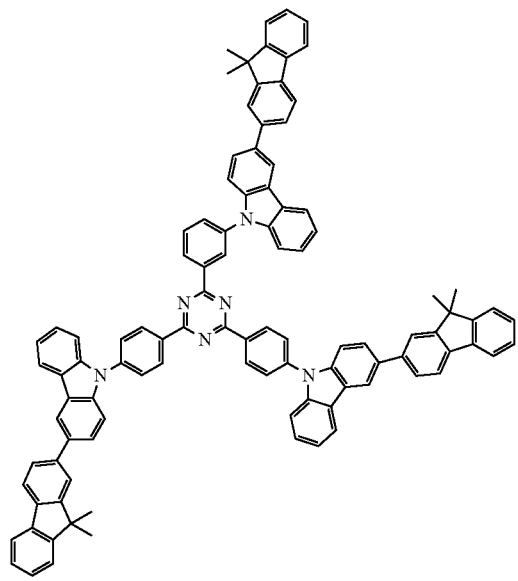
-continued
1566
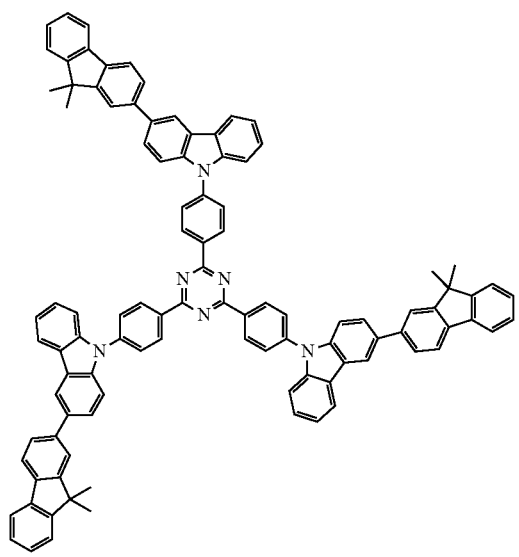
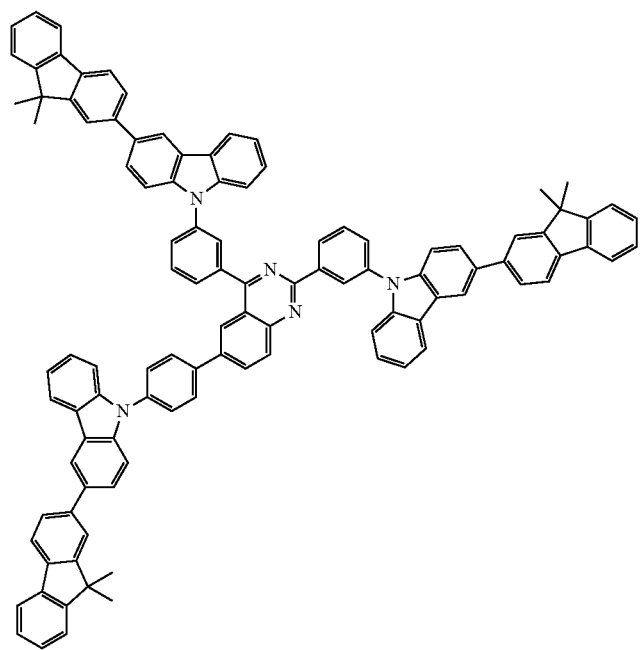 [SMILES: CC1(C)c2ccccc2-c2ccc(-c3ccc4c(c3)c3ccccc3n4-c3ccc(-c4ccc5nc(-c6cccc(-n7c8ccccc8c8cc(-c9ccc%10c(c9)C(C)(C)c9ccccc9-%10)ccc87)c6)nc(-c6cccc(-n7c8ccccc8c8cc(-c9ccc%10c(c9)C(C)(C)c9ccccc9-%10)ccc87)c6)c5c4)cc3)cc21]

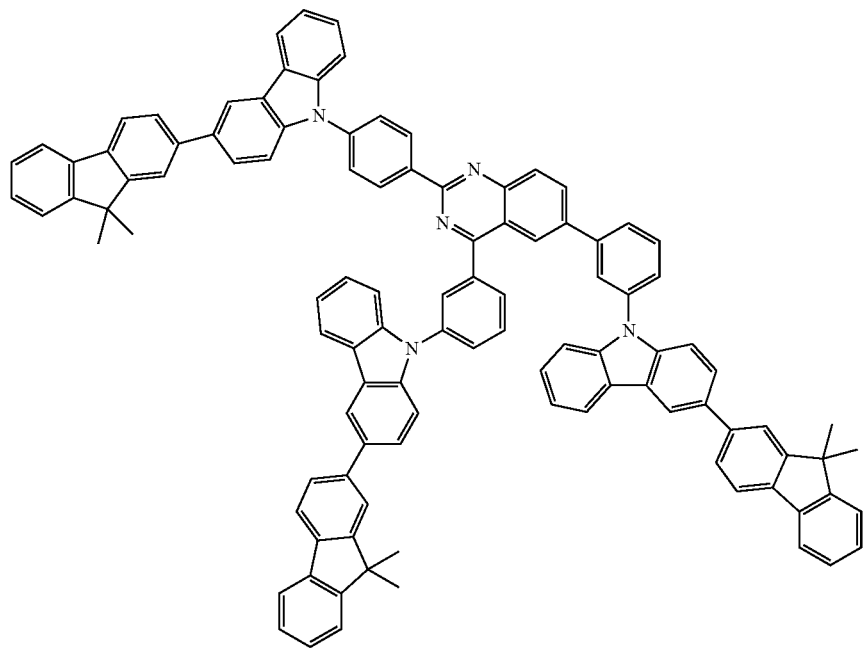 [SMILES: CC1(C)c2ccccc2-c2ccc(-c3ccc4c(c3)c3ccccc3n4-c3ccc(-c4nc(-c5cccc(-n6c7ccccc7c7cc(-c8ccc9c(c8)C(C)(C)c8ccccc8-9)ccc76)c5)c5cc(-c6cccc(-n7c8ccccc8c8cc(-c9ccc%10c(c9)C(C)(C)c9ccccc9-%10)ccc87)c6)ccc5n4)cc3)cc21]
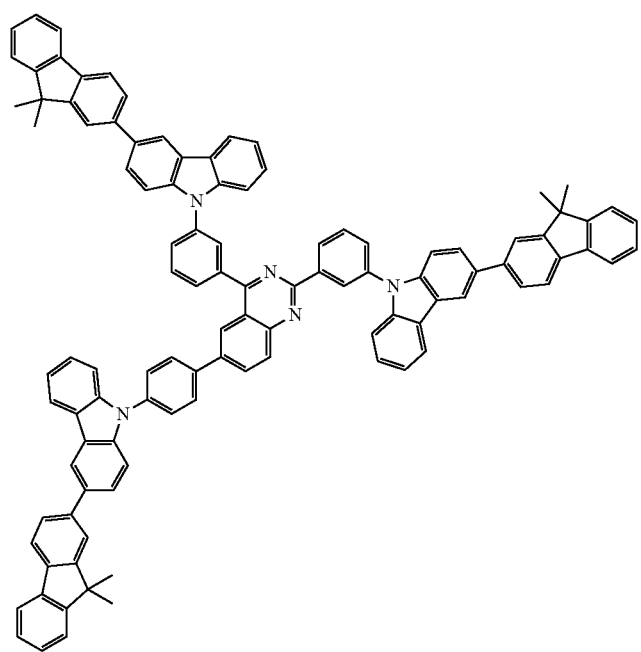 [SMILES: CC1(C)c2ccccc2-c2ccc(-c3ccc4c(c3)c3ccccc3n4-c3ccc(-c4ccc5nc(-c6cccc(-n7c8ccccc8c8cc(-c9ccc%10c(c9)C(C)(C)c9ccccc9-%10)ccc87)c6)nc(-c6cccc(-n7c8ccccc8c8cc(-c9ccc%10c(c9)C(C)(C)c9ccccc9-%10)ccc87)c6)c5c4)cc3)cc21]

1569 1570
-continued
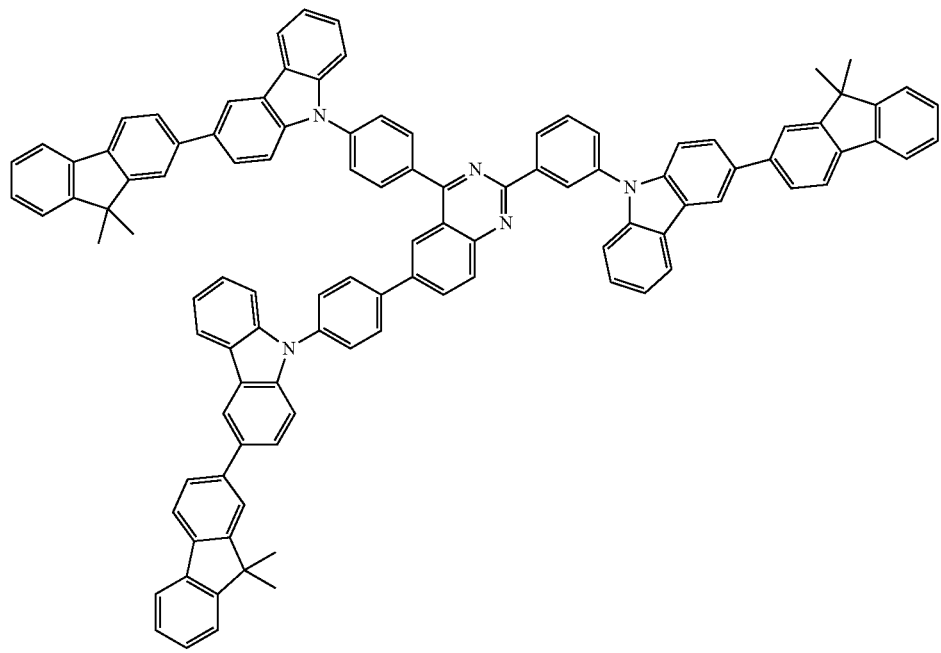 [SMILES: CC1(C)c2ccccc2-c2ccc(-c3ccc4c(c3)c3ccccc3n4-c3ccc(-c4ccc5nc(-c6cccc(-n7c8ccccc8c8cc(-c9ccc%10c(c9)C(C)(C)c9ccccc9-%10)ccc87)c6)nc(-c6ccc(-n7c8ccccc8c8cc(-c9ccc%10c(c9)C(C)(C)c9ccccc9-%10)ccc87)cc6)c5c4)cc3)cc21]
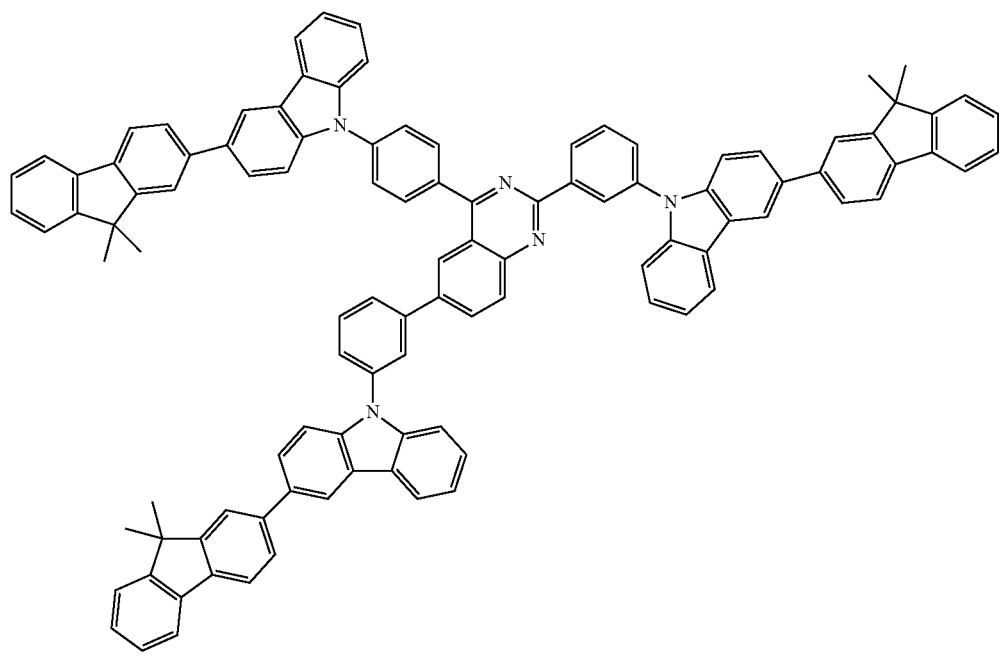 [SMILES: CC1(C)c2ccccc2-c2ccc(-c3ccc4c(c3)c3ccccc3n4-c3ccc(-c4nc(-c5cccc(-n6c7ccccc7c7cc(-c8ccc9c(c8)C(C)(C)c8ccccc8-9)ccc76)c5)nc5ccc(-c6cccc(-n7c8ccccc8c8cc(-c9ccc%10c(c9)C(C)(C)c9ccccc9-%10)ccc87)c6)cc45)cc3)cc21]

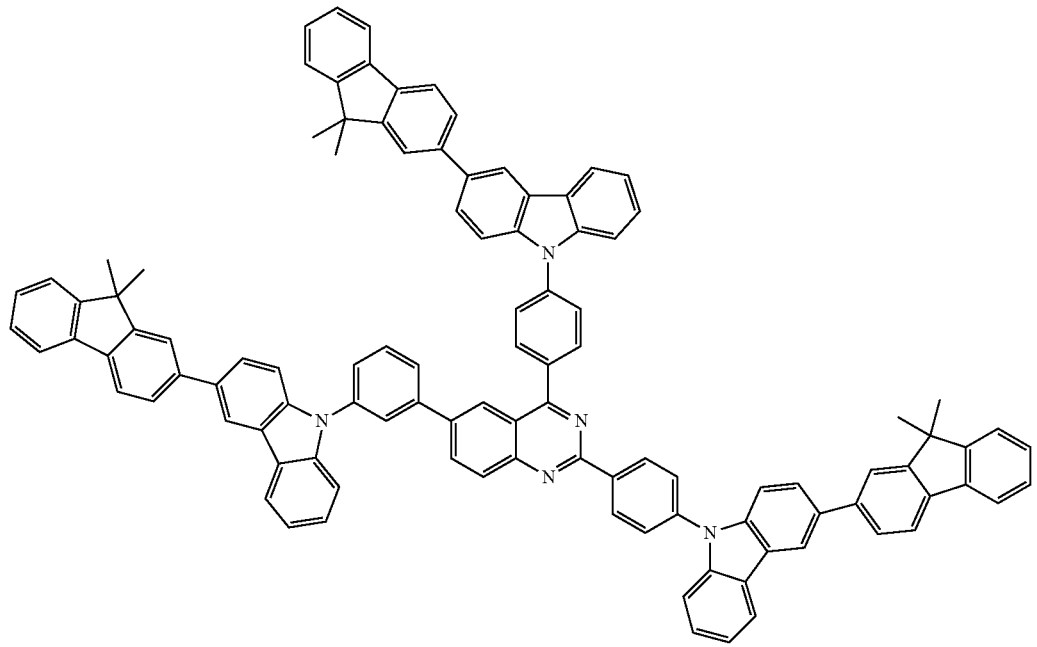
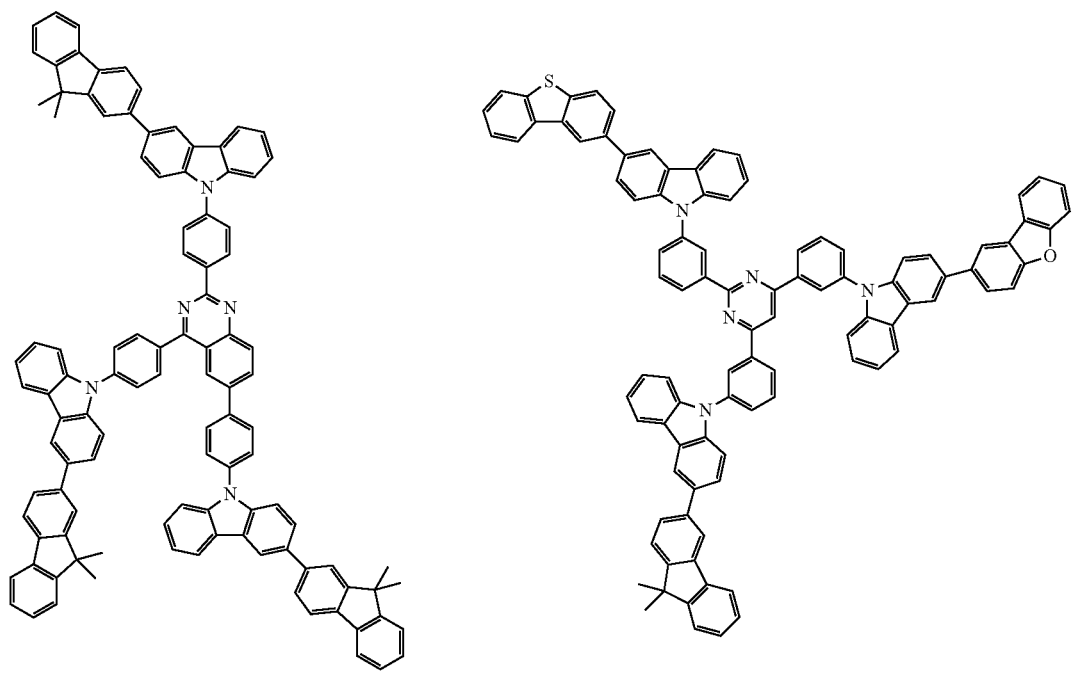

-continued
1573
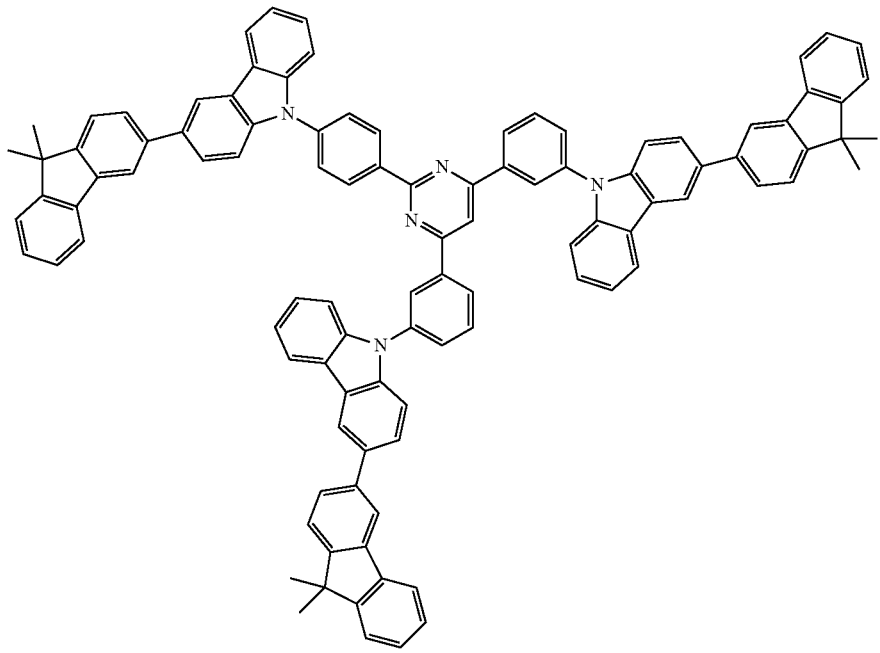
1574
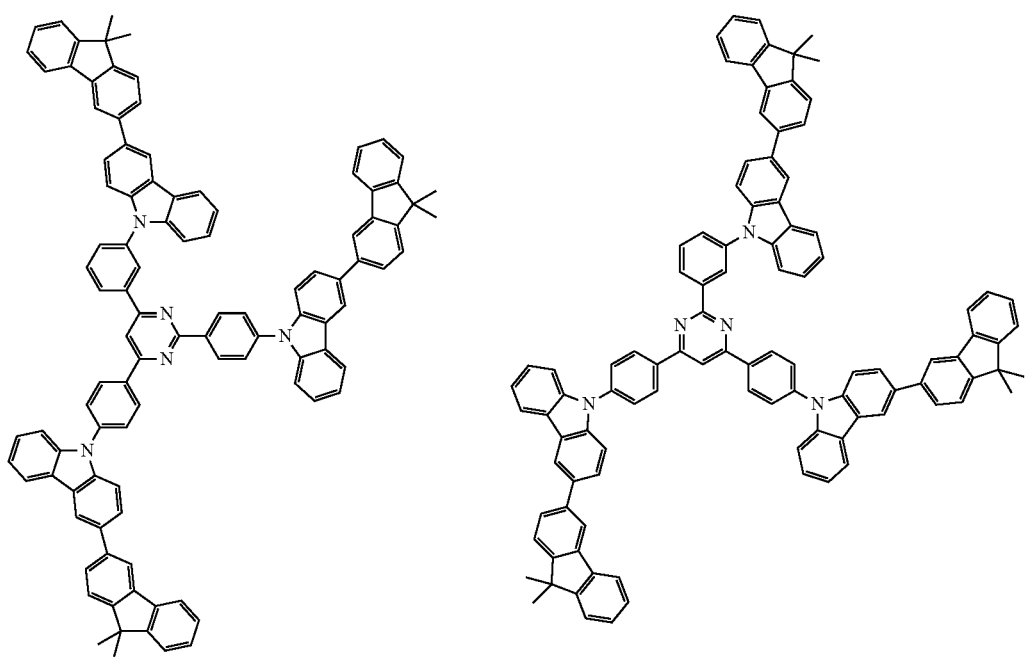

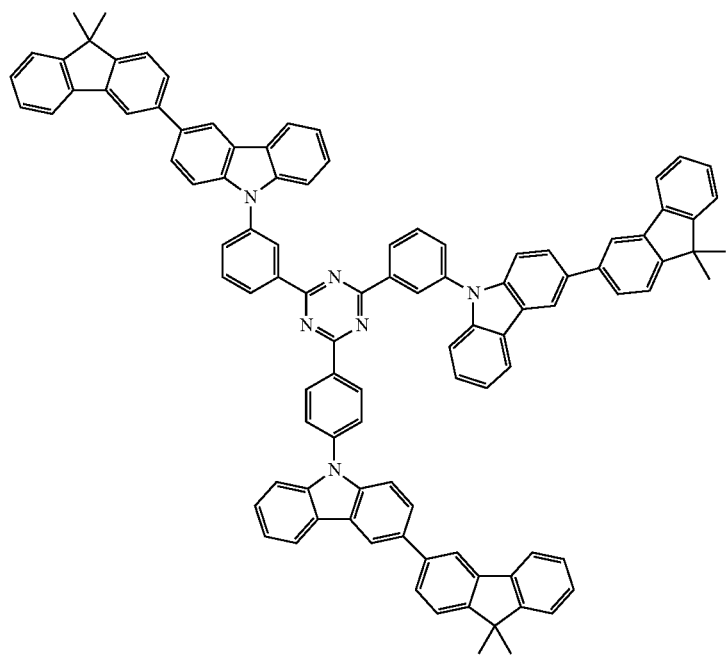
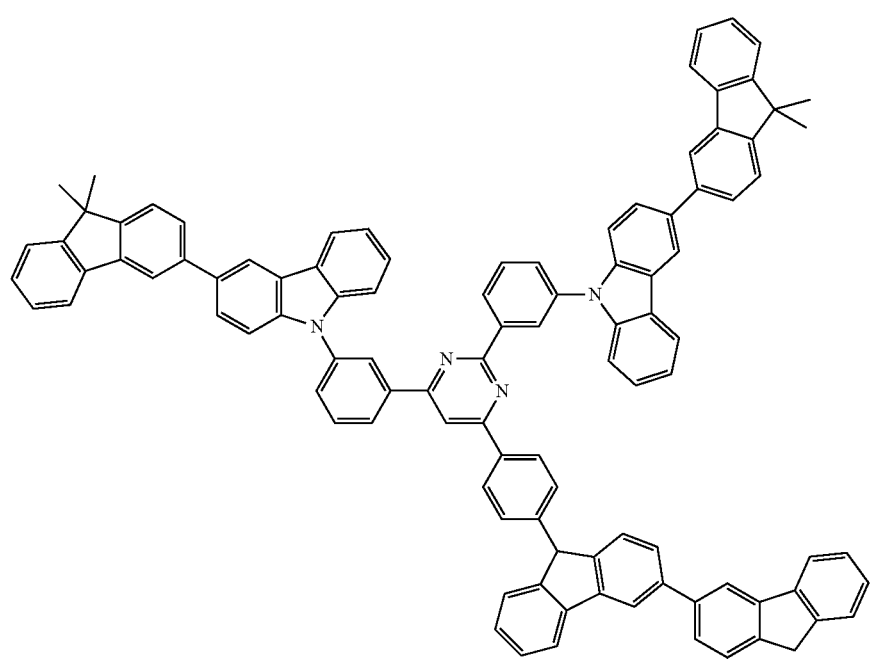

1577
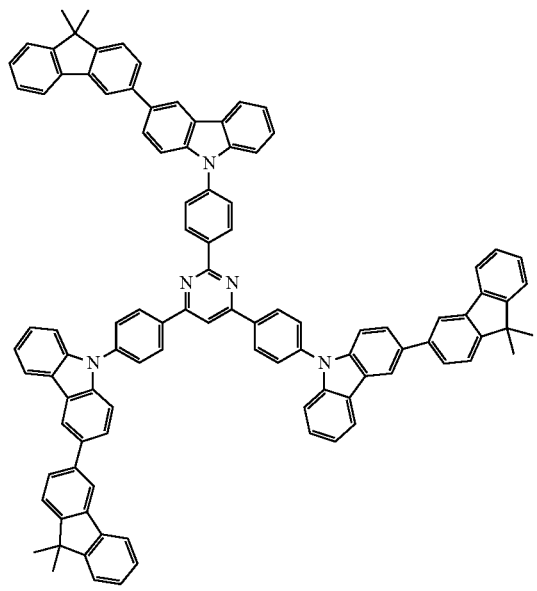
1578
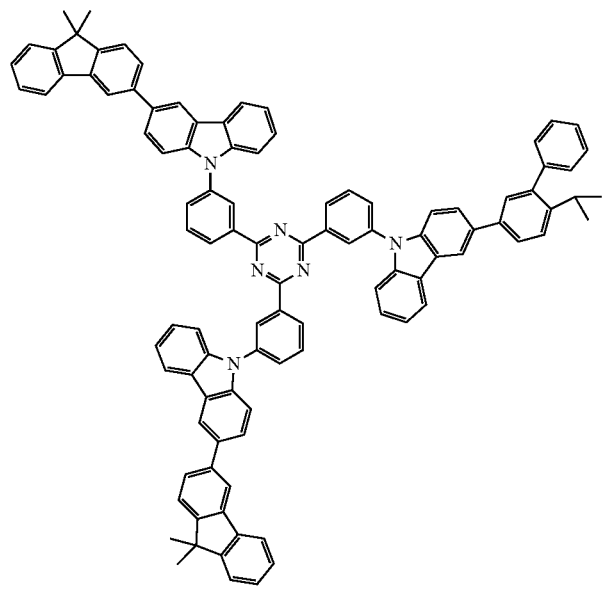
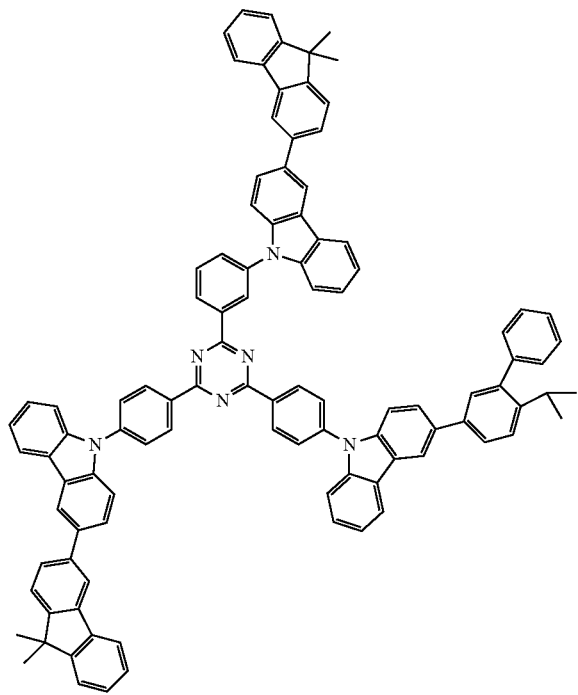
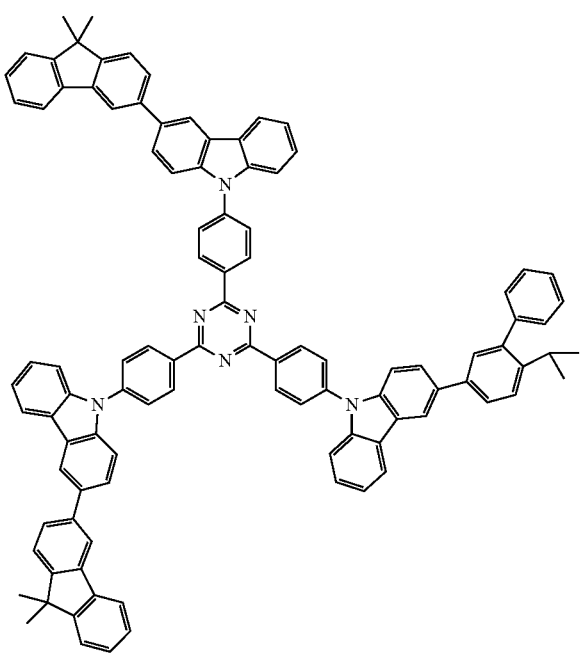

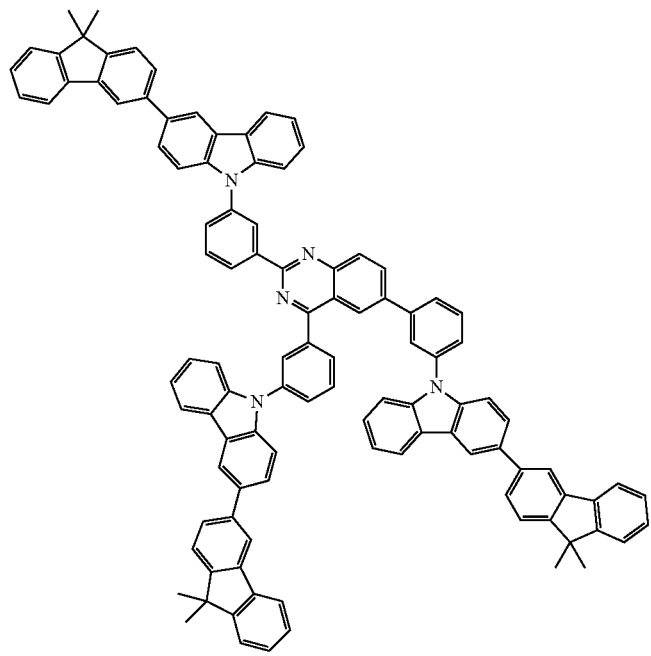 [SMILES: CC1(C)c2ccccc2-c2cc(-c3ccc4c(c3)c3ccccc3n4-c3cccc(-c4ccc5nc(-c6cccc(-n7c8ccccc8c8cc(-c9ccc%10c(c9)-c9ccccc9C%10(C)C)ccc87)c6)nc(-c6cccc(-n7c8ccccc8c8cc(-c9ccc%10c(c9)-c9ccccc9C%10(C)C)ccc87)c6)c5c4)c3)ccc21]
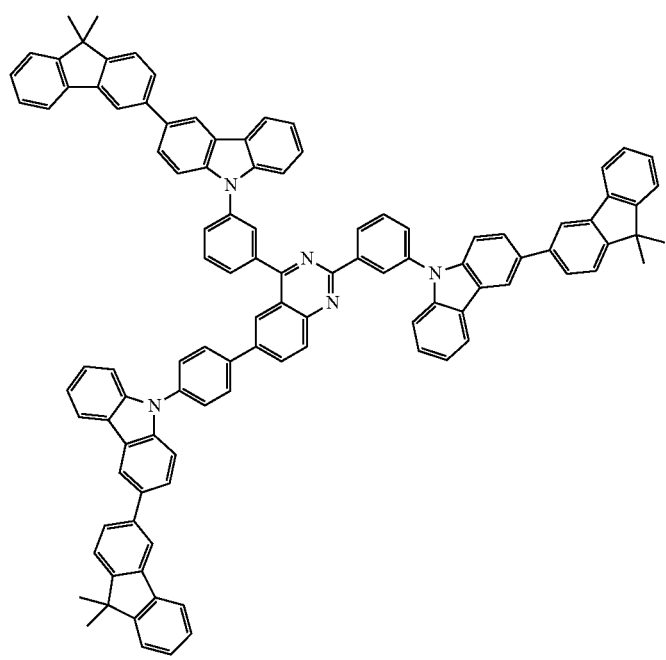 [SMILES: CC1(C)c2ccccc2-c2cc(-c3ccc4c(c3)c3ccccc3n4-c3ccc(-c4ccc5nc(-c6cccc(-n7c8ccccc8c8cc(-c9ccc%10c(c9)-c9ccccc9C%10(C)C)ccc87)c6)nc(-c6cccc(-n7c8ccccc8c8cc(-c9ccc%10c(c9)-c9ccccc9C%10(C)C)ccc87)c6)c5c4)cc3)ccc21]

-continued
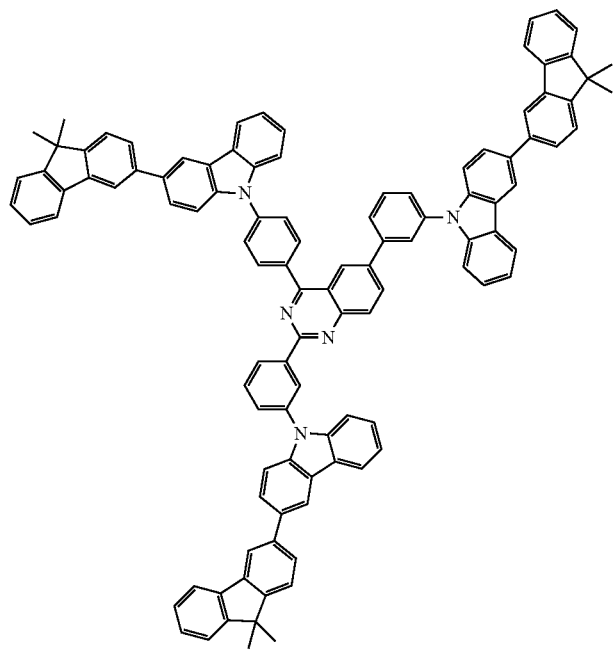 [SMILES: CC1(C)c2ccccc2-c2cc(-c3ccc4c(c3)c3ccccc3n4-c3ccc(-c4nc(-c5cccc(-n6c7ccccc7c7cc(-c8ccc9c(c8)-c8ccccc8C9(C)C)ccc76)c5)nc5ccc(-c6cccc(-n7c8ccccc8c8cc(-c9ccc%10c(c9)-c9ccccc9C%10(C)C)ccc87)c6)cc45)cc3)ccc21]
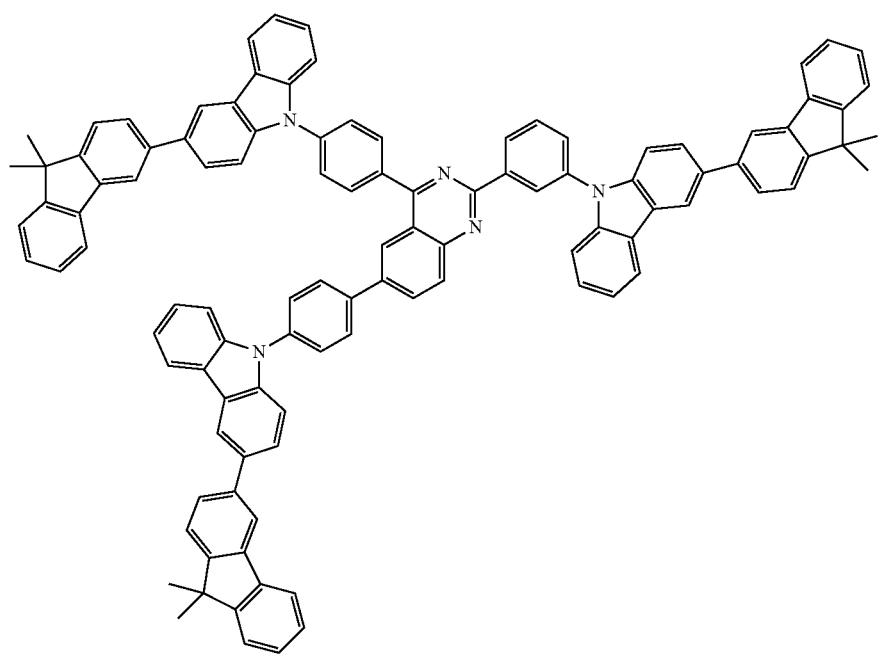

1583
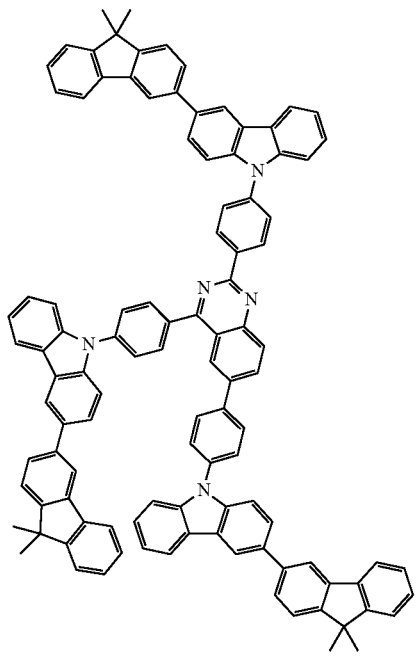
1584
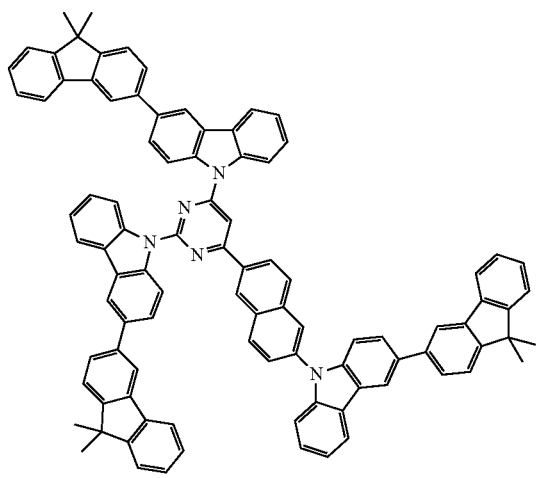
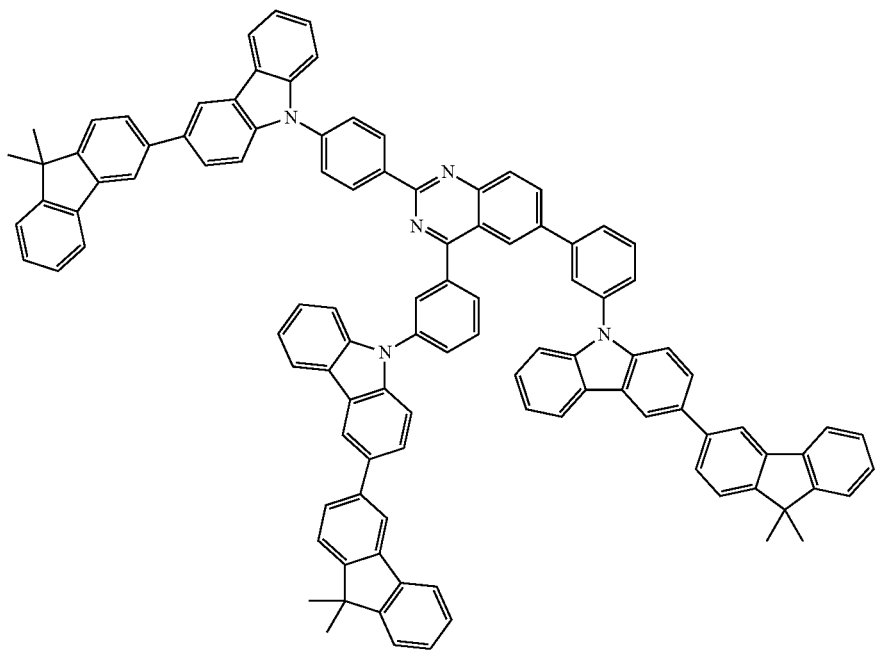

1585 1586
-continued
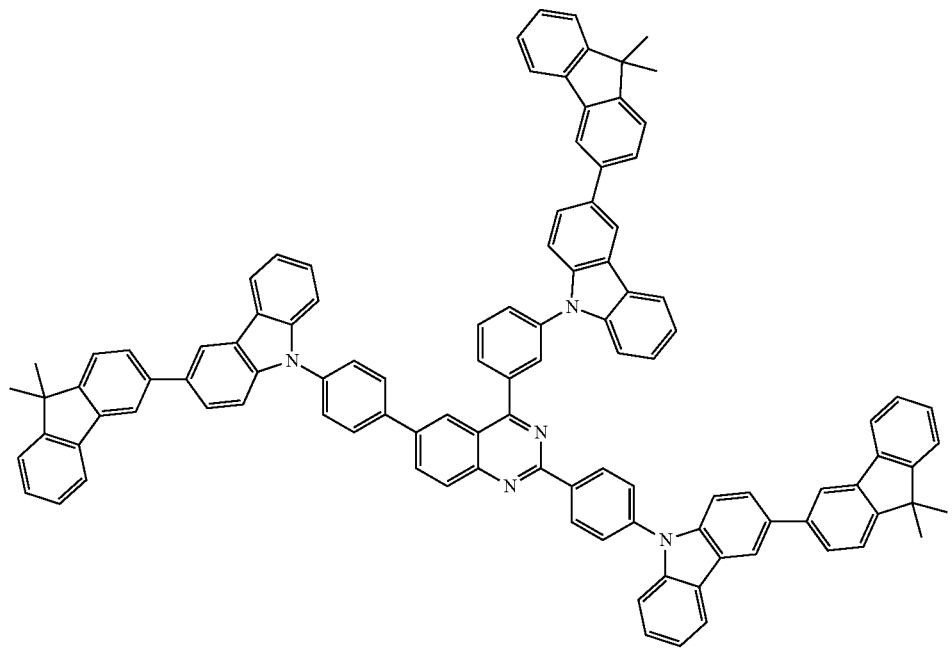
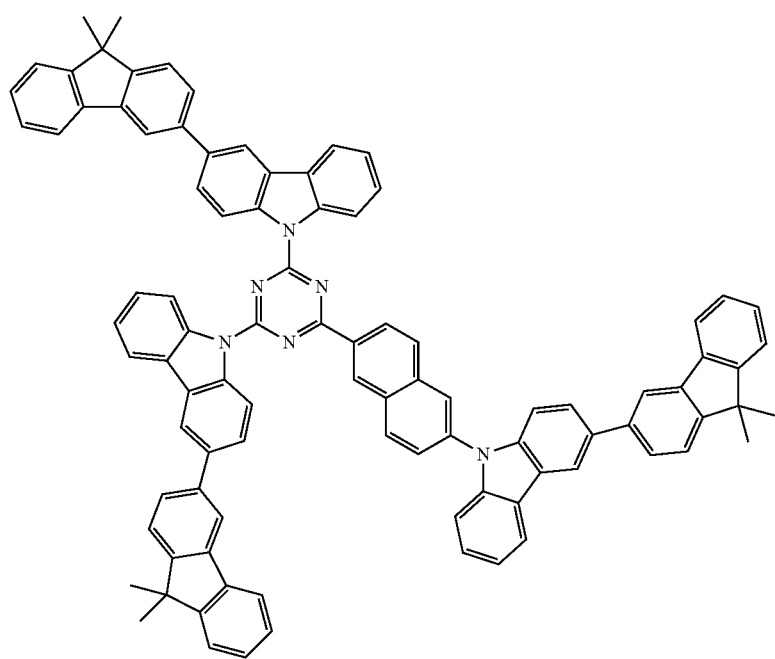

-continued
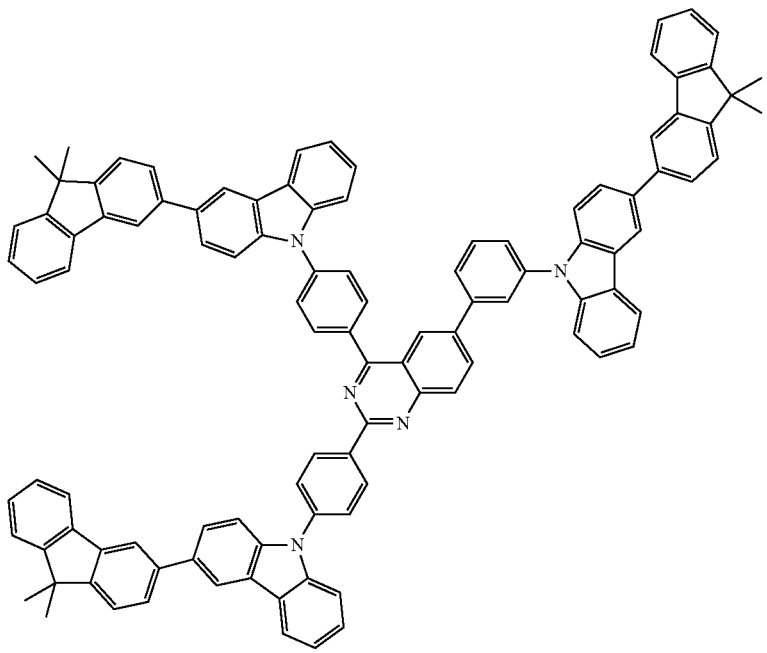
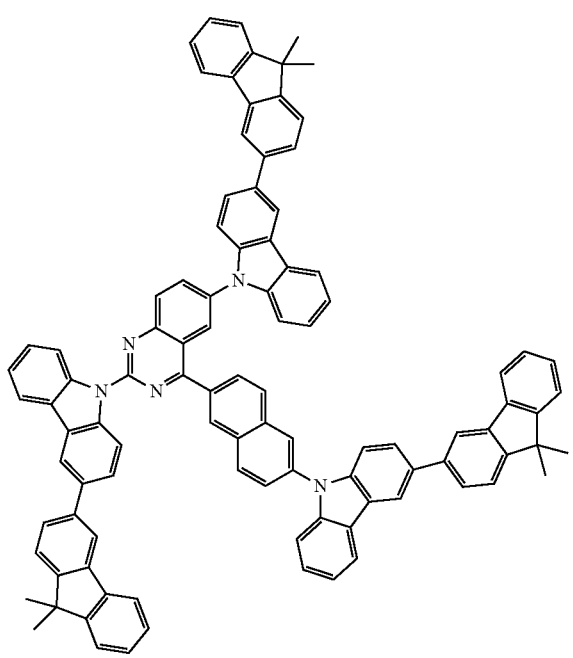

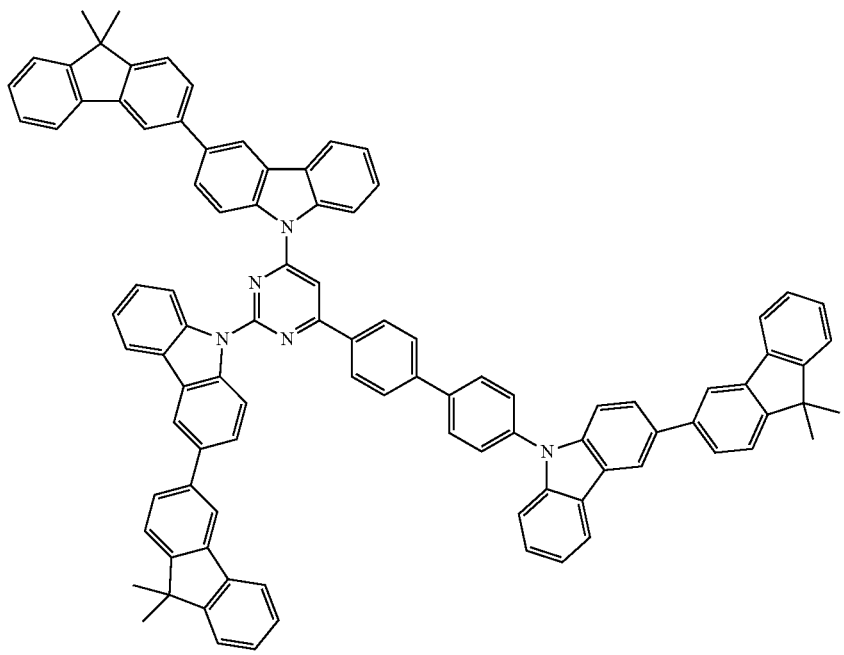
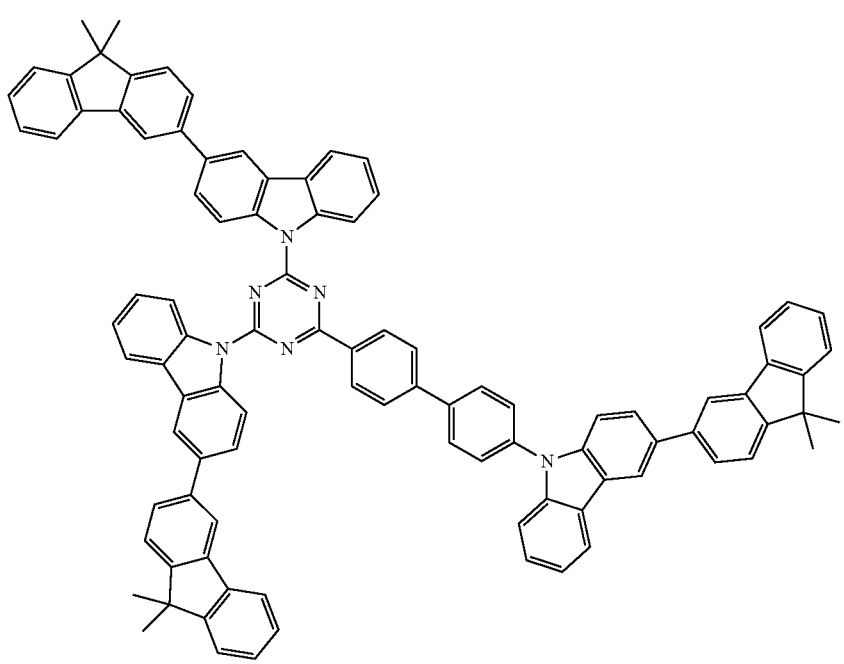

1591
1592
-continued
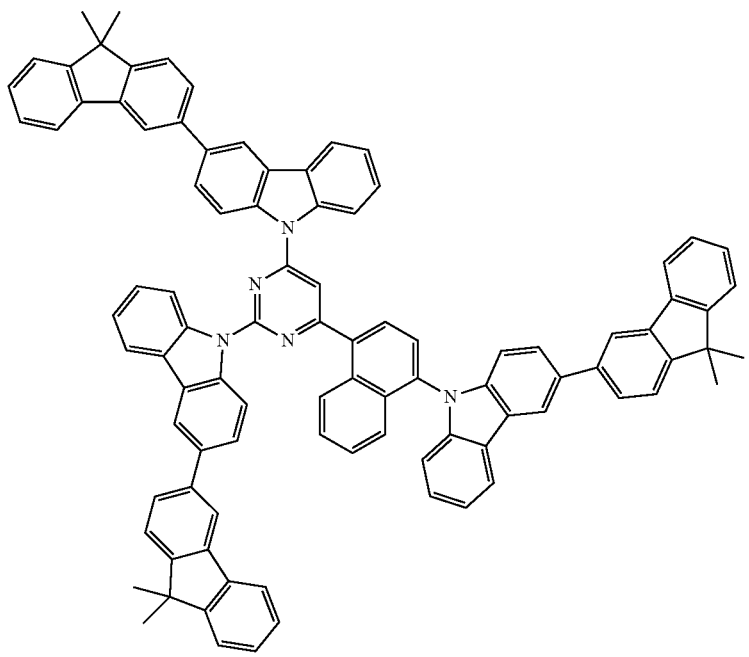
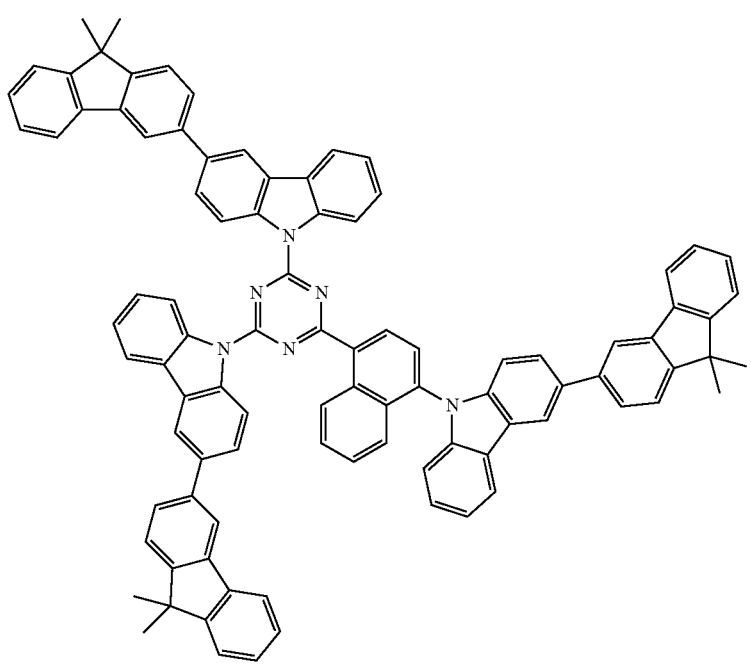

1593
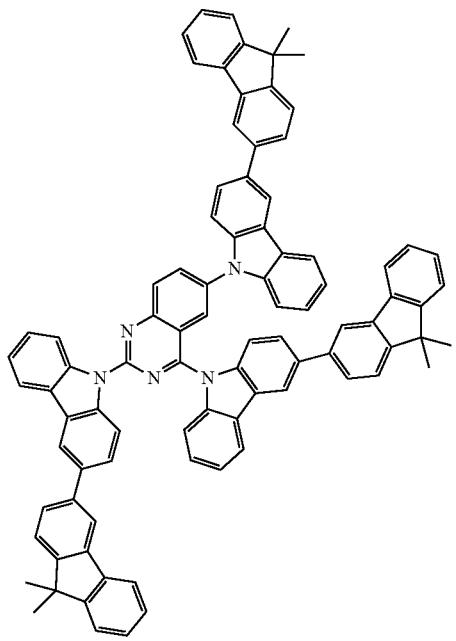
1594
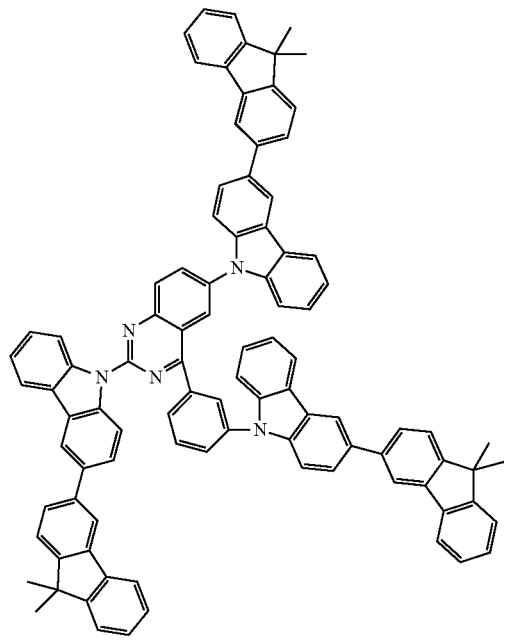
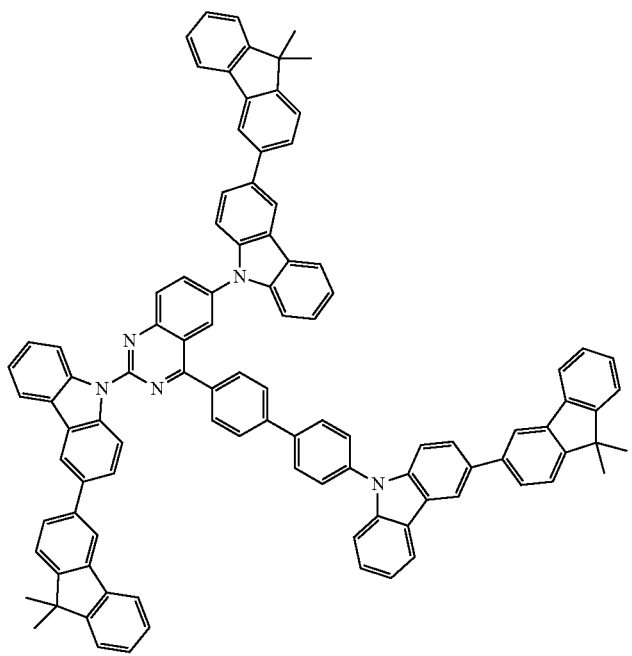

1595
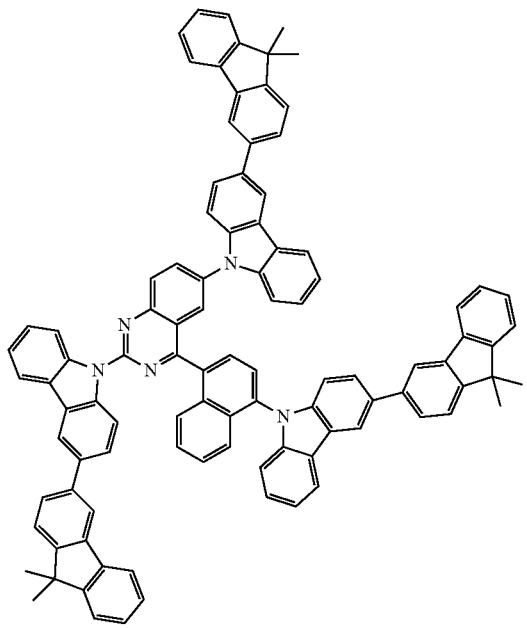
1596
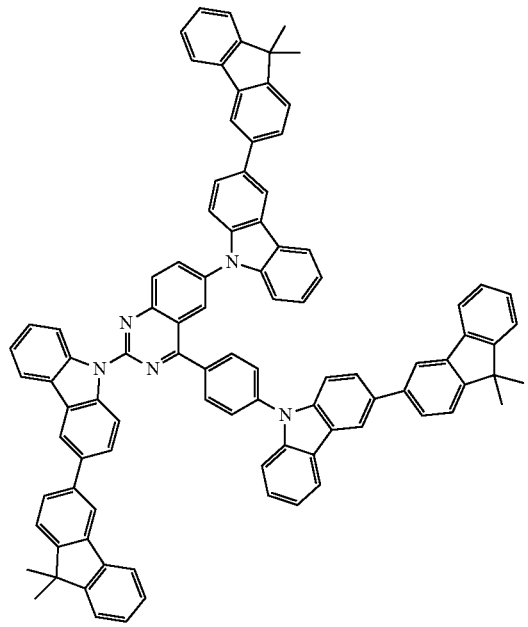
-continued
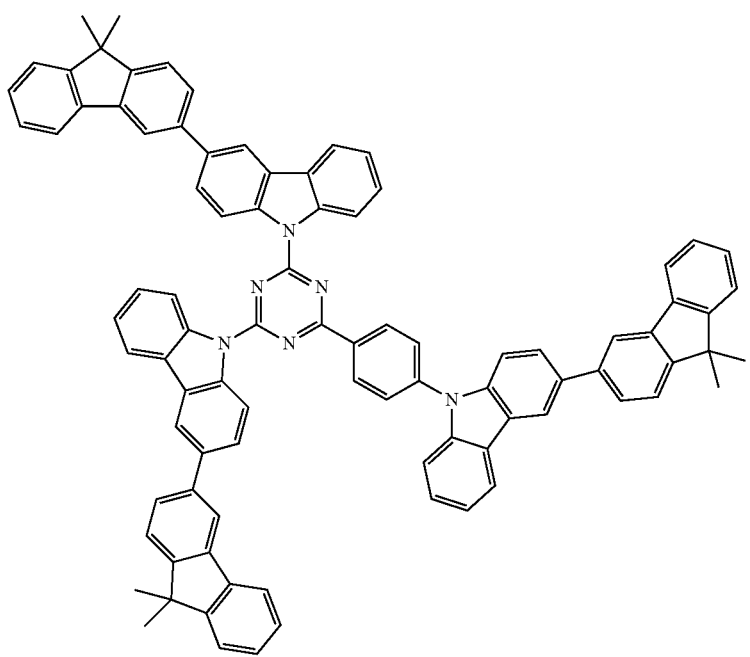

1597
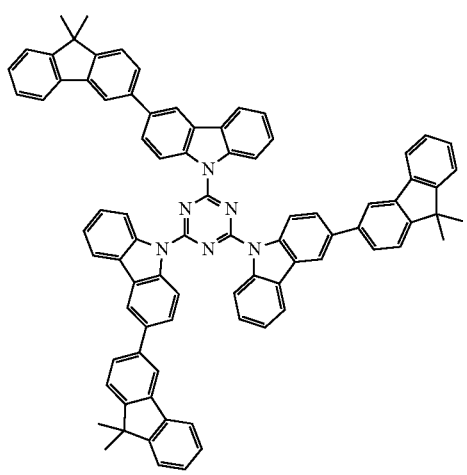
1598
-continued
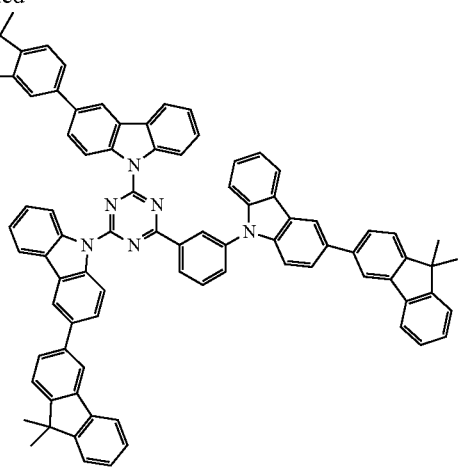
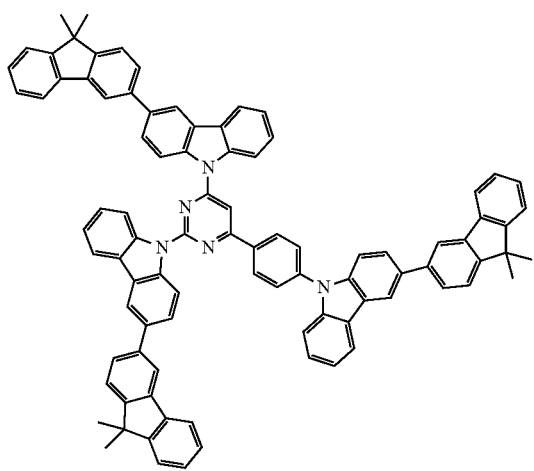
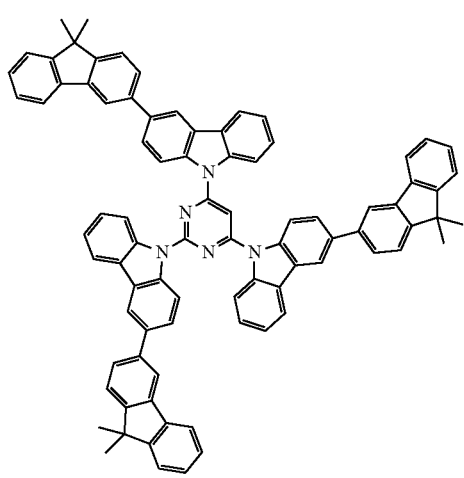
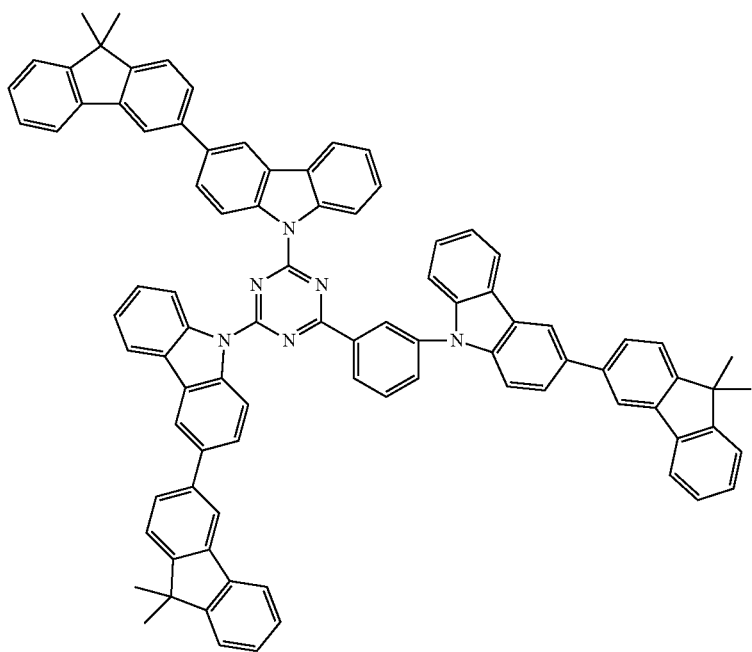

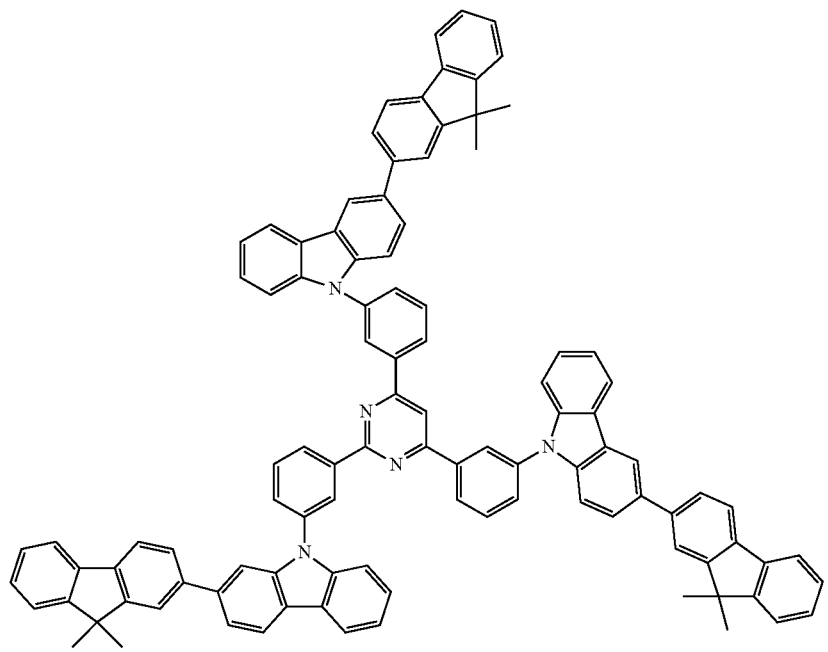
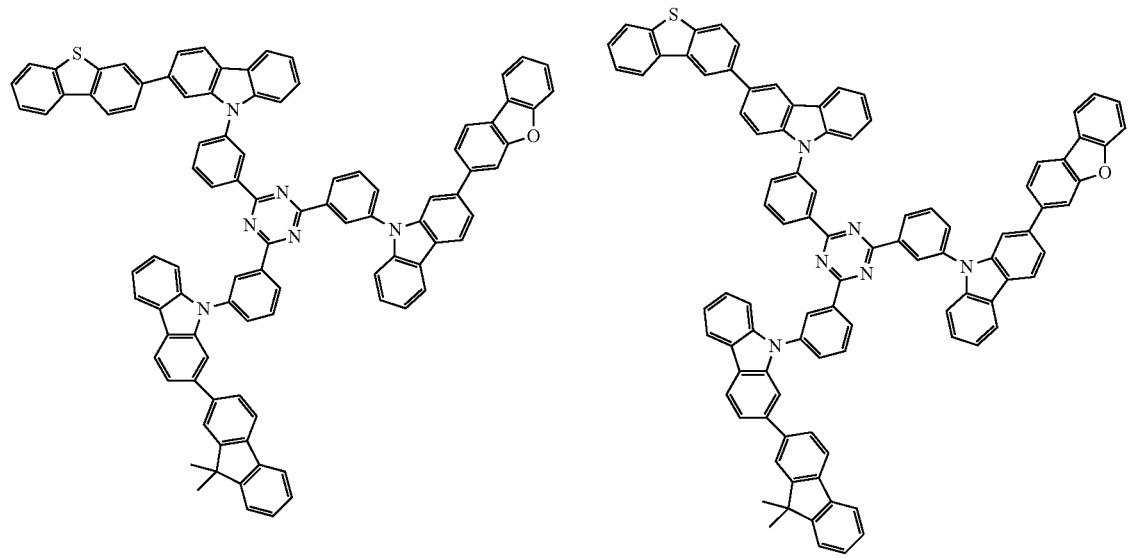 [SMILES: CC1(C)c2ccccc2-c2ccc(-c3ccc4c5ccccc5n(-c5cccc(-c6nc(-c7cccc(-n8c9ccccc9c9ccc(-c%10ccc%11c(c%10)oc%10ccccc%10%11)cc98)c7)nc(-c7cccc(-n8c9ccccc9c9ccc(-c%10ccc%11c(c%10)sc%10ccccc%10%11)cc98)c7)n6)c5)c4c3)cc21 ; CC1(C)c2ccccc2-c2ccc(-c3ccc4c5ccccc5n(-c5cccc(-c6nc(-c7cccc(-n8c9ccccc9c9cc(-c%10ccc%11sc%12ccccc%12c%11c%10)ccc98)c7)nc(-c7cccc(-n8c9ccccc9c9ccc(-c%10ccc%11c(c%10)oc%10ccccc%10%11)cc98)c7)n6)c5)c4c3)cc21]

1601
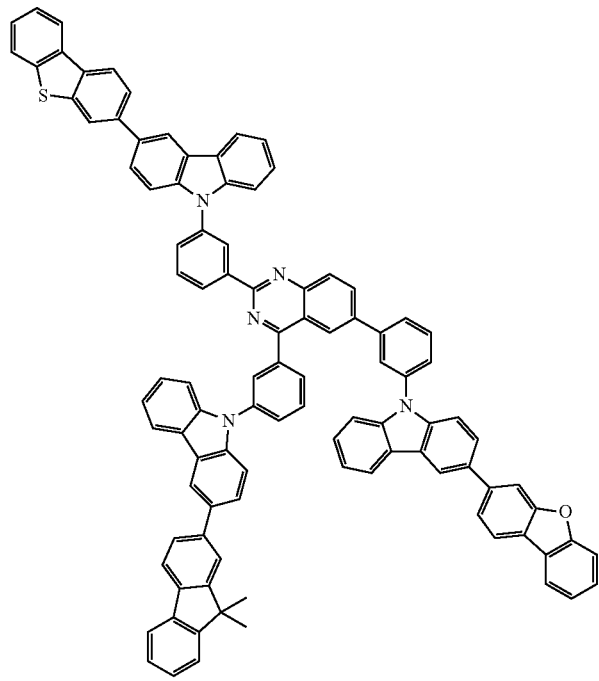
1602
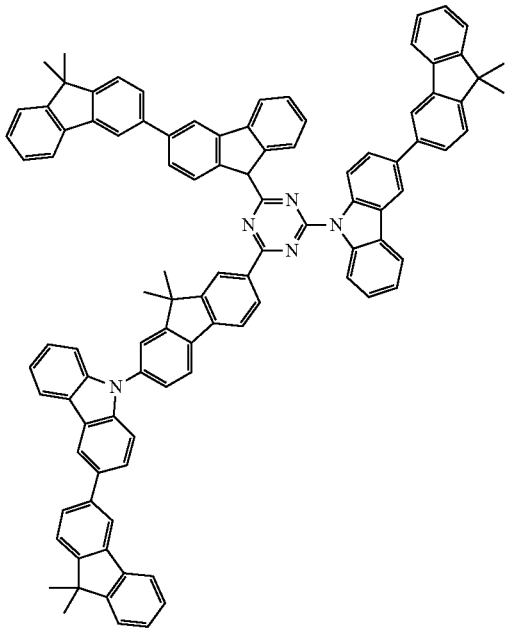
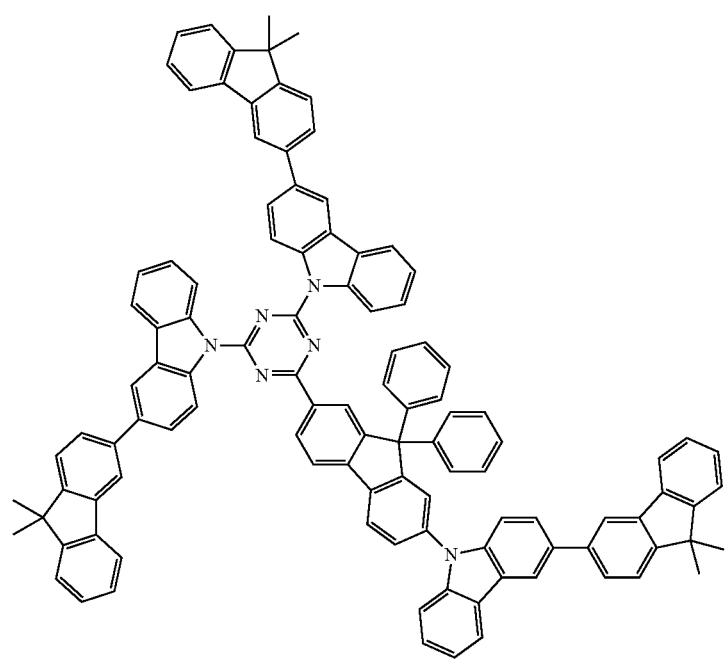

1603
1604
-continued
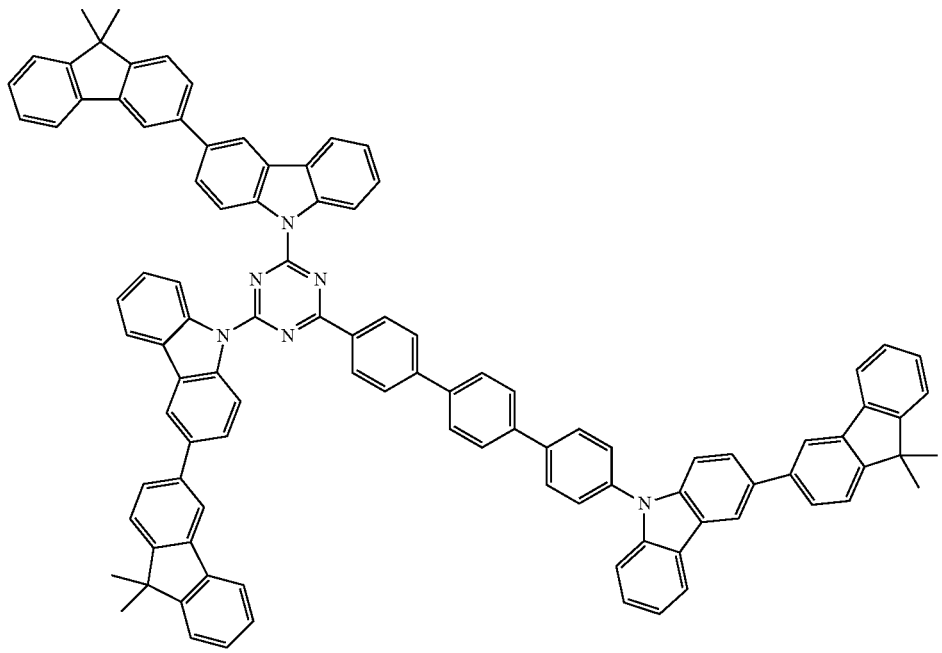 [SMILES: CC1(C)c2ccccc2-c2cc(-c3ccc4c(c3)c3ccccc3n4-c3ccc(-c4ccc(-c5ccc(-c6nc(-n7c8ccccc8c8cc(-c9ccc%10c(c9)-c9ccccc9C%10(C)C)ccc87)nc(-n7c8ccccc8c8cc(-c9ccc%10c(c9)-c9ccccc9C%10(C)C)ccc87)n6)cc5)cc4)cc3)ccc21]
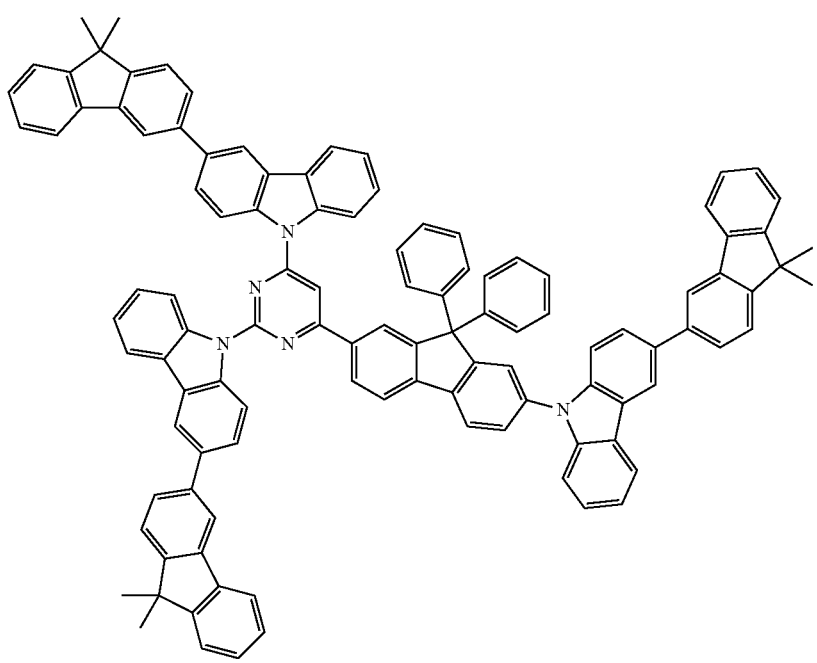

-continued
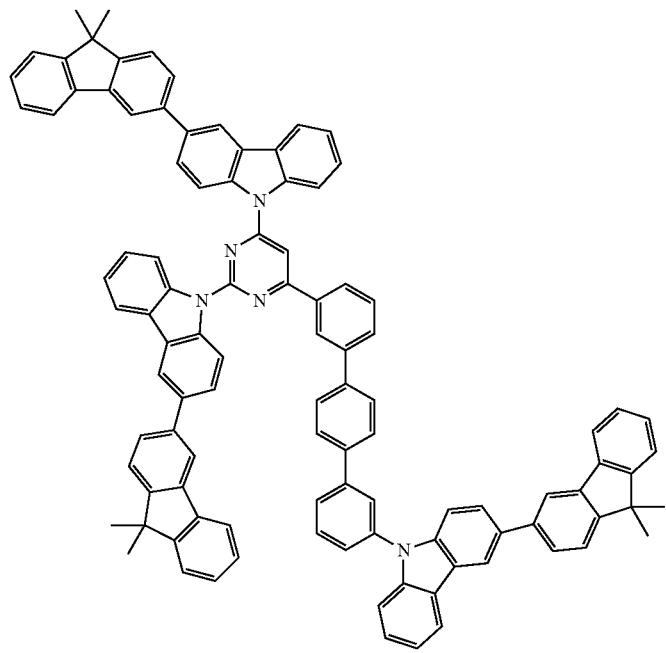
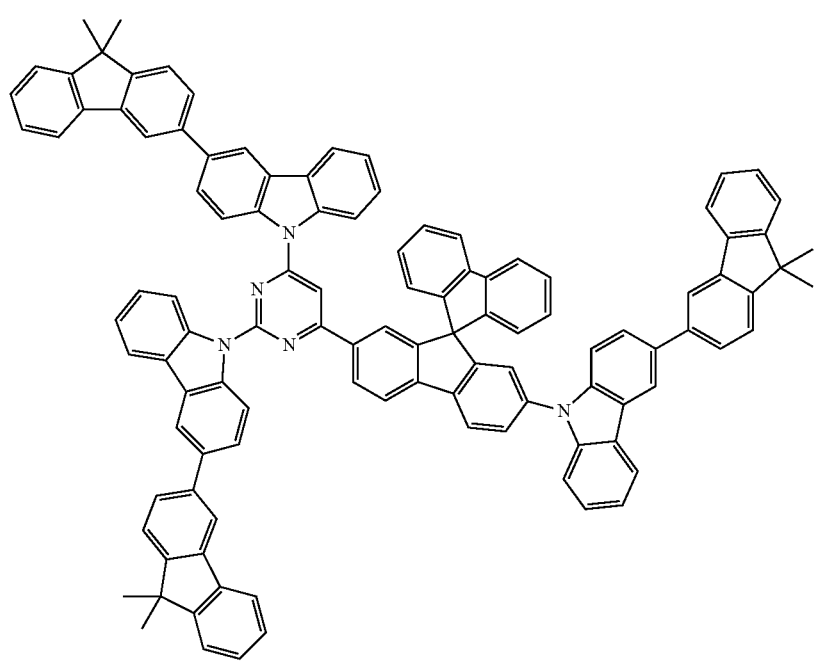

-continued
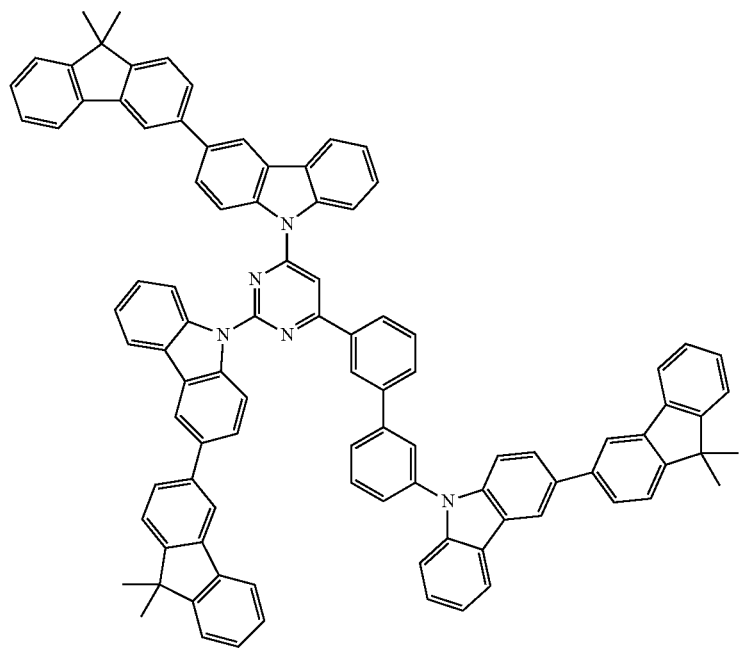
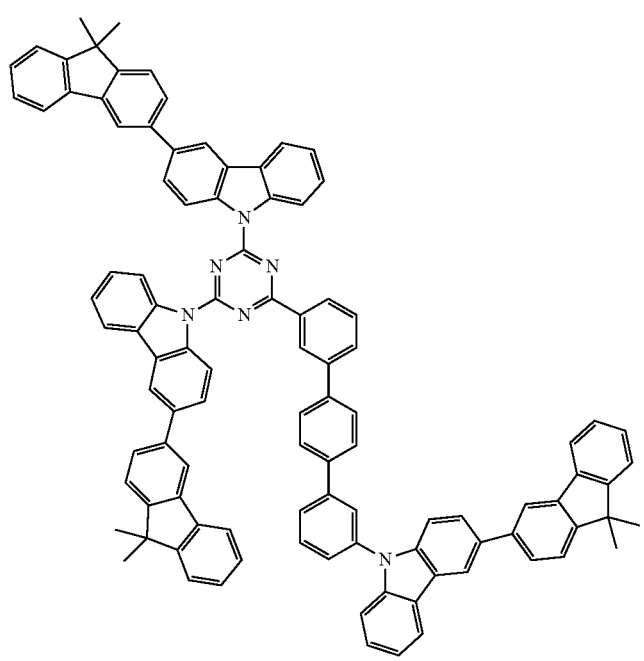

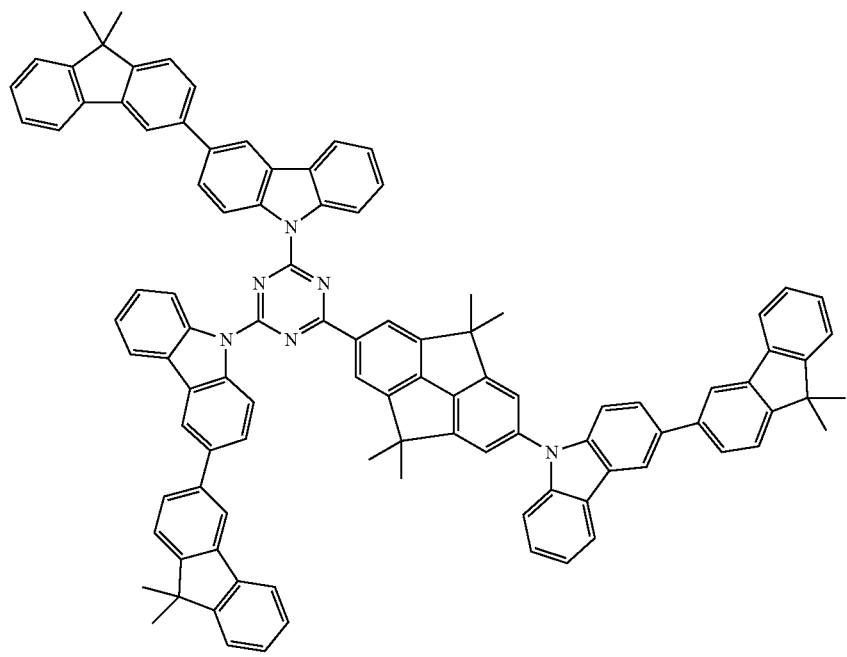
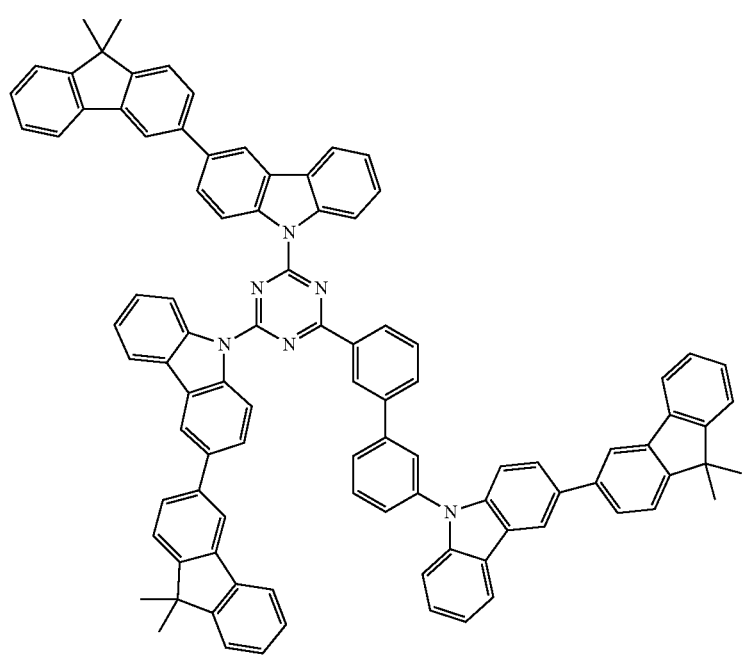

1611
1612
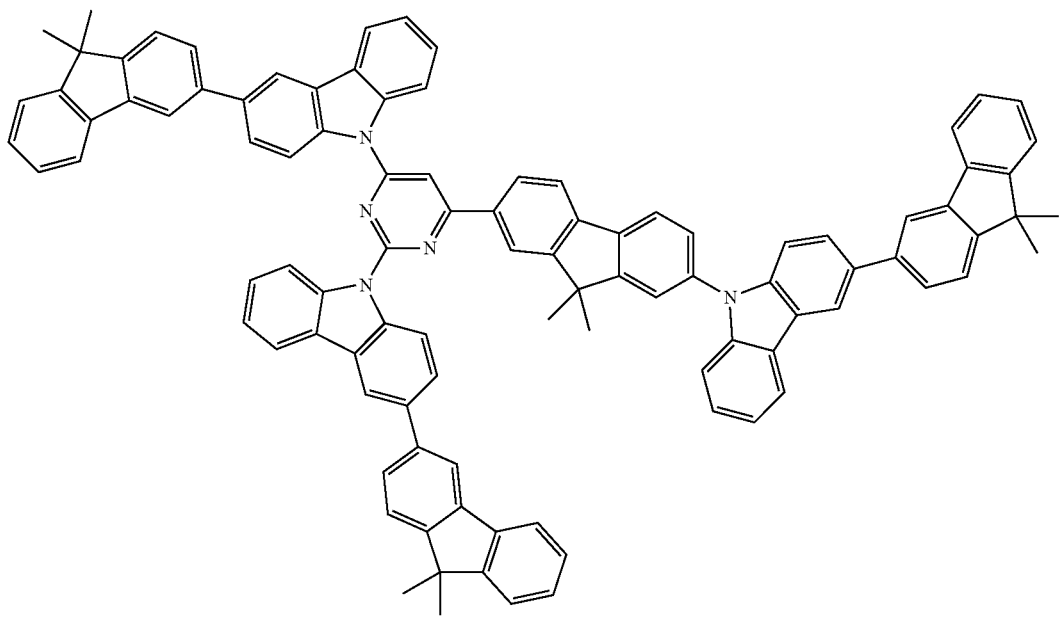
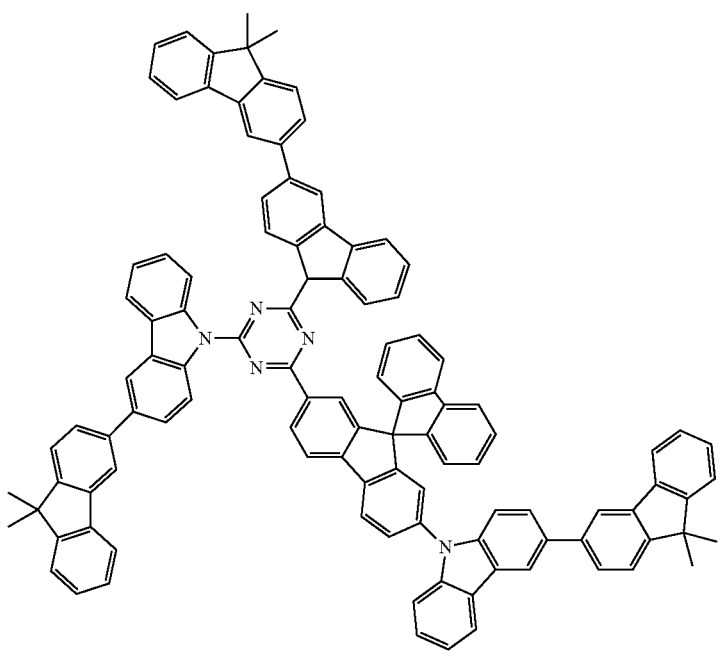

-continued
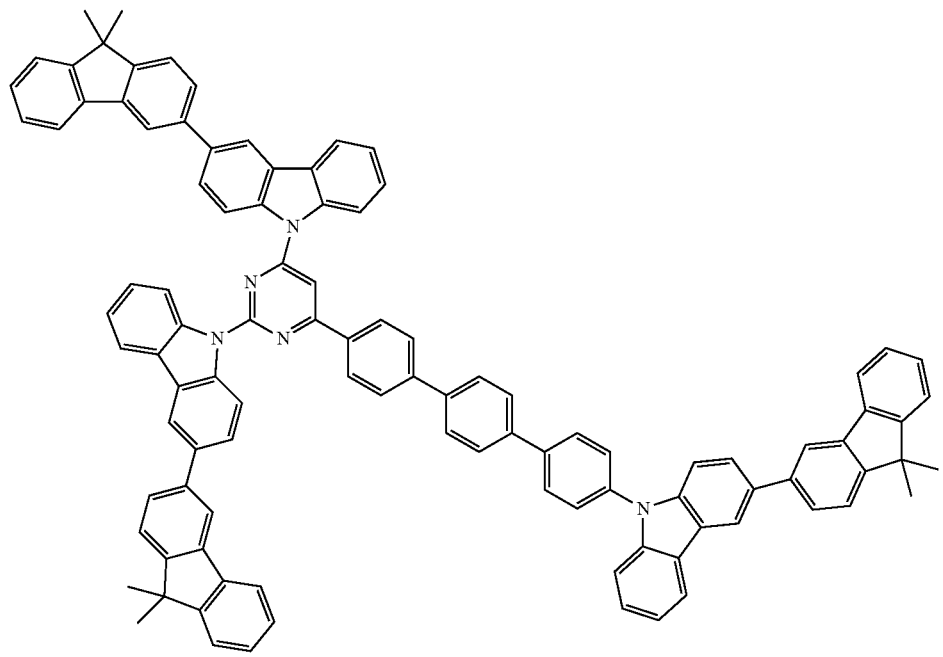
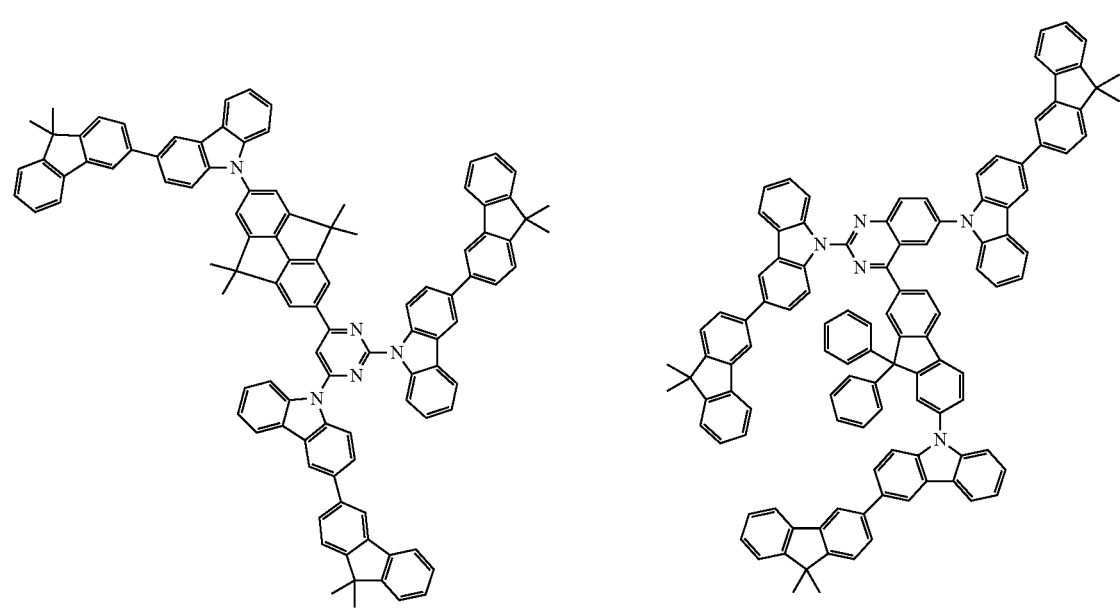

1615 1616
-continued
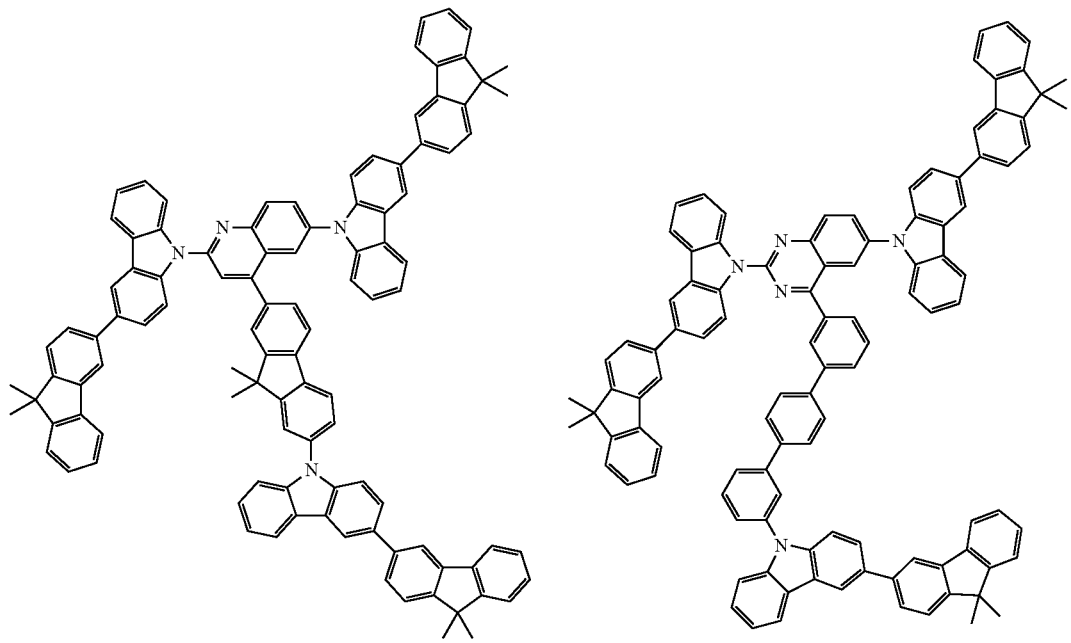
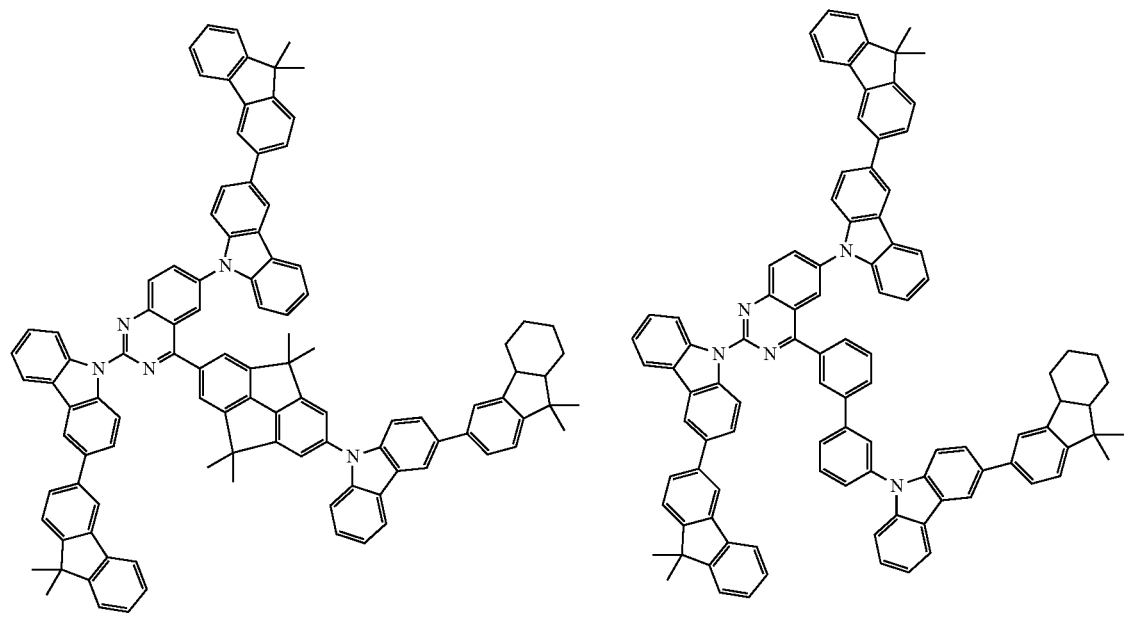 [SMILES: CC1(C)c2ccccc2-c2cc(-c3ccc4c(c3)c3ccccc3n4-c3ccc4nc(-n5c6ccccc6c6cc(-c7ccc8c(c7)-c7ccccc7C8(C)C)ccc65)nc(-c5cc6c7c(c5)C(C)(C)c5cc(-n8c9ccccc9c9cc(-c%10ccc%11c(c%10)C%10CCCCC%10C%11(C)C)ccc98)cc(c5-7)C6(C)C)c4c3)ccc21 ; CC1(C)c2ccccc2-c2cc(-c3ccc4c(c3)c3ccccc3n4-c3ccc4nc(-n5c6ccccc6c6cc(-c7ccc8c(c7)-c7ccccc7C8(C)C)ccc65)nc(-c5cccc(-c6cccc(-n7c8ccccc8c8cc(-c9ccc%10c(c9)C9CCCCC9C%10(C)C)ccc87)c6)c5)c4c3)ccc21]

1617
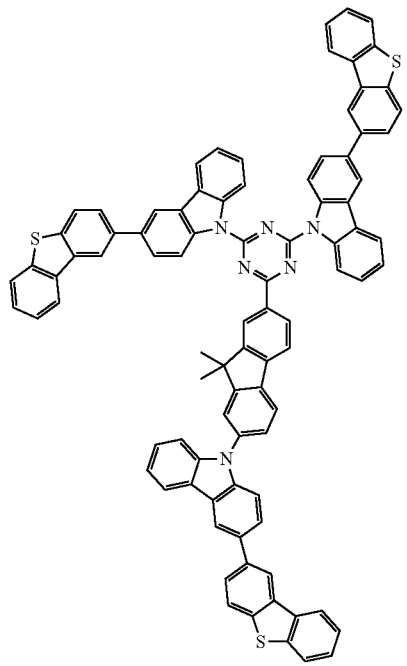
1618
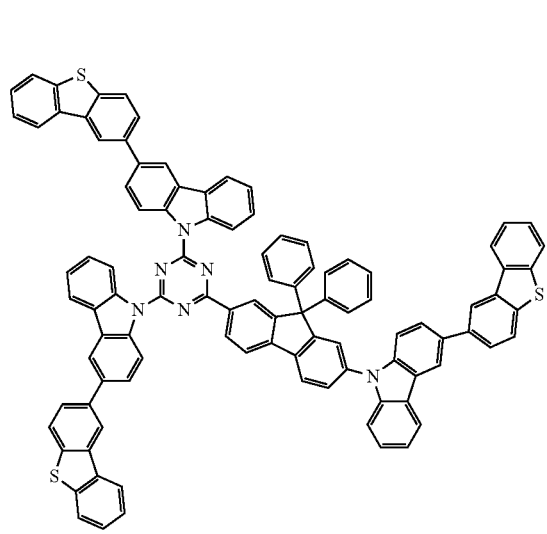
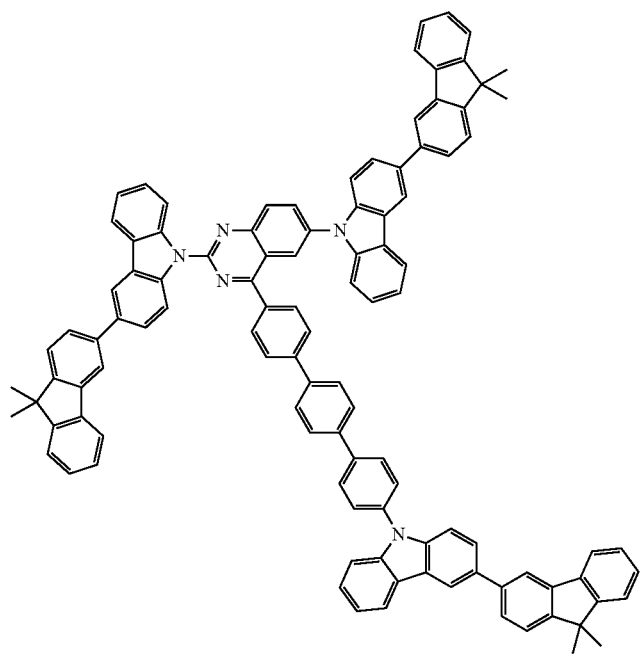 [SMILES: CC1(C)c2ccccc2-c2cc(-c3ccc4c(c3)c3ccccc3n4-c3ccc(-c4ccc(-c5ccc(-c6nc(-n7c8ccccc8c8cc(-c9ccc%10c(c9)-c9ccccc9C%10(C)C)ccc87)nc7ccc(-n8c9ccccc9c9cc(-c%10ccc%11c(c%10)-c%10ccccc%10C%11(C)C)ccc98)cc67)cc5)cc4)cc3)ccc21]

1619 1620
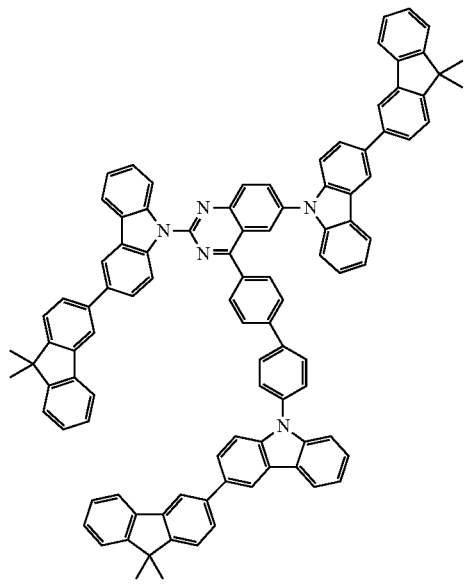
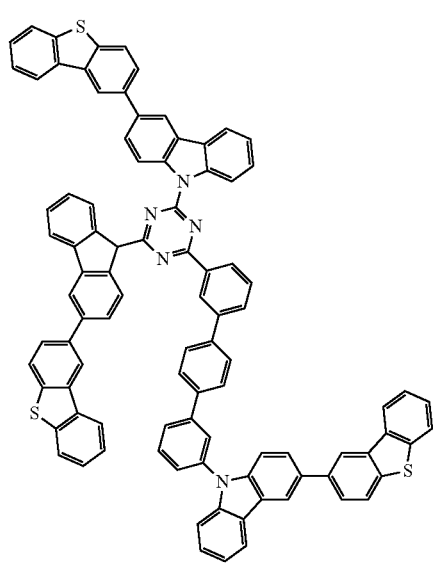
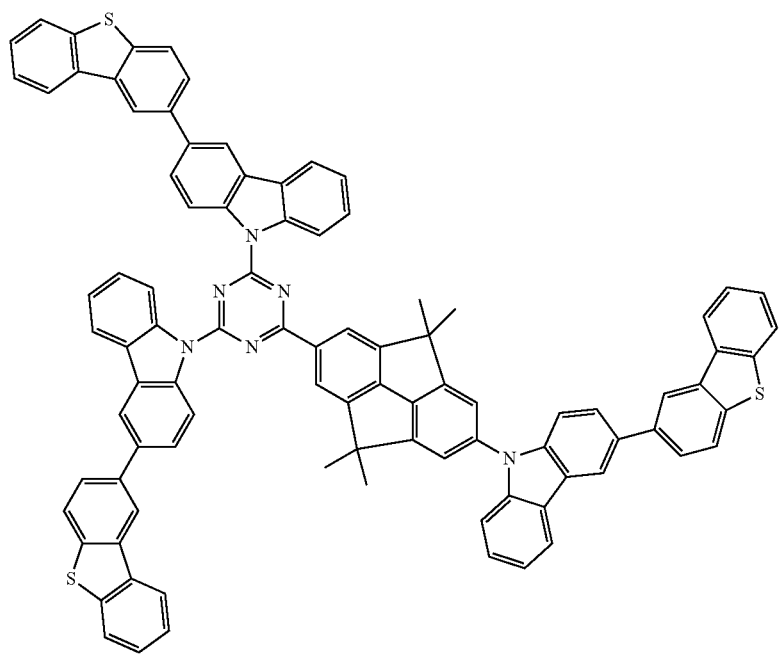

1621
-continued
1622
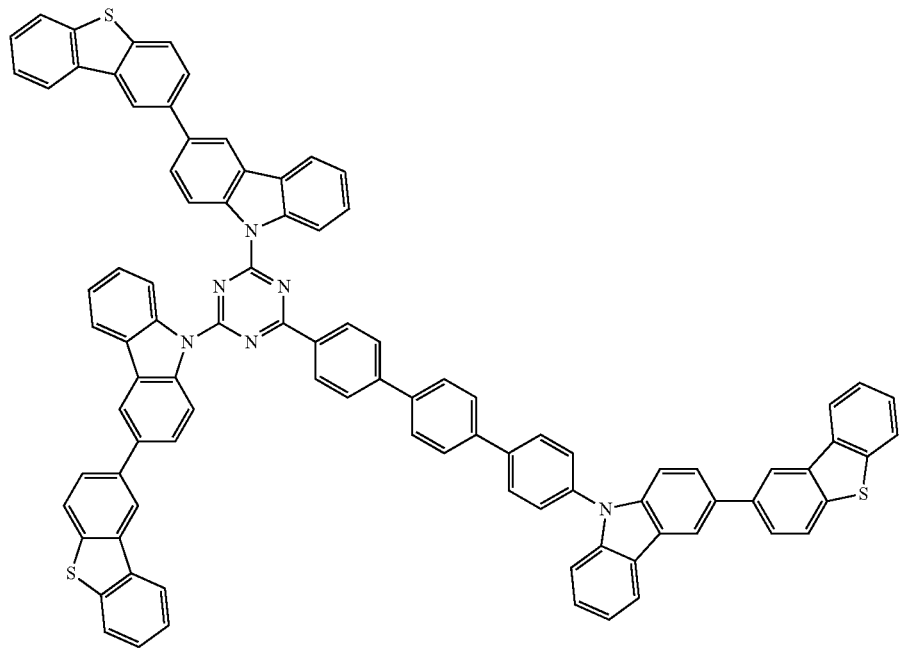
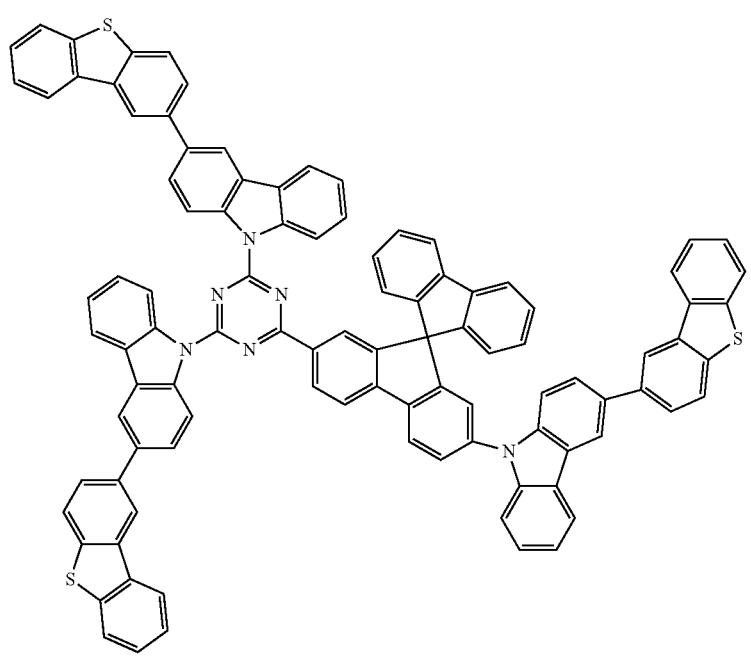

1623
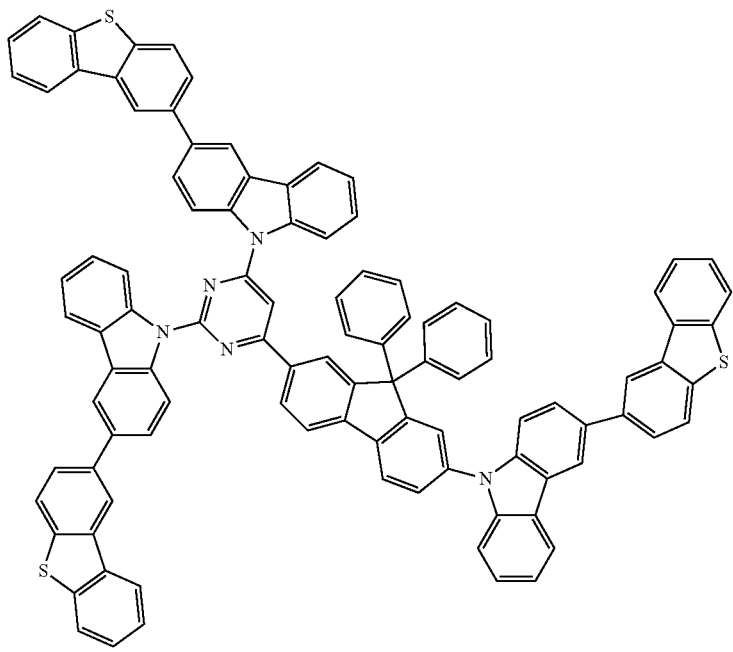
1624
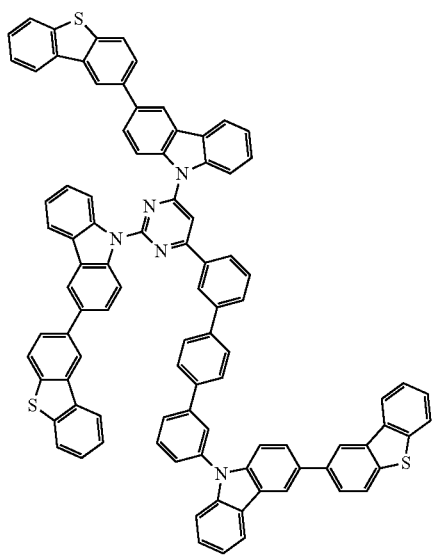
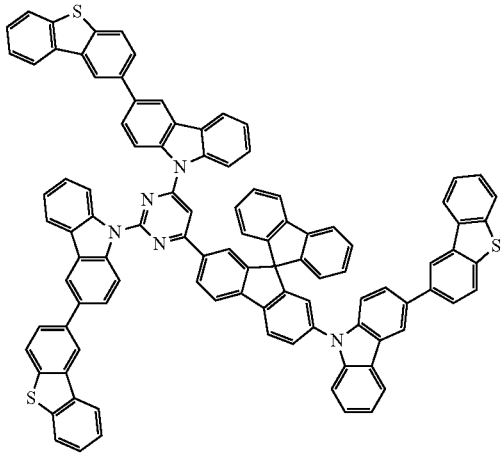

1625
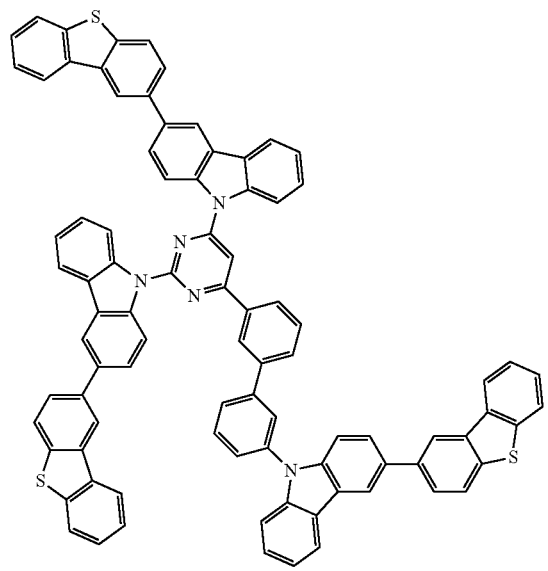
1626
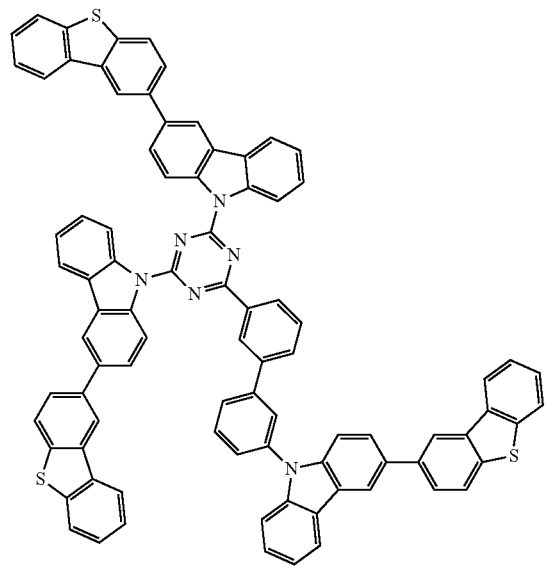
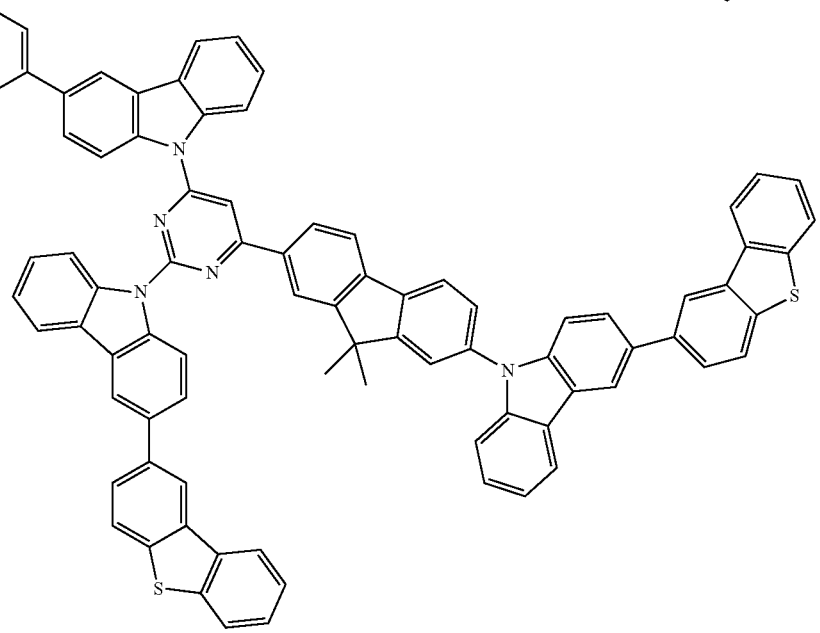
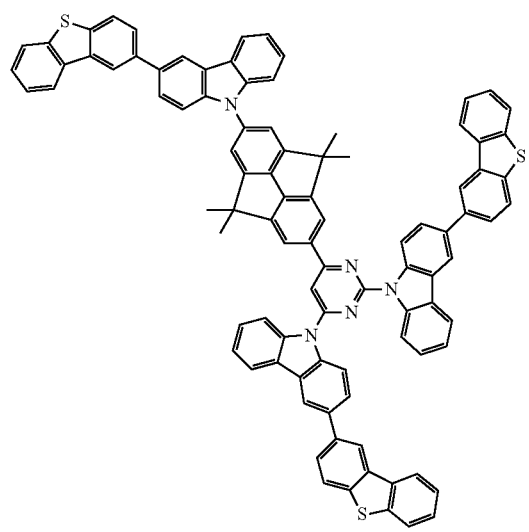
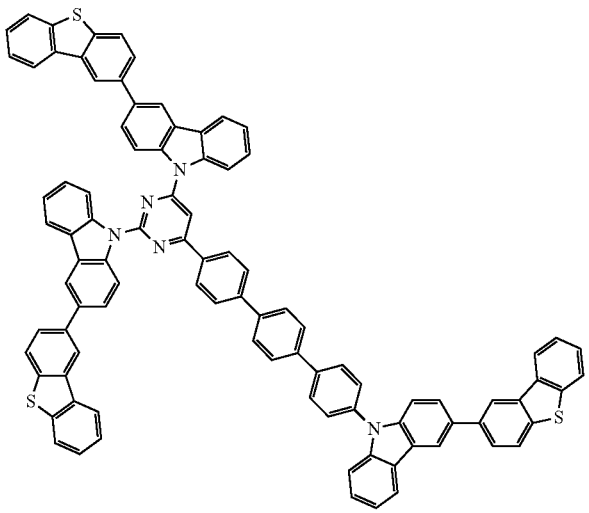

1627
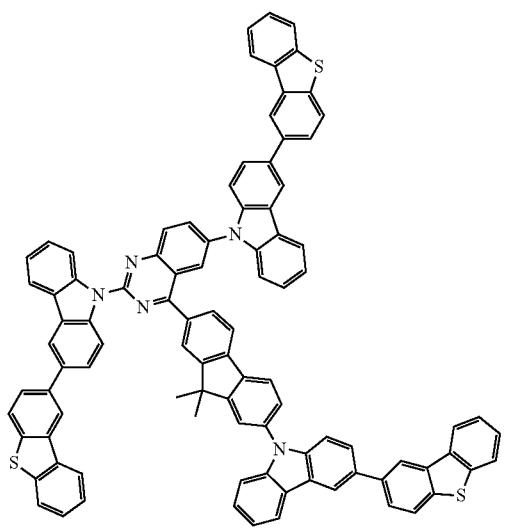
1628
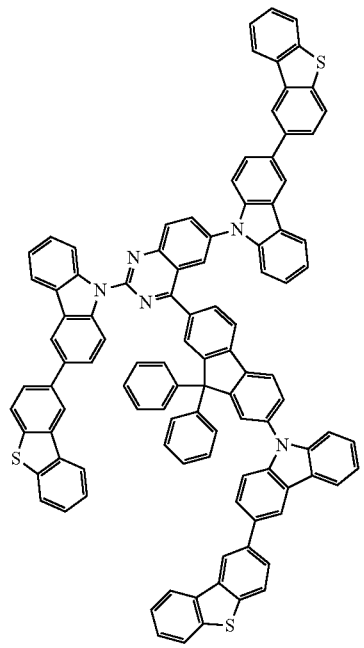
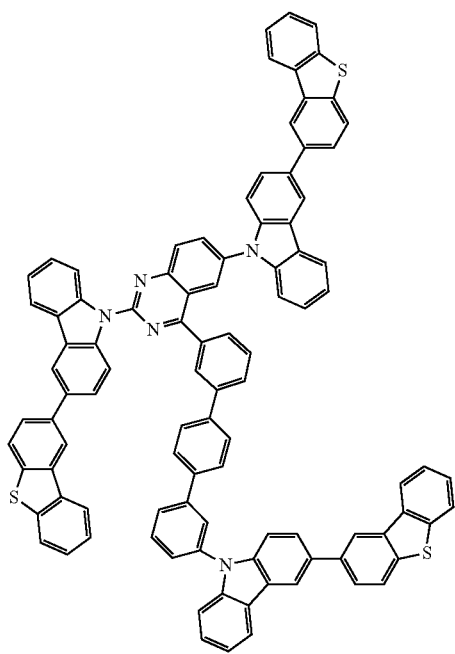

1629 1630
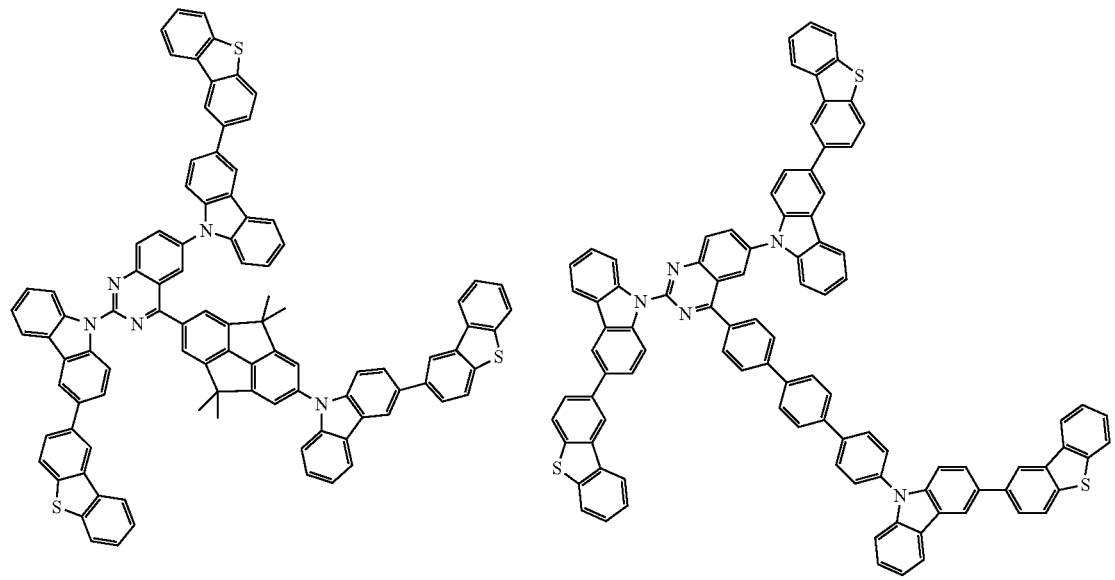 [SMILES: CC1(C)c2cc(-c3nc(-n4c5ccccc5c5cc(-c6ccc7sc8ccccc8c7c6)ccc54)nc4ccc(-n5c6ccccc6c6cc(-c7ccc8sc9ccccc9c8c7)ccc65)cc34)cc3c2-c2c1cc(-n1c4ccccc4c4cc(-c5ccc6sc7ccccc7c6c5)ccc41)cc2C3(C)C ; c1ccc2c(c1)sc1ccc(-c3ccc4c(c3)c3ccccc3n4-c3ccc(-c4ccc(-c5ccc(-c6nc(-n7c8ccccc8c8cc(-c9ccc%10sc%11ccccc%11c%10c9)ccc87)nc7ccc(-n8c9ccccc9c9cc(-c%10ccc%11sc%12ccccc%12c%11c%10)ccc98)cc67)cc5)cc4)cc3)cc12]
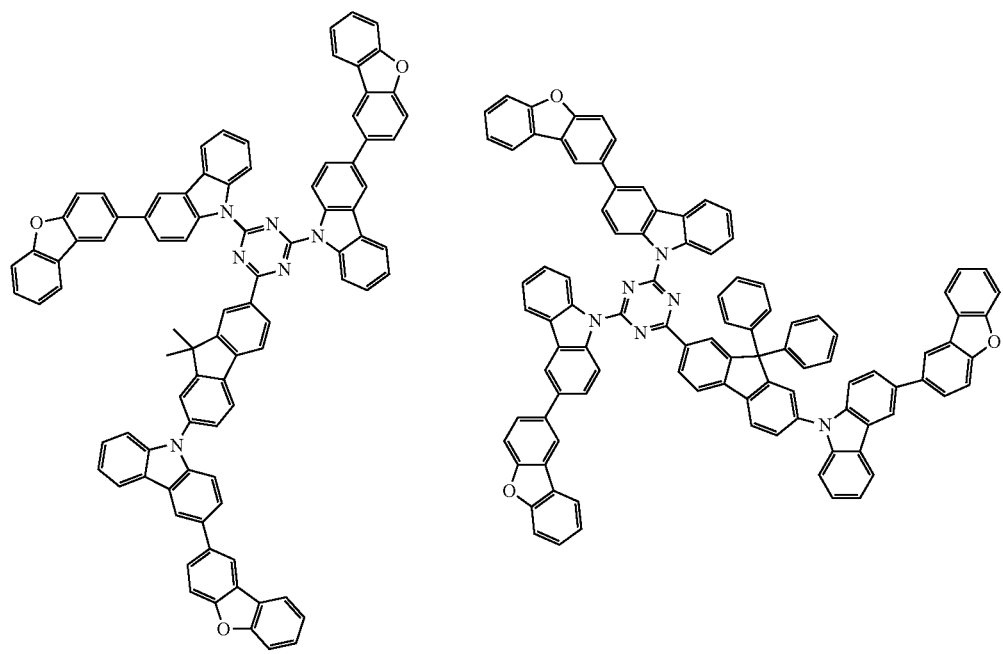

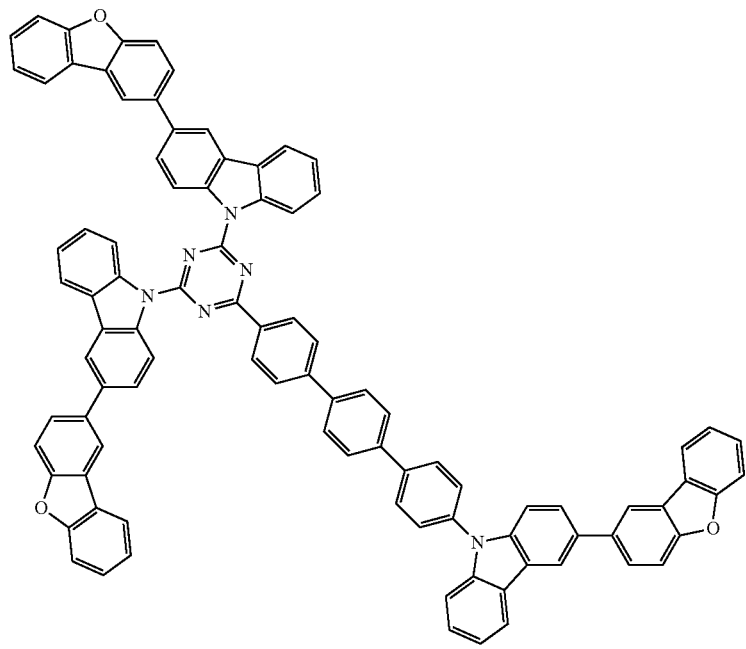
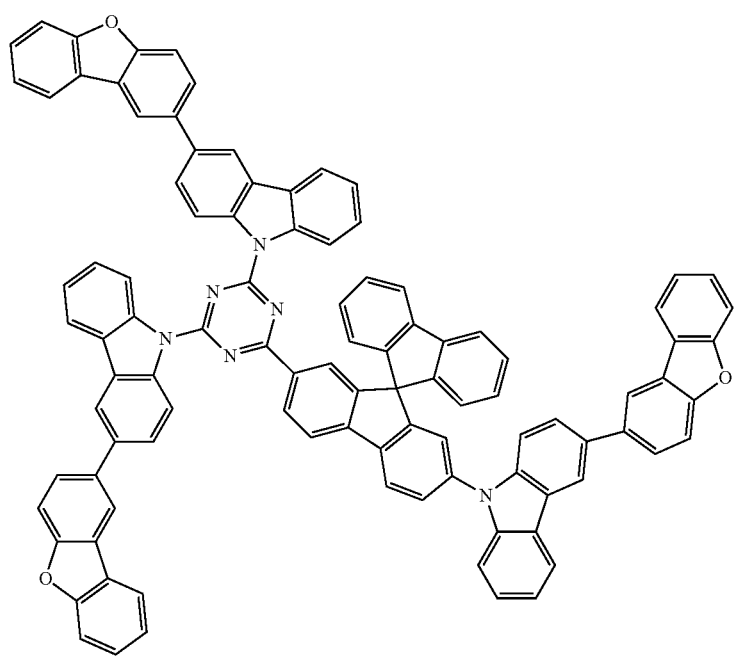

1633 1634
-continued
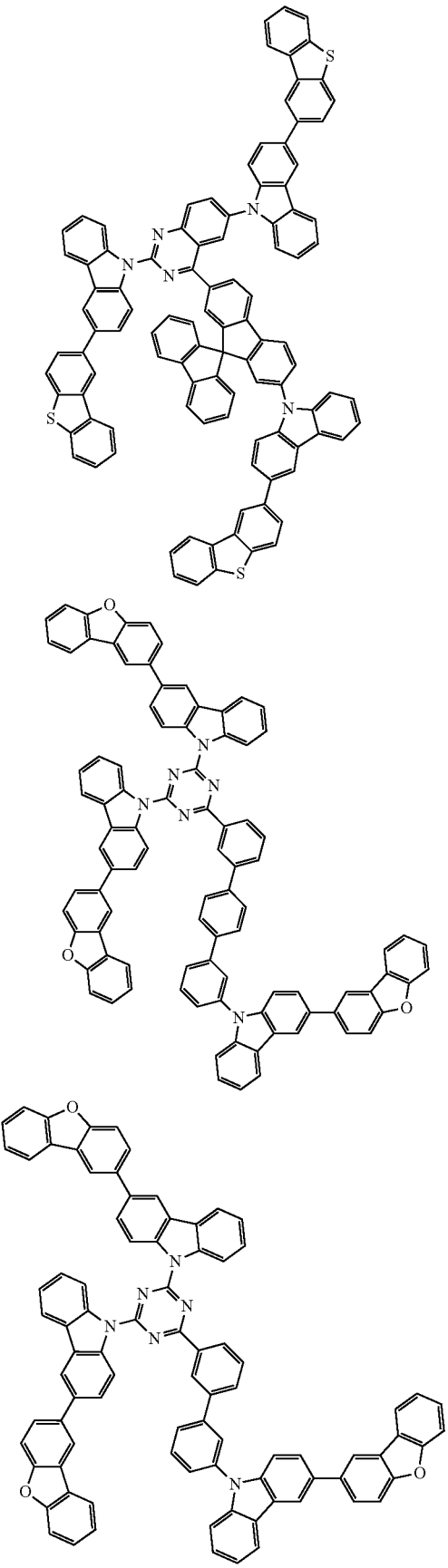
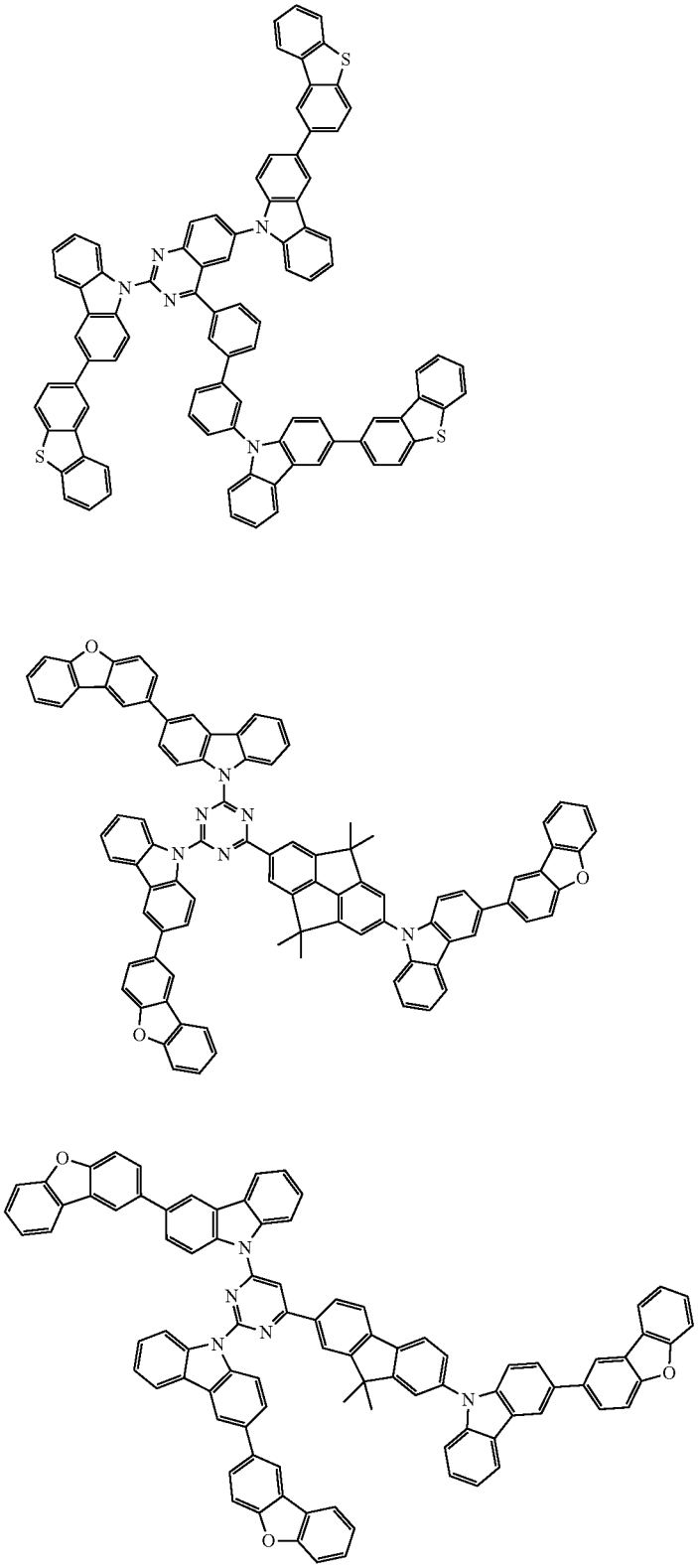

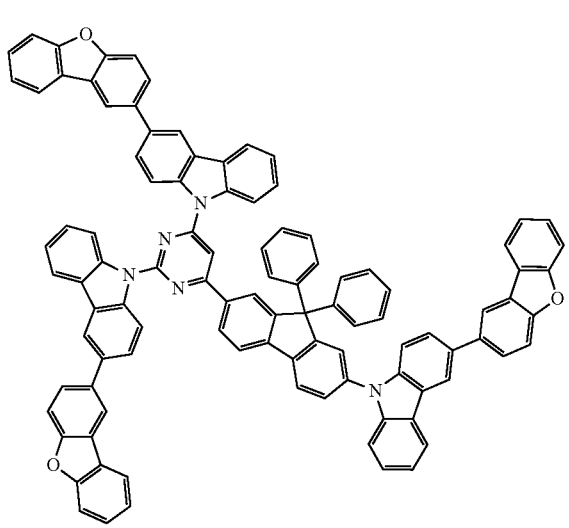
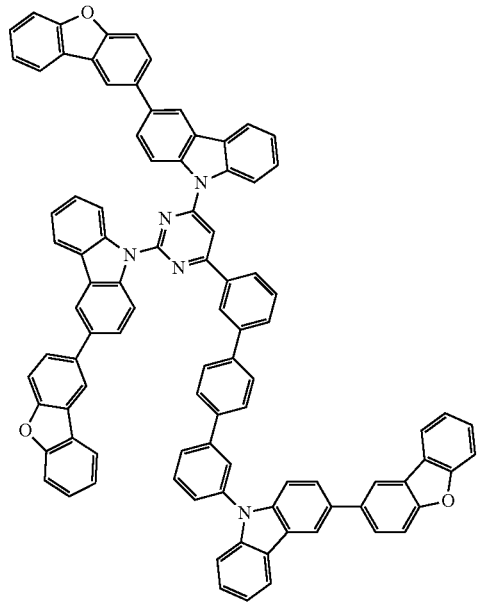
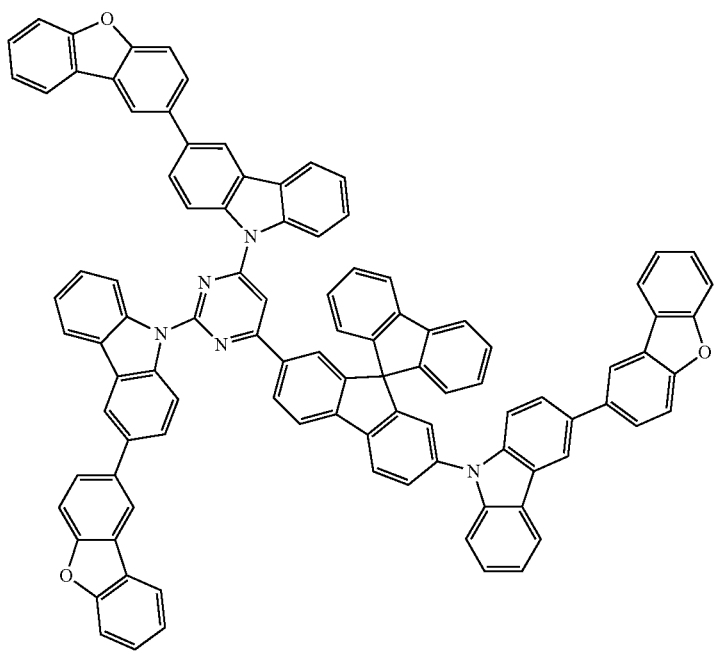

1637
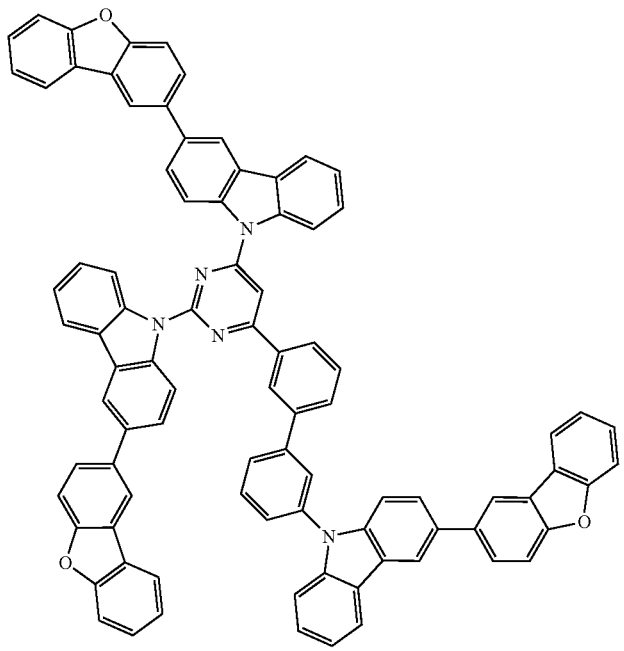
1638
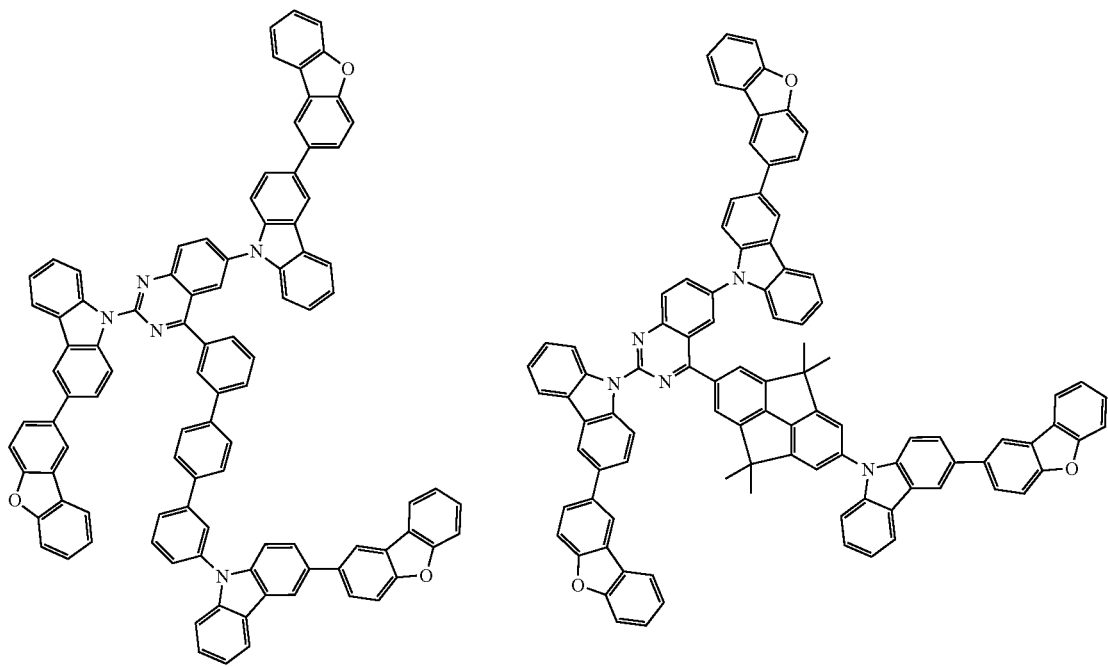 [SMILES: c1cc(-c2ccc(-c3cccc(-n4c5ccccc5c5cc(-c6ccc7oc8ccccc8c7c6)ccc54)c3)cc2)cc(-c2nc(-n3c4ccccc4c4cc(-c5ccc6oc7ccccc7c6c5)ccc43)nc3ccc(-n4c5ccccc5c5cc(-c6ccc7oc8ccccc8c7c6)ccc54)cc23)c1 ; CC1(C)c2cc(-c3nc(-n4c5ccccc5c5cc(-c6ccc7oc8ccccc8c7c6)ccc54)nc4ccc(-n5c6ccccc6c6cc(-c7ccc8oc9ccccc9c8c7)ccc65)cc34)cc3c2-c2c1cc(-n1c4ccccc4c4cc(-c5ccc6oc7ccccc7c6c5)ccc41)cc2C3(C)C]

1639 1640
-continued
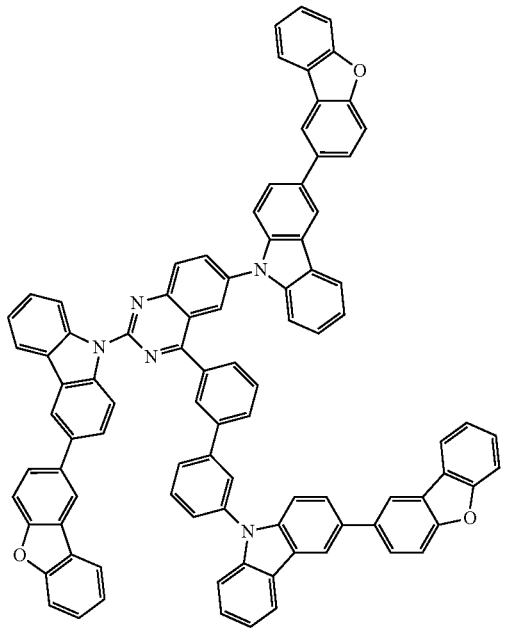
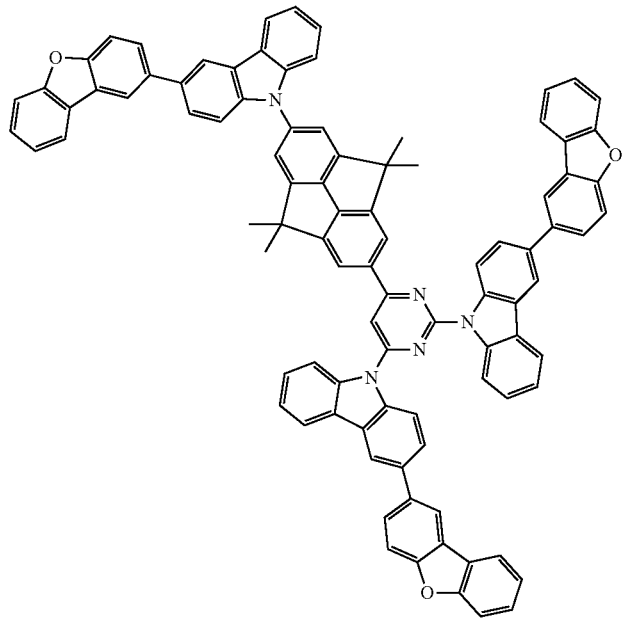
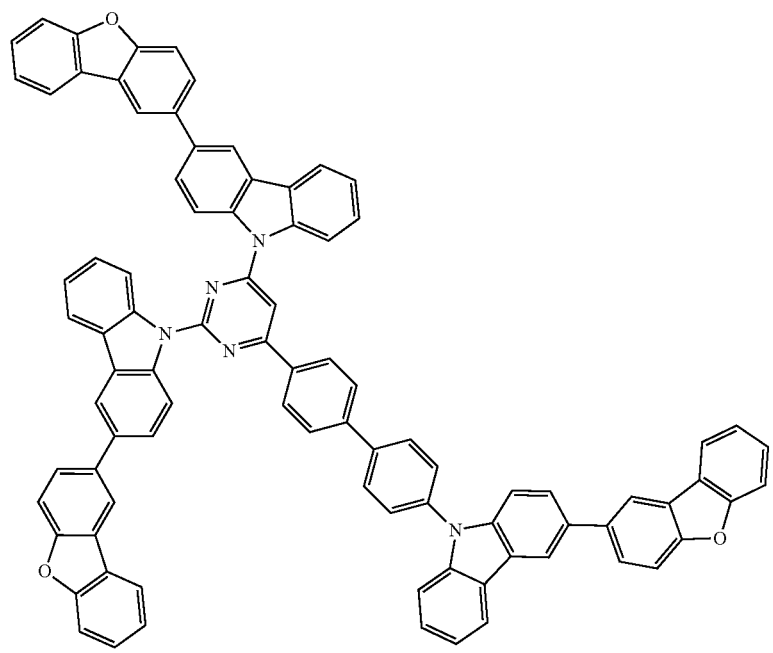

| 1641 | 1642 |
|---|---|
| 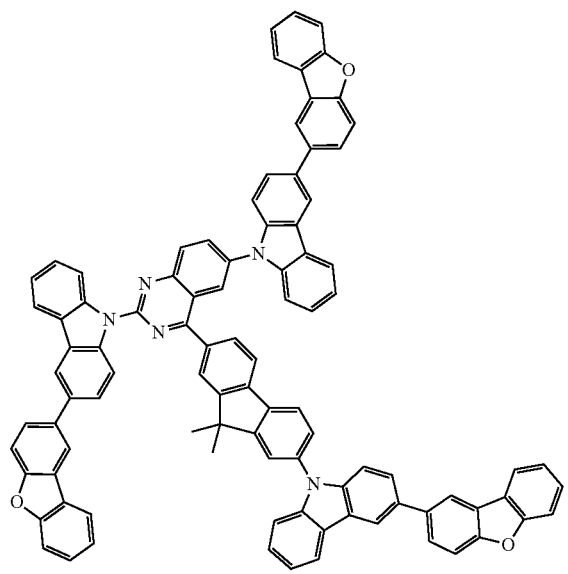 | 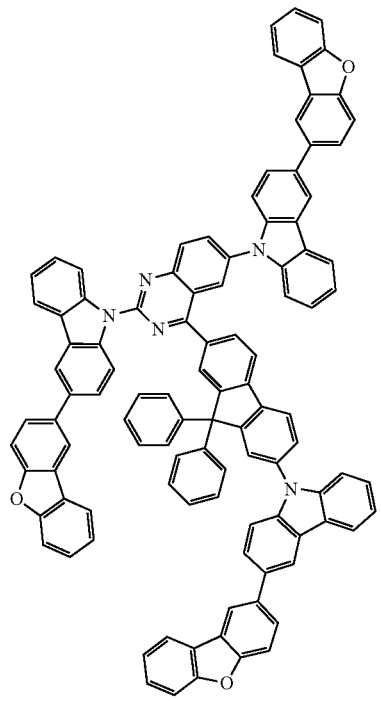 |
| 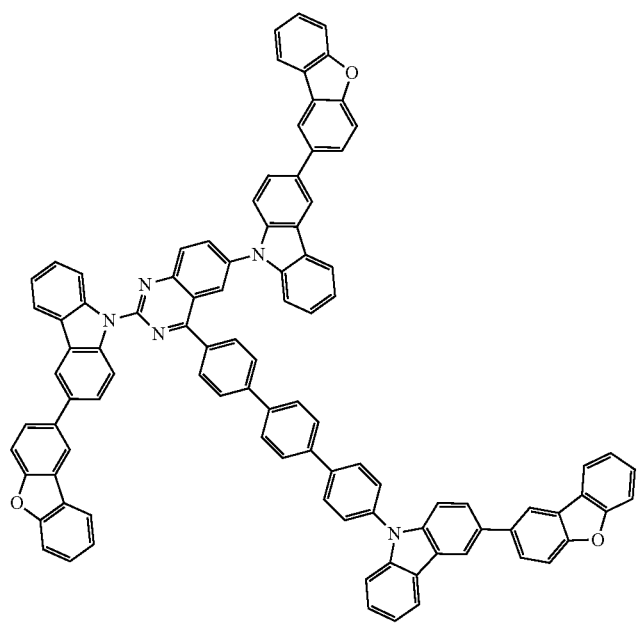 | 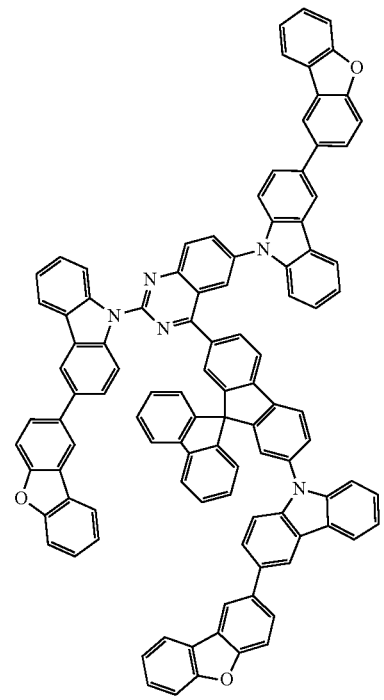 |

1643
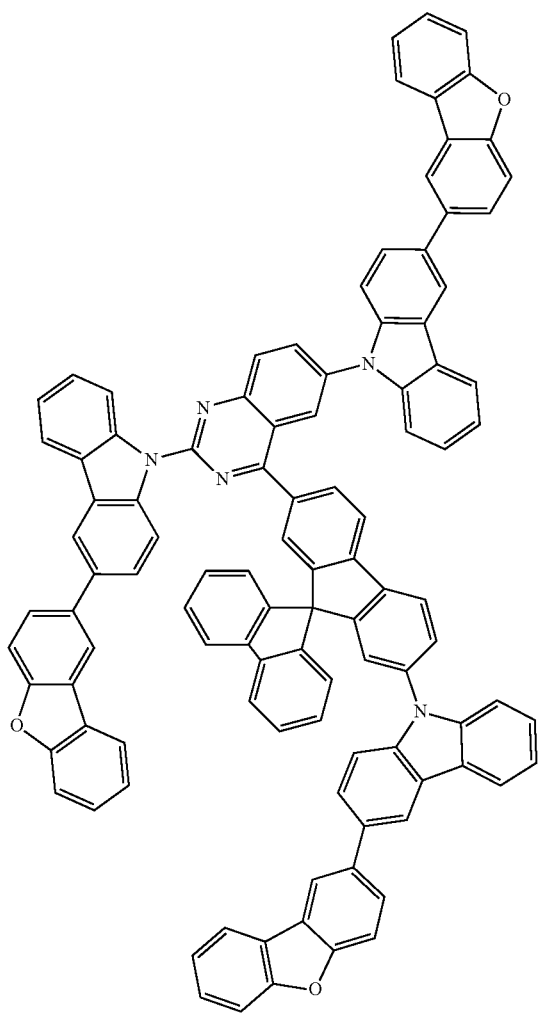
1644
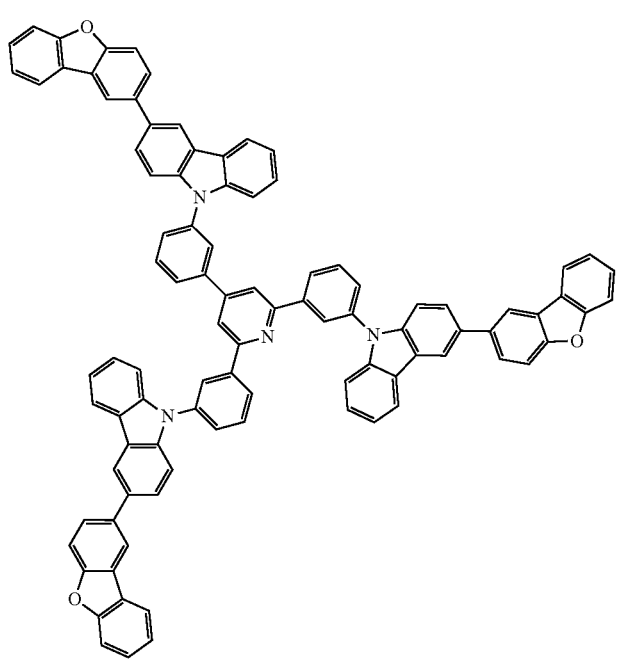
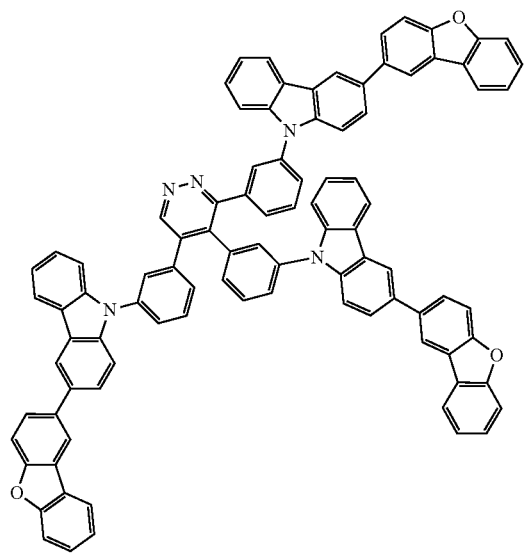

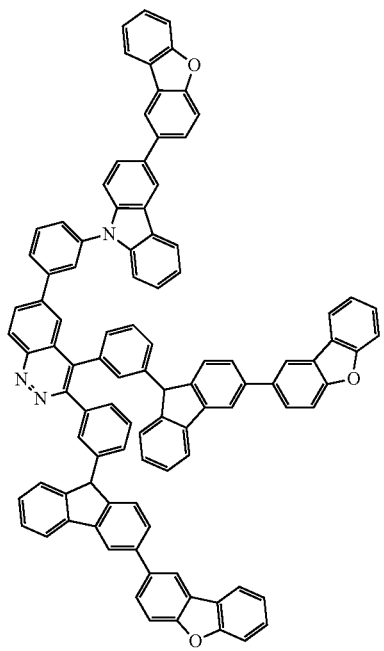
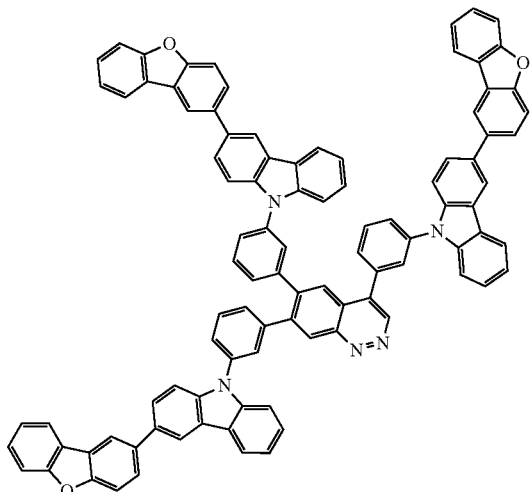
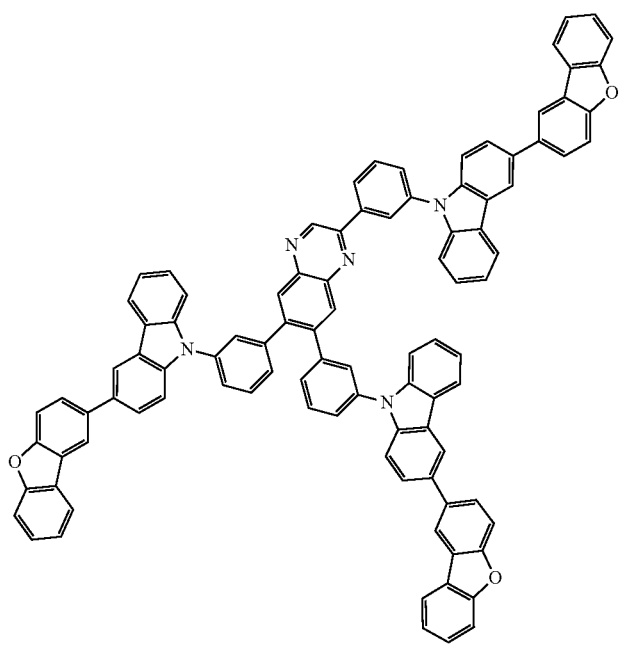

-continued
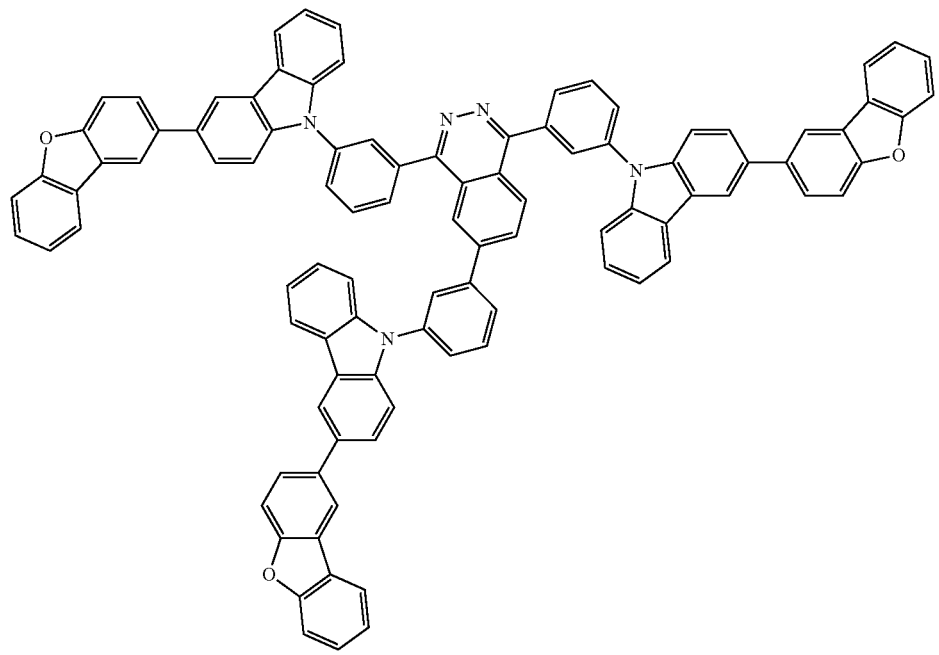
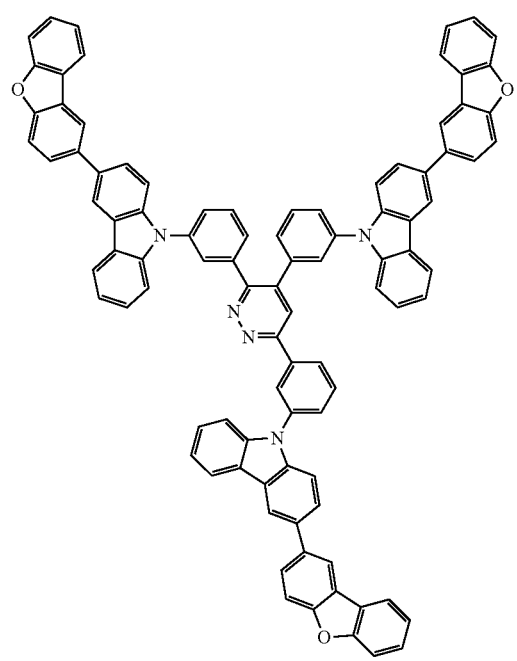

1649 1650
-continued
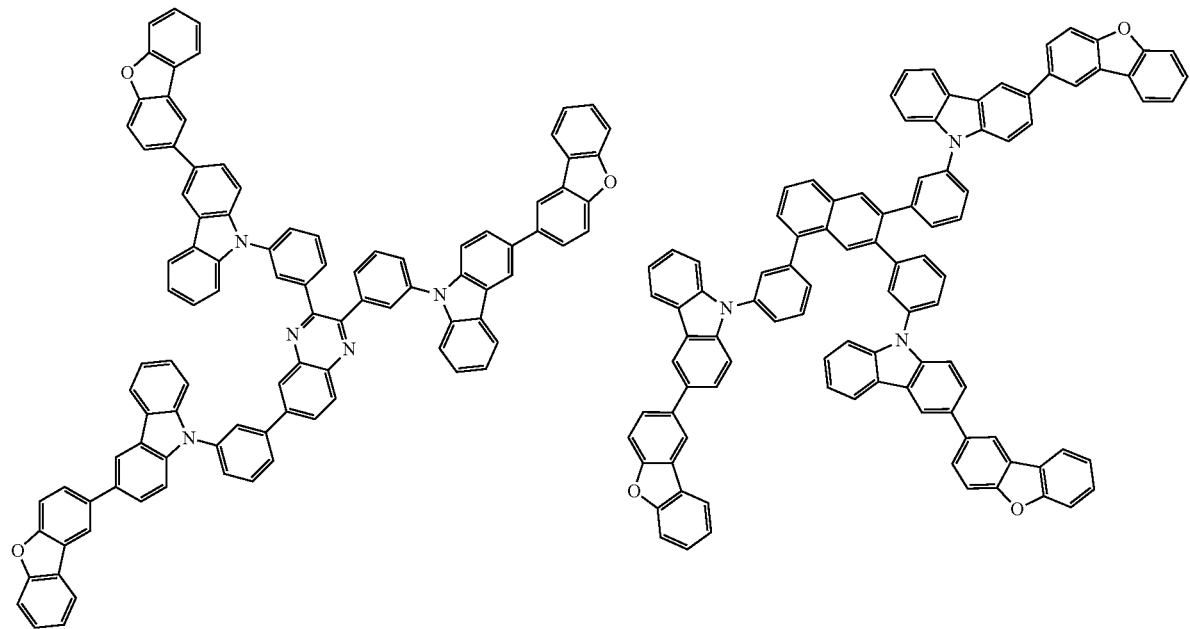 [SMILES: c1cc(-c2ccc3nc(-c4cccc(-n5c6ccccc6c6cc(-c7ccc8oc9ccccc9c8c7)ccc65)c4)c(-c4cccc(-n5c6ccccc6c6cc(-c7ccc8oc9ccccc9c8c7)ccc65)c4)nc3c2)cc(-n2c3ccccc3c3cc(-c4ccc5oc6ccccc6c5c4)ccc32)c1 ; c1cc(-c2cc3cccc(-c4cccc(-n5c6ccccc6c6cc(-c7ccc8oc9ccccc9c8c7)ccc65)c4)c3cc2-c2cccc(-n3c4ccccc4c4cc(-c5ccc6oc7ccccc7c6c5)ccc43)c2)cc(-n2c3ccccc3c3cc(-c4ccc5oc6ccccc6c5c4)ccc32)c1]
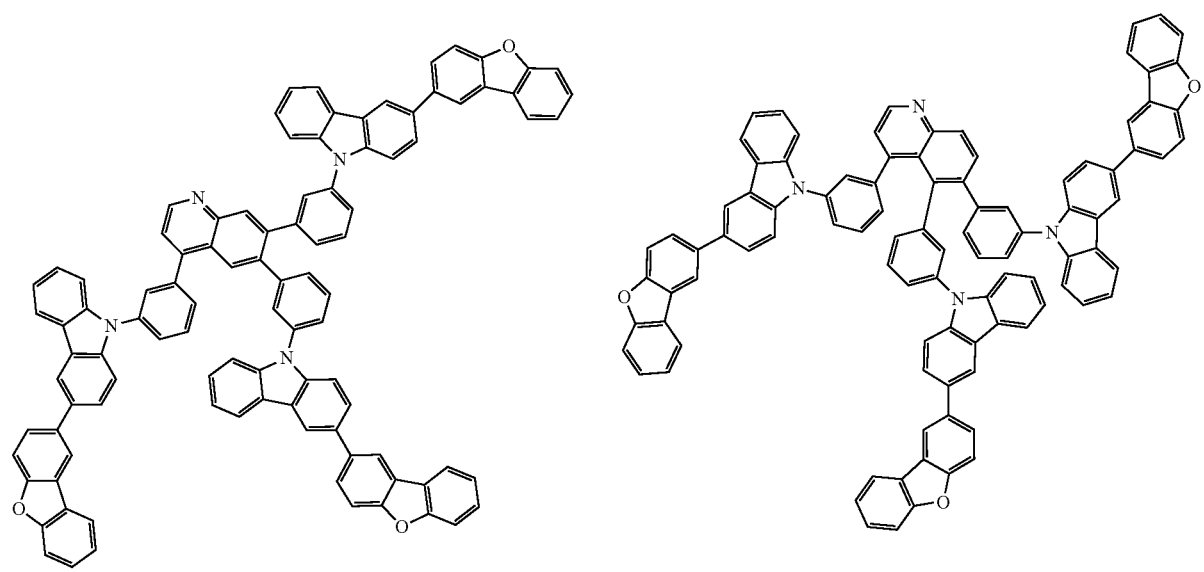 [SMILES: c1cc(-c2cc3nccc(-c4cccc(-n5c6ccccc6c6cc(-c7ccc8oc9ccccc9c8c7)ccc65)c4)c3cc2-c2cccc(-n3c4ccccc4c4cc(-c5ccc6oc7ccccc7c6c5)ccc43)c2)cc(-n2c3ccccc3c3cc(-c4ccc5oc6ccccc6c5c4)ccc32)c1 ; c1cc(-c2ccc3nccc(-c4cccc(-n5c6ccccc6c6cc(-c7ccc8oc9ccccc9c8c7)ccc65)c4)c3c2-c2cccc(-n3c4ccccc4c4cc(-c5ccc6oc7ccccc7c6c5)ccc43)c2)cc(-n2c3ccccc3c3cc(-c4ccc5oc6ccccc6c5c4)ccc32)c1]

1651 1652
-continued
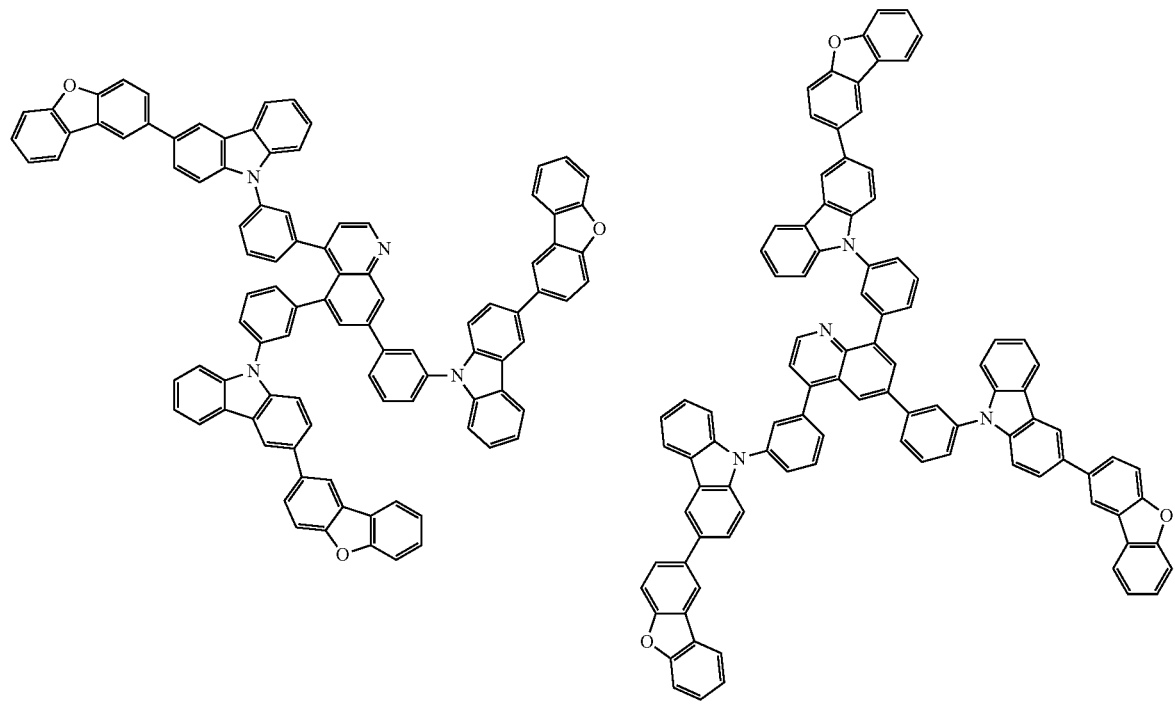 [SMILES: c1cc(-c2cc(-c3cccc(-n4c5ccccc5c5cc(-c6ccc7oc8ccccc8c7c6)ccc54)c3)c3c(-c4cccc(-n5c6ccccc6c6cc(-c7ccc8oc9ccccc9c8c7)ccc65)c4)ccnc3c2)cc(-n2c3ccccc3c3cc(-c4ccc5oc6ccccc6c5c4)ccc32)c1 ; c1cc(-c2cc(-c3cccc(-n4c5ccccc5c5cc(-c6ccc7oc8ccccc8c7c6)ccc54)c3)c3nccc(-c4cccc(-n5c6ccccc6c6cc(-c7ccc8oc9ccccc9c8c7)ccc65)c4)c3c2)cc(-n2c3ccccc3c3cc(-c4ccc5oc6ccccc6c5c4)ccc32)c1]
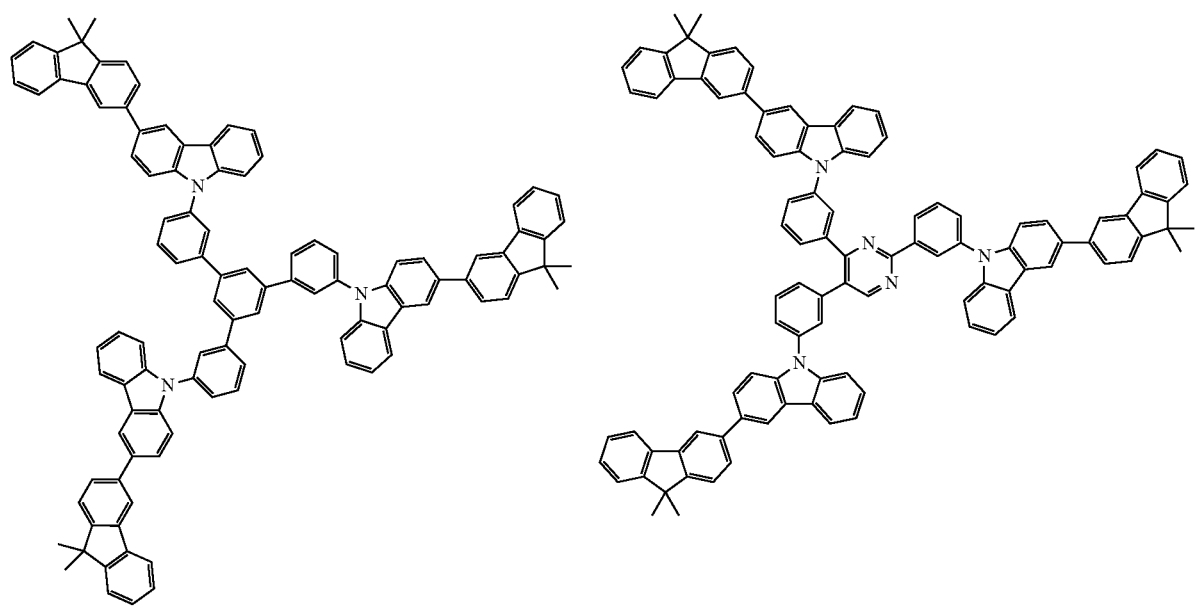 [SMILES: CC1(C)c2ccccc2-c2cc(-c3ccc4c(c3)c3ccccc3n4-c3cccc(-c4cc(-c5cccc(-n6c7ccccc7c7cc(-c8ccc9c(c8)-c8ccccc8C9(C)C)ccc76)c5)cc(-c5cccc(-n6c7ccccc7c7cc(-c8ccc9c(c8)-c8ccccc8C9(C)C)ccc76)c5)c4)c3)ccc21 ; CC1(C)c2ccccc2-c2cc(-c3ccc4c(c3)c3ccccc3n4-c3cccc(-c4ncc(-c5cccc(-n6c7ccccc7c7cc(-c8ccc9c(c8)-c8ccccc8C9(C)C)ccc76)c5)c(-c5cccc(-n6c7ccccc7c7cc(-c8ccc9c(c8)-c8ccccc8C9(C)C)ccc76)c5)n4)c3)ccc21]

1653
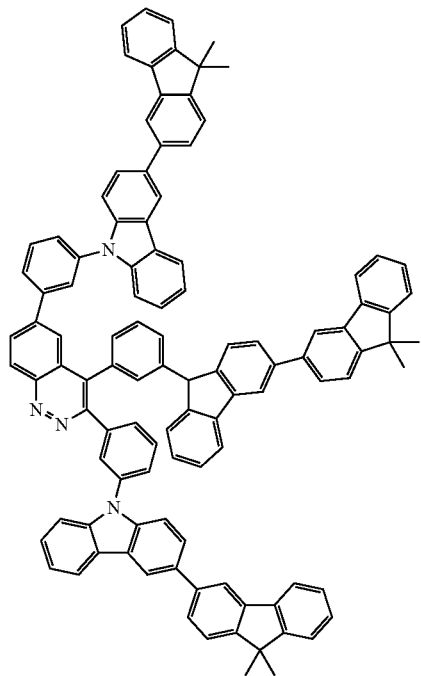
1654
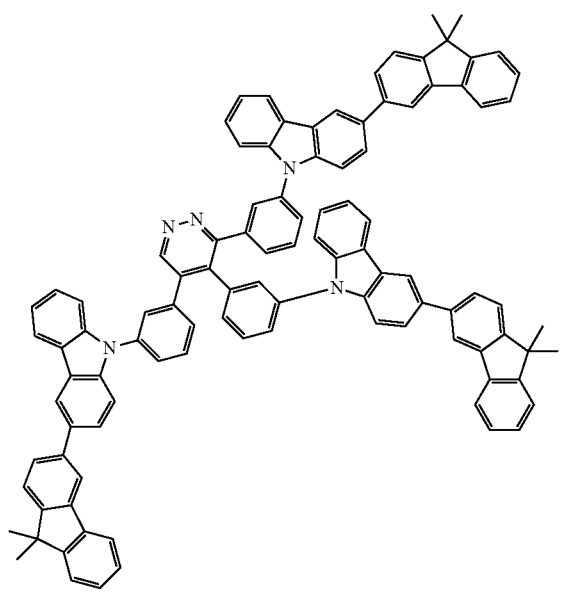
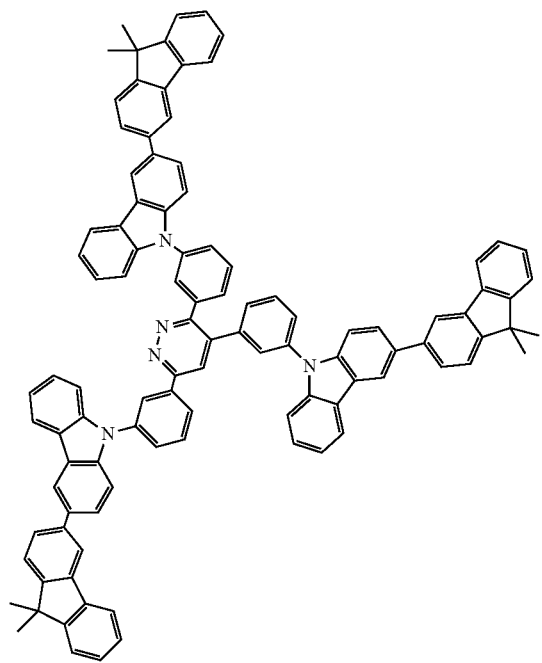

1655 1656
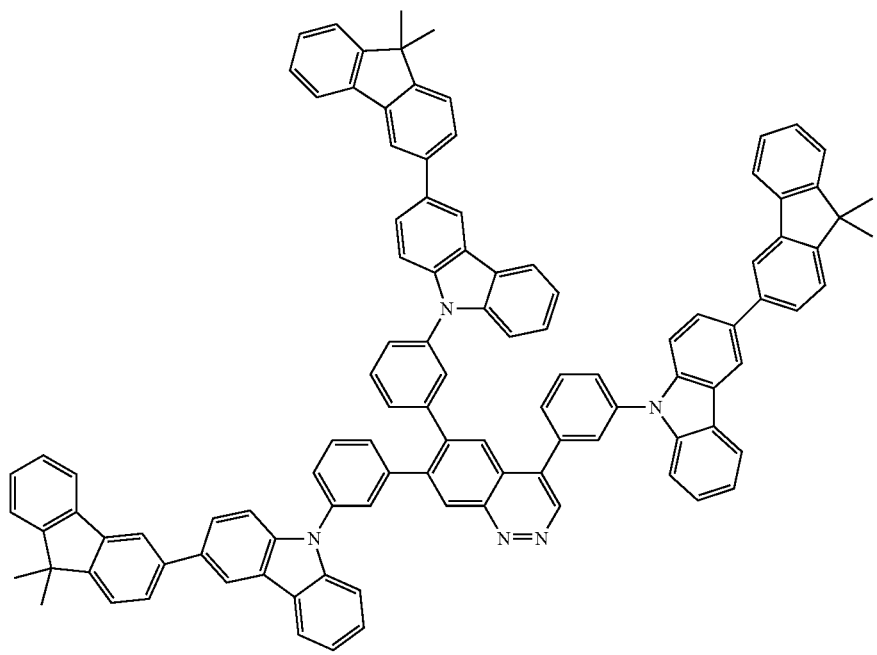
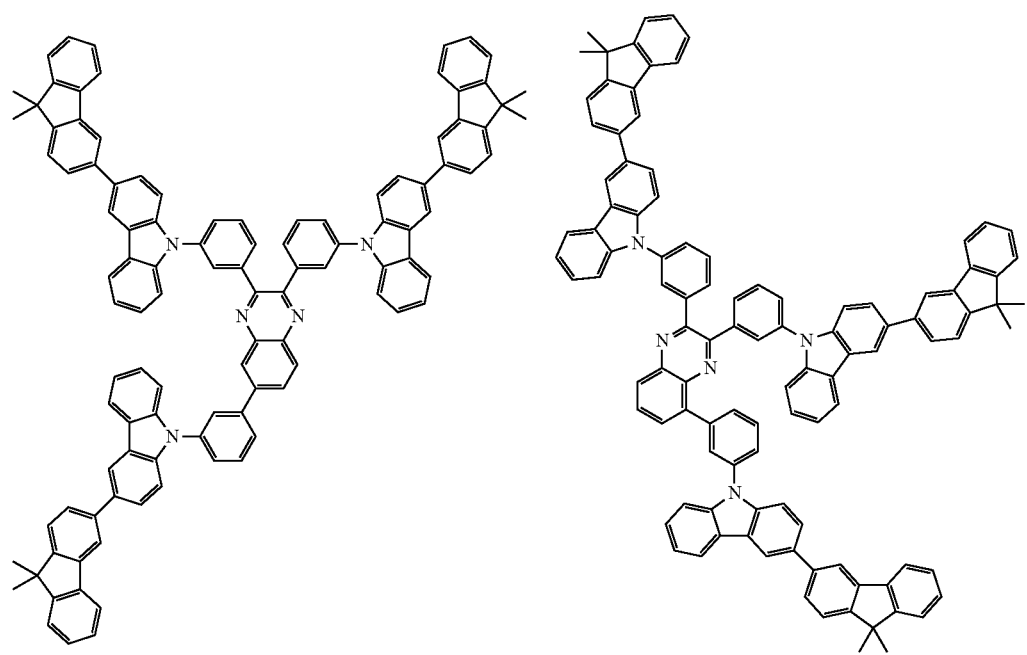

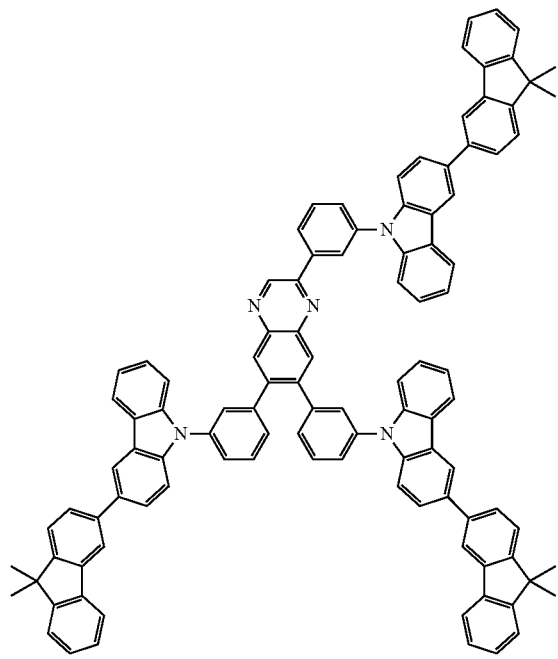
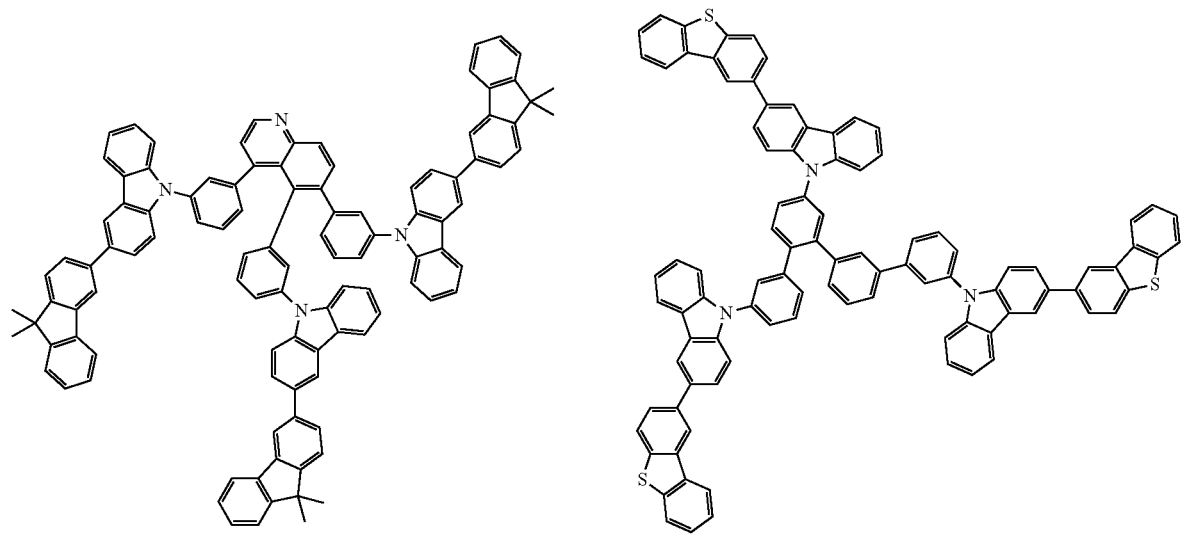

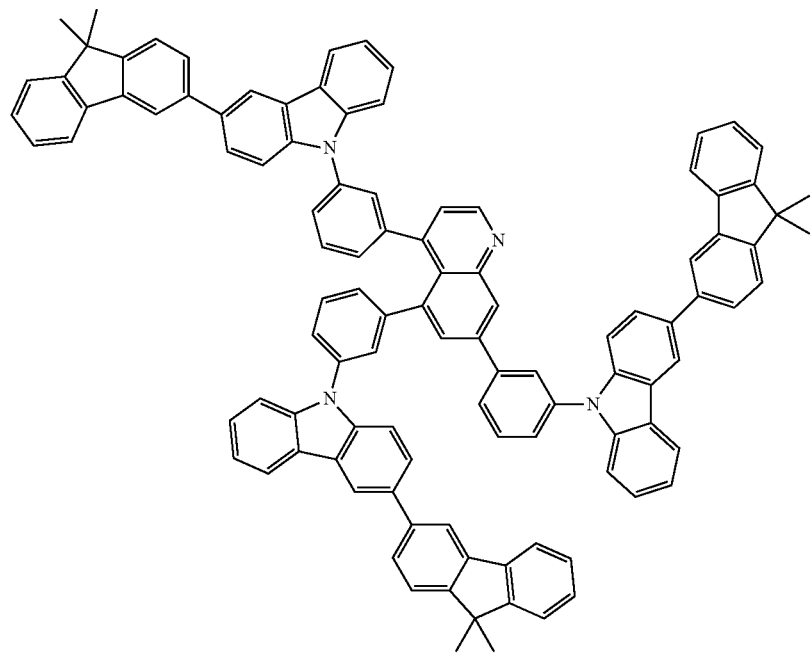
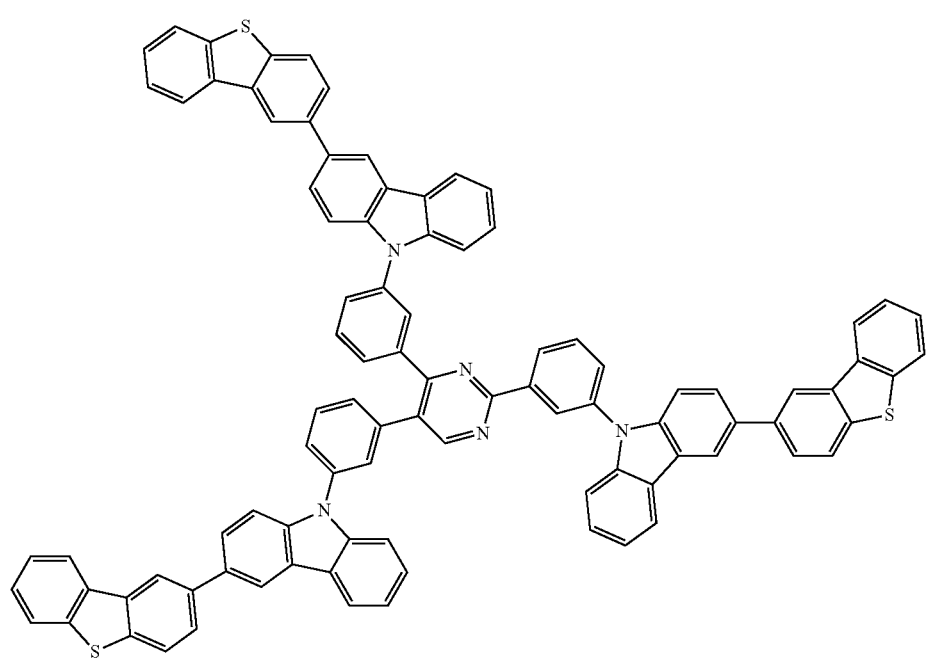

-continued
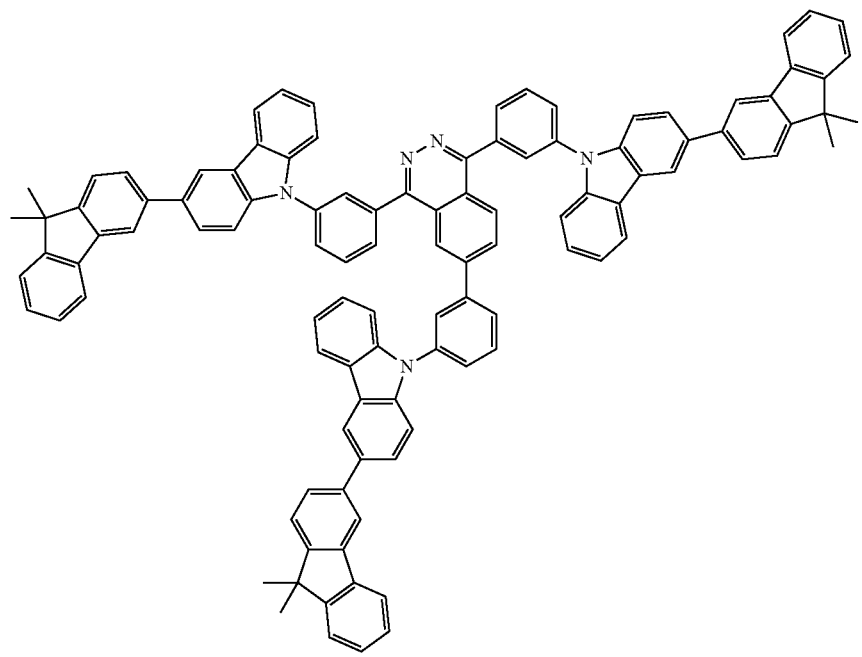
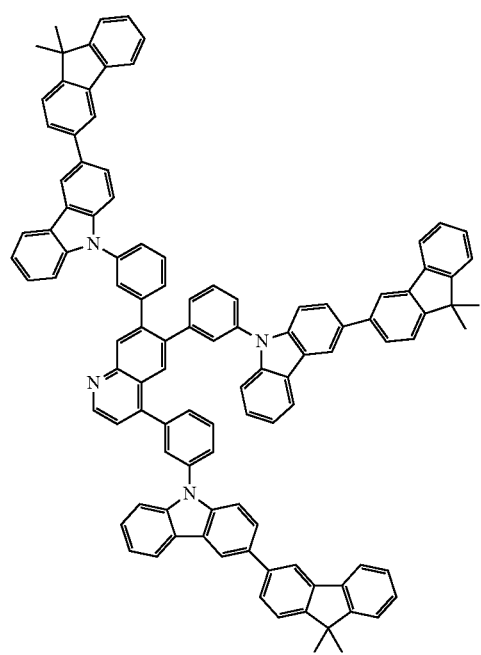

1663 | 1664
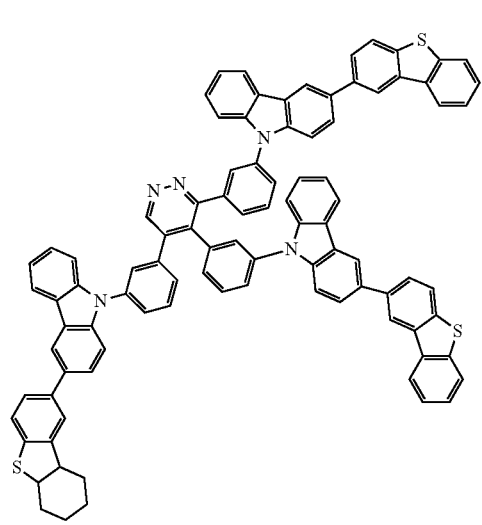
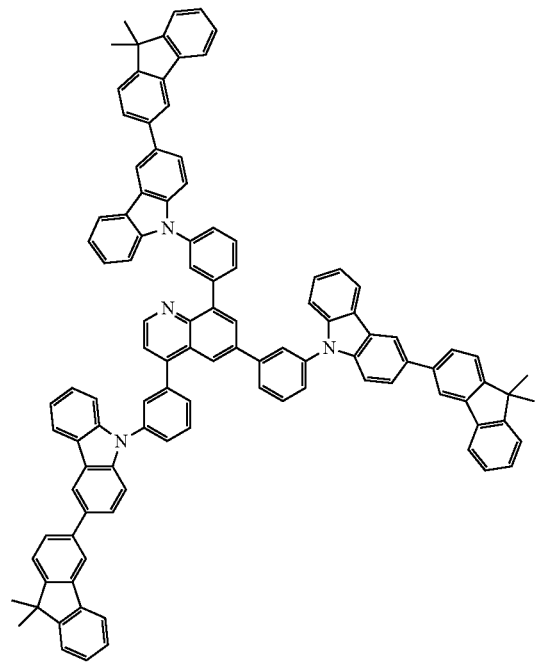
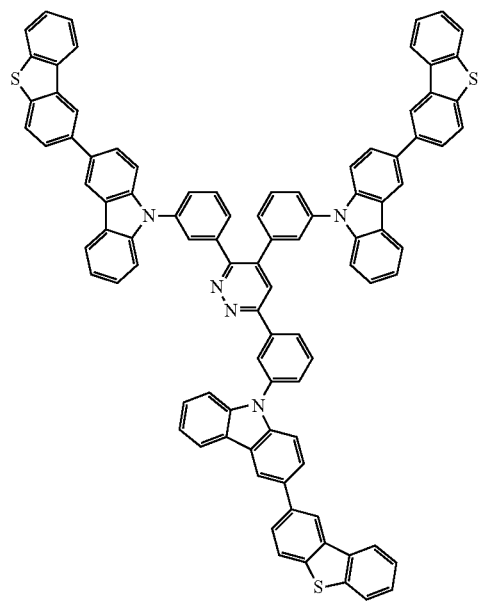
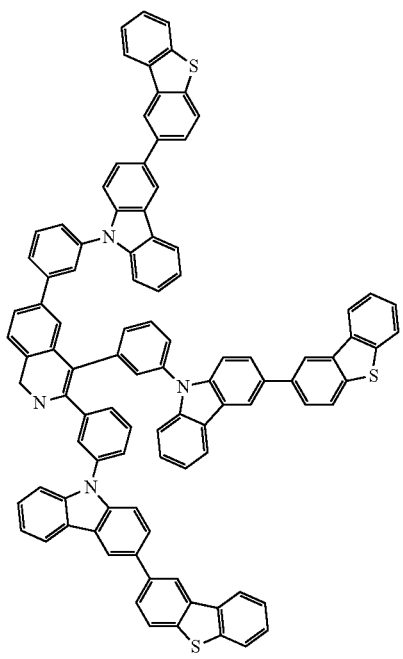

-continued
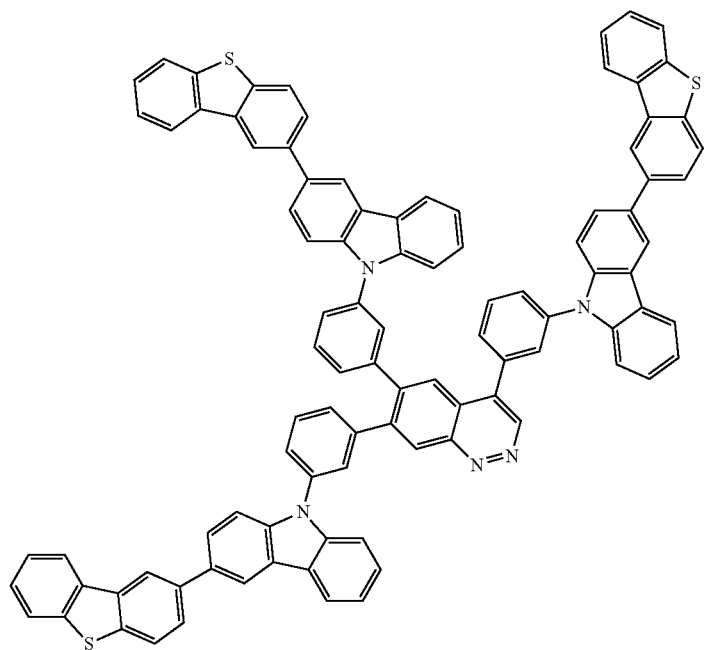
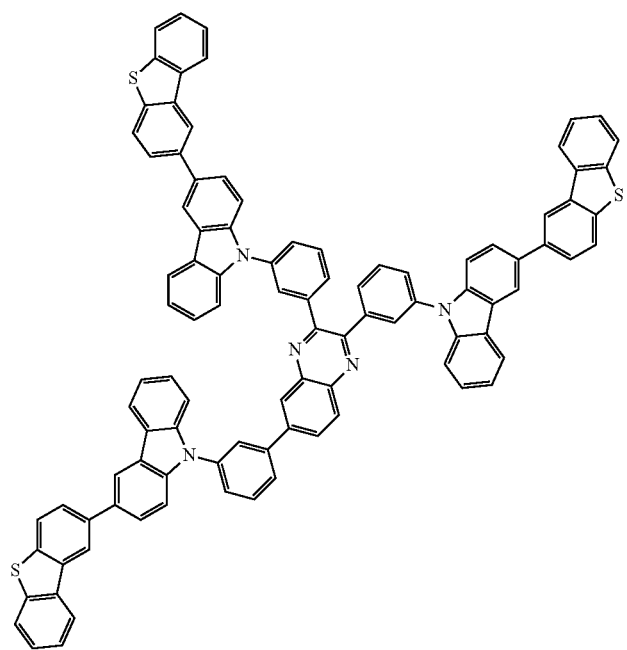

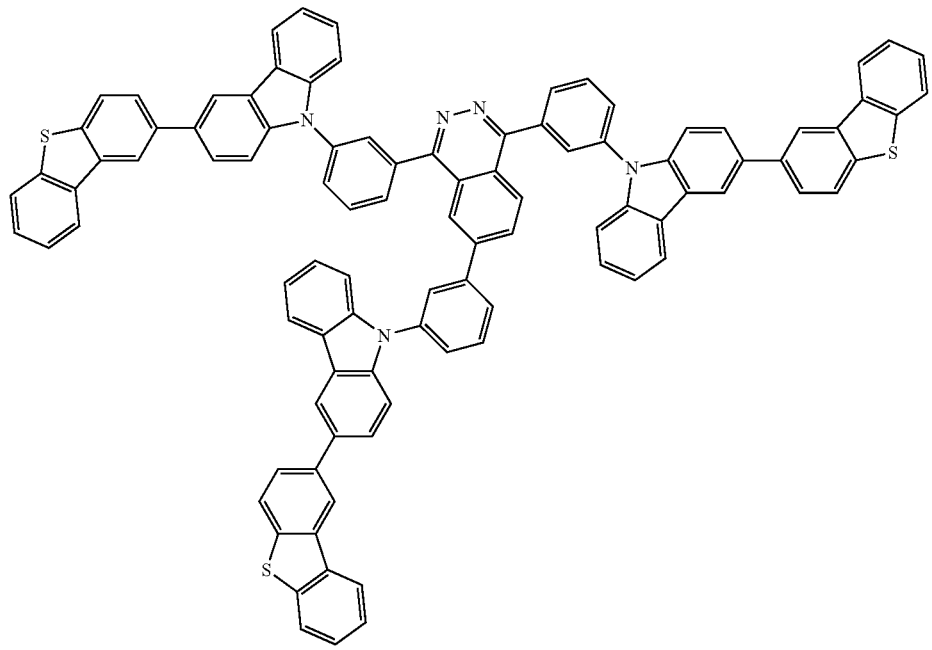
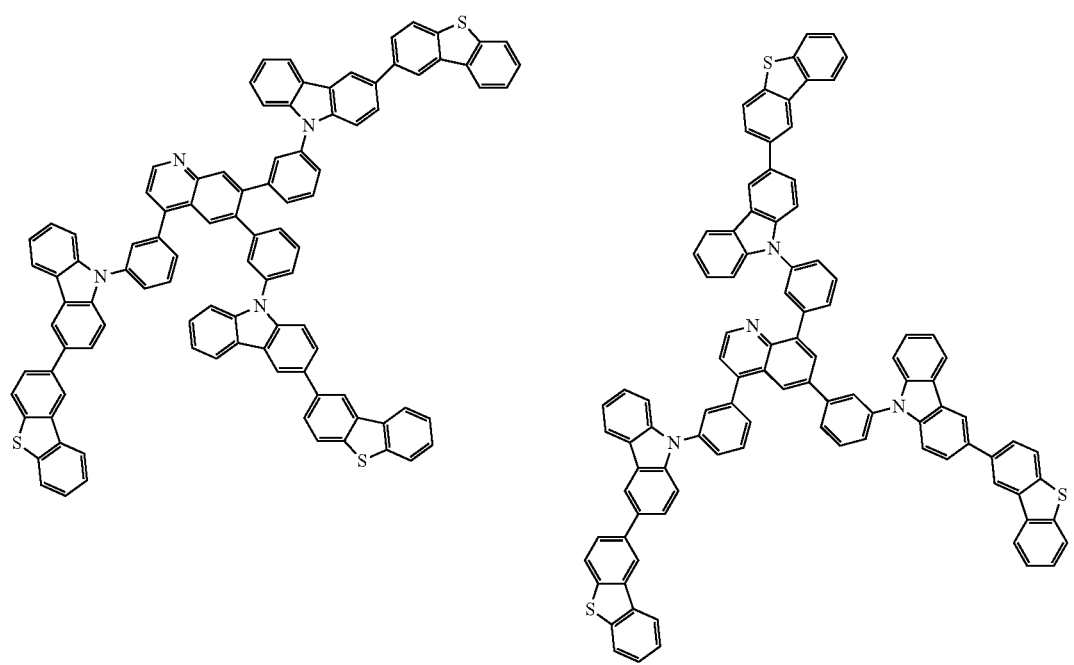 [SMILES: c1cc(-c2cc3nccc(-c4cccc(-n5c6ccccc6c6cc(-c7ccc8sc9ccccc9c8c7)ccc65)c4)c3cc2-c2cccc(-n3c4ccccc4c4cc(-c5ccc6sc7ccccc7c6c5)ccc43)c2)cc(-n2c3ccccc3c3cc(-c4ccc5sc6ccccc6c5c4)ccc32)c1 ; c1cc(-c2cc(-c3cccc(-n4c5ccccc5c5cc(-c6ccc7sc8ccccc8c7c6)ccc54)c3)c3nccc(-c4cccc(-n5c6ccccc6c6cc(-c7ccc8sc9ccccc9c8c7)ccc65)c4)c3c2)cc(-n2c3ccccc3c3cc(-c4ccc5sc6ccccc6c5c4)ccc32)c1]

1669
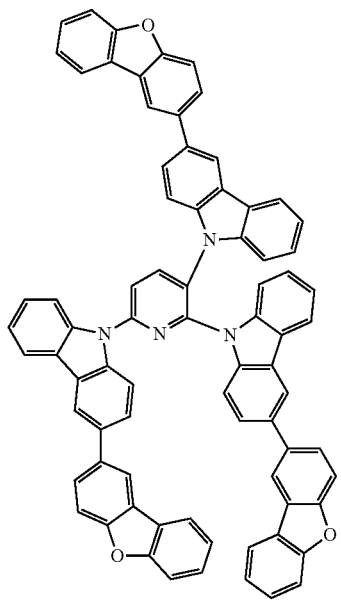
1670
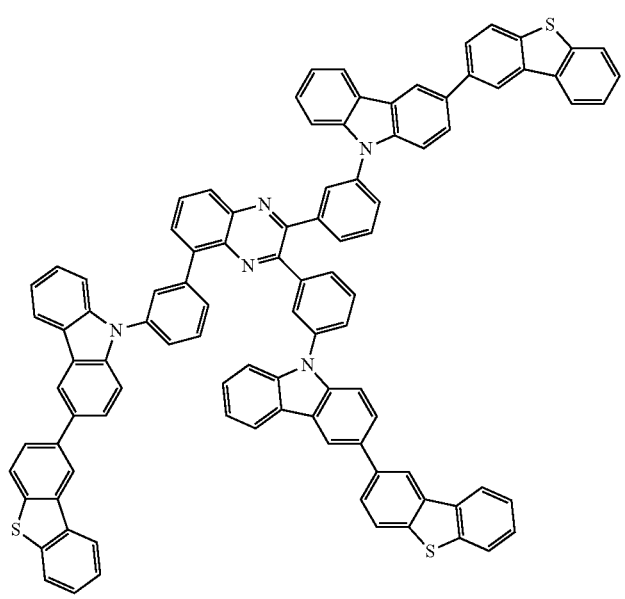
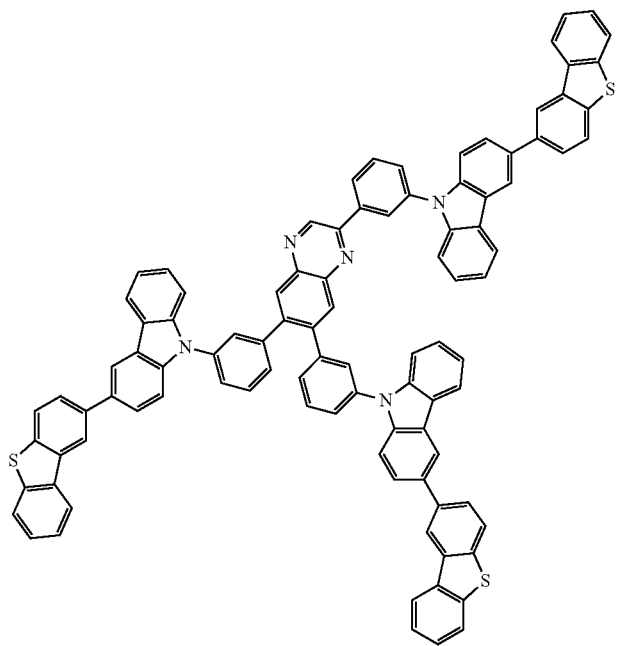

-continued
1671     1672
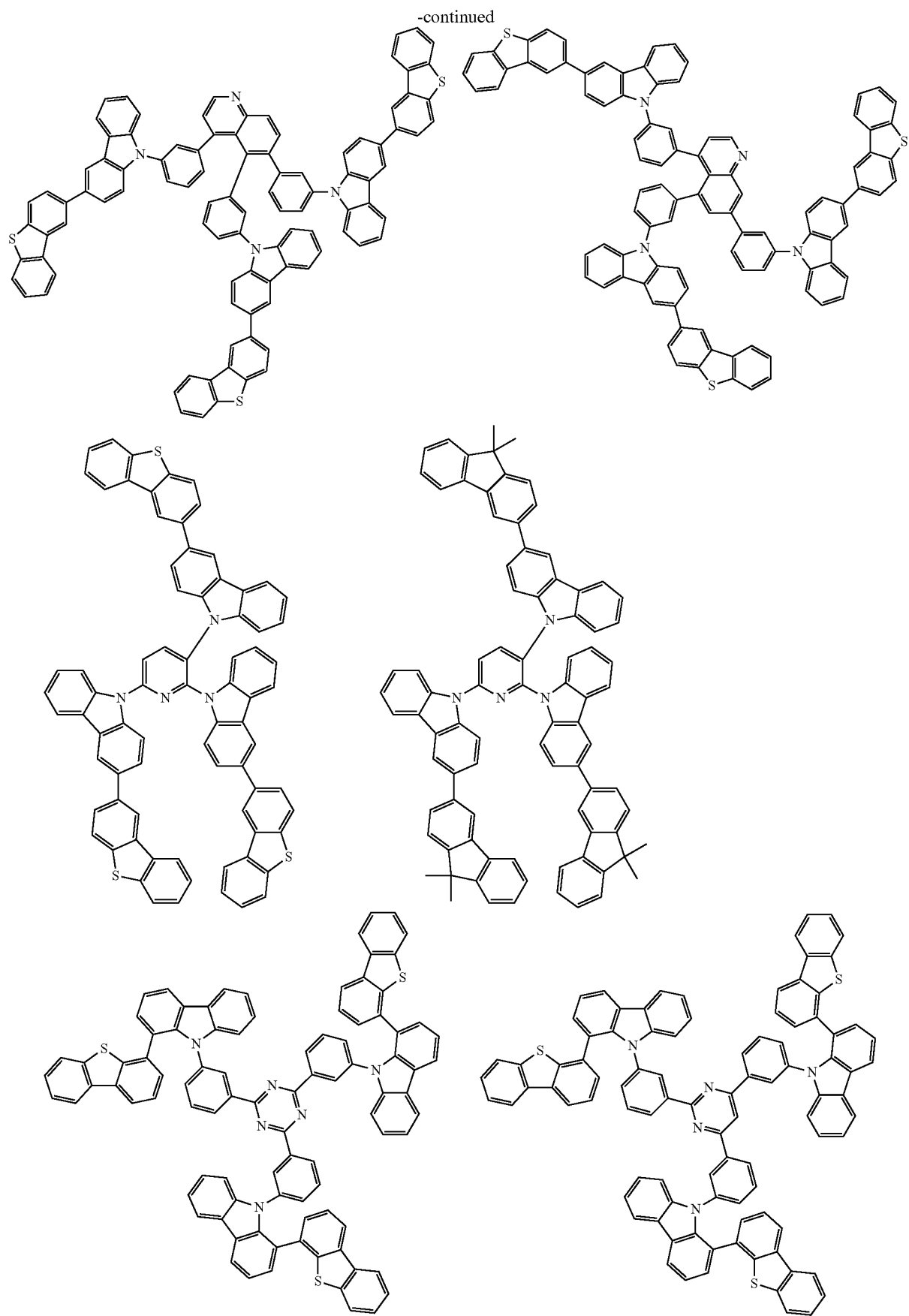

1673
1674
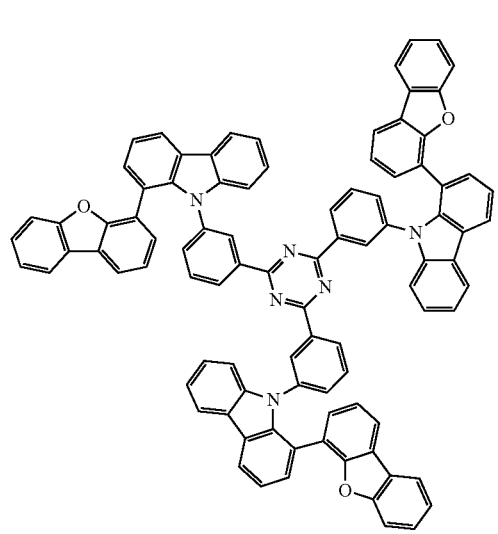
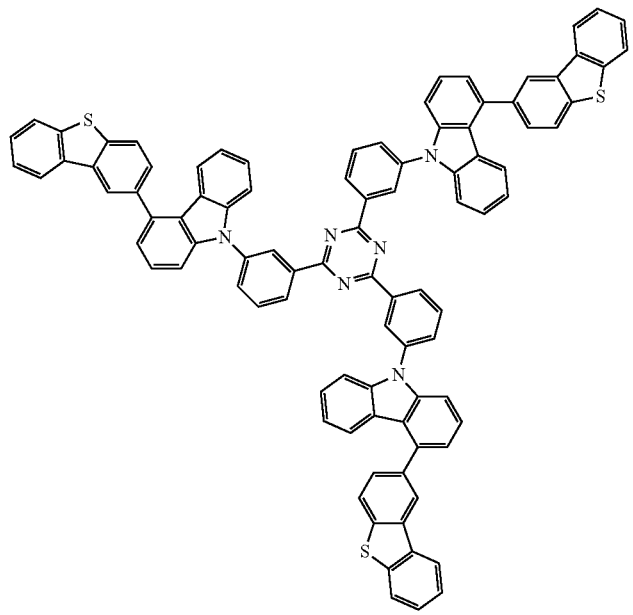
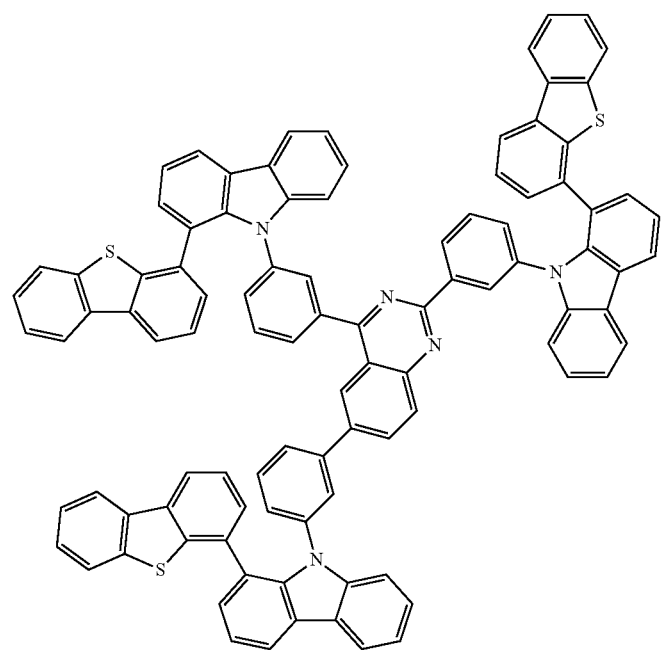

-continued
| 1675 | 1676 |
|---|---|
| 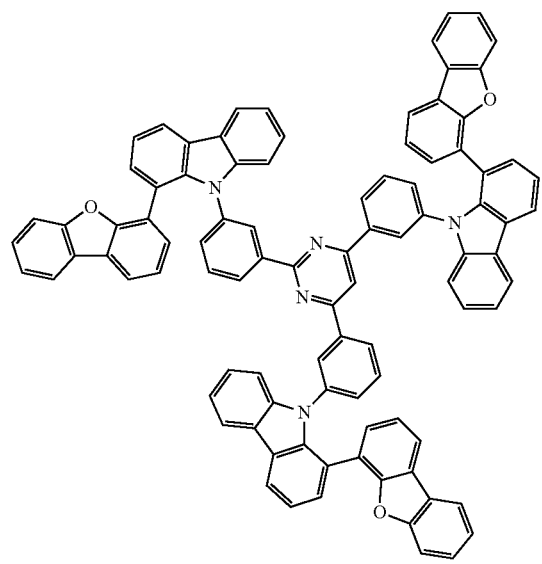 | 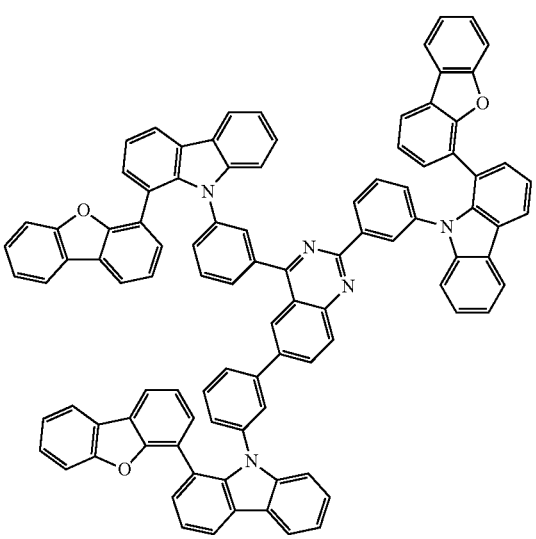 |
| 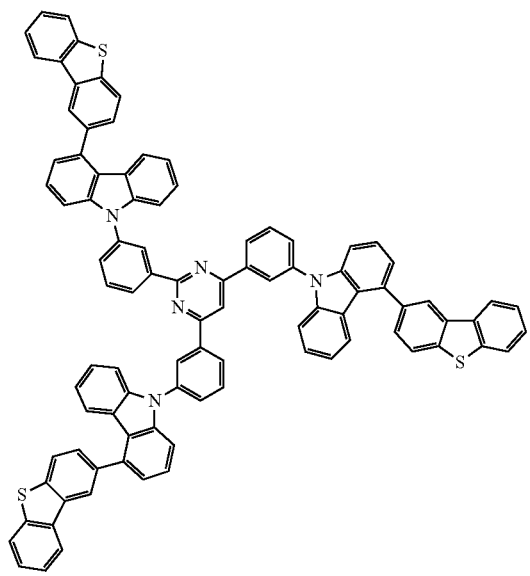 | 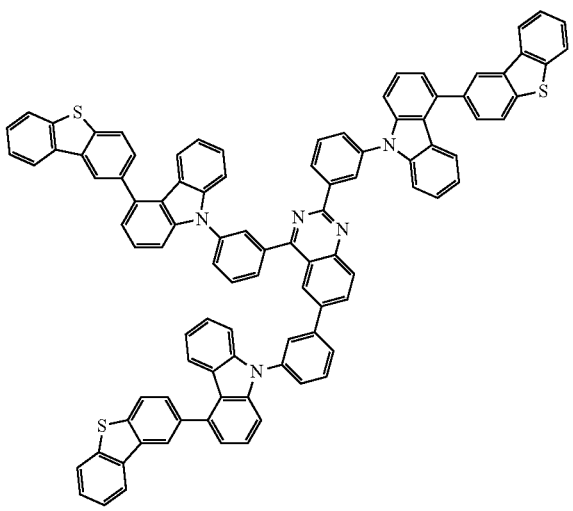 |
| 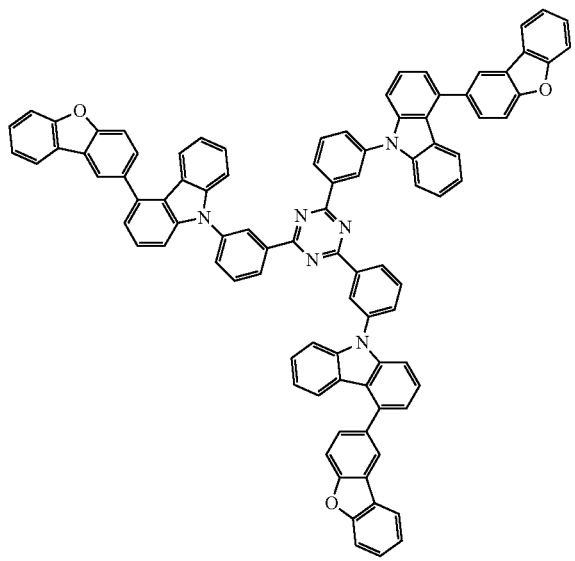 | 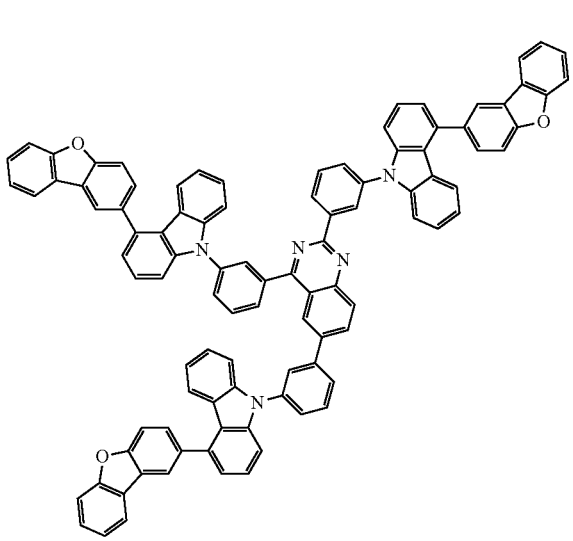 |

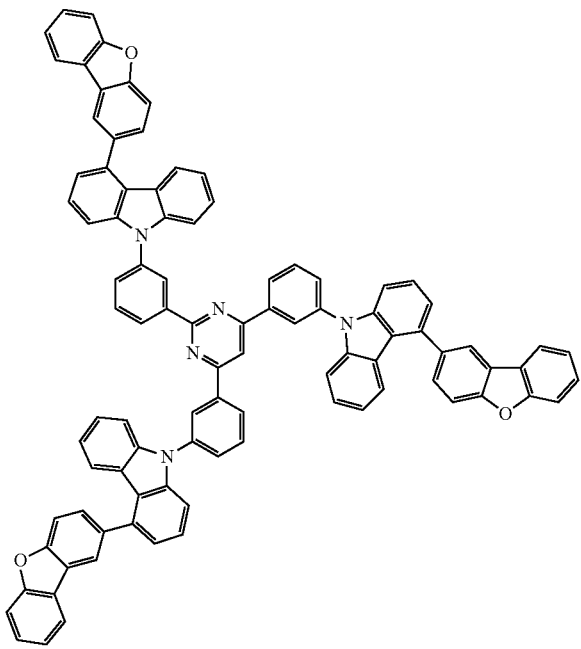

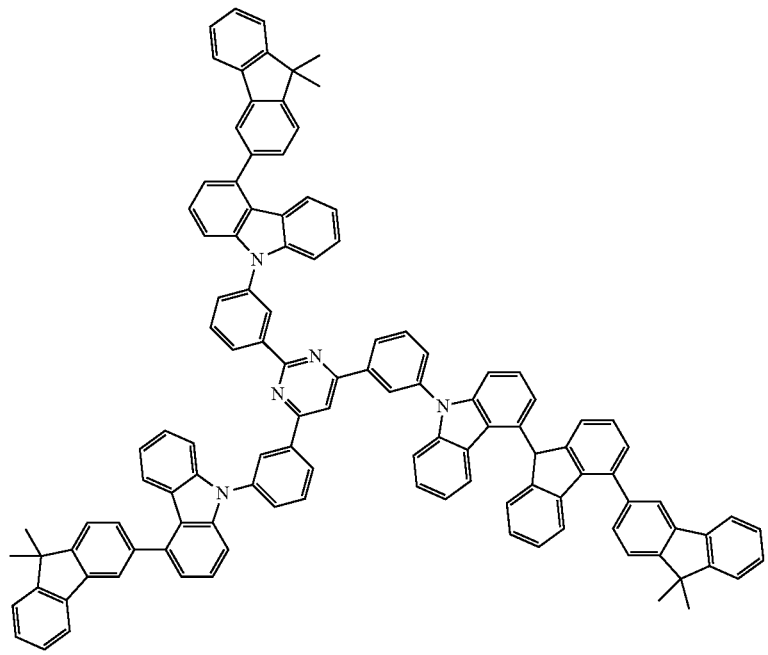
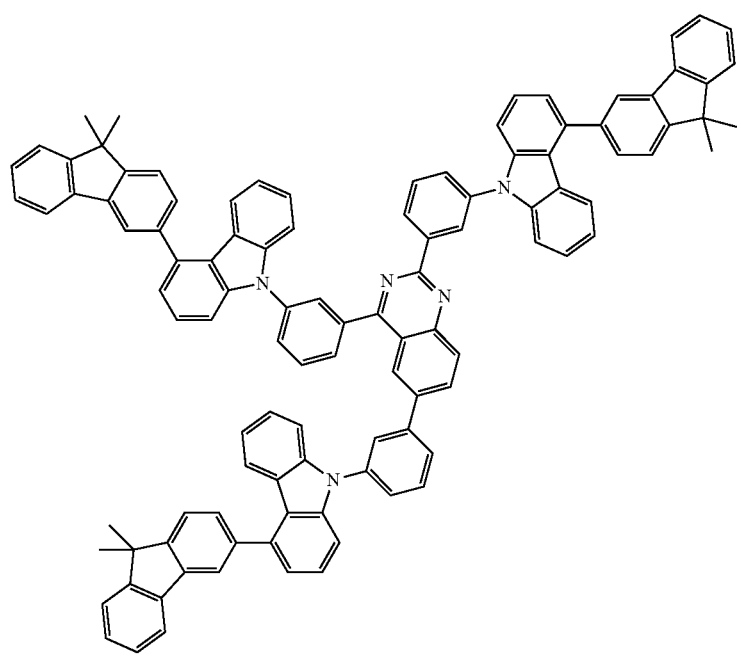

1681
1682
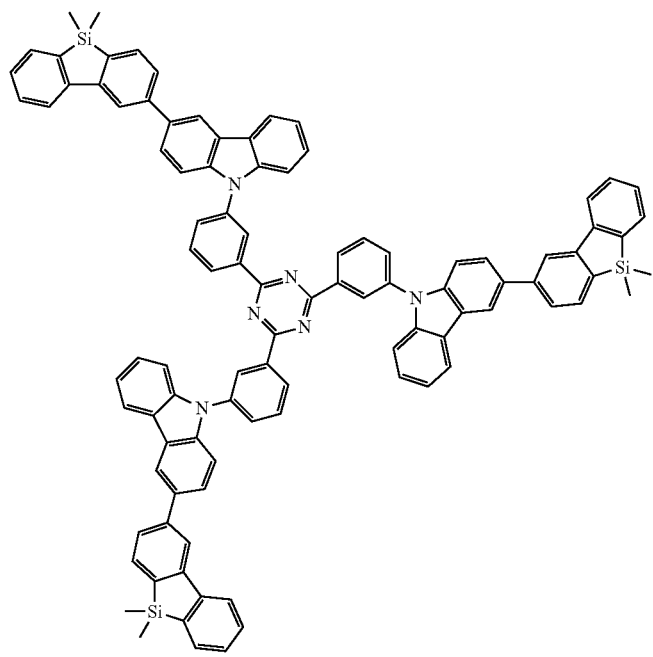
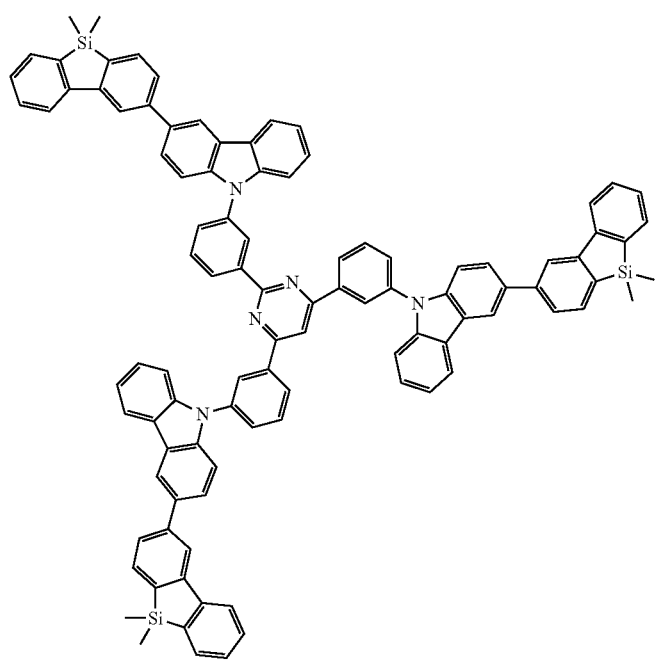

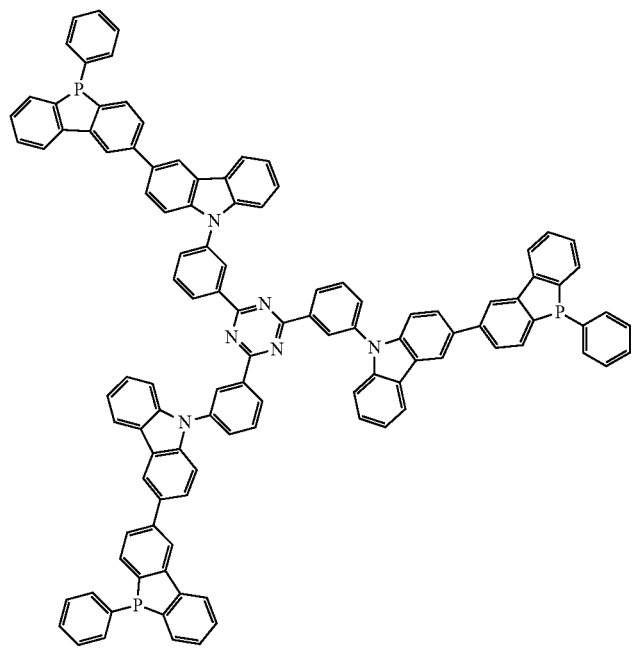 [SMILES: c1ccc(-p2c3ccccc3c3cc(-c4ccc5c(c4)c4ccccc4n5-c4cccc(-c5nc(-c6cccc(-n7c8ccccc8c8cc(-c9ccc%10c(c9)c9ccccc9p%10-c9ccccc9)ccc87)c6)nc(-c6cccc(-n7c8ccccc8c8cc(-c9ccc%10c(c9)c9ccccc9p%10-c9ccccc9)ccc87)c6)n5)c4)ccc32)cc1]
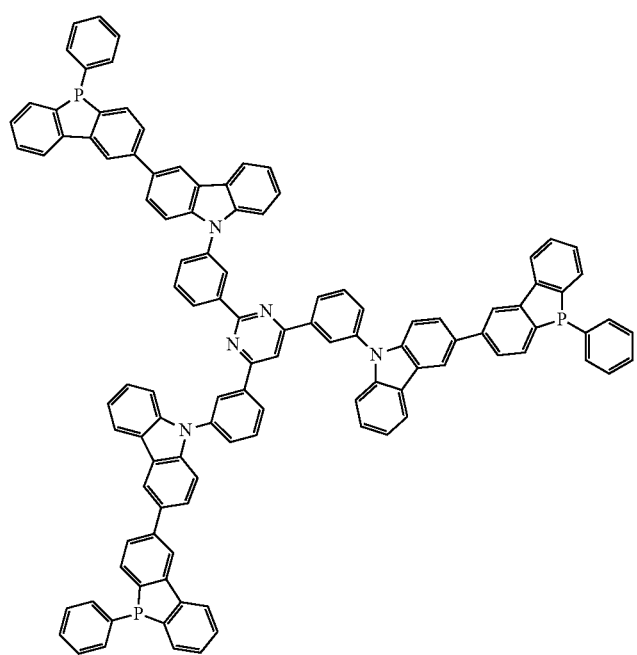 [SMILES: c1ccc(-p2c3ccccc3c3cc(-c4ccc5c(c4)c4ccccc4n5-c4cccc(-c5cc(-c6cccc(-n7c8ccccc8c8cc(-c9ccc%10c(c9)c9ccccc9p%10-c9ccccc9)ccc87)c6)nc(-c6cccc(-n7c8ccccc8c8cc(-c9ccc%10c(c9)c9ccccc9p%10-c9ccccc9)ccc87)c6)n5)c4)ccc32)cc1]

-continued

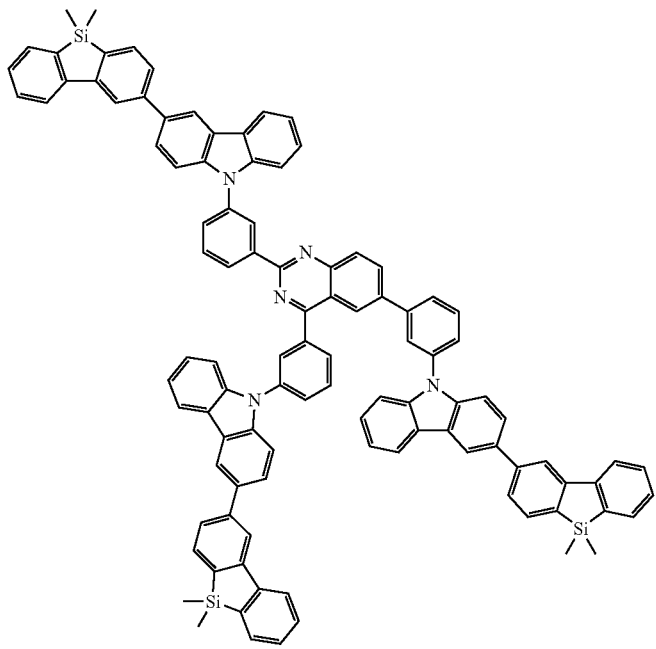 [SMILES: C[Si]1(C)c2ccccc2-c2cc(-c3ccc4c(c3)c3ccccc3n4-c3cccc(-c4ccc5nc(-c6cccc(-n7c8ccccc8c8cc(-c9ccc%10c(c9)-c9ccccc9[Si]%10(C)C)ccc87)c6)nc(-c6cccc(-n7c8ccccc8c8cc(-c9ccc%10c(c9)-c9ccccc9[Si]%10(C)C)ccc87)c6)c5c4)c3)ccc21]

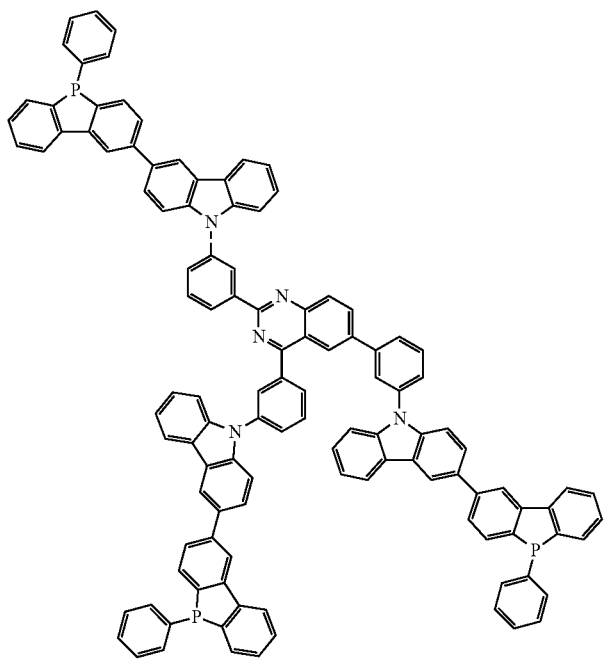 [SMILES: c1ccc(-p2c3ccccc3c3cc(-c4ccc5c(c4)c4ccccc4n5-c4cccc(-c5ccc6nc(-c7cccc(-n8c9ccccc9c9cc(-c%10ccc%11c(c%10)c%10ccccc%10p%11-c%10ccccc%10)ccc98)c7)nc(-c7cccc(-n8c9ccccc9c9cc(-c%10ccc%11c(c%10)c%10ccccc%10p%11-c%10ccccc%10)ccc98)c7)c6c5)c4)ccc32)cc1]

Compound Represented by Formula 1[V]

In an aspect, the invention provides a compound represented by formula 1[V] (also referred to as "compound 1[V]"). The compound is suitable for use in forming the layer of organic EL device by a coating method and is useful as a material for organic electroluminescence devices.

Compound 1[V] corresponds to compound (1) wherein at least two selected from $D^1$ to $D^3$ are selected from different groups of Group A to Group D.

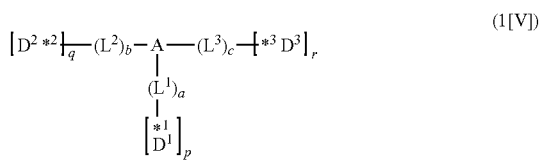

(1[V])

in formula 1[V],

A represents a substituted or unsubstituted nitrogen-containing heteroaromatic hydrocarbon group having 5 to 30 ring atoms;

$L^1$ to $L^3$ each independently represent a substituted or unsubstituted aromatic hydrocarbon group having 6 to 30 ring carbon atoms, a substituted or unsubstituted heterocyclic group having 5 to 30 ring atoms, or a group wherein 2 to 4 groups selected from the preceding groups are bonded to each other;

a to c each independently represent 0 or 1;

p to r each independently represent an integer of 0 to 3, p+q+r=3, and two or more groups $D^1$, two or more groups $D^2$ and two or more groups $D^3$ when p, q or r is 2 or 3 may be the same or different, respectively;

*1 to *3 are respectively bonded to $D^1$ to $D^3$;

$D^1$ to $D^3$ each independently represent a substituent selected from Group A to Group D each independently represented by formulae ($D^A$) to ($D^D$), and at least two of $D^1$ to $D^3$ are selected from different groups of Group A to Group D:

$Ar^1$ and $Ar^2$ each independently represent a substituted or unsubstituted aryl group having 6 to 30 ring carbon atoms or a substituted or unsubstituted heteroaryl group having 5 to 30 ring atoms one of $X^1$ to $X^4$ and one of $X^{13}$ to $X^{16}$ represent carbon atoms which are respectively bonded to *10 and *11, and the other six each independently represent C(R) or a nitrogen atom;

one of $X^9$ and $X^{12}$ and one of $X^{21}$ to $X^{24}$ represent carbon atoms which are respectively bonded to *12 and *13, and the other six each independently represent C(R) or a nitrogen atom;

$X^5$ to $X^8$ and $X^{17}$ to $X^{20}$ each independently represent C(R) or a nitrogen atom; and R represents a hydrogen atom or a substituent, two or more groups R may be the same or different, and two selected from groups R may be bonded to each other to form a ring;

in formula ($D^B$) which represents the substituent belonging to Group B,

Group A

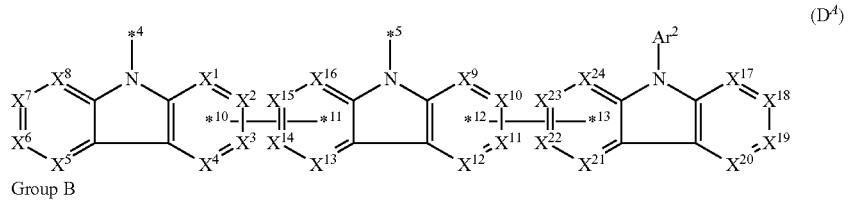

Group B

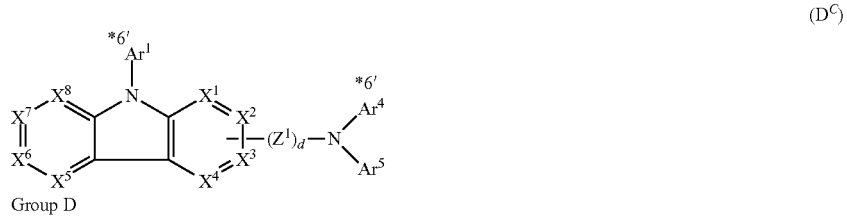

Group C

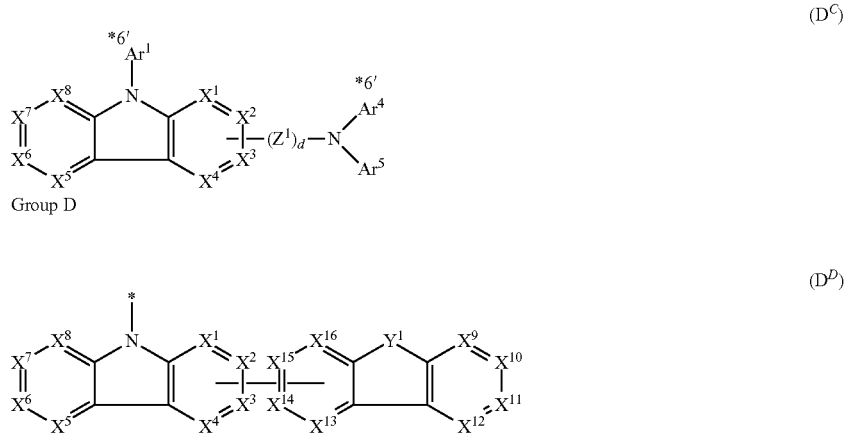

Group D in formula ($D^A$) which represents the substituent belonging to Group A, one of *4 and *5 is bonded to one of *1 to *3 of formula 1[V] and the other is bonded to $Ar^1$;

two of $X^1$ to $X^4$ represent carbon atoms which are respectively bonded to *21 and *22 and the other two independently represent C(R) or a nitrogen atom;

$X^5$ to $X^{12}$ each independently represent C(R) or a nitrogen atom;

R represents a hydrogen atom or a substituent, two or more groups R may be the same or different, and two selected from groups R may be bonded to each other to form a ring;

$Y^1$ represents an oxygen atom, a sulfur atom, —C($R^A$)($R^B$)—, —Si($R^C$)($R^D$)—, —P($R^E$)—, —P(=O)($R^F$)—, —S(=O)$_2$—, —P(=S)($R^G$)—, or —N($R^H$)—;

$R^A$ to $R^H$ each independently represent a hydrogen atom or a substituent, and $R^A$ and $R^B$, and $R^C$ and $R^D$ may be bonded to each other to form a ring; and

* is bonded to one of *1 to *3 of formula 1[V];

in formula ($D^C$) which represents the substituent belonging to Group C, $X^1$ to $X^8$ each represent $C(R^1)$ to $C(R^8)$, respectively, or a nitrogen atom;

$R^1$ to $R^8$ each independently represent a hydrogen atom or a substituent, provided that one of $X^1$ to $X^4$ represents a carbon atom which is directly bonded to $Z^1$ or the nitrogen atom to which $Ar^1$ and $Ar^6$ are bonded, and two selected from $R^1$ to $R^8$ not involved in the above direct bonding may be bonded to each other to form a ring;

$Ar^1$, $Ar^4$ and $Ar^5$ each independently represent a substituted or unsubstituted aryl group having 6 to 30 ring carbon atoms or a substituted or unsubstituted heteroaryl group having 5 to 30 ring atoms;

$Z^1$ independently represents a substituted or unsubstituted aromatic hydrocarbon group having 6 to 30 ring carbon atoms, a substituted or unsubstituted heterocyclic group having 5 to 30 ring atoms, or a group wherein 2 to 4 groups selected from the preceding groups are bonded to each other;

d is 0 or 1; and one of *1 to *3 of formula 1[V] is directly bonded to a nitrogen atom from which one of $Ar^1$ and $Ar^4$ indicated by *6' is removed; and in formula ($D^D$) which represents the substituent belonging to Group D, $X^1$ to $X^{16}$ each represent $C(R^1)$ to $C(R^{16})$, respectively, or a nitrogen atom;

$R^1$ to $R^{16}$ each independently represent a hydrogen atom or a substituent, provided that one of $X^1$ to $X^4$ represents a carbon atom which is directly bonded to a carbon atom represented by one of $X^{13}$ to $X^{16}$, and tow selected from $R^1$ to $R^8$ and two selected from $R^9$ to $R^{16}$, each not involved in the above direct bonding, may be bonded to each other to form a ring $Y^1$ represents an oxygen atom, a sulfur atom, $C(R^A)(R^B)$, $Si(R^C)(R^D)$, $P(R^E)$, $P(=O)(R^F)$, $S(=O)_2$, $P(=S)(R^G)$, or —N($R^H$)—;

$R^A$ to $R^H$ each independently represent a hydrogen atom or a substituent;

$R^A$ and $R^B$, and $R^C$ and $R^D$ may be bonded to each other to form a ring; and

* is bonded to one of *1 to *3 of formula 1[V].

Description of A in Formula 1[V]

The nitrogen-containing heteroaromatic hydrocarbon group for A of formula 1[V] has 5 to 30, preferably 6 and 20, and more preferably 6 to 14 ring carbon atoms.

The nitrogen-containing heteroaromatic hydrocarbon group is preferably a monocyclic group or a fused ring group comprising two or three fused rings.

The nitrogen-containing heteroaromatic hydrocarbon group contains preferably 1 to 3 and more preferably 2 or 3 nitrogen atoms. Particularly, the nitrogen-containing heteroaromatic hydrocarbon group contains preferably 2 or 3 and more preferably 3 nitrogen atoms when it is a monocyclic group, and preferably 2 nitrogen atoms when it is a fused ring group having two or three fused rings.

The nitrogen-containing heteroaromatic hydrocarbon group may contain a hetero atom other than a nitrogen atom, such as an oxygen atom, a sulfur atom, a silicon atom, and selenium atom, but preferably contains only a nitrogen atom as the heteroatom.

Examples of the nitrogen-containing heteroaromatic hydrocarbon group for A in formula 1[V] includes residues of compounds selected from pyrrole, pyridine, pyridazine, pyrimidine, pyrazine, triazine, imidazole, pyrazole, oxadiazole, thiadiazole, triazole, tetrazole, indole, isoindole, indolizine, quinolizine, quinoline, isoquinoline, naphthyridine, cinnoline, phthalazine, quinazoline, benzo[f]quinazoline, benzo[h]quinazoline, quinoxaline, benzimidazole, indazole, carbazole, biscarbazole, phenanthridine, acridine, phenanthroline, phenazine, azatriphenylene, diazatriphenylene, hexaazatriphenylene, azacarbazole, azadibenzofuran, azadibenzothiophene, and dinaphtho[2',3': 2,3:2',3': 6,7]carbazole.

The residue is a mono valent or more valent group obtained by removing one or more hydrogen atoms from the above compound. The valency of the nitrogen-containing heteroaromatic hydrocarbon group, i.e., the valency of "A" corresponds to the value of "a+b+c" in formula 1[V].

The nitrogen-containing heteroaromatic hydrocarbon group mentioned above is preferably a residue of the following compounds:

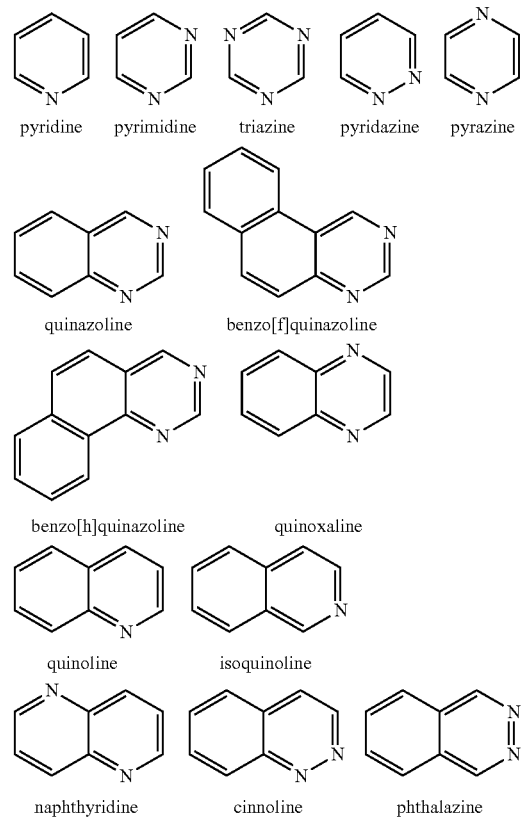

In an aspect of the invention, the nitrogen-containing heteroaromatic hydrocarbon group for A is preferably a residue of the nitrogen-containing heterocyclic ring represented by formula (A1):

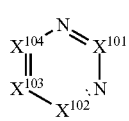

(A1)

in formula (A1), $X^{101}$ to $X^{104}$ each represent $C(R^{101})$ to $C(R^{104})$, respectively, or a nitrogen atom; $R^{101}$ to $R^{104}$ each independently represent a hydrogen atom or a substituent; and two selected from $R^{102}$ to $R^{104}$ may be bonded to each other to form a ring.

In an aspect of the invention, the nitrogen-containing heteroaromatic hydrocarbon group for A is more preferably a residue of the nitrogen-containing heterocyclic ring represented by any of formulae (A2) to (A4):

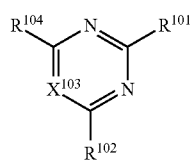

(A2)

in formula (A2), $X^{103}$ represents $C(R^{103})$ or a nitrogen atom; $R^{101}$ to $R^{104}$ each independently represent a hydrogen atom or a substituent; and two selected from $R^{102}$ to $R^{104}$ may be bonded to each other to form a ring;

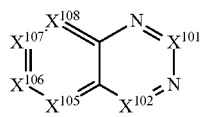

(A3)

in formula (A3), $X^{101}$, $X^{102}$, and $X^{105}$ to $X^{108}$ each represent $C(R^{101})$, $C(R^{102})$, or $C(R^{105})$ to $C(R^{108})$, respectively, or a nitrogen atom; $R^{101}$, $R^{102}$, and $R^{105}$ to $R^{108}$ each independently represent a hydrogen atom or a substituent; and two selected from $R^{102}$ and $R^{105}$ to $R^{108}$ may be bonded to each other to form a ring; and

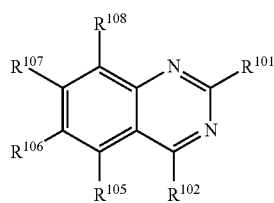

(A4)

in formula (A4), $R^{101}$, $R^{102}$, and $R^{105}$ to $R^{108}$ each independently represent a hydrogen atom or a substituent; and two selected from $R^{102}$ and $R^{105}$ to $R^{108}$ may be bonded to each other to form a ring.

The nitrogen-containing heteroaromatic hydrocarbon group for A in formula 1[V] may have a substituent. Examples of the substituent of the nitrogen-containing heteroaromatic hydrocarbon group include the substituents mentioned above and also include the following substituents (a) to (d):

(a): an (aza)carbazolyl group having two (aza)carbazolyl substituents and an aryl group or a heteroaryl group each having an (aza)carbazolyl substituent which further has two (aza)carbazolyl substituents;

(b): an (aza) carbazolyl group wherein two substituents are bonded to each other to form a ring and an aryl group or a heteroaryl group each having an (aza) carbazolyl substituent wherein two substituents are bonded to each other to form a ring;

(c): a 9-carbazolyl group having a substituted amino substituent; a substituted amino group having a carbazolyl substituent; a 9-carbazolyl group having an aryl substituent or a heteroaryl substituent, each further having a substituted amino substituent; a substituted amino group having an aryl substituent or a heteroaryl substituent, each further having a carbazolyl substituent; and an aryl group or a heteroaryl group having a substituent selected from the above substituted 9-carbazolyl group or substituted amino group; and (d): a 9-carbazolyl group having an aryl substituent or a heteroaryl substituent and an aryl group or a heteroaryl group having a 9-carbazolyl substituent which further has an aryl substituent or a heteroaryl substituent.

Description of "$L^1$ to $L^3$" in formula 1[V]

In formula 1[V], the aromatic hydrocarbon group for $L^1$ to $L^3$ has 6 to 30, preferably 6 to 18, more preferably 6 to 13, still more preferably 6 to 12, and particularly preferably 6 to 10 ring carbon atoms.

In an aspect of the invention, at least one of the aromatic hydrocarbon groups for $L^1$ to $L^3$ is preferably a di- to tetravalent residue of any of the following compounds, and more preferably $L^1$ to $L^3$ are all di- to tetravalent residues of any of the following compounds:

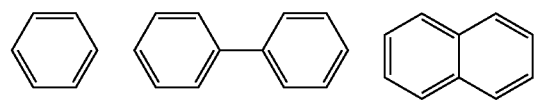

wherein each carbon atom in the compound may have a substituent.

In an aspect of the invention, at least one of the aromatic hydrocarbon groups for $L^1$ to $L^3$ is preferably a group represented by any of the following formulae, and more preferably $L^1$ to $L^3$ are all groups represented by any of the following formulae:

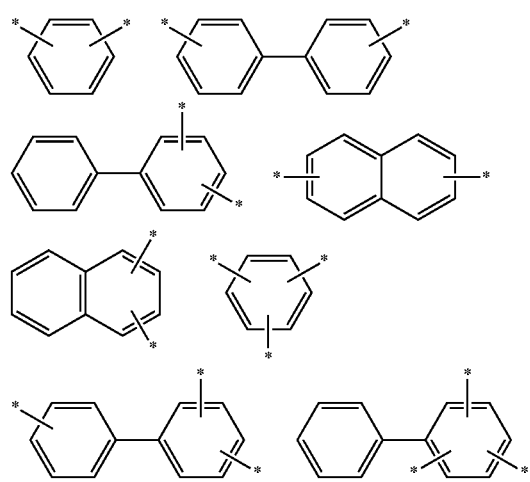

-continued

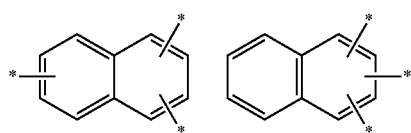

wherein * indicates a bonding site and each carbon atom other than that at the bonding site may have a substituent.

More preferably, at least one of the aromatic hydrocarbon groups for $L^1$ to $L^3$ is a group represented by any of the following formulae, and still more preferably $L^1$ to $L^3$ are all groups represented by any of the following formulae:

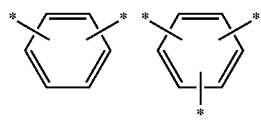

wherein * indicates a bonding site and each carbon atom other than that at the bonding site may have a substituent.

More preferably, at least one of the aromatic hydrocarbon groups for $L^1$ to $L^3$ is a group represented by any of the following formulae, and still more preferably $L^1$ to $L^3$ are all groups represented by any of the following formulae:

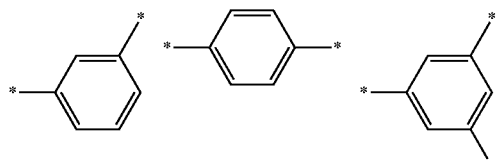

wherein * indicates a bonding site and each carbon atom other than that at the bonding site may have a substituent.

In addition to the above groups, the aromatic hydrocarbon group for $L^1$ to $L^3$ may include the groups represented by the following formulae:

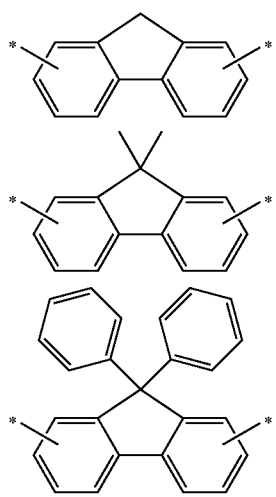

-continued

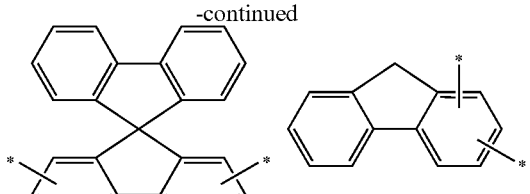

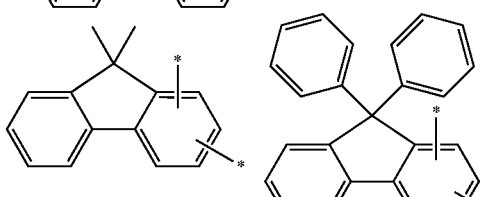

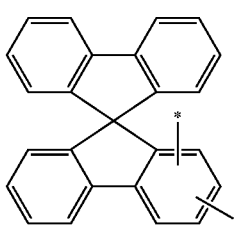

wherein * indicates a bonding site and each carbon atom other than that at the bonding site may have a substituent.

Examples of the divalent aromatic hydrocarbon group for $L^1$ to $L^3$ include the following groups:

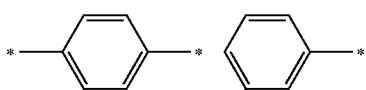

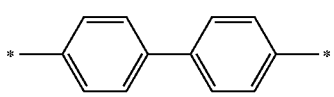

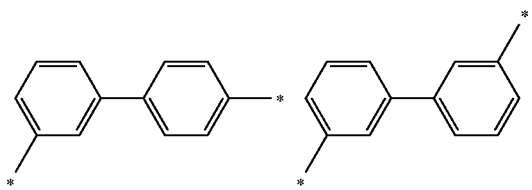

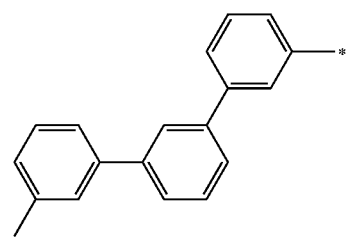

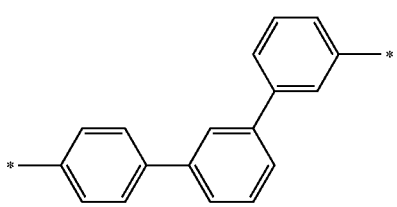

-continued

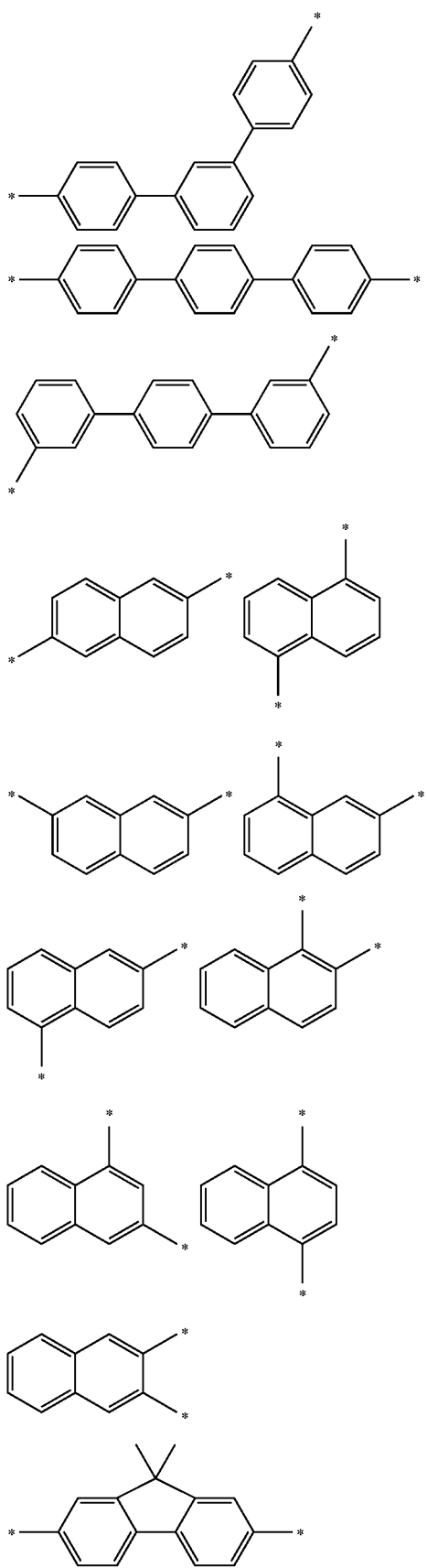

-continued

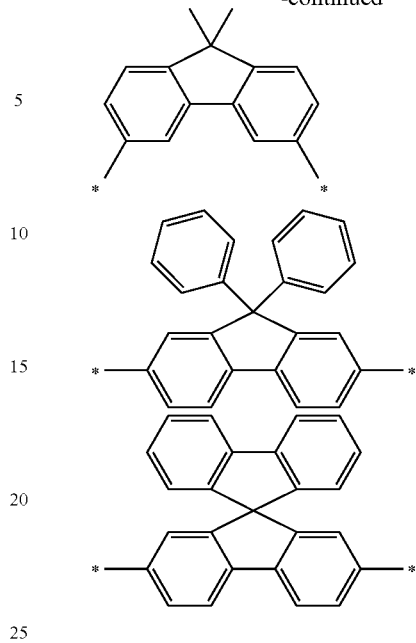

wherein * indicates a bonding site and each carbon atom other than that at the bonding site may have a substituent.

In formula 1[V], the heterocyclic group for $L^1$ to $L^3$ has 5 to 30, preferably 5 to 18, more preferably 5 to 13, particularly preferably 5 to 10 ring atoms.

Examples of the heterocyclic group include a residue of a nitrogen-containing heterocyclic compound, such as pyrrole, pyridine, imidazopyridine, pyrazole, triazole, tetrazole, indole, isoindole, and carbazole; a residue of an oxygen-containing heterocyclic compound, such as furan, benzofuran, isobenzofuran, dibenzofuran, oxazole, oxadiazole, benzoxazole, benzonaphthofuran, and dinaphthofuran; and a residue of a sulfur-containing heterocyclic compound, such as thiophene, benzothiophene, dibenzothiophene, thiazole, thiadiazole, benzothiazole, benzonaphthothiophene, and dinaphthothiophene.

The "group wherein 2 to 4 groups selected from the preceding groups are bonded to each other" for $L^1$ to $L^3$ is a group wherein 2 to 4 groups selected from a substituted or unsubstituted aromatic hydrocarbon group having 6 to 30 ring carbon atoms and a substituted or unsubstituted heterocyclic group having 5 to 30 ring atoms are bonded to each other. The 2 to 4 groups to be selected may be bonded to each other to form a ring structure. The order of bonding the groups selected from the aromatic hydrocarbon group and heterocyclic group is not particularly limited.

In particular, each of $L^1$ to $L^3$ is preferably a substituted or unsubstituted aromatic hydrocarbon group having 6 to 30 ring carbon atoms. The aromatic hydrocarbon group more preferred is as described above.

Description of "a to c" in Formula 1[V]

In formula 1[V], a to c each independently represent 0 or 1.

When a is zero, $L^1$ is not present, i.e., A is directly bonded to the group in [ ]. When a is 1, A is bonded to the group in [ ] via $L^1$. The same applies to b and c.

Description of "p to r" in Formula 1[V]

As described above, p to r in formula 1[V] each independently represent an integer of 0 to 3, and p+q+r is 3. Preferably, two selected from p to r cannot be 0 at the same time, although not particularly limited thereto.

When p, q or r is 2 or 3, 2 or 3 groups in each [ ] may be the same or different.

Description of "$D^1$ to $D^3$" in Formula 1[V]

In formula 1[V], *1 to *3 are respectively bonded to $D^1$ to $D^3$.

$D^1$ to $D^3$ each independently represent a substituent selected from Group A to Group D each respectively represented by formulae ($D^A$) to ($D^D$), and at least two thereof are selected from different groups of Group A to Group D.

The words, "at least two thereof are selected from different groups of Group A to Group D" mean that $D^1$ to $D^3$ cannot be all selected from the same Group. Therefore, $D^1$ to $D^3$ represent substituents belonging to at least two of Group A to Group D.

In a preferred aspect of the invention, two of D to $D^3$ are selected from the same Group and the other one is selected from the other three Groups.

In another preferred aspect of the invention, $D^1$ to $D^3$ are selected from three different Groups, respectively.

In another preferred aspect of the invention, at least one selected from $D^1$ to $D^3$ is selected from Group A.

Group A to Group D respectively represented by formulae ($D^A$) to ($D^D$) for $D^1$ to $D^3$ are described below.

Description of Substituents Belonging to Group a Represented by Formula ($D^A$)

In formula ($D^A$), one of *4 and *5 is bonded to one of *1 to *3 in formula 1[V], and the other is bonded to $Ar^1$.

In an aspect of the invention, *5 is preferably bonded to one of *1 to *3, and *4 is preferably bonded to $Ar^1$.

$Ar^1$ and $Ar^2$ each independently represent a substituted or unsubstituted aryl group having 6 to 30 ring carbon atoms or a substituted or unsubstituted heteroaryl group having 5 to 30 ring atoms.

The aryl group for $Ar^1$ and $Ar^2$ has 6 to 30, preferably 6 to 18, more preferably 6 to 15, still more preferably 6 to 12, particularly preferably 6 to 10 ring carbon atoms.

The aryl group may be any of a non-fused aryl group, a fused aryl group, and a combination thereof.

Examples of the aryl group include a phenyl group, a biphenylyl group, a terphenylyl group, a quaterphenylyl group, a quinquephenylyl group, a naphthyl group (a 1-naphthyl group, a 2-naphthyl group), an acenaphthylenyl group, an anthryl group, a benzanthryl group, an aceanthryl group, a phenanthryl group, a benzophenanthryl group, a phenalenyl group, a fluorenyl group (inclusive of a 9,9-dimethylfluorenyl group, a 9,9-diphenylfluorenyl group, and a 9,9'-spirobifluorenyl group), a benzofluorenyl group, a dibenzofluorenyl group, a picenyl group, a pentaphenyl group, a pentacenyl group, a pyrenyl group, a chrysenyl group, a benzochrysenyl group, a fluoranthenyl group, a benzofluoranthenyl group, a tetracenyl group, a perylenyl group, a coronyl group, a dibenzanthryl group, a naphthylphenyl group, a s-indanyl group, an as-indanyl group, a triphenylenyl group, and a benzotriphenylenyl group. The above groups include isomeric groups, if any.

The aryl group for $Ar^1$ and $Ar^2$ is preferably selected from the following groups:

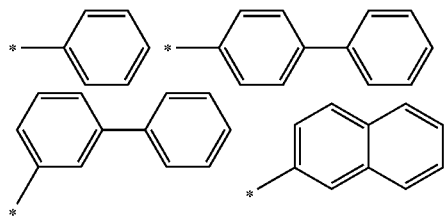

-continued

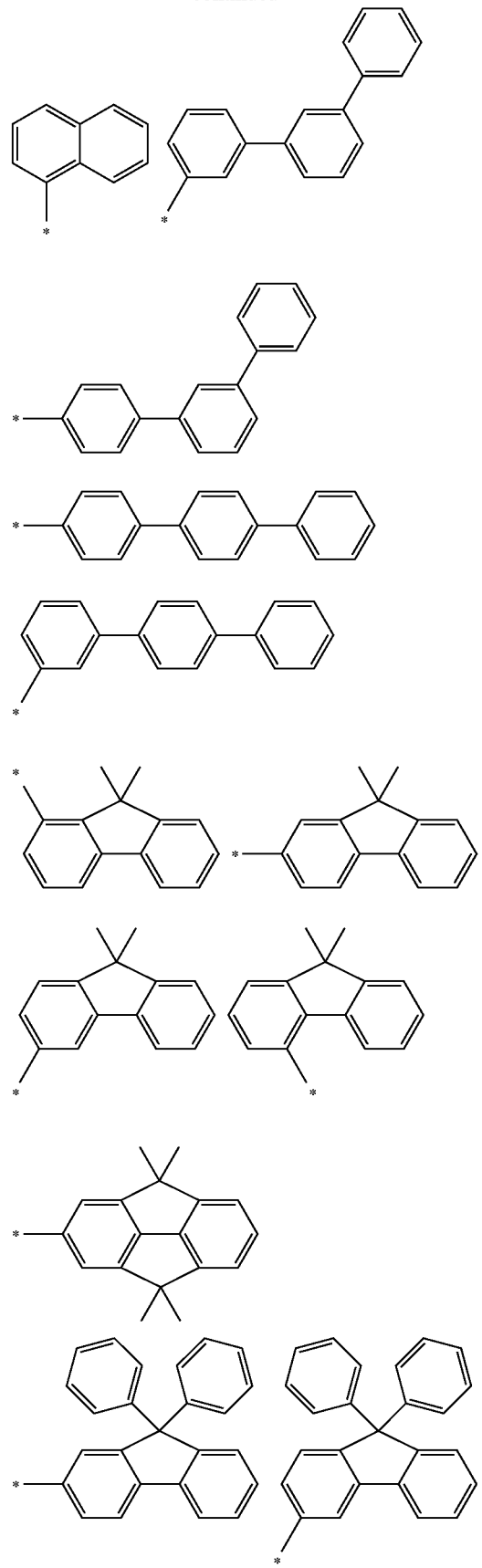

-continued

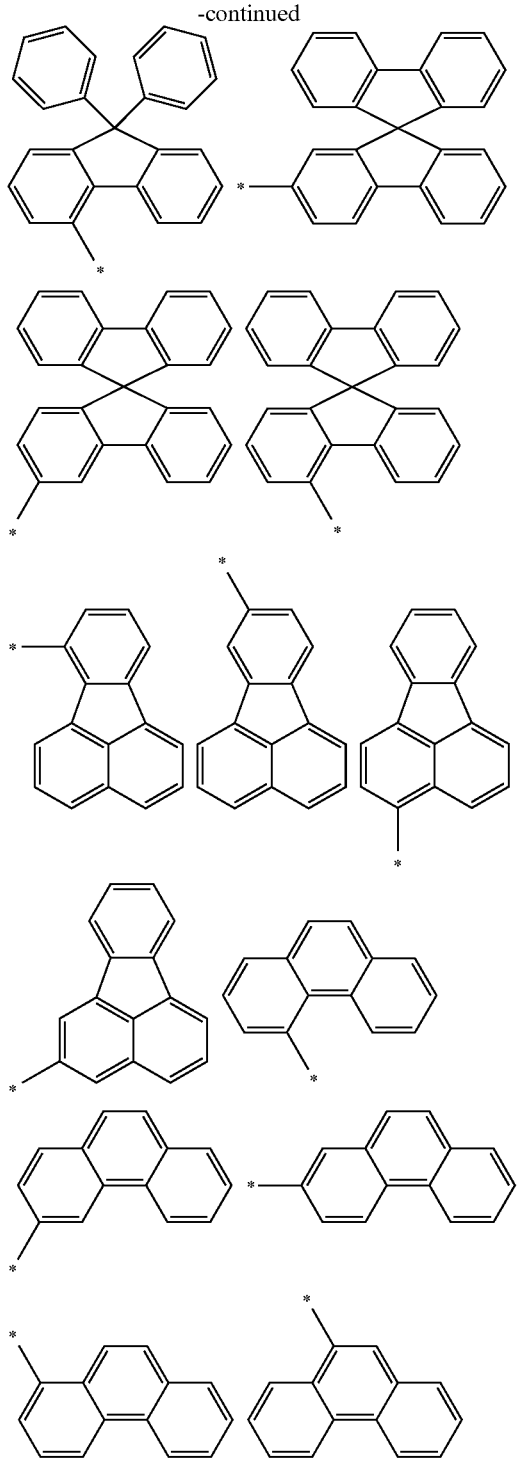

wherein * indicates a bonding site and each carbon atom other than that at the bonding site may have a substituent.

The heteroaryl group for $Ar^1$ and $Ar^2$ has 5 to 30, preferably 5 to 20, more preferably 5 to 14, and still more preferably 5 to 10 ring atoms.

The heteroaryl group contains at least one, preferably 1 to 5, more preferably 1 to 3, and still more preferably 1 to 2 hetero atoms which may be the same or different.

Examples of the heteroaryl group include a pyrrolyl group, a furyl group, a thienyl group, a pyridyl group, a pyridazinyl group, a pyrimidinyl group, a pyrazinyl group, a triazinyl group, an imidazolyl group, an oxazolyl group, a thiazolyl group, a pyrazolyl group, an isoxazolyl group, an isothiazolyl group, an oxadiazolyl group, a thiadiazolyl group, a triazolyl group, a tetrazolyl group, an indolyl group, an isoindolyl group, a benzofuranyl group, an isobenzofuranyl group, a benzothiophenyl group, an isobenzothiophenyl group, an indolizinyl group, a quinolizinyl group, a quinolyl group, an isoquinolyl group, a cinnolyl group, a phthalazinyl group, a quinazolinyl group, a quinoxalinyl group, a benzimidazolyl group, a benzoxazolyl group, a benzothiazolyl group, an indazolyl group, a benzisoxazolyl group, a benzisothiazolyl group, a dibenzofuranyl group, a dibenzothiophenyl group, a carbazolyl group, a biscarbazolyl group, a phenanthridinyl group, an acridinyl group, a phenanthrolinyl group, a phenazinyl group, a phenothiazinyl group, a phenoxazinyl group, an azatriphenylenyl group, a diazatriphenylenyl group, a xanthenyl group, an azacarbazolyl group, an azadibenzofuranyl group, an azadibenzothiophenyl group, a benzofuranobenzothiophenyl group, a benzothienobenzothiophenyl group, a dibenzofuranonaphthyl group, a dibenzothienonaphthyl group, a dinaphthothienothiophenyl group, and dinaphtho[2',3': 2,3:2',3': 6,7]carbazolyl group.

Each of $Ar^1$ and $Ar^2$ is preferably a substituted or unsubstituted aryl group having 6 to 30 ring carbon atoms. More preferred examples of the aryl group are as described above.

In formula ($D^4$), one of $X^1$ to $X^4$ and one of $X^{13}$ to $X^{16}$ represent carbon atoms which are respectively bonded to *10 and *11, and the other six each independently represent $C(R)$ or a nitrogen atom.

One of $X^9$ and $X^{12}$ and one of $X^{21}$ to $X^{24}$ represent carbon atoms which are respectively bonded to *12 and *13, and the other six each independently represent $C(R)$ or a nitrogen atom.

The above limitations are described below with reference to, for example, the limitation to "$X^1$ to $X^4$ and $X^{13}$ to $X^{16}$." Assuming that $X^1$ is a carbon atom bonded to *10 and $X^{13}$ is a carbon atom bonded to *11, two carbon atoms represented by $X^1$ and $X^{13}$ are bonded to each other, thereby linking two (aza)carbazolyl groups. The other six, i.e., $X^2$ to $X^4$ and $X^{14}$ to $X^{16}$ each independently represent $C(R)$ or a nitrogen atom. The same applies to the other limitations.

Namely, each of *10 and *12 in formula ($D^4$) is bonded to a carbon atom at 1-position, 2-position, 3-position or 4-position of the respective (aza)carbazolyl group, i.e., one of $X^1$ to $X^4$ and one of $X^9$ to $X^{12}$, respectively.

On the other hand, each of *11 and *13 in formula ($D^4$) is bonded to a carbon atom at 5-position, 6-position, 7-position, or 8-position of the respective (aza)carbazolyl group, i.e., one of $X^{13}$ to $X^{16}$ and one of $X^{21}$ to $X^{24}$, respectively.

Thus, two (aza)carbazolyl groups are linked by each of *10-*11 and *12-*13.

In formula ($D^4$), $X^5$ to $X^8$ and $X^{17}$ to $X^{20}$ each independently represent $C(R)$ or a nitrogen atom.

Namely, $X^1$ to $X^{24}$ not involved in the linking between two (aza)carbazolyl groups each independently represent $C(R)$ or a nitrogen atom, with each being preferably $C(R)$ in an aspect of the invention.

R represents a hydrogen atom or a substituent, two or more groups R may be the same or different, and two selected from groups R may be bonded to each other to form a ring.

In the compound in an aspect of the invention, two selected from groups R are preferably not bonded to each other, thereby failing to form a ring.

In an aspect of the invention, the group represented by formula ($D^4$) is preferably a group represented by formula ($D^{41}$):

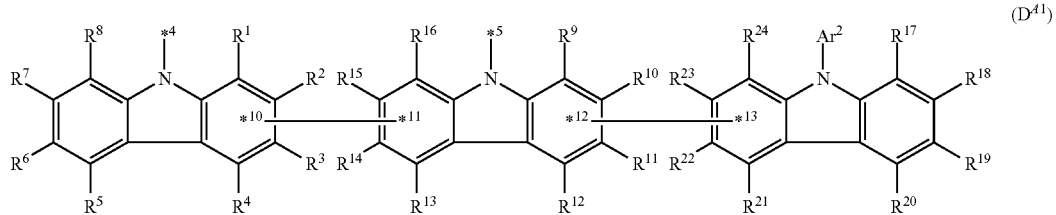

(D^{41})

in formula (D$^{41}$), R$^1$ to R$^{24}$ may be the same or different and each independently represent a hydrogen atom or a substituent; two selected from R$^1$ to R$^{24}$ may be bonded to each other to form a ring; and the other symbols are as defined above in formula (D$^4$).

*10-*11 is a bond between carbon atoms from which one of R$^1$ to R$^4$ and one of R$^{13}$ to R$^{16}$ are removed, and *12-*13 is a bond between carbon atoms from which one of R$^9$ to R$^{12}$ and one of R$^{21}$ to R$^{24}$ are removed.

Namely, each of *10 and *12 is bonded to a carbon atom at 1-position, 2-position, 3-position or 4-position of a carbazolyl group, and each of *11 and *13 is bonded to a carbon atom at 5-position, 6-position, 7-position or 8-position of another carbazolyl group, thereby linking two carbazolyl groups via *10-*11 and *12-*13, respectively.

In an aspect of the invention, the group represented by formula (D$^{41}$) is preferably a group represented by formula (D$^{41}$-1) and more preferably a group represented by any of formulae (D$^{41}$-1-1) to (D$^{41}$-1-6):

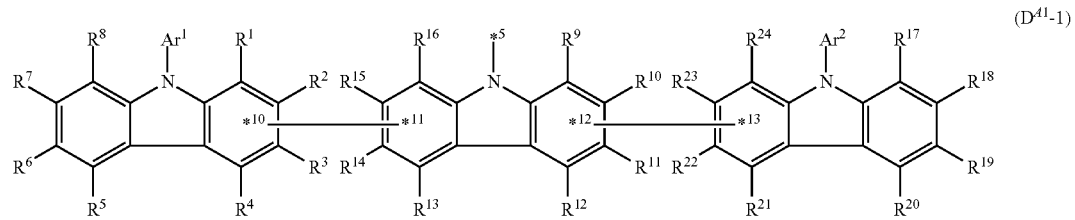

(D$^{41}$-1)

in formula (D$^{41}$-1), each symbol is as defined above in formula (D$^{41}$); and

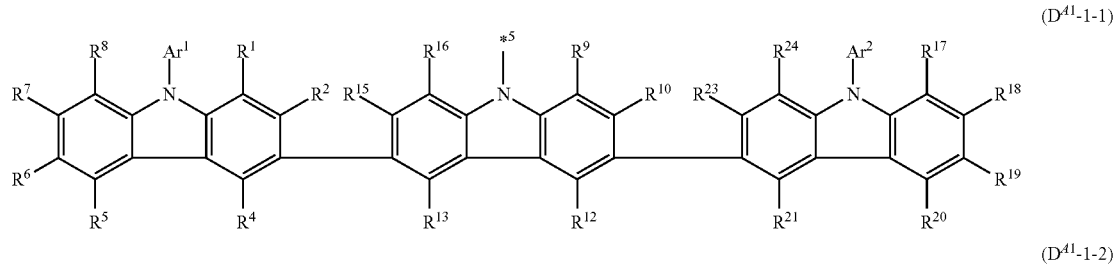

(D$^{41}$-1-1)

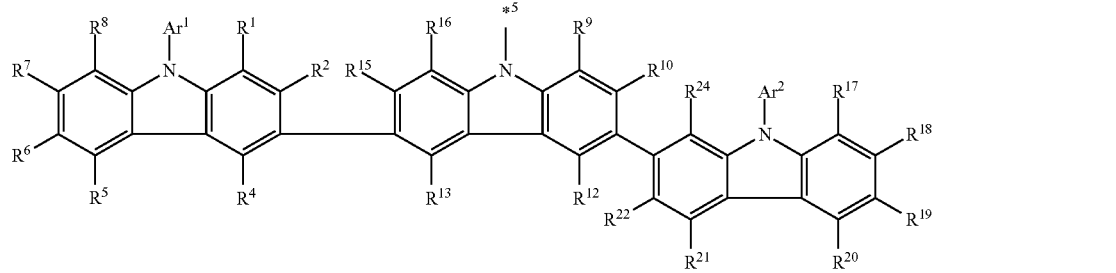

(D$^{41}$-1-2)

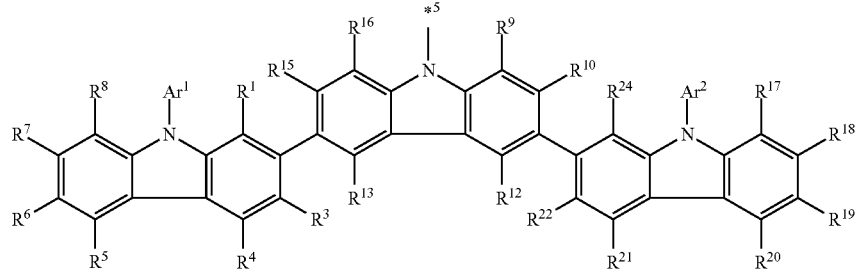

(D$^{41}$-1-3)

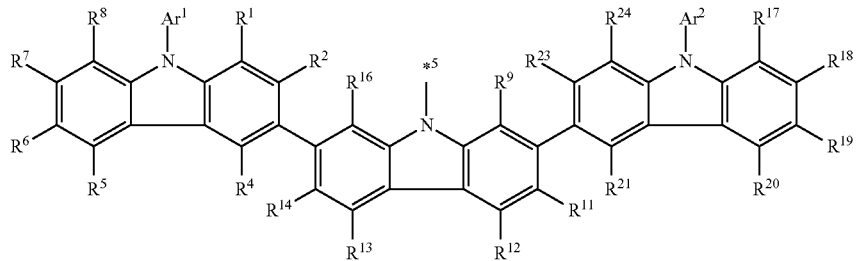
(D^{41}-1-4)

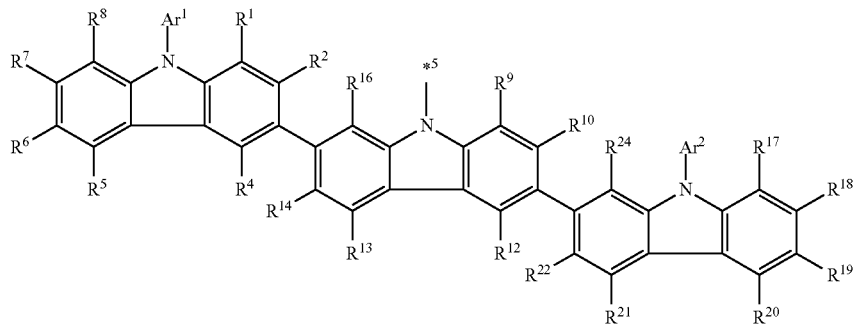
(D^{41}-1-5)

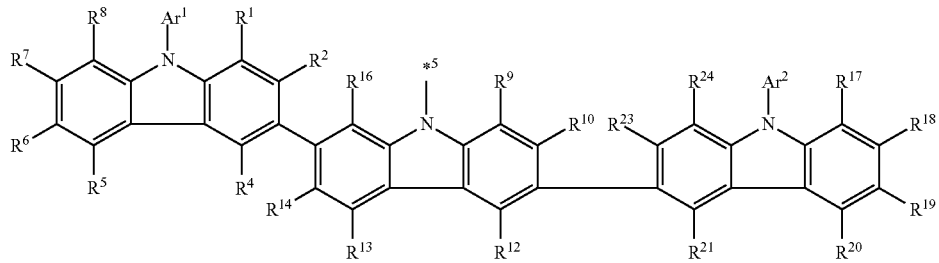
(D^{41}-1-6)

in formulae ($D^{41}$-1-1) to ($D^{41}$-1-6), each symbol is as defined above in formula ($D^{41}$).

When two selected from $R^1$ to $R^{24}$ in formula ($D^4$) are bonded to each other to form a ring, one or more pairs selected from $R^5$ and $R^6$, $R^6$ and $R^7$, $R^7$ and $R^8$, $R^{17}$ and $R^{18}$, $R^{18}$ and $R^{19}$, and $R^{19}$ and $R^{20}$ are preferably bonded to each other to form a ring.

In the compound in an aspect of the invention, two selected from $R^1$ to $R^{24}$ in formula ($D^4$) are preferably not bonded to each other, thereby failing to form a ring, and the group represented by formula ($D^4$) is preferably a group represented by formula ($D^{42}$):

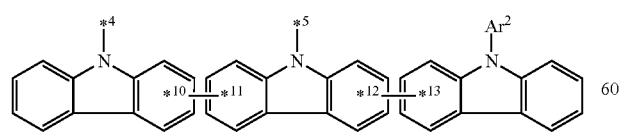
($D^{42}$)

in formula ($D^{42}$), each of *10-*11 and *12-*13 is a bond between carbon atoms in each benzene ring from which hydrogen atoms are removed, and the other symbols are as defined above in formula ($D^4$).

Examples of the group represented by formula ($D^{41}$) are preferably selected from the following groups, wherein * represents a bonding site to one of *1 to *3 in formula 1[V], and a hydrogen atom bonded to a carbon atom may be substituted with the substituent mentioned above.

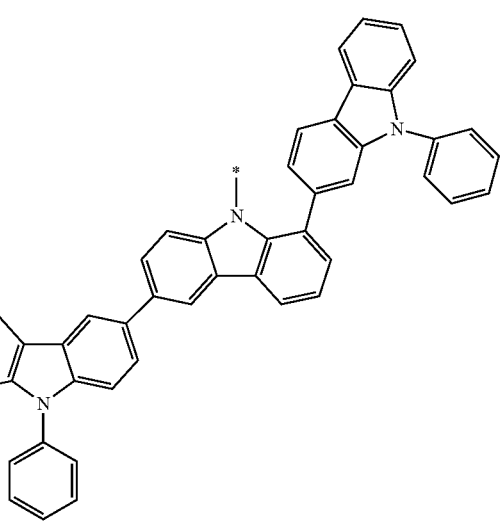

1705
-continued
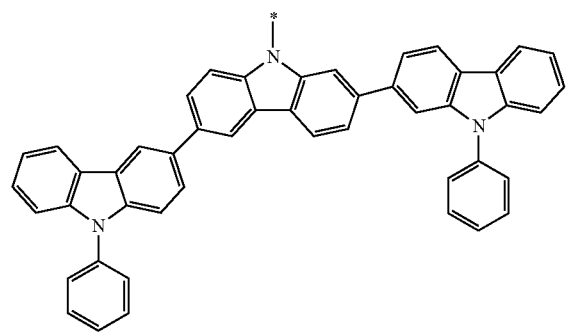
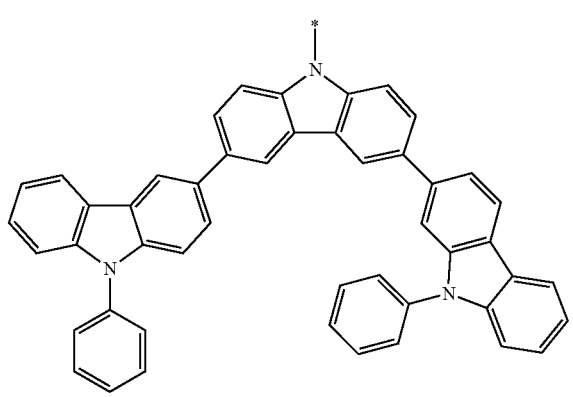
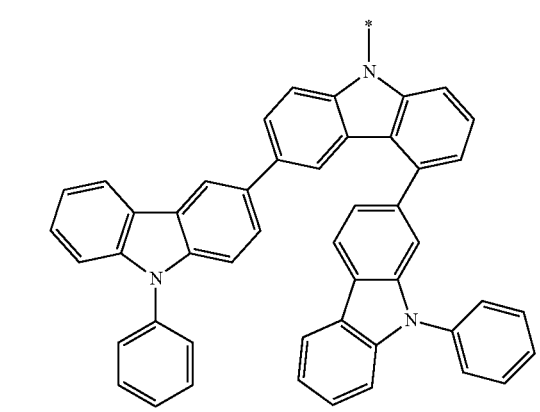
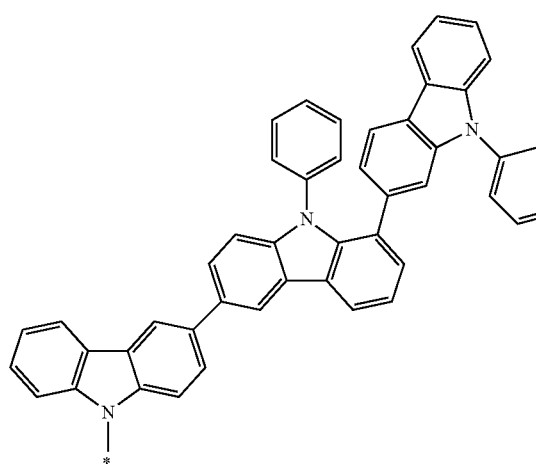
1706
-continued
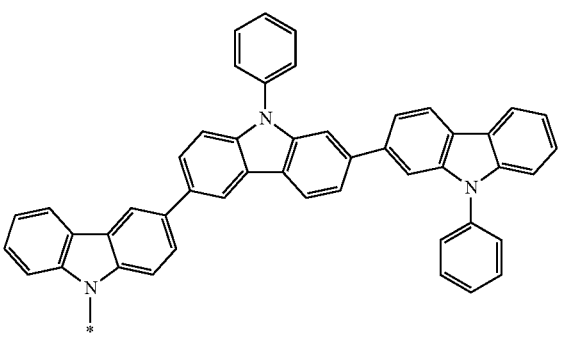
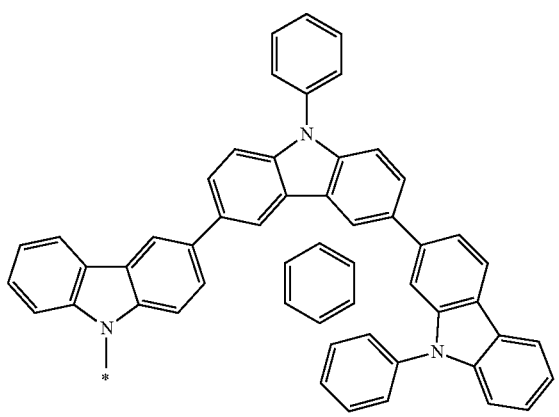
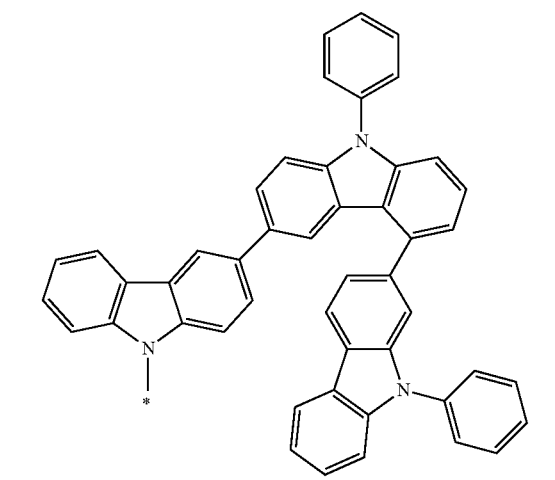

1707
-continued
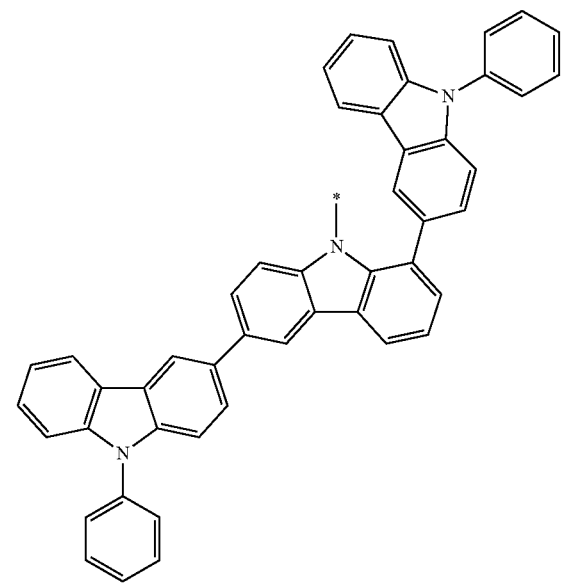
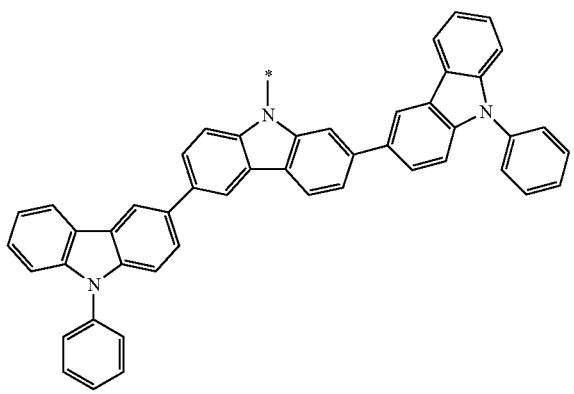
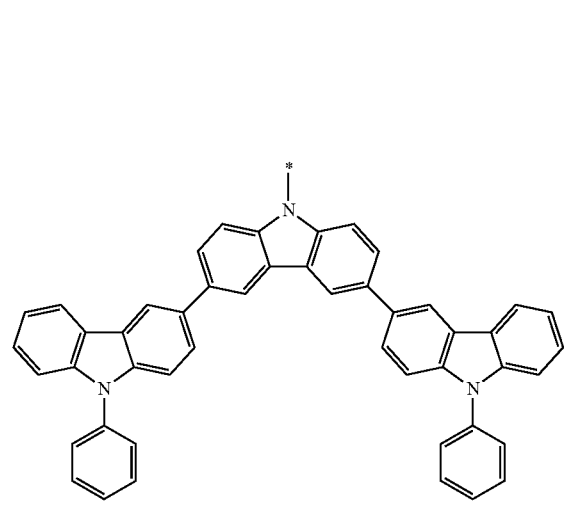
1708
-continued
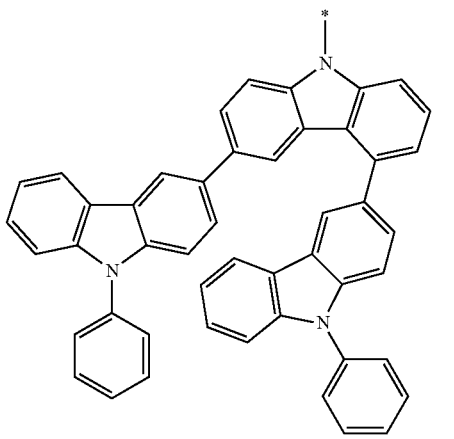
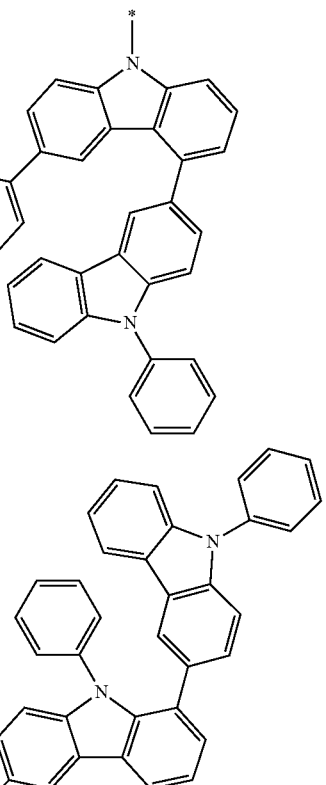
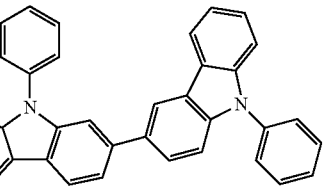
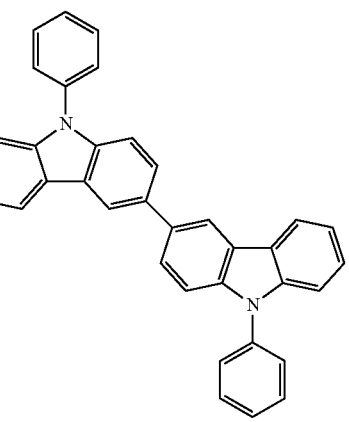

1709
-continued
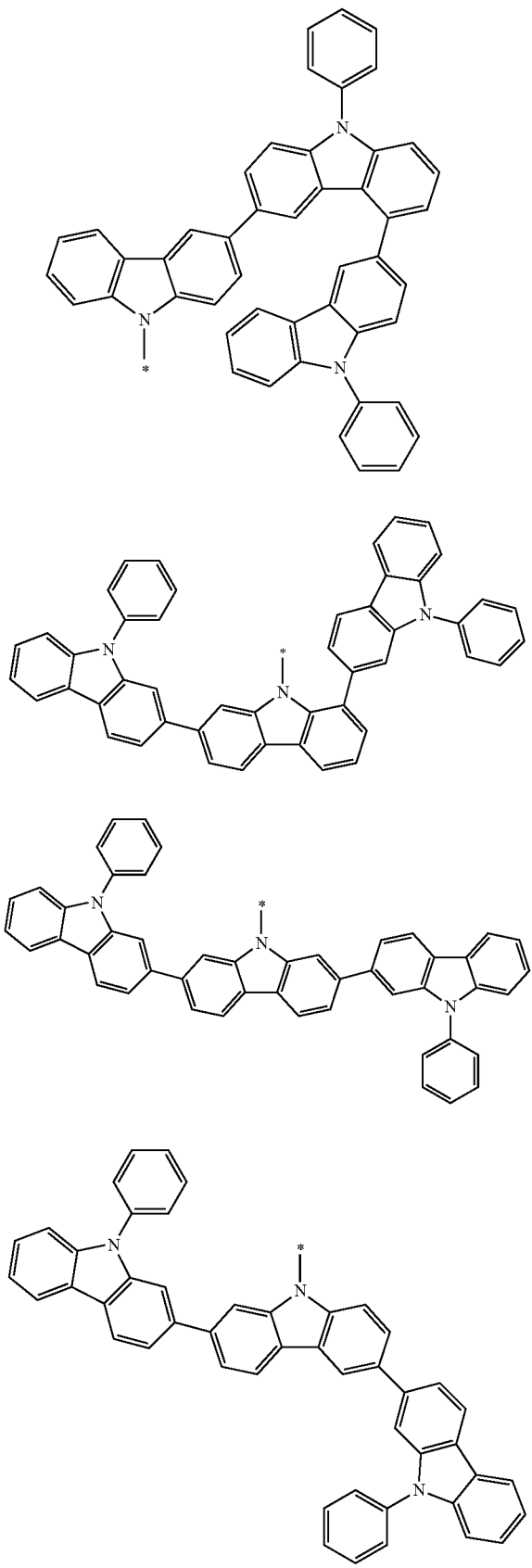
1710
-continued
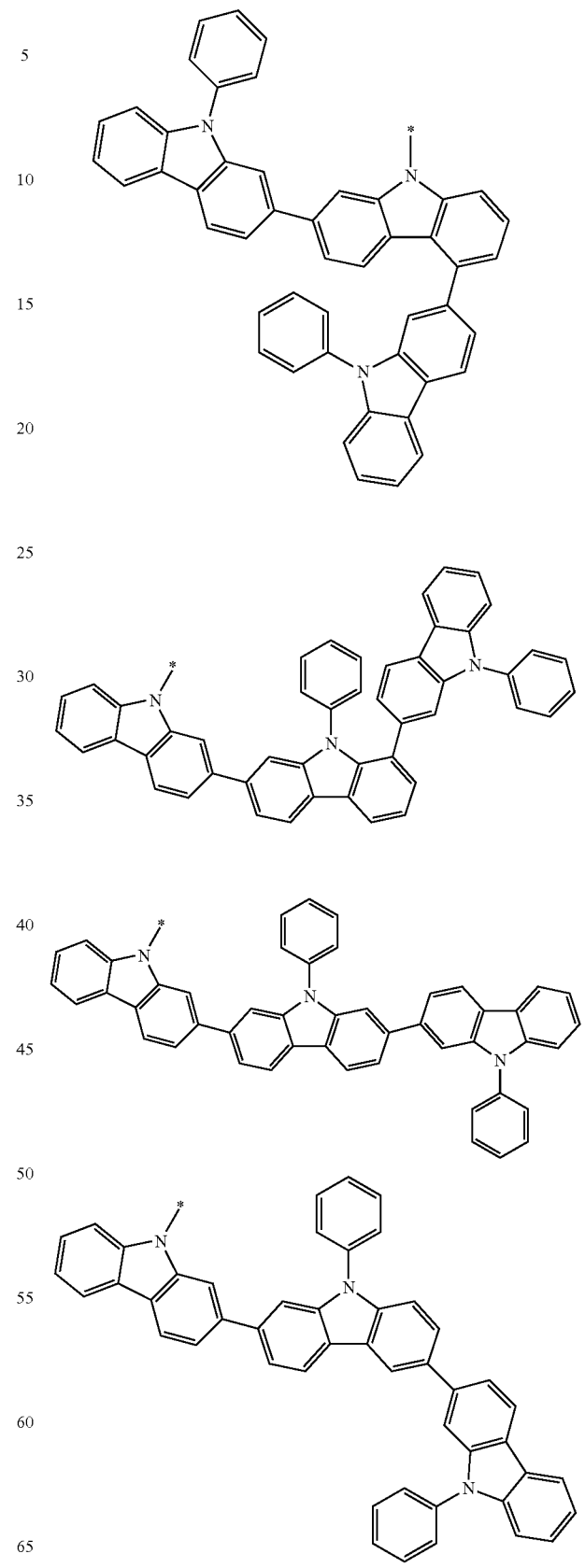

1711
-continued
1712
-continued
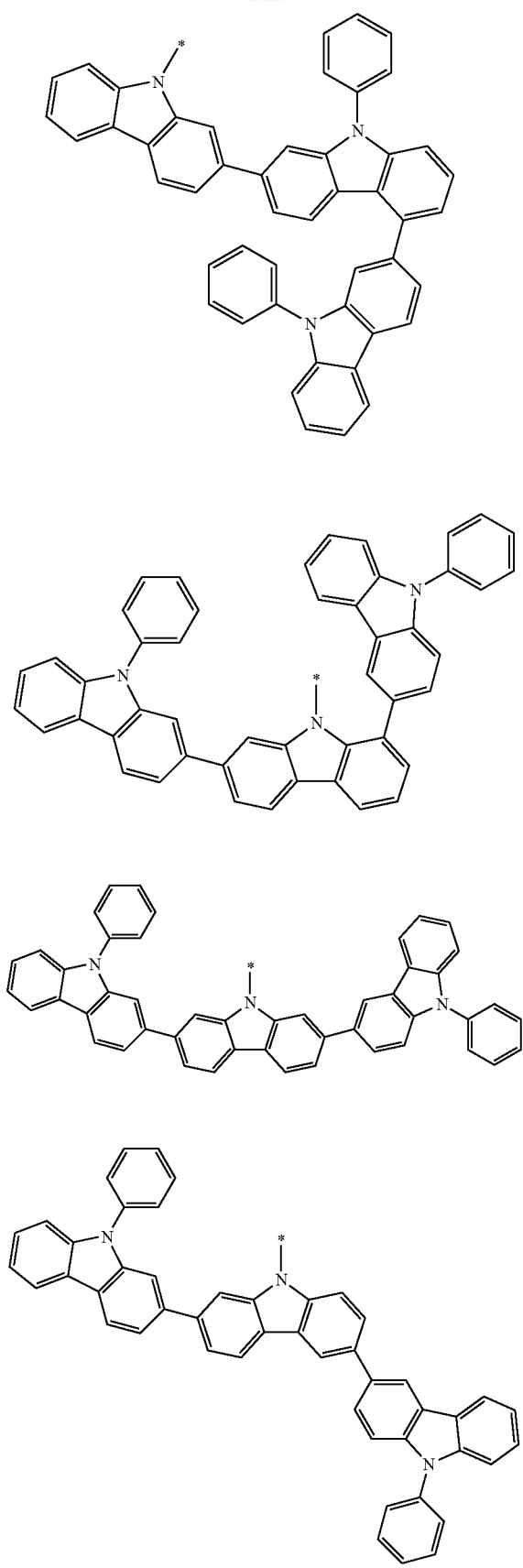
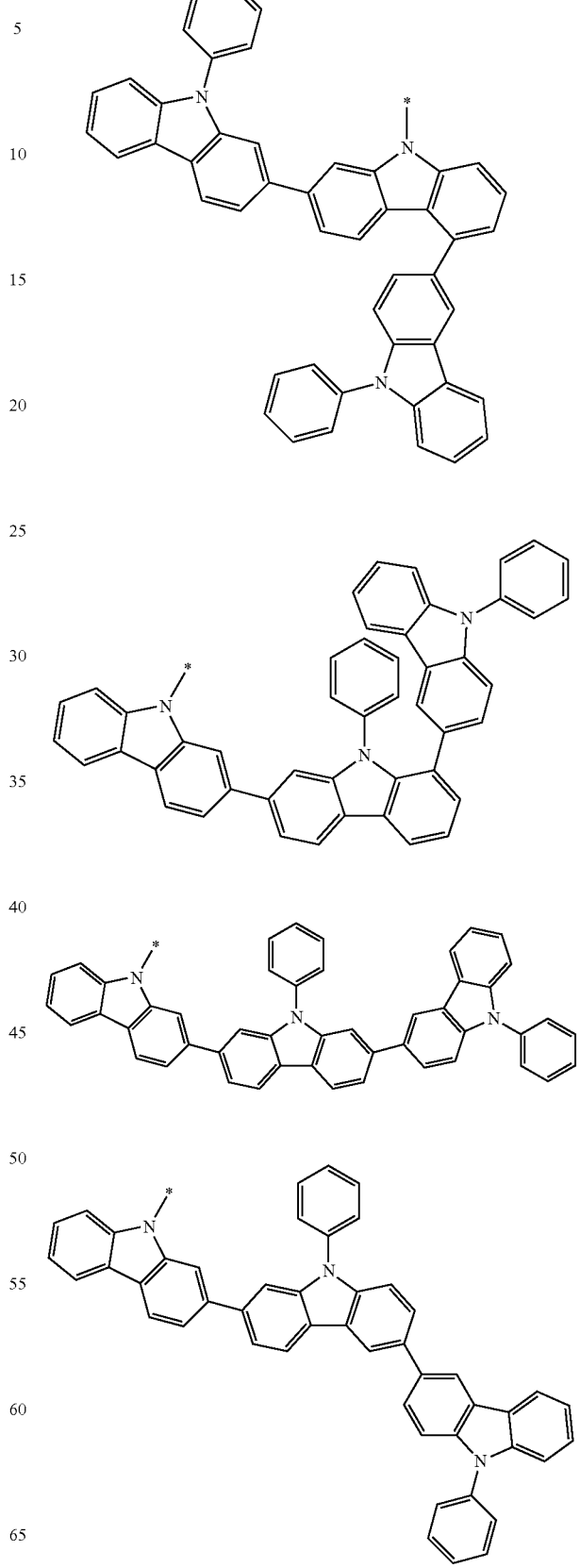

1713
-continued
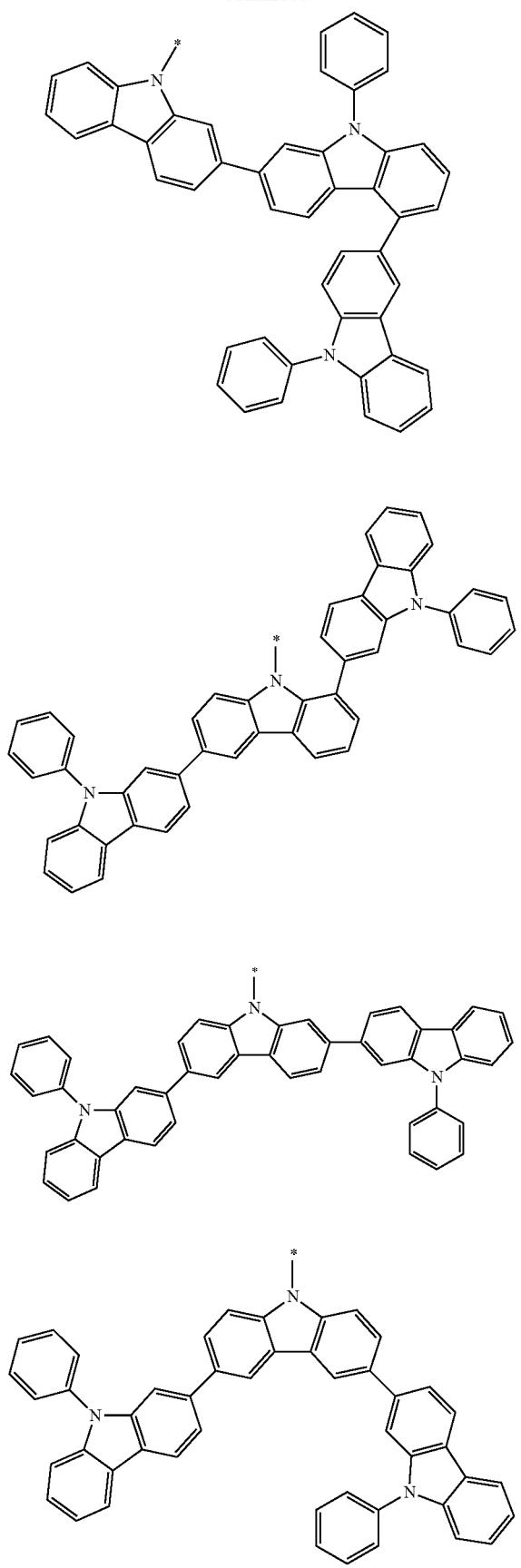
1714
-continued
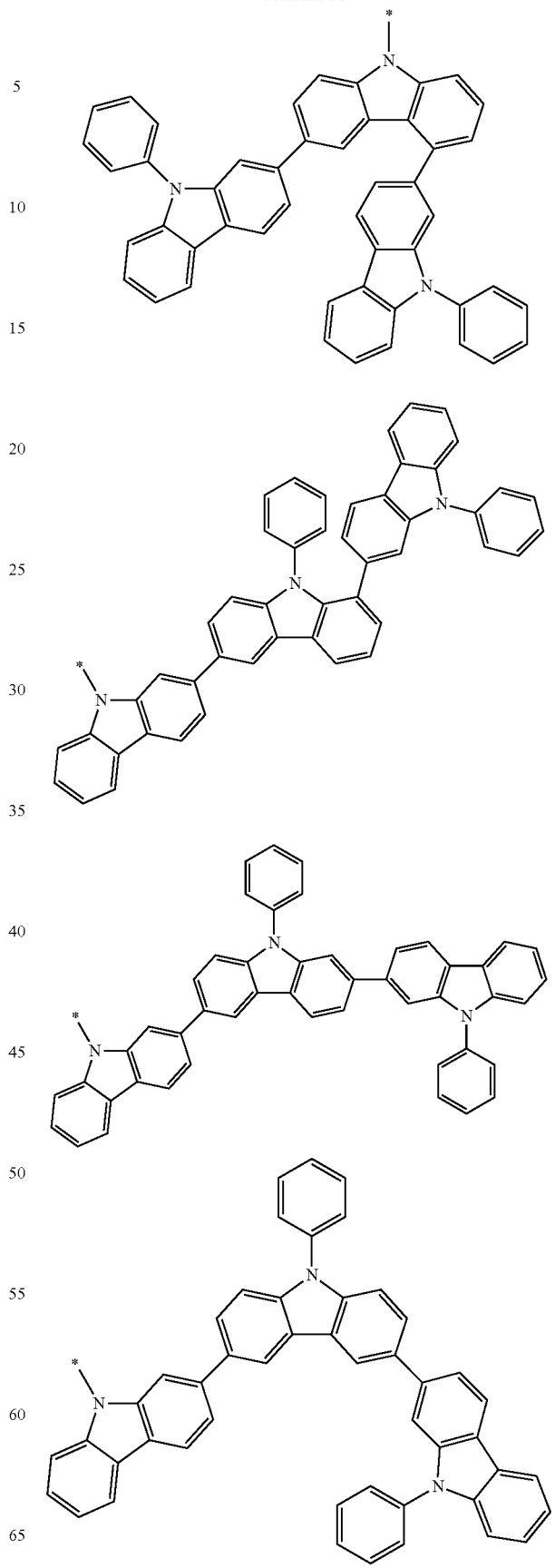

1715
-continued
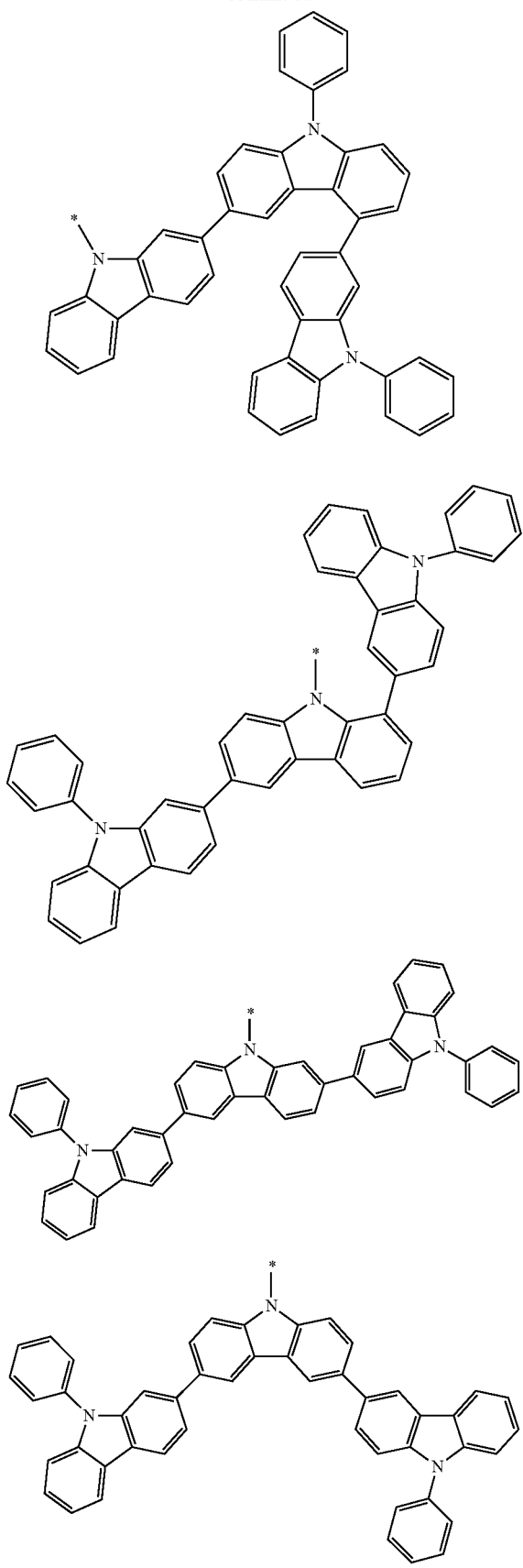
1716
-continued
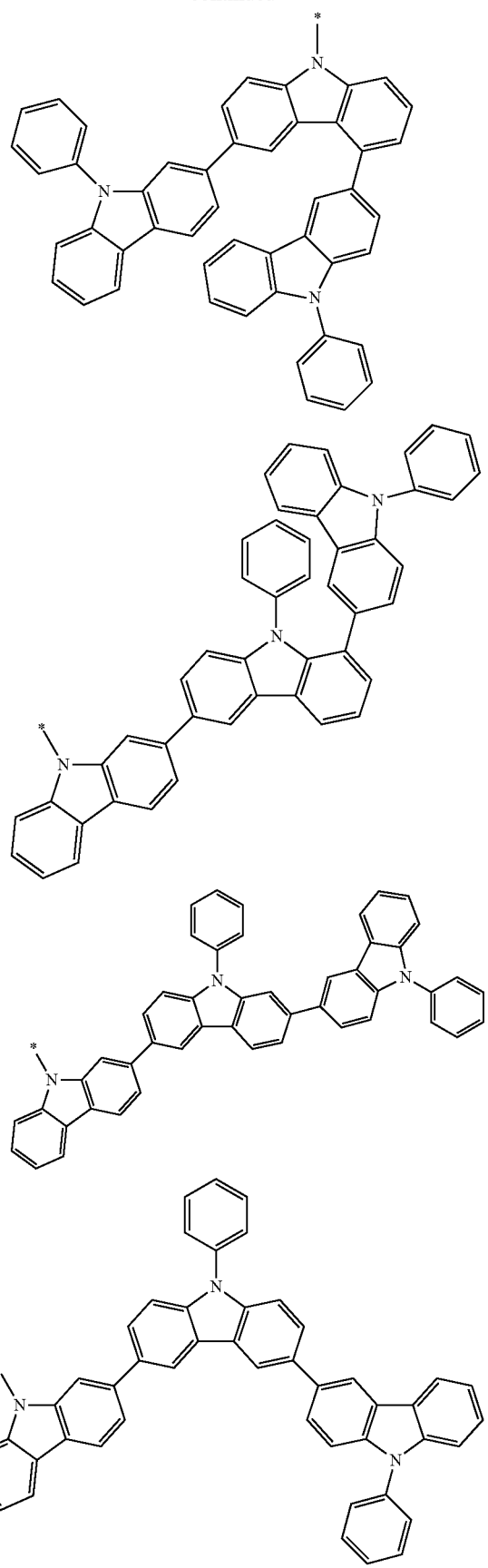

1717
-continued
1718
-continued
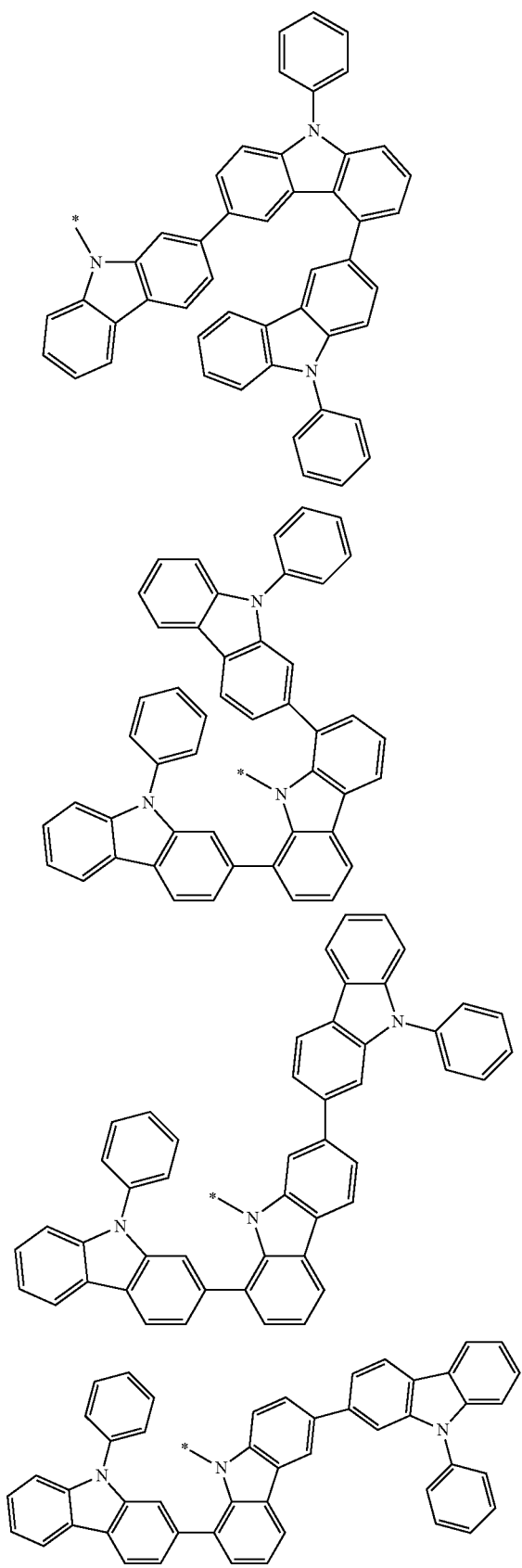
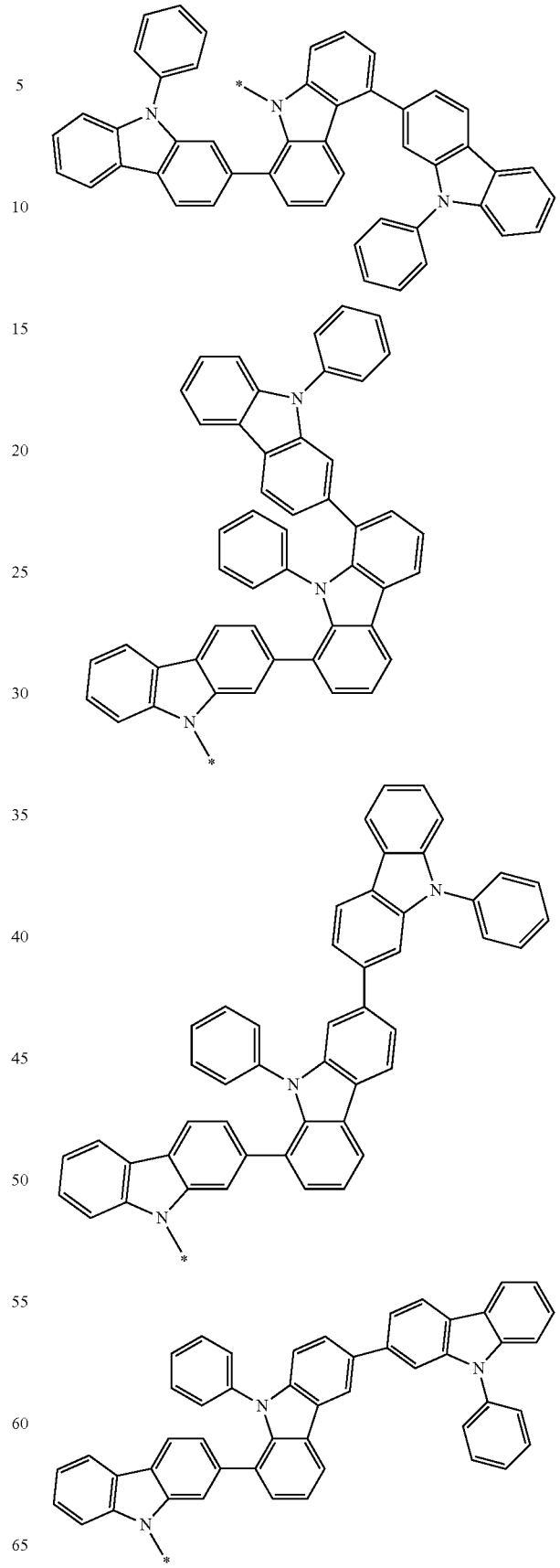

1719
-continued
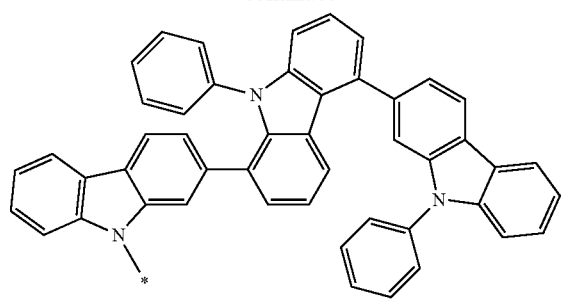
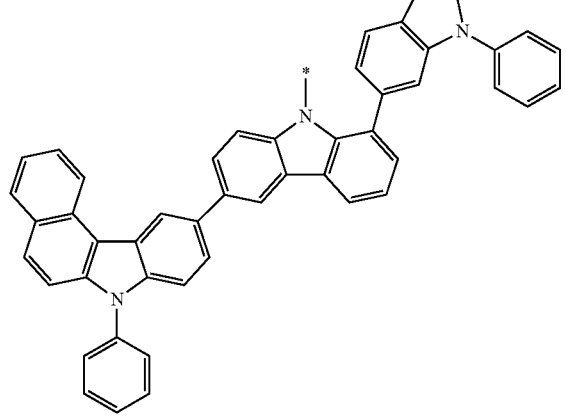
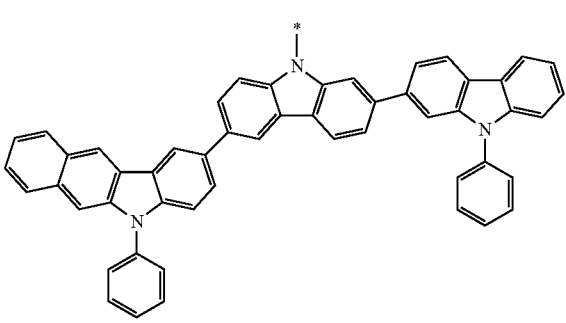
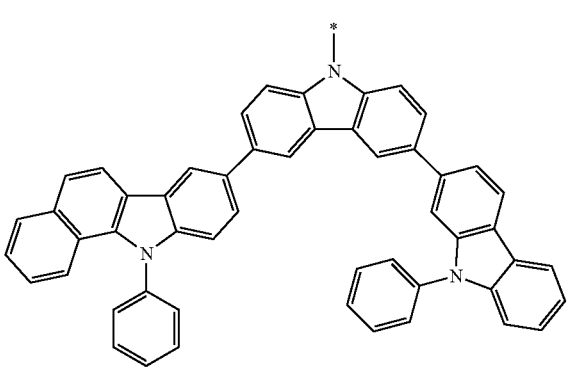
1720
-continued
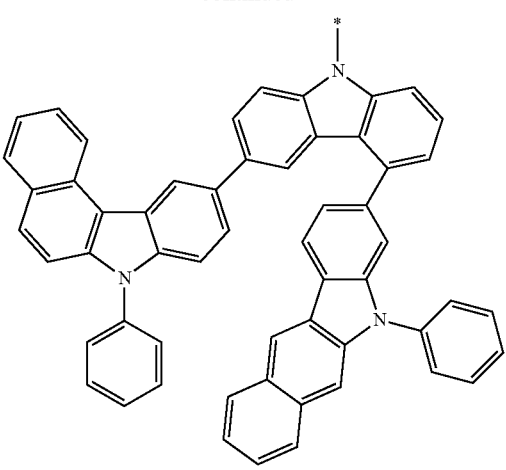
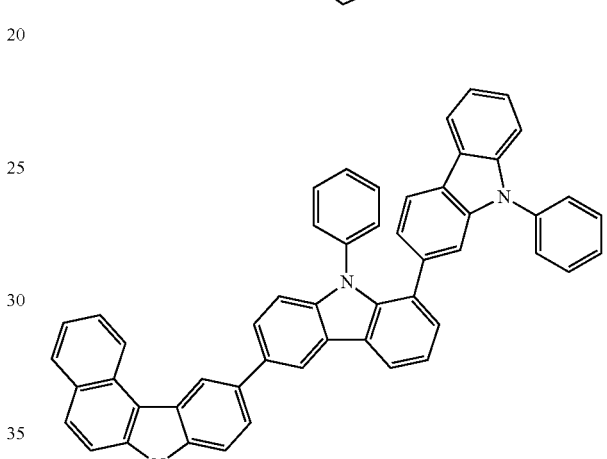
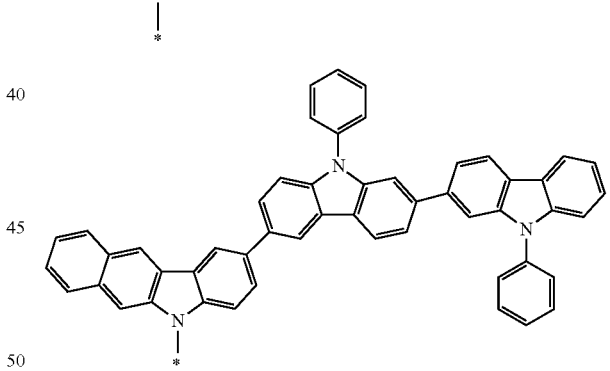
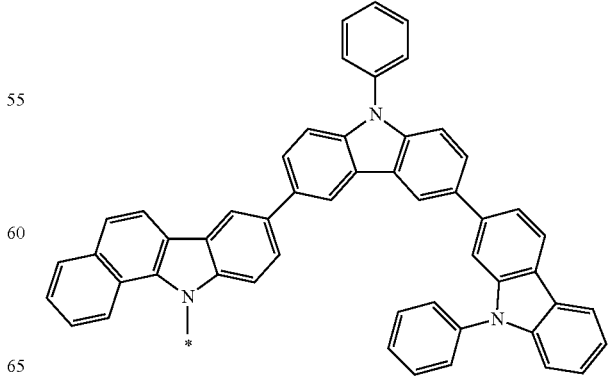

1721
-continued
1722
-continued
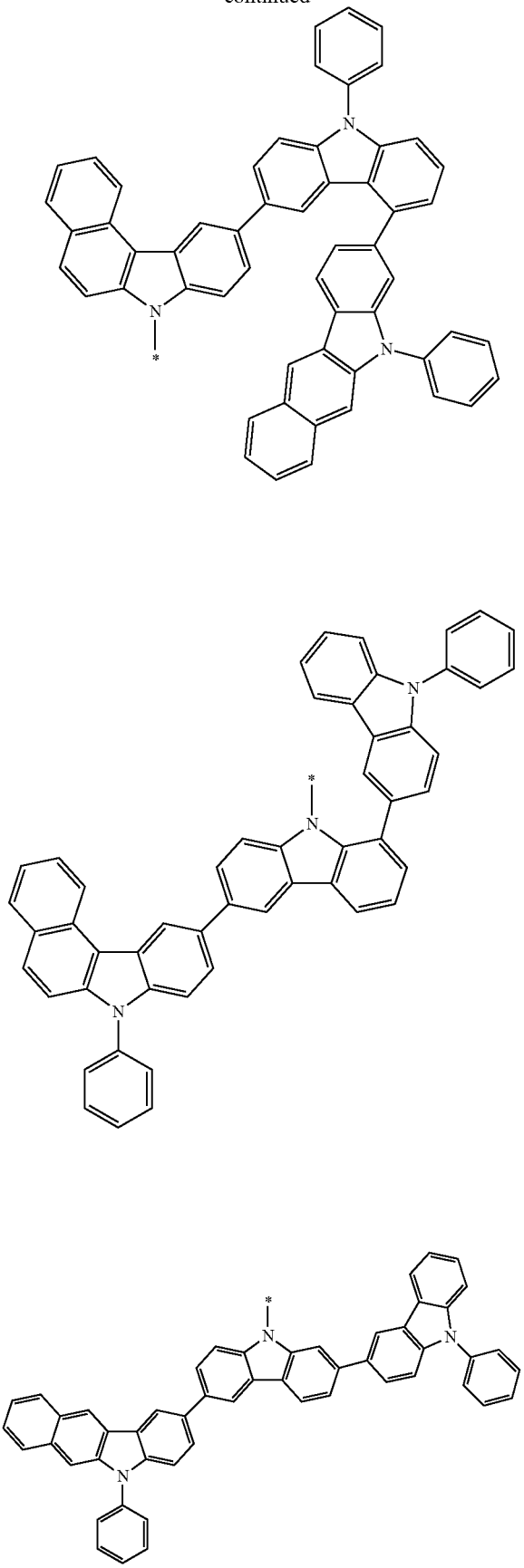
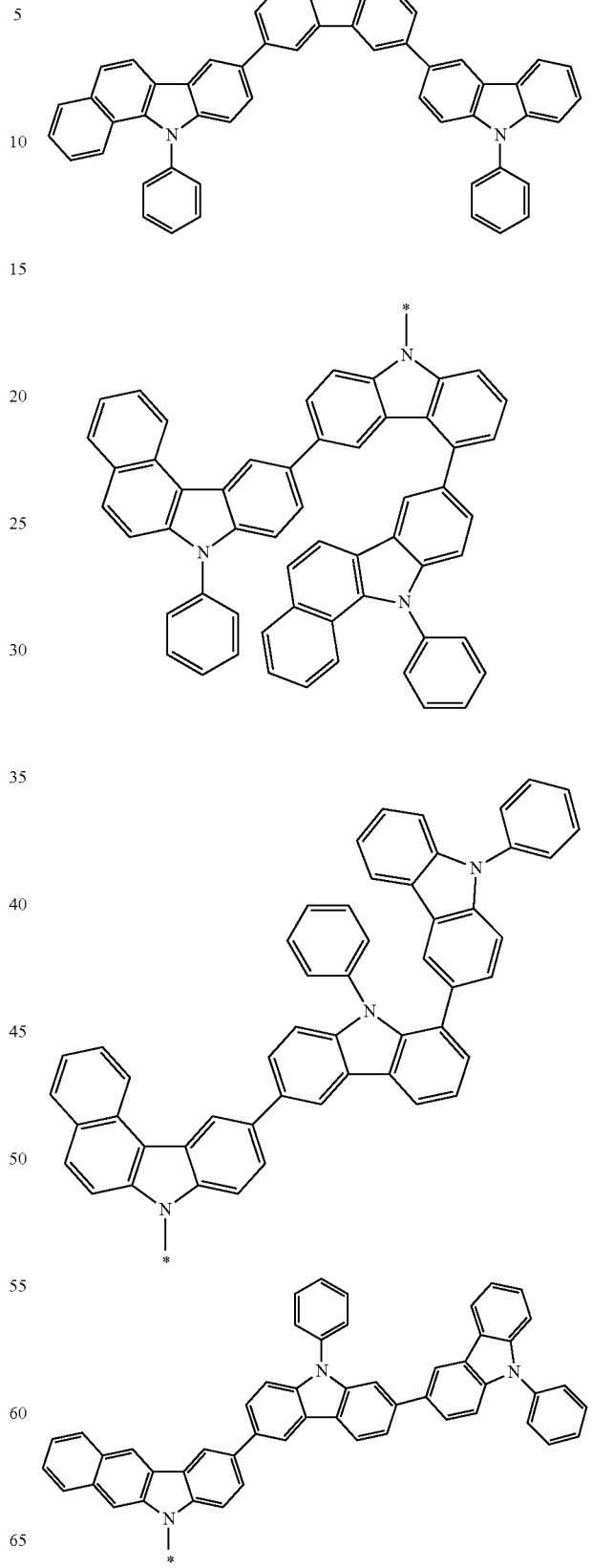

-continued

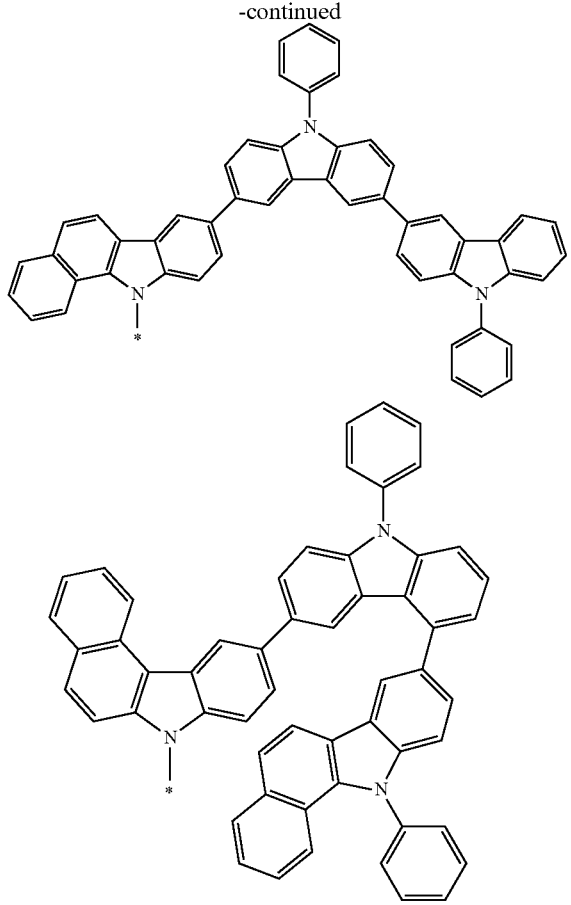

Description of Substituents Belonging to Group B Represented by Formula ($D^B$)

In formula ($D^B$), two of $X^1$ to $X^4$ represent carbon atoms which are respectively bonded to *21 and *22, and the other two independently represent C(R) or a nitrogen atom.

In an aspect of the invention, two of $X^1$ to $X^4$ which represent carbon atoms bonded to *21 and *22 are preferably selected from $X^1$ and $X^2$, $X^2$ and $X^3$, and $X^3$ and $X^4$.

$X^5$ to $X^{12}$ each independently represent C(R) or a nitrogen atom.

Namely, $X^1$ to $X^{12}$ not involved in the formation of the ring structure specified in formula ($D^B$) each independently represent C(R) or a nitrogen atom, with each being preferably C(R) in an aspect of the invention.

R represents a hydrogen atom or a substituent, two or more groups R may be the same or different, and two selected from groups R may be bonded to each other to form a ring.

In an aspect of the invention, two selected from groups R are preferably not bonded to each other, thereby failing to form a ring.

$Y^1$ in formula ($D^B$) represents an oxygen atom, a sulfur atom, —C($R^A$)($R^B$)—, —Si($R^C$)($R^D$)—, —P($R^F$)—, —P(=O)($R^F$)—, —S(=O)$_2$—, —P(=S)($R^G$)—, or —N($R^H$)—.

$R^A$ to $R^H$ each independently represent a hydrogen atom or a substituent, and $R^A$ and $R^B$, and $R^C$ and $R^D$ may be bonded to each other to form a ring.

* is bonded to one of *1 to *3 in formula 1[V].

The substituent for $R^A$ to $R^G$ is selected from those mentioned above, preferably a substituted or unsubstituted aryl group having 6 to 30 ring carbon atoms or a substituted or unsubstituted heteroaryl group having 5 to 30 ring atoms and more preferably a substituted or unsubstituted aryl group having 6 to 30 ring carbon atoms.

The aryl group for $R^A$ to $R^G$ has 6 to 30, preferably 6 to 18, more preferably 6 to 13, still more preferably 6 to 12, and particularly preferably 6 to 10 ring carbon atoms. The aryl group may be any of a non-fused aryl group, a fused aryl group, and a combination thereof.

The heteroaryl group for $R^A$ to $R^G$ has 5 to 30, preferably 5 to 20, more preferably 5 to 14, and still more preferably 5 to 10 ring atoms.

The heteroaryl group contains at least one, preferably 1 to 5, more preferably 1 to 3, and still more preferably 1 to 2 hetero atoms which may be the same or different.

Examples and preferred examples of the aryl group and the heteroaryl group for $R^A$ to $R^G$ are as described above with respect to $Ar^1$ and $Ar^2$ in formula ($D^A$).

In an aspect of the invention, the group represented by formula ($D^B$) is preferably a group represented by formula ($D^{B1}$):

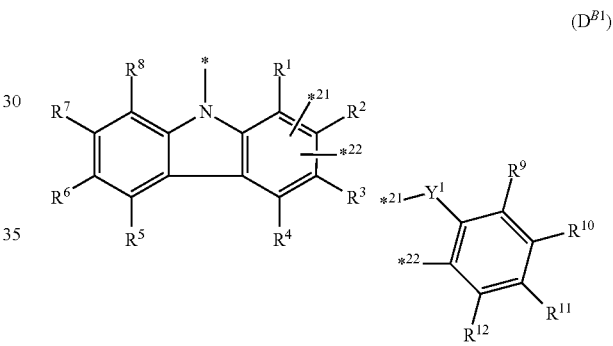

($D^{B1}$)

In formula ($D^{B1}$), $R^1$ to $R^{12}$ may be the same or different and each independently represent a hydrogen atom or a substituent; two selected from $R^1$ to $R^{12}$ may be bonded to each other to form a ring; and the other symbols are as defined above in formula ($D^B$).

Two carbon atoms from which two selected from $R^1$ to $R^4$ are removed are bonded to *21 and *22, respectively.

In an aspect of the invention, the group represented by formula ($D^{B1}$) is a group represented by any of formulae ($D^{B1}$-1) to ($D^{B1}$-6):

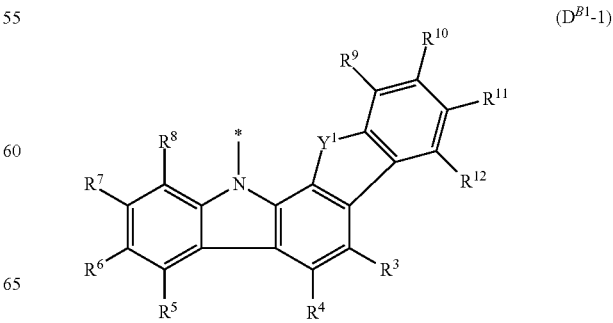

($D^{B1}$-1)

-continued

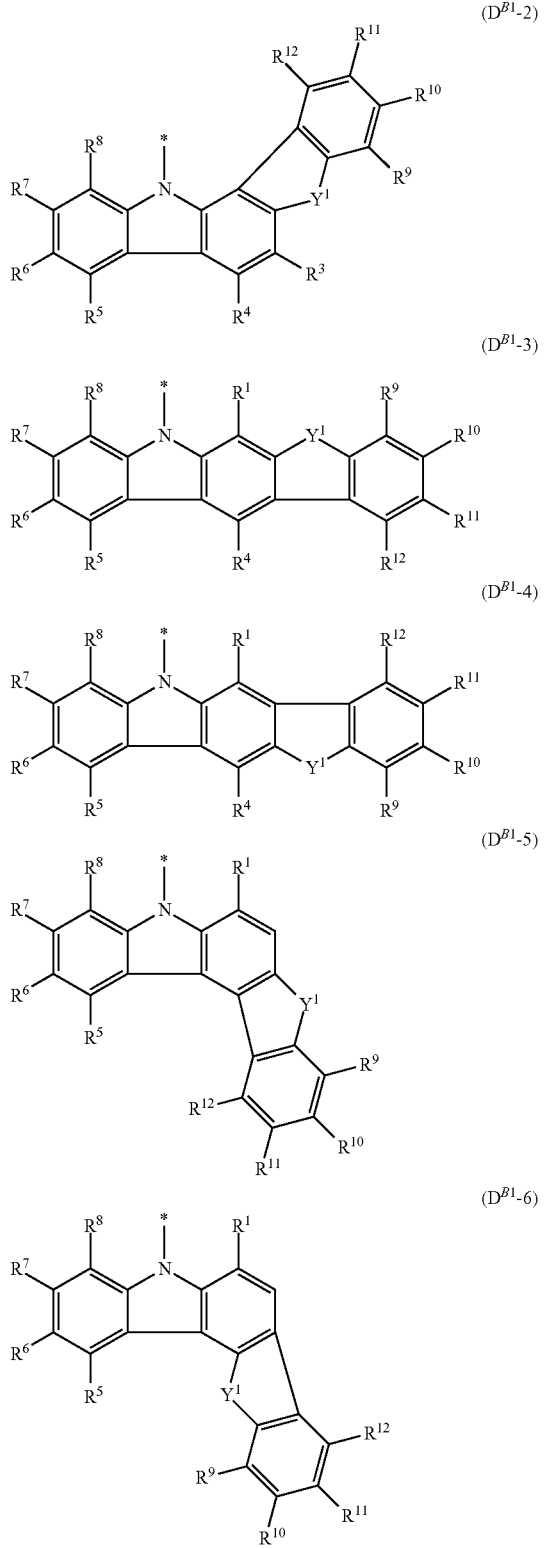

in formulae ($D^{B1}$-1) to ($D^{B1}$-6), each symbol is as defined above in formula ($D^{B1}$).

In formula ($D^B$), when two selected from $R^1$ to $R^{24}$ are bonded to each other to form a ring, one or more pairs selected from $R^5$ and $R^6$, $R^6$ and $R^7$, and $R^7$ and $R^8$ are preferably bonded to form a ring.

In the compound in an aspect of the invention, two selected from $R^1$ to $R^{24}$ in formula ($D^B$) are preferably not bonded to each other, thereby failing to form a ring, and the group represented by formula ($D^B$) is more preferably a group represented by formula ($D^{B2}$):

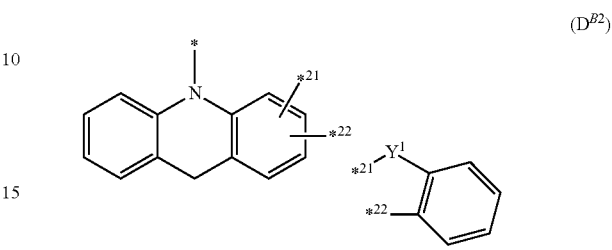

In formula ($D^{B2}$), two of the carbon atoms at 1-position, 2-position, 3-position and 4-position of the carbazolyl group from which hydrogen atoms are removed are bonded to *21 and *22, respectively, and the other symbols are as defined above in formula ($D^B$).

The group represented by formula ($D^B$) is preferably selected from the following groups, wherein * represents a bonding site to one of *1 to *3 in formula 1[V] and a hydrogen atom bonded to a carbon atom may be substituted with the substituent mentioned above.

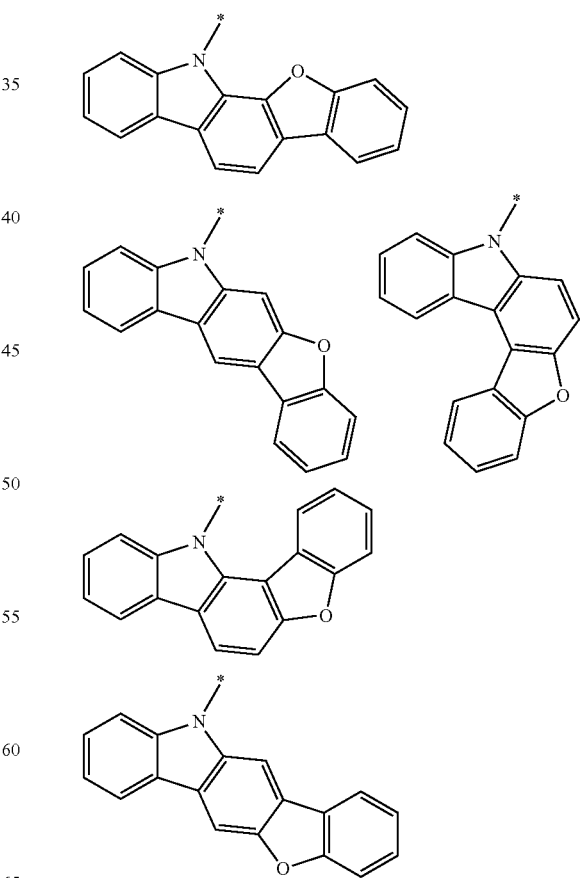

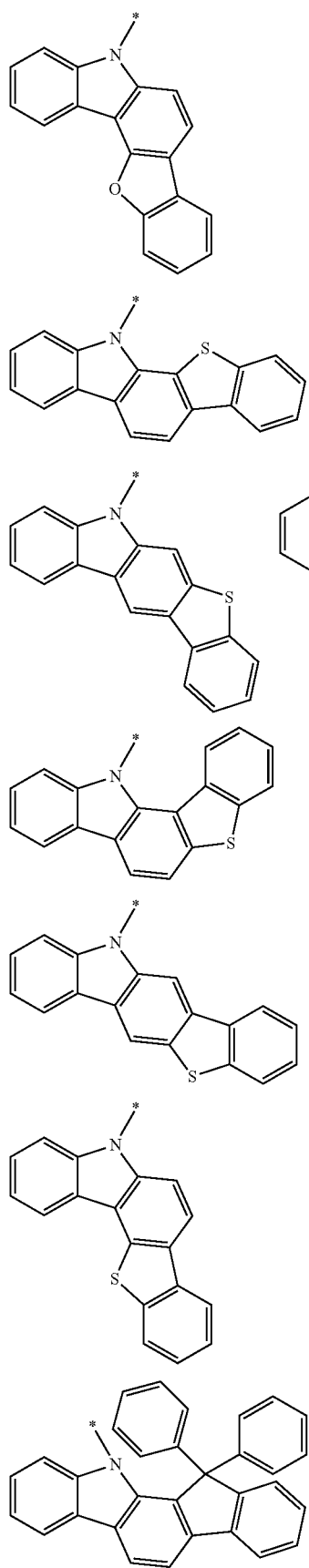
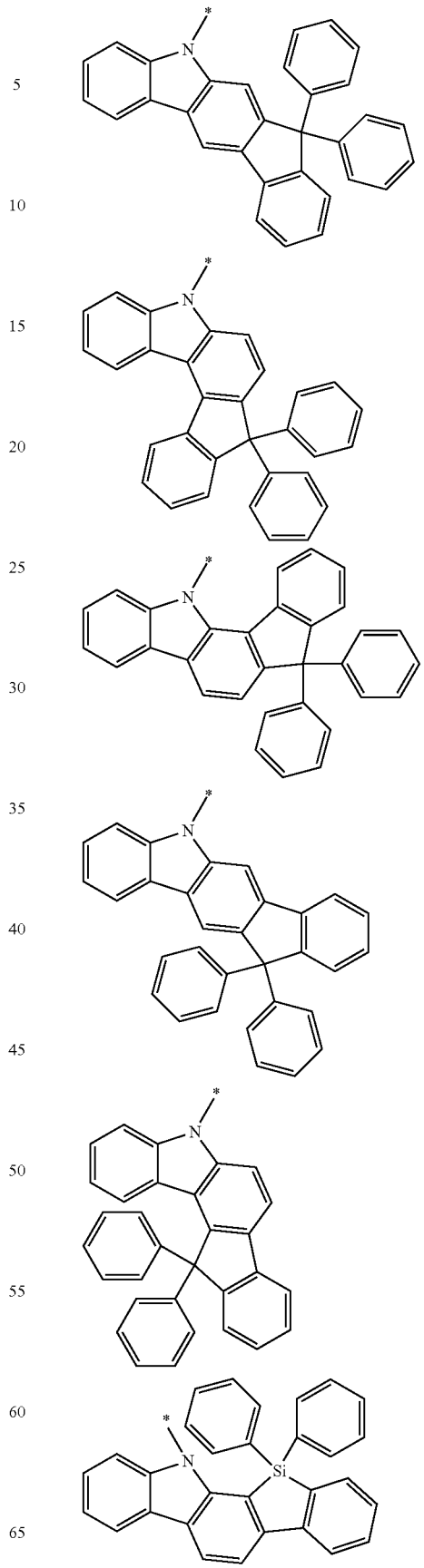

1729
-continued
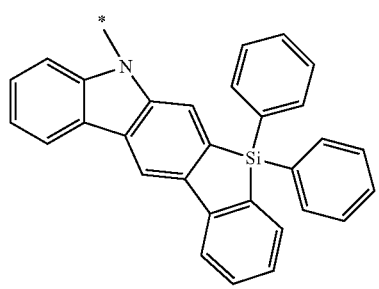
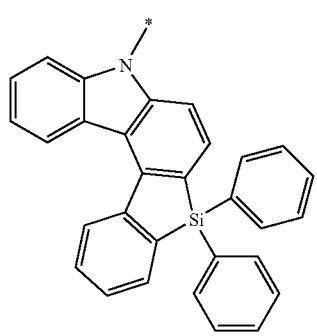
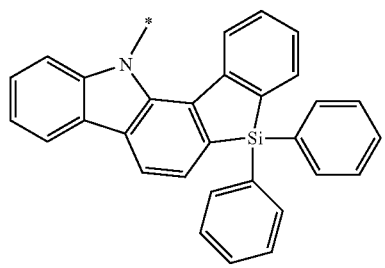
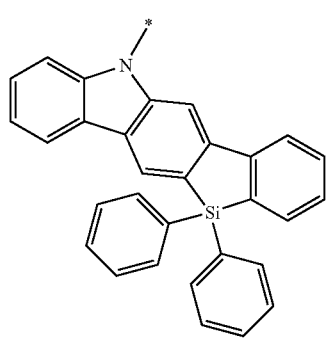
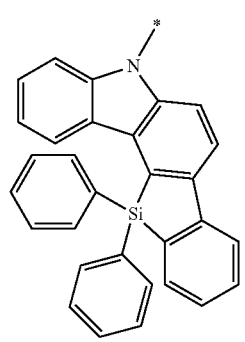
1730
-continued
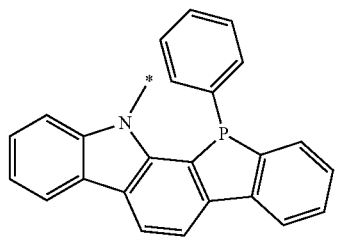
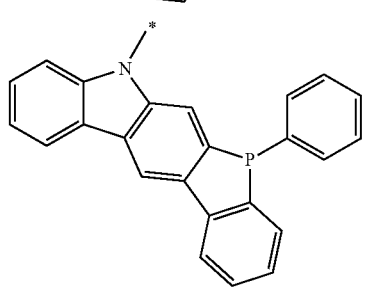
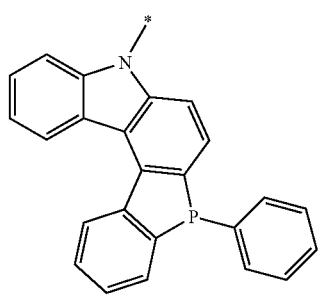
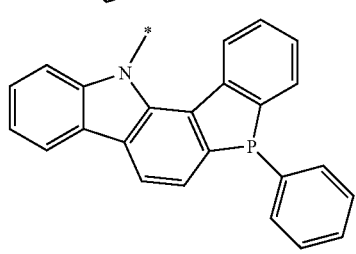
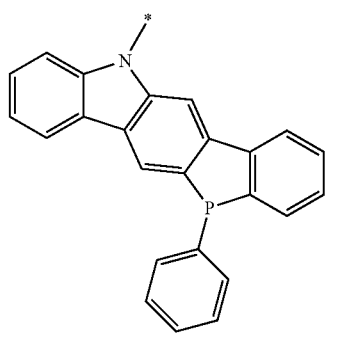
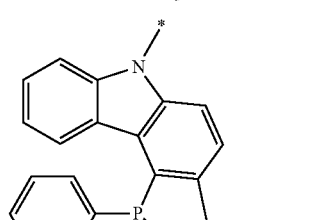

1731
-continued
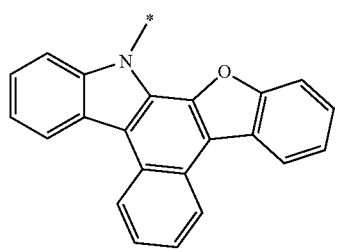
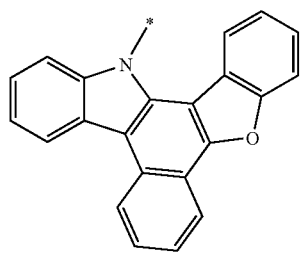
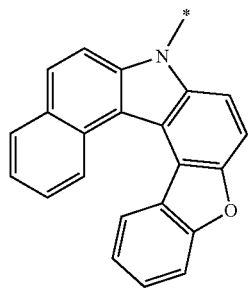
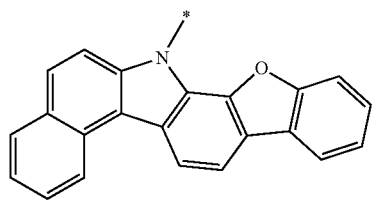
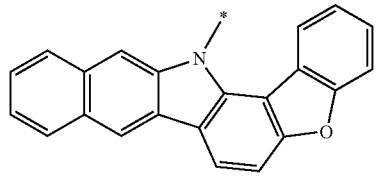
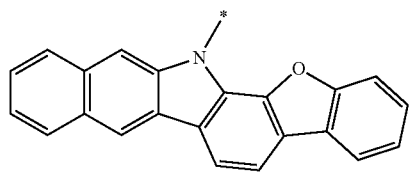
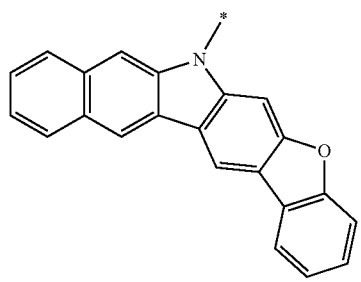
1732
-continued
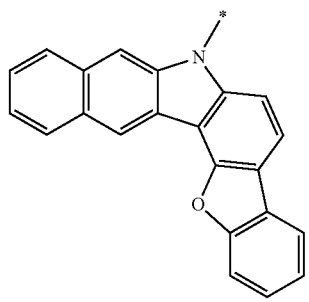
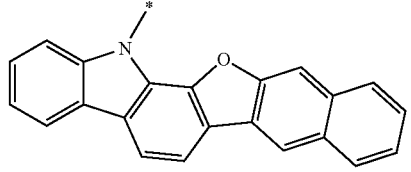
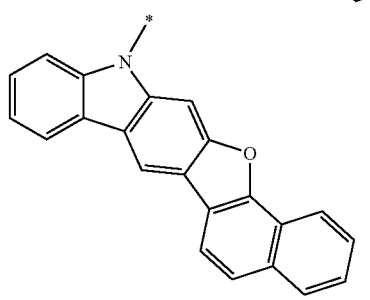
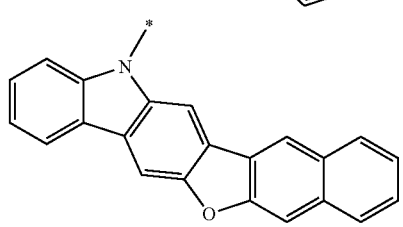
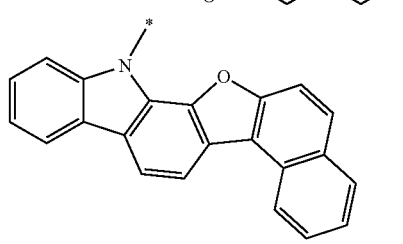

1733
-continued
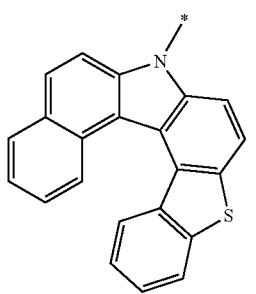
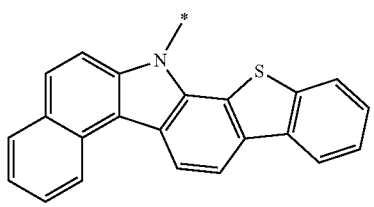
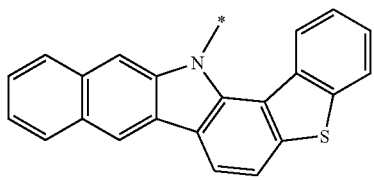
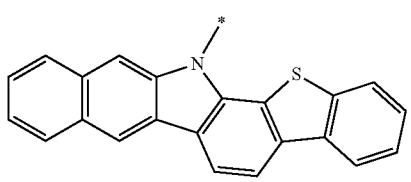
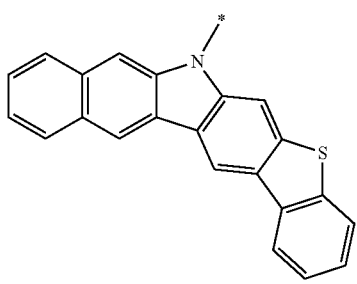
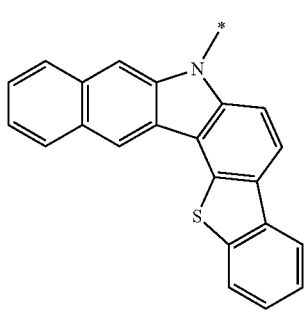
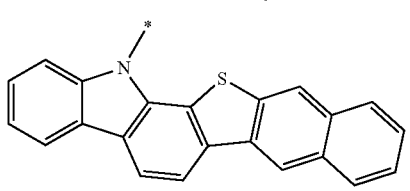
1734
-continued
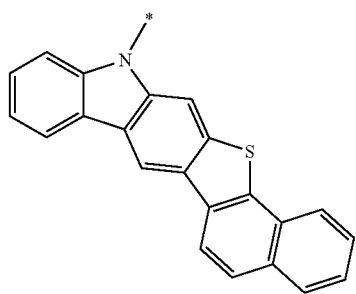
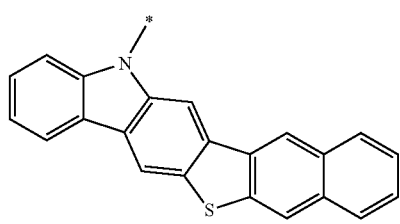

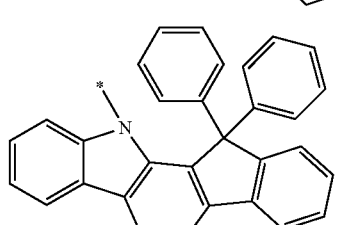
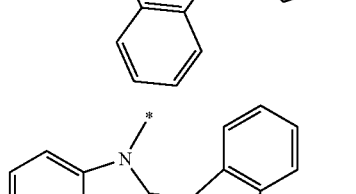
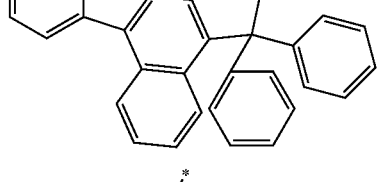
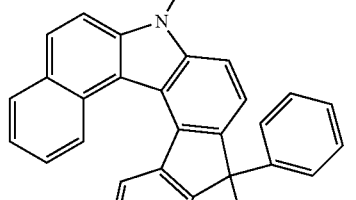

1735
-continued
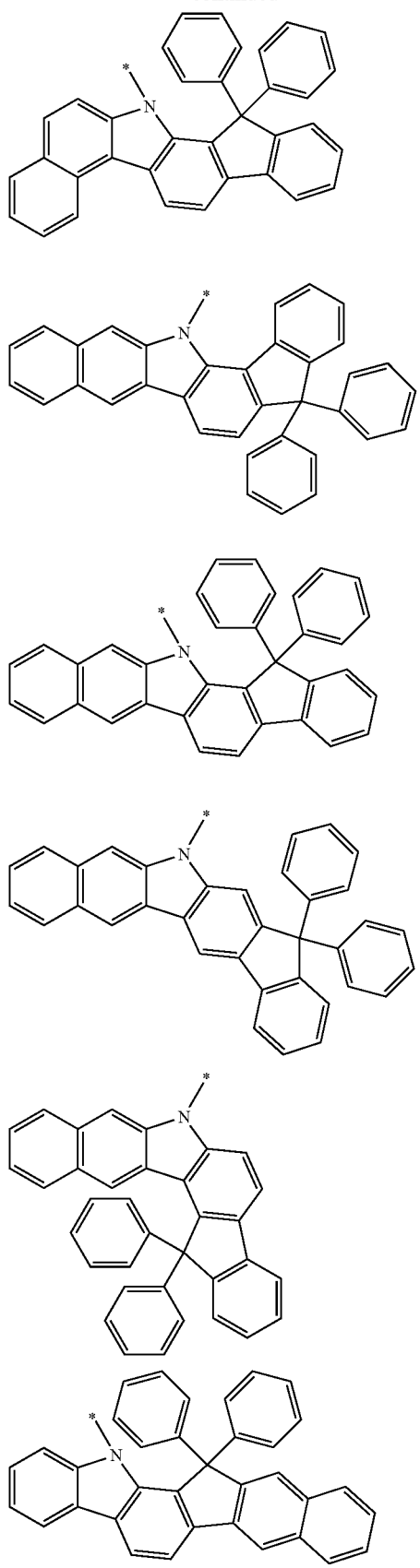
1736
-continued
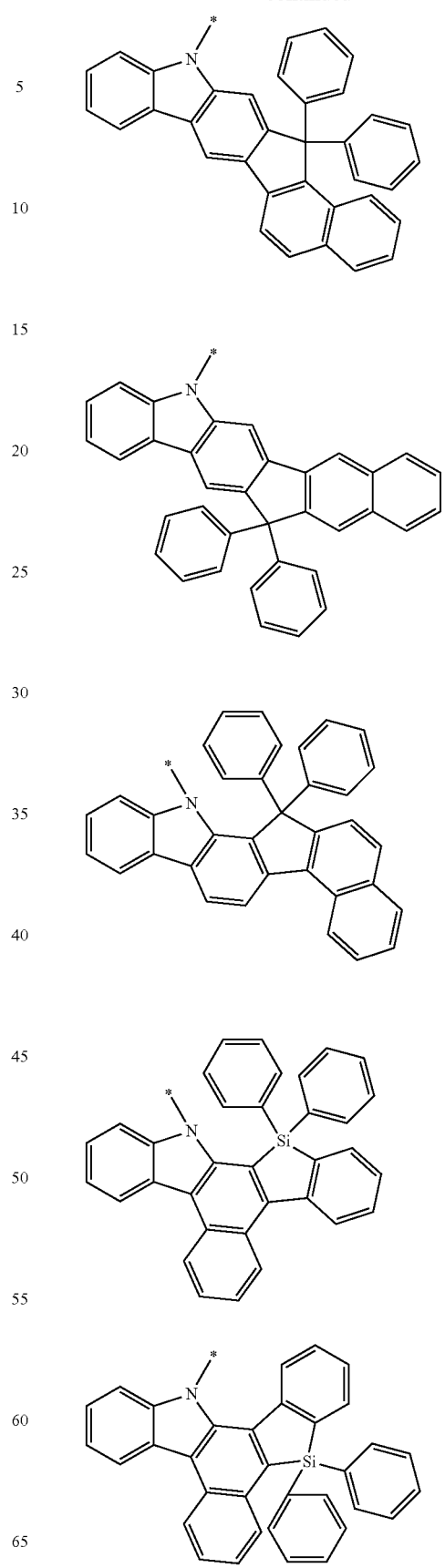

1737
-continued
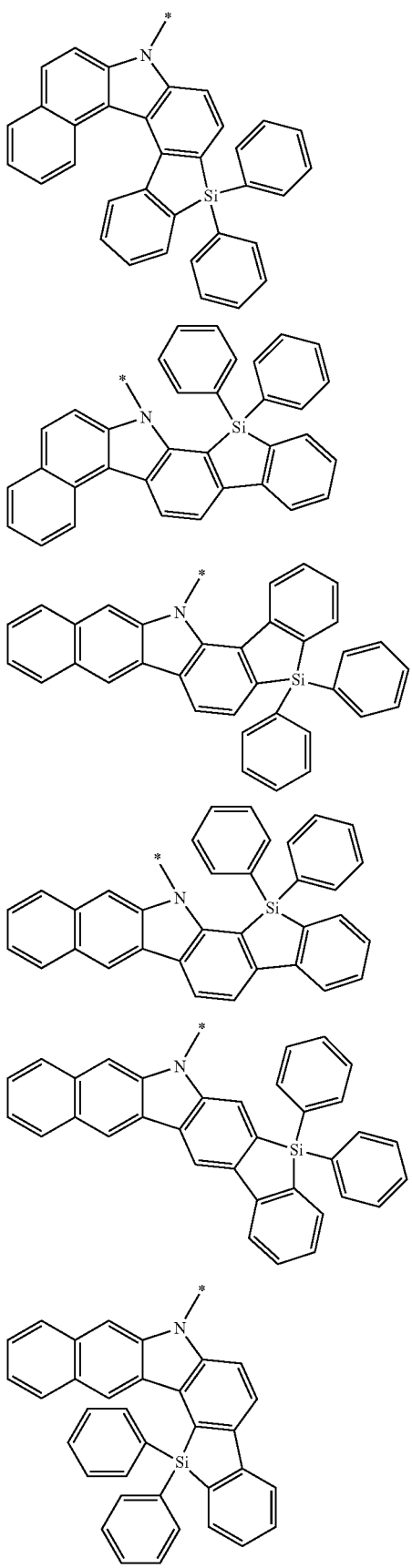
1738
-continued
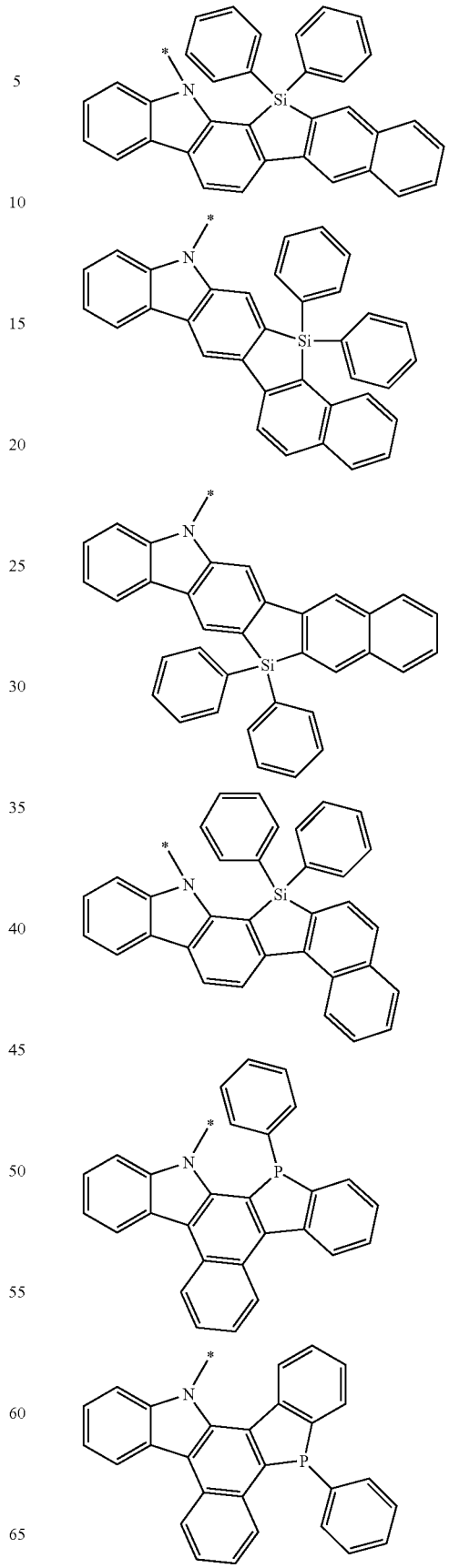

1739
-continued
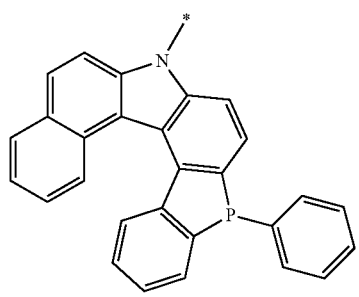
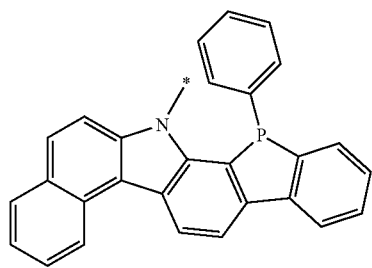
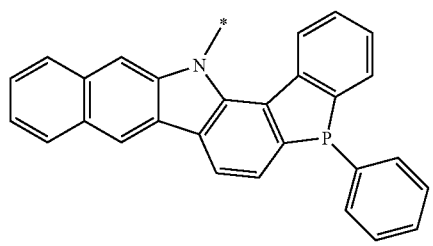
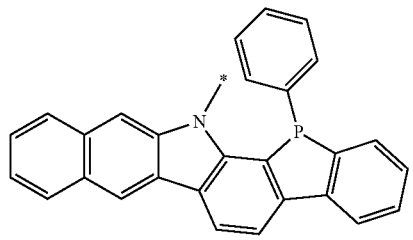
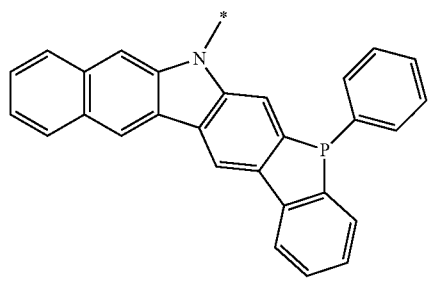
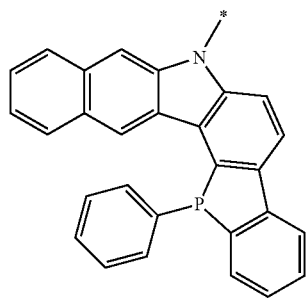
1740
-continued
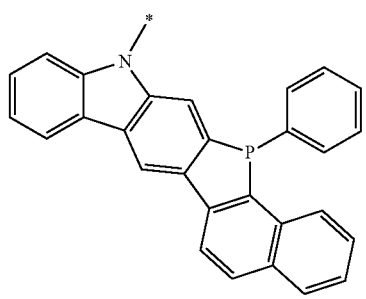
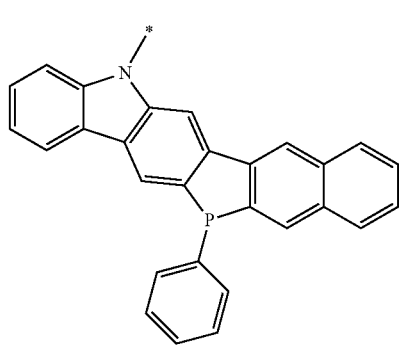
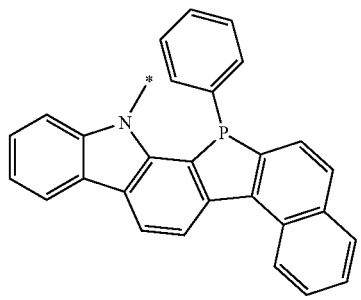
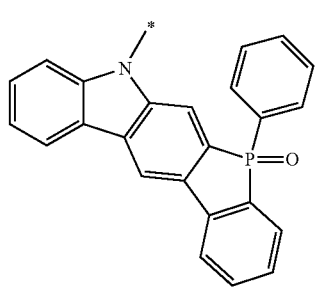

1741
-continued
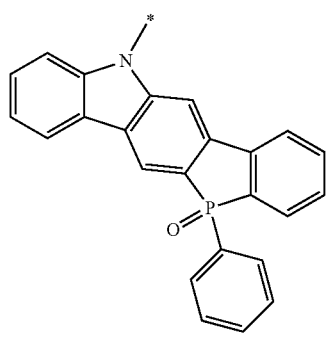
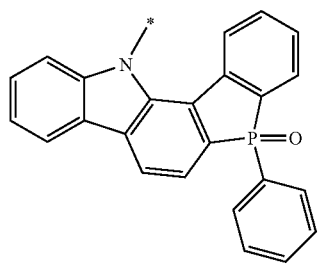
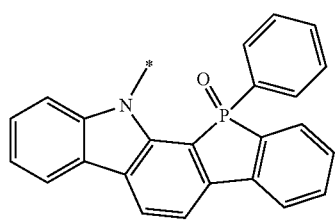
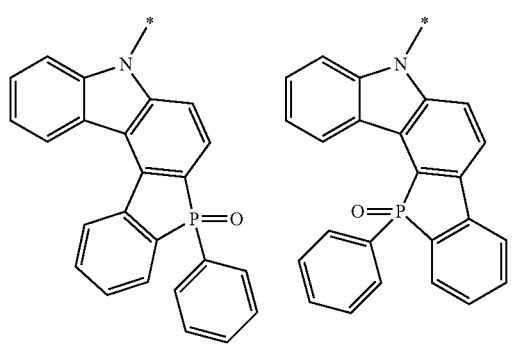
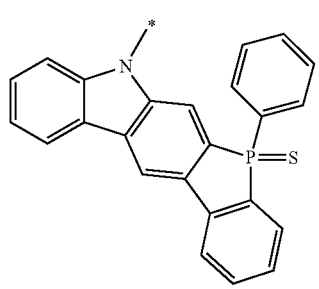
1742
-continued
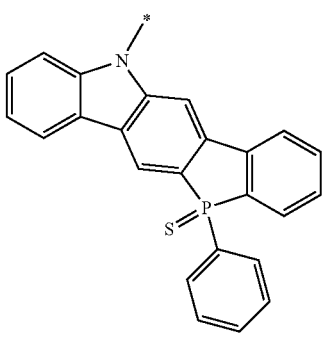
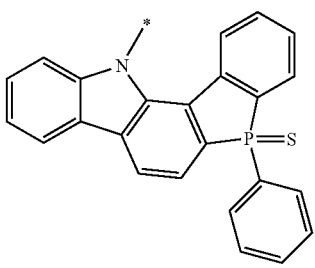
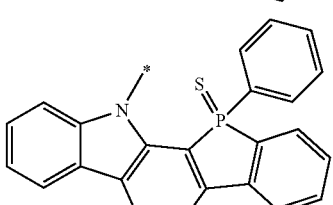
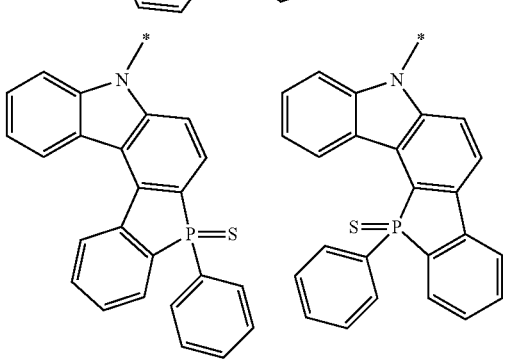
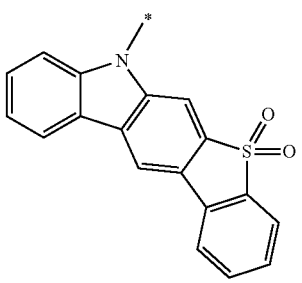
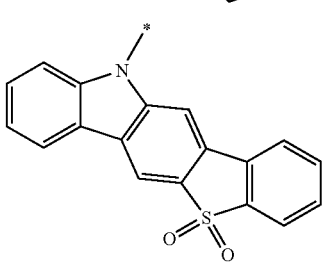

1743
-continued
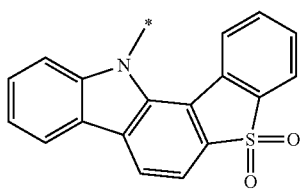
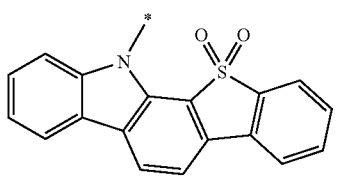
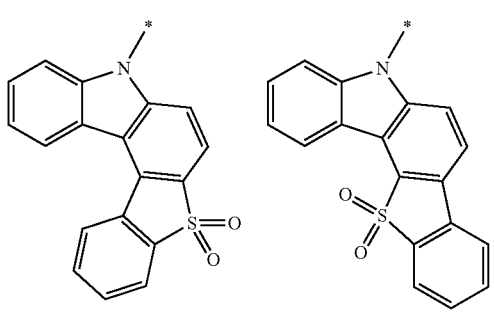
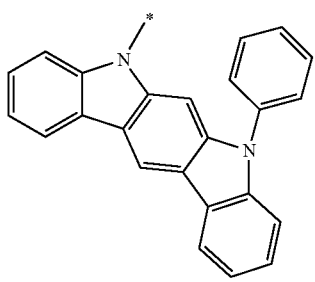
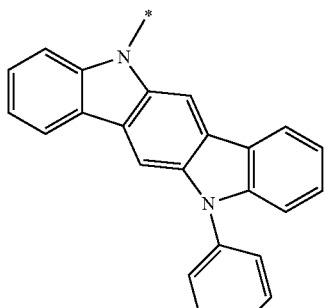
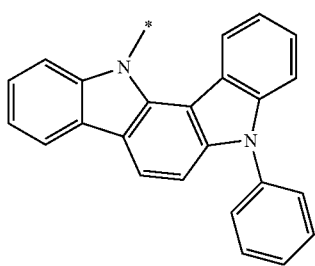
1744
-continued
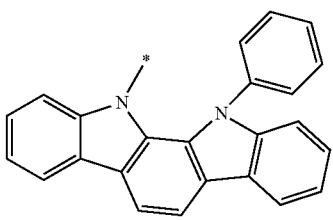
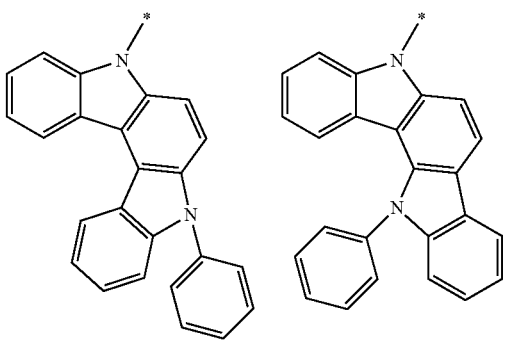
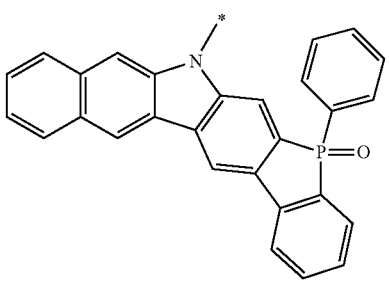
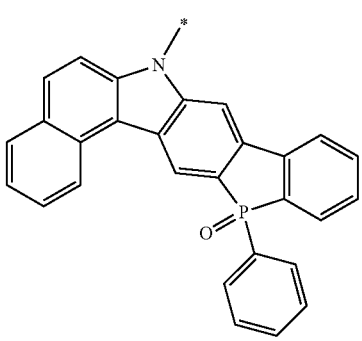
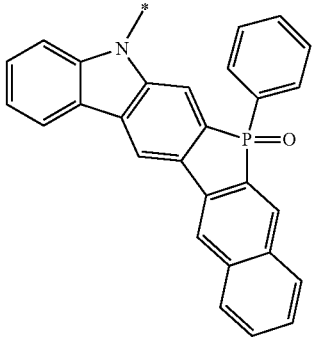

1745
-continued
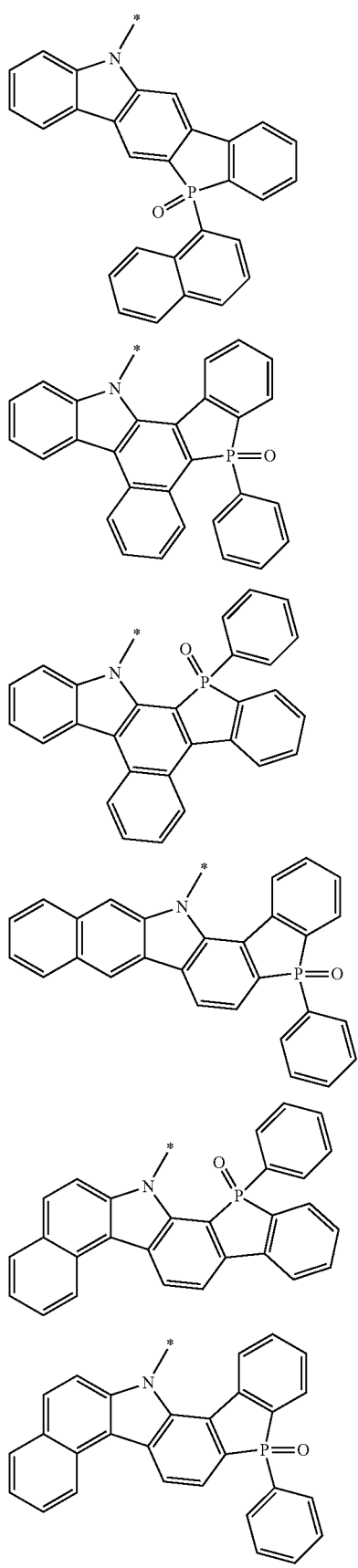
1746
-continued
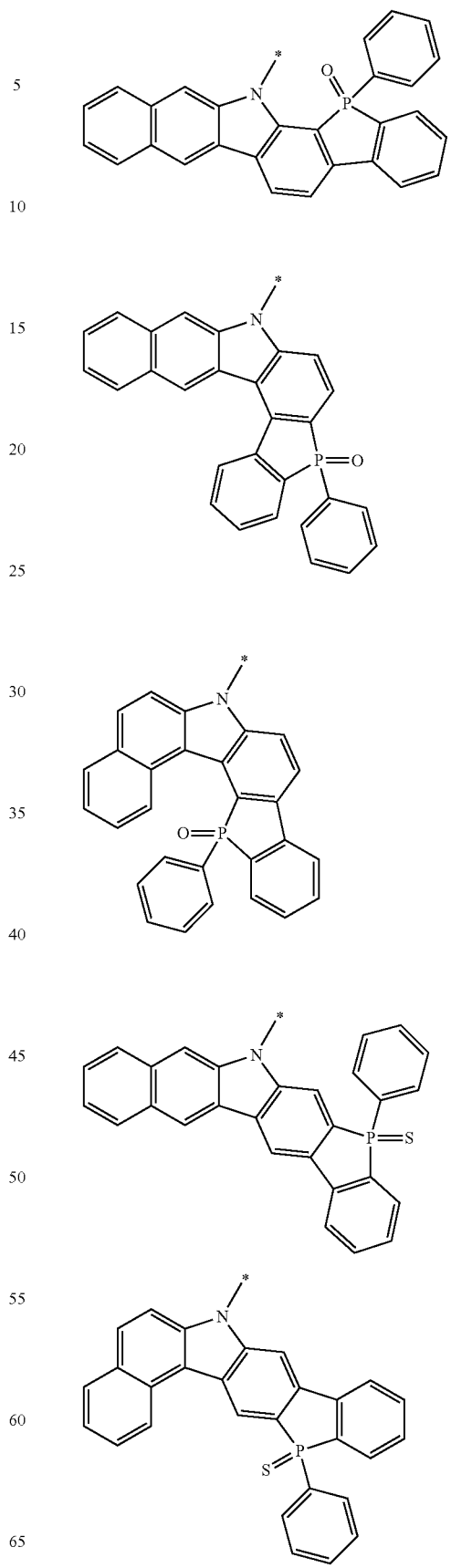

1747
-continued
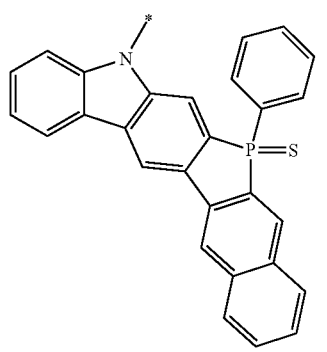
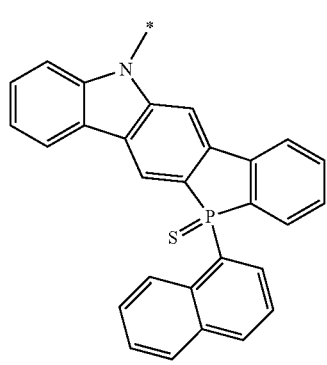
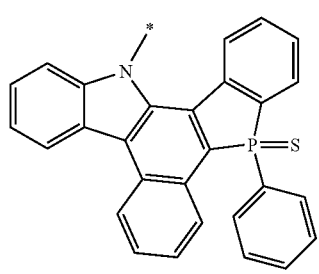
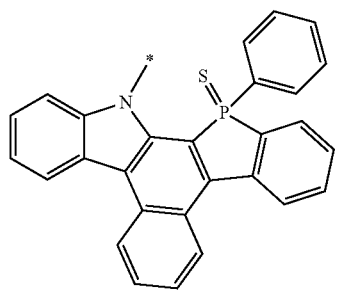
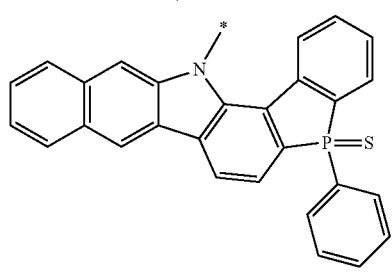
1748
-continued
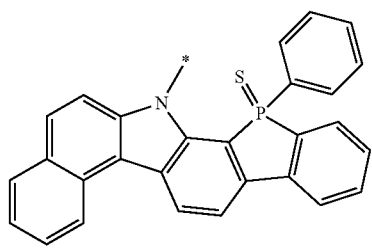
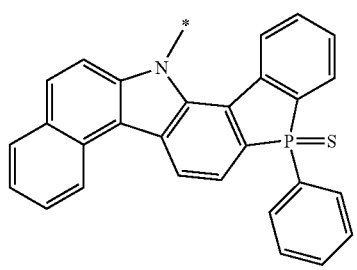
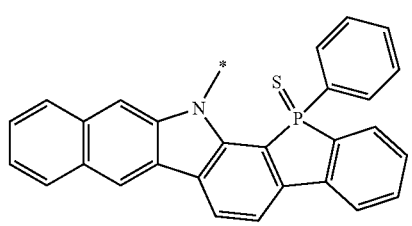
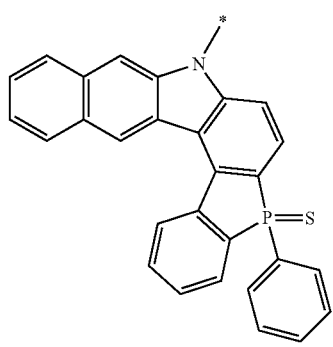
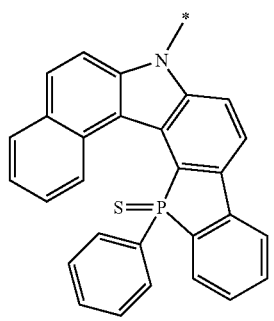 [SMILES: Cn1c2ccc3c(c2c2c4ccccc4ccc21)P(=S)(c1ccccc1)c1ccccc1-3]
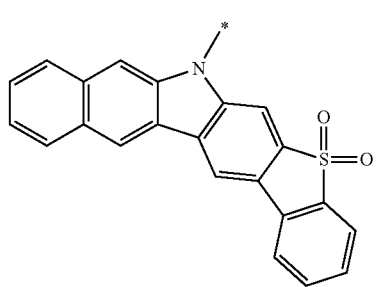

-continued
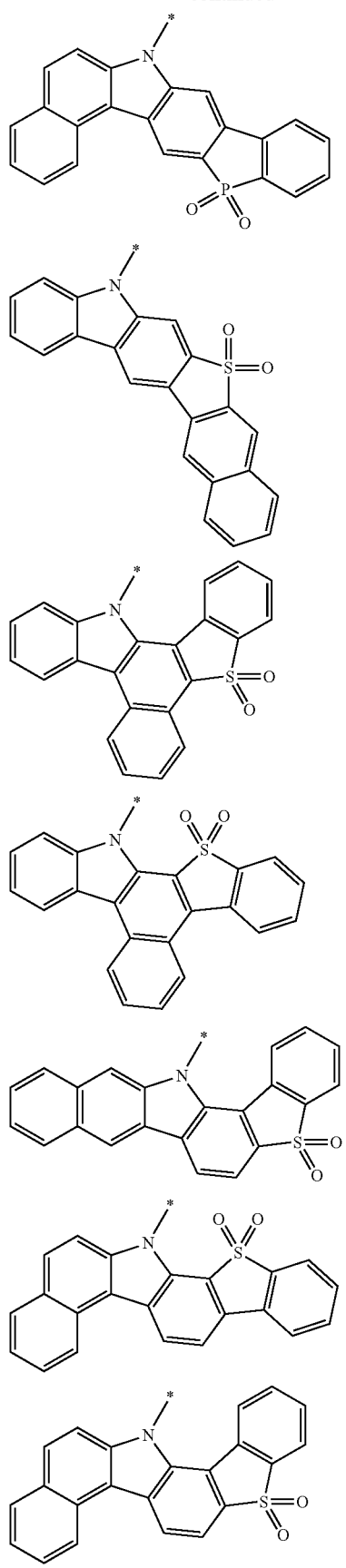
-continued
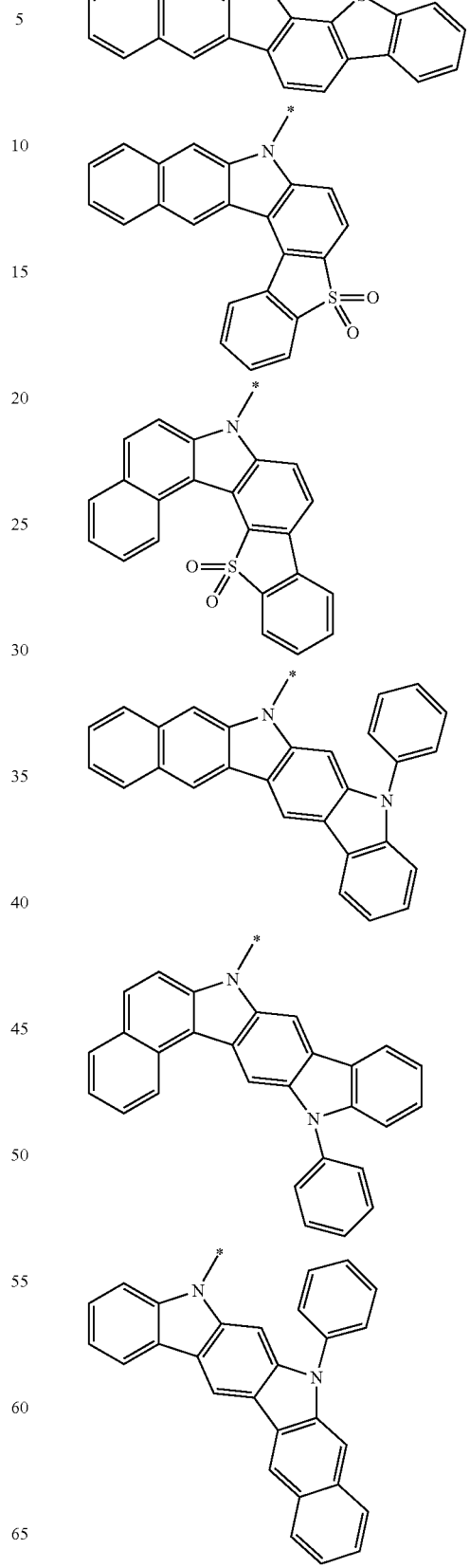

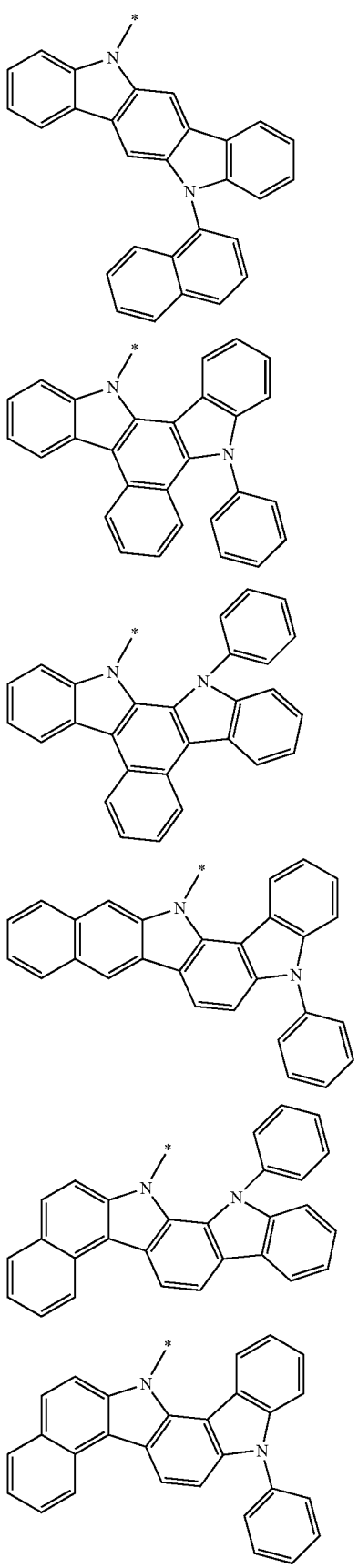

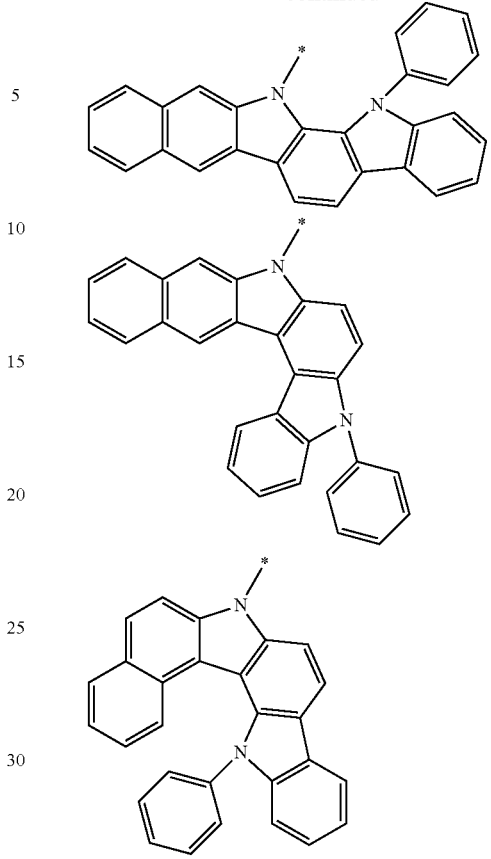

Description of Substituents Belonging to Group C Represented by Formula ($D^C$)

In formula ($D^C$), $X^1$ to $X^8$ each represent $C(R^1)$ to $C(R^8)$, respectively, or a nitrogen atom, and $R^1$ to $R^8$ each independently represent a hydrogen atom or a substituent.

One of $X^1$ to $X^4$ represents a carbon atom which is directly bonded to $Z^1$ or the nitrogen atom to which $Ar^4$ and $Ar^5$ are bonded. Namely, one of $X^1$ to $X^4$ is a carbon atom directly bonded to the nitrogen atom to which $Ar^4$ and $Ar^5$ are bonded when d is 0, and a carbon atom directly bonded to $Z^1$ when d is 1.

Two selected from $R^1$ to $R^8$, each not involved in the above direct bonding, may be bonded to each other to form a ring. In an aspect of the invention, two selected from $R^1$ to $R^8$, each not involved in the above direct bonding, are preferably not bonded to each other, thereby failing to form a ring.

The "direct bond" used herein is generally called a "single bond" in some cases.

$X^1$ to $X^8$ are each preferably $C(R^1)$ to $C(R^8)$, and more preferably $R^1$ to $R^8$ are all hydrogen atoms.

In formula ($D^C$), $Ar^1$, $Ar^4$ and $Ar^5$ each independently represent a substituted or unsubstituted aryl group having 6 to 30 ring carbon atoms or a substituted or unsubstituted heteroaryl group having 5 to 30 ring atoms.

The aryl group for $Ar^1$, $Ar^4$ and $Ar^5$ has 6 to 30, preferably 6 to 18, more preferably 6 to 13, still more preferably 6 to 12, and particularly preferably 6 to 10 ring carbon atoms. The aryl group may be any of a non-fused aryl group, a fused aryl group, and a combination thereof.

The heteroaryl group for $Ar^1$, $A^4$ and $Ar^5$ has 5 to 30, preferably 5 to 20, more preferably 5 to 14, and still more preferably 5 to 10 ring atoms.

The heteroaryl group contains at least one, preferably 1 to 5, more preferably 1 to 3, and still more preferably 1 to 2 hetero atoms which may be the same or different. The hetero atom may include, for example, a nitrogen atom, a sulfur atom, an oxygen atom, and a phosphorus atom, and preferably selected from these atoms.

Examples and preferred examples of the aryl group and the heteroaryl group for $Ar^1$, $Ar^4$ and $Ar^5$ are as described above with respect to $Ar^1$ and $Ar^2$ in formula ($D^4$).

In formula ($D^C$), $Z^1$ independently represents a substituted or unsubstituted aromatic hydrocarbon group having 6 to 30 ring carbon atoms, a substituted or unsubstituted heterocyclic group having 5 to 30 ring atoms, or a group wherein 2 to 4 groups selected from the preceding groups are bonded to each other.

The aromatic hydrocarbon group, the heterocyclic group, the group wherein 2 to 4 groups selected from the preceding groups are bonded to each other for Z in formula ($D^C$), and preferred examples thereof are as described above with respect to $L^1$ to $L^3$. The aromatic hydrocarbon group for $Z^1$ to $Z^3$ is preferably a phenylene group and a naphthylene group and more preferably a phenylene group.

$Z^1$ is preferably a substituted or unsubstituted aromatic hydrocarbon group having 6 to 30 ring carbon atoms. The aromatic hydrocarbon group more preferred is as described above.

In formula ($D^C$), d is 0 or 1.

One of *1 to *3 of formula 1[V] is directly bonded to a nitrogen atom from which one of $Ar^1$ and $Ar^4$ indicated by *6' in formula ($D^C$) is removed.

For example, formula 1[V] wherein *1 is directly bonded to a nitrogen atom from which $Ar^1$ indicated by *6' is removed is represented by the following formula (shown partially):

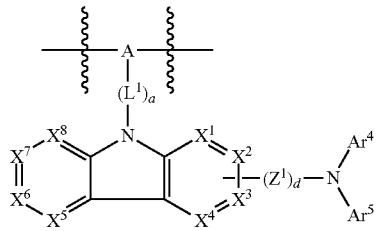

When *1 is directly bonded to a nitrogen atom from which $Ar^4$ indicated by *6' is removed, formula 1[V] is represented by the following formula (shown partially):

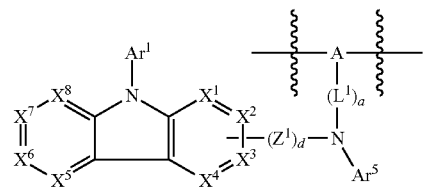

In an aspect of the invention, the group represented by formula ($D^C$) is preferably a group represented by formula ($D^{C1}$):

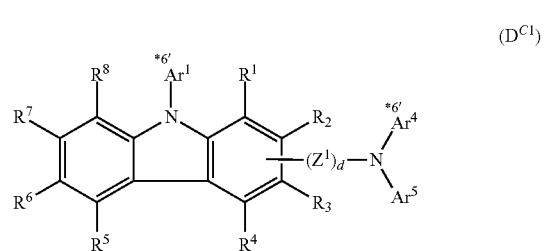

in formula ($D^{C1}$), each symbol is as defined above in formula ($D^C$).

In an aspect of the invention, the group represented by formula ($D^C$) is preferably a group represented by formula ($D^{C2}$):

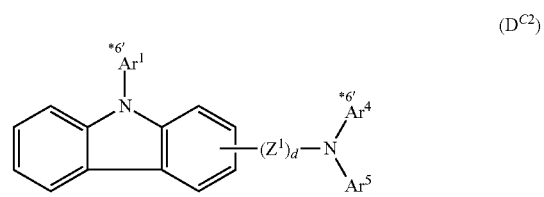

in formula ($D^{C2}$), each symbol is as defined above in formula ($D^C$).

Examples of the group represented by formula ($D^C$) are preferably selected from the following groups, wherein a hydrogen atom bonded to a carbon atom may be substituted with the substituent mentioned above.

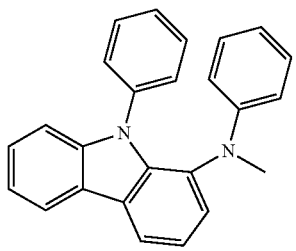
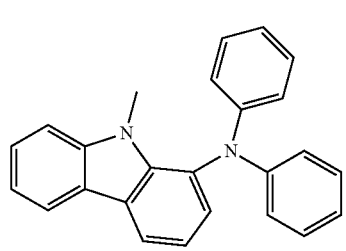
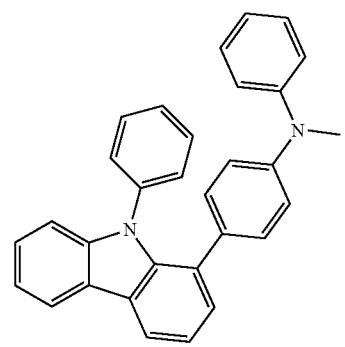

-continued
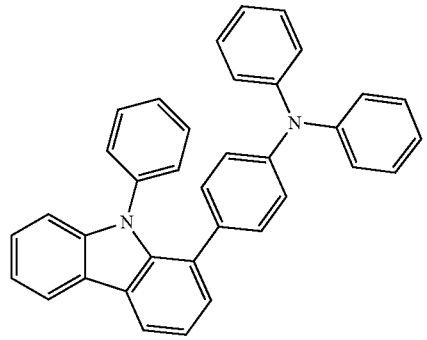
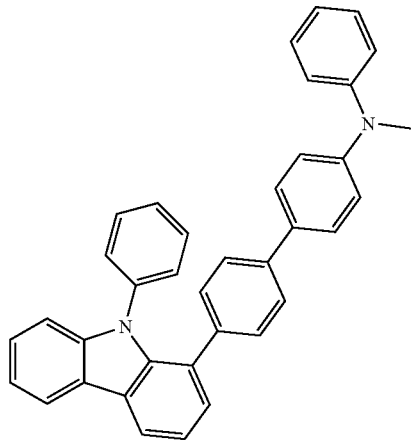
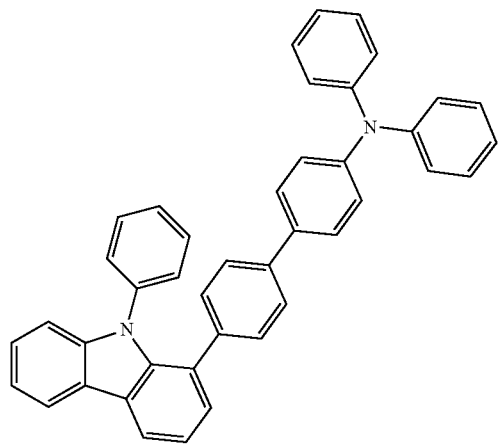
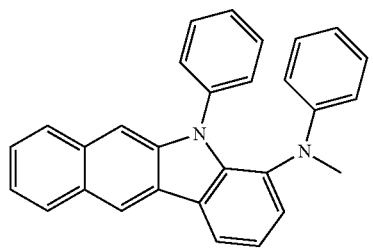
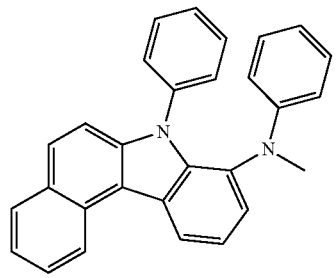
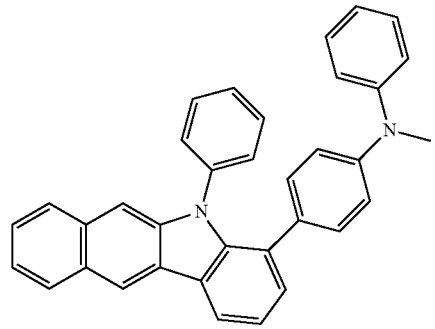
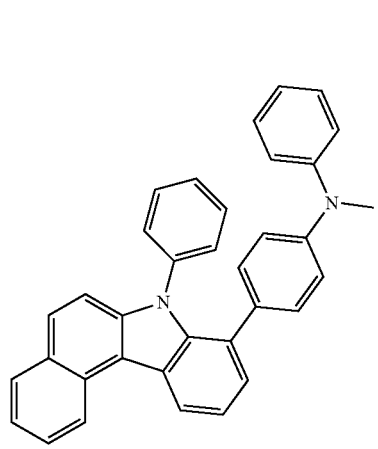
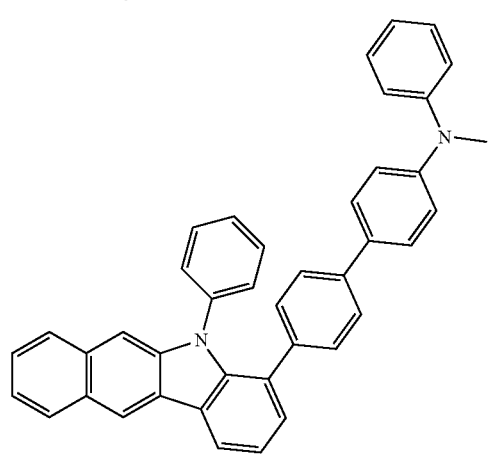

-continued
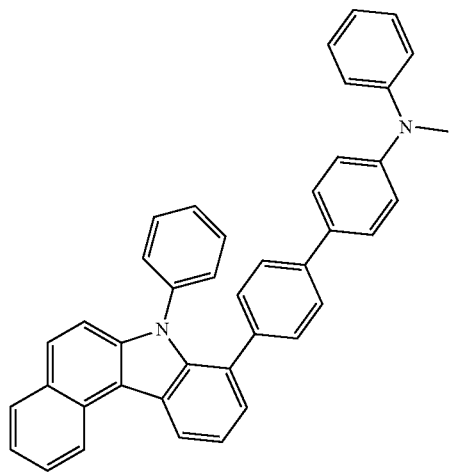
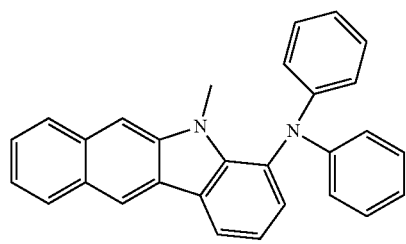
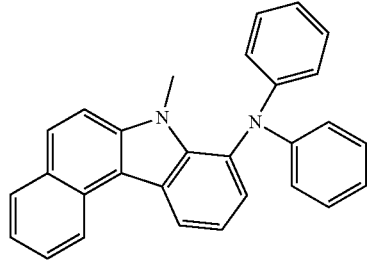
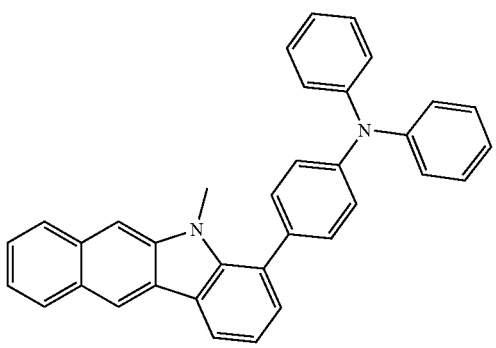
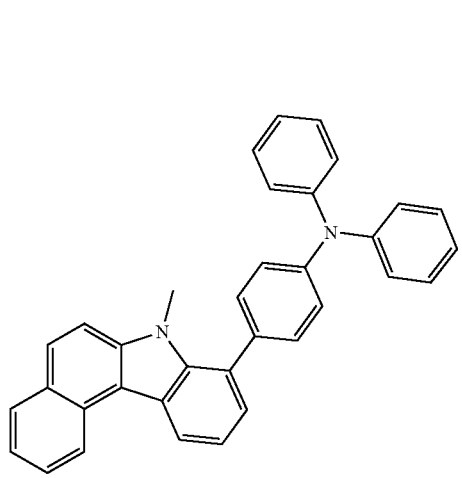
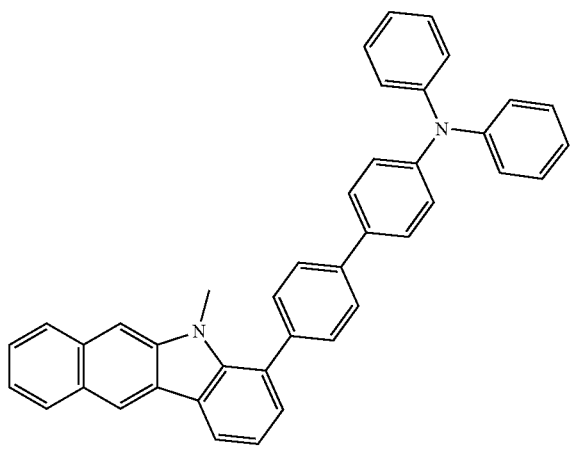

-continued
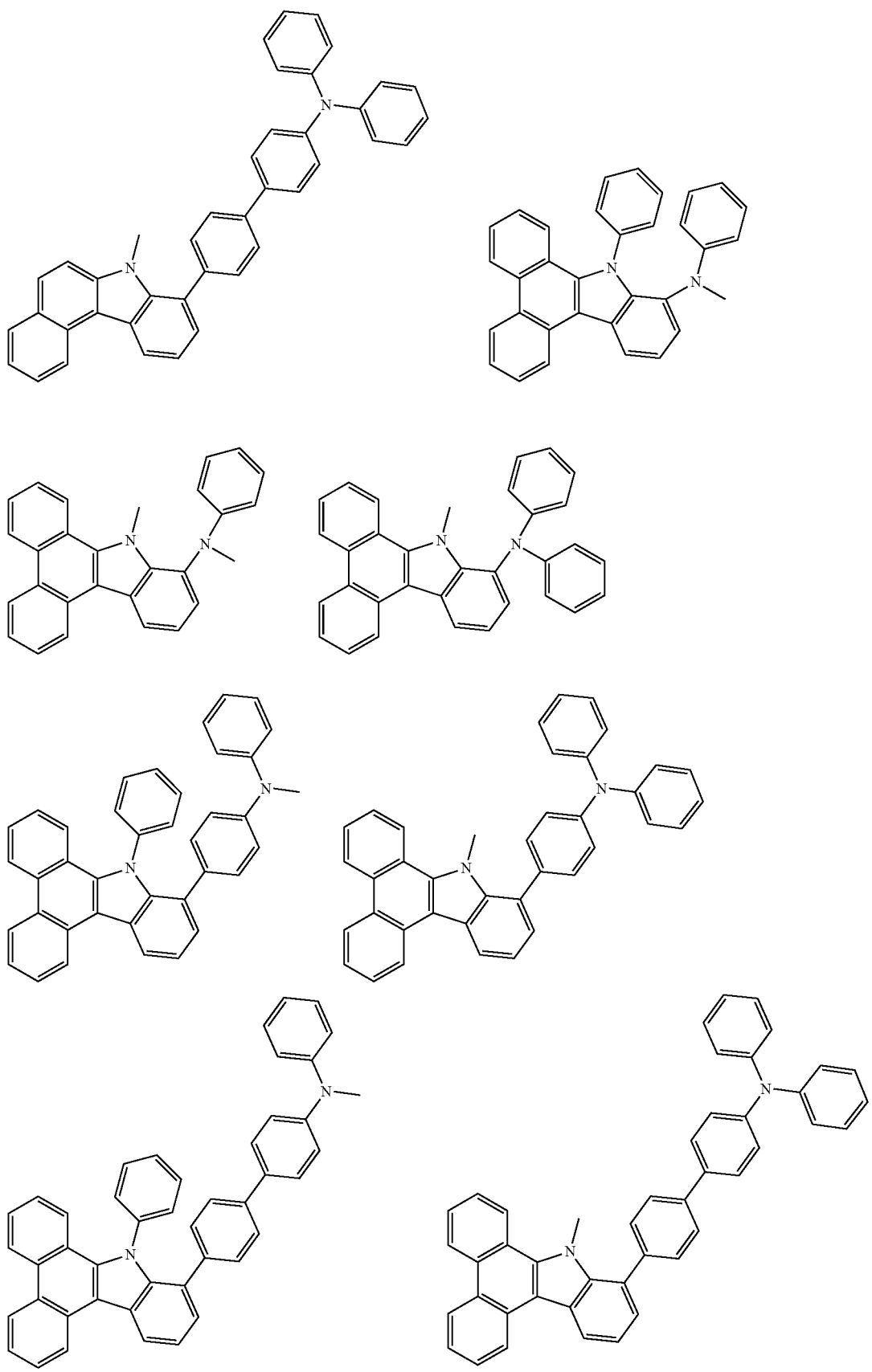

1761
-continued
1762
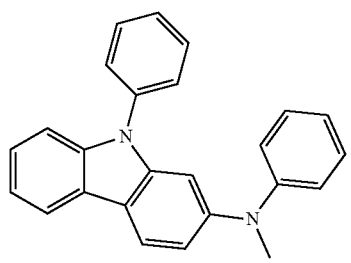
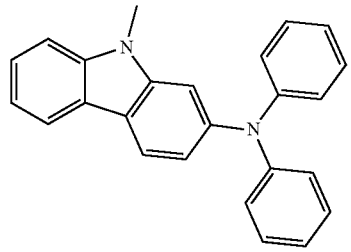
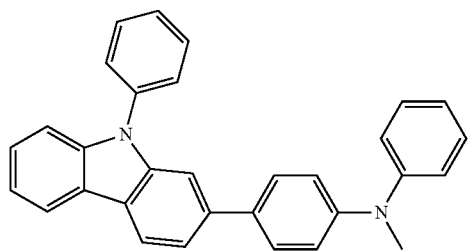
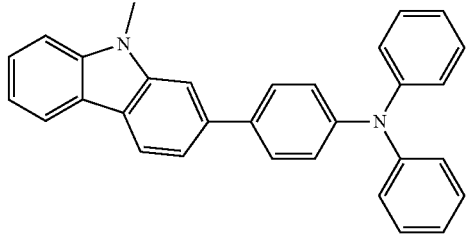
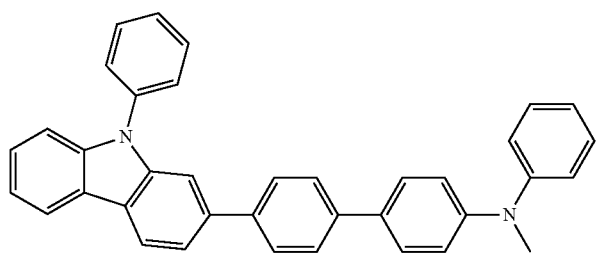
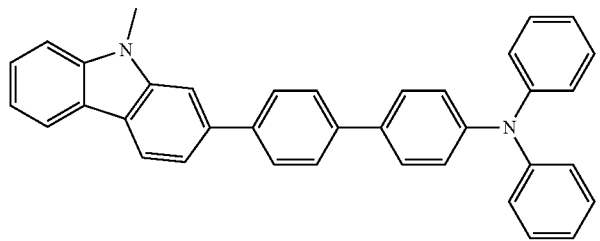
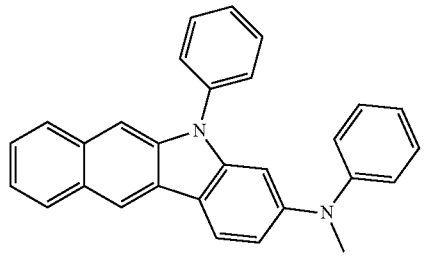
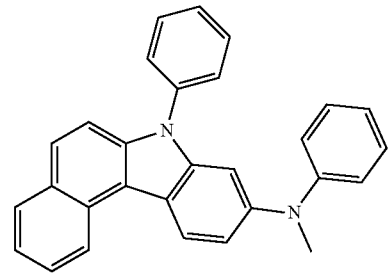
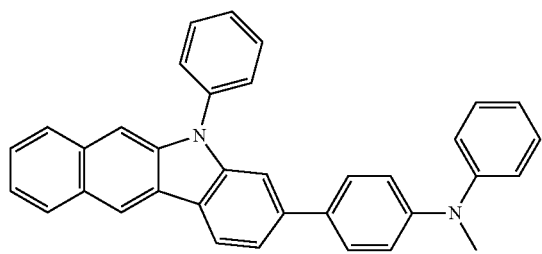
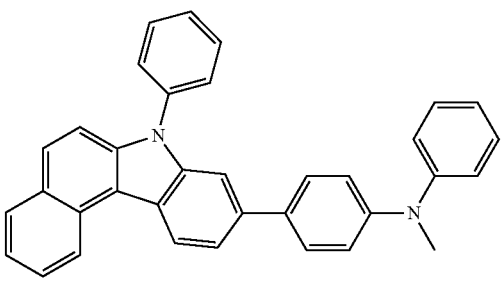

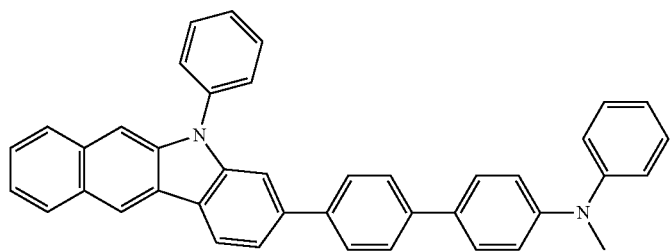
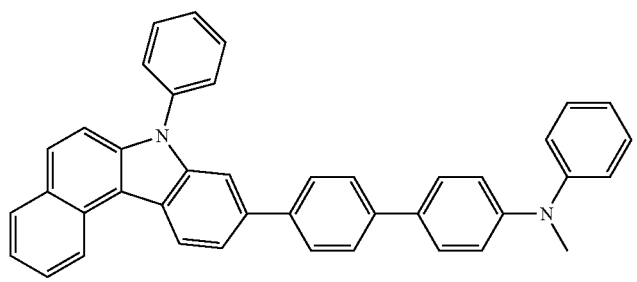
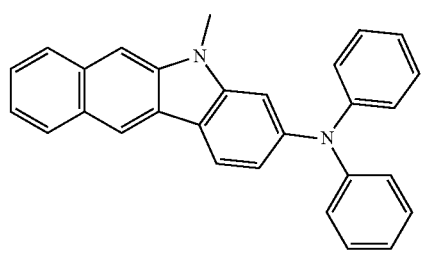
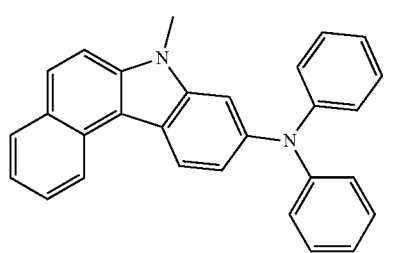
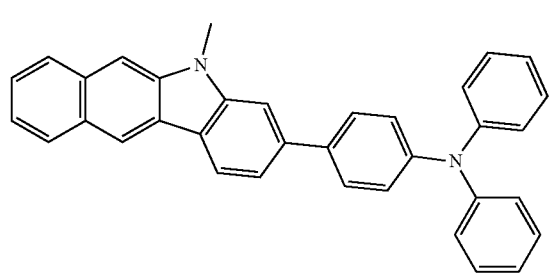
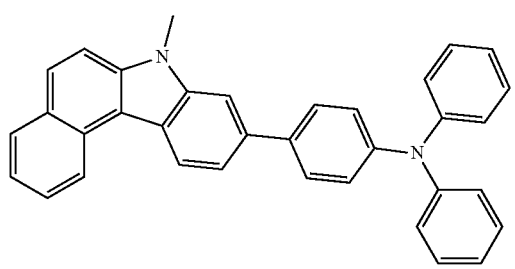
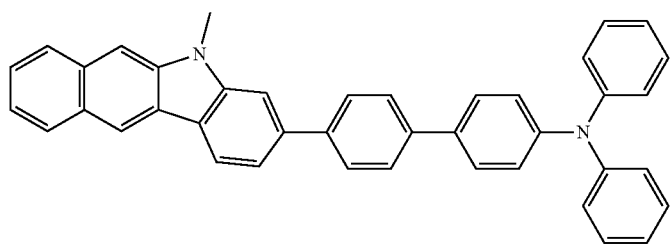
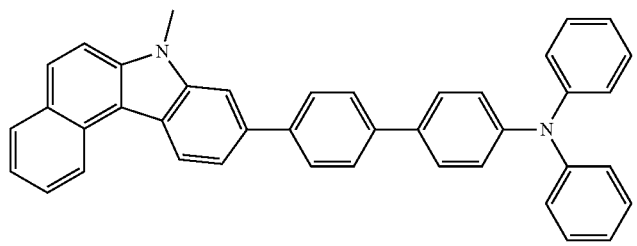

-continued
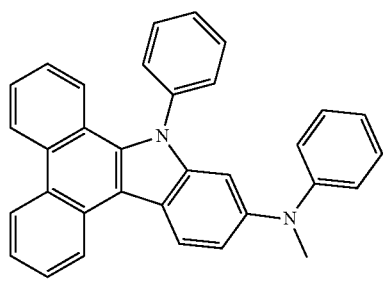
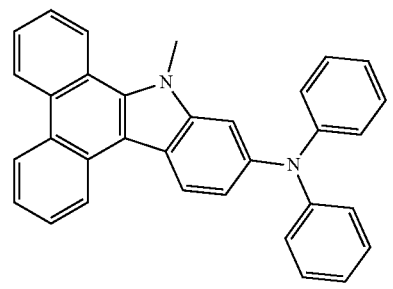
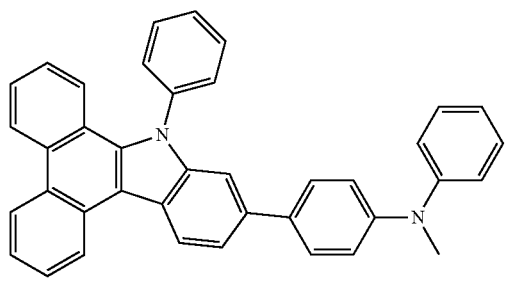
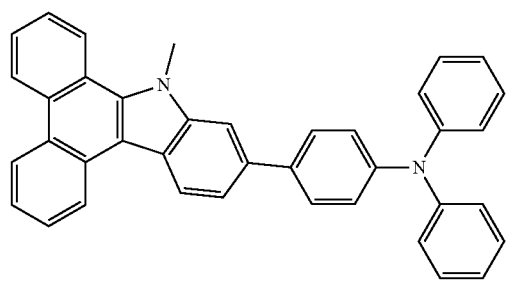
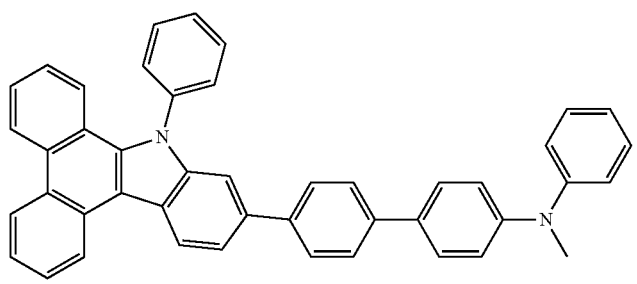
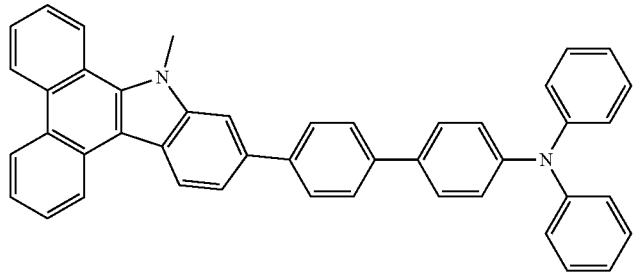
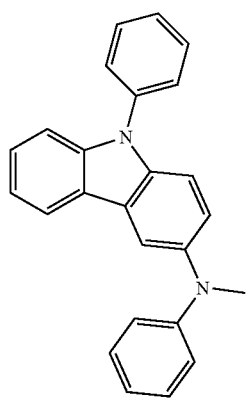
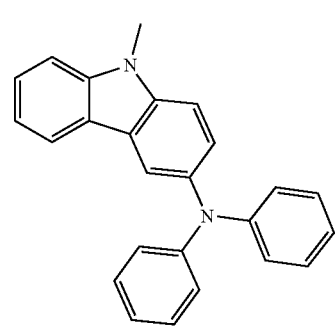
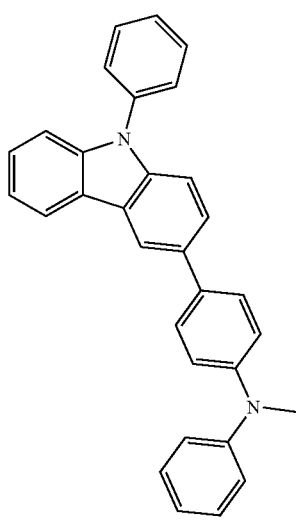

1767 1768
-continued
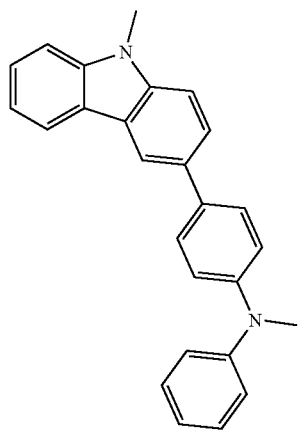
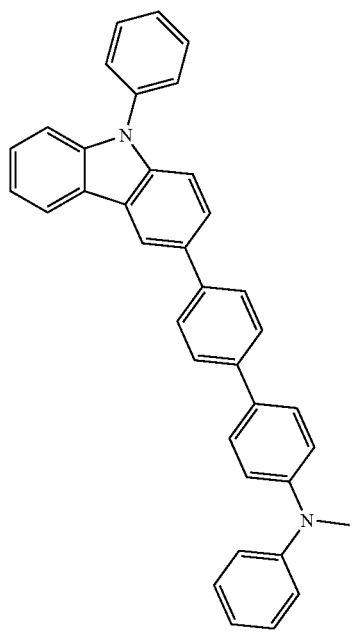
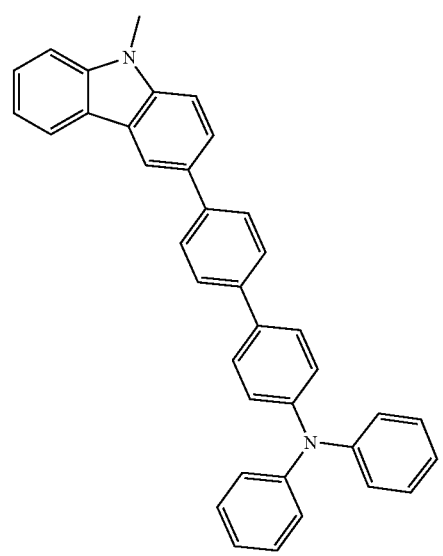
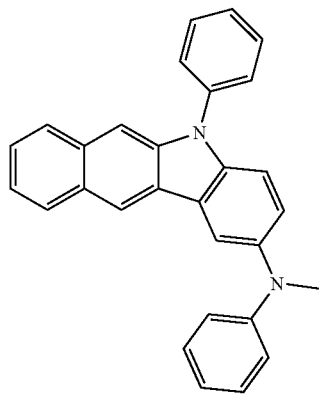
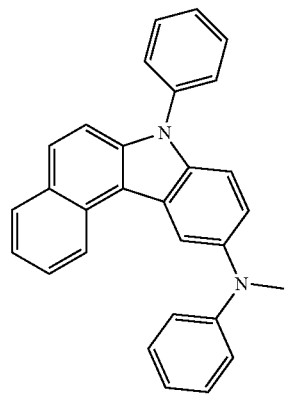
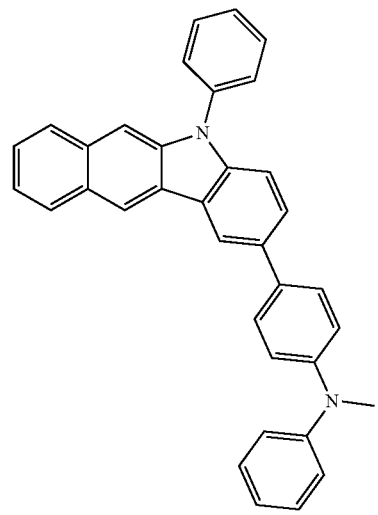

-continued
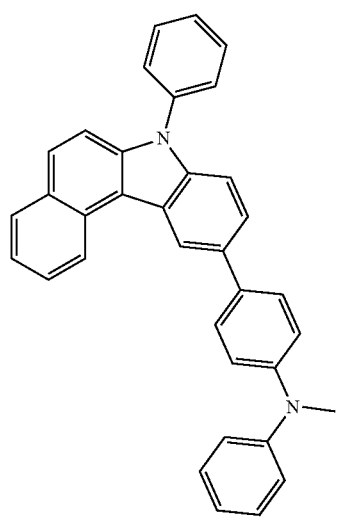
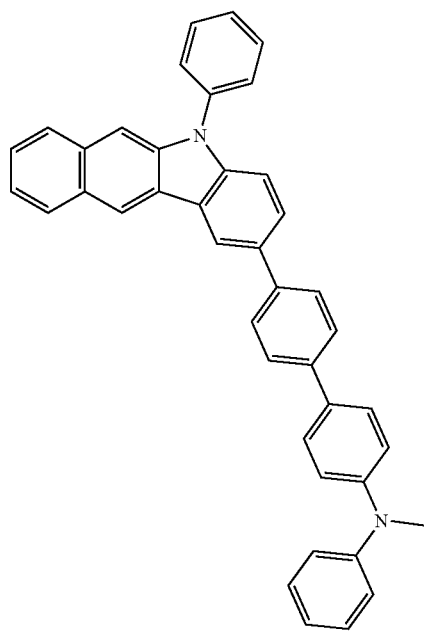
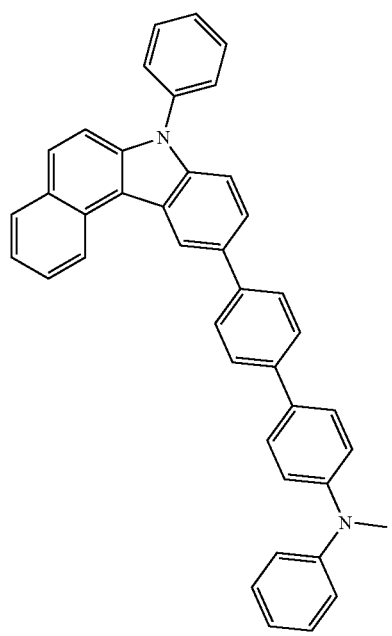
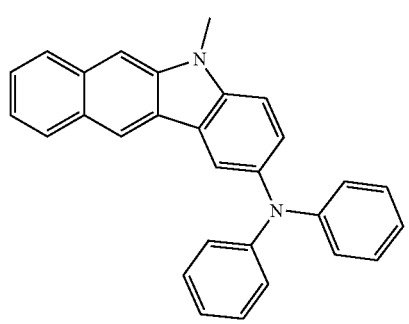
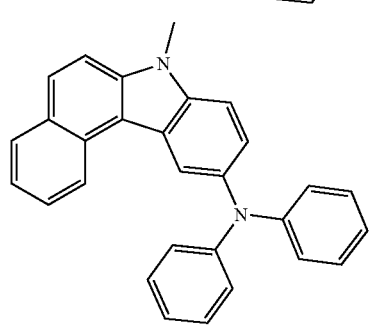
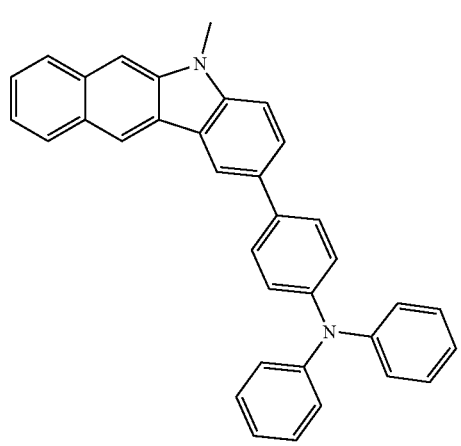

1771
1772
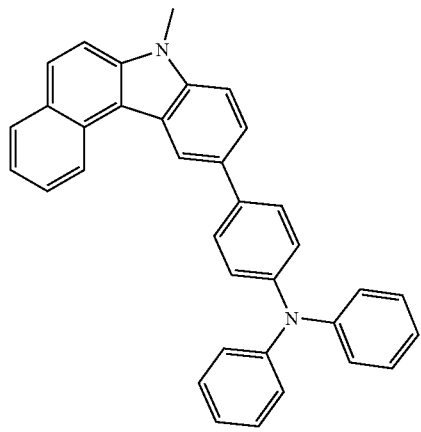
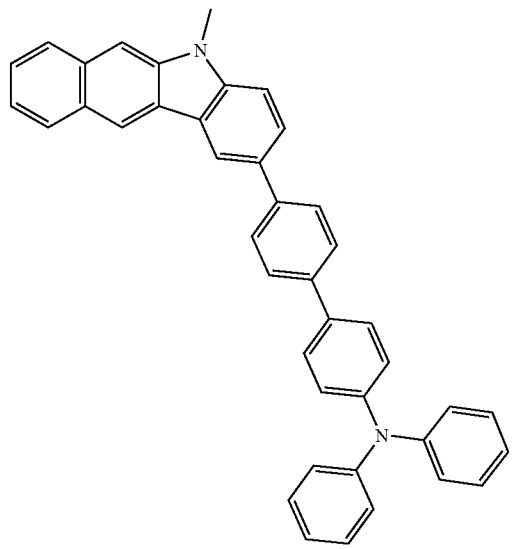
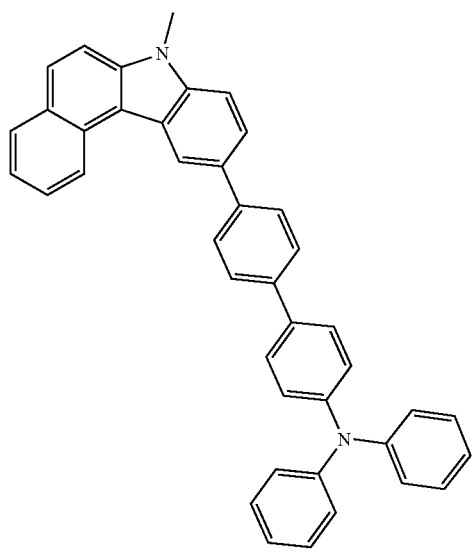
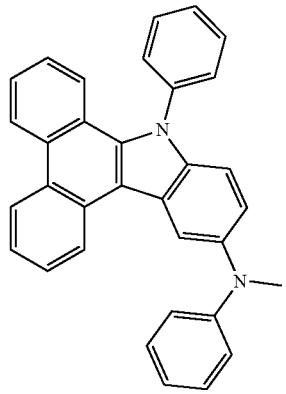
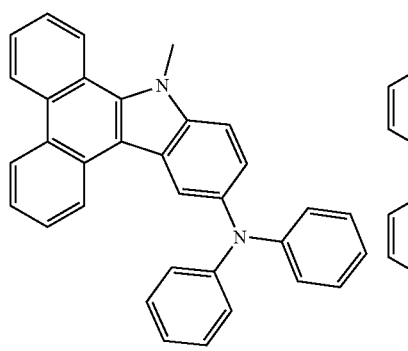
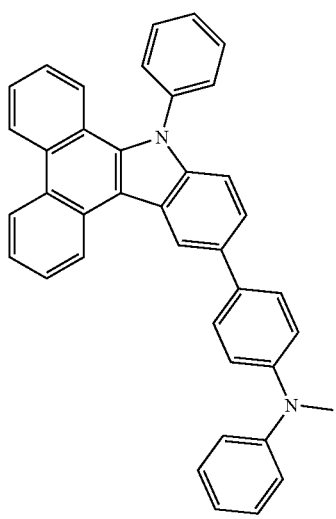
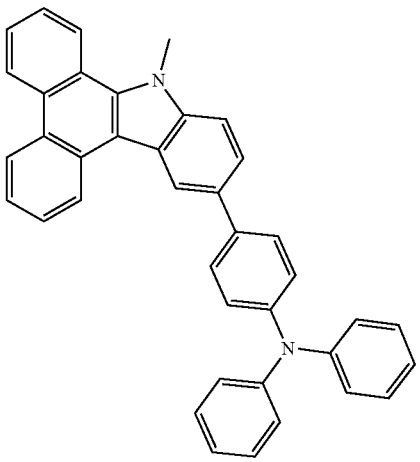

1773 1774
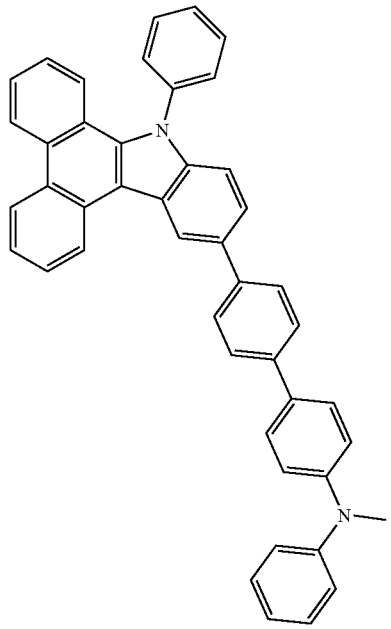
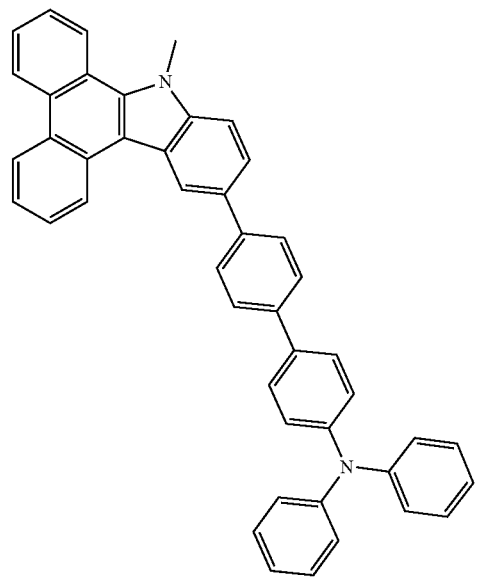
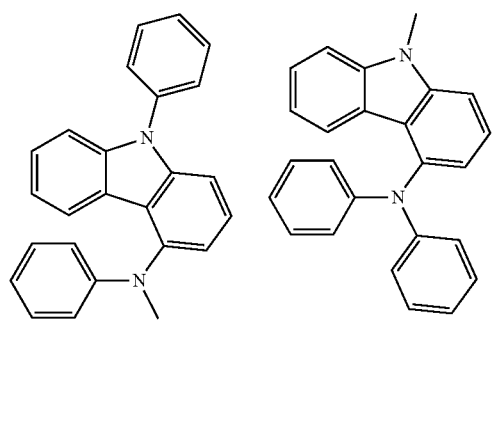
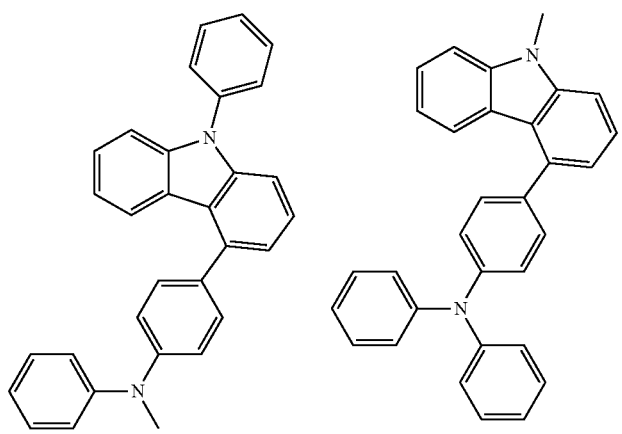
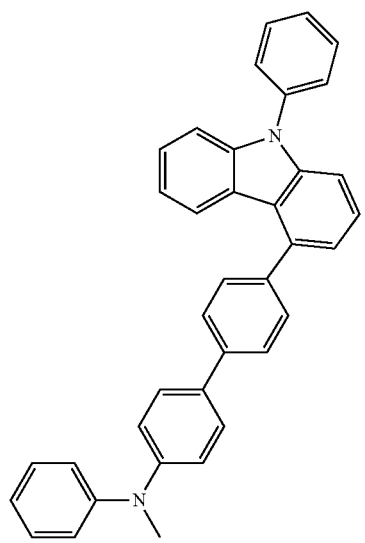
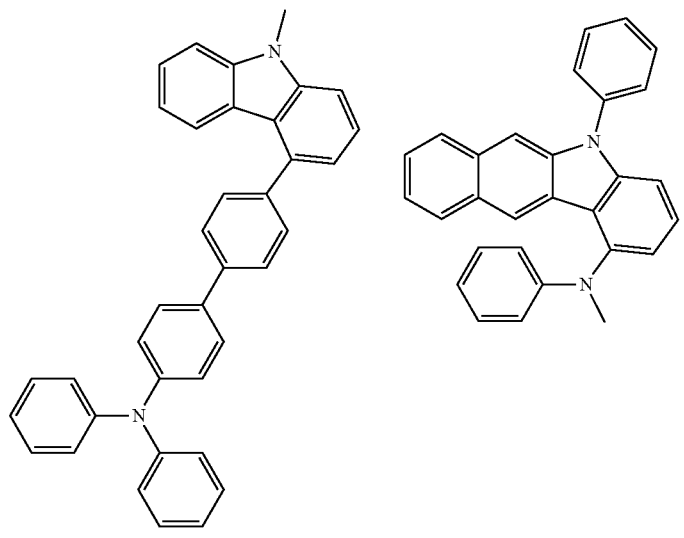

-continued
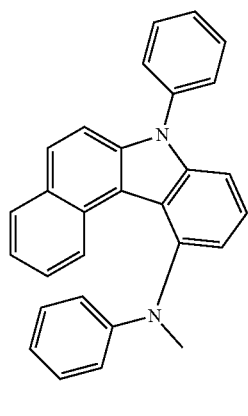 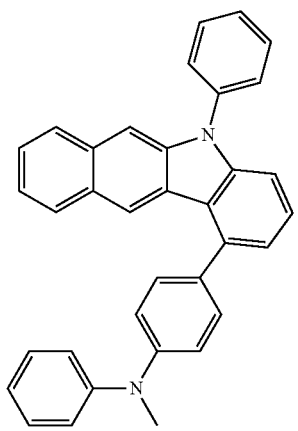 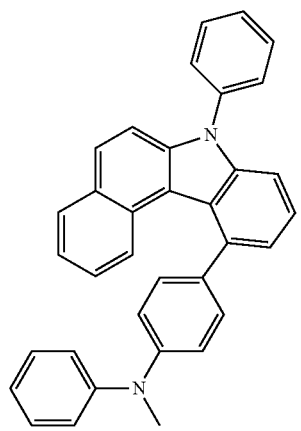
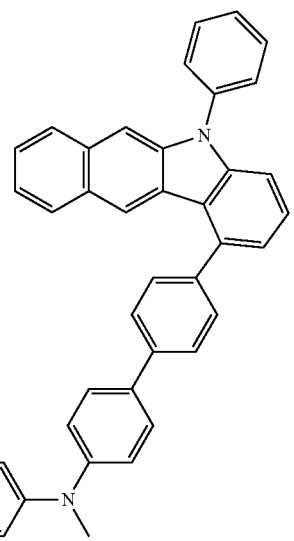 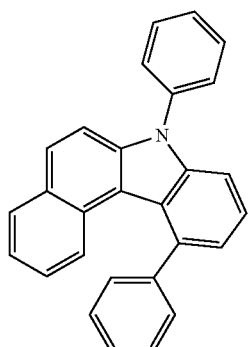 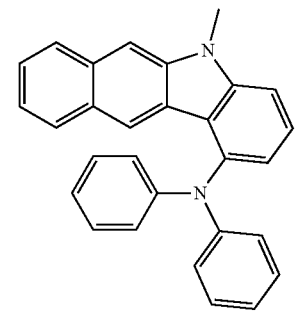
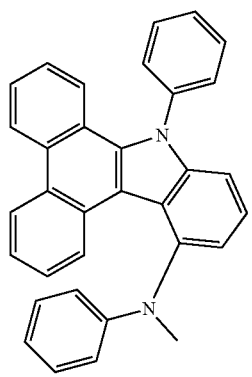 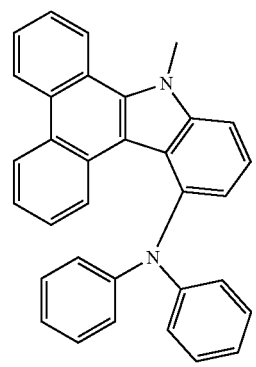 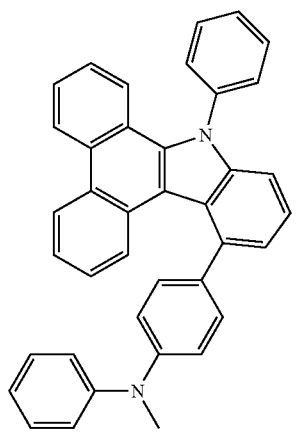 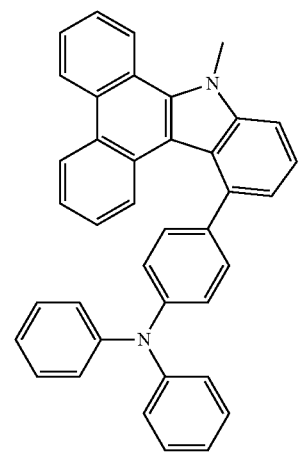

1777                                    1778

-continued

-continued
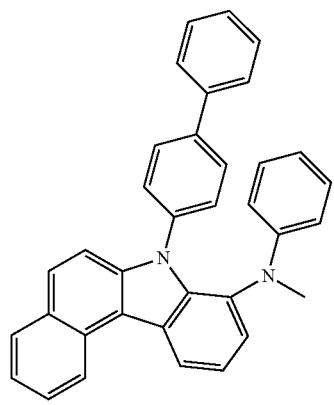
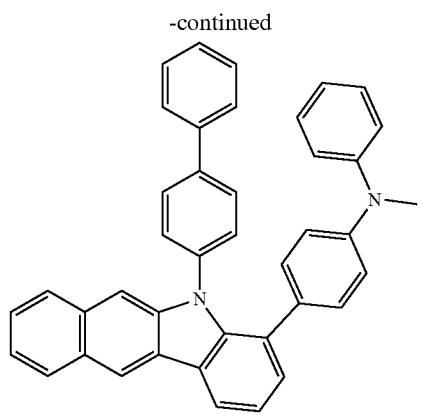
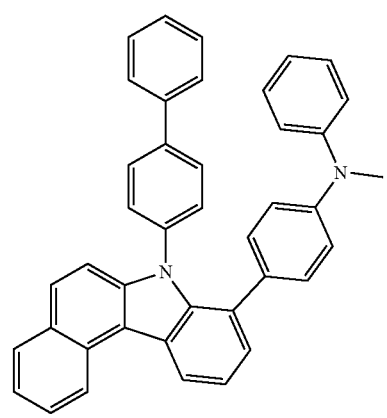
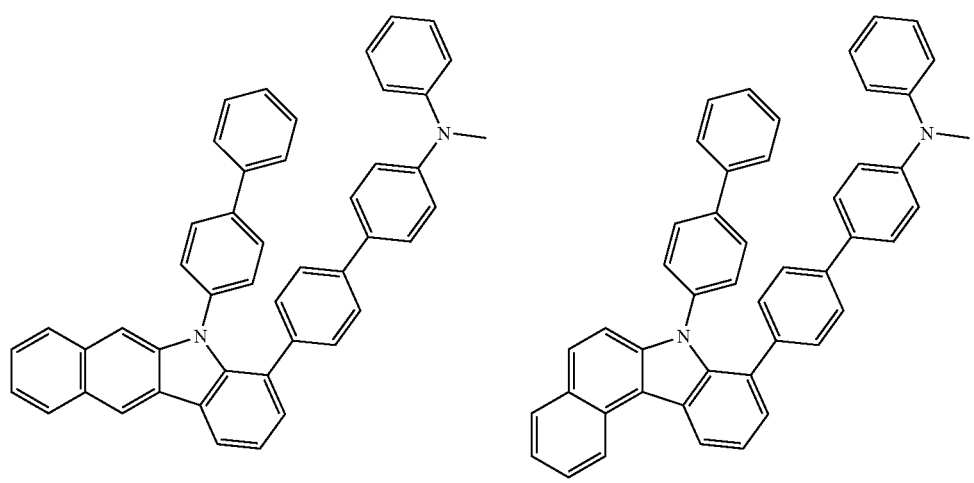
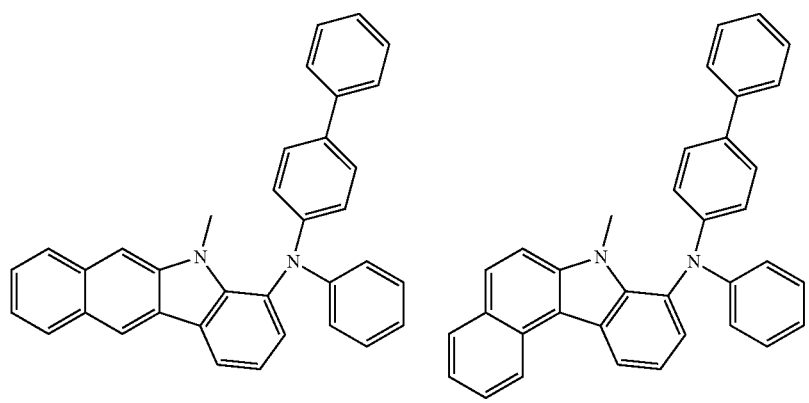

1781 1782
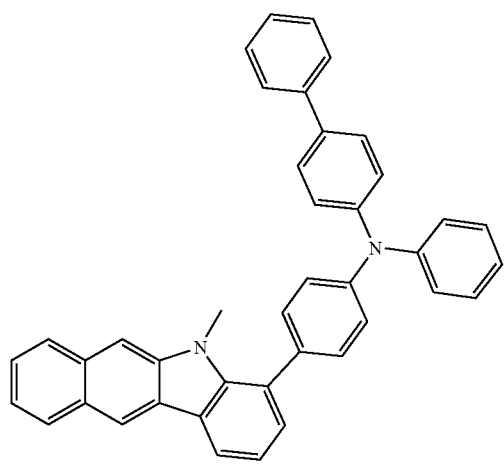 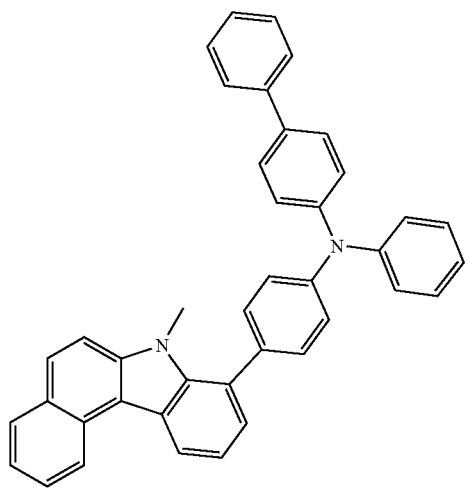
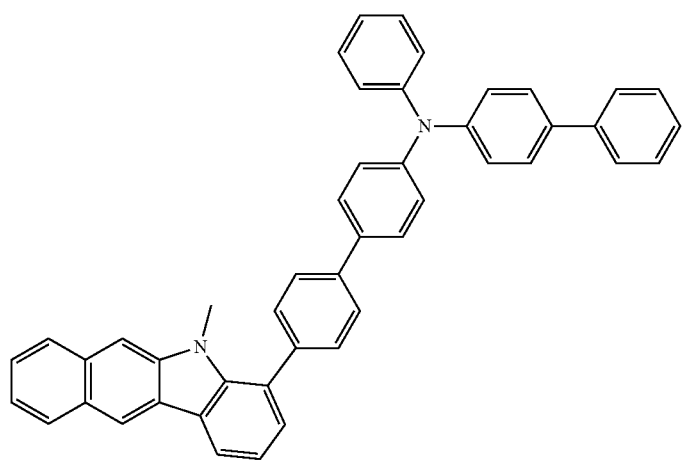
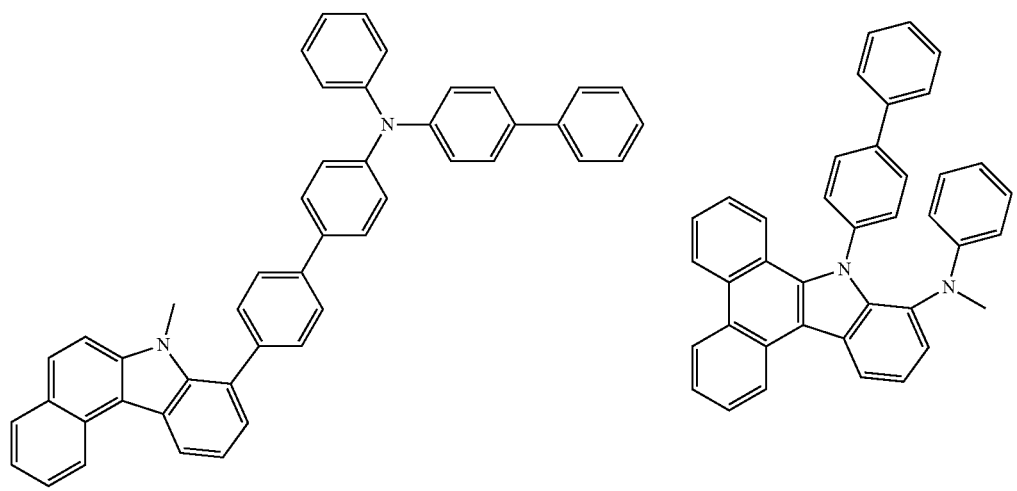

1783
-continued
1784
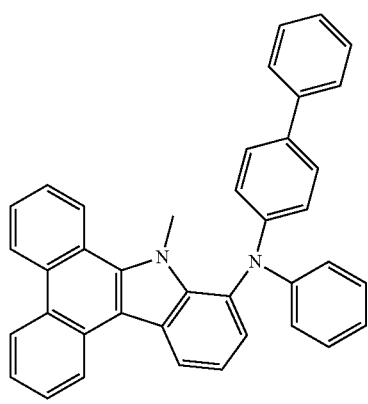
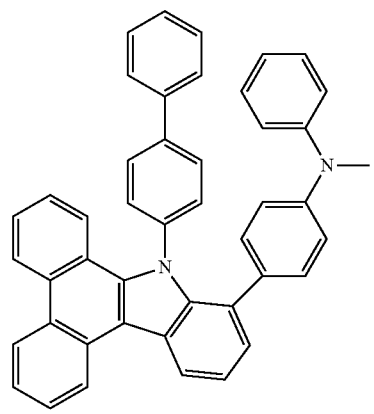
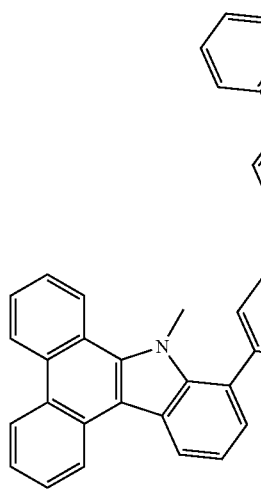
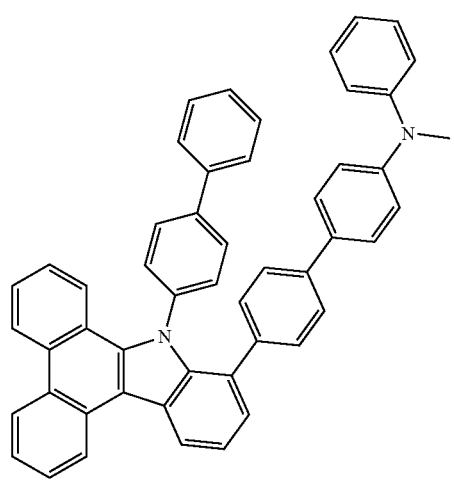
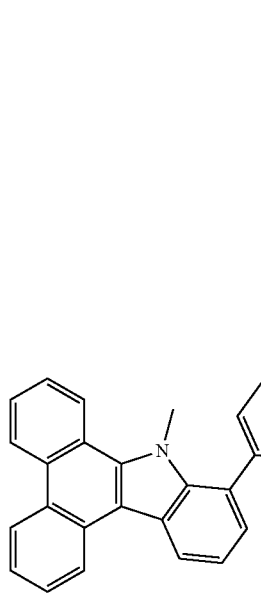
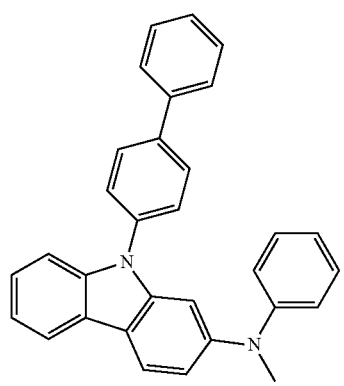

1785
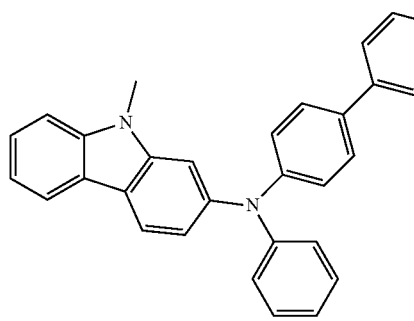
1786
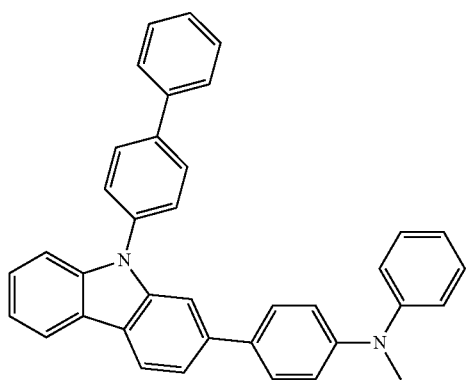
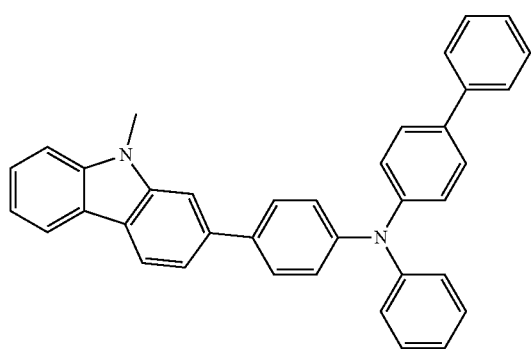
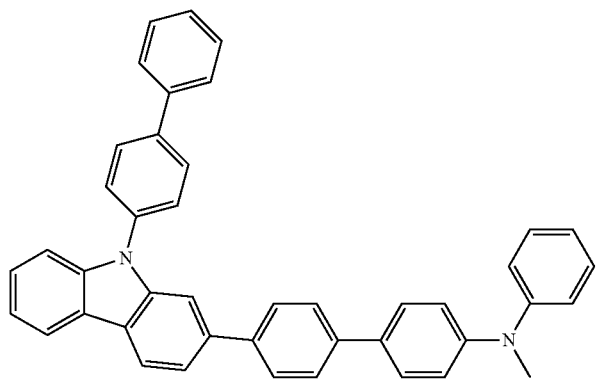
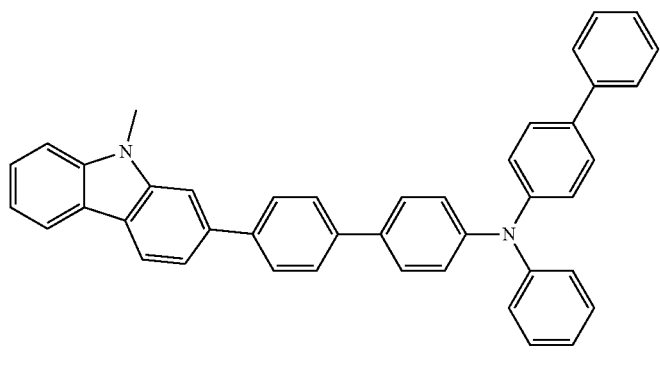
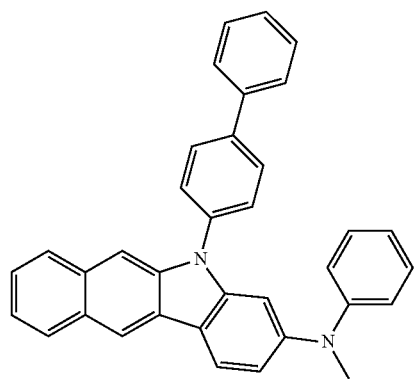

-continued
| 1787 | 1788 |
|---|---|
| 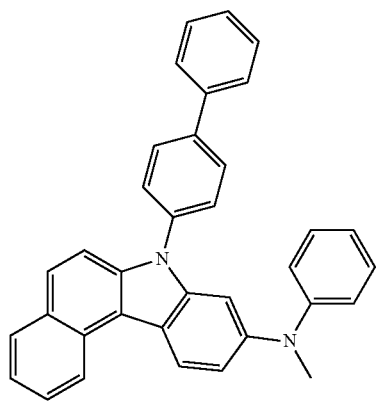 | 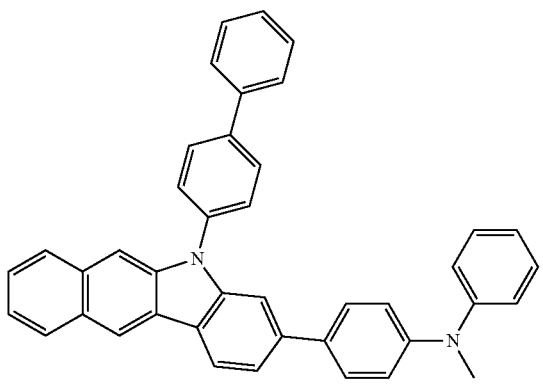 |浙
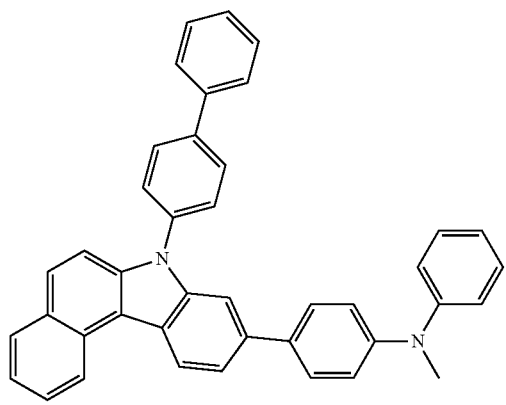
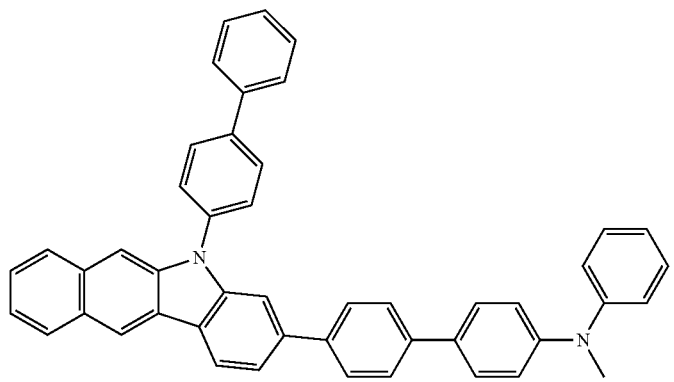
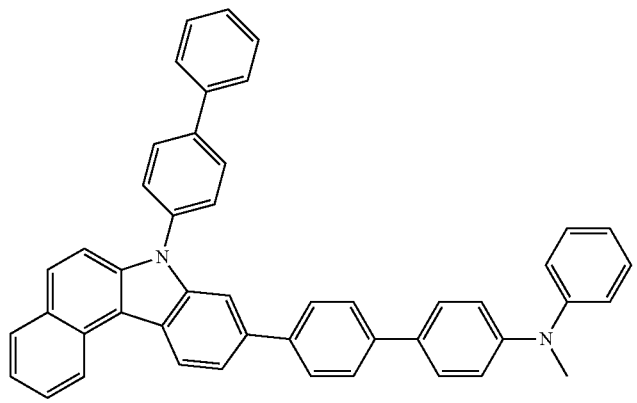
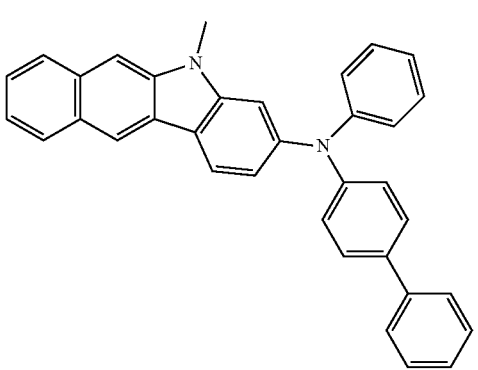

| 1789 | 1790 |
|---|---|
| 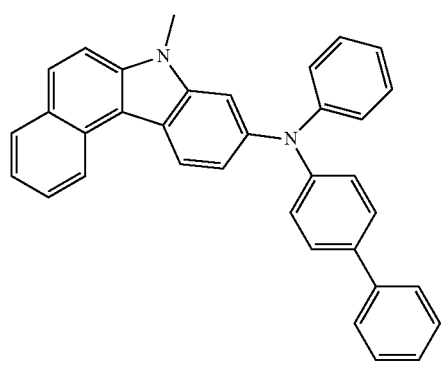 | 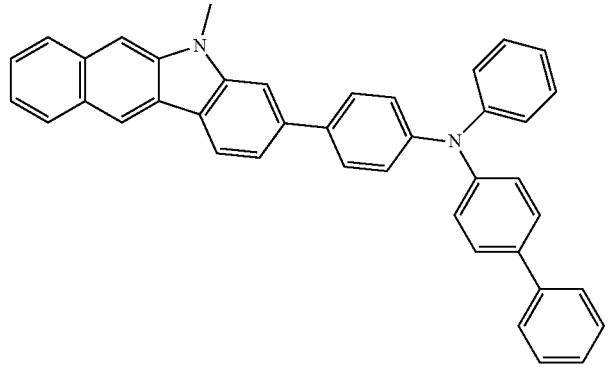 |
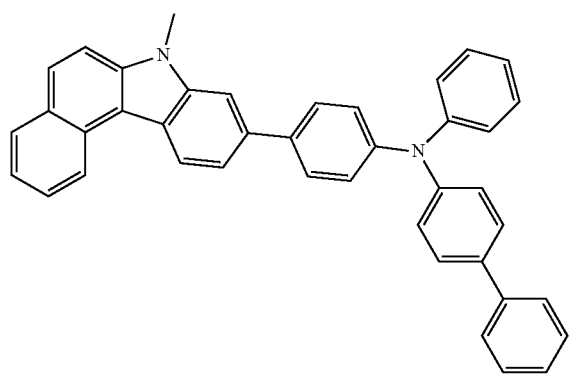
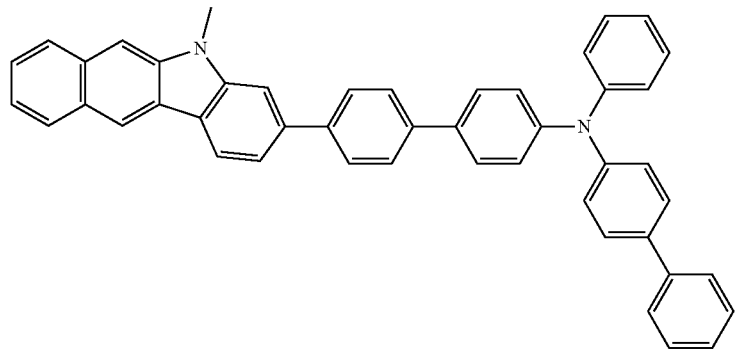
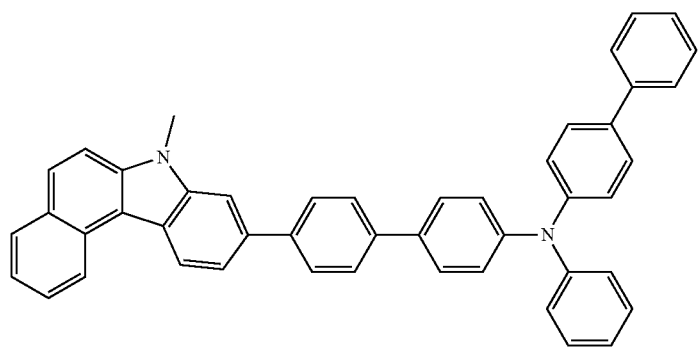

-continued
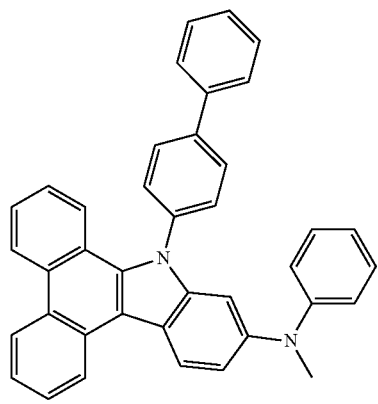
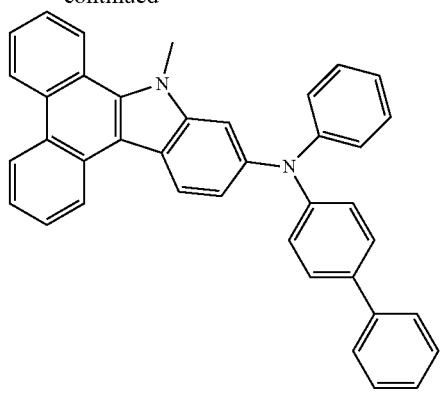
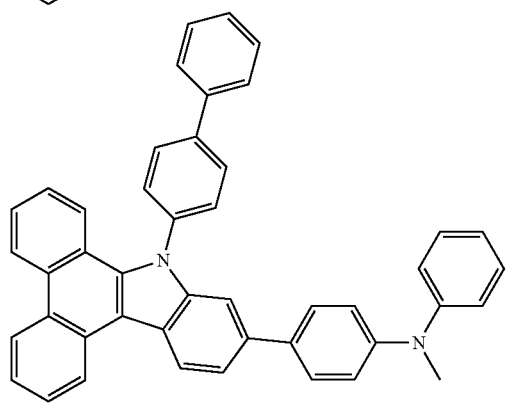
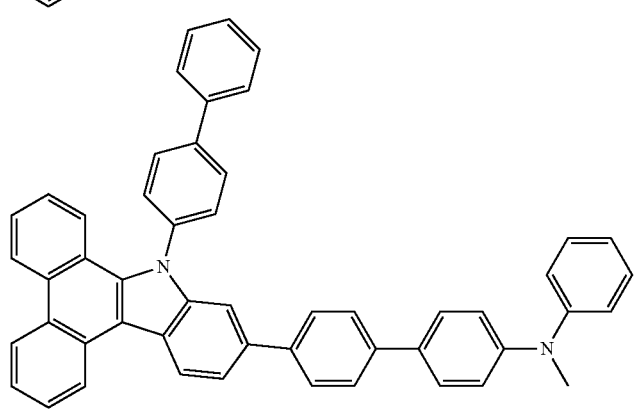
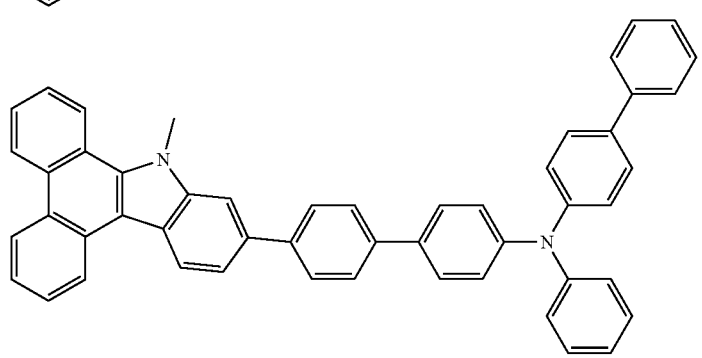
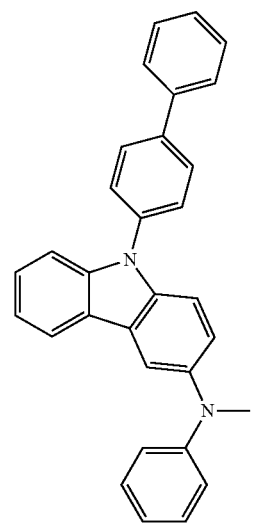

-continued
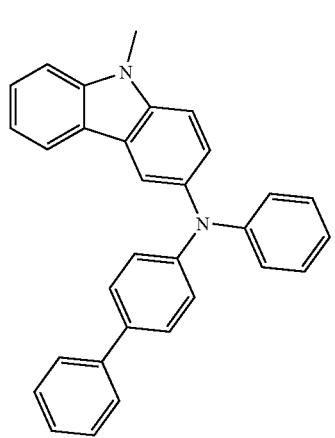
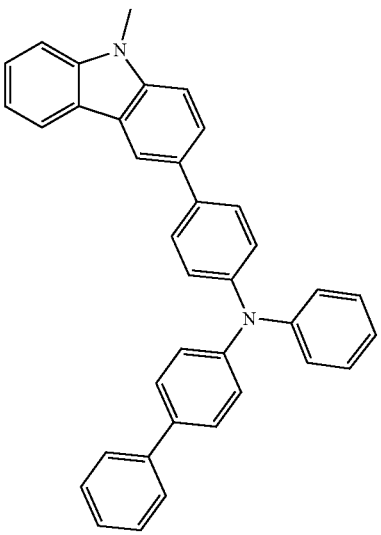
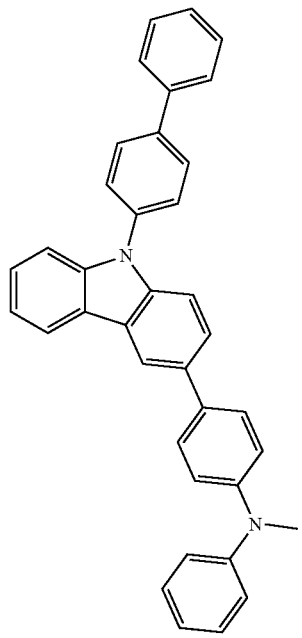
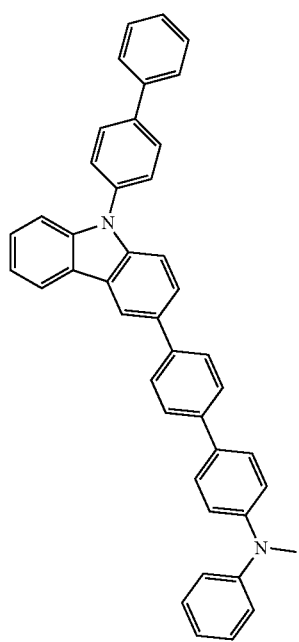
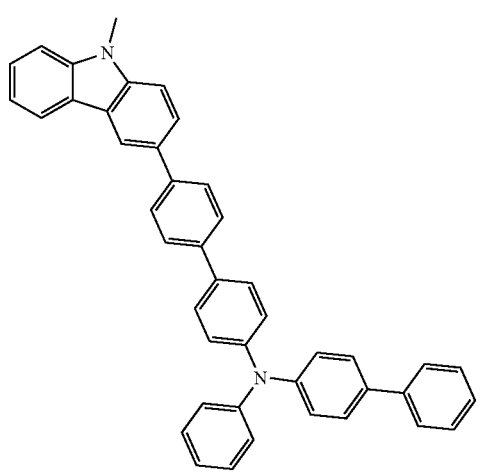
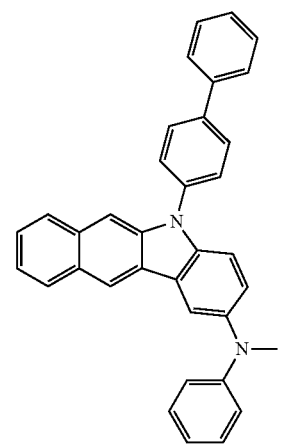

1795
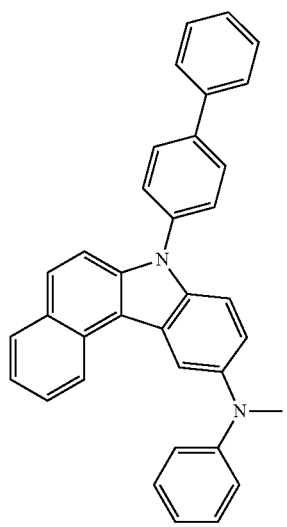
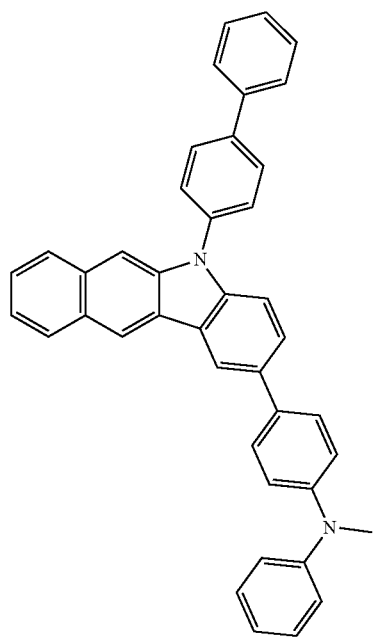
1796
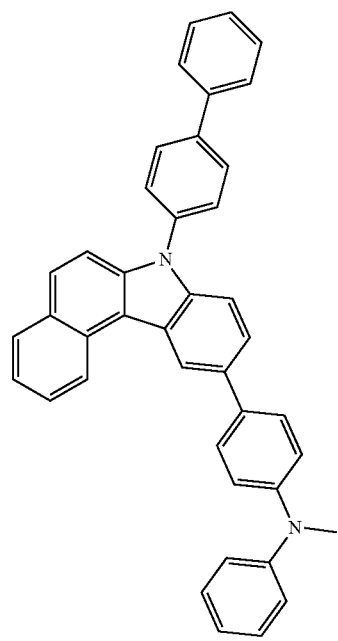
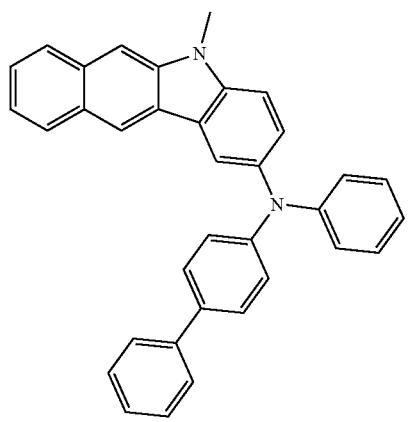
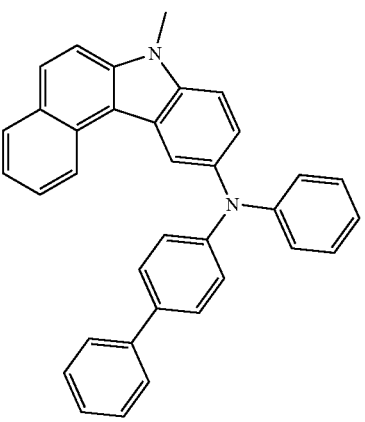
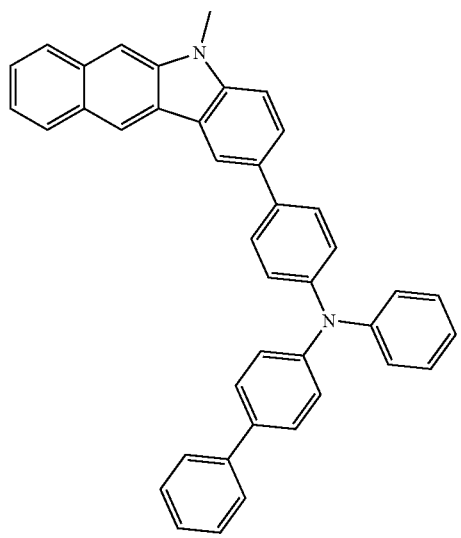
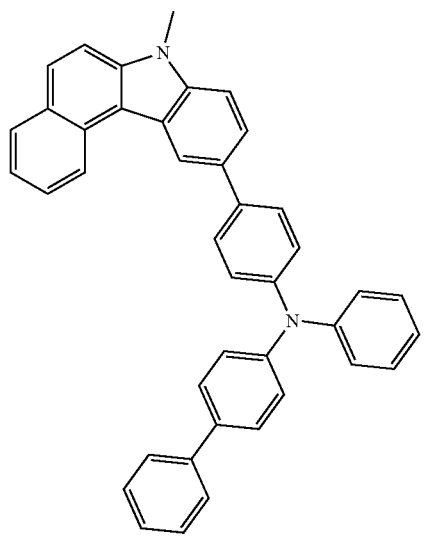

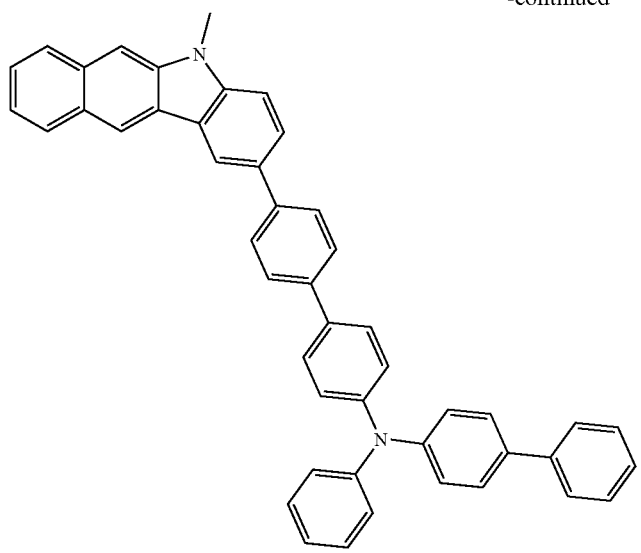
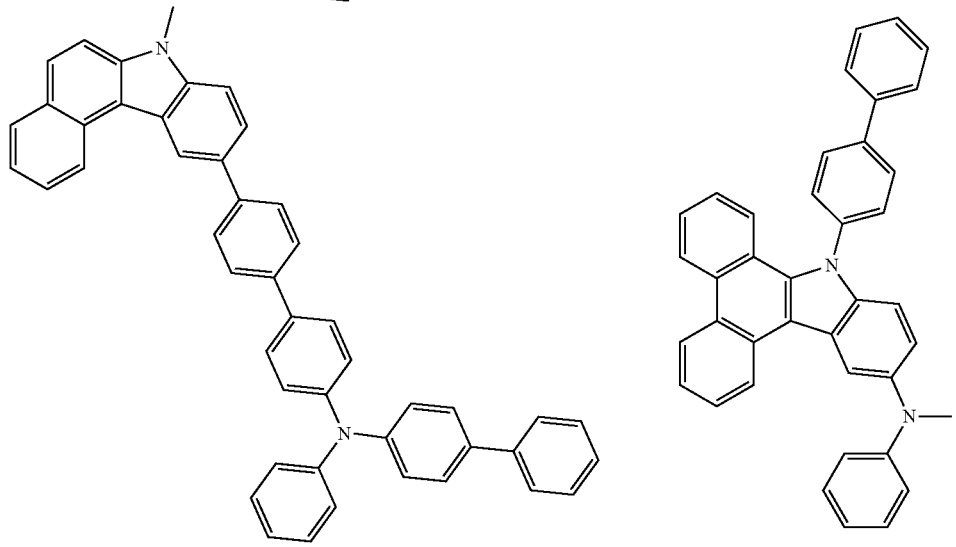
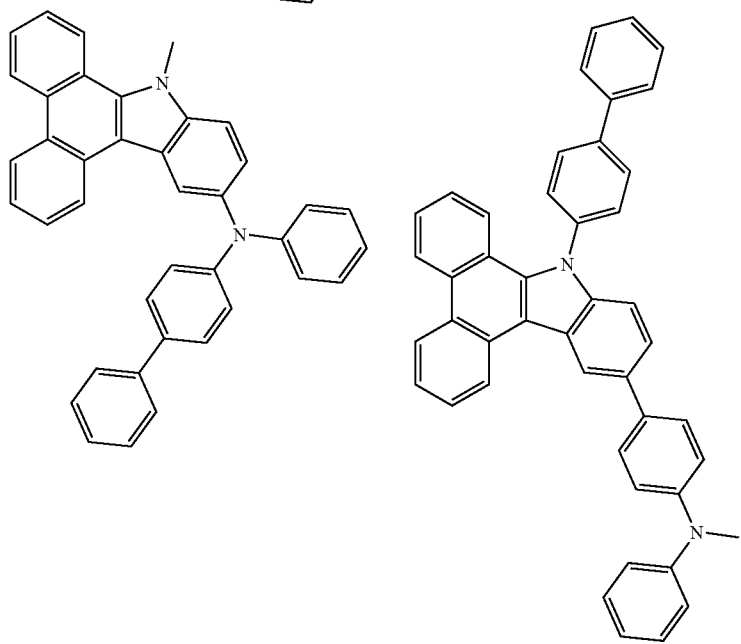

1799　　　1800
-continued
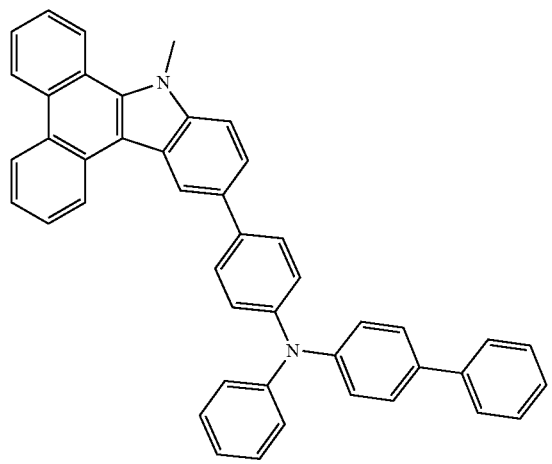
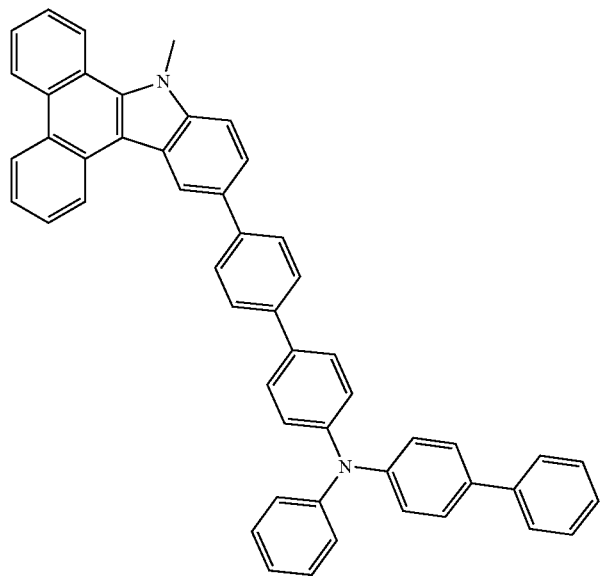
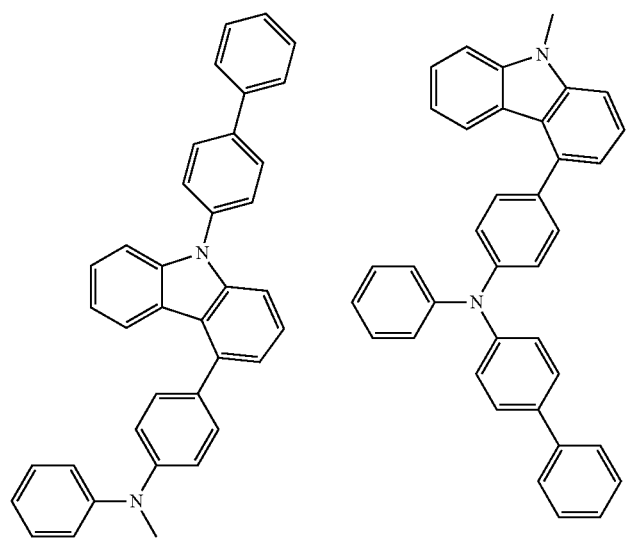
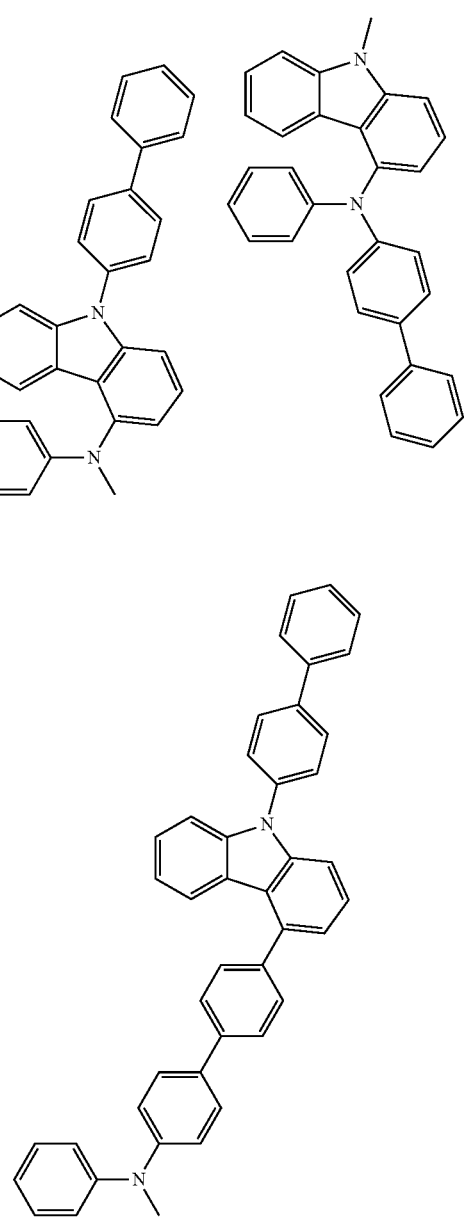

1801
1802
-continued
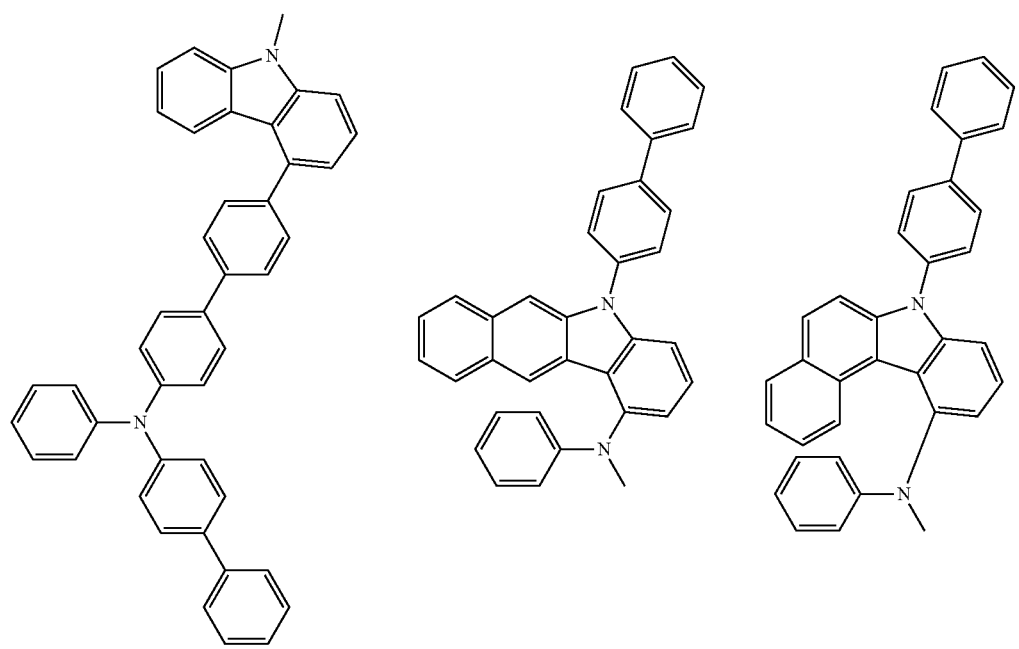
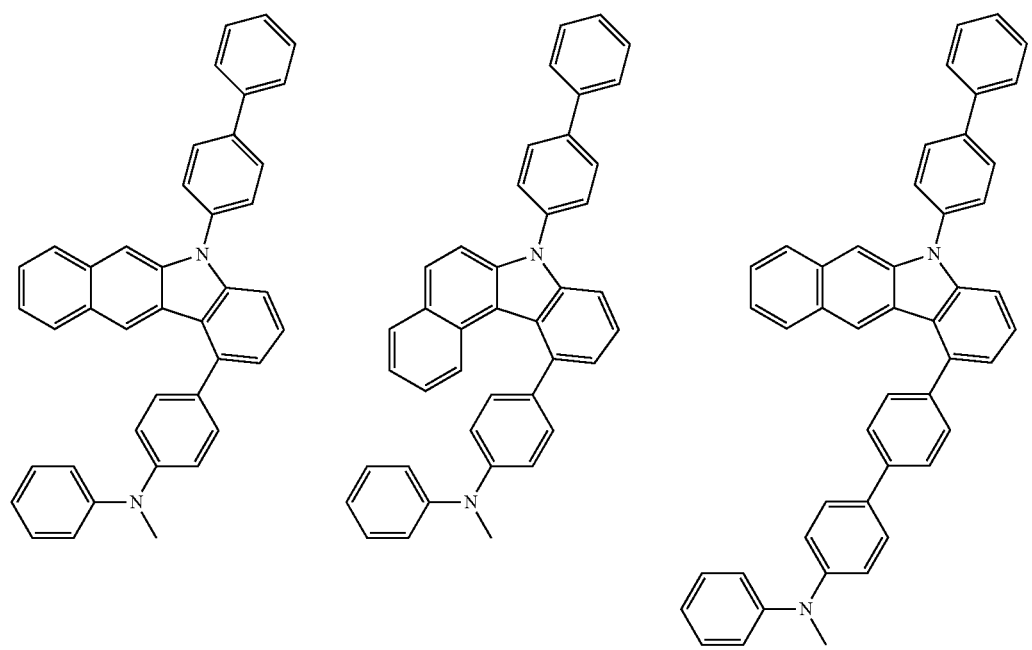

1803 1804
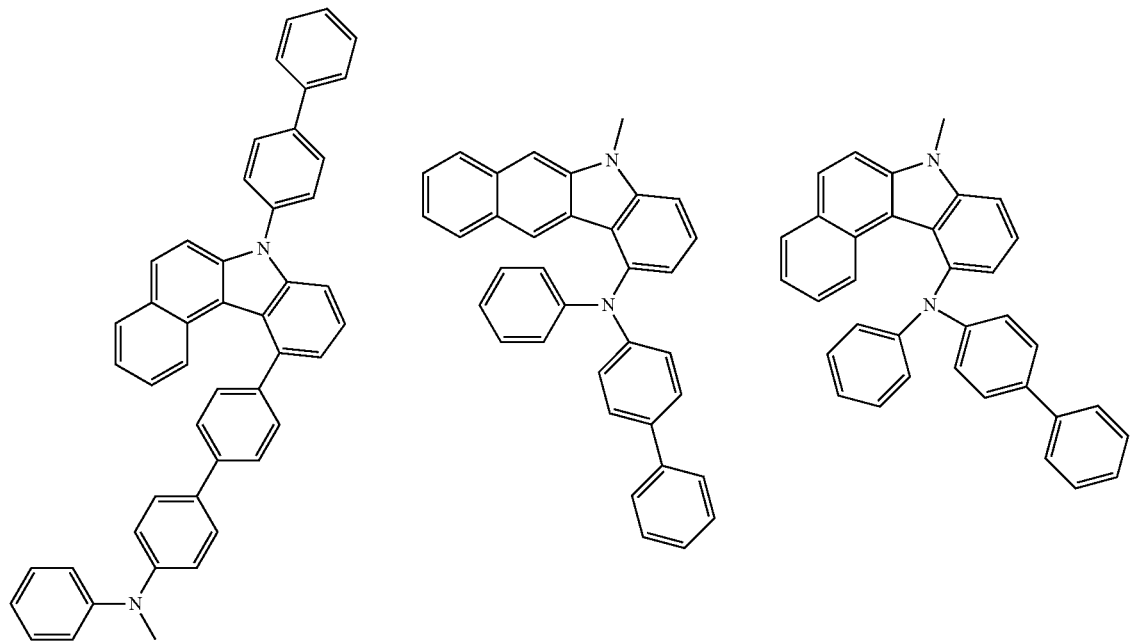
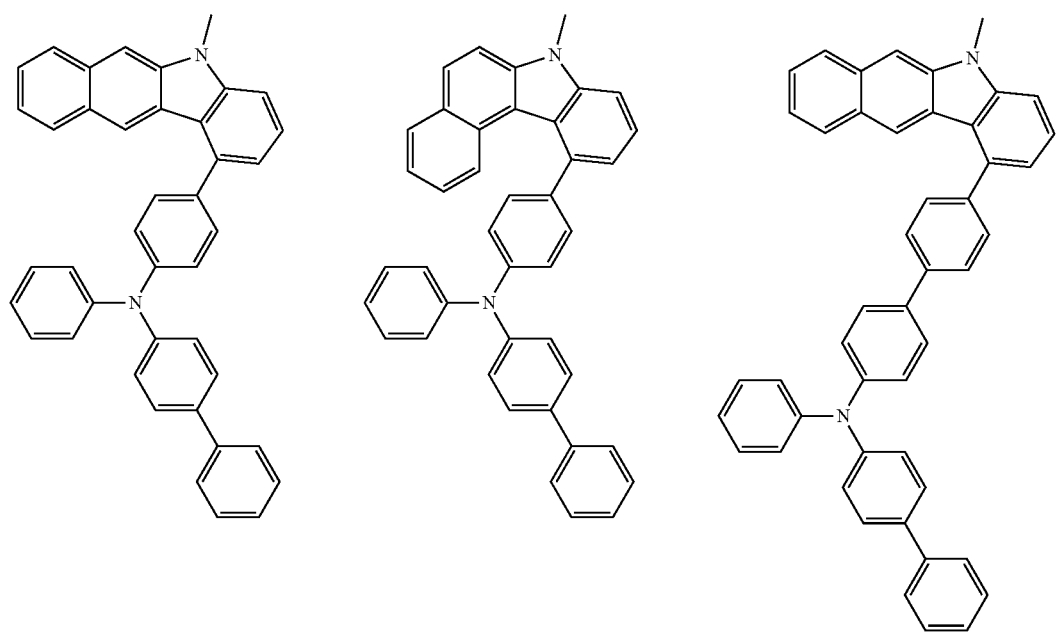

1805 1806
-continued
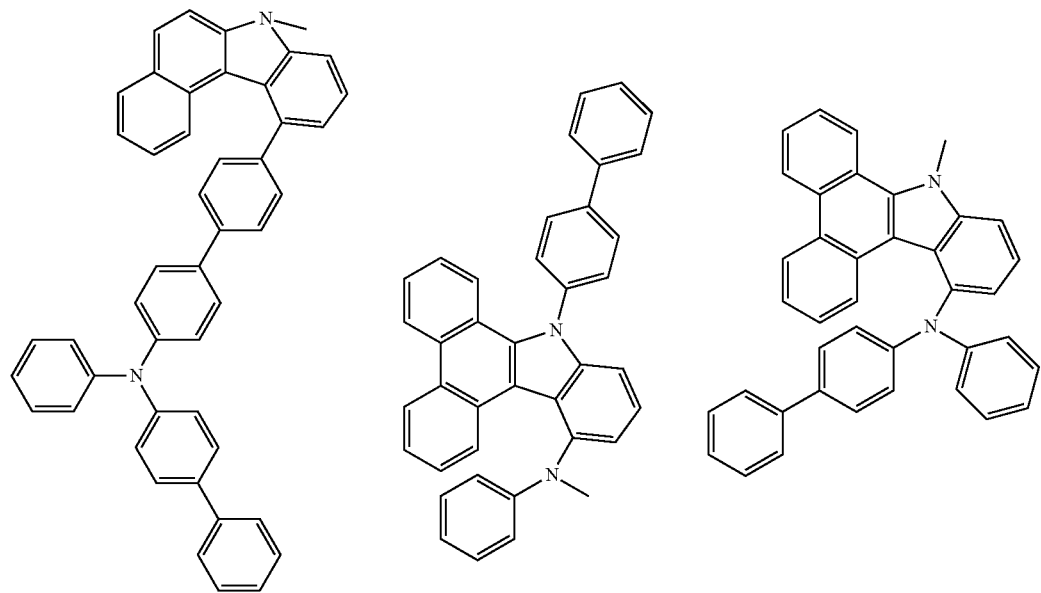
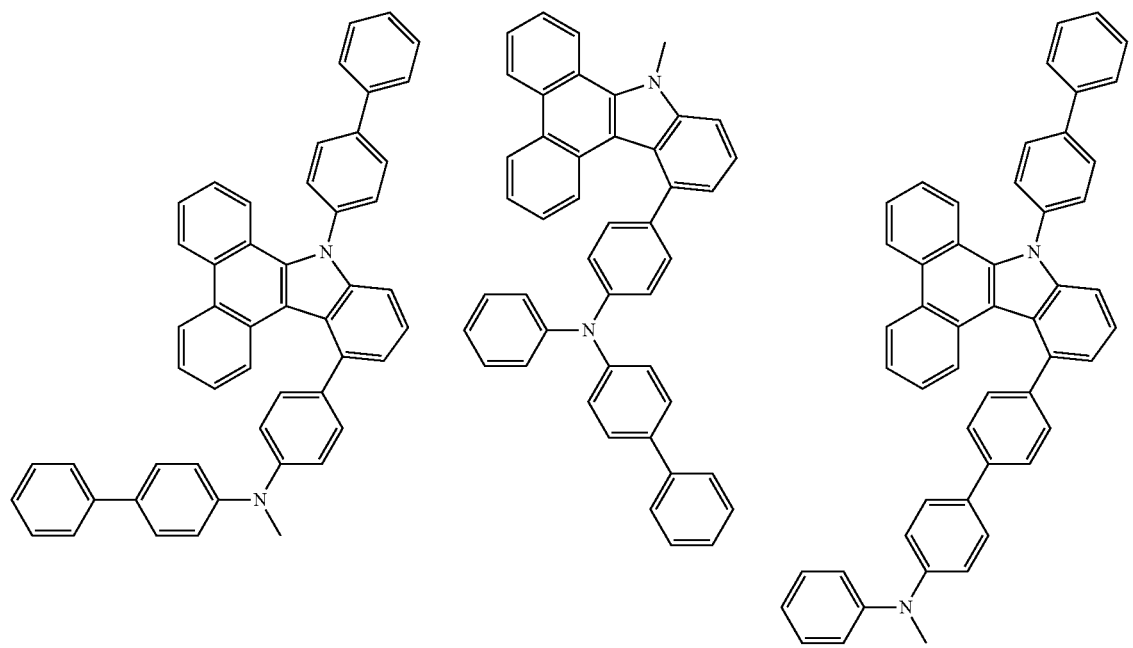

1807 1808
-continued
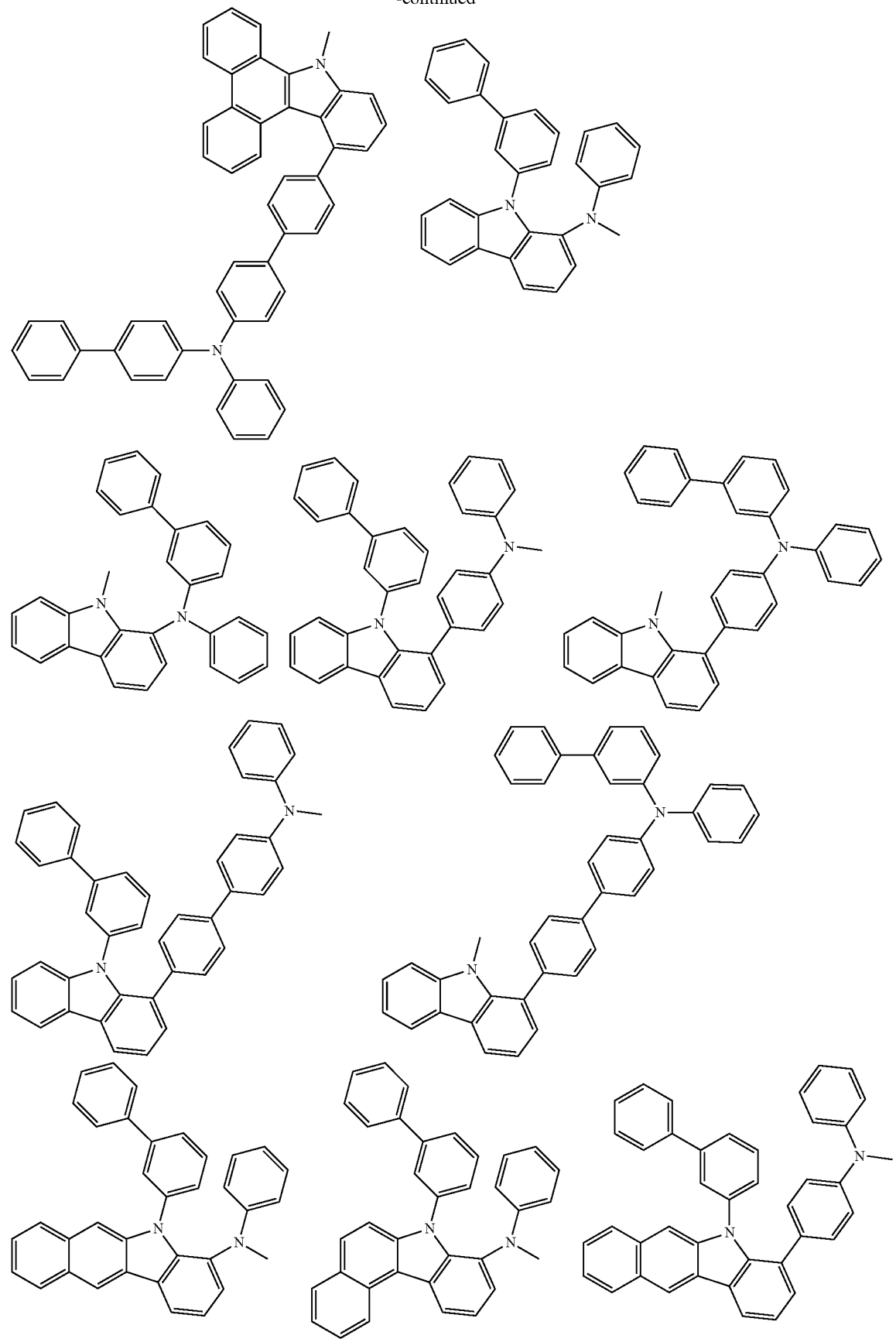

1809                                                    1810
-continued
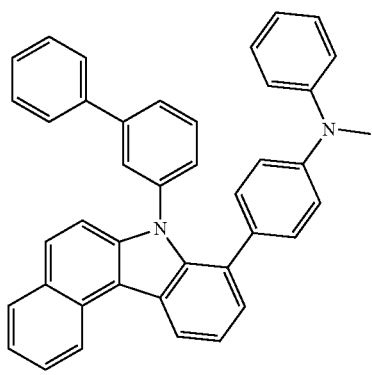
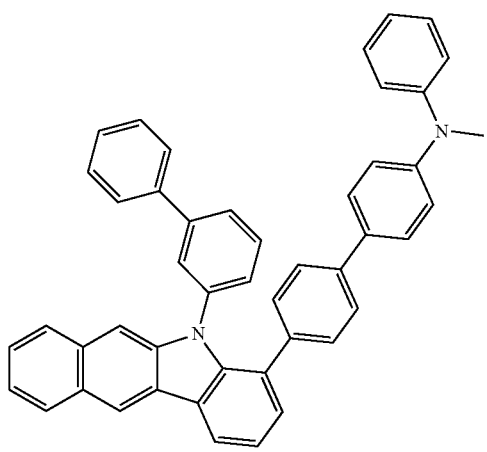
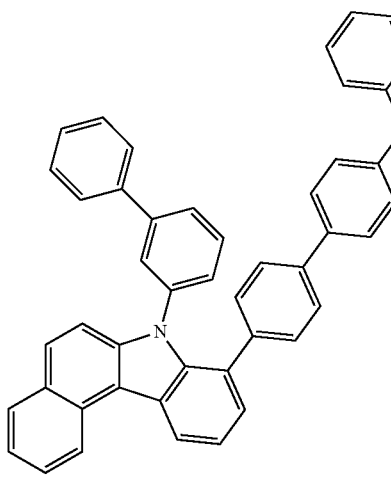
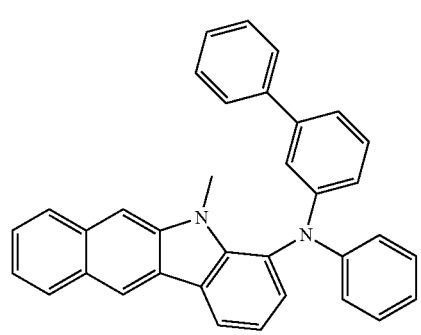
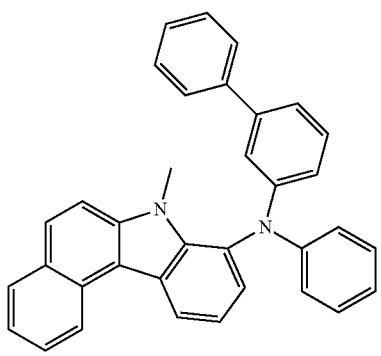
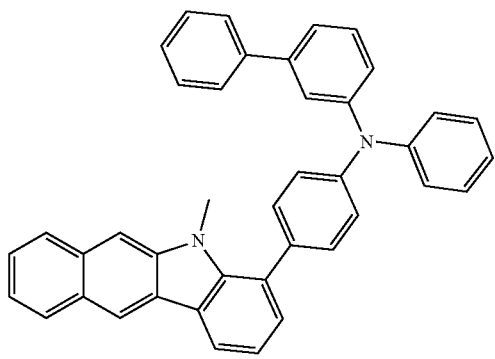

-continued
1811          1812
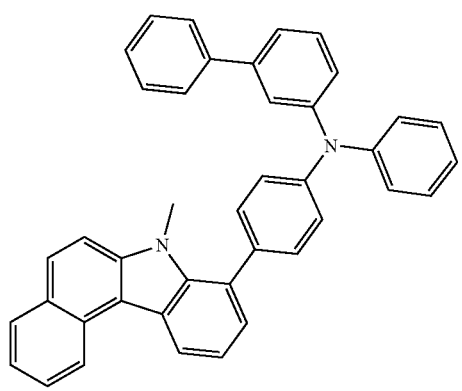
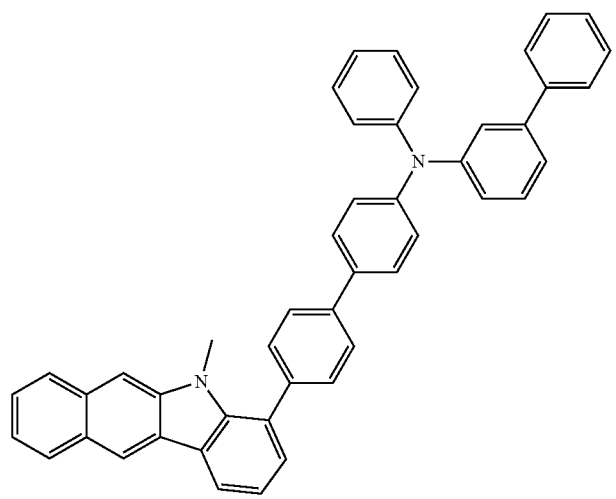
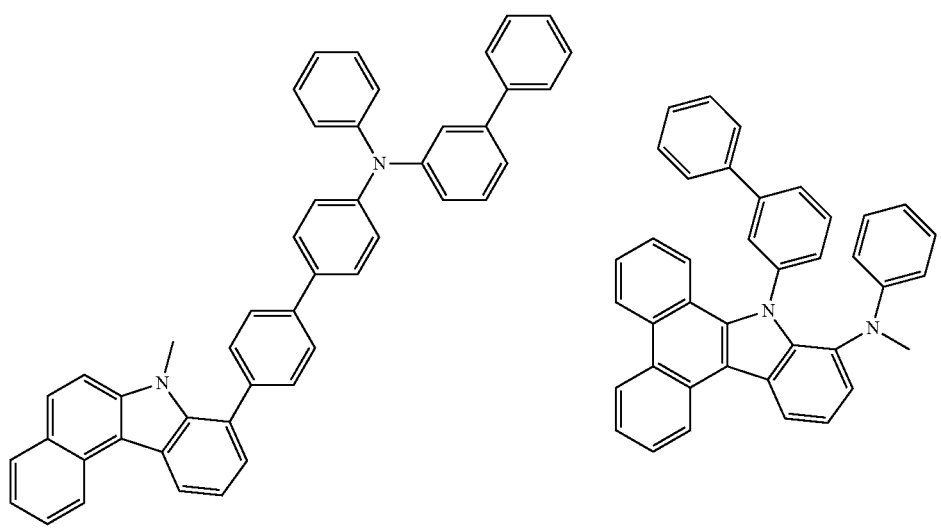
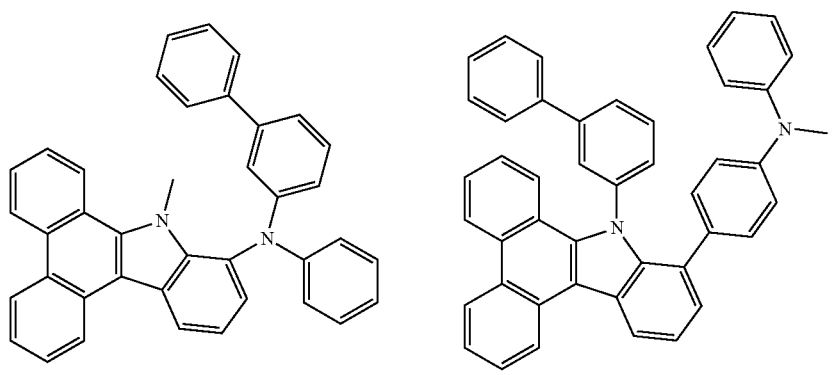

-continued
| 1813 | 1814 |
|---|---|
| 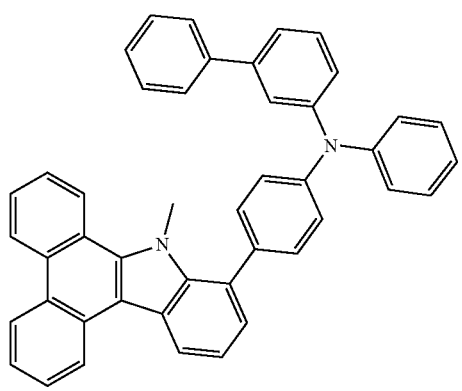 | 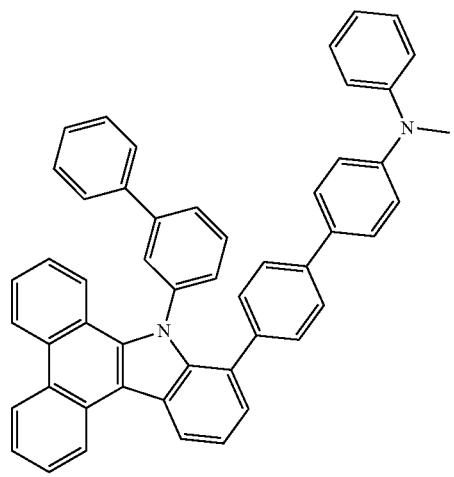 |
| 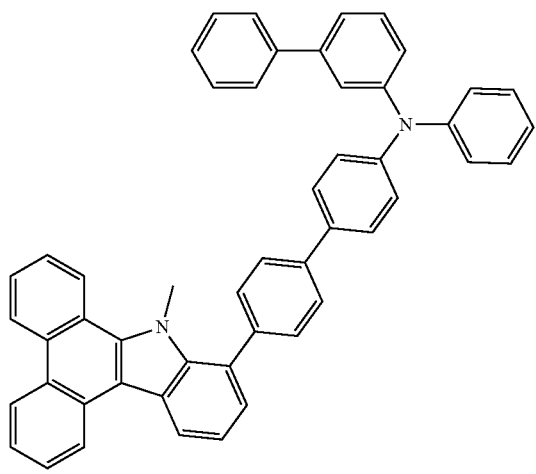 | 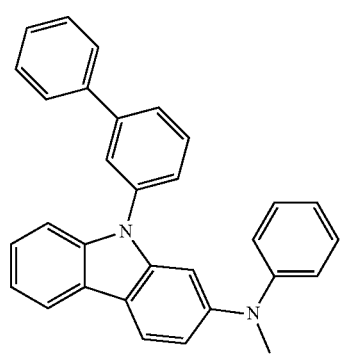 |
| 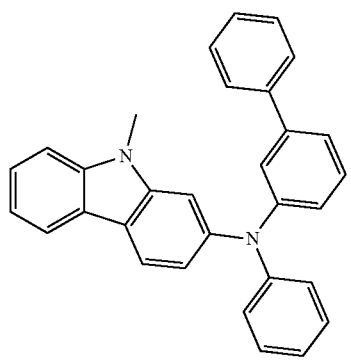 | 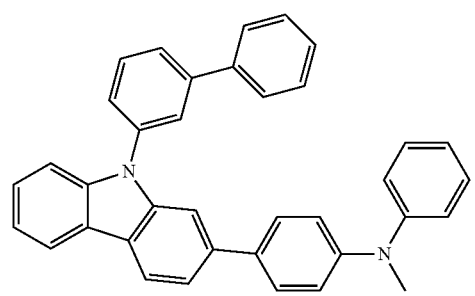 |
| 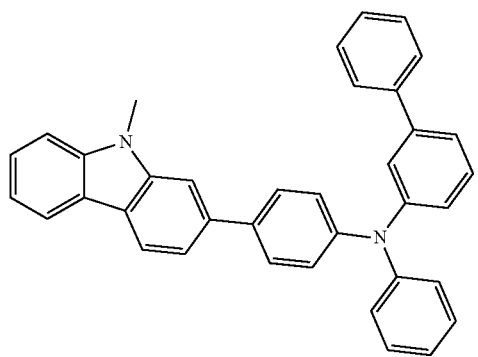 | 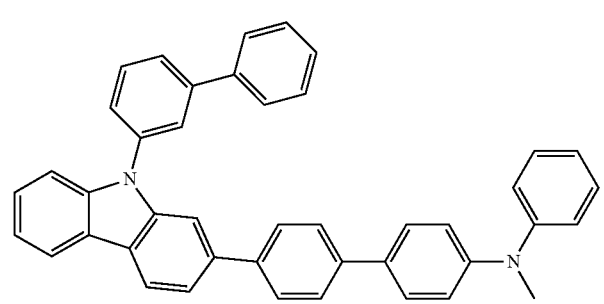 |

1815 -continued 1816
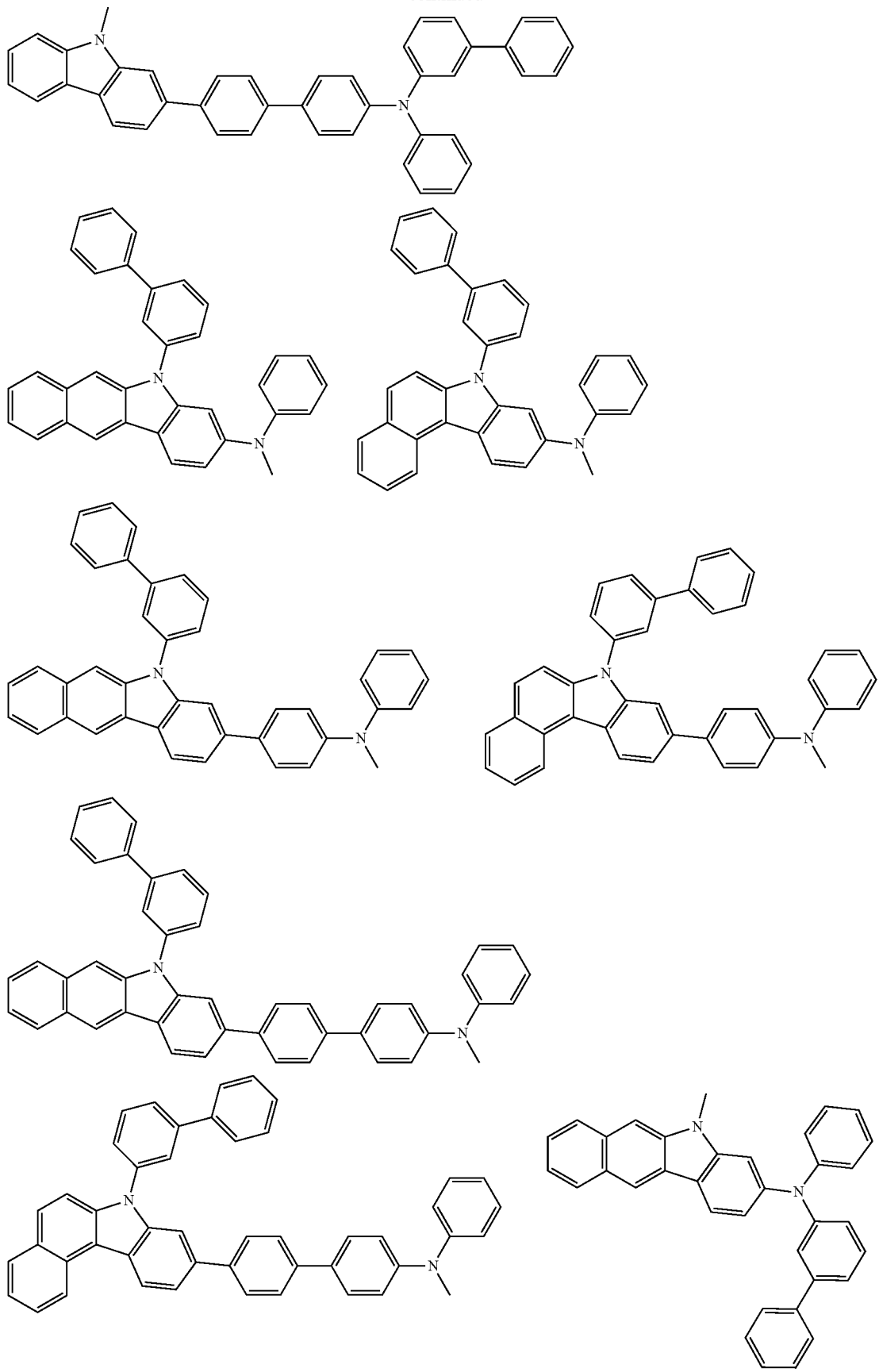

-continued
| 1817 | 1818 |
|---|---|
| 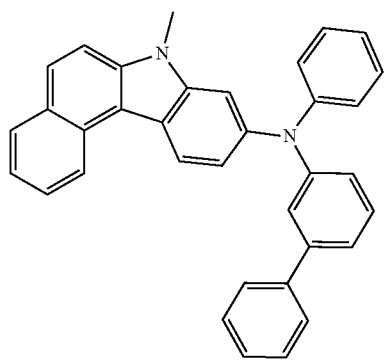 | 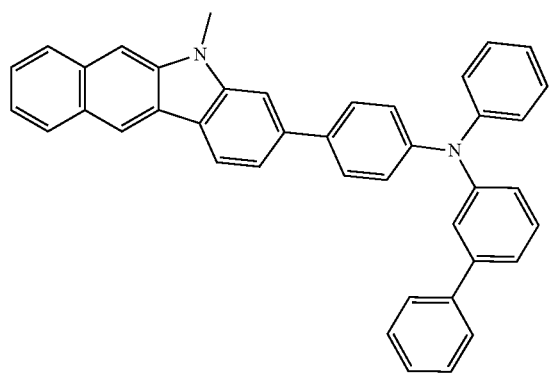 |
| 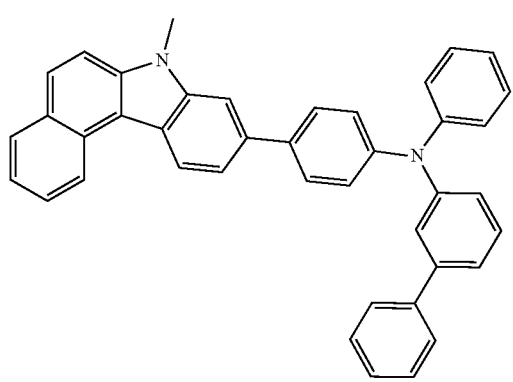 | |
| 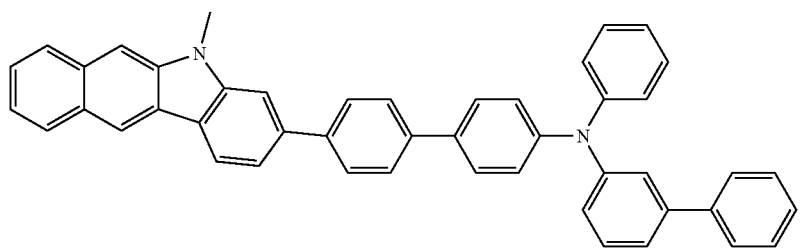 | |
| 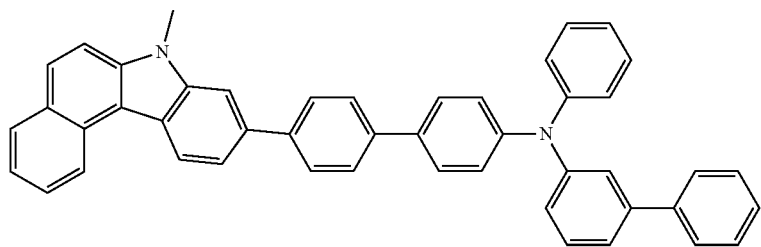 | |
| 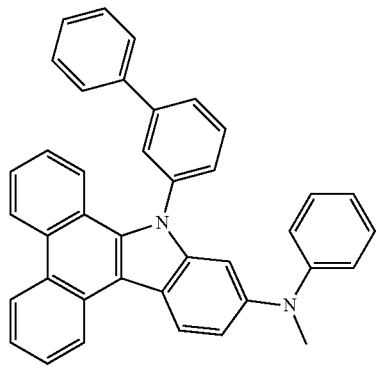 | 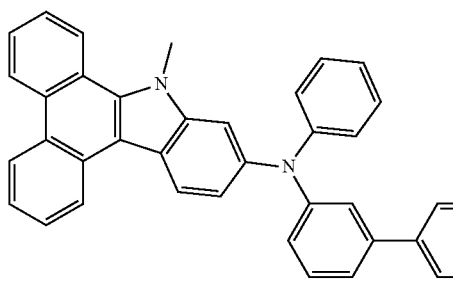 |

-continued
| 1819 | 1820 |
|---|---|
| 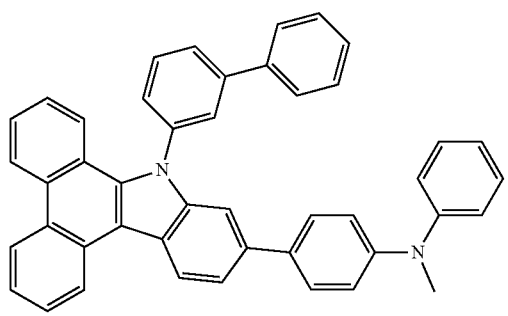 | 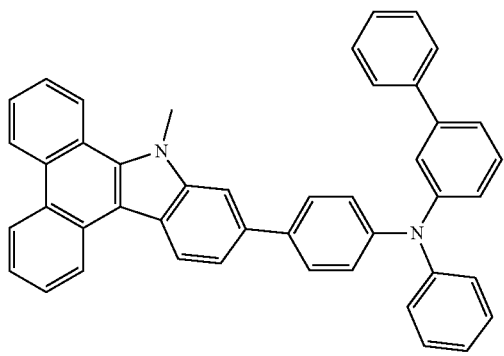 |
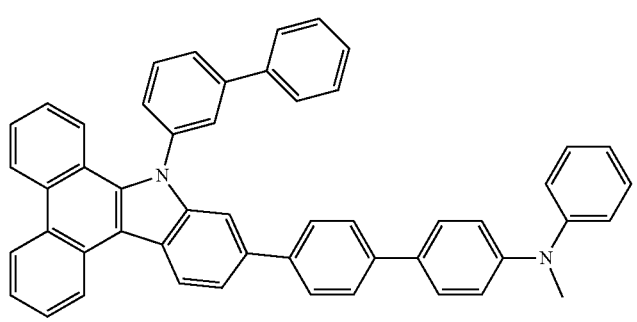
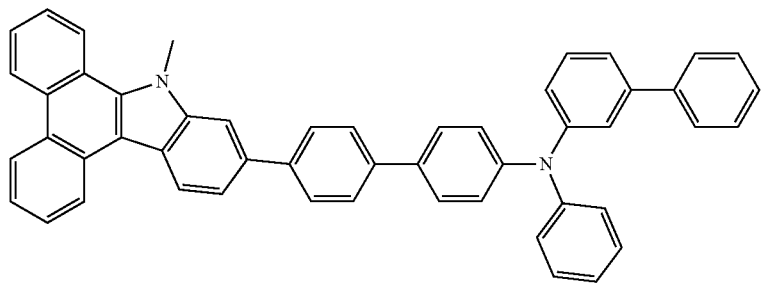
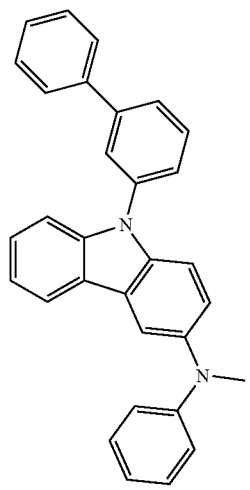 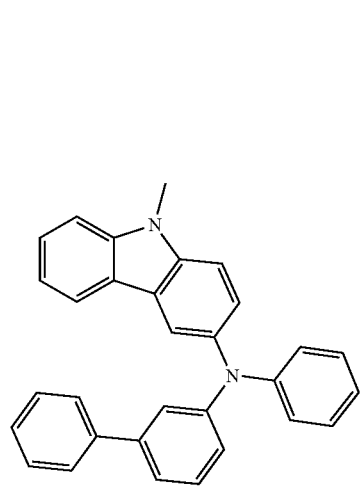 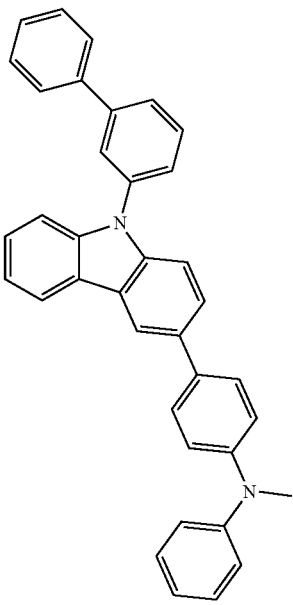

1821 1822
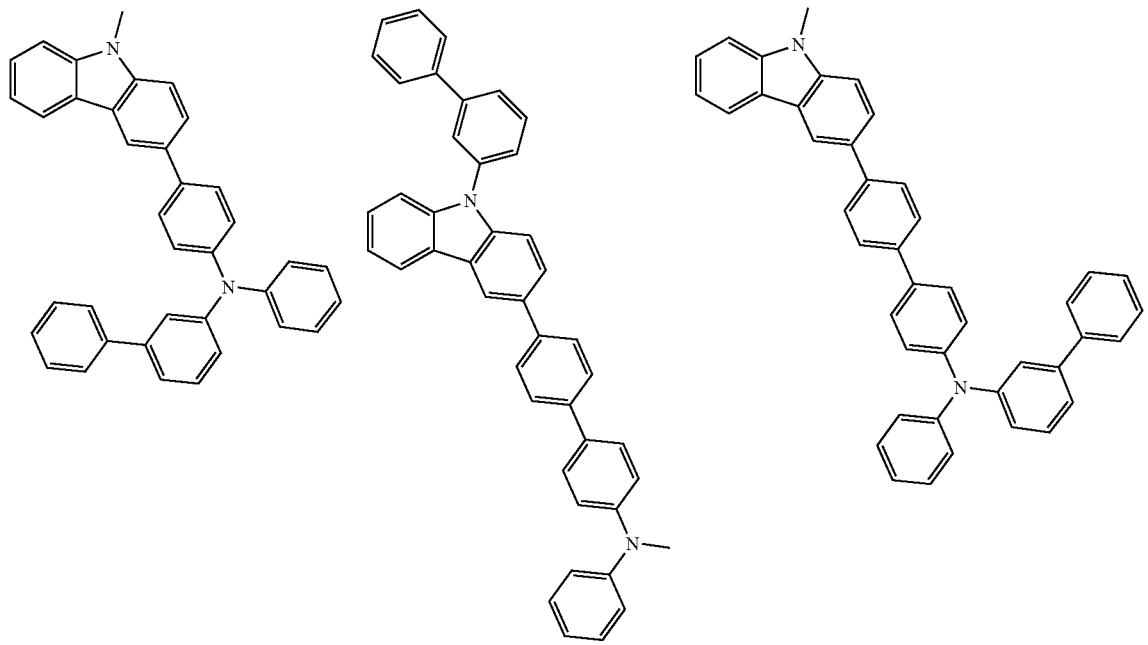
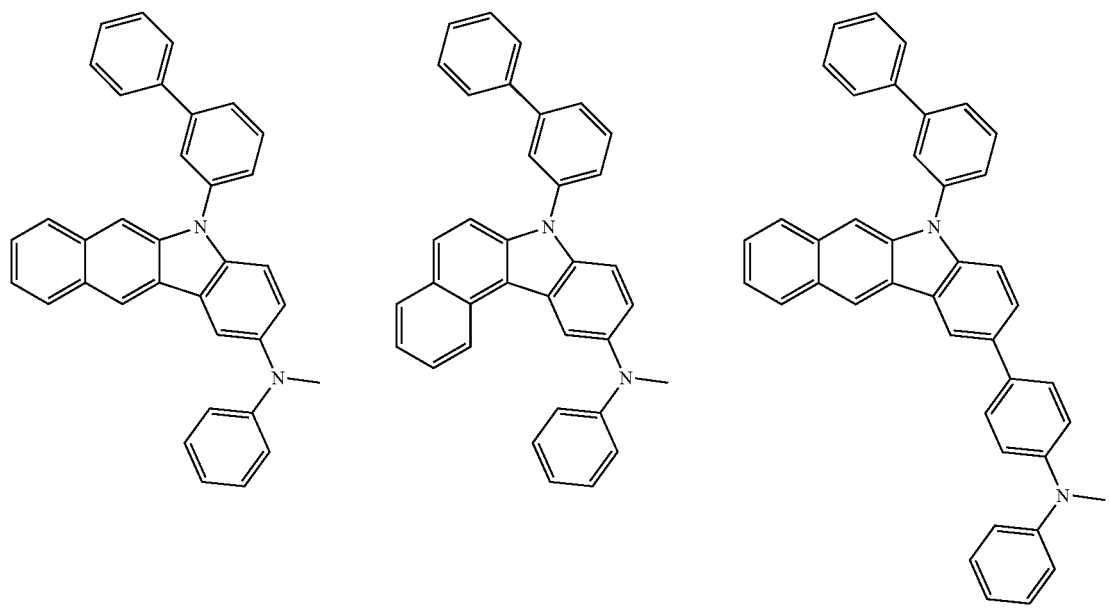

1823
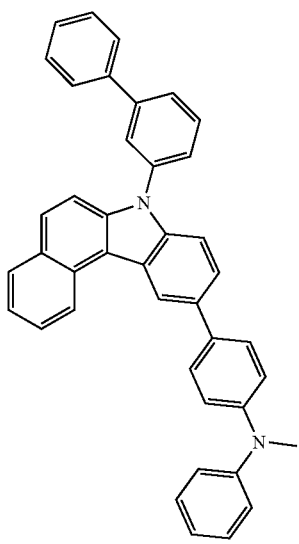
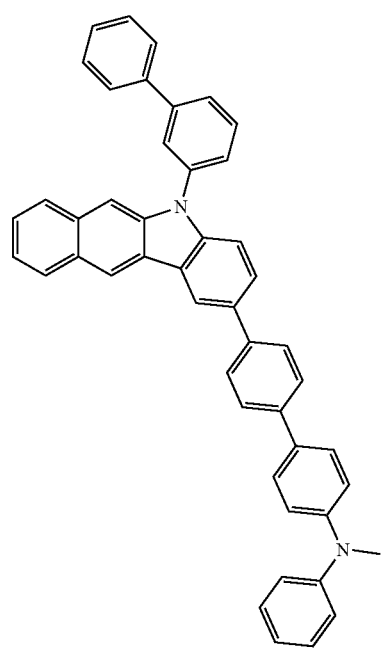
-continued
1824
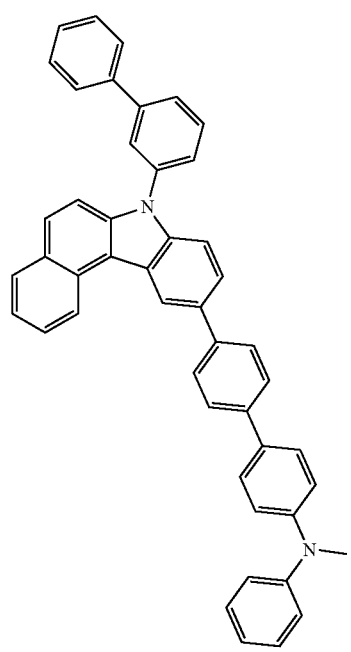
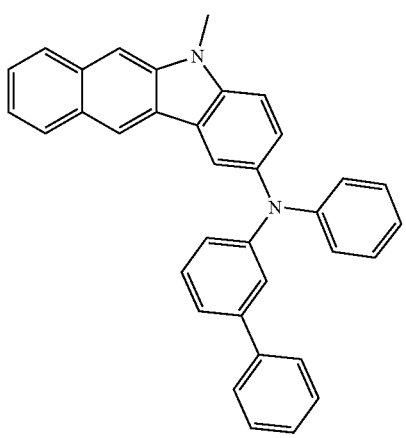
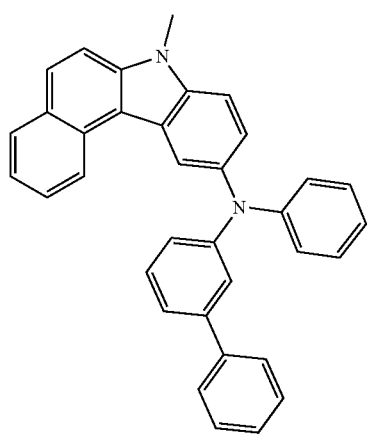
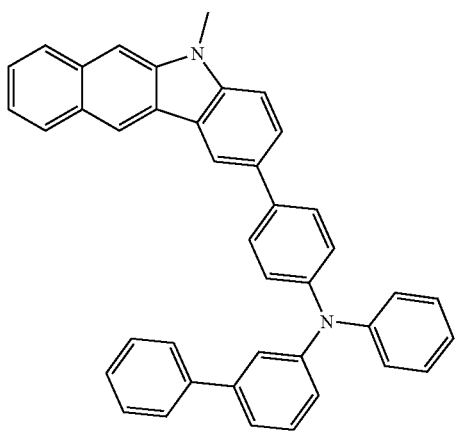
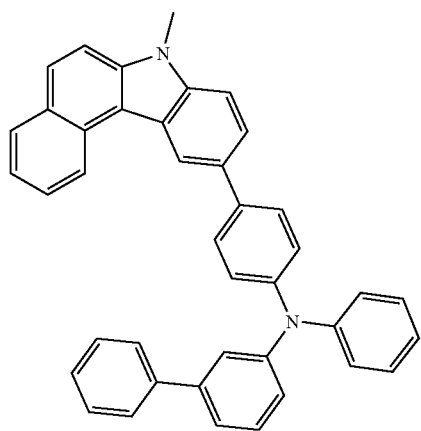

1825 1826
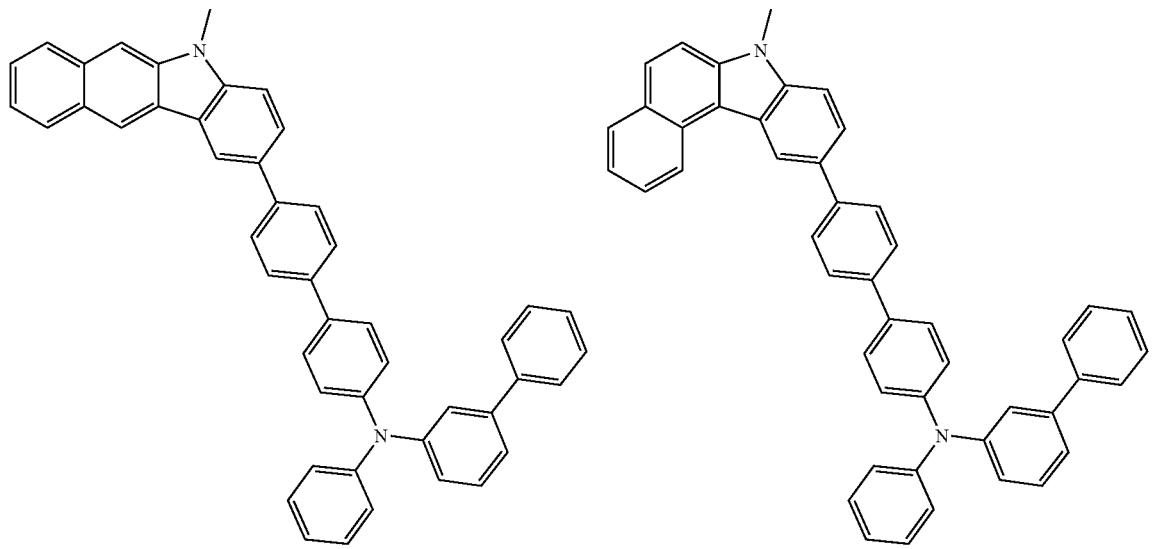
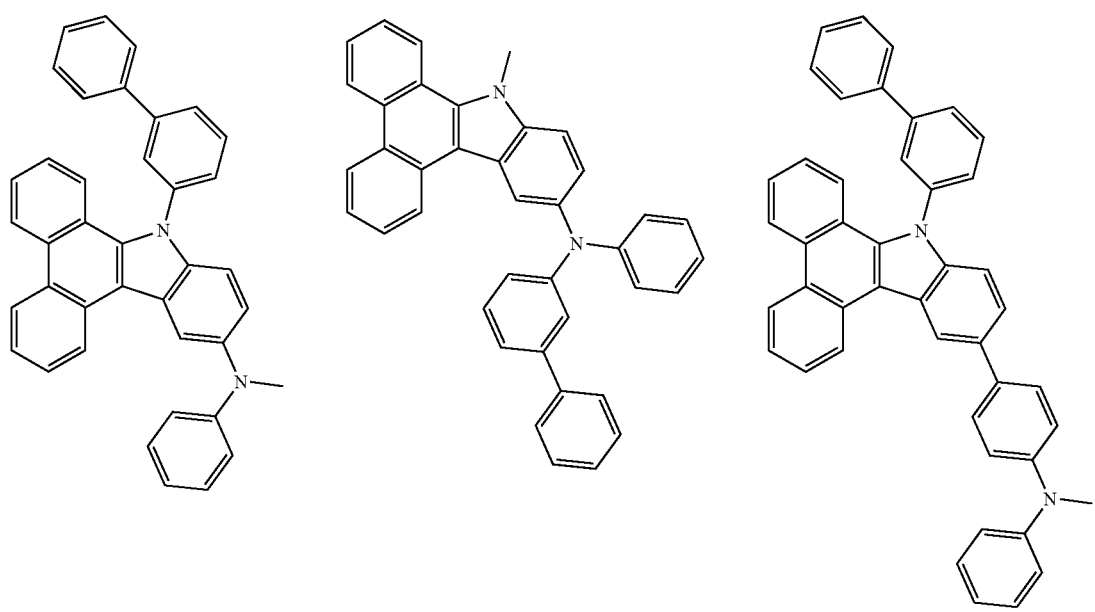

1827
1828
-continued
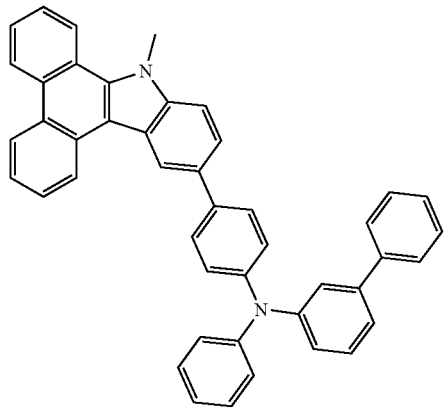
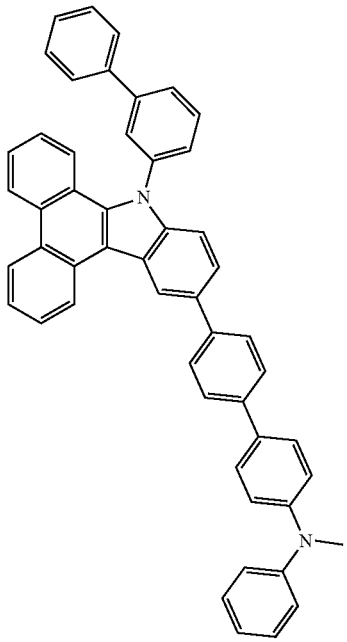
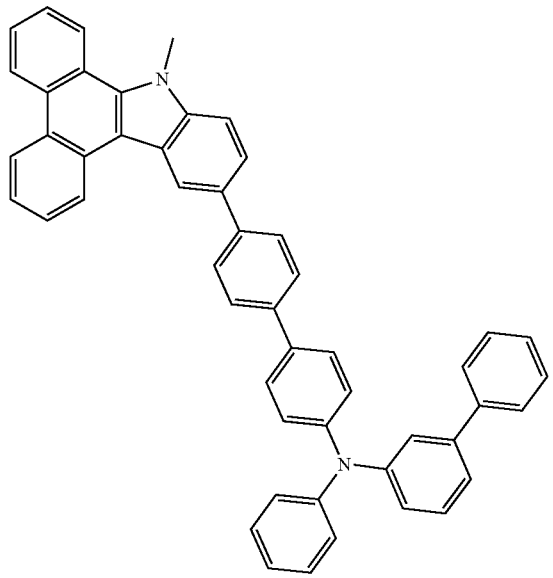
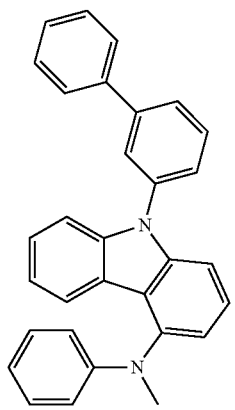
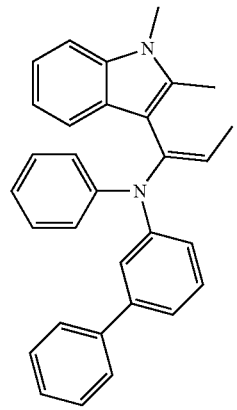

1829
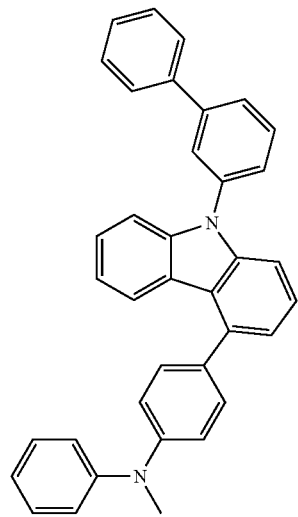 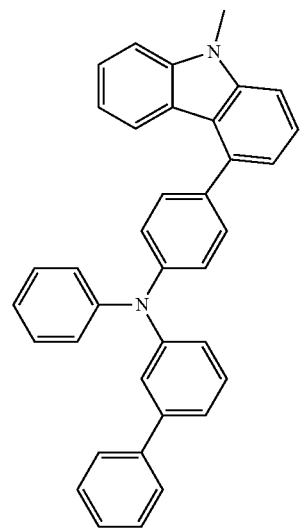
1830
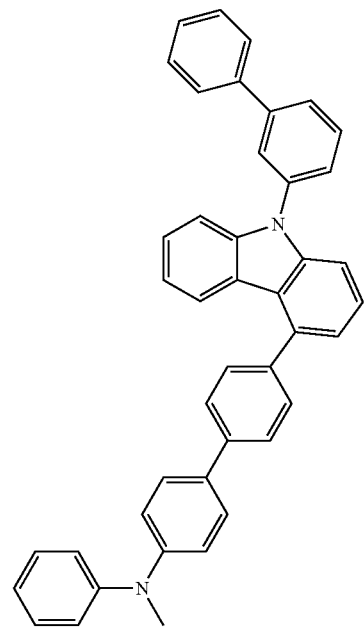
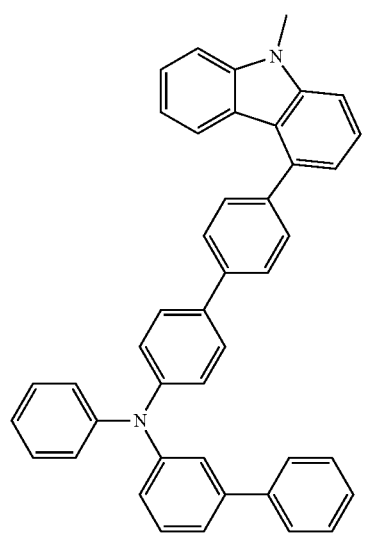 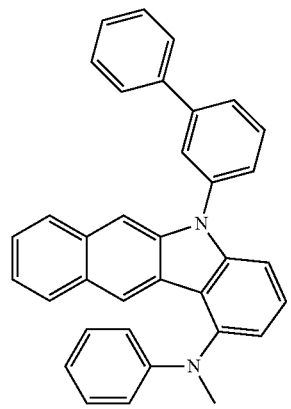 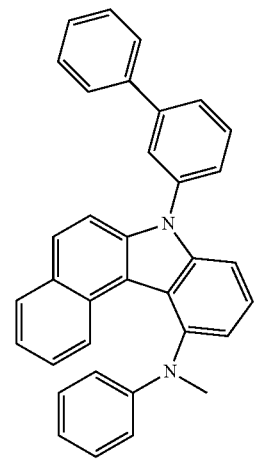

-continued
| 1831 | | 1832 |
|---|---|---|
| 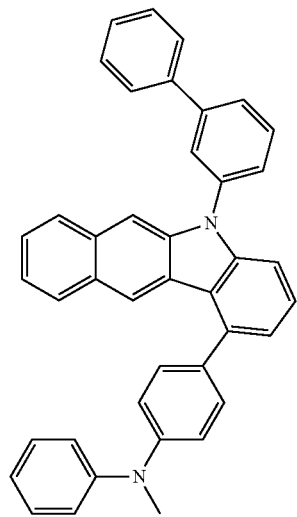 | 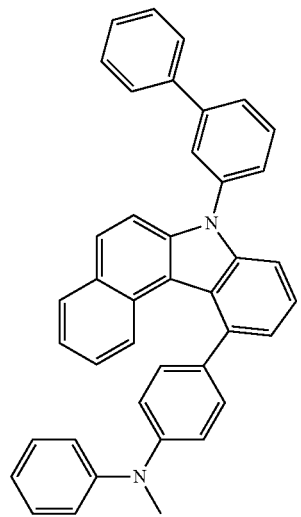 | 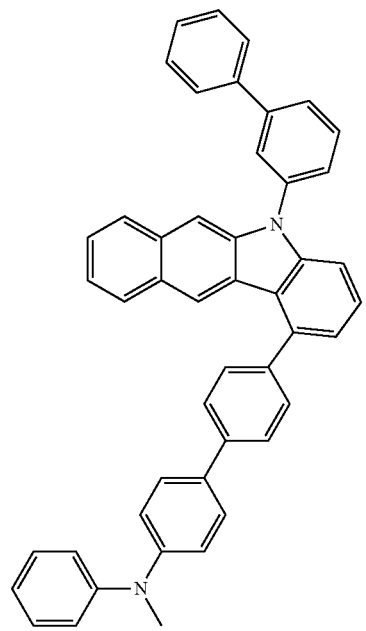 |
| 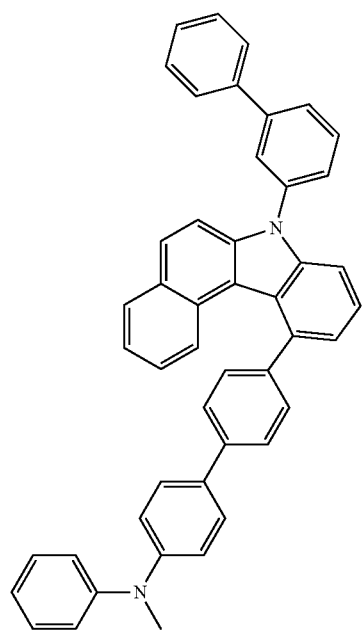 | 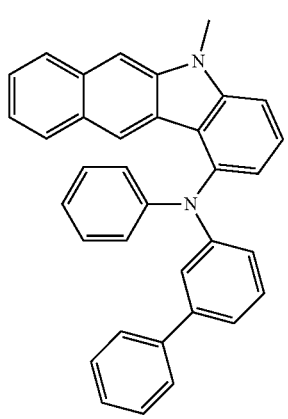 | 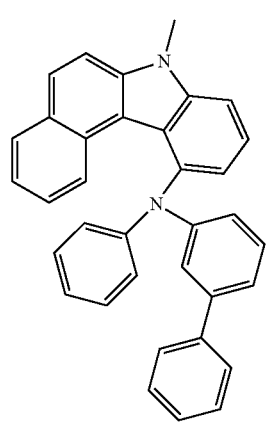 |

1833
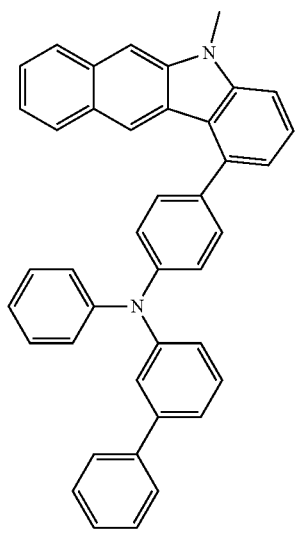
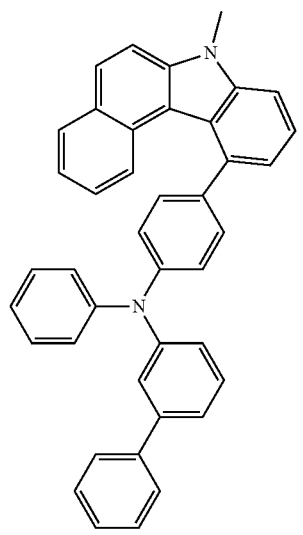
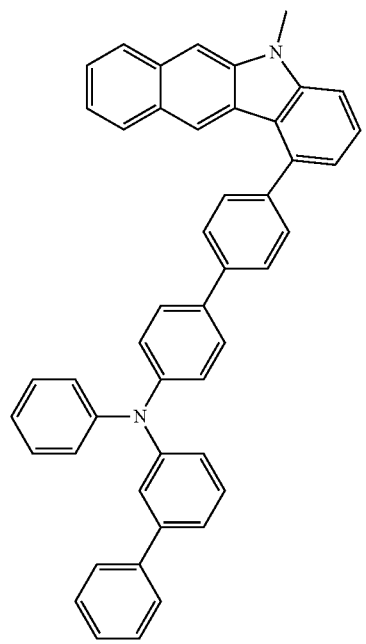
1834
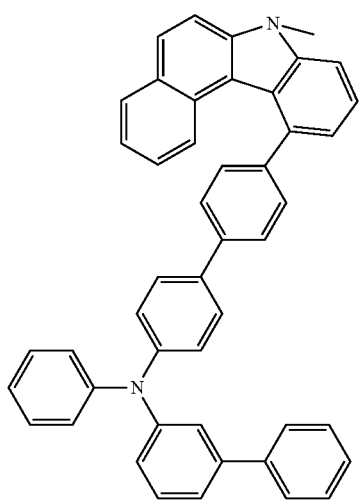
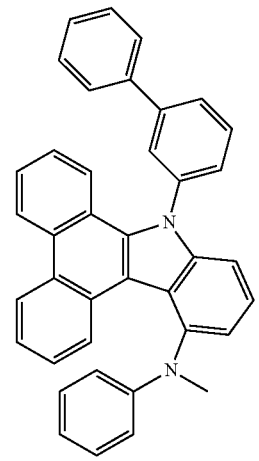
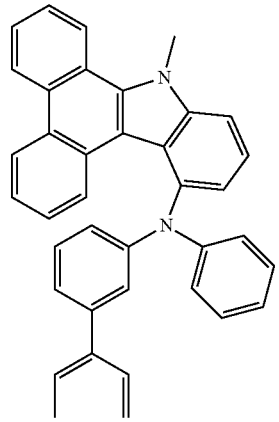

1835
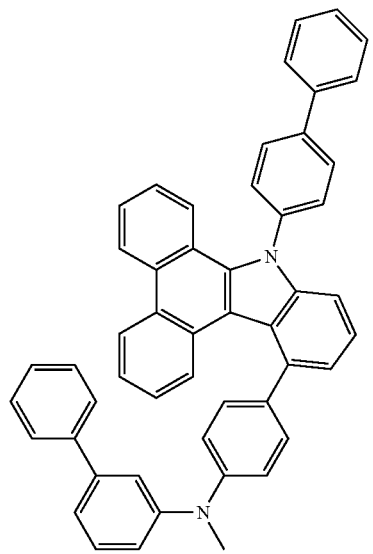
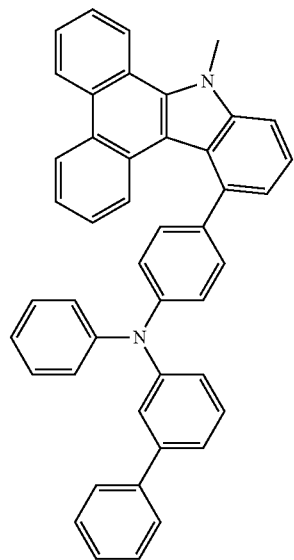
1836
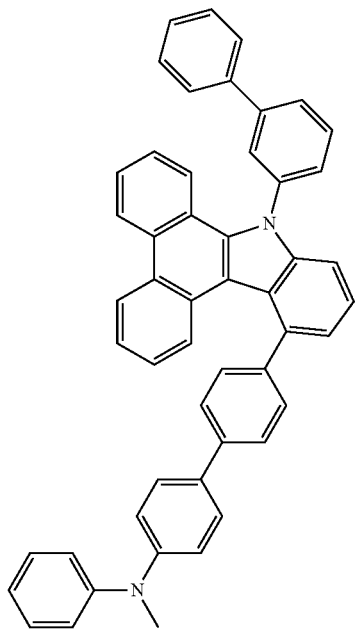
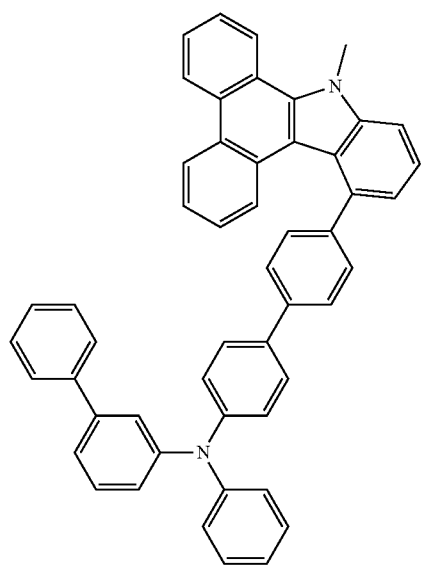
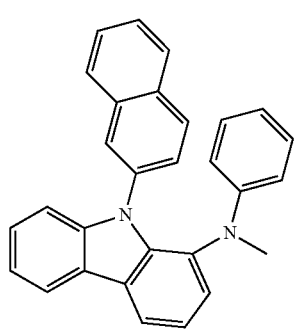
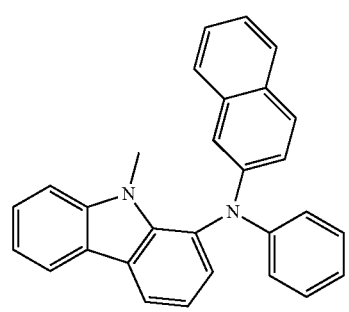
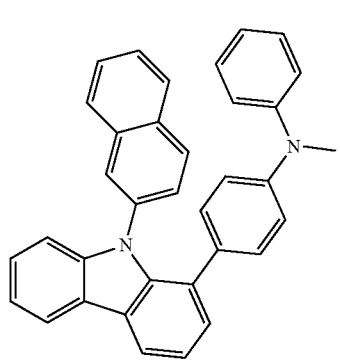
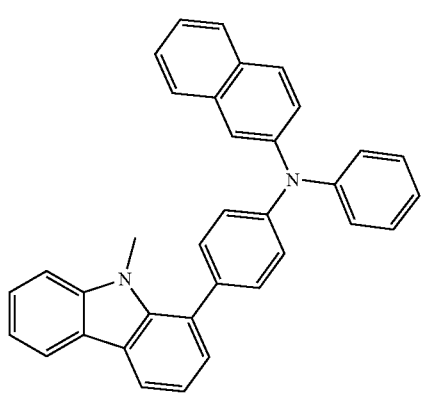

1837                               1838
-continued
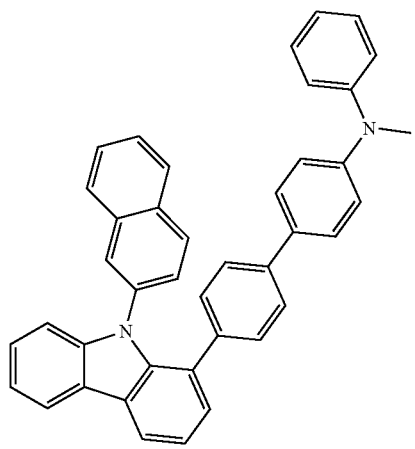
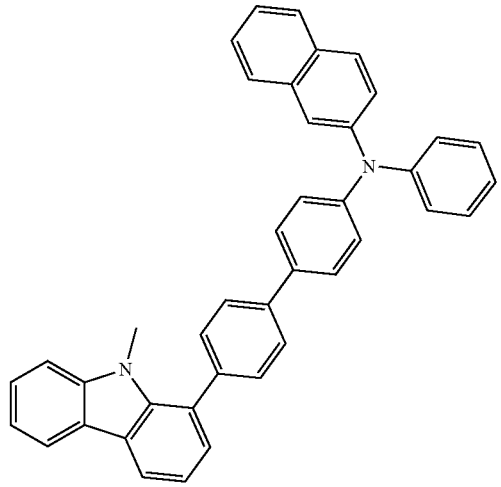
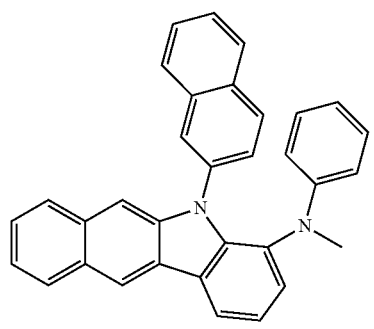
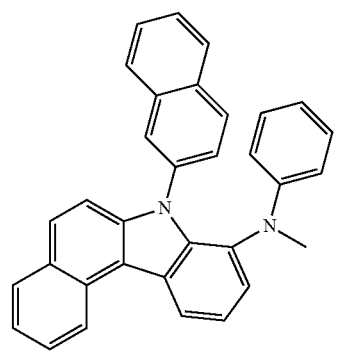
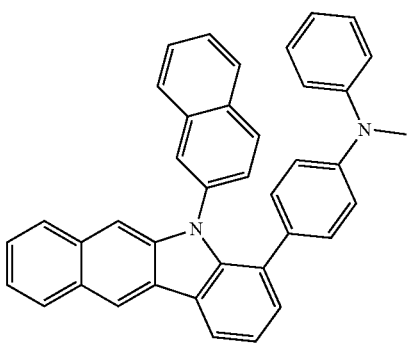
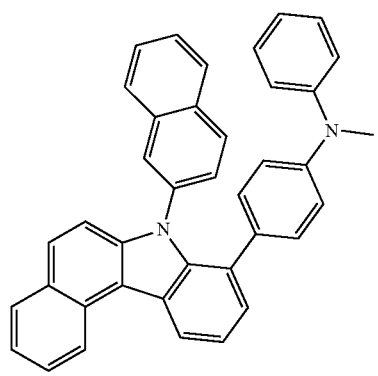
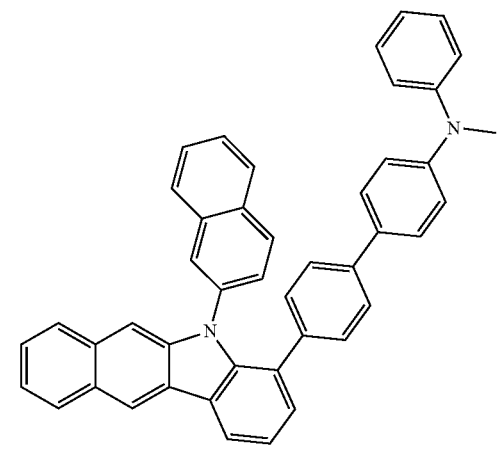

-continued
1839
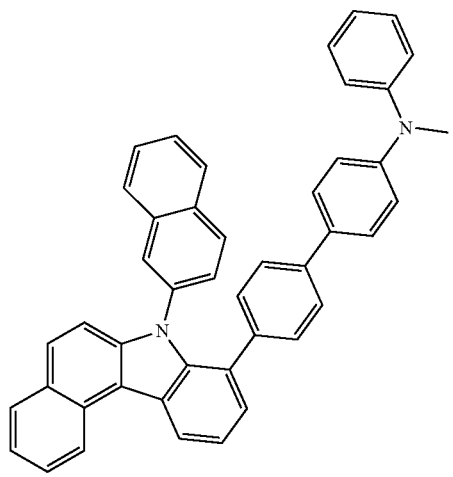
1840
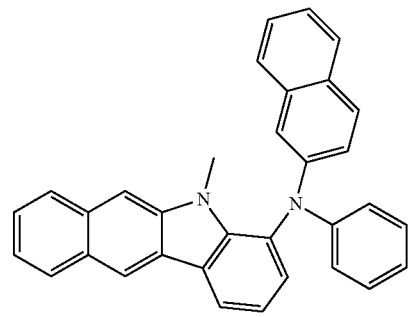
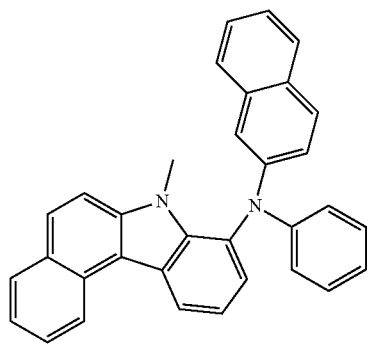
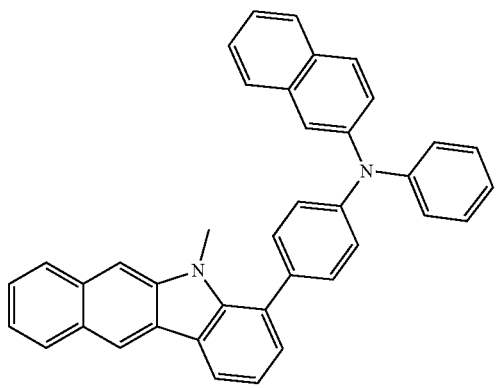
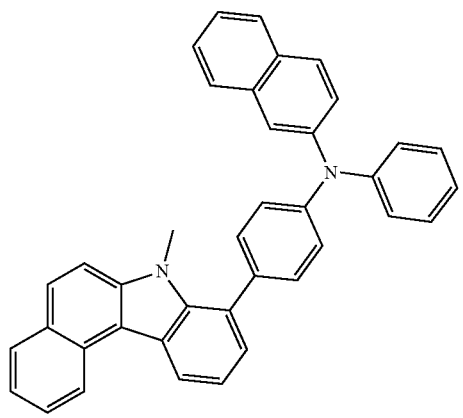
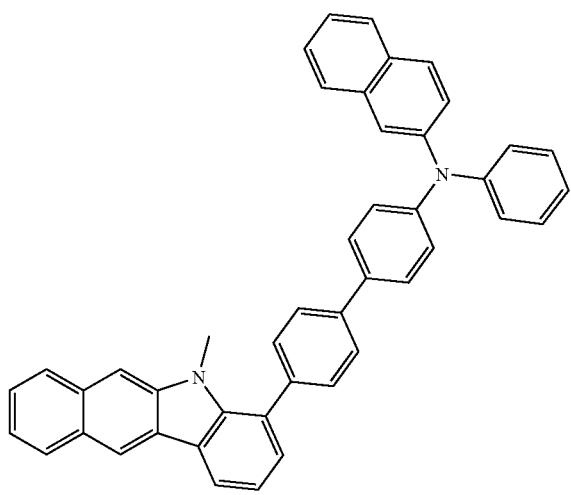

1841
1842
-continued
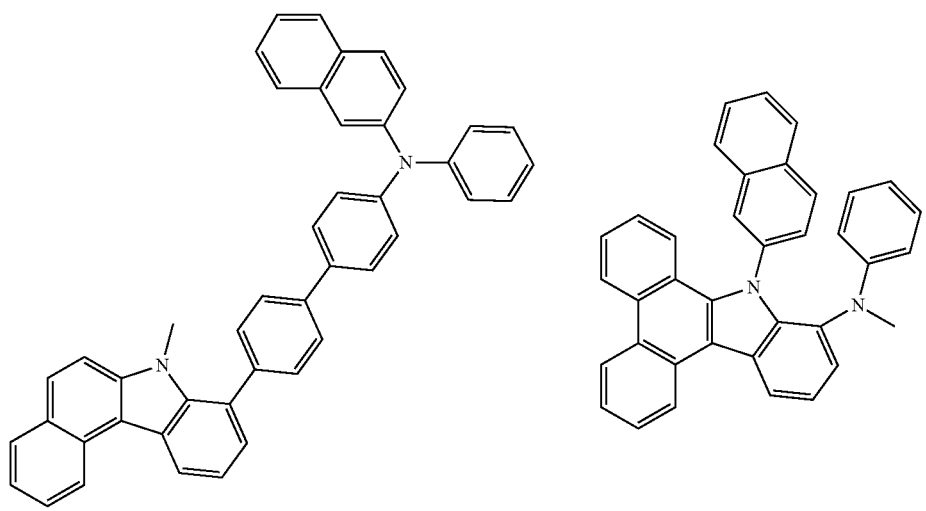
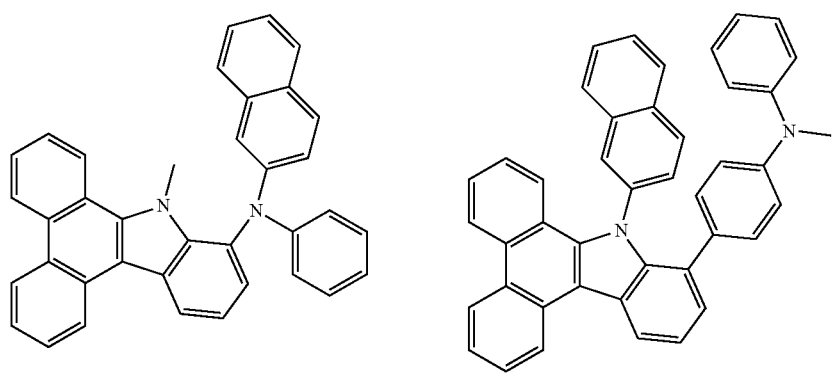
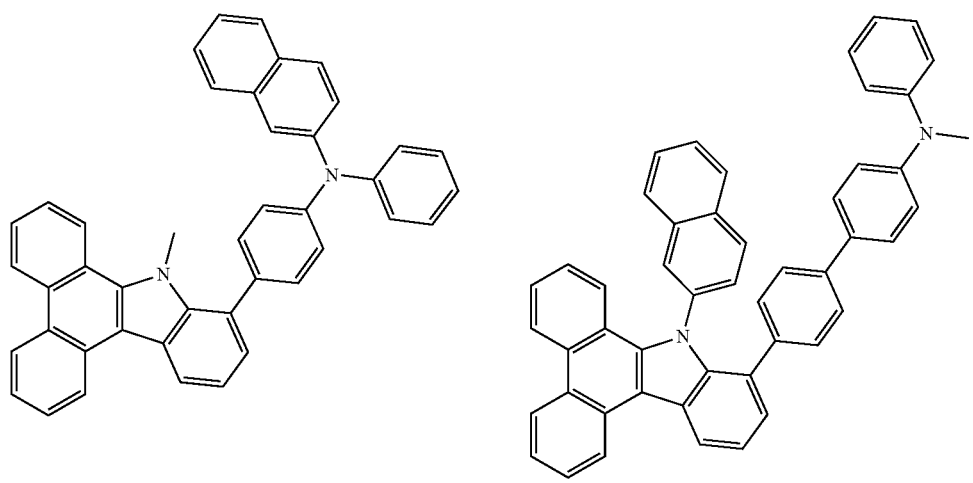

1843 1844
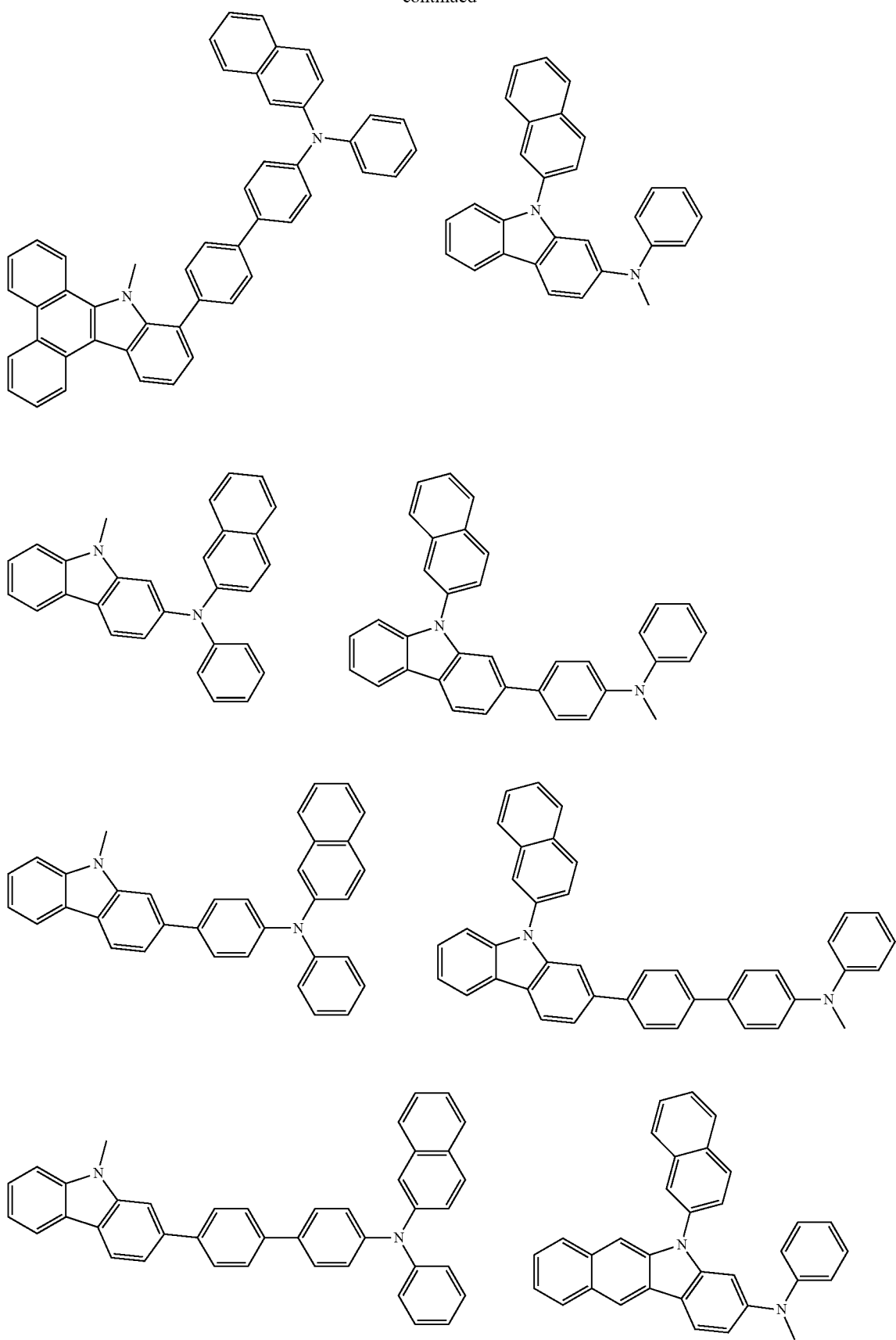

-continued
1845
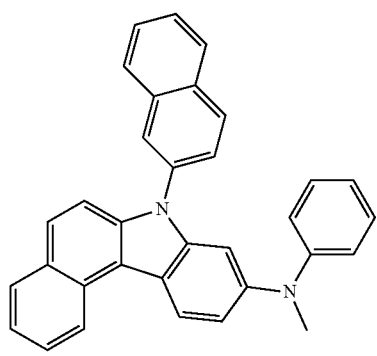
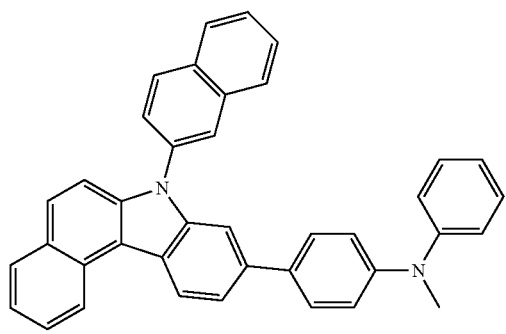
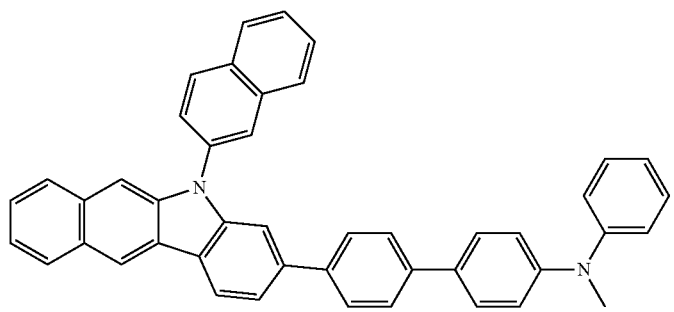
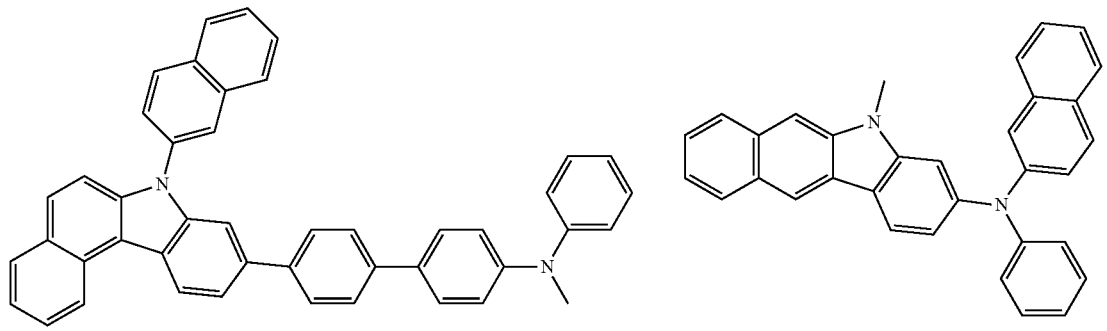
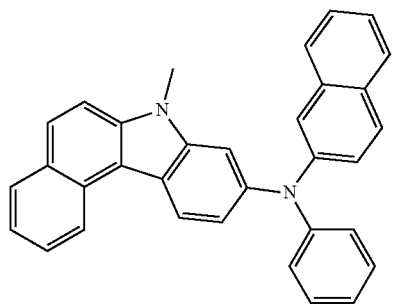
1846
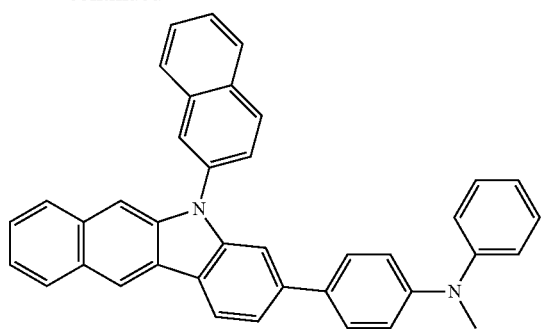
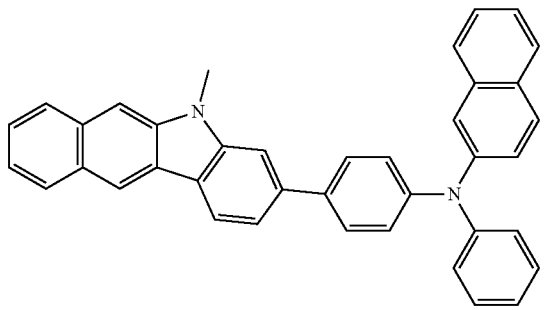

1847
-continued
1848
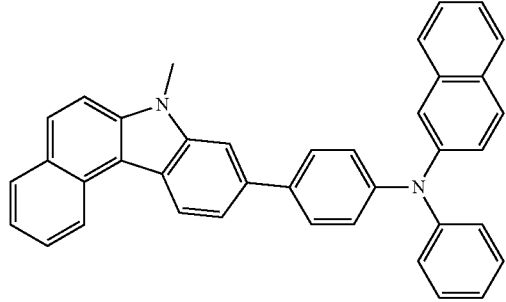
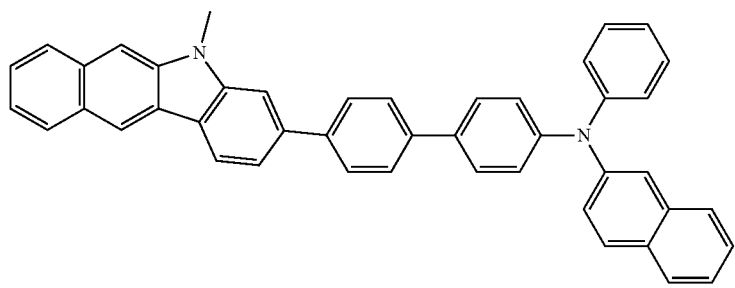
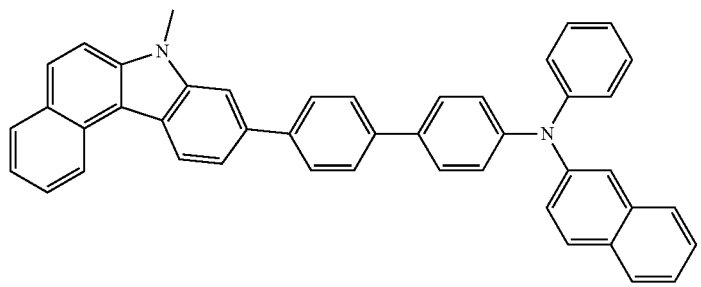
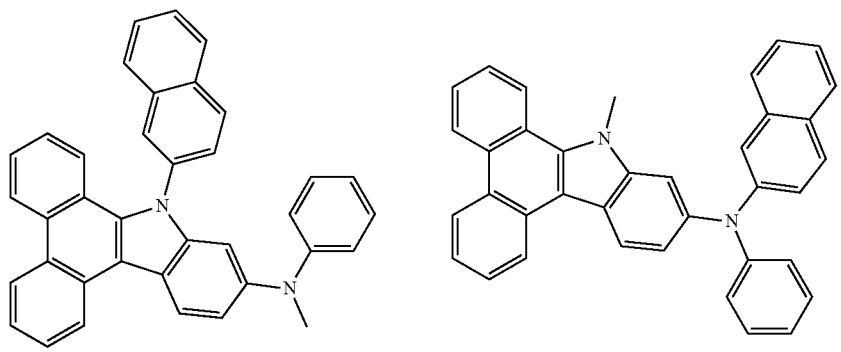
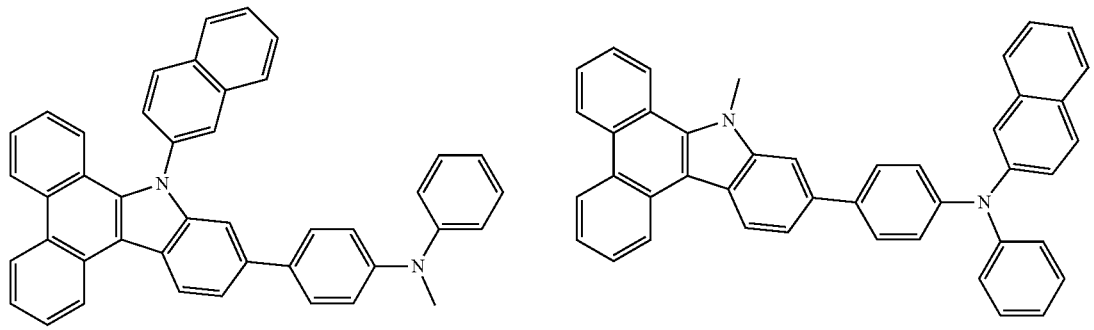

1849
1850
-continued
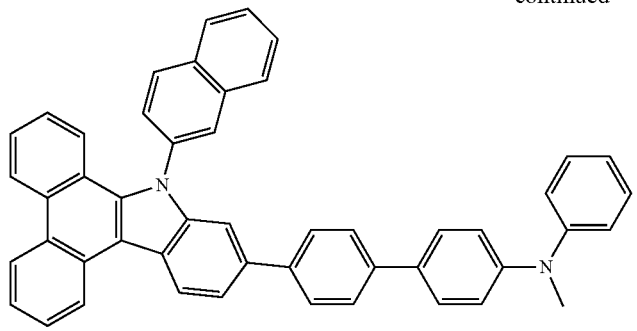
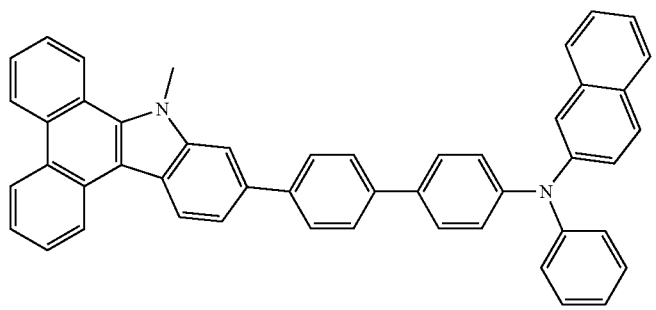
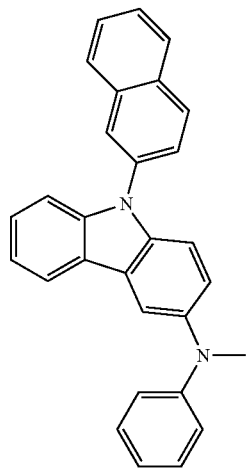
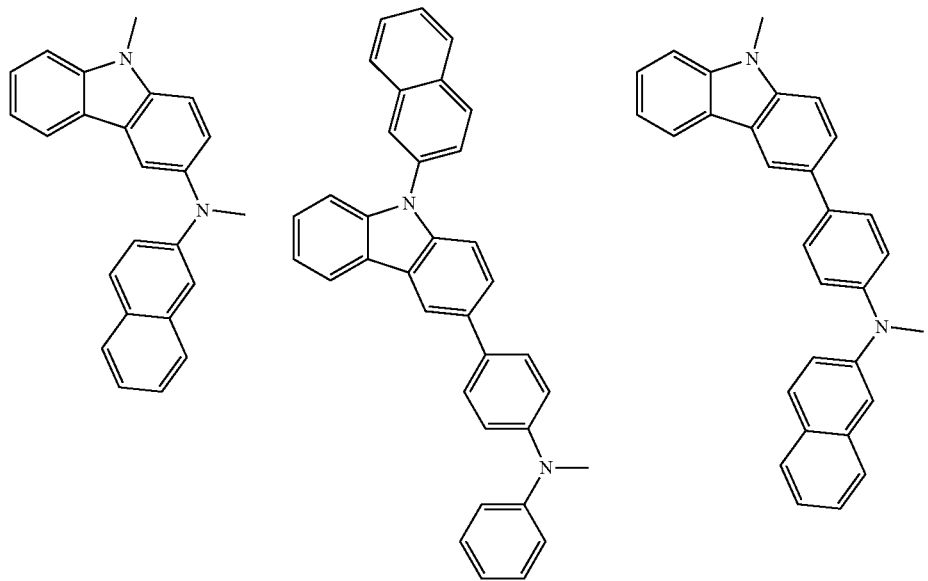

1851
1852
-continued
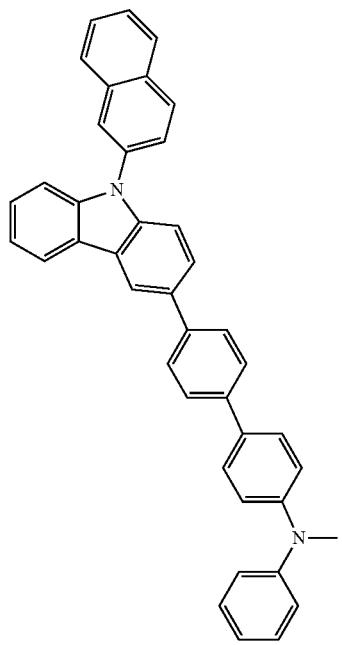
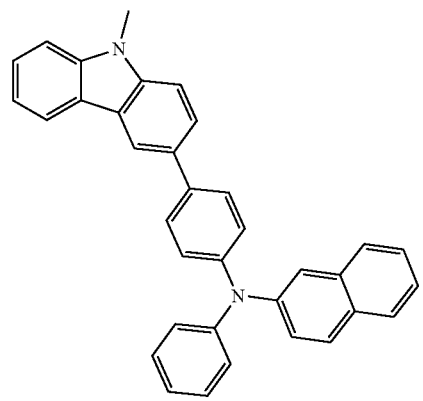
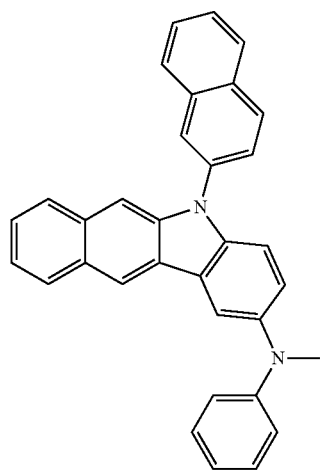
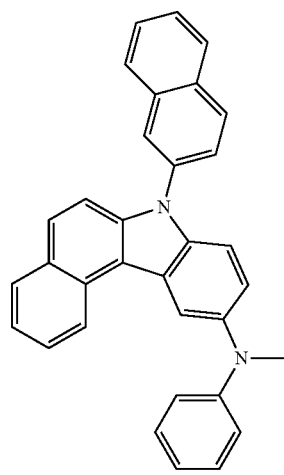
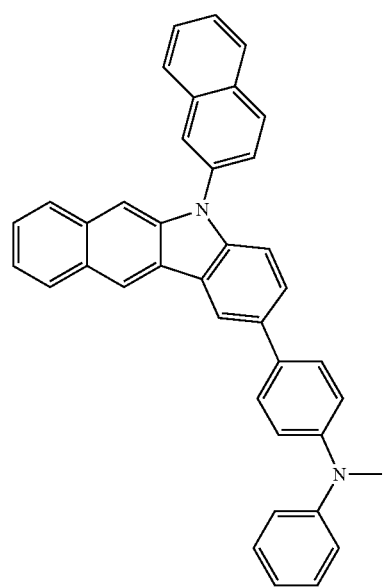

1853
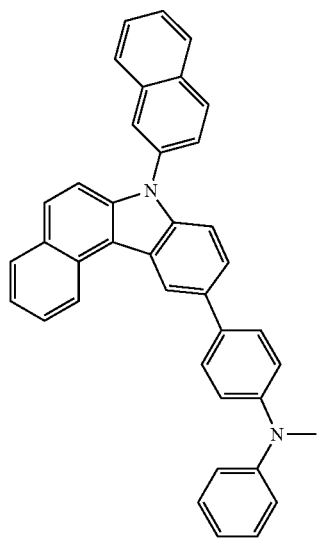
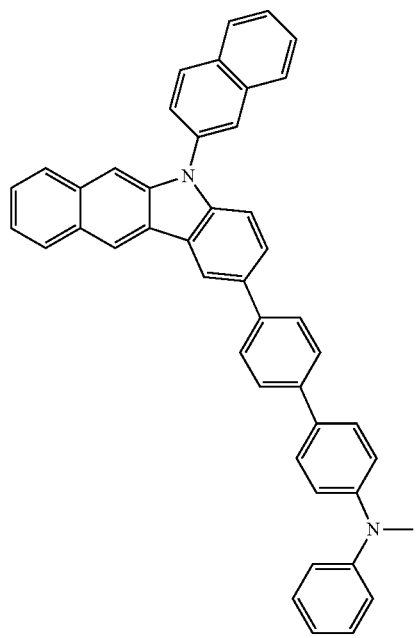
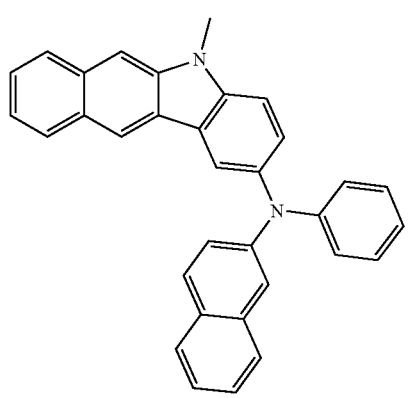
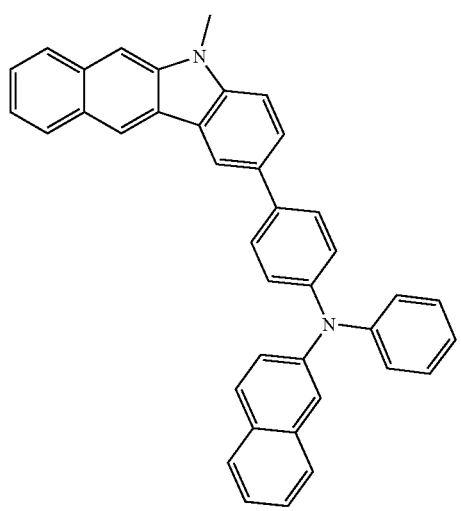
1854
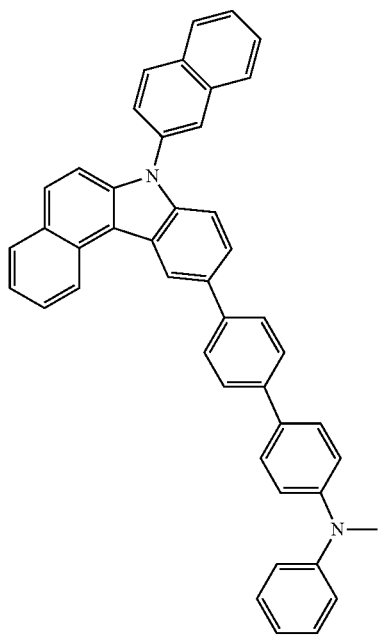
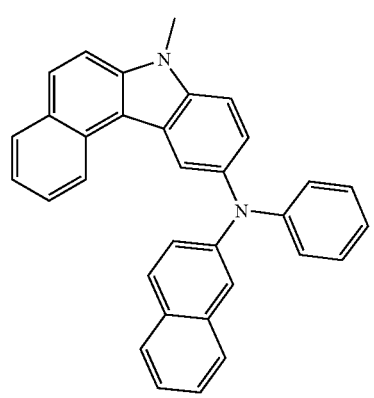
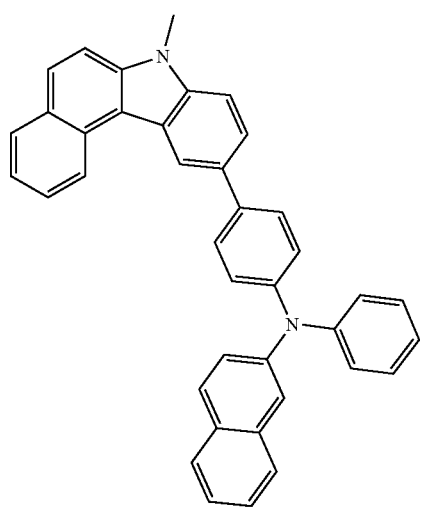

-continued
| 1855 | 1856 |
|---|---|
| 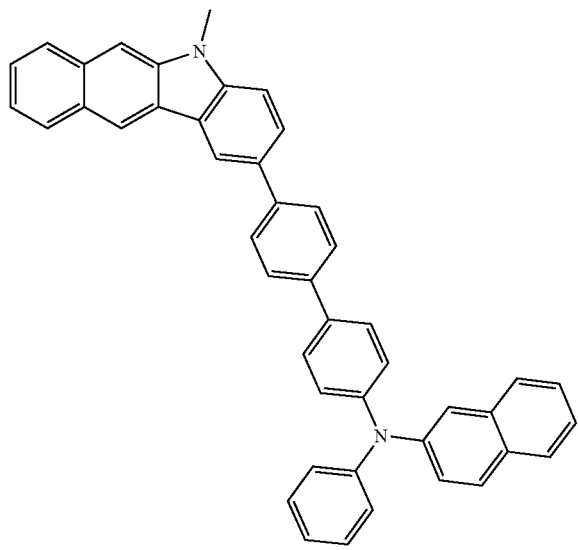 | 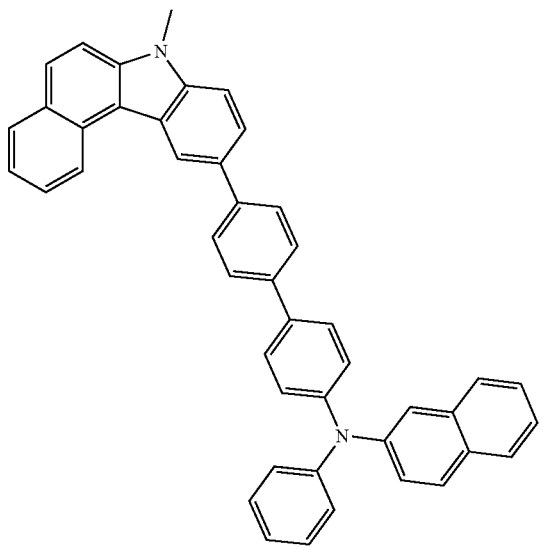 |
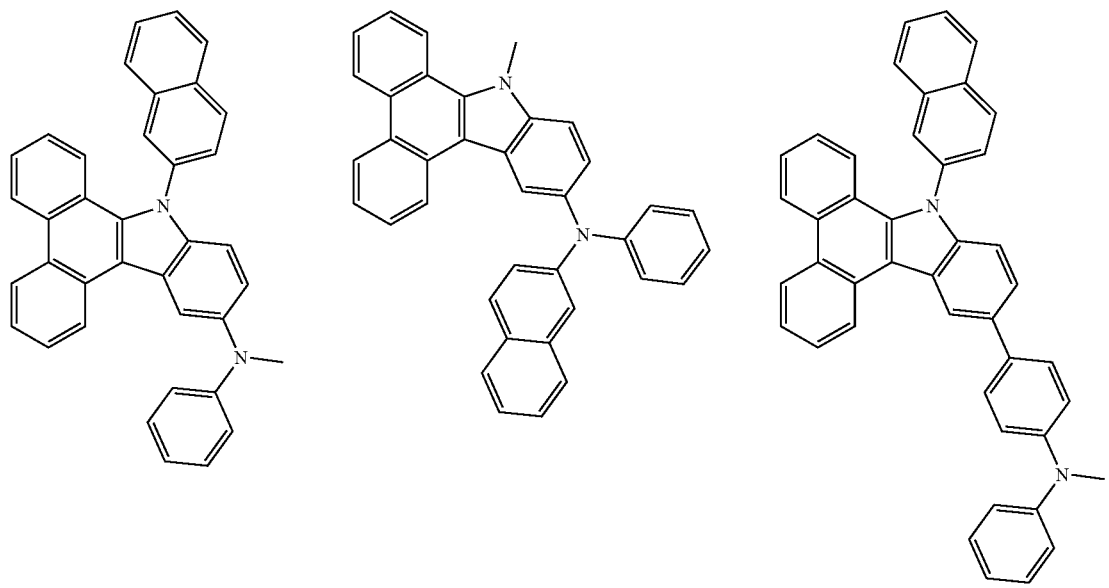

-continued
| 1857 | 1858 |
|---|---|
| 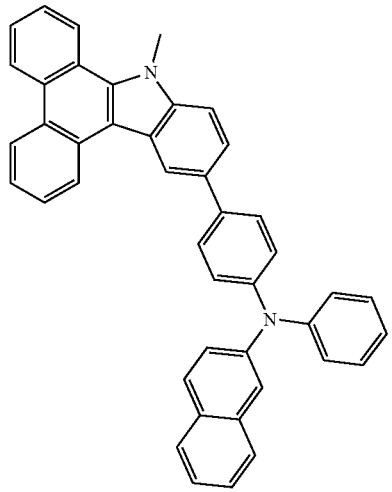 | 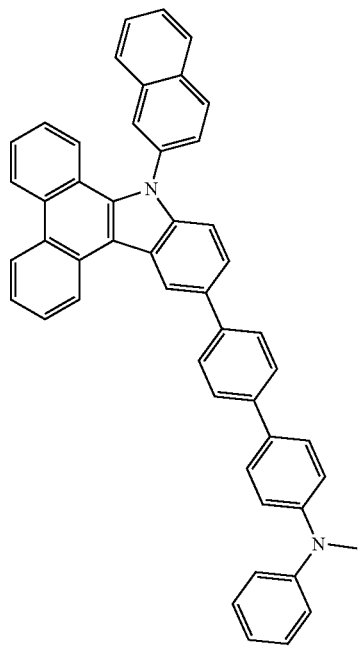 |
| 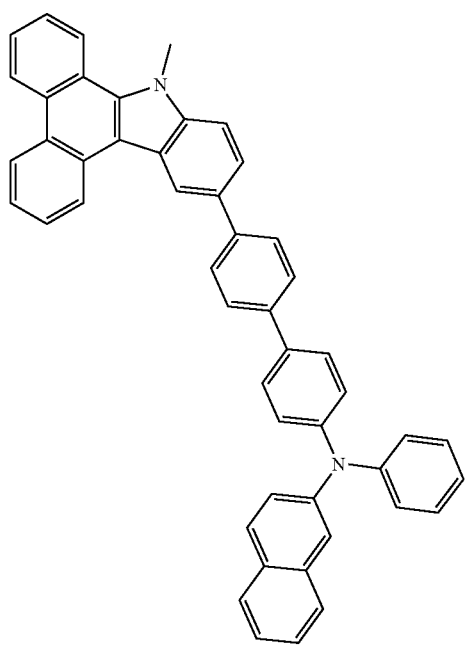 | 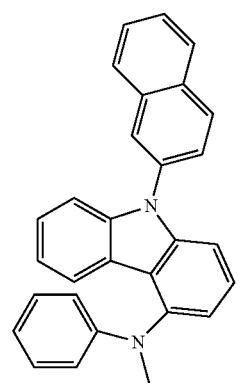 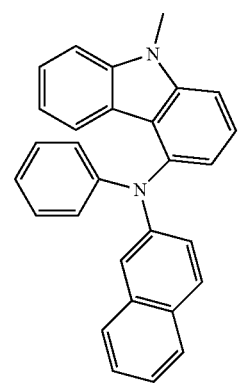 |

1859
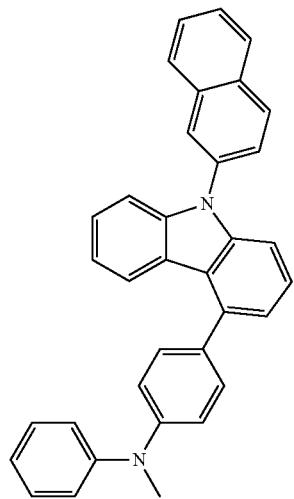
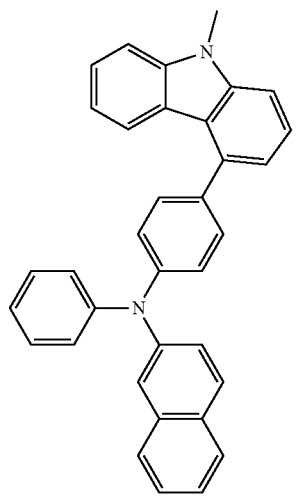
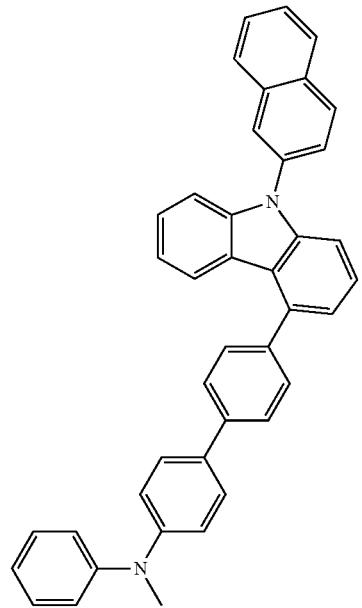
1860
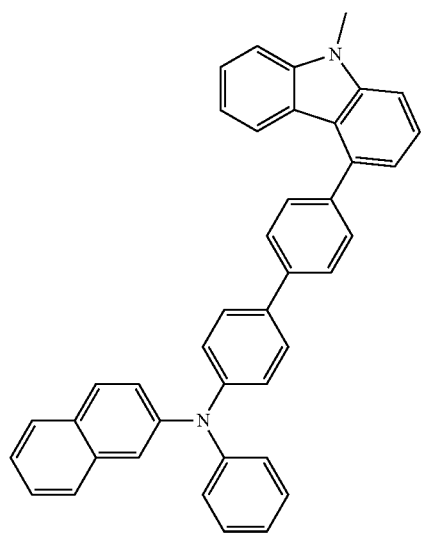
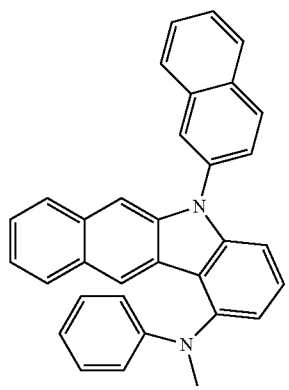
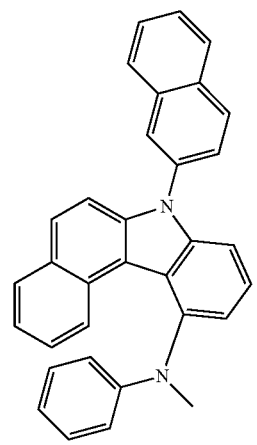

1861
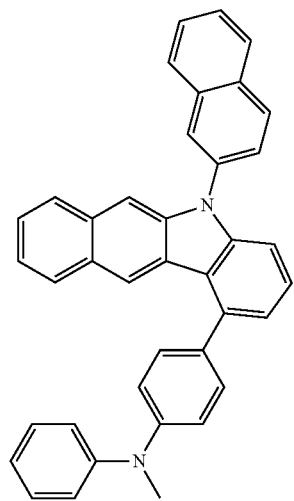
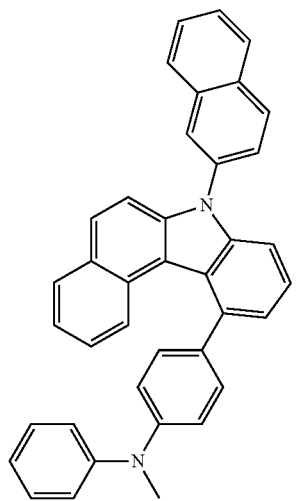
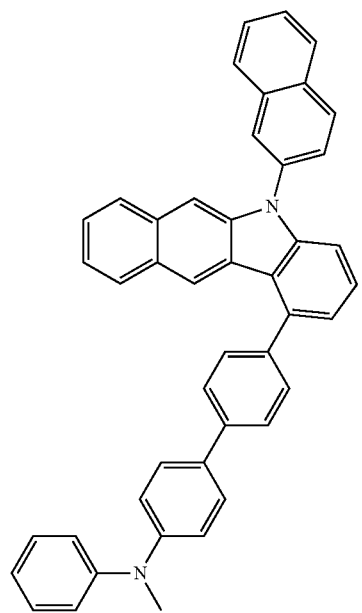
1862
-continued
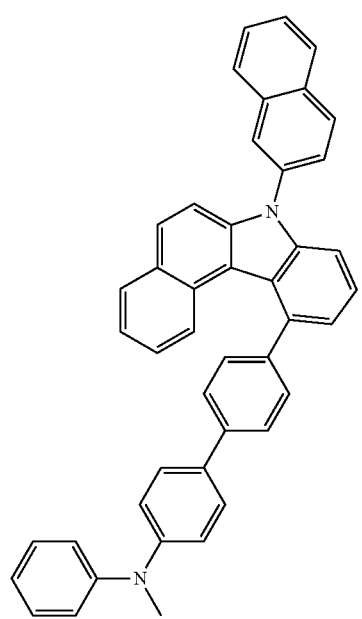
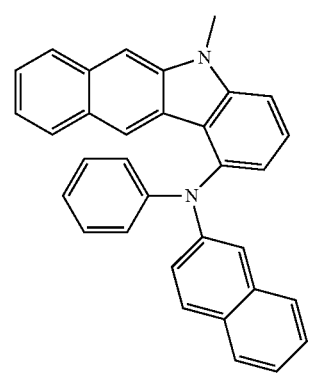
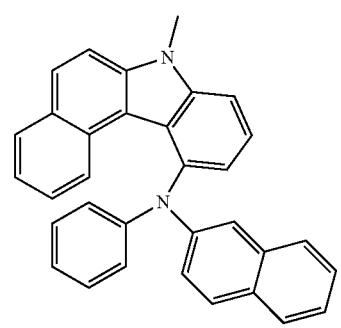

1863
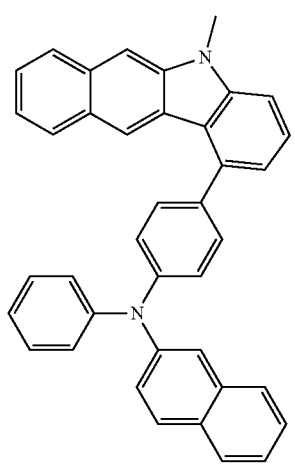
-continued
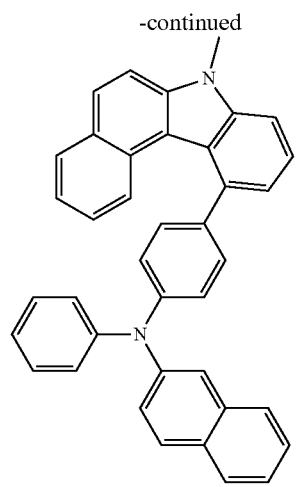
1864
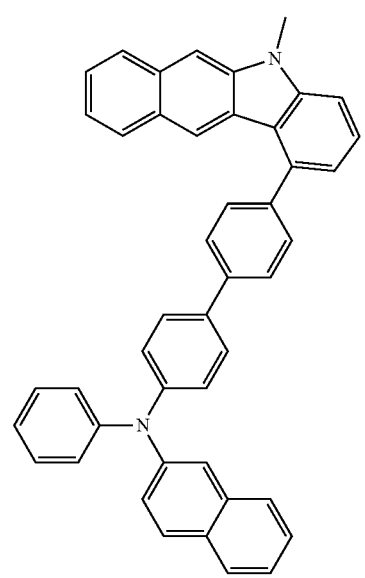
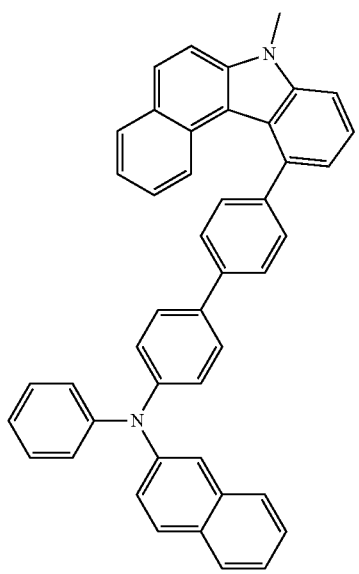
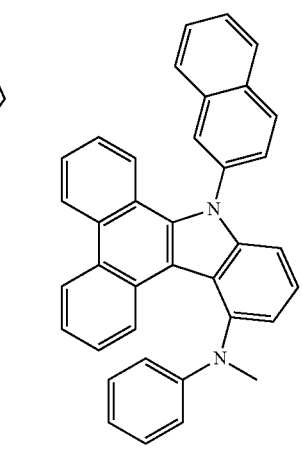
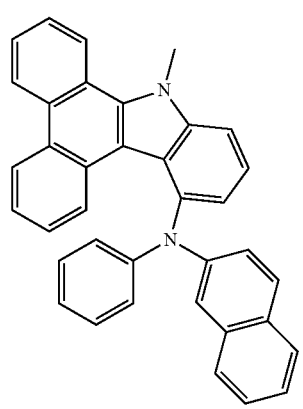
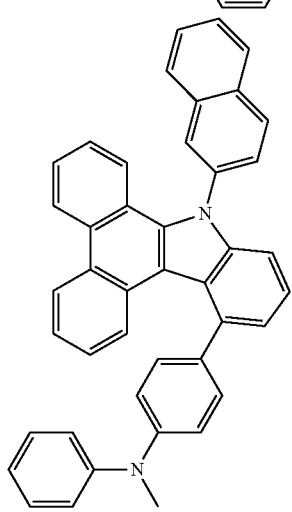
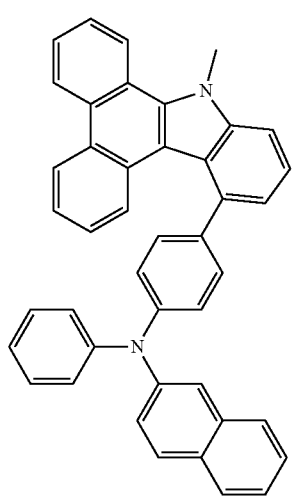
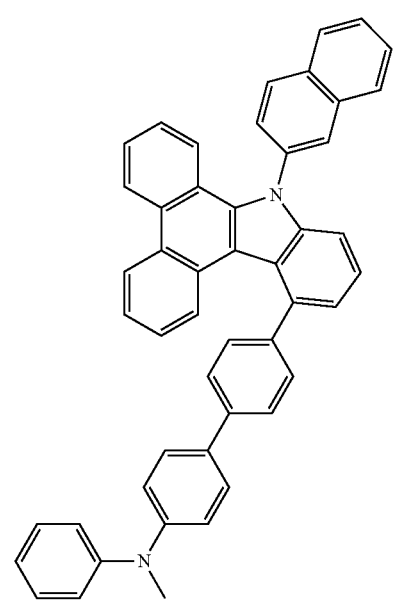

-continued
1865　　　　　1866
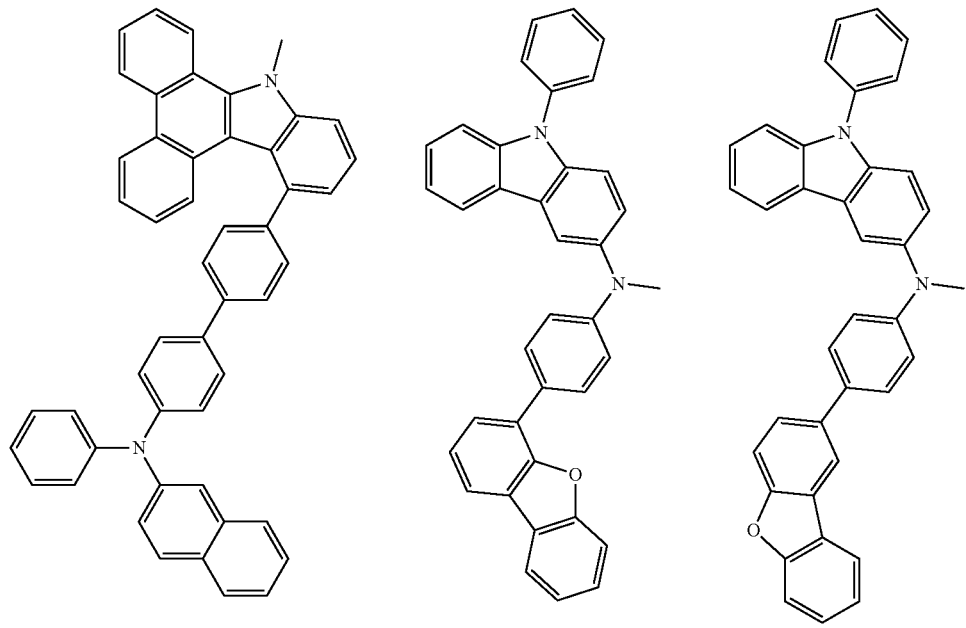
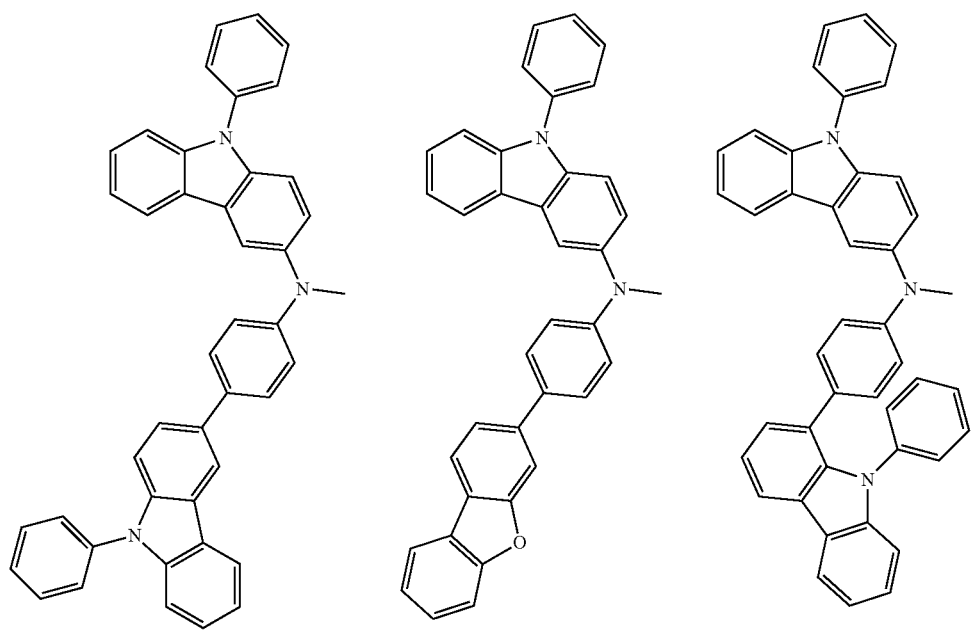

1867
-continued
1868
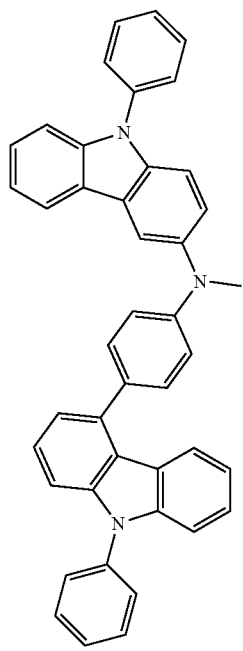
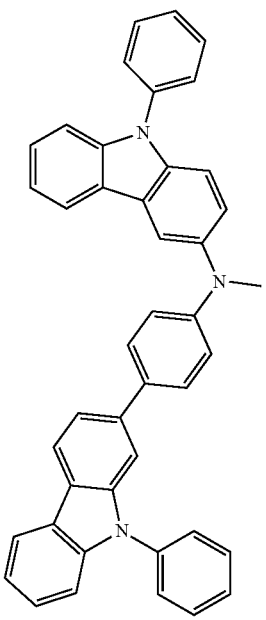
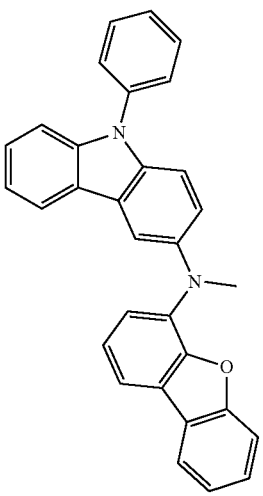
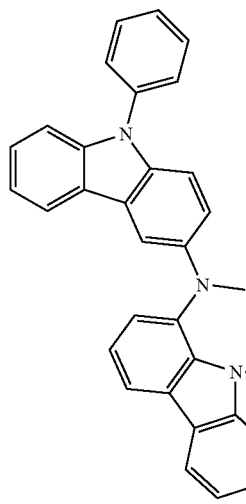
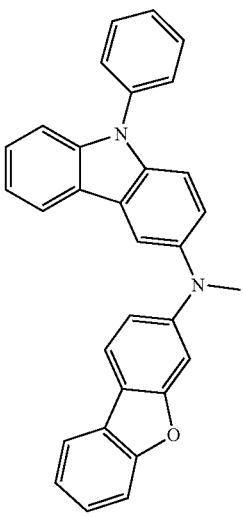
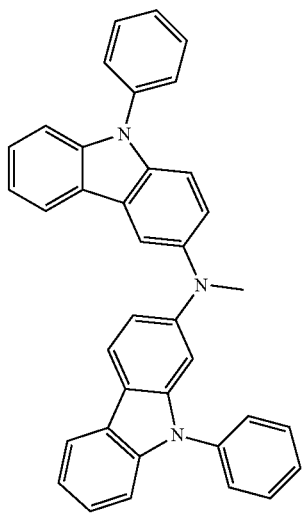
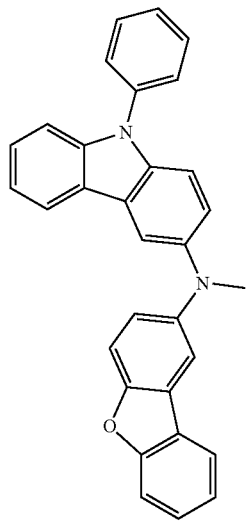
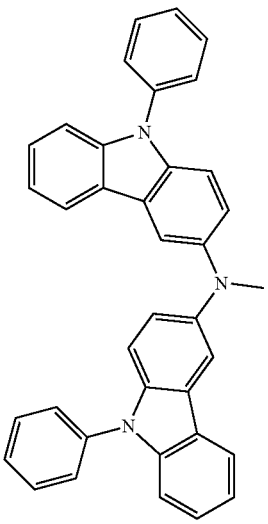
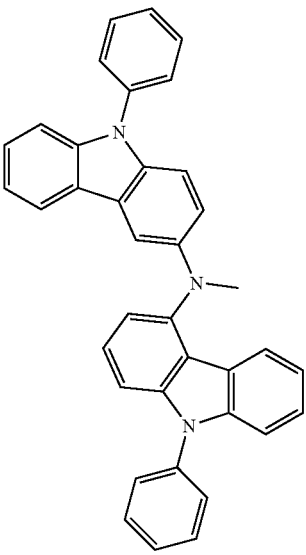

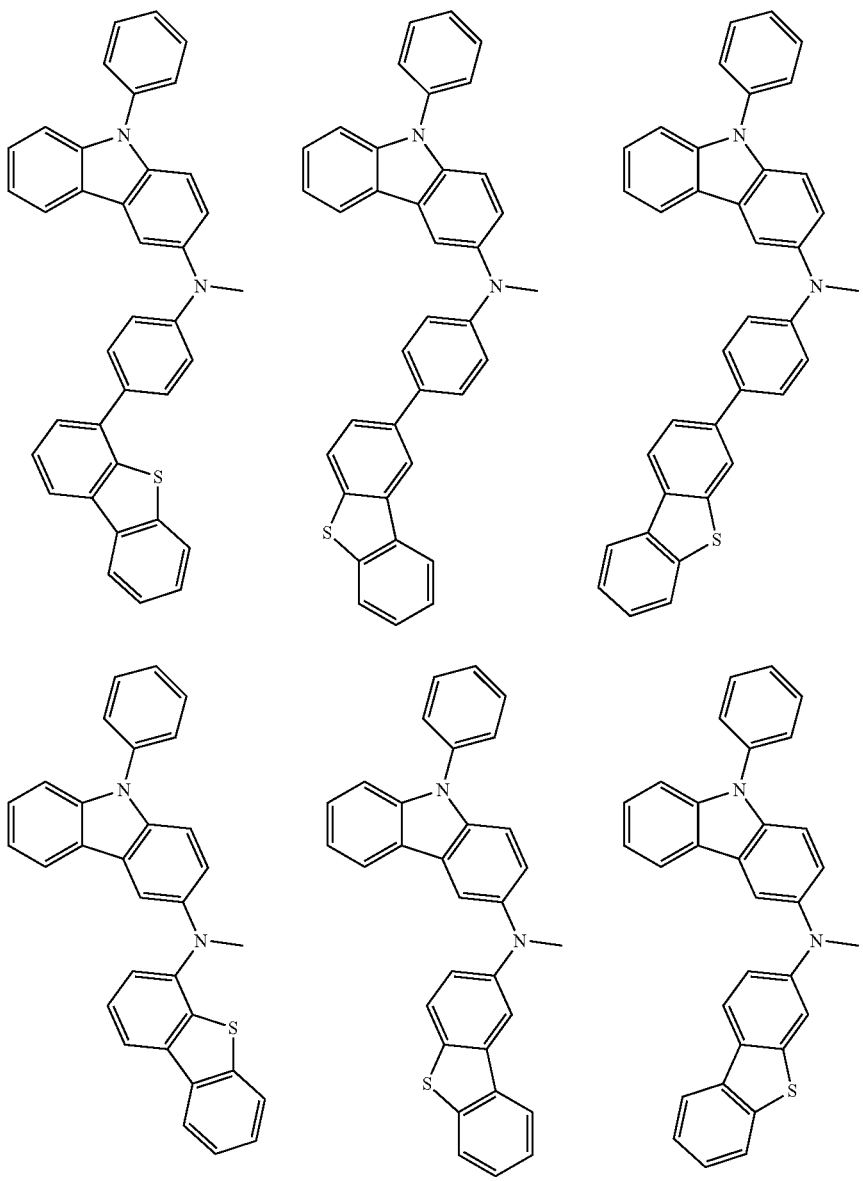

Description of Substituents Belonging to Group D Represented by Formula ($D^D$)

In formula ($D^D$), $X^1$ to $X^{16}$ each represent $C(R^1)$ to $C(R^{16})$, respectively, or a nitrogen atom, and $R^1$ to $R^{16}$ each independently represent a hydrogen atom or a substituent.

One of $X^1$ to $X^4$ represents a carbon atom which is directly bonded to a carbon atom represented by one of $X^{13}$ to $X^{16}$.

Two selected from $R^1$ to $R^8$ and two selected from $R^9$ to $R^{16}$ each not involved in the above direct bonding may be bonded to each other to form a ring.

In an aspect of the invention, two selected from $R^1$ to $R^8$ and two selected from $R^9$ to $R^{16}$, each not involved in the above direct bonding, are preferably not bonded to each other, thereby failing to form a ring.

The "direct bond" used herein is generally called a "single bond" in some cases.

$X^1$ to $X^{16}$ are each preferably $C(R^1)$ to $C(R^{16})$, respectively, and more preferably $R^1$ to $R^{16}$ are all hydrogen atoms.

In formula ($D^D$), $Y^1$ represents an oxygen atom, a sulfur atom, $C(R^A)(R^B)$, $Si(R^C)(R^D)$, $P(R^E)$, $P(=O)(R^F)$, $S(=O)_2$, $P(=S)(R^G)$, or —$N(R^H)$—, with an oxygen atom or a sulfur atom being preferred.

$R^A$ to $R^H$ each independently represent a hydrogen atom or a substituent. $R^A$ and $R^B$, and $R^C$ and $R^D$ may be bonded to each other to form a ring.

* is bonded to one of *1 to *3 in formula 1[V].

$R^A$ to $R^H$ each preferably represent an aryl group, which is preferably selected from the following aryl groups:

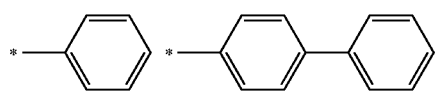

1871
-continued
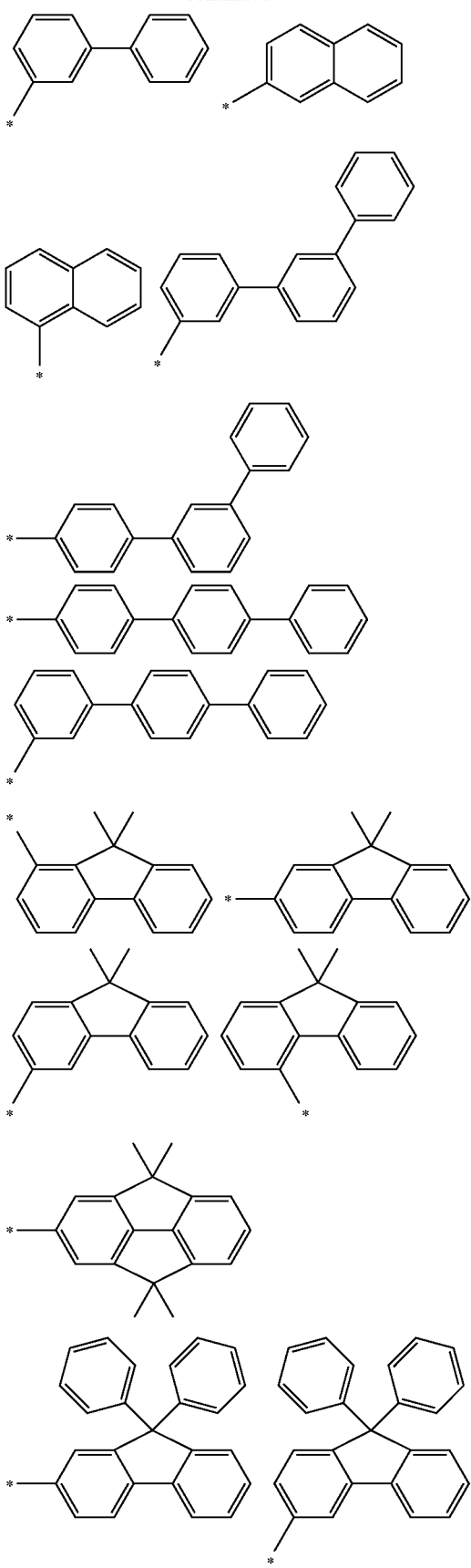
1872
-continued
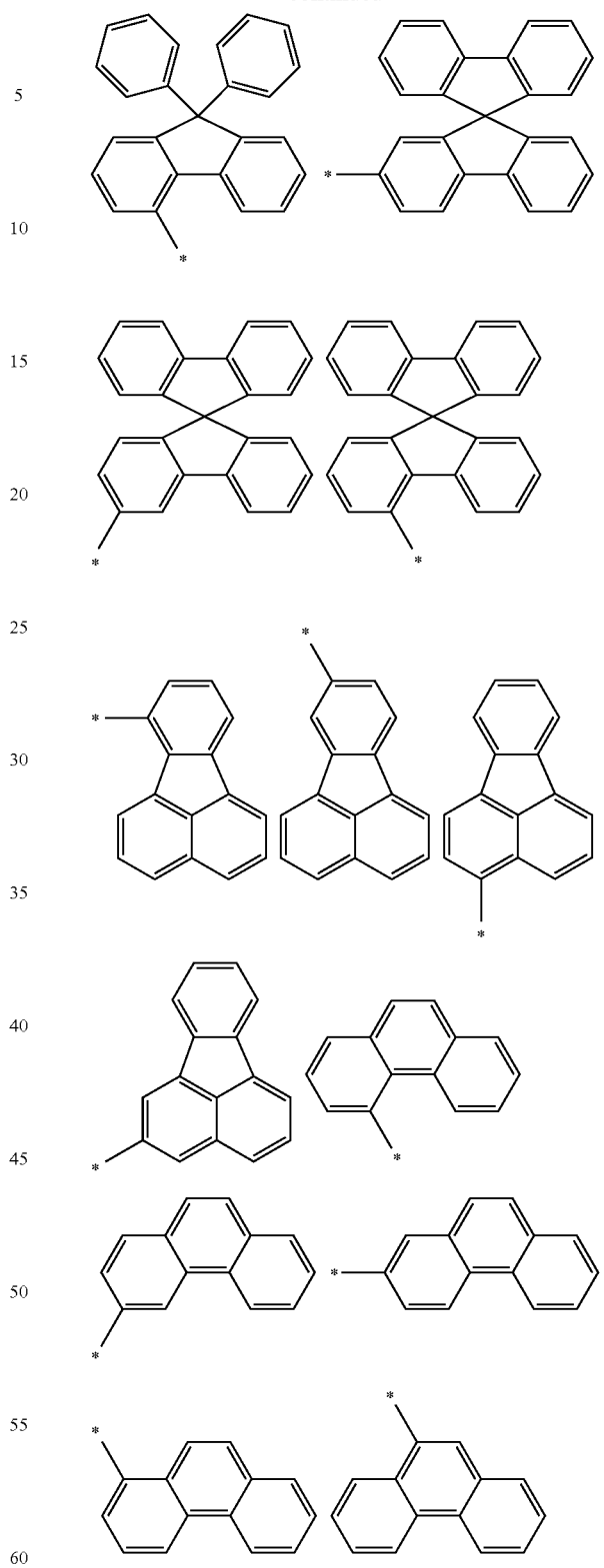
wherein * indicates a bonding site and each carbon atom other than that at the bonding site may have a substituent.
The structures wherein $R^A$ and $R^B$ in $C(R^A)(R^B)$ or $R^C$ and $R^D$ in $Si(R^C)(R^D)$ are bonded to each other to form a ring are shown below:

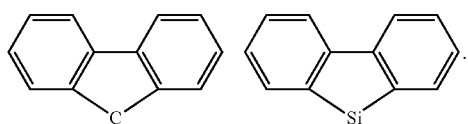

In an aspect of the invention, the group represented by formula ($D^D$) is preferably a group represented by formula ($D^{D1}$):

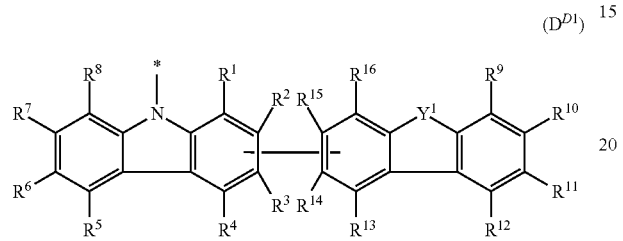

(D$^{D1}$)

in formula ($D^{D1}$), each symbol is as defined above in formula ($D^D$).

In an aspect of the invention, the group represented by formula ($D^D$) is preferably a group represented by formula ($D^{D2}$):

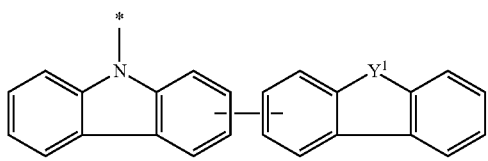

(D$^{D2}$)

in formula ($D^{D2}$), each symbol is as defined above in formula ($D^D$).

Examples of the group represented by formula ($D^D$) are preferably selected from the following groups, wherein a hydrogen atom bonded to a carbon atom may be substituted with the substituent mentioned above.

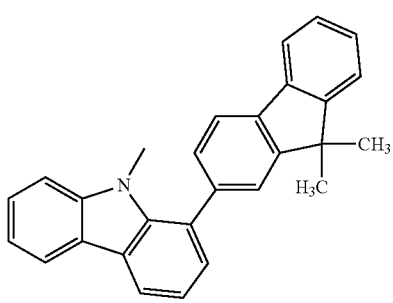

-continued

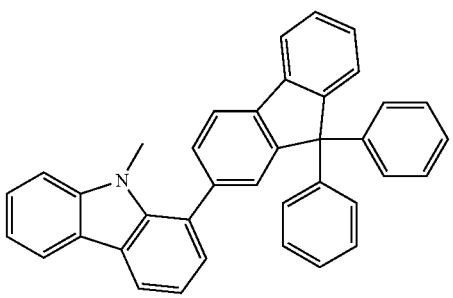

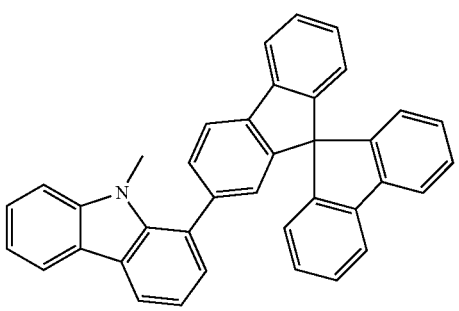

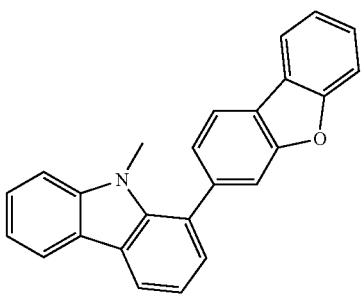

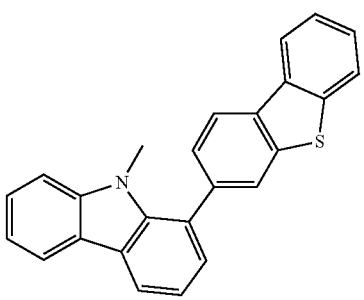

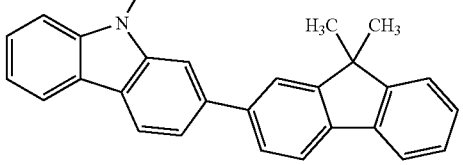

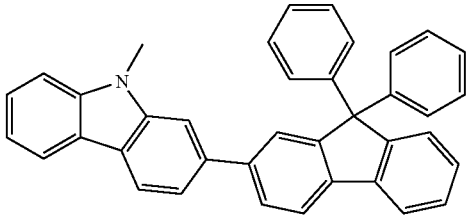

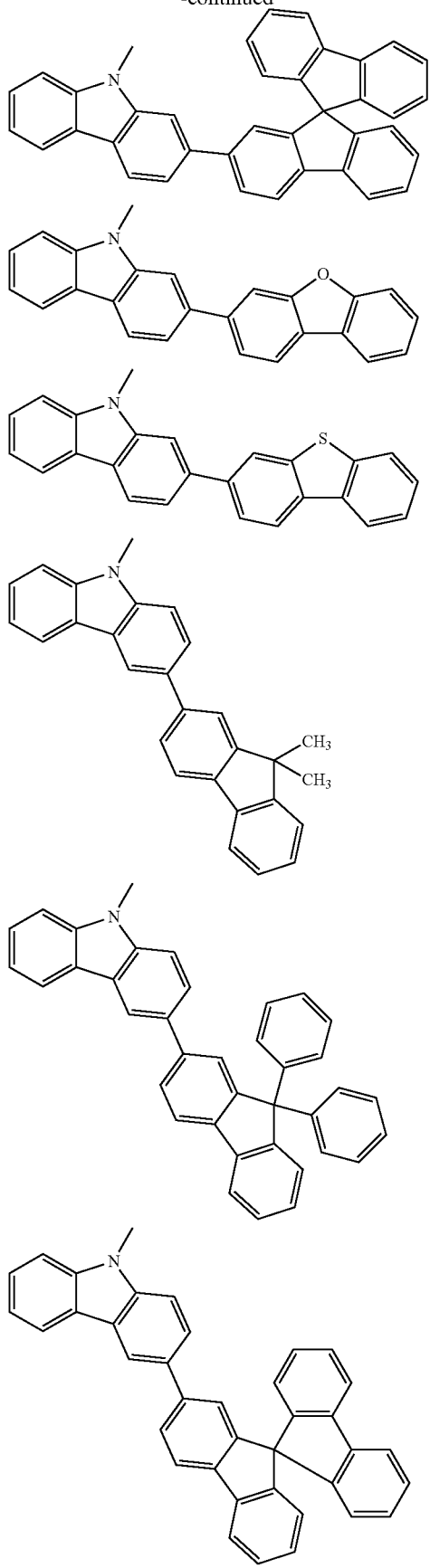
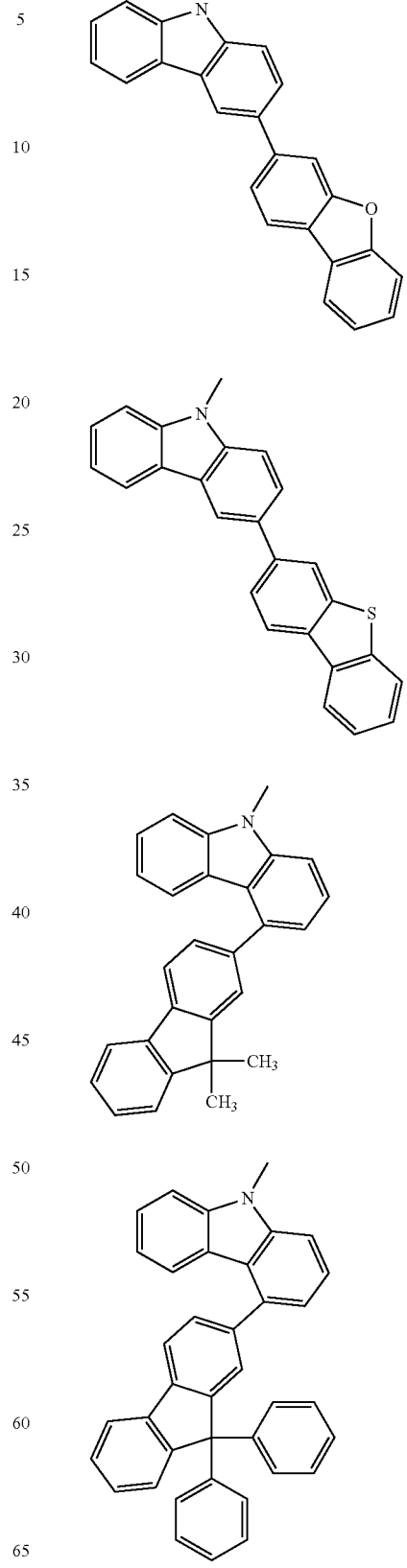

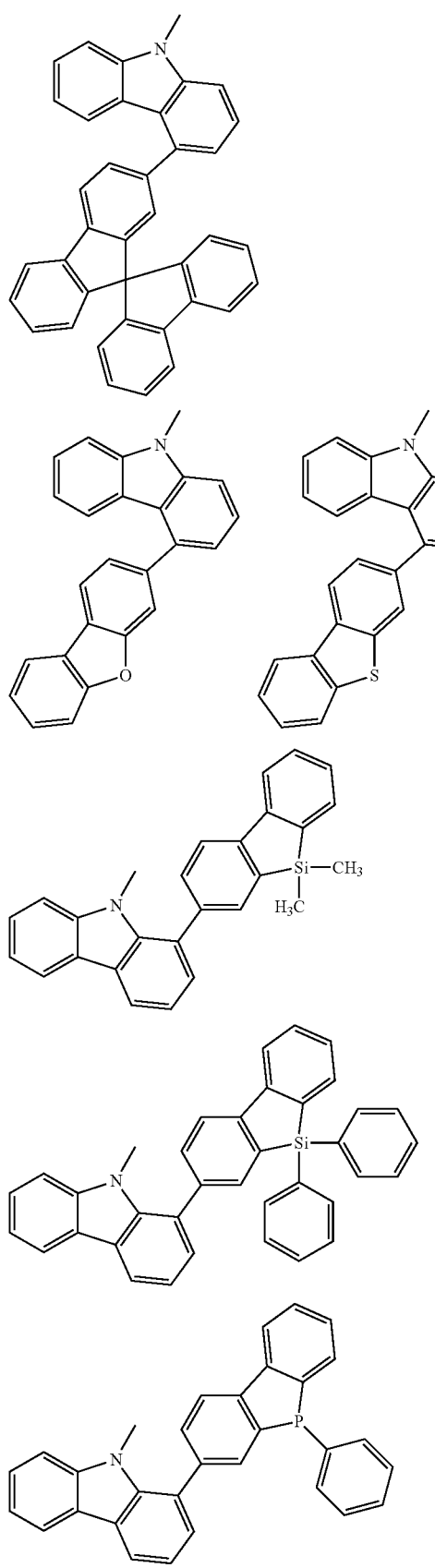
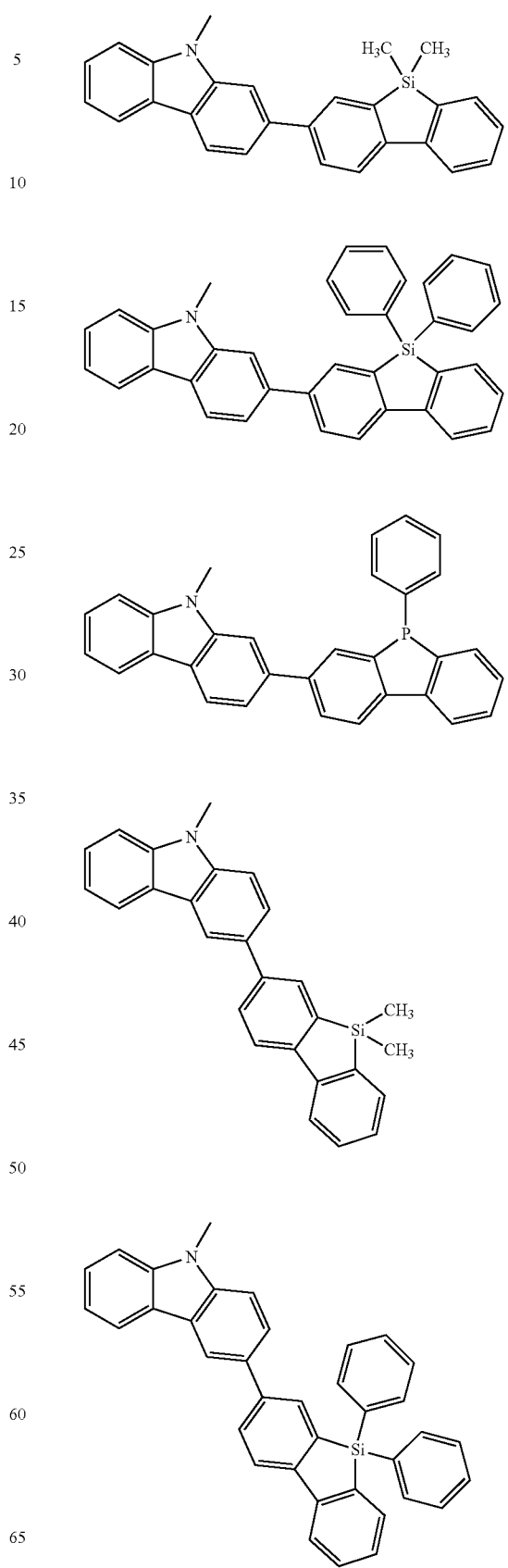

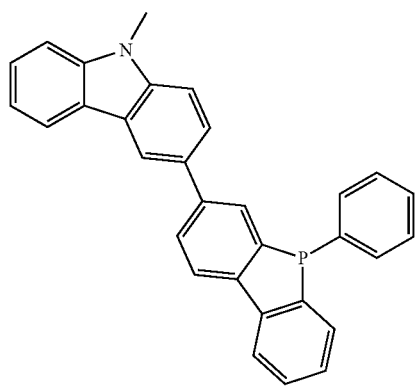
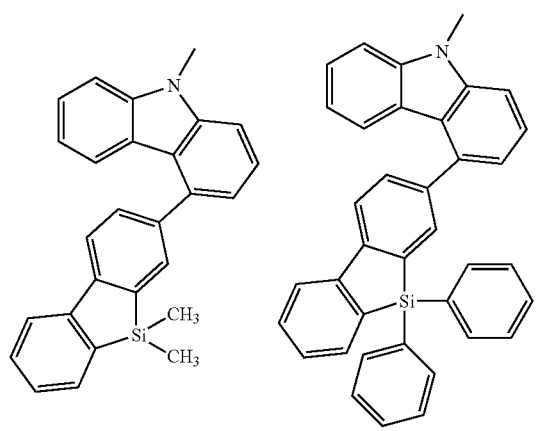

1881
-continued
1882
-continued
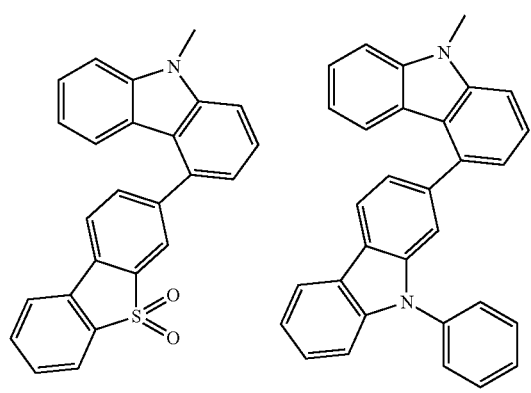
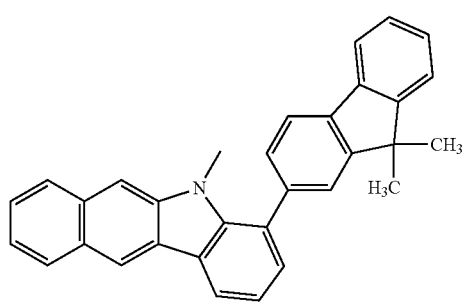
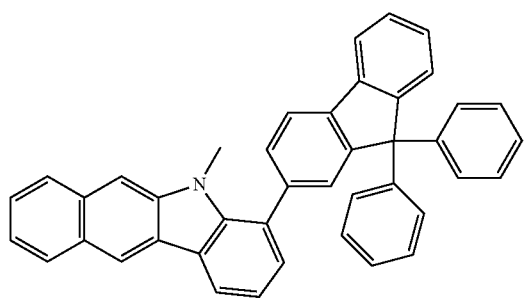
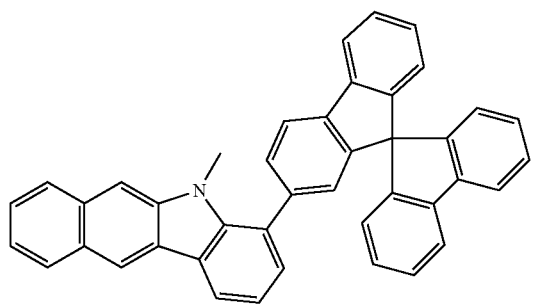
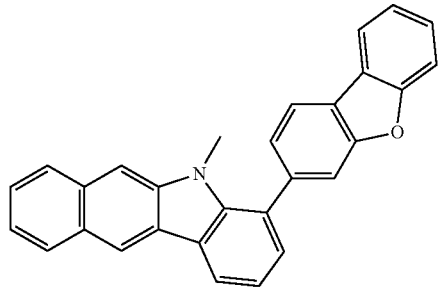
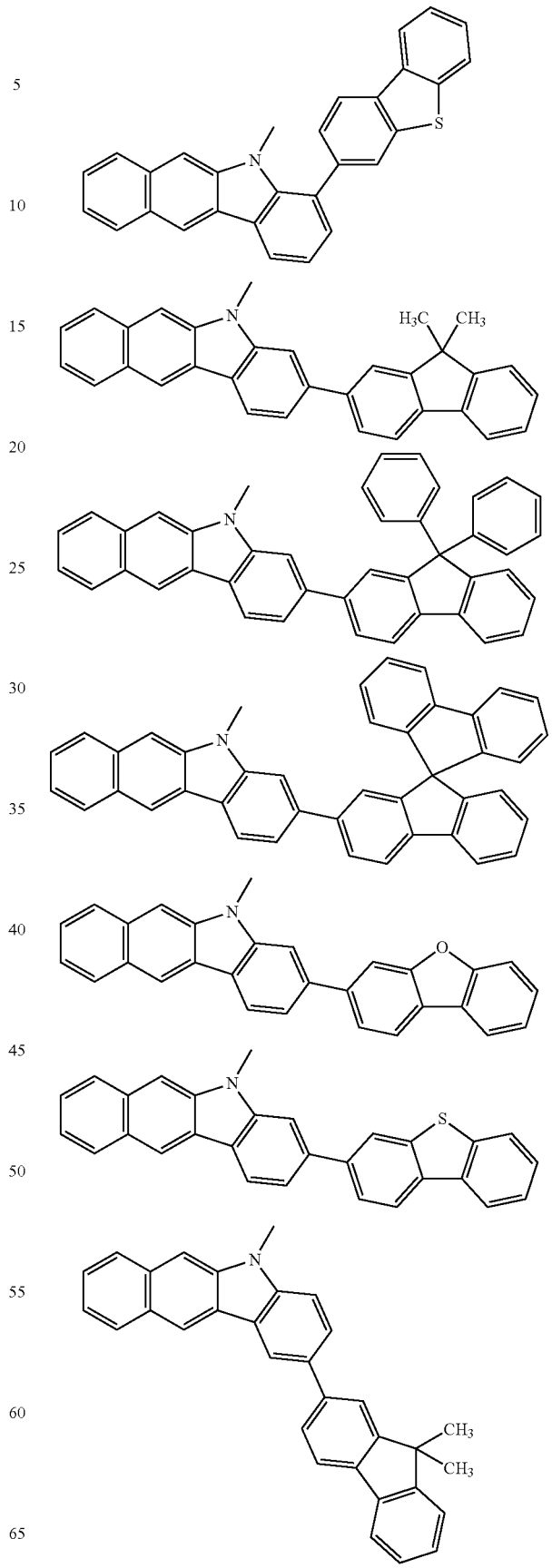

1883
-continued
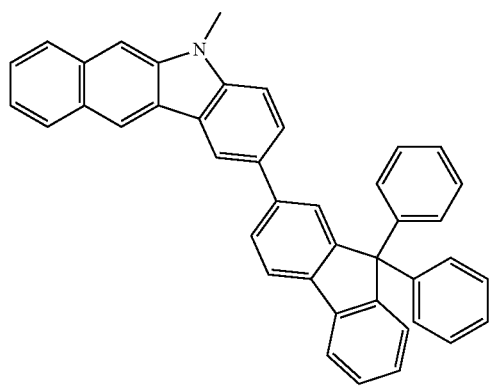
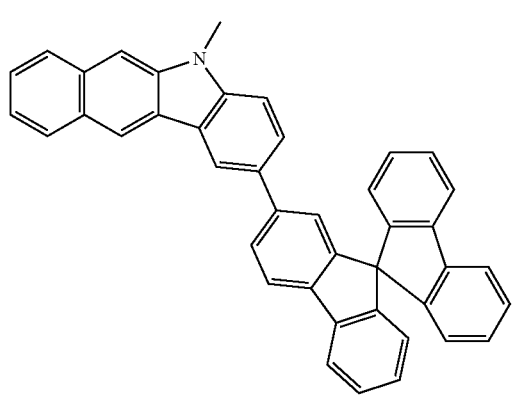
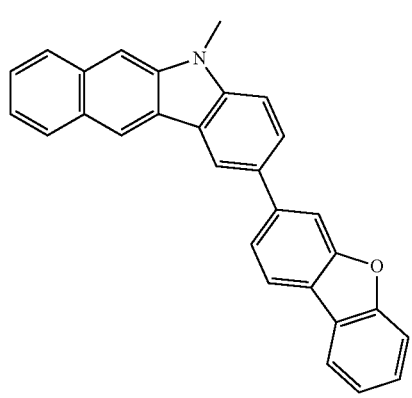
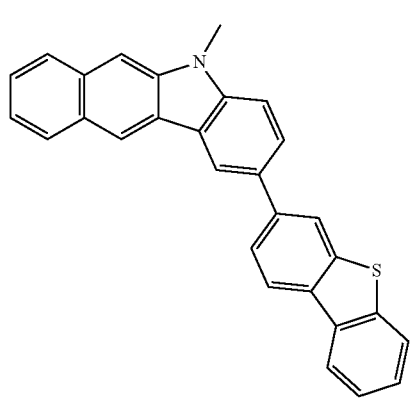
1884
-continued
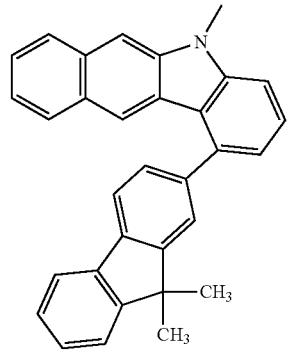
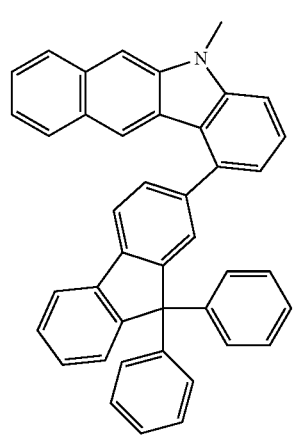
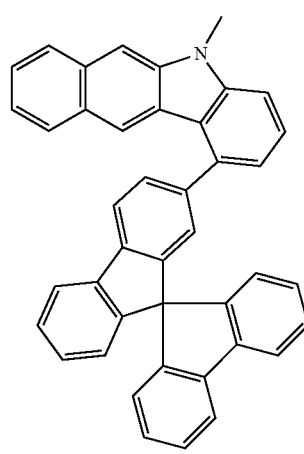
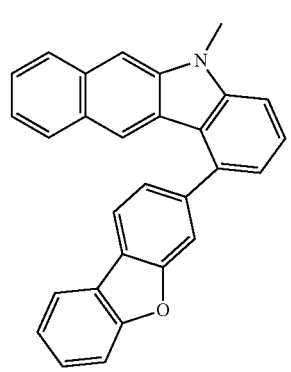

1885
-continued
1886
-continued
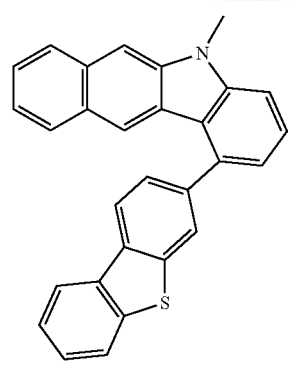
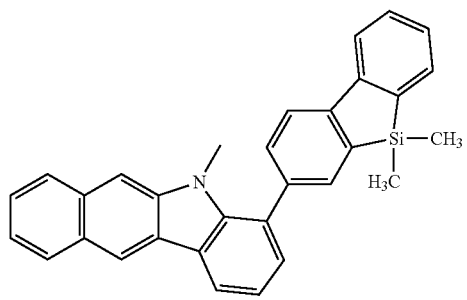
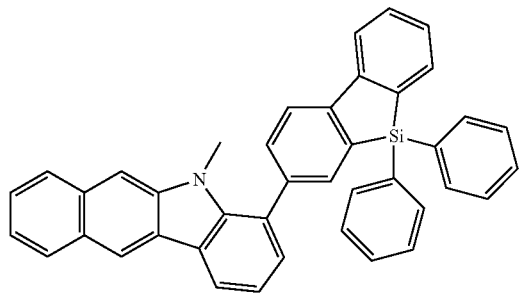
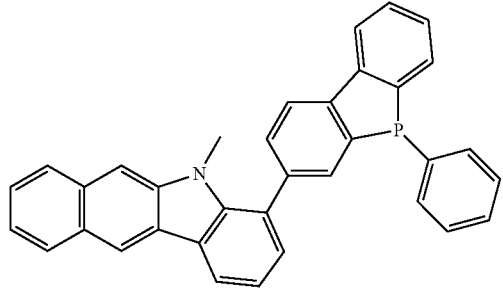
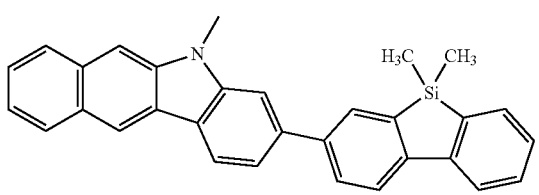
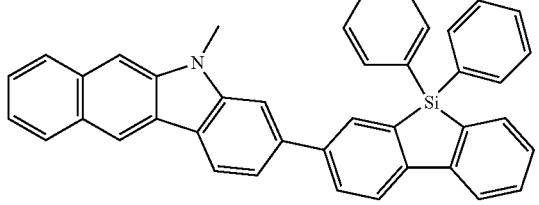
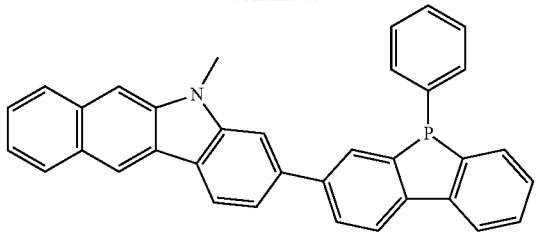
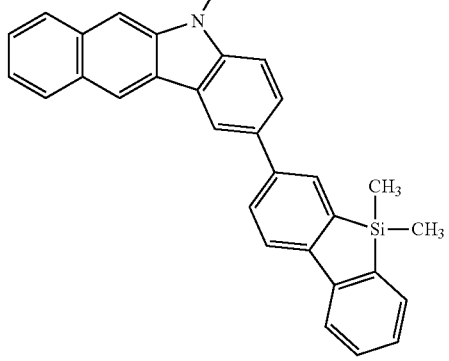
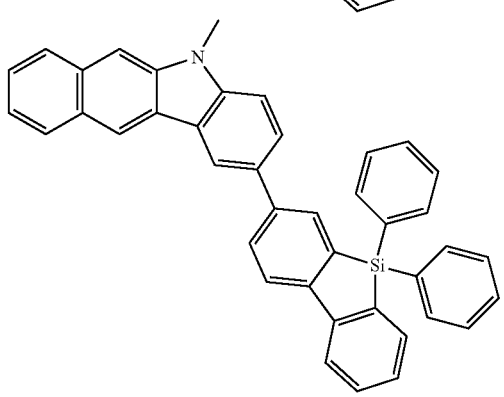
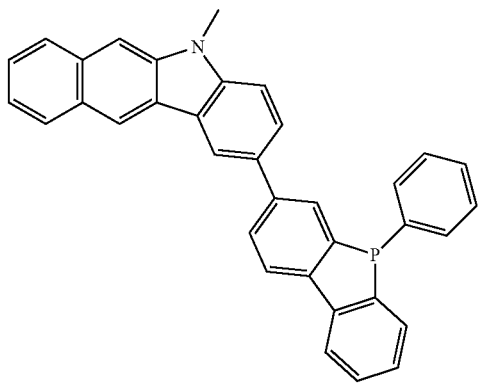
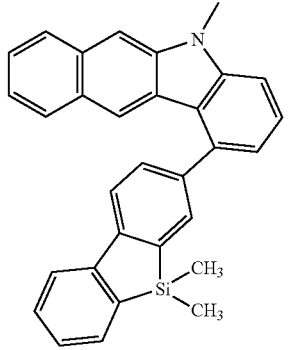

1887
-continued
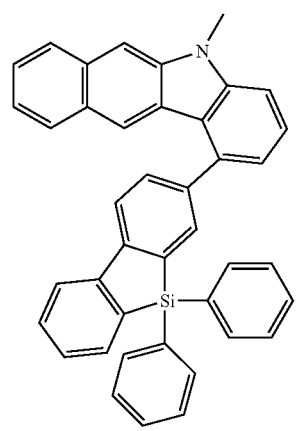
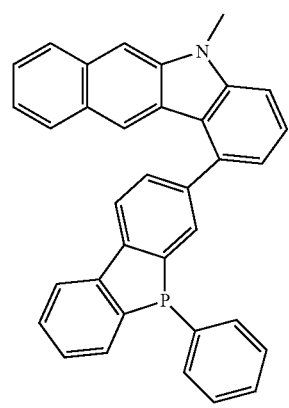
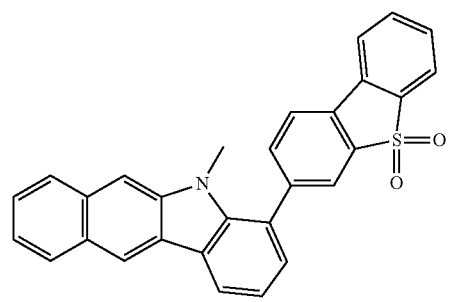
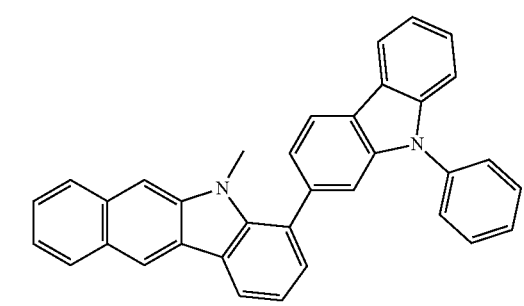
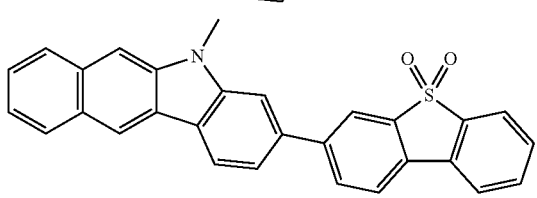
1888
-continued
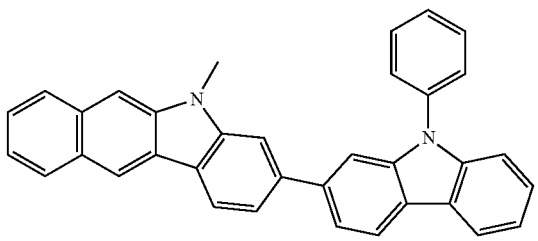
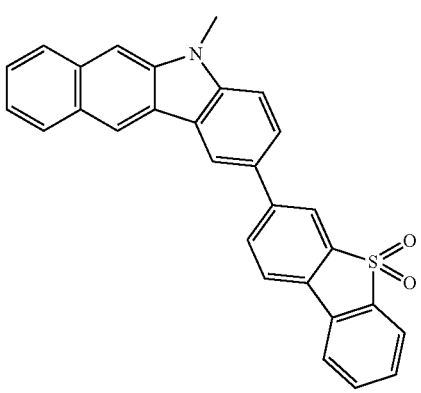
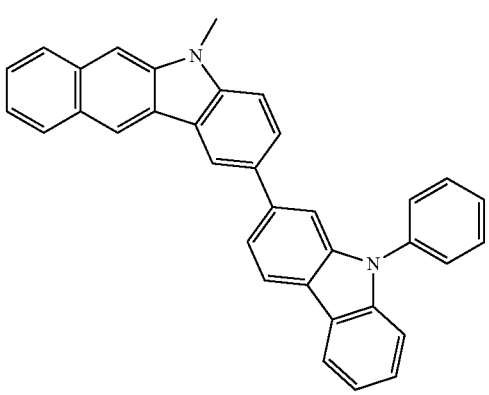
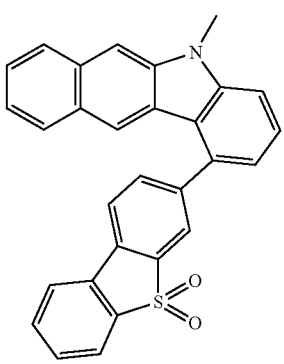

1889
-continued
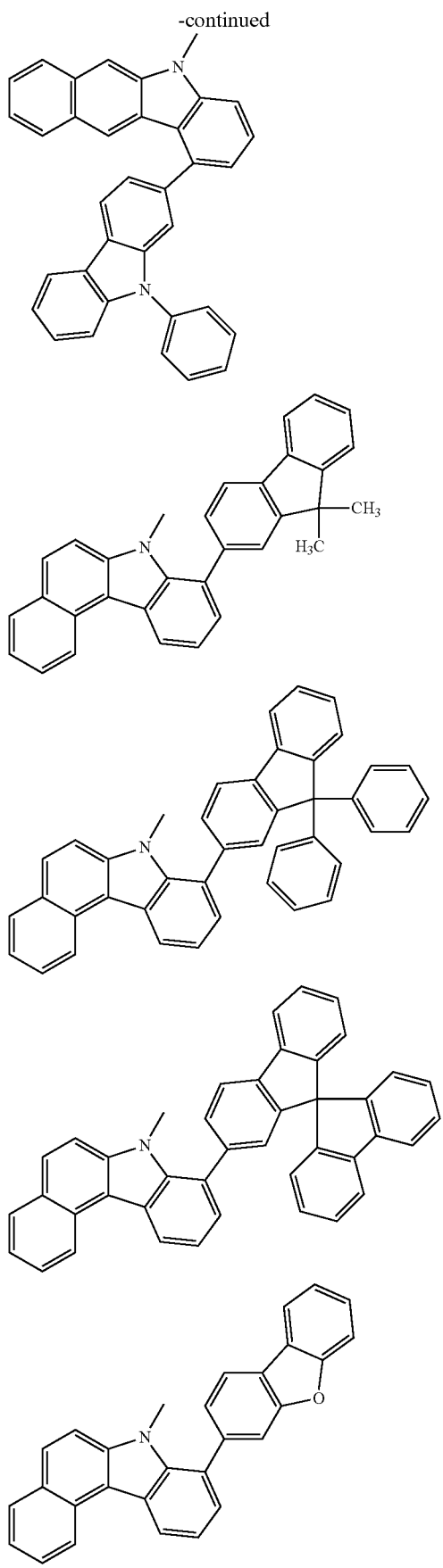
1890
-continued
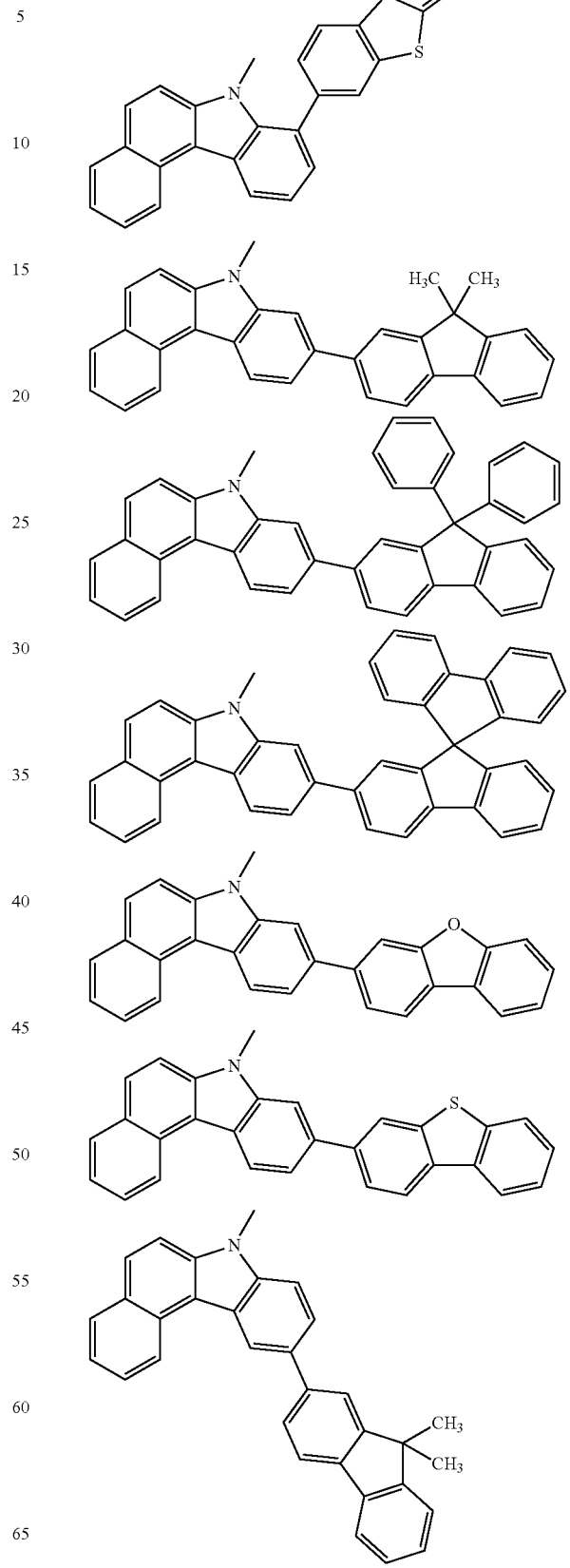

1891
-continued
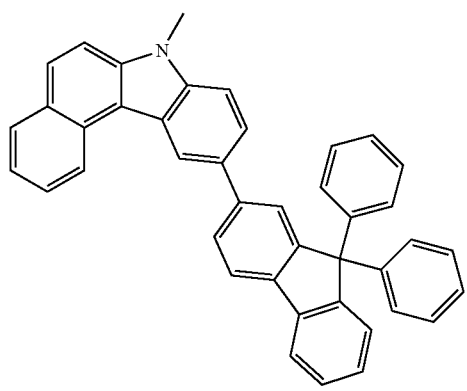
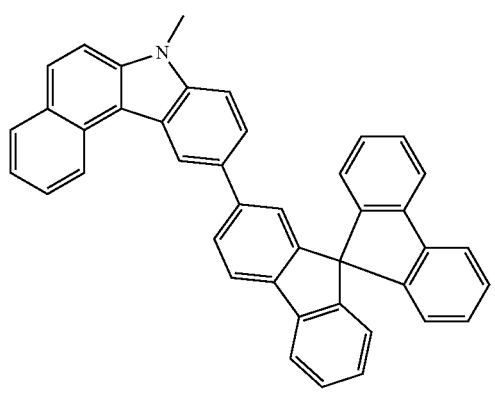
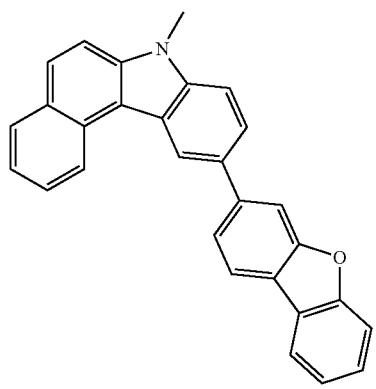
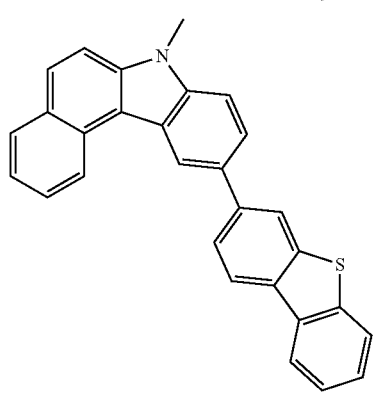
1892
-continued
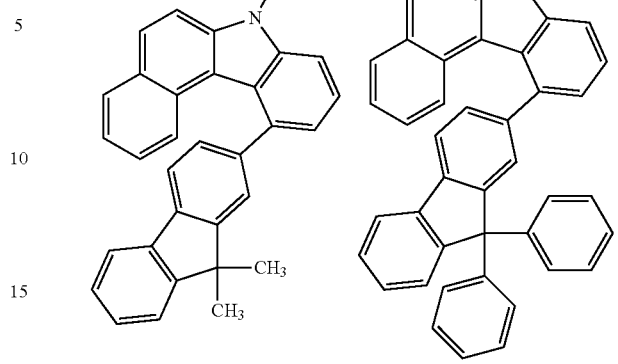
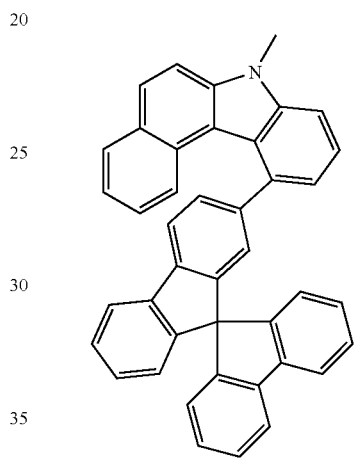
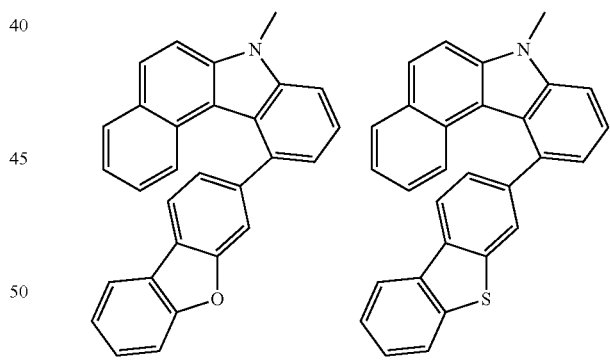
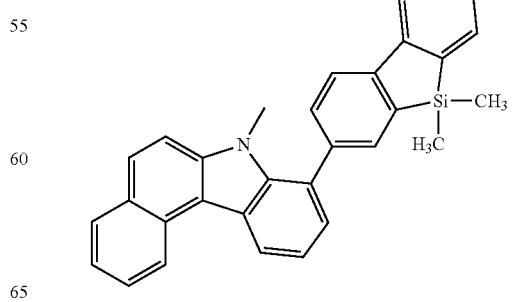

1893
-continued
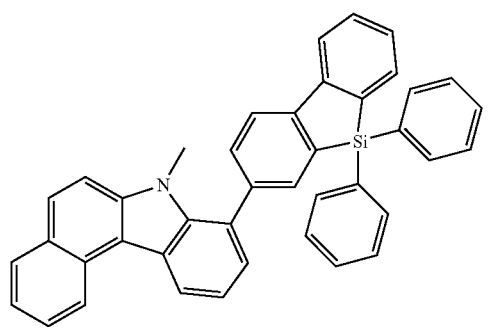
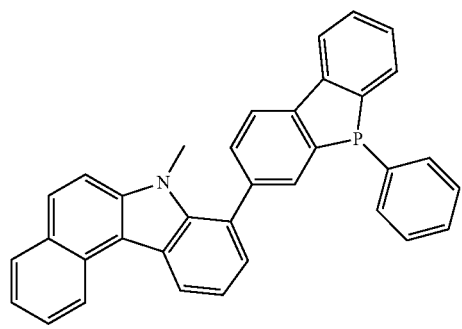
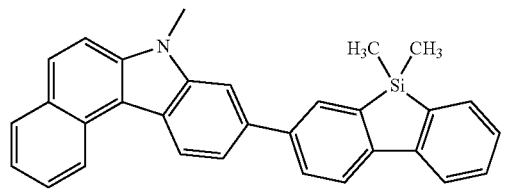
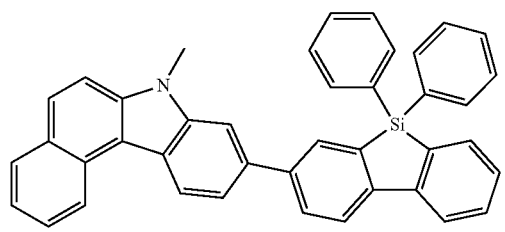
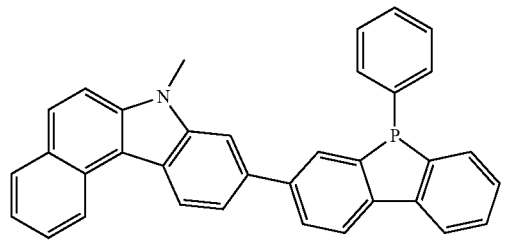
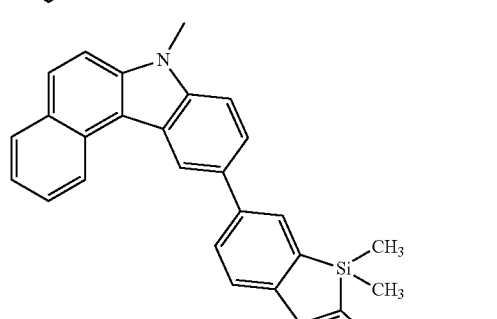
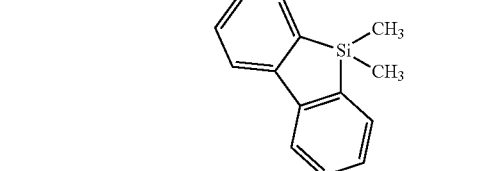
1894
-continued
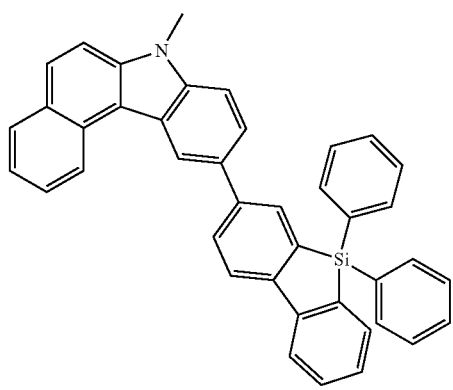
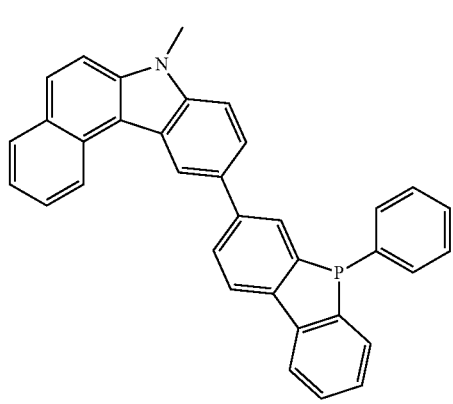
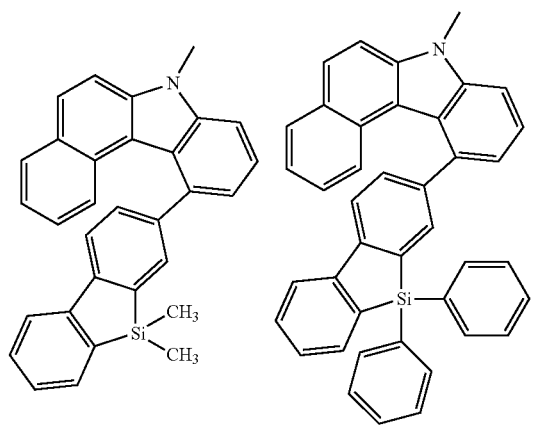
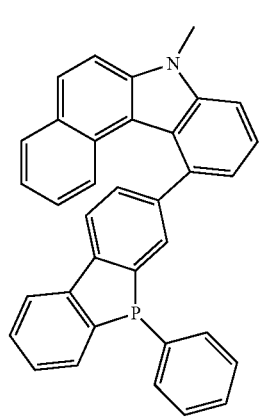

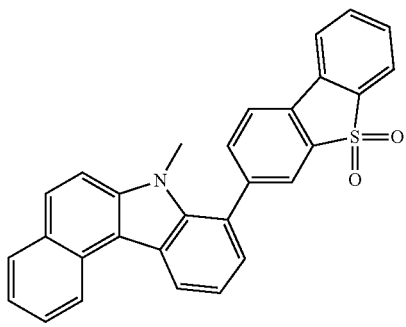
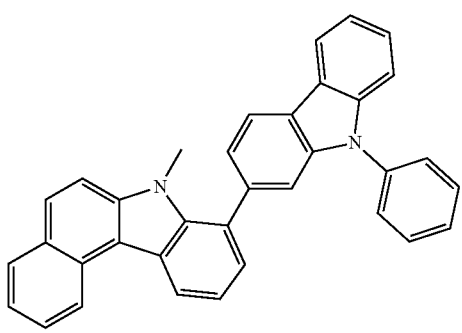
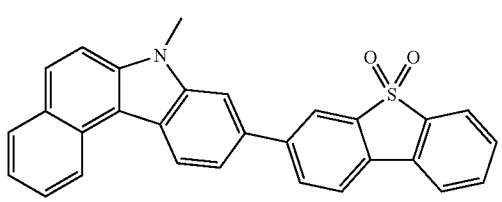
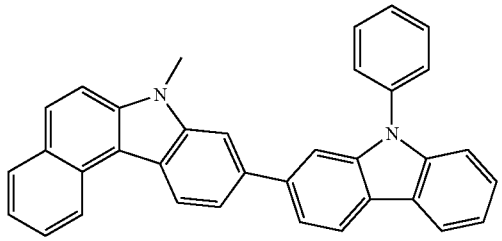
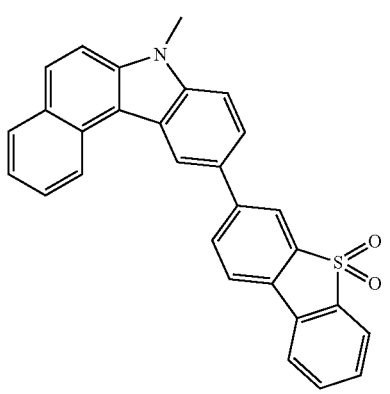
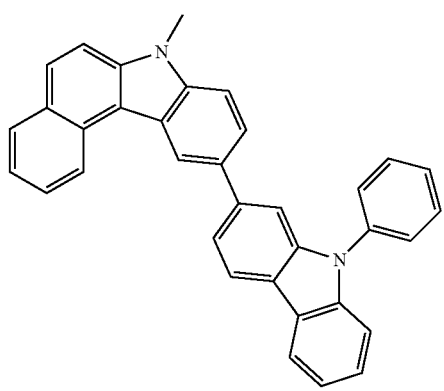
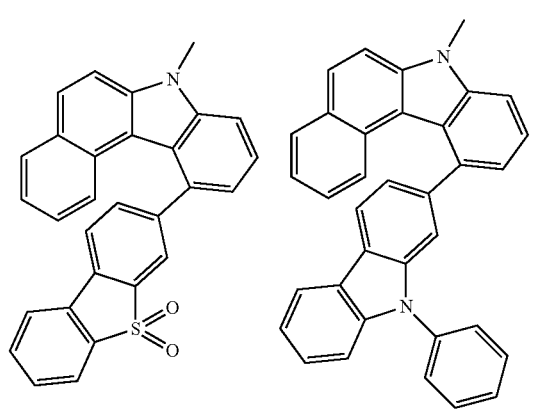
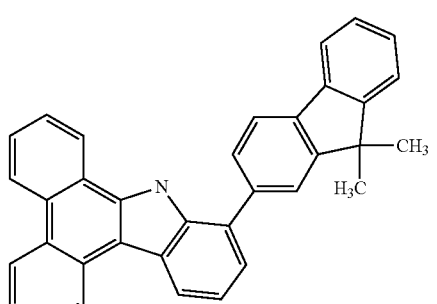
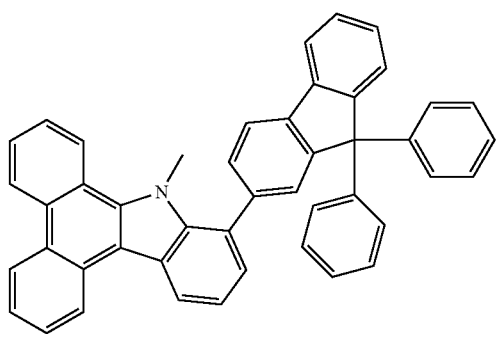

1897
-continued
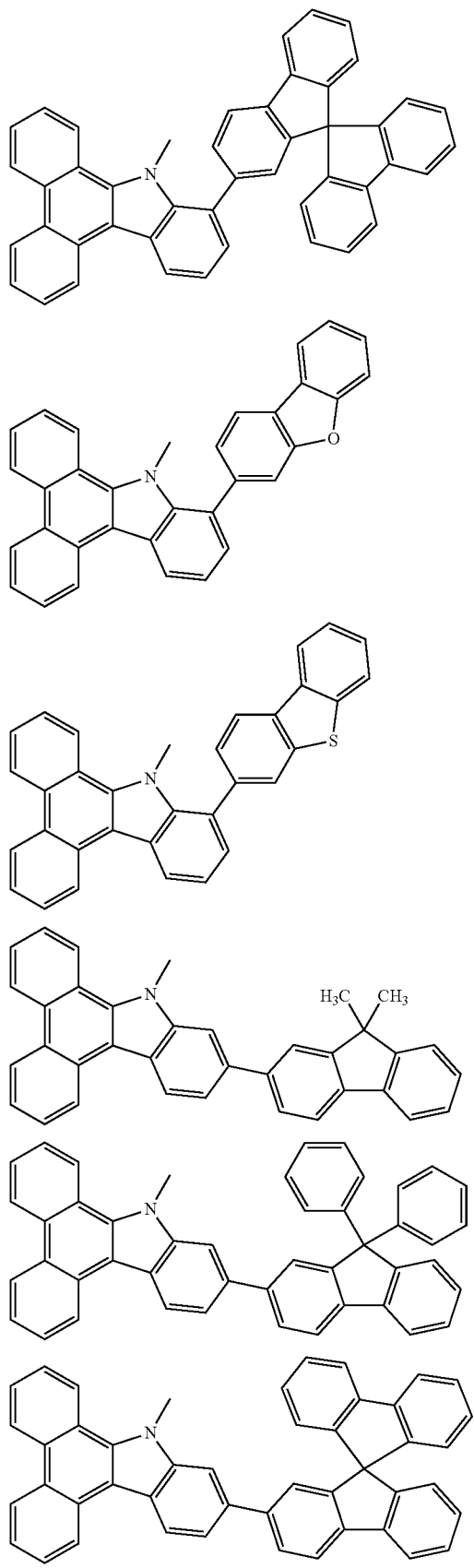
1898
-continued
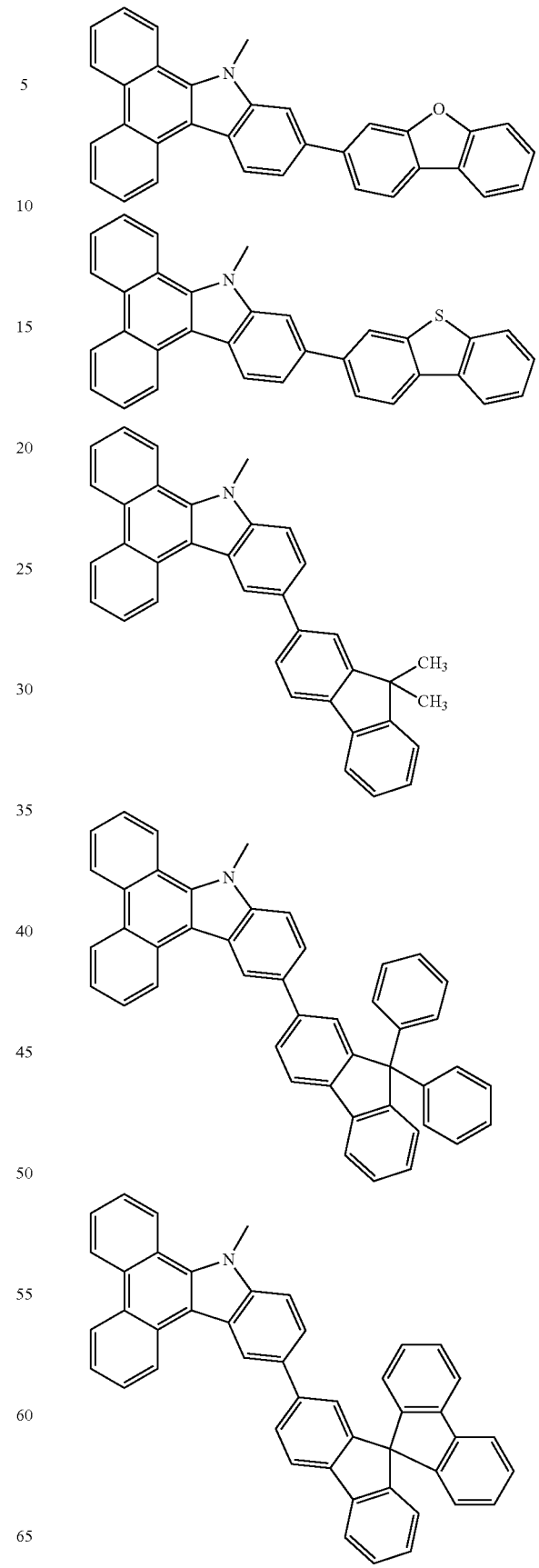

1899
-continued
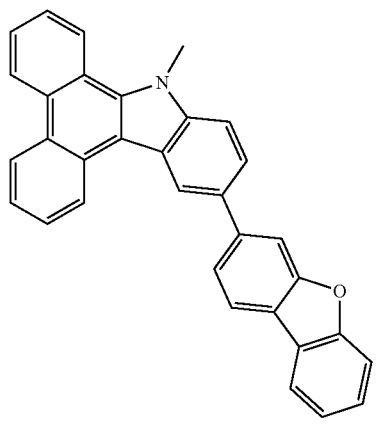
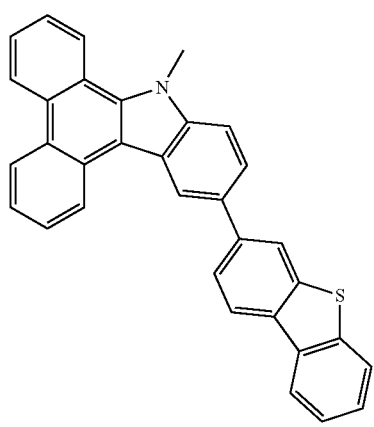
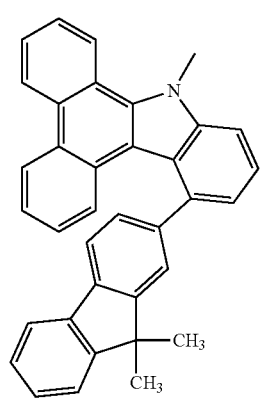 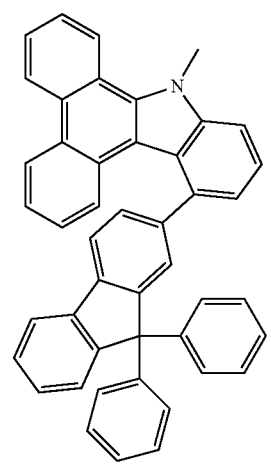
1900
-continued
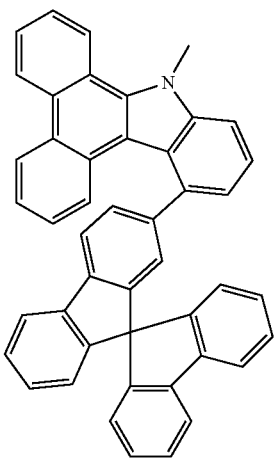
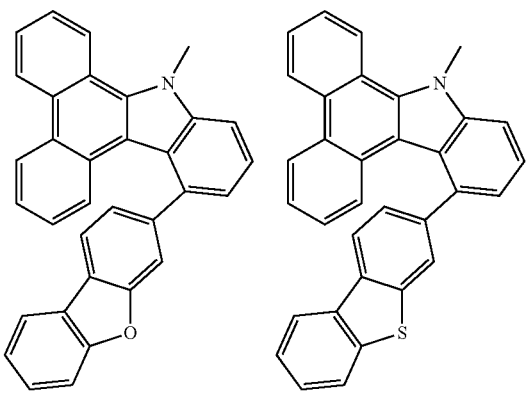
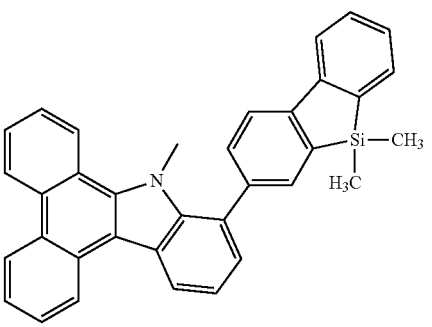
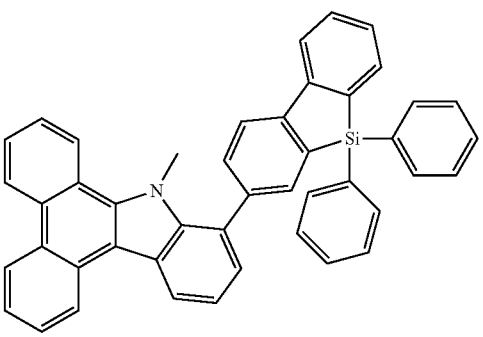

1901
-continued
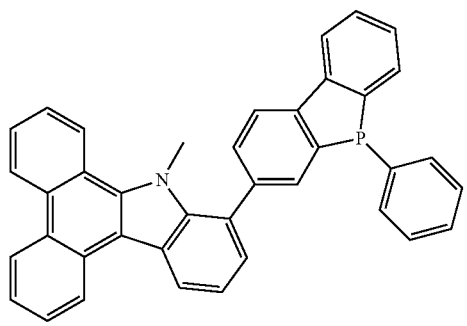
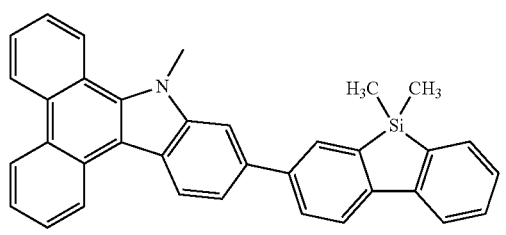
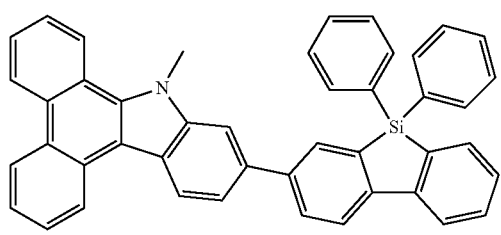
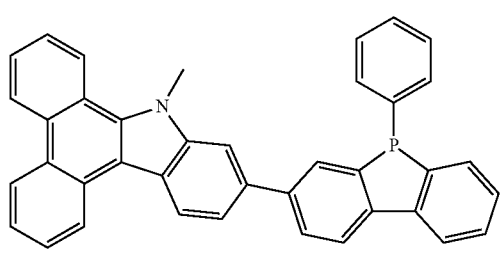
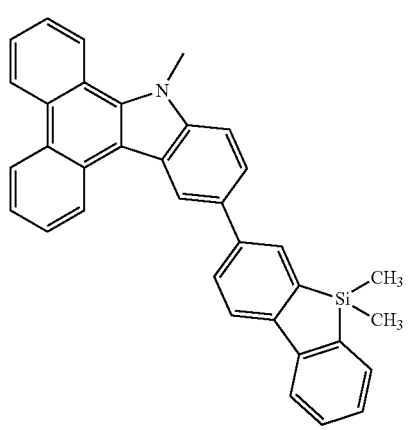
1902
-continued
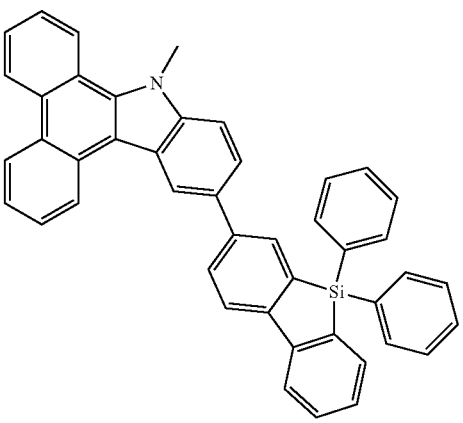
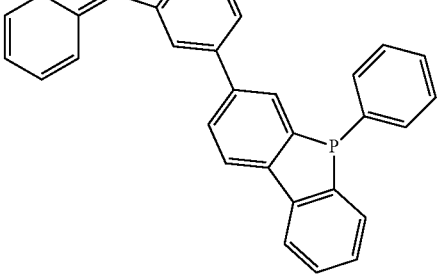
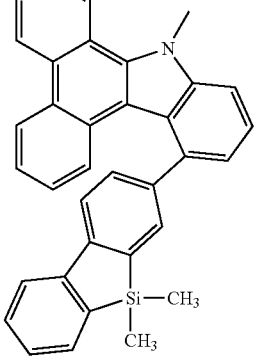
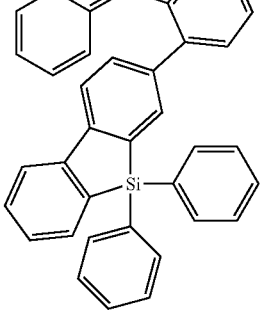

-continued
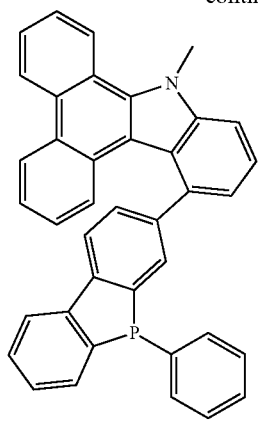
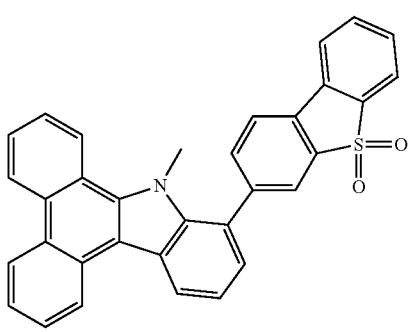
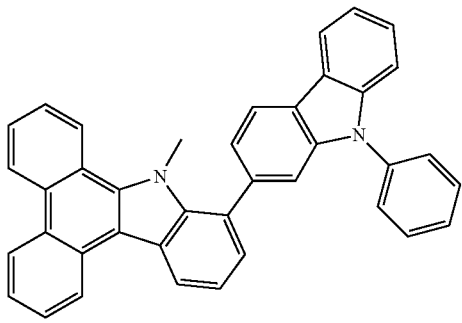
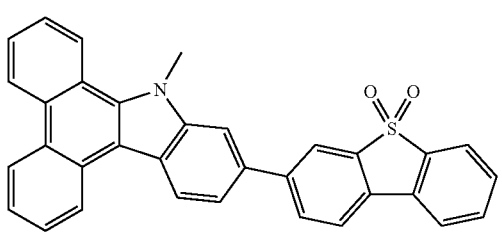
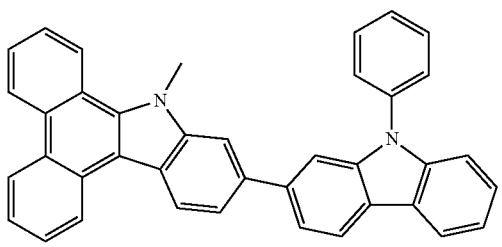
-continued
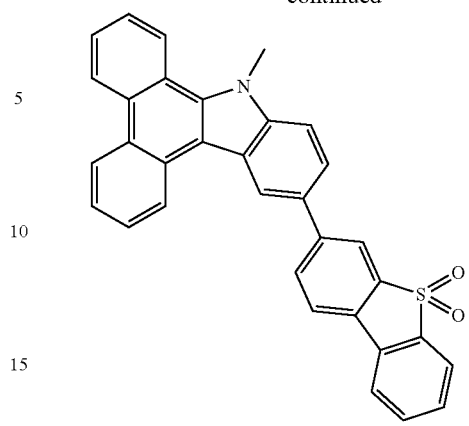
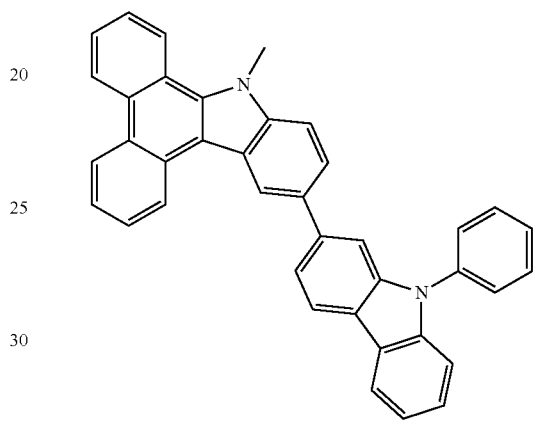
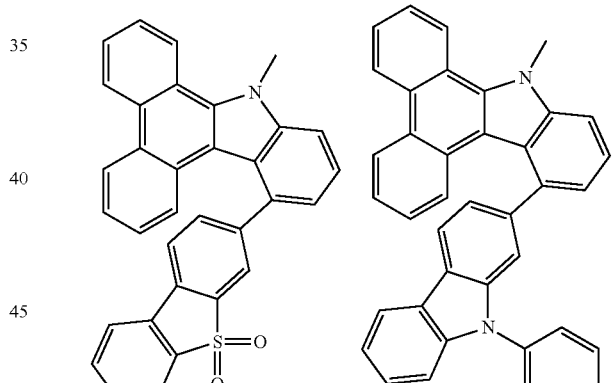
Compound in an Aspect of the Invention
In an aspect, the compound of the invention is preferably a compound represented by formula 1a[V] (also referred to as "compound 1a[V]"):
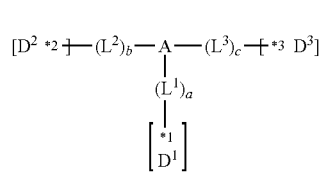
(1a[V])
in formula 1a[V], each symbol is as defined above in formula 1[V].

In an aspect, the compound (1a) of the invention is more preferably a compound represented by any of formulae 1a-1[V] to 1a-4[V] (also referred to as "compounds 1a-1[V] to 1a-4[V]"):

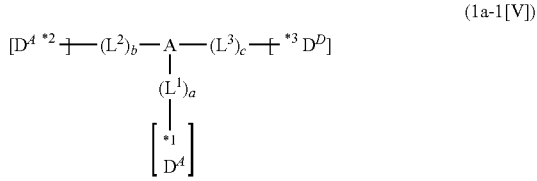
(1a-1[V])

in formula 1a-1[V], $D^A$ represents a group represented by formula ($D^A$) which is belong to Group A described in formula 1[V], $D^D$ represents a group represented by formula ($D^D$) which is belong to Group D described in formula 1[V], and the other symbols are as defined above in formula 1[V];

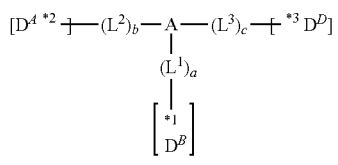
(1a-2[V])

in formula 1a-2[V], $D^A$ represents a group represented by formula ($D^A$) which is belong to Group A described in formula 1[V], $D^B$ represents a group represented by formula ($D^B$) which is belong to Group B described in formula 1[V], $D^D$ represents a group represented by formula ($D^D$) which is belong to Group D described in formula 1[V], and the other symbols are as defined above in formula 1[V];

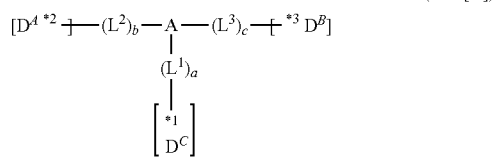
(1a-3[V])

in formula 1a-3[V], $D^A$ represents a group represented by formula ($D^A$) which is belong to Group A described in formula 1[V], $D^B$ represents a group represented by formula ($D^B$) which is belong to Group B described above in formula 1[V], $D^C$ represents a group represented by formula ($D^C$) which is belong to Group C described in formula 1[V], and the other symbols are as defined above in formula 1[V]; and

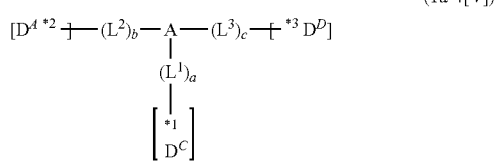
(1a-4[V])

in formula 1a-4[V], $D^A$ represents a group represented by formula ($D^A$) which is belong to Group A described in formula 1[V], $D^C$ represents a group represented by formula ($D^C$) which is belong to Group C described in formula 1[V], $D^D$ represents a group represented by formula ($D^D$) which is belong to Group D described in formula 1[V], and the other symbols are as defined above in formula 1[V].

In an aspect of the invention, the compound 1[V] or the compound 1a[V] is more preferably a compound represented by formula 1a-i[V] (also referred to as "compound 1a-i[V]"):

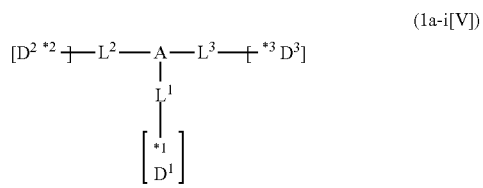
(1a-i[V])

in formula 1a-i[V], each symbol is as defined above in formula 1[V].

In an aspect of the invention, the compound 1a-i[V] is more preferably a compound represented by formula 1a-4-i[V] (also referred to as "compound 1a-4-i[V]"):

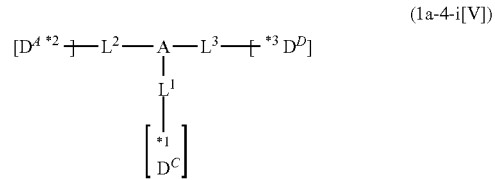
(1a-4-i[V])

in formula 1a-4-i[V], $D^A$ represents a group represented by formula ($D^A$) which is belong to Group A described with respect to formula 1[V], $D^C$ represents a group represented by formula ($D^C$) which is belong to Group C described with respect to formula 1[V], $D^D$ represents a group represented by formula ($D^D$) which is belong to Group D described with respect to formula 1[V], and the other symbols are as defined above in formula 1[V].

In an aspect of the invention, the compound 1[V] or the compound 1a[V] is more preferably a compound represented by formula 1a-ii[V] (also referred to as "compound 1a-ii[V]"):

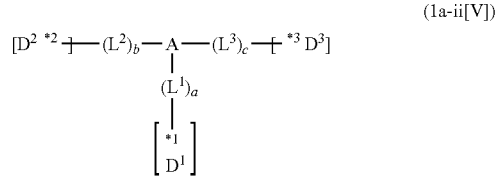
(1a-ii[V])

in formula 1a-ii[V], each symbol is as defined above in formula 1[V].

In an aspect of the invention, the compound 1[V] or the compound 1a[V] is more preferably a compound represented by formula 1a-iii[V] (also referred to as "compound 1a-iii[V]"):

(1a-iii[V])

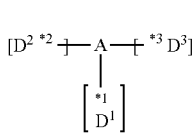

in formula 1a-iii[V], each symbol is as defined above in formula 1[V].

In an aspect of the invention, the compound 1a-iii[V] is more preferably a compound represented by any of formulae 1a-1-iii[V] to 1a-3-iii[V] (also referred to as "compounds 1a-1-iii[V] to 1a-3-iii[V]"):

(1a-1-iii[V])

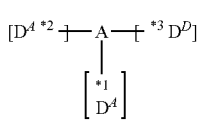

in formula 1a-1-iii[V], $D^A$ represents a group represented by formula ($D^A$) which is belong to Group A described with respect to formula 1[V], $D^D$ represents a group represented by formula ($D^D$) which is belong to Group D described with respect to formula 1[V], and the other symbols are as defined above in formula 1[V];

(1a-2-iii[V])

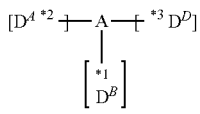

in formula 1a-2-iii[V], $D^A$ represents a group represented by formula ($D^A$) which is belong to Group A described with respect to formula 1[V], $D^B$ represents a group represented by formula ($D^B$) which is belong to Group B described above with respect to formula 1[V], $D^D$ represents a group represented by formula ($D^D$) which is belong to Group D described with respect to formula 1[V], and the other symbols are as defined above in formula 1[V]; and (1a-3-iii[V])

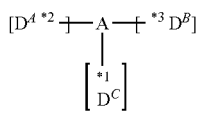

in formula 1a-3-iii[V], $D^A$ represents a group represented by formula ($D^A$) which is belong to Group A described with respect to formula 1[V], $D^B$ represents a group represented by formula ($D^B$) which is belong to Group B described above with respect to formula 1[V], $D^C$ represents a group represented by formula ($D^C$) which is belong to Group C described with respect to formula 1[V], the other symbols are as defined above in formula 1[V].

In an aspect of the invention, the compound 1[V] or the compound 1a[V] is more preferably a compound represented by formula 1a-iv[V] (also referred to as "compound 1a-iv[V]"):

(1a-iv[V])

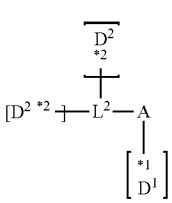

in formula 1a-iv[V], each symbol is as defined above in formula 1[V].

In an aspect of the invention, the compound 1[V] is more preferably a compound represented by any of formulae 1b-i[V] to 1b-iv[V] (also referred to as "compounds 1b-i[V] to 1b-iv[V]"):

(1b-i[V])

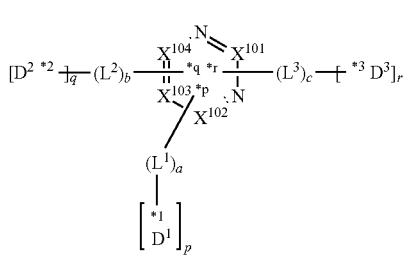

in formula 1b-i[V], each symbol is as defined above in formula 1[V]; $X^{101}$ to $X^{104}$ each represent a carbon atom bonded to one of *p to *r, C(Rx), or a nitrogen atom; Rx represents a hydrogen atom or a substituent; two or more groups Rx may be the same or different; and two selected from groups Rx may be bonded to each other to form a ring;

(1b-ii[V])

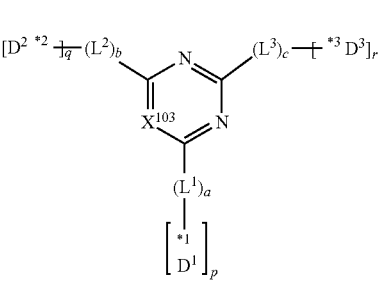

in formula 1b-ii[V], each symbol is as defined above in formula 1[V]; $X^{103}$ represents C(Rx) or a nitrogen atom, and Rx represents a hydrogen atom or a substituent;

(1b-iii[V])

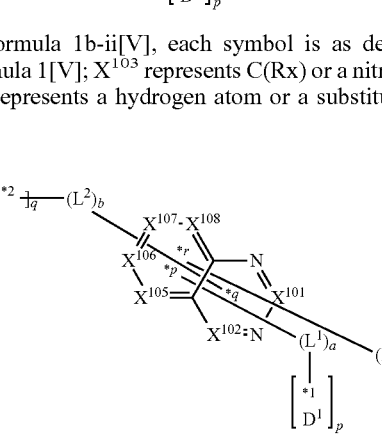

in formula 1b-iii[V], each symbol is as defined above in formula 1[V]; $X^{101}$, $X^{102}$, and $X^{105}$ to $X^{108}$ each represent a carbon atom bonded to one of *p to *r, C(Rx), or a nitrogen atom; Rx represents a hydrogen atom or a substituent, two or more groups Rx may be the same or different, and two selected from groups Rx may be bonded to each other to form a ring; and

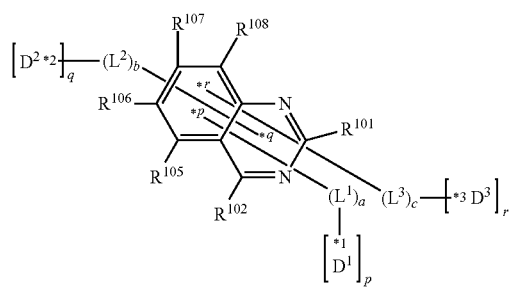

(1b-iv[V])

in formula 1b-iv[V], each symbol is as defined above in formula 1[V]; 1 to 3 carbon atoms from which one to three selected from $R^{101}$, $R^{102}$, and $R^{105}$ to $R^{108}$ are removed are each bonded to one of *p to *r; the others each independently represent a hydrogen atom or a substituent; and two selected from $R^{102}$ and $R^{105}$ to $R^{108}$ may be bonded to each other to form a ring.

Examples of the compound 1[V] in an aspect of the invention are shown below, although not limited thereto.

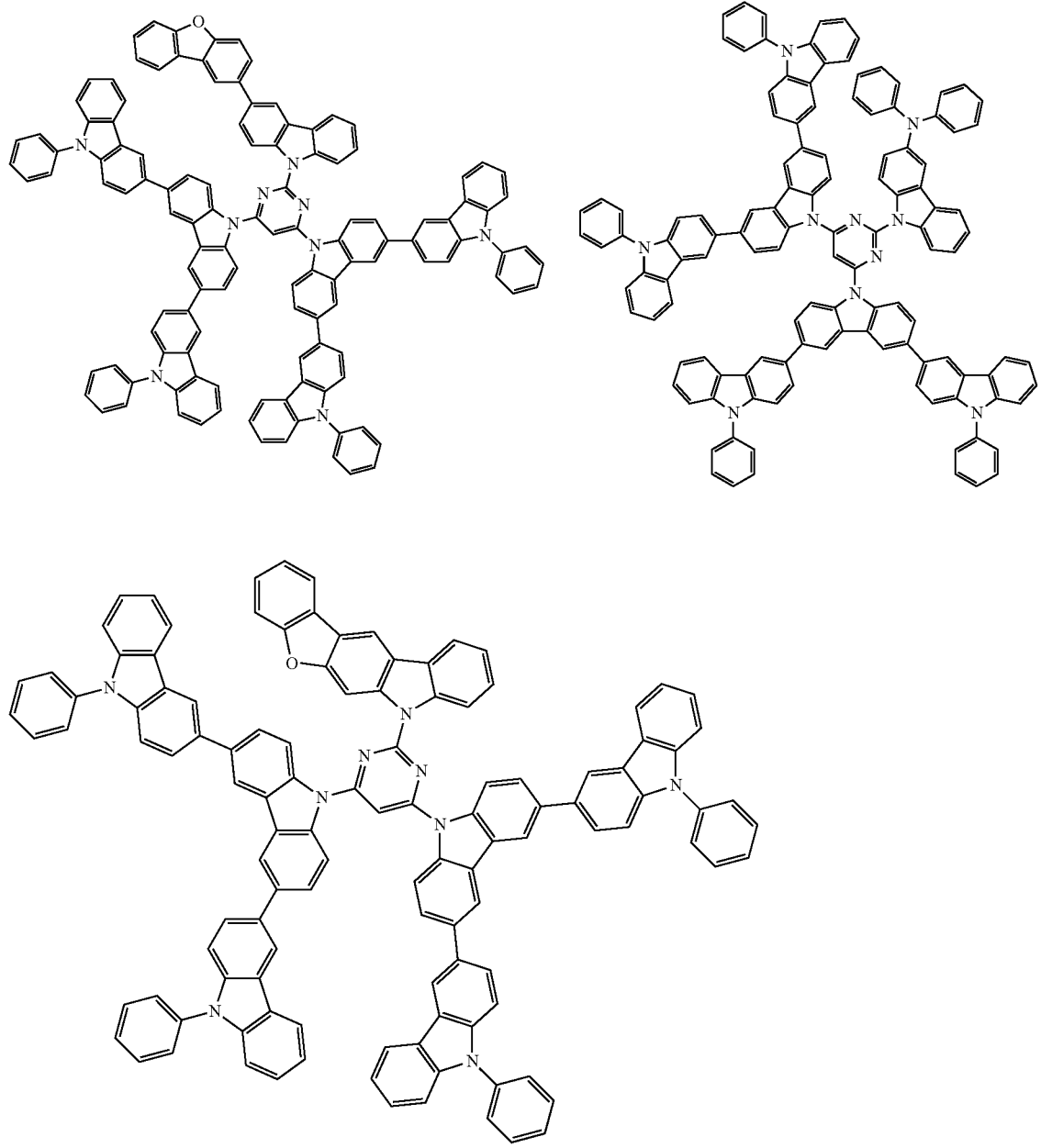

1911
1912
-continued
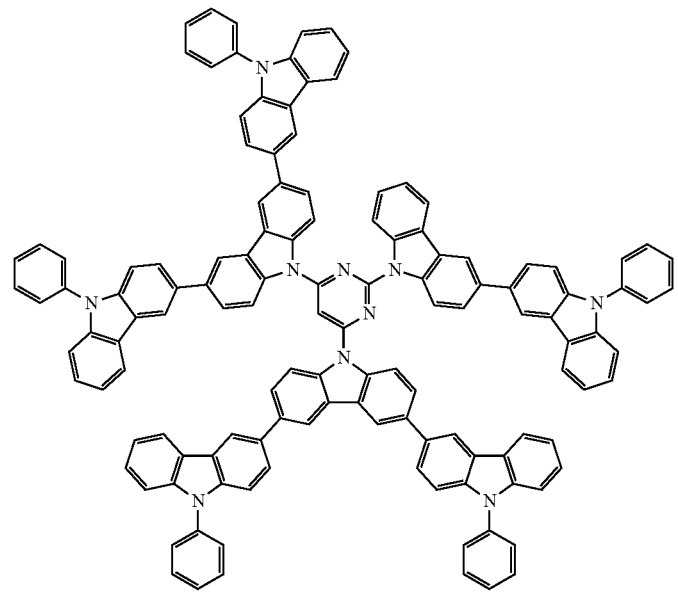
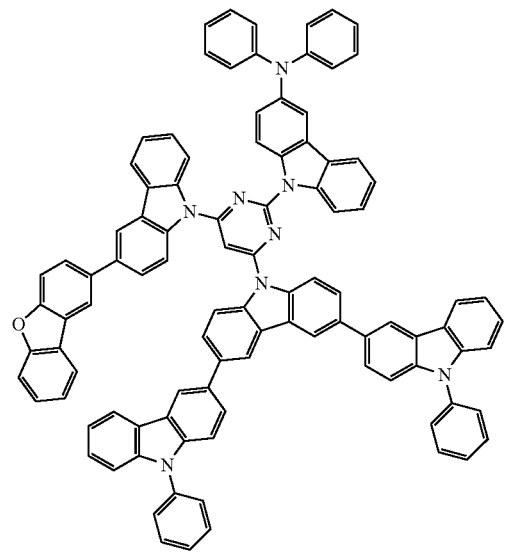
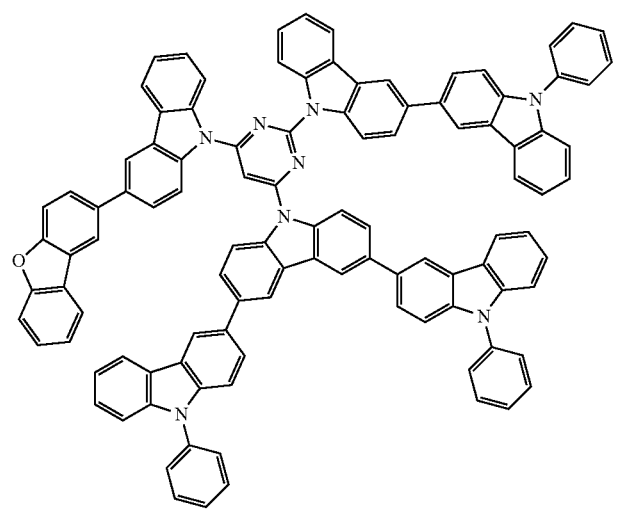
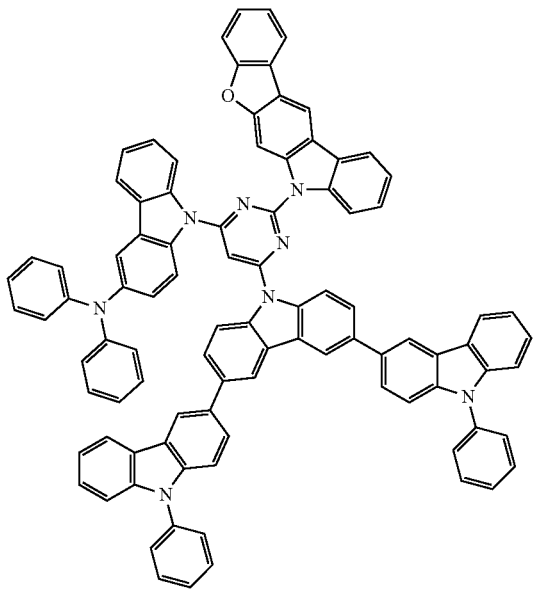

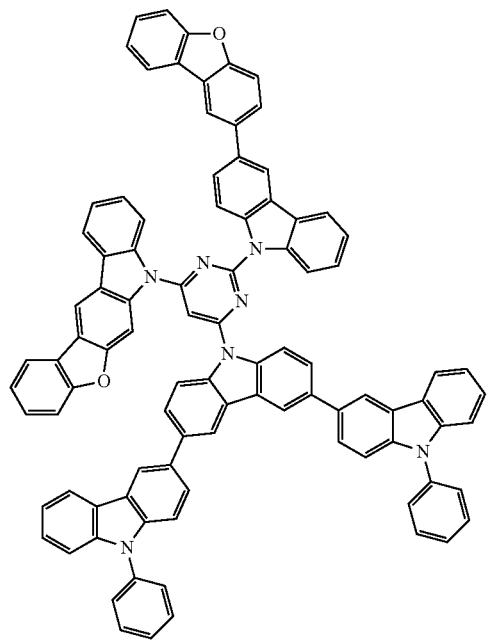
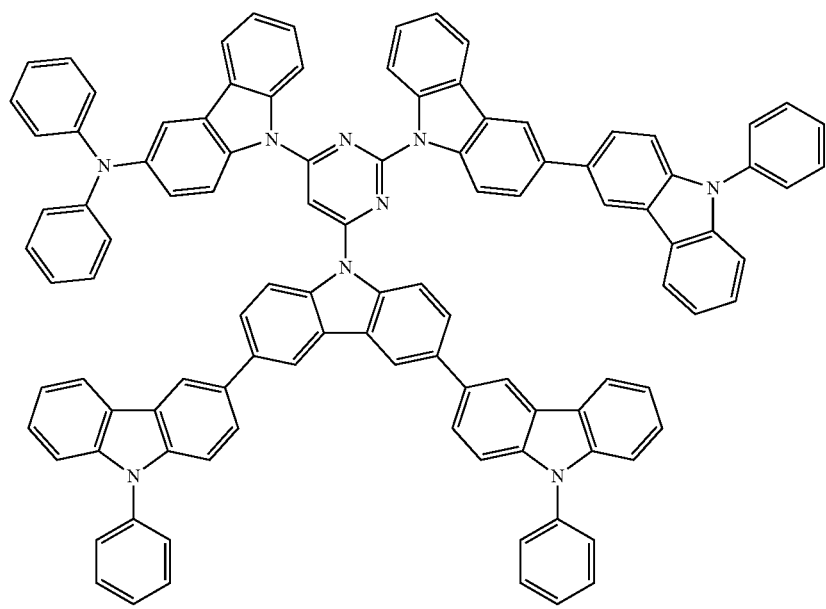

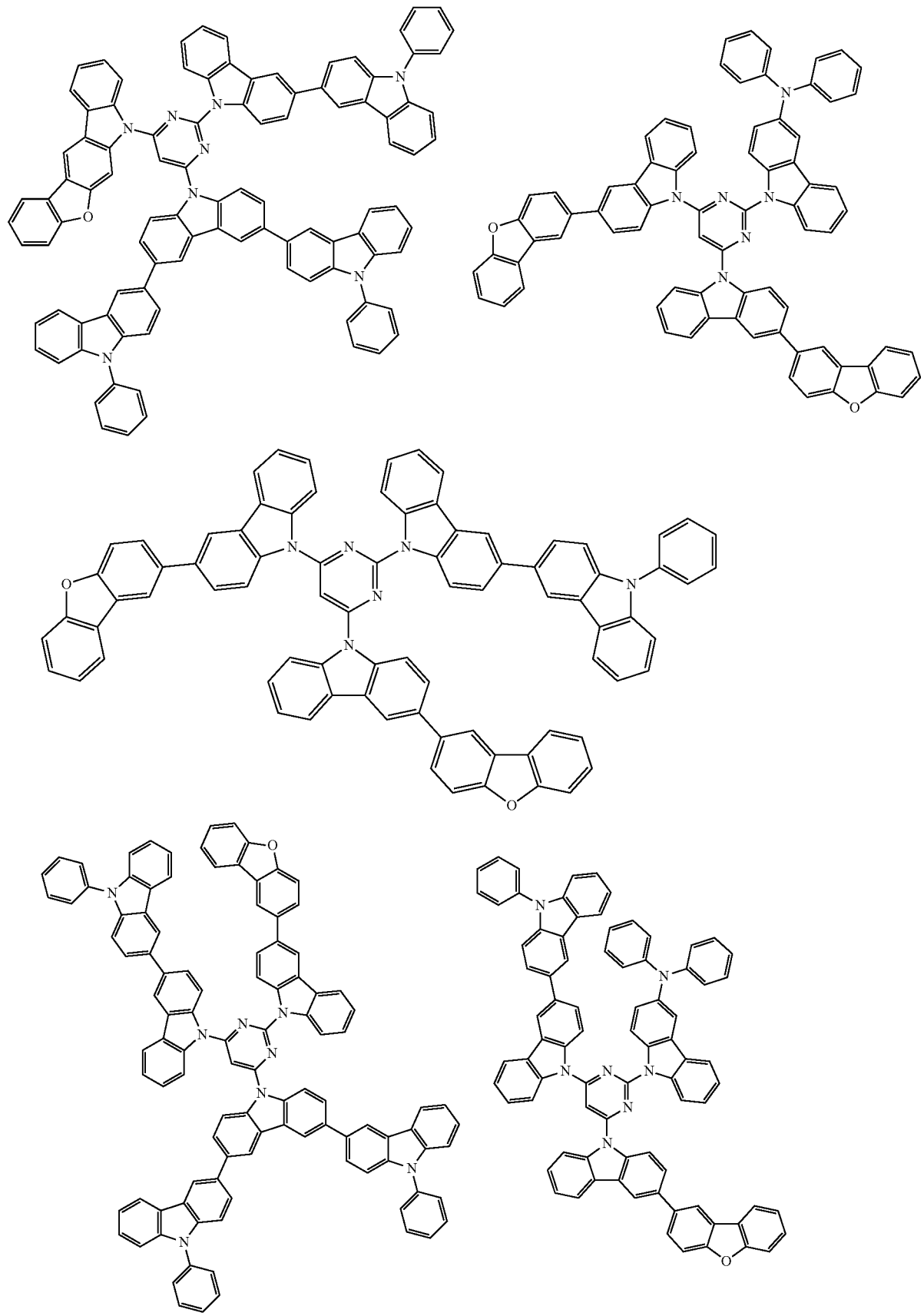

-continued
1917
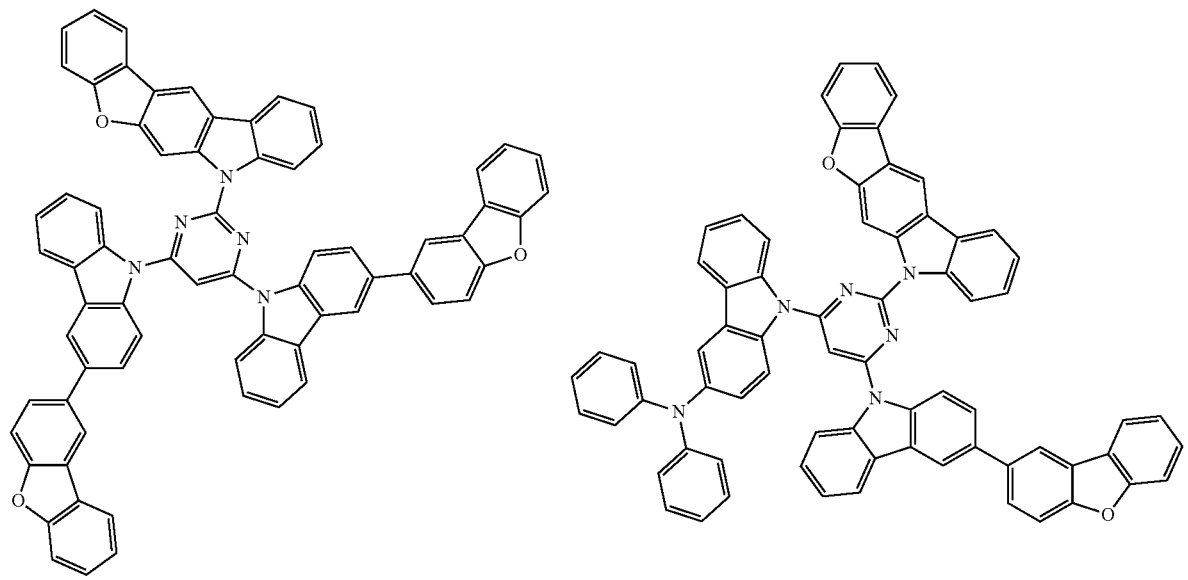
1918
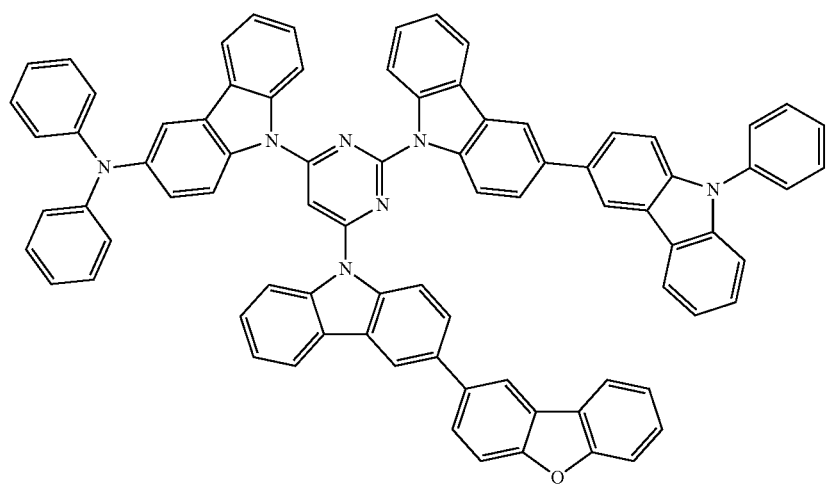
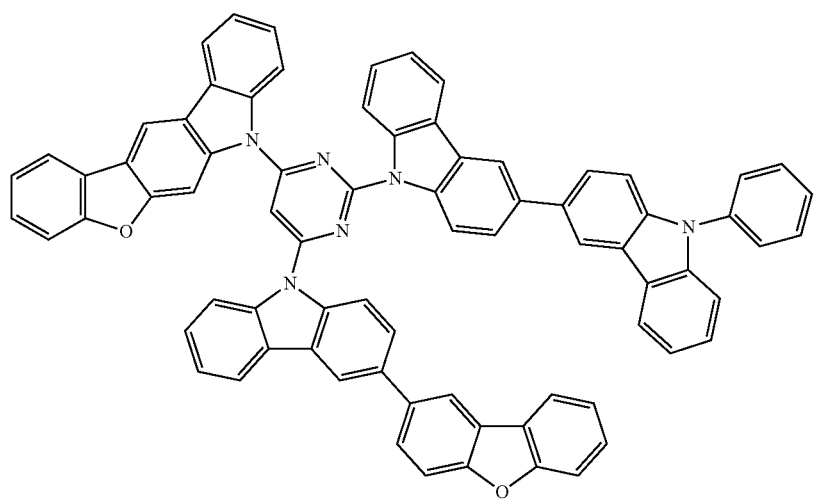

-continued
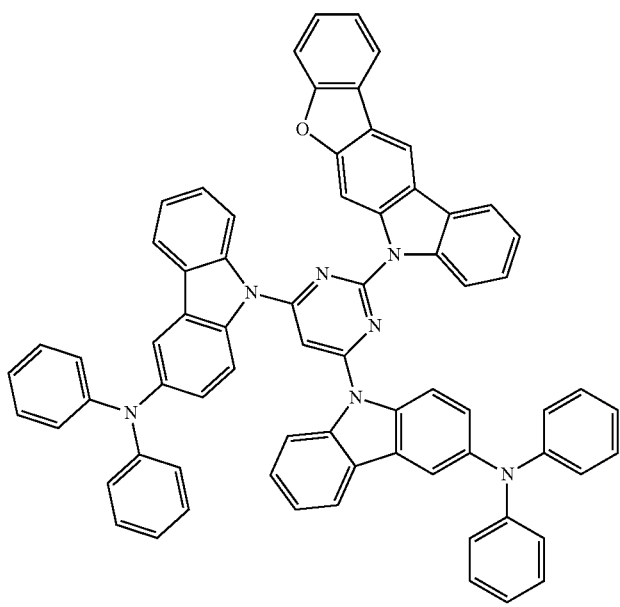
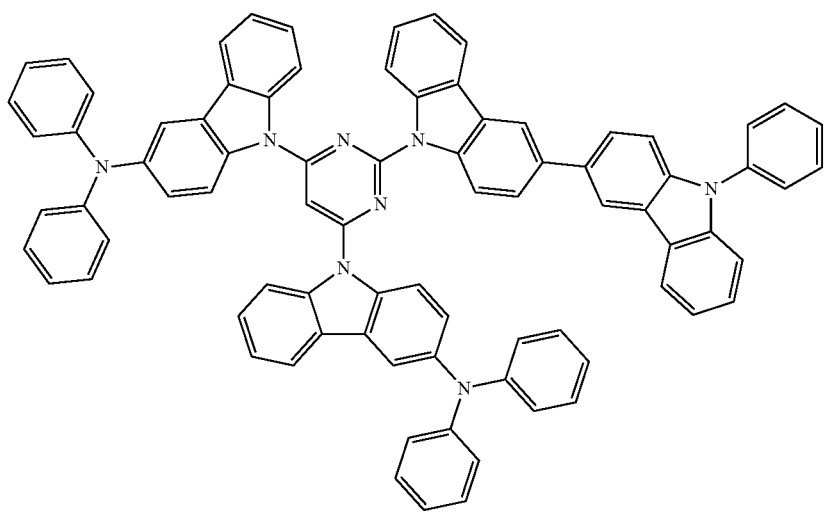
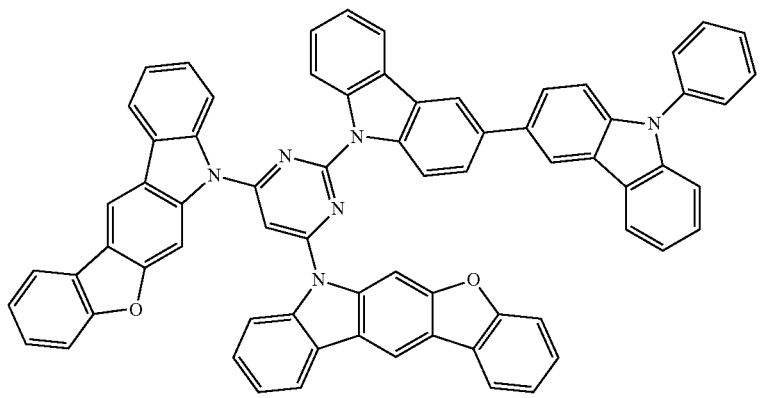

-continued
| 1921 | 1922 |
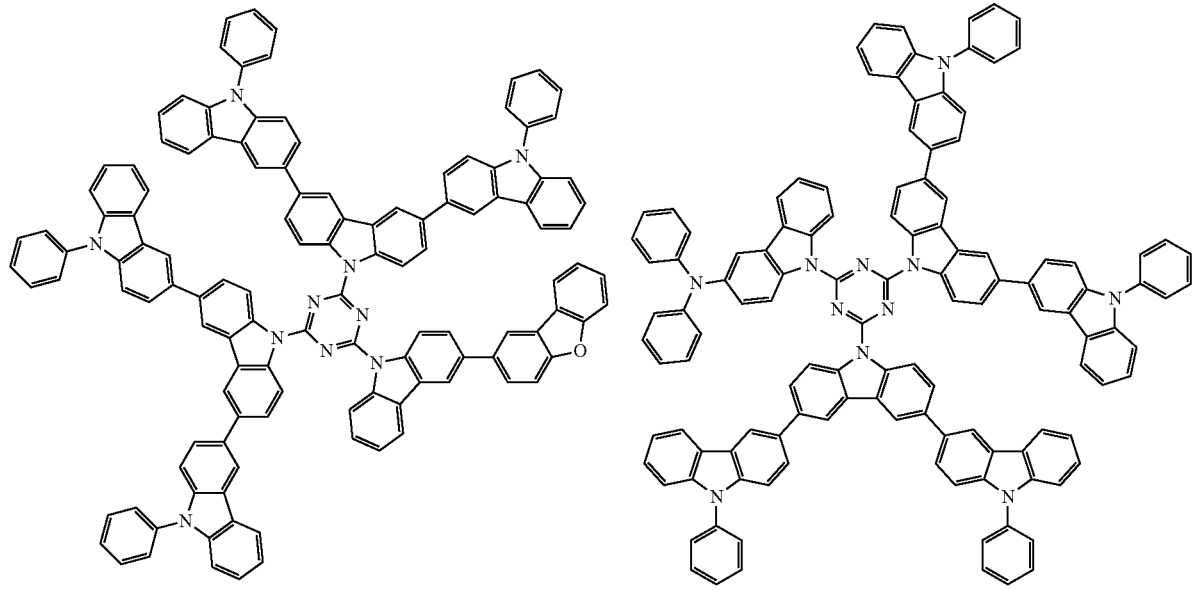
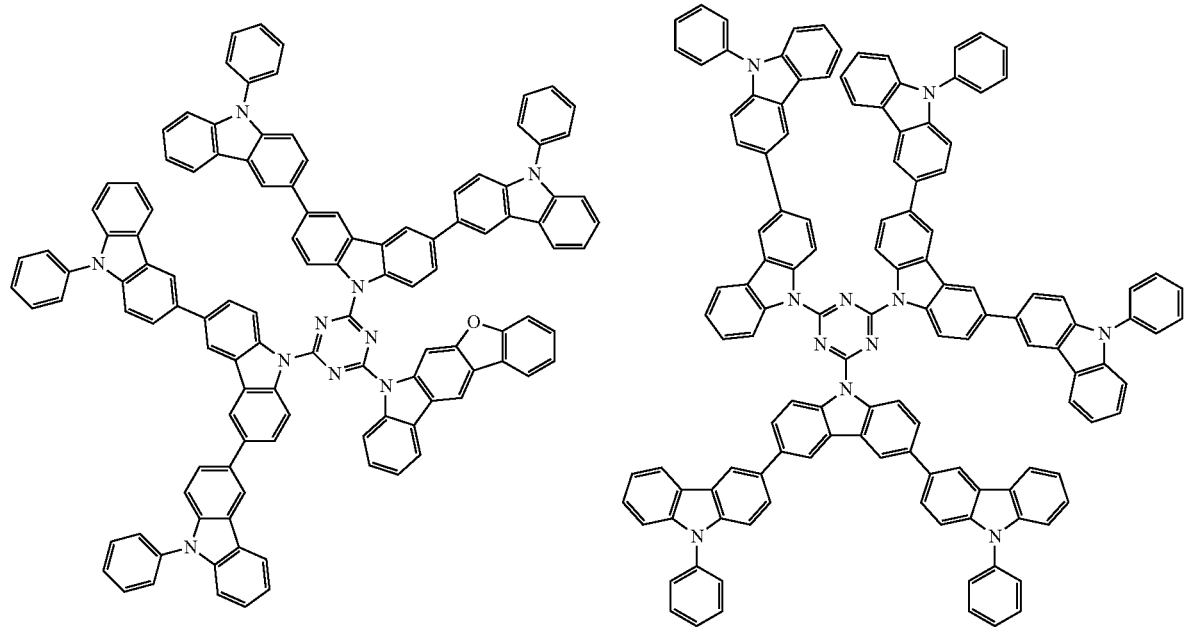

1923
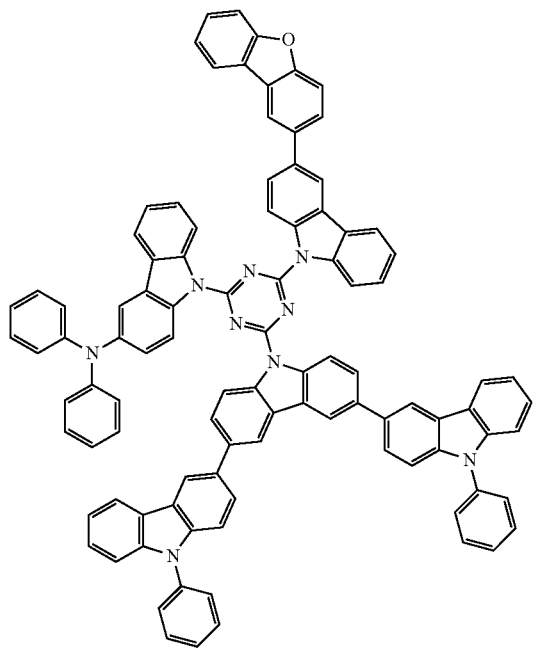
1924
-continued
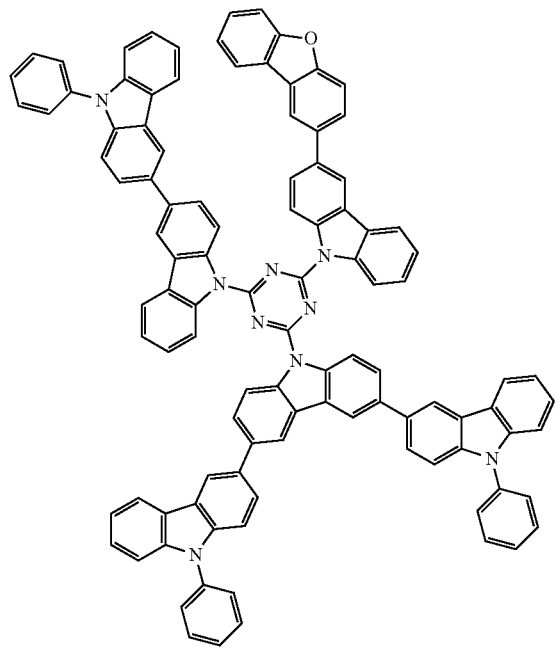
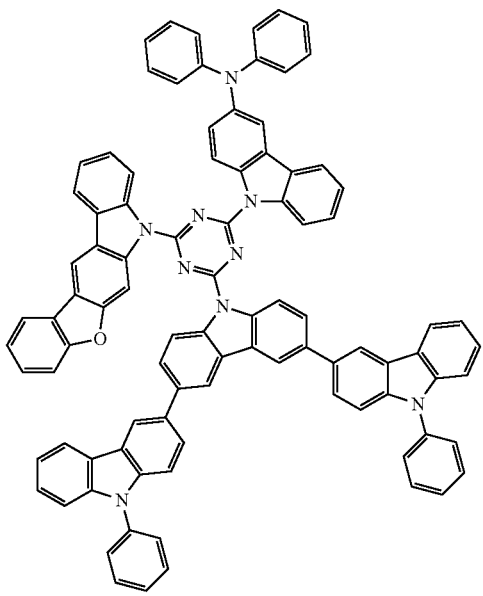

1925
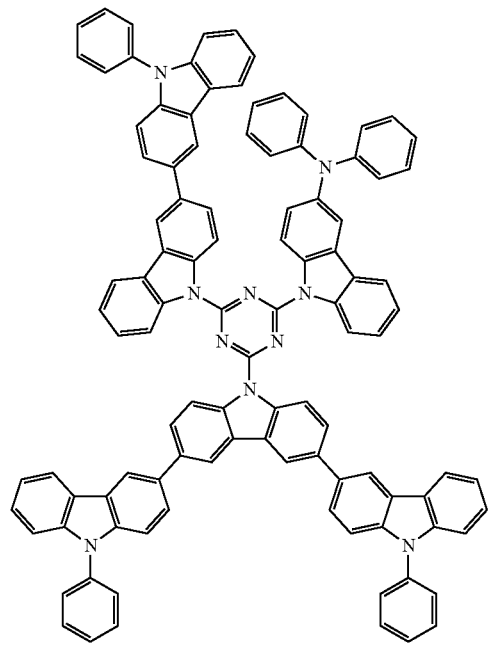
1926
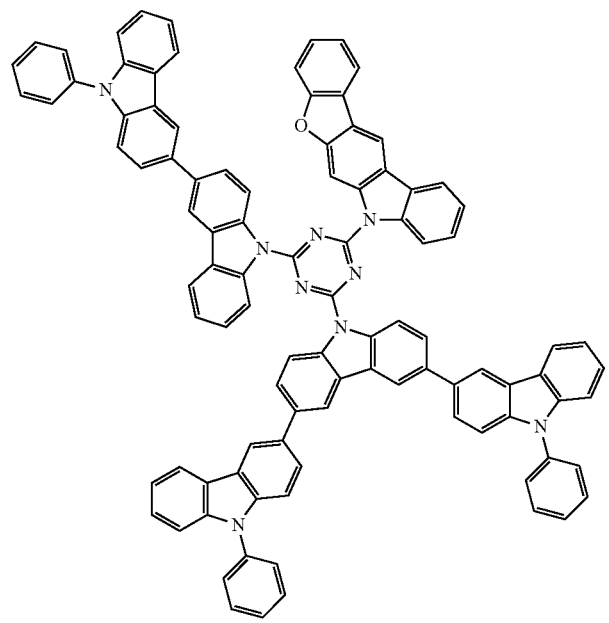
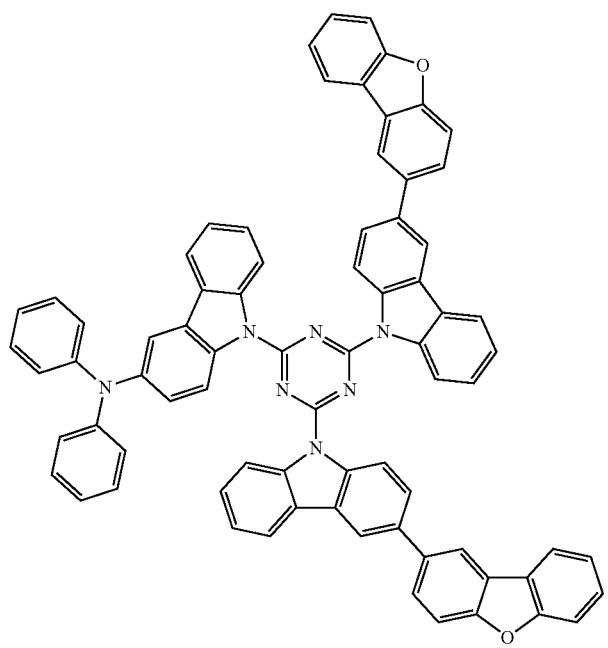
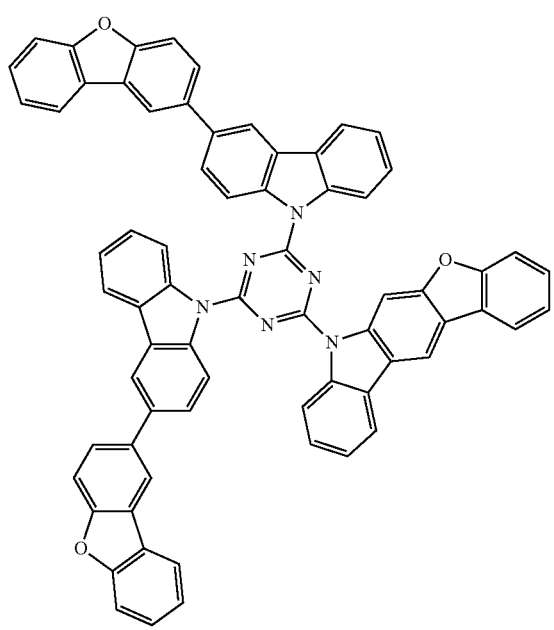

1927
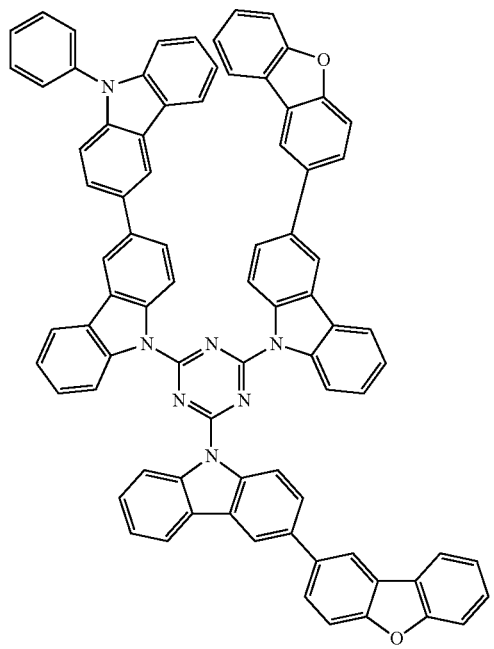
1928
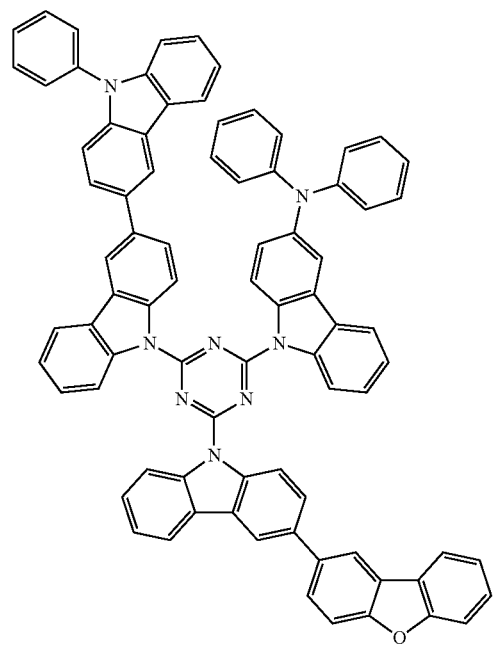
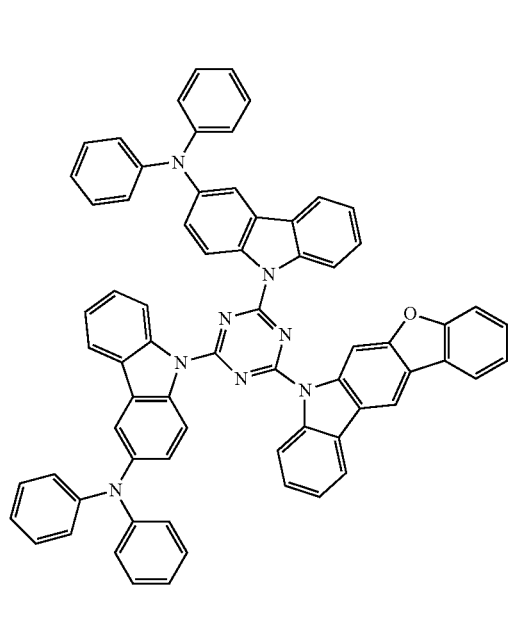
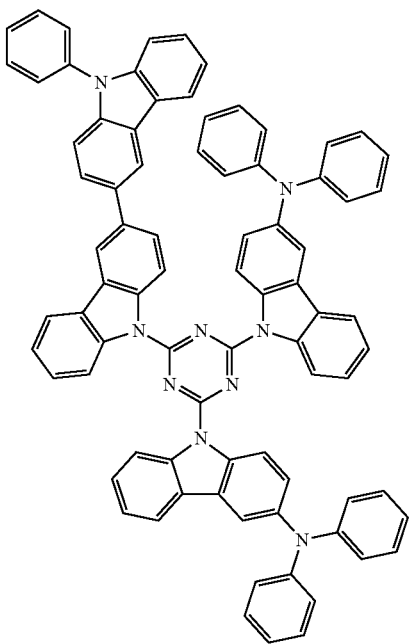

-continued
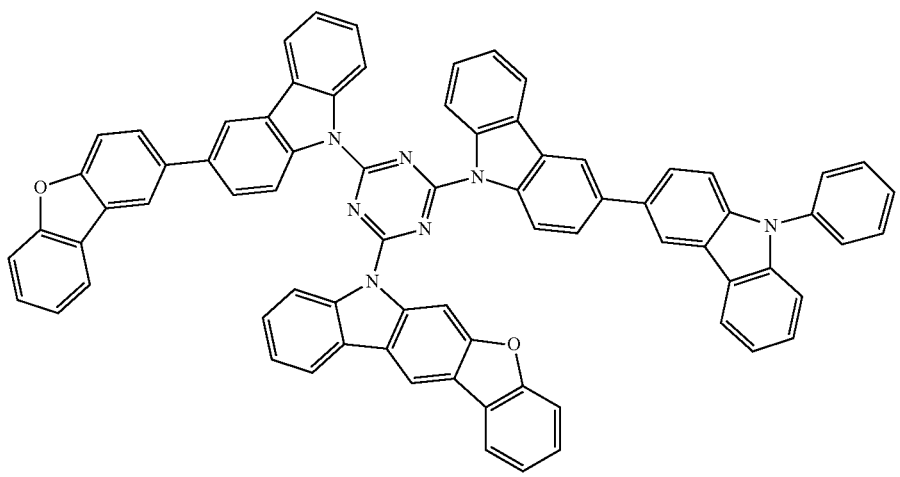
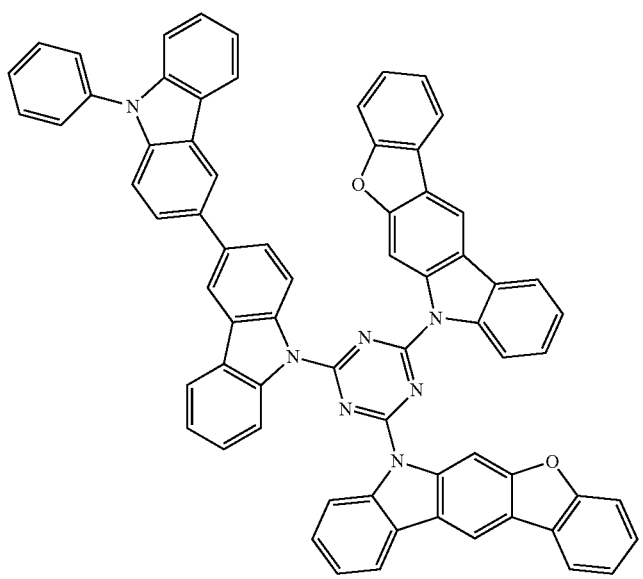
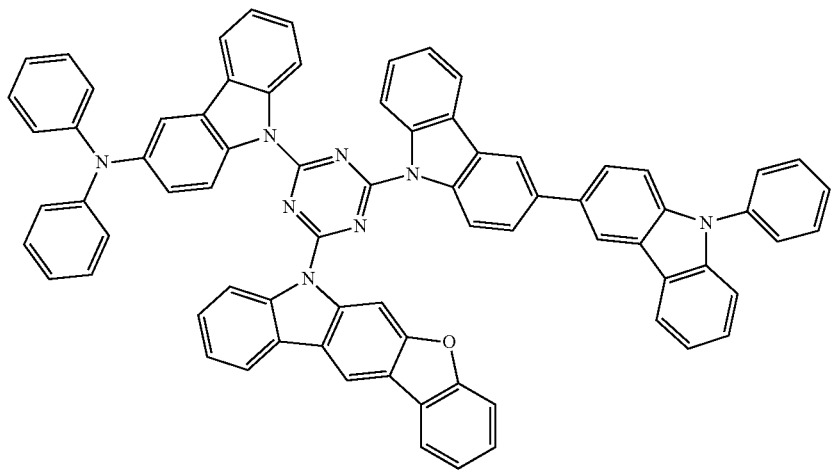

1931 1932
-continued
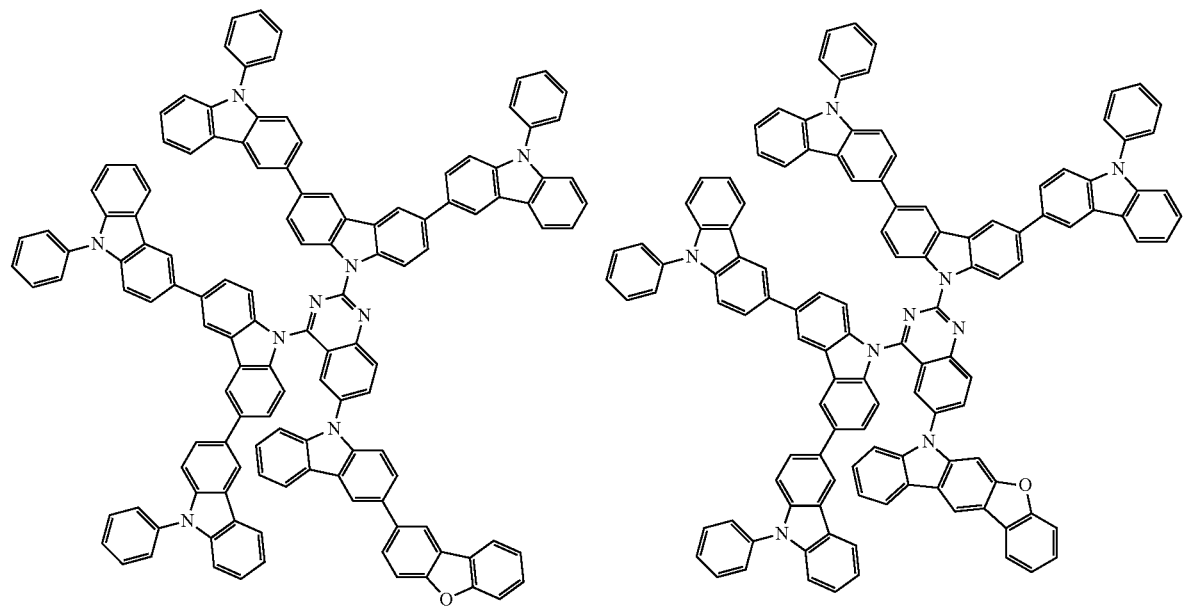
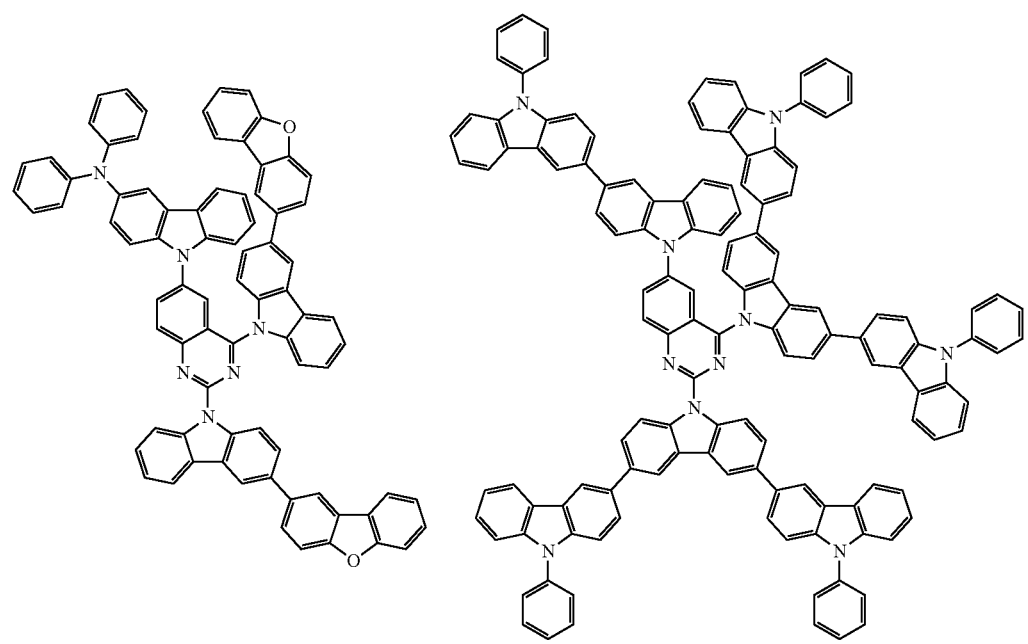

1933
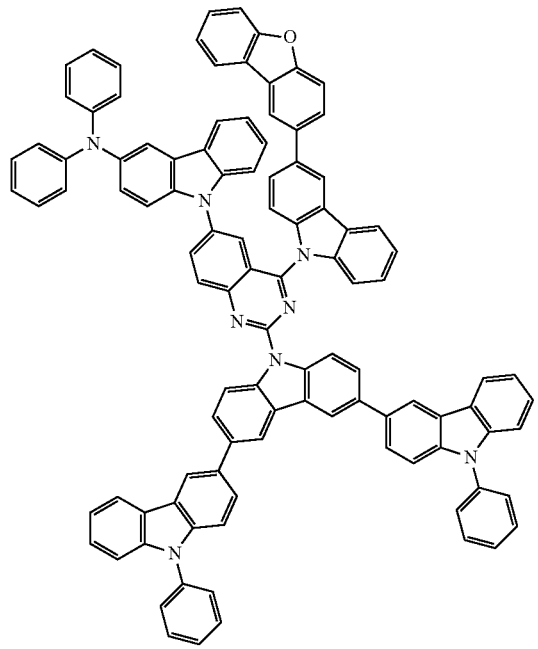
1934
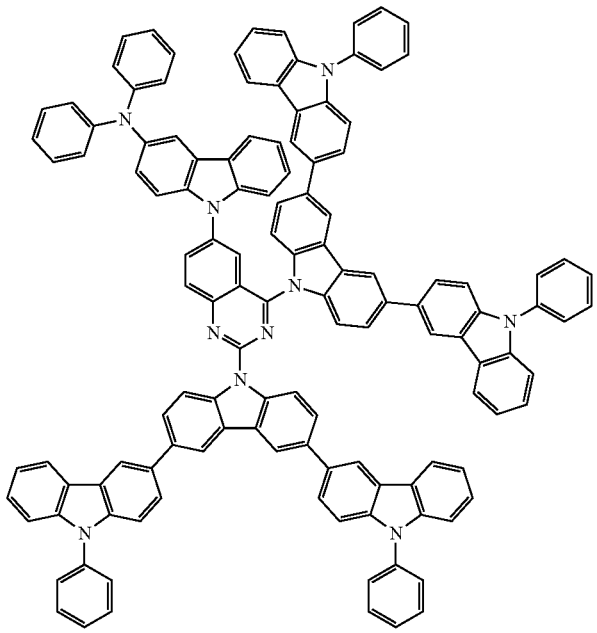
-continued
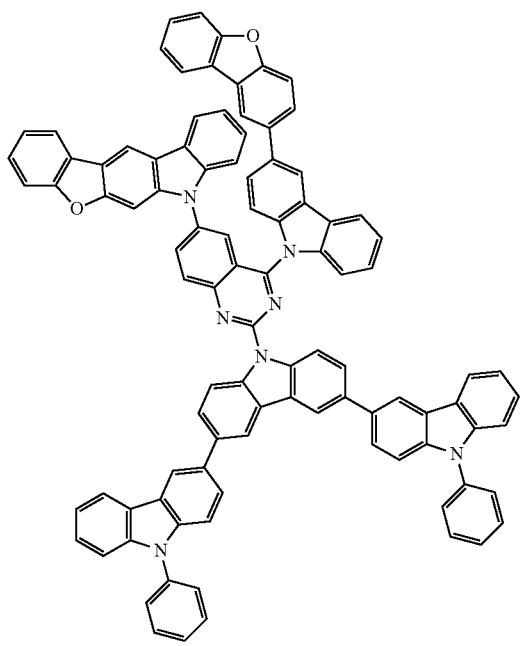
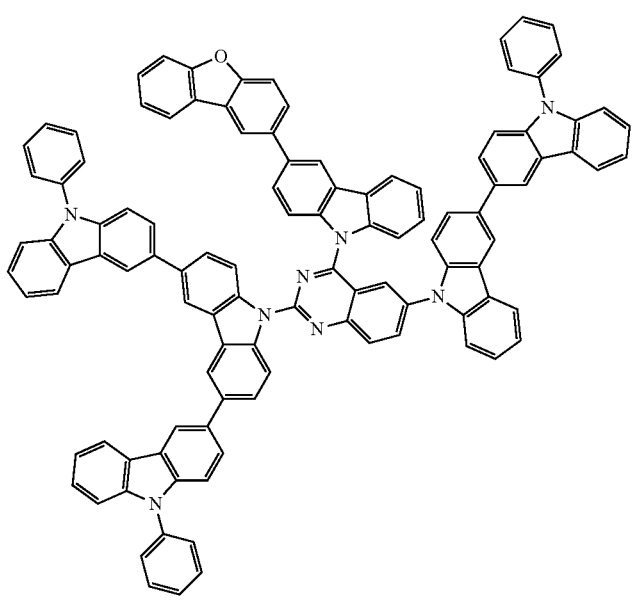

1935 1936
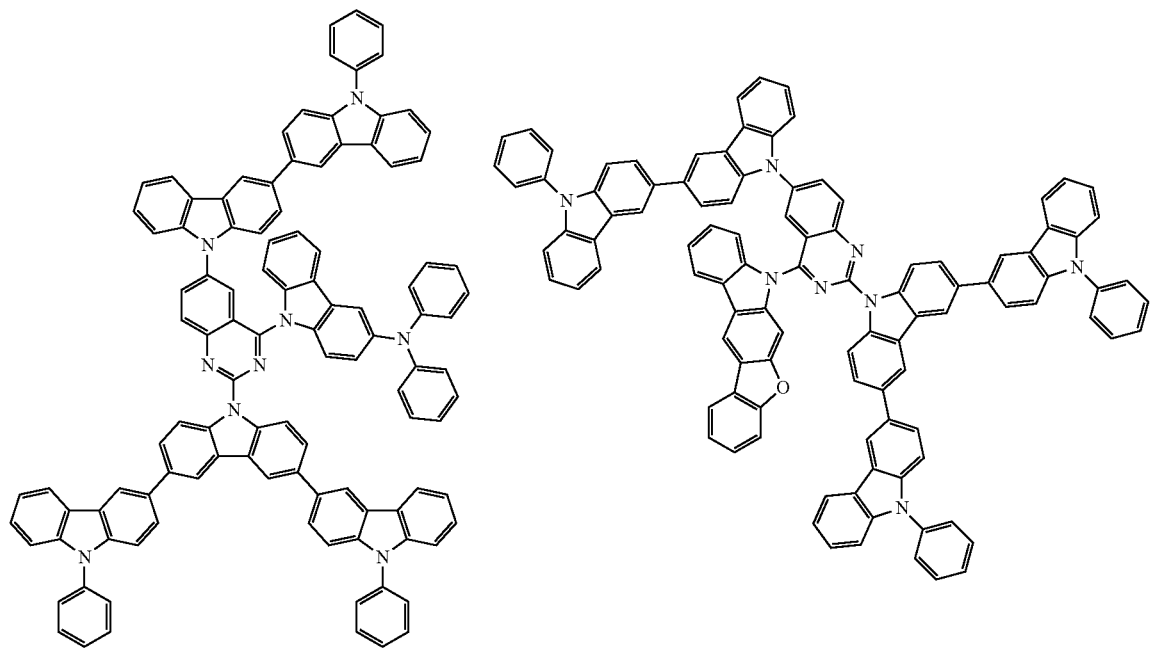
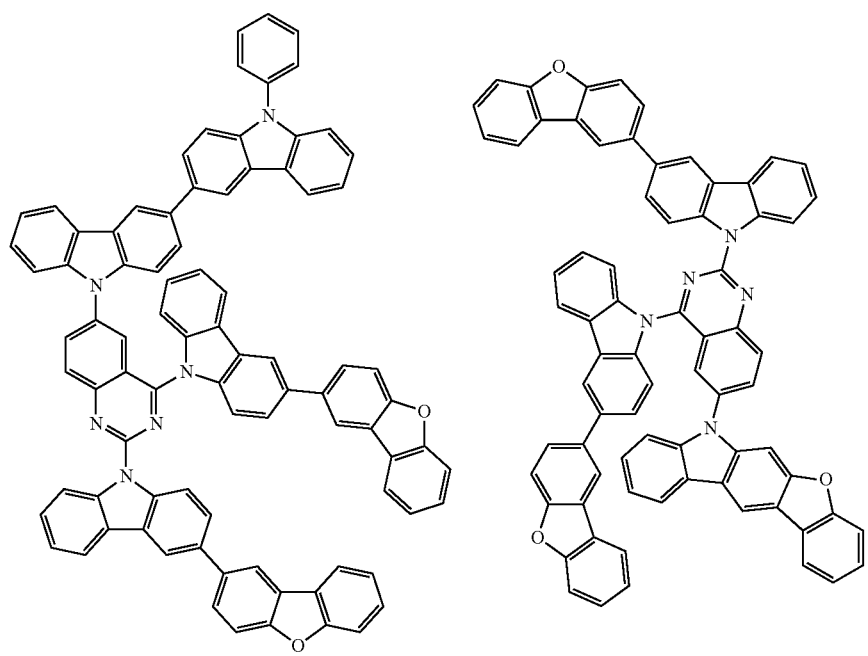

1937 1938
-continued
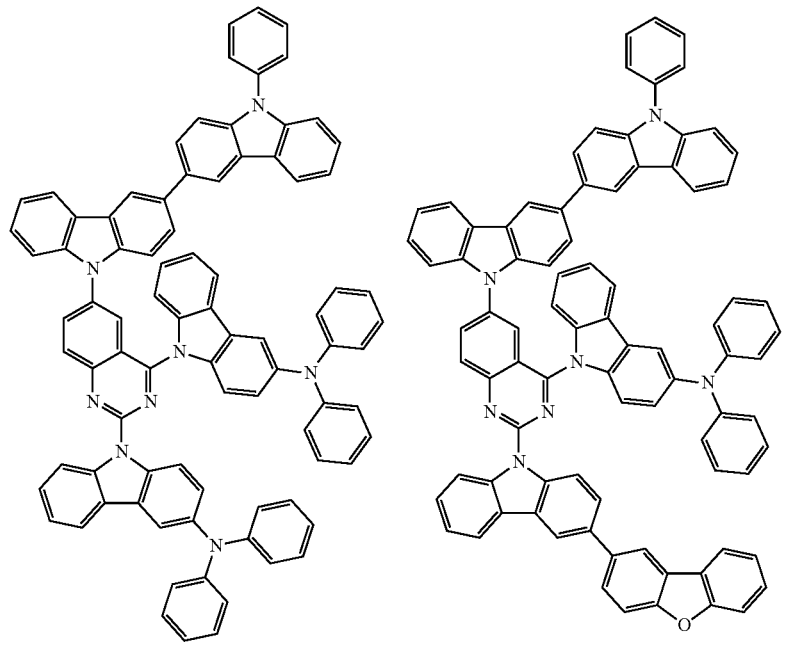
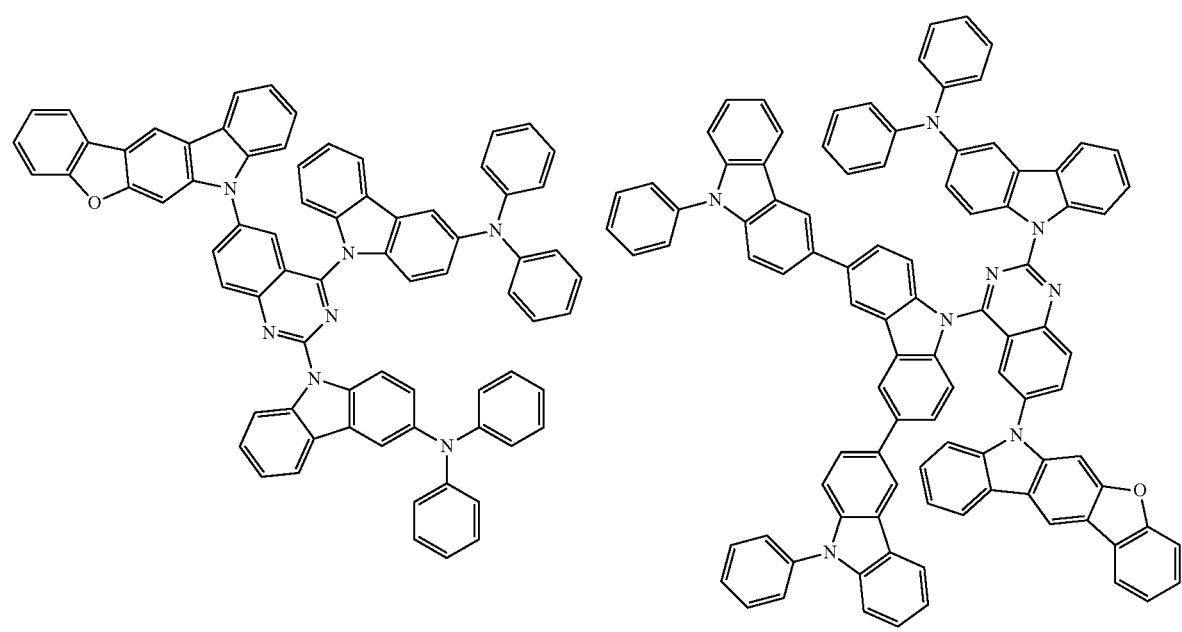

1939
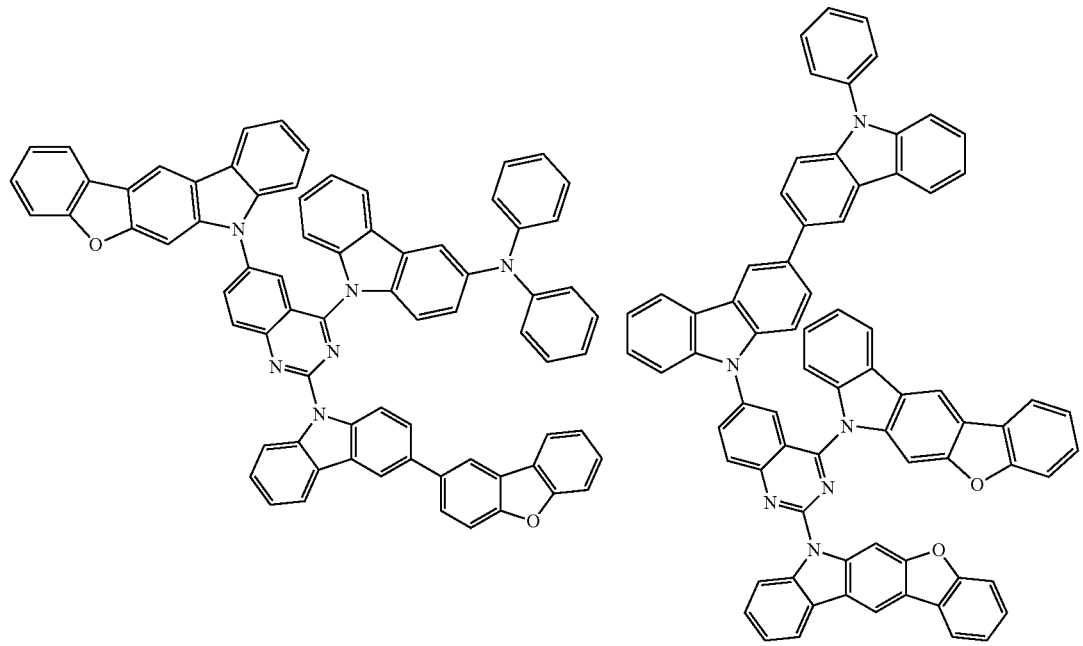
1940
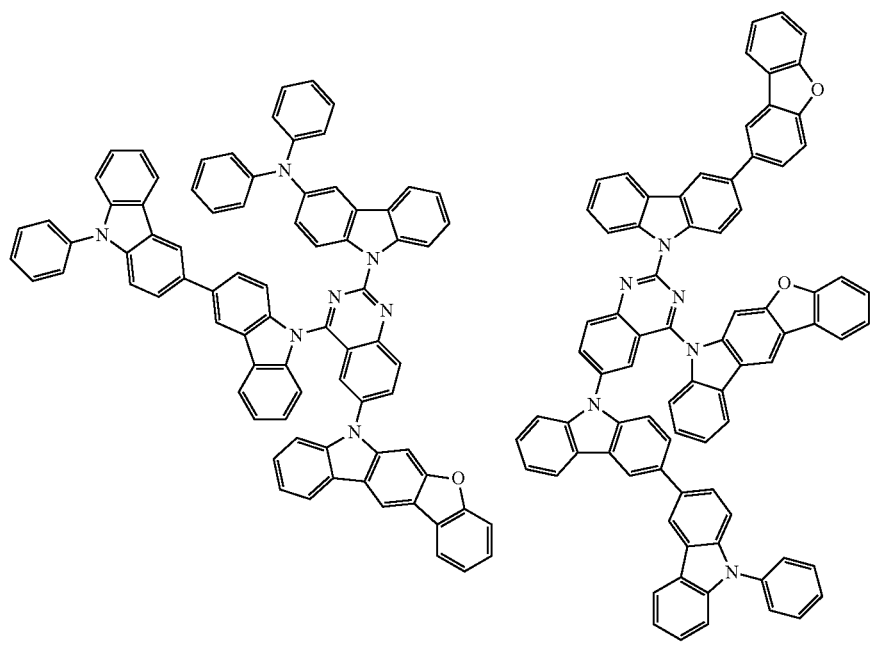

1941 1942
-continued
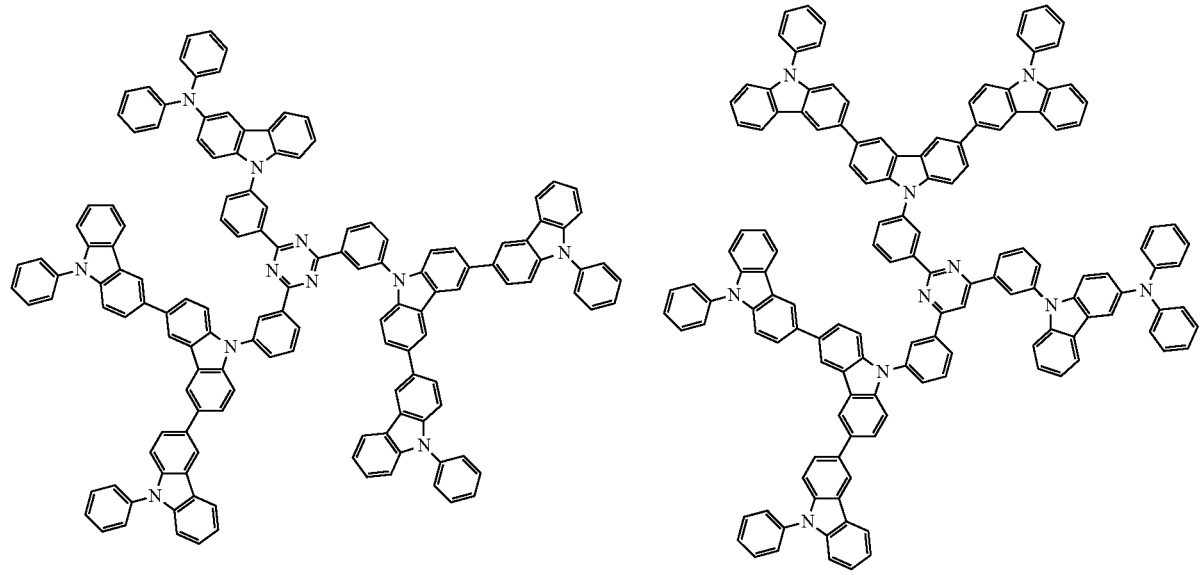
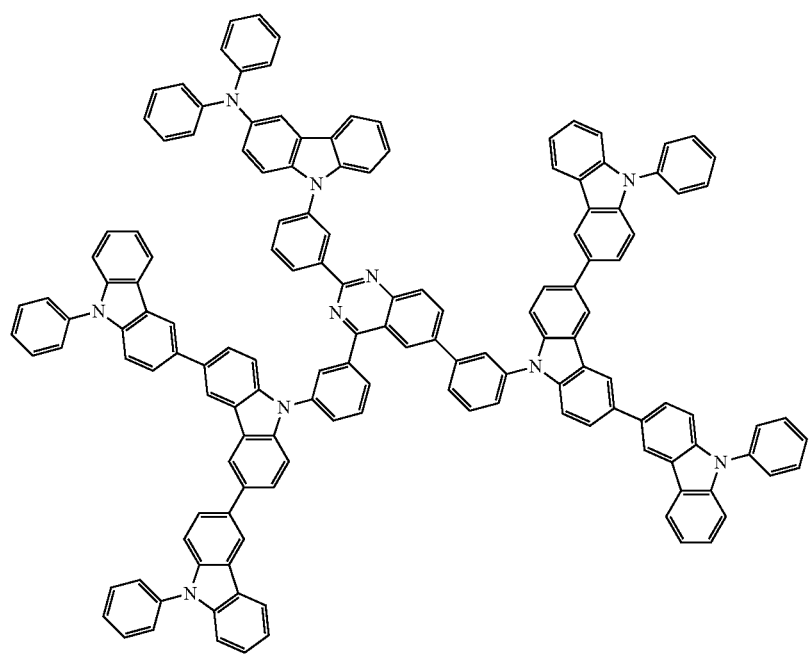

1943 1944
-continued
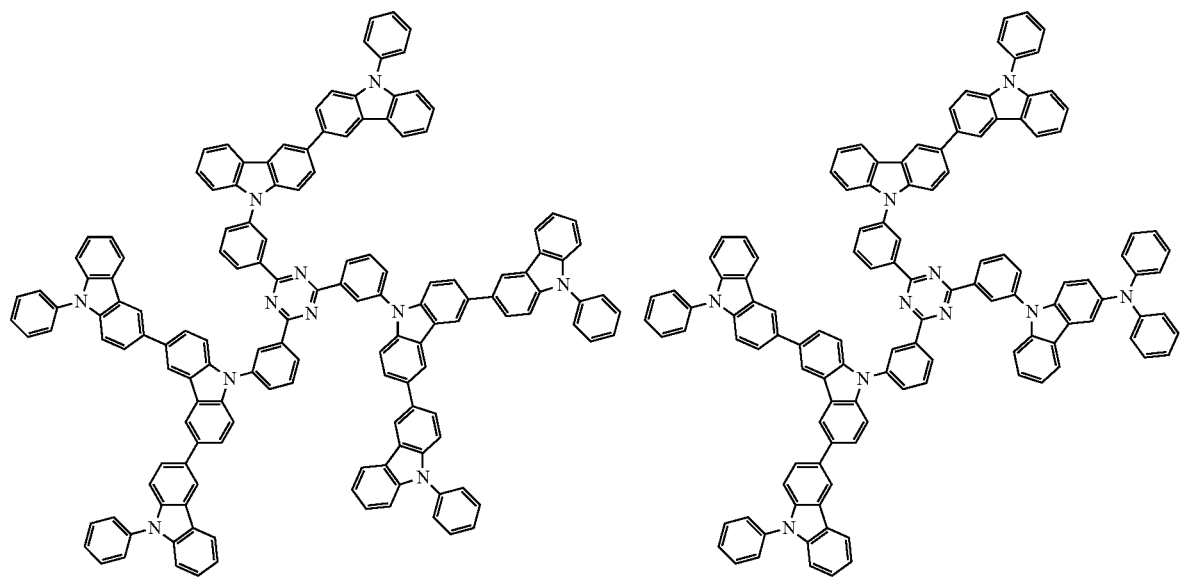
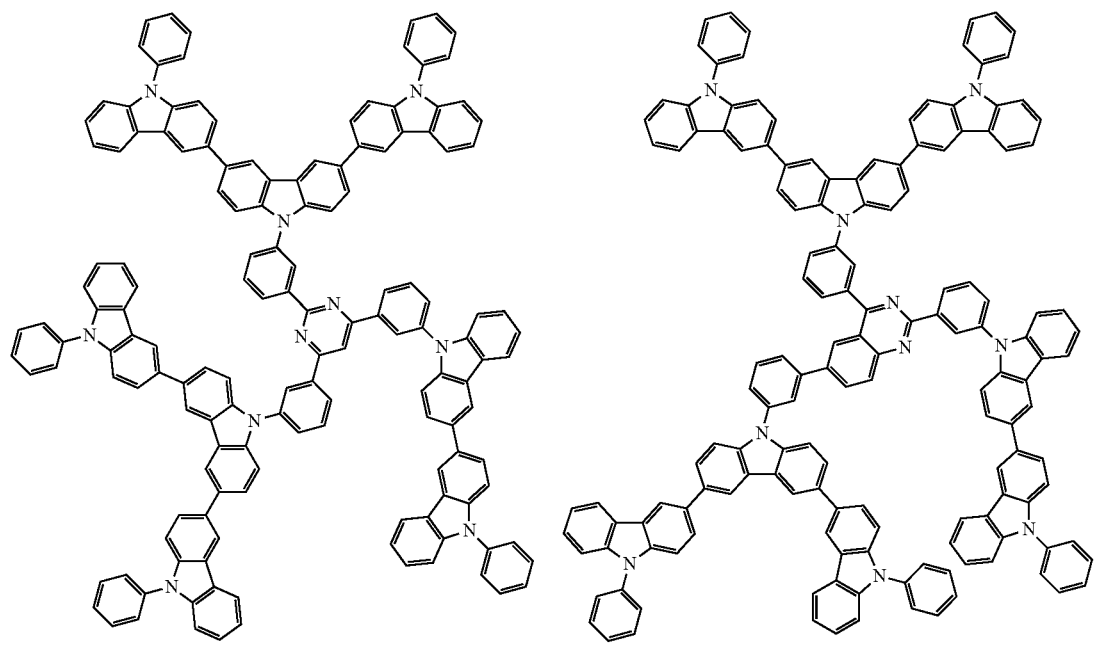

1945 1946
-continued
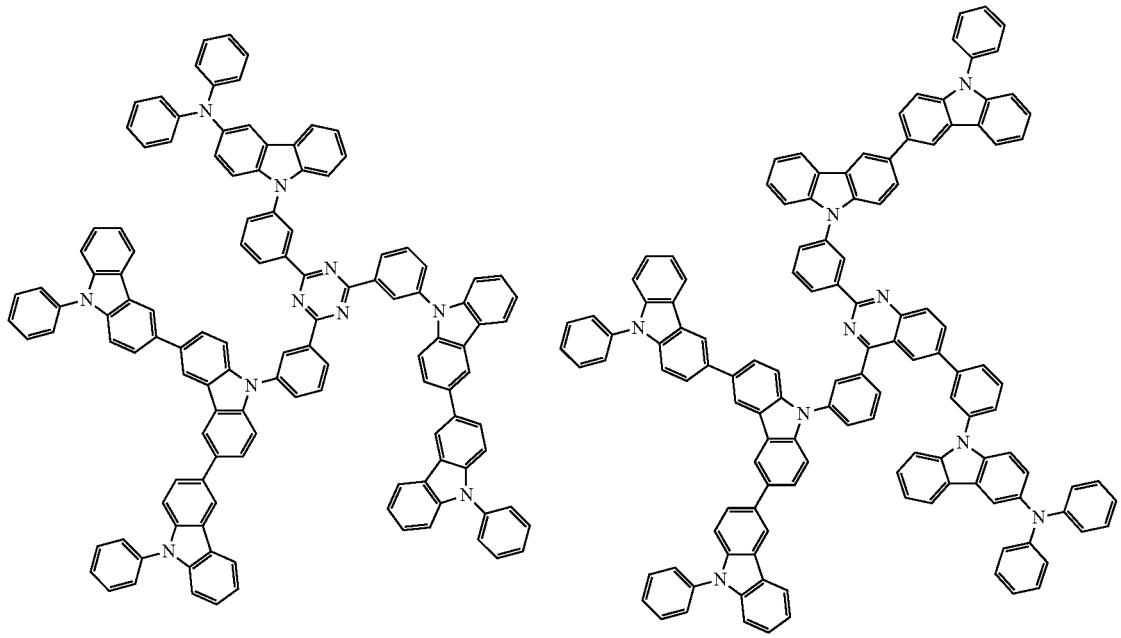
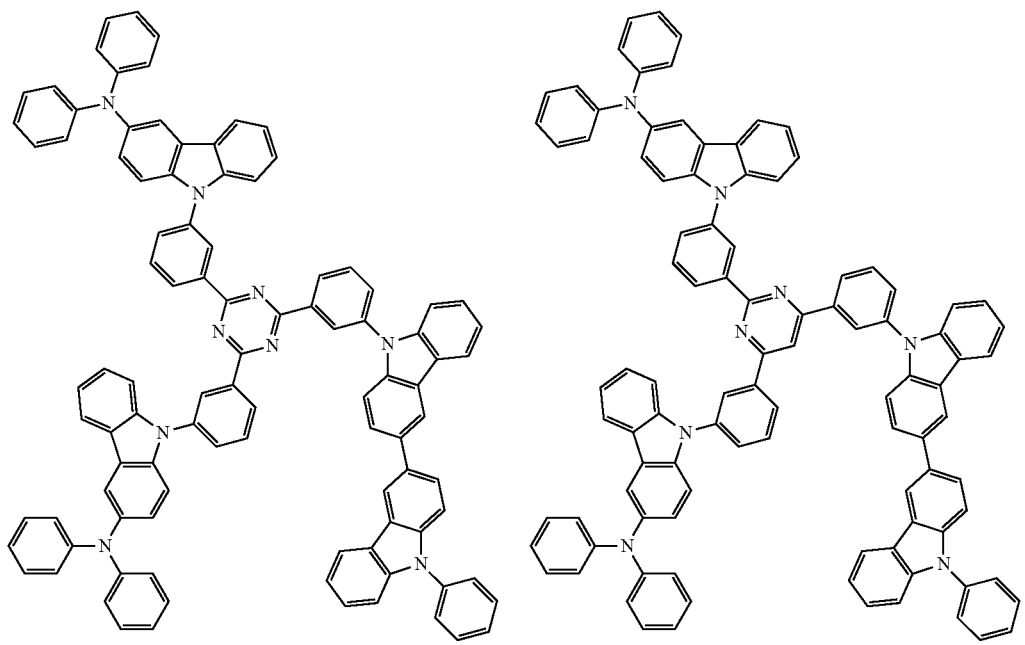

1947　　　1948
-continued
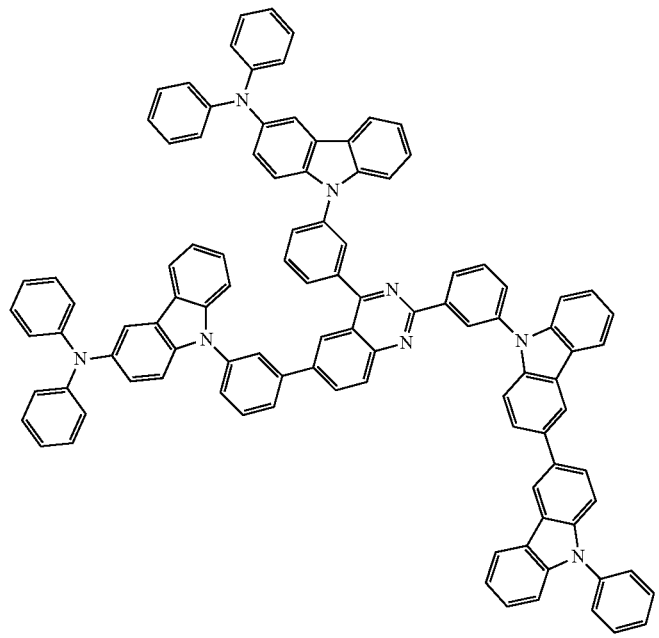
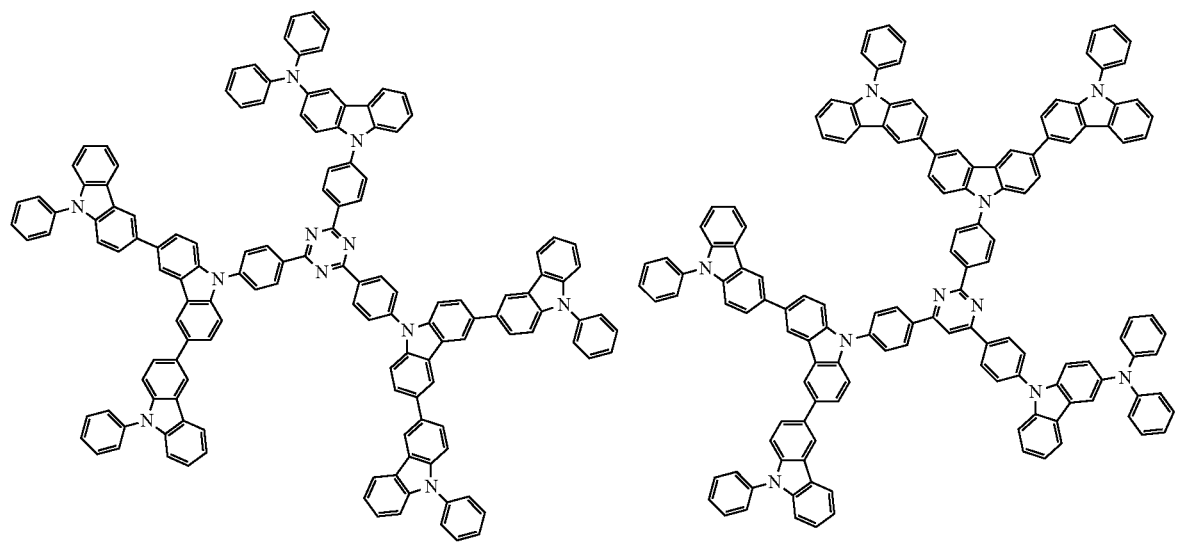

1949                    1950
-continued
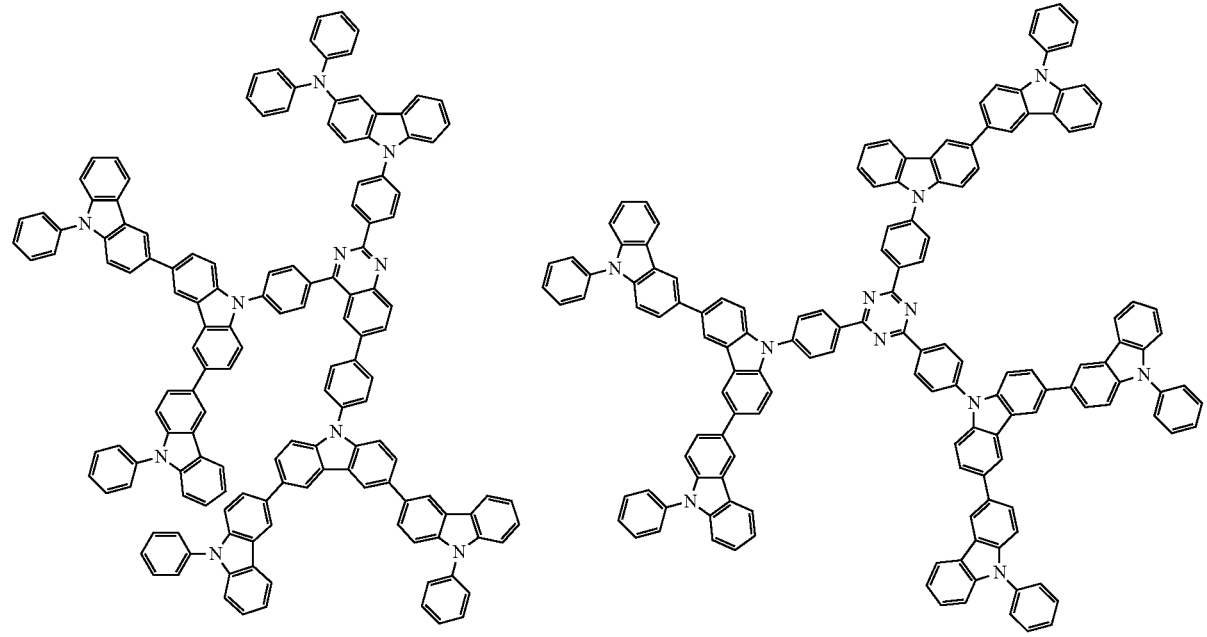
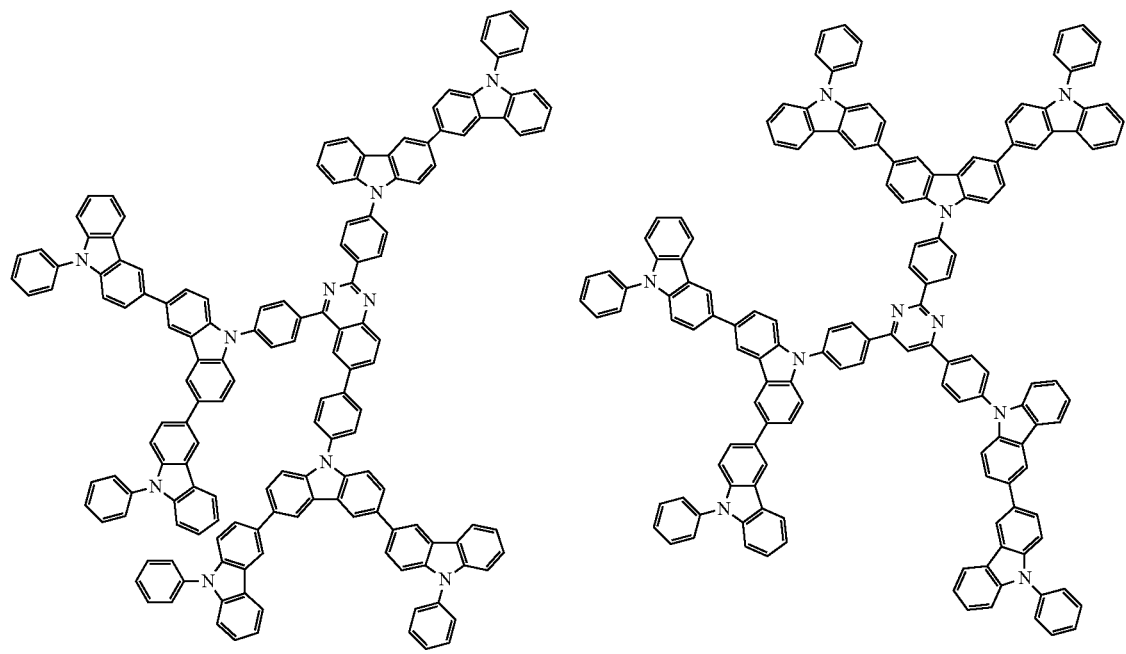

1951 1952
-continued
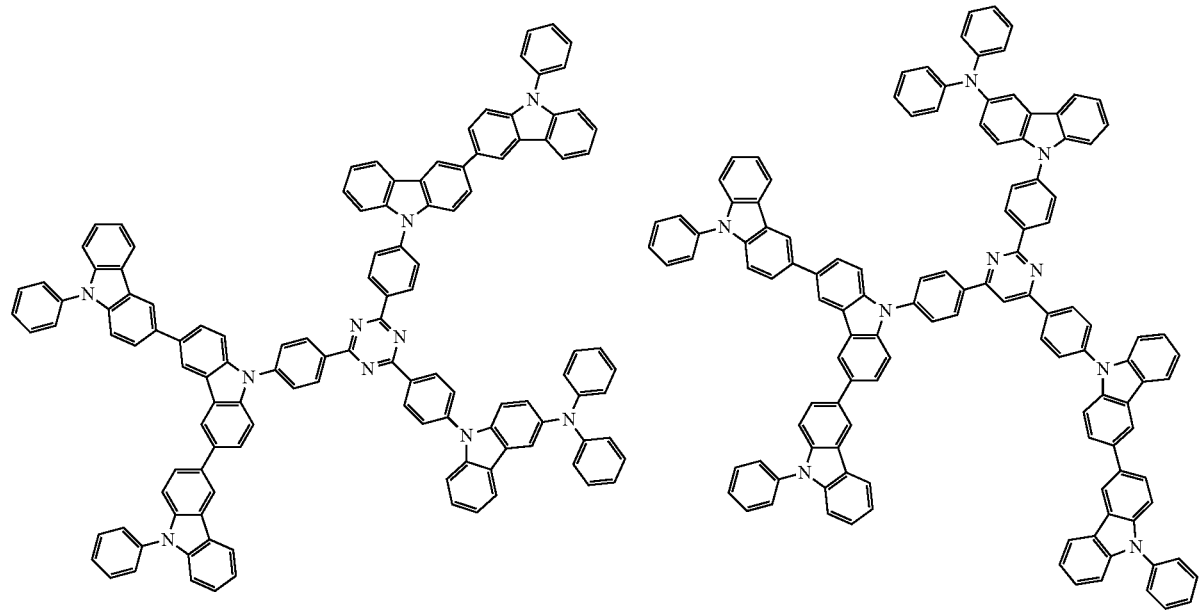
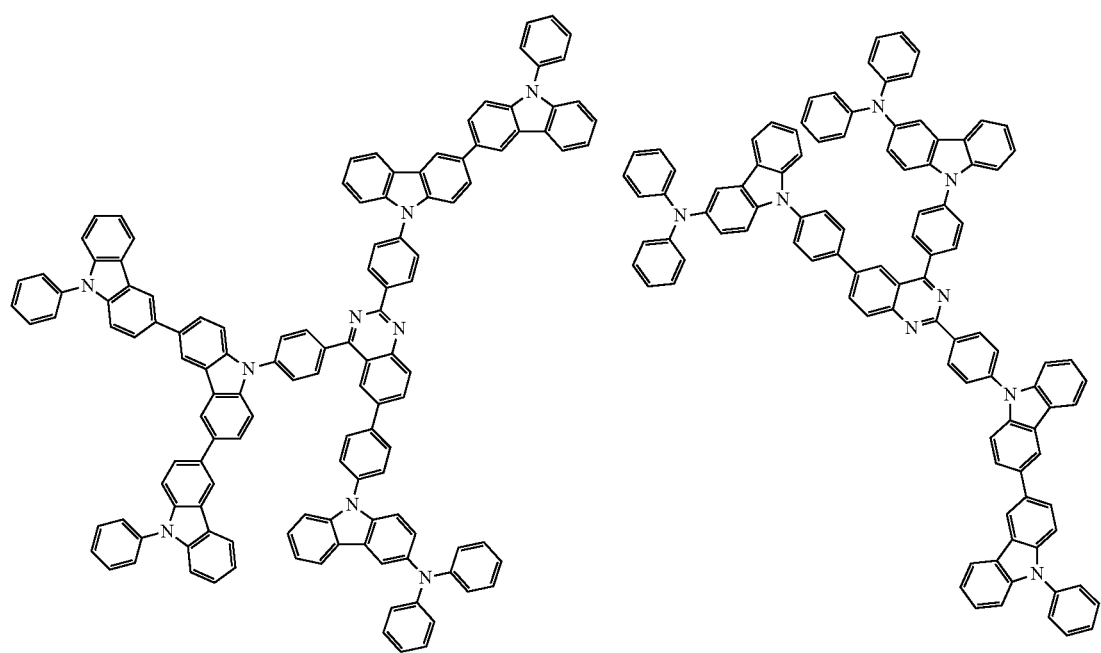

1953 1954
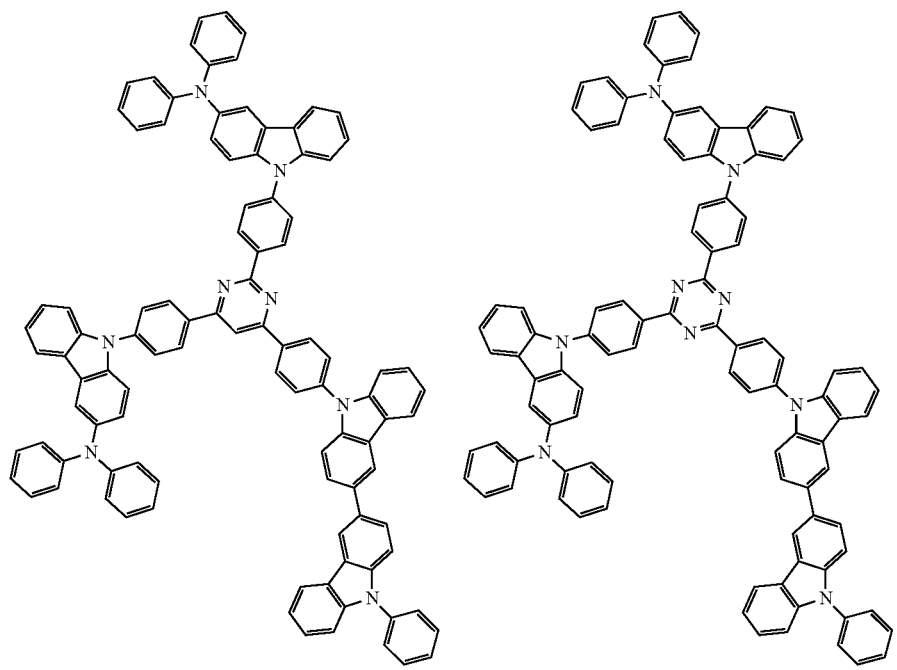
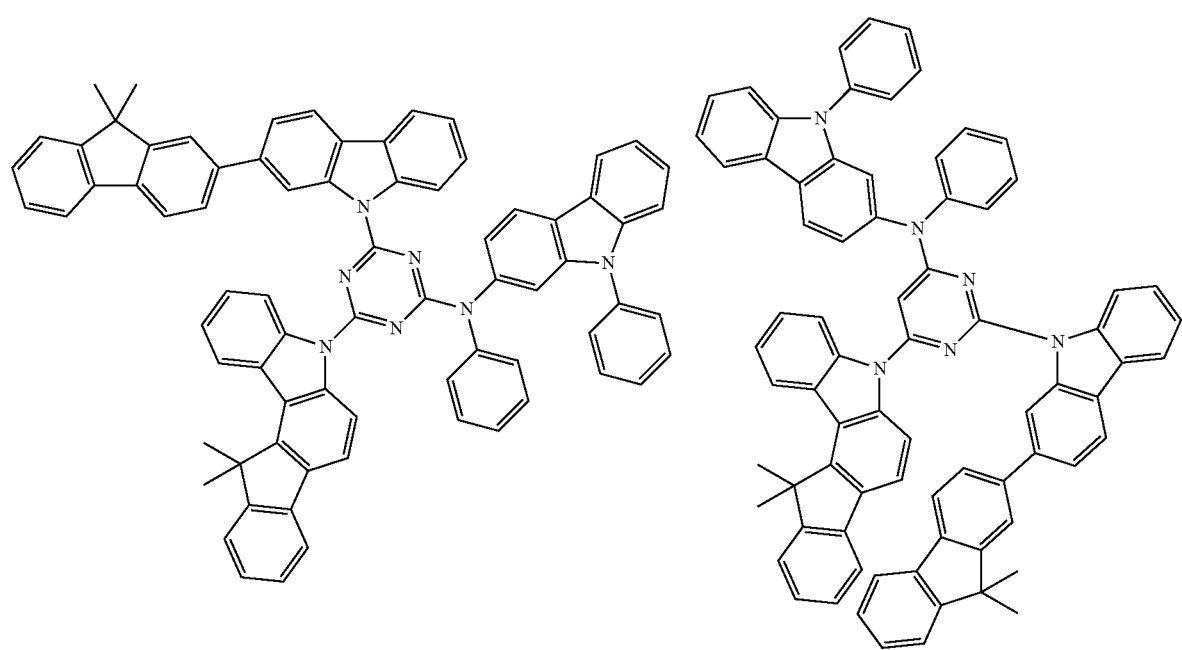

| 1955 | 1956 |
|---|---|
| 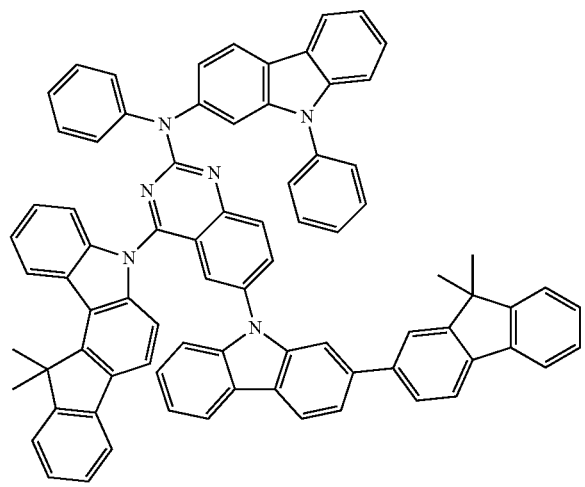 | 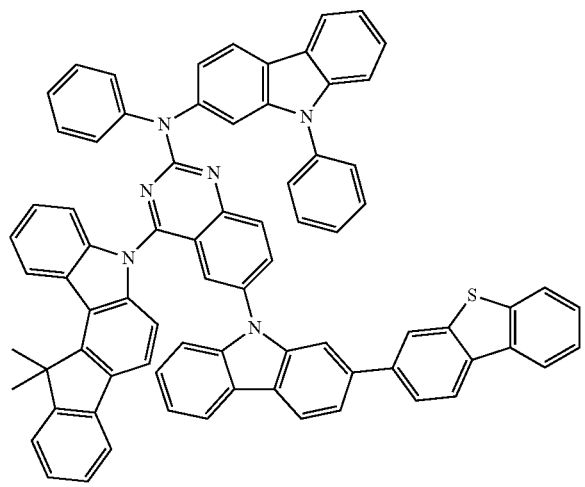 |
| 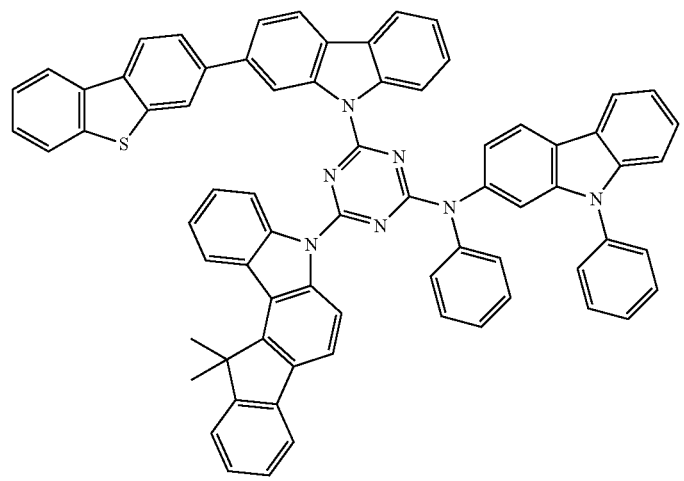 | 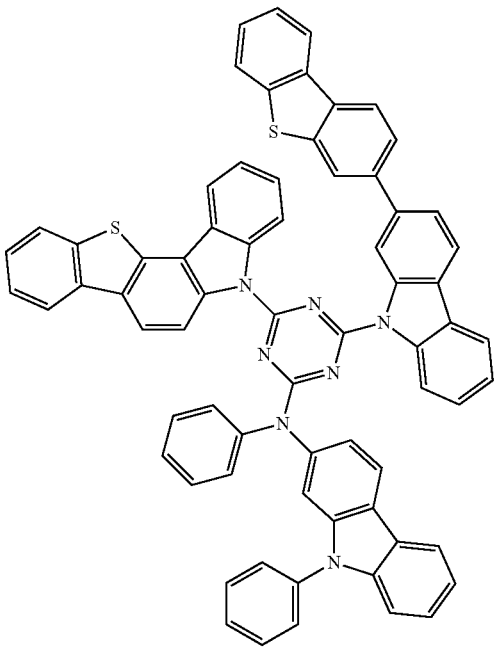 |
| 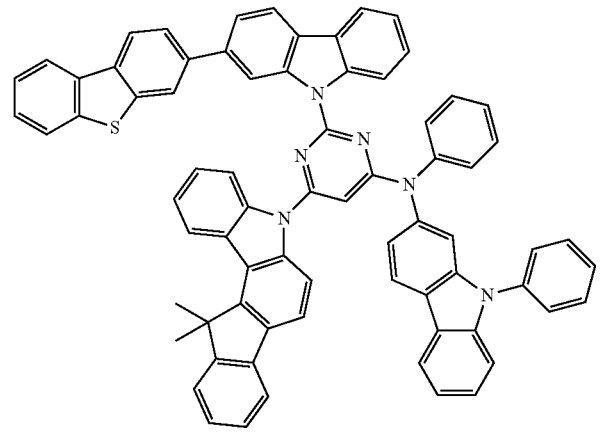 | 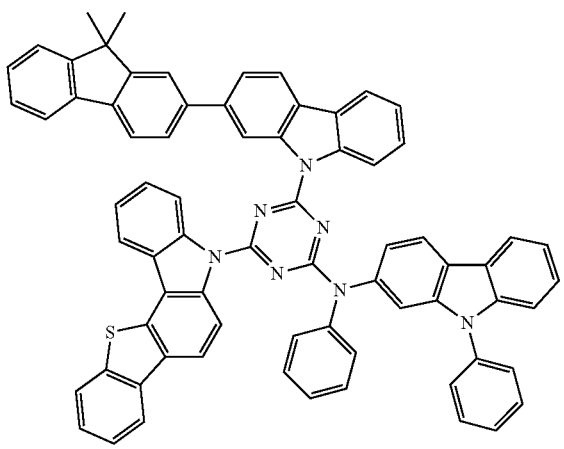 |

| 1957 | 1958 |
-continued
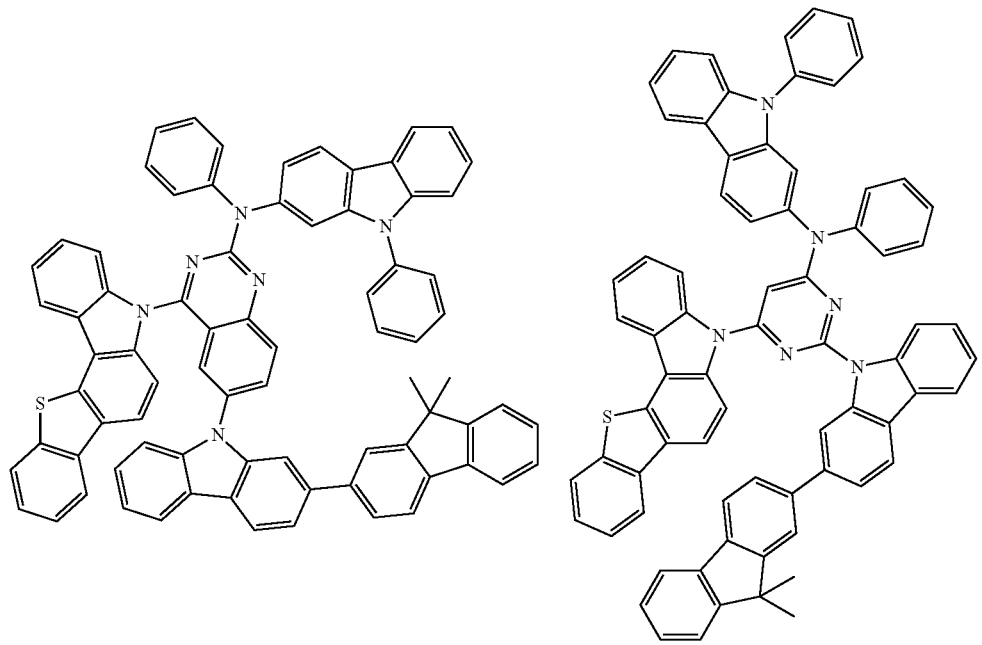
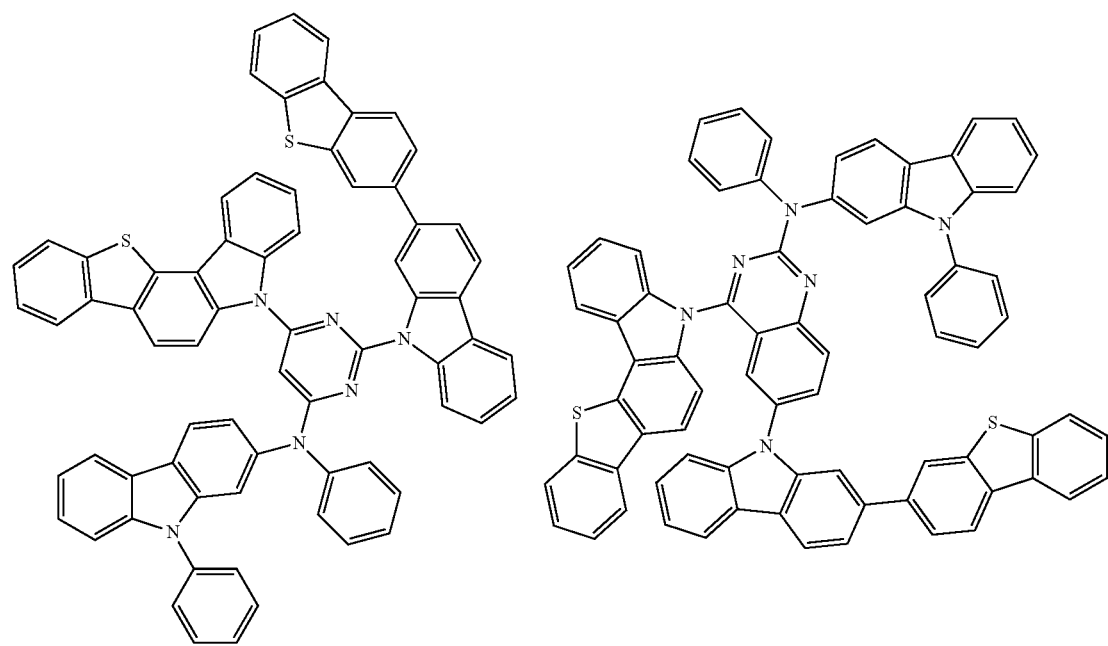

-continued
| 1959 | 1960 |
|---|---|
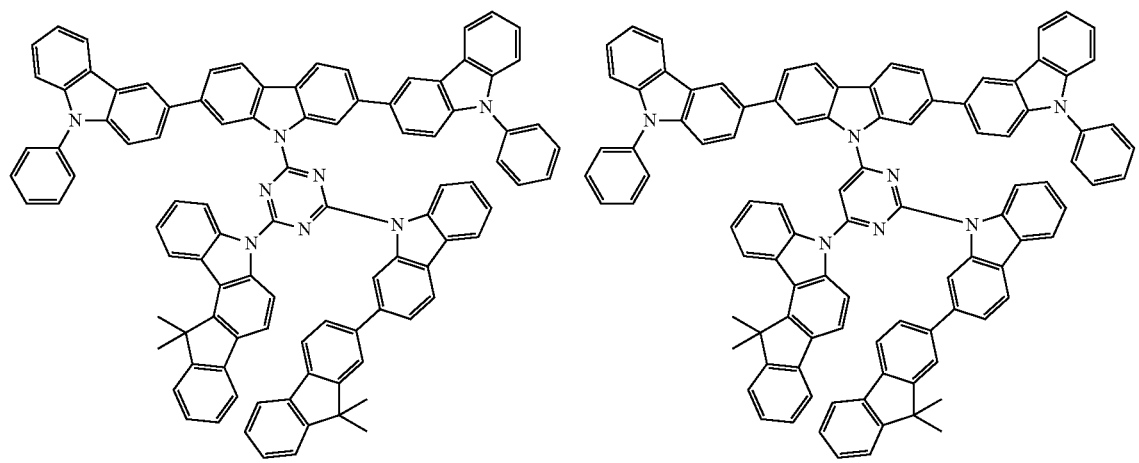
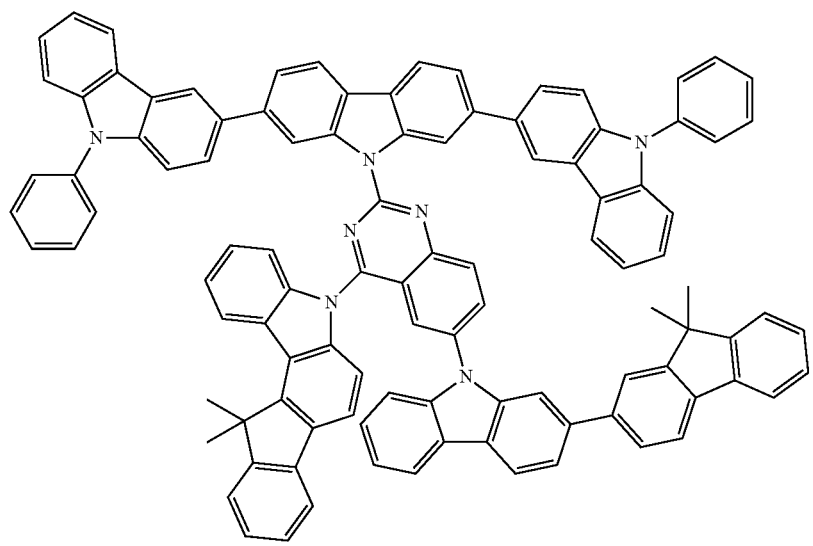
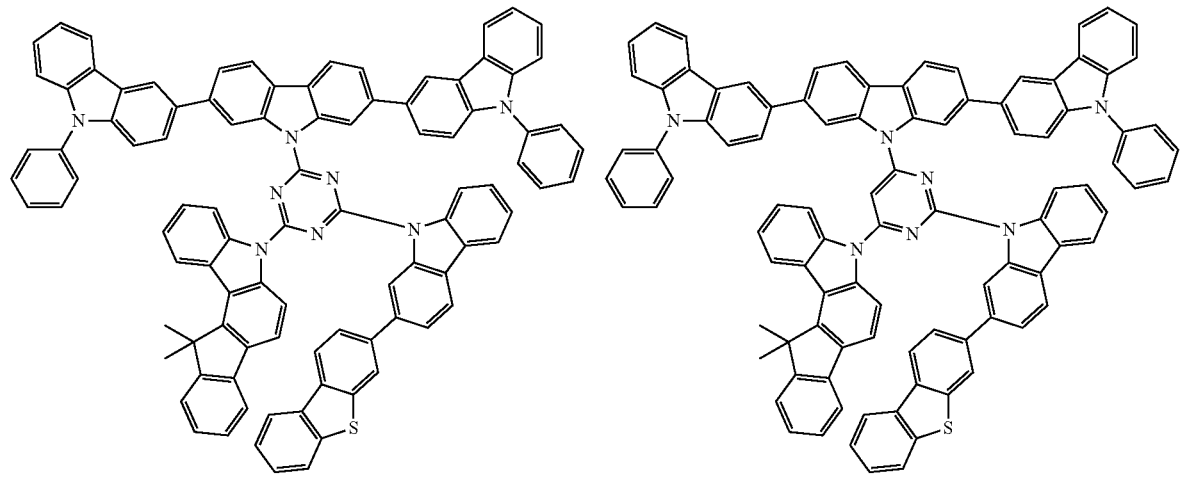

1961 1962
-continued
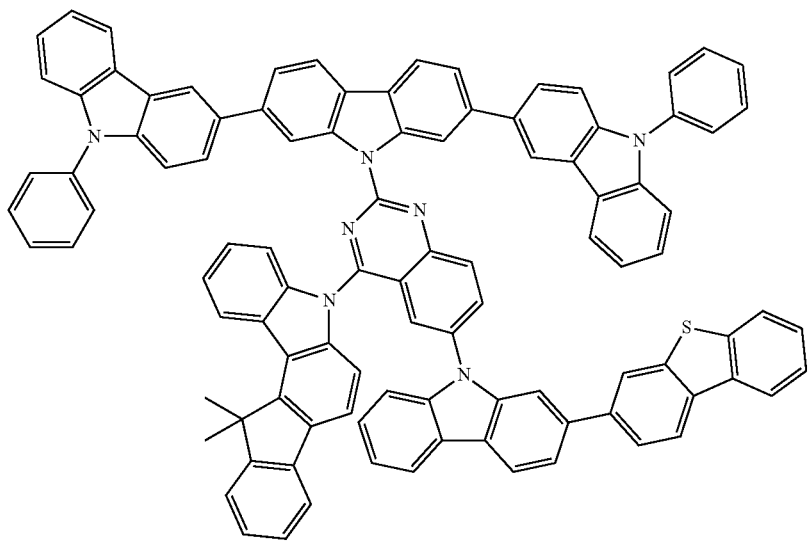
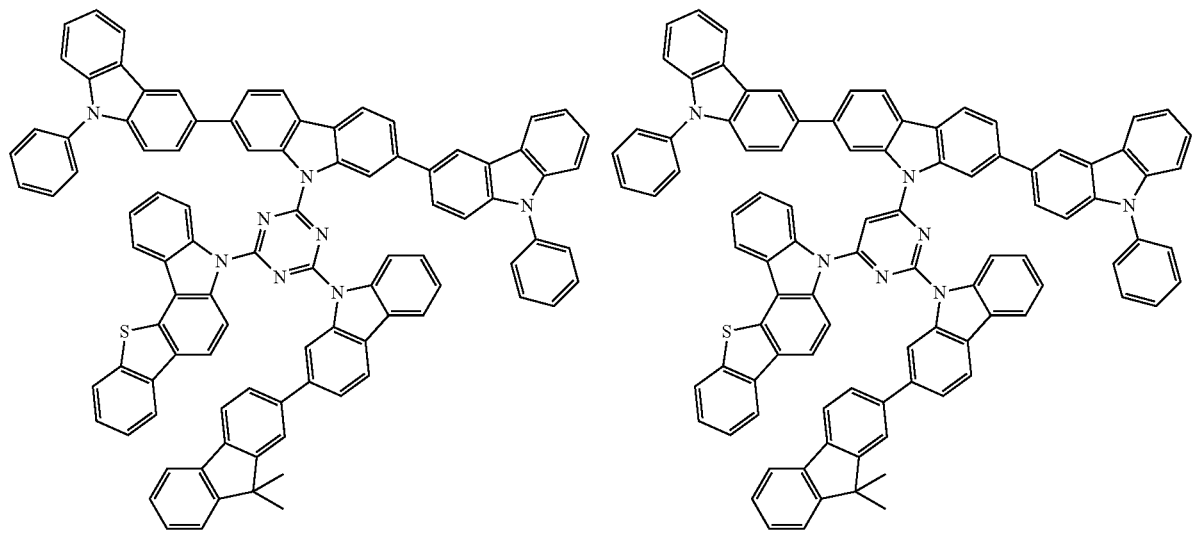
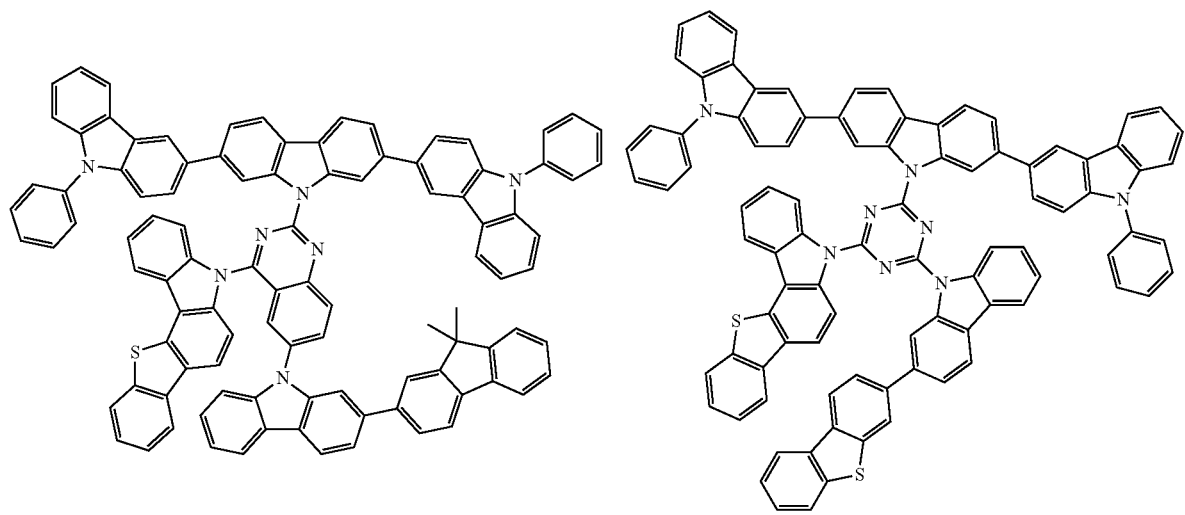

1963 1964
-continued
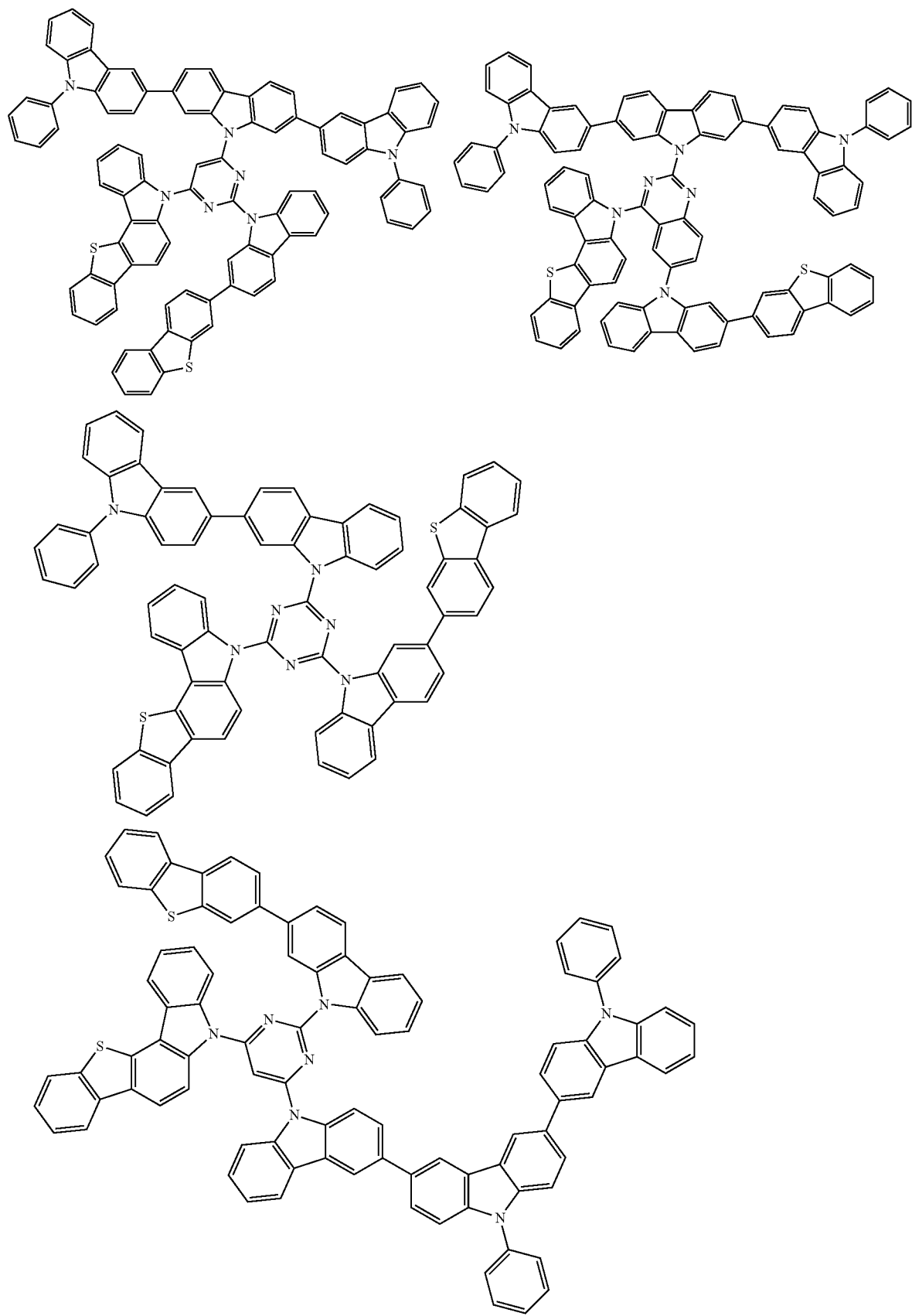

1965 1966
-continued
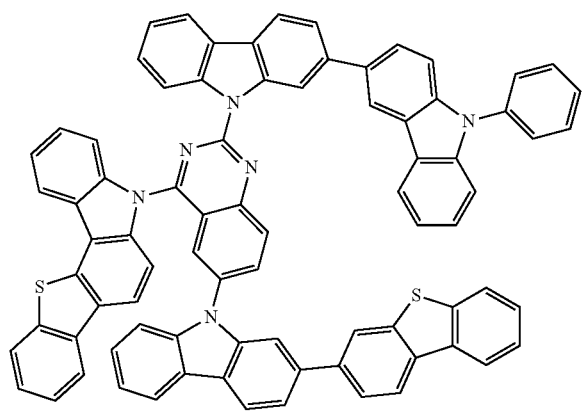
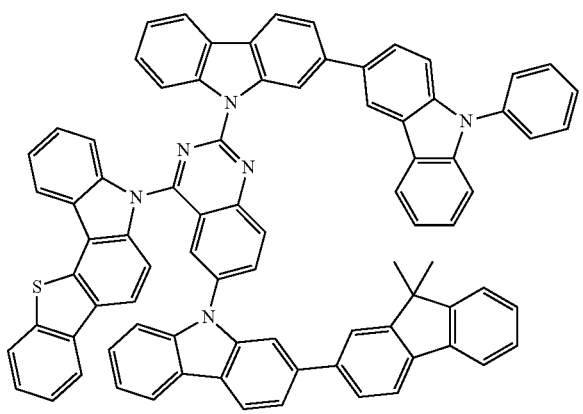
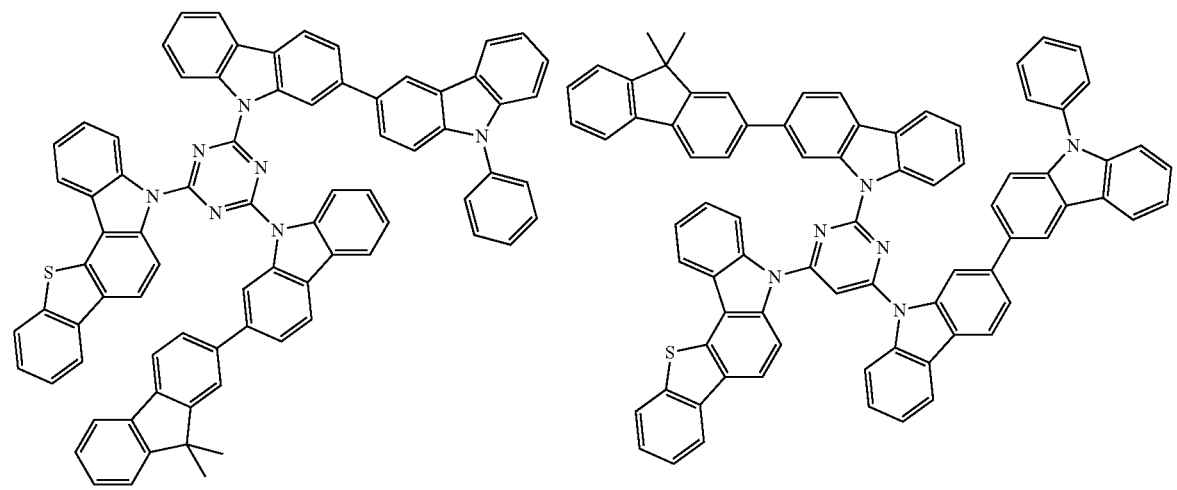
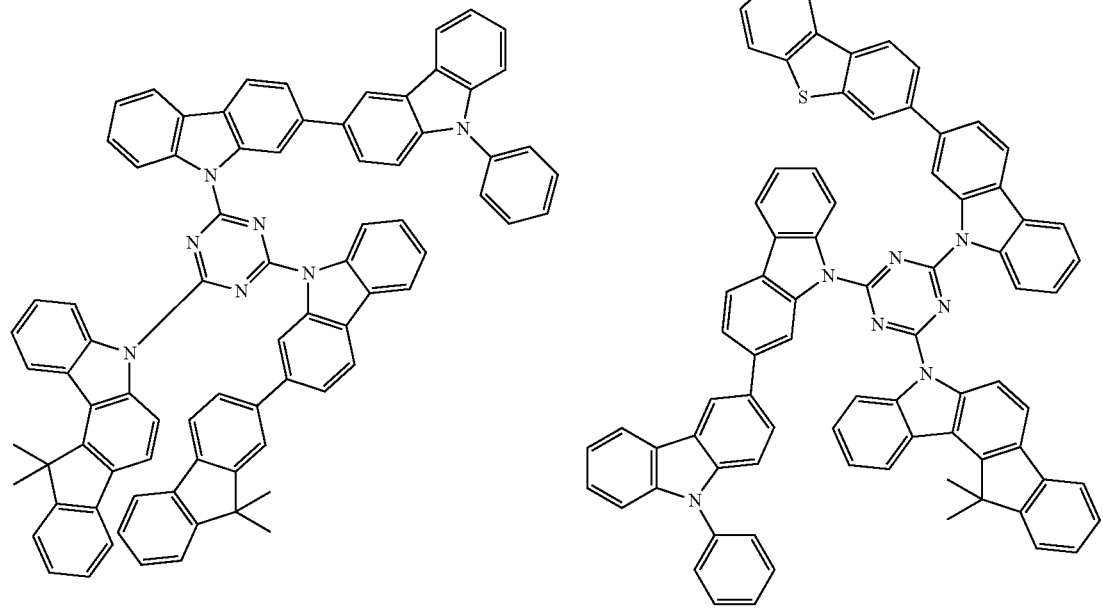

1967    1968
-continued
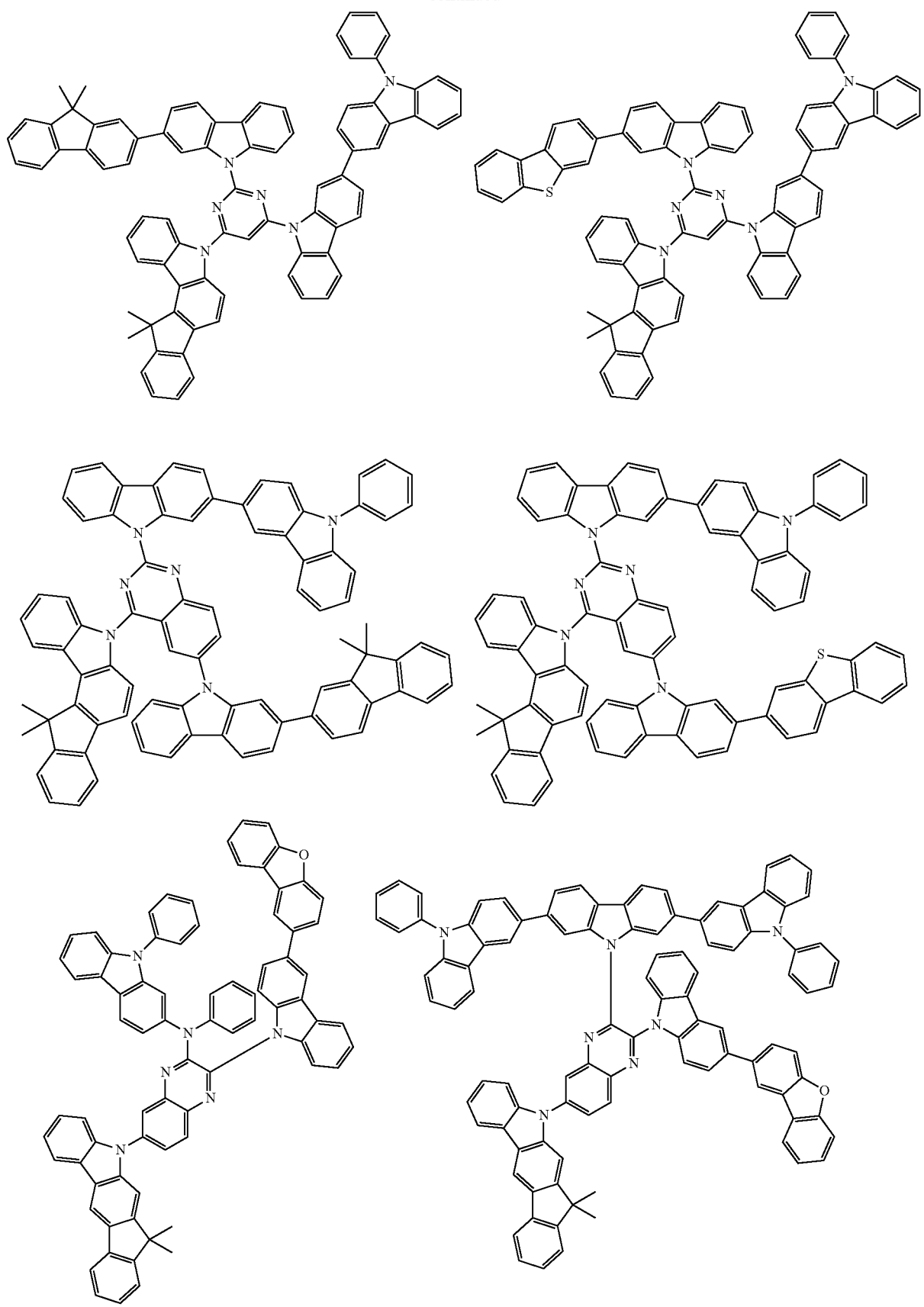

| 1969 | 1970 |
|---|---|
-continued
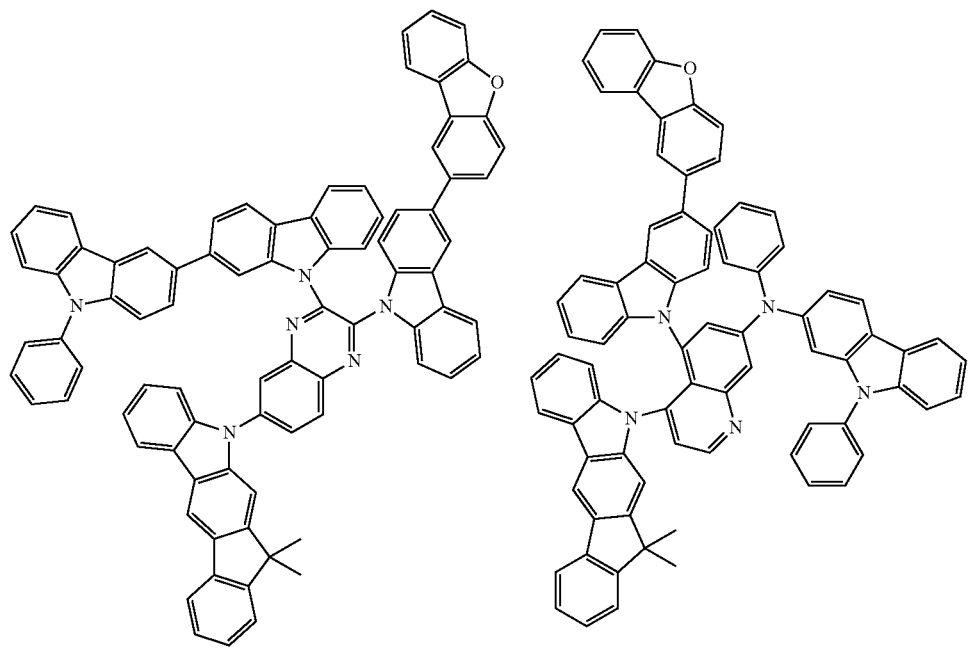
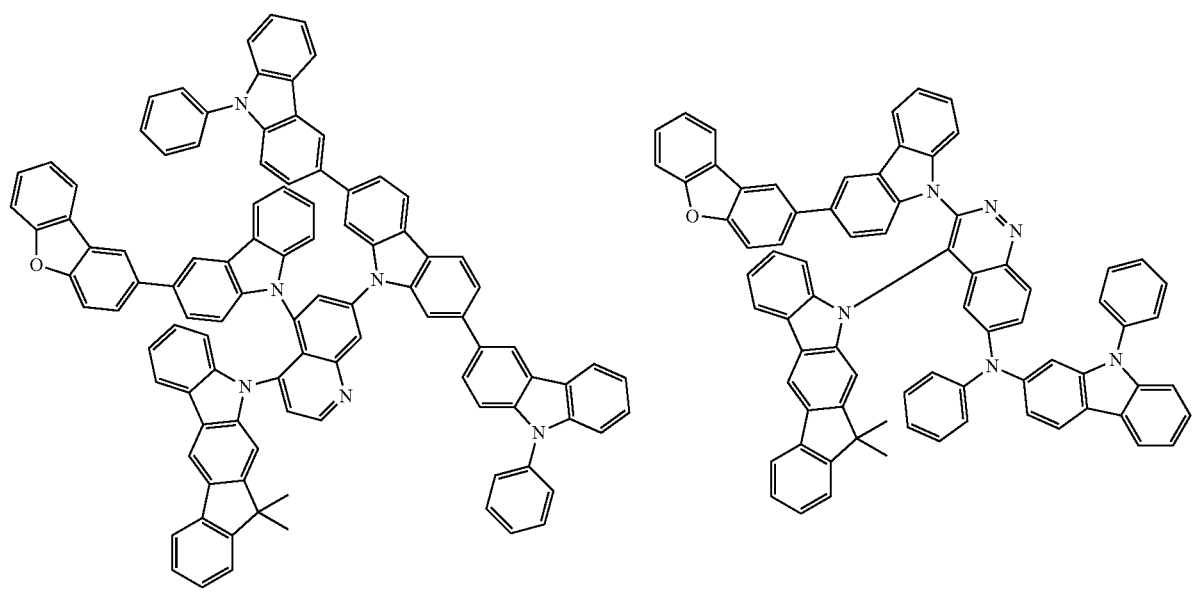

-continued
1971
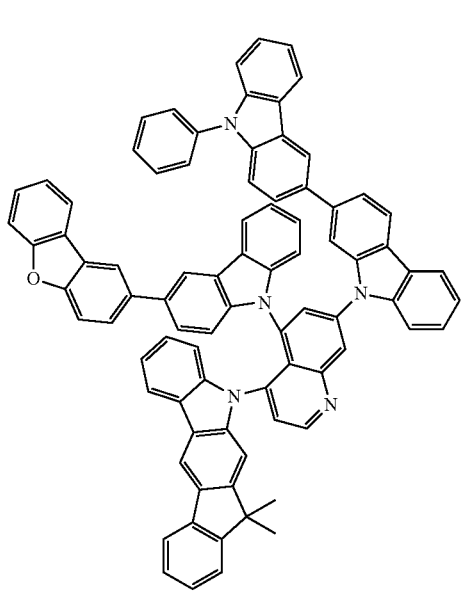
1972
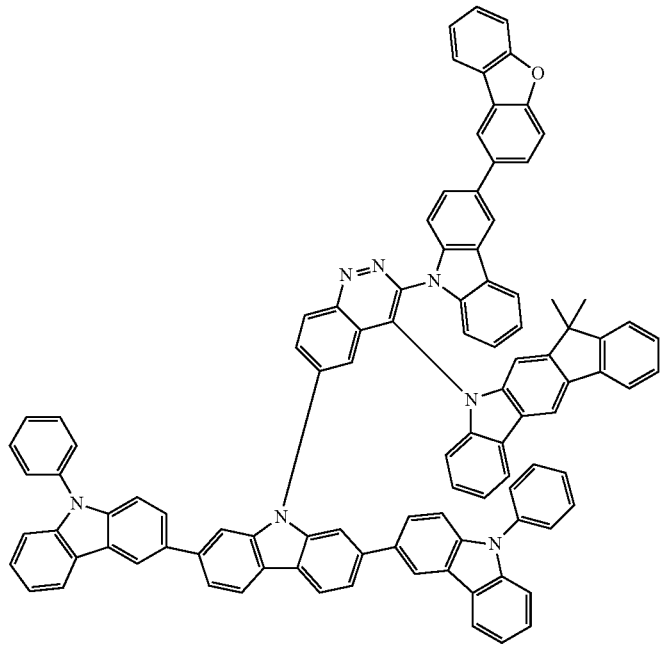
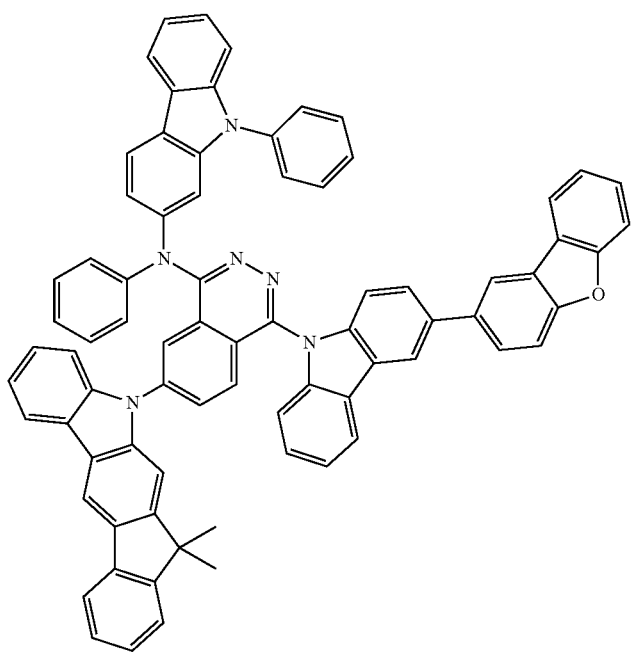

1973 1974
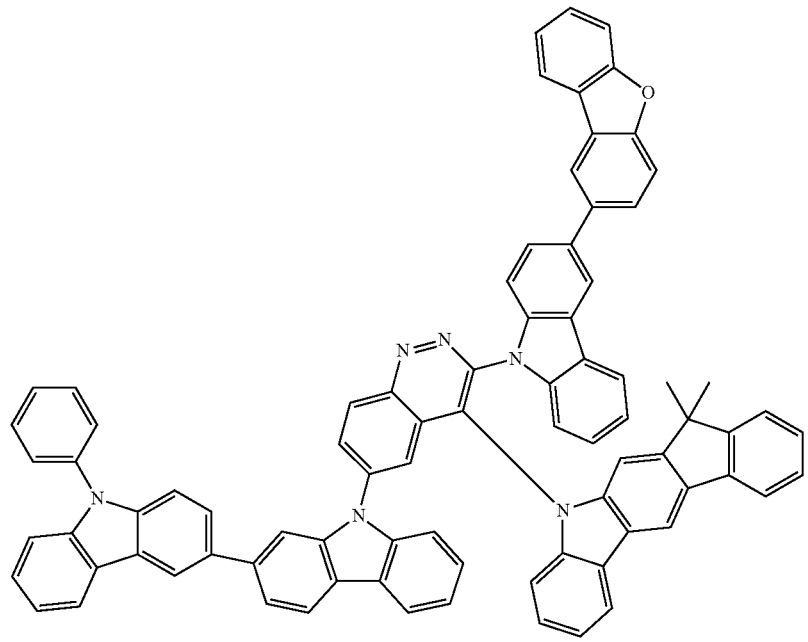
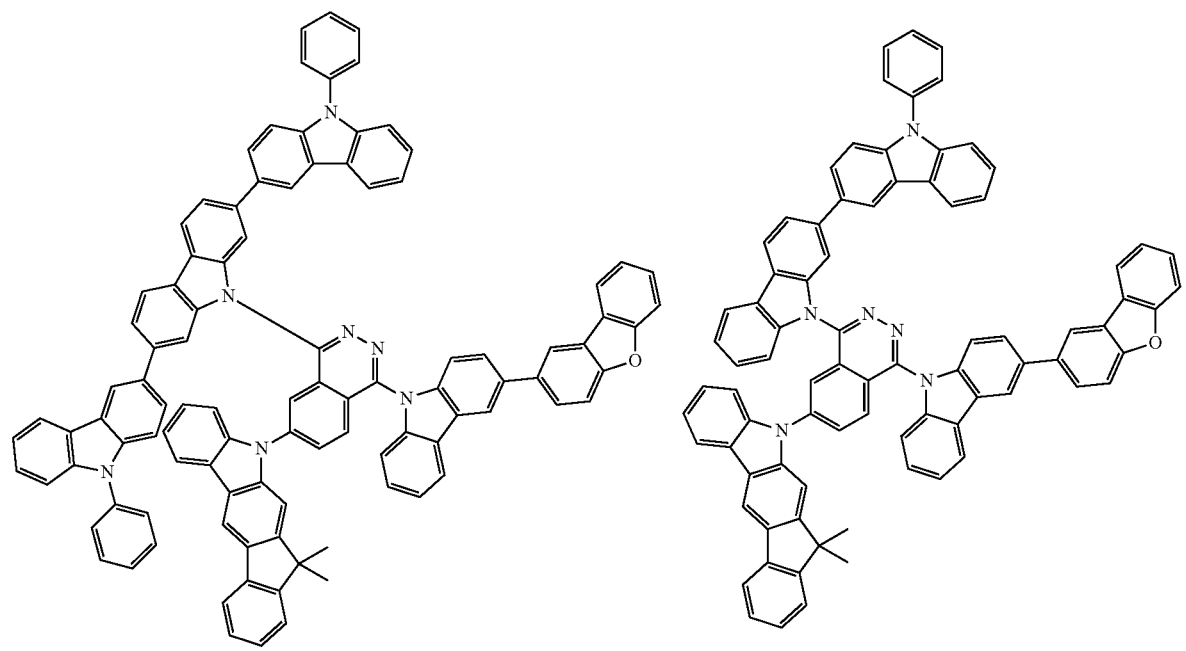

1975 1976
-continued
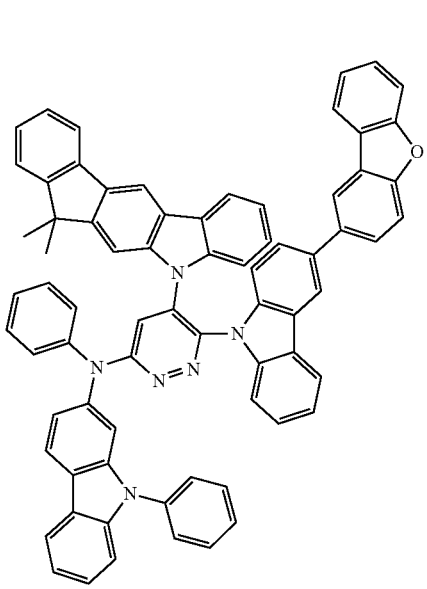
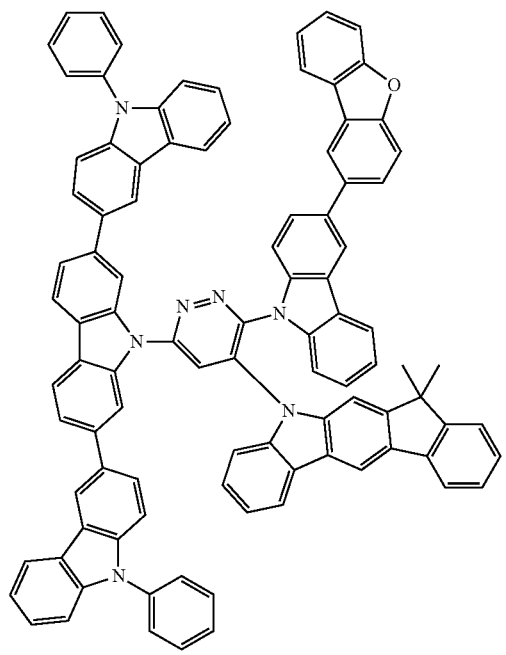
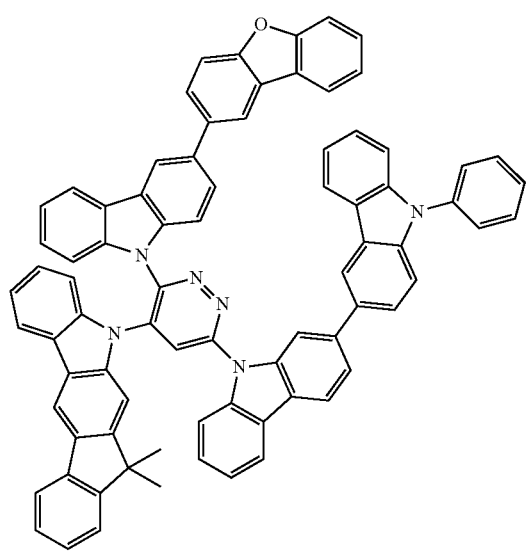
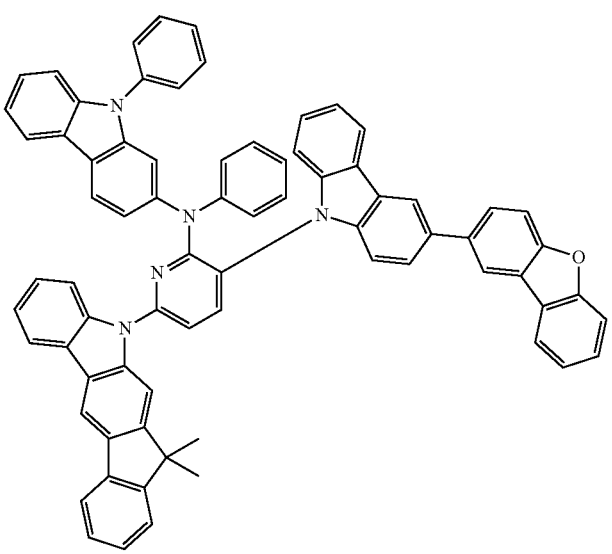

-continued
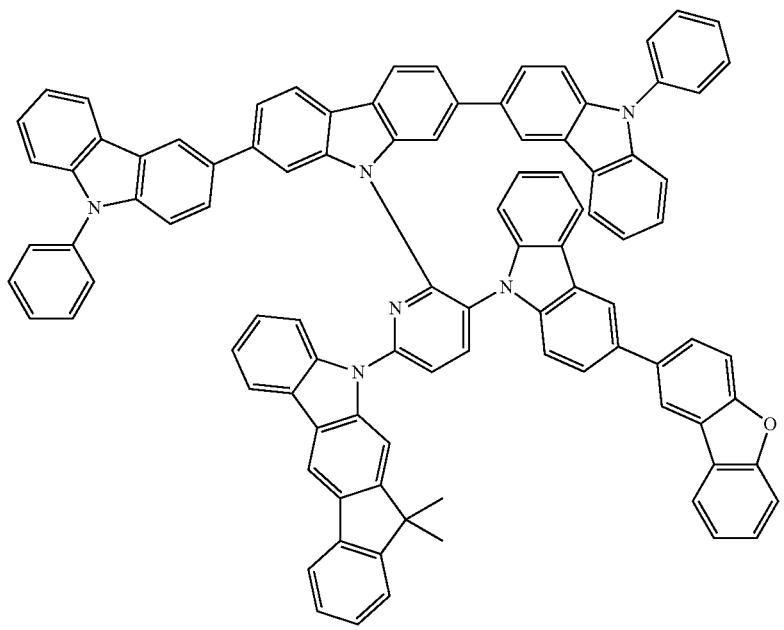
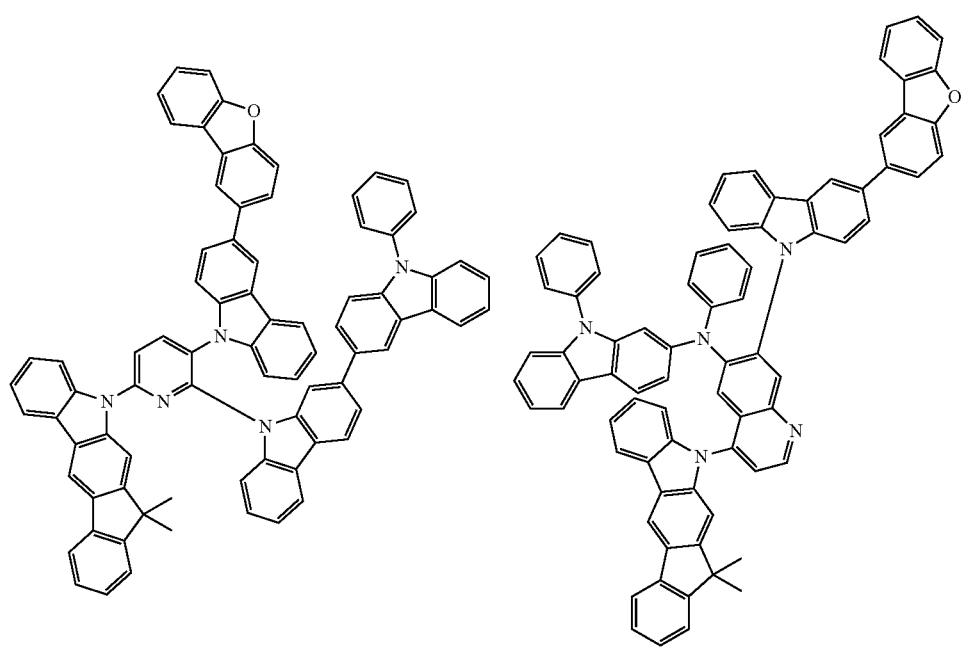

-continued
1979 1980
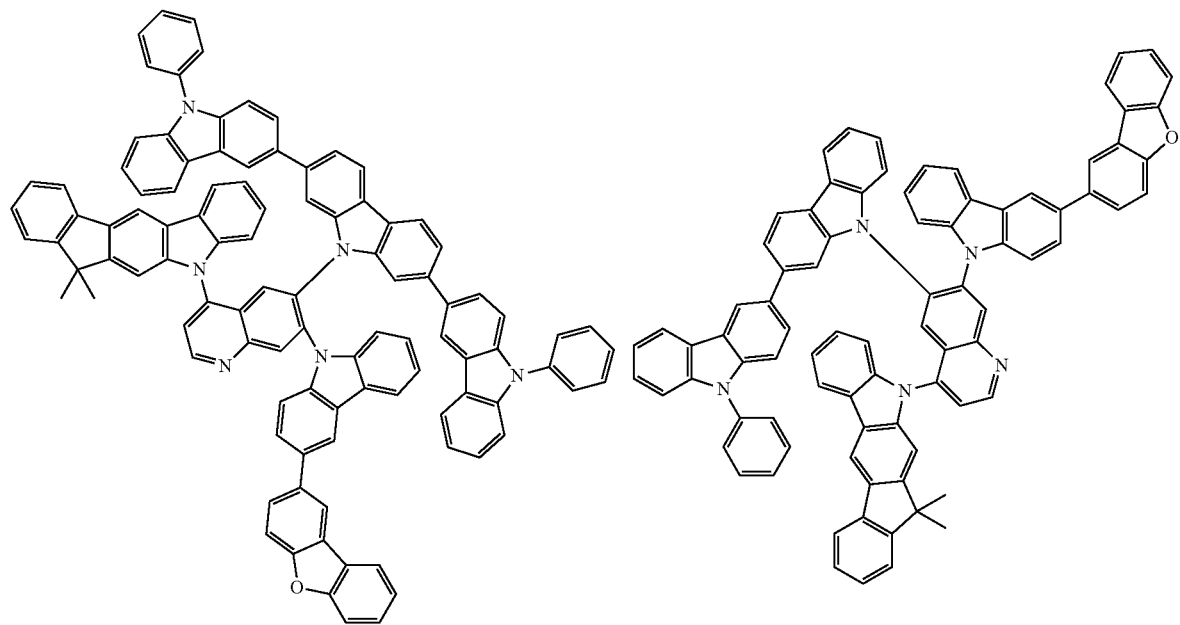
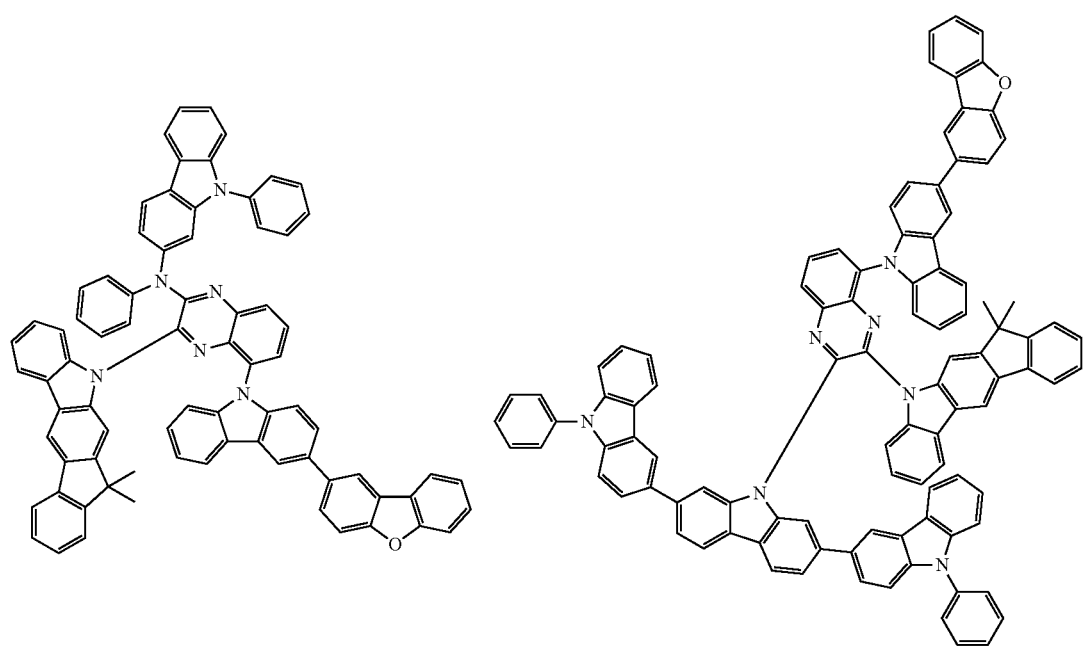

| 1981 | 1982 |
|---|---|
-continued
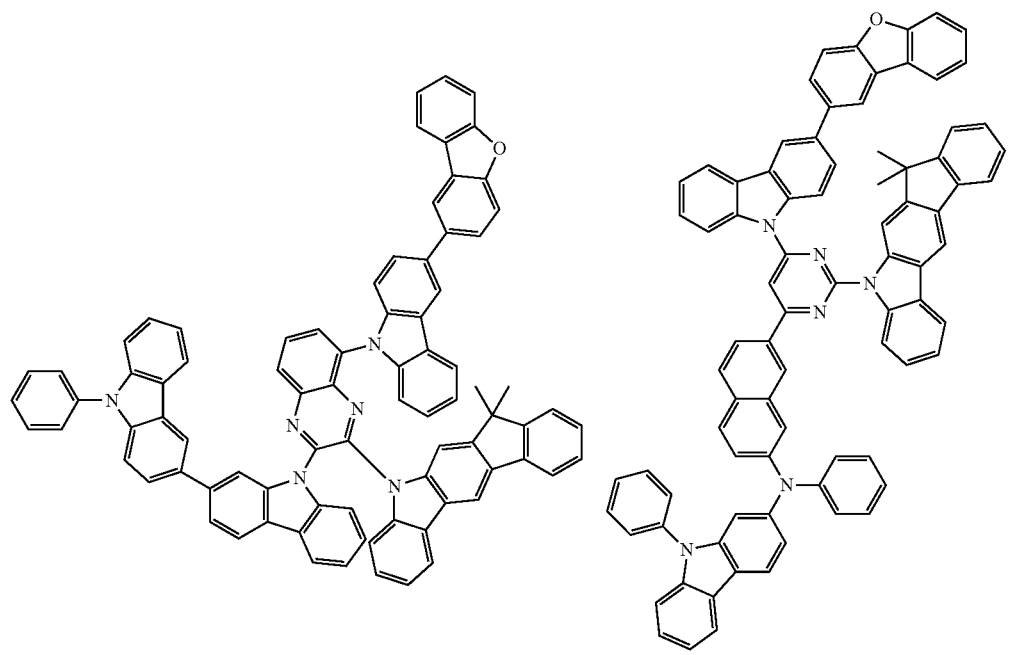
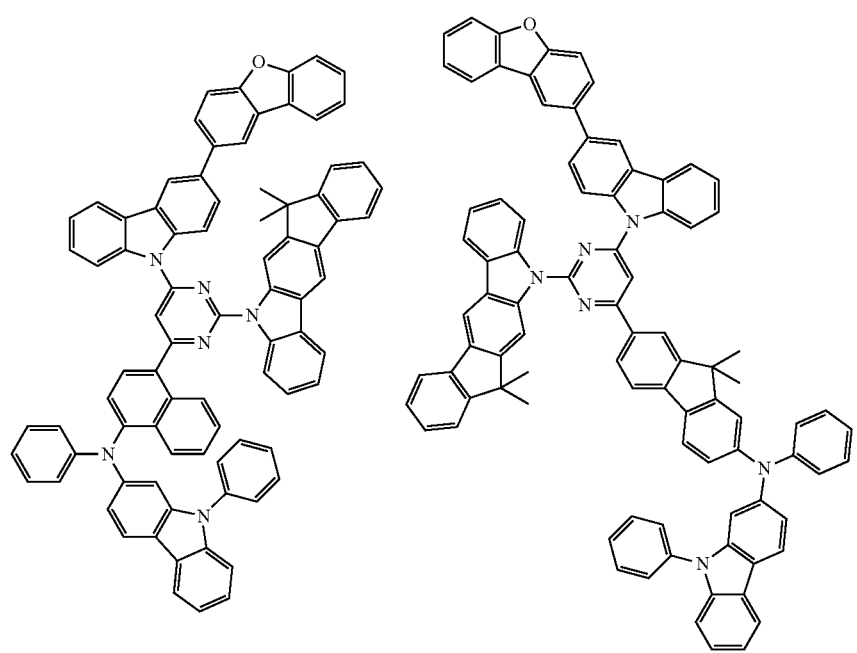

1983 1984
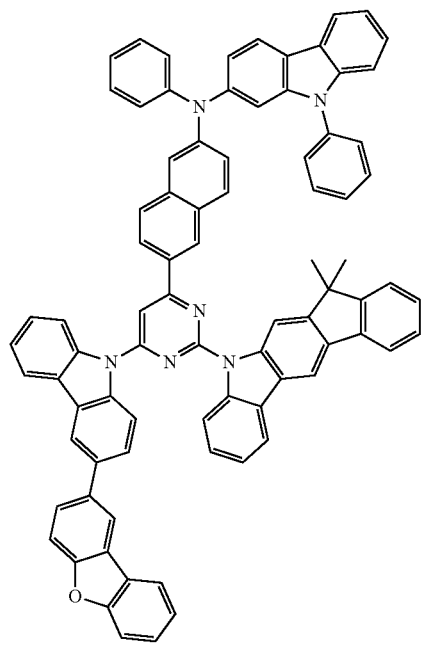
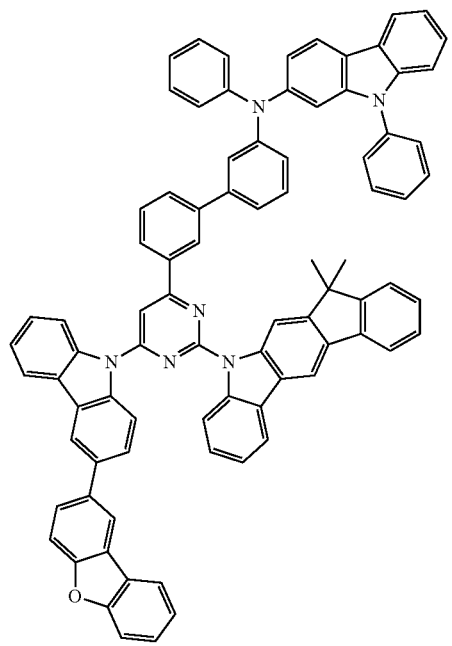
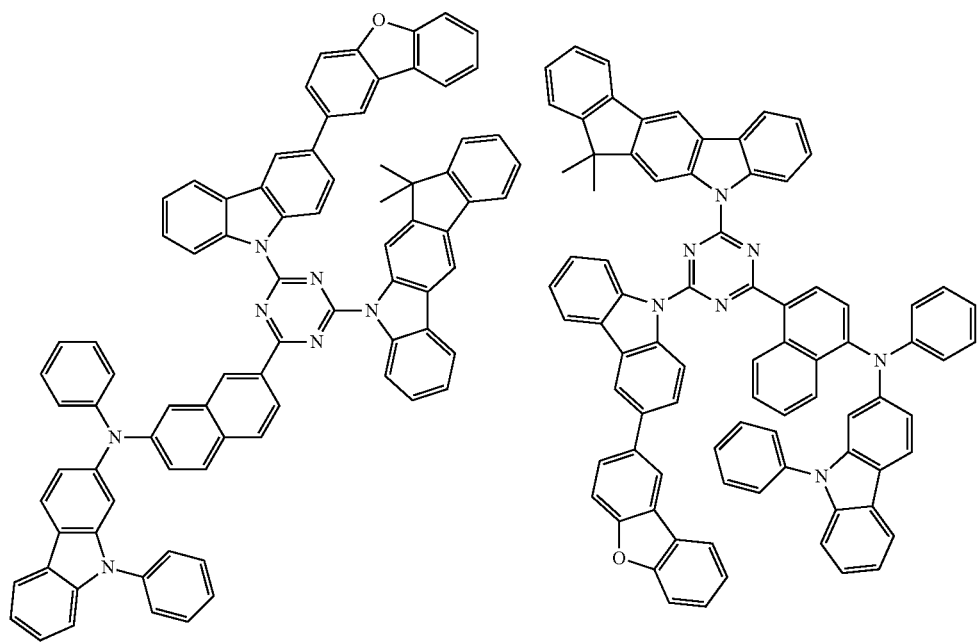

1985 1986
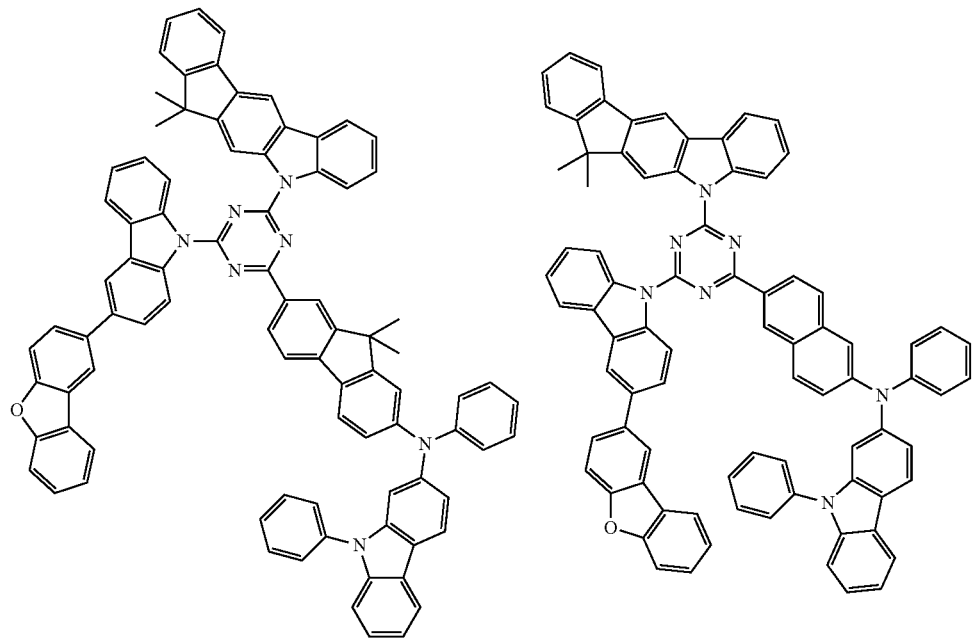
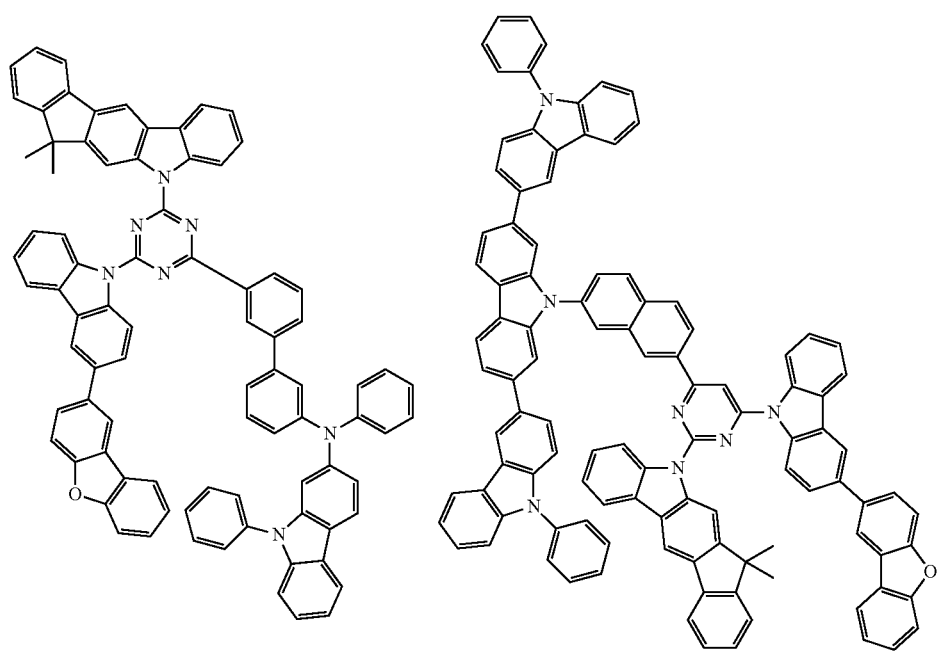

1987  1988
-continued
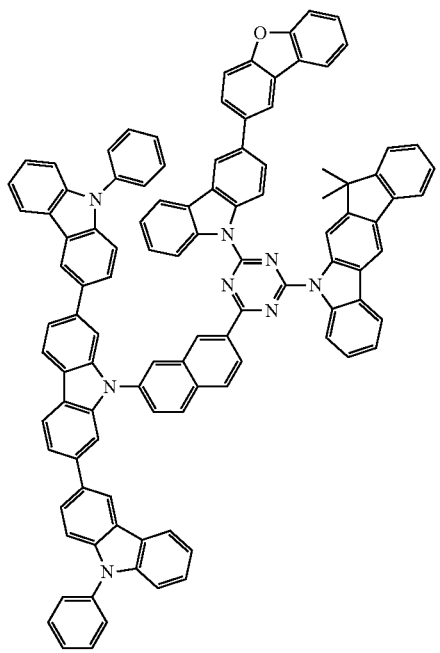
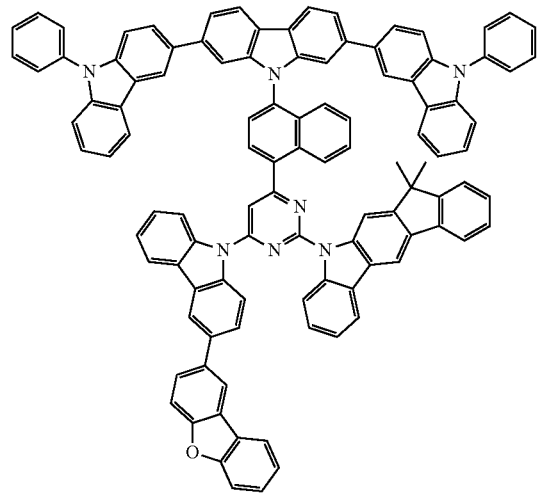
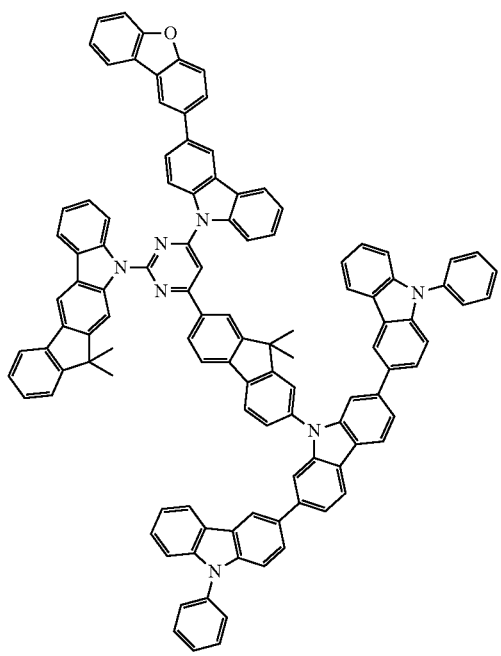
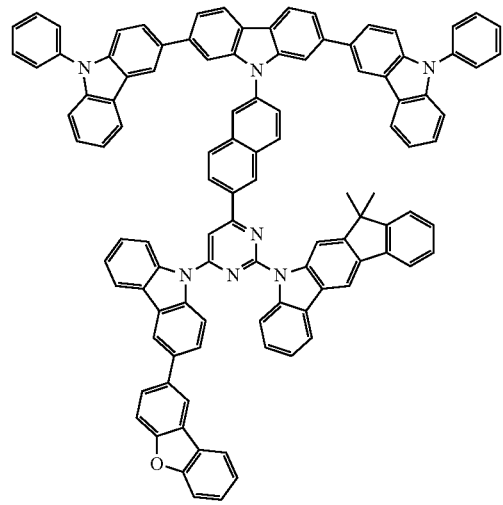

1989 1990
-continued
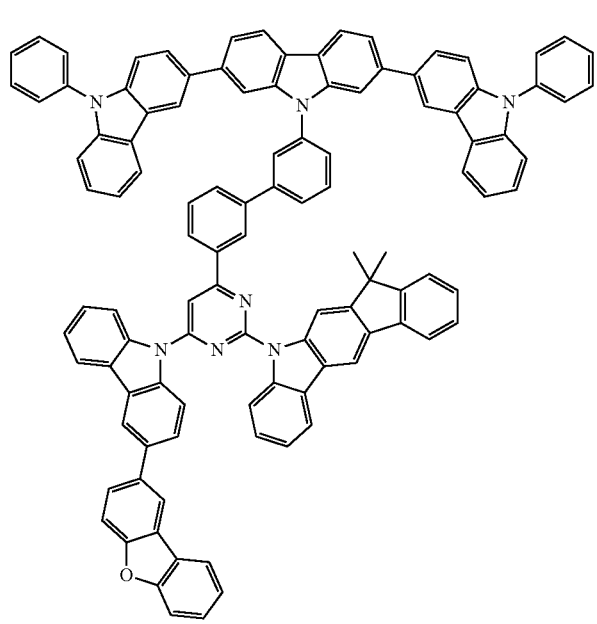
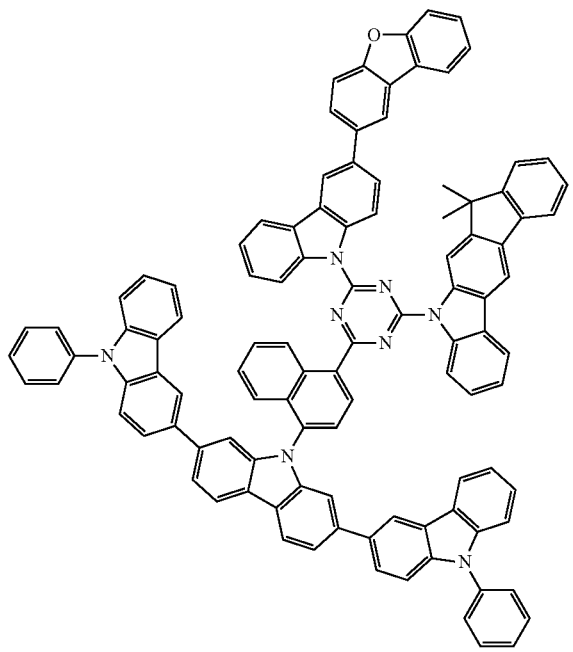
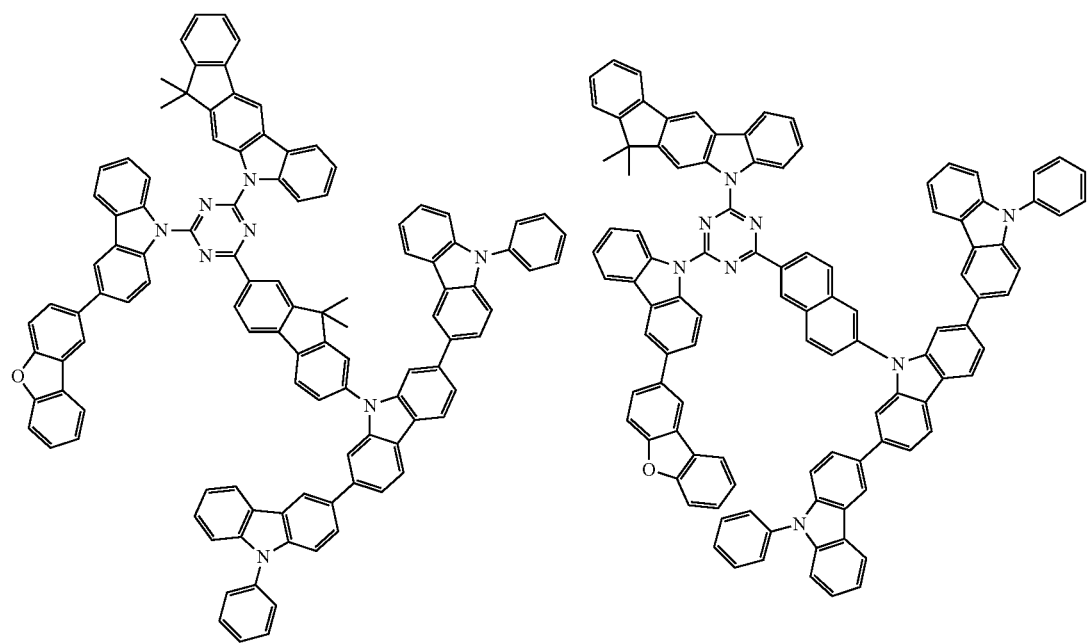

1991 1992
-continued
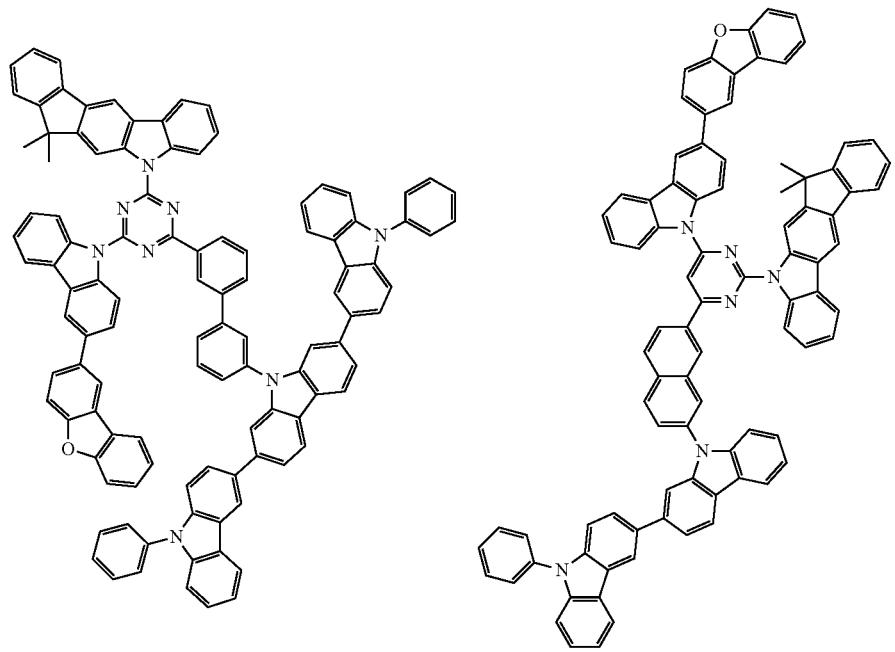
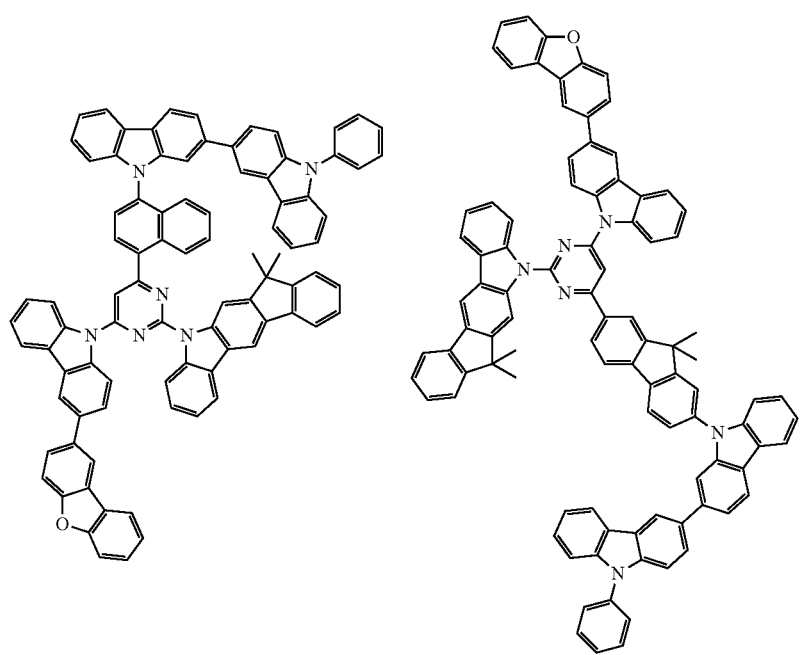

1993  1994
-continued
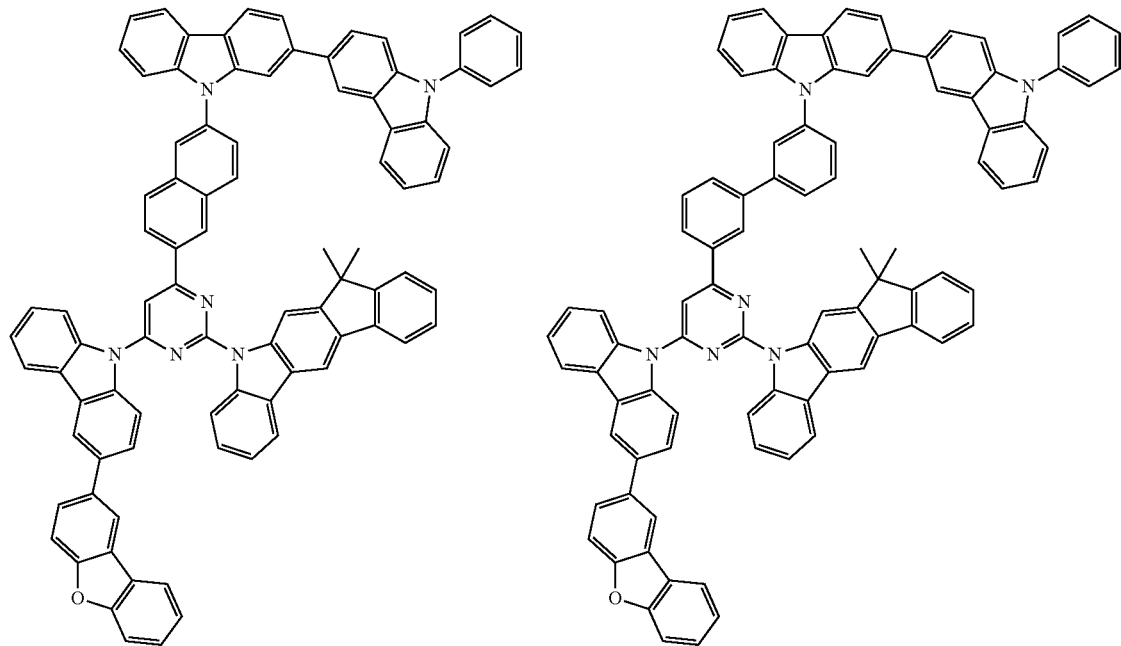
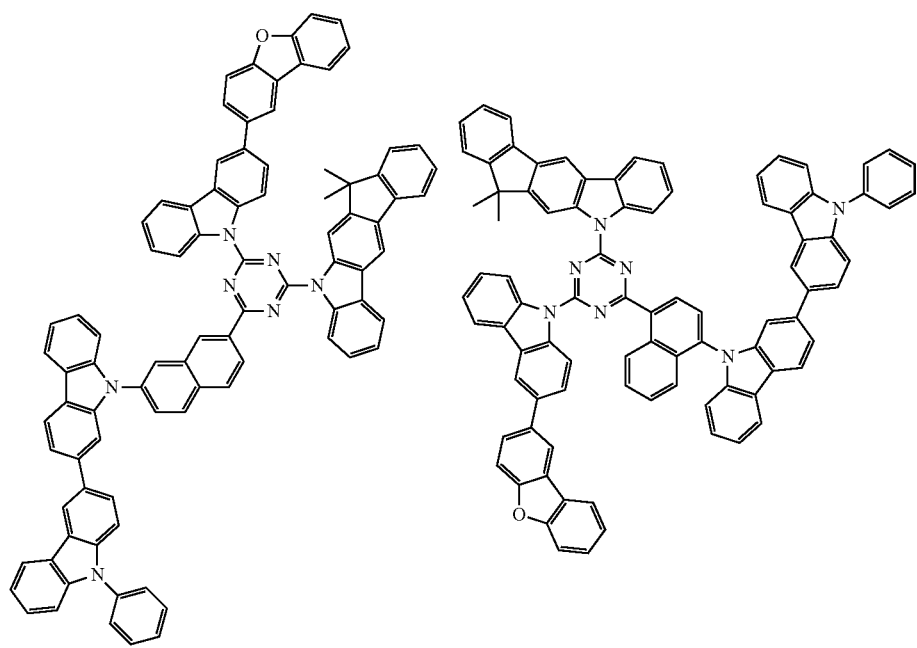

1995 1996
-continued
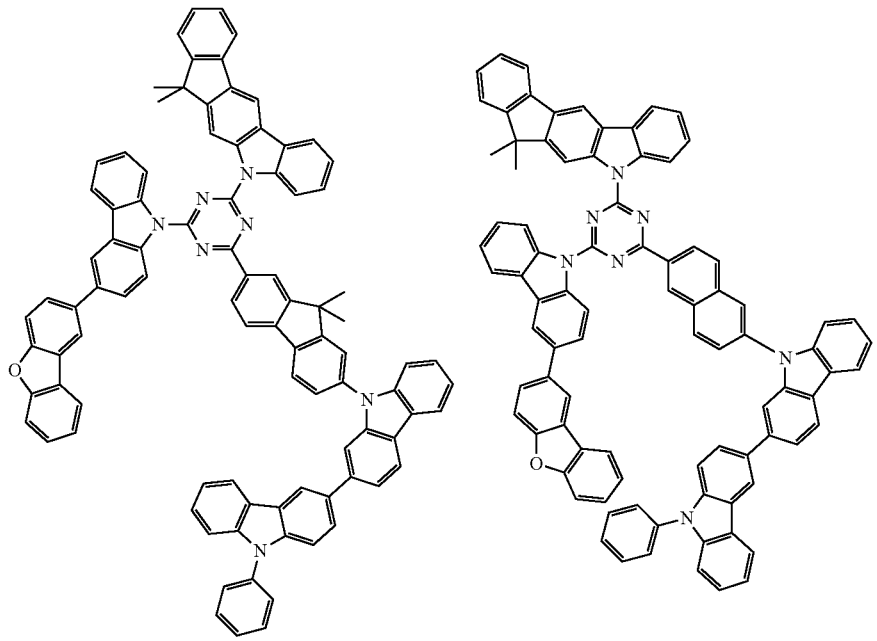
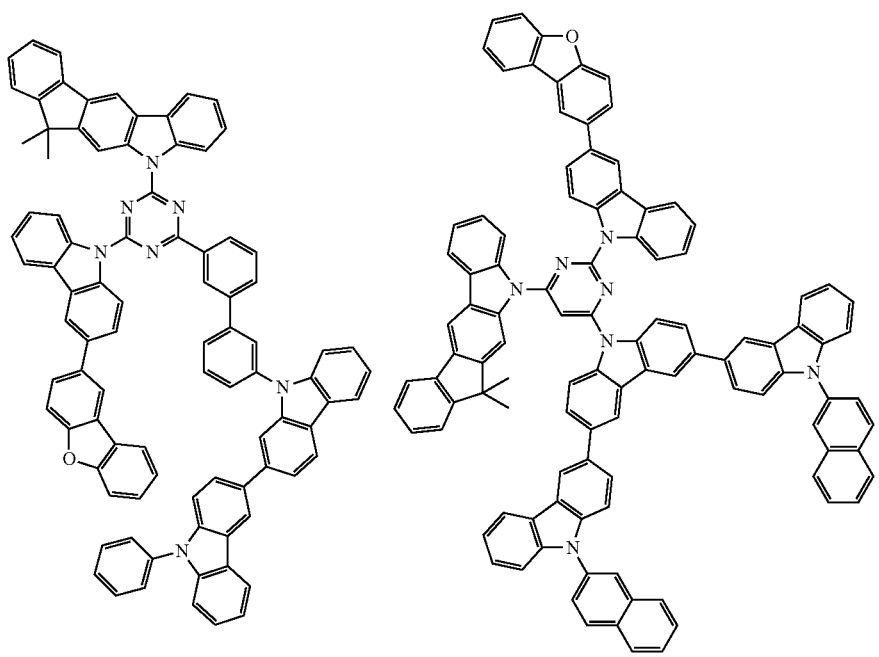

1997 1998
-continued
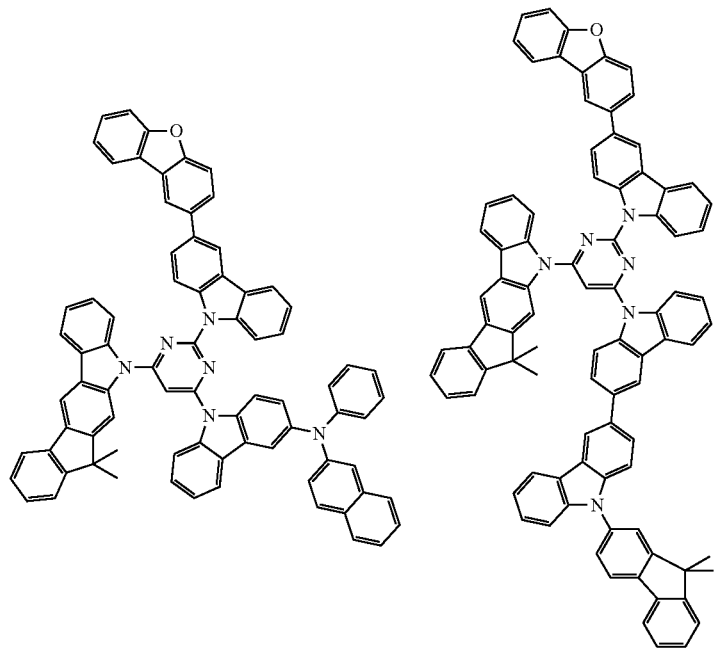
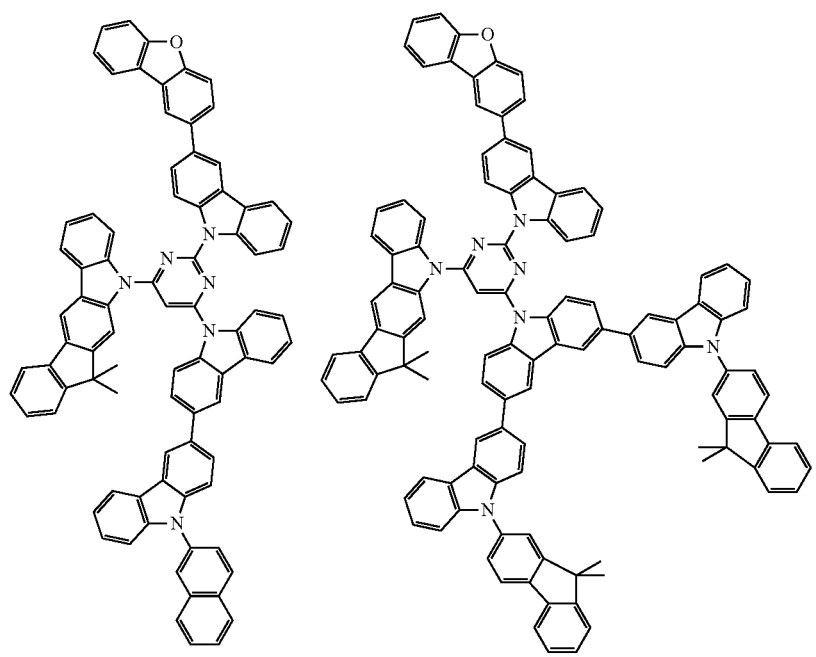

1999        2000
-continued
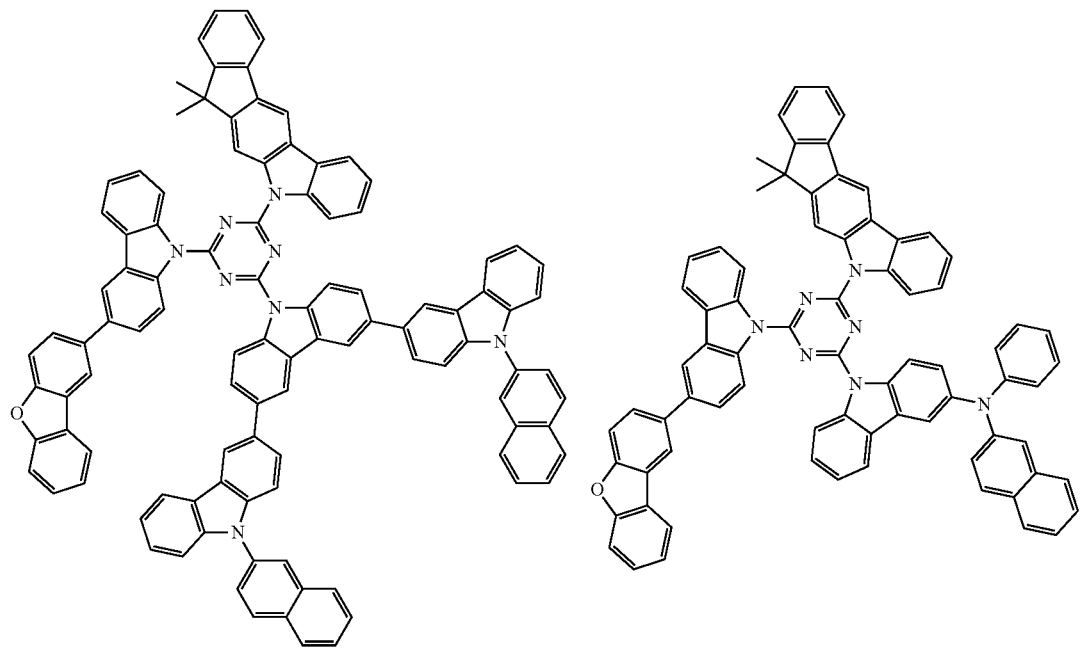
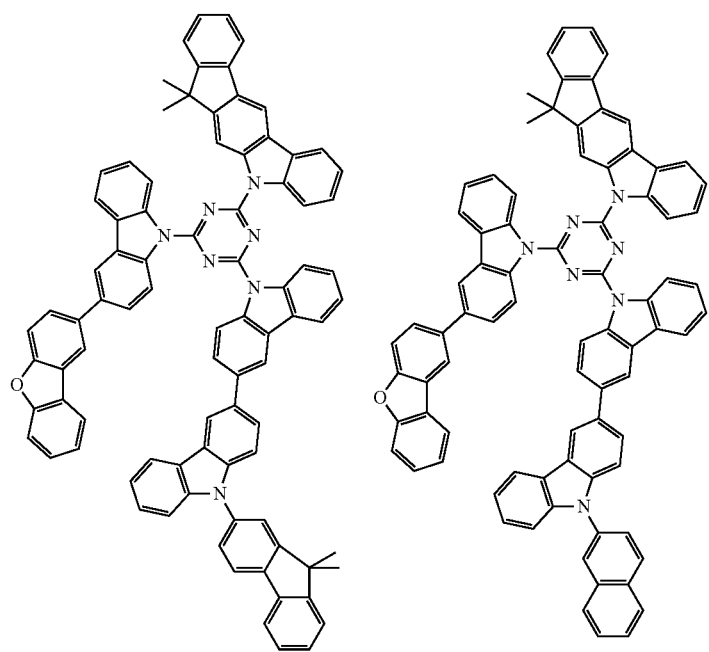

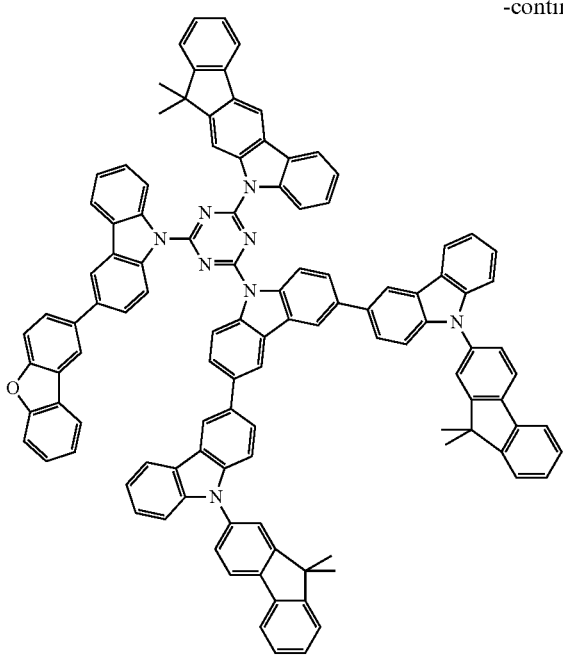

As described above, in an aspect of the invention, the invention relates to a composition comprising the compound of the invention mentioned above and at least one compound selected from the compounds represented by any of formulae (CH1), (CH3), (CH4), (CH5), (CH6), (CH14), and (CH15) (also referred to as compound (CH1), compound (CH3), compound (CH4), compound (CH5), compound (CH6), compound (CH14), and compound (CH15), respectively.

However, the compound (CH1), the compound (CH3), the compound (CH4), the compound (CH5), the compound (CH6), the compound (CH14), and the compound (CH15) are different form the compound of the invention mentioned above. Therefore, the compound overlapped with the compound of the invention is removed from the scope of each of the formulae (CH1), (CH3), (CH4), (CH5), (CH6), (CH14), and (CH15).

In the composition, the ratio of the compound of the invention and at least one compound selected from the compound (CH1), the compound (CH3), the compound (CH4), the compound (CH5), the compound (CH6), the compound (CH14), and the compound (CH15) is not particularly limited. In an aspect of the invention, the ratio of (compound of the invention):(at least one compound selected from the compound (CH1), the compound (CH3), the compound (CH4), the compound (CH5), the compound (CH6), the compound (CH14), and the compound (CH15)) is preferably 5:95 to 95:5, more preferably 10:90 to 90:10, still more preferably 20:80 to 80:20, and particularly preferably 40:60 to 60:40, each based on mass.

In another aspect of the invention, the ratio of (compound of the invention):(at least one compound selected from the compound (CH1), the compound (CH3), the compound (CH4), the compound (CH5), the compound (CH6), the compound (CH14), and the compound (CH15)) is preferably 5:95 to 90:10, more preferably 10:90 to 60:40, and still more preferably 20:80 to 40:60, each based on mass.

In another aspect of the invention, the ratio of (compound of the invention):(at least one compound selected from the compound (CH1), the compound (CH3), the compound (CH4), the compound (CH5), the compound (CH6), the compound (CH14), and the compound (CH15)) is preferably 10:90 to 95:5, more preferably 40:60 to 90:10, and still more preferably 60:40 to 80:20, each based on mass.

In the composition, the total content of the compound of the invention and at least one compound selected from selected from the compound (CH1), the compound (CH3), the compound (CH4), the compound (CH5), the compound (CH6), the compound (CH14), and the compound (CH15) is preferably 20% by mass or more, more preferably 50% by mass or more, still more preferably 70% by mass or more, still further preferably 80% by mass or more, particularly preferably 90% by mass or more, and most preferably substantially 100% by mass.

The compound (CH1), the compound (CH3), the compound (CH4), the compound (CH5), the compound (CH6), the compound (CH14), and the compound (CH15) are described below.

Compound (CH1)

Compound (CH1) preferably combines a hole transporting skeleton and an electron transporting skeleton in its molecule. More preferably, the structure B comprises a hole transporting skeleton and the structure A comprises an electron transporting skeleton.

$$A\text{-}(\text{-}L^1\text{-}B)_m \qquad (\text{CH1})$$

in formula (CH1),

A represents a substituted or unsubstituted aromatic heterocyclic group;

$L^1$ represents a single bond, a substituted or unsubstituted aromatic hydrocarbon group, or a substituted or unsubstituted aromatic heterocyclic group; and B represents a residue of a structure represented by formula (CH2) described below.

The subscript m represents an integer of 2 or more. The upper limit of m depends on the structure of A and is preferably 2 to about 10 in view of increasing a glass transition temperature and more preferably 2 or 3, although not particularly limited thereto. The composition of the invention is preferably capable of forming the layer of an organic EL device by a coating method, in which an organic thin film is generally formed by forming a coating film and then evaporating the solvent under heating. A material having a high glass transition temperature is advantageous for forming an amorphous organic thin film.

Two or more groups $L^1$ may be the same or different, and two or more groups B may be the same or different. In view of solubility, two or more structures -$L^1$-B are preferably different so as to make the compound asymmetric with respect to A.

The compound (CH1) is preferably a compound represented by formula (CHi) or (CH1-A):

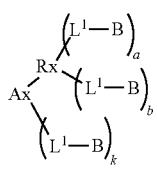

(CH1-A')

in formula (CH1-A'), a represents an integer of 1 or more; b represents an integer of 1 or more; a+b is m−k in formula (CH1-A); Ax, Rx, $L^1$, B, and k are as defined above in formula (CH1-A); two or more groups $L^1$ may be the same or different; and two or more groups B may be the same or different.

Formula (CH2) will be described below, in which $Z^1$, $X^1$, $Y^1$, $Z^2$, $X^2$, $Y^2$, or $L^2$ is bonded to $L^1$ or A when $L^1$ is a single bond to form a compound of formula (CH1).

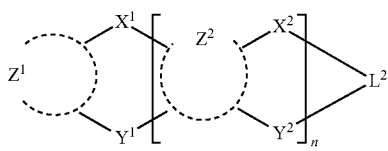

(CH2)

In formula (CH2), one of $X^1$ and $Y^1$ represents a single bond, —$CR_2$—, —NR—, —O—, —S—, or —$SiR_2$— and the other represents —NR—, —O—, —S— or —$SiR_2$—; and one of $X^2$ and $Y^2$ represents a single bond, —$CR_2$—, —NR—, —O—, —S—, or —$SiR_2$— and the other represents —NR—, —O—, —S—, or —$SiR_2$—.

R represents a hydrogen atom, a substituted or unsubstituted alkyl group, a substituted or unsubstituted cycloalkyl group, a substituted or unsubstituted aromatic hydrocarbon group, or a substituted or unsubstituted aromatic heterocyclic group.

$Z^1$ and $Z^2$ each independently represent a substituted or unsubstituted aliphatic hydrocarbon group, a substituted or unsubstituted aliphatic heterocyclic group, a substituted or unsubstituted aromatic hydrocarbon group, or a substituted or unsubstituted aromatic heterocyclic group.

$L^2$ represents a linking group, for example, —$CR_2$—, —$CR_2CR_2$—, —CR=CR—, —NR—, —N=CR—, a substituted or unsubstituted aliphatic hydrocarbon group, a substituted or unsubstituted aliphatic heterocyclic group, a substituted or unsubstituted aromatic hydrocarbon group, or a substituted or unsubstituted aromatic heterocyclic group.

R in $L^2$ is as defined above with respect to R in $X^1$, $X^2$, $Y^1$ and $Y^2$.

The subscript n represents an integer of 0 to 5, preferably 0 to 2, and particularly preferably 0 or 1. When n is an integer of 2 or more, two or more groups $Z^2$ may be the same or different, two or more groups $X^2$ may be the same or different, and two or more groups $Y^2$ may be the same or different.

The structure represented by formula (CH2) is preferably a structure represented by formula (CH2-a) or (CH2-b). The compound represented by formula (CH1) may comprise both the structure represented by formula (CH2-a) and the structure represented by formula (CH2-b).

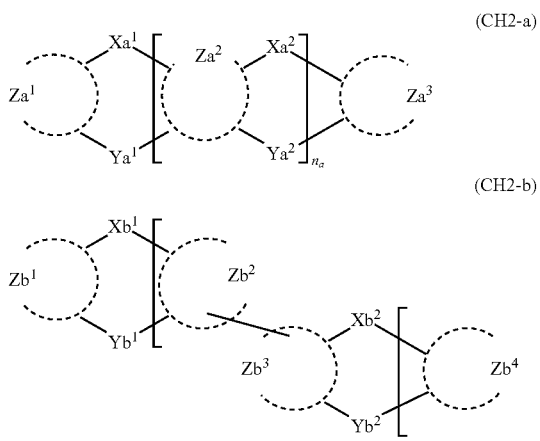

Formula (CH2-a) will be described below, which corresponds to formula (CH2) wherein $L^2$ is $Za^3$. One of $Za^1$, $Xa^1$, $Ya^1$, $Za^2$, $Xa^2$, $Ya^2$, and $Za^3$ in formula (CH2-a) is bonded to $L^1$ or A when $L^1$ is a single bond to form a compound of formula (CH1).

One of $Xa^1$ and $Ya^1$ represents a single bond, —$CR_2$—, —NR—, —O—, —S—, or —$SiR_2$—, and the other represents —NR—, —O—, —S—, or —$SiR_2$—.

One of $Xa^2$ and $Ya^2$ represents a single bond, —$CR_2$—, —NR—, —O—, —S—, or —$SiR_2$—, the other represents —NR—, —O—, —S—, or —$SiR_2$—.

R in $Xa^1$, $Xa^2$, $Ya^1$, and $Ya^2$ is as defined above with respect to R in $X^1$, $X^2$, $Y^1$, and $Y^2$ of formula (CH2).

$Za^1$, $Za^2$ and $Za^3$ each independently represent a substituted or unsubstituted aliphatic hydrocarbon group, a substituted or unsubstituted aliphatic heterocyclic group, a substituted or unsubstituted aromatic hydrocarbon group, or a substituted or unsubstituted aromatic heterocyclic group.

The subscript $n_a$ represents an integer of 0 to 5, preferably 0 to 2, and particularly preferably 0 or 1. When $n_a$ is an integer of 2 or more, two or more groups $Za^2$ may be the same or different, two or more groups $Xa^2$ may be the same or different, and two or more groups $Ya^2$ may be the same or different.

Formula (CH2-b) will be described below, which corresponds to formula (CH2) wherein n is 0 and $L^2$ is an aromatic hydrocarbon ring group or an aromatic heterocyclic group each having a substituent comprising 3 or more fused rings. One of $Zb^1$, $Xb^1$, $Yb^1$, $Zb^2$, $Zb^3$, $Xb^2$, $Yb^2$, and $Zb^4$ is bonded to $L^1$ or A when $L^1$ is a single bond to form the compound of formula (CH1). The ring $Zb^2$ and the ring $Zb^3$ are bonded to each other via a single bond. In view of the solubility, formula (CH2-b) is preferred.

One of $Xb^1$ and $Yb^1$ represents a single bond, —$CR_2$—, —NR—, —O—, —S—, or —$SiR_2$—, and the other represents —NR—, —O—, —S—, or —$SiR_2$—.

One of $Xb^2$ and $Yb^2$ represents a single bond, —$CR_2$—, —NR—, —O—, —S—, or —$SiR_2$—, and the other represents —NR—, —O—, —S—, or —$SiR_2$—.

R in $Xb^1$, $Xb^2$, $Yb^1$, and $Yb^2$ is as defined above with respect to R in $X^1$, $X^2$, $Y^1$, and $Y^2$ of formula (CH2).

$Zb^1$, $Zb^2$, $Zb^3$, and $Zb^4$ each independently represent a substituted or unsubstituted aliphatic hydrocarbon group, a substituted or unsubstituted aliphatic heterocyclic group, a substituted or unsubstituted aromatic hydrocarbon group, or a substituted or unsubstituted aromatic heterocyclic group.

The structure represented by formula (CH2-a) wherein $n_a$ is 1 is preferably a structure represented by any of formulae (CH2-a-1) to (CH2-a-6), which correspond to formula (CH2-a) wherein $n_a$ is 1, each of $Za^1$, $Za^2$, and $Za^3$ is a benzene ring, one of $Xa^1$ and $Ya^1$ is a single bond, and one of $Xa^2$ and $Ya^2$ is a single bond.

(CH2-a-1)

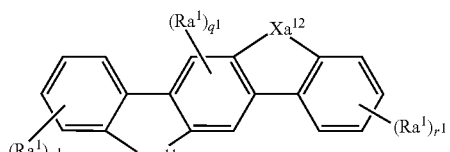

(CH2-a-2)

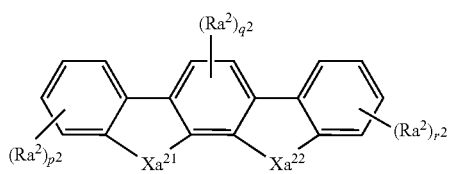

(CH2-a-3)

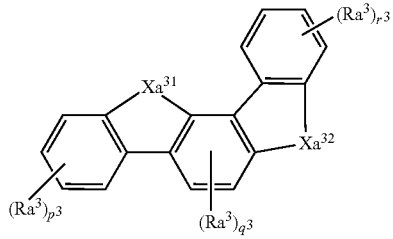

(CH2-a-4)

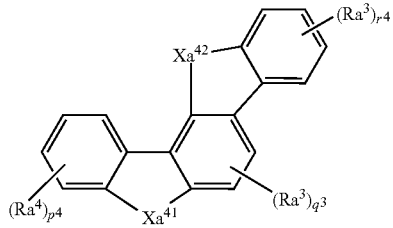

(CH2-a-5)

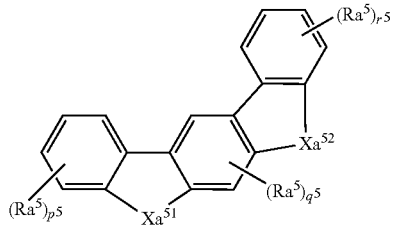

(CH2-a-6)

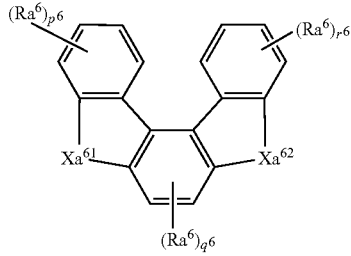

In the above formulae, $Xa^{11}$ and $Xa^{12}$ in formula (CH2-a-1), $Xa^{21}$ and $Xa^{22}$ in formula (CH2-a-2), $Xa^{31}$ and $Xa^{32}$ in formula (CH2-a-3), $Xa^{41}$ and $Xa^{42}$ in formula (CH2-a-4), $Xa^{51}$ and $Xa^{52}$ in formula (CH2-a-5), and $Xa^{G1}$ and $Xa^{G2}$ in formula (CH2-a-6) each independently represent —$CR_2$—, —NR—, —O—, —S—, or —$SiR_2$—.

R in $Xa^{11}$, $Xa^{12}$, $Xa^{21}$, $Xa^{22}$, $Xa^{31}$, $Xa^{32}$, $Xa^{41}$, $Xa^{42}$, $Xa^{51}$, $Xa^{52}$, $Xa^{61}$, and $Xa^{62}$ is as defined above with respect to R in $X^1$, $X^2$, $Y^1$, and $Y^2$ of formula (CH2).

$Ra^1$ in formula (CH2-a-1), $Ra^2$ in formula (CH2-a-2), $Ra^3$ in formula (CH2-a-3), $Ra^4$ in formula (CH2-a-4), $Ra^5$ in formula (CH2-a-5), and $Ra^6$ in formula (CH2-a-6) each independently represent a substituted or unsubstituted alkyl group having 1 to 20 carbon atoms, a substituted or unsubstituted cycloalkyl group having 3 to 20 ring carbon atoms, a substituted or unsubstituted alkoxy group having 1 to 20 carbon atoms, a substituted or unsubstituted aralkyl group having 7 to 24 carbon atoms, a substituted or unsubstituted silyl group, a substituted or unsubstituted aromatic hydrocarbon ring group having 6 to 24 ring carbon atoms, or a substituted or unsubstituted aromatic heterocyclic group having 2 to 24 ring carbon atoms.

Two or more groups $Ra^1$ may be the same or different, two or more groups $Ra^2$ may be the same or different, two or more groups $Ra^3$ may be the same or different, two or more groups $Ra^4$ may be the same or different, two or more groups $Ra^5$ may be the same or different, and two or more groups $Ra^6$ may be the same or different.

In Formulae (CH2-a-1) to (CH2-a-6), $p^1$ in formula (CH2-a-1), $p^2$ in formula (CH2-a-2), $p^3$ in formula (CH2-a-3), $p^4$ in formula (CH2-a-4), $p^5$ in formula (CH2-a-5), and $p^6$ in formula (CH2-a-6) each independently represent an integer of 0 to 4;

$q^1$ in formula (CH2-a-1), $q^2$ in formula (CH2-a-2), $q^3$ in formula (CH2-a-3), $q^4$ in formula (CH2-a-4), $q^5$ in formula (CH2-a-5), and $q^6$ in formula (CH2-a-6) each independently represent an integer of 0 to 2; and $r^1$ in formula (CH2-a-1), $r^2$ in formula (CH2-a-2), $r^3$ in formula (CH2-a-3), $r^4$ in formula (CH2-a-4), $r^5$ in formula (CH2-a-5), and $r^6$ in formula (CH2-a-6) each independently represent an integer of 0 to 4.

In view of increasing the solubility, the structure represented by formula (CH2-b) is more preferably a structure represented by formula (CH2-b-1), which corresponds to formula (CH2-b) wherein each of $Zb^1$, $Zb^2$, $Zb^3$, and $Zb^4$ is a benzene ring, one of $Xb^1$ and $Yb^1$ is a single bond, and one of $Xb^2$ and $Yb^2$ is a single bond.

(CH2-b-1)

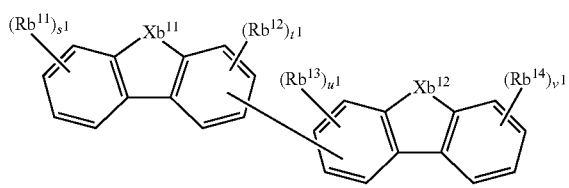

in formula (CH2-b-1), $Xb^{11}$ and $Xb^{12}$ each independently represent —NR—, —O—, —S—, or —SiR$_2$—;
R is as defined above with respect to R in $X^1$, $X^2$, $Y^1$, and $Y^2$ of formula (CH2);
$Rb^{11}$, $Rb^{12}$, $Rb^{13}$, and $Rb^{14}$ each independently represent a substituted or unsubstituted alkyl group having 1 to 20 carbon atoms, a substituted or unsubstituted cycloalkyl group having 3 to 20 ring carbon atoms, a substituted or unsubstituted alkoxy group having 1 to 20 carbon atoms, a substituted or unsubstituted aralkyl group having 7 to 24 carbon atoms, a substituted or unsubstituted silyl group, a substituted or unsubstituted aromatic hydrocarbon ring group having 6 to 24 ring carbon atoms, or a substituted or unsubstituted aromatic heterocyclic group having 2 to 24 ring carbon atoms;
$s^1$ represents an integer of 0 to 4 and two or more groups $Rb^{11}$ when $s^1$ is an integer of 2 or more may be the same or different;
$t^1$ represents an integer of 0 to 3 and two or more groups $Rb^{12}$ when $t^1$ is an integer of 2 or more may be the same or different;
$u^1$ represents an integer of 0 to 3 and two or more groups $Rb^{13}$ when $u^1$ is an integer of 2 or more may be the same or different; and
$v^1$ represents an integer of 0 to 4 and two or more groups $Rb^{14}$ when $v^1$ is an integer of 2 or more may be the same or different.
B in formula (CH1) is preferably a group represented by formula (CH2-A) or (CH2-B):

(CH2-A)

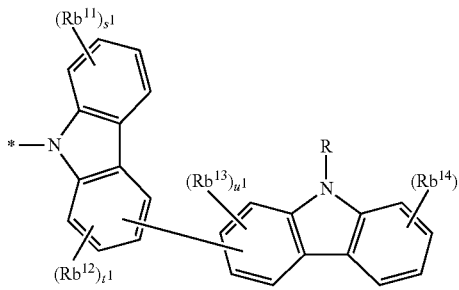

(CH2-B)

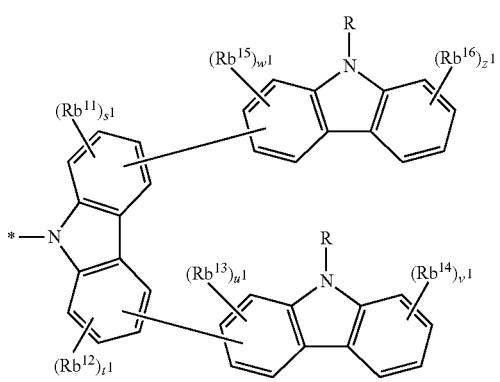

in formula (CH2-A), $Xb^{12}$, $Rb^{11}$, $Rb^{12}$, $Rb^{13}$, $Rb^{14}$, $s^1$, $t^1$, $u^1$ and $v^1$ are as defined above in formula (CH2-b-1), and * represents a bonding site to $L^1$ of formula (CH1); and in formula (CH2-B),
$s^1$ represents an integer of 0 to 3;
$Xb^{12}$, R, $Rb^{11}$, $Rb^{12}$, $Rb^{13}$, $Rb^{14}$, $t^1$, $u^1$, and $v^1$ are as defined above in formula (CH2-b-1), with $Xb^{12}$ being preferably NR in view of increasing the solubility; and
* represents a bonding site to $L^1$ of formula (CH1).
R in formula (CH2-B) is preferably a substituted or unsubstituted alkyl group, a substituted or unsubstituted cycloalkyl group, a substituted or unsubstituted aromatic hydrocarbon group, or a substituted or unsubstituted aromatic heterocyclic group.
The group represented by formula (CH2-A) is preferably a group represented by formula (CH2-A-i) or (CH2-A-ii):

(CH2-A-i)

(CH2-A-ii)

In formula (CH2-A-i),
$Rb^{11}$, $Rb^{12}$, $Rb^{13}$, $Rb^{14}$, $s^1$, $t^1$, $u^1$, and $v^1$ are as defined above in formula (CH2-A); and
R is as defined above with respect to R in $X^1$, $X^2$, $Y^1$, and $Y^2$ of formula (CH2);
* represents a bonding site to $L^1$ of formula (CH1).
R in formula (CH2-A-i) is preferably a substituted or unsubstituted alkyl group, a substituted or unsubstituted cycloalkyl group, a substituted or unsubstituted aromatic hydrocarbon group, or a substituted or unsubstituted aromatic heterocyclic group.
In formula (CH2-A-ii),
$s^1$ represents an integer of 0 to 3;
$Rb^{11}$, $Rb^{12}$, $Rb^{13}$, $Rb^{14}$, $t^1$, $u^1$, and $v^1$ are as defined above in formula (CH2-A);
$Rb^{15}$ and $Rb^{16}$ each independently represent a substituted or unsubstituted alkyl group having 1 to 20 carbon atoms, a substituted or unsubstituted cycloalkyl group having 3 to 20 ring carbon atoms, a substituted or unsubstituted alkoxy group having 1 to 20 carbon atoms, a substituted or unsubstituted aralkyl group having 7 to 24 carbon atoms, a substituted or unsubstituted silyl group, a substituted or unsubstituted aromatic hydrocarbon ring group having 6 to 24 ring carbon atoms, or a substituted or unsubstituted aromatic heterocyclic group having 2 to 24 ring carbon atoms;

R is as defined above with respect to R of $X^1$, $X^2$, $Y^1$, and $Y^2$ in formula (CH2), with a substituted or unsubstituted alkyl group, a substituted or unsubstituted cycloalkyl group, a substituted or unsubstituted aromatic hydrocarbon group, or a substituted or unsubstituted aromatic heterocyclic group being preferred;

$w^1$ represents an integer of 0 to 3 and two or more groups $Rb^{15}$ when $w^1$ is an integer of 2 or more may be the same or different;

$z^1$ represents an integer of 0 to 4 and two or more groups $Rb^{16}$ when $z^1$ is an integer of 2 or more may be the same or different; and

* represents a bonding site to $L^1$ of formula (CH1).

The group represented by formula (CH2-A-i) is preferably a group represented by any of formulae CH2-A-1) to (CH2-A-3):

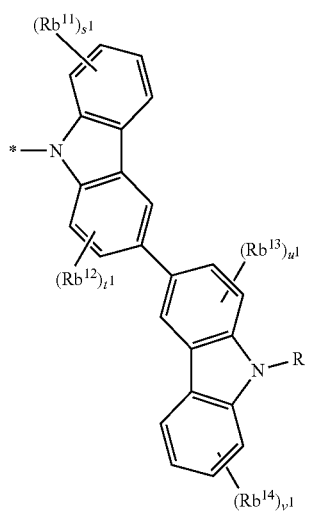

(CH2-A-1)

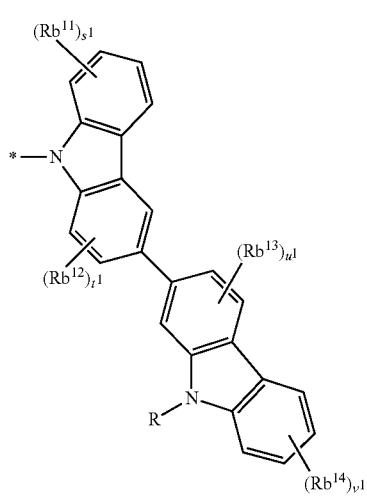

(CH2-A-2)

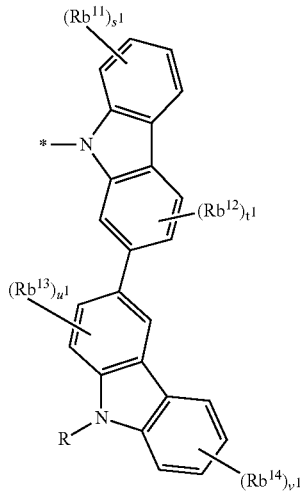

(CH2-A-3)

in formulae (CH2-A-1) to (CH2-A-3), R, $Rb^{11}$, $Rb^{12}$, $Rb^{13}$, $Rb^{14}$, $s^1$, $t^1$, $u^1$, and $v^1$ are as defined above in formula (CH2-b-1), and * represents a bonding site to $L^1$ of formula (CH1).

R in formulae (CH2-A-1) to (CH2-A-3) is preferably a substituted or unsubstituted alkyl group, a substituted or unsubstituted cycloalkyl group, a substituted or unsubstituted aromatic hydrocarbon group, or a substituted or unsubstituted aromatic heterocyclic group.

The group represented by formula (CH2-B) is a group represented by formula (CH2-B-i) or (CH2-B-ii):

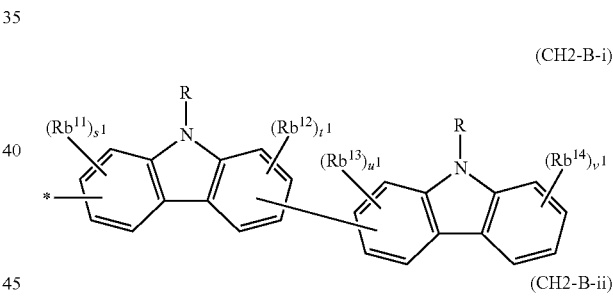

(CH2-B-i)

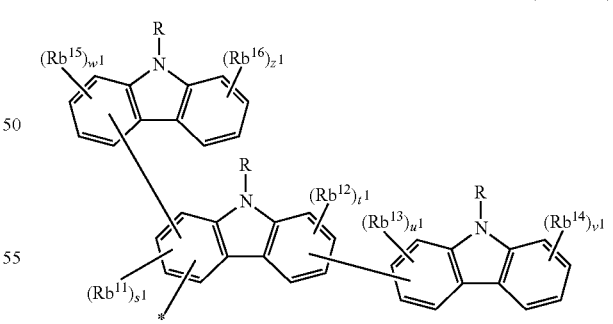

(CH2-B-ii)

In formula (CH2-B-i), R, $Rb^{11}$, $Rb^{12}$, $Rb^{13}$, $Rb^{14}$, $s^1$, $t^1$, $u^1$, and $v^1$ are as defined above in formula (CH2-B), and * represents a bonding site to $L^1$ of formula (CH1).

R in formula (CH2-B-i) is preferably a substituted or unsubstituted alkyl group, a substituted or unsubstituted cycloalkyl group, a substituted or unsubstituted aromatic hydrocarbon group, or a substituted or unsubstituted aromatic heterocyclic group.

In formula (CH2-B-ii), $s^1$ represents an integer of 0 to 2;

R, $Rb^{11}$, $Rb^{12}$, $Rb^{13}$, $Rb^{14}$, $t^1$, $u^1$, and $v^1$ are as defined above in formula (CH2-B);

$Rb^{15}$ and $Rb^{16}$ each independently represent a substituted or unsubstituted alkyl group having 1 to 20 carbon atoms, a substituted or unsubstituted cycloalkyl group having 3 to 20 ring carbon atoms, a substituted or unsubstituted alkoxy group having 1 to 20 carbon atoms, a substituted or unsubstituted aralkyl group having 7 to 24 carbon atoms, a substituted or unsubstituted silyl group, a substituted or unsubstituted aromatic hydrocarbon ring group having 6 to 24 ring carbon atoms, or a substituted or unsubstituted aromatic heterocyclic group having 2 to 24 ring carbon atoms;

$w^1$ represents an integer of 0 to 3 and two or more groups $Rb^{15}$ when $w^1$ is an integer of 2 or more may be the same or different;

$z^1$ represents an integer of 0 to 4 and two or more groups $Rb^{16}$ when $z^1$ is an integer of 2 or more may be the same or different; and

* represents a bonding site to $L^1$ of formula (CH1).

R in formula (CH2-B-ii) is preferably a substituted or unsubstituted alkyl group, a substituted or unsubstituted cycloalkyl group, a substituted or unsubstituted aromatic hydrocarbon group, or a substituted or unsubstituted aromatic heterocyclic group.

B in formula (CH1) is more preferably a group represented by formula (CH2-C) or (CH2-D):

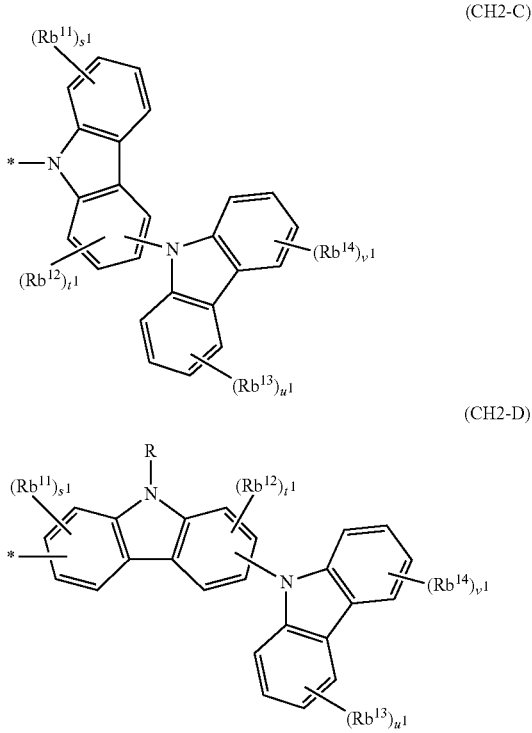

in formula (CH2-C), $u^1$ represents an integer of 0 to 4;

$Rb^{11}$, $Rb^{12}$, $Rb^{13}$, $Rb^{14}$, $s^1$, $t^1$, and $v^1$ are as defined above in formula (CH2-b-1); and

* represents a bonding site to $L^1$ of formula (CH1); and in formula (CH2-D), $s^1$ represents an integer of 0 to 3;

$u^1$ represents an integer of 0 to 4;

R, $Rb^{11}$, $Rb^{12}$, $Rb^{13}$, $Rb^{14}$, $t^1$, and $v^1$ are as defined above in formula (CH12-b-1); and

* represents a bonding site to $L^1$ of formula (CH1).

R in formula (CH2-D) is preferably a substituted or unsubstituted alkyl group, a substituted or unsubstituted cycloalkyl group, a substituted or unsubstituted aromatic hydrocarbon group, or a substituted or unsubstituted aromatic heterocyclic group.

The group represented by formula (CH2-C) is more preferably a group represented by formula (CH2-C-1) or (CH2-C-2):

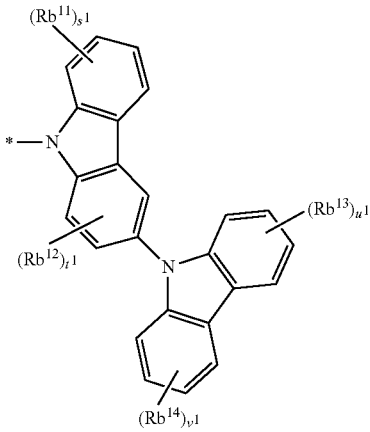

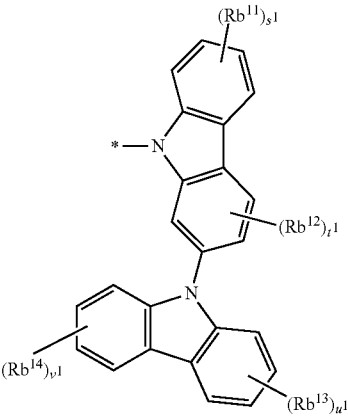

In formula (CH2-C-1),

R, $Rb^{11}$, $Rb^{12}$, $Rb^{13}$, $Rb^{14}$, $s^1$, $t^1$, and $v^1$ are as defined above in formula (CH2-b-1);

$u^1$ represents an integer of 0 to 4; and

* represents a bonding site to $L^1$ of formula (CH1).

R in formula (CH2-C-1) is preferably a substituted or unsubstituted alkyl group, a substituted or unsubstituted cycloalkyl group, a substituted or unsubstituted aromatic hydrocarbon group, or a substituted or unsubstituted aromatic heterocyclic group.

In formula (CH2-C-2),

R, $Rb^{11}$, $Rb^{12}$, $Rb^{13}$, $Rb^{14}$, $s^1$, $t^1$, and $v^1$ are as defined above in formula (CH2-b-1);

$u^1$ represents an integer of 0 to 4; and

* represents a bonding site to $L^1$ of formula (CH1).

R in formula (CH2-C-2) is preferably a substituted or unsubstituted alkyl group, a substituted or unsubstituted cycloalkyl group, a substituted or unsubstituted aromatic hydrocarbon group, or a substituted or unsubstituted aromatic heterocyclic group.

B in formula (CH1) is more preferably a group represented by formula (CH2-E) or (CH2-F):

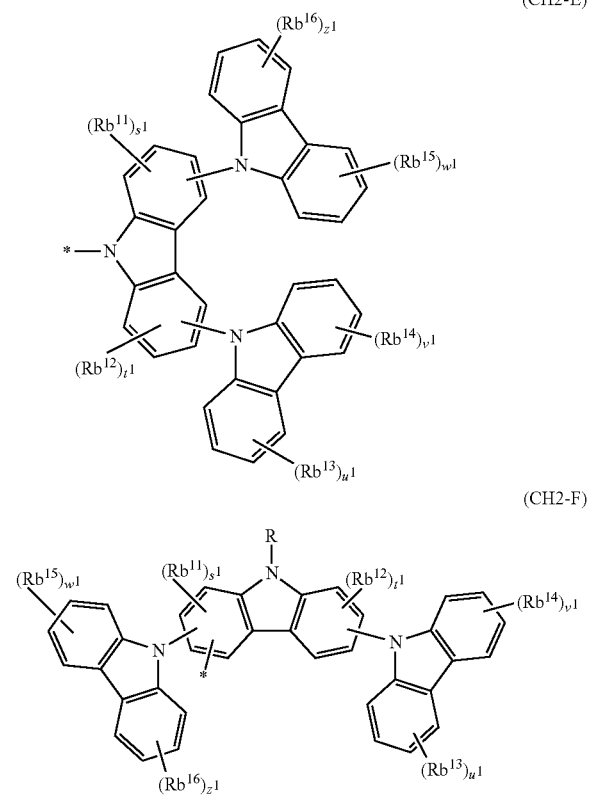

in formula (CH2-E),
$s^1$ represents an integer of 0 to 3;
$u^1$ represents an integer of 0 to 4;
$w^1$ represents an integer of 0 to 4;
$Rb^{11}$, $Rb^{12}$, $Rb^{13}$, $Rb^{14}$, $t^1$, and $v^1$ are as defined above in formula (CH2-b-1):
$Rb^{15}$ and $Rb^{16}$ each independently represent a substituted or unsubstituted alkyl group having 1 to 20 carbon atoms, a substituted or unsubstituted cycloalkyl group having 3 to 20 ring carbon atoms, a substituted or unsubstituted alkoxy group having 1 to 20 carbon atoms, a substituted or unsubstituted aralkyl group having 7 to 24 carbon atoms, a substituted or unsubstituted silyl group, a substituted or unsubstituted aromatic hydrocarbon ring group having 6 to 24 ring carbon atoms, or a substituted or unsubstituted aromatic heterocyclic group having 2 to 24 ring carbon atoms;
R is as defined above with respect to R of $X^1$, $X^2$, $Y^1$, and $Y^2$ in formula (CH2), with a substituted or unsubstituted alkyl group, a substituted or unsubstituted cycloalkyl group, a substituted or unsubstituted aromatic hydrocarbon group, or a substituted or unsubstituted aromatic heterocyclic group being preferred;
$w^1$ represents an integer of 0 to 4 and two or more groups $Rb^{15}$ when $w^1$ is an integer of 2 or more may be the same or different;
$z^1$ represents an integer of 0 to 4 and two or more groups $Rb^{16}$ when $z^1$ is an integer of 2 or more may be the same or different; and
* represents a bonding site to $L^1$ of formula (CH1); and
in formula (CH2-F),
$s^1$ represents an integer of 0 to 2;
$u^1$ represents an integer of 0 to 4;
$Rb^{11}$, $Rb^{12}$, $Rb^{13}$, $Rb^{14}$, $t^1$, and $v^1$ are as defined above in formula (CH2-b-1);
$Rb^{15}$ and $Rb^{16}$ are as defined above in formula (CH2-E);
R is as defined above with respect to R of $X^1$, $X^2$, $Y^1$, and $Y^2$ in formula (CH2), with a substituted or unsubstituted alkyl group, a substituted or unsubstituted cycloalkyl group, a substituted or unsubstituted aromatic hydrocarbon group, or a substituted or unsubstituted aromatic heterocyclic group being preferred;
$w^1$ represents an integer of 0 to 4 and two or more groups $Rb^{15}$ when $w^1$ is an integer of 2 or more may be the same or different;
$z^1$ represents an integer of 0 to 4 and two or more groups $Rb^{16}$ when $z^1$ is an integer of 2 or more may be the same or different; and
* represents a bonding site to $L^1$ of formula (CH1).

The details of each group represented by symbol in the above formulae are described below.

Preferably, the substituted or unsubstituted aromatic hydrocarbon group for $L^1$ in formula (CH1); $L^1$ in formula (CHi); $L^1$ in formula (CH1-A); $L^1$ in formula (CH1-A'); R, $Z^1$, $Z^2$, and $L^2$ in formula (CH2); R and $Za^1$ to $Za^3$ in formula (CH2-a); R and $Zb^1$ to $Zb^4$ in formula (CH2-b); R in formulae (CH2-a-1) to (CH2-a-6); R in formula (CH2-b-1); R in formula (CH2-A); R in formula (CH2-B); R in formula (CH2-D); R in formula (CH2-F); R in formula (CH2-A-i); R in formula (CH2-A-ii); R in formula (CH2-B-i); R in formula (CH2-B-ii); and R in formulae (CH2-A-1) to (CH2-A-3) is each independently a residue of a substituted or unsubstituted aromatic hydrocarbon ring having 6 to 30 ring carbon atoms.

Examples of the aromatic hydrocarbon ring having 6 to 30 ring carbon atoms include benzene, naphthalene, biphenyl, terphenyl, fluorene, phenanthrene, triphenylene, perylene, chrysene, fluoranthene, benzofluorene, benzotriphenylene, benzochrysene, anthracene, benzene-fused analogues thereof, and cross-linked analogues thereof, with benzene, naphthalene, biphenyl, terphenyl, fluorene, and phenanthrene being preferred.

Preferred examples of the aromatic hydrocarbon ring group having 6 to 30 ring carbon atoms for $L^1$ in formula (CH1), $L^1$ in formula (CHi), $L^1$ in formula (CH1-A), and $L^1$ in formula (CH1-A') include a m-phenylene group, a p-phenylene group, a 4,4'-biphenylene group, a 4,3'-biphenylene group, a 1,4-naphthylene group, and a 2,6-naphthylene group.

The aromatic hydrocarbon ring having 6 to 30 ring carbon atoms for R in formula (CH2); R in formula (CH2-a) or (CH2-b); R in formulae (CH2-a-1) to (CH2-a-6); R in formula (CH2-b-1); R in formula (CH2-A) or (CH2-B); R in formula (CH2-D); R in formula (CH2-F); R in formula (CH2-A-i); R in formula (CH2-A-ii); R in formula (CH2-B-i); R in formula (CH2-B-ii); and R in formulae (CH2-A-1) to (CH2-A-3) is preferably a benzene which may have an electron transporting substituent, for example, a cyano group.

The aromatic hydrocarbon ring having 6 to 30 ring carbon atoms for $Z^1$ and $Z^2$ in formula (CH2); $Za^1$ to $Za^3$ in formula (CH2-a); and $Zb^1$ to $Zb^4$ in formula (CH2-b) is preferably a benzene ring.

Preferably, the substituted or unsubstituted aromatic heterocyclic group for A and $L^1$ in formula (CH1); A and $L^1$ in formula (CHi); Ax and $L^1$ in formula (CH1-A); Ax and $L^1$ in formula (CH1-A'); R, $Z^1$, $Z^2$, and $L^2$ in formula (CH2); R and $Za^1$ to $Za^3$ in formula (CH2-a); R and $Zb^1$ to $Zb^4$ in formula (CH2-b); R in formulae (CH2-a-1) to (CH2-a-6); R in formula (CH2-b-1); R in formula (CH2-A); R in formula (CH2-B); R in formula (CH2-D), R in formula (CH2-F); R in formula (CH2-A-i); R in formula (CH2-A-ii); R in formula (CH2-B-i); R in formula (CH2-B-ii); and R in formulae (CH2-A-1) to (CH2-A-3) independently represents a residue of a substituted or unsubstituted aromatic heterocyclic group having 2 to 30 ring carbon atoms.

Examples of the aromatic heterocyclic group having 2 to 30 ring carbon atoms include pyrrole, pyridine, pyrazine, pyrimidine, pyridazine, triazine, indole, isoindole, quinoline, isoquinoline, quinoxaline, acridine, pyrrolidine, dioxane, piperidine, morpholine, piperazine, carbazole, phenanthridine, phenanthroline, furan, benzofuran, isobenzofuran, thiophene, oxazole, oxadiazole, benzoxazole, thiazole, thiadiazole, benzothiazole, triazole, imidazole, benzimidazole, pyran, dibenzofuran, dibenzothiophene, azafluorene, benzo[f]quinazoline, benzo[h]quinazoline, azafluoranthene, diazafluoranthene, azacarbazole, benzene-fused analogues thereof, and cross-linked analogues thereof.

Examples of the aromatic heterocyclic group having 2 to 30 ring carbon atoms for A in formula (CH1); A in formula (CHi); Ax in formula (CH1-A); and Ax in formula (CH1-A') preferably include pyridine, pyrazine, pyrimidine, pyridazine, triazine, quinoline, isoquinoline, quinoxaline, quinazoline, aziridine, azaindolizine, indolizine, imidazole, indole, isoindole, indazole, purine, pteridine, β-carboline, naphthyridine, benzo[f]quinazoline, benzo[h]quinazoline, azafluoranthene, diazafluoranthene, pyrazole, tetrazole, quinolizine, cinnoline, phthalazine, biscarbazole, phenazine, azatriphenylene, diazatriphenylene, hexaazatriphenylene, azacarbazole, azadibenzofuran, azadibenzothiophene, and dinaphtho[2',3': 2,3:2',3': 6,7]carbazole, with the residue of the compound selected from the following group being more preferred:

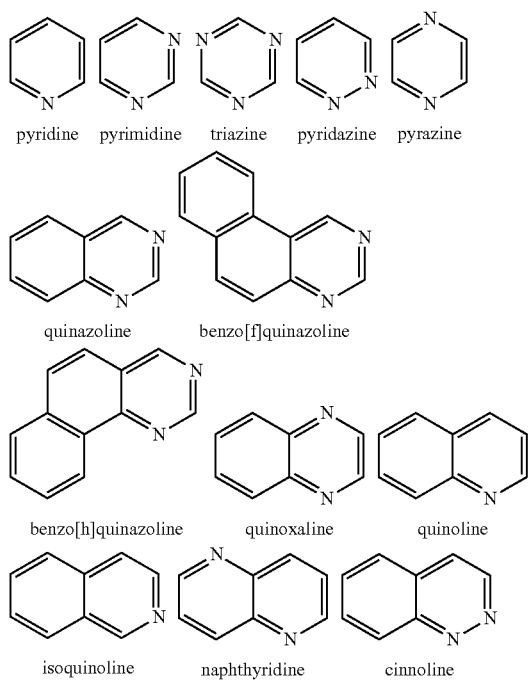

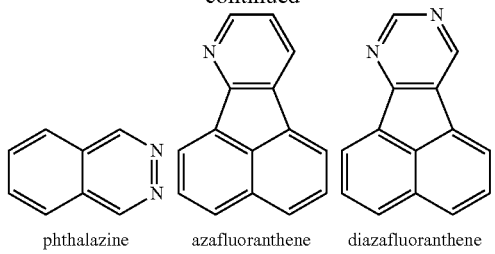

phthalazine    azafluoranthene    diazafluoranthene wherein pyridine, pyrimidine, triazine, quinoline, isoquinoline, quinoxaline, and quinazoline are still more preferred, and pyrimidine and triazine are particularly preferred.

Preferably, the substituted or unsubstituted alkyl group for R in formula (CH2); R in formula (CH2-a); R in formula (CH2-b); R in formulae (CH2-a-1) to (CH2-a-6); R in formula (CH2-b-1); R in formula (CH2-A); R in formula (CH2-B); R in formula (CH2-D); R in formula (CH2-F); R in formula (CH2-A-i); R in formula (CH2-A-ii); R in formula (CH2-B-i); R in formula (CH2-B-ii); and R in formulae (CH2-A-1) to (CH2-A-3) is independently a substituted or unsubstituted alkyl group having 1 to 30 carbon atoms.

Examples of the alkyl group having 1 to 30 carbon atoms preferably include a methyl group, an ethyl group, a propyl group, an isopropyl group, a n-butyl group, a s-butyl group, an isobutyl group, a t-butyl group, a n-pentyl group, a n-hexyl group, a n-heptyl group, a n-octyl group, a n-nonyl group, a n-decyl group, a n-undecyl group, a n-dodecyl group, a n-tridecyl group, a n-tetradecyl group, a n-pentadecyl group, a n-hexadecyl group, a n-heptadecyl group, a n-octadecyl group, a neopentyl group, a 1-methylpentyl group, a 2-methylpentyl group, a 1-pentylhexyl group, a 1-butylpentyl group, a 1-heptyloctyl group, and a 3-methylpentyl group, with a methyl group, an ethyl group, a propyl group, an isopropyl group, a n-butyl group, a s-butyl group, an isobutyl group, and a t-butyl group being preferred.

The substituted or unsubstituted cycloalkyl group for R in formula (CH2); R in formula (CH2-a); R in formula (CH2-b); R in formulae (CH2-a-1) to (CH2-a-6); R in formula (CH2-b-1); R in formula (CH2-A); R in formula (CH2-B); R in formula (CH2-D); R in formula (CH2-F); R in formula (CH2-A-i); R in formula (CH2-A-ii); R in formula (CH2-B-i); and R in formula (CH2-B-ii); R in formulae (CH2-A-1) to (CH2-A-3) is independently represent a substituted or unsubstituted cycloalkyl group having 3 to 30 ring carbon atoms. Examples of the cycloalkyl group having 3 to 30 ring carbon atoms preferably include a cyclopropyl group, a cyclobutyl group, a cyclopentyl group, a cyclohexyl group, a cyclooctyl group, and an adamantyl group, with a cyclopentyl group and a cyclohexyl group being more preferred.

Preferably, the substituted or unsubstituted aliphatic hydrocarbon group for $Z^1$, $Z^2$ and $L^2$ in formula (CH2); $Za^1$ to $Za^3$ in formula (CH2-a); and $Zb^1$ to $Zb^4$ in formula (CH2-b) is independently represent is a residue of a substituted or unsubstituted cycloalkane having 3 to 30 ring carbon atoms or a residue of a substituted or unsubstituted cycloalkene having 3 to 30 ring carbon atoms.

Examples of the cycloalkane having 3 to 30 ring carbon atoms include cyclopropane, cyclobutane, cyclopentane, cyclohexane, cyclooctane, and adamantane, with cyclopentane and cyclohexane being preferred.

Examples of the cycloalkene having 3 to 30 ring carbon atoms include cyclopropene, cyclobutene, cyclopentene, cyclohexene, and cyclooctene, with cyclopentene and cyclohexene being preferred.

Preferably, the substituted or unsubstituted aliphatic heterocyclic group for $Z^1$, $Z^2$ and $L^2$ in formula (CH2); $Za^1$ to $Za^3$ in formula (CH2-a); and $Zb^1$ to $Zb^4$ in formula (CH2-b) is independently a group derived from the substituted or unsubstituted aliphatic hydrocarbon group mentioned above by replacing one or more ring carbon atoms with a hetero atom, such as an oxygen atom, a nitrogen atom, and a sulfur atom.

Examples of the alkyl group having 1 to 20 carbon atoms in the substituted or unsubstituted alkyl group having 1 to 20 carbon atoms for $Ra^1$ in formula (CH2-a-1); $Ra^2$ in formula (CH2-a-2); $Ra^3$ in formula (CH2-a-3); $Ra^4$ in formula (CH2-a-4); $Ra^5$ in formula (CH2-a-5); $Ra^6$ in formula (CH2-a-6); $Rb^{11}$ to $Rb^{14}$ in formula (CH2-b-1); $Rb^{11}$ to $Rb^{14}$ in formula (CH2-A); $Rb^{11}$ to $Rb^{14}$ in formula (CH2-B); $Rb^{11}$ to $Rb^{14}$ in formula (CH2-C); $Rb^{11}$ to $Rb^{14}$ in formula (CH2-D); $Rb^{11}$ to $Rb^{16}$ in formula (CH2-E); $Rb^{11}$ to $Rb^{16}$ in formula (CH2-F); $Rb^{11}$ to $Rb^{14}$ in formula (CH2-A-i); $Rb^{11}$ to $Rb^{16}$ in formula (CH2-A-ii); $Rb^{11}$ to $Rb^{14}$ in formula (CH2-B-i); $Rb^{11}$ to $Rb^{16}$ in formula (CH2-B-ii); $Rb^{11}$ to $Rb^{14}$ in formula (CH2-A-1); $Rb^{11}$ to $Rb^{14}$ in formula (CH2-A-2); $Rb^{11}$ to $Rb^{14}$ in formula (CH2-A-3); $Rb^{11}$ to $Rb^{14}$ in formula (CH2-C-1); and $Rb^{11}$ to $Rb^{14}$ in formula (CH2-C-2) include a methyl group, an ethyl group, a propyl group, an isopropyl group, a n-butyl group, a s-butyl group, a t-butyl group, an isobutyl group, a n-pentyl group, a n-hexyl group, a n-heptyl group, a n-octyl group, a n-nonyl group, a n-decyl group, a n-undecyl group, a n-dodecyl group, a n-tridecyl group, a n-tetradecyl group, a n-pentadecyl group, a n-hexadecyl group, a n-heptadecyl group, a n-octadecyl group, a neopentyl group, a 1-methylpentyl group, a 2-methylpentyl group, a 1-pentylhexyl group, a 1-butylpentyl group, a 1-heptyloctyl group, and a 3-methylpentyl group. Preferred examples are a methyl group, an ethyl group, a propyl group, an isopropyl group, a n-butyl group, a s-butyl group, an isobutyl group, a t-butyl group, a n-pentyl group, a n-hexyl group, a n-heptyl group, a n-octyl group, a n-nonyl group, a n-decyl group, a n-undecyl group, a n-dodecyl group, a n-tridecyl group, a n-tetradecyl group, a n-pentadecyl group, a n-hexadecyl group, a n-heptadecyl group, a n-octadecyl group, a neopentyl group, a 1-methylpentyl group, a 1-pentylhexyl group, a 1-butylpentyl group, and a 1-heptyloctyl group.

Examples of the cycloalkyl group having 3 to 20 carbon atoms in the substituted or unsubstituted cycloalkyl group having 3 to 20 ring carbon atoms for $Ra^1$ in formula (CH2-a-1); $Ra^2$ in formula (CH2-a-2); $Ra^3$ in formula (CH2-a-3); $Ra^4$ in formula (CH2-a-4); $Ra^5$ in formula (CH2-a-5); $Ra^6$ in formula (CH2-a-6); $Rb^{11}$ to $Rb^{14}$ in formula (CH2-b-1); $Rb^{11}$ to $Rb^{14}$ in formula (CH2-A); $Rb^{11}$ to $Rb^{14}$ in formula (CH2-B); $Rb^{11}$ to $Rb^{14}$ in formula (CH2-C); $Rb^{11}$ to $Rb^{14}$ in formula (CH2-D); $Rb^{11}$ to $Rb^{16}$ in formula (CH2-E); $Rb^{11}$ to $Rb^{16}$ in formula (CH2-F); $Rb^{11}$ to $Rb^{14}$ in formula (CH2-A-i); $Rb^{11}$ to $Rb^{16}$ in formula (CH2-A-ii); $Rb^{11}$ to $Rb^{14}$ in formula (CH2-B-i); $Rb^{11}$ to $Rb^{16}$ in formula (CH2-B-ii); $Rb^{11}$ to $Rb^{14}$ in formula (CH2-A-1); $Rb^{11}$ to $Rb^{14}$ in formula (CH2-A-2); $Rb^{11}$ to $Rb^{14}$ in formula (CH2-A-3); $Rb^{11}$ to $Rb^{14}$ in formula (CH2-C-1); and $Rb^{11}$ to $Rb^{14}$ in formula (CH2-C-2) include a cyclopropyl group, a cyclobutyl group, a cyclopentyl group, and a cyclohexyl group, with a cyclobutyl group, a cyclopentyl group and a cyclohexyl group being preferred.

Examples of the alkoxy group having 1 to 20 carbon atoms in the substituted or unsubstituted alkoxy group having 1 to 20 carbon atoms for $Ra^1$ in formula (CH2-a-1); $Ra^2$ in formula (CH2-a-2); $Ra^3$ in formula (CH2-a-3); $Ra^4$ in formula (CH2-a-4); $Ra^5$ in formula (CH2-a-5); $Ra^6$ in formula (CH2-a-6); $Rb^{11}$ to $Rb^{14}$ in formula (CH2-b-1); $Rb^{11}$ to $Rb^{14}$ in formula (CH2-A); $Rb^{11}$ to $Rb^{14}$ in formula (CH2-B); $Rb^{11}$ to $Rb^{14}$ in formula (CH2-C); $Rb^{11}$ to $Rb^{14}$ in formula (CH2-D); $Rb^{11}$ to $Rb^{16}$ in formula (CH2-E); $Rb^{11}$ to $Rb^{16}$ in formula (CH2-F); $Rb^{11}$ to $Rb^{14}$ in formula (CH2-A-i); $Rb^{11}$ to $Rb^{16}$ in formula (CH2-A-ii); $Rb^{11}$ to $Rb^{14}$ in formula (CH2-B-i); $Rb^{11}$ to $Rb^{16}$ in formula (CH2-B-ii); $Rb^{11}$ to $Rb^{14}$ in formula (CH2-A-1); $Rb^{11}$ to $Rb^{14}$ in formula (CH2-A-2); $Rb^{11}$ to $Rb^{14}$ in formula (CH2-A-3); $Rb^{11}$ to $Rb^{14}$ in formula (CH2-C-1); and $Rb^{11}$ to $Rb^{14}$ in formula (CH2-C-2) include a methoxy group, an ethoxy group, an isopropoxy group, a n-propoxy group, a n-butoxy group, a s-butoxy group, and a t-butoxy group, with a methoxy group, an ethoxy group, an isopropoxy group, and a n-propoxy group being preferred.

Examples of the aralkyl group having 7 to 24 carbon atoms in the substituted or unsubstituted aralkyl group having 7 to 24 carbon atoms for $Ra^1$ in formula (CH2-a-1); $Ra^2$ in formula (CH2-a-2); $Ra^3$ in formula (CH2-a-3); $Ra^4$ in formula (CH2-a-4); $Ra^5$ in formula (CH2-a-5); $Ra^6$ in formula (CH2-a-6); $Rb^{11}$ to $Rb^{14}$ in formula (CH2-b-1); $Rb^{11}$ to $Rb^{14}$ in formula (CH2-A); $Rb^{11}$ to $Rb^{14}$ in formula (CH2-B); $Rb^{11}$ to $Rb^{14}$ in formula (CH2-C); $Rb^{11}$ to $Rb^{14}$ in formula (CH2-D); $Rb^{11}$ to $Rb^{16}$ in formula (CH2-E); $Rb^{11}$ to $Rb^{16}$ in formula (CH2-F); $Rb^{11}$ to $Rb^{14}$ in formula (CH2-A-i); $Rb^{11}$ to $Rb^{16}$ in formula (CH2-A-ii); $Rb^{11}$ to $Rb^{14}$ in formula (CH2-B-i); $Rb^{11}$ to $Rb^{16}$ in formula (CH2-B-ii); $Rb^{11}$ to $Rb^{14}$ in formula (CH2-A-1); $Rb^{11}$ to $Rb^{14}$ in formula (CH2-A-2); $Rb^{11}$ to $Rb^{14}$ in formula (CH2-A-3); $Rb^{11}$ to $Rb^{14}$ in formula (CH2-C-1); and $Rb^{11}$ to $Rb^{14}$ in formula (CH2-C-2) include a benzyl group, a phenethyl group, and a phenylpropyl group, with a benzyl group being preferred.

Examples of the substituted or unsubstituted silyl group for $Ra^1$ in formula (CH2-a-1); $Ra^2$ in formula (CH2-a-2); $Ra^3$ in formula (CH2-a-3); $Ra^4$ in formula (CH2-a-4); $Ra^5$ in formula (CH2-a-5); $Ra^6$ in formula (CH2-a-6); $Rb^{11}$ to $Rb^{14}$ in formula (CH2-b-1); $Rb^{11}$ to $Rb^{14}$ in formula (CH2-A); $Rb^{11}$ to $Rb^{14}$ in formula (CH2-B); $Rb^{11}$ to $Rb^{14}$ in formula (CH2-C); $Rb^{11}$ to $Rb^{14}$ in formula (CH2-D); $Rb^{11}$ to $Rb^{16}$ in formula (CH2-E); $Rb^{11}$ to $Rb^{16}$ in formula (CH2-F); $Rb^{11}$ to $Rb^{14}$ in formula (CH2-A-i); $Rb^{11}$ to $Rb^{16}$ in formula (CH2-A-ii); $Rb^{11}$ to $Rb^{14}$ in formula (CH2-B-i); $Rb^{11}$ to $Rb^{16}$ in formula (CH2-B-ii); $Rb^{11}$ to $Rb^{14}$ in formula (CH2-A-1); $Rb^{11}$ to $Rb^{14}$ in formula (CH2-A-2); $Rb^{11}$ to $Rb^{14}$ in formula (CH2-A-3); $Rb^{11}$ to $Rb^{14}$ in formula (CH2-C-1); and $Rb^{11}$ to $Rb^{14}$ in formula (CH2-C-2) include an alkylsilyl group having 1 to 10, preferably 1 to 5 carbon atoms and an arylsilyl group having 6 to 30, preferably 6 to 18 ring carbon atoms. Examples of the alkylsilyl group having 1 to 10 carbon atoms include a trimethylsilyl group and a triethylsilyl group. Examples of the arylsilyl group having 6 to 30 ring carbon atoms include a triphenylsilyl group.

Examples of the aromatic hydrocarbon ring group having 6 to 24 ring carbon atoms for $Ra^1$ in formula (CH2-a-1); $Ra^2$ in formula (CH2-a-2); $Ra^3$ in formula (CH2-a-3); $Ra^4$ in formula (CH2-a-4); $Ra^5$ in formula (CH2-a-5); $Ra^6$ in formula (CH2-a-6); $Rb^{11}$ to $Rb^{14}$ in formula (CH2-b-1); $Rb^{11}$ to $Rb^{14}$ in formula (CH2-A); $Rb^{11}$ to $Rb^{14}$ in formula (CH2-B); $Rb^{11}$ to $Rb^{14}$ in formula (CH2-C); $Rb^{11}$ to $Rb^{14}$ in formula (CH2-D); $Rb^{11}$ to $Rb^{16}$ in formula (CH2-E); $Rb^{11}$ to $Rb^{16}$ in formula (CH2-F); $Rb^{11}$ to $Rb^{14}$ in formula (CH2-A-i); $Rb^{11}$ to $Rb^{16}$ in formula (CH2-A-ii); $Rb^{11}$ to $Rb^{14}$ in formula (CH2-B-i); $Rb^{11}$ to $Rb^{16}$ in formula (CH2-B-ii); $Rb^{11}$ to $Rb^{14}$ in formula (CH2-A-1); $Rb^{11}$ to $Rb^{14}$ in formula (CH2-

A-2); $Rb^{11}$ to $Rb^{14}$ in formula (CH2-A-3); $Rb^{11}$ to $Rb^{14}$ in formula (CH2-C-1); and $Rb^{11}$ to $Rb^{14}$ in formula (CH2-C-2) include a residue of an aromatic hydrocarbon ring, such as benzene, naphthalene, biphenyl, terphenyl, fluorene, phenanthrene, triphenylene, perylene, chrysene, fluoranthene, benzofluorene, benzotriphenylene, benzochrysene, and anthracene, with a residue of benzene, naphthalene, biphenyl, terphenyl, fluorene or phenanthrene being preferred.

Examples of the aromatic heterocyclic group having 2 to 24 ring carbon atoms for $Ra^1$ in formula (CH2-a-1); $Ra^2$ in formula (CH2-a-2); $Ra^3$ in formula (CH2-a-3); $Ra^4$ in formula (CH2-a-4); $Ra^5$ in formula (CH2-a-5); $Ra^6$ in formula (CH2-a-6); $Rb^{11}$ to $Rb^{14}$ in formula (CH2-b-1); $Rb^{11}$ to $Rb^{14}$ in formula (CH2-A); $Rb^{11}$ to $Rb^{14}$ in formula (CH2-B); $Rb^{11}$ to $Rb^{14}$ in formula (CH2-C); $Rb^{11}$ to $Rb^{14}$ in formula (CH2-D); $Rb^{11}$ to $Rb^{16}$ in formula (CH2-E); $Rb^{11}$ to $Rb^{16}$ in formula (CH2-F); $Rb^{11}$ to $Rb^{14}$ in formula (CH2-A-i); $Rb^{11}$ to $Rb^{16}$ in formula (CH2-A-ii); $Rb^{11}$ to $Rb^{14}$ in formula (CH2-B-i); $Rb^{11}$ to $Rb^{16}$ in formula (CH2-B-ii); $Rb^{11}$ to $Rb^{14}$ in formula (CH2-A-1); $Rb^{11}$ to $Rb^{14}$ in formula (CH2-A-2); $Rb^{11}$ to $Rb^{14}$ in formula (CH2-A-3); $Rb^{11}$ to $Rb^{14}$ in formula (CH2-C-1); and $Rb^{11}$ to $Rb^{14}$ in formula (CH2-C-2) include a residue of an aromatic heterocyclic ring, such as pyridine, pyridazine, pyrimidine, pyrazine, 1,3,5-triazine, carbazole, dibenzofuran, dibenzothiophene, phenoxazine, phenothiazine, and dihydroacridine, with a residue of pyridine, pyridazine, pyrimidine, pyrazine, carbazole, dibenzofuran, dibenzothiophene, phenoxazine, or dihydroacridine being preferred.

Examples of the compound (CH1) are described below, although not limited thereto.

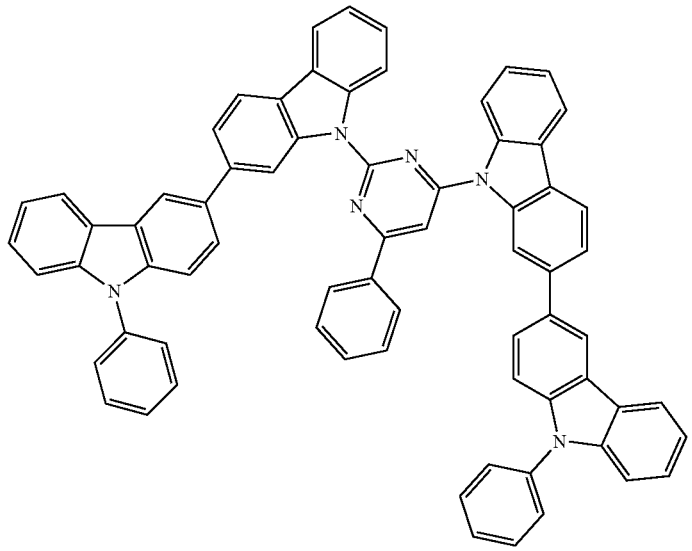

A-1

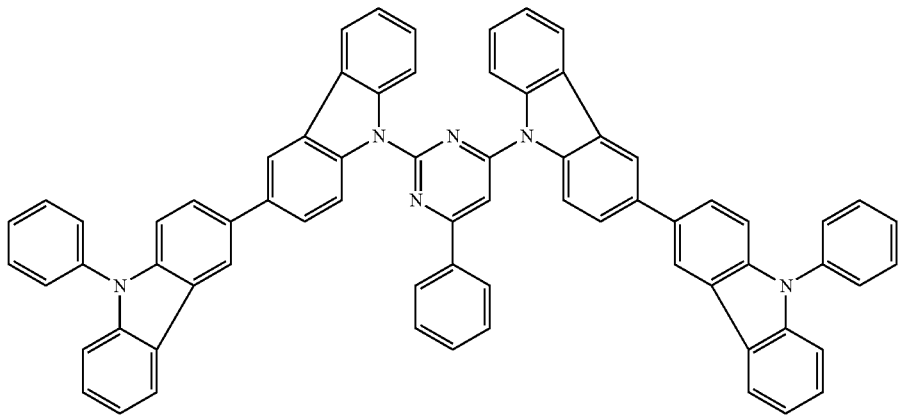

A-2

-continued
A-3
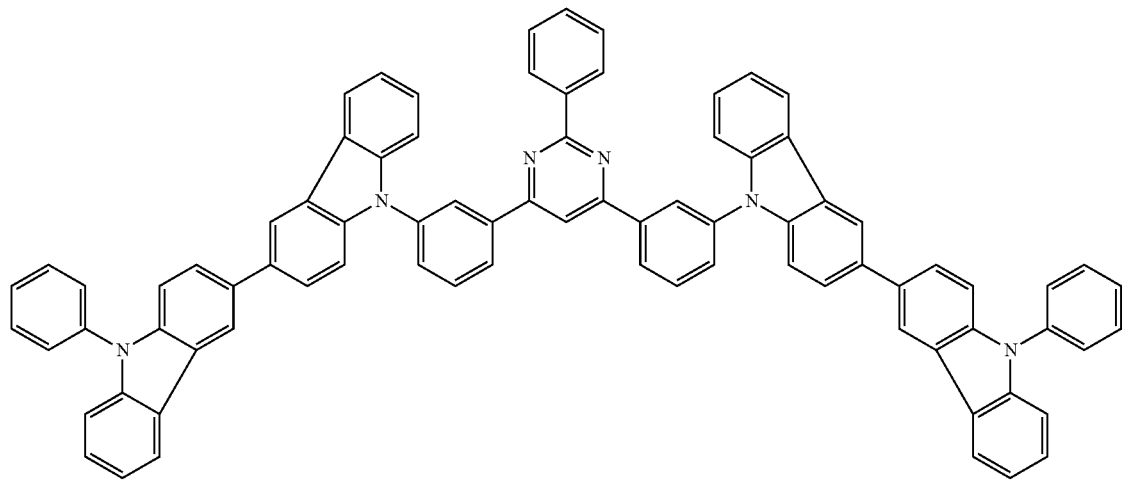
A-4
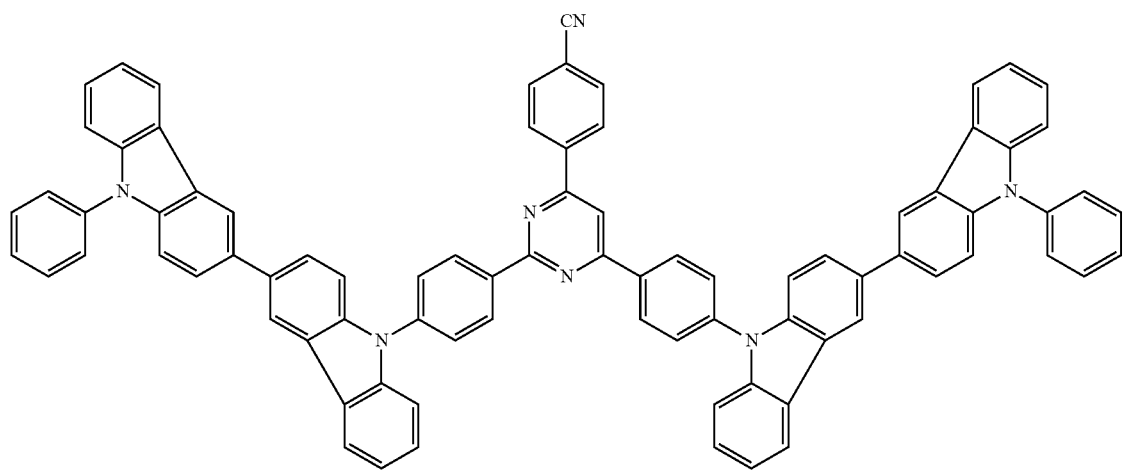
A-5
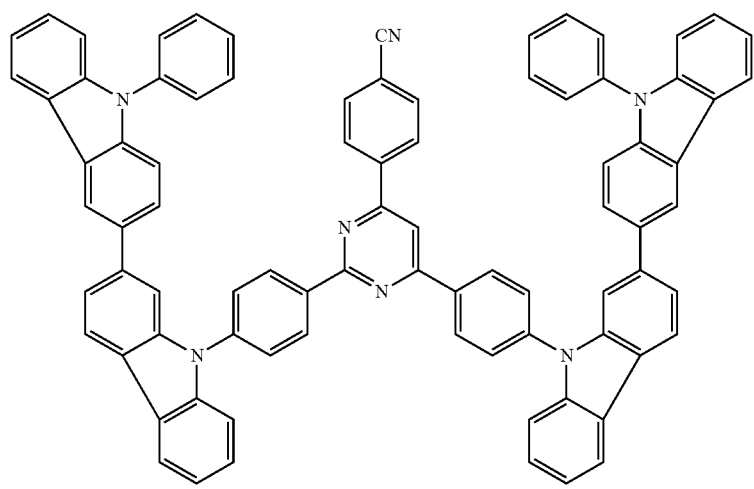

-continued
A-6
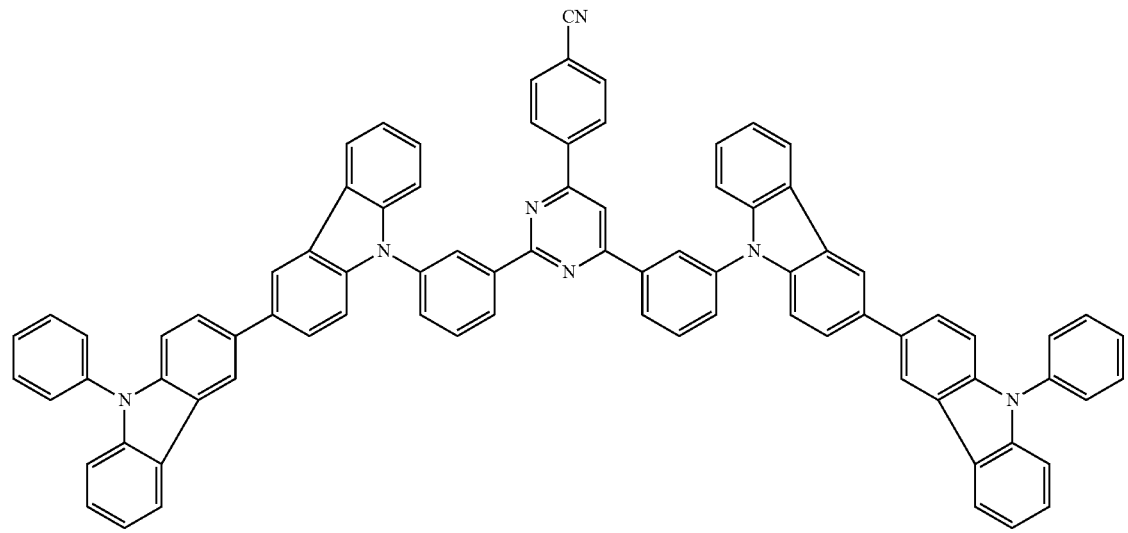
A-7
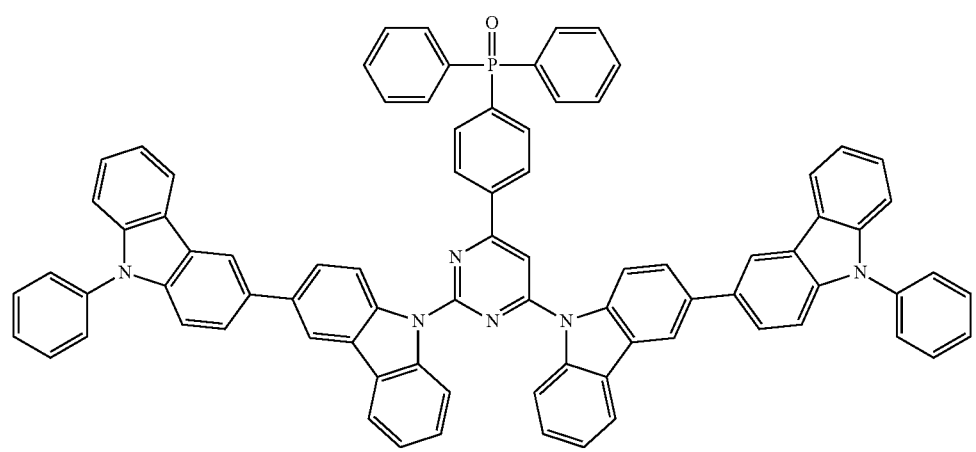
A-8
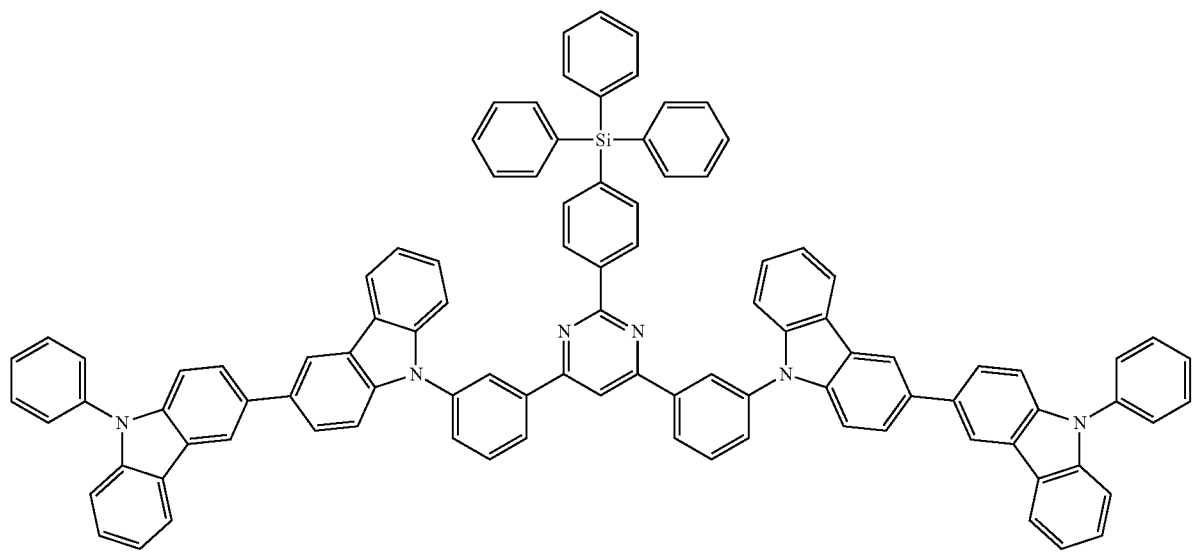

-continued
A-9
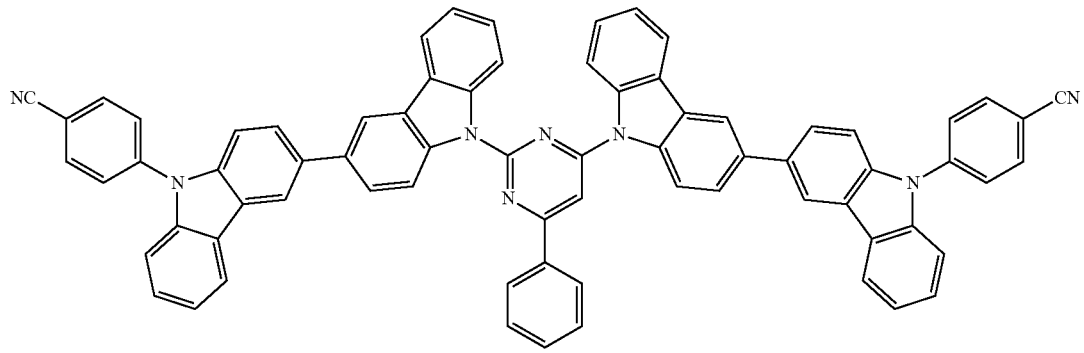
A-10
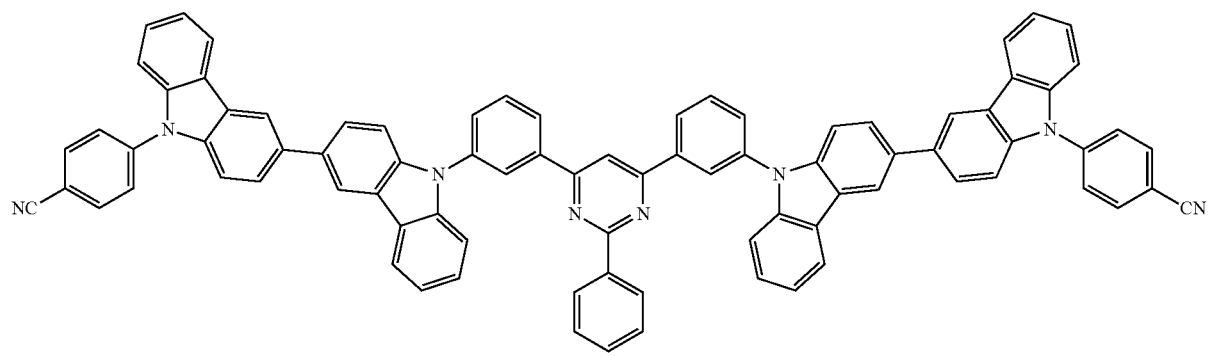
A-11
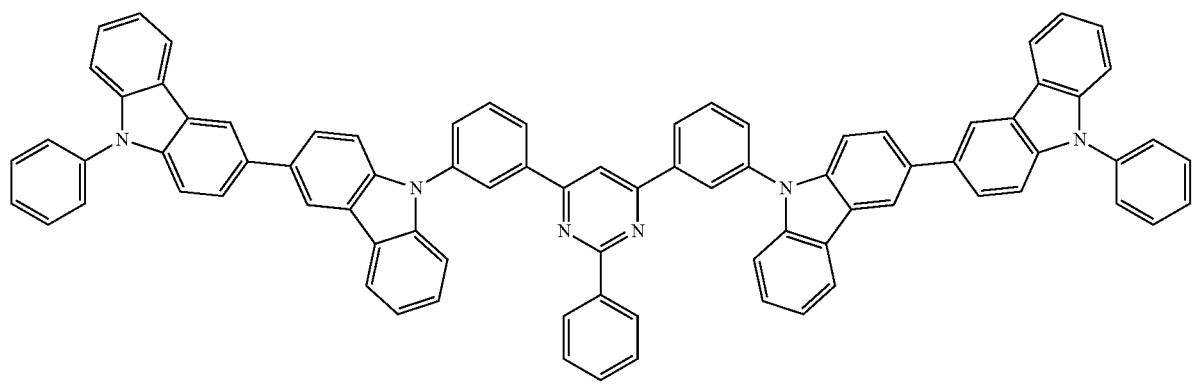
A-12
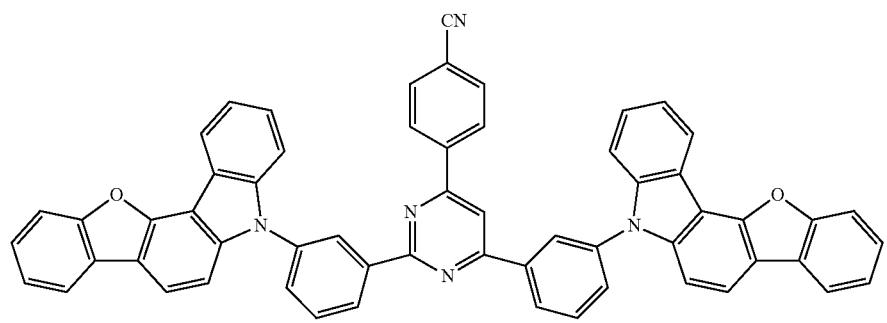

-continued
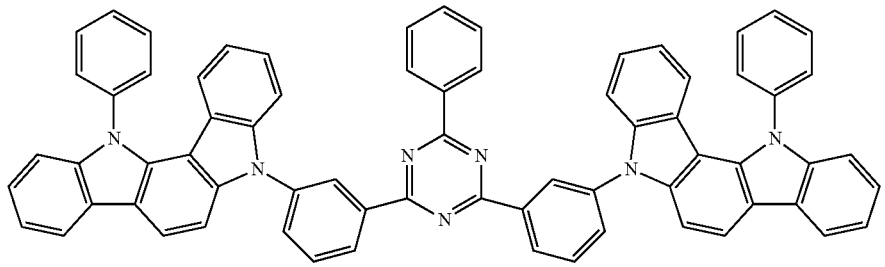
A-13
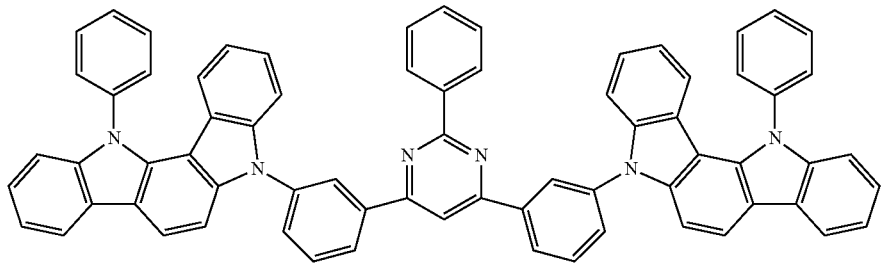
A-14
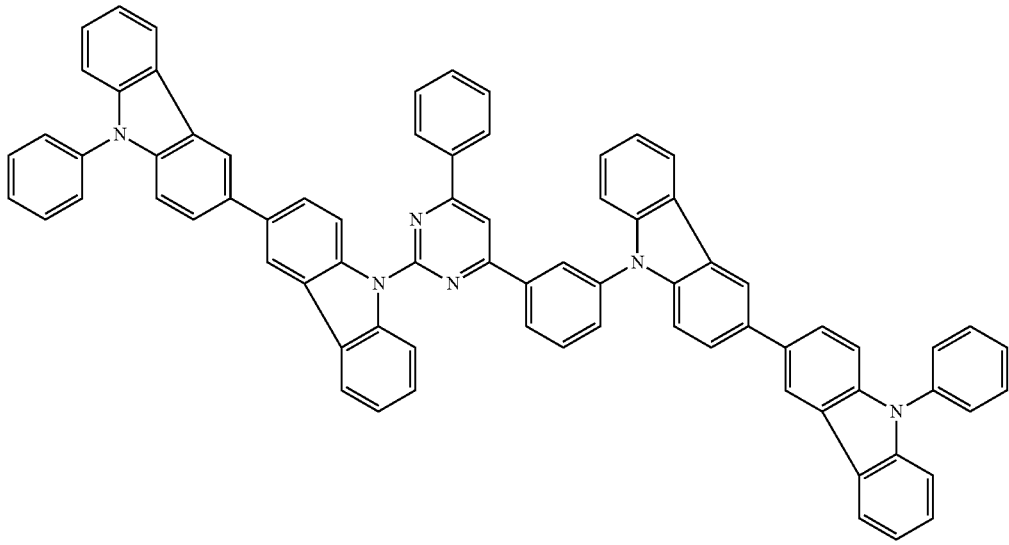
A-15
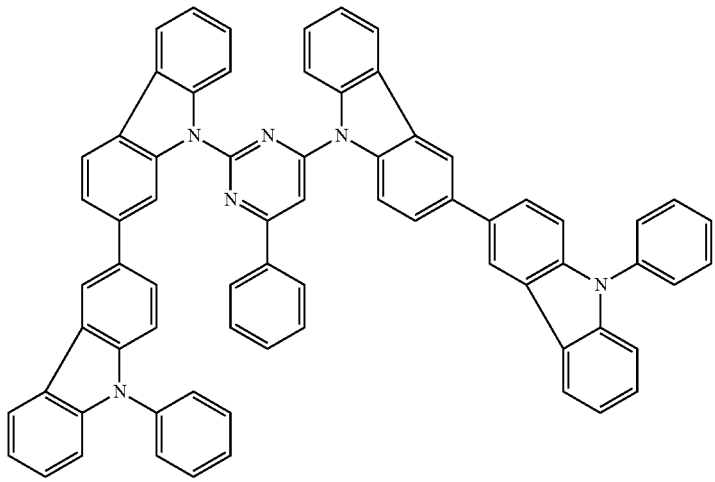
A-16

-continued
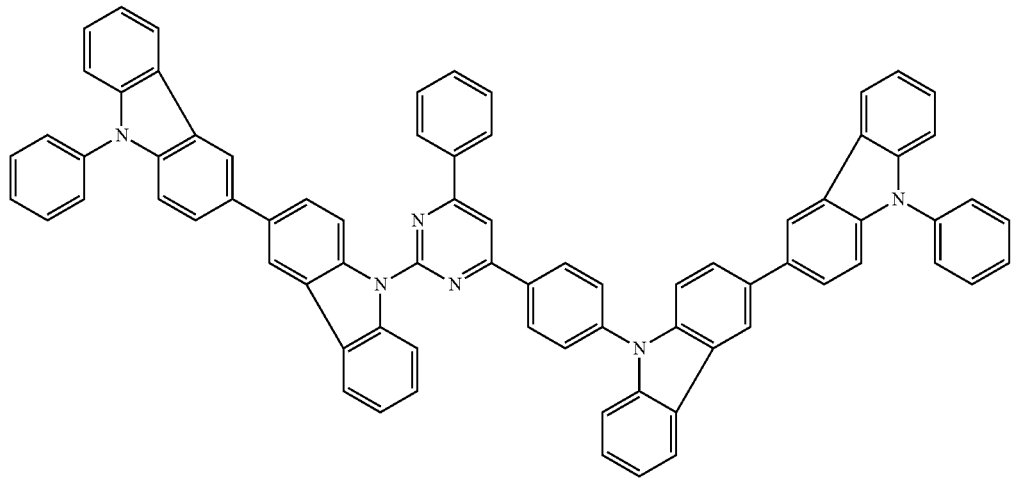
A-17
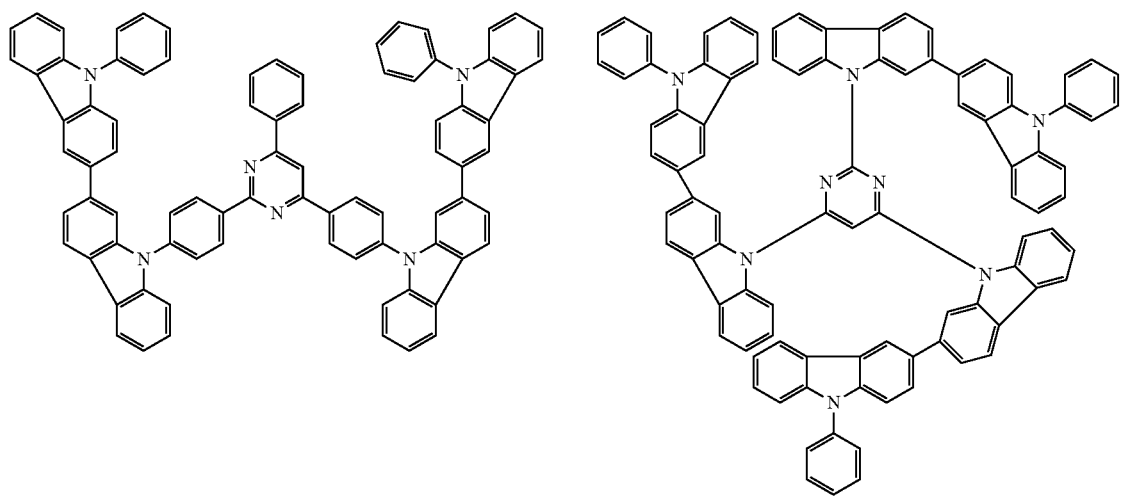
A-18
A-19
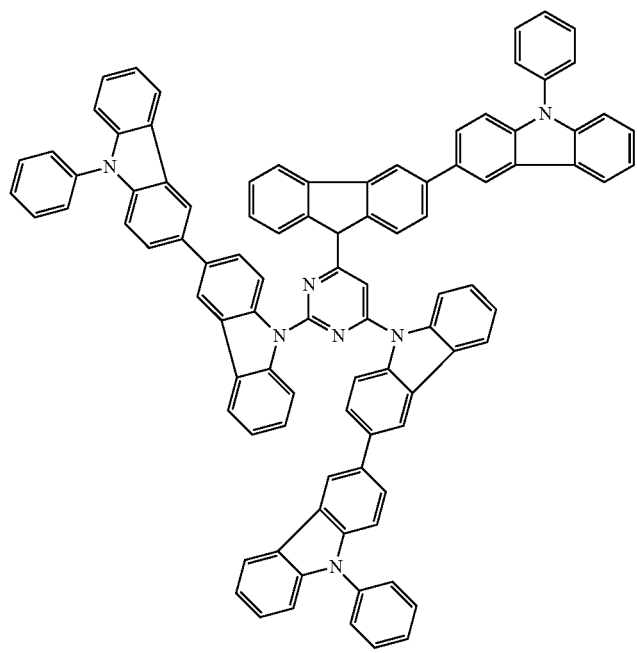
A-20

-continued
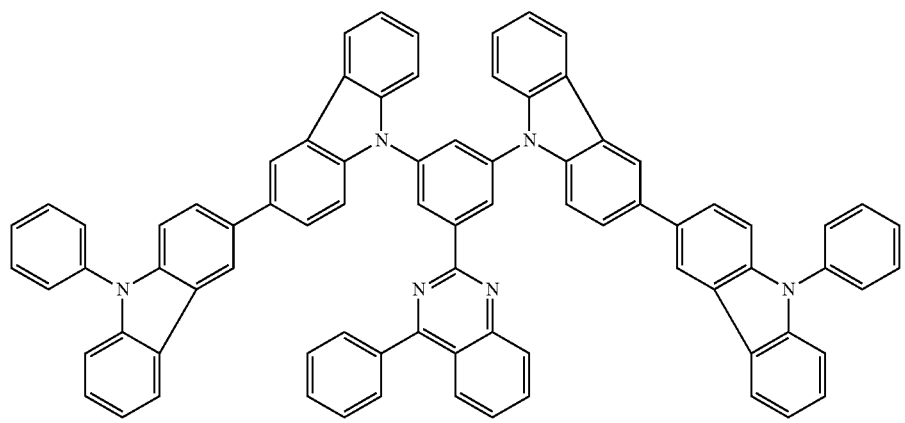
A-21
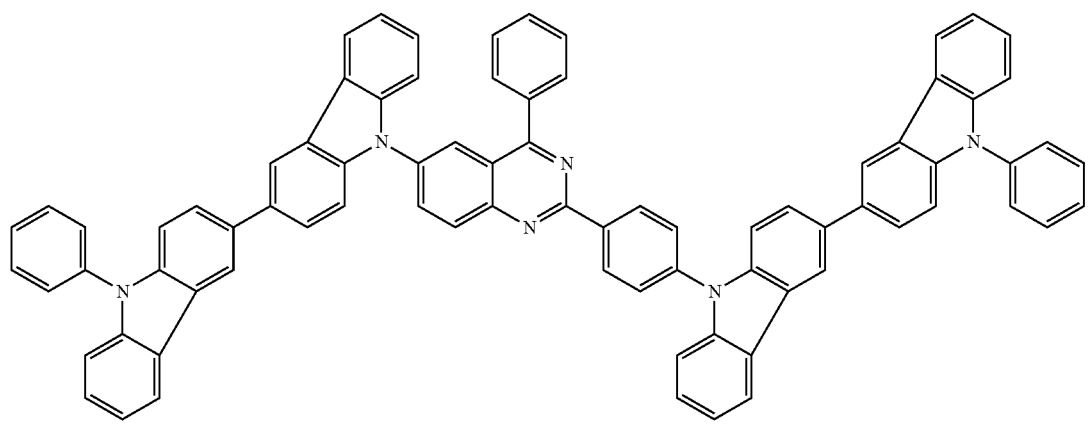
A-22
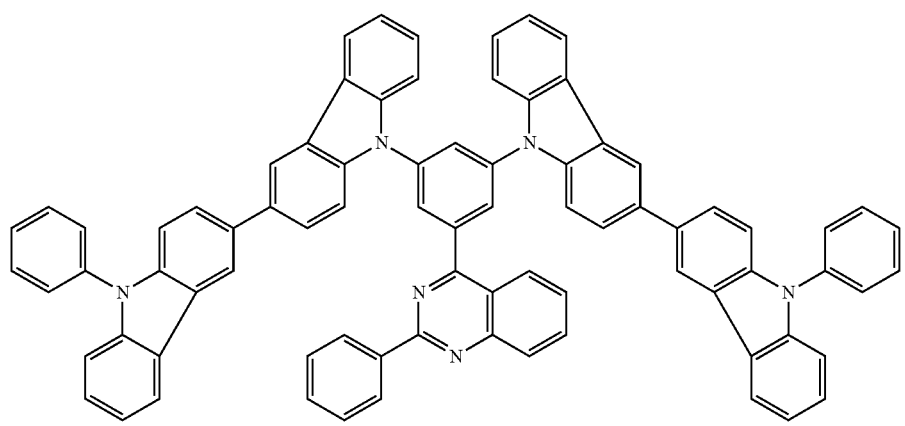
A-23

-continued
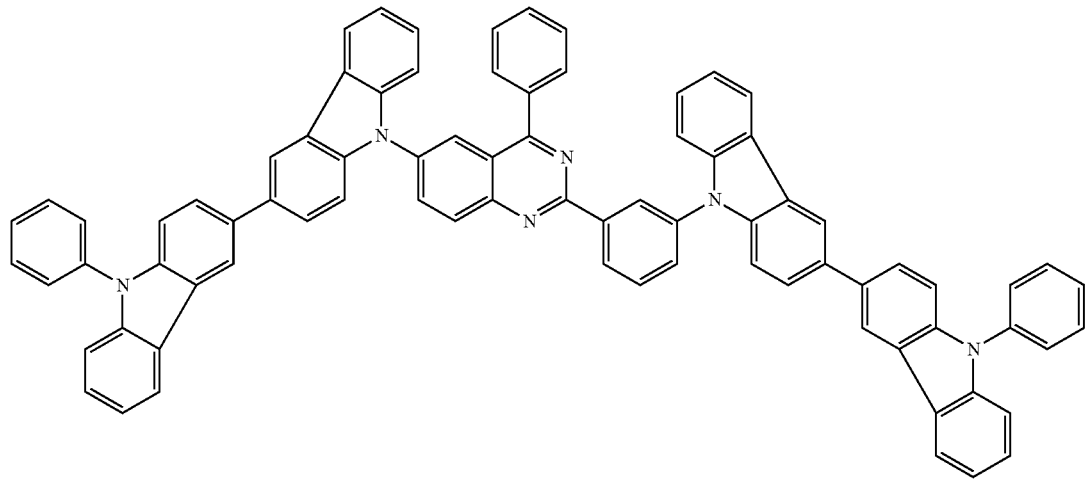
A-24
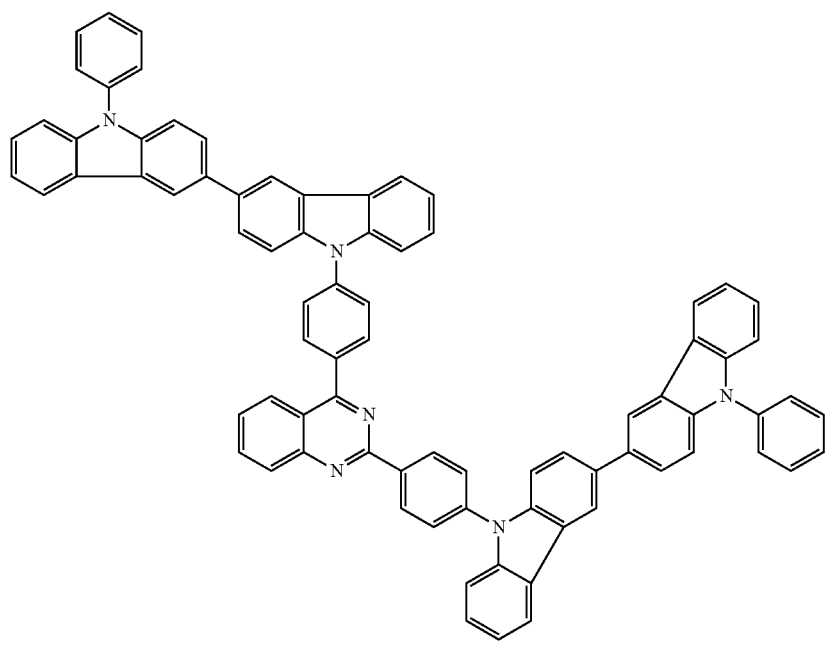
A-25

-continued
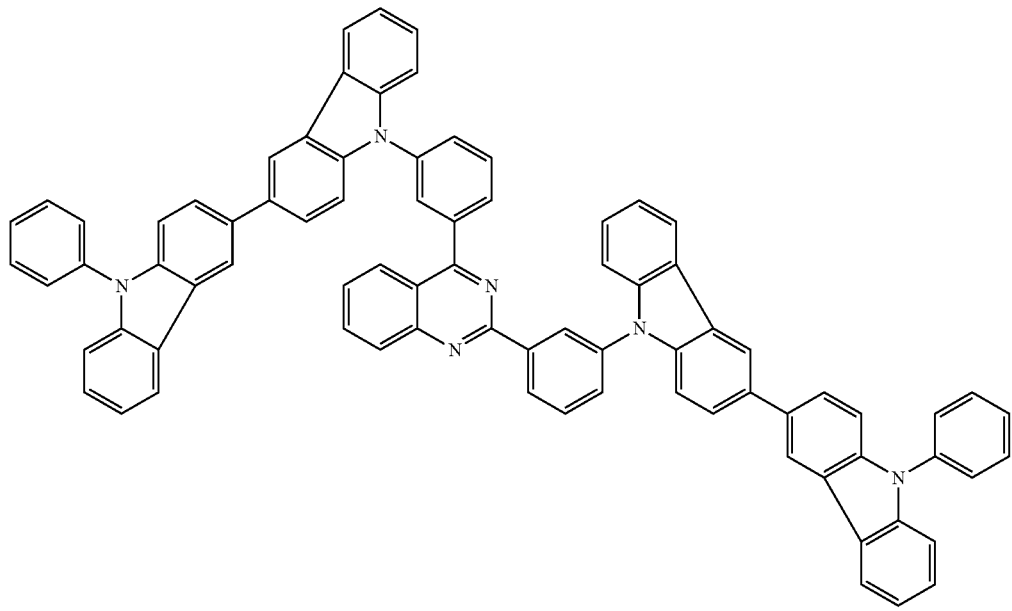
A-26
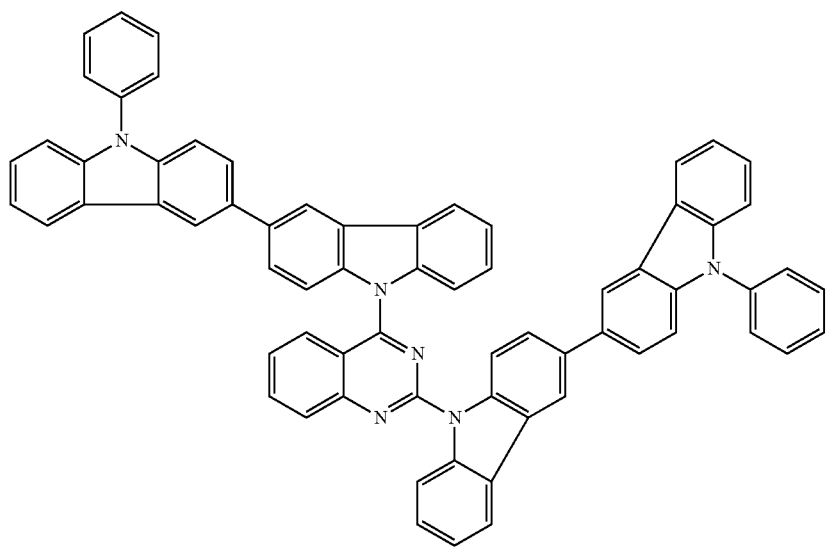
A-27

-continued
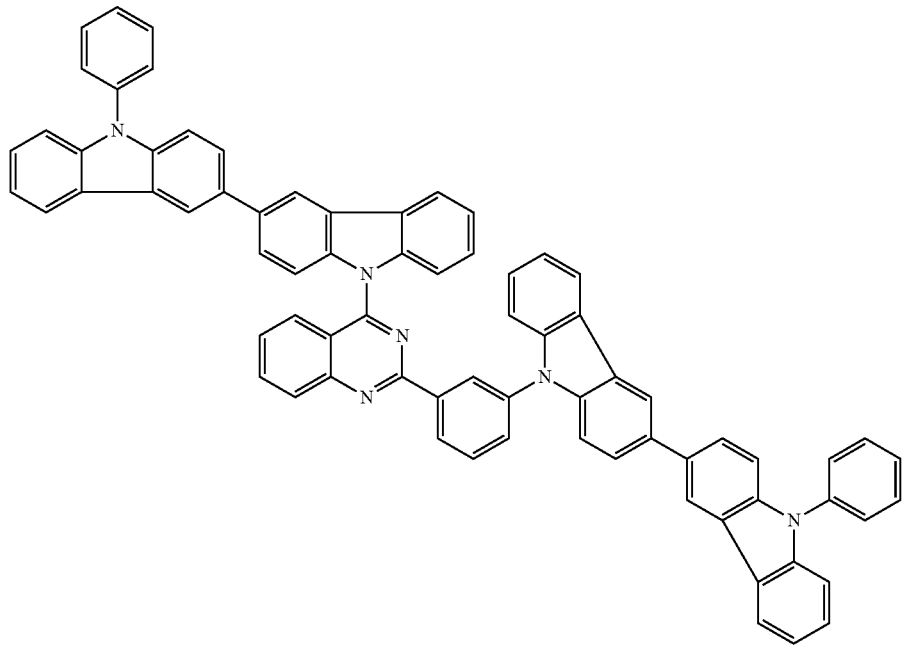
A-28
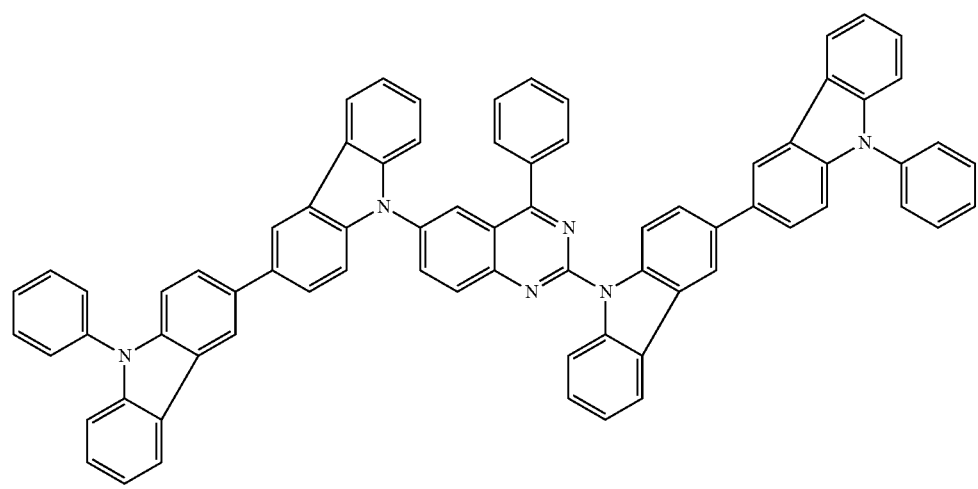
A-29

-continued
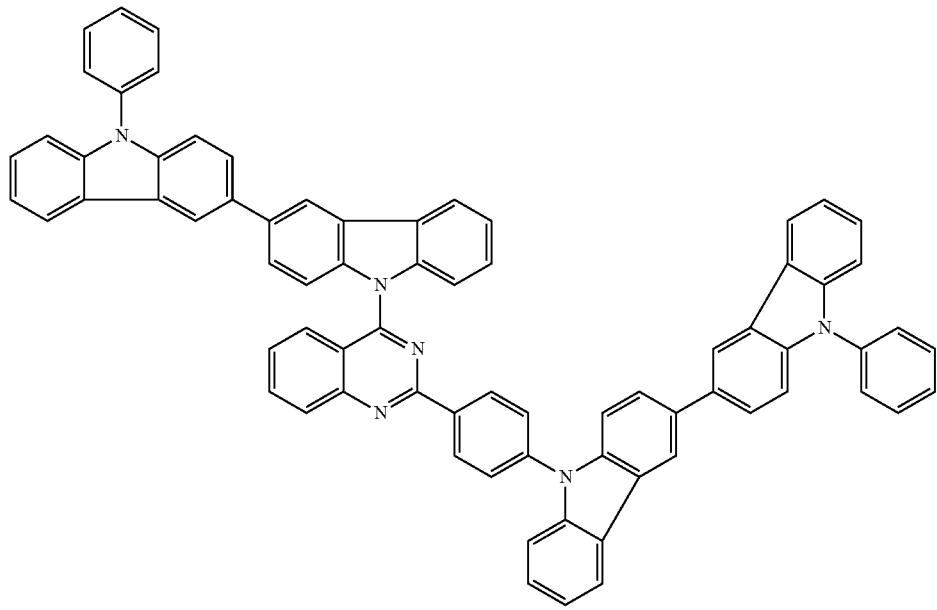
A-30
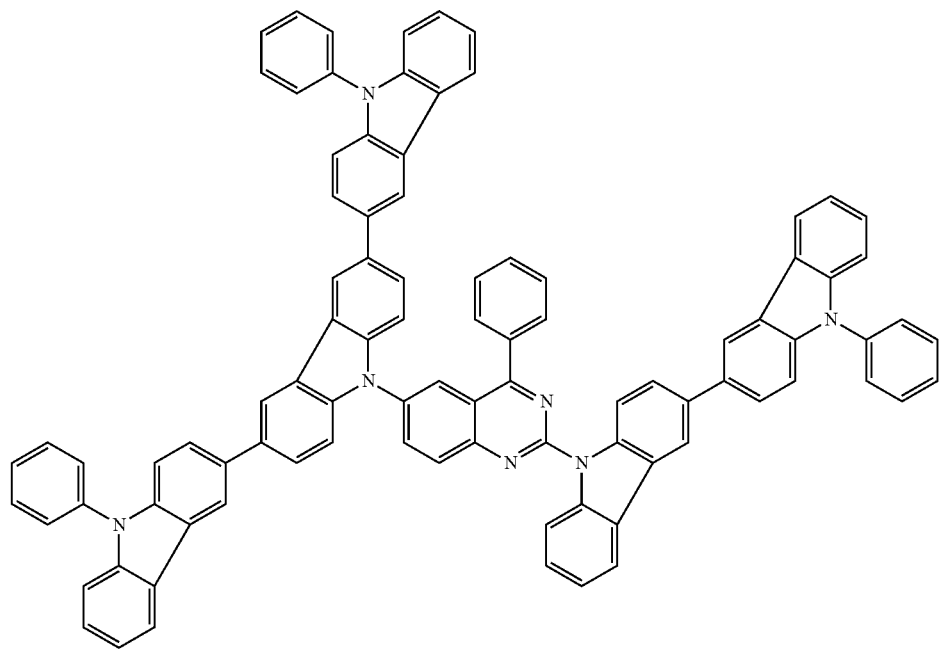
A-31

-continued
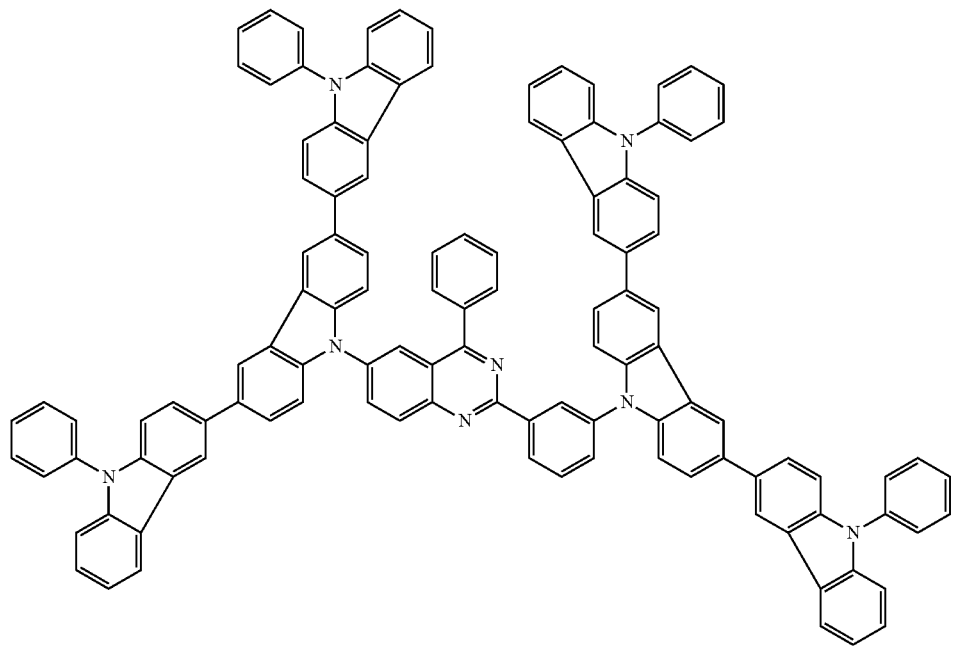
A-32
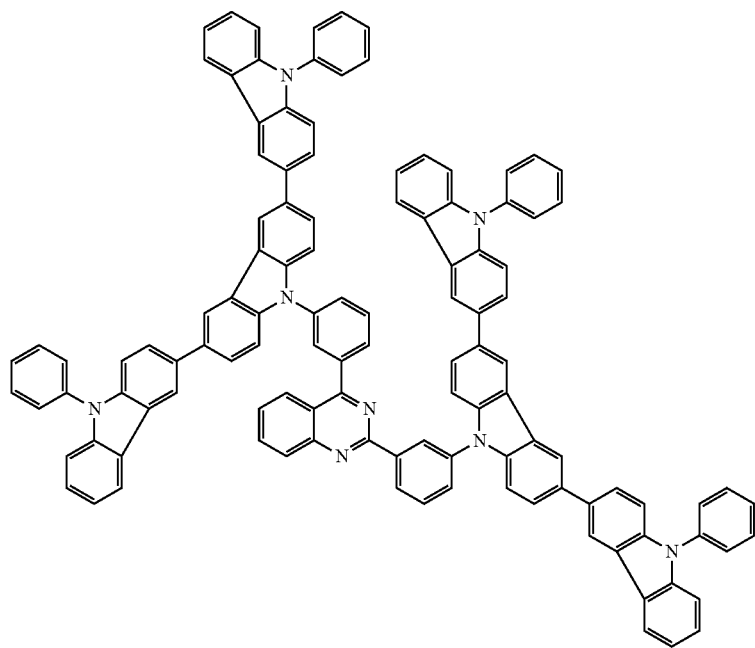
A-33

-continued
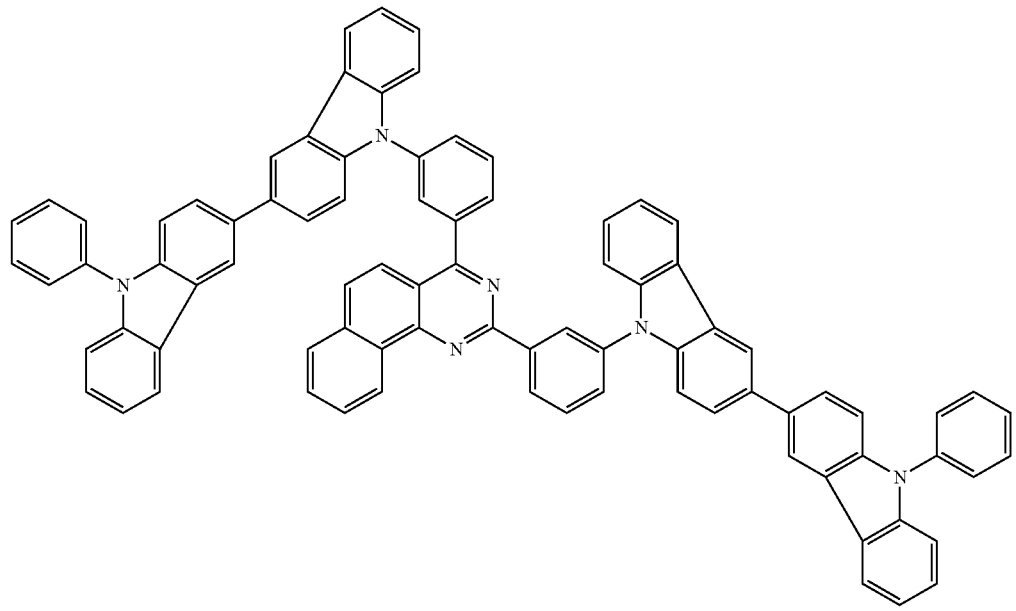
A-34
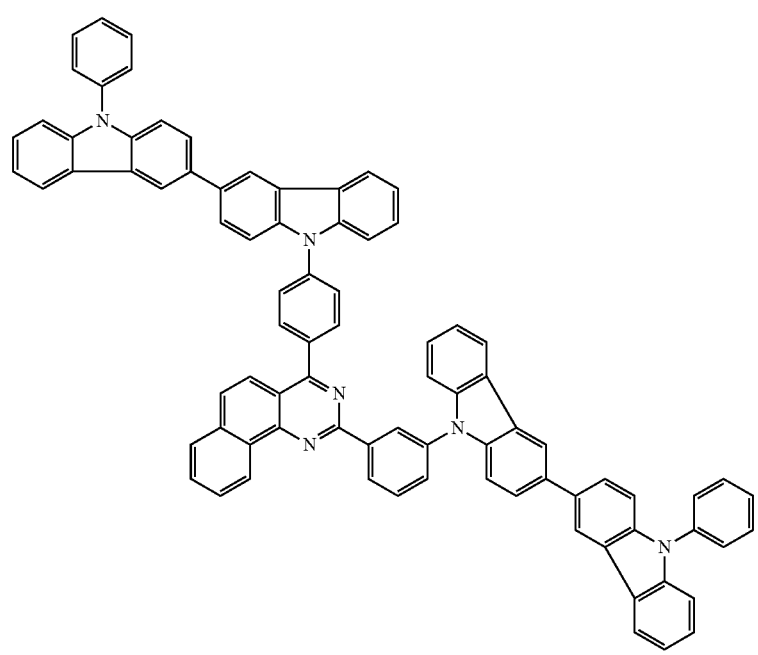
A-35

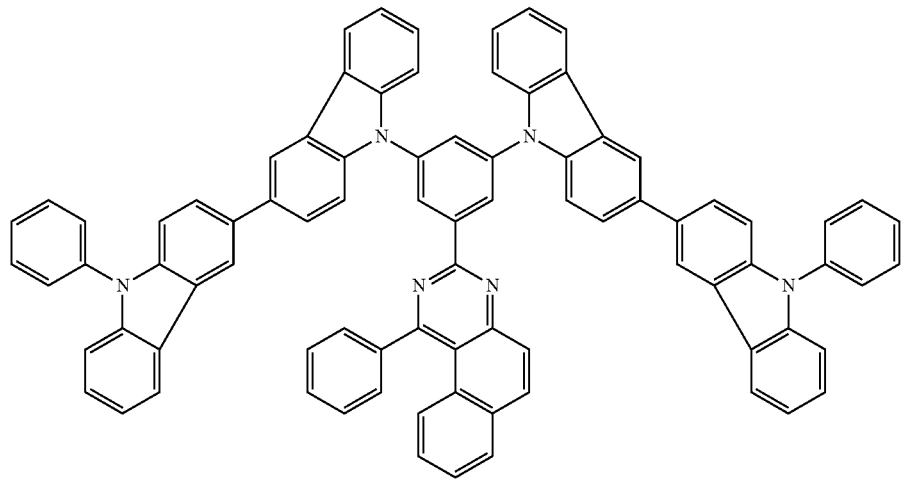
A-36
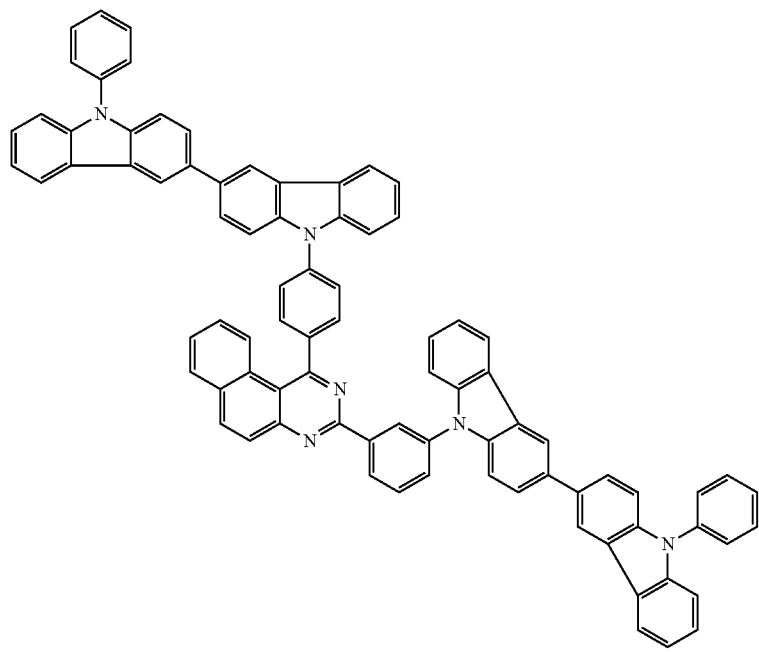
A-37

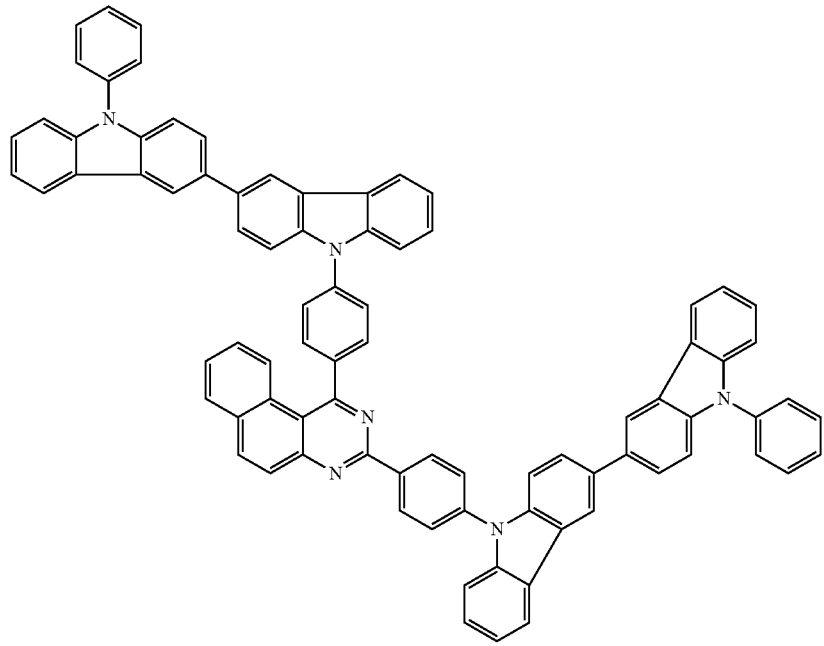
A-38
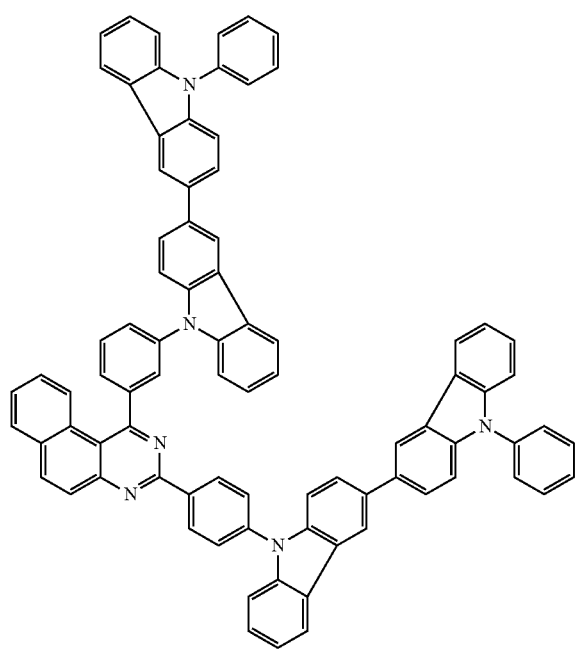
A-39

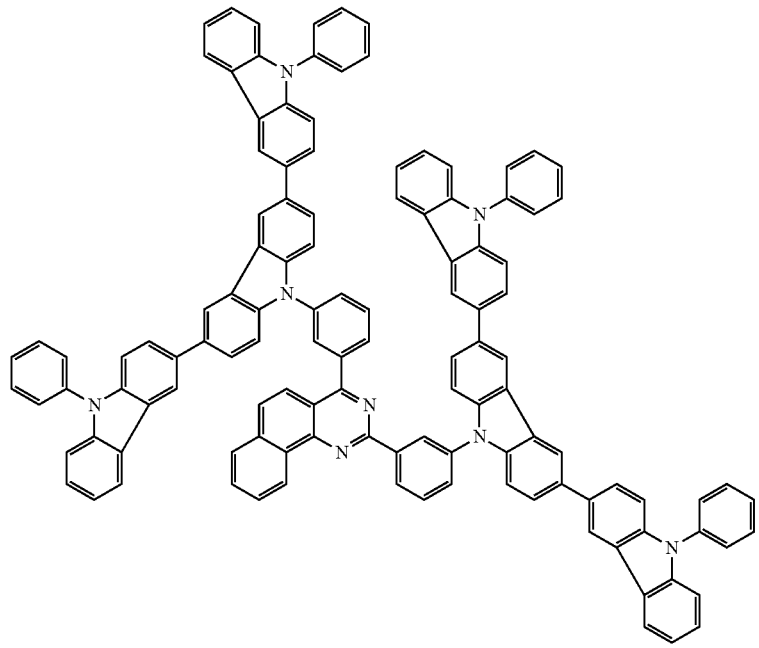
A-40
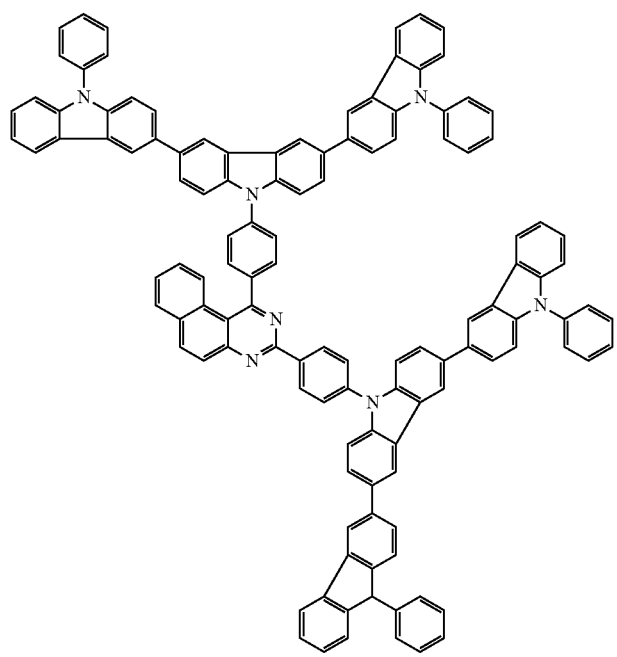
A-41

-continued
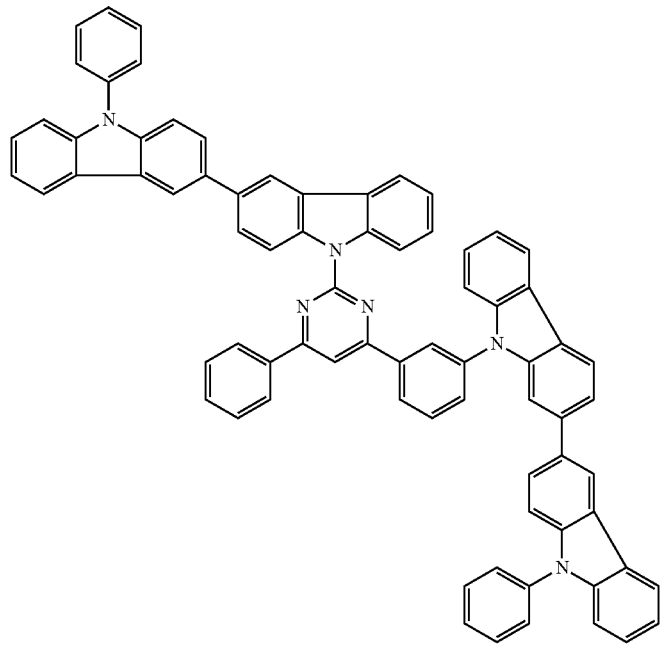
A-42
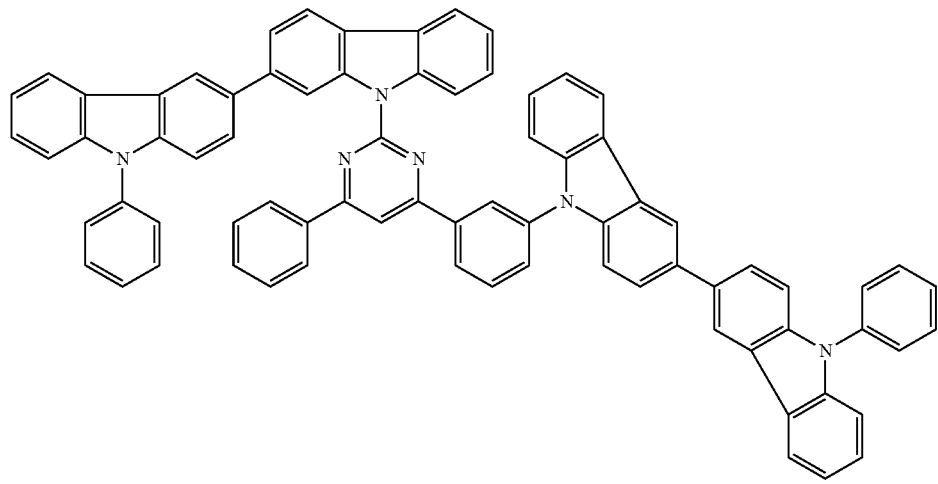
A-43

-continued
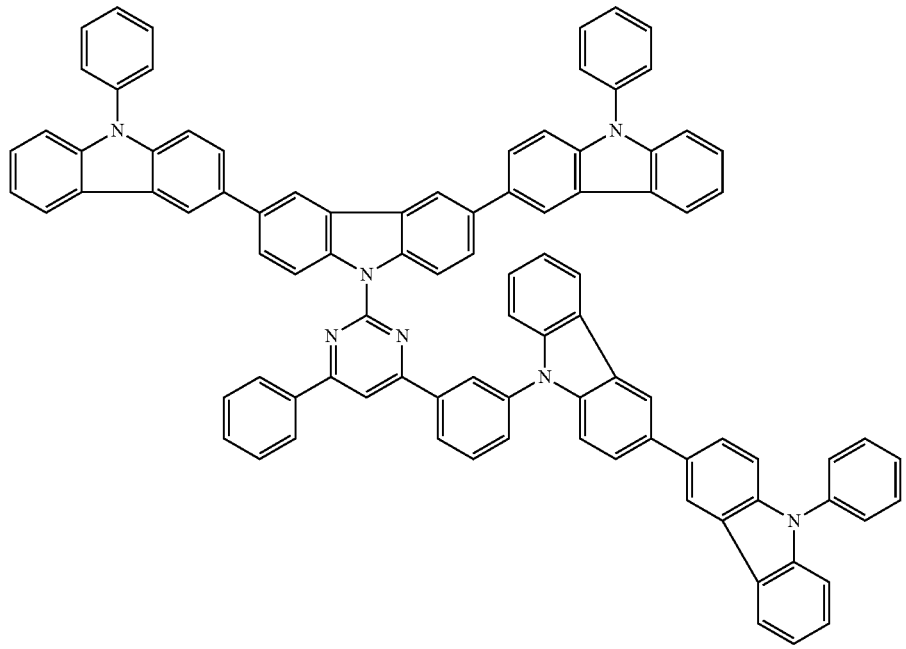
A-44
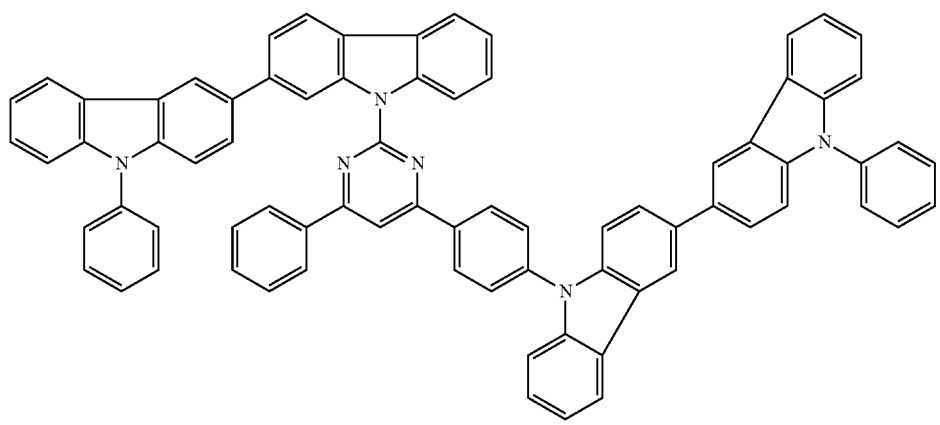
A-45
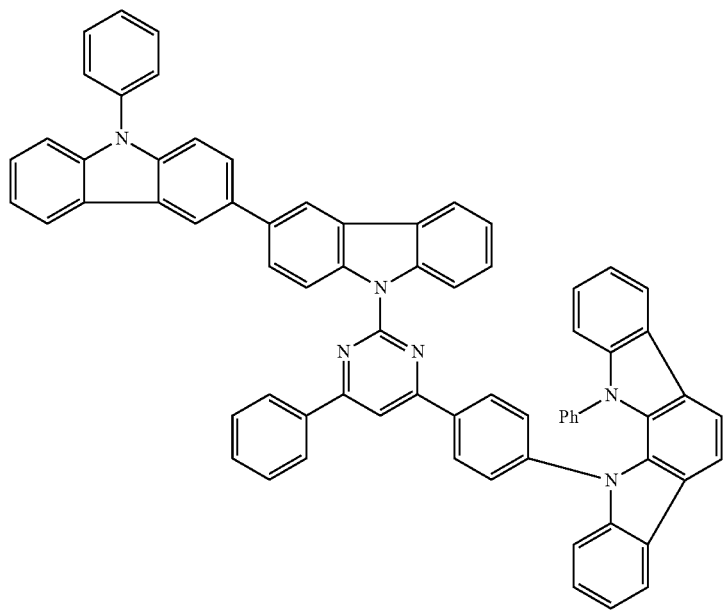
A-46

-continued
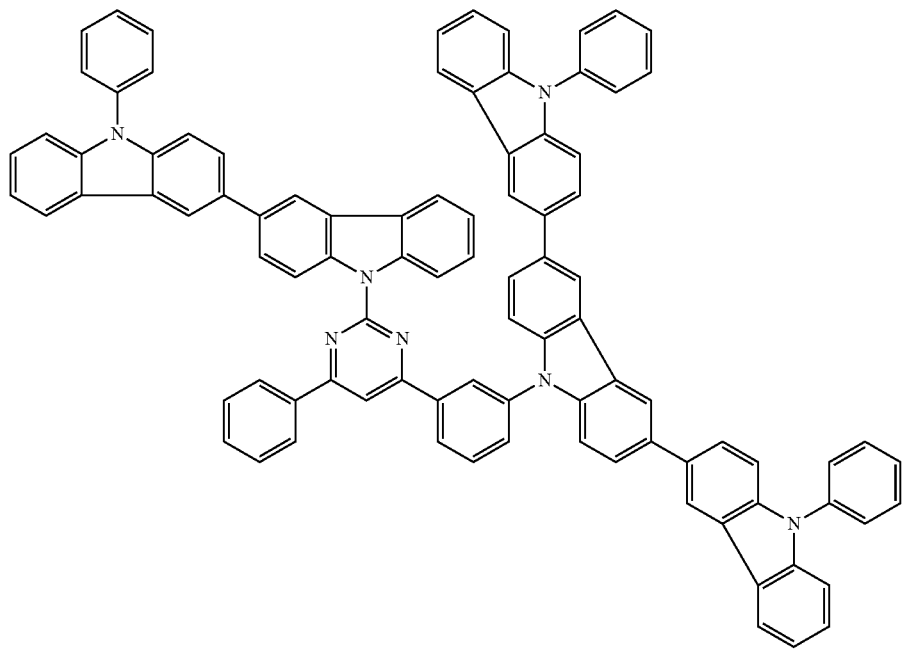
A-47
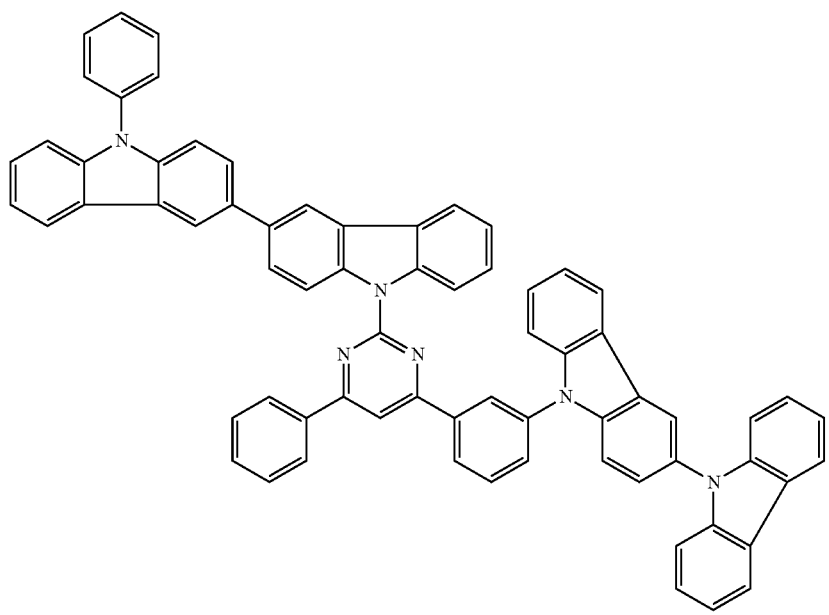
A-48

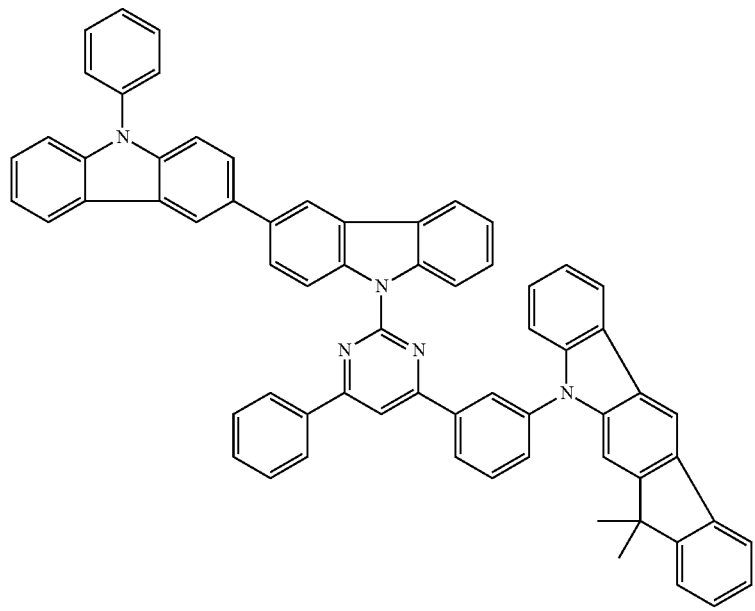
A-49
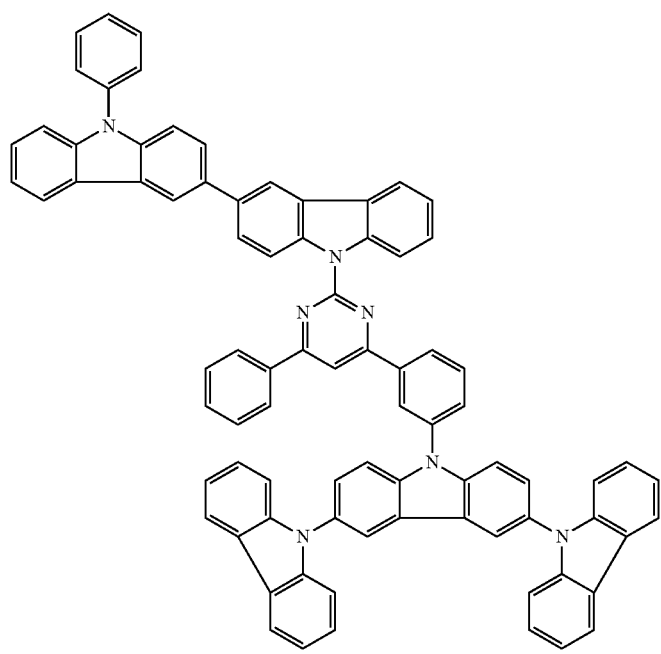
A-50

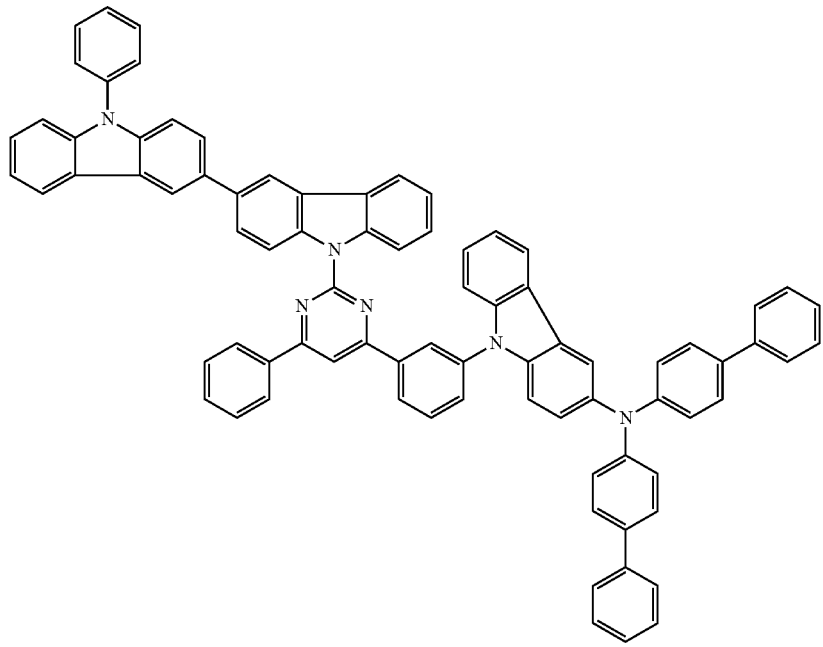
A-51
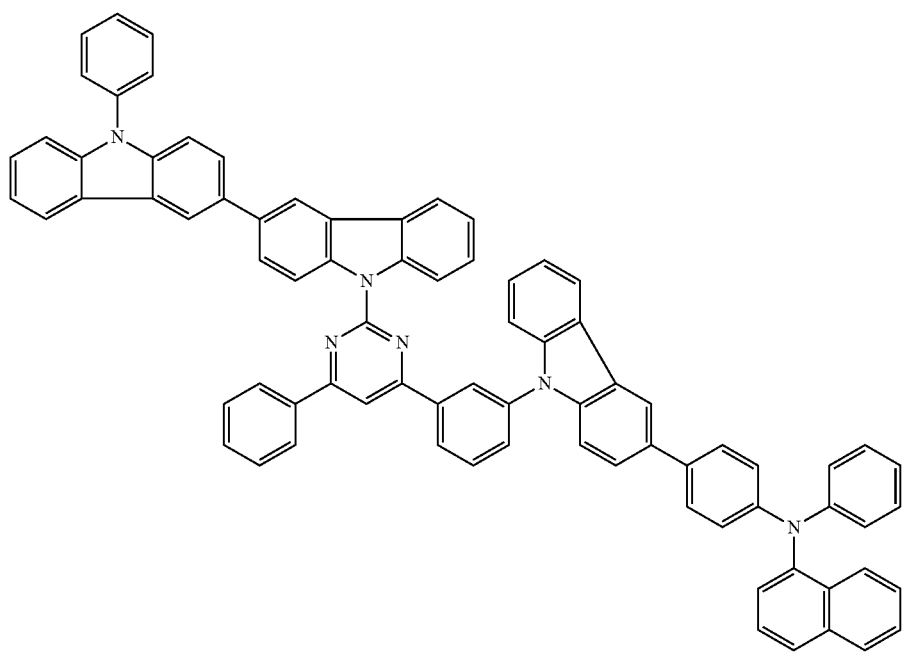
A-52

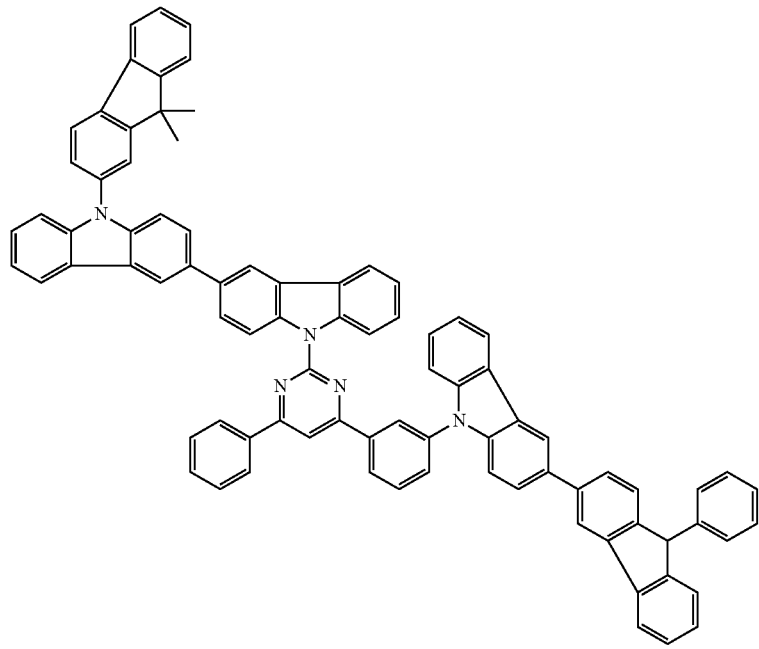
A-53
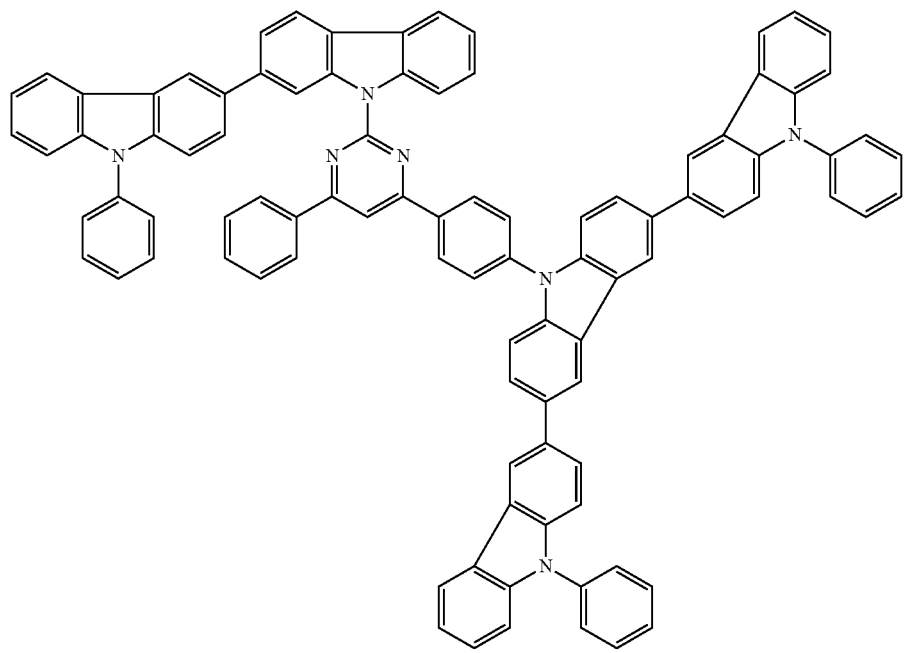
A-54

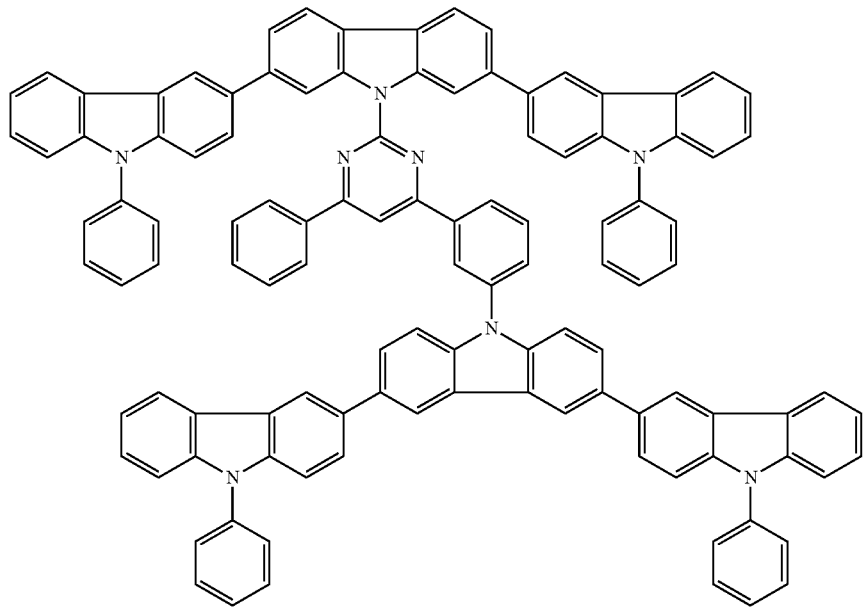
A-55
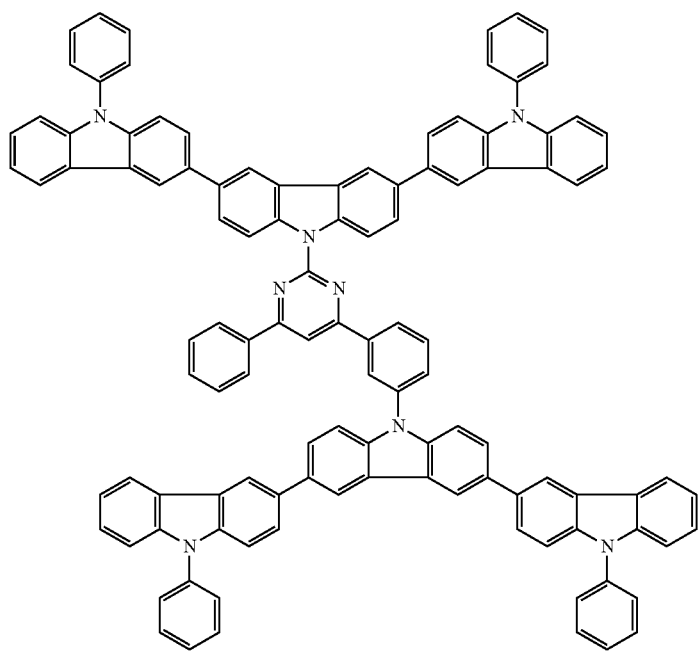
A-56

-continued
A-57
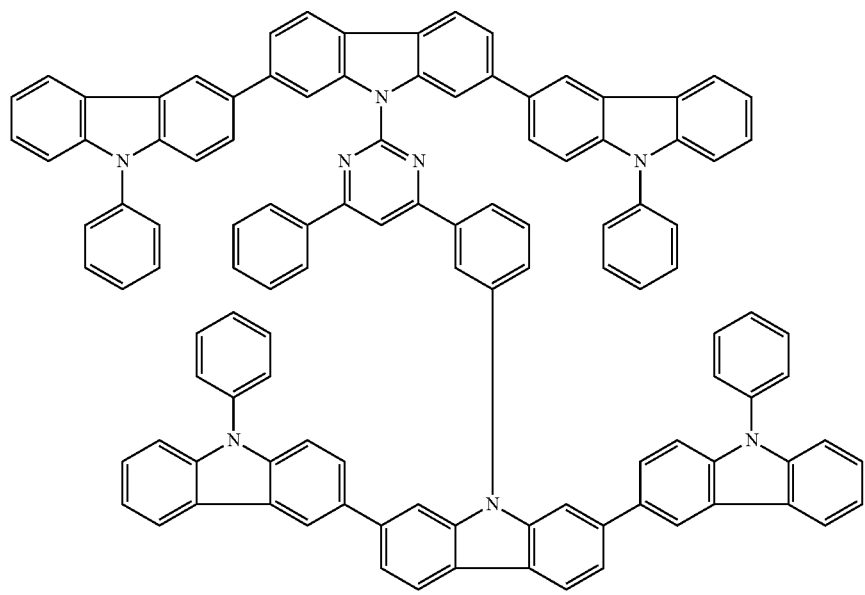
A-58
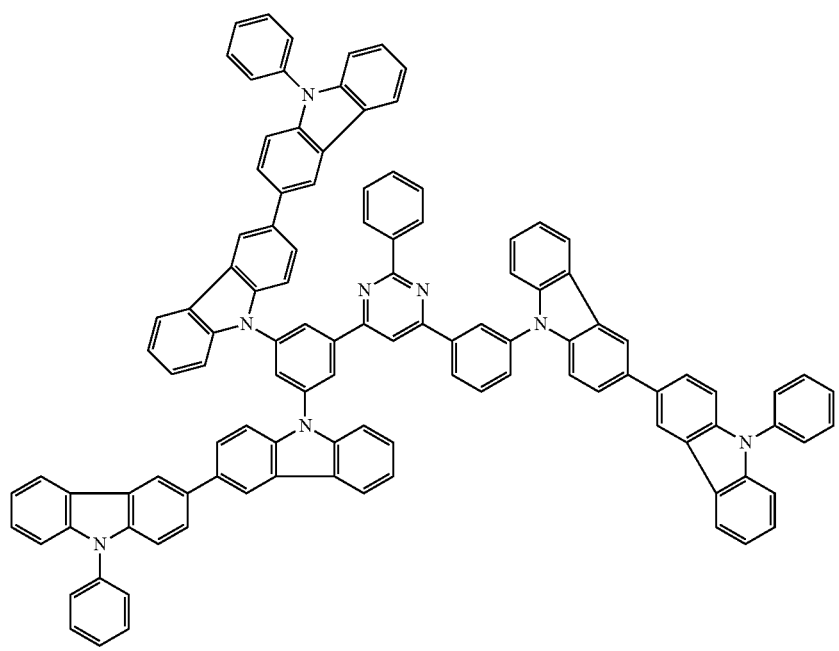
A-59
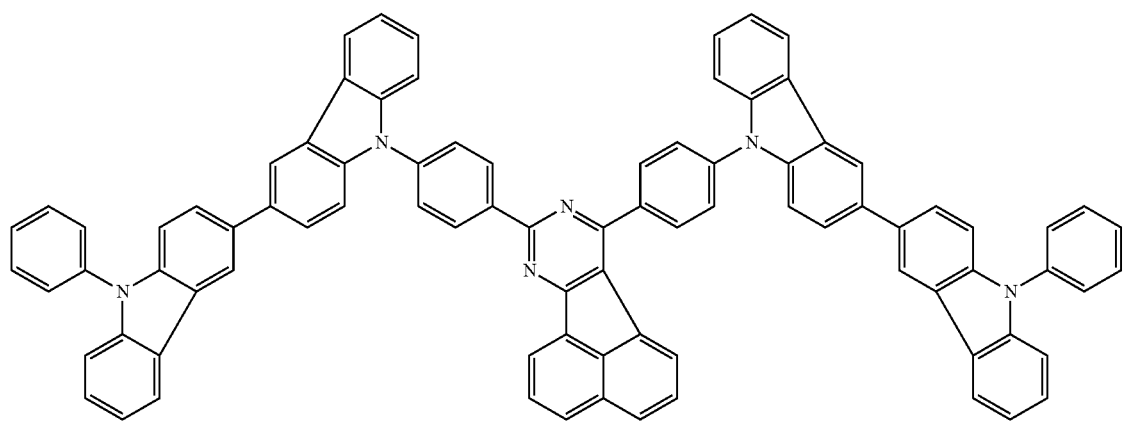

-continued
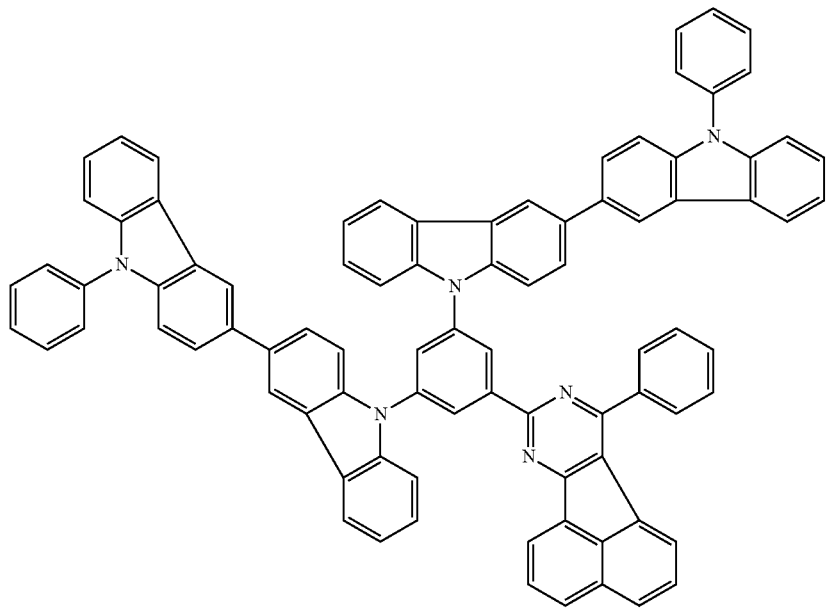
A-60
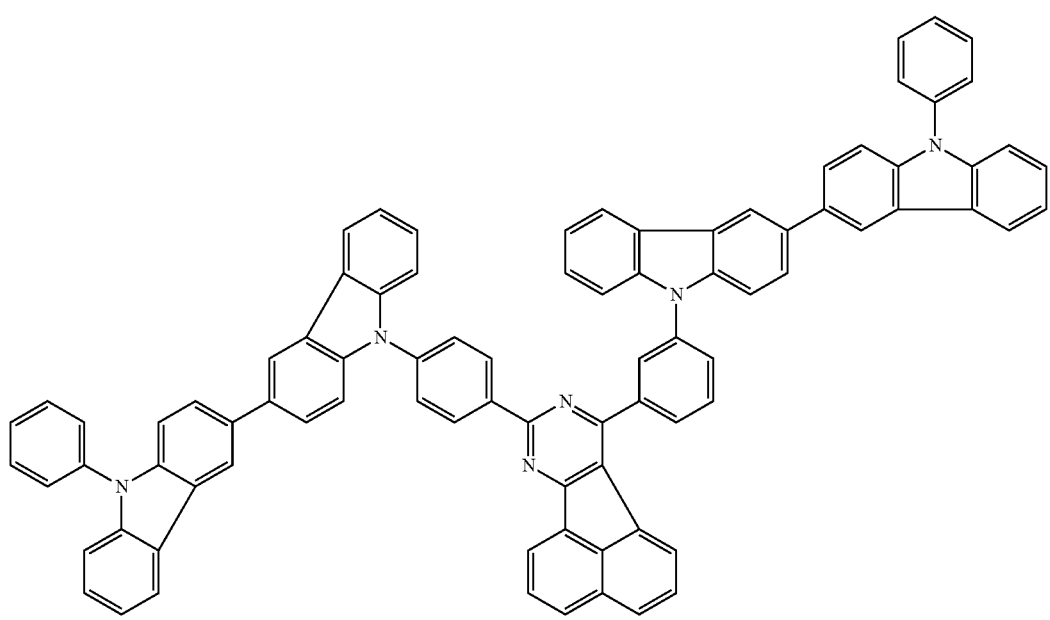
A-61

-continued
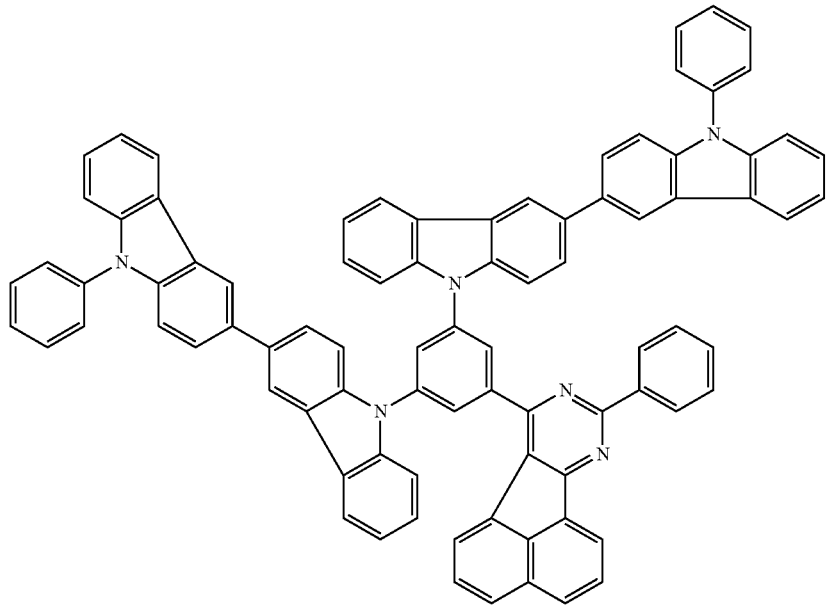
A-62
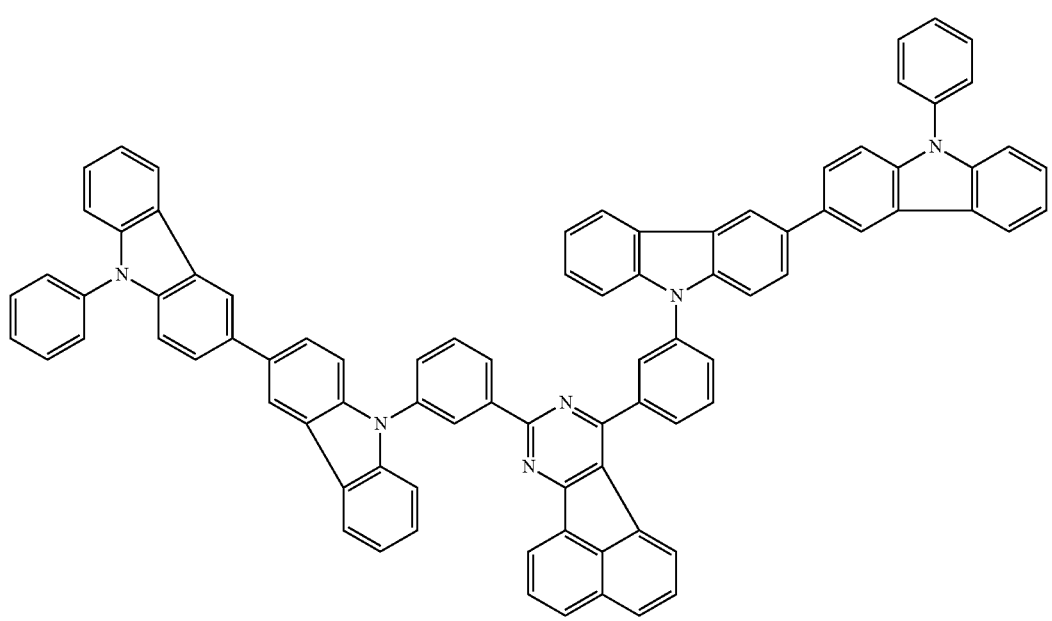
A-63

-continued
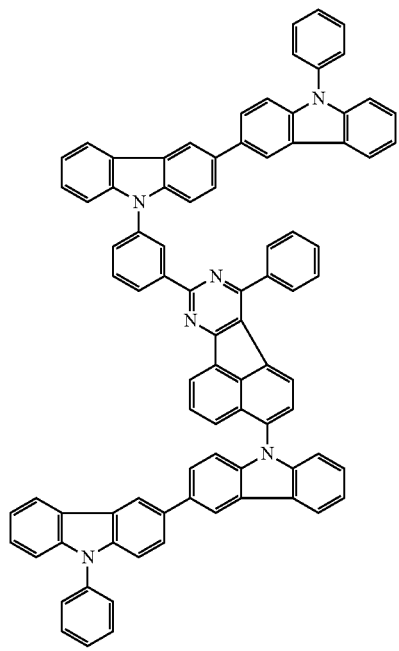
A-64
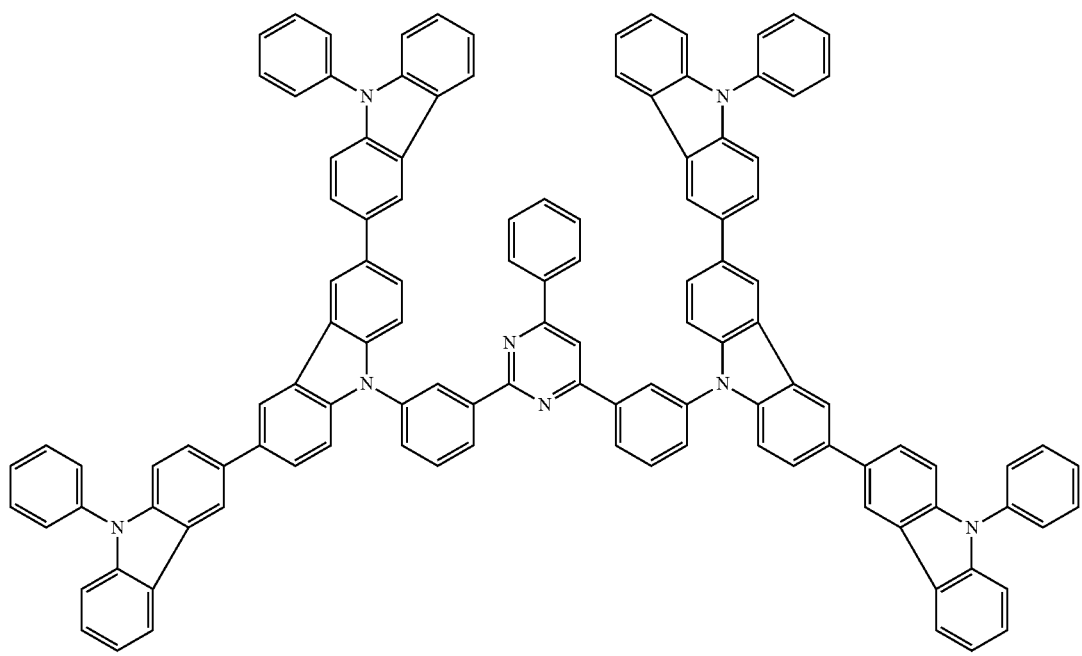
A-65

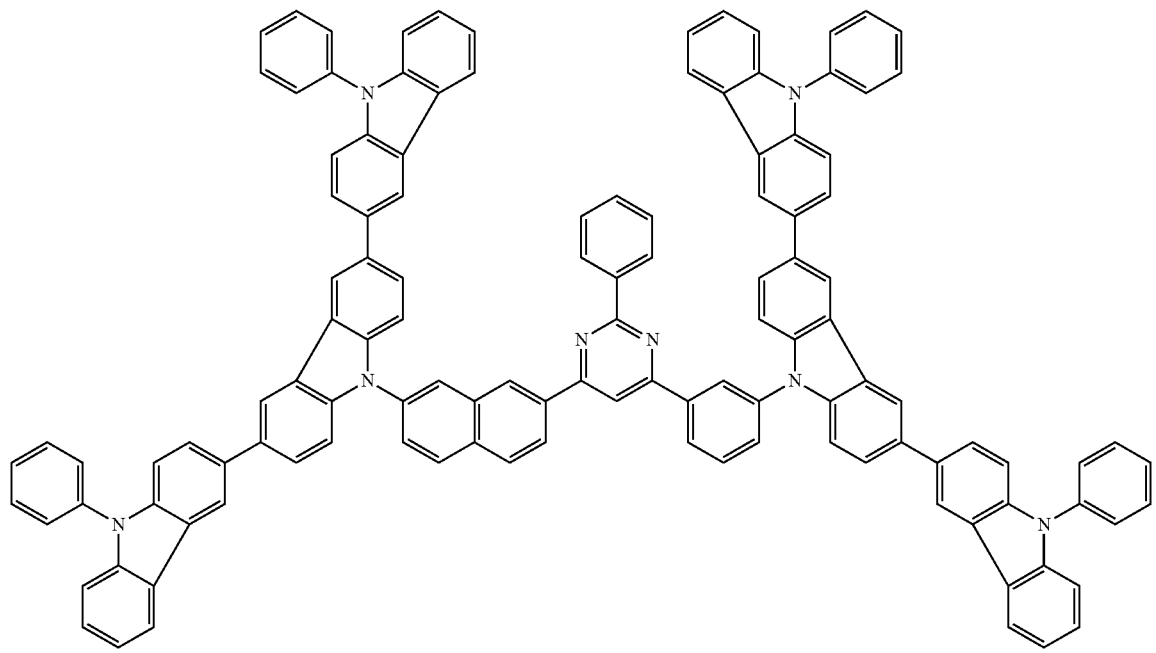
A-66
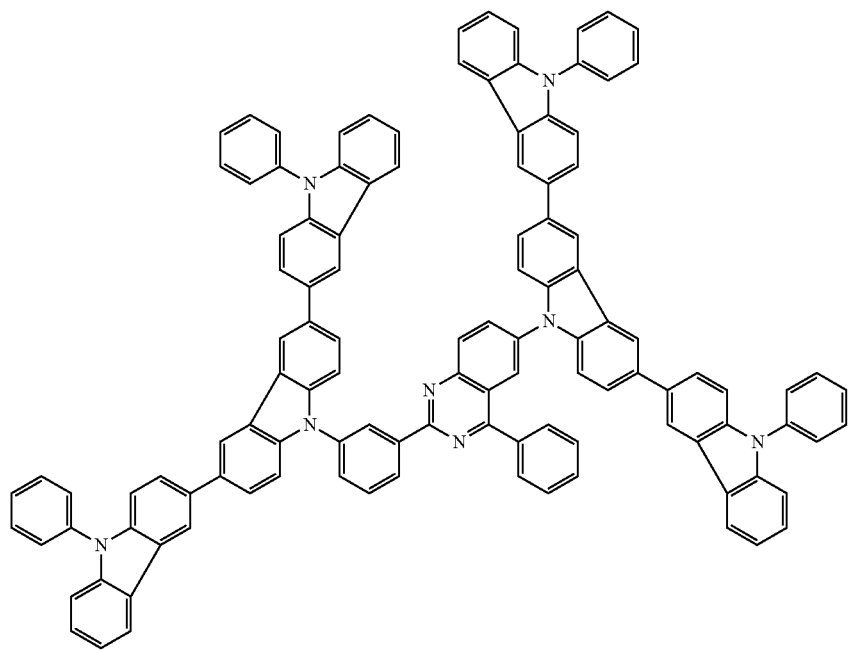
A-67

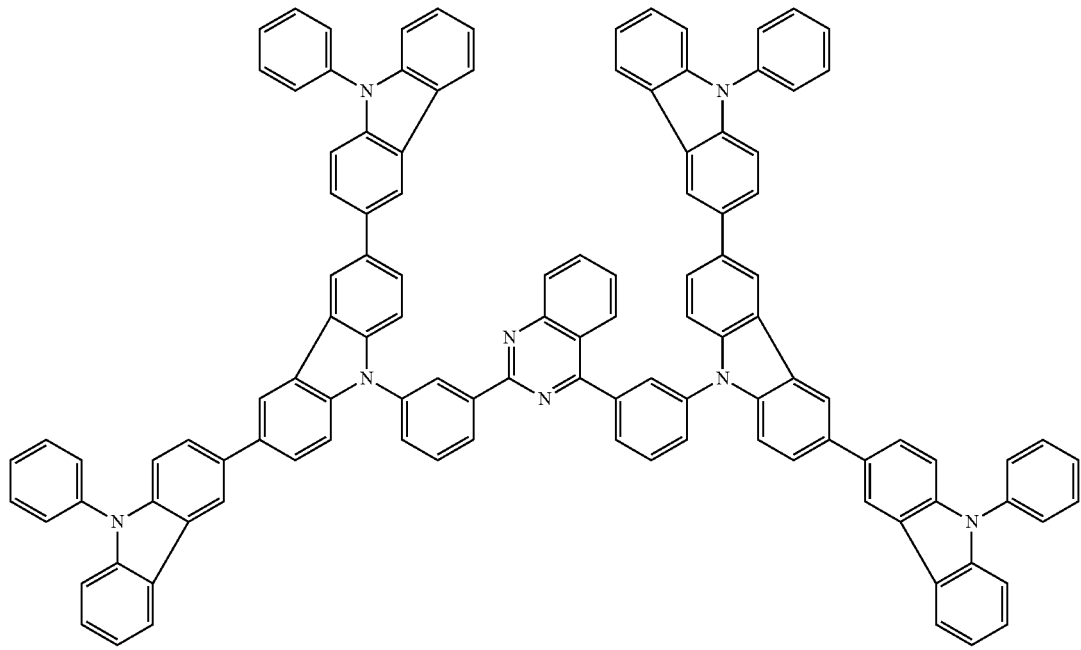
A-68
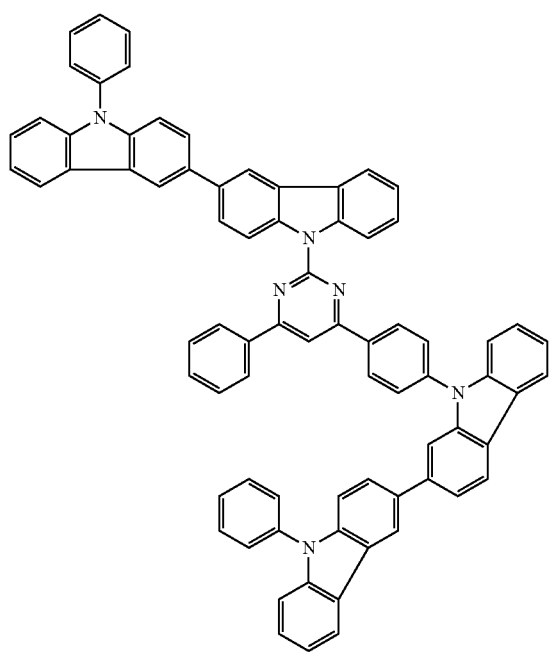
A-69

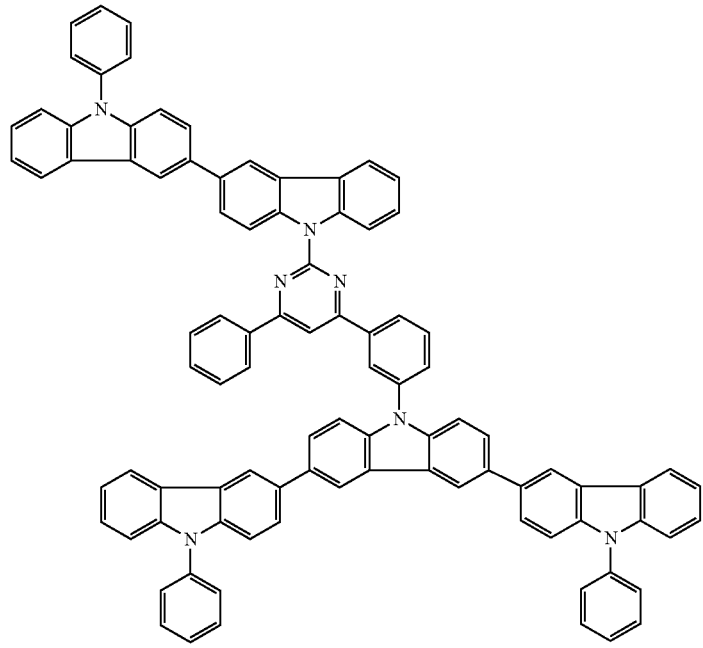
A-70
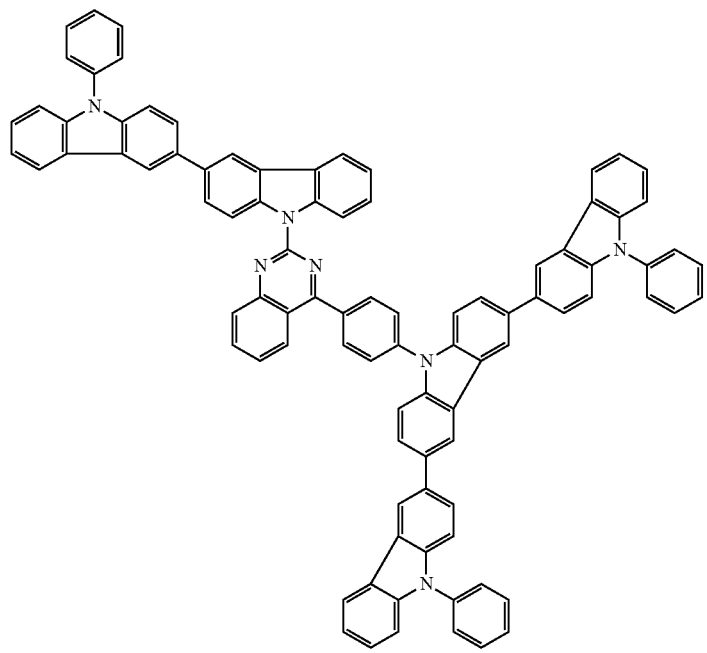
A-71

-continued
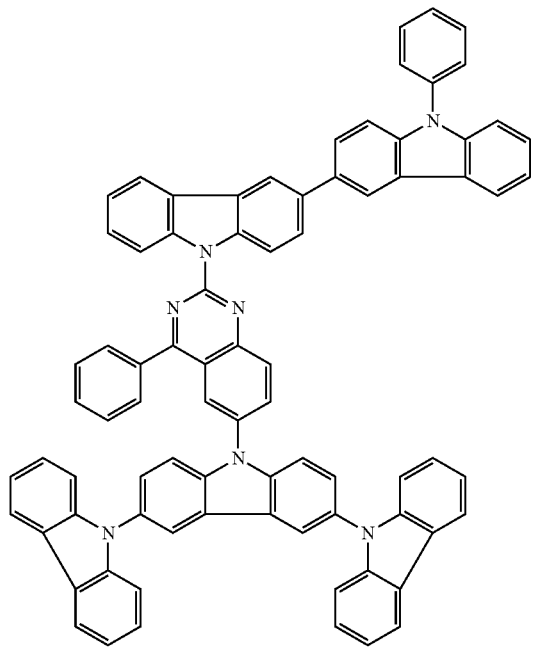
A-72
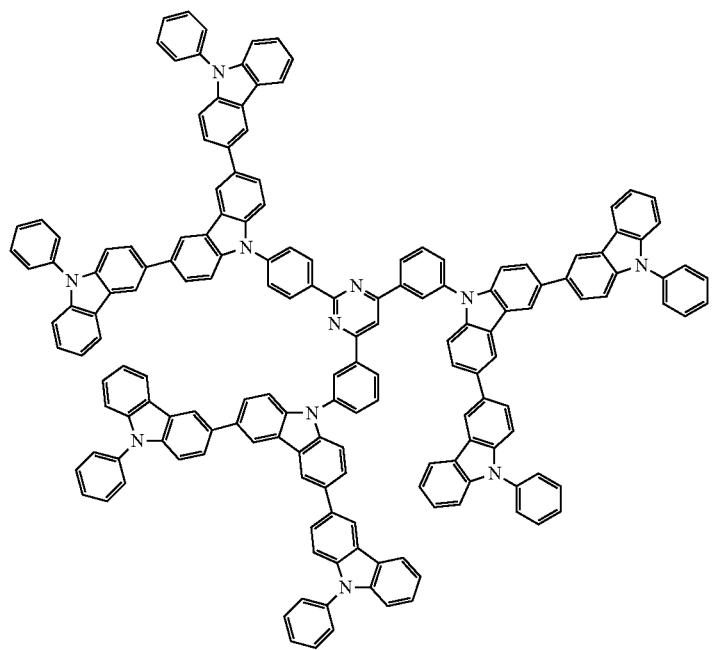
A-73

-continued
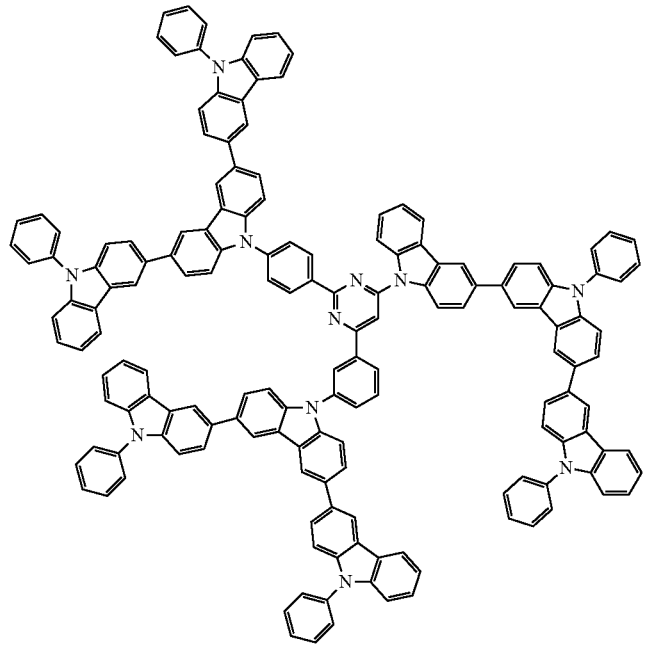
A-74
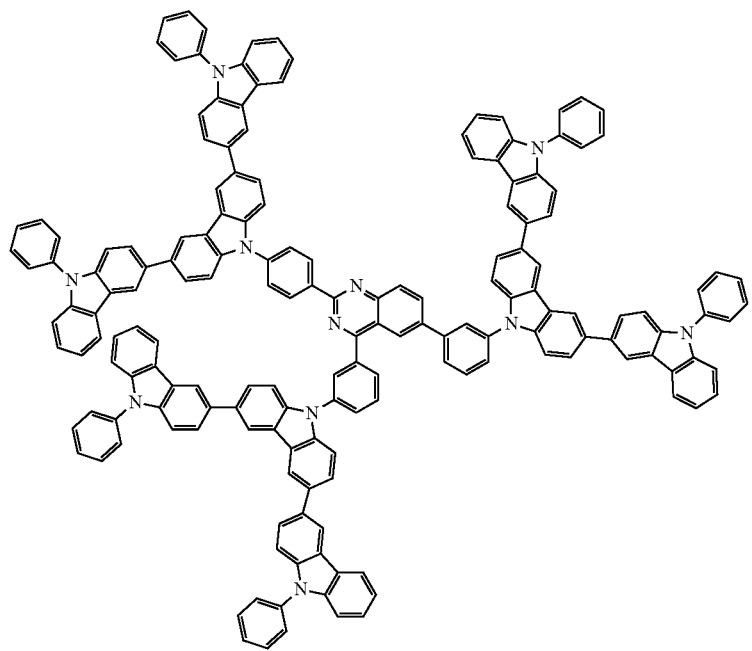
A-75

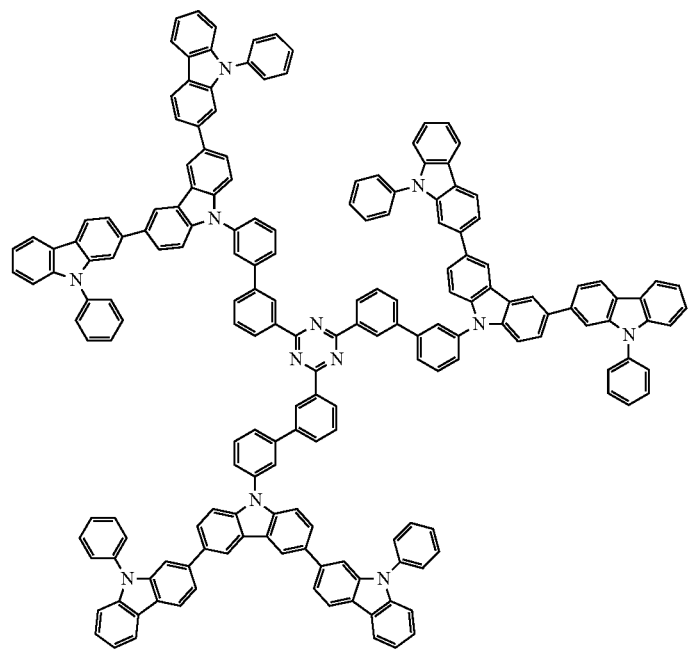
A-76
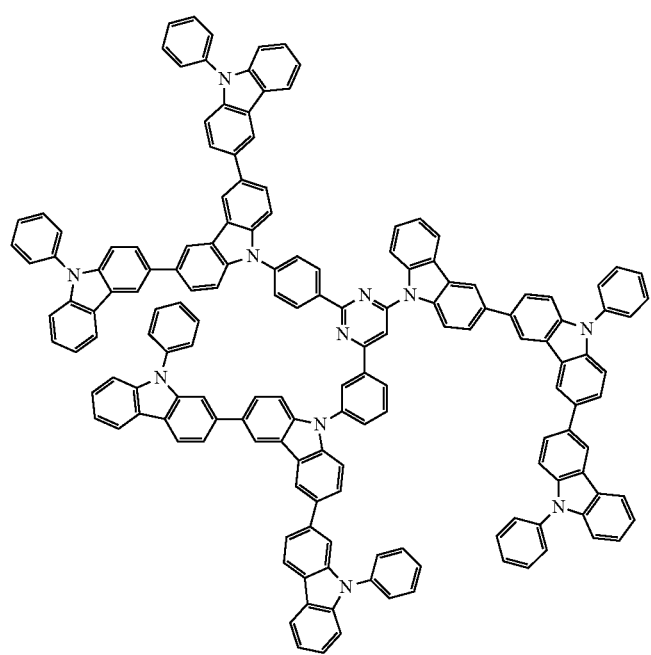
A-77

-continued
A-78
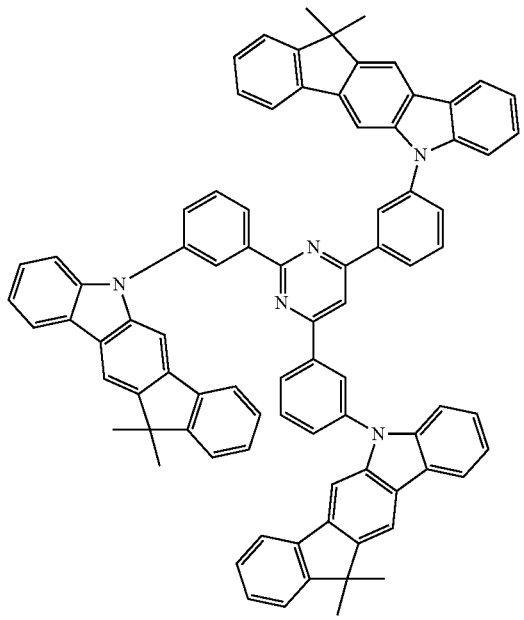
A-79
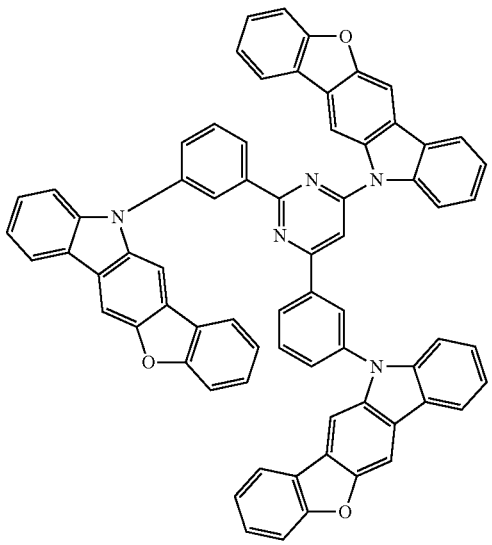
A-80
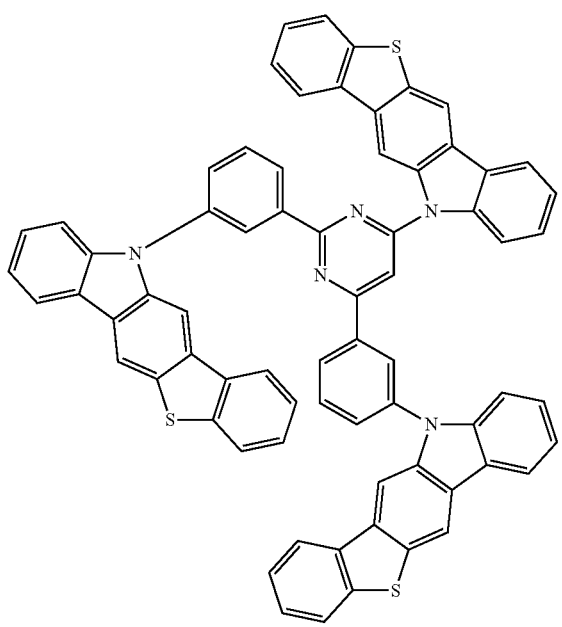

-continued
A-81
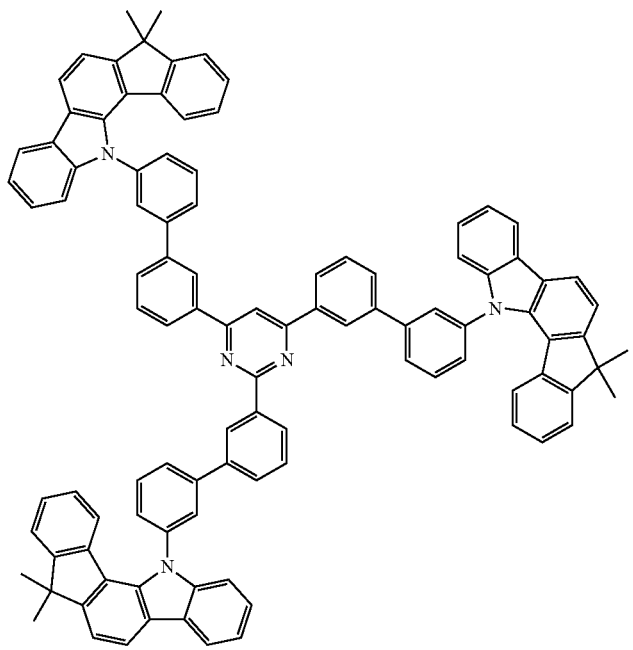
A-82
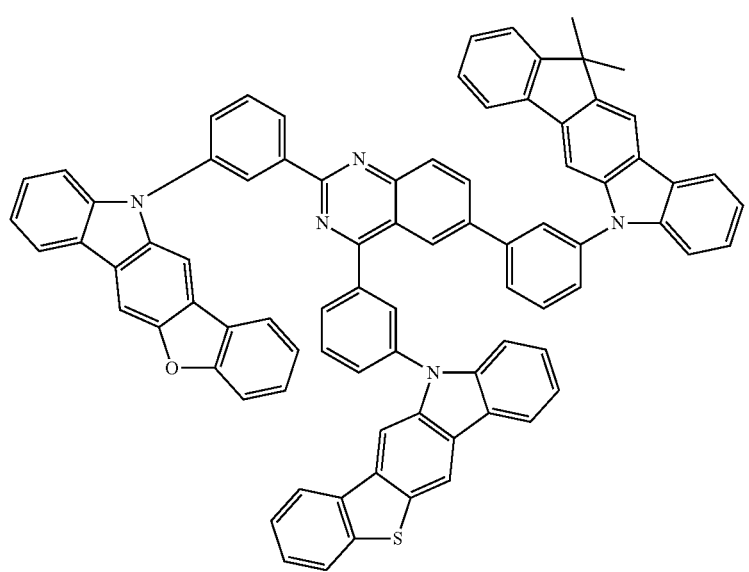

A-83
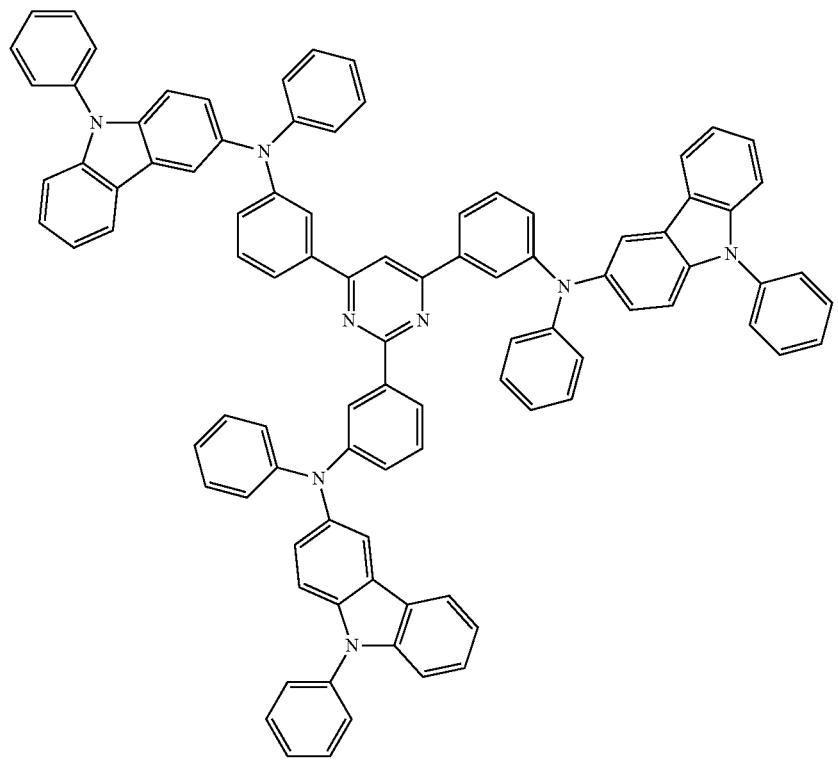
A-84
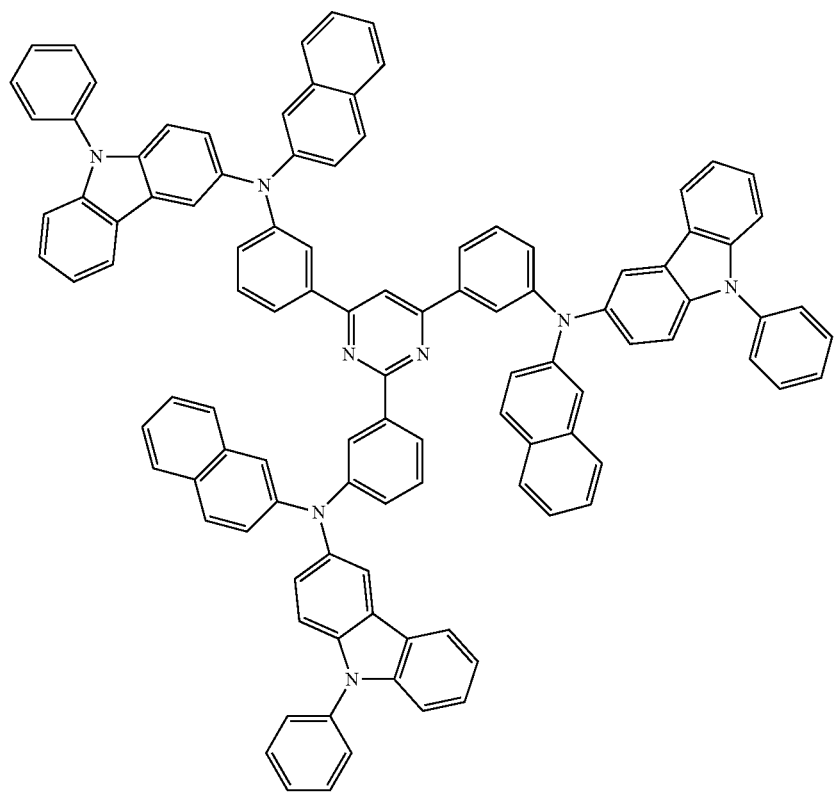

A-85
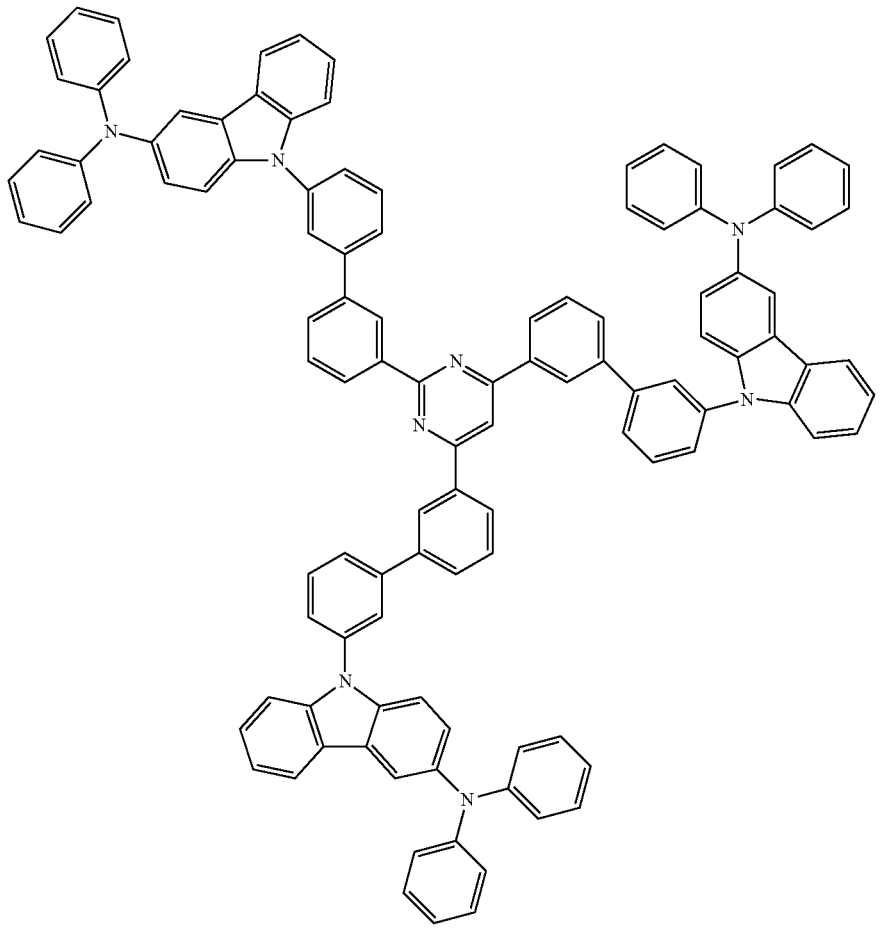
A-86
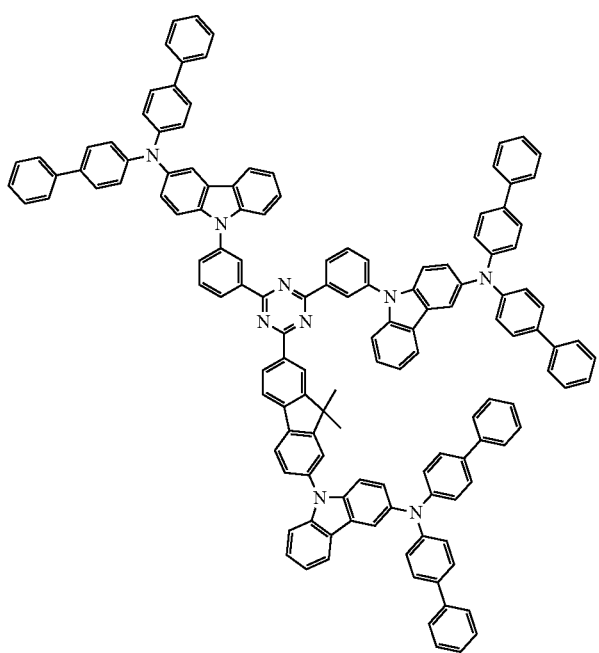

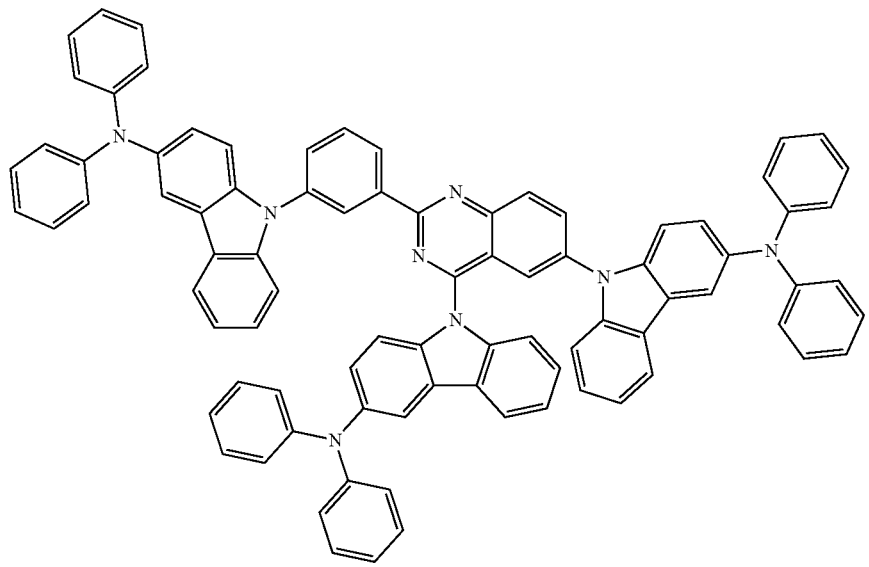
A-87
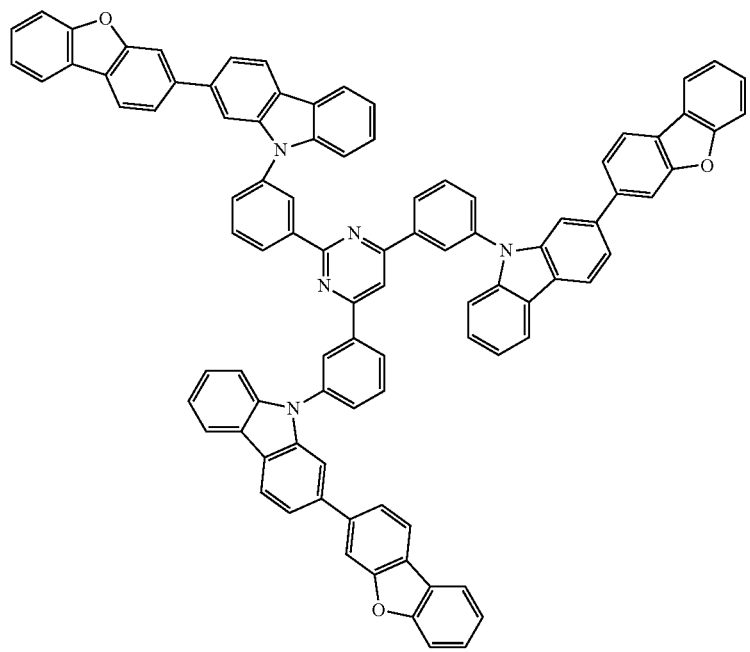
A-88

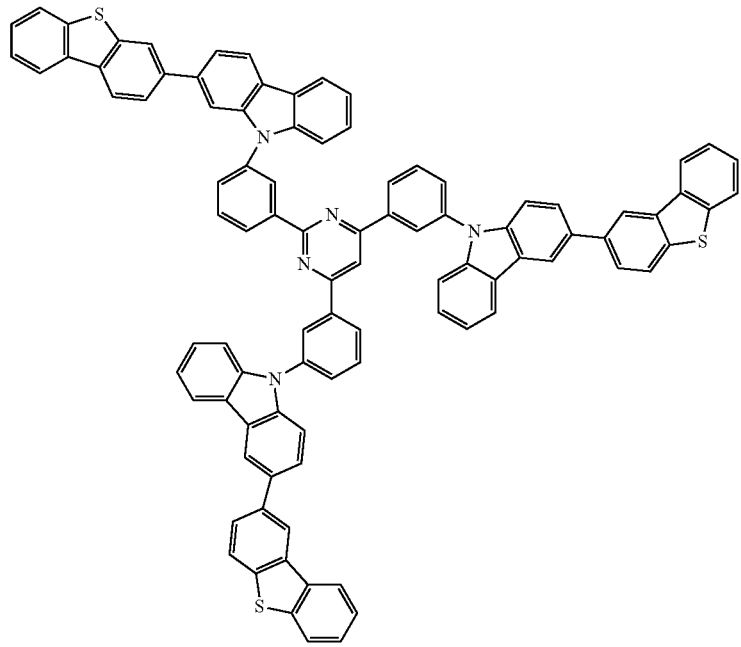
A-89
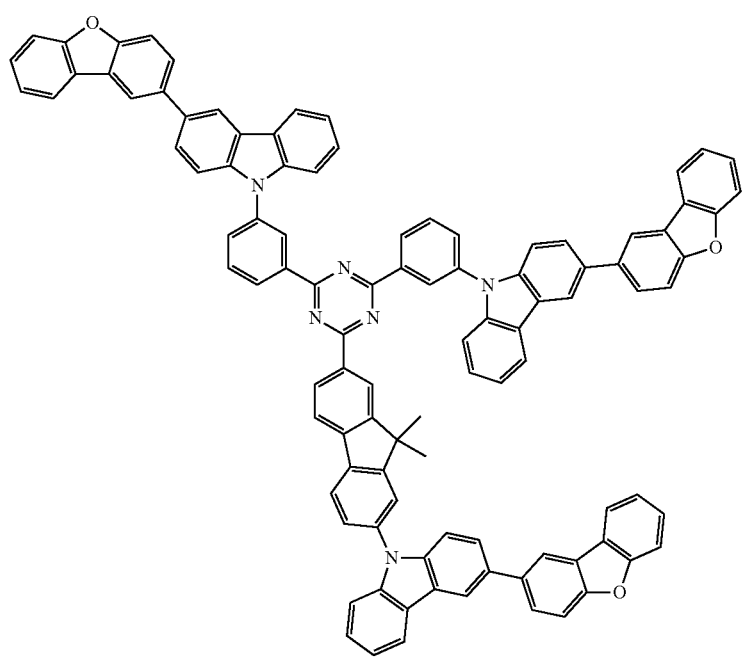
A-90

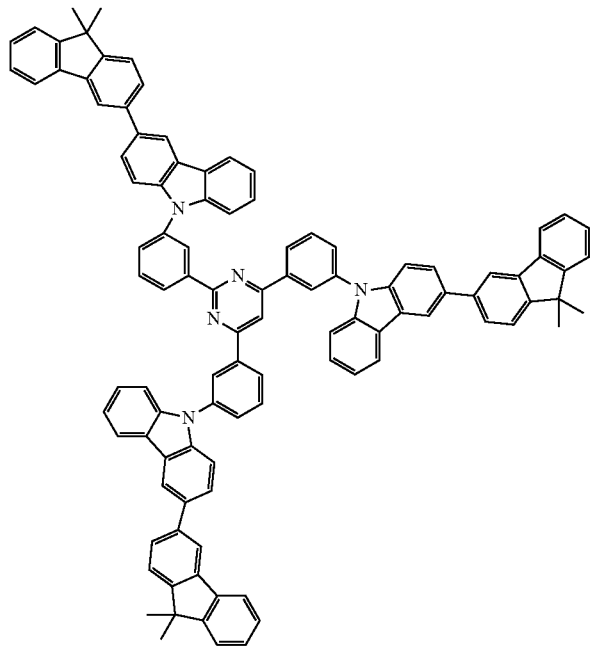
A-91
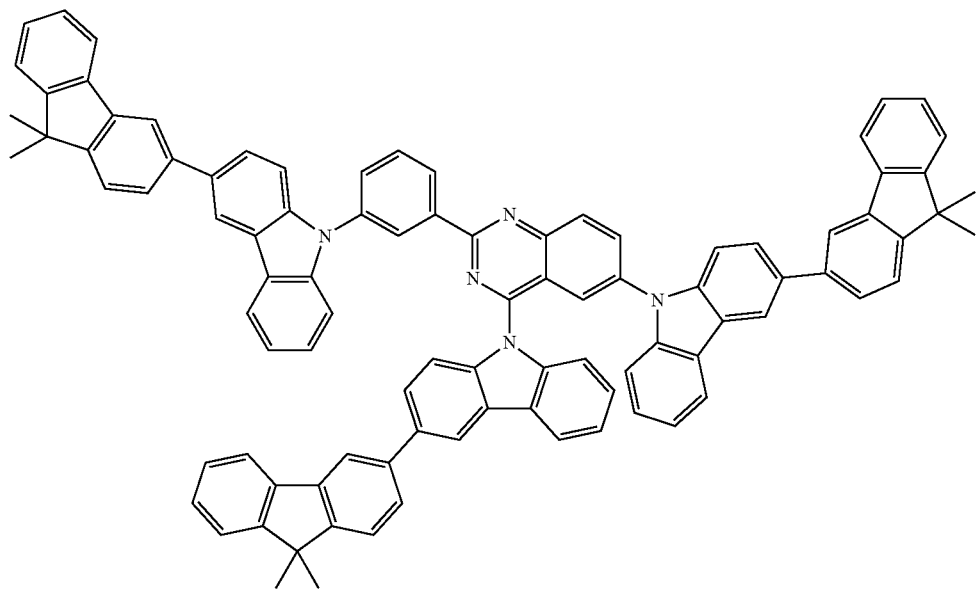
A-92

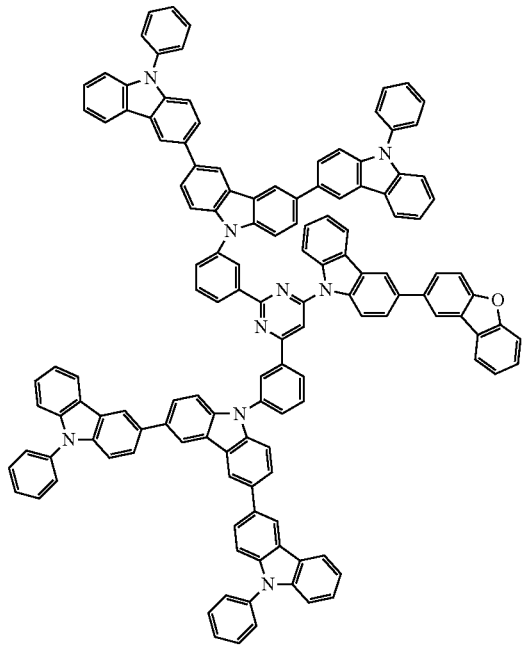
A-93
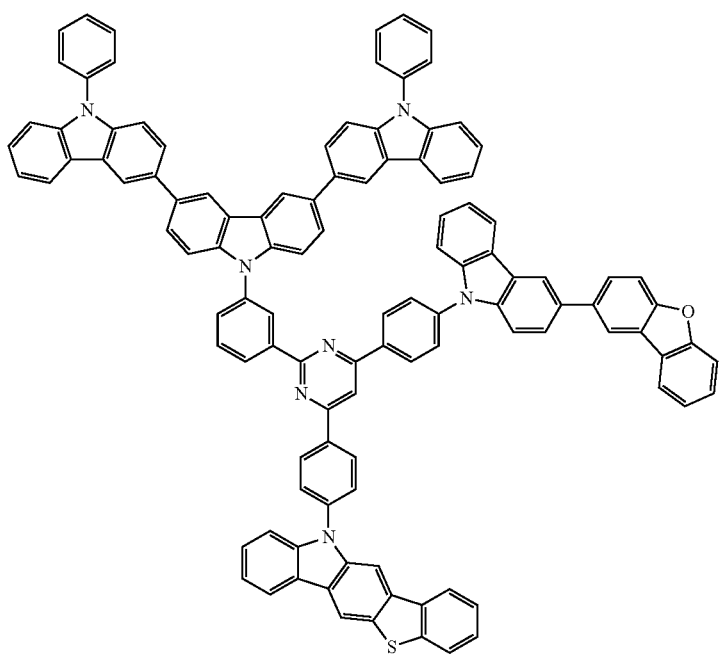
A-94

-continued
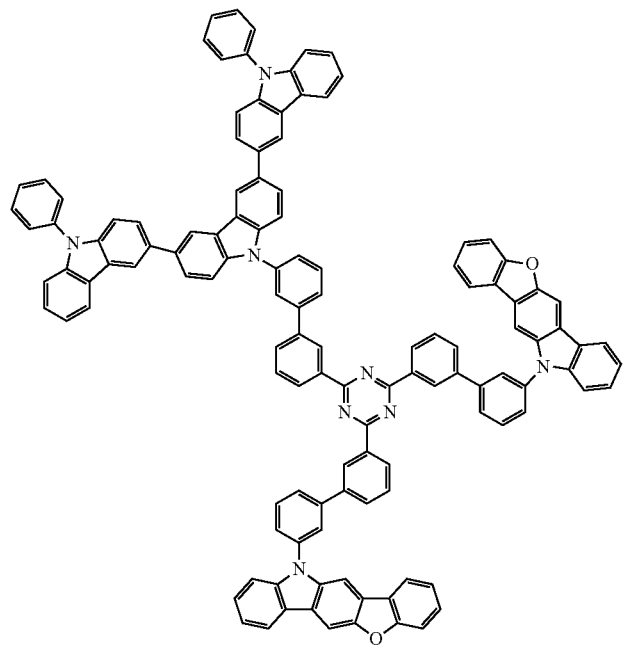
A-95
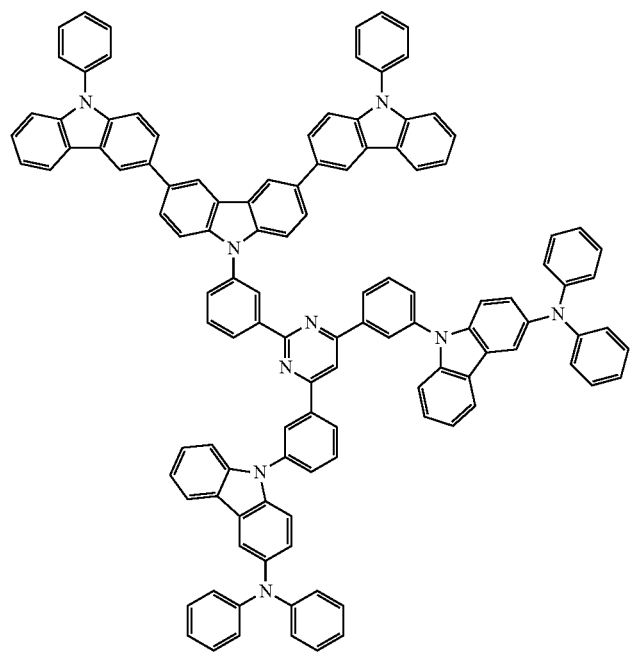
A-96

-continued
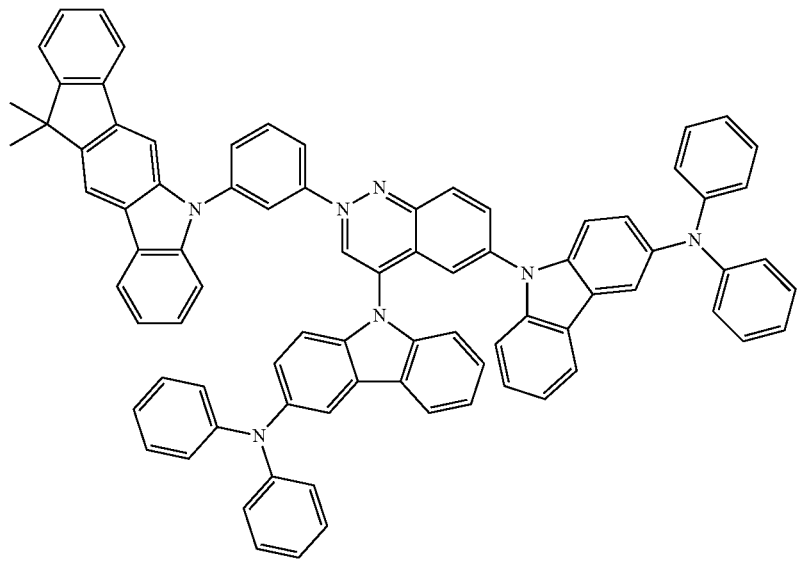
A-97
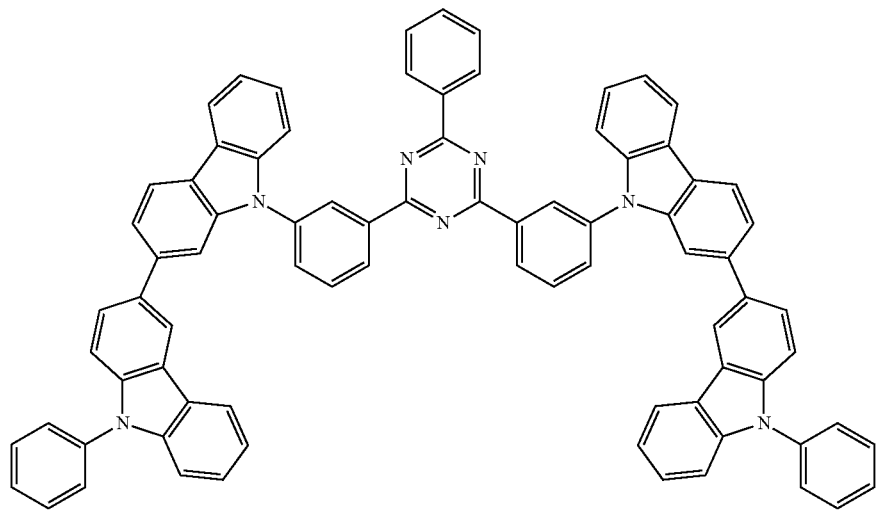
A-98

A-99

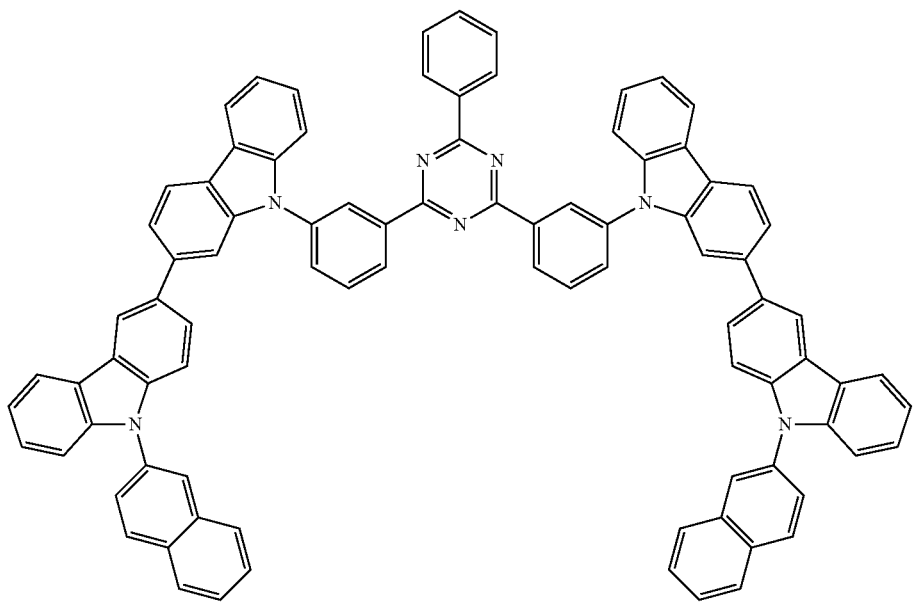

The production method of compound (CH1) is not particularly limited and compound (CH1) can be produced by a known method, for example, by Ullmann reaction or Buchwald reaction generally used in the reaction between a halogen compound and carbazole or a reaction between a halogen compound and a salt of carbazole which is formed by eliminating a hydrogen atom by a base, such as sodium hydride and potassium carbonate.

For example, the method described in WO 2012/086170 is applicable.

Compound (CH3)

Compound (CH3) will be described below. Compound (CH3) has an effect of facilitating the generation of excitons to increase the emission efficiency of organic EL devices.

In an aspect, compound (CH3) preferably comprises an electron transporting skeleton. In another aspect, compound (CH3) is preferably free from an amino group, such as a triarylamino group.

The electron transporting skeleton is a skeleton in which the electron transporting ability is dominant to the hole transporting ability, for example, a nitrogen-containing aromatic heterocyclic ring and a cyano group.

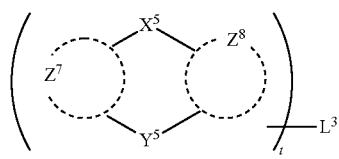

(CH3)

In formula (CH3), one of $Z^7$, $X^5$, $Y^5$, and $Z^8$ is bonded to $L^3$.

$X^5$ and $Y^5$ each represent a single bond, —CR$_2$—, —NR—, —O—, —S—, or —SiR$_2$—, provided that $X^5$ and $Y^5$ cannot all be single bonds. R is as defined above and examples thereof include those described above with respect to formula (CH2).

In view of increasing the energy gap between the excited state and the ground state, at least one of $X^5$ and $Y^5$ is preferably —NR—. To prevent the increase in the hole transporting ability, R is preferably a residue of an electron transporting skeleton, such as pyridine, pyrazine, pyrimidine, pyridazine, and triazine. The residue may have a substituent, such as a phenyl group, a biphenyl group, and a fluorenyl group. The residue of an electron transporting skeleton may be bonded to the nitrogen atom via a linking group, such as a phenylene group. A phenyl group having a phenyl substituent or a cyano substituent is also preferred as R.

$Z^7$ and $Z^8$ are the same as defined with respect to $Z^1$ and $Z^2$. However, each of $Z^7$ and $Z^8$ does not represent an alicyclic hydrocarbon group having three or more fused rings, an aliphatic heterocyclic group having three or more fused rings, an aromatic hydrocarbon ring group having three or more fused rings, or an aromatic heterocyclic group having three or more fused rings. Examples thereof include those described above with respect to formula (CH2) except for excluding, for example, an aromatic heterocyclic ring having three fused rings, such as carbazole, dibenzofuran, and dibenzothiophene.

The subscript t is an integer of 1 or more. The upper limit of t is determined depending on the structure of $L^3$ and t is preferably 1 to 4 and more preferably 1 to 3, although not limited thereto.

$L^3$ represents a single bond, a substituted or unsubstituted aromatic hydrocarbon ring group, or a substituted or unsubstituted aromatic heterocyclic group. Examples thereof include those described above with respect to the aromatic hydrocarbon ring group and the unsubstituted aromatic heterocyclic group for $L^1$ of formula (CH1). When t is 1, $L^3$ is not a single bond.

When $L^3$ represents a substituted or unsubstituted aromatic hydrocarbon ring group or a substituted or unsubstituted aromatic heterocyclic group, the substituent may be a heteroaryl group having 2 to 30, preferably 2 to 18 ring carbon atoms mentioned above which may have an aromatic hydrocarbon substituent having 6 to 20, preferably 6 to 18 ring carbon atoms. Examples of the aromatic hydrocarbon substituent include a phenyl group, a biphenyl group, a 9,9-dimethylfluorenyl group, and a phenyl group having a 9,9-dimethylfluorenyl substituent.

The compound represented by formula (CH3) is preferably a compound represented by formula (CH3-A):

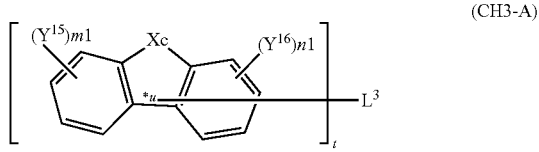

(CH3-A)

in formula (CH3-A), t and $L^3$ are as defined above in formula (3);

Xc represents —$CR_2$—, —NR—, —O—, —S—, or —$SiR_2$—, wherein R represents a single bond which is directly bonded to $L^3$ at position *u, a hydrogen atom, a substituted or unsubstituted alkyl group, a substituted or unsubstituted cycloalkyl group, a substituted or unsubstituted aromatic hydrocarbon ring group, or a substituted or unsubstituted aromatic heterocyclic group;

$Y^{15}$ and $Y^{16}$ each independently represent a single bond which is directly bonded to $L^3$ at position *u, a hydrogen atom, a fluorine atom, a cyano group, a substituted or unsubstituted alkyl group having 1 to 20 carbon atoms, a substituted or unsubstituted alkoxy group having 1 to 20 carbon atoms, a substituted or unsubstituted haloalkyl group having 1 to 20 carbon atoms, a substituted or unsubstituted haloalkoxy group having 1 to 20 carbon atoms, a substituted or unsubstituted alkylsilyl group having 1 to 20 carbon atoms, a substituted or unsubstituted arylsilyl group having 6 to 30 carbon atoms, a substituted or unsubstituted aromatic hydrocarbon ring group having 6 to 30 ring carbon atoms, a substituted or unsubstituted fused aromatic hydrocarbon ring group having 6 to 30 ring carbon atoms, a substituted or unsubstituted aromatic heterocyclic group having 2 to 30 ring carbon atoms, or a substituted or unsubstituted fused aromatic heterocyclic group having 2 to 30 ring carbon atoms;

adjacent groups $Y^{15}$ and adjacent groups $Y^{16}$ may be bonded to each other to form a linking group, provided that adjacent groups $Y^{15}$ and adjacent groups $Y^{16}$ do not form an alicyclic hydrocarbon group having two or more fused rings, an aliphatic heterocyclic group having two or more fused rings, an aromatic hydrocarbon ring group having two or more fused rings, and an aromatic heterocyclic group having two or more fused rings;

m1 is an integer of 1 to 4;

when R is a single bond which is directly bonded to $L^3$ at position *u, n1 is an integer of 1 to 3, and when R is not a single bond which is directly bonded to $L^3$ at position *u, n1 is an integer of 1 to 4; and when m1 is 2 or more, two or more groups $Y^{15}$ may be the same or different, and when n1 is 2 or more, two or more groups $Y^{16}$ may be the same or different.

The compound represented by formula (CH3-A) is preferably a compound represented by formula (CH3-A-1):

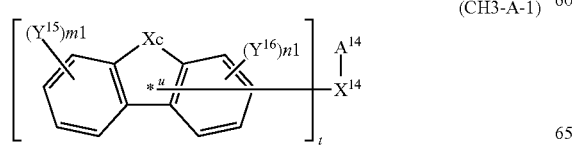

(CH3-A-1)

in formula (CH3-A-1), t, Xc, $Y^{15}$, $Y^{16}$, m1, and n1 are as defined above in formula (CH3-A);

$A^{14}$ represents a substituted or unsubstituted nitrogen-containing heterocyclic group having 1 to 30 ring carbon atoms; and $X^{14}$ represents a single bond or a residue of a ring selected from a substituted or unsubstituted aromatic hydrocarbon ring having 6 to 30 ring carbon atoms, a substituted or unsubstituted fused aromatic hydrocarbon ring having 6 to 30 ring carbon atoms, a substituted or unsubstituted aromatic heterocyclic ring having 2 to 30 ring carbon atoms, and a substituted or unsubstituted fused aromatic heterocyclic ring having 2 to 30 ring carbon atoms.

The compound represented by formula (CH3-A) is preferably a compound represented by formula (CH3-A-2):

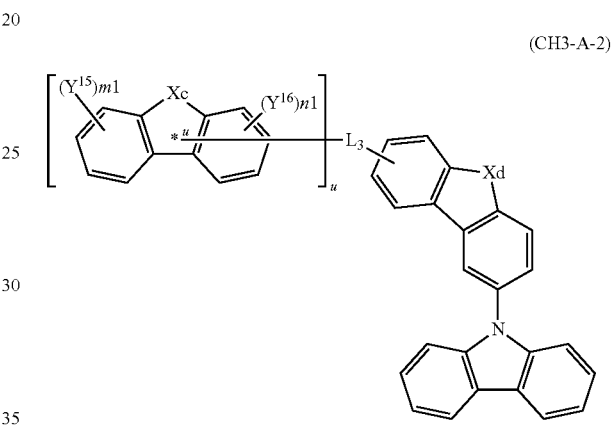

(CH3-A-2)

in formula (CH3-A-2), $L^3$, Xc, $Y^{15}$, $Y^{16}$, m1, and n1 are as defined in formula (CH3-A);

u represents an integer of 1 or more;

Xd represents —$CR_2$—, —NR—, —O—, —S—, or —$SiR_2$—; and

R represents a hydrogen atom, a substituted or unsubstituted alkyl group, a substituted or unsubstituted cycloalkyl group, a substituted or unsubstituted aromatic hydrocarbon ring group, or a substituted or unsubstituted aromatic heterocyclic group.

Also, the compound represented by formula (CH3) is preferably a compound represented by formula (CH8) or (CH9). Formula (CH8) corresponds to formula (CH3) wherein t is 2, $L^3$ is a single bond, and one of groups $X^5$ is NAr. Formula (CH9) corresponds to formula (CH3) wherein t is 2 and $X^5$ is N.

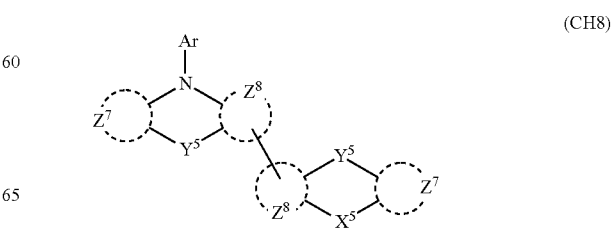

(CH8)

-continued (CH9)

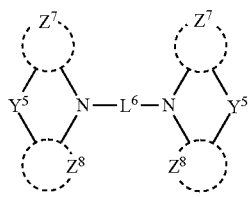

in formula (CH8) or (CH9), $X^5$, $Y^8$, $Z^7$, and $Z^8$ are as defined above in formula (CH3), examples thereof include those described above with respect to formula (CH3), and two or more groups $Y^5$, two or more groups $Z^7$, and two or more groups $Z^8$ may be the same or different, respectively;

$L^6$ represents a substituted or unsubstituted aromatic hydrocarbon ring group, a substituted or unsubstituted aromatic heterocyclic group, or a combination thereof, and examples thereof include those mentioned above with respect to the aromatic hydrocarbon ring group and the aromatic heterocyclic group of $L^1$ of formula (CH1); and Ar represents a substituted or unsubstituted alicyclic hydrocarbon group, a substituted or unsubstituted aliphatic heterocyclic group, a substituted or unsubstituted aromatic hydrocarbon ring group, or a substituted or unsubstituted aromatic heterocyclic group, and examples thereof include monovalent groups corresponding to the groups mentioned above with respect to R and $Z^1$ of formula (CH2).

Also, the compound represented by formula (CH3) is preferably a compound represented by formula (CH10) or (CH1):

(CH10)

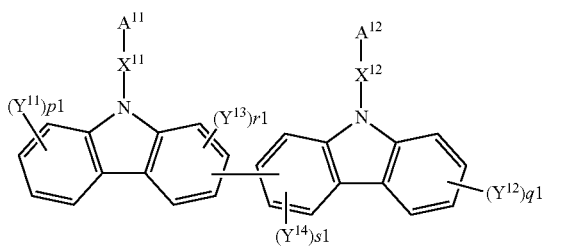

(CH11)

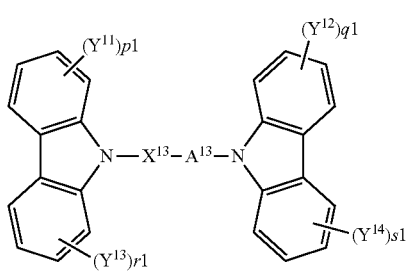

in formula (CH10) and (CH11), $A^{11}$ represents a substituted or unsubstituted nitrogen-containing heterocyclic group having 1 to 30 ring carbon atoms;

$A^{13}$ represents a substituted or unsubstituted nitrogen-containing divalent heterocyclic group having 1 to 30 ring carbon atoms or a substituted or unsubstituted oxygen-containing divalent heterocyclic group having 2 to 30 ring carbon atoms;

$A^{12}$ represents a substituted or unsubstituted aromatic hydrocarbon ring group having 6 to 30 ring carbon atoms or a substituted or unsubstituted nitrogen-containing heterocyclic group having 2 to 30 ring carbon atoms;

$X^{11}$, $X^{12}$ and $X^{13}$ each represents a linking group and each independently represent a single bond, a substituted or unsubstituted divalent aromatic hydrocarbon ring group having 6 to 30 ring carbon atoms, a substituted or unsubstituted divalent fused aromatic hydrocarbon ring group having 6 to 30 ring carbon atoms, a substituted or unsubstituted divalent aromatic heterocyclic group having 2 to 30 ring carbon atoms, or a substituted or unsubstituted divalent fused aromatic heterocyclic group having 2 to 30 ring carbon atoms;

$X^{13}$ of formula (11) preferably represents a substituted or unsubstituted divalent aromatic hydrocarbon ring group having 6 to 30 ring carbon atoms;

$Y^{11}$ to $Y^{14}$ each independently represent a hydrogen atom, a fluorine atom, a cyano group, a substituted or unsubstituted alkyl group having 1 to 20 carbon atoms, a substituted or unsubstituted alkoxy group having 1 to 20 carbon atoms, a substituted or unsubstituted haloalkyl group having 1 to 20 carbon atoms, a substituted or unsubstituted haloalkoxy group having 1 to 20 carbon atoms, a substituted or unsubstituted alkylsilyl group having 1 to 20 carbon atoms, a substituted or unsubstituted arylsilyl group having 6 to 30 carbon atoms, a substituted or unsubstituted aromatic hydrocarbon ring group having 6 to 30 ring carbon atoms, a substituted or unsubstituted fused aromatic hydrocarbon ring group having 6 to 30 ring carbon atoms, a substituted or unsubstituted aromatic heterocyclic group having 2 to 30 ring carbon atoms, or a substituted or unsubstituted fused aromatic heterocyclic group having 2 to 30 ring carbon atoms;

adjacent groups of $Y^{11}$ to $Y^{14}$ may be bonded to each other to form a linking group;

p1 and q1 are each an integer of 1 to 4 and r1 and s1 are each an integer of 1 to 3; and two or more groups $Y^{11}$ to $Y^{14}$ when p1, q1, r1, and s1 are each 2 or more may be the same or different, respectively.

Examples of the aromatic hydrocarbon ring group for $A^{12}$ include those mentioned above with respect to R and $Z^1$ of formula (CH2).

Examples of the nitrogen-containing heterocyclic group for $A^{11}$ and $A^{12}$ include monovalent residues of pyrrole, pyridine, pyrazine, pyridine, pyrimidine, pyridazine, triazine, indole, isoindole, indazole, purine, pteridine, β-carboline, naphthyridine, quinoline, isoquinoline, quinoxaline, quinazoline, aziridine, azaindolizine, indolizine, acridine, pyrrolidine, piperidine, morpholine, piperazine, carbazole, phenanthridine, phenanthroline, oxazole, oxadiazole, benzoxazole, thiazole, thiadiazole, benzothiazole, triazole, imidazole, benzimidazole, azafluorene, azacarbazole, a benzene-fused analogue thereof, and a crosslinked analogue thereof.

Of the above, preferred are pyridine, pyrazine, pyrimidine, pyridazine, triazine, quinoline, isoquinoline, quinoxaline, quinazoline, aziridine, azaindolizine, indolizine, imidazole, indole, isoindole, indazole, purine, pteridine, β-carboline, and naphthyridine; more preferred are pyridine, pyrimidine, triazine, quinoline, isoquinoline, quinoxaline, and quinazoline; and particularly preferred are pyrimidine and triazine.

Examples and preferred examples of the divalent nitrogen-containing heterocyclic group for $A^{13}$ include divalent residues of the nitrogen-containing heterocyclic group mentioned above with respect to $A^{11}$ and $A^{12}$. Examples and preferred examples of the oxygen-containing divalent heterocyclic group for $A^{13}$ include a dibenzofuranylene group.

Examples of the aromatic hydrocarbon ring group and the fused aromatic hydrocarbon ring group for $X^{11}$, $X^{12}$ and $X^{13}$ include divalent residues corresponding to those exemplified as the aromatic hydrocarbon ring group for R and $Z^1$ of formula (CH2). Examples of the aromatic heterocyclic group and the fused aromatic heterocyclic group for $X^{11}$, $X^{12}$ and $X^{13}$ include divalent residues corresponding to those exemplified as the aromatic heterocyclic group for R and $Z^1$ of formula (CH2). Preferred examples of $X^{11}$ and $X^{12}$ include a m-phenylene group, a p-phenylene group, a 4,4'-biphenylene group, a 4,3'-biphenylene group, a 1,4-naphthylene group, and a 2,6-naphthylene group.

Examples of the alkyl group for $Y^{11}$ to $Y^{14}$ include those mentioned above in formula (CH2). Examples of the alkoxy group and the thioalkoxy group include those wherein the alkyl groups mentioned above are bonded to an oxygen atom or a sulfur atom. Examples of the haloalkyl group and the haloalkoxy group include those derived from the above alkyl groups and the above alkoxy groups by replacing a hydrogen atom with a halogen atom. Examples of the alkylsilyl group include a trimethylsilyl group, a triethylsilyl group, a tributylsilyl group, a dimethylethylsilyl group, a dimethylisopropylsilyl group, a dimethylpropylsilyl group, a dimethylbutylsilyl group, a dimethyl-t-butylsilyl group, and a diethylisopropylsilyl group. Examples of the arylsilyl group include a phenyldimethylsilyl group, a diphenylmethylsilyl group, a diphenyl-t-butylsilyl group, and a triphenylsilyl group.

Examples of the aromatic hydrocarbon ring group and the fuse aromatic hydrocarbon ring group represented by $Y^{11}$ to $Y^{14}$ include those exemplified as the aromatic hydrocarbon ring group for R and $Z^1$ of formula (CH2). Examples of the aromatic heterocyclic group and the fused aromatic heterocyclic group for $X^{11}$ and $X^{12}$ include those exemplified as the aromatic heterocyclic group for R and $Z^1$ of formula (CH2).

The compound of formula (CH10) is preferably represented by any of formulae (CH10-1) to (CH10-4):

(10-1)

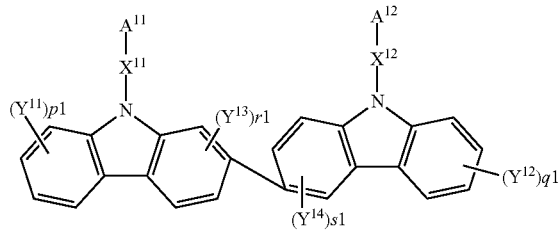

(10-2)

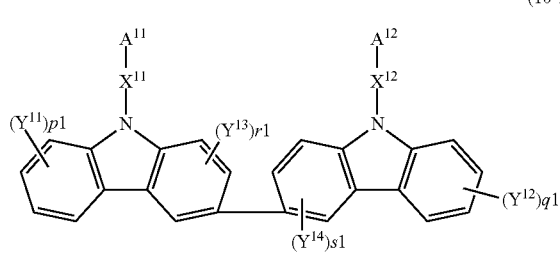

(10-3)

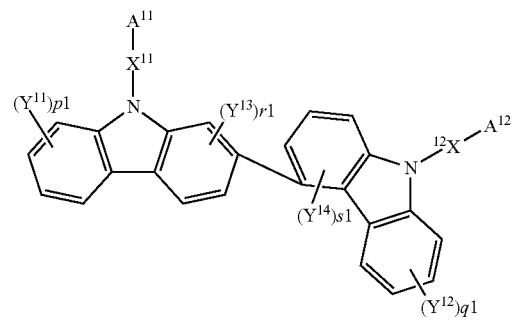

(10-4)

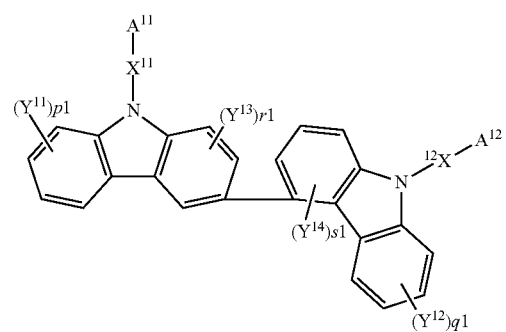

Examples of the compound of formula (CH3) are shown below, although not limited thereto.

B-1

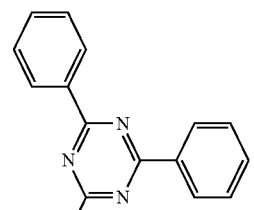
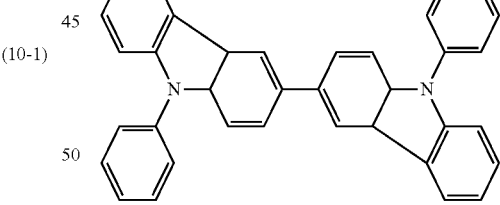

B-2

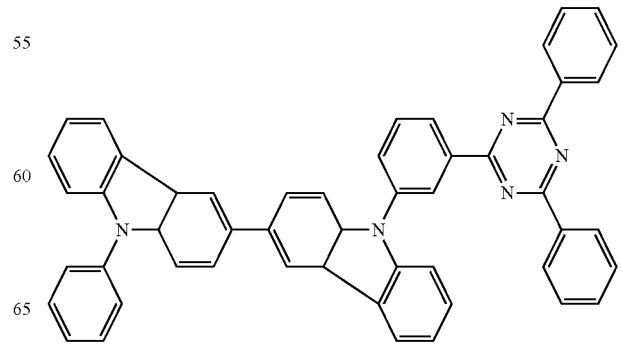

B-3
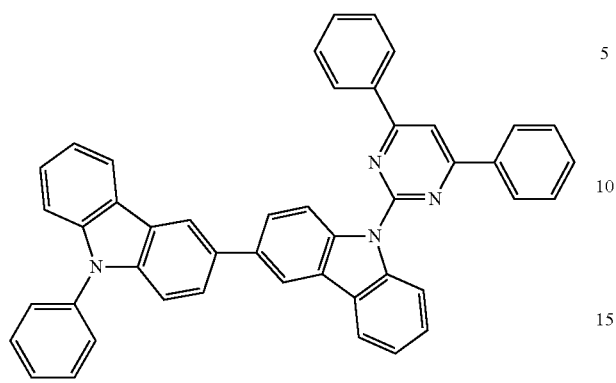
B-4
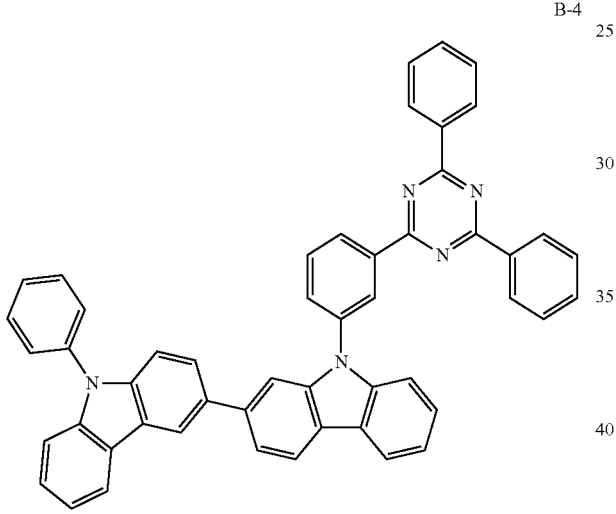
B-5
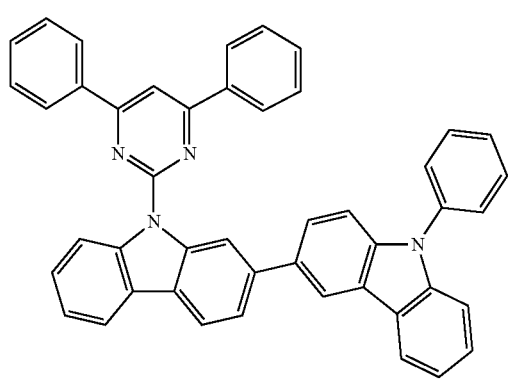
B-6
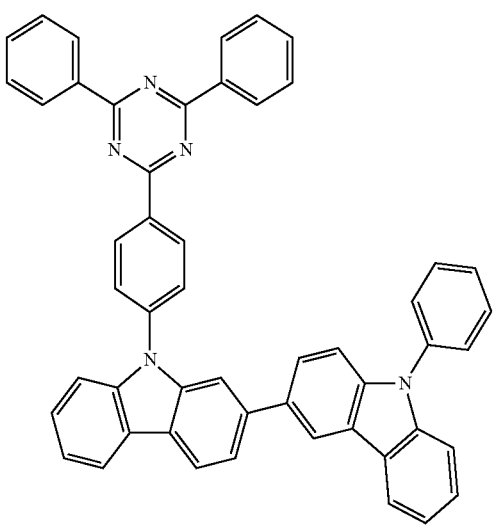
B-7
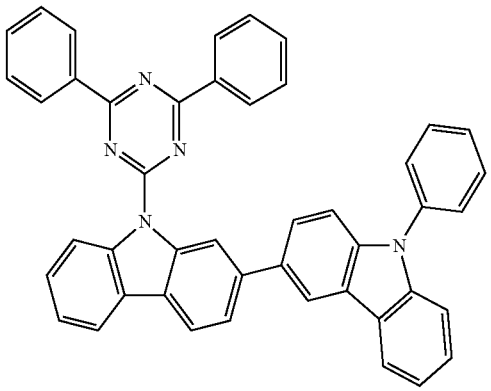
B-8
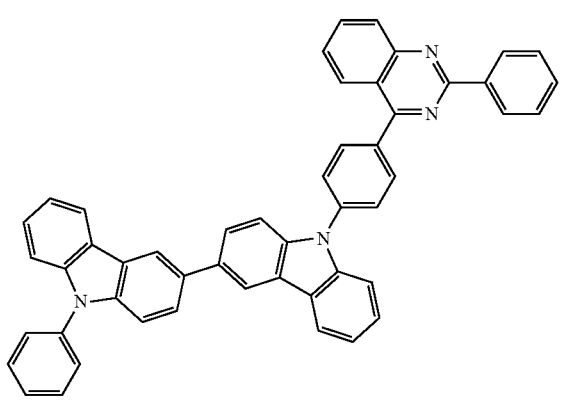

B-9
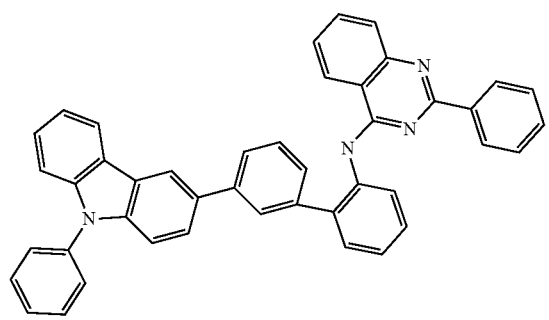
B-10
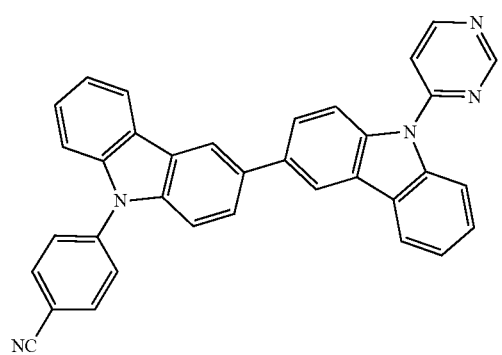
B-11
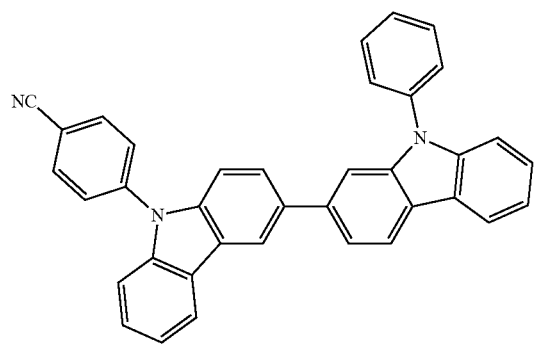
B-12
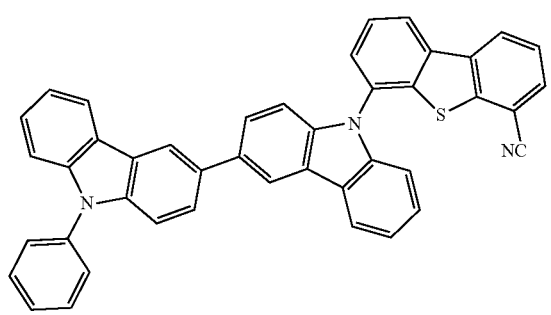
B-13
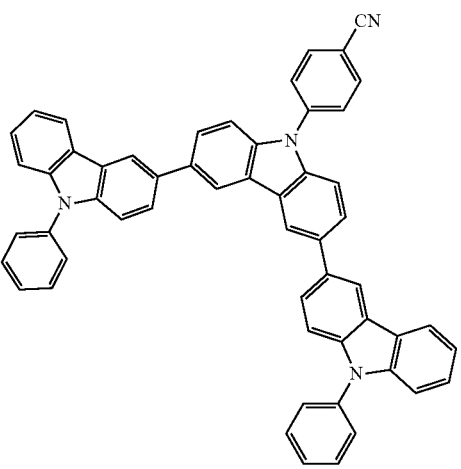
B-14
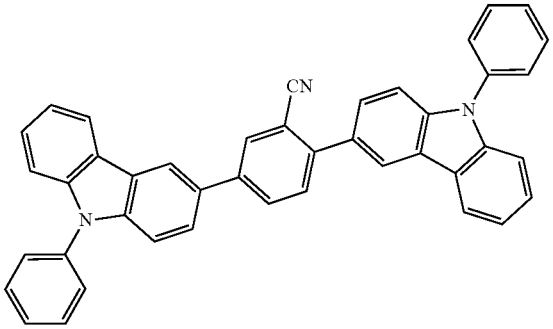
B-15
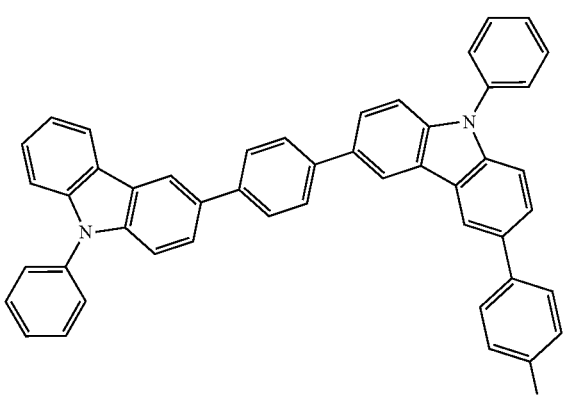

B-16
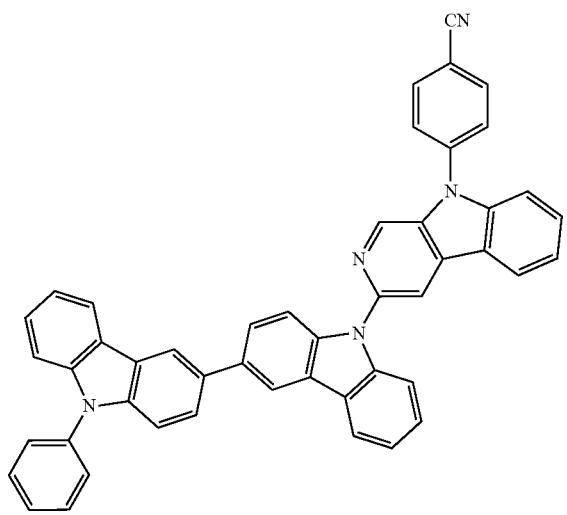
B-19
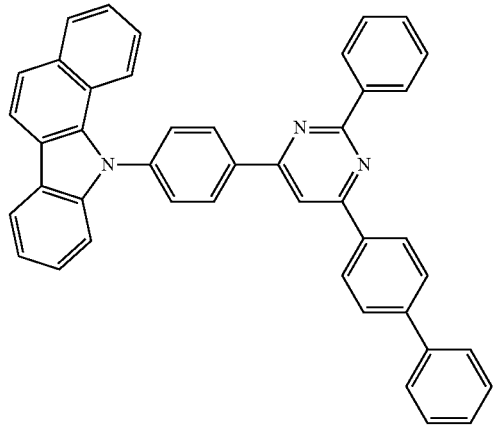
B-17
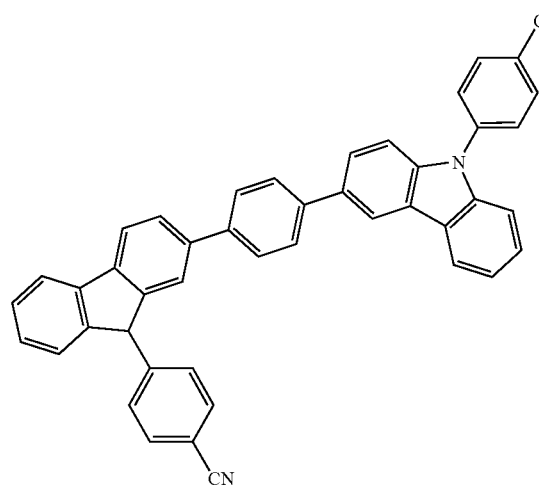
B-20
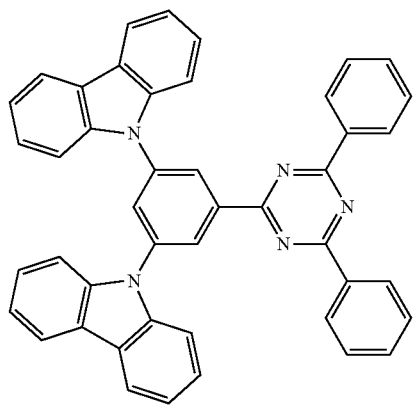
B-18
B-21
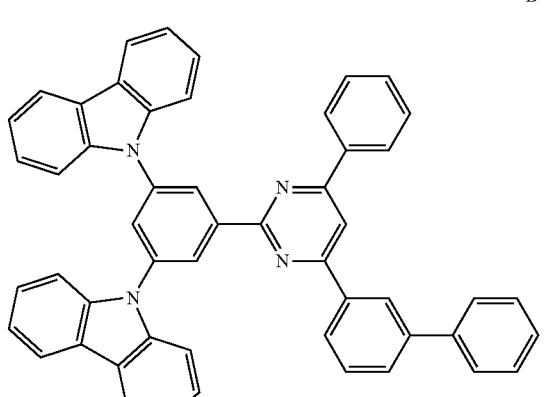

B-22
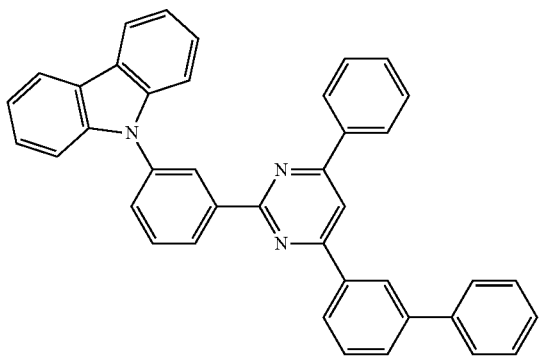
B-23
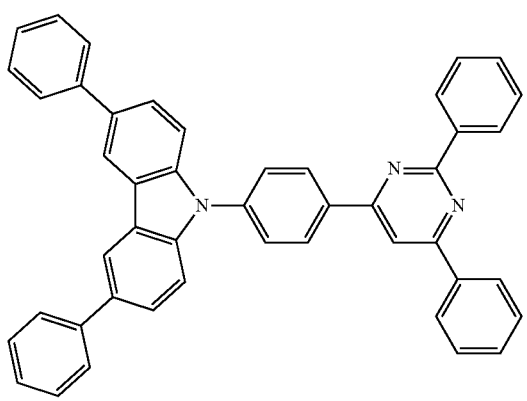
B-24
B-25
B-26
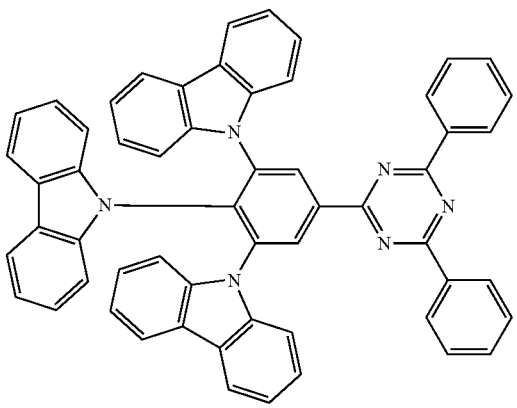
B-27
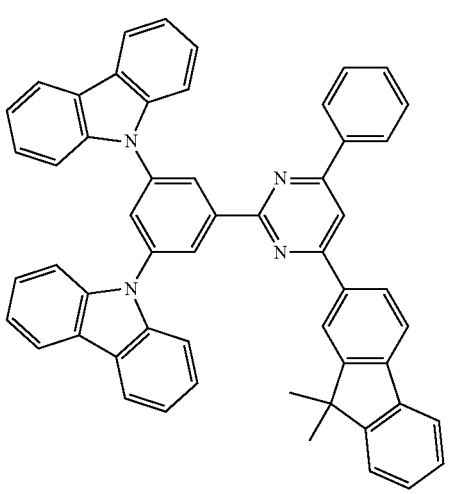
B-28
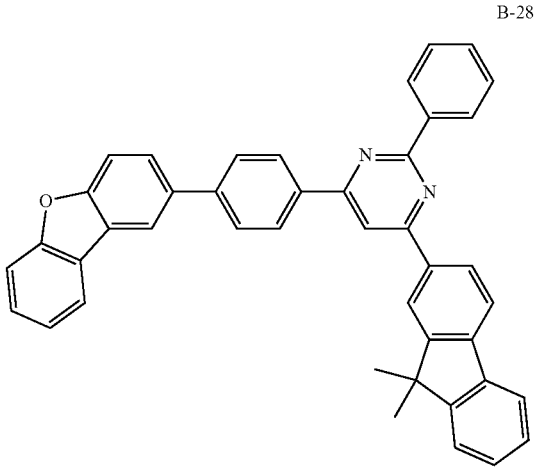

B-29
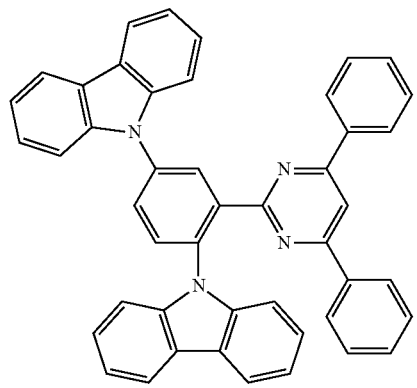
B-32
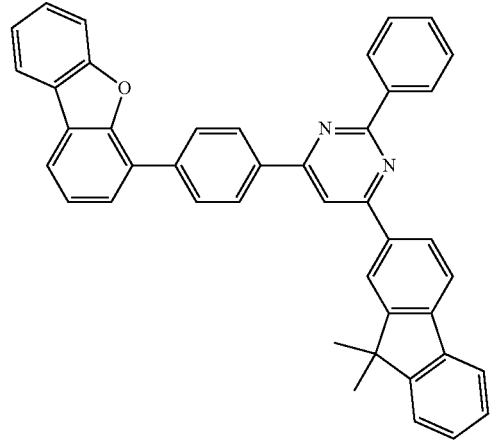
B-30
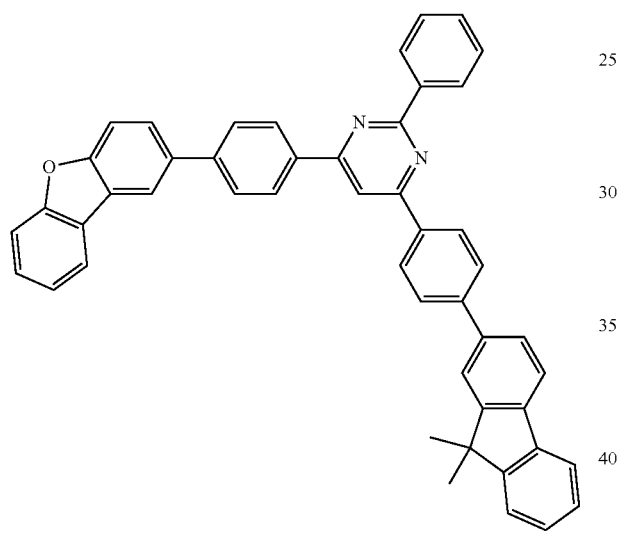
B-31
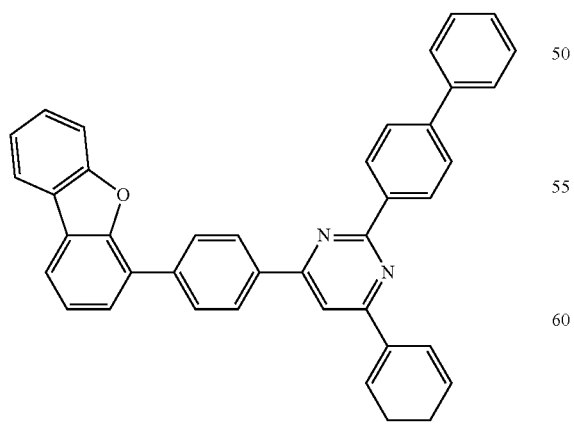
B-33
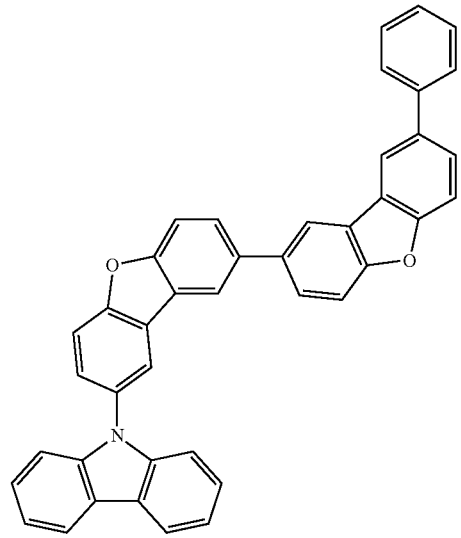

2123
-continued
B-34
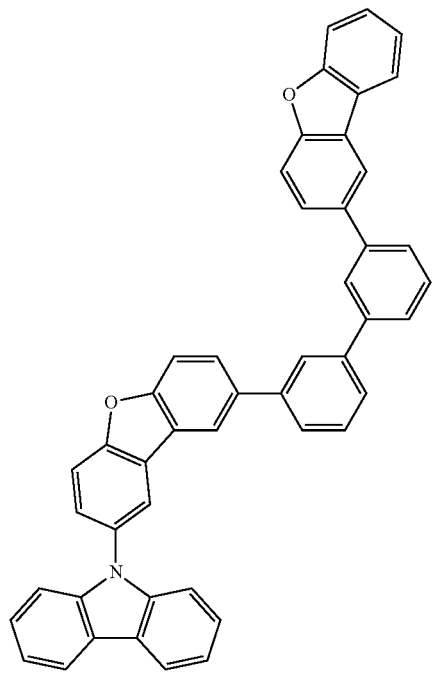
B-35
2124
-continued
B-36
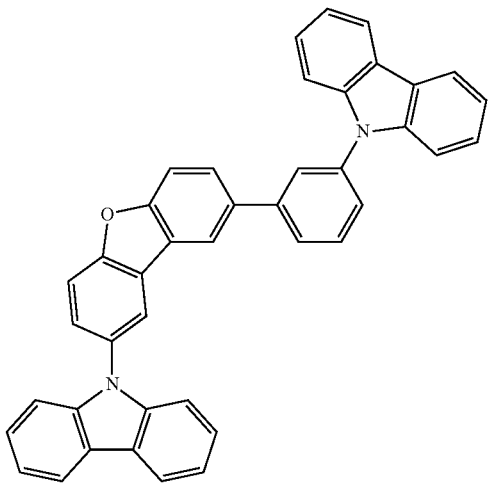
B-37
B-38

B-39
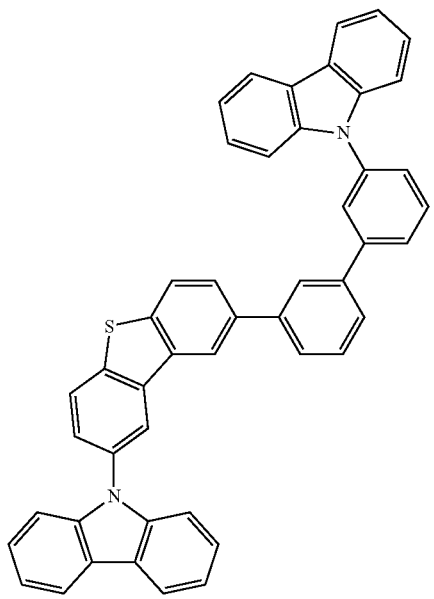
B-42
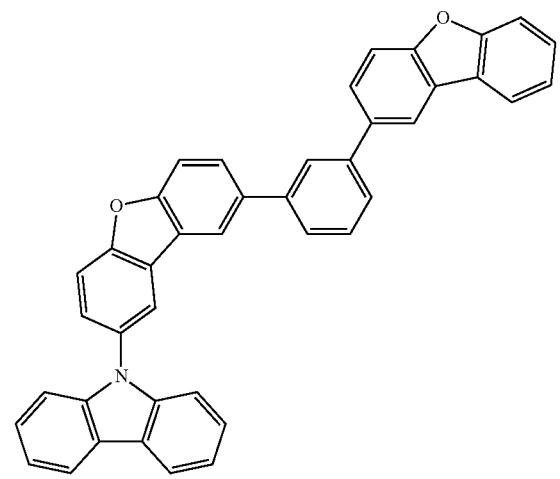
B-40
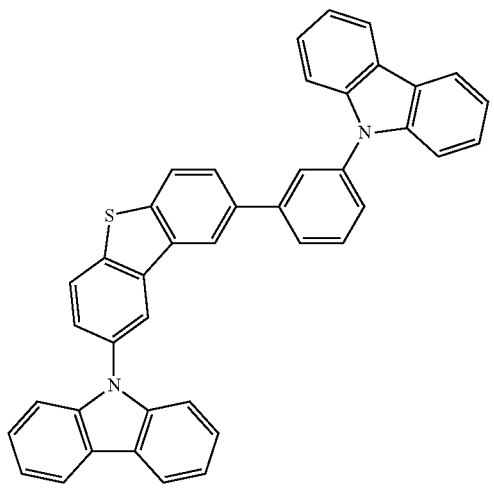
B-43
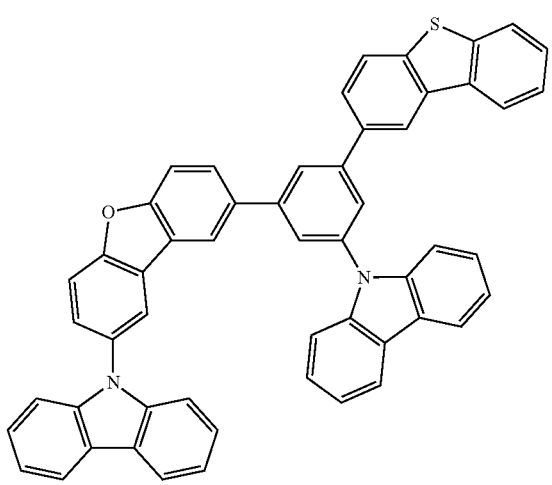
B-41
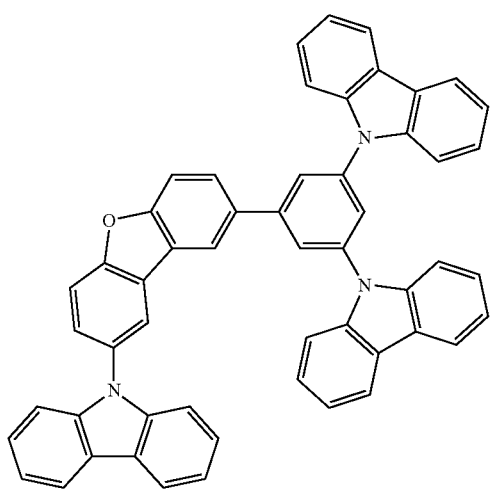
B-44
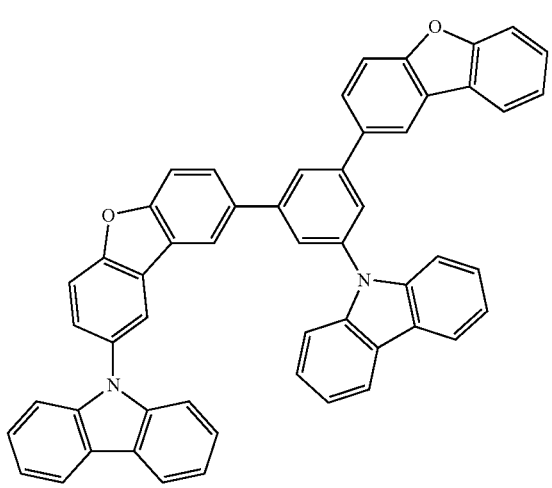

B-45
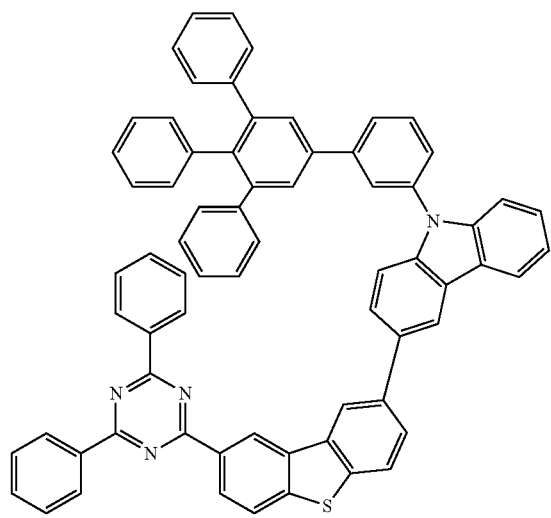
B-46
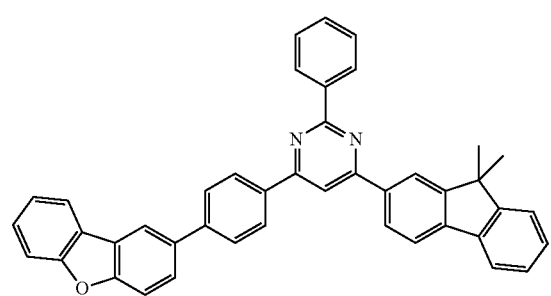
B-47
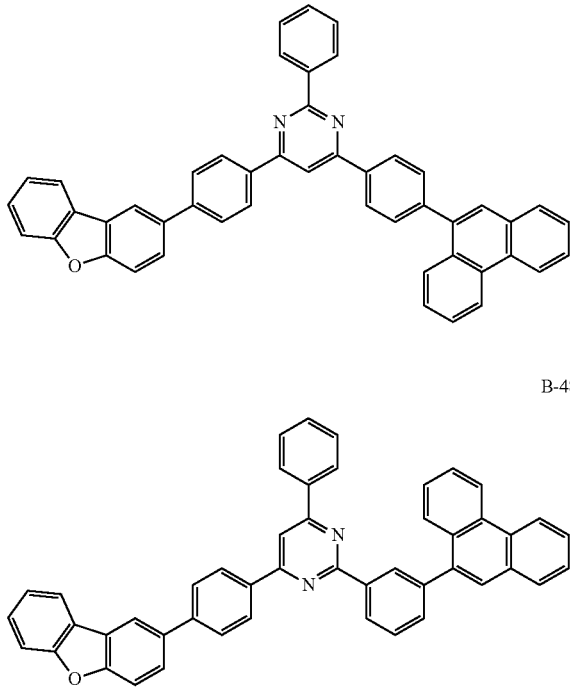
B-48
B-49
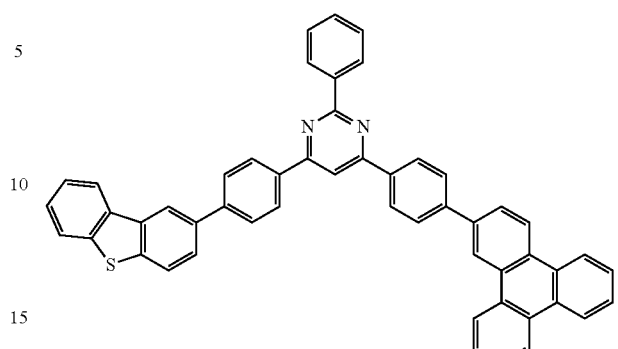
B-50
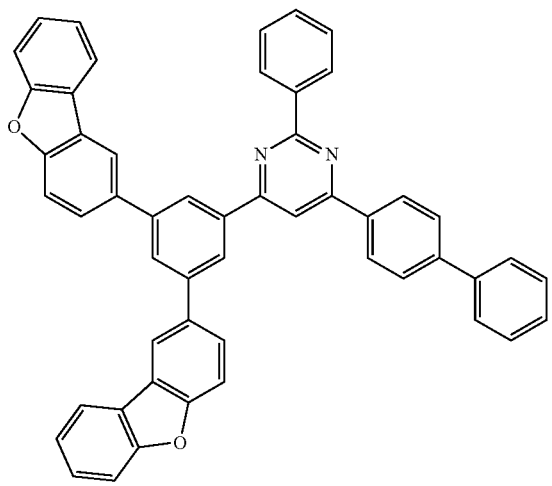
B-51
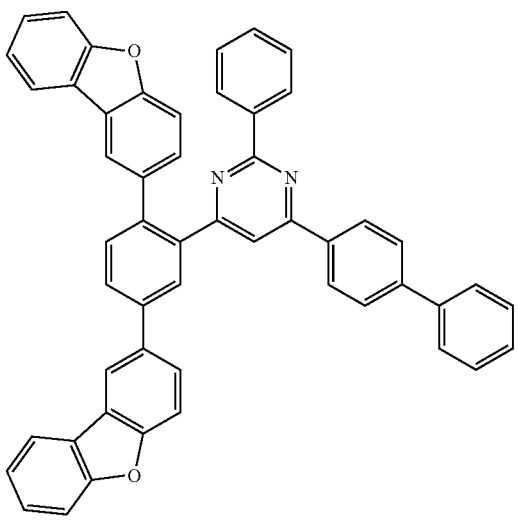

B-52
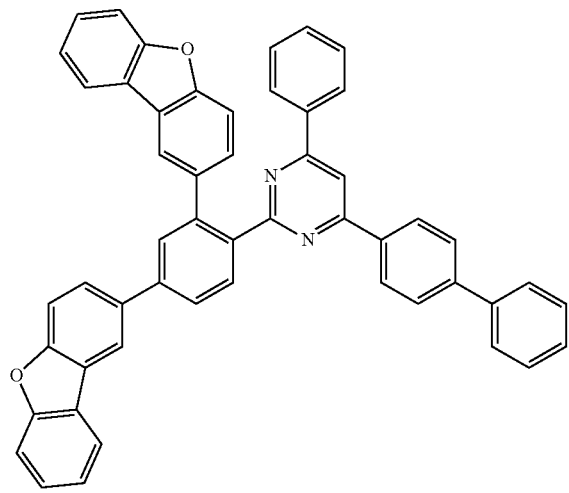
B-55
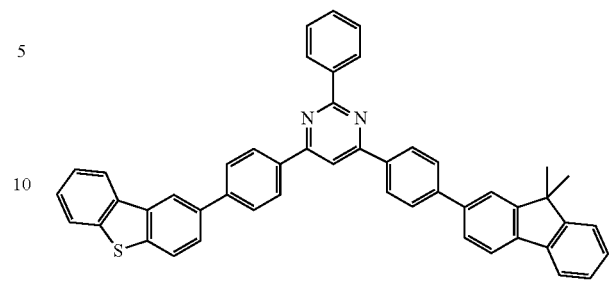
B-53
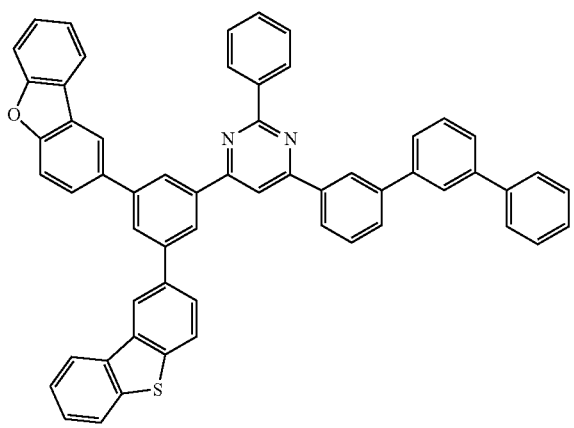
B-56
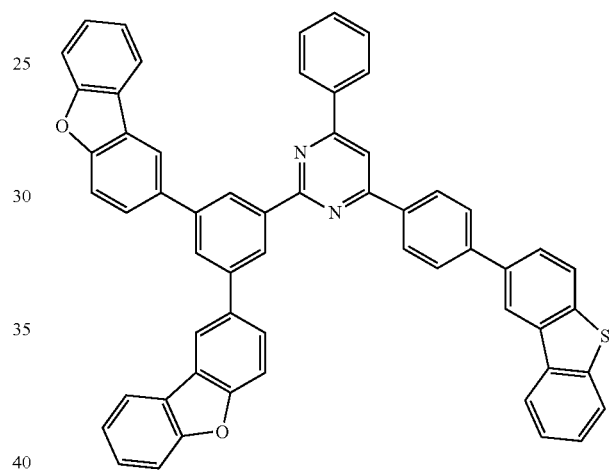
B-54
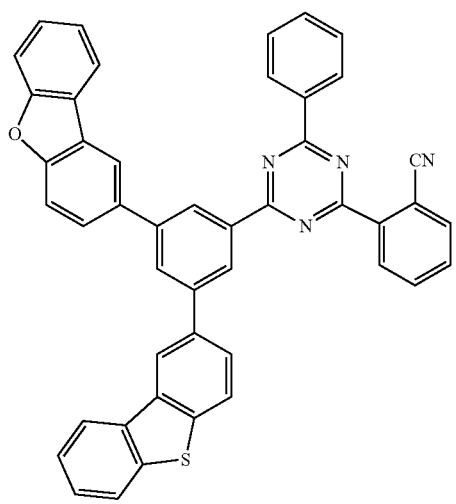
B-57
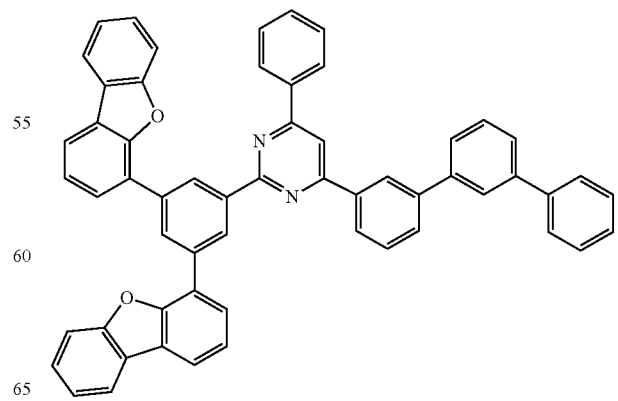

B-58
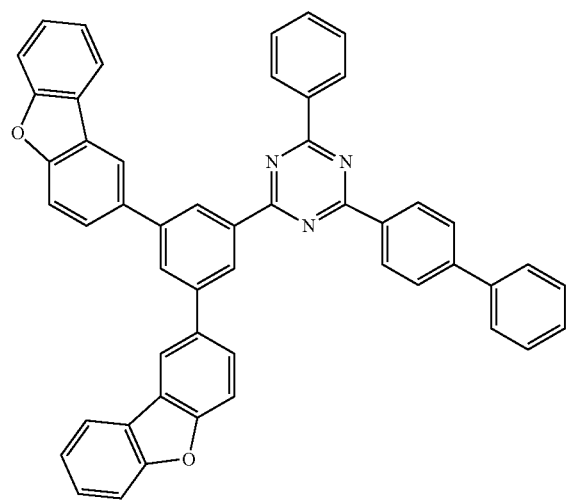
B-60
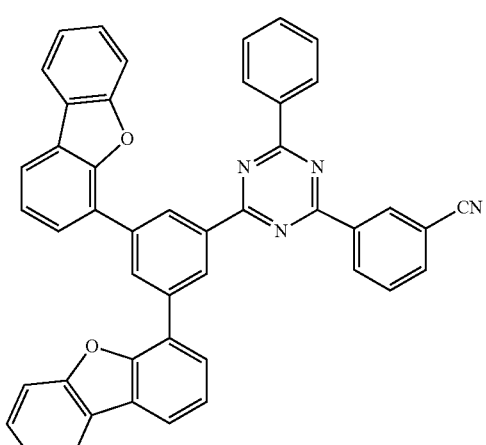
B-59
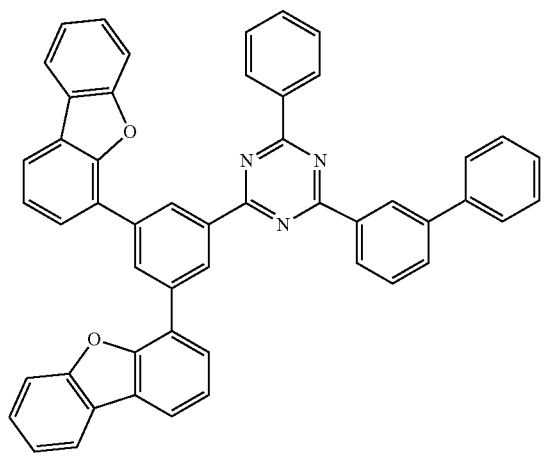
B-61
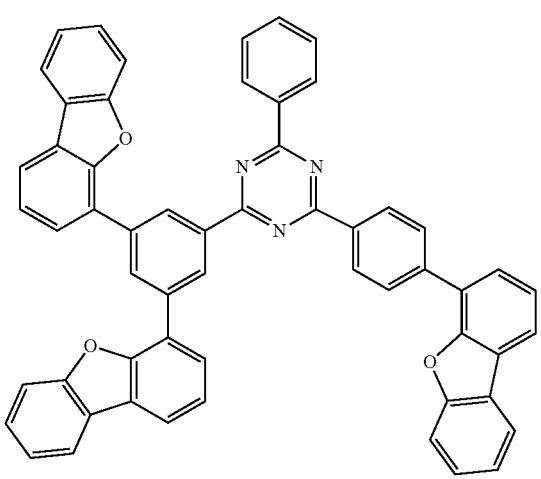
B-59
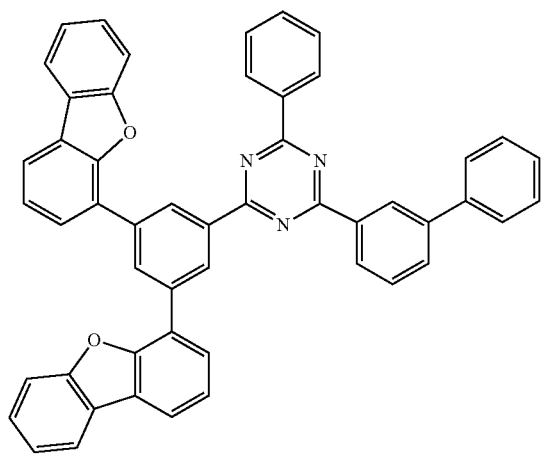
B-62
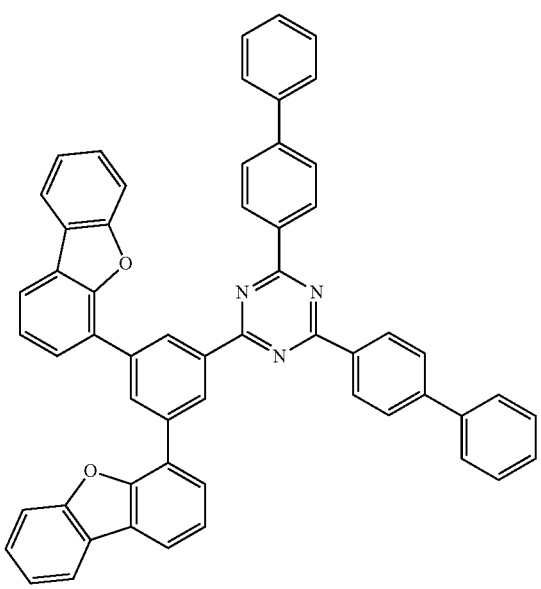

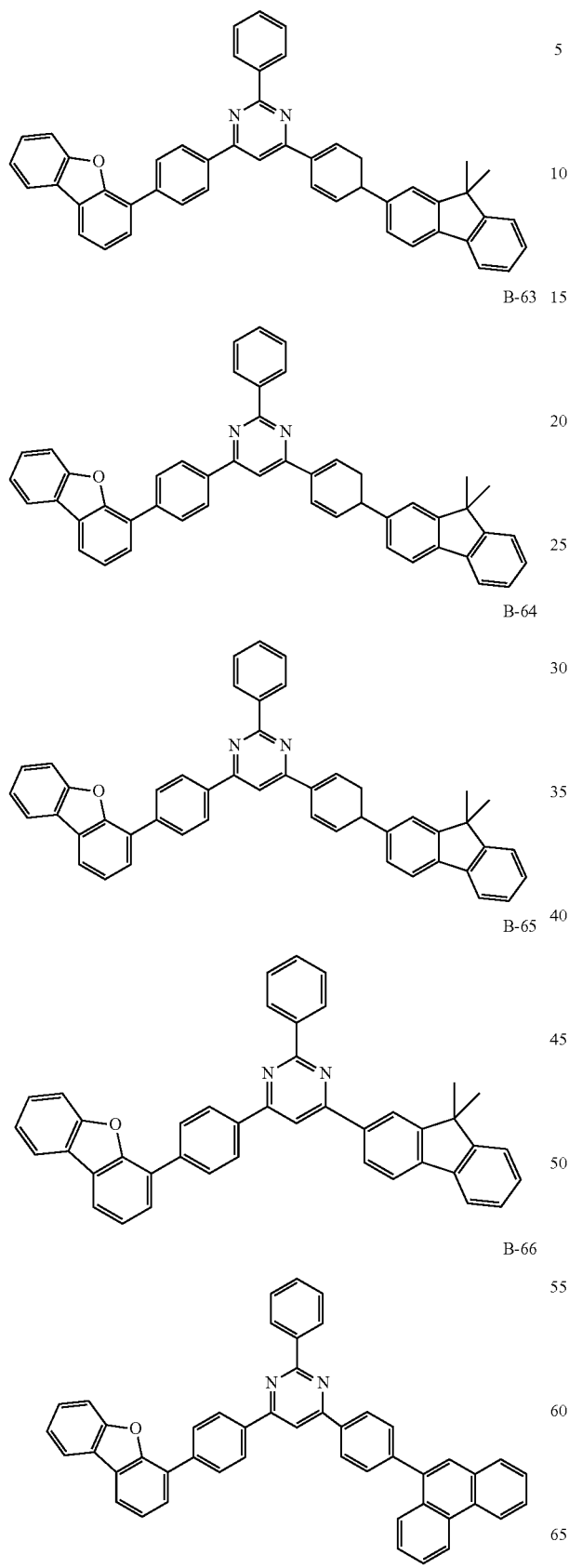
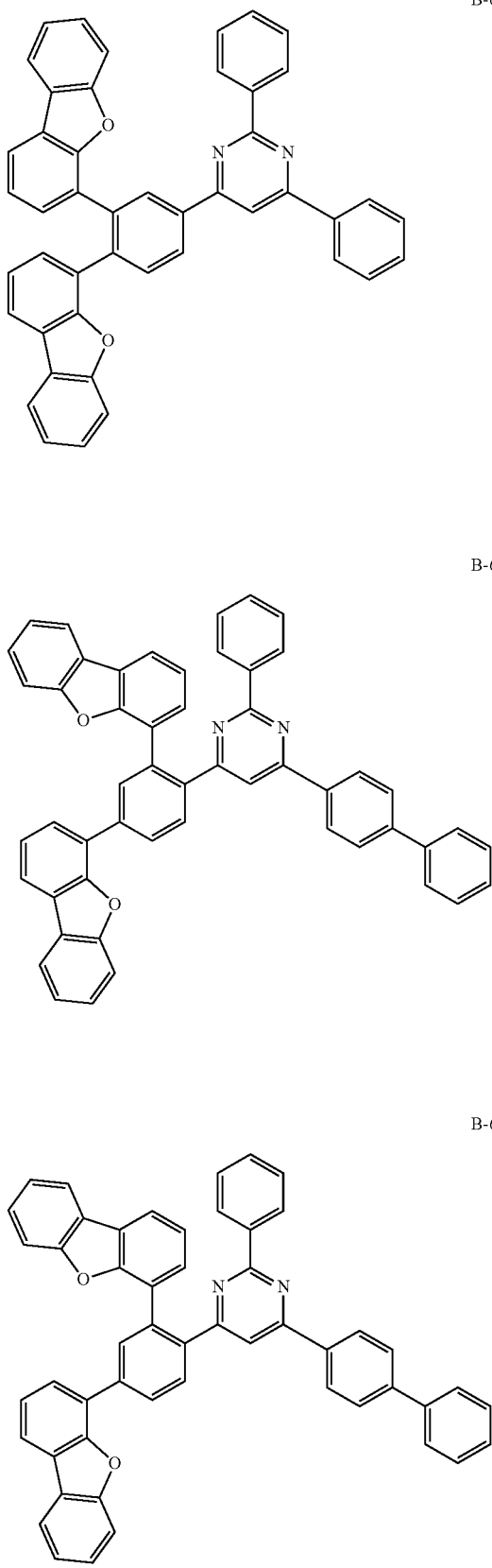

B-69
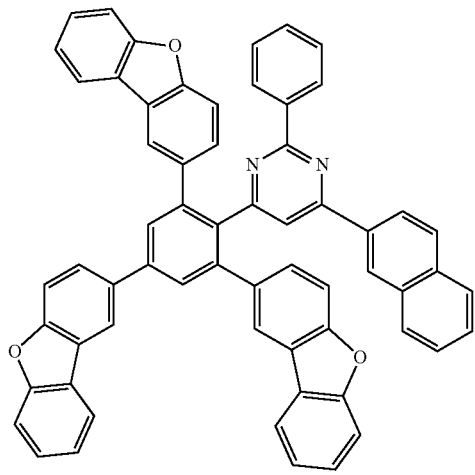
B-70
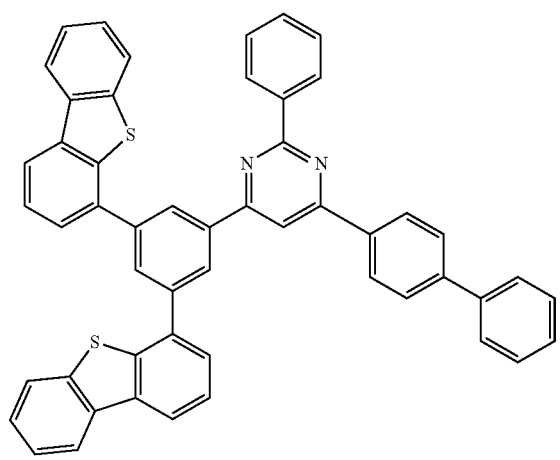
B-71
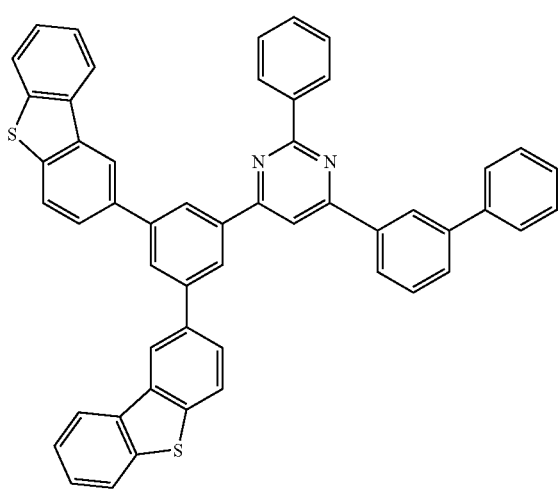
B-72
B-72
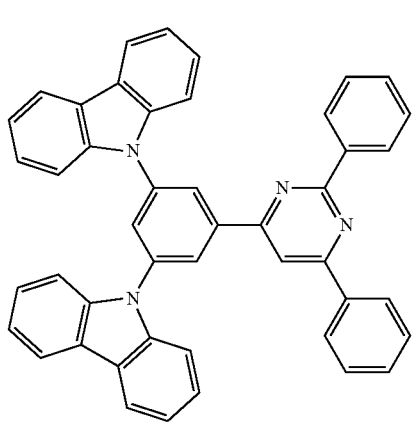
B-73
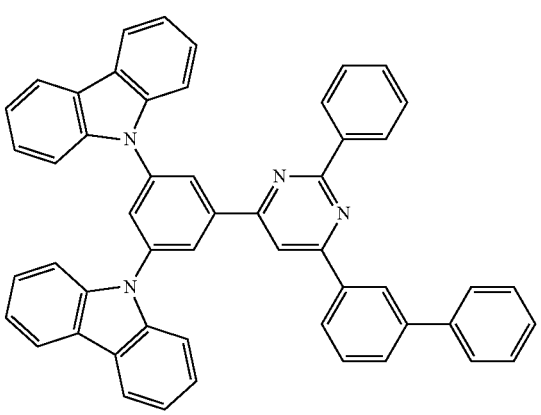

-continued

B-74

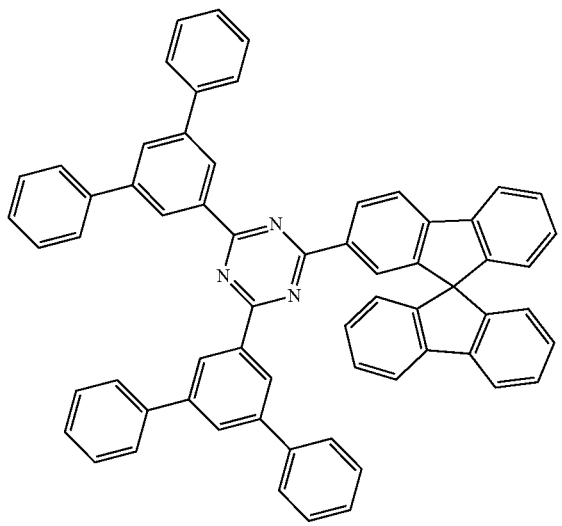

A polymer comprising a unit corresponding to formula (CH3) may be also usable as compound (CH3). However, a low molecular compound is preferred, because the balance between the structure contributing to hole transport and the structure contributing to electron transport can be finely controlled.

The compound represented by formula (3) is also preferably a compound represented by formula (CH12) or (CH13):

(CH12)

(CH13)

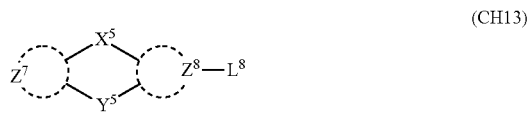

in formulae (CH12) and (CH13), $X^5$, $Y^5$, $Z^7$, and $Z^8$ are as defined above in formula (CH3) and examples thereof include those mentioned above with respect to formula (CH2); and $L^7$ and $L^8$ each represent a substituted or unsubstituted aliphatic hydrocarbon group, a substituted or unsubstituted aliphatic heterocyclic group, a substituted or unsubstituted aromatic hydrocarbon group, or a substituted or unsubstituted aromatic heterocyclic group, and examples thereof include those mentioned above with respect to R and $Z^1$ of formula (CH2).

The compound of formula (CH3) can be produced by the same method as described above with respect to the production of the compound of formula (CH1). In addition, it can be produced by a coupling reaction, for example, a coupling reaction of a carbazole compound and a halogenated aromatic compound in the presence of a copper catalyst described in Tetrahedron, 40 (1984), 1433 to 1456 or Journal of the American Chemical Society, 123(2001), 7727 to 7729.

Compounds (CH4) to (CH6) will be explained below. These compounds are characterized by an arylamino group and a carbazolyl group in their chemical structures. In an organic EL device produced by forming the composition of the invention into a film by a coating method (one of the embodiments for using the composition), it is advantageous in some cases to localize the emission region in the light emitting layer at a distance from the hole transporting layer. In this case, a compound having a group contributing to hole transport is effective and a composition comprising a compound represented by any of formulae (CH4) to (CH6) is preferably used.

Compound (CH4)

The compound of formula (CH4) will be described below.

(CH4)

I formula (CH4), $A^1$ to $A^3$ each represent a substituted or unsubstituted aromatic hydrocarbon ring group or a substituted or unsubstituted aromatic heterocyclic group and preferably a substituted or unsubstituted aromatic hydrocarbon ring group having 6 to 30 ring carbon atoms. Examples thereof include monovalent residues mentioned above with respect to $Z^1$ and $Z^2$ in formula (CH2), and preferably a phenyl group, a biphenyl group, a terphenyl group, a quaterphenyl group, a naphthyl group, a phenanthryl group, and fluorenyl group, each optionally having a substituent. Examples of the substituent include those mentioned above with respect to formula (CH1), with a heteroaryl group having 2 to 30 ring carbon atoms being preferred and a heteroaryl group having 2 to 18 ring carbon atoms being more preferred. Such a substituent includes a carbazolyl group and a dibenzofuranyl group.

Compound (CH5)

The compound of formula (CH5) will be described below.

(CH5)

In formula (CH5), $L^4$ represents a substituted or unsubstituted divalent group wherein 1 to 4 aromatic hydrocarbon rings are bonded to each other or included or a substituted or unsubstituted divalent group wherein 1 to 4 aromatic heterocyclic rings are bonded to each other. $L^4$ may comprise an aromatic hydrocarbon ring and an aromatic heterocyclic ring combinedly. $A^4$ to $A^6$ each represent a substituted or unsubstituted aromatic hydrocarbon group or a substituted or unsubstituted aromatic heterocyclic group. $A^4$ and $A^5$ may be bonded to each other to form a ring structure.

Examples of $L^4$ include those wherein the aromatic hydrocarbon ring groups and the aromatic heterocyclic groups mentioned above with respect to $Z^1$ and $Z^2$ of formula (CH2) are linked together, such as divalent residues of benzene, naphthalene, biphenyl, terphenyl, fluorene, phenanthrene, triphenylene, binaphthalene, bianthracene, perylene, chrysene, fluoranthene, benzofluorene, benzotriphenylene, benzochrysene, anthracene, pyrrole, pyridine, pyrazine, pyridine, pyrimidine, pyridazine, triazine, indole, isoindole, quinoline, isoquinoline, quinoxaline, acridine, pyrrolidine, dioxane, piperidine, morpholine, piperazine, carbazole, phenanthridine, phenanthroline, furan, benzofuran, isobenzofuran, thiophene, oxazole, oxadiazole, benzoxazole, thiazole, thiadiazole, benzothiazole, triazole, imidazole, benzimidazole, pyran, dibenzofuran, dibenzothiophene, azafluorene, biazacarbazole, benzene-fused analogues thereof, and cross-linked analogues thereof. Preferred are a phenylene group, a biphenylene group, and a fluorenylene group.

Examples of $A^4$ to $A^6$ include monovalent residues mentioned above with respect to $Z^1$ and $Z^2$ of formula (CH2). Preferred are those mentioned above with respect to $A^1$ to $A^3$ of formula (CH4).

Examples of compound (CH4) and compound (CH5) are shown below, although not limited thereto.

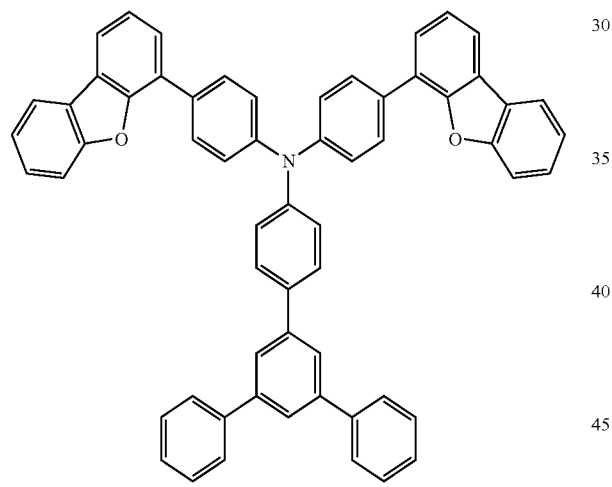

C-101

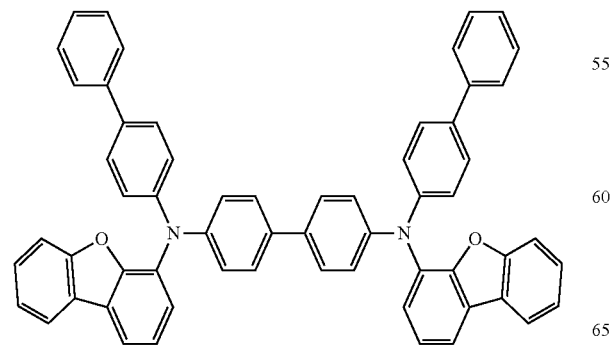

C-102

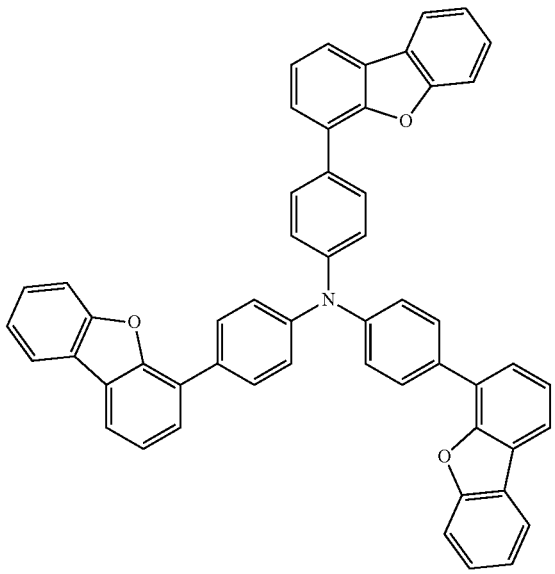

C-103

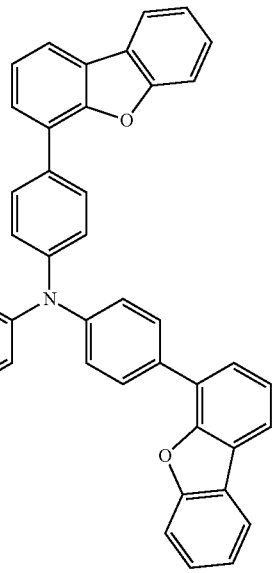

C-104

C-105
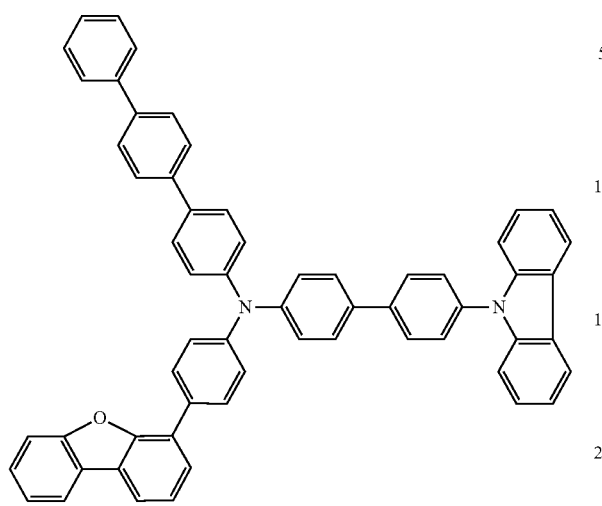
C-106
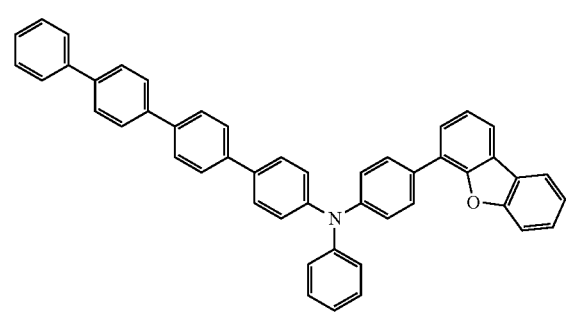
C-107
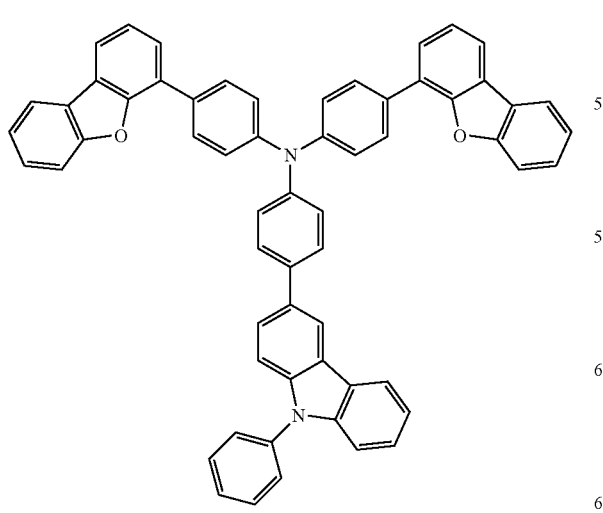
C-108
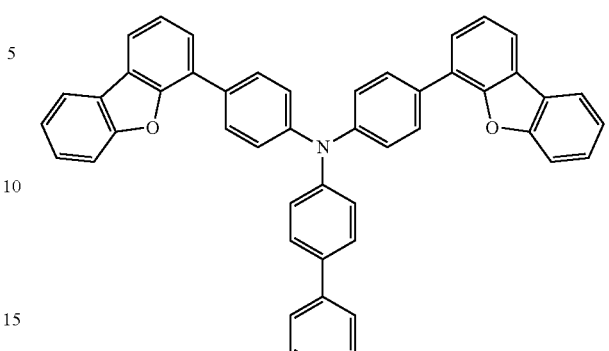
C-109
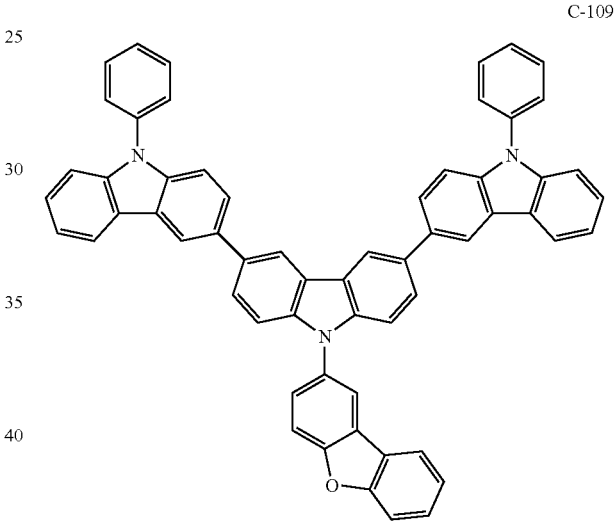
C-110
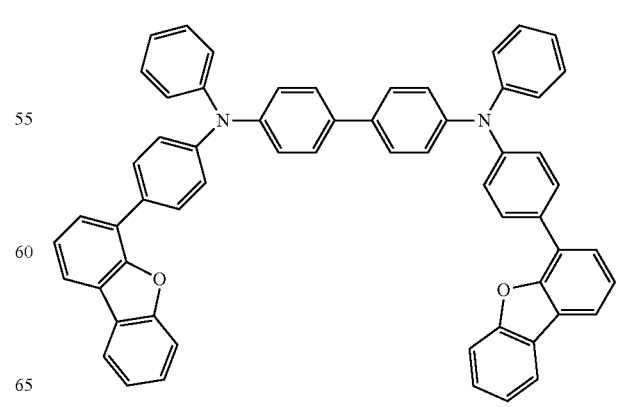

C-111
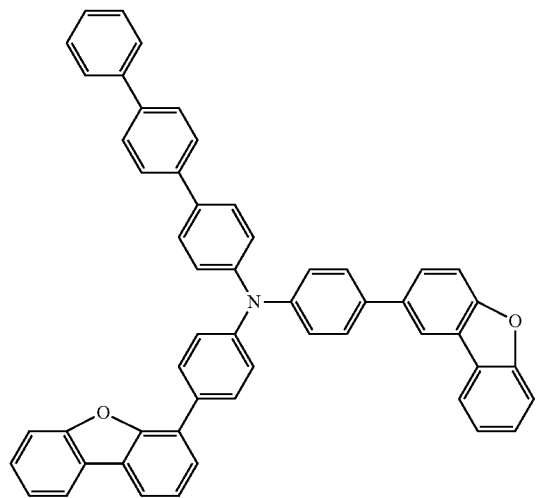
(2-97)
(2-98)
(2-99)
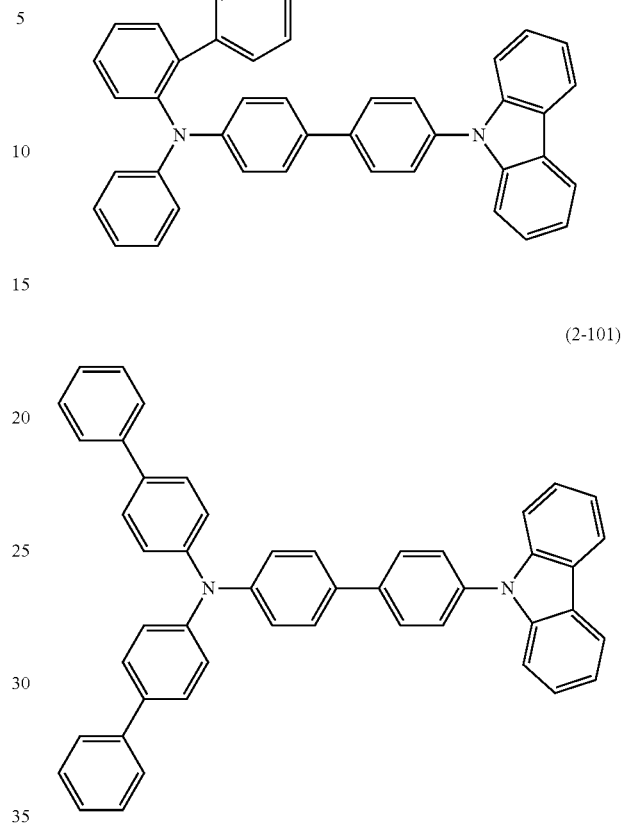
(2-100)
(2-101)
(2-102)
(2-103)
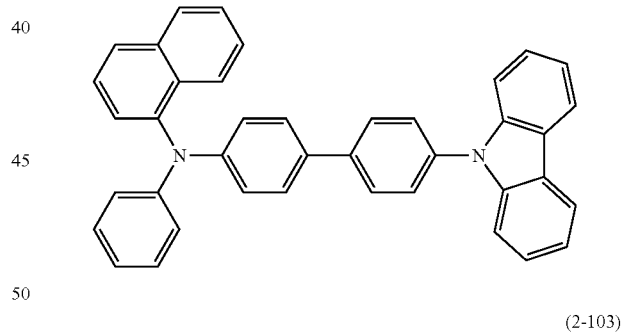
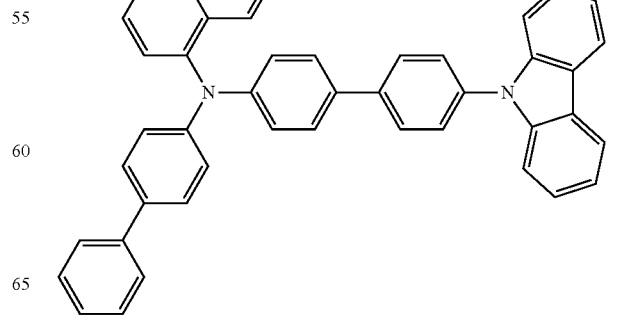

(2-104)
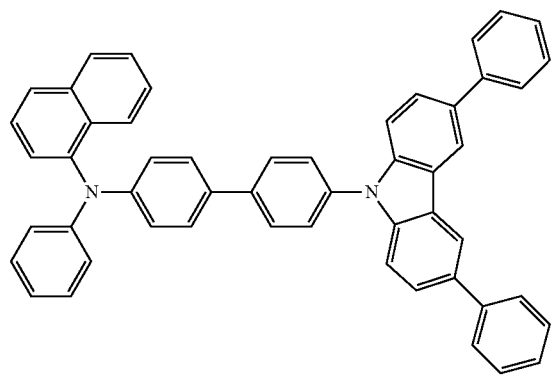
(2-105)
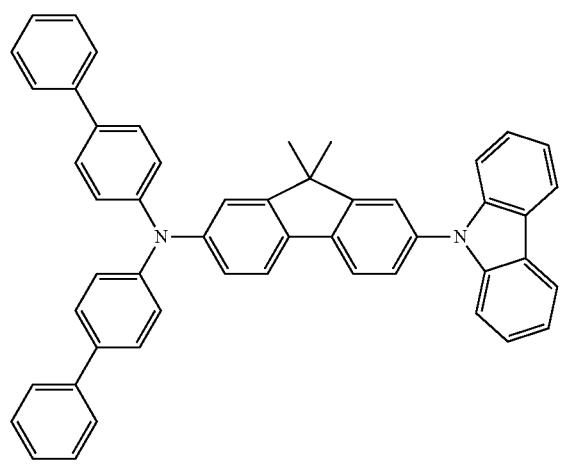
(2-106)
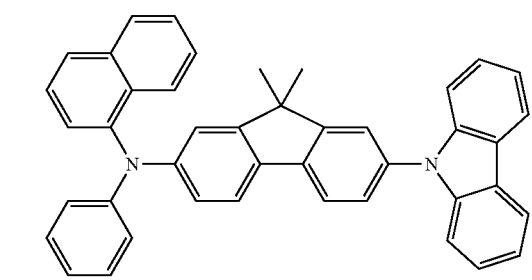
(2-107)
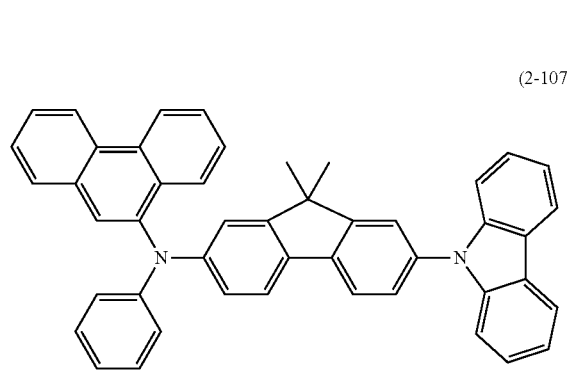
(2-108)
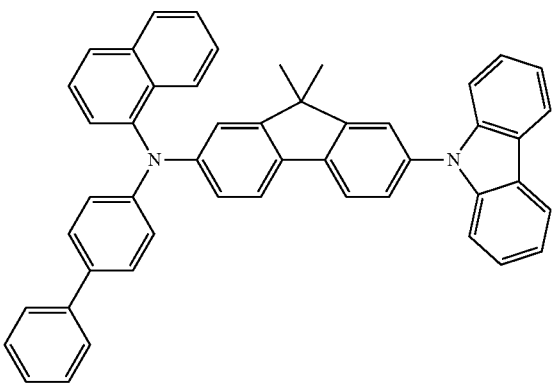
(2-109)
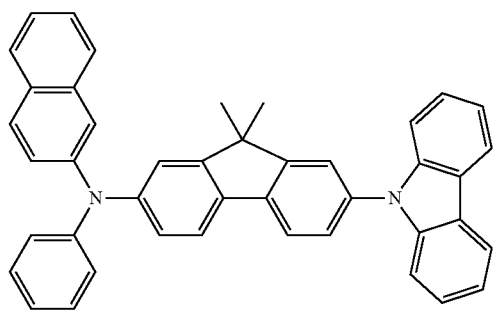
(2-110)
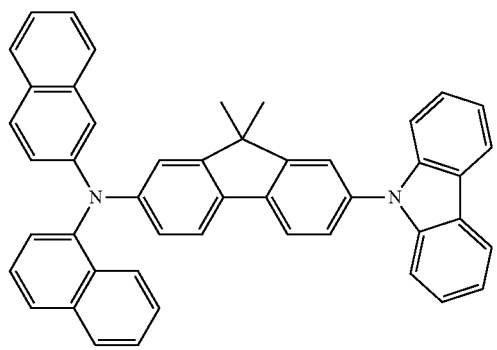
(2-111)
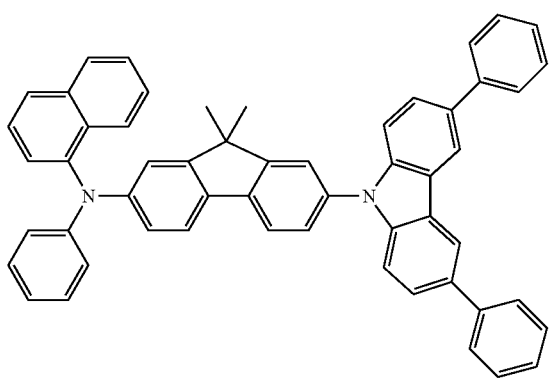

(2-112)
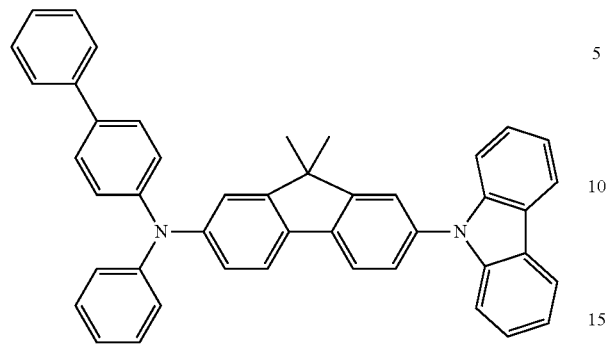
C-221
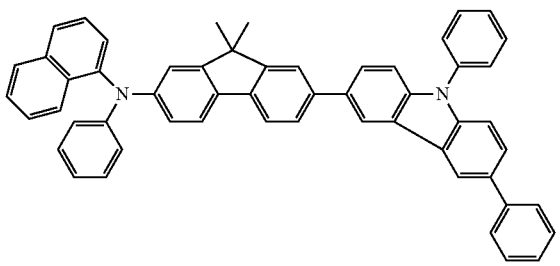
C-217
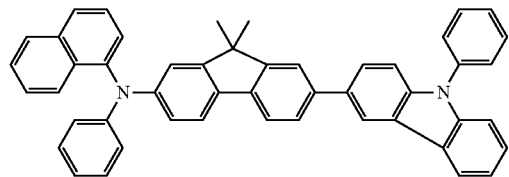
C-218
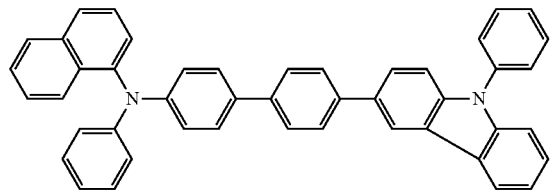
C-222
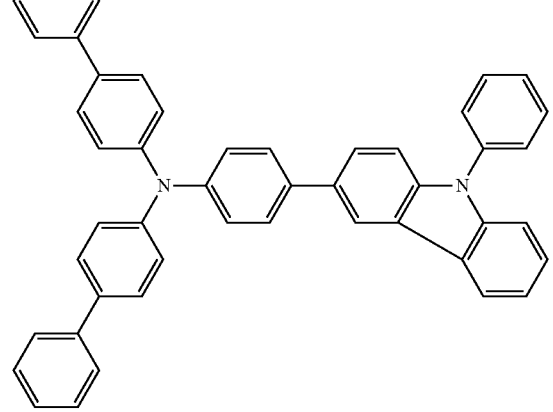
C-219
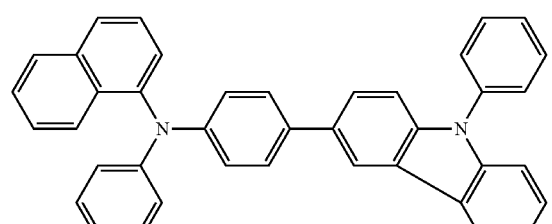
C-220
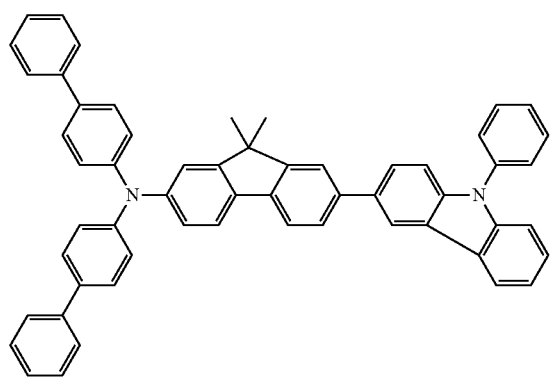
C-223
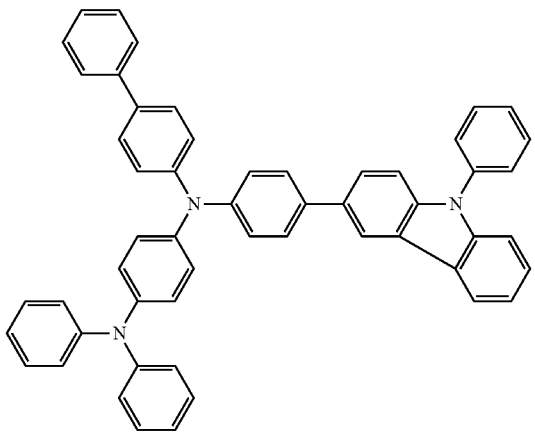

C-224

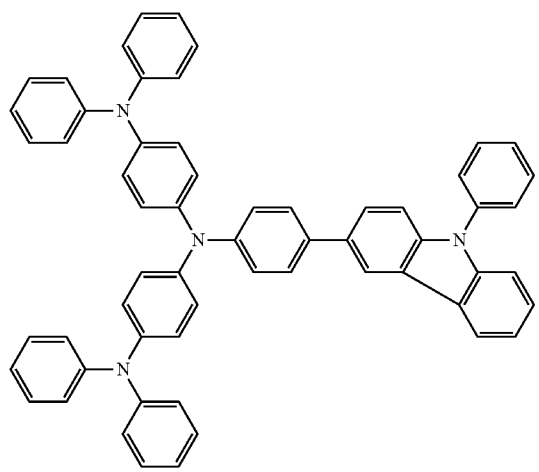

C-225

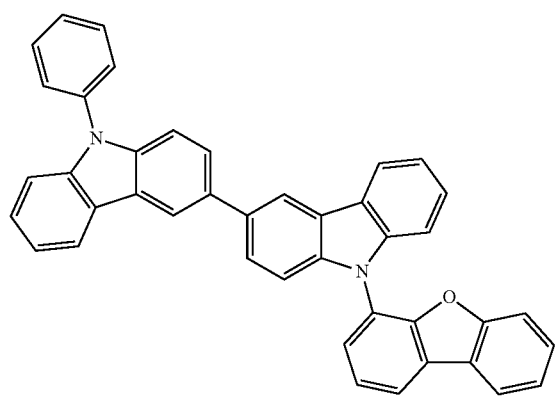

pyridine, pyrimidine, pyridazine, triazine, indole, isoindole, quinoline, isoquinoline, quinoxaline, acridine, pyrrolidine, dioxane, piperidine, morpholine, piperazine, carbazole, phenanthridine, phenanthroline, furan, benzofuran, isobenzofuran, thiophene, oxazole, oxadiazole, benzoxazole, thiazole, thiadiazole, benzothiazole, triazole, imidazole, benzimidazole, pyran, dibenzofuran, dibenzothiophene, azafluorene, azacarbazole, benzene-fused analogues thereof, and cross-linked analogues thereof. Preferred are divalent residues of benzene, biphenyl, spirofluorene, dibenzofuran, and dibenzothiophene.

Examples of $A^7$ to $A^{10}$ include monovalent groups wherein 1 to 10 rings selected from the aromatic hydrocarbon rings and the aromatic heterocyclic rings described above with respect to $Z^1$ and $Z^2$ in formula (CH2) are linked together, for example, monovalent groups of benzene, naphthalene, biphenyl, terphenyl, fluorene, phenanthrene, triphenylene, binaphthalene, bianthracene, perylene, chrysene, fluoranthene, benzofluorene, benzotriphenylene, benzochrysene, anthracene, pyrrole, pyridine, pyrazine, pyridine, pyrimidine, pyridazine, triazine, indole, isoindole, quinoline, isoquinoline, quinoxaline, acridine, pyrrolidine, dioxane, piperidine, morpholine, piperazine, carbazole, phenanthridine, phenanthroline, furan, benzofuran, isobenzofuran, thiophene, oxazole, oxadiazole, benzoxazole, thiazole, thiadiazole, benzothiazole, triazole, imidazole, benzimidazole, pyran, dibenzofuran, dibenzothiophene, azafluorene, azacarbazole, benzene-fused analogues thereof, and cross-linked analogues thereof. Preferred are those mentioned above with respect to $A^1$ to $A^3$ in formula (CH5). A dibenzofuranyl group is also preferred.

Examples of the compound of formula (CH6) are shown below, although not limited thereto.

Compound (CH6)
Compound (CH6) will be described below.

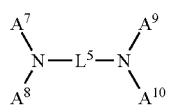

(CH6)

In formula (CH6), $L^5$ represents a substituted or unsubstituted divalent group wherein 1 to 6 aromatic hydrocarbon rings are bonded to each other or included or a substituted or unsubstituted divalent group wherein 1 to 6 aromatic heterocyclic rings are bonded to each other. $L^5$ may comprise an aromatic hydrocarbon ring and aromatic heterocyclic ring combinedly. $A^7$ to $A^{10}$ each represent a group in which 1 to 10 substituted or unsubstituted aromatic hydrocarbon rings are linked together or a group in which 1 to 10 substituted or unsubstituted aromatic heterocyclic rings are linked together.

Examples of $L^5$ include those wherein the aromatic hydrocarbon ring group and the aromatic heterocyclic group mentioned above with respect to $Z^1$ and $Z^2$ in formula (CH2) are linked together, for example, divalent residues of benzene, naphthalene, biphenyl, terphenyl, fluorene, phenanthrene, triphenylene, binaphthalene, bianthracene, perylene, chrysene, fluoranthene, benzofluorene, benzotriphenylene, benzochrysene, anthracene, pyrrole, pyridine, pyrazine,

C-301

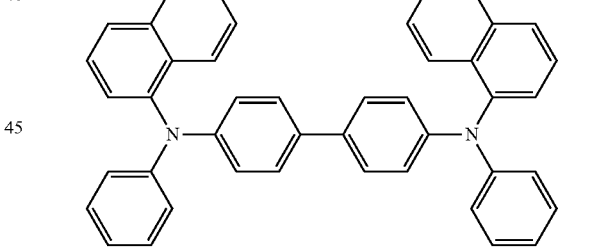

C-302

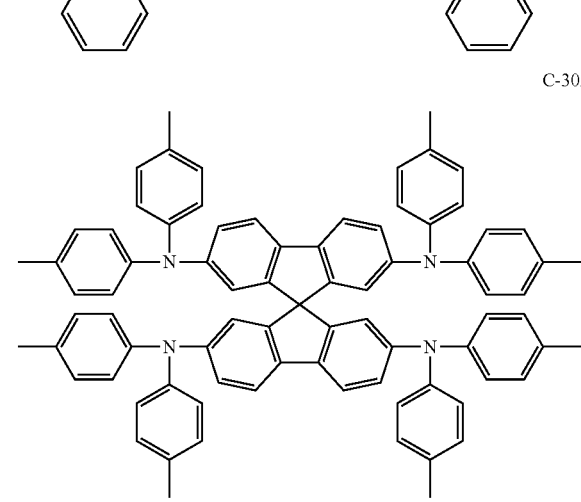

C-303

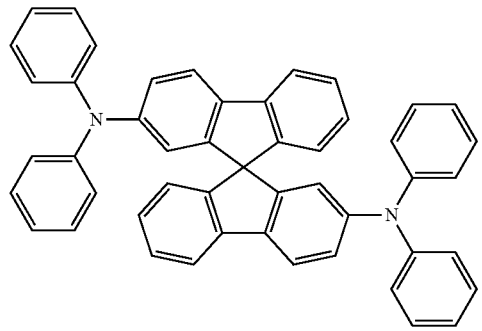

C-304

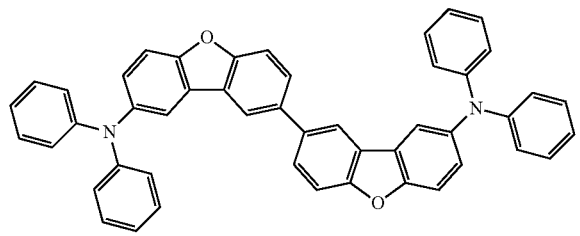

C-305

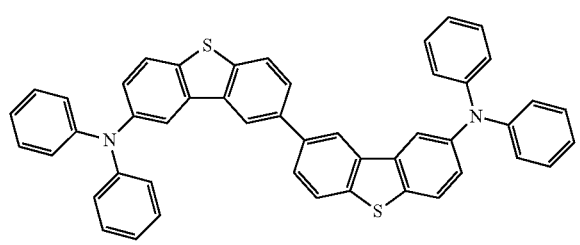

C-306

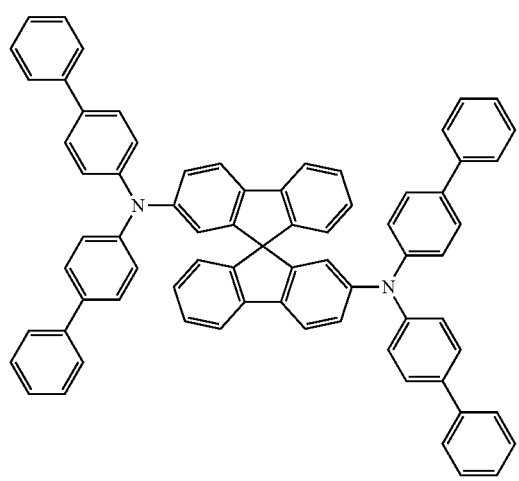

C-307

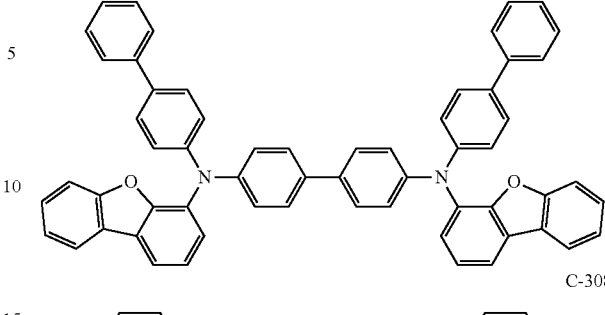

C-308

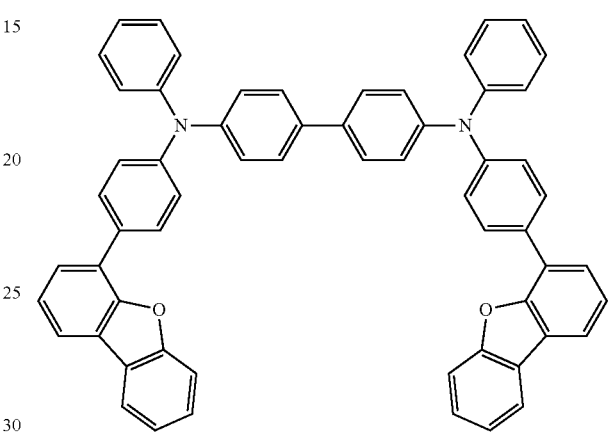

The compounds of formulae (CH4) to (CH6) can be produced according to a known production method, for example, the production method described in WO 2010/061824.

Compound (CH7).

Formula (CH7) will be explained below. The compound of formula (CH7) is excellent in the stability and contributes to improvement of the durability.

$$Ar^1—Ar^2—Ar^3 \qquad (CH7)$$

In formula (CH7), $Ar^1$ and $Ar^3$ each represent a substituted or unsubstituted monovalent aromatic hydrocarbon ring group or a substituted or unsubstituted monovalent aromatic heterocyclic group, and $Ar^2$ represents a divalent group wherein 1 to 10 substituted or unsubstituted aromatic hydrocarbon rings are linked together or 1 to 10 substituted or unsubstituted aromatic heterocyclic rings are linked together. In view of the stability, $Ar^1$, $Ar^2$, and $Ar^3$ are preferably all aromatic hydrocarbon groups.

Examples of $Ar^1$ and $Ar^3$ include monovalent residues described with respect to $Z^1$ and $Z^2$ in formula (CH2), and examples of $Ar^2$ include divalent residues wherein 1 to 10 rings selected from the rings described above with respect to $Z^1$ and $Z^2$ of formula (CH2) are linked together. $Ar^2$ is preferably a divalent residue comprising one or two aromatic hydrocarbon groups which are linked together. $Ar^1$ to $Ar^3$ each preferably represent a residue of a benzene ring, a naphthalene ring, a benzophenanthrene ring, a dibenzophenanthrene ring, a chrysene ring, a benzochrysene ring, a dibenzochrysene ring, a fluoranthene ring, a benzofluoranthene ring, a triphenylene ring, a benzotriphenylene ring, a dibenzotriphenylene ring, a picene ring, a benzopicene ring, or a dibenzopicene ring, because an organic EL device with a high emission efficiency is obtained when combinedly used with a phosphorescent emitting material.

The compound of formula (CH7) can be synthesized by Suzuki-Miyaura cross-coupling reaction, for example, according to the following reaction scheme:
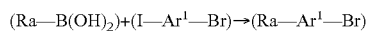
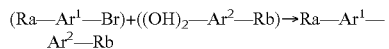
For example, the method described in WO 2009/008215 may be employed.
Examples of the compound of formula (CH7) are shown below, although not limited thereto.
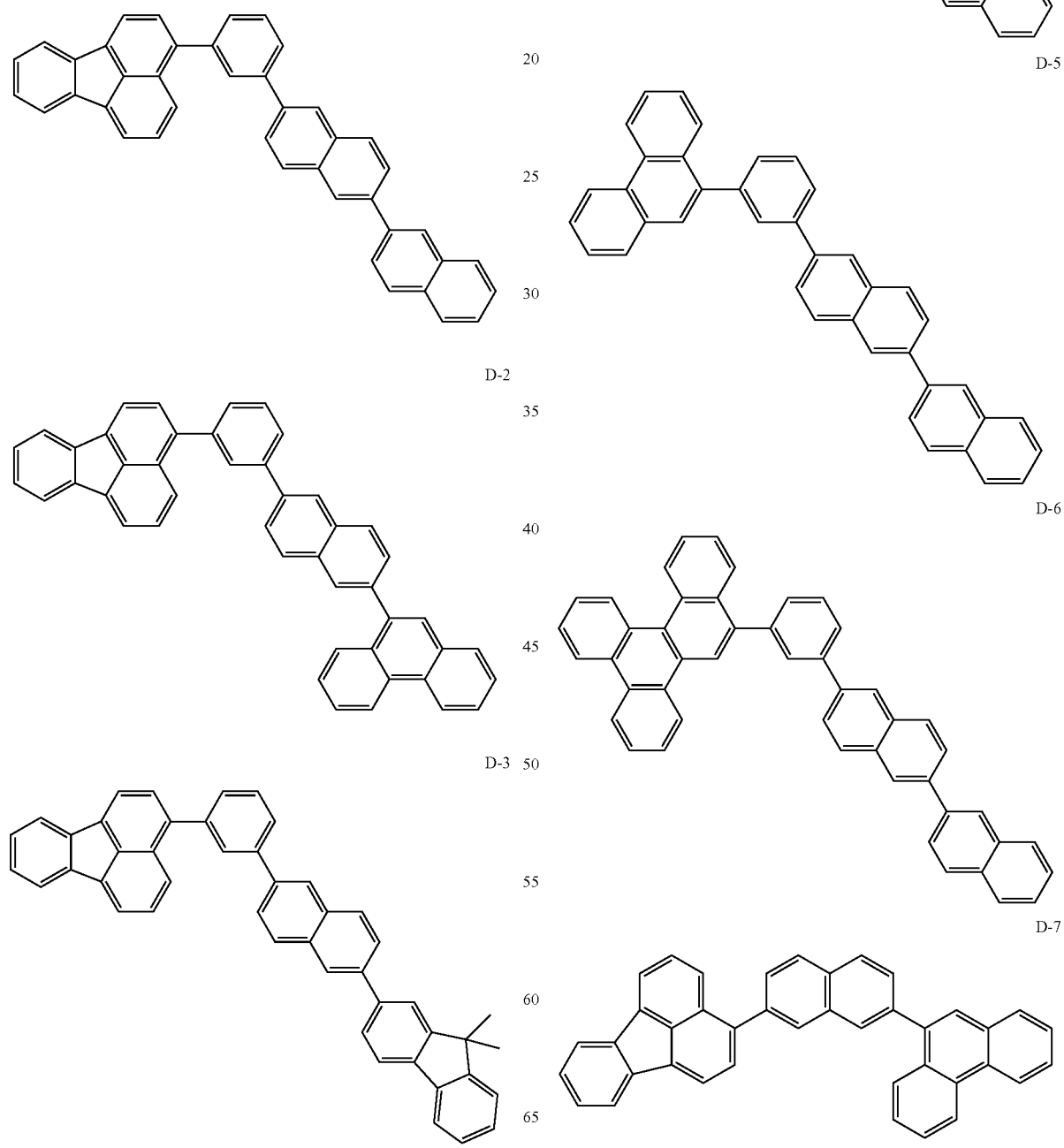
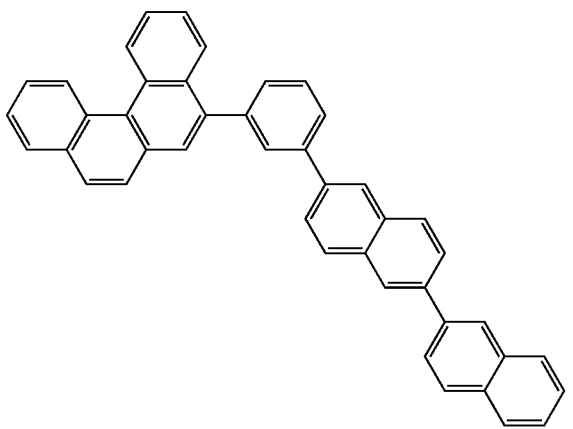

-continued

D-8

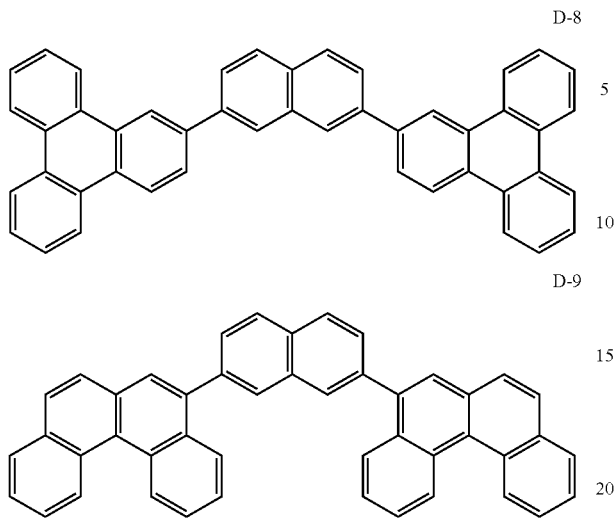

D-9

Compound (CH14)

Compound (CH14) will be described below.

(CH14)

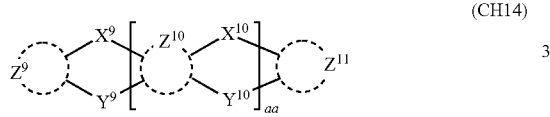

In formula (CH14), $X^9$, $X^{10}$, $Y^9$, and $Y^{10}$ each represent a single bond, —CR$_2$—, —NR—, —O—, —S—, —PR—, or —SiR$_2$—, and cannot all be single bonds. R is as defined above in formula (CH2) and examples thereof include those described with respect to formula (CH2).

$Z^9$, $Z^{10}$, and $Z^{11}$ are as defined above with respect to $Z^1$ and $Z^2$ of formula (CH2) and examples thereof include those described with respect to formula (CH2).

aa is an integer of 1 to 5, preferably an integer of 1 to 2, and particularly preferably 1, and when aa is 2 or more, two or more groups $Z^{10}$ may be the same or different, two or more groups $X^{10}$ may be the same or different, and two or more groups $Y^{10}$ may be the same or different.

Formula (CH14) dose not include the compound represented by formula (CH1).

The compound represented by formula (CH14) is preferably represented by any of formulae (CH14-a-1) to (CH14-a-6) which correspond to formula (CH14) wherein aa is 1, $Z^9$, $Z^{10}$, and $Z^{11}$ are each a benzene ring, one of $X^9$ and $Y^9$ is a single bond, and one of $X^{10}$ and $Y^{10}$ is a single bond.

(CH14-a-1)

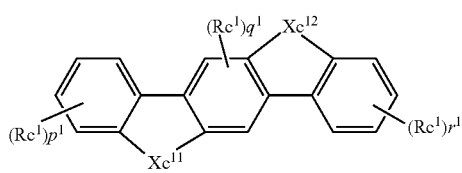

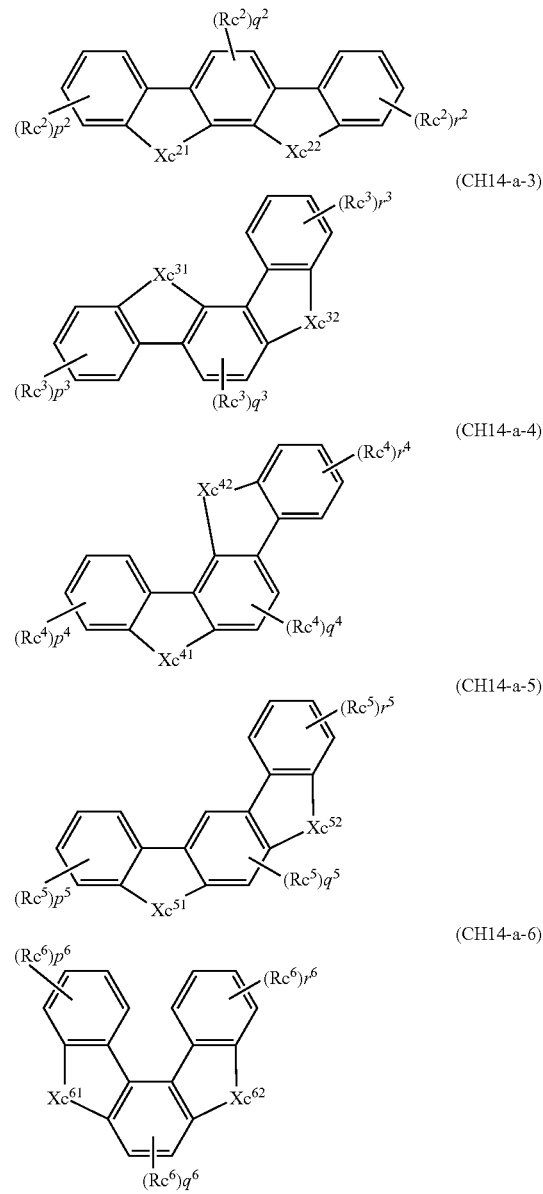

Xc$^{11}$ and Xc$^{12}$ in formula (CH14-a-1), Xc$^{21}$ and Xc$^{22}$ in formula (CH14-a-2), Xc$^{31}$ and Xc$^{32}$ in formula (CH14-a-3), Xc$^{41}$ and Xc$^{42}$ in formula (CH14-a-4), Xc$^{51}$ and Xc$^{52}$ in formula (CH14-a-5), and Xc$^{61}$ and Xc$^{62}$ in formula (CH14-a-6) each independently represent —CR$_2$—, —NR—, —O—, —S—, —PR—, or —SiR$_2$—.

R in Xc$^{11}$, Xc$^{12}$, Xc$^{21}$, Xc$^{22}$, Xc$^{31}$, Xc$^{32}$, Xc$^{41}$, Xc$^{42}$, Xc$^{51}$, Xc$^{52}$, Xc$^{61}$, and Xc$^{62}$ is as defined above with respect to R in $X^1$, $X^2$, $Y^1$, and $Y^2$ of formula (CH2).

Rc$^1$ in formula (14-a-1), Rc$^2$ in formula (14-a-2), Rc$^3$ in formula (14-a-3), Rc$^4$ in formula (14-a-4), Rc$^5$ in formula (14-a-5), and Rc$^6$ in formula (14-a-6) each independently represent a substituted or unsubstituted alkyl group having 1 to 20 carbon atoms, a substituted or unsubstituted cycloalkyl group having 3 to 20 ring carbon atoms, a substituted or unsubstituted alkoxy group having 1 to 20 carbon atoms, a substituted or unsubstituted aralkyl group having 7 to 24 carbon atoms, a substituted or unsubstituted amino group, a substituted or unsubstituted silyl group, a substituted or unsubstituted aromatic hydrocarbon ring group having 6 to 24 ring carbon atoms, or a substituted or unsubstituted aromatic heterocyclic group having 2 to 24 ring carbon atoms.

Rc$^1$ present in two or more occurrences may be the same or different, Rc$^2$ present in two or more occurrences may be the same or different, Rc$^3$ present in two or more occurrences may be the same or different, Rc$^4$ present in two or more occurrences may be the same or different, Rc$^5$ present in two or more occurrences may be the same or different, and Rc$^6$ present in two or more occurrences may be the same or different.

p$^1$ in formula (CH14-a-1), p$^2$ in formula (CH14-a-2), p$^3$ in formula (CH14-a-3), p$^4$ in formula (CH14-a-4), p$^5$ in formula (CH14-a-5), and p$^6$ in formula (CH14-a-6) each independently represent an integer of 0 to 4.

q$^1$ in formula (CH14-a-1), q$^2$ in formula (CH14-a-2), q$^3$ in formula (CH14-a-3), q$^4$ in formula (CH14-a-4), q$^5$ in formula (CH14-a-5), and q$^6$ in formula (CH14-a-6) each independently represent an integer of 0 to 2.

r$^1$ in formula (CH14-a-1), r$^2$ in formula (CH14-a-2), r$^3$ in formula (CH14-a-3), r$^4$ in formula (CH14-a-4), r$^5$ in formula (CH14-a-5), and r$^6$ in formula (CH14-a-6) each independently represent an integer of 0 to 4.

Examples of the compound of formula (CH14) are shown below, although not limited thereto.

E-1

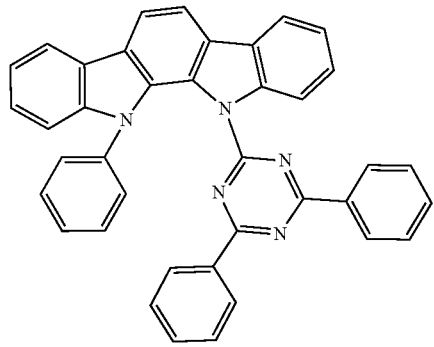

E-2

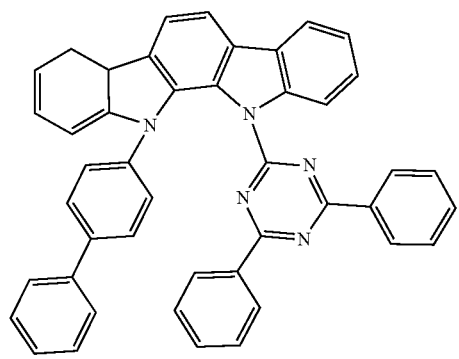

E-3

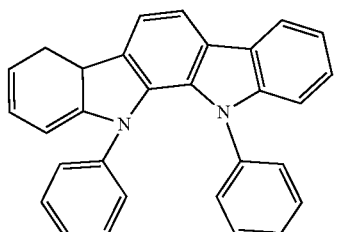

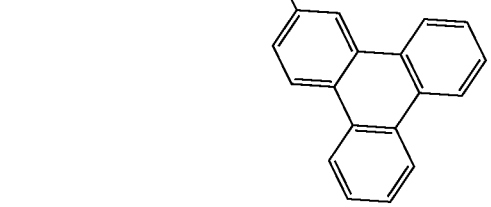

E-4

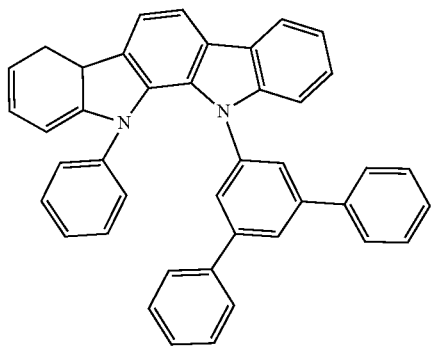

E-5

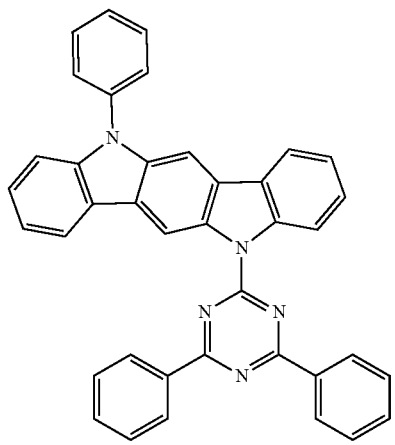

E-6
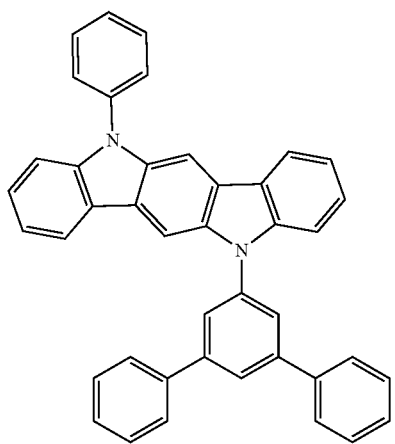
E-7
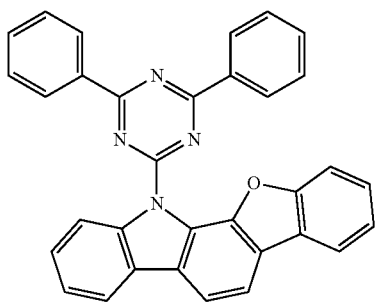
E-8
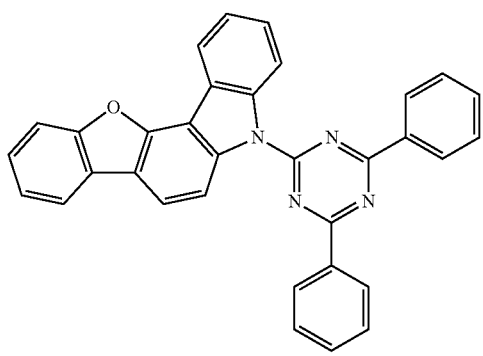
E-9
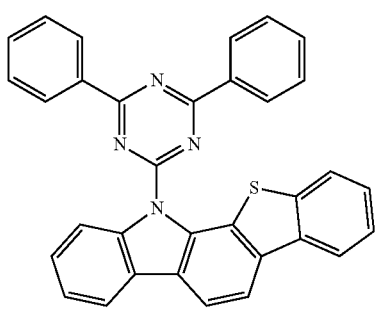
E-10
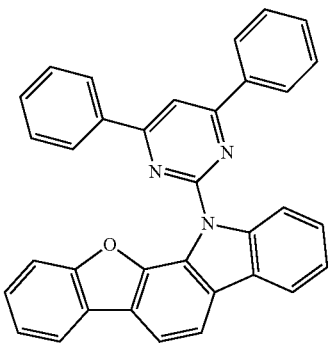
E-11
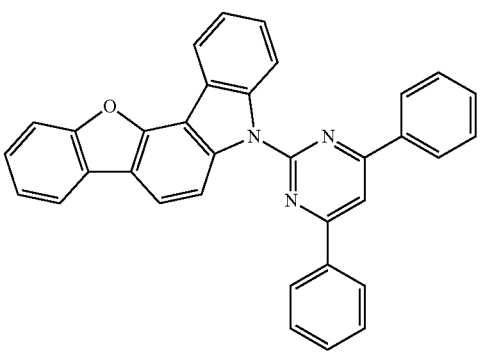
E-12
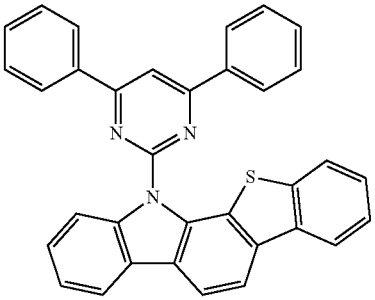
F-1
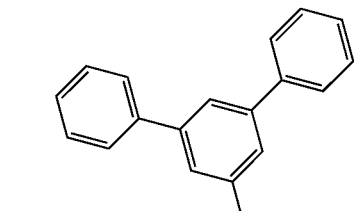

-continued
F-2
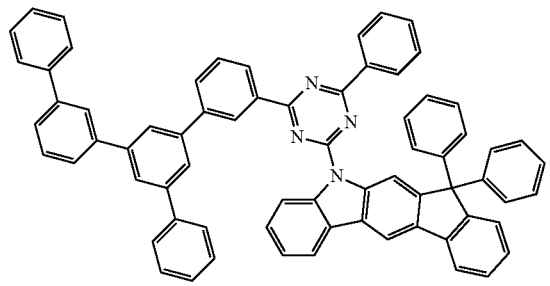
F-3
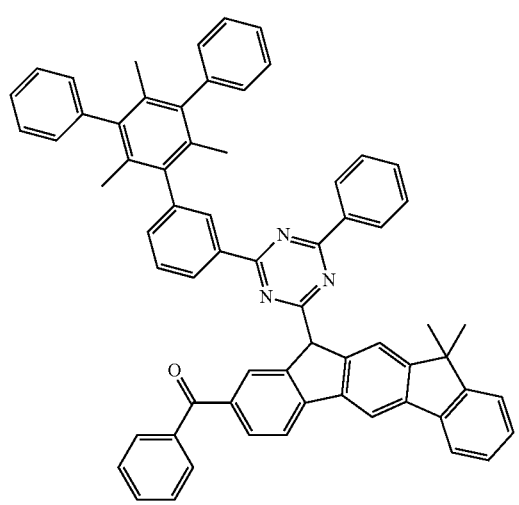
F-4
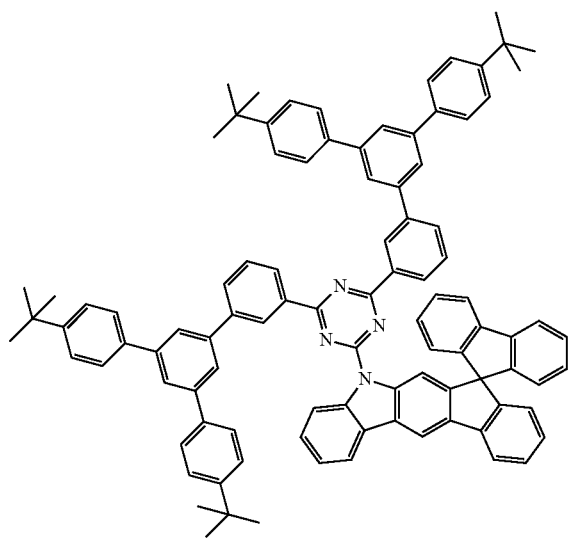
-continued
F-5
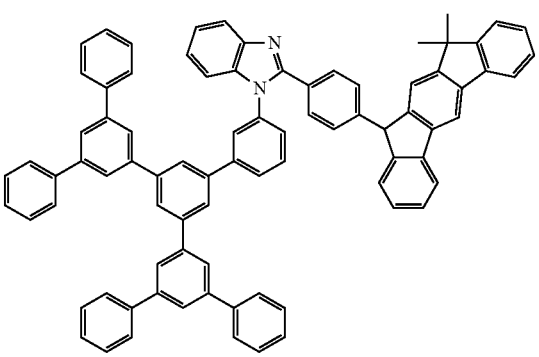
F-6
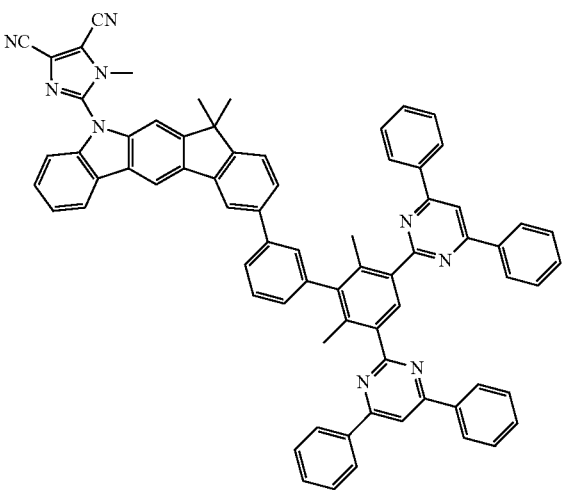
F-7
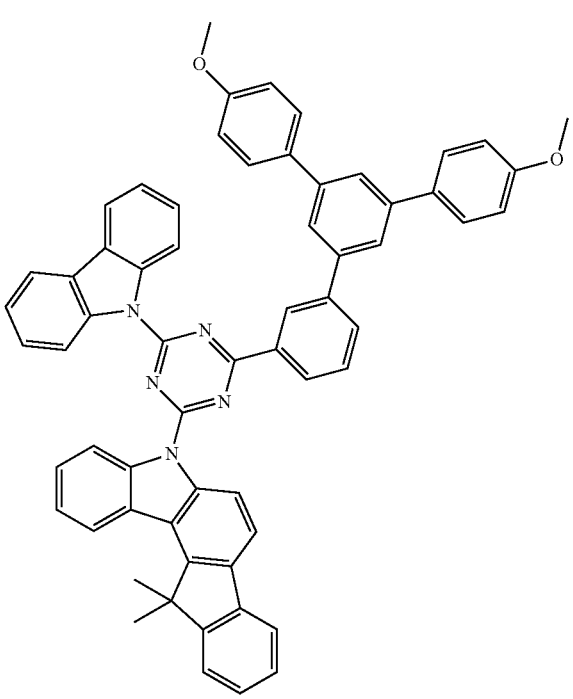

F-8
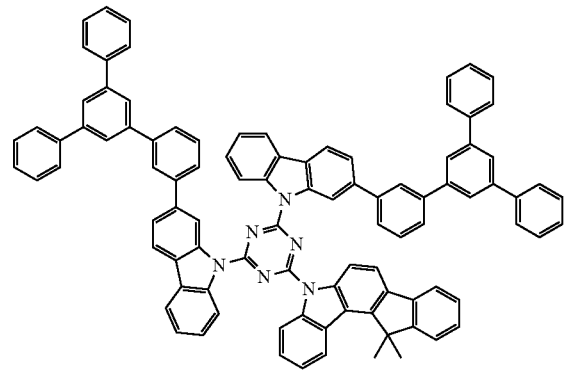
F-9
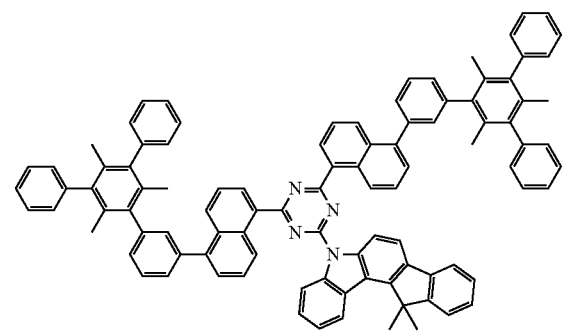
F-10
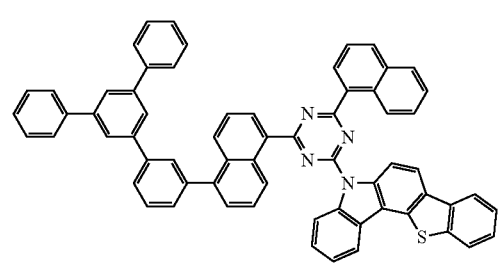
F-11
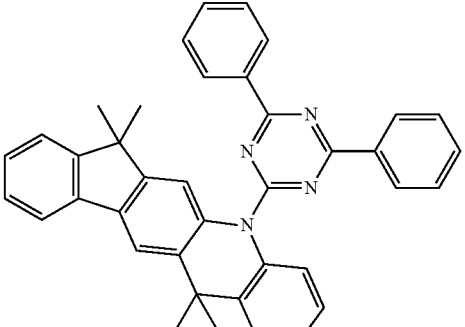
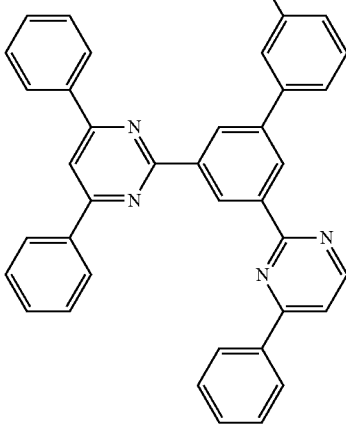
F-12
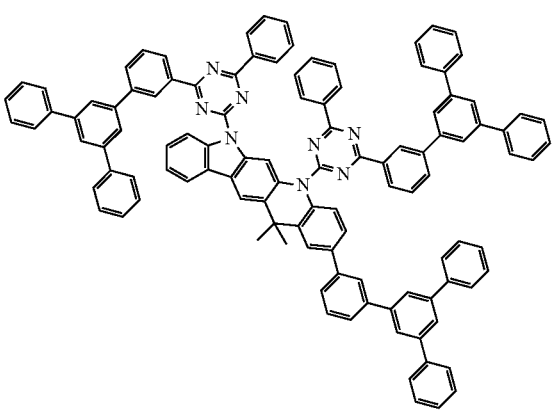

F-13
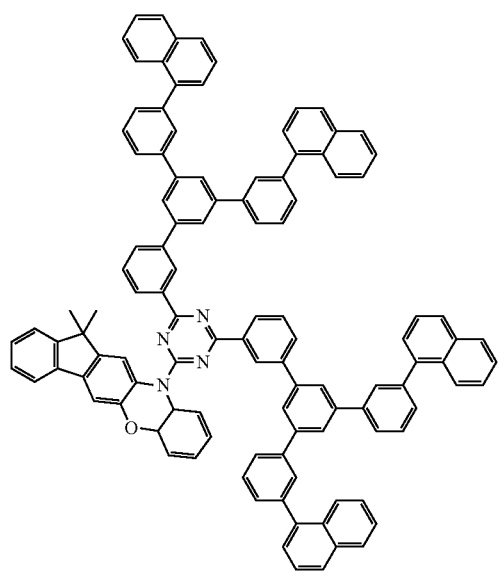
F-14
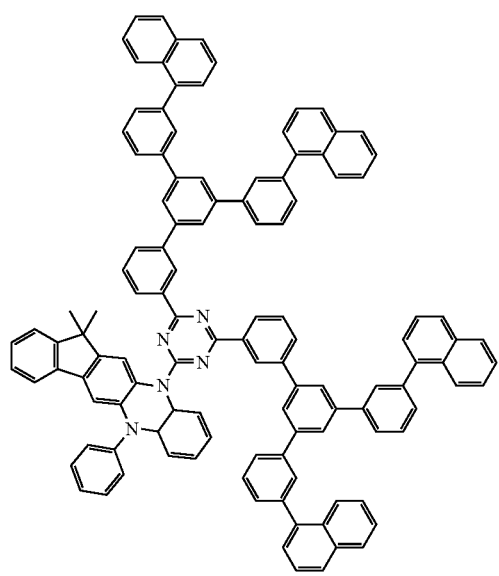
F-15
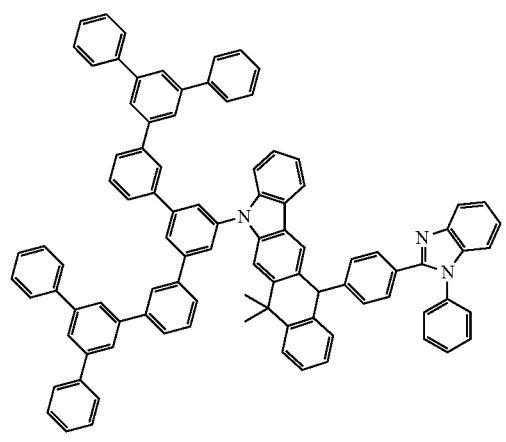
F-16
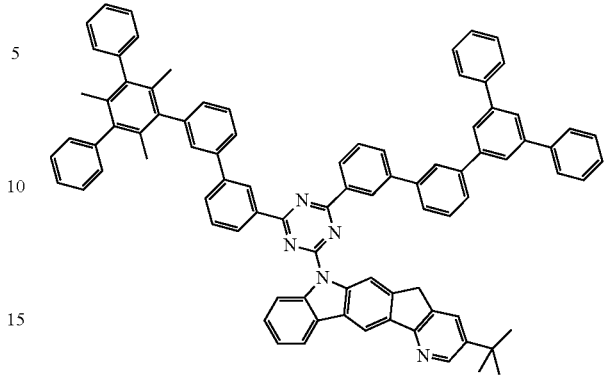
F-17
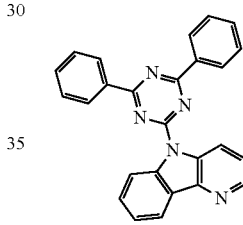 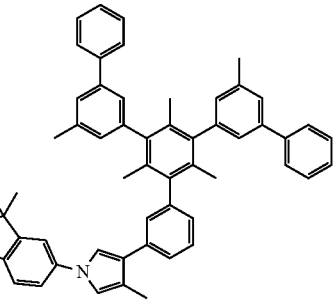
F-18
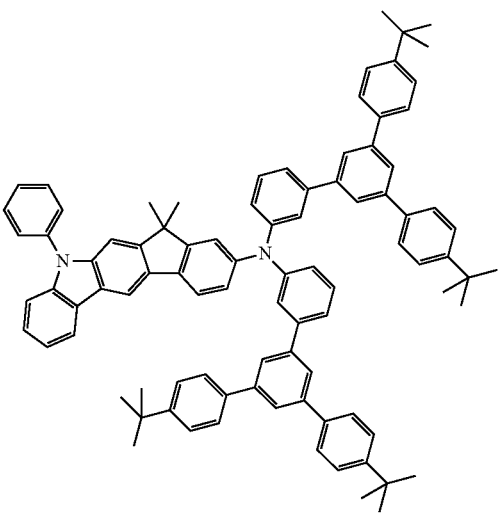

F-19
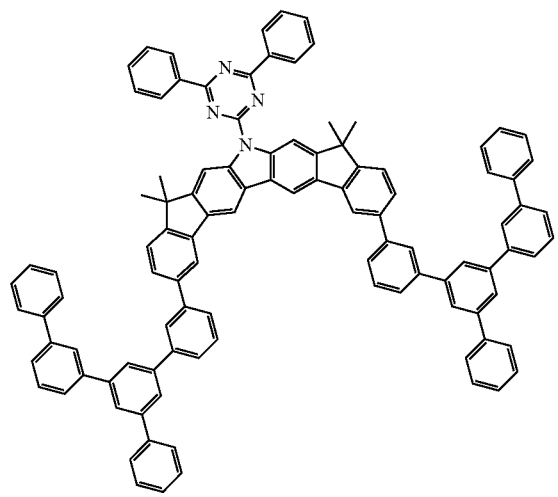
F-20
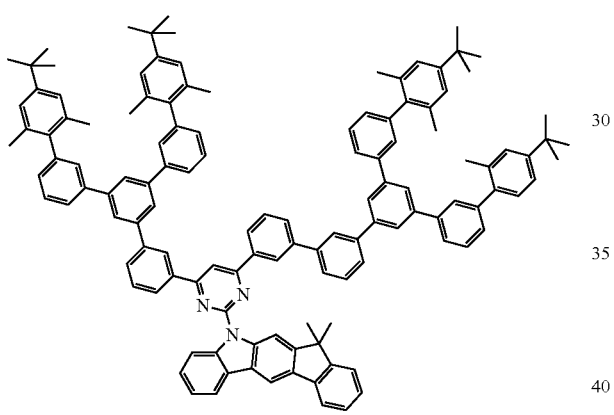
F-21
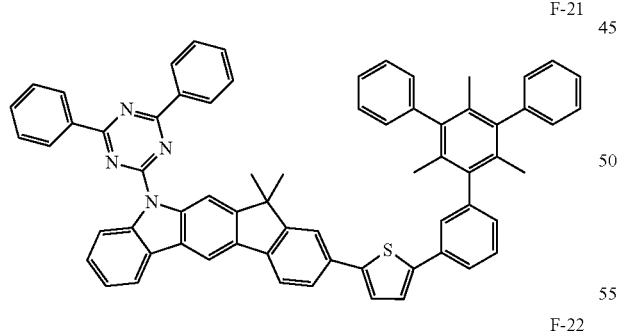
F-22
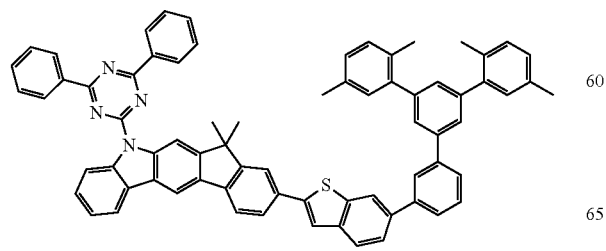
F-23
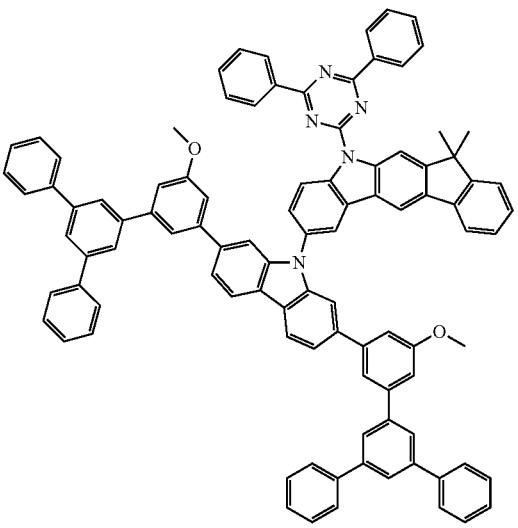
F-24
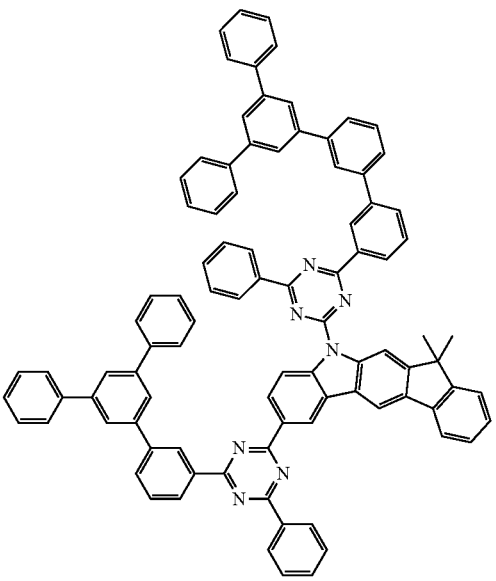

-continued
F-25
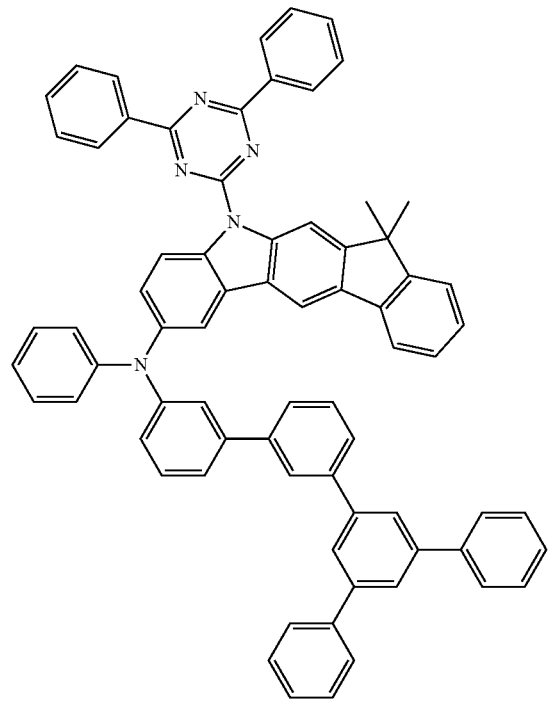
F-26
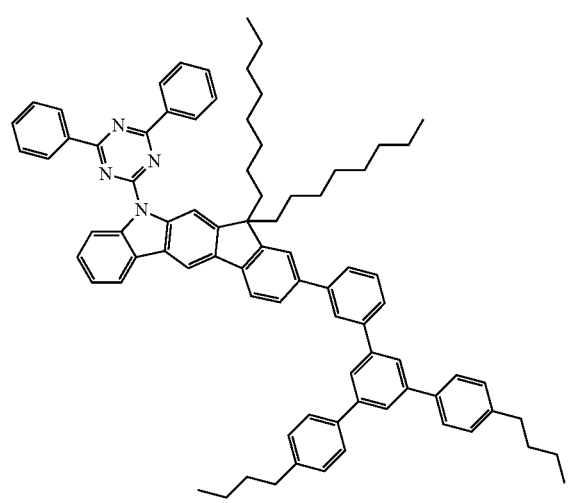
-continued
F-27
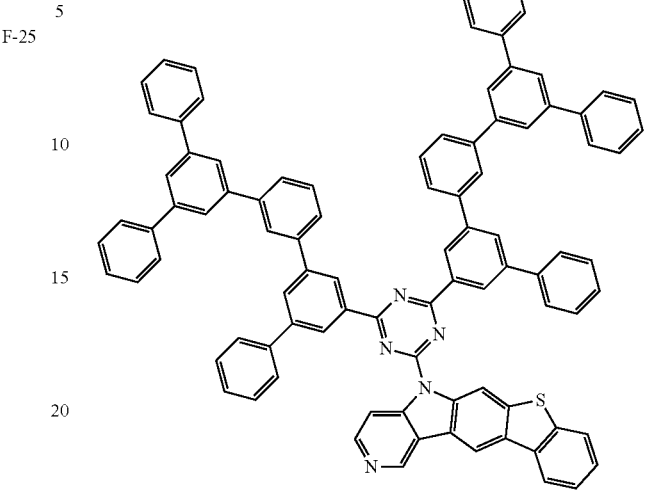
F-28
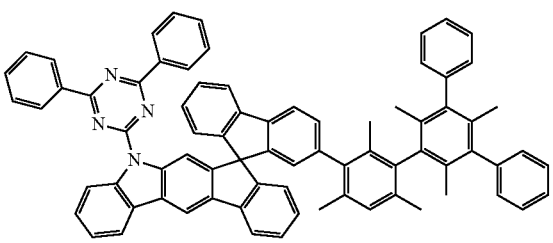
F-29

F-30
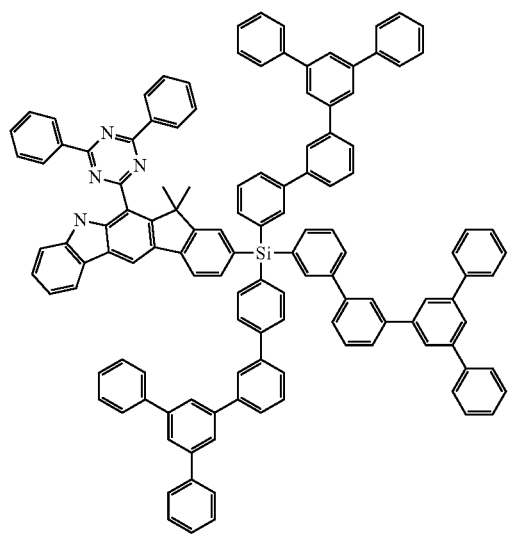
F-31
F-32
F-33
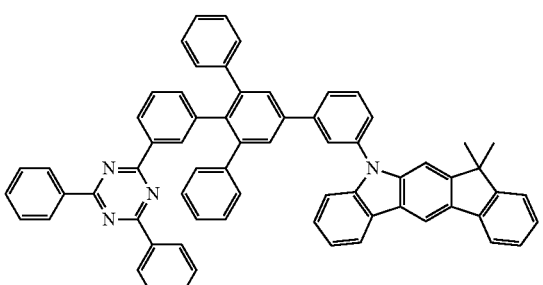
F-34
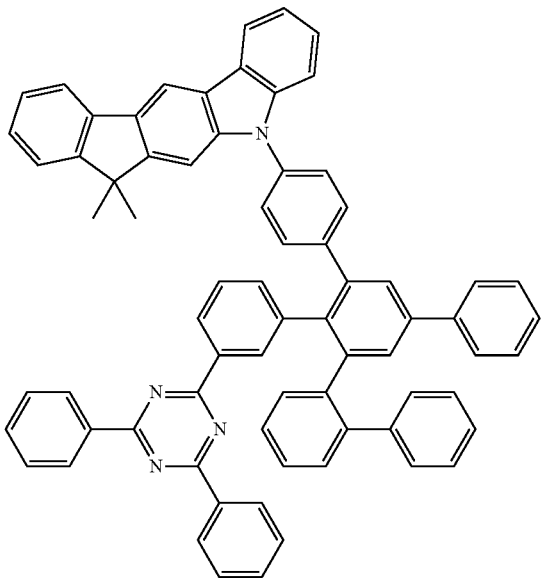
F-35
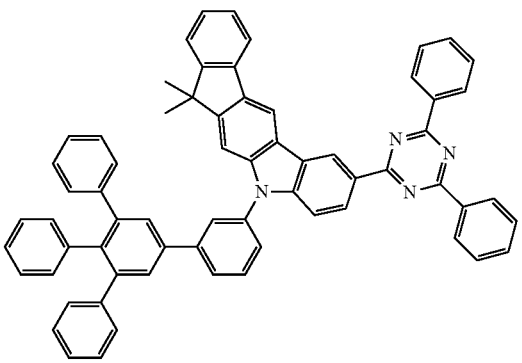

F-36
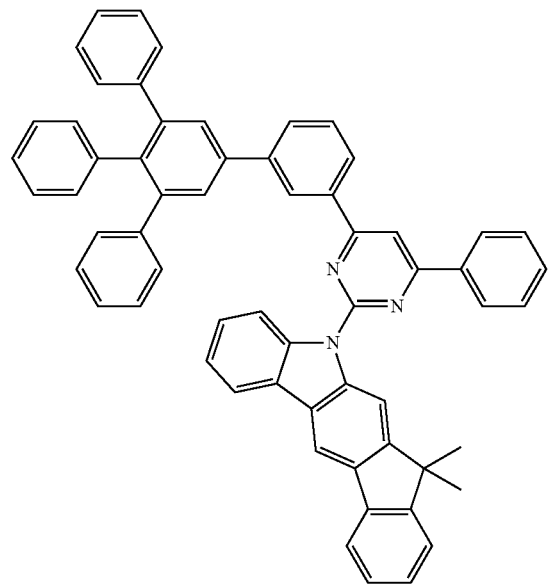
F-37
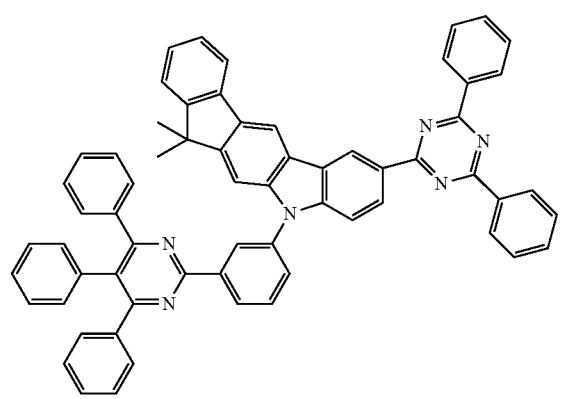
F-38
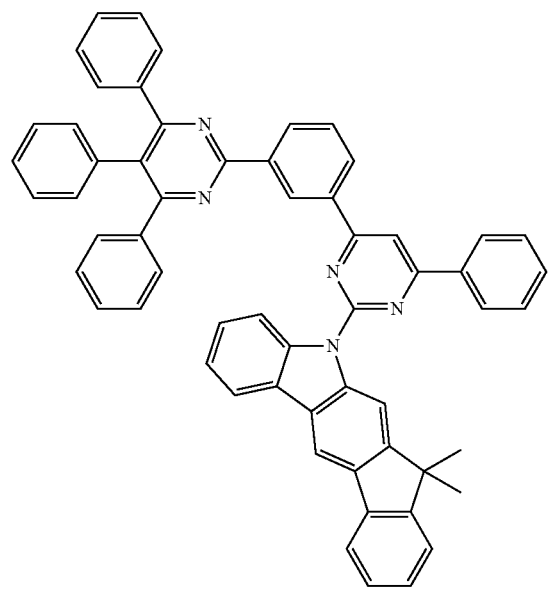
F-39
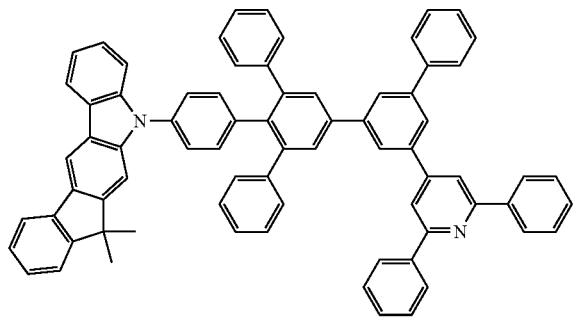
F-40
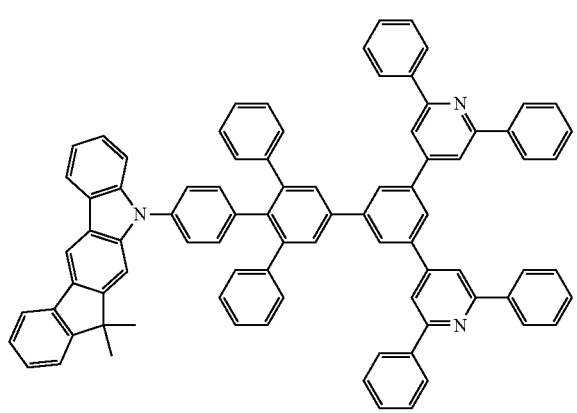
F-41
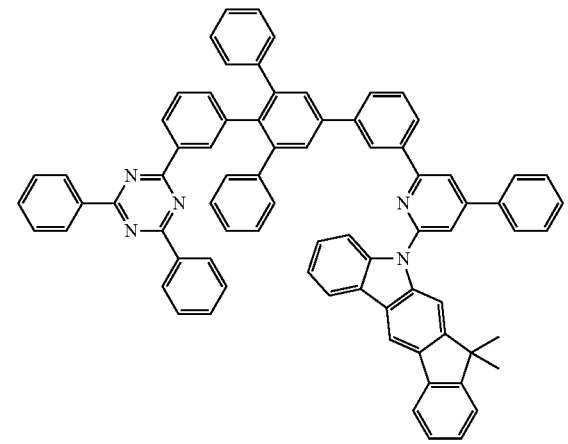

F-42
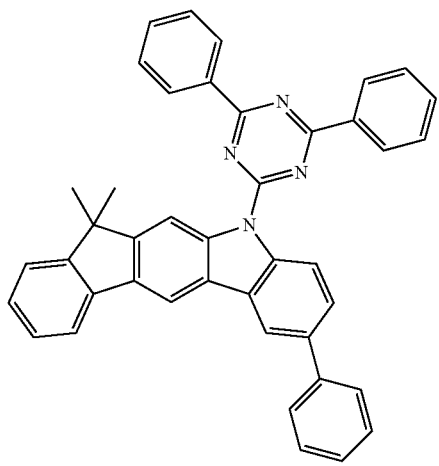
F-43
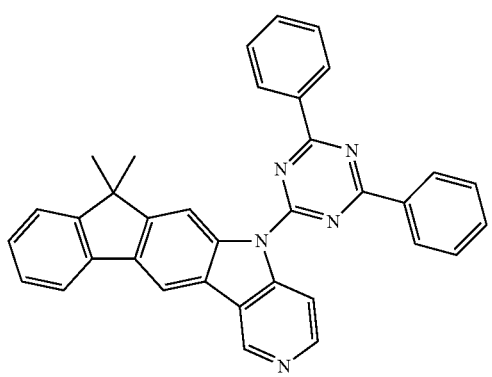
F-44
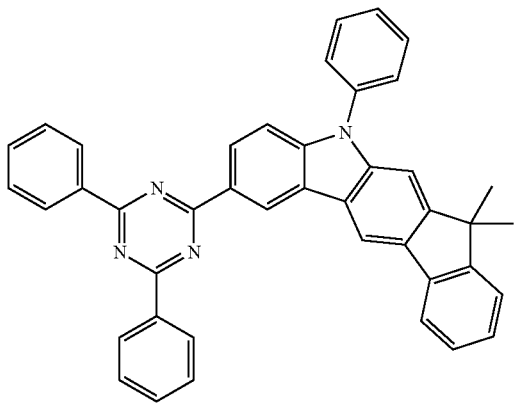
F-45
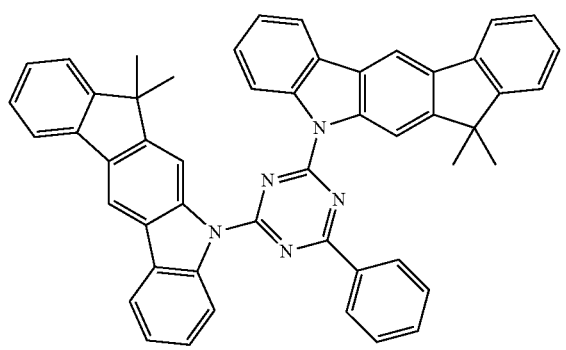
F-46
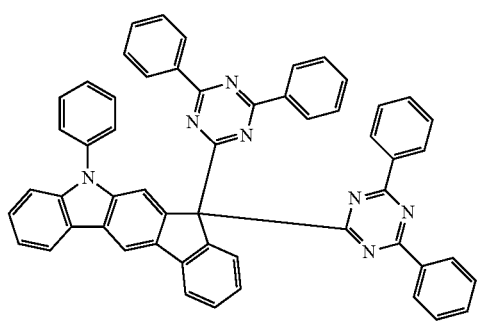
F-47
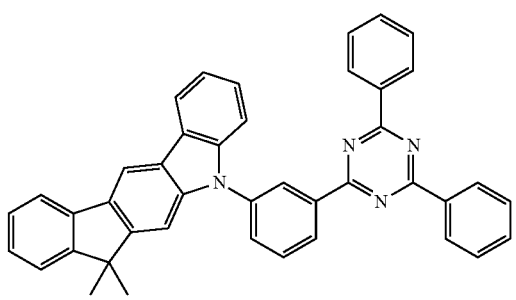
F-48
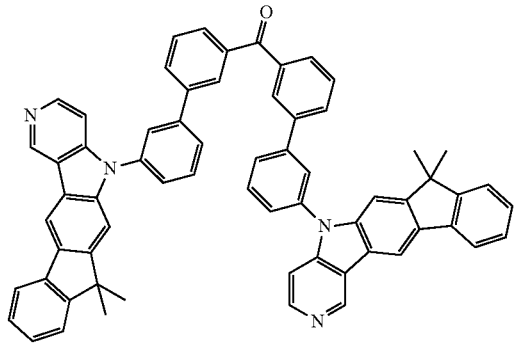
F-49
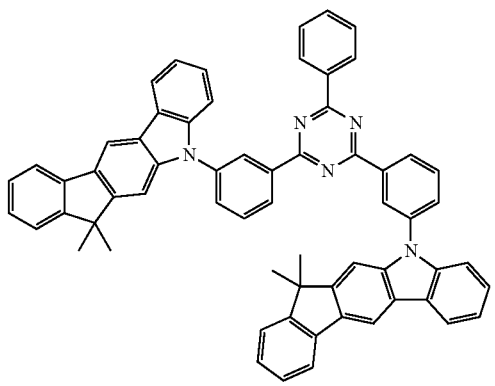

-continued
F-50
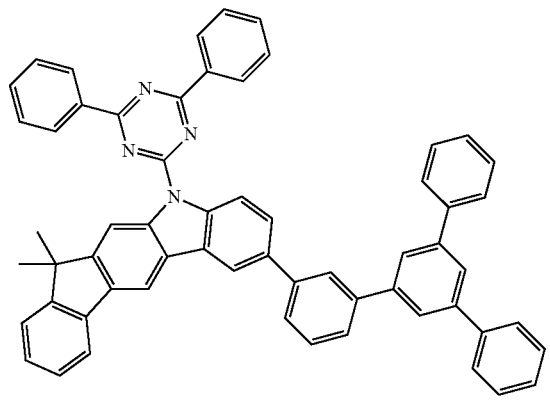
F-51
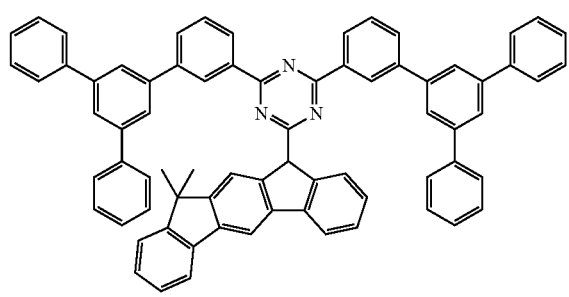
F-52
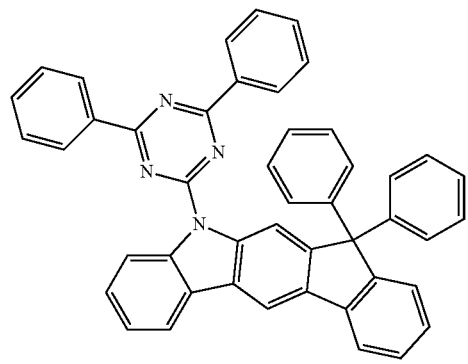
F-53
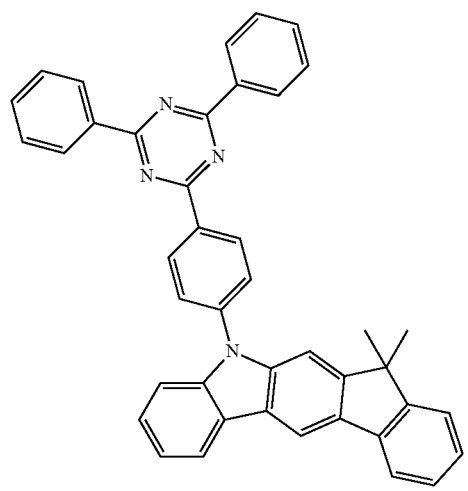
-continued
F-54
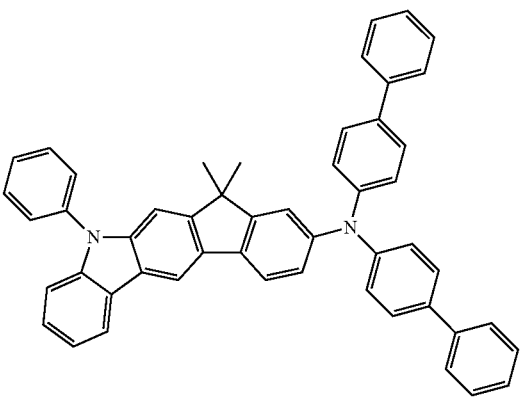
F-55
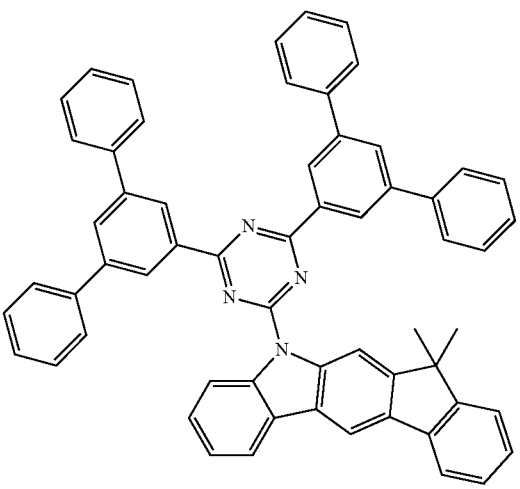
F-56
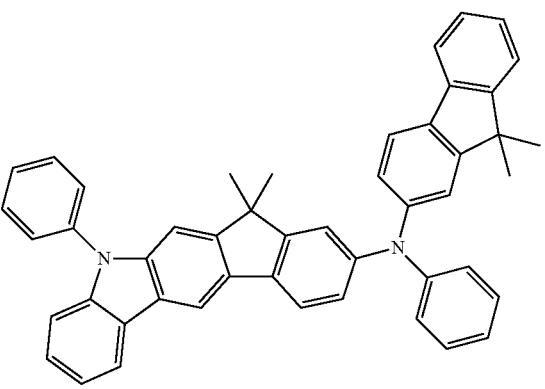

F-57

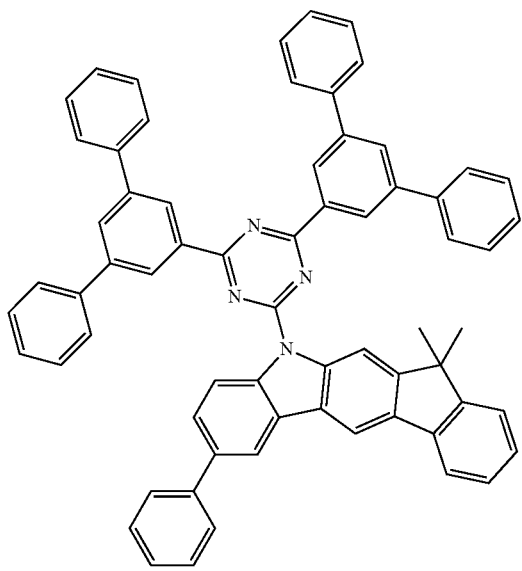

F-58

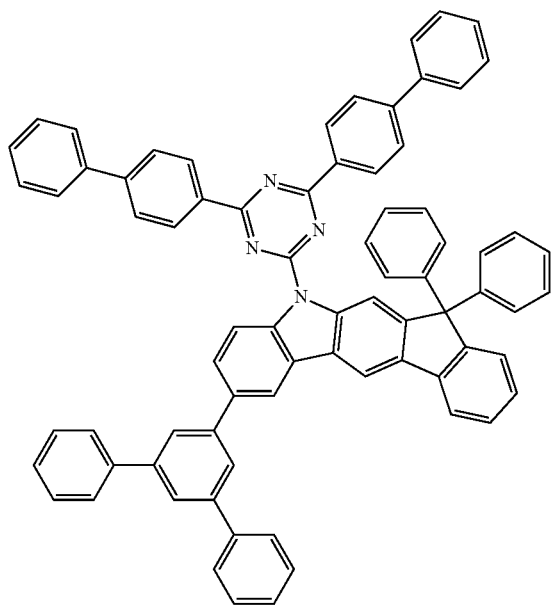

Compound (H15)

The compound of formula (CH15) preferably comprises both a hole transporting skeleton and an electron transporting skeleton in its molecule. More preferably, $B_2$ comprises a hole transporting skeleton and Aa comprises an electron transporting skeleton.

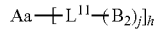 (CH15)

Formula (CH15) is described below.

Aa is as defined above with respect to A of formula (CH1), $L^{11}$ is as defined above with respect to $L^1$ of formula (CH1), and $B_2$ is a residue of the structure represented by formula (CH2);

h is an integer of 1 or more and an upper limit of h is determined according to the structure of Aa, with 1 to 10 being preferred, 1 to 3 being more preferred, and 1 or 2 being still more preferred, although not particularly limited thereto;

j is an integer of 1 or more and an upper limit of j is determined according to the structure of $L^{11}$, with 2 or 3 being preferred, although not limited thereto;

h+j is an integer of 3 or more; and two or more groups $L^{11}$ may be the same or different and two or more groups $B_2$ may be the same or different.

In view of the solubility, a compound asymmetric with respect to Aa wherein the structures formed by $L^{11}$ and $B_2$ are different from each other is preferred.

The compound represented by formula (CH15) is preferably a compound represented by formula (CH15-i) or (CH15-ii):

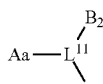 (CH15-i)

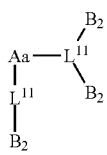 (CH15-ii)

in formula (CH15-i), Aa, $L^{11}$, and $B_2$ are as defined above in formula (CH15), two or more groups $L^{11}$ may be the same or different, and two or more groups $B_2$ may be the same or different; and in formula CH15-ii), Aa, $L^{11}$, and $B_2$ are as defined above in formula (CH15), two or more groups $L^{11}$ may be the same or different, and two or more groups $B_2$ may be the same or different.

Organic Electroluminescence Device

The organic EL device in an aspect of the invention will be described below.

The organic EL device comprises a cathode, an anode, and one or more organic thin film layers between the cathode and the anode. The one or more organic thin film layers comprise a light emitting layer, and at least one layer of the one or more organic thin film layers comprises the composition of the invention or the compound of the invention.

Examples of the organic thin film layer which comprises the composition or compound of the invention include an anode-side organic thin film layer formed between an anode and a light emitting layer (hole transporting layer, hole injecting layer, etc.), a light emitting layer, a cathode-side organic thin film layer formed between a cathode and a light emitting layer (electron transporting layer, electron injecting layer, etc.), a space layer, and a blocking layer, although not limited thereto. The composition or compound of the invention may be used in any of the above layers and is usable as, for example, a host material or a dopant material for use in a light emitting layer of a fluorescent emission unit, a host material for use in a light emitting layer of a phosphorescent emission unit, and a hole transporting layer material or an electron transporting layer material in an emission unit.

In an aspect of the invention, the organic EL device may be any of a fluorescent or phosphorescent single color emitting device, a white-emitting device of fluorescent-phosphorescent hybrid type, a simple-type emitting device having a single emission unit, and a tandem emitting device having two or more emission units, with a phosphorescent device being preferred. The "emission unit" referred to herein is the smallest unit for emitting light by the recombination of injected holes and injected electrons, which comprises one or more organic layers wherein at least one layer is a light emitting layer.

Representative device structures of the simple-type organic EL device are shown below:

(1) Anode/Emission Unit/Cathode

The emission unit may be a laminated unit comprising two or more layers selected from a phosphorescent light emitting layer and a fluorescent light emitting layer. A space layer may be disposed between the light emitting layers to prevent the diffusion of excitons generated in the phosphorescent light emitting layer into the fluorescent light emitting layer. Representative layered structures of the emission unit are shown below:

(a) hole transporting layer/light emitting layer (/electron transporting layer);
(b) hole transporting layer/first phosphorescent emitting layer/second phosphorescent emitting layer (/electron transporting layer);
(c) hole transporting layer/phosphorescent emitting layer/space layer/fluorescent emitting layer (/electron transporting layer);
(d) hole transporting layer/first phosphorescent emitting layer/second phosphorescent emitting layer/space layer/fluorescent emitting layer (/electron transporting layer);
(e) hole transporting layer/first phosphorescent emitting layer/space layer/second phosphorescent emitting layer/space layer/fluorescent emitting layer (/electron transporting layer);
(f) hole transporting layer/phosphorescent emitting layer/space layer/first fluorescent emitting layer/second fluorescent emitting layer (/electron transporting layer);
(g) hole transporting layer/electron blocking layer/light emitting layer (/electron transporting layer);
(h) hole transporting layer/light emitting layer/hole blocking layer (/electron transporting layer); and
(i) hole transporting layer/fluorescent emitting layer/triplet blocking layer (/electron transporting layer).

The emission color of the fluorescent emitting layer and that of the phosphorescent emitting layer may be different. For example, the layered structure of the laminated emission unit (d) may be hole transporting layer/first phosphorescent emitting layer (red emission)/second phosphorescent emitting layer (green emission)/space layer/fluorescent emitting layer (blue emission)/electron transporting layer.

An electron blocking layer may be disposed between the light emitting layer and the hole transporting layer or between the light emitting layer and the space layer, if necessary. Also, a hole blocking layer may be disposed between the light emitting layer and the electron transporting layer, if necessary. With such an electron blocking layer or a hole blocking layer, electrons and holes are confined in the light emitting layer to increase the charge recombination in the light emitting layer, thereby improving the emission efficiency.

Representative device structure of the tandem-type organic EL device is shown below:

(2) Anode/First Emission Unit/Intermediate Layer/Second Emission Unit/Cathode.

The layered structure of the first emission unit and the second emission unit may be selected from those described above with respect to the emission unit.

Generally, the intermediate layer is also called an intermediate electrode, an intermediate conductive layer, a charge generation layer, an electron withdrawing layer, a connecting layer, or an intermediate insulating layer. The intermediate layer may be formed by known materials which can supply electrons to the first emission unit and holes to the second emission unit.

A schematic structure of an example of the organic EL device is shown in FIG. 1, wherein the organic EL device 1 comprises a substrate 2, an anode 3, a cathode 4, and an emission unit 10 disposed between the anode 3 and the cathode 4. The emission unit 10 comprises a light emitting layer 5 which comprises at least one phosphorescent emitting layer comprising a phosphorescent host material and a phosphorescent dopant material (phosphorescent material). A hole injecting/transporting layer 6 (anode-side organic thin film layer) may be disposed between the light emitting layer 5 and the anode 3, and an electron injecting/transporting layer 7 (cathode-side organic thin film layer) may be disposed between the light emitting layer 5 and the cathode 4. An electron blocking layer (not shown) may be disposed on the side of anode 3 of the light emitting layer 5, and a hole blocking layer (not shown) may be disposed on the side of cathode 4 of the light emitting layer 5. With these blocking layers, electrons and holes are confined in the light emitting layer 5 to increase the exciton generation in the light emitting layer 5.

In the present specification, a host is referred to as a fluorescent host when combinedly used with a fluorescent dopant (fluorescent emitting material) and as a phosphorescent host when combinedly used with a phosphorescent dopant. Therefore, the fluorescent host and the phosphorescent host are not distinguished from each other merely by the difference in their molecular structures. Namely, in the present invention, the term "phosphorescent host" means a material for constituting a phosphorescent emitting layer containing a phosphorescent dopant and does not mean a material that cannot be utilized as a material for a fluorescent emitting layer. The same applies to the fluorescent host.

Substrate

The substrate is a support for the emitting device and made of, for example, glass, quartz, and plastics. The substrate may be a flexible substrate, for example, a plastic substrate made of, for example, polycarbonate and poly vinyl chloride.

Anode

The anode is formed on the substrate preferably from a metal, an alloy, an electrically conductive compound, and a mixture thereof, each having a large work function, for example, a work function of 4.5 eV or more. Examples of the material for the anode include indium oxide-tin oxide (ITO: Indium Tin Oxide), indium oxide-tin oxide containing silicon or silicon oxide, indium oxide-zinc oxide, tungsten oxide, indium oxide containing zinc oxide, and grapheme. In addition, gold (Au), platinum (Pt), and metal nitride (for example, titanium nitride) are also usable.

Cathode

The cathode is formed preferably from a metal, an alloy, an electrically conductive compound, and a mixture thereof, each having a small work function, for example, a work function of 3.8 eV or less. Examples of the material for the cathode include a metal belonging to the group 1 or 2 of the periodic table, for example, an alkali metal, such as lithium (Li) and cesium (Cs), an alkaline earth metal, such as magnesium (Mg), an alloy containing these metals (for example, MgAg and AlLi), a rare earth metal, and an alloy containing a rare earth metal.

Guest Material for Light Emitting Layer

The light emitting layer may comprise a highly light-emitting substance and may be formed from a various kind of materials. For example, a fluorescent compound and a phosphorescent component are usable as the highly light-emitting substance. The fluorescent compound is a compound capable of emitting light from a singlet excited state and the phosphorescent compound is a compound capable of emitting light from a triplet excited state.

Example of blue fluorescent material usable in the light emitting layer includes a pyrene derivative, a styrylamine derivative, a chrysene derivative, a fluoranthene derivative, a fluorene derivative, a diamine derivative, and a triarylamine derivative, such as, N,N'-bis[4-(9H-carbazole-9-yl)phenyl]-N,N'-diphenylstilbene-4,4'-diamine (YGA2S), 4-(9H-carbazole-9-yl)-4'-(10-phenyl-9-anthryl)triphenylamine (YGAPA), and 4-(10-phenyl-9-anthryl)-4'-(9-phenyl-9H-carbazole-3-yl)triphenylamine (PCBAPA).

Example of green fluorescent material usable in the light emitting layer includes an aromatic amine derivative, such as N-(9,10-diphenyl-2-anthryl)-N,9-diphenyl-9H-carbazole-3-amine (2PCAPA), N-[9,10-bis(1,1'-biphenyl-2-yl)-2-anthryl]-N,9-diphenyl-9H-carbazole-3-amine (2PCAB-PhA), N-(9,10-diphenyl-2-anthryl)-N,N',N'-triphenyl-1,4-phenylenediamine (abbreviated as 2DPAPA), N-[9,10-bis(1,1'-biphenyl-2-yl)-2-anthryl]-N,N',N'-triphenyl-1,4-phenylenediamine (2DPABPhA), N-[9,10-bis(1,1'-biphenyl-2-yl)]-N-[4-(9H-carbazole-9-yl)phenyl]-N-phenylanthracene-2-amine (2YGABPhA), and N,N,9-triphenylanthracene-9-amine (DPhAPhA).

Example of red fluorescent material usable in the light emitting layer includes a tetracene derivative and a diamine derivative, such as N,N,N',N'-tetrakis(4-methylphenyl)tetracene-5,11-diamine (p-mPhTD) and 7,14-diphenyl-N,N,N',N'-tetrakis(4-methylphenyl)acenaphtho[1,2-a]fluoranthene-3,10-diamine (p-mPhAFD).

Examples of blue phosphorescent emitting material usable in the light emitting layer include a metal complex, such as an iridium complex, an osmium complex, and a platinum complex, with an ortho-metallated complex of iridium, osmium or platinum. Examples thereof include bis[2-(4',6'-difluorophenyl)pyridinato-N,C2']iridium(III) tetrakis(1-pyrazolyl)borato (FIr$_6$), bis[2-(4',6'-difluorophenyl)pyridinato-N,C2']iridium(III) picolinato (FIrpic), bis[2-(3',5'-bistrifluoromethylphenyl)pyridinato-N,C2']iridium (III) picolinato (Ir(CF$_3$ppy)$_2$(pic)), and bis[2-(4',6'-difluorophenyl)pyridinato-N,C2']iridium(III) acetylacetonato (FIracac).

Examples of green phosphorescent emitting material usable in the light emitting layer include an iridium complex, such as tris(2-phenylpyridinato-N,C2')iridium(III) (Ir(ppy)$_a$), bis(2-phenylpyridinato-N,C2')iridium(III) acetylacetonato (Ir(ppy)$_2$(acac)), bis(1,2-diphenyl-1H-benzimidazolato)iridium(III) acetylacetonato (Ir(pbi)$_2$ (acac)), and bis(benzo[h]quinolinato)iridium(III) acetylacetonato (Ir(bzq)$_2$(acac)).

Examples of red phosphorescent emitting material usable in the light emitting layer include a metal complex, such as an iridium complex, a platinum complex, a terbium complex, and a europium complex. Examples thereof include an organometallic complex, such as bis[2-(2'-benzo[4,5-α]thienyl)pyridinato-N,C3']iridium(III) acetylacetonato (Ir(btp)$_2$ (acac)), bis(1-phenylisoquinolinato-N,C2')iridium(III) acetylacetonato (Ir(piq)$_2$(acac)), (acetylacetonato)bis[2,3-bis(4-fluorophenyl)quinoxalinato]iridium(III) (Ir(Fdpq)$_2$ (acac)), and 2,3,7,8,12,13,17,18-octaethyl-21H,23H-porphyrin platinum(II) (PtOEP).

The following rare earth metal complex, such as tris(acetylacetonato) (monophenanthroline)terbium(III) (Tb(acac)$_3$(Phen)), tris(1,3-diphenyl-1,3-propanedionato)(monophenanthroline)europium(III) (Eu(DBM)$_3$(Phen)), and tris[1-(2-thenoyl)-3,3,3-trifluoroacetonato](monophenanthroline)europium(III) (Eu(TTA)$_3$(Phen)), are also usable as a phosphorescent emitting compound, because these complexes emit light from the rare earth metal ion (electron transition between different multiple states).

Host Material for Light Emitting Layer

The light emitting layer may be formed by dispersing the highly light-emitting material (guest material) mentioned above in another material (host material). The material in which the highly light-emitting material is to be dispersed may be selected from various kinds of materials and is preferably a material having a lowest unoccupied molecular orbital level (LUMO level) higher than that of the highly light-emitting material and a highest occupied molecular orbital level (HOMO level) lower than that of the highly light-emitting material.

The composition or compound of the invention is preferably used as the material in which the highly light-emitting material is to be dispersed.

In addition to the compound of the invention, also usable are, for example, (1) a metal complex, such as an aluminum complex, a beryllium complex, and a zinc complex; (2) a heterocyclic compound, such as an oxadiazole derivative, a benzimidazole derivative, and a phenanthroline derivative; (3) a fused aromatic compound, such as a carbazole derivative, an anthracene derivative, a phenanthrene derivative, a pyrene derivative, and a chrysene derivative; and (4) an aromatic amine compound, such as a triarylamine derivative and a fused aromatic polycyclic amine derivative. Examples thereof include a metal complex, such as tris(8-quinolinolato)aluminum (III) (Alq), tris(4-methyl-8-quinolinolato)aluminum(III) (Almq$_3$), bis(10-hydroxybenzo[h]quinolinato)beryllium (II) (BeBq$_2$), bis(2-methyl-8-quinolinolato)(4-phenylphenolato)aluminum(III) (BAlq), bis(8-quinolinolato)zinc(II) (Znq), bis[2-(2-benzoxazolyl)phenolato]zinc(II) (ZnPBO), and bis[2-(2-benzothiazolyl)phenolato]zinc(II) (ZnBTZ); a heterocyclic compound, such as 2-(4-biphenylyl)-5-(4-tert-butylphenyl)-1,3,4-oxadiazole (PBD), 1,3-bis[5-(p-tert-butylphenyl)-1,3,4-oxadiazole-2-yl]benzene (OXD-7), 3-(4-biphenylyl)-4-phenyl-5-(4-tert-butylphenyl)-1,2,4-triazole (TAZ), 2,2',2"-(1,3,5-benzenetriyl)tris(1-phenyl-1H-benzimidazole) (TPBI), bathophenanthroline (BPhen), and bathocuproin (BCP); a fused aromatic compound, such as 9-[4-(10-phenyl-9-anthryl)phenyl]-9H-carbazole (CzPA), 3,6-diphenyl-9-[4-(10-phenyl-9-anthryl)phenyl]-9H-carbazole (DPCzPA), 9,10-bis(3,5-diphenylphenyl)anthracene (DPPA), 9,10-di(2-naphthyl)anthracene (DNA), 2-tert-butyl-9,10-di(2-naphthyl)anthracene (t-BuDNA), 9,9'-bianthryl (BANT), 9,9'-(stilbene-3,3'-diyl)diphenanthrene (DPNS), 9,9'-(stilbene-4,4'-diyl)diphenanthrene (DPNS2), 3,3',3"-(benzene-1,3,5-triyl)tripyrene (TPB3), 9,10-diphenylanthracene (DPAnth), and 6,12-dimethoxy-5,11-diphenylchrysene; and an aromatic amine compound, such as N,N-diphenyl-9-[4-(10-phenyl-9-anthryl)phenyl]-9H-carbazole-3-amine (CzA1PA), 4-(10-phenyl-9-anthryl)triphenylamine (DPhPA), N,9-diphenyl-N-[4-(10-phenyl-9-anthryl)phenyl]-9H-carbazole-3-amine (PCAPA), N,9-diphenyl-N-{4-[4-(10-phenyl-9-anthryl)phenyl]phenyl}-9H-carbazole-3-amine (PCAPBA), N-(9,10-diphenyl-2-anthryl)-N,9-diphenyl-9H-carbazole-3-amine (2PCAPA), NPB (or α-NPD), TPD, DFLDPBi, and BSPB. The material (host material) for dispersing the highly light-emitting material (guest material) may be used alone or in combination of two or more.

Electron Transporting Layer

The electron transporting layer comprises a highly electron-transporting material, for example, (1) a metal complex, such as an aluminum complex, a beryllium complex, and a zinc complex, (2) a heteroaromatic compound, such as an imidazole derivative, a benzimidazole derivative, an azine derivative, a carbazole derivative, and a phenanthroline derivative, and (3) a macromolecular compound.

Electron Injecting Layer

The electron injecting layer comprises a highly electron-injecting material, for example, an alkali metal, an alkaline earth metal, and a compound of these metals, such as lithium (Li), lithium fluoride (LiF), cesium fluoride (CsF), calcium fluoride (CaF2), and lithium oxide (LiOx).

Hole Injecting Layer

The hole injecting layer is comprises a highly hole-transporting material, for example, molybdenum oxide, titanium oxide, vanadium oxide, rhenium oxide, ruthenium oxide, chromium oxide, zirconium oxide, hafnium oxide, tantalum oxide, silver oxide, tungsten oxide, manganese oxide, an aromatic amine compound, and a macromolecular compound, such as oligomer, dendrimer, and polymer.

Hole Transporting Layer

The hole transporting layer comprises a highly hole-transporting material, for example, an aromatic amine compound, a carbazole derivative, an anthracene derivative, and a macromolecular compound, such as poly(N-vinyl carbazole) (abbreviated as PVK) and poly(4-vinyltriphenylamine) (abbreviated as PVTPA). Other materials are also usable if their hole transporting ability is higher than their electron transporting ability. The layer comprising a highly hole-transporting material may be a single layer or a laminate of two or more layers each comprising the highly hole-transporting material.

In an aspect of the invention, each layer of the organic EL device can be formed by a known method, such as a vacuum vapor deposition method and a spin coating method. For example, each layer can be formed by a known method, such as a vacuum vapor deposition method, a molecular beam evaporation method (MBE method), and a coating method using a solution of the compound for forming the layer, such as a dipping method, a spin coating method, a casting method, a bar coating method, and a roll coating method.

The thickness of each organic thin film layer is not particularly limited and preferably several nanometers to 1 μm, because an excessively small thickness may cause defects such as pin holes and an excessively large thickness may require a high driving voltage.

The layer containing the composition or compound of the invention (a light emitting layer, a hole transporting layer, and an electron transporting layer) is preferably formed by a coating method using a solution (ink composition) comprising a solvent and the composition or compound of the invention. The solution may comprise another material, such as dopant, if necessary.

The coating method is preferably a wet film-forming method, for example, a letterpress printing method, an intaglio printing method, a lithographic printing method, a stencil printing method, a combination of the preceding methods with an offset printing method, an inkjet printing method, a dispenser coating method, a spin coating method, a bar coating method, a dip coating method, a spray coating method, a slit coating method, a roll coating method, a cap coating method, a rotogravure roll coating method, and a meniscus coating method. If a fine patterning is required, a letterpress printing method, an intaglio printing method, a lithographic printing method, a stencil printing method, a combination of the preceding methods with an offset printing method, an inkjet printing method, and a dispenser coating method are preferred. A transfer coating method is also usable, in which the polymer is preformed into a film on a substrate by the wet film-foaming method described above and then the preformed film is transferred onto a substrate having an electrode printed thereon by a laser light or hot press.

The film formation by the above methods can be made under the conditions well known to a person skilled in the art and the details thereof are omitted for conciseness.

The coating liquid (ink composition) for use in the coating method is not particularly limited as long as it contains at least one kind of the composition and compound of the invention, and may be in the form of either a solution or a dispersion.

The content of the composition or compound of the invention in the coating liquid (ink composition) is preferably 0.1 to 15% by mass, more preferably 0.1 to 10% by mass, still more preferably 0.3 to 5% by mass, and particularly preferably 0.3 to 3% by mass, each based on the total of the coating liquid.

An organic solvent is preferably used as the solvent. Examples of the organic solvent include a chlorine-containing solvent, such as chloroform, chlorobenzene, chlorotoluene, chloroxylene, chloroanisole, dichloromethane, dichlorobenzene, dichlorotoluene, dichloroethane, trichloroethane, trichlorobenzene, trichloromethylbenzene, bromobenzene, dibromobenzene, and bromoanisole; an ether solvent, such as tetrahydrofuran, dioxane, dioxolane, oxazole, methylbenzoxazole, benzisoxazole, furan, furazan, benzofuran, and dihydrobenzofuran; an aromatic hydrocarbon solvent, such as ethylbenzene, diethylbenzene, triethylbenzene, trimethylbenzene, trimethoxybenzene, propylbenzene, isopropylbenzene, diisopropylbenzene, dibutylbenzene, amylbenzene, dihexylbenzene, cyclohexylbenzene, tetramethylbenzene, dodecylbenzene, benzonitrile, acetophenone, methylacetophenone, methoxyacetophenone, ethyl toluate, toluene, ethyltoluene, methoxytoluene, dimethoxytoluene, trimethoxytoluene, isopropyltoluene, xylene, butylxylene, isopropylxylene, anisole, ethylanisole, dimethylanisole, trimethylanisole, propylanisole, isopropylanisole, butylanisole, methylethylanisole, anethole, anisyl alcohol, methyl benzoate, ethyl benzoate, propyl benzoate, butyl benzoate, diphenyl ether, butyl phenyl ether, benzyl methyl ether, benzyl ethyl ether, methylenedioxybenzene, methylnaphthalene, tetrahydronaphthalene, aniline, methylaniline, ethylaniline, butylaniline, biphenyl, methylbiphenyl, and isopropylbiphenyl; an aliphatic hydrocarbon solvent, such as cyclohexane, methylcyclohexane, n-pentane, n-hexane, n-heptane, n-octane, n-nonane, n-decane, tetradecane, decalin, and isopropylcyclohexane; a ketone solvent, such as acetone, methyl ethyl ketone, cyclohexanone, and acetophenone; an ester solvent, such as ethyl acetate, butyl acetate, ethyl cellosolve acetate, methyl benzoate, and phenyl acetate; a polyhydric alcohol and its derivatives, such as ethylene glycol, ethylene glycol monobutyl ether, ethylene glycol monoethyl ether, ethylene glycol monomethyl ether, dimethoxyethane, propylene glycol, diethoxymethane, triethylene glycol monoethyl ether, glycerin, and 1,2-hexanediol; an alcoholic solvent, such as methanol, ethanol, propanol, isopropanol, and cyclohexanol; a sulfoxide solvent, such as dimethyl sulfoxide; and an amide solvent, such as N-methyl-2-pyrrolidone and N,N-dimethylformamide. These solvents may be used alone or in combination of two or more.

Of the above solvents, in view of solubility, uniform film formation, viscosity, etc., a solvent comprising at least one selected from toluene, xylene, ethylbenzene, amylbenzene, anisole, 4-methoxytoluene, 2-methoxytoluene, 1,2-dimethoxybenzene, mesitylene, tetrahydronaphthalene, cyclohexylbenzene, 2,3-dihydrobenzofuran, cyclohexanone, and methylcyclocyclohexanone is preferred.

The coating liquid (ink composition) for film formation may include, if necessary, a viscosity modifier, a surface tension modifier, a crosslinking initiator, or a crosslinking catalyst, which are preferably selected from those not adversely affecting the device performance even if remaining in the film or those capable of removing from the film during the film formation.

In an aspect of the invention, the organic electroluminescence device can be used in an electronic device, for example, as display parts, such as organic EL panel module, display devices of television sets, mobile phones, personal computer, etc., and light emitting sources of lighting equipment and vehicle lighting equipment.

EXAMPLES

The invention will be described in more detail with reference to the examples and comparative examples. It should be noted that the scope of the invention is not limited to the following examples.

(1) The synthesis method of compound 1[I], the production method of organic EL devices employing compound 1[I], and the evaluation results thereof are described below.

Compound 1[I]

Synthesis Example 1[I](Synthesis of Compound H-1[I])

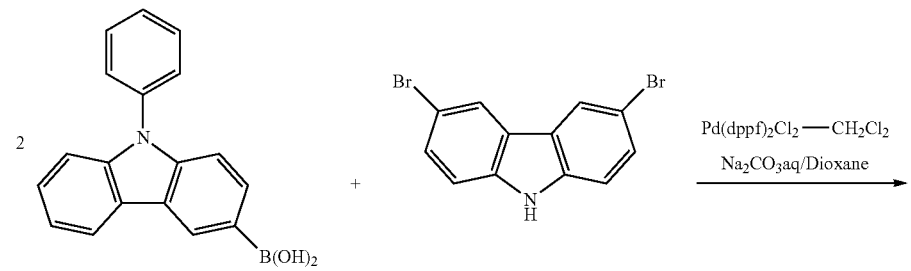

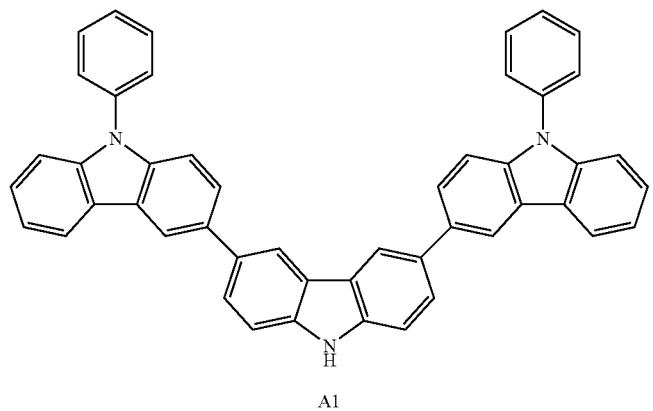

A1

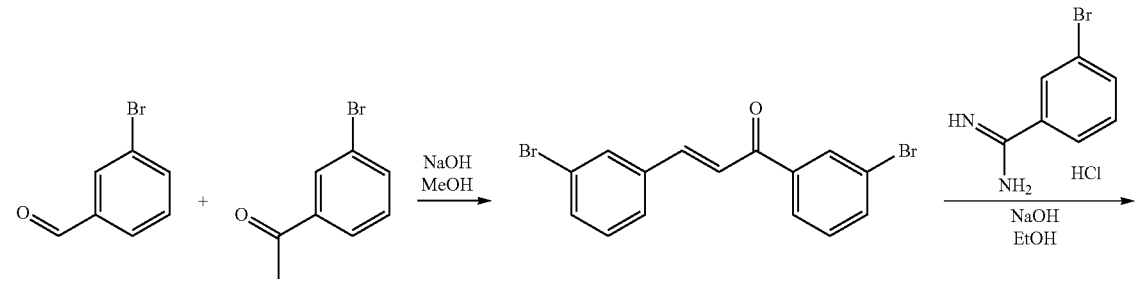

-continued
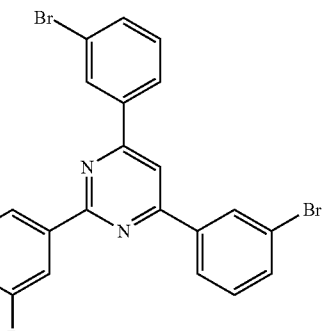
B1
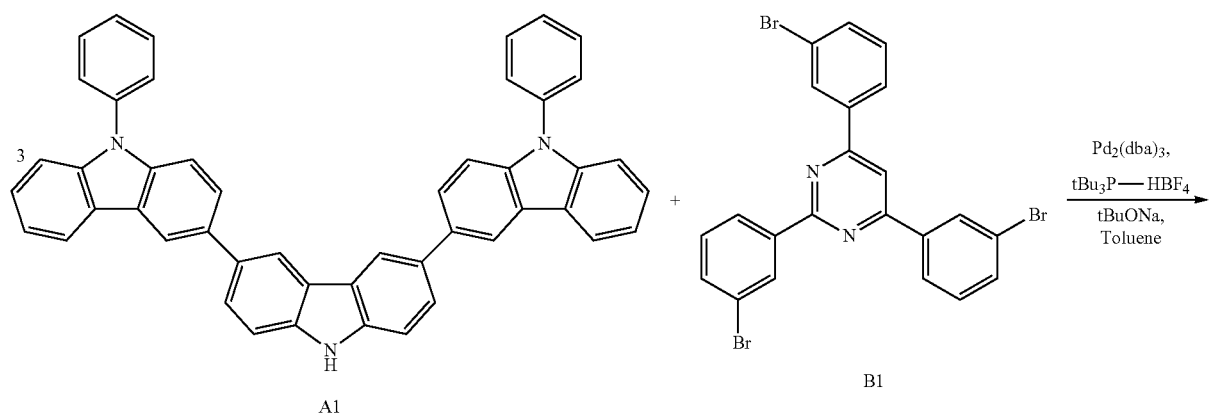
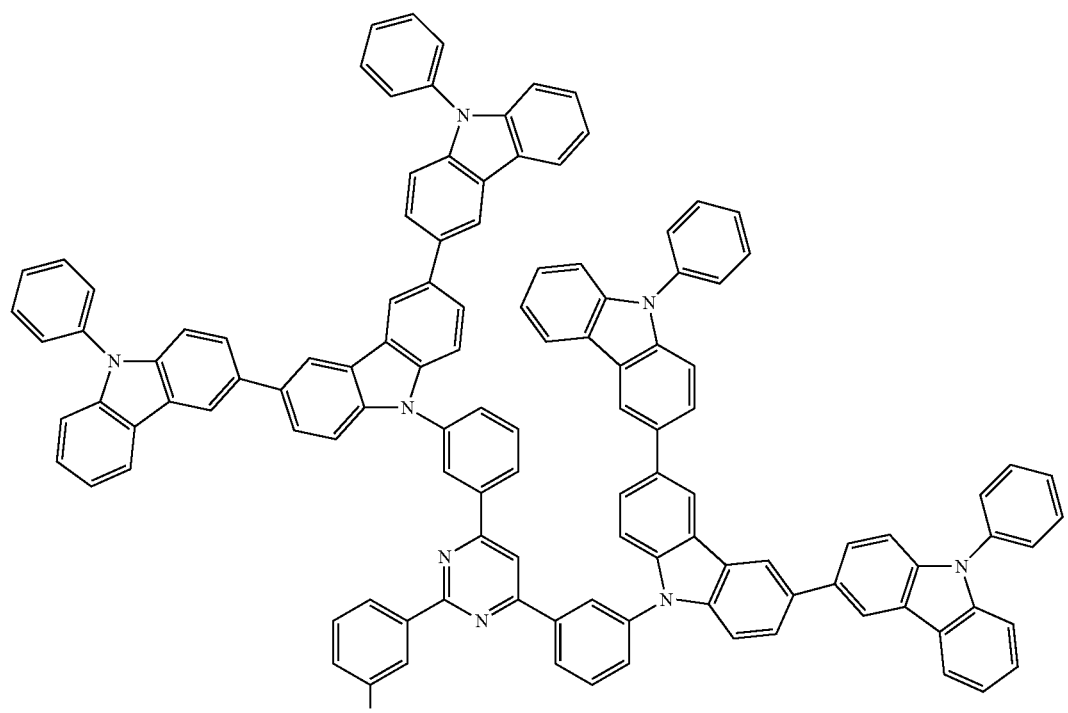

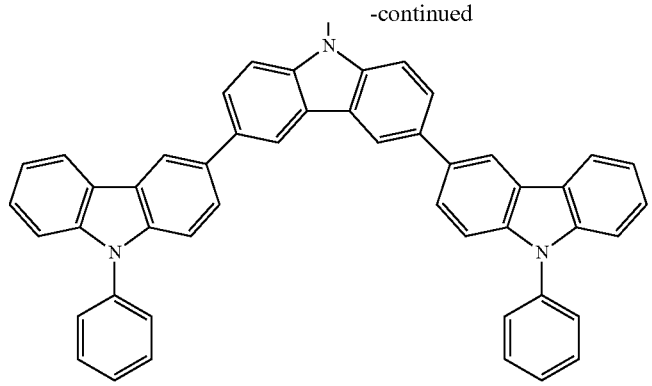

H-1 [I]

Under argon atmosphere, 9-phenylcarbazole-3-boronic acid (12.06 g, 42 mmol), 3,6-dibromocarbazole (5.60 g, 20 mmol), dichloro(diphenylphosphinoferrocene)palladium-methylene chloride complex (0.32 g, 0.4 mmol), 1,4-dioxane (60 mL), and a 2 M aqueous solution of sodium carbonate (60 mL) were successively mixed, and the resultant mixture was refluxed under heating for 7 h.

After cooling the reaction liquid to room temperature, the precipitated solid was collected by filtration, washed with 1,4-dioxane and then water, and dried under reduced pressure. The obtained residue was purified by silica gel column chromatography and then recrystallized from 1,4-dioxane to obtain tricarbazolyl intermediate A1 (11.05 g, yield: 85%).

After adding sodium hydroxide (0.584 g, 14.6 mmol) to a solution of 3-bromobenzaldehyde (17.0 mL, 146 mmol) and 3-bromoacetophenone (19.3 mL, 146 mmol) in methanol (300 mL), the resultant solution was stirred at room temperature for 10.5 h.

The precipitated solid was collected by filtration, washed with methanol, and then dried under vacuum to obtain a cream-colored powder (47.8 g, yield: 90%).

After adding sodium hydroxide (0.745 g, 18.6 mmol) and then ethanol (35 mL) to a mixture of the obtained powder (12.4 g, 33.9 mmol) and 3-bromobenzamidine hydrochloride (4.00 g, 16.9 mmol), the reaction was allowed to proceed for 12.5 h while refluxing under heating. The white powder formed was collected by filtration, washed with ethanol until the washings were made colorless, further washed with water and then ethanol, and then dried under vacuum to obtain target pyrimidine intermediate B1 (5.75 g, yield: 62%).

Under argon atmosphere, tricarbazolyl intermediate A1 (3.58 g, 5.50 mmol), pyrimidine intermediate B1 (1.00 g, 1.83 mmol), tris(dibenzylideneacetone)dipalladium (0.0336 g, 0.0732 mmol), tri-t-butylphosphonium tetrafluoroborate (0.269 g, 0.293 mmol), sodium t-butoxide (0.528 g, 9.0 mmol), and anhydrous toluene (36 mL) were successively mixed, and the resultant mixture was refluxed for 11 h under heating.

After cooling the reaction liquid to room temperature, the insolubles were removed by filtration, and the organic solvent was evaporated off under reduced pressure. The obtained residue was purified by silica gel column chromatography to obtain compound H-1[I] (2.25 g, yield: 55%).

The results of analysis by HPLC (High Performance Liquid Chromatography) and LC-MS (Liquid Chromatography-Mass Spectrometry) on compound H-1[I] are shown below.

HPLC purity: 99.0%

LC-MS: calcd for $C_{166}H_{103}N_{11}$=2249.

found m/z=2249 (M+, 100).

Synthesis Example 2[I](Synthesis of Compound H-2[I])

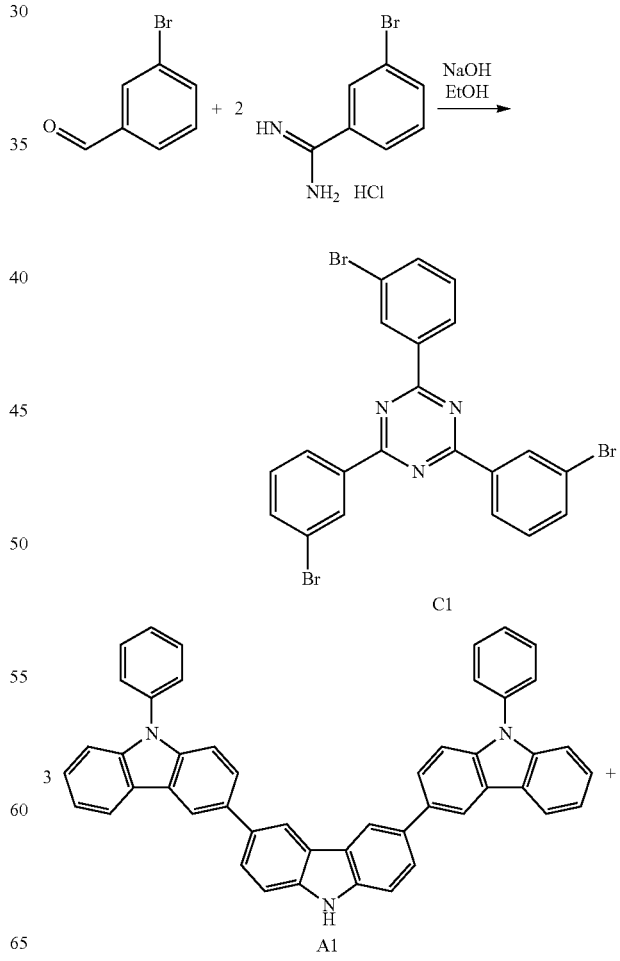

-continued

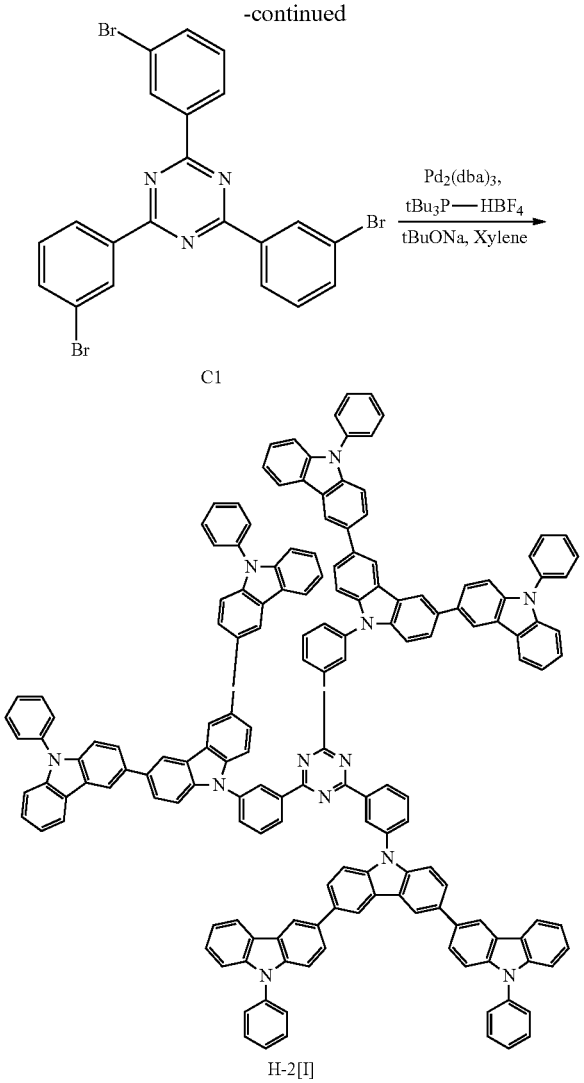

C1

H-2[I]

After mixing 3-bromobenzaldehyde (1.85 g, 10.0 mmol), 3-bromobenzamidine hydrochloride (4.71 g, 20.0 mmol), sodium hydroxide (1.20 g, 30.0 mmol), and ethanol (200 mL), the reaction was allowed to proceed for 7 h while refluxing under heating. The solid formed was collected by filtration. The filtrate was evaporated off under reduced pressure, and chloranil (0.776 g, 3.16 mmol) and dichloromethane (120 mL) were added to the obtained solid. The resultant mixture was stirred at room temperature for one hour. The solid formed was collected by filtration, combined with the solid obtained previously, and recrystallized twice from dichloromethane and then ethanol. The precipitated white powder was collected by filtration and dried under vacuum to obtain target triazine intermediate C1 (4.44 g, yield: 81%).

Under argon atmosphere, tricarbazolyl intermediate A1 (5.30 g, 8.13 mmol), triazine intermediate C1 (1.48 g, 2.71 mmol), tris(dibenzylideneacetone)dipalladium (0.0993 g, 0.108 mmol), tri-t-butylphosphonium tetrafluoroborate (0.126 g, 0.433 mmol), sodium t-butoxide (0.78 g, 8.13 mmol), and anhydrous xylene (50 mL) were successively mixed, and the resultant mixture was refluxed for 8 h under heating.

After cooling the reaction liquid to room temperature, the insolubles were removed by filtration, and the organic solvent was evaporated off under reduced pressure. The obtained residue was purified by silica gel column chromatography to obtain compound H-2[I] (4.27 g, yield: 70%).

The results of analysis by HPLC (High Performance Liquid Chromatography) and LC-MS (Liquid Chromatography-Mass Spectrometry) on compound H-2[I] are shown below.

HPLC purity: 99.0%

LC-MS: calcd for $C_{165}H_{102}N_{12}$=2250.

found m/z=2250 (M+, 100).

Synthesis Example 3[I](Synthesis of Compound H-3[I])

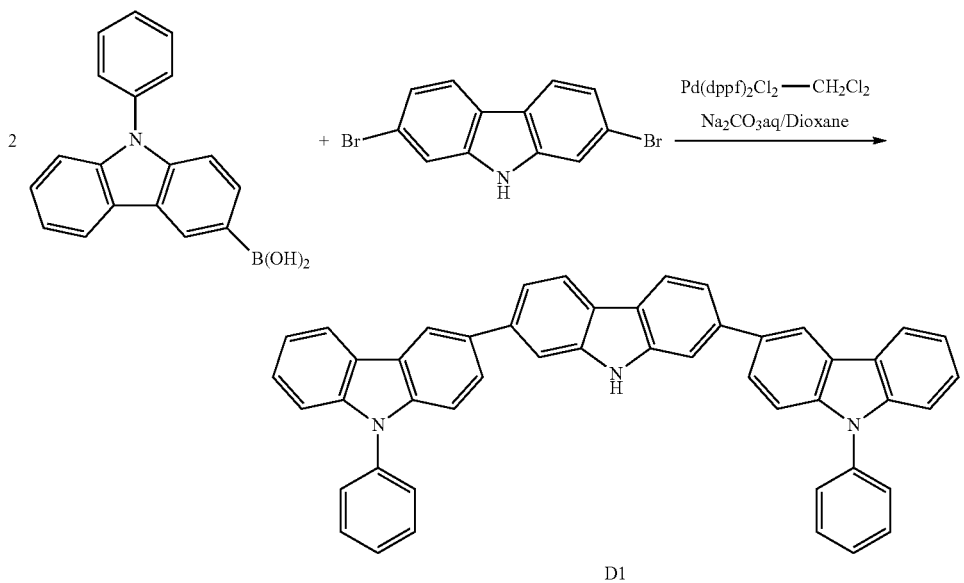

D1

-continued
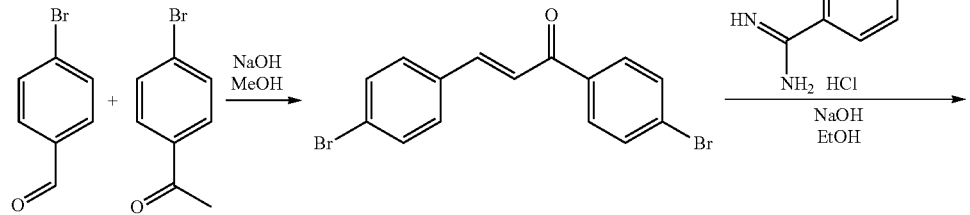
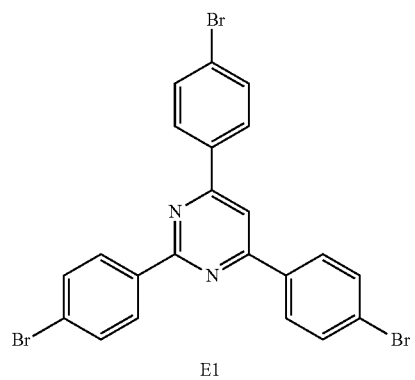
E1
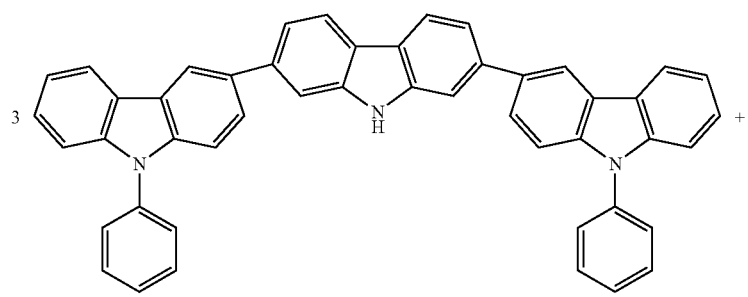
D1
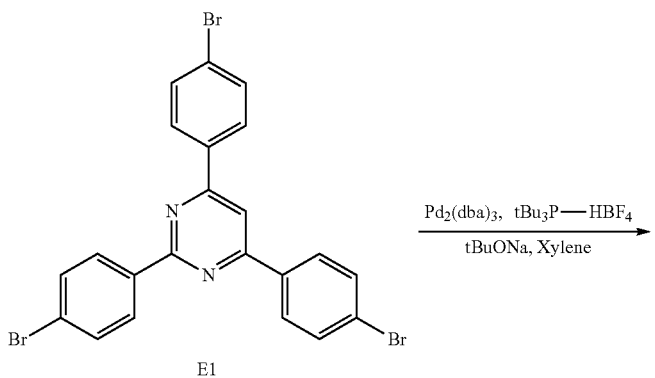
E1
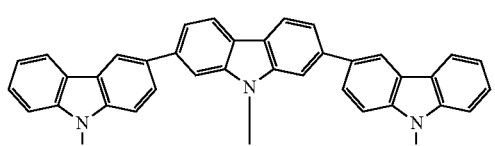

-continued

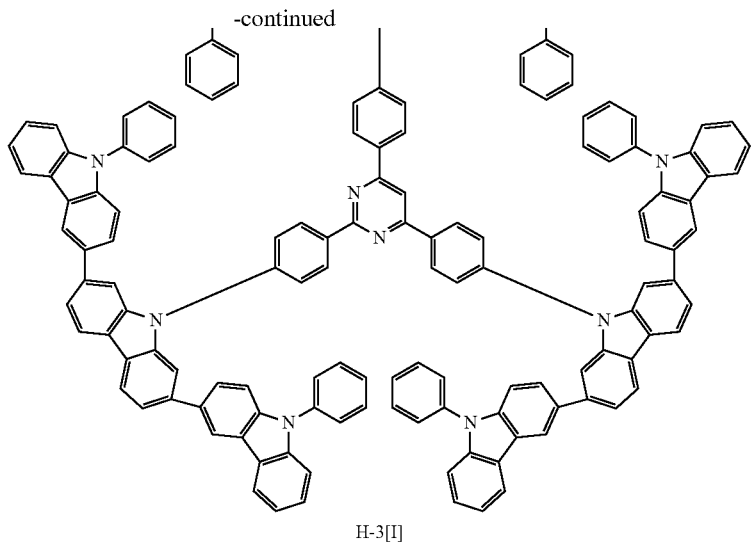

H-3[I]

Under argon atmosphere, 9-phenylcarbazole-3-boronic acid (12.06 g, 42 mmol), 2,7-dibromocarbazole (5.60 g, 20 mmol), dichloro(diphenylphosphinoferrocene)palladium-methylene chloride complex (0.320 g, 0.4 mmol), 1,4-dioxane (60 mL), and a 2 M aqueous solution of sodium carbonate (60 mL) were successively mixed, and the resultant mixture was refluxed under heating for 7 h.

After cooling the reaction liquid to room temperature, the precipitated solid was collected by filtration, washed with 1,4-dioxane and then water, and dried under reduced pressure. The obtained residue was purified by silica gel column chromatography to obtain tricarbazolyl intermediate D1 (9.00 g, yield: 69%).

After adding sodium hydroxide (0.584 g, 14.6 mmol) to a solution of 4-bromobenzaldehyde (17.0 mL, 146 mmol) and 4-bromoacetophenone (19.3 mL, 146 mmol) in methanol (300 mL), the resultant solution was stirred at room temperature for 10.5 h.

The precipitated solid was collected by filtration, washed with methanol, and then dried under vacuum to obtain a powder (47.8 g, yield: 90%).

After adding 4-bromobenzamidine hydrochloride (4.00 g, 16.9 mmol) and sodium hydroxide (0.745 g, 18.6 mmol) and then ethanol (35 mL) to the obtained powder (12.4 g, 33.9 mmol), the reaction was allowed to proceed for 12.5 h while refluxing under heating. The white powder formed was collected by filtration, washed with ethanol until the washings were made colorless, further washed with water and then ethanol, and then dried under vacuum to obtain target pyrimidine intermediate E1 (7.42 g, yield: 80%).

Under argon atmosphere, tricarbazolyl intermediate D1 (3.58 g, 5.50 mmol), pyrimidine intermediate E1 (1.00 g, 1.83 mmol), tris(dibenzylideneacetone)dipalladium (0.0336 g, 0.0732 mmol), tri-t-butylphosphonium tetrafluoroborate (0.269 g, 0.293 mmol), sodium t-butoxide (0.528 g, 9.0 mmol), and anhydrous toluene (36 mL) were successively mixed, and the resultant mixture was refluxed for 11 h under heating.

After cooling the reaction liquid to room temperature, the insolubles were removed by filtration, and the organic solvent was evaporated off under reduced pressure. The obtained residue was purified by silica gel column chromatography to obtain compound H-3[I] (2.86 g, yield: 70%).

The results of analysis by HPLC (High Performance Liquid Chromatography) and LC-MS (Liquid Chromatography-Mass Spectrometry) on compound H-3[I] are shown below.

HPLC purity: 99.0%
LC-MS: calcd for $C_{166}H_{103}N_{11}$=2249.
found m/z=2249 (M+, 100).

Synthesis Example 4[I] (Synthesis of Compound H-4[I])

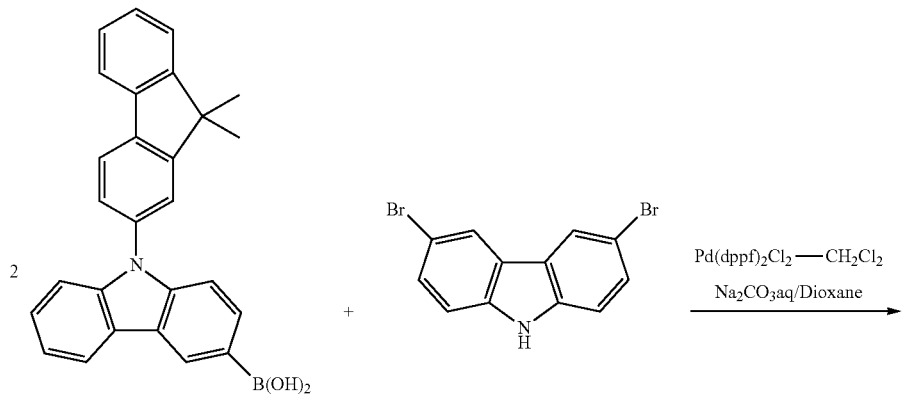

F1

-continued
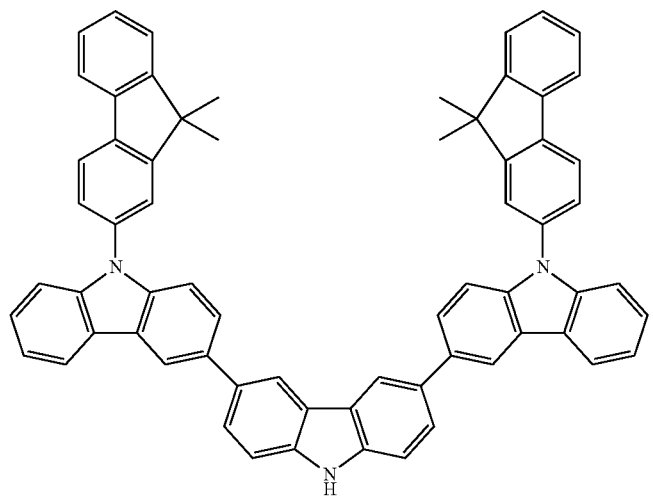
G1
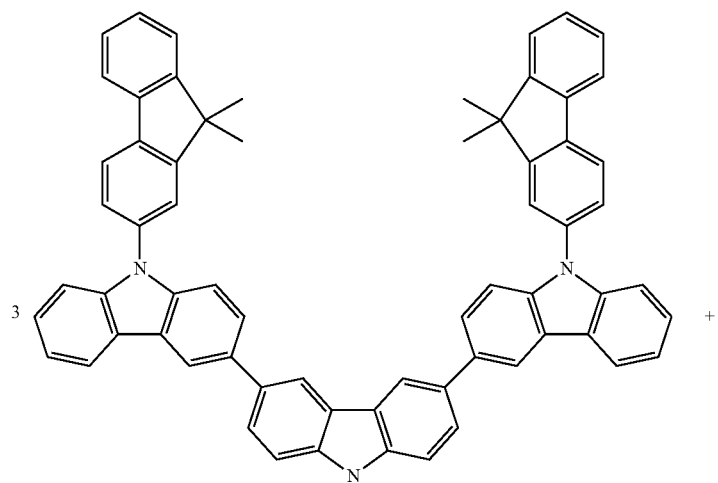
3       G1       +
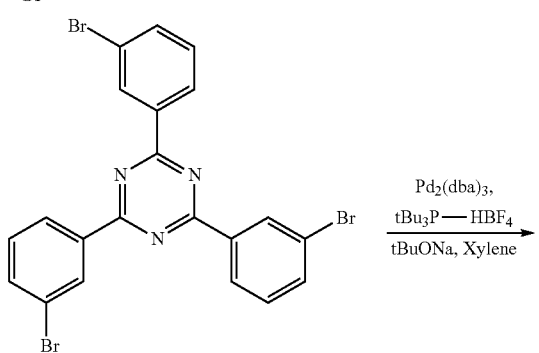
C1
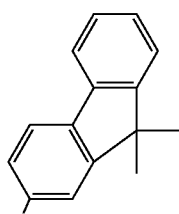

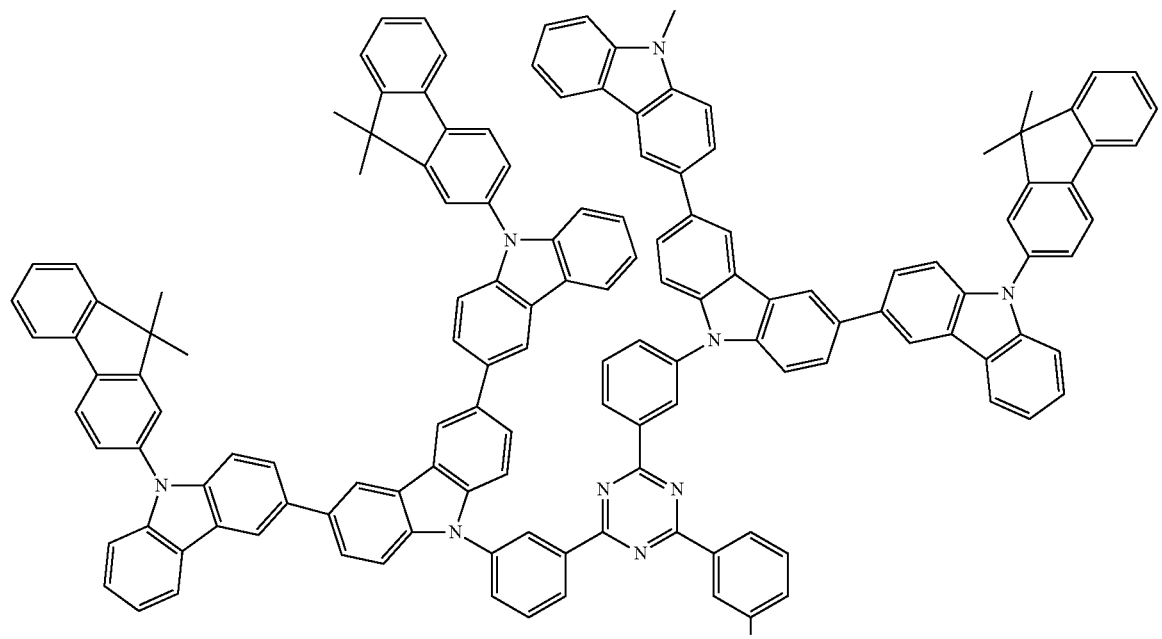

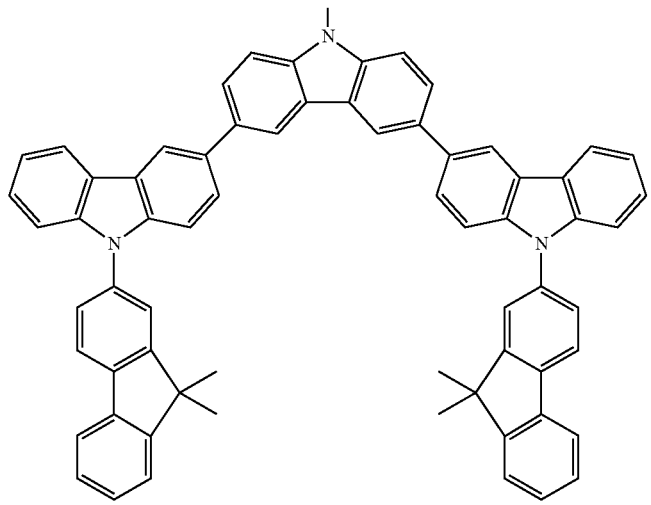

H-4 [I]

Under argon atmosphere, boronic acid F1 (14.00 g, 37.3 mmol), 3,6-dibromocarbazole (5.77 g, 17.8 mmol), dichloro(diphenylphosphinoferrocene)palladium-methylene chloride complex (0.290 g, 0.355 mmol), 1,4-dioxane (90 mL), and a 2 M aqueous solution of sodium carbonate (55 mL) were successively mixed, and the resultant mixture was refluxed for 10 h under heating.

After cooling the reaction liquid to room temperature, the precipitated solid was collected by filtration, washed with 1,4-dioxane and then water, and dried under reduced pressure. The obtained residue was purified by silica gel column chromatography to obtain tricarbazolyl intermediate G1 (12.1 g, yield: 77%).

Under argon atmosphere, tricarbazolyl intermediate G1 (5.29 g, 6.00 mmol), triazine intermediate C1 (1.09 g, 2.00 mmol), tris(dibenzylideneacetone)dipalladium (0.0733 g, 0.0800 mmol), tri-t-butylphosphonium tetrafluoroborate (0.0928 g, 0.320 mmol), sodium t-butoxide (0.577 g, 6.0 mmol), and anhydrous xylene (40 mL) were successively mixed, and the resultant mixture was refluxed for 11 h under heating.

After cooling the reaction liquid to room temperature, the insolubles were removed by filtration and the organic solvent was evaporated off under reduced pressure. The obtained residue was purified by silica gel column chromatography to obtain compound H-4[I] (3.83 g, yield: 65%).

The results of analysis by HPLC (High Performance Liquid Chromatography) and LC-MS (Liquid Chromatography-Mass Spectrometry) on compound H-4[I] are shown below.

HPLC purity: 98.6%

LC-MS: calcd for $C_{219}H_{150}N_{12}$=2948.

found m/z=2948 (M+, 100).

Synthesis Example 5[I](Synthesis of Compound H-5[I])
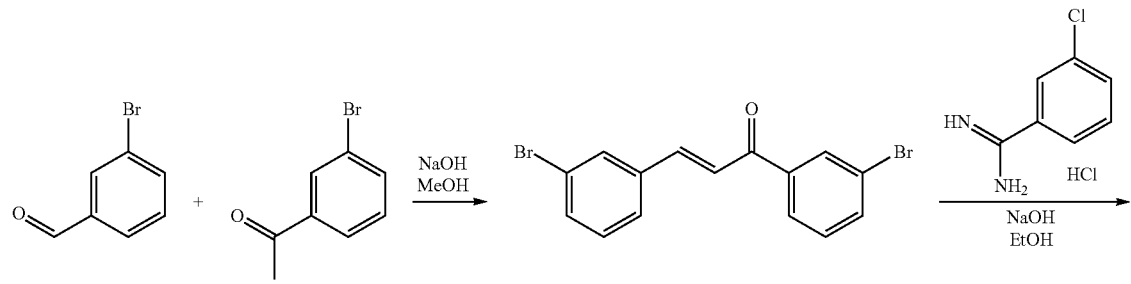
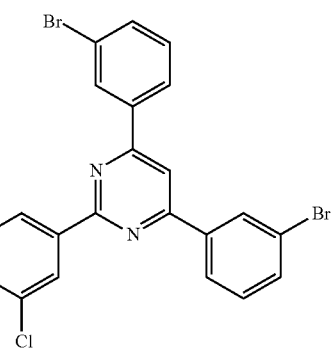
J1
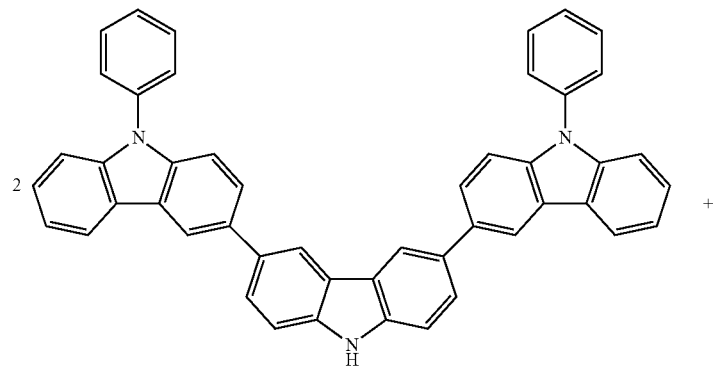
A1
+
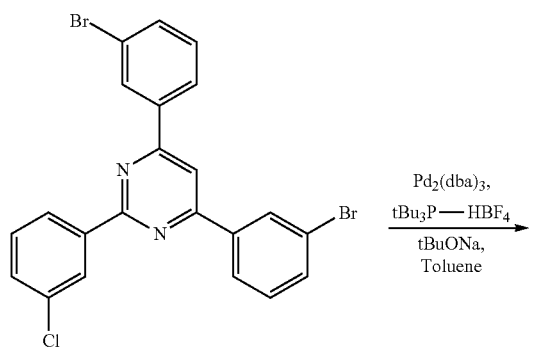
J1

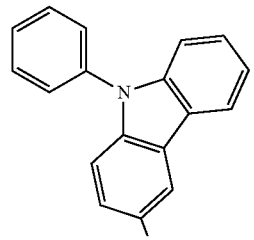
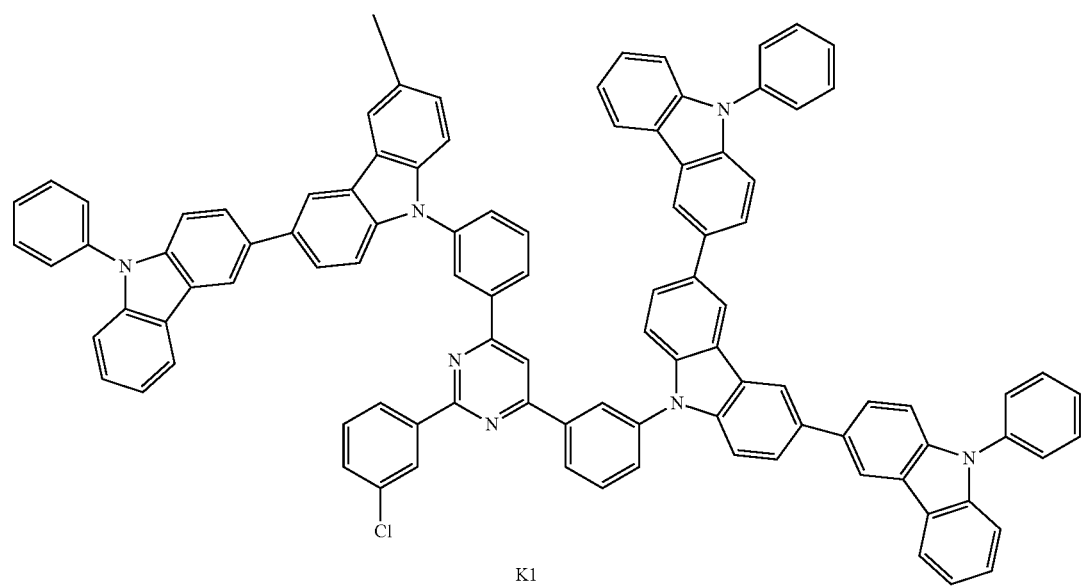
K1
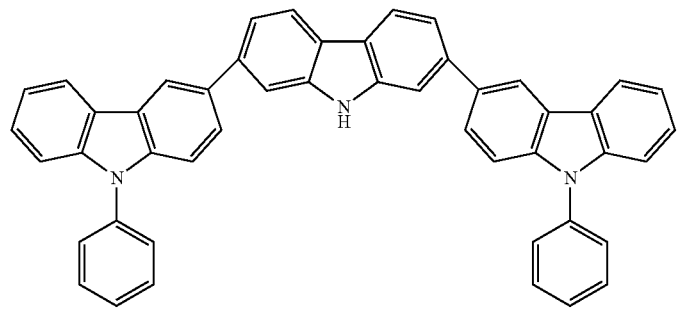
D1
+
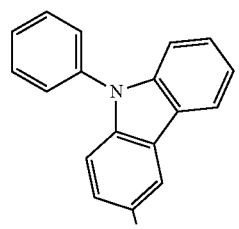

-continued

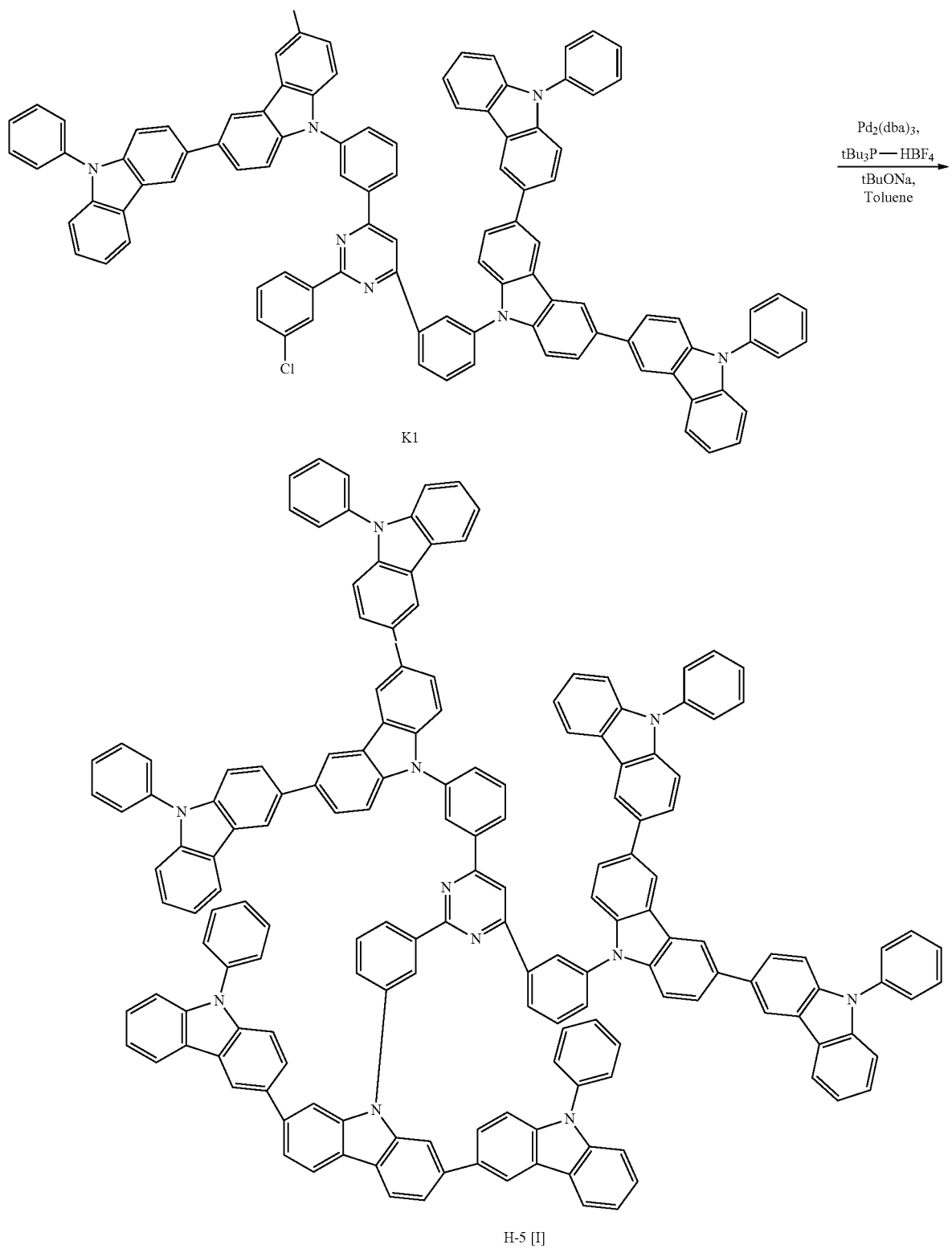

K1

H-5 [I]

After adding sodium hydroxide (0.584 g, 14.6 mmol) to a solution of 3-bromobenzaldehyde (17.0 mL, 146 mmol) and 3-bromoacetophenone (19.3 mL, 146 mmol) in methanol (300 mL), the resultant solution was stirred at room temperature for 10.5 h.

The precipitated solid was collected by filtration, washed with methanol, and then dried under vacuum to obtain a cream-colored powder (47.8 g, yield: 90%).

After adding 3-chlorobenzamidine hydrochloride (3.23 g, 16.9 mmol) and sodium hydroxide (0.745 g, 18.6 mmol) and then ethanol (35 mL) to the obtained powder (12.4 g, 33.9 mmol), the reaction was allowed to proceed for 12.5 h while refluxing under heating. The white powder formed was collected by filtration, washed with ethanol until the washings were made colorless, further washed with water and then ethanol, and then dried under vacuum to obtain the target pyrimidine intermediate J1 (5.25 g, yield: 62%).

Under argon atmosphere, tricarbazolyl intermediate A1 (3.90 g, 6.00 mmol), pyrimidine intermediate J1 (1.50 g, 3.00 mmol), tris(dibenzylideneacetone)dipalladium (0.110 g, 0.120 mmol, tri-t-butylphosphonium tetrafluoroborate (0.139 g, 0.48 mmol), sodium t-butoxide (0.288 g, 3.00 mmol), and anhydrous toluene (60 mL) were successively mixed, and the resultant mixture was refluxed for 11 h under heating.

After cooling the reaction liquid to room temperature, the insolubles were removed by filtration and the organic solvent was evaporated off under reduced pressure. The obtained residue was purified by silica gel column chromatography to obtain compound K1 (2.70 g, yield: 55%).

Under argon atmosphere, compound K1 (2.70 g, 3.00 mmol), carbazolyl intermediate D1 (1.95 g, 3.00 mmol), tris(dibenzylideneacetone)dipalladium (0.110 g, 0.120 mmol), tri-t-butylphosphonium tetrafluoroborate (0.139 g, 0.48 mmol), sodium t-butoxide (0.288 g, 3.00 mmol), and anhydrous toluene (60 mL) were successively mixed, and the resultant mixture was refluxed for 11 h under heating.

After cooling the reaction liquid to room temperature, the insolubles were removed by filtration and the organic solvent was evaporated off under reduced pressure. The obtained residue was purified by silica gel column chromatography to obtain compound H-5[I] (5.74 g, yield: 85%).

The results of analysis by HPLC (High Performance Liquid Chromatography) and LC-MS (Liquid Chromatography-Mass Spectrometry) on compound H-5[I] are shown below.

HPLC purity: 99.0%

LC-MS: calcd for $C_{166}H_{103}N_{11}$=2249.

found m/z=2249 (M+, 100).

Synthesis Example 6[I](Synthesis of Compound H-6[I])

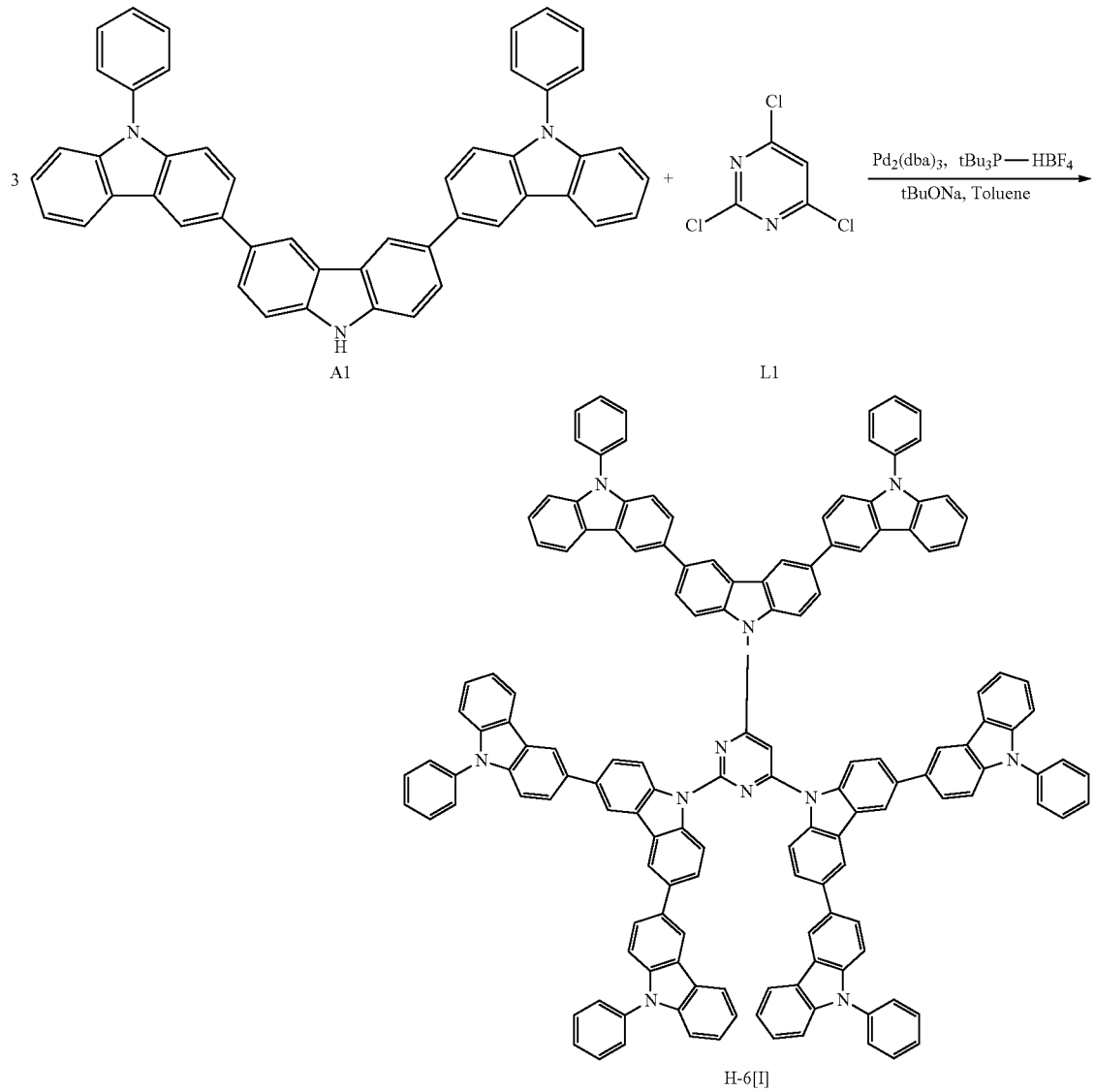

Under argon atmosphere, tricarbazolyl intermediate A1 (5.85 g, 9.00 mmol), pyrimidine intermediate L1 (0.550 g, 3.00 mmol), tris(dibenzylideneacetone)dipalladium (0.110 g, 0.120 mmol), tri-t-butylphosphonium tetrafluoroborate (0.139 g, 0.48 mmol), sodium t-butoxide (0.288 g, 3.00 mmol), and anhydrous toluene (60 mL) were successively mixed, and the resultant mixture was refluxed for 11 h under heating.

After cooling the reaction liquid to room temperature, the insolubles were removed by filtration, the organic solvent was evaporated off under reduced pressure. The obtained residue was purified by silica gel column chromatography to obtain compound H-6[I] (4.86 g, yield: 80%).

The results of analysis by HPLC (High Performance Liquid Chromatography) and LC-MS (Liquid Chromatography-Mass Spectrometry) on compound H-6[I] are shown below.

HPLC purity: 99.0%
LC-MS: calcd for $C_{148}H_{91}N_{11}$=2021.
found m/z=2021 (M+, 100).

The compounds within the scope of the claims of this application can be synthesized by referring to the above synthetic reactions while using a known synthetic reaction and a starting material in accordance with the target compound.

Example 1[I]

Cleaning of Substrate

A glass substrate of 25 mm×25 mm×1.1 mm thickness having an ITO transparent electrode (product of Geomatec Company) was cleaned by ultrasonic cleaning in isopropyl alcohol for 5 min and then UV ozone cleaning for 5 min.

Formation of Underlayers

Clevious AI4083 (tradename) manufactured by Heraeus as a hole transporting material was spin-coated on the ITO substrate to form a hole transporting layer with a thickness of 30 nm. Thereafter, unnecessary portion was removed by acetone and then a base substrate was produced by baking in air for 10 min on a hot plate at 200° C.

Formation of Light Emitting Layer

A 1.6% by mass toluene solution containing the compound H-1[I] obtained in Synthesis Example 1[I] as a host material and the following compound D-i as a dopant material was prepared in a mixing ratio of compound H-1[I]:compound D-i=95:5 by mass. The toluene solution was spin-coated on the base substrate into a thickness of 50 nm. Thereafter, unnecessary portion was removed by toluene and then the coated film was dried under heating at 150° C. on a hot plate to obtain a coat-laminated substrate having a light emitting layer. The film-forming operations for forming the light emitting layer were all conducted in a glove box under a nitrogen atmosphere.

Vapor Deposition and Sealing

The coat-laminated substrate was conveyed into a vapor deposition chamber and the following compound ET-1 as an electron transporting material was vapor-deposited into a thickness of 50 nm to form an electron transporting layer. Then, lithium fluoride was vapor-deposited into a thickness of 1 nm and aluminum was vapor-deposited into a thickness of 80 nm. After completing all the vapor deposition processes, the substrate with laminated films was sealed with a bored glass in a glove box under a nitrogen atmosphere to produce an organic EL device.

Evaluation of Device

By driving at a direct current, the obtained organic EL device was allowed to emit light to measure the external quantum efficiency (EQE) at a current density of 10 mA/cm$^2$. The result is shown in Table 1.

An organic EL device was produced in the same manner as described above except for drying the coated film at 200° C. under heating in the formation of the light emitting layer. The obtained organic EL device was measured for the external quantum efficiency (EQE) in the same manner as described above. The result is shown in Table 1.

Example 2[I]

Each organic EL device wherein the coated film was dried at 150° C., or 200° C. under heating was produced in the same manner as in Example 1[I] except for using compound H-2[I] obtained in Synthesis Example 2[I] as a host material. The measured external quantum efficiency (EQE) of each organic EL device is shown in Table 1.

Example 3[I]

Each organic EL device wherein the coated film was dried at 150° C., or 200° C. under heating was produced in the same manner as in Example 1[I] except for using compound H-3[I] obtained in Synthesis Example 3[I] as a host material. The measured external quantum efficiency (EQE) of each organic EL device is shown in Table 1.

Example 4[I]

Each organic EL device wherein the coated film was dried at 150° C., or 200° C. under heating was produced in the same manner as in Example 1[I] except for using compound H-4[I] obtained in Synthesis Example 4[I] as a host material. The measured external quantum efficiency (EQE) of each organic EL device is shown in Table 1.

Example 5[I]

Each organic EL device wherein the coated film was dried at 150° C., or 200° C. under heating was produced in the same manner as in Example 1[I] except for using compound H-5[I] obtained in Synthesis Example 5[I] as a host material. The measured external quantum efficiency (EQE) of each organic EL device is shown in Table 1.

Example 6[I]

Each organic EL device wherein the coated film was dried at 150° C., or 200° C. under heating was produced in the same manner as in Example 1[I] except for using compound H-6[I] obtained in Synthesis Example 6[I] as a host material. The measured external quantum efficiency (EQE) of each organic EL device is shown in Table 1.

Comparative Example 1[I]

An organic EL device wherein the coated film was dried at 150° C. under heating was produced in the same manner as in Example 1[I] except for using compound Q-1[I] described in WO 2012/086170 as a host material. The measured external quantum efficiency (EQE) of the organic EL device is shown in Table 1.

Comparative Example 2[I]

Each organic EL device wherein the coated film was dried at 150° C., or 200° C. under heating was produced in the same manner as in Example 1[I] except for using compound Q-2[I] as a host material. The measured external quantum efficiency (EQE) of each organic EL device is shown in Table 1.

2213    2214
D-i
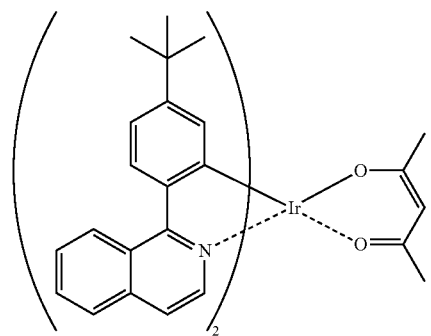
ET-1
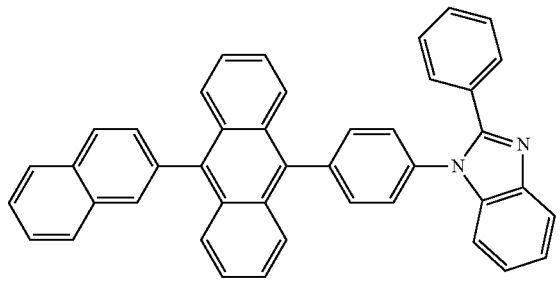
Q-1[I]
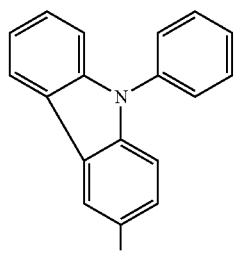
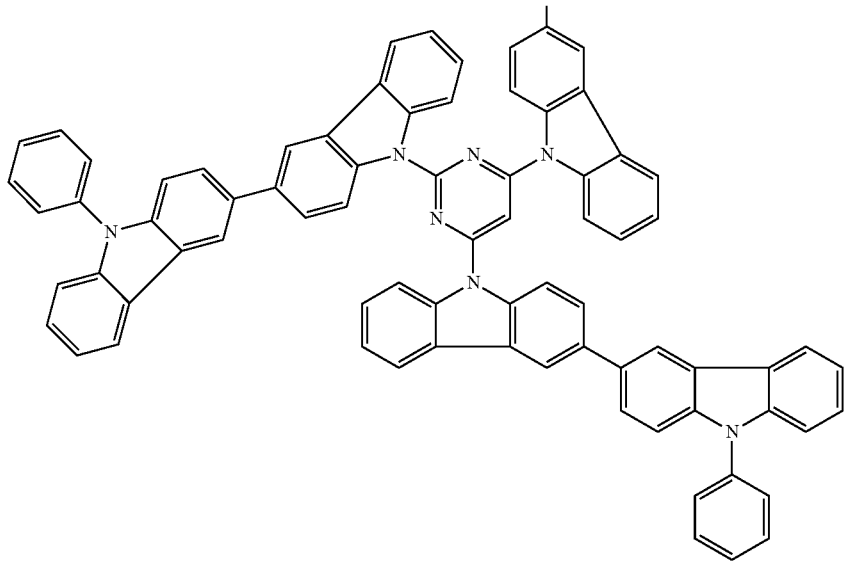
Q-2[I]
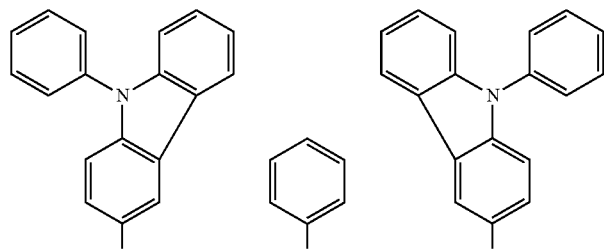

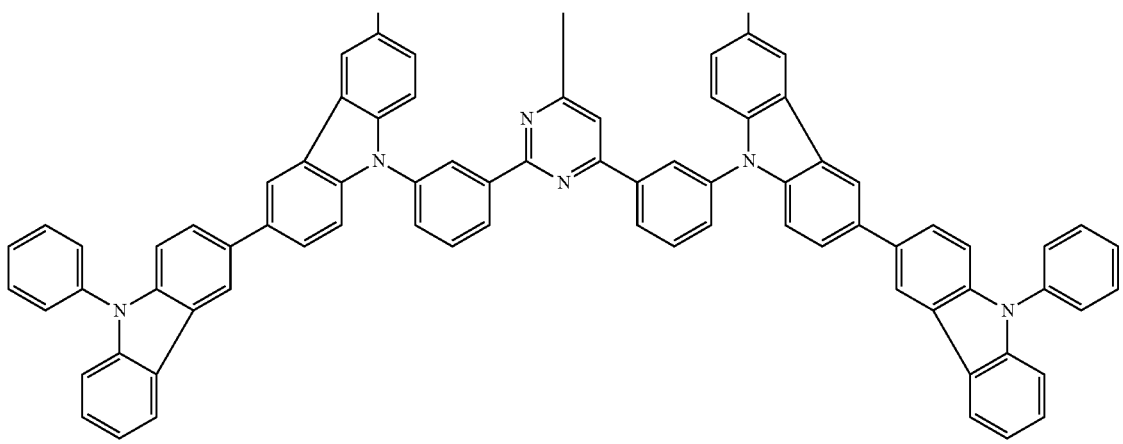

| | Host material | External quantum efficiency (%) | |
|---|---|---|---|
| | | dried at 150° C. | dried at 200° C. |
| Example 1[I] | H-1[I] | 5.1 | 4.9 |
| Example 2[I] | H-2[I] | 5.2 | 5.0 |
| Example 3[I] | H-3[I] | 4.3 | 4.3 |
| Example 4[I] | H-4[I] | 4.9 | 4.7 |
| Example 5[I] | H-5[I] | 4.7 | 4.6 |
| Example 6[I] | H-6[I] | 4.5 | 4.1 |
| Comparative Example 1[I] | Q-1[I] | 2.1 | —*1 |
| Comparative Example 2[I] | Q-2[I] | 4.8 | 2.7 |

*1 not measured because the external quantum efficiency was low when dried at 150° C.

(2) Next, the synthesis method of compound 1[II], the production method of organic EL devices employing compound 1[II], and the evaluation results thereof are described below.

Compound 1[II]

Synthesis Example 1[II] (Synthesis of Compound H-1[II])

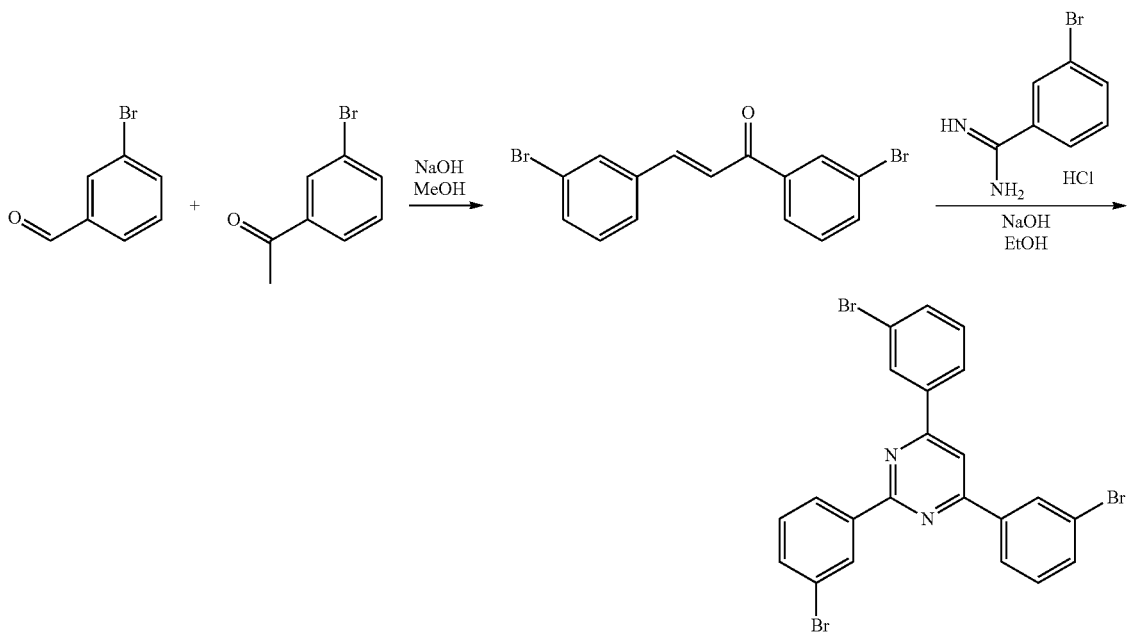

A1

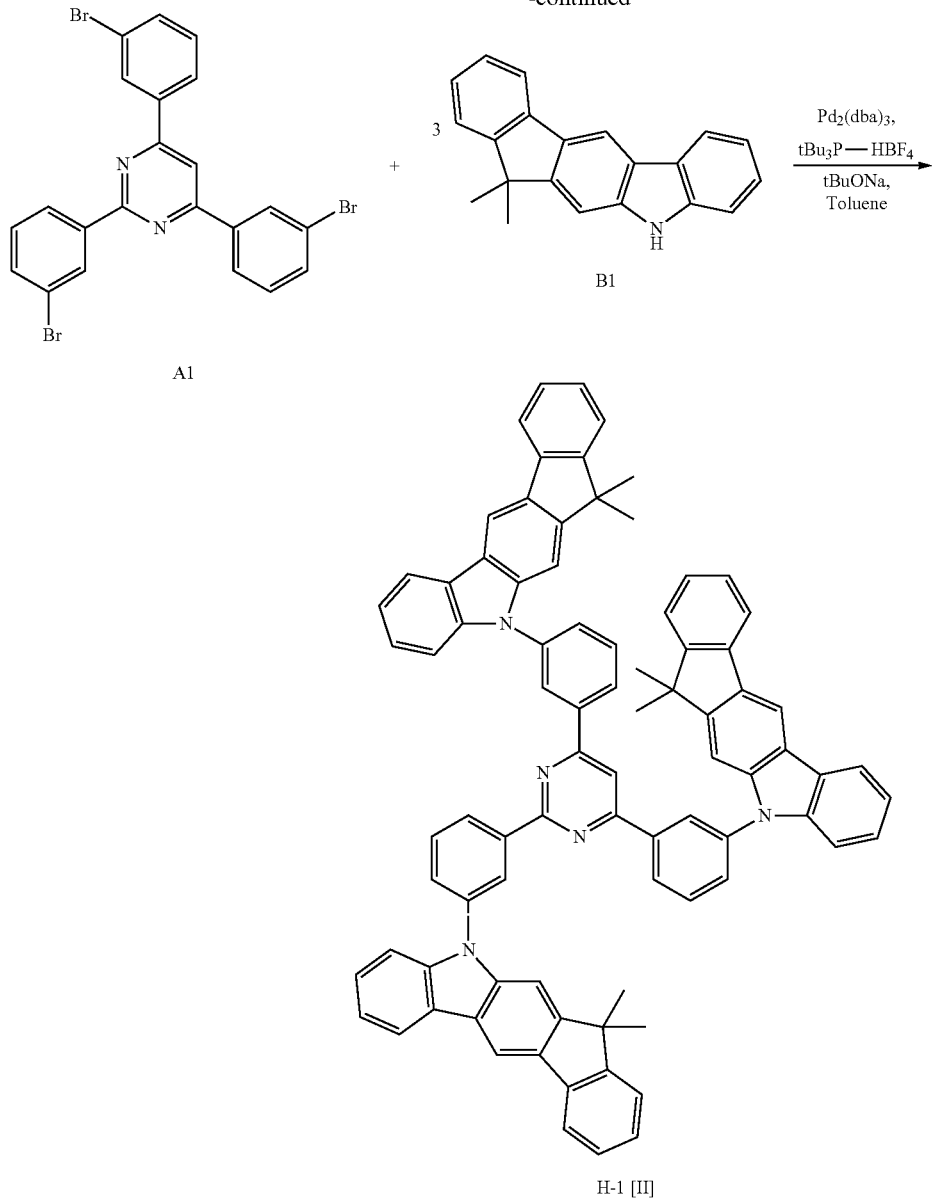

After adding sodium hydoxide (0.584 g, 14.6 mmol) to a solution of 3-bromobenzaldehyde (17.0 mL, 146 mmol) and 3-bromoacetophenone (19.3 mL, 146 mmol) in methanol (300 mL), the resultant solution was stirred at room temperature for 10.5 h.

The precipitated solid was collected by filtration, washed with methanol, and then dried under vacuum to obtain a powder (47.8 g, yield: 90%).

Then, after adding 3-bromobenzamidine hydrochloride (4.00 g, 16.9 mmol) and sodium hydroxide (0.745 g, 18.6 mmol) and then ethanol (35 mL) to the obtained powder (12.4 g, 33.9 mmol), the reaction was allowed to proceed for 12.5 h while refluxing under heating. The white powder formed was collected by filtration, washed with ethanol until the washings were made colorless, further washed with water and then ethanol, and then dried under vacuum to obtain target pyrimidine intermediate A1 (7.42 g, yield: 80%).

Under argon atmosphere, carbazolyl intermediate B1 (2.55 g, 9.00 mmol), pyrimidine intermediate A1 (1.64 g, 3.00 mmol), tris(dibenzylideneacetone)dipalladium (0.110 g, 0.120 mmol), tri-t-butylphosphonium tetrafluoroborate (0.139 g, 0.480 mmol), sodium t-butoxide (0.965 g, 9.00 mmol), and anhydrous toluene (60 mL) were successively mixed, and the resultant mixture was refluxed for 8 h under heating.

After cooling the reaction liquid to room temperature, the insolubles were removed by filtration, and the organic solvent was evaporated off under reduced pressure. The obtained residue was purified by silica gel column chromatography to obtain compound H-1[II] (2.25 g, yield: 65%).

The results of analysis by HPLC (High Performance Liquid Chromatography) and LC-MS (Liquid Chromatography-Mass Spectrometry) on compound H-1[II] are shown below.

HPLC purity: 99.2%

LC-MS: calcd for $C_{85}H_{61}N_5$=1151.

found m/z=1151 (M+, 100).

Synthesis Example 2[II](Synthesis of Compound H-2[II])
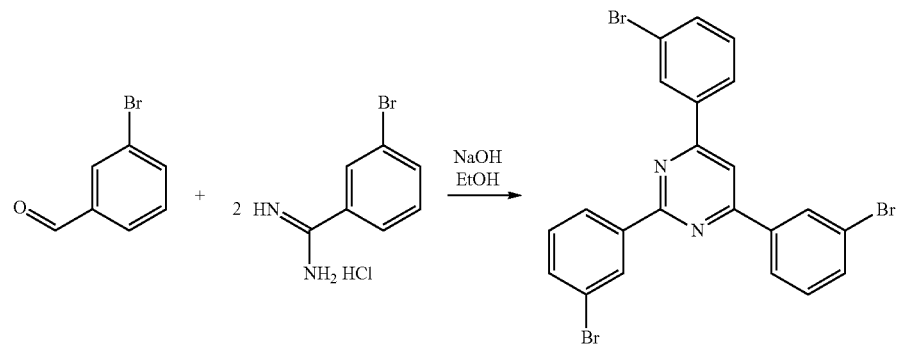
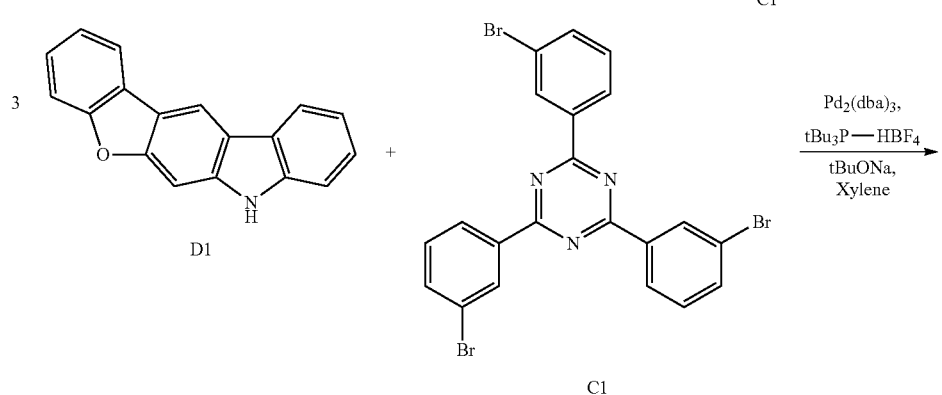
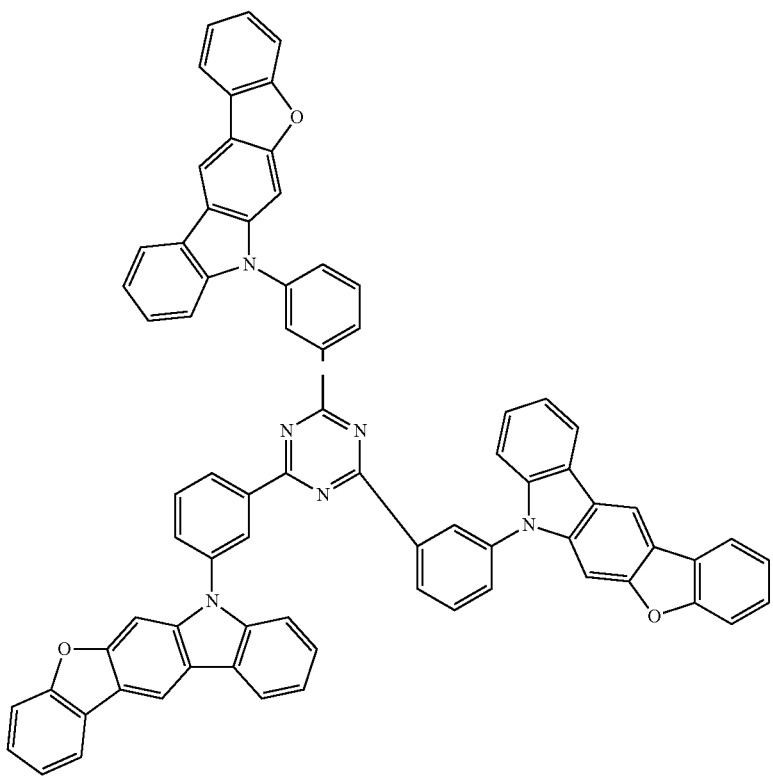
H-2 [II]

After mixing 3-bromobenzaldehyde (1.85 g, 10.0 mmol), 3-bromobenzamidine hydrochloride (4.71 g, 20.0 mmol), sodium hydroxide (1.20 g, 30.0 mmol), and ethanol (200 mL), the reaction was allowed to proceed for 7 h while refluxing under heating. The solid formed was collected by filtration. The filtrate was evaporated off under reduced pressure, and chloranil (0.776 g, 3.16 mmol) and dichloromethane (120 mL) were added to the obtained solid. The resultant mixture was stirred at room temperature for one hour. The solid formed was collected by filtration, combined with the solid obtained previously, and recrystallized twice from dichloromethane and then ethanol. The precipitated white powder was collected by filtration and dried under vacuum to obtain target triazine intermediate C1 (4.44 g, yield: 81%).

Under argon atmosphere, carbazolyl intermediate D1 (2.32 g, 9.00 mmol), triazine intermediate C1 (1.64 g, 3.00 mmol), tris(dibenzylideneacetone)dipalladium (0.110 g, 0.120 mmol), tri-t-butylphosphonium tetrafluoroborate (0.139 g, 0.480 mmol), sodium t-butoxide (0.965 g, 9.00 mmol), and anhydrous xylene (60 mL) were successively mixed, and the resultant mixture was refluxed for 8 h under heating.

After cooling the reaction liquid to room temperature, the insolubles were removed by filtration, and the organic solvent was evaporated off under reduced pressure. The obtained residue was purified by silica gel column chromatography to obtain compound H-2[II] (2.26 g, yield: 70%).

The results of analysis by HPLC (High Performance Liquid Chromatography) and LC-MS (Liquid Chromatography-Mass Spectrometry) on compound H-2[II] are shown below.

HPLC purity: 99.4%

LC-MS: calcd for $C_{75}H_{42}N_6O_3$=1074.

found m/z=1074 (M+, 100).

Synthesis Example 3[II](Synthesis of Compound H-3[II])

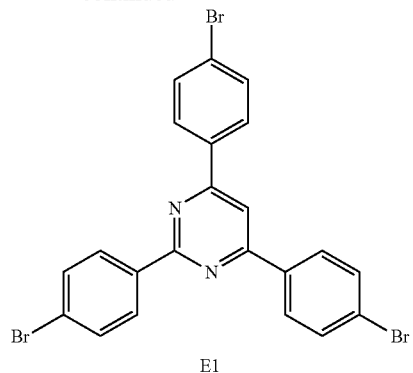

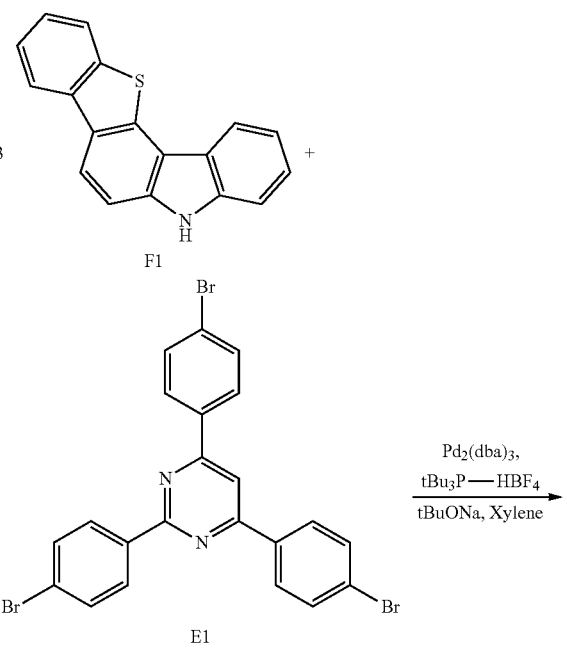

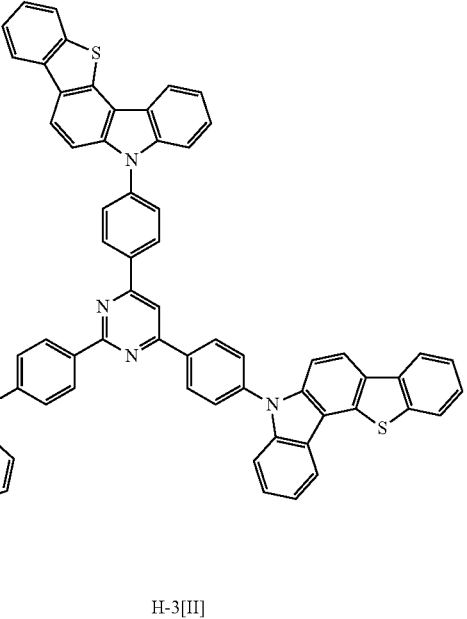

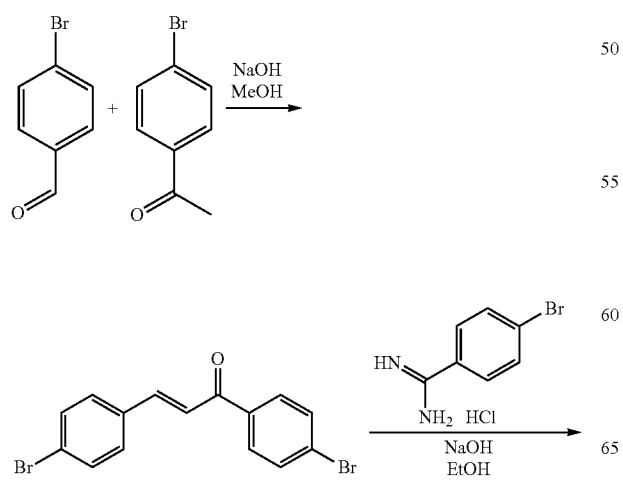

After adding sodium hydroxide (0.584 g, 14.6 mmol) to a solution of 4-bromobenzaldehyde (17.0 mL, 146 mmol)

and 4-bromoacetophenone (19.3 mL, 146 mmol) in methanol (300 mL), the resultant solution was stirred at room temperature for 10.5 h.

The precipitated solid was collected by filtration, washed with methanol, and then dried under vacuum to obtain a powder (47.8 g, yield: 90%).

Then, after adding 4-bromobenzamidine hydrochloride (4.00 g, 16.9 mmol) and sodium hydroxide (0.745 g, 18.6 mmol) and then ethanol (35 mL) to the obtained powder (12.4 g, 33.9 mmol), the reaction was allowed to proceed for 12.5 h while refluxing under heating. The white powder formed was collected by filtration, washed with ethanol until the washings were made colorless, further washed with water and then ethanol, and then dried under vacuum to obtain target pyrimidine intermediate E1 (7.42 g, yield: 80%).

Under argon atmosphere, carbazolyl intermediate F1 (2.46 g, 9.00 mmol), pyrimidine intermediate E1 (1.64 g, 3.00 mmol), tris(dibenzylideneacetone)dipalladium (0.110 g, 0.120 mmol, tri-t-butylphosphonium tetrafluoroborate (0.139 g, 0.480 mmol), sodium t-butoxide (0.965 g, 9.00 mmol), and anhydrous xylene (60 mL) were successively mixed, and the resultant mixture was refluxed for 8 h under heating.

After cooling the reaction liquid to room temperature, the insolubles were removed by filtration, the organic solvent was evaporated off under reduced pressure. The obtained residue was purified by silica gel column chromatography to obtain compound H-3[II] (2.19 g, yield: 65%).

The results of analysis by HPLC (High Performance Liquid Chromatography) and LC-MS (Liquid Chromatography-Mass Spectrometry) on compound H-3[II] are shown below.

HPLC purity: 99.2%
LC-MS: calcd for $C_{76}H_{43}N_5S_3$=1121.
found m/z=1121 (M+, 100).

Synthesis Example 4[II](Synthesis of Compound H-4[II])

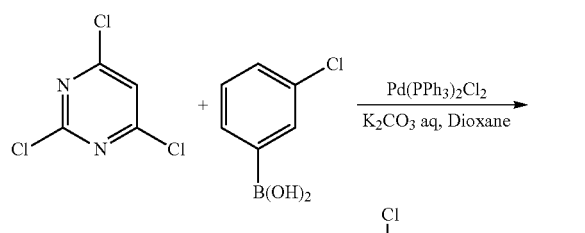

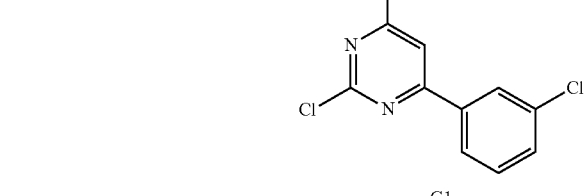

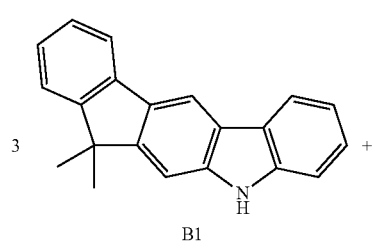

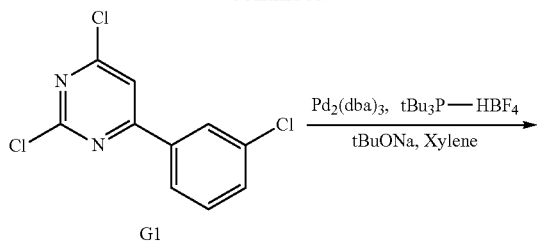

G1

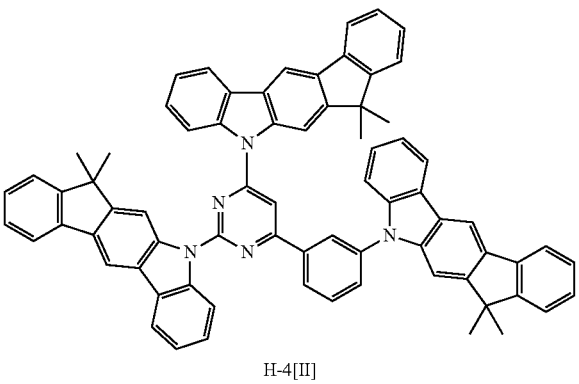

H-4[II]

Under argon atmosphere, 2,4,6-trichloropyrimidine (3.67 g, 20 mmol), 3-chlorophenylboronic acid (3.13 g, 20 mmol), dichloro(bistriphenylphosphine)palladium complex (0.351 g, 0.5 mmol), 1,4-dioxane (80 mL), and a 2 M aqueous solution of potassium carbonate (40 mL) were successively mixed, and the resultant mixture was refluxed for 8 h under heating. After cooling to room temperature, the reaction liquid was diluted with toluene, washed with water, and dried under reduced pressure. The obtained residue was purified by silica gel column chromatography to obtain pyrimidine intermediate G1 (4.05 g, yield: 78%).

Under argon atmosphere, carbazolyl intermediate B1 (2.55 g, 9.00 mmol), pyrimidine intermediate G1 (0.779 g, 3.00 mmol), tris(dibenzylideneacetone)dipalladium (0.110 g, 0.120 mmol), tri-t-butylphosphonium tetrafluoroborate (0.139 g, 0.480 mmol), sodium t-butoxide (0.965 g, 9.00 mmol), and anhydrous xylene (60 mL) were successively mixed, and the resultant mixture was refluxed for 8 h under heating.

After cooling the reaction liquid to room temperature, the insolubles were removed by filtration, and the organic solvent was evaporated off under reduced pressure. The obtained residue was purified by silica gel column chromatography to obtain compound H-4[II] (1.65 g, yield: 55%).

The results of analysis by HPLC (High Performance Liquid Chromatography) and LC-MS (Liquid Chromatography-Mass Spectrometry) on compound H-4[II] are shown below.

HPLC purity: 98.6%
LC-MS: calcd for $C_{73}H_{53}N_5$=999.
found m/z=999 (M+, 100).

Synthesis Example 5[II](Synthesis of Compound H-5[II])
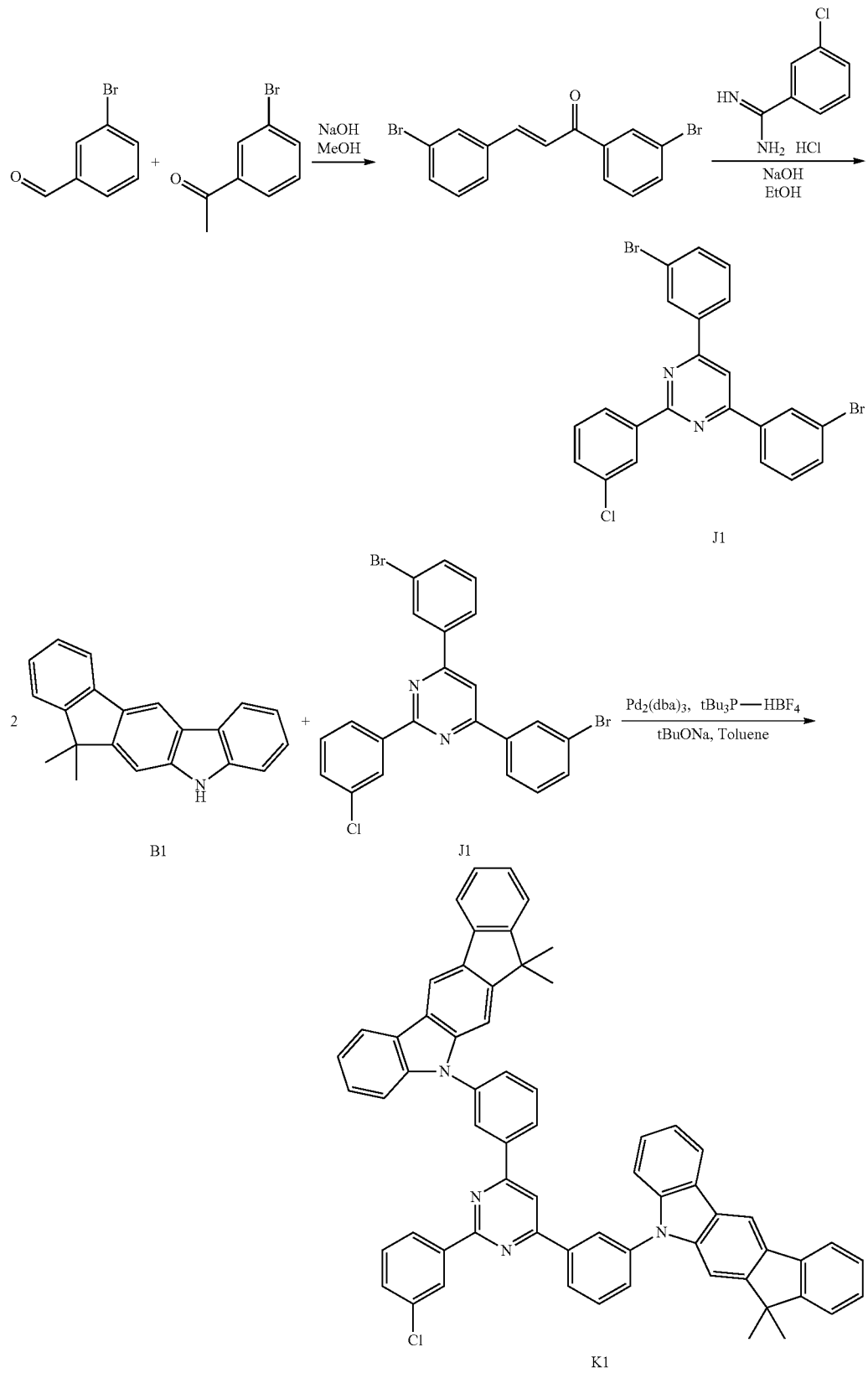

-continued

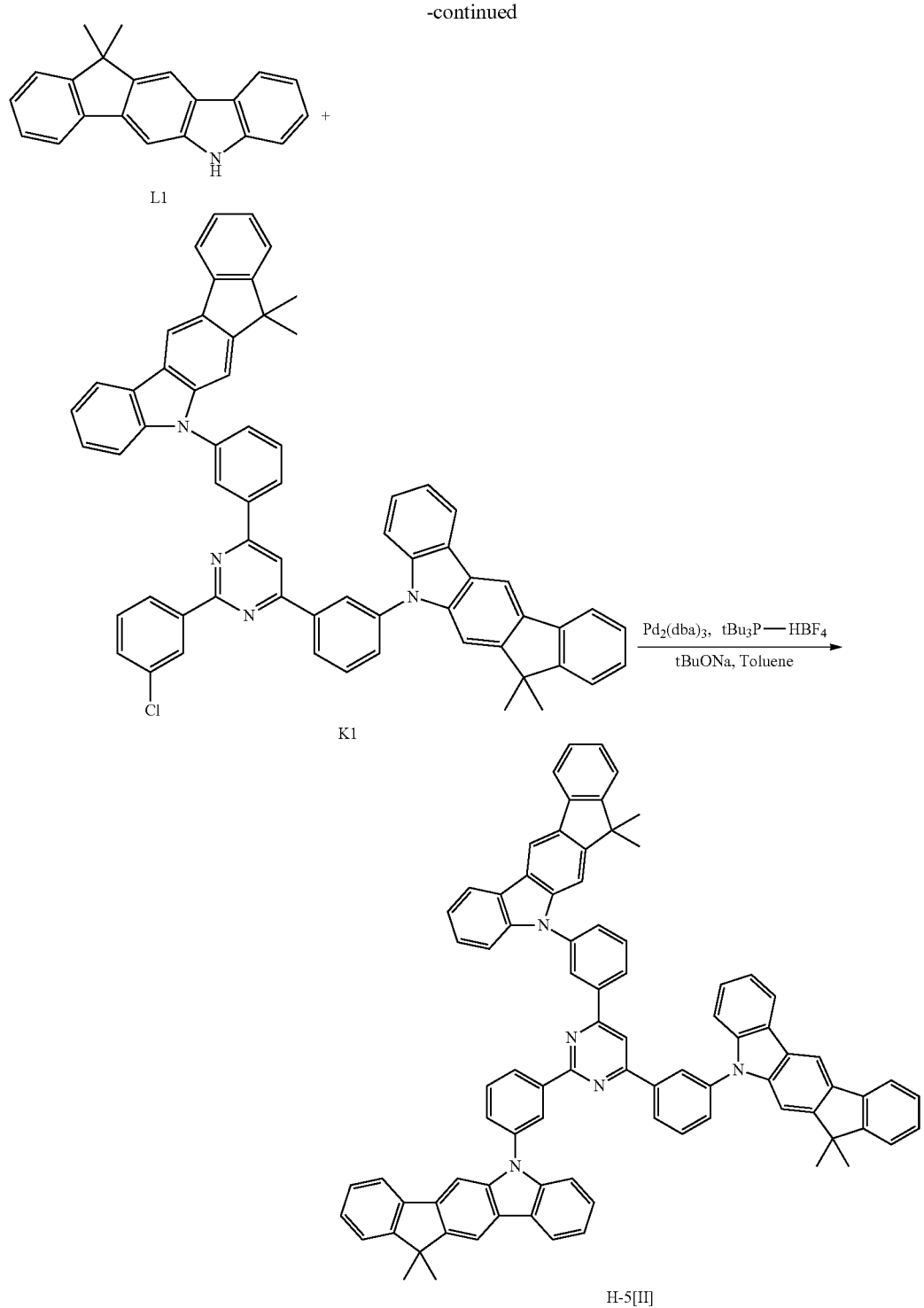

After adding sodium hydroxide (0.584 g, 14.6 mmol) to a solution of 3-bromobenzaldehyde (17.0 mL, 146 mmol) and 3-bromoacetophenone (19.3 mL, 146 mmol) in methanol (300 mL), the resultant solution was stirred at room temperature for 10.5 h.

The precipitated solid was collected by filtration, washed with methanol, and then dried under vacuum to obtain a cream-colored powder (47.8 g, yield: 90%).

Then, after adding 3-chlorobenzamidine hydrochloride (3.23 g, 16.9 mmol), sodium hydroxide (0.745 g, 18.6 mmol) and then ethanol (35 mL) to the obtained powder (12.4 g, 33.9 mmol), the reaction was allowed to proceed for 12.5 h while refluxing under heating. The white powder formed was collected by filtration, washed with ethanol until the washings were made colorless, further washed with water and then ethanol, and then dried under vacuum to obtain target pyrimidine intermediate J1 (5.25 g, yield: 62%).

Under argon atmosphere, carbazolyl intermediate B1 (1.70 g, 6.00 mmol), pyrimidine intermediate J1 (1.50 g, 3.00 mmol), tris(dibenzylideneacetone)dipalladium (0.110 g, 0.120 mmol), tri-t-butylphosphonium tetrafluoroborate (0.139 g, 0.48 mmol), sodium t-butoxide (0.288 g, 3.00 mmol), and anhydrous toluene (60 mL) were successively mixed, and the resultant mixture was refluxed for 11 h under heating.

After cooling the reaction liquid to room temperature, the insolubles were removed by filtration, and the organic solvent was evaporated off under reduced pressure. The obtained residue was purified by silica gel column chromatography to obtain compound K1 (1.90 g, yield: 70%).

Under argon atmosphere, compound K1 (1.90 g, 3.00 mmol), carbazolyl intermediate L1 (0.850 g, 3.00 mmol), tris(dibenzylideneacetone)dipalladium (0.110 g, 0.120 mmol), tri-t-butylphosphonium tetrafluoroborate (0.139 g, 0.48 mmol), sodium t-butoxide (0.288 g, 3.00 mmol), and anhydrous toluene (60 mL) were successively mixed, and the resultant mixture was refluxed for 11 h under heating.

After cooling the reaction liquid to room temperature, the insolubles were removed by filtration, and the organic solvent was evaporated off under reduced pressure. The obtained residue was purified by silica gel column chromatography to obtain compound H-5[II] (2.94 g, yield: 85%).

The results of analysis by HPLC (High Performance Liquid Chromatography) and LC-MS (Liquid Chromatography-Mass Spectrometry) on compound H-5[II] are shown below.

HPLC purity: 99.0%

LC-MS: calcd for $C_{85}H_{61}N_5$=1151.

found m/z=1379 (M+, 100).

Synthesis Example 6[II](Synthesis of Compound H-6[II])

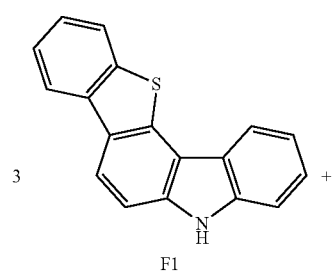

F1

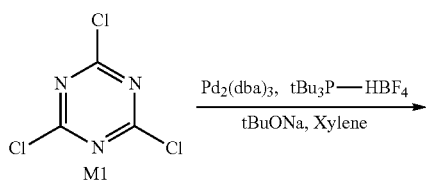

M1

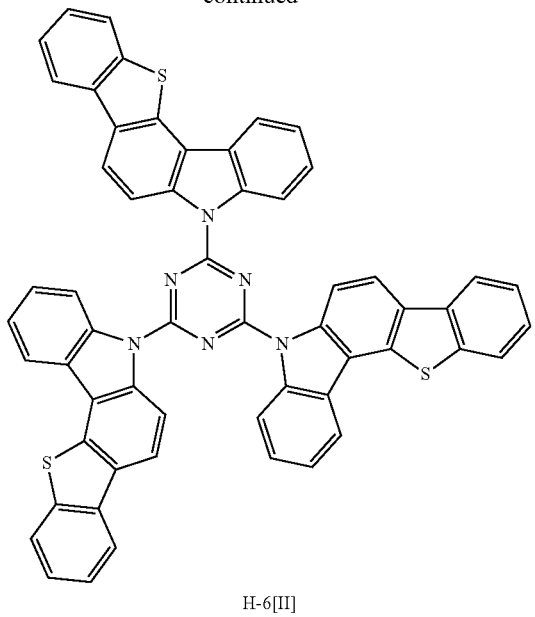

H-6[II]

Under argon atmosphere, carbazolyl intermediate F1 (2.46 g, 9.00 mmol), triazine intermediate M1 (0.553 g, 3.00 mmol), tris(dibenzylideneacetone)dipalladium (0.110 g, 0.120 mmol), tri-t-butylphosphonium tetrafluoroborate (0.139 g, 0.48 mmol), sodium t-butoxide (0.288 g, 3.00 mmol), and anhydrous xylene (60 mL) were successively mixed, and the resultant mixture was refluxed for 11 h under heating.

After cooling the reaction liquid to room temperature, the insolubles were removed by filtration, and the organic solvent was evaporated off under reduced pressure. The obtained residue was purified by silica gel column chromatography to obtain compound H-6[II] (2.15 g, yield: 80%).

The results of analysis by HPLC (High Performance Liquid Chromatography) and LC-MS (Liquid Chromatography-Mass Spectrometry) on compound H-6[II] are shown below.

HPLC purity: 99.0%

LC-MS: calcd for $C_{57}H_{30}N_6S_3$=894.

found m/z=894 (M+, 100).

The compounds within the scope of the claims of this application can be synthesized by referring to the above synthetic reactions while using a known synthetic reaction and a starting material in accordance with the target compound.

Example 1[II]

Cleaning of Substrate

A glass substrate of 25 mm×25 mm×1.1 mm thickness having an ITO transparent electrode (product of Geomatec Company) was cleaned by ultrasonic cleaning in isopropyl alcohol for 5 min and then UV ozone cleaning for 5 min.

Formation of Underlayers

Clevious AI4083 (tradename) manufactured by Heraeus as a hole transporting material was spin-coated on the ITO substrate to form a hole transporting layer with a thickness of 30 nm. Thereafter, unnecessary portion was removed by acetone and then a base substrate was produced by baking in air for 10 min on a hot plate at 200° C.

Formation of Light Emitting Layer

A 1.6% by mass toluene solution containing the compound H-1[II] obtained in Synthesis Example 1[II] as a host material and the following compound D-ii as a dopant material was prepared in a mixing ratio of compound H-1[II]:compound D-ii=90:10 by mass. The toluene solution was spin-coated on the base substrate into a thickness of 50 nm. Thereafter, unnecessary portion was removed by toluene and then the coated film was dried under heating at 150° C. on a hot plate to obtain a coat-laminated substrate having a light emitting layer. The film-forming operations for forming the light emitting layer were all conducted in a glove box under a nitrogen atmosphere.

Vapor Deposition and Sealing

The coat-laminated substrate was conveyed into a vapor deposition chamber and the following compound ET-1 as an electron transporting material was vapor-deposited into a thickness of 50 nm to form an electron transporting layer. Then, lithium fluoride was vapor-deposited into a thickness of 1 nm and aluminum was vapor-deposited into a thickness of 80 nm. After completing all the vapor deposition processes, the substrate with laminated films was sealed with a bored glass in a glove box under a nitrogen atmosphere to produce an organic EL device.

Evaluation of Device

By driving at a direct current, the obtained organic EL device was allowed to emit light to measure the external quantum efficiency (EQE) at a current density of 10 mA/cm$^2$. The organic EL device was further allowed to continuously emit light by driving at a direct current, and the time taken until the luminance was reduced from 1000 cd/m$^2$ to 800 cd/m$^2$ (LT80) was measured. The results are shown in Table 2.

An organic EL device was produced in the same manner as described above except for drying the coated film at 200° C. under heating in the formation of the light emitting layer. The obtained organic EL device was measured for the external quantum efficiency (EQE) in the same manner as described above. The result is shown in Table 2.

Example 2[II]

Each organic EL device wherein the coated film was dried at 150° C., or 200° C. under heating was produced in the same manner as in Example 1[II]except for using compound H-2[II] obtained in Synthesis Example 2[II] as a host material. The evaluation results obtained in the same manner as in Example 1[II] are shown in Table 2.

Example 3[II]

Each organic EL device wherein the coated film was dried at 150° C., or 200° C. under heating was produced in the same manner as in Example 1[II] except for using compound H-3[II] obtained in Synthesis Example 3[II] as a host material. The evaluation results obtained in the same manner as in Example 1[II] are shown in Table 2.

Example 4[II]

Each organic EL device wherein the coated film was dried at 150° C., or 200° C. under heating was produced in the same manner as in Example 1[II] except for using compound H-4[II] obtained in Synthesis Example 4[II] as a host material. The evaluation results obtained in the same manner as in Example 1[II] are shown in Table 2.

Example 5[II]

Each organic EL device wherein the coated film was dried at 150° C., or 200° C. under heating was produced in the same manner as in Example 1[II] except for using compound H-5[II] obtained in Synthesis Example 5[II] as a host material. The evaluation results obtained in the same manner as in Example 1[II] are shown in Table 2.

Example 6[II]

Each organic EL device wherein the coated film was dried at 150° C., or 200° C. under heating was produced in the same manner as in Example 1[II] except for using compound H-6[II] obtained in Synthesis Example 6[II] as a host material. The evaluation results obtained in the same manner as in Example 1[II] are shown in Table 2.

Comparative Example 1[II]

Each organic EL device wherein the coated film was dried at 150° C., or 200° C. under heating was produced in the same manner as in Example 1[II] except for using compound Q-1[II] described in WO 2012/086170 as a host material. The evaluation results obtained in the same manner as in Example 1[II] are shown in Table 2.

Comparative Example 2[II]

Each organic EL device wherein the coated film was dried at 150° C., or 200° C. under heating was produced in the same manner as in Example 1[II] except for using compound Q-2[II] described in WO 2011/108902 as a host material. The measured external quantum efficiency (EQE) of each organic EL device is shown in Table 2.

Comparative Example 3[II]

It was tried to produce an organic EL device in the same manner as in Example 1[II] except for using compound Q-3[II] described in WO 2007/063754. However, the solubility to toluene was low and a device capable of emitting light was not obtained.

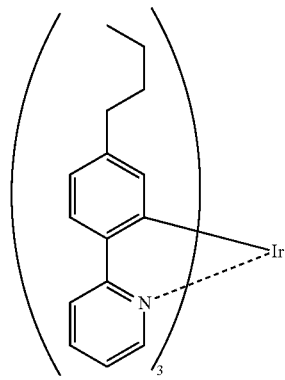

D-ii

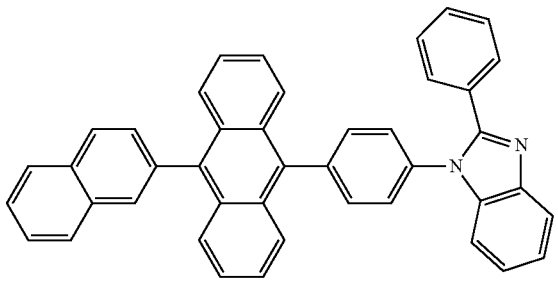

ET-1

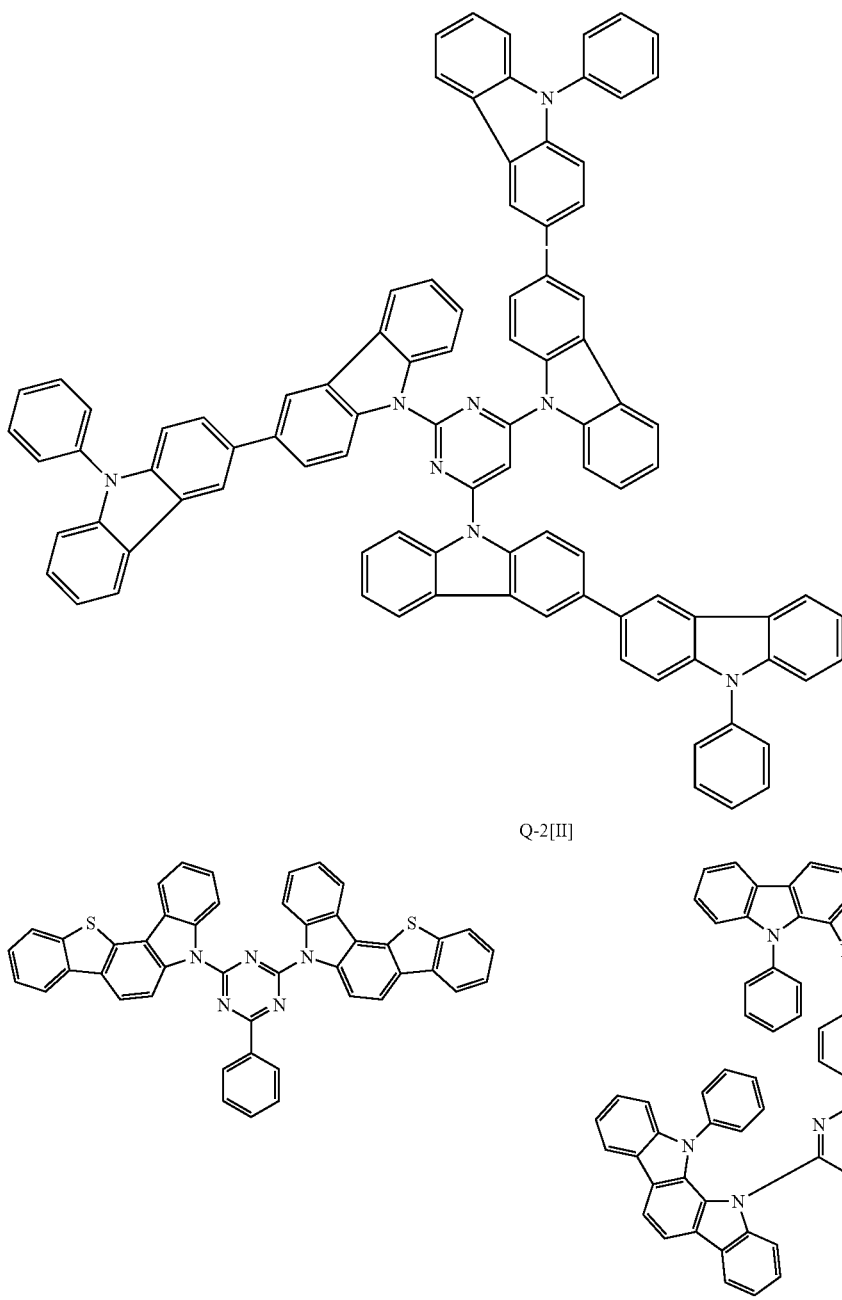

(3) Next, the synthesis method of compound 1[III], the production method of organic EL devices employing compound 1[III], and the evaluation results thereof are described below.

TABLE 2

| | Host material | External quantum efficiency (%) | | LT(80) (h) |
|---|---|---|---|---|
| | | dried at 150° C. | dried at 200° C. | |
| Example 1[II] | H-1[II] | 7.1 | 7.2 | 47 |
| Example 2[II] | H-2[II] | 6.9 | 7.0 | 44 |
| Example 3[II] | H-3[II] | 6.5 | 6.4 | 48 |
| Example 4[II] | H-4[II] | 7.9 | 8.1 | 42 |
| Example 5[II] | H-5[II] | 8.0 | 7.9 | 50 |
| Example 6[II] | H-6[II] | 7.1 | 6.5 | 46 |
| Comparative Example 1[II] | Q-1[II] | 7.6 | 7.3 | 5 |

TABLE 2-continued

| | Host material | External quantum efficiency (%) | | LT(80) (h) |
|---|---|---|---|---|
| | | dried at 150° C. | dried at 200° C. | |
| Comparative Example 2[II] | Q-2[II] | 6.8 | 3.2 | — |

Compound 1[III]

Synthesis Example 1[III](Synthesis of Compound H-1[III])

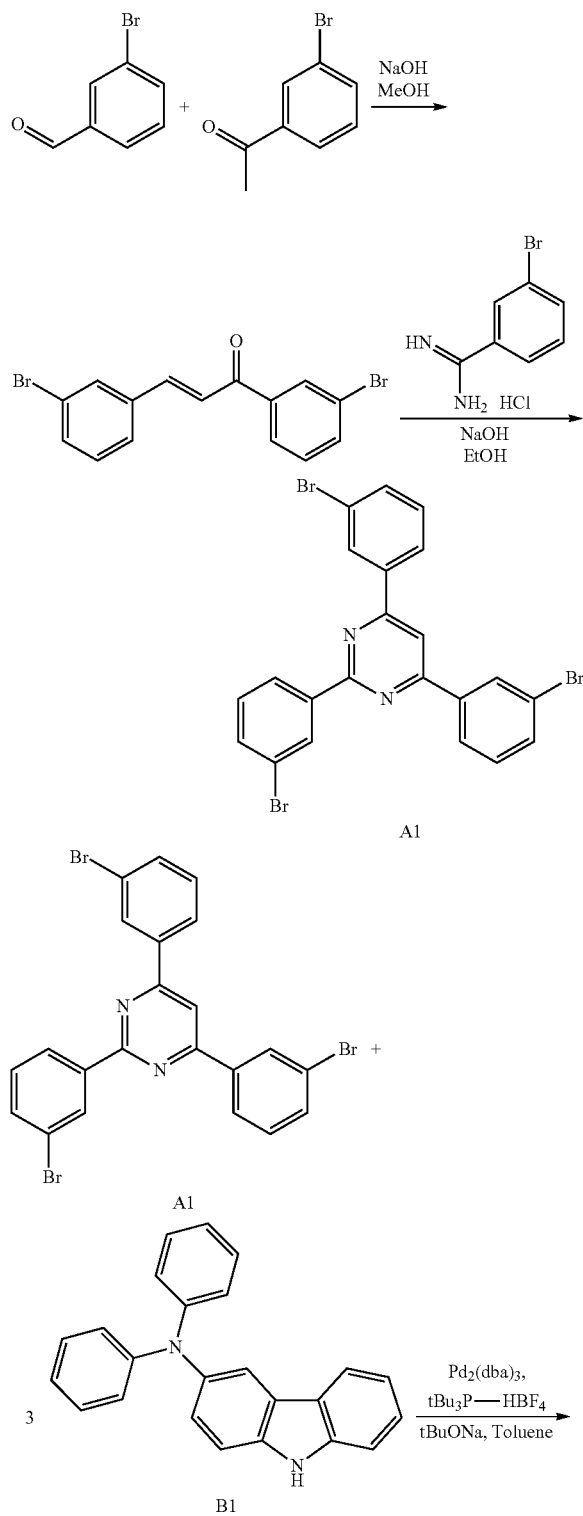

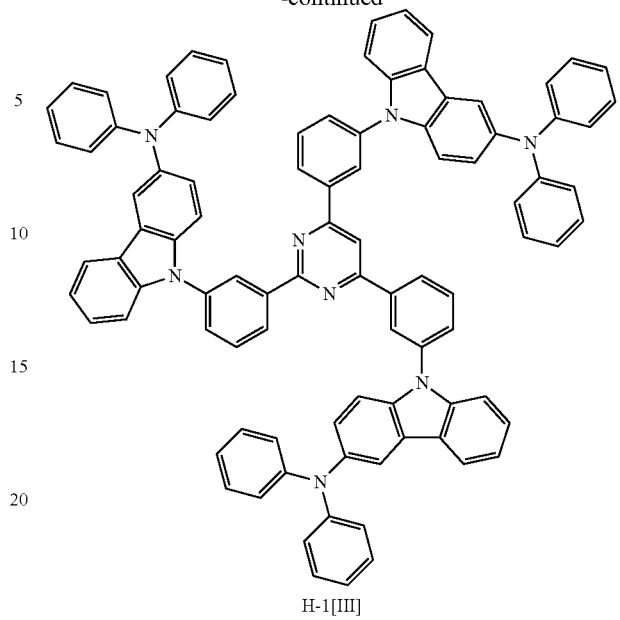

H-1[III]

After adding sodium hydroxide (0.584 g, 14.6 mmol) to a solution of 3-bromobenzaldehyde (17.0 mL, 146 mmol) and 3-bromoacetophenone (19.3 mL, 146 mmol) in methanol (300 mL), the resultant solution was stirred at room temperature for 10.5 h.

The precipitated solid was collected by filtration, washed with methanol, and then dried under vacuum to obtain a cream-colored powder (47.8 g, yield: 90%).

Then, after adding 3-bromobenzamidine hydrochloride (4.00 g, 16.9 mmol) and sodium hydroxide (0.745 g, 18.6 mmol) and then ethanol (35 mL) to the obtained powder (12.4 g, 33.9 mmol), the reaction was allowed to proceed for 12.5 h while refluxing under heating. The white powder formed was collected by filtration, washed with ethanol until the washings were made colorless, further washed with water and then ethanol, and then dried under vacuum to obtain target pyrimidine intermediate A1 (5.75 g, yield: 62%).

Under argon atmosphere, carbazolyl intermediate B1 (4.91 g, 9.00 mmol), pyrimidine intermediate A1 (1.23 g, 3.00 mmol), tris(dibenzylideneacetone)dipalladium (0.110 g, 0.120 mmol), tri-t-butylphosphonium tetrafluoroborate (0.139 g, 0.480 mmol), sodium t-butoxide (0.965 g, 9.00 mmol), and anhydrous toluene (60 mL) were successively mixed, and the resultant mixture was refluxed for 8 h under heating.

After cooling the reaction liquid to room temperature, the insolubles were removed by filtration, and the organic solvent was evaporated off under reduced pressure. The obtained residue was purified by silica gel column chromatography to obtain compound H-1[III] (3.22 g, yield: 70%).

The results of analysis by HPLC (High Performance Liquid Chromatography) and LC-MS (Liquid Chromatography-Mass Spectrometry) on compound H-1[III] are shown below.

HPLC purity: 99.0%

LC-MS: calcd for $C_{112}H_{76}N_8$=1532.

found m/z=1532 (M+, 100).

Synthesis Example 2[III](Synthesis of Compound H-2[III])

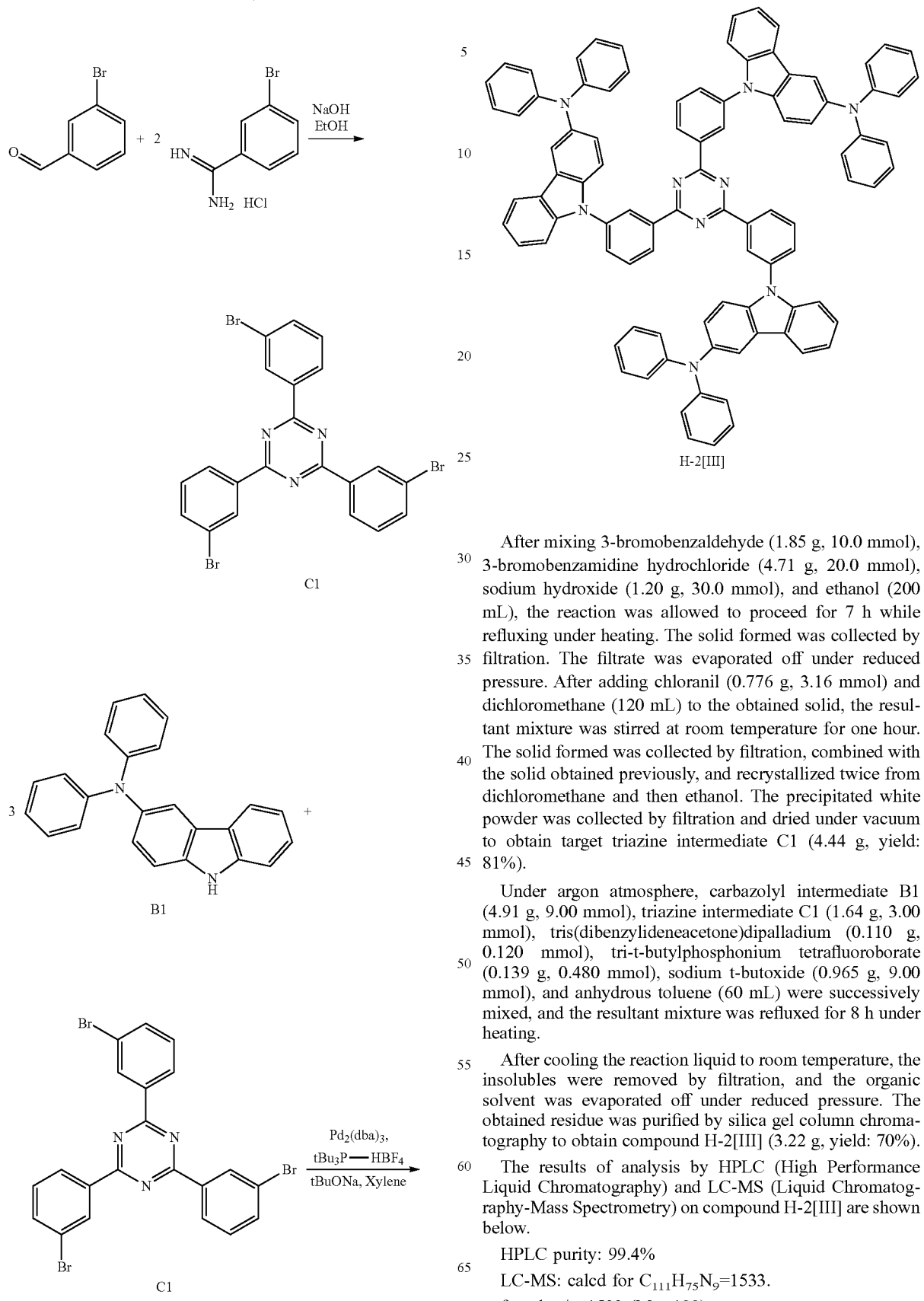

After mixing 3-bromobenzaldehyde (1.85 g, 10.0 mmol), 3-bromobenzamidine hydrochloride (4.71 g, 20.0 mmol), sodium hydroxide (1.20 g, 30.0 mmol), and ethanol (200 mL), the reaction was allowed to proceed for 7 h while refluxing under heating. The solid formed was collected by filtration. The filtrate was evaporated off under reduced pressure. After adding chloranil (0.776 g, 3.16 mmol) and dichloromethane (120 mL) to the obtained solid, the resultant mixture was stirred at room temperature for one hour. The solid formed was collected by filtration, combined with the solid obtained previously, and recrystallized twice from dichloromethane and then ethanol. The precipitated white powder was collected by filtration and dried under vacuum to obtain target triazine intermediate C1 (4.44 g, yield: 81%).

Under argon atmosphere, carbazolyl intermediate B1 (4.91 g, 9.00 mmol), triazine intermediate C1 (1.64 g, 3.00 mmol), tris(dibenzylideneacetone)dipalladium (0.110 g, 0.120 mmol), tri-t-butylphosphonium tetrafluoroborate (0.139 g, 0.480 mmol), sodium t-butoxide (0.965 g, 9.00 mmol), and anhydrous toluene (60 mL) were successively mixed, and the resultant mixture was refluxed for 8 h under heating.

After cooling the reaction liquid to room temperature, the insolubles were removed by filtration, and the organic solvent was evaporated off under reduced pressure. The obtained residue was purified by silica gel column chromatography to obtain compound H-2[III] (3.22 g, yield: 70%).

The results of analysis by HPLC (High Performance Liquid Chromatography) and LC-MS (Liquid Chromatography-Mass Spectrometry) on compound H-2[III] are shown below.

HPLC purity: 99.4%

LC-MS: calcd for $C_{111}H_{75}N_9$=1533.

found m/z=1533 (M+, 100).

Synthesis Example 3[III](Synthesis of Compound H-3[III])

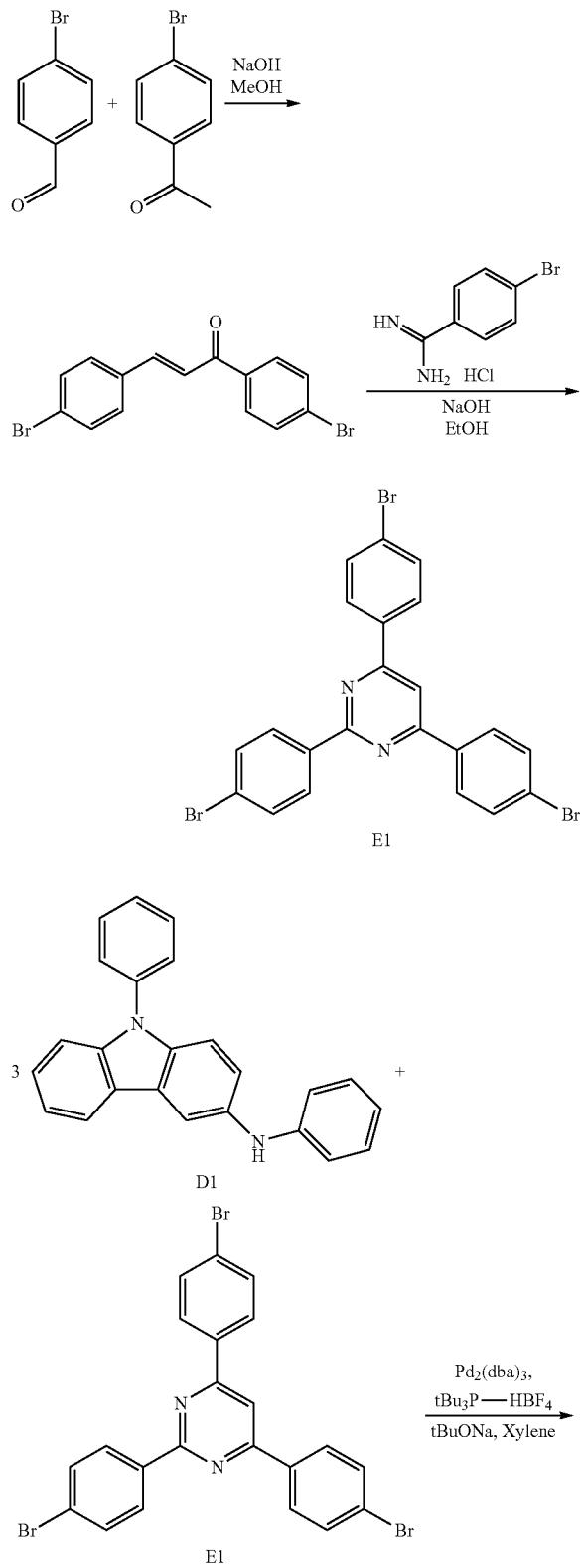

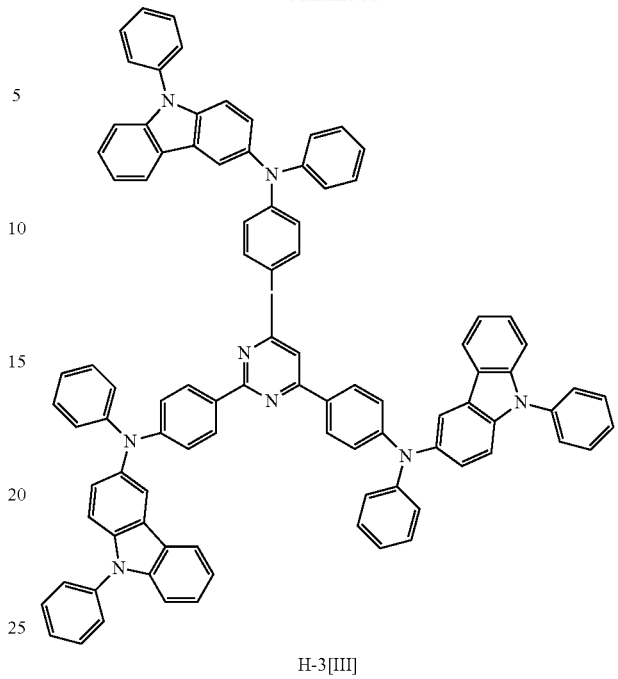

H-3[III]

After adding sodium hydroxide (0.584 g, 14.6 mmol) to a solution of 4-bromobenzaldehyde (17.0 mL, 146 mmol) and 4-bromoacetophenone (19.3 mL, 146 mmol) in methanol (300 mL), the resultant solution was stirred at room temperature for 10.5 h.

The precipitated solid was collected by filtration, washed with methanol, and then dried under vacuum to obtain a powder (47.8 g, yield: 90%).

Then, after adding 4-bromobenzamidine hydrochloride (4.00 g, 16.9 mmol) and sodium hydroxide (0.745 g, 18.6 mmol) and then ethanol (35 mL) to the obtained powder (12.4 g, 33.9 mmol), the reaction was allowed to proceed for 12.5 h while refluxing under heating. The white powder formed was collected by filtration, washed with ethanol until the washings were made colorless, further washed with water and then ethanol, and then dried under vacuum to obtain target pyrimidine intermediate E1 (7.42 g, yield: 80%).

Under argon atmosphere, carbazolyl intermediate D1 (3.01 g, 9.00 mmol), pyrimidine intermediate E1 (1.23 g, 3.00 mmol), tris(dibenzylideneacetone)dipalladium (0.110 g, 0.120 mmol), tri-t-butylphosphonium tetrafluoroborate (0.139 g, 0.480 mmol), sodium t-butoxide (0.965 g, 9.00 mmol), and anhydrous toluene (60 mL) were successively mixed, and the resultant mixture was refluxed for 8 h under heating.

After cooling the reaction liquid to room temperature, the insolubles were removed by filtration, and the organic solvent was evaporated off under reduced pressure. The obtained residue was purified by silica gel column chromatography to obtain compound H-3[III] (2.55 g, yield: 65%).

The results of analysis by HPLC (High Performance Liquid Chromatography) and LC-MS (Liquid Chromatography-Mass Spectrometry) on compound H-3[III] are shown below.

HPLC purity: 99.2%
LC-MS: calcd for $C_{94}H_{64}N_8$=1304.
found m/z=1304 (M+, 100).

Synthesis Example 4[III](Synthesis of Compound H-4[III])

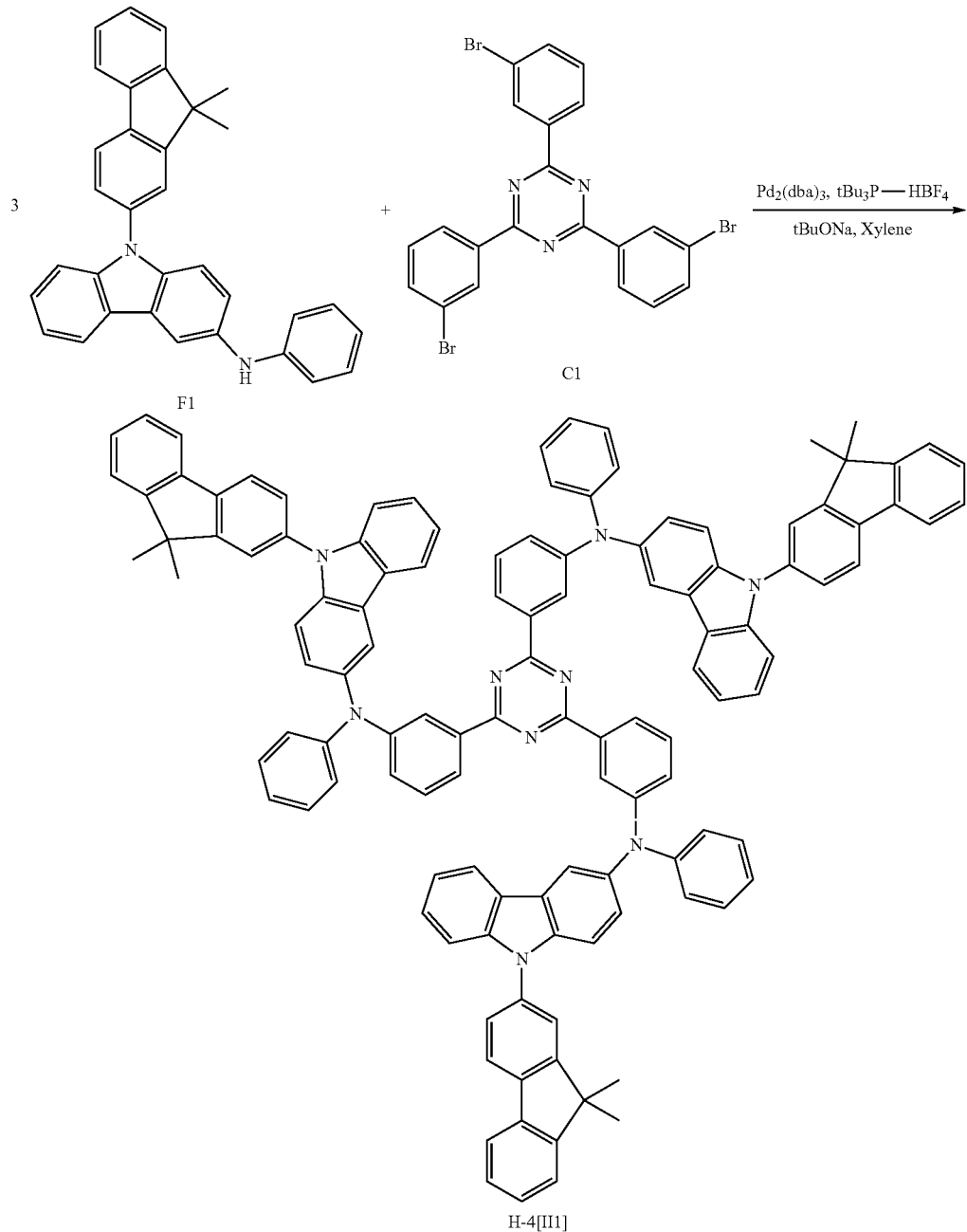

Under argon atmosphere, carbazolyl intermediate F1 (4.06 g, 9.00 mmol), triazine intermediate C1 (1.64 g, 3.00 mmol), tris(dibenzylideneacetone)dipalladium (0.110 g, 0.120 mmol), tri-t-butylphosphonium tetrafluoroborate (0.139 g, 0.480 mmol), sodium t-butoxide (0.965 g, 9.00 mmol), and anhydrous toluene (60 mL) were successively mixed, and the resultant mixture was refluxed for 8 h under heating.

After cooling the reaction liquid to room temperature, the insolubles were removed by filtration, and the organic solvent was evaporated off under reduced pressure. The obtained residue was purified by silica gel column chromatography to obtain compound H-4[III] (2.73 g, yield: 55%).

The results of analysis by HPLC (High Performance Liquid Chromatography) and LC-MS (Liquid Chromatography-Mass Spectrometry) on compound H-4[III] are shown below.

HPLC purity: 98.6%

LC-MS: calcd for $C_{120}H_{87}N_9$=1653.

found m/z=1653 (M+, 100).

Synthesis Example 5[III](Synthesis of Compound H-5[III])
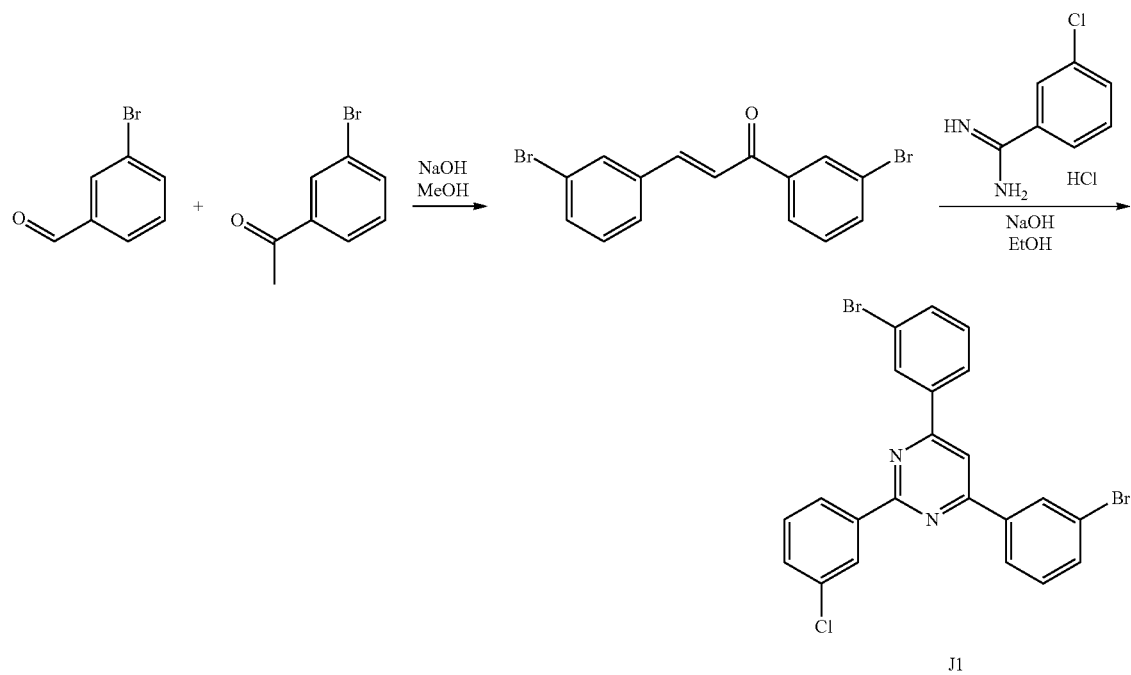
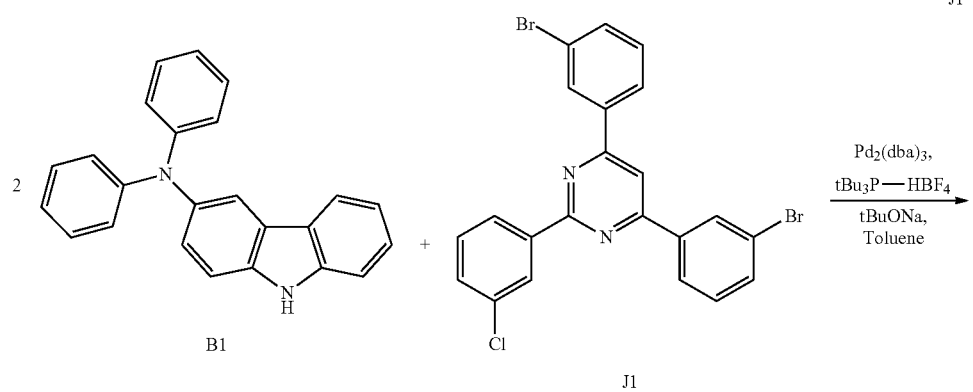
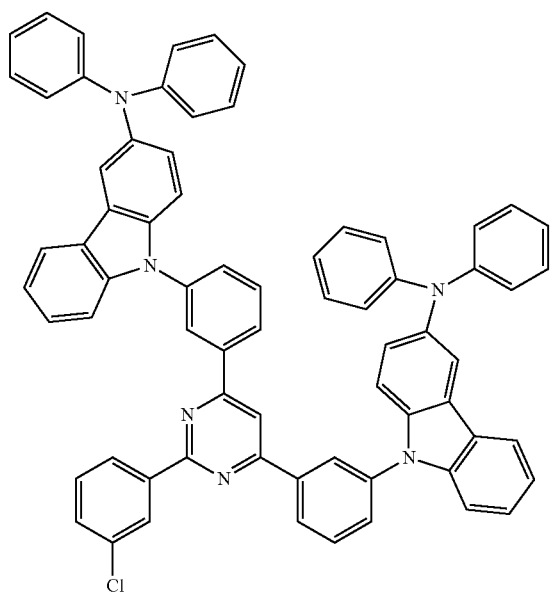

-continued
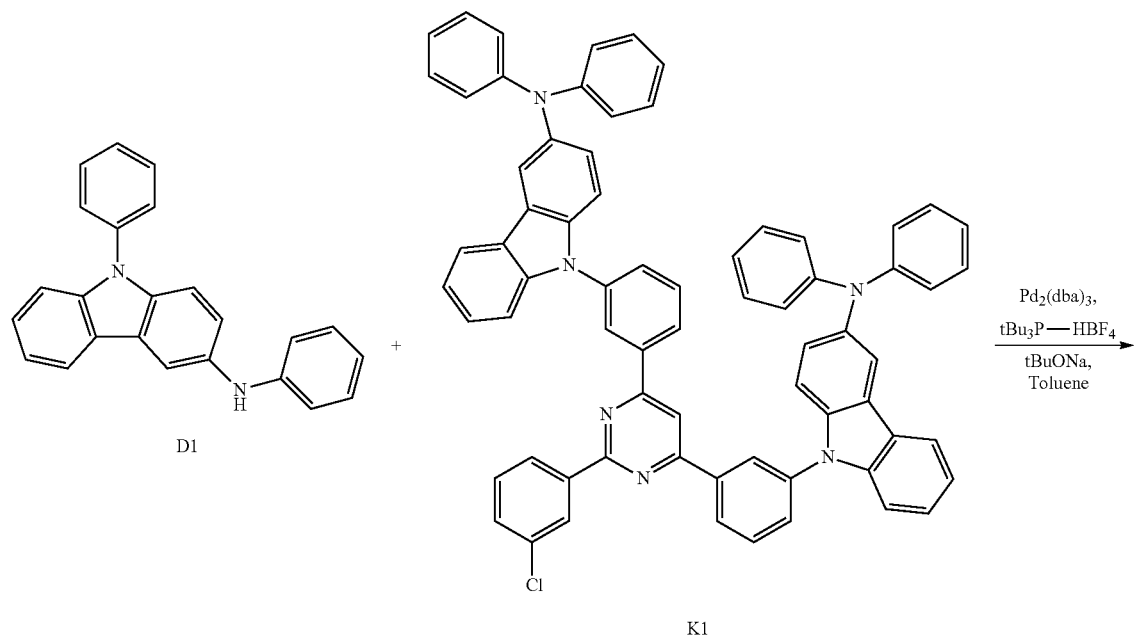
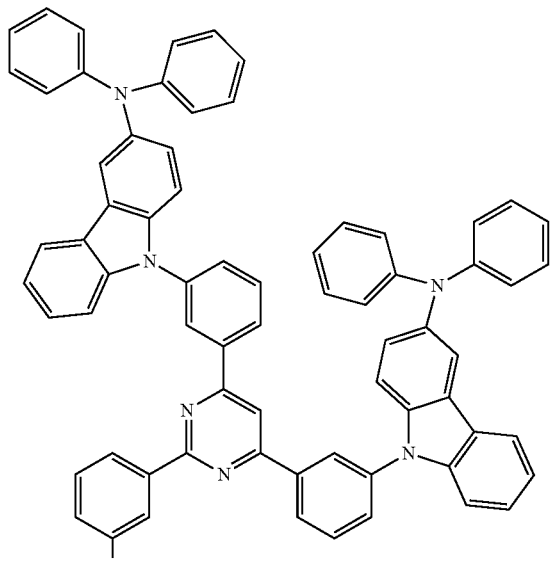
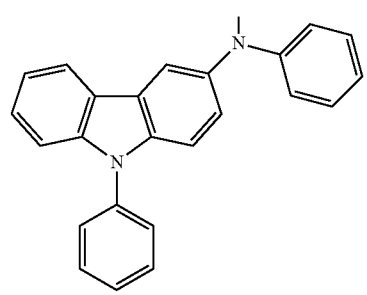
H-5 [III]

After adding sodium hydroxide (0.584 g, 14.6 mmol) to a solution of 3-bromobenzaldehyde (17.0 mL, 146 mmol) and 3-bromoacetophenone (19.3 mL, 146 mmol) in methanol (300 mL), the resultant solution was stirred at room temperature for 10.5 h.

The precipitated solid was collected by filtration, washed with methanol, and then dried under vacuum to obtain a cream-colored powder (47.8 g, yield: 90%).

Then, after adding 3-chlorobenzamidine hydrochloride (3.23 g, 16.9 mmol) and sodium hydroxide (0.745 g, 18.6 mmol) and then ethanol (35 mL) to the obtained powder (12.4 g, 33.9 mmol), the reaction was allowed to proceed for 12.5 h while refluxing under heating. The white powder formed was collected by filtration, washed with ethanol until the washings were made colorless, further washed with water and then ethanol, and then dried under vacuum to obtain target pyrimidine intermediate J1 (5.25 g, yield: 62%).

Under argon atmosphere, carbazolyl intermediate B1 (2.46 g, 6.00 mmol), pyrimidine intermediate J1 (1.50 g, 3.00 mmol), tris(dibenzylideneacetone)dipalladium (0.110 g, 0.120 mmol), tri-t-butylphosphonium tetrafluoroborate (0.139 g, 0.48 mmol), sodium t-butoxide (0.288 g, 3.00 mmol), and anhydrous toluene (60 mL) were successively mixed, and the resultant mixture was refluxed for 11 h under heating.

After cooling the reaction liquid to room temperature, the insolubles were removed by filtration, and the organic solvent was evaporated off under reduced pressure. The obtained residue was purified by silica gel column chromatography to obtain compound K1 (1.91 g, yield: 55%).

Under argon atmosphere, compound K1 (1.91 g, 3.00 mmol), carbazolyl intermediate D1 (1.00 g, 3.00 mmol), tris(dibenzylideneacetone)dipalladium (0.110 g, 0.120 mmol), tri-t-butylphosphonium tetrafluoroborate (0.139 g, 0.48 mmol), sodium t-butoxide (0.288 g, 3.00 mmol), and anhydrous toluene (60 mL) were successively mixed, and the resultant mixture was refluxed for 11 h under heating.

After cooling the reaction liquid to room temperature, the insolubles were removed by filtration, and the organic solvent was evaporated off under reduced pressure. The obtained residue was purified by silica gel column chromatography to obtain compound H-5[III] (3.72 g, yield: 85%).

The results of analysis by HPLC (High Performance Liquid Chromatography) and LC-MS (Liquid Chromatography-Mass Spectrometry) on compound H-5[III] are shown below.

HPLC purity: 99.0%
LC-MS: calcd for $C_{106}H_{72}N_8$=1456.
found m/z=1456 (M+, 100).

Synthesis Example 6[III](Synthesis of Compound H-6[III])

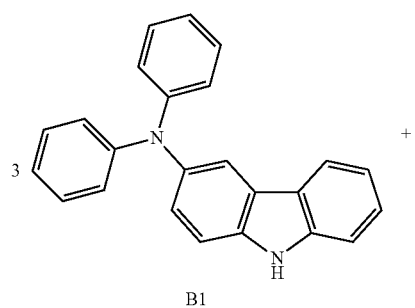

B1

+

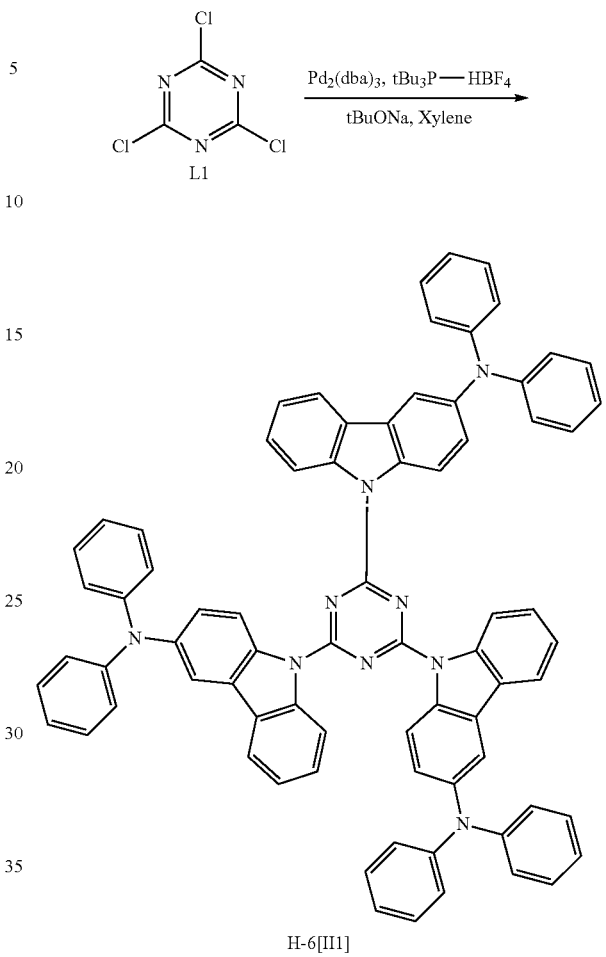

H-6[III]

Under argon atmosphere, carbazolyl intermediate B1 (3.01 g, 9.00 mmol)), triazine intermediate L1 (0.553 g, 3.00 mmol), tris(dibenzylideneacetone)dipalladium (0.110 g, 0.120 mmol), tri-t-butylphosphonium tetrafluoroborate (0.139 g, 0.48 mmol), sodium t-butoxide (0.288 g, 3.00 mmol), and anhydrous xylene (60 mL) were successively mixed, and the resultant mixture was refluxed for 11 h under heating.

After cooling the reaction liquid to room temperature, the insolubles were removed by filtration, and the organic solvent was evaporated off under reduced pressure. The obtained residue was purified by silica gel column chromatography to obtain compound H-6[III] (2.59 g, yield: 80%).

The results of analysis by HPLC (High Performance Liquid Chromatography) and LC-MS (Liquid Chromatography-Mass Spectrometry) on compound H-6[III] are shown below.

HPLC purity: 99.0%
LC-MS: calcd for $C_{75}H_{51}N_9$=1077.
found m/z=1077 (M+, 100).

The compounds within the scope of the claims of this application can be synthesized by referring to the above synthetic reactions while using a known synthetic reaction and a starting material in accordance with the target compound.

Example 1[III]

Cleaning of Substrate

A glass substrate of 25 mm×25 mm×1.1 mm thickness having an ITO transparent electrode (product of Geomatec Company) was cleaned by ultrasonic cleaning in isopropyl alcohol for 5 min and then UV ozone cleaning for 5 min.

Formation of Underlayers

Clevious AI4083 (tradename) manufactured by Heraeus as a hole transporting material was spin-coated on the ITO substrate to form a hole transporting layer with a thickness of 30 nm. Thereafter, unnecessary portion was removed by acetone and then a base substrate was produced by baking in air for 10 min on a hot plate at 200° C.

Formation of Light Emitting Layer

A 1.6% by mass toluene solution containing the compound H-1[III] obtained in Synthesis Example 1[III] as a host material and the following compound D-i as a dopant material was prepared in a mixing ratio of compound H-1[III]:compound D-i=95:5 by mass. The toluene solution was spin-coated on the base substrate into a thickness of 50 nm. Thereafter, unnecessary portion was removed by toluene and then a coat-laminated substrate with a light emitting layer was obtained by drying under heating at 150° C. on a hot plate. The film-forming operations for forming the light emitting layer were all conducted in a glove box under a nitrogen atmosphere.

Vapor Deposition and Sealing

The coat-laminated substrate was conveyed into a vapor deposition chamber and the following compound ET-1 as an electron transporting material was vapor-deposited into a thickness of 50 nm to form an electron transporting layer. Then, lithium fluoride was vapor-deposited into a thickness of 1 nm and aluminum was vapor-deposited into a thickness of 80 nm. After completing all the vapor deposition processes, the substrate with laminated films was sealed with a bored glass in a glove box under a nitrogen atmosphere to produce an organic EL device.

Evaluation of Device

By driving at a direct current, the obtained organic EL device was allowed to emit light to measure the external quantum efficiency (EQE) at a current density of 10 mA/cm$^2$. The result is shown in Table 3.

An organic EL device was produced in the same manner as described above except for drying the coated film at 200° C. under heating in the formation of the light emitting layer. The obtained organic EL device was measured for the external quantum efficiency (EQE) in the same manner as described above. The result is shown in Table 3.

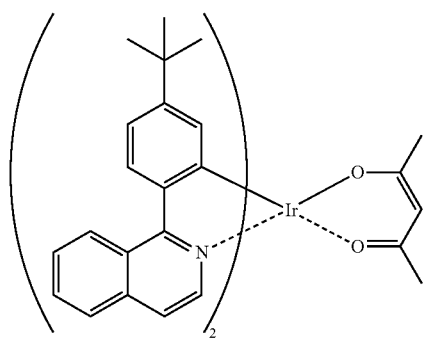

D-i

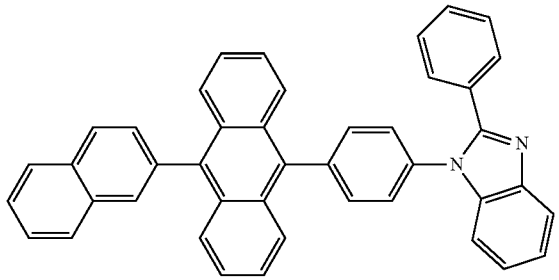

ET-1

Example 2[III]

Each organic EL device was produced in the same manner as in Example 1[III] except for using compound H-2[III] obtained in Synthesis Example 2[III] as a host material. The results are shown in Table 3.

Example 3[III]

Each organic EL device was produced in the same manner as in Example 1[III] except for using compound H-3[III] obtained in Synthesis Example 3[III] as a host material. The results are shown in Table 3.

Example 4[III]

Each organic EL device was produced in the same manner as in Example 1[III] except for using compound H-4[III] obtained in Synthesis Example 4[III] as a host material. The results are shown in Table 3.

Example 5[III]

Each organic EL device was produced in the same manner as in Example 1[III] except for using compound H-5[III] obtained in Synthesis Example 5[III] as a host material. The results are shown in Table 3.

Example 6[III]

Each organic EL device was produced in the same manner as in Example 1[III] except for using compound H-6[II] obtained in Synthesis Example 6[II] as a host material. The results are shown in Table 3.

Comparative Example 1[III]

Each organic EL device was produced in the same manner as in Example 1[II] except for using compound Q-1[III] described in WO 2012/086170 as a host material. The results are shown in Table 3.

Comparative Example 2[III]

Each organic EL device was produced in the same manner as in Example 1[III] except for using compound Q-2[III] described in WO 2013/081088 as a host material. The results are shown in Table 3.

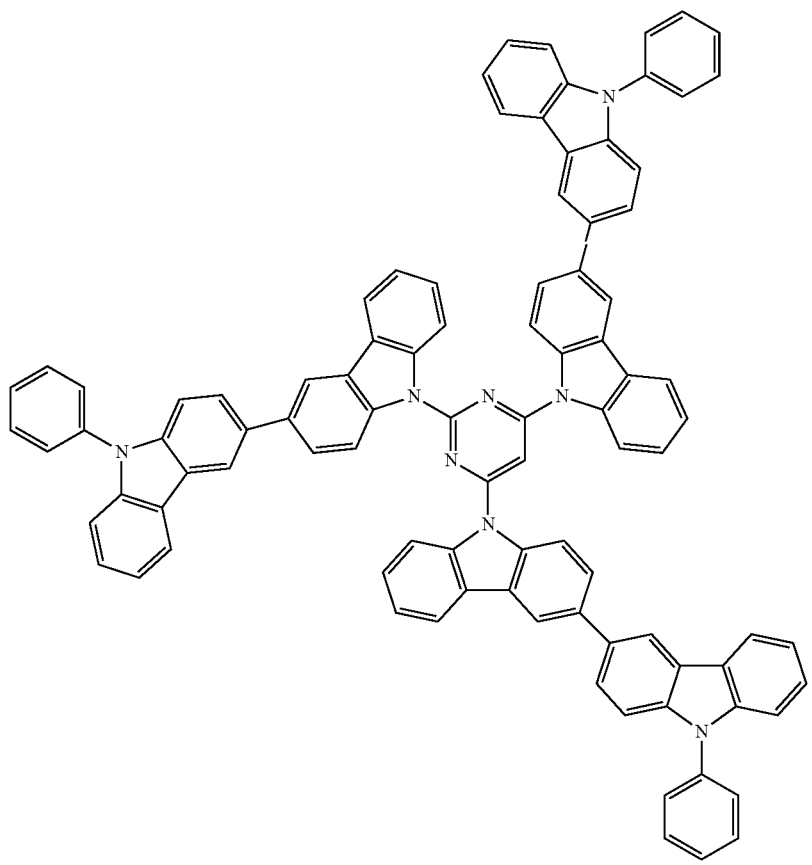
Q-1[III]
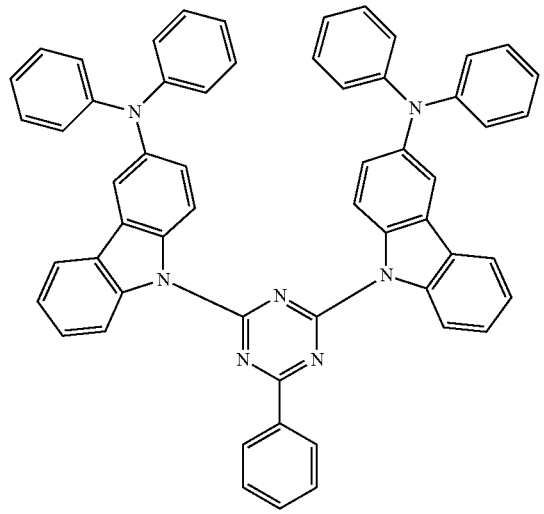
Q-2[III]
| | TABLE 1 | | |
|---|---|---|---|
| | Host material | External quantum efficiency (%) | |
| | | dried at 150° C. | dried at 200° C. |
| Example 1[III] | H-1[III] | 4.8 | 4.8 |
| Example 2[III] | H-2[III] | 4.9 | 4.7 |
| Example 3[III] | H-3[III] | 4.3 | 4.2 |
| Example 4[III] | H-4[III] | 4.4 | 4.2 |
| Example 5[III] | H-5[III] | 4.6 | 4.5 |
| Example 6[III] | H-6[III] | 4.4 | 4.3 |
| Comparative Example 1[III] | Q-1[III] | 2.1 | —*1 |

TABLE 1-continued

| | | External quantum efficiency (%) | |
|---|---|---|---|
| | Host material | dried at 150° C. | dried at 200° C. |
| Comparative Example 2[III] | Q-2[III] | 4.3 | 2.3 |

*[1]not measured because the external quantum efficiency was low even when dried at 150° C.

(4) Next, the synthesis method of compound 1[IV], the production method of organic EL devices employing compound 1[IV], and the evaluation results thereof are described below.

Compound 1[IV]

Synthesis Example 1[IV](Synthesis of Compound H-1[IV])

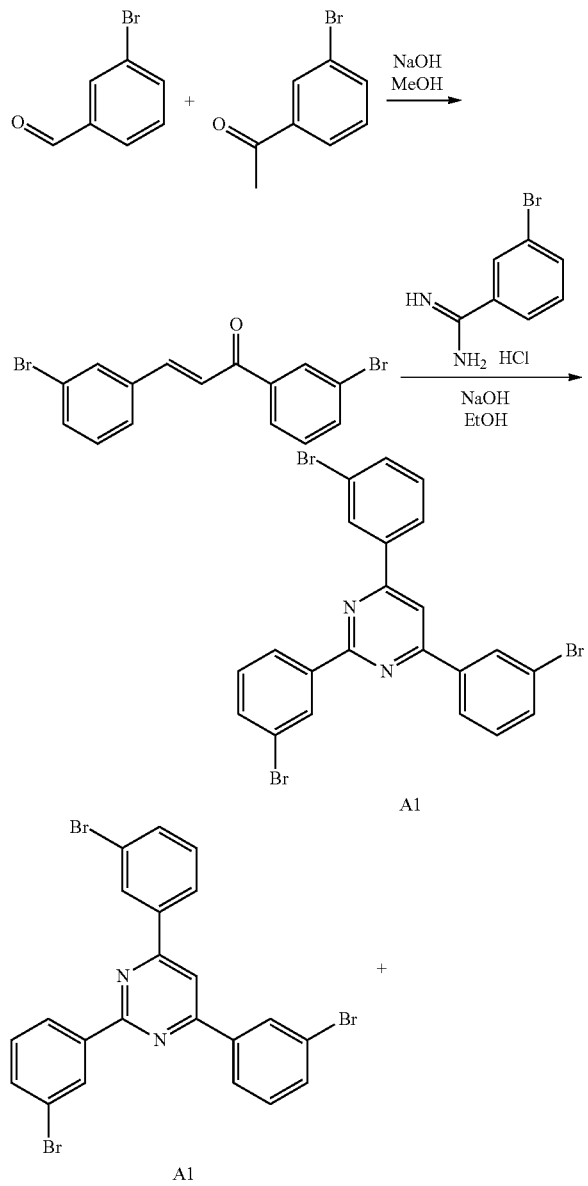

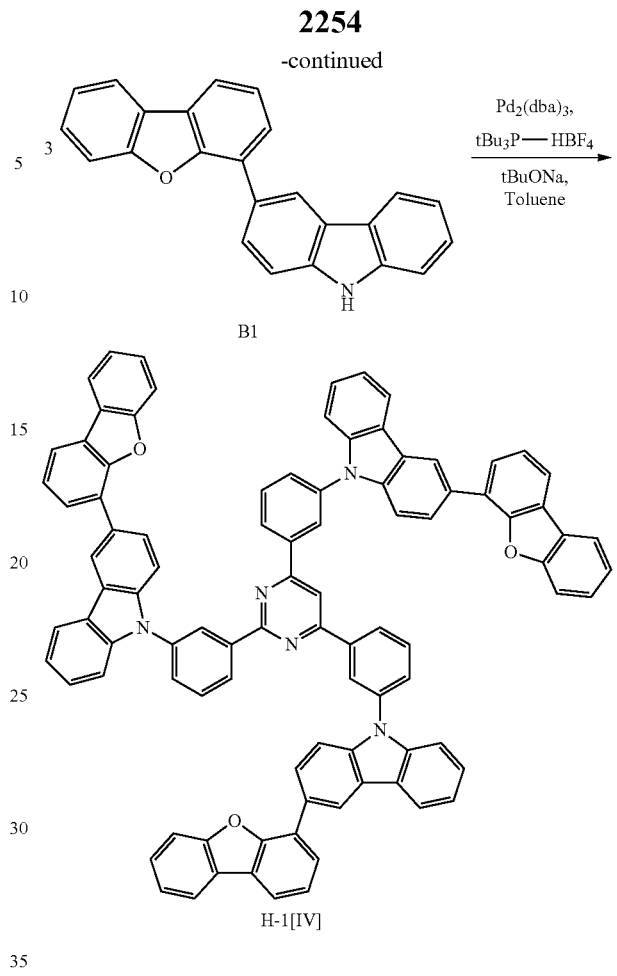

After adding sodium hydroxide (0.584 g, 14.6 mmol) to a solution of 3-bromobenzaldehyde (17.0 mL, 146 mmol) and 3-bromoacetophenone (19.3 mL, 146 mmol) in methanol (300 mL), the resultant solution was stirred at room temperature for 10.5 h.

The precipitated solid was collected by filtration, washed with methanol, and then dried under vacuum to obtain a cream-colored powder (47.8 g, yield: 90%).

Then, after adding 3-bromobenzamidine hydrochloride (4.00 g, 16.9 mmol) and sodium hydroxide (0.745 g, 18.6 mmol) and then ethanol (35 mL) to the obtained powder (12.4 g, 33.9 mmol, the reaction was allowed to proceed for 12.5 h while refluxing under heating. The white powder formed was collected by filtration, washed with ethanol until the washings were made colorless, further washed with water and then ethanol, and then dried under vacuum to obtain target pyrimidine intermediate A1 (5.75 g, yield: 62%).

Under argon atmosphere, carbazolyl intermediate B1 (3.00 g, 9.00 mmol), pyrimidine intermediate A1 (1.23 g, 3.00 mmol), tris(dibenzylideneacetone)dipalladium (0.110 g, 0.120 mmol, tri-t-butylphosphonium tetrafluoroborate (0.139 g, 0.480 mmol), sodium t-butoxide (0.965 g, 9.00 mmol), and anhydrous toluene (60 mL) were successively mixed, and the resultant mixture was refluxed for 8 h under heating.

After cooling the reaction liquid to room temperature, the insolubles were removed by filtration, and the organic solvent was evaporated off under reduced pressure. The obtained residue was purified by silica gel column chromatography to obtain compound H-1[IV] (2.74 g, yield: 70%).
The results of analysis by HPLC (High Performance Liquid Chromatography) and LC-MS (Liquid Chromatography-Mass Spectrometry) on compound H-1[IV] are shown below.
HPLC purity: 99.0%
LC-MS: calcd for $C_{94}H_{55}N_5O_3$=1301.
found m/z=13012 (M+, 100).
Synthesis Example 2[IV](Synthesis of Compound H-2[IV])
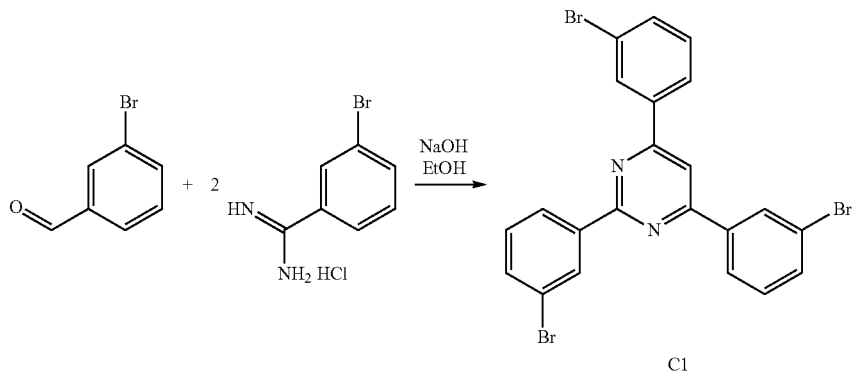
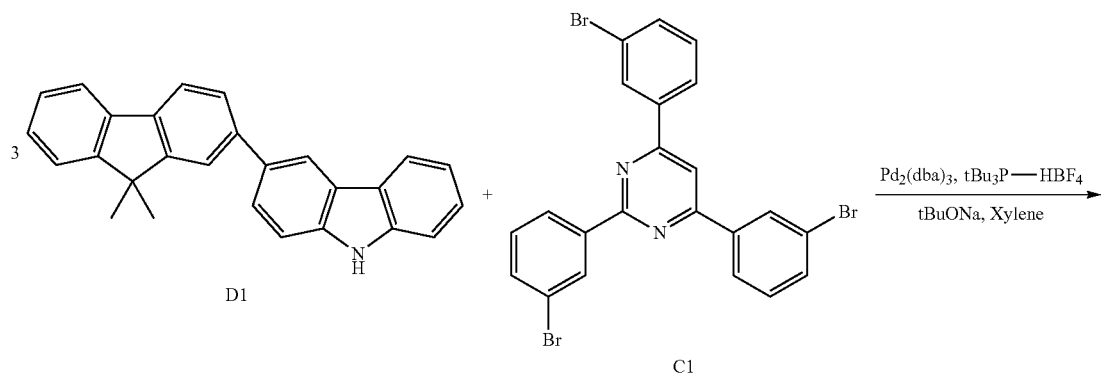
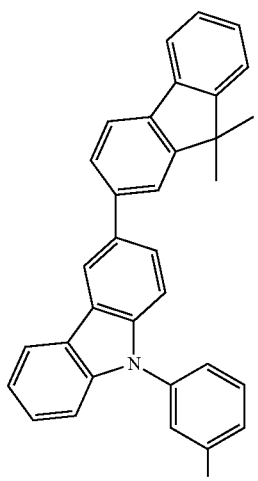

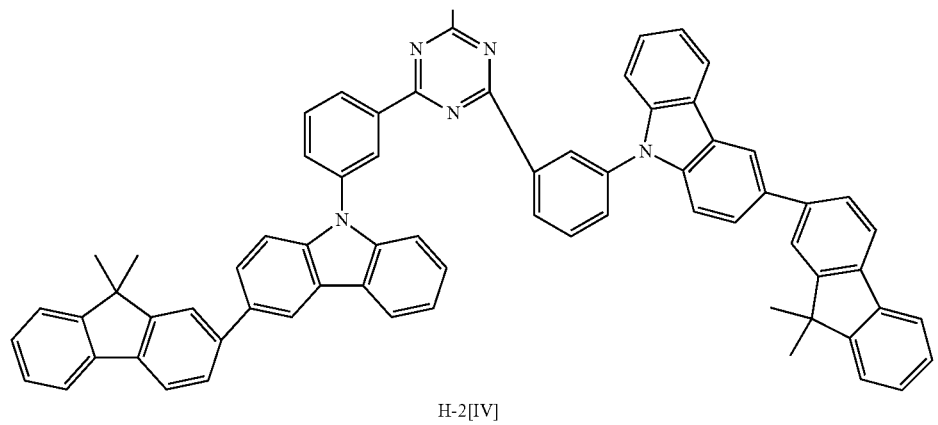

H-2[IV]

After mixing 3-bromobenzaldehyde (1.85 g, 10.0 mmol), 3-bromobenzamidine hydrochloride (4.71 g, 20.0 mmol), sodium hydroxide (1.20 g, 30.0 mmol), and ethanol (200 mL), the reaction was allowed to proceed for 7 h while refluxing under heating. The solid formed was collected by filtration. The filtrate was evaporated off under reduced pressure. After adding chloranil (0.776 g, 3.16 mmol) and dichloromethane (120 mL) to the obtained solid, the resultant mixture was stirred at room temperature for one hour. The solid formed was collected by filtration, combined with the solid obtained previously, and recrystallized twice from dichloromethane and then ethanol. The precipitated white powder was collected by filtration and dried under vacuum to obtain target triazine intermediate C1 (4.44 g, yield: 81%).

Under argon atmosphere, carbazolyl intermediate D1 (3.24 g, 9.00 mmol), triazine intermediate C1 (1.64 g, 3.00 mmol), tris(dibenzylideneacetone)dipalladium (0.110 g, 0.120 mmol), tri-t-butylphosphonium tetrafluoroborate (0.139 g, 0.480 mmol), sodium t-butoxide (0.965 g, 9.00 mmol), and anhydrous toluene (60 mL) were successively mixed, and the resultant mixture was refluxed for 8 h under heating.

After cooling the reaction liquid to room temperature, the insolubles were removed by filtration, and the organic solvent was evaporated off under reduced pressure. The obtained residue was purified by silica gel column chromatography to obtain compound H-2[IV] (2.90 g, yield: 70%).

The results of analysis by HPLC (High Performance Liquid Chromatography) and LC-MS (Liquid Chromatography-Mass Spectrometry) on compound H-2[IV] are shown below.

HPLC purity: 99.4%
LC-MS: calcd for $C_{102}H_{72}N_6$=1380.
found m/z=1380 (M+, 100).

Synthesis Example 3[IV](Synthesis of Compound H-3[IV])

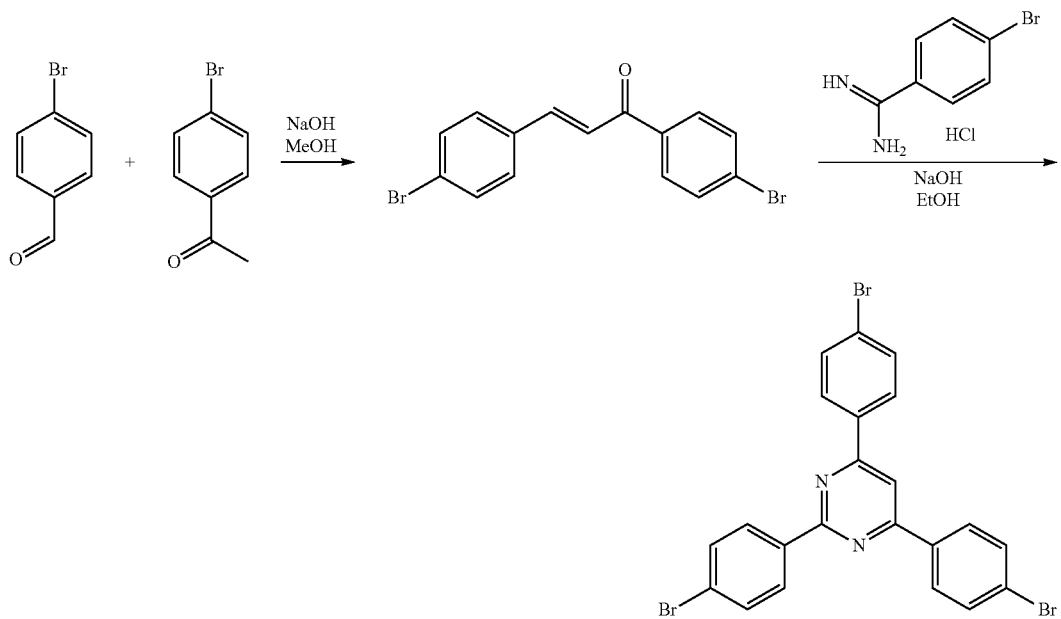

E1

-continued

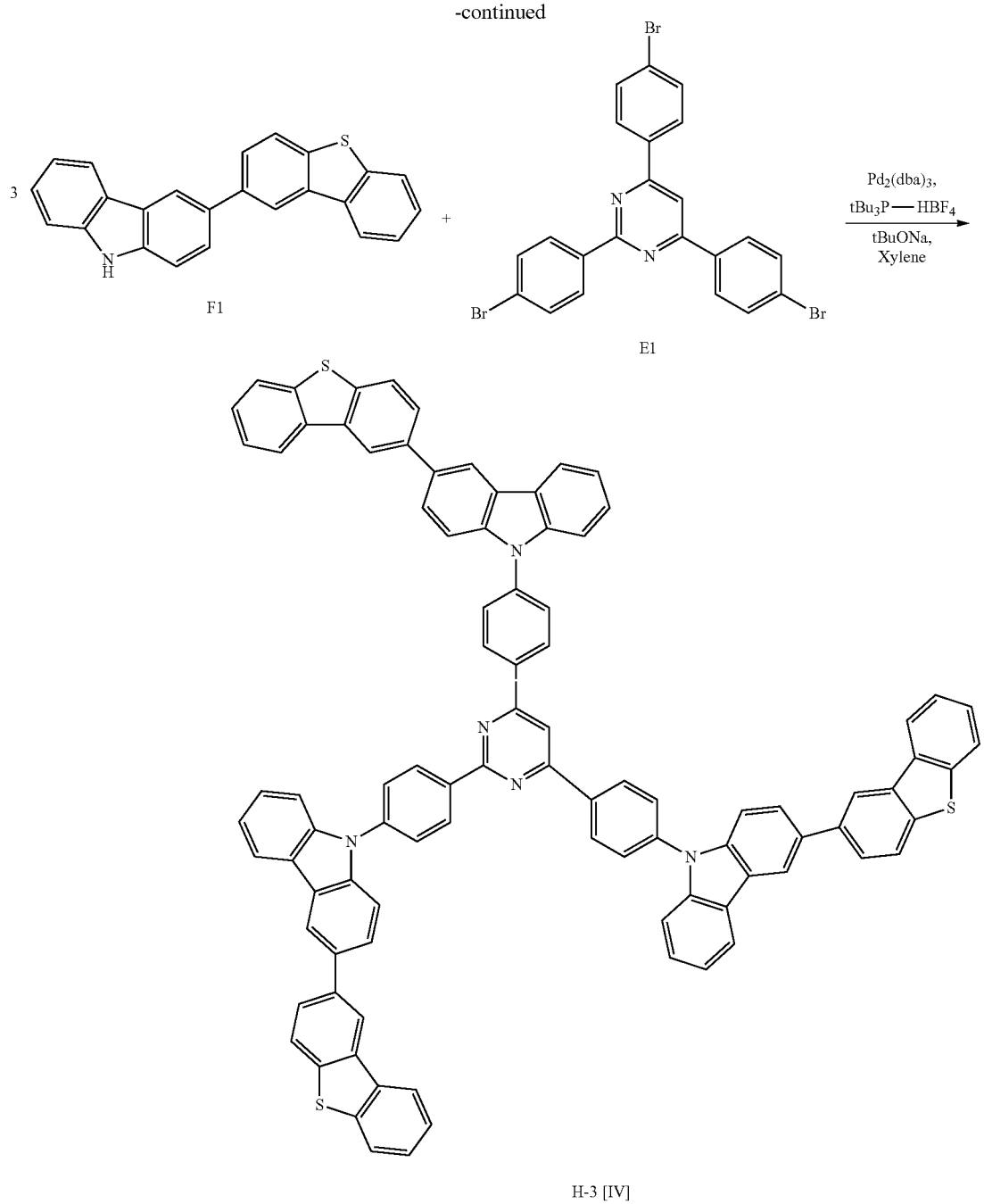

H-3 [IV]

After adding sodium hydroxide (0.584 g, 14.6 mmol) to a solution of 4-bromobenzaldehyde (17.0 mL, 146 mmol) and 4-bromoacetophenone (19.3 mL, 146 mmol) in methanol (300 mL), the resultant solution was stirred at room temperature for 10.5 h.

The precipitated solid was collected by filtration, washed with methanol, and then dried under vacuum to obtain a powder (47.8 g, yield: 90%).

Then, after adding 4-bromobenzamidine hydrochloride (4.00 g, 16.9 mmol) and sodium hydroxide (0.745 g, 18.6 mmol) and then ethanol (35 mL) to the obtained powder (12.4 g, 33.9 mmol), the reaction was allowed to proceed for 12.5 h while refluxing under heating. The white powder formed was collected by filtration, washed with ethanol until the washings were made colorless, further washed with water and then ethanol, and then dried under vacuum to obtain target pyrimidine intermediate E1 (7.42 g, yield: 80%).

Under argon atmosphere, carbazolyl intermediate F1 (3.15 g, 9.00 mmol), pyrimidine intermediate E1 (1.23 g, 3.00 mmol), tris(dibenzylideneacetone)dipalladium (0.110 g, 0.120 mmol), tri-t-butylphosphonium tetrafluoroborate (0.139 g, 0.480 mmol), sodium t-butoxide (0.965 g, 9.00 mmol), and anhydrous toluene (60 mL) were successively mixed, and the resultant mixture was refluxed for 8 h under heating.

After cooling the reaction liquid to room temperature, the insolubles were removed by filtration, and the organic solvent was evaporated off under reduced pressure. The obtained residue was purified by silica gel column chromatography to obtain compound H-3[IV] (2.63 g, yield: 65%).

The results of analysis by HPLC (High Performance Liquid Chromatography) and LC-MS (Liquid Chromatography-Mass Spectrometry) on compound H-3[IV] are shown below.

HPLC purity: 99.2%
LC-MS: calcd for $C_{94}H_{55}N_5S_3$=1349.
found m/z=1349 (M+, 100).

Synthesis Example 4[IV](Synthesis of Compound H-4[IV])

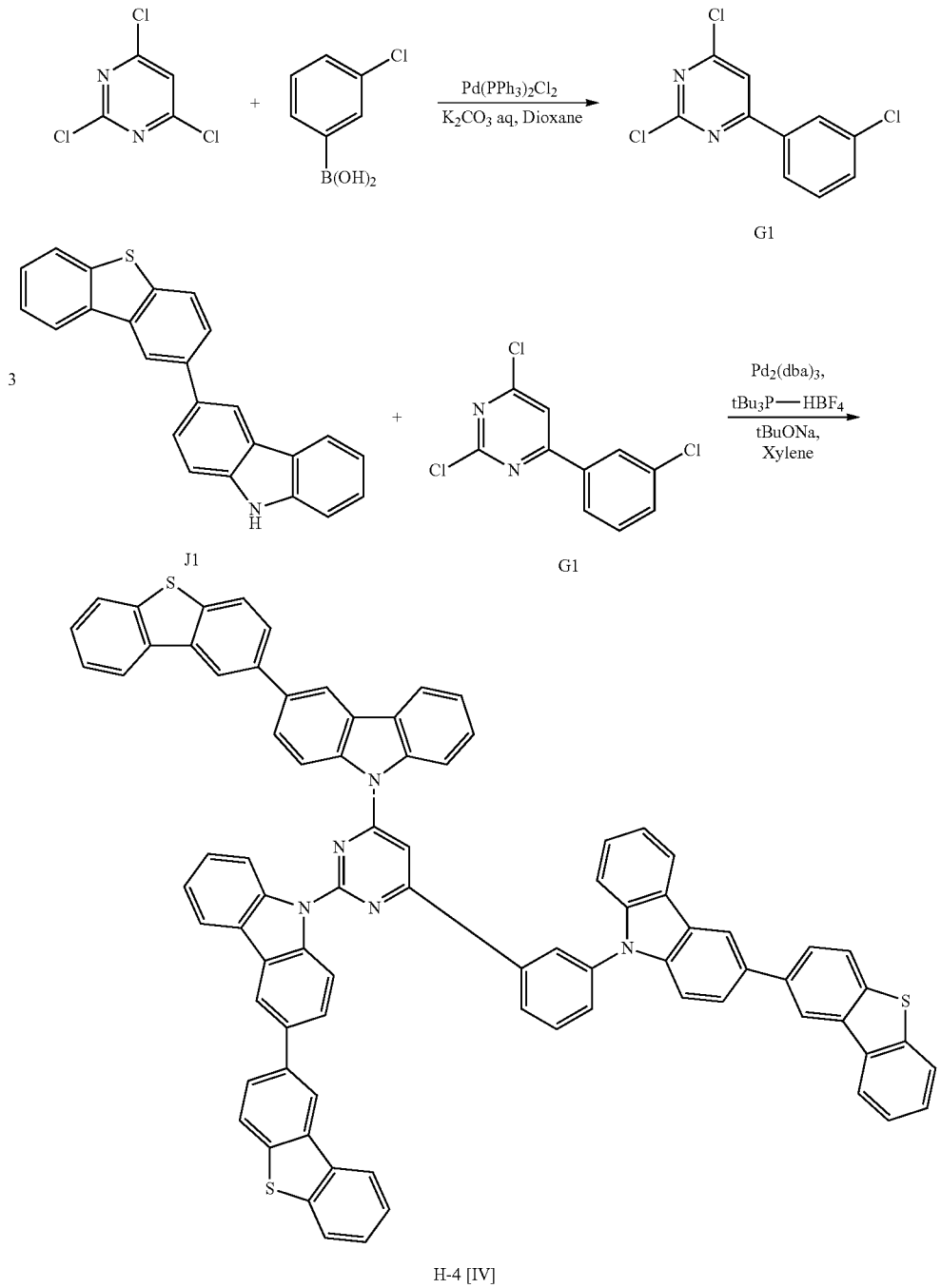

H-4 [IV]

Under argon atmosphere, 2,4,6-trichloropyrimidine (3.67 g, 20 mmol), 3-chlorophenylboronic acid (3.13 g, 20 mmol), dichloro(bistriphenylphosphine)palladium complex (0.351 g, 0.5 mmol), 1,4-dioxane (80 mL), and a 2 M aqueous solution of potassium carbonate (40 mL) were successively mixed, and the resultant mixture was refluxed for 8 h under heating. After cooling to room temperature, the reaction liquid was diluted with toluene, washed with water, and dried under reduced pressure. The obtained residue was purified by silica gel column chromatography to obtain pyrimidine intermediate G1 (4.05 g, yield: 78%).

Under argon atmosphere, carbazolyl intermediate J1 (3.15 g, 9.00 mmol), pyrimidine intermediate G1 (0.779 g, 3.00 mmol), tris(dibenzylideneacetone)dipalladium (0.110 g, 0.120 mmol), tri-t-butylphosphonium tetrafluoroborate (0.139 g, 0.480 mmol), sodium t-butoxide (0.965 g, 9.00 mmol), and anhydrous toluene (60 mL) were successively mixed, and the resultant mixture was refluxed for 8 h under heating.

After cooling the reaction liquid to room temperature, the insolubles were removed by filtration, and the organic solvent was evaporated off under reduced pressure. The obtained residue was purified by silica gel column chromatography to obtain compound H-4[IV] (1.98 g, yield: 55%).

The results of analysis by HPLC (High Performance Liquid Chromatography) and LC-MS (Liquid Chromatography-Mass Spectrometry) on compound H-4[IV] are shown below.

HPLC purity: 98.6%
LC-MS: calcd for $C_{82}H_{47}N_5S_3$=1197.
found m/z=1197 (M+, 100).

Synthesis Example 5[IV](Synthesis of Compound H-5[IV])

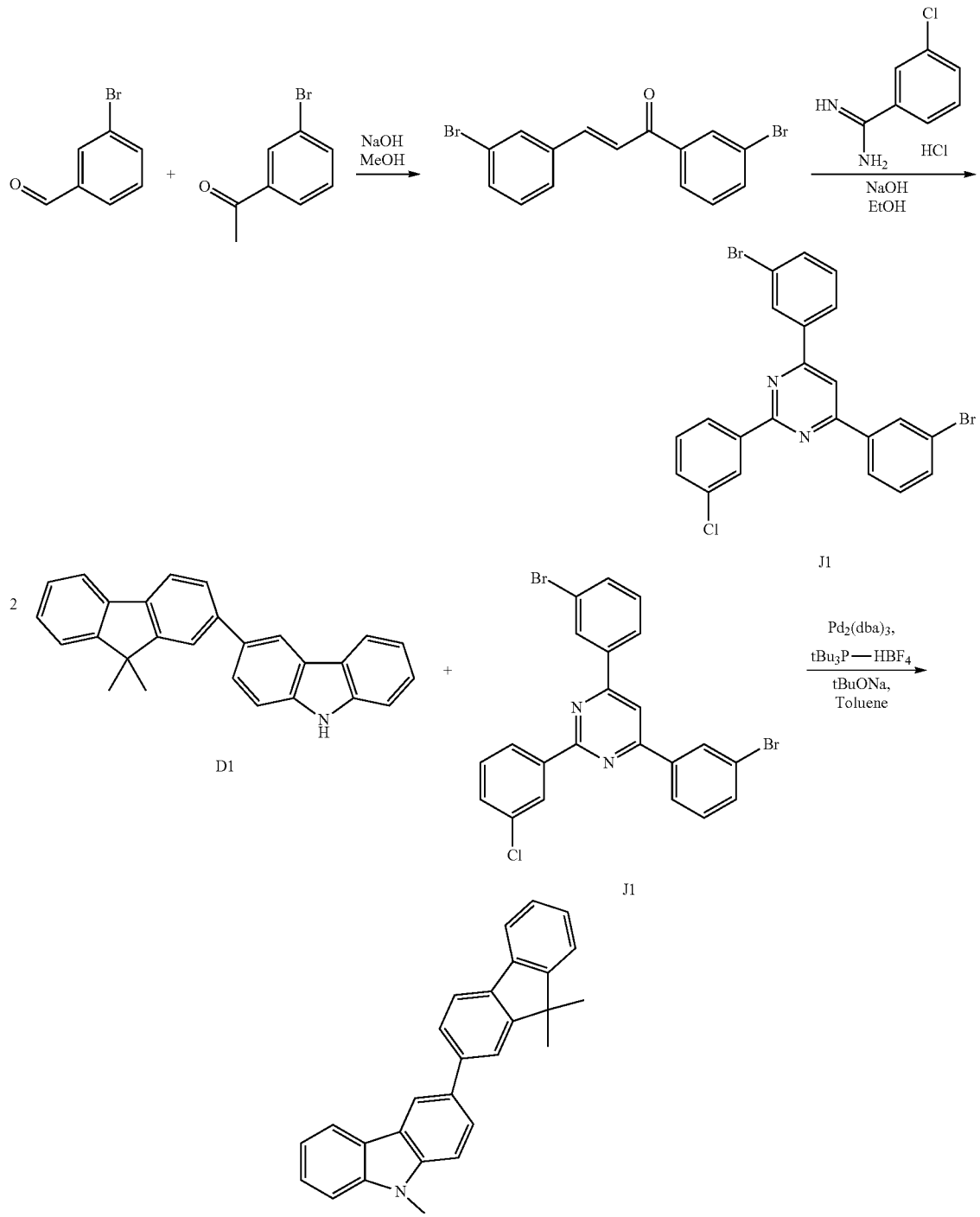

-continued
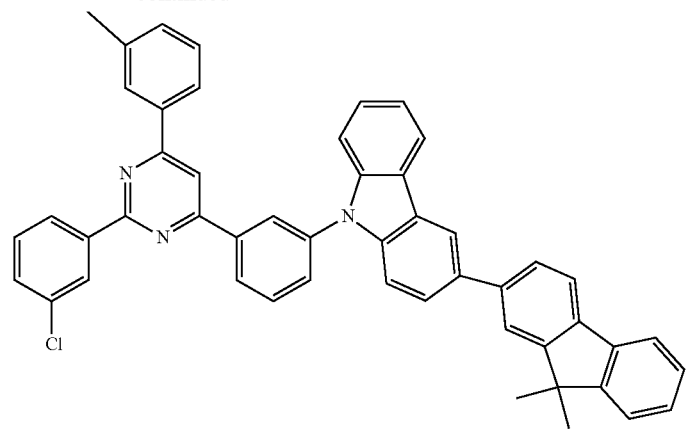
K1
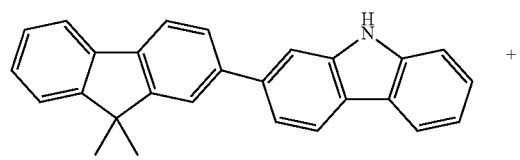 +
L1
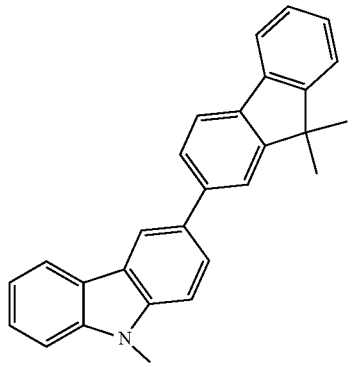
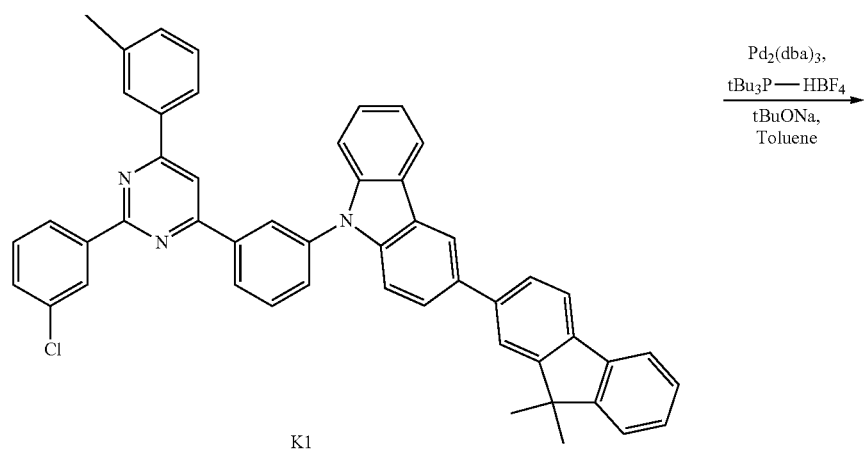
K1

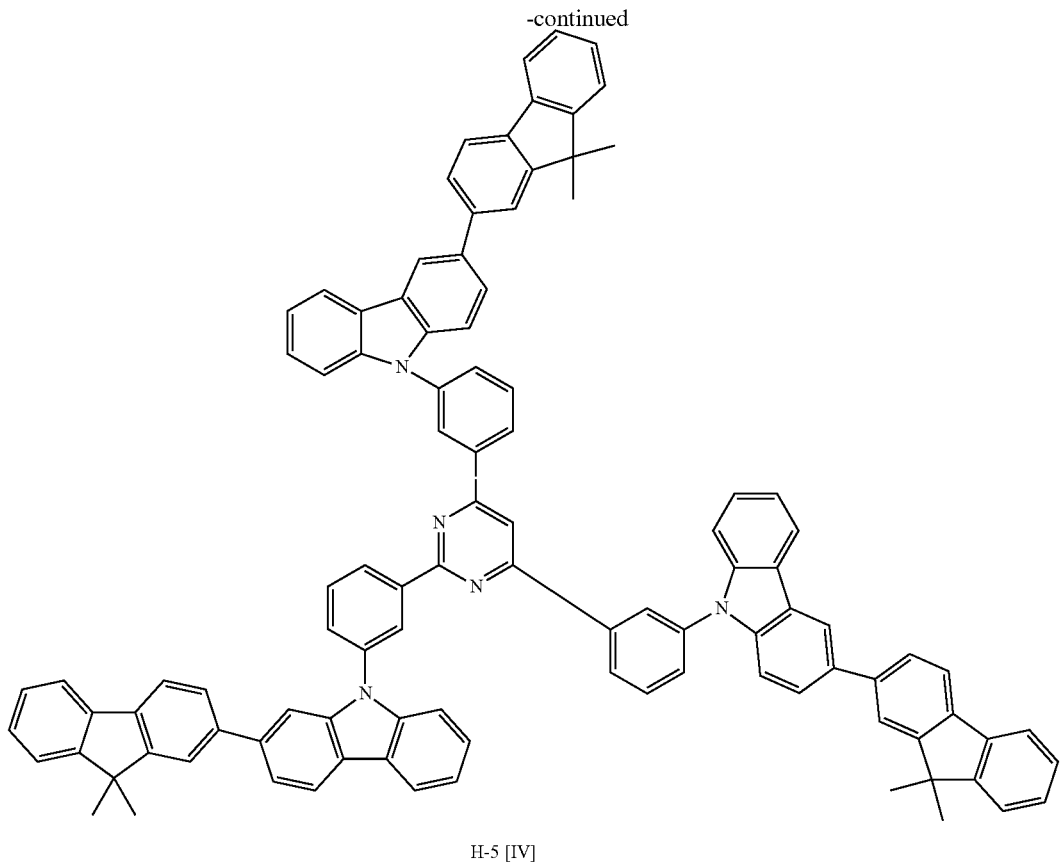

H-5 [IV]

After adding sodium hydroxide (0.584 g, 14.6 mmol) to a solution of 3-bromobenzaldehyde (17.0 mL, 146 mmol) and 3-bromoacetophenone (19.3 mL, 146 mmol) in methanol (300 mL), the resultant solution was stirred at room temperature for 10.5 h.

The precipitated solid was collected by filtration, washed with methanol, and then dried under vacuum to obtain a cream-colored powder (47.8 g, yield: 90%).

Then, after adding 3-chlorobenzamidine hydrochloride (3.23 g, 16.9 mmol) and sodium hydroxide (0.745 g, 18.6 mmol) and then ethanol (35 mL) to the obtained powder (12.4 g, 33.9 mmol), the reaction was allowed to proceed for 12.5 h while refluxing under heating. The white powder formed was collected by filtration, washed with ethanol until the washings were made colorless, further washed with water and then ethanol, and then dried under vacuum to obtain target pyrimidine intermediate J1 (5.25 g, yield: 62%).

Under argon atmosphere, carbazolyl intermediate D1 (2.16 g, 6.00 mmol), pyrimidine intermediate J1 (1.50 g, 3.00 mmol), tris(dibenzylideneacetone)dipalladium (0.110 g, 0.120 mmol), tri-t-butylphosphonium tetrafluoroborate (0.139 g, 0.48 mmol), sodium t-butoxide (0.288 g, 3.00 mmol), and anhydrous toluene (60 mL) were successively mixed, and the resultant mixture was refluxed for 11 h under heating.

After cooling the reaction liquid to room temperature, the insolubles were removed by filtration, and the organic solvent was evaporated off under reduced pressure. The obtained residue was purified by silica gel column chromatography to obtain compound K1 (2.22 g, yield: 70%).

Under argon atmosphere, compound K1 (2.22 g, 3.00 mmol), carbazolyl intermediate L1 (1.08 g, 3.00 mmol), tris(dibenzylideneacetone)dipalladium (0.110 g, 0.120 mmol), tri-t-butylphosphonium tetrafluoroborate (0.139 g, 0.48 mmol), sodium t-butoxide (0.288 g, 3.00 mmol), and anhydrous toluene (60 mL) were successively mixed, and the resultant mixture was refluxed for 11 h under heating.

After cooling the reaction liquid to room temperature, the insolubles were removed by filtration, and the organic solvent was evaporated off under reduced pressure. The obtained residue was purified by silica gel column chromatography to obtain compound H-5[IV] (3.52 g, yield: 85%).

The results of analysis by HPLC (High Performance Liquid Chromatography) and LC-MS (Liquid Chromatography-Mass Spectrometry) on compound H-5[IV] are shown below.

HPLC purity: 99.0%

LC-MS: calcd for $C_{103}H_{73}N_5$=1379.

found m/z=1379 (M+, 100).

Synthesis Example 6[IV](Synthesis of Compound H-6[IV])

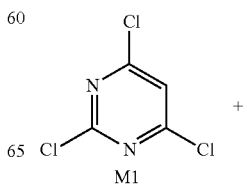

M1

-continued

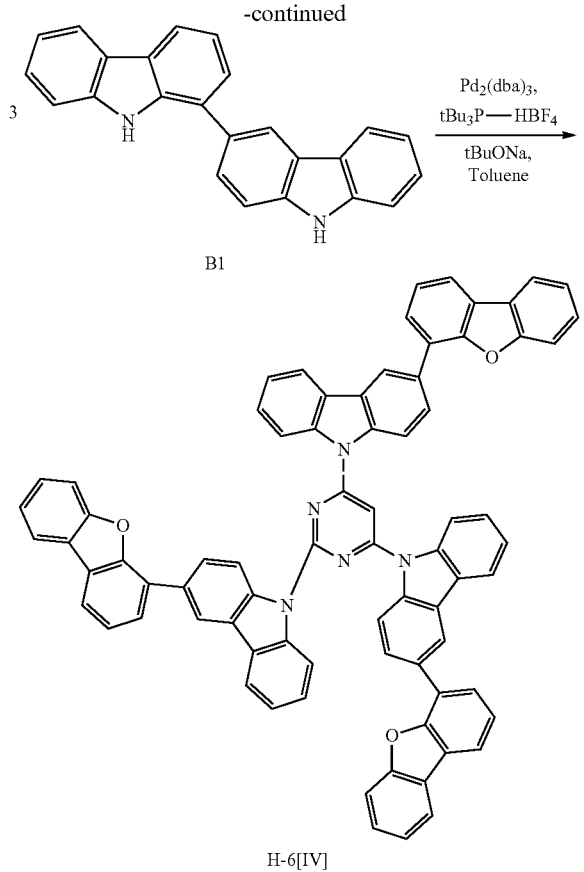

B1

H-6[IV]

Under argon atmosphere, carbazolyl intermediate B1 (3.00 g, 9.00 mmol), pyrimidine intermediate M1 (0.550 g, 3.00 mmol), tris(dibenzylideneacetone)dipalladium (0.110 g, 0.120 mmol), tri-t-butylphosphonium tetrafluoroborate (0.139 g, 0.48 mmol), sodium t-butoxide (0.288 g, 3.00 mmol), and anhydrous toluene (60 mL) were successively mixed, and the resultant mixture was refluxed for 11 h under heating.

After cooling the reaction liquid to room temperature, the insolubles were removed by filtration, and the organic solvent was evaporated off under reduced pressure. The obtained residue was purified by silica gel column chromatography to obtain compound H-6[IV] (2.58 g, yield: 80%).

The results of analysis by HPLC (High Performance Liquid Chromatography) and LC-MS (Liquid Chromatography-Mass Spectrometry) on compound H-6[IV] are shown below.

HPLC purity: 99.0%
LC-MS: calcd for $C_{76}H_{43}N_5O_3$=1073.
found m/z=1073 (M+, 100).

The compounds within the scope of the claims of this application can be synthesized by referring to the above synthetic reactions while using a known synthetic reaction and a starting material in accordance with the target compound.

Example 1[IV]

Cleaning of Substrate

A glass substrate of 25 mm×25 mm×1.1 mm thickness having an ITO transparent electrode (product of Geomatec Company) was cleaned by ultrasonic cleaning in isopropyl alcohol for 5 min and then UV ozone cleaning for 5 min.

Formation of Underlayers

Clevious AI4083 (tradename) manufactured by Heraeus as a hole transporting material was spin-coated on the ITO substrate to form a hole transporting layer with a thickness of 30 nm. Thereafter, unnecessary portion was removed by acetone and then a base substrate was produced by baking in air for 10 min on a hot plate at 200° C.

Formation of Light Emitting Layer

A 1.6% by mass toluene solution containing the compound H-1[IV] obtained in Synthesis Example 1[IV] as a host material and the following compound D-ii as a dopant material was prepared in a mixing ratio of compound H-1[IV]:compound D-ii=90:10 by mass. The toluene solution was spin-coated on the base substrate into a thickness of 50 nm. Thereafter, unnecessary portion was removed by toluene and then the coated film was dried under heating at 150° C. on a hot plate to obtain a coat-laminated substrate having a light emitting layer. The film-forming operations for forming the light emitting layer were all conducted in a glove box under a nitrogen atmosphere.

Vapor Deposition and Sealing

The coat-laminated substrate was conveyed into a vapor deposition chamber and the following compound ET-1 as an electron transporting material was vapor-deposited into a thickness of 50 nm to form an electron transporting layer. Then, lithium fluoride was vapor-deposited into a thickness of 1 nm and aluminum was vapor-deposited into a thickness of 80 nm. After completing all the vapor deposition processes, the substrate with laminated films was sealed with a bored glass in a glove box under a nitrogen atmosphere to produce an organic EL device.

Evaluation of Device

By driving at a direct current, the obtained organic EL device was allowed to emit light to measure the external quantum efficiency (EQE) at a current density of 10 mA/cm$^2$. The result is shown in Table 4.

The organic EL device was further allowed to continuously emit light by driving at a direct current, and the time taken until the luminance was reduced from 1000 cd/m$^2$ to 800 cd/m$^2$ (LT80) was measured. The result is shown in Table 4.

An organic EL device was produced in the same manner as described above except for drying the coated film at 200° C. under heating in the formation of the light emitting layer. The obtained organic EL device was measured for the external quantum efficiency (EQE) in the same manner as described above. The result is shown in Table 4.

D-ii

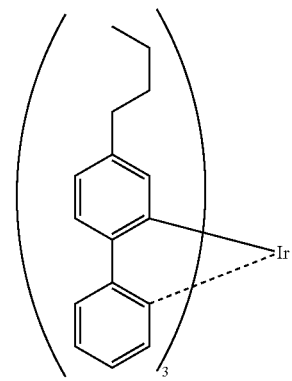

-continued

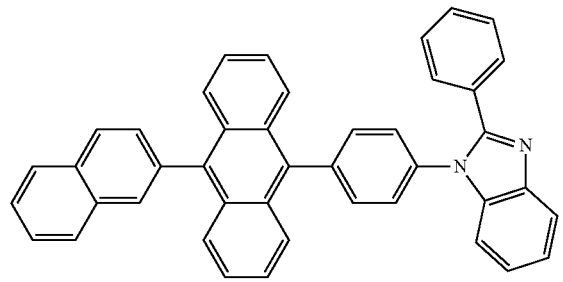

ET-1

Example 2[IV]

Each organic EL device was produced in the same manner as in Example 1[IV] except for using compound H-2[IV] obtained in Synthesis Example 2[IV] as a host material. The results are shown in Table 4.

Example 3[IV]

Each organic EL device was produced in the same manner as in Example 1[IV] except for using compound H-3[IV] obtained in Synthesis Example 3[IV] as a host material. The results are shown in Table 4.

Example 4[IV]

Each organic EL device was produced in the same manner as in Example 1[IV] except for using compound H-4[IV] obtained in Synthesis Example 4[IV] as a host material. The results are shown in Table 4.

Example 5[IV]

Each organic EL device was produced in the same manner as in Example 1[IV] except for using compound H-5[IV] obtained in Synthesis Example 5[IV] as a host material. The results are shown in Table 4.

Example 6[IV]

Each organic EL device was produced in the same manner as in Example 1[IV] except for using compound H-6[IV] obtained in Synthesis Example 6[IV] as a host material. The results are shown in Table 4.

Comparative Example 1[IV]

Each organic EL device was produced in the same manner as in Example 1[IV] except for using compound Q-1[IV] described in WO 2012/086170 as a host material. The results are shown in Table 4.

Comparative Example 2[IV]

Each organic EL device was produced in the same manner as in Example 1[IV] except for using compound Q-2[IV] described in WO 2013/081088 as a host material. The results are shown in Table 4.

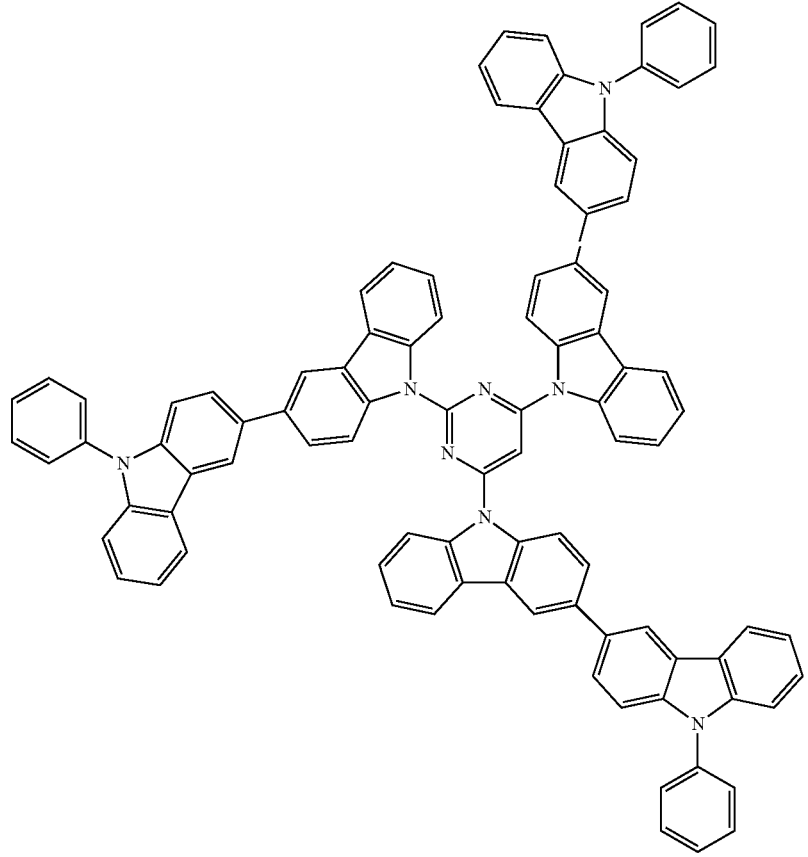

Q-1[IV]

-continued

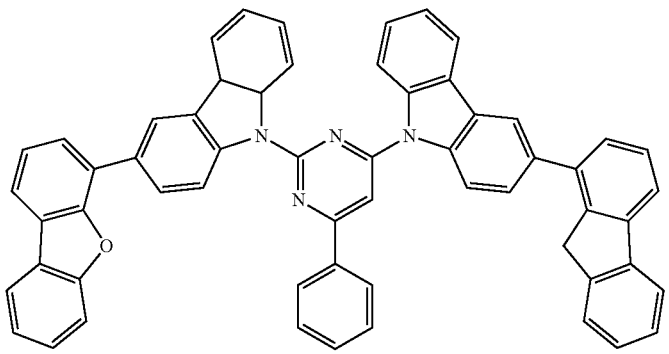

Q-2[IV]

TABLE 4

| | | External quantum efficiency (%) | | |
|---|---|---|---|---|
| | Host material | dried at 150° C. | dried at 200° C. | LT(80) (h) |
| Example 1[IV] | H-1[IV] | 7.2 | 7.1 | 55 |
| Example 2[IV] | H-2[IV] | 7.1 | 6.9 | 58 |
| Example 3[IV] | H-3[IV] | 7.8 | 7.3 | 60 |
| Example 4[IV] | H-4[IV] | 7.7 | 7.6 | 54 |
| Example 5[IV] | H-5[IV] | 7.7 | 7.8 | 49 |
| Example 6[IV] | H-6[IV] | 7.3 | 7.0 | 48 |
| Comparative Example 1[IV] | Q-1[IV] | 7.6 | 7.3 | 5 |

TABLE 4-continued

| | | External quantum efficiency (%) | | |
|---|---|---|---|---|
| | Host material | dried at 150° C. | dried at 200° C. | LT(80) (h) |
| Comparative Example 2[IV] | Q-2[IV] | 7.4 | 3.8 | — |

(5) Next, the synthesis method of compound 1[V], the production method of organic EL devices employing compound 1[V], and the evaluation results thereof are described below.

Compound 1[V]

Synthesis Example 1[V](Synthesis of Compound H-1[V])

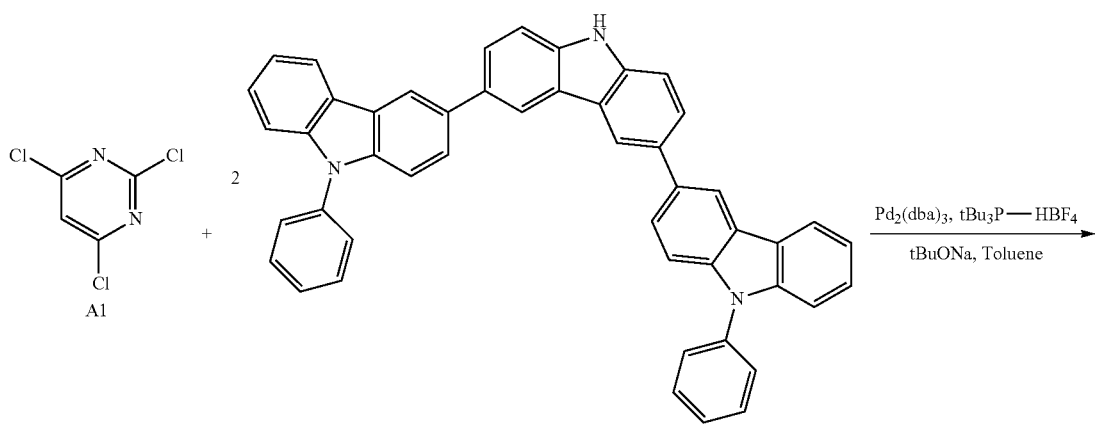

-continued
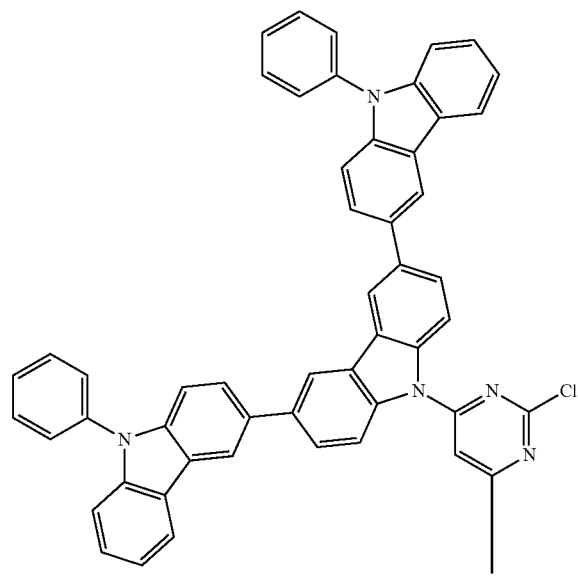
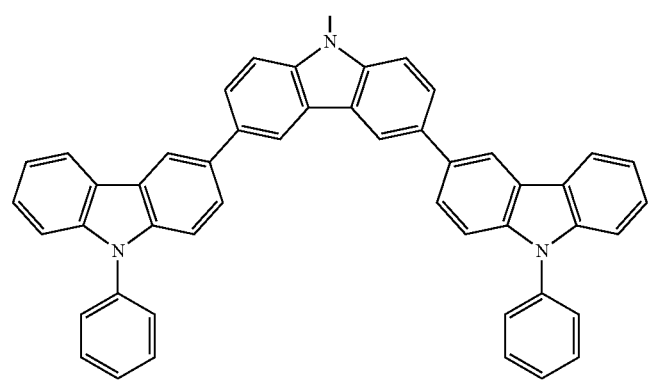
C1

-continued
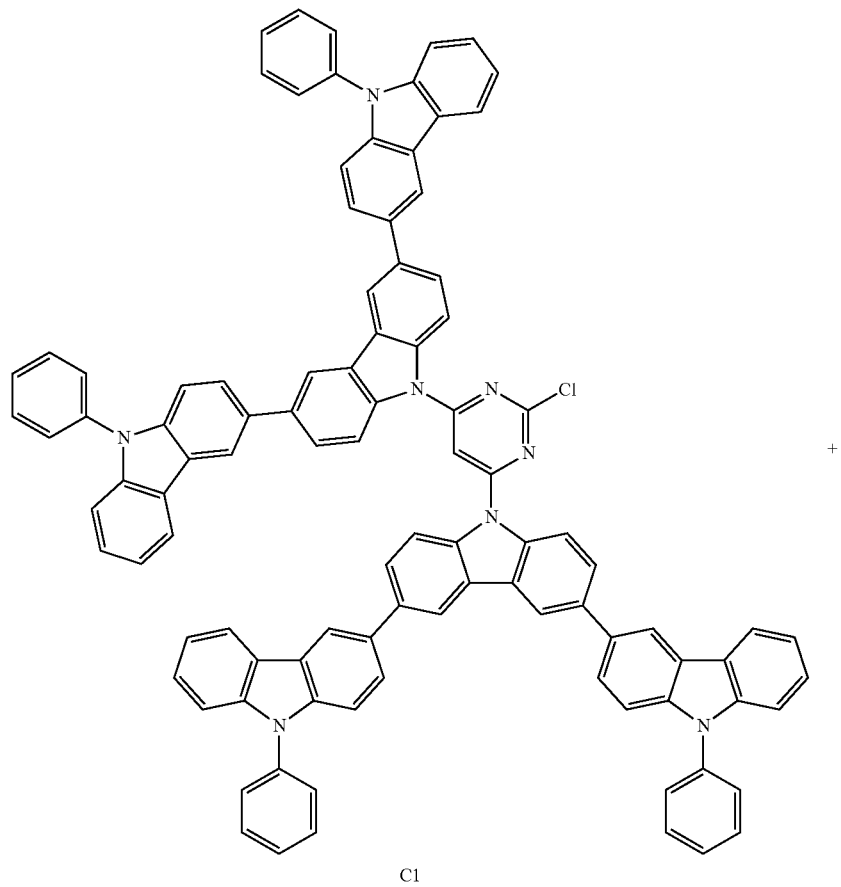
C1
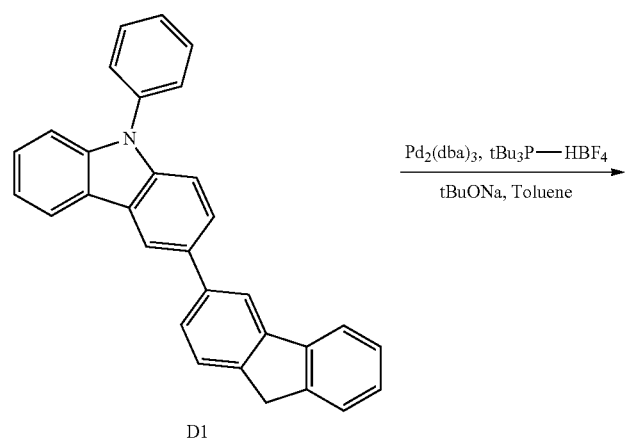
D1

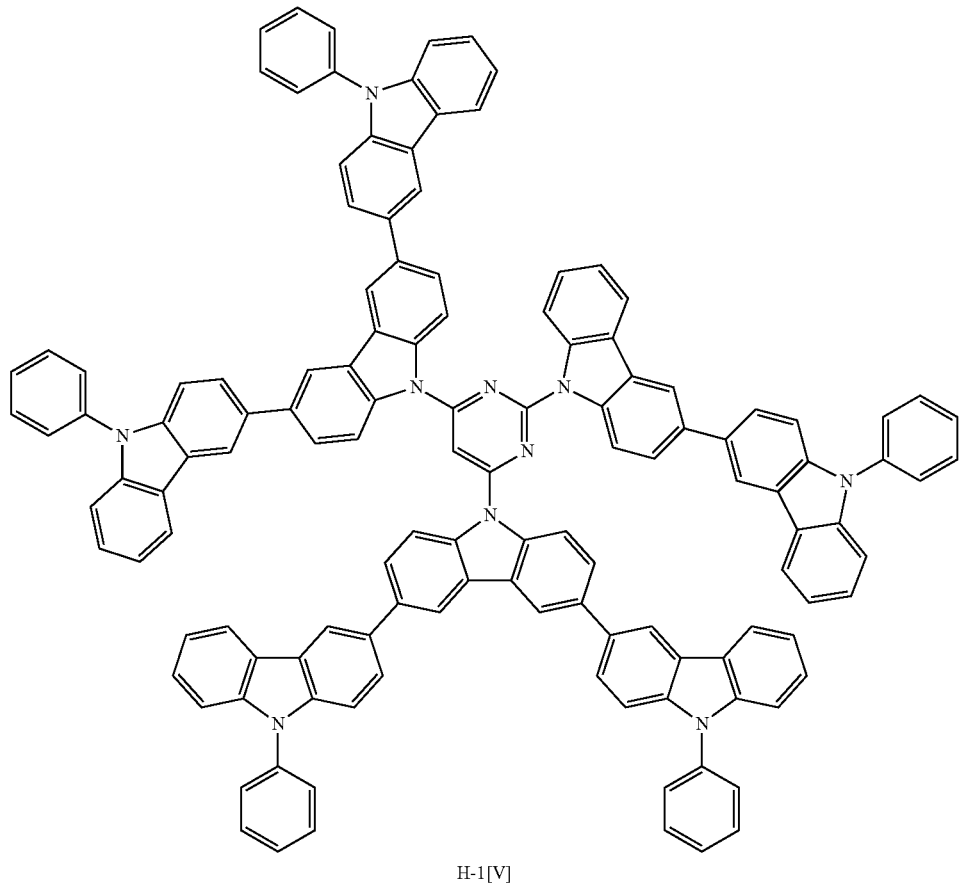

H-1[V]

Under argon atmosphere, compound A1 (0.550 g, 3.00 mmol), carbazolyl intermediate B1 (3.90 g, 6.00 mmol), tris(dibenzylideneacetone)dipalladium (0.110 g, 0.120 mmol), tri-t-butylphosphonium tetrafluoroborate (0.139 g, 0.48 mmol), sodium t-butoxide (0.288 g, 3.00 mmol), and anhydrous toluene (60 mL) were successively mixed, and the resultant mixture was refluxed for 11 h under heating.

After cooling the reaction liquid to room temperature, the insolubles were removed by filtration, and the organic solvent was evaporated off under reduced pressure. The obtained residue was purified by silica gel column chromatography to obtain compound C1 (3.60 g, yield: 85%).

Under argon atmosphere, compound C1 (3.60 g, 3.00 mmol), carbazolyl intermediate D1 (1.23 g, 3.00 mmol), tris(dibenzylideneacetone)dipalladium (0.110 g, 0.120 mmol), tri-t-butylphosphonium tetrafluoroborate (0.139 g, 0.48 mmol), sodium t-butoxide (0.288 g, 3.00 mmol), and anhydrous toluene (60 mL) were successively mixed, and the resultant mixture was refluxed for 11 h under heating.

After cooling the reaction liquid to room temperature, the insolubles were removed by filtration, and the organic solvent was evaporated off under reduced pressure. The obtained residue was purified by silica gel column chromatography to obtain compound H-1[V] (4.54 g, yield: 85%).

The results of analysis by HPLC (High Performance Liquid Chromatography) and LC-MS (Liquid Chromatography-Mass Spectrometry) on compound H-1[V] are shown below.

HPLC purity: 99.0%
LC-MS: calcd for $C_{130}H_{80}N_{10}$=1780.
found m/z=1780 (M+, 100).

Synthesis Example 2[V](Synthesis of Compound H-2[V])
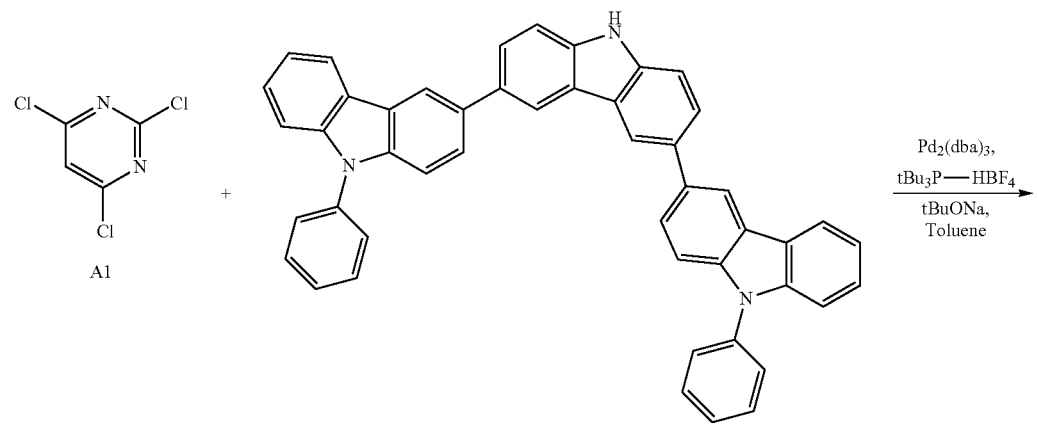
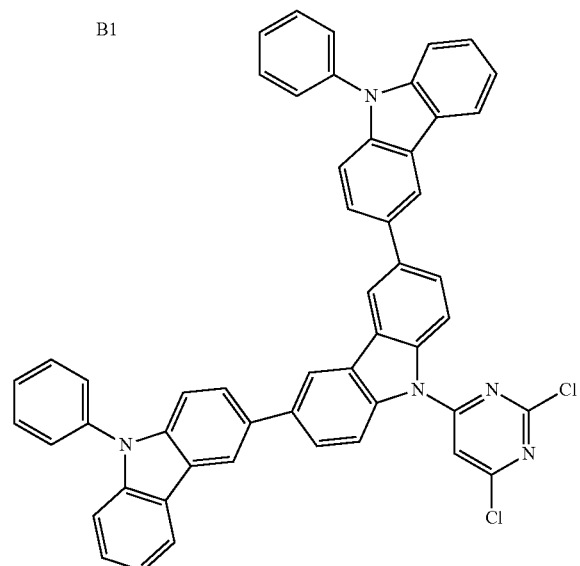
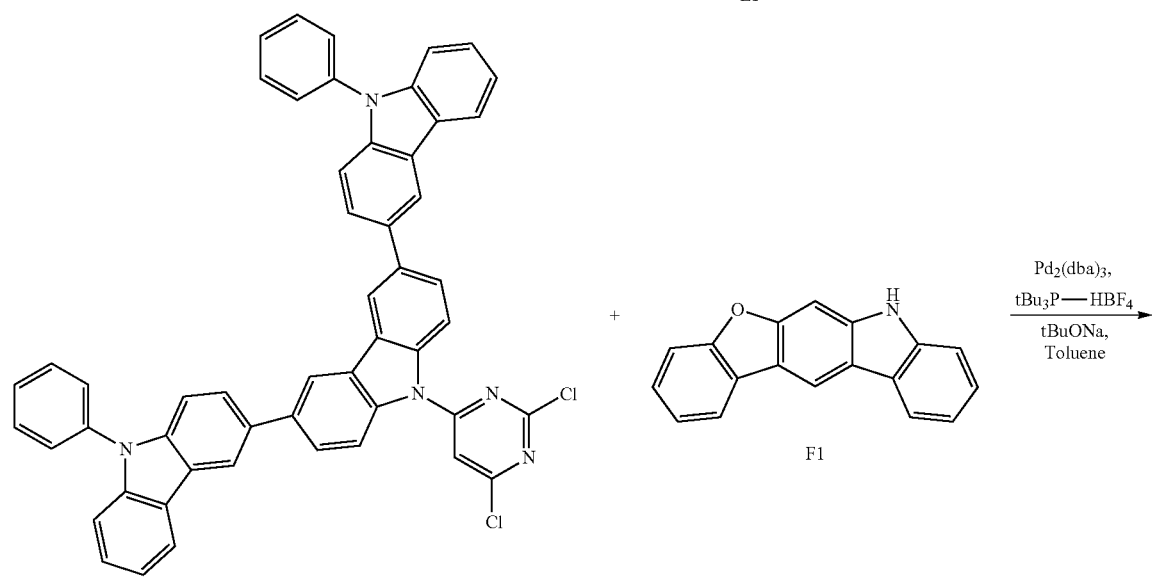

-continued
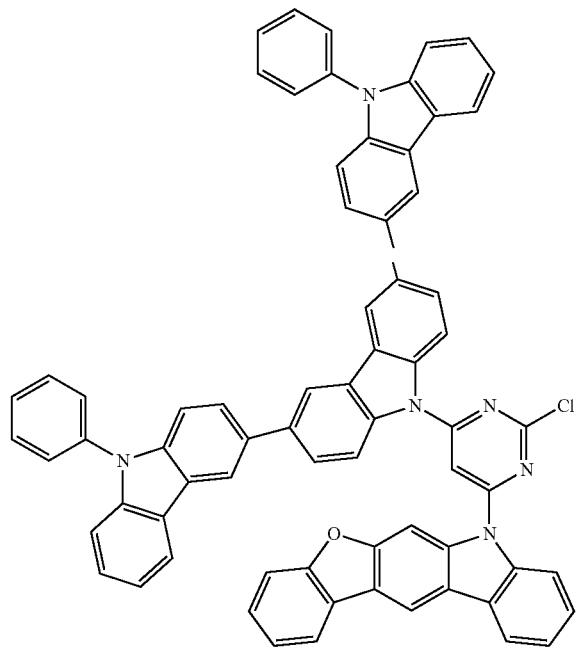
G1
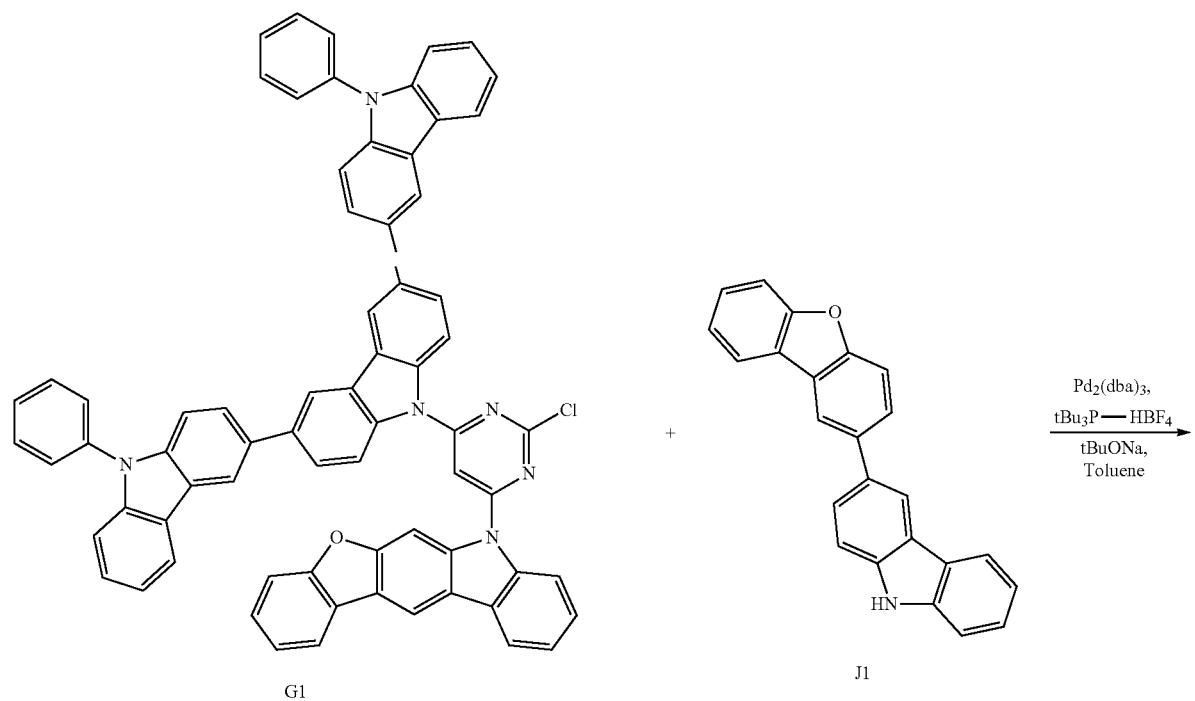
G1            J1
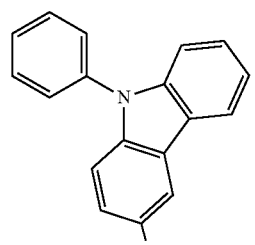

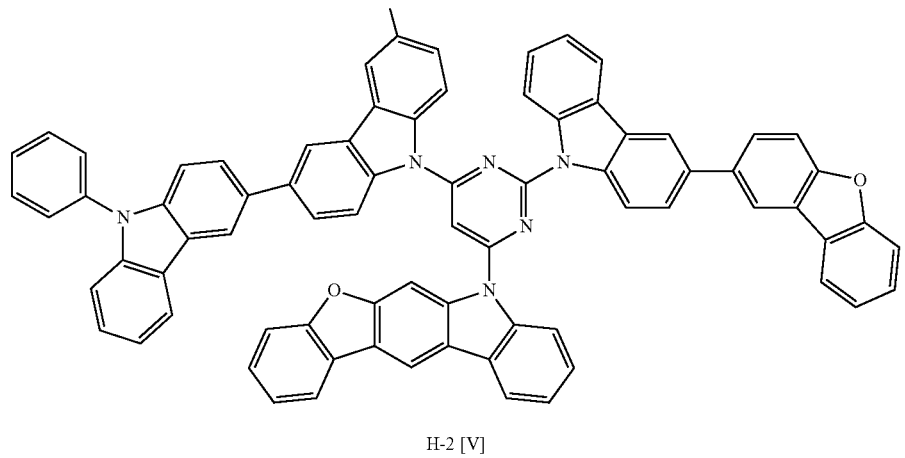

H-2 [V]

Under argon atmosphere, compound A1 (0.550 g, 3.00 mmol), carbazolyl intermediate B1 (1.95 g, 3.00 mmol), tris(dibenzylideneacetone)dipalladium (0.110 g, 0.120 mmol), tri-t-butylphosphonium tetrafluoroborate (0.139 g, 0.48 mmol), sodium t-butoxide (0.288 g, 3.00 mmol), and anhydrous toluene (60 mL) were successively mixed, and the resultant mixture was refluxed for 11 h under heating.

After cooling the reaction liquid to room temperature, the insolubles were removed by filtration, and the organic solvent was evaporated off under reduced pressure. The obtained residue was purified by silica gel column chromatography to obtain compound E1 (1.91 g, yield: 80%).

Under argon atmosphere, compound E1 (1.91 g, 3.00 mmol), carbazolyl intermediate F1 (0.771 g, 3.00 mmol), tris(dibenzylideneacetone)dipalladium (0.110 g, 0.120 mmol), tri-t-butylphosphonium tetrafluoroborate (0.139 g, 0.48 mmol), sodium t-butoxide (0.288 g, 3.00 mmol), and anhydrous toluene (60 mL) were successively mixed, and the resultant mixture was refluxed for 11 h under heating.

After cooling the reaction liquid to room temperature, the insolubles were removed by filtration, and the organic solvent was evaporated off under reduced pressure. The obtained residue was purified by silica gel column chromatography to obtain compound G1 (2.44 g, yield: 80%).

Under argon atmosphere, compound G1 (2.44 g, 3.00 mmol), carbazolyl intermediate J1 (1.00 g, 3.00 mmol), tris(dibenzylideneacetone)dipalladium (0.110 g, 0.120 mmol), tri-t-butylphosphonium tetrafluoroborate (0.139 g, 0.48 mmol), sodium t-butoxide (0.288 g, 3.00 mmol), and anhydrous toluene (60 mL) were successively mixed, and the resultant mixture was refluxed for 11 h under heating.

After cooling the reaction liquid to room temperature, the insolubles were removed by filtration, and the organic solvent was evaporated off under reduced pressure. The obtained residue was purified by silica gel column chromatography to obtain compound H-2[V] (3.15 g, yield: 80%).

The results of analysis by HPLC (High Performance Liquid Chromatography) and LC-MS (Liquid Chromatography-Mass Spectrometry) on compound H-2[V] are shown below.

HPLC purity: 99.0%
LC-MS: calcd for $C_{94}H_{55}N_7O_2$=1313.
found m/z=1313 (M+, 100).

Synthesis Example 3[V](Synthesis of Compound H-3[V])

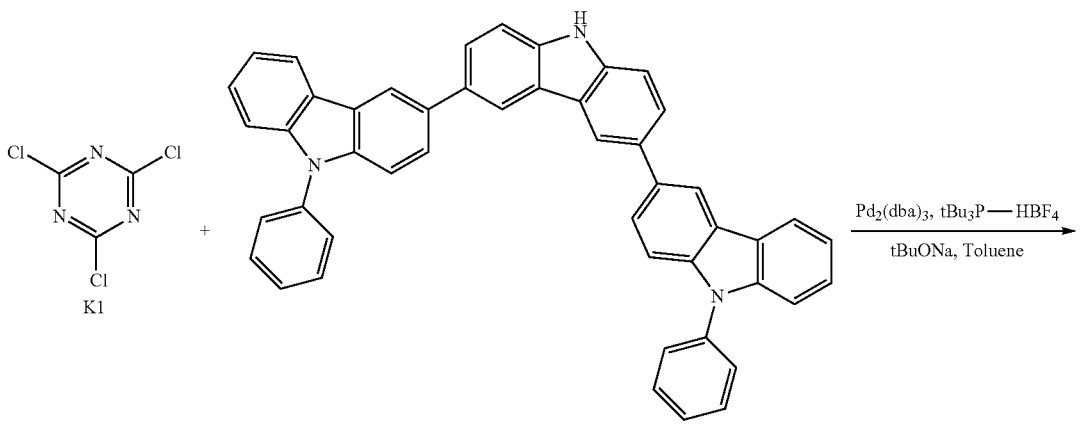

-continued
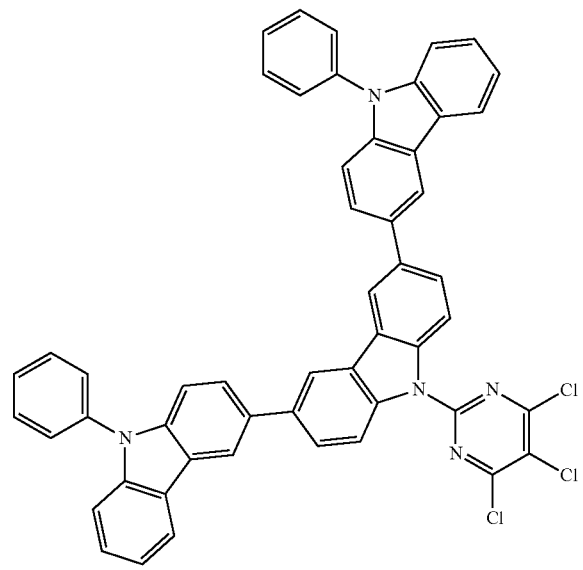
L1
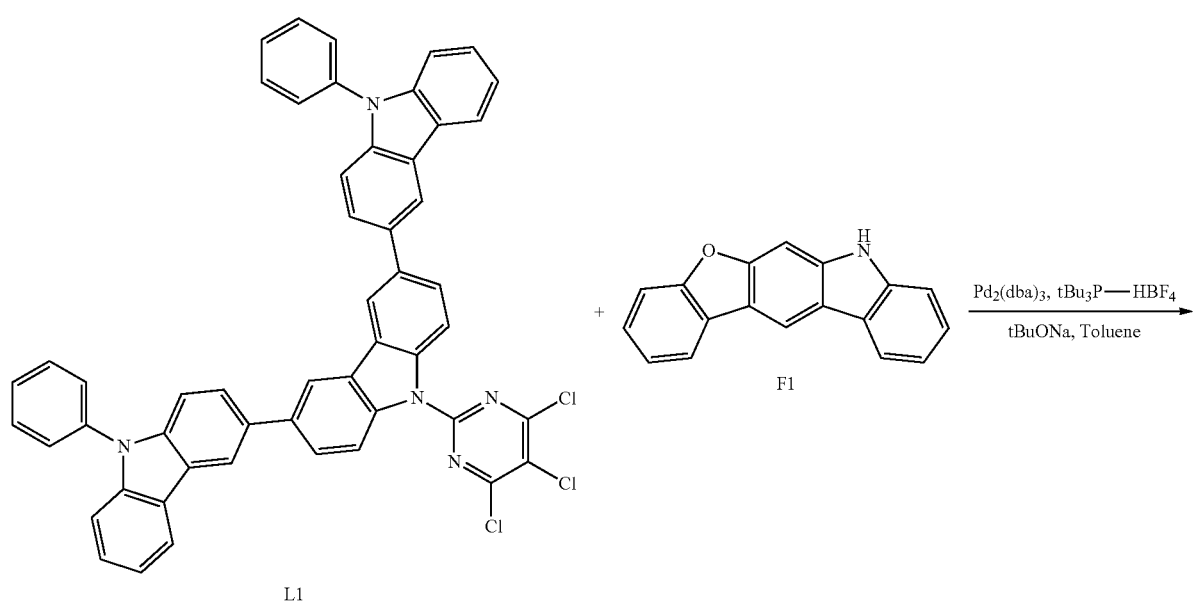
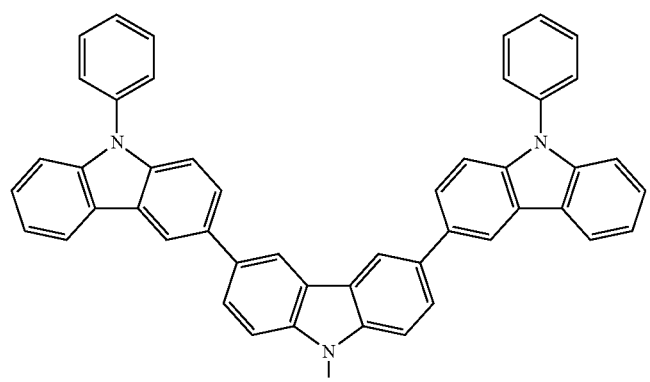

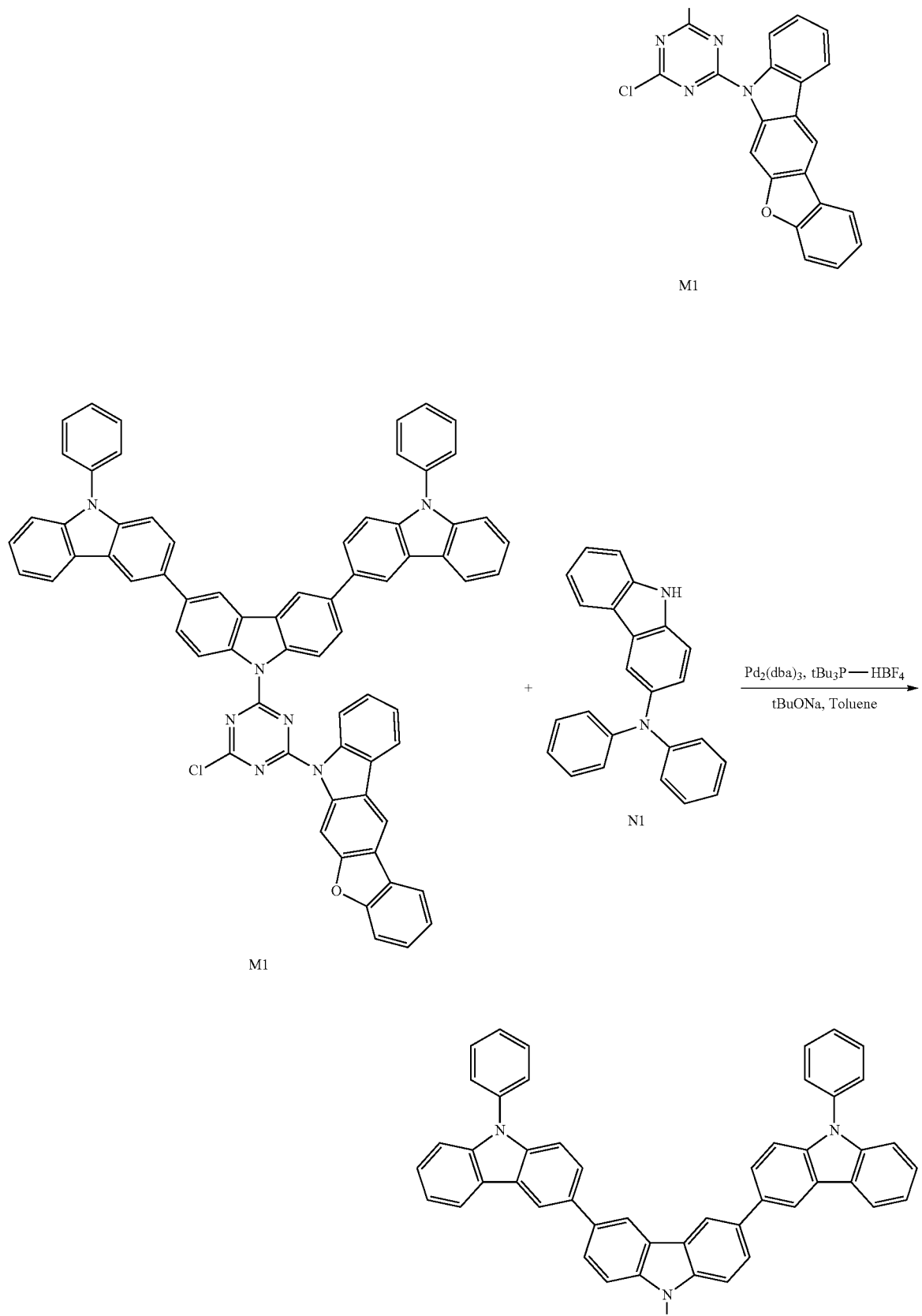

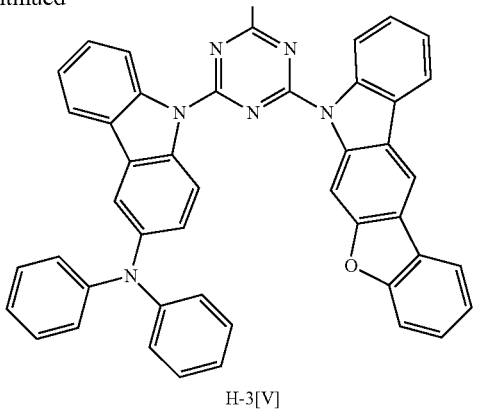

H-3[V]

Under argon atmosphere, compound K1 (0.553 g, 3.00 mmol), carbazolyl intermediate B1 (1.95 g, 3.00 mmol), tris(dibenzylideneacetone)dipalladium (0.110 g, 0.120 mmol), tri-t-butylphosphonium tetrafluoroborate (0.139 g, 0.48 mmol), sodium t-butoxide (0.288 g, 3.00 mmol), and anhydrous toluene (60 mL) were successively mixed, and the resultant mixture was refluxed for 11 h under heating.

After cooling the reaction liquid to room temperature, the insolubles were removed by filtration, and the organic solvent was evaporated off under reduced pressure. The obtained residue was purified by silica gel column chromatography to obtain compound L1 (1.91 g, yield: 80%).

Under argon atmosphere, compound L1 (1.91 g, 3.00 mmol), carbazolyl intermediate F1 (0.772 g, 3.00 mmol), tris(dibenzylideneacetone)dipalladium (0.110 g, 0.120 mmol), tri-t-butylphosphonium tetrafluoroborate (0.139 g, 0.48 mmol), sodium t-butoxide (0.288 g, 3.00 mmol), and anhydrous toluene (60 mL) were successively mixed, and the resultant mixture was refluxed for 11 h under heating.

After cooling the reaction liquid to room temperature, the insolubles were removed by filtration, and the organic solvent was evaporated off under reduced pressure. The obtained residue was purified by silica gel column chromatography to obtain compound M1 (2.44 g, yield: 80%).

Under argon atmosphere, compound M1 (2.44 g, 3.00 mmol), carbazolyl intermediate N1 (1.00 g, 3.00 mmol), tris(dibenzylideneacetone)dipalladium (0.110 g, 0.120 mmol), tri-t-butylphosphonium tetrafluoroborate (0.139 g, 0.48 mmol), sodium t-butoxide (0.288 g, 3.00 mmol), and anhydrous toluene (60 mL) were successively mixed, and the resultant mixture was refluxed for 11 h under heating.

After cooling the reaction liquid to room temperature, the insolubles were removed by filtration, and the organic solvent was evaporated off under reduced pressure. The obtained residue was purified by silica gel column chromatography to obtain compound H-3[V] (3.16 g, yield: 80%).

The results of analysis by HPLC (High Performance Liquid Chromatography) and LC-MS (Liquid Chromatography-Mass Spectrometry) on compound H-3[V] are shown below.

HPLC purity: 99.0%

LC-MS: calcd for $C_{93}H_{57}N_9O$=1315.

found m/z=1315 (M+, 100).

Synthesis Example 4[V](Synthesis of Compound H-4[V])

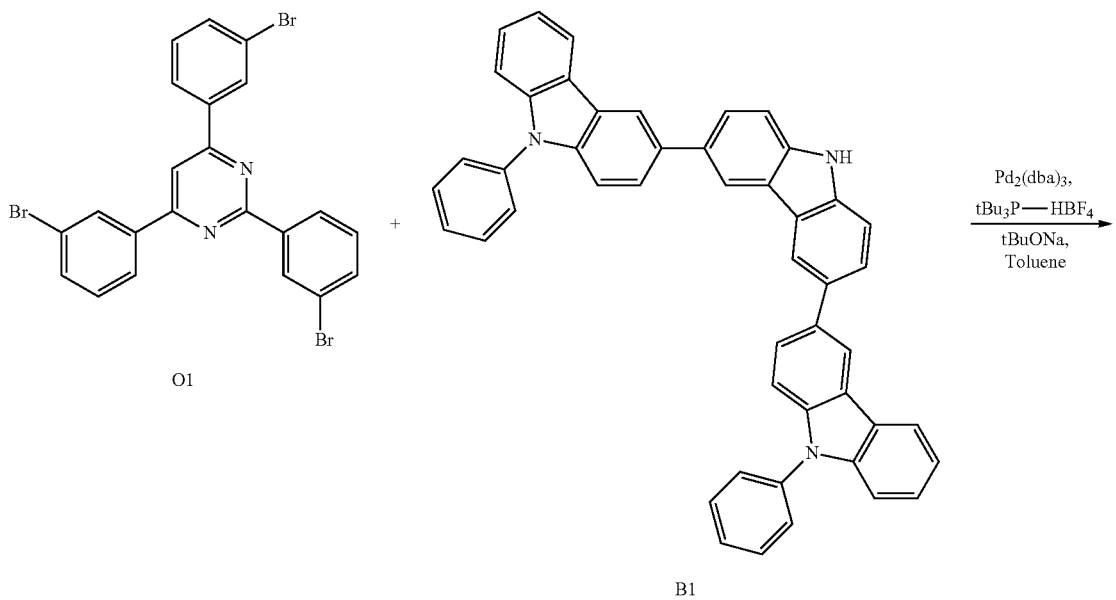

-continued
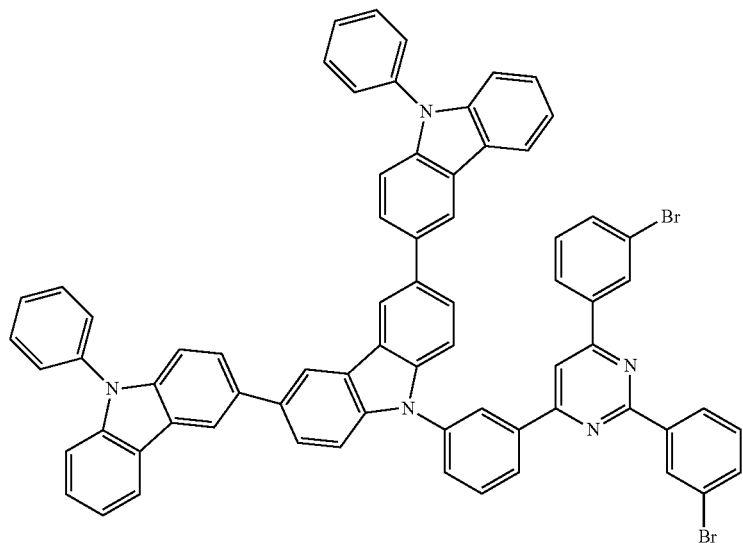
P1
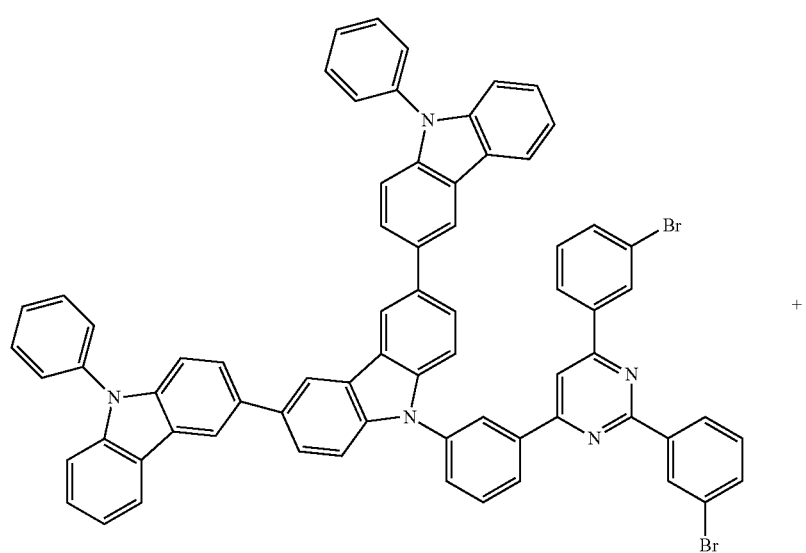
P1    +
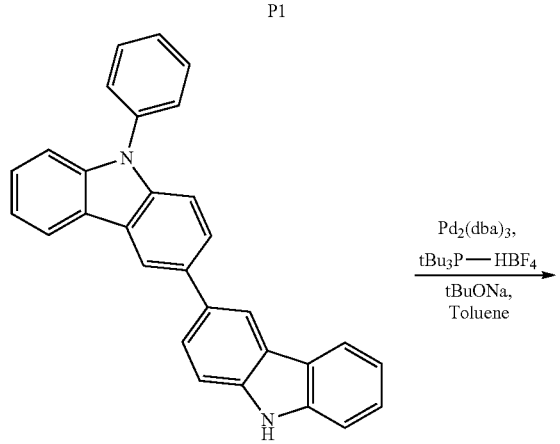
D1

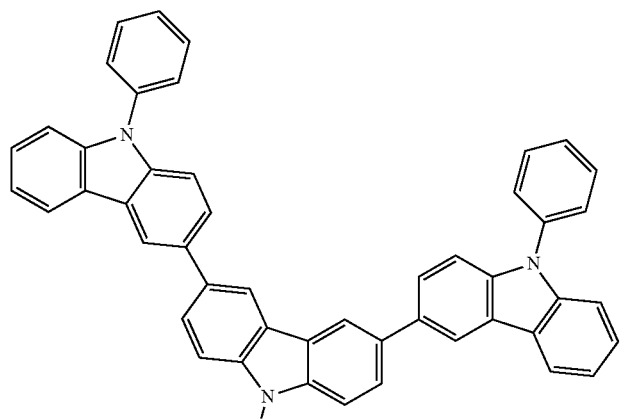
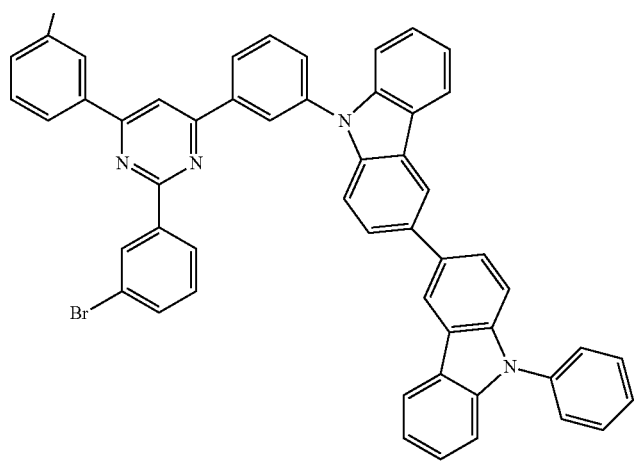
Q1
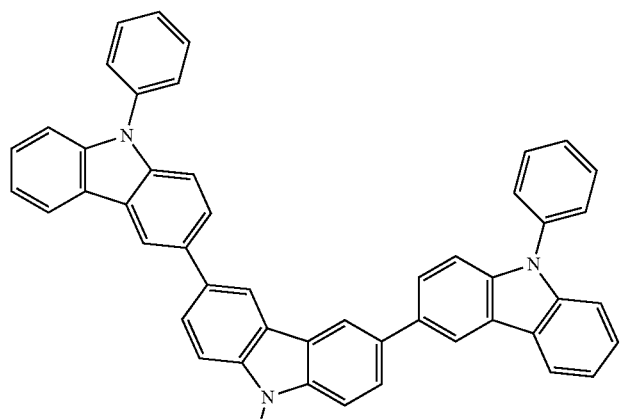

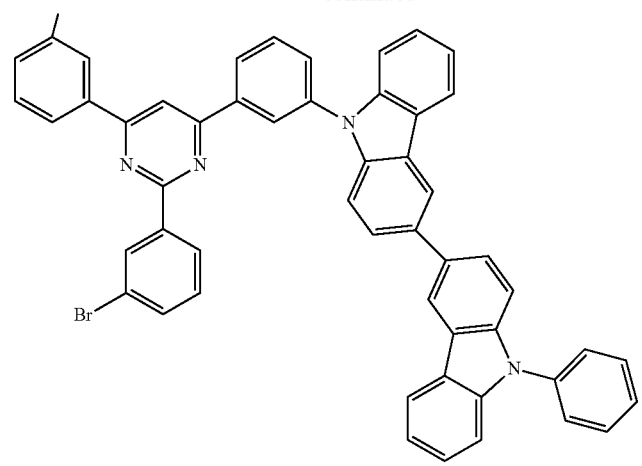
Q1
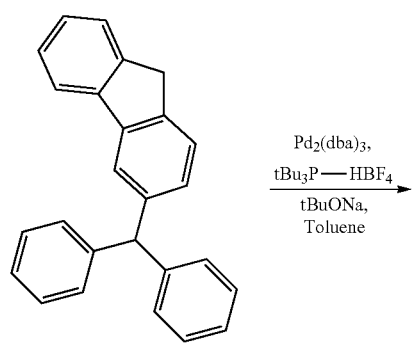
N1
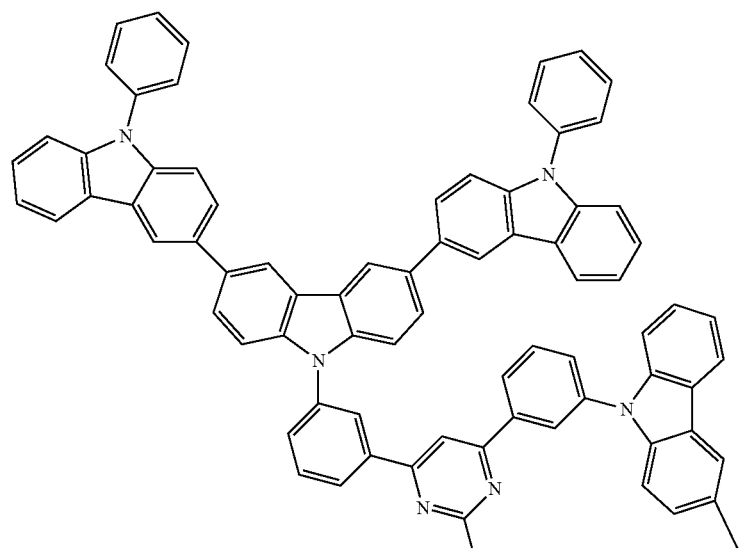

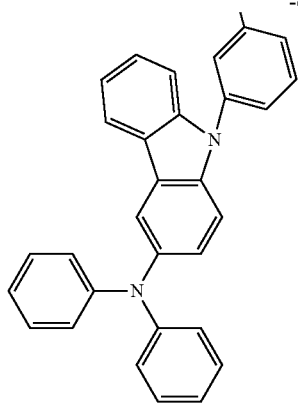

H-4 [V]

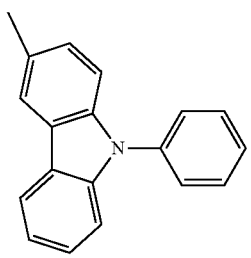

Under argon atmosphere, compound 01 (1.64 g, 3.00 mmol), carbazolyl intermediate B1 (1.95 g, 3.00 mmol), tris(dibenzylideneacetone)dipalladium (0.110 g, 0.120 mmol), tri-t-butylphosphonium tetrafluoroborate (0.139 g, 0.48 mmol), sodium t-butoxide (0.288 g, 3.00 mmol), and anhydrous toluene (60 mL) were successively mixed, and the resultant mixture was refluxed for 11 h under heating.

After cooling the reaction liquid to room temperature, the insolubles were removed by filtration, and the organic solvent was evaporated off under reduced pressure. The obtained residue was purified by silica gel column chromatography to obtain compound P1 (2.67 g, yield: 80%).

Under argon atmosphere, compound P1 (2.67 g, 3.00 mmol), carbazolyl intermediate D1 (1.23 g, 3.00 mmol), tris(dibenzylideneacetone)dipalladium (0.110 g, 0.120 mmol), tri-t-butylphosphonium tetrafluoroborate (0.139 g, 0.48 mmol), sodium t-butoxide (0.288 g, 3.00 mmol), and anhydrous toluene (60 mL) were successively mixed, and the resultant mixture was refluxed for 11 h under heating.

After cooling the reaction liquid to room temperature, the insolubles were removed by filtration, and the organic solvent was evaporated off under reduced pressure. The obtained residue was purified by silica gel column chromatography to obtain compound Q1 (3.46 g, yield: 80%).

Under argon atmosphere, compound Q1 (3.46 g, 3.00 mmol), carbazolyl intermediate N1 (1.00 g, 3.00 mmol), tris(dibenzylideneacetone)dipalladium (0.110 g, 0.120 mmol), tri-t-butylphosphonium tetrafluoroborate (0.139 g, 0.48 mmol), sodium t-butoxide (0.288 g, 3.00 mmol), and anhydrous toluene (60 mL) were successively mixed, and the resultant mixture was refluxed for 11 h under heating.

After cooling the reaction liquid to room temperature, the insolubles were removed by filtration, and the organic solvent was evaporated off under reduced pressure. The obtained residue was purified by silica gel column chromatography to obtain compound H-4[V] (4.07 g, yield: 80%).

The results of analysis by HPLC (High Performance Liquid Chromatography) and LC-MS (Liquid Chromatography-Mass Spectrometry) on compound H-4[V] are shown below.

HPLC purity: 99.0%
LC-MS: calcd for $CH_{124}H_{79}N_9$=1693.
found m/z=1693 (M+, 100).

The compounds within the scope of the claims of this application can be synthesized by referring to the above synthetic reactions while using a known synthetic reaction and a starting material in accordance with the target compound.

Example 1[V]

Cleaning of Substrate

A glass substrate of 25 mm×25 mm×1.1 mm thickness having an ITO transparent electrode (product of Geomatec Company) was cleaned by ultrasonic cleaning in isopropyl alcohol for 5 min and then UV ozone cleaning for 5 min.

Formation of Underlayers

Clevious AI4083 (tradename) manufactured by Heraeus as a hole transporting material was spin-coated on the ITO substrate to form a hole transporting layer with a thickness of 30 nm. Thereafter, unnecessary portion was removed by acetone and then a base substrate was produced by baking in air for 10 min on a hot plate at 200° C.

Formation of Light Emitting Layer

A 1.6% by mass toluene solution containing the compound H-1[V] obtained in Synthesis Example 1[V] as a host material and the following compound D-ii as a dopant material was prepared in a mixing ratio of compound H-1[V]:compound D-ii=90:10 by mass. The toluene solution was spin-coated on the base substrate into a thickness of 50 nm. Thereafter, unnecessary portion was removed by toluene and then the coated film was dried under heating at 150° C. on a hot plate to obtain a coat-laminated substrate having a light emitting layer. The film-forming operations for forming the light emitting layer were all conducted in a glove box under a nitrogen atmosphere.

Vapor Deposition and Sealing

The coat-laminated substrate was conveyed into a vapor deposition chamber and the following compound ET-1 as an electron transporting material was vapor-deposited into a thickness of 50 nm to form an electron transporting layer. Then, lithium fluoride was vapor-deposited into a thickness of 1 nm and aluminum was vapor-deposited into a thickness of 80 nm. After completing all the vapor deposition processes, the substrate with laminated films was sealed with a bored glass in a glove box under a nitrogen atmosphere to produce an organic EL device.

Evaluation of Device

By driving at a direct current, the obtained organic EL device was allowed to emit light to measure the external quantum efficiency (EQE) at a current density of 10 mA/cm². The result is shown in Table 5.

Example 2[V]

An organic EL device was produced in the same manner as in Example 1[V] except for using compound H-2[V] obtained in Synthesis Example 2[V] as a host material. The obtained organic EL device was allowed to emit light by driving at a direct current to measure the external quantum efficiency (EQE) at a current density of 10 mA/cm². The result is shown in Table 5.

Example 3[V]

An organic EL device was produced in the same manner as in Example 1[V] except for using compound H-3[V] obtained in Synthesis Example 3[V] as a host material. The obtained organic EL device was allowed to emit light by driving at a direct current to measure the external quantum efficiency (EQE) at a current density of 10 mA/cm². The result is shown in Table 5.

Example 4[V]

An organic EL device was produced in the same manner as in Example 1[V] except for using compound H-4[V] obtained in Synthesis Example 4[V] as a host material. The obtained organic EL device was allowed to emit light by driving at a direct current to measure the external quantum efficiency (EQE) at a current density of 10 mA/cm². The result is shown in Table 5.

Example 5[V]

An organic EL device was produced in the same manner as in Example 1[V] except for using compound D-i as a dopant material in a host material to dopant material ratio of 90:10 by mass. The obtained organic EL device was allowed to emit light by driving at a direct current to measure the external quantum efficiency (EQE) at a current density of 10 mA/cm². The result is shown in Table 5.

Example 6[V]

An organic EL device was produced in the same manner as in Example 2[V] except for using compound D-i as a dopant material in a host material to dopant material ratio of 90:10 by mass. The obtained organic EL device was allowed to emit light by driving at a direct current to measure the external quantum efficiency (EQE) at a current density of 10 mA/cm². The result is shown in Table 5.

Example 7[V]

An organic EL device was produced in the same manner as in Example 3[V] except for using compound D-i as a dopant material in a host material to dopant material ratio of 90:10 by mass. The obtained organic EL device was allowed to emit light by driving at a direct current to measure the external quantum efficiency (EQE) at a current density of 10 mA/cm². The result is shown in Table 5.

Example 8[V]

An organic EL device was produced in the same manner as in Example 4[V] except for using compound D-i as a dopant material in a host material to dopant material ratio of 90:10 by mass. The obtained organic EL device was allowed to emit light by driving at a direct current to measure the external quantum efficiency (EQE) at a current density of 10 mA/cm². The result is shown in Table 5.

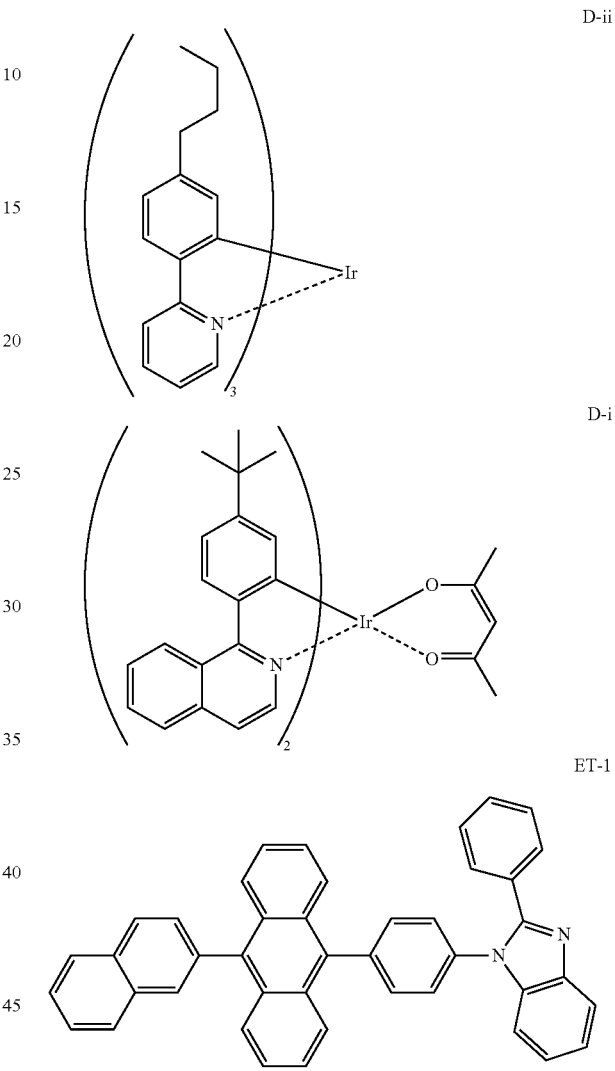

TABLE 5

| | Host material | Dopant material | EQE (%) |
|---|---|---|---|
| Example 1[V] | H-1[V] | D-ii | 9.2 |
| Example 2[V] | H-2[V] | D-ii | 8.7 |
| Example 3[V] | H-3[V] | D-ii | 10.1 |
| Example 4[V] | H-4[V] | D-ii | 9.8 |
| Example 5[V] | H-1[V] | D-i | 5.9 |
| Example 6[V] | H-2[V] | D-i | 6.2 |
| Example 7[V] | H-3[V] | D-i | 7.1 |
| Example 8[V] | H-4[V] | D-i | 6.7 |

Examples 1 to 66

Cleaning of Substrate

A glass substrate of 25 mm×25 mm×1.1 mm thickness having an ITO transparent electrode (product of Geomatec Company) was cleaned by ultrasonic cleaning in isopropyl alcohol for 5 min and then UV ozone cleaning for 5 min.

Formation of Underlayers

Clevious AI4083 (tradename) manufactured by Heraeus as a hole transporting material was spin-coated on the ITO substrate to form a hole transporting layer with a thickness of 30 nm. Thereafter, unnecessary portion was removed by acetone and then a base substrate was produced by baking in air for 10 min on a hot plate at 200° C.

Formation of Light Emitting Layer

A 1.6% by mass toluene solution containing two host materials (1:1 by mass) and the following compound D-ii as a dopant material was prepared in a mixing ratio of host materials:compound D-ii=90:10 by mass. The toluene solution was spin-coated on the base substrate into a thickness of 50 nm. Thereafter, unnecessary portion was removed by toluene and then the coated film was dried under heating at 150° C. on a hot plate to obtain a coat-laminated substrate having a light emitting layer. The film-forming operations for forming the light emitting layer were all conducted in a glove box under a nitrogen atmosphere.

Vapor Deposition and Sealing

The coat-laminated substrate was conveyed into a vapor deposition chamber and the following compound ET-1 as an electron transporting material was vapor-deposited into a thickness of 50 nm to form an electron transporting layer. Then, lithium fluoride was vapor-deposited into a thickness of 1 nm and aluminum was vapor-deposited into a thickness of 80 nm. After completing all the vapor deposition processes, the substrate with laminated films was sealed with a bored glass in a glove box under a nitrogen atmosphere to produce an organic EL device.

Evaluation of Device

By driving at a direct current, the obtained organic EL device was allowed to emit light to measure the external quantum efficiency (EQE) at a current density of 10 mA/cm$^2$. The results are shown in Tables 6 and 7.

TABLE 6

| | Host material | Dopant material | EQE (%) |
|---|---|---|---|
| Example 1 | H-1[I] | A-2 | D-ii | 7.6 |
| Example 2 | H-1[I] | B-1 | D-ii | 6.8 |
| Example 3 | H-1[I] | B-4 | D-ii | 7.2 |
| Example 4 | H-1[I] | B-10 | D-ii | 7.3 |
| Example 5 | H-1[I] | B-13 | D-ii | 7.4 |
| Example 6 | H-1[I] | B-32 | D-ii | 6.5 |
| Example 7 | H-1[I] | C-219 | D-ii | 5.8 |
| Example 8 | H-1[I] | C-222 | D-ii | 5.7 |
| Example 9 | H-1[I] | C-225 | D-ii | 6.7 |
| Example 10 | H-1[I] | D-2 | D-ii | 6.0 |
| Example 11 | H-1[I] | D-3 | D-ii | 6.1 |
| Example 12 | H-2[I] | A-2 | D-ii | 7.3 |
| Example 13 | H-2[I] | B-1 | D-ii | 6.5 |
| Example 14 | H-2[I] | B-4 | D-ii | 7.1 |
| Example 15 | H-2[I] | B-10 | D-ii | 7.2 |
| Example 16 | H-2[I] | B-13 | D-ii | 7.1 |
| Example 17 | H-2[I] | B-32 | D-ii | 6.4 |
| Example 18 | H-2[I] | C-219 | D-ii | 5.4 |
| Example 19 | H-2[I] | C-222 | D-ii | 5.7 |
| Example 20 | H-2[I] | C-225 | D-ii | 6.6 |
| Example 21 | H-2[I] | D-2 | D-ii | 5.9 |
| Example 22 | H-2[I] | D-3 | D-ii | 6.0 |
| Example 23 | H-5[II] | A-2 | D-ii | 8.0 |
| Example 24 | H-5[II] | B-1 | D-ii | 7.9 |
| Example 25 | H-5[II] | B-4 | D-ii | 7.8 |
| Example 26 | H-5[II] | B-10 | D-ii | 7.9 |
| Example 27 | H-5[II] | B-13 | D-ii | 7.7 |
| Example 28 | H-5[II] | B-32 | D-ii | 7.7 |
| Example 29 | H-5[II] | C-219 | D-ii | 6.5 |
| Example 30 | H-5[II] | C-222 | D-ii | 6.5 |
| Example 31 | H-5[II] | C-225 | D-ii | 6.7 |
| Example 32 | H-5[II] | D-2 | D-ii | 5.8 |
| Example 33 | H-5[II] | D-3 | D-ii | 5.8 |

TABLE 7

| | Host material | Dopant material | EQE (%) |
|---|---|---|---|
| Example 34 | H-4[III] | A-2 | D-ii | 6.7 |
| Example 35 | H-4[III] | B-1 | D-ii | 6.3 |
| Example 36 | H-4[III] | B-4 | D-ii | 6.6 |
| Example 37 | H-4[III] | B-10 | D-ii | 6.6 |
| Example 38 | H-4[III] | B-13 | D-ii | 6.3 |
| Example 39 | H-4[III] | B-32 | D-ii | 6.2 |
| Example 40 | H-4[III] | C-219 | D-ii | 5.3 |
| Example 41 | H-4[III] | C-222 | D-ii | 5.2 |
| Example 42 | H-4[III] | C-225 | D-ii | 5.8 |
| Example 43 | H-4[III] | D-2 | D-ii | 5.2 |
| Example 44 | H-4[III] | D-3 | D-ii | 5.3 |
| Example 45 | H-1[IV] | A-2 | D-ii | 6.7 |
| Example 46 | H-1[IV] | B-1 | D-ii | 6.8 |
| Example 47 | H-1[IV] | B-4 | D-ii | 6.3 |
| Example 48 | H-1[IV] | B-10 | D-ii | 6.2 |
| Example 49 | H-1[IV] | B-13 | D-ii | 6.2 |
| Example 50 | H-1[IV] | B-32 | D-ii | 6.1 |
| Example 51 | H-1[IV] | C-219 | D-ii | 6.0 |
| Example 52 | H-1[IV] | C-222 | D-ii | 5.9 |
| Example 53 | H-1[IV] | C-225 | D-ii | 5.4 |
| Example 54 | H-1[IV] | D-2 | D-ii | 4.8 |
| Example 55 | H-1[IV] | D-3 | D-ii | 5.0 |
| Example 56 | H-1[V] | A-2 | D-ii | 7.4 |
| Example 57 | H-1[V] | B-1 | D-ii | 7.4 |
| Example 58 | H-1[V] | B-4 | D-ii | 7.1 |
| Example 59 | H-1[V] | B-10 | D-ii | 7.0 |
| Example 60 | H-1[V] | B-13 | D-ii | 7.1 |
| Example 61 | H-1[V] | B-32 | D-ii | 7.2 |
| Example 62 | H-1[V] | C-219 | D-ii | 6.1 |
| Example 63 | H-1[V] | C-222 | D-ii | 6.0 |
| Example 64 | H-1[V] | C-225 | D-ii | 6.3 |
| Example 65 | H-1[V] | D-2 | D-ii | 5.9 |
| Example 66 | H-1[V] | D-3 | D-ii | 5.8 |

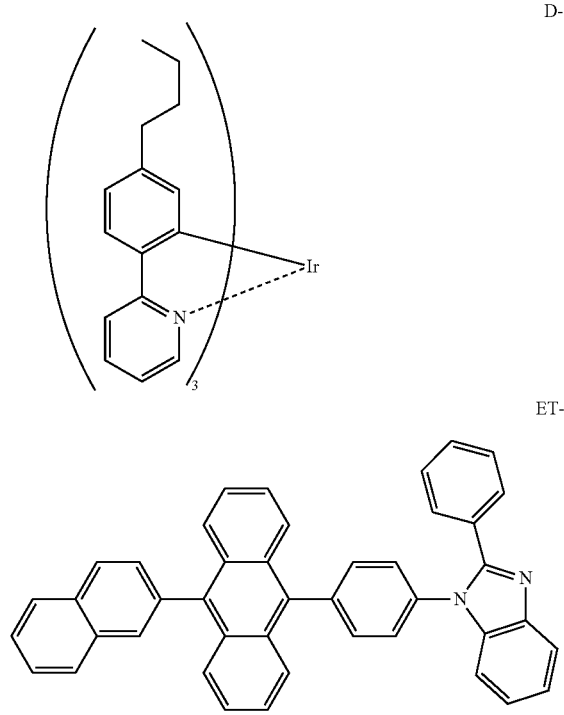

D-ii

ET-1

REFERENCE SIGNS LIST

1. Organic EL device
2. Substrate
3. Anode
4. Cathode
5. Light emitting layer
6. Anode-side organic thin film layer
7. Cathode-side organic thin film layer
10. Emission unit

What is claimed is:
1. A compound represented by formula 1[I]:

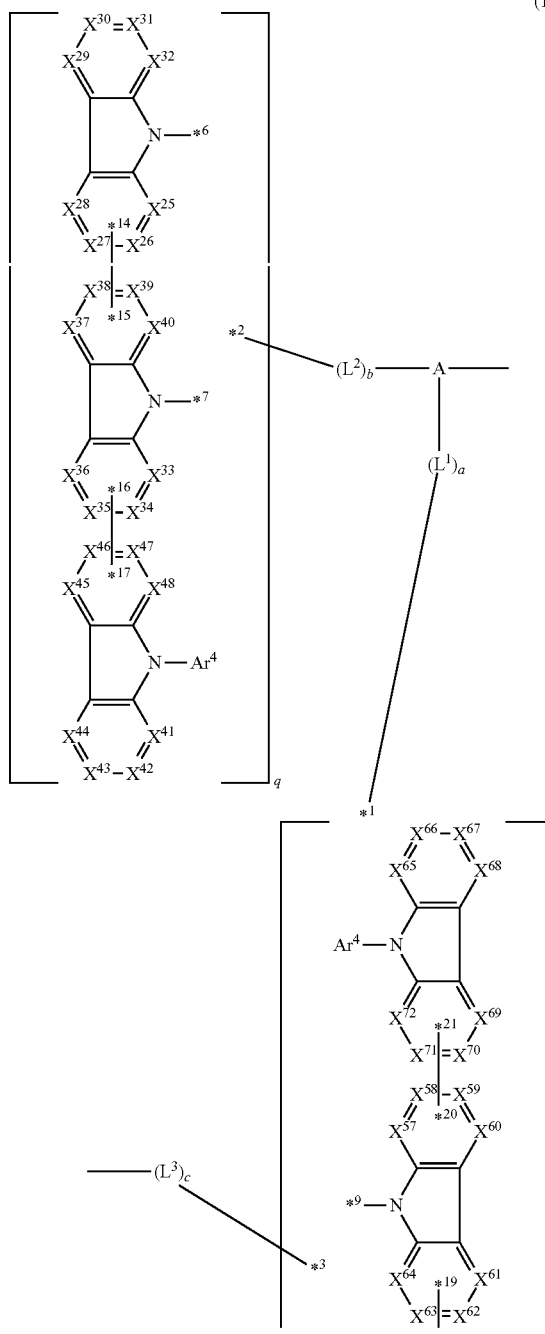

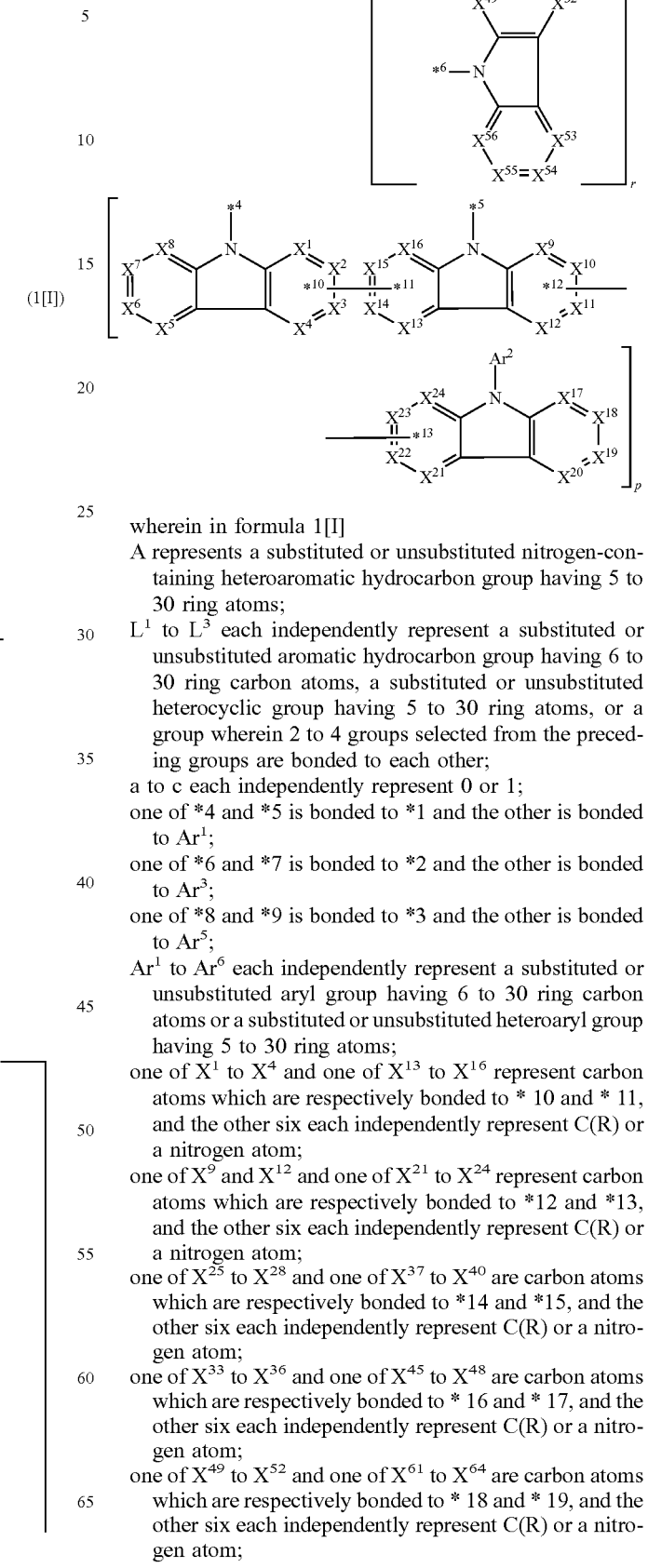

wherein in formula 1[I]

A represents a substituted or unsubstituted nitrogen-containing heteroaromatic hydrocarbon group having 5 to 30 ring atoms;

$L^1$ to $L^3$ each independently represent a substituted or unsubstituted aromatic hydrocarbon group having 6 to 30 ring carbon atoms, a substituted or unsubstituted heterocyclic group having 5 to 30 ring atoms, or a group wherein 2 to 4 groups selected from the preceding groups are bonded to each other;

a to c each independently represent 0 or 1;

one of *4 and *5 is bonded to *1 and the other is bonded to $Ar^1$;

one of *6 and *7 is bonded to *2 and the other is bonded to $Ar^3$;

one of *8 and *9 is bonded to *3 and the other is bonded to $Ar^5$;

$Ar^1$ to $Ar^6$ each independently represent a substituted or unsubstituted aryl group having 6 to 30 ring carbon atoms or a substituted or unsubstituted heteroaryl group having 5 to 30 ring atoms;

one of $X^1$ to $X^4$ and one of $X^{13}$ to $X^{16}$ represent carbon atoms which are respectively bonded to *10 and *11, and the other six each independently represent C(R) or a nitrogen atom;

one of $X^9$ and $X^{12}$ and one of $X^{21}$ to $X^{24}$ represent carbon atoms which are respectively bonded to *12 and *13, and the other six each independently represent C(R) or a nitrogen atom;

one of $X^{25}$ to $X^{28}$ and one of $X^{37}$ to $X^{40}$ are carbon atoms which are respectively bonded to *14 and *15, and the other six each independently represent C(R) or a nitrogen atom;

one of $X^{33}$ to $X^{36}$ and one of $X^{45}$ to $X^{48}$ are carbon atoms which are respectively bonded to *16 and *17, and the other six each independently represent C(R) or a nitrogen atom;

one of $X^{49}$ to $X^{52}$ and one of $X^{61}$ to $X^{64}$ are carbon atoms which are respectively bonded to *18 and *19, and the other six each independently represent C(R) or a nitrogen atom;

one of $X^{57}$ to $X^{60}$ and one of $X^{69}$ to $X^{72}$ are carbon atoms which are respectively bonded to *20 and *21, and the other six each independently represent C(R) or a nitrogen atom;

$X^5$ to $X^8$, $X^{17}$ to $X^{20}$, $X^{29}$ to $X^{32}$, $X^{41}$ to $X^{44}$, $X^{53}$ to $X^{56}$, and $X^{65}$ to $X^{68}$ each independently represent C(R) or a nitrogen atom;

R represents a hydrogen atom or a substituent, two or more groups R may be the same or different, and two selected from groups R may be bonded to each other to form a ring; and p to r each independently represent an integer of 0 to 3, p+q+r=3, and when p, q or r is 2 or 3, 2 or 3 groups in each [ ] may be the same or different, respectively.

2. A composition comprising the compound of claim 1 and at least one selected from the group of compounds represented by formulae (CH1), (CH3), (CH4), (CH5), (CH6), and (CH14);

wherein (CH1) is:

(CH1)

wherein A represents a substituted or unsubstituted aromatic heterocyclic group; $L^1$ represents a single bond, a substituted or unsubstituted aromatic hydrocarbon group, or a substituted or unsubstituted aromatic heterocyclic group; B represents a residue of a structure represented by formula (CH2); m represents an integer of 2 or more; two or more groups $L^1$ may be the same or different; and two or more groups B may be the same or different;

wherein (CH2) is:

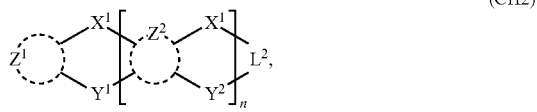

(CH2)

wherein one of $X^1$ and $Y^1$ represents a single bond, —$CR_2$—, —NR—, —O—, —S—, or —$SiR_2$— and the other represents —NR—, —O—, —S— or —$SiR_2$—; one of $X^2$ and $Y^2$ represents a single bond, —$CR_2$—, —NR—, —O—, —S—, or —$SiR_2$— and the other represents —NR—, —O—, —S—, or —$SiR_2$—; R represents a hydrogen atom, a substituted or unsubstituted alkyl group, a substituted or unsubstituted cycloalkyl group, a substituted or unsubstituted aromatic hydrocarbon group, or a substituted or unsubstituted aromatic heterocyclic group; $Z^1$ and $Z^2$ each independently represent a substituted or unsubstituted aliphatic hydrocarbon group, a substituted or unsubstituted aliphatic heterocyclic group, a substituted or unsubstituted aromatic hydrocarbon group, or a substituted or unsubstituted aromatic heterocyclic group; $L^2$ represents a linking group; n represents an integer of 0 to 5, and when n is two or more, two or more groups $Z^2$ may be the same or different two or more groups $X^2$ may be the same or different, and two or more groups $Y^2$ may be the same or different;

wherein (CH3) is:

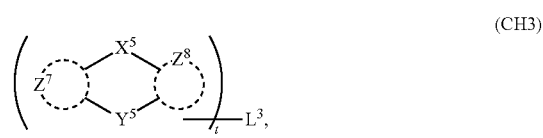

(CH3)

wherein X5 and Y5 each represent a single bond, —$CR_2$—, —NR—, —O—, —S—, or —$SiR_2$—, and $X^5$ and $Y^5$ cannot all be single bonds; R is as defined above; $Z^7$ and $Z^8$ are as defined above with respect to $Z^1$ and $Z^2$, provided that each of $Z^7$ and $Z^8$ cannot be an aliphatic hydrocarbon ring group having 3 or more fused rings, an aliphatic heterocyclic group having 3 or more fused rings, an aromatic hydrocarbon ring group having 3 or more fused rings, or a aromatic heterocyclic group having 3 or more fused rings; t represents an integer of 1 or more; $L^3$ represents a single bond, a substituted or unsubstituted aromatic hydrocarbon group, a substituted or unsubstituted aromatic heterocyclic group, or a combination thereof, provided that when t is 1, $L^3$ is not a single bond;

wherein (CH4) is:

(CH4)

wherein $A^1$ to $A^3$ each represent a substituted or unsubstituted aromatic hydrocarbon group or a substituted or unsubstituted aromatic heterocyclic group;

wherein (CH5) is:

(CH5)

wherein $L^4$ represents a substituted or unsubstituted divalent group wherein 1 to 4 aromatic hydrocarbon rings are bonded to each other or included or a substituted or unsubstituted divalent group wherein 1 to 4 aromatic heterocyclic rings are bonded to each other; $A^4$ to $A^6$ each represent a substituted or unsubstituted aromatic hydrocarbon group or a substituted or unsubstituted aromatic heterocyclic group; and $A^4$ and $A^5$ may be bonded to each other to form a ring structure;

wherein (CH6) is:

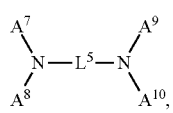

(CH6)

wherein $L^5$ represents a substituted or unsubstituted divalent group wherein 1 to 6 aromatic hydrocarbon rings are bonded to each other or included or a substituted or unsubstituted divalent group wherein 1 to 6 aromatic heterocyclic rings are bonded to each other; $A^7$ to $A^{10}$ each represent a substituted or unsubstituted group wherein 1 to 10 aromatic hydrocarbon rings are bonded to each other or a substituted or unsubstituted group wherein 1 to 10 aromatic heterocyclic rings are bonded to each other;

wherein (CH14) is:

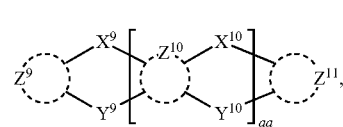

(CH14)

wherein $X^9$, $X^{10}$, $Y^9$, and $Y^{10}$ each represent a single bond, —$CR_2$—, —NR—, —O—, —S—, —PR—, or —$SiR_2$—, and cannot all be single bonds; R is as defined above with respect to R of $X^1$, $X^2$, $Y^1$, and $Y^2$ in formula (CH2); $Z^9$, $Z^{10}$, and $Z^{11}$ are as defined above with respect to $Z^1$ and $Z^2$ of formula (CH2); and aa is an integer of 1 to 5, and when aa is an integer of 2 or more, two or more groups $Z^{10}$ may be the same or different, two or more groups $X^{10}$ may be the same or different, and two or more groups $Y^{10}$ may be the same or different.

3. The compound according to claim 1, wherein the compound is represented by formula 1a[I]:

(1a[I])

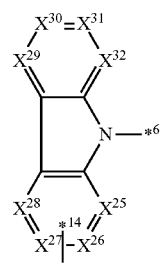

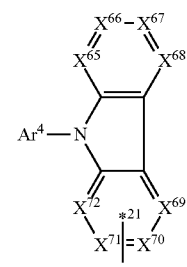

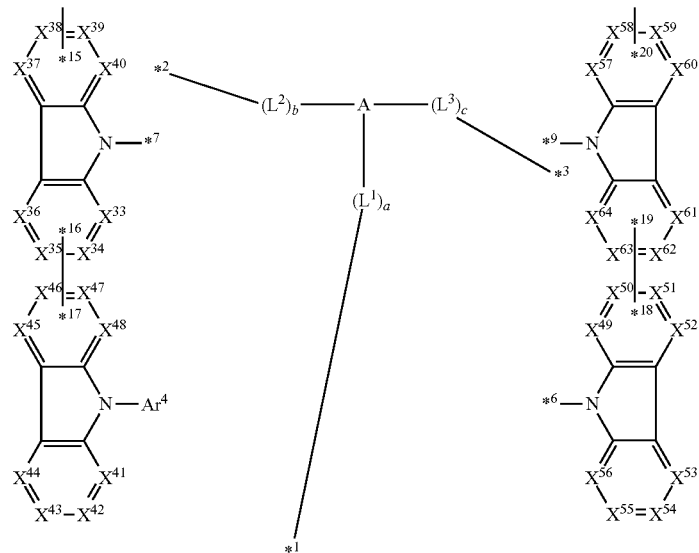

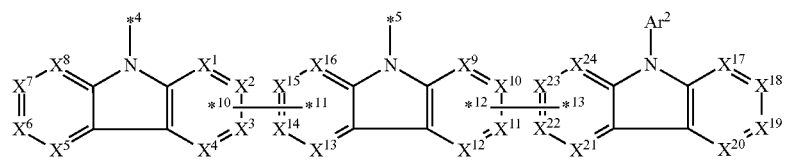

in formula 1a[I], A, $L^1$ to $L^3$, a to c, $X^1$ to $X^{72}$, *1 to *21, $Ar^2$, $Ar^4$, and $Ar^6$ are as defined in claim 1.

4. The compound according to claim 3, wherein the compound is represented by formula 1a-i[I]:

14-*15 is a bond between carbon atoms from which one of $R^{25}$ to $R^{28}$ and one of $R^{37}$ to $R^{40}$ are removed;

16-*17 is a bond between carbon atoms from which one of $R^{33}$ to $R^{36}$ and one of $R^{45}$ to $R^{48}$ are removed;

(1a-i[I])

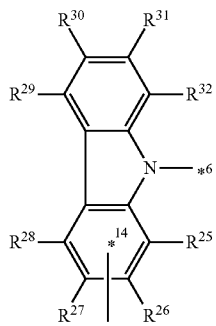
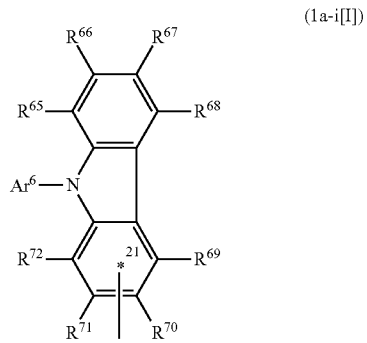
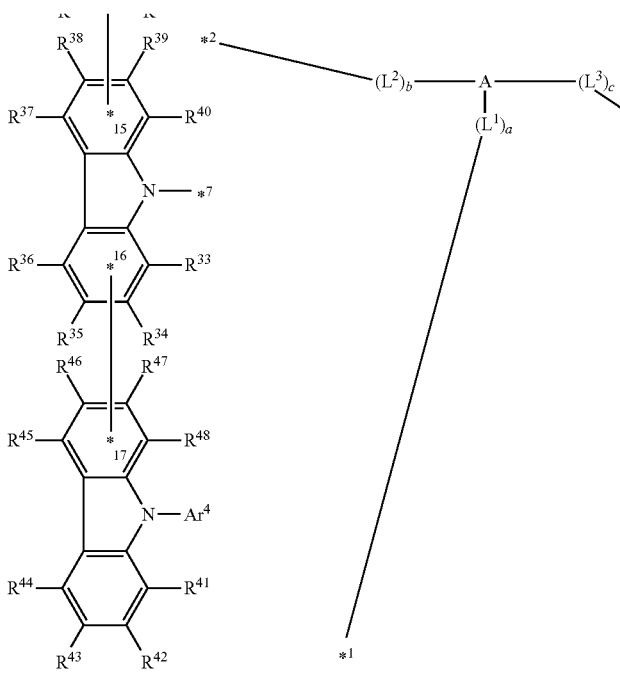
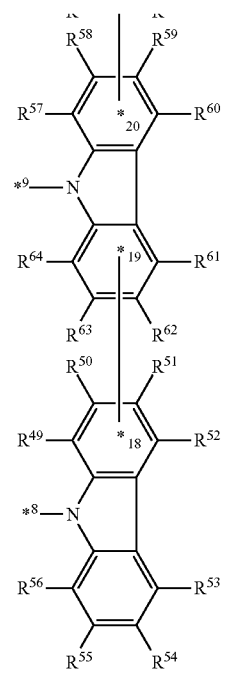
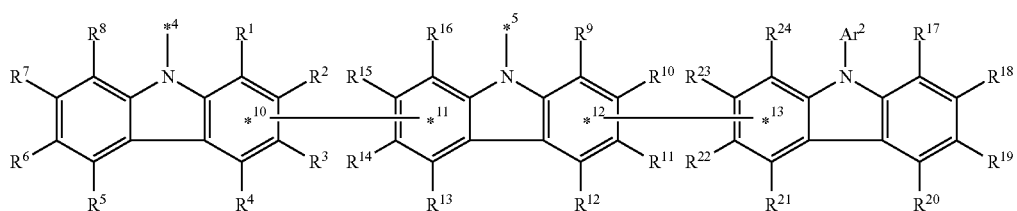

wherein in formula 1a-i[I],

10-*11 is a bond between carbon atoms from which one of $R^1$ to $R^4$ and one of $R^{13}$ to $R^{16}$ are removed;

12-*13 is a bond between carbon atoms from which one of $R^9$ to $R^{12}$ and one of $R^{21}$ to $R^{24}$ are removed;

18-*19 is a bond between carbon atoms from which one of $R^{49}$ to $R^{52}$ and one of $R^{61}$ to $R^{64}$ are removed; and 20-*21 is a bond between carbon atoms from which one of $R^{57}$ to $R^{60}$ and one of $R^{69}$ to $R^{72}$ are removed.

5. The compound according to claim 4, wherein the compound is represented by formula 1a-ii[I]:
(1a-ii[I])
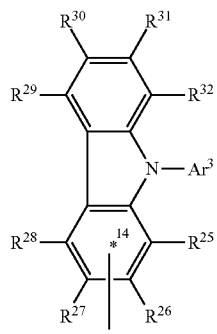
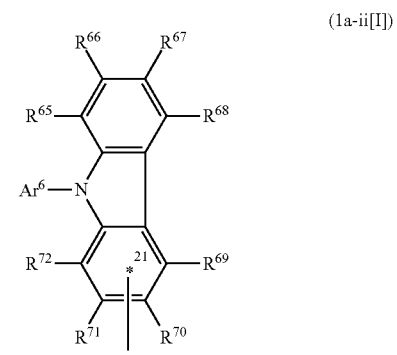
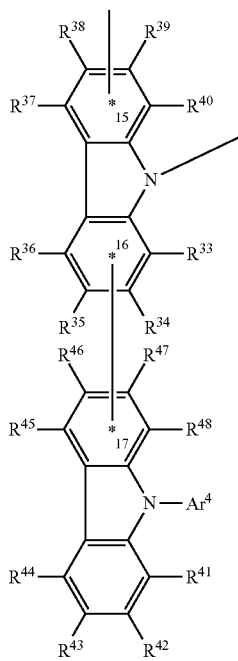
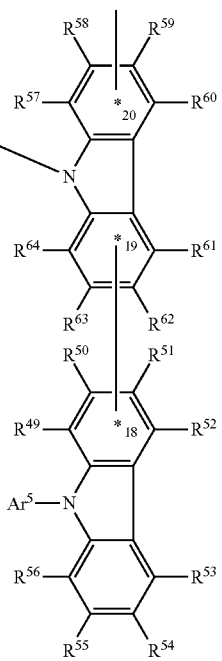
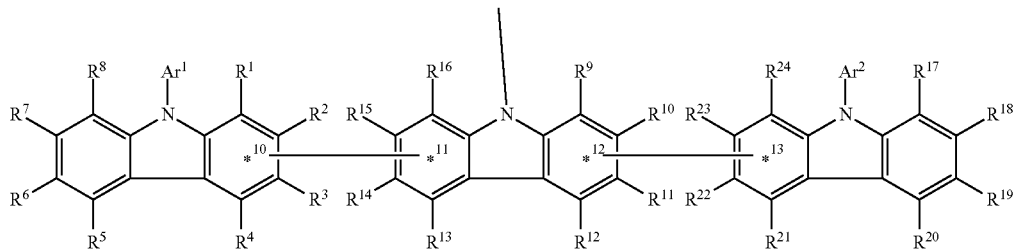
6. The compound according to claim 5, wherein the compound is represented by any of formulae 1a-ii-1[I] to 1a-ii-6[I]:

(1a-ii-1 [I])
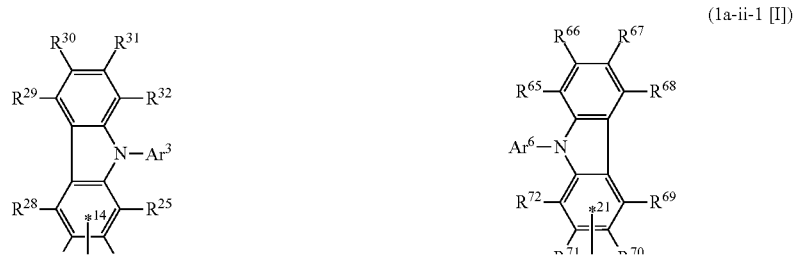
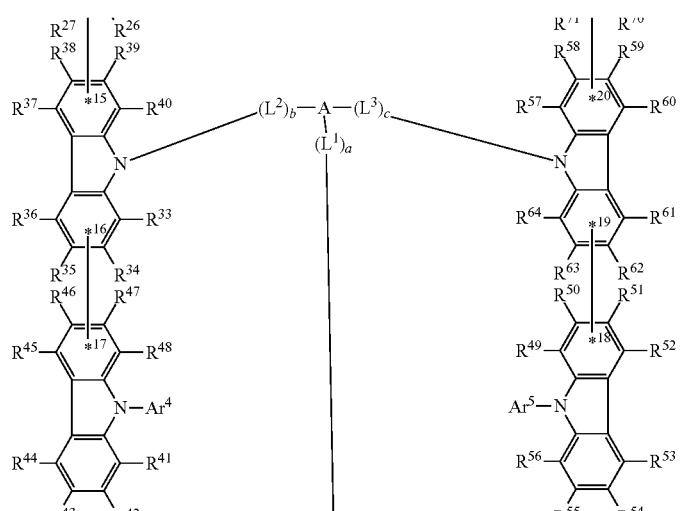
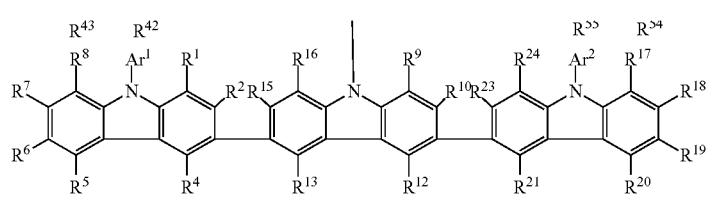

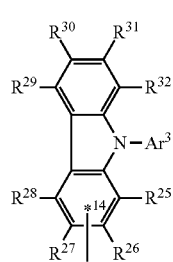
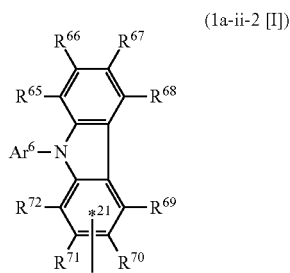
(1a-ii-2 [I])
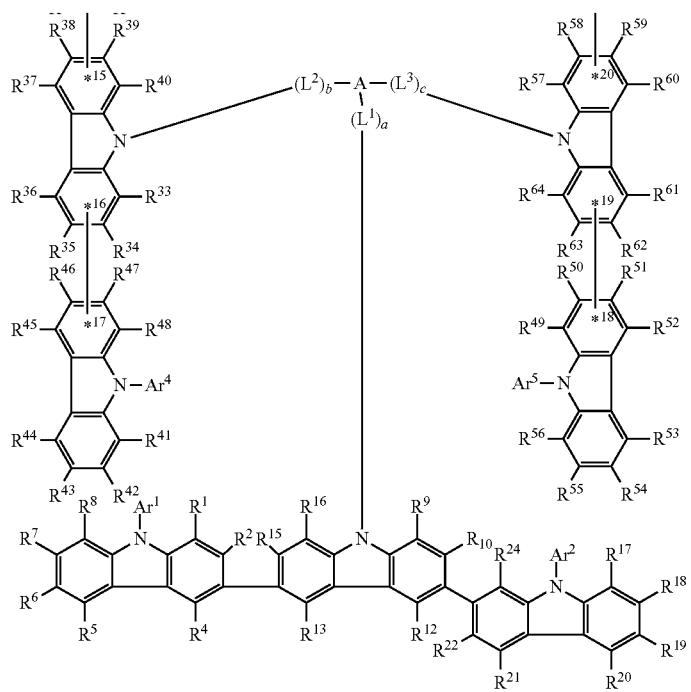

(1a-ii-3 [I])
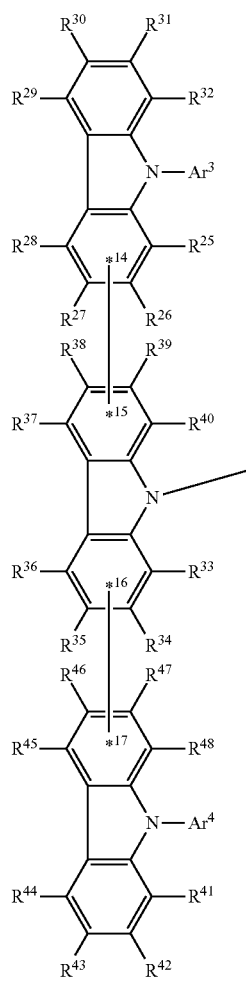
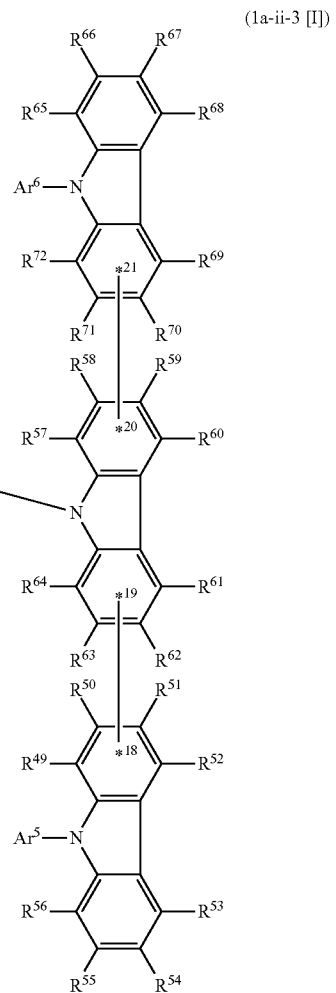
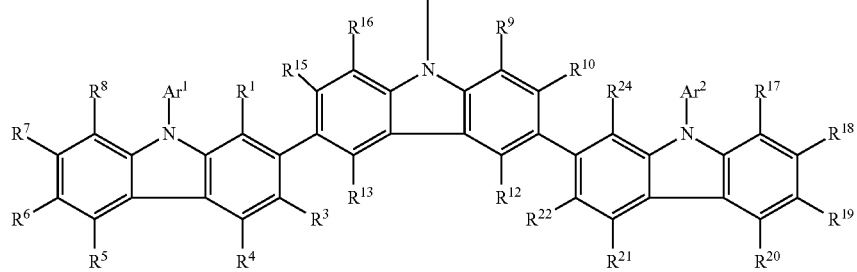
(1a-ii-4 [I])
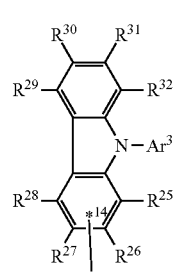
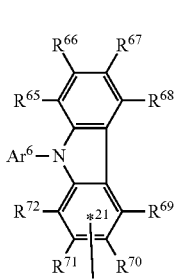

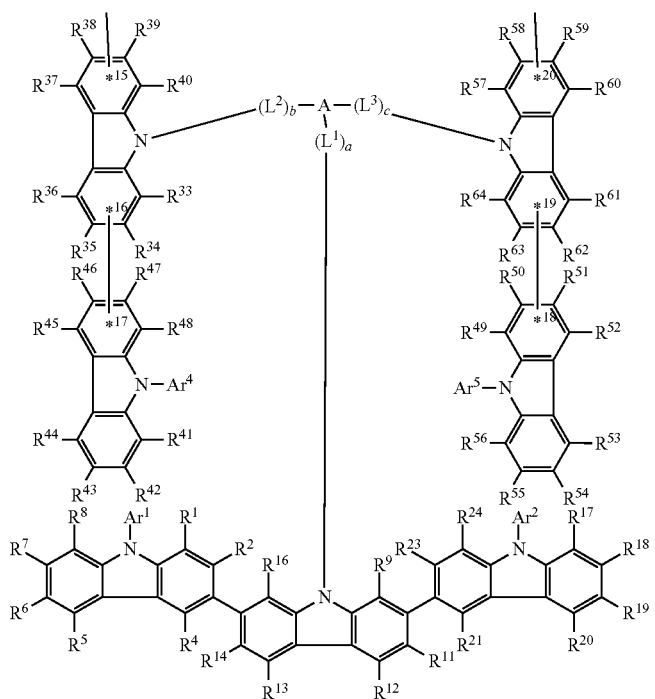
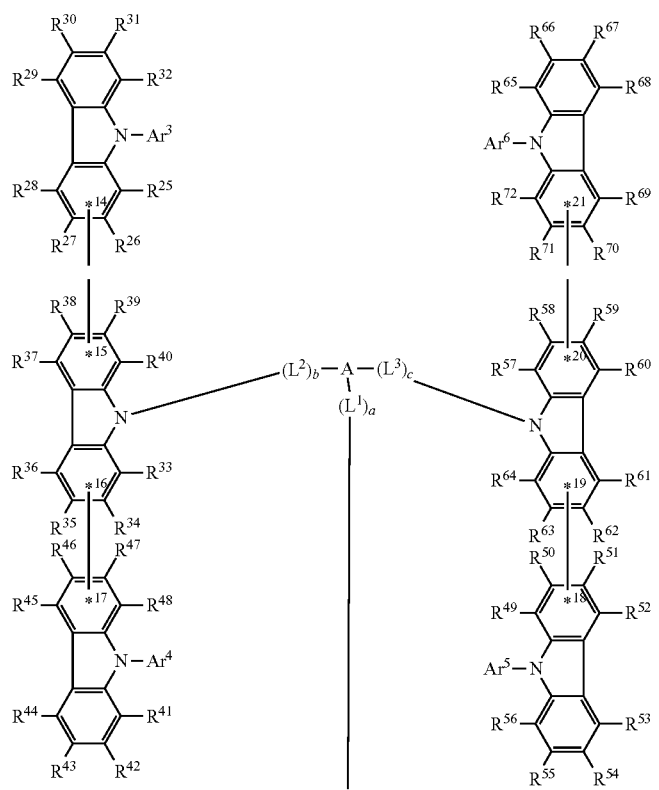
(1a-ii-5 [I])

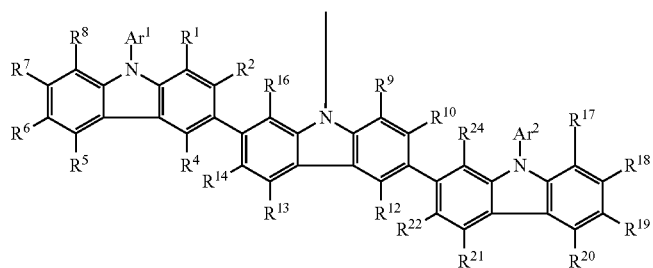
(1a-ii-6 [I])
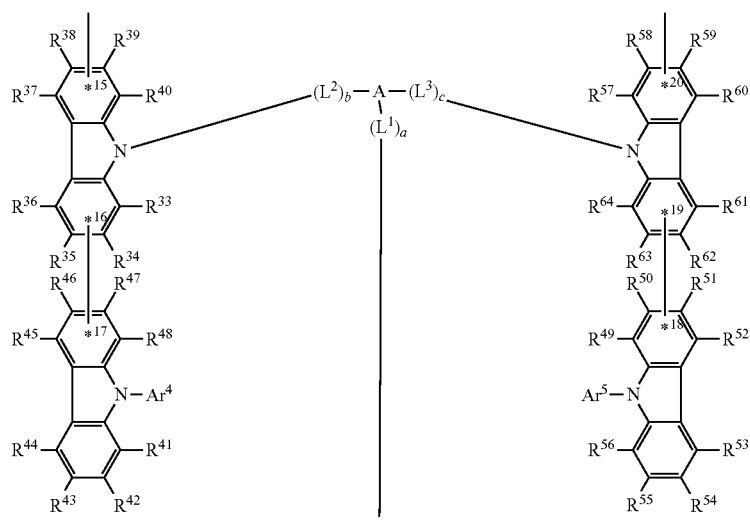
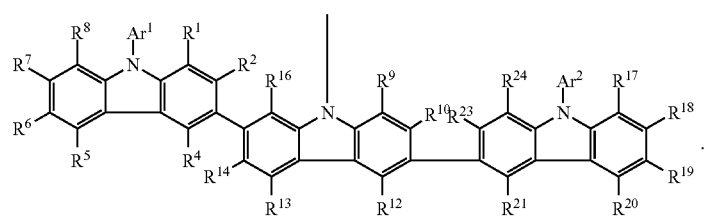
7. The compound according to claim 4, wherein the compound is represented by formula 1a-iii[I]:

2325　　　　　　　　　　　　　　　　2326
(1a-ii[I]i)
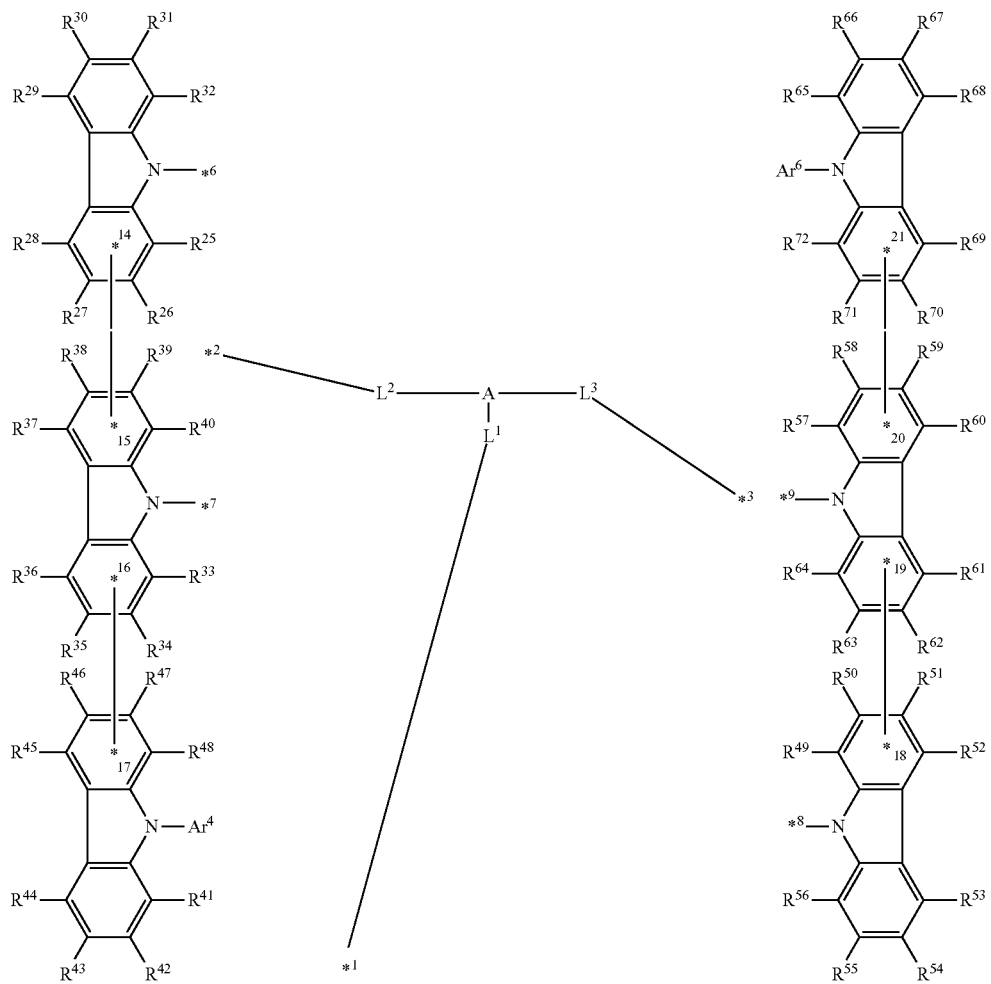
8. The compound according to claim 4, wherein the compound is represented by formula 1a-iv[I]:
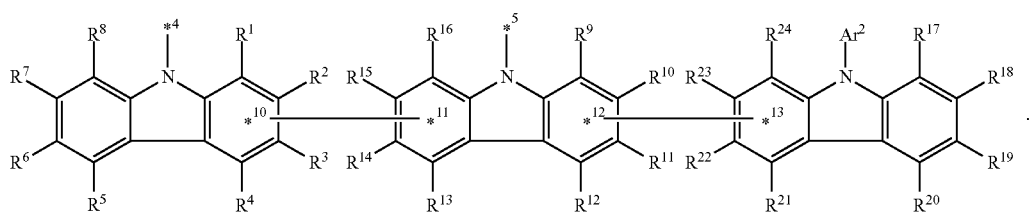

2327
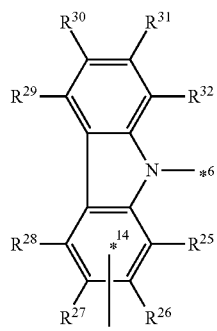
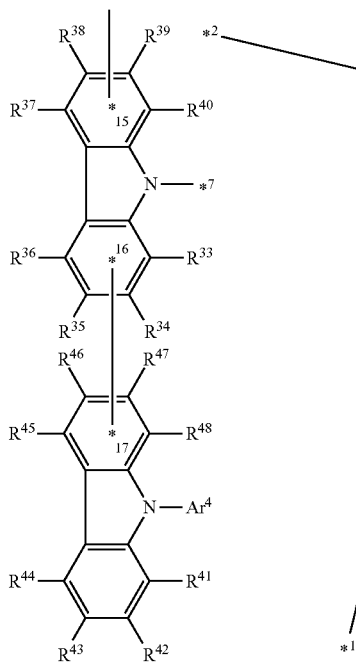
2328
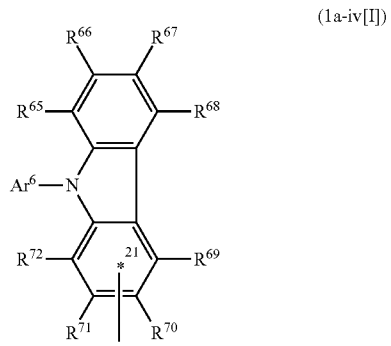
(1a-iv[I])
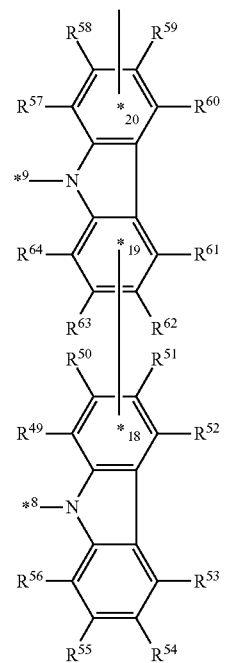
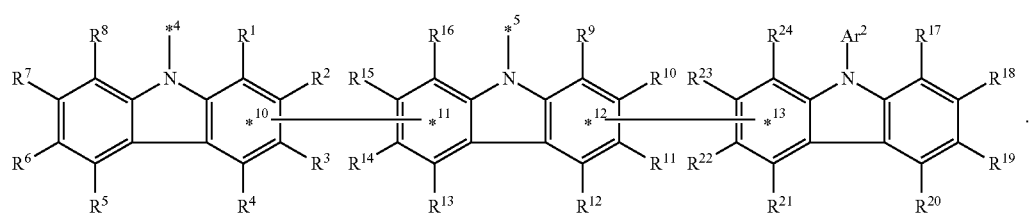
9. The compound according to claim 4, wherein the compound is represented by formula 1a-v[I]:

2329                                                2330
(1a-v[I])
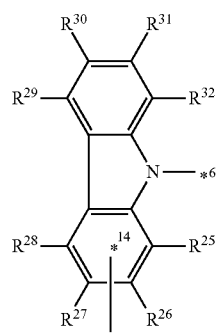
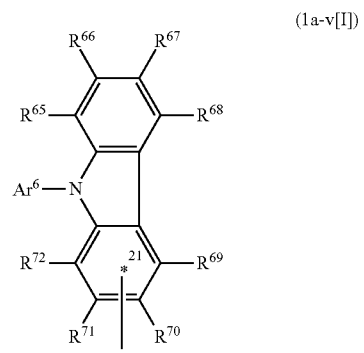
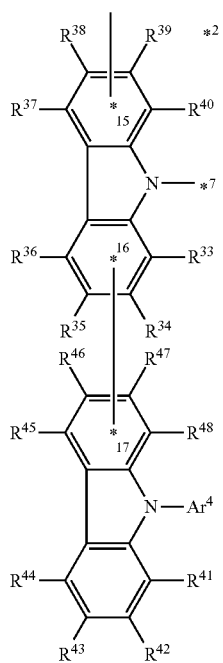
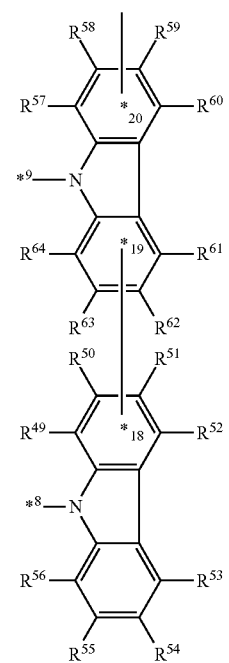
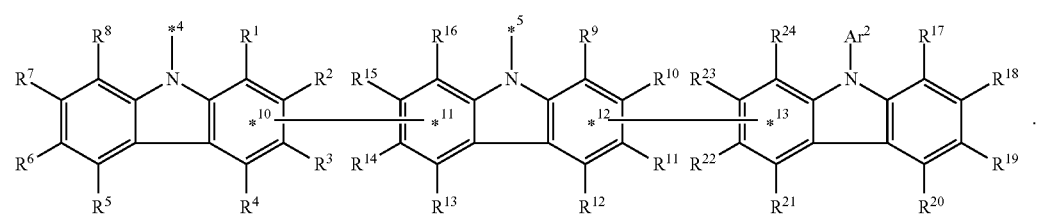

10. The compound according to claim 1, wherein the compound is represented by formula 1b[I]:

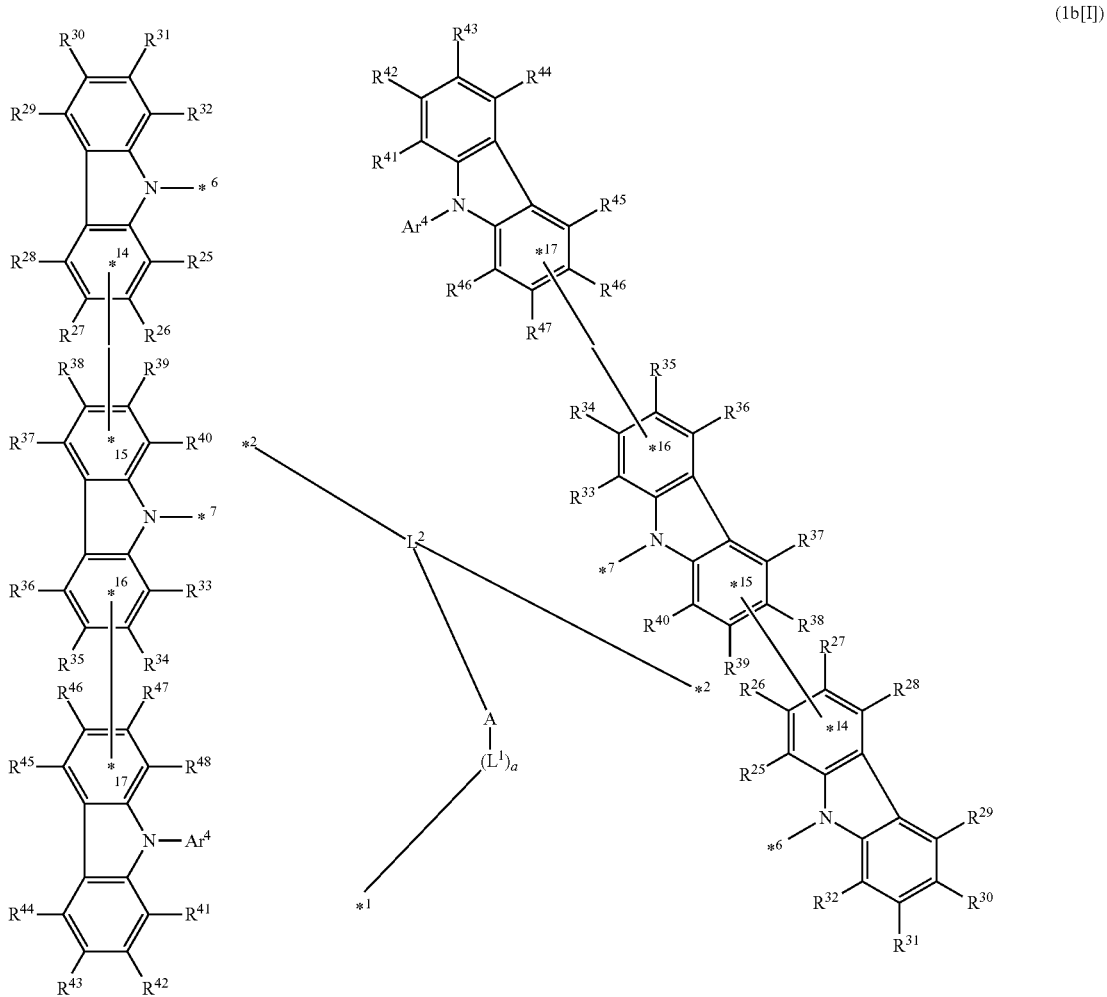

(1b[I])

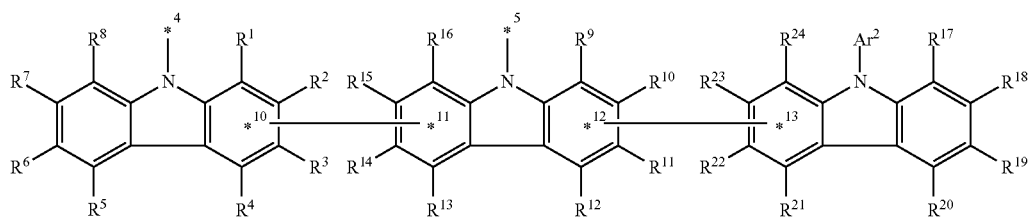

in formula 1b[I],

A, $L^1$, $L^2$, a, to *7, $Ar^2$, and $A^r$ are as defined in claim 1;

$R^1$ to $R^{48}$ are as defined above with respect R of claim 1;

10-*11 is a bond between carbon atoms from which one of $R^1$ to $R^4$ and one of $R^{13}$ to $R^{16}$ are removed;

12-*13 is a bond between carbon atoms from which one of $R^9$ to $R^{12}$ and one of $R^{21}$ to $R^{24}$ are removed;

14-*15 is a bond between carbon atoms from which one of $R^{25}$ to $R^{28}$ and one of $R^{37}$ to $R^{40}$ are removed; and 16-*17 is a bond between carbon atoms from which one of $R^{33}$ to $R^{36}$ and one of $R^{45}$ to $R^{48}$ are removed.

11. The compound according to claim 1, wherein two selected from groups R are not bonded to each other, thereby failing to form a ring.

12. The compound according to claim 1, wherein the compound is represented by formula 1a-vi[I]:

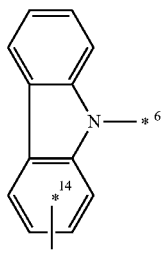
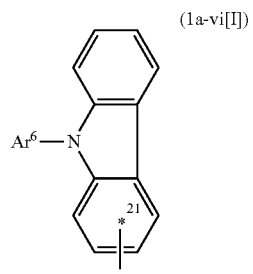
(1a-vi[I])
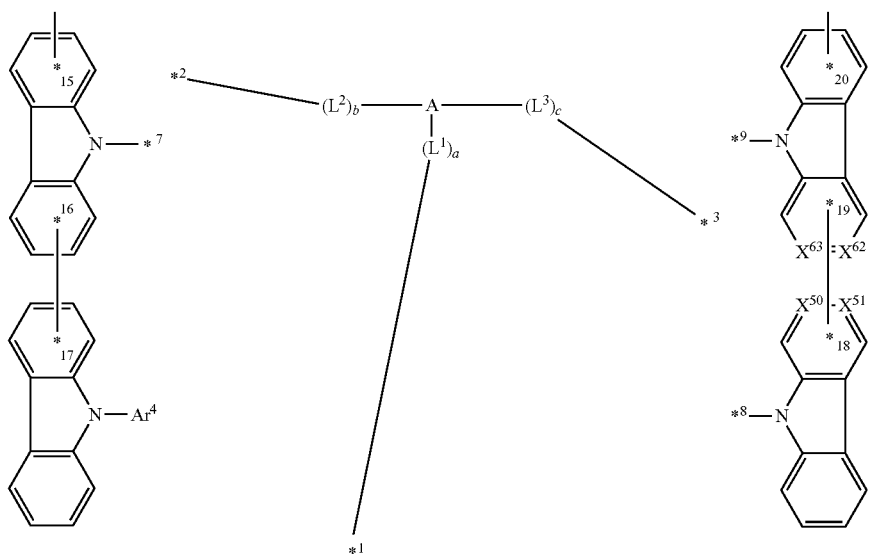
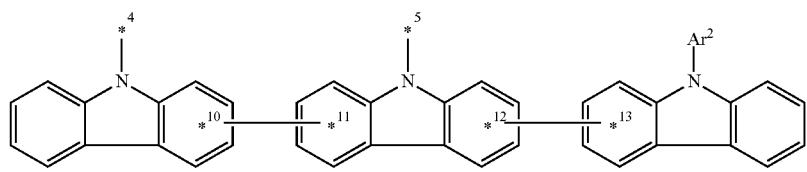
in formula 1a-vi[I],
A, $L^1$ to $L^3$, a to c, *1 to *9, $Ar^2$, $Ar^4$, and $Ar^6$ are as defined in claim 1; and
*10-*11, *12-*13, *14-*15, *16-*17, *18-*19, and *20-*21 each represent a bond between carbon atoms in each benzene ring from which hydrogen atoms are removed.
13. The compound according to claim 1, wherein the compound is represented by formula 1b-i[I]:
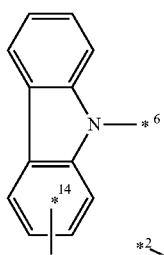
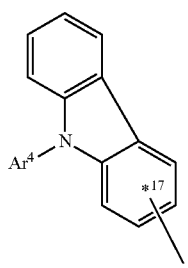
(1b-i[I])

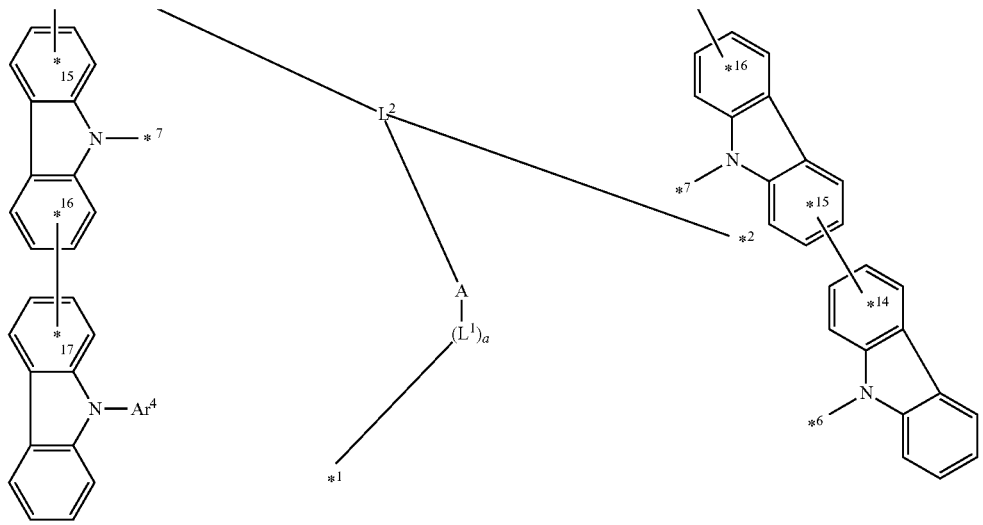
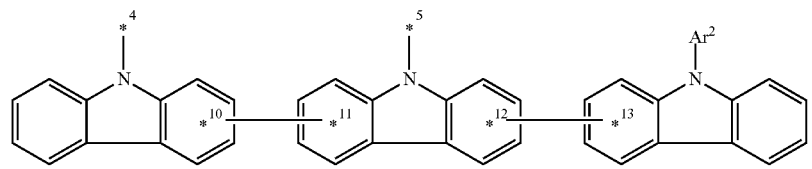
in formula 1b-i[I],
A, $L^1$, $L^2$, a, *1 to *7, $Ar^2$, $Ar^4$ are as defined in claim 1; and
*10-*11, *12-*13, *14-*15, and *16-*17 each represent a bond between carbon atoms in each benzene ring from which hydrogen atoms are removed.
14. The compound according to claim 1, wherein the compound is represented by formula 1c-i[I]:

-continued

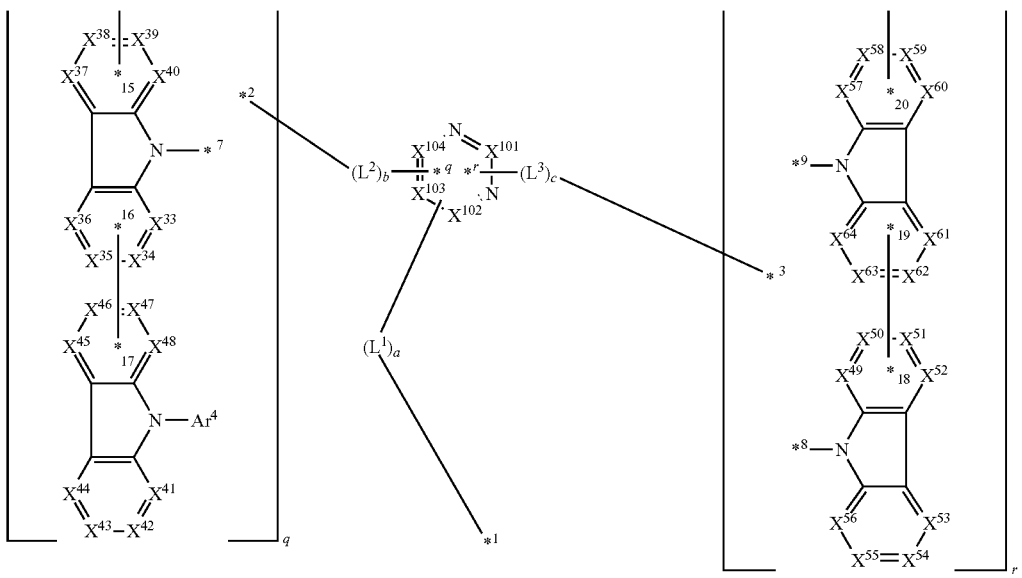

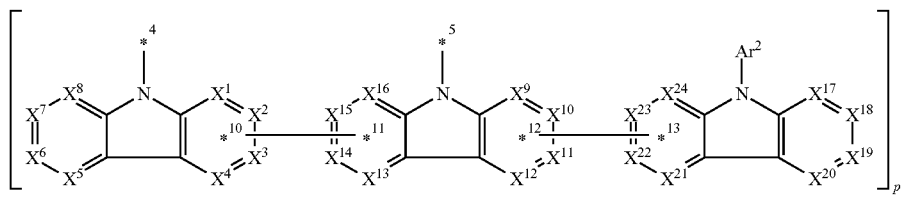

in formula 1c-i[I], $L^1$ to $L^3$, a to c, $X^1$ to $X^{72}$, *1 to *21, $Ar^2$, $Ar^4$, and $Ar^6$ are as defined in claim 1;

$X^{101}$ to $X^{104}$ each represent a carbon atom bonded to one of *p to *r, C(Rx), or a nitrogen atom; and Rx represents a hydrogen atom or a substituent, two or more groups Rx may be the same or different, and two selected from groups Rx may be bonded to each other to form a ring.

15. The compound according to claim 1, wherein the compound is represented by formula 1c-ii[I]:

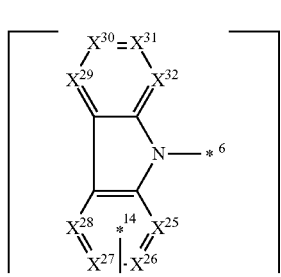 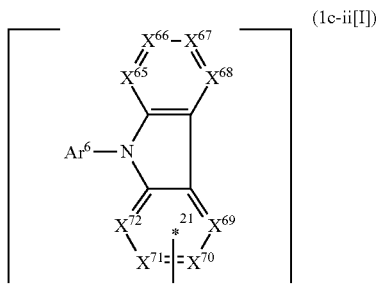

(1c-ii[I])

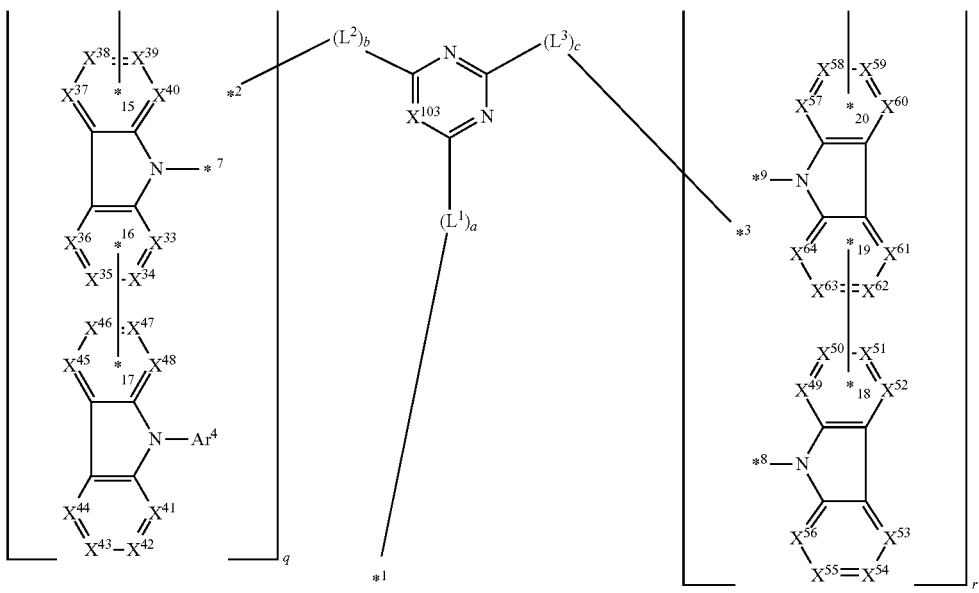
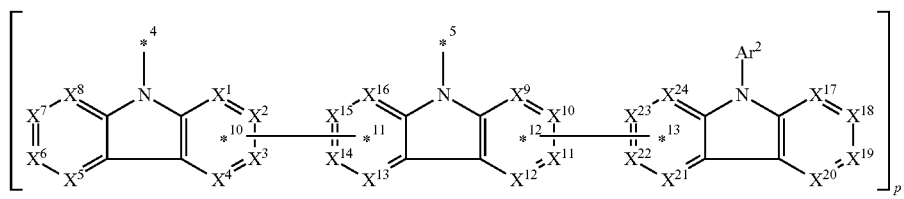
in formula 1c-ii[I],
$L^1$ to $L^3$, a to c, $X^1$ to $X^{72}$, *1 to *21, $Ar^2$, $Ar^4$, and $Ar^6$ are as defined in claim 1;
$X^{103}$ represents C(Rx) or a nitrogen atom; and
Rx represents a hydrogen atom or a substituent.
16. The compound according to claim 1, wherein the compound is represented by formula 1c-iii[I]:
(1c-iii[I])

-continued

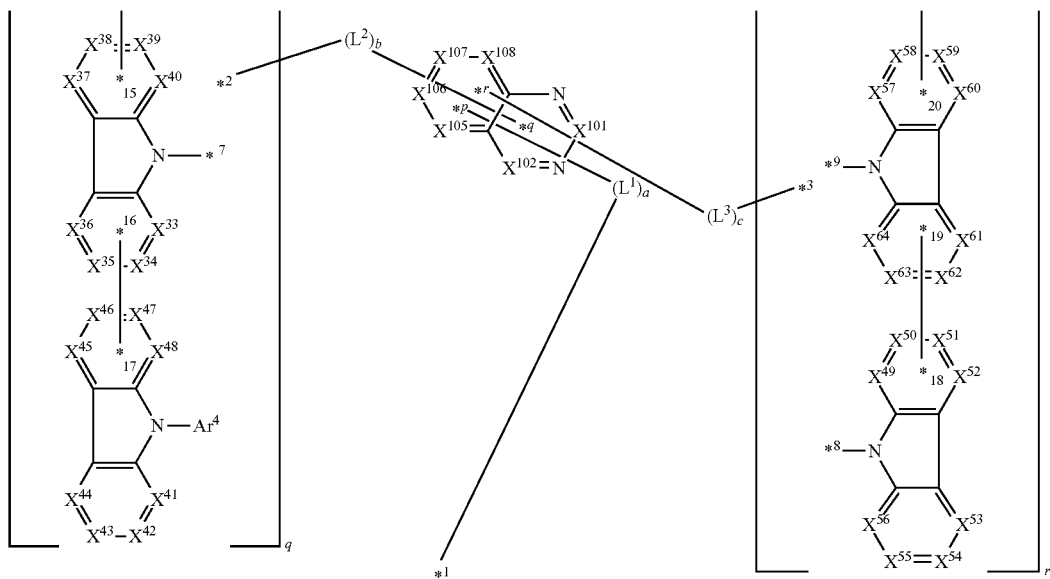

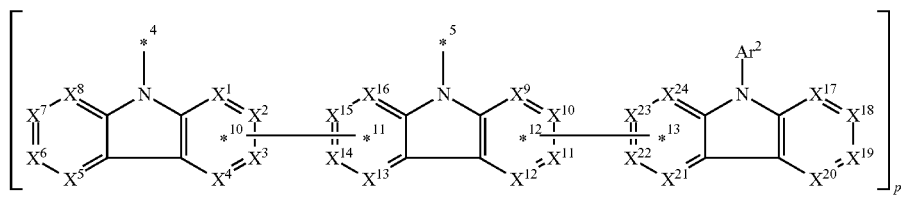

in formula 1c-iii[I],
L$^1$ to L$^3$, a to c, X$^1$ to X$^{72}$, *1 to *21, Ar$^2$, Ar$^4$, and Ar$^6$ are as defined in claim 1;
X$^{101}$, X$^{102}$, and X$^{105}$ to X$^{108}$ each represent a carbon atom bonded to one of *p to *r, C(Rx), or a nitrogen atom;

Rx represents a hydrogen atom or a substituent, two or more groups Rx may be the same or different, and two selected from groups Rx may be bonded to each other to form a ring.

17. The compound according to claim 1, wherein the compound is represented by formula 1c-iv[I]:

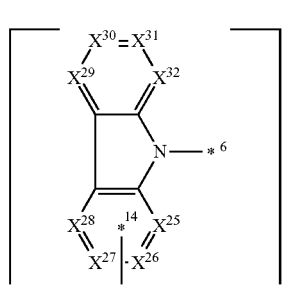

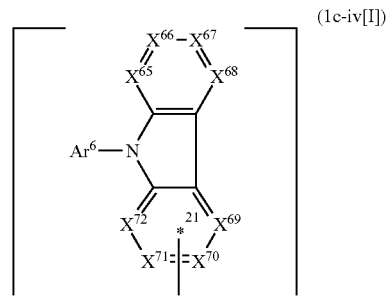

(1c-iv[I])

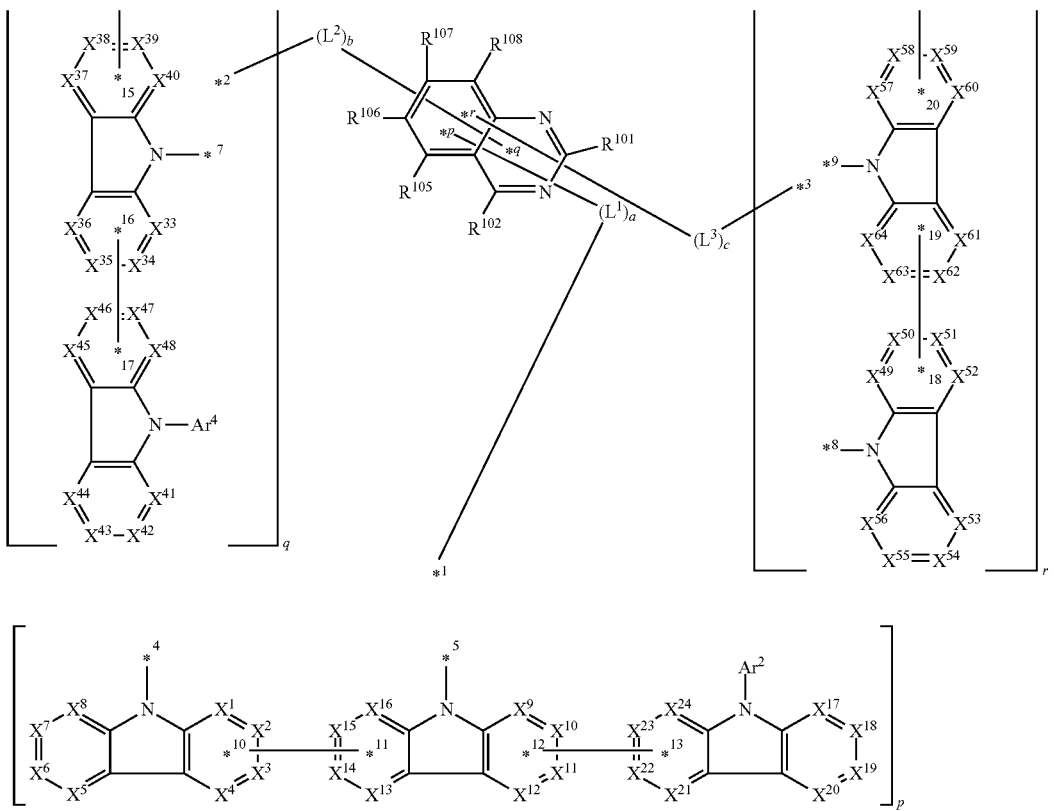

in formula 1c-iv[I], $L^1$ to $L^3$, a to c, $X^1$ to $X^{72}$, *1 to *21, $Ar^2$, $Ar^4$, and $Ar^6$ are as defined in claim 1;

1 to 3 carbon atoms from which one to three selected from $R^{101}$, $R^{102}$, and $R^{105}$ to $R^{108}$ are removed are each bonded to one of *p to *r, and the others each independently represent a hydrogen atom or a substituent; and two selected from $R^{102}$ and $R^{105}$ to $R^{108}$ may be bonded to each other to form a ring.

18. The compound according to claim 1, wherein each of $Ar^1$ to $Ar^6$ represents a substituted or unsubstituted aryl group having 6 to 30 ring carbon atoms.

* * * * *

UNITED STATES PATENT AND TRADEMARK OFFICE
CERTIFICATE OF CORRECTION

PATENT NO. : 10,290,815 B2
APPLICATION NO. : 15/125085
DATED : May 14, 2019
INVENTOR(S) : Taro Yamaki et al.

It is certified that error appears in the above-identified patent and that said Letters Patent is hereby corrected as shown below:

In the Claims

Column 2305, Line 52, Claim 1, formula (1[I]), "Ar$^4$",

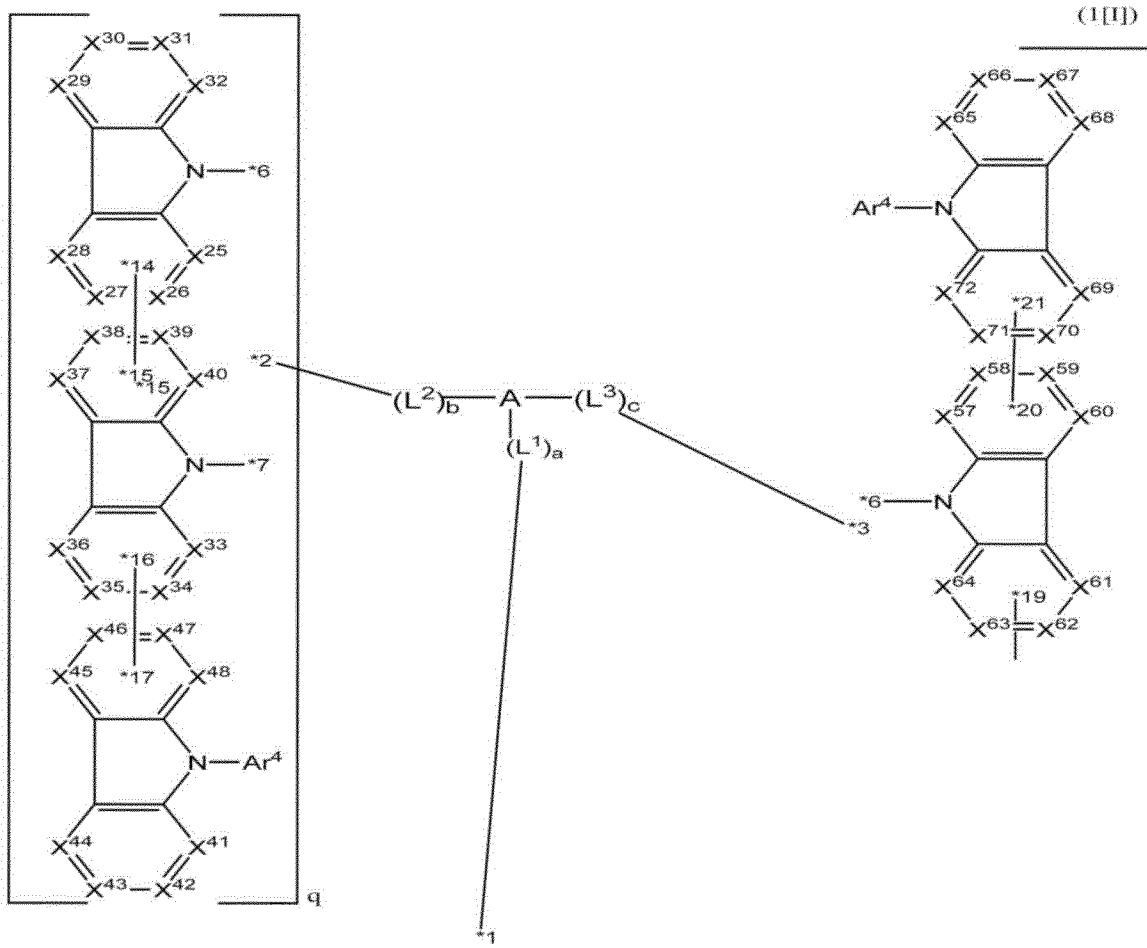

Signed and Sealed this
Fifteenth Day of September, 2020

Andrei Iancu
*Director of the United States Patent and Trademark Office* should read --Ar⁶--.
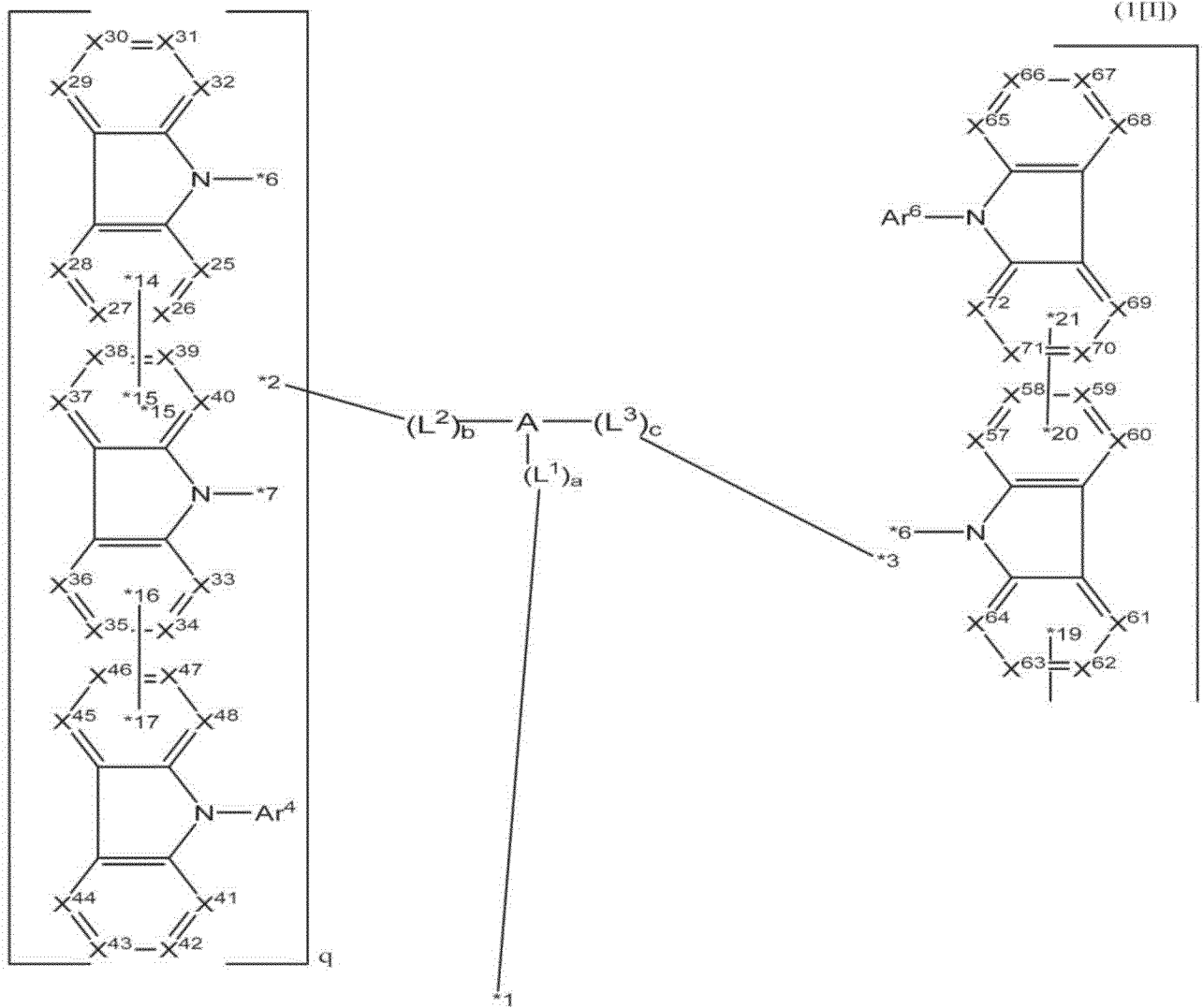
Column 2307, Line 5, Claim 1, "$X^5$ to $X^8$, $X^{17}$ to $X^{20}$, $X^{29}$ to $X^{32}$, $X^{41}$ to $X^{44}$, $X^{53}$ to $X^{36}$,": should read --$X^5$ to $X^8$, $X^{17}$ to $X^{20}$, $X^{29}$ to $X^{32}$, $X^{41}$ to $X^{44}$, $X^{53}$ to $X^{55}$,--.
Column 2307, Line 24, Claim 2, formula (CH1),
" 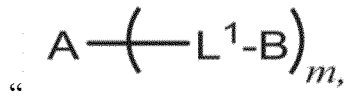 " should read
-- 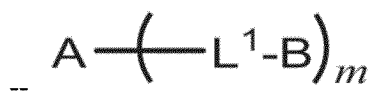 --.

CERTIFICATE OF CORRECTION (continued)
U.S. Pat. No. 10,290,815 B2

Page 3 of 27

Column 2307, Line 42, Claim 2, formula (CH2),

" 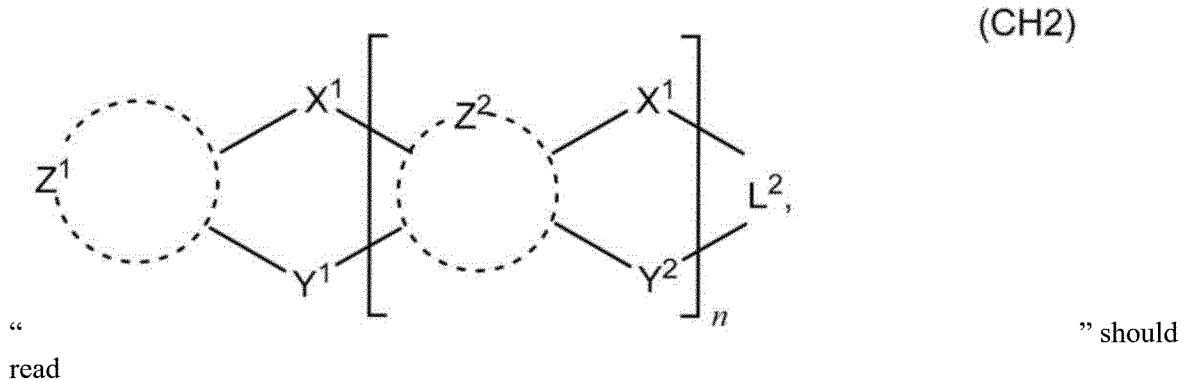 (CH2)

" should read

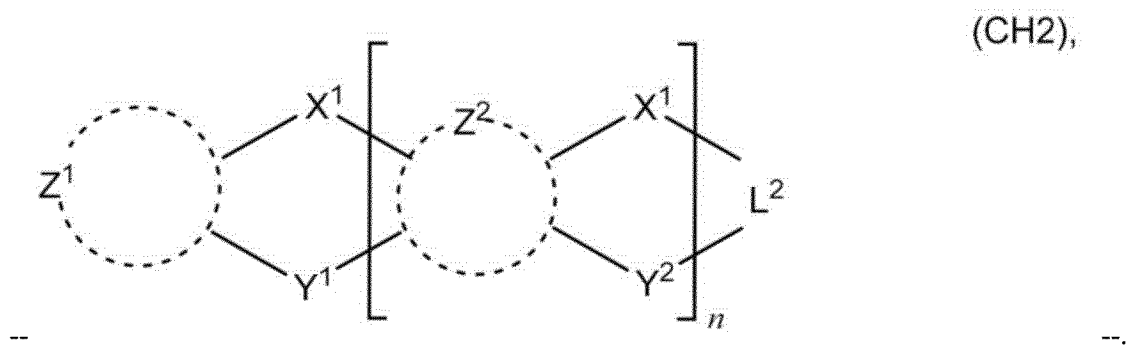 (CH2),

--    --.

Column 2308, Line 11, Claim 2, formula (CH3),

" 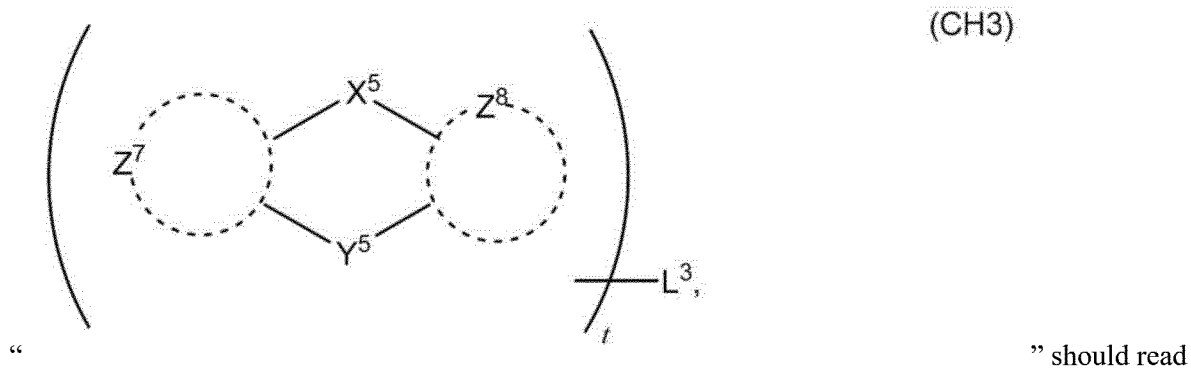 (CH3)

" should read

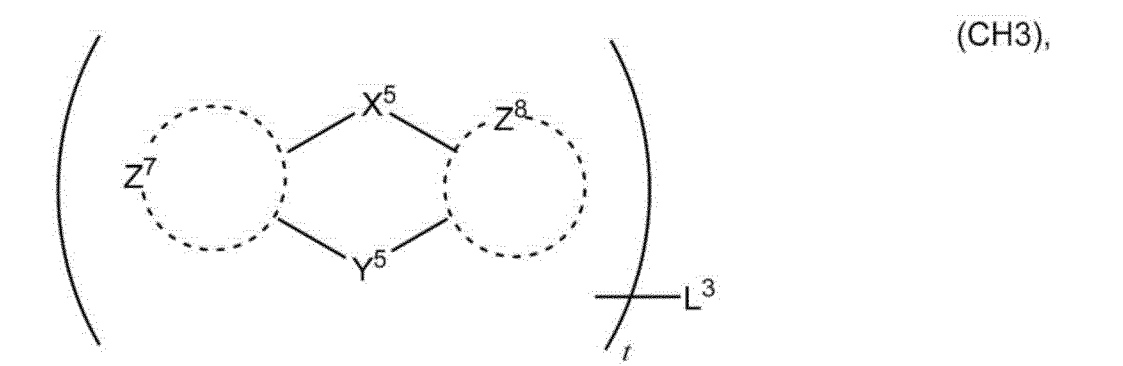 (CH3),

--    --.

Column 2308, Line 40, Claim 2, formula (CH4),
"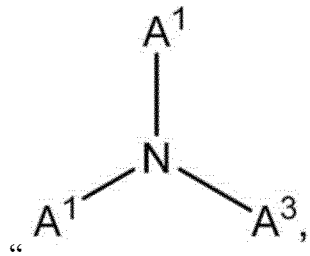" should read
--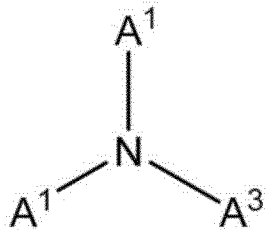--.
Column 2308, Line 52, Claim 2, formula (CH5),
"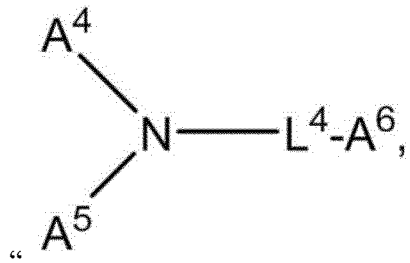" should read
--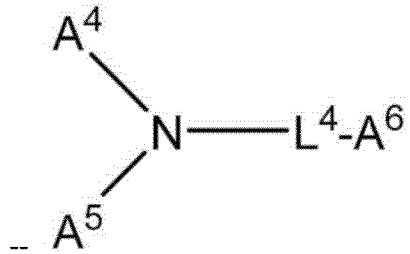--.

Column 2309, Line 4, Claim 2, formula (CH6),
" 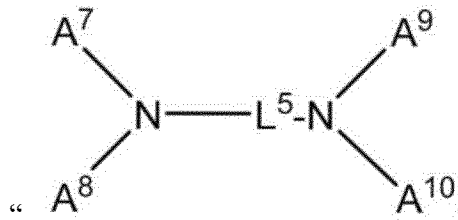 " should read
-- 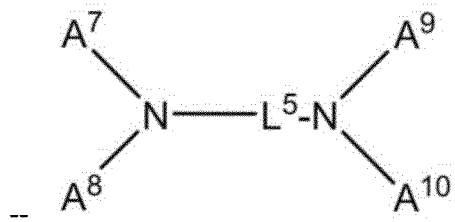 --.
Column 2310, Line 4, Column 2, formula (CH14),
" 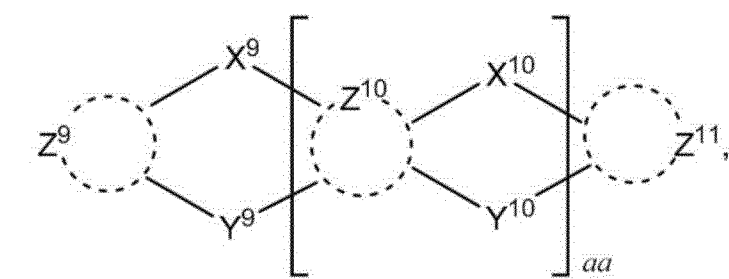 " should read
-- 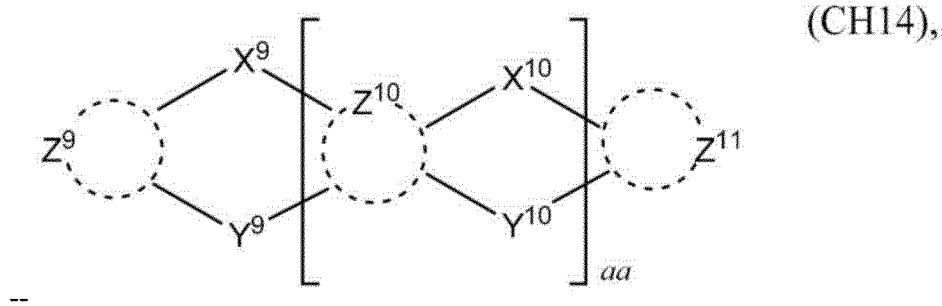 --.

CERTIFICATE OF CORRECTION (continued)
U.S. Pat. No. 10,290,815 B2

Columns 2309 and 2310, Line 22, Claim 3, formula (1a[I]),

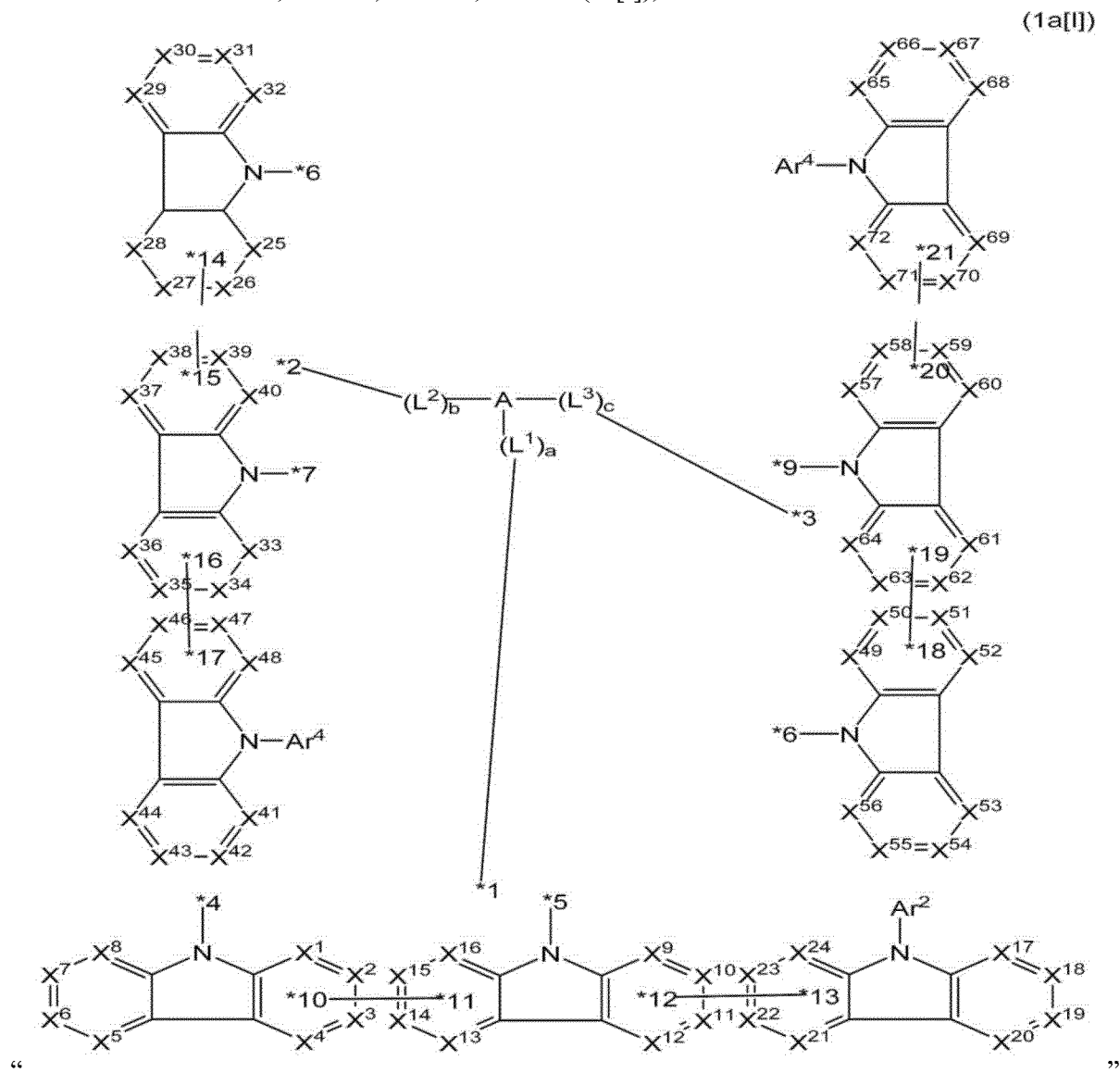

" "

should read
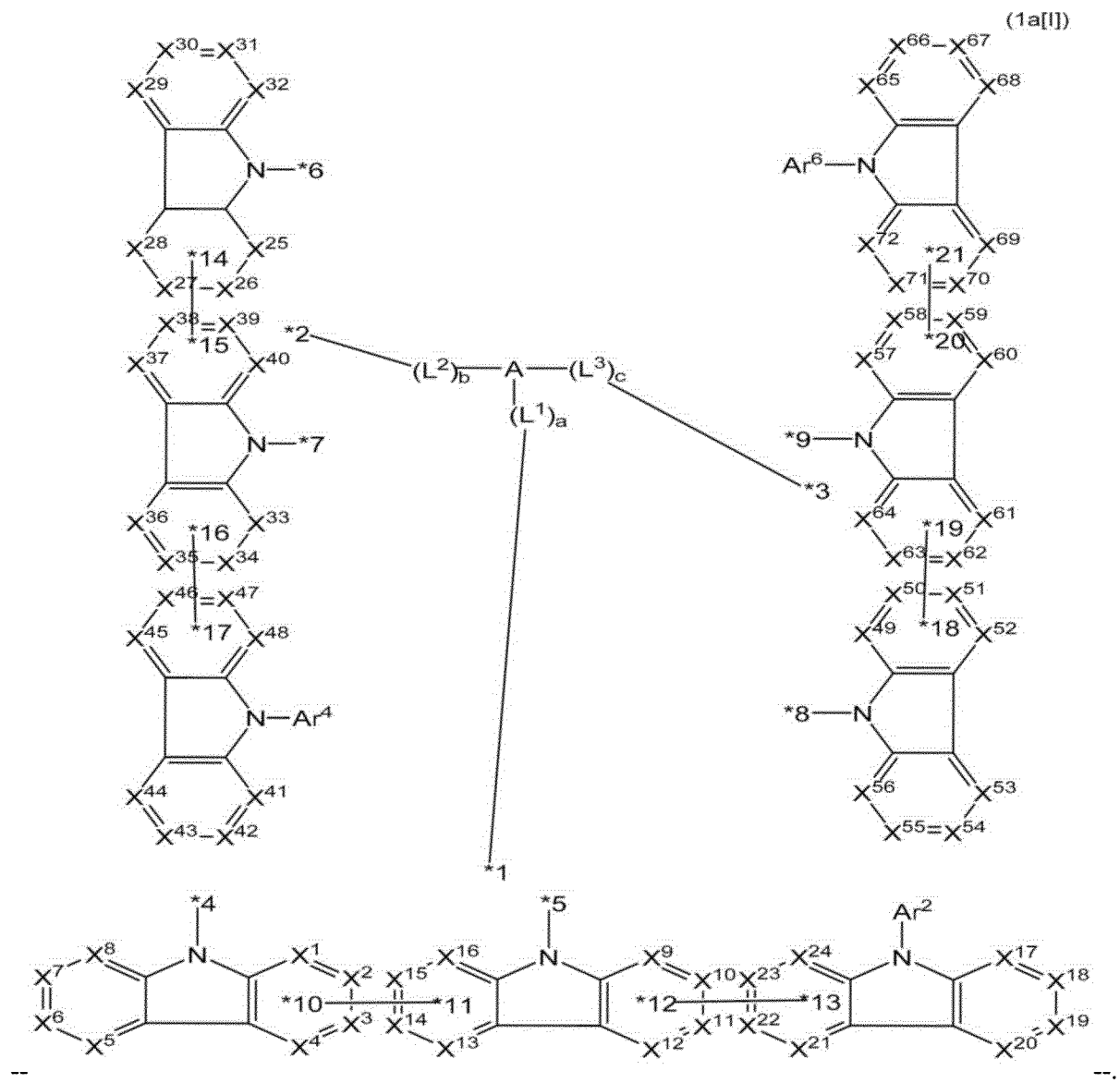

Columns 2311 and 2312, Line 5, Claim 4, formula (1a-i[I]):
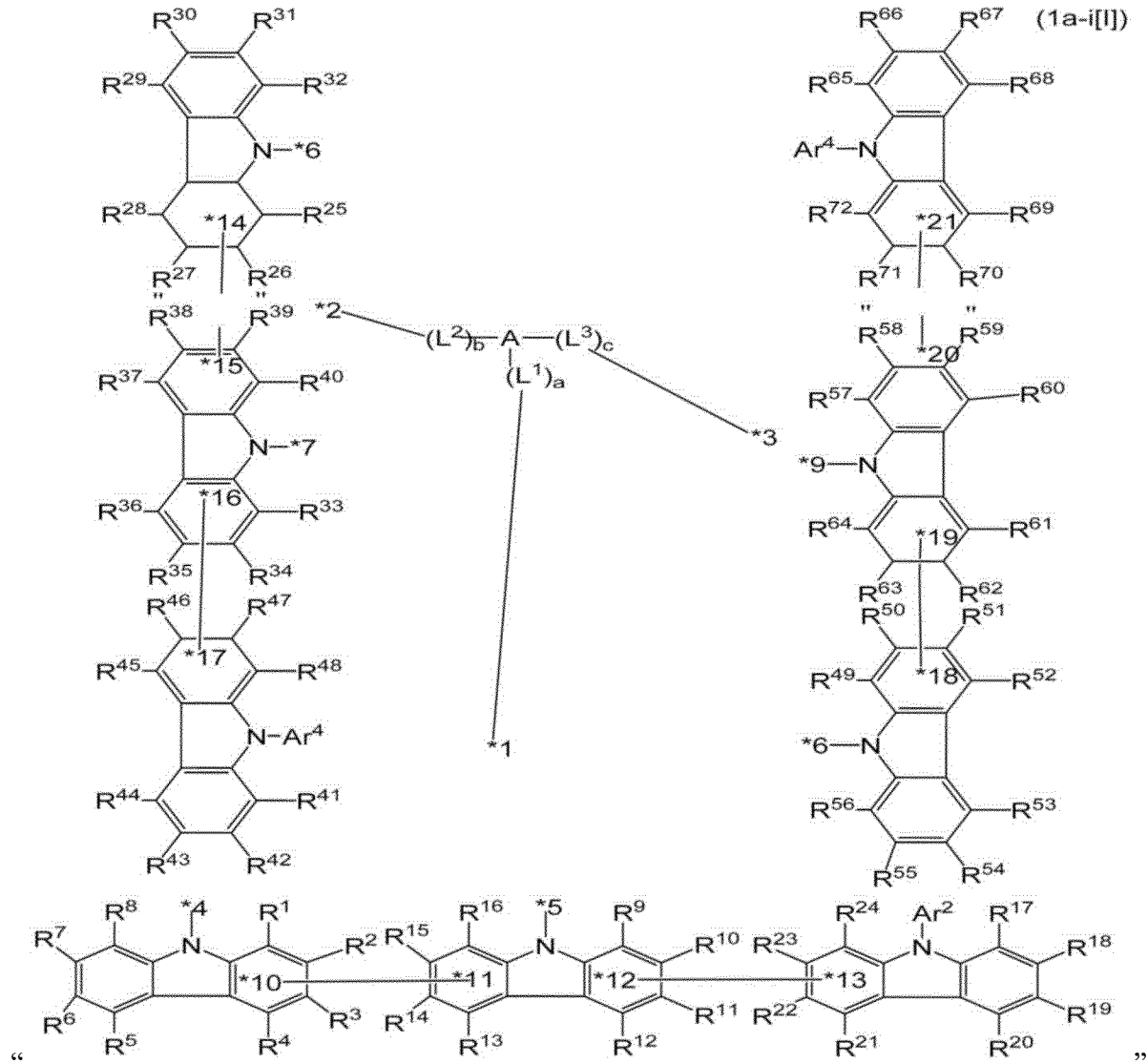

should read
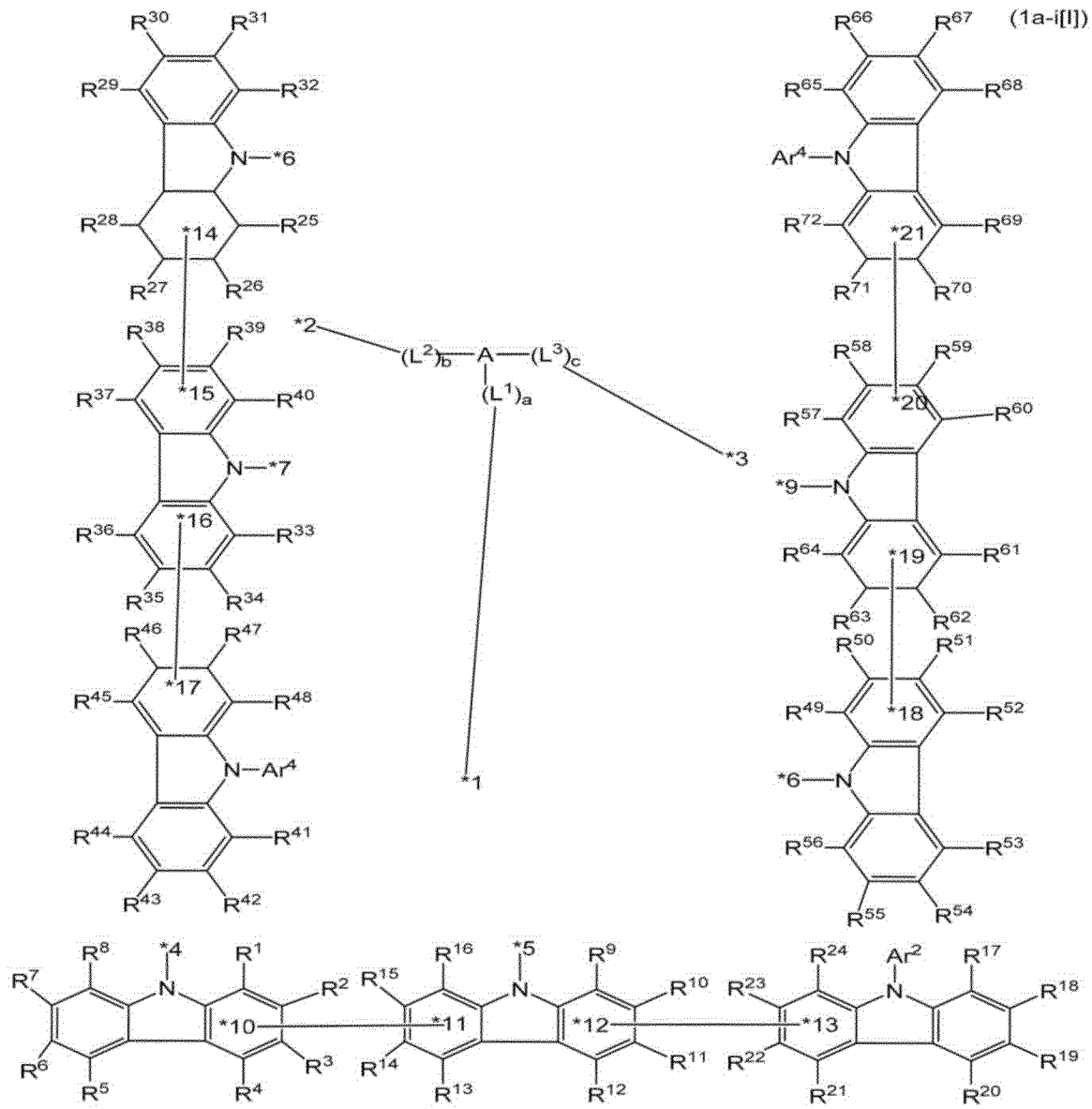
--                                                                                     --.
Column 2311, Claim 4, Line 64, "10-*11" should read --*10-*11--;
    Claim 4, Line 66, "12-*13" should read --*12-*13--;
Column 2312, Claim 4, Line 1, "14-*15" should read --*14-*15--;
    Claim 4, Line 3, "16-*17" should read --*16-*17--;
    Claim 4, Line 63, "18-*19" should read --*18-*19--;
    Claim 4, Line 66, "20-*21" should read --*20-*21--.

Columns 2313 and 2314, Line 3, Claim 5, formula (1a-ii[I]),
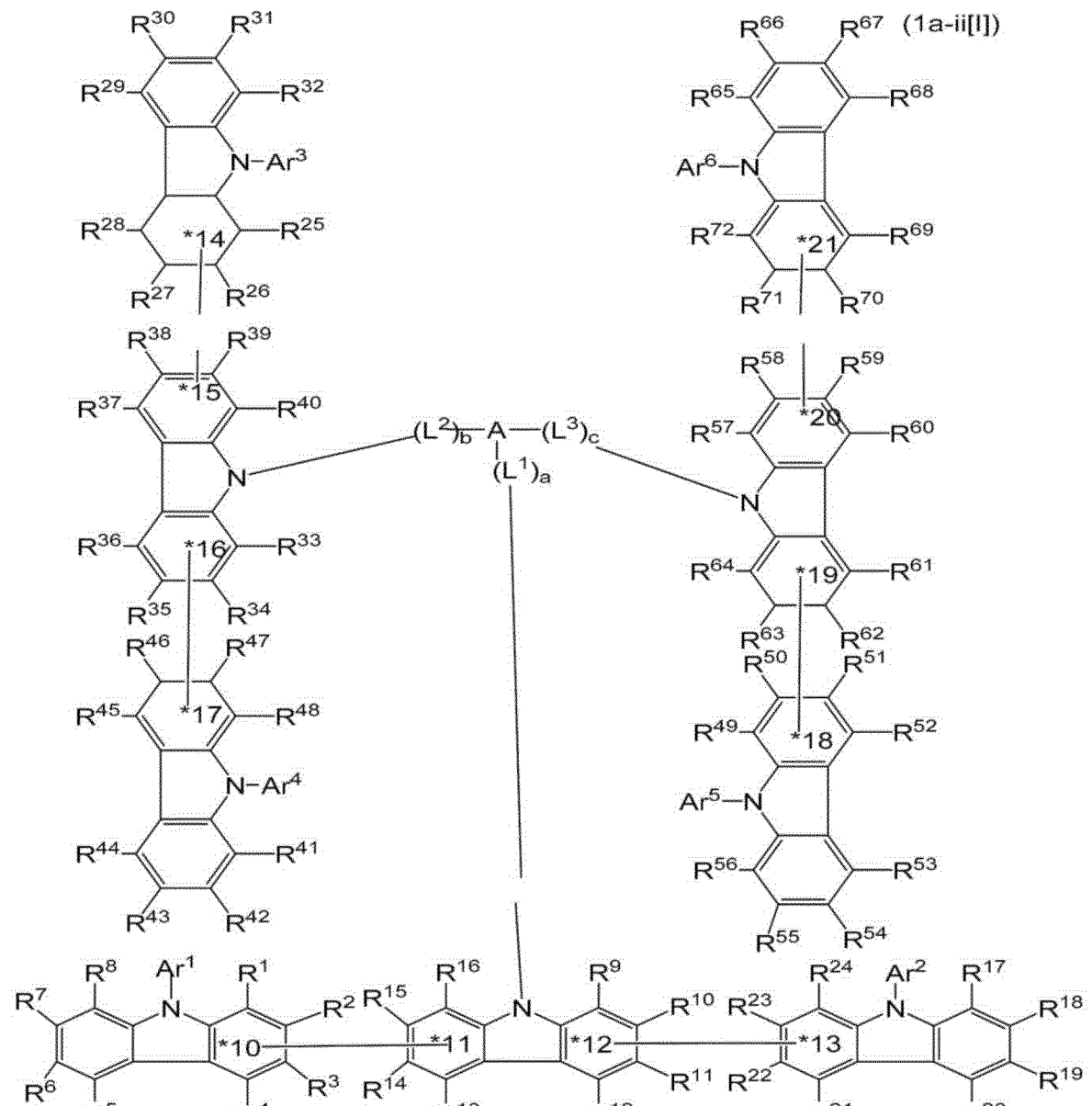
" "

should read
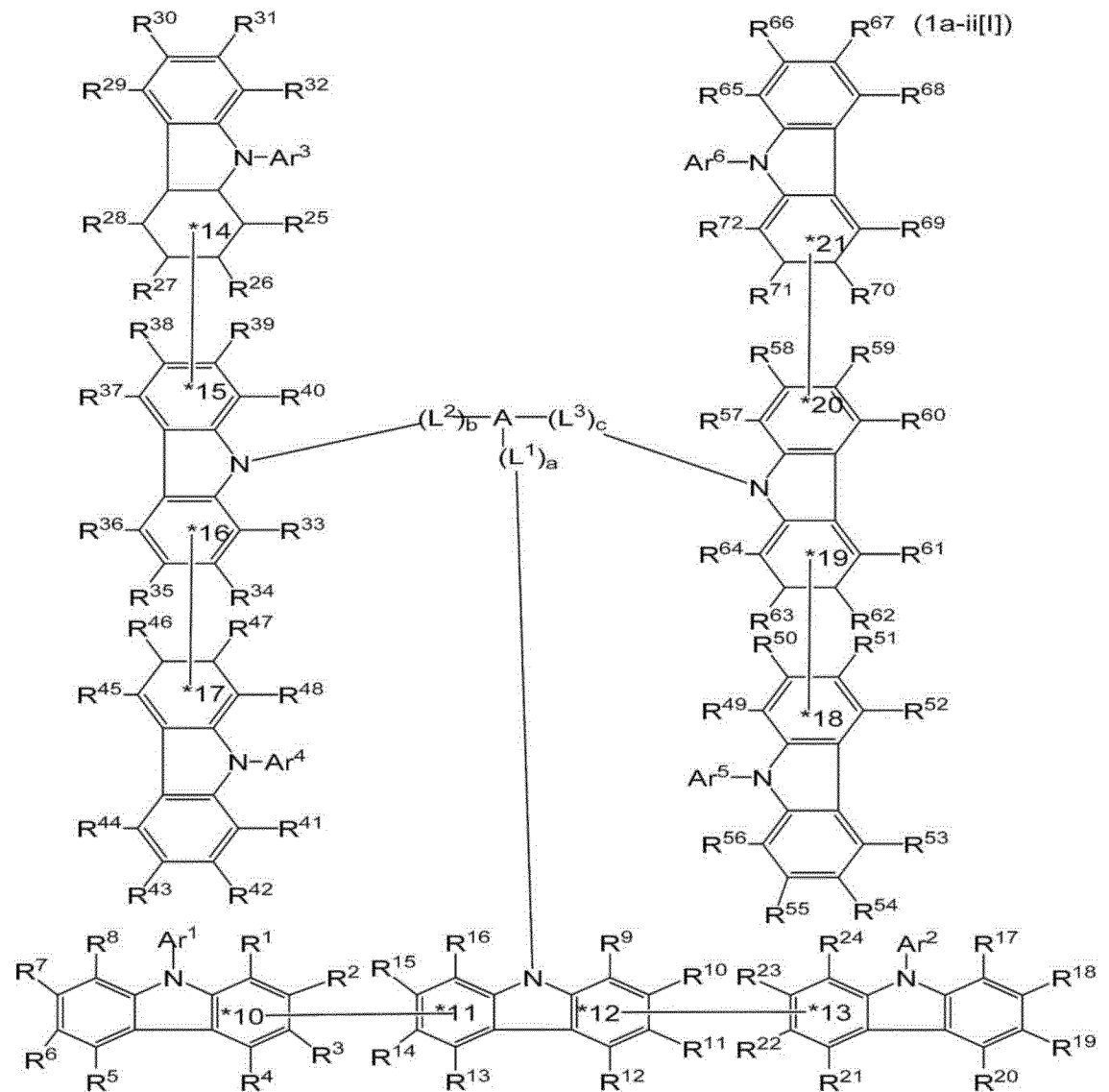
--

Columns 2315 and 2316, Claim 6, formula (1a-ii-1[I]),
" 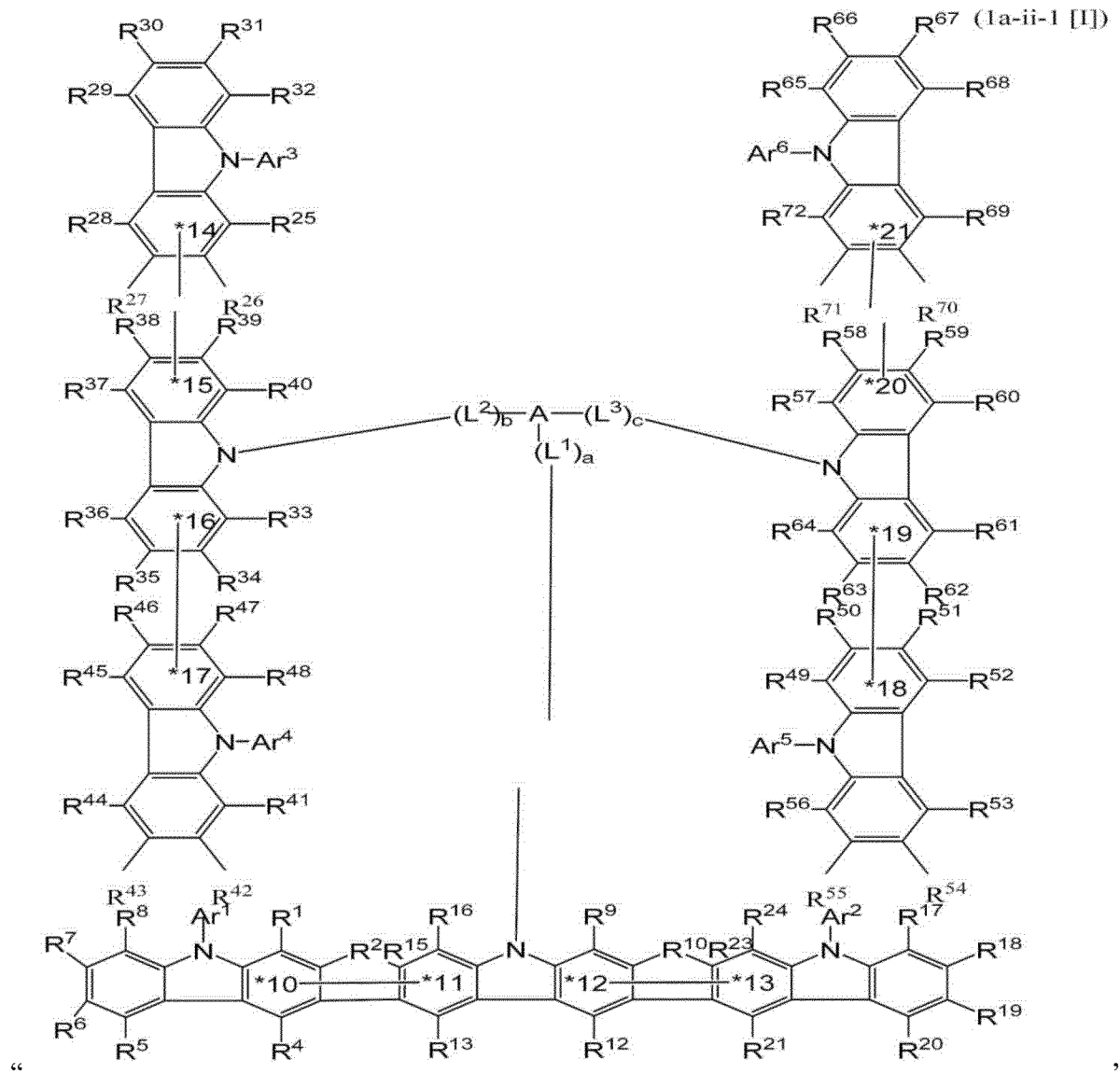 "

should read
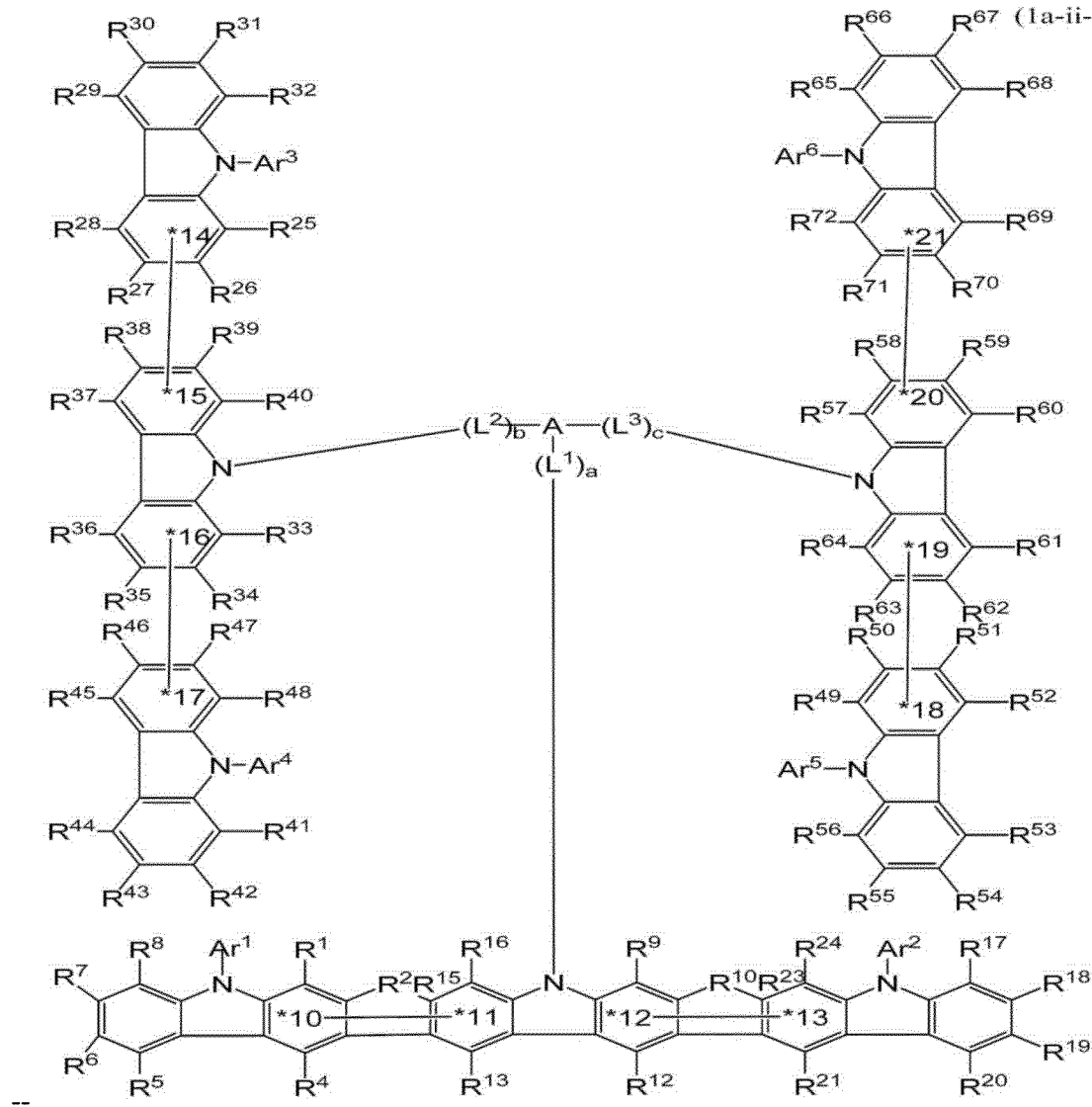
--.

Columns 2317 and 2318, Claim 6, formula (1a-ii-2[I]),
" 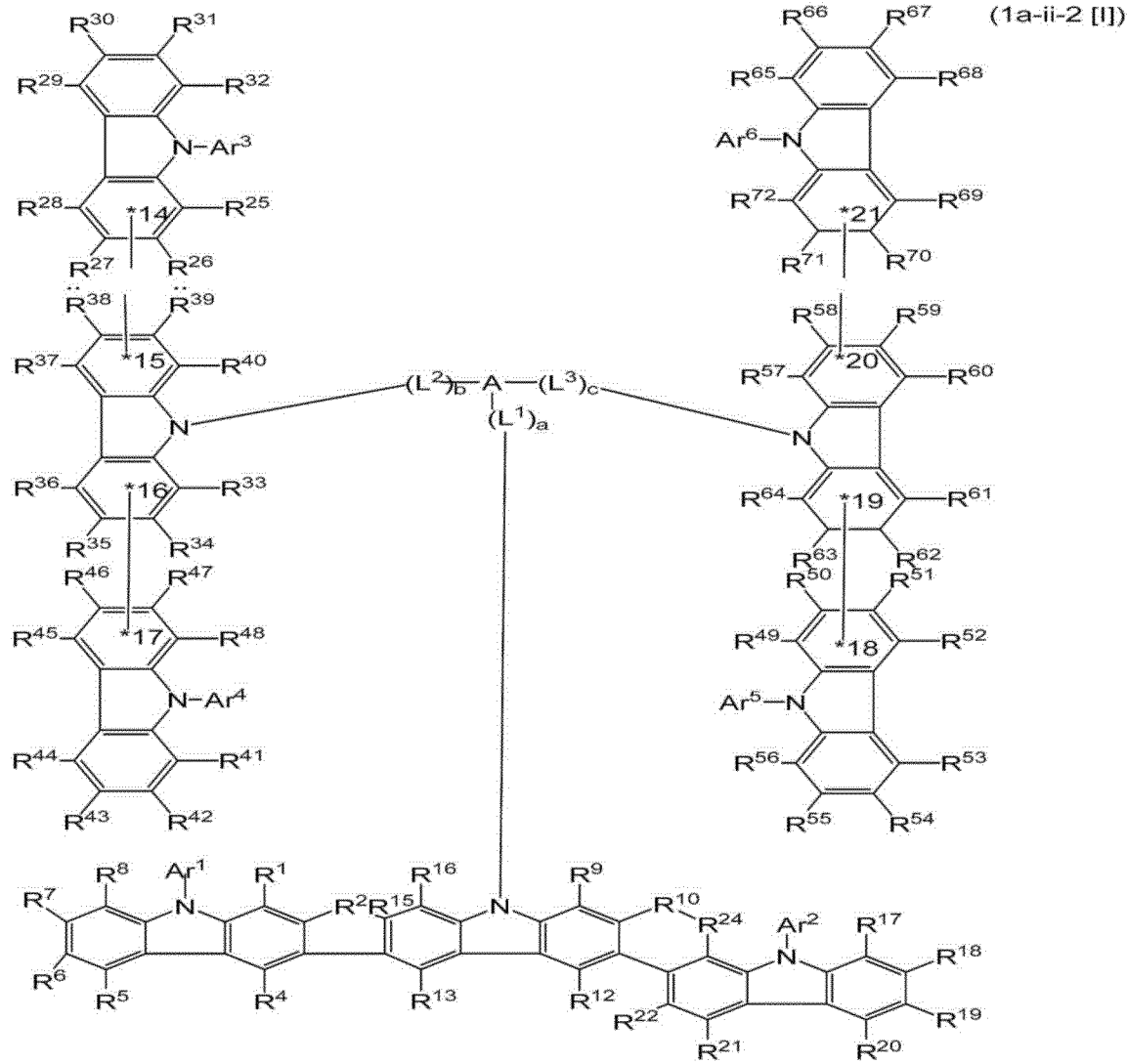 "

should read
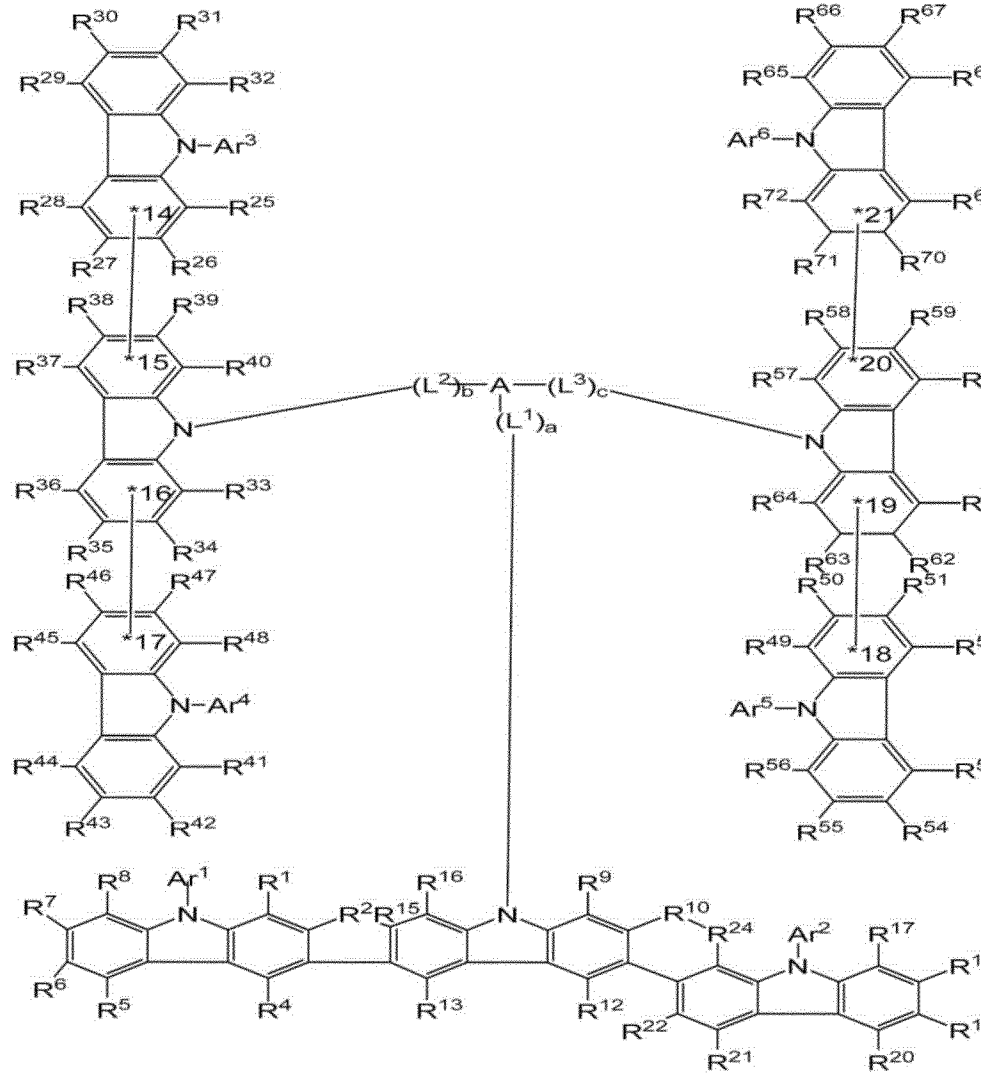
--                                                                                                                                                                                       --.

Columns 2321 and 2322, Claim 6, formula (1a-ii-5[I]),
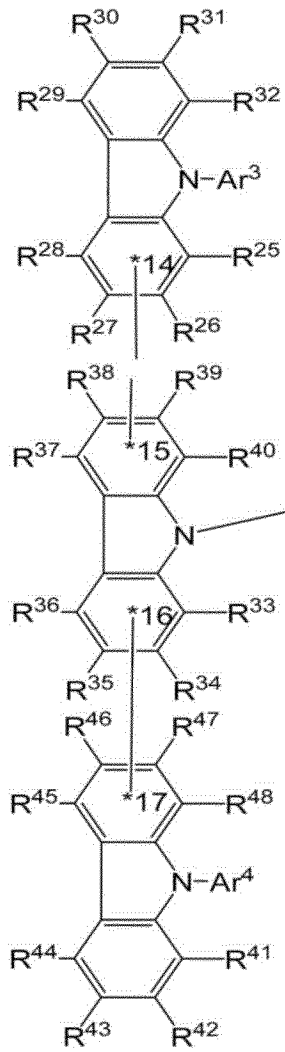
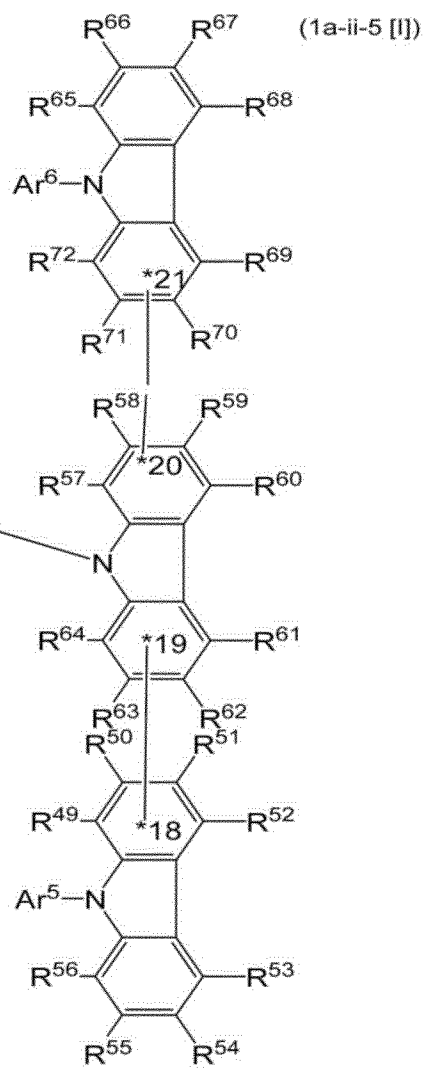
" "

should read
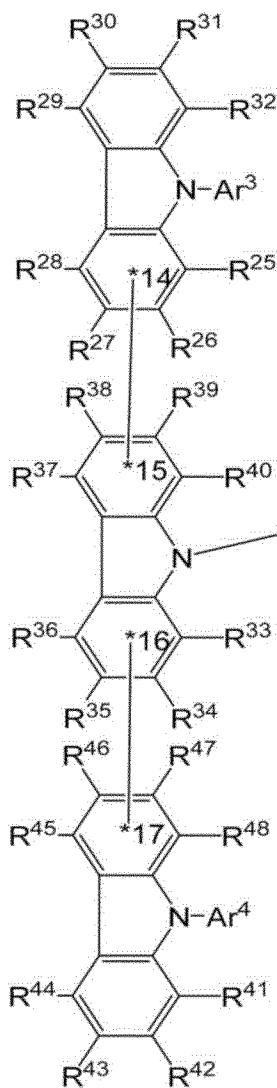
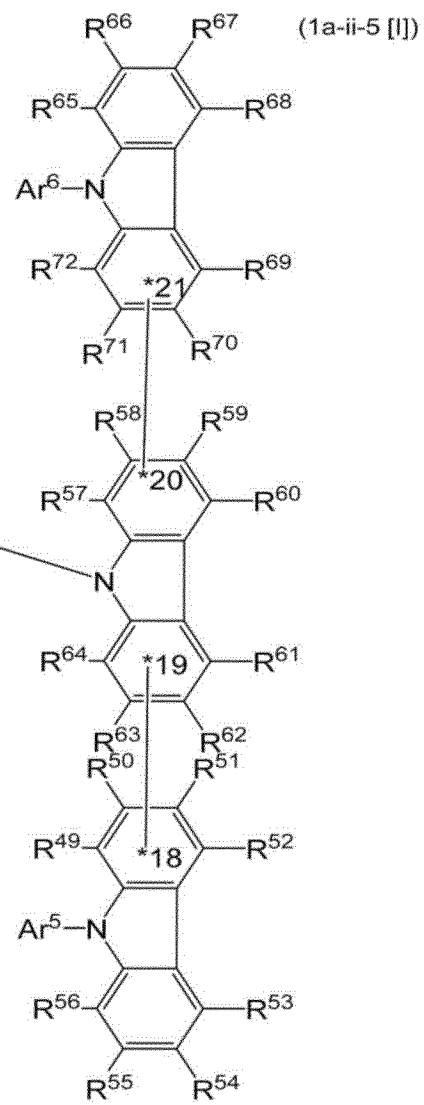
(1a-ii-5 [I])
--                                                                                      --.

Columns 2323 and 2324, Claim 6, formula (1a-ii-6[I]),
" 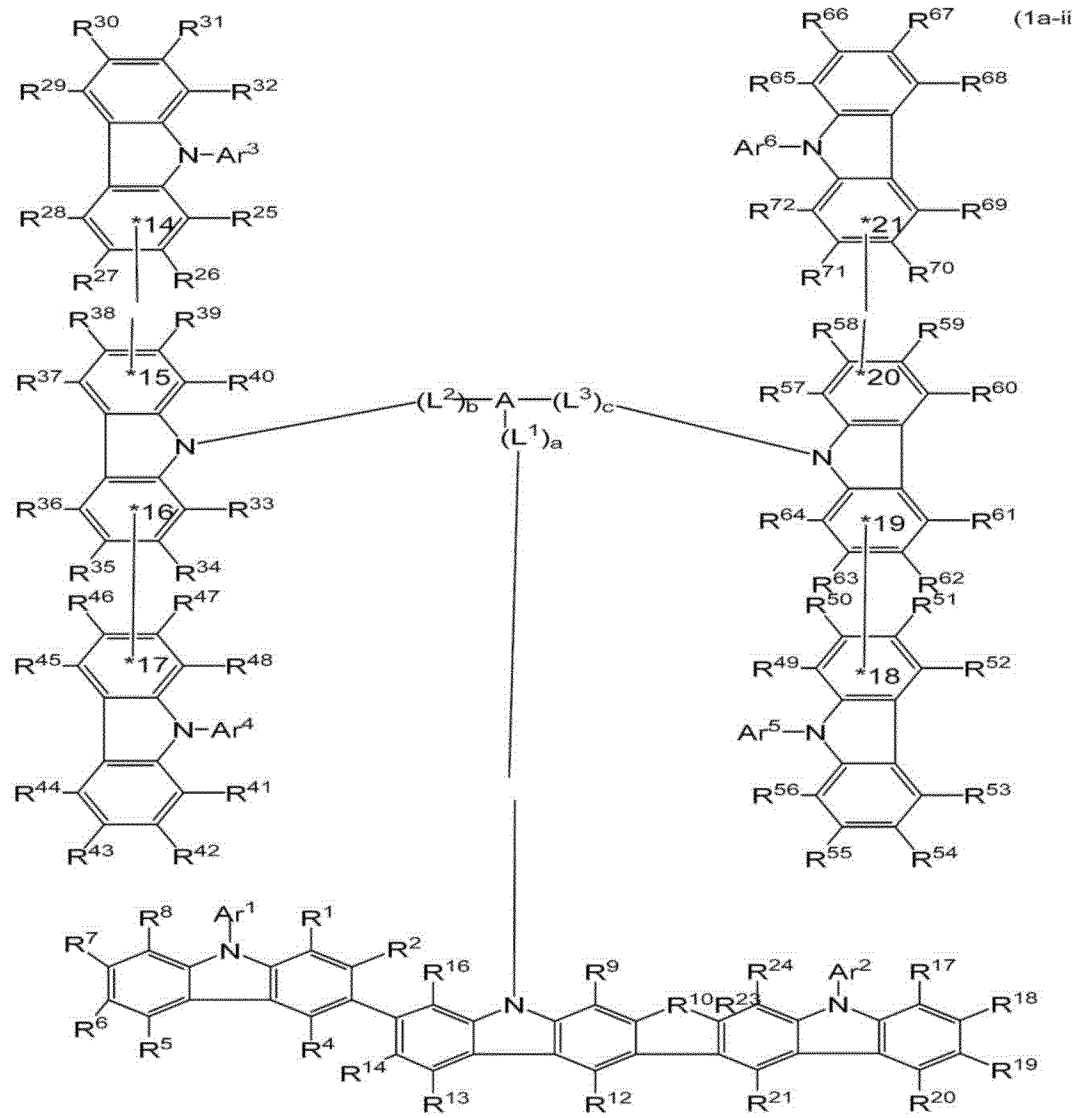 "

should read
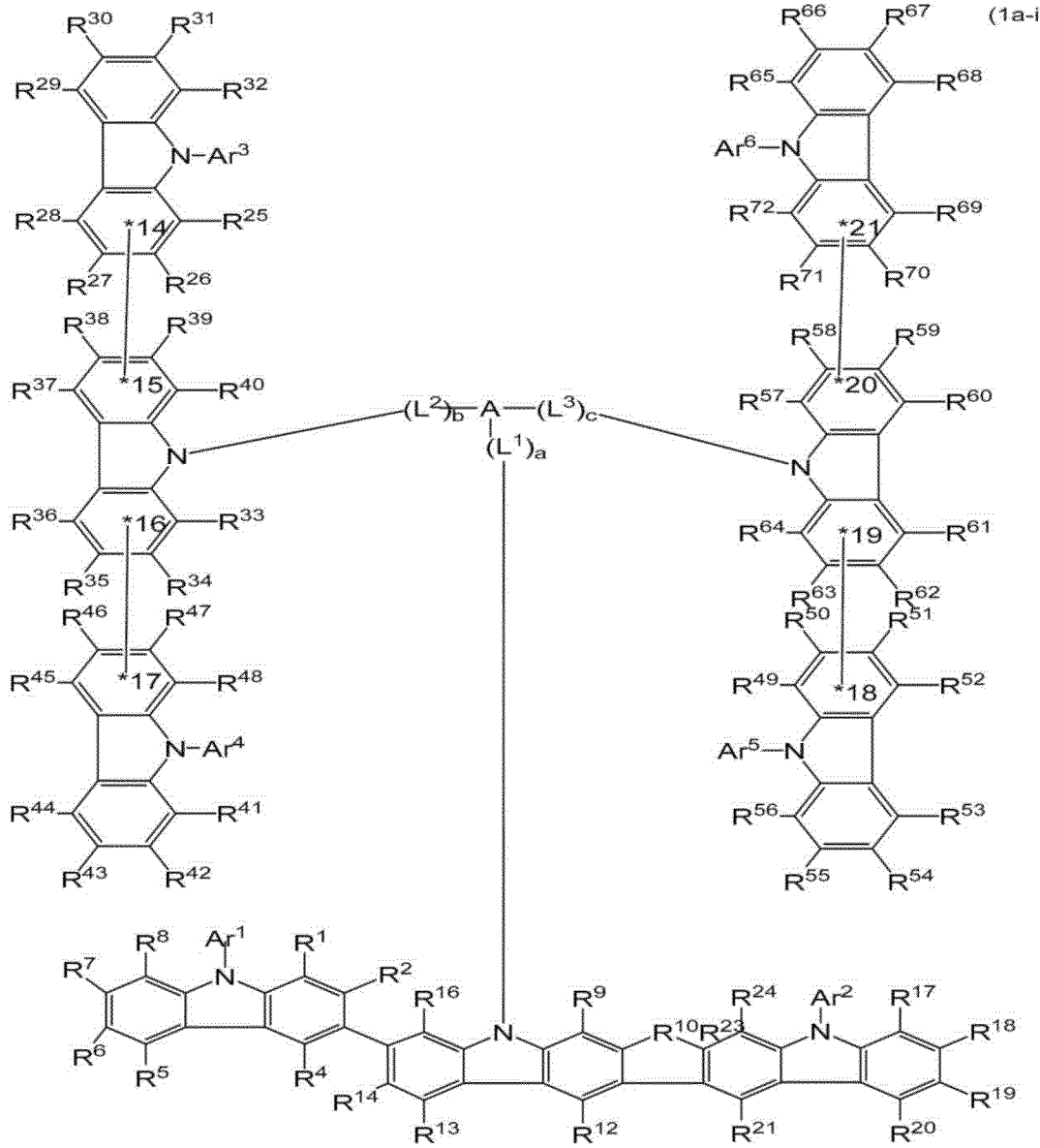
Column 2326, Line 1, Claim 7, "(1a-ii[I]i)" should read --(1a-iii[I])--.

Columns 2327 and 2328, Claim 8, formula (1a-iv[I]),
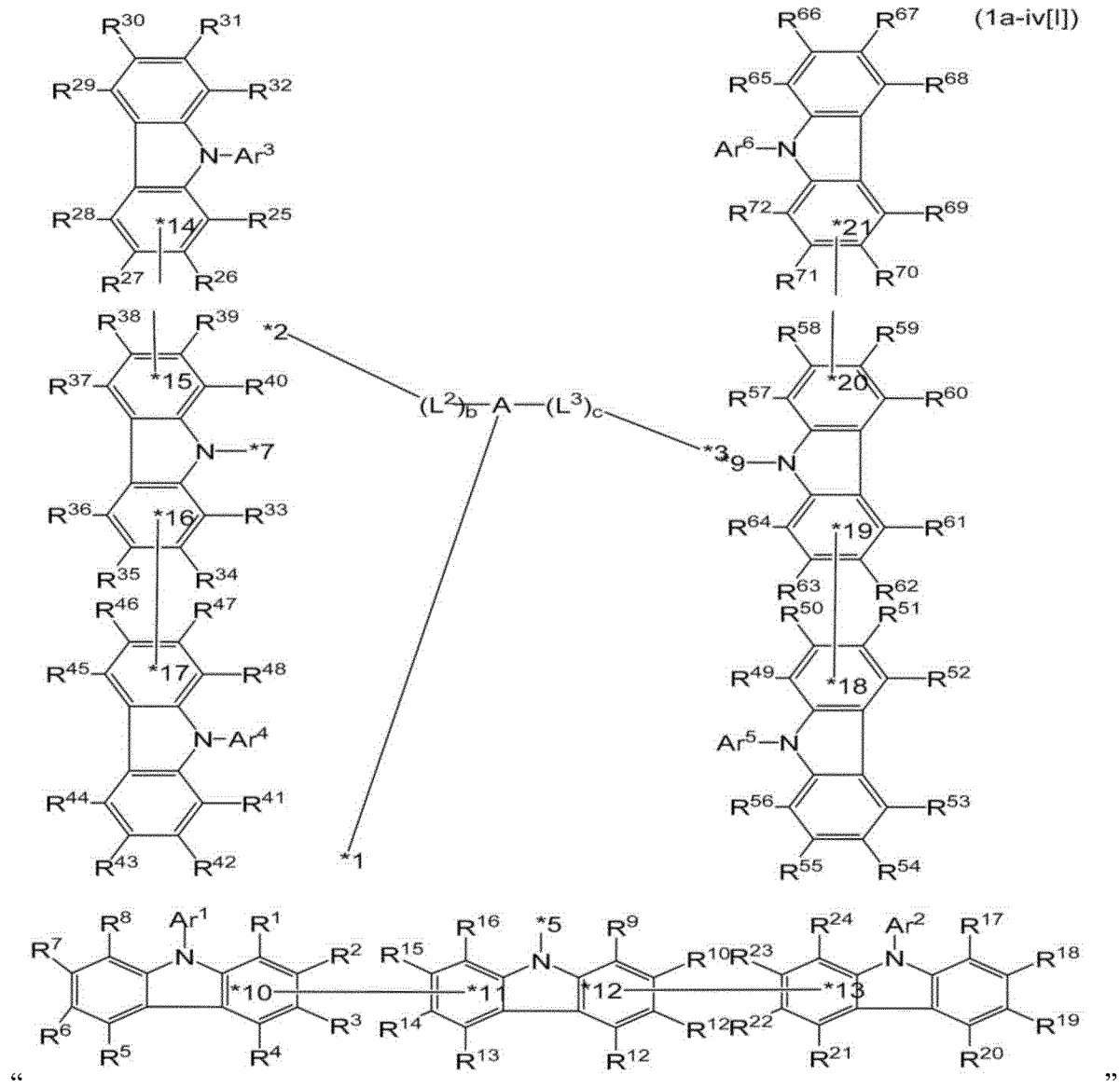
" "

should read
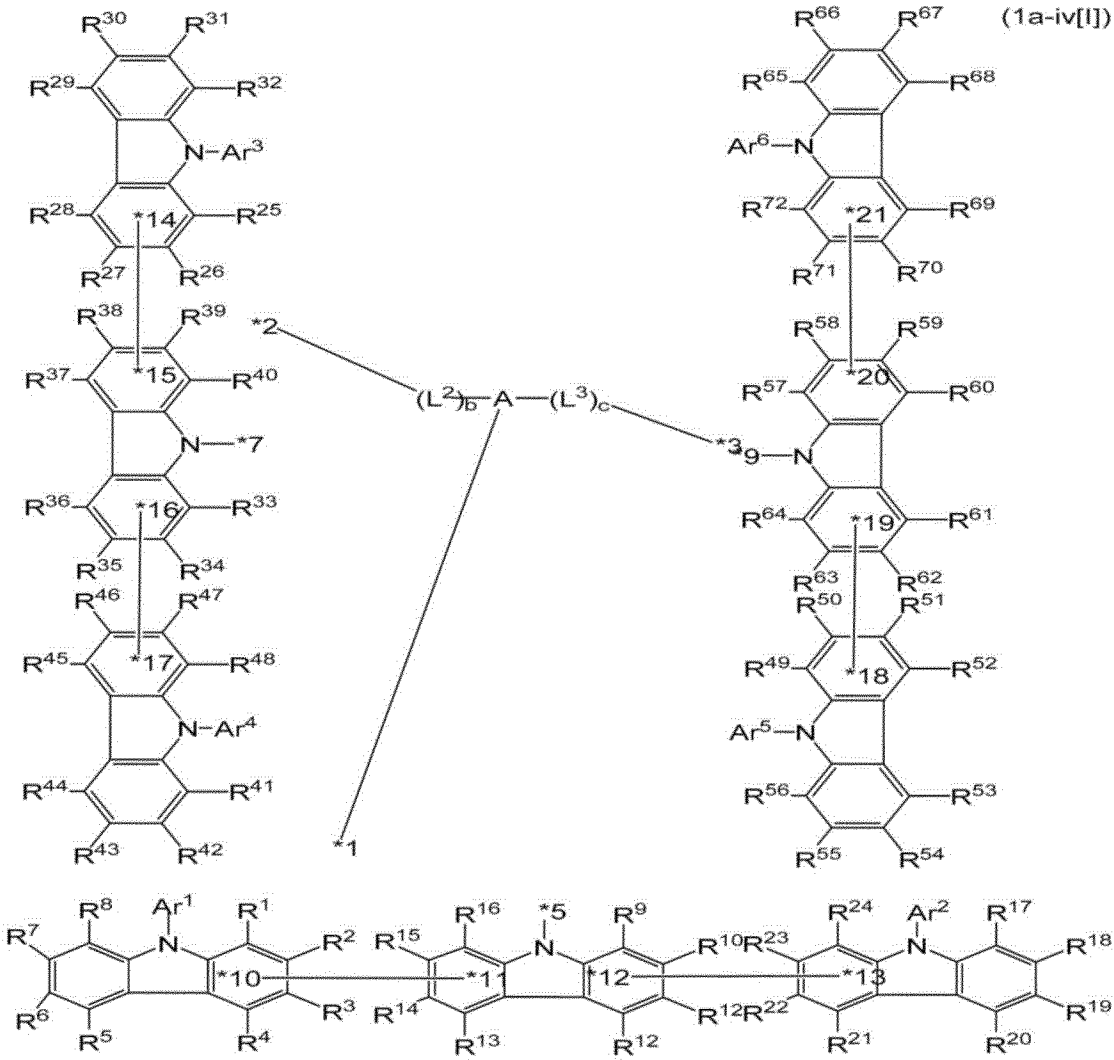
--                                                                                                        --.

Columns 2329 and 2330, Claim 9, formula (1a-v[I]),
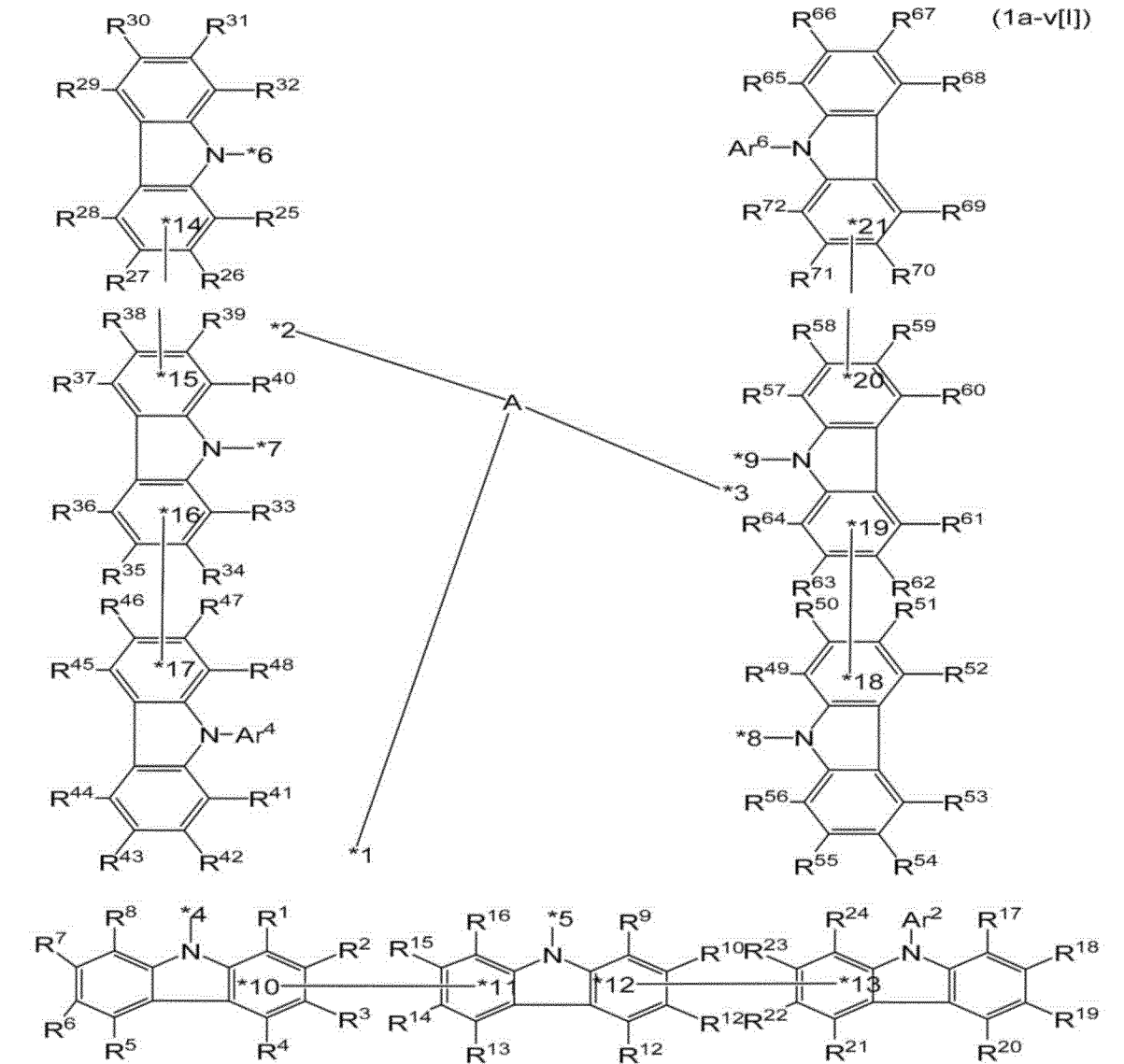
"                                                                                                                          "

should read
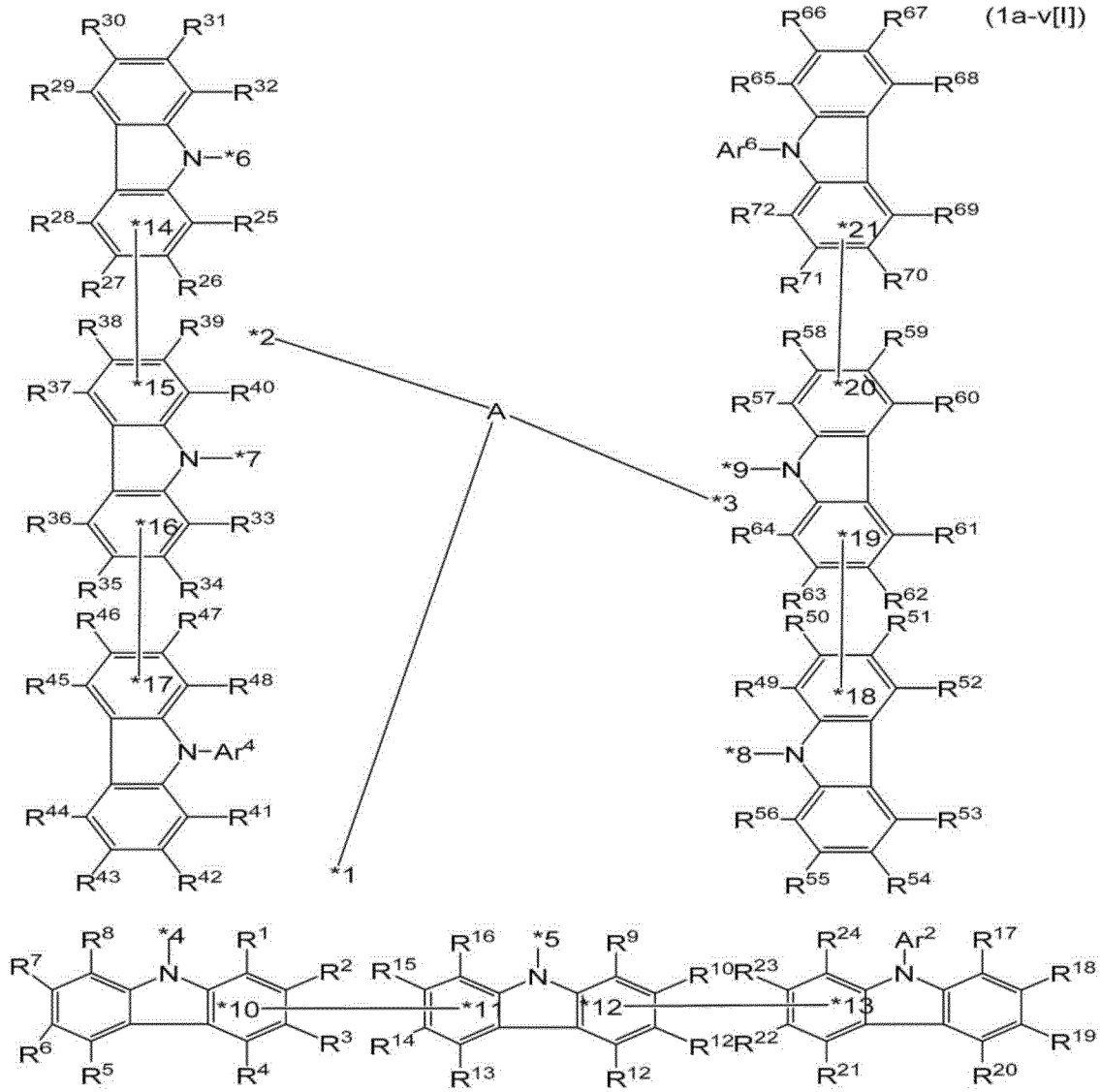
--.

CERTIFICATE OF CORRECTION (continued)
U.S. Pat. No. 10,290,815 B2

Columns 2331 and 2332, Claim 10, formula (1b[I]), "$R^{46}$"

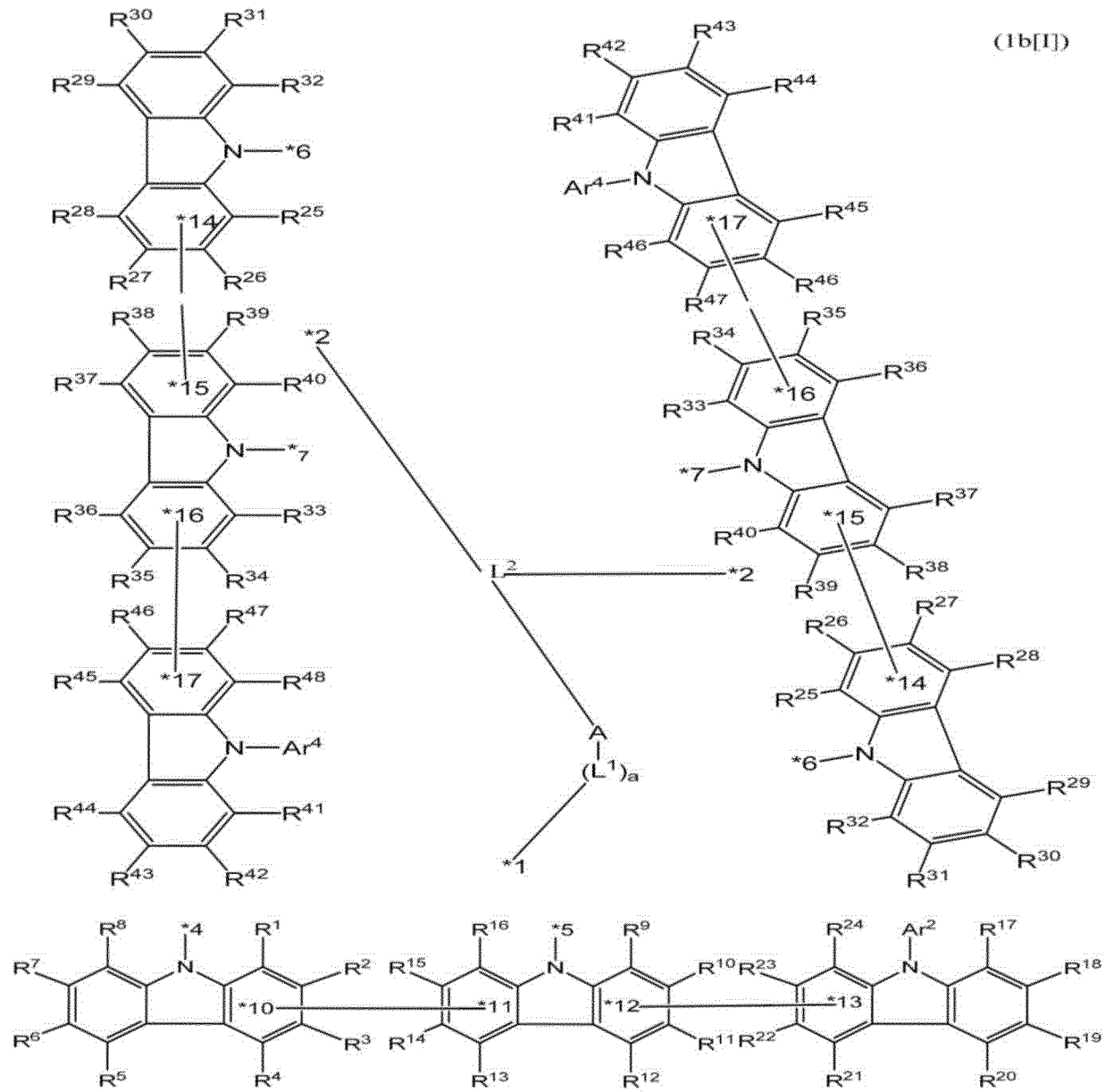

should read --$R^{48}$--.
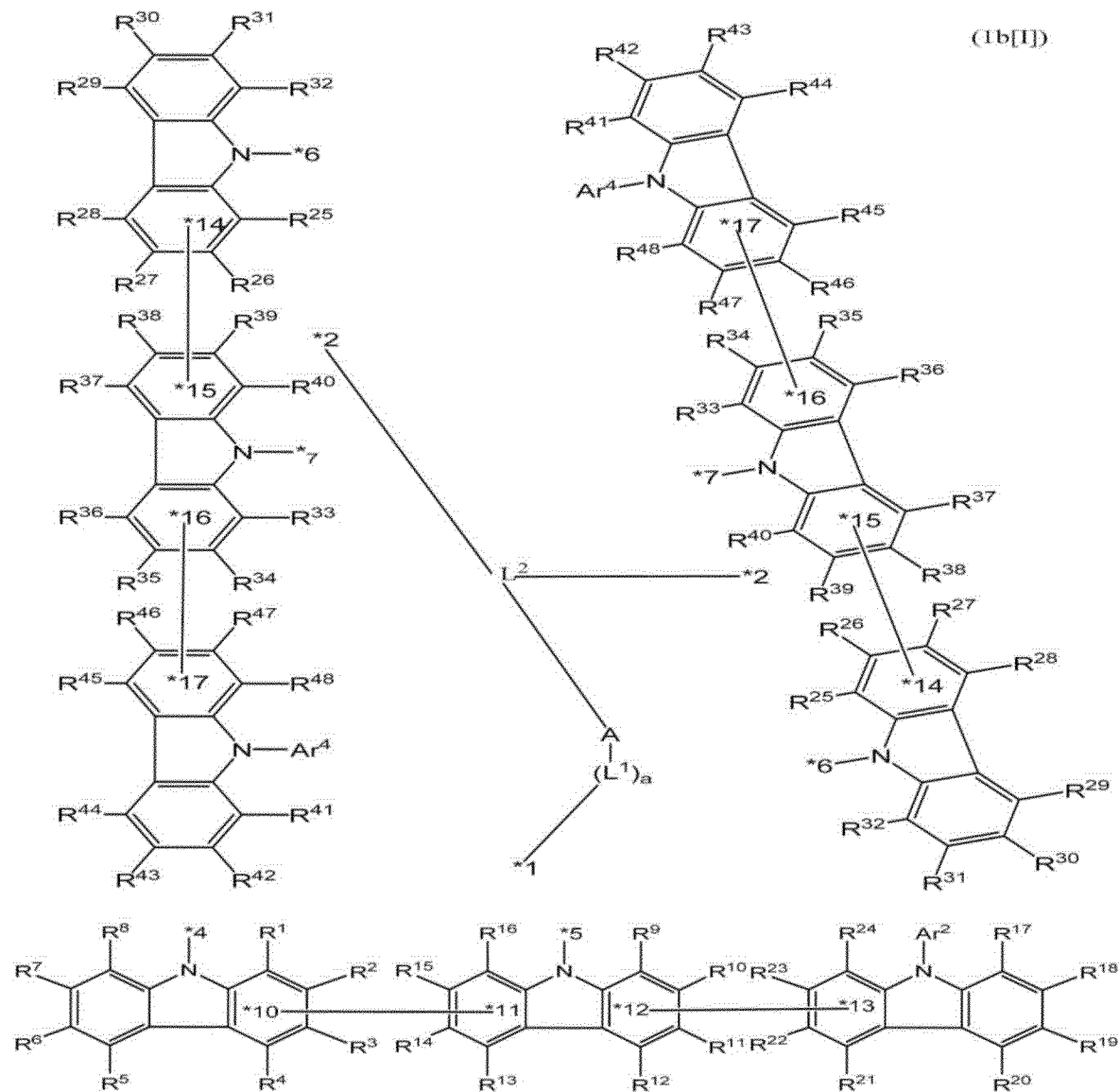
Column 2331, Line 59, Claim 10, "A, $L^1$, $L^2$, a, to *7, $Ar^2$", and A' are" should read --A, $L^1$, $L^2$, a, *1 to *7, $Ar^2$, and $Ar^4$ are--.
Column 2331, Claim 10, Line 63, "10-*11" should read --*10-*11--;
   Claim 10, Line 66, "12-*13" should read --*12-*13--;
Column 2332, Claim 10, Line 58, "14-*15", should read --*14-*15--;
   Claim 10, Line 61, "16-*17", should read --*16-*17--.

Columns 2333 and 2334, Claim 12, formula (1a-vi[I]),
"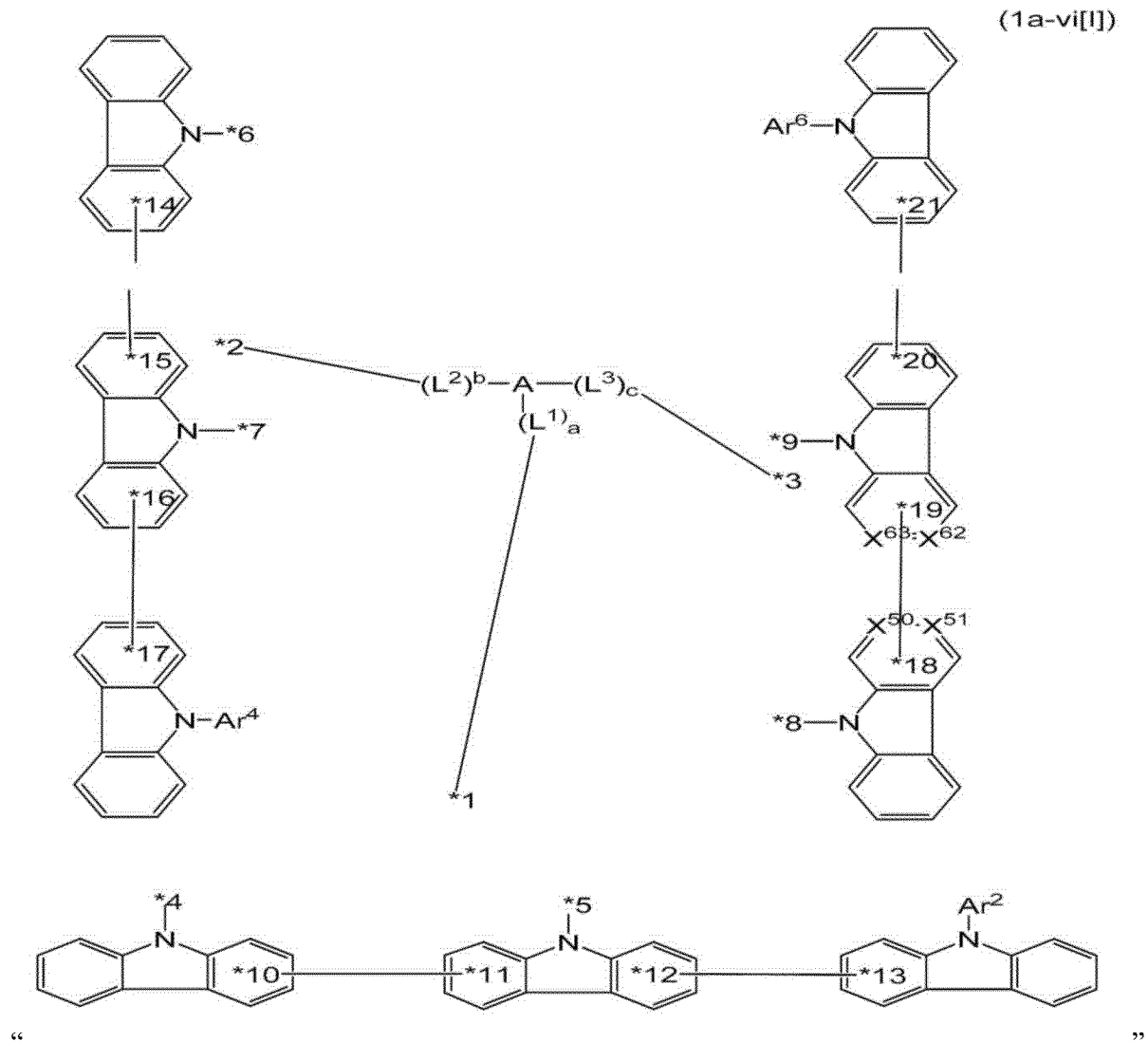"

should read
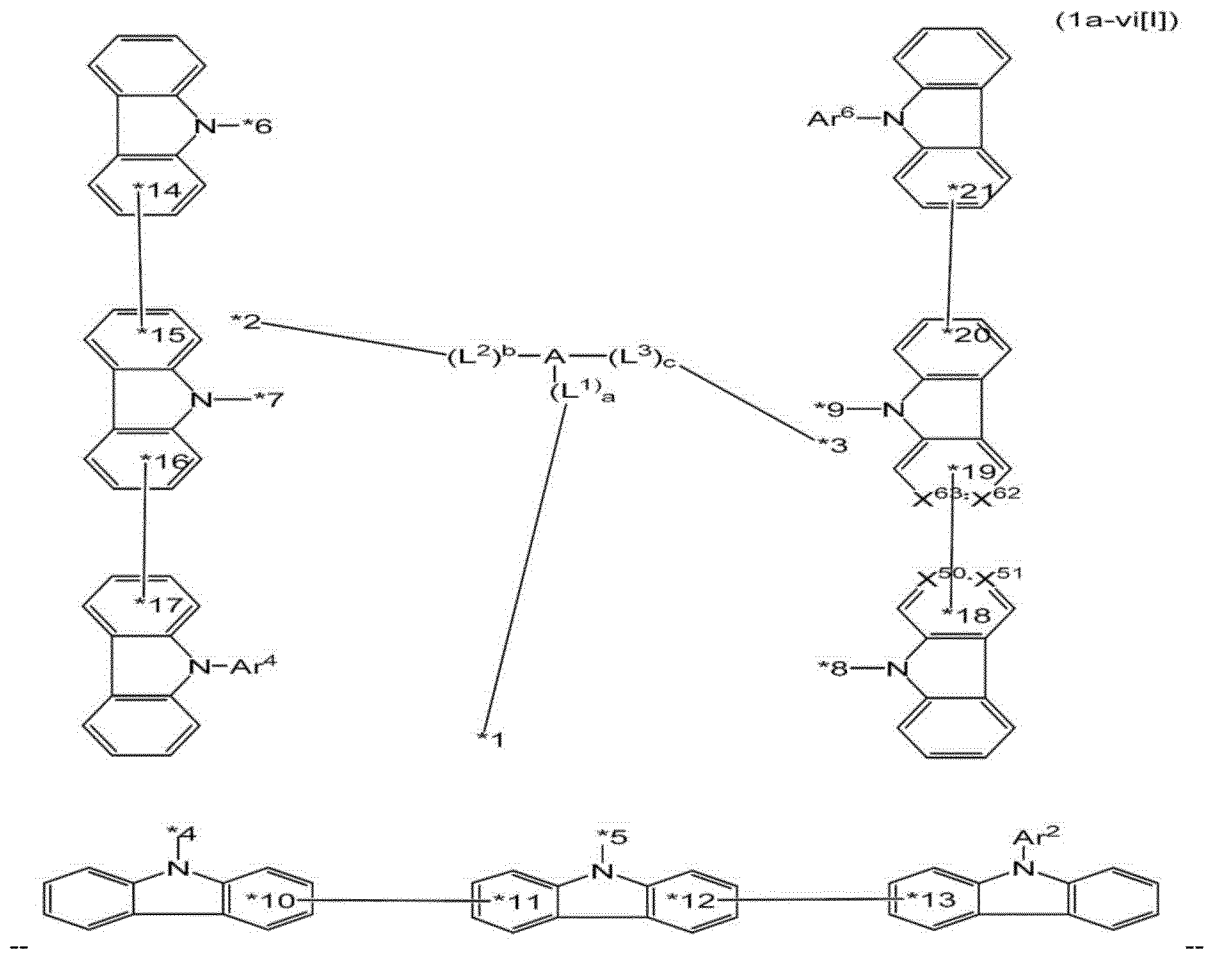
Column 2333, Line 51, Claim 12, "10-*11, *12-*13, * 14-*15, * 16-*17, * 18-*19, and" should read --*10-*11, *12-*13, *14-*15, *16-*17, *18-*19, and--;
Column 2339, Line 45, Claim 15, "are as defined in claim 1;" should read --are as defined in claim 1,--.